(12) United States Patent
Goldsmith

(10) Patent No.: US 11,389,171 B2
(45) Date of Patent: Jul. 19, 2022

(54) INTEGRATED SYSTEM FOR THE INFIXION AND RETRIEVAL OF IMPLANTS

(71) Applicant: David S. Goldsmith, Atlanta, GA (US)

(72) Inventor: David S. Goldsmith, Atlanta, GA (US)

(*) Notice: Subject to any disclaimer, the term of this patent is extended or adjusted under 35 U.S.C. 154(b) by 491 days.

(21) Appl. No.: 15/932,172

(22) Filed: Feb. 14, 2018

(65) Prior Publication Data

US 2019/0247050 A1 Aug. 15, 2019
US 2021/0145445 A9 May 20, 2021

Related U.S. Application Data

(63) Continuation-in-part of application No. 13/694,835, filed on Jan. 9, 2013, now abandoned, which is a
(Continued)

(51) Int. Cl.
*A61B 17/12* (2006.01)
*A61B 17/34* (2006.01)
*A61F 2/82* (2013.01)
*A61B 17/00* (2006.01)
*A61B 18/18* (2006.01)

(52) U.S. Cl.
CPC .... *A61B 17/12118* (2013.01); *A61B 17/0057* (2013.01); *A61B 17/00491* (2013.01); *A61B 17/12181* (2013.01); *A61B 17/3468* (2013.01); *A61B 18/18* (2013.01); *A61F 2/82* (2013.01); *A61B 2017/0065* (2013.01); *A61B 2017/00411* (2013.01); *A61B 2017/00876* (2013.01); *A61B 2017/1205* (2013.01)

(58) Field of Classification Search
CPC ...... A61F 2/06; A61F 2/82; A61F 2/90; A61F 2/91; A61F 2002/821; A61F 2002/823; A61F 2002/825; A61F 2002/826; A61F 2002/828; A61B 17/00491; A61B 17/0057; A61B 17/12181; A61B 17/3468
See application file for complete search history.

(56) References Cited

U.S. PATENT DOCUMENTS 6,030,334 A * 2/2000 Cox .......................... A61N 2/02
600/12
2002/0151760 A1* 10/2002 Paturu ........................ A61F 5/41
600/15
(Continued)

*Primary Examiner* — Tuan V Nguyen
(74) *Attorney, Agent, or Firm* — Meunier Carlin & Curfman LLC

(57) ABSTRACT

Described are coordinated apparatus and methods for drug targeting, clearing the lumen, placing implants within the wall of, and stenting, as necessary, any tubular anatomical structure with single luminal entry. Miniature balls, or miniballs, are introduced into the wall aeroballistically from within the lumen, or small arcuate bands called stays inserted through the outer tunic by means of a hand tool. When miniballs must be placed too closely together to be controlled by hand, a positional control system assists in discharge. Implantation within or proximal to diseased tissue targeting, and thus concentrating the medication in that tissue, miniballs and stays can be used to deliver and controllably release multiple drugs, a radionuclide, or an open or closed loop smart-pill, for example. A glossary of terms follows the specification. Balance of abstract appended to the section entitled Summary of the Invention.

6 Claims, 29 Drawing Sheets

Related U.S. Application Data continuation-in-part of application No. 11/986,021, filed on Nov. 19, 2007, now abandoned.

(60) Provisional application No. 60/860,392, filed on Nov. 21, 2006.

(56) References Cited

U.S. PATENT DOCUMENTS

| | | | | |
|---|---|---|---|---|
| 2005/0143801 A1* | 6/2005 | Aboul-Hosn | ............ | A61F 2/07 623/1.11 |
| 2005/0149002 A1* | 7/2005 | Wang | ...................... | A61L 29/18 606/1 |
| 2006/0041182 A1* | 2/2006 | Forbes | ...................... | A61F 2/82 600/12 |
| 2006/0129228 A1* | 6/2006 | Golesworthy | ............ | A61F 2/07 623/1.16 |
| 2008/0101677 A1* | 5/2008 | Maschke | ............ | A61B 5/02007 382/131 |
| 2012/0277774 A1* | 11/2012 | Guo | ...................... | A61B 17/11 606/153 |
| 2014/0163664 A1* | 6/2014 | Goldsmith | ....... | A61B 17/12181 623/1.11 |

* cited by examiner

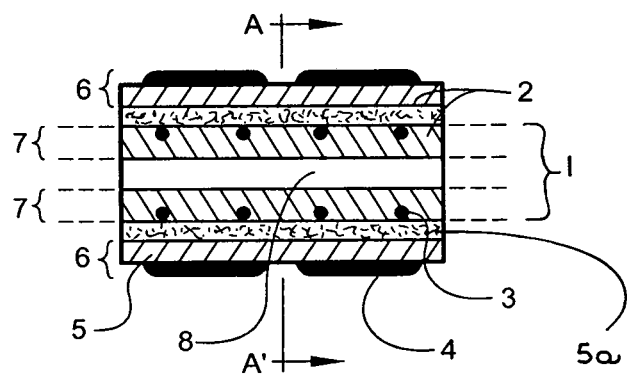
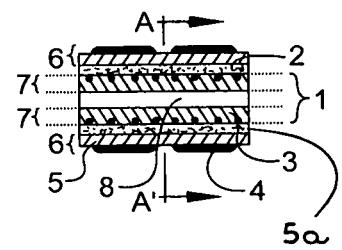
Fig.2          Fig.3
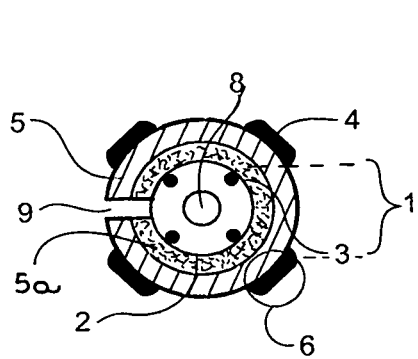
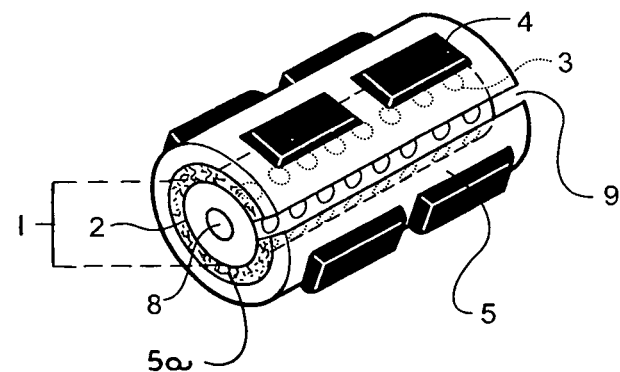
Fig.4          Fig.5

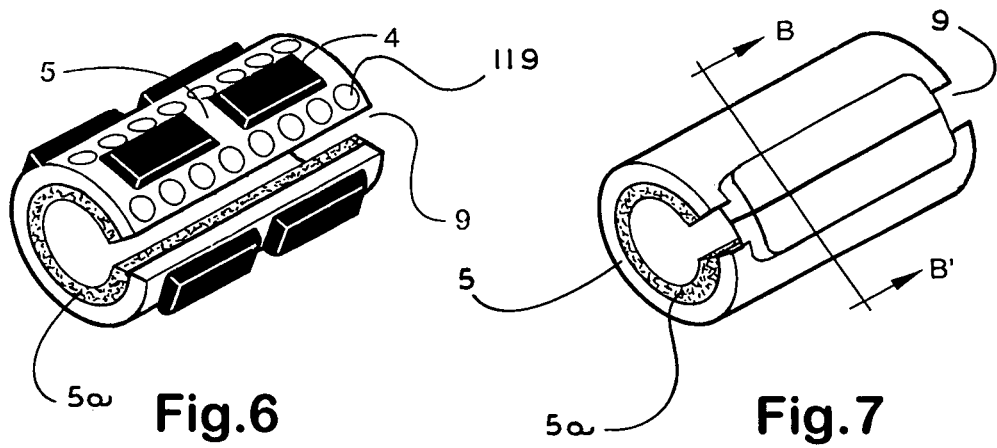
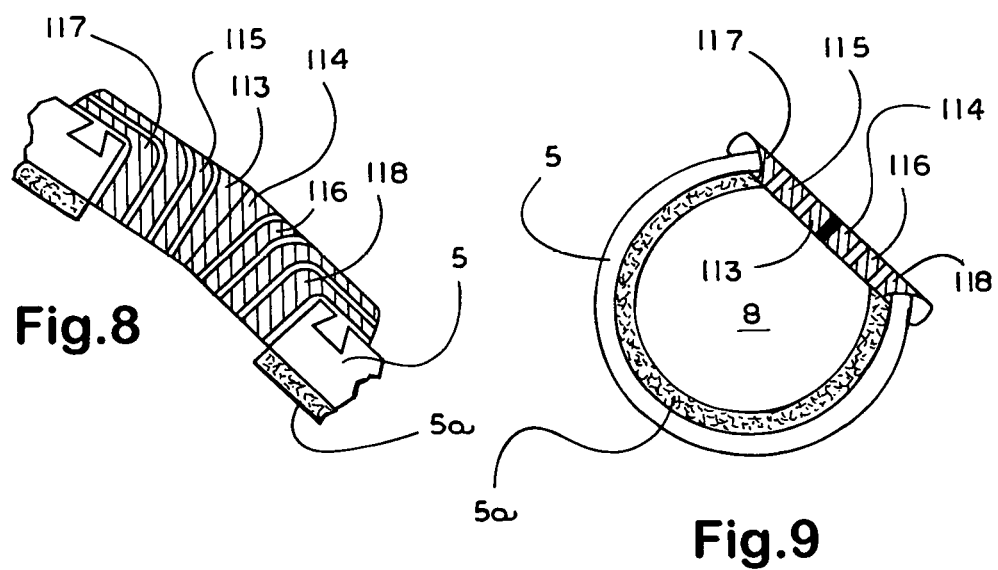

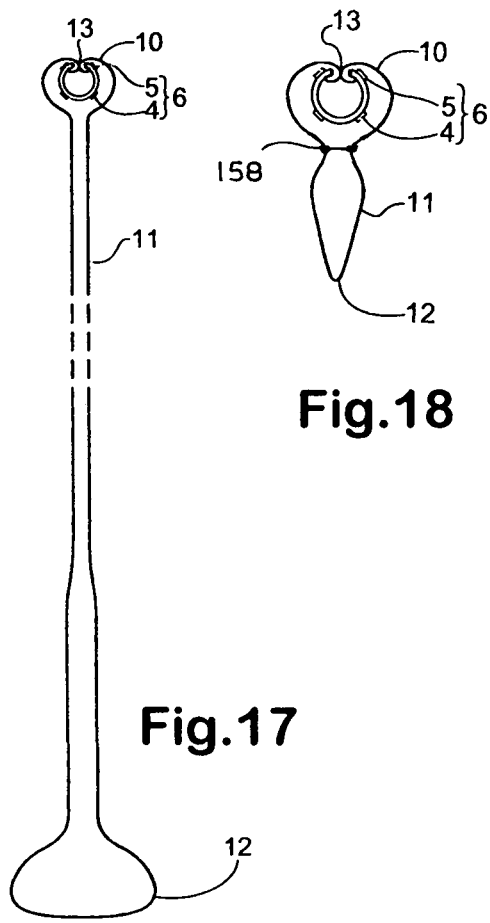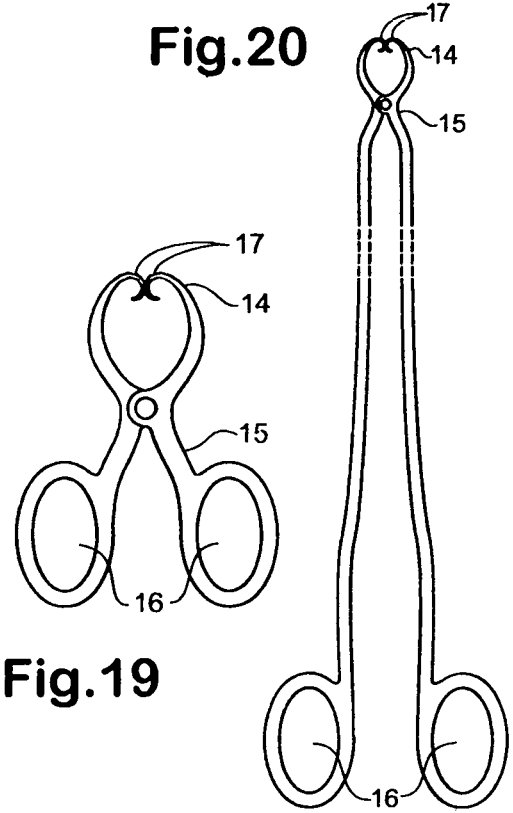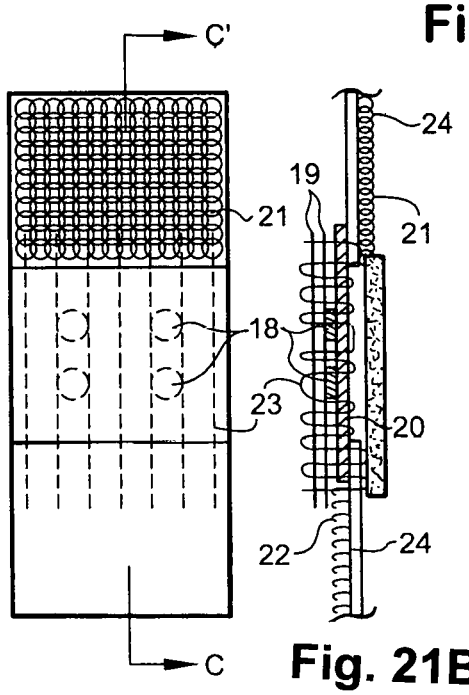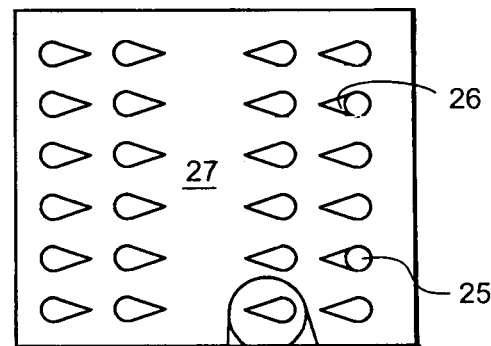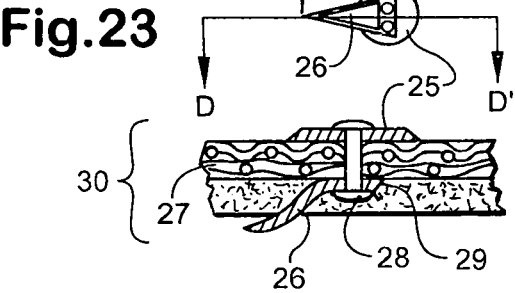
Fig.17 Fig.18 Fig.19 Fig.20 Fig.21A Fig.21B Fig.22 Fig.23 Fig.24

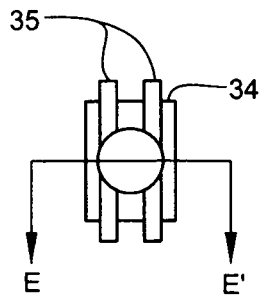
Fig.25
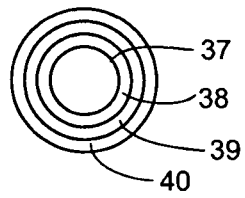
Fig.27
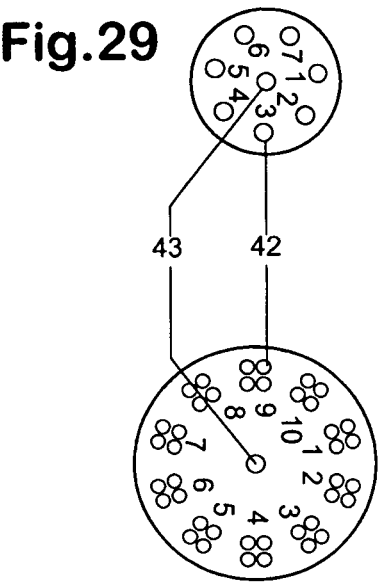
Fig.29
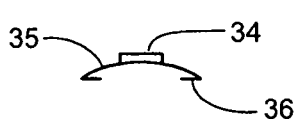
Fig.26
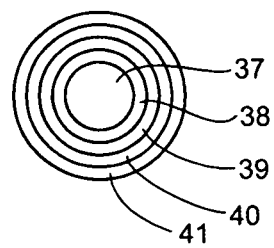
Fig.28
Fig.30
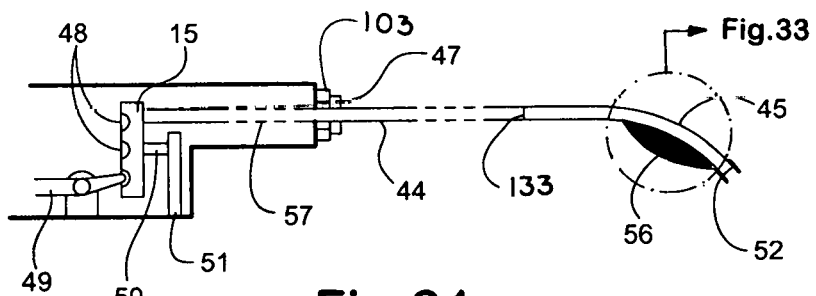
Fig.31
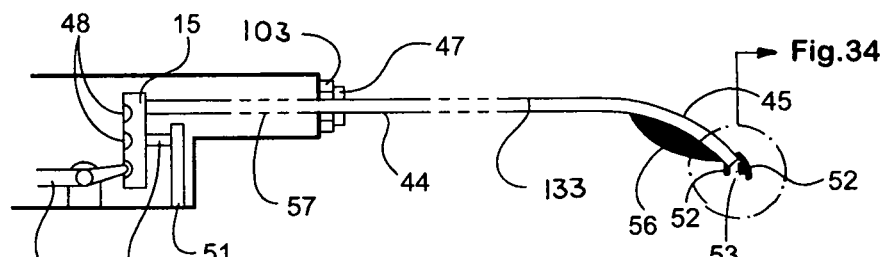
Fig.32

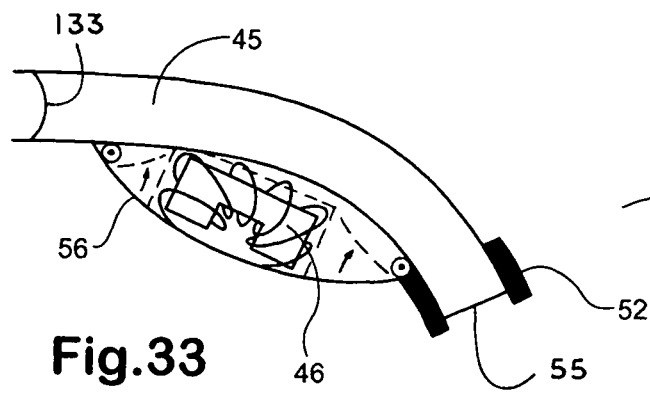
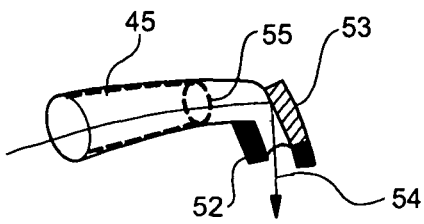
Fig.33  Fig.34
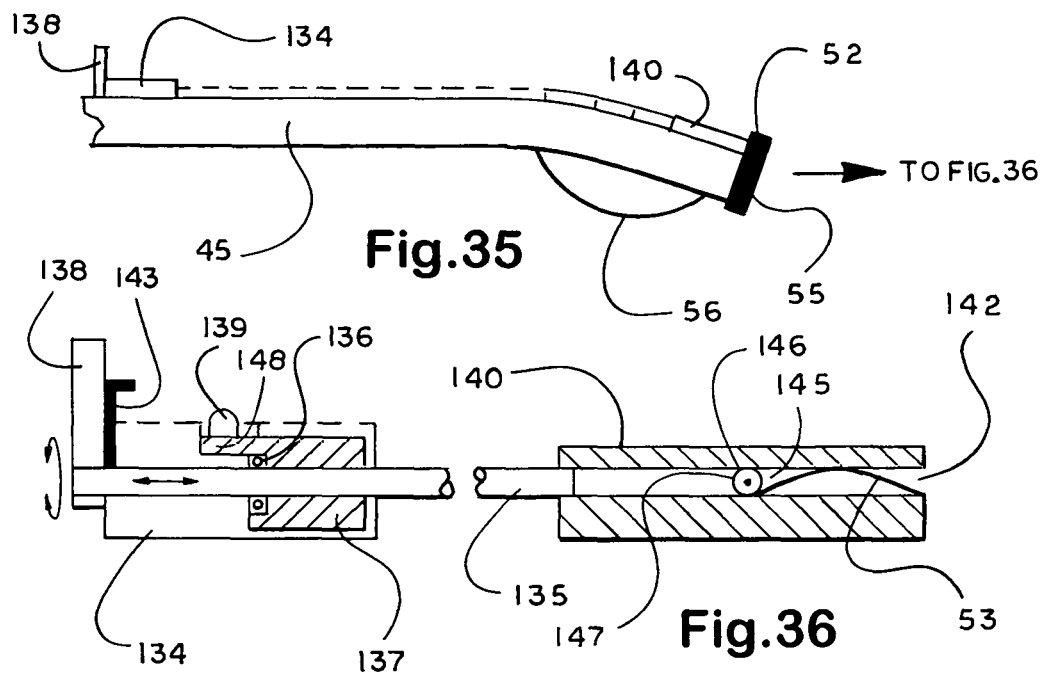
Fig.35
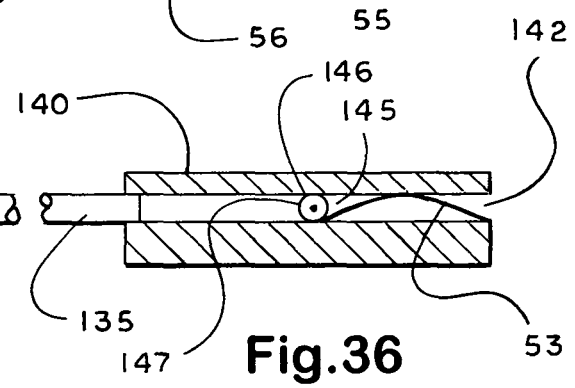
Fig.36
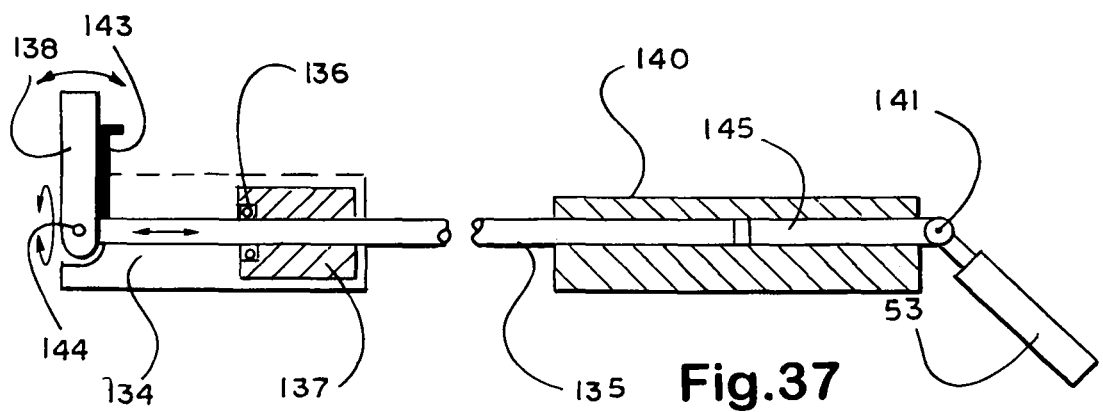
Fig.37

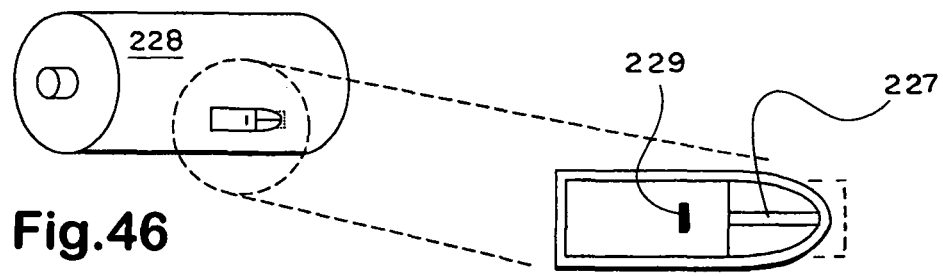
Fig.46
Fig.47
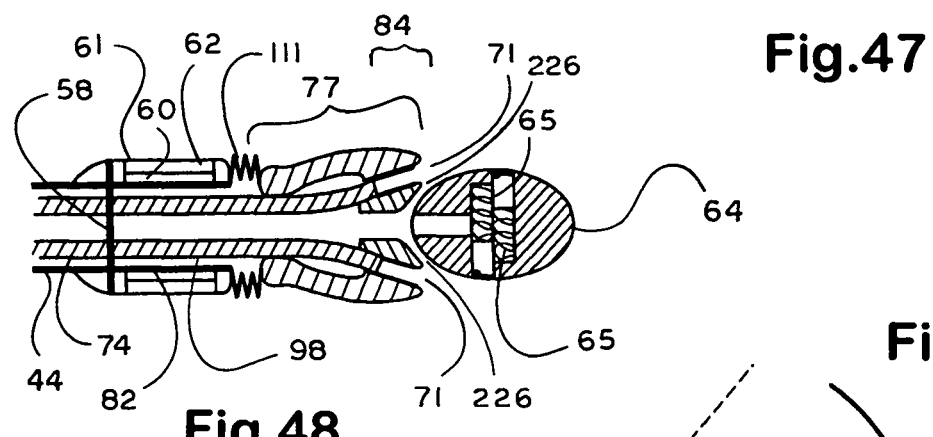
Fig.48
Fig.50
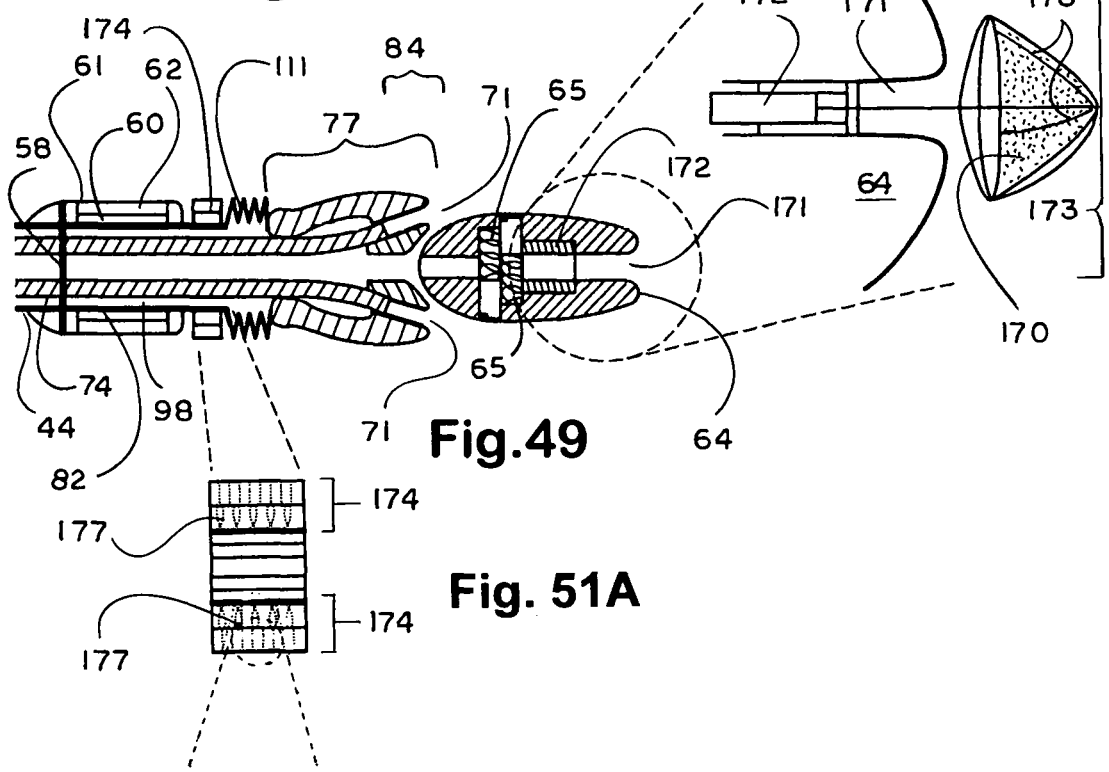
Fig.49
Fig. 51A
Fig. 51B  Fig. 51C
Fig. 51D  Fig. 51E

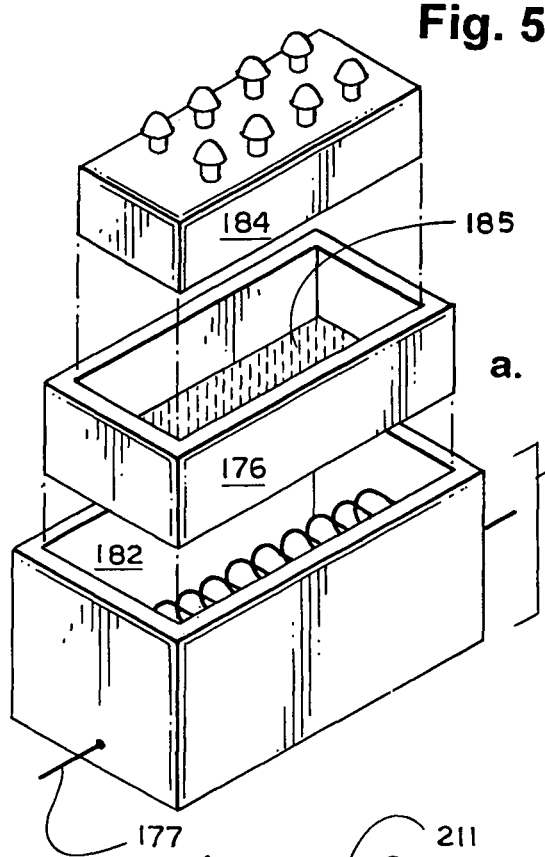
Fig. 53A
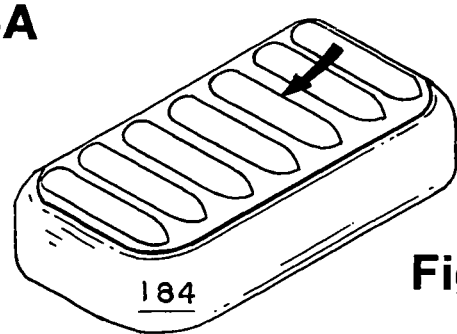
Fig. 53B
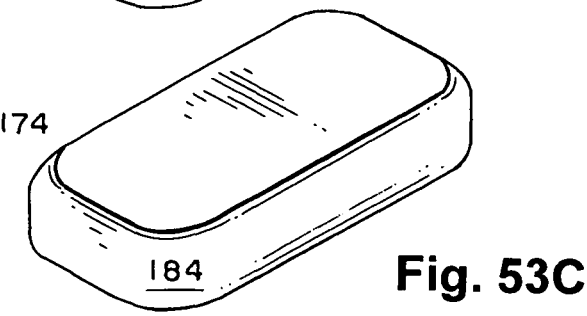
Fig. 53C
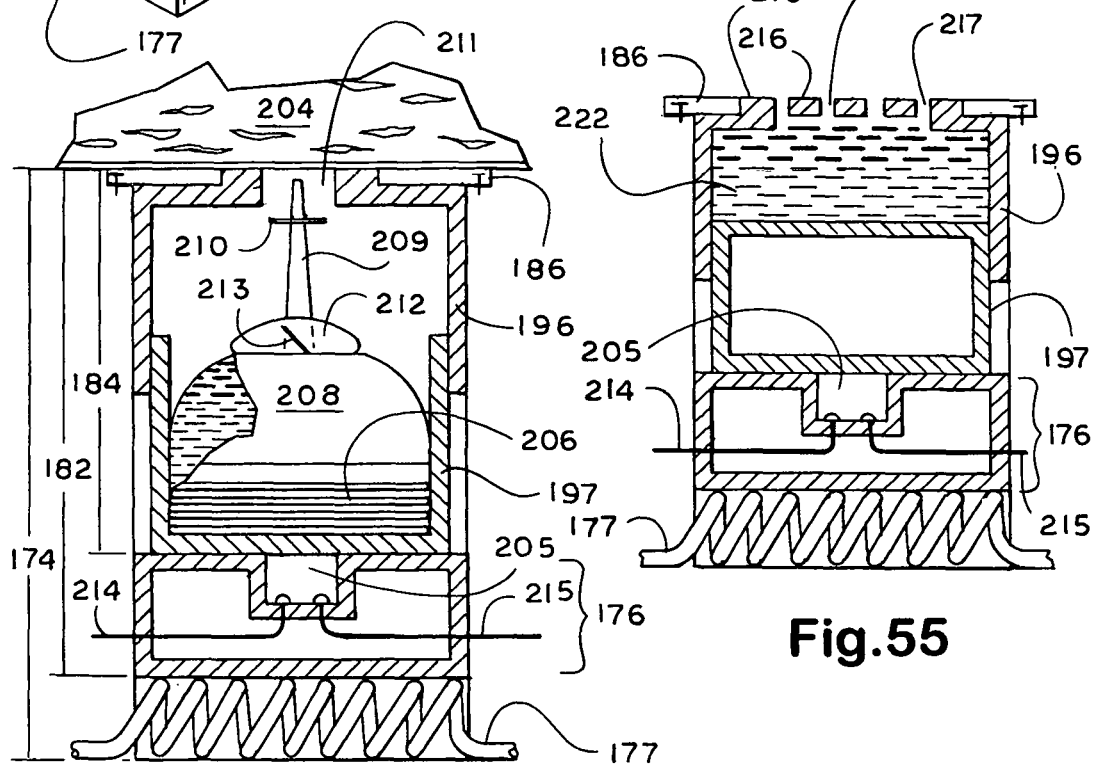
Fig.54
Fig.55

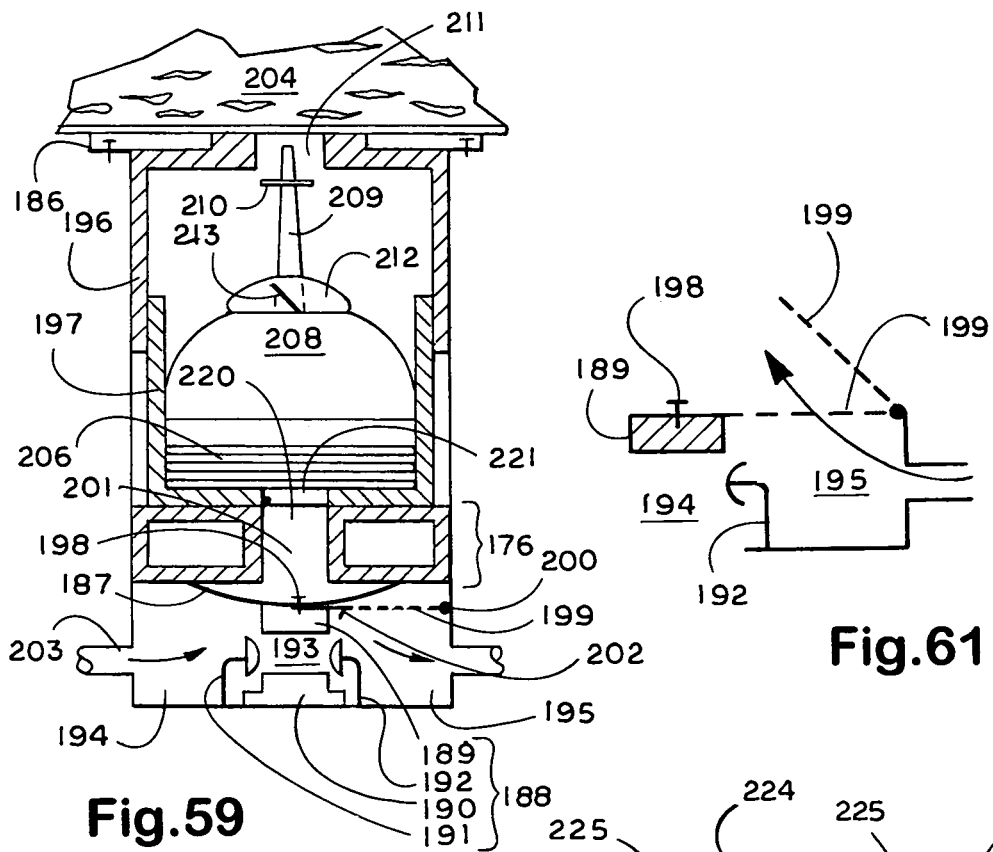
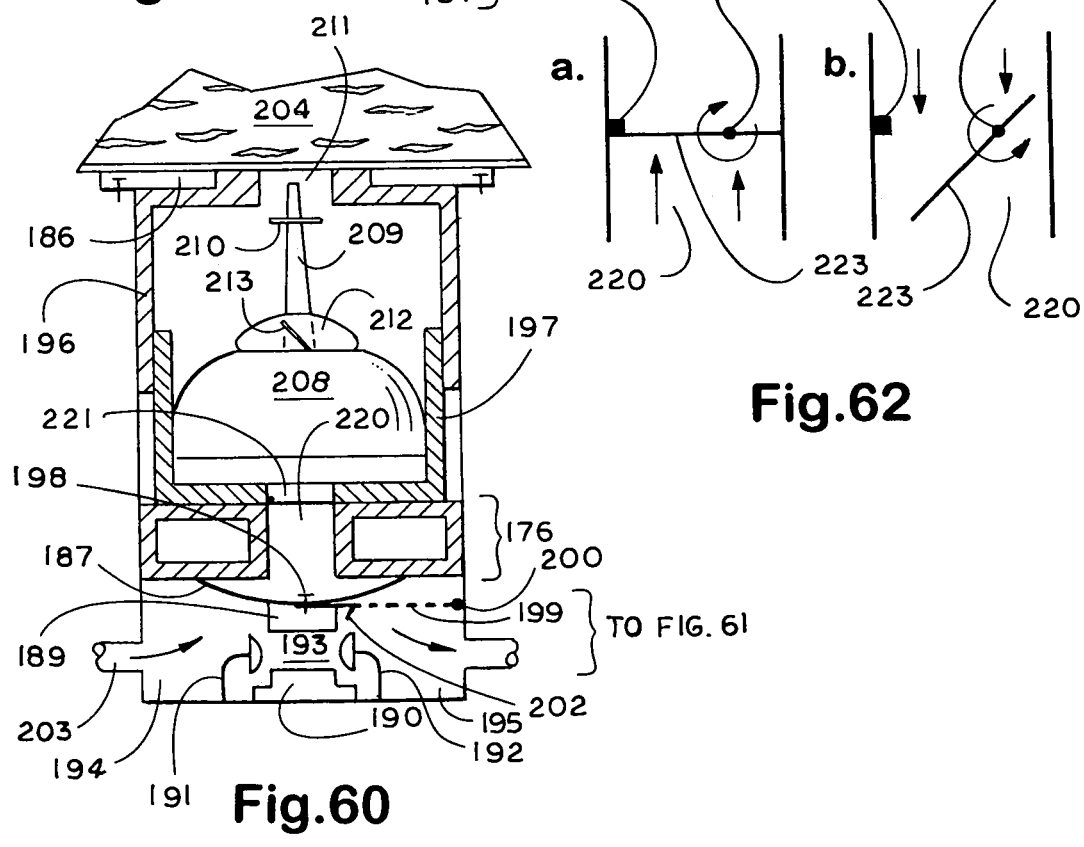
Fig.59
Fig.61
Fig.60
Fig.62

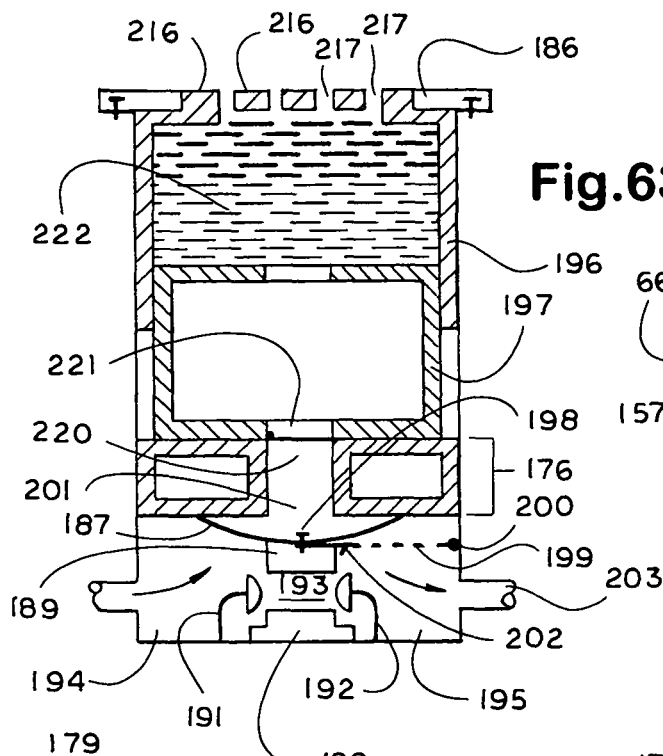
Fig.63
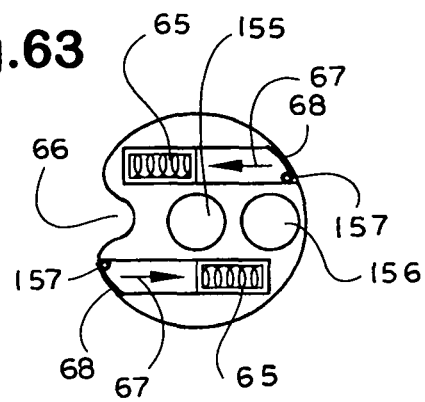
Fig.67
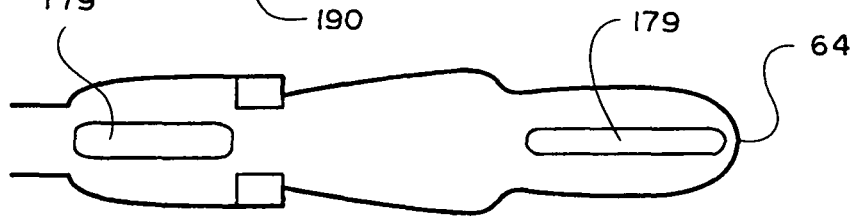
Fig.64
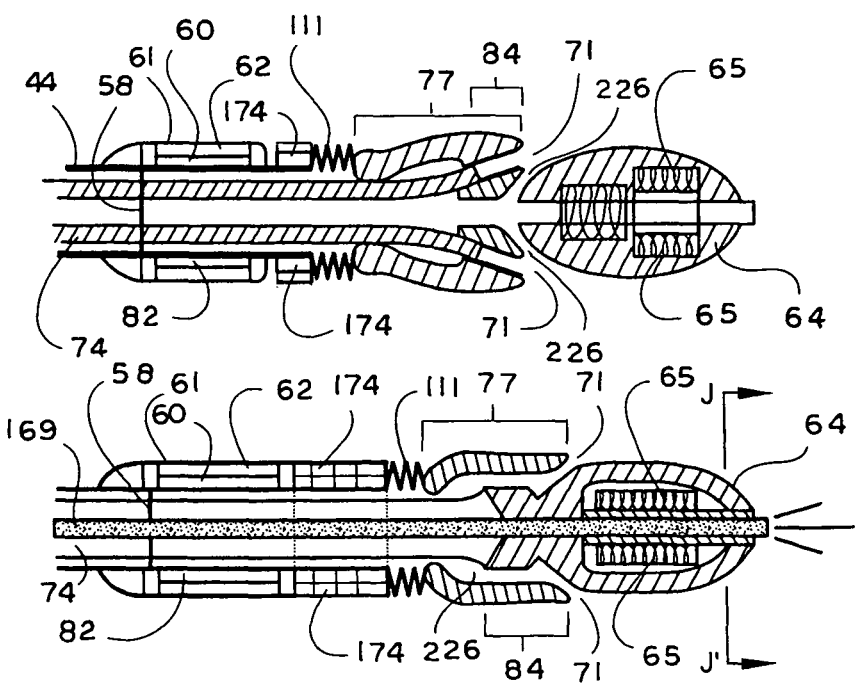
Fig.65
Fig.66

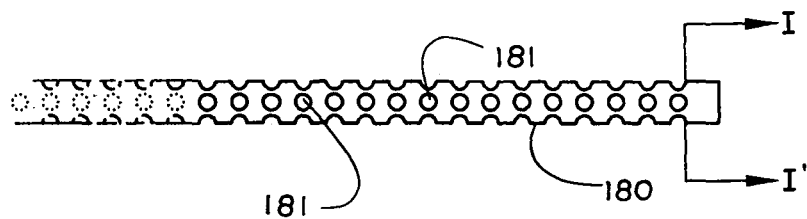
Fig.68  Fig.69
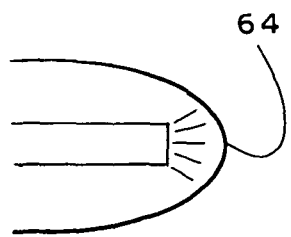
Fig.70
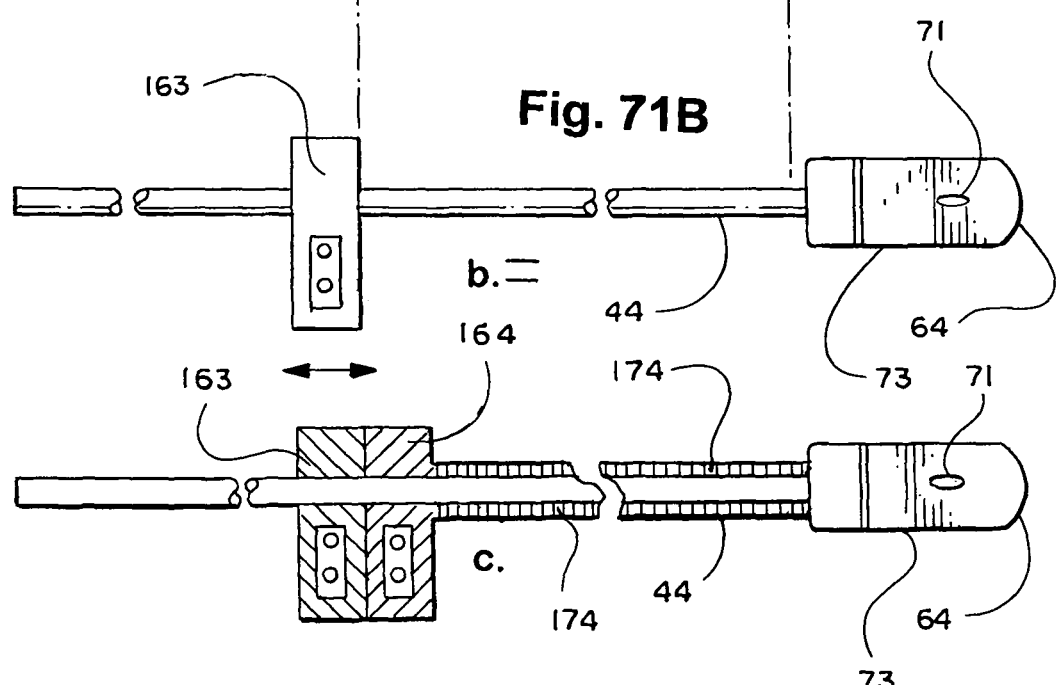
Fig. 71A
Fig. 71B
Fig. 71C

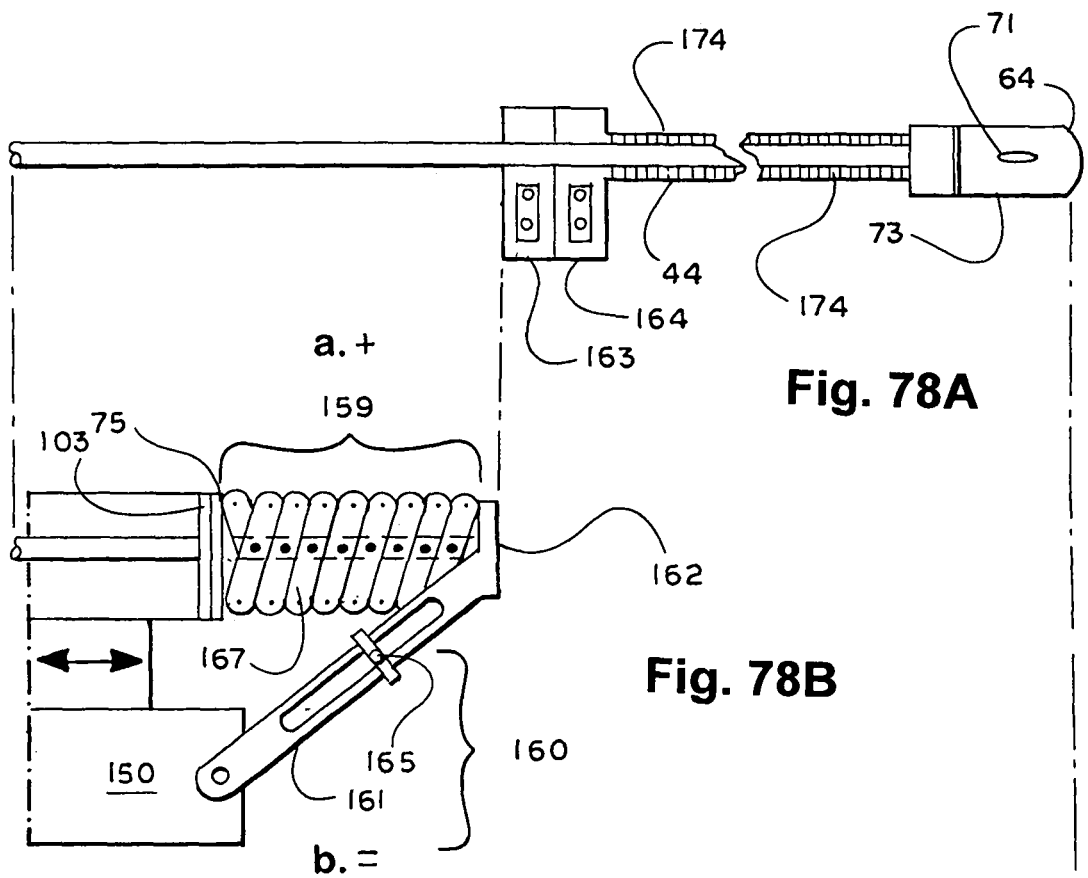
Fig. 78A
Fig. 78B
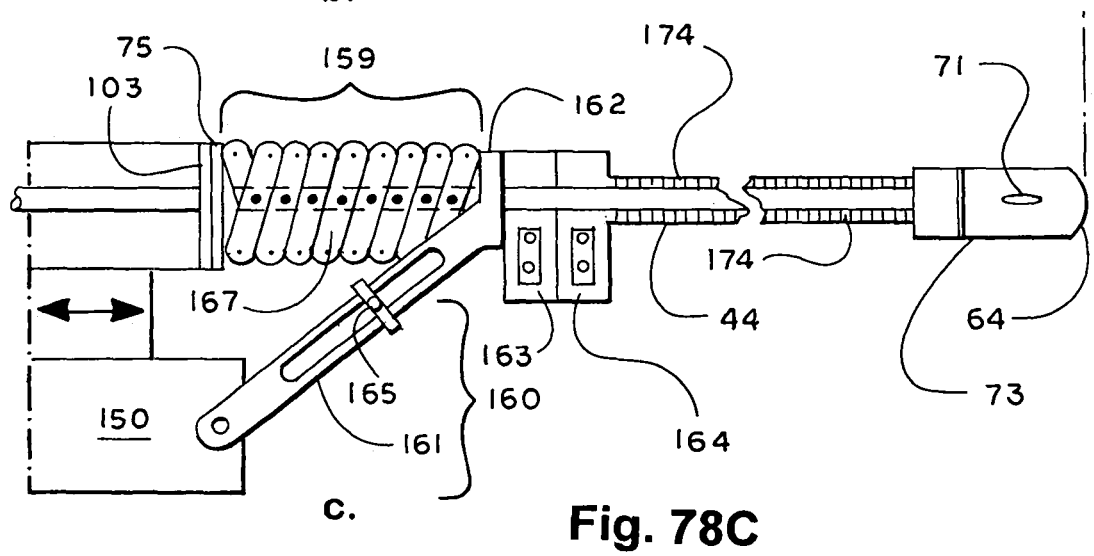
Fig. 78C

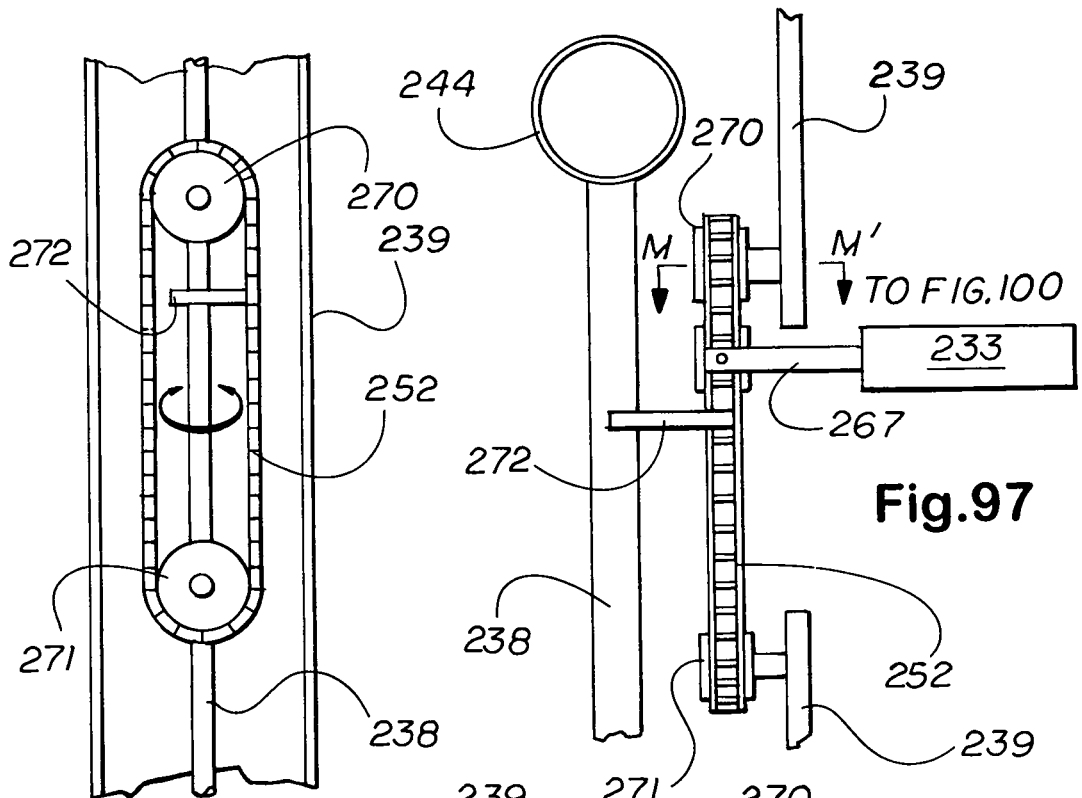
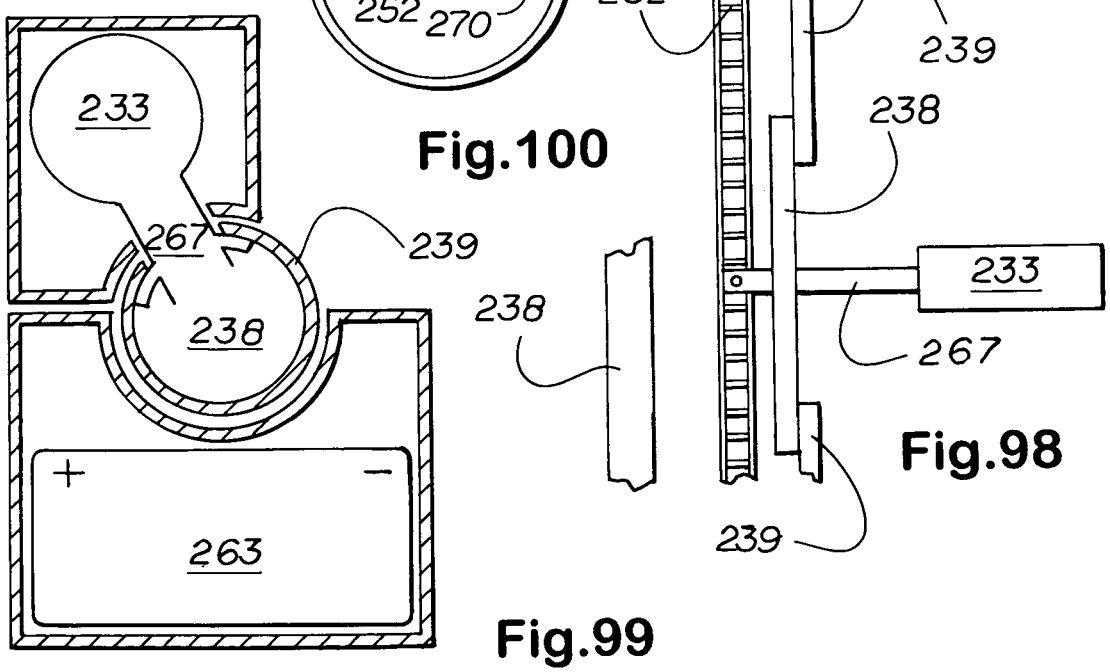
Fig.96 Fig.97 Fig.98 Fig.99 Fig.100

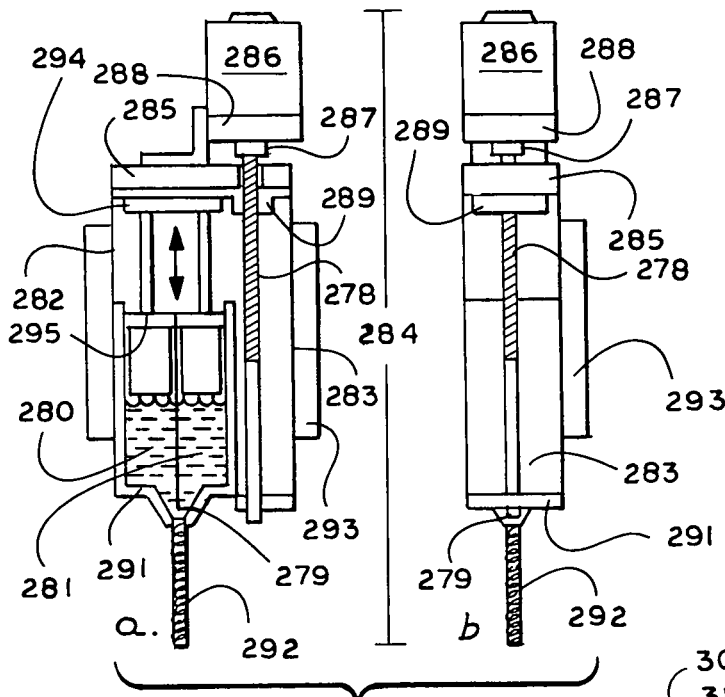
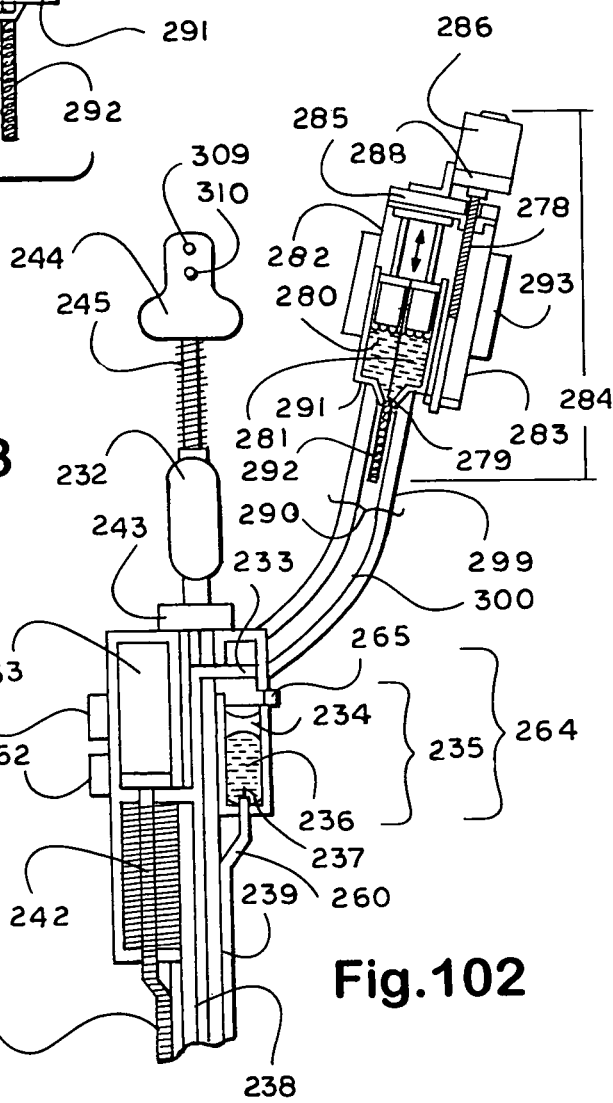

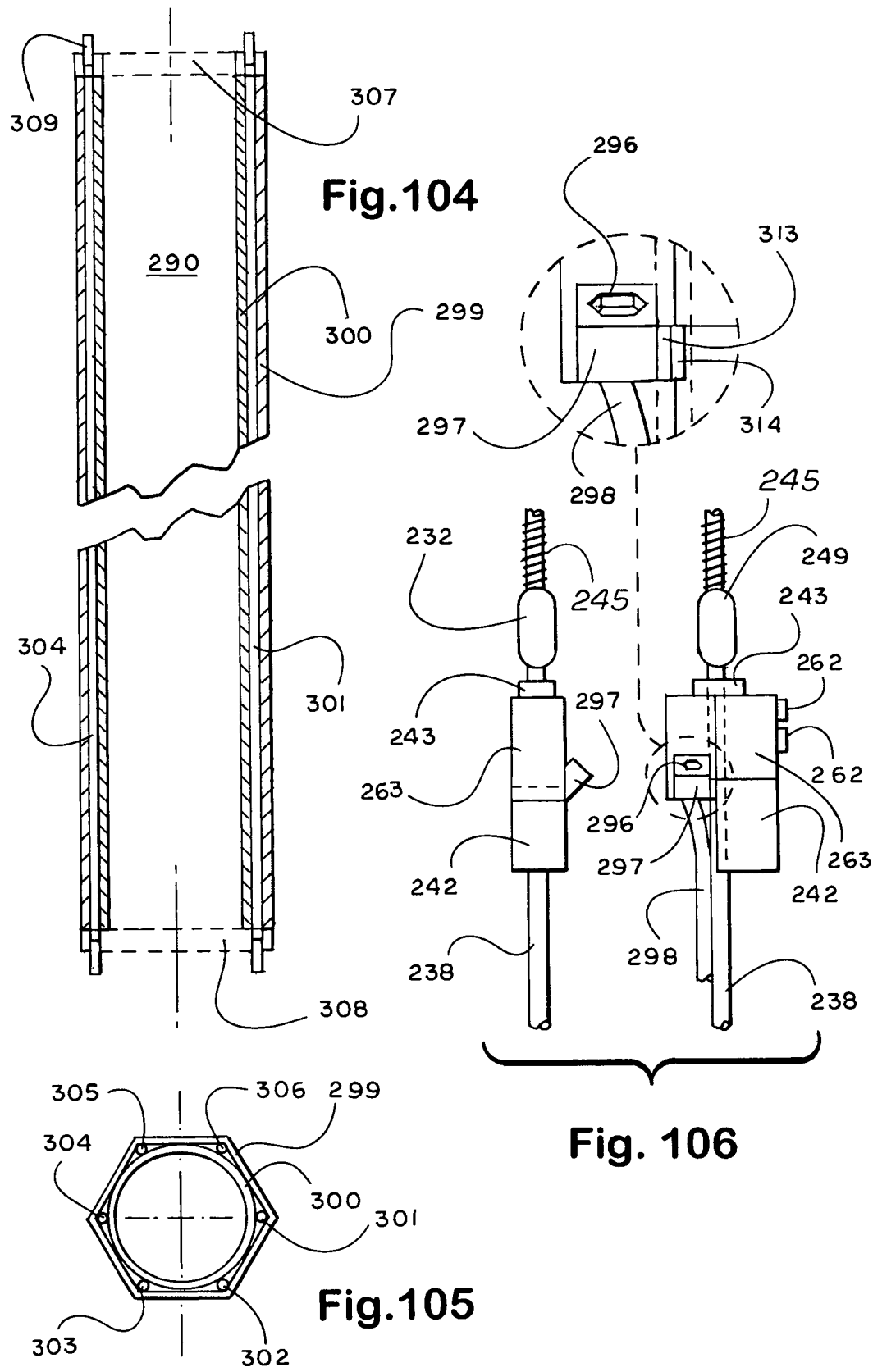

PIT-PUMP INTAKE TURRET
POT-PUMP OUTLET TURRET

INTEGRATED SYSTEM FOR THE INFIXION AND RETRIEVAL OF IMPLANTS

CROSS REFERENCE TO RELATED APPLICATION

This application is a continuation-in-part of parent application Ser. No. 11/986,021, filed on 19 Nov. 2007 and published on 11 Nov. 2010 as 20100286791 under the title Integrated System for the Ballistic and Nonballistic Infixion and Retrieval of Implants and also continuation-in-part application Ser. No. 13/694,835, filed on 9 Jan. 2013 and published on 12 Jun. 2014 as 2014/0163664 under the title Integrated System for the Ballistic and Nonballistic Infixion and Retrieval of Implants with or without Drug Targeting. Parent application Ser. No. 11/986,021 succeeded and claimed the benefit of Disclosure Document 565662, filed on 21 Nov. 2004, and Provisional Patent Application 60/860,392, filed on 21 Nov. 2006 under 35 U.S.C. 119(e), the content of these earlier disclosures incorporated by reference. This continuation-in-part application supersedes parent application Ser. No. 11/986,021 and continuation-in-part application Ser. No. 13/694,835, these earlier applications herewith abandoned.

TABLE OF CONTENTS
CROSS REFERENCE TO RELATED APPLICATION
TABLE OF CONTENTS
BACKGROUND OF THE INVENTION
1. Field of the invention
2. Preliminary description of the invention
3. Terminology
4. Concept of the ductus-intramural implant
4a. Tissue acceptance of ductus-intramural implant
4a(1). Significance of sterile antixenic immune tissue reaction
4a(2). Duration, extent, and outcome of sterile tissue reaction
4a(3). Tissue reaction ameliorative measures
4b. Medicinal and medicated miniballs and stays
4b(1). Drug-releasing and irradiating miniballs, stays, and ferrofluids
4b(2). Local release of miniballs and stays
4b(3). Use of drug-releasing ductus-intramural implants to locally counteract or reinforce angiogenic or other systemic medication
4b(4). System implant magnetic drug and radiation targeting
4b(5). Circulating drug-blocking and drug interaction avoidance
4b(6). Drug-targeting miniballs and stays
4c. Implants that radiate heat on demand
4d. Chemical adjuvants and precautionary measures
4d(1). Administration of target and target-adjacent implantation-preparatory substances
4d(2). Ductus wall tumefacients
4d(3). Nontumefacient enables attainment of implantable ductus-intramural thickness
4e. Stabilization of the implant insertion site
4e(1). Gross positional stabilization (immobilization) of the implant insertion site
4e(2). Tissue stabilization at the treatment site
4e(2)(a). Temperature stabilization
4e(2)(b). Removal of vulnerable plaque or accreted material at the implant insertion site
4f. Abrupt closure with thrombus and vasospasm
4f(1). Risk of abrupt closure with thrombus and vasospasm
4f(2). Prevention of abrupt closure with thrombus and vasospasm
4g. Emergency recovery of miniballs and stays
5. Means for the placement of ductus-intramural implants
6. Endoluminal prehension of miniballs and ferrofluids
7. Comparison with prior art angioplasty
8. Concept of the extraluminal stent
8a. Basic strengths and weaknesses of prior are stenting in vascular, tracheobronchial, gastrointestinal, and urological interventions
8b. The extraluminal stent
8b(1). The intraductal component of the extraluminal stent and the means for its insertion
8b(1)(a). Types of ductus-intramural implants used for stenting
8b(1)(b). Use of ductus-intramural implants for stenting
8(2). The extraductal component of the extraluminal stent and the means for its insertion
8(2)(a). Types of stent-jacket
8(2)(a)(i). Extrinsically magnetized stent-jackets
8(2)(a)(ii). Intrinsically magnetized stent-jackets
8(2)(a)(iii). Hybrid extrinsically and intrinsically magnetized stent-jackets
8(2)(a)(iv). Quasi-intrinsically magnetized stent-jackets
8(2)(a)(v). Laminated stent-jackets
8(2)(a)(vi). Spine and ribs-type stent-jackets
8(2)(a)(vii). Absorbable stent-jackets
8(2)(a)(vii). Radiation shield-jackets and radiation shielded stent-jackets absorbable and absorbable
8c. Placement of the extraluminal stent
8c(1). Considerations as to access
8c(2). Means for the placement of the stent-jacket
8d. Closer comparison of extraluminal to endoluminal, or conventional, stenting
8e. Accommodation of the adventitial vasculature, innervation, and perivascular fat
8f. Necrosis and atherogenesis-noninducing conformation of stent-jackets
8g. Means for accommodating the vasa and nervi vasora with special reference to the end-arterial form and neovascularization of the coronary arteries
8h. Requirement for moisture barrier-coated viscoelastic polyurethane foam linings
8i. Positional stabilization of implants
8i(1). Use of solid protein solders
8i(2). Means for inducing the formation of a strong implant-tissue bond
9. Minimizing the risk of rebound
10. Concept of ballistic insertion
11. Use of a positional control system
12. Concept of the impasse-jacket
13. Concept of the magnet-wrap
14. Concept of the nonjacketing side-entry connector
15. System requirements
16. System features
OBJECTS OF THE INVENTION
SUMMARY OF THE INVENTION
BRIEF DESCRIPTION OF THE DRAWINGS
DESCRIPTION OF THE PREFERRED EMBODIMENTS
I. STENT-JACKETS AND STENT-JACKET SUPPORTING ELEMENTS
I1. General considerations to include insertion
I2. Structural and functional considerations
I3. Order of stent-jacket placement
I3a. Circumstances recommending the use of a shield-jacket or preplacement of the stent-jacket I3b. Sequence of stent-jacket placement and implantation I3c. Sequence of stent-jacket placement and implantation in relation to trap-extractor (recovery) electromagnet susceptibility and field intensity I4. Internal environment-resistant base-tube polymers, metals, and combinations thereof I5. Protective encapsulation of the stent-jacket I6. Stent-jackets with sling string pull opener I7. Stent and shield-jacket protective linings I7a. Double-wedge stent- and shield-jacket rebound-directing linings I7a(1). Conformation of double-wedge linings I7a(2). Functional background to double-wedge linings I7a(3). Materials suitable for rebound-directing double-wedge linings I7a(4). Nonmagnetized base-tube and double-wedge shield-jackets I7b. Stent- and shield-jacket moisture barrier-coated viscoelastic polyurethane foam linings I7c. Stent- and shield-jacket anti-migration linings I8. Radiation shielded stent-jackets I9. Jacket end-ties and side-straps I9a. Form of end-ties I9b. Use of end-ties I10. Absorbable extraluminal magnetic stent-jackets and materials I10a. Absorbable base-tube and stent-jacket, miniball, stay, and clasp-magnet matrix materials I10b. Noninvasive dissolution on demand of absorbable stent-jackets, base-tubes, radiation shields, and miniballs I10c. Absorbable and nonabsorbable periductal jackets with medicated linings

I11. STENT-JACKET EXPANSION INSERTS

I11a. Expansion inserts absorbable, meltable, and comminutable for time-discrete decremental contraction of stent-jackets I11b. Intracavitary infusion of fluid for lithotriptor dissolution of long-term controlled destruction-time expansion inserts or a final stone base-tube bonded layer in multilayered expansion inserts I11c. Absorbable stent-jacket expansion insert materials with relatively short breakdown times I11d. Lithotriptor-destructible stone stent-jacket expansion inserts and differentially destructible expansion insert layers I11e. Expansion insert bonding agents (adhesives)

I11e(1). Intrinsic shorter-term insert-to-base-tube and segment-to-segment bonding agents I11e(2). Longer-term expansion insert-to-base-tube and layer-to-layer bonding agents I11e(3). Extrinsic shorter-term (absorbable) to longer-term (stone) layer bonding agents I12. Retardation in the dissolution of absorbable stent-jackets, stent-jacket expansion inserts, and stays I13. Alternative procedure to the use of expansion inserts

I14. SECTIONAL, OR CHAIN-STENTS, SEGMENTED AND ARTICULATED

I14a. Purposes and types of chain-stent

I14b. Procedure for placement of a chain-stent

I15. MINIBALL AND FERROFLUID-IMPASSABLE JACKETS, OR IMPASSE-JACKETS

I15a. Uses of impasse-jackets

I15b. Structure of impasse-jackets

I15c. Braced, compound, and chain impasse-jackets

I15d. Cooperative use of impasse-jackets in pairs and gradient arrays

I15e. Direct lines from the body surface to and from impasse- and other type jackets I15f. Single and plural circuit pumping through direct lines to jackets

I16. STENT-JACKET INSERTION TOOLS

I16a. Insertion tool structure

I16b. Use of the stent-jacket insertion tool

II. CLASP-MAGNETS

II1. Subcutaneous, suprapleural, and other organ-attachable clasp- or patch-magnets II2. Chemical isolation of patch-magnet and other implanted components

III. MAGNET-WRAPS

III1. Use of a magnet-wrap

III2. Magnet-wrap structure

IV. CLASP-PATCHES AND CLASP-WRAPS

IV1. Creation of a magnetically retractable surface layer

IV2. Use of a clasp-wrap

IV3. Clasp-wrap-alternative methods for achieving adhesion to the outer surface of the ductus IV3a. Stays configured and/or coated to promote tissue infiltration and adhesion IV3b. Injectable magnetic fluids

V. MINIBALLS

V1. Miniature ball implants

V2. Miniball types, radiation-emitting, medication, drug-eluting magnetized, and magnetized V3. Medication (nonstent) implants and medication-coated miniballs, implants, and prongs V4. Medication-coated miniballs, stays, and prongs with a heat-activated (-melted, -denatured) tissue adhesive-hardener or binder-fixative V5. Heating control over implants and coated implants, to include miniballs, stays, and prongs V5a. Heating of implants and coated implants, to include miniballs, stays, and prongs using implant-passive ductus-external or extrinsic means V5b. Extracorporeal energization of intrinsic means for radiating heat from within medication implants and medication and/or the tissue bonding-coatings of implants V6. Chemical control over implants and coated implants, to include miniballs, stays, and prongs V7. Radiation-emitting (brachytherapeutic, endocurietherapeutic, sealed source radiotherapeutic, internal radiation therapy) miniballs V8. Temporary (absorbable) ferromagnetic miniballs and other implants

VI. ROTARY MAGAZINE CLIPS

VII. BARREL-ASSEMBLIES

VII1. Types and capabilities of barrel-assemblies

VII1a. Types of barrel-assemblies

VII1b. Capabilities of different type barrel-assemblies

VII2. Ablation and angioplasty-incapable barrel-assemblies

VII2a. Simple pipe barrel-assemblies

VII2b. Simple pipe ablation and angioplasty-incapable barrel-assembly muzzle-heads VII2b(1). Simple pipe barrel-assembly with bounce-plate VII2b(1)(a). Intracorporeally nondeployable nor adjustable bounce-plate attachment VII2b(1)(b). Intracorporeally controllable bounce-plates VII2b(1)(b)(i). Intracorporeally controllable bounce-plate with limited adjustability in elevation VII2b(1)(b)(ii). Intracorporeally controllable bounce-plate with precision adjustment in rebound elevation and rotation VII2b(2). Trap and extraction recovery tractive electromagnets for the recovery of loose and extraction of mispositioned miniballs VII2c. Application of simple pipe-type barrel-assembly to the magnetic correction of tracheal and bronchial collapse (veterinary)

VII2c(1). Treatment of tracheal collapse in the cervical segments, i.e., cephalad or anterior to the thoracic inlet VII2c(1)(a). Use of a magnet-wrap about the esophagus to treat tracheal collapse in a small dog, for example VII2c(1)(b). Use of a simple pipe barrel-assembly to treat tracheal collapse in a small dog, for example VII2c(2). Treatment of tracheal collapse in the thoracic segments, i.e., caudad, or posterior, to the thoracic inlet VII2d. Ablation and angioplasty-incapable radial discharge barrel-assemblies VII2d(1). Limited purpose single barrel (monobarrel) radial discharge barrel-assembly VII2d(2). Multiple radial discharge barrel-assemblies with one- to four- or more-way radial discharge muzzle-heads VII2d(3). Ablation and angioplasty-incapable radial discharge barrel-assembly muzzle-heads VII2d(3)(a). Monobarrel radial discharge barrel-assembly muzzle-head VII2d(3)(a)(i). Structure of monobarrel radial discharge barrel-assemblies VII2d(3)(a)(ii). Materials of radial discharge barrel-assemblies VII2d(3)(b). Muzzle-head turret-motor (turret-servomotor)

VII2d(3)(c). Muzzle-head servomotor (turret-motor) desiderata

VII2d(3)(d). Turret-motor operational modes

VII2d(3)(d)(i). Turret-motor rotational mode

VII2d(3)(d)(ii). Turret-motor oscillatory mode

VII2d(3)(d)(iii). Turret-motor heating mode

VII2d(3)(e). Radial discharge barrel-assembly working arc

VII2d(3)(f). Rotation of working arc

VII2d(3)(g). Control of muzzle-head turret-motor angle within working arc

VII2d(3)(h). Factors that affect muzzle-head nosing length or reach, steerability, and trackability VII2d(3)(i). Trap and extraction recovery tractive electromagnets in radial discharge barrel-assemblies for the recovery of loose and extraction of mispositioned miniballs VII2d(3)(j). Blood-grooves on muzzle-heads for use in blood vessels VII2d(4). Forward drive and sag leveling and stabilizing device VII2d(4)(a). Use of a forward drive stabilizer VII2d(4)(b). Structure of forward drive stabilizing and leveling extension linkage VII2d(5). Direction of radial discharge barrel-assembly muzzle-head on discharge as antegrade (advancing, forward, distad) or retrograde (withdrawing, backward, proximad)

VII2e. Simple pipe and radial discharge barrel-assembly common elements

VII2e(1). Barrel-catheters, barrel-tubes, and barrel-assemblies

VII2e(2). Connectors (couplings) for quick release and reconnection of the barrel-assembly to the airgun with proper alignment VII2e(3). Twist-to-stop and lock connector (twist lock connector, keyed spring lock connector)

VII2e(4). Engagement of the barrel-assembly in the airgun

VII2e(5). Barrel-assembly end-plate

VII2e(6). Electrical connection of the barrel-assembly to the airgun

VII2f. Radial discharge barrel-assembly elements

VII2f(1). Tube polymer nonintrinsic barrel-catheter flexibility (bendability, trackability) setting and altering elements VII2f(1)(a). Tubing materials for barrel-catheters and radial discharge barrel-tubes VII2f(1)(b). Centering devices (centering disks)

VII2f(2). Embolic trap filter in radial discharge muzzle-heads for use in the vascular tree VII2f(2)(a). Trap filter deployment and retrieval mechanism VII2f(2)(b). Automatic disabling of implant-discharge, radial projection units, and turret-motor VII2f(3). Blood-tunnels VII2f(4). Incorporation of a bounce-plate into radial discharge barrel-assemblies VII2f(5). Use of minimally and fully angioplasty-capable radial discharge barrel-assemblies VII2f(6). Ablation and angioplasty-incapable barrel-assembly controls on the airgun VII2g. Minimally ablation or ablation and angioplasty-capable barrel-assemblies VII2g(1). Minimally thermal ablation or angioplasty-capable barrel-assemblies VII2g(2). Minimally ablation or ablation and angioplasty-capable barrel-assembly side-socket VII2g(3). Minimally and fully (airgun-independent) ablation or ablation and angioplasty-capable radial discharge muzzle-heads VII2g(3)(a). Rapid cooling catheter and cooling capillary catheter for cooling heated turret-motor, electrically operated radial projection unit lifting thermal expansion wires and heaters, and recovery magnets VII2g(3)(b). Turret-motor and recovery electromagnet insulation, leads, and control of winding temperatures when used as a heating elements in ablation or ablation and angioplasty-capable barrel-assemblies VII2g(3)(c). Thermal conduction windows (heat-windows) and insulation of the muzzle-head body in minimally or fully thermal ablation and thermal ablation and angioplasty-capable (independently usable) barrel-assemblies VII2g(3)(d). RADIAL PROJECTION UNITS VII2g(3)(d)(i). Structure of radial projection units VII2g(3)(d)(i)(1). Structure of electrically operated radial projection units VII2g(3)(d)(i)(2). Structure of fluidically and microfluidically operated radial projection units VII2g(3)(d)(i)(3). Extended projection scissors lift-platform mechanism VII2g(3)(e). RADIAL PROJECTION UNIT TOOL-INSERTS VII2g(3)(e)(i). Types and functions of radial projection unit tool-inserts, electrical and fluidic or Piped VII2g(3)(e)(ii). Self-contained electrical/fluid system-neutral tool-inserts, to include injection and ejection syringes VII2g(3)(e)(iii). Self-contained electrical/fluid system-neutral tool-insert internal stopping membranes and lifting springs VII2g(3)(e)(iv). Electrical and electrochemical tool-inserts, to include gas discharged injection and ejection syringes VII2g(3)(e)(v). Temperature control in electrical tool-inserts VII2g(3)(e)(vi). Fluid-operated tool-inserts, to include ejector-irrigator-aspirators and injectors VII2g(3)(e)(vii). Use of flow-reversible tool-inserts for microaspiration VII2g(3)(e)(viii). Temperature control in fluid (piped) tool-inserts VII2g(3)(e)(ix). Doublet irrigator-aspirator tool-inserts, or point-washers VII2g(3)(e)(x). Elimination of gases from fluid radial projection unit lines VII2g(3)(f). Radial projection unit control and control panels, elecrical and fluidic or piped VII2g(3)(g). Coordinated use of aspiration and piped radial projection units to remove diseased tissue or obtain tissue samples for analysis VII2g(4). Minimally ablation and ablation and angioplasty-capable barrel-assembly control panels VII2h. ABLATION AND ABLATION AND ANGIOPLASTY-CAPABLE BARREL-ASSEMBLIES VII2h(1). Distinction in ablation or ablation and angioplasty-capable barrel-assemblies as unitary or bipartite VII2h(2). Specific advantages in the elimination or minimization of connection to the airgun (tethering)

VII2h(3). The radial discharge barrel-assembly as a separate and independent angioplasty device VII2h(4). Componentry required for airgun-independent use VII2h(5). Thermal ablation and angioplasty-(lumen wall priming searing- or cautery-) capable barrel-assemblies VII2h(6). Ablation and ablation and angioplasty-capable barrel-assembly end-sockets VII2h(7). Ablation and ablation and angioplasty-capable barrel-assembly side-socket s VII2h(8). BARREL-ASSEMBLY POWER AND CONTROL HOUSING VII2h(8)(a). Connection of the power and control housing to the airgun VII2h(8)(b). Slidable ablation or ablation and angioplasty-capable barrel-assembly power and control housing VII2h(8)(c). Universal barrel-assembly power and control housing VII2h(8)(d). Rechargeable battery pack local to the electrical terminals VII2h(9)(e). Ablation and ablation and angioplasty-capable onboard barrel-assembly control VII2h(9)(f). Ablation and ablation and angioplasty-capable barrel-assembly onboard control Panel VII2h(10). Control of transluminal rate of translation VII2i. Procedure for the extraluminal stenting of a smaller vas using the apparatus described herein VII2j. THROUGH-BORE, OR COMBINATION-FORM, BARREL-ASSEMBLIES VII2j(1). Incorporation of adscititious capabilities into barrel-assemblies VII2j(2). Accommodation of rotational ablating and atherectomizing side-cutting devices in combination-forms VII2j(3). Types of combination-form barrel-assemblies VII2j(4). Forward-directed clearing (ablation and angioplasty) means for integration into the muzzle-Head VII2j(5). Barrel-assembly with built in excimer laser VII2j(6). Barrel-assembly with exchangeable or built in rotational atherectomy burr VII2j(7). Flow-through barrel-assembly for use in blood vessels VII2j(8). Widely applicable barrel-assembly

VIII. RADIAL PROJECTION CATHETERS

VIII1. Types of radial projection catheters

VIII2. Simple, or noncombination-form, radial projection catheters

VIII3. THROUGH-BORE, OR COMBINATION-FORM, RADIAL PROJECTION CATHETERS

VI114. Slidable projection catheter power and control housing

VI115. Fabrication of radial projection catheters

IX. SIDE-PORTS

IX1. Proximal side-ports in angioplasty-capable barrel-assemblies

IX2. Proximal side-ports in combination-form barrel-assemblies and combination-form radial projection catheters IX3. Distal side-ports in combination-form barrel-assemblies and combination-form radial projection catheters X. Steering and emergency recovery of implants with the aid of an external (extracorporeal) Electromagnet X1. Use of an external electromagnet to assist in steering or in freeing the muzzle-head X2. Use of an external electromagnet to assist in mishap recovery X2a. Interception and recovery of a miniball entering the circulation X2a(1). Midprocedural interception and recovery of a miniball entering the circulation X2a(2). Postprocedural recovery of a miniball in the vascular tree X2b. Stereotactic resituation of a mispositioned miniball X2c. Stereotactic arrest and extraction of a circulating, dangerously mispositioned, or embolizing miniball X2d. Downstream disintegration of a circulating miniball X3. Perforations along the gastrointestinal tract

XI. HYPDXIA AND ISCHEMIA-AVERTING ELEMENTS

XI1. Blood-grooves

XI2. Blood-tunnels

XI3. Flow-through bore in combination-form barrel-assemblies and combination-form radial projection catheters used in blood vessels XI4. Push-arm radial projection unit tool-inserts

XII. SERVICE-CATHETERS

XII1. Service-catheters, service-channels, and use of the barrel-assembly as a guide-catheter XII2. Muzzle-head access through a service-channel without the aid of and by means of inserting a service-catheter XII3. Cyanoacrylate cement injection service-catheter XII4. Service-channel adhesive delivery line XII5. Cooling catheters (temperature-changing service-catheters)

XII6. Preparation of service-catheters for use as trans-barrel-assembly hypotubes XII7. Use of the barrel-assembly as an aspirator or transluminal extraction catheter for the removal of soft plaque or mispositioned miniballs XII8. Use of the barrel-assembly as an aspirator or transluminal extraction catheter to retrieve biopsy samples XII9. Rotation of muzzle-heads with unused barrel-tubes for use as a guide-catheters XII10. Delivery of a measured quantity of a liquid through a service-channel XII11. Delivery of a measured quantity of a gas through a service-channel XII12. Delivery of a measured quantity of a powder through a service-channel XII13. Midprocedural delivery of lubricant to the muzzle-head

XIII. AIRGUNS

XIII1. Operational requirements

XIII2. Modification of commercial airguns

XIII2a. Simple airgun modified to allow limited application

XIII2b. Simple airgun modified to allow wider application

XIII2c. Control of propulsive force (exit velocity) by means of a calibrated slide cover over a slit cut into the valve body XIII2d. Docking stations for modified commercial airguns XIII2e. Positioning modes of operation XIII2e(1). Positioning with a simple pipe XIII2e(2). Automated positioning with a radial discharge barrel-assembly

XIII3. DEDICATED INTERVENTIONAL AIRGUNS

XIII3a. Operational requirements

XIII3b. Interventional airgun with liquid vaporization-upon-release cartridge or compressed gas cylinder connected directly to the valve body inlet suitable for use over a range of exit velocities (forces of penetration) in quick succession with moderate redundancy as to points of control over discharge XIII3c. Interventional airgun suitable for procedures involving the treatment of different tissues to different depths in quick succession with redundant points of control to adjust the exit velocity XIII3d. Interventional airgun with multiple exit velocity control points for quick midprocedural adjustment, using rotary magazine clips, and with an automatic positional control system suitable for implanting the wall of a blood vessel XIII3e. Linear positioning stage or table airgun mount XIII3f. Positioning of the barrel-assembly with the linear positioning table and turret-motor XIII3f(1). Type and efficiency of control XIII3f(2). Airgun control panel XIII3f(3). Relation of control panels to the turret-motor and airgun linear positioning table axes, to discharge, and to one another XIII3f(4). Automatic close-formation pattern implantation XIII4. Pairing of barrel-assembly and airgun XIII5. Remote controls

XIV. MODES OF FAILURE

XIV1. Failure to properly discharge

XIV2. Shallow termination into the lumen wall or other tissue of the trajectory

XIV3. Perforations

XIV4. Jamming

XIV5. Premature follow-on discharge

XIV6. Endothelial cling and seizure

XIV7. Radial projection unit lift-platform malfunction

XIV8. Entry of a miniball into the bloodstream

XV. ARCUATE STAYS

XV1. Medication or radiation (nonstent), and medication-coated stays

XV2. Arcuate stent-stays (stent-ribs) for use with magnetic stent-jackets

XV3. Structure of stays

XV4. Partially and completely absorbed stays

XV5. Circumstances dissuading or recommending the use of stays

XV6. Stays coated with a heat-activated (-melted, -denatured) tissue adhesive-hardener, or binder-fixative XV7. Stays coated with a solid protein solder coating and cyanoacrylate cement XV8. Use of cement and solder coated stays XV9. Specification of cyanoacrylate tissue sealants and bonding agents XV10. Practitioner preference for cyanoacrylate tissue sealant

XVI. STAY INSERTION TOOLS

XVI1. Stay insertion tool structure

XVI2. Stay insertion tool inmate stay recall (retraction) and recovery electromagnet XVI3. Stay insertion tool inmate tissue sealant and/or medication delivery line XVI4. Sealing of stay insertion incisions XVI4a. Cement-before insertion (cement-ahead operation)

XVI4b. Sealant cartridges and sealants (adhesives)

XVI4c. Mechanism for adjustment in stay insertion tool ejection cycle inmate cement delivery Interval XVI4d. Control over the quantity of fluid discharged XVI4e. Mechanism for switching from cement-ahead to cement-follower operation XVI5. Stay insertion tool with pivoting base XVI6. Butt-pad with retractable slitting edge XVII. Stay insertion tool-inserts and extension devices XVI8. Use of multiple component adhesives with a stay insertion tool XVI9. Powered stay insertion tool holder for the attachment of medication or tissue sealant syringes whether single, dual, or multi-chambered as supplied, for tool slave-follower or independent use XVI9a. Use of commercial syringes and extension tubes XVI9b. Avoidance of remote syringe placement and long adhesive delivery lines XVI9c. STAY INSERTION TOOL AUXILIARY SYRINGES XVI9c(1). Control of auxiliary syringes XVI9c(2). Tissue sealant syringe holder (holding frame) and attachment XVI9c(3). Structure of tissue sealant syringe holder XVI9c(4). Stay insertion tool auxiliary syringe holding frame attachment XVI9c(5). Connection of the holding frame to the stay insertion tool XVI9c(6). Supporting arm and connecting cable XVI9c(7). Control of auxiliary syringe eject-ahead or eject-after with determinate timing XVI9c(8). Independent and subordinated control of a stay insertion tool auxiliary syringe holding Frame

XVI10. BINDING OF LINES AND CABLES ALONGSIDE THE STAY INSERTION TOOL

XVI10a. Uses of stay insertion tool mounting clips and bands

XVI10b. Use of stay insertion tool side mounting clips to juxtaposition (fasten alongside) an endoscope XVI10c. Use of stay insertion tool side mounting clips to juxtaposition (fasten alongside) a vacuum (aspiration, suction) line XVI10d. Use of stay insertion tool side mounting clips to juxtaposition (fasten alongside) a CO2 cylinder or cold air gun line XVI11. USE OF STAY INSERTION TOOL
XVII. TESTING AND TESTS
XVII1. Need of a means for testing the resistance to puncture, perforation, and delamination of tissue requiring treatment
XVII2. Midprocedural preinsertion testing
XVII3. Confirmation of terminus
XVII4. In situ test on endoluminal approach for susceptibility of the ductus wall to puncture, penetration, and perforation
XVII5. In situ test on endoluminal approach for intra- or inter-laminar separation (delamination, laminar avulsion)
XVII6. Endoluminal approach test for intra- or inter-laminar separation following the insertion of a test miniball
XVII7. In situ test on extraluminal approach for intra- or inter-laminar separation (delamination, avulsion)
XVII8. In situ test on endoluminal approach for intra- or inter-laminar separation following the insertion of a test miniball
XVII9. In situ test on extraluminal approach for resistance to centrifugal pull-through
XVII10. Interconvertibility of results among tests
XVII11. In situ muzzle-head adhesion test
XVIII. Followup examination
XIX. STERILIZATION
XX. EXEMPLARY CHANNEL OF CONTROL IN A FULLY IMPLANTED AMBULATORY ADAPTIVE HIERARCHICAL CONTROL SYSTEM FOR AUTOMATIC RESPONSE TO A COMORBID CONDITION
XXI. FULLY IMPLANTED AMBULATORY ADAPTIVE HIERARCHICAL CONTROL SYSTEMS FOR AUTOMATIC RESPONSE TO A COMORBID CONDITION
XXII. GLOSSARY OF TERMS
CLAIMS
ABSTRACT OF THE DISCLOSURE

BACKGROUND OF THE INVENTION

1. Field of the Invention

The apparatus and methods to be described are intended for use by veterinary specialists, pulmonologists, interventional radiologists and cardiologists, cardiovascular, thoracic, and neurological surgeons, gastroenterologists, and urologists to:

1. Target medication and/or therapeutic substances into the wall surrounding a lumen by radially directed or side-looking injection from within the lumen, with retention by radially outward attraction by a magnetized jacket, or by embedding tiny implants within this or any other diseased tissue. Few drugs released into the circulation have a natural affinity for the organ or tissue intended as iodine has for the thyroid gland. Instead, the drug is delivered to all the tissues of the body at the dose required to treat the intended organ or tissue, even though exposure to the drug of other tissue may be harmful. This is usually the cause of adverse side effects, drug-drug, and drug-food interactions. Moreover, when not targeted, efficacy necessitates that the dose required be much larger and therefore more costly. Accordingly, one object here is to provide means that allow squarely targeting a specific organ, segment along a tubular anatomical structure, or tissue.

2. Ablate diseased and/or obstructive tissue from or angioplasty the walls surrounding a bodily conduit, that is, the passageway or lumen through a tubular anatomical structure, whether that of a blood vessel, a duct, ureter, vas deferens, fallopian tube, the gut, trachea, or a bronchus, for example, any of which may be properly referred to as a vas, vessel, ductus, duct, canal, or channel 3. Position increasingly magnetized spherules, stays, impasse-, or stent-jackets along a ductus in the antegrade (anterograde) direction to draw and concentrate ferromagnetic carrier-bound drugs from the passing circulation into the lumen wall.

4. Position these minute implants so as to target a specific segment of a ductus or an organ, and if necessary.

5. Embed implants containing sufficient ferromagnetic material to serve as the intraductal component of an extraluminal stent, where any or all of the foregoing functions can be accomplished in any combination or sequence with single entry. Small implants consisting almost entirely of medication can be implanted in any tissue, to include the wall surrounding a lumen, or can be positionally stabilized inside the lumen alongside a diseased segment.

6. Target drugs within supply conduits, such as arteries, by suspending these as magnetically susceptible carrier superparamagnetic nanoparticles or microparticles within a magnetic jacket encircling the conduit, either a stent-jacket, or if to be extracted to the perivascular space, an impasse-jacket, so that the drug or drugs are drawn against or into the lesioned wall of the lumen, or if contained within a miniball or microsphere shell but not inseparably bound to the magnetically susceptible particles, or ferro co-bound, the drug or drugs are released into the lumen. More specifically, as will be described, when a drug is to be directly delivered to the target organ, tissue, or segment along a tubular anatomical structure through the circulation, uptake from an infused or injected drug dispersed in a ferrofluid is through a port at the body surface, thence through a fluid line leading to the tissue with uptake by detention at the target segment and absorption through the endothelium or urothelium, for example, by means of an impasse-jacket. An electromagnetized jacket allows the drug to be drawn into the intima or suburothelium, for example. When the drug is to be delivered to an organ, for example, delivery is into the lumen of the organ blood supply through a ductus side-entry jacket or if into the parenchyma, a nonjacketing side-entry connector as described in copending applications specified below.

7. Where the substance, usually a drug must be prevented from further circulation, position a final impasse-jacket downstream or at the outflow, such as venous, of the target organ to suspend within the lumen a reversal agent (counteractant, antidote, neutralizing agent) to the drug released by the upstream implant or by positioning increasingly magnetized implants about the lumen to truncate its continued flow to nontargeted tissue.

Presented here will be a form of magnetic stenting which is fundamentally superior to any endoluminal or intravascular magnetic stent, or any endoluminal stent intended to be attracted to a magnetic field generated from outside the stented conduit, or ductus. More specifically, the type stent described is superior to any endoluminal stent magnetic or not. That is, whether the lumen of a blood vessel, the airway, the digestive tract, urogenital (or urinogenital), tract, or an endocrine duct, magnetically susceptible endoluminal stents and coiled stents positioned inside the lumen to achieve the pushing outward of the wall surrounding an inflamed, constricted, or obstructed lumen when attracted to an extraluminal magnet are fundamentally inferior to the intramural, or infixed within the lumen wall, means described herein. The reasons for this superiority are sufficiently pertinent from a medical standpoint as to warrant preliminary comment.

First, where intramurally positioned implants, ordinarily distributed uniformly about the lumen wall for attraction to a magnetized jacket surrounding the ductus or conduit, uniformly expand the lumen radially outward in all directions, endoluminal magnetic stents only pull at the substrate conduit or ductus in the direction of attraction. The tiny magnetically susceptible intramural implants used to impart patency to a constricted lumen, which can incorporate or be coated with medication of any kind, are positioned entirely about the lumen wall, and rather than drawn to an extracorporeal magnet, are surrounded by an implanted foam-lined jacket (collar, mantle) in immediate contact with the substrate ductus. When spherical, these implants are referred to as miniballs; when band (strip, tang)-shaped, the term used is stays. In comparison, endoluminal magnetic stents are incapable of treating the radial asymmetries or eccentricities characteristic of angiosclerotic lesions or plaques discriminately, instead covering over unaffected radii about the arterial wall.

The jacket is magnetized perpendicularly to the long axis of the conduit or ductus and may be rolled from magnetized stainless steel sheet, or as shown in FIGS. 2 thru 6, comprise a polymeric base-tube having small permanent magnets or electromagnets affixed thereto. When drawn to an outside magnet, an endoluminal magnetic stent is drawn up against the ipsilateral luminal wall, imposing a significant indenting force thereupon in excess of the outward force an endoluminal stent must exert to prevent migration under any circumstances. This is a potential source of serious complications that a stent having no part within the lumen can never present. Recovery of an endoluminal stent is by reentry and surgical cut-down, which is why once placed, an endoluminal stent is removed only when removal cannot be avoided.

An endoluminal stent has one means for avoiding migration—protrusion into the surrounding lumen lining. The struts of a scaffold type stent or the wire of a coiled stent must be made thinner to further protrude into the lining Properly placed, an intraluminal stent cannot migrate. The intraluminal component is embedded within the lumen wall, and located outside the substrate ductus or vessel, the magnetized stent-jacket can be fixed in position in several ways. Small optional suture loops or eyelets integral with the jacket allow suture to be passed through for fixation to neighboring tissue.

When suture is riveted or already connected by suture loops to the ends of the jacket (referred to as end-ties) as manufactured, the suture can be used as indicated, wrapped about the substrate ductus beyond the jacket margins, or both. Where vasotonic is pronounced or the activity of the patient is conducive to displacement, one or two outrigger or dummy collars, shown as parts of an impasse-jacket described below in sections 12 entitled Concept of the Impasse-jacket and I15 entitled Miniball and Ferrofluid-impassable Jackets, or Impasse-jackets can be provided, and both the stent-jacket proper and the outriggers can be fastened as stated with suture.

Magnetically susceptible endoluminal stents are usually widely open pitched (space wound, open wound) non-overwound coils, that is, single turn or single wrap coils having wide gaps between the consecutive turns (winds, wraps), precluding drug elution as a partially remediating measure for the chronic irritation caused. A distinct irritant, endoluminal stents in the vascular tree—of all kinds, but especially those susceptible to a magnetic field—have the potential not only to stimulate intimal hyperplasia leading to restenosis, but accelerate atherosclerosis, better endoluminal stents ameliorating the problem with drugs such as everolimus.

Rapamycin-derived drugs such as everolimus are used primarily as immunosuppressants, of special benefit with an endoluminal stent, which to prevent migration, must maintain firm contact with the surrounding luminal wall, thereby provoking a foreign body adverse tissue reaction or immune response. Even in a nonallergic patient, such reactions are unavoidable; however, the contact area with the surrounding tissue of miniballs and stays is much less than that of an endoluminal stent, and these too can be coated with drugs such as everolimus. In most cases, the immune system will encapsulate the protrusive surfaces of a foreign body such as an endoluminal stent or an intraluminal implant in a vascular and collagenous fibrous capsule, the process known as the foreign body response or foreign body granuloma.

However, formation of this isolating layer is typically 50-200 micrometers in thickness—enough to isolate an implant chemically, but even with the high level of motion about a stent to stimulate an increase in this thickness, not enough to afford sufficient protection against the mechanical forces imposed upon the tissue in contact with the stent (see, for example, de la Oliva, N., Navarro, X., and Del Valle, J. 2018. "Time Course Study of Long-term Biocompatibility and Foreign Body Reaction to Intraneural Polyimide-based Implants," *Journal of Biomedical Materials Research. Part A* 106(3):746-757; Klopfleisch, R. and Jung, F. 2017. "The Pathology of the Foreign Body Reaction Against Biomaterials," *Journal of Biomedical Materials Research. Part A* 105(3):927-940; Wang, Y., Vaddiraju, S., Gu, B., Papadimitrakopoulos, F., and Burgess, D. J. 2015. "Foreign Body Reaction to Implantable Biosensors: Effects of Tissue Trauma and Implant Size," *Journal of Diabetes Science and Technology* 9(5):966-977; Wazen, R. M., Currey, J. A., Guo, H., Brunski, J. B., Helms, J. A., and Nanci, A. 2013. "Micromotion-induced Strain Fields Influence Early Stages of repair at Bone-implant Interfaces," *Acta Biomaterialia* 9(5):6663-6674; Morais, J. M., Papadimitrakopoulos, F., and Burgess, D. J. 2010. "Biomaterials/Tissue Interactions: Possible Solutions to Overcome Foreign Body Response," *American Association of Pharmaceutical Scientists Journal* 12(2): 188-196).

It is during the granulation and maturation phase leading up to formation of the capsule—variable in duration depending upon the material used, but generally taking about 2 to 4 weeks—that the tissue in contact with the stent is especially vulnerable. "Biomaterial surface properties play an important role in modulating the foreign body reaction in the first two to four weeks following implantation of a medical device, even though the foreign body reaction at the tissue/material interface is present for the in vivo lifetime of the medical device." (Anderson, J. M., Rodriguez, A., and Chang, D. T. 2008. "Foreign Body Reaction to Biomaterials," *Seminars in Immunology* 20(2):86-100).

However, the fibrous tissue with an endoluminal stent will be continuous over the length of the stent, interfering with endothelial or urothelial function, and only the endoluminal stent will remain within the lumen to pose the risk of migration and present a distinct obstruction to any later transluminal procedure. Before fibrous encapsulation forms, a stent placed within any native lumen presents the potential for ischemia-inducing intramedial protrusion, which can lead to an erosion, incision, and fistulation (fistulization) responsive to continuous irritation of physiologically active tissue. That this is virtually certain with a direct blow and impossible when no stent is in the lumen is clear.

Endoluminal stents are potentially more injurious than medicinal treatment without stenting; local adaptation notwithstanding, continued force of indentation, aggravated by the normal intrinsic vasotonic and pulsatile or peristaltic motility of the conduit increases the risk of infection, interferes with, impairs the function of, and injures the endothelium, urothelium, or other lining, thereby interfering with normal endothelial, urothelial, or digestive enzymatic function, and creating the risks of fistulation and perforation. In the arterial tree, such risk includes incisions, aneurysm, pseudoaneurysm, and migration. The guide wire used to deliver an endoluminal stent to the target level is itself a source of numerous complications to include perforations, fracture, and migration, to which the blunt or bull-nosed leading tip of the delivery means described here—a barrel-assembly—is not. To recover an errant endoluminal stent or guidewire can involve greater surgical risk than the risk the stent was placed to ameliorate.

Endothelial dysfunction is central in causing coronary artery disease and other expressions of chronic arterial inflammation. In any situation where the force of the magnetic field would adversely extract spherical implants, wide band- or tongue-shaped implants are used, the means for the insertion thereof—stay insertion tools—described herein. Where an endoluminal stent is in contact with the surrounding lumen wall, it blocks not only endothelial effusion into the lumen of prostacyclin, endothelin, and locally controlling angiotensin-II, but the vasodilator nitric oxide. Also denied over the contact area is access to the passing luminal contents, those native, blood, urine, endocrine secretion, gametes, or food, enzymes, hormones, other proteins, and therewith, nonendogenous agents, meaning medication.

Whether coiled or scaffold in type, when attracted by an external magnet, an endoluminal stent is pulled further into the lumen wall. In marked contrast to such endoluminal stents, intramural stents lie outside the lumen; the magnetically susceptible component comprises a uniformly spaced grouping of tiny implants infixed within the lumen wall where the nonliving connective tissue elastic laminae protect the other laminae (tissue layers, tunics) consisting of living cells which comprise the lumen wall from injury. Migration or dislodgement a serious risk with any endoluminal stent, such is not possible when no stent is inside the lumen. That the tiny intramurally positioned susceptible implants are uniformly distributed over the area stented is of fundamental significance.

Disposed thus, attraction by an external magnet, rather than concentrating the attractive force over a small contact area between the stent and the lumen wall, uniformly lifts the wall abaxially or outward as a continuous sheet over the completely surrounding area of the stent rather than concentrating a force of indentation in excess of that imposed by an endoluminal stent under any circumstances over a restricted area, increasing the risks of injury and incision. Such a stent can, however, accommodate eccentric or asymmetrical lesions according to the distribution of the implants. In most cases, however, the jacket entirely surrounding the substrate native conduit or ductus, the magnetic attraction is uniformly exerted entirely about the conduit or ductus. Accordingly, rather than for the stent to be forcibly attracted into the lumen wall, intramurally positioned implants lift the lumen wall uniformly round and about toward the surrounding magnetized jacket.

In the trachea, where an intramural magnetically susceptible stent as described herein is superior to the considerably traumatic conventional surgical procedure for correction, an endoluminal stent obstructs mucociliary clearance, facilitating the accumulation of debris, increasing the risk of infection. In a neonate, in whom tracheomalacia infrequently appears as a condition encountered when the tracheal cartilages remain premature at birth, the short-term placement of an endoluminal stent when there is a risk of suffocation then prudent. However, in veterinary practice, where any of numerous animals in whom tracheal collapse is progressive and the conventional remedy is surgical, an endoluminal stent that must be placed in lieu of surgery because the animal is too debilitated to tolerate the procedure must remain in place indefinitely as an increasingly injurious obtrusion.

That a magnetic intraluminal stent avoids both the problems of an endotracheal stent and the need for critically more traumatic surgery is clear. Unless springy with restorative force such that the contralateral side of the stent remains in contact with the contralateral wall, the contralateral side of the stent is drawn away from the contralateral wall and further into the lumen. This adaxial shifting only increases interference with free luminal flow-through of any endoluminal stent. Even when remaining in flush contact with the contralateral wall, numerous problems arise from the presence in a native lumen of a foreign object, interference if not prevention of subsequent transluminal treatment not the least of these. For this reason, the advantage in an extraluminal stent increases in proportion to the probability that the patient will require a followup transluminal intervention.

The incorporation of magnetically susceptible matter in an implant allows the implant not only to attracted to a magnet, but when placed in a radiofrequency alternated magnetic field, allows the implant to be heated. Thermoplastic ablation by impregnating a neoplasm with susceptible implants and placing the patient in such a field has long been standard practice. The application of heat of value in numerous other contexts—site specifically controlling drugs or surgical adhesives, for example—scaffold or coiled endoluminal stents heat the lumen wall not uniformly, but disproportionately where the struts or turns are in direct contact with the lumen wall. Moreover, even though the lesion to be heated is eccentric, such stents are limited to the application of heat in this disjointed way without deviation from radial or rotational symmetry, thus heating sectors of the ductus not beneficially and perhaps adversely affected thus. By contrast, intramural stenting allows discretionary eccentric or radially asymmetrical heating.

The miniballs, or tiny spherules, and bands, or stays, referred to herein can consist of magnetically susceptible matter, usually encapsulated, medication, radiation emitting 'seeds,' or any of these in combination. To impart targetability to medication spherules, for example, a magnetized ductus side-entry jacket or nonjacketing connector is positioned at the target site, and magnetically susceptible matter, usually magnetite, maghemite, or iron powder, added to the spherules. Ferrofluids conveying magnetically carried drugs ratioactive or not can thus be steered to the treatment site without the need for intrinsic affinity, such as that of iodine for the thyroid gland. All drugs harbor adverse side effects and have toxic dose limits. Two types of drugs in particular are, however, more injurious when admitted into the general circulation.

These are immunosuppressives, which expose the patient to infection, and anticancer drugs, which are toxic to normal as well as malignant tissue. Minimally invasive and minor surgical procedures make possible the implantation of magnetically susceptible drug-carrier releasing and attracting implants that allow treatments intermediate between medical management and open surgery. More specifically, by allowing the circumscription of target tissue for the delivery of drugs or other therapeutic substances, minor surgery to place such implants can be used to significantly expand the reach of medical management. The methods described herein represent a level of treatment intermediate between medical management and surgery, that of medical surgery, or surgery to enable or facilitate medical management.

The presupposition that surgery should always be considered the last resort so that the administration of drugs, all potentially harmful, to temporarily alleviate the symptoms of chronic disorders on a long-term if not life-long basis is superior therapy compared to performing a one-time relatively safe surgical procedure is often misconceived. Examples are many and apply to almost if not all drugs used thus, the most common being:

a. Antacids in lieu of endoscopic repair of an hiatus hernia, and/or highly selective vagotomy, or the placement of a special esophagogastric collar about the lower esophageal sphincter, or transoral incisionless endoscopic fundoplication (see, for example, Fass, R. 2017. "An Overview of Transoral Incisionless Fundoplication and Magnetic Sphincter Augmentation for GERD," *Gastroenterology and Hepatology* (New York, N.Y.) 13(1):50-52; Trad, K. S., Fox, M. A., Simoni, G., Shughoury, A. B., Mavrelis, P. G., and 3 others 2017. "Transoral Fundoplication Offers Durable Symptom Control for Chronic GERD: 3-year Report from the TEMPO [Transoral incisionless fundoplication] EsophyX vs Medical Proton Pump Inhibitor Open Label Trial] Randomized Trial with a Crossover Arm," *Surgical Endoscopy* 31(6):2498-2508; Huang, X., Chen, S., Zhao, H., Zeng, X., Lian, J., Tseng, Y., and Chen, J. 2017. "Efficacy of Transoral Incisionless Fundoplication (TIF) for the Treatment of GERD: A Systematic Review with Meta-analysis," *Surgical Endoscopy* 31(3):1032-1044; Stefanidis, G., Viazis, N., Kotsikoros, N., and Tsoukalas, N., Lala, E., and 3 others 2017. "Long-term Benefit of Transoral Incisionless Fundoplication Using the Esophyx Device for the Management of Gastroesophageal Reflux Disease Responsive to Medical Therapy," *Diseases of the Esophagus* 30(3):1-8; Fass, R. 2017. "An Overview of Transoral Incisionless Fundoplication and Magnetic Sphincter Augmentation for GERD," *Gastroenterology and Hepatology* (New York, N.Y.) 13(1): 50-52; Trad, K. S., Barnes, W. E., Simoni, G., Shughoury, A. B., Mavrelis, P. G., and 4 others 2015. "Transoral Incisionless Fundoplication Effective in Eliminating GERD Symptoms in Partial Responders to Proton Pump Inhibitor Therapy at 6 Months: the TEMPO Randomized Clinical Trial," *Surgical Innovation* 22(1):26-40; Bonavina, L., Saino, G., Lipham, J. C., and Demeester, T. R. 2013. "LINX(®) Reflux Management System in Chronic Gastroesophageal Reflux: A Novel Effective Technology for Restoring the Natural Barrier to Reflux," *Therapeutic Advances in Gastroenterology* 6(4):261-268) to alleviate gastroesophageal reflux or to cure an ulcer, which at the least allows the administration of such drugs to be significantly reduced in dose and frequency.

Chronic use of antacids can lead to achlorhydria, the absence, or hypochlorhydria, a deficiency, of hydrochloric acid in the gastric juice, defeating an important mechanism of the immune system for eradicating pathogenic microbiota from food, which can lead to bacterial overgrowth of the small intestine, interfering with the absorption of iron and other nutrients, and promoting intestinal metaplasia, degenerative conversion of the stomach lining to resemble that of the small intestine, or atrophic gastritis. The overgrowth is likely to lead to gastric infection, the interference with iron absorption to iron deficiency anemia, possibly pica, the interference with vitamin $B_3$ (niacin) absorption to pellagra, and the metaplasia to additional malabsorption such as the loss of parietal cells, hence, gastric intrinsic factor needed to absorb vitamin $B_{12}$ (cobalamin).

This then can lead to pernicious anemia, megaloblastic anemia, and gastric adenocarcinoma, as well as open the way for numerous additional gastrointestinal, neuropsychiatric, and systemic disorders. Untreated, this degenerative cascade results in death. However, the administration of antibiotics to compensate for infectious consequences of the reduction in stomach acidity also destroys beneficial intestinal microbiota (dysbiosis, dysbacteriosis), risking leaky gut syndrome. This also allows pathogenic microbiota unaffected by the antibiotic to survive, reproduce, and become more resistant to the antibiotic, a misapplication of antibiotics that contributes to the growing problem of drug resistant pathogens, and may prompt the administration of probiotics to repopulate the gut with beneficial microbiota.

Especially in patients with health problems, probiotics occasionally cause adverse sequelae, to include undesirable gene transfer, digestive problems, systemic infections, equivocally, endocarditis, bloating, flatulence, in larger doses, diarrhea, an increase in gastroesophageal reflux, and/or other problems (see, for example, Aaron, J. G., Sobieszczyk, M. E., Weiner, S. D., Whittier, S., and Lowy, F. D. 2017. "Lactobacillus rhamnosus Endocarditis after Upper Endoscopy," *Open Forum Infectious Diseases* 4(2): ofx085; Isidro, R. A., Lopez, A., Cruz, M. L., Gonzalez Tones, M. I., Chompre, G., Isidro, A. A., and Appleyard, C. B. 2017. "The Probiotic VSL #3 Modulates Colonic Macrophages, Inflammation, and Microflora in Acute Trinitrobenzene Sulfonic Acid Colitis," *Journal of Histochemistry and Cytochemistry* 65(8):445-461; Encarnacion, C. O., Loranger, A. M., Bharatkumar, A. G., and Almassi, G. H. 2016. "Bacterial Endocarditis Caused by Lactobacillus acidophilus Leading to Rupture of Sinus of Valsalva Aneurysm," *Texas Heart Institute Journal* 43(2):161-164.; Doron, S. and Snydman, D. R. 2015. "Risk and Safety of Probiotics," *Clinical Infectious Diseases* 60 Supplement 2:S129-S134; Verna, E. C. and Lucak, S. 2010. "Use of Probiotics in Gastrointestinal Disorders: What to Recommend?," *Therapeutic Advances in Gastroenterology* 3(5):307-319; Marteau, P. and Seksik, P. 2004. "Tolerance of Probiotics and Prebiotics," *Journal of Clinical Gastroenterology* 38(6 Supplement):S67-S69).

Upon discontinuation after daily use, nonsteroidal antacids such as proton pump inhibitors educe pronounced rebound acid hypersecretion sensed as 'heartburn' (see, for example, Zdilla, M. J. 2015. "Metformin with Either Histamine H2-receptor Antagonists or Proton Pump Inhibitors: A Polypharmacy Recipe for Neuropathy via Vitamin $B_{12}$ Depletion," *Clinical Diabetes* 33(2):90-95; Reimer, C., Sondergaard, B., Hilsted, L., and Bytzer, P. 2009. "Proton-pump Inhibitor Therapy Induces Acid-related Symptoms in Healthy Volunteers after Withdrawal of Therapy," *Gastroenterology* 137(1):80-87, 87.e1; Nwokolo, C. U., Smith, J. T., Sawyerr, A. M., and Pounder, R. E. 1991. "Rebound Intragastric Hyperacidity After Abrupt Withdrawal of Histamine H2 Receptor Blockade," *Gut* 32(12):1455-1460).

Proton pump inhibitors such as omeprazole have been linked to the development of dementia (see, for example, Clouston, S. A. P., Shapira, O., Kotov, R., Lei, L., Waszczuk, M., Bromet, E. J., and Luft, B. J. 2017. "Proton Pump Inhibitors and the Risk of Severe Cognitive Impairment: The Role of Posttraumatic Stress Disorder," *Alzheimers and Dementia* (New York, N.Y.) 3(4):579-583; Wijarnpreecha, K., Thongprayoon, C., Panjawatanan, P., and Ungprasert, P.

2016. "Proton Pump Inhibitors and Risk of Dementia," *Annals of Translational Medicine* 4(12):240), Gomm, W., von Holt, K., Thomé, F., Broich, K., Maier, W., and 3 others 2016. "Association of Proton Pump Inhibitors with Risk of Dementia: A Pharmacoepidemiological Claims Data Analysis," *Journal of the American Medical Association Neurology* 73(4):410-416; hypomagnesemia and kidney disease (see, for example, Toth-Manikowski, S. and Grams, M. E. 2017. "Proton Pump Inhibitors and Kidney Disease—GI Upset for the Nephrologist?," *Kidney International Reports* 2(3):297-301; Cheungpasitporn, W., Thongprayoon, C., Kittanamongkolchai, W., Srivali, N., Edmonds, P. J. and 4 others 2015. "Proton Pump Inhibitors linked to Hypomagnesemia: A Systematic Review and Meta-analysis of Observational Studies," *Renal Failure* 37(7):1237-1241), . . . . "*Clostridium difficile* infection, community-acquired pneumonia, fractures of the hip and spine." (Toth-Manikowski, S. and Grams, M. E. 2017, Op cit., cites references for each).

As to *C. difficile* (see, for example, Oshima, T., Wu, L., Li, M., Fukui, H., Watari, J., and Miwa H. 2018. "Magnitude and Direction of the Association Between Clostridium difficile Infection and Proton Pump Inhibitors in Adults and Pediatric Patients: A Systematic Review and Meta-analysis," *Journal of Gastroenterology* 53(1):84-94; Trifan, A., Stanciu, C., Girleanu, I., Stoica, O. C., Singeap, A. M., and 4 others 2017. "Proton Pump Inhibitors Therapy and Risk of *Clostridium difficile* Infection: Systematic Review and Meta-analysis," *World Journal of Gastroenterology* 23(35): 6500-6515; Scarpignato, C., Gatta, L., Zullo, A., Blandizzi, C.; with 9 collaborators 2016. "Effective and Safe Proton Pump Inhibitor Therapy in Acid-related Diseases—A position Paper Addressing Benefits and Potential Harms of Acid Suppression," *BioMed Central Medicine* 14(1): 179).

Histamine $H_2$ receptor antagonists (cimetidine, ranitidine, famotidine, nizatidine) risk numerous adverse side effects and drug interactions (see, for example, Upadhyay, K. J., Parmar, S. J. 1, Parikh, R. P. 1, Gauswami, P. K., Dadhaniya, N., and Surela, A. 2015. "Intravenous Ranitidine: Rapid Bolus Can Lead to Cardiac Arrest," *Journal of Pharmacology and Pharmacotherapeutics* 6(2):100-102; Zdilla, M. J. 2015. "Metformin with Either Histamine H2-receptor Antagonists or Proton Pump Inhibitors: A Polypharmacy Recipe for Neuropathy via Vitamin B12 Depletion," *Clinical Diabetes* 33(2):90-95; Lee, T. H., Vega, K. J., and El Khoury, J. G. 2010. "Ranitidine Induced Hepatitis," *Journal of Gastrointestinal and Liver Disease* 19(3):337-338; Ramrakhiani, S., Brunt, E. M., and Bacon, B. R. 1998. "Possible Cholestatic Injury from Ranitidine with a Review of the Literature," *American Journal of Gastroenterology* 93(5): 822-826; García Rodríguez, L. A., Wallander, M. A., and Stricker, B. H. 1997. "The Risk of Acute Liver Injury Associated with Cimetidine and Other Acid-suppressing Anti-ulcer Drugs," *British Journal of Clinical Pharmacology* 43(2):183-188; Kallal, S. M. and Lee, M. 1996. "Thrombotic Thrombo-cytopenic Purpura Associated with Histamine H2-receptor Antagonist Therapy," *Western Journal of Medicine* 164(5):446-448; García Rodríguez, L. A. and Jick, H. 1994. "Risk of Gynaecomastia Associated with Cimetidine, Omeprazole, and Other Antiulcer Drugs," *British Medical Journal* (clinical research) 308(6927):503-506; Sabesin, S. M. 1993. "Safety Issues Relating to Long-term Treatment with Histamine H2-receptor Antagonists," *Alimentary Pharmacology and Therapeutics* 7 Supplement 2:35-40; Vial, T., Goubier, C., Bergeret, A., Cabrera, F., Evreux, J. C., and Descotes, J. 1991. "Side Effects of Ranitidine," *Drug Safety* 6(2):94-117; Andersen, M. and Schou, J. S. 1991. "Adverse Effects of Ulcer drugs before and after Release of Cimetidine, Ranitidine and Sucralfate for Over-the-counter Sale," (in Danish with abstract in English at Pubmed), *Ugeskrift for Laeger* [Weekly Journal for Physicians] 153(20):1410-1413; Berardi, R. R., Tankanow, R. M., and Nostrant, T. T. 1988. "Comparison of Famotidine with Cimetidine and Ranitidine," *Clinical Pharmacy* 7(4):271-284; Aymard, J. P., Aymard, B., Netter, P., Bannwarth, B., Trechot, P., and Streiff, F. 1988. "Haematological Adverse Effects of Histamine H2-receptor Antagonists," *Medical Toxicology and Adverse Drug Experience* 3(6):430-448; Lewis, J. H. 1987. "Hepatic Effects of Drugs Used in the Treatment of Peptic Ulcer Disease," *American Journal of Gastroenterology* 82(10):987-1003; Schunack, W. 1987. "What are the Differences Between the H2-receptor Antagonists?," *Alimentary Pharmacology and Therapeutics* 1 Supplement 1:493S-503S; Black, M. 1987. "Hepatotoxic and Hepatoprotective Potential of Histamine (H2)-receptor Antagonists," *American Journal of Medicine* 83(6A):68-75; Sax, M. J. 1987. "Clinically Important Adverse Effects and Drug Interactions with H2-receptor Antagonists: An Update," *Pharmacotherapy* 7(6 Part 2):110S-115S; Penston, J. and Wormsley, K. G. 1986. "Adverse Reactions and Interactions with H2-receptor Antagonists," *Medical Toxicology* 1(3):192-216; Kirch, W., Spahn, H., Köhler, H., and Mutschler, E. 1983. "Accumulation and Adverse Effects of Metoprolol and Propranolol after Concurrent Administration of Cimetidine," *Archives of Toxicology. Supplement* 6:379-383; Hughes, J. D., Reed, W. D., and Serjeant, C. S. 1983. "Mental Confusion Associated with Ranitidine," *Medical Journal of Australia* 2(1):12-13; Tosi, S., and Cagnoli, M. 1982. "Painful Gynecomastia with Ranitidine," *Lancet* 2(8290):160; Schifman, C. 1983. "Gynecomastia and Bradycardia: Side Effects of Ranitidine?," *Clinical Pharmacy* 2(3):209; Camarri, E., Chirone, E., Fanteria, G., and Zocchi, M. 1982. "Ranitidine-induced Bradycardia," *Lancet* 2(8290): 160).

Patient specific allergic reactions such as urticaria, or hives, dyspnea, and facial swelling, for example, aside, famotidine is less prone to provoke adverse side effects than other drugs in its class but is not without its own risks (see, for example, Gupta, N., Patel, C., and Panda, M. 2009. "Hepatitis Following Famotidine: A Case Report," *Cases Journal* 2009 2(1):89; Scheinfeld, N., Wesson, K., Perry, P., and Weinberg, J. 2003. "Acute Generalized Exanthematous Pustulosis Resembling Toxic Epidermal Necrolysis Caused by Famotidine," *Acta Dermato-venereologica* 83(1):76-77; Marcus, E. L., Clarfield, A. M., Kleinman, Y., Bits, H., Darmon, D., Da'as, N. 2002. "Agranulocytosis Associated with Initiation of Famotidine Therapy," *Annals of Pharmacotherapy* 36(2):267-271; von Einsiedel, R. W., Roesch-Ely, D., Diebold, K., Sartor, K., Mundt, C., and Bergemann, N. 2002. "H(2)-histamine Antagonist (Famotidine) Induced Adverse CNS Reactions with Long-standing Secondary Mania and Epileptic Seizures," *Pharmacopsychiatry* 35(4): 152-154; Yuan, R. Y., Kao, C. R., Sheu, J. J., Chen, C. H., and Ho, C. S. 2001. "Delirium Following a Switch from Cimetidine to Famotidine," *Annals of Pharmacotherapy* 35(9):1045-1048; Rodgers, P. T. and Brengel, G. R. 1998. "Famotidine-associated Mental Status Changes," *Pharmacotherapy* 18(2):404-407; Odeh, M. and Oliven, A. 1998. "Central Nervous System Reactions Associated with Famotidine: Report of Five Cases," *Journal of Clinical Gastroenterology* 27(3):253-254; Brunner, M., Vardarman, E., Goldermann, R., Goerz, G., Niederau, D., Merk, H. F., and Scharffetter-Kochanek, K. 1995. "Toxic Epidermal Necrolysis (Lyell Syndrome) Following Famotidine Administration," *British Journal of Dermatology* 133(5):814-815;

Ament, P. W., Roth, J. D., and Fox, C. J. 1994. "Famotidine-induced Mixed Hepatocellular Jaundice," *Annals of Pharmacotherapy* 28(1):40-42; Ahmad, S. 1991. "Famotidine and Cardiac Arrhythmia," *Drug Intelligence and Clinical Pharmacy: The Annals of Pharmacotherapy* 25(3):315; Norwood, J., Smith, T. M., and Stein, D. S. 1990. "Famotidine and Hyperpyrexia," *Annals of Internal Medicine* 112(8):632; Henann, N. E., Carpenter, D. U., and Janda, S. M. 1988. "Famotidine-associated Mental Confusion in Elderly Patients," *Drug Intelligence and Clinical Pharmacy* 22(12):976-978). Famotidine induces urticaria in those allergic but has value in the treatment of urticaria (Fedorowicz, Z., van Zuuren, E. J., and Hu, N. 2012. "Histamine H2-receptor Antagonists for Urticaria," *Cochrane Database of Systematic Reviews* (3):CD008596; Watson, N. T., Weiss, E. L., and Harter, P. M. 2000. "Famotidine in the Treatment of Acute Urticaria," *Clinical and Experimental Dermatology* 25(3):186-189).

Famotidine may be of greater value for off-label than conventional use (Joe, S., Kim, E., Park, J., Lee, D., Son, J., and Kim, H. 2017. "Famotidine-induced Reversal of Meperidine-related Serotonin Syndrome: A Case Report" *Korean Journal of Anesthesiology* 70(2):221-223; Meskanen, K., Ekelund, H., Laitinen, J., Neuvonen, P. J., Haukka, J., Panula, P., and Ekelund, J. 2013. "A Randomized Clinical Trial of Histamine 2 Receptor Antagonism in Treatment-resistant Schizophrenia," *Journal of Clinical Psychopharmacology* 33(4):472-478; Rosenberg, P. B., Rosse, R. B., John, S. K., Kendrick, K., Fay-McCarthy, M., and 4 others 1996. "Smooth Pursuit Eye Movements in the Evaluation of Famotidine Adjunctive Therapy of Schizophrenia: A Preliminary Report," *Clinical Neuropharmacology* 19(3):276-281).

b. Nasal decongestants in lieu of balloon rhinoplasty or outfracture of the swollen lower turbinates with widening of the nasal passages through cautery. Oxymetazoline hydrochloride, for example, is associated with numerous systemic side effects (see, for example, Dokuyucu, R., Gokce, H., Sahan, M., Sefil, F., Tas, Z. A., and 4 others 2015. "Systemic Side Effects of Locally Used Oxymetazoline," *International Journal of Clinical and Experimental Medicine* 8(2):2674-2678; Ramey, J. T., Bailen, E., and Lockey, R. F. 2006. "Rhinitis Medicamentosa," *Journal of Investigational Allergology and Clinical Immunology* 16(3):148-155; Graf, P. 1997. "Rhinitis Medicamentosa: Aspects of Pathophysiology and Treatment," *Allergy* 52(40 Supplement):28-34; Graf, P. and Hallén, H. 1996. "Effect on the Nasal Mucosa of Long-term Treatment with Oxymetazoline, Benzalkonium Chloride, and Placebo Nasal Sprays," *Laryngoscope* 106(5 Part 1):605-609; Graf, P., Hallén, H., and Juto, J. E. 1995. "Four-week Use of Oxymetazoline Nasal Spray (Nezeril) Once Daily at Night Induces Rebound Swelling and Nasal Hyperreactivity," *Acta Otolaryngologica* 115(1):71-75).

Most nasal decongestants provoke rebound vasodilative congestive swelling of the mucosa, or rhinitis medicamentosa. Other side effects of a1 adrenergic receptor agonists and α2 adrenergic receptor partial agonists such as oxymetazoline, xylometazoline, naphazoline, and phenylephrine are drowsiness, epistaxis (nosebleed), rebound inflammation, nasal dryness, and some effect on hearing (Teixeira, M. S., Alper, C. M., Martin, B. S., Helal, N., Doyle, B. M., and Doyle, W. J. 2016. "Oxymetazoline Applied Topically to the Nasal Mucosa Decreases Trans-mucosal Nitrous Oxide Exchange for the Middle Ear," *Annals of Otology, Rhinology, and Laryngology* 125(5):400-407). Phenylephrine hydrochloride can cause bradycardia. (Farkas, A., Dempster, J., and Coker, S. J. 2008. "Importance of Vagally Mediated Bradycardia for the Induction of Torsade de Pointes in an In Vivo Model," *British Journal of Pharmacology* 154(5):958-970).

Steroid nasal sprays can cause burning, itching, and dryness of the nasal and pharyngeal mucosae, cephalalgia, or headache, epistaxis, or nosebleed, running nose, sneezing, immunosuppression leading to infection, serious effects on vision such as glaucoma, hives, angioedema, anaphylaxis, dysmenorrhea, and endocrine problems such as weight gain (Mangan, T. 2017. "Side Effects of Nasal Steroid Spray," at https://www.livestrong.com/article/234291-types-of-prescription-nasal-sprays/). Discrete organs can be targeted with any drug that can be prepared for delivery to and release by an impasse-jacket placed at an inlet to the organ such as the renal artery to target a kidney or other inlet such as a ureter to target the bladder. If take-up of the drug by the target organ would leave a potentially harmful residue pass into the outflow, then an impasse-jacket at the outlet is used to release a reversal agent, thus circumscribing a delimited portion of the circulation and its territory for exposure to the drug.

These examples are cited to make the general point that minor surgery should not perfunctorily be relegated to the course of last resort, without regard to remedies for these conditions specifically using means described herein, conventional measures for alleviating hyperacidity and nasal congestion without the use of drugs specified above. Endogenous histamine type $H_2$ is a causative agent for hyperchlorhydria (hyperacidity, 'heat burn') (see, for example, Mejia, A. and Kraft, W. K. 2009. "Acid Peptic Diseases: Pharmacological Approach to Treatment," *Expert Review of Clinical Pharmacology* 2(3):295-314; Scarpignato, C., Pelosini, I., and Di Mario, F. 2006. "Acid Suppression Therapy: Where Do We Go From Here?," *Digestive Diseases* (Basel, Switzerland) 24(1-2):11-46; Beales, I. L. 2002. "Easy as 1, 2, 3? Histamine Receptors and Gastric Acid," *Gut* 50(6):747-748).

Histamine Types $H_1$ and $H_3$ are the causative agents for swollen nasal membranes (see, for example, Bosma, R., Witt, G., Vaas, L. A. I., Josimovic, I., Gribbon, P., and 3 others 2017. "The Target Residence Time of Antihistamines Determines Their Antagonism of the G Protein-Coupled Histamine H1 Receptor," *Frontiers in Pharmacology* 8:667; Procopiou, P. A., Ford, A. J., Gore, P. M., Looker, B. E., Hodgson, S. T., and 7 others 2017. "Design of Phthalazinone Amide Histamine H1 Receptor Antagonists for Use in Rhinitis," *American Chemical Society Medicinal Chemistry Letters* 8(5):577-581; Khanfar, M. A., Affini, A., Lutsenko, K., Nikolic, K., Butini, S., and Stark, H. 2016. "Multiple Targeting Approaches on Histamine H3 Receptor Antagonists," *Frontiers in Neuroscience* 10:201; Slack, R. J., Russell, L. J., Hall, D. A., Luttmann, M. A., Ford, A. J., and 5 others 2011. "Pharmacological Characterization of GSK1004723, a Novel, Long-acting Antagonist at Histamine H(1) and H(3) Receptors," *British Journal of Pharmacology* 164(6):1627-1641; Lieberman, P. 2009. "The Role of Antihistamines in the Treatment of Vasomotor Rhinitis," *World Allergy Organization Journal* 2(8):156-161; Taylor-Clark, T., Sodha, R., Warner, B., and Foreman, J. 2005. "Histamine Receptors that Influence Blockage of the Normal Human Nasal Airway," *British Journal of Pharmacology* 144(6):867-874).

For most conditions, the means described herein provide alternatives to the administration of potentially harmful drugs on a long-term if not lifelong basis. Less serious conditions, where surgical access to the nidal site or sites is relatively direct, are treated by connecting a jacket for the directly targeted release of drugs, for example, into one or more supply arteries proximate to the affected organ or tissue. Alternatively, a tissue surface connector is affixed to the surface of the affected organ or tissue so that the styloid device it mounts, such as a hollow needle, angioscope, charge coupled device camera (charge coupled device camera, or fluorescence lifetime imaging microscopy (see below in section 4d(3), entitled Nontumefacient Enabled Attainment of Implantable Ductus-intramural Thickness), intravascular ultrasound probe, high intensity forcused ultrasound probe, or excimer laser, is stably oriented, or aimed, within the substrate organ or tissue. Therapeutic and diagnostic apparatus using a nonimplanable conrol console are attached to the implant system through a socket in the body surface port.

The placement of these involves relatively minor surgery performed under local anesthesia. More serious conditions warrant more intricate surgery under general anesthesia; however, in all cases, the fact that drugs and other treatment modalities are directly targeted means that adverse side effects are minimized if not eliminated. This may make possible the problem-free use of long available drugs to which many patients have an adverse reaction over time and for which certain patients have little if any tolerance when the drugs are systemically circulated. Similar to opting for the use of nontargeted, systemically circulated drugs is the use of appliances that pose the risk of complications.

c. In veterinary practice, for example, the postponing of surgery, instead opting for the use of a tracheal stent to suppress the symptoms associated with tracheal collapse (the progressive loss in resilience of the tracheal cartilage rings) interferes with mucociliary clearance, promoting the accumulation of mucus and the inviting of infection. In this case, however, the conventional surgical remedy calls for extensive incision, dissection, and stitching. While requiring general anesthesia, the alternative remedy set forth herein, delineated below in sections VII2c(1)(a) and VII2c(1)(b), for the alleviation of tracheal collapse involves minimal surgery. This condition, which presents in animals, is not the same as the trachemalacia occasionally seen in an infant. The latter spontaneously resolves of its own accord as the tracheal rings, premature and lacking in resilience at birth, develop resilience so that no surgical remedy should be attempted. In this instance, the short-term placement of a stent with close monitoring of the condition is justified to eliminate the risk of suffocation.

d. Another example of the eventual harm which can accrue if effective measures are not taken at the outset is the placement of a conventional stent or stent-graft to correct a more severe coarctation of the aorta where surgical reconstruction ab initio, while itself subject to adverse sequelae, is currently still the more reliable approach for long term repair, especially in the young if not too ill to tolerate the surgery, then justifying the placement of a covered stent or stent-graft (see, for example, Promphan, W. and Qureshi, S. A. 2016. "What Interventional Cardiologists are Still Leaving to the Surgeons?," *Frontiers in Pediatrics* 4:59; Torok, R. D., Campbell, M. J., Fleming, G. A., and Hill, K. D. 2015. "Coarctation of the Aorta: Management from Infancy to Adulthood," *World Journal of Cardiology* 7(11):765-775; Bruckheimer, E. and Pedra, C. A. C. 2013. "Stenting Options for Coarctation of the Aorta," *Interventional Cardiology Clinics* 2(1):115-129; Luijendijk, P., Bouma, B. J., Groenink, M., Boekholdt, M., Hazekamp, M. G., and 4 others 2012. "Surgical Versus Percutaneous Treatment of Aortic Coarctation: New Standards in An Era of Transcatheter Repair," *Expert Review of Cardiovascular Therapy* 10(12):1517-1531; Kische, S., Schneider, H., Akin, I., Ortak, J., Rehders, T. C., Chatterjee, T., Nienaber, C. A., and Ince, H. 2010. "Technique of Interventional Repair in Adult Aortic Coarctation," *Journal of Vascular Surgery* 51(6): 1550-1559; Egan, M. and Holzer, R. J. 2009. "Comparing Balloon Angioplasty, Stenting and Surgery in the Treatment of Aortic Coarctation," *Expert Review of Cardiovascular Therapy* 7(11):1401-1412), would prove more sufficient and durable.

Often effective for avoiding a more radical coarctoplasty or coarterectomy in an adult, in a neonate or infant, conventional covered self-expanding stents or stent grafts may not hold fast and migrate as the aorta grows, migration occasionally occuring in an adult as well (see, for example, Rad, E. M., Mortezaeian, H., Pouraliakbar, H. R., and Hijazi, Z. M. 2017. "Pitfalls of Stenting Coarctation of an Angulated Right Circumflex Aortic Arch in Goldenhar Syndrome," *Annals of Pediatric Cardiology* 10(2):194-196; Jha, N. K., Tofeig, M., Kumar, R. A., ElTahir, A., Athar, S. M., AlHakami, A., Khan, A., and Khan, M. D. 2016. "Stent Dilatation of Atretic Aortic Coarctation in an Adult—Case report and Literature Review," *Journal of Cardiothoracic Surgery* 11:10; Forbes, T. J. and Gowda, S. T. 2014. "Intravascular Stent Therapy for Coarctation of the Aorta," *Methodist Debakey Cardiovascular Journal* 10(2):82-87; Ang, H. L., Lim, C. W., Hia, C., Yip, J., and Quek, S. C. 2014. "Coarctation of the Aorta: Nonsurgical Treatment Using Stent Implantation," *Singapore Medical Journal* 55(6):302-304; Ringel, R. E., Vincent, J., Jenkins, K. J., Gauvreau, K., Moses, H., Lofgren, K., and Usmani, K. 2013. "Acute Outcome of Stent Therapy for Coarctation of the Aorta: Results of the Coarctation of the Aorta Stent Trial," *Catheterization and Cardiovascular Interventions* 82(4):503-510; Yaylali, Y. T., Evrengul, H., and Uludag, B. 2013. "Successful Management of a Proximally Migrated Stent in a Middle-aged Woman with Unnoticed Native Aortic Coarctation," *International Journal of Cardiology* 168(1):e19-21; Kannan, B. R. and Srinivasan, M. 2012. "Stent Migration During Transcatheter Management of Coarctation of Aorta," *Catheterization and Cardiovascular Interventions* 79(3): 408-413; Nikolov, D., Grigorova, V., Petrov, I., and Ivanov, V. 2011. "Emergency Surgical Intervention After Unsuccessful Percutaneous Transluminal Angioplasty and Stenting of Aortic Coarctation," *Interactive Cardiovascular and Thoracic Surgery* 13(1):98-100; Forbes, T. J., Garekar, S., Amin, Z., Zahn, E. M., Nykanen, D., and 19 others 2007. "Procedural Results and Acute Complications in Stenting Native and Recurrent Coarctation of the Aorta in Patients over 4 Years of Age: A Multi-institutional Study," *Catheterization and Cardiovascular Interventions* 70(2):276-285; Karl, T. R. 2007. "Surgery is the Best Treatment for Primary Coarctation in the Majority of Cases," *Journal of Cardiovascular Medicine* (Hagerstown, Md.) 8(1):50-56). Coarctation is further addressed below.

While in an adult, growth is not a risk for dislodgement so that stenting is more dependable than in an infant, in the young, stenting may be chosen as a bridging (holding, salvaging) strategy until the patient, usually very ill, is ready to undergo reconstructive surgery (see, for example, Bugeja, J., Cutajar, D., Zahra, C., Parascandalo, R., Grech, V., and DeGiovanni, J. V. 2016. "Aortic Stenting for Neonatal Coarctation of the Aorta—When Should this be Considered?," *Images in Paediatric Cardiology* 18(3):1-4; Haponiuk, I., Chojnicki, M., Steffens, M., Jaworski, R., Szofer-Sendrowska, A., and 5 others 2013. "Miniinvasive Interventional Bridge to Major Surgical Repair of Critical Aortic Coarctation in a Newborn with Severe Multiorgan Failure" *Wideochirurgia Inne Techniki Maloinwazyjne* [Videosurgery and Other Miniinvasive Techniques] 8(3):244-248; Sreeram, I., Sreeram, N., and Bennink, G. 2012. "Palliative Stent Implantation for Coarctation in Neonates and Young Infants," *Annals of Pediatric Cardiology* 5(2): 145-150).

Other growth-related problems threaten the young patient following surgical repair: especially when ductal (ductus arteriosus) tissue is not completely resected, surgery is not necessarily free of numerous growth-related adverse sequelae (Torok, R. D., Campbell, M. J., Fleming, G. A., and Hill, K. D. 2015. "Coarctation of the Aorta: Management from Infancy to Adulthood," *World Journal of Cardiology* 7(11): 765-775; Vergales, J. E., Gangemi, J. J., Rhueban, K. S., and Lim, D. S. 2013. "Coarctation of the Aorta—The Current State of Surgical and transcatheter Therapies," *Current Cardiology Reviews* 9(3):211-219; Rosenthal, E. 2005. "Coarctation of the Aorta from Fetus to Adult: Curable Condition or Life Long Disease Process?," *Heart* (journal of the British Cardiac Society) 91(11):1495-1502; Head, C. E., Jowett, V. C., Sharland, G. K., and Simpson, J. M. 2005. "Timing of Presentation and Postnatal Outcome of Infants Suspected of Having Coarctation of the Aorta During Fetal Life," *Heart* (journal of the British Cardiac Society) 91(8): 1070-1074; Backer, C. L., Mavroudis, C., Zias, E. A., Amin, Z., and Weigel, T. J. 1998. "Repair of Coarctation with Resection and Extended End-to-end Anastomosis," *Annals of Thoracic Surgery* 66(4):1365-1371; Van Son, J. A., Falk, V., Schneider, P., Smedts, F., and Mohr, F. W. 1997. "Repair of Coarctation of the Aorta in Neonates and Young Infants," *Journal of Cardiac Surgery* 12(3):139-146; Rajasinghe, H. A., Reddy, V. M., van Son, J. A., Black, M. D., McElhinney, D. B., Brook, M. M., and Hanley, F. L. 1996. "Coarctation Repair Using End-to-side Anastomosis of Descending Aorta to Proximal Aortic Arch," *Annals of Thoracic Surgery* 61(3):840-844; Rubay, J. E., Sluysmans, T., Alexandrescu, V., Khelif, K., Moulin, D., Vliers, A., Jaumin, P., and Chalant, C. H. 1992. "Surgical Repair of Coarctation of the Aorta in Infants Under One Year of Age. Long-term Results in 146 Patients Comparing Subclavian Flap Angioplasty and Modified End-to-end Anastomosis," *Journal of Cardiovascular Surgery* (Turin, Italy) 33(2):216-222), this in addition to the risks besides abnormal blood pressure following surgery for adults (see, for example, Bruckheimer, E. and Pedra, C. A. C. 2013, Op cit.).

e. Yet another example of the eventual harm which accrues if effective measures are not taken at the outset is reconstruction of a severely malformed neonate or infant heart when a replacement is available. No repair of more complex congenital heart defects however skilled achieves normal circulatory function, surgical remediation often properly relegated to a bridging procedure until a replacement heart can be found. So long as development continues with a badly defective heart, the lack of normal circulation is propagated throughout the body as a chronic hypoxia that results in progressive multiple, indeed global, organ damage, severely affecting the brain, liver, and kidneys, and a life limited by a continuous and inexorable increase in left ventricular load that comes with growth to add to the intrinsic antecedent dysfunction until left ventricular overload can no longer be withstood.

That following replacement, using the means described herein, immunosuppressive, antimicrobial, and anti-inflammatory drugs can be automatically and directly targeted to the transplant substantially diminishes the quality of life-degrading need for the patient to self-administer these for life, and the fact that drug delivery is directly pipe-targeted to the transplant with or without a background systemic dose means that the severe side effects of immunosuppressives with increased exposure to infection is minimized if not eliminated.

Prompt replacement of a univentricular or otherwise severely malformed and not adequately repairable heart in the young has inadequate durability. Although less so with increasing pharmaceutical experience, remedial procedures only alter, but do not dispel, the pulmonary vascular resistance and hypertension that makes the condition harmful and precarious. By instantly and precisely responding to alterations in adverse pulmonary arterial indicia with new and improved drugs, an automatic prosthetic disorder response system should significantly lessen hypertension at every stage in treatment, extend the periods between successive stages in surgical correction, and if not accomplished at the outset, transplantation and if still necessary, retransplantation. The overall result is an extended and less oppressive life.

A completed Fontan repair ameliorates but does not alleviate the key problem of pulmonary vascular resistance, and its reinstatement following transplantation combined with growth will eventually necessitate retransplantation (see, for example, Hauck, A., Porta, N., Lestrud, S., and Berger, S. 2017. "The Pulmonary Circulation in the Single Ventricle Patient," *Children* (Basel, Switzerland) 4(8). pii: E71; Egbe, A. C., Connolly. H. M., Miranda, W. R., Ammash, N. M., Hagler, D. J., Veldtman, G. R., and Borlaug, B. A. 2017. "Hemodynamics of Fontan Failure: The Role of Pulmonary Vascular Disease," *Circulation. Heart Failure* 10(12). pii: e004515; Kindel, S. J. and Everitt, M. D. 2016. "A Contemporary Review of Paediatric Heart Transplantation and Mechanical Circulatory Support," *Cardiology in the Young* 26(5):851-859; Fredenburg, T. B., Johnson, T. R., and Cohen, M. D. 2011. "The Fontan Procedure: Anatomy, Complications, and Manifestations of Failure," *Radiographics* 31(2):453-463; Maxwell, B. G., Sheikh, A. Y., Ajuba-Iwuji, C. C., Heitmiller, E. S., and Vricella, L. A. 2015. "Pulmonary Vascular Resistance Index and Mortality after Paediatric Heart Transplant," *Cardiology in the Young* 25(6):1141-1147; Snarr, B. S., Paridon, S. M., Rychik, J., and Goldberg, D. J. 2015. "Pulmonary Vasodilator Therapy in the Failing Fontan Circulation: Rationale and Efficacy," *Cardiology in the Young* 25(8):1489-1492; Michielon, G., Carotti, A., Pongiglione, G., Cogo, P., anf Parisi, F. 2011. "Orthotopic Heart Transplantation in Patients with Univentricular Physiology," *Current Cardiology Reviews* 7(2):85-91; Gazit, A. Z. and Canter, C. E. 2011. "Impact of Pulmonary Vascular Resistances in Heart Transplantation for Congenital Heart Disease," *Current Cardiology Reviews* 7(2):59-66).

Even with banding of the pulmonary artery to suppress hypertension and a superior cavopulmonary connection operation, leaving otherwise untreated a univentricular heart results in the progressive degradation and maldevelopment of all organ systems from the moment of birth (Al-Dairy, A., Dehaki, M. G., Omrani, G., Sadeghpour, A., Jalali, A. H., and 3 others 2017. "The Outcomes of Superior Cavopulmonary Connection Operation: A Single Center Experience," *Brazilian Journal of Cardiovascular Surgery* 32(6):503-507; Kalantre, A., Sunil, G. S., and Kumar, R. K. 2016. "Pulmonary Venous Hypertension May Allow Delayed Palliation of Single Ventricle Physiology with Pulmonary Hypertension," *Annals of Pediatric Cardiology* 9(2):147-152; Alsoufi, B., McCracken, C., Schlosser, B., Sachdeva, R., Well, A., and 3 others 2016. "Outcomes of Multistage Palliation of Infants with Functional Single Ventricle and Heterotaxy Syndrome," *Journal of Thoracic and Cardiovascular Surgery* 151(5):1369-1377.e2; Alsoufi, B., Manlhiot, C., Ehrlich, A., Oster, M., Kogon, B., and 4 others 2015. "Results of Palliation with an Initial Pulmonary Artery Band in Patients with Single Ventricle Associated with Unrestricted Pulmonary Blood Flow," *Journal of Thoracic and Cardiovascular Surgery* 149(1):213-220; Schwartz, M. C., Sullivan, L., Cohen, M. S., Russo, P., John, A. S., Guo, R., Guttenberg, M., and Rand, E. B. 2012. "Hepatic Pathology May Develop Before the Fontan Operation in Children with Functional Single Ventricle: An Autopsy Study," *Journal of Thoracic and Cardiovascular Surgery* 143(4):904-909; Alsoufi, B., Manlhiot, C., Awan, A., Alfadley, F., Al-Ahmadi, M., and 3 others 2012. "Current Outcomes of the Glenn Bidirectional Cavopulmonary Connection for Single Ventricle Palliation," *European Journal of Cardiothoracic Surgery* 42(1):42-49; Bove, E. L. 1986. "Cardiac Surgery for the Adolescent with Univentricular Heart," *Pediatrician* 13(4):171-179), essentially forcing either a Fontan procedure to ameliorate but not eliminate the progressive degradation, or if a replacement heart is available, a heart transplantation, which conventionally supported, substantially discontinues most organ system breakdown and provided the baby is closely monitored and the drug regimen adhered to, reduces but does not eliminate pulmonary vascular resistance.

Because it responds instantly and precisely at any time in any place with repair, usually a Fontan, modified, or hybrid, superior cavopulmonary connection operation (see, for example, Al-Dairy, A., Dehaki, M. G., Omrani, G., Sadeghpour, A., Jalali, A. H., and 3 others 2017, Op cit.), or septation procedure to divide the one functional ventricle (Bove, E. L. 1986, Op cit.), or a transplant, an automatic adaptive disorder response system as delineated in sections XX and XX below will provide better support before or with any resolution.

More specifically, the controlling program adaptive, once placed in a prenate or neonate, the system will continuously optimize medicinal therapy at every succeeding stage in the disease and its treatment, to include that preceding any treatment, that following preliminary procedures such as banding and cavopulmonary connection, and any measures applied thereafter to include Fontan-preparatory (Norwood, Hemi-Fontan, or Glenn) (see, for example, Liang, F., Senzaki, H., Yin, Z., Fan, Y., Sughimoto, K., and Liu, H. 2013. "Transient Hemodynamic Changes upon Changing a BCPA [bidirectional cavopulmonary (Glenn) anastomosis] into a TCPC [total cavopulmonary connection] in Staged Fontan Operation: A Computational Model Study," *Scientific World Journal* 2013:486815; Podzolkov, V. P., Zelenikin, M. M., Yurlov, I. A., Kovalev, D. V., Mchedlishvili, K. A., Putiato, N. A., and Zaets, S. B. 2011. "Immediate Results of Bidirectional Cavopulmonary Anastomosis and Fontan Operations in Adults," *Interactive Cardiovascular and Thoracic Surgery* 12(2):141-145; Giglia, T. M. and Humpl, T. 2010. "Preoperative Pulmonary Hemodynamics and Assessment of Operability: Is There a Pulmonary Vascular Resistance that Precludes Cardiac Operation?," *Pediatric Critical Care Medicine* 11(2 Supplement):S57-S69), then a Fontan, and with the means described herein, best followed by a transplant.

That is, the will adaptively dispense medication to optimize circulation before repair or replacement. Quick to adapt, it therefore better sustains the pre- and post-Fontan or other repair in preparation for a transplant, and then better sustains the transplant, extending the time until—at the present state in development of transplant support—the effects of residual pulmonary hypertension necessitate retransplantation. In favorable circumstances and with optimized pharmacy, the need for a retransplantation might be avoided.

Deferral of transplantation following a Fontan repair can actually preclude transplantation (see, for example, Dijkstra, H., Wolff, D., van Melle, J. P., Bartelds, B., Willems, T. P., and 6 others 2017. "Diminished Liver Microperfusion in Fontan Patients: A Biexponential DWI [iffusion-weighted imaging] Study," *Public Library of Science One* 12(3): e0173149; Greenway, S. C., Crossland, D. S., Hudson, M., Martin, S. R., Myers, R. P., and 3 others 2016. "Fontan-associated Liver Disease: Implications for Heart Transplantation," *Journal of Heart and Lung Transplantation* 35(1): 26-33; Michielon, G., Carotti, A., Pongiglione, G., Cogo, P., and Parisi, F. 2011, Op cit.—"It is erroneous to assume that because a Fontan patient is alive, the pulmonary vascular resistance is low enough to tolerate an OHT [orthotopic heart transplantation];" see also Giglia, T. M. and Humpl, T. 2010, Op cit.). Moreover, the combination of nontargeted immunosuppressive and pulmonary impairment promotes infection (Michielon, G., Carotti, A., Pongiglione, G., Cogo, P., anf Parisi, F. 2011, Op cit. —"Intolerance to Fontan physiology with prolonged pleural effusions, ascites, lymphopenia and protein dispersion can predispose to life-threatening infections that are triggered by post-OHT immunosuppression").

While it is possible to support a Fontan procedure with such an implanted automatic adaptive response system to deliver respiration and circulation supportive drugs (see, for example, Dasse, K. A., Petit, P. C., Fine, D. H., and Vasquez, G. 2017. Method and Apparatus for Administering Nitric Oxide with Supplemental Drugs, World Intellectual Property Organization Patent Application 2017/116,776; Oldenburger, N. J., Mank, A., Etnel, J., Takkenberg, J. J., and Helbing, W. A. 2016. "Drug Therapy in the Prevention of Failure of the Fontan Circulation: A Systematic Review," *Cardiology in the Young* 26(5):842-850; Mori, H., Park, I. S., Yamagishi, H. 1, Nakamura, M., Ishikawa, S., and 5 others 2016. "Sildenafil Reduces Pulmonary Vascular Resistance in Single Ventricular Physiology," *International Journal of Cardiology* 221:122-127; Butts, R. J., Chowdhury, S. M., Baker, G. H., Bandisode, V., Savage, A. J., and Atz, A. M. 2016. "Effect of Sildenafil on Pressure-volume Loop Measures of Ventricular Function in Fontan Patients," *Pediatric Cardiology* 37(1):184-191; Bosc, L. V. G., Maston, L. D., and Rest, T. 2016. Compositions and Methods for Treatment of Pulmonary Hypertension, World Intellectual Property Organization Patent Application 2016/176,399; Coyle, K., Coyle, D., Blouin, J., Lee, K., Jabr, M. F., and 4 others 2016. "Cost Effectiveness of First-line Oral Therapies for Pulmonary Arterial Hypertension: A Modelling Study," *PharmacoEconomics* 34(5):509-520; Hebert, A., Mikkelsen, U. R., Thilen, U., Idorn, L., Jensen, A. S., and 4 others 2014. "Bosentan Improves Exercise Capacity in Adolescents and Adults after Fontan Operation: The TEMPO (Treatment with Endothelin Receptor Antagonist in Fontan Patients, a Randomized, Placebo-controlled, Double-blind Study Measuring Peak Oxygen Consumption) Study," *Circulation* 130(23):2021-2030; Chen, Y. F., Jowett, S., Barton, P., Malottki, K., Hyde, C., and 5 others 2009. "Clinical and Cost-effectiveness of Epoprostenol, Iloprost, Bosentan, Sitaxentan and Sildenafil for Pulmonary Arterial Hypertension within Their Licensed Indications: A Systematic Review and Economic Evaluation," *Health Technology Assessment* (Winchester, England) 13(49):1-320; Simmonds, J., Burch, M., Dawkins, H., and Tsang, V. 2008. "Heart Transplantation after Congenital Heart Surgery: Improving Results and Future Goals," *European Journal of Cardiothoracic Surgery* 34(2):313-317), when a replacement heart is available, it is preferable to replace the defective heart ab initio.

However, if a replacement is unavailable, since it is likely that the speed and accuracy of response will better sustain a Fontan until a replacement heart becomes available, the system is best implanted to support the Fontan and then reprogrammed to support the new heart. Such reprogramming does not include the drug response to the pulmonary hypertension induced by the pretransplantation pulmonary vascular resistance, to which the adaptive system will spontaneously adjust, but rather the addition of immunosuppressives and anti-inflammatories, for example, as pertinent.

An automatic prosthetic disorder response system as delineated below in sections XX entitled Exemplary Channel of Control in a Fully Implanted Ambulatory Adaptive Hierarchical Control System for Automatic Response to a Comorbid Condition and XXI entitled Fully Implanted Ambulatory Adaptive Hierarchical Control Systems for Automatic Response to a Comorbid Condition in combination with new and improved drugs for immunosuppression also beneficiates transplantation otherwise jeopardized by two other key deterrents—drug regimen noncompliance and imunosuppresive side effects.

This is because the system directly pipe-targets the drugs to the treatment site, sparing other organs and tissue—and regimen noncompliance the second most significant cause of failure—because it dispenses the drugs the moment the need therefor is reported by the implanted sensors to the implanted microprocessor—anywhere, anytime—in the middle of the night while the baby is asleep, before the baby senses any experiential correlate, before there is any realization of such need, and without a clinician present. Equally important, the system adaptively dispenses the drugs on the basis of the previous diagnostic-to-medication relationship data it has accumulated, thus assuring not only immediate but theranostic drug delivery under any circumstances.

More specifically, since the system is adaptive, this applies with the system placed in the neonate or infant prior to and following surgical repair, then following heart transplantation if applicable, and in some cases, liver transplantation, the system designed to remain in place with the ability to accommodate growth for years. Some babies will require a replacement heart, liver, and lungs, which should be staged over intervals sufficient for full recovery. The sites of flexibility that allow for growth are summarized below toward the end of section XXI, for example, entitled Fully Implanted Ambulatory Adaptive Hierarchical Control Systems for Automatic Response to a Comorbid Condition.

However, in contrast to attempts at surgical repair, prompt transplantation with proper pharmaceutical management of pulmonary vascular resistance better supports early development where a nominally repaired and still defective heart does not, and later transplantation of an inadequately repaired congenital heart can never return to normal all other organ systems that had been left to develop abnormally (see, for example, Kelly, C. J., Makropoulos, A., Cordero-Grande, L., Hutter, J., Price, A., and 15 others 2017. "Impaired Development of the Cerebral Cortex in Infants with Congenital Heart Disease is Correlated to Reduced Cerebral Oxygen Delivery," *Scientific Reports* 7(1):15088; Puelz, C., Acosta, S., Rivière, B., Penny, D. J., Brady, K. M., and Rusin, C. G. 2017. "A Computational Study of the Fontan Circulation with Fenestration or Hepatic Vein Exclusion," *Computers in Biology and Medicine* 89:405-418; Goldberg, D. J., Surrey, L. F., Glatz, A. C., Dodds, K., O'Byrne, M. L., and 6 others 2017. "Hepatic Fibrosis is Universal Following Fontan Operation, and Severity is Associated with Time from Surgery: A Liver Biopsy and Hemodynamic Study," *Journal of the American Heart Association* 6(5); Dijkstra H., Wolff, D., van Melle, J. P., Bartelds, B., Willems, T. P., and 6 others 2017, Op cit.; Ohuchi, H. 2017. "Where is the "Optimal" Fontan Hemodynamics?," *Korean Circulation Journal* 47(6):842-857; Morton, P. D., Korotcova, L., Lewis, B. K., Bhuvanendran, S., Ramachandra, S. D., and 7 others 2017. "Abnormal Neurogenesis and Cortical Growth in Congenital Heart Disease," *Science Translational Medicine* 9(374). pii: eaah7029; Fidai, A., Dallaire, F., Alvarez, N., Balon, Y., Clegg, R., and 11 others 2017. "Non-invasive Investigations for the Diagnosis of Fontan-associated Liver Disease in Pediatric and Adult Fontan Patients," *Frontiers in Cardiovascular Medicine* 4:15; Hilscher, M. B., Johnson, J. N., Cetta, F., Driscoll, D. J. 3, Poterucha, J. J., and 3 others 2017. "Surveillance for Liver Complications after the Fontan Procedure," *Congenital Heart Disease* 12(2):124-132; Oh, C., Youn, J. K., Han, J. W., Kim, G. B., Kim, H. Y., and Jung, S. E. 2016. "Hepatocellular Carcinoma after the Fontan Procedure in a 16-year-old Girl: A Case Report," *Medicine* (Baltimore, Md.) 95(41):e4823; Josephus Jitta, D., Wagenaar, L. J., Mulder, B. J., Guichelaar, M., Bouman, D., and van Melle, J. P. 2016. "Three Cases of Hepatocellular Carcinoma in Fontan Patients: Review of the Literature and Suggestions for Hepatic Screening," *International Journal of Cardiology* 206:21-26; Takuma, Y., Fukada, Y., Iwadou, S., Miyatake, H., Uematsu, S., and 7 others 2016. "Surgical Resection for Hepatocellular Carcinoma with Cardiac Cirrhosis after the Fontan Procedure," *Internal Medicine* (Tokyo, Japan) 55(22):3265-3272; Chen, B., Schreiber, R. A., Human, D. G., Potts, J. E., and Guttman, O. R. 2016. "Assessment of Liver Stiffness in Pediatric Fontan Patients Using Transient Elastography," *Canadian Journal of Gastroenterology and Hepatology* 2016:7125193; Wolff, D., van Melle, J. P., Dijkstra, H., Bartelds, B., Willems, T. P., and 5 others 2016. "The Fontan Circulation and the Liver: A Magnetic Resonance Diffusion-weighted Imaging Study," *International Journal of Cardiology* 202:595-600; Kwon, S., Scovel, L., Yeh, M., Dorsey, D., Dembo, G., and 6 others 2015. "Surgical Management of Hepatocellular Carcinoma after Fontan Procedure," *Journal of Gastrointestinal Oncology* 6(3):E55-E60; Wu, F. M., Jonas, M. M., Opotowsky, A. R., Harmon, A., Raza, R., and 6 others 2015. "Portal and Centrilobular Hepatic Fibrosis in Fontan Circulation and Clinical Outcomes," *Journal of Heart and Lung Transplantation* 2015 34(7):883-891; Assenza, G. E., Graham, D. A., Landzberg, M. J., Valente, A. M., Singh, M. N., and 6 others 2013. "MELD-XI [Model for End-stage Liver Disease eXcluding International Normalization Ratio score] Score and Cardiac Mortality or Transplantation in Patients after Fontan Surgery," *Heart* (British Cardiac Society) 99(7):491-496; Rychik, J., Veldtman, G., Rand, E., Russo, P., Rome, J. J., and 4 others 2012. "The Precarious State of the Liver after a Fontan Operation: Summary of a Multidisciplinary Symposium," *Pediatric Cardiology* 33(7):1001-1012; Goldberg, C. S., Mussatto, K., Licht, D., and Wernovsky, G. 2011. "Neurodevelopment and Quality of Life for Children with Hypoplastic Left Heart Syndrome: Current Knowns and Unknowns," *Cardiology in the Young* 21 Supplement 2:88-92; Ghaferi, A. A. and Hutchins, G. M. 2005. "Progression of Liver Pathology in Patients Undergoing the Fontan Procedure: Chronic Passive Congestion, Cardiac Cirrhosis, Hepatic Adenoma, and Hepatocellular Carcinoma," *Journal of Thoracic and Cardiovascular Surgery* 129(6): 1348-1352).

Nevertheless, the prompt replacement of a severely defective heart in utero or shortly postpartum averts operative and postoperative complications which can result from preceding attempts at reconstruction, to include the adverse respiratory effects of Fontan circulation, obscuring scarring, adhesions (Lamour, J. M., Kanter, K. R., Naftel, D. C., Chrisant, M. R., Morrow, W. R., Clemson, B. S., and Kirklin, J. K. 2009. "The Effect of Age, Diagnosis, and Previous Surgery in Children and Adults Undergoing Heart Transplantation for Congenital Heart Disease," *Journal of the American College of Cardiology* 54(2):160-165), as well as delay a proper correction as damage caused by faulty circulation continues to accumulate, significantly increasing the need while decreasing the prospects for successful transplantation at a later time (see, for example, Alsoufi, B., Mahle, W. T., Manlhiot, C., Deshpande, S., Kogon, B., McCrindle, B. W., and Kanter, K. 2016. "Outcomes of Heart Transplantation in Children with Hypoplastic Left Heart Syndrome Previously Palliated with the Norwood Procedure," *Journal of Thoracic and Cardiovascular Surgery* 151(1):167-175.el-e2; Schumacher, K. R. and Goldberg, D. J. 2016. "Biomarkers and the Fontan Circulation," *Journal of the American Heart Association* 5(1). pii: e002926; Lang, S. M., Frazier, E. A., and Collins, R. T. 2nd 2016. "Aortic Complications following Pediatric Heart Transplantation: A Case Series and Review," *Annals of Pediatric Cardiology* 9(1):42-45; Alsoufi, B., Deshpande, S., McCracken, C., Kogon, B., Vincent, R., Mahle, W., and Kanter, K. 2015. "Results of Heart Ttransplantation Following Failed Staged Palliation of Hypoplastic Left Heart Syndrome and Related Single Ventricle Anomalies," *European Journal of Cardiothoracic Surgery* 48(5):792-799, also cited below; Kanter, K. R., Mahle, W. T., Vincent, R. N., and Berg, A. M. 2011. "Aortic Complications after Pediatric Cardiac Transplantation in Patients with a Previous Norwood Reconstruction," *Seminars in Thoracic and Cardiovascular Surgery. Pediatric Cardiac Surgery Annual* 14(1):24-28; Simmonds, J., Burch, M., Dawkins, H., and Tsang, V. 2008, Op cit.).

To the foregoing can be added the preference in every instance for endoluminal over extraluminal stents, the deterrent consisting of the need for a small incision and some relatively minor dissection to proceed directly to the level along the ductus to be treated. The added trauma to gain access is compensated for by an outcome more reliable over the long term. When the lumen contains no stent, in-stent restenosis, for example, is impossible, this but one of numerous risks associated with the use of guidewires and allowing a foreign object to remain in the lumen, as will be delineated herein. For example, the presence of a stent in the lumen jeopardizes the subsequent use of an atherectomy rotablator which can jam and deform the stent so that it no longer serves its purpose. Rotablator jamming is addressed below in section VII2j(1) entitled Incorporation of Adscititious Capabilities into Barrel-assemblies.

Blocked by the sternum, direct access to the right coronary artery or branch thereof for placement of an extraluminal stent is not through a more traumatic median sternotomy (midsternal thoracotomy, "zipper" incision), but rather through a trephine sternotomy with a low speed, high torque trephine drill under saline irrigation, the plug returned to the opening upon withdrawal and closing. Means for minimizing the risk of adverse events sequelary to penetration of the sternum are available (see, for example, Asakura, Y., Kinoshita, M., Kasuya, Y., Sakuma, S., and Ozaki, M. 2017. "Ultrasound-guided Sternal Bone Marrow Aspiration," *Blood Research* 52(2):148-150; Friedlis, M. F. and Centeno, C. J. 2016. "Performing a Better Bone Marrow Aspiration," *Physical Medicine and Rehabilitation Clinics of North America* 27(4):919-939).

Broadly, poor outcomes often eventuate with transluminal procedures opted for purely on the basis of minimal invasiveness. For a debilitated patient less able or unable to tolerate an open procedure, less traumatic procedures are approariate. However, when this is not the case, an open procedure more likely to finally end the problem is to be preferred, some added trauma notwithstanding. This applies to small arterial stents and aortic sent grafts as addressed below. The misguided approach is clearly seen when failure of the transluminal repair necessitates open repair later anyway—when the patient has further deteriorated.

Adverse sequelae to surgical breech of the sternum, such as pericardial tamponade, are rare and have established remedies (see, for example, Golota, J. J., Orlowski, T., Iwanowicz, K., Snarska, J. 2016. "Air Tamponade of the Heart," *Kardiochirurgia i Torakochirurgia Polska* [Polish Journal of Cardiothoracic Surgery] 13(2):150-153; Santavy, P., Troubil, M., and Lonsky, V. 2013. "Pericardial Tamponade: A Rare Complication of Sternal Bone Marrow Biopsy," *Hematology Reports* 5(3):e13; Inoue, H., Nakasato, T., Yamauchi, K., Nakamura, Y., Oshida, S., and Ehara, S. 2010. "Risk Factors Concerning Sternal Bone Marrow Aspiration and Patient Safety in Japan," *Internal Medicine* (Tokyo, Japan) 49(12):1089-1095; Jarry, J., Lang-Lazdunski, L., Perez, J. P., Barthelemy, R., Berets, O., and Jancovici, R. 2004. "A Serious Complication of Sternal Puncture: Ppenetrating Injury of the Ascending Thoracic Aorta," in French with Engish abstract at Pubmed, *Presse Medicale* 33(1):22-24).

Relative efficacy as between minimally invasive transluminal procedures and surgical intervention is not static but subject to new developments, is gradually shifting in favor of more conservative transluminal approaches over time. For example, carotid endarterectomy, which may be untenably risky with severely impaired patients posing a significant surgical risk, has been found to result in better outcomes than does carotid artery stenting, which is better tolerated, and coronary artery bypass grafting has historically provided better outcomes than does balloon angioplasty. This is, however, gradually changing with the advent of improved medical management and apparatus such as drug eluting stents and cerebral embolic protective devices, addressed below in several sections but especially in section 4d(2) entitled Ductus Wall Tumefacients, and flow reversal, addressed below in section X2b entitled Stereotactic Resituation of a Mispositioned Miniball.

The prepositioning of impasse-jackets described herein and ductus side-entry jackets as described in copending application Ser. No. 14/121,365 published as 20160051806, on pedicles or stumps in organ transplantation allows the targeted delivery of graft sustaining antigenotherapy and if necessary, immunosuppressive drugs, and thus significant reduction if not elimination in the systemic dose of potentially harmful immunosuppressive drugs such as aclizumab, basiliximab, eculizumab, daclizumab, infliximab, alemtuzumab, and other immunosuppressives which reduce patient resisance to infectious disease (see, for example, Shao, M., Tian, T., Zhu, X., Ming, Y., Iwakiri, Y., Ye, S., and Ye, Q. 2017. "Comparative Efficacy and Safety of Antibody Induction Therapy for the Treatment of Kidney: A Network Meta-analysis," *Oncotarget* 8(39):66426-66437; Zheng, J. and Song, W. 2017. "Alemtuzumab Versus Antithymocyte Globulin Induction Therapies in Kidney Transplantation Patients: A Systematic Review and Meta-analysis of Randomized Controlled Trials," *Medicine* (Baltimore, Md.) 96(28):e7151; Hill, P., Cross, N. B., Barnett, A. N., Palmer, S. C., and Webster, A. C. 2017. "Polyclonal and Monoclonal Antibodies for Induction Therapy in Kidney Transplant Recipients," *Cochrane Database of Systematic Reviews* 1:CD004759; Haynes, R., Harden, P., Judge, P., Blackwell, L., Emberson, J., Landray, M. J., Baigent, C., Friend, P. J., and 154 collaborators 2014. "Alemtuzumab-based Induction Treatment Versus Basiliximab-based Induction Treatment in Kidney Transplantation (the 3C [Campath, Calcineurin Inhibitor Reduction and Chronic Allograft Nephropathy] Study): A Randomised Trial," *Lancet* 384(9955):1684-1690; Vazquez, J. A., Miceli, M. H., and Alangaden, G. 2013. "Invasive Fungal Infections in Transplant Recipients," *Therapeutic Advances in Infectious Disease* 1(3):85-105; Hanaway, M. J., Woodle, E. S., Mulgaonkar, S., Peddi, V. R., Kaufman, D. B., First, M. R., Croy, R., and Holman, J. 2011. "Alemtuzumab Induction in Renal Transplantation," *New England Journal of Medicine* 364(20):1909-1919; Safdar, N., Smith, J., Knasinski, V, Sherkow, C., Herrforth, C., Knechtle, S., and Andes, D. 2010. "Infections After the Use of Alemtuzumab in Solid Organ Transplant Recipients: A Comparative Study," *Diagnostic Microbiology and Infectious Disease* 66(1):7-15) with an antibiotic or antiviral when indicated, such as when the donor is cytomegalovirus-seropositive and the recipient cytomegalovirus-seronegative, azathioprine, basiliximab, cyclosphosphamide, cyclosporine, tacrolimus, everolimus, sirolimus, steroids, and so on, or radionuclides with or without an inherent affinity for the organ, to only the transplanted organ without suppression of the immune system for other disease, eliminates the need for separate incisional access.

Generally, even though the directly targeted dose can be more highly concentrated than if dispersed through the general circulation, any fraction not taken up within the treatment site or nidus will quickly become so diluted within the bloodstream as not to pose the prospect of injury to upsteam tissue. If this is not so, as when the drug is radioactive, the drug is delivered in magnetically susceptible form so that the residue is stopped from further travel downstream by forcible detention, either against the endothelium or urothelium. If the passing blood is not significantly irradiated, the downstream ductus side-entry impasse-jacket includes a permanent magnet sub-shell layer magnetized perpendicular to the bloodstream to hold the drug against the endothelium.

When drug delivery is directly pipe or feedline-targeted to the nidus or lesion, medication that is radioactive or otherwise potentially harmful introduced through the pipe or feedline in a ferrofluid bypasses the upstream circulation and the tissue it supplies. If radioactive, the feedline, as shown in copending application Ser. No. 14/121,365, FIGS. 5, 6, and Ser. No. 14/998,495 FIGS. 10A and 10B is shielded. If administration of the drug is to continue over a long term, a small port at the body surface is used as the drug entry point. If uptake at the lesion is not complete and a radioactive residue is not to continue past the drug delivery target, the residue is curtailed from continuation through the bloodstream by a sub-shell electromagnet layer in the side-entry jacket, piped impasse-jacket, or nonjacketing side-entry connector to project an attractive field perpendicular or normal to the long central axis of the substrate vessel.

The field strength of the electromagnet layer is set to no greater than is necessary to draw the drug into the intima or equivalent layer. If the drug is not harmful to normal tissue and is to be drawn against rather than through the endothelium or urothelium, for example, an impasse-jacket with permanent magnet layer as shown in FIGS. 16A, 16B, and 16C and described below in sections 12 and I15 is used. If harmful to normal tissue aside from the target lesion, the magnetically carried residue can be extracted through the grid of the impasse-jacket into the perivascular far or equivalent tissue with the aid of a powerful external (extracorporeal) tractive electromagnet.

A nonradioactive but potentially harmful residue is neutralized through the release through a downstream ductus side-entry jacket of a reversal agent. If delivery is automatic by a microprocessor as addressed below in sections XX and XXI, then the delivery of both the drug and the reversal agent or antidote is automated. If not, then the residue is manually introduced immediately after the drug. If no reversal agent is available, further passage through the bloodstream is prevented by introducing the drug as magnetically carried for recovery by a downstream impasse-jacket. Nanoparticulate drugs can be indissolubly or dissolubly encapsulated to prevent or detain dissolution.

Because drugs are directly pipe-targeted to the treatment site, were the donor cytomegalovirus-seropositive and the recipient cytomegalovirus-seronegative, for example, then provided the efficacy of such treatment had been established, antivirals and immunosuppressive drugs such as azathioprine, basiliximab, cyclosphosphamide, cyclosporine, everolimus, tacrolimus, sirolimus, methotrexate, steroids, and/or radionuclides with or without an inherent affinity for the organ, can be targeted to the graft without injury to other tissue or impairment to the immune system as would expose the patient to pathogens.

Means for the automatic delivery of antimicrobial and rejection-counteractive substances to sustain a transplant on a continuous basis and alleviate dependency upon potentially toxic systemic doses of immunosuppressive drugs are described in copending application Ser. No. 14/121,365 published as 20160051806, entitled Ductus Side-entry Jackets and Prosthetic Disorder Response Systems, which describes a belt-supported power, control, and pump/reservoir pack that delivers drugs through a small port at the body surface, and application Ser. No. 14/998,495 published as 20170197028 entitled Nonjacketing Side-entry Connectors and Prosthetic Disorder Response Systems, which describes the implantation of these components with transdermal energy transfer for closed body ambulatory operation and telemetric data transfer to the clinic.

Such communication can transmit both command and diagnostic signals (see, for example, Mirbozorgi, S. A., Bahrami, H., Sawan, M., Rusch, L. A., and Gosselin, B. 2016. "A Single-Chip Full-duplex High Speed Transceiver for Multi-site Stimulating and Recording Neural Implants," *Institute of Electrical and Electronics Engineers Transactions on Biomedical Circuits and Systems* 10(3):643-653; Hannan, M A., Abbas, S. M., Samad, S. A., and Hussain, A. 2012. "Modulation Techniques for Biomedical Implanted Devices and Their Challenges," *Sensors* (Basel, Switzerland) 12(1):297-319). While a centralized computer to administer patient-specific prescription programs would eliminate the need for a microcontroller implant in each patient or included in a carried power and control pack, current telemetric communication between the centralized controller and each patient falls far short of the dependability required in such an arrangement.

The same may be said for transdermal or transcutaneous charging of the implanted or carried battery, distance considerations for the transmission of power thus currently limiting charging to an at-home or clinic function. Eventually, large regions may be administered by centralized computers. The current state of the medical data telemetric and transcutaneous charging capabilities is addressed below in the section entitled Exemplary Channel of Control in a Fully Implanted Ambulatory Adaptive Hierarchical Control System for Automatic Response to a Comorbid Condition.

Ductus side-entry jackets and nonjacketing side-entry connectors are adaptations of the jackets or collars described herein, to allow the direct piping of drugs, metabolites, enzymes, hormones, temperature sensor/heating or cooling devices, and miniature cabled devices, such as lasers, electrostimulatory, or neuromodulatory, electrodes, intravascular ultrasound viewing, or high-intensity focused ultrasound, or ultrasonic histotripsy, ablation, probes to be fully implanted and stably positioned over an indefinitely long period. Piping is addressed below in section I15e entitled Direct Lines from the Body Surface to and from Impasse- and Other Type Jackets. An exemplary automatic disorder response system is addressed in section XX below and FIG. 107, with the control of such an implanted arrangement addressed in section XXI and FIG. 108.

Using magnetic force to restrict delivery of graft antigens, counteractive antibodies and immunosuppressive medication to and concentrate these in a targeted segment or organ, for example, leaves the rest of the body substantially immunocompetent, reducing the risk of transplant infection with an immunosuppression-opportunistic cytomegalovirus, Epstein-Barr virus, which poses the threat of post transplantation lymphoproliferative disease that can lead to non-Hodgkin's lymphoma and death (see, for example, Martinez, O. M. and Krams, S. M. 2017. "The Immune Response to Epstein Barr Virus and Implications for Posttransplant Lymphoproliferative Disorder," *Transplantation* 101(9): 2009-2016; Bishnoi, R., Bajwa, R., Franke, A. J., Skelton, W. P. 4th, Wang, Y., and 4 others 2017. "Post-transplant Lymphoproliferative Disorder (PTLD): Single Institutional Experience of 141 Patients," *Experimental Hematology and Oncology* 6:26; Das, B., Morrow, R., Huang, R., and Fixler, D. 2016. "Persistent Epstein-Barr Viral Load in Epstein-Barr Viral Naïve Pediatric Heart Transplant Recipients: Risk of Late-onset Post-transplant Lymphoproliferative Disease," *World Journal of Transplantation* 6(4):729-735; "Dharnidharka, V. R., Webster, A. C., Martinez, O. M., Preiksaitis, J. K., Leblond, V. 5., and Choquet, S. 2016. "Post-transplant Lymphoproliferative Disorders," *Nature Reviews. Disease Primers* 2:15088; Jha, H. C., Pei, Y., and Robertson, E. S. 2016. "Epstein-Barr Virus: Diseases Linked to Infection and Transformation," *Frontiers in Microbiology* 7:1602; Lynch, J. P. 3rd, Sayah, D. M., Belperio, J. A., and Weigt, S. S. 2015 "Lung Transplantation for Cystic Fibrosis: Results, Indications, Complications, and Controversies," *Seminars in Respiratory and Critical Care Medicine* 36(2):299-320; San-Juan, R., Manuel, O., Hirsch, H. H., Fernández-Ruiz, M., López-Medrano, F., and 4 others with 105 collaborators 2015. "Current Preventive Strategies and Management of Epstein-Barr Virus-related Post-transplant Lymphoproliferative Disease in Solid Organ Transplantation in Europe. Results of the ESGICH [European Study Group of Infections in Compromised Hosts] Questionnaire-based Cross-sectional Survey," *Clinical Microbiology and Infection* 21(6):604.e1-9; San-Juan, R., Comoli, P., Caillard, S., Moulin, B., Hirsch, H. H., and Meylan, P. 2014. "Epstein-Barr Virus-related Post-transplant Lymphoproliferative Disorder in Solid Organ Transplant Recipients," *Clinical Microbiology and Infection* 20 Supplement 7:109-118; Green, M. and Michaels, M. G. 2013. "Epstein-Barr Virus Infection and Posttransplant Lymphoproliferative Disorder," *American Journal of Transplantation* 13 Supplement 3:41-54; Allen, U. D., Farkas, G., Hébert, D., Weitzman, S., Stephens, D., and 6 others 2005. "Risk Factors for Post-transplant Lymphoproliferative Disorder in Pediatric Patients: A Case-control Study," *Pediatric Transplantation* 9(4):450-455; Allen, U., Alfieri, C., Preiksaitis, J., Humar, A., Moore, D., and 8 others 2002. "Epstein-Barr Virus Infection in Transplant Recipients: Summary of a Workshop on Surveillance, Prevention, and Treatment," *Canadian Journal of Infectious Diseases* 13(2):89-99; Aris, R. M., Maia, D. M., Neuringer, I. P., Gott, K., Kiley, S., Gertis, K., and Handy, J. 1996. "Post-transplantation Lymphoproliferative Disorder in the Epstein-Ban Virus-naïve Lung Transplant Recipient," *American Journal of Respiratory and Critical Care Medicine* 154(6 Part 1):1712-1717).

Polyoma papovavirus, usually BK virus [from the initials of a renal transplant patient]), or *Polyomavirus hominis* type 1 infection is another significant threat (see, for example, Ambalathingal, G. R., Francis, R. S., Smyth, M. J. 2, Smith, C., and Khanna, R. 2017. "BK *Polyomavirus*: Clinical Aspects, Immune Regulation, and Emerging Therapies," *Clinical Microbiology Reviews* 30(2):503-528; Abend, J. R., Changala, M., Sathe, A., Casey, F., Kistler, A., Chandran, S., Howard, A., and Wojciechowski, D. 2017. "Correlation of BK Virus Neutralizing Serostatus with the Incidence of BK Viremia in Kidney Transplant Recipients," *Transplantation* 101(6):1495-1505; Kable, K., Davies, C. D., O'connell, P. J., Chapman, J. R., and Nankivell, B. J. 2017. "Clearance of BK Virus Nephropathy by Combination Antiviral Therapy with Intravenous Immunoglobulin," *Transplantation Direct* 3(4):e142; Sharma, R., Tzetzo, S., Patel, S., Zachariah, M., Sharma, S., and Melendy, T. 2016. "BK Virus in Kidney Transplant: Current Concepts, Recent Advances, and Future Directions," *Experimental and Clinical Transplantation* 14(4):377-384; Jamboti, J. S. 2016. "BK Virus Nephropathy in Renal Transplant Recipients," *Nephrology* (Carlton, Victoria, Australia) 21(8):647-654; Vigil, D., Konstantinov, N. K., Barry, M., Harford, A. M., Servilla, K. S., and 4 others 2016. "BK Nephropathy in the Native Kidneys of Patients with Organ Transplants: Clinical Spectrum of BK Infection," *World Journal of Transplantation* 6(3):472-504; Umbro, I., Tinti, F., Muiesan, P., and Mitterhofer, A. P. 2016. "Different Behaviour of BK-virus Infection in Liver Transplant Recipients," *World Journal of Gastroenterology* 22(4): 1532-1540; Huang, G., Wang, C. X., Zhang, L., Fei, J. G., Deng, S. X., and 5 others 2015. "Monitoring of *Polyomavirus* BK Replication and Impact of Preemptive Immunosuppression Reduction in Renal-transplant Rrecipients in China: A 5-year Single-center Analysis," *Diagnostic Microbiology and Infectious Disease* 81(1):21-26; Pham, P. T., Schaenman, J., and Pham, P. C. 2014. "BK Virus Infection Following Kidney Transplantation: An Overview of Risk Factors, Screening Strategies, and Therapeutic Interventions," *Current Opinion in Organ Transplantation* 19(4): 401-412; Huang, G., Zhang, L., Liang, X., Qiu, J., Deng, R., and 4 others 2014. "Risk Factors for BK Virus Infection and BK Virus-associated Nephropathy Under the Impact of Intensive Monitoring and Pre-emptive Immunosuppression Reduction," *Transplantation Proceedings* 46(10):3448-3454; Hirsch, H. H. and Snydman, D. R. 2005. "BK Virus: Opportunity Makes a Pathogen," *Clinical Infectious Diseases* 41(3):354-360; Finberg, R. and Fingeroth, J. 2005. "Infections in Transplant Recipients," Chapter 117 in *Harrison's Principles of Internal Medicine*, 16th Edition, New York, N.Y.: McGraw-Hill, pages 781-789; Koukoulaki, M., Grispou, E., Pistolas, D., Balaska, K., Apostolou, T., and 7 others 2009. "Prospective Monitoring of BK Virus Replication in Renal Transplant Recipients," *Transplant Infectious Disease* 11(1):1-10), resulting in irremediable graft sloughing.

*The Merck Manual of Diagnosis and Therapy*, Edition 18, Chapter 166, "Transplantation," page 1369 enumerates viral, bacterial, fungal, and parasitic organisms found to infect immunocompromised recipients. If necessary, the same or another impasse-jacket at the arterial inlet is used to release a viricide. Regardless of the projected time or times for release, the impasse-jacket or jackets are fixed in position just after the organ is removed and before completing the graft. Thereafter, release using any of several mechanisms addressed in sections herein on impasse-jackets can be preemptive, prophylactic, or both.

Transplant harvesting preserves sufficient connections or pedicles including major arteries and veins to allow the placement of entry (inlet, inflow) and exit (outlet, outflow) impasse-jackets, so that these are introduced having already been applied to the target organ. A kidney, for example, is harvested with its renal artery, renal vein, and ureter remaining attached. Perigraft infection should it ensue can be treated using the same impasse-jacket or jackets. When graft antigens, counteractive antibodies, immunosuppressive, and antibiotic drugs, for example, must be delivered to different ductus, Ommaya-type reservoirs, subcutaneous infusion set cannulae with catheters leading to the respective jackets, or similar access portals at the body surface are spaced apart to reduce the chance for human error in administering the medication.

Direct piping from the body surface, addressed below in the sections entitled Direct Lines from the Body Surface to and from Impasse- and Other Type Jackets and Single and Plural Circuit Pumping through Direct Lines to Jackets makes it possible to selectively target each impasse-jacket with the substance intended by direct piping. Syringe refill cartridges or portable miniature metering pumps connected to the access portals or infusion cannulae at the body surface selectively supply the drug for each target impasse-jacket. Access to intermittent segments along a ductus, such as unresected skip lesions of Crohn's disease, or regional enteritis, or with atherosclerotic plaques where remodeling discourages transluminal treatment, the chronic condition warrants the implantation of fluid feedlines with a small port at the body surface.

Branching the feedline distal to the port opening allows the use of a single opening in the port at the body surface. If medication is to be administered automatically, then a controlling microprocessor and associated components as appropriate and delineated in sections XX and XXI below are implanted. When the delivery line is branched, the microprocessor actuates the one small flat drug reservoir pump to medicate the lesions at once. Likewise to reserve port openings for other drugs in comorbidity, when a given drug or other therapeutic substance would best be delivered to separate points in a particular order, successive side branches from a common line may be used, whether the takeoffs follow in anterograde or retrograde order.

An unmagnetized inlet jacket directly piped to from a portal at the body surface can deliver a drug and when necessary, an outlet jacket similarly piped can deliver a reversal agent. Where dosing would best respond quickly to changing physiological criteria such as pulse rate or blood pressure, sensors placed to transmit the pertinent data to the pump can be used to administer the medication automatically. Direct line feed to impasse-jackets and/or their outriggers or dummy collars from the body surface is addressed below in the section of like title. Either or both impasse-jackets and dummy collars can be directly supplied or lumen contents drawn by a portable pump connected to an infusion set cannula with catheter leading to the jacket or an Ommaya reservoir type connector implanted at the body surface.

Single, dual, and multipump circuits are delineated below in the section entitled Single and Plural Circuit Pumping through Direct Lines to jackets. The jackets and/or other implants described herein, to include patch-magnets, and magnet-wraps, and bonding of the drug to the magnetic drug carrier then serve to steer the medication into the lumen wall, the anastomosis, or parenchyma. Broadly, impasse-jackets for later use are easily prepositioned as a part of any open procedure where an eventual need for drug targeting is probable—essentially, always. When the initial medication requires only an entry jacket but the prospective need for another drug that would generate a residue requiring reversal or neutralization is present, an exit jacket is prepositioned without being charged, or loaded with the reversal agent.

Magnetic drug-targeting implants applied to the ileum and colon, for example, make it possible to direct corticosteroids, immunomodulators, antiinfectives, gene therapy vehicles, vaccines, antineoplastic drugs, enzymes, cytokines, whether as 'smart pills,' for example, to only those segments affected by regional enteritis most often seen as ileocolitis or Crohn's disease, in high concentration with minimal delivery to the rest of the body. When tight control over distribution is not critical, passive apportionment among a number of jackets is sometimes possible at less risk and expense; however, when it is essential, more extended coverage is achieved by direct line delivery to any or all of a plurality of impasse-jackets. The strength of magnetization or degree of tractive force from collar to collar is increased in the Proximodistal, or antegrade, direction.

Particles with a greater mass of ferromagnetic or susceptible content will generally decrease from jacket to jacket. When the particles are equally susceptible, the distribution results from chance proximity to each pole traversed. Provided care is given to avoiding interactions between different ductus treated thus and recurving of the same ductus, this allows a range of tractive force over the distance covered by the array or arrays at different levels along the ductus. While the contingency of drug-carrier particle proximity to each collar along the gut requires that the apportionment of the drug among the collars deviate from the ideally uniform or aliquot, the statistical apportionment among collars of the array gradient is sufficient to treat each segment affected. Once placed, the jackets are prepositioned for followup dosage at any later time.

Ending the array with a jacket, an exit-jacket, that releases a reversal agent allows drugs so highly toxic that even a residue in the bloodstream can prove problematic, notably those chemotherapeutic, to be restricted to the target segment with an exit impasse-jacket or exit jacket to release a reversal agent to eliminate any residue when a recommended precaution. Similarly, placing a drug trapping and releasing impasse-jacket at the inlet to an organ and an exit jacket at the outlet allows the selective targeting of that organ. Whether impasse-jackets, addressed below in the sections entitled Concept of the Impasse-jacket, Miniball and Ferrofluid-borne Particle-impassable Jackets, or Impasse-jackets, and Cooperative Use of Impasse-jackets in Pairs and Gradient Arrays, or stent-jackets, addressed below in the section entitled Stent-jackets and Stent-jacket Supportng Elements, a collar side-slot accommodates a running attachment of connective tissue, for example.

When it is realized that many ailments can be treated through the differential delivery of drugs to ductus such as blood vessels as these enter and depart a target organ, a lesioned segment, or different segments of a lumen, the potential significance of such means becomes clear. When the medication is encapsulated in the form of microspheres or miniballs, it is also possible with the aid of an external electromagnet to extract these should some mishap occur or some unforeseen eventuality arise. The term 'barrel-assembly' used to denote a catheteric extension to the barrel of a specially adapted, or interventional, airgun and 'muzzle-head' or 'muzzle-probe,' its distal terminus, when the medication is in the form of a ferrofluid, recovery is by means of an endoscope with a magnetized tip or the recovery tractive electromagnets in the muzzle-head of a barrel-assembly, as will be described.

Although treatment is targeted at a certain organ or segment, associated symptoms, however remote, induced by the primary pathology, that is, secondary or sequelary, derived from those primary, rather than parallel or pleiotropic, are inhibited from spreading as well. With respect to the Crohn's example, the disease appears to involve an abnormal immune response of multifactorial genetic basis to the normal flora occupying the gut, so that associated symptoms, to include those concomitant or antecedent, however remote, would appear to be co-original.

Bowel disorders briefly addressed below, extraintestinal symptoms, more frequent with perianal Crohn's disease (see, for example, Mahmoud, N. N., Halwani, Y., Montbrun, S., Shah, P. M., Hedrick, T. L. and 8 others 2017. "Current Management of Perianal Crohn's Disease," *Current Problems in Surgery* 54(5):262-298; Klag, T., Goetz, M., Stange, E. F., and Wehkamp, J. 2015. "Medical Therapy of Perianal Crohn's Disease," *Viszeralmedizin* (Visceral Medicine) 31(4):265-272; Freidman, S. and Blumberg, R. S. 2005. "Inflammatory Bowel Disease," "in *Harrison's Principles of Internal Medicine*, 16th Edition, New York, N.Y.: McGraw-Hill, page 1783; Galandiuk, S., Kimberling, J., Al-Mishlab, T. G., and Stromberg, A. J. 2005. "Perianal Crohn Disease: Predictors of Need for Permanent Diversion," *Annals of Surgery* 241(5):796-802), include those ocular, arthritic, hepatic, hematologic, and cobalamin (vitamin $B_{12}$) deficiency (Babior, B. M. and Bunn, H. F. 2005. "Megaloblastic Anemias," in Harrison's op cit., Page 604), posing a risk for atrophic gastritis, and if not corrected, gastric adenocarcinoma, magaloblastic anemia, achlorhydria predisposing to salmonellosis, and neurologic dysfunction, among others (see, for example, Del Valle, J. 2005. "Peptic Ulcer Disease and Related Disorders," in Harrison's op cit., Page 1761; *The Merck Manual of Diagnosis and Therapy,* 18th Edition, 2006, Section 2, Gastrointestinal Disorders, Subsection 18, "Inflammatory Bowel Disease," page 149 and Section 14, Infectious Diseases, Subsection 167, "Biology of Infectious Diseases," page 1387).

Extraintestinal symptoms appearing before frank ileocolitis should prompt consideration of placing collars to pre-emptively inhibit spread of the disease to the mesentery, for example. Such implants also allow the controlled and targeted release and suppression of released drugs or other substances from outside the body. Different layers or concentric shells of drugs in miniball or microsphere implants as well as those applied as coatings to other type implants such as absorbable stent-jackets and magnet-wraps, to be described herein can be released by:

1. Spontaneous dissolution at body temperature, accelerated by the blood washing over the implant when suspended in the bloodstream.

2. Exposing the layer to another agent whether released from a second such implant whether by the same or different means, such as infused, injected, or ingested, that induces the dissolution of the layer.

3. With the use of an alternating magnetic or electromagnetic field, induction heating each successive magnetically susceptible nanoparticle-bound drug or radioisotope carrier-incorporating layer to its respective temperature of dissolution 4. When the implant is sufficiently stable in position, using a constant magnetic field to break up each layer. 5. Providing each layer or shell with a proportionally distinct mass of magnetically susceptible matter to allow that layer to be disintegrated through a combination of heating, traction, and/or exposure to another chemical in any combination.

Stent- and impasse-jackets provide such a constant magnetic field and allow endoluminally implanted drugs to be aligned to lesions. If placed near to the body surface, noninjurious heating can be accomplished by means of an aquathermia pad, hot air gun, or hand held blow dryer. In addition to thermoelectric heat induction by placement in a radiofrequency alternating magnetic field, the dissolution of more deeply placed biodegradable (absorbable) implants with or without the release of therapeutic substances, such as those encapsulated or entrapped within a polyanhydride, can be effected with conventional electromagnetic eddy current induction heating (see, for example, Hartshorn, L. 1949. *Radio-frequency Heating*, London, England: Allen and Unwin).

Since ductus-intramural implants incorporate sufficient ferrous content to allow their magnetic relocation or extraction at any moment if necessary, the ferrous content is usually sufficient for heat induction as well. The potential applications for the heating of implants are numerous and will be specified. Where arrestability and recoverability of a miniball that enters the circulation are satisfied by the incorporation of sufficient superparamagnetic magnetite or maghemite nanoparticles or finely grained powder, induction more effective with larger grains. Powder and grains both present sufficient surface area for quick absorption at a subtoxic level. The formulation of ductus-intramural implants and miniballs in particular, is addressed below in the section entitled Noninvasive Dissolution on Demand of Absorbable Stent-jackets, Base-tubes, Radiation Shields, and Miniballs.

With release controllable from outside the body, the layers can represent doses of the same drug, or a drug, chemical, or enzyme, for example, released to supplement or counter-act one released earlier. Sequential release from the same implant, such as a ductus-intramurally implanted stay or miniball or a lumen suspended miniball can then be coordinated between and among any such implants. Different implants can be controlled in a coordinated and timed manner to release chemicals that combine to form a therapeutic compound or mixture or which act synergistically. Such capability is expected to prompt the development of magnetically susceptible nanoparticle bound drugs specially formulated for such delivery. Situating magnetized miniballs, stays, arrays thereof, or jackets along a section of a ductus allows targeting a drug or drugs to that segment for controlled uptake from outside the body with or without such timed and coordinated release.

Once the blood-borne overload passing through the liver reaches a threshold, the significance of iron as a carcinogen is established; however, here thr blood concentration of iron cannot rise to the level of toxicity, even when the tiny miniballs or stays are not encapsulated within a polymeric outer jacket or shell; using the methods described herein should not release an absolute amount of iron into the bloodstream as would even rise to the level of medical significance. Much pertinent research is open to question in any event (see, for example, Deugnier, Y. and Loréal, O. 2000. "Iron as a Carcinogen," Chapter 22, pages 239-249 in Barton, J. C. and Edwards, C. Q. (eds.), *Hemochromatosis: Genetics, Pathophysiology, Diagnosis and Treatment*, Cambridge, England: Cambridge University Press. When containing radioisotopes, an absorbable radiation shield-jacket with dissolution time keyed to the half-life of the radioisotope is used, as addressed below in the section entitled Radiation Shield-jackets and Radiation Shielded Stent-jackets Absorbable and Nonabsorbable.

Due to dilution, any conventional drug that is highly concentrated for the lesioned segment that may continue in the circulation will be innocuous. Reciprocally, dependency upon circulation of the drug eliminated, first pass or presystemic metabolic reduction is avoided so that its concentration or dose can be keyed to that optimal for direct delivery to the lesion without a need to reduce the level to avoid adverse side effects risked when it is circulated. When available, unconventional drugs that despite dilution would be toxic are neutralized by the release from a segment exit or outlet jacket of a reversal or neutralizing agent, as addressed below in the section entitled Cooperative Use of Impasse-jackets in Pairs and Higher Combinations, among others allows a concentration of the drug in the lesion.

For toxic antineoplastic drugs, release is initiated at the start of the segment or inlet of the organ to be treated. Provided a counteractant is available, any residue can be neutralized by a counteractant released from an exit jacket at the end of the segment or outlet of the organ. Targeted chemotherapy through the application of magnetic force, with or without surgery or radiation to treat localized (nondisseminated, nonmetastazized, nonmetastatic) as opposed to a systemic disease thus averts the need to moderate the dose, instead allowing the drug to be administered at the optimal concentration for the lesion in virtually any patient regardless of performance status. Whether given as neoadjuvant, or before surgery to enhance resectability and/or preserve local organ function (*Merck Manual of Diagnosis and Therapy*, 18th edition, page 1167), or additionally administered as a precaution, only the backup or adjuvant chemotherapeutic level of the drug circulated requires the application of toxicity-averting dose-interval strategy that currently dominates the use of such drugs.

Equally important, the elimination or substantial elimination of a drug from the bloodstream also avoids the liver and eliminates drug-drug interactions, not only allowing concomitant treatment of a systemic comorbidity with a drug that must be circulated, but keeping the bloodstream free of a drug that would later become a deterrent to the use of another drug to treat an unforeseeable intercurrent systemic disease. Drug-drug interactions are then limited to the targeted lesion. The use of drug miniballs, stays, and impasse-jackets to treat a local area by direct breakdown, elution, or attracting a magnetized carrier-bound drug from the passing blood, and impasse-jackets in pairs, for example, to mark off a segment of a ductus or an entire organ is not intended to affect liver metabolism or the systemic serum level of a constituent or constituents known harmful for the diseased area defined thus, but rather to block the transport of these harmful substances across cell membranes at the locus, segment, or organ.

The apparatuses described herein are determined in size by the diameter of the lumen to be treated and ultimately limited in this regard by the degree of miniaturization that can be achieved. While implantation within the walls of lumina is specifically addressed, limitation to such use and not to other organs is not to be imputed. Embodiments for use in the trachea, bronchi, or gastrointestinal tract, which are relatively large, can incorporate components which for use in smaller blood vessels and ureters, for example, will demand greater miniaturization over time. Such components include plural implant discharge channels, or barrel-tubes, to allow the delivery of multiple implants per discharge, and a central passageway to accommodate a commercial cabled device, such as an endoscope, laser, or rotational tool. Where possible, control electronics that can compensate for components too large to fit inside the endoluminal portion of the apparatus are relegated to an extracorporeal power and control housing.

An example is the use of an embedded mixed-signal microcontroller to regulate the temperature of heating elements using the equivalent direct electrical current, thus eliminating the need to position temperature feedback sensors inside the catheteric member. Suitable microcontrollers are produced by Microchip Technology, Atmel, Freescale Semiconductor, and Texas Instruments corporations, for example. Remote control by a centralized computer and charging of the implanted battery by distributed charging stations is briefly addressed above in this section and below in the section entitled Exemplary Channel of Control in a Fully Implanted Ambulatory Adaptive Hierarchical Control System for Automatic Response to a Comorbid Condition.

The applicability of the system described herein to ductus with weak, disease-weakened or malacotic walls, such as of veins and atheromatous arteries, wherewith remodeling has atrophied the media (see, for example, Glagov, S., Weisenberg, E., Zarins, C. K., Stankunacius, R., and Kolettis, G. J. 1987. "Compensatory Enlargement of Human Atherosclerotic Coronary Arteries," *New England Journal of Medicine* 316(22):1371-1375), and the tunica adventitia (tunica externa) appears too weak to compensate (Haurani, M. J. and Pagano, P. J. 2007. "Adventitial Fibroblast Reactive Oxygen Species as Autacrine and Paracrine Mediators of Remodeling: Bellwether for Vascular Disease?," *Cardiovascular Research* 75(4):679-689), for example, is extended by the capability to include a suitable thickness of tissue surrounding the ductus.

Calcification introduces a factor of unpredictability that requires testing of the vessel or other ductus wall strength as addressed below in section XVII entiled Testing and Tests (see also Kolossváry, M., Szilveszter, B., Merkely, B., and Maurovich-Horvat, P. 2017. "Plaque Imaging with CT—A Comprehensive Review on Coronary CT Angiography Based Risk Assessment," *Cardiovascular Diagnosis and Therapy* 7(5):489-506; Obaid, D. R., Calvert, P. A., Gopalan, D., Parker, R. A., Hoole, S. P., and 4 others 2013. "Atherosclerotic Plaque Composition and Classification Identified by Coronary Computed Tomography: Assessment of Computed Tomography-generated Plaque Maps Compared with Virtual Histology Intravascular Ultrasound and Histology," *Circulation. Cardiovascular Imaging* 6(5):655-664; Matsuo, Y., Takumi, T., Mathew, V., Chung, W. Y., Barsness, G. W., and 8 others 2012. "Plaque Characteristics and Arterial Remodeling in Coronary and Peripheral Arterial Systems," *Atherosclerosis* 223(2):365-371). If necessary, some thickness of the tissue surrounding the ductus can be hardened, or sclerosed, and made strongly adherent to the adventitia by microinjection with a tissue adhesive-hardener or binder-fixative effectively increasing the thickness and strengthening the wall. The least effective magnetic force used, this will often allow the lumen wall to accommodate and retain magnetically retracted ductus-intramural implants without delamination, or the separation or avulsion of the tunics or tissue layers of the ductus, here veins.

Tissue which surrounds and participates in the physiology of the ductus as to support normal function as addressed below in the section entitled Accommodation of the Adventitial Vasculature, Innervation, and Perivascular Fat, is usually not to be treated thus; however, perivascular fat that is responsible for endothelial dysfunction is best included in the hardened tissue thus adding thickness and reducing the adverse effect at the same time (see, for example, Kennedy, S. and Salt, I. P. 2017. "Molecular Mechanisms Regulating Perivascular Adipose Tissue—Potential Pharmacological Targets?," *British Journal of Pharmacology* 174(20):3385-3387; Zaborska, K. E., Wareing, M., and Austin, C. 2017. "Comparisons Between Perivascular Adipose Tissue and the Endothelium in Their Modulation of Vascular Tone," *British Journal of Pharmacology* 174(20):3388-3397; Akoumianakis, I., Tarun, A., and Antoniades, C. 2017. "Perivascular Adipose Tissue as a Regulator of Vascular Disease Pathogenesis: Identifying Novel Therapeutic Targets," *British Journal of Pharmacology* 174(20):3411-3424; Ayala-Lopez, N. and Watts, S. W. 2017. "New Actions of An Old Friend: Perivascular Adipose Tissue's Adrenergic Mechanisms," *British Journal of Pharmacology* 174(20):3454-3465; Nosalski, R. and Guzik, T. J. 2017. "Perivascular Adipose Tissue Inflammation in Vascular Disease," *British Journal of Pharmacology* 174(20):3496-3513; Srikakulapu, P., Upadhye, A., Rosenfeld, S. M., Marshall, M. A., McSkimming, C., and 6 others 2017. "Perivascular Adipose Tissue Harbors Atheroprotective IgM-Producing B Cells," *Frontiers in Physiology* 8:719; Horimatsu, T., Kim, H. W., and Weintraub, N. L. 2017. "The Role of Perivascular Adipose Tissue in Non-atherosclerotic Vascular Disease," *Frontiers in Physiology* 8:969; Ramirez, J. G., O'Malley, E. J., and Ho, W. S. V. 2017. "Pro-contractile Effects of Perivascular Fat in Health and Disease," *British Journal of Pharmacology* 174(20):3482-3495; Li, C., Wang, Z., Wang, C., Ma, Q., and Zhao, Y. 2015. "Perivascular Adipose Tissue-derived Adiponectin inhibits Collar-induced Carotid Atherosclerosis by Promoting Macrophage Autophagy," *Public Library of Science One* 10(5):e0124031; Villacorta, L. and Chang, L. 2015. "The Role of Perivascular Adipose Tissue in Vasoconstriction, Arterial Stiffness, and Aneurysm," *Hormone Molecular Biology and Clinical Investigation* 21(2):137-147; Manka, D., Chatterjee, T. K., Stoll, L. L., Basford, J. E., Konaniah, E. S., and 6 others 2014. "Transplanted Perivascular Adipose Tissue Accelerates Injury-induced Neointimal Hyperplasia: Role of Monocyte Chemoattractant Protein-1," *Arteriosclerosis, Thrombosis, and Vascular Biology* 34(8): 1723-1730; Payne, G. A. 2010. *Contribution of Perivascular Adipose Tissue to Coronary Vascular Dysfunction*, Dissertation, Indiana University; Payne, G. A., Bohlen, H. G., Dincer, U. D., Borbouse, L., and Tune, J. D. 2009. "Periadventitial Adipose Tissue Impairs Coronary Endothelial Function via PKC-beta-dependent Phosphorylation of Nitric Oxide Synthase," *American Journal of Physiology. Heart and Circulatory Physiology* 297(1):H460-H465; Payne, G. A., Borbouse, L., Bratz, I. N., Roell, W. C., Bohlen, H. G., Dick, G. M., and Tune, J. D. 2008. "Endogenous Adipose-derived Factors Diminish Coronary Endothelial Function via Inhibition of Nitric Oxide Synthase," *Microcirculation* 15(5):417-426; Dick, G. M., Katz, P. S., Farias, M. 3rd, Morris, M., James, J., Knudson, J. D., and Tune, J. D. 2006. "Resistin Impairs Endothelium-dependent Dilation to Bradykinin, but Not Acetylcholine, in the Coronary Circulation," *American Journal of Physiology. Heart and Circulatory Physiology* 291(6):H2997-H3002).

A small or miniature spine and ribs type stent-jacket, described below in the section entitled Spine and Ribs-type Stent-jacket, is used to avoid any blood vessels or nerves. The fast initial setting and curing times of long chain cyanoacrylate cements allows the incorporation into stay insertion tools of an applicator to coat each stay with cement on ejection. Testing methods to assist in determining whether preparatory remedial measures are necessary to stent an artery weakened by disease, for example, are delineated below in the section entitled Testing and Tests.

In instances where arterial shrinkage and enlargement produce irregularity in the luminal diameter or radial symmetry of the luminal wall (see, for example, de Groot, P. and Veldhuizen, R. W. 2006. "Human Coronary Artery Remodeling, Beginning and End of the Atherosclerotic Process," *Public Library of Science One* 1:e91; Smits, P. C., Bos, L. Quarles van Ufford, M. A., Eefting, F. D., Pasterkamp, G., and Borsta, C. 1998. "Shrinkage of Human Coronary Arteries is an Important Determinant of de Novo Atherosclerotic Luminal Stenosis: An in Vivo Intraductal Ultrasound Study," *Heart* 79(2):143-147; Prati, F., Mallus, M. T., Parma, A., Lioy, E., Pagano, A., and Boccanelli, A.1998. "Incidence of Compensatory Enlargement and Paradoxical Shrinkage of Coronary Arteries in Presence of Atherosclerotic Lesions: An Intracoronary Ultrasound Study Based on Multiple Cross-section Analysis Per Artery," *Giornale Italiano di Cardiologia* 28(10):1063-1071; Birnbaum, Y., Fishbein, M. C., Luo, H., Nishioka, T., and Siegel, R. J. 1997. "Regional Remodeling of Atherosclerotic Arteries: A Major Determinant of Clinical Manifestations of Disease," *Journal of the American College of Cardiology* 30(5):1149-1164), an extraluminal stent with foam lining and spring hinge enabled expandability can maintain patency with less trauma and disruption to normal physiology than can an endoluminal stent.

To accommodate a tapered segment along a ductus and its lumen, an endoluminal or intravascular stent may flex to some extent, but the margins and body must exert sufficient outward force to prevent migration. If to complement the lumen, the ends were made unequal in diameter, the sides would incline between the two diameters; by contrast, extraluminal stent-jackets can adjust for variation in the diameter of the substrate ductus the jacket encircles by altering the strength of, mgnetization along the length of the jacket, which is uniform in diameter from end to end.

That is, while ordinarily made to standard dimensions and field strengths rather than customized, extraluminal stent-jackets conform to all but the most pronounced changes in diameter of the substrate ductus due to the compliance of the foam lining, and past that degree of change in diameter, itself unlikely, the jacket can be differentially magnetized from one segment to another along the jacket length without affecting stent diameter. An extraluminal stent does not have margins unlike or less flexible than intervening segments and can be adjusted in strength of magnetization in any segment. The ductus-intramural implants for insertion in the arterial tree contain sufficient ferrous content to assure retrieval by prepositioned means. Such implants can incorporate medication, non-drug therapeutic substances, a radiation emitting seed, or protein solder, for example, in any combination.

When not specifically encapsulated to prevent dissolution, iron-containing absorbable implants described herein will leave an iron residue too small to produce iron overload. When the sum quantity of iron would exceed the 5 or so grams that induce exogenous or secondary acquired iron overload with tissue damage (hemochromatosis), the ferromagnetic material is chemically isolated by encapsulation metallic or polymeric. The source of iron overload known, limited, and temporary rather than diagnostic for chronic defective hematopoesis, anemia, (*The Merck Manual of Diagnosis and Therapy,* 18th edition, pages 1131-1133) or infection, so long as deposition remains at a concentration too small to do tissue damage (hemosiderosis), treatment is not necessary.

Laser welding surgical tissue solder polymers (see, for example, ACS [American Chemical Society] News Service Weekly PressPac 2013. "Improved Material for 'Laser Welding' of Tissue in Intestinal Surgery," *ACS News Service Weekly PressPac* Wed May 8, at https://www.acs.org/content/acs/en/pressroom/presspacs/2013/acs-presspac-may-8-2013/improved-mater-ial-for-laser-welding-of-tissue-in-intestinal-surgery.html) can release therapeutic drugs not altered by the heat used to flow the solder (see, for example, Prosperi, D., Colombo, M., Zanoni, I., and Granucci, F. 2017. "Drug Nanocarriers to Treat Autoimmunity and Chronic Inflammatory Diseases," *Seminars in Immunology* 34:61-67; Mundargi, R. C., Babu, V. R., Rangaswamy, V., Patel, P., d Aminabhavi, T. M. 2008 "Nano/Micro Technologies for Delivering Macromolecular Therapeutics Using Poly(D,L-lactide-co-glycolide) and Its Derivatives," *Journal of Controlled Release* 125(3):193-209; Perugini, P., Genta, I., Conti, B., Modena, T., and Pavanetto, F. 2001. "Long-term Release of Clodronate from Biodegradable Microspheres," *Pharm Sci Tech* 2(3):E10). Small miniballs and stays can include or consist of long-term drug release microspheres (see, for example, Varde, N. K. and Pack, D. W. 2004. "Microspheres for Controlled Release Drug Delivery, *Expert Opinion on Biological Therapy* 4(1):35-51) or nano or microparticles (see, for example, Ravi Kumar, M. N. 2000. "Nano and Microparticles as Controlled Drug Delivery Devices," *Journal of Pharmacy and Pharmaceutical Sciences* 3(2): 234-58).

As used here, the term medication includes those—all of which pose the risk of adverse side effects that if directly targeted through use of the means described herein—would be significantly lessened, antiangiogenic (antivasofactive), proangiogenic, proneurogenic, chemotherapeutic, oncolytic viral, antibiotic, precursory (prodrug, proenzyme, prohormone), nanomedical, gene therapeutic to include ataxia-telangiectasia mutated protein activating (see, for example, Comunanza, V. and Bussolino, F. 2017. "Therapy for Cancer: Strategy of Combining Anti-angiogenic and Target Therapies," *Frontiers in Cell and Developmental Biology* 5:101; Kachaamy, T., Gupta, D., Edwin, P., and Vashi, P. 2017. "Safety of Endoscopy in Cancer Patients on Antiangiogenic Agents: A retrospective Multicenter Outcomes Study," *Public Library of Science One* 12(5):e0176899; Tanabe, K., Maeshima, Y., Sato, Y., and Wada, J. 2017. "Antiangiogenic Therapy for Diabetic Nephropathy," *BioMed Research International* 2017:5724069; Rajabi, M. and Mousa, S. A. 2017. "The Role of Angiogenesis in Cancer Treatment," *Biomedicines* 5(2). pii: E34; Cao, Y. 2016. "Future Options of Anti-angiogenic Cancer Therapy," *Chinese Journal of Cancer* 35:21; Zhang, Q., Cao, J., Xue, K., Liu, X., Ji, D., Guo, Y., and Hong, X. 2016. "Recombinant Human Endostatin in Combination with CHOP [cyclophosphamide, doxorubicin, vincristine and prednisone] Regimen for Peripheral T cell Lymphoma," *OncoTargets and Therapy* 10:145-151; Vecchio, D. and Frosina, G. 2016. "Targeting the Ataxia Telangiectasia Mutated Protein in Cancer Therapy," *Current Drug Targets* 17(2):139-153; Kumar, A., Purohit, S., and Sharma, N. K. 2016. "Aberrant DNA Double-strand Break Repair Threads in Breast Carcinoma: Orchestrating Genomic Insult Survival," *Journal of Cancer Prevention* 21(4):227-234; Ye, B., Hou, N., Xiao, L., Xu, Y., Xu, H., and Li, F. 2016. "Dynamic Monitoring of Oxidative DNA Double-strand Break and Repair in Cardiomyocytes," *Cardiovascular Pathology* 25(2):93-100; Farooqi, A. A., Attar, R., Arslan, B. A., Romero, M. A., ul Haq, M. F., and Qadir, M. I. 2014. "Recently Emerging Signaling Landscape of Ataxia-telangiectasia Mutated (ATM) Kinase," *Asian Pacific Journal of Cancer Prevention* 15(16):6485-6488; Andrs, M., Korabecny, J., Nepovimova, E., Jun, D., Hodny, Z., and 3 others 2014. "The Development of Ataxia Telangiectasia Mutated Kinase Inhibitors," *Mini Reviews in Medicinal Chemistry* 14(10):805-811; Vasudev, N. S. and Reynolds, A. R. 2014. "Anti-angiogenic Therapy for Cancer: Current Progress, Unresolved Questions, and Future Directions," *Angiogenesis* 17(3):471-494; Elice, F. and Rodeghiero, F. 2012. "Side Effects of Anti-angiogenic Drugs," *Thrombosis Research* 129 Supplement 1:S50-S53; Elice, F. and Rodeghiero, F. 2010. Bleeding Complications of Antiangiogenic Therapy: Pathogenetic Mechanisms and Clinical Impact," *Thrombosis Research* 125 Suppl 2:S55-S57; Abdollahi, A. and Folkman, J. 2010. "Evading Tumor Evasion: Current Concepts and Perspectives of Anti-angiogenic Cancer Therapy," *Drug Resistance Updates* 13(1-2):16-28; Alexander, A., Cai, S. L., Kim, J., Nanez, A., Sahin, M., and 9 others 2010. "ATM [ataxia-telangiectasia mutated] Signals to TSC2 [tuberin, tuberous sclerosis complex 2 protein encoded by the TSC2 gene] in the Cytoplasm to Regulate mTORC1 [mammalian, or mechanistic, target of rapamycin complex 1 protein] in Response to ROS [reactive oxygen species]," *Proceedings of the National Academy of Sciences of the United States of America*; Sordet, O., Redon, C. E., Guirouilh-Barbat, J., Smith, S., Solier, S., and 8 others 2009. "Ataxia Telangiectasia Mutated Activation by Transcription- and Topoisomerase I-induced DNA Double-strand Breaks," *European Molecular Biology Organization Reports* 10(8):887-893; Morio, T. and Kim, H. 2008. "Ku, Artemis, and Ataxia-telangiectasia-mutated: Signalling Networks in DNA Damage," *International Journal of Biochemistry and Cell Biology* 40(4):598-603; Juang, S. H., Lung, C. C., Hsu, P. C., Hsu, K. S., Li, Y. C., and 16 others 2007. "D-501036, a Novel Selenophene-based Triheterocycle Derivative, Exhibits Potent in Vitro and in Vivo Antitumoral Activity which Involves DNA Damage and Ataxia Telangiectasia-mutated Nuclear Protein Kinase Activation," *Molecular Cancer Therapeutics* 6(1):193-202; Ismail, I. H., Nyström, S., Nygren, J., and Hammarsten, O. 2005. "Activation of Ataxia Telangiectasia Mutated by DNA Strand Break-inducing Agents Correlates Closely with the number of DNA Double Strand Breaks," *Journal of Biological Chemistry* 280(6): 4649-4655).

Also included is in vivo magnetic assisted transfection of small interfering (short interfering, silencing, knockdown) ribonucleic acid (see, for example, Covarrubias, S., Robinson, E. K., Shapleigh, B., Vollmers, A., Katzman, S., and 4 others 2017. "CRISPR/Cas [clustered regularly-interspaced short palindromic repeats/CRISPR-associated]-based Screening of Long Non-coding RNAs (lncRNAs) in Macrophages with an NF-κB [nuclear factor kappa-light-chain-enhancer of activated B cells] Reporter," *Journal of Biological Chemistry* 292(51):20911-20920; Unniyampurath, U., Pilankatta, R., and Krishnan, M. N. 2016. "RNA Interference in the Age of CRISPR: Will CRISPR Interfere with RNAi?," *International Journal of Molecular Sciences* 17(3): 291; Mykhaylyk, O., Sanchez-Antequera, Y., Vlaskou, D., Cerda, M. B., Bokharaei, M., and 3 others 2015. "Magnetic Nanoparticle and Magnetic Field Assisted siRNA [small interfering or interference] Delivery in Vitro," *Methods in Molecular Biology* (Clifton, N.J.) 1218:53-106; Boettcher, M. and McManus, M. T. 2015. "Choosing the Right Tool for the Job: RNAi [RNA interference], TALEN [transcription activator-like effector nucleases], or CRISPR [clustered regularly-interspaced short palindromic repeats]," *Molecular Cell* 58(4):575-585; Laurentt, N., Sapet, C., Le Gourrierec, L., Bertosio, E., and Zelphati, O. 2011. "Nucleic Acid Delivery Using Magnetic Nanoparticles: The Magnetofection Technology," *Therapeutic Delivery* 2(4):471-482; Plank, C., Zelphati, O., and Mykhaylyk, O. 2011. "Magnetically Enhanced Nucleic Acid Delivery. Ten Years of Magnetofection-progress and Prospects," *Advanced Drug Delivery Reviews* 63(14-15):1300-1331; Mykhaylyk, O., Zelphati, O., Hammerschmid, E., Anton, M., Rosenecker, J., and Plank, C. 2009. "Recent Advances in Magnetofection and Its Potential to Deliver siRNAs siRNA [small interfering or interference] in Vitro," *Methods in Molecular Biology* (Clifton, N.J.) 487:111-146; Mykhaylyk, O., Zelphati, O., Rosenecker, J., and Plank, C. 2008. "siRNA Delivery by Magnetofection," *Current Opinion in Molecular Therapeutics* 10(5):493-505; Kawakami, S. and Hashida, M. 2007. "Targeted Delivery Systems of Small Interfering RNA by Systemic Administration," *Drug Metabolism and Pharmacokinetics* 22(3):142-151), mutant human tumor necrosis factor (Liu, X., Zhang, X. F., Zheng, Z. W., Lu, H., Wu, X., Huang, C., Wang, C., and Guang, G. 2004. "The Effect of Chemotherapy Combined with Recombination Mutant Human Tumor Necrosis Factor on Advanced Cancer," *Journal of Translational Medicine* 2(1):33), glutamate antagonistic, and/or irradiating.

Whether containing an irradiating seed, the surface of stay and miniball implants, metallic, absorbable, or having an outer absorbable layer or layers can be prepared to emit radiation (see, for example, Cardoso, R. M., de Souza, C. D., Rostelato, M. E., and Araki, K. 2017. "Highly Efficient Method for Production of Radioactive Silver Seed Cores for Brachytherapy," *Applied Radiation and Isotopes* 120:76-81; Li, Z. Y., Langhans, L., Klausen, T. L., Tvedskov, T. F., Talman, M. L., Oturai, P. S., Vejborg, I., Kroman, N., and Hesse, B. 2016. "Preparation and Administration of I-125 Labeled Seeds for Localization of Nonpalpable Breast Lesions," *Current Radiopharmaceuticals* 9(2):143-149; Gao, H. B., Deng, X. S., Zhou, L., Zhang, W. H., Han, L. G., Jin, X. H., and Cui, H. P. 2015. "Preparation of (103)Pd Brachytherapy Seeds by Electroless Plating of (103)Pd onto Carbon Bars," *Applied Radiation and Isotopes* 103:128-130; Lee, J. H., Choi, K. H., and Yu, K. H. 2014. "Surface Treatments of Silver Rods with Enhanced Iodide Adsorption for I-125 Brachytherapy Seeds," *Applied Radiation and Isotopes* 85:96-100; Otani, Y., Yamada, T., Kato, S., Shikama, N., Funakoshi, K., and 5 others 2013. "Source Strength Assay of Iodine-125 Seeds Sealed within Sterile Packaging," *Journal of Applied Clinical Medical Physics* 2013 14(2):4082; Fischell, T. A. and Hehrlein, C. 1998. "The Radioisotope Stent for the Prevention of Restenosis," *Herz* 23(6):373-379; Sekina, T., Watanabe, S., Osa, A., Ishioka, N., Koizumi, M. and 8 others 2001. "Xenon 133 Radioactive Stent for Preventing Restenosis of Blood Vessels and a Process for Producing the Same," U.S. Pat. No. 6,192,095). Apparatus according to the invention allow the targeted delivery of medication into luminal lesions endoluminally.

One type, barrel-assemblies, are catheteric extensions to the barrel of a modified or special purpose interventional airgun. This introduces the medication in the form of tiny spherules or miniballs. Another type, radial projection assemblies or catheters deliver medication endoluminally using side-looking, or luminal wall-directed, injection microsyringes or hypotubers. Yet another apparatus is a stay insertion hand tool that allows injection extraluminally. The endoluminal types include barrel assemblies such as shown in FIGS. 31 thru 35, and 38 thru 49 and 71*b*, and radial projection catheters such as shown in FIG. 71*a*.

As shown in FIG. 71, which shows how these need not be mutually exclusive, the radial projection catheter in FIG. 71*a*, for example, devised to slide over, thereby to ensheath the barrel-assembly of complementary conformation shown in FIG. 71*b* to constitute a composite, duplex, or bipartite combination radial projection catheter/barrel-assembly shown in FIG. 71*c* such the two can be used separately or as unitized. In numerous alternative configurations where these are independent, either can include features of the other. Such multifeatured transluminal catheters are always ablation and angioplasty capable. The implants can consist purely of medication or of ferrous cores or radiation-emitting seeds enveloped within layers of medication, for example.

By including ferromagnetic material, implants that are mispositioned, dropped, or due for removal because the period for treatment has ended are made retrievable or prevented from continued movement with the aid of a magnet. Where barrel assemblies are transluminal devices that introduce spherical implants into the wall surrounding the lumen radially outward and forward at an acute angle by aeroballistic ejection from within the lumen, stay insertion devices insert tiny band shaped implants into the luminal wall from outside the ductus. As addressed in section XV5 below entitled Circumstances Dissuading or Recommending the Use of Stays, this ability of the integrated system set forth herein to accomplish implantation either from within or without the ductus makes possible the secure and well placed positioning of the implants in any anatomical context.

Since the stent-jacket must be placed from outside the ductus in any event, the use of stays eliminates the need for double, or transluminal approach, as well. In some anatomical and pathological situations, one and the same ductus might best be treated in part by either type device. As explicated herein, provided it is warranted by the severity of the condition, the advantages of a periductal stent-jacket over a conventional endoluminal stent justify the dissection required to place the jacket. By the same token, the endoluminal/extraluminal double approach provided by the system described means that often, extensive perivascular dissection to place magnetically susceptible implants can be avoided. This double approach capability also means that implantation can span the length of the defect and avoid problems of conventional stenting, such as migration.

Endoluminal stent migration is no less a risk in the aortic arch (see, for example, Rad, E. M., Mortezaeian, H., Pouraliakbar, H. R., and Hijazi, Z. M. 2017, Op cit.; van den Hoven, A. T., Duijnhouwer, A. L., Eicken, A., Aboulhosn, J., de Bruin, C., and 9 others 2017. "Adverse Outcome of Coarctation Stenting in Patients with Turner Syndrome," *Catheterization and Cardiovascular Interventions* 89(2): 280-287; Yaylali, Y. T., Evrengul, H., and Uludag, B. 2013. "Successful Management of a Proximally Migrated Stent in a Middle-aged Woman with Unnoticed Native Aortic Coarctation," *International Journal of Cardiology* 168(1):e19-21;

Kannan, B. R. and Srinivasan, M. 2012. "Stent Migration During Transcatheter Management of Coarctation of Aorta," *Catheterization and Cardiovascular Interventions* 79(3): 408-413; Forbes, T. J., Garekar, S., Amin, Z., Zahn, E. M., Nykanen, D., and 19 others 2007, Op cit.).

Whether additionally coated with medication or radioactive, for example, miniballs, stays, magnet-jackets, stent-jackets, and impasse-jackets can all be used to concentrate a drug carrier nanoparticle or ferrofluid-bound drug or other therapeutic substance such as small interfering ribonucleic acid passing in the circulation and draw the drug abaxially (away from the long axis, lateral, peripheral, outward) through the lumen wall into the lesion. Permanent encirclement of the ductus by an expandable collar, or stent-jacket, having a lining to protect the fine vessels and nerves that surround the ductus and tiny magnets mounted about its outer surface allows the implants to serve as the intraductal component of an extraluminal stent. A structure requiring stenting may have collapsed, become constricted (stenosed, stenotic, stegnotic, strictured, coarctated, narrowed), or have been alleviated of constriction or occlusion (blockage) where the patency achieved must now be sustained.

Validation of stenting as efficacious in the treatment of coarctation of the aorta extends the application of stents to this congenital or 'native' form of narrowing (stenosis, stricture, constriction) (Bassiri, H. A., Abdi, S., Shafe, O., and Sarpooshi, J. 2017. "Early and Midterm Results Following Interventional Coarctoplasty: Evaluation of Variables that Can Affect the Results," *Korean Circulation Journal* 47(1):97-106; Georgescu, A., Onorato, E., Nicolae, S., and Balnescu, S. 2015. "Aortic Coarctation Treated by PTA and Stenting: A Case Presentation and Literature Review," *Maedica* (Bucharest, Romañia) 10(4):342-347; Forbes, T. J. and Gowda, S. T. 2014, Op cit.; Forbes T J, Kim D W, Du W, Turner D R, Holzer R. J., Amin Z, Hijazi Z, and 18 others 2011. "Comparison of Surgical, Stent, and Balloon Angioplasty Treatment of Native Coarctation of the Aorta: An Observational Study by the CCISC (Congenital Cardiovascular Interventional Study Consortium)," *Journal of the American College of Cardiology* 58(25):2664-2674; Holzer, R. J., Qureshi, S., Ghasemi, A., Vincent, J., Sievert, H., Gruenstein, D., Weber, H., and 6 others 2010. "Stenting of Aortic Coarctation: Acute, Intermediate, and Long-term Results of a Prospective Multi-institutional Registry—Congenital Cardiovascular Interventional Study Consortium (CCISC)," *Catheterization and Cardiovascular Interventions* 76(4):553-563).

If not conclusively successful, such application pertains not only to neonates but to critically ill premature infants as a bridging measure pending surgical reconstruction or recorrection thereof where an earlier coarctectomy or repair of the interrupted aortic arch had failed. Imperiling the left ventricle, which in an effort of compensation to pass sufficient blood into the systemic circulation, progressively weakens and hypertrophies, prominently presenting as syncope, dyspnea, epistaxis, vertigo, hypertension of the arms and hypotension of the legs, as well as other indications of weakness (van den Hoven, A. T., Duijnhouwer, A. L., Eicken, A., Aboulhosn, J., de Bruin, C., and 9 others 2017. "Adverse Outcome of Coarctation Stenting in Patients with Turner Syndrome," *Catheterization and Cardiovascular Interventions* 89(2):280-287; Gorenflo, M., Boshoff, D. E., Forbes, T. J. and Gowda, S. T. 2014. "Intravascular Stent therapy for Coarctation of the Aorta," *Methodist Debakey Cardiovascular Journal* 10(2):82-87; Heying, R., Eyskens, B., Rega, F., Meyns, B., and Gewillig, M. 2010. "Bailout Stenting for Critical Coarctation in Premature/Critical/Complex/Early Recoarcted Neonates," *Catheterization and Cardiovascular Interventions* 75(4):553-561; Bentham, J., Shettihalli, N., Orchard, E., Westaby, S., and Wilson, N. 2010. "Endovascular Stent Placement is an Acceptable Alternative to Reoperation in Selected Infants with Residual or Recurrent Aortic Arch Obstruction," *Catheterization and Cardiovascular Interventions* 76(6): 852-859)

Pediatric application has also been successfully extended to coronary and venous stenoses (see, for example, Aldoss, O., Arain, N., Menk, J., Kochilas, L., and Gruenstein, D. 2014. "Endovascular Stent Provides More Effective Early Relief of SVC [superior vena caval Obstruction Compared to Balloon Angioplasty," *Catheterization and Cardiovascular Interventions* 83(7):E272-E276; Bratincsák, A., Salkini, A., El-Said, H. G., and Moore, J. W. 2012. "Percutaneous Stent Implantation into Coronary Arteries in Infants," *Catheterization and Cardiovascular Interventions* 79(2):303-311; Stanfill, R., Nykanen, D. G., Osorio, S., Whalen, R., Burke, R. P., and Zahn, E. M. 2008. "Stent Implantation is Effective Treatment of Vascular Stenosis in Young Infants with Congenital Heart Disease: Acute Implantation and Long-term Follow-up Results," *Catheterization and Cardiovascular Interventions* 71(6):831-841; Moodie, D. 2008. "Stent Implantation as Effective Treatment of Vascular Stenosis in Young Infants with Congenital Heart Disease: Acute Implantation and Follow-up," *Catheterization and Cardiovascular Interventions* 71(6):842;). With an extraluminal stent of the kind to be described, ferromagnetic implants positioned beneath or subjacent to the outer fibrous coat or tunic if not within deeper, that is, more adluminal or medial, tissue of a tubular anatomical structure can be placed under the sustained retractive force of minute surrounding magnets to maintain the patency and thus sustain the movement of contents through the structure.

The subject of stent migration addressed below, extraluminal stents are easily provided with suture loops or suture eyelets and end-ties for use as necessary to reinforce the positional stability afforded by the spring hinges joining the half-cylinders and the resistance to sliding afforded by the foam jacket lining. Except in large gastrointestinal stents, such collateral tethering is not possible when the stent is endoluminal, conventional stents sometimes migrating to pose significant danger (see, for example, Orellana-Barrios, M., Patel, N., Arvandi, A., Paone, R., and Santana, D. 2017. "Venous Stent Migration into Right Ventricle," *Cureus* 9(8): e1583; Hayashi, T., Akhtar, S., and Alwi, M. 2017. "Stent Migration After Right Ventricular Outflow Tract Stenting in the Severe Cyanotic Tetralogy of Fallot Case," *Annals of Pediatric Cardiology* 10(2):206-208; Garbey, M., Salmon, R., Fikfak, V., and Clerc, C. O. 2016. "Esophageal Stent Migration: Testing Few Hypothesis with a Simplified Mathematical Model," *Computers in Biology and Medicine* 79:259-265; Moltzer, E., Ouhlous, M., Roos-Hesselink, J. W., Bogers, A. J., and Witsenburg, M. 2013. "Proximal Aortic Stent Migration," *Netherlands Heart Journal* 21(11): 517-519; Kobayashi, D., Singh, H. R., Turner, D. R., Forbes, T. J., and Gowda, S. T. 2012. "Transcatheter Retrieval and Repositioning of Embolized Stent from the Right Ventricle in an Infant," *Texas Heart Institute Journal* 39(5):639-643).

For ductus that require clearing prior to stenting implantation, the endoluminal apparatus incorporates radially protrusible tools that can prepare the wall for treatment by injection or wetting, for example, then shave, abrade, or scrape (curet, evide) away adhesions or plaque along the lumen wall. The extraluminal stents described herein eliminate the need to situate a foreign object within the lumen and are intended to be usable in any vas or ductus of any vertebrate that is wide enough in diameter to admit the apparatus used to place the implants and provides a wall thickness sufficient to accommodate these. That an endoluminal stent must clog in the airway, especially when used for a chronic congestive condition such as bonchiectasis, is indisputable. Any endoluminal stent, regardless of the type ductus in which it is placed, is susceptible to accretions, irritation, occlusion, and migration (dislocation, displacement), and any of these, much less its fracture, can result in serious consequences.

In the digestive tract, an endoluminal stent is often pushed along by the passing contents as well as peristalsis, making migration common unless the stent is fixed in position by stapling or the use of more than one stent. Just as endoluminal stents, extraluminal stents can be used to alleviate the symptoms of tracheal or bronchial stenosis or collapse, obturate fistulas, preserve the patency of blood vessels, and maintain the patency of ureters and gamete transporting ducts, for example. Stenotic conditions amenable to treatment with a stent exclude noncompliant constrictions of the lumen due to a congenital malformation. Elimination from the lumen eliminates contact with the healing endothelium as well as the risks assocated with migration, fracture, or fragmentation, and allows the stent to expand and contract without stressing or deforming the ductus.

Intrinsically and quasi-intrinsically magnetized stent-jackets, addressed below in the section entitled Types of Stent-jacket, eliminate permanent magnets mounted about the outer surface of a stent-jacket. The thinner stent-jacket with no outward projections can be fitted to arteries ensheathed within muscle, notably, to treat peripheral artery disease. Prepositioned impasse-jackets allow continued drug targeting at any level along any ductus to include such locations, as well as protect against embolism by a miniball whether mid- or postprocedurally, and whether the result of human error or a direct blow. Medicated and irradiated stent-jackets are less and less limited to the palliative and more and more able to effect an actual cure.

2. Preliminary Description of the Invention

Brief summaries are provided above in the abstract and below in the section entitled Summary of the Invention. The invention pertains to means for ablation or angioplasty as appropriate, the targeting of drugs, and the infixion of tiny implants within organs and in particular, into the walls of tubular anatomical structures, to treat lesions or pathological conditions thereof, such as stenosis or collapse. Whether the contents are medicinal, irradiating, and/or ferromagnetic, the implants meant for infixion within tissue such as ductus-intramural are distinguished by type based upon conformation as either miniature balls, or miniballs, which are spherules introduced from within the lumen, or as small arcuate bands, or stays, which are introduced from outside the outer fibrous jacket or tunic, the tunica fibrosa or adventitia, of the organ, vessel, or duct. Such implants can be used for drug delivery, drug targeting, and/or to stent.

Other implants to be described are collars or jackets for placement about ductus which are used with these infixed implants to retract the implants and thus act as a stent and/or to attract drug delivery nanoparticles, microspheres, or miniballs via the lumen. Miniballs and stays are alike only in positioning and general functions. Miniballs are quickly placed from within the lumen without the need for local access through a small or laparoscopic incision. Placement thereof is prompted when an antecedent procedure such as an angioplasty necessitates transluminal (transcatheter) treatment in any event. Spheroidal for ballistic delivery but poor for magnetic susceptibility, miniballs are placed in relatively tight formation to uniformly distribute the tractive force and avoid pull-through or delamination.

An extraluminal stent in the vascular tree leaves no foreign object in the lumen, which is the central source of adverse sequelae with endoluminal stents, to include reocclusion. Unless placed in a surgical field opened for another reason, stays are less quickly placed through an incision at the body surface than are miniballs. Stenting with stays or miniballs not only avoids the need to situate a foreign object in the lumen, but avoids the lumen entirely. The result is a stent which is less likely to perpetuate the chronic endothelial dysfunction that led to inflammation and atheroma, fibroatheroma, or more complicated lesion, which intervention and endoluminal stenting reinforces (see, for example, Cui, Y., Liu, Y., Zhao, F., Shi, D., and Chen, K. 2016. "Neoatherosclerosis after Drug-Eluting Stent Implantation: Roles and Mechanisms," *Oxidative Medicine and Cellular Longevity* 2016:5924234; Veerasamy, M., Bagnall, A., Neely, D., Allen, J., Sinclair, H., and Kunadian, V. 2015. "Endothelial Dysfunction and Coronary Artery Disease: A State of the Art review," *Cardiology in Review* 23(3):119-129; Komiyama, H., Takano, M., Hata, N., Seino, Y., Shimizu, W., and Mizuno, K. 2015. "Neoatherosclerosis: Coronary Stents Seal Atherosclerotic Lesions but Result in Making a New Problem of Atherosclerosis," *World Journal of Cardiology* 7(11):776-783; Rudolph, A., Teske, M., Illner, S., Kiefel, V., Sternberg, K., and 3 others 2015. "Surface Modification of Biodegradable Polymers Towards Better Biocompatibility and Lower Thrombogenicity," *Public Library of Science One* 10(12):e0142075; Wang, X., Zachman, A, L., Chun, Y. W., Shen, F. W., Hwang, Y. S., and Sung, H. J. 2014. "Polymeric Stent Materials Dysregulate Macrophage and Endothelial Cell Functions: Implications for Coronary Artery Stent," *International Journal of Cardiology* 174(3):688-695; "Murase, S., Suzuki, Y., Yamaguchi, T., Matsuda, O., Murata, A., and Ito, T. 2014. "The Relationship Between Re-endothelialization and Endothelial Function After DES [drug-eluting stent] Implantation: Comparison Between Paclitaxcel-eluting Stent and Zotarolimus-eluting Stent," *Catheterization and Cardiovascular Interventions* 83(3):412-417; Minami, Y., Kaneda, H., Inoue, M., Ikutomi, M., Morita, T., and Nakajima, T. 2013. "Endothelial Dysfunction Following Drug-eluting Stent Implantation: A Systematic Review of the Literature," *International Journal of Cardiology* 165(2):222-228; Gutiérrez, E., Flammer, A. J., Lerman, L. O., Elízaga, J., Lerman, A., and Fernández-Avilés, F. 2013. "Endothelial Dysfunction Over the Course of Coronary Artery Disease," *European Heart Journal* 34(41):3175-3181; Nakazawa, G., Otsuka, F., Nakano, M., Vorpahl, M., Yazdani, S. K., and 4 others 2011. "The Pathology of Neoatherosclerosis in Human Coronary Implants Bare-metal and Drug-eluting Stents," *Journal of the American College of Cardiology* 57(11):1314-1322; Kim, J. W., Suh, S. Y., Choi, C. U., Na, J. O., Kim, E. J., and 4 others 2008. "Six-month Comparison of Coronary Endothelial Dysfunction Associated with Sirolimus-eluting Stent Versus Paclitaxel-eluting Stent," *Journal of thd American College of Cardiology Cardiovascular Interventions* 1(1):65-71; Caramori, P. R. A.; Lima, V. C.; Seidelin, P. H.; Newton, G. E; Parker, J. D; Adelman, A. G. 1999. "Long-term Endothelial Dysfunction after Coronary Artery Stenting," *Journal of the American College of Cardiology* 34(6): 1675-1679; van Beusekom, H. M., Whelan, D. M., Hofma, S. H., Krabbendam, S. C., van Hinsbergh, V. W., Verdouw, P. D., and van der Giessen, W. J. 1998. "Long-term Endothelial Dysfunction is More Pronounced after Stenting than after Balloon Angioplasty in Porcine Coronary Arteries," *Journal of the American College of Cardiology* 32(4): 1109-1117).

Some endothelial dysfunction is to be expected from intervention of any kind (see, for example, Borovac, J. A., D'Amario, D., and Niccoli, G. 2017. "Neoatherosclerosis and Late Thrombosis After Percutaneous Coronary Intervention: Translational Cardiology and Comparative Medicine from Bench to Bedside," *Yale Journal of Biology and Medicine* 90(3):463-470; Rudolph, A., Teske, M., Illner, S., Kiefel, V., Sternberg, K., and 3 others 2015, Op cit.); however, this should be significantly less with extraluminal means, and remedial meaures are becoming apparent (see, for example, Liu, H., Ba, P., Li, L., Wang, Y., Xu, C., Deng, M., Zhang, J., and Zhao, X. 2017. "Pitavastatin Nanoparticle-engineered Endothelial Progenitor Cells Repair Injured Vessels," *Scientific Reports* 7(1):18067; Lu, Q., Ye, F., Yang, X., Gu, Q., Wang, P., Zhu, J., Shen, L., and Gong, F. 2015. "Accelerated Recovery of Endothelium Function After Stent Implantation with the Use of a Novel Systemic Nanoparticle Curcumin," *Biomed Research International* 2015:291871; Cerrato, E., Echavarria-Pinto, M., Tandjung, K., Macaya, C., and Escaned, J. 2014. "Optimizing Vessel Healing Following Drug Eluting Stent Implantation with Biodegradable Polymer DES [drug-eluting stent]," *Minerva Cardioangiologica* 62(5):407-420; Hu, C. H., Ke, X., Chen, K., Yang, D. Y., Du, Z. M., and Wu, G. F. 2013. "Transplantation of Human Umbilical Cord-derived Endothelial Progenitor Cells Promotes Re-endothelialization of the Injured Carotid Artery After Balloon Injury in New Zealand White Rabbits," *Chinese Medical Journal* (in English) 126(8):1480-1485; van den Heuvel, M., Sorop, O., van Beusekom, H. M., and van der Giessen, W. J. 2009. "Endothelial Dysfunction After Drug Eluting Stent Implantation," *Minerva Cardioangiologica* 57(5):629-643).

Extended circumferentially and parallel to the substrate ductus, stays provide more continuous expansive lifting and have greater retentive ability, especially when coated with a cement that prevents ductus wall failure. Nonabsorbable miniballs and stays to be integrated into the surrounding tissue are provided with an undercut textured surface. Stays are automatically coated with a cement when ejected from the insertion tool that incorporates tissue stimulating substances to encourage the gradual infiltration and supplantation of the cement by tissue. To deliver the cement with miniballs without fouling the airgun requires followup injection with the aid of side-looking radial projection unit injection tool-inserts, as addressed below in the section entitled Self-contained Electrical/Fluid System-neutral Tool-inserts, to Include Injection and Ejection Syringes or a service catheter hypotube injector, as mentioned below in the section entitled Risk of Abrupt Closure with Thrombus and Vasospasm.

This depiction of a stent-jacket in FIG. 5 with small permanent magnets mounted about its outer surface is presented for clarity of the underlying concept; most stent-jacket achieve uniformity of the magnetic tractive force without outward protrusion of discrete magnets by embedding the magnetized material within the jacket, as explained below in the section entitled Types of Stent-jacket. Any of the implants to be described can be magnetized for drug-targeting. If accidently dropped or mispositioned, medicinal and/or irradiating miniballs and stays include sufficient superparamagnetic magnetite or maghemite nanoparticles or finely grained powder to allow instant arrest and retrieval using the recovery electromagnets of the recovery and extraction miniball electromagnet assembly built into the insertion apparatus, a separate caheteric probe with magnetized tip, impasse-jackets prepositioned downstream precisely to truncate further migration, or if necessary such as if embolizing, a powerful external electromagnet positioned to suddenly pull the implant outside of the ductus or other structure.

Stent-jackets, addressed in the sections below entitled Concept of the Extraluminal Stent and The Extraductal Component of the Extraluminal Stent and the Means for Its Insertion among others, rib-jackets addressed in the section below entitled Spine and Ribs-type Stent-jackets, and magnet-jackets, or magnet-wraps, addressed below in the section entitled Concept of the Magnet-wrap represent a graduated series of type jackets based upon firmness or backing firmness. Stent-jackets must possess the longitudinal and circumferential firmness to stent, that is, to not flex inward under the magnetic attractive force needed to draw the encircled or substrate ductus-intramural implants radially outward. Stent-jackets need not, however, be more firm than is necessary to accomplish this as is based upon the retractive force needed to keep the ductus patent.

Rib jackets are firm or firmly backed circumferentially but not longitudinally as complies with peristalsis along the gastrointestinal tract, or in miniature form, ureters and fallopian tubes. Magnet jackets are stretchable in all directions as allows complete compliance with the intrinsic movement within the substrate ductus where the attractive force is applied at a distance to affect magnetically susceptible implants fastened to or infixed within distant tissue or draw susceptible matter such as miniballs or nanoparticles from the substrate lumen contents where that ductus is not collapsed, malacotic, or constricted. In magnetic stenting or tissue retraction applications, the ductus-intramural or intra-ductal implants include nonmagnetized magnetically susceptible (ferrous) material, and are attracted or drawn rather than attracting or drawing. That this relationship might be reversed so that the implants were magnetized is considered obvious. Miniballs and stays are not limited to magnetic stenting or the retraction of tissue using magnetic force.

Either can incorporate ferromagnetic material for use with a magnetic stent-jacket, medication, concentric layers of different medication, a radionuclide, or a protein solder, for example, in any combination, as well as include magnetically attracting or attracted material for retrievability if dropped or mispositioned. Implants to be fully absorbed omit magnetized content, which a toxic lanthanoid (see, for example, Donohue, V. E., McDonald, F., and Evans, R. 1995. "In Vitro Cytotoxicity Testing of Neodymium-Iron-Boron Magnets," *Journal of Applied Biomaterials* 6(1):69-74), is encapsulated for chemical isolation, usually with gold plate, which is further treated to eliminate any voids or surface residue, as addressed below in the section entitled Stent-jackets and Stent-jacket Supportng Elements and is preferred to the poly(p-xylylene®) AF-4 polymer (Paralyne) passivation thin film commonly used to coat stents or polytetrafluoroethylene (see, for example, Oje, A. M. and Ogwu, A. A. 2017. "Chromium Oxide Coatings with the Potential for Eliminating the Risk of Chromium Ion Felease in Orthopaedic Implants," *Royal Society Open Science* 4(7): 170218; Aramesh, M., Tong, W., Fox, K., Turnley, A., Seo, D. H., Prawer, S., and Ostrikov, K. K. 2015. "Nanocarbon-coated Porous Anodic Alumina for Bionic Devices," *Materials* (Basel, Switzerland) 8(8):4992-5006; Liao, W. H., Lin, C. R., Wei, D. H., Shen, Y. R., Li, Y. C., Lee, J. A., and Liang, C. Y. 2012. "Concurrent Improvement in Biocompatibility and Bioinertness of Diamond-like Carbon Films with Nitrogen Doping," *Journal of Biomedical Materials Research. Part A* 100(11):3151-3156; Wang, G. and Zreiqat, H. 2010. "Functional Coatings or Films for Hard-tissue Applications," *Materials* (Basel, Switzerland) 3(7):3994-4050; Hinüber, C., Kleemann, C., Friederichs, R. J., Haubold, L., Scheibe, H. J., and 3 others 2010. "Biocompatibility and Mechanical Properties of Diamond-like Coatings on Cobalt-chromium-molybdenum Steel and Titanium-aluminum-vanadium Biomedical Alloys," *Journal of Biomedical Materials Research. Part A* 95(2):388-400; Roy, R. K. and Lee, K. R. 2007. "Biomedical Applications of Diamond-like Carbon Coatings: A Review," *Journal of Biomedical Materials Research. Part B, Applied Biomaterials* 83(1):72-84; Ahmad, K. A., Drummond, J. L., Graber, T., and BeGole, E. 2006. "Magnetic Strength and Corrosion of Rare Earth Magnets," *American Journal of Orthodontics and Dentofacial Orthopedics* 130(3):275.e11-5; Noar, J. H., Wahab, A., Evans, R. D., and Wojcik, A. G. 1999. "The Durability of Parylene Coatings on Neodymium-iron-boron Magnets," *European Journal of Orthodontics* 21(6):685-693).

Not limited to the walls of ductus, miniballs and stays can be implanted anywhere in the body. The major categories of miniballs and stays are absorbable (temporary, usually medicinal), combination absorbable-nonabsorbable, which have a permanent or intravascular ferromagnetic core, and nonabsorbable or permanent used to secure a magnetic extraluminal stent of the kind to be described. Temporary (absorbed) miniballs contain medication, adhesives, or both. Temporary (absorbed) stays made of the same materials that are used to make absorbable suture and tissue engineering scaffolds can be used as buttress supports to sustain the patency of a collapsed or stenosed lumen over the dissolution period.

Any kind of stay can incorporate or be coated with medication, foreign body tissue reaction suppressive substances, such as dexamethasone, or an adhesive, or any combination of these. Including sufficient ferromagnetic material such as magnetite or maghemite nanoparticles or finely grained powder in an absorbable stay or miniball assures retractability with a magnet. Ductus-intramural implants (stays and miniballs) used as the intraductal component of a magnetic stent contain a ferromagnetic material, usually in the form of a core encapsulated within a biocompatible chemical isolation layer. The core can be overlain with additional layers of medication, a tumefacient, sclerosant, adhesive, or any combination of these.

Such constituents can be dispersed or noncontinuous and intermingled, so that rather than homogeneous, each layer might include particles, microspheres, or nanorods of various therapeutic substances (see, for example, Nabar, G. M., Mahajan, K. D., Calhoun, M. A., Duong, A. D., Souva, M. S., and 6 others 2018. "Micelle-templated, Poly(lactic-co-glycolic Acid) Nanoparticles for Hydrophobic Drug Delivery," *International Journal of Nanomedicine* 13:351-366; Zhu, X., Liu, C., Duan, J., Liang, X., Li, X., Sun, H., Kong, D., and Yang, J. 2016. "Synthesis of Three-arm Block Copolymer Poly(lactic-co-glycolic Acid)-poly(ethylene Glycol) with Oxalyl Chloride and Its Application in Hydrophobic Drug Delivery," *International Journal of Nanomedicine* 11:6065-6077; Cho, H., Gao, J., and Kwon, G. S. 2016. "PEG-b-PLA Micelles and PLGA-b-PEG-b-PLGA Sol-gels for Drug Delivery," *Journal of Controlled Release* 240:191-201; McKenzie, M., Betts, D., Suh, A., Bui, K., Tang, R., and 4 others 2016. "Proof-of-concept of Polymeric Sol-Gels in Multi-Drug Delivery and Intraoperative Image-guided Surgery for Peritoneal Ovarian Cancer," *Pharmaceutical Research* 33(9):2298-2306; Mundargi, R. C., Babu, V. R., Rangaswamy, V., Patel, P., and Aminabhavi, T. M. 2008. "Nano/Micro Technologies for Delivering Macromolecular Therapeutics Using Poly(D,L-lactide-co-glycolide) and Its Derivatives," *Journal of Controlled Release* 125(3):193-209). The entire implant or its outer layer can release a chemotherapeutic drug that also radiosensitizes the targeted tissue, such as cisplatin, nimorazole, or cetuximab. Just as with prior art seeds, radiation stays can incorporate metals to aid in targeting intensity-modulated radiation therapy (IMRT), for example.

Stays containing a radioactive seed also contain ferromagnetic material, which if sufficient allows these to be used as the intraductal component of a magnetic stent. Such stays can likewise be coated with concentric layers each containing a drug or drugs and/or other therapeutic substances. In the trachea and bronchi, gastrointestinal tract, and many muscular arteries, ferrous content allows any number of irradiating seed stays of higher dose-rate than could be used if irretrievable to be recovered at any time. Moreover, seed stays are implantable in ductus walls more quickly than could be accomplished using conventional means when these are even capable of placement thus. Furthermore, unlike conventional seed implant devices, regardless of its content, only the miniball or stay enters the tissue to be treated, so that the penetration path or trajectory is no larger in cross-section than is the implant itself.

By entering suddenly at high velocity, miniballs preempt the evasive receding of flaccid tissue to effect infixion with minimal tearing or stretching injury through a trajectory no wider than the miniball itself. The sudden extraction or evulsion of a miniball as addressed in section X2c below entitled Stereotactic Arrest and Extraction of a Circulating, Dangerously Mispositioned, or Embolizing Miniball is similarly intended to reverse the action of aeroballistic infixion by preempting any ability of intervening tissue to resist perforation. Loaded with sharp stays, a quick action of the hand on the insertion tool produces the same result. Properly applied, perforations of the ductus wall should seldom occur. Stent-jacket and stay insertion tools generally incorporate clips not included in the drawing figures for attaching alongside a fine gauge endocscope with illumination, aspiration, cautery, cryogenic, or heating line, or laser, for example, as necessary.

Regardless of content, wider stays with a nonabsorbable exterior and/or nonmagnetic can be used to maintain the patency of a collapsed ductus by acting as mechanical supporting buttresses without the need for a circumductal or extravascular collar type stent component. In a magnetic stent, the ferromagnetic material in the implant is attracted to small chemically isolated neodymium iron boron lanthanoid magnets mounted:

1. About an encircling (periductal, perivascular, circumductal, circumvascular) stent-jacket, or 2. To small platform base plates with prongs described below in the section entitled Subcutaneous, Suprapleural, and Other Organ-attachable Clasp- or Patch-magnets, or 3. To magnet-wraps, described below in the section of like title. As addressed below in the section entitled Significance of SterileAntixenic Immune Tissue Reaction, to delay if not prevent a foreign body reaction, implants and prongs that penetrate tissue to secure implant backings in place are coated with reaction-suppressive substances, such as phosphorylcholine, dexamethasone, and/or curcumin.

The various components used may be classified as 1. Transluminal, to include special catheters used as airgun barrels (some also made angioplasty capable); 2. Intraductal, to include miniballs and stays; or 3. Extraductal, to include stent-jackets, clasp-wraps, and magnet-wraps. Completely extracorporeal are modified commercial and dedicated interventional airguns and stay insertion tools, to be described. Stent-jackets may be made adaptive to the reduction in caliber of vasa with subsidence (detumescence, regression) in an initially enlarged condition thereof, while stays may be adaptive in partial or complete dissolution over a controllable period. Stays and miniballs can additionally be made to release medication or radiation. FIG. 1 shows the interrelations among the different type implants described herein.

Pursuant to 37 CFR 1.475, the apparatus and methods go to a group of interrelated devices and procedures that respond to a single generative inventive concept and so conform to the requirement for unity of invention. According to the medical necessity, each and every element of the invention can have an immediate and compulsory relation of combination with any of the others, and none is used with devices not included in the system. Self-contained and independent from the prior art, the system provides all of the means essential to accomplish the type of implantation it makes possible, to include site preparation, implant infixion, and the implants themselves. Site preparation includes the delivery of medication, atherectomy (atherotomy), angioplasty, and ablation.

Other means described herein are ancillary but essential to support these type implants, whether as insertion tools, adjuvant medication, or as means for pretesting patient tissue in situ in order to ascertain as best one might the prospective safety in using these means, for example. Consistent with this unity in conception, the various instruments and supplies described herein can be combined in different ways, the medical circumstances determining such use. That the attracting and attracted elements described herein, specifically, magnets and nonmagnetized ferromagnetic miniballs and stays respectively, could be reversed to obtain the same result is considered obvious.

Implantation of miniballs by means of a specially adapted, or interventional, airgun not only overcomes tissue flaccidity but affords an implant loading point that proximate to the operator or an assistant, allows immediate adaptation to the conditions actually encountered following entry without the need to withdraw. The implants tiny, such work is generally accomplished under magnification, any accidental perforations quickly sealed interventionally if not spontaneously. In most instances, the implants will consist entirely of medication or of radiation-emitting seeds with surrounding coats of medication for localized placement within a circumscribed area, usually within the wall of a tubular anatomical structure. The dose is thus concentrated in or adjacent to the targeted tissue and minimized for nontargeted tissue, whether by diffusion or through the circulation. Reducing systemic dispersion before take-up allows considerable reduction in the overall dose.

Delivery in this manner allows medication currently high in cost, such as time-released trastuzumab with paclitaxel, for example, conventionally administered by intravenous infusion with a cremophore-containing vehicle that can cause hypersensitivity reactions injection, or by release from an endoluminal drug-eluting stent to treat an atheromatous lesion (Sauseville, E. A. and Longo, D. L. 2005. "Principles of Cancer Treatment: Surgery, Chemotherapy, and "Biologic Therapy," in Kaspar, D. L, Braunwald, E., Fauci, A. S., Hauser, S. L., Longo, D. L., and Jameson, J. L., *Harrison's Principles of Internal Medicine,* 16th Edition, New York, N.Y.: McGraw-Hill, page 477), to be used efficiently, kept away from nontargeted tissue, and applied to lesions surrounding lumina not previously targetable. Dose minimization by targeting also results in a reduction in side effects.

The use of an impasse-jacket as a holding jacket, as addressed below in the section entitled Endoluminal Prehension of Miniballs and Ferrofluids, to retain or draw a drug such as paclitaxel administered in the form of a drug carrier nanoparticle containing ferrofluid or in encapsulated microspheres from the bloodstream for local infusion into an atheromatous plaque or carcinoma is addressed in the sections below entitled Concept of the Impasse-jacket and Interception and Recovery of a Miniball Entering the Circulation. Implants containing ferromagnetic material can be retrieved if dropped or if used to fully or paritally encircle a ductus so that its wall can be retracted by means of a mantling (periductal, perivascular, circumductal, circumvascular) pliant jacket with a slit along one side having tiny permanent magnets mounted about its outer surface.

The implants then constitute the intraductal or ductus-intramural component of an extraluminal stent, the extraductal component consisting of the immediately periductal stent-jacket having the small permanent magnets mounted about it or of small but slightly more powerful magnets implanted at a greater distance by means of patch-magnets or magnet-jackets to be described. To freely expand with the pulse and not interfere with the contractive waves of peristalsis passing through, stent-jackets are sized for the quiescent outer diameter of the ductus to be treated, and for minimal mass and intracorporeal obstrusiveness as might encroach upon or abrade neighboring structures, the bar magnets mounted about the outer surface of the resilient segment of tubing, or the base-tube, part number 5 in the drawing figures, are of high energy product neodymium iron boron, which allows these to be small and unobtrusive.

When properly matched to the collapsed or stenotic ductus, the stent-jacket retracts the implanted wall outwards to the proper quiescent diameter. Elastic, the jacket expands up to the maximum diameter of the ductus (such as on the systoles). Because veins are substantialliy inert, stent-jackets, clasp-wraps, and magnet-jackets placed on veins, unlike arteries and peristaltic ductus, can be coated on the inner surface with a surgical adhesive when placed. A stent-jacket used as a circumvascular or circumtracheal stent can be inserted through one or two incisions that are smaller than the incisions required by conventional open procedures and secured by means of end-ties (addressed below). Because repair tends to be deferred until the patient is older and impaired, the lesser trauma is significant.

The nontransluminally delivered extraductal components to be described herein—stent-jackets, stays, clasp-wraps, and so on—allow passage through an entry wound smaller in size than does conventional open repair, typically a small (stab, "keyhole," "bandaid," or laparoscopic) incision, or microincision. Applied to a procedure of like objective as a surgical atherectomy, an atherectomy accomplished transluminally avoids the need for an incision, and also allows extraluminal stenting through such a small incision. When for any reason ballistic implantation is contraindicated, a plurality of arcuate stent-stays containing ferrous metal or a clasp-wrap, likewise used with a stent-jacket, can be manually inserted into the wall of the ductus through a local incision, stays by means of special hand tools to be described.

Endoluminal and extraluminal tests are provided in the sections below entitled In Situ Test upon Endoluminal Approach for Intra- or Inter-laminar Separation (Delamination, Laminar Avulsion) and in Situ Test upon Extraluminal Approach for Intra- or Inter-laminar Separation (Delamination, Avulsion) for separation within a tunic (intralaminar or intratunical separation) or between tunics (interlaminar or intertunical separation, dilaceration, or avulsion, decollement; delamination), such as between the adventitia and the media. The test is intended to determine whether spherules, stays, or a clasp-wrap, can be used at all, if so, at what depth into the ductus wall the type that is most suitable should be implanted, with or without the aid of a surgical adhesive. The result may determine, for example, that no type of implant can be placed subadventitially, so that the implant must be implanted within the media.

When transluminal access is best avoided, stays, which are placed inside the ductus wall, or a clasp-wrap, which that encircles and engages the ductus from without, each of which is inserted through the same local incision as the stent-jacket, are used. A clasp-wrap, as addressed below in the section of like title, is an alternative means for introducing ferromagnetic implants into the wall of a ductus when the adventitia is too weakened (softened, malacotic, malacic) for ballistic implantation. Clasp-wraps are similar to stays in being applied from outside the ductus, which eliminates the need for transluminal access. However, these differ in attaching the ferromagnetic implants to an elastic backing that aids retention by a weakened adventitia, and in applicability only to ductus which can be fully encircled.

In most situations, especially when to serve as the intraductal component of a magnetic stent, either miniballs or stays will be better suited to the condition presented, the use of both exceptional, and in the same ductus, seldom to be expected; however, individual implants of the kind chosen can differ in medication or other therapeutic substances contained. When an open surgical field has not already been cleared, to implant stays requires access to the target ductus through a small incision from outside the body. Approach thus avoids the lumen entirely both during placement and as infixed. This means that no foreign object is inserted into the lumen, and that in a blood vessel, the compresence of an infectious pathogen bacterial, mycotic, or viral, will not provide a pathway into the ductus wall.

For the placement of medication implants which are fully absorbed, access through an external incision is generally less attractive than is the endoluminal delivery of miniballs. For stenting, however, especially where an angioplasty is unnecessary, the intraductal component is usually permanent, and to place the stent-jacket requires an incision from the outside anyway, making the use of stays overall less intrusive. Unless the miniball or stay subadventital or subfibrosal implants are drawn outwards towards the inner surface of the stent-jacket noncompressively with little damage to vasa and nervi vasorum, the adverse sequelae of endothelial dysfunction, atheromatous lesioning, and a loss in wall strength will ensue. Damage to the vasa vasorum in third stage syphilis, for example, results in aortic aneurysm.

Lining the side-slitted and perforated jacket with moisture barrier-coated nonbiodegradable or bioresistant moisture barrier moisture protection-coated visco-elastic polyurethane, or viscoelastic polyurethane foam, for example, averts perivascular or periductal compression of the microvasculature and small nerves about the periphery of the ductus, and providing cutouts (perforations, portals), allows some nonenclosure of the outer surface of the ductus, allowing gas exchange and evaporation from the outer surface of the ductus, or adventia.

While shape memory is not synonymous with fine shape accommodation or compliance, alternative shape-memory materials are under development which do or should eventually satisfy this requirement (see, for example, Zhang, K., Feng, X., Ye, C., Hempenius, M. A., and Vancso, G. J. 2017. "Hydrogels with a Memory: Dual-Responsive, Organometallic Poly(ionic Liquid)s with Hysteretic Volume-Phase Transition," *Journal of the American Chemical Society* 139(29):10029-10035; Lowenberg, C., Balk, M., Wischke, C., Behl, M., and Lendlein, A. 2017. "Shape-memory Hydrogels: Evolution of Structural Principles to Enable Shape Switching of Hydrophilic Polymer Networks," *Accounts of Chemical Research* 50(4):723-732; Landsman, T. L., Touchet, T., Hasan, S. M., Smith, C., Russell, B., and 3 others 2017. "A Shape Memory Foam Composite with Enhanced Fluid Uptake and Bactericidal Properties as a Hemostatic Agent," *Acta Biomaterialia* 47:91-99; Walker, R. M., Gillespie, B. M., Thalib, L., Higgins, N. S., and Whitty, J. A. 2017. "Foam Dressings for Treating Pressure Ulcers," *Cochrane Database of Systematic Reviews* 10:CD011332; Chan, B. Q., Low, Z. W., Heng, S. J., Chan, S. Y., Owh, C., and Loh, X. J. 2016. "Recent Advances in Shape Memory Soft Materials for Biomedical Applications," *American Chemical Society Applied Materials and Interfaces* 8(16):10070-10087; Hardy, J. G., Palma, M., Wind, S. J., and Biggs, M. J. 2016. "Responsive Biomaterials: Advances in Materials Based on Shape-memory Polymers," *Advanced Materials* (Deerfield Beach, Fla.) 28(27): 5717-5724; Ebara, M. 2015. "Shape-memory Surfaces for Cell Mechanobiology," *Science and Technology of Advanced Materials* 16(1):014804).

Absorbable materials of this kind are also under development (see, for example, Balk, M., Behl, M., Wischke, C., Zotzmann, J., and Lendlein, A. 2016. "Recent Advances in Degradable Lactide-based Shape-memory Polymers," *Advanced Drug Delivery Reviews* 107:136-152). Absorbable stent and impasse-jackets use biodegradable shape memory foam (Peterson, G. I., Dobrynin, A. V., and Becker, M. L. 2017. "Biodegradable Shape Memory Polymers in Medicine," *Advanced Healthcare Materials* 6(21); Singhal, P., Small, W., Cosgriff-Hernandez, E., Maitland, D. J., and Wilson, T. S. 2014. "Low Density Biodegradable Shape Memory Polyurethane Foams for Embolic Biomedical Applications," *Acta Biomaterialia* 10(1):67-76).

The moisture barrier prevents the breakdown products of the viscoelastic polyurethane foam from being released into the surrounding tissue and bloodstream where it is toxic, as was the problem with earlier breat implants. Any polymerization process residue or plasticizer must be thoroughly removed. The presence of toxic residues from polymerization of moisture barrier-coated viscoelastic polyurethane foam linings can be averted with suitable preliminary cleaning of the material (see Maxwell, G. P. and Gabriel, A. 2017. "Breast Implant Design," *Gland Surgery* 6(2):148-153; Daka, J. N. and Chawla, A. S. 1993. "Release of Chemicals from Polyurethane Foam in the Même Breast Implant," *Biomaterials, Artificial Cells, and Immobilization Biotechnology;* 21(1):23-46).

The polyurethane foam used in stent- and impasse-jackets is enveloped within a shape compliant moisture barrier that affords additional protection from any breakdown products of the primary component. Even were the same polyurethane foam used as that in the breast implants withdrawn from the market in 1991, the release of 2,4-toluenediamine (TDA) from the foam lining of a stent-jacket, impassejacket, or outrigger, which is minute in amount compared to that in a breast implant, would be too little to act as a carcinogen. That is, the absolute volume of the material in any of the jackets described herein is minute compared to that in a breast implant, making it improbable that its degredation would release an amount of the material that would accede to a toxic burden (see, for example, Pompei, S., Evangelidou, D., and Ferrante, G. 2017. "Comments on "Commentary On: The Modern Polyurethane-coated Implant in Breast Augmentation: Long-term Clinical Experience," *Aesthetic Surgery Journal* 37(5):NP56-NP57; Frame, J. 2016. "Commentary On: The Modern Polyurethane-coated Implant in Breast Augmentation: Long-term Clinical Experience," *Aesthetic Surgery Journal* 36(10): 1130-1132; Pompei, S., Evangelidou, D., Arelli, F., and Ferrante, G. 2016. "The Modern Polyurethane-coated Implant in Breast Augmentation: Long-term Clinical Experience," *Aesthetic Surgery Journal* 36(10):1124-1129; Vazquez, G. and Pellón, A. 2007. "Polyurethane-coated Silicone Gel Breast Implants Used for 18 Years," *Aesthetic Plastic Surgery* 31(4):330-336; Kulig, K. 1998. "Lifetime Risk from Polyurethane Covered Breast Implants," *Environmental Health Perspectives* 106(11):A526-A527; Hester, T. R. Jr., Ford, N. F., Gale, P. J., Hammett, J. L., Raymond, R., Turnbull, D., Frankos, V. H., and Cohen, M. B. 1997. "Measurement of 2,4-toluenediamine in Urine and Serum Samples from Women with Même or Replicon Breast Implants," *Plastic and Reconstructive Surgery* 100(5):1291-1298). Signifiantly, as addressed below in the sections entitled Absorbable Base-tube and Stent-jacket; Miniball, Stay, and Clasp-magnet Matrix Materials; Significance of Sterile Antixenic Immune Tissue Reaction; and Materials Suitable for Rebound-directing Double-wedge Linings, among others, means for encouraging or forestalling attack by the immune system allow the rate of breakdown and persistence of implanted polyurethane to be widely adjusted.

Furthermore, a rate of chemical breakdown of 0.8 percent per year (Benoit, F. M. 1993. "Degradation of Polyurethane Foams Used in the Même Breast Implant," *Journal of Biomedical Materials Research* 27(10):1341-1348) or alteration in cushioning properties exhibited by existing materials allows many years of use, and the presence of TDA or any other toxic product of foam degradation is readily detectable through urinalysis (Shanmugam, K., Subrahmanyam, S., Tarakad, S. V., Kodandapani, N., and Stanly, D. F. 2001. "2,4-Toluene Diamines—Their Carcinogenicity, Biodegradation, Analytical Techniques and an Approach towards Development of Biosensors," *Analytical Sciences* 17(12):1369-1374; Santerre, J. P., Woodhouse, K., Laroche, G., and Labow, R. S. 2005. "Understanding the Biodegradation of Polyurethanes: From Classical Implants to Tissue Engineering Materials," *Biomaterials* 26(35):7457-7470). Soy based foam is rejected as allergenic. Continued work should further improve the longevity of polyurethane foam (see, for example, Puskas, J. E. and Luebbers, M. T. 2012. "Breast Implants: The Good, the Bad and the Ugly. Can Nanotechnology Improve Implants?," *Wiley Interdisciplinary Reviews. Nanomedicine and Nanobiotechnology* 4(2): 153-168, bottom left page 155; Handel, N. 2006. "Long-term Safety and Efficacy of Polyurethane Foam-covered Breast Implants," *Aesthetic Surgery Journal* 26(3):265-274).

As used here, tissue reaction and infiltration into the closed cell material should not be problems as require surface treatment to lessen if not prevent; the foam is not embedded within but merely makes contact with the tissue, and the tissue contacted is intact, not injured, or granulated, and rapidly proliferating to heal at the interface with the foam. The same nonembedded condition that tends to retard the spontaneous absorption of absorbable materials also alleviates degradation of the urethane.

Furthermore, the junction between adventitia and foam is not compressive as with 'negative pressure wound therapy' where bandage lining ingrowth discourages the use of urethane. Whether to use miniballs or stays is determined on the basis of the overall medical considerations to include site accessibility. When not practically accessible from without (extracorporeally), implantation is of miniballs translumi- nally by means of a special catheter devised to serve as an extension to the barrel of a specially adapted semiautomatic gas-operated implant insertion airgun.

Such a specialized catheter, consisting of a unitized barrel-catheter and distal muzzle-head, is referred to as a barrel-assembly. Practical barrel-assemblies encompass multiple endoluminal capabilities. The airgun projects the spherules through the barrel-assembly and out the muzzle-head at its distal end at an acute forward angle, preferably to a point subjacent to (underlying) the outer fibrous sheath of the ductus, the tunica adventitia or tunica fibrosa in the trachea, or the tunica adventitia or tunica externa in blood vessels, for example. When the discharge velocity is set within the allowable range, which is tested beforehand, the elastic layers in the wall of the ductus prevent puncture. The miniballs are so small that unless the patient has been heavily anticoagulated, spontaneous sealing is prompt. Also, the risk of injury to neighboring tissue is negligible. Exceptionally, the implants are placed more deeply (adluminally, medially).

Viscoelastic polyurethane foam linings are addressed below in the sections entitled Requirement for Moisture Barrier-coated Viscoelastic Polyurethane Foam Linings and Stent- and Shield-jacket Moisture Barrier-coated Viscoelastic Polyurethane Foam Linings. When placed in a wet location, such linings have a typically vapor-deposited or sputtered moisture barrier. Not introduced into the bloodstream, stays reduce if not eliminate the need for systemic medication to suppress clotting, and are therefore to be preferred when the prospect of surgery is pronounced. When such is not the case, the length of the segment to be implanted is extensive, and procedural time with general anesthesia would best be minimized, miniballs are preferable to stays.

In that case, combinations of a systemically circulated anticoagulant where each implant has been coated with a reversal agent for hemostasis in the event of an accidental perforation—such as warfarin-vitamin K as phytonadione, anti-inhibitor coagulant complexes, or systemic heparin with protamine sulfate—will be too slow-acting. Provided it is sufficiently pliant to comply in investing the small vessels and nerves about the ductus, the hermetic, such as chemical vapor deposited highly plasticized (Parylene® C or N), coating, which completely biocompatible, is used to coat numerous implants such as stents (see, for example, Schwarz, J. A., Contescu, C. I., and Putyera, K. 2004. *Dekker Encyclopédia of Nanoscience and Nanotechnology*, Volume 1, page 263, Boca Raton, Fla.: Chemical Rubber Company Press), protects the foam from moisture breakdown.

The same treatment when applied to the outside of the jackets described herein will inhibit the deposition of clot, and prevent the catching onto or abrasion of neighboring tissue, as well as prevents fluid infiltration. In the mainlines, this prevents extravasation, and in the sidelines, fluid infiltration or leakage, assuring that dosing is accurate. Such a physical vapor deposited coating can be provided by several companies to include Acree Technologies Incorporated, Concord, Calif., Para-Coat Technologies, Johnstown, Pa., and KDF Electronic and Vacuum Services Incorporated, Rockleigh, N.J. Where the ductus is sufficiently exposed to serous fluid, for example, as to be quite wet, a hand dryer is used to remove most of the moisture before placing the side-entry jacket or nonjacketing side-entry connector.

Instead, a systemic antiplatelet blocker is administered and the miniballs coated with a fast-acting reversal agent or hemostat, such as kaolin (Al2Si2O5(OH)4) (Trabattoni, D., Gatto, P., and Bartorelli, A. L. 2012. "A New Kaolin-based Hemostatic Bandage Use after Coronary Diagnostic and Interventional Procedures," *International Journal of Cardiology* 156(1):53-54; Kheirabadi, B. S., Scherer, M. R., Estep, J. S., Dubick, M. A., and Holcomb, J. B. 2009. "Determination of Efficacy of New Hemostatic Dressings in a Model of Extremity Arterial Hemorrhage in Swine," *Journal of Trauma* 67(3):450-460; Politi, L., Aprile, A., Paganelli, C., Amato, A., Zoccai, G. B., and 5 others 2011. "Randomized Clinical Trial on Short-time Compression with Kaolin-filled Pad: A New Strategy to Avoid Early Bleeding and Subacute Radial Artery Occlusion after Percutaneous Coronary Intervention," *Journal of Interventional Cardiology* 24(1):65-72; Griffin, J. H. 1978. "Role of Surface in Surface-dependent Activation of Hageman Factor (Blood Coagulation Factor XII;" *Proceedings of the National Academy of Sciences of the United States of America* 75(4):1998-2002; Walsh, P. N. 1972. "The Effects of Collagen and Kaolin on the Intrinsic Coagulant Activity of Platelets. Evidence for an Alternative Pathway in Intrinsic Coagulation Not Requiring Factor XII," *British Journal of Haematology* 22(4):393-405) or methyl prednisolone (Qureshi, A. I. and Suri, M. F. 2008. "Acute Reversal of Clopidogrel-related Platelet Inhibition Using Methyl Prednisolone in a Patient with Intracranial Hemorrhage," *American Journal of Neuroradiology* 29(10):e97).

More specifically, the coating includes adenosine diphosphate, fibrin, and a kaolinite-derived aluminosilicate nanoparticlate. The insoluble kaolin coagulant is chemically inert and becomes embedded within the surrounding tissue. In an extraction from an impasse-jacket using a powerful external electromagnet, the extraction is stereotactically oriented to avoid any vulnerable structures. In blood vessels no anticoagulant is administered, and sealing occurs quickly. In other type ductus, problematic leakage can be averted by placing an absorbable shield-jacket. If the application involves the placement of a circumvascular jacket, the extent of dissection is much the same whether stays or miniballs are used. Accidental perforation through the ductus wall by a miniball discharged at too high a velocity or normal to (perpendicular) to the axis of the ductus ordinarily seals spontaneously as to pose no threat. If, however, a vulnerable neighboring structure such as a ganglion might be struck or septic contents allowed to spill out of the lumen, a shield-jacket is used. Radiation shield-jackets can be used with seed stays as well as miniballs.

Broadly, the apparatus used to place the implants of the ductus-intramural component of the extraluminal magnetic stents to be described and the applications most suited to various embodiments of these fall into three categories:

1. The air pistol as modified for interventional use, addressed below in the section entitled Modification of Commercial Airguns, with a simple pipe-type barrel-assembly, addressed below in the section entitled Simple Pipe Type Barrel-assemblies, suitable, for example, for use in the airway where a. The anatomy is differentiated or structured, b. The implants must be accurately placed in relation thereto with the exit port easily viewed, c. The larger size of the lumen allows the apparatus to be positioned without injury to the lumen wall, and d. Sufficient speed with precision does not require multiple discharge. To make possible the accuracy required, a simple pipe will usually have a fiberoptic endoscope, or angioscope, permanently attached, or where the viewing device is costly and wanted for use with more than one barrel-assembly, lashed alongside. As with the wires for the recovery electromagnet and any bounce-plate device as shown in FIGS. 35, 36, and 37, these cannot continue into the airgun barrel. The electrical connection for the electromagnet is of the form shown in FIG. 75.

2. The dedicated interventional airgun with a radial discharge barrel-assembly, generally for use in a lumen that unlike the trachea, for example, is relatively undifferentiated or uniform in structure, wherein the need for speed is greatest in blood vessels, the carotid and coronary arteries in particular. Ablation and ablation and angioplasty-capable barrel-assembly muzzle-heads enclose the barrel-tubes within a torpedo-shaped outer shell and discharge radially, or more accurately, frontoradially. To be usable in blood vessels, barrel-assemblies must include gas pressure diversion channels. Thus, a barrel-assembly capable of performing an angioplasty will always be capable of performing an ablation in a ductus of arterial diameter. Ablation and ablation and angioplasty-capable barrel-assemblies are also classified according to whether these are for use during and solely as an adjunct to discharge while engaged in and dependent upon the airgun for power and control, or whether these can be used as standalone means for ablation or angioplasty.

3. The manual insertion of stays, which inserted from outside the ductus, avoids not only the numerous disadvantages of placement of a foreign body within the lumen but also any complications that might arise from the ballistic placement of miniballs in a lumen carrying infectious or septic contents. Placed with less speed, stays avoid the lumen entirely, can often be placed laparoscopically under a local anesthetic, and therefore mitigate the need for speed.

A more detailed breakdown of barrel-assemblies by type is provided below in the section entitled Types of Barrel-assemblies. An ablation or ablation and angioplasty-capable barrel-assembly is equipped to perform an endoluminal ablation or an angioplasty or atherectomy independently of and without connection to an airgun. Another device, a radial projection catheter, addressed below in the section entitled Radial projection catheters, when matched in size to the barrel-assembly, can be slid over to ensheath, or ensleeve, the barrel-assembly, thereby supplementing the number of side-looking (lumen wall-radially directed) ablation or angioplasty tool lift-shafts integral to the barrel-assembly muzzle-head.

To allow discharge at a greater distance down a narrowing lumen, the portion of the muzzle-head distal to or forward of the miniball discharge exit-port or ports is kept short. Keeping the muzzle-head small in diameter allows access to lumina of smaller caliber and allows the pulse to force blood past a muzzle-head that completely occludes the lumen of a nonarteriosclerosed elastic artery. Bipartite or duplex radial projection catheters can be slid over the barrel-catheter of a barrel-assembly to add radial projection units or be used separately to perform an angioplasty. In nonelastic arteries, occlusive diameter must be compensated for with blood-grooves that run the length of the muzzle-head, for example. Radial projection unit push-arm tool-inserts can nudge the muzzle-head to a side to let blood pass.

Combination-forms with side-ports can pass blood through the bore, and provided the lumen wall stength test addressed below under the section entitled In Situ Test on Endoluminal Approach for Susceptibility of the Ductus Wall to Puncture, Penetration, and Perforation indicates that the ductus is unlikely to incur stretching or dissection injury, a hand-held external electromagnet as specified below in the section entitled Use of an External Electromagnet to Assist in Steering or in Freeing the Muzzle-head can be used as addressed below in this section to increase or create a gap for lumen contents to pass. Multiple push-arm type radial projection unit tool-inserts, addressed below in the sections entitled Push-arm Radial Projection Unit Tool-inserts and Ablation and Angioplasty-incapable Radial Discharge Barrel-assembly Muzzle-heads, among others can be used to like effect.

Such a combination constitutes a bipartite or duplex ablation or ablation and angioplasty-capable barrel-assembly, in which the apportionment of side-looking tool lift-shafts, or radial projection units, as between the muzzle-head and radial projection catheter vary inversely within the sum total for the two as a unit. Thus, at one extreme, the muzzle-head might include so large a number of radial projection units as never to require supplementation by ensheathment within a radial projection catheter, while at the opposite extreme, the muzzle-head includes no radial projection units, so that any must be obtained through ensheathment. A radial projection catheter at this level of sufficiency can perform an ablation or an angioplasty as an independent device; however, it is not a barrel-assembly and cannot implant miniballs.

To minimize hindrance in steering, and tracking, the unsheathed component of a bipartite or duplex barrel-assembly is usually first positioned at the treatment site, after which the matching radial projection cathetetic component is slid over the barrel-catheter using it as a guide wire to abut against the rear of the muzzle-head. The radial projection catheter can then be withdrawn and replaced with the same or another sheath without moving the muzzle-head. Unless the radial projection catheter is of the through-bore or combination-form type, it must be withdrawn to allow a barrel-assembly to be introduced for initiating stenting discharge.

By contrast, whether an ablation or an ablation and angioplasty-capable barrel-assembly achieves this capability with radial projection units built into its muzzle-head or by acquiring these through the addition of a radial projection catheter, it need not be withdrawn from the ductus and reinserted through the introducer sheath before the muzzle-head at its distal end is passed transluminally to the segment to be treated to initiate stenting implantation. Radial projection catheters are addressed below in the section of like title. Following treatment with the ablation or ablation and angioplasty-capable barrel-assembly while unconnected to the airgun, the free (proximal, extracorporeal) end of an barrel-assembly is inserted into the barrel of the airgun.

Such a barrel-assembly to which is added a through-and-through passageway or central channel along the central axis and an extracorporeal end- or side-socket through which to pass a cable from a control console is referred to as a through-bore or combination-form barrel-assembly. Such a barrel-assembly allows the insertion through the central bore of a fiberoptic or video endoscope, rotational atherectomy burr, or excimer laser, for example. Even though a negligible accumulation of debris generally exerts little practical effect on miniball exit velocity, the barrel-assembly must be configured to minimize the entry of debris through the exit ports during transluminal advancement.

To minimize the risk of hypoxia, gas embolism, traumatizing parectasia (overdistention, overstretching), and dissections, a barrel-assembly for use in the vascular tree must further incorporate internal gas pressure relief and other features to be described, platelet blockade used to prevent the formation of microthrombi at the sites of miniball entry. Venting the column of air in the barrel-tube or tubes also reduces resistance to miniball travel, especially when the barrel-assembly is inserted against the flow and discharged during the pulse, thereby allowing the use of an airgun that generates expulsive force less than would be necessary otherwise.

Transluminal movement to another site for implantation is usually by means of a stepper or 3-phase brushless synchronous iron core linear motor-driven precision machining linear positioning stage (linear stage, translation stage, linear table). Positional control also makes it possible to lay down tight formations of miniballs for the more uniform distribution of magnetic pull, and if the miniballs are coated, then a more even distribution and accurate targeting of the coating substances. Conventional vascular cryoplasty and thermoplasty consist of running chilled or heated fluid through an angioplasty balloon with the primary object of structurally degrading the plaque so that dissections are minimized and the dilatation forces exerted by the balloon meet with less resistance to produce a more uniform distention.

If sufficiently hot, the balloon probably does destroy some potentially embolizing debris that would have been discharged were a vulnerable or unstable plaque (see Maseri, A. and Fuster, V. 2003. "Is There a Vulnerable Plaque?," *Circulation* 107(16):2068-2071) to rupture; however, the plaque is mostly just crushed against the lumen wall (see, for example, Algowhary, M., Matsumura, A., Hashimoto, Y., and Isobe, M. 2006. "Poststenting Axial Redistribution of Atherosclerotic Plaque into the Reference Segments and Lumen Reduction at the Stent Edge: A Volumetric Intravascular Ultrasound Study," *International Heart Journal* 47(2): 159-171; *American Journal of Cardiology* 89(4):368-371; Hong, M. K., Park, S. W., Lee, C. W., Kim, Y. H., Song J. M., and 4 others 2002. "Relation Between Residual Plaque Burden after Stenting and Six-month Angiographic Restenosis," Honda, Y., Yock, P. G., and Fitzgerald, P. J. 1999. "Impact of Residual Plaque Burden on Clinical Outcomes of Coronary Interventions," *Catheterization and Cardiovascular Interventions* 46(3):265-276; Alfonso, F., García, P., Pimentel, G., Hernández, R., Sabaté, M., Escaned, J., Bañuelos, C., Fernández, C., and Macaya, C. 2003. "Predictors and Implications of Residual Plaque Burden after Coronary Stenting: An Intravascular Ultrasound Study," *American Heart Journal* 145(2):254-261).

The failure to actually remove plaque not only impairs healing, exacerbates the disease, and promotes restenosis, but can result in the prolapse of residual tissue through the stent struts, as addressed below in the section entitled Basic Strengths and Weaknesses of Prior Art Stenting in Vascular, Tracheobronchial, Gastrointestinal, and Urological Interventions, among others. When the plaque and subjacent tissue are too hard to be smashed or reduced, the balloon accomplishes luminal dilation by tearing circumferential fibers. This is often the basis for the stretching injury which results in endothelial dysfunction and induces the intimal (endangial) and medial hypoplasia that ensue.

The means to be described removes plaque through cutting, abrasion, thermoplasty, cryoplasty, or any combination of these. Theremoplasty, for example, is routinely used to destroy potentially embolizing debris that might be discharged by the rupture of erodable fibrous, vulnerable, or unstable plaque by the passing muzzle-head. In Barrel-assemblies which incorporate fluidically operated radial projection units, addressed below in the section entitled Radial Projection Units, cryoplasty, believed to retard intimal (internal lining, Bichat's tunic) hyperplasia, is also available. Where disease is extensive, thermoplasty is used as a precaution over the entire length of the artery, usually not as a preliminary procedure but just in advance of implant discharge.

When the application of any of these ablative or angioplasty means to include heat, cold, abrasion, and cutting or shaving is continuous over a significant length of the lumen, the speed of travel, or rate of transluminal advancement of the muzzle-head over the internal surface of the ductus, is set for the prescribed time of exposure for the diagnosis. Cryoplasty, for example, is performed at minus 10 degrees centigrade for 20 seconds. Executing a tightly controlled rate of travel, hence, time of exposure is usually entrusted to a variable speed linear positioning stage. Off-pump use in the coronaries and use in the carotids especially demands a muzzle-head that least interferes with perfusion. Despite the features incorporated into the muzzle-head to minimize obstruction summarized below in the section entitled Hypoxia and Ischemia-averting Elements, a muzzle-head of a diameter suitable for use in a peripheral artery of the same diameter would be too large.

At the same time, minimizing procedural duration and achieving uniformity of implant placement are all the more important in these arteries, making the use of multibarrel-tube barrel-assemblies, which must be larger in diameter, under automatic machine control desirable. Vasodilators can be used to reduce the limitation on gauge of the muzzle-head and minimize if not eliminate the need for extracorporeal oxygenation. The concurrent use of nonvasodilating (nonantgiotensive, nonvasotensive) inotropic medication to increase the force of the heart contraction without interfering with the vasodilation is additionally helpful. When the degree of dilation sought is greater, more extended in length, and more demanding in terms of speed, the medication is administered by infusion.

Otherwise, the muzzle-head can itself be used to deliver medication as it approaches, the rate of advancement adjusted to accommodate the medication response time. Vasospasm reflexive to the presence of the muzzle-head, for example, should it arise, is prevented through the site specific release of antispasmodic or spasmolytic drugs. Ordinarily through an open-ended service catheter to preserve use of the barrel-tube for miniball discharge or ballistic implantation, the muzzle-head could be used to deliver liver metabolism nondependent vasodilators highly localized to the treatment site, such as adenosine, nitrates (nitroglycerin, nitroprusside, isosorbide mono or dinitrate), mannitol, hydralazine hydrochloride, nicardipine, nesiritide, nimodipine, verapamil, milrinone, trimethaphan, fasudil, and colforsin daropate, as well as platelet blockade or heparin, for example.

Application thus can be accomplished in any of several ways, to include ejection by ejection tool-inserts, injection by injection tool-inserts, and ejection by open or injection by hypotube-ended service catheter syringes, all to be addressed. Prepositioned impasse-jackets whether used to prepare a segment of a ductus for discharge implantation in advance in the manner addressed in the sections below entitled Concept of the Impasse-jacket and Miniball and Ferrojluid-borne Particle-impassable jackets, or Impasse-jackets, do not interfere with the use of a barrel-assembly. With the availability in the form of impasse-jacket held miniballs of a counteractant or reversal, that is, neutralizing or scavenging agent, such as mannitol dehydrogenase or mannitol 2-dehydrogenase, the localized (nonsystemic, targeted) application of mannitol, for example, can be delivered at a high dose as localized that is systemically minute.

Delivered peripherally or otherwise distant from the coronary arteries, mannitol, for example, can be administered to patients with advanced coronary disease, if distant from the heart, to those with heart failure, if distant from the kidneys, to those with renal insufficiency, and if distant from the lungs, to those with pulmonary vascular congestion, (see, for example, *The Merck Manual of Diagnosis and Therapy*, 18th Edition, 2006, page 2578), while avoiding unwanted side-effects such as diarrhea (*Merck Manual*, pages 78 and 84), gastric upset (nausea, vomiting), diuresis, for which the dose of mannitol as a dehydrating agent and osmotic diuretic must be larger, headache, confusion, hyperglycemia, and allergic reactions, among others. Unlike a radially symmetrical balloon, the muzzle-head, which is contrast marked to assist in its orientation, can be used to treat radially asymmetrical, or eccentric, lesions in a discretionary manner provided these can be clearly seen.

Impasse-jackets can suspend drug carrier nanoparticles in a ferrofluid or medication miniballs, to include those comprising 'smart pills,' in the lumen that will release medication only when signaled or stimulated to do so from outside the body. The jacket is then reloaded as necessary. Self-reloading of the impasse-jacket, magnetized miniballs, stays, arrays thereof, patch-magnet, or magnet-jacket of a drug carrier nanoparticulate or miniballs outside the clinic to reach a level along the gastrointestinal tract is by ingestion, with a followup triggering substance administered likewise as needed. Magnetically susceptible nanoparticle-bound drugs that can be ingested to pass through the gut and liver and into the bloodstream are under development. Secondary triggering as needed or prescribed makes it possible for the patient to initiate the release of a prepositioned drug outside the clinic preferably by ingesting or otherwise injecting a triggering substance or solvent and/or by applying heat at the treatment site for example.

Delivery to the trachea and bronchi is by inhalation of the nanoparticulate-bound drug as a metered dose inhaler-delivered aerosol. Charging and triggering along the vascular tree are preferably by ingestion, or if necessary, by injection or subcutaneously implanted access portals (ports, porta-caths) or peripherally entered central catheters (*The Merck Manual of Diagnosis and Therapy*, page 1161), these latter also suited to allow direct access to urinogenital (urogenital, genitourinary) ductus. Recharging and triggering are addressed below in the sections entitled System Implant Magnetic Drug and Radiation Targeting and Cooperative Use of Impasse-jackets in Pairs and Gradient Arrays, among others.

Unlike the implantation of spherules (miniature balls, miniballs), stays, or implants in the form of tiny arcuate bands, are nonballistically inserted into the wall of the ductus from the outside by means of a special hand tool to be described. When the ductus to receive the implants is already exposed or can be accessed with trauma justified within the medical context, a hand tool is used to implant the stay or stays through an incision little more than microscopic in length. Existing means for delivering drugs ballistically are not endoluminal (see, for example, Kendall, M. A. 2010. "Needle-free Vaccine Injection," *Handbook of Experimental Pharmacology*(197):193-219; Liu, Y. 2007. "Impact Studies of High-speed Micro-particles Following Biolistic Delivery," *Institute of Electrical and Electronics Engineers Transactions on Biomedical Engineering.* 54(8):1507-1513; Kendall, M., Mitchell, T., and Wrighton-Smith, P. 2004. "Intradermal Ballistic Delivery of Micro-particles into Excised Human Skin for Pharmaceutical Applications," *Journal of Biomechanics* 37(11):1733-1741), which distinction is critical for the treatment of disease affecting any tubular structure (see, for example, Kendall, M., Mitchell, T., and Wrighton-Smith, P. 2004, Op cit.).

The terms ballistic or biolistic in relation to gene alteration and treatments with gene guns and the delivery of drugs through the skin are thus unrelated to the content herein. An extraluminal stent leaves the lumen free and clear of any foreign object and is substantially compliant with the functional changes in gauge of the ductus. It therefore less alters flow-through, does not contact, much less chronically irritate the lumen lining, and less interferes with subsidence in inflammation and healing. Avoiding the implantation of a foreign object within the lumen and interference with the expansion, contraction, and flexion of the ductus is critical for accommodating normal physiology while maintaining patency. The citation of drugs herein is for the purpose of suggesting applications related to the apparatus described and not an endorsement or recommendation.

Veterinary drugs are regulated by the Department of Agriculture Center for Veterinary Biologics, or the Food and Drug Administration Center for Veterinary Medicine, and may not undergo multiple extensive clinical trials; as is applied to drugs for use in man, drug testing results obtained with animals is tentative. While the propulsive force specified herein is supplied as in most airguns by pressurized gas, such as compressed air or carbon dioxide ($CO_2$) delivered from a cylinder (which may be referred to as a tank, canister, powerlet, pistolet, capsule, or cartridge), alternative propulsive means, such as a spring-piston or an internal air column that is pressurized by a hand pump as in pneumatic airguns could be similarly applied. Some stents can release medication as they disintegrate. Whether this effects a cure depends upon the lesion and the patient. With the exception that stents which release medication and/or radiation have the potential to effect a cure, to the extent they are mechanical scaffolds, stents are nosotropic or symptomatically corrective through mechanical means, not etiotropic or curative.

No claim beyond this is made for any of the means to be described. However, patency is always essential to sustain function and life, making the capability to do so with fewer sequelae over a long period important. Stenting does not supplant but complements concurrent medical management; the decision to insert a stent to maintain luminal patency in cases of bronchiectasis, for example, will depend upon the variable symptoms of specific patients. Moreover, noninvasive management cannot duplicate the remedial effect of a stent, is seldom any more able to effect a cure, and always carries the risk of side effects. The apparatus to be described targets medication at or into the lesion, minimizing the dose and promoting local uptake thus avoiding the circulation, and is able to apply various therapeutic treaments as well as introduce the intraductal component of an extraluminal stent.

While never used in extraluminal stents, magnets have been used intracorporeally to induce compression necrosis, anastomosis, and other purposes for decades and continues in use (see, for example, Jansen, A., Keeman, J. N., Davies, G. A., and Klopper, P. J. 1980. "Early Experiences with Magnetic Rings in Resection of the Distal Colon," *Netherlands Journal of Surgery* 32(1):20-27; Cope, C. 1995. "Creation of Compression Gastroenterostomy by Means of the Oral, Percutaneous, or Surgical Introduction of Magnets: Feasibility Study in Swine," *Journal of Vascular and Interventional Radiology* 6(4):539-545; Yamanouchi, E., Kawaguchi, H., Endo, I., and Arakawa, H., Yamaguchi, T., Sakuyama, K, et al. 1998. "A New Interventional Method: Magnetic Compression Anastomosis with Rare-earth Magnets," *Cardiovascular and Interventional Radiology* 21(Supplement1):S155; Okajima, H., Okajima, H., Kotera, A., Takeichi, T., Ueno, M., Ishiko, T., and 4 others 2005. "Magnet Compression Anastomosis for Bile Duct Stenosis after Duct-to-duct Biliary Reconstruction in Living Donor Liver Transplantation," *Liver Transplantation* 11(4):473-475; Kaidar-Person, O., Rosenthal, R. J., Wexner, S. D., Szomstein, S., and Person, B. 2008. "Compression Anastomosis: History and Clinical Considerations," *American Journal of Surgery* 195(6):818-826; Jamshidi, R., Stephenson, J. T., Clay, J. G., Pichakron, K. O., and Harrison, M. R. 2009. "Magnamosis: Magnetic Compression Anastomosis with Comparison to Suture and Staple Techniques," *Journal of Pediatric Surgery* 44(1):222-228; Jang, S. I., Kim, J. H., Won, J. Y., Lee, K. H., and 4 others 2011. "Magnetic Compression Anastomosis is Useful in Biliary Anastomotic Strictures after Living Donor Liver Transplantation," *Gastrointestinal Endoscopy* 74(5):1040-1048).

3. Terminology

'Proximal' and 'distal' are used in relation to the operator, not the treatment site. 'Vessel,' 'vas,' 'ductus,' and 'conduit' all denote tubular anatomical structures, but 'vessel' is generally understood and is used here to refer to blood vessels rather than to other kinds of vessels. Terms derived from 'vessel,' such as 'intravascular,' extravascular,' 'intravasated,' and 'extravasated' pertain to blood vessels. 'Ductus' is used to refer to any kind of tubular structure and not just a duct leading away from a gland, for example, and the terms 'intraductal' and 'extraductal' are used with respect to any type ductus. 'Miniball' as used herein refers to millimetric range spherules for implantation to treat disease with no relation to ammunition.

The term 'base-tube' denotes a platform for magnets; nonplatform jackets such as intrinsically susceptible to magnetic tractive force are not base-tubes but stent-jackets in themselves. Where greater tractive force is required to draw the susceptible matter into the wall of the ductus, either type jacket can be used. The context will make it plain whether use of the term 'flow reversal' pertains to a. Carotid angioplasty and stenting, addressed below in section VII2j(1) entitled Incorporation of Adscititious Capabilities into Barrel-assemblies, b. Aortic regurgitation on the diastoles due to aortic valve impairment, or c. Switching from outflow, ejection, or irrigation to inflow or aspiration in the use tool-inserts, addressed below in section VII2g(3)(e)(vi), entitled Fluid-operated Tool-inserts, to Include Ejector-irrigator-aspirators and Injectors.

Terms pertaining to detailed parts of components are presented in the respective section describing the component and not anticipated. The superior thoracic aperture is the thoracic inlet of the anatomist and thoracic outlet of the clinician. Reference herein to the thoracic inlet is to designate this axial level in a dog or other quadruped with tracheal collapse. The term 'propulsive force' applies to the momentum imparted to a miniball by the gas pressure that drives it forward through the barrel-assembly and to the force imparted to a bolus advanced through the digestive tract, the context making which meaning pertains clear. 'Thermoplastic' and 'thermoplasty' pertain to thermal angioplasty, not viscosity, hardness, or cosmetic surgery. Consistent therewith, while any tubular anatomical structure may be referred to as a vas or ductus, the term 'endovascular,' for example, because it is derived from 'vascular,' implies limitation to an arterial or a venous stent and is therefore avoided.

When used as an anatomical term, the plural for ductus is ductus (pronounced ducktoose, not "ducti")." An implant placed within the wall of a ductus is in the ductus but not within the lumen of the ductus, which distinction is here significant. 'Wider' is short for larger in diameter, and 'narrower' for smaller in diameter, gauge, or caliber. 'Hypoxia' is used to denote an insufficiency of oxygen due to obstruction whether caused by intrinsic endoluminal deformation or by apparatus in the airway or the bloodstream, whereas 'ischemia' refers only to obstruction of the blood supply.

As used herein, the term 'implant' denotes solid objects or pre-solid infusions or injections that aggregate together and cure to become solid or semisolid objects introduced and/or positioned using means set forth herein. Such placement is either within the wall surrounding a lumen or other tissue, or is in surrounding, or periductal, relation to the native tubular anatomical structure or condit, as is the case with stent- and impasse-jackets. Unless absorbable, implants are to remain inside the body following placement. Nonperiductal, or intralmural, implants consist of medication and/or magnetically susceptible matter in the relative proportion optimal for the site of treatment. In this context, optimization comprises structural correction, medical remediation, and the inclusion of only so much magnetically susceptible content as is necessary to assure implant retractability or recoverability should the need arise.

Not referred to as 'implants' are tools used to place implants, to include stay insertion devices, barrel-assemblies, and combination form barrel-assemblies. The lack of prior art for methods and means of treatment directed toward the placement of implants within the walls of ductus is reflected in an inadequacy of established terms. 'Endoluminal,' indicates that the referent (usually a stent) is not simply intraductal but within the lumen; when dealing with extraluminal stents, which include a collective or distributed intraductal component which is extraluminal as situated within the lumen wall but otherwise external to the ductus as consisting of a circumvascular component, the term 'endoluminal' serves to distinguish prior art stents from the extraluminal stents described herein.

Except in using the standard term 'intraductal brachytherapy,' intraductar is used to mean within the wall of the ductus, not passed through its lumen. Because the recognized terms 'intraductal,' 'intratubal,' 'intraluminal,' or applying the term more generally than to the subarachnoid or subdural spaces, 'intrathecal,' do not distinguish 'within a ductus from 'within the lumen of the ductus, here the more recently recognized (included in medical dictionaries) but long commonly used and immediately understood terms 'endoluminal' and 'extraluminal' are used. The term 'intraluminal' had already been accepted, but its complement, 'extraluminal,' had not.

The term 'endoluminal' is not widely recognized as combining a Greek prefix with a Latin stem word or root, but the term 'endovascular (endoluminal vascular),' of like composition, has more recently been accepted through common use as necessary and obvious in meaning. Suture loops, or suture eyelets, are small optional handles integral with the stent-jacket for passing through suture in order to stabilize the stent-jacket in position by attachment to neighboring tissue in locations where pronounced vasotonic, peristaltic, or bodily movement might otherwise cause the stent-jacket to become displaced, or migrate. End-ties are suture, usually prefastened to the stent-jacket, either with rivets or through suture loops or suture eyelets for wrapping about the ends of a stent-jacket to the substrate ductus beyond the end margins to fix the stent-jacket in position.

'Endomural' and 'endoparietal' likewise combine a Greek prefix with Latin suffixes, and are not conventionally applied to ductus, so that an implant within the wall of a ductus is left to be 'intramural' or 'intraparietal,' the conventional pertinence to a wall surrounding a cavity forgone. The recognized term 'endoprosthesis' and unrecognized term 'endostent' as a contraction for endovascular or endoluminal, stent to denote a conventional or intraluminal stent, can be used for brevity; however, since an extraluminal stent of the kind to be described herein is not entirely extraductal, the contractions 'extrastent' and 'exostent' are rejected as misleading in addition to lacking acceptance.

An 'extraluminal' stent consists of subadventitial (perimedial) or medial, hence, intraductal but extraluminal spherule implants, and an extraductal, specifically circumductal or periductal, a fortiori, extraluminal, stent-jacket, magnet-jacket (magnet-wrap), or otherwise, subcutaneous or suprapleural clasp-magnets. The term "external stent" as previously used applies to various cuffs and sheaths that in application, structure, and function are fundamentally different from the extraluminal stents to be described herein. A ductus is effectively 'stented' whether the extraluminal intraductal component consists of ferromagnetic miniballs, stays, a clasp-jacket, or a combination of these, and whether the extraductal component consists of a periductal (circumductal) stent-jacket, more remotely placed patch-magnets, magnet-wraps, or a combination of these.

'Abluminar' means 'more distant from the ductus or its central axis. Inside the lumen, 'abluminal' means farther from the longitudinal central axis, hence, closer to the lumen wall, whereas outside the ductus, 'abluminal' means farther from the lumen wall. 'Adluminal' 'means the opposite— closer to the ductus or to its central axis; outside the ductus, 'adluminal' means closer to the lumen wall or outer tunic, and within the lumen, away from the lumen wall or inner tunic and toward the lumen axis. 'Luminal' means of or about the lumen; 'adluminal,' never "luminal" used herein to denote closer to the central axis of the lumen. These terms are purely directional, hence, nonspecific as to the layer, depth, or distance.

The terms 'circumluminal' and 'periluminal' are neither recognized nor clear in distinguishing whether the surrounding is of or along the internal surface of the lumen, within the wall about the lumen, or about the ductus as a whole. The term 'subadventitial' as used herein denotes the depth into the lumen wall at which the material of the wall becomes the peripheral connective tissue comprised of the external elastic lamina (lamina elastica externa) just outside of the smooth muscle and inside the tunica adventitia or outer fibrous jacket. 'Ferromagnetic' denotes drawn to a magnet, or magnetizable. The term 'magnetized' denotes intrinsic magnetization or provided with magnets.

A barrel-assembly uses a narrow pliant catheter to extend the muzzle of an airgun forward or distad allowing transluminal passage and endoluminal discharge. Since the effective muzzle is no longer that of the airgun, the term 'muzzle-head' is used to denote the displaced or effective muzzle, 'exit port' or 'exit-hole' to denote the aperture of projectile release, and 'exit velocity' used in lieu of muzzle velocity. The term 'bore' is not literally applicable to the internal diameter of a barrel-tube, which is an extrusion, but is nevertheless useful to denote the lumen or diameter (gauge, caliber) thereof 'Port' and 'portal' refer to the entry incision or wound, not a sleeve inserted to expedite passage therethrough. While no guidewire is used, the terms 'steerability' and 'trackability' are used to denote the same attributes in relation to a barrel-assembly or radial projection catheter.

'Torqueability' denotes the resistance of a catheter to twisting or helical deformation when rotated at the manipulated or proximal end. Parenthetically, in the present context, when the need for steerability outweighs the need for torqueability, the pliancy required results in a loss of torqueability, necessitating the incorporation of a hard-wire remotely controlled electrical motor to rotate the distal muzzle-head of the barrel-assembly. 'Injectant' is used to refer to any substance to be injected—not just an allergen. The term 'orthosis' suggestive of artificial limbs, the term 'prosthesis' is used to denote a device that does not necessarily replace, but rather augments or supports a part that failed due to disease, such use conventional. 'Thermal-window' and 'heat-window' denote a temperature changing window whether used for heating or chilling.

Most often the term 'heat-window' will refer to a heat conduction plate overlying an electrical winding used as the heat source. The term 'ablation' as conventionally used is not limited to the removal of tissue by means of cutting, and here, consistent therewith, denotes the destruction of tissue protrusive into a lumen whether by means of thermal (thermocautery) or cryogenic cautery (cryocautery) or by cutting (shaving) or abrasive action. The term "barrel" as denoting a cylindrical form or cylindrically formed part of a larger structure is in standard use relative to guns, eyelets, rivets, syringes, springs, and plating equipment, all directly involved herein, the context making it clear which of these meanings is intended.

Most often the term 'barrel' will pertain to that of a commericial airgun or the primary vertical member in a control syringe-type stay insertion tool. Exceptionally, the 'barrel' in an ejection or injection tool-insert refers to function as a piston or plunger receiving component, regardless of cross section, which can be other than circular. The term 'barrel-catheter' as used herein, if not unique, is believed to have little prior use, but the term 'barrel-assembly' is commonly used with respect to firearms, extruders, hydraulic pistons, microscopes, syringes, door curtain supports, and many other devices not related to the apparatus to be described.

Depending upon the context, 'clip' denotes a magazine clip used to load spherule implants in an interventional airgun for discharge, strips of stays for loading into and sequential ejection from a stay insertion tool in a manner analogous to office staples, or spring clips for fastening attachments alongside a stay insertion tool, all to be described. Even though clasp-magnets and clasp-wraps attach to tissue with clasps or prongs, these are not referred to as 'clips.' The term 'magazine' used alone likewise refers to a container for a load of projectible implants queued for discharge from an airgun or a stay insertion tool. The term 'eccentric' with respect to vascular lesions denotes radially asymmetrical, and with respect to the axle in a miniature fluid damper-valve to be described, off-center.

'Impasse-jacket' denotes an impasse-jacket with any associated dummy collars or outriggers. An 'airgun' or 'air gun' discharges implants as projectiles; a vortex tube-based cooling and heating device is referred to by the standard industrial term 'cold air gun.' 'Applicator' herein refers to a syringe, such as one used to dispense a surgical cement or tissue sealant as a whole and not just the nozzle, outlet tube, or 'tip' thereof, nor a separate spatula or brush for spreading a cement, or to a tool-insert type syringe, as will be described. The traditional meaning of 'percutaneous' as passing through without breaking the skin (transcutaneous; transdermic; diadermic) is no longer restricted in meaning thus, the very term 'percutaneous transluminal coronary angioplasty' for procedures that require entry by incision and arteriotomy making the point.

The unrecognized terms 'permural' and 'perparial' are commonly used to refer to the walls of body cavities and organs but not the walls of ductus. 'Parietal' as it pertains, for example, to cells of the stomach lining, (parietal cells, acid cells, oxyntic cells) is used to refer to the lining of a ductus when an outpocketing of a cavity, such as the inside of the stomach, but not the vascular endothelium or intima. The term 'ductus-intramural' is used herein to denote a position within the wall about a lumen. Until changed by adjustment of the controller (indexer) or changing the step mode at the driver (amplifier), a stepper motor rotates by a consistent angle as would move or 'increment' a linear positioning table (linear positioning stage) by the equivalent constant linear distance, here along the lumen of a ductus.

To distinguish between these 'increments' as elementary rotatory steps set by the step-angle from the overall segment or distance along the lumen traversed as the sum of these elementary steps, the term 'step' is limited to the action of the stepper motor, and the term 'increment' applied to the transluminal segment traversed as the sum of these steps. The term 'torquer' is used to describe both a kind of electrical motor and knobs used to rotate catheters, the term 'cure' used for the setting time of an adhesive and the time to heal, the context making it clear which of these meanings is intended. The specification of a stepper motor as linear stage driver is based upon the prevalence of such application and not to be taken in a limiting sense. 'Atherectomy' denotes a form of angioplasty that unlike the compression of plaque by a balloon, cuts the plaque away.

Thermal and laser catheters actually remove (ablate, atherectomize) rather than merely crush plaque or effect luminal distention by tearing circumferential fibers, but cutting as suggested by the suffix -'ectomy' is uninvolved, so that these methods are usually referred to as forms of angioplasty. The angioplasty-capable barrel-assemblies and radial projection catheters to be described can eliminate plaque by different means, to include cutting action with radial projection unit tool-inserts, which constitutes a form of atherectomy literally understood, but also by thermal, cryogenic, or laser action, for example, which are more accurately referred to as types of angioplasty. Since the term 'angioplasty' is applied to atherectomy but the reverse is not true, the one term that covers both actions of a barrel-assembly used as an independent plaque-removal device is 'angioplasty,' prompting the term 'angioplasty-capable barrel-assembly' or 'angioplasty barrel-assembly.'

The term 'cavitation' in engineering denotes the generation of bubbles in a fluid medium, whereas in medical use, the same term denotes the formation of vacuities, vacuoles, or cavities whether normal or pathological. The term 'sweep,' as in 'side-sweeper,' is used to mean to pass over, to sweep past or across, whether with a hot gas, fluid medication, a shaving or an abrading head, only the last of these applying a brushing action and not necessarily using bristles. The term 'recovery' applied to electromagnets denotes applicability to retrieve dropped (intravasated, escaped) or extract mispositioned miniballs or stays, sparing all of 'recovery and extraction miniball electromagnet assembly.'

Whereas the electronic components in positional control systems were once separate and distinct, miniaturization has led to miniaturized combinations of these that obscure the functional distinctness of each component. These include a manually operated positional command (set point, zero point) input device, or control, such as a digital encoder or an analogue (resolver or synchro), a programmed motion instruction director or controller, a differential (comparator), servomotor (actuator), machine table, shaft, or other driven member, and output or positional difference (displacement) measuring device, usually of the same kind as the command input device, that provides the signal fed back to the differential.

This combination and integration has resulted in much confused terminology, such as use of the term 'amplifier,' normally synonymous with 'driver,' to denote an apparatus that actually includes the control or controller. Herein, the terms 'controller' or 'servocontroller' denote the set point positional director or controller, and the other terms are specific, so that 'amplifier' or 'servoamplifier' denotes the amplifier, 'differential' the differential, and so on. The simplest barrel-assemblies consist of only a ballistic component. More advanced barrel-assemblies add components inside of, that is, centrally or medially to, and/or outside of, that is, peripherally to, the ballistic component. The ballistic component consists of the barrel-tube or tubes, one or more recovery tractive electromagnets, and in barrel-assemblies for use in the bloodstream, gas pressure relief or diversion channels.

In a radial projection catheter, which specifically lacks a ballistic component, there are only inner and outer components. When more than one barrel-tube is present, the gas pressure diversion channel is usually shared by and positioned between or amid the barrel-tubes. While central and referred to as the central canal, it is not a central component but rather part of the ballistic component. To allow for the incorporation of a central component, the gas pressure diversion channel is divided as to be respective of each barrel-tube, displacing these ballistic components peripherally, as seen in an edge-discharge barrel-assembly. When displaced peripherally thus, a single central gas pressure diversion channel, or central canal, is no longer present.

A central component is a commercial device, such as a laser or atherectomy cutting tool, to which is applied the least modification that will allow it to be incorporated into the ballistic catheter, or barrel-assembly. A barrel-asembly that includes a central channel for a permanent central component or interchageable central components is a combination-form barrel-assembly, the central component occupying the central channel, passage, or passageway. Combination-form barrel-assemblies include central and ballistic components, and unless omitted to allow additional cross sectional area for these, a peripheral component. Thus, only a combination-form barrel-assembly can include a central, and therewith, all three components. A peripheral component consists of radial projection units, which belong to one or more circuits electrical and/or fluidic.

The term 'fluidic' herein is applied not only to a fluid circuit but to components that are inserted into a fluid line. When the ballistic component is omitted, the apparatus is not a barrel-assembly but a specialized radial projection catheter and the terms central, ballistic, and peripheral do not apply. Structurally isolated from other components, such is no longer a component or peripheral. However, if a central component in the form of a laser, thrombectomizer, or atherectomizer, for example is incorporated into a radial projection catheter, central and peripheral components are included in a catheteric device which is not a barrel-assembly. 'Stereotactic' or 'stereotaxic' denotes the precise positioning of a removal path for a miniball to be relocated or removed through the use of three-dimensional coordinates, suitable imaging machine, contrast dye, and a powerful extracorporeal electromagnet.

Such extended use to parts of the body other than the brain appears in use of the term 'stereotactic mammography,' for example. A ballistic catheter includes only the ballistic component, making terms pertaining to relative position among components inapplicable. A ballistic catheter can be a simple pipe or a radial discharge barrel-assembly, which consists of a barrel-tube or tubes jacketed about to avoid injury to narrow ductus. Simple pipes and radial discharge barrel-assemblies with a single barrel-tube are monobarrels. Radial discharge monobarrels and multibarrels for use in the bloodstream include one or more gas pressure diversion channels. Since the jacket and gas diversion channels are parts of the ballistic component, a basic radial discharge barrel-assembly, even when a multibarrel, includes only a ballistic component.

'Gas-operated' in the present context denotes only that pressurized gas rather than a spring mechanism, for example, is used to propel the miniball implants, and not that the exhaust gas of the preceding discharge is used to chamber the next miniball as in the blowback operation of a firearm. Use of the term 'discharge' to denote actions so different as the sudden expulsion of miniballs and the relatively quiescent release of substances from syringes accords with convention. The terms 'aspiration' and 'microaspiration' as used herein denote and are consistent with the processes used to study embryos, for example, and not factors in pulmonary or airway disease.

Miniball-impassable jackets, or magnetized impasse-jackets, are singular or simple; simple-extended or braced when effectively elongated for positional stability through the addition of unmagnetized dummy-collars fastened by rigid bridging arms at either or both ends; compound when two magnetized jackets are included, or chained when including more than two, such latter triple, quadruple, and so on. Since the addition of dummy-collars imparts both stabilizing elongation and multipartedness, braced jackets are technically compound and compound jackets 'braced;' however, it being superfluous, compound impasse-jackets are not referred to as braced nor braced jackets as compound.

'Chain' jackets refers to impasse-jackets that include more than two dummy-collars and 'compound' jackets that include two or more constituent jackets. 'Composite' or 'mixed' refers to compound or chain jackets in which one or more of the constituent jackets is used to trap any passing miniball, that is, as a 'trap-jacket,' while one or more is used to retain a radiation or drug-releasing miniball or miniballs at a certain level in the lumen as a 'holding jacket.' 'Gastrointestinal' as used herein refers to the entire digestive tract inferior to the cricoid cartilage, and not just the stomach and intestines as the literal meaning would suggest.

4. Concept of the Ductus-Intramural Implant

The four methods for placing magnetically susceptible implants within the wall surrounding the lumen of a tubular anatomical structure (conduit, ductus, vas, vessel) are specified below in section XXII, entitled Glossary of Terms. Clotting, problem bleeding following the administration of anticlotting drugs, and accidental intraysation or the entry of a miniball into the circulation are addressed in several sections. Provided the protective measures indicated are employed, these potential deterrents will be kept to a minimum if not eliminated and should pose no greater hazard than do existing standard of care measures.

Miniballs and stays can be placed in a preliminary procedure and allowed to become integrated into, that is, infiltrated or ingrown by and adherent to the surrounding tissue; over an interval, the use of tissue binding agents and cellular proliferation-accelerating substances applied when the need for stenting is urgent. Since stays used to stent are introduced through the same small access portal (keyhole incision, laparascopic entry wound) as is the stent-jacket, to place both during a single procedure is preferred. When necessary, however, the incision is left to heal by tertiary intention or delayed primary closure, thus preserving access without the need for reincision to introduce the stent-jacket at a later date.

Local subcutaneous injection of methylprednisolone acetate (Depo-Medrol® Pfizer) synthetic glucocorticosteroid can be used to further retard union, oral retinoids (Wicke, C., Halliday, B., Allen, D., Roche, N. S., Scheuenstuhl, H., Spencer, M. M., Roberts, A. B., and Hunt, T. K. 2000. "Effects of Steroids and Retinoids on Wound Healing," *Archives of Surgery* 135(11):1265-1270) and/or possibly the infusion of IGF-I into the wound chamber (Suh, D. Y., Hunt, T. K., and Spencer, E. M. 1992. "Insulin-like Growth Factor-I Reverses the Impairment of Wound Healing Induced by Corticosteroids in Rats," *Endocrinology* 131(5): 2399-2403) used to reverse the effect if necessary. Properly used and disinfected, the risk of infection is slight even if months pass until the stent-jacket is inserted.

4a. Tissue Acceptance of Ductus-Intramural Implants

4a(1). Significance of Sterile Antixenic Immune Tissue Reaction

An adverse or allergic tissue reaction that is not temporary will result in implantation failure, making materials testing critical. Ductus-intramural implants include miniballs and stays. The immune response to sterile implants is not confined to individual hypersensitivity or allergic reactions to certain proteins but can occur upon introduction of any implant into the body as foreign (see, for example, Malik, A. F., Hogue, R., Ouyang, X., Ghani, A., Hong, E., and 8 others 2011. "Inflammasome Components Asc and Caspase-1 Mediate Biomaterial-induced Inflammation and Foreign Body Response," *Proceeding of the National Academy of Sciences of the United States of America* 108(50): 20095-20100; Anderson, J. M., Rodriguez, A., and Chang, D. T. 2008. "Foreign Body Reaction to Biomaterials," *Seminars in Immunology* 20(2):86-100; Wilson, C. J., Clegg, R. E., Leavesley, D. I., and Pearcy, M. J. 2005. "Mediation of Biomaterial-cell Interactions by Adsorbed Proteins: A Review," *Tissue Engineering* 11(1-2):1-18; Hu, W-J., Eaton, J. W., Ugarova, T. P., and Tang, L. 2001. "Molecular Basis of Biomaterial-mediated Foreign Body Reactions," *Blood* 98(4):1231-1238; Kao, W. J., Lee, D., Schense, J. C., and Hubbell, J. A. 2001. Fibronectin Modulates Macrophage Adhesion and FBGC Formation: The Role of RGD, PHSRN, and PRRARV Domains," *Journal of Biomedical Materials Research* 55(1):79-88; Jenney, C. R. and Anderson, J. M. 2000. "Adsorbed Serum Proteins Responsible for Surface Dependent Human Macrophage Behavior," *Journal of Biomedical Materials Research* 49(4):435-447; van der Giessen, W. J., Lincoff, A. M., Schwartz, R. S., van Beusekom, H. M., Serruys, P. W., Holmes, D. R. Jr., Ellis, S. G., and Topol, E. J. 1996. "Marked Inflammatory Sequelae to Implantation of Biodegradable and Nonbiodegradable Polymers in Porcine Coronary Arteries," *Circulation* 94(7): 1690-1697; Tang, L. and Eaton, J. W. 1995. "Inflammatory Responses to Biomaterials," *American Journal of Clinical Pathology* 103(4):466-471).

Immune system macrophage attack of implanted polyurethanes in nonductus-intramural implants such as base-tubes and the linings thereof is inhibited by means addressed below in the sections below entitled Internal Environment-resistant Base-tube Polymers, Metals, and Combinations Thereof and Materials Suitable for Rebound-directing Double-wedge Linings. For medication implants that will be dissipated or assimilated through dissolution, enzymatic action, and sometimes hydrolysis and not subject to tractive force except when any must be recovered, tissue reactions are usually temporary and of negligible consequence. For stenting stays, which will be subjected to mild tractive force, where a treatment unrelated weakening condition following insertion is anticipated, the stays are coated with a tissue hardening and bonding agent, wetted with an adverse tissue reaction counteractant, and time time allowed for tissue integration until placement of the stent-jacket in a second procedure.

Counteractants are addressed below in the section entitled Tissue Reaction Ameliorative Measures. Various means for warming the site to accelerate the release of stay contents and uptake are addressed herein, and keeping the site warm should accelerate healing and tissue acceptance. The interval between placement of the stays and placement of the stent-jacket must be sufficient to allow tissue integration and not just acceptance and healing. Unless deterred, a foreign body reaction to a nonabsorbable implant can be acute and chronic, resulting in implant failure and harm to the patient. Stenting is but one application for miniballs, which have multiple drug, radiation, and other therapeutic agent-delivery applications that may or may not include stenting.

All ductus-intramural implants contain sufficient ferromagnetic content to allow retrieval should any be dropped, mispositioned, or require emergency recovery. Miniballs used for magnetic drug-targeting and/or to stent generally require more magnetically susceptible content. While it should seldom prove necessary, if the mass of lanthanoid needed to achieve the magnetic susceptibility required were to demand miniballs too large for the application, then any other space-taking agent coatings to be delivered in other miniballs or would be introduced not as outer layers but rather through endoluminal injection by tool-inserts, as addressed below in the section entitled Radial Projection Unit Tool-inserts, a coating of protein solder being an exception. Not subsumed by stenting, implantation and miniballs should be considered as capable of supporting stenting as but one application therefor.

Prepositioning of the stent-jacket, addressed below in the section entitled Circumstances Recommending the Use of a Shield-jacket or Preplacement of the Stent-jacket, usually restricted to the use of wide stays with greater adherent surface than miniballs in any event, will be limited to wide stays where healing time is extended and it is sought to avoid the long term systemic administration of resolvent (anti-inflammatory) medication. A coating containing microspheres of time-released dexamethasone, for example, to defer a foreign body reaction is valuable in allowing an interval for recovery from the immediate trauma associated with insertion; however, a coating of implant fibrinogin adsorption-averting serum, albumin, or hypofibrinogenemic plasma can ameliorate if not eliminate such a reaction (Hu, W-J., Eaton, J. W., Ugarova, T. P., and Tang, L. 2001. "Molecular Basis of Biomaterial-mediated Foreign Body Reactions," *Blood* 98(4):1231-1238).

An additional measure for deterring if not eliminating a detrimental reaction, surface modification, is applicable to the permanent outer surface of miniballs to serve as the intravascular component of a magnetic stent even when overlain by an absorbable layer or layers (Nair, A., Zou, L., Bhattacharyya, D., Timmons, R. B., Tang, L. 2008. "Species and Density of Implant Surface Chemistry Affect the Extent of Foreign Body Reactions," *Langmuir* 24(5):2015-2024; Anderson, J. M. and Jones, J. A. 2007. "Phenotypic Dichotomies in the Foreign Body Reaction," *Biomaterials* 28(34): 5114-5120), perhaps the simplest being polishing (De Scheerder, I., Verbeken, E., and Van Humbeeck, J. 1998. "Metallic Surface Modification," *Seminars in Interventional Cardiology* 3(3-4):139-144).

The need to further defer the onset of a foreign body reaction with systemic medication will depend upon the risk of stent failure due to such a reaction; integration of the sterile intraductal implants should allow a gradual toughening of the tissue between the implant and the magnet (references at the section entitled Stent-jacket Expansion Inserts), whereas an application of excessive tractive force while the tissue remains unaccepting of the implant increases the risk of pull-through or delamination.

4a(2). Duration, Extent, and Outcome of Sterile Tissue Reaction

The duration, extent, and outcome of tissue reaction must be considered over the range of variability for different individuals, tissues, and pathology for implants with a surface of bare metal, a protein solder doped onto a polymer scaffold, the same impregnated with any of many different types of medication in any of a number of different particulate conformations or combinations thereof, and any of the foregoing with an outer coating of a given surgical cement. Depending upon the specific application, the impact upon the implants and any coatings of the tissue response and internal environment over the long term must be considered (see, for example, Kirkpatrick, C. J., Krump-Konvalinkova, V., Unger, R. E., Bittinger, F., Otto, M., and Peters, K. 2002. "Tissue Response and Biomaterial Integration: The Efficacy of in Vitro Methods," *Biomolecular Engineering* 19(2-6): 211-217).

Miniballs and stays that emit radiation can also be prepared, for example, by ion surface engineering (see, for example, Fortin, M. A., Paynter, R. W., Sarkissian, A., and Stansfield, B. L. 2006. "Radioactive Sputter Cathodes for 32P Plasma-based Ion Implantation," *Applied Radiation and Isotopes* 64(5):556-562). Implants that emit radiation superimpose upon the foregong additional variables consisting of the numerous differences among individuals in the reaction of different tissues to radiation (see, for example, Li, X. A., O'Neill, M., and Suntharalingam, M. 2005. "Improving Patient-specific Dosimetry for Intravascular Brachytherapy," *Brachytherapy* 4(4):291-297; Bentzen, S. M. and Overgaard, J. 1994. "Patient-to-Patient Variability in the Expression of Radiation-Induced Normal Tissue Injury." *Seminars in Radiation Oncology* 4(2):68-80). Variables arise when the radiation responds to carcinoma (see, for example, Andreassen, C. N. and Alsner, J. 2009. "Genetic Variants and Normal Tissue Toxicity after Radiotherapy: A Systematic Review," *Radiotherapy and Oncology* 92(3):299-309).

Predictive capability for individual reaction differences not sufficiently developed (see, for example, Bentzen, S. M., Parliament, M., Deasy, J. O., Dicker, A., Curran, W. J., Williams, J. P., and Rosenstein, B. S. 2010. "Biomarkers and Surrogate Endpoints for Normal-Tissue Effects of Radiation Therapy: The Importance of Dose-volume Effects," *International Journal of Radiation Oncology, Biology, and Physics* 76(3 Supplement):S145-150; Popanda, O., Marquardt, J. U., Chang-Claude, J., and Schmezer, P. 2009. "Genetic Variation in Normal Tissue Toxicity Induced by Ionizing Radiation," *Mutation Research* 667(1-2):58-69; Williams, J. R., Zhang, Y., Zhou, H., Russell, J., Gridley, D. S., Koch, C. J., and Little J. B. 2008. "Genotype-dependent Radiosensitivity: Clonogenic Survival, Apoptosis and Cell-cycle Redistribution," *International Journal of Radiation Oncology, Biology, and Physics* 84(2):151-164; Williams, J. R., Zhang, Y., Zhou, H., Gridley, D. S., Koch, C. J., Slater, J. M., and Little J. B. 2008. "Overview of Radiosensitivity of Human Tumor Cells to Low-dose-rate Irradiation.," *International Journal of Radiation Oncology, Biology, and Physics* 72(3): 909-917), whenever possible, preliminary testing should be done using long established methods.

In empirical pretesting, a miniball of the kind contemplated for use can also be implanted in superficial skeletal muscle or in the submandibular salivary gland, which relatively superficial, includes much smooth muscle tissue. The internal anal spincter provides superficial smooth muscle of sufficient thickness and continuity for testing but is adversely located from the standpoint of risking infection. The inclusion of superparamagnetic magnetite or maghemite nanoparticles or finely grained powder allows quick retrieval of the test miniball. For testing, miniballs of identical composition as the stays actually proposed are used (Sigler, M., Paul, T., and Grabitz, R. G. 2005. "Biocompatibility Screening in Cardiovascular Implants," *Zeitschrift für Kardiologie* 94(6):383-391).

4a(3). Tissue Reaction Ameliorative Measures

Substances incorporated into implants or the coatings thereof may be distinguished as either therapeutic or as intended to counteract an adverse tissue response evoked by the implant itself. Since the outer surface of each implant can consist of bare metal or layers and an outer coating of substances that are different and numerous, the duration for tissue subsidence and accommodation or acceptance and integration will be variable. While controlled release from the implants can extend the term over which dexamethasone, for example, can continue to be delivered, eventual exhaustion may require systemic administration (see, for example, Vacanti, N. M., Cheng, H., Hill, P. S., Guerreiro, J. D., Dang, T. T., and 5 others 2012. "Localized Delivery of Dexamethasone from Electrospun Fibers Reduces the Foreign Body Response," *Biomacromolecules* 13(10):3031-3038; Bhardwaj, U., Sura, R., Papadimitrakopoulos, F., and Burgess, D. J. 2010. "PLGA/PVA Hydrogel Composites for Long-term Inflammation Control Following S. C. [Subcutaneous] implantation," *International Journal of Pharmaceutics* 384(1-2):78-86; Patil, S. D., Papadmitrakopoulos, F., and Burgess, D. J. 2007. "Concurrent Delivery of Dexamethasone and VEGF for Localized Inflammation Control and Angiogenesis," *Journal of Controlled Release* 117(1):68-79; Patil, S. D., Papadimitrakopoulos, F., and Burgess, D. J. 2004. "Dexamethasone-loaded Poly(lactic-co-glycolic) Acid Microspheres/Poly(vinyl alcohol) Hydrogel Composite Coatings for Inflammation Control," *Diabetes Technology and Therpeutics* 6(6): 887-897).

However, the implant itself or nearby magnetized miniballs, stays, impasse-jackets, magnet-wraps, and patch-magnets, for example, can attract a magnetically susceptible drug carrier bound nanoparticlate, for example, that incorporates any of numerous adverse tissue response counteractants from the passing blood or other luminal contents for concentration at the area required, as addressed below in the sections entitled Concept of the Impasse-jacket and Cooperative Use of Impasse-jackets in Pairs and Gradient Arrays, among others. More specifically, strongly magnetized implants, such as magnet-wraps generally and miniballs, stays, and impasse-jackets positioned to attract drug carrier binding nanoparticles will attract such a counteractant whether administered separately from or as cobound with a primary agent, whereas stent-jackets, which must be less strongly magnetized to avoid delamination and pull-through are initially coated with the agent and supplemented at the sides with more strongly magnetized miniballs or stays for this purpose.

When the ductus-intramural or intravascular component of the extraluminal stent consists of miniballs, the outriggers are most easily placed at the start and end of implantation discharge; when stays, the more strongly magnetized stays are placed at the distal and proximal sides of the other stays. When a preparatory angioplasty or ablation can be avoided, the use of stays exclusively allows avoiding the lumen entirely; however, if miniball implantation follows a transluminal step, then stays are just as easily placed to either side of the stent-jacket when it is introduced. Broad stays afford a volume that allows these to be coated with other reaction countering and other biological and/or nonbiological pharmaceuticals. The outer surface of the implants will often require a coating that incorporates multiple substances, typically, one to avert inter or intratunical delamination, another infection, and yet another to moderate any adverse tissue reaction.

One solution is to incorporate substances that pure or admixed, will not break down when one constituent, such as an outer coating of a solid protein solder formulated to flow or denature at a low temperature, still has a relatively high melting point (see Bogni, S., Stumpp, O., Reinert, M., and Frenz, M. 2010. "Thermal Model for Optimization of Vascular Laser Tissue Soldering," *Journal of Biophotonics* 3(5-6):284-295). Current solders into which other substances have been blended may still impose the risk of injury when used to bond arteries (Bregy, A., Bogni, S., Bernau, Vajtai, I., and 6 others 2008. "Solder Doped Polycaprolactone Scaffold Enables Reproducible Laser Tissue Soldering," *Lasers in Surgery and Medicine* 40(10):716-725). Protein solders usually consist of bovine serum albumin containing a dye to enhance laser absorption at the wavelength employed (see Maitz, P. K. M., Trickett, R. I. Tos, P. Lanzetta, M. Owen, E. R., Dekker, P. Dawes, J. M., and Pipet, J. A. 2000. ""Tissue Repairs Using a Biodegradeable Laser-activated Solid Protein Solder," *IEEE Lasers and Electro-Optics Conference Proceedings*, pages 446-447; Maitz, P. K., Trickett, R. I., Dekker, P., Tos, P., Dawes, J. M., Piper, J. A., Lanzetta, M., and Owen, E. R. 1999. "Sutureless Microvascular Anastomoses by a Biodegradable Laser-activated Solid Protein Solder," *Plastic and Reconstructive Surgery* 104(6):1726-1731).

Any proteinaceous material that thermally denatures upon heating can be used as a soldering agent, to include any serum protein, such as albumin, fibronectin, Von Willebrand factor, vitronectin, or any mixture of proteins or peptides (Gregory, K. W. 1998. "Method of Producing Biomaterials," Patent WO/1998/036707). Any or all of these materials can evoke an adverse tissue reaction. For cohesion and pliability, the proteinaceous material is applied or doped onto a synthetic polymer such as glycolic (alpha-hydroxyacetic) acid as a scaffold (backing, basement layer). Such scaffolding will usually contain alpha-hydroxy polyesters (see, for example, Andrade, M. G. S., Weissman, R., and Reis, S. R. A. 2006. "Tissue Reaction and Surface Morphology of Absorbable Sutures after in Vivo Exposure," *Journal of Materials Science: Materials in Medicine* 17(10):949-961 Bostman, O., Partio E., Hirvensalo, E., and Rokkanen, P. 1992. "Foreign-body Reactions to Polyglycolide Screws: Observations in 24/216 Malleolar Fracture Cases," *Acta Orthopaedica* 63(2):173-176). Solders that heat by photosensitizing absorption of light at a certain frequency recommend the use of combination-form barrel-assembly or radial projection catheter with a fiber optic catheter or fiberoptic endoscope, or angioscope, can be used to activate a photosensitive ingredient. The same action at the same or a different frequency can be used to release medication.

Curcumin has been demonstrated to reduce the inflammatory response associated with poly(L-lactic acid (Dende, C., Meena, J., Nagarajan, P., Nagaraj, V. A., Panda, A. K., and Padmanaban, G. 2017. "Nanocurcumin is Superior to Native Curcumin in Preventing Degenerative Changes in Experimental Cerebral Malaria," *Scientific Reports* 7(1): 10062; Flora, G., Gupta, D., and Tiwari, A. 2013. "Nanocurcumin: A Promising Therapeutic Advancement Over Native Curcumin," *Critical Reviews in Therapeutic Drug Carrier Systems* 30(4):331-368; Jurenka, J. S. 2009. "Anti-inflammatory Properties of Curcumin, a Major Constituent of Curcuma Longa: A Review of Preclinical and Clinical Research" *Alternative Medicine Review* 14(2):141-53; erratum at 14(3):277; Su, S. H., Nguyen, K. T., Satasiya, P., Greilich, P. E., Tang, L., and Eberhart, R. C. 2005. "Curcumin Impregnation Improves the Mechanical Properties and Reduces the Inflammatory Response Associated with Poly(L-lactic Acid) Fiber," *Journal of Biomaterials Science. Polymer Edition* 16(3):353-370; Chainani-Wu, N. 2003. "Safety and Anti-inflammatory Activity of Curcumin: A Component of Tumeric (Curcuma Longa)," *Journal of Alternative and Complementary Medicine* 9(1): 161-168).

As with any substance to be implanted, to minimize if not avert an adverse tissue response to the solder, its coatings, or inclusions, the patient is pretested for sensitivity to various formulations of these materials. Adverse tissue reactions can be forestalled and possibly moderated if not eliminated to afford an implant to dissolve, become absorbed, or intentionally extracted through an impasse-jacket, for example, or to permit an initial interval for tissue integration, by jacketing the implants within a coating of scaffold material containing or itself coated with substances such as phosphorylcholine, and/or dexamethasone, or curcumin.

When fluid, these are used to wet implants such as miniballs, stays, and stent-, impasse-, and magnet-jackets. Otherwise, the retardant is prepared in the form of implant-coated or embedded particles, microspheres, or nanorods (see, for example, Mercanzini, A., Reddy, S. T., Velluto, D., Colin, P., Maillard, A., Bensadoun, J. C., Hubbell, J. A., and Renaud, P. 2010. "Controlled Release Nanoparticle-embedded Coatings Reduce the Tissue Reaction to Neuroprostheses," *Journal of Controlled Release* 145(3):196-202; Bhardwaj, U., Papadimitrakopoulos, F., and Burgess, D. J. 2008. "A Review of the Development of a Vehicle for Localized and Controlled Drug Delivery for Implantable Biosensors," *Journal of Diabetes Science and Technology* 2(6):1016-1029; Bhardwaj, U., Sura, R., Papadimitrakopoulos, F., and Burgess D. J. 2007. "Controlling Acute Inflammation with Fast Releasing Dexamethasone-PLGA Microsphere/PVA Hydrogel Composites for Implantable Devices," *Journal of Diabetes Science and Technology* 1(1):8-17; Patil, S. D., Papadimitrakopoulos, F., and Burgess, D. J. 2004. "Dexamethasone-loaded Poly(lactic-co-glycolic) Acid Microspheres/Poly(vinyl alcohol) Hydrogel Composite Coatings for Inflammation Control," *Diabetes Technology and Therapeutics* 6(6):887-897; Hickey, T., Kreutzer, D., Burgess, D. J., and Moussy, F. 2002. "In Vivo Evaluation of a Dexamethasone/PLGA Microsphere System Designed to Suppress the Inflammatory Tissue Response to Implantable Medical Devices," *Journal of Biomedical Materials Research* 61(2):

180-187). See also the section below entitled Medication Implants and Medicated Implants and Prongs.

For miniballs and stays, which actually penetrate through the substrate tissue, surface treatment to moderate the reaction that ensues following the initial adsorption of endogenous proteins is difficult to avoid but is likely to prove critical for tissue acceptance (see, for example, Nilsson, B., Korsgren, O., Lambris, J. D., and Ekdahl, K. N. 2010. "Can Cells and Biomaterials in Therapeutic Medicine be Shielded from Innate Immune Recognition?," *Trends in Immunology* 31(1):32-38; Jones, K. S. 2008. "Effects of Biomaterial-induced Inflammation on Fibrosis and Rejection," *Seminars in Immunology* 20(2):130-136; Tang, Land Hu, W-J. 2005. "Molecular Determinants of Biocompatibility," *Expert Review of Medical Devices*. 2(4):493-500; Hu, W-J., Eaton, J. W., Ugarova, T. P., and Tang, L. 2001. "Molecular Basis of Biomaterial-mediated Foreign Body Reactions," *Blood* 98(4):1231-1238; Tang, L. and Eaton, J. W. 1995. "Inflammatory Responses to Biomaterials," *American Journal of Clinical Pathology* 103(4):466-471).

Protein adhesion a given, the surface chemistry and topography of miniballs and stays is devised to maximize tissue acceptance (see, for example, Morais, J. M., Papadimitrakopoulos, F., and Burgess, D. J. 2010. "Biomaterials/Tissue Interactions: Possible Solutions to Overcome Foreign Body Response," *American Association of Pharmaceutical Scientists Journal* 12(2):188-196; Zaveri, T. D., Dolgova, N. V., Chu, B. H., Lee, J., Wong, J., Lele, T. P., Ren, F., and Keselowsky, B. G. 2010. "Contributions of Surface Topography and Cytotoxicity to the Macrophage Response to Zinc Oxide Nanorods," *Biomaterials* 31(11): 2999-3007 Kalasin, S. and Santore, M. M. 2009. "Nonspecific Adhesion on Biomaterial Surfaces Driven by Small Amounts of Protein Adsorption," *Colloids and Surfaces. B. Biointerfaces* 73(2):229-236; Lee, J., Kang, B. S., Hicks, B., Chancellor, T. F Jr., Chu, B. H., Wang, H. T., Keselowsky, B. G., Ren, F., and Lele, T. P. 2008. "The Control of Cell Adhesion and Viability by Zinc Oxide Nanorods," *Biomaterials* 29(27):3743-3749; Thevenot, P., Hu, W., and Tang, L. 2008. "Surface Chemistry Influences Implant Biocompatibility," *Current Topics in Medicinal Chemistry* 8(4):270-280; Tang, L. and Hu, W. 2005. "Molecular Determinants of Biocompatibility," *Expert Review of Medical Devices* 2(4): 493-500; Kao, W. J., Liu, Y., Gundloori, R., Li, J., Lee, D., Einerson, N., Burmania, J., and Stevens, K. 2002. "Engineering Endogenous Inflammatory Cells as Delivery Vehicles," *Journal of Controlled Release* 78(1-3):219-233; Jenney, C. R. and Anderson, J. M. 1999. "Alkylsilane-modified Surfaces: Inhibition of Human Macrophage Adhesion and Foreign Body Giant Cell Formation," *Journal of Biomedical Materials Research* 46(1):11-21; Kao, W. J., Hubbell, J. A., and Anderson, J. M. 1999. "Protein-mediated Macrophage Adhesion and Activation on Biomaterials: A Model for Modulating Cell Behavior," *Journal of Materials Science. Materials in Medicine* 10(10/11):601-605).

4b. Medicinal and Medicated Miniballs and Stays

4b(1). Drug-Releasing and Irradiating Miniballs, Stays, and Ferrofluids

The means described herein allow the placement of implants in the form of miniballs or stays in locations, such as within the walls of muscular arteries and the ureters, inaccessible to any means of the prior art such as endoscopic. Placed thus, these implants can be used to release any therapeutic substance which can be prepared for release thus, or to stent, or both. Depending upon the specific application, long- or short-term (absorbed), miniballs and stays may be made capable of spontaneously adaptive ('smart,' closed-loop, self-adjusted) drug release in response to the instant milieu, or, based upon the results of follow-up examinations, controlled from outside the body. Implants within atheromas and tumors, for example, can be used to release antiangiogenic medication or nanoprobes from successive or interleaved layers or shells, for example.

Control using direct or induced heat is addressed below in the sections entitled Implants that Radiate Heat on Demand; Medication-coated Miniballs, Stays, and Prongs with a Heat-activated (-melted, -denatured) Tissue Adhesive-hardener or Binder-fixative; Heating Control over Implants and Coated Implants, to Include Miniballs, Stays, and Prongs; Heating of Implants and Coated Implants, to Include Miniballs, Stays, and Prongs Using Implant-passive Ductus-external or Extrinsic Means; Extracorporeal Energization of Intrinsic Means for Radiating Heat from Within Medication Implants and Medication and/or the Tissue Bonding-coatings of Implants; and Chemical Control over Implants and Coated Implants, to Include Miniballs, Stays, and Prongs; among others.

The stent-unrelated, or drug delivery applications of the miniballs and stays, or ductus-intramural implants to be described, for example, will allow medication to be released from within or adjacent to a lesion in the wall of an anatomical structure. The implants to be described herein can incorporate irradiating seeds and/or medication, whether time released (prolonged release), for insertion within a ductus wall. By contrast, long-term or sustained delivery of a drug would require an invasive procedure for each dose, so that for this purpose, the implants are magnetized and placed once to attract the magnetically susceptible nonoparticle-bound or cobound drug or drugs, as will be addressed. While individual miniballs and stays can serve more than one purpose, such as to stent, release, and attract medication and/or radiation, these functions are more economically assigned to neighboring, less specialized implants.

Noncombinatory implants are readily producible in large numbers at relatively little cost, allow a larger dose to mass ratio, and can be arranged in pattern, making these more versatile than specially formulated implants. All of the drug targeting means and procedures described herein have the object of medical management where minor surgery is essential to gain access to the treatment site. The interventional means for administering medication to be described extend to new pharmacological agents, to include gene therapeutic and nanotechnological, for example, thus extending for the foreseeable future the continuation of interventional methods. Ballistic implantation not only allows temporary or permanent seed-containing miniballs to be placed where conventional seeds can only with difficulty if at all, but reduces the cross sectional area of the penetration path to that of the miniball.

Drug delivering implants can be used independently of or in conjunction with a magnetic stent-jacket (see, for example, Faxon, D. P. (ed.) 2001. *Restenosis: A Guide to Therapy*, London, England: Martin Dunitz/Informa Health Care. ISBN: 1-85317-897-7; Gruberg, L., Waksman, R., Satler, L. F., Pichard, A. D., and Kent, K. M. 2000. "Novel Approaches for the Prevention of Restenosis," *Expert Opinion on Investigational Drugs* 9(11):2555-2578) or drug-eluting (drug coated, medicated) (see, for example, Moses, J. W., Kipshidze, N., and Leon, M. B. 2002. "Perspectives of Drug-eluting Stents: The Next Revolution," *American Journal of Cardiovascular Drugs* 2(3):163-172; Nowak, B., Meyer, J. M., Goergen, T., Fluehs, D., Block, S., Guenther, R. W, Hoecker, H., and Buell U. 2001. "Dosimetry of a 188rhenium-labeled Self-expanding Stent for Endovascular Brachytherapy in Peripheral Arteries," *Cardiovascular Radiation Medicine* 2(4):246-253). Miniballs and stays can be open or closed-loop 'smart pills,' for permanent or temporary placement (Bawa, P., Pillay, V., Choonara, Y. E., and du Toit, L. C. 2009. "Stimuli-responsive Polymers and Their Applications in Drug Delivery," *Biomedical Materials* 4(2):022001; Alvarez-Lorenzo, C. and Concheiro, A. 2008. "Intelligent Drug Delivery Systems: Polymeric Micelles and Hydrogels," *Mini Reviews in Medicinal Chemistry* 8(11): 1065-1074); Traitel, T., Goldbart, R., and Kost, J. 2008. "Smart Polymers for Responsive Drug-delivery Systems," *Journal of Biomaterials Science. Polymer Edition* 19(6): 755-767; Moschou, E. A., Madou, M. J., Prescott, J. H., Lipka, S., Baldwin, S., Sheppard, N. F. Jr, and 5 others 2006. "Chronic, Programmed Polypeptide Delivery from an Implanted, Multireservoir Microchip Device," *Nature Biotechnology* 24(4):437-438; Bachas, L. G., and Daunert, S. 2006. "Voltage-switchable Artificial Muscles Actuating at Near Neutral pH," *Sensors and Actuators B: Chemical* 115(1):379-383; Xu, H., Wang, C., Wang, C., Zoval, J., and Madou, M. 2006. "Polymer Actuator Valves Toward Controlled Drug Delivery Application," *Biosensors and Bioelectronics* 21(11):2094-2099).

In addition to drugs already mentioned, numerous other substances have been implemented or proposed for inhibiting intimal (endarterial) thickening, to include growth factor blockers (see, for example, Asada, Y., Tsuneyoshi, A., Marutsuka, K, and Sumiyoshi, A. 1994. "Suramin Inhibits Intimal Thickening Following Intimal Injury in the Rabbit Aorta in Vivo," *Cardiovascular Research* 28(8):1166-1169), policosanol (Noa, M., Más, R., and Mesa, R. 1998. "Effect of Policosanol on Intimal Thickening in Rabbit Cuffed Carotid Artery," *International Journal of Cardiology* 67(2): 125-132; Noa, M., Más, R., and Lariot, C. 2007. "Protective Effect of Policosanol on Endothelium and Intimal Thickness Induced by Forceps in Rabbits," *Journal of Medicinal Food* 10(3):452-459), glycoprotein IIb/IIIa receptor antagonists, nitric oxide (nitrogen monoxide, an endothelium-derived relaxing factor) donors (see Lefkovits, J. and Topol, E. J. 1997. "Pharmacological Approaches for the Prevention of Restenosis after Percutaneous Coronary Intervention," *Progress in Cardiovascular Diseases* 40(2):141-158), and vascular neutral endopeptidase (Barber, M. N., Kanagasundaram, M., Anderson, C. R., Burrell, L. M., and Woods, R. L. 2006. "Vascular Neutral Endopeptidase Inhibition Improves Endothelial Function and Reduces Intimal Hyperplasia," *Cardiovascular Research* 71(1): 179-188). Vascular endothelial growth factor receptor 2 has been found to retard atherogenesis in mice (Hauer, A. D., van Puijvelde, G. H., Peterse, N., de Vos, P., and eight other authors, 2007. "Vaccination Against VEGFR2 Attenuates Initiation and Progression of Atherosclerosis," *Arteriosclerosis, Thrombosis, and Vascular Biology* 27(9):2050-2057).

Except when accidently released, dropped, or mispositioned, implants other than temporary irradiating seeds, which are exceptional, are not intended for recovery. If necessary, any miniball or stay can include ferrous matter and be recovered using the recovery electromagnet built into same barrel-assembly or that of the same stay insertion tool that was used to place the implant, whether immediately as when mispositioned, or at a later date, such as with a temporary seed on the basis of results at an interval following placement. Provided sufficient continuous ferromagnetic material is incorporated into a medication miniball, for example, the miniball can be remotely, noninvasively, heated by placing the patient in a radiofrequency alternating magnetic or electromagnetic field. Induction heating further allows the noninvasive detection of implant temperature by means of an equivalent temperature calibrated eddy current detector.

In extraluminal stent-jackets, this allows the postprocedural thermoplasty of reobstructive hyperplasia by noninvasive heating of the jacket with the temperature noninvasively read by means of an equivalent temperature calibrated eddy current detector. Moreover, because the intensity of induction can be increased as necessary, stent-jackets intended to be noninvasively heatable need not coordinate the number of 'breathing' perforations seen as 119 in FIGS. 6, 13, 14, and 15 with resistance to eddy current circuits. Dipolar polymers such as acetates, polyvinyl chloride, and polyamides, notably nylon, which are likewise heated when placed in a radio frequency alternating magnetic or electromagnetic field are avoided when their resilience, springiness, or shape-restorative property is used.

When heated in the internal environment, some plastics may additionally release harmful degradation products. Stretched segments anticipated to reocclude can thus be preemptively jacketed to counter this eventuality even where no ductus-intramural implants have been placed. The noninvasive heating of nonabsorbable and absorbable implants has many applications, to include on-demand dissolution, release of medication, accelerated drug uptake and healing, pain reduction, and reducing the setting and curing times of a surgical cement, and. Unless rippled to increase the surface area for quicker dissolution, nonpermanent or absorbable implants, usually medicinal, are smooth and include ferrous material only to allow magnetic recovery if necessary.

In absorbable implants such as medication miniballs and stays, the polymer of the matrix or polymers of the layers thereof, or the medication or layers thereof whether time-released, or any combination of the foregoing, set the period or successive intervals for dissolution. The depth of the layer that incorporates superparamagnetic magnetite or maghemite nanoparticles or finely grained powder, for example, depends upon the potential need to retrieve what remains of the implant were it to become mispositioned. That is, retrievability is lost upon dissolution of the deepest layer containing ferromagnetic material. Implants intended for use as the intraductal component of an extraluminal magnetic stent require a higher proportion of ferrous material, generally not dispersed superparamagnetic magnetite or maghemite nanoparticles or finely grained powder, but rather conformed for optimal susceptibility to magnetic tractive force and chemically isolated as a core for permanence.

A stent, or stenting, miniball can be given outer layers of therapeutic substances, of course. Such substances when present directly support implantation, and typically include antiseptics, antibiotics, lubricants, tissue cements, protein solders, and numerous others singly or severally. Permanent implants include the intravascular components of magnetic stents and/or nontemporary (low dose-rate) irradiating seeds, which can also be enclosed within layers of therapeutic agents. The permanent or nonabsorbable surface of a permanent implant is given a deeply textured surface and otherwise treated to encourage tissue adhesion, infiltration, and integration. To the extent that a dense and deep surface texture allows propulsive gas to escape about the miniball periphery during discharge, the loss in expulsive force must be compensated for by increasing the exit velocity ('muzzle velocity'). To offset losses in exit velocity due to leakage or adjust for differences in tissue hardness, an interventional airgun must allow regulation of the expulsive force.

This capability also allows reducing the velocity to control the depth of miniball penetration and avoid perforations. Where the length of the ductus to be implanted with medication or radiation seeds, for example, is large, but focused drug targeting or irradiation is wanted, nonstenting medication or radiation seed miniballs, which do not require local percutaneous entry either to gain access as do stays nor to place a jacket, are used. This eliminates any extensive percutaneous access. Whereas to place any number, size, or type of miniballs necessitates single percutaneous entry and withdrawal and can be accomplished with accuracy in a relatively short time, the prior art alternative of placing multiple endoluminal stents requires but single femoral, cubital, or brachial (radial) entry, but repeated withdrawal and reentry to separately place each stent.

Repeated withdrawal and entry increases the risk of entry wound hematoma and infection and increases procedural time. If the miniballs are to be used for stenting, then depending upon how closely together extraluminal stents are to be placed, a separate access incision at the body surface allows placement of from 1 to 3 extraluminal stents without repeated irritation of a single entry wound. With a barrel-assembly equipped with a built-in wide angle fiberoptic endoscope or angioscope or a combination-form barrel-assembly with such a device inserted through its central channel to afford a clear view, miniballs can be accurately placed. If the ductus is malacotic, determined by the means described in the section below entitled Testing and Tests, implantation by ballistic means may be discounted and stays, which involve no transluminal component to place, are used.

If the number of ductus-intramural implants is relatively few, a malacotic ductus may be implanted if first treated to strengthen or bind it, as addressed below in the section entitled Medication-coated Miniballs, Stays, and Prongs with a Heat-activated (-melted, -denatured) Tissue Adhesive-hardener or Binder-fixative. If only slightly malacotic, a tissue hardener and prepositioned double-wedge stent-jacket rebound-directing lining insert, as addressed below in the section of like title may be used to prevent perforations. The terms 'tissue hardener' and 'sclerosant' in this context refer to stiffening agents that indurate malacotic tissue, not to agents used to embolize a varicosity or a polyp, for example. The means to be described provide additional methods of treatment using radiation (brachytherapy endocurietherapy, sealed source radiotherapy).

Currently, high dose-rate treatment is applied with a remote afterloader, which has limited organ applicability, and must be withdrawn leaving no radioactive substance in the patient. This denies the ability to terminate the treatment based upon reexaminations at intervals without the need to repeat the procedure. The embedding and suturing of multiple interstitial high dose-rate catheter sleeves or trocars and the passing therethrough of source guides, for example, is sufficiently intricate as to discourage repeated treatments thus. Aside from the relative difficulty, longer procedural time, and greater trauma of introducing conventional seeds, especially into the walls of lumina, low dose-rate conventional seeds, as well as stents, are implanted with no expectation of recovery following treatment, limiting the dose-rate.

Affording comparable results at greater convenience to the patient, the use of a higher dose-rate has been recommended over lower dose-rate brachytherpy in the treatment of cervical cancer, for example (see, for example, Wang, X., Liu, R., Ma, B., Yang, K., Tian, J., and 7 others 2010. "High Dose Rate Versus Low Dose Rate Intracavity Brachytherapy for Locally Advanced Uterine Cervix Cancer," *Cochrane Database of Systematic Reviews* (online) 7:CD007563; Viani, G. A., Manta, G. B., Stefano, E. J., and de Fendi, L. I. 2009. "Brachytherapy for Cervix Cancer: Low-dose Rate or High-dose Rate Brachytherapy—A Meta-analysis of Clinical Trials," *Journal of Experimental and Clinical Cancer Research* 5; 28:47). In addition to directly targeted treatment, malignant tumors that shed 'daughter' cells which travel through the bloodstream to induce metastases elsewhere in the body, and persist after the primary tumor has been eliminated, require systemic chemotherapy.

However, because nontargeted tissue is little exposed, the less so when a counteractant is available, a directly targeted tumor can be treated with more concentrated and if appropriate, radioactive medication As addressed above in the section entitled Field of the Invention and in the sections below in order entitled Drug-releasing and Irradiating Miniballs, Stays, and Ferrofluids, Drug-targeting Miniballs and Stays, 80 and Cooperative Use of Impasse-jackets in Pairs and Gradient Arrays, among others, isolated lesions can be magnetically targeted for chemotherapy as well as radiation and/or surgery and for neoadjuvant chemotherapy preparatory to surgical resection of a tumor. The spherical seed miniballs are magnetically extracted through penetration paths no greater in cross sectional area than the seeds. If the coating of platelet blockade about the seed-miniballs is not sufficient to suppress thrombosis on insertion, then systemic medication is required as when the miniballs are eventually recovered.

Higher dose-rates have also been shown more effectively palliative for the treatment of advanced carcinoma (see, for example, Skowronek, J., Piotrowski, T., and Zwierzchowski, G. 2004. "Palliative Treatment by High-dose-rate Intraluminal Brachytherapy in Patients with Advanced Esophageal Cancer," *Brachytherapy* 3(2):87-94; Skowronek, J., Piotrowski, T., Mlynarczyk, W., and Ramlau, R. 2004. "Advanced Tracheal Carcinoma—Therapeutic Significance of HDR Brachytherapy in Palliative Treatment," *Neoplasma* 51(4):313-318; Churn, M., Jones, B., and Myint, A. S. 2002. "Radical Radiotherapy Incorporating a Brachytherapy Boost for the Treatment of Carcinoma of the Thoracic Oesophagus: Results from a Cohort of Patients and Review of the Literature," *Clinical Oncology* (Royal College of Radiology). 14(2):117-122; Sur, R. K., Donde, B., Levin, V. C., and Mannell, A. 1998. "Fractionated High Dose Rate Intraluminal Brachytherapy in Palliation of Advanced Esophageal Cancer," *International Journal of Radiation Oncology, Biology, and Physics* 40(2):447-453). Used in arteries, radioactive stents have been found to cause narrowing at the margins and substantially eliminated from use (Waksman, R. 2006. "Catheter-Based Radiation," in Ellis, S. G. and Holmes, D. R. Jr. *Strategic Approaches in Coronary Intervention*, Philadelphia, Pa.: Lippincott Williams and Wilkins, page 161).

Intermediate dose-rate implants are not introduced with the expectaton of retrieval based upon followup diagnostics at intervals following implantation. Additionally, whereas an irremovable dose-rate limited irradiating stent is endoluminal and interferes with vasomotility and the passing through of contents, a radiation emitting seed-stay is extraluminal (ductus-intramural). Irradiating miniballs, whether containing a seed-core or a radiactive coating, can be implanted in the walls of the gastrointestinal tract, for example, then recovered with slight trauma based upon the results of followup examinations. By contrast, once decayed, conventional seeds are left implanted.

The Cordis Checkmate™ System—P990036 uses seeds to treat in-stent restenosis (see, for example, Waksman, op cit, page 162). Unlike radiation seeds, which left in place, are limited to low dose-rates or radionuclides (radioisotopes) of short half-life such as Xenon-133 (see, for example, Sekine, T., Watanabe, S., Osa, A., Ishioka, N., and nine other inventors, 2001. "Xenon-133 Radioactive Stent for Preventing Restenosis of Blood Vessels and a Process for Producing the Same," U.S. Pat. No. 6,192,095), ductus-intramurally placed stays and miniballs are practicably recoverable and thus usable for delivering medication or radiation in higher doses for a limited period.

In more advanced disease, external beam radiation may be essential to supplement the radiation provided by seeds. In the irradiation intervening tissue, this negates the key benefit in the use of seeds over external irradiation or delivery through the systemic circulation by infusion or ingestion. The means to be described assume the recoverable implantation of variable dose-rate miniballs or stays, making extended exposure to radiation possible without the need to introduce additional irrecoverable seeds or stents, and without the need for any foreign object in the lumen where it interferes with the pulse or peristalsis and can result in numerous complications.

Existing nominally permanent seeds implanted in patients previously treated for a malignancy can, if infrequently, demand periodic reexamination or surgical excision (see, for example, Sachdeva, S., Udechukwu, N. S., Elbelasi, H., Landwehr, K. P., St Clair, W. H., and Winkler, M. A. 2016. "Prostate Brachytherapy Seed Migration to the Heart Seen on Cardiovascular Computed Tomographic Angiography," *Radiology Case Reports* 12(1):31-33; Calvert, A. D., Dyer, A. W., and Montgomery, V. A. 2016. "Embolization of Prostatic Brachytherapy Seeds to Pulmonary Arteries: A Case Study," *Radiology Case Reports* 12(1):34-38; Nguyen, B. D., Schild, S. E., Wong, W. W., and Vora, S. A. 2009. "Prostate Brachytherapy Seed Embolization to the Right Renal Artery," *Brachytherapy* 8(3):309-312; Stewart, A. J., O'Farrell, D. A., Mutyala, S., Bueno, R., Sugarbaker, D. J., Cormack, R. A., and Devlin, P. M. 2007. "Severe Toxicity after Permanent Radioactive Seed Implantation for Mediastinal Carcinoid Tumors," *Brachytherapy* 6(1):58-61; Ankem, M. K., DeCarvalho, V. S., Harangozo, A. M., Hartanto, V. H., Perrotti, M., and 8 others 2002. "Implications of Radioactive Seed Migration to the Lungs after Prostate Brachytherapy," *Urology* 59(4):555-559).

The miniballs or stays can contain a seed-core, carry a radioactive coating, or have a surface that has been ion impregnated. Stay insertion tools as shown in FIGS. 87, 88 thru 91, with a detailed view provided in FIG. 95 and described in section below entitled XVI. Stay Insertion Tools, incorporate a surgical cyanoacrylate cement stay coater to positionally stabilize each stay, extending the time for fibrous encapsulation. Almost all miniballs and stays incorporate sufficient ferromagnetic material to allow recovery. The use of these in high motility ductus such as the gastrointestinal tract makes possible, for example, the placement of higher dose-rate seeds on a temporary basis. Another advantage of implants other than irretrievable endoluminal stents are adaptability to normal growth, changes in the pathology, or both.

Existing radioactive seeds and stents are not readily adapted for use in the luminal walls of most structures, such as the great vessels and heart (see, for example, Talukder, M. Q., Deo, S. V., Maleszewski, J. J., and Park, S. J. 2010. "Late Isolated Metastasis of Renal Cell Carcinoma in the Left Ventricular Myocardium," *Interactive Cardiovascular and Thoracic Surgery* 11(6):814-816; Omura, A., Tobe, S., Yoshida, K., and Yamaguchi, M. 2008. "Surgical Treatment for Recurrent Pulmonary Artery Sarcoma," *General Thoracic and Cardiovascular Surgery* 56(1):28-31 Rastan, A. J., Walther, T., Mohr, F. W., and Kostelka, M. 2004. "Leiomyosarcoma—An Unusual Cause of Right Ventricular Outflow Tract Obstruction," *Thoracic and Cardiovascular Surgeon* 52(6):376-377; Sánchez-Muñoz, A., Hitt, R., Artiles, V., López, A., Hernández, R., Cortés-Funes, H., and Colomer, R. 2003. "Primary Aortic Sarcoma with Widespread Vascular Embolic Metastases," *European Journal of Internal Medicine* 14(4):258-261; Ceccaldi, B., Dourthe, L. M., Garcin, J. M., Vergeau, B., Chanudet, X., and Larroque, P. 2000. "Léiomyosarcome cardiaque du ventricule droit [Leiomyosarcoma of the Right Ventricle]," (in French with abstract in English at Pubmed) *Bulletin du Cancer* (Bulletin of Cancer) 87(7-8):547-550; al-Robaish, A., Lien, D. C., Slatnik, J., and Nguyen, G. K. 1995. "Sarcoma of the Pulmonary Artery Trunk: Report of a Case Complicated with Hemopericardium and Cardiac Tamponade," *Canadian Journal of Cardiology* 11(8):707-709; Thijs, L. G., Kroon, T. A., and van Leeuwen, T. M. 1974. "Leiomyosarcoma of the Pulmonary Trunk Associated with Pericardial Effusion," *Thorax* 29(4):490-494).

Within an artery, the traveling radial excursion and return of the wall by the pulse is not large enough to result in significant implant mispositionings. Moreover, in a coronary artery, the muzzle-head moves closely enough with the beating heart that wobble does not affect implant positioning to any significant extent. Thus, as with conventional interventional apparatus, substantially conjoint movement with the containing coronary artery allows procedures to be performed off-pump. The movement of blood past the muzzle-head by the pulse is dependent upon the diameter and length of the muzzle-head, whether the muzzle-head incorporates a bypass groove or grooves, is of the combination-form type with an unoccupied bore to allow blood to pass through, the elasticity of the artery, and the blood pressure.

By contrast, the insertion of stays in a coronary artery must be performed on-pump. Except in the trachea and gastrointestinal tract, to which access does not require incision, the administration of medication in the form of miniballs or stays is normally undertaken as secondary to and supportive of an antecedent or primary reason for entry, usually to ablate and/or stent; generally, only a localized and exigent condition such as a tumor justifies administration thus. Unlike parenteral administration whether oral, by injection, or infusion, medicinal implants of the kind to be described impart the ability to target diseased tissue within the wall of a ductus, for example, at too awkward an angle and in too small as size as would allow injection endoscopically. This allows the use of a small but concentrated dose with less systemic dispersion. Existing methods do not allow injection much less quick shot-delivery into the walls of small lumina.

The ability to target medication poses benefits in terms of efficacy and reducing side effects, as well as in economy and efficiency, and should continue to be of benefit long past the age of mechanical intervention for most other purposes when nanotechnological and gene therapeutic modalities will be prevalent. The simplest and least expensive barrel-assemblies provide this capability. Whether a miniball introduced from within the lumen or a stay introduced through the outer tunic, the lesion or tissue targeted implant is formulated using methods already known in the pharmaceutical field to release different contents at the same or different intervals and rates. Following placement, the implant can be acted upon extracorporeally such as through the application of heat, to effect its dissolution or the release of constituents in a temperature selective manner, for example. The concentric layering of medication for differential release after infixion when desired by magnetic force, heat, or chemical exposure, for example, are all possible.

The selective breakdown of microspheres or nanotubes within layers or of continuous layers one or more at a time at later dates allows medication to be prepositioned for dispersal as periodic followup reevaluations indicate. The combination of medication miniballs, and magnetically susceptible drug carrier bound nanoparticles introduced in a ferrofluid, for example, with impasse-jackets expands the scope of drug delivery. Different forms of drug targeting are described. Miniballs and stays can deliver a drug or other therapeutic substance from a point by simple or time-prolonged (time-released) dissolution or by elution. Miniballs and stays include sufficient superparamagnetic magnetite or maghemite nanoparticles or finely grained powder or magnetically susceptible content for retrieval if misplaced, and increasing this content allows initiating and/or accelerating drug delivery by direct or induction heating.

Since an invasive procedure is required and the site of release cannot be replenished at will as can an impasse-jacket, this form of drug targeting is almost always limited to incidental or adjunct application during a primary invasive procedure catheteric or through open exposure that is essential. Miniballs that consist of a drug or drugs can be interspersed among stenting miniballs, for example. Whereas implanted miniballs and stays are embedded within the diseased tissue, limiting followup access to these by absorption through the lumen wall or injection with the aid of radial projection unit (side-looking) injection tool-inserts, a miniball, for example, suspended in the lumen by an impasse-jacket remains accessible to substances administered at a later time whether orally or by injection to end or modify its action.

That is, an impasse-jacket allows follow-up access to the suspendant and is rechargeable (replenishable) to allow continued or adjusted administration of a drug or drugs as necessary. Injected miniballs, microspherules, and prospectively, ingested drug carrier nanoparticles can be trapped and suspended in the lumen by an impasse-jacket to deliver a drug through any of the foregoing processes repeatedly at any time. Lumen side-looking injectors, radial discharge barrel-assemblies, and impasse-jackets able to deliver mediation into the wall surrounding a delimited segment of even a small ductus where no means could do so before, the facility of treatment may be critically augmented. With certain conditions, this can justify the invasive procedure to place the jacket.

Atherosclerosis consists of a systemic inflammation throughout the arterial tree but most prominent and vulnerable at discrete sites where the forces generated by lumen conformation and flow produces lesions the location of which are predictable at bifurcations. The object in treatment should be to reinstate normal endothelial function and the healing of frank lesions. This is accomplished with a statin (3-hydroxy-3-methylglutaryl-coenzyme A (or HMG-CoA) reductase inhibitor) in the systemic circulation and the singling out lesions for special treatment. While mildly inflamed intima treated only medically should re-endothelialize and recover without scarring or the formation of neointima, severely diseased tissue warrants elimination to avert an acute event despite the probability that the condition itself and the treatment will detain if not preclude eventual healing of which the lesion was probably incapable in any event.

One means for the spot treatment of lesions that reduces the risk for thrombogenesis is thermoplasty (see, for example, Lawrence, J. B., Prevosti, L. G., Kramer, W. S., Smith, P. D., Bonner, R. F., Lu, D. Y., and Leon, M. B. 1992. "Pulsed Laser and Thermal Ablation of Atherosclerotic Plaque: Morphometrically Defined Surface Thrombogenicity in Studies Using an Annular Perfusion Chamber," *Journal of the American College of Cardiology* 19(5):1091-1100; Lawrence, J. B., Prevosti, L. G., Kramer, W. S., Lu, D. Y., and Leon, M. B. 1989. "Platelet Adherence and Thrombus Formation with Flowing Human Blood on Atherosclerotic Plaque: Reduced Thrombogenicity of Watanabe-heritable Hyperlipidemic Rabbit Aortic Subendothelium," *Thrombosis Research* 54(2):99-114).

Targeted statin delivery, for which impasse-jackets, for example, can be pre-positioned, allows a considerably reduced serum or systemic background level of a statin to be administered, minimizing adverse side effects, while segments which are already or can be predicted to become severely atheromatous can be given a concentrated dose. The background or systemically circulated statin enhances the catabolism of low density lipoprotein by the liver, whereas that targeted at the atheromatous lesion delivers other beneficial effects of the statin.

In atherosclerosis, endothelial activation and dysfunction lead to chronic intimal inflammation and atheromatous lesioning (Alom-Ruiz, S. P., Anilkumar, N., and Shah, A. M. 2008. "Reactive Oxygen Species and Endothelial Activation," *Antioxidants and Redox Signaling* 10(6): 1089-1100). Atheromatous lesions and transluminal interventions are both associated with endothelial dysfunction (Padfield, G. J., Newby, D. E., and Mills, N. L. 2010. Understanding the Role of Endothelial Progenitor Cells in Percutaneous Coronary Intervention," *Journal of the American College of Cardiology* 55(15):1553-1565; Caramori, P. R. A.; Lima, V. C.; Seidelin, P. H.; Newton, G. E; Parker, J. D; Adelman, A. G. 1999. "Long-term Endothelial Dysfunction after Coronary Artery Stenting," *Journal of the American College of Cardiology* 34(6): 1675-1679).

However, if reinstatable to normal endothelial function, sites of vulnerable plaque may take a long time to do so, and in the meantime pose an immediate risk of rupture with dangerous consequences, as to demand active intervention. Whether intimal tissue in a state of chronic inflammation or frankly atheromatous has the potential to recover to a state of normal endothelial function with treatment would appear to depend upon how severe are the disease and how traumatizing the treatment. Statins having been shown to exert a considerable healing effect on diseased intima, searing and/or targeting of atheromatous lesions with a statin at a concentration higher than should be circulated with a background of circulated statin to treat chronically inflamed intima is an approach that the inventive system makes possible.

A statin applied directly to an atheromatous segment without passing through or being limited to the liver provides direct benefits for the consequences of protracted elevated serum cholesterol and not just a reduction in serum cholesterol production as such, as well as exercises a demonstrable healing function in vascular tissue (see, for example, Mitsuhashi, T., Uemoto, R., Ishikawa, K., Yoshida, S., Ikeda, Y., and 4 others 2018. "Endothelial Nitric Oxide Synthase-independent Pleiotropic Effects of Pitavastatin against Atherogenesis and Limb Ischemia in Mice," *Journal of*

*Atherosclerosis and Thrombosis* 25(1):65-80; Gavazzoni, M., Gorga, E., Derosa, G., Maffioli, P., Metra, M., and Raddino, R. 2017. "High-dose Atorvastatin Versus Moderate Dose on Early Vascular Protection after ST-elevation Myocardial Infarction," *Drug Design, Development, and Therapy* 11:3425-3434; Balan, A., Szaingurten-Solodkin, I., Swissa, S. S., Feinshtein, V., Huleihel, M., and 3 others 2017. "The Efects of Pravastatin on the Normal Human placenta: Lessons from ex-vivo models," *Public Library of Science One* 12(2):e0172174; Akarsu, M., Saygun, O., Aydinuraz, K., Aydin, O., Daphan, C. E., and 3 others 2017. "The Effects of Simvastatin on Ischemia Reperfusion Injury in an Experimental Colon Anastomosis Model," *Indian Journal of Surgery* 79(5):390-395; Owens, A. P. 3rd, Passam, F. H., Antoniak, S., Marshall, S. M., McDaniel, A. L., Rudel, L., Williams J. C., and 15 others 2012. "Monocyte Tissue Factor-dependent Activation of Coagulation in Hypercholesterolemic Mice and Monkeys is Inhibited by Simvastatin," *Journal of Clinical Investigation* 122(2):558-568; Silverstein, R. L. 2012. "Teaching an Old Dog New Tricks: Potential Antiatherothrombotic Use for Statins," *Journal of Clinical Investigation* 122(2):478-481; Marzilli, M. 2010. "Pleiotropic Effects of Statins: Evidence for Benefits Beyond LDL-cholesterol Lowering.," *American Journal of Cardiovascular Drugs* 10 Supplement 1:3-9; Pedersen, T. R. 2010. "Pleiotropic Effects of Statins: Evidence Against Benefits Beyond LDL-cholesterol Lowering," *American Journal of Cardiovascular Drugs* 10 Supplement 1:10-17; Smaldone, C., Brugaletta, S., Pazzano, V., and Liuzzo, G. 2009. "Immunomodulator Activity of 3-hydroxy-3-methilglutaryl-CoA Inhibitors," *Cardiovascular and Hematological Agents in Medicinal Chemistry* 7(4):279-94; Ii, M. and Losordo, D. W. 2007. "Statins and the Endothelium," *Vascular Pharmacology* 46(1):1-9; Dilaveris, P., Giannopoulos, G., Riga, M., Synetos, A., and Stefanadis, C. 2007. "Beneficial Effects of Statins on Endothelial Dysfunction and Vascular Stiffness," *Current Vascular Pharmacology* 5(3):227-237; Calabrò, P. and Yeh, E. T. 2005. "The Pleiotropic Effects of Statins," *Current Opinion in Cardiology* 20(6):541-546).

The pleiotropic or liver metabolism-independent/local application potential of relatively new drugs, such as proprotein convertase subtilisin/kexin type 9 (PCSK9) inhibitors and investigatory or experimental small interference RNA PCSK9 messenger RNA inhibitor (inclisiran) (see, for example, Fitzgerald, K., White, S., Borodovsky, A., Bettencourt, B. R., Strahs, A., and 10 others 2017. "A Highly Durable RNAi Therapeutic Inhibitor of PCSK9," *New England Journal of Medicine* 376(1):41-51; Ray, K. K., Landmesser, U., Leiter, L. A., Kallend, D., Dufour, R., and 8 others 2017. "Inclisiran in Patients at High Cardiovascular Risk with Elevated LDL Cholesterol," *New England Journal of Medicine* 376(15):1430-1440; Hadjiphilippou, S. and Ray, K. K. 2017. "PCSK9 Inhibition and Atherosclerotic Cardiovascular Disease Prevention: Does Reality Match the Hype?," *Heart* (British Cardiac Society) 103(21):1670-1679; Shah, P., Glueck, C. J., Goldenberg, N., Min, S., Mahida, C., and 4 others 2017. "Efficacy, Safety, Low Density Lipoprotein Cholesterol Lowering, and Calculated 10-year Cardiovascular Risk Reduction of Alirocumab and Evolocumab in Addition to Maximal Tolerated Cholesterol Lowering Therapy: A Post-commercialization Study," *Lipids in Health and Disease* 16(1):19; Choi, J., Khan, A. M., Jarmin, M., Goldenberg, N., Glueck, C. J., anf Wang, P. 2017. "Efficacy and Safety of Proprotein Convertase Subtilisin-Kexin Yype 9 (PCSK9) Inhibitors, Alirocumab and Evolocumab, a Post-commercialization Study," *Lipids in Health and Disease* 16(1):141; Wiciński, M., Żak, J., Malinowski, B., Popek, G., and Grześk, G. 2017. "PCSK9 Signaling Pathways and Their Potential Importance in Clinical Practice," *European Predictive Medicine Association Journal* 8(4):391-402; Schulz, R. and Schlüter, K. D. 2017. "PCSK9 Targets Important for Lipid Metabolism," *Clinical Research in Cardiology Supplements* 12(Supplement 1):2-11; Glerup, S., Schulz, R., Laufs, U., and Schlüter, K. D. 2017. "Physiological and Therapeutic Regulation of PCSK9 Activity in Cardiovascular Disease," *Basic Research in Cardiology* 112(3):32; Seidah, N. G. 2016. "New Developments in Proprotein Convertase Subtilisin-Kexin 9's Biology and Clinical Implications," *Current Opinion in Lipidology* 27(3):274-281; Gupta, S. 2016. "Development of Proprotein Convertase Subtilisin/Kexin Type 9 Inhibitors and the Clinical Potential of Monoclonal Antibodies in the Management of Lipid Disorders," *Vascular Health and Risk Management* 12:421-433; McDonagh, M., Peterson, K., Holzhammer, B., and Fazio, S. 2016. "A Systematic Review of PCSK9 Inhibitors Alirocumab and Evolocumab," *Journal of Managed Care and Specialty Pharmacy* 22(6):641-653q; Zhang, L., Song, K., Zhu, M., Shi, J., Zhang, H., Xu, L., and Chen, Y. 2016. "Proprotein Convertase Subtilisin/Kexin Type 9 (PCSK9) in Lipid Metabolism, Atherosclerosis, and Ischemic Stroke," *International Journal of Neuroscience* 126(8):675-680; Urban, D., Pöss, J., Böhm, M., and Laufs, U. 2013. "Targeting the Proprotein Convertase Subtilisin/Kexin Type 9 for the Treatment of Dyslipidemia and Atherosclerosis," *Journal of the American College of Cardiology* 62(16):1401-1408; Steinberg, D. and Witztum, J. L. 2009. "Inhibition of PCSK9: A Powerful Weapon for Achieving Ideal LDL Cholesterol Levels," *Proceedings of the National Academy of Sciences of the United States of America* 106(24):9546-9547), cholesterylester transfer protein (CETP) inhibitors (see, for example, Han, S., Levoci, L., Fisher, P., Wang, S. P., and 7 others 2012. "Inhibition of Cholesteryl Ester Transfer Protein by Anacetrapib Does Not Impair the Anti-inflammatory Properties of High Density Lipoprotein," *Biochimica et Biophysica Acta* December 23 pii: S1388-1981(12)00262-00264; Nicholls, S. J., Brewer, H. B., Kastelein, J. J., Krueger, K. A., Wang, M. D., and 4 others 2011. "Effects of the CETP Inhibitor Evacetrapib Administered as Monotherapy or in Combination with Statins on HDL and LDL Cholesterol: A Randomized Controlled Trial," *Journal of the American Medical Association* 306(19):2099-2109), such as anacetrepib (Merck), evacetrapib (Lilly), currently under clinical trials, or isolated ethyl eicosapentaenoic acid (Vascepa® (Amarin), Epadel® (Mochida) to function locally or pleiotropically as do statins appears not as yet to have been investigated.

In addition to raising high density lipoprotein, this class of drugs appears to decrease low density lipoprotein more than the reduction obtained with a statin alone, and may prove valuable on that basis. However, the drug-induced high density lipoprotein produced appears dissimilar from that originated in the gut and liver (see, for examples, Rader, D. J. and Hobbs, H. H., 2005. "Disorders of Lipoprotein Metabolism," Chapter 335, page 2288, in *Harrison's Principles of Internal Medicine*, New York, N.Y.: McGraw-Hill) and relatively ineffective at recovering cholesterol and other lipids, to include that within atheromatous tissue, and transporting it to the liver for reformulation or breakdown and disposal, which subject is under study (see, for example, Nicholls, S. J., Gordon, A., Johannson, J., Ballantyne, C. M., Barter, P. J., Brewer, H. B., Kastelein, J. J., Wong, N. C., Borgman, M. R., and Nissen, S. E. 2012. "ApoA-I Induction as a Potential Cardioprotective Strategy: Rationale for the SUSTAIN and ASSURE Studies," *Cardiovascular Drugs and Therapy* 26(2): 181-187).

Rather than to force the natural production of defective high density lipoprotein, one approach would be to directly synthesize a molecule identical to natural high density lipoprotein and directly pipe it to the circulatory system through a nonmagnetized or magnetized jacket from a portal implanted at the body surface as described herein. Awareness of the pleiotropic effects of statins has existed for years (Lahera, V., Goicoechea, M., de Vinuesa, S. G., Miana, M., de las Heras, N., Cachofeiro, V., and Luño, J. 2007. "Endothelial Dysfunction, Oxidative Stress and Inflammation in Atherosclerosis: Beneficial Effects of Statins," *Current Medicinal Chemistry* 14(2):243-248; Sipahi, I., Nicholls, S. J., Tuzcu, E. M., and Nissen, S. E. 2006. "Coronary Atherosclerosis Can Regress with Very Intensive Statin Therapy," *Cleveland Clinic Journal of Medicine* 73(10): 937-944; Nissen, S. E., Nicholls, S. J., Sipahi, I., Libby, P., Raichlen J. S, Ballantyne C M, Davignon J, and 9 other ASTEROID Trial Investigators 2006. "Effect of Very High-intensity Statin Therapy on Regression of Coronary Atherosclerosis: The ASTEROID Trial," *Journal of the American Medical Association* 295(13):1556-1565; Arnaud, C., Veillard, N. R., Mach, F. 2005. "Cholesterol-independent Effects of Statins in Inflammation, Immunomodulation and Atherosclerosis," *Current Drug Targets. Cardiovascular and Haematological Disorders* 5(2):127-134; Sorrentino, S. and Landmesser, U. 2005. "Nonlipid-lowering Effects of Statins," *Current Treatment Options in Cardiovascular Medicine* 7(6):459-466; Calabrò, P. and Yeh, E. T. 2005. "The Pleiotropic Effects of Statins," *Current Opinion in Cardiology* 20(6):541-546; Davignon, J. 2004. "Atherosclerosis: Evolving Vascular Biology and Clinical Implications. Beneficial cardiovascular pleiotropic effects of statins," *Circulation* 109(23 Supplement 1):III39-III43; Walter, D. H., Zeiher, A. M., and Dimmeler, S. 2004. "Effects of Statins on Endothelium and Their Contribution to Neovascularization by Mobilization of Endothelial Progenitor Cells," *Coronary Artery Disease* 15(5):235-242; Walter, D. H., Rittig, K., Bahlmann, F. H., Kirchmair, R., Silver, M., and 5 others 2002. "Statin Therapy Accelerates Reendothelialization: A Novel Effect Involving Mobilization and Incorporation of Bone marrow-derived Endothelial Progenitor Cells," *Circulation* 105(25):3017-3024).

That the non-LDL-Cholesterol-lowering or pleiotropic effects of statins, to include anti-inflammatory, immunomodulatory, and antithrombotic, may not reduce the incidence of acute events (see, for example, Robinson, J. G., Smith, B., Maheshwari, N., and Schrott, H. 2005. "Pleiotropic Effects of Statins: Benefit Beyond Cholesterol Reduction? A Meta-Regression Analysis," *Journal of the American College of Cardiology* 46(10):1855-1862) may not equate to a lack of benefit for reducing inflammation leading to healing in less severely diseased and iatrogenically affected tissue. The benefits of statins by direct application are also addressed below in the section entitled Cooperative Use of Impasse-jackets in Pairs and Gradient Arrays.

Vascular endothelial growth factor (see, for example, Asahara, T., Bauters, C., Pastore, C., Kearney, M., Rossow, S., Bunting, S., Ferrara, N., Symes, J. F., and Isner, J. M.1995. "Local Delivery of Vascular Endothelial Growth Factor Accelerates Reendothelialization and Attenuates Intimal Hyperplasia in Balloon-injured Rat Carotid Artery," *Circulation* 91(11):2793-2801), thrombospondin blockade (see Chen, D., Asahara, T., Krasinski, K., Witzenbichler, B., Yang, J., and 5 others 1999. "Antibody Blockade of Thrombospondin Accelerates Reendothelialization and Reduces Neointima Formation in Balloon-injured Rat Carotid Artery," *Circulation* 100(8):849-854), estrogen receptor alpha (see Brouchet, L., Krust, A., Dupont, S., Chambon, P., Bayard, F., and Arnal, J. F. 2001. "Estradiol Accelerates Reendothelialization in Mouse Carotid Artery through Estrogen Receptor-alpha but Not Estrogen Receptor-beta," *Circulation* 103(3):423-428), estrogen receptor modulators (see, for example, Christodoulakos, G. E., Lambrinoudaki, I. V., and Botsis, D. C. 2006. "The Cardiovascular Effects of Selective Estrogen Receptor Modulators," *Annals of the New York Academy of Sciences* 1092:374-384; Savolainen-Peltonen, H., Luoto, N. M., Kangas, L., and Häyry, P. 2004. "Selective Estrogen Receptor Modulators Prevent Neointima Formation after Vascular Injury," *Molecular and Cellular Endocrinology* 227(1-2):9-20; Yue, T. L., Vickery-Clark, L., Louden, C. S., Gu, J. L., Ma, X. L., Narayanan, P. K., and 6 others "Selective Estrogen Receptor Modulator Idoxifene Inhibits Smooth Muscle Cell Proliferation, Enhances Reendothelialization, and Inhibits Neointimal Formation in Vivo after Vascular Injury," *Circulation* 2000 102(19 Supplement 3):III281-III288) and endothelial progenitor cells (see Chen L, Wu F, Xia W H, Zhang Y Y, Xu S Y, and 5 others 2010. "CXCR4 Gene Transfer Contributes to in Vivo Reendothelialization Capacity of Endothelial Progenitor Cells," *Cardiovascular Research* 88(3):462-470) as well as other substances have been found to expedite healing in lower mammals.

The capability for impasse-jackets, medication ductus-intramural implants, patch-magnets, and magnet-jackets to implement the local delivery of medication is a primary object of the inventive system as delineated in the sections respective of each type implant. Analogously, local and regional cancer is treated with radiation and surgery, whereas systemic cancer is treated by chemotherapy. The benefits of statins have been noted as pleiotropic for the treatment of cancer as well as atheromatous disease (see, for example, Gazzerro P, Proto M C, Gangemi G, Malfitano A M, Ciaglia E, and 4 others. 2012. "Pharmacological Actions of Statins: A Critical Appraisal in the Management of Cancer," *Pharmacological Reviews* 64(1):102-146; Zeichner, S., Mihos, C. G., and Santana, O. 2012. "The Pleiotropic Effects and Therapeutic Potential of the Hydroxy-methyl-glutaryl-CoA Reductase Inhibitors in Malignancies: A Comprehensive Review," *Journal of Cancer Research and Therapeutics* 8(2):176-183). The toxicity and adverse side effects of chemotherapy are serious and can begin with extravasation during infusion of a vesicant drug that leads to tissue necrosis (see, for example, Ener, R. A., Meglathery, S. B., and Styler, M. 2004. "Extravasation of Systemic Hemato-oncological Therapies," *Annals of Oncology* 15(6): 858-862).

However, magnetized miniballs, stays, impasse-jackets, and patch-magnets make it possible to isolate a tumor in a context of systemic disease for receiving a high concentration of the anticancer drug, thus allowing the systemic dose to be reduced, while local and regional tumors can be treated by targeted chemotherapy by means of magnetic force that allows the systemic dose to be eliminated. Magnetically targeted chemotherapy may seek to kill tumor cells directly—through mitotoxicity, cytotoxicity, antiangionicity, metabolic mechanism, and so on by antineoplastic drugs otherwise delivered systemically—or indirectly, by enhancing susceptibility of tumor cells to radiation, or both, again using known systemic drugs for the purpose.

Implanting medication miniballs and stays to deliver a statin or an antineoplastic drug, for example, makes it possible to concentrate the drug or drugs within the wall surrounding a susceptible segment, allowing a background serum level of the drug if any, and therewith, unwanted side effects, to be reduced accordingly, the overall reduction in the amount of the drug used considerable. For drugs needed over a brief period to treat a temporary condition, the sum dose that can be delivered within the lumen wall of a more acutely affected segment by medication miniballs or stays, whether at once or time-released, can often be made sufficient to allow effective treatment. However, the administration of a statin and other drugs to treat a condition that results from a metabolic disorder, even when concentrated at the lesion and formulated for release at a slow rate or only when heated, will not provide a beneficial effect unless sustained indefinitely, as is the disorder.

To deliver drugs on a sustained basis, the implants are not used to release the drugs but rather to attract the drugs from the passing lumen contents. The magnetized implants are placed in a one-time invasive procedure that will allow the effective targeting of a certain segment indefinitely, whenever the drug is taken, preferably by mouth. The magnetically susceptible carrier-bound drugs may be added to food for treating an esophageal neoplasm or formulated into capsules that will release a ferrofluid which will pass into the bloodstream to be trapped along a more severely diseased segment of an artery. Once in the bloodstream, the nanoparticle carrier ferrobound drug moves until it reaches the segment that has the magnetized miniballs, stays, impassejackets, stent-jackets, or magnet-wrap. To define a segment, the implants are arranged along that segment or if the lesion is eccentric, then according to the eccentricity, in order of increased strength of magnetization in the antegrade direction.

A more even distribution of the drug is also obtained when the drug carrier is likewise graduated in magnetic susceptibility. The carrier-bound drug is then drawn from the passing blood into the wall surrounding the segment defined for treatment. Any residue, indeed, the entire dose, of any conventional drug that continues past the target segment, even though concentrated for the segment, will be so diluted as rarely if ever pose a risk of unwanted side effects. The addition of a terminal or exit impasse-jacket (exit-jacket) allows the release of a reversal agent to counteract a drug so toxic or radioactive that even the diluted residue might do harm. Such a drug will usually be an anticancer chemotherapeutic, but might also be a drug needed to treat a localized nematodiasistic, protozoan, mycotic, or other infection that is resistant to conventional therapy, for example. An exit jacket is placed and charged or loaded with the reversal agent or counteractant first.

Since any local point of release or reversal can be initially or subsequently affected through the application of heat, irreversible electroporation, or by administering other substances, the possibilities comprehended are too numerous to enumerate in any detail. For example, different melting points or fracture resistances to a magnetic field of the superparamagnetic magnetite or maghemite nanoparticles or finely grained powder-including encapsulating layer can be used to cause a prepositioned implant to release a layer of medication. This makes it possible to release selectable medication from a prepositioned locus in response to diagnostic testing according to a prescribed timetable as dictated by the course of the condition.

The overall dose of each constituent at a given interval is determined by the number of implants placed at the site and the concentration and rates of release of the different constituents, the selective release of each limited only by the kinds and intensities of energy used to release it. If noncritical and simply accomplished, the patient can be contacted to perform the necessary action at home. Releasing a selectable number of layers allows controlling the dose or the specific medication or medications according to the results of periodic diagnostic testing. Combining separate hemispheres to make the miniballs or separate halves to make stays doubles the absolute number of substances that might be released from each implant and allows different substances to be released together and simultaneously or sequentially.

Extracorporeal control over the dissolution of medication-containing implants or side-looking syringe injector tool-insert injectants previously introduced into a tumor or plaque, for example, can be used to generate heat within and thereby release an antitumor agent within or ablate a tumor (see, for example, Thomas, C. R., Ferris, D. P., Lee, J. H., Choi, E., Cho, M. H., and 5 others 2010. "Noninvasive Remote-controlled Release of Drug Molecules in Vitro Using Magnetic Actuation of Mechanized Nanoparticles," *Journal of the American Chemical Society* 132(31):10623-10625; Hayashi, K., Ono, K., Suzuki, H., Sawada, M., Moriya, M., Sakamoto, W., and Yogo, T. 2010. "High-frequency, Magnetic-field-Responsive Drug Release from Magnetic Nanoparticle/Organic Hybrid Based on Hyperthermic Effect," *American Chemical Society Applied Materials and Interfaces* 2(7):1903-1911; Richter, H., Kettering, M., Wiekhorst, F., Steinhoff, U., Hilger, I., and Trahms, L. 2010. "Magnetorelaxometry for Localization and Quantification of Magnetic Nanoparticles for Thermal Ablation Studies," *Physics in Medicine and Biology* 55(3):623-633; Hilger, I., Hiergeist, R., Hergt, R., Winnefeld, K., Schubert, H., and Kaiser, W. A. 2002. "Thermal Ablation of Tumors Using Magnetic Nanoparticles: an in Vivo Feasibility Study," *Investigative Radiology* 37(10):580-586; Babincová, M., Cicmanec, P Altanerová, V., Altaner, C., and Babinec, P. 2002. "AC-magnetic Field Controlled Drug Release from Magnetoliposomes: Design of a Method for Site-specific Chemotherapy," *Bioelectrochemistry* 55(1-2): 17-19).

Any of the implants and means for implanting these described herein can be used for magnetic hyperthermia apart from the flowing of any outer layers. Several methods for the release on command of drugs previously implanted exist. Where the inclusion within the implants of ferromagnetic material precludes the use of magnetic force with distinctions in field strength as would allow either retrieval of the intact implant or the release of a drug from within it, externally applied heating such as with ultrasound can be used to effect the release of therapeutic agents on a selective basis (see, for example, Frenkel, V. 2008. "Ultrasound Mediated Delivery of Drugs and Genes to Solid Tumors," *Advanced Drug Delivery Reviews* 60(10):1193-1208; Dromi, S., Frenkel, V., Luk, A., Traughber, B., Angstadt, M., and 6 others 2007. "Pulsed-high Intensity Focused Ultrasound and Low Temperature-Sensitive Liposomes for Enhanced Targeted Drug Delivery and Antitumor Effect," *Clinical Cancer Research* 13(9):2722-2727; Iga, K., Ogawa, Y., and Toguchi, H. 1992. "Heat-induced Drug Release Rate and Maximal Targeting Index of Thermosensitive Liposome in Tumor-bearing Mice," *Pharmaceutical Research* 9(5): 658-662).

Release triggering also includes activation following placement using ultrasound (see, for example, Tachibana, K., Feril, L. B. Jr., and Ikeda-Dantsuji, Y. 2008. "Sonodynamic Therapy," *Ultrasonics* 48(4):253-259; Staples, M., Daniel, K., Cima, M. J., and Langer, R. 2006. "Application of Micro- and Nano-electromechanical Devices to Drug Delivery," *Pharmaceutical Research* 23(5):847-863; Liu, Y., Miyoshi, H., and Nakamura, M. 2006. "Encapsulated Ultrasound Microbubbles: Therapeutic Application in Drug/Gene Delivery," *Journal of Controlled Release* 114(1):89-99; Tachibana, K. 2004. "Emerging Technologies in Therapeutic Ultrasound: Thermal Ablation to Gene Delivery," *Human Cell* 17(1):7-15; Unger, E. C., Hersh, E., Vannan, M., Matsunaga, T. O., and McCreery, T. 2001. "Local Drug and Gene Delivery through Microbubbles," *Progress in Cardiovascular Diseases* 44(1):45-54; Tachibana, K. and Tachibana, S. 1998. "Application of Ultrasound Energy as a New Drug Delivery System," (in Japanese with abstract in English at Pubmed), *Nippon Rinsho* [Japanese Journal of Clinical Medicine] 56(3):584-588).

As with photosensitizer inclusive protein solder, where adequate absorption can be achieved, a combination-form barrel-assembly or radial projection catheter with a fiberoptic endoscope, angioscope, or laser can be used to activate a photosensitive ingredient (see, for example, Cheng, F. Y., Su, C. H., Wu, P. C., and Yeh, C. S. 2010. "Multifunctional Polymeric Nanoparticles for Combined Chemotherapeutic and Near-infrared Photothermal Cancer Therapy in Vitro and in Vivo," *Chemical Communications* 46(18):3167-3169).

4b(2). Local Release of Drugs by Miniballs and Stays

Antiangiogenic drugs such as interferon alpha, antiangiogenic antithrombin, angiostatin, endostatin, vasculostatin, and so on, have two distinct applications in connection with the implants to be described herein. The first is for incorporation into or the coating of miniballs and stays for subadventitial implantation at the site of an atheromatous plaque or tumor for the purpose of inhibiting neovascularization of the vasa vasorum. The systemic administration of such drugs typically covers a period of months, its timing a central consideration (see, for example, Duda, D. G. 2007. "American Association for Cancer Research 98th Annual Meeting. Angiogenesis and Anti-angiogenesis in Cancer," *IDrugs* 10(6):366-369; Goh, P. P., Sze, D. M., and Roufogalis, B. D. 2007. "Molecular and Cellular Regulators of Cancer Angiogenesis," *Current Cancer Drug Targets* 7(8): 743-758; van Kempen, L. C. and Leenders, W. P. 2006. "Tumours Can Adapt to Anti-angiogenic Therapy Depending on the Stromal Context: Lessons from Endothelial Cell Biology," *European Journal of Cell Biology* 85(2):61-68; Novak, K. 2002. "Angiogenesis Inhibitors Revised and Revived at the AACR" [American Association for Cancer Research], *Nature Medicine* 8(5):427). The controlled release of such agents close to or at the site of the lesion with focal concentration should allow the use of much less of the agent relative to body mass, minimizing any side effects and reducing the cost of treatment. Whether due to disease or normal function, where the luminal contents are infectious or septic, stays, described below, which are inserted from outside the ductus, are used.

Proangioangenic, neurogenic, and antineuropathic drugs with wide application for promoting healing will more often be associated with absorbable implants that consist solely of medication. Growth trajectory-determining proteins have both mitogenic and mitoinhibitory potential (see, for example, Wilson, B. D., M., Park, K. W., Suli, A., Sorensen, L. K., and 11 other authors, 2006. "Netrins Promote Developmental and Therapeutic Angiogenesis," *Science* 313 (5787):640-644; Park, K. W., Crouse, D., Lee, M., Karnik, S. K., Sorensen, L. K., Murphy, K. J., Kuo, C. J., and Li, D. Y. 2004. "The Axonal Attractant Netrin-1 is an Angiogenic Factor," *Proceedings of the National Academy of Sciences of the United States of America* 101(46):16210-16215). Local or short path targeting, that is, placement of the implant within or adjacent to the lesion, of oncolytic viruses (see, for example, Kinoh, H. and Inoue, M. 2008. "New Cancer Therapy Using Genetically-engineered Oncolytic Sendai Virus Vector," *Frontiers in Bioscience* 13:2327-2334; Davydova, J., Le, L. P., Gavrikova, T., Wang, M., Krasnykh, V., and Yamamoto, M. 2004. "Infectivity-enhanced Cyclooxygenase-2-based Conditionally Replicative Adenoviruses for Esophageal Adenocarcinoma Treatment," *Cancer Research* 64(12):4319-4327) avoids systemic dispersion, concentrates a small dose in the target tissue, minimizes the action onset interval, or delay before the agent takes effect, reduces systemic dispersal, and therefore the likelihood of unwanted side-effects.

The number of implants used is one factor in determining the local dosage. Once expended, drug-containing miniballs and stays are fully absorbed and left in place, superparamagnetic magnetite or maghemite nanoparticles or finely grained powder included to allow recovery if necessary likewise dissipated. Targeted administration should reduce the neovascularization already undergone as an inherent result of the disease process and any interventional measures, and where applicable, to counteract the effect of more widely dispersed angiogenic medication. The other application of antiangiogenic drugs is as a coating on ferromagnetic miniballs and stays for reducing any neovascularization following placement of a stent-jacket. The citation of statins herein as affording benefits when locally targeted to avoid the liver and systemic circulation is exemplary of innumerable other drugs administered to smaller populations. Due to the size of the population prescribed statins, the incidence of side effects in absolute numbers is considerable despite relatively infrequent occurrence by percent.

Drugs cited as specifically antiatherogenic in collared hypercholesterolemic rabbits include isradipine and lacidipine (Donetti, E., Fumagalli, R., Paoletti, R., and Soma, M. R. 1997. "Direct Antiatherogenic Activity of Isradipine and Lacidipine on Neointimal Lesions Induced by Perivascular Manipulation in Rabbits," *Pharmacological Research* 35(5):417-422), bosentan (Marano, G., Palazzesi, S., Bernucci, P., Grigioni, M., Formigari, R., and Ballerini, L. 1998. "ET(A)/ET(B) Receptor Antagonist Bosentan Inhibits Neointimal Development in Collared Carotid Arteries of Rabbits," *Life Sciences* 63(18):PL259-266, TAK-044; Reel, B., Ozkal, S., Islekel, H., Ozer, E., Oktay G, and five other authors, 2005. "The Role of Endothelin Receptor Antagonism in Collar-induced Intimal Thickening and Vascular Reactivity Changes in Rabbits," *Journal of Pharmacy and Pharmacology* 57(12):1599-1608), the selective estrogen receptor modulator raloxifene (Bellosta, S., Baetta, R., Canavesi, M., Comparato, C., and 6 others, 2007. "Raloxifene Inhibits Matrix Metalloproteinases Expression and Activity in Macrophages and Smooth Muscle Cells," *Pharmacological Research* 56(2):160-167), and lercanidipine (Soma, M. R., Natali, M., Donetti, E., Baetta, R., and five other authors, 1998. "Effect of Lercanidipine and Its (R)-enantiomer on Atherosclerotic Lesions Induced in Hypercholesterolemic Rabbits," *British Journal of Pharmacology* 1998 125(7):1471-1476).

Drugs that have been cited as inhibiting atherogenesis include, among others, bevacizumab (Stefanadis, C., Toutouzas, K., Stefanadi, E., Tsiamis, E., Vavuranakis, M., and Kipshidze, N. 2008. "Avastin-eluting Stent: Long-term Angiographic and Clinical Follow-up," *Hellenic Journal of Cardiology* 49(3):188-90), statins (Moulton, K. S., Heller, E., Konerding, M. A., Flynn, E., Palinski, W., and Folkman, J. 1999. Angiogenesis Inhibitors Endostatin or TNP-470

Reduce Intimal Neovascularization and Plaque Growth in Apolipoprotein E-deficient Mice," *Circulation* 99(13):1726-1732; Wilson, S. H., Herrmann, J., Lerman, L. O., Holmes, D. R. Jr., Napoli, C., Ritman, E. L., and Lerman, A. 2002. "Simvastatin Preserves the Structure of Coronary Adventitial Vasa Vasorum in Experimental Hypercholesterolemia Independent of Lipid Lowering," *Circulation* 105(4):415-418; Baetta, R., Camera, M., Comparato, C., Altana, C., Ezekowitz, M. D., and Tremoli, E. 2002. "Fluvastatin Reduces Tissue Factor Expression and Macrophage Accumulation in Carotid Lesions of Cholesterol-Fed Rabbits in the Absence of Lipid Lowering," *Arteriosclerosis, Thrombosis, and Vascular Biology* 1; 22(4):692-698) the antiinflammatory dexamethazone (Hagihara et al. 1991, cited above), antioxidants (see, for example, Wu, T. C., Chen, Y. H., Leu, H. B., Chen, Y. L., Lin, F. Y., Lin, S. J., and Chen, J. W. 2007. "Carvedilol, a Pharmacological Antioxidant, Inhibits Neointimal Matrix Metalloproteinase-2 and -9 in Experimental Atherosclerosis," *Free Radical Biology and Medicine* 43(11):1508-1522), and/or estrogen (see Akishita, M., Ouchi, Y., Miyoshi, H., Kozaki, K., Inoue, S., Ishikawa, M., Eto, M., Toba, K., and Orimo, H. 1997. "Estrogen Inhibits Cuff-induced Intimal Thickening of Rat Femoral Artery: Effects on Migration and Proliferation of Vascular Smooth Muscle Cells," *Atherosclerosis* 130(1-2):1-10). Drug miniballs and stays can release drugs in situ and magnetized ones and impasse-jackets can be used to draw magnetized carrier-bound drugs from the passing blood.

Selective Inhibitors of Protein Kinase C may be used to inhibit the proliferation of smooth muscle cells (see, for example, Tardif, J. C. 2010. "Emerging High-density Lipoprotein Infusion Therapies: Fulfilling the Promise of Epidemiology?," *Journal of Clinical Lipidology* 4(5):399-404; Newby, A. C., Lim, K., Evans, M. A., Brindle, N. P. J., and Booth, R. F. G. 1995. "Inhibition of Rabbit Aortic Smooth Muscle Cell Proliferation by Selective Inhibitors of Protein Kinase C," *British Journal of Pharmacology* 114(8):1652-1656). More recently, apolipoprotein A-1 in a single low dose has been cited as inhibiting acute common carotid artery inflammation in normocholesterolemic Dow Corning Silastic® collared rabbits (see, for example, Tardif, J. C., Heinonen, T., and Noble, S. 2009. "High-density Lpoprotein/Apolipoprotein A-I Infusion Therapy," *Current Atherosclerosis Reports* 11(1):58-63; Puranik, R., Bao, S., Nobecourt, E., Nicholls, S. J., Dusting, G. J., Barter, P. J., Celermajer, D. S., and Rye, K. A. 2008. "Low Dose Apolipoprotein A-I Rescues Carotid Arteries from Inflammation in Vivo," *Atherosclerosis* 196(1):240-247; Nicholls, S. J., Dusting, G. J., Cutri, B., Bao, S., Drummond, G. R., Rye, K. A., Barter, P. J. 2005. "Reconstituted High-density Lipoproteins Inhibit the Acute Pro-oxidant and Proinflammatory Vascular Changes Induced by a Periarterial Collar in Normocholesterolemic Rabbits," *Circulation* 111(12):1543-1550).

The efficacy of lipoprotein A-1 for reversing atherosclerosis in man has not been established. As an alternative to transluminal approach, whereby miniballs are implanted ballistically from within the lumen producing minute puncture and trajectory wounds impelling the use of antiplatelet medication, when the lumen would best be avoided entirely, speed is not critical, and the anatomy and apparatus permit, stays are implanted by extraductal approach. Miniballs can, however, include antithrombogenic medication, usually as an outer coating.

Other substances proposed for the prevention and possible treatment of atherosclerosis as can be mediated by segment or organ delivery by impasse-jackets in concentrated and replenishable dosage within circumscribed sites averting side effects include, among others, lacidipene (Soma, M. R., Donetti, E., Seregni, R., Barberi, L., Fumagalli, R., Paoletti, R., and Catapano, A. L. 1996. "Effect of Lacidipine on Fatty and Proliferative Lesions Induced in Hypercholesterolaemic Rabbits," *British Journal of Pharmacology* 118(2):215-219) isradipine (Donetti, E. et al. op cit. 1997), lercanidipine (Soma, M. R., et al. op cit. 1998), carvedilol (Wu, T. C., Chen, Y. H., Leu, H. B., Chen, Y. L., Lin, F. Y., Lin, S. J., and Chen, J. W. 2007. "Carvedilol, A Pharmacological Antioxidant, Inhibits Neointimal Matrix Metalloproteinase-2 and -9 in Experimental Atherosclerosis," *Free Radical Biology and Medicine* 43(11):1508-1522), probucol (Donetti, E., Soma, M. R., Barberi, L., Paoletti, R., Fumagalli, R., Roma, P., and Catapano, A. L. 1998. "Dual Effects of the Antioxidant Agents Probucol and Carvedilol on Proliferative and Fatty Lesions in Hypercholesterolemic Rabbits," *Atherosclerosis* 141(1):45-51; Kuzuya, M. and Kuzuya, F. 1993. "Probucol as An Antioxidant and Antiatherogenic Drug," *Free Radical Biology and Medicine* 14(1):67-77), BO-653 (2,3-dihydro-5-hydroxy-2,2-dipentyl-4,6-di-tert-butylbenzofuran) (Cynshi O, Kawabe Y, Suzuki T, Takashima Y, Kaise H, Nakamura M, and 12 others 1998. "Antiatherogenic Effects of the Antioxidant BO-653 in Three Different Animal Models," *Proceedings of the National Academy of Sciences of the United States of America* 95(17):10123-10128), and gene transfer administered interleukin 10 (von der Thüsen, J. H., Kuiper, J., Fekkes, M. L., de Vos, P., van Berkel, T. J., and Biessen, E. A. 2001. "Attenuation of Atherogenesis by Systemic and Local Adenovirus-mediated Gene Transfer of Interleukin-10 in LDLr−/− Mice," *Federation of American Societies for Experimental Biology Journal* 15(14):2730-2732).

4b(3). Use of Drug-Releasing Ductus-Intramural Implants to Locally Counteract or Reinforce Angiogenic or Other Systemic Medication The reciprocal use of drugs that are released from tiny miniball or stay conformed implants at fixed sites to locally inhibit or counteract the action of an injected or intravenously infused drug that diffuses through the region has no less potential. As with any medication or combination thereof, the miniballs or stays can be open or closed-loop sources. The focused use of counteractants or inhibitors to blank out or exclude a delimited site has numerous potential applications. For example, atherogenesis involves the elaboration of the vasa vasorum with the proliferation of microvessels into the plaque for commensurate perfusion and drainage as a plaque continues to develop.

Any substance in liquid or semiliquid form can also be introduced at a preferred temperature into the lumen by side-looking ejection syringes, or ejectors, or into the lumen wall by side-looking injection syringes, or radial projection unit tool-insert injectors, whether electrical/fluid system-neutral or operated fluidically, as addressed below in the section entitled Radial Projection Units. These disease process generated microvessels tend to be weak and probably render the plaque more readily susceptible to rupture or erosion. The rupture or erosion of such a vulnerable or unstable plaque produces a breach in the intima that prompts the formation of a thrombus, which if not the direct cause, can nevertheless precipitate an acute cardiac event, most often through the release of embolizing debris (see, for example, Frink, R. J., Trowbridge, J. O., and Rooney, P. A. Jr. 1978. "Nonobstructive Coronary Thrombosis in Sudden Cardiac Death," *American Journal of Cardiology* 42(1):48-51).

Thus, in direct intramyocardial injection of an angiogenic agent such as vascular endothelial growth factor or its genetic precursor (see, for example, Kleiman, N. S., Patel, N. C., Allen, K. B., Simons, M., Ylä-Herttuala, S., Griffin, E., and Dzau, V. J. 2003. "Evolving Revascularization Approaches for Myocardial Ischemia," *American Journal of Cardiology* 92(9B):9N-17N) to encourage the development of collateral circulation, the ability to place implants that release antiangiogenic medication ductus-intramurally, that is, within the wall of an atherosclerosed coronary artery situated at the vulnerable or unstable plaque, makes it possible to suppress the concomitant neovascularization of the vasa vasorum. The coexpression of a counteractant to exclude certain targets from reaction is exhibited by malignant tumors, which release antiangiogenic factors that suppress the growth of metastases while releasing vascular endothelial growth factor to stimulate the proximate formation of vessels essential for the primary tumor to expand.

The ability to differentially eliminate a response of plaque vasa vasora to angiogenetic agents administered to treat vascular disease by blocking out local areas has potential value even where surgery is uninvolved (see, for example, Ylä-Herttuala, S. and Baker, A. H. 2017. "Cardiovascular Gene Therapy: Past, Present, and Future," *Molecular Therapy* 25(5):1095-1106; Stewart, D. J., Hilton, J. D., Arnold, J. M., Gregoire, J., and sixteen other authors 2006. "Angiogenic Gene Therapy in Patients with Nonrevascularizable Ischemic Heart Disease: A Phase 2 Randomized, Controlled Trial of AdVEGF(121) (AdVEGF121) [vascular endothelial growth factor delivered in adenovirus] Versus Maximum Medical Treatment," *Gene Therapy* 13(21):1503-1511; Penny, W. F. and Hammond, H. K. 2004. "Clinical Use of Intracoronary Gene Transfer of Fibroblast Growth Factor for Coronary Artery Disease," *Current Gene Therapy* 4(2):225-230; Mukherjee, D. 2004. "Current Clinical Perspectives on Myocardial Angiogenesis," *Molecular and Cellular Biochemistry* 264(1-2):157-167; Freedman, S. B. 2002. "Clinical Trials of Gene Therapy for Atherosclerotic Cardiovascular Disease," *Current Opinion in Lipidology* 13(6): 653-661).

Generally, the ability to block out a circumscribed segment of a vessel wall from uptake of a regionally diffused drug has numerous potential applications in the gastrointestinal tract and airway as well as in the vascular tree. In bypass graft vessels, for example, placing angiogenic agent time-releasing implants at the anastomoses can encourage revascularization of the graft or grafts while other implants that release antiangiogenic agents prevent neovascularization of the vasa vasorum of nonoperated arteries (see, for example, George, S. J., Channon, K. M., and Baker, A. H. 2006. "Gene Therapy and Coronary Artery Bypass Grafting: Current Perspectives," *Current Opinion in Molecular Therapeutics* 8(4):288-294). Similarly, in hybrid revascularization combining bypass surgery with angioplasty (see, for example, Byrne, J. G., Leacche, M., Vaughan, D. E., and Zhao, D. X. 2008. "Hybrid Cardiovascular Procedures," *Journal of the American College of Cardiology Cardiovascular Interventions* 1(5):459-468) where the use of endothelial growth factor is favorable for the bypass but not for the balloon dilation-stressed or stretched artery, the ability to differentially suppress neovascularization of the vessel plaque vasa vasora is advantageous.

Implanted perpendicularly to the longitudinal axis of the ductus, stays do not interfere with smooth muscle function, and nonabsorbed drug-releasing stays with a deeply textured surface become integrated so as never to require recovery once the medication has been expended. Miniballs of like function could also remain. Unlike radiation seeds, which left in place, are limited to low dose-rates or radionuclides (radioisotopes) of short half-life such as Xenon-133 (see, for example, Sekine, T., Watanabe, S., Osa, A., Ishioka, N., and nine other inventors, 2001. "Xenon-133 Radioactive Stent for Preventing Restenosis of Blood Vessels and a Process for Producing the Same," U.S. Pat. No. 6,192,095), ductus-intramurally placed stays and miniballs are practicably recoverable and thus usable for delivering medication or radiation in higher doses for a limited period. In more advanced disease, external beam radiation may be essential to supplement the radiation provided by seeds. In the irradiation intervening tissue, this negates the key benefit in the use of seeds over external irradiation or delivery through the systemic circulation by infusion or ingestion.

In transmyocardial laser revascularization (see, for example, Bhimji, S. 2006. "Transmyocardial Laser Revascularization," *eMedicine*) performed in conjunction with coronary artery bypass surgery (see, for example, Allen, K. B., Kelly, J., Borkon, A. M., Stuart, R. S., Daon, E., Pak, A. F., Zorn, G. L., and Haines, M. 2008. "Transmyocardial Laser Revascularization: From Randomized Trials to Clinical Practice. A Review of Techniques, Evidence-based Outcomes, and Future Directions," *Anesthesiology Clinics* 26(3):501-519; Atluri, P., Panlilio, C. M., Liao, G. P., Suarez E E, and seven other authors, 2008. "Transmyocardial Revascularization to Enhance Myocardial Vasculogenesis and Hemodynamic Function," *Journal of Thoracic and Cardiovascular Surgery* 135(2):283-291; Horvath, K. A. 2008. "Transmyocardial Laser Revascularization," *Journal of Cardiac Surgery* 23(3):266-276; Spiegelstein, D., Kim, C., Zhang, Y., Li, G., Weisel, R. D., Li, R. K., and Yau, T. M. 2007. "Combined Transmyocardial Revascularization and Cell-based Angiogenic Gene Therapy Increases Transplanted Cell Survival," *American Journal of Physiology. Heart and Circulatory Physiology* 293(6):H3311-H3316); Horvath, K. A., Lu, C. Y., Robert, E., Pierce, G. F., Greene, R., Sosnowski, B. A., and Doukas, J. 2005. "Improvement of Myocardial Contractility in a Porcine Model of Chronic Ischemia Using a Combined Transmyocardial Revascularization and Gene Therapy Approach," *Journal of Thoracic and Cardiovascular Surgery* 129(5):1071-1077; Heilmann, C. A., Attmann, T., von Samson, P., Göbel, H., Marmé, D., Beyersdorf, F., and Lutter, G. 2003. "Transmyocardial Laser Revascularization Combined with Vascular Endothelial Growth Factor 121 (VEGF121) Gene Therapy for Chronic Myocardial Ischemia—Do the Effects Really Add Up?," *European Journal of Cardiothoracic Surgery* 23(1):74-80), for example, the direct, nondiffuse, fully contained or circumscribed if not time-released introduction of an angiogenic agent such as matrix metalloproteinase-9 (Johnson, C., Sung, H. J., Lessner, S. M., Fini, M. E., and Galis, Z. S. 2004. "Matrix Metalloproteinase-9 is Required for Adequate Angiogenic Revascularization of Ischemic Tissues: Potential Role in Capillary Branching," *Circulation Research* 94(2):262-268) into the myocardium overlooking the left ventricle would further encourage the formation of capillaries about the lased channels and at the ends of the anastomoses.

Then diffusion to the vasa vasorum of the left anterior descending coronary artery, for example (whether untreated, angioplastied, or stented), would be avoided; however, continued administration of angiogenic agents could be systemic, and if so, likely to encourage further harmful expansion of the vasa vasorum supplying the plaques of the ungrafted, unaffected, or angioplastied arteries. The graft itself will most likely be an internal thoracic artery, which little dependent upon a vasa vasorum, should not require antiangiogenic implants. In this situation, the ability to inhibit an angiogenic response locally within the walls of the coronary arteries by prepositioning artery-intramural implants releasing angiogenic agent inhibitor at the sites of the vasa vasora would assist to truncate continued atheromatous lesioning.

If the nongrafted arteries had been angioplastied, then this procedure may itself have promoted vasal neovascularization. Were a means found for causing the channels to remain patent (see, for example, Krabatsch, T., Schäper, F., Leder, C., Tülsner, J., Thalmann, U., and Hetzer, R. 1996. "Histological Findings after Transmyocardial Laser Revascularization," *Journal of Cardiac Surgery* 11(5):326-331) if not expand into sinuses as earlier postulated, then the epithelialization of the sinuses would likely serve more functional perfusion. Then artery-intramural antiangiogenic implants at the sites or potential sites of plaques would serve to counteract the angiogenic agent or agents while angiogenic agent releasing implants at the anastomoses of the graft or grafts would allow local zones of reinforcement to the angiogenic agent or agents injected or infused to promote revascularization.

4b(4). System Implant Magnetic Drug and Radiation Targeting

Whether additionally coated with medication or radioactive, for example, magnetized miniballs, stays, clasp-jackets, and all stent-jackets, impasse-jackets, and magnet-jackets can be used to concentrate a drug carrier particle or nanoparticle-bound drug and/or radionuclide passing through the circulation, food or chyme bolus, gland exudate, or urine, for example, and draw the drug abaxially through the lumen wall into the lesion (see, for example, Alexiou, C., Jurgons, R., Schmid, R. J., Bergemann, C., Henke, J., and 3 others, 2003. "Magnetic Drug Targeting—Biodistribution of the Magnetic Carrier and the Chemotherapeutic Agent Mitoxantrone after Locoregional Cancer Treatment," *Journal of Drug Targeting* 11(3):139-149; Alexiou, C., Schmid, R. J., Jurgons, R., Bergemann, C., Arnold, W., and Parak, F. G. 2003. "Targeted Tumor Therapy with 'Magnetic Drug Targeting:' Therapeutic Efficacy of Ferrofluid Bound Mitoxantrone," in Odenbach, S. (ed.), *Ferrofluids: Magnetically Controllable Fluids and their Applications, Lecture Notes in Physics* 594:233-251; Lübbe, A. S., Alexiou, C., and Bergemann, C. 2001. "Clinical Applications of Magnetic Drug Targeting," *Journal of Surgical Research* 95(2):200-206; Alexiou, C., Arnold, W., Klein, R. J., Parak, F. G., Hulin, P., and 4 others, 2000. "Locoregional Cancer Treatment with Magnetic Drug Targeting," *Cancer Research* 60(23):6641-6648; Deleporte, A., Flamen, P., and Hendlisz, A. 2010. "State of the Art: Radiolabeled Microspheres Treatment for Liver Malignancies," *Expert Opinion on Pharmacotherapy* 11(4):579-586; Vente, M. A., Hobbelink, M. G., van Het Schip, A. D., Zonnenberg, B. A., and Nijsen, J. F. 2007. "Radionuclide Liver Cancer Therapies: From Concept to Current Clinical Status," *Anticancer Agents in Medicinal Chemistry* 7(4):441-459).

Medication miniballs and stays can thus release medication within the implanted tissue or when suspended within an impasse-jacket, as addressed below in the section entitled Concept of the Impasse-jacket, or within a magnet-wrap, addressed below in the section entitled Concept of the magnet-wrap, or a stent-jacket, and highly magnetized miniballs and stays can be used to attract drugs bound to or with magnetically susceptible carriers. The use of magnetized ductus-intramural implants to define a segment of a ductus for delivery of a drug or drugs is the same as described below for impasse-jackets in the section entitled Cooperative Use of Impasse-jackets in Pairs and Gradient Arrays and same for magnet-wraps, which are limited to large ductus.

The drawing from the circulation of magnetically susceptible drug carrier nanoparticles by a stent- or impasse-jacket, for example, can be used to deliver a drug into the adluminal lesion or simply to prevent the drug from continued travel through the circulation. Interception of a drug before reaching the liver or another structure or organ is one approach to minimizing adverse drug interactions. As addressed below in the section entitled Cooperative Use of Impasse-jackets in Pairs and Gradient Arrays, whether through miniball or stay insertion, lumen segment specification, or magnetic, drug-targeting allows the focused delivery of medication into a lesion that if circulated would indiscrimately disperse the drug throughout the entire body, allow it to interact with other drugs and food, in all cases increasing the risks for producing adverse side-effects.

With a systemic condition such as atherosclerosis where certain segments are acutely affected, a statin is both circulated and concentrated in the lesions by binding only a fraction of the dose to magnetic dose carrier nanoparticles. Situating progressively more strongly magnetized jackets proximadistad, or in order of increasing strength along the bloodstream, some of the drug is delivered to each jacket. In this way, the magnetic field strength of any jacket is kept beneath the value that would cause the lumen to become clogged. Equally contributing to differential delivery when necessary, the drug carrier particles consist of a mixture of separately prepared portions or fractions, each differing in its magnetically susceptible content.

Magnetic marker monitoring (see, for example, Laulicht, B., Gidmark, N. J., Tripathi, A., and Mathiowitz, E. 2011. "Localization of Magnetic Pills," *Proceedings of the National Academy of Sciences of the United States of America* 108(6):2252-2257 Weitschies W, Blume H, Mönnikes H. 2010. "Magnetic Marker Monitoring: High Resolution Real-time Tracking of Oral Solid Dosage Forms in the Gastrointestinal Tract," *European Journal of Pharmaceutics and Biopharmaceutics* 74(1):93-101; Bergstrand, M., Söderlind, E., Weitschies, W., and Karlsson, M. O. 2009. "Mechanistic Modeling of a Magnetic Marker Monitoring Study Linking Gastrointestinal Tablet Transit, in Vivo Drug Release, and Pharmacokinetics," *Clinical Pharmacology and Therapeutics* 86(1):77-83; Corá, L. A., Romeiro, F. G., Américo, M. F., Oliveira, R. B., Baffa, O., Stelzer, M., and Miranda, J. R. 2006. "Gastrointestinal Transit and Disintegration of Enteric Coated Magnetic Tablets Assessed by AC Biosusceptometry," *European Journal of Pharmaceutical Sciences* 27(1):1-8) makes it possible to identify the level or levels along the gastrointestinal tract for optimal absorption of magnetic drug-targeting ferrofluid-bonded drugs (see, for example, Saravanan, M., Bhaskar, K., Maharajan, G., and Pillai, K. S. 2011. "Development of Gelatin Microspheres Loaded with Diclofenac Sodium for Intra-articular Administration" *Journal of Drug-targeting* 19(2):96-103).

Optimization of these agents for absorption will make oral administration possible (see, for example, Cai, Z., Wang, Y., Zhu, L. J., and Liu, Z. Q. 2010. "Nanocarriers: A General Strategy for Enhancement of Oral Bioavailability of Poorly Absorbed or Pre-systemically Metabolized Drugs," *Current Drug Metabolism* 11(2):197-207; Yamanaka, Y. J. and Leong, K. W. 2008. "Engineering Strategies to Enhance Nanoparticle-mediated Oral Delivery," *Journal of Biomaterials Science. Polymer Edition* 19(12):1549-1570; Florence, A. T. 2004. "Issues in Oral Nanoparticle Drug Carrier Uptake and Targeting," *Journal of Drug-targeting* 12(2):65-

70; Florence, A. T. and Hussain, N. 2001. "Transcytosis of Nanoparticle and Dendrimer Delivery Systems: Evolving Vistas," *Advanced Drug Delivery Reviews* 50(Supplement 1):569-889; Florence, A. T. 1997. "The Oral Absorption of Micro- and Nanoparticulates: Neither Exceptional nor Unusual," *Pharmaceutical Research* 14(3):259-266; Thomas, N. W., Jenkins, P. G., Howard, K. A., Smith, M. W., Lavelle, E. C., Holland, J., and Davis, S. S. 1996. "Particle Uptake and Translocation across Epithelial Membranes," *Journal of Anatomy* 189 (Part 3):487-490).

Insertion of a magnetized endoluminal stent for the purpose of targeting drug carrier particles into a lesion or neoplasm appears in the literature no later than 2004 (see, for example, Chen, H., Ebner, A. D., Rosengart, A. J., Kaminski M. D., and Ritter, J. A. 2004. "Analysis of Magnetic Drug Carrier Particle Capture by a Magnetizable Intravascular Stent: 1. Parametric Study with Single Wire Correlation," *Journal of Magnetism and Magnetic Materials* 284:181-194; Chen, H., Ebner, A. D., Kaminski M. D., Rosengart, A. J., and Ritter, J. A. 2005. "Analysis of Magnetic Drug Carrier Particle Capture by a Magnetizable Intravascular Stent: 2: Parametric Study with Multi-wire Two-dimensional Model," *Journal of Magnetism and Magnetic Materials* 293(1): 616-632; Avilés, M. O., Chen, H., Ebner, A. D., Rosengart, A. J., Kaminski, M. D., and Ritter, J. A. 2007. "In Vitro Study of Ferromagnetic Stents for Implant Assisted-magnetic Drug-targeting," *Journal of Magnetism and Magnetic Materials* 311(1):306-311, *Proceedings of the Sixth International Conference on the Scientific and Clinical Applications of Magnetic Carriers*).

While entailing a minor surgical procedure, an extraluminal magnetic stent or impasse-jacket as described herein leaves the lumen clear, the stent not within the lumen so that it attracts the drug carrier nanoparticle-bound drug to itself but rather draws the drug into the lesion or neoplasm, and can usually occupy the spatial volume needed to bring far greater local field intensity than the endoluminal space would allow (see, for example, Polyak, B. and Friedman, G. 2009. "Magnetic Targeting for Site-specific Drug Delivery: Applications and Clinical Potential," *Expert Opinion on Drug Delivery* 6(1):53-70, also cited above in the section entitled Concept of the Impasse-jacket and that below entitled Interception and Recovery of a Miniball Entering the Circulation).

By comparison, an endoluminal paclitaxel eluting stent allows the blood to wash away some of the drug. With a magnetized implant such as an impasse-jacket, magnet-wrap, patch-magnet, or magnetized miniball, stay or array thereof positioned to target the treatment site, ingestible drugs formulated for such use in the vascular tree will free magnetic drug-targeting from the need for an external magnet or magnets and therewith, the clinic. Other routes for vascular or other system ductus delivery amenable to self-administration are subcutaneously implanted direct and central catheter access injection and/or infusion portals. Then, while to emplace a patch-magnet, stent-jacket, or impasse-jacket, for example, will involve a minor surgical procedure, once accomplished, it will be possible to administer a magnetically targetable drug by mouth that on circulating, will be drawn from the bloodstream to the lesion or neoplasm targeted.

In single stage magnetic drug-targeting, a magnetized collar such as a stent- or impasse-jacket is placed in encircling relation to the segment of an artery to be treated, for example. Since the jacket is placed circumadventitially, it draws the ferromagnetic or superparamagnetic drug carrier nanoparticles, for example, into the lesion in the wall of the artery, not to an in the way endoluminal stent. The latter blocks the further passage of the drug into the lesion and is too limited in available space to generate a high gradient local field.

In dual or 2-stage magnetic drug-targeting as an example of multistage magnetic drug-targeting, a first extraluminal intrinsic motion compliant stent or impasse-jacket assists to draw the orally administered drug with carrier nanoparticles toward the villi of an optimal segment of the gastrointestinal tract for passage into the bloodstream (see, for example, Cherry, E. M., Maxim, P. G., and Eaton, J. K. 2010. "Particle Size, Magnetic Field, and Blood Velocity Effects on Particle Retention in Magnetic Drug-targeting," *Medical Physics* 37(1):175-182; Shaw, S. and Murthy, P. V. S. N. 2010. "Magnetic Drug-targeting in the Permeable Blood Vessel—The Effect of Blood Rheology," *Journal of Nanotechnology in Engineering and Medicine* 1(2):021001-021012; Cheng, J., Teply, B. A., Yoon Jeong, S., Yim, C. H., Ho, D., Sherifi, I., and 4 others, 2006. "Magnetically Responsive Polymeric Microparticles for Oral Delivery of Protein Drugs," *Pharmaceutical Research* 23(3):557-564; des Rieux, A., Fievez, V., Garinot, M., Schneider, Y. J., and Préat, V. 2006 "Nanoparticles as Potential Oral Delivery Systems of Proteins and Vaccines: A Mechanistic Approach," *Journal of Controlled Release* 116(1):1-27; Ito, R., Machida, Y., Sannan, T., and Nagai, T. 1990. "Magnetic Granules: A Novel System for Specific Drug Delivery to Esophageal Mucosa in Oral Administration," *International Journal of Pharmaceutics* 61(1-2): 109-117), and a second such implant placed about the target segment along the ductus draws the nanoparticles into the lesion or neoplasm.

The first implant does not allow passage through the villi that the chemistry and shape of the nanoparticles would disallow or disfavor but rather accelerates the congregation over the villi surfaces of the particles and prevents the loss of particles by continued passage through the gastrointestinal tract. Similarly, a duct, artery, or vein of a gland or organ can be collared with an extraluminal magnetic stent-jacket, impasse-jacket, or magnet-wrap (magnet-jacket) to target a hormone, enzyme, or the section associated with that structure. The avoidance of clogging or embolization is achieved by administration in sub-embolic doses. Nonmetallic stent-jackets and impasse-jackets are nonabsorbable; limited-term administration of such medication may use an absorbable jacket as addressed below in the sections on stent and impasse-jackets.

Significantly, stent-jacket, impasse-jackets, and magnet-jackets can all be used to draw and concentrate magnetic drug carrier particles, which most often will be moving through the blood vessel these encircle even though having been implanted with no forethought as to such use. The multimodal potential offered by nanotubules, nanoparticles, and microspheres containing iron oxide or magnetically susceptible metals (cobalt, iron, or cobalt-iron) for concurrent nanoimaging, magnetic drug-targeting, and extracorporeal or remote heat induction applies to miniballs, stays, and the other implants described herein. Extracorporeal heat-ability in turn enables the release or accelerated release of a drug from a drug eluting or drug coated implant, or accelerated uptake of a drug or increased rate of chemical action of a therapeutic substance in the tissue treated.

Heating a miniball or stay, for example, can be used to accelerate the denaturing of a proteinaceous coating such as a tissue solder or the initial setting or curing of a surgical adhesive, for example. Miniballs can implant and radial projection unit side-looking injection tool-inserts can inject medication ductus-intramurally independently of magnetic force, and as addressed below in the section entitled Cooperative Use of Impasse-jackets in Pairs and Gradient Arrays, impasse-jackets can be paired as entry and exit jackets to stipulate the starting and stopping points (levels) for exposure of the lumen to a drug. These techniques allow the local release or the extraction and accumulation from the circulation of a drug or drugs that if circulated would be toxic. Statins are used as exemplary of closely targeted drug delivery, because of the prevalence of arterial disease; virtually every therapeutic substance poses a risk of unwanted side effects if allowed access to the tissue susceptible thus.

Magnetic drug and/or radioisotope (radionuclide) targeting can compensate for or eliminate the requirement for the intrinsic affinity or normal uptake of the drug or therapeutic substance by the target organ or tissue such as radiolabeled iodine by the thyroid gland. Other examples that might be cited are the systemic administration of bevacizumab to target endoglin, thereby to suppress angiogenesis in colon and lung cancer (Wood, L. M., Pan, Z. K., Guirnalda, P., Tsai, P., Seavey, M., and Paterson, Y. 2011. "Targeting Tumor Vasculature with Novel Listeria-based Vaccines Directed against CD105," *Cancer Immunology and Immunotherapy* 60(7):931-942), and the use of Listeria-based vaccines to target breast cancer (Kim, S. H., Castro, F., Paterson, Y., and Gravekamp, C. 2009. "High Efficacy of a Listeria-based Vaccine against Metastatic Breast Cancer Reveals a Dual Mode of Action," *Cancer Research* 69(14): 5860-5866).

That an impasse-jacket will stop any magnetically susceptible matter regardless of its chemistry or physiological association means that drugs and/or others pharmaceuticals or therapeutic substances can be delivered to it in any combination in any sequence. Varying the susceptible content of the miniball and/or the strength of magnetization of successive impasse-jackets allows some measure of direction to one of several impasse-jackets when present; however, multiple jackets are reliably addressed by direct injection. Until means for the oral administration of the substance or load intended for delivery to a given jacket are available, Impasse-jackets used at the inlet and outlet of a luminal segment, organ, or gland that necessitate frequent dosing will require a lead-in catheter with injection portal at the body surface. Application to the thyroid gland is briefly mentioned in the sections below entitled Stent-jackets and Stent-jacket Supporting Elements: Structural and Functional Considerations and Subcutaneous, Suprapleural, and Other Organ-attachable Clasp- or Patch-magnets.

Radionuclide carrier nanoparticles or microspheres, for example, can be introduced by infusion or injection upstream from a stent-, impasse-, magnet-jacket, or patch-magnet, for example, to be drawn from the passing blood up against and into the lesion. Clasp- or patch-magnets applied to the surface of an organ can be used to draw drug carrier nanoparticles from the blood. This brute-force approach can be used to deliver antineoplastic drugs to the affected organ with or without matter for concurrent or subsequent radiofrequency hyperthermia or thermablation. This differs from the metabolic targeting of an organ to deliver radiofrequency heatable particles in necessitating a preliminary invasive procedure to place the magnetic implants, which can, however, be made to disintegrate without necessitating a second procedure to remove it.

By comparison, metabolic targeting is completely noninvasive, but dependent upon the development of substances naturally drawn to the target organ (see, for example, Kennedy, L. C., Bickford, L. R., Lewinski, N. A., Coughlin, A. J., Hu, Y., Day, E. S., West, J. L., and Drezek, R. A. 2011. "A New Era for Cancer Treatment: Gold-nanoparticle-mediated Thermal Therapies," *Small* 7(2):169-183; Cherukuri, P. and Curley, S. A. 2010. "Use of Nanoparticles for Targeted, Noninvasive Thermal Destruction of Malignant Cells," *Methods in Molecular Biology* 624:359-373; Cherukuri, P., Glazer, E. S., and Curley, S. A. 2010. "Targeted Hyperthermia Using Metal Nanoparticles," *Advanced Drug Delivery Reviews* 62(3):339-345; Cardinal, J., Klune, J. R., Chory, E., Jeyabalan, G., Kanzius, J. S., Nalesnik, M., and Geller, D. A. 2008. "Non-invasive Radiofrequency Ablation of Cancer Targeted by Gold Nanoparticles," *Surgery* 144 (2):125-132; Curley, S. A., Cherukuri, P., Briggs, K., Patra, C. R., Upton, M., Dolson, E., and Mukherjee, P. 2008. "Noninvasive Radiofrequency Field-induced Hyperthermic Cytotoxicity in Human Cancer Cells Using Cetuximab-targeted Gold Nanoparticles," *Journal of Experimental Therapeutics and Oncology* 7(4):313-326; Gannon, C. J., Cherukuri, P., Yakobson, B. I., Cognet, L., Kanzius, J. S., Kittrell, C., Weisman, B., Pasquali, M., Schmidt, H. K., Smalley, R. E., and Curley, S. A. 2007. "Carbon Nanotube-enhanced Thermal Destruction of Cancer Cells in a Noninvasive Radiofrequency Field," *Cancer* 110(12):2654-2665; Klune, J. R., Jeyabalan, G., Chory, E., Kanzius, J. S., and Geller, D. A. 2007. "Pilot Investigation of a New Instrument for Non-invasive Radiowave Ablation of Cancer," *Journal of Surgical Research* 137:263).

Seed and irradiated stays or miniballs implanted within or close to the lesion ab initio can emit radiation as well. Except for those with a punched (perforated) base-tube, a stent-jacket can provide not only the magnetic field for use with an implant or an injected or infused drug and/or radioisotope-bound nanoparticle-containing ferrofluid, for example, but can be coated with tissue-isolating radiation shielding. The shielding, to which body tissues will be exposed if incorporated into the absorbable matrix of an absorbable stent-jacket, for example, once dissipated, can consist of an overlapping gold or platinum particulate. Other shielding materials, tungsten, iridium, and osmium, are toxic and require nonabsorbable encapsulation for chemical isolation such as with gold.

Bioabsorbable polymers are numerous and addressed below in the section entitled Absorbable Base-tube and Stent-jacket, Miniball, Stay, and Clasp-magnet Matrix Materials. To allow addition to any preexisting stent-jacket, the shielding is glued to the outer surface of the stent-jacket as an elastic polymeric matrix layer containing one or a combination of the foregoing materials embedded as an overlapping particulate. If the stent-jacket is absorbable, then the matrix of the shield layer is absorbable as well. Unlike gold compounds administered orally in the form of a powder, residual elemental gold or platinum are not absorbed and not toxic. If an absolute amount of a potentially toxic particulate is used in an absorbable implant such as a stent-jacket, then it is chemically isolated by nonabsorbable encapsulation, metallic or polymeric.

If the use of large or multiple absorbable shielded stents pose the risk of toxicity and the particulate is not to remain as a residue but be absorbed at a rate subtoxic for the specific substance, then different thicknesses of a shield particle-encapsulating coating polymer and/or polymers with different rates of absorption are used to stage dissolution in fractions. The same measures pertain to the dissipation of ferromagnetic particulate embedded in an absorbable stent-jacket, which if iron must be controlled in rate and if sintered lanthanoid must be permanently encapsulate, as addressed below in the section entitled Absorbable Base-tube and Stent-jacket, Miniball, Stay, and Clasp-magnet Matrix Materials. Within the size constraints imposed, plastic radiation barriers do not afford adequate shielding. Radiation shielding for higher dose-rate emissive material is also addressed below in the section entitled Stent-jackets and Stent-jacket Supporting Elements.

The thickness of the shielding layer applied to the base-tube is varied in proportion to the level of radiation to be shielded up to the point where pliancy sufficient to comply with the intrinsic action in the substrate ductus is significantly degraded. An impasse-jacket encircles the ductus in a magnetized grid that allows the use of a powerful external (extracorporeal) electromagnet to extract a trapped miniball or any magnetically susceptible residue. Where circumductal space is inadequate, the fine gauge and round contour of the wires of the extraction grid, both of which factors may militate against achieving the required field strength to stop a passing microsphere or nanoparticle containing magnetically susceptible matter when intrinsically magnetized, even with a magnetized coating, a chemical isolation-encapsulated neodymium bar magnetized normal to the lumen axis is fused or bonded to the exterior surface of the grid in long coaxial relation and aside from the potential extraction path.

If necessary, more distant but more powerful patch-magnets can also be placed with magnetic field oriented perpendicularly to the jacket. Like stent-jackets, impasse and magnet-jackets can also include some tissue surrounding the ductus. For stenting, this allows the use of a tissue hardener to allow placing the intravascular component of the extraluminal stent or ductus-intramural implants (miniballs or stays) when the wall of the ductus is too thin to be implanted or too weak to withstand the tractive force applied to the ductus-intramural implants to open the lumen. Unless a stent-jacket is absorbable so that an underlying extraction grid will be exposed upon its dissolution, it cannot, as does an impasse-jacket, allow a suspended miniball to be noninvasively extracted, but can incorporate radiation shielding.

High dose-rate stays, or seed-stays, and the shield-jacket or shielded stent-jacket are placed and removed through the same local percutaneous incision, so that even though the stays must be inserted first, the time other tissue is exposed to the radiation is slight. Since the radiation shield-jacket or shielded stent-jacket encloses the stays, removal of the stays would ordinarily require that the jacket be removed first. However, the need for recovery is avoided by using an absorbable shield and absorbable stays, of which the toxic shielding particles, usually tungsten, are encapsulated in gold. Radiation shielded stent-jackets can be incorporated into a chain with any other type stent or impasse-jackets where each jacket is selected to treat the segment it encircles.

When miniballs, placement requires triple access, transluminal for the miniballs, through a local incision for the local shielding stent-jacket, and another incision to place a second shielded stent-jacket or impasse-jacket with absorbable shield downstream to trap any miniball that accidentally enters the bloodstream. The latter is placed first, the local shielding jacket second, and the miniballs last. Reasons for placing the jacket first, primarily to serve as a barrier to protect against a perforation or radiation on discharge, are addressed below in the section entitled Sequence of Stent-jacket Placement and Implantation. A nonabsorbable local stent-jacket with a radiation shield can be left in place after nonabsorbable seed miniballs have recovered with the tractive electromagnets in the muzzle-head.

When not supported by a downstream external electromagnet to arrest and extract a miniball and/or impasse trap-jacket that accidently enters the circulation, radiation shield-jackets and seed miniballs contain sufficient ferrous matter to assure that the miniballs will remain fixed in place without exerting deflective force on the muzzle-head. Thus, while radiation or seed miniballs that are encapsulated in gold need never be removed, local and usually downstream jackets are still placed for shielding and for positional security. Nonabsorbable radiation shield-jackets and shielded stent-jackets can likewise be left in place, or alternatively, these jackets can be made to be absorbed.

Inasmuch as noninvasive extraction necessitates an uninterrupted path from the adventitia to the extraction end-point outside the ductus or to the exterior, an impasse-jacket provides an extraction grid of fine wire strongly magnetized at a strength normal to the longitudinal axis that drops off moving away to either side from the center. In an impasse-jacket to serve as a trap-jacket, the strength of magnetization about the circumference may be uniform, or to favor attraction to the arc closer to the body surface through which a prospective extraction would be performed, eccentric. Similarly, in impasse-jackets to draw medication from the passing luminal contents, the strength of magnetization is eccentric according to the arcuate distribution of the lesion targeted. A radiation shield, however, must be continuous, so that when the shield is nonabsorbable, the requirements for radiation shielding and extractability directly conflict.

For this reason, the radiation shield is usually made to break up after the radiation has become depleted or is made noninvasively destructible on demand through the inclusion of continuous ferrous matter to allow magnetic or electromagnetic heat induction, as addressed above in the sections entitled Field of the Invention and Implants that Radiate Heat On Demand, among others Destruction thus requires that the shield layer incorporate sufficient continuous ferrous matter to allow noninvasive dissolution by magnetic or electromagnetic heat induction. An absorbable stent-jacket can incorporate an extraction grid, but practical extraction grids must usually be made of magnetizable stainless steel, which unlike magnesium, for example, is not absorbable.

To avoid tunical delamination or pull-through or the extraction of the ductus-intramural implants through the adventitia, stent-jackets should exert the least magnetic tractive force, whereas impasse-jackets must provide sufficient force to extract relatively low susceptibility particles, for example. Neodymium magnets should not demagnetize over time as to necessitate compensatory overmagnetization for use in the very young. If after decades this becomes a concern, the stent-jacket should be recovered and replaced. Thus, stent-jackets but not impasse-jackets, which are devised to allow extraction out the sides, can be shielded. To strengthen the tractive force, the gauge of the grid wire in an impasse-jacket must be increased.

An impasse-jacket of this kind can also serve as a stent-jacket only so long as this increase does not significantly affect its compliance with the action in the ductus. That requires dispensing with an intrinsically flexible base-tube and instead using spring hinges as used in impasse-jackets generally. Where injury to the surrounding tissue is not a concern, such as when the segment treated extends past the jacket margins and the lesion is thick enough to absorb the radiation, an impasse-jacket can be used with high dose-rate miniballs to expedite extraction following short-term exposure. However, it is not able to provide shielding. Depending upon the surrounding anatomy, retrieval can be conventional through the grid with the use of a high power external electromagnet or transluminal using the recovery electromagnets in the barrel-assembly muzzle-head.

Shielding is, however, compatible with the application of a high intensity radiofrequency alternating magnetic field for the purpose of heating implants containing ferrous and/or cobalt-chromium alloy matter, for example, encircled within the shielded stent-jacket to accelerate the release and/or uptake of a drug applied as a coating to miniballs, for example, as addressed below in the section entitled Extracorporeal Energization of Intrinsic Means for Radiating Heat from within Medication Implants and Medication and/or the Tissue bonding-Coatings of Implants. Unless exceptionally the stent-jacket has been placed solely to attract and shield against radiation emitting matter for a limited time after which it is intended to be removed, the incorporation of a shielding layer or layers in the base-tube is practicably incompatible with direct extraction.

Instead, the recovery electromagnets in a barrel-assembly would have to extract the implants endoluminally, requiring reentry. An impasse-jacket is configured to allow radially outward extraction of a miniball from within the lumen to the exterior with the aid of an extracorporeal electromagnet and cannot be continuously shielded over any portion of the circumference essential for extraction. Because it still presents obstructive areas at the surface, even a stent-jacket without a continuous layer of shielding and having a punched base-tube is unsuited to the direct extraction of miniballs or carrier nanoparticles.

4b(5). Circulating Drug-Blocking and Drug Interaction Avoidance

Drug-targeting through local release and uptake not only focuses drug delivery in the diseased tissue, but by substantially withholding the drug from the circulation, minimizes the potential for adverse interactions with any other drug or nutrient in the circulation. Reciprocally, an unpaired impasse-jacket, for example, can be positioned to remove a drug from the circulation thereby preventing a lesion or structure from exposure to that drug. Provided the substances essential are available, a segment of an artery, the liver, or a kidney, for example, can be targeted for receiving or for not receiving a drug, for example.

Removal can be through the release of a second substance such as by the infusion, injection, or injection of a third substance and/or heat that reverses, counteracts, or neutralizes the first or by extracting the first substance by the magnetic field of the magnetized miniball, stay, array thereof, impasse-, stent-, or magnet-jacket, or patch-magnet. The avoidance of adverse side effects and drug-drug interactions is addressed above in the section entitled Field of the Invention and below in the section entitled Cooperative Use of Impasse-jackets in Pairs and Gradient arrays, among others.

Magnetic drug carrier nanoparticles used to treat lesions in the lumen wall are ferrobound so that upon release from a miniball suspended in the lumen by an impasse-jacket, for example, upon dissolution by the passing blood, infusion of another substance, and/or the application of heat, the drug is drawn by the magnetically susceptible component against the lumen wall and into the lesion. By contrast, particles used to treat organs can be ferro co-bound so that only the susceptible component of or enclosed with the particles are drawn to the impasse-jacket, while the drug or radionuclide is carried forward in the bloodstream, for example, into the target organ.

A second impasse-jacket at the end of the treatment segment or target organ can release a reversal or neutralizing substance, whether released by the first substance or another chemical or an enzyme. The ability to selectively pass and prevent certain drugs from continued passage to or from the liver in particular has profound drug interaction implications. If the dose is large enough to risk clogging an impasse- or stent-jacket, for example, then successive jackets along the artery, for example, are positioned in order of increasing field strength for the expected range in blood pressure.

The field strength produced by the jackets must also take the blood pressure, velocity, and posture into account (see, for example, Cherry, E. M., Maxim, P. G., and Eaton, J. K. 2010, op cit; Haverkort, J. W., Kenjeres, S., and Kleijn, C. R. 2009. "Computational Simulations of Magnetic Particle Capture in Arterial Flows," *Annals of Biomedical Engineering* 37(12):2436-2448). Magnetic drug-targeting, for example, is addressed above in the section entitled Drug-targeting Miniballs and Stays and below in the sections entitled Concept of the Impasse-jacket and Miniball and Ferrofluid-borne Particle-impassable Jackets, or Impasse-jackets, among others.

That drugs posing a risk to a certain organ or lesion can be prevented from reaching that part where drug interaction is uninvolved is obvious. The blocking of a particular organ or luminal lesion from exposure to a drug in the circulation by removing the drug before it reaches that structure pertains to larger lumina and structures so that where the drug is not re-released past the structure, collateral circulation should still deliver the drug past that blocked out. Adverse interaction avoidance is pertinent whether the drugs are to treat the same condition, the condition is ductus situated, to treat independent and unrelated (trans-nosological), or interactive (trans-syndromal) comorbidity (see, for example, McCarthy, C., Clyne, B., Corrigan, D., Boland, F., Wallace, E., and 5 others 2017. "Supporting Prescribing in Older People with Multimorbidity and Significant Polypharmacy in Primary Care (SPPiRE): A Cluster Randomised Controlled Trial Protocol and Pilot," *Implementation Science* 12(1):99; Stokes, J., Kristensen, S. R., Checkland, K., Cheraghi-Sohi, S., and Bower, P. 2017. "Does the Impact of Case Management Vary in Different Subgroups of Multimorbidity? Secondary Analysis of a Quasi-experiment," *BioMed Central Health Services Research* 17(1):521; Smith, S. M., Wallace, E., O'Dowd, T., and Fortin, M. 2016. "Interventions for Improving Outcomes in Patients with Multimorbidity in Primary Care and Community Settings," *Cochrane Database of Systatic Reviews* 3:CD006560; Valderas, J. M., Starfield, B., Sibbald, B., Salisbury, C., and Roland, M. 2009. "Defining Comorbidity: Implications for Understanding Health and Health Services," *Annals of Family Medicine* 7(4):357-363). Care in comorbidity may differ in a system of socialized medicine (see, for example, Meranius, M. S. and Josefsson, K. 2017. "Health and Social Care Management for Older Adults with Multimorbidity: A Multiperspective Approach," *Scandinavian Journal of Caring Sciences* 31(1): 96-103).

The risk of rhabdomyolysis when both statins and fibrates and/or niacin are administered, for example, is addressed below in the section entitled Cooperative Use of Impasse-jackets in Pairs and Gradient Arrays. Numerous methods are provided herein for accelerating uptake, to include drug carrier nanoparticles that allow not only drawing the drug toward an impasse-jacket surrounding the lesioned segment, for example, but also allow the medication to be heated with the aid of a high intensity alternating magnetic field, as addressed in in the section below entitled System Implant Magnetic Drug and Radiation Targeting, among others. Unlike a radio frequency alternating magnetic field, high intensity focused ultrasound directly heats tissue rather than a target containing ferrous or titanium matter implanted within the tissue.

4b(6). Drug-Targeting Miniballs and Stays

Miniballs and stays that generate a magnetic field of the required strength can be used to attract magnetic drug and/or radionuclide carrier nanoparticles, microspheres, or miniballs containing such particles from the passing luminal contents. This is especially valuable along the bloodstream, but also along a peristaltic ductus such as the digestive tract, where an endoluminal stent fails to comply with if not resists peristalsis, and usually causes significant chronic irritation at the margins. An endoluminal stent is also likely to have too little space to include sufficient magnetic material and draws the drug carrier particles to itself, obstructing and thus minimizing if not preventing delivery to the target tissue behind (outside, beyond, surrounding) it.

A holding impasse-jacket can be used, for example, to preposition a smart pill by suspension within the circulation for response to a programmed condition of blood chemistry should such arise, without the need for monitoring. Unlike those suspended in the bloodstream by means of impasse-jackets, addressed below in the section entitled Concept of the Impasse-jacket, miniballs and stays used without a holding jacket must be implanted ductus-intramurally. Magnetized stays and miniballs can be used in multistage drug targeting where the other components placed at intervals along the lumen are impasse-jackets or patch-magnets, for example.

Other sections herein pertaining to this include, in order, System Implant Magnetic Drug and Radiation Targeting, Circulating Drug Blocking and Drug Interaction Avoidance, Endoluminal Prehension of Miniballs and Ferrofluids, Concept of the Impasse-jacket, Uses of Impasse-jackets, Cooperative Use of Impasse-jackets in Pairs and Gradient Arrays, and Chemical Control over Implants and Coated Implants, to Include Miniballs, Stays, and Prongs. To achieve the least weight and size that will be fully dependable; neodyimium iron boron, that material currently known with the highest energy product, or magnetic field strength per unit mass, is incorporated, usually as a continuous core.

This material toxic and an outer layer aiding to produce a deeply textured surface, magnetized miniballs and stays are biocompatibly coated by plating, Microfusion®, as addressed below in the section entitled Stent-jackets and Stent-jacket Supporting Elements, or polymeric encapsulation. Except for a coating of surgical cement, the space constraints will usually disallow any significant outer layering with medication. All miniballs and stays for retentive infiltration by the surrounding tisssue are given a deeply textured surface which also helps to retain any cement used and gradually replaced by the tissue. Once a miniball with deep surface texture becomes infiltrated with tissue, an impasse-jacket allows its extraction with the aid of an external electromagnet; otherwise, such miniballs should be left in place. If a need for resonance imaging arises, the miniball is extracted by means of a sudden pulse from a powerful external electromagnet.

Magnetized miniballs are oriented to be attracted by, that is, for opposite polarity to, an external electromagnet as might later be needed to extract these. Immediately after placement, an external magnet is used to orient the miniball or miniballs before the surrounding cellular exudate has the time to congeal, or coagulate. All but the largest stays are magnetized along their average or implied long axis, so that attractants are drawn to their tips. Such stays can also incorporate separate magnets toward the tips. Longitudinally extended and allowing some clearance from the outer surface of the ductus, a magnetized collar or extraluminal stent, whether an impasse-jacket or a stent-jacket with tiny magnets mounted about its outer surface, does not have the flexibility to conform to the passing constrictive wave as the outer surface of the gut, for example, is drawn inward (centrally) away from the collar.

Although the stent-jacket base-tube or the impasse-jacket wire mesh does not conform to the inward or central excursion of peristalsis, it does comply with any outward excursion and is therefore nonconstrictive. The increase in field strength required to keep the susceptible matter within range due to wall recession as the wave passes is insignificant even for the treatment of Crohn's disease, much less esophageal cancer. For nonadvanced regional enteritis, it can be significant. In critical contrast to an extraluminal stent, an endoluminal stent draws drug/or radionuclide carrier particles entirely through the lumen wall; however, the abluminal tractive reach limited by the force exerts, a magnetized miniball or stay does not draw carrier particles beyond (radially outward from) its own position as would an impasse-jacket that encircled the ductus.

For intramural delivery, the drug carrier particles or microspheres are formulated for quick dissolution and release, whereas for delivery beyond the stent requires a fraction or a separate dose formulated for delayed release. If disease would spread from the outer surface of the gut to the mesentery (*The Merck Manual of Diagnosis and Therapy*, 18th Edition, 2006, Section 2, Gastrointestinal Disorders, Section 18, "Inflammatory Bowel Disease," page 152), for example, an extraluminal chain-stent, because it substantially surrounds the lesion, reduces access of the disease to healthy tissue outside the stent. With respect to the Crohn's example mentioned in the section above entitled Field of the Invention, extraintestinal symptoms resulting from the spread of disease from the gut are restrained, but not symptoms that appear separately.

The systemic medication necessary to suppress the separate symptoms should be less. As any magnetic drug carrier particle attractor, intravascular, miniballs and stays draw carrier particles up to the radial distance at which these are infixed but then obstruct the drug and/or radionuclide from being drawn beyond itself to the exterior surface of the ductus, much less beyond. So long as disease is confined to portions of the ductus adluminal to the miniballs or stays, drug-targeting magnetic miniballs or stays should suffice for medical management. Here too, either an initial nonmagnetic coating or delayed dissolution and release of the magnetic carrier bound drug allows the delivery of the drug or drugs radially outward from the stay or miniball as the target. Disease that is transmural, that is, which has progressed to involve the ductus wall through and through justifies the addition of an extraluminal stent through a small laparoscopic entry portal local to the lesion.

Miniballs should be marked to indicate the north pole, and the magnetic orientation of intraluminal and extralumal implants should be coordinated. In the gut, the barrel-assembly is introduced rectally as is an endoscope with no incision involved. Individual drug-targeting stays are placed laparoscopically with a suitable pliars-configured or stay insertion tool as described below in the section of like title. Miniballs and stays have no significant longitudinal extension, so that used in a peristaltic ductus, whether the gut, a ureter, or gamete tube, both comply with the passing wave while drawing magnetically susceptible matter from the passing lumen contents, but except as indicated above, no farther radially than their own position. Miniballs and stays that are dropped are readily recovered with the immediately present tool that is used to place these, that is, the recovery electromagnets in the barrel-assembly muzzle-head or the stay insertion tool, or a magnet-tipped catheter, or probe.

Magnetized miniballs and stays coated with an initial dose to treat the abluminal portions of the ductus or achieve good concentration at the treatment site immediately can be left in place and thereafter used to attract subsequent doses whenever administered, whether by infusion, injection, or ingestion. A multiple radial discharge barrel-assembly with the recovery electromagnets momentarily switched off driven by a linear positioning stage can place miniballs in a close or high density formation to concentrate the substance or substances drawn into a lesion having longitudinal extension. Using miniballs, an external electromagnet is used to align the field of each before the landing point of each has had the opportunity to coagulate or congeal. Asymmetrical, the fields of stays spontaneously align.

4c. Implants that Radiate Heat on Demand

Implants, to include those ductus-intramural, or miniballs and stays, containing continuous ferromagnetic material such as in the form of encapsulated plates can be heated by placing the patient in a radiofrequency alternating magnetic or electromagnetic field, the temperature noninvasively monitored by means of an equivalent temperature-calibrated eddy current detector. While more pertinent to stent-jackets, ductus-intramural implants that radiate heat on demand from outside the body can also be used for hyperthermic therapy, to apply followup thermoplasty to noninvasively debulk postprocedural hyperplasia, accelerate the dissolution and/or uptake of drugs at the implant site, initiate or accelerate the dissolution of an absorbable implant, and/or to release or accelerate the setting time of an adhesive or protein solder, for example.

Stent-jackets for noninvasive heating incorporate as many gas exchange perforations as necessary, resistance posed to the eddy currents compensated for by increasing the intensity of induction. Implants encompass both those circumductal, such as stent-jackets, impasse-jackets, and claspmagnets, as well as those ductus-intramural, consisting of miniballs and stays. Shallow implants are usually warmed (or chilled) directly with the aid of a vortex tube-based, nominally 'cold,' air gun, which is equally usable for heating, or an electrical hand dryer, for example, while remote heating of more deeply placed implants is usually by means of induction in a ferromagnetic particulate embedded within the material of the implant by placing the patient in a radiofrequency alternating magnetic field, the means for accomplishing this magnetically addressed below in the section entitled Heating of Implants and Coated Implants, to Include Miniballs, Stays, and Prongs Using Implant-passive Ductus-external or Extrinsic Means.

This property in a temporary or absorbable implant can be used to direct dissolution of the implant on demand. While most often pertinent to stent-jackets, remote warming and dissolution apply to every type implant described herein. The eventual object of oral administration will allow self medication by the patient away from the clinic, without the need for infusion or injection through a subcutaneously implanted portal, as addressed above in the section above entitled System Implant Magnetic Drug and Radiation Targeting and in the section below entitled Cooperative use of impasse-jackets in pairs and gradient arrays. When the implant collars about the ductus, drug carrier nanoparticles, for example, injected upstream will be drawn up against the lumen wall within the collared segment.

Absorbable implants that are made to radiate heat on demand can also be dissipated on demand, with drugs or other therapeutic substances incorporated into the absorbed matrix released as well. To do this, heating is not to the tissue injuring melting point but to only the temperature needed to release bound water with or without dissolution enzymes from a hydrogel likewise embedded in the matrix. Implants remotely energized to radiate heat in situ are addressed below in the section entitled Extracorporeal Energization of Intrinsic Means for Radiating Heat from within Medication Implants and Medication and/or the Tissue Bonding-coatings of Implants.

The same nanoparticles that allow heating in an alternating magnetic field produced with a magnetic resonance machine or high amplitude alternating magnetic field generator make possible magnetic drug-targeting in a nonalternating magnetic field. With an extraluminal stent encircling the ductus (usually a blood vessel) without, rather than an endoluminal stent, which inside the lumen draws drug carrier nanoparticles, for example, to itself rather than into the tissue adluminal to it, the drug is drawn into the diseased tissue. The distinction between heating implants by radiation or conduction from an extrinsic heat source and including means within the implants that allow intrinsic heat generation is addressed below in the section entitled Extracorporeal Energization of Intrinsic Means for Radiating Heat from within Medication Implants and Medication and/or the Tissue Bonding Coatings of Implants.

Thus, miniballs and drug carrier nanoparticles are first drawn to the stent-jacket, holding jacket, or magnet-jacket collaring about a blood vessel, for example, whereupon heating the jacket and apposed drug delivery agent or agents implants accelerates the dissolution and uptake of the medication by the lesion. When the core of a miniball with multiple layers of medication or other therapeutic substance such as a surgical cement, for example, is made to radiate heat, the layer having the lowest breakdown or melting point will liquify or melt first, allowing drugs or other therapeutic substances with different breakdown points to be sequenced for delivery. Applying the medication or other therapeutic substance with the lowest melting point as the outermost layer results in the release of that substance first. By shutting off and restarting the alternating magnetic field, each successive layer can be heat-released at any interval desired. Alternatively, each layer can be formulated to dissolve at successive intervals postoperatively.

The use of a magnetic resonance machine or a high amplitude alternating magnetic field applicator to heat the implants described herein is also addressed below in the section entitled Extracorporeal Energization of Intrinsic Means for Radiating Heat from within Medication Implants and Medication and/or the Tissue bonding-Coatings of Implants. Made of or coated to include materials that can be excited when placed in an extracorporeal magnetic field alternated at a radiofrequency, the implants described herein, to include miniballs, stays, and holding jackets, for example, can be made to radiate heat through oscillation and eddy current induction. In such use, the impasse-jacket is given an absorbable polymeric coating that incorporates the nanoparticles. When this matrix can be raised in temperature to a sufficiently molten or fluid state, physical alternation of the nanoparticles also contributes to heating.

Remote heating by such means has been widely studied (see, for example, Purushotham, S., Chang, P. E., Rumpel, H., Kee, I. H., Ng, R. T., Chow, P. K., Tan, C. K., and Ramanujan, R. V. 2009. "Thermoresponsive Core-shell Magnetic Nanoparticles for Combined Modalities of Cancer Therapy," *Nanotechnology* 20(30):305101. Luo, Y. L., Fan, L. H., Gao, G. L., Chen, Y. S., and Shao, X. H. 2009. "Fe3O4/PANI/P(MAA-co-NVP) Multilayer Composite Microspheres with Electric and Magnetic Features: Assembly and Characterization," *Journal of Nanoscience and Nanotechnology* 9(11):6439-6452; Dennis, C. L., Jackson, A. J., Borchers, J. A., Hoopes, P. J., Strawbridge, R. and 4 others 2009. "Nearly Complete Regression of Tumors via Collective Behavior of Magnetic Nanoparticles in Hyperthermia," *Nanotechnology* 20(39):395103; Li, F. R., Yan, W. H., Guo, Y. H., Qi, H., and Zhou, H. X. 2009. "Preparation of Carboplatin-Fe@C-loaded Chitosan Nanoparticles and Study on Hyperthermia Combined with Pharmacotherapy for Liver Cancer," *International Journal of Hyperthermia* 25(5):383-391; Maier-Hauff, K., Rothe, R., Scholz, R., Gneveckow, U., Wust, P., and 6 others 2007. "Intracranial Thermotherapy Using Magnetic Nanoparticles Combined with External Beam Radiotherapy: Results of a Feasibility Study on Patients with Glioblastoma Multiforme," *Journal of Neuro-oncology* 81(1):53-60; Baker, I., Zeng, Q., Weidong, L., and Sullivan, C. R. 2006. "Heat Deposition in Iron Oxide and Iron Nanoparticles for Localized Hyperthermia," *Journal of Applied Physics* 99(8) 08H106-08H109; Zhao, D. L., Zhang, H. L., Zeng, X. W., Xia, Q. S., and Tang, J. T. 2006. "Inductive Heat Property of Fe3O4/Polymer Composite Nanoparticles in an AC Magnetic Field for Localized Hyperthermia," *Biomedical Materials* 1(4):198-201; Kawashita, M., Tanaka, M., Kokubo, T., Inoue, Y., Yao, T., Hamada, S., and Shinjo, T. 2005. "Preparation of Ferrimagnetic Magnetite Microspheres for in Situ Hyperthermic Treatment of Cancer," *Biomaterials* 26(15):2231-2238; Ramachandran, N. and Mazuruk, K. 2004. "Magnetic Microspheres and Tissue Model Studies for Therapeutic Applications," *Annals of the New York Academy of Sciences* 1027:99-109; R., DeNardo, S. J., Daum, W., Foreman, A. R., Goldstein, R. C., Nemkov, V. S., and DeNardo, G. L. 2005. "Application of High Amplitude Alternating Magnetic Fields for Heat Induction of Nanoparticles Localized in Cancer," *Clinical Cancer Research* 11(19 Part 2):7093s-7103s; Muraoka, A., Takeda, S., Matsui, M., Shimizu, T., Tohnai, I., Akiyama, S., and Nakao, A. 2004. "Experimental Study of a Novel Thermotherapy for Hepatocellular Carcinoma Using a Magnesium Ferrite Complex Powder that Produces Heat under a Magnetic Field," *Hepatogastroenterology* 51(60):1662-1666; Kobayashi, T., Tanaka, T., Kida, Y., Matsui, M., and Ikeda, T. 1989. "Interstitial Hyperthermia of Experimental Brain Tumor Using Implant Heating System," *Journal of Neuro-oncology* 7(2):201-208).

Ordinarily, ferromagnetic implants disallow the use of magnetic resonance equipment. This is because the axial field places tractive force on the implants risking injury, while the radiofrequency alternating field induces heat that results in burns. However, use of an alternating magnetic field only can also serve as a means for intentionally heating an implant directly or by exciting a resonant circuit embedded within the implant (Niwa, T., Takemura, Y., Inoue, T., Aida, N., Kurihara, H., and Hisa, T. 2008. "Implant Hyperthermia Resonant Circuit Produces Heat in Response to MRI Unit Radiofrequency Pulses," *British Journal of Radiology* 81(961):69-72, available at http://bjr.birjournals.org/cgi/content/full/81/961/69; Morita, M., Inoue, T., Yamada, T., Takemura, Y., and Niwa, T. 2005. "Resonant Circuits for Hyperthermia Excited by RF Magnetic Field of MRI," *INTERMAG Asia Magnetics Conference* 953-954). Digests of the IEEE International).

The resonant circuit is interposed or sandwiched between a double layered mesh in the half-cylinder to be placed more deeply or on the side that will lie more distant from the external extraction electromagnet, for example. Unlike stent-jackets, which use multiple miniballs implanted relatively close to the outer tunic of the ductus where each is drawn by a magnetic force which is close and normal to it, a holding jacket will often secure but a single miniball within the lumen through which contents flow over the additional distance that separates the perimedial from an endoluminal position when the magnetized segment of the jacket is central and less extended.

For use in the gastrointestinal tract, ureters, and gamete-transporting ductus, the magnetic strength must be additionally strong enough to overcome the adaxial (toward the long axis, medial, central, inward) increase in distance due to retraction by the passing contractive waves. In the esophagus and gut, the immediately preceding passage of the bolus poses yet an additional force promoting dislodgement. However, the impasse-jacket strength of magnetization must not be so great as to interfere with ductus-intrinsic muscular action to a degree that would induce dyspagia, for example. Whether a radially symmetrical arrangement of miniballs suspended within the lumen would less likely produce disabling consequences warrants study.

4d. Chemical Adjuvants and Precautionary Measures

4d(1). Administration of Target and Target-Adjacent Implantation-Preparatory Substances Radial projection unit injection tool-inserts allow the local injection of therapeutic substances such as drugs, hormones, enzymes, or a surgical cement into the target and nearby tissue to prepare the ductus for ballistic implantation. Avoidance of the lumen a key object in the use of stays, the extraluminal application of medication is preferred with stays. Therapeutic substances can also be administered systemically or released onto the endothelium through a non-injecting ejection tool-inserts or through a barrel-tube or tubes used as service channels. In addition to conventional types of medication such as antibiotics and antithrombogenics, to better resist migration, delamination, or pull-through, tissue hardening agents that induce the formation of strong tissue about the implants and strong adhesion of the tissue to the implants is used.

Due to the thrombogenicity (thromboplasticity) of introducing multiple punctures through the intima and media, miniballs for implantation into the walls of arteries are given an outer coating of an antiplatelet agent, such as a glycoprotein IIB/IIA inhibitor (abciximab, eptifibatide, tirofiban, lamifiban), or adenosine uptake inhibitor (dipyridamole), and those for veins with an anticoagulant or 'blood thinner,' such as the vitamin K antagonists or coumarins (warfarin and/or heparin) and non vitamin K antagonists (see, for example, De Caterina, R., Husted, S., Wallentin, L., Andreotti, F., Arnesen, H., and 11 others 2012. "New Oral Anticoagulants in Atrial Fibrillation and Acute Coronary Syndromes: ESC [European Society of Cardiology] Working Group on Thrombosis-Task Force on Anticoagulants in Heart Disease Position Paper," *Journal of the American College of Cardiology* 2012 59(16):1413-1425; Weitz, J. I. 2012. "New Oral Anticoagulants: A View from the Laboratory," *American Journal of Hematology* 87 Supplement 1:S133-S136; Bauer, K. A. 2011. "Recent Progress in Anticoagulant Therapy: Oral Direct Inhibitors of Thrombin and Factor Xa," *Journal of Thrombosis and Haemostasis* 9 Supplement 1:12-9; Weitz, J. I., Hirsh, J., and Samama, M. M. 2004. "New Anticoagulant Drugs," *Chest* 126(3):Supplement 265S-286S), thus allowing the systemic dose to be reduced relative to that conventional, and reducing the risk for prolematic bleeding. On healing an extraluminal, with no presence within the lumen, ceases to pose a threat of thrombosis.

Ductus prone to swell if struck from within necessitate the use of miniballs that also contain anti-inflammatory medication, the NSAIDs diclofenac, indometacin, ibuprofen and sulindac, for example, having been found to additionally exert an antiproliferative effect on the smooth muscle cells of the media (Muñoz, E., Valero, R. A., Quintana, A., Hoth, M., Núñez, L., and Villalobos, C. 2011. "Nonsteroidal Anti-inflammatory Drugs Inhibit Vascular Smooth Muscle Cell Proliferation by Enabling the Ca2+-dependent Inactivation of Calcium Release-activated Calcium/Orai Channels Normally Prevented by Mitochondria," *Journal of Biological Chemistry* 286(18):16186-16196; Brooks, G., Yu, X. M., Wang, Y., Crabbe, M. J., Shattock, M. J., and Harper, J. V. 2003. "Non-steroidal Anti-inflammatory Drugs (NSAIDs) Inhibit Vascular Smooth Muscle Cell Proliferation via Differential Effects on the Cell Cycle," *Journal of Pharmacy and Pharmacology* 55(4):519-526). To reduce the risk of infection-mediated pull-through, the implants are additionally coated with an antibiotic, a dose adjusted systemic antibiotic administered as well.

Other measures for reducing the risk of pull-through include use of the minimal retractive magnetic field strength, implants having a textured surface to encourage tissue adhesion and infiltration, or ingrowth, the application of phosphorylcholine and/or dexamethasone or curcumin (references provided below in the section entitled Tissue Reaction Ameliorative Measures), and various bonding agents, such as protein solder or tissue cement, dependent upon the response to be expected for the type and depth of tissue based upon the results of pretesting as addressed below in the section entitled Testing and Tests. Due to the constant replenishment of tissue, adhesives are chosen that will allow infiltration during dissolution so that the implant will become securely anchored and integrated in position.

In the form of smaller miniballs or stays, these substances are solid and can consist of a single or multiple drugs. The heating of solder coated implants following insertion can be used both to release drugs and bind tissue. To minimize the exposure of surrounding tissue to this heat, electrically or fluidically heated heat-windows, as addressed below in the section entitled Thermal Conduction Windows (Heat-windows) and Insulation of the Muzzle-head Body, or syringe solder injectors, as addressed below under the heading Radial Projection Units are used. Alternatively, external ultrasound can be used for heating. Other preparatory agents allow the intentional swelling of the ductus wall, as next addressed, to make thin-walled ductus easier if not possible to implant.

The moisture barrier protected viscoelastic polyurethane (memory) foam lining of the stent-, impasse, and magnet-jackets described facilitate the inclusion of adherent tissue surrounding the outer ductus when thin-walled due to normal anatomy or disease. The treatment of short segments will often recommend the use of stays, as addressed below in the section entitled Circumstances Dissuading or Recommending the Use of Stays. When the same means for inserting ferromagnetic implants to draw a magnetic stent-jacket can be used to introduce the preparatory medication, the treatment site can often be targeted with negligible systemic dispersion. When the drug action response time allows, use of the same barrel-assembly allows single entry and withdrawal.

When a pretest reveals that the wall of the ductus is susceptible to inter or intralaminal separation, small implants consisting of an absorbable and tissue infiltratable solid protein solder can be implanted adjacent to the site to be implanted with the solder melted (denatured) and made to flow by muzzle-head or piped radial projection unit heat-windows, by feeding heated gas down a barrel-tube, or through use of external ultrasound. Following any step involving heating, a cooling catheter, as addressed below in the section entitled Cooling Catheters (Temperature-changing Service-catheters), can be used to hasten the return of heated tissue to body temperature. When the cooling catheter is prepared by having been stored filled with water in a freezer and the same barrel-tube is to be used for discharge, the cooling catheter should be capped to prevent melt water from entering the barrel-tube.

Deeply textured implants can deliver surface depression adherent liquid or semiliquid substances forward into the ductus wall. Using a barrel-assembly, a service-catheter, as addressed below in the section of like title, and using a stay insertion tool, auxiliary syringes, as addressed below in the section entitled Stay Insertion Tool Auxiliary Syringes, make it possible to supplement or coat implants. Outside the bloodstream, a service-catheter also allows the delivery of a gas or an aerosol (mist) whether irradiated or having a fine powder dispersed in it. With the latter, cohesiveness among particles or adhesion to the barrel-tube as service channel without a service-catheter will result in clogging, limiting continued use of any one barrel-tube.

Barrel-tubes as service channels and service-catheters can deliver compatible substances jointly, but unless more than one service-channel—as addressed below in the sections entitled Muzzle-head Access through a Service-channel without the Aid of and by Means of Inserting a Service-catheter and Thermal Ablation or angioplasty- (Lumen Wall Priming Searing- or Cautery-) capable Barrel-assemblies— is available, to deliver substances to be kept separated during delivery requires separation through the use of separate service-channels or service-catheters in sequence.

4d(2). Ductus Wall Tumefacients

Whether the result of disease, an angioplasty, or an atherectomy, excessive thinness of the luminal wall can prohibit implantation to introduce medication or to apply a magnetic stent. Otherwise, numerous vessels, especially veins and elastic arteries having a thin wall and media, even a carotid, may prove difficult or impossible to implant thus. In some instances, implantation is made possible by producing a short-lived or reversible increase in medial thickness. Provided the tenuity is not so extreme or intrinsic strength so lacking that upon subsidence, the implants, even with a fill-coat of protein solder, would perforate through the adventitia, into the lumen, or both, some walls can be brought up to an implantable thickness if tumefied (swollen).

Long-term fillers as opposed to short term swellants are addressed below in the section entitled The Extraductal Component of the Extraluminal Stent and the Means for its Insertion. Administration of a tumefacient specified in this section and drugs specified in the section that follows is begun sufficiently in advance of the procedure that requires it. In muscular arteries, tumefacients, or swelling agents, which increase lumen wall thickness by contracting the smooth muscle cells, are vasoconstrictors that will reduce the diameter of the lumen. This can be a consideration in selecting a barrel-assembly or radial projection catheter of given caliber but will rarely if ever affect the use of stays. Tumefacients not only increase the thickness of the luminal wall allowing it to be implanted but affect other properties of the ductus.

Tumefacients that work by inducing the contraction of medial smooth muscle, for example, increase resistance of the wall to perforation and reduce the luminal diameter.

Tumefacients that work in other ways may not affect luminal diameter but will affect the mechanical properties of the luminal wall. In some instances, the primary object in using a tumefacient may be unrelated to wall thickness. This interaction of key determinants as to the barrel-assembly and exit velocity to be used means that the tests described below in the section entitled Testing and Tests should be performed both before and after any tumefacient contemplated is applied. Tumefacients that affect the ductus over a longer interval that wanted must have an associated counteractant. This can be done to thicken a wall that is or is not too thin to implant but not too weak to retain an implant once inserted.

Tumefaction does not involve the permanent implantation of autologous tissue or a polymer between the intima and adventitia but swelling that is temporary to allow or expedite insertion. Otherwise, liposuctioned fat, for example, can be injected through a service-catheter (qv.) with a hypotube, or with an injection tool-insert (qv.) before implantation. Depending upon lumen caliber, the tumefacient can be released along the lumen wall through the working channel of a fiberoptic endoscope, a barrel-tube used as a service-channel, a service catheter routed through a barrel-tube, or an ejection tool-insert. If not extremely thin-walled, the use of an injection tool-insert or service-catheter with a hypotube at the distal end is possible.

Following the procedure, the wall reverts to its preprocedural condition, the implant or implants retained for a time if necessary with the aid of a surgical cement or protein solder outer layer pending tissue integration. Low melting point solder on miniballs or stays and cyanoacrylate cement on stays can be heated endoluminally by muzzle-head heat-windows or hot-plate tool-inserts. Heating thus is focused or aimed and relatively circumscribed. Heating from outside the body using ultrasound, for example, is unfocused and contraindicated for any site close to a developmental ossification or nervous center, for example. When stays are to be used or the ductus is to be stented so that extraluminal access will be required in any event, the tumefacient can be applied to or through the adventitia.

Various approaches to thickening the media include inducing: a. A buildup of osmotic pressure that causes the smooth muscle of the media to contract (see, for example, Ding, Y., Schwartz, D., Posner, P., and Zhong, J. 2004. "Hypotonic Swelling Stimulates L-type Ca2+ Channel Activity in Vascular Smooth Muscle Cells Through PKC [Protein Kinase]," *American Journal of Physiology. Cell Physiology* 2004 287(2):C413-C421); b. A short-lived or reversible swelling reaction to a drug or combination of drugs; c. Sterile inflammation as an immune response; d. Reaction to a change in temperature, e. Reaction to a flow of current at the target site, f. Mechanical irritation through brief oscillation of the target site, and injection of a nonirritating absorbable filler such as used in facial cosmetic surgery.

In an atheromatous artery to receive miniballs, embolic protective devices such as proximal and distal balloon occluders and embolic filters (see, for example, section 4d(2) entitled Ductus Wall Tumefacients and Kobayashi, T. anf Giri, J. 2017. "The Role of Embolic Protection in Carotid Stenting Progress in Cardiovascular Diseases (PCVD)," *Progress in Cardiovascular Diseases* 59(6):612-618; Velasco, A. and Mosimann, P. J. 2013. "Distal Cerebral Protection Device Filled with Calcified Plaque Debris after Carotid Stenting," *Journal of the American College of Cardiology. Cardiovascular Interventions* 6(4):e22-e23; Macdonald, S. 2011. "New Embolic Protection Devices: A Review," *Journal of Cardiovascular Surgery* (Turin, Italy) 52(6):821-827; Eskandari, M. K. 2005. "Cerebral Embolic Protection," *Seminars in Vascular Surgery* 18(2):95-100; Sangiorgi, G. and Colombo, A. 2003. "Embolic Protection Devices," *Heart* (London, England) 89(9):990-992) that is, a potentially embolizing atheromatous debris-intercepting trap-filter or balloon deployed from the nose of the muzzle-head can be prepositioned proximal or distal to or downstream from the site to be treated.

No embolization device completely eliminates the passage of microemboli; however, the number which pass is much reduced (Vos, J. A. 2017. "Evidence Overview: Benefit of Cerebral Protection Devices During Carotid Artery Stenting," *Journal of Cardiovascular Surgery* (Turin, Italy) 58(2):170-177; Kassavin, D. S. and Clair, D. G. 2017. "An Update on the Role of Proximal Occlusion Devices in Carotid Artery Stenting," *Journal of Vascular Surgery* 65(1): 271-275; Knur, R. 2014. "Technique and Clinical Evidence of Neuroprotection in Carotid Artery Stenting," *VASA. Zeitschrift für Gefässkrankheiten* [Journal for Vascular Diseases] 43(2):100-112; Atkins, M. D. and Bush, R. L. 2007. "Embolic Protection Xevices for Carotid Artery Stenting: Have They Made a Significant Difference in Outcomes?," *Seminars in Vascular Surgery* 20(4):244-251). Walls too thin to implant must first be made thicker. Since injection of the ductus wall with a tumefacient or fill-tissue will affect its mechanical properties, the applicable pretest or pretests are performed at the site following injection to thicken, for example. Testing is addressed below in the section entitled Testing and Tests. The results of testing will determine the need for a target tissue binder or hardener, implants with a layer of protein solder or tissue cement, for example, then used.

4d(3). Nontumefacient Enabled Attainment of Implantable Ductus-Intramural Thickness Infrequently, a disease condition, such as inflammation as swelling, a lesion, or inflammation that follows treatment of the lesion will result in a wall thickness sufficient for implantation, although this will usually be at the expense of strength. A malacotic condition can be overcome by using a radial projection catheter to inject an absorbable tissue hardener or fixative, or filler of the kind used in facial cosmetic surgery. An intravascular ultrasound probe, charge coupled device camera, or fluorescence lifetime imaging microscopy, or angioscope—either as a separate device or incorporated into a combination form barrel-assembly—can be used to examine the reaction of the lumen wall to the procedure just completed (see, for example, Savastano, L. E. and Seibel, E. J. 2017. "Scanning Fiber Angioscopy: A Multimodal Intravascular Imaging Platform for Carotid Atherosclerosis," *Neurosurgery* 64(CN Supplement 1):188-198; Savastano, L. E., Chaudhary, N., Murga-Zamalloa, C., Wang, M., Wang, T., and Thompson, B. G. 2017. "Diagnostic and Interventional Optical Angioscopy in Ex Vivo Carotid Arteries," *Operative Neurosurgery* (Hagerstown, Md.) 13(1):36-46; Savastano, L. E., Zhou, Q., Smith, A., Vega, K., Murga-Zamalloa, C., and 11 others 2017. "Multimodal Laser-based Angioscopy for Structural, Chemical and Biological Imaging of Atherosclerosis," *Nature Biomedical Engineering* 1. pii: 0023; Savastano, L. E., Smith, A., Vega, K., Murga-Zamalloa, C., Gordon, D., and 4 others 2016. "Multimodal Endovascular Endoscopy in Carotid Atherosclerotic Disease," *Neurosurgery* 63 Supplement 1:146; Packard, R. R., Zhang, X., Luo, Y., Ma, T., Jen, N., and 7 others 2016. "Two-point Stretchable Electrode Array for Endoluminal Electrochemical Impedance Spectroscopy Measurements of Lipid-laden Atherosclerotic Plaques,"

*Annals of Biomedical Engineering* 44(9):2695-2706; Ma, T., Yu, M., Li, J., Munding, C. E., Chen, Z., Fei, C., Shung, K. K., and Zhou, Q. 2015. "Multi-frequency Intravascular Ultrasound (IVUS) Imaging," *Institute of Electrical and Electronics Engineers Transactions on Ultrasonics, Ferroelectrics, and Freqency Control* 62(1):97-107; McVeigh, P. Z., Sacho, R., Weersink, R. A., Pereira, V. M., Kucharczyk, W., Seibel, E. J., Wilson, B. C., and Krings, T. 2014. "High-resolution Angioscopic Imaging During Endovascular Neurosurgery," *Neurosurgery* 75(2):171-180; Suter, M. J., Nadkarni, S. K., Weisz, G., Tanaka, A., Jaffer, F. A., Bouma, B. E., and Tearney, G. J. 2011. "Intravascular Optical Imaging Technology for Investigating the Coronary Artery," *Journal of the American College of Cardiology. Cardiovascular Imaging* 4(9):1022-1039; Chou, T. M., Fitzgerald, P. J., and Yock, P. G. 2000. "Intravascular Ultrasound," *Chapter* 19 in Baim, D. S. and Grossman, W., *Grossman's Cardiac Caherterization, Angiography, and Intervention*, Philadelphia, Pa.: Lippincott Williams and Wilkins). With a combination-form radial projection catheter, a small intravascular ultrasound probe passed down the bore pre or midprocedurally can be used to observe the effect on wall thickness of the atherectomy just completed using the projection catheter, an angioscope useful to examine the lumen interior.

The administration of a nominally nontumefacient drug specified in this section is begun sufficiently in advance to obtain the desired effect by the time of the procedure. If additional thickness is necessary, projection catheter radial projection unit injection tool-inserts, for example, can be used to deliver a tumefacient and the intravascular ultrasound or angioscope used to confirm the result. The ultrasound cable is then withdrawn and the barrel-assembly passed down through the bore to initiate miniball discharge. In this process, the radial projection catheter is not withdrawn but remains as both atherectomy device and guide catheter. If the pretest prescribed below in the section entitled Testing and Tests indicates a lack of strength that will subside on healing, consideration may be given to using a quick-acting tissue binder-hardener rather than aborting implantation.

The use of a bipartite combination-form angioplasty-capable barrel-assembly represents a reciprocal arrangement, whereby the barrel-assembly is used to perform the atherectomy or other treatment with a viewing probe in its bore. However, in this case, the probe need not be withdrawn; if additional radial projection units are need, a matching combination-form radial projection catheter is slid over the barrel-catheter as guide wire. Vasodilators relax the walls of vessels, which temporarily reduces the intimal-medial thickness, while vasoconstictors (vasopressors) effectively toughen the media, due both to increased medial thickness and vasotension.

Here the application of medication is targeted, the tumefacient, as can any other fluid or semifluid therapeutic substance, injected into the site along the lumen wall to be treated by an injection syringe tool-insert, as addressed below in the section entitled Radial Projection Unit Tool-Inserts, so that the hypertensive effect is substantially confined to the treatment site, making the use of potent hypertensives applicable to patients in whom the systemic use of the same drugs would be ill-advised and avoiding vasoconstriction that reducing the luminal diameter, would hinder intervention. Where apposite, preparatory systemic medication may be prescribed to increase vascular tonus and wall thickness.

Over time, some vasoconstrictors, such as urotensin II, directly stimulate cell proliferation rather than produce this result only indirectly as a consequence of having increased the blood pressure (see, for example, Zhang, Y. G., Li, J., Li, Y. G., and Wei, R. H. 2008. "Urotensin II Induces Phenotypic Differentiation, Migration, and Collagen Synthesis of Adventitial Fibroblasts from Rat Aorta," *Journal of Hypertension* 26(6):1119-1126; Tamura, K., Okazaki, M., Tamura, M., Isozumi, K., Tasaki, H., and Nakashima, Y. 2003. "Urotensin II-induced Activation of Extracellular Signal-regulated Kinase in Cultured Vascular Smooth Muscle Cells: Involvement of Cell Adhesion-mediated Integrin Signaling," *Life Sciences* 72(9): 1049-1060).

Where its systemic use is not contraindicated, urotensin II may effectively contribute needed strength in the airway, for example, (see, for example, Chen, Y. H., Zhao, M. W., Yao, W. Z., Pang, Y. Z., and Tang, C. S. 2004. "The Signal Transduction Pathway in the Proliferation of Airway Smooth Muscle Cells Induced by Urotensin II," [in English] *Chinese Medical Journal* 117(1):37-41). Systemic hypertensives are not used where hypertension and stenosis are primary complaints; however the one-time and highly localized use of a quick-acting tonus-increasing drug poses little risk. The object is to thicken and effectively strengthen the arterial wall so that it can be implanted and not to strengthen the wall postprocedurally. The short-term and localized hypertension subsides following the procedure and does not represent the postprocedural strength of the vessel wall, which is measured using procedures described below in the section entitled Testing and Tests.

Testing is performed in preparation for implantation following angioplasty or atherectomy, if applicable, and before and after administering the drug. The postprocedural administration of a systemic vasoconstrictor is unacceptable with most vascular disease. An alternative approach for sustaining strength long enough to allow tissue recovery without delamination or pull-through is to surround the implant with a surgical cement or protein solder that bonds the implant to and hardens the surrounding tissue. Any stiffening in the ductus wall is tightly focused with little effect on the intrinsic motility of the smooth muscle.

Drugs distinct in pharmacological action, response time, and persistence with the individual or combined potential to cause the ductus wall to increase in thickness more quickly when applied topically (through a service-catheter or auxiliary syringe to be described) include zymosan; carrageenan, dextran, uric acid, adrenalin, tumor necrosis factor-alpha, sterile lipopolysaccharide and lipo-oligo-saccharide endotoxins (see, for example, Kitazawa, M., Oddo, S., Yamasaki, T. R., Green, K. N., and LaFerla, F. M. 2005. "Lipopolysaccharide-induced Inflammation Exacerbates Tau Pathology by a Cyclin-dependent Kinase 5-mediated Pathway in a Transgenic Model of Alzheimer's Disease," *Journal of Neuroscience* 25(39):8843-8853). If necessary, once the thickness will admit implants, the implants can carry a coating of these.

Endotoxins should be kept away from the bloodstream. Antidotes are discussed in the literature (see, for example, Jiang, Z., Hong, Z., Guo, W., Xiaoyun, G., Gengfa, L., Yongning, L., and Guangxia, X. 2004. "A Synthetic Peptide Derived from Bactericidal/Permeability-increasing Protein Neutralizes Endotoxin in Vitro and in Vivo," *International Immunopharmacology* 4(4):527-537; Bhor, V. M., Thomas, C. J., Surolia, N., and Surolia, A. 2005. "Polymyxin B: An Ode to an Old Antidote for Endotoxic Shock," *Molecular BioSystems* 1(3):213-222; Ren, J. D., Gu, J. S., Gao, H. F., Xia, P. Y., and Xiao, G. X. 2008. "A Synthetic Cyclic Peptide Derived from Limulus Anti-lipopolysaccharide Factor Neutralizes Endotoxin in Vitro and in Vivo," *International Immunopharmacology* 8(6):775-781).

Other drugs with the potential to cause an increase in intimal-medial thickness as ligands that bind to Toll-like receptors and thus activate immune cell responses include midazoquinoline, loxoribine, bropirimine, sterile profilin, sterile flagellin (see, for example, Neish, A. S. 2006. "TLRS [Toll-like Receptors] in the Gut. II. Flagellin-induced Inflammation and Antiapoptosis," *American Journal of Physiology. Gastrointestinal and Liver Physiology* 292(2): G462-G466), and polyglycolic acid (see, for example, Ceonzo, K., Gaynor, A., Shaffer, L., Kojima, K., Vacanti, C. A., and Stahl, G. L. 2006. "Polyglycolic Acid-induced Inflammation: Role of Hydrolysis and Resulting Complement Activation," *Tissue Engineering* 12(2):301-308).

Yet other drugs with the potential to cause an increase in intimal-medial thickness are oxysterols (oxidized cholesterol) (see, for example, Lemaire-Ewing, S., Prunet, C., Montange, T., Vejux, A., and six other authors 2005. "Comparison of the Cytotoxic, Pro-oxidant and Pro-inflammatory Characteristics of Different Oxysterols," *Cell Biology and Toxicology* 2005 21(2):97-114; Joffre, C., Leclère, L., Buteau, B., Martine, L., and seven other authors 2007. "Oxysterols Induced Inflammation and Oxidation in Primary Porcine Retinal Pigment Epithelial Cells," *Current Eye Research* 32(3):271-280), thromboxane $B_2$, aldosterone (see, for example, Sun, Y., Zhang, J., Lu, L., Chen, S. S., Quinn, M. T., and Weber, K. T. 2002. "Aldosterone-induced Inflammation in the Rat Heart: Role of Oxidative Stress," *American Journal of Pathology* 161(5):1773-1781), and prostaglandin $E_2$ (see, for example, Lees, P., McKellar, Q. A., Foot, R., and Gettinby, G. 1998. "Pharmacodynamics and Pharmacokinetics of Tolfenamic Acid in Ruminating Calves: Evaluation in Models of Acute Inflammation," *Veterinary Journal* 155(3):275-288; Sidhu, P. K., Landoni, M. F., and Lees, P. 2006. "Pharmacokinetic and Pharmacodynamic Interactions of Tolfenamic Acid and Marbofloxacin in Goats," *Research in Veterinary Science* 80(1):79-90).

Both miniballs and stays can consist of a single drug or aggregations or concentric layers of drugs and can be implanted adjacent or proximal to the site for implantation making it possible to deliver a concentrated dose to a targeted location. Still other drugs with the potential to cause an increase in intimal-medial thickness are fibrinogen, sterile lipoproteins, glycolipids, lipteichoic acid, heparan sulphate fragments, hyaluronic acid fragments, and imiquimod.

4e. Stabilization of the Implant Insertion Site

4e(1). Gross Positional Stabilization (Immobilizaton) of the Implant Insertion Site Peristalsis and the pulse change the radial distance between the target and the longitudinal axis of the lumen, changing the miniball aiming point or the stay insertion site. This must be considered for both arteries and contactile ducti from within the lumen for miniballs and from outside the ductus for stays. Generally, the pulse is frequent but can seldom result in misplacements of any significance, even when implantation is under unpaced automatic positional and discharge control. A reduction in motility can be brought about by numerous drugs, mechanical interventions, and changes in temperature, which latter can be used to reduce motility at the gross, histologic, and metabolic levels.

The use of temperature is addressed below in the section entitled Temperature Stabilization. Where the pulse interferes, a primary method for slowing the heart is chilling; where local anesthesia cannot be used in any event, this method should be considered. Even when treating a coronary artery or vein graft, on-pump operation should seldom prove necessary. Gastrointestinal tract, ureteric, bile, and gamete conduit duct (vasa deferentia, fallopian tubes) peristalsis, however, generate displacements that can result in the longitudinal misplacement of miniballs and the misplacement in depth of stays.

However, peristalsis, while different in form in different type ductus (see, for example, Woodburne, R. T. and Lapides, J. 1972. "The Ureteral Lumen during Peristalsis," *American Journal of Anatomy* 133(3):255-258), is intermittent and if necessary, readily suppressed. With stays, peristalsis is less problematic, because it is usually quelled as an inherent consequence of manipulating the ductus. When access to the outside of the ductus has not been created to insert a stent-jacket, medication is used. In the gut, the contractive waves are slow enough to avoid, and if necessary, temporary suppression or immobilization by neural blockade or a drug such as glucagon or Valeant Pharmaceuticals International Motofen® is accepted practice.

The coronary arteries not only pulsate but move with the heart, except in the most practiced hands, precluding the off-pump use of stays. On the systoles, the highly elastic pulmonary artery expands 20-25 percent in diameter (see, for example, Lin, K. and Can, J. C. 2015. "MR Imaging of the Coronary Vasculature: Imaging the Lumen, Wall, and Beyond," *Radiologic Clinics of North America* 53(2):345-353; Ishida, M. and Sakuma, H. 2014. "Magnetic Resonance of Coronary Arteries: Assessment of Luminal Narrowing and Blood Flow in the Coronary Arteries," *Journal of Thoracic Imaging* 29(3):155-162; Lin, K., Lloyd-Jones, D. M., Liu, Y., Bi, X., Li, D., and Carr, J. C. 2011. "Noninvasive Evaluation of Coronary Distensibility in Older Adults: A Feasibility Study with MR Angiography," *Radiology* 261 (3):771-778; Weissman, N. J., Palacios, I. F., and Weyman, A. E. 1995. "Dynamic Expansion of the Coronary Arteries: Implications for Intravascular Ultrasound Measurements," *American Heart Journal* 130(1):46-51; Shelton, D. K. Jr. and Olson, R. M. 1972. "A Nondestructive Technique to Measure Pulmonary Artery Diameter and Its Pulsatile Variations," *Journal of Applied Physiology* 33(4):542-544.). A muscular artery more amenable of stenting as the treatment by the means described herein expands to a lesser degree, and less still when sclerosed (see, for example, Numao, T., Ogawa, K., Fujinuma, H., and Furuya, N. 1997. "Pulsatile Diameter Change of Coronary Artery Lumen Estimated by Intraductal Ultrasound." *Journal of Cardiology* (Amsterdam, Holland) 30(1):1-8 (in Japanese with abstract in English at Pubmed).

The difference in miniball impact force required to perforate rather than to penetrate the luminal wall of most ductus is sufficiently large that perforations should seldom occur. Except in the gastrointestinal tract, where to prevent infection, a perforation demands immediate intervention, such tiny perforations self seal quickly. Because the targeted application of anti-clotting medication allows the systemic dose to be minimized if not eliminated, bleeding should not be a problem. If stent-jacketed, over or under-shots beyond the intended margins can be recovered or made functional by extending the stent-jacket. The discharge control described herein is usually accomplished as an auxiliary function of the automatic positioning system and not synchronized to the phase of the pulse at the aiming point.

To provide an automatic ballistic triggering system to actively adapt the timing of discharge to the instantaneous position of the aiming point can be achieved by controlling both the heart rate and discharge by pacing circuitry. This may become necessary with a pulse too irregular for the operator to negotiate manually. Disease may further complicate the variability in frequency, amplitude, and tonicity of smooth muscle action. More significantly, such a system is adaptable to the discharge of the airgun, with which it is not essential, but not a stay insertion tool, which is manually triggered based upon touch. Stabilization of an insertion site may involve retarding the rate of intracellular chemical activity as well as gross immobilization. If needed, current cardiopulmonary bypass machines filter out the microembolisms responsible for postperfusion syndrome.

If not to synchronize the action of the smooth muscle itself, automatic means for effecting discharge would have to synchronize to that action, which is achievable but should seldom prove essential. In an artery, absolute radial displacement of the wall by a pulse of reasonably normal amplitude will be too slight to cause the target lesion to be missed, so that unsynchronized or mistimed discharges are seldom likely to result in mispositioning in such degree as to necessitate recovery of the implant. While a hampering pulse is ordinarily dealt with using, automatic means for controlling both the pulse and discharge of miniballs based upon pacemaking circuitry avoids the need for sensing and synchronizing discharge to the intrinsic motility as an adaptive function. The use a bypass machine is avoided when possible but may be necessary to avert hypoxia by luminal obstruction of the barrel-assembly as well as to achieve stabilization.

Such circuitry can achieve a speed of discharge that compensates for the loss in time had discharge to be limited to the diastoles as with manual triggering. Thus, in most situations, whether because the action is slow enough that the operator can adapt, or, as is usual, the level (position along the ductus) of placement is not so critical that the phase angle at the instant of discharge must be taken into account, or because the intensity and/or frequency can be suppressed with drugs or mechanical means, the need for either an automatic sensing and triggering system for adapting to peristalsis can be avoided whether stays or miniballs are used. When miniballs must be positioned precisely, mistiming the discharge in relation to the pulse phase will result in mispositioning; however, the end positions of the miniballs will not be affected by the infolding or pleating of the intima during diastoles.

The difference in the mechanical properties of ductus in the elderly, especially in the arterial tree (see, for example, Fonck, E., Prod'hom, G., Roy, S., Augsburger, L., Rüfenacht, D. A., and Stergiopulos, N. 2007. "Effect of Elastin Degradation on Carotid Wall Mechanics as Assessed by a Constituent-based Biomechanical Model," *American Journal of Physiology. Heart and Circulatory Physiology* 292 (6):H2754-763; Samila, Z. J. and Carter, S. A. 1981. "The Effect of Age on the Unfolding of Elastin Lamellae and Collagen Fibers with Stretch in Human Carotid Arteries," *Canadian Journal of Physiology and Pharmacology* 59(10): 1050-1057) are inherently adjusted for by the preliminary, in situ testing prescribed below in the section entitled Testing and Tests.

The avoidance of instrumentation affords considerable simplification. The stay insertion tool is weighted and made with a base (working end, distal end) configured to effect subadventitial insertion when passively resting upon the ductus and elevated by the pulse. Even when the surrounding tissue encroaches upon or clings to the tool altering its effective weight (which can be eliminated through use of a lubricant), the pulse, transmitted as tactual feedback, is clearly superimposed upon the restraint, adjustment accomplished if not spontaneously, then with the aid of a tonometric or pressure sensing device. Extension or retraction of the entry wound should not be necessary.

The pulse is felt over an interval sufficient to anticipate successive peaks despite any extrasystoles, ectopic beats, or other arrhythmial (arrhythmical) concomitant. Should a rapid or erratic pulse not have responded to medication given in preparation for the procedure and make it necessary, a hemostat (hemostatic clamp, arterial forceps) introduced through a second laparoscopic incision is used to clamp off the segment to be treated no longer than it takes to insert one stay; the recovery of a mispositioned stay posing no need to move the insertion tool or to suppress the pulse, clamping is immediately released following ejection of the stay. Ballistic insertion is normally guided visually, adjustment for the delay of airgun chamber to treatment site transit time spontaneous and the practical effect of inaccuracies insignificant.

Arteries are implanted on the pulse and the gastrointestinal tract aside from any contractive wave. Unless tissue to the sides is permitted to interfere with the passive resting of the tool on the ductus, the stays enter to the correct depth without lifting or downward force by the operator. Stay insertion tools are made in different sizes and weighted for the median bearing force ordinarily required to implant ductus of given types to subadventital or subfibrosal depth. Certain positions, pathology, and the use of attachments such as auxiliary syringes necessitate adjustment in the weight or bearing force, which is applied by the operator spontaneously or with the aid of a tonometer or pressure gauge.

Greater precision in the size of adjustment to the passive weight required can be achieved with the aid of a tonometer or pressure gauge as described below in the section entitled In situ test on extraluminal approach for proper stay insertion bearing force. Since removing weights will not adjust for the weight of attachments, the adjustment is applied with the aid of the same force gauge used to conduct the test. To minimize inadvertent changes in bearing force during tool actuation, the tool presents the least resistance possible, and to allow the range of adjustment necessary to treat ductus of given size and type regardless of condition, control by test and touch, or if necessary, with the aid of a pressure measuring device, is preferred to remote triggering.

The difference in downward force to infix the stay to a significantly greater depth is sufficiently large that the variance in downward force resulting from the attachment of auxiliary syringes and, unless excessive, that applied by the operator, should rarely result in excessively adluminal insertion much less penetration into the lumen. Remote actuation in order to avoid excessive weight from being brought to bear down on the tool is therefore unnecessary. If necessary, verification of depth can be obtained with the aid of intravascular ultrasound; however, this negates an advantage in the use of stays, which is complete avoidance of the lumen.

Similarly, a catheteric device is not introduced into the lumen to support the arterial wall from within. This is done, however, in the gastrointestinal tract where entry is nonincisional. In blood vessels, increased resistance to compression can often be accomplished merely by pinching the ductus without the trauma of entry. Since stay insertion is best timed to the distention maxima or outward force exerted by the smooth muscle, smooth muscle suppressive measures, whether relaxants, cuffing, or clamping, are best avoided in arteries but may be advantageous in the ureters or gastrointestinal tract.

Unless otherwise inadvisable, when the pulse is weak or the artery sclerosed, as addressed below in the section entitled Blood-grooves on Muzzle-heads for Use in Blood Vessels, medication to raise the blood pressure is beneficial (see, for example, McEniery, C. M., Yasmin, K., Maki-Petaja, M., McDonnell, B. J., Munnery, M., and 4 others 2010. "The Impact of Cardiovascular Risk Factors on Aortic Stiffness and Wave Reflections Depends on Age: The Anglo-Cardiff Collaborative Trial (ACCT III)," *Hypertension* 2010 56(4):591-597; Vyssoulis, G. P., Pietri, P. G., Karpanou, E. A., Vlachopoulos, C. V., and 4 others 2010. "Differential Impact of Metabolic Syndrome on Arterial Stiffness and Wave Reflections: Focus on Distinct Definitions," *International Journal of Cardiology* 138(2):119-125; Haynes, F. W., Ellis, L. B., and Weiss, S. 1936. "Pulse Wave Velocity and Arterial Elasticity in Arterial Hypertension, Arteriosclerosis, and Related Conditions," *American Heart Journal* 11(4): 385-401; Bramwell, J. C. McDowall, R. J. S., and McSwiney, B. A. 1923. "The Variation of Arterial Elasticity with Blood Pressure in Man (Part I)," *Proceedings of the Royal Society of London. Series B*, 94(656):i-vi).

Ballistic insertion, from within the ductus, is timed reciprocally for the maximum resistance looking radially outward. Peristaltic action is usually slow enough to allow insertion with stays or miniballs without drugs (spasmolytics, antispasmodics, antispasmogenics—loperamide, salbutamol, co-phenotrope, dicyclomine, hyoscyamine, propantheline bromide, atropine sulfate, and opioids). When the onset time of the drug allows, the procedure may commence with the implanting of stays or miniballs that consist of or include this medication. If necessary, the rate and force of peristalsis can be adjusted. Adjustment in the rate and force of peristalsis may be necessary to achieve precise placement during ductus-intramural implantation or to propel drug carrier nanoparticles, for example, past less to more strongly magnetized impasse-jackets placed at intervals along the tract.

Adjustment takes the form of medication, which can be locally introduced in a targeted manner by injection syringe tool-inserts or as medication miniballs, for example, or the introduction of contents into the lumen. In the digestive tract, the latter will usually involve simply ingesting ordinary food supplemented to include agents that support the procedure. Whether in the gastrointestinal tract, ureters, or gamete transport conduits, peristalsis is rarely so fast as to interfere with miniball discharge when adequate viewing means are present, or stay insertion using touch. When the ductus is manipulable, merely handling it will often suppress peristalsis. Arresting movement in any ductus through upsteam clamping should not be necessary. Arteries can usually be clamped long enough for each stay to be inserted.

Applied from within the lumen, ballistic implantation preparatory to the placement of a magnetic stent allows prepositioning of the stent-jacket, which can then serve as a motility restraining mantle or cuff; the stent-jacket side-straps, or belt-straps, are tightened only so long as it is necessary to prevent the slide-slit or side-slot from opening in response to the pulse. Once implantation has been completed, the barrel-assembly is withdrawn and the fabric backed hook and loop (such as Velcro®, made by the firm of the same name) belt-straps loosened or cut off to allow the side-slit or side-slot to comply with the pulse. For ballistic implantation, cuffing in this manner is better than clamping, because it eliminates movement of the lumen wall without completely cutting off circulation past the cuff as well as protects against the possibility of a perforation if the exit velocity has been set too high.

The use of a cuff to suppress a problematic pulse requires that the muzzle-head be small enough in diameter to allow some blood to move past it through the stent-jacketed segment containing the muzzle-head while tightened without injury to the lumen wall. Adenosine and various drugs, such as esmolol allow slowing the pulse, others slow peristalsis, and opioids can stop peristalsis outright. Such a drug can be introduced into the lumen wall as a stay, radial projection unit injection tool-insert injectant, or fully absorbable medication miniball preceding stenting implantation proper. In a bypass-angioplasty mixed procedure where the chest is open, the use of a stabilizer apparatus is standard, and a coronary artery can usually be further stabilized by lifting it away from the surface of the heart and securing it in position with tape or stitches.

When the pulse is erratic, one way to avoid the use of circuitry to automatically synchronize discharge to the pulse during automatic (machine-controlled) discharge in an artery is to make the incision for inserting the stent-jacket prior to discharge, then using a mosquito (Halsted, Kelly, Rochester) forceps or hemostat, for example, to compress or clamp the artery only so much and briefly enough to suppress the pulse. This is not recommended when a barrel-assembly is used to implant medication and/or other therapeutic substance-containing miniballs, which does not necessitate outside access or incision at any time to place implants which are completely absorbed.

The use of stays necessitates access by means of a local incision in any event. Initiating a $\beta_1$- or cardioselective beta-blocker (beta adrenergic blocker), such as atenolol (Tenormin®); a calcium channel blocker, such as diltiazam (Cardizem®, Dilacor®) or verapamil (Calan®, Isoptin®); or digoxin (Lanoxin®) over the period preparatory to the procedure serves to moderate a problematically fast or erratic heart rate or high blood pressure (see, for example, Landauer, A. A., Pocock, D. A., and Prott, F. W. 1979. "Effects of Atenolol and Propranolol on Human Performance and Subjective Feelings," *Psychopharmacology* 60(2):211-215).

4e(2). Tissue Stabilization at the Treatment Site

4e(2)(a). Temperature Stabilization

Thermal and cryogenic methods to include thermoplasty and cryoplasty have long been used to remove diseased tissue. However, subinjurious chilling of targeted tissue can also be used to increase its mechanical and chemical, or metabolic, stability, that is, reduce:

1. The mobility (plasticity, deformability, nonfixation) of soft tissue such as mucosal as a hindrance to shaving or abrasive removal (Chick, H. and Lubrzynska, E. 1914. "The Viscosity of Some Protein Solutions," *Biochemical Journal* 8(1): 59-69), and the rate of chemical activity within the tissue (see, for example, Yang, W. J. and Mochizuki, S. 2003. "Low Temperature and Cryogenic Applications in Medicine and Surgery," in Kakaç, S., Avelino, M. R. and Smirnov, H. F. Low Temperature and Cryogenic Refrigeration, Dordrecht Holland: Kluwer Academic Publishers).

2. The magazine clip to slightly reduce miniballs in diameter.

3. The muzzle-head, or

4. The entire barrel-assembly can be used to promote luminal contraction about the muzzle-head as well as reduce the rate of metabolic activity in the cells.

Change in temperature, whether an increase or decrease, stimulates smooth muscle to contract (see, for example, Tsai, C. S. and Ochillo, R. F. 1989. "Low Temperature and Muscarinic Receptor Activities," *Cryobiology* 26(5):485-95; Holzer, P. and Lembeck, F. 1979. "Longitudinal Contraction of Isolated Guinea-pig Ileum Induced by Rapid Cooling," *Naunyn-Schmiedeberg's Archives of Pharmacology* 310(2): 169-174). Such contraction is usually transient rather than sustained as seen in refractory vasospasm. Should vasospasm ensue with the barrel-assembly endoluminal, nitrates and/or calcium channel blockers can be locally injected by radial projection unit injection syringe tool-inserts, service-catheter hypotubes, or released along the internal surface of the lumen by radial projection unit emission syringe tool-inserts or through an available barrel-tube used as a service-channel Local release allows targeting a much smaller amount of a drug at a lesion in a much higher concentration than might be administered systemically so that the entire body would be exposed. In a harvested graft, contraction responsive to change in temperature can be blocked with glyceryl trinitrate (apaverine and calcium channel blockers less effective, and phenoxybenzamine ineffective) (Oo, A. Y., Conant, A. R., Chester, M. R., Dihmis, W. C., and Simpson, A. W. M. 2007. "Temperature Changes Stimulate Contraction in the Human Radial Artery and Affect Response to Vasoconstrictors," *Annals of Thoracic Surgery* 83(1): 126-132).

However, hypoxia or the release of endogenous prostanoids may also effect a radial artery that has been harvested for a coronary graft (Perrault, L. P. and Mommerot, A. 2007. "Invited Commentary" [on Oo, Conant, et al. 2007, op cit. this paragraph], *Annals of Thoracic Surgery* 83(1): 132-133; see also Conant et al. 2003 in the section below entitled Risk of Abrupt Closure). Reduction in temperature can be used to proportionally reduce the rate of drug uptake. The chilling means described herein can be used to lower the temperature of drugs delivered through injection tool-inserts and hypotubes. Projection of the cold to the surrounding lumen wall is prevented when preferred by using insulated components.

For the insertion of stay implants from outside the ductus, a cold air delivery catheter (thermal catheter, 'cooling'-catheter) whether connected to a $CO_2$ cylinder or cold air gun, for example, is easily fastened by means of the clips addressed below in the section entitled Use of Stay Insertion Tool Side Mounting Clips to Juxtaposition (Fasten Alongside) a $CO_2$ Cylinder or Cold Air Gun Line alongside the stay insertion tool. While the sustained exposure of skin to a stream of pressurized CO2 will result in frostbite, the momentary exposure of miniballs to chilling during propulsion from this source is not significant.

Firming the target tissue and chilling, slightly reducing the miniball in diameter, yields 'cleaner' trajectories but may require supplementation with a tumefaciant as addressed above in the section entitled Ductus Wall Tumefacients. Together, these measures will often make possible the implanting of a ductus wall that would otherwise be too thin to implant at body temperature. Heat-windows, the heating of turret-motor and recovery electromagnet windings, 'cooling' catheters (temperature changing catheters which actually allow heating no less than cooling), connection of a cold air gun, and so on are addressed below. Discharge concurrent with thermal or cryogenic ablation or angioplasty can be used to introduce medication.

4e(2)(b). Removal of Vulnerable Plaque or Accreted Material at the Implant Insertion Site Except for protrusive angiosteosic (calcified) plaque which must first be removed, the force of impact of the miniball is sufficient to penetrate the lumen wall despite the presence of any but stony intervening material, lumen contents, or contraction in the lumen wall. However, the miniballs must enter without delivering adherent matter in any significant degree and must be as well positioned as possible. Minimizing if not averting mispositioning due to the pulse or smooth muscular action is addressed in the section immediately preceding. The force of impact of the miniball is sufficient to penetrate almost any debris at the lumen surface, certainly when harder debris has already been removed by an angioplasty or an atherectomy.

A higher exit velocity averts a failure to penetrate or to rebound (ricochet), and in most instances, the spherical contour will minimize the adhesion and carrying forward into the lumen wall of debris. The effect is minimal when the miniball has a metal surface that is additionally wetted; however, when the miniball has an outer surface that is deeply textured or tacky, it is possible for its leading face to carry debris that was within or at the internal surface of the lumen into the wall, although infected blood would inoculate the wall in any event. The high exit velocity of the miniball also minimizes exposure to the blood for adhesion by clotting and militates against the adhesion of pathogens in infected blood. Coatings of an antibiotic, antiviral, and thrombolytic must follow from the clinical situation.

Combination-form barrel-assemblies use an edge-discharge muzzle-head that unlike a center-discharge muzzle-head, makes the central canal available. The central canal can permanently or interchangeably channel an imaging device, commercially available laser, or any of a number of atherectomy or thrombectomy devices. In addition to the multiple components provided for atherectomy in angioplasty-capable barrel-assemblies, the bores of combination-form barrel-assemblies, as addressed below in the section entitled Through-bore, or Combination-form, Barrel-assemblies, and combination-form radial projection catheters, as addressed in the section below entitled Through-bore, or Combination-form, Radial Projection Catheters, allow the insertion therethrough of various cabled atherectomy devices, to include a laser or directional cutter, for example.

The use of either type combination-form significantly increases the ability to minimize any residual debris or mineral deposits, obtain a biopsy sample, or use the barrel-assembly as a guide-catheter for administering medication, for example, without the need to withdraw and reenter before initiating stenting discharge. With respect to any ductus, the preliminary removal of obstructive tissue from the lumen reduces the internal diameter of the stent-jacket to which the wall must be outwardly retracted. With arteries, a transluminal angioplasty or atherectomy additionally reduces the risk of erosion or rupture of thin-capped fibroatheromatous plaques with the release of potentially embolizing debris.

Less forceful retraction reduces interference with normal smooth muscle function and increases the minimum magnetic field or tractive strength exerted on the implants essential to preserve patency. Ideally, the wall is not retracted beyond its quiescent or diastolic diameter. Less forceful retraction also reduces the risk of miniball pull-through or delamination, preserving the usability of miniballs where otherwise, as in stenting without previous angioplasty or atherectomy, wide stent-stays would be needed.

4f. Abrupt Closure with Thrombus and Vasospasm

4f(1). Risk of Abrupt Closure with Thrombus and Vasospasm

Abrupt closure can result in infarction, necessitate emergency bypass surgery, and result in death. The use of prior art apparatus and methods results in mid or postprocedural abrupt closure in some four percent of angioplasties and atherectomies overall. Following incisions caused by balloon overinflation, abrupt closure results when a loose flap suddenly occludes the lumen, whereas following directional atherectomy, for example, obstruction usually results from the formation of a thrombus (see, for example, Topol, E. J.

2003. *Textbook of Interventional Cardiology*, Philadelphia, Pa.: Saunders, pages 528-530). The muzzle-head is slippery and blunt-nosed so as not to catch, snag, or gouge, making incisions improbable, and the use of medication to control clotting should further reduce if not eliminate the risk of abrupt closure.

Most vasospasms and outer diametrical contracture is found with incipient atherosclerosis (Hong, M. K., Park, S. W., Lee, C. W., Ko, J. Y., Kang, D. H., Song, J. K, Kim, J. J., Mintz, G. S., Park, S. J. 2000. "Intraductal Ultrasound Findings of Negative Arterial Remodeling at Sites of Focal Coronary Spasm in Patients with Vasospastic Angina," *American Heart Journal* 140(3):395-401). Antiproliferative medication to treat atheromas or neoplasms that induce vasospasm unresponsive to nitrates (nitrovasodilators), such as nitroglycerin, or glyceryl trinitrate, and calcium channel blockers (see, for example, *The Merck Manual of Diagnosis and Therapy,* 18th Edition, page 599) usually require stenting.

With balloon angioplasty, arterial dissections occur more frequently with calcified plaques (see Potkin, B. N., Keren, G., Mintz, G. S., Douek, P. C., Pichard, A. D., Satler, L. F., Kent, K. M., and Leon, M. B. 1992. "Arterial Responses to Balloon Coronary Angioplasty: An Intravascular Ultrasound Study," *Journal of the American College of Cardiology* 20(4):942-951), making beneficial the removal of such plaque with an ultrasonic catheter or rotational atherectomizer, which can be incorporated into a combination-form barrel-assembly, as addressed below in the section entitled Comparison with Prior Art Angioplasty. These conditions should be treatable with less injury to the vessel by extraluminal stenting.

Vasospasm can lead to more serious consequences than angina and can kill even in the absence of arterial disease (see, for example, Alcalde, O., Domingo, E., and Figueras, J. 2010. "Recurrent Severe Acute Pulmonary Edema Caused by Transient Left Ventricular Insufficiency with Mitral Regurgitation Related to Severe Coronary Artery Spasm," *Circulation. Heart Failure* 3(2):332-335; Igarashi, Y., Tamura, Y., Suzuki, K., Tanabe, Y., Yamaguchi, T., Fujita, T., Yamazoe, M., Aizawa, Y., and Shibata, A. 1993. "Coronary Artery Spasm is a Major Cause of Sudden Cardiac Arrest in Survivors without Underlying Heart Disease," *Coronary Artery Disease* 4(2):177-185). The use of a balloon is suspected also to evoke postprocedural vasospasm, or vasoconstriction (Fischell, T. A., Nellessen, U., Johnson, D. E., and Ginsburg, R. 1989. "Endothelium-dependent Arterial Vasoconstriction after Balloon Angioplasty," *Circulation* 79(4):899-910; Fischell, T. A., Derby, G., Tse, T. M., and Stadius, M. L. 1988. "Coronary Artery Vasoconstriction Routinely Occurs after Percutaneous Transluminal Coronary Angioplasty. A Quantitative Arteriographic Analysis," *Circulation* 78(6):1323-1334), with injury to the smooth muscle of the media (Fischell, T. A., Grant, G., and Johnson, D. E. 1990. "Determinants of Smooth Muscle Injury during Balloon Angioplasty," *Circulation* 82(6):2170-2184).

As addressed below in the section entitled Strengths and Weaknesses of Prior Art Stenting in Vascular, Tracheobronchial, and Urological Interventions, conventional endoluminal stents (see, for example, Celik, T., lyisoy, A., Yüksel, U. Ç., Bugan, B., and Ersoy, I. 2009. "Stent-edge Vasospasm after Bare Metal Stent Implantation: A Case Report and Review of the Literature," *Gülhane Tıp Dergisi* 51:174-176; Wong, A., Cheng, A., Chan, C., and Lim, Y. L. 2005. "Cardiogenic Shock Caused by Severe Coronary Artery Spasm Immediately after Coronary Stenting," *Texas Heart Institute Journal* 32(1):78-80), and not just those drug-eluting (see, for example, Tomassini, F., Varbella, F., Gagnor, A., Infantino, V., Luceri, S., and Conte, M. R. 2009. "Severe Multivessel Coronary Spasm after Sirolimus-eluting Stent Implantation," *Journal of Cardiovascular Medicine* (Hagerstown) 10(6):485-488; Brott, B. C., Anayiotos, A. S., Chapman, G. D., Anderson, P. G., and Hillegass, W. B. 2006. "Severe, Diffuse Coronary Artery Spasm after Drug-eluting Stent Placement," *Journal of Invasive Cardiology* 18(12):584-592; Togni, M. and Eberli, F. R. 2006. "Vasoconstriction and Coronary Artery Spasm after Drug-eluting Stent Placement," *Journal of Invasive Cardiology* 18(12):593), are used to suppress vasospasm (see, for example, Van Spall, H. G., Overgaard, C. B., and Abramson, B. L. 2005. "Coronary Vasospasm: A Case Report and Review of the Literature," *Canadian Journal of Cardiology* 21(11):953-957), but, as can guide wires, induce vasospasm on insertion, and those drug-eluting, well afterwards.

While an endoluminal stent can sometimes control spasm (see, for example, Warner, J. J. and Bashore, T. M. 2001. "Diagnostic and Interventional Cardiac Catheterization," in Estafanous, F. G., Barash, P. G., and Reves, J. G. (eds.), *Cardiac Anesthesia: Principles and Clinical Practice*, Philadelphia, Pa.: Lippincott Williams and Wilkins, page 136), one implanted to suppress a refractory spasm constrains the spasm up to its distal margins, inflicting injury and endothelial dysfunction (see, for example, Celik, T. et al. 2009 op cit.). Atheromatous lesions increase the odds for aneurysm and vasospasm, and are the direct cause of negative remodeling. In negatively remodeled arteries following the removal of diseased tissue by the means described herein, smooth muscle proliferation, or neointimal hyperplasia (see, for example, Guérin, P., Rondeau, F., Grimandi, G., Heymann, M. F., and 6 others 2004. "Neointimal Hyperplasia after Stenting in a Human Mammary Artery Organ Culture," *Journal of Vascular Research* 2004 41(1):46-53), should be less than tends to ensue following balloon angioplasty.

While vasospasm is commonly associated with abrupt closure (see, for example, Fischell et al. 1989 op cit.), it can arise as a separate entity, even remotely from the treatment site (see, for example, Tomassini, F., Varbella, F., Gagnor, A., Infantino, V., Luceri, S., and Conte, M. R. 2009. "Severe Multivessel Coronary Spasm after Sirolimus-eluting Stent Implantation" *Journal of Cardiovascular Medicine* (Hagerstown) 10(6):485-488; Tani, S., Watanabe, I., Kida, T., Ishikawa, K., Iida, K., and 7 others 2005. "Unexpected Coronary Vasospasm of a Contralateral Artery during Balloon Angioplasty" *Heart and Vessels* 20(2):82-84) and therefore remains as a threat.

Vasospasm is usually alleviated by nitrates and calcium channel blockers; however, when not prevented, vasospasm can disable a magnetic stent by delamination of the vascular tunics or pull-through, that is, the perforation of a miniball or miniballs through the adventitia resulting in a loss of lumen-patenting retraction. The risk of incisions by a muzzle-head of unsuitable size or of thrombosis as the result of introducing small punctures and narrow trajectories through the intima and media should be significantly less than it is with the guide wires and the catheteric means in conventional use. Because the lumen is never entered, medication stays or stent-stays implanted without an angioplasty avoid the risk of thrombosis. Antithrombic medication administered to protect against accidental perforation into the lumen is can be delivered locally as a coating on the stays rather than systemically as could create a problem with bleeding.

Similarly, using miniballs, the puncture sites are thrombogenic; however, miniballs coated with antithrombogenic medication should allow significant reduction in the systemic dose. The propensity for abrupt closure with or without thrombogenesis and/or reflexive recoil or spasm responsive to ballistic entry if any, with and without preprocedural administration of nitrates and calcium channel blockers, for example, has not been established. The availability of numerous spasmogenic drugs notwithstanding, the range of actual or absolute forces generated in vasospasm with and without various drugs having been administered is unaddressed in the literature, probably because nitroglycerin succeeds in suppressing most spasm. Anti spasmodics for use in other type ducti include beladonna in the gastrointestinal tract and hyocine in the biliary and urinary as well as the gastrointestinal tract, for example.

Chemically mediated within the wall (see, for example, Humphrey, J. D., Baek, S., and Niklason, L. E. 2007. "Biochemomechanics of Cerebral Vasospasm and Its Resolution: I. A New Hypothesis and Theoretical Framework," *Annals of Biomedical Engineering.* 35(9):1485-1497 and "II. Constitutive Relations and Model Simulations," 35(9): 1498-1509), vasospasm may be forcibly resisted by an endoluminal stent, but not without trauma at the margins. Neither is mitigation in remodelling and the vasospasm that remodelling is suspected to engender (see, for example, Zhang, Z. D. and Macdonald, R. L. 2006. "Contribution of the Remodeling Response to Cerebral Vasospasm," *Neurological Research* 28(7):713-720; Hong, M. K., Park, S. W., Lee, C. W., Ko, J. Y., Kang, D. H., Song, J. K, Kim, J. J., Mintz, G. S., Park, S. J. 2000. "Intraductal Ultrasound Findings of Negative Arterial Remodeling at Sites of Focal Coronary Spasm in Patients with Vasospastic Angina," *American Heart Journal* 140(3):395-401) to be expected.

Complete dependency upon any kind of stent to control continued spasm such as of variant angina that persists past eradication of the lesion or lesions with which it is associated is likely to result in trauma to the artery if not failure of the stent, the need for lifelong maintenance medication indicated. An extraluminal stent intended to resist spasmodic constriction without delamination or pull-through is best full-round with the intravascular (intraductal) component preferably cyanoacrylate cement-coated wide stays placed more deeply adluminal than where spasm is medically suppressible and not of immediate concern. Placement subjacent (adluminally) with respect to the bulk of the contractile tissue reduces the risks of delamination or pull-through.

Only stays can be coated with cyanoacrylate cement prior to implantation, although immediate followup injection by hypotube service catheter or radial projection unit injection syringe tool-insert allows such treatment with miniballs. Contrast dye is essential to achieve proximity to the implant. Side-looking (radially directed) injection tool-insert can also inject nitroglycerin, for example. Miniballs can be coated with a solid protein solder and a glyceryl trinitrate, for example, a brief interval allowed for nitrate uptake, then the solder denatured (liquified) by heat-windows in the muzzle-head. The heat-windows do not approach the autoignition temperature of nitroglycerin, which is 270 degrees Celsius or 518 degrees Fahrenheit, even before the addition of desensitizing additives.

Medical preparations of nitroglycerin are effectively nonexplosive. Broad stays coated with cyanoacrylate cement will resist delamination, and miniballs coated with protein solder pull-through, up to a certain restraining (radially outward pulling) force, beyond which one of the other will disable the stent; however, an extraluminal stent cannot fracture and migrate as have endoluminal stents under the force of contraction that drives the stent margins into the intima and can even crush the stent. Rather than used to apply a coating of cement, the built in stay insertion tool coating mechanism can be used to further cover solder-coated stays with nitroglycerin ointment, for example.

A radially symmetrical extraluminal stent requires a slitted or narrowly slotted fully encircling (complete, full-round) stent-jacket, so that dissection to free the outside of the ductus in order to place broad stays along the far (opposite, deep) side should not necessitate additional dissection. Where an artery gives off plunging branches to be left intact at intervals too small to allow its rotation for proper positioning of the stay insertion tool without the imposition of torsion trauma, miniballs are placed in the far side. Segmented stent-jackets as addressed in the section below entitled Sectional, or Chain-stents, Segmented and Articulated, afford versatility in clearing plunging offshoots as well as far-side running attachments.

4f(2). Prevention of Abrupt Closure with Thrombus and Vasospasm

While not a balloon, an ablation or angioplasty-capable barrel-assembly can be equipped with radial projection unit blank push-arm tool-inserts, addressed in the section below entitled Comparison with Prior Art Angioplasty, among others, to exert radially outward force when using a microwave probe (applicator, antenna) or laser, for example. Such a cabled device can be built into a noncombination-form barrel-assembly or temporarily inserted in the central channel of a combination-form type. With balloon angioplasty and to a lesser extent with rotational atherectomy devices, abrupt closure usually results when a flap created by incisions occludes the lumen, usually bolstered by thrombus and spasmic contracture, or vasoconstriction.

Reducing if not eliminating the thrombus and spasm reduces the obstruction. The risk of and amelioration of abrupt closure when tiny puncture wounds are placed in the intima and media of a muscular artery must be taken into account. Stretching injury (parectasia, parectasis) and dissections resulting from use of the apparatus of invention are improbable; however, thrombus remains a threat that justifies the use of a platelet blockade. The preprocedural administration of systemic platelet blockade to avert thrombogenesis, nitroglycerin or an alternative vasorelaxant as specified below to avert spasm, and optionally, a thrombolytic, is routine.

By insertion in the central channel, barrel-assemblies can incorporate radiofrequency (Barry, K. J., Kaplan, J., Connolly, R. J., Nardella, P., Lee, B. I., Becker, G. J., Waller, B. F., and Callow, A. D. 1989. "The Effect of Radiofrequency-generated Thermal Energy on the Mechanical and Histologic Characteristics of the Arterial Wall in Vivo: Implications for Radiofrequency Angioplasty," *American Heart Journal* 117(2):332-341), laser (Cheong, W. F., Spears, J. R., and Welch, A. J. 1991. "Laser Balloon Angioplasty," *Critical Reviews in Biomedical Engineering* 19(2-3):113-146), and microwave (Landau, C., Currier, J. W., Haudenschild, C. C., Minihan, A. C., Heymann, D., and Faxon, D. P. 1994. "Microwave Balloon Angioplasty Effectively Seals Arterial Dissections in an Atherosclerotic Rabbit Model," *Journal of the American College of Cardiology* 23(7):1700-1707; Nardone, D. T., Smith, D. L., Martinez-Hernandez, A., Consigny, P. M., Kosman, Z., Rosen, A., and Walinsky, P. 1994. "Microwave Thermal Balloon Angioplasty in the Atherosclerotic Rabbit," *American Heart Journal* 127(1):198-203; see also the section below entitled System Features) thermal angioplasty or thermoplasty devices claimed capable of fusing or welding loose flaps, which along with other benefits claimed would reduce if not eliminate the incidence of abrupt closures.

The ability to target the area for treatment with medication-coated implants midprocedurally, however, allows a significant reduction in the preprocedural systemic dose. Placement of the stent-jacket prior to introducing the barrel-assembly, which is slippery and without projections, as addressed below in the section entitled Circumstances Recommending the Use of a Shield-jacket or Preplacement of the Stent-jacket, should also aid in reducing if not eliminating the risk of mid or postprocedural abrupt closure. Vasospasm due to Prinzmetal (variant, vasospastic) angina that recurs well after angioplasty despite the eradication of triggering plaque at the time of the procedure is primarily controlled with nitrates.

Vasospasm as a factor contributing to abrupt closure (see, for example, Kern, M. J. 2004. The Interventional Cardiac Catheterization Handbook, Philadelphia, Pa.: Mosby Elsevier, pages 163-175; Landau, C., Lange, R. A., and Hillis, L. D. 1994. "Percutaneous Transluminal Coronary Angioplasty," *New England Journal of Medicine* 330(14):981-993; Lazzam, C., Forster, C Gotlieb, A., Dawood, F., Schwartz, L., and Liu, P. 1992. "Impaired Vascular Reactivity Following Angioplasty is Mainly Due to Endothelial Injury," *Experimental and Molecular Pathology* 56(2):153-162; Laurindo, F. R., da Luz, P. L., Uint, L., Rocha, T. F., Jaeger, R. G., and Lopes, E. A. 1991. "Evidence for Superoxide Radical-dependent Coronary Vasospasm after Angioplasty in Intact Dogs," *Circulation* 83(5):1705-1715) can be ameliorated if not eliminated with an antispasmodic, or angiotonic relaxant (vasodilator, angiotensin counteractant, angiorelaxant, spasmolytic, hypotensive agent), such as nitroglycerin (short-acting), isosorbide dinitrate (long-acting), verapamil, adenosine, nitroprusside, papaverine or hydralazine (apresoline).

Unless administered for a collateral purpose, the direct targeting obtained through the use of coated stays or miniballs or radial projection unit injection syringe tool-inserts in the barrel-assembly muzzle-head or radial projection catheter allow the elimination or a significant reduction in the preprocedural or preparatory systemic dose. Miniballs and stays can be jacketed with solid-state drugs, and through use of the exit-coating feature of the stay insertion tool, stays can additionally be given a coating of any drug in a semiliquid state. Stays with a deeply textured surface are used to retain much of the coating even when insertion is resistive. To resist if not avert vasospasm mid- and for an interval post-procedurally, broad stays or miniballs implanted are coated with one or more of these drugs for targeted delivery.

With transluminal approach, the use of side-looking (radially directed) injection tool-inserts, as addressed below in the section entitled Radial Projection Unit Tool-inserts, allows a significant increase in a targeted dose of these drugs in liquid or semiliquid form. The retractive field strength of a stent-jacket must be kept less than would result in the extraction of the miniballs through the adventitia or in the delamination of the lumen wall. This strength may be less than that required to maintain the vessel patent mid-spasm, so that the contractive force of vasospasm which a stent-jacket can overcome must be limited. When vasospasm is refractory or resistant to suppression by drugs, broad stays coated with cyanoacrylate cement are preferred, because these are subjacent to and bondable and attracted over the largest area cutting through the lines of force.

Broad stays can therefore be subjected to stronger field strengths without failure and are the most resistant to being pulled through under the spasmic constrictive force (contractive force of the spasm). Reduction in the effectively retractive field strength also recommends application of relaxant medication to the implants if not systemically. Means for testing the resistance to delamination of the lumen wall and pullout through the adventitia are addressed below in the section entitled Testing and Tests. The use of a muzzle-head not so large in diameter as to stretch the lumen wall as might a balloon and less occlusive should reduce in incidence if not eliminate abrupt closures. While the barrel-assembly remains endoluminal, the muzzle-head is positioned to prevent any significant constriction, and the muzzle-head remains within the segment until the circumferentially full complement of miniballs has been placed.

As with endoluminal stenting, the stent itself can often maintain patency once placed. Continued vasospasm that proves refractory to routine thrombolytic and antispasmodic or vasorelaxant medication and appears sufficiently strong to cause pull-through or delamination leading to retractive failure is treated with Bosentan® (Actelion Pharmaceuticals) (Krishnan, U., Win, W., and Fisher, M. 2010. "First Report of the Successful Use of Bosentan in Refractory Vasospastic Angina," *Cardiology* 116(1):26-28), and if nonextensive, may in some instances justify crushing or severing vasa vasora over a very limited segment before stenting of any kind is abandoned.

In addition to intimal injury, abrupt closure is associated with and medial injury and elevation in myocardial band (MB) serum creatine kinase (CK, phosphocreatine kinase, creatine phosphokinase) isoenzyme, and troponin T, but a cause or effect relationship between abrupt closure and elevated CK-MB has not been determined (Cavallini, C., Rugolotto, M., Savonitto, S. 2005. "Prognostic Significance of Creatine Kinase Release after Percutaneous Coronary Intervention," *Italian Heart Journal* 6(6):522-529). The prevention of a thrombogenic component in abrupt closure is sought through the administration of drugs that can be applied to the miniball and stay implants described herein or prepared in liquid form for injection by means of injection tool-inserts for targeted delivery, if necessary, in combination with systemic administration which can then be of lower dose, the highly localized concentration serving to reduce the risk of bleeding problems.

Conventional antithrombogenic measures include the use of antiplatelet (antithrombocyte) medication (platelet receptor blockers, inhibitors; platelet antiaggregants, aggregation counteractants), such as aspirin, clopidogrel, ticlopidine, thienopyridines, and glycoprotein IIb/IIIa (gpIIb/IIIa, integrin $\alpha_{IIb}\beta_3$) receptor antagonists or inhibitors, such as abciximab, eptifibatide and tirofiban. In arteries, clotting is less inhibited by anticoagulants, such as warfarin, intravenous heparin (or argatroban, efegatran, inogatran, napsagatran, fondaparinux, or idraparinux); while a spasmodic component is suppressed with vasodilatory drugs, such as glyceryl trinitrate (nitroglycerin), phenoxybenzamine, papaverine, and calcium channel blockers, or antagonists, such as diltiazem, verapamil, and nifedipine.

If refractory to calcium channel blockers, then (per Skillings at http://www.medscape.com/viewarticle/413564) amiodarone: (Rutitzky, B., Girotti, A. L., Rosenbaum, M. B. 1982. "Efficacy of Chronic Amiodarone Therapy in Patients with Variant Angina Pectoris and Inhibition of Ergonovine Coronary Constriction," *American Heart Journal* 103(1): 38-43), or if pregnant or subject to become pregnant, the α2 adrenergic agonist clonidine, or guanethidine (Frenneaux, M., Kaski, J. C., Brown, M., and Maseri, A. 1988. "Refractory Variant Angina Relived by Guanethidine and Clonidine," *American Journal of Cardiology* 62(10 Part 1):832-833) is used.

Whether during or following an angioplasty, an atherectomy, or stenting, that thrombogenesis is a central factor in abrupt closure is attested to by the effectiveness of such antithrombotic (antithrombogenic) drugs such as aspirin, abciximab, and dipyridamole in reducing the gravity of this complication. (see, for example, Heintzen, M. P., Heidland, U. E., Klimek, W. J., Leschke, M., and five other authors, 2000. "Intracoronary Dipyridamole Reduces the Incidence of Abrupt Vessel Closure Following PTCA: A Prospective Randomised Trial," *Heart* 83(5):551-556; Schillinger, M. and Minar, E. 2007. *Complications in Peripheral Vascular Interventions*, London, England: Informa Healthcare, page 190).

When angioplasty is opted against, the use of stays avoids luminal entry entirely. Vasospasm, or vasoconstriction, induced by endothelial injury are also implicated (see, for example, Lazzam, C., Forster, C., Gotlieb, A., Dawood, F., Schwartz, L., and Liu, P. 1992. "Impaired Vascular Reactivity Following Angioplasty is Mainly Due to Endothelial Injury," *Experimental and Molecular Pathology* 56(2):153-162; Vassanelli, C., Menegatti, G., Zanolla, L., Molinari, J., Zanotto, G., and Zardini, P. 1994. "Coronary Vasoconstriction in Response to Acetylcholine after Balloon Angioplasty: Possible Role of Endothelial Dysfunction," *Coronary Artery Disease* 5(12):979-986). Whether thermoplasty, cryoplasty, or electrical discharge have any particular effect that would serve to incite and predesensitize and thus suppress if not prevent abrupt closure is elusive of a testing method and unaddressed in the literature.

Using conventional apparatus, trauma responsive vasospasm can arise as the result of a more extended dissection due to balloon overinflation during angioplasty or with directional atherectomy, where injury due to the bulkiness of older models of such a device has been hypothesized to result in an increased rate of distal embolization (Abdelmeguid, A. E., Whitlow, P. L., Sapp, S. K., Ellis, S. G., and Topol, E. J. 1995. "Long-term Outcome of Transient, Uncomplicated, In-laboratory Coronary Artery Closure Circulation 91(11):2733-2741, whose attribution to spasm as weakly predictive of acute sequelae compared to elevation in serum muscle enzyme levels is at odds with the findings of Piana, R. N., Ahmed, W. H., Chaitman, B., Ganz, P., Kinlay, S., Strony, J., Adelman, B., and Bittl, J. A. 1999. "Effect of Transient Abrupt Vessel Closure During Otherwise Successful Angioplasty for Unstable Angina on Clinical Outcome at Six Months," *Journal of the American College of Cardiology* 33(1):79-81) in both instances, especially when insufficient glycoprotein IIb/IIIa antagonist (inhibitor) has been administered to deter platelet-rich thrombi.

When the object of the procedure is to stent the vessel, abrupt closure at levels (stretches, segments) beyond that to be stented poses the greater risk. Based upon the occasional appearance of an abrupt closure in an untreated artery, a certain percentage of abrupt closures during angioplasty or stenting may be unavoidable regardless of the apparatus used (see, for example, Moukarbel, G. V. and Dakik, H. A. 2003. "Diffuse Coronary Artery Spasm Induced by Guidewire Insertion," *Journal of Invasive Cardiology* 15(6):353-354; Takahashi, M., Ikeda, U., Sekiguchi, H., Fujikawa, H., Shimada, K., and Ri, T. 1996. "Guide Wire-induced Coronary Artery Spasm During Percutaneous Transluminal Coronary Angioplasty. A Case Report," *Angiology* 47(3):305-309; additional references, to include Lauribe et al. 1993, below in this section).

However, plaque-crushing and/or circumferential fiber tearing angioplasty is more likely to produce dissections and induce coronary vasospasm than is touching the lumen wall, much less in a different artery, with a guidewire, which is rare, and vasodilators as specified below in this section are available to ameliorate if not dispel vasospasm as a complication. The tiny puncture wounds produced by the miniballs as these enter the intima and the trajectories through the media are quite unlike dissections in extent or form, and the barrel-assembly, while larger in diameter than a balloon while uninflated, is fully rounded and smooth surfaced as not to gouge, nor is it so large as to seize onto or stretch the lumen wall.

Absent dissection that leads to an abrupt closure, balloon (compressive, atheroma-crushing) angioplasty still injures the endothelium, and "endothelial dysfunction can promote both restenosis and coronary spasm" (Chandrasekar, B., Nattel, S., and Tanguay, J. F. 2001. "Coronary Artery Endothelial Protection After Local Delivery of 17Beta-Estradiol During Balloon Angioplasty in a Porcine Model: A Potential New Pharmacologic Approach to Improve Endothelial Function," *Journal of the American College of Cardiology* 38(5): 1570-1576).

The injury produced by ballistic implantation or stay insertion, which is discontinuous and small in extent, is considerably less than that of intentional subintimal or of vessel size-adapted angioplasty. A subintimal recanalization, or percutaneous intentional extraluminal recanalization (or revascularization) (PIER), which produces far larger puncture wounds through the lumen wall, may be performed in a lower extremity (such as in the iliac artery to salvage a kidney or leg) even when, albeit difficult, a strictly endoluminal angioplasty is possible.

Nevertheless, extraluminal recanalization is gaining in acceptance relative to strictly endoluminal angioplasty, despite the puncture wounds (see, for example, Scott, E. C., Biuckians, A., Light, R. E., Scibelli, C. D., Milner, T. P., Meier, G. H. 3rd, and Panneton, J. M. 2007. "Subintimal Angioplasty for the Treatment of Claudication and Critical Limb Ischemia: 3-year Results," *Journal of Vascular Surgery* 46(5):959-964; Ko, Y. G., Kim, J. S., Choi, D. H., Jang, Y., Shim, W. H. 2007. "Improved Technical Success and Midterm Patency with Subintimal Angioplasty Compared to Intraluminal Angioplasty in Long Femoropopliteal Occlusions," *Journal of Endovascular Therapy* 14(3): 374-381; Cho, S. K., Do, Y. S., Shin, S. W., Park, K. B., Kim, D. I., Kim, Y. W., Kim, D. K., Choo, S. W., and Choo, I. W. 2006. "Subintimal Angioplasty in the Treatment of Chronic Lower Limb Ischemia" *Korean Journal of Radiology* 7(2):131-138; Mishkel, G. and Goswami, N. J. 2005. "A Practical Approach to Endovascular Therapy for Infrapopliteal Disease and the Treatment of Critical Leg Ischemia: Savage or Salvage Angioplasty?," *Journal of Invasive Cardiology* 17(1):45-51).

Specific risks with 'therapeutic dissections' and size-adapted angioplasty are addressed below in the section entitled Basic Strengths and Weaknesses of Prior Art Stenting in Vascular, Tracheobronchial, and Urological Interventions. "Cocktails" of verapamil, heparin, and nitroglycerin (Saland, K. E., Cigarroa, J. E., Lang, e R. A., and Hillis, L. D. 2000. "Rotational Atherectomy," *Cardiology in Review* 8(3):174-179) and nicardipine and adenosine (Fischell, T. A., Haller, S., Pulukurthy, S., and Virk, I. S. 2008. "Nicardipine and Adenosine "Flush Cocktail" to Prevent No-reflow During Rotational Atherectomy," *Cardiovascular Revascularization Medicine* 9(4):224-228) recommended for use during rotational atherectomy may suppress a tendency to thrombogenic vasospasm with abrupt closure.

Essentially the same technique as a subintimal recanalization, or percutaneous intentional extraluminal recanalization (or revascularization) in a peripheral artery, subintimal tracking and reentry is gaining acceptance for use in coronary arteries that have become completely blocked Colombo, A., Mikhail, G. W., Michev, I., Iakovou, I., Airoldi, F., Chieffo, A., Rogacka, R., Carlino, M., Montorfano, M., Sangiorgi, G. M., Corvaja, N., Stankovic, G. 2005. "Treating Chronic Total Occlusions Using Subintimal Tracking and Reentry: The STAR Technique," *Catheterization and Cardiovascular Interventions* 64(4):407-412) and controlled antegrade and retrograde subintimal tracking (Katoh, O. and Ogata, W. 2007. "Recanalizing Occluded Vessels Using Controlled Antegrade and Retrograde Tracking," World Intellectual Property Organization Patent WO/2007/095191; Surmely, J. F., Tsuchikane, E., Katoh, O., Nishida, Y., Nakayama, M., Nakamura, S., Oida, A., Hattori, E., and Suzuki, T. 2006. "New Concept for CTO [Chronic Total Occlusion] Recanalization Using Controlled Antegrade and Retrograde Subintimal Tracking: The CART Technique," *Journal of Invasive Cardiology* 18(7):334-338).

At least as traumatizing as the apparatus and methods described herein, atheromatous arteries have been claimed to demonstrate the potential for recovery from the more severe intraparietal, or ductus-intramural, laminar separations, perforations, and dissections imposed by the preceding techniques (Schroeder, S., Baumbach, A., Mahrholdt, H., Haase, K. K., Oberhoff, M., Herdeg, C., Athanasiadis, A., and Karsch, K. R. 2000. "The Impact of Untreated Coronary Dissections on Acute and Long-term Outcome after Intraductal Ultrasound guided PTCA," *European Heart Journal* 21(2):137-145 and 21(2):92-94; Schroeder, S., Baumbach, A., Haase, K. K., Oberhoff, M., Marholdt, H., Herdeg, C., Athanasiadis, A., and Karsch, K. R. 1999. "Reduction of Restenosis by Vessel Size Adapted Percutaneous Transluminal Coronary Angioplasty Using Intraductal Ultrasound," *American Journal of Cardiology* 83(6):875-879) and adapt to sustained forcible distention (Dirsch, O., Dahmen, U., Fan, L. M., Gu, Y. L., Shen, K., Wieneke, H., and Erbel, R. 2004. "Media Remodeling—The Result of Stent Induced Media Necrosis and Repair," *Vasa* 33(3):125-129).

Comparative data for relative frequency of vasospasm attendant upon arterial thermoplasty or cryoplasty do not appear in the literature; however, considering spasm has been known to arise where the vessel has not even been touched, endothelial injury due to balloon compressive, atheroma-crushing angioplasty would appear equally if not more likely to induce vasospasm. While rare, a mechanical force exerted in an artery other than that treated (see, for example, Lauribe, P., Benchimol, D., Duclos, F., Benchimol, A., Bonnet, J., Levy, S., and Bricaud, H. 1993. "Spasme occlusif d'une artère coronaire non abordée au cours d'une angioplastie. A propos d'une observation" ["Occlusive Spasm of a Coronary Artery Not Treated During Angioplasty. Apropos of a Case"], *Annales de cardiologie et d'angéiologie* 42(2):89-92) can induce spasm. Such an aberration aside, spasm often follows stretching injury.

The mechanism has been hypothesized to involve the imparting of hyper-reactivity to acetylcholine (Nishijima, H. Meno, H., Higashi, H., Yamada, K., Hamanaka, N., and Takeshita, A. 1996. "Coronary Vasomotor Response to Acetylcholine Late After Angioplasty," *Japanese Circulation Journal* 60(10):789-796; Osborn, L. A. and Reynolds, B. 1998. "Vagally Mediated Multivessel Coronary Artery Spasm During Coronary Angiography," *Catheterization and Cardiovascular Diagnosis* 44(4):423-426), perhaps by relation to the superoxide radical (see for example, Laurindo, F. R., da Luz, P. L., Uint, L., Rocha, T. F., Jaeger, R. G., and Lopes, E. A. 1991. "Evidence for Superoxide Radical-dependent Coronary Vasospasm after Angioplasty in Intact Dogs," *Circulation* 83(5):1705-1715; Ferrer, M., Tejera, N. Marin, J. and Balfagon, G. 1999. "Androgen Deprivation Facilitates Acetylcholine-induced Relaxation by Superoxide Anion Generation," *Clinical Science* 97(6): 625-631; Rubanyi, G. M. and Vanhoutte, P. M. 1986. "Superoxide Anions and Hyperoxia Inactivate Endothelium-derived Relaxing Factor," *American Journal of Physiology* 250(5 Part 2):H822-H827). This is the likely explanation for the occurrence of vasospasmodic response with angioplasty even in another artery, much less when dissection has not occured (see Fischell, T. A. 1990. "Coronary Artery Spasm After Percutaneous Transluminal Angioplasty: Pathophysiology and Clinical Consequences," *Catheterization and Cardiovascular Diagnosis* 19(1):1-3).

The causes for abrupt closure when using conventional means aside, the appearance of vasospasm is usually deterrable through the preprocedural inception of systemic arterial spasmodic counteractive drugs, such as nitrovasodilators (glyceryl trinitrate, nitroglycerin, intracoronary infusion of isosorbide dinitrate) (see, for example, Moukarbel, G. V. and Dakik, H. A. 2003. "Diffuse Coronary Artery Spasm Induced by Guidewire Insertion," *Journal of Invasive Cardiology* 15(6):353-354; Lauribe et al. 1993, cited above), calcium antagonists (calcium channel blockers), such as diltiazem (e.g., Cardizem®, Dilzem®, Herben®, Viazem®) or verapamil (e.g., Bosoptin®, Calan®, Isoptin®, Verelan®) (see, for example, Pomerantz, R. M., Kuntz, R. E., Diver, D. J., Safian, R. D., and Baim, D. S. 1991. "Intracoronary Verapamil for the Treatment of Distal Microvascular Coronary Artery Spasm Following PTCA," *Catheterization and Cardiovascular Diagnosis* 24(4):283-285; Caputo, M., Nicolini, F., Franciosi, G., and Gallotti, R. 1999. "Coronary Artery Spasm after Coronary Artery Bypass Grafting," *European Journal of Cardiothoracic Surgery* 15(4):545-548) or a dilute intravenous solution of an opium alkaloid such as papaverine and a calcium channel blocker such as nicardipine, as well as platelet glycoprotein IIb/IIIa antagonist. Injection a local dose by means of radial projection unit injection syringe tool-inserts allows significant reduction if not elimination of the preprocedural systemic dose. Alpha blocker antispasmodics include phenoxybenzamine (Dibenzyline®), Doxazosin (Cardura®), and Prazosin (Minipress®).

For reducing spasm in radial artery grafts, recent papers incline toward a preference for verapamil-glycerine trinitrate solution (see, for example, Attaran, S., John, L., and El-Gamel, A. 2008. "Clinical and Potential Use of Pharmacological Agents to Reduce Radial Artery Spasm in Coronary Artery Surgery," *Annals of Thoracic Surgery* (4):1483-1489; Yoshizaki, T., Tabuchi, N., and Toyama, M. 2008. "Verapamil and Nitroglycerin Improves the Patency Rate of Radial Artery Grafts," *Asian Cardiovascular and Thoracic Annals* 16(5):396-400). Others find phenoxybenzamine preferable as having prolonged duration of action (Kulik, A., Rubens, F. D., Gunning, D., Bourke, M. E., Mesana, T. G., and Ruel, M. 2007. "Radial Artery Graft Treatment with Phenoxybenzamine is Clinically Safe and May Reduce Perioperative Myocardial Injury," *Annals of Thoracic Surgery* 83(2):502-509; Mussa, S., Guzik, T. J., Black, E., Dipp, M. A., Channon, K. M., and Taggart, D. P. 2003. "Comparative Efficacies and Durations of Action of Phenoxybenzamine, Verapamil/Nitroglycerin Solution, and Papaverine as Topical Antispasmodics for Radial Artery Coronary Bypass Grafting," *Journal of Thoracic and Cardiovascular Surgery* 126(6):1798-1805; Taggart, D. P., Dipp, M., Mussa, S., and Nye, P. C. G. 2000. "Phenoxybenzamine Prevents Spasm in Radial Artery Conduits for Coronary Artery Bypass Grafting," *Journal of Thoracic and Cardiovascular Surgery* 120:815-817).

Still others warn against the use of phenoxybenzamine (Pai, R. K., Conant, A. R., and Dihmis, W. C. 2008. "Treatment with Phenoxybenzamine May Lead to Loss of Endothelial Viability in Radial Artery," *Annals of Thoracic Surgery* 86(1):350-351 in response to Kulik et al. above with reply by author following; Conant, A. R., Shackcloth, M. S., Oo, A. Y., Chester, M. R., Simpson, A. W. M., and Dihmis, W. C. 2003. "Phenoxybenzamine Treatment is Insufficient to Prevent Spasm in the Radial Artery: The Effect of Other Vasodilators," *Journal of Thoracic and Cardiovascular Surgery* 126:448-454). The evidence implicates lumen-obstructing flaps with thrombus as the primary cause of abrupt closure with vasospasm an aggravating but secondary factor.

That abrupt closure is often accompanied by but never reducible to vasospasm as might be induced by the sudden impact of a projectile is also suggested by evidence that heparin anticoagulation as measured by the activated clotting time appears to reduce the risk of abrupt closure during angioplasty in proportion to the dosage without increasing the risk of major bleeding complications (Narins, C. R., Hillegass, W. B., Jr, Nelson, C. L., Tcheng, J. E., Harrington, R. A., Phillips, H. R., Stack, R. S., and Califf, R. M. 1996. "Relation Between Activated Clotting Time During Angioplasty and Abrupt Closure," *Circulation* 93(4):667-671; Bittl, J. A. and Ahmed, W. H. 1998. "Relation Between Abrupt Vessel Closure and the Anticoagulant Response to Heparin or Bivalirudin during Coronary Angioplasty," *American Journal of Cardiology* 82(8B):50P-56P). The use of both heparin and abciximab reduce the incidence of abrupt closure and implicate thrombus as a factor.

However, with the sudden impact of a projectile, both heparin anticoagulant-induced thrombocytopenia can remain threats (see, for example, Ahmed, I., Majeed, A., and Powell, R. 2007. Heparin Induced Thrombocytopenia: Diagnosis and Management Update," *Postgraduate Medical Journal* 83(983):575-582) and platelet blockade nonanticoagulant-induced thrombocytopenia (see, for example, Jubelirer, S. J., Koenig, B. A., and Bates, M. C. 1999. "Acute Profound Thrombocytopenia Following C7E3 Fab (Abciximab) Therapy: Case Reports, Review of the Literature and Implications for Therapy," *American Journal of Hematology* 61(3):205-208).

The use of a direct thrombin inhibitor appears to reduce the risk of this complication should it arise (see, for example, Gurm, H. S. and Bhatt, D. L. 2005. "Thrombin, An Ideal Target for Pharmacological Inhibition: A Review of Direct Thrombin Inhibitors," *American Heart Journal* 149(1 Supplement):543-53; Di Nisio, M., Middeldorp, S., and Buller, H. R. 2005. "Direct Thrombin Inhibitors," *New England Journal of Medicine* 353(10):1028-1040, erratum 353(26):2827; Arora, U. K. and Dhir, M. 2005. "Direct Thrombin Inhibitors (Part 1 of 2)," *Journal of Invasive Cardiology* 17(1):34-38, "Direct Thrombin Inhibitors (Part 2 of 2)," 17(2):85-91; French, M. H. and Faxon, D. P. 2002. "Current Anticoagulation Options in Percutaneous Intervention: Designing Patient-specific Strategies," *Reviews in Cardiovascular Medicine* 3(4): 176-182).

In addition to systemic administration, miniballs can be coated with antithrombogenic, anti-inflammatory, and/or intimal hyperplasia-suppressing medication, for example, as described below in the section entitled Medication (Nonstent) Implants and Medication-coated Miniballs, Implants, and Prongs. The risk of mortality and complications, to include cerebral hemorrhage, is stated to be reduced the earlier coronary reperfusion is initiated (Cannon, C. P. 2001. "Importance of TIMI-3 Flow," *Circulation* 104(6):624-626). Should such a response occur, miniballs with an outer coating to deliver these drugs in situ are used, with any collateral intravenous or oral dosage restricted to subhypotensive levels. Counterintuitively, because it is instantaneous, clean, bloodless, and limited to the tissue within and immediately surrounding the trajectory, implantation by such means should eventuate as minimally traumatizing with secondary swelling if any moderate and manageable.

4g. Emergency Recovery of Miniballs and Stays

The loss of a miniball into the lumen whether from the exit port or recovery magnet miniball trap or antechambers at the front of the muzzle-head is precluded both by the pull of the electromagnets and the fact that the antechambers are closed off by spring-loaded doors, and such an eventuality is immediately arrestable and the miniball recoverable by magnetic interception and recovery, as addressed in this section as well as several others. When a trapped miniball could be lost due to brushing against the lumen wall or due to jerking of the muzzle-head, the resting field strength is increased. Miniballs and stays include sufficient ferromagnetic content to allow retrieval regardless of the inclusion thereof for drug-targeting and/or stenting.

If an immediate need for stenting is not evident, the application of a stent-jacket is deferred to a later procedure contingent upon confirmation of the need therefor. When the eventual need for a stent-jacket can be discounted with relative confidence, the superparamagnetic magnetite or maghemite nanoparticles or finely grained powder content of the miniballs or stays is to allow recovery and can be dispersed through the miniball or stay in an absorbable matrix. The spherical form and small size of a miniball, even one made entirely of a magnetic stainless steel, for example, requires the use of a powerful magnetic field in order to apprehend it.

When loss would pose a risk, medication miniballs discharged for interspersal among stenting miniballs and stays positioned likewise to be encircled within a stent-jacket, and radiation seed-miniballs and stays to be encircled within a radiation shielded stent-jacket must have sufficient ferromagnetic content to allow retrieval but not so much as would induce pull-through or delamination; recovery applies greater field strength than does static traction. When the eventual need for a stent-jacket cannot be discounted, the ferrous content of the miniballs or stays preplaced initially should be nonabsorbably encapsulated, no stent-jacket placed until a later procedure following confirmation of the need therefor.

Broadly then, antiproliferative or chemotherapeutic medication is delivered in the form of miniballs or stays that preposition ferrous material for the eventual placement of a stent-jacket, with no placement of a stent-jacket until the need therefor has been confirmed. Once a miniball or stay with a deep surface texture becomes infiltrated by and integrated into the surrounding tissue, it is innocuous, and does not demand extraction. If the threat of burning surrounding tissue during essential magnetic resonance imaging arises, the stabilized miniball is extracted by means of a sudden pulse from a powerful external electromagnet. Nonabsorbed portions of miniballs or stays can remain implanted indefinitely, so that precautionary implantation never compels the placement of a stent-jacket not otherwise required.

When, as in a smaller artery, the miniballs or stays cannot be large or numerous enough to provide the dose-rate desired in addition to the prepositioned ferrous cores, an irradiating stent-jacket, as addressed below in the section entitled Radiation Stent-jackets, is used. Briefly, in a radiation stent-jacket, which can be provided with an absorbable surrounding shield as described below in the section entitled Radiation Shield-jackets and Radiation Shielded Stent-jackets Absorbable and Nonabsorbable, if necessary, the seeds are bonded in interleaved or sandwiched relation between the lining and the base-tube. Thus, in an artery, a stent-jacket is used only when needed for retraction to counteract shrinkage and/or for antiproliferative irradiation when irradiating miniballs or stays would be too small and/or numerous.

In descending order of preference, the six means provided for preventing the loss of a miniball in the circulation are: 1. The recovery electromagnets built into the muzzle-head of every radial discharge barrel-assembly; 2. An impasse-jacket prepositioned downstream from the treatment site; 3. The coincidental presence of a downstream stent-jacket or magnet-jacket that would seize the miniball in any event; 4. An external electromagnet to intercept and if necessary, extract the miniball; 5. Aspiration through a barrel-tube or fluid operated aspiration tool-insert, and 6. A run-ahead embolic trap-filter, which distal to the nose of the muzzle-head, is well removed from the line of discharge.

Midprocedurally, a downstream stent-jacket or magnet-jacket allows endoluminal recovery with the recovery electromagnets in the muzzle-head; however, unlike an impasse-jacket, these are not configured to allow extraction with the aid of an external electromagnet. This means that postprocedurally, a barrel-assembly would have to be introduced to retrieve a miniball from within a stent-jacket. Since a stent-jacket 1. Primarily serves to draw stenting miniballs radially outward toward itself; 2. The miniballs are introduced at an acute angle and seated subadventitially; and 3. The miniballs are conformed and treated for optimal integration into and adhesion to the surrounding tissue, the odds that a miniball would be released into the bloodstream postprocedurally are slight. Nevertheless, different methods for intercepting and retrieving a dropped miniball are addressed below.

Especially when a multiple discharge barrel-assembly is used, an impasse-jacket should be prepositioned downstream to trap any miniballs that enter the circulation. Midprocedurally, miniballs or stays are normally retrieved with the recovery electromagnets immediately present as built into the muzzle-head of every barrel-assembly and stay insertion tool. Removal by recovery electromagnet seizure directly from the lumen or from the downstream impasse-jacket is preferred as completely endoluminal, substantially atraumatic, and avoiding the need for transmural extraction (through the lumen wall and out the side). Impasse-jackets are dependable, but any barrel-assembly used to remove a miniball from an impasse-jacket must have recovery electromagnets with the field strength necessary to overcome the hold of the impasse-jacket.

For postprocedural emergency recovery, the risk of trauma to the ductus is minimized by prepositioning a miniball-impassable collar, or impasse-jacket, downstream from the implantation site. The postprocedural extraction of miniballs trapped in an impasse-jacket, if necessary, is best accomplished with the aid of an external electromagnet as the least complicated, noninvasive, and quickest method; the use of a barrel-assembly then only slightly less traumatic, an new entry incision and introducer sheath required. Barring malfunctioning of the apparatus preferred, the use of a spare barrel-tube or fluid tool-insert suction line to recover a loose miniball through aspiration is not recommended as awkward, undependable, and obscured by drawing in blood as well.

While unlikely, the accidental introduction of a miniball into the bloodstream by a barrel-assembly in use in another ductus due to an airgun malfunction or human error is responded to by the noninvasive extraluminal means for recovery next to be described. For midprocedural emergency recovery under adverse circumstances, such as when the ductus follows a deep and/or tortuous course, a powerful and tightly focused external electromagnet is prepositioned and when possible, pre-energized in addition to the trap-jacket. Either the jacket or the electromagnet then stops the miniball, with the external magnet used to extract the miniball from the trap-jacket if necessary. Miniball-impassable jackets are addressed below in the section entitled Miniball and Ferrofluid-borne Particle-impassable Jackets, or Impasse-jackets.

Applied and positioned without luminal entry, stays are not likely to enter the lumen, but may be defectively positioned. Ordinarily, a mispositioned stay can be disregarded. However, means must be provided for the removal of a stay that would detract from or pose a risk to proper function. Stays not completely ejected from the insertion tool can be retracted by the electromagnet built into the tool for this purpose. If completely ejected into an objectionable position, a more powerful extracorporeal electromagnet is used to pull the stay into a safe location. That miniballs, which tiny and spherical, can be extracted entirely outside the body with little risk may be intuited, stays, have pointed ends that would appear to require resituation to a safer position inside the body.

However, stays are also tiny and while more incisive during a forcible extraction than miniballs, are little capable of imparting significant trauma. Stays and miniballs generally have a surface texture to retain fluid coatings such as drugs and to encourage tissue integration for positional stability. Postprocedural extraction of miniballs associated with a stent-jacket that has failed due to pull-through, or of miniballs or stays where failure resulted from delamination so that the implants remain inside the stent-jacket, require that the stent-jacket be removed first, which must be accomplished surgically. The use of wide stays coated with bonding agents such as surgical cement or protein solder should make such occurrences rare.

Whereas a miniball that enters the lumen of a ureter, the gut, or fallopian tube, for example, will usually not become embedded in the lumen wall but be swept through and passed (voided) without the need for intervention, one released into a blood vessel will eventually reach its luminal diameter and occlude. When miniballs are implanted in the wall of an artery, midprocedural or postprocedural embolization must be prevented. To this end, an impasse-jacket used as a trap- or guard-jacket is prepositioned downstream. The noninvasive extraction of a miniball well before it reaches the level of embolization mid or postprocedurally otherwise requires the use of a powerful extracorporeal electromagnet, as addressed below in section X2c entitled Stereotactic Arrest and Extraction of a Circulating, Dangerously Mispositioned or Embolizing Miniball.

The midprocedural and nonemergency postprocedural interception and recovery by extraction, or evulsion, of miniballs that escape into the bloodstream is noninvasive, an external electromagnet used to withdraw the miniball through the lumen wall and mesh to a safe location, as explained just below. Endoluminal means for the recovery of miniballs mispositioned midprocedurally are not only the recovery tractive electromagnets built into the muzzle-head but include additional means summarized in the section below entitled Use of the Barrel-assembly as an Aspirator or Transluminal Extraction Catheter for the Removal of Soft Plaque or Mispositioned Miniballs.

The pertinent apparatus is also covered in respective sections directed to recovery electromagnets, trap-filters, and the use of a free barrel-tube or service-channel for aspiration. While medication miniballs that completely dissolve are uniformly seeded with superparamagnetic magnetite or maghemite nanoparticles or finely grained powder for midprocedural extraction or given a ferromagnetic core, for optimized magnetic susceptibilty, nonabsorbable stenting miniballs meant for long-term or permanent implantation best include a prismoidal core. A miniball caught in an impasse-jacket is noninvasively retracted to a safe location, generally just outside the treatment ductus, by means of a powerful external electromagnet.

When an angioplasty or atherectomy is unavoidable or the circumstances recommend endoluminal treatment with miniballs rather than stays, extraction is usually accomplished most quickly with the recovery tractive electromagnets built into the muzzle-head. Such circumstances may include an anomalous coronary artery that tunnels through the subjacent myocardium to be bridged over by a band of superjacent myocardium for more than 20 millimeters at a depth of more than 5 millimeters (See, for example, Garde, P. S., Karandikar, A. A., Tavri, O. J., Patkar, D. P. and Dalal, A. K. 2006. "Tunneled CoronaryArtery: Case Report," *Indian Journal of Radiology and Imaging* 16(3):283-284; additional references cited below in the section entitled Considerations as to Access) or a ductus that pursues a normal course through a connective sheath that passes amid skeletal muscles as in the extremities.

When the degree of accuracy required for implantation is uninvolved significantly reducing if not eliminating the need for extraction, extraction by an extraluminal route is manipulatively simpler and quicker. Except when the need for retrieval arises midprocedurally with the barrel-assembly endoluminal, extraction through the lumen wall is quicker to achieve, noninvasive, and less susceptible to mishaps. Moreover, since the trajectory of retraction is the same diameter as the miniball itself and spontaneously closes in behind the passing miniball to seal the tiny trajectory path, forcible extraction of a miniball through the lumen wall to a safe location is not only noninvasive but minimally traumatizing.

The diameters of the miniballs and impasse-jackets used to treat a given ductus or segment thereof proportional in dimensions and magnetic properties, unless the ductus wall is inordinately resistant to perforation as with advanced sclerosis or hard lesioning, the open mesh of an impasse-jacket is little larger than the diameter of the largest miniball placed upstream. For this reason, the retractive force exerted on a miniball to be extracted by an external electromagnet does not pull a significant area of the ductus wall through the mesh stretching or notching it. Rather, the tractive force is effective at the intended puncture site. This results in a clean perforation, making nonendoluminal (nontransluminal) approach preferable for recovery.

When no stent-jacket must be recovered, irradiating and medication miniballs containing ferrous matter such as superparamagnetic magnetite or maghemite nanoparticles or finely grained powder for the express purpose of recovery may be retrieved noninvasively through the application of a powerful external magnetic field, stereotactic arrest and extraction used when exceptionally necessary to avoid injury to structures along the retraction path. The use of an external electromagnet to interdict and/or extract a problem miniball is addressed below in the section entitled Steering and Emergency Recovery of Implants with the Aid of an External (Extracorporeal) Electromagnet. Miniballs for use with a magnetic stent-jacket generally release neither radiation nor drugs.

Whether implanting elemental superparamagnetic magnetite or maghemite nanoparticles or finely grained powder in the wall of a ductus would in practice reach a level that resulted in a functionally significant iron overload, hemosiderosis, or hemochromatosis, or additional iron resulting from the extravasation of erythrocytes from the vasa vasora of larger arteries during insertion could produce such a result is unlikely. Gold specified herein is not in compound form, is noble or nonreactive, and without toxic potential. Since erroneously placed ferromagnetic miniballs will seldom interfere with normal function, those mispositioned in preparation to place a stent-jacket can usually be left as is. The likelihood of mispositioning the stent-jacket is slight, but provided with a moisture barrier-coated viscoelastic polyurethane foam or other slide-resistant lining and endties to prevent migration, the jacket will require reentry to correct.

Outside the vascular tree, the miniature balls and stays to be described can omit magnetic content when the use thereof for retrieval will be unnecessary. The implants then consist purely of medication, which can incorporate time-released layers, for example, or radiation-emitting seeds coated with medication whether multiple which is unaffected by the radiation. Conventional seeds are not absorbed, but absorbable polymers can be coated or impregnated with radioactive nuclides for complete absorption. Such combinations are considered minor variants substantially consistent with established pharmaceutical practice. Similarly, stent-jackets are most often, but not always, of the magnetic type. In FIG. 1, the relation shown between implants that attract or draw and those attracted or drawn is often reversible; that the components in either column may represent either the magnets or the components attracted to the magnets is considered obvious.

5. Means for the Placement of Ductus-Intramural Implants

The intraductal elements consist of miniballs, placed with a barrel-assembly, and arcuate stays, placed with a stay insertion hand tool, all addressed below in the respective section of like title. With sufficient ferrous content, miniballs and stays can serve as the intraductal component of a magnetic extraluminal stent; however, neither miniballs nor stays need have any relation to stenting. Either type intraductal element can consist of medication and/or other therapeutic substances, such as tissue bonding, or surgical, cement, hardening (sclerotic), or swelling (tumefacient) agents, and the nonintraductal implants described herein can also be coated thus. For recoverability with the aid of an external electromagnet if unintentionally released (dropped) or mispositioned, virtually all of these implants, to include those fully absorbable, contain some ferrous matter.

The luminal diameter, and if containing axially protrusive hard (calcified, petrous, angiosteosic) matter, the degree of luminal obstruction, will set a limit to the diameter of the barrel-assembly that can pass, while the strength and tortuosity of the ductus wall, if any, will determine how flexible the barrel-assembly must be. The treatment required determining the kind of radial projection units needed, both the limitation on diameter and flexibility will determine whether the barrel-assembly can be of the multibarrel type; or ensheathed within a matching combination-form radial projection catheter, and/or be of the combination-form type, and whether ensheathment can be accomplished before rather than after the muzzle-head has been moved to the treatment site.

To the extent that the foregoing determinants allow, radial projection units of the kind and range of functional capability needed can be integral to the muzzle-head, or the need for bendability may require that a luminally size-matched combination-form radial projection catheter be added after the unsheathed barrel-assembly muzzle-head has been positioned at the treatment site. Thus, small gauge lumina, those surrounded by weak or tortuous walls, and those obstructed are first negotiated with a barrel-assembly of small diameter having at least a thermoablating heat-window at the nose. If rock-hard calcified plaque obstructs a lumen too narrow to accommodate a combination-form barrel-assembly with a rotational or linear cutter inserted, then a separate cutter is used prior to insertion of the barrel-assembly. Less highly calcified plaque can also be removed with an excimer laser or ultrasonic probe. It will now be understood that any increment in diameter and wall strength will admit of a significant increase in the means described herein for treating the ductus.

6. Endoluminal Prehension of Miniballs and Ferrofluids

Impasse-jackets, addressed below in the section entitled Concept of the Impasse-jacket and Miniball and Ferrofluid-borne Particle-impassable Jackets, or Impasse-jackets among others, serve primarily as downstream guard- or stopping-jackets to trap a loose miniball or miniballs and thus interdict these from further passage through the circulation. The impasse-jacket is designed to comply with the intrinsic motility in the ductus and is placed to encircle the ductus with minimal injury to the adventitia or fibrosa. Circumferentially magnetized normal to its central axis and having a cylindrical open mesh body, the impasse-jacket used as a stopping-jacket allows a trapped miniball to be extracted with the aid of an external electromagnet through the ductus wall to a location outside the ductus with minimal trauma.

Other means for retrieving loose miniballs in the circulation include the recovery electromagnets built into the muzzle-head of the miniball implanting barrel-assembly itself, the use of a prepositioned external electromagnet, and if so equipped, the aspirators incorporated into the radial projection system. Impasse-jackets also serve as holding jackets for suspending a medication or radiation-emitting miniball in the lumen or for attracting a drug or nucleotide-bound ferrofluid, for example, within the lumen at the level desired. In order to direct the medication into the arc containing the lesion to be treated, these are more likely to incorporate asymmetrical magnetization; however, their use as trap-jackets is unaffected, the trapped miniball or miniballs directed to the arc of greater field strength.

Magnetic drug-targeting is addressed in the section above entitled System Implant Magnetic Drug and Radiation Targeting and in the sections below entitled Concept of the Impasse-jacket and Miniball and Ferrofluid-borne Particle-impassable Jackets, or Impasse-jackets, among others. While the extraluminal stent requires minor surgery to place, it is superior to an endoluminal stent for the drawing drug carrier magnetized particles and nanoparticles, because it leaves the lumen clear, can present a far more powerful magnetic field than an endoluminal stent can achieve within such a limited space, and outside the ductus pulls the ferrofluid-bound drug into the lesion or neoplasm. With an external extraction electromagnet, an accidental or idiopathic overdose can be withdrawn instantly through the mesh of the holding jacket.

Holding jackets are addressed below in the section entitled Miniball and Ferrofluid-borne Particle-impassable-jackets, or Impasse-jackets. Holding jackets allow medication miniballs containing statin drugs, for example, to be suspended within the bloodstream. In this way, treatment is targeted at the endothelium within an artery, for example. Such dosing is generally repetitive over a limited term, recommending the use of absorbable materials that eliminate the need for recovery once placed through a small incision. To leave no magnetized material once its useful life has passed, the jacket mesh is made of an absorbable polymer and its magnetization is of the polymer-incorporated biocompatible particulate of which the mesh consists or is coated.

As addressed below in the section entitled Implants that Radiate Heat on Demand, an impasse-jacket can also incorporate means for generating heat when energized from outside the body. Small-scale and substantially lesion-restricted drug-targeting within a lesioned blood vessel, for example, allows drug concentrations that if circulated would be toxic. Either the endothelium or deeper layers can be targeted over a defined segment in any of several ways. Treatment of the endothelium is by positioning an impasse-holding jacket as an exit jacket to suspend a miniball with a central core or distributed array of tissue compatibly encapsulated ferrous matter at the end of the segment so that the miniball dissolves to release a substance or substances that directly disable or reverse, counteract, or neutralize the drug or drugs injected or infused upstream at the start of the segment.

In this case, magnetism serves only to retain the neutralizing miniball in position, the drugs used conventional. The drug targeting of a defined segment of a ductus or an organ is addressed below in the section entitled Cooperative Use of impasse-jackets in Pairs and Gradient Arrays, among others. To free the patient from the clinic, the inception of the segment can also be represented by an entry-jacket, which once implanted, can then be made to retain a miniball suspended therein for breakdown and the release of medication on demand such as when the patient ingests a miniball-disintegrating or activating substance. When necessary, the drug is self-administered by injection or infusion through a subcutaneously implanted portal.

In the digestive tract, for example, contents are also needed to carry the medication forward; when necessary to achieve the necessary propulsive force relative to the degree of magnetic susceptibility, the ductus may be injected with a substance to fill it and/or accelerate or intensify the force of its motility. Depending upon the function of the medication, however, dissolution of the start of segment miniball may be too slow. Then accelerating release from the entry jacket and/or activating the drug to intensify or deactivating the drug to mollify its effect may necessitate the addition of another agent by injection, infusion, and/or heating by placement in an alternating magnetic field, for example, conventionally tied to the clinic.

That miniballs or their contents in either or both entry and exit jackets can be affected in the time of drug release or that the properties of the therapeutic and if used, neutralizing drug can often be adjusted in effective concentration, for example, by introducing an additional agent or heat is obvious, as is the fact that start of segment sites difficult to reach by direct injection or infusion may warrant the pre-placement of an entry-jacket. To treat deeper or abluminal layers along a defined segment of a ductus, usually a blood vessel, the medication introduced at the start of the segment is locally injected as a ferrofluid or as absorbable microspheres or miniballs containing drug carrier particles or nanoparticles.

Since the drug-component is bound to the carrier particle, the drug in such a ferrofluid is described as ferrobound and is drawn to an impasse-jacket by relative strength of the vectors that result from contents propulsion that would push the particles past the impasse-jacket and the magnetic field strength which would attract the particles, which is incrementally increased in the antegrade direction. When the drug released from a disintegrating miniball is intended for uptake into a lesion within the lumen wall against the propulsive force of the lumen contents by attraction to perivascular impasse-jackets, or is intended for uptake by an organ that does not normally take up the drug or substance to which the drug is bound, the drug is ferrobound.

By contrast, drugs confined but not combined with or bound to the susceptible particulate component in the ferrofluid, microspheres, or shell of the miniball, for example, as to be separated and carried forward when released are described as ferro co-bound, which are not drawn to impasse-jackets. Drugs for treating the internal surface of the lumen or an organ will often be of this type without magnetic susceptibility. The use of an absorbable drug-releasing endoluminal stent as the start of segment drug release device is not preferred, primarily because of the interference with intrinsic motility it causes and the sequelae to which this can lead. While a more precise starting point necessitates the preplacement of a microsphere or miniball-suspending holding jacket, when accessible, direct injection or infusion upstream from the first impasse-jacket is used. The point of infusion or injection may not represent the start of the segment to be treated but only the entry point for loading or charging the entry-jacket.

When a ferrobound drug, for example, is released, the initial fraction taken up by the entry jacket itself is that least magnetically susceptible, each successive fraction targeted distally more susceptible and/or each successive jacket moving distad more strongly magnetized. So that to the extent possible successive fractions will be drawn into the lumen wall by the progressively stronger impasse-jackets encountered in the correct proportion, the particles are graduated in magnetic susceptibility, and if necessary, the jackets increased in strength of magnetization. Used in these ways, impasse-jackets make possible the targeting of a selectable segment, not just a focal point of a ductus, and can accomplish this for magnetic drug-targeting using ferrofluids and drug and/or radioactive miniball guidance on a very small-scale.

A holding jacket for use to suspend microspheres or a miniball will generally tend to concentrate the magnetization at its longitudinal center, whereas one for use with ferrofluids will generally be uniformly magnetized along its length. As but one example of such use, statins (3-hydroxy-3-methylglutaryl coenzyme A reductase inhibitors) are suspected by some to reduce the inflammation of atherosclerosis through mechanisms not dependent upon a reduction in serum cholesterol or triglycerides, and in so doing, are accepted to preserve the remaining kidney function in diabetics. The application of holding jackets to the use of statins is addressed below in the section entitled Cooperative Use of Impasse-jackets in Pairs and Gradient Arrays. Atherosclerosis is a systemic condition that will usually call for a background systemic dose of the statin; however, the ability to target acute lesions has therapeutic value.

7. Comparison with Prior Art Angioplasty

Crushing plaque and subjecting the luminal wall to stretching injury, conventional balloon angioplasty promotes neointimal hyperplasia and medial cell proliferation, which the irritation of an endoluminal stent probably increases. The methods and apparatus described herein are intended to reduce reinflammation, lesioning, and restenosis. Compliant with intrinsic expansion and contraction, and not excessively distending the ductus to preclude migration, an extraluminal stent is not a chronic irritant that promotes reocclusion and is susceptible to clogging. Removing most if not all of the stimulus to restenosis can be further supported through the use of medicated or time-released medicated ductus-intramural implants, or lesion-targeted injection using syringe injector tool-inserts, as will be described.

The higher concentration of drugs than might be introduced into the systemic circulation allowed by the drug targeting means described herein should reduce the need for stenting of any kind. By avoiding balloon injury to an artery as may result in inflammation entirely through its wall, an atherectomy performed by the means to be described facilitates treatment by the extraluminal stenting means to be described, which include stent-stays and clasp-wraps that avoid the lumen entirely. Balloon angioplasty compresses soft atheroma more than hard plaque, leaving an irregular surface that induces turbulent flow increasing thrombogenicity. The compressed tissue often 'recoils,' that is, resiliently re-expands, to partially re-obstruct the lumen.

To this partial closure is then added the intimal hyperplasia induced by balloon stretching injury (see, for example, Luo; H., Nishioka; T., Eigler; N. L., Forrester; J. S., Fishbein; M. C., Berglund; H., and Siegel, R. J. 1996. "Coronary Artery Restenosis after Balloon Angioplasty in Humans is Associated with Circumferential Coronary Constriction," *Arteriosclerosis, Thrombosis, and Vascular Biology.* 16(11): 1393-1398; Currier, J. W. and Faxon, D. P. 1995. "Restenosis after Percutaneous Transluminal Coronary Angioplasty: Have We Been Aiming at the Wrong Target?," *Journal of the American College of Cardiology* 25(2):516-520), and the degree of closure becomes significant even without completion by an embolism (atheroembolism). Balloon stretching can produce restenosis, incisions, abrupt closure, and vasospasm.

Whereas the conventional reduction of obstructive tissue within arteries by balloon angioplasty differs from the ablative means conventionally used with other type ductus, the inventive apparatus consistently ablates obstructive tissue in arteries as well by any of a number of means to include thermoplasty, curettage, and cryoplasty. The newer devices for use in arteries which actually ablate rather than merely crush atheromatous lesions, such as cutting balloons, rotational atherectomizers, directional atherectomizers, and excimer lasers, have become several, but require that the angioplasty be completed in an initial transluminal pass before reentry to stent can commence.

Neither do these allow the targeted application of medication or other agents to or into the luminal wall, much less during angioplasty or stenting. Means for performing a thermal angioplasty (thermoplasty, thermocautery angioplasty) are incorporated into angioplasty-capable barrel-assemblies and radial projection catheters and can be incorporated into minimally angioplasty-capable barrel-assemblies. The object is to prevent the erosion of fibrous plaque exposed to low density lipoprotein heavy blood that would prove thrombogenic or release embolizing debris on rupturing vulnerable plaque.

A preemptive pass, preferably not separate but integrated, is performed at 85 to 90 degrees centrigrade to destroy the plaque and its contents by cautery (Post, M. J., de Graaf-Bos, A. N., Posthuma, G., de Groot, P. G., Sixma, J. J., and Borst, C. 1996. "Interventional Thermal Injury of the Arterial Wall: Unfolding of von Willebrand Factor and Its Increased Binding to Collagen After 55 Degrees C.[elsius] Heating," *Thrombosis and Haemostasis* 75(3):515-519; Nardone, D. T., Smith, D. L., Martinez-Hernandez, A., Consigny, P. M., Kosman, Z., Rosen, A., and Walinsky, P. 1994. "Microwave Thermal Balloon Angioplasty in the Atherosclerotic Rabbit," *American Heart Journal* 127(1): 198-203). Preferably, the cautery is accomplished in the same pass as any other therapeutic process the radial projection catheter or barrel-assembly is used for.

This temperature is based upon the literature, and if in need of correction, the content hereof is not dependent thereupon. A distal embolic trap-filter to catch debris is redundant but can be used if deployed far enough ahead of the nose heat-window. Angioplasty-capable barrel-assemblies can also accept connection to sources of cold fluid to perform a cryoplasty through service catheters passed through barrel-tubes and/or fluid-operated tool-inserts. Angioplasty systemic, a preemptive pass as continuous or applied to sites of vulnerable plaque is addressed below in the section entitled Thermal Ablation and Angioplasty- (Lumen Wall Priming Searing- or Cautery-) Capable Barrel-assemblies.

Endothelial dysfunction and atherosclerosis as an inflammatory process both systemic, function is impaired on presentation, leaving the issue of the extent of impairment or additional impairment to result from treatment problematic. The ablation and angioplasty means provided herein include radially outward-directed or side-looking cutting, heating (thermoplasty), and chilling (cryoplasty) radial projection unit tool-inserts or canisters attachable to the barrel-assembly or to the radial projection assembly, and barrel-assembly-incorporated excimer (excited dimer) lasers or rotatatory blade atherectomizers, described in sections to follow. If not inherently eradicated by such means, removed tissue is aspirated or trapped beneath the cutting tool.

By contrast, conventional balloon angioplasty does not remove but rather redistributes plaque to clear a passageway or channel through the lumen by crushing the plaque between the endothelium and the internal elastic lamina, injuring both (see, for example, the background section in Chigogidze, N. A. 1997. "Device and Method for Dynamic Dilation of Hollow Organs with Active Perfusion and Extraction," U.S. Pat. No. 5,695,508) and inducing luminally obstructive cell proliferation, consisting primarily of intimal hyperplasia (see, for example, Harnek, J., Zoucas, E., Stenram, U., Cwikiel, W. 2002. "Insertion of Self-expandable Nitinol Stents without Previous Balloon Angioplasty Reduces Restenosis Compared with PTA Prior to Stenting," *Cardiovascular and Interventional Radiology* 25(5):430-436).

Rotational atherectomy, which can be incorporated into a combination-form barrel-assembly or a radial projection catheter, as addressed below in sections of like title, not only allows the removal of highly calcified plaque, but is claimed to stimulate intimal hyperplasia to a lesser degree (McKenna, C. J., Wilson, S. H., Camrud, A. R., Berger, P. B., Holmes, D. R. Jr., and Schwartz, R. S. 1998. "Neointimal Response Following Rotational Atherectomy Compared to Balloon Angioplasty in a Porcine Model of Coronary In-stent Restenosis," *Catheterization and Cardiovascular Diagnosis* 45(3):332-336). Some methods in actual practice impose greater trauma and risk of complications than do the means for accomplishing an angioplasty and stenting described herein.

Those documented in the literature include percutaneous intentional extraluminal recanalization (revascularization, subintimal angioplasty) (see Scott et al. 2007, Ko et al. 2007, Cho et al. 2006, Mishkel et al. 2005 referred to under the section above entitled Risk of Abrupt Closure) and vessel size-adapted angioplasty pursuant to a concept of 'therapeutic dissections,' addressed below in the section below entitled Basic Strengths and Weaknesses of Prior Art Stenting in Vascular, Tracheobronchial, Gastrointestinal, and Urological Interventions, among others. Other cabled cabled devices that can be included in a combination-form barrel-assembly for removing calcified plaque include lasers and ultrasonic probes.

The inability of a laser catheter to remove more than moderately calcified plaque by cavitation, thermal breakdown, and vaporization (see, for example, Vorwerk, D., Zolotas, G., Kohnemann, R., Hessel, S., Adam, G., and Günther, R. W. 1990. "Laserangioplastie und Abtragung kalzifizierter Plaques, Eine In-vitro-Studie" [Laser Angioplasty and the Removal of Calcified Plaques. An in Vitro Study], in German with abstract in English at Pubmed, *RöFo.: Fortschritte auf dem Gebiete der Rontgenstrahlen und der Nuklearmedizin* (RöFo [Röntgenstrahlen Fortschritte]: Advances in the Field of X-rays and Nuclear Medicine) 152(6):693-697) and of a 2.1 micron holmium laser to do so at fluences per pulse of less than 205 Joules per square centimeter (see Vorwerk, D., Zolotas, G., Hessel, S., Adam, G., Wondrazek, F., and Günther, R. W. 1991. "In Vitro Ablation of Normal and Diseased Vascular Tissue by a Fiber-transmitted Holmium Laser," *Investigative Radiology* 26(7):660-664) has been contradicted by others (see Ben-Dor, I., Maluenda, G., Pichard, A. D., Satler, L. F., Gallino, R., Lindsay, J., and Waksman, R. 2011. "The Use of Excimer Laser for Complex Coronary Artery Lesions," *Cardiovascular Revascularization Medicine* 12(1):69.e1-e8; Bilodeau, L., Fretz, E. B., Taeymans, Y., Koolen, J., Taylor K., and Hilton, D. J. 2004. "Novel Use of a High-energy Excimer Laser Catheter for Calcified and Complex Coronary Artery Lesions," *Catheterization and Cardiovascular Interventions* 62(2): 155-161).

Another cabled device that can be incorporated into a combination-form barrel-assembly is an ultrasonic catheter, likewise claimed effective at removing calcified plaque (Siegel, R. J. 1996. *Ultrasound Angioplasty*, Boston, Mass.: Kluwer Academic Publishers/Springer; Siegel, R. J., Gaines, P., Crew, J. R., and Cumberland, D. C. 1993. "Clinical Trial of Percutaneous Peripheral Ultrasound Angioplasty," *Journal of the American College of Cardiology* 22(2):480-488; Chikada, M. 2004. "An Experimental Study of Surgical Ultrasonic Angioplasty: Its Effect on Atherosclerosis and Normal Arteries," *Annals of Thoracic Surgery* 77(1):243-246; Gavin, G. P., McGuinness, G. B., Dolan, F., and Hashmi, M. S. J. 2005. "Development and Performance Characteristics of an Ultrasound Angioplasty Device," Dublin Institute of Technology School of Manufacturing and Design Engineering, *Bioengineering Conference Papers*, available at http://arrow.ditie/engschmanconn/2; Wylie, M., McGuinness, G. B., and Gavin, G. P. 2009. "Therapeutic Ultrasound Angioplasty: The Risk of Arterial Perforation. An in Vitro Study," Dublin Institute of Technology School of Manufacturing and Design Engineering, Bioengineering Conference Papers, available at http://arrow.ditie/engschmanconn/7).

Applied to a chronic total occlusion of a coronary artery, revascularization by such means is more likely to result in restenosis concurrent with atrophy of the collateral circulation that developed to adapt to the occlusion, with the consequence catastrophic (see, for example, Pohl, T., Hochstrasser, P., Billinger, M., Fleisch, M., Meier, B., and Seiler, C. 2001. "Influence on Collateral Flow of Recanalising Chronic Total Coronary Occlusions: A Case-control Study," *Heart* 86(4):438-443). Abrupt closure with vasospasm, or vasoconstriction, as the result of balloon overstretching or following placement of a drug-eluting stent is addressed above in the section entitled Risk of Abrupt Closure with Thrombus and Vasospasm. Passage of severely stenosed and tortuous stretches by a barrel-assembly muzzle-head of suitable diameter is by slippage (slip-through, slide-through), the nose convex or spheroconical (torpedo or bullet-nosed) and lubricious.

The risk of abrupt closure with or without concomitant vasospasm using the apparatus described herein is addressed in the section above of like title. If not creating a flap that results in an abrupt closure, balloon angioplasty with an oversized balloon or overinflation can produce stretching injury, dissections, and thrombus, and with underinflation too narrow a lumen, in either contingency, leading to subacute closure (Cheneau, E., Mintz, G. S., Leborgne, L., Kotani, J., Satler, L. F., Ajani, A. E., Weissman, N. J., Waksman, R., and Pichard, A. D. 2004. "Intraductal Ultrasound Predictors of Subacute Vessel Closure After Balloon Angioplasty or Atherectomy," *Journal of Invasive Cardiology* 16(10):572-574; Cheneau, E., Leborgne, L., Mintz, G. S., Kotani, J., Pichard, A. D., Satler, L. F., Canos, D., Castagna, M., Weissman, N. J., and Waksman, R. 2003. "Predictors of Subacute Stent Thrombosis: Results of a Systematic Intraductal Ultrasound Study," *Circulation* 108 (1):43-47).

Removal of tissue protrusive into the lumen is primarily through the application of heat directed, or of cutting or abrasive tools projected, radially outward from the muzzle-head or radial projection catheter. Cold is obtained by attaching a source of $CO_2$ or a chilled liquid to the barrel-assembly. Eliminating a guidewire eliminates the potential for guidewire breakage, which can result in the intra-arterial loss of a fragment and gouging or rupture of the vessel wall. Such incidents and the complications to which these give rise are rare but continue to be reported in the literature (references provided below under the section entitled Strengths and Weaknesses of Conventional Interventions). Additional complications from guidewires are addressed below in this section. Using the apparatus to be described, plaque is removed rather than crushed, which is injurious when a balloon is overinflated.

Atherectomy performed by any of the foregoing means with medical follow-up actually removes the plaque or other occlusive matter, and therefore would appear to have the potential to reduce if not eliminate the need for stenting (see Sharma, S. K., Kini, A., Mehran, R., Lansky, A., Kobayashi, Y., and Marmur, J. D. 2004. "Randomized Trial of Rotational Atherectomy versus Balloon Angioplasty for Diffuse In-stent Restenosis (ROSTER)," *American Heart Journal* 147(1):16-22; Shafique, S., Nachreiner, R. D., Murphy, M. P., Cikrit, D. F., Sawchuk, A. P., and Dalsing, M. C. 2007. "Recanalization of Infrainguinal Vessels: Silverhawk, Laser, and the Remote Superficial Femoral Artery Endarterectomy," *Seminars in Vascular Surgery* 20(1):29-36).

In practice, however, no means for reinstating patency completely avoids the risk of restenosis. Endoluminal stenting may serve balloon angioplasty by covering over any dissections, to include loose flaps that would induce an abrupt closure, that may have resulted from overinflation and by retaining or 'tacking up' debris compressed against the lumen wall, thus preventing debris greater in diameter than 5 micrometers, which is too large to pass through capillaries, from passing downstream. By contrast, extraluminal stenting as described herein does not achieve patency by endoluminal scaffolding and therefore does not simply force debris up against the lumen wall merely to counteract balloon damage and its sequelae of hyperplasia, shrinkage, and spasm.

Combined nonatherectomizing angioplasty and endoluminal stenting usually results in the inward protrusion through the stent struts of the unremoved atheroma. The advent of absorbable endoluminal stents may discourage this practice, since any residual diseased tissue that had been compressed could be released to embolize downstream as the stent is absorbed. Since in some patients, even with medication, the sites, such as bifurcations and oscula, but not the interval preceding the development of lesions can be predicted, absorbable stents cannot be used preventively. By contrast, the extraluminal stents described herein can be placed at any time, retain patenting effectiveness indefinitely, and can therefore be prepositioned to preventive effect. Drugs such as statins alone can reduce the inflammation associated with arterial disease and detain the emergence but not dissolve atheromas.

Omitting a preliminary angioplasty may interfere with absorption of the stent into the luminal wall. The minimally invasive use without an antecedent angioplasty of an everolimus-eluting absorbable stent, for example, therefore recommends either an angioplasty prior to insertion or that the stent also be irradiated. The more invasive implantation of irradiating seeds to suppress restenosis before the stent is absorbed is unrealistic, a suitable means for introducing such necessitating the use of a stay insertion tool or barrel-assembly as described herein. The barrel-assemblies described herein include ablative capability in a type device that can be used with single entry and withdrawal for that limited purpose or to implant any luminal wall with medication and/or ferromagnetic material as well at any moment in any order. Such supplants the need for a separate and inherently inferior form of angioplasty and the use of an inherently inferior endoluminal stent.

Moreover, by changing the magazine clip or removing the barrel-assembly from one airgun and inserting it into another, the type miniball implants as medicinal, consisting of or containing binding agents, tissue hardeners, tumefacients, irradiating seeds, or any combination thereof can be changed in an instant. Similarly, stays can be loaded into the insertion tool in any sequence or a tool containing one type stay can be withdrawn and another introduced. Not intended to trap smashed atheromas up against lumen walls in order to secondarily compensate for a deficiency of balloon angioplasty, extraluminal stenting is paired primarily with thermoablation and vibratory cutting tools, which can be used in combination and do not apply outward radial force against the wall of the lumen merely to crush, rather than to actually remove, plaque or obstructive tissue (see, for example, Heintzen, M. P., Aktug, O., and Michel, C. J. 2002. "Debulking Prior to Stenting—A Worthwhile Effort?," *Zeitschrift für Kardiologie* 91 Suppl 3:72-76).

The actual removal of diseased tissue such as atheromata or plaque (atheroablation), as opposed to its mere crushing and displacement through balloon angioplasty preferable, and endoluminal stenting being a multirisk-laden underpinning or 'crutch' for balloon angioplasty as an inferior method for clearing the lumen, the pairing of a photoablative laser with extraluminal stenting comprehends major improvements of both, making the accommodation by the barrel-assembly of a laser beneficial. Since thermoplasty and oscillatory ablative capabilities are built into ablation and ablation and angioplasty-capable barrel-assemblies, atherectomy and implantation of the intraductal component of the extraluminal stent is accomplished with single entry. Cutting tools if any retracted, the turret-motor drive can be programmed for oscillation to assist passage through tortuous stretches, and trackability can be further expedited through the release of a lubricant from the muzzle-head.

The release of fluid substances into the lumen wall using radial projection units is addressed below in the section entitled Radial Projection Unit Tool-inserts and in sections pertaining to injection tool-inserts. Release into the lumen is through electrically, electrochemically, or fluidically operated tool-insert ejection syringes or a barrel-tube. The barrel-assembly provides multiple means for removing plaque or other diseased tissue and/or adherent material in other type ductus. Through-bore or combination-form barrel-assemblies and radial projection catheters can incorporate a laser for photoablation or a rotational cutting tool for atherectomy. For use as a separate device, an ablation or ablation and angioplasty-capable barrel-assembly demands free and independent mobility.

To this end, the power and control housing can be slid along the barrel-catheter into position just short of the length of the barrel-assembly that will be inserted into the barrel of the airgun. A control panel for ablative and angioplastic functions is mounted to the side of the housing. When mated to an ensheathing, or ensleeving, radial projection catheter thereby to constitute a duplex (composite, bipartite) barrel-assembly, the power and control housings of each can be slid along the shafts of both in adjacent relation. These ballistic implantation-preparatory or end-purpose ablation or angioplasty controls include those for heating the turret-motor stator and for heating either or both of the recovery electromagnet windings, deploying the radial projection unit tool-inserts, rotating the turret-motor, and thus directing (rotating) an eccentric (slot or slit shaped) turret-motor heat-window and/or radial projection unit tool-inserts, for example.

Encouraging preemptive thermoplasty by nose and other heat-windows in the muzzle-head is the finding that an acute event most often results from sudden thrombogenic occlusion attendant upon the release of necrotic core material following the rupture of a fatty atheromatous plaque or a thin fibrous capped atheroma, or fibroatheroma, exposed to low density lipoprotein laden blood (Virmani, R., Burke, A. P., Farb, A., and Kolodgie, F. D. 2006. "Pathology of the Vulnerable Plaque," *Journal of the American College of Cardiology* 47(8 Supplement):C13-18; Virmani, R., Burke, A. P., Kolodgie, F. D., and Farb, A. 2002. "Vulnerable Plaque: The Pathology of Unstable Coronary Lesions," *Journal of Interventional Cardiology* 15(6):439-446; Burke, Farb, A., Malcom, G. T., Liang, Y. H., Smialek, J., and Virmani, R. 1997. "Coronary Risk Factors and Plaque Morphology in Men with Coronary Disease Who Died Suddenly," *New England Journal of Medicine* 336(18): 1276-1282Farb, A., Burke, A. P., Tang, A. L., Liang, T. Y., Mannan, P., Smialek, J., and Virmani, R. 1996. "Coronary Plaque Erosion Without Rupture into a Lipid Core. A Frequent Cause of Coronary Thrombosis in Sudden Coronary Death," *Circulation* 93(7):1354-1363;) or the rupture of vulnerable plaque where the reduction in flow has not yet been compensated for by the development of collateral circulation; by contrast, a gradual cutoff of flow through the lumen due to a plaque that has gradually come to protrude into the lumen to a greater extent is so compensated. For this reason, a vessel with chronic total occlusion can be asymptomatic and one slightly protrusive can cause death. An angioplasty that discourages the development of collateral circulation can be counterproductive.

Smashing plaque that is not vulnerable but merely protrudes into the lumen can actually cause an infarction, and this consequence is more likely when the plaque is indeed vulnerable (Waksman, R. Serruys, P. W., and Schaar, J. 2007. *Handbook of the Vulnerable Plaque*, London, England: Informa Healthcare; Waxman, S., Ishibashi, F., and Muller, J. E. 2006. "Detection and Treatment of Vulnerable Plaques and Vulnerable Patients: Novel Approaches to Prevention of Coronary Events," *Circulation* 114(22):2390-2411; Naghavi, M.; Libby, P; Falk, and 55 others 2003. "From Vulnerable Plaque to Vulnerable Patient: A Call for New Definitions and Risk Assessment Strategies: Part I," *Circulation* 108(14):1664-1672; Libby, P. and Aikawa, M. 2002. "Stabilization of Atherosclerotic Plaques: New Mechanisms and Clinical Targets," *Nature Medicine* 8(11) 1257-1262, erratum 9(1):146; Moreno, P. R. 2001. "Pathophysiology of Plaque Disruption and Thrombosis in Acute Ischemic Syndromes," *Journal of Stroke and Cerebrovascular Disease* 10(2 Part 2):2-9; Muller, J. E. Abela, G. S. Nesto, R. W. and Tofler, G. H. 1994. "Triggers, Acute Risk Factors and Vulnerable Plaques: The Lexicon of a New Frontier," *Journal of the American College of Cardiology* 23(3):809-813; Ley, O. and Kim, T. 2007. "Calculation of Arterial Wall Temperature in Atherosclerotic Arteries: Effect of Pulsatile Flow, Arterial Geometry, and Plaque Structure," *Biomedical Engineering Online* 6:8; ten Have, A. G., Gijsen, F. J., Wentzel, J. J., Slager, C. J., and van der Steen, A. F. 2004. "Temperature Distribution in Atherosclerotic Coronary Arteries: Influence of Plaque Geometry and Flow (a Numerical Study)," *Physics in Medicine and Biology* 49(19):4447-4462; Shah, P. K. 2002. "Pathophysiology of Coronary Thrombosis: Role of Plaque Rupture and Plaque Erosion," *Progress in Cardiovascular Diseases* 44(5):357-368).

When collateral circulation is insufficient, reperfusion or recanalization to the Thrombolysis in Myocardial Infarction study-defined Grade III (TIMI III, normal) flow is known to produce a more favorable prognosis the more promptly it is accomplished. However, when collateral circulation is sufficient, even coronary total occlusion (see, for example, Waksman, R. (ed.) 2009. *Chronic Total Occlusions*, Hoboken, N.J.: Wiley-Blackwell) may be disserved by angioplasty, which given a heavy burden of plaque, can reduce if not eliminate the collateral circulation by involution (Pohl, T., Hochstrasser, P., Billinger, M., Fleisch, M., Meier, B., and Seiler, C. 2001. "Influence on Collateral Flow of Recanalising Chronic Total Coronary Occlusions: A Case-control Study," *Heart* 86(4):438-443) or embolization (Meier, B. 1989/2005. "Angioplasty of Total Occlusions: Chronic Total Coronary Occlusion Angioplasty," *Catheter-* ization and Cardiovascular Diagnosis 17(4):212-217; Kahn, J. K. 1995/2005. "Collateral Injury by Total Occlusion Angioplasty: Biting the Hand that Feeds Us," *Catheterization and Cardiovascular Diagnosis* 34 (3): 65-66; Ha, J. W., Cho, S. Y., Chung, N., Choi, D. H., Choi, B. J., Jang, Y., Shim, W. H., and Kim, S. S. 2002. "Fate of Collateral Circulation After Successful Coronary Angioplasty of Total Occlusion Assessed by Coronary Angiography and Myocardial Contrast Echocardiography," *Journal of the American Society of Echocardiography* 15(5):389-395; Waser, M., Kaufmann, U., and Meier, B. 1999. "Mechanism of Myocardial Infarction in a Case with Acute Reocclusion of a Recanalized Chronic Total Occlusion: A Case Report," *Journal of Interventional Cardiology* 12 (2), 137-140. Stone, G. W., Kandzari, D. E., Mehran, R., Colombo, A., and 23 Other Authors 2005. "Percutaneous Recanalization of Chronically Occluded Coronary Arteries: A Consensus Document, Part I," *Circulation* 112(15):2364-2372).

Thus, the need for stenting is often the direct result of and used to cover over inadequacies of balloon angioplasty, which rather than to remove, only crushes plaque and can subject the lumen wall to stretching injury and dissections that can resit in an abrupt closure (see, for example, cases 3-5 in Farb, A., Lindsay, J. Jr., and Virmani, R. 1999. "Pathology of Bailout Coronary Stenting in Human Beings," *American Heart Journal* 137(4 Part 1):621-631 and 579-581; Marti, V., Montiel, J., Aymat, R. M., García, J., Guiteras, P., Kozak, F., and Augé, J. M. 1999. "Expanding Subintimal Coronary Dissection Under a Stent-covered Arterial Segment: Serial Intraductal Ultrasound Observations," *Catheterization and Cardiovascular Interventions* 48(3):308-311 Alfonso, F., Hernandez, R., Goicolea, J., Segovia, J., Perez-Vizcayno, M. J., Bañuelos, C., Silva, J. C., Zarco, P., and Macaya, C. 1994. "Coronary Stenting for Acute Coronary Dissection after Coronary Angioplasty: Implications of Residual Dissection," *Journal of the American College of Cardiology* 24(4):989-995) that stimulate constrictive remodeling, or arterial shrinkage as " . . . the predominant factor responsible for luminal narrowing after balloon angioplasty" and the stimulant for intimal hyperplasia (Pasterkamp, G., Mali, W. P., and Borst, C. 1998. "Application of Intraductal Ultrasound in Remodelling Studies," *Seminars in Interventional Cardiology* 2(1):11-18); see also Smits, P. C., Bos, L. Quarles van Ufford, M. A., Eefting, F. D., Pasterkamp, G., and Borsta, C. 1998. "Shrinkage of Human Coronary Arteries is an Important Determinant of de Novo Atherosclerotic Luminal Stenosis: An in Vivo Intraductal Ultrasound Study," *Heart* 79(2):143-147; Narins, C. R., Holmes, D. R. Jr., and Topol, E. J. 1998. "A Call for Provisional Stenting: The Balloon is Back!," *Circulation* 97(13):1298-1305; Teo, K. K. 1998. "Clinical Review: Recent Advances, Cardiology," *British Medical Journal* 316(7135):911-915).

Unlike balloon angioplasty, which crushes vulnerable or unstable plaque, allowing it to release embolizing debris, ablation, such as through thermoablation, destroys the debris, reducing the risk of inducing an ischemic event. Occlusive events range from the stunned myocardium (postischemic contractile dysfunction, or if stunned repeatedly, prolonged postischemic ventricular dysfunction of viable myocardium) (see, for example, Braunwald, E. and Kloner, R. A. 1982. "The Stunned Myocardium: Prolonged, Postischemic Ventricular Dysfunction," *Circulation* 66(6): 1146-1149; Bolli, R. 1992. "Myocardial 'Stunning' in Man," *Circulation* 86(6):1671-1691) to a cardiac arrest or a myocardial infarction; from a temporary ischemic attack to a cerebral infarction (stroke); or to an infarction elsewhere in the body.

Some endorse 'therapeutic dissections' whereby " . . . substantial dissections following PTCA [percutaneous transluminal coronary angioplasty using 'vessel size-adapted PTCA;' that is, dilation using a large balloon based upon measurements gained by intraductal ultrasound], which do not diminish antegrade blood flow, do not lead to an increase in acute or long-term events," (Schroeder, S., Baumbach, A., Mahrholdt, H., Haase, K. K., Oberhoff, M., Herdeg, C., Athanasiadis, A., and Karsch, K. R. 2000. "The Impact of Untreated Coronary Dissections on Acute and Long-term Outcome after Intraductal Ultrasound guided PTCA," *European Heart Journal* 21(2):137-145 and 21(2):92-94; Schroeder, S., Baumbach, A., Haase, K. K., Oberhoff, M., Marholdt, H., Herdeg, C., Athanasiadis, A., and Karsch, K. R. 1999. "Reduction of Restenosis by Vessel Size Adapted Percutaneous Transluminal Coronary Angioplasty Using Intraductal Ultrasound," *American Journal of Cardiology* 83(6):875-879). However, dissection resulting in abrupt closure can occur even with a smaller balloon (references above in the section entitled Risk of Abrupt Closure), as can a ductus-intramural or intraparietal hematoma (see Werner, G. S., Figulla, H. R., Grosse, W., and Kreuzer, H. 1995. "Extensive Intramural Hematoma as the Cause of Failed Coronary Angioplasty: Diagnosis by Intraductal Ultrasound and Treatment by Stent Implantation," *Catheterization and Cardiovascular Diagnosis* 36(2): 173-178).

More aggressive angioplasty can also produce a pseudoaneurysm (see, for example, Lell, E., Wehr, G., and Sechtem, U. 1999. "Delayed Development of a Coronary Artery Pseudoaneurysm after Angioplasty," *Catheterization and Cardiovascular Interventions* 47(2):186-190), followup stenting notwithstanding (see, for example, Cafri, C., Gilutz, H., Kobal, S., Esanu, G., Weinstein, J. M., Abu-Ful, A., and Ilia, R. 2002. "Rapid Evolution from Coronary Dissection to Pseudoaneurysm after Stent Implantation: A Glimpse at the Pathogenesis Using Intraductal Ultrasound," *Journal of Invasive Cardiology* 14(5):286-289; Kitzis, I., Kornowski, R., and Miller, H. I. 1997. "Delayed Development of a Pseudoaneurysm in the Left Circumflex Artery Following Angioplasty and Stent Placement, Treated with Intraductal Ultrasound-guided Stenting," *Catheterization and Cardiovascular Diagnosis* 42(1):51-53), aneurysm (see, for example, Berkalp, B., Kervancioglu, C., and Oral, D. 1999. "Coronary Artery Aneurysm Formation after Balloon Angioplasty and Stent Implantation," *International Journal of Cardiology* 69(1):65-70), and an aneurysm that ruptured (see, for example, Chou, T. M., Amidon, T. M., and Ports, T. A. 1993. "Contained Rupture Following Percutaneous Transluminal Coronary Angioplasty: Long-term Outcome," *Catheterization and Cardiovascular Diagnosis* 28(2):152-154). An intrinsic defect of some balloons remains focal expansion, or disproportionate expansion over the surface of the balloon so that different areas of the vessel wall are subjected to greater outward radial force (see, for example, Kokish, A. 2002. "Balloon with the Variable Radial Force Distribution," U.S. Pat. No. 6,391,002).

The outer shell of the muzzle-head is made of or coated with a low friction fluoropolymer and has a bullet or torpedo-configured nose to move through the lumen without catching (seizing, clinging) or pulling. If necessary, the muzzle-head is wetted with a lubricant during use with an interventional lubricant by means within it, such as those specified in the section below entitled Sectional, or Chain-stents, Segmented and Articulated, for example. Furthermore, the vibratory or oscillatory mode discussed under the sections below entitled Turret-motor Operational Modes among others is also available to assist in negotiating tight curves otherwise difficult to traverse. Thus, in contrast to the expansion of a balloon to apply outward force against the lumen wall, the highly lubricious (slippery, slick) and non-expanding muzzle-head does not cause stretching injury, even when negotiating sharp curves and tortuous stretches.

While the superiority of atherectomy over balloon angioplasty has been argued against (see, for example, Douglas, J. S. Jr. and King, S. B. III 2008. "Percutaneous Coronary Intervention," in Fuster, V., O'Rourke, R. A., Walsh, R., Poole-Wilson, P., (eds.), *Hurst's The Heart*, New York, N.Y.: McGraw-Hill; Bittl, J. A., Chew, D. P., Topol, E. J., Kong, D. F., and Califf, R. M. 2004. "Meta-analysis of Randomized Trials of Percutaneous Transluminal Coronary Angioplasty versus Atherectomy, Cutting Balloon Atherotomy, or Laser Angioplasty," *Journal of the American College of Cardiology* 43(6):936-942; Mauri, L., Reisman, M., Buchbinder, M., Popma, J. J., Sharma, S. K., Cutlip, D. E., Ho, K. K., Prpic, R., Zimetbaum, P. J., and Kuntz, R. E. 2003. "Comparison of Rotational Atherectomy with Conventional Balloon Angioplasty in the Prevention of Restenosis of Small Coronary Arteries: Results of the Dilatation vs Ablation Revascularization Trial Targeting Restenosis (DART)," *American Heart Journal* 145(5):847-854), this may have been due to inadequacy in the volume of tissue removed (Haager, P. K., Schiele, F., Buettner, H. J., Garcia, E., and ten other authors 2003. "Insufficient Tissue Ablation by Rotational Atherectomy Leads to Worse Long-term Results in Comparison with Balloon Angioplasty Alone for the Treatment of Diffuse In-stent Restenosis: Insights from the Intraductal Ultrasound Substudy of the ARTIST Randomized Multicenter Trial," *Catheterization and Cardiovascular Interventions* 60(1):25-31; Safian, R. D., Freed, M., Lichtenberg, A., May, M. A., Juran, N., Grines, C. L., and O'Neill, W. W. 1993. "Are Residual Stenoses after Excimer Laser Angioplasty and Coronary Atherectomy Due to Inefficient or Small Devices? Comparison with Balloon Angioplasty," *Journal of the American College of Cardiology* 22(6): 1628-1634).

However, if trauma is the cause of restenosis (see, for example, Ahn, S. S. and Ro, K. M. 2004. "Peripheral Atherectomy," in Hobson, R. W. II, Wilson, S. E. and Veith, F. J., *Vascular Surgery Principles and Practice*, New York, N.Y.: Marcel Dekker Division, Taylor and Francis, pages 359-360), then the medication and/or radiation used to suppress restenosis warrant further study. While at least for use in the carotid arteries reservations appear in the literature (see, for example, Vijayvergiya, R., Otaal, P. S., Bagga, S., and Modi, M. 2010. "Symptomatic Carotid Vasospasm Caused by a Distal-Protection Device during Stent Angioplasty of the Right Internal Carotid Artery," *Texas Heart Institute Journal* 37(2):226-229; Schirmer, C. M., Hoit, D. A., and Malek, A. M. 2008. "Iatrogenic Vasospasm in Carotid Artery Stent Angioplasty with Distal Protection Devices," *Neurosurgical Focus* 24(2):E12; Iyer, V., de Donato, G., Deloose, K., Peeters, P., Castriota, F., Cremonesi, A., Setacci, C., and Bosiers, M. 2007. "The Type of Embolic Protection Does Not Influence the Outcome in Carotid Artery Stenting.," *Journal of Vascular Surgery* 46(2):251-256), another problem with directional atherectomy, embolization by debris, can be ameliorated through the use of a distal embolic protective filter (see, for example, section 4d(2) entitled Ductus Wall Tumefacients and Shammas, N. W., Deppel, E. J., Coiner, D., Shammas, G. A., Jerin, M., and Kumar, A. 2008. "Preventing Lower Extremity Distal Embolization Using Embolic Filter Protection: Results of the PROTECT Registry," *Journal of Endovascular Therapy* 15(3):270-282).

Combination-form barrel-assemblies and radial projection catheters, addressed below in sections of like respective title, can accommodate a rotational atherectomy cutting head. The problem is less pronounced, but a filter would likely prove of benefit with a rotatory burr as well (see, for example, Friedman, H. Z., Elliott, M. A., Gottlieb, G. J., and O'neill, W. W. 1989. "Mechanical Rotary Atherectomy: The Effects of Microparticle Embolization on Myocardial Blood Flow and Function," *Journal of Interventional Cardiology* 2(2):77-83). At least immediately following the procedure, the actual excision of plaque by atherectomy results in a larger luminal cross-sectional area than does balloon angioplasty (Ikeno, F., Braden, G. A., Kaneda, H., Hongo, Y., Hinohara, T., Yeung, A. C., Simpson, J. B., and Kandzari, D. E. 2007. "Mechanism of Luminal Gain with Plaque Excision in Atherosclerotic Coronary and Peripheral Arteries: Assessment by Histology and Intraductal Ultrasound," *Journal of Interventional Cardiology* 20(2):107-113), and the gain appears to be attributable to the removal of plaque rather than its compression at the cost of luminal stretching (Marsico, F., Kubica, J., De Servi, S., Angoli, L., Bramucci, E., Costante, A. M., and Specchia, G. 1995. "Influence of Plaque Morphology on the Mechanism of Luminal Enlargement after Directional Coronary Atherectomy and Balloon Angioplasty," *British Heart Journal* 74(2): 134-139).

In concept, atherectomy should eventually prove inherently superior in terms of long-term results as well (see, for example, Garcia, L. A. and Lyden, S. P. 2009. "Atherectomy for Infrainguinal Peripheral Artery Disease," *Journal of Endovascular Therapy* 16(2 Supplement 2):II105-II115; Repetto, A., Ferlini, M., Ferrario, M., Angoli, L., and Bramucci, E. 2005. "Directional Coronary Atherectomy in 2005," *Italian Heart Journal* 6(6):494-497). Directional atherectomy is also able to deal with openings (ostia) and bifurcations that a balloon cannot articulate (Favero, L., Simpson, J. B., and Reimers, B. 2004. "Treatment of an Ostial and a Bifurcation Lesion with a New Directional Atherectomy Device," *Heart* 90(8):e46; Ho, G. H. and Moll, F. L. 1999. "Disobliteration Techniques," in White, R. A. and Fogarty, T. J. (eds.), *Peripheral Endovascular Interventions*, New York, N.Y.: Springer).

Almost always incorporated into the muzzle-head will also be two or more radial projection units containing side-looking (side-sweeping, stiff brush, or écouvillonage) type tool-inserts, as addressed below in the section entitled Radial Projection Units. Side-sweeping or brush type tool-inserts have variously configured tips on shafts of variable length similar to bristles or blades. Brush and swab (écouvillon) type tool-inserts are limited to the removal of material adherent to or beneath the intima softer than calcified plaque or oxalate salt, for example. Any kind of radial projection unit tool-insert can be deployed during manual or linear positioning stage mediated advancement or withdrawal of the barrel-assembly. An angioplasty-capable barrel-assembly, as addressed below in the section of like title, can incorporate a run-ahead protective embolic filter.

Then, to preclude downstream embolization by debris generated by the tool-inserts, the same switch used to deploy and retract the radial projection unit tool-inserts can be made to control a run-ahead embolic trap-filter that is stowed (stored) within a sheath or silo in the nose of the muzzle-head when not deployed. Addressed below in the section entitled Ablation or Ablation and Angioplasty-capable Barrel-assembly Onboard Control Panel, these switches are included in the barrel-assembly ablation or angioplasty control panel. Side-sweeping tool-inserts or side-sweepers, addressed below under the section entitled Radial Projection Unit Tool-inserts, can be configured as cytological sample collection brushes, for example. To avoid the need to withdraw the barrel-assembly in order to recover the tissue sample, the brushed surface is aspirated.

To do this, the closest barrel-tube or, when the sample would not be drawn out through the barrel-tube under a slight vacuum, then a barrel-tube insert lining, or service-catheter, is passed over the brushed surface to aspirate additional tissue for analysis. In order of increased control over the vacuum force used, this is done by bulb or syringe pipetting, a bulb expelled of air, or a suction (aspiration) pump. Aspiration is also possible through fluidically operated, or piped, radial projection units, as addressed in the section of like title. Depending primarily upon tissue hardness, the radial projection units positioned about the muzzle-head can be engaged with tool-inserts having bristle projections of different length and tip shape or razor edges, so that one type, for example, can be used to obtain a tissue sample for brush or slide cytology prior to resuming the procedure, as others are used to remove plaque.

Using fluidically operated tool-insert or barrel-tube aspiration, endoluminal lavage for washing and/or, diagnosis, or antisepsis can be performed midprocedurally without withdrawal before or after this action, as addressed below in the section entitled Service-catheters and Use of the Barrel-assembly as a Guide-catheter. When stenting is to follow angioplasty or atherectomy without withdrawal, a barrel-assembly is used; otherwise, a radial projection catheter can be used. A benefit in the use of an ablation or ablation and angioplasty-capable barrel-assembly, and a combination-form barrel-assembly in particular, is that it contains multiple tools for dealing with differently diseased tissues or plaque.

The operator can therefore proceed from one segment to the next with the means for dealing with differing plaque already available without the need for withdrawal and reentry. While a muzzle-head with radial projection unit brush and razor edge tool-inserts can accomplish the removal of soft plaque, the combination-form barrel-assemblies as described below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy, can accommodate a laser catheter, directional, or rotational atherectomy burr.

These allow the prominences when hardened, confluent, and protruding into the lumen to be removed, while radial projection unit tool-inserts of a bristle hardness or tip type selected for the specific plaque are used to reduce the plaque that tends to include discrete particulate calcifications beneath the lumen surface where it is more amenable to being swept and aspirated away. As most arteries are too narrow to use a combination form barrel-assembly that incorporates a laser; the use of a laser often necessitate an initial entry with a conventional (independent) laser prior to insertion of the barrel-assembly. Laser atherectomy is able to remove moderately calcified lesions by actually cavitating, disintegrating, and vaporizing the occlusive material.

Also in an artery too small to pass a combination-form barrel-assembly, when plaque is so calcified that a laser cannot remove it, the preceding use of a rotational burr is indicated. However, when a combination-form will pass, a laser can be withdrawn and replaced by a rotational burr without withdrawing the barrel-assembly. Calcification of plaque tending to increase adaxially, or the more toward the long axis of the lumen, when the degree of calcification does not disallow, a laser catheter incorporated into the barrel-assembly as described in the section below on combination-forms is used in a forward direction, or distad, without deployment of the side-brushes and trap-filter. When the direction is reversed to proximad, side-brushes, embolic filter, and optionally, the turret-motor or miniball recovery and extraction tractive electromagnets for thermal angioplasty, are actuated.

Otherwise unused barrel-tubes or fluidic tool-inserts can be used to aspirate. Accomplished thus, the forward pass addresses plaque more adaxial (central) in the lumen, while the return pass addresses that more abaxial (peripheral). When the plaque is stony, a rotational burr is used for the first or distad pass. Since the embolic filter cannot be deployed ahead of a laser, the concurrent use of side-brushes with the laser requires that the laser destroy any debris liberated by the side-brushes. Thus, normally whenever the laser and side-brushes are actuated together, the simultaneous deployment of the trap-filter with the side-brushes is electronically overriden. Otherwise, the trap-filter is separately actuable for deployment as desired.

Mineralization at the cap has been hypothesized by some to make plaque less and by other more vulnerable (see, for example, Li, Z. Y., Howarth, S., Tang, T., Graves, M., U-King-Im, J., and Gillard, J. H. 2007. "Does Calcium Deposition Play a Role in the Stability of Atheroma? Location May be the Key," *Cerebrovascular Disease* 24(5):452-459), and by others, less vulnerable (see, for example, Miralles, M., Merino, J., Busto, M., Perich, X., Barranco, C., and Vidal-Barraquer, F. 2006. "Quantification and Characterization of Carotid Calcium with Multi-detector CT-Angiography," *European Journal of Vascular and Endovascular Surgery* 32(5):561-567). Different imaging methods allow the distribution of calcium to be detected (see, for example, Moselewski, F., O'Donnell, C. J., Achenbach, S., Ferencik, M., Massaro, J., Nguyen, A., Cury, R. C., Abbara, S., Jang, I. K., Brady, T. J., and Hoffmann, U. 2005. "Calcium Concentration of Individual Coronary Calcified Plaques as Measured by Multidetector Row Computed Tomography," *Circulation* 111(24):3236-3241; Wexler, L., Brundage, B., Crouse, J., Detrano, R., Fuster, V., Maddahi, J., Rumberger, J., Stanford, W., White, R., and Taubert K. 1996. "Coronary Artery Calcification: Pathophysiology, Epidemiology, Imaging Methods, and Clinical Implications," *Circulation* 94(5): 1175-1192).

The apparatus suitable for use with plaque depends upon the degree and distribution of mineralization revealed by electron beam, helical (spiral) computed tomography, or optical coherence tomography (see, for example, Kubo, T., Imanishi, T., Takarada, S., Kuroi, A., and nine other authors 2007. "Assessment of Culprit Lesion Morphology in Acute Myocardial Infarction: Ability of Optical Coherence Tomography Compared with Intraductal Ultrasound and Coronary Angioscopy," *Journal of the American College of Cardiology* 50(10):933-939). A combination-form barrel-assembly, radial projection catheter, or either component in a duplex (composite, bipartite) barrel-assembly, as addressed below in the section entitled Distinction in Ablation or Ablation and Angioplasty-capable Barrel-assemblies as Unitary or Bipartite, can thus serve midprocedurally, in effect, as a kind of guide catheter for original equipment manufacturer cabled devices.

Depending upon the type ductus and barrel-assembly, these include a laser, rotational burr or cutting blade, suction hose, aspiration line, as a passageway through which a outlet hose connected to the muffler of a vortex tube can be passed to direct either chilled or heated air at the rear surface of the muzzle-head nose for performing a precautionary angioplasty, for example, or as a channel to allow blood to flow through and past. When unoccupied by a cabled device such as for atherectomy or thrombectomy, the bore through the combination-form barrel-assembly, or its central channel, can accommodate the silo for stowing an embolic trap-filter and its actuating direct current powered plunger (push-type, reciprocating armature or slug, punching, linear) solenoid, which is simpler and less expensive to produce than an off-center silo, as will be described in the section below entitled Embolic Trap Filter in Radial Discharge Muzzleheads for Use in the Vascular Tree.

Used manually apart from an airgun, a radial projection catheter or a barrel-assembly with radial projection unit tool-inserts such as side-sweepers with or without a trap-filter and a heatable turret-motor can serve as an independent apparatus for mechanical atherectomy and thermal angioplasty. The barrel-catheter of a duplex barrel-assembly allows size-matched, or complementary, projection catheters to be slid over the barrel-assembly as a sleeve that can be retracted to exchange the tool-inserts midprocedurally without the need to withdraw the barrel-assembly. The reverse arrangement, passing a barrel-assembly though the bore of a combination-form radial projection catheter, is possible but space demanding, awkward, and having limited application. Certain embodiments allow a carbon or nitrous oxide cartridge to be plugged into the proximal end-plate for cryoablation (cryocautery) or the chilling of tissue for metabolic stabilization (chemical retardation).

The incorporation of a laser catheter allows a barrel-assembly to remove plaque that is somewhat calcified and a rotational atherectomy burr plaque that is stony (hydroxyapatite). An angioplasty-capable barrel-assembly could be used to prepare the lumen for the introduction of a conventional or endoluminal stent. However, it is intended to prepare for an extraluminal stent, then to implant the intraductal component of that stent with single entry and withdrawal. Not expandable as is a balloon, for angioplasty, the body or shell of the muzzle-head is limited to lumina that match or slightly exceed it in diameter and are affected by soft atheromatous lesions. Although paths are provided for blood to pass the muzzle-head even when these diameters match, below a certain minimum diameter, obstruction to the flow of blood using a muzzle-head must prove unavoidable.

Even when flow-around is good, minimizing intracorporeal time should lead to better results, and several features have been incorporated to accomplish this. When the diameter of the muzzle-head is the same or slightly smaller than the diameter of the lumen, deploying the radial projection units around the muzzle-head allows an abrasive scrubbing or scraping (curettage, evidement) action of the surrounding lumen wall. Reciprocal movement of the barrel-assembly, radial projection catheter, or duplex barrel-assembly by hand or with the aid of a linear positioning stage then scrubs down the internal surface of the lumen in a manner analogous to that of a test-tube brush.

Depending upon the relative diameter of the apparatus and lumen, the material properties and adhesion of the lesion, and the tip type of the brush or side-sweeper type tool-inserts engaged in the radial projection units, addressed below in the section entitled Radial Projection Unit Tool-inserts, a side-sweeping type tool-insert, with or without the aid of an external electromagnet to urge it against a preferred arc of the surrounding lumen wall, can be used to obtain a powerful scrubbing or scraping action over the surrounding wall or an arc thereof. An extracorporeal electromagnet can aid in steering the muzzle-head or radial projection catheter, making it easier to pass curved segments.

As an adjunct to the capabilities for performing an angioplasty built into the barrel-assembly, an external magnet can be used with the turret-motor or rotation by hand to urge a certain arc of the muzzle-head against a certain arc of the lumen wall. The same does not apply to an independent radial projection catheter and is not used to ensleeve a barrel-catheter as the duplex counterpart thereto, which does not have a turret-motor. If the muzzle-head has clearance all around, this will consolidate and to the extent short of injury, increase the cross section for blood to pass. When applied to the proximate side, extension allows increasing the force applied to the working (cutting, shaving, abrading, or swabbing) face of the tool-insert on the opposite side, and when applied to retraction on the near side, reducing this force.

Extension of near side push-arm (blank) tool-inserts and those with brush-like tips too dense to perforate the lumen wall can be used to push the muzzle-head or projection catheter in the opposite direction and/or to allow blood to pass. When using an external magnet, the abruptness of magnetic attraction when the effective tractive force is reached risks stretching injury and dissection, recommending restriction of the field strength. The use of an external electromagnet is therefore limited to ductus or lengths thereof which have not become significantly weakened by disease or significantly larger in diameter than the muzzle-head or projection catheter. Excessive distance between the outside of the apparatus and the wall of the lumen can allow a buildup of momentum sufficient to deliver a blow to the lumen wall.

If desired, however, an external magnet allows urging the muzzle-head against the inside of the lumen wall with greater force. Depending upon the relative diameter of the lumen and the muzzle-head or projection catheter and the distance to which the radial projection unit or units can be extended on the near side, the application of mild pressure to the opposite lumen wall can be accomplished with less force than through the use of an external magnet. In contrast, however, the use of an external magnet to stop and extract a loose miniball is accomplished least traumatically the more suddenly the tissue is penetrated; slower extraction is liable to pull, stretch, or tear the adjacent tissue.

Accordingly, to extract a miniball, the field strength is set at the maximum, extraction entirely outside the body or to a safe location outside the ductus determined by the duration, rate, and number of pulsed magnet energizations. Whether the same or different magnets are used for such purposes, the controls should permit the kinds of adjustments indicated. Further to avoid dissections and tears, steering of the muzzle-head with the aid of an extracorporeal hand-held electromagnet or the probe of a large electromagnet is limited to plaque that does not present calcified prominences and does not pose excessive resistance to pass. Another limitation is that setting the field strength too high risks the extracting of miniballs already implanted on the opposite side.

The barrel-assembly incorporates several means for accomplishing angioplasty to ameliorate the limitations imposed by the restrictedness of the lumen diameter and the hardness of some lesions. The deployment of radial projection units along any arc of the barrel-assembly or radial projection catheter can also be used to nudge the muzzle-head in the opposite direction. When the radial projection units do not encircle the muzzle-head or are not situated along the radii desired, the turret-motor is used to rotate the muzzle-head before the tool-inserts are extended. This allows the working or blank face of the radial projection unit tool-insert on the opposite side to be applied with greater force against the lumen wall but must not be used for steering.

Radial projection tool-inserts are addressed below under the section of like title and include electrically and fluidically operated ejection types that can release a lubricant, liquid drugs, and/or other therapeutic substances against the lumen wall, as can unused barrel-tubes. Based upon a preliminary determination of the distribution and character, that is, the histology, pathology, and hardness of the plaque (usually by computed tomography), radial projection unit abrading or brush type tool-inserts having, for example, bristles of suitable stiffness and tip conformation are mounted in the radial projection unit wells (sockets, recesses) about the muzzle-head.

Then, using controls onboard the barrel-assembly or the radial projection catheter rather than an external electromagnet, the deployment of the radial projection unit or units to one side of the muzzle-head or catheter allows it to be nudged in the opposite direction. This allows applying the working or blank faces of the radial projection unit tool-inserts extended on that side to be applied with greater force against the lumen wall. Erosive or ablative action can also be intensified by using the turret-motor to quickly rotate the muzzle-head or oscillate it by means of vibratory motion that has been programmed or obtained through servo destabilization, as discussed below in the section entitled Turret-motor Operational Modes.

When different type tool-inserts, such as shavers (skivers) and brushes, are inserted into the radial projection unit lift-platforms about the muzzle-head, differential deployment followed by rotation using the turret-motor or by hand enables the bringing to bear of tool-inserts in any available combination or sequence to a given lesion. To avoid perforating the wall, this is generally limited to flat-faced (push-arm, blank) tool-inserts and those with aristae or bristles without sharp tips, and those too dense to puncture. With or without additional force, the side-sweeper type radial projection unit tool-inserts in an ablation and angioplasty-capable barrel-assembly or a radial projection catheter, whether brushes as such or cutting tools, can be used to perform an ablation or an angioplasty with the barrel-assembly or catheter moved transluminally by hand or with the aid of a linear positioning stage.

When the apparatus is a barrel-assembly, the tool-inserts can be rotated at any level manually or with the turret-motor, which primarily to support the use of injection syringe tool-inserts, also allows fine adjustment in rotational angle. With the barrel-assembly not removed from the airgun, which would free its proximal end and length adjacent thereto for manual use, the airgun linear positioning table (linear positioning stage) can be used to move the muzzle-head. The base upon which the linear positioning stage is mounted positions the airgun in the proximodistal direction. Thus, provided the barrel-assembly is not already fully intromittent (intracorporeal), an additional length of barrel-catheter needed to further advance transluminally is made available by shifting the airgun mounting closer to the patient with the positioning stage.

Angioplasty or any other treatment, such as injection or ablation, can therefore be resumed with the barrel-assembly left in the airgun, that is, without detaching the barrel-assembly after it has already been inserted into the airgun: Most ablation and angioplasty can be accomplished manually with the barrel-assembly separate from an airgun; adjustment in transluminal positioning requiring precision as to recommend mechanical positioning pertains primarily to discharge and further discharge in a uniform dense pattern. When the barrel-assembly is already fully intromittent up to the power and control housing and must be advanced further distally, the housing is shifted back, or slid proximally, along the barrel-catheter to provide an additional length of barrel-catheter to its fore for intromission.

The opposite situation of requiring continued withdrawal of the muzzle-head past the retractive range of the linear stage is handled the same way but in the opposite direction. The linear positioning stage used should have a sufficient range (throw, bed length) to move the barrel-assembly muzzle-head or the radial projection catheter across the entire treatment site. However, if the stage, which supports and is attached to the airgun, has already reached the distal limit of its range, resumption in the use of the linear stage requires shifting the base upon which the stage is mounted closer to the patient.

Whether to shift the stage base distally (forward) or backward (proximally), this action must be accomplished without disturbing or affecting the transluminal position of the muzzle-head. To do this, the otherwise stationary base or bed of the linear stage, which is slidably joined to the stage, must be repositioned in the distal direction (closer to the patient) without affecting the position of the airgun or the stage. The simplest way to accomplish this is by gently lifting the airgun with attached linear stage free of the cart surface manually, and then using the stage control to shift (translate) the base of the linear stage distally (closer to the patient) leaving the airgun unaffected in position.

That is, whereas with the linear stage in contact with the cart the base remains stationary and drives the stage with attached airgun, by lifting the base free of the cart, the airgun with attached linear stage remain stationary as the base moves forward. When the airgun with stage and mounting are set down, the stage will be positioned to allow a resumption in forward (distal) motion. To accomplish the same action without manual intervention, the linear stage must be provided with an additional joint or planar interface on its underside, that without affecting the position of the airgun, allows the separate linear translation of the base between the stage above and cart below. To do this, the base is attached down to a position controllable motorized carriage or creeper with a continuous loop or full track conveyor belt beneath that circulates between pulleys at either end.

Such a device, effectively an inverted linear stage which is not limited in range of linear motion, could replace the linear stage, but is less precise than a stage, not a standard component for motional control applications, and is not needed when the distance to be covered falls within the range of the stage, as is usual. The upper stage repositions the airgun to a point in its range that will allow continued travel in the direction required while the base mover simultaneously repositions the upper stage in the opposite direction. The result is that the upper stage is shifted as needed without movement of the airgun. To carry the stage and airgun, the motor used to drive the base must be as or slightly more powerful than that built into the stage. Both motors, usually stepper motors, are controlled by the same signal.

The base can now crawl or creep along the surface of the cart in synchrony with the corresponding (equal but opposite) repositioning of the stage, thus repositioning the stage to resume movement of the barrel-catheter past either the proximal or distal limit of its integral bed. The additional axis and control electronics therefor add complexity and expense viewed as nonessential. Ablation and ablation and angioplasty-capable barrel-assemblies include components, to include radial projection units, heatable turret-motors, and recovery (tractive) electromagnet windings, that can be used to perform an ablation, atherectomy, or angioplasty by hand with the barrel-assembly separate from the airgun. As opposed to its heating or thermal mode of operation, the turret-motor positioning and oscillatory functions are disabled during discharge.

Heating during discharge will, however, necessitate adjustment in the propulsive force of discharge, which to avert human error, is best incorporated into the control circuitry as automatic. While oscillatory movement can be programmed, the oscillatory capability of the turret-motor inheres in closed loop control by intentional overamplification and does not require additional parts or modifications. Driven as is a membrane peeler-cutter or microscissors for intraocular surgery, the viscous or dashpot damped trap-filter plunger (punching, push-type, reciprocating armature or slug) solenoid in the nose of the muzzle-head can be made to linearly reciprocate at a high frequency in the longitudinal axis. Such action can be used to add a reciprocating oscillatory component at the nose of the muzzle-head to that rotatory obtained through use of the turret-motor.

Alternative methods for inducing oscillation of the muzzle-head include movably mounting each recovery electromagnet so that the pull of each acts upon the other and sidewise upon the plunger solenoid as it reciprocates to vibrate the nose of the muzzle-head. Positional control of the turret-motor defines the limits of rotation that if exceeded would cause distortion of the barrel-tubes leading to constriction or jamming during discharge. Stops on the shell of the muzzle-head further protect against excessive rotation in the event of a malfunction. Control within the permissible rotational angle of the muzzle-head during an angioplasty, for example, allows eccentric lesions to be targeted for treatment with adjacent arcs affected less if at all.

With adequate contrast, the point of injection can be adequately limited, whereas less focused treatments, such as the application of heat or cold, will spread or spill over in proportion to the intensity thereof. Control over the turret-motor, thus the muzzle-head rotational angle, allows directing a heat-window or windows or a tool-insert or inserts to a certain arc. Programmed vibratory motion with the rate of reciprocation controlled or intentionally induced turret-motor control circuit servo-oscillation can be used to provide a scrubbing or swabbing action for use with deployed (extended, projected) abrading, cutting, or swabbing tool-inserts as appropriate.

The same action can be used to assist in passing a tortuous stretch of ductus with or without the release of a catheteric lubricant from ejection tool-inserts, through barrel-tubes, or if a combination-form barrel-assembly or radial projection catheter, the central bore or channel. Suitable lubricants are specified in the section below entitled Multiple Radial Discharge Barrel-assemblies with One- to Four- or More-way Radial Discharge Muzzle-heads. By comparison, a balloon used for arterial thermoplasty or cryoplasty is not compartmentalized to deal with eccentric lesions. By definition, an ablation or angioplasty-capable barrel-assembly must be self-contained for use independently of an airgun without regard to previous or subsequent use for ballistic implantation.

Such capability necessitates an onboard control panel and electrical power source. An onboard rechargeable lithium-ion polymer electrolyte (lithium polymer, Li-poly, LiPo) battery pack, preferably of the thin film kind for increased charge-discharge cycles, allows an ablation or ablation and angioplasty-capable barrel-assembly to be used independently of the airgun or other power supply and without a power cord. Angioplasty or ablation with the barrel-assembly is thus performed manually without restraint due to connection at the rear. When matched with a combination-form radial projection catheter to constitute a duplex or bipartite ablation or angioplasty-capable barrel-assembly, the control housings of the two components, each slidable along the length of its respective component, are placed in apposite or ganged relation.

In addition to these ablation and angioplasty-supporting operational modes of the turret-motor, both it and the tractive electromagnets within the barrel-assembly support discharge, recommending the incorporation of controls on a panel mounted to the outside of the airgun with an independent power source housed within. Whether duplicated on the airgun, mounted onboard the barrel-assembly, these controls allow directing the turret-motor to execute changes in rotational angle for aiming or targeting, and allow separate variability in the field strength of either tractive electromagnet within the barrel-assembly for recovery or extractive use. The barrel-assembly is used apart from the airgun for ablation or angioplasty and must be inserted into the airgun only to discharge miniballs, whether stenting or therapeutic.

The manual use of a separate combination-form radial projection catheter that is the complement to a duplex barrel-assembly which remains engaged in the airgun and is passed through the projection catheter so that the muzzle-head is brought to the position at which discharge is to be initiated as necessary is also possible. The proximal end of an ablation or angioplasty-capable barrel-assembly can be inserted into the interventional airgun for stenting at any time during as well as following a preparatory angioplasty performed manually with the same apparatus. If the angioplasty is performed using the positional control system, then the barrel-assembly will already have been engaged in the airgun.

While balloon angioplasty alone can return the lumen to substantial concentricity, the sites of harder lesions experience greater radial force, sometimes resulting in dissections leading to increased arterial shrinkage, or constrictive remodelling, and intimal hyperplasia. A preliminary reduction of prominences by means of cutter balloon or rotational, directional, ultrasonic, or laser-catheter atherectomy reduces the risk of this eventuality, and this has encouraged the development of catheter-based devices that cut and then reduce rather than merely smash plaque whether a stent is then used, which can serve to hold the resultant debris in place. Especially when equipped with radial projection units or as combination-forms that incorporate a laser or cutting tool, ablation or ablation and angioplasty-capable barrel-assemblies can be used to perform an ablation or an angioplasty or atherectomy independently of an airgun.

Using either an edge- or center-discharge muzzle-head, these differ from the use of balloons in ways that as an alternative technology and methodology, offer advantages as compared to the use of balloons. Not inflated and not over-inflatable, provided it is properly sized, the muzzle-head is less prone to cause dissections and does not require to be withdrawn through the introducer sheath for reentry to introduce a stent. Instead, stenting is initiated without a second radial inflation against the lumen wall in order to expand an endoluminal stent with sufficient force to prevent migration; to initiate stenting, the free end of the barrel-assembly is plugged into the airgun. By the same token, the muzzle-head is not deflatable, which capability of a balloon reduces the risk of tears and ischemia.

Commercial cabled devices incorporated into a barrel-assembly, radial projection catheter, or a combination-form thereof with a central bore, such as a laser or rotational atherectomizer requiring connection to an original manufacturer equipment control console will continue to necessitate cabling. Tethering by means of a loose cable connected to the rear (proximal end) of the barrel-assembly is less restraining than is immobilization of the proximal end by virtue of insertion into the airgun barrel. When the barrel-assembly incorporates a laser or atherectomy device, the cable for these is used as well. Directly connecting the components in the barrel-assembly to the airgun power supply by means of a cable without the need to insert the barrel-assembly into the airgun barrel allows the barrel-assembly to be made at lower cost.

However, this difference is generally not considered sufficient to offset the loss in the barrel-assembly as a stand-alone or independent device. Otherwise, cabled devices can almost always be adapted to incorporate the control electronics and power source within the onboard control housing. Accordingly, in an ablation or ablation and angioplasty-capable barrel-assembly which can be used separately from the airgun, the controls for use of the components included are located on a control panel mounted to the side of the onboard power and control housing. These controls allow heating the turret-motor stator, deploying radial projection unit tool-inserts, and the use of any other components. Control panels are addressed below in the section entitled Ablation and Ablation and Angioplasty-capable Barrel-assembly Onboard Control Panel and the housing below in the section entitled Barrel-assembly Power and Control Housing.

Radial projection catheters have a similar housing and control panel, which is adjacent to that of the barrel-assembly when these are mated in a duplex type barrel-assembly. For heating the turret-motor, the motor drive electronics that ordinarily convert the applied dc into 3 phase current is bypassed. A radial projection catheter is capable of performing any endoluminal procedure, and an ablation or angioplasty-capable barrel-assembly can also place (implant) the intravascular component of any number of extraluminal stents. Neither uses a guide wire. The deflatability of a balloon minimizes the risk of occlusive hypoxia and enhances movement past stenotic and tortuous stretches, but is associated with the need for a guide wire and the risks a guide wire carries.

Neither does a balloon make possible the integration of additional function beyond thermoplasty by running a heated liquid or cryoplasty by running a chilled liquid through it. A cutting balloon can also atherectomize, but no balloon can perform an angioplasty or an atherectomy and then stent without the need to withdraw and reenter, thus reducing the risk of entry wound complications. A balloon can stent without an angioplasty, but, the endoluminal stent it places will often create problems later than an extraluminal stent will not. By the same token, the endoluminal stent does not require extraluminal as well as endoluminal access. Catheter-based devices currently in use do not lend themselves to such a combination of functions or to the ability to place multiple stents. Apart from difficulties in integrating the devices mechanically, some are not reusable.

A distinguishing attribute of the apparatus to be described is the possibility of integrating numerous therapeutic functions. While relaxed or having had the normal angiotensive or contractive force exerted by the smooth muscle in the wall of the vessel reduced by administering medication, the lumen wall allows transluminal access to narrower portions of the vascular tree with a barrel-assembly of given diameter. Once placed, however, an extraluminal stent should require relatively little medication. A barrel-assembly that is wider in diameter can incorporate more features and deliver more miniballs per discharge, reducing procedural time. The narrowness of the lumina in the vascular tree makes a safe means of dilatation advantageous.

The blunt and slippery nose of the muzzle-head poses little risk of perforations, and made of tough, flexible, and strongly bonded polymer tubing, the entire apparatus less still of fractures. The barrel-assembly is thus capable of traversing tortuous stretches of vessels that a guide wire could perforate. Without a guidewire, the application of an off-the-shelf magnetic navigation system such as provided by Stereotaxis, Inc., St. Louis, Mo. and IntraLuminal Therapeutics Division, Kensey Nash, Inc., Carlsbad, Calif., now Spectranetics, Inc., Colorado Springs, Colo., is to the muzzle-head itself, which can be coordinated with the positional control system.

Except in certain combination-form barrel-assemblies, the elimination of a guidewire offers the benefit of eliminating various complications, which infrequent, can prove catastrophic when these occur, to include:

a. Perforations (see, for example, Störger, H. and Ruef, J. 2007. "Closure of Guide Wire-induced Coronary Artery Perforation with a Two-component Fibrin Glue," *Catheterization and Cardiovascular Interventions* 70(2):237-240; Shirakabe, A., Takano, H., Nakamura, S., and thirteen other authors 2007. "Coronary Perforation During Percutaneous Coronary Intervention," *International Heart Journal* 48(1): 1-9; Axelrod, D. J., Freeman, H., Pukin, L., Guller J., and Mitty, H. A. 2004. "Guide Wire Perforation Leading to Fatal Perirenal Hemorrhage from Transcortical Collaterals after Renal Artery Stent Placement," *Journal of Vascular and Interventional Radiology* 15(9):985-987; Naik, M., Lau, K.-W., and Chua Y.-L. 2001. "Guidewire Perforation during PTCA with Subsequent Off-Pump Bypass Surgery," Texas Heart Institute Journal 2001 28(1):70-71; Witzke, C. F., Martin-Herrero, F., Clarke, S. C., Pomerantzev, E., and Palacios, I. F. 2007. "The Changing Pattern of Coronary Perforation During Percutaneous Coronary Intervention in the New Device Era," *Journal of Invasive Cardiology* 16(6): 257-301; Kent, J. and Nedumpara, T. 2007. "Perforation of the Gall Bladder by a Peripherally Inserted Central Catheter Guidewire: 'If it Can Happen it Will,'" *Australia-New Zealand Journal of Surgery* 77(3):190-191; Ogino, H., Miki, S., Ueda, Y., Tahata, T., Morioka, K., and Sakai, T. 1995. "A Rare Case of Coronary Artery Perforation by a PTCA Guide Wire Complicated by Postinfarction Cardiac Rupture after Thrombolytic Therapy," (in Japanese) *Nippon Kyobu Geka Gakkai Zasshi* 43(8):1151-1154).

b. Fractures (see, for example, Kilic, H., Akdemir, R., and Bicer, A. 2008. "Rupture of Guide Wire During Percutaneous Transluminal Coronary Angioplasty, a Case Report," *International Journal of Cardiology* 128(3):e113-e114; Collins, N., Horlick, E., and Dzavik, V. 2007. "Triple Wire Technique for Removal of Fractured Angioplasty Guidewire," *Journal of Invasive Cardiology* 19(8):E230-234; Vrolix, M., Vanhaecke, J., Piessens, J., and De Geest, H. 2005. "An Unusual Case of Guide Wire Fracture during Percutaneous Transluminal Coronary Angioplasty," *Catheterization and Cardiovascular Diagnosis* 15(2):99-102; Gavlick, K. and Blankenship, J. C. 2005. "Snare Retrieval of the Distal Tip of a Fractured Rotational Atherectomy Guidewire: Roping the Steer by its Horns," *Journal of*

*Invasive Cardiology* 17(12):E55-E58; Kim, J. Y., Yoon, J., Jung, H. S., Kim, W. J., Yoo, B. S., Lee, S. H., and Choi, K. H. 2005. "Broken Guidewire Fragment in the Radio-brachial Artery During Transradial Sheath Placement: Percutaneous Retrieval via Femoral Approach," *Yonsei Medical Journal* 28; 46(1):166-168).

c. Fractures necessitating emergency surgical retrieval (see, for example, Modi, A., Zorinas, A., Vohra, H. A., and Kaarne, M. 2011. "Delayed Surgical Retrieval of Retained Guidewire Following Percutaneous Coronary Intervention," *Journal of Cardiac Surgery* 26(1):46-48; Demirsoy, E., Bodur, H. A., Arbatli, H., Yağan, N., Yilmaz, O., Tükenmez, F., Oztürk, S., and Sönmez, B. 2005. "Surgical Removal of Fractured Guidewire with Ministernotomy," (in English) *Anadolu Kardiyoloji Dergisi* (*Anatolian Journal of Cardiology*) 5(2): 145-477 (available at http://www.anakarder.com/sayilar/21/2005-145-147.pdf).

d. Entrapment with or without fracture necessitating emergency surgical extraction and a coronary artery bypass graft (Capuano, F., Simon, C., Roscitano, A., and Sinatra, R. 2008. "Percutaneous Transluminal Coronary Angioplasty Hardware Entrapment: Guidewire Entrapment," *Journal of Cardiovascular Medicine* (Hagerstown) 9(11):1140-1141; Darwazah, A. K., Abu Sham'a, R. A., Yassin, I. H., and Islim, I. 2007. "Surgical Intervention to Remove an Entrapped Fractured Guidewire during Angioplasty," *Journal of Cardiac Surgery* 22(6):526-528; Kim, C. K., Beom Park, C., Jin, U., and Ju Cho, E. 2006. "Entrapment of Guidewire in the Coronary Stent During Percutaneous Coronary Intervention," *Thoracic and Cardiovascular Surgeon* 54(6):425-426).

e. Fractures with entrapment (see, for example Marti, V. and Markarian, L. 2007. "Atrapamiento de la guia de angioplastia después de la implantación de un stent: Descripción de dos casos y revisión de la literatura," ("Angioplasty Guidewire Entrapment Following Implantation of a Stent: Description of Two Cases and a Review of the Literature") *Archivos de cardiología de México* 77(1):54-57; Kim, C. K., Beom Park, C., Jin, U., and Ju Cho, E. 2006. "Entrapment of Guidewire in the Coronary Stent During Percutaneous Coronary Intervention," *Thoracic and Cardiovascular Surgeon* 54(6):425-426; Ozkan, M., Yokusoglu, M., and Uzun, M. 2005. "Retained Percutaneous Transluminal Coronary Angioplasty Guidewire in Coronary Circulation," *Acta Cardiologica* 60(6):653-654; Khambekar, S., Hudson, I., and Kovac, J. 2005. "Percutaneous Coronary Intervention to Anomalous Right Coronary Artery and Retained Piece of Guidewire in the Coronary Vasculature," *Journal of Interventional Cardiology* 18(3):201-204;

f. Fractures with entrapment necessitating emergency percutaneous retrieval (see, for example Khong, P. L. and John, P. R. 1997. "Percutaneous Retrieval of a Fractured Biliary Guidewire from a Reduced Liver Graft," *Pediatric Radiology* 27(3):253-254; Pande, A. K. and Doucet, S. 1998. "Percutaneous Retrieval of Transsected Rotablator Coronary Guidewire Using Amplatz "Goose-Neck Snare"," *Indian Heart Journal* 50(4):439-442; Savas, V., Schreiber, T., and O'Neill, W. 1991. "Percutaneous Extraction of Fractured Guidewire from Distal Right Coronary Artery," *Catheterization and Cardiovascular Diagnosis* 22(2): 124-126).

g. Fractures with entrapment necessitating emergency surgical intervention (see, for example, Darwazah, A. K., Abu Sham'a, R. A., Yassin, I. H., and Islim, I. 2007. "Surgical Intervention to Remove an Entrapped Fractured Guidewire During Angioplasty," *Journal of Cardiac Surgery* 22(6):526-528; Goksin, I., Baltalarli, A., Semiz, E., Gurses, E., Sacar, M., Ozcan, V., and Sungurtekin, H. "Catheter Entrapment During Balloon Angioplasty in Patient with In-stent Restenosis: An Unusual Complication and Its Surgical Management," *Journal of Cardiac Surgery* 2007 22(2): 160-162).

A similar set of risks pertains to balloon catheters (see, for example, Hung, C. L., Tsai, C. T., and Hou, C. J. 2004. "Percutaneous Transcatheter Retrieval of Retained Balloon Catheter in Distal Tortuous Coronary Artery: A Modified Double-helix Approach," *Catheterization and Cardiovascular Interventions* 62(4):471-475; Hwang, M. H., Hsieh, A. A., Silverman, P., and Loeb, H. S. 1994. "The Fracture, Dislodgement and Retrieval of a Probe III Balloon-on-a-Wire Catheter," *Journal of Invasive Cardiology* 6(5):154-156). Thus, whenever a combination-form barrel-assembly can be made to duplicate the function of a normally independent guidewire-directed device, it is preferred to incorporate the function into the barrel-assembly without the guidewire. Numerous such devices, to include radio frequency ablative guidewires and excimer lasers can be readily incorporated without a guidewire.

A combination-form barrel-assembly with side-socket can nevertheless be used with proprietary devices such as the optical coherence reflectometry-guided Safe-Cross® Radiofrequency Total Occlusion Crossing System from Spectranetics, Incorporated. Except through tortuous stretches, such function would more often be obtained through use of a laser that has been built into an ablation and angioplasty-capable or inserted into a combination-form barrel-assembly or radial projection catheter. The use of an extracorporeal electromagnet, hand-held or mounted, is described below in the section entitled Steering and Emergency Recovery of Implants with the Aid of an External (Extracorporeal) Electromagnet. The magnet is adjusted to the minimal field strength sufficient to act as an aid to steering. Such use is addressed above in the section entitled Administration of Target and Target-adjacent Implantation Preparatory Substances.

In addition to the use of an external electromagnet, the muzzle-head, while greater in mass as to necessitate a stronger magnetic field, is compatible with recent advancements in magnetic navigation (see, for example, Rivero-Ayerza, M., Jessurun, E., Ramcharitar, S., van Belle, Y., Serruys, P. W., and Jordaens, L. 2008. "Magnetically Guided Left Ventricular Lead Implantation Based on a Virtual Three-dimensional Reconstructed Image of the Coronary Sinus," *Europace* 10(9):1042-1047; Kiemeneij, F., Patterson, M. S., Amoroso, G., Laarman, G., and Slagboom, T. 2008. "Use of the Stereotaxis Niobe Magnetic Navigation System for Percutaneous Coronary Intervention: Results from 350 Consecutive Patients," *Catheterization and Cardiovascular Interventions* 71(4):510-517; Schneider, M. A., Hoch, F. V., Neuser, H., Brunn, J., and 5 others, 2008. "Magnetic-guided Percutaneous Coronary Intervention Enabled by Two-dimensional Guidewire Steering and Three-dimensional Virtual Angioscopy: Initial Experiences in Daily Clinical Practice," *Journal of Interventional Cardiology* 21(2):158-166).

A magnetic navigation system can also be coordinated with the use of the positional control system. The latter does not steer but rather transluminally moves the muzzle-head while controlling its angular orientation. Such use is appropriate when the muzzle-head is narrower than the lumen and drawing the exit port flush against the lumen wall does not irremediably compress the lumen wall so that it is too narrow to implant, as will be addressed. The relative merits of femoral and radial access have been widely studied (see, for example, Archbold, R. A., Robinson, N. M., Schilling, R.

J. 2004. "Radial Artery Access for Coronary Angiography and Percutaneous Coronary Intervention," *British Medical Journal* 329(7463):443-446; Louvard, Y., Lefèvre, T., Allain, A., and Morice, M. 2001. "Coronary Angiography through the Radial or the Femoral Approach: The CARAFE Study," *Catheterization and Cardiovascular Interventions* 52(2):181-187; Kiemeneij, F., Laarman, G. J., Odekerken, D., Slagboom, T., van der Wieken, R. 1997. "A Randomized Comparison of Percutaneous Transluminal Coronary Angioplasty by the Radial, Brachial and Femoral Approaches: The Access Study," *Journal of the American College of Cardiology* 29(6):1269-1275. Angioplasty preceding stenting is preferably accomplished with an angioplasty-capable barrel-assembly, which can proceed from or switch between the one process and other without the need to withdraw and reenter.

Whenever preceded by a conventional (balloon) angioplasty, access, whether percutaneous or open, is preferably at the same groin (inguinal, femoral) entry wound as was used for the angioplasty, with the administration of heparin having been stopped. This is because 1. Proximal, meaning brachial or 'axillary' (high brachial), much less radial access poses a greater risk of complications, 2. Groin (femoral artery or vein) compression closure aids such as the FemoStop®Plus,Angio-Seal®STS Plus and Millenium platforms, and Perclose®A-T have become available to deal with oozing or hematoma, 3. Stenting almost always follows balloon angioplasty or rotational (rotablation), directional, or transluminal extraction coronary atherectomy, and requiring withdrawal and reentry takes more time and can aggravate the entry wound, 4. The muzzle-head at the end of the barrel-assembly is generally 8-10 French, recommending an entry wound of larger size, 5. A point of entry other than inguinal increases the possibilities for puncture site complications and postoperative morbidity. When the angioplasty is accomplished using an angioplasty-capable barrel-assembly, removal of one catheter and insertion of another is unnecessary.

8. Concept of the Extraluminal Stent

Three basic types of extravascular (circumvascular, circumductal, periductal, perivascular) stent component are addressed. These include ordinary stent-jackets, which are based upon a length of elastic tubing that if not intrinsically magnetized, laminated, or encased within a coating that incorporates a magnetized lanthanoid, for example, are provided with small permanent magnets mounted about the outer surface. Intrinsically and quasi-intrinsically magnetized components offering no visible indication of magnetization, for clarity, extrinsic magnets are shown in the drawing figures; however, for compactness and to avoid encroaching upon neighboring tissue, most practical components are intrinsically or quasi-intrinsically magnetized.

A second type is the longitudinally segmented, or spine and ribs-configured stent-jacket for use along peristaltic ductus, where a stent-jacket that is able to comply only circumferentially would lack the flexibility needed to comply with longitudinally consecutive extremes in radial excursion. Impasse-jackets are primarily devised for use other than to keep a lumen patent, but when necessary or beneficial, can also be used to stent. A fourth type, the magnet-jacket, is devised to be placed about a substrate ductus for directing magnetic force radially outward; if used for its inward force, it is a stent-jacket. In many locations, a nonabsorbable endoluminal stent that will be needed over a longer period than an absorbable stent would last is practically irretrievable.

This is due more to the trauma that recovery would produce than it is to a desire to avoid subjecting the patient to a second invasive procedure, despite the potential harm that leaving the stent in might cause and the benefit that removing it would provide. The chronic irritation and physiological disruption caused by an endoluminal stent stimulates the ductus to adapt; however, adaptation equates to suboptimal function, can itself cause complications, may be inadequate, or prove adequate for only a limited time. The advent of absorbable endoluminal stents will eliminate some problems encountered with nonabsorbable endoluminal stents, but introduce others. Once absorbed, the patient is left entirely and interminably dependent upon a statin, and for about a year following, a platelet blocker.

A chronic condition such as vasospasm refractory to drugs or a condition that for pathophysiological or genetic reasons is predicted but not as to time, cannot be preempted at potential points of critical blockage by prepositioning an absorbable stent. As a mechanical means for maintaining patency without interfering with intrinsic motility, an extraluminal stent affords a measure of protection against restenosis that should allow reducing the frequency of drug use. This is especially true when the intravascular component consists of stays, which are introduced from outside the artery so that the lumen is entered only when a preparatory angioplasty is performed. Stays may allow the use of a platelet blocker to be avoided.

The use of impasse-jackets as delineated below in the sections entitled Concept of the Impasse-jacket and Cooperative Use of Impasse-jackets in Pairs and Gradient Arrays, among others, presents means that allow the highly localized administration of a statin in higher concentration than could be introduced into the systemic circulation without risking liver and muscle complications. Platelet blockers such as clopidogrel, aspirin, and others indicated above in the section entitled Prevention of Abrupt Closure with Thrombus and Vasospasm should be avoided with a patient prone to peptic ulcer disease and/or hypersensitivity to these. Clopidogrel and similar drugs pose a risk of intracranial hemorrhage, can create a bleeding problem for emergency surgery, and can cause hypertension, hypercholesterolemia, upper respiratory or urinary tract infection, bronchitis, chest and/or musculoskeletal pain, headache, dizziness, diarrhea, epistaxis, purpura, pruritis, rash, edema, nausea, and emesis.

Vorapaxar (Merck Sharp Dohme/Schering-Plough), a thrombin receptor antagonist, can cause bleeding as may disallow use in patients with a history of stroke. Unlike an implantable cardioverter-defibrillator, for example, an absorbable stent is not prepositionable to protect against a post absorption condition for which the patient is at risk or when the need for a stent can be predicted, as will become more significant when genomic diagnosis attains confidence. An absorbable stent is also useless with a condition that proves refractory to medication as do some cases of coronary vasospasm. Where an absorbable stent is indicated, an absorbable extraluminal stent can be used, as addressed above in the section entitled Absorbable Stent-jackets, among others.

Furthermore, the development of endoluminal stents that are absorbed more slowly will not change the basic mechanics, although these might leave the ductus having adapted with limited ability to readapt when the stent is gone. By contrast, once healed, an extraluminal stent does not disrupt function, certainly not approaching that of an endoluminal stent, so that the patient seldom gains benefit from its removal. Moreover, since absorbable extraluminal stents can be provided, even the negligible disruption an extraluminal stent might induce can be avoided. That once the ductus fully heals an extraluminal stent would seldom warrant removal attests to a compliance with physiological function and avoidance of chronic irritation such that to remove it would not benefit the patient.

Ordinary stent-jackets are addressed below in the section entitled Stent-jackets and Stent-jacket Supportng Elements among others; rib and spine-type stent-jackets for use along the digestive tract, in the section below entitled The Extraductal Component of the Extraluminal Stent and the Means for its Insertion, among others; and impasse-jackets, used to hold or trap miniballs or drug carrier bound drugs, in the sections entitled Concept of the Impasse-jacket and Miniball and Ferrofluid-borne Particle-impassable Jackets, or Impasse-jackets, among others. The primary advantage in extraluminal or circumductal stents is the elimination from within the lumen of a foreign object, which is the source of the adverse sequelae experienced with these.

Absence from the lumen means that no obstruction to future transluminal treatment has been introduced. This is true not only of stent-jacket but impasse-jackets as well. Extraluminal stents can incorporate radioisotope and medicinal means to suppress reocclusion. Where these are inadequate and the adventitial or fibrosal and abaxial tissue subjacent thereto would not be irrecoverably injured, another major advantage is that the extraluminal stent can incorporate sufficient continuous magnetically permeable material that reocclusion in the mantled segment can later be cleared by noninvasive thermoplasty accomplished by placing the patient in a high frequency alternating magnetic or lower frequency electromagnetic induction field.

Stent-jackets must not be so strongly magnetized as to pull miniballs through the adventitia or fibrosa or cause the wall of a ductus to delaminate. Use with clasp-wraps requires stronger magnetization, making stent-jackets used to stent incompatible with these. The use of a stent-jacket to attract susceptible matter from the lumen likewise tends to require stronger magnetization than is used to pull the miniball or stay ductus-intramural implants radially outward, making such application dependent upon the magnetic susceptibility of the dispersant within the lumen. At the same time, such warming can be used to accelerate the uptake of therapeutic substances, such as a statin drug. Uptake can be further accelerated by attaching the drug to magnetically susceptible drug carrier particles or nanoparticles.

Where injury to the intervening adventitia is risked, reocclusion is can be reduced by periodic imaging and the application of the inductive field to raise the temperature to no higher than needed to arrest mitosis (see, for example, Sushkov, F. V. and V. V. Portugalov 1975. "Temperature Limits of Mitosis in Mammalian Cell Cultures," *Bulletin of Experimental Biology and Medicine* 80(6):1491-1493, Suga, E., Kenji, K., Futami, H., Yamashita, E., and Arai, T. 2005. "Prevention of Intimal Hyperplasia Using Short-period Vascular Heating Without Surrounding Tissue Injury: In Vitro/In Vivo Experiments and Thermal Conduction Calculation," Society of Photo-Optical Instrumentation Engineers Conference Volume 5686, *Photonic Therapeutics and Diagnostics* 5686:48-446; Edwards, M. J., Mulley, R., Ring, S., and Wanner, R. A. 1974. "Mitotic Cell Death and Delay of Mitotic Activity in Guinea-pig Embryos Following Brief Maternal Hyperthermia," *Journal of Embryology and Experimental Morphology* 32(1):593-602).

The onset of restenosis following transluminal procedures is immediate and usually realized fully within the succeeding six months (see, for example, Tamai, H., Berger, P. B., Tsuchikane, E., Suzuki, T., Nishikawa, H., Aizawa, T., and 6 others 2004. "Frequency and Time Course of Reocclusion and Restenosis in Coronary Artery Occlusions after Balloon Angioplasty versus Wiktor Stent Implantation: Results from the Mayo-Japan Investigation for Chronic Total Occlusion (MAJIC) Trial," *American Heart Journal* 147(3):E9; Nakagawa, Y., Iwasaki, Y., Kimura, T., Tamura, T., Yokoi, H., and 4 others 1996. "Serial Angiographic Follow-up after Successful Direct Angioplasty for Acute Myocardial Infarction," *American Journal of Cardiology* 78(9):980-984). Subsequent chilling allows mitotic arrest by means of heat shock (see, for example, Bergan, P. 1960. "Blocking of Mitosis by Heat Shock," *Nature* 186:905-906; Vidair, C. A., Doxsey, S. J., and Dewey, W. C. 1993. "Heat Shock Alters Centrosome Organization Leading to Mitotic Dysfunction and Cell Death," *Journal of Cellular Physiology* 154(3):443-455; Connolly, E. M., Kelly, C. J., Chen, G., O'grady, T., Kay, E., Leahy, A., and Bouchier-Hayes, D. J. 2003. "Pharmacological Induction of HSP27 Attenuates Intimal Hyperplasia in Vivo," *European Journal of Vascular and Endovascular Surgery* 25(1):40-471).

The application of heat has many other uses palliative and therapeutic, as addressed below in the section entitled Laminated Stent-jackets, for example. Field strength, or frequency and amplitude versus temperature data are provided with the implant, which may be any of those described herein, to include stent-jackets, impasse-jackets, magnetwraps, clasp-magnets, miniballs, and stays. That extraluminal placement eschews the drawbacks of endoluminal placement means that extraluminal placement offers preventive measures not available using conventional means. For example, the operator who stretches a segment of the ductus can preposition a chain-stent over the affected segment less corresponding ductus-intramural implants, allowing later thermoplasty to remedy the reocclusion due to hyperplasia that is predictable in such a case.

If necessary, the stent prepositioned for thermoplasty can be supplemented by placing the miniballs that had been omitted so that the jacket is secondarily converted into the extraductal (extravascular) component of an extraluminal stent. In situations where a permanent endoluminal stent as a preventive measure would be contraindicated, an absorbable endoluminal stent could be applied only if the period it would be required and its persistence were known. In such situation, an extraluminal stent, the presence of which should rarely pose the risk of complications, can be used. A uniform subadventitial distribution of superparamagnetic magnetite or maghemite nanoparticles or finely grained powder would evenly distribute the tension on the retracted tissue under the force of the magnets, but to accomplish implantation thus is needlessly complex.

Unencapsulated elemental iron in the body is readily oxidized, dispersed, and absorbed and therefore requires a protective coating regardless of conformation. When an intrinsically or impregnated coating magnetized stent-jacket cannot be used, small neodymium magnets are used not to obtain forceful fields, but to minimize the size of the magnets necessary to produce the usually mild pulling force required. With the extraluminal stents described herein, the ductus is neither compressed nor stretched (forcibly dilated, forcibly distended) but held to its normal quiescent or diastolic outer diameter to expand with the pulse or to allow peristaltic contraction within.

A permanent elastic polyester or polyether-polyurea copolymeric (spandex, Elastane®, Lycra®, etc.) jacket can also be applied to prevent the growth in an incipient aneurysm; in this case, however, the jacket is secured in place by means described below in the section entitled Jacket End-ties and Side-straps, without ferromagnetic implants introduced into the arterial wall. In treating an artery with negative remodeling, stenosis which prompts stenting that includes a reduction in outer diameter, as a precaution, some miniballs or portions thereof will usually include antiproliferative or antirestenotic medication and/or a radioisotope as well as encapsulated nonabsorbable ferromagnetic content (usually superparamagnetic magnetite or maghemite nanoparticles or finely grained powder) used to draw the ductus wall out to the stent-jacket. Situated entirely outside the lumen, an extraluminal stent used to treat atheromatous tissue is not subject to in-stent restenosis, so that antiproliferative medication can be reduced if not eliminated.

By contrast, endoluminal stents that do not release antiproliferative medication tend to become clogged through in-stent restenosis, even though the antiproliferative elutants themselves or their polymeric platforms can induce vasospasm (see, for example, Watanabe, K., Nakamura, N. Kikuta, K., Matsubara, J., Okuyama E., and Katayama, T. 2010. "A Case of Newly Demonstrated Coronary Spasm 4 Months after Paclitaxel-eluting Stent Implantation for In-stent Restenosis," *Journal of Cardiology Cases* 1(1): e33-e36; Tomassini, F., Varbella, F., Gagnor, A., Infantino, V., Luceri, S., and Conte, M. R. 2009. "Severe Multivessel Coronary Spasm after Sirolimus-eluting Stent Implantation," *Journal of Cardiovascular Medicine* 10(6):485-488; Lee, T. K., Lee, H. C., Hwang, K. W., Chun, K. J., Hong, T. J., and Shin, Y. W. 2008. "A Case of Late Recurrent Vasospasm after Sirolimus-eluting Stent Implantation," *Korean Circulation Journal* 38(3):174-178).

8a. Basic Strengths and Weaknesses of Prior Art Stenting in Vascular, Tracheobronchial, Gastrointestinal, and Urological Interventions To prevent dislodgement, or migration, an endoluminal stent must exert circumferentially outward force. Whether in an artery or different structure, it acts as a chronic local restraint upon the ability of the substrate segment to adjust in gauge. Unless it is absorbable, this restraint will persist, whether the stent becomes endothelialized and incorporated into the lumen wall or not. That the artery can adapt by remodeling does not equate to a normal end condition. Moreover, often more than a single stent must be placed. Endoluminal stenting is less adaptable than is extraluminal stenting to the ductus and its condition. This results in a uniformity and simplicity that comes with the lack of an option selection process pertaining to the kind of stent and means of insertion to be used.

All but ureteral endoluminal stents are structurally alike and placed with a balloon in the same manner, reducing the 'learning curve.' However, this simplicity only reflects an inability to tailor the stent to the actual condition. Whether following a balloon angioplasty, to place a conventional or endoluminal stent is in itself a one step procedure and requires but one, not two entry points, which imposes less trauma than alternative treatments to include placement of an extraluminal stent. Metal stents used for single entry stenting, or stenting without an angioplasty, compress and trap the plaque against the lumen wall.

The stent then remains to pose a permanent risk of fracture, migration, and other complications. An extraluminal stent- or impasse-jacket can be made nonabsorbable or absorbable. Existing absorbable stents lack sufficient strength and require an antecedent angioplasty or atherectomy. When the time needed for any implant described herein is limited, the implant is preferably either absorbable or allowed to remain indefinitely. Placement when recovery will necessitate a second invasive procedure is justified when the reason for intervention warrants. The removal of an extraluminal stent can be deferred until well after placement.

Unlike an endoluminal stent which must parectasically press into the luminal wall exerting high circumferential stresses to avoid migrating (dislodging, displacement) and is substantially static rather than compliant with ductus expansion and contraction, disrupting the physiology and potentially aiding the spread of infection into the dutus wall, an extraluminal stent dynamically expands and contracts with the ductus (see, for example, Moore, J. E. Jr. "Biomechanical Issues in Endovascular Device Design," *Journal of Endovascular Therapy* 2009 16 Supplement 111-11; Bedoya, J., Meyer, C. A., Timmins, L. H., Moreno, M. R., and Moore, J. E. 2006. "Effects of Stent Design Parameters on Normal Artery Wall Mechanics," *Journal of Biomechanical Engineering* 128(5):757-765; Cervera, J. J. B. 2006. Stent Design and Arterial Mechanics: Parameterization Tools Using the Finite Element Method, Thesis, Biomechanical Engineering, Texas Agriculture and Mining University; Holzapfel, G. A., Stadler, M., and Gasser, T. C., 2005. "Changes in the Mechanical Environment of Stenotic Arteries during Interaction with Stents: Computational Assessment of Parametric Stent Designs," *Journal of Biomechanical Engineering* 127(1):166-180; Vernhet, H., Demaria, R., Pérez-Martin, A., Juan, J. M., Oliva-Lauraire, M. C., Marty-Double, C., Sénac, J. P., and Dauzat, M. 2003. "Wall Mechanics of the Stented Rabbit Aorta: Long-term Study and Correlation with Histological Findings," *Journal of Endovascular Therapy* 10(3):577-584; Rolland, P. H., Charifi, A. B., Verrier, C., Bodard, H., Friggi, A., Piquet, P., Moulin, G., and Bartoli, J. M. 1999. "Hemodynamics and Wall Mechanics after Stent Placement in Swine Iliac Arteries: Comparative Results from Six Stent Designs," *Radiology* 213(1):229-246).

This is typified by the fact that, an absorbable copolymer, not magnesium, which lacks the mechanical properties essential for dynamic performance, is used in a temporary extraluminal stent. Outside the ductus, the extraluminal stent is less constrained in diameter, and an absorbable stent or impasse-jacket can leave behind nontoxic constituents that would embolize if released into the bloodstream. Not constantly washed over by blood, the period pending dissolution can be longer, and ingredients can be incorporated that will allow dissolution controlled from outside the body. Magnesium in an absorbable extraluminal, as opposed to an endoluminal stent (see, for example, Erbel, R., Di Mario, C., Bartunek, J., Bonnier, J., and 12 other authors 2007. "Temporary Scaffolding of Coronary Arteries with Bioabsorbable Magnesium Stents: A Prospective, Non-randomised Multicentre Trial," *Lancet* 369(9576): 1839-1840), lacks the pliancy, resilience, fatigue endurance limit, nontoxically alloyed, the strength required, and as an electromagnetic shielding material inconsistent with the ability to warm the implant by induction heating.

A functional stent of magnesium basis would have to be alloyed for resilience and embedded with encapsulated magnetized rare earth (lanthanoid) for magnetic strength. Neither can an absorbable stent be used to protect against plaques that are likely to appear at a later date, as addressed in the section below entitled Comparison of Extraluminal with Endoluminal, or Conventional, Stenting. The small luminal calibers in the vascular tree make any approach that removes a prosthesis from the lumen and resituates it to the perivascular space superior. There are basic physiological and medical advantages, first in the removal and then in the resituation to a location outside the vessel that allows more material to be used.

For example, even made with neodymium, currently the highest energy product material available for a magnet, an endoluminal stent must be too small to contain enough of the material to generate the field strength required to attract blood borne ferromagnetically susceptible drug carrier nanoparticles. Instead, a powerful external magnet must be used to induce the field within the body. An endoluminal stent also stands between the drug and the lesion to be treated and attracts the drug to itself. Any robustness in the stent from added thickness means that to preserve a minimum luminal cross section, the stent must press more into the lumen wall. Historically, endoluminal stents offered distinct advantages over treatment that necessitated open exposure.

However, an extraluminal stent can usually be introduced through a small incision. The superior efficacy of an extraluminal magnetic stent that draws or releases drugs from the bloodstream or the intravascular component of the stent, meaning miniballs or stays, compared to a drug-eluting endoluminal stent is addressed below in several sections, to include that entitled Miniball and Ferrofluid-borne Particle-impassable Jackets, or Impasse-jackets. An endoluminal stent promotes the need for revascularization, which procedure it will also hinder. If magnetized, it draws a drug carrier nanoparticle or ferrofluid-bound drug to itself, diverting the drug from the lesion abluminal to (outside, beyond, behind) it.

In marked contrast, an extraluminal stent or impasse-jacket leaves the lumen free of any foreign object, and positioned outside the ductus, usually an artery, can usually take whatever volume of space is required to present the field strength necessary to attract the ferrofluid through the endothelium and into the plaque or other lesion to any depth within the lumen wall. Since it generates as high gradient a field as necessary at the treatment site, no external magnet is necessary to induce a high gradient field in an endoluminal stent deep within the body. Once emplaced, the patient thereafter appears as necessary for a ferrofluid injection and is free to depart.

Occasional injury from balloon overinflation or a special insertion device notwithstanding, placed transluminally, conventional or endoluminal stents are prosthetic linings that compared to open surgery, confer luminal patency and symptomatic palliation with serious trauma rare. An endoluminal stent is more easily introduced into any deep-lying vessel or ductus that is connected to neighboring tissue that should be left intact or closely surrounded by tissue such as skeletal muscle and has a lumen large enough to admit it. Endoluminal stents are also more widely applicable to veins, often too thinly walled and inappositely located to be stented by the extraluminal means described herein; however, larger veins may be treated thus, and the endoluminal processes possible with angioplasty-capable barrel-assemblies and radial projection catheters described herein are applicable to veins.

Endoluminal stents make possible telemetric monitoring (see, for example, Ferguson, J. E. and Redish, A. D. 2011. "Wireless Communication with Implanted Medical Devices Using the Conductive Properties of the Body," *Expert Review of Medical Devices* 8(4):427-433; Chow, E. Y., Chlebowski, A. L., Chakraborty, S., Chappell, W. J., and Irazoqui, P. P. 2010. "Fully Wireless Implantable Cardiovascular Pressure Monitor Integrated with a Medical Stent," *Institute of Electrical and Electronics Engineers Transactions on Biomedical Engineering* 57(6):1487-1496). Telemetric feedback from an extraluminal stent would originate from a vantage point outside and out of contact with the blood or other luminal contents. However, the pressure within the lumen is no less measurable from outside the ductus. Not only can an extraluminal stent concentrate a drug carrier nanoparticle-bound drug passing in the circulation and draw the drug abaxially through the lumen wall into the lesion, but magnetized miniballs, stays, magnet-jackets, and impasse-jackets can also be used thus, and any of these can also be coated with medication or radioactive.

When excessive periadventitial fat, tunneling, or a lack of clearance that necessitates much dissection interferes with the placement of an extraluminal jacket, the degree of urgency, the age and the condition of the patient will determine whether the superior function of an extraluminal stent over time should be chosen over an endoluminal stent as more expedient. Lower in the body, the femoral, popliteal, and tibial arteries are often affected by vascular disease. Ensheathed amid muscle, these necessitate dissection to encircle. For vessels and ducts that lack circumvascular clearance and require dissection, a purely transluminal approach, with or without the introduction of an endoluminal stent, is preferable, adverse sequelae then less likely. This admits of using a radial projection catheter with side-looking syringe tool-inserts to inject lesions along the lumen wall or a barrel-assembly to implant medication miniballs into lesions within such ductus, but disallows the application of an extraluminal stent.

As the pulse or peristaltic wave traverses the stent, the noncompliant margins of the stent can 'dig into' and otherwise irritate the lumen wall (see, for example, Kim, S. M. and Park, S. Y. 2006. "A Study on the Stent Expansion Behavior of the Human Artery Based on Finite Element Analysis," *Key Engineering Materials* 326-328:747-750; Ballyk, P. D. 2006. "Intramural Stress Increases Exponentially with Stent Diameter: A Stress Threshold for Neointimal Hyperplasia," *Journal of Vascular and Interventional Radiology* 17(7):1139-1145; Gunn, J., Arnold, N., Chan, K. H., Shepherd, L., Cumberland, D. C., and Crossman, D. C. 2002. "Coronary Artery Stretch Versus Deep Injury in the Development of In-stent Neointima," *Heart* 88(4):401-405; Taylor, A. J., Gorman, P. D., Kenwood, B., Hudak, C., Tashko, G., and Virmani, R. 2001. "A Comparison of Four Stent Designs on Arterial Injury, Cellular Proliferation, Neointima Formation, and Arterial Dimensions in an Experimental Porcine Model," *Catheterization and Cardiovascular Interventions* 53(3):420-425).

Depending upon the specific condition, location, and clearance available for placing an intrinsically magnetized thin stainless stent-jacket, the arteries in the extremities, which course through sheaths amid muscles, will be better served by an extraluminal stent with a thinner intrinsically or quasi-intrinsically magnetized stent-jacket, as described below in the section entitled Types of Stent-jacket, than an endoluminal stent. Patient age is a significant factor in deciding whether the clear lumen and superior performance over time of the extraluminal stent justifies surgical access. A lack of circumvascular clearance would interfere with compliance of the stent-jacket to the movement of the ductus, which is a key advantage in the use of an extraluminal stent.

Rather than to compress the substrate ductus with inadequate clearance, the stent-jacket serves precisely to prevent compression. It can also be used to prevent rubbing by neighboring tissue, prevent and seal a fistula, and protect against strangulation by a vascular ring. Sufficient clearance assumes that there is no encroachment upon a neighboring nerve or vein. The types of stent-jacket, the shape and distribution of magnets when used, and the compressibility of skeletal muscle even when flexed mean that clearance should almost always be sufficient. The extraluminal stenting of anomalous coronary arteries which course or tunnel through the myocardium where it is bridged over by myocardial tissue over a length greater than 20 millimeters, then emerges onto the epicardium, is best accomplished without dissection.

The tunneled segment tends not to be susceptible to atherosclerosis but may be to spasm (references cited below in the section entitled Considerations as to Access). Patch-magnets on the pericardium can serve to attract miniballs placed in the anterior (ventral) wall of the artery. Inserting stays requires dissection sufficient to expose the outer surface of the artery. If the age of the patient and spasmodic or stenotic condition justify it, the artery is shallow and relatively simple to free, and clearance can be created for a stent-jacket, then a tunneling coronary artery should be considered for dissecting free. Means exist to locate the artery (see Kikuchi, K., Makuuchi, H., Murakami, H., Suzuki, T., Oono, M., and Chiba, K. 2006. "Use of an Audible Ultrasonic Flowmeter to Locate Deeply Buried Coronary Arteries for Off-pump Coronary Artery Bypass Grafting.," *Japanese Journal of Thoracic and Cardiovascular Surgery* 54(2):75-77).

Use of the magnetic stenting to be described, which necessitates the implantation of ferromagnetic miniballs or stays within the wall of the ductus also necessitate that the ductus wall have a at least minimal thickness and strength, for which testing methods are addressed below in the section entitled Testing and Tests. An endoluminal stent can be used despite delamination (tunic avulsion) without leakage or a moderate degree of malacia in the wall of a blood vessel, although this is less of a concern in the trachea, for example. Whereas modern endoprostheses and stents are made of materials such as titanium and polymers that are nonferromagnetic or are at most weakly ferromagnetic as not to disallow the use of magnetic resonance imaging (MRI), the present means inherently demand the use of ferromagnetic materials that once applied disallow the use of magnetic resonance imaging when heating the implants is contraindicated.

However, where appropriate, the nonintrusive heating of the implants has considerable potential to accelerate the release and uptake of drugs, subject diseased tissue to cytotoxic temperatures as a deliberate means of interstitial magnetic hyperthermic therapy, denature coatings, such as solid protein solders, accelerate the initial setting time of surgical adhesives, and has other applications. While able to reduce restenosis, drug-eluting stents remain susceptible to thrombosis and impaired re-endothelialization (Inoue, T., Croce, K., Morooka, T., Sakuma, M., Node, K., and Simon, D. I. 2011. "Vascular Inflammation and Repair: Implications for Re-endothelialization, Restenosis, and Stent Thrombosis," *Journal of the American College of Cardiology. Cardiovasc Interventions* 4(10):1057-1066; Pilgrim, T. and Windecker, S. 2009. "Drug-eluting Stent Thrombosis," *Minerva Cardioangiologica* 57(5):611-620; Gupta, S. and Gupta, M. M. 2008. "Stent Thrombosis," *Journal of the Association of Physicians of India* 56:969-979; Garg, P. and Mauri, L. 2007. "The Conundrum of Late and Very Late Stent Thrombosis Following Drug-eluting Stent Implantation," *Current Opinion in Cardiology* 22(6):565-571; Kawaguchi, R., Angiolillo, D. J., Futamatsu, H., Suzuki, N., Bass, T. A., and Costa, M. A. 2007. "Stent Thrombosis in the Era of Drug Eluting Stents," *Minerva Cardioangiologica* 55(2): 199-211; Daemen, J., Wenaweser, P., Tsuchida, K., Abrecht, L., and 12 other authors, 2007. "Early and Late Coronary Stent Thrombosis of Sirolimus (rapamycin)-eluting and Paclitaxel-eluting Stents in Routine Clinical Practice: Data from a Large Two-institutional Cohort Study," *Lancet* 369 (9562):667-678; Urban P. and De Benedetti, E. 2007. "Thrombosis: The Last Frontier of Coronary Stenting? [Comment on Daemen et al., preceding]" *Lancet* 369(9562): 619-621); Iakovou, I., Schmidt, T, Bonizzoni, E., Ge, L., and 12 other authors, A.2005. "Incidence, Predictors, and Outcome of Thrombosis After Successful Implantation of Drug-eluting Stents," *Journal of the American Medical Association* 293(17): 2126-2130).

More recent literature brings into question the sustained efficacy of drug eluting stents on several grounds (see, for example, Tung, R., Kaul, S., Diamond, G. A., and Shah, P. K. 2006. "Narrative Review: Drug-eluting Stents for the Management of Restenosis: A Critical Appraisal of the Evidence," *Annals of Internal Medicine* 144(12):913-919). Any endoluminal stent remains within the vessel where it can prompt thrombosis at any time following insertion (see, for example, Kaul, S., Shah, P. K., and Diamond, G. A. 2007. "As Time Goes By: Current Status and Future Directions in the Controversy over Stenting," *Journal of the American College of Cardiology* 50(2):128-137). Such a consequence may not appear for years. While rare, this proves fatal in one third of cases (http://www.ptca.org/des.html). Protection against late thrombosis necessitates the long-term administration of antiplatelet medication, which can induce an allergic reaction or gastrointestinal erosion (gastritis, ulcer) and create a bleeding problem.

By contrast, the implants to be described herein are not contained within the lumen, are not exposed to and not in contact with the blood flowing past, are incapable of movement relative to the ductus wall, and so cannot be thrombogenic, rub, or dislodge. Once placed, an endoluminal stent in a coronary artery and the supportive medication it requires complicates surgery any surgery to follow (see, for example, Wijeysundera, D. N., Wijeysundera, H. C., Yun, L., Wasowicz, M., Beattie, W. S., Velianou, J. L., and Ko, D. T. 2012. "Risk of Elective Major Noncardiac Surgery after Coronary Stent Insertion: A Population-based Study," *Circulation* 126(11):1355-1362; Dweck, M. R. and Cruden, N. L. 2012. "Noncardiac Surgery in Patients with Coronary Artery Stents," *Archives of Internal Medicine* 172(14):1054-1055; Gupta, A. D., Streiff, M., Resar, J., and Schoenberg, M. 2012. "Coronary Stent Management in Elective Genitourinary Surgery," *British Journal of Urology International* 110(4):480-484; Gandhi, N. K., Abdel-Karim, A. R., Banerjee, S., and Brilakis, E. S. 2011. "Frequency and Risk of Noncardiac Surgery after Drug-eluting Stent Implantation," *Catheterization and Cardiovascular Interventions* 77(7): 972-976; Albaladejo, P., Marret, E., Samama, C. M., Collet, J. P., Abhay, K., and 6 others 2011. "Non-cardiac Surgery in Patients with Coronary Stents: The RECO Study," *Heart* 97(19):1566-1572; Savonitto, S., Caracciolo, M., Cattaneo, M., and De Servi, S. 2011. "Management of Patients with Recently Implanted Coronary Stents on Dual Antiplatelet Therapy Who Need to Undergo Major Surgery," *Journal of Thrombosis and Haemostasis* 9(11):2133-2142; Sonobe, M., Sato, T., Chen, F., Fujinaga, T., Shoji, T., Sakai, H., and 4 others 2011. "Management of Patients with Coronary Stents in Elective Thoracic Surgery," *General Thoracic and Cardiovascular Surgery* 59(7):477-482; Berger, P. B., Kleiman, N. S., Pencina, M. J., Hsieh, W. H., and 6 others 2010. "Frequency of Major Noncardiac Surgery and Subsequent Adverse Events in the Year after Drug-eluting Stent Placement Results from the EVENT (Evaluation of Drug-Eluting Stents and Ischemic Events) Registry," *Journal of the American College of Cardiology. Cardiovascular Interventions* 3(9):920-927; Cruden, N. L., Harding, S. A., Flapan, A. D., Graham, C., Wild, S. H., Slack, R., Pell, J. P., and Newby, D. E. 2010. "Previous Coronary Stent Implantation and Cardiac Events in Patients Undergoing Noncardiac Surgery," *Catheterization and Cardiovascular Interventions* 3(3):236-242; Savonitto, S., D'Urbano, M., Caracciolo, M., Barlocco F., and 4 others 2010. "Urgent Surgery in Patients with a Recently Implanted Coronary Drug-eluting Stent: A Phase II Study of 'Bridging' Antiplatelet Therapy with Tirofiban during Temporary Withdrawal of Clopidogrel," *British Journal of Anaesthesia* 104(3):285-291; Schouten, O., Bax, J. J., and Poldermans, D. 2007. "Management of Patients with Cardiac Stents Undergoing Noncardiac Surgery," *Current Opinion in Anaesthesiology* 20(3):274-278; Brilakis, E. S., Banerjee, S., and Berger, P. B. 2007. "The Risk of Drug-eluting Stent Thrombosis with Noncardiac Surgery," *Current Cardiology Reports* 9(5):406-411).

The use of a stent, necessarily oversized and substantially noncompliant, inside an artery presumes a narrowing of the lumen as the result of negative remodeling, and in most instances, an antecedent angioplasty or atherectomy to have reduced that stenosis (constriction, narrowing). Alternatively, a stent may be placed to avert abrupt flap thrombosis and/or spasmodic closure. A healthy artery that has not been angioplastied much less balloon injured appears able to adapt to an oversized endoluminal stent (Dirsch, O., Dahmen, U., Fan, L. M., Gu, Y. L., Shen, K., Wieneke, H., and Erbel, R. 2004. "Media Remodeling—The Result of Stent Induced Media Necrosis and Repair," *Vasa* 33(3):125-129). While complication-free insertion of an endoluminal stent is routinely less traumatic than is the placement of an extraluminal stent, an endoluminal stent must be fixed in position by exerting outward force against the surrounding wall of the ductus, which ipso facto will have been diseased and usually angioplastied.

In an extraluminal stent, the lumen wall is drawn against the internal surface of the stent-jacket, which prevents a dissection or rupture. Drug-eluting stents reduce the need for reintervention but have not demonstrated a long-term reduction in subsequent myocardial infarction or death (Steinberg, D. H. and Satler, L. F. 2008. "Drug-eluting Stent Thrombosis," *Minerva Cardioangiologica* 56(1):127-137; Chen, J. P. 2008. "Safety and Efficacy of the Drug-eluting Stent: A Double-edged Sword?," *Southern Medical Journal* 101(2): 174-178; 123-124; Jaffe, R. and Strauss, B. H. 2007. "Late and Very Late Thrombosis of Drug-eluting Stents: Evolving Concepts and Perspectives," *Journal of the American College of Cardiology* 50(2):119-127; Valimigli, M. 2006. *High-Risk Percutaneous Intervention in the Drug-Eluting Stent Era*, Doctoral Dissertation, Erasmus University, Rotterdam, Holland).

Drug eluting stents, notably those that deliver sirolimus (rapamycin, Rapamune®), have also been reported to fracture and become partially if not fully occluded (see, for example, Canan, T. and Lee, M. S. 2010. "Drug-eluting Stent Fracture: Incidence, Contributing Factors, and Clinical Implications," *Catheterization and Cardiovascular Interventions* 75(2):237-245; Chhatriwalla, A. K., Cam, A., Unzek, S., Bhatt, D. L., and 6 others 2009. "Drug-eluting Stent Fracture and Acute Coronary Syndrome," *Cardiovascular Revascularization Medicine* 10(3):166-171; Jin, X., Zhang, S., Xie, H., Wang, C., Fan, Z., Zeng, Y., Shen, Z., and Fang, Q. 2007. "Strut Fracture of DES: An Increasing Problem?," *International Journal of Cardiology* 118(2):e54-e56; Kim, E. J., Rha, S. W., Wani, S. P., Suh, S. Y., Choi, C. U., Kim, J. W., Park, C. G., Seo, H. S., and Oh, D. J. 2007. "Coronary Stent Fracture and Restenosis in the Drug-eluting Stent Era: Do We Have Clues of Management?," *International Journal of Cardiology* 120(3):417-419; Lee, M. S., Jurewitz, D., Aragon, J., Forrester, J., Makkar, R. R., and Kar, S. 2007. "Stent Fracture Associated with Drug-eluting Stents: Clinical Characteristics and Implications," *Catheterization and Cardiovascular Interventions* 69(3): 387-394).

Drug-eluting stents also appear to lead to a weakening of the arterial wall that can result in an aneurysm (see, for example, Luthra, S., Tatoulis, J., and Warren, R. J. 2007. "Drug-eluting Stent-induced Left Anterior Descending Coronary Artery Aneurysm: Repair by Pericardial Patch—Where Are We Headed?," *Annals of Thoracic Surgery* 83(4):1530-1532; Panja, M., Basu, S., and Mondol, S. 2005 "A Case of Giant Aneurysm Following Percutaneous Coronary Intervention," *Indian Heart Journal* 7(6):731-733). Endoluminal stents containing nonferrous metals, drug-eluting or not, can elicit a severe allergic reaction (see Almpanis, G. C., Tsigkas, G. G., Koutsojannis, C., Mazarakis, A., Kounis, G. N., and Kounis, N. G. 2010. "Nickel Allergy, Kounis Syndrome and Intracardiac Metal Devices," *International Journal of Cardiology* 145(2):364-365), and in association with allergic inflammatory reactions, drug-eluting stents can induce thrombosis (Virmani, R, Guagliumi, G., Farb, A., Musumeci, G., Grieco, N., Motta, T., Mihalcsik, L., Tespili, M., Valsecchi, O., and Kolodgie, F. D. 2004. "Localized Hypersensitivity and Late Coronary Thrombosis Secondary to a Sirolimus-Eluting Stent: Should We Be Cautious?," *Circulation* 109(6):701-705. The action associated with the placement of a conventional endoluminal stent can produce the conditions that result in restenosis (see, for example, Anderson, H. V. and Carabello, B. A. 2000. "Provisional versus Routine Stenting: Routine Stenting is Here to Stay," *Circulation* 102(24):2910-2914), and once placed, the stent that was required for sequelae which were the direct result of balloon angioplasty is not just susceptible to but becomes itself an additional factor that provokes restenosis.

By comparison, a stent with no endoluminal presence cannot clog, much less stimulate a response that would clog it. In order to minimize the risk of migration whenever the artery expands, an endoluminal stent must exceed the lumen in its expanded diameter. In the gastrointestinal tract, a ureter, or gamete duct, the stent must exceed the resting diameter, thus interfering with peristalsis. Endoluminal stents for use in the gastrointestinal tract will usually have pronounted prominences about the circumference to avert migration by peristalsis. Not allowing either an artery or the gut to contract, an endoluminal stent remains as a chronic source of noncompliance or nonadaptive restraint and irritation.

If temporary (absorbable), the rate of dissolution is not likely to match that required, even when this period can be predicted. Moreover, if underexpanded in an artery, subacute thrombosis can develop in the gaps that separate the stent from the vessel wall. In contrast, an extraluminal stent-jacket, is pliable and matched in diameter to the resting diameter of the substrate ductus. It then expands and contracts along with the pulse and frees the gut to contract inside it. At least in the carotid arteries, the disruption of forced distention imposed by an endoluminal stent appears to subside during the first few weeks following placement, vessels suited to higher pressures apparently able to adapt (see, for example, Dirsch et al. 2004, cited above).

Adapted to or not, the widened diameter of the lumen and resistance to migration imparted by overexpansion (see, for example, Rogers, C., Tseng, D. Y., Squire, J. C., and Edelman, E. R. 1999. "Balloon-Artery Interactions During Stent Placement: A Finite Element Analysis Approach to Pressure, Compliance, and Stent Design as Contributors to Vascular Injury," *Circulation Research* 84(4):378-83) do little to reduce thrombosis and restenosis (Lally, C., Dolan, F., and Prendergast, P. J. 2004. "Cardiovascular Stent Design and Vessel Stresses: A Finite Element Analysis," *Journal of Biomechanics* 38(8):1574-1581; Rogers, C. and Edelman, E. R. 1995. "Endovascular Stent Design Dictates Experimental Restenosis and Thrombosis," *Circulation* 91(12):2995-3001; Gunn, J., Arnold, N., Chan, K. H., Shepherd, L., Cumberland, D. C., and Crossman, D. C. 2002, cited in the preceding paragraph).

Furthermore, the clinical results seen in the coronary arteries may differ markedly from those obtained with peripheral arteries (see, for example, Dube, H., Clifford, A. G., Barry, C. M., Schwarten, D. E., and Schwartz, L. B. 2007. "Comparison of the Vascular Responses to Balloon-Expandable Stenting in the Coronary and Peripheral Circulations: Long-term Results in an Animal Model Using the TriMaxx Stent," *Journal of Vascular Surgery* 45(4):821-827; Krueger, K. D., Mitra, A. K., DelCore, M. G., Hunter, W. J. 3rd, and Agrawal, D. K. 2006. "A Comparison of Stent-induced Stenosis in Coronary and Peripheral Arteries," *Journal of Clinical Pathology* 59(6):575-579, which agree as to there being differences but contradict one another as to whether the severity is greater in peripheral than in coronary arteries).

In the vasculature, chronic contact with the luminal endothelium probably excites the subjacent layers to proliferate—"It is believed that the central role of the vascular endothelium is to maintain quiescence of the underlying media and adventitia" (Aoki, J., Serruys, P. W., van Beusekom, H., Ong, A. T., McFadden, E. P., Sianos, G., van der Giessen, W. J., Regar, E., de Feyter, P. J., Davis, H. R., Rowland, S., and Kutryk, M. J. 2005. "Endothelial Progenitor Cell Capture by Stents Coated with Antibody Against CD34: The HEALING-FIM (Healthy Endothelial Accelerated Lining Inhibits Neointimal Growth-First In Man) Registry," *Journal of the American College of Cardiology* 45(10):1574-1579).

Whether in the vascular tree, the tracheobronchial tree, the bile, or urinogenital ducts, endoluminal stents cover over and compress portions of the internal surface or endothelium of the lumen, necessarily interfering with normal lumen wall physiology at every level from the biochemical, to the microscopic, to the gross anatomical. The portions of the lumen wall in contact with the stent are blocked off from the normal chemical and physiological environment at the same time that the portions of the stent in contact with the contents flowing through serve as a platform for the deposition of occlusive matter, whether salts in the ureters or platelets and fat in the bloodstream.

An endoluminal stent forcibly interferes with normal vasomotion, and to this, a drug-eluting stent can add chemical interference (see, for example, Tomassini, F., Varbella, F., Gagnor, A., Infantino, V., Luceri, S., and Conte, M. R. 2009. "Severe Multivessel Coronary Spasm after Sirolimus-eluting Stent Implantation," *Journal of Cardiovascular Medicine* 10(6):485-488; Brott, B. C., Anayiotos, A. S., Chapman, G. D., Anderson, P. G., and Hillegass, W. B. 2006. "Severe, Diffuse Coronary Artery Spasm after Drug-eluting Stent Placement," *Journal of Invasive Cardiology* 18(12): 584-592; Hamilos, M., Sarma, J., Ostojic, M., Cuisset, T., Sarno, G., and 9 others 2008. "Interference of Drug-eluting Stents with Endothelium-dependent Coronary Vasomotion: Evidence for Device-specific Responses," *Circulation. Cardiovascular Interventions* 2008 1(3):193-200; El-Bialy, A., Shenoda, M., and Caraang, C. 2006. "Refractory Coronary Vasospasm Following Drug-eluting Stent Placement Treated with Cyproheptadine," *Journal of Invasive Cardiology* 18(2):E95-98). Endoluminal stents also pose a risk of late thrombosis that necessitates the long term administration of platelet blockade medication.

Endoluminal stents placed to treat vasospastic angina may induce or displace spasm at the margins (see, for example, Kaku, B., Honin, K., Horita,Y., Uno, Y., Yamazaki, T., Funada, A., and Ohka, T. 2005. "The Incidence of Stent-edge Spasm after Stent Implantation in Patients with or without Vasospastic Angina Pectoris," *International Heart Journal* 46(1):23-33; Celik, T., Iyisoy, A., Yüksel, U. Ç., Bugan, B., and Ersoy, I. 2009. "Stent-edge Vasospasm after Bare Metal Stent Implantation: A Case Report and Review of the Literature," *Gülhane Tip Dergisi* 51:174-176). Unlike an extraluminal stent with the aid of suitable medication such as nicorandil, trihexyphenidyl hydrochloride, or denopamine., an endoluminal stent is susceptible to deformation from severe spasm (Yoshida, T., Kobayashi, Y., Nakayama, T., Kuroda, N., Komiyama, N., and Komuro, I. 2006. "Stent Deformity Caused by Coronary Artery Spasm," *Circulation Journal* 70(6):800-801). Neither would an extraluminal stent be likely to induce thrombosis or spasm as have drug-eluting endoluminal stents (Brott, B. C., Anayiotos, A. S., Chapman, G. D., Anderson, P. G., and Hillegass, W. B. 2006. "Severe, Diffuse coronary Artery Spasm after Drug-eluting Stent Placement," *Journal of Invasive Cardiology* 18(12):584-592).

In the airway, contact of the lumen wall with the stent blocks out oxygenated air abaxially (inward through the endothelium), secretion adaxially (outward from the endothelium onto the internal surface of the lumen), as well as transport along the lumen wall. Similarly, a stent in the vasculature obliterates the two-way blood-endothelial interface, resulting in long term endothelial dysfunction (see, for example, Celik et al. 2009 op cit.; Caramori, P. R., Lima, V. C., Seidelin, P. H., Newton, G. E., Parker, J. D., and Adelman, A. G. 1999. "Long-term Endothelial Dysfunction after Coronary Artery Stenting," *Journal of the American College of Cardiology* 34(6): 1675-1679;). Endothelial secretory dysfunction is a significant factor in much vascular pathology.

Where endothelial dysfunction exits due to an antecedent acute cardiac event, an endoluminal stent is likely to add further to the dysfunction (Akcakoyun, M., Kargin, R., Tanalp, A. C., Pala, S., Ozveren, O., Akcay, M., Barutcu, I., and Kirma, C. 2008. "Predictive Value of Noninvasively Determined Endothelial Dysfunction for Long-term Cardiovascular Events and Restenosis in Patients Undergoing Coronary Stent Implantation: A Prospective Study," *Coronary Artery Disease* 19(5):337-343). Broadly, a mechanical expedient essential to meet the priimary requirement of maintaining patency, endoluminal stents are otherwise noncompliant with and disruptive of ductus physiology in every way.

In the airway, secretory and mucociliary (mucociliary 'escalator') action, the action of alveolar macrophages and tissue histiocytes, normal exposure to oxygen and moisture, other chemical interaction at the surface of the lumen such as the local secretion of immunoglobulins (*The Merck*

Manual of Diagnosis and Therapy, 18th Edition, page 1387), and smooth muscle action are all disrupted. Interference with the normal physiology of the tracheobronchial tree can exert a significant nonmechanical secondary effect in impairing immunomodulatory function. The thicker walls along the gastrointestinal tract accommodate ductus-intramural implants without the need for tumefacients, for example.

Whether in the vascular or bronchial tree, the minimum caliber of a ductus tractable to the placement of an extraluminal stent primarily depends upon the ability of the ductus wall to accept and retain the implants and secondarily upon the availability of a barrel-assembly or stay insertion tool small enough to accomplish implantation. Wall insufficiency will generally precede the inability to produce a muzzlehead small that is enough to fit. In the bronchial tree, the tertiary bronchi, which must adapt in gauge necessitating smooth muscle, usually represent this limit. An extraluminal stent that leaves the lumen clear avoids the restriction to smooth muscle action, blockage to secretion, and functioning of the mucociliary escalator. The vasospasm of asthma affects the bronchioles at the junction with the alveoli where the size and distribution of the tissue affected rule out treatment by means other than the use of drugs.

Stenting has, however, been used to treat asthma comorbidity (see, for example, Ernst, A., Majid, A., Feller-Kopman, D., Guerrero, J., Boiselle, P., and 6 others, 2007. "Airway Stabilization with Silicone Stents for Treating Adult Tracheobronchomalacia: A Prospective Observational Study," *Chest* 132(2):609-616). Endoluminal stents in the airway often cause chronic irritation and are subject to fracture (Mittleman, E., Weisse, C., Mehler, S. J., and Lee, J. A. 2004. "Fracture of an Endoluminal Nitinol Stent Used in the Treatment of Tracheal Collapse in a Dog," *Journal of the American Veterinary Medical Association* 225(8): 1196, 1217-1221; Woo, H. M., Kim, M. J., Lee, S. G., Nam, H. S., Kwak, H. H., Lee, J. S., Park, I. C., and Hyun, C. 2007. "Intraluminal Tracheal Stent Fracture in a Yorkshire Terrier," *Canadian Veterinary Journal* 48(10):1063-1066) and some types are liable to migrate (see, for example, Noppen, M., Meysman, M., Claes, I., D'Haese, J., and Vincken, W. 1999. "Screw-thread vs Dumon Endoprosthesis in the Management of Tracheal Stenosis," *Chest* 115(2):532-535; Kitanosono, T., Honda, M., Matsui, S., Hashimoto, T., Munechika, H., Hishida, T., Okubo, K., and Koizumi, K. 1997. "Migration of Gianturco Expandable Metallic Stents in the Upper Trachea," *Cardiovascular and Interventional Radiology* 20(3):216-218).

In the trachea or bronchi, much less the gut, a conventional stent, in contrast to subfibrosally implanted minispheres or stays, which are substantially isolated from the lumen and its contents, can serve as a scaffold for the spread of infection to include tubercular (Casal, R. F. 2010. "Update in Airway Stents," *Current Opinionin Pulmonary Medicine* 16(4):321-328; Agrafiotis, M., Siempos, I. I., and Falagas, M. E. 2009. "Infections Related to Airway Stenting: A Systematic Review," *Respiration* 78(1):69-74; Park, K. Y. and Park, C. H. 2005. "Candida Infection in a Stent Inserted for Tracheal Stenosis after Heart Lung Transplantation," *Annals of Thoracic Surgery* 79(3):1054-1056; Bautista, M., Greenberg, A., and Weissman, P. 2002. "Expansion of a Lung Abscess after Stent Closure of a Bronchoesophageal Fistula," *Gastrointestinal Endoscopy* 55(2):281-283).

In muscular arteries, the use of stays avoids the lumen entirely, eliminating direct contact with the bloodstream as an avenue for the systemic spread of infection (see, for example, Chambers, C. E., Eisenhauer, M. D., McNicol, L. B., Block, P. C., Phillips, W. J., Dehmer, G. J., Heupler, F. A., and Blankenship, J. C. 2006. "Infection Control Guidelines for the Cardiac Catheterization Laboratory: Society Guidelines Revisited," *Catheterization and Cardiovascular Interventions* 67(1):78-86; Ramsdale, D. R., Aziz, S., Newall, N., Palmer, N., and Jackson, M. 2004. "Bacteremia Following Complex Percutaneous Coronary Intervention," *Journal of Invasive Cardiology* 16(11):632-634, available at http://www.invasivecardiology.com/article/3330; Culver, D. A., Chua, J., Rehm, S. J., Whitlow, P., and Hertzer, N. R. 2002. "Arterial Infection and Staphylococcus Aureus Bacteremia after Transfemoral Cannulation for Percutaneous Carotid Angioplasty and Stenting," *Journal of Vascular Surgery* 35(3):576-579; Muñoz, P., Blanco, J. R., Rodríguez-Creixéms, M., García, E., Delcan, J. L., and Bouza, E. 2001. "Blood Stream Infections after Invasive Nonsurgical Cardiology Procedures," *Archives of Internal Medicine* 161(17): 2110-2115; Samore, M. H., Wessolossky, M. A., Lewis, S. M., Shubrooks, S. J. Jr., and Karchmer, A. W. 1997. "Frequency, Risk Factors, and Outcome for Bacteremia after Percutaneous Transluminal Coronary Angioplasty," *American Journal of Cardiology* 79(7):873-877; Shea, K. W., Schwartz, R. K., Gambino, A. T., Marzo, K. P., and Cunha, B. A. 1995. "Bacteremia Associated with Percutaneous Transluminal Coronary Angioplasty," *Catheterization and Cardiovascular Diagnosis* 36(1):5-10).

In any lumen, an endoluminal stent accumulates debris and pathogens, increasing the risk of infection, local and spreading. Esophageal stents have been suspected to spread infection to the spine (see, for example, Mullen, T. D., Sharma, A. K., and Varma, A. K. 2012. "Cervical Osteomyelitis after Placement of a Self-expanding Plastic Stent for Palliation of Dysphagia Associated with Chemoradiation-induced Esophageal Strictures," *Head and Neck* in press February 2012; Li, C. Y., Chen, W. C., Yang, S. H., and Lee, Y. C. 2009. "A Rare Complication of Esophageal Stent: Spinal Epidural Abscess," *Annals of Thoracic Surgery* 88(5):1700-1702Lloyd, D. and Smith, D. 2002. "Cervical Discitis in a Patient with an Oesophageal Stent for Carcinoma," *Rheumatology* 41(12): 1453, although the spread of infection to the meninges can occur following a spontaneous perforation of the esophagus (Boerhaave's syndrome) (Jurani, C. C., Early, G. L., and Roberts, S. R. 2002. "Spontaneous Esophageal Perforation Presenting as Meningitis," *Annals of Thoracic Surgery* 3(4):1294-1296), and may be promoted by poststenting chemoradiation (Christie, N. A., Buenaventura, P. O., Fernando, H. C., Nguyen, N. T., Weigel, T. L., Ferson, P. F., and Luketich, J. D. 2001. "Results of Expandable Metal Stents for Malignant Esophageal Obstruction in 100 Patients: Short-term and Long-term Follow-up," *Annals of Thoracic Surgery* 71(6):1797-1802).

The risk of migration that necessitates a large diameter with outward radial force to disrupt function and assist in inoculating the ductus wall should the stent become infected is primarily the result of the propulsive or propagative action of the contents passed. Mass flow through the stent undiminished, even when expanded just enough to preclude migration, an endoluminal stent interrupts and thus interferes with the radial movements in the ductus wall beginning at both the proximal and distal stent margins. In the vascular tree and ureters, the endoluminal stent acts as a scaffold for the deposition of matter out of the passing fluid. In a ureter, urinary salts accrete on the stent, which to prevent total occlusion must be replaced every few months.

In the vascular tree, an endoluminal stent disrupts laminar or streamline flow, the turbulence predisposing to thrombus formation and rarely, infection (see, for example, Gonda, E., Edmundson, A., and Mann, T. 2007. "Late Coronary Stent Infection: A Unique Complication after Drug-eluting Stent Implantation," *Journal of Invasive Cardiology* 19(10):E307-E308 Kaufmann, B. A., Kaiser, C., Pfisterer, M. E., and Bonetti, P. O. 2005. "Coronary Stent Infection: A Rare but Severe Complication of Percutaneous Coronary Intervention," *Swiss Medical Weekly* 135(33-34):483-487; Chambers, S. T. 2005. "Diagnosis and Management of Staphylococcal Infections of Vascular Grafts and Stents," *Internal Medicine Journal* 35 Supplement 2:S72-S78; Dieter, R. S. 2000. "Coronary Artery Stent Infection," *Clinical Cardiology* 23(11):808-810; Latham, J. A. and Irvine, A. 1999. "Infection of Endovascular Stents: An Uncommon but Important Complication," *Cardiovascular Surgery* 7(2): 179-182; Deiparine, M. K., Ballard, J. L., Taylor, F. C., and Chase, D. R. 1996. "Endovascular Stent Infection," *Journal of Vascular Surgery* 23(3):529-533). An extraluminal stent avoids the foregoing problems.

Additionally providing support from about the outer surface and interposing a shield or physical barrier between the ductus and surrounding tissue, an extraluminal stent interferes with the spread of infection and reduces the risk of rupture as typified by the carotid blowout syndrome (see, for example, Broomfield, S. J., Bruce, I. A., Luff, D. A., Birzgalis, A. R., and Ashleigh, R. J. 2006. "Endovascular Management of the Carotid Blowout Syndrome," *Journal of Laryngology and Otology* 120(8):694-697; Chaloupka, J. C., Putman, C. M., Citardi, M. J., Ross, D. A., and Sasaki, C. T. 1996. Endovascular Therapy for the Carotid Blowout Syndrome in Head and Neck Surgical Patients: Diagnostic and Managerial Considerations," *American Journal of Neuroradiology* 17(5):843-852). Moreover, as addressed below in the section entitled Radiation Shield-jackets and Radiation Shielded Stent-jackets Absorbable and Nonabsorbable, an extraluminal stent can provide radiation shielding (see, for example, McDonald, M. W., Moore, M. G., and Johnstone, P. A. 2012. "Risk of Carotid Blowout after Reirradiation of the Head and Neck: A Systematic Review," *International Journal of Radiation Oncology Biology Physics* 82(3):1083-1089). The impulse to prevent migration by overly expanding a stent in particular can result in chronic restraint-irritation and injury of the ductus leading to delayed and long term sequelae.

More specifically, an endoluminal stent introduces wave reflection sites at the stent entrance and exit (see, for example, Alderson, H. and Zamir, M. 2004. "Effects of Stent Stiffness on Local Haemodynamics with Particular Reference to Wave Reflections," *Journal of Biomechanics* 37(3): 339-348; Seo, T., Schachter, L. G., and Barakat, A. I. 2005. "Computational Study of Fluid Mechanical Disturbance Induced by Endovascular Stents," *Annals of Biomedical Engineering* 33(4):444-456; Bedoya, J., Meyer, C. A., Timmins, L. H., Moreno, M. R., and Moore, J. E. 2006. "Effects of Stent Design Parameters on Normal Artery Wall Mechanics," *Journal of Biomechanical Engineering* 128(5):757-765), centrifugally agitating platelets and other blood cells that normally move axially in laminar flow (see, for example, He, Y., Duraiswamy, N., Frank, A. O., and Moore, J. E. Jr. 2005. "Blood Flow in Stented Arteries: A Parametric Comparison of Strut Design Patterns in Three Dimensions," *Journal of Biomechanical Engineering* 127(4):637-647; Porth, C. M. 2004. *Pathophysiology: Concepts of Altered Health States*, Philadelphia, Pa.: Lippincott Williams and Wilkins), therewith inducing the thrombogenicity associated with turbulent flow.

With a stent that lies entirely outside the lumen, the lifelong use of a statin drug that results from this turbulence is avoided. Essentially, an endoluminal stent not only obstructs, occludes, irritates, and creates stenosis, but forces the propulsive forces in the lumen wall to make the ductus injure itself. Practically irrecoverable, endoluminal stents can be life-saving upon insertion only to produce serious if not life-threatening complications later. A stent within an artery, especially one made of metal, encourages the clotting and adhesion to its surface of blood, prompting the administration of platelet blockade or anticoagulants to high levels conducive to bleeding problems.

Except where an absorbable stent can be used (see, for example, Erbel, R., Di Mario, C., Bartunek, J., Bonnier, J., and 12 other authors 2007. "Temporary Scaffolding of Coronary Arteries with Bioabsorbable Magnesium Stents: A Prospective, Non-randomised Multicentre Trial," *Lancet* 369(9576): 1839-1840), once placed, an endoluminal stent is removed when it must but is then usually replaced, prompting the administration of antiplatelet medication on an extended if not lifelong basis. While configured unlike a vascular stent but much longer in the form of a catheter, a ureteric stent likewise encourages the deposition and accretion of debris upon it, in this case, calcium oxalate, calcium phosphate, and ammonium magnesium phosphate salts.

Situated thus, the contents, if not positively induced to precipitate onto the foreign surface, can additionally be trapped inside and clog the stent. Unlike endoureteral stents, an extraureteral stent is not susceptible to encrustation, bacterial colonization, clogging, or enstonement that necessitates replacement every three months, which can be operatively difficult if not painful. Except for those made of tantalum or platinum, endoluminal stents are poorly radiopaque, and should one in the arterial tree be dropped from the balloon (Hubner, P. J. B. 1998. *Guide to Coronary Angioplasty and Stenting*, Amsterdam, Holland: Harwood Academic Publishers, page 108), will usually prove difficult if not impossible to locate much less retrieve without open exploratory surgery. Historically, the main problem with stenting in the vascular tree—restenosis—was to an extent ameliorated with the appearance of the Palmaz-Schatz stent.

However, the central joint or articulation in this endoluminal stent, which is provided to allow some flexion for trackability, is a point of weakness that fails to adequately retain the subjacent lumen wall, which under intraductal ultrasound is seen to prolapse into the joint and constrict the lumen (see, for example, Kim, S. W., Mintz, G. S., Ohlmann, P., Hassani, S. E., Fernandez, S., Lu, L., Chu, W. W., and 9 others 2006. "Frequency and Severity of Plaque Prolapse within Cypher and Taxus Stents as Determined by Sequential Intravascular Ultrasound Analysis," *American Journal of Cardiology* 98(9):1206-1211; Prendergast, P. J., Lally, C., Daly, S., Reid, A. J., Lee, T. C., Quinn, D., and Dolan, F. 2003. "Analysis of Prolapse in Cardiovascular Stents: A Constitutive Equation for Vascular Tissue and Finite-Element Modelling," *Journal of Biomechanical Engineering* 125(5):692-699).

In fact, " . . . the stent has poor trackability and is best used for proximal lesions in straight vessels, free from disease down to the lesion," (Hubner, Op. cit., page 107). Such a consequence also speaks to the advantage of plaque removal through atherectomy rather than balloon crushing, with medical and not just mechanically adverse consequences of the merely displaced plaque addressed in the sections above entitled Drug-releasing and Irradiating miniballs, Stays, and Ferrofluids, and Basic Strengths and Weaknesses of Prior Art Stenting in Vascular, Tracheobronchial, Gastrointestinal, and Urological Interventions, among others.

In the effort to suppress the restenosis of an endovascular stent, an angiotensin converting enzyme inhibitor (angiotensin receptor antagonist or blocker—see for example, Traub, Y. and Shapiro, A. P. 1997, "Management of Hypertension with Particular Attention to the Renin-Angiotensin System," in Glew, R. H. and Ninomiya, Y., *Clinical Studies in Medical Biochemistry*, New York, N.Y.: Oxford University Press), such as valsartan)(Diovan®, an angiotensin receptor blocker that acts as a cytokine gene expression inhibitor, such as tacrolimus; or candesartan cilexetil; or an angiotensin II receptor antagonist or blocker and cytostatic immunosuppressant, such as sirolimus (rapamycin, Rapamune®) is often administered, even though the efficacy in long term use of immunosuppressants or anti-hypertensives for this purpose remains unproven.

A more recent version of the Palmaz-Schatz stent, the Palmaz-Schatz Crown stent, has two spiral articulations, and while more trackable, still suffers from the common problems associated with endoluminal vascular placement, as do the most advanced endovascular stents. If the lumen is obstructed, some tend to drop from the balloon. If the stent becomes stuck and an effort is made to withdraw it, or if the balloon is withdrawn, single wire coil stents may uncoil, and rarely, catheter components, to include guidewires, Rotablator® Systems, and stents, become entrapped during cardiologic interventions, causing life-threatening complications and the need for emergency cardiac surgery (Alexiou, K., Kappert, U., Knaut M., Matschke, K., and Tugtekin, S. M. 2006. "Entrapped Coronary Catheter Remnants and Stents: Must They Be Surgically Removed?," *Texas Heart Institute Journal* 33(2):139-142.

With several endovascular stents, the delivery catheter balloon may fail to deflate, making withdrawal difficult. In some instances, this has led to serious complications requiring coronary artery bypass surgery or to death. One factor in the promotion of intimal hyperplasia by an endoluminal stent is that it creates an abrupt change in the internal diameter of the lumen (see, for example, Adam, A., Dondelinger, R. F., and Mueller, P. R. (editors) 1997. *Textbook of Metallic Stents*, London, England: Informa HealthCare, page 179). In any endoluminal stent, a larger mesh or grid gap improves side branch accessibility to a guidewire, but only at the risk of lumen wall prolapse due to a lack of support (Hubner, op cit. page 114). Furthermore, situated at or beside the ostium, the grid is more thrombogenic, making a large mesh risky for spanning a side branch. Inducing patency by extraluminal means will not eschew all limitations and sequelae, but it will these.

The thrombogenic, spasm inducing, and narrowing that can result from allowing a rare fractured guidewire to remain in a coronary artery demand surgical removal (Demirsoy, E., Bodur, H. A., Arbatli, H., Yağan, N., Yilmaz, O., Tükenmez, F., Ozturk, S., and Sönmez, B. 2005. "Surgical Removal of Fractured Guidewire with Ministernotomy," (in English) *Anatolian Journal of Cardiology (Anadolu Kardiyoloji Dergisi)* 5(2):145-147, also cited above). Radially and longitudinally rigid and continuous in structure, most endoluminal stents are noncompliant to physiological changes in vascular gauge and unaccommodating of gross movement. Thus, to span or straddle branches or to bend, separate stents must be used to either side of the branch or point of flexion, presenting the multiple thrombogenic edges, or margins, of two or more stents. Even rimless, or uniform in gauge out to the edges, an endoluminal stent compresses the tissue it restrains, creating inconsistencies in lumen diameter and turbulent flow at either end.

The tendency for the edges of endovascular (endoluminal) stents to irritate and induce the formation of thrombi is increased with multiple stents, as when used to anchor the ends of an endovascular graft (see Parodi, J. C., Veith, F. J., and Marin, M. L. 1998. Endovascular Grafting Techniques, Baltimore, Md.: Williams and Wilkins, page 128, figure 15.5), or in treating either intermittent segments of vessels diseased over lengths considered too small and not sufficiently deteriorated to justify excision and anastomosis or the insertion of a graft, or segments to either side of a branch or point of flexion. Largely dependent upon caliber, that the margins of an endovascular stent are noncompliant both inwardly and outwardly means that the stent will act as a factor in its restenosis and then make the transluminal removal of the blockage difficult.

Lacking a side-hole wherewith to straddle or span T-junctions of which the orifices (ostia, entries) are notably susceptible to atherogenesis, endoluminal stents necessitate the use of two stents, thus leaving the segment of the vessel wall opposite and subtended by the opening to the branch, or ostium, unstented. Since the proximating ends of endoluminal stents to either side of the branch opening usually maintain the diameter of the lumen past the opening over the distance separating the two, this usually is not problematic. Even then, however, placing endoluminal stents to either side of a T-branch also results in the presentation of four thrombogenic edges in positions of maximum nonlaminar flow and shear stress favorable to the formation of thrombi and lesions.

Furthermore, "evidence is emerging that the abrupt compliance mismatch that exists at the junction between the stent ends and the host arterial wall disturbs both the vascular hemodynamics and the natural wall stress distribution" (Berry, J. L., Manoach, E., Mekkaouri, C., Rolland, P. H., Moore, J. E., and Rachev, A. 2002. "Hemodynamics and Wall Mechanics of a Compliance Matching Stent: in Vitro and in Vivo Analysis," *Journal of Vascular and Interventional Radiology* 13(1):97-105; for the effect of shear stress on in-stent restenosis, see Wentzel, J. J., Krams, R., Schuurbiers, J. C. H.; Oomen, J. A. Kloet, J., van der Giessen, W. J., Serruys, P. W., and Slager, C. J., 2001. "Relationship between Neointimal Thickness and Shear Stress after Wallstent Implantation in Human Coronary Arteries," *Circulation* 103(13):1740-1745 and Sanmartin, M., Goicolea, J., Garcia, C., Garcia, J., Crespo, A., Rodriguez, J., and Goicolea, J. M. 2006. "Influencia de la tensión de cizallamiento en la reestenosis intra-stent: estudio in vivo con reconstrucción 3D y dinámica de fluidos computacional," [Influence of Shear Stress on in-Stent Restenosis: in Vivo Study Using 3D Reconstruction and Computational Fluid Dynamics]," *Revista española de cardiología* (Spanish Journal of Cardiology) 59(1):20-27, in Spanish with abstract in English at Pubmed).

Arteries that support a pronounced pulse are stated to adapt to forced distention over time (see, for example, Dirsch, O., Dahmen, U., Fan, L. M., Gu, Y. L., Shen, K., Wieneke, H., and Erbel, R. 2004. "Media Remodeling—The Result of Stent Induced Media Necrosis and Repair," *Vasa* 33(3):125-129); however, this is but one of several abnormal conditions imposed by an endoluminal stent. Endoluminal stents are incapable of treating the radial asymmetries or eccentricities characteristic of angiosclerotic lesions discriminately, instead covering over unaffected portions entirely about the arterial wall. A distinct irritant, endoluminal stents in the vascular tree not only stimulate intimal hyperplasia leading to restenosis, but accelerate atherosclerosis, and can result in ischematizing intramedial protrusion sometimes leading to erosions, fistulization, or fistulation, responsive to the chronic irritation of physiologically active tissue or infection, and interference with normal intrinsic (vasotonic and pulsatile) motility.

An extraluminal stent is not susceptible to adhesion of luminal contents, clogging, tumor ingrowth whether during adjuvant therapy, or erosion, ulceration, perforation, or fistulatization of the substrate (encircled, underlying) ductus, for example, with or without infection, and is not capable of " . . . compressive action of the stent into the mediastinum leading to more disease invasion and metastatic spread in addition to more difficult resection . . . ." (Griffiths, E. A. and Powell, S. L. 2012. "Comment Re Gastric Ulceration Following Oesophageal Stent Migration [Markar et al. 2012 cited below] Interactive Cardiovascular Thoracic Surgery 15(2):322; van Hooft, J. E., Bemelman, W. A., Oldenburg, B., Marinelli, A. W., Holzik, M. F., and 4 others 2011. "Colonic Stenting Versus Emergency Surgery for Acute Left-sided Malignant Colonic Obstruction: A Multicentre Randomised Trial," Lancet Oncology 12(4): 344-352). Griffiths and Powell wrote to dissuade the use of stents in the digestive tract entirely.

Metastasis is more effectively averted when stays, which avoid the lumen altogether, are used as the intravascular component. Neither might the intravascular component of an extraluminal stent (miniballs or stays) migrate, and proper securing of the stent-jacket precludes its migration. Where clearance is slight, the jacket is minimized in thickness to avert encroachment upon or abrasion of adjacent tissue. Endoluminal stents in the trachea or esophagus interfere with normal function inside and within (through) the lumen wall in every way. The literature seldom limited to a single complication, a categorization is at best based upon relative stress.

Endoluminal stents in the gastrointestinal tract that must be left in place over an extended rather than a brief interval (see, for example, van Boeckel, P. G., Dua, K. S., Weusten, B. L., Schmits, R. J., Surapaneni, N., Timmer, R., Vleggaar, F. P., and Siersema, P. D. 2012. "Fully Covered Self-expandable Metal Stents (SEMS), Partially Covered SEMS and Self-expandable Plastic Stents for the Treatment of Benign Esophageal Ruptures and Anastomotic Leaks," BMC [BioMed Central (London)] Gastroenterology 12:19; van Boeckel, P. G., Sijbring, A., Vleggaar, F. P., and Siersema, P. D. 2011. "Systematic Review: Temporary Stent Placement for Benign Rupture or Anastomotic Leak of the Oesophagus," Alimentary Pharmacology and Therapeutics 33(12): 1292-1301; Langer, F. B., Schoppmann, S. F., Prager, G., Tomaselli, F., Pluschnig, U., Hejna, M., Schmid, R., and Zacherl, J. 2010. "Temporary Placement of Self-expanding Oesophageal Stents as Bridging for Neo-adjuvant Therapy," Annals of Surgical Oncology 17(2):470-475; Small, A. J., Coelho-Prabhu, N., and Baron, T. H. 2010. "Endoscopic Placement of Self-expandable Metal Stents for Malignant Colonic Obstruction: Long-term Outcomes and Complication Factors," Gastrointestinal Endoscopy 71(3):560-572) risk numerous complications directly attributable to occupancy within the lumen that an extraluminal stent avoids (see, for example, Park, S., Shin, S. J., Ahn, J. B., Jeung, H-C., and 3 others 2009. "Benefits of Recurrent Colonic Stent Insertion in a Patient with Advanced Gastric Cancer with Carcinomatosis Causing Colonic Obstruction," Yonsei Medical Journal 50(2): 296-299; Soto, S., López-Rosés, L., González-Ramírez, A., Lancho, A., Santos, A., and Olivencia, P. 2006. "Endoscopic Treatment of Acute Colorectal Obstruction with Self-expandable Metallic Stents: Experience in a Community Hospital," Surgical Endoscopy 20(7): 1072-1076; Homs, M. Y., Steyerberg, E. W., Kuipers, E. J., van der Gaast, A., Haringsma, J., van Blankenstein, M., and Siersema, P. D. 2004. "Causes and Treatment of Recurrent Dysphagia after Self-expanding Metal Stent Placement for Palliation of Esophageal Carcinoma," Endoscopy 36(10): 880-886; Cheng, Y. S., Li, M. H., Chen, W. X., Chen, N. W., Zhuang, Q. X., and Shang, K. Z. 2004. "Complications of Stent Placement for Benign Stricture of Gastrointestinal Tract," World Journal of Gastroenterology 10(2):284-286; Patel, S., Patwardhan, R. and Levey, J. 2003. "Endoscopic Stenting: An Overview of Potential Complications," Practical Gastroenterology 27(6):44-54; Singh, S. and Gagneja, H. K. 2002. "Stents in the Small Intestine," Current Gastroenterology Reports 4(5):383-391; Christie, N. A., Buenaventura, P. O., Fernando, H. C., Nguyen, N. T., Weigel, T. L., Ferson, P. F., and Luketich, J. D. 2001. "Results of Expandable Metal Stents for Malignant Esophageal Obstruction in 100 Patients: Short-term and Long-term Follow-up," Annals of Thoracic Surgery 71(6):1797-1802), to include:

a. Migration (dislocation, displacement) (see, for example, Macdonald, A. J., Drummond, R. J., and Wright, D. M. 2007. "Migration of a Metal Esophageal Stent Presenting as Obstruction at the Ileocecal Valve 2 Years Postinsertion," Endoscopy 39 Supplement 1:E190; Maetani, I., Isayama, H., and Mizumoto, Y. 2007. "Palliation in Patients with Malignant Gastric Outlet Obstruction with a Newly Designed Enteral Stent: A Multicenter Study," Gastrointestinal Endoscopy 66(2):355-360; Ho, H. S. and Ong, H. S. 2004. "A Rare Life-threatening Complication of Migrated Nitinol Self-expanding Metallic Stent (Ultraflex)," Surgical Endoscopy 18(2):347; Di Fiore, F., Lecleire, S., Antonietti, M., Savoye, G., and Savoye-Collet C, and 4 others 2003. "Spontaneous Passage of a Dislocated Esophageal Metal Stent: Report of Two Cases," Endoscopy 35:(3)223-225; De Palma G D, Iovino P, and Catanzano C. 2001. "Distally Migrated Esophageal Self-expanding Metal Stents: Wait and See or Remove? Gastrointestinal Endoscopy 53:(1)96-98).

b. Migration of a primary gastrointestinal or enteral stent (one originally placed in rather than migrating into the digestive tract) resulting in perforation (see, for example, Morikawa, S., Suzuki, A., Nakase, K., and Yasuda, K. 2012. "Palliation of Malignant Upper Gastrointestinal Obstruction with Self-expandable Metal Stent," Korean Journal of Radiology 13 Supplement 1:S98-103; Havemann, M. C., Adamsen, S., and Wøjdemann, M. 2009. "Malignant Gastric Outlet Obstruction Managed by Endoscopic Stenting: A Prospective Single-centre Study," Scandinavian Journal of Gastroenterology 44(2):248-251; Mosler, P., Mergener, K. D., Brandabur, J. J., Schembre, D. B., and Kozarek, R. A. 2005. "Palliation of Gastric Outlet Obstruction and Proximal Small Bowel Obstruction with Self-expandable Metal Stents: A Single Center Series," Journal of Clinical Gastroenterology 39(2):124-128; Thumbe, V. K., Houghton, A. D., and Smith, M. S. 2000. "Duodenal Perforation by a Wallstent," Endoscopy 32(6):495-497; von Schönfeld, J. 2000. "Endoscopic Retrieval of a Broken and Migrated Esophageal Metal Stent," Zeitschrift für Gastroenterologie 38(9): 795-798). Duodenal perforation by migration of a biliary stent is addressed below.

c. Migration resulting in fistulization (Melendez, J., Chu, D., Bakaeen, F. G., and Casal, R. F. 2011. "Tracheoesophageal Fistula Due to Migration of a Self-expanding Esophageal Stent Successfully Treated with a Silicone "Y" Tracheobronchial Stent," Journal of Thoracic and Cardiovascular Surgery 141(6):e43-e44; Furlong, H., Nasr, A., and Walsh, T. N. 2009. "Gastropleural Fistula: A Complication of Esophageal Self-expanding Metallic Stent Migration," *Endoscopy* 41 Supplement 2:E38-E39).

d. Migration resulting in ulceration (Markar, S. R., Ross, A., and Low, D. E. 2012. "Gastric Ulceration Following Oesophageal Stent Migration Complicating Surgical Management of Oesophageal Cancer," *Interactive Cardiovascular and Thoracic Surgery* 15(2):320-322; Rao, K. V., Beri, G. D., and Wang, W. W. 2010. "Trimming of a Migrated Metal Stent for Malignant Colonic Stricture Using Argon Plasma Coagulation," *World Journal of Gastrointestinal Endoscopy* 2(2):75-76; Molina-Infante, J., Mateos-Rodriguez, J. M., Fernandez-Bermejo, M., Perez-Gallardo, B., and Hernandez-Alonso, M. 2010. "Endoscopic Trimming of an Embedded Distally Migrated Metallic Rectal Stent with Argon Plasma Coagulation," *Surgical Laparoscopy, Endoscopy and Percutaneous Techniques* 20(2):e73-e75).

e. Direct (in place, at the location where originally implanted, nonmigratory) perforation (Dittmar, Y., Rauchfuss, F., Schmidt, C., and Settmacher, U. 2011. "Abdominothorakale Ösophagusresektion wegen Ösophagusstentperforation bei metastasiertem Magenkarzinomrezidiv im Stadium der kompletten Remission—eine Kasuistik," [Palliative Abdominothoracic Resection for Stent-induced Perforation of the Oesophagus in a Patient with Recurrent Metastatic Gastric Cancer with Complete Remission—A Case Report] *Zentralblatt für Chirurgie* 6 April ISSN 1438-9592; Jung, G. S., Park, S. D., and Cho, Y. D. 2008. "Stent-induced Esophageal Perforation: Treatment by Means of Placing a Second Stent after Removal of the Original Stent," *Cardiovascular and Interventional Radiology* 31(3):663-668; Ely, C. A. and Arregui, M. E. 2003. "The Use of Enteral Stents in Colonic and Gastric Outlet Obstruction," *Surgical Endoscopy* 17(1):89-94; Christie et al. 2001 op cit.).

f. Direct fistulization (Guarner-Argente, C., Chandrasekhara, V., Levine, M. S., Marcotte, P. J., Weinstein, G. S., and Ginsberg, G. G. 2011. "Esophageal Stent-induced Fistulization to an Anterior Cervical Plate," Gastrointestinal Endoscopy 74(1):219-221; Han, Y., Liu, K., Li, X., Wang, X., Zhou, Y., and 6 others 2009. "Repair of Massive Stent-induced Tracheoesophageal Fistula," *Journal of Thoracic and Cardiovascular Surgery* 137(4): 813-817; Schowengerdt, C. G. 1999. "Tracheoesophageal Fistula Caused by a Self-expanding Esophageal Stent," *Annals of Thorac Surgery* 67(3):830-831).

g. Direct ulceration (Wei, W., Ramaswamy, A., de la Torre, R., and Miedema, B. W. 2012. "Partially Covered Esophageal Stents Cause Bowel Injury when Used to Treat Complications of Bariatric Surgery," Surgical Endoscopy 27 June [e-publication ahead of print]; Wai, C. T., Khor, C., Lim, S. E., and Ho, K. Y. 2005. "Post-metallic Stent Placement Bleeding Caused by Stent-induced Ulcers," *World Journal of Gastroenterology* 11(36):5739-5741).

h. Tumor ingrowth that can make removal of the stent impossible without much dissection (Griffiths, E. A. and Powell, S. L. 2012 op cit.] *Interactive Cardiovascular Thoracic Surgery* 15(2):322; Lopera, J. E. and de Gregorio, M. A. 2010. "Fluoroscopic Management of Complications after Colorectal Stent Placement," *Gut and Liver* 4(Supplement 1):59-518; Kang, S-G., Jung, G. S., Cho, S. G., Kim, J. G., Oh, J. H., Song, H. Y., and Kim, E. S. 2002. "The Efficacy of Metallic Stent Placement in the Treatment of Colorectal Obstruction," *Korean Journal of Radiology* 3(2): 79-86; Scheider, D. M., Siemens, M., Cirocco, M., Haber, G. B., Kandel, G., Kortan, P., and Marcon, N. E. 1997. "Photodynamic Therapy for the Treatment of Tumor Ingrowth in Expandable Esophageal Stents," *Endoscopy* 29(4):271-274).

i. The accumulation of detritus and clogging or impaction (see, for example, Loffeld, R. J. L. F. and Dekkers, P. E. P. 2012. "Palliative Stenting of the Digestive Tract: A Case Series of a Single Centre." *Journal of Gastrointestinal Oncology* August [available at http://www.thejgo.org/article/view/497]; de Gregorio, M. A., Laborda, A., Tejero, E., Miguelena, J. M., Carnevale, F. C., and 4 others 2011. "Ten-year Retrospective Study of Treatment of Malignant Colonic Obstructions with Self-expandable Stents," *Journal of Vascular and Interventional Radiology* 22(6):870-878; de Gregorio, M. A., Mainar, A., Rodriguez, J., Alfonso, E. R., and 4 others 2004. "Colon Stenting: A Review," *Seminars in Interventional Radiology* 21(3):205-216).

Endoluminal biliary stents require to be changed every 3 to 6 months and bring complications to include those associated with primary enteral stents (see, for example, Kida, M., Miyazawa, S., Iwai, T., Ikeda, H., Takezawa, M., and 4 others 2011. "Endoscopic Management of Malignant Biliary Obstruction by Means of Covered Metallic Stents: Primary Stent Placement Vs. Re-intervention," *Endoscopy* 43(12):1039-1044; Brinkley, M., Wible, B. C., Hong, K., and Georgiades, C. 2009. "Colonic Perforation by a Percutaneously Displaced Biliary Stent: Report of a Case and a Review of Current Practice," *Journal of Vascular and Interventional Radiology* 20(5):680-683; Arhan, M., Odemiş, B., Parlak, E., Ertuğrul, I., and Başar, O. 2009. "Migration of Biliary Plastic Stents: Experience of a Tertiary Center," *Surgical Endoscopy* 23(4):769-775; Lee, T. H, Park, D. H., Park, J. Y., Lee, S. H., Chung, I. K., Kim, H. S., Park, S. H., and Kim, S. J. 2008. "Aortoduodenal Fistula and Aortic Aneurysm Secondary to Biliary Stent-induced Retroperitoneal Perforation," *World Journal of Gastroenterology* 14(19):3095-3097; Namdar, T., Raffel, A. M., Topp, S. A., Namdar, L. and 4 others 2007. "Complications and Treatment of Migrated Biliary Endoprostheses: A Review of the Literature," *World Journal of Gastroenterology* 13(40): 5397-5399; Suk, K. T., Kim, J. W., Kim, H. S., Baik, S. K., Oh, S. J., and 5 others 2007. "Human Application of a Metallic Stent Covered with a Paclitaxel-incorporated Membrane for Malignant Biliary Obstruction: Multicenter Pilot Study," *Gastrointestinal Endoscopy* 66(4):798-803; Paikos, D., Gatopoulou, A., Moschos, J., Soufleris, K., Tarpagos, A., and Katsos, I. 2006. "Migrated Biliary Stent Predisposing to Fatal ERCP-related Perforation of the Duodenum," *Journal of Gastrointestinal and Liver Diseases* 15(4):387-388; Matsushita, M., Takakuwa, H., Nishio, A., Kido, M., and Shimeno, N. 2003. "Open-biopsy-forceps Technique for Endoscopic Removal of Distally Migrated and Impacted Biliary Metallic Stents," *Gastrointestinal Endoscopy* 58(6):924-927; Galandi, D., Schwarzer, G., Bassler, D., and Allgaier, H. P. 2002. "Ursodeoxycholic Acid and/or Antibiotics for Prevention of Biliary Stent Occlusion," *Cochrane Database of Systematic Reviews* (3):CD003043; Yau, K. K., Tang, C. N., Chau, C. H., Siu, W. T., Fung, K. H., and Li, M. K. 2000. "Nonoperative Management of Biliary Stent-induced Duodenal Perforation," *Endoscopy* 32(8):S47; Yarze, J. C., Poulos, A. M., Fritz, H. P., and Herlihy, K. J. 1997. "Treatment of Metallic Biliary Stent-induced Duodenal Ulceration Using Endoscopic Laser Therapy," *Digestive Diseases and Sciences* 42(1):6-9).

Obstruction or perforation of the gut by a biliary stent that migrated is heavily reported in the literature (see, for example, Bharathi, R. S., Rao, P. P., and Ghosh, K. 2008. "Intra-peritoneal Duodenal Perforation Caused by Delayed Migration of Endobiliary Stent: A Case Report," *International Journal of Surgery* 6(6):478-480; Melita, G., Currò, G., Iapichino, G., Princiotta, S., and Cucinotta, E. 2005. "Duodenal Perforation Secondary to Biliary Stent Dislocation: A Case Report and Review of the Literature," *Chirurgia Italiana* 57(3):385-388). Attempts to devise an endoluminal biliary stent less susceptible to clogging (Raju, G. S., Sud, R., Elfert, A. A., Enaba, M., Kalloo, A., and Pasricha, P. J. 2006. "Biliary Drainage by Using Stents Without a Central Lumen: A Pilot Study," *Gastrointestinal Endoscopy* 63(2):317-320) appear to pose greater risk of incisions and perforations.

Side by side placement poses inordinate difficulty and risks (Lee, T. H., Park, D. H., Lee, S. S., Choi, H. J., Lee, J. K. and 5 others 2012. "Technical Feasibility and Revision Efficacy of the Sequential Deployment of Endoscopic Bilateral Side-by-Side Metal Stents for Malignant Hilar Biliary Strictures: A Multicenter Prospective Study," *Digestive Diseases and Sciences*, e-pub ahead of print August 2011). Stents with side holes has been tried and did not eliminate clogging (Coene, P. P., Groen, A. K., Cheng, J., Out, M. M., Tytgat, G. N., and Huibregtse, K. 1990. "Clogging of Biliary Endoprostheses: A New Perspective," *Gut* 31(8):913-917).

Notwithstanding, endoluminal stenting of the gastrointestinal tract to include the esophagus and small intestine is often effectively palliative for treating malignant stenosis (see, for example, Mergener, K. and Kozarek, R. A. 2002. "Stenting of the Gastrointestinal Tract," *Digestive Diseases* 20(2):173-181; Guo, J. H., Teng, G. J., Zhu, G. Y., He, S. C., Fang, W., Deng, G., and Li, G. Z. 2008. "Self-expandable Esophageal Stent Loaded with 125 I Seeds: Initial Experience in Patients with Advanced Esophageal Cancer," *Radiology* 247(2):574-581). However, no limitation to malignancies should be assumed even for metal stents (see, for example, Small, A. J., Young-Fadok, T. M., and Baron, T. H. 2008. "Expandable Metal Stent Placement for Benign Colorectal Obstruction: Outcomes for 23 Cases," *Surgical Endoscopy* 22(2):454-462; Evrard, S., Le Moine, O., Lazaraki, G., Dormann, A., El Nakadi, I., and Devière, J. 2004. "Self-expanding Plastic Stents for Benign Esophageal Lesions," *Gastrointestinal Endoscopy* 60(6):894-900; Dormann, A. J., Deppe, H., and Wigginghaus, B. 2001. "Self-expanding Metallic Stents for Continuous Dilatation of Benign Stenoses in Gastrointestinal Tract—First Results of Long-term Follow-up in Interim Stent Application in Pyloric and Colonic Obstructions," (in English) *Zeitschrift für Gastroenterologie* 39(11):957-960).

Whether due to primary deformity or pathological deterioration, protracted impairment in physiological function from immobilization over time further destroys normal structure and function in the lumen wall. Even though the smooth muscle has deteriorated or atrophied, a stent that complies in expansion and contraction without irritation assists to preserve what normal vascular physiology remains. The thrombogenic turbulent flow at its margins aggravated by the thrombophilic metal surface of every practical endoluminal stent from the moment of placement poses the risk of thrombosis as long as the stent remains, which almost always, is to the end of life (see for example, Manjappa, N., Agarwal, A., and Cavusoglu, E. 2006. "Very Late Bare-metal Stent Thrombosis. A Case Report and Review of the Literature," *Journal of Invasive Cardiology* 18(7): E203-E206).

An endoluminal stent thus requires antithrombotic (antithrombogenic) medication in addition to the statin that would be necessary to control the dyslipidemic (hypercholesterolemic) etiological condition in any event. An extraluminal stent allows dispensing with the lifelong administration of antithrombotic medication and the bleeding problems to which this can predispose. Furthermore, magnetic drug targeting makes it possible to limit exposure to the statin to localized segments. For a younger patient, this allows the myopathic effect associated with long term use of a statin to be avoided. In addition to disrupting endothelial function, endoluminal stents conflict with autonomic (vasotonic angiotonic) adjustment in lumen diameter to adjust the blood pressure (arterial tension) by direct mechanical interference.

Compliance in caliber is indissociable from changes in the pulse. The presence of an endoluminal stent can interfere with the re-treatment that will most often be due to the etiology, which no stent, even one drug-eluting or radiation-emitting, can ordinarily more than palliate, and the stent may itself have aggravated if not precipitated the condition. Retrieval, however, usually bodes significant trauma. Thousands of references on file at the U.S. National Library of Medicine document the fracture, fragmentation, migration, clogging, and susceptibility to act as a scaffold for the deposition of constituents out of the passing fluid of an endoluminal stent of any kind in any kind of ductus. In producing these consequences, endoluminal stents introduce mechanical as well as physiological complications that often precipitate the need for a second procedure, sometimes involving open surgery, to effect their removal.

8b. The Extraluminal Stent

An extraluminal stent consists of an intravascular component, which is multiple, and a singular extravascular component that mantles about or ensheaths the intravascular component. The intravascular component consists of stays or miniballs. The extravascular component, or stent-jacket, is used to maintain the stenosed or collapsed ductus at its normal quiescent caliber without interfering with its normal expansion and contraction. If stenosed as plaque laden, an angioplasty is normally performed so that the lumen will be adequate. Nonvascular ductus are analogously rid of obstructive matter or tissue through ablation. The magnetic function is directed inward, or adaxially, using the axially directed poles of the permanent magnets about the jacket, with the jacket itself limiting expansion to the extent normal.

The radially outward attractive field generated by a stent-jacket are seldom used, and then with the aid of ferromagnetic implants placed in the tissue to be pulled at, whether to pull either the other structure or the encircled or substrate ductus itself aside when one or the other follows a course correctible thus or encroaches on adjacent tissue, for example. Only tissue to be acted upon as positioned along the magnetic path or circuit, not an encircled ductus used as a magnet mounting platform to pull or be pulled, need have ferromagnetic implants. That by incorporating nonmagnetized bars, pellets, disks, or if quasi-intrinsic, an embedded particulate, stent-jackets and magnet-wraps which use the substrate ductus only as a mounting platform can serve as the attracted rather than the attracting component, is obvious. Attraction is then in the direction set by the magnetized magnet-wrap, patch-magnet, or stent-jacket used to attract the nonmagnetically mantled ductus.

A stent-jacket placed about a nearby vessel or duct can also be used, for example, to concentrate drug carrier particles in an organ or a certain area within that organ. Radially outward function in larger vessels and ducts is accomplished with the aid of a discrete magnet stent-jacket, or if more distant, then a magnet-wrap, which is essentially a stent-jacket that has been modified to incorporate larger discrete magnets. When the mounting platform for effecting distant retraction or drug targeting is not tubular, patch-magnets are used. In order to encircle (girdle, mantle, jacket, or grasp about) a tubular structure or ductus of which the deep side would best be left attached, the side-slit of the base-tube is expanded into a side-slot wide enough to clear (straddle) the attachment.

A side-slot constitutes an enlarged side-slit or longitudinal expansion gap that is usually but not always situated at the deep side. Such a stent-jacket with a longitudinal strip removed is a partial stent-jacket. Unlike an endoluminal stent, the extraluminal stent need not impose sufficient radially outward force at the margins to prevent dislodgement (migration). Small branches at the slit can be accommodated either with a cutout at the slit or by expanding the slit into a slot, that is, extending the cutout sideways out to the ends. Cutouts to clear larger branches and expansion inserts to clear a swollen ductus apply equally to full and partial stent-jackets. By contrast, existing endoluminal stents are continuous in structure and unable to retain structural integrity when a void must be introduced to span a branch, for example.

Complementary thereto, in placing an intravascular component consisting of miniballs, a void is accommodated by temporarily replacing a rotary magazine clip feeding multiple radially directed barrel-tubes in the airgun chamber with one that blanks out the barrel-tubes directed toward the void of the ostium (the opening into the branch). While the angle separating the exit-ports about the muzzle-head is not variable, the exit-ports that discharge at a given time is instantly changeable. For a given arrangement of exit-ports, blanking out the hole in the rotary clip for loading the miniballs for each to exit through its corresponding barrel-tube allows each barrel-tube to be fed or left unfed per discharge on discharge by discharge discretionary basis.

This allows changing the discharge pattern as to arcuate distribution at any moment such as to target or to avoid an eccentric lesion or ostium, for example. Significantly, it does this without the need to withdraw one radial discharge barrel-assembly and replace it with another. A barrel-assembly is generally made to a certain gauge, any additional features provided to allow use in the vascular tree. Barrel-assembly versatility means sufficiency that eliminates the need for withdrawal and reentry, which expedites completion of a procedure, significantly reduces the risks of hematoma and infection at the entry wound, and materially reduces the number of different Barrel-assemblies which must be produced or purchased. Stays are similarly placed to avoid the blanked out area.

In treating eccentric lesions, note is taken of the positions of the lesions throughout the course of the vascular system to be treated and the choice of a fully radially discharging muzzle assembly with occasional blanked out rotary magazine clips or partially radially discharging muzzle assembly with exit ports at a different, usually smaller angle, made on this basis. Minimizing the duration of the procedure and any further trauma to the usually inguinal or brachial point of entry, the choice is based upon avoiding the need to withdraw one barrel-assembly and replace it with another. To keep the size and mass of the stent-jacket to a minimum as least to encroach upon or rub against adjacent tissue, the magnets should be as diminutive as possible consistent with the magnetic force required.

To this end, small sintered neodymium iron boron ($Nd_2Fe_{14}B$) permanent bar magnets of megagauss oersted (MGO) 50 or higher grade material are used. The magnets are magnetized parallel to their thickness, or normal to their plane; that is, the lines of force run radial in relation to the long axis of the ductus to be treated. Readily corroded, neodymium iron boron magnets are often available already nickel plated in a length that spans the implanted miniballs lengthwise, or running parallel to the axis of the tubing. However, commercially available neodymium magnets are not made in the tiny sizes required, and neither neodymium iron boron nor nickel is biocompatible (see International Standards Organization standard series 10993, *Biological Evaluation of Medical Devices*.

Bioinertness is attained by overlayment or encapsulation of the bar magnets in gold, tantalum, titanium, or any of the large number of nondegrading bioinert plastic polymer resins. The use of other noble metals, such as platinum, rhodium, and alloys of platinum and rhodium are needlessly expensive. The magnets are drilled through toward each of their ends or perimeters prior to being coated or encapsulated for bioinertness, then fastened to the base-tube with rivets or eyelets. Since placing the stent-jacket about the ductus with the insertion tool to be described may necessitate the application of lateral force to the sides the magnets with end of a probe, and the magnets must not come loose during application or at any time thereafter, wider flange rivets or eyelets are used.

Tantalum coating the magnets enhances radiopacity making radiological visualization and if necessary, retrieval, easier. The cylindrical base-tube is relatively stiff lengthwise, but unless too thick, long, or made of stiffer material, flexible circumferentially about the side-slit as to comply with the pulse. Within the constraints imposed by the need to generate sufficient field strength, this isolates longer magnets from flexing forces, allowing the use of magnets that are thin for clearance and to avoid encroachment upon neighboring tissue. Otherwise, the brittleness of sintered neodymium iron boron, even when nickel plated and encapsulated for bioinertness in gold plate further sputter coated or microfused would allow thin magnets to quickly fail.

The lack of sufficient strength is more pronounced for gross movement at points of flexion where the material and dimensions do not add sufficient ultimate strength or resistance to breaking stress for the bending load. Resistance to magnet fracture and longitudinal flexibility without resistance to bending by a long base-tube that spans a point of flexion is obtained by segmenting the stent-jacket, as addressed below in the section entitled Sectional, or Chain-stents, Segmented and Articulated. However, whether preaneurysmally, where disease has weakened the arterial wall, longitudinal segmentation of the magnets on an especially flexible continuous and longer base-tube can offer compliance with the pulse while jacketing about the vessel to prevent its rupture.

Compliance with the pulse or smooth muscle action is obtained through the use of suitable stent-jacket base-tube materials, which may be coextruded or as addressed below in the section entitled Laminated Stent-jackets, laminated (layered), varying the relative thicknesses of the layers, and if necessary, using shorter bar magnets or segmented stent-jackets. If necessary, the magnets can be strengthened by using thicker and/or stronger encapsulation materials of gold, tantalum, titanium, and a bioinert plastic polymer resin, alone or in combination posing a spectrum of choices. Endoluminal stents cannot be used to reduce the risk of rupture and are noncompliant with intrinsic movement.

8b(1). The Intraductal Component of the Extraluminal Stent and the Means for its Insertion 8b(1)(a). Types of Ductus-Intramural Implants Used for Stenting The intraductal component of a magnetic extraluminal stent consists of an array of miniballs or stays containing sufficient magnetically susceptible material, typically ferromagnetic, to maintain the lumen in a patent condition. Stenting miniballs and stays can include drugs, other therapeutic substances, bonding agents, or a radiation-emitting seed.

8b(1)(b). Use of Ductus-Intramural Implants for Stenting

Miniballs are implanted with a barrel-assembly, stays with a stay insertion tool. Ductus-intramural implants and implantation for stenting are no different than when stenting is uninvolved, the differences pertaining to higher ferromagnetic content and the additional need to place a stent-jacket. Stays used to attract a drug carrier particulate must also contain more ferromagnetic content, which must be magnetized. For stenting, miniballs are attracted, not attracting. Stays, however, which asymmetrical, pose no problem of magnetic orientation, can attract a ferrous stent-jacket, but unless also used to attract a drug carrier particulate, are constituted as would miniballs.

Each type apparatus is variously configurable for different purposes, as addressed below in sections on each type apparatus. When the lumen wall is weakened, wide stays coated with cyanoacrylate cement when ejected from the stay insertion tool are used. Either type implant can include medication, any of numerous other therapeutic substances, and/or incorporate a radionuclide with or without radiation shielding. Stays highly magnetized radially in relation to the long axis of the ductus can also be used to draw magnetically susceptible drug carrier nanoparticles from the passing contents, the ductus usually an artery and the contents blood. Miniballs are not used thus due to the need to orient these with an external electromagnet, risking extraction.

If the stays emit radiation, then the surrounding tissue and nanoparticles can be irradiated upon arriving in the target lesion. The density, or number of implants per unit area of the wall, is proportional to the reduction in wall strength and coordinated with the extraluminal component to avoid the concentration of tractive force on any one stay. A ductus too weak to be stented in this way is probably too weak to be stented in any way, and should be replaced with a graft. When the outer layer of a ductus lacks sufficient strength to sustain the tractive force needed to maintain patency, a ferromagnetic wrap-surround is engaged by means of ferromagnetic stainless steel or superparamagnetic magnetite or maghemite nanoparticles or finely grained powder impregnated plastic prongs (anchors, clasps) into the tunica media to provide a prosthetic adventitia.

Implantation at body temperature of medicated miniballs with a thermal or cryogenic ablation or ablation and angioplasty-capable barrel-assembly makes implantation followup measures immediately available without the need for withdrawal and reentry. Whether following a thermal or cryogenic ablation or angioplasty, thermal or cryogenic use of the same barrel-assembly can be used to initiate the release of medication or time-release medication from implanted miniballs, to accelerate the dissolution of either by melting or contraction fracture of a miniball coating, or by the use of heat to accelerate the dissolution of the implant through the hydrolysis of ester bonds, for example.

The same processes are applicable to stays and stent-jacket expansion inserts as addressed below in the section entitled Expansion Inserts Absorbable, Meltable, and Comminutable for Time-discrete Decremental Contraction of Stent-Jackets. These various implants can be not only irradiative and/or coated with medication, but incorporate agents to control their dissolution, which agents can also liberate medication. Stays and miniballs to serve as irradiating seeds need not contain ferromagnetic material as is necessary for use with a stent-jacket. However, the inclusion of ferrous material such as superparamagnetic magnetite or maghemite nanoparticles or finely grained powder in seeds makes it possible to recover the seeds after any interval with the aid of a magnet stronger than those placed about stent-jackets.

From the standpoint of timing, miniballs and stays that incorporate ferrous material can be placed for use as seeds, and once depleted of radiation, whereupon the neoplasm should have subsided, can be used as the intraductal components of a stent-jacket. Conventional seeds imaged ultrasonographically or by means of computed tomography, seed-stays not conventionally marked or coated for radiopacity can be encapsulated with a layer that includes a gamma emitting isotope for gamma camera viewing. Within the size constraints, stays can be encapsulated with medicine. Miniballs of like purpose can be of like composition as stays.

The use of the methods and apparatus described herein to implant spherules that consist solely of medication and/or serve as a substrate for the emission of radiation from a highly localized site within the wall of a tubular anatomical structure, for example, are addressed above in the section entitled Drug-releasing and Irradiating Ductus-intramural Implants and below in the sections entitled Radiation-emitting (Brachytherapeutic, Endocurietherapeutic, Sealed source Radiotherapeutic, Internal Radiation Therapy) Miniballs and Medication Miniballs.

Any barrel-tube can be used to infix a medicated, multiple concentric medicated, and/or irradiating implant along the wall of a ductus thus causing the medication to be eluted or radiation to be emitted in a highly localized, discretionary manner, rather than circulated throughout the bloodstream. In the coronary arteries, most other vessels, and other type narrow gauge ductus, the transluminal advancement of a multibarrel radial discharge barrel-assembly by means of an automatic positional control system, as will be described, allows a higher density and uniform spacing between adjacent miniballs than might be achieved with direct manual control.

A uniform distribution of millimetric or smaller miniballs draws the diseased or weakened wall of the ductus more as a sheet, minimizing the concentration of tractive force on certain miniballs, and thus reduces for any of these to be pulled entirely through the adventitia, referred to as pull-through, or avulse the abaxial tunic or tunics, referred to as delamination. Failure by pull-through or delamination of a threshold proportion of miniballs produces stent failure (breakdown, loss of retraction). High density ductus-intramural implantation also allows placement within the same area of a larger number, hence greater diversity of miniballs to allow a larger amount or variety of medication and/or other therapeutic substances.

Miniballs can be formulated to spontaneously release medication known to be effective or to become released and physiologically activated only in response to external control on an as needed basis through direct or induction heating or the ingestion, injection, or infusion of another substance as appropriate, these various methods of attack delineated in sections of appropriate title. Since it better resists pull-through, the use of a larger number of miniballs to cover the same area is less susceptible to deterioration of the stent and the patency the stent will continue to provide. When apposite, a thermal angioplasty performed after discharge can be used to flow a solid protein solder outer shell applied to miniballs with an undercut-textured surface.

Protein solder or any other bonding agent used in the body will eventually be dissipated and lose all bonding value; however, through the infiltration and replacement of the solder by tissue that fills the fissures or channels at the surface, the miniballs become integrated into the tissue. When the condition permits, this process is allowed to be completed before the stent-jacket is applied. By allowing successive discharges to be made quickly and accurately, the use of a positional control system allows the use of a barrel-assembly having the largest number of barrel-tubes that the diameters of the miniballs and ductus to be implanted will allow. With the possible exception of off-pump warm treatment in the coronary or carotid arteries, the resulting reduction in procedural time is considerable and should allow operation under conditions of brief if substantial occlusion.

Since the miniball implants are encapsulated for bioinertness and small (typically 0.4-1.0 millimeter in a ureter or artery, for example), a perforation is quickly and spontaneously sealed; unless septic contents are released, the loss of a miniball into the surrounding body cavity, for example, will have little significance. Also militating against pull-through in an artery is the fitting of the stent-jacket for the diastoles or as little more distended than any post ablation, angioplasty or atherectomy residual narrowing of the lumen will allow. In the gastrointestinal tract, the release of cell contents along the trajectory of the miniball contributes tack that congeals and is gradually replaced so that the miniball is left integrated into healthy tissue.

One or more barrels, or barrel-tubes, housed within an gas embolism-averting gas pressure equalizing enclosure, or barrel-catheter, discharge forward and radially through a distal muzzle-probe or muzzle-head. The leading, or distal, component through which the spherules are discharged, or muzzle-head, is usually placed in flush or slightly less than flush relation to the wall of an arterial lumen (channel, passageway), the passing pulse expands the vessel about the muzzle-head. The muzzle-head also has grooves to allow blood to pass, albeit with some impedance and shear stress compared to the unobstructed condition.

However, the procedure is completed too quickly to allow shear much less stretching injury, especially when discharge is semiautomatic. Multiple discharge capability and the application of a positional control system also serve to minimize procedural time. When the muzzle-head is of the kind that delivers a plurality of spherule implants each in a different direction with each discharge, eccentricity of the muzzle-head within the lumen on passage of the pulse has little effect upon the spherule impact force. In most instances, the density of implants will also compensate for minor differences in the aiming point that results from excursion of the lumen wall about the muzzle-head.

8b(2). The Extraductal Component of the Extraluminal Stent and the Means for its Insertion 8b(2)(a). Types of Stent-Jacket So that the operator or a technician can adapt standardized stent- and perforation shield-jackets to the conditions encountered, these are generally supplied without expansion inserts or straight-line and double-wedge linings inserted. Expansion inserts to be bonded along one or both edges of the side-slit or side-slot and lap over a length of the outer surface for bonding without encroaching upon the lining along the inner surface are likewise supplied separately for preprocedural selection as appropriate. Unless used other than to prevent a perforation from striking neighboring tissue, such as to provide warming by neat induction at a later date, shield-jackets are placed only midprocedurally, so that an expansion insert is not pertinent to this type jacket. The incorporation of silicon-iron crystal into implants to be magnetically susceptible affords reduction in the mass and space taken up by both the attracting jacket or its bar magnets or electromagnets and the attracted implant and is therefore taken advantage of to the extent possible.

Nonmagnetic shield-jackets and magnetic stent-jackets must incorporate a side slit or slotted elastic sheath, a component to exert magnetic force over the surface of the sheath, and a moisture barrier-coated viscoelastic polyurethane foam lining, the latter perforated in alignment but not encapsulated with the others and left out of consideration as to whether a stent-jacket is categorized as laminated. Provided the ductus will not be adversely affected by denial of exposure to the chemical milieu, any stent-jacket can have a radiation shield added by lamination. When the period for shielding is limited, even a shielded jacket can be made to absorbed, either spontaneously or by dissolution on demand, as addressed below. The layers less moisture barrier-coated viscoelastic polyurethane foam lining are usually encapsulated within a chemically isolating and cushioning coating of a plastisol-like or rubbery polymer or copolymer.

For a single layer to provide both the sheath and magnetism, it must be intrinsically or quasi-intrinsically magnetized. To the extent that a magnet-wrap, or magnet-jacket, addressed below in the section entitled Magnet-wraps, is used to direct tractive force radially inward toward the long axis of the lumen (adaxially, axipetally, centripetally), it is a kind of stent-jacket, addressed above in the section entitled Concept of the Extraluminal Stent and below in the section entitled Stent-jackets and Stent-jacket Supporting Elements, or impasse-jacket, as addressed below in the sections entitled Concept of the Impasse-jacket and Miniball and Ferrofluid-borne Particle-impassable Jackets, or Impasse-jackets.

Abaxial or centrifugal traction, that is, toward a periductal sheath-mounted magnet, from the long axis of the lumen and jacket, as opposed to adaxial or centripetal traction toward the magnet and axis from the surrounding area is relegated to magnet-wraps and seldom other than an inherent byproduct of using a stent- or impasse-jacket. Stent- and impasse-jackets differ from magnet-wraps in having a backing that is more resilient, slit or slotted to allow the expansion and contraction of the encircled or substrate ductus, and usually, in magnetization entirely about the circumference. The intentional use of a magnet-wrap, impasse-jacket, or stent-jacket for the tractive force at both adaxial and abaxial poles is practicable but exceptional, the use of a stent- or impasse-jacket for its adaxial attraction even more so.

A stent-jacket must maintain luminal patency without contact between, significant stress to, or deformation of the internal (endothelial) surface of the lumen. If to remain in use temporarily, as during healing, the stent-jacket is not retrieved invasively but absorbed. Absorbable stent-jackets are addressed below in the section entitled Absorbable Base-tube and Stent-jacket, Miniball, Stay, and Clasp-magnet Matrix Materials. If the period for the need of a stent is known not to be permanent but broadly indeterminable, then the stent-jacket is chemically formulated to dissolve noninvasively on demand, as addressed below in the section entitled Noninvasive Dissolution on Demand of Absorbable Stent-jackets Base-tubes and Radiation Shields.

When an intrinsically or quasi-intrinsically magnetized stent-jacket or a radiation shield is bonded to a polymeric base-tube to produce an extrinsically magnetized stent-jacket, the whole is a laminated stent-jacket, addressed below. A shielded stent-jacket can also be made absorbable, but the 'breathing' perforations of the underlying stent layer will be closed over. This reduction in exposed surface lengthens the spontaneous absorption time, further prompting means for directing dissolution from outside the body. The term 'stent-jacket' denotes a device that incorporates all of the properties essential in the extravascular component of an extraluminal stent. When added for magnetization such a layer may not be suitable for use alone as an intrinsically or quasi-intrinsically magnetized stent-jacket as lacking resilience.

An intrinsically or quasi-intrinsically magnetized layer in an extrinsically magnetized stent-jacket is generally specialized for supplementary or complementary use and depends upon the base-tube layer for the nonmagnetic properties. Reciprocally, adding a layer to a self-sufficient stent-jacket will result in stiffness and/or a strength of magnetization as would risk pull-through. Even though it does not add to the magnetic strength and can be made pliant, the addition of a radiation shield must take this into account. By contrast, a stand-alone single-layer intrinsically or quasi-intrinsically magnetized stent-jacket provides all of the properties required. Devised for different treatment sites, the need to laminate an intrinsically or quasi-intrinsically magnetized stent-jacket for increased magnetic strength, resilience, or both, as by laminating two of the same or similar stent-jackets would be exceptional.

The addition of a radiation shielding layer is seldom required, and always produces a laminated base-tube mounting discrete magnets or a laminated stent-jacket. Stent-jackets suitable for radiation shielding are intrinsically, quasi-intrinsically, or lamination-magnetized, but not extrinsically magnetized. Others are extrinsically magnetized, one layer, the base-tube, an elastic sheath described as discretely magnetized when it mounts bar magnets about its outer surface and laminated, if it mounts an intrinsically or quasi-intrinsically magnetized layer. Discretely, intrinsically, and quasi-intrinsically magnetized stent-jackets are unlaminated. Lamination can also be used to increase the elasticity and/or the magnetic force of an intrinsically or a quasi-intrinsically magnetized stent-jacket.

Lamination may include layers both of which provide magnetization and elasticity where the combination serves to adjust these values; otherwise intrinsically and quasi-intrinsically magnetized stent-jackets are not laminated. The addition or radiation shielding yields a laminated stent-jacket wherein to avoid excessive thickness, the other layer is almost always intrinsically or quasi-intrinsically magnetized. These various alternatives make it possible to achieve any practical combination of properties in the thickness needed for circumductal clearance. The rate of spontaneous demagnetization of current permanent magnets allows permanent implantation. Magnetic stent-jackets are also characterized as slit, or full-round, or slotted, or partially round.

8b(2)(a)(i). Extrinsically Magnetized Stent-Jackets

Extrinsically magnetized stent- and impasse-jackets derive tractive force through the fastening about the outer surface of the jacket base-tube of permanent or electromagnets. Where a consistent minimal field force is to be increased for certain attractants infused in a ferrofluid, small electromagnets are added to the permanent magnets to comprise a hybrid type jacket. Control of electromagnets is by an implanted microprocessor as addressed below in sections XXI and XXII. Mounting tiny bar magnets about a length of elastic tubing with the tractive force oriented perpendicularly (radially) to the tube, or base-tube, provides a circumductal (periductal, circumvascular, perivascular) sheath (sleeve, surround), or stent-jacket.

Slit along one side, such a sleeve is able to expand and contract, hence, comply with changes in the diameter or gauge of a tubular structure whether tonic, pulsatile, or peristaltic. To avoid gouging of the surrounding tissue, the magnets are flattened, and to prevent abrasion, the edges are rounded and encapsulated. The surrounding tissue in contact with the ductus adapted to comply with its intrinsic movement, where such contact exists, the magnets are surface textured to encourage tissue adhesion, infiltration, and stabilization, thus warding off abrasive irritation. Nonabsorbable stent-jackets are encapsulated in a chemically isolating biocompatible polymeric coating and lined with moisture barrier-coated viscoelastic polyurethane foam.

An intrinsically magnetized stent-jacket of stainless steel has the distinct advantage of immunity to the development of microfractures with a consequent loss in resilience or a loss in magnetization either of which would result in a loss of function. The vessel or duct is kept patent by a mild outward pull upon the lumen wall toward the internal surface of the surrounding circumvascular stent-jacket. The ability of an extraluminal stent to move with the intrinsic movement in the ductus stands in marked contrast to the fixation in diameter and outward radial force against the lumen wall imposed by endoluminal stents.

While endoscopic coagulation or embolization remain preferable for treating ectasic (distended, dilated) blood vessels where collateral circulation allows these to be eliminated, an extravascular stent with or without magnetization, as appropriate, is applicable to reducing the luminal diameter of other ectasic ductus, whereas an endoluminal stent is not. A general awareness as to the potential of percutaneously introduced circumvascular sheaths to treat embedded vessels is evidenced by the awarding by the Radiological Society of North America of research grants in 2001 and 2002 for a project entitled Percutaneous Placement of Extraluminal Stent-Graft: A New Concept for Treatment of Occlusive Disease in the Superficial Femoral Artery. To date, the project has not yielded published results.

Such anastomosis and containment by extraductal sheaths, stents, or stent-grafts does not include bar magnets on the outer surface or ferromagnetic ductus intramural implants and has little if any relation to the stent-jackets to be described herein. A base-tube with spaced apart or discrete bar magnets applied to its outer surface, or an extrinsically magnetized stent-jacket, has the advantages of 1. Virtually unlimited magnetic force for applications such as attracting drug carrier nanoparticles from a ferrofluid with slight if any effect upon jacket elasticity, 2. Avoiding the need to a. Impregnate the polymeric base-tube itself with a magnetized particulate, thus reducing the relative proportion of continuous tubing material essential for longer life in a jacket of given thickness; or b. Adding another layer consisting of intrinsically magnetized metal tubing or a magnetized particulate-impregnated polymeric layer, which laminated, adds to the thickness of the base-tube, and 4. Assembly from off-the-shelf or standard components.

For high visibility, when encapsulated for chemical isolation within gold, for example, the tiny bar magnets are contrast marked with a coating of tantalum, for example. When the magnets and substrate base-tube are encapsulated together, the marking material such as tantalum is used to outline the magnets by vapor or sputter deposition onto the outer surface of the outer coating of the polyethylene terephthalate, for example, used to encapsulate the stent-jacket for chemical isolation. In no instance is the moisture barrier-coated viscoelastic polyurethane foam lining encapsulated. A polymeric base-tube laminated with intrinsically magnetized metal tubing or a magnetized particulate-impregnated polymeric layer is also extrinsically magnetized; however, lamination is its most salient characteristic and used to classify it as extrinsically magnetized laminated, or extrinsic laminated.

A nonlaminated, extrinsically magnetized stent-jacket has the disadvantages of at least slight protrusion radially outwards of the magnets, creating the potential for the jacket to rub against and abrade the surrounding tissue, nonuniform distribution of the tractive force over the base-tube, a conformation unamenable to the addition of a radiation shield by lamination, and if the magnets are stronger, can deflect the muzzle-head interfering with discharge accuracy forcing the use of an intrinsically or quasi-intrinsically magnetized stent-jacket or the use of stays rather than miniballs. The thinness of intrinsically and quasi-intrinsically magnetized stent-jackets is advantageous where completely uniform slight to moderate field strength is required.

Such pertains, for example, to stenting of the coronary arteries, which course through a thin layer of fatty connective tissue between the visceral pericardium or epicardium and the myocardium, and peripheral arteries that course through a sheath amid the muscles of the limb. Because it eliminates these deterrents, a quasi-intrinsically magnetized stent-jacket, addressed below, which additionally eschews the pliancy-thickness to achieve the ferromagnetic mass required factor posed by of an intrinsically magnetized stent-jacket such as one made of thin stainless steel sheet, is that most widely applicable. The extrinsic type is that shown in the drawing figures for reasons of pictorial clarity. Whether discrete magnets are advantageous or disadvantageous depends upon the need for concentrating the tractive force. When magnets and implants are properly aligned and it is desired that the traction be concentrated on these implants, and/or a drug carrier particulate is to be drawn, the use of discrete magnets is beneficial.

However, discrete magnets generally distribute magnetic traction less evenly about the ductus, so that if the magnets and susceptible miniballs or stays are not radially aligned, tangential vectors will urge the miniballs or stays sideways as well as radially outwards. If pronounced, this will interfere with compliance of the stent to the expansion and contraction of the ductus. The fewer and more clearly marked are magnets and miniballs, the less difficult will it be to align these, but the greater will be the concentration of traction. When a multibarrel radial discharge barrel-assembly under the control of a positional control system is used to lay down a tight formation of miniballs for the purpose of evenly distributing the traction on diseased or malacotic tissue, the misalignment of those more axial ductus-intramural implants will be less, but the greater will be the traction on the miniballs aligned to the axes or poles of the magnets.

Nonuniform tractive force increases the risk for pullthrough, or pulling the miniballs entirely out the side of the ductus wall resulting in stent failure. Spaced apart magnets will also yield the uneven uptake of a magnetic carrier particle-delivered drug into the ductus wall. The term 'base-tube' denotes a platform for magnets; nonplatform stent-jackets such as intrinsic, addressed next, are properly designated not base-tubes but stent-jackets. Generally, extrinsically laminated stent-jackets include a discretely magnetized layer only when the circumductal or perivascular clearance poses no concern for abrasion of the surrounding tissue.

Affording adjustability of the tractive force exerted on magnetically susceptible implants and constituents within ferrofluids, jackets rendered magnetic by affixing electromagnets about the outside of the base-tube are of special value in stent- and impasse-jackets. As with permanent magnet jackets, progressively increasing the field strength moving along the jacket as a gradient array allows a more uniform uptake along the luminal wall of a susceptible component introduced into the circulation as superparamagnetic iron oxide nanoparticles or microparticles, for example, and whereas the tractive force exerted is fixed with permanent or bar magnets, intrinsically magnetized base-tubes, and these combined in hybrid jackets, direct current electromagnets allow adjustment in the tractive force exerted by each of the successive magnets in accordance with the susceptibility of the attractant.

An important factor in avoiding patient discomfort, electromagnets for implantation, especially when wound with silver wire, can be made to generate considerable field strength while much lighter in weight than the equivalent neodymium magnets, for example. Unlike permanent and intrinsic/permanent stent- and impasse-jackets, electromagnets are not limited to a minimum residual field force beyond a slight bias following degaussing, or demagnetization, easily obtained by automatically passing direct current through the magnets in reverse. That is, compelled to project a minimum field, permanent and hybrid intrinsic/permanent and intrinsic/electromagnet jackets are limited in adjustability at the low end to some positive value, and since almost any intended field strength would be greater, this represents a considerable limitation.

The ability to effectively eliminate the magnetic field is important in allowing infusants to pass jackets magnetized thus and instead continue through the circulation, urinary, or digestive tract to the jacket at the treatment site intended. The adjustability in field strength of electromagnets allows susceptible infusants and treatment sites to be matched in attracter/attractant pairs, so that each susceptible infusant in a 'cocktail' of infusants or numerous infusants consecutively administered effectively seek out the jacket at the treatment site for which that infusant is intended. Selective targeting thus is of particular value in the treatment of comorbidity where numerous drugs must be targeted to different organs or tissues and the atradtion of any of these to the wrong jacket could result in complications.

When necessary to minimize outward protrusion about the jacket, electromagnets are wound with silver wire and the attractant or attractants provided with only so much subembolic micrometric Si—Fe crystal as sufficiently enhances magnetic susceptibility for the electromagnets to draw these into the lumen wall, for example. Adjustability in field strength allows fine tuning or 'trimming' for the susceptibility of the attractant and conditions such velocity of passage through the bloodstream and intermingling with food without the need to impose upon the patient to first purge the digestive tract with polyethelene glycol and electrolytes, for example.

Control over the shape of traction to meet the instant need is structural and established by the angle at which the jacket is applied to the substrate ductus, which the force to exerted responsive to a given infusant is encoded in the prescription program. The efficiency of stent and impasse-jackets, allowing their minimization in size and mass, is economically increased by including silicon-iron crystal in the attractants. To treat eccentric lesions, both permanent and electromagnets can be aligned along one side of the jacket; otherwise, the magnets are arranged however best responds to the conformation of the lesion to be treated. When remodeling or the antecedent therapy alters the conformation of the lesion, a distribution of magnets about the jacket can be changed in energization to complement the concomitant geometry.

Electromagnets allow such flexibility where intrinsically magnetic jackets do not. Conventional solenoid electromagnets are conformed for attachment to the base-tube with the coil winding arranged lengthwise, allowing it to be rounded flush to the base-tube for minimal radially outward protrusion; compactness in implants vitiates the risk of abrading contact with neighboring tissue, producing chronic irritation and raising concerns for fistulation and other complications. The coils are always enclosed within a shell to cover over sharp edges, corners, and any protrusions.

Depending upon the space constraints, electromagnets can be conventional solenoid, spiral, bifilar, or Ayrton-Perry wound bifilar (see, for example, Caverhill-Godkewitsc, S. 2015. *Modeling of Integrated Microfluidics-CMOS Lab-on-chip* Technology, Thesis, Department of Electrical and Computer Engineering, University of Alberta, section 3.8.1. "CMOS Spiral Electromagnet," page 52; Santra, A., Chakraborty, N., and Ganguly, R. 2009. "Analytical Evaluation of Magnetic Field by Planar Micro-electromagnet Spirals for MEMS [microelectromechanical systems] Applications," *Journal of Micromechanics and Microengineering* 19(8):10 pages, online; Beyzavi, A. and Nguyen, N.-T. 2008. "Modeling and Optimization of Planar Microcoils," *Journal of Micromechanics and Microengineering* 18(9):8 pages, online; Choi, J. W., in Minteer, S. D. (ed.) 2006. *Microfluidic Techniques: Reviews and Protocols*, Totowa, N.J.: Humana Press, section 3, page 70; Lund-Olesen 2005. *Integrated Microfluidic Mixer and Magnetic Bead Separator, Thesis, Institute of Micro and Nanotechnology, Technical University of Denmark*; Choi, J. W., Liakopoulos, T. M., and Ahn, C. H. 2001. "An On-chip Magnetic Bead Separator Using Spiral Electromagnets with Semi-encapsulated Permalloy," *Biosensors and Bioelectronics* 16(6):409-416; Kirschvink, J. L. 1992. "Uniform Magnetic Fields and Double-wrapped Coil Systems: Improved Techniques for the Design of Bioelectromagnetic Experiments," Bioelectromagnetics 13(5):401-411). To present a minimized cross section as not to encroach upon neighboring tissue, these are rounded for flush application around the outer surface of the base-tube.

Where the function of the stent-jacket is substantially consistent with an occasional need for increased tractive force, electromagnets can be added to an intrinsically magnetized jacket to constitute a type of hybrid stent-jacket as addressed below in section 8b(2)(a)(iii), entitled Hybrid Extrinsically and Intrinsically Magnetized Stent-jackets. Electromagnets added to an extrinsically magnetized jacket with permanent magnets allow discriminatory adjustments in field strength to differentially draw attractants of different susceptibility. When the individual components, both intrinsic jackets and electromagnets, are in regular production, such a hybrid can be made smaller in size and mass and at less expense. An intrinsically magnetic jacket can be magnetized to treat an eccentric lesion. The addition of small electromagnets to an intrinsically magnetic jacket, however, allows adjusting the jacket to treat the lesion following remodeling or a subsidence in eccentricity.

As addressed below in sections XX, entitled Exemplary Channel of Control in a Fully Implanted Ambulatory Adaptive Hierarchical Control System for Automatic Response to a Comorbid Condition and XXI, entitled Fully Implanted Ambulatory Adaptive Hierarchical Control Systems for Automatic Response to a Comorbid Condition, exclusively and hybrid electromagnet stent-jackets can be controlled by an implant microprocessor. Such control is governed by a prescription-program that automatically adjust each electromagnet of the stent-jacket in accordance with the medication or agent administered through a small port at the body surface.

When the microprocessor directs the outlet motors of implanted small flat drug reservoirs to release the medication so that the identity and dose of each drug is known to it, the prescription program automatically adjusts the field strength of the magnets accordingly. When the drugs are injected through the body surface port, the identity and dose of each drug is typed into the microcontroller with a computer tablet. Electromagnets also represent an additional mode of susceptible matter recovery, especially important were a potentially embolizing miniball to pass into the circulation, other methods of recovery addressed at numerous points herein.

8b(2)(a)(ii). Intrinsically Magnetized Stent-Jackets

In an intrinsically magnetized stent-jacket, the tubing material is itself magnetized and does not require the addition of magnetic material whether in the form of permanent magnets mounted about the outer surface or, as in a quasi-intrinsically magnetized stent-jacket, by embedding, laminating, or adding a coating of another susceptible material. Intrinsically magnetized stent-jackets uniformly project tractive magnetic force over the length of the jacket. This is suitable for radially symmetrical but not eccentric lesions, adjustability obtained by adding small neodymium permanent or electromagnets, for example.

Numerous magnetic polymers and metals available and under development can be used (see, for example, Giżynski, K., Lee, T., and Grzybowski, B. A. 2017. "Dynamic Self-assembly of Magnetic/Polymer Composites in Rotating Frames of Reference," *Advanced Materials* (Deerfield Beach, Fla.) 29(33); Kalia, S., Kango, S., Kumar, A., Haldorai, Y., Kumari, B., and Kumar, R. 2014. "Magnetic Polymer Nanocomposites for Environmental and Biomedical Applications," *Colloid and Polymer Science* 292(9): 2025-2052; Thévenot, J., Oliveira, H., Sandre, O., and Lecommandoux, S. 2013. "Magnetic Responsive Polymer Composite Materials," *Chemical Society Reviews* 42(17): 7099-7116; Philippova, O., Barabanova, A., Molchanov, V., and Khokhlov, A. 2011. "Magnetic Polymer Beads: Recent Trends and Developments in Synthetic Design and Applications," *European Polymer Journal* 47(4):542-559; Nishide, H. and Suga, T. 2011. "Magnetic Polymers," *Encyclopeda of Polymer Science and Technology* online at http://onlinelibrary.wiley.com/doi/10.1002/0471440264; Masi, J. V. 2007. "New Magnetic Polymers," in *Institute of Electrical and Electronics Engineers* 2007 *Electrical Insulation Conference and Electrical Manufacturing Expo*[sition] at http://ieeexplore.ieee.org/document/4562641/; Zaidi, N. A., Giblin, S. R., Terry, I., and Monkman, A. P. 2004. "Room Temperature Magnetic Order in an Organic Magnet Derived from Polyaniline," *Polymer* 45(16):5683-5689).

To augment its magnetic force, iron powder dispersed in a polyvinyl acetate matrix can be coated onto an otherwise intrinsically magnetized thin stainless steel or polymeric core. Rolled magnetic or nonmagnetic stainless steel or polymer sheet can be laminated with iron powder in a matrix of polyvinyl acetate, for example, encapsulated for chemical isolation and this in turn supplemented with permanent or electromagnets.

Materials currently under development may make it possible to consolidate an intrinsically magnetized base-tube and foam lining in a single material (see, for example, Fafenrot, S., Grimmelsmann, N., Wortmann, M., and Ehrmann, A. 2017. "Three-dimensional (3D) Printing of Polymer-metal Hybrid Materials by Fused Deposition Modeling," *Materials* (Basel, Switzerland) 10(10). Eventually, a single material may also be capable of drug release, although nonreplenishably, that is, to a finite limit (see, for example, Alhijjaj, M., Belton, P., and Qi, S. 2016. "An Investigation into the Use of Polymer Blends to Improve the Printability of and Regulate Drug Release from Pharmaceutical Solid Dispersions Prepared via Fused Deposition Modeling (FDM) 3D Printing," *European Journal of Pharmaceutics and Biopharmaceutics* 108:111-125).

Intrinsically and quasi-intrinsically magnetized stent-jackets can eliminate a clearance problem that would present were an extrinsically magnetized stent-jacket used. Unlike austenitic or nickel-containing 300 series stainless steels, martensitic and most precipitation carbon hardenable nickel free stainless steels, to include types 410, 416, 420, 440B, 440C, and 17-4, when magnetized in the hardened condition, are capable of permanent magnetization. A less strongly magnetizable stainless spring steel such as 18-8 at spring temper may require the addition of a nonabsorbable polymer coating with embedded chemically isolated neodymium granules.

An intrinsically magnetized stent-jacket is cut from a length of thin martensitic stainless steel flat sheet stock cold worked to impart a mildly shape restorative or springy character, uniformly pre-magnetized, and thereafter formed into the short tube so that the tractive force is oriented radially or normal to the long axis of the base-tube and the ductus it is to encircle. Intrinsically magnetized stent-jackets can be made of very thin sheet or tubing to achieve the thinnest profile of any such jacket. This increases the applicability of these and quasi-intrinsically magnetized stent-jackets next to be described, which are almost as thin, to peripheral arteries, for example, where circumvascular clearance makes the placement of discretely magnetized jackets inadvisable.

Unlike discrete magnet stent-jackets, which produce a nonuniform field with a focus at each of the magnets, intrinsically and quasi-intrinsically magnetized stent-jackets produce a field that is uniform and well matched to a dense formation of miniballs used precisely to avoid a concentration of tractive force on one or a few implants as might then pull through or result in delamination. Shaping into a tube is by forming over a mandrel while heating to a sub-Curie temperature of about 200 to 300 degrees centigrade, then oil quenching. The temperature will depend upon the metallurgy and thickness, but should be less than 310 to 400 degrees centigrade for $Nd_2Fe_{14}B$ (sintered) or 800 degrees centigrade for Sm(Co, Fe, Cu, Zr) (sintered).

In some instances exceeding the Curie temperature will not prevent the spontaneous recovery of domain alignment and magnetization once the material cools. The slit or slot where the long edges oppose serves as the expansion joint. The sheet must be sufficiently resilient to compensate for the repulsion of like poles in diametric opposition entirely about the jacket. The same material can be punched and magnetized in halves to form the extraction grid of an impasse-jacket. The primary considerations are compliance with the motility of the substrate (treated) ductus and use of the least magnetic force that will maintain the lumen in an undistended or stretched patent condition.

Since jacket resilience and the repulsion should balance out leaving the pulse or peristalsis as the driving force, the primary objective of compliance should not significantly limit the resilience or restorative force of the jacket needed to compensate for the circular repulsion whether due to its thickness or metallurgy. It has the advantages of unobtrusive thinness and a substantially even distribution of magnetic force entirely about the ductus as complements a close and even distribution of miniballs placed by a multibarrel radial discharge barrel-assembly under the control of a positional control system. This is generally less important for application along the gastrointestinal tract where the forces, thickness and strength of the tissue, and clearance afforded are considerable but critical for the treatment of a diseased artery, for example.

Such uniformity of the tractive force may be essential when treating a diseased ductus that would otherwise be further aggravated and/or a malacotic ductus that would be ruptured. However, due to the thinness essential for flexibility, the mass of ferromagnetic material is limited and the special magnetization required must be accomplished upon manufacture. Nevertheless, with diseased and/or malacotic tissue, mild stenting traction may be suitable. An intrinsically magnetized stent-jacket can represent a component layer in a laminated stent-jacket, referred to as intrinsically magnetized laminated, or intrinsic laminated, wherein the other layer is usually polymeric or quasi-intrinsically magnetized, and discretely magnetized only when the circumductal clearance poses no concern for abrasion of the surrounding tissue.

The development of magnetic polymers that can be made to specified mechanical properties at room temperature and implanted with or without a chemically isolating encapsulating outer layer will make possible not only novel microspheres and nanoparticles but intrinsically magnetized stent-jackets of a polymeric rather than metallic basis (see, for example, Fu, H. H., Yao, K. L., and Liu, Z. L. "Magnetic Properties of Very-high-Spin Organic Pi-conjugated Polymers Based on Green's Function Theory," *Journal of Chemical Physics* 2008 129(13):134706; Naveed, A., Zaidi, S. R., Giblin, I., Terry, and Monkman, A. P. 2004. "Room Temperature Magnetic Order in an Organic Magnet Derived from Polyaniline," *Polymer* 45(16): 5683-5689; Rajca, A., Wongsriratanakul, J., Rajca, S., and Cerny, R. L. 2004. "Organic Spin Clusters: Annelated Macrocyclic Polyarylmethyl Polyradicals and a Polymer with Very High Spin S=6-18," *Chemistry* 10(13):3144-3157; Rajca, A., Wongsriratanakul, J., and Rajca, S. 2001. "Magnetic Ordering in an Organic Polymer", *Science* 294(5546):1503-1505; Thorpe, M. F. 1976. "Magnetic Polymers," in *Proceedings, 34th Conference, American Institute of Physics*, Issue 5, Volume 22, page 13, Ann Arbor, Mich.: University of Michigan Press). This would allow increased latitude in the relation between strength of magnetization and stent-jacket thickness and elasticity while eliminating the surrounding clearance limitation with extrinsically magnetized stent-jackets.

8b(2)(a)(iii). Hybrid Extrinsically and Intrinsically Magnetized Stent-Jackets

Hybrid extrinsically and intrinsically magnetized stent-jackets are briefly addressed above in section 8b(2)(a)(i), entitled Extrinsically Magnetized Stent-jackets. Intrinsically magnetic jackets represent the form factor of least mass and volume but generally limited in field strength, intrinsically magnetic jackets may necessitate the incorporation of silicon-iron crystal in the attractant. This is of cardinal importance in applications involving small children and wherever the jacket, even though encapsulated to smooth over sharp edges and corners would otherwise encroach on neighboring tissue.

8b(2)(a)(iv). Quasi-Intrinsically Magnetized Stent-Jackets

A quasi-intrinsically magnetized stent-jacket incorporates magnetic material by embedment, lamination, or jacketing rather than by mounting permanent magnets about its outer surface. As it substantially distributes the tractive force uniformly notwithstanding the minimal number and size of perforations to expose the underlying tissue to its normal milieu, is readily laminated, does not tie flexibility to the thickness required to achieve the necessary magnetic strength, can be made with smooth faces, and affords numerous options in detailed formulation, this is the most common form of stent-jacket. A quasi-intrinsically magnetized stent-jacket consists of a length of polymeric flat sheet stock with a ferromagnetic particulate embedded in the polymer or copolymer which is then sectioned with each section formed into a mildly resilient side-slit or slotted cylinder with a side-slit or side-slot, the heat used to form the tubes well below the Curie temperature.

Intrinsically and quasi-intrinsically magnetized stent-jackets are superior to the discrete magnet type when uniform magnetization and traction are desired. Magnetization while the material remains flat allows the particulate to be uniformly magnetized and oriented, so that the tractive force will be exerted radially or normal to the long axis of the base-tube entirely about the circumference and thus entirely about the ductus it will encircle. The particulate is added while the polymer matrix remains amorphous (semi-molten, fluid). When the matrix material resists shaping into mildly resilient tubes by applying heat, the tubes are formed ab initio by extrusion, then temporarily held opened flat to uniformly magnetize the ferrous particulate added to the mix while amorphous. For a given thickness, the discontinuity among embedded particles less reduces jacket flexibility than does the continuous metal in an intrinsically magnetized stent-jacket.

Radiation shielding can be integrated into the jacket in the form of particulate tungsten, for example, which nonmagnetic, will not affect the magnetic character of the jacket but necessarily continuous, will add to jacket thickness and resilience as it relates to ductus compliance as the primary requirement. To reduce the number of distinctive stent-jackets and for simplicity, radiation shielding is applied by laminating a preexisting quasi-intrinsic stent-jacket with a separate layer of shielding material, usually tungsten. The sandwiching with or addition of an intrinsically magnetized stent-jacket to a polymeric jacket or to a quasi-intrinsically magnetized stent-jacket yields a compound intrinsically and polymeric or quasi-intrinsically magnetized laminated stent-jacket. Extrinsic magnetization is used when greater magnetic force must be exerted in a targeted manner.

For uniform distribution of the tractive force, thinness, and amenability to lamination such as to add a radiation shield layer, most stent-jackets are single layered, or intrinsically or quasi-intrinsically magnetized. These retain the limitation on the thickness of the intrinsically magnetized component that will allow the degree of flexibility required. Lamination of a quasi-intrinsically magnetized stent-jacket with a plain polymeric layer yields a quasi-intrinsically magnetized laminated, or quasi-intrinsic laminated stent-jacket. The other layer is discrete extrinsic magnetized only when the circumductal clearance poses no concern for abrasion of the surrounding tissue. If the quasi-intrinsically magnetized stent-jacket is absorbable, then seeds other than the magnetized particulate embedded within the base-tube may be used to accelerate its dissolution when heated, for example. One such approach is to prompt a chemical reaction that releases water within the jacket, expediting its dissolution through hydrolysis.

Other polymers may call for the release of an enzyme, for example. An absorbable quasi-intrinsically magnetized stent-jacket normally uses magnesium as the metal matrix. The magnetized particulate is a compound of iron or a lanthanoid. Extraluminal, the iron and any nontoxic magnesium alloy ingredients for imparting resilience to the magnesium are not absorbed through the gut and dissolve at a rate too slow to reach a serum concentration that is toxic. An absorbable stent-jacket can be used with absorbable stays or miniballs, likewise consisting of a glycolic acid derived polymer or copolymer, such as polylactic coglycolic polymer with embedded ferrous matter encapsulated as necessary for chemical isolation. Larger total amounts of iron or a more toxic particulate, such as one of neodymium iron boron, must be overlain with a nonabsorbable polymeric coating suitable for implantation.

8b(2)(a)(v). Laminated Stent-Jackets

Lamination allows adding numerous capabilities, modifications, or combinations of these to a base layer or an existing stent-jacket. These include increased resilience by adding another simple, compound, particulate and/or mesh-containing polymeric and/or metallic layer. Adding a layer containing sufficiently continuous electrically conductive ferromagnetic material allows remote, noninvasive, heating of the jacket by placing the patient in a radiofrequency alternating magnetic or electromagnetic field. The material is added by mixing granular elemental iron or small ferrous plates into the amorphous polymer matrix before extrusion.

The temperature attainable depends upon the strength and frequency of the magnet as well as the overall mass, continuity, and distribution of the iron. The same composition pertains to other components such as miniballs, as addressed below in the section entitled Noninvasive Dissolution on Demand of Absorbable Stent-jackets, Base-tubes, Radiation Shields, and Miniballs. Encapsulation in an absorbable jacket is essential only if the potential serum concentration of iron might obtain. The frequency and amplitude of the heat generating eddy current inducing alternating magnetic or electromagnetic field must be increased to compensate for resistance due to particulate discontinuity and the number of 'breathing' perforations in the stent-jacket to allow gas exchange.

Remote heatability can be used to release or accelerate the release of a drug, of water and/or an enzyme thereby enabling the dissolution on demand of the layer itself or of an absorbable jacket as a whole; reduce pain or discomfort as heat or hyperthermic therapy; accelerate drug uptake and healing, reduce surgical adhesive setting and curing times; flow a protein solder of low denaturing temperature; or these in any combination. This property is valuable for applying thermoplasty where followup examination reveals reobstruction such as due to intimal or medial hyperplasia. More specifically, incorporating ferrous plates or adding a layer containing overlapped elevated temperature-tolerant chemical isolation-encapsulated tungsten particulate in a nonresilient matrix layer need not significantly reduce the flexibility, hence, compliance with the motility of the substrate ductus, while providing remote heatability and radiation shielding in a layer that can be nonabsorbable for long term use, absorbable, or absorbable on demand.

An added layer can be used to increase the strength of magnetization of and/or add a radiation shield to a base-layer intrinsically or quasi-intrinsically magnetized stent-jacket. Adding a second intrinsically or quasi-intrinsically magnetized layer to an existing intrinsically or quasi-intrinsically magnetized stent-jacket of like polarity can be used to increase, or if of opposing polarity, then to reduce, the magnetic strength. This ability to supplement or modify an existing stent-jacket allows greater versatility at less cost than producing myriad specialized single-layer stent-jackets, and can be used to avoid the protrusion of discrete magnets mounted about the outer surface of the base-tube. When necessary; lamination allows adding resilience; however, the compliance of the resulting combination to the autonomic action in the substrate ductus must not be significantly degraded.

Extrinsic magnetization or the use of permanent magnets pertains when the circumductal clearance poses no concern for abrasion of the surrounding tissue, the addition of an outer lamina is uninvolved, and contrast marking the magnets is unproblematic. When the jacket as a whole is radiopaque, contrast marking, generally with tantalum, is applied to the outer coating applied for chemical isolation. The magnets tiny, rounded in peripheral contour, and cushioned by the encapsulating coating, encroachment is seldom a problem. If absorbable, an additional embedded particulate can be incorporated into the stent-jacket to accelerate its dissolution such as when heated. If metal, the base-tube consists of magnesium alloyed for resilience where the alloy substances are nontoxic. A radiation shielded stent-jacket is laminated. The material of the shield layer is intrinsic, such as tungsten, or is quasi-intrinsic as embedded in a matrix.

8b(2)(a)(vi). Spine and Ribs-Type Stent-Jackets

Spine and ribs-type stent-jackets are a variant of the segmented stent-jacket of the kind shown in FIG. 13 where the width of the segments is smaller or the rate of interruption increased to allow the ribs to better comply with peristalsis and accommodate vessels or nerves that would pass through the intervening spaces. The viscoelastic polyurethane lining and division into radiating fingers or ribs at intervals serve to reduce encroachment upon the small nerves, microvasculature, and vasa recta (see, for example, Kolton, W. A. and Pappas, T. N. 1997. "Anatomy and Physiology of the Small Intestine," in Greenfield, L. J., Mulholland, M. W., Oldham, K. T., Zelenock, G. B., and Lillemoe, K. D. (eds.), *Surgery: Scientific Principles and Practice*, Section D, Small Intestine, Chapter 26, pages 805-817) associated with gastrointestinal tract as might precipitate dysphagia or odynophagia. The esophagus, for example, is profusely innervated by branches and plexus of the vagus nerve.

The distance of excursion posed by peristalsis significant along the gastrointestinal tract, for example, spine and ribs-configured stent-jacket or rib jacket is intended to provide highly resolved compliance to the intrinsic motion of the ductus in the longitudinal direction. Compliance thus is essential to avoid dysphagia, for example. Miniature versions of this kind of stent-jacket can be applied to vessels where preservation of vessel support as acts to sustain endothelial function is important. Conforming to any of the variants described above in the section entitled Types of Stent-jacket, most often, such a stent-jacket will be intended for application to larger ductus such as those comprising the digestive tract. The spine is configured to allow the degree of flexion necessary. For such application, the stent-jacket will usually consist of an elastic (flexible, flexile, pliant) continuous longitudinal connecting or communicating bridge or band with elastic side fingers at intervals to reach about the substrate ductus which is used to encircle the ductus at its quiescent outer diameter.

In essence, it is a stent-jacket with slits or slots along the length added to that longitudinal for increased compliance notwithstanding being monolithic, that is, cut into a single piece of material. Because each longitudinally successive pair of fingers contracts and expands independently of the others, more highly resolved compliance in gauge along the stent-jacket is obtained than might be obtained from a length of continuous elastic tubing. This sequential flexibility makes a spine and ribs-configured stent-jacket suitable for placement along the digestive tract, wherein the form of peristalsis consists of successive traveling contractive waves that propel the lumen contents forward, often producing a bulge ahead of the contraction. Spine and ribs type stent-jackets can be radiation shielded. Extension of the jacket beyond the source of radiation at either end allows some negligible breathing or exchange of gases to the ductus surface, as addressed below in the section entitled Radiation Shield-jackets and Radiation Shielded Stent-jackets Absorbable and Nonabsorbable.

The resolution of compliance is set by the width of and the distance that separates the consecutive ribs or fingers, which like the contractive waves accommodated, are equidistant. Lined with moisture barrier-coated viscoelastic polyurethane foam, the ribs or fingers are widely variable in width, present no sharp edges, and have free ends slightly recurved to minimize injury to neighboring tissue. The dual agonistic and antagonistic action of factors released by periadventitial adipose tissue and the disruption in endothelial function when fat is excessive are addressed below in the section entitled Accommodation of the Adventitial Vasculature, Innervation, and Perivascular Fat. To assist in dissecting away excess surrounding fat and thus eliminate prominences from within the stent-jacket while leaving a uniform thickness of proximate fat that may contribute to endothelial function, a miniature spine and ribs-type stent-jacket for placement about an artery can be provided with razor sharp edges. The ribs are placed to avoid any significant vasa or nervora, the foam lining also serving to accommodate the gradual reduction in diameter along the gut.

Reference to such a form as a 'jacket' despite continuity limited to the connecting spine is prompted by its function as a unit and by analogy with elastic tube-type stent-jackets. Such a stent-jacket is usually cut from a continuous length of thin and pliant magnetizable stainless steel tubing by numerically controlled hydrojet, then lined with moisture barrier-coated viscoelastic polyurethane foam as necessary. Where compliance demands a thinness that is inconsistent with the strength of magnetization required, the metal form is coated with a polymer having particles of neodymium iron boron or other lanthanoid, for example, embedded. Polymeric materials of rubbery consistency are too soft and lack sufficient resilience for such use; however, if coated with an outer layer containing magnetized particles, any biocompatible harder plastic material of suitable flexibility and thickness can be used. In that case, the stent can be produced as a continuous strip analogous to a segmented stent-jacket.

Distinction among stent-jackets by the form of magnetization is addressed above in the section entitled Types of Stent-jacket. While most often intrinsically or quasi-intrinsically magnetized as are other stent-jackets, spine and ribs-configured stent-jackets can also be extrinsically magnetized or magnetized by lamination, as dictated by the clearance surrounding the treated segment. A stainless steel that can be magnetized to the field strength required within the thickness that provides the proper resilience is suitable. A moisture barrier-coated viscoelastic polyurethane foam lining is provided to protect the fine nerves and vessels that enter and depart from the outer surface of the ductus. If used to stent, the restorative force of the stent material should be no more than is necessary to retain the external surface of the substrate ductus flush against the foam lining. Also to prevent pull-through, broad stays, which pose greater resistance to pull-through than do miniballs, are used.

Then insertion of both the ductus-intramural and extravascular components is through a local access portal usually an incision of 5 centimeters, the need for endoluminal access eliminated and therewith, any deflection of the muzzle-head as the magnetized arms are passed as could detract from discharge accuracy. If used to attract drug carrier nanoparticles from a passing ferrofluid, then no more resistance to flexion than would induce dysphagia is applied. Insertion is through a laparoscopic portal, the ribs sufficiently retracted and held open by spanning these over the outer surface of the spine with pressure sensitive tape with a nonadherent tab at one end. Once positioned with the internal surface of the spine lining against the ductus, the tape is peeled away by grasping the tab with a tweezers or biopsy forceps to free the ribs to close about the ductus. All of the absorbable components addressed herein, whether ductus-intramural implants, jackets, or shield-jackets, can be formulated to break down spontaneously by hydrolysis and/or enzymatic action or incorporate substances susceptible to solvents that allow early or discretionary dissolution on demand.

8b(2)(a)(vii). Absorbable Stent-Jackets

Absorbable stent-jackets and other type implants described herein must be exposed to hydrolytic and enzymatic breakdown and are not encapsulated in a chemically isolating and cushioning nonabsorbable polymeric capsule, casing, or coating. Chemical isolation is therefore limited to encapsulating any particulates embedded within a quasi-intrinsic stent-jacket as matrix or applied to a base-tube as a coating thereto that are toxic, adversely reactive, or abrasive, such as magnetic lanthanoid or sintered osmium powder particulate used as radiation shielding, which spontaneously oxidizes to osmium tetroxide, which is toxic.

Absorbable extraluminal magnetic stent-jackets and base-tubes are addressed below in the sections entitled Absorbable Extraluminal Magnetic Stent-jackets and Materials and Absorbable Base-tube and Stent-jacket, Miniball, Stay, and Clasp-magnet Matrix Materials. Absorbable materials are always subject to premature dissolution under conditions of fever, infection, or an accumulation of aqueous fluid as in edema or ascites. An absorbable jacket that both retracts subadventitial implants and provides radiation shielding is laminated of bonded or fused component lamina of which the inner provides stenting and the outer shielding.

A fully absorbable extraluminal stent can also use absorbable implants in or to abut against the lumen wall. These can be placed with any kind of barrel-assembly as shown in FIGS. 31, 32, 38, 39, 48, 49, 65, 66, 71, and 78 or any kind of stay insertion device as shown in FIGS. 87 thru 91 Alternatively, when an intravascular component is to dissolve while in abutting relation with the lesion, a permanent magnet stent-jacket is first endoscopically positioned about the substrate ductus and the intraluminal component infused as microspherules or in a ferrofluid as fused superparamagnetic iron oxide nanoparticles.

When the intravascular component is to be drawn into the lumen wall, the stent-jacket is provided with small electromagnets. To minimize outward protrusion about the jacket, these electromagnets are wound with silver wire and the implants incorporate only so much subembolic micrometric Si—Fe crystals as sufficiently enhances attractability for the electromagnets to draw these into the lumen wall. Any of these temporary stent intravascular components can and usually do incorporate anti-inflammatory and other medication.

8b(2)(a)(viii). Radiation Shield-Jackets and Radiation Shielded Stent-Jackets Absorbable and Nonabsorbable A radiation shield or absorbable radiation shield can be applied to any stent-jacket, whether extrinsically, intrinsically, or quasi-intrinsically magnetized and whether the underlying stent-jacket consists of a length of elastic tubing or is of the spine and ribs configuration. Since the field strength required to attract a ferromagnetic nanoparticle, microspherule, or miniball dispersant will ordinarily result in pull-through or delamination with stent failure, the use of a stent-jacket with shield is substantially limited to highly sclerosed ductus. When directly laminated to the underlying stent-jacket, the increased resilience of combined layers must be taken into account, as must the breach in shielding created by the slit and potential damage to the fine vessels and nerves of the adventitia that may result from ensheathment within a not otherwise perforated, 'breathing' restrictive if not eliminating covering that does not break down with depletion of the radiation.

Atherosclerotic sequelae, for example, are avoided by using an absorbable radiation shield that will break down spontaneously or sooner by direction from outside the body. The underlying stent-jacket itself perforated and slit, the interposition between the outer surface of the stent-jacket and internal surface of the encircling shield allows the stent-jacket an extent of movement independently of the shield, providing a method for reducing overall resilience other than changes in materials or thicknesses of the layers. Since the gap between stent-jacket and shield allows the stent-jacket to expand within, the shield can be bonded shut; however, it still must be sufficiently pliant to allow encirclement of the ductus. Newer open cell materials do allow gases to pass through, but for the present application, do so to a practical extent only when limited to cuffs toward the end margins, interposed between the inner jacket and outer shield. For most purposes here, closed cell material is preferable as minimizing infiltration with blood, serous fluid, or tissue. At least in a spine and ribs type stent-jacket, increasing the thickness of these cuffs allows the ribs to move more freely and the adventitia to breath.

Because the shield must be compliant, a stony, stiff, or rigid monolithic structure can be used only when space permits the interposition of a sufficient thickness of a sufficiently gas permeable foam lining to accommodate movement intrinsic in the substrate ductus. Then only may lithotripsy be used to effect dissolution. The ability to limit exposure allows the use of higher dose-rate seed miniballs or stays than might otherwise be allowable. Absorption on demand is addressed below in the section entitled Noninvasive Dissolution on Demand of Absorbable Stent-jackets and Base-tubes, and applies no less to the matrix of a radiation shield. The ability to segregably disintegrate a radiation shield needed only until the radioactive seed miniballs or stays decay such that the underlying stent-jacket lamina with perforations can be exposed on demand is accelerated by means of heat alternating magnetic or electromagnetic eddy current heat induction is addressed below in the section entitled Noninvasive Dissolution on Demand of Absorbable Stent-jackets, Base-tubes, Radiation Shields, and Miniballs.

Radiation seed miniballs can be left in place when expended, which always pertains when a stenting function is present as well, or be retrieved endoluminally with the recovery electromagnets in a barrel-assembly muzzle-head—usually the same barrel-assembly used to place the miniballs—or extraluminally by means of an extracorporeal electromagnet, both addressed herein. Stays are not recovered, but except for the seed contained, can be absorbable. The addition of shielding should least detract from the flexibility or add to the thickness of the stent-jacket. Mass and thickness are minimized by using the heaviest materials, such as tungsten, gold, platinum, iridium, osmium, and platinum-osmium alloy, only the elemental noble or nonreactive metals not requiring chemical isolation encapsulation. Tungsten has the added advantage that when placed in a radiofrequency alternating magnetic or electromagnetic field, the shield can also be heated, whether to accelerate the metabolic rate, healing, relieve discomfort, rate of drug release and/or uptake, or the rate of prompt dissolution of the layer if absorbable.

Heating can release bound water embedded within the layer itself or that to which it is bonded. Lamina devised to disintegrate or release medication are bonded to the base layer by means of an adhesive. Lamina such as nonabsorbable radiation shields not susceptible to degradation or disintegration by heating can be bonded by any of a number of long established methods, to include induction welding by doping the layer with a ferromagnetic particulate and heating the layers in an induction furnace, for example. Provided the particulate is chemically isolation-coated as to remain such, the toxicity of these materials does not preclude their use for radiation shielding when embedded within an absorbable matrix layer. When not administered in the form of powdered compounds, gold and platinum have the advantage of being nonreactive or noble, hence, nontoxic. To allow flexibility consistent with continuity, the protectively encapsulated particles are embedded within the polymeric matrix in overlapping relation within a nonresilient polymeric matrix.

The addition of a radiation shield, addressed above in the section entitled System Implant Magnetic Drug and Radiation Targeting, is by lamination to an existing stent-jacket. This affords versatility, the alternative being the production of special shielded quasi-intrinsic stent-jackets that include both shielding and magnetized particulates, for example. Lamination is to an intrinsically, quasi-intrinsically, or absorbable quasi-intrinsically magnetized stent-jacket, lamination to a stent-jacket with discrete magnets avoided as yielding unwanted thickness. An absorbable radiation shield can be laminated to an absorbable or a permanent stent-jacket that is to continue as a stent, but an absorbable stent-jacket is always laminated with an absorbable shield. Lamination is by adhesive bonding, methods such as the use of heat or plastic welding usually inapplicable. Radiation shielding is addressed below in the section entitled Radiation Shielding Stent-jackets.

8c. Placement of the Extraluminal Stent

8c(1). Considerations as to Access

An advantage afforded by an ablation or angioplasty-capable barrel-assembly being the capability to perform an ablation or angioplasty without the need for withdrawal in order to stent, points of entry are mentioned above in the section entitled Comparison with Prior Art Angioplasty. Laparoscopic techniques have made it possible to access vessels and ducts without extensive incision, making the placement of stays and stenting that necessitates local entry for circumvascular access less objectionable than when more extensive exposure was necessary. Rarities such as tunneling coronary arteries not amenable to being dissected free excepted, practically any ductus can be extraluminally stented; seldom if ever will a ductus or its sheath be so closely surrounded by skeletal muscle or other tissue that an intrinsically magnetized thin stainless steel or soft and biocompatible polymer-coated stent-jacket or other extraluminal implant described herein of smooth outer contour would result in abrasion or encroachment.

Neither are most ductus unsuitably positioned or weak-walled over a length such that the remedial measures to be described herein cannot be applied. Dissection for circumvascular application of a stent or impasse-jacket should seek to minimize compression or abrasion of the adjacent tissue. Extraluminal stenting of the trachea requires access by 'keyhole' incision and of the bronchi by 'keyhole' thoracotomy or trephine sternotomy to place the stent-jacket, which carries some risk (Walser, E. M. 2005. "Stent Placement for Tracheobronchial Disease," *European Journal of Radiology* 55(3):321-330) and is no less susceptible to bacterial colonization (Noppen, M., Piérard, D., Meysman, M., Claes, I. and Vincken, W. 1999. "Bacterial Colonization of Central Airways after Stenting," *American Journal of Respiratory and Critical Care Medicine* 1999 160(2):672-677). Luminal obstruction that results purely from internal swelling, such as asthma or bronchitis, is a matter for medical management and not suitable for extraluminal stenting, which should seldom if ever be used to distend a ductus beyond its normal outer diameter. Also not targeted is the bronchomalacia of infants, which seldom fails to resolve spontaneously and does not justify percutaneous access.

However, where the condition involves collapse or weakening, such as a persistent adult tracheomalacia (see, for example, Kandaswamy, C. and Balasubramanian, V. 2009. "Review of Adult Tracheomalacia and its Relationship with Chronic Obstructive Pulmonary Disease," *Current Opinion in Pulmonary Medicine* 15(2):113-119; Murgu, S. D. and Colt, H. G. 2006. "Treatment of Adult Tracheobronchomalacia and Excessive Dynamic Airway Collapse: an Update," *Treatments in Respiratory Medicine* 5(2):103-115), an extraluminal stent, because it leaves the lumen clear, will not promote the development of granulation tissue that can bury an endoluminal stent its precluding removal (Antón-Pacheco, J. L., Cabezalí, D., Tejedor, R., López, M., Luna, C., Comas, J. V., and de Miguel, E. 2008. "The Role of Airway Stenting in Pediatric Tracheobronchial Obstruction," *European Journal of Cardiothoracic Surgery* 33(6):1069-1075, Section 3.3. Complications; Filler, R. M., Forte, V., and Chait, P. 1998. "Tracheobronchial Stenting for the Treatment of Airway Obstruction," *Journal of Pediatric Surgery* 33(2): 304-311) and should not interfere with respiratory epithelial secretion and the immune function of the mucociliary 'escalator.'

To avert migration, endoluminal bronchial stents must have posts, rings, or struts that protrude into and thus anchor or brace the stent in the airway lining. Tracheal collapse can affect any avian or mammalian species. Several are referenced in the section below entitled Application of Simple Pipe-type Barrel-assembly to the Magnetic Correction of Tracheal and Bronchial Collapse (Veterinary). Valuable zoo specimens, livestock, and mammals kept as pets are often the subjects of corrective procedures. Compared to the extent and complexity of dissection required to place a graft, that required to place an implant described herein is slight. Access to the external surface of the ductus to be treated is essential to apply a stent-jacket, stays, or a clasp-jacket.

About 27 percent of coronary arteries are surrounded by muscle, the consequence for the development of atherosclerosis in dispute (see, for example, Ishikawa, Y., Kawawa, Y., Kohda, E., Shimada, K., and Ishii, T. 2011. "Significance of the Anatomical Properties of a Myocardial Bridge in Coronary Heart Disease," *Circulation Journal* 75(7):1559-1566; Saidi, H., Ongeti, W. K., and Ogeng'o, J. 2010. "Morphology of Human Myocardial Bridges and Association with Coronary Artery Disease," *African Health Sciences* 10(3): 242-247; Ishikawa, Y., Akasaka, Y., Suzuki, K., Fujiwara, M., Ogawa, T., and 20 others 2009. "Anatomic Properties of Myocardial Bridge Predisposing to Myocardial Infarction," *Circulation* 120(5):376-383; Duygu, H., Zoghi, M., Nalbantgil, S., Kirilmaz, B., Turk, U., Ozerkan, F., Akilli, A., and Akin, M. 2007. "Myocardial Bridge: A Bridge to Atherosclerosis," [in English] *Anadolu Kardiyoloji Dergisi* 7(1): 12-16; Ishii, T., Asuwa, N., Masuda, S., and Ishikawa, Y. 1998. "The Effects of a Myocardial Bridge on Coronary Atherosclerosis and Ischaemia," *Journal of Pathology* 185 (1):4-9), tunneling considered to be anomalous remains intramyocardial for more than 20 millimeters at a depth of greater than 5 millimeters.

The arteries in the extremities are ensheathed and will usually provide sufficient clearance to be encircled by at least a very thin intrinsically magnetized stainless stent-jacket. Access to the coronary arteries is through a small, typically less than 5 centimeter, left or right, third or fourth intercostal minimal port or 'keyhole' mini-thoracotomy (see, for example, Landreneau, R. J., Mack, M. J., Magovern, J. A., Acuff, T. A., Benckart, D. H., Sakert, T. A., Fetterman, L. S., and Griffith, B. P. 1996. "Keyhole" Coronary Artery Bypass Surgery," *Annals of Surgery* 224(4).453-462), small or burr sternotomy, or ministernotomy. Another angle of approach is directly through the sternum by means of a craniotome or trephine (surgical hole saw). If necessary, an accessory intercostal port is used for video assist. The one access site allows both stays and a stent-jacket to be applied, so that when preparatory treatment such as an angioplasty is excluded, the artery is never entered; "direct stenting" is addressed above in the section entitled Closer Comparison of Extraluminal to Endoluminal, or Conventional, Stenting.

Anomylous arteries that course through muscle, specifically submyocardial tunneling or 'myocardial bridging' coronary arteries (Alegria, J. R., Herrmann, J., Holmes, D. R. Jr., Lerman, A., and Rihal, C. S. 2005. "Myocardial Bridging," *European Heart Journal* 26:1159-1168); Sundaram, B., Patel, S., Bogot, N., and Kazerooni, E. A. 2009. "Anatomy and Terminology for the Interpretation and Reporting of Cardiac MDCT: Part 1, Structured Report, Coronary Calcium Screening, and Coronary Artery Anatomy," *American Journal of Roentgenology* 192(3):574-583) should not be stent-jacketed. However, these arteries appear not to exceed 12 percent (Ricciardi, M. J., Beohar, N., and Davidson, C. J. 2005. "Cardiac Catheterization and Coronary Angiography," in Rosendorff, C. (ed.), *Essential Cardiology: Principles and Practice*, Totowa, N.J.: Humana Press, page 208), and with a radial projection catheter or barrel-assembly containing sufficient radial projection units, can be angioplastied and/or otherwise treated with any tool or therapeutic substance.

For conditions that reduce the outer diameter of the ductus, primarily tracheal or bronchial collapse, arterial shrinkage (negative remodeling, contracture), and persistent localized arterial vasospasm, the immediate advisability of applying outward traction may warrant the placement of an extraluminal stent ab initio. Access to place a stent of the kind described is less traumatic than the open surgical procedure that must be performed to place a tracheal extraluminal stent made of rings cut from an injection syringe or to place a graft or stent-graft; however, it is more traumatic than the transluminal delivery of an endoluminal stent, which is, however, basically inferior.

8c(2). Means for the Placement of the Stent-Jacket

The stent-jacket is placed through a laparoscopic entry wound a few centimeters long. When the risk of injury to underlying structures is higher, entry with a trocar should be avoided. Once incised, a trocar can be inserted to retract the tissue surrounding the incision. Existing surgical and microsurgical instruments are not configured for expeditious placement of a stent-jacket and require extension of the entry wound. For that reason, special hand tools, described below in the section entitled Stent-Jacket Insertion Tools, are provided. The same tools are used to place any type stent or impasse-jacket.

8d. Closer Comparison of Extraluminal to Endoluminal, or Conventional, Stenting

Two critical distinctions between an endoluminal and an extraluminal stent are that an extraluminal stent avoids the numerous complications associated with sustained intrusion in the lumen, and unlike the endoluminal stent, complies with movement or muscular action in the wall of the ductus. The use of stays can make it possible to avoid entry into the lumen entirely. In the circulatory system, the problems produced by an endoluminal stent include immune rejection and adverse tissue reaction responses to the presence of alien matter, an initial immune followed by an adaptation response to the obtrusive presence of a foreign object, and misinterpretation by cytokines that the source of localized turbulent flow represents a breach. With an extraluminal stent, the dyslipidemia associated with the atherosclerosis will continue to require the use of a statin, but anticoagulative medication need not be taken for life.

Where an endoluminal stent must exert radially outward force to prevent migration, an extraluminal stent provides radially inward support of the already diseased ductus, which may additionally have undergone an atherectomy or angioplasty, further weakening it. In an artery, this can be the difference between encouraging and preventing aneurysmal failure. Situated outside the lumen, an extraluminal stent avoids the clogging, migration, loss, fracture, deformation, and other hazards that persist with the use of endoluminal stents and guidewires (references below). When a preparatory angioplasty is waived, stays eliminate the need for entry into the lumen altogether. Once implanted along the vascular tree, an extraluminal stent averts thrombogenic disruption to the streamline or laminar flow of blood and chronic irritation as induces in-stent restenosis.

Balloon expansion not preceded by in situ testing, the endoluminal stent affords slight if any ability to adjust the force of patenting restraint to that least necessary. Diseased or healing tissue is intruded upon by a hard and noncompliant scaffold that protrudes into, stretches, and irritates it. An endoluminal stent always protrudes into the intima and can even protrude into tissue surrounding the ductus. When this results in chronic irritation as sustained pressure or tissue on tissue rubbing, an erosive lesion or fistula can form. Endoluminal stents in adjacent relation, such as segments of the trachea and the esophagus, are infrequently required, but can place the structures in a rubbing and erosive relation. By contrast, extraluminal stent-jackets in adjacent relation can no more than rub against one another, each enclosing its responective substrate adventitia, holding it at a distance from its neighbor, and thus preventing abrasion.

Additional hazards include deformation, fracture, and migration, all more likely should the stent incur an accidental impact. Regardless of the cause, protracted impairment in physiological function due to chronic immobilization of the treatment site (motional interference, motile suppression) induces a tissue reaction, first of immune rejection, then of adaption, and destroys normal structure and function in the lumen wall. Even though the smooth muscle had deteriorated or atrophied, a stent that is able to comply in expandability and contractility can be significant in preserving residual vascular physiology, and if sufficient, even promote recovery. In any ductus, the fact that no foreign object occupies the lumen means that the passage of contents is less if at all impeded and the mechanics of the wall little if at all affected.

In end to end anastomotic tuboplasty, for example, where an endoluminal stent can migrate (see, for example, Jurema, M. W. and Vlahos, N. P. 2003. "An Unusual Complication of Tubal Anastomosis," *Fertility and Sterility*79(3):624-627) and plain polytetrafluoroethylene tubing may be used as an endoluminal stent (see, for example, Roland, M. and Leisten, D. 1977. "Advances in Tuboplasty," *Acta Obstetricia et Gynecologica Scandinavica* 56(4):419-426), or following balloon tuboplasty where swelling that would obstruct the lumen is prevented by placing a stent (see, for example, Kerin, J. F. and Surrey, E. S. 1992. "Tubal Surgery from the Inside Out: Falloposcopy and Balloon Tuboplasty," *Clinical Obstetrics and Gynecology.* 35(2):299-312), the reinstatement of normal function at every level to include peristalsis, much less the recovery of fertility, remains impossible until the endothelium overlying and rigid tubing is removed, whereupon swelling and constriction might occur or reoccur.

By contrast, an extraluminal stent leaves the lumen free and clear and can be left in place to preserve patency indefinitely. Where an antecedent procedure that interrupted fertility was uninvolved, as in the treatment of salpingitis or a tuboovarian abscess where the chance of obstruction is a concern, an extraluminal stent in conjunction with the administration of antibiotics does not disrupt ovarian steroid production that can reduce swelling and improves the odds for preserving fertility (Wiesenfeld, H. C and Sweet, R. L. 1993. "Progress in the Management of Tuboovarian Abscesses," *Clinical Obstetrics and Gynecology.*36(2):433-444; Akyol, D., Özcan, U., Ekin M., Güngör, T., and Gökmen, O. 1998. "Tubo Ovarian Abscess: Risk Factors and Clinical Features in Turkish Population," *Turkish Journal of Medical Sciences* 28:691-692). The intraductal component of the extraluminal stent can consist of or include stays or miniballs that incorporate medication and/or irradiating seeds to treat the lesion and maintain patency.

Even if not significantly injured, angioplasty in itself stimulates the proliferation of smooth muscle cells in and infiltration of leukocytes into the media, and endoluminal stenting induces inflammation that predisposes toward in-stent lesion development (Miyahara, T., Koyama, H., Miyata, T., Shigematsu, H., Inoue, J., Takato, T., and Nagawa, H. 2006. "Inflammatory Responses Involving Tumor Necrosis Factor Receptor-associated Factor 6 Contribute to In-stent Lesion Formation in a Stent Implantation Model of Rabbit Carotid Artery," *Journal of Vascular Surgery* 43(3):592-600).

With an extraluminal stent, in-stent restenosis as the result of the same forces impossible. Leaving the lumen clear, an extraluminal stent used in place of an endoluminal stent following an angioplasty that resulted in a dissection, for example, tends less to induce proliferative or thrombogenic sequelae as contribute to the need for, complicate, and interfere with retreatment for restenosis. When the extraluminal stent uses stays, which are inserted from outside of the ductus and through the adventitia or fibrosa, the avoidance of contact with the inner surface of the lumen wall leaves the endothelium substantially if not completely intact. An extraluminal stent poses no obstruction to any later transluminal procedure. An extraluminal stent in the airway or gastrointestinal tract cannot accumulate detritus.

The recovery of an endoluminal stent that has migrated, fractured, or is repeatedly clogged or lined with accreted matter or detritus is seldom practicable (see, for example, Liermann, D. and Kirchner, J. 2004. "Foreign Body and Stent Retrieval," Chapter 26 in Heuser, R. R. and Henry, M., *Textbook of Peripheral Vascular Interventions*, London, England: Informa Health Care; Almeida, R. M. S. de, Bastos, L. C., Lima, J. D. Jr., and Jorge, A. C. 1997. ""Retrieval of a Migrated Coronary Stent by Cardiopulmonary Bypass," *Internet Journal of Thoracic and Cardiovascular Surgery* 2(1):18). Instead, when necessary, the stent is repositioned and fixed in place with a second stent (see, for example, Meisel, S. R, DiLeo, J., Rajakaruna, M., Pace, B., Frankel, R., and Shani, J. 2000. "A Technique to Retrieve Stents Dislodged in the Coronary Artery Followed by Fixation in the Iliac Artery by Means of Balloon Angioplasty and Peripheral Stent Deployment," *Catheterization and Cardiovascular Interventions* 49(1):77-81), thus further aggravating normal function.

Avoiding the need for extraductal access, endoluminal stents are more widely applicable than are extraluminal stents and involve less trauma to place; however, endoluminal stents, especially in the ureters, for example, are short-lived, obstructive, smooth muscle-restraining, endothelium and lamina propria irritants, hence palliative, but only at considerable expense. For the purpose of implanting medication-eluting or irradiating seed miniballs or stays and/or stays as buttresses within the wall of a lumen where the need for an extraluminal component or stent-jacket does not exist, location of a lesion that precludes encirclement by a stent-jacket or patch-magnets does not limit use of the means described. To prevent migration, any endoluminal stent, to include those absorbable pending absorption, must exert radially outward force over the entire circumference. This precludes the design latitude essential to configure the stent to accommodate lesion eccentricities as well as interferes with endothelial function.

Neither do endoluminal absorbable stents allow preventive use by allowing preplacement at points where reocclusion is likely to ensue due to cellular proliferation despite the use of a statin drug, such as bifurcations in the arterial tree (see, for example, Koutouzis, M., Paraskevas, K. I., Rallidis, L. S., Barbatis, C., Nomikos, A., and 7 others 2008. "Statin Treatment, Carotid Atherosclerotic Plaque Macrophage Infiltration and Circulating Inflammatory Markers," *Open Cardiovascular Medicine Journal* 2:110-114; Shukla, A., Sharma, M. K., Jain, A., and Goel, P. K. 2005. "Prevention of Atherosclerosis Progression Using Atorvastatin in Normolipidemic Coronary Artery Disease Patients—A Controlled Randomized Trial," *Indian Heart Journal* 57(6):675-680; Nicolaides, A., Beach, K. W., Kyriacou, E., and Pattichis (eds.) 2012. *Ultrasound and Carotid Bifurcation Atherosclerosis*, London, England: Springer; Suri, J. S., Kathuria, C., and Molinari, F. (eds.) 2010. *Atherosclerosis Disease Management*, New York, N.Y.: Springer), or where a progressive condition of collapse is encountered, such as in the airway, as addressed below in the section entitled Magnetic Correction of Airway Collapse and described beginning with the section below entitled Treatment of Tracheal Collapse in the Cervical Segments, i.e., Cephalad, or Anterior, to the Thoracic Inlet.

The need for stenting substantially pertinent to ductus with an exclusive supply territory (without collateral circulation) where magnetic stenting is uninvolved so that the application of a circumvascular stent-jacket is not required, stays can be used regardless of the lumen diameter, and miniballs can be implanted within any ductus large enough to admit the barrel-assembly. The ductus-intramural implants leave the lumen clear, and when placed for stenting, are attracted radially outward or centrifugally by a magnetic field no stronger than is necessary to maintain patency. Coating the internal or adluminal surface of the stent-jacket with a surgical cement is unnecessary and discouraged as immobilizing. The use of cements for other nonimmobilizing purposes is addressed below under such sections as that entitled Sealing of Stay Insertion Incisions with Cyanoacrylate Cement, and the use of protein solders below under the section entitled Use of Solid Protein Solder.

Whether congenital or the result of dissection or infection, for example, eccentric lesions other than atheromatous, can also appear in any ductus or blood vessel (see, for example, Russo, C. P. and Smoker, W. R. 1996. "Nonatheromatous Carotid Artery Disease," *Neuroimaging Clinics of North America* 6(4):811-830). Numerous conditions prompt hyperplasia, and previous radiotherapy or chemotherapy can induce hardening. Fluid infiltration, hypervascularization, atrophy, and pyogenic arteritis can produce malacia (softening). All of these alterations tend to be radially asymmetrical, or eccentric. The neovascularized artery is usually eccentric (see, for example, Hayden, M. R. and Tyagi, S. C. 2004. "Vasa Vasorum in Plaque Angiogenesis, Metabolic Syndrome, Type 2 Diabetes Mellitus, and Atheroscleropathy: A Malignant Transformation," *Cardiovascular Diabetology* 4; 3:1). In fact, different type lesions in different type ductus, to include atheromatous and neoplastic, before and after treatment, tend to be radially asymmetrical, or eccentric, with the ductus wall variable in tenderness and strength about the circumference.

Diseased tissue tending toward eccentricity, an improved stent should allow eccentricities to be dealt with in a discriminate manner. Unlike endoluminal stents, extraluminal stents can accommodate side branches, attachments, and lesions which are eccentric, as is usually the case. Unless intracranial or otherwise denying circumvascular clearance, the vessel will be accessible to encirclement with a stent-jacket. Furthermore, continuous variability characterizing diseased tissue, the need for in situ testing to evaluate the puncture and penetration resistance of the lesion in the patient is clear. An improved stent should also provide the means to test the mechanical properties of lesions. Testing methods and apparatus are addressed below in the section entitled Testing and Tests. The turret-motor allowing immediate change in the rotational angle of the muzzle-head and thus rotation of the exit-port or ports, and the rotary magazine clip instantly changed to blank out any barrel-tube or tubes and thus arc, eccentric lesions are readily avoided or implanted with miniballs.

This remains the case even with lesions that change in circumferential placement longitudinally, that is, spread to or recede from the adjacent arcs from segment one segment or level to the next. Muzzle-heads with muzzle-ports separated by less than 45 degrees are therefore not only unchangeable midprocedurally without withdrawal and reentry but nonessential. Vessels too small in gauge to admit a multibarrel barrel-assembly are negotiated with a radial discharge monobarrel equipped with a turret-motor. With an imaging technique that allows distinguishing arcs about the lumen, the angioplasty, atherectomy, and implantation means provided herein complement these capabilities. Leaving the lumen clear, an extraluminal stent affords discriminatory treatment of eccentric lesions both during angioplasty or atherectomy and any subsequent therapy.

The magnetic extraluminal stents described herein differ from endoluminal stents not only in the ability to include or avoid areas about the lumen in an absolute sense, but in the ability to apply differential patenting force (magnetic field strength) to different arcs at different levels; an magnetic extraluminal stent can apply tractive force asymmetrically both longitudinally and circumferentially. Such can serve to increase the retractive force acting upon a stricture with the strength to retain the ductus-intramural implants, or to minimize irritation to diseased or healing tissue. This is accomplished simply by varying the ferromagnetic content or number of the implants and/or the strengths or number of the magnets about the base-tube. Depending upon the pattern of the lesions and lumen wall strength, limited areas of the wall can be omitted from subjection to a tractive patenting force if increasing the force on neighboring areas will serve to maintain patency. Strength pattern coordinated ductus-intramural implants and stent-jackets asymmetrical with respect to magnetic strength are marked to assure proper orientation.

Eccentric and pathologically distinct lesions within the same vessel or duct can also be dealt with through the use of differently medicated or irradiative miniball implants. Eccentric and pharmacologically differential treatment can usually be accomplished without the need to withdraw one barrel-assembly and replace it with another having a differently configured muzzle-head. Not only does this reduce procedural time, but the sum duration of transient ischemia due to blockage of the vessel by the apparatus and of injury to the inguinal or brachial point of entry is significantly reduced. Whereas endoluminal stenting imposes some clotting for endothelial recovery, stays avoid the lumen. Properly inserted stays produce no endothelial injury or exposure of collagen that leads to scarring. An endoluminal stent, especially one with a bare metal surface, facilitates the thrombogenicity associated with any antecedent angioplasty that resulted in a dissection of the lumen wall, additionally promoting intimal hyperplasia and constrictive remodelling.

An endoluminal stent in the airway or the esophagus can serve as a scaffold for the spread of infection; the stent accumulates detritus, and if protruding into, chronically irritating, and thus eventually breaking through the lumen lining, will inoculate the lumen wall. Sterile miniballs and stays implanted subadventitiously or subfibrosally under sterile conditions will cannot act to spread infection. The means described herein necessitate the administration of clot-preventing medication (platelet blockade); however, without a metal object left within the lumen, the duration for such treatment is much shorter. Absorbable endoluminal stents avoid protracted thrombogenicity also but should not be used for combined or single pass stenting angioplasty, and cannot be used to prevent stenoses at locations where these can be anticipated, as addressed below in this section.

In contrast to an endoluminal stent, a circumvascular elastic stent that complies with changes in caliber of the substrate vessel or duct without compressing the adventitia is not a constant source of irritation. Especially for vasculopathy that calls for stenting alone, extraluminal stenting, because it leaves the lumen clear, is less susceptible to adverse sequelae. The measures employed to avert embolism are discussed below. The typically submillimetric, sometimes no larger than 0.4 millimeter or 400 micrometer trajectories of miniballs quickly seal and quickly heal, and even though recommending the short-term administration of anti-platelet agents and anti-coagulants, do not represent a source of continued irritation or thrombogenicity. Necessarily depending upon the dimensions of the ductus where potential applications encompass those pediatric and veterinary, those in the vascular tree, the airway, and the gastro-intestinal tract, estimated in the abstract, miniballs, for example, can range in diameter anywhere from around 0.1 to 4.0 millimeters.

Stenting of the superior vena cava that avoids the lumen without encroaching upon the ascending aorta, for example, can avert the adverse sequelae of endoluminal stenting, to include aortic perforation, migration, reocclusion (Kappert, U., Schulz, C. G., Waldow, T., Tugtekin, S. M., Alexiou, C., and Matschke, K. 2006. "Perforation of the Ascending Aorta: A Late Complication of Superior Vena Cava Stenting," *Thoracic and Cardiovascular Surgeon* 54(1):63-65), albeit rare, pericardial tamponade (Martin, M., Baumgartner, I., Kolb, M., Triller, J., and Dinkel, H. P. 2002. "Fatal Pericardial Tamponade after Wallstent Implantation for Malignant Superior Vena Cava Syndrome," *Journal of Endovascular Therapy* 9(5):680-684), and similar injuries (Recto, M. R., Bousamra, M., and Yeh, T. Jr. 2002. Late Superior Vena Cava Perforation and Aortic Laceration after Stenting to Treat Superior Vena Cava Syndrome Secondary to Fibrosing Mediastinitis," *Journal of Invasive Cardiology* 14(10):624-629).

While inflammation is often pan-arteritic (see, for example, Higuchi, M. L., Gutierrez, P. S., Bezerra, H. G., Palomino, S. A., Aiello, V. D., Silvestre, J. M., Libby, P., Ramires, J. A. 2002. "Comparison Between Adventitial and Intimal Inflammation of Ruptured and Nonruptured Atherosclerotic Plaques in Human Coronary Arteries," *Arquivos Brasileiros Cardiologia* 79(1):20-24), and prior to atherectomy, adventitial inflammation might conceivably contribute to plaque instability (see, for example, Hu, C. L., Xiang, J. Z., Hu, F. F., and Huang, C. X. 2007. "Adventitial Inflammation: A Possible Pathogenic Link to the Instability of Atherosclerotic Plaque," *Medical Hypotheses* 68(6): 1262-1264), avoidance of the lumen eschews the many additional complications that may arise within the lumen and is advantageous in certain conditions that involve inflammation of the intima, such as Takayasu disease (Takayasu arteritis, brachiocephalic arteritis, Martorell;'s syndrome, reversed coarctation, pulseless disease, aortic arch syndrome, occlusive thromboaortopathy) when in-stent restenosis could otherwise pose a problem (Mieno, S., Horimoto, H., Arishiro, K., Negoro, N., Hoshiga, M., Ishihara, T., Hanafusa, T., and Sasaki, S. 2004. "Axillo-axillary Bypass for in-Stent Restenosis in Takayasu Arteritis," *International Journal of Cardiology* 94(1):131-132) and antiphospholipid (Hughes) syndrome (see, for example, Ben-Ami, D., Bar-Meir, E., and Shoenfeld, Y. 2006. "Stenosis in Antiphospholipid Syndrome: A New Finding with Clinical Implications," *Lupus* 15(7):466-472).

Outside the lumen. not interfering with flow-through and little if at all with motility, an extraluminal stent in the gut, unlike an endoluminal stent, does not serve as a scaffold for the accumulation if not accretion of debris, and outside the forceful contractive waves, is inherently less susceptible to migration (Suzuki, N., Saunders, B. P., Thomas-Gibson, S., Akle, C., Marshall, M., and Halligan, S. 2004. "Colorectal Stenting for Malignant and Benign Disease: Outcomes in Colorectal Stenting," *Diseases of the Colon and Rectum* 47(7):1201-1207). End-ties, end-straps, and sectional stent-jackets increase resistance to displacement. The advantage in an absorbable stent being that it does not remain as a permanent irritant and cause of adverse sequelae, no endoluminal stent is suited to preventing stenoses at locations where the appearance of a threatening lesion can be anticipated.

The ability to do so is of long standing, based upon such factors as hemodynamic sheer stress (see, for example, Malek, A. M., Alper, S. L., and Izumo, S. 1999. "Hemodynamic Shear Stress and Its Role in Atherosclerosis," *Journal of the American Medical Association* 282(21):2035-2042; Malek, A. M. and Izumo, S. 1995. "Control of Endothelial Cell Gene Expression by Flow," *Journal of Biomechanics* 28(12):1515-1528; Hugh, A. E. and Fox, J. A. 1970. "The Precise Localisation of Atheroma and Its Association with Stasis at the Origin of the Internal Carotid Artery—A Radiographic Investigation," *British Journal of Radiology* 43(510):377-383) and wall structure (see, for example, Langheinrich, A. C., Michniewicz, A., Bohle, R. M., and Ritman, E. L. 2007. "Vasa Vasorum Neovascularization and Lesion Distribution Among Different Vascular Beds in ApoE-/-/LDL-/- Double Knockout Mice," *Atherosclerosis* 191(1):73-81; Tracy, R. E. 2005. "Evidence Concerning Resistance to Atheroma by Media-like Islands in the Intima of Coronary Arteries," *Atherosclerosis* 178(1):49-56).

Current absorbable stents also tend to lack adequate strength and disintegrate too slowly, restenosis rates are high, and making these drug-eluting will likely result in additional endothelial dysfunction. Whereas endoluminal stents are placed translumenally with only one entry portal required, the extraluminal stents to be described require direct access to the treatment site to place stays and the stent-jacket. Where a preliminary ablation or angioplasty is not performed, those using stays involve no transluminal component and require no separate radial, brachial, or femoral entry. Those that use miniball implants require both transluminal access and separate direct entry through a small incision and dissection to allow the vessel or duct to be mantled about with the stent-jacket, clasp-jacket, or impasse-jacket.

Extraluminal stenting is unintended for use with ductus invested within tissue, such as the pancreatic duct or an anomalously submyocardial coronary artery that courses (tunnels, bridges) through muscle. However, ablation and ablation and angioplasty-capable barrel-assemblies can be used to ablate or atherectomize, and/or implant medication or irradiating seeds within the walls of ductus however intimately surrounded by tissue. When more distantly mounted patch or clasp-magnets or a magnet-jacket, as addressed below in sections of like title, cannot be used, an endoluminal stent must be used instead.

The uncomplicated placement of an extraluminal stent initially imposes more trauma than does the uncomplicated insertion of a properly sized endoluminal stent; however, this trauma heals quickly, and once placed, the extraluminal stent remains substantially risk-free. Improved outcomes can justify incisional over transluminal procedures (see, for example, Derksen, W. J., Gisbertz, S. S., Pasterkamp, G., De Vries, J. P., and Moll, F. L. 2008. "Remote Superficial Femoral Artery Endarterectomy," *Journal of Cardiovascular Surgery* (Turin, Italy) 49(2):193-198). By contrast, the trauma associated with the placement of an endoluminal stent consists of injury to the intima; however, if the long-term prognosis is essentially the same, the ability to avoid surgery is an advantage.

The trauma of inserting an extraluminal stent consists of the small incision and dissection to gain access to the tunica fibrosa or adventitia of the ductus to be stented, and injury, rarely significant, to the periductal vasculature and innervation—in blood vessels, the vasa and nervi vasora, which will usually be too profuse, dispersed, and obscured to avoid completely, especially since the vasa vasorum of a diseased vessel is likely to have become elaborated through neovascularization (see, for example, Di Stefano, R., Felice, F., and Balbarini, A. 2009. "Angiogenesis as Risk Factor for Plaque Vulnerability," *Current Pharmaceutical Design* 15(10): 1095-1106; Doyle, B. and Caplice, N. 2007. "Plaque Neovascularization and Antiangiogenic Therapy for Atherosclerosis," *Journal of the American College of Cardiology* 49(21):2073-2080; Jain, R. K., Finn, A. V., Kolodgie, F. D., Gold, H. K., and Virmani, R. 2007. "Antiangiogenic Therapy for Normalization of Atherosclerotic Plaque Vasculature: A Potential Strategy for Plaque Stabilization," *Nature Clinical Practice. Cardiovascular Medicine* 4(9): 491-502; Ritman, E. L. and Lerman, A. 2007. "The Dynamic Vasa Vasorum," *Cardiovascular Research* 75(4):649-658; Moreno, P. R., Purushothaman, K. R., Zias, E., Sanz, J., and Fuster, V. 2006. "Neovascularization in Human Atherosclerosis," *Current Molecular Medicine* 6(5):457-447; Virmani, R., Kolodgie, F. D., Burke, A. P., Finn, A. V., Gold, H. K., Tulenko, T. N., Wrenn, S. P., and Narula, J. 2005. "Atherosclerotic Plaque Progression and Vulnerability to Rupture: Angiogenesis as a Source of Intraplaque Hemorrhage," *Arteriosclerosis, Thrombosis, and Vascular Biology* 25(10): 2054-2061; Heistad, D. D. and Armstrong, M. L. 1986. "Blood Flow Through Vasa Vasorum of Coronary Arteries in Atherosclerotic Monkeys," *Arteriosclerosis* 6(3):326-331).

Since at least 1996, the application of an external stent has been known to reduce intimal thickening in vein grafts (Izzat, M. B., Mehta, D., Bryan, A. J., Reeves, B., Newby, A. C., and Angelini, G. D. 1996. "Influence of External Stent Size on Early Medial and Neointimal Thickening in a Pig Model of Saphenous Vein Bypass Grafting," *Circulation* 94(7):1741-1745; Angelini, G. D., Izzat, M. B., Bryan, A. J., and Newby, A. C. 1996. "External Stenting Reduces Early Medial and Neointimal Thickening in a Pig Model of Arteriovenous Bypass Grafting," *Journal of Thoracic and Cardiovascular Surgery* 112(1):79-84; Vijayan, V., Shukla, N., Johnson, J. L., Gadsdon, P., Angelini, G. D., Smith, F. C., Baird, R., and Jeremy, J. Y. 2004. "Long-term Reduction of Medial and Intimal Thickening in Porcine Saphenous Vein Grafts with a Polyglactin Biodegradable External Sheath," *Journal of Vascular Surgery* 40(5):1011-1019; Jeremy, J. Y., Bulbulia, R., Johnson, J. L., Gadsdon, P., Vijayan, V., Shukla, N., Smith, F. C., and Angelini, G. D. 2004. "A Bioabsorbable (Polyglactin), Nonrestrictive, External Sheath Inhibits Porcine Saphenous Vein Graft Thickening," *Journal of Thoracic and Cardiovascular Surgery* 127(6): 1766-1772. The effect is probably due to structural reinforcement by the stent of the graft vessel wall, which eliminates the need for adaptive strengthening by proliferation of smooth muscle cells.

Such external stents, absorbable or simple tubes that are usually made of woven polyethylene terephthalate (polyester, Terylene®, Dacron®), are fundamentally different than the stent-jackets described herein, and none of the claims appended hereto would read upon any such prior art device. Prior art external stents, some absorbable, are inwardly restraining but not lumen-patenting, and those made of solid plastic tubing are incapable of adapting to and remaining with the substrate ductus while complying with its autonomic movement during overall enlargement (expansion) or reduction (contraction). By contrast, the extraluminal stents to be described are elastic and restrained inwardly, in minimal diameter, while compliant outwardly.

Specifically, such a stent girds about an artery at its diastolic (narrowest, quiescent) diameter and complies with, that is, expands in response to, the outward force exerted by the pulse. In the esophagus and gut, a special spine and ribs or reach-around arms configured stent-jacket as described above in the sections entitled Concept of the Extraluminal Stent, Spine and Ribs Type Stent-jackets, and The Extraductal Component of the Extraluminal Stent and the Means for its Insertion is matched in diameter to the gauge of the ductus when contracted but expands to the larger quiescent diameter and even that of an expanding bolus without physiologically significant resistance. The outward retractive force imposed by the stent is easily overcome by that of the peristaltic waves that pass therethrough.

However, in structure, function, and application, the circumductal (periductal), specifically venous as well as arterial circumvascular (perivascular, periductal) stents to be described herein are fundamentally different from the various cuffs and sheaths to which similar terminology has been applied in the past (see, for example, Zou, R. J., Zou, L. J., Huang, S. D., Wang, Y., Han, L., Ji, G. Y., and Xu, Z. Y. 2007. "Effect of External Stents on Prevention of Intimal Hyperplasia in a Canine Vein Graft Model," *Chinese Medical Journal* (in English) 120(24):2264-2267; Izzat, M. B., Teng, Z. Z., Ji, G. Y., Chu, H. J., Li, Z. Y., Zou, L. J., Xu, Z. Y., and Huang, S. D. 2007. "Does PGA External Stenting Reduce Compliance Mismatch in Venous Grafts?," *Biomedical Engineering Online* 6:12; Jeremy et al. 2004 cited above; Izzat et al. 1996 cited above; Froehlich, P., Seid, A. B., Kearns, D. B., Pransky, S. M., and Morgon, A. 1995. "Use of Costal Cartilage Graft as External Stent for Repair of Major Suprastomal Collapse Complicating Pediatric Tracheotomy," *Laryngoscope* 105(7 Part 1):774-775).

While free to expand and contract and thus comply with pulsatile and vasotonic-autonomic-renin-angiotensin system regulated changes in gauge, the elastic circumvascular stent-jacket, in marked contrast to a conventional endoluminal stent, is not susceptible to deformation with possible migration, deformation or ensuing migration induced abrupt closure and infarction (see, for example, Nakahara, T., Sakamoto, S., Hamasaki, O., and Sakoda, K. 2003. "Double Wire Technique for Intracranial Stent Navigation," *Journal of Vascular and Interventional Radiology* 14(5):667-668), and thrombogenesis from an impact, the intromission of a catheter (Brilakis, E. S., Roesle, M., and Banerjee, S. 2007. "Stent Deformation after Catheter Advancement through a Recently Deployed Self-expanding Stent: Diagnosis, Mechanism and Correction," *Journal of Invasive Cardiology* 19(1):46), or during balloon expansion if not spontaneously following placement (Yallampalli, S., Zhou, W., Lin, P. H., Bush, R. L., and Lumsden, A. B. 2006. "Delayed Deformation of Self-expanding Stents after Carotid Artery Stenting for Postendarterectomy Restenoses," *Journal of Vascular Surgery* 44(2):412-415; Rosenfield, K., Schainfeld, R., Pieczek, A., Haley, L., and Isner, J. M. 1997. "Restenosis of Endovascular Stents from Stent Compression," *Journal of the American College of Cardiology* 1997 29(2):328-338; Johnson, S. P., Fujitani, R. M., Leyendecker, J. R., and Joseph, F. B. 1997. "Stent Deformation and Intimal Hyperplasia Complicating Treatment of a Post-carotid Endarterectomy Intimal Flap with a Palmaz Stent," *Journal of Vascular Surgery* 25(4):764-768). Extraluminal, a stent-jacket can be flexible and compliant in any length, can be varied in thickness from end to end or side-slit edge to side-slit edge, or can be varied thus by heat treatment, meaning mold-shape biased to provide flexibility or compliance that is nonuniform or eccentric even through curves.

Implantation with stays avoids the lumen entirely. A recent trend favoring stenting without a preceding angioplasty ("direct stenting") (see, for example, Kiemeneij, F, Serruys P W, Macaya C, Rutsch W, Heyndrickx G, and 10 other authors, 2001. "Continued Benefit of Coronary Stenting Versus Balloon Angioplasty: Five-year Clinical Follow-up of Benestent-I Trial," *Journal of the American College of Cardiology* 37(6):1598-1603; Versaci, F., Gaspardone, A., Tomai, F., Proietti, I., Ghini, A. S., Altamura, L., Andò, G., Crea, F., Gioffrè, P. A., and Chiariello, L. 2004. "A Comparison of Coronary Artery Stenting with Angioplasty for Isolated Stenosis of the Proximal Left Anterior Descending Coronary Artery: Five Year Clinical Follow-up," *Heart* 90(6):672-675; Versaci, F., Gaspardone, A., Tomai, F., Crea, F., Chiariello, L., and Gioffrè, P. A. 1997. "A Comparison of Coronary-artery Stenting with Angioplasty for Isolated Stenosis of the Proximal Left Anterior Descending Coronary Artery," *New England Journal of Medicine* 336(12):817-822) minimizes if it does not eliminate endothelial injury, and would be enhanced were the transluminal step eliminated entirely. Minimizing the number of passes through the entry wound reduces operating time and probably the potential for injury to the endothelium and irritation of the access wound (see, for example, Archbold, R. A., Robinson, N. M., Schilling, R. J. 2004. "Radial Artery Access for Coronary Angiography and Percutaneous Coronary Intervention," *British Medical Journal* 329(7463):443-446).

8e. Accommodation of the Adventitial Vasculature, Innervation, and Perivascular Fat Larger ductus may have an adventitial vasculature that must not be constricted or injured longer than would quickly recover. The coronary arteries in particular, have vasa vasora that centrally implicated in the development of atherosclerosis and atherothrombosis (see, for example, Langheinrich, A. C, Kampschulte, M., Buch, T., and Bohle, R. M. 2007. "Vasa Vasorum and Atherosclerosis—Quid novi?," *Thrombosis and Haemostasis* 97(6):873-879; Langheinrich, A. C., Michniewicz, A., Sedding, D. G., Walker, G., Beighley, P. E., Rau, W. S., Bohle, R. M., and Ritman, E. L. 2006. "Correlation of Vasa Vasorum Neovascularization and Plaque Progression in Aortas of Apolipoprotein E(-/-)/Low-density Lipoprotein(-/-) Double Knockout Mice," *Arteriosclerosis, Thrombosis, and Vascular Biology* 26(2): 347-352), must be accommodated and not induced to perpetuate disease through compression by a continuous collar.

Perivascular fat, support vasa and nervora of which the function is essential to the health of the substrate ductus is avoided through the use of a small segmented or spine and ribs type stent-jacket. This way, only so much of the surrounding tissue as is necessary to gain thickness and hardenable tissue for ductus-intramural implantation is included with the ductus in the stent. Perivascular fat appears to be essential to normal endothelial function but harmful when excessive (Szasz, T. and Webb, R. C. 2012. "Perivascular Adipose Tissue: More than Just Structural Support," *Clinical Science* (London) 122(1):1-12; Miao, C. Y. and Li, Z. Y. 2012. "The Role of Perivascular Adipose Tissue in Vascular Smooth Muscle Cell Growth," *British Journal of Pharmacology* 165(3):643-658; Lu, C., Su, L. Y., Lee, R. M., and Gao, Y. J. 2010. "Mechanisms for Perivascular Adipose Tissue-mediated Potentiation of Vascular Contraction to Perivascular Neuronal Stimulation: The Role of Adipocyte-derived Angiotensin II," *European Journal of Pharmacology* 634(1-3):107-112; Payne et al. Op cit., section above entitled Field of the Invention; Gao, Y. J. 2007. "Dual Modulation of Vascular Function by Perivascular Adipose Tissue and Its Potential Correlation with Adiposity/Lipoatrophy-related Vascular Dysfunction," *Current Pharmaceutical Design* 13(21):2185-2192).

For a defined segment, the relative contribution to endothelial function by periadvental fat as a sum over the arterial tree and that local to the segment longitudinally and radially has not been defined. In this circumstance, a coronary artery heavily invested in fat is dissected free of all the fat but that proximate before jacketed. The difficulty of access due to tunneling, adhesions, or a lack of clearance, and the extent of dissection allowed must rest upon clinical judgment. In an elderly patient, the expediency of endoluminal stenting will normally override the object of imparting better function over the long term. To expedite placement by eliminating prominences of nonadventitial tissue surrounding the ductus which would compress the ductus if included within the stent-jacket, the edges of the stent-jacket can be made incisive. If metal, the tips of the ribs in a spine and ribs configured stent-jacket can be honed, for example.

Atherosclerosis of the coronary arteries being the condition most often demanding the reinstatement and sustainment of luminal patency, these arteries are at the same time those ductus most likely to benefit from and challenging to extraluminal stenting. Even though the adventitia and perivascular fat are actively involved in vascular physiology and pathology, a stent outside the flow of contents, without radially outward protrusion into the intima, and posing negligible perivascular compression should prove overall advantageous. Provided the extraluminal stent is properly configured, is compliant both circumferentially and longitudinally, and is nonconstricting, the injured tissue regenerates and adapts to its presence. Supported medically, generally to include a statin drug, the disease-angioproliferated vasa vasorum should regress.

Applied to a coronary artery, for example, use of the minimal effective magnetic field strength, inclusion of side-openings (perforations, fenestrae), and a base-tube of suitable resilience in the correct internal diameter with cushion lining as addressed below in the section entitled Necrosis- and Atherogenesis-noninducing Conformation, results in the imposition of little if any compressive force against the adventitial microvasculature. Further to avoid compressing the vasa vasorum if necessary, extraluminal segmental or chain-stents, addressed below in the section entitled Sectional, or Chain-stents, Segmented and Articulated, which subdivide a continuous stent into short sections or substents, can be used. Regardless of the type or size ductus treated, the continuous span (length) of adventitia enclosed can be minimized by using a stent-jacket with perforations through the base-tube and cushion lining and/or one divided longitudinally into an articulated train of sub-stents, as addressed below in the same section.

A foam lining allows slight protrusions of the jacket adaxially that would otherwise irritate the substrate ductus and accommodates deviation from cylindricality of the segment to be encircled. For the present purpose, it allows some tissue surrounding the ductus to be included within the stent- or impasse-jacket whether perivascular fat surrounding an artery or tissue surrounding a vein, as addressed below in the section entitled Stent- and Shield-jacket Moisture barrier-coated viscoelastic polyurethane foam Linings. An extraluminal stent of larger internal diameter can be chosen to allow a uniform layer of white perivascular (periadventitial) fat through which the vasa vasorum courses to be included without hypoxic consequence or loss in intrinsic vasodilatory (vasohypotonic) support; indeed, the fat contributes additional cushioning.

Incised vasa vasora regenerate (see, for example, Santilli, S. M., Wernsing, S. E., and Lee, E. S. 2000. "Transarterial Wall Oxygen Gradients at a Prosthetic Vascular Graft to Artery Anastomosis in the Rabbit," *Journal of Vascular Surgery* 31(6):1229-1239). With a stent-jacket that minimally interferes with healing, unavoidable trauma to the perivascular microvasculature should prove sustainable and heal in less than two months. Much if not all of the vasa vasorum and vascular innervation invested within periadventitial fat can be included within the stent-jacket. Alternatively, based upon the 'perivascular adipose tissue dysfunction' concept (Guzik, T. J., Marvar, P. J., Czesnikiewicz-Guzik, M., and Korbut, R. 2007. Perivascular Adipose Tissue as a Messenger of the Brain-vessel Axis: Role in Vascular Inflammation and Dysfunction," *Journal of Physiology and Pharmacology* 58(4):591-610), and provided that to do so would not result in untenable injury upon the substrate artery of the vasa vasorum, functionally altered and pathologically destructive fat can be removed before the stent-jacket is applied (see Chaldakov, G. N., Tonchev, A. B., Stankulov, I. S., Ghenev, P. I. Fiore, M., Aloe, L., Rančič, G., Panayotov, P., and Kostov, D. D. 2007. "Periadventitial Adipose Tissue (Tunica Adiposa): Enemy or Friend Around?," *Archives of Pathology and Laboratory Medicine* 131(12):1766-1767; Pagano, P. J. and Gutterman, D. D. 2007. "The Adventitia: The Outs and Ins of Vascular Disease," *Cardiovascular Research* 75(4):636-639; Gao, Y. J., Lu, C., Su, L. Y., Sharma, A. M., and Lee, R. M. 2007. "Modulation of Vascular Function by Perivascular Adipose Tissue: The Role of Endothelium and Hydrogen Peroxide," *British Journal of Pharmacology* 151(3):323-331; Stern, N. and Marcus, Y. 2006. "Perivascular Fat: Innocent Bystander or Active Player in Vascular Disease?," *Journal of the Cardiometabolic Syndrome* 1(2): 115-120).

In the rabbit carotid artery, opening the sides of the collar when the inlet and outlet remain flush to the adventitia does not avert neointimal thickening (De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930). Neither constriction nor constraint toward the margins apply to the extraluminal stent described herein, which should not induce neointimal thickening.

Residual muscle cell proliferation and neovascularization left by the disease which did not spontaneously regress over time is reduced with the aid of drugs. Once placed, an extraluminal stent avoids the inner (adluminal) laminae of the lumen wall and should become integrated into the tissue as to cause little if any irritation. In an artery, avoidance of the lumen and minimization of irritation afford the intima and media the opportunity to heal from intrinsic as well as responding iatrogenic insults. Any ductus that requires treatment is likely to present an adluminal condition that makes preferable the placement of a stent peripheral or abluminal thereto and away from the passage of contents.

8f. Necrosis and Atherogenesis-Noninducing Conformation of Stent-Jackets

The advantages in using stays to avoid the lumen or miniballs to minimize its involvement once placed notwithstanding, the fact that collaring the normal rabbit carotid artery with a closed silicone elastomer (Dow Corning Silastic®) collar is precisely a standard method for quickly inducing atherosclerosis in the laboratory (see, for example, Hirosumi, J., Nomoto, A., Ohkubo, Y., Sekiguchi, C., Mutoh, S., Yamaguchi, I., and Aoki, H. 1987. "Inflammatory Responses in Cuff-induced Atherosclerosis in Rabbits," *Atherosclerosis* 64(2-3):243-254; Booth, R. F. G., Martin, J. F., Honey, A. C., Hassall, D. G., Beesley, J. E., and Moncada, S. 1989. "Rapid Development of Atherosclerotic Lesions in the Rabbit Carotid Artery Induced by Perivascular Manipulation," *Atherosclerosis* 76(2-3):257-268; Kockx, M. M., De Meyer, G. R. Y., Jacob, W. A., Bult, H., and Herman, A. G. 1992. "Triphasic Sequence of Neointimal Formation in the Cuffed Carotid Artery of the Rabbit," *Arteriosclerosis and Thrombosis* 12(12):1447-1457; Puranik, R., Bao, S., Nobecourt, E., Nicholls, S. J., Dusting, G. J., Barter, P. J., Celermajer, D. S., and Rye, K. A. 2008. "Low Dose Apolipoprotein A-I Rescues Carotid Arteries from Inflammation in Vivo," *Atherosclerosis* 196(1):240-247), would appear to nullify any potential benefit from a circumvascular stent (see also von der Thüsen, J. H., van Berkel, T. J. C., and Biessen, E. A. L. 2001. "Induction of Rapid Atherogenesis by Perivascular Carotid Collar Placement in Apolipoprotein E-deficient and Low-density Lipoprotein Receptor-deficient Mice," *Circulation* 103(8):1164-1170; Reel, B., Ozkal, S., Islekel, H., Ozer, E., and 5 others 2005. "The Role of Endothelin Receptor Antagonism in Collar-induced Intimal Thickening and Vascular Reactivity Changes in Rabbits," *Journal of Pharmacy and Pharmacology* 57(12):1599-1608).

However, even though medial smooth muscle cell proliferation, negligible interruption to transmural flow (De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930), and the infiltration of leukocytes into the media (Hagihara, H., Nomoto, A., Mutoh, S., Yamaguchi, I., and Ono, T. 1991. "Role of Inflammatory Responses in Initiation of Atherosclerosis: Effects of Anti-inflammatory Drugs on Cuff-induced Leukocyte Accumulation and Intimal Thickening of Rabbit Carotid Artery," *Atherosclerosis* 91(1-2):107-116) might not be completely eliminated, a perivascular collar with open sides and wider ends was found to minimize if not eliminate the adverse consequences obtained when the collar was close-sided with ends that fit flush to the artery (De Meyer et al. 1997).

Unlike atherogenesis inducing collars, the stent-jackets, clasp-jackets, and impasse-jackets described herein are not flush fit at the ends thus, and are lined with viscoelastic or low-resilience polyurethane foam (moisture barrier-coated viscoelastic polyurethane foam). The cushioned vasa vasorum should adapt to negligible variation in pressure with the pulse, and the fibrous adventitia proper should see little if any variation as would excite a proliferative response at all (see, for example, Haurani, M. J. and Pagano, P. J. 2007. "Adventitial Fibroblast Reactive Oxygen Species as Autacrine and Paracrine Mediators of Remodeling: Bellwether for Vascular Disease?," *Cardiovascular Research* 75(4): 679-689). With a suitably configured jacket, smooth muscle cell proliferation and obstruction to transmural fluid transport as leads to the retention of toxic metabolites and/or cytokines (De Meyer et al. 1997) should not occur. The susceptibility to medical management of adverse sequelae in the rabbit model is addressed below in the section entitled Local Release of Drugs by Miniballs and Stays.

That the vasa vasorum must not be stripped away (Wilens, S. L., Malcolm, J. A., and Vasquez. J. M 1965. "Experimental Infarction (Medial Necrosis) of the Dog's Aorta," *American Journal of Pathology* 47(4):695-711) compressed (Ritman, L. and Lerman, A. 2007. "The Dynamic Vasa Vasorum," *Cardiovascular Research* 75(4):649-658) or obstructed (see, for example, Ravnskov, U. and McCully, K. S. 2009. "Review and Hypothesis: Vulnerable Plaque Formation from Obstruction of Vasa Vasorum by Homocysteinylated and Oxidized Lipoprotein Aggregates Complexed with Microbial Remnants and LDL Autoantibodies," *Annals of Clinical and Laboratory Science* 39(1):3-16; Martin, J. F., Booth, R. F., and Moncada, S. 1991. "Arterial Wall Hypoxia Following Thrombosis of the Vasa Vasorum is an Initial Lesion in Atherosclerosis," *European Journal of Clinical Investigation* 21(3):355-359; Martin, J. F., Booth, R. F., and Moncada, S. 1990. "Arterial Wall Hypoxia Following Hyperfusion Through the Vasa Vasorum is an Initial Lesion in Atherosclerosis," *European Journal of Clinical Investigation* 20(6):588-592; with additional references to follow) imposes severe constraints on the design of a perivascular stent.

Probably anything that interferes with the release of nitric oxide from the endothelium initiates atherosclerosis, and the arterial walls of the coronary and carotid artery are subject to inflammation and occlusion from both outside (vasa vasora) and inside (from within the lumen). Compression from outside not only deprives the substrate vessel of oxygen and nutrients but nitric oxide. Endoluminally, the shear stress at bifurcations such as at the branching of the common into the internal and external carotids and the abdominal aorta into the iliac and then again into the right and left internal and external iliac arteries likewise pose compression inimical to the unimpeded delivery of saturated blood to which the incidence of plaque at these sites attest.

For this reason, stent-jackets always incorporate a moisture barrier moisture protected lining of viscoelastic polyurethane foam to gently envelope rather than compress the fine vessels serving substrate ductus. Sufficient retractive force must be exerted to preserve luminal patency without compressing the vasa vasorum of blood vessels or the small vessels that supply the walls of larger vessels, the airway, esophagus, and gut, for example. Absent means for preventing compression of its peripheral blood supply, no segment of any ductus greater in extent than receives collateral circulation should be compressed.

The avoidance of mechanical distortion by compression or distention, perhaps the more so in a coronary artery with its profuse and endarterially configured (citations below) vasa vasorum (see Kwon, H. M., Sangiorgi, G., Ritman, E. L., Lerman, A., McKenna, C., Virmani, R., Edwards, W. D., Holmes, D. R., and Schwartz, R. S. 1998. "Adventitial Vasa Vasorum in Balloon-injured Coronary Arteries: Visualization and Quantitation by a Microscopic Three-dimensional Computed Tomography Technique," *Journal of the American College of Cardiology* 32(7):2072-2080), necessitates the use of minimal magnetic field intensity combined with side openings and a base-tube lined with a suitable cushioning material such as a high density moisture barrier-coated viscoelastic polyurethane foam (viscoelastic flexible polyurethane foam, slow recovery foam, temper foam) of lower indentation force deflection (indentation load deflection) and higher phase relaxation (phase change) temperature in a thickness sufficient to minimize if not eliminate perivascular compression.

The use of chain-stents also serve to minimize the extent of adventitia closed off from its normal surrounding. While the mechanism whereby the collar induces intimal thickening remains to be fully elucidated, the substantial alleviation in adverse consequences of placing a collar about an artery when the collar is open-sided or perforated has been well established empirically (De Meyer et al. 1997); George, S. J., Izzat, M. B., Gadsdon, P., Johnson, J. L., Yim, A. P., Wan, S., Newby, A. C., Angelini, G. D., and Jeremy, J. Y. 2001. "Macro-porosity is Necessary for the Reduction of Neointimal and Medial Thickening by External Stenting of Porcine Saphenous Vein Bypass Grafts," *Atherosclerosis* 155(2): 329-336; Mehta, D., George, S. J., Jeremy, J. Y., Izzat, M. B., Southgate, K. M., Bryan, A. J., Newby, A. C., and Angelini, G. D. 1998. "External Stenting Reduces Long-term Medial and Neointimal Thickening and Platelet Derived Growth Factor Expression in a Pig Model of Arteriovenous Bypass Grafting," *Nature Medicine* 4(2):235-239).

With the extraluminal form of stenting described, differential movement between the stent-jacket and the adventitia is minimized, so that rather than to pulsate within a substantially stationary collar, for example, the artery pulsates with little resistance from the circumvascular stent, which acts as if it were a part of the vessel wall, the pulse seeing no significant resistance passing through the stented segment. Perforation and segmentation of longer base-tubes, to include the foam lining, into a train of joined substents, or a chain-stent, allows the adventitia contact with the surrounding environment but reduces the resilience of the base-tube, weakens it, and if not encapsulated within a protective polymeric coating, exposes more of its surface to chemical attack.

Breakdown of the base-tube not only interferes with stent function but can initiate a pathogenic cascade that can lead to necrosis. Exposure to the acidity and enzymes of the internal environment places a demand upon the material of the base-tube for retaining chemical integrity and pliancy. A thicker base-tube or one made of a more resilient material or combination of materials such as a suitable coextrusion is used. Newer materials suitable for making base-tubes able to withstand the internal environment for a long time are specified below in the section entitled Internal Environment-resistant Base-tube Polymers, Metals, and Combinations Thereof.

8g. Means for Accommodating the Vasa and Nervi Vasora with Special Reference to the End-Arterial Form and Neo-vascularization of the Coronary Arteries Even an extraluminal stent that is fully compliant with pulsatile and tonic function and nonconstrictive is likely to be more challenging to apply to a coronary artery than to any other type ductus, to include other arteries, because:

a. The vasa vasora of the coronary arteries tend to be even more profuse than are those of arteries generally (Hildebrandt, H. A., Gössl, M., Mannheim, D., Versari, D., and seven other authors 2008. "Differential Distribution of Vasa Vasorum in Different Vascular Beds in Humans," *Atherosclerosis* 2008 199(1):47-54; Galili, O., Herrmann, J., Woodrum, J., Sattler, K. J., Lerman, L. O., and Lerman, A. 2004. "Adventitial Vasa Vasorum Heterogeneity Among Different Vascular Beds," *Journal of Vascular Surgery* 40(3):529-535; Galili, O., Sattler, K. J., Herrmann, J., Woodrum, J., Olson, M., Lerman, L. O., and Lerman, A. 2005. "Experimental Hypercholesterolemia Differentially Affects Adventitial Vasa Vasorum and Vessel Structure of the Left Internal Thoracic and Coronary Arteries," *Journal of Thoracic and Cardiovascular Surgery* 129(4):767-772), and, b. The vessels of coronary artery vasa vasora are end-arterial, or tree-, rather than network- or plexus-configured (Gössl, M., Malyar, N. M., Rosol, M., Beighley, P. E., and Ritman, E. L. 2003. "Impact of Coronary Vasa Vasorum Functional Structure on Coronary Vessel Wall Perfusion Distribution," *American Journal of Physiology. Heart and Circulatory Physiology* 285(5):H2019-H2026; Gössl, M., Rosol, M., Malyar, N. M., Fitzpatrick, L. A., Beighley, P. E., Zamir, M., and Ritman, E. L. 2003. "Functional Anatomy and Hemodynamic Characteristics of Vasa Vasorum in the Walls of Porcine Coronary Arteries," *Anatomical Record. Part A, Discoveries in Molecular, Cellular, and Evolutionary Biology* 272(2):526-537; Kwon et al. 1998. "Adventitial Vasa Vasorum in Balloon-injured Coronary Arteries: Visualization and Quantitation by a Microscopic Three-dimensional Computed Tomography Technique," *Journal of the American College of Cardiology* 32(7):2072-2080; Järvilehto, M. and Tuohimaa, P. 2009. "Vasa Vasorum Hypoxia:

Initiation of Atherosclerosis," *Medical Hypotheses* 73(1): 40-41; Ravnskov and McCully 2009 op cit.), and c. An artery suited for treatment with the means described herein will almost always be atheromatous, the vasa vasorum having already undergone neovascularization (Granada, J. F. and Feinstein, S. B. 2008. "Imaging of the Vasa Vasorum," *Nature Clinical Practice. Cardiovascular Medicine Supplement* 2:S18-S25; Kerwin, W. S., Oikawa, M., Yuan, C., Jarvik, G. P., and Hatsukami, T. S. 2008. "MR Imaging of Adventitial Vasa Vasorum in Carotid Atherosclerosis," *Magnetic Resonance in Medicine* 59(3):507-514; Goertz, D. E., Frijlink, M. E., Krams, R., de Jong, N., and van der Steen, A. F. 2007. "Vasa Vasorum and Molecular Imaging of Atherosclerotic Plaques Using Nonlinear Contrast Intraductal Ultrasound," *Netherlands Heart Journal* 15(2):77-80), making the vasa vasorum more difficult to mantle about.

An end-arterial blood supply connotes a lesser degree if not a complete lack of overlap in the perfusion areas or territories of adjacent root segments of the vasa vasorum tree, hence, a relative lack of collateral circulation in the perfusion and drainage areas of the substrate arterial wall. Apparently unique in this regard, even if experiments on the aorta, carotid, or internal thoracic arteries, for example, disclosed an ability to adapt to a properly configured extraluminal stent, these results would not necessarily apply to the coronary arteries. The moisture barrier-coated viscoelastic polyurethane foam sufficiently accommodates the vasa so that the vasa can adapt to the small force applied to it by the stent. When unavoidable, a special coronary arterial chain-stent consisting of millimetric-gauged substents strung along a flexible tie line is contemplated.

However, this requires that the operator, working with the aid of a high magnification varifocal binocular endoscope (boroscope), sequentially position each substent, sliding it along the tie line to a position to least encroach upon the vasa before setting that substent in position around the substrate artery. To avoid the profuse vasa would, however, be a tedious and almost certainly imperfect exercise that would significantly increase procedural time. For this reason, the placement of a longitudinally continuous stent-jacket with lining and side openings or perforations as adequately accommodates and does not completely obstruct the vasa vasorum so that it can adaptively recover is preferred.

8h. Requirement for Moisture Barrier-Coated Viscoelastic Polyurethane Foam Linings The implants described herein have a lining of nonbiodegradable or bioresistant viscoelastic polyurethane moisture barrier-coated viscoelastic polyurethane foam. Such a lining not only cushions the substrate (treated) ductus, allowing some latitude in the design of the implant, which can therefore include slight adaxial protrusions if necessary, but protects the tissue at the outer surface of the ductus and spontaneously adapts to out of round and noncylindrical ductus without necessitating the custom making of devices to accommodate these. The microvasculature of the adventitia such as the vasa vasora and small nerves of larger vessels to include the nervi vasora and plexuses of larger vessels, such as those of the common, internal, and external carotid arteries, must be protected from compression or tamponade as would obstruct the supply of oxygen and nutrients to the cells of the luminal wall and remove wastes.

As indicated by the results of experiments cited above in the section entitled Necrosis and Atherogenesis-noninducing Conformation of Stent-jackets, an unfenestrated silicone elastomeric cuff placed about the common carotid artery of a rabbit plays a role in initiating the atherogenetic process. Obstruction to the fine subsidiary vessels supplying a larger artery, whether the consequence of protracted elevated serum cholesterol in the vasa vasora, encroachment upon the microvasculature that supplies the esophagus or trachea by an adjacent tumor, possibly constriction by a vascular ring, or a noncompliant stent-jacket is likely to aggravate the disease. Likewise, sustained compression of the fine nerves of the outer tunic will impair medial smooth muscle function within the wall.

Stent and impasse-jackets are fenestrated and provided with a special lining. Existing viscoleastic polyurethane foams, or 'memory' foams, have a useful life proportional to the material density of many years and newer such material can be made with closed cells that minimize infiltration with blood, serous fluid, or tissue, gas exchange with the internal environment or 'breathing' accomplished with the fenestrae, eliminating the need for open cell material. The foam lining provides numerous benefits related to eliminating the need for complete complementarity of conformation at the interface between the internal surface of the jacket and external surface of the ductus. The lining prevents compression of the fine vessels and nerves by holding the internal surface of the base-tube or radially outward lining at a distance. To maximize perforations through the stent-jacket thereby exposing the adventitia to its normal milieu as much as possible, the moisture barrier-coated viscoelastic polyurethane foam lining is as discontinuous as its function in the specific stent-jacket will allow.

A similar lining is used in an impasse-jacket wherein it is confined to the margins. The atrophy, hypoxia, and toxicity of obstructing the microvasculature is especially true of the coronary arteries, which have vasa vasora that end-arterial, afford relatively little collateral circulation and in atherosclerosis will have grown dense. The foam lining accommodates reductions in gauge following a subsidence in swelling too slight to require the use of an expansion insert, minor changes in gauge due to flaring, and allows impasse-jacket designs that call for some slight inward protrusions of the jacket. Another purpose of the moisture barrier-coated viscoelastic polyurethane foam lining with an expansion insert and/or somewhat larger base-tube is to allow for growth in a younger patient by using a thicker growth compensating layer of the foam to take up the space between the adventitia and the internal surface of the stent-jacket oversized pending acquisition of the adult gauge.

The same latitude will accommodate hyperplasia or swelling at a later time regardless of the cause. Except for a rare pediatric patient with a progeroid syndrome, the pathology will be other than atherosclerotic. The ductus must afford sufficient circumvascular clearance for an adult sized stent-jacket to be placed. The same accommodation would apply were the ductus subject to later inflammation. Yet another value in a foam lining is that it allows the application to the internal surface of an intrinsically magnetized stent or impasse-jacket of non-round material to increase the tractive force exerted. Moisture barrier-coated viscoelastic polyurethane foam linings are addressed above in the section entitled Preliminary Description of the Invention and below in the section entitled Stent- and Shield-jacket Moisture barrier-coated viscoelastic polyurethane foam Linings.

8i. Positional Stabilization of Implants

Reduction in the risk of stent failure by adventitial or medial delamination or the loss of retention of miniballs or stays as the ductus-intramural intravascular component of an extraluminal stent under the constant if minimized outward pulling force of the stent-jacket, can be enhanced by giving these a surface texture that encourages tissue infiltration.

Miniballs can be coated with a solder made to flow when placed in an alternating magnetic field, and stays can be treated thus and/or coated with cement on ejection from the stay insertion tool. The bonding agent is not intended to survive the internal environment, but rather to allow the surrounding tissue to infiltrate and replace it, thereby perpetuating cohesion. Dense connective tissue, such as tendons, which strengthen under stress, consist of parallel type I collagen fibers bound together by other proteins.

The adventitial or fibrosal tunic, which consists largely of type I collagen fibers at different angles and elastin fibers in proportion to the elasticity of the ductus, should likewise respond to the transverse magnetic field force on the implants by strengthening and aligning to better resist the centrifugal (sideways, axifugal) force imposed. Means for testing the strength of the ductus wall and a tendency to delaminate are provided below in the section entitled Testing and Tests. A nonoriented arrangement of fibers may necessitate an interim augmentation in retentive strength that affords sufficient elasticity for the intrinsic fibers to adapt. Bonding agents eliminate elasticity in their immediate vicinity but not in adjacent tissue. Stays offer the advantage of insertability with a coating of surgical cement at room temperature that if necessary, can be reduced in curing time by warming.

An accessory syringe holder can be attached to the stay insertion tool to deliver cements that consist of more than one component. Miniballs jacketed within a layer of a quick setting surgical cement formulated to melt when warmed, or a protein solder to denature (flow), at a temperature low enough to avoid weakening the intrinsic fibers following insertion are options. Another is to use electrically or fluidically heated injection syringe tool-inserts, as addressed below in the section Radial Projection Units, to deliver fluid cement or a molten solder before or after implantation. The bonding agent is kept warm by a coil in the syringe before use, targeted injection and the thermal insulation value of the polymeric body of the tool-insert serving to minimize the heat distributed to the surrounding tissue.

Except in a blood vessel where ischemia is a constant threat, an interval for initial setting can be gained by leaving the barrel-assembly in position following injection during which the stent-jacket is applied. The barrel-assembly is thus prepositioned so that a slight transluminal retraction places the discharge exit port or ports at the site for implantation. The need for short initial setting and curing times encourages the use of cyanoacrylate cements over alternative bonding agents, although some others set quickly when heated. The conduction of potentially thrombogenic temperatures is abated by means of a cooling catheter or by passing chilled fluid past a syringe type heated injector when a fluid system is used. Made of heat-resistant polysiloxanes or silicone polymer, for example, the body of the injector is inherently insulated.

When the implants are miniballs, such immediate coordination between heated tool-insert injection syringes and the discharge of miniballs is an example of the single entry and withdrawal advantage provided by a barrel-assembly having the radial projection units needed built into it or ensheathable in a size-matched slip-over combination-form radial projection catheter to constitute a bipartite or duplex barrel-assembly, as addressed below in the section entitled Distinction in Ablation or Ablation and Angioplasty-capable Barrel-assemblies as Unitary or Bipartite. In the same way, a barrel-assembly equipped with one or more injection tool-inserts can introduce a quick acting tumefacient to allow a lumen wall that has become too thin due to remodelling to be implanted without the need to withdraw and reenter. Similarly, when discharge implantation is uninvolved, a radial projection catheter (radial projection assembly), allows the application of whatever therapeutic means are appropriate, eliminating the need to withdraw one assembly and reenter with another, much less having to repeatedly alternate between two or more.

8i(1). Use of Solid Protein Solders

Several means for overcoming delamination or laminar avulsion under the tractive force placed on the ductus-intramural implants are provided. This risk inheres in perimedial or medial placement with the ductus-intramural implants under constant if minimal outward tractive force where it does not pertain to an endoluminal stent. However, an endoluminal stent poses more numerous and serious problems, to include endothelial dysfunction and clogging. Susceptibility to delamination is evaluated by a pretest described below in the section entitled Testing and Tests, and prevented through use of one or a combination of special measures to be described. The stays or miniballs can, for example, be coated with a eutectic solid protein solder that is heated to flow (melt when denatured) with means for applying heat that are incorporated into the apparatus or by placement in an alternating magnetic field, for example. Solders are addressed below in numerous sections, to include Medication-coated Miniballs, Stays, and Prongs with a Heat-activated (-melted, -denatured) Tissue Adhesive-hardener or Binder-fixative and Stays Coated with a Solid Protein Solder Coating and Cyanoacrylate Cement.

Since the avoidance of higher temperatures is desirable in all solder tissue bonding (see, for example, McNally, K. M., Sorg, B. S., Welch, A. J., Dawes, J. M., and Owen, E. R. 1999. "Photothermal Effects of Laser Tissue Soldering," *Physics in Medicine and Biology* 44(4):983-1002; erratum 44(6):1579; Soller, E. C., Hoffman, G. T., McNally-Heintzelman, K. M. 2002. "Use of an Infrared Temperature Monitoring System to Determine Optimal Temperature for Laser-solder Tissue Repair," *Biomedical Sciences Instrumentation* 38:339-344), the continued development of solders with lower melting points is critical to their use and may be considered a certainty. For ductus outside the vascular tree, newer eutectic solders that flow at lower, less injurious temperatures are under development (Lauto, A., Hook, J., Doran, M., Camacho, F., Poole-Warren, L. A., Avolio, A., and Foster L. J. 2005. "Chitosan Adhesive for Laser Tissue Repair: In Vitro Characterization," *Lasers in Surgery and Medicine* 36(3):193-201). Advancement is also being made with respect to increasing bond strength (Lauto, A., Foster, L. J., Ferris, L., Avolio, A., Zwaneveld, N., and Poole-Warren, L. A. 2004. "Albumin-genipin Solder for Laser Tissue Repair," *Lasers in Surgery and Medicine* 35(2): 140-145).

Differentially melting the solder layer about a miniball or stay in vivo without causing heat injury to the surrounding tissue is made possible, for example, by including different additives or inclusions in the solder. Targeted heating can be achieved using focused ultrasound (see, for example, O'Neill, B. E. and Li, K. C. 2008. "Augmentation of Targeted Delivery with Pulsed High Intensity Focused Ultrasound," *International Journal of Hyperthermia* 24(6): 506-520). Another approach uses the differential absorption of laser generated near-infrared radiation by multiwalled carbon nanotubes (see Ghosh, S., Dutta, S., Gomes, E., Carroll, D., D'Agostino, R. Jr., Olson, J., Guthold, M., and Gmeiner, W. H. 2009. "Increased Heating Efficiency and Selective Thermal Ablation of Malignant Tissue with DNA-encased Multiwalled Carbon Nanotubes," *ACS* [American Chemical Society] *Nano* 3(9):2667-2673).

Other processes which involve the use of magnetism may dictate placement of the stent-jacket only after placement of the implants, precluding use of a stent-jacket or a specially adapted stent-jacket as a heat shield or as addressed in the section below entitled Double-wedge Stent and Shield-jacket Rebound-directing Linings as a means for preventing perforations during airgun implantation (see, for example, Steinke, F., Andrä, W., Heidec, R., Wernera, C., and Bellemann, M. E. 2007. "Rotating Magnetic Macrospheres as Heating Mechanism for Remote Controlled Drug Release," *Journal of Magnetism and Magnetic Materials* 311(1):216-218). Solder coated miniballs can be heated from without, which heats intervening tissue, or magnetically excited by an external source to radiate heat from within.

Using the latter, a solder with a low melting point makes it possible to denature (melt) the solder coating while minimizing the diffusion of heat to the surrounding tissue. Where unavoidable, potentially injurious heat is quickly lowered to body temperature by passing chilled gas down a barrel-tube. In a blood vessel, this is done with a temperature-changing, or 'cooling' catheter such as a rod kept in a refrigerator or freezer which does not use or emit gas. Cooling catheters pertain equally to barrel-assemblies and stay insertion tools, which include side mounted spring clips for attaching auxiliary lines or cables for fiberoptic endoscopes, lasers, or cooling catheters, for example. Cooling catheters are addressed below in the section entitled Cooling Catheters (Temperature-changing Service-catheters).

Soldering is performed at between 50 and 100 degrees centigrade (Hoffman, G. T., Byrd, B. D., Soller, E. C., Heintzelman, D. L., and McNally-Heintzelman, K. M. 2003. "Effect of Varying Chromophores Used in Light-activated Protein Solders on Tensile Strength and Thermal Damage Profile of Repairs," *Biomedical Sciences Instrumentation* 39:12-17), and thus spans a temperature of 90 degrees centigrade at which thrombogenesis appears to be minimal (Post, M. J., de Graaf-Bos, A. N., Posthuma, G., de Groot, P. G., Sixma, J. J., and Borst, C. 1996. "Interventional Thermal Injury of the Arterial Wall: Unfolding of von Willebrand Factor and its Increased Binding to Collagen after 55 Degrees C. Heating," *Thrombosis and Haemostasis* 75(3):515-519). The temperature stated herein is based upon the references cited and not to be interpreted in a limiting sense.

8i(2). Means for Inducing the Formation of a Strong Implant-Tissue Bond

Specific substances for inducing the formation of a strong implant-tissue bond are addressed in several sections below, to include those entitled Specification of Cyanoacrylate Tissue Sealants and Bonding Agents and Medication-coated Miniballs, Stays, and Prongs with a Heat-activated (-melted, -denatured) Tissue Adhesive-hardener or Binder-fixative. A strong ductus-intramural implant-tissue bond discourages migration, delamination, and pull-through. Such an agent must strengthen the surrounding tissue and not just provide a strongly adherent bond at the implant-tissue interface. The implants generally are given a textured surface that includes undercuts to improve initial adhesion, then tissue infiltration, and when applicable, the uptake of medication incorporated into or applied beneath the outer bonding agent.

While wiped away from the outermost prominences of the stay as it enters, the deep surface texture of the stays retains and carries the coating to the implantation site. The inclusion or collateral implantation of a drug or drugs to toughen the surrounding tissue and thus impart resistance to pull-through by inducing cell proliferation, the formation and transport of fibroblasts, or the thickening of connective tissue fibers, for example, cannot be depended upon. This is because a. For the drug or drugs to exert the desired effect takes too long, b. To implant the drug or drugs through an intrusive procedure as a pretreatment at an earlier date unduly imposes upon the patient, d. May detain therapy needed promptly, and d. The toughening obtained might subside as the drug is dissipated. The use of tissue hardening and bonding agents with an immediate fixative and stabilizing effect is thus preferable.

If not intended to increase initial retentive strength but rather to impart additional strength over time, various substances are available (see, for example, Hunter, W. L., Gravett, D. M., Toleikis, P. M., Maita, A., Signore, P. E., Liggins, R. T., and Guan, D. 2007. "Medical Implants and Fibrosis-inducing Agents," U.S. Pat. No. 7,166,570). 'Fibrosing' as incorrectly denoting scarring would, however, be weakening. By contrast, tissue hardening and bonding agents as discussed below can be formulated to provide an immediate increase in strength and encourage infiltration and gradual replacement by the surrounding tissue. A service-catheter used in a barrel-assembly can similarly be multiluminal, and fed from separate syringes, reservoirs, or containers can be open or hypotube-ended. With miniballs, more than one service-channel may be disallowed as restricting the size of the miniballs that can be used; however, a multiluminal catheter will always provide an adequate flow rate for any fluid substance passed therethrough with sufficient force.

Whether encapsulated within solder, stays are readily coated with any other fluid agent or combination thereof by separately controlled auxiliary syringe holding frames, as addressed below in the section entitled Stay Insertion Tool Auxiliary Syringes. An insertion tool with two holding frames attached is especially versatile for combining various liquid or semiliquid substances as adjunctive to implantation. For example, a tunica media swelling agent can be delivered from an auxiliary syringe attached at one side of the tool, and a tissue hardener from an auxiliary syringe attached at the other side. Using a stay insertion tool, the delivery of a gas, aerosol, gas with a fine powder dispersed in it, or a slurry is accomplished by attaching a delivery line (catheter) to the tool with spring clips provided on the tool, as described below in the section entitled Stay Insertion Tool Mounting Spring Clips.

Compatible liquid or semiliquid substances from separate syringes can be delivered together through the one line leading from either holding frame to the tool. The same limitation in size pertains to auxiliary syringe holding frame delivery tubes or service catheters affixed to one or both sides of a stay insertion tool by means of spring clips, which must have outlet ends small enough to position over the stay ejection slot. When the contents of the holding frame to either side must be deposited on the stays as each is ejected, then both holding frames must feed open tubes or injection needle-ended hypotubes suspended over the stay or the same single or multilumen line as it is emitted. Unless each holding frame feeds one of the two lumens in a distal segment of the line made of dual lumen tubing or the tube ends are small enough to be juxtaposed, the exit tip of one must be nudged aside to allow the overlying position for the other.

As with discretionary injection, this requires a larger access incision. However, even though the diameter is limited, whether a service catheter in a barrel-tube or attached alongside a stay insertion tool, each lumen in a multiple lumen tube can be supplied from a separate syringe, canister, or other source. The distal or working ends of the syringe delivery or service catheters wet the stays as these are ejected or can end as hypotube injection needles ridgidly angled for injection with each stay as it is inserted. The distal segment of the hypotube can also be left flexible for discretionary use. Discretionary will require a larger entry wound to accommodate a hemostat or other forcep, pliars, or tweezer-configured tool for maneuvering the injection needle.

Unlike a stay coating line, a hypotube injection lines and open ended service catheters used to eject or spray fluid into the entry portal are not limited by the space available over the stay ejection slot hence, in diameter and rate of outflow. Interchangeable ending segments, open and hypotube soft and angle-ended, are more versatile and no more demanding on entry portal size than would be a separate line likewise adapted to accept ejection and injection distal segments. Connection of a narrower open ended tube to a hypotube line is by means of a size adapter. Injection tool-inserts in barrel-assemblies and radial projection catheters can likewise be used to deliver any fluid substance or substances in any combination. Miniballs must likewise have a deeply textured surface for wetting just prior to insertion to be carried to the implant site; otherwise, miniballs incorporate constituents as solids. Versatility in wet coating upon insertion is, however, a relatively minor consideration in choosing stays over miniballs.

9. Minimizing the Risk of Rebound

To minimize the risk of rebounding from, penetration, or puncture of the fibrous outer layer or sheath of the vessel or duct while taking advantage of the elasticity of the lumen wall, miniball discharge is at a 45 degree or less, i.e., acute, angle. Compared to a trajectory perpendicular to the lumen surface, penetration at an acute angle aids implantation by undercutting the media with less risk of perforating the tunica adventitia, which includes collagen fibers at angles and is tougher than the subjacent tissue. The longer trajectory extends the resultant trauma and inflammation; however, the reobstruction if not abrupt closure that appears to vary with the extent of vessel wall damage by balloon over-inflation and dissection is quite different in form and much more extensive than is the suddenly introduced and highly circumscribed penetration of the intima and media by the miniature balls.

An adventitia weakened by disease can sometimes be strengthened chemically and/or bolstered through the application of an elastic clasp-jacket of which the lining is coated with a tissue hardener-adhesive. A double-wedge lined stent-jacket, as addressed below in the section entitled Double-Wedge Stent- and Shield-jacket Rebound-Directing Linings, placed before initiating discharge both prevents perforations and redirects the miniball away from the lumen and into the lumen wall. Few bonding or hardening agents will hold up to the internal environment wherein enzymes, oxidation, and constant tissue replacement will eventually eliminate most; the use of these substances applies when the healing process is expected to re-establish the strength that had been lost to disease. Success is optimized by efficient technique that minimizes operating time. As in conventional endovascular interventions, general anesthesia is usually unnecessary.

In patients for whom an antecedent angioplasty has recovered adequate luminal diameter and throughflow, the apparatus is devised to implant the miniballs in the least amount of time. Positioning the muzzle-head and exit-ports to place the miniball implants in a tight uniform pattern too difficult and time-consuming for manual control, function thus is relegated to a semiautomatic positional control and discharge system. Whether control is manual or automatic, superior steerability, rotatability, ability to place multiple implant miniballs per discharge and contrast enhancement for clear viewability of the angular and transluminal position of the muzzle-head and implants allow efficient positioning that likewise reduce procedure times.

Hence the incorporation into the muzzle-head of a flexible joint and turret-motor, for example. One means for urging the muzzle-head toward a certain arc of the wall if necessary is addressed above in the sections entitled Comparison of Extraluminal with Endoluminal, or Conventional, Stenting and Steering and Emergency Recovery of Implants with the Aid of an External (Extracorporeal) Electromagnet. This measure reduces the likelihood of completely cutting off the circulation during the ballistic implantation of an artery. As addressed below in the section entitled Double-wedge Stent- and Shield-jacket Rebound-directing Linings, when the risk of rebound is pronounced or intolerable, a special stent-jacket lining is employed. Such a lining can be wetted with a coagulant, other therapeutic substance or substances, and/or medication.

Wherever a risk of rebound into the circulation of an implant or tissue sealant exists, a means for countering this risk is provided, to include the incorporation of innocuous ferrous matter to allow magnetic removal. Should a miniball enter the circulation, it is immediately trapped and held in an impasse-jacket prepositioned upstream or with the aid of an external electromagnet, such use addressed in sections of appropriate title. Impasse-jackets incorporate an extraction grid to allow pulsing a powerful extracorporeal electromagnet to move the trapped miniball to a distance outside the ductus or entirely outside of the body, which rarely if ever necessary, can be accomplished safely.

10. Concept of Ballistic Insertion

Ballistic implantation and its opposite, sudden extraction using a powerful extracorporeal electromagnet are intended to overcome the puncture and penetration resistance of the target tissue so suddenly and forcefully that an elastic reaction of displacement and resistance to stretching around the entry hole and the penetration trajectory is eliminated and injury to the circumjacent cells minimized. The lumen wall is struck too suddenly to displace or deform; that is, the rate of deformation or strain rate is exceeded, precluding compression of the tissue rather than its sudden puncture and penetration, even without affecting the temperature of the tissue. Moreover, the diameter of the wound trajectory is that of the miniball implant alone without increase due to the need for an insertion instrument.

Stent implantation by such means should affect only the tissue in and immediately surrounding the trajectory, the latter closing in and releasing exudate to contain the miniball implant and commence the healing process. In addition to extracorporeal means of imaging, the devices used to accomplish ballistic insertion, barrel-assemblies, incorporate aids to the obtaining of a clear view such as an angioscope or intravascular ultrasound probe within the state of miniaturization. FIG. 66 shows an edge-discharge muzzle-head configured to allow the axial insertion of a cabled device to include those used to assist viewing. An adapted semiautomatic repeat action gas-operated airgun with single or multiple barrel-tube barrel-assembly can be made to affect miniball implantation with relatively tight control over the exit velocity and impact force.

Above a certain exit velocity, the miniball will perforate entirely through the wall of the ductus. For the purpose of extraction, this level of momentum is always applied, but in pulses brief enough to allow control over the distance the miniball is drawn with each pulse, the absolute distance changing according to the type and condition of the tissue traversed. For infixion, however, there will be a range of lower exit velocities and momentum such that the adaxial layers or tunics in the ductus wall will dissipate some of the momentum to more impede the miniball the further it penetrates with the fibrous outer layer bringing the miniball to a stop.

In an artery, for example, the layers of the vessel wall include the smooth muscle of the tunica media, the internal elastic lamina inside (surrounded by, medial or adaxial to) the tunica media, and the external elastic lamina outside (surrounding, external or abaxial to) the tunica media, each posing resistance to penetration (Holzapfel, G. A. and R. W. Ogden 2010. "Constitutive Modelling of Arteries," *Proceedings of the. Royal Society, Series A. Mathematical, Physical & Engineering Sciences* 466(2118): 1551-1597). The tunica adventitia or outer fibrous layer of the vessel then poses an additional layer of resistance to penetration which prevents the miniball from perforating. Another moderating factor is discharge at an acute forward or distal abaxial angle, which increases the distance through the wall and reduces the perpendicular vector.

Continued travel down the interface between the media and the adventitia will have been predetermined and compensated for. The cells in the trajectory are crushed, with the cytoplasm and membranes troweled against the sides or wall of the trajectory. The release of fluid contents and inflammatory swelling quickly backfill the trajectory and seal the miniball at the terminus. Provided a type tissue is disease-free, the range of variation in mechanical properties from one conspecific or congeneric individual to the next will be small; the tissue having to satisfy the same physiological requirements in both individuals (Humphrey, J. D. 2003. "Review Paper: Continuum Biomechanics of Soft Biological Tissues," *Proceedings of the. Royal Society, Series A. Mathematical, Physical & Engineering Sciences* 459(2029) 3-46; Fung, Y.-C. 1993. *Biomechanics: Mechanical Properties of Living Tissues*, New York, N.Y.: Springer-Verlag).

Allowing for age, behavior, and genetics, this is even true across vertebrate classes. Bulk and shear modulus, elasticity, resistance to puncture and penetration, and so on, establish a range of exit velocities for properly seating the miniballs in normal tissue. However, disease-free tissue almost never warrants implantation, while diseased tissue is associated with a breakdown in physiological function, hence, deviation from the normal range of values for tissue strength, making in situ testing at the prospective implantation site imperative. Based upon in situ tissue testing as addressed below in the section entitled Testing and Tests, the discharge velocity is set to penetrate to and be stopped by the adventitia. Only diseased tissue requires medication or the application of retractive force for restoration to a functional conformation. Unlike healthy tissue, diseased tissue varies over a wide range of hardness and strength from malacotic to sclerotic or indurated.

For example, treatment of an artery with ductus-intramural implants, especially those to be subjected to the tractive force of a magnetic field, warrants cautious application to patients susceptible to spontaneous rupture of the elastic laminae and those in whom an antecedent conventional angioplasty resulted in balloon overstretching. The in situ tests provided will uncover such a condition. The progressive mineralization of vascular plaque by calcification can make it as hard as concrete, necessitating a preliminary atherectomy, usually with a rotatory grinding burr type cutting tool. That in direct stenting, stays, which are inserted from outside the adventitia can avoid such preparatory treatment of the internal surface of the ductus, which carries the risk of perforation, is mentioned above in the section entitled Circumstances Dissuading or Recommending the Use of Stays. Wide variation in tissue hardness is no less pertinent to implantation of medication miniballs as miniballs that represent or additionally represent the intraductal component of a magnetic stent.

To test diseased tissue of the same kind and degree of advancement in different subjects immediately upon death as to minimize the effects of autolysis indicates the range in exit velocity to implant and not perforate for that condition, and such results for different conditions over the malacotic-sclerotic range establish the overall gross range for the initial control settings required by the apparatus. Within this overall range, different pathology and individual variation will dictate the resolution or fine adjustment required. Even tissue immediately adjacent to a lesion will not exhibit the same mechanical properties as will the lesion itself. Even though miniballs are bioinert, and with the exception of the largest for use in the gastrointestinal tract, airway, and organs, tiny, so that a perforation would not result in serious injury, testing is not accomplished through test discharges.

The reason is that while a single test discharge could do little injury, but multiple test discharges could do serious injury. Accordingly, methods and apparatus for establishing the penetration, perforation, and patenting forces best to apply along different areas about the circumference of the diseased ductus tissue to be implanted are obtained. Distinctions among arcs are ascertained because these can be translated into a discretionary distribution of forces to be applied to each area, the means employed not limited to a uniform application of forces all around. If to be stented, the intrinsic magnetization of the thin stainless stent-jacket or of the small bar magnets mounted about the outer surface of the polymeric stent-jacket can be varied in magnetic force or some can be omitted. The base-tube can be varied in thickness, in material or materials, hence, resilience, can be perforated, or a side-slot used to clear an attachment.

Any type ductus may present an eccentric condition best treated were medication and/or radiation closely targeted at a certain arc. Any barrel-assembly can accomplish eccentric discharge. With a simple pipe type, rotation is manual. In radial discharge barrel-assemblies, one or more exit-ports about the circumference of the muzzle-head can be rotated clockwise or counterclockwise with the turret-motor, and the rotary magazine clips can be instantly changed to change which barrel-tubes discharge a miniball. To clear an attachment of connective tissue, for example, the holes in the rotary clip feeding the barrel-tube or tubes directed at the area are left blank or plugged. If stenting is involved, then a stent-jacket with a cut out or a wider side-slit, or side-slot, is used to straddle the omitted or blanked out arc. Concerns pertinent to miniballs include perforations, pulling through the superjacent tissue under the constant if weak tractive force of the stent-jacket resulting in stent failure, mispositionings, entry into the lumen, and if the lumen of a blood vessel, then embolization.

Wide stays coated with cyanoacrylate cement, which are not likely to pull through, are more appropriate for weaker tissue; but were this to occur, retrieval would require minor surgery. All are responded to with multiple preventive and corrective measures, and none pertain to any meaningful extent to stays. Implanted ballistically, the use of miniballs arouses concern that either because of proximity to neighboring structures, a perforation with continued travel of the miniball would pose an inordinate risk, or that the arterial wall may have already become (see, for example, Richardson, P. D. 2003. "Elliptic Delamination as an Early Stage in Atherosclerotic Plaque Evolution: Fluid Mechanical Aspects," *Biorheology* 40(1-3):417-421) or will become so weakened as to become susceptible to rupture, stretching, or aneurysmal failure. Weakening of the lumen wall is more likely to arise when a positional control system has been used to place the miniballs in a close formation.

Means for preventing adverse consequences are incorporated in the inventive system in the form of emergency recovery means, such as the recovery electromagnets in the muzzle-head or stay insertion tool, the prepositioning of stent-jackets and downstream impasse-jackets, and a method for adapting a magnetic resonance machine for emergency interception and resituation or extraction of a problem miniball specified in section X2c below entitled Stereotactic Arrest and Extraction of a Circulating, Dangerously Mispositioned, or Embolizing Miniball. Emergency extraction consists of pulling the miniball from its instant position whether moving or having been stopped by a jacket or embolic filter with a powerful external electromagnet stereotactically positioned to extract the miniball through the least injurious trajectory into neighboring tissue where it will be harmless, to a more accessible location for recovery, or entirely outside the body.

When trapped by the recovery electromagnets in the muzzle-head, no further action is required. Pull-through relates to miniballs and delamination to ductus-intramural implants of any kind. Vulnerable structures along the trajectory will be apparent, the absolute size of the projectile limits the injury that can result, and perforations tend to seal quickly. A primary reason for ballistic implantation is precisely the fact that the access path is no larger than that of the implant itself, is therefore minimally injurious, quickly seals, and quickly heals. While perforation by the largest miniballs might injure a ganglion, nerve, lymph node, or blood vessel, regeneration and redundancy would make permanent damage even from these, much less smaller miniballs, virtually impossible. Smaller miniballs shot entirely through the adult body should produce little damage.

For a miniball to gain entry into the lumen of a blood vessel other than that treated is improbable, for the level of embolization by the minute miniball to be associated with an exclusive territory so that tissue supplied is dependent upon it as lacking collateral circulation is improbable, and for the miniball not to be instantly extractable through the use of an external magnet before any significant injury resulted is impossible. More specifically, a perforation will tear through capillaries, venules, muscle and nerve fibers along the trajectory, but due to the absolute diameter of the trajectory, produce negligible trauma. Interposed vessels and organs that were perforated would quickly seal themselves and heal, and the severing of nerve fibers that produced some functional impairment internally or that resulted in an area of cutaneous numbness would soon regenerate. Even without the multiple precautionary elements built into the apparatus, a loose miniball that entered the bloodstream, could be stopped with an extracorporeal hand-held electromagnet.

When the muzzle-head is not too large in diameter to approach the miniball where the external extracorporeal electromagnet intercepted it, raising the current to the inmate tractive electromagnets in the muzzle-head while deenergizing the external magnet will force the miniball into the antemagnet chamber. Viewed throughout with suitable contrast and imaging equipment, were the exit velocity set too low so that miniballs failed to penetrate the lumen wall, for these to intravasate or enter the bloodstream unseen and not otherwise noticed is improbable, and for a miniball to move past the partially energized recovery electromagnets much less an embolic filter (trap-filter) at the front of the muzzle-head is more improbable. For a miniball to move past an impasse-jacket that had been designed and prepositioned precisely to stop and hold it is virtually impossible, and for retrieval to take more than a few seconds is most improbable.

To maximize miniball selectivity, the probe of the stereotactic extraction armature is drawn down to a fine needle. Nevertheless, so that miniballs successfully placed, especially in a tight formation, are not also extracted or dislodged, stereotactic extraction is best reserved for a miniball sufficiently distant from any others. However, the first discharge is that most susceptible to miscalculation in the exit velocity, so that the problem miniball will tend to be isolated. Also, to reduce the risk of the miniball implants being pulled entirely through the adventitia by the stent-jacket as would result in stent failure, the tractive force applied to the miniballs is kept to the minimum and evenly distributed by positioning the miniballs in a uniform pattern as would tend to lift the wall as a sheet without the tractive force concentrated on one or a few ductus-intramural implants.

To accomplish uniform distancing between adjacent miniballs at the small dimensions involved, especially at high speed to minimize hypoxia, exceeds the precision that can be achieved under manual control and therefore necessitates the use of an automatic positional control system, as addressed in the section to follow among others. Perforations can be prevented by preplacing the stent-jacket. A miniball that perforates through a stent-jacket or impasse-jacket encircled, or substrate, ductus on discharge or at a later time due to pull-through becomes embedded in the moisture barrier-coated viscoelastic polyurethane foam lining of the jacket and is not a chronic irritant for the adventitia. More specifically, were a miniball to pull through the adventitia to become insinuated between the adventitia and the lining of the stent-jacket despite the uniform positioning that deters disproportionate traction on one or a few miniballs afforded by positional system controlled discharge, then irritation to the adventitia is at most short lived.

If the miniball remains aligned to the exit-hole, then continued traction pulls the miniball away from the adventitia and into the moisture barrier-coated viscoelastic polyurethane foam lining of the stent- or shield-jacket, allowing the adventitia to seal behind it. If gravity or movement of the surrounding tissue causes the miniball move aside from the exit-hole, then the outward force exerted by the adventitia and traction drive the miniball into the lining. Embedded within the lining, the bioinertly encapsulated submillimetric miniball is innocuous. Hence, once the stent-jacket has been placed, the gradual pull-through of one or a few miniballs is unlikely to produce chronic irritation or failure of the stent.

Even without a stent-jacket prepositioned to prevent perforation, the actual hazard posed by a miniball of millimetric diameter that perforates is nugatory. Rebound into the lumen when penetration into the base-tube is incomplete is addressed below in the section entitled Double-wedge Stent- and Shield-jacket Rebound-directing Linings. Provided the use of anticlotting medication has not been excessive, a perforation through an artery seals quickly, the prepositioned stent-jacket also absorbing any minor leak. A change in moisture barrier-coated viscoelastic polyurethane foam lining conformability due to the absorption of blood which then dries and hardens is reduced by coating the inner surface with enzymes and hydrogen peroxide. Potentially septic leaks from the gut, for example, are treated conventionally by suturing or cementing the perforation shut when the site is approached to place the stent-jacket.

Perforations of the gut or vessels containing infectious blood, for example, are implanted with stays, significantly reducing the risk of perforations, or with miniballs with the stent-jacket, a shield-jacket, or impasse-jacket within an absorbable shield-jacket prepositioned over the segment to be treated. Coating the internal surface of the stent-jacket with a surgical cement or tissue sealant is not preferred as obviating the conformability of the moisture barrier-coated viscoelastic polyurethane foam lining desired to protect the microvasculature and nervelets that enter and depart from the outer surface or adventitia of the ductus. Provided the test prescribed below in the section entitled In Situ Test upon Endoluminal Approach for Susceptibility of the Ductus Wall to Puncture, Penetration, and Perforation is conducted, a perforation that occurred nevertheless would require an error in adjusting the exit velocity or in having selected points for testing that missed a transition to a softer condition. Misaiming and improper setting of the exit velocity will usually be the result of inadequate knowledge or skill.

Other causes can relate to airgun malfunctions, but with the means for prevention provided, most causes will be the result of human error. Airgun malfunctions are dealt with in the section below entitled Modes of Failure. Given that the stent-jacket can be prepositioned to preclude such an eventuality, the extent of the diseased segment based upon testing can be confirmed through gross inspection and the collateral use of contrast dye in imaging, and can be further confirmed through the detection of fine differences in temperature and electrical properties, misjudging the resistance to perforation at the treatment site is unlikely. Unless irradiated, a sterile and biocompatibly encapsulated miniball can do no damage in the surrounding body cavity. The recovery of radioactive and medication miniballs is addressed below. To injure, much less puncture or penetrate a neighboring structure or penetrate into the lumen of a neighboring ductus, the miniball would have to retain the momentum needed.

Miniballs and stays can be coated with a cyanoacrylate cement that quickly achieves an initial set to preserve wall integrity pending healing. Whereas stays are coated as each is ejected from the insertion tool, miniballs must not be coated with a liquid glue until after discharge by injection using an injection tool-insert or a hypotube-ended service catheter run through an available barrel-tube used as a service channel following placement. Midprocedural entry into the lumen is immediately corrected using the recovery electromagnets in the muzzle-head of the barrel-assembly, the embolic filter if the barrel-assembly is so equipped and the filter is deployed, and a prepositioned extracorporeal electromagnet. Mid- and postprocedural interception, even in the circulation, such as might result from disease progression or the contracting of a secondary condition, is accomplished by the prepositioning upstream of an impasse-jacket.

As can the primary stent-jacket, an impasse-jacket can also be used at any later time for magnetic drug targeting. When magnetic drug targeting would necessitate a field strength that would pull the miniballs through the superjacent adventitia, the magnetic susceptibility of the drug carrier particles is increased by providing these with higher ferrous content. The midprocedural loss of a miniball into a nonvascular lumen is instantly correctible using the system components indicated. The postprocedural extraction of a miniball stopped in the circulation by an impasse-jacket is noninvasive, an external electromagnet pulsed to extract the miniball from the jacket to a safe location in increments or left energized to suddenly remove it from the body altogether. The entry of a miniball into the gastroinstestinal tract has little significance, and one loose in the airway or a ureter, for example, is quickly extractable at a clinic. When a clinic will not be available, an impasse-jacket is placed.

Constant movement of the lumen wall is prevented from making discharge or other treatment under direct manual control excessively difficult by means addressed below in the section entitled Gross Positional Stabilization (Immobilizaton) of the Implant Insertion Site. Up to the peak systolic diameter, the cross-sectional area of the lumen not taken up by the muzzle-head will be available for blood to pass, and the barrel-assembly incorporates blood passing features, as addressed below in sections respective of each and summarized in the section entitled Hypoxia and Ischemia-averting Elements. Discharge is effected during diastole, the systoles used to reposition the muzzle-head. However, as prepositioning and tightening the stent-jacket may be used when an arrhythmic (irregular) or tachycardic (accelerated) pulse makes timing discharge difficult, the muzzle-head must be of an outer diameter that allows it to be repositioned with the stent-jacket tightened.

While some oxygenated blood is able to pass whether the muzzle-head is stationary or in motion, ischemia will limit the narrowness of the vessel that can be treated; however, small vessels do not develop plaques. Reduction in diameter or length of the muzzle-head will reduce it as an obstruction to the flow of blood but reduce the angioplasty and atherectomy components it can incorporate. Reduction in size will also reduce the maximum diameter or number of barrel-tubes, hence, the number of miniballs that can be discharged simultaneously, which factor reduces the implantation rate. It will also require the turret-motor windings to be increased in length in order to generate a given torque output, and reduce the maximum field strength that can be developed by the recovery electromagnets, whose windings are not amenable of lengthening.

This is because in any barrel-assembly for use in the bloodstream, the recovery electromagnets must be distal to the exit-ports. Lengthening these lengthens the nose and thus reduces the forward reach of the muzzle-head, that is, reduces the distance to which the exit-ports can be advanced down a narrowing vessel to align the exit-ports with tissue to be implanted. With a monobarrel, which is suited to use in more narrow vessels, positioning the exit-port against the arc to be implanted distends the wall in contact with the muzzle-head to no more than its systolic displacement, with the luminal cross-section for blood to pass shifted toward the arc not in contact with the muzzle-head. This allows relative movement between the muzzle-head and the wall to be suppressed stabilizing (immobilizing) the lumen wall during discharge while increasing the passage of blood past other side.

The temporary stabilization of the lumen wall at the treatment site also allows ablation or brush cytology, for example, to be accomplished and avoids the difficulties and uncertainties of synchronizing discharge to the pulse. Abaxial angular shifting of the muzzle-head and applying pressure against the lumen wall can be aided by radial projection unit push-arm tool-inserts, an external magnet, or an inmate steering system. For the purpose of stabilizing the wall to implant it, this urging is best kept least compressive as possible. The use of these is, however, primarily intended as an aid to angioplasty or atherectomy. The external electromagnet, which can be hand-held, attracts the cores or armatures in the muzzle-head, which unlike the silver windings, must be ferromagnetic.

For use in the bloodstream, resistance to the advancement of the miniballs by the air trapped in the barrels demands pressure relief to prevent air or propulsive gas, normally $CO_2$, from entering the bloodstream during discharge. It is also important to minimize any inflow of blood into the muzzle-head through the exit ports during the intervals between discharges. In vascular applications, the ballistic implantation of miniballs, whether as a method for introducing medication, a radionuclide, and/or other therapeutic substances, and/or as the intravascular component of an extraluminal stent, usually follows an angioplasty or atherectomy, whether thermal, cryogenic, or mechanical. An angioplasty-capable barrel-assembly can be used to apply any of these and then be engaged within the interventional airgun to effect discharge implantation without the need for withdrawal.

When stenting is to be direct, or not preceded by an angioplasty as not to require entry into the lumen, then the use of stays rather than miniballs allows the lumen to be avoided for stenting as well. When stays are used to target medication, radiation, and/or for stenting so that the lumen is avoided, the need for platelet blockade is periprocedural and eliminated shortly thereafter. With ballistic implantation, the thrombogenic period associated with intimal healing is longer, so that antiocoagulative medication is given longer. However, once healed, no stent occupies the lumen, and this medication is stopped. Otherwise, the methods described herein warrant the perioperative management prompted by transluminal procedures.

This includes medication for managing the sequelae normally associated with catheter-based procedures, such as the administration of a calcium antagonist to reduce risk of coronary artery spasm. Whereas relaxation in an artery is associated with contraction, in peristalsis, expansion is associated with relaxation or distention due to the passage of a large bolus. While the timing and form of peristalsis in different type ductus such as the gastrointestinal tract and ureters differs, for a certain target location, the muzzle-head is repositioned during contraction, with discharge effected at the moments of relaxation. Means for facilitating implantation whether under direct manual or semiautomatic control are addressed below in the section entitled Motional Stabilization of the Implant Insertion Site.

11. Use of a Positional Control System

The use of a stepper motor to advance a catheter goes back at least to the mid-1970s (see, for example, Clark, J. S. and Fan, F. L 1978. "Alveolar Gas Sampling System and Method," [U.S. Pat. No. 4,220,162]; Bradley, W. E Klatt, W. M., Kuyava, C. C., and Dreher, R. D. 1980. "Urethral Catheter Puller," [U.S. Pat. No. 4,233,991], and a catheter-based transducer through the lumina of vessels at millimetric intervals was accomplished not later than 1994 (Matar, F. A., Mintz, G. S., Douek, P., Farb, A., Virmani, R., Javier, S. P., Popma, J. J., Pichard, A. D., Kent, K. M., Satler, L. F., Keller, M. and Leon, M. B. 1994. Coronary Artery Lumen Volume Measurement Using Three-dimensional Intraductal Ultrasound: Validation of a New Technique," *Catheterization and Cardiovascular Diagnosis* 33(3):214-220; Liu, J. B., Bonn, J., Needleman, L., Chiou, H. J., Gardiner, G. A. Jr., and Goldberg, B. B. 1999. "Feasibility of Three-dimensional Intraductal Ultrasonography: Preliminary Clinical Studies," *Journal of Ultrasound in Medicine* 18(7):489-495).

The application of a positional control system to the transluminal and rotatory control of a catheter as an aid to intravascular or endoluminal intervention, however, does not appear in the literature. Since the degree of precision needed for conventional procedures is less, this is to be expected. To the extent possible, the object is to have multiple implants together lift the lumen wall as a uniform sheet, so that even though magnet pole foci of attraction exist, the force of attraction on any one implant, even at the magnetic poles or apices of the foci, will not be sufficiently disproportionate to pull implants through or tear the adventitia and media if implanted therein, or prompt an avoidance of placing implants within areas of focal field intensity.

For placing miniballs to serve as the intravascular component of a magnetic extraluminal stent, a close and uniform spacing of miniballs more evenly distributes the magnetic traction, reducing the likelihood for pull-through. To achieve fine incremental repositioning with uniform spacing, much less quickly to minimize procedural time, exceeds manual ability even with the benefit of high resolution imaging equipment. Another application for implants in tighter formations is to allow implants that consist entirely or peripherally of medication and/or radionuclide miniballs (radiation emitting seeds) to deliver a higher dose over a circumscribed area. However, precisely uniform spacing is not essential for these, the absolute distance between adjacent miniballs will be larger, and the sum of these will usually be relatively few in number.

Another use for fine control over the positioning of implants is to make possible the dispersal of miniballs so as to minimize the resistance to penetration of medication through atherosclerotic or neoplastic tissue (see, for example, Ghosn, M. G., Carbajal, E. F., Befrui, N. A, Tellez, A., Granada, J. F., and Larin, K. V., 2008. "Permeability of Hyperosmotic Agent in Normal and Atherosclerotic Vascular Tissues," *Journal of Biomedical Optics* 13(1): 010505; Larin, K. V., Ghosn, M. G., Ivers, S. N., Tellez, A., and Granada, J. F., 2007. "Quantification of Glucose Diffusion in Arterial Tissues by Using Optical Coherence Tomography, *Laser Physics Letters* 4(4):312-317). The character of the tissue to be implanted determines the dispersal pattern as to uniform, nonuniform, concentrated at or about a focal point, or some combination thereof. The distribution at controlled interrelated distances throughout a tumor, for example, of miniballs that release various drugs, combinations of drugs in various doses, other therapeutic substances and/or radiation avoids the need for diffusion through the circulatory system.

The object therewith is to establish a local or more extended field for the placement of medication or other therapeutic miniballs in a pattern that will compensate for an impeding delivery diffusion gradient. Each miniball releases a dose or radiation dose-rate that is taken up proportionally less as it diffuses away from the point of origin or focal source. Dissolution or disintegration of medication implants can be by conventional time-release formulation or by extracorporeal action at intervals based upon periodic diagnostic results, as addressed in the section below entitled Extracorporeal Energization of Intrinsic Means for Radiating Heat from within Medication Implants and Medication and/or the Tissue Bonding-coatings of Implants, to Include Miniballs, Stays, and Prongs, such as to control the dissolution thereof.

When miniballs for stenting are medicated, uniformity of distribution takes precedence; if a focused gradient for the associated medication is desired, then the dose applied to the miniballs is progressively reduced moving outward from the focal center. It is simpler to adjust the dose in each miniball than to implant an intricate formation. While the endoscopic placement of irradiating seeds in the gastrointestinal tract has long been practiced, implantation by the means described herein is more precise and allows individual seeds to be placed in close proximity through trajectories or entry paths that no larger than the implants themselves, quickly seal and heal. The delivery of medication other than by injection allows considerably greater control over the area exposed to the drug and the delivery rate. The release of medication can be time delayed and the density of implants can be used as one way to control the dose.

A related but distinct purpose for using an automatic positional control system is to place the exit velocity as well as the linear stage and turret-motor under control, thus making possible side-looking discharge of medication and/or radiation seed miniballs at a high rate and in a pattern of variable depth and sidewise or abaxial deviation. Miniballs for uniform placement are almost always implanted within uniform tissue without the need to adjust the exit velocity from one to the next. If needed, the adjustments are accomplished manually. The distribution at controlled relative distances throughout a tumor, for example, of miniballs that release various drugs, combinations of drugs in various doses, other therapeutic substances and/or radiation is presaged in the carcinolytic radioactive seeding of organs, the prostate gland being that most familiar. Use thus essentially adds depth of penetration as the third dimension to the two dimensions involved in achieving uniform distribution to the same depth within the lumen wall.

For tumor-seeding, the pattern of placement in depth and lateral displacement is the object, with uniform distancing but one possible pattern of distribution sought. For drug and/or radiation tumor-seeding, the barrel-assembly is usually a monobarrel, or one with only a single barrel-tube, and achieving a certain pattern of distribution in depth and lateral displacement is the object. The distribution pattern is based upon the constituents of the miniballs, with uniform distance but one possible pattern. Once implanted, each miniball releases its medication or other substance within the tumor at a predetermined distance from the others, and the contribution of each may relate to that of the others as providing dose uniformity, a combined effect, or adjuvant action, usually, in proportion to the relative proximity of each to the others. Since the barrel-assembly uses the lumen as its track so that endoluminal containment stabilizes the muzzle-head in position relative to the atheroma or neoplasm, the concept pertains primarily to tumors of ductus or vessel walls.

When judged unsuitable for immediate excision, as in late stage metastatic disease or when chemotherapy and/or radiation are thought capable of effecting a cure, such lesions include colorectal and extrahepatic bile duct carcinomas, secondary metastases to blood vessels, and other periductal tumors which have depth, are relatively small, and/or awkwardly situated for access with an endoscope (which is not capable of the treatment modality indicated in any event), and tend to resist penetration or infiltration by medication (see Qiao, Y., Huang, X., Nimmagadda, S., Bai, R., Staedtke, V., Foss, C. A., and 9 others 2011. "A Robust Approach to Enhance Tumor-selective Accumulation of Nanoparticles," *Oncotarget* 2011 2(1-2):59-68; Baish, J. W., Stylianopoulos, T., Lanning, R. M., Mamoun, W. S., Fukumura, D., Munn, L. L., and Jain, R. K. 2011. "Scaling Rules for Diffusive Drug Delivery in Tumor and Normal Tissues," *Proceedings of the National Academy of Sciences of the United States of America* 108(5): 1799-1803; Trédan, O., Galmarini, C. M., Patel, K., and Tannock, I. F. 2007. "Drug Resistance and the Solid Tumor Microenvironment," *Journal of the National Cancer Institute* 99(19):1441-1454; Kyle, A. H., Huxham, L. A., Yeoman, D. M., and Minchinton, A. I. 2007. "Limited Tissue Penetration of Taxanes: A Mechanism for Resistance in Solid Tumors," *Clinical Cancer Research* 13(9):2804-2810; Minchinton, A. I. and Tannock, I. F. 2006. "Drug Penetration in Solid Tumours," *Nature Reviews. Cancer* 6(8):583-592; Grantab, R., Sivananthan, S., and Tannock, I. F. 2006. "The Penetration of Anticancer Drugs through Tumor Tissue as a Function of Cellular Adhesion and Packing Density of Tumor Cells," *Cancer Research* 66(2): 1033-1039; Tannock, I. F., Lee, C. M., Tunggal, J. K., Cowan, D. S. M., and Egorin, M. J. 2002. "Limited Penetration of Anticancer Drugs through Tumor Tissue: A Potential Cause of Resistance of Solid Tumors to Chemotherapy," *Clinical Cancer Research* 8(3):878-884; Lankelma, J. 2002. "Tissue Transport of Anti-cancer Drugs," *Current Pharmaceutical Design* 8(22):1987-1993).

Provided a motorized positioning system is available, the implantation of nonstenting miniballs can benefit from semiautomatic discharge when this added capability is available, but if not, these can be precisely targeted manually on an individual basis. That is, while both stenting and nonstenting discharge benefit from semiautomatic machine control support, precise positioning of the airgun exit-hole or holes usually demands a degree of precision and speed that necessitates automatic support where the discharge of medication miniballs or positioning of tool-inserts for an angioplasty, for example, do not. Accordingly, for higher density implantation at a higher rate, machine support must afford the additional capability of semiautomatic discharge sequencing keyed to transluminal or linear stage and rotatory or turret-motor displacement whereby the operator can trigger a uniformly spaced pattern of miniballs at one time rather than the discharge of a single miniball or shot-group. The need for an automatic positional control system is thus not created by a need for close spacing in general but rather uniform close point to point spacing at a high rate.

The controls provided for the operator are addressed below in the sections entitled Ablation and Ablation and Angioplasty-capable Barrel-assembly Onboard Control Panel and Barrel-assembly Power and Control Housing, among others. Antecedent to any use of automatic control, the stepper motor-driven linear positioning stage or table is signalled to advance or retreat and the turret-motor to assume a rotatory angle in timed coordination with the successive discharges of an interventional airgun or if precise motional control is necessary, for positioning a tool-insert injector or abrader, for example. The airgun is mounted on a linear positioning stage, which typically allows continuous movement of about 15 centimeters without the need for repositioning. This distance is generally greater than that needed to move from one lesion to the next over the affected segments of a vessel but may be needed when the benefit of additional angioplasty or the administration of a drug by injection tool-insert, for example, becomes apparent after miniball discharge has been initiated.

The airgun settings for moment of discharge, and when adjusted, the exit velocity, are controlled as auxiliary functions of the automatic positioning control system. At normal (nontachycardic) heart rates to which the operator or an assistant can respond manually, complex synchronization circuitry such as that incorporated in cardioverter defibrillators or the use of imaging machines (see, for example, Souchon, R., Gennisson, J. L., Tanter, M., Salomir, R., Chapelon, J. Y., and Rouviere, O. 2012. "Measurement of Pulsatile Motion with Millisecond Resolution by MRI," *Magnetic Resonance in Medicine* 67(6):1787-1793), for example, should not be needed. If the area for secondary or touch-up treatment is more extended, then repositioning can be accomplished by disengaging the barrel-assembly from the airgun freeing it for independent manual advancement or withdrawal, then reinserting it in the airgun.

Provided the view afforded is adequate, direct manual control of the linear (transluminal) stepper and turret motors will usually allow fine adjustments in position sufficient for precise such miniball targeting or injection by an injector tool-insert, for example, without the aid of a positional control system much less one under automatic control. As one factor in reducing procedural times, rotary magazine clips that provide ten or more discharges of four or more shots to the shot-group per discharge, for example, support the loading requirements for high-density implantation. However, even with multiple implants delivered per discharge, to minimize intraluminal time also requires speed and accuracy of discharge while, moreover, withdrawing or advancing the barrel-assembly by quick steps.

This, and if necessary, the release from injection tool-inserts of a lubricant and/or nitric oxide, serve to minimize any tendency toward endothelial cling (adhesion) or impedance from encroachment against the sides of the muzzle-head by the lumen wall as could result in stretching injury if not a perforation. Semiautomatic discharge consists of the operator manually triggering a sequence of discharges that proceeds automatically. During stenting miniball discharge, to achieve uniform positioning of implants in a close formation, the control of transluminal positioning, whether discharge is triggered manually or semiautomatically, is generally relegated to a linear positioning stage, and rotatory positioning to the turret-motor. Due to the small angular adjustments that may be required, semiautomatic discharge usually includes control over the turret-motor.

In arteries, stays are inserted on the systoles, miniballs on the diastoles. The rate of discharge is not significantly impeded when the immediately preceding miniballs or sequence thereof must be allowed to seat, or reach the trajectory end-points or termini during a diastole, before the following discharge is triggered on the next diastole. The coordinated use of imaging equipment and resynchronization technology makes possible the automatic synchronization of discharge to the pulse or peristalsis; however, even without means for adapting to the physiological action when arrhythmic (erratic), to do this necessitates a level of complexity and expense that should seldom prove necessary. Repositioning of the muzzle-head over distances of several centimeters is usually accomplished manually whether the barrel-assembly remains inserted in the airgun barrel.

When the condition of the lumen wall is nonuniform, each discharge is confirmed as satisfactory before proceeding to the next. When the lumen wall is uniform, the discharge sequence, usually that provided by the rotary magazine clip, is confirmed. Each rotary clip can completely change the type and number of the miniballs, no two of which need be the same except in caliber, those of the barrel-tubes not changeable midprocedurally without withdrawal and reentry. Whether the miniballs are discharged manually or semiautomatically, to allow the immediate application of remedial measures in the event of a mishap, it is preferred that each discharge or discharge sequence be visually confirmed as having been properly placed before proceeding to the next discharge.

When the stent-jacket or segmental stent-jacket is prepositioned to prevent a perforation, imaging includes an endoluminal viewing device, such as a fiberoptic endoscope or angioscope built into the barrel-assembly or inserted through the central channel of a combination-form barrel-assembly to emerge through the nose-hole thereof. A fine gauge intravascular ultrasound catheter can be incorporated thus but is costly. These are described in the section below entitled Types of Barrel-assemblies. The rate of sequence discharge is not significantly affected by barrel-tube transit time or the transit therein of two or more miniballs therethrough at the same time. For simplicity, the section below entitled Positioning of the Muzzle-assembly with the Linear Positioning Table and Turret-motor recommends a pulse synchronization that is most comfortable to the operator based upon the available view.

While food intake can be stopped in advance, and drugs are available to reduce or stop movement in the gut, peristalsis is usually not so fast as to thwart calculating predictive discharge. The specific procedure as including implant insertion, ablation, or injection, for example, will determine whether the flaccidity of drug induced enteroparesis or the tonus sustained by its avoidance will best serve. To accomplish fine incremental advancement or withdrawal, the patient and barrel-assembly are positioned on the same height from the floor as the airgun barrel. A semiautomatically operated single-axis linear positioning stage or linear positioning table with the airgun to mounted atop it is used to withdraw or advance the barrel-assembly by a distance (increment, interval) with each discharge, usually the same distance.

When discharges follow in rapid succession, implantation follows each triggering of the airgun by the short interval that it takes for the projectile implants to transit the barrel-tubes and reach the trajectory end-point. Incremental movement of the linear positioning table and discharge need not be detained for each such recurrence. For simplicity and safety, successive manual triggering of each discharge and incrementing of the table are timed to confirm the proper seating of the implants before continuing. Discharge when the ductus is relatively quiescent reduces the continuous fluctuations in target position and mechanical properties but a flaccid condition that equates to laxness of the smooth muscle can effectively reduce the hardness and penetrability of the tissue.

When used in an artery, greater control and precision is attained when discharge occurs during the end-diastoles than when the wall expands during systoles, which intervals expedite and are used for repositioning of the muzzle-head and allowing blood to pass. In smaller vessels, the limited number of barrel-tubes that can be used underscores the value in automated positional control for optimizing the rate of discharge as well as achieving precision in close formation of the implants at a much higher rate than might be achieved by manual targeting, thus minimizing the risk of inducing ischemia during implant delivery. The synchronization of implantation to the intrinsic motility in the ductus during discharge of the airgun under direct manual control is facilitated through means addressed in the section below entitled Stabilization of the Implant Insertion Site.

The positional control to be described is primarily used to execute brief, usually repetitive, point-to-point discharge-move (advance, withdraw, and/or rotate)-discharge patterns with a dimensional resolution that exceeds manual ability. Otherwise, the apparatus is fully responsive to the instant command of the operator, who triggers the execution of each such pattern. Control thus is semi-rather than fully automatic. Fully automatic control is seldom employed as relinquishing operator discretion, and as with any machine action, can be halted instantly by pressing the cancel or 'kill' switch on the control panel. The action can then be resumed where it was left off or terminated.

Because both the implants and stent-jacket are inserted through the same small incision, 'direct stenting' of an atheromatous artery or a partially encrusted ureter, for example, by implanting stent-stays without endoluminal preparation through ablation, atherectomy, or an angioplasty, eliminates the need for a transluminal procedural component altogether. A test for wall strength is provided below in the section entitled Testing and Tests. Concerns for a lumen wall that having been angioplastied requires support to preserve patency but is too weak to withstand outward retraction is to avert implant pull-through or a rupture by placing a magnetic stent-jacket coated internally with a surgical cement or tissue sealant first and using broad cyanoacrylate coated stent-stays instead of deferring ballistic implantation to a later date. A cement almost in the internal environment is broken down over time; however, this should allow sufficient time for healing.

12. Concept of the Impasse-Jacket

Impasse-jackets, addressed below in the section entitled Miniball and Ferrofluid-borne Particle-impassable Jackets, or Impasse-jackets, are magnetized collars for prepositioning about a ductus to trap loose, or to hold, a miniball or microspherules in the bloodstream or along the digestive or reproductive tract, for example, or to attract magnetic drug or radionuclide carrier bound nanoparticles from the passing lumen contents, usually blood. That an impasse-jacket will stop any magnetically susceptible matter means that drugs and/or others pharmaceuticals or therapeutic substances can be delivered to it in any combination in any sequence. As is true of stent-jackets used with stays and clasp-jackets, impasse-jackets are placed without endoluminal entry. The potential applications of impasse-jackets to reduce the risk of occlusion which the family history and genome indicate that risk approaches certainty is high are many.

For example, the prepositioning of impasse-jackets on the carotids of adolescent heterozygous familial hypercholesterolemics and sitosterolemics, or phytosterolemics, to locally release a statin thereby supplementing the systemic with a concentrated local dose, can be used to reduce the risk of stroke while avoiding a systemic level that induces adverse side effects. Such direct delivery to an affected segment, for example, takes advantage of the nonhepatic benefits afforded by statins as addressed above in the section entitled Drug-releasing and Irradiating Miniballs, Stays, and Ferrofluids, among others, and may avert the need for an endarterectomy in later life. If a reversal agent is necessary, a downstream impasse-jacket is used to release 3-hydroxy 3-methylglutaryl coenzyme A reductase to take up any residual portion of its inhibitor.

An impasse-jacket can be positioned upstream of a stent-jacket to release a statin or other therapeutic substance to flow over the lumen wall thereby to treat the stented segment. The releasant if drug carrier nanoparticle bound is drawn into the stented segment; if not, then the statin flows over the stented lumen surface. If a statin, then any residue can be allowed to add to the systemic dose, or if to be neutralized, then a second impasse-jacket downstream from the stent-jacket can release 3-hydroxy-3-methylglutaryl-coenzyme A reductase as a reversal agent to take up the inhibitor, as well as stand positioned to trap any miniball that might enter from upstream. Analogous applications are numerous. Unless fully charged or loaded, any holding jacket will trap a passing miniball, and any trap-jacket with the loading space available can be used to release medication as a holding jacket.

In most if not all such applications, the last, or reversal agent-releasing, and trap-jacket jacket is implanted first. To avert migration without constricting the substrate ductus, the impasse-jacket is selected for an internal diameter that matches the quiescent or end-diastolic outer diameter of the artery or other type ductus, closes under the restorative force of a spring-loaded hinge, and is lined with nonbiodegradable or bioresistant viscoelastic polyurethane moisture barrier-coated viscoelastic polyurethane foam. The impasse-jacket thus expands and contracts with the substrate ductus, as do stent-jackets, clasp-wraps, and magnet-wraps. Impasse-jackets differ from stent-jackets in attracting miniballs against rather than within the lumen wall. Impasse-jackets used protectively to interdict a loose miniball in the bloodstream from embolizing downstream or limit the transit of a medication miniball that should not be allowed past a certain level are trap-jackets.

Holding jackets will retain a 'smart pill' or miniball for the targeted release of a drug or drugs at a later time when needed by external control, magnetic, electromagnetic, microwave, or the ingestion, injection, or infusion, such as central venous or subclavian, of a triggering substance. Those used for medicinal rather than protective purposes catch and hold medication miniballs delivered through the lumen are structurally the same of very similar and referred to as holding jackets. The distinction between trapping and holding is intended only to indicate a primary function; trap-jackets hold, and holding jackets trap, but some trap-jackets are intended only to trap, and so on. The ability to target a drug therapeutically also constitutes an in vivo pharmacological development test for the effect of the drug on a particular normal or diseased tissue organ, or a tumor.

Magnetic components such as impasse-jackets can be used to target a segment of a ductus or an organ for the receipt or the sequestration (isolation) from a particular drug or other therapeutic substance. The impasse-jacket is configured to allow the trapped or suspended medication and/or radiation releasing miniball to be noninvasively extracted at any time by a powerful extracorporeal magnet, usually with relatively short term and minimal interference with the intrinsic action in the ductus. In a blood vessel, an impasse-jacket serves to trap a loose miniball from continued movement through the circulation and/or acts to draw magnetic drug carrier particles from the blood into the wall of the lumen it encircles. An impasse-jacket placed about an incipient or early stage aneurysm will both restrain its enlargement and serve as a drug releasing point.

Placement along the arterial tree sets the territory supplied with the drug, so that placed about the aorta, the systemic circulation carries the drug to the body with little sent to the lungs, whereas placement about the pulmonary artery targets the lungs. Similarly, placing the jacket about the superior or inferior mesenteric artery would target the portion of the gut supplied. Depending upon whether the drug is dissolubly bound to the drug carrier nanoparticle, it can be drawn into the wall or released into the circulation. Aneurysms are exceptional in susceptibility only to systemically distributed antihypertensives, beta and/or angiotensin II receptor blockers with a statin helpful from the standpoint of lowing blood fats; however, most nonaneurysmal lesions affecting ductus can be locally targeted.

Impasse-jackets can be made to be absorbed when no longer needed. In an absorbable impasse-jacket, the extraction grid is made of a magnesium alloy of appropriate life in the internal environment, magnetization is by means of chemical isolation-encapsulated granular neodymium lanthanoid that will be innocuous when a residue, and the moisture barrier-coated viscoelastic polyurethane foam is treated to encourage disintegration by the immune system. An absorbable impasse-jacket such as one placed to suspend medication miniballs at a certain level over a limited period is, however, the exception; most must remain to guard against future embolization should a stenting miniball enter the bloodstream as the result of a direct blow, for example, or the jacket may need to be recharged with medication miniballs for an indeterminate period into the future.

Direct lines to impasse-jackets and/or their outriggers or dummy collars from the body surface is addressed below in the sections entitled Direct Lines from the Body Surface to and from Impasse- and Other Type Jackets and Single and Plural Circuit Pumping through Direct Lines to Jackets. Stent-jackets can also trap and retain susceptible miniballs or a ferrofluid to interdict further passage or allow spontaneous or controlled release of the contents; however, these do not incorporate a grid or grate barrel that allows the use of a powerful magnetic field to extract the susceptible matter to a position outside the ductus, and most exert field strength only sufficient to exert the minimum tractive force on the miniballs used to preserve luminal patency without tunical delamination or pull-through. Miniballs in noncirculatory ductus are readily recoverable, so that the use of impasse-jackets as traps is substantially confined to the circulatory system.

Unlike impasse-jackets, stent-jackets are not configured to allow the noninvasive removal of a suspended miniball or microsphere at any time. The perforated collar required disallows the addition of a radiation attenuating shield, for example. Medication and/or time-release medication miniballs, microspheres, drug carrier particle-containing ferrofluid, or spherules containing these always include sufficient ferrous content to assure recoverability. These are infused or injected directly into the bloodstream upstream to the jacket. For use in the digestive tract, this material is swallowed. A medication miniball or microsphere intentionally directed to and held suspended in an impasse-jacket may be used to initiate the release of a ferrous-unattached drug or other therapeutic substance into the circulation at that level, or to release magnetic drug-carrier particles for direct attraction into the surrounding lumen wall by the impasse-jacket that encircles the wall.

Impasse-jackets and stent-jackets that can be used as suspension or holding jackets can be used to trap ferrofluid-bound drugs and/or radionuclides, and encapsulated microspheres or miniballs incorporating these approaching through the bloodstream. Release of a drug from a microsphere or miniball can take any of numerous forms, to include time separated dissolution of the shells thereof, and can do so in response to a number of inducing conditions ranging from the mere flow of blood to the injection of a breakdown or dissolution agent, and/or the application of heat. When prepositioned to inhibit a disease of known course from spreading, a drug held within the lumen encircled by an impasse-jacket can be activated at any later time to serve a preventive, abating, or palliative function.

Since an unmetered or abrupt filling (loading, charging) of a holding jacket by a large number of miniballs might obstruct it, the medication is ordinarily concentrated in small sphericles, vesicles, or a fluid vehicle. Like stent-jackets, impasse-jackets can be chained, with each sub jacket selected for the segment of the ductus will appose and treat before it is connected into the chain, and a chain can incorporate both stent-jackets and impasse-jackets thereby gaining the special capabilities of either type jacket as specified above in the section entitled System Implant Magnetic Drug and Radiation Targeting, among others. Midprocedurally, an impasse-jacket prepositioned upstream from the treatment site can be used to intercept a miniball loose in the bloodstream, and when necessary, an external electromagnet with probe directed toward the impasse-jacket can be used to extract the miniball or other ferrous matter containing contents intercepted and held by the jacket.

The field strength exerted by the jacket-centered semicircumferentially magnetized magnet or magnets is chosen for the least magnetically susceptible miniball or drug carrying microsphere or particles to be stopped. Because the suddenness of extraction does not allow the miniball to pull at and tear away adjacent tissue, even when an external magnet alone is used to extract a miniball loose in the circulation, the exit perforation through the lumen wall will be relatively 'clean' and little if at all productive of debris. By framing about the miniball, the grid of an impasse-jacket further protects the tissue surrounding the extraction trajectory from stretching injury. The cellular exudate released and any neighboring body fluid spontaneously seal the perforation. The risk of thrombosis is reduced by coating the miniball with platelet blockade and usually, administering a systemic antithrombogenic agent.

Miniball interception and suspension within a trap-jacket does not equate to a need to extract the miniball; when there is no interference with circulation and the strength of retention is sufficient, the miniball can be left in the jacket interminably or for removal at a later date. Much of the utility of impasse-jackets will be realized as a result of the ongoing development of orally administered magnetically susceptible carrier nanoparticle-bound drugs. As opposed to the injection of a ferrofluid and use of a powerful external electromagnet to draw the drug carrier particles into the tissue to be treated, an immediately prepositioned magnetized jacket is present continuously, dispensing with the need for a properly adjusted extracorporeal magnet available only at a clinic; however, regardless of the magnetic source employed, drug administration that requires injection or infusion will continue to depend upon self-administration through a subcutaneously implanted portal or tie the patient to the clinic.

Until orally administered magnetically and/or metabolically targeted drugs appear, administration is usually by upstream injection directly into the artery or other ductus. How close to the stopping point the medication is introduced is determined by the rate of spontaneous dissolution if applicable, the degree of invasiveness required, and the benefit in avoiding the upstream circulation. Except in an open surgical field, the extravascular implants described herein such as impasse-jackets are introduced through a laparoscopic stab or 'keyhole' incision. By minimizing stretching about the exit-hole, the wire grid-surround favors clean extraction. The grid-surround should not be so elastic as to collapse or the grid perforation borders so lacking in stiffness (rigidity) or elastic as not to further suppress stretching injury during extraction.

However, this necessitates that it be sufficiently robust to not collapse under the pull of the extraction electromagnet. This strength requirement has no effect on small impasse-jackets, which are inserted with the length normal to and through a keyhole incision. However, to collapse for insertion through a small incision, a large impasse-jacket, such as one with an internal diameter of 7 centimeters for placement about the colon, must be collapsible. The simplest resolution for these contradictory requirements is to insert the grid-surround with end bumpers through the entry incision as four cylindrical quadrant hinged bifolds that are placed to progressively encircle the ductus by connection together with hinges. Once completed, the cylinder is encircled by hinged snap rings (hinged key rings, looseleaf book rings) held in channels continuous around the bifolds once assembled about the ductus.

Whether an impasse-jacket or a stent-jacket, when made of material intrinsically magnetized, each half cylinder is magnetized by rotation before the magnetizer separately; continued rotation of a complete cylinder would partially demagnetize the opposite half cylinder. Unlike magnetized miniballs and stays, addressed above in the section entitled Drug-targeting Miniballs and Stays, which can be used to like purpose, an impasse-jacket eliminates the need to introduce implants ductus-intramurally. This factor makes it possible to use impasse-jackets with tissue too weakened by diseased to retain these. The impasse-jacket can be used to draw any therapeutic substance, such as a tissue hardener, ductus-intramurally. In situ tests for ductus wall strength are addressed below in the section entitled Testing and Tests.

Once placed, the jacket is positioned for any later administration of suitably formulated medication or other therapeutic substance, such as a radionuclide, hormone, or enzyme. The same is true of a stent-jacket, which lacking suitable openings does not, however, permit miniball extraction, cannot incorporate a radiation shield for use with a radionuclide of high dose rate, and generally must exert less magnetic strength for stenting. Since the wire grid surround must allow the use of an external magnet to extract a miniball held within the jacket without collapsing despite its opposing polarization, and making it of stock that is rectilinear in cross section could result in the catching hold and trapping of a miniball on the adluminal face, a rounded interface is used.

Similarly to the magnets mounted about the base-tube of a stent-jacket, the impasse-jacket grid surround is magnetized axipetally (radially, centripetally) to its central longitudinal axis, which will be that of the lumen to be encircled. With intrinsically magnetized stent and impasse-jackets, thickness, flexibility, and magnetized face contour must be coordinated. Increasing the thickness of the magnetized portion of the jacket reduces flexibility and may necessitate machining longitudinal furrows to allow the degree of flexion needed. For ease of manufacture, intrinsically magnetized stent and impasse-jackets are made of sheet stock with the perforations punched therein, then rolled to produce the side-slitted or -slotted cylinder. The flat but rounded conformation is more effective for reducing stretching of the tissue surrounding the exit trajectory but less effective for exerting tractive force.

The interposition of a moisture barrier-coated viscoelastic polyurethane foam lining between the adventitia and the internal surface of the jacket allows flat-faced slats or stock generally pyramidal with the apices directed toward the long axis of the lumen to be applied internally but adds expense. The gauge of cylindrical stock in a practical grid must support the magnetic strength required; the wire grid shown in FIG. 16 conforms to the performance conditions required at the treatment site for which it is intended. By placing the patient in an alternating magnetic field, ductus intramurally implanted medication or medicated miniballs and miniballs suspended in the bloodstream in an impasse or stent holding jacket containing magnetically susceptible nano- or microparticle-bound drugs can be heated. Thus, depending upon the specific drugs, any coatings, and/or the medium in which the drugs are suspended, the dissolution temperature can be raised to control or accelerate the release of each drug.

Unless thermally-insulated by a polymeric coating, the magnetic material of stent- and impasse-jackets and the mesh of an impasse-jacket when magnetically susceptible will also warm the ductus from the outside. Upon cessation of the alternating magnetic field, the traction exerted by the jacket accelerates layer breakup, drawing the particle bound drug or radionuclide against and into the diseased tissue. When the ferrous matter in the jacket is also heated, the combination of tissue warming and magnetic attraction will usually further enhance local uptake of the drug or drugs released. Particles, microspheres, and miniballs in tissue or suspended in the lumen, and impasse-jackets themselves, can be heated to release coatings and contents, or to apply magnetic hyperthermia. The jacket outside the lumen wall, the effect does not apply to thermoablation.

The temperatures involved in heating thus fall well below the Curie temperature that would demagnetize the jacket. An absorbable stent-jacket of polylactic coglycolic acid can incorporate magnetized iron particulate that will provide the magnetic force and when noninvasively heated by placing the patient in a radiofrequency alternating magnetic field, will be heated to melt a coating on the particulate that will enzymatically or hydrolytically effect the breakdown or accelerate the dissipation of the jacket or other absorbable components when extraluminal where the spontaneous rate of dissolution is usually less. In nonabsorbable jackets, embedment thus can be used for hyperthermia, to initiate or accelerate the release of a drug or its rate of uptake, or to heat drug carrier nanoparticles once drawn into the lumen wall whether as hyperthermia, to initiate or increase the rate of drug uptake, or to dissipate or, or any of these purposes in combination, for example.

The same pertains to other implants such as stays and miniballs where it can be used to flow a bonding agent such as a eutectic protein solder or release a drug as well as accelerate its uptake, and miniballs whether ductus-intramurally implanted or suspended in an impasse-jacket. Where ductus-intramural layer and or melting point distinct dissolution is temperature controlled, ductus-intramural miniballs and stays and endoluminal miniballs can be used in coordination for timed delivery of different drugs or combinations of drugs, those successive combining with, supplementing, reversing, or counteracting such as by breaking down to inactivate or neutralize, those released previously, as addressed below in the section entitled Cooperative Use of Impasse-jackets in Pairs and Gradient Arrays.

The system described herein allows temperature control through multiple means, to include 'cooling' catheters, which are equally usable to raise the temperature in a barrel-tube, addressed below in the sections entitled Rapid Cooling Catheter and Cooling Capillary Catheter for Cooling Heated Turret-motor, Electrically Operated Radial Projection Unit Lifting Thermal Expansion Wires and Heaters, and Recovery Magnets and Cooling Catheters (Temperature-Changing Service-catheters), among others, and inmate heat-windows, addressed below in the section entitled Thermal Conduction Windows (Heat-windows) and Insulation of the Muzzle-head Body in Minimally or Fully Thermal Ablation and Thermal Ablation and Angioplasty-capable (Independently Usable) Barrel-assemblies, among others.

Although the miniballs, stays, stent-jackets, impasse-jackets, and patch-magnets described herein are novel, that these implants when containing ferrous matter or a resonant circuit would be heated by placement in a magnetic field alternated at radio frequency is uninventive. All of the magnetized implants described herein, to include impasse-jackets, stent-jackets, magnet-jackets, and patch-magnets support the magnetic drug and/or radionuclide targeting of a length along a lumen or an entire organ. With an endoluminal lesion, the drug is drawn against the endothelium and directly into the lesion with or without the addition of heat. For attraction against and into the lumen wall, the drug, radionuclide, or other therapeutic agent is ferrobound, that is, bound to magnetically susceptible carrier nanoparticles and therefore drawn along with the susceptible carrier, which can, for example, be contained in a ferrofluid or within the absorbable envelope of a miniball that is dissolved by the introduction of another substance and/or heat, for example.

When intended for release into the circulation, the substance for targeted delivery is ferro co-bound, that is, not indissolubly bound to magnetically susceptible particles, as this would draw the substance against and into the lumen wall encircled within the jacket. Instead, the delivering container, such as a miniball or microspheres with an absorbable outer layer, incorporate a magnetically susceptible core. The dissolution of the outer layer that liberates the substance may be formulated to be dissolved by the passing blood, with the subsequent, hence, time controllable, administration of an agent that acts as a solvent, or by heating at the level for release, such as by a heat-window or a heat noninsulated tool-insert. Jacketing an artery that supplies an organ, for example, allows the release of drugs, nutrients, or other substances at the level of the jacket.

If the substance to be restricted to only the targeted tissue is not taken up by it, that is, not assimilated, absorbed, or catabolized within the parenchyma, then the outflow through the jugular veins is jacketed when necessary to eliminate any unwanted residue by releasing a drug molecule-cleaving, binding, inverse agonist acting, or otherwise neutralizing or inactivating substance (reversal agent). Impasse-jackets used to treat the brain are solely for whole-brain treatment with one jacket releasing medication from miniballs it holds at the inlet (internal carotid artery) and when necessary, another jacket at the outlet (the jugulars) to release a reversal agent, counteractant, or neutralizing substance. Also, for incorporation into microspherules or miniballs, the drugs must be capable of high concentration. The uses of impasse-jackets is, then, fundamentally different in application from those of percutaneous transluminal microcatheters, which are passed up into a vessel within the brain to target a glioblastoma with a large volume of a mannitol and after a few minutes, an antiangiogenic drug, for example.

A stereotactic magnetic guidance system for the delivery of drugs within the brain is based upon a separate technology (see, for example, Abrishamkar, S., Moin, H., Safavi, M., Honarmand, A., Hajibabaie, M., Haghighi, E. K., and Abbasifard, S. 2011. "A New System for Neuronavigation and Stereotactic Biopsy Pantograph Stereotactic Localization and Guidance System," *Journal of Surgical Technique and Case Report* 3(2):87-90; Leach, J. H. 2003. *Magnetic Targeted Drug Delivery*, Masters Thesis, Virginia Polytechnic Institute and State University, Blacksburg, Va.; McNeil, R. G., Ritter, R. C., Wang, B., Lawson, M. A., Gillies, G. T., Wika, K. G., Quate, E. G., Howard, M. A., III, and Grady, M. S. 1995. "Functional Design Features and Initial Performance Characteristics of a Magnetic-Implant Guidance System for Stereotactic Neurosurgery," *Institute of Electrical and Electronics Engineers Transactions on Biomedical Engineering* 42(8):793-801; McNeil, R. G., Ritter, R. C., Wang, B., Lawson, M. A., Gillies, G. T., Wika, K. G., Quate, E. G., Howard, M. A., III, and Grady, M. S. 1995. "Characteristics of an Improved Magnetic-implant Guidance System," *Institute of Electrical and Electronics Engineers Transactions on Biomedical Engineering* 42(8):802-808). If implemented, the helmet based system would be limited to the administration of drugs in the clinic.

Once an impasse-jacket has been implanted, a drug can be released directly into the bloodstream noninvasively with a quicker response time obtained by collateral intramuscular injection. A patient could, for example, trigger the release of an anticonvulsant by warming the implantation site with an electrical heater or by self injection. The prepositioning of different drugs using such means is intended to allow targeted, quicker, finer, and tighter control over the release of drugs, usually on a small scale, than can be achieved through intramuscular injection. Tiny patch-magnets used to hold miniballs of which the contents can be released by heating or by exposure to another chemical, for example, can be inserted within a parenchyma during open surgery when the organ has been exposed if not entered for a primary procedure.

A drug-binding ferrofluid released upstream into the circulation, whether by intravenous infusion, injection, or ingestion, or microspheres or miniballs suspended within entry impasse-jackets placed about the internal carotid arteries, for example, will upon dissolution release drugs into the bloodstream. If the outflow from the brain contains any of the drug but the drug is neutralized, this substantially isolates and targets the brain, the reduction in exposure of other head and neck structures to the medication dependent upon the proximity to the brain along the common then internal carotid artery. Limitation of delivery to the brain will not avert psychological or hormonal side-effects that also originate within the brain; however, avoiding the systemic circulation substantially eliminates brain-unrelated side effects, as well as allows the overall dose to be significantly reduced. Isolation of the brain contemplates the use of antineoplastic, germicidal, and antiparasitic drugs.

Thus, most of the adverse side effects associated with antipsychotic or neuroleptic drugs, such as tardive dyskinesia, weight gain, and akathisia, originate in or involve the brain; however, non-brain-derived side effects such as agranulocytosis may be avoidable if the systemic circulation is avoided. Other organs can be isolated in an analogous manner. Closer approximation to the brain along the internal carotid artery increases the dissection needed to place the jacket. However, less proximate placement, even though it less minimizes delivery to the non-brain parts of the head and neck, avoids the greater trauma of more proximate placement and still allows a significant reduction in overall dose compared to that required for delivery through the systemic circulation. Release of the drug from an entry jacket must be justified on this basis.

Whether released into the systemic circulation or at the inlet to the brain, the drug must then be drawn into the brain. Magnetic means alone will not overcome the blood-brain and blood cerebrospinal fluid barriers, although in some instances, such means can be adapted to accelerate the uptake of a drug carrier substance such as nanoparticle-bound leukotriene C4 to temporarily disrupt the barrier and/or a drug formulated to pass the barrier. When no brain tissue has been removed, patch- or clasp-magnets are placed in a sulcus (fissure, anfractuosity) between gyri or in a subarachnoid cistern. In situations where tissue has been resected or there is sufficient atrophy, intracranial (endoencephalic) space will already have been created.

The feasibility of using an intracranial implant for infusing medication directly into the brain, referred to as intracranial or subarachnoid pharmacotherapy, goes back two decades (see, for example, Smith, D. C., Krahl, S. E., Browning, R. A., and Barea, E. J. 1993, "Rapid Cessation of Focally Induced Generalized Seizures in Rats through Microinfusion of Lidocaine Hydrochloride into the Focus," *Epilepsia* 34(1):43-53). However, compared to the impasse-jackets and patch-magnets described herein, the apparatus used was massive (see, for example, Fischell, R. E. Fischell, D. R. and Upton, A. R. M. 2000. "Responsive Implantable System for the Treatment of Neurological Disorders," U.S. Pat. No. 6,134,474; Ludvig, N. and Kovacs, L. 2002. "Hybrid Neuroprosthesis for the Treatment of Brain Disorders," U.S. Pat. No. 6,497,699; Ludvig, N. 2010. "Subarachnoid Pharmacotherapy for Maximizing Recovery after Cortical Ischemic Stroke," *Journal of Experimental Stroke and Translational Medicine* 3(2): 13-21; Ludvig, N., Medveczky, G., French, J. A., Carlson, C., Devinsky, O, and Kuzniecky, R. I. 2010. "Evolution and Prospects for Intracranial Pharmacotherapy for Refractory Epilepsies: The Subdural Hybrid Neuroprosthesis," *Epilepsy Research and Treatment Hindawi Publishing* 2010:1-11; Kahn, A. R., Chow, E. Y., Abdel-Latief, O., and Irazoqui, P. P. 2010. "Low-power, High Data Rate Transceiver System for Implantable Prostheses," *International Journal of Telemedicine and Applications* 2010:563903).

Drugs to pass through the barrier can be bound to a glucose or amino acid carrier or a large lipophilic moiety, for example, (see, for example, de Boer, A. G. and Gaillard, P. J. 2007. "Strategies to Improve Drug Delivery across the Blood-brain Barrier," *Clinical Pharmacokinetics* 46(7):553-576; Nestler, E. J., Hyman, S. E., and Malenka, R. C. 2001. *Molecular Neuropharmacology: A Foundation for Clinical Neuroscience*, New York, N.Y.: McGraw-Hill, pages 29-32; Pardridge, W. M. 1998. "CNS Drug Design Based on Principles of Blood-Brain Barrier Transport" *Journal of Neurochemistry* 70(5):1781-1782).

That passage through the barrier of a magnetically susceptible drug carrier nanoparticle-bound lipophilic molecule, such as nitorosoureas or procarbazine (Fetell, M. R., 1995. "Gliomas," in Rowland, M. P. (ed.), *Merritt's Textbook of Neurology*, Media, Pa.: Williams and Wilkins, pages 341-342) would be accelerated without the aid of adjuvant nitric oxide-generating compounds, leukotriene C4, cyclic guanosine monophosphate-specific phossphodiesterase 5 inhibitors through the oral administration of sildenafil or vardenafil (see, for example, Black, K. L., Yin, D., Ong, J. M., Hu, J., Konda, B. M., and 7 others 2008. "PDE5 Inhibitors Enhance Tumor Permeability and Efficacy of Chemotherapy in a Rat Brain Tumor Model," *Brain Research* 1230:290-302) or bradykinin, and/or calcium-activation of potassium channels with metastatic brain tumors (see, for example, (see, for example, Hu, J., Yuan, X., Ko, M. K., Yin., D., Sacapano, M. R., and 7 others 2007. "Calcium-activated Potassium Channels Mediated Blood-brain Tumor Barrier Opening in a Rat Metastatic Brain Tumor Model," *Molecular Cancer March* 14; 6:22), for example, is not suggested.

The use of prepositioned precursory drugs (see, for example, Rautio, J., Laine, K., Gynther, M., and Savolainen, J. 2008. "Prodrug Approaches for CNS Delivery," *American Association of Pharmaceutical Scientists Journal* 10(1):92-102), is addressed below in the section entitled Chemical Control over Implants and Coated Implants, to Include Miniballs, Stays, and Prongs. When uptake is incomplete as to leave a residue best prevented from entry into the systemic circulation, drug carrier nanoparticles or microspheres or miniballs containing these, for example, suspended within exit impasse-jackets placed about the jugular veins proximate to the outflow from the brain can be used to chemically and/or thermally neutralize the residue, such as by binding with or cleaving the drug or drugs.

By reducing the accumulation of drug carrier nanospheres in neighboring nontargeted, healthy or less severely diseased tissue, the use of small magnetized implants should also increase the efficacy as well as the sufficiency of treatment (see, for example, Pathan, S. A., Iqbal, Z., Zaidi, S. M, Talegaonkar, S., and 7 others 2009. "CNS Drug Delivery Systems: Novel Approaches," *Recent Patents on Drug Delivery and Formulation* 3(1):71-89; Silva, G. A. 2008. "Nanotechnology Approaches to Crossing the Blood-brain Barrier and Drug Delivery to the CNS," *BioMed Central Neuroscience* 10; 9 Supplement 3:S4; Brigger, I., Morizet, J., Aubert, G., Chacun, H., Terrier-Lacombe, M. J., Couvreur, P., and Vassal, G. 2002. "Poly(ethylene Glycol)-coated Hexadecylcyanoacrylate Nanospheres Display a Combined Effect for Brain Tumor Targeting," *Journal of Pharmacology and Experimental Therapeutics* 303 (3): 928-936).

Even without complete absorption or catabolic breakdown by the target tissue or organ, or neutralization of an outflow residue, the dose, generally tiny compared to the equivalent systemic dose even when much more highly concentrated for the target segment or organ, once entering the systemic circulation is quickly diluted to an innocuous level. Thus, when the agent used has no neutralizing substance and is resistant to heat, dilution by release into the systemic circulation can almost always be relied upon without the use of an exit-jacket. Such means are capable of targeting medication in a more focused manner than can an intrathecal pump. Moreover, administration is without the internal storage, potential for mechanical malfunctioning, and medical complications associated with a pump implant. Similarly, using a jacket on the renal artery and another on the renal vein, a kidney can be selectively targeted to the substantial exclusion of the systemic circulation. Keeping furosemide from reaching the cochleae nullifies its potential as an ototoxin, the number of potential examples myriad.

The need for a magnetic drug carrier attracting clasp or patch-magnet on the organ fibrosa or the equivalent between the entry, and if necessary, an exit-jacket, exists when the pathology itself does not result in a reduction in the level of resistance to penetration by and uptake of the drug. For example, while the blood-brain barrier appears to prevent oncolytic drugs such as paclitaxel from reaching therapeutic levels in normal brain tissue, therapeutic levels are achieved with gliomas (Shen, Y., Pi, Z., Yan, F., Yeh, C. K., Zeng, X., and 5 others 2017. "Enhanced Delivery of Paclitaxel Liposomes Using Focused Ultrasound with Microbubbles for Treating Nude Mice Bearing Intracranial Glioblastoma Xenografts," *International Journal of Nanomedicine* 12:5613-5629; Heimans, J. J., Vermorken, J. B., Wolbers, J.

G., Eeltink, C. M., Meijer, O. W., Taphoorn, M. J., and Beijnen, J. H. 1994. "Paclitaxel (Taxol) Concentrations in Brain Tumor Tissue," *Annals of Oncology* 5(10):951-953).

Where tumor uptake is less, pressure within the tumor and its effect on blood flow phenomena may limit penetration (Stewart, D. J. 1994. "A Critique of the Role of the Blood-brain Barrier in the Chemotherapy of Human Brain Tumors," *Journal of Neurooncology* 20(2):121-139). Restricted perfusion can to an extent be compensated for by increasing the strength of magnetization of the patch-magnet or magnets. Entry or inflow, and if necessary, exit or outflow jackets, can thus be used to concentrate a taxane, for example, in the brain while substantially sparing the rest of the body from exposure to such an antimitotic drug. A mitosis inhibitor or antimitotic suppresses cell division, and thus the division of tumor and intimal hyperlastic cells, but also other cells with a higher turnover rate, producing adverse side effects.

The high rate of cell division in hair follicles, for example, results in the alopecia or hair loss seen during chemotherapy with vinblastine, paclitaxel, and docetaxel, for example (*The Merck Manual of Diagnosis and Therapy*, 18th edition, Table 149-2). Significantly reducing if not eliminating the amount of drug that reaches the hair follicles should eliminate this side effect along with others of like cause. Contrariwise, drugs best prevented from entering the brain include ifosfamid, fludarabine phosphate, cisplatin, and nitrosourea carmustine, for example (Fetell, M. R. and Balmaceda, C. M. 1995. "Complication of Cancer Chemotherapy," in Rowland, M. P. (ed.), *Merritt's Textbook of Neurology*, Media, Pa.: Williams and Wilkins, page 984).

Thus, by using a higher concentration than could be used systemically and substantially restricting the release of the drug to the brain by placing the entry impasse-jackets on the internal carotids and releasing magnetic drug carrier bound medication from encapsulated microspheres seized from the passing blood, the neutropenia, anemia, myelosuppression, neutrotoxicity, peripheral neuropathy presenting as numbness of the skin on the hands and feet, paresthesia, bradycardia, and rarely, heartblock, which can be induced by paclitaxel; the fatigue, nausea, and rash sometimes induced by gemcitabine; and the constipation, nausea, diarrhea, myelosuppression, neuropathy, dizziness, hypersensitivity reactions in the form of bronchospasm, dyspnea, and hypotensionfluid retention, rash, and stomatitis associated with docetaxal (Sauseville, E. A. and Longo, D. L. 2005. "Principles of Cancer Treatment: Surgery, Chemotherapy, and "Biologic Therapy," in Kaspar, D. L, Braunwald, E., Fauci, A. S., Hauser, S. L., Longo, D. L., and Jameson, J. L., *Harrison's Principles of Internal Medicine*, 16th Edition, New York, N.Y.: McGraw-Hill, page 477), for example, if not eliminated, should be significantly reduced, along with the hair loss and other possible side-effects of anticancer drugs.

That this means can be used to prevent drugs from reaching the liver is especially significant for the reduction of adverse side effects. Exit jackets are generally reserved for releasing reversal agents or substances to neutralize or otherwise counteract those released at the start of segment or organ inlet or inflow when necessary. Such a substance may have been released to accelerate the dissolution of a miniball or miniball coating in the entry jacket when the use of heat was best avoided or may have been used in combination with heat. Focused and able to deliver a higher concentration of a drug, targeting remains applicable despite metastasis, in which case, impasse-jackets and/or clasp-magnets are applied to the other sites, and a collateral systemic dose administered to restrain further spread of the disease. When impasse-jackets are spaced at intervals along a ductus, the drug is preferably introduced upsteam of each impasse-jacket rather than upstream of the entire array.

Alternatively, injection or infusion upstream of the array or a subset of jackets for auto-apportionment requires that the drug carrier magnetic susceptibility, density of these, and the tractive force of each jacket allow the blood pressure to drive some microspheres or miniballs forward to the next impasse-jacket. To this end, different fractions of the injectant can be made to differ in magnetic susceptibility, and/or successive jackets can be made to exert a stronger magnetic field than that preceding. A rate of microsphere or miniball delivery that could clog a jacket for more than a moment before the pulse force the miniball forward is avoided. Since until metabolized, drugs magnetically held within the targeted tissue will remain, and any residue that passes through the target segment or organ would be immediately diluted, an exit impasse-jacket to release a neutralizing substance is often unnecessary.

Applicable no less to a delimited segment of a ductus or its luminal endothelium than to an organ, targeting allows the use of a drug to treat plaque, a tumor, or other lesion, and at a concentration that if circulated would be toxic. In all applications, the release of drugs and/or radiation from layered miniballs using differential temperature and magnetic targeting can be used. As addressed below in the section entitled Miniature Ball Implants, an alternating magnetic field can be used to achieve extracorporeal non-invasive control on a time-coordinated basis. Release at the inflow jacket can be through spontaneous or time released dissolution into the passing blood, or the drug can be formulated to dissolve in a controllable manner in response to the addition of a second drug, a nondrug chemical agent, and/or heat. These possibilities make possible follow-up treatment at any time over the period that the original miniball persists.

After that, continued treatment requires the infusion or injection of another miniball, whether one of like or of different formulation. That release can be triggered over a variable interval allows prepositioning for scheduled dosing over an indefinite period or emergency use. Release or accelerated release and uptake through placement of the patient in an alternating magnetic field to remotely heat the miniballs ties the patient to the clinic, but another chemical administered orally as preferred or by injection or infusion through a subcutaneously implanted portal to effect dissolution of the trapped miniball does not. Impasse-jackets and other magnetized implants are described and their applications delineated; however, the potential number of combinations and permutations of drugs, release or triggering mechanisms at both inflow or entry and outflow or exit jackets, and the anatomical structures to which these apply is potentially limitless so as not to be enumerable herein.

13. Concept of the Magnet-Wrap

A magnet-jacket, or magnet-wrap, comprises an array of small permanent magnets mounted on a spandex backing with hook and loop fasteners for wrapping about the ductus. It is usually intended to optimize the radially outward directed attractive force over a relatively large distance. It can be used to pull another ductus toward it or to pull the ductus it encircles toward the attracting magnet-wrap, patch-magnet, or simple magnetized and coated tab inserted under the outer layer of other tissue. Applied thus, a magnet-wrap, like a patch-magnet, must exert tractive force over a greater distance than must a stent-jacket placed in close proximity to the miniballs or stays it is to draw. A magnet-wrap is different than a stent-jacket in that the stretchable backing provided to allow longitudinal and circumferential compliance with motility in the substrate ductus supplants a more rigid backing as is necessary to draw ductus-intramural implants toward it, urging the ductus into luminal patency.

Stretchability also requires the use of discrete magnets, as defined above in the section entitled Types of Stent-jacket. In general, a magnet-wrap or patch-magnet is more strongly magnetized than is a stent-jacket. That either or both the structure attracted and attracting can be magnetized is obvious. That if to be drawn to a side or diverted in response to force imposed by a magnet or magnets over a distance the jacket need not incorporate magnets but only magnetically susceptible material is obvious. The radially inward directed poles of the magnets can also be used to attract underlying ductus-intramural implants or drug carrier nanoparticles, but such use is extraordinary, just as is the use of a stent-jacket for its outward directed poles.

Just as the contradictory distinctions in function that distinguish stent- from impasse-jackets makes the attempt to consolidate these into a single form inadvisable by degrading performance in both functions, attempting to mechanically optimize the form of an encircling sleeve for optimal use of both its inward and outward directed poles yields a device suboptimal for both. A stent-jacket can be used as a magnet mount to divert the vessel it encircles or to draw other tissue radially inward or adaxially toward it, and a magnet-wrap to attract in the radially outward or abaxial direction. Magnet-wraps used to attract the clasps of a clasp-wrap or miniballs over a distance may be strongly magnetized and used for large ductus where extraction will not be necessary. As is generally true of the components described herein, either the miniballs or the jacket can represent the magnetized or the susceptible factor. In the digestive or the urinary tract, the release of a magnetized miniball or miniballs from a ferromagnetic jacket through demagnetization would result in its spontaneous elimination.

However, while the temperature required could be reached by placing the patient in a radiofrequency alternating magnetic field, for example, the demagnetizing or Curie temperature will be too high for use inside the body, no material, much less one functionally compatible with the need for absorption or elution, for example, available that would insulate a core heated to 590 degrees Fahrenheit. When usable for this auxiliary purpose as well, stays, which have a conformation better suited to sustaining a magnetic circuit of high flux density than miniballs, will usually be needed. The ductus wall must be confirmed as able to support the increased tractive force involved. However, more reliable function in the radially outward or adaxial direction (which uses the abaxially facing pole) is obtained with a magnet-wrap (magnet-jacket, magnet-collar, magnet-sleeve, magnet-cuff, magnet-mantle, magnet-wrap-surround, magnet-bandage).

In contrast to stent- and impasse-jackets, a magnet-wrap uses the outward facing or abaxial poles of discrete magnets to exert tractive force in the radially inward (adaxial, axipetal, centripetal) direction. This force is applied to ferromagnetic implants infixed within another structure, discrete magnets providing the mass necessary to act over a distance. Unlike jackets for optimizing application of the inward looking poles to treat the substrate ductus itself, a magnet-wrap is unslit, without resilient backing, and almost never magnetized over more than a restricted arc about its circumference. It uses the substrate or encircled (ensheathed, mantled, enwrapped) ductus as but a mounting platform, itself not ordinarily under treatment.

The adaxial poles of the magnets can of course be used as well, to attract a drug carrier particulate, for example, but abaxial force is more uniformly applied by a stent- or impasse-jacket. The tissue drawn may be that of another ductus implanted with miniballs or stays or encircled by a clasp-wrap, described below in the section of like title, or nonductal tissue implanted with magnetically susceptible matter, which can consist of as a simple iron tab with or without a chemically isolating coating infixed within it. Since an affected ductus would normally be treated with a stent-jacket, and a stent-jacket can be used to exert ductus wall retractive force entirely about the circumference or over any arc desired, a magnet-wrap is used either to deflect either the platform or drawn ductus from its course or to draw nonductal tissue.

For example, within the constraint imposed upon the amount of force that may be used by the need to avert dysphagia, a magnet-wrap might be used to encircle the esophagus, thereby to exert patenting force on the trachea when collapsed or stenosed. Here it is ordinarily the roof or dorsal ligament (dorsal membrane) of the trachea that drops down into and obstructs the airway because the cartilage 'rings' have lost or not gained the strength required to support it, so that retractive or lifting force between apposite, or juxtaposed, sides of the two ductus would clear the airway. The stent-jacket can retract any arc about a ductus wall or draw it outwards circumferentially, and concentric, is closest, allowing the local use of the smallest possible ferromagnetic elements.

However, in some situations, alternative means for the support of the magnets will be necessary, specifically, for example, when traction that entirely surrounds the vessel or duct to be treated is not necessary and embedment within the surrounding tissue, attachment, or adhesions preferred left in place necessitates excessive dissection for the ductus to be approached and encircled. Such a ductus can be implanted with miniballs transluminally, and drawn from without by means of a magnet-wrap, clasp-magnet, or a simple tab magnet implant. In other use, the ductus, other tissue, either the substrate ductus or the structure drawn may have developed or become deviated, displacing or encroaching upon other tissue where the passage of magnetic lines of force through intervening tissue achieves the same retraction or fixation as would surgery but with less trauma, suture incapable of direct traction thus.

When, for example, the presence of an intervening structure precludes fixation with suture in the direction preferred, placing a clasp-wrap, ductus-intramural implants (miniballs or stays) or introducing ferromagnetic suture (see, for example, Slatter, D. H. 2002. *Textbook of Small Animal Surgery*, Oxford, England: Elsevier Health Sciences/Saunders, page 146) or staples, for example, allows the use of a magnet-wrap or clasp-magnets to retract the tissue instead. A collapsed ductus secured by connective tissue along one side as not to require retraction in that direction requires tractive force that is arcuate or directed rather than circumvascular. For example, having longitudinal muscle and diffuse connective tissue peripherally rather than a harder outer layer, the esophagus, as can be true of any diseased malacotic vessel, does not lend itself to implantation.

Nevertheless, a magnet-wrap can be used, for example, to suspend miniballs implanted along dorsolateral lines of the collapsed trachea in a toy breed dog from ventrolateral magnets along complementary parallel lines of magnets held within a magnet-jacket or jackets wrapped around the esophagus. Eccentric lesions in the vasculature are generally not anchored along one side so that tugging at a vessel would, arising concern for the affect on hydrodynamic blood flow through the ductus, its endothelial or vasotonic function, as well as compression on tissue bounding the side pulled. With other ductus, the concern will be the possibility of disrupting peristalsis. If not sufficiently immobile, the mounting platform looked to for positional stability may require some sutures or a more powerful permanent magnet to fixate. Then, depending which ductus is fixated, either the magnet-wrapped ductus or that drawn by it can be aligned or diverted.

Unless the field is already exposed for another surgical procedure, a magnet-wrap, clasp-wrap, and stays are inserted by laparoscopic entry. Such a less traumatic solution can be used to defer surgery until the patient can tolerate it or as a palliative measure for a patient with little time left. Traction exerted by a magnet-wrap used thus will almost always apply in a circumferentially limited (eccentric, radially asymmetrical) way as not to require magnets or magnetized content entirely about the circumference. Accordingly, adaxial or magnet-wraps differ from abaxial stent- and impasse-jackets in having a nonslitted and less resilient backing and far more often, exertion of magnetic force that is circumscribed or arcuate rather than entirely about the circumference. Magnet-wraps are addressed below in the section of like title. Generally not anchored along one side, tugging at a vessel with an eccentric lesion may affect hydrodynamic blood flow through the vessel, its endothelial or vasotonic function, as well as compress the tissue at the pulled side.

14. Concept of the Nonjacketing Side-Entry Connector

Ductus side-entry jackets about either or both internal carotid arteries allow the directly pipe-targeted delivery to the brain of any drug, whether psychotropic or oncolytic, for example, to the brain, for example. Brain tumors commonly require treatment with detumescent and anticonvulsant as well as chemotherapeutic medication. The side-entry connector can deliver drugs or electrostimulation with any pattern of stimulatory pulsation, such as alternating electric field therapy through an electrode and/or the semicircular needles used to anchor the connector. Once placed, drug delivery and fluid aspiration are not through the scalp but rather through the fluid lines connected to one or more subdermally placed small drug reservoir pumps and/or electrical lines entered through a small surface port addressed below.

More circumscribed targeting should seldom prove necessary, but can be accomplished by trephination and attachment of a nonjacketing side-entry connector directly to the surface of the dura mater or the cortex itself. Aside from the automatic control system with which a side-entry connector, unlike an Ommaya reservoir, is compatible, the connector itself is more versatile, in that it can deliver targeted molecular as well as well as electrostimulatory, cautery, hormonal, nanoengineered enzyme, and/or cytotoxic therapy. The catheter can be used as might an Ommaya reservoir to aspirate or release drugs into intraventricular cerebrospinal fluid, or the tip of the catheter, probe, cautery device, electrode, laser, fiber optic endoscopic viewer, or other miniature cabled device can be aimed at or inserted into a tumor such as an astrocytoma or glioblastoma multiforme. Automatic adaptive disorder response systems are addressed in sections XX. and XXI. below.

Use thus of a nonjacketing side-entry connector is described and illustrated in copending application Ser. No. 14/998,495, FIGS. 13A and 13B. As shown in FIGS. 14 thru 16 therein, any catheteric or styloid device can be motorized to gradually pass into or through the tumor. Bidirectional fluid lines for aspiration and drug delivery and electrical lines are led from a small drug entry port or, if no electrical lines are required, a conventional portacath or mediport implanted subdermally in the pectoral region to the connector beneath the dermis and scalp. When an electrical socket and one or more button cell batteries are needed, a port of the kind shown in copending application Ser. No. 14/121, 365, FIGS. 27 and 28 is used.

Whether adjunctive to primary external beamed radiation, to convey radioactive substances of small to moderate dose rates, the nonjacketing connector can be radiation shielded as shown in FIGS. 10A and 10B of the same application. The connector thus allows radiation as well as chemotherapy. For attachment to the cortex, the semicircular anchoring needles can be replaced with prongs to obtain positional stability with minimal penetration. As shown in copending application Ser. No. 14/121,365, FIGS. 9 and 11, the anchoring needles can be hollow to inject drugs into the substrate tissue and/or electrified to deliver electrostimulation. If not manual by injection into the subdermal port, the timing of drug delivery through the main catheter or stylus and/or the anchoring needles is governed by the prescription program executed by a microprocessor, which controls the tiny outlet pumps of the drug reservoirs to which the opening in the surface port are connected by catheters.

When the surface port is used only for injection, the openings are subdermal with tiny tattoos to indicate the injection points. A surface port to house a battery and/or serve for aspiration is mounted on the skin. The prescription program can coordinate the automatic treatment local to the brain with that systemic and/or involving other tissues or organs. This capability is beneficial when a brain tumor, for example, has metastasized from another part of the body, most often, a lung, which would similarly be treated locally, as well as with circulated chemotherapeutics and external beam therapy, and so on, to truncate further metastasis. Such an automatic disorder response system can administer drugs locally and systemically to treat comorbid conditions whether malignant or benign in a coordinated manner as to best maintain homeostasis. This capability expands upon conventional means for targeting nidi or lesions and functions independently of the ability of the patient to adhere to a treatment regimen, especially one complicated as comorbidity demands.

15. System Requirements

The essential system requirements are best set forth in terms of use in the vasculature as presenting that environment most demanding. Use in the respiratory, gastrointestinal, urinary, and genital tracts will encompass a subset of features, and use to introduce implants into tissue not lining a ductus will dispense with most of these requirements. In arteries, especially the coronaries and the internal carotids, the essential requirements for the apparatus and methods include minimizing the risk of a midprocedural crisis due to perforations, dissections, or ischemia due to obstruction of the lumen, whether the result of occlusion by the apparatus itself, an abrupt closure, thrombus, thromboembolism, gas embolism, swelling, and/or vasospasm whether the result of aeroballistic implantation. An angioplasty-capable barrel-assembly must be capable of performing an angioplasty by different means, to include cutting, shaving, abrasion by brushing or scraping (curettage, evidement), and those thermoplastic, radiofrequency and laser methods optional.

In veins, minimizing the potential for protracted obstruction, to include blockage by the apparatus, thrombus, embolism, and gas embolism is imperative. Embolism includes that intrinsic (thromboembolitic or coagulative), that due to a release of debris from a ruptured plaque, that due to intravasation or accidental entry of a miniball into the bloodstream, and the foregoing in any combination. Thrombogenicity is reduced by minimizing or eliminating metal surfaces in contact with the blood, avoiding thrombogenic operating temperatures, preventing blood from entering and clotting in the openings of the muzzle-head, and the use as necessary of adjuvant medication, such as a platelet blockade, nitrates, and/or an anticoagulant. To reduce the risk of perforations and dissections, the muzzle-head must be free of any protrusions, present a blunt-ended torpedo nose and rounded contour over the trailing shell. The muzzle-head must and slippery and not seize, pull, gouge, or cling to the endothelium.

Intravasated miniballs must be instantly arrested and recovered, and mispositioned or embolizing miniballs must be immediately recoverable. To allow precise aiming in the structurally differentiated tracheal lumen, an easily viewed singular exit-port at the distal end is essential. Such a simple pipe type muzzle-head is without the torpedo-shaped shell or envelope needed for transluminal movement within a smaller and structurally undifferentiated ductus such as a blood vessel or ureter. Except for use in the airway, the muzzle-head is contained within a torpedo shaped shell and can be made capable of delivering multiple implants per discharge. Pull-through denoting the gradual penetration and eventual perforation through the tunica adventitia or fibrosa of a miniball under the sustained magnetic traction needed to retract a stenosed lumen wall and/or to attract a magnetic drug-carrier from the passing contents of the lumen (usually blood), the forces involved in airgun discharge and magnetic traction must be minimized to prevent perforations during and pull-through following discharge.

To this end, the system must be capable of placing miniballs ductus-intramurally at close and uniformly spaced intervals as will evenly distribute rather than concentrate the tractive force on any one or a few. Such precise placement cannot be achieved under manual control, much less at a rate to minimize procedural time. To overcome this limitation necessitates the application of a positional control system. The apparatus must make possible the use of tissue bonding agents to overcome delamination in the form of inter- or intratunical separation and pull-through, both of which would result in stent failure. An ablation-capable barrel-assembly must be capable of ablating hyperplastic or neoplastic tissue and accreted matter obstructive of the lumen by those means stated for an angioplasty-capable barrel-assembly. The barrel-assembly must be sufficiently flexible to track and steer without winding or twisting when torqued.

To optimize the reach of a muzzle-head of given size down a narrowing ductus, the miniball discharge exit-port or ports (exit-holes) must be placed as far distad (forward) as the incorporation of recovery electromagnets will allow. Almost all muzzle-heads will also incorporate a front end heat-window, and many, a fiberoptic endoscope, angioscope, laser photoablater, and/or an embolic filter stowed in the part of the muzzle-head forward of the exit-port or ports, or the nose. Extraluminal stents must comply with angiotensive adjustments in caliber of the encircled vessel and with expansion and contraction in the encircled ductus, whether peristaltic, tonic, or pulsatile. Intrinsically magnetized stent-jackets must exert sufficient tractive force on the miniball or stay implants to maintain luminal patency while remaining thin enough to comply with expansion and contraction in the substrate ductus.

Polymeric stent-jacket base-tubes must resist chemical breakdown and not lose pliancy in the internal environment as to necessitate revision (replacement) at intervals of less than several years. A moisture barrier-coated viscoelastic polyurethane foam lining is essential to provide the encircled ductus with clearance for the passage of small nerves and vessels into and out of the adventitia. The stent-jacket lining must impose no more than negligible and adaptable pressure against this perivascular microvasculature, or vasa vasora, and nervelets, or nervi vasora. An expansion insert is necessary to allow adjustment to a reduction in swelling over time. All of the materials used must be bioinert, sterilizable, or disposable, and capable of remaining implanted over a period of years. The essential design of a type barrel-assembly should be capable of enlargement or miniaturization without significant degradation in performance.

Means must be provided for testing the penetration and puncture resistance of the actual tissue to be implanted with miniballs. This information will assist to determine whether miniballs can be used, and if so, the setting for the airgun exit velocity. Stays are essential for tissue that is too malacotic to retain miniballs. Testing must be provided to gauge the resistance to delamination and pull-through of the actual tissue to be implanted with stays. This will determine whether stays can be used, if so, how wide the stays should be, and whether coating the stays with a tissue bonding agent is necessary to prevent tunical delamination. Mispositioned stays must be instantly recoverable. The stay insertion tool must minimally interfere with the use of imaging equipment to confirm the substantial concentricity of ductus-intramural insertion. Interventional airguns must be capable of quickly repeating discharge (or 'firing' rate) without deviation in exit velocity. Except where the type of miniballs used is to be changed, the need for reloading should be minimized.

16. System Features

The capabilities imparted by the system apparatus and methods exceed these requirements. For use in a structured lumen or to target an organ, the barrel-assembly has the form of a pipe which is usually curved toward the distal end. The pipe is in effect a singular barrel-tube, the portion of the pipe distal to the curve representing the muzzle-head and its open distal tip the exit-port. For use in a generally small-diameter undifferentiated lumen wherein one or more miniballs can be released with each discharge, the barrel-tube or tubes are enclosed within a protective shell having a rounded torpedo contour that serves to reduce the risk of perforations or incisions. Gas is prevented from entering the bloodstream during discharge by equalizing differences in internal pressure, which is maintained to prevent the inflow of blood into the exit-ports (exit-holes) and airgun gas pressure relief channels where it would coagulate to form clots and affect performance.

The use of a muzzle-head inmate turret-motor allows rotation without torquing, hence, sufficient flexibility for tracking and steering. The barrel-assembly can be used to target lesions for the delivery of miniballs containing any medication and/or numerous other therapeutic substances which may or may not relate to stenting, thus eliminating the dilution and risk of side-effects of a larger and more costly dose injected or infused into the circulation rather than targeted. Ablation or angioplasty-capable barrel-assemblies can function independently to perform an ablation or an angioplasty, and then be inserted into an airgun to deliver miniballs without the need to withdraw and reenter. This factor not only reduces procedural time but minimizes entry wound irritation and the risk of hematoma and infection. Medication miniballs are implanted into or adjacent to circumscribed lesions, tissue strength pretesting used to determine the exit velocity needed for placement at the desired depth.

Miniballs can be radioactive seeds, magnetized, and/or release any therapeutic substance to include a magnetic drug carrier-binding particles in a ferrofluid to be drawn into tissue between the releasing and a magnetized stay or stays, miniball, patch-magnet, of any combination of these. The ferrofluid can also be administered by infusion, injection, or orally to treat one or more circumscribed sites, which the implants can also be used to warm. Stenting miniballs are placed subadventitially or perimedially in ductus and subfibrosally in organs. When not precluded by the structured anatomy of the lumen, procedural duration is also reduced by discharging multiple miniballs simultaneously. Mounting the airgun on a linear positioning stage moved by a positional control system not only speeds up implantation but makes possible a degree of transluminal precision that is essential but unattainable with manual control, the successive discharges implantable uniformly at millimetric intervals.

An ablation or ablation and angioplasty-capable barrel-assembly can be made as two complementary components, each usable independently of one another or an airgun. Such a duplex composite or bipartite barrel-assembly consists of a radial discharge barrel-assembly and a size-matched combination-form radial projection catheter with a central channel used to ensheath the barrel-assembly. To change the tool-inserts midprocedurally with relatively little irritation to the entry wound, the outer sheath or radial projection catheter is withdrawn and reintroduced using the stationary barrel-assembly as a guide. A slidable ablation or ablation and angioplasty-capable barrel-assembly power and control housing allows the quick addition to or removal from the barrel-assembly of a combination-form radial projection catheter and the ability to grasp the barrel-assembly at a consistent distance from the introducer sheath while eliminating joints in the barrel-tube or tubes. Providing each apparatus with its own control panel significantly reduces the chances for human error.

By omitting miniballs, an extraluminal stent can omit weaker portions of the lumen wall from patenting traction. Attachments and ostia can be accommodated. Radial projection units can accept tool-inserts that eject any therapeutic substance into the lumen, or inject any therapeutic substance into, heat, chill, ablate, or abrade the lumen wall. Spring-released or electrical/fluid system-neutral syringe radial projection unit tool-inserts allow fluid medication or other therapeutic substances to be delivered through electrically operated radial projection units whether the radial projection units are in the barrel-assembly muzzle-head, in an ensheathing combination-form radial projection catheter, or in a separate radial projection catheter. The incorporation of direction of flow-driven fluid resistors allows the same fluid-operated tool-inserts to irrigate with water or a therapeutic fluid, deliver a therapeutic fluid, or irrigate or aspirate intermittently or continuously as necessary. Incorporating two or more fluid radial projection circuits allows concurrent irrigation and aspiration.

A fluid-operated tool-insert can be preloaded to deliver an initial dose of medication and thereafter be used to irrigate with water or a therapeutic fluid or deliver a therapeutic fluid, irrigate or aspirate intermittently or continuously as necessary. The muzzle-head can be furnished with spring-released or electrical/fluid system-neutral syringe radial projection unit tool-inserts which can be used to coat the lumen wall with a lubricant. A lubricant can also be spread onto the lumen wall by means of a piston plunger or elongated injection syringe type service catheter having a membrane slit at its distal end. The service catheter is inserted (run, snaked) through an unused barrel-tube. Turret-motor functionality is optimized by using its windings as heating elements and to oscillate the muzzle-head. The lubricant can be used with the oscillatory modes of the turret-motor to expedite passage through tortuous stretches. The recovery electromagnet windings are also used as heating elements.

The heating elements have multiple uses, to include accelerating the setting of cements, the rate of drug uptake, and thermoplasty (thermal angioplasty). The barrel-assembly itself and/or the lumen into which it is inserted can also be heated or chilled by attaching a nitrous oxide or carbon dioxide cartridge or a vortex tube 'cold' air gun connected to a tank of compressed air to a socket on the side or proximal end of barrel-assembly. In any ductus, heat can be used for thermoablation and cold for cryoablation. An ablation or angioplasty-capable barrel-assembly can thus remove diseased tissue from the lumen by mechanical or temperature means. The motion and temperature functions have separate clearly marked controls, so that sending current to the windings of the electromechanical actuators within the muzzle-head, which are also used for positional control and implant recovery respectively, does not promote operator errors. With identical radial projection unit lifting mechanisms in a given electrical or fluid circuit, variable lifting or projection force is relegated to the radial projection unit tool-inserts.

Electrically operated ejection and injection tool-inserts can warm their contents. Electrical tool-inserts can be hot plates, and fluid operated tool-inserts can be hot or cold plates. Using a turret-motor to rotate the muzzle-head allows the barrel-assembly the flexibility needed for tracking and steering. The ability to achieve oscillatory action is prompted by the fact that whereas slower machine speeds tend to promote snagging with stretching and incisions, high speeds and sharp cutting, shaving, or abrading tool edges reduce the risk of trauma. An elastomeric flexible joint in the muzzle-head enhances trackability and supports turret-motor induced muzzle-head oscillation as programmed or through intentional derivative gain overdrive through damping and compliance. Rotation its only degree of freedom, oscillation of the turret-motor supports radial projection tool-inserts having circumferentially but not longitudinally oriented cutting edges or working faces.

Unless driven by a linear motor eliminating the need to convert to linear motion, the limitation to rotation also applies to the linear stage motor, of which the rotation is fixedly (structurally, kinematically) converted to longitudinal with high stiffness, or little if any play. Transluminal or reciprocating oscillation of tool-insert working faces or cutting edges is therefore obtained by intentionally overdriving the linear positioning stage motor regardless as to type as direct current closed loop (nonstepping), stepper, or linear. When the motor and stage are capable of achieving oscillatory frequencies in response to control instructions, transluminal or reciprocating motion to support transluminally oriented cutting or abrasive action can be obtained by incorporation into the instruction set or programming To avert injury to the vasa and nervi vasora of arteries and the equivalent fine structures about the outer tunic of other kinds of ductus treated, the extraluminal component of the magnetic stent, or stent-jacket, is lined with polyurethane moisture barrier-coated viscoelastic polyurethane foam.

So that the caliber of the stent-jacket will change in pace with the substrate ductus, stent-jackets can be provided with expansion inserts that are absorbed or crushed on demand as swelling or inflammation of the ductus subsides. The system provides multiple implant recovery and 'bailout' strategies, to include recovery electromagnets in muzzle-heads and stay insertion tools, impasse-jackets, and adaptation of an external electromagnet. A combination-form barrel-assembly has a central bore or channel for incorporating a cabled device such as a rotational or directional atherectomy or a thrombectomy cutter or an excimer laser. Such devices can be exchanged midprocedurally without withdrawal or any one such device can be installed permanently.

A radial discharge barrel-assembly with a built in angioscope or fiberoptic endoscope or laser, for example, is technically a combination-form, although the term pertains more to use of the central channel interchangeably and mostly to incorporate rotational tools such as atherectomizers and thrombectomizers. Whether a given cabled device is installed permanently or interchangeably with others depends upon the number of its applications where switching to another cabled device midprocedure is unnecessary. When the cabled devices are permanently installed, one barrel-assembly must be withdrawn and another inserted, which is not preferred. Cabled devices that can be built into or interchanged in barrel-assemblies for thermoangioplasty include those using radiofrequency, laser, and ultrasound. Those using fulgurating (electrofulgurating, electrodessicating) electrode based thermoablation are suitable for use in nonvascular ductus such as to perform a bronchial thermoplasty.

A radiofrequency thermoplasty probe can serve not only to eliminate vulnerable plaque, but to reduce the degree of restenosis, yield a larger lumen, and fuse ductus-intramural delaminations and dissections, to include flaps that induce abrupt closures. Microwave balloon angioplasty is likewise claimed to seal arterial dissections (Landau, C., Currier, J. W., Haudenschild, C. C., Minihan, A. C., Heymann, D., and Faxon, D. P. 1994. "Microwave Balloon Angioplasty Effectively Seals Arterial Dissections in an Atherosclerotic Rabbit Model," *Journal of the American College of Cardiology* 23(7):1700-1707) and yield increased luminal diameter (Nardone, D. T., Smith, D. L., Martinez-Hernandez, A., Consigny, P. M., Kosman, Z., Rosen, A., and Walinsky, P. 1994. "Microwave Thermal Balloon Angioplasty in the Atherosclerotic Rabbit," *American Heart Journal* 127(1): 198-203).

More specifically, with the lumen wall under low compression (see, for example, Fram, D. B., Gillam, L. D., Aretz, T. A., Tangco, R. V., Mitchel, J. F., and 5 others named, et al. 1993. "Low Pressure Radiofrequency Balloon Angioplasty: Evaluation in Porcine Peripheral Arteries," *Journal of the American College of Cardiology* 21(6):1512-1521) achieved through the use of an oversized muzzle-head and preplaced stent-jacket, radiofrequency thermoplasty fuses or welds tunics (see, for example, Kaplan, J., Barry, K. J., Connolly, R. J., Nardella, P. C., Hayes, L. L., Lee, B. I., Waller, B. F., Becker, G. J., and Callow, A. D. 1993. "Healing after Arterial Dilatation with Radiofrequency Thermal and Nonthermal Balloon Angioplasty Systems," *Journal of Investigative Surgery* 6(1):33-52; Becker, G. J., Lee, B. I., Waller, B. F., Barry, K. J., Kaplan, J., Connolly, R., Dreesen, R. G., and Nardella, P. 1990. "Potential of Radio-frequency Balloon Angioplasty: Weld Strengths, Dose-response Relationship, and Correlative Histology," *Radiology* 174(3 Part 2):1003-1008; Lee, B. I., Becker, G. J., Waller, B. F., Barry, K. J., Connolly, R. J., Kaplan, J., Shapiro, A. R., and Nardella, P. C. 1989. "Thermal Compression and Molding of Atherosclerotic Vascular Tissue with Use of Radiofrequency Energy: Implications for Radiofrequency Balloon Angioplasty," *Journal of the American College of Cardiology* 13(5):1167-1175; Barry, K. J., Kaplan, J., Connolly, R. J., Nardella, P., Lee, B. I., Becker, G. J., Waller, B. F., and Callow, A. D. 1989. "The Effect of Radiofrequency-generated Thermal Energy on the Mechanical and Histologic Characteristics of the Arterial Wall in Vivo: Implications for Radiofrequency Angioplasty," *American Heart Journal* 117(2):332-341) confirmed by imaging to have delaminated, which condition left untreated precludes magnetic extraluminal stenting.

Laser thermoplasty has been credited with these benefits as well (see, for example, Cheong, W. F., Spears, J. R., and Welch, A. J. 1991. "Laser Balloon Angioplasty," *Critical Reviews in Biomedical Engineering* 19(2-3):113-146; Geschwind H. 1989. "Laser Angioplasty," in French with English abstract at Pubmed, *Annales de cardiologie et d'angéiologie*. (Paris, France) 38(8):445-448) as has thermoplasty with the aid of an ultrasound probe (Rosenschein, U. und Budde-Schwartzman, B. 1997. "Koronare Ultraschallangioplastie: Standpunkt und neue klinische Aspekte," ("Ultrasound Coronary Angioplasty: State of the Art and New Clinical Aspects"), in German with English abstract at Pubmed, *Herz* (Heart) 22(6):308-317).

OBJECTS OF THE INVENTION

1. A central object of the invention is to make possible the targeting of medication, another therapeutic substance, and/or a radioactive seed into any tissue, but especially into, adjacent to, or past a lesion in the wall surrounding a lumen, thus avoiding systemic dispersal with the indiscriminate exposure of other tissue and the risk of side effects.

2. Another object of the invention is to provide for magnetic extraluminal stenting that eliminates the need to place a foreign object within a diseased lumen, thus avoiding a chronic irritant and scaffold for accumulating occlusive matter.

3. Yet another object of the invention is to reduce the need for a percutaneous transluminal reintervention or surgical revascularization made necessary by the intimal hyperplasia that follows luminal stretching by a balloon through the use of alternative means for performing an angioplasty, which uninflated, are less likely to cause incisions that result in an abrupt closure.

4. Another object of the invention is to provide extraluminal stents and ductus-intramural implants that also allow magnetic drug-targeting by exerting magnetic force to extract a ferrofluid-bound drug from the passing blood, thus concentrating the drug in the lesion encircled by the stent.

5. Another object of the invention is to augment the treatment options for the many conditions that stenose, weaken, or collapse the different types of tubular anatomical structures.

6. A further object of the invention is to provide a long term if not permanent stent, which vasomotility compliant, can be used preventively by extension to portions of the ductus expected to necessitate treatment in the future.

7. Yet another object of the invention is to provide a stent that can adapt to changes in caliber of the treated ductus.

Further objects of the invention include the provision of:

8. Implantation by means of a special airgun of spherules, or miniature balls, containing therapeutic ingredients whereby penetration is so sudden that tissue trauma and implant mispositioning are minimized, the entry punctures, no wider than the implants, immediately sealing and quickly healing.

9. Peradventitial rather than ballistic infixion of ductus-intramural implants containing ferrous matter and optionally, therapeutic substances, for release into the surrounding tissue in the form of stays, which can be circumfugally attracted to stent, and additionally used to attract ferrofluid-bound drug carrier particles from the passing blood while avoiding the lumen entirely.

10. Implantation with repeatable control over the force of impact, so that allowing for the variability in mechanical properties of diseased tissue, a consistency in depth of penetration can be achieved that to attempt to duplicate with a hand tool would pose difficulty and prompt hesitancy likely to result in increased injury.

11. Simple in situ tissue testing and procedural means that intuitive and empirical, eliminate complications such as the need for computation, and are quickly accomplished pre- or midprocedurally, thus minimizing the chances for human error.

12. Apparatus that is intuitive and simple to use thereby minimizing the chances for human error.

13. Angioplasty catheters that do not use a balloon and can be inserted into an airgun to initiate the discharge of miniballs to implant and/or to draw and concentrate medication and/or to serve as the ductus-intramural component of an extraluminal magnetic stent immediately, without the need to withdraw and introduce a second stent delivering balloon catheter, thus averting luminal stretching as well as repeated passage through and irritation to the entry wound.

14. Angioplasty catheters which incorporate components that allow atheroablation and can additionally incorporate a prior art cabled device, such as a laser or rotational burr for removing calcified plaque, rather than crushing plaque up against the lumen wall, thus yielding an overall result more durable than that obtained through prior art angioplasty and atherectomy.

15. Systems and methods that adapt the stenting means described herein for alleviating tracheal collapse in small dogs, for example, thus averting the need for an open surgical procedure that demands extensive dissection and poses jeopardy to the tracheal vasculature and neurology at a time when the operative risk is greatest and the trauma least tolerable.

16. Further to alleviate collapsed trachea without the need for a thoracotomy, a new form of stent that is placed through a small incision to encircle the trachea, and thus not susceptible to the accumulation of mucus that necessitates frequent reinspection, withdrawal, and revision (replacement).

17. Systems and methods that reduce or eliminate the sequelae associated with endoluminal stenting, to include restenosis in vessels and reocclusion in other tubular anatomical structures to which the stent is itself a contributing factor if not the triggering or sole cause, fracture, fragmentation, migration as intact or following breakage, clogging, and erosive irritation to the portions of the lumen in contact with the stent, thereby achieving stenting action that remains trouble-free even to the end of life.

18. Interventional procedures that compared to ablation or angioplasty and stenting by conventional means, yield a relatively low incidence of adverse sequelae, and compared to open surgery, are significantly less traumatizing, making these procedures applicable to a larger patient population.

19. Limited purpose interventional airguns at relatively low cost through modification of off the shelf airguns.

20. Special interventional airguns that provide finer control through multiple control points that reduce the dependency of adjustment on any single control point and make possible the quick and precise adjustment of the exit velocity and force of penetration.

21. Interventional apparatus and procedures that allow angioplasty, atherectomy, and stenting with single endoluminal entry, minimizing intracorporeal time and entry wound trauma and complications.

22. Apparatus for use in the vascular tree that affords operative speed with minimal ischemia and without a thrombogenic metal in the lumen.

23. Extraluminal stenting that complies with the intrinsic motility in the ductus wall, leaves the lumen clear of any foreign object in the form of an artificial lining, or stent, that can clog, fracture, migrate, migrate and induce an abrupt closure that could result in an infarction and death, is a source of chronic irritation, interferes with normal function, and perpetuate the need for adjunctive medication such as antithrombogenic, anticoagulative, or thrombolytic posing a bleeding threat that would complicate any surgical procedure to follow.

24. Targeted implantation in the walls of ductus of radioactive seeds, which low dose-rate, can be left in place or high dose-rate, can be recovered at will, using the same apparatus that was used to implant the seeds.

25. A periductal or circumductal prosthesis that expands and contracts with the arterial wall so as to cause the least low oscillating shear stress and turbulence in the flow of blood and does not compress the vasa vasora to induce atheromatous lesioning (as seen in Silastic® collar experiments), and which when applied to other type ductus, complies with peristalsis, and remains chemically isolated from the surrounding environment.

26. Prepositioned means for preventing embolization or the spread to nontargeted tissue of radiation or medication by any miniballs that should enter the lumen.

27. Apparatus for use in the vascular system that allows lower doses and periprocedural limiting of anticlotting drugs, hence, shorter infusion of abciximab and oral administration of clopidogrel times of platelet inhibitor-type anti-thrombogenics, or aggregation counteractants and anti-inflammatory corticosteroids, for example.

28. The foregoing where the use of conventional stenting poses the risks of bleeding or stent thrombosis for surgery following stent placement.

29. Methods and apparatus that afford fine discretionary control over the location and intensity of treatment, thereby minimizing iatrogenic interference with the intrinsic potential of the vessel or organ to heal and recover normal function.

30. Lay the groundwork for the direct piping to the treatment site through stent-jackets as described herein as modified in copending application Ser. No. 14/121,365 to receive drug and other agent feedlines from a small port a the body surface, for example, as well as through tissue surface connectors as described in copending application Ser. No. 14/998,495.

31. Lay the groundwork for the application of adaptive hierarchical control to the automatic treatment of morbidity and coordinated treatment of comorbidities.

32. Set forth the concept of adaptive hierarchical control systems for the automatic treatment of a morbid disorder and coordinated treatment of comorbidities which fully implanted or nearly so, are ambulatory, with implanted sensors able to detect the earliest indications of deviations from the normal range in therapeutically relevant physiological functions and initiate the directly targeted delivery of drugs to reverse these, often before symptoms appear to consciousness, in accordance with the prescription program executed by the implanted microprocessor.

These and other objects and advantages of the invention will become apparent from the following specification and accompanying drawings. Further scope in the applicability of the invention will become apparent from the detailed descriptions of the preferred combinations of components, assemblies, and methods, or the embodiments to be described herein. Since various modifications in keeping with the concept and scope of the invention will be evident, the detailed specification is given only by way of illustration. The invention accordingly comprises the features of construction, combination of elements, and arrangement of parts exemplified in the constructions hereinafter set forth, and the scope of the invention will be indicated in the claims.

All drugs which can be put in biocompatible solution can be pipe-targeted, to include glycoprotein IIb/IIIa receptor blockade or antagonist (abciximab), and lower doses of thrombolytic drugs, thus reducing the risk of bleeding complications (see also, for example, Lebozec, K., Jandrot-Perrus, M., Avenard, G., Favre-Bulle, O., and Billiald, P. 2017. "Design, Development and Characterization of ACT017, a Humanized Fab that Blocks Platelet's Glycoprotein VI Function Without Causing Bleeding Risks," *Monoclonal Antibodies* 9(6):945-958; Bosch, X., Marrugat, J., and Sanchis, J. 2013. "Platelet Glycoprotein IIb/IIIa Blockers During Percutaneous Coronary Intervention and as the Initial Medical Treatment of Non-ST Segment Elevation Scute Coronary Syndromes," *Cochrane Database of Systematic Reviews* (11):CD002130; Lenderink, T., Boersma, E., Ruzyllo, W., Widimsky, P., Ohman, E. M., Armstrong, P. W., Wallentin, L., Simoons, M. L. 2004. "Bleeding Events with Abciximab in Acute Coronary Syndromes Without Early Revascularization: An Analysis of GUSTO IV-ACS [Global Utilization of Strategies To open Occluded arteries-Intravasular-Acute Coronary Syndrome-intravascular-acute coronary syndrome]," *American Heart Journal* 147(5):865-873; Cote, A. V, Berger, P. B., Holmes, D. R., Scott, C. G., and Bell, M. R. 2001. "Hemorrhagic and Vascular Complications after Percutaneous Coronary Intervention with Adjunctive Abciximab," *Mayo Clinic Proceedings* 76(9): 890-896; Jong, P., Cohen, E. A., Batchelor, W., Lazzam, C., Kreatsoulas, C., Natarajan, M. K., and Strauss, B. H. 2001. "Bleeding Risks with Abciximab After Full-dose Thrombolysis in Rescue or Urgent Angioplasty for Acute Myocardial Infarction," *American Heart Journal* 141(2):218-225). In lower doses, these drugs are of critical value perioperatively (see, for example, Tcheng, J. E., Kandzari, D. E., Grines, C. L., and 11 other authors 2003. "Benefits and Risks of Abciximab Use in Primary Angioplasty for Acute Myocardial Infarction: The Controlled Abciximab and Device Investigation to Lower Late Angioplasty Complications (CADILLAC) Trial," *Circulation* 108(11):1316-1323).

SUMMARY OF THE INVENTION

The foregoing objects as pertain to stenting are accomplished in accordance with the invention by means of miniature balls called miniballs or arcuate bands called stays. These include ferrous matter and are implanted just beneath the outer tunic of a ductus or organ. This position is outside the physiologically more active inner layers, and inside the more fibrous outer layers that serve to retain the miniballs or stays. Miniballs and stays can consist primarily of a therapeutic substance, time-released drug or drugs, or a radionuclide in any combination, the ferrous content allowing the quick recovery of any miniballs or stays that are dropped or mispositioned. The apparatus for infixing each type implant is described. Implanting stays avoids the lumen entirely. The apparatus for implanting miniballs incorporates non-balloon means for performing an ablation or an angioplasty, allowing the lumen to be prepared and implanted with single entry and withdrawal.

Provided with a short side connector or connectors, stent and impasse-jackets as described herein, as well as those described in copending application Ser. No. 14/121,365 and Ser. No. 14/998,495, can be connected by catheter or catheters to a small port at the body surface with protected openings to allow the directly targeted infusion of different drugs, for example, in isolation from one another, the bloodstream, and tissue along the route to different jackets and connectors. Delivery thus can be placed under the control of an automatic drug delivery response system wherein an implanted microprocessor taking inputs from sensor implants directs the dispensing of drugs according to the prescription program it executes, monitors the results, and registers this data, thus implementing an adaptive hierarchical control system. In this way, drug delivery is coordinated to approximate normal homeostasis as can best be accomplished given the overall condition of the patient. By connection to the blood supply and/or the organ or tissue itself, these jackets and connectors allow the direct delivery of drugs to any organ or tissue.

(Balance of abstract) System components make possible drug targeting by implantation within the walls surrounding lumina, a segment of a ductus, an entire organ, or a portion thereof. Implants that include ferromagnetic material can be recovered or used for extraluminal stenting. A magnetic extraluminal stent consists of an intravascular component in the form of perimedially or medially implanted miniballs or stays and an extravascular magnetized collar or mantle that is pliant, protectively lined, and slit along one side. The use of more distant magnet implants likewise leaves the lumen free of any foreign object. The unrestraining and vasomotion-compliant stent can remain in place indefinitely and be applied, for example, to as yet unaffected segments of an artery to prevent a need for revascularization; however, should another transluminal procedure be needed, the lumen will be clear. Extraluminal stents can be used to attract magnetic drug or radioisotope carrier particles, adapted to allow for changes in caliber, and linked to negotiate bends or accommodate flexion.

Delivery targeted, the dose is optimal with dispersion to nontargeted tissue and side effects minimized. When magnetized, these and the other type implants described can be used to attract drug carrier particles passing through the lumen. When drawn radially outward toward a compliant mantle that is itself magnetized or has magnets mounted about its outer surface, the implants are drawn to the mantle and therefore draw the wall of a stenosed or collapsed ductus outward with a force just sufficient to maintain the lumen patent. The ductus-intramural implants then act as the intravascular and the mantle as the extravascular components of an extraluminal stent that leaves the lumen free of any foreign object. Multiple means for preventing a miniball loose in the circulation from embolizing are provided.

BRIEF DESCRIPTION OF THE DRAWINGS

A more complete understanding of the invention can be obtained by reference to the accompanying drawings of which:

FIG. 2 is a diagrammatic longitudinal section view of a vas or ductus such as the trachea with ferromagnetic spherules implanted just within the tunica adventitia or tunica fibrosa which are drawn outward toward a circumvascular jacket of the extrinsic spaced apart magnet type with tiny magnets mounted about its outer surface. For simplicity and generalization to allow applicability to different type ductus, histological detail has been omitted.

FIG. 3 is a diagrammatic longitudinal section view of a vessel, such as an artery or ureter, mantled about by a side-slit or side-slotted circumvascular stent-jacket of the extrinsic spaced apart magnet type, the increased density and uniform distribution of ferromagnetic miniball implants accomplished with the aid of a positional control system serving to reduce the risk of pull-through. For simplicity and generalization to allow applicability to different type ductus, histological detail has been omitted.

FIG. 4 is a diagrammatic cross sectional view of the lumen taken along line A-A' in FIGS. 2 and 3 with ferromagnetic spherules or miniballs implanted just inside the fibrous outermost layer, or tunica adventitia, which is mantled about by a stent-jacket of the extrinsic spaced apart magnet type as shown in FIGS. 2 and 3.

FIG. 5 is an angular perspective show-through or ghost view of the full-round extraductal stent-jacket component of an extraluminal stent for a vessel or duct that can be fully encircled as shown in FIGS. 2 and 3 showing the apposed or facing relation between the subadventitial implants and the magnets surrounding the base-tube in the extrinsic spaced apart magnet type stent-jacket with gas exchange apertures or perforations as shown in FIG. 6 omitted for clarity.

FIG. 6 is an angular perspective view of a stent-jacket for a vessel or ductus which cannot be fully encircled without a widened side-slit, or side-slot, for clearing a connective tissue attachment wished preserved or a branch or branches, for example, of the treated ductus. The gas-exchange or 'breathing' perforations shown can be of any shape or number and incorporated into any stent-jacket.

FIG. 7 is an angular perspective view of a stent-jacket with a nonlayered expansion insert in its side-slit or side-slot to allow approximation of the side-slit or side-slot apposing edges once swelling of the ductus subsides. Magnets as shown in FIGS. 2 thru 6, 'breathing' holes as shown in FIG. 6, and optional side-straps shown as in FIGS. 13 thru 15 have been omitted.

FIG. 8 is a cross-sectional detail view taken along line B-B' in FIG. 7 of a bilaterally symmetrical multilayered stent-jacket expansion insert for insertion in the side-slit or side-slot of a stent-jacket that opens at the center to accommodate expansion of the substrate ductus, wherein the more medial layers are absorbed at progressively slower rates and the more lateral layers are lithotriptor-destructible on demand.

FIG. 9 is a cross sectional view taken along line B-B' in FIG. 7 of an extended stent-jacket expansion insert wherein the medial layers are absorbable and the lateral layers lithotriptor-destructible on demand. The quasi-intrinsically magnetized stent-jacket incorporates encapsulated neodymium iron boron granules (not depicted).

FIG. 17 is a side view of a long-handle tweezers- or tongs-configured (thumb forceps) stent-jacket applicator, or base-tube slit-expansion and mantling hand tool for use with deep lying ductus, in which the restorative or spring force intrinsic in the junction joining the arms forces open the stent-jacket for placement about the ductus when compression of the tool arms between the thumb and index finger is released.

FIG. 18 is a side view of a short-handle tweezers or tongs-type (thumb forceps) stent-jacket insertion tool, applicator, or base-tube slit-expansion and mantling hand tool for use with ductus that lie close to the surface of the body, in which the restorative or spring force intrinsic in the junction joining the arms forces open the stent-jacket for placement about the ductus when compression of the tool arms between the thumb and index finger is released.

FIG. 19 is a side view of a short forceps-type or scissors, crile, or needle holder-configured stent-jacket insertion tool, applicator, or base-tube slit-expansion tool, for use with ductus that lie near the body surface.

FIG. 20 is a side view of a long-handle forceps or scissors, crile, or needle holder-configured stent-jacket insertion tool, applicator, or base-tube slit-expansion and stent- or impasse-jacket mantling tool for use with deep lying ductus.

FIG. 21A is a full face-on view of an unwrapped, laid opened flat magnet-wrap.

FIG. 21B is a left edge-on longitudinal section view taken along line C-C' in FIG. 21A showing the plies separated and moisture barrier-coated viscoelastic adventitia or fibrosa-protective polyurethane foam lining to the right.

FIG. 22 is a full-face view of an open clasp-wrap.

FIG. 23 is a detailed overhead or plan view of a single clasp in the clasp-wrap shown in FIG. 22.

FIG. 24 is a detailed cross-sectional view along line D-D' of the individual clasp shown in FIG. 23 with moisture barrier-coated viscoelastic polyurethane foam lining.

FIG. 25 is a full face overhead or plan view of a patch- or clasp-magnet for attracting ferromagnetic ductus-intramural implants, drug-carrier nanoparticles, or a clasp-wrap by attachment suprapleurally or to epimycial or visceral fascia whether subcutaneous, for example.

FIG. 26 is cross sectional view taken along line E-E' in FIG. 25 of a patch-magnet shown without the moisture barrier-coated viscoelastic polyurethane foam lining, for attracting ferromagnetic ductus-intramural implants, drug-carrier nanoparticles, or a clasp-wrap by attachment suprapleurally or to epimycial or visceral fascia whether subcutaneous, for example.

FIG. 27 is a cross-sectional view through a miniball which contains magnetically susceptible ferrous matter and can include a radiation-emitting seed or a heat-radiating radiofrequency alternating magnetic field resonant circuit as or within its ferromagnetic core and concentric layers of medication.

FIG. 28 is a cross-sectional view through a miniball which can incorporate a radioactive seed or a heat-radiating radiofrequency alternating magnetic field resonant circuit in the core (not shown) such as that shown in FIG. 27, with additional sequentially released layers of medication, other therapeutic substances, and a solid protein solder outer envelope that flows when heated.

FIG. 29 is a full-face view of a 7-shot rotary magazine clip for use in a single barrel (single barrel-tube, monobarrel) radial discharge barrel-assembly.

FIG. 30 is a full-face view of a 10-multishot rotary magazine clip for use in a four barrel-tube or four-way radial discharge barrel-assembly.

FIG. 31 is a longitudinal section view of a simple pipe-type monobarrel barrel-assembly suitable for use in the tracheobronchial tree, wherein the anatomy is structurally differentiated or where each miniball implant should be precisely located in relation to the lesion, shown without side-clips for attaching a laser sight and fiberoptic bronchoscope or endoscope.

FIG. 32 is a longitudinal section view of a simple pipe-type barrel-assembly with a deflection- or bounce-plate attachment for reversing the direction of the trajectory of a miniball at an angle equal and opposite to that of the initial impact against the bounce-plate, shown without side-clips for attaching a laser sight and fiberoptic bronchoscope or endoscope.

FIG. 33 is a detailed view longitudinal section through the miniball recovery electromagnet enclosure and recovery electromagnet affixed within the concavity of the distal curve of a simple pipe type barrel-assembly such as those shown in FIGS. 31 and 32.

FIG. 34 is a perspective detail view, partly in section, of the muzzle-head of the simple pipe barrel-assembly with a slip-on type bounce-plate seen in the overall view of FIG. 32, showing the reversal of the miniball trajectory at an angle equal and opposite to that of the strike against the bounce-plate.

FIG. 35 shows a side view of a simple pipe barrel-assembly such as that shown in FIG. 31, equipped with an endoluminal bounce-plate deployment and retraction control mechanism of the kinds shown in greater detail in FIGS. 36 and 37.

FIG. 36 is a longitudinal section through a curved spring-steel, or spring-plate type bounce-plate mechanism for use in a simple pipe-type barrel-assembly, which can be deployed, rotated, and retracted, but not adjusted in deflection angle while the pipe is endoluminal or intracorporeal, the bounce-plate straightened when retracted or ensheathed.

FIG. 37 shows a longitudinal section through a simple pipe barrel-assembly bounce-plate mechanism that hinged, allows the bounce-plate not only to be deployed, rotated, and retracted but adjusted in deflection angle while endoluminal or intracorporeal.

FIG. 46 is a perspective view of an airgun valve-body that incorporates a sliding pressure-bleed valve.

FIG. 47 shows a detail view of the sliding pressure-bleed valve shown in FIG. 46.

FIG. 48 is a mid-longitudinal section through a 2- or 4-barrel-tube ablation or angioplasty-incapable center-discharge muzzle-head with recovery electromagnets oriented or chambered normal to the long axis of the barrel-assembly.

FIG. 49 is a mid-longitudinal section through a 2- or 4-barrel-tube ablation and angioplasty-capable center-discharge muzzle-head with radial projection units and recovery electromagnets oriented or chambered normal to the long axis of the barrel-assembly, and equipped with an embolic trap-filter which as shown in FIG. 50 is deployed or in this Fig. unstowed (retracted, stowed) by means of the plunger solenoid 172 at the bottom of the filter silo in the extended nose.

FIG. 50 is a diagrammatic detail view of the nose of a barrel-assembly muzzle-head showing the embolic trap-filter 173 and plunger solenoid 172 used to unstow or deploy and stow or retrieve the trap-filter shown in FIG. 49 with the trap-filter deployed.

FIG. 51A is an exploded or breakout schematized detail view of a radial projection unit, the hatch lines indicating its position in the ablation and angioplasty-capable center-discharge muzzle-head shown in FIG. 49, part number 174 designating a tool-insert raised into projected working position by coiled thermal expansion wire 177.

FIG. 51B is a diagrammatic view of the first of four differently configured projection bristles or aristae working tips of a curettage (evidement, scraper abrader-type) tool-insert shown, the action of which depends upon the motion imparted to it by the turret motor, such as rotational or oscillatory.

FIG. 51C is a diagrammatic view of the second of four differently configured projection bristles or aristae working tips of a curettage (evidement, scraper abrader-type) tool-insert shown, the action of which depends upon the motion imparted to it by the turret motor, such as rotational or oscillatory.

FIG. 51D is a diagrammatic view of the third of four differently configured projection bristles or aristae working tips of a curettage (evidement, scraper abrader-type) tool-insert shown, the action of which depends upon the motion imparted to it by the turret motor, such as rotational or oscillatory.

FIG. 51E is a diagrammatic view of the fourth of four differently configured projection bristles or aristae working tips of a curettage (evidement, scraper abrader-type) tool-insert shown, the action of which depends upon the motion imparted to it by the turret motor, such as rotational or oscillatory.

FIG. 53A shows an exploded perspective view of the expansion wire electrically operated radial projection unit shown in FIG. 52A with the lift-shaft 174 lumen-adaxial (at the bottom), the tool-insert holding and lift platform 176 radially outward thereto (above the lift-shaft, at the center), and evidement or scraper abrader-type ablation interchangeable tool-insert 184 lumen-abaxial thereto adintimal, adendothelial (at the top of the figure) inserted into lift-shaft 176 at the center of the figure.

FIG. 53B shows an alternatively insertable cutter-shaver type tool-insert 184 in lieu of that shown in FIG. 53A.

FIG. 53C shows a blank or push-arm type tool-insert used to push against the intima thereby to nudge the barrel-assembly muzzle-head (or radial projection catheter if so equipped) in the opposite direction.

FIG. 54 shows a thermal expansion wire electrically operated (tool-insert lifting and lowering) radial projection unit with a spring discharged electrical/fluid system-neutral injection syringe tool-insert engaged in the tool-insert holding and lift-platform. The tool-insert is not in use and retracted but positioned flush against the lumen wall, having been lifted by the thermal expansion wire at the bottom of the lift-shaft. The electrical socket in the lift-platform is provided for use with other interchangeable tool-inserts that require electrical power to operate internal functions.

FIG. 55 shows an electrically operated (tool-insert lifting and lowering) radial projection unit with a mechanical ejection syringe tool-insert inserted therein, so that lifting is by the coiled thermal expansion wire at the bottom, the electrical socket for use with other interchangeable tool-inserts and therefore not used.

FIG. 59 shows a fluidically operated radial projection unit with a spring discharged compound mechanical electrical/fluid system-neutral injection syringe inserted therein.

FIG. 60 shows a fluidically operated radial projection unit with an initial prefill-delivering and thereafter fluid line flow-through fed injection tool-insert inserted therein, the arrows designating the antegrade direction of flow, which would be reversed during retrograde flow.

FIG. 61 is a detail of a perforated passive fluid resistor roof-plate for the outlet chamber of a fluid radial projection unit lifting mechanism as incorporated into the fluidically operated radial projection units shown in FIGS. 59 and 60, which is hinged and has a wing or foil to pull the plate down and close it during injection (antegrade, forward) flow and partially push up to lift it up out of the fluid path during aspiration (retrograde, reverse) flow, thereby increasing the interval the resistor remains unclogged by a buildup of debris.

FIGS. 62 panel A and 62 panel B show a perforated damper-configured passive fluid resistor ejection-aspiration switching valve as incorporated into the fluid operated radial projection units shown in FIGS. 59, 60, and 63, hinged to cant adaxially or downward toward the fluid supply line during aspiration, as shown in FIG. 62 panel B, thus avoiding clogging by debris, but to swing upward until stopped during ejection when needed as a fluid resistor, as shown in FIG. 62 panel A.

FIG. 63 shows a fluidically operated radial projection unit with an initial prefill-delivering and thereafter fluid line flow-through fed delivering ejection-irrigation-aspiration tool-insert inserted therein, the arrows designating the antegrade direction of flow, which would be reversed during retrograde flow.

FIG. 64 is a full face external view of a center-discharge ablation and angioplasty-capable center-discharge muzzle-head body such as that shown in FIG. 49 to show slit (rather than all-around) type heat-windows overlying the turret-motor and forward recovery and filter deployment plunger solenoid electromagnets.

FIG. 65 is a mid-longitudinal or median section through the center-discharge muzzle-head of a 2- or 4-barrel-tube ablation and angioplasty-capable barrel-assembly equipped with radial projection units, recovery electromagnets oriented in parallel relation to the long axis of the barrel-assembly with miniball recovery magnet trap-chambers or antechambers oriented as shown in the cross-section of FIG. 67 (not shown as lying perpendicular to the plane of section), and a trap-filter as shown in FIGS. 49 and 50 that is unstowed or deployed from and retracted into or stowed in a silo within the nose of the muzzle-head by a plunger solenoid.

FIG. 66 is a mid-longitudinal or median section through the edge-discharge muzzle-head of a 2- or 4-barrel-tube combination-form ablation and angioplasty-capable edge-discharge barrel-assembly equipped with radial projection units, miniball recovery electromagnets and trap-chambers or antechambers oriented in parallel relation to the long axis of the barrel-assembly with recovery magnet trap antechambers oriented as shown in the cross-section of FIG. 67 (not shown as lying outside the plane of section), passed through the central channel FIG. 67 is a diagrammatic cross-section through the distal section of the muzzle-head in an ablation and angioplasty-capable combination-form (edge-discharge) barrel-assembly such as that shown in FIG. 66 along line J-J' showing the eccentric (off-axis, lateral) location of the trap-filter silo when the central channel is taken up by a fiberoptic endoscope, cabled ablation, or atherectomy device, whether the miniball recovery electromagnets are parallel or perpendicular to the longitudinal axis of the muzzle-head.

FIG. 68 is a mid-longitudinal or median section through a capped side-emitting type cooling catheter.

FIG. 69 is a cross-section along line I-I' through the cooling catheter of FIG. 68.

FIG. 70 is a diagrammatic mid-longitudinal or median section through a heat-window created by passing a 'cooling' (temperature-changing) catheter connected to a vortex tube 'cold' air gun down the central channel of an edge-discharge type muzzle-head such as shown in FIG. 66 to the nose.

FIG. 71A is a radial projection catheter with its own unitized power and control housing allowing its use separately from the barrel-assembly shown in FIG. 71B, but also combinable therewith to constitute the duplex, or bipartite, ablation and angioplasty-capable barrel-assembly shown in FIG. 71C.

FIG. 71B is a barrel-assembly with its own unitized power and control housing complementary or matched in size to the radial projection catheter shown in FIG. 71A so that when slid over and along the proximal end of barrel-catheter 44, the combination of the radial projection catheter shown in FIG. 71A and the barrel-assembly shown in FIG. 71B constitute the duplex, or bipartite, ablation and angioplasty-capable barrel-assembly shown in FIG. 71C.

FIG. 71C is a duplex or bipartite ablation and angioplasty-capable barrel-assembly comprised of the radial projection catheter shown in FIG. 71A and the barrel-assembly shown in FIG. 71B.

FIG. 78A shows the duplex or bipartite ablation and angioplasty-capable barrel-assembly comprised of the radial projection catheter shown in FIG. 71A and the barrel-assembly shown in FIG. 71B then shown combined in FIG. 71C before being further integrated into the forward drive, sag-leveling, and stabilizing linkage device shown in FIGS. 77B and 77C airgun barrel as shown in FIG. 78C for stabilized precise control to allow the laying down of a tight shot group pattern into the intima to avoid inequalities in spacing and tension that would facilitate incisions.

FIG. 78B is a side view of the forward drive, sag-leveling, and stabilizing linkage device shown in FIGS. 77B and 77C engaged in the linear stage extension and retraction driver before insertion of the barrel of the duplex, or bipartite, ablation and angioplasty-capable barrel-assembly shown in FIGS. 71C and 78A.

FIG. 78C is a side view of the duplex, or bipartite, ablation and angioplasty-capable barrel-assembly shown in FIGS. 71C and 78A and the forward drive, sag-leveling, and stabilizing linkage device engaged in the linear stage extension and retraction driver when fully assembled.

FIG. 96 shows a sectional side view of the cement-ahead/cement-after subminiature sprocket and up or down run of sprocket chain selection switching mechanism used to reverse the direction as up or down of the cement pressurization piston which is permanently fastened to one side of the chain when the thumb-ring, and thus the small catch arm on the plunger-rod (plunger-slide, slide, thumb rod, thumb shaft; thumb plunger; thumb plunger-rod; plunger shaft; thumb plunger shaft), is rotated from one side of the chain to the other.

FIG. 97 shows an overall side sectional view of the cement-ahead/cement-after selection switching mechanism shown in FIG. 96.

FIG. 98 shows an enlarged detailed sectional view at the sprocket level of the cement ahead/cement-after selection switching mechanism shown in FIGS. 96 and 97.

FIG. 99 is a cross-section through the upper portion of a control syringe-configured release to inject stay insertion tool along line L-L' in FIG. 87.

FIG. 100 shows a cross-section of the cement ahead/cement-after switching mechanism along line M-M' in FIGS. 97 and 98.

FIG. 101A is a full-face frontal longitudinal section view through a stay insertion tool auxiliary syringe holder mounting frame and motor for attaching a commercial tissue sealant or medication syringe which provides latitude in the number of syringes or syringe chambers.

FIG. 101B is a face-on view of the right side of the stay insertion tool auxiliary syringe holder mounting frame and motor shown in FIG. 101A for attaching a commercial tissue sealant or medication syringe which provides latitude in the number of syringes or syringe chambers.

FIG. 102 shows a side view, as in FIG. 87, showing the attachment to a stay insertion tool of an auxiliary syringe holding frame and motor such as that shown in FIG. 101 by means of a mounting cable-delivery extension line such as that shown in FIGS. 104 and 105, with the connection socket at the rear shown in FIG. 106.

FIG. 103 shows a left side sectional view of a stay insertion tool auxiliary syringe holding frame and motor such as shown in FIG. 102, showing at the bottom of the drawing, the attachment of the frame and motor to the mounting cable-delivery extension line.

FIG. 104 shows a detailed longitudinal sectional view of a stay insertion tool auxiliary syringe mounting cable-delivery extension line such as shown in FIGS. 102 and 103.

FIG. 105 shows a cross-section through the stay insertion tool auxiliary syringe holding frame supporting arm and connecting cable shown in FIGS. 102, 103, and 104.

FIG. 106 shows a detailed view of the right side and full face rear views of the socket used to connect the auxiliary syringe shown in FIGS. 101 thru 103 to a stay insertion tool showing the break-contact terminals used to initiate the timing of tissue sealant and/or medication delivery by controlling the electrical current to the dual interval delay/on-timing module in slave mode.

Figure 107:
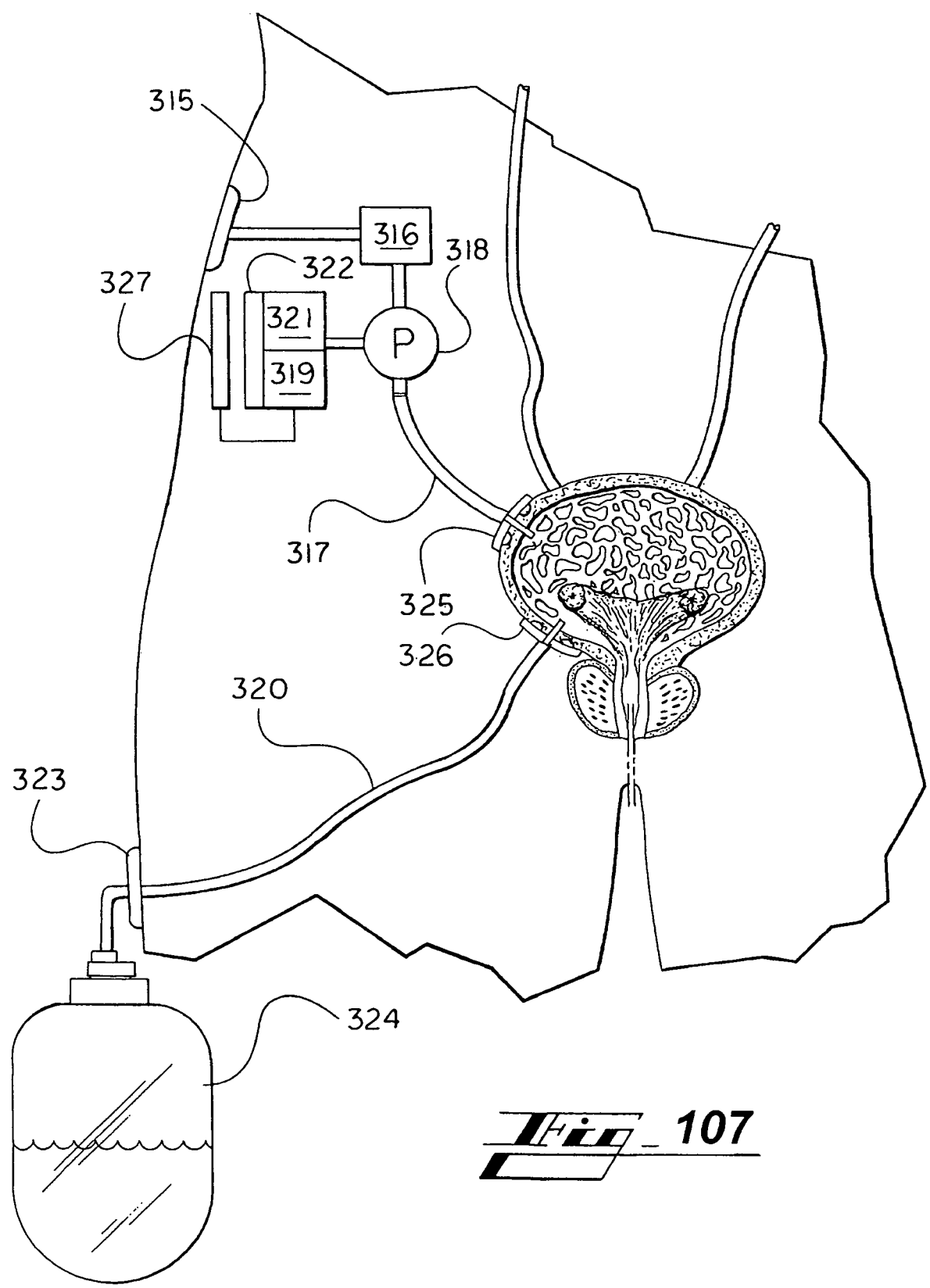

FIG. 107 shows a schematic for a single channel of control in a fully implanted ambulatory adaptive hierarchical control system for automatic response to a comorbid condition, wherein medication is automatically dispensed from flat reservoirs placed subdermally in the pectoral region for targeting directly to side-entry jackets along one or more organ systems through piping, this channel one of a number under adaptive or 'self tuned' hierarchical control of which the governing prescription program is discharged by an implanted microcontroller.

Figure 108:
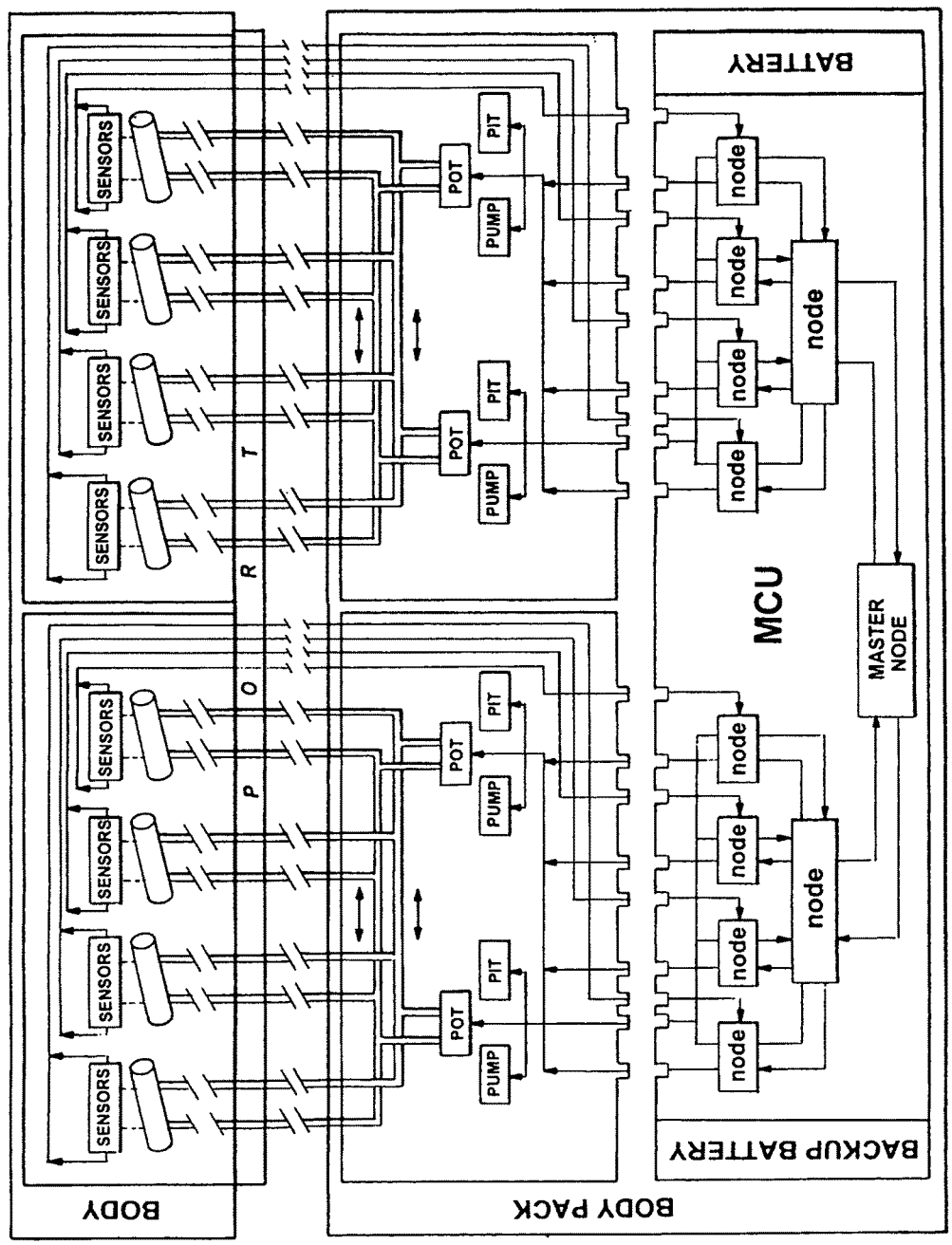

FIG. 108 shows the overall plan of a fully implanted adaptive ambulatory prosthetic disorder response system governed by a control system organized hierarchically to provide a dedicated channel of control to each of several different treatment sites or organ systems as components of a comorbid condition, such control discharged by an implanted microcontroller according to a prescription program that coordinates the directly targeted delivery of drugs to side-entry jackets such as that shown in FIG. 107, coordination among the channels directed to the optimal sustainment of homeostasis.

DESCRIPTION OF THE PREFERRED EMBODIMENTS

Figure 1:
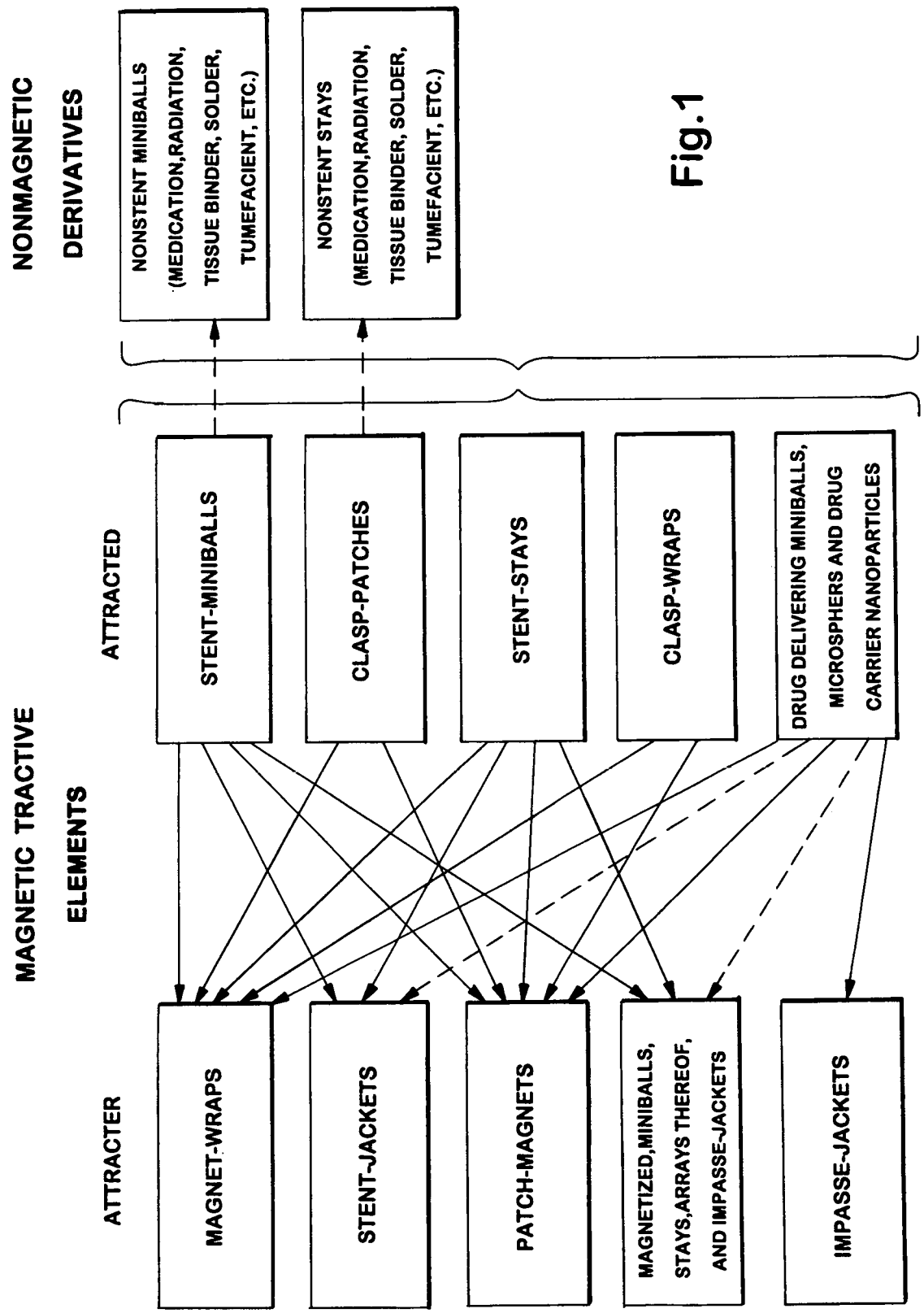
FIG. 1 depicts the interrelations among the various components described herein as constituting an integrated system.

FIG. 1 depicts the interrelations among the different types of implants, and FIGS. 2 thru 5 one end-condition sought through use of the methods and apparatus to be described. To apply to any tubular anatomical structure, viz. any vas (vessel), or ductus (duct), of adequate diameter, the figures omit histological detail. Accordingly, FIGS. 2, 4, and 5 may be taken to represent the lumen of a ureter, the esophagus, colon, trachea, or bronchus, and FIGS. 3, 4 and 5, which use the same part numbers for equivalent parts, show the lumen of an artery or vein following treatment with the apparatus and method to be described. Such treatment is not limited to implantation, but depending upon the specific apparatus, can include or consist of an ablation or an angioplasty using any or a combination of several means, and the application or injection of medication and/or any other fluid therapeutic substance, to include a test solution, stain (dye, contrast), or a cement for example.

FIG. 2 shows the extravascular component of an extraluminal magnetic stent, or stent-jacket, with intravascular component consisting of miniballs or stays about a generalized ductus, such as a ureter, FIG. 3 the same with a more dense formation of implants in a generalized vas, such as an artery or vein with the stent-jacket about the vas or ductus, in longitudinal section, while FIG. 4 shows this in cross section.

With a barrel-assembly that incorporates radial projection units and heat-windows—and if a combination-form barrel-assembly, a cabled device, such as an excimer laser, ultrasound angioplasty probe, or directional or rotational cutting tool atherectomy device—stenting discharge is initiated following preparation of the lumen immediately, without the need to withdraw and reenter. A simple barrel-assembly allows stenting without preparatory treatment, or direct stenting, or stenting following ablation or conventional balloon angioplasty, atherectomy, or both.

In FIGS. 2 thru 5, vas or ductus 1 has implanted just inside the outer fibrous layer, whether tunica fibrosa or adventitia 2 of its wall 7, ferromagnetic spherules or miniballs 3. Pulled outward by small bar magnets 4, usually made of neodymium iron boron lanthanoid mounted about the outer surface of surrounding length of pliant tubing, or base-tube 5, miniballs 3 draw the ductus wall 7 outward and so maintain the passageway or channel that courses through the ductus 8, or its lumen, open, or patent. Extravascular or extraductal stent component, referred to as a stent-jacket, 6 consists of base-tube 5 with moisture barrier-coated viscoelastic polyurethane foam lining 5a and magnets 4.

The magnets are magnetized in the radial direction and mounted longitudinally with a cement that extends the bond beyond tangent contact. An alternative stent-jacket (not shown) consists of a short length of thin tubing made of magnetizable stainless steel, for example. This is slit along one side and magnetized normal to the long axis. When the elasticity required calls for tubing too thin and/or not sufficiently magnetizable to support the magnetic field strength required, it is given an outer layer of a polymeric matrix with embedded neodymium iron boron particles prior to magnetization. The addition of a second such outer layer to serve as radiation shield for use with radiation-emitting stays or miniballs must likewise not detract from compliance as primary.

Ferromagnetic stays relate to the stent-jacket just as do miniball type implants but are inserted from outside the ductus allowing the lumen to be avoided during and following stenting, so that in direct stenting without antecedent atherectomy or angioplasty, the lumen is avoided entirely with stenting sustained by extraluminal components. An alternative stent-jacket consists of a length of thin intrinsically magnetized spring stainless steel tubing as addressed below in the section entitled Stent-jackets and Stent-jacket Supportng Elements. To allow flexibility, longer stent-jackets, whether polymeric with tiny permanent magnets mounted about the outer surface, or metal, consist of a series of elastic tubes joined or articulated by Palmaz-Schatz-type connections, as described below under the section entitled Sectional, or Chain-stents, Segmented and Articulated. Such a stent-jacket can be made to any length.

Ordinarily; the magnets are equal in strength and positioned uniformly about the base-tube; however, the strength of the magnets or magnetization over an affected area can be keyed to the subjacent condition, and for eccentric lesions, only those areas superjacent to the unaffected or affected area of the ductus need be subjected to tractive force to be drawn outwards. The magnetic field strength is strong enough to urge the adventitia 2 into contact with it but not to significantly interfere with the smooth muscle action in the ductus wall 7. The different kinds of stent-jacket are described above in the section entitled Types of Stent-jacket. The stent-jacket base-tube 5 is pliant and slit 9 longitudinally along one side but not so pliant that the lumen 8 can revert to its former stenosed or constricted condition.

The object is not merely to reinstate passability through the lumen of the air, blood, food, urine or other substance that is obstructed, but to do so with the least trauma essential to obtain results that will not pose complications over a longer term than does conventional or endoluminal stenting. A basically cylindrical conformation can be flared. Branches and bends are conformed to with chain-stents. To allow compliance to the pulse or intrinsic motility of the ductus and to avert the inducement of atheromatous lesioning by constriction of the microvessels and nerves of the adventitia, base-tube 5 of stent-jacket 6, described below, is slit, or if more clearance is needed, then slotted, and perforated.

The essential compliance will almost always be achieved with elastomeric or metal tubing of appropriate flexibility, thickness, and perforation pattern, but can also use compound or plied tubing of different materials or a compound extrusion, or coextrusion. Unless the tissue is severely malacotic or sclerotic, the number and distribution pattern of the magnets mounted about the stent-jacket is adapted to attract the intravascular miniballs or stays in a uniform manner. When a spring metal stent-jacket with intrinsic magnetization as will be described is used, such openings are likewise necessary. Perforation of the base-tube other than to adjust its restorative force, such as to allow the adventitia to 'breathe,' engage in ion exchange, and allow tissue infiltration to avert migration, when more extensive, will reduce its restorative force, which must not require a thickness that with magnets unacceptably encroaches upon the adjacent tissue.

Base tubes may comprise a polymeric tube to the surface of which have been fastened permanent bar magnets or smaller encased electromagnets. Smaller thickness, of value where any protrusion abaxially from the long central axis of the base tube would encroach upon and press or rub against neighboring tissue is obtained through use of a base tube comprising a thin magnetizable metal, for example, magnetized perpendicularly to the long axis of the substrate ductus. Base-tube perforations are usually open. By serving as a matrix or scaffold for infiltration by the surrounding tissue, absorbable adhesives and protein solders can be used for migration resisting adhesion followed by tissue integration.

These methods are capable of bolstering fixation periadventitially, and contact permitting, at the outer surface of the stent-jacket. Side-straps, described below in the sections entitled Jacket End-ties and Side-straps, The Extraductal Component of the Extraluminal Stent and the Means for its Insertion and Gross Positional Stabilization (Immobilizaton) of the Implant Insertion Site, allow adjustment in the cinching tautness of the jacket. End-ties, described below in the section entitled Jacket end-ties and Side-straps substantially eliminate the chance of migration, even should the stent take a direct blow.

Miniballs and stays likewise have external treatments to encourage integration into the surrounding tissue. For these subadventitially (perimedially) placed implants to become dislodged and enter the lumen before becoming integrated into the surrounding tissue is, based on this position, improbable. When such is a concern, an impasse-jacket, addressed above in the section entitled Concept of the Impasse-jacket and below in the section entitled Miniball and Ferrojluid-borne Particle-impassable Jackets, or Impasse-jackets, prepositioned downstream will stop and retain any miniballs indefinitely. Notwithstanding, any miniballs that do become trapped in an impasse-jacket can be noninvasively extracted at a later date if desired, as explained in the same sections.

The primary purpose of impasse-jackets, which applies to an extent to stent-jackets, magnet-jackets, and patch-magnets, however, is small-scale drug targeting a certain segment of a ductus or an organ. Unmagnetized base-tubes and spandex wrap-surrounds can be used, for example, to reduce an aneurysm incidentally diagnosed during imaging while still incipient but confirmed enlarging. When reducible thus, the shear forces within the weakened segment are restored to the essentially normal, and the jacket expands and contracts with the pulse. The restorative force used to contract the weakened artery to a smaller diameter is intrinsic in the materials of the base-tube, which can, however, be modified by incorporating perforations for 'breathing' or a mechanical or medication retaining texture embossed on the internal surface. The elastic side-straps used to prevent migration can be tightened to adjust jacket compliance.

Such base-tubes differ are made to a prescribed elasticity or resilience for compliance with the pulse or smooth muscle action and in incorporating apertures and a moisture barrier-coated viscoelastic polyurethane foam lining. To achieve the desired restorative force within the desired dimensions, selection of the base-tube material on the basis of intrinsic elasticity and resilience must therefore consider the most effective internal surface conformation, which may include undercuts, etching, or deeper texture for increased bonding surface area of an expansion insert, texturing or embossing for tissue infiltration and integration, perforations for gas exchange or breathing, for better adhesion of a surface film of medication, adhesive, perforation sealant, and so on, as described below.

In stent-jackets intended for noninvasive heating to reverse postprocedural reocclusion due to hyperplasia by means of noninvasive thermoplasty, the number, size, and distribution of 'breathing' holes as a source of resistance to eddy currents is compensated for when the temperature is noninvasively measured by means of an equivalent temperature calibrated eddy current detector. Stent-jackets placed before initiating discharge in order to avoid the risk of a perforation can be conventional or as addressed below in the section entitled Double-wedge Stent and Shield-jacket Rebound-directing Linings, but whose presence risks miniball rebound into the lumen, are made with a softer stent-jacket internal surface layer that is textured to serve the purposes indicated, and is backed by a flat-faced layer of greater resilience which is inclined distoradially to direct rebounds subadventitially or medially to remain functional for stenting and thus away from the lumen and toward a functional subadventitial or medial location for stenting purposes.

Figure 10:
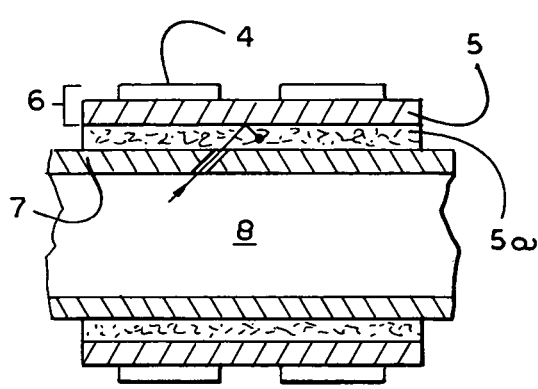
FIG. 10 is a diagrammatic longitudinal section view through a stent-jacket of the extrinsic spaced apart permanent bar magnet type with a longitudinally noninclined lining of moisture barrier-coated viscoelastic polyurethane foam showing a miniball that has perforated through the adventitia and rebounded off the internal surface of the base-tube without sufficient residual momentum to escape entrapment within the moisture barrier-coated viscoelastic polyurethane foam and penetrate into the lumen.

More specifically, as seen in FIG. 10, a miniball discharged through error at an exit velocity significantly greater than the results of the testing method provided in the section below entitled Testing and Tests indicates will perforate through the ductus wall, become embedded, and trapped within the foam lining. However, as in FIG. 11, at less excessive levels of momentum, the miniball can drive the wall of the ductus into the foam lining compressing it against the more resilient internal surface of the stent-jacket without perforating it. In that case, it is likely to rebound at the equal but opposite angle into the lumen.

Figure 12:
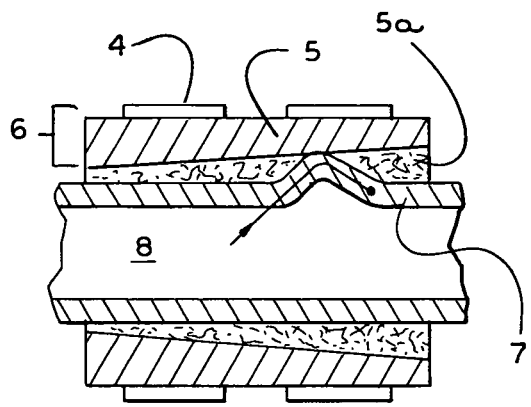
FIG. 12 is a diagrammatic longitudinal section view through a stent-jacket of the extrinsic spaced apart magnet type with a base-tube that increases in thickness from one end to the other and an angularly complementary or wedge-shaped moisture barrier-coated viscoelastic polyurethane foam lining where a miniball has forced the adventitia through the foam lining against the internal surface of the base-tube with sufficient momentum to rebound toward the lumen but deflected at the equal but opposite angle by the inclined surface to become embedded within the ductus wall rather than perforate into the lumen.

For the exit velocity to have been set so erroneously high that the miniball having perforated the ductus wall and entered the foam lining would have sufficient remaining momentum to rebound off the internal surface of the base-tube and then reperforate the ductus wall in the opposite direction and then rebound into the lumen is essentially impossible with nonmetal base-tubes and improbable even with metal ones; few if any miniballs are entirely metal; coatings of medication, and other therapeutic substances usually impart a softer, less resilient surface. A double-wedge lining as shown in FIG. 12 is intended steer the rebounding miniball away from the lumen and thereby preserve the functionality of a miniball that drives the ductus wall against the internal surface of the base-tube. The double-wedge lining accomplishes this by redirecting the miniball to a point farther down but still within the ductus wall and jacket.

In the circulatory system, a powerful extracorporeal electromagnet and/or an impasse-jacket is always prepositioned downstream to trap any miniball that might enter the circulation. In a double-wedge stent-jacket, a more resilient layer, which becomes thinner moving distad, is placed subjacent (outside, lateral, centrifugal) to its superjacent (inner) softer layer, which becomes thicker moving distad, so that these layers together constitute one continuous layer of which these halves are complementary to form a layer of uniform thickness. In a nonsubminiature or readily manipulable size, the inner layer would seem relatively 'hard.' A miniball rebounded off of the distally receding harder backing layer thus does so at an angle that is more acute in relation to the central axis of the lumen than were the reflecting surface parallel to the axis. The prepositioning of a stent-jacket solely to insulate a site for thermal angioplasty is unnecessary, and necessitates access to the treatment site through a second incision at the treatment site, needlessly increasing the procedural time.

A miniball that strikes the more resilient layer through the softer layer and rebounds at the equal and opposite angle will now be directed abaxially in relation to the angle that would have resulted were the surface rebounded off of parallel to the central axis of the lumen. When the area to be treated is extended, an extraluminal stent-jacket consisting of a train of sections connected by Palmaz-Schatz type stent connections, for example, can be made in any length. When the condition varies along the length, the individual sub-stents are varied accordingly. While intrinsically magnetized and thin neodymium magnets make possible extraluminal stents that encroach on neighboring structures minimally if at all, when perivascular placement should be avoided, an alternative to a surrounding stent-jacket is the magnet-wrap, or wrap-surround. A magnet-wrap is placed about a neighboring structure with magnets or if sufficiently proximate, intrinsic magnetization directed toward the miniballs or stays within the target ductus.

Application thus will usually respond to a need for radially asymmetrical or eccentric retraction of the ductus wall as in tracheal collapse, for example. However, both stent-jackets and magnet-wraps can be prepared to treat the ductus wall whether the condition is symmetrical or asymmetrical. A clasp-wrap (clasp-jacket, wrap-surround), addressed below in the section of like title, is in effect an artificial adventitia or fibrosa with ferromagnetic clasps for placement about a ductus that lacks an outer layer of sufficient intrinsic strength to retain implanted miniballs or stays under even a mild tractive force. Small opposing clasps, which may be coated with cyanoacrylate cement, mounted to a wrap made of spandex secured with hook and loop side-straps, for example, are used both to anchor the wrap into the outer surface of the ductus and substitute for the intravascular component of the extraluminal stent. The clasps are usually much more closely spaced together than are miniballs or stays, but can be asymmetrically to accommodate an asymmetrical condition.

When even this distribution would fail to prevent the mild tractive force from pulling the clasp-wrap away from the adventitia, a bonding agent that includes cyanoacrylate cement and is formulated to encourage tissue infiltration is applied to the internal surface of the wrap, thereby avoiding the need for a preliminary procedure to place the jacket and wait for integration to develop. The use of a clasp-wrap is also applicable when the diameter of the ductus makes the use of miniballs or stays too difficult. As does insertion by anastomosis of a graft, a clasp-wrap necessitates local access, but is applied much more quickly and with less trauma. Avoiding the risks of a graft and involving no entry as could leak or introduction of a foreign object into the lumen as would accumulate accreted matter, the use of a clasp-wrap or compound clasp-wrap with branches should be considered even when these alternatives are not contraindicated.

Just as miniballs and stays, a clasp-wrap can be used with either an immediately circumvascular stent-jacket, usually for all-around or almost all-around retraction, or with a magnet-wrap, usually for retraction from a distance of an arc of a stenotic or collapsed vessel or duct when intervening tissue in abutting relation to that to be drawn interferes with the placement of a stent-jacket, A stent-jacket can also accommodate asymmetrical or eccentric retraction and is indicated to prevent vasospasm, which demands circumferential retention. Magnetic force is able to retract and fixate ductus and tissues as not to encroach on neighboring tissue, for example, through intervening structures and along lines and over distances that suture cannot traverse.

A stent-jacket limits the radially outward excursion of the miniballs due to the magnetic or patenting force, hence, the resultant expansion or dilatation of the ductus due to this force, eliminating any risk of stretching injury. The stent-jacket is also elastic to accommodate the expansion and contraction of the ductus. A more resilient stent-jacket to limit expansion is readily producible but exceptional. If the tractive force is too great, either will pull through subadventital or subfibrosal implants or avulse (pull away) a clasp-jacket causing the stent to fail. Patch-magnets placed subcutaneously or suprapleurally, as described below in the section entitled Subcutaneous, Suprapleural, and Other Organ-attachable Clasp- or Patch-magnets can also be used for eccentric or arcuate retraction.

Once tissue alongside the sagging dorsal membrane (ligament) of the collapsed trachea in a small dog, for example, has been implanted with miniballs clear of the recurrent laryngeal nerves, the membrane can be lifted out of the lumen, alleviating the obstruction. This can be accomplished by magnets in a stent-jacket immediately surrounding the trachea, or situated along longitudinal ventrolateral lines of a magnet-wrap surrounding the esophagus, or placed subcutaneously along the neck and shoulders, or suprapleurally above the ceiling of a collapsed bronchus.

Where dysphagia is less of a risk, magnetized miniballs can be implanted along longitudinal ventrolateral lines within the esophagus itself. This variability in the components expedites treatment of tracheal segments both above and below the thoracic inlet. One example of the combined use of these variants is the application of jointed (articulated or segmented) stent-jackets to support the dorsal membrane of the trachea anterior to the thoracic inlet with subcutaneously or suprapleurally placed magnets used to support the ceiling when collapse extends into the bronchi where these are embedded in lung tissue and no longer encircleable by a stent-jacket.

I. Stent-Jackets and Stent-Jacket Supportng Elements

I1. General Considerations to Include Insertion

Stent-jackets are placed in encircling relation to ductus with the aid of stay insertion hand tools, as addressed below in the section entitled Stent-jacket Insertion Tools. Stent-jackets and impasse-jackets, as addressed below in the sections entitled Concept of the Impasse-jacket and Miniball and Ferrofluid-borne Particle-impassable-jackets, or Impasse-jackets overlap in function, but only an impasse-jacket is devised to allow the extraction of a miniball it has suspended within the lumen by means of an external electromagnet, for example. The extraductal or extravascular component, the stent-jacket, consists of a sleeve of resilient tubing that is slit along one side and when not magnetized intrinsically, by coating, or lamination, has tiny permanent magnets, currently made of neodymium iron boron lanthanoid, mounted about its outer surface. Temporary shield-jackets and stent-jackets are placed with the aid of a stent-jacket expansion or insertion tool, addressed below in the section of like title.

The tool is made with side-slit edge-engaging (hooking, working) ends for jackets of a certain thickness; the lining continues to the edge of the side-slit or side-slot, so that the jacket does not provide unlined edges or segments along the edges to accommodate an insertion tool with edge-engaging ends of one and the same size. In an extraluminal stent that is also to allow the extraction from the blood, for example, of magnetically susceptible drug carrier nanoparticles, for example, to achieve the tractive force required, the magnets will generally be somewhat larger. The magnets, which will normally consist of toxic neodymium lanthanoid, are first encapsulated for chemical isolation and cushioning with a coating of a plastisol-like or rubbery polymer or copolymer, then marked, usually by means of vapor deposition or sputtering, with an imaging marker, such as tantalum, tungsten, gold, molybdenum, and alloys thereof, or a biostable biocompatible radiopaque polymer.

The stent-jacket is introduced through a small incision and placed about the vessel or duct in encircling (perivascular, circumvascular) relation. The (intravascular) component of the stent consists of subadventitially or perimedially placed spherule or stay implants. The magnets mounted about the outer surface of a magnetic stent-jacket exert the minimum static centrifugal (circumferentially outward) magnetic retractive force on the intraductal (intravascular, ductus-intramural) component necessary to draw the adventitia of the ductus at its quiescent (resting, end-diastolic, unexpanded, smallest) outer diameter up against the inner surface of the stent-jacket, which is cushioned with a moisture barrier-coated viscoelastic polyurethane foam lining to minimize injury to any perivascular vessels and nerves.

The elastic and side-slit stent-jacket thus poses little resistance to the vasotonic and pulsatile expansion and contraction of arteries or the transit of the contractive waves of peristalsis. When the sole object is to preserve patency, the stent-jacket is fitted to the ductus so that the surface of the moisture barrier-coated viscoelastic polyurethane foam lining is maintained flush to the adventitia under the least effective force of attraction by the magnets surrounding the base-tube, the adventitial blood and nervous supplies impressed within the moisture barrier-coated viscoelastic polyurethane foam. Providing the highest energy product currently available, such magnets deliver adequate ductus wall retractive force in tiny sizes that suitably shaped and chemically isolated by encapsulation cause little if any irritation to neighboring tissue.

For use with arteries, a polymeric base-tube with magnets mounted about its outer surface can sometimes be replaced with a tube of thin sheet stock stainless steel that is intrinsically magnetized normal (radially in relation to) its long axis and slit to allow compliance with the pulse. Various strategies for building up the tractive force of the tube through the application of coatings that incorporate lanthanoid to allow the tube to remain thin for elasticity are addressed below in the section entitled Stent-jackets and Stent-jacket Supportng Elements. However, in a peristaltic ductus, the retractive force must be small enough and the stent-jacket base-tube pliant enough to pose minimal resistance to the inward excursion of the traveling contractive wave, which is usually more powerful than the stenosis or constriction produced by a disease without or following surgical treatment.

The internal diameter of the stent-jacket is matched to the external diameter of the ductus when quiescent, so that this retraction restores luminal patency. Intrinsic motility in the esophagus is not simply inward but involves the squeezing downward by the traveling wave of contraction of larger boli that produce an outward bulging of the esophagus just ahead of (addressed below) the contractive wave. The action travels down the organ as a circumferential expansion followed by a contraction. Irritation free conformity to this continuous action is elusive to any means of mechanical compliance or tracking; however, in the esophagus, the action occurs only during deglutition (swallowing). Lower in the tract, compliance is difficult due to the absolute excursion rather than the more clearly defined character of the action.

Compliance with this action without resistance as would induce dysphagia demands a long fatigue life thin walled polymeric base-tube with elasticity in the long dimension such as of an open mesh polyester reinforcing braid incorporated within the walls of silicone tubing as produced by NewAge Industries, Southampton, Pa. or Aesthetic and Reconstructive Technologies, Reno, Nev., for example, or of tubing made of a nickel titanium rings attached by longitudinal elastic ribs of plastic, for example, fastened about a tube of elastic polyester or polyurethane-polyurea copolymer spandex (Elastane® Lycra®), for example (see for example, Watanabe, M., Sekine, K., Hori, Y., Shiraishi, Y., Maeda, T., Honma, D., Miyata, G., Saijo, Y., and Yambe, T. 2005. "Artificial Esophagus with Peristaltic Movement," *Journal of the American Society for Artificial Internal Organs* 51(2): 158-161), magnets with longitudinal extension as does not interfere with this flexion, and application of the optimal magnet strength to maintain the retractive force required.

The noncollapsible, flexible, and side-slitted circumvascular stent-jacket limits closure of the substrate vas or ductus to the smallest normal diameter while allowing the ductus to expand. More specifically, the descending bulge and contraction of the esophagus during swallowing can be conformed to by a stent-jacket in the form of reach-around arms (ribs, tracheal cartilages) consisting of incomplete rings or broken bands of magnetized spring steel encapsulated for chemical inertness or magnetizable spring stainless steel, for example connected by a narrow spine located diametrically opposite to the aligned breaks in the rings. To allow optimal flexibility of the reach-around arms, the spine is kept proportionally narrow.

Expansion of the stent-jacket to position it about the esophagus requires that the breaks in the bands, that is, the space separating the free edges at the ends of the ribs, or side-slots, be aligned, and to preclude migration and present as a unit for expeditious placement, the bands must be longitudinally connected. Any rounding contour will interfere with band flexibility. The bands are therefore ground smooth at the edges. The appliance can be rotated to treat an eccentric lesion or made as long as necessary. Whether inserted by means of a stay insertion tool or barrel-assembly, the ductus-intramural implants are prepositioned to match the fitting of the appliance to the lesion.

When a bolus passes, the changes in distance between adjacent edges of neighboring bands increases as the free ends of the side-slots are approached, and is reduced as the spine is approached. The spine is therefore made as flexible in the longitudinal direction as possible, but will define the center of the least compliant arc. The circumferential positioning of the spine, whether it and the portions of the spines beside it are magnetized and the subjacent substrate ductus is implanted in radial alignment thereto depends upon the amenability or tolerance of the lesioned tissue to such treatment. When the lesion is eccentric (radially asymmetrical), the spine and adjacent portions of the ribs will therefore not mount magnets, have been intrinsically magnetized, or overly implanted tissue, and will be positioned diametrically opposite to the lesion.

When reduced compliance along the spine is not a problem and some retractive force is desirable to maintain luminal patency, the spine is made sufficiently magnetic for this purpose. Such a stent-jacket is suitable for stenting other portions of the gastrointestinal tract, for example. Accordingly, the breaks, or side-slots, in the thin-stock bands are situated diametrically opposite to the spine and are large enough to allow the bands to contract with the esophagus as the descending wave propels the bolus downward passes. The bands likewise pose little resistance to expansion by a large bolus and resumption of the quiescent diameter.

When the bands cannot be intrinsically magnetized to exert sufficient tractive force sufficient to maintain luminal patency and contract with the intrinsic action, small permanent magnets are mounted about the outer surface of each band in radial alignment to the ductus-intramurally implanted miniballs or stays. The elastic stent-jacket thus complies with pulsatile, tonic, or peristaltic expansion and allows the discretionary treatment of eccentric lesions. When the ductus is enlarged or swollen, a stent-jacket is chosen that incorporates an absorbable or percutaneous ultrasonic lithotriptor-destructible expansion insert. Expansion inserts are addressed below in the section entitled Expansion Inserts Absorbable, Meltable, and Comminutable for Time-discrete Decremental Contraction of Stent-Jackets.

An expansion insert glued along one side of the side slit so that the stent-jacket can still comply as slightly expanded allows the stent-jacket to contract in step with subsidence (regression, resolution) in the enlarged (dilated, distended, swollen, or ectasic) ductus. The advent of endoscopic means to minimize the trauma of exposure significantly augments the practicability and preferability of circumvascular over endoluminal stents in many locations and treatment situations. Access to the coronary arteries, for example, no longer necessitates a median sternotomy (midsternal thoracotomy, "zipper" incision), clamshell, anterolateral, or hemiclamshell thoracotomy. In the chest, remotely controlled robotic means materially advance the capability to minimize the access portal through a ministerotomy.

Access to the external surface of a coronary artery is usually direct through the divided sternum but can be accomplished with a craniotome or trephine. When possible, a minimal incision thoracotomy, such as is used in minimally invasive direct coronary artery bypass (MIDCAB; limited access coronary artery bypass; 'keyhole' incision heart surgery) to expose the left anterior descending artery and its diagonal branches on the front of the heart, is performed. Robotically assisted coronary artery bypass (RACAB) allows access to the coronary arteries without the need for a midsternal thoracotomy that would increase trauma and healing time. For endoscopic and robotic technology to allow the placement of a stent-jacket, magnet-surround, or miniball-surround requires configuration of the insertion tool for such use.

Retention of the wall of the ductus by means of subadventitial implants peripheral to the more vital tissue of the lumen lining under minimal retractive force averts compression necrosis and fistulization; subjected to strong mechanical forces, fibrous connective tissue substantially omits living cells. The extraluminal stent accomplishes this while leaving the lumen free and clear of any foreign object. The risks of necrosis and fistulization rise in proportion to an increase in adluminal placement, prompting means such as the application of an adhesive to prevent delamination within the lumen wall. The unobstructed and object free lumen is less likely to restenose, and should reintervention become necessary, the lumen will not be obstructed by a stent. The catheter-based apparatus described may be used with the patient inside the tunnel (gantry, bore) of a tomograph.

In structure, function, and application, the extraluminal stents to be described herein are fundamentally different from the various cuffs and sheaths to which such terminology has been applied in the past (see, for example, Zou, R. J., Zou, L. J., Huang, S. D., Wang, Y., Han, L., Ji, G. Y., and Xu, Z. Y. 2007. "Effect of External Stents on Prevention of Intimal Hyperplasia in a Canine Vein Graft Model," *Chinese Medical Journal* (in English) 120(24):2264-2267; Izzat, M. B., Teng, Z. Z., Ji, G. Y., Chu, H. J., Li, Z. Y., Zou, L. J., Xu, Z. Y., and Huang, S. D. 2007. "Does PGA External Stenting Reduce Compliance Mismatch in Venous Grafts?," *Biomedical Engineering Online* 6:12; Jeremy et al. 2004 cited above; Izzat et al. 1996 cited above; Froehlich, P., Seid, A. B., Kearns, D. B., Pransky, S. M., and Morgon, A. 1995. "Use of Costal Cartilage Graft as External Stent for Repair of Major Suprastomal Collapse Complicating Pediatric Tracheotomy," *Laryngoscope* 105(7 Part 1):774-775).

Compression of the microvasculature and tiny nerves that supply the outer tunics, or vasa and nervi vasora, is minimized by lining the stent-jacket with biocompatible padding in the form of a viscoelastic polyurethane foam (moisture barrier-coated viscoelastic polyurethane foam). Necrosis is also minimized by the tiny size of the intraductal implants, such that the immune system is able to eliminate the consequences of cells crushed during implantation or by mechanical stress. The size and mass of the magnets used in stent-jackets, magnet-wraps, and patch-magnets is minimized through the use of high energy product sintered neodymium iron boron ($Nd_2Fe_{14}B$; NIB; NdFeB, or "neo") magnets. Such magnets are commonly available with a plating of nickel and outer plating of gold.

With sufficient compliance to accommodate normal (tonic, pulsatile, or peristaltic) changes in caliber, a stent-jacket sized for the normal diameter of an artery will also contain and adjust to the reduction in ductus diameter of an incipient aneurysm as the aneurysm heals and subsides (shrinks, subsides resolves, regresses). A jacket without magnets or intraductal implants can be used to contain an incipient aneurysm before a more advanced fusiformation or sacculation that if left untreated would become lined with a laminar thrombus, or to shield against the striking of neighboring tissue by a miniball that perforates when discharged, for example. Unlike a noncompliant external stent of the prior art that must be secured with sutures at points over its entire surface, the stent-jacket is secured by means of elastic side-straps that do not add to the length of the small laparoscopic entry portal required for insertion. If the ductus to be stented is curved or must flex, a sectional or chain-stent, that is, one segmented or articulated is used.

By definition, an incipient aneurysm poses no risk of obstruction due to involution (infolding) or rupture when reduced by the stent-jacket, which can therefore include perforations or breathing holes to allow access to the outer surface of the artery, often the aorta. Even though circumvascular placement averts numerous drawbacks to endoluminal placement, in the case of an aneurysm, unless diagnosed before progressed to the point that placement is difficult if not dangerous, the use of an extraductal stent is to be avoided. Unlike an endoluminal stent-graft, use of a circumvascular stent to contain an aneurysmal artery becomes more difficult, less feasible, and less effective as the condition progresses. The larger the diameter of the aneurysm, the more difficult is opening a stent-jacket of suitable diameter to surround it, and the greater the risk of rupture, as well as the risk of reducing a thrombus within that could result in complete obstruction and the liberation of embolizing debris.

If there is no accumulation within, then the wall becomes too slack and subject to obstructive infolding if reduced from without. Whether the result of a fistula, accidental perforation, or incision, surgical repair and not a stent-jacket is used to seal a leaking ductus. Application of an external jacket without an intraductal component is addressed in the section above entitled Stent-jackets Used with Miniballs, this section, and the sections to follow entitled Means for Inducing the Formation of a Strong Implant-Tissue Bond, Description of the Preferred Embodiments, Expansion Inserts Absorbable, Meltable, and Comminutable for Time-discrete Decremental Contraction of Stent-Jackets, and Alternative Procedure to the Use of Expansion Inserts.

However, if initially sized to accommodate autonomic expansion in an already enlarged condition, then following subsidence, the end internal diameter of the stent-jacket will remain too large. The stent-jacket should not remain larger in internal diameter than the outer diameter in its resting phase of the ductus once healed. When the aneurysm is larger within the healable range, a stent-jacket with an expansion insert, as addressed below in the section entitled Expansion Inserts Absorbable, Meltable, and Comminutable for Time-discrete Decremental Contraction of Stent-Jackets, is used. With such an insert, the initial diameter of the stent-jacket accommodates the ductus and gradually contracts with the ductus to its end diameter. The use of a larger stent-jacket that would leave the stent-jacket slightly oversized once healing is complete is not preferred.

When the ending diameter of the ductus exceeds that expected by not more than 20 percent, the lack of full encirclement exerts a negligible effect on the ability of the stent to comply with the movement intrinsic in the ductus. If end-ties for preventing migration, as will be described, are contraindicated, but sufficient lengths of healthy tissue extend beyond the ends of an affected segment, then bridging or overextension of the stent-jacket or articulated stent-jacket onto the healthy tissue allows magnets and implants to be used over such nonaneurysmal or otherwise unaffected segments, and in contrast to an endoluminal stent used in a similar way, without encroachment upon the physiologically more active inner layers of the vessel. The use of a chain-stent, as addressed below in the section entitled Sectional, or Chain-stents, Segmented and Articulated, is indicated.

If the quiescent diameter of the ductus following healing might exceed the normal by more than 20 percent, an expansion insert that is spontaneously absorbed and/or can be actively reduced at a controlled rate over the period predicted for subsidence is used. This adaptability in diameter obviates the need to choose between a stent-jacket that fits initially but will be too small or too large following subsidence. Enclosing the vessel or duct within a compliant mantle that retracts the wall round and about both maintains the lumen patent and restrains the ductus from outward collapse or rupture. An extraluminal stent can therefore be used for structural failure whether inward or outward, and supports the wall during expansion and contraction with either. When significant, accurate placement of the miniballs requires that discharge be timed to the pulse. The momentum of discharge negates any resistance to penetration by the small infoldings or pleats that line the lumen on contraction.

When an additional object is to use the stent-jacket for followup magnetic drug-targeting, the magnetic force of the magnets about the base-tube is increased to the level necessary to attract the magnetically susceptible ferrobound particles passing through the bloodstream, usually injected in the form of a ferrofluid. Concerns about tunical delamination warrant testing as addressed below in the section entitled In Situ Test on Endoluminal Approach for Intra- or Inter-laminar Separation (Delamination, Laminar Avulsion). Delamination propensity testing and countermeasures addressed in the sections below entitled Use of Solid Protein Solders and Stays Coated with a Solid Protein Solder Coating and Cyanoacrylate Cement among others have been devised for application at the time of implantation to obviate the need for reentry.

When the drug or drugs are most effectively delivered to the treatment site at a concentration too high for systemic dispersal, the stent-jacket is provided with magnets strong enough to also support drug-targeting. A degenerative condition that would bode delamination at a later date if left untreated generally warrants the use of medication and/or brachytherapeutic implants with this capability. Only in situ testing will allow the strength of magnetization that would not pull through or cause delamination.

Should delamination occur, a barrel-assembly with a muzzle-head that is magnetically susceptible for steering, as addressed in the section below entitled Use of an External Electromagnet to Assist in Steering or in Freeing the Muzzle-head, and/or equipped with push-arm radial projection units, as addressed below in the section entitled Push-arm Radial Projection Unit Tool-inserts, or a radial projection catheter similarly equipped, as addressed in the section below entitled Radial Projection Catheters, is used to push the lumen wall radially outward after the same apparatus has been used to inject a cement into the delamination interface. If prepositioned, the stent-jacket can be used to back up the wall brought flush against the base-tube lining to compress the separated layers.

When the ductus expands during systoles or peristalsis and contracts during the passage of peristaltic waves, the microvasculature and innervation are accommodated within the moisture barrier-coated viscoelastic polyurethane foam lining and by the flexibility of the base-tube. The thickness of the lining is selected to minimize if not eliminate the long-term restriction or compression associated with expansion. This action demands a base-tube material capable of constant flexion in the internal environment with no significant loss in pliancy. Materials currently available that allow this are specified in the section below entitled Internal Environment-resistant Base-tube Polymers, Metals, and Combinations Thereof.

While not a direct object of the present invention, recent research indicates that a static magnetic field, previously thought to be completely noninteractive with tissue, reduces inflammation (see Morris, C. E. and Skalak, T. C. 2008. "Acute Exposure to a Moderate Strength Static Magnetic Field Reduces Edema Formation in Rats," *American Journal of Physiology. Heart and Circulatory Physiology* 294 (1):H50-H57; Morris, C. E. and Skalak, T. C. 2007. "Chronic Static Magnetic Field Exposure Alters Microvessel Enlargement Resulting from Surgical Intervention," *Journal of Applied Physiology* 103(2):629-636; Morris, C. E. and Skalak, T. C. 2005. "Static Magnetic Fields Alter Arteriolar Tone in Vivo," *Bioelectromagnetics* 26(1): 1-9).

It has been asserted that subjection to a static magnetic field reduces vasotonicity (see Gmitrov, J. 2013. "Static Magnetic Field Effect on Microcirculation, Direct Versus Baroreflex-mediated Approach," *Electromagnetic Biology and Medicine* 32(4):448-462; Albuquerque, W. W., Costa, R. M., Fernandes Tde, S., and Porto, A. L. 2016. "Evidences of the Static Magnetic Field Influence on Cellular Systems," *Progress in Biophysics and Molecular Biology* 121(1):16-28; Gmitrov, J. 2010. "Static Magnetic Field Blood Pressure Buffering, Baroreflex vs. Vascular Blood Pressure Control Mechanism," *International Journal of Radiation Biology* 86(2):89-101; Gmitrov, J. 2007. "Static Magnetic Field Effect on the Arterial Baroreflex-mediated Control of Microcirculation: Implications for Cardiovascular Effects Due to Environmental Magnetic Fields," *Radiation and Environmental Biophysics* 46(3):281-290; Gmitrov, J. 2007. "Geomagnetic Field Modulates Artificial Static Magnetic Field Effect on Arterial Baroreflex and on Microcirculation," *International Journal of Biometeorology* 51(4):335-345; Gmitrov, J., Ohkubo, C., and Okano, H. 2002. "Effect of 0.25 T Static Magnetic Field on Microcirculation in Rabbits," *Bioelectromagnetics* 23(3):224-229; Gmitrov, J., Ivanco, I., and Gmitrová, A. 1990. "Magnetic Field Effect on Blood Pressure Regulation," [in English] *Physiologia Bohemoslovaca* 39(4):327-334).

The detailed configuration of stent-jackets in dimensions, width of side-slit or side-slot, positioning about the outer surface of magnets, and whether the base-tube is sectional or segmental is keyed to the application. An advantageous attachment of the ductus is not dissected but accommodated by being straddled or spanned over with a side-slot. Eliminating ductus-intramural implants and magnets at the attachment not only preserves the attachment but averts the risk of erosive injury or fistula generative irritation to the tissue at and about the attachment. The side-slot is not targeted and not a likely area for a perforation. A stent-jacket that does not accommodate an attachment fully encircles the substrate ductus and can be provided with ductus wrap-around hook and loop straps, or side-straps (belt-straps, straps, side-belts).

addressed below in the section entitled Gross Positional Stabilization (Immobilizaton) of the Implant Insertion Site, when a fast or erratic pulse makes gauging the diastoles difficult, the stent-jacket, of which the internal diameter should match the outer diameter of the artery, is prepositioned with side-straps fastened to prevent the side-slit or side-slot from opening. Temporarily reducing or eliminating expansion and contraction allows greater accuracy in placing the implants, and temporarily reducing or eliminating expansion of the side-slit reduces or eliminates the risk of perforation therethrough. Following discharge, the straps are loosened so that the stent-jacket is free to expand with the artery. Accordingly, the barrel-assembly should allow blood to pass at the end-diastoles. Despite the measures addressed below in the section entitled Hypoxia and Ischemia-averting Elements, this factor will limit the muzzle-head that can be used in outer diameter.

End-ties, as addressed below in the section entitled Jacket end-ties and Side-straps, are end-tethers of suture which are fastened to the base-tube by sewing or riveted at or near to the ends of the base-tube. Stent-jackets with nonabsorbable suture end-ties can be tied around the substrate ductus at or beyond the sides of the base-tube or sutured to neighboring tissue. With large ductus, the end-ties can be passed through connecting tissue and self-attached with the hook and loop fasteners provided. A side-slot can also be used to blank out a longitudinal arc along a side of the base-tube that would abut on tissue which should be avoided. Magnets that despite their minute size, soft outer coating, and rounded edges arouse concern for encroachmemt upon and irritation of neighboring tissue are situated aside from the side-slot.

This will usually be the case with a coronary artery where the magnets would abut upon the heart. Following healing and cessation in the use of platelet blockades in arteries or anticoagulants in veins, an extraluminal stent is athrombogenic. Exceptionally, all types of thrombotic accidents warrant antiplatelet blockade for prevention (Adams, R. D., Victor, M., and Ropper, A. H. 1997. "Cerebrovascular Diseases," Chapter 34, pages 819-821), but anticoagulants rather than platelet blockades are used with established stoke (Adams, R. D. et al. 1997, op cit., page 819; Yatsu, F. M. 1995. "Treatment and Prevention of Stroke," in Rowland, L. P. (ed.), *Merritt's Textbook of Neurology*, Media, Pa.: Williams and Wilkins, page 273).

Numerous problems encountered with endoluminal stents are addressed above in the section entitled Background of the Invention. 2. Preliminary Description of the Invention. Introduced from outside the ductus, three types of device to be described, stays, clasp-wraps, and impasse-jackets, avoid the lumen entirely. When used in the vascular tree, these avoid the problems associated with placement of a foreign object in the lumen, disruption to the flow of blood, and the adverse consequences such disruption can induce (see, for example, Shive, M. S., Salloum, M. L., and Anderson, J. M. 2000. "Shear Stress-induced Apoptosis of Adherent Neutrophils: A Mechanism for Persistence of Cardiovascular Device Infections," *Proceedings of the National Academy of Sciences of the United States of America* 97(12):6710-6715; Shive, M. S., Brodbeck, W. G., Anderson, J. M. 2002. "Activation of Caspase 3 During Shear Stress-induced Neutrophil Apoptosis on Biomaterials," *Journal of Biomedical Materials Research* 62(2):163-168).

The ability to stent a ductus without the need to enter the lumen when using stays eliminates the potential for adverse sequelae, to include the reduction if not elimination of elastic recoil, stretching, dissection injury, and the ability to treat and maintain patent a lumen too tortuous to have been tracked transluminally. The means to be described for magnetic extraluminal stenting are equally usable for inserting implants that consist entirely of medication or irradiating seeds into the wall of any ductus. The ability to quickly implant one or several drugs and/or seeds having localized action with little effect on neighboring tissue can eliminate the need for systemic administration that would disperse medication throughout the body or extracorporeal administration that would demand a higher dose.

Since it compresses the lumen wall from within, tearing circumferential fibers or crushing any prominences and trapping debris between the stent and the intima, endoluminal stenting is more often applicable than is extraluminal stenting to stenting without first performing an angioplasty. In ballistic implantation, the muzzle-head could dislodge debris, whereas using stays, the lumen would not be entered at all. Since imaging cannot be depended upon to rule out the risk of liberating potentially embolizing debris, endoluminal stenting in the arterial tree assumes its previous removal (see the section below entitled Thermal ablation and angioplasty—(Lumen Wall Priming Searing- or Cautery-) capable Barrel-assemblies). Neither would insufficiency of intimal-medial thickness needed to place ductus-intramural implants be suitably remedied by allowing plaque to remain.

In this circumstance, the plaque is eliminated and sufficient wall thickness obtained with the aid of tumefacient drugs that temporarily cause the lumen wall to swell providing the needed thickness, or injectable fillers, such as collagen, hyaluronic acid, a gelatin powder-autologous blood mixture, or fat, which preserve wall thickness for months, or polycrylamide-water, viscid silicone oil, polymethylmethacrylate bead-collagen, and polyalkylimide-water mixtures, which for such application, must be highly viscous to provide a long term effect. Provided the ductus-intramural implants have become integrated into the tissue, that repeated compression on the systoles can eventually disperse and flatten the injectant is of nugatory consequence. Such injection is performed with radial projection unit injection tool-inserts, as addressed below in the section entitled Radial Projection Unit Tool-Inserts.

The use of an absorbable endoluminal stent (see, for example, Bundhun, P. K., Janoo, G., Yanamala, C. M., and Huang, F. 2017. "Adverse Cardiovascular Events Associated with Biodegradable Polymer Drug-eluting Stents and Durable Polymer Everolimus-eluting Stents: A Systematic Review and Meta-analysis of 10 Randomized Controlled Trials," *Medicine* (Baltimore, Md.) 96(28):e7510; Bundhun, P. K., Yanamala, C. M., and Huang, W. Q. 2017. "Comparing Stent Thrombosis Associated with Zotarolimus Eluting Stents Versus Everolimus Eluting Stents at 1 Year Follow up: A Systematic Review and Meta-analysis of 6 Randomized Controlled Trials," *BioMed Central Cardiovascular Disorders* 17(1):84; Bundhun, P. K., Bhurtu, A., Pursun, M., Soogund, M. Z. S., Teeluck, A. R., and Huang, W. Q. 2017. "Long-term (2-5 years) Adverse Clinical Outcomes Associated with ZES [zotarolimus-eluting stents] versus SES [sirolimus-eluting stents], PES [paclitaxel-eluting stents] and EES [everolimus-eluting stents]: A Meta-Analysis," *Scientific Reports* 7(1):6385; Kalra, A., Rehman, H., Khera, S., Thyagarajan, B., Bhatt, D. L., Kleiman, N. S., and Yeh, R. W. 2017. "New Generation Coronary Stents: Current Data and Future Directions," *Current Atherosclerosis Reports* 19(3):14; Alraies, M. C., Darmoch, F., Tummala, R., and Waksman, R. 2017. "Diagnosis and Management Challenges of In-stent Restenosis in Coronary Arteries," *World Journal of Cardiology* 9(8):640-651; Cui, Y., Liu, Y., Zhao, F., Shi, D., and Chen, K. 2016. "Neoatherosclerosis after Drug-Eluting Stent Implantation: Roles and Mechanisms," *Oxidative Medicine and Cellular Longevity* 2016:5924234 (also cited above in the section entitled Backgrond of the Invention. 2. Preliminary Description of the Invention); Pandya, B., Gaddam, S., Raza, M., Asti, D., and Nalluri, N., 2016. "Biodegradable Polymer Stents vs Second Generation Drug Eluting Stents: A Meta-analysis and Systematic Review of Randomized Controlled Trials," *World Journal of Cardiology* 8(2):240-246; Araki, T., Nakamura, M., and Sugi, K. 2014. "Characterization of In-stent Neointimal Tissue Components Following Drug-eluting Stent Implantation According to the Phase of Restenosis Using a 40-MHz Intravascular Ultrasound Imaging System," *Journal of Cardiology* 64(6):423-429; Ramcharitar, S. and Serruys, P. W. 2008. "Fully Biodegradable Coronary Stents: Progress to Date," *American Journal of Cardiovascular Drugs* 8(5): 305-314; Di Mario, C. and Ferrante, G. 2008. "Biodegradable Drug-eluting Stents: Promises and Pitfalls," *Lancet* 371(9616):873-874; Ormiston, J. and Webster, M. 2007. "Absorbable coronary stents," *Lancet* 369(9576):1839-1840) is not preferred, in part, because this requires the use of a balloon following withdrawal of the barrel-assembly.

In many instances, the use of stays can allow avoiding luminal entry altogether, which the use of an endoluminal stent negates. In a patient with atherosclerosis, plaque not already present is likely to develop at predictable locations, such as at branches, the carotid a prominent example. Since it will be absorbed, even if the patient is undergoing treatment in the catheterization laboratory, a drug-eluting biodegradable or absorbable stent cannot be placed as a preventive or ameliorative measure for plaque not yet materialized. The stent might detain or reduce the inflammation for a time but then disappear, allowing the progressive blockage to resume unimpeded. To the extent that dependence for attenuating the disease process is placed upon the drug eluted from a nonabsorbable stent, only a finite amount of the drug will be available.

Broadly, while absorbable stents of magnesium (see, for example, Waksman, R., Erbel, R., Di Mario, C., Bartunek, J., de Bruyne, B., and 10 other authors, 2009. "Early- and Long-term Intraductal Ultrasound and Angiographic Findings after Bioabsorbable Magnesium Stent Implantation in Human Coronary Arteries," *Journal of the American College of Cardiology: Cardiovascular Interventions* 2(4):312-320) are for this purpose depleted over a suitable interval, polymer stents (see, for example, Stinson, J. S. 2001. "Bioabsorbable Self-expanding Stent," U.S. Pat. No. 6,245,103) generally do so slowly. A subsidiary application of the present invention contemplates the use of a stent-jacket base-tube with end-ties (addressed below) and without magnets to truncate an incipient aneurysm from further distention. The incipient aneurysm will not encroach on adjacent structures or noticeably pulsate.

Asymptomatic, it must be detected during imaging for an unrelated purpose or specifically to catch subclinical pathology. When spontaneous or treated subsidence is improbable, the cost of repeated tomography or ultrasonography high, the trauma to enter deemed warranted, and the risk of enlargement high, active suppression by placement of a stent-jacket must be considered preferable to active surveillance (previously referred to as 'watchful waiting'). In such use, the resilient base-tube can be inserted and maneuvered into circumvascular position through one or two relatively small incisions. The quantity of periadventitial or perivascular fat about the aorta often substantial, only so much fat is trimmed away as will keep the aorta from being constricted under the retentive force of the nonmagnetic stent-jacket.

The availability of less radical procedures encourages earlier intervention. Placement of a stent-graft, much less conventional open repair, posing a poor risk to benefit ratio and the odds for rupture slight so long as the condition has not advanced, accepted doctrine is that an abdominal aortic aneurysm be monitored until it attains a diameter of five centimeters or more, produces discomfort, or enlarges. These can, however, arise at any time, the need for periodic reexamination is open-ended. A simpler endoscopic repair allows this abiding concern to be reduced with reexamination needed only to confirm that the integrity and placement of the reducing wrap persist. If not detected and treated earlier, the condition may progress until markedly fusiform or saccular, in some cases having accumulated a laminated thrombus lining.

Figures 14, 15:
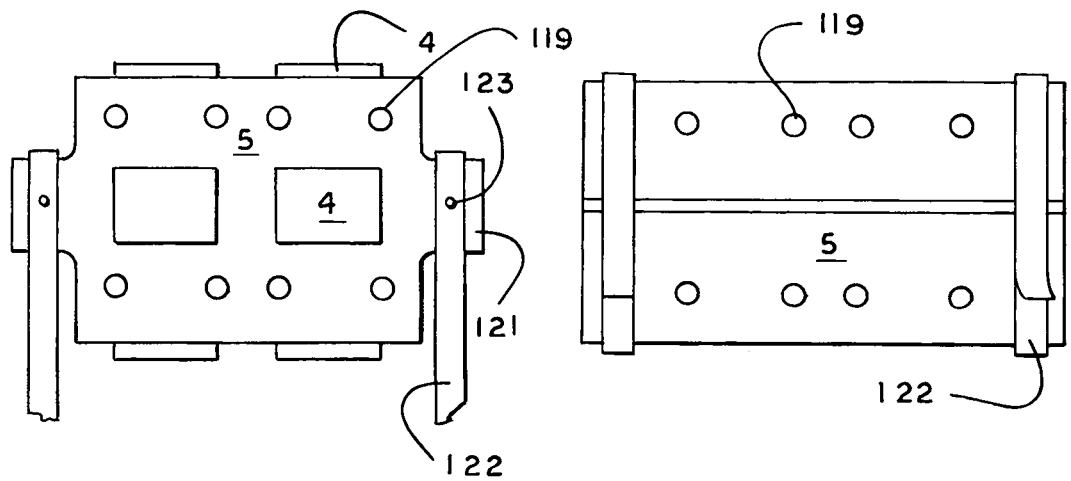
FIG. 14 is a longitudinal side view of a single extrinsically magnetized stent-jacket module segment or substent which has been cut from the continuous segmented stent-jacket shown in FIG. 13 by placing cuts midway between the adjacent end-straps.
FIG. 15 is a side view showing a nonmagnetized jacket, which can be a module cut from a segmented chain-stent, that varies in that the straps used to gird about or cinch the ductus are side-straps rather than end-straps, hence, suitable for containing an incipient aneurysm.

The thrombus affords no protection against rupture adjacent to the sac, and once thrombosed, intervention of any kind risks embolization. FIG. 15 shows a constraint for laparoscopic insertion that can be placed before a diameter that warrants surgical repair is attained. Aneurysms do not resolve spontaneously, and except for an accumulation of thrombus that may obstruct rupture, preserve the rate of flow-through, blood pressure, and luminal diameter preventing thromboembologenic turbulence, any change will be for the worse. Worse still, the mortality rate at 10 years following surgical repair is up to 50 percent (*The Merck Manual of Diagnosis and Therapy,* 18th Edition, Section 7, Cardiovascular Disorders, section 79, "Aneurysms," page 741). For that reason, intervention in a young patient while the aneurysm is still small enough to be reduced without serious risk of complications is prudent.

To reduce the chances for an asymptomatic aneurysm to go unnoticed, thoracic imaging should specifically check for such a condition. The jacket must be lined with nonbiodegradable or bioresistant viscoelastic polyurethane, or moisture barrier-coated viscoelastic polyurethane foam, and include perforations to expose the outer tunic to the surrounding gas. A cloth bandage if used to reduce an incipient aneurysm is critically lacking in that it may 'breath,' but as addressed above in the section entitled Accommodation of the Adventitial Vasculature, Innervation, and Perivascular Fat, will induce atherosclerosis quickly if it constricts supportive microvessels and nerves.

Early detection and containment with less trauma would truncate the degenerative process and the risk of rupture. So long as the enlargement has not spread to the common iliac arteries or become thrombosed and the available length of aorta superior and inferior to the aneurysm, or 'necks,' 'are at least 1.5 centimeters, an elastic base-tube without ductus-intramural ferromagnetic or magnet implants and including cut-outs to clear any branches can be maneuvered into position. While limited to aneurysms diagnosed prior to any significant enlargement, such a stent-jacket is not limited to an aneurysm in any particular location, so that an abdominal aortic aneurysm, for example, need not be infrarenal. Not a magnetic stent, minimizing the thickness of the base-tube and magnets to avoid rubbing against the surrounding tissue is not a factor.

While the matter remains in dispute as to reintervention, the realization is increasing that compared to conventional surgical repair the endovascular treatment of an aneurysm should commence promptly (Deery, S. E., O'Donnell, T. F. X., Bodewes, T. C. F., Dalebout, B. A., Pothof, A. B., and 3 others 2018. "Early Reintervention after Open and Endovascular Abdominal Aortic Aneurysm Repair is Associated with High Mortality," *Journal of Vascular Surgery* 67(2): 433-440.e1; Qiu, J., Shu, C., Cai, W., Li, M., and Li, Q. 2017. "Early Intervention Effects of Open Repair and Endovascular Aortic Repair on Patients Suffering from 40-54 mm Abdominal Aortic Aneurysms: Single Center Experience," *Minerva Chirurgia* 72(5):391-396; Deery, S. E., Soden, P. A., Zettervall, S. L., Shean, K. E., Bodewes, T. C., and 3 others 2017. "Sex Differences in Mortality and Morbidity Following Repair of Intact Abdominal Aortic Aneurysms," *Journal of Vascular Surgery* 65(4):1006-1013; Ulug, P., Sweeting, M. J., von Allmen, R. S., Thompson, S. G., Powell, J. T. and 8 collaborators 2017. "Morphological Suitability for Endovascular Repair, Non-intervention Rates, and Operative Mortality in Women and Men Assessed for Intact Abdominal Aortic Aneurysm Repair: Systematic Reviews with Meta-analysis," *Lancet* 389(10088):2482-2491; Canadian Task Force on Preventive Health Care 2017. "Recommendations on Screening for Abdominal Aortic Aneurysm in Primary Care," *Canadian Medical Association Journal* 189(36):E1137-E1145; Zarins, C. K., Crabtree, T., Bloch, D. A., Arko, F. R., Ouriel, K., and White, R. A. 2006. "Endovascular Aneurysm Repair at 5 Years: Does Aneurysm Diameter Predict Outcome?," *Journal of Vascular Surgery* 44(5):920-931; Flores, J., Kunihara, T., Shiiya, N., Yoshimoto, K., Matsuzaki, K., and 8 others 2005. "Importance of Early Repair of Isolated Abdominal Aortic Dissecting Aneurysm," *Vasa* 34(2):118-122) a conventional endovascular stent-graft can cause as many problems as it alleviates (below and see, for example, Rutherford, R. B. 2006. "Randomized EVAR [endovascular aneurysm repair] Trials and Advent of Level I Evidence: A Paradigm Shift in Management of Large Abdominal Aortic Aneurysms?," *Seminars in Vascular Surgery* 19(2):69-74) recommending early intervention all the more. Segmented and articulated or jointed stent-jackets allow flexion and the clearing of side branches without resistance, bulging, or buckling regardless of length, allowing application to any conduit however extended is the ectasia in length.

The placement of a stent-jacket along the abdominal aorta, where the pulse, hence, vasotonic migratory forces are marked, is positionally stabilized by passing suture through suture loops, or suture eyelets, integral with the jacket, usually with suture end-ties prefastened thereto to anchor the jacket to surrounding tissue at several points above and below where the suture is of sufficient elasticity (see, for example, Branco, P. S., Cardoso Junior, M., Rotbande, I., Ciraudo, J. A., Silva, C. R., and Leal, P. C. 2017. "Elastic Suture (Shoelace Technique) for Fasciotomy Closure after Treatment of Compartmental Syndrome Associated to Tibial Fracture," *Revista Brasileira de Ortopedia* [Brazilian Journal of Orthopedics] 52(1):103-106; Lambertz, A., Vogels, R. R., Busch, D., Schuster, P., Jockenhövel, S., and 3 others 2015. "Laparotomy Closure Using an Elastic Suture: A Promising Approach," *Journal of Biomedical Materials Research. Part B, Applied Biomaterials* 103(2):417-423; Simón-Allué, R., Pérez-López, P., Sotomayor, S., Peña, E., Pascual, G., Bellón, J. M., and Calvo, B. 2014. "Short- and Long-term Biomechanical and Morphological Study of New Suture Types in Abdominal Wall Closure," *Journal of the Mechanical Behavior of Biomedical Materials* 37:1-11; Bellón, J. M., Pérez-López, P., Simón-Allue, R., Sotomayor, S., Pérez-Köhler, B., and 3 others 2014. "New Suture Materials for Midline Laparotomy Closure: An Experimental Study," *BioMed Central Surgery* 14:70) as not to significantly pull at and injure the tissue.

Figures 16A, 16B, 16C:
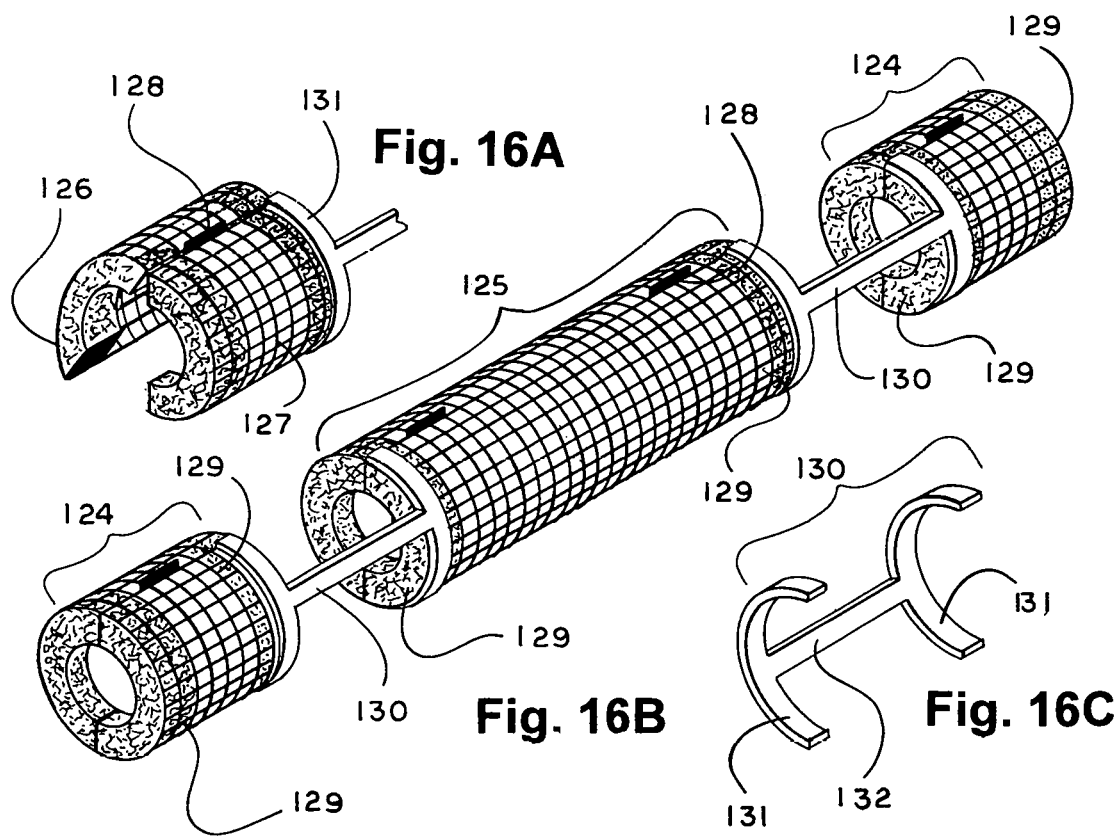
FIG. 16A is a perspective view of the proximal stabilizing dummy collar, or outrigger, of a compound impasse-jacket shown in its entirety in FIG. 16B.
FIG. 16B is a perspective view of a compound impasse-jacket shown in its entirety.
FIG. 16C is a perspective view of one of the bendable bridges used to join stabilizing dummy collars, that proximal shown in FIG. 16A, of a compound impasse-jacket to the impasse-jacket proper shown in FIG. 16B.

The need for outrigger stabilizers or dummy collars as shown in FIG. 16, part number 124 in addition to suture loops (or suture eyelets), or end-ties should prove seldom necessary. By comparison, endoluminal stents provide no way to prevent migration other than by protrusion of relatively thin struts, wire, or prongs into the endothelium or urothelium, for example, which then acts as a chronic irritant to the substrate ductus.

Without stabilizing means, migration is a problem whether the means of aneurysmal containment is extra or endoluminal (see, for example, Filis, K. A., Galyfos, G., Sigala, F., Tsioufis, K., Tsagos, I., and 3 others 2017. "Proximal Aortic Neck Progression: Before and After Abdominal Aortic Aneurysm Treatment," *Frontiers in Surgery* 4:23; Spanos, K., Karathanos, C., Saleptsis, V., and Giannoukas, A. D. 2016. "Systematic Review and Meta-analysis of Migration after Endovascular Abdominal Aortic Aneurysm Repair," *Vascular* 24(3):323-336; Pintoux, D., Chaillou, P., Azema, L., Bizouarn, P., Costargent, A., Patra, P., and Gouëffic, Y. 2011. "Long-term Influence of Suprarenal or Infrarenal Fixation on Proximal Neck Dilatation and Stentgraft Migration after EVAR [endovascular aortic repair]," *Annals of Vascular Surgery* 25(8):1012-1019; Benharash, P., Lee, J. T., Abilez, O. J., Crabtree, T., Bloch, D. A., and Zarins, C. K. 2007. "Iliac Fixation Inhibits Migration of Both Suprarenal and Infrarenal Aortic Endografts," *Journal of Vascular Surgery* 45(2):250-257; Litwinski, R. A., Donayre, C. E., Chow, S. L., Song, T. K., Kopchok, G., Walot, I., and White, R. A. 2006. "The Role of Aortic Neck Dilation and Elongation in the Etiology of Stent Graft Migration after Endovascular Abdominal Aortic Aneurysm Repair with a Passive Fixation Device," *Journal of Vascular Surgery* 44(6):1176-1181; Zarins, C. K., Bloch, D. A., Crabtree, T., Matsumoto, A. H., White, R. A., and Fogarty, T. J. 2003. "Stent Graft Migration after Endovascular Aneurysm Repair: Importance of Proximal Fixation," *Journal of Vascular Surgery* 38(6):1264-1272).

Not requiring tissue perforation with suture or incision, infection is less likely, and sealing the aneurysmal segment round and about, continued enlargement (see, for example, Nakai, M., Ikoma, A., Sato, H., Sato, M., Nishimura, Y., and Okamura, Y. 2015. "Risk Factors Associated with Late Aneurysmal Sac Expansion after Endovascular Abdominal Aortic Aneurysm Repair," *Diagnostic and Interventional Radiology* 21(3):195-201; Dubenec, S. R., White, G. H., Pasenau, J., Tzilalis, V., Choy, E., and Erdelez, L.2003. "Endotension. A Review of Current Views on Pathophysiology and Treatment," *Journal of Cardiovascular Surgery* (Turin, Italy) 44(4):553-557) is counteracted.

Continued enlargement is suppressed whether the cause is endoleakage or endotension, the latter hypothesized to result from either an imperceptible endoleak (Lin, P. H., Bush, R. L., Katzman, J. B., Zemel, G., Puente, O. A., Katzen, B. T., Lumsden, A. B. 2003. "Delayed Aortic Aneurysm Enlargement Due to Endotension after Endovascular Abdominal Aortic Aneurysm Repair," *Journal of Vascular Surgery* 38(4):840-842; Veith, F. J. and Baum, R. A. (eds.) 2002. *Endoleaks and Endotension: Current Consensus on Their Nature and Significance*, New York, N.Y.: Informa HealthCare) or increased graft permeability (Kougias, P., Lin, P. H., Dardik, A., Lee, W. A., El Sayed, and H. F., Zhou, W. 2007. "Successful Treatment of Endotension and Aneurysm Sac Enlargement with Endovascular Stent Graft Reinforcement," *Journal of Vascular Surgery* 46(1): 124-127).

Certain circumstances do recommend endovascular repair (see, for example, Zettervall, S. L., Ultee, K. H., Soden, P. A., Deery, S. E., Shean, K. E., and 3 others 2017. "Predictors of Renal Dysfunction after Endovascular and Open Repair of Abdominal Aortic Aneurysms," *Journal of Vascular Surgery* 65(4):991-996; Spanos, K., Karathanos, C., Athanasoulas, A., Saleptsis, V., Vasilopoulos, I., and 3 others 2017. "Renal Function Impairment in Patients Undergoing Elective EVAR vs. Elective Open Repair During Follow up Period: A Systematic Review of the Literature," *Current Vascular Pharmacology* 15(2): 103-111).

Where the kidneys are distant, however, likely the result of presuming that with a transluminal procedure available, an open procedure should be avoided at all costs, a failure to fully envelop the aneurysm within a nonself-expanding, unyielding, nonstretchable jacket (which can be curved for use in the thorax or bifurcated for use in the abdomen) or by conventional open surgical repair, using a conventional endoluminal stent graft, continued enlargement and even rupture of both abdominal and thoracic aortic aneurysms is indeed possible (see, for example, Ultee, K. H. J., Zettervall, S. L., Soden, P. A., Darling, J., Verhagen, H. J. M., and Schermerhorn, M. L. 2017. "Perioperative Outcome of Endovascular Repair for Complex Abdominal Aortic Aneurysms," *Journal of Vascular Surgery* 65(6):1567-1575; Ultee, K. H., Soden, P. A., Zettervall, S. L., Darling, J., Verhagen, H. J., and Schermerhorn, M. L. 2016. "Conversion from Endovascular to Open Abdominal Aortic Aneurysm Repair," *Journal of Vascular Surgery* 64(1):76-82; Kasahara, H., Hayashi, I., and Haijima, N. 2015. "Aneurysm Growth after Late Conversion of Thoracic Endovascular Aortic Repair," *SAGE* [Publications] *Open Medical Case Reports* 3:2050313X14565422; Dalainas, I. and Xiromeritis, K. 2010. "Aortic Neck Dilatation and Endograft Migration after EVAR [endovascular aortic repair]," *Journal of Endovascular Therapy* 17(6):685-686; Oberhuber, A., Schwarz, A., Hoffmann, M. H., Klass, O., Orend, K. H., and Mühling, B. 2010. "Influence of Different Self-expanding Stent-graft Types on Remodeling of the Aortic Neck after Endovascular Aneurysm Repair," *Journal of Endovascular Therapy* 17(6):677-684; Moulakakis, K. G., Dalainas, I., Mylonas, S., Giannakopoulos, T. G., Avgerinos, E. D., and Liapis, C. D. 2010. "Conversion to Open Repair after Endografting for Abdominal Aortic Aneurysm: A Review of Causes, Incidence, Results, and Surgical Techniques of Reconstruction," *Journal of Endovascular Therapy* 17(6): 694-702; Thomas, B. and Sanchez, L. 2009. "Proximal Migration and Endoleak: Impact of Endograft Design and Deployment Techniques," *Seminars in Vascular Surgery* 22(3):201-206; Orra, H. A., Puech-Leão, P., Silva, E. S., and Silva, D. G. 2008. "Aneurysm Pulsatility after Endovascular Exclusion—An Experimental Study Using Human Aortic Aneurysms," *Clinics* (Sao Paulo, Brazil) 63(1):67-70; Lin, P. H., Bush, R. L., Katzman, J. B., Zemel, G., Puente, O. A., Katzen, B. T., and Lumsden, A. B. 2003. "Delayed Aortic Aneurysm Enlargement Due to Endotension after Endovascular Abdominal Aortic Aneurysm Repair," *Journal of Vascular Surgery* 38(4):840-842).

While an incipient aneurysm would shrink if bypassed or excluded with a stent-graft, under the guidelines stated above, it would not be treated at this early stage. The aneurysmal wall is reduced to some extent with an endovascular lining (endograft, internal bypass graft; endoprosthesis) in place, but recovery is necessarily without exposure to the flow of blood, and the various means stated are for all practical purposes irrecoverable once applied. Neither is there reason to assume that the earliest intervention would allow an aneurysm to actually heal and regain wall strength rather than just shrink so that a temporary (absorbable) stent-jacket could be used to contain it only so long as sufficient strength took to develop. Indeed, the repair of an aneurysm at one location may lead to another at the next weakest point along the vessel. Circumductal (periductal) stents, with or without implants or circumvascular bonding but with a side-slit and thus compliant with smooth muscle action, can also be used to close off fistulae.

In veterinary practice, a less radical than conventional highly traumatic procedure for the repair of tracheal collapse would likewise encourage intervention before this invariably progressive condition could result in asphyxia. Whereas the preceding applications involve containment, stenotic conditions, to include tracheal collapse, require that the wall of the ductus be retracted radially outwards. The radical surgery normally performed to accomplish this is avoided by laproscopically inserting wide, usually cyanoacrylate cement-coated, ferromagnetic stays along and to either side of the collapsed dorsal ligament and a base-tube surrounding the ductus having tiny magnets with which to draw the spherules outwards. Since the flaccidity tends to gain in length, the segment included is deliberately overextended. Implantation from within the lumen into the wall of the ductus of small ferromagnetic spherules requires greater skill.

To reduce the risk of migration, the stent-jacket:

1. Resiliently grasps about the vessel or duct with the least magnetic force.

2. Can often be safely extended over a greater length than an endoluminal stent. 3. Can thus have a greater contact area while less aggressively maintaining the ductus patent.

4. Is lined with a moisture barrier-coated viscoelastic polyurethane foam cushion, firmer but nonincisive projections, gauze, or a surface that is textured, which also increases the surface area for tissue integration by infiltration and adhesion of a sealant, adhesive, antibiotic, or other medicated coating.

5. Can be bonded in whole or part to the outer surface of the substrate ductus regardless of the lining used, and 6. Have wrap-around straps or ties (end-ties, end tethers) at one or both ends. An individual stent-jacket spans side branches with a hole at the end of a slit cut from the side-slit or side-slot with no risk as there is with an endoluminal stents that the lumen wall might prolapse through the mesh.

Alternatively, articulated and special purpose stent-jackets can span side-branches, attachments, bends, and points of flexion with no less compliance to peristalsis or the pulse. The spherules and/or the internal surface of the stent-jacket can be medicated or irradiating. The stent-jacket lining is bonded inside the base-tube by ultrasonic welding or an adhesive. Adhesives for bonding gauze within the stent-jacket, for example, are specified below in the section entitled Stent- and Shield-jacket Anti-migration Linings. The apparatus to be described includes means for adding a tough outer layer about a weak or malacotic vas or ductus without the strength required to support a tractive magnetic force, means for recovering loose and for extracting mispositioned spherules or stays, for testing airgun control settings for the force of impact necessary to seat the spherule implants in the diseased tissue encountered in situ quickly, and for motorization of the muzzle-head.

The ability to induce an implant to generate heat noninvasively has numerous applications. Applying such function to a ductus not open to the exterior and precluded from the use of magnetic resonance for imaging where collateral heating of the implant could prove harmful (see, for example, Prasad, S. K. and Pennell, D. J. 2004. "Safety of Cardiovascular Magnetic Resonance in Patients with Cardiovascular Implants and Devices," *Heart* 90(11):1241-1244), demands an assessment as to the prospective need for such imaging and the difficulty of recovering the implant in that event; recovery like placement necessitates exposure through a small incision and the need to dissect the ductus to allow its partial or complete encirclement by the stent-jacket, or extraductal component of an extraluminal stent.

Older technology pacemaker and cardioverter defibrillator implants may require any device incorporating a permanent magnet to be kept at a minimum distance. When undesirable, heating can be reduced if not eliminated (see, for example, McElcheran, C. E., Yang, B., Anderson, K. J., Golenstani-Rad, L., and Graham, S. J. 2015. "Investigation of Parallel Radiofrequency Transmission for the Reduction of Heating in Long Conductive Leads in 3 Tesla Magnetic Resonance Imaging," *Public Library of Science One* 10(8): e0134379).

I2. Structural and Functional Considerations

A description of stent-jackets in terms of parts is provided in the sections above entitled The Extraductal Component of the Extraluminal Stent and the Means for its Insertion and Description of the Preferred Embodiments. The materials of and various modifications to stent-jackets are no less significant. In an extrinsic stent-jacket, the magnets are preferably unitized with the base-tube before the lining is bonded to its internal surface by dip or spin coating polymer encapsulation. To allow portions of the base-tube to be snipped away to clear attachments, for example, the base-tube must be approved for implantation without the protective coating.

Stent-jackets consist of a base-tube, part number 5 in FIGS. 2 thru 7, made of rolled, intrinsically magnetized, metal sheet, or comprise polymer sheet with small permanent or electromagnets fastened about the outer surface. When the intraluminal susceptible matter, usually consisting of microspherules comprising compacted superparamagnetic iron oxide nanoparticles, a stent-jacket with permanent magnets is used to cause the microspherules to abut in pressing relation against the endothelium or urothelium, for example.

When the intraluminal susceptible matter is to be drawn into the intima, the stent-jacket has small electromagnets fastened about the outer surface of the base-tube. Further structural details pertaining to stent-jackets and the means for imparting high tractive force to small electromagnets appear herein in several locations. A radial projection catheter can be used to inject susceptible matter with or without medication adherent to or impregnated therein into the intima with any type stent-jacket or impasse-jacket.

Pending unitization thus, the magnets are tacked in position with cyanoacrylate cement, or if larger in diameter, a viscous cement that will take up the nontangent interface between the magnet edges and the base-tube. Since removal to fit may approach the magnets, these must have been chemically isolated such as by vapor deposition or plating with titanium or gold, for example, before encapsulation, and the tacking cement must have been approved for implantation. Loctite Hysol Cool Melt®, which melts at 250 degrees Fahrenheit, well below the Curie temperature of neodymium iron boron magnets, to cite but one commercial adhesive, and cyanoacrylate cements generate relatively negligible exothermic heat during polymerization (setting), which varies as the setting time, can be used.

The surface of the base-tube to which the magnets are to be bonded are etched or scored with surface undercuts for more secure adhesion. The magnets should not require to be specially molded to create an arcuate internal surface or the base-tube specially extruded or machined with longitudinal planar arcs for attachment of the magnets; when the thickness of the stent-jacket must be minimized, the use of an intrinsically magnetized stent-jacket is indicated. The base-tube 5 with magnets 4 and any rivets is chemically isolated by polymeric dip-coating encapsulation before the lining is bonded to its internal surface.

Once completed, individual stent-jackets may be strung together into a linked succession of stent- and/or impasse-jackets of like or different kinds as dictated by the medical requirements. To assure the versatility demanded, such a linked succession, as addressed below in the sections entitled Sectional, or Chain-stents, Segmented and Articulated and Braced, Compound, and Chain Impasse-jackets, is not presequenced and chemically isolated as an intact train of manufacture but is freely assembled. For inserting rivets to secure jacket to jacket connecting wires, jackets to be connected are punched with a single pair of bilateral holes toward the ends of the base-tube, breaking the chemically isolating seal of the encapsulating coating.

To provide chemical isolation for the chain, flat flanged short straight barrel rivets of titanium anodized aluminum, another nonferrous metal, or nonmagnetic stainless steel are used to attach the thin bilateral nonmagnetic stainless steel wires used to connect one jacket to the next. Further protection against a break in the isolating seal is attained through the use of base-tube materials approved for medical use by the Food and Drug Administration, such as Polymer Technology Group, Incorporated Bionate® polycarbonate based polyurethane copolymer of durometer D-scale 55 and silicone-urethane copolymers. Since pressing the rivets closed is likely to produce microfractures in a plated surface exposing a non-biocompatible substrate, material, conventional electroplating is avoided, although certain types of vapor deposition such as addressed below in this section may prove satisfactory.

The rivets should be pressed in with enough force to draw the heads on the internal surface of the base-tube up into the lining and flush to the inner surface as not to protrude through the lining and into the encircled adventitia or fibrosa. Consistent with the need for compliance with expansion and contraction of the substrate ductus and to minimize tangent separation at the magnet ends, the magnets are applied to the outer surface of the base-tube longitudinally along the length of the base-tube. The magnets or intrinsic magnetization of the jacket is normal to the long axis. Within the constraint that the flexibility of the base-tube should not significantly impeded, using more expansive magnets reduces the criticality of magnet positioning relative to the miniball or stay implants.

Since stays have circumferential extension, these are easier to overlay with magnets mounted to a base-tube than are miniballs. When magnet overlay alignment is problematic, an additional measure is to use an intrinsically magnetized stent-jacket. Distinctions in magnetic strength along a single stent-jacket to accommodate variability in the retentive strength (resistance to pull-through) of the tissue treated is seldom appropriate; wide differences in the magnetic strength suitable for proximate locations bode not just implant local pull-through but more extensive rupture, so that only the least functional strength is uniformly applied. Disease-weakened eccentric (radially asymmetrical) tissue is omitted from implantation and subjection to tractive force, the stent-jacket with a magnet-blanked area positioned with the aid of continuous fluoroscopic monitoring.

Offset stretches of a stenosed ductus that vary in wall strength among affected segments are treated with a segmented or chain-stent wherein the sub-stents are selected for the safe strength to be used as are questions of least functional strength generally, based upon the results of the in situ test described below in the section entitled Testing and Tests. If distinctions in magnetic strength along a single stent-jacket are felt justified, placing miniballs or stays of different magnetic strength and then positioning a stent-jacket with uniformly strong magnets is easier and more economical than is the opposite of apposing magnets of different strength to designated ductus-intramural implants. Either approach demands the use of continuous fluoroscopic monitoring to reveal the position of the ductus-intramural implants as the jacket is placed and allow the apposition required.

Expansion inserts are addressed below in the section entitled Expansion Inserts Absorbable, Meltable, and Comminutable for Time-discrete Decremental Contraction of Stent-Jackets and shown in FIGS. 7 thru 9. A side-slot provides a greater width than a side-slit to allow the stent-jacket to clear a connective tissue attachment or adhesion wanted preserved, so that the slot is unavailable for an expansion insert. When clearance must be provided to pass a nervelet, for example, a portion of the base-tube bordering the edge of the slit is nibbled or snipped away. Expansion inserts are intended to be temporary and most are intended to be disintegrated by exposure to the internal environment, so that these are applied only after the base-tube with magnets has been encapsulated as are linings Stent-jackets and articulated stent-jackets placed in locations that pose conditions with inordinate potential to displace these have side-straps and/or end-ties as described below as an additional precaution against migration (lateral displacement along the substrate ductus). Stent-jackets serve the primary purpose of maintaining the patency of the substrate ductus and can serve a secondary purpose in attracting and thus targeting magnetic drug carriers into the encircled wall. Where stenting is uninvolved, impassable holding jackets, as addressed above in the section entitled Endoluminal Prehension of Miniballs and Ferrofluids, among others, and/or strongly magnetized miniballs or stays, as addressed above in the section entitled Drug-targeting Miniballs and Stays, among others, are preferable for attracting, trapping, or suspending drug delivering miniballs and attracting magnetic drug carrier particles.

As addressed above in the section entitled Concept of the Extraluminal Stent and the Means for its Placement, the use of an extraluminal magnetic stent to include both the extravascular and intravascular components, is generally limited to conditions that make its use advantageous if not imperative, usually to maintain patency of the affected ductus with minimal impact on normal function. Once placed in a minor surgical procedure involving a local incision without a transluminal component, the extravascular component of an extraluminal stent, consisting of the polymeric base-tube with magnets or a magnetized jacket alone can thereafter be used as would an impasse-jacket for magnetic drug or radionuclide targeting.

Should the ductus become stenosed, the intravascular component of the magnetic stent consisting of stenting miniballs can be placed transluminally at any later date. Stays, by contrast, whether medicinal, magnetized, radiation-emitting, and/or to serve as the intravascular component of a magnetic stent, are placed through the same access portal as the stent-jacket and then blocked from access unless the interposed stent-jacket is removed. As the circumductal (perivascular) component of an extraluminal magnetic stent, stent-jackets can be used to maintain the patency of any tubular anatomical structure that can be encircled (collared, mantled) without the need for more dissection than a side-slot or cut-outs would allow.

Virtually all stent-jackets, whether polymeric with applied bar magnets or made of magnetized metal, include apertures to provide contact between the adventitia or fibrosa and the surrounding chemical milieu as well as to discourage atherogenesis (see, for example, De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930). Apertures are omitted from FIG. 5 to allow the intraductal miniballs to be seen through the stent-jacket.

Any stent- or impasse-jacket can be prepositioned about the site of an incipient, advanced, or anticipated lesion or neoplasm, or one pending or following excision or resection to apply or support treatment not involving the placement of intraductal miniballs for an indeterminate period, if ever. Unlike an absorbable stent, once placed alone, a stent-jacket can be used at any future time. Unlike an endoluminal stent, an extraluminal stent leaves the lumen clear so that magnetic drug carrier particle or nanoparticle medication or radiation, for example, is not drawn to the stent but rather up against and into the lesion. Leaving the lumen clear, transluminal procedures are not hampered by the earlier placement of even several extraluminal stents.

For use with radiation-emitting miniballs and ferrofluids, the tissue of the ductus wall must be confirmed to be strong enough to prevent pull-through. A barrel-assembly can pass without obstruction other than might be posed by the lesion itself, which the barrel-assembly is equipped to negotiate by ejecting a lubricant, oscillating the muzzle-head, and/or through thermal or mechanical ablation. Any stent-jacket can have an outer radiation shield heat or adhesive bonded or plastic welded to it as a flexible outer layer containing overlapping shielding particulates of tungsten, platinum, gold, or an alloy thereof in a polymeric matrix, as addressed above in the section entitled System Implant Magnetic Drug and Radiation Targeting. Due to toxicity and scarcity, osmium and osmium-iridium alloys are not used.

Materials preferred for radiation shielding exclude lead, depleted uranium, and depleted plutonium as toxic, the first also decidedly suboptimal in shielding efficiency for the tiny dimensions involved. The shielding particulate is tightly but flexibly embedded in overlapping relation within a chemically isolating matrix layer of a rubbery polymer. Such a shield serves both to reduce the dose received by the ductus from externally applied radiation and to protect the tissue surrounding the ductus from radiation emitted by radioactive miniballs or stays, for example. Depending upon the type of radiation, a shield of overlapping particulate tungsten should almost never interfere with the ability to heat the magnets mounted about the base-tube of a polymeric or a ferrous metal base-tube for the purpose of warming the adventitia.

A radiofrequency alternating magnetic field can be used to warm the jacket and therewith, the adventitia with imaging used to view the muzzle-head, which can be aligned to the stent-jacket within the lumen to heat the lumen wall from within at the same time or for applying any emissive, ejective, ablative, or angioplastic process of which it is possible. Stent- and impasse-jackets can be heated to warm the encircled ductus for magnetic hyperthermia, or to heat miniballs or microspheres suspended by a jacket in the lumen to initiate or accelerate the release of a drug or its rate of uptake, or to heat drug carrier nanoparticles once drawn into the lumen wall whether as hyperthermia, to initiate or increase the rate of drug uptake, or to dissipate or accelerate the dissipation of absorbable components, or any of these purposes in combination.

Heat may be used to flow a bonding agent such as a protein solder or release a drug from a miniball or stay, for example. Outside the lumen, an absorbable jacket or component thereof is less exposed to the enzymatic and hydrolytic action that causes its breakdown. The application of heat can be used to dissipate or accelerate the rate of chemical action involved in its dissipation and thus compensate for the reduced exposure of extraluminal placement. Absorbable elements can be seeded, doped, or chemically incorporate a substance that when warmed is released and dissolves the breakdown of the structure incorporating it. Whereas a stent-jacket with a polymeric base-tube inherently provides thermal insulation for circumvascular tissue when the muzzle-head is used to apply heat, an intrinsically magnetized stent-jacket must have a polymeric layer added to its outer surface; conversely, the latter can serve as a bidirectional heat-sink when desired.

With or without a radiation shield, the outer surface of a stent-jacket with a polymeric base-tube can be increased in thermal insulation by adding a suitable polymeric coating. If drawing magnetically susceptible drug- or radiation-emitting carrier particles or nanoparticles by the jacket without magnetic retraction and thus without a transluminal component fails to preclude stenosis, then a barrel-assembly is used to introduce miniballs to stent the ductus with or without continuing the same or different medication and/or radiation. If miniballs are placed immediately, then the stent-jacket will also serve to draw supportive medication infused upstream. The advent of orally administered magnetic drug-targeting as addressed above in the section entitled System Implant Magnetic Drug and Radiation Targeting, will increase the applications for impasse- and stent-jackets.

Such prepositioning is accomplished when a ductus lumen-intramural lesion such as cancerous or atheromatous, for example, is discovered and to stage treatment by deferring a transluminal procedure until necessary, would spare the patient discomfort. To include larger ductus, such as the abdominal aorta, trachea, and gastrointestinal tract, a shielding stent-jacket can be used to protect the ductus from radiation applied externally to treat circumvascular tissue, or reciprocally, to protect the surrounding tissue from radiation, such as applied to the wall of the ductus. Involving no a transluminal component, the prepositioned jacket can be used to trap an oncolytic radionuclide- (radioisotope-) when infused upstream in microspheres or a ferrofluid. Once placed the jacket need not be recovered but can remain in place indefinitely where it will support retreatment at a later date.

Magnetic drug and radionuclide-bound drug carrier nanoparticle or microsphere targeting can be used to supplement or eliminate the requirement for intrinsic affinity-based chemical, physiological, or metabolic uptake of the drug or therapeutic substance by the target organ or tissue. The placement of small neodymium patch-magnets beside the lobes of the thyroid gland, for example, allows limitation to iodine-125 or iridium-192 isotope, for example, to be expanded to any magnetically susceptible or susceptibly carried substance (see, for example, Kaufman, H. L, Wadler, S., and Antman, K. (eds.) 2008. *Molecular Targeting in Oncology*, Totowa, N.J.: Humana Press) and a nonphysiologic agent used instead. By the same token, the bonding of a radionuclide to a substance normally assimilated by a certain organ, such as is Iodine-125 or 131 by the thyroid gland, historically intentional, can be averted were it introduced before it reaches the thyroid and drawn into other tissue.

Uptake by the thyroid gland could be much reduced if not eliminated and redirected to a kidney by injecting the ferrofluid-borne iodine isotope-bound drug carrier nanoparticulate directly into the renal artery, for example, with uptake by the kidney mechanically enhanced by a clasp-magnet or magnets, addressed above in the section entitled Clasp-magnets, fixed to the renal fibrosa. The delivery of drugs to the thyroid gland with or without iodine is by fastening tiny patch-magnets to the fascia overlying the infrahyoid and if necessary, sternocleidomastoideus muscles. These implants can be almost entirely absorbable, only small spherules of neodymium iron boron within a chemically isolating shell remaining. Incorporating ferrous metal in these spherules makes it further possible to use a powerful external electromagnet to extract these entirely out of the body, the tiny perforations readily disinfected and healing.

Extraction thus is effected with a very powerful pulse that accelerates the spherules to a velocity that shock perforates the integument at the triangle rather than pulls the tissue abaxially until its bursting strength is exceeded. If the condition treated warrants deeper dissection, impasse-jackets are placed at the inlets to the gland on the paired superior and inferior thyroid arteries and infrequently, the unpaired or paired thyroidea ima (artery of Neubauer, thyroid artery of Neubauer, lowest thyroid artery). These vessels anastomose over the surface of the gland; however, by singling out a particular artery for impasse-jacketing and/or the placement of a patch-magnet if applicable, the drug can be skewed toward the area predominantly supplied by that vessel.

Placement follows the condition treated, a unilateral condition generally suited to the unilateral placement of a holding jacket. Impasse-jackets to release a reversal agent to counter any residue are placed on the superior and inferior thyroid veins only to prevent adverse side effects when necessary. Where the drug or drugs must be administered three times a day, local release from a holding jacket is not feasible, the oral route requiring introduction as a ferrofluid devised to pass through the gut, the liver, and into the systemic circulation. Drugs not requiring frequent dosing can be directly injected into the external carotid and if necessary, the thyrocervical trunk, again based upon the regional concentration desired within the thyroid.

The severity of the condition must justify laparoscopic placement of a clasp-magnet or impasse-jacket; however, once accomplished, either can be left in place indefinitely for later use to cause the uptake by the kidney of the same of any other magnetic drug carrier bound substance. When the need for future reimaging is prognostic, Iodine 123 used for myocardial perfusion imaging can be concentrated with magnetic targeting that uses an impasse-jacket or clasp-magnet. Shielded stent-jackets, addressed above in the section entitled System Implant Magnetic Drug and Radiation Targeting, also allow the use of miniballs and stays of higher dose-rate, but lacking the grid of an impasse-jacket provided to allow noninvasive extraction with the aid of an external electromagnet, constitute an obstruction if these are to be extracted prior to decaying.

Unlike impasse-jackets, stent-jackets are not configured for extraction of the trapped or held miniball or miniballs through an open mesh wire grid with the aid of an external electromagnet, nor can these incorporate a radiation shield. Since a shielded jacket must be accessed for retrieval through a local incision and the radiation miniballs, whether ductus-intramural or suspended within the lumen can only be safely recovered with the recovery electromagnets in a barrel-assembly muzzle-head, local reentry for retrieval is avoided and vacated shielded stent-jacket left in place. Vascular radiation is typically obtained from phosphorus, yttrium, strontium, and rhenium radioisotopes, for example.

The shielding and extraction described herein accordingly allow dispensing with repeated invasive treatment in order to employ more intensive radiation (see, for example, Wade, J., Krause, B. J., Nusser, T., Kochs, M., and Höher, M. 2006. "Repeat Intracoronary Beta-brachytherapy Using a Rhenium-188-filled Balloon Catheter for Recurrent Restenosis in Patients who Failed Intracoronary Radiation Therapy," *Cardiovascular Revascularization Medicine* 7(1):2-6; Chu, W. W., Torguson, R., Pichard, A. D., Satler, L. F., Chan, R., and 4 others 2005. "Drug-eluting Stents Versus Repeat Vascular Brachytherapy for Patients with Recurrent In-stent Restenosis after Failed Intracoronary Radiation," *Journal of Invasive Cardiology* 17(12):659-662; Kuchulakanti, P., Torguson, R., Canos, D., Satler, L. F., Suddath, W., and 8 others 2005. "Optimizing Dosimetry with High-dose Intracoronary Gamma Radiation (21 Gy) for Patients with Diffuse In-stent Restenosis," *Cardiovascular Revascularization Medicine* 6(3):108-112; Eeckhout, E., Roguelov, C., Berger, A., Lyon, X., Imsand, C., Girod, G., and Coucke, P. 2005.

"Repeated Beta Irradiation for Failed Intracoronary Radiation Therapy in Patients with In-stent Restenosis," *Heart* 91(6):823-824; Waksman, R., Lew, R., Ajani, A. E., Pichard, A. D., Satler, L. F., and 9 others 2003. "Repeat Intracoronary Radiation for Recurrent In-stent Restenosis in Patients Who Failed Intracoronary Radiation," *Circulation* 108(6): 654-656).

An endoluminal stent difficult and risky to retrieve, a shielded jacket allows the use of more intense radiation than an endoluminal stent can be allowed to emit (see, for example, Cervinka, P., Stásek, J., Costa, M. A., Stursa, J., Fiser, M., and 5 others 2004. "Intravascular Ultrasound Study of the Effect of Beta-emitting ((55)Co) Stents on Vascular Remodeling and Intimal Proliferation," *Catheterization and Cardiovascular Interventions* 61(3):320-325; Cervinka, P., St'ásek, J., Costa, M. A., Stursa, J., Fiser, M., and 5 others 2004. The "Edge Effect" after Implantation of Beta-emitting (55Co) Stents with High Initial Activity," *Acta Medica* (Czech Republic) 47(1):37-42; Wardeh, A. J., Albiero, R., Kay, I. P., Knook, A. H., Wijns, W., and 7 others 2002. "Angiographical Follow-up after Radioactive "Cold Ends" Stent Implantation: A Multicenter Trial," *Circulation* 105(5):550-553; Kay, I. P., Wardeh, A. J., Kozuma, K., Foley, D. P., Knook, A. H., and 5 others 2001. "Radioactive Stents Delay But Do Not Prevent In-stent Neointimal Hyperplasia," *Circulation* 103(1):14-17; Albiero, R. and Colombo, A. 2000. "European High-activity (32)P radioactive Stent Experience," *Journal of Interventional Cardiology* 12(8):416-421; Coen, V. L., Knook, A. H., Wardeh, A. J., van der Giessen, W. J., De Pan, C., and 6 others 2000. "Endovascular Brachytherapy in Coronary Arteries: The Rotterdam Experience," *Cardiovascular Radiation Medicine* 2000 2(1):42-50; Hehrlein, C. and Kübler, W. 1997. "Advantages and Limitations of Radioactive Stents," *Seminars in Interventional Cardiology* 2(2):109-113; Hehrlein, C., Gollan, C., Donges, K., Metz, J., Riessen, R., Fehsenfeld, P., von Hodenberg, E., and Kübler, W. 1995. "Low-dose Radioactive Endovascular Stents Prevent Smooth Muscle Cell Proliferation and Neointimal Hyperplasia in Rabbits," *Circulation* 92(6):1570-1575).

Once placed, a stent-jacket as well as a magnet-jacket and an impasse-jacket, designed for the purpose, can serve as a holding jacket, as addressed above in the section entitled Concept of the Impasse-jacket, and below in the section entitled Miniball and Ferrojluid-borne Particle-impassable Jackets, or Impasse-jackets, that allows:

1. The magnetic targeting of drug carrier nanoparticles, as addressed above in the section entitled System Implant Magnetic Drug and Radiation Targeting, differential targeting achieved by graduating the amount of magnetically susceptible content of the drug carrier particles and/or the strength of magnetization of the stent-, magnet-, and/or impasse-jackets along the ductus, and 2. Stopping and retaining any miniball that enters the circulation upstream. Should this occur midprocedurally, the barrel-assembly will be positioned to move through the prepositioned stent-jacket using its recovery electromagnets to retrieve the seized miniball; otherwise, a stent-jacket is not configured for extraction.

If the radioisotope has a longer half-life than would decay within a safe interval, it is removed postprocedurally with the recovery electromagnets in a barrel-assembly. Once placed, a stent-jacket, impasse-jacket, or magnet-jacket constitutes a prepositioned magnetic drug-carrier particle targeting device (see, for example, Kumar, A., Jena, P. K., Behera, S., Lockey, R. F., Mohapatra, S., and Mohapatra S. 2010. "Multifunctional Magnetic Nanoparticles for Targeted Delivery," *Nanomedicine* 6(1):64-69). In this capacity, it may be used alone or with other such jackets for staged targeting, as addressed above in the section entitled System Implant Magnetic Drug and Radioisotope Targeting. The magnetic strength required to extract bloodborne drug carrier nanoparticles is greatest.

The magnetic strength required to extract blood-borne drug carrier nanoparticles is greatest. If the strength required exceeds that of pull-through obtained by testing as addressed below in the section entitled Testing and Tests, then an impasse-jacket is used. A stent-jacket placed as a radiation shield is thus seldom used with ductus-intramural implants to stent. An impasse-jacket is not designed for stenting and is used without ductus-intramural implants. Impasse-jackets, or impasse and extraction jackets, are not configured to present a local magnetic field of uniform magnitude from one end of the jacket to the other. While the two types of jacket share some capabilities such as supporting magnetic drug-targeting requiring less tractive force, attempting to consolidate the two into a single device only degrades the special capabilities of both.

When despite smooth encapsulation, because of its thickness and/or prominences, a stent-jacket mounting magnets about a length of polymeric tubing such as shown in FIGS. 2 thru 7 would encroach upon and irritate tissue surrounding the ductus, an alternative base-tube made of spring strip metal intrinsically magnetized normal (radially, perpendicularly) to the longitudinal axis of the ductus is used. Such a base-tube, coated or encapsulated for chemical isolation if necessary, allows the small magnets used with a polymeric base-tube to be eliminated, giving a thinner profile or cross-section. When compliance with the action in the ductus requires the intrinsically magnetized stent-jacket to be made of stock too thin to provide the strength of magnetization required, the base-tube or another of more compliant plastic is encapsulated within a polymer layer containing magnetized neodymium iron boron lanthanoid.

Reciprocally, when the strength of magnetization required in all metal stent-jacket necessitates the use of tube stock that is too thick to comply with the action in the ductus and the coating method alluded to above is not employed, the jacket must incorporate spring hinges as in ordinary impasse-jackets. Where a somewhat greater thickness can be fitted, a metallic stent-jacket with intrinsic magnetization can enclose a radiofrequency resonant circuit between inner and outer surfaces that can be heated by means of an extracorporeal source of radiofrequencies, the heat used to treat the ductus or miniballs implanted within it. Another method for achieving the compliance required is that addressed just below as applied to impasse-jackets whereby spring-hinges join two semicylindrical base-tube halves which need not be flexible and can therefore be made as thick as the magnetization requires.

That hybrid type stent-jackets with spring hinges and a surrounding or outer layer of polymer embedded lanthanoid or another that consists of a length of lanthanoid-embedded polymer tubing are also possible is considered obvious. With openings to reduce enclosure of the adventita, such stent-jackets resemble impasse-jackets, as addressed below in the section entitled Miniball and Ferrofluid-borne Particle-impassable Jackets, or Impasse-jackets; however, impasse-jackets must provide the resistance to deformation under the pull of a powerful external electromagnet required for miniball extraction, and are limited to magnetization that to prevent the loss of a suspended miniball increases toward the longitudinal center and does not extend out to the ends, or margins. For application where the open mesh wire grid can be adequately magnetized over a sufficient length for stenting and strong enough to allow extraction, such an impasse-jacket can serve as a stent-jacket without radiation shield.

Broadly, attempting to combine the features of stent-jackets, made to retract implants within the lumen wall, and impasse-jackets, made to suspend miniballs and magnetically susceptible particles within the lumen and allowing these to be noninvasively extracted, into a single device has the effect of degrading the performance of the device for both functions. Distinct and hybrid types all require a moisture barrier-coated viscoelastic polyurethane foam lining. Made of stock sufficiently thin, an intrinsically magnetized metal base-tube is preferable for use where there may be little clearance around the ductus for even small magnets with rounded corners, as arises, for example, in peripheral arteries, which course through a compartmentalized sheath amid other fascial compartments. Access is by dissection that to the extent possible moves to the pertinent septum with minimal cutting of muscle.

Such strip-spring ferrous metal base-tubes with intrinsic magnetization oriented transversely to the long axis of the tube are not to be conflated with the alternative spring strip nonmagnetic metal alloy and polymer combinations for use with magnets mentioned below. All stent- and shield-jackets as well as some magnet- and clasp-jackets are provided with a moisture barrier-coated viscoelastic polyurethane foam lining, and all but shielded apertures, and side-straps, and/or end-ties to prevent migration as necessary, and are inserted with a stent-jacket insertion tool. Thin spring metal stock can be used to make a base-tube or used as an internal reinforcement to an outer layer or layers of the polymeric materials to be specified.

Nonmagnetic magnet-mounting metallic base-tube materials made of cobalt-nickel-based or copper-beryllium alloy strip sheeting, for example, with good fatigue resistance can be used as base-tube materials, as can a specialty nonmagnetic stainless strip spring steel such as Sandvik Aktiebolag 13RM19. Encapsulation for chemical isolation is based upon potential toxicity. That to achieve the desired restorative force, for example, the base-tube might combine layers of different metallic and polymeric materials is obvious. A ferrous metal strip spring base-tube magnetized normal to the longitudinal axis of the ductus and encapsulated for chemical isolation allows elimination of the small magnets used with a polymeric base-tube.

A polymeric layer applied to the outer surface of a stent-jacket whether shielded but not an impasse-jacket provides thermal insulation for the surrounding tissue when the jacket is intentionally heated (well below the Curie temperature) by placement in a radiofrequency alternating magnetic field. Increasing the thickness of the encapsulation coating can serve this purpose as well. Heating can be to warm the ductus noninvasively for hyperthermia, accelerate the dissolution and uptake of medication held by the jacket within the lumen, flow a protein solder outer coating or accelerate the initial setting time of a cement applied to the miniballs or stays, or accomplish followup thermoplasty to eliminate intimal or medial hyperplasia, for example.

Whether the base-tube is metallic, polymeric, or layers of each, the need for apertures and a lining of moisture barrier-coated viscoelastic polyurethane foam as explained in the sections above entitled Summary Description of the Invention and Accommodation of the Adventitial Vasculature, Innervation, and Perivascular Fat applies. Individual subsidiary stents, or sub-stents, chain-stent as addressed in the section below entitled Sectional, or Chain-stents, Segmented and Articulated, can have base-tubes of different materials. A chain-stent is assembled of sub-stents each selected on the basis of the segment it is to encircle. A chain combines the antimigrative value of each component. That is, each substent and/or impasse-jacket contributes to the retentive forces stabilizing the formation as a whole. At the same time, it allows each sub-stent or impasse-jacket to be matched to the medical condition at its respective location.

Numerous materials are available for use as the base-tube, and sensitivity reactions to different materials through patch testing should be performed before implanting the jacket or jackets. Since the foam lining prevents contact with the substate ductus, contact is substantially limited to the outer surface of the jacket when the magnetized content is not embedded or sandwiched in the base-tube. Direct contacy easily avoided, complications that arise with base-tubes made of polymeric materials such as silicone elastomer involve contact of the material directly upon cut tissue surfaces, especially in a patient who is allergic to the material (see, for example, Lee, Y., Song, S. E., Yoon, E. S., Bae, J. W., and Jung, S. P. 2017. "Extensive Silicone Lymphadenopathy after Breast Implant Insertion Mimicking Malignant Lymphadenopathy," *Annals of Surgical Treatment and Research* 93(6):331-335; Zambacos, G. J., Molnar, C., and Mandrekas, A. D. 2013. "Silicone Lymphadenopathy after Breast Augmentation: Case Reports, review of the Literature, and Current Thoughts," *Aesthetic Plastic Surgery* 37(2):278-289; Winkler, P. A, Herzog, C., Weiler, C., and Krishnan, K. G. 2000. "Foreign-body Reaction to Silastic Burr-hole Covers with Seroma Formation: Case Report and Review of the Literature," *Pathology Research and Practice* 196(1):61-66), and the lack of openings along the sides (De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930), none of which applies to the base-tubes described herein, which if ever made of a silicone elastomer, would be isolated from the surrounding tissue.

The issue of adverse tissue reaction when the implant is sterile is addressed above in the section entitled Significance of SterileAntixenic Immune Tissue Reaction. A separate stent-jacket consisting of a single length of side-slit tubing is referred to as simple, one of a succession of separate stents connected together in a chain as articulated or jointed with each component stent-jacket a substent, and a succession of stent-jackets cut into a continuous length of tubing, segmented. Whereas an articulated chain-stent is assembled or compiled of individual stent-jackets as manufactured for the individual application, a segmented stent is manufactured as continuous thus and trimmed for the individual application. Trimming consists of snipping away nonessential intervening substents, snipping away a strip of material adjacent to the side-strip to create a side-slot, or cutting a single or successive number of substents off the continuous length as manufactured, for example.

Thus, both simple and jointed stent-jackets can include full round substents to fully encircle the ductus, and partially round or eliminations of substents to avoid attachments or adhesions to substrate or adjacent tissue, for example. To prevent injury to the vasculature supplying the ductus, stent- and impasse-jackets are lined with visco-elastic, usually, polyurethane moisture barrier-coated viscoelastic polyurethane foam. This lining leaves clear perforations or grid openings, so that in a stent-jacket, only 'air holes' are not lined, whereas in an impasse-jacket, the lining is placed only at the margins and a few circumferential grid lines as necessary to prevent contact with the adventitia.

The base-tube is elastic, slit along the side, and sized to accommodate the pulse or peristalsis. The diameter of the jacket is based upon the quiescent diameter of the ductus and must expand to the maximum distended diameter without posing resistance. The magnetic traction exerted upon the ductus intramural implants (miniballs or stays) is no more than that essential to preserve retraction of the ductus against the internal surface of the stent-jacket. Exceptionally, when the jacket is additionally to draw drug-carrier particles or miniballs from the lumen contents, usually blood, the magnetic strength is increased as necessary but not so much that pull-through or tunical delamination would result.

The untreated resistance of the tissue to failure thus is obtained by means of in-situ testing as addressed below in the section entitled Testing and Tests, and the prospective resistance following different treatments through previous experimentation. When the malacotic condition is more extensive, avoiding pull-through may necessitate the use of a clasp-jacket lined with a surface texture and a bonding agent that includes tissue engineering scaffolding material to support tissue infiltration and encourage the development of a permanent bond. The clasp-jacket is extended lengthwise to encircle tissue of normal strength.

The spandex base should include perforations as not to completely close off the surface of the ductus. Since both a ductal component consisting of a clasp-jacket or stays and the extraductal stent-jacket can be inserted through a single incision, the need for a second procedure to allow sufficient time for the necessary strength of adhesion to develop before the stent-jacket can be inserted is sought to be avoided. When the malacotic condition is less extensive, stays can be coated with tissue infiltration and bonding agents such as delineated in the section below entitled Medication-coated Miniballs, Stays, and Prongs with a Heat-activated (-melted, -denatured) Tissue Adhesive-hardener or Binder-fixative, among others.

If deeply situated and used with a stent-jacket having a base-tube of intrinsically magnetized spring metal, then placing the patient in a radiofrequency alternating magnetic field can be used to accelerate bonding by warming the jacket once in position. If not too deep, warming is by electrical blow drying. As the initial retractive force required to overcome the stenosis or collapse increases, the risk that the adventitia will delaminate from the subjacent tissue increases as well. However, the mild resistive force of stenting retraction should cause the smooth muscle and connective tissue in a ductus that had stenosed to strengthen.

Furthermore, whether the intrinsic strength of the wall will eventually become sufficient to preserve the integrity of the wall without any exogenous means of support, to reduce the risk of inter- or intratunical delamination, various tissue hardener and binder fixative agents, to include cements, protein solders and the use of implants with surface textures devised to encourage tissue infiltration are provided. Coating the internal surface of the base-tube with a cement that becomes inelastic upon setting should be disallowed as reducing the freedom of expansion and contraction. The moisture barrier-coated viscoelastic polyurethane foam lining and in some instances, the addition of a soft gauze lining as an additional antimigratory measure also contribute to mobility.

Furthermore, given the adaptive responses exhibited by many ductus, notably arteries (see, for example, Dirsch, O., Dahmen, U., Fan, L. M., Gu, Y. L., Shen, K., Wieneke, H., and Erbel, R. 2004. "Media Remodeling—The Result of Stent Induced Media Necrosis and Repair," *Vasa* 33(3):125-129), depending upon the medical condition and previous treatment of the artery, any patenting restraint at the interface separating the adventitia from the outer surface or magnetic field-projecting layer in the base-tube is likely to prompt a compensatory strengthening of the ductus. Some strengthening of the smooth muscle to less than a hyperplastic extent is desirable. Patenting restraint will tend to be less at the side-slit or side-slot. A through-thickness magnetized stainless steel base-tube can be made thinner to avoid encroachment on neighboring tissue, and lined with polyurethane foam, is less likely to provoke local adverse tissue reactions.

Strengthening should result in some thickening of the wall phenotype but not a substantial proliferative hyperplasia (see, for example, Richard, M. N., Deniset, J. F., Kneesh, A. L., Blackwood, D., and Pierce, G. N. 2007. "Mechanical Stretching Stimulates Smooth Muscle Cell Growth, Nuclear Protein Import, and Nuclear Pore Expression Through Mitogen-activated Protein Kinase Activation," *Journal of Biological Chemistry* 282(32):23081-23088; Qu, M. J., Liu, B., Wang, H. Q., Yan, Z. Q., Shen, B. R., and Jiang, Z. L. 2007. "Frequency-dependent Phenotype Modulation of Vascular Smooth Muscle Cells Under Cyclic Mechanical Strain," *Journal of Vascular Research* 2007 44(5):345-353). The stent-jacket lining and miniballs or stays can be coated with counterproliferative medication (see, for example, Sakamoto, K., Murata, T., Chuma, H., Hori, M., and Ozaki, H. 2005. "Fluvastatin Prevents Vascular Hyperplasia by Inhibiting Phenotype Modulation and Proliferation Through Extracellular Signal-regulated Kinase 1 and 2 and p38 Mitogen-activated Protein Kinase Inactivation in Organ-cultured Artery," *Arteriosclerosis, Thrombosis, and Vascular Biology* 25(2): 327-333).

The material of the internal surface of the base-tube can be treated to suppress sliding migration along the ductus by incorporating a frictional base-tube lining that is textured or made of gauze, for example. The application of a tissue sealant to the internal surface of the base-tube, such as to seal a perforation left by a fistula, can prevent movement between the ductus and base-tube at and around the bond, and is likely to disintegrate according to the turnover rate of the tissue; the approach is can be used to gain time where the temporary fixation would allow healing. Where potentially fistulizing friction against an adjacent ductus is a possibility, the stent-jacket with bar magnets if any can be encapsulated as perforated within a tissue compatible and enzyme resistant cushioning coat of a rubbery or plastisol-like material.

A soft silicone rubber or thermoplastic polyurethane, such as Bayer Material Science Texin or Desmopan® can also incorporate ferrous particulate to expedite warming as well as chemically isolate the base tube. Such a coating can be formulated to adjust the elasticity of the base-tube. At a curing temperature of around 350 degrees Fahrenheit, such a coating is applied at well below the Curie temperature of the magnets, which depending upon the exact lanthanoid, is around 590 degrees Fahrenheit. Although durable materials are used for the base-tube, in a young patient, such a barrier can be used to further forestall any breakdown and the formation of base-tube microfractures that would progressively reduce its resilience, and if containing embedded particles, for example, break the chemically isolating seal.

Such an outer coating can also be used to a. Cushion the already rounded edges of the magnets, further protecting against abrasive injury, b. Whether to cover the entire surface of the stent-jacket as by adding barium sulphate to the resin, or limited to its ends, side-slit, and/or magnets as with tantalum, incorporate radiological contrast dye markings, c. Contain embedded lanthanoid or radiation shielding particles such as tungsten, and d Enhance adhesion to the internal surface of a lining, such as one consisting of a solid protein solder tissue adhesive as addressed below in the section entitled Specification of Cyanoacrylate Tissue Sealants and Bonding Agents and/or a double-wedge lining as addressed below in the section entitled Double-wedge Stent- and Shield-jacket Rebound-directing Linings.

The linings prescribed herein are sufficiently compliant circumferentially that an internal surface need not be made of a low friction fluoropolymer, for example, to accommodate the free movement of the ductus when changing in gauge as would bode against antimigratory stability. Implantable coatings continue to be advanced (see, for example, Ding, N. 2007. "Poly(vinyl Acetal) Coatings for Implantable Medical Devices," U.S. Pat. No. 7,294,329). The restorative force of the stent-jacket base-tube, which is the product of the intrinsic elastomeric properties of the material and its thickness, or if a coextrusion, the combination of materials and thicknesses, is selected for close compliance with the pulse or smooth muscle action passing through the ductus and not so resistant to such action that the margins (end rims) dig into the outer surface of the ductus. In some instances, chain-stents are used to achieve this action.

The stent-jacket lining must possess the elasticity to yield at the point of impact of the miniballs when placed at the correct angle at the correct exit velocity prior to implantation and not present a mechanical or chemical irritant on its inner surface or at its margins. Linings to protect against perforations resulting from errors in these factors are addressed below in the section entitled Double-wedge Stent- and Shield-jacket Rebound-directing Linings. The avoidance of the lumen made possible by using stays averts significant sequelae (see, for example, Tesfamariam, B. and DeFelice, A. F. 2007. "Endothelial Injury in the Initiation and Progression of Vascular Disorders," *Vascular Pharmacology* 46(4):229-237). Stay insertion tools are designed to allow stay insertion with minimal if any compression of the ductus as would bend the intima. The deformation in the cross section of a vessel by atheromatous tissue that can promote thrombogenic turbulent flow is reduced by magnetic traction to the circular internal surface of the stent-jacket.

The base-tube of an extraluminal stent-jacket can be punched or slotted to expose the outer surface of the ductus to its normal environment or to reduce the resilience of a base-tube when encapsulated or equipped with a lining, or to provide clearance for a portion of the tunica fibrosa or adventitia, for example. Ideally, both the base-tube and encapsulating layer added to the base-tube to provide a softer outer surface and unitize the magnets and base-tube consist of materials established to remain inert in the internal environment and free of adverse tissue reactions, as addressed above in the section entitled Tissue Acceptance of Ductus-Intramural Implants. Should the underlying base-tube be implicated in adverse tissue reactions, then rather than to expose the base-tube, the outer layer is applied after apertures or perforations have been punched or cutouts for nerves or vessels nibbled away. Suitable materials are addressed below in the section entitled Internal Environment-resistant Base-tube Polymers, Metals, and Combinations Thereof.

A side-slit or full-round stent-jacket is shown in FIGS. 2 thru 5, 7 and 9, the parts thereof enumerated in the section above entitled Description of the Preferred Embodiments. A full round stent-jacket is used when the vessel or duct can be completely encircled, allowing miniballs or stays to be subadventitially or medially implanted and retract the ductus wall entirely about the periphery. When stenosis or collapse is eccentric, a full found stent-jacket is still placed as countermigratory. A partial stent-jacket, or partially round or side-slotted stent-jacket, consists of the same parts with a side-slit widened as a slot, and is shown in FIG. 6 with a perforated base-tube. When the side-slot is used to avoid needlessly dissecting subjacent tissue such as to straddle a running attachment, for example, the tissue interposed in the side-slot stabilizes the jacket. Other countermigratory measures include, as necessary, side-straps, end-ties, and nonsliding linings.

In the trachea, for example, depending upon the suitability of a stent-jacket or chain-stent over the affected segment, subcutaneous or suprapleural patch-magnets, as addressed below in the section entitled Subcutaneous, Suprapleural, and Other Organ-attachable Clasp- or Patch-magnets, can be used to retract miniball or stay implants. Tangential traction is avoided through radial alignment of the subadventitially or medially placed miniballs or stays and the bar magnets mounted about the base-tube. A benefit in the use of an intrinsically magnetized base-tube is the radial neutrality that eliminates any need for radial alignment, making such a base-tube more convenient to place when retraction is to be eccentric (not radially symmetrical).

With a discretely magnetized stent-jacket, radially aligning more sparsely placed subadventitial or medial miniballs or stays with the bar magnets mounted about the base-tube minimizes nonradial or tangential vectors. To reduce the risk of tunical delamination and pull-through, the radially aligned magnets should exert the least functional tractive force as determined by in situ testing, addressed below in the section entitled Testing and Tests. An advantage of intrinsically or quasi-intrinsically magnetized stent-jackets, as described above in the section entitled Types of stent-jacket, is uniform magnetic traction over the entire surface of the stent-jacket. In an intrinsically magnetized stent-jacket, the magnetic tractive force is due to the magnetic mass and domains of the ferromagnetic material, which in quasi-intrinsically magnetized stent-jackets, is contained within the particulate embedded in the matrix.

Whether contained within particles, domains are in effect many more and more closely juxtaposed permanent magnets that project force with a uniformity that is unapproachable using discrete bar magnets. The uniformity of magnetization in a quasi-intrinsically magnetized stent-jacket depends upon the density and distribution pattern of the embedded magnetized particulate. A large number and proximity of poles reduces the magnitude of the tractive force and minimizes the concentration of traction on those ductus-intramural implants radially axial to each pole and circumjacent thereto. Except in exceptional circumstances where the tractive force is intended to be focused, this eliminates the need to radially align the magnetic poles to the implants, making such a base-tube more convenient to place.

If lesion eccentricity or a malacotic condition recommend avoiding implantation in a certain arc or segment, then that area is not implanted, and the use of a stent-jacket which more uniformly distributes a mild tractive force, that is, one intrinsically or quasi-intrinsically magnetized, is used to reduce pulling at the affected area by the adjacent implants. Absorbable base-tube and matrix materials with the mechanical properties needed are addressed below in the section entitled Absorbable Base-tube and Stent-jacket, Miniball, Stay, and Clasp-magnet Matrix Materials. In any stent-jacket or base-tube, sufficiency of resilience denotes synchronous expansion and contraction with the ductus, hence, continuous apposition of ductus and jacket with countermigratory contact and constancy of tractive force maintained.

While expansion inserts, as addressed below in the section entitled Expansion Inserts Absorbable, Meltable, and Comminutable for Time-discrete Decremental Contraction of Stent-Jackets, have been shown as applied to side-slit, or full-round stent-jackets, these are no less applicable to side-slotted, or partially-round stent-jackets. In using a multiple barrel-tube barrel-assembly, less than fully circumferential discharge can be accomplished by blanking out one or more of the barrel holes in the rotary magazine clip. The manufacture of barrel-assemblies with muzzle-heads having eccentric muzzle-ports or muzzle-ports limited to a certain arc about the periphery is negated by the ability of the turret-motor to rotate the muzzle-head with or without multiple muzzle-ports.

When diagnosed early, a nonmagnetic loosely woven spandex or perforated resilient polymer based stent-jacket with a side-slit and stretch compliant side-straps as shown in FIG. 15 can be applied to an incipiently aneurysmal abdominal aorta, for example. A jacket of this kind applied thus are ancillary to the central content addressed herein. The object in such treatment is to actively truncate enlargement preserving nonthrombogenic laminar flow rather than to passively watch and wait, depending upon the cause, allow the vessel an opportunity to recover, and avoid the eventual need for insertion of an endoluminal stent-graft with the risks of an endoleak, kinking, thrombosis, angulation, and migration, or excision and insertion of a synthetic graft (*The Merck Manual of Diagnosis and Therapy,* 18th edition, page 740).

Usually associated with distributed vascular disease, early correction should not affect a propensity for spread or the separate appearance of an iliac or femoral aneurysm. A circumvascular jacket is not susceptible thus, leaves the lumen free of a foreign object, need flex to a lesser extent, can have small side branches should the aneurysm extend to the renal arteries, and is removable. It has been demonstrated in an endovascular stent-graft bifurcated for extension down into the iliac arteries that the ability to flex improves the outcome of an abdominal aortic aneurysm (Arko, F. R., Lee, W. A., Hill, B. B., Cipriano, P., Fogarty, T. J., and Zarins, C. K. 2001. "Increased Flexibility of AneuRx Stent-graft Reduces Need for Secondary Intervention Following Endovascular Aneurysm Repair," *Journal of Endovascular Therapy* 8(6):583-591). Flexion should not be confused with laxity that allows continued enlargement of the aneurysm, as addressed above in section I1 entitled General Considerations to Include Insertion.

Such nonmagnetic wrap-surround stent-jackets can be longitudinally split and optionally connected together to straddle points of flexion. Peripheral arterial aneurysms are not reported to appear at points of flexion. In a magnetic stent-jacket, the resilience of the base-tube for longitudinally mounting the tiny bar magnets varies with the material and its dimensions. The tubing can be simple or compound (coextruded), expanding the range of properties to include the restorative force. The addition of an internal layer within a stent-jacket to moderate rebound when the stent-jacket is placed prior to discharge in order to prevent perforation, for example, is addressed below in the section entitled Sequence of Stent-jacket Placement and Implantation.

Means for preventing the escape of a miniball are addressed below in the sections entitled Multiple Radial Discharge Barrel-assemblies with One- to Four- or More-way Radial Discharge Muzzle-heads and Embolic Trap Filter in Radial Discharge Muzzle-heads for Use in the Vascular Tree. Prior to placement about the implanted site, the inner surface of the stent-jacket can be wetted with a coagulant, antibiotic, anti-inflammatory, tissue reaction counteractant, or other medication, the use of an adhesive generally temporary. Unless made of an intrinsically magnetized material, one encapsulated within a soft bioinert plastic resin that sufficiently blunts the exposed edges of the bar magnets, or the latter with embedded magnetized particulate, the edges the magnets are rounded prior to plating and replating, or plating and Microfusion®.

The latter is a proprietary plasma-based ion deposition or physical vapor thin film vacuum coating form of metastable phase synthesis available from Implant Sciences Corporation, Wakefield, Mass. Replating or a process such as sputtering or Microfusion®, for example, can be used to cover over any microfractures that remain following plating, as well as to intensify radiopacity (see Sahagian, R. 1999. "Critical Insight: Marking Devices with Radiopaque Coatings," *Medical Device and Diagnostic Industry Magazine*, Canon Communications, May 1999 available at http://www.devicelink.com/mddi/archive/99/05/011.html and http://www.implantsciences.com/pdf/orthodontic.pdf).

Microfusion® or a similar process is an outgrowth of nonplasma (discrete, directed beam) ion deposition (see, for example, Hirvonen, J. K. 1991. "Ion Beam Assisted Deposition," *Material Science Reports* 6 (6):215-274; Nastasi, M. A., Mayer, J. W., and Hirvonen, J. K. 1996. *Ion-Solid Interactions: Fundamentals and Applications*, New York, N.Y.: Cambridge University Press). Both plating and ion deposition are convenient methods for bringing implants up to a certain mass to adjust the discharge momentum, for example. Compared to replating, Microfusion® or a similar process generally allows equal if not finer control over deposition thickness, hence, mass.

Such a process can be used for the primary object of providing high radiopacity markings in lieu of painting or banding, the inclusion in components of a metal powder based paint such as barium or tungsten, electroplating, chemical vapor desposition, high vacuum thin film coating, cold process physical vapor deposition, plasma vapor, or sputter-coating, for example, wherever the marking of components described herein is necessary. A ductus that varies in diameter or treatable condition along its length can be treated with a sectional or chain stent-jacket, which can also incorporate impasse-jackets as necessary, mentioned above.

Such a train consists of distinct unit jackets, so that ordinarily, a change in diameter of the treated ductus is not treated with a continuous jacket of flaring diameter but sub-stents of different diameter at intervals. Where a continuous jacket is necessary, one longer with a thicker moisture barrier-coated viscoelastic polyurethane foam lining is used. The rate of change must be high to require that the thickness of the foam lining be cut to change likewise. Atheromatous disease tends to favor entries into bifurcations and openings to side branches, or ostia, as points of increased shear stress. To clear a side-branch, the stent-jacket expansion slit is nibbled away with complementary semicircles into the opposing edges.

This is generally done at the time of insertion when the jacket can be placed against the ductus to confirm the diameter and position of the hole required. To clear a bifurcation, a separate stent-jacket is positioned about each branch; however, when to properly fit these makes it necessary, a Y-shaped jacket with a Y-shaped side-slit is used. Similarly, stent-jackets can be made in shapes other than cylindrical, such as one tee-shaped to encircle a trunk and branch. Silicone-urethane copolymers are antioxidative, elastic, and resilient at body temperature as to exhibit 'memory,' have a coefficient of friction that combined with the other countermeasures to be described are consistent with resistance to migration, and have already met the federally mandated criteria for implantable material.

Bioinert polymeric materials suitable for the base-tubes of stent-jackets with magnets mounted to the outer surface are numerous, and include silicone, expanded polytetrafluororethylene, polyfluoroethylene, other fluoropolymers, polyetherurethane, polycarbonateure-thane, polysiloxaneurethane, silicone-polyurethane copolymers and hydrogenated poly(styrene-butadiene) copolymer. Recent improvements in these materials such as those addressed below in the section entitled Internal Environment-resistant Base-tube Polymers, Metals, and Combinations Thereof mean that replacement should not become necessary for years if ever. Clearance by the neighboring anatomy permitting, varying the restorative force required to fit the ductus treated is readily accomplished by changing the material or wall thickness of the tubing.

I3. Order of Stent-Jacket Placement

I3a. Circumstances Recommending the Use of a Shield-Jacket or Preplacement of the Stent-Jacket An absorbable (temporary) or nonabsorbable shield-jacket, stent-jacket, or impasse-jacket with absorbable shield can be placed prior to initiating discharge. In addition to serving as a physical barrier or shield, the jacket can be made remotely heatable, allowing the ductus to be warmed, the release or uptake of a drug to be accelerated, or the jacket to be disintegrated on demand, for example. Preplacement of the jacket can serve to avert:

1. Perforation (the penetration through-and-through) or puncture (partial penetration) through the ductus wall. 2. The striking of a vulnerable structure, such as a nerve, ganglion, or vessel near to the treated ductus on perforation or by approximation of the adventitia at the point where the lumen wall has been struck or punctured within.

3. Rebound of the miniball to a nonfunctional (nonretracting) location or even the lumen, avertable through the use of a stent-jacket with double-wedge lining described below in the section entitled Double-wedge Stent- and Shield-jacket Rebound-directing Linings; or to 4. Counteract abrupt closure with or without vasospasm, or reflexive contracture, whether due to endothelial dysfunction, reflexive of ballistic insertion, or both when vasodilators alone cannot be depended upon; or 5. Provide a backing against which the adhesive or tissue hardening agent injected wall can be compressed by the injecting barrel-assembly or radial projection catheter within the lumen made necessary by internal weakening or delamination within the wall of the ductus. The prevention of perforation is most important when the lumen contents are septic, as in the colon or an artery when the blood is infected or suspected to transport metastatic cells shed by a primary tumor. The risk of perforation is much less with stays, which are inserted from outside the ductus.

Other reasons for placing the stent-jacket prior to discharge are to:

6. Take advantage of the outward tractive force exerted by the stent-jacket in order to prevent the dislodging of an implanted miniball, especially when the need arises to pass an implanted miniball with the tractive recovery electromagnets energized.

7. Take advantage of a tantalum coated stent-jacket as an imaging marker of high radiopacity to reduce any difficulty in locating and observing the work site.

8. Preclude a weakening of the luminal wall by implantation sufficiently dense, such as miniball discharge under automatic positional and discharge control to evenly distribute the field force, that if eccentric could progress to a saccular, or if circumferential, a fusiform aneurysm.

9. Magnetically attract drug carrier nanoparticles or magnetically susceptible microspheres at any time after placement.

10. Shield the surrounding tissue from radiation when the stent-jacket includes radiation shielding and is used to support magnetically targeted radioisotope-bound drug carrier magnetically susceptible nanoparticles or microspheres.

11. Cinch about the ductus with a jacket having side-straps, thereby reducing its motility, allowing greater discharge accuracy; and 12. To allow the use of an oversized muzzle-head for compression under heat supplied by a nose radiofrequency probe or other type thermoplasty window when used with a preplaced stent-jacket to fuse the laminae, when imaging confirms delamination in the wall of the ductus (see, for example, Kaplan, J., Barry, K. J., Connolly, R. J., Nardella, P. C., Hayes, L. L., and 4 others 1993. "Healing after Arterial Dilatation with Radiofrequency Thermal and Nonthermal Balloon Angioplasty Systems," *Journal of Investigative Surgery* 6(1):33-52; Resar, J. R., Wolff, M. E., Hruban, R. H., and Brinker, J. A. 1993. "Endoluminal Sealing of Vascular Wall Disruptions with Radiofrequency-heated Balloon Angioplasty," *Catheterization and Cardiovascular Diagnosis* 29(2):161-167; Barry, K. J., Kaplan, J., Connolly, R. J., Nardella, P., Lee, B. I., Becker, G. J., Waller, B. F., and Callow, A. D. 1989. "The Effect of Radiofrequency-generated Thermal Energy on the Mechanical and Histologic Characteristics of the Arterial Wall in Vivo: Implications for Radiofrequency Angioplasty," *American Heart Journal* 117 (2):332-341).

The increase in susceptibility of an already diseased ductus wall to aneurismal failure following an atherectomy and/or the placement of ductus intramural implants is unpredictable; however, such risk is minimized by preplacement of the stent-jacket, which can precede not only ballistic (but not stay) implantation, but angioplasty. This condition is most prominent when miniballs are implanted in a close formation under machine control precisely to achieve a uniform distribution of the tractive force, in which case an intrinsically or quasi-intrinsically magnetized stent-jacket is preplaced as the complement to field uniformity. In such instances, the foam lining should be rather firm to support the weakened wall. Outward failure in the form of delamination is likewise discouraged.

An endoluminal stent is incapable of providing inward constraint, and since it must exert radially outward force to avoid migration, would promote failure. The multiple reasons for preplacement notwithstanding, in locations when perforation is of less concern, placing the jacket only after discharge eliminates the possibility of rebound, which may require extraction, increasing procedural time. Thus, preplacement of a stent-jacket may serve purposes related or unrelated to extraluminal magnetic stenting; depending upon the application, such placement can be accomplished where no ductus-intramural implants are to be placed, or at any time before or after ductus-intramural implants are placed, whether drug or radiation miniballs or magnetically susceptible nanoparticle-bound radiation drugs, for example, introduced into the bloodstream, for example.

Stent-jacket placement can be followed by the infixion of miniballs or introduction of drug carrier nanoparticles, for example, immediately or at any later date. When part of a magnetic stent, this makes possible the targeting of followup adjuvant medication, for example, at any time without the need for any additional measure. A temporary (absorbable) stent-jacket placed solely to shield against a perforation or punching injury is best eliminated prior to withdrawal by accelerating dissolution through the use of the heating elements in the muzzle-head, to include heat-windows. The preplacement of a more strongly magnetized or magnetically susceptible stent-jacket reduces the risk of miniball rebound into the lumen, making the preplacement of a radiation shielded stent-jacket a valuable precaution when magnetically targeted radioisotope-bound drug carrier nanoparticles or radioactive stays or miniballs are used.

Due to the small diameter of miniballs and the intrinsic ability of most ductus to seal a perforation quickly, a perforation, should it occur, should seldom pose a problem. Absorbable stent- and impasse-jackets leave behind the moisture barrier-coated viscoelastic polyurethane foam lining as an innocuous vestige. Those that include radiation shielding can be made fully absorbable, as addressed above in the section entitled System Implant Magnetic Drug and Radiation Targeting, among others. Melting a solder coating applied to a ductus-intramural implant may require heat shielding to protect the surrounding tissue, for example. Preplacement of a stent-jacket can therefore be used to shield surrounding tissue from an injurious temperature or radiation, whether along a certain arc or entirely about the substrate ductus.

In arteries, however, platelet blockade will have been administered to avert the risk of thromboembolism due to the rupture of vulnerable plaque or the punctures at the points of miniball entry, and the peak in blood pressure with each systole means that a perforation could result in bleeding (extravasation, exsanguination) that must be prevented. A stent-jacket placed prior to miniball discharge is usually intended to block or shield against any miniball that would perforate through the outer fibrosal or adventitial tunic and into the surrounding tissue or body cavity. Should a miniball perforate, it becomes trapped in the foam lining, and embedded therein, will not irritate the ductus. More often, the stent-jacket absorbs much of the impact so that a perforation is prevented.

When higher discharge velocities are required predisposing toward rebound, a prepositioned double-wedge-lined stent-jacket, addressed below in the section entitled Double-wedge Stent- and Shield-jacket Rebound-directing Linings, is used to deflect the miniball toward a functional ductus-intramural location rather than reentry into the lumen. The release of blood into the lining of the stent-jacket as the result of a perforation is unlikely to exert any significant or persistent alteration in its mechanical properties. Minimizing the entry of blood into the lining of a prepositioned stent-jacket will depend upon the condition of the blood due to the administration of an anticoagulant or platelet blockade for the procedure. If a concern, then prior to placement, the lining is wetted or coated with a coagulant, such as chitosan (Celox®, Medtrade Biopolymers Incorporated, Crewe, England) and/or a synthetic derivative of volcanic rock (Quik-Clot®, Z-Medica Corporation, Wallingford, Conn.). The same applies whether the stent-jacket is double-wedge lined.

I3b. Sequence of Stent-Jacket Placement and Implantation

Perforation with continued travel into the surrounding tissue or cavity should rarely if ever result in a longer term adverse consequence; however, the transaction of a nerve fiber can cause short-term numbness or partial dysfunction. Weighing this risk in context and the relative benefit and detractions in using a protective shield during discharge must be on a case by case basis. Preplacement of the stent-jacket does not apply to the use of stays, which inserted from outside the ductus through the adventitia, must be placed before the stent-jacket, which if placed first would block access. When the only reason prompting preplacement is to avoid a perforation, the use of stays may be considered. When another reason, such as to be able to noninvasively warm the substrate (treated) ductus by induction heating the stent-jacket before initiating or during discharge implantation, then ab initio, stays have been discounted.

However, a stent-jacket applied after stays have been inserted can be heated at any later date. Various circumstances recommend placing the stent-jacket before initiating miniball discharge. These include preventing perforations, reducing the risk of punctures through the intima that result in continued travel between separated layers through the ductus wall by applying temporary compression reducing the extent of any inter- or intralaminal separations as might occur, and compensating for weakness or a malacotic condition predisposing to the development of an aneurysm; the stent-jacket may be placed first to structurally support a segment weakened by pathology, and in so doing, shield against perforations through the segment. Acting on the basis of in situ testing and careful examination of the initial discharge, the penetrability of the lesioned and adjacent areas to be implanted dictate the exit velocities appurtenant of each and the need to preplace the stent-jacket.

The preplacement of a stent-jacket, addressed above in the section entitled Circumstances Recommending the Use of a Shield-jacket or Preplacement of the Stent-jacket, can also serve to insulate and increase the conduction of heat delivered by the barrel-assembly heat-windows or heated gas delivery connections, such as when used to accelerate the setting of a surgical cement or flow a solid protein solder coating on a miniball. If it incorporates continuous ferrous material, the stent-jacket can be independently heated noninvasively by heat induction by placing the patient in an alternating magnetic or electromagnetic field, as addressed above in the section entitled Implants that Radiate Heat on Demand, among others. To the extent possible, the aim should be to use components that are absorbable and extracorporeally (noninvasively) controllable, or 'smart.'

When a perforation could result in the striking of a ganglion or the perforation and entry into the lumen of a neighboring vessel, the stent-jacket should be placed prior to implantation. While an effective method for preventing such eventualities, when it obstructs a clear view of the work area, preplacement is not recommended. A stent-jacket to treat a radially asymmetrical or eccentric lesion along a ductus wall will usually limit magnetization to the arc affected. Unless the need to preplace such an eccentric stent-jacket is compelling, placement is deferred until after the miniballs have been placed. Even when the stent-jacket is preplaced, so long as the strength of magnetization is not high, the muzzle-head is not significantly smaller in diameter than the lumen, the arc to be implanted is not too compressed to be implanted, and only the treated arc is to be implanted with miniballs, the attraction of the muzzle-head, which contains the ferromagnetic cores of the turret-motor and recovery electromagnets, toward this arc is seldom a problem.

A drug avoidance means for reducing the intensity and radial excursion of intrinsic movement in the lumen wall that interferes with accuracy is to preplace the stent-jacket, if necessary, with the belt-straps temporarily adjusted to retain the side-slit flush. Noninvasive heating of a stent-jacket by heat induction in an alternating magnetic or electromagnetic field to melt a coating such as an adhesive or release and accelerate the uptake of a therapeutic substance such as a drug requires that the stent-jacket have already been put into position. A stent-jacket preplaced to guard against perforation when nonstenting medication miniballs are used should be absorbable, preferably, absorbable on demand by means of noninvasive heat induction when desired, as addressed above in the section entitled Implants that Radiate Heat on Demand, among others.

When the miniballs include a radioactive seed, the jacket can also include an absorbable radiation shield, as addressed above in the section entitled Radiation Shield-jackets and Radiation Shielded Stent-jackets Absorbable and Nonabsorbable. The need to control miniball rebound is determined by applying the delamination susceptibility testing procedure provided below in the section entitled Testing and Tests, and one means for achieving such control addressed above in the section entitled Double-wedge Stent- and Shield-jacket Rebound-directing Linings. The risk of delamination between or within tunics is increased when miniballs are discharged in close proximity by an automatic positional control system. While perforation (through-and-through penetration and extraductal emergence) of a miniball is always to be avoided, the diameter of the miniballs is so small that a perforation does not result in significant injury.

Due to the small diameter of miniballs, perforations are spontaneously sealed immediately by proteinaceous exudation, endoplasmic or serous, axons regenerate at about one millimeter per day, nerve cell nuclei have redundancy sufficient to overcome the small scale damage, and spillage from the gut, addressed in the section below entitled Uses of Impasse-jackets, is slight and manageable. Larger diameter miniballs are inappropriate for use in arteries; if used where coagulation expedites the sealing of a perforation (hemostasis), preplacement of a stent-jacket allows doses of platelet blockade and anticoagulant to be reduced thus reducing the risk of unwanted bleeding Application of a topical coagulant to the internal surface of the jacket or to the exterior of the vessel exerts no effect upon the concurrent circulation of a platelet blocker or anticoagulant as to reduce the risk of thrombogenesis within the lumen. The permanent lodging within the foam lining of a stent-jacket or tissue of a sterile bioinert miniball is innocuous.

Embolization by entry into the circulation is prevented by a number of means using magnetic arrest and recovery, such as delineated above in section 4g entitled Emergency Recovery of Miniballs and Stays. The propensity of the layers within the ductus wall for separation can be predetermined through the test described below in the section entitled In Situ Test on Extraluminal Approach for Intra- or Interlaminar Separation (Delamination). When proximity to a vulnerable neighboring structure such as a ganglion does dictate, perforation is prevented from leading to the puncture of the neighboring structure that would ensue were the perforation not trapped within the moisture barrier-coated viscoelastic polyurethane foam lining outside the adventitia. In such use, the innermost moisture barrier-coated viscoelastic polyurethane foam lining of the stent- or shield-jacket exhibits the yielding or nonresilience to minimize rebound, which could result in the entry of a miniball into the lumen as well as the shape memory to protect the vasa and nervi vasorum.

A magnetic stent-jacket also assists in minimizing if not eliminating rebound and in retaining the implanted miniballs in position by magnetic traction; from this standpoint, a stent-jacket functions as a less powerfully magnetized impasse-jacket. Another use for placing the jacket first is to damp discharge-induced asymmetrical jerking of the ductus. Provided the muzzle-head contacts the lumen wall round and about, even eccentric discharge, or discharge not force counterbalanced, produces no appreciable abrupt accelerations (jerking, recoil) as might dislodge a properly seated miniball or shake loose one trapped between the muzzle-port and the lumen wall. In this circumstance, to reduce the risk of being implanted miniballs, the stent-jacket is placed prior to withdrawal. Yet another reason for placing the stent-jacket prior to initiating discharge is to take advantage of the site-marking radiopacity of a stent-jacket coated with contrast, such as of tantalum.

When it is desired to chill a ductus with a stent-jacket preplaced to prevent a perforation or reinforce a weak portion of the wall of the ductus, for example, during transluminal ballistic discharge, then chilling must be provided by the barrel-assembly. This can be accomplished with a capless cooling catheter, as addressed below in the section entitled Cooling Catheters (Temperature-changing Service-catheters, connected to a cold air gun or liquified gas cartridge as addressed below in the section entitled Turret-motor Operational Modes, that discharges cold air, another gas, or water against the nose heat-window of an edge-discharge barrel-assembly). Whether implanted with miniballs or stays, when the ductus is not yet mantled about, cold line access can be from outside the vessel through the same incision as will be used to insert the stent-jacket.

Even though the implants may be miniballs, a stay insertion tool with lamp or endoscope and cold air line attached, as described below in the section entitled Binding of Lines and Cables Alongside the Stay Insertion Tool, can be inserted through the incision to effect chilling. Whether this should preclude placement of the stent-jacket prior to discharge must be left to clinical judgment. A stent-jacket placed prior to discharge will safely trap within its lining outside the adventitia a miniball that perforates due to an unexpected deviation in wall strength. If the stent-jacket is more strongly magnetized, a miniball that does not fully puncture through the adventitia will be held where the tractive electromagnets can be used to recover it rather than allowed to rebound into the lumen.

In the vascular tree, an impasse-jacket positioned downstream to will avert entry into the circulation of a miniball. Miniballs are generally small in diameter as not to embolize tissue without collateral circulation and are readily retrievable, as addressed above in section 4g entitled Emergency Recovery of Miniballs and Stays and below in section X2a(1) entitled Midprocedural Interception and Recovery of a Miniball Entering the Circulation, among others. That precaution taken, a stent-jacket or a separate shield-jacket, addressed below in the section entitled Nonmagnetized Base-tubes and Double-Wedge Shield-jackets, with a double-wedge lining, addressed below in the section entitled Double-wedge Stent- and Shield-jacket Rebound-directing Linings, intended to redirect a rebounded miniball back into the lumen wall, can eliminate the need for recovery.

Whether placed before or after discharge, wetting the interior of the stent-jacket with a vascular hemostat, such as vasopressin, epinephrine, or gamma-aminobutyric acid, and/or a plasma coagulant, such as thrombin, will arrest bleeding from a perforation that the systemic (circulating) anticoagulant and/or platelet blockade administered would otherwise perpetuate. Whether in direct stenting without ablation or angioplasty or following ablation or angioplasty immediately or after an interval, disease process induced circumferential eccentricities and longitudinal inconsistencies (differences, nonuniformities) in the mechanical properties of the ductus wall will include strength, elasticity, and resilience.

When implantation is ballistic, the initial or tentative settings for the airgun controls are determined by means of testing addressed below in the section entitled Testing and Tests, with confirmation of the settings as achieving the desired result by means of test discharges. Since most lesions are eccentric and manual control allows the procedure to be discontinued at any moment to allow the results of each discharge to be evaluated for perforations or delamination, the first few discharges are triggered manually and examined whether discharge is to be manual or thereafter accomplished at a high rate under machine control. Testing discharges should be few but cover different arcs and levels along the segment to be implanted. When only absorbable, such as medicinal, miniballs are to be implanted, the dose will be too small and the consequences in terms of trauma too insignificant to justify the use of a temporary shield-jacket.

In most cases, the exit velocity will not require adjustment from the lowest effective setting; while in others, the need for adjustment should be few. While a temporary shield-jacket or stent-jacket can be used during either manual or machine discharge, when testing reveals significant deviations in mechanical properties with a propensity for an occasional perforation at the lowest effective exit velocity, implantation discharge when automatic at high density that would tolerate a few misses is usually performed uniformly at that exit velocity with a temporary shield-jacket or preplaced stent-jacket to take up any perforations. If manual, then discharge is usually stopped and the adjustment made as necessary.

When significant differences are noted, implantation should be manual, allowing not only the exit velocity to be adjusted but the miniballs to be varied in magnetically susceptible content, keeping stent-jackets uniform in strength of magnetization reducing the cost of production. By contrast with this discretionary approach, conventional or endoluminal stents are radially symmetrical, and except for the margins, longitudinally uniform, so that even when the stent will yield beyond a certain resistance, all portions of the lumen lining surrounding the stent are treated nondifferentially. Using the various means described herein, the condition of the lumen interior can be differentially treated, and it is this capability that prompts detailed examination and testing.

The availability of intravascular ultrasound (IVUS) to allow evaluation of the vessel wall can serve as a valuable adjunct to angioscopy, which allows evaluation of the lumen, except this will generally add time to the procedure, albeit negligible. When placing nonabsorbable miniballs, based upon the uniform appearance of the lumen, the in situ test, and a test discharge that confirms the airgun settings as correct, the risk and/or consequence of a perforation is considered slight as not to warrant more detailed examination, whether to use a temporary shield-jacket or preplace the stent-jacket with hemostat-wetted lining is a clinical decision. If the miniballs are absorbable such as medicinal so that only a transluminal approach is necessary, then precautions such as intravascular ultrasound and the use of any kind of jacket may be dispensed with.

Since cytoplasm from the broken cells immediately runs into the penetration path or trajectory, a pinhole-sized perforation through the wall of an artery seals quickly without the precaution of a hemostat-wetted jacket lining, even though a systemic platelet blocker and/or anticoagulant and blood pressure-reducing medication have been administered. In an open surgical field or when an access incision has been made that allows the ductus to be visually examined, most locations will allow a deliberate perforation to confirm that sealing is quick. Unless immediately retrievable or posing a risk of problematic enstonement, errant miniballs as may have dropped into or landed in the pericardial space or a body cavity remain innocuous as boinert and best disregarded.

More numerous eccentricities in the medical condition and mechanical properties of the ductus wall can be dealt with without the need to withdraw and reenter, irritating the entry wound by changing the exit velocity and/or rotary magazine clip in the airgun chamber to allow separate implantation into the differing segments or arcs thereof. Each rotary clip can load a different number, diameter, and/or type of miniballs for discharge together as a shot-group, the turret-motor and the use of a barrel-assembly with at least 3 barrel-tubes allows discharge in any radius, and the rotary clips can be changed for each discharge, unneeded rotary clip holes left out of the clip or plugged to conserve the propulsive force.

That is, a barrel-assembly with a given number of barrel-tubes can discharge a miniball into each sector or arc of the surrounding lumen wall, where the sectors are defined according to the circumferential spacing between the exit-holes. A four-way barrel-assembly with exit-holes evenly spaced about the circumference, for example, will discharge one miniball into the center of each quadrant. Avoiding certain sectors requires only that the corresponding hole in the shot-group on the rotary clip be blanked out. With rotation by the turret-motor, traversing tighter bends in the anatomy that would preclude bodily rotation or torquing of the barrel-assembly as a whole can have little if any effect on the ability to rotate the muzzle-head and therewith, the angle of each successive discharge.

Unlimited choice of miniballs, rotary magazine clips, and continuous variability in the exit velocity, combined with the ability to rotate the muzzle-head eliminates any need for barrel-assemblies with radially asymmetrical or eccentric exit-holes. A four-way radial discharge barrel-assembly having already been introduced into the lumen, for example, allows changing from single or one-way miniball discharge to three-way or triple discharge with each rotary magazine clip. This allows successive circumferences to be implanted with unlimited variability in the miniballs delivered, while adjusting the exit velocity allows corresponding adjustment in the force of penetration. The exit velocity can be adjusted for each shot group within a rotary magazine clip but not each shot within a shot group.

With multiple variables involved and ultimate control unattainable, the ability to preplace a shield or stent-jacket to protect against inadvertent perforations is a significant consideration to justify a discharge by discharge discretionary approach. If the number of spots that warrant testing is prohibitive and changes must be frequent so that uncertainties persist, such as then control over discharge should be manual with a shield-jacket or preplaced stent-jacket in position. Alternatively, the use of wide stays, which are not susceptible to perforation, are inserted one at a time under the direct control of the operator, and can differ in numerous ways from one to the next.

Stays are also considerably less susceptible to pull-through, are not subject to differences in the force required to achieve insertion worthy of note, and thus avoid the uncertainties associated with discharge implantation. When the lumen is not characterized by numerous and marked differences, machine control with a gravity fed chamber rather than rotary magazine clips, as shown in the accompanying drawing figures of interventional airguns, can lay down a dense formation of miniballs of like diameter and mass at high speed to achieve uniform distribution of the tractive force, especially when combined with an intrinsic or quasi-intrinsic stent-jacket.

A proportion of these like sized miniballs can differ in composition such as to include or consist of medication, thus allowing uniformity in the delivery of a drug, for example, but not uniformity at a level equal to coating every miniball alike. When the wall of the ductus is too thin or tenuous to use either miniballs or stays, a clasp-jacket is applied with the inner surface coated with a surgical adhesive-sealant. Clasps that must enter the lumen of a blood vessel because the wall has become so thin must be nonthrombogenic, that is, polymeric, not metallic. In this case, placement of the stent-jacket must follow immediately rather than deferred to later date.

I3c. Sequence of Stent-Jacket Placement and Implantation in Relation to Trap-Extractor (Recovery) Electromagnet Susceptibility and Field Intensity A more strongly magnetized stent-jacket may suddenly deflect the muzzle-head even with the recovery electromagnets turned off, and attempting to offset or balance the pull will prove difficult and usually ineffective. Miniballs will also be accelerated by the pull, and if a magnetized stent-jacket rather than a nonmagnetized shield-jacket with double-wedge lining is used, the resilience of the materials of the double-wedge must the added acceleration on approach and deceleration on rebound, as addressed below in the section entitled Stent- and Shield-jacket Moisture barrier-coated viscoelastic polyurethane foam Linings The procedure will be simplified and reduced in duration when the permanent or absorbable magnetized stent-jacket can be placed ab initio. The section below entitled Nonmagnetized Base-tubes and Double-Wedge Shield-jackets addresses jackets placed temporarily during discharge implantation to protect against perforations.

To minimize abrupt deflections of the muzzle-head as would detract from accuracy, the stent-jacket, usually one intrinsically or quasi-intrinsically magnetized, is magnetized uniformly. Intrinsic and quasi-intrinsic stent-jackets present a more dense, evenly distributed, and radially symmetrical magnetization, making these preferable to the use of discrete or spaced apart magnet type stent-jackets when, albeit exceptional, magnetic strength of a field intensity as would deflect the muzzle-head is required. Eccentric retraction of a collapsed or stenosed lumen wall is accomplished by placing the ductus-intramural implants in conformity to the eccentricity without complementary eccentricity in the stent-jacket also reduces the need for specially configured stent-jackets to treat different eccentric conditions and the greater cost to produce these.

The need for such strength is greater when the magnetization is radially asymmetrical or eccentric as is associated with placement to attract drug carrier nanoparticles in a ferrofluid passing through the lumen against or into a lesion, and rarely if ever with the degree of tractive force necessary to maintain patency in a stenosed lumen. Intended to act over a distance, a magnet-wrap or magnet-jacket usually incorporates more powerful spaced apart magnets; however, it is not ordinarily used in encircling relation to miniballs and therefore not transluminally or intromission traversed by a muzzle-head. When encircled by more powerful magnets, sudden displacement of the muzzle-head and compression of the contact tissue will occur regardless how axially centered or flush to the internal surface of the lumen wall the muzzle-head appears fluoroscopically or otherwise radiologically.

There are, however, circumstances in which it is preferable to place the stent-jacket before initiating discharge. For example, the attractive force on the muzzle-head can be used to achieve flush or even compressive placement of the muzzle-head against the lumen wall, such as to flow and hold flush separated lamina pending setting of a protein cement used as a tissue binder while heated by a heat-window in the muzzle-head and/or heat induction of the stent-jacket. In some cases, a stent-jacket with more powerful separated magnets may be preplaced precisely to take advantage of this detention at intervals, which is readily amplified to achieve variability in the compressive force by adjusting the recovery electromagnets in field strength and polarity as necessary.

Broadly, when discharge implantation is involved and the pathology has produced marked differences in tissue penetrability about the lumen wall, then the stent-jacket, which will present magnetization conformant to this eccentricity, rather than contributing yet another eccentricity by virtue of pulling at the muzzle-head, should be placed after implantation. When offsetting factors justify preplacement of the jacket despite this difficulty, then counteracting magnetic repulsion supplied by the tractive electromagnets or an external electromagnet may of assistance. The coordinated use of two or more moving magnetic fields must anticipate abrupt sidewise deflections.

To avoid abrupt shifts of the muzzle-head, which contains magnetically susceptible matter such as the ferromagnetic cores of the turret-motor and recovery electromagnet, as it moves among the magnetic fields of an extrinsically magnetized stent-jacket with stronger spaced apart bar magnets mounted about the outer surface of the base-tube, the stent-jacket is usually placed after the miniballs. The effect of stronger separate bar magnets mounted about the outer surface of the base-tube on the muzzle-head can to some extent be moderated by varying the polarity and intensity of the fields generated by the miniball recovery tractive electromagnets, (trap-extractor) magnets.

When the stent-jacket is placed prior to discharge implantation, access to the ductus from the outside will have been established, allowing the use of the recovery electromagnet in a stay insertion tool to steer the muzzle-head when it would be drawn aside by another less powerful magnetic field. Rotating an eccentric stent-jacket about an artery to steer a muzzle-head or another catheteric device is difficult, injures the adventitial innervation and vascularization, and when an external electromagnet can be used to obtain the same control noninvasively, is unnecessary. Where this factor is contextually less significant, as in implanting the trachea of a small dog with a collapsed dorsal ligament, care must still be given to avoid the recurrent laryngeal nerve.

So long as the effect of compression with any offsetting or countering attractive forces can be duplicated and evaluated before discharge by in situ testing described below in the section entitled Testing and Tests and is not so forceful as precludes implantation, the nonuniformity in exit velocity to achieve penetration is treated no differently than are differences in impact force required by pathology. Implantation is keyed to preserving patency, which normally requires retraction of the obstructive lesion. Generally, stenting miniballs that include medication and/or radiation are infixed within the lesion, while those used purely to retract are infixed alongside or opposite the lesion.

If muzzle-head deflection is significant and a monobarrel radial discharge muzzle-head that resists rotation by the turret-motor or a multiple radial discharge barrel-assembly is to implant medication miniballs, for example, in another arc, then a midprocedurally lubricated muzzle-head of larger diameter or a stent-jacket with opposing magnetization is used. A muzzle-head with ferrous material omitted could be made, for example, by transfer-molding and machining polytetrafluoroethylene. Omitting recovery electromagnets and a turret-motor, such a muzzle-head would avert not only the unfavorable but also the favorable effects of magnetic attraction and do so with a critical loss in controllability.

A combination-form barrel-assembly with an empty through and through central channel using such a muzzle-head would allow the insertion of a service catheter with iron head (distal end) as needed to allow the use of an external electromagnet to assist in steering the muzzle-head through tighter curves or to bring the muzzle-head into contact or closer contact with the tissue to be treated. However, even though such a device could be torqued to the rotator angle needed and alternative measures described herein would still allow the arrest and recovery of a dropped miniball, the loss of recovery electromagnet and turret-motor function is insupportable. The steering and abutting use of an external electromagnet is no less applicable to a fully appointed muzzle-head, but is unusable with any kind of muzzle-head when the tractive force required would result in the dislodgement or extraction of miniballs.

I4. Internal Environment-Resistant Base-Tube Polymers, Metals, and Combinations Thereof The primary object in base-tube and nonabsorbable stent-jacket matrix structure is to achieve the required compliance with smooth muscle action over a long service life. For a stent-jacket to encircle a ductus embedded or invested within tissue rather than situated within a body cavity, structural breakdown with the formation of tiny cracks that progressively reduce the elasticity and resilience of an implanted polymer is accelerated. When chemical isolation and magnetization are imparted by encapsulation within a nonreactive outer coating, any material or combination of materials that afford the requisite elasticity and resilience are also suitable.

Base-tube, part number 5 in FIGS. 2 thru 7, may comprise intrinsically magnetizable rounded polymeric or metal sheet stock, or nonmagnetizable rounded polymeric sheet stock to which small permanent, usually neodymium magnets encapsulated to assure chemical isolation of the toxic neodymium shown as part number 4 in FIGS. 2 thru 7, or small electromagnets are fastened about the outer surface. Magnetization is perpendicular to the longitudinal axis of the substrate conduit or ductus, meaning the conduit or ductus the jacket is positioned to encircle.

Base-tubes are perforated entirely through the outer shell and closed cell viscoelastic polyurethane foam part number 5*a* in FIGS. 2 thru 7 lining down to the outer surface of the substate ductus with holes, or fenestrae, sufficiently large to assure shape compliance, or shape accommodation, with the vasa vasora and nervora that would otherwise be compressed and obstructed from the environment, and to assure gas exchange between the substrate adventitia and the surrounding internal environment, communication thus essential to avoid the prompt inducement of atherosclerotic degeneration (see, for example, De Meyer, G. R. Y., Van Put, D. J., Kockx, M. M., Van Schil, P., Bosmans, R., Bult, H., Buyssens, N., Vanmaele, R., and Herman, A. G. 1997. "Possible Mechanisms of Collar-induced Intimal Thickening," *Arteriosclerosis, Thrombosis, and Vascular Biology* 17(10):1924-1930). The fenestrae can be any shape but should be as large as possible.

With any material, as the base-tube is made thicker, flexibility is reduced along and by extension outward from the longitudinal line opposite the side-slit or side-slot. Suitable encapsulation materials must also therefore not only exhibit resistance to phagocytic, hydrolytic and enzymatic breakdown but afford flexibility consistent with compliance to the smooth muscle action in the substrate ductus and do so in a thickness that will withstand frequent flexion without fatigue for a period of years, and preferably, to the end of life. A nonencapsulated stent-jacket base-tube with encapsulated bar magnets mounted about its outer surface and a nonencapsulated nonabsorbable matrix of a quasi-intrinsically magnetized stent-jacket must be made of implantable tubing that withstands the intracorporeal environment.

Whereas an intrinsically magnetized stent-jacket of thin ferromagnetic stainless spring steel is likely to last throughout life, a loss in polymeric base-tube resilience due to the development of microfractures and chemical breakdown in the internal environment will disable an extraluminal stent of the spaced apart magnet or quasi-intrinsically magnetized types described above in the section entitled Types of stent-jacket. The moisture barrier-coated viscoelastic polyurethane foam lining of stent- or shield-jacket also has a life of many years inside the body. Moreover, this degradation will be accelerated in proportion to the size and number of perforations provided to allow gas and other chemical exchange at the outer surface of the ductus.

In considering uncoated or bare base-tube materials, inert silicone elastomers such as those of polydimethylsiloxane sold by Dow Corning under the trade name Silastic and Bluestar Silicones under the trade name Silbione have a long record of extended life without significant foreign body reaction when implanted (see, for example, Sincoff, E. H., Liu, J. K., Matsen, L., Dogan, A., Kim, I., McMenomey, S. O., and Delashaw, J. B. Jr. 2007. "A Novel Treatment Approach to Cholesterol Granulomas. Technical Note," *Journal of Neurosurgery* 107(2):446-450; Máchler, H. E., Schmidt, C. H., Neuner, P., Iberer, F., Anelli-Monti, M., Dacar, D., Rigler, B., and Kraft-Kinz, J. 1993. Twenty-four Years' Implant Duration of the Aortic Starr-Edwards Silastic Ball Prosthesis: A Valve of the Past?," *European Journal of Cardiothoracic Surgery* 7(3):114-116). Means for discouraging the formation of foreign body giant cells on materials containing polyurethane are addressed below in the section entitled Materials Suitable for Rebound-directing Double-wedge Linings.

The reputation of silicone is due at least in part to leakage from breast implants and the injection of nonmedical grade material for cosmetological purposes, often by incompetent practitioners (see, for example, Schwartzfarb, E. M., Hametti, J. M., Romanelli, P., and Ricotti, C. 2008. "Foreign Body Granuloma Formation Secondary to Silicone Injection," *Dermatology Online Journal* 14(7):20; Narins, R. S. and Beer, K. 2006. "Liquid Injectable Silicone: A Review of Its History, Immunology, Technical Considerations, Complications, and Potential," *Plastic and Reconstructive Surgery* 118(3 Supplement):77S-84S). However, the attribution of adverse results to impurity and/or incompetency of liquid silicone has been cited as exaggerated (Chasan, P. E. 2007.

The History of Injectable Silicone Fluids for Soft-tissue Augmentation," *Plastic and Reconstructive Surgery* 120(7): 2034-2043).

Other more recent materials are significantly increasing potential longevity within the internal environment (see, for example Pinchuk, L. 1998. "Biostable Elastomeric Polymers Having Quaternary Carbons," U.S. Pat. No. 5,741,331). Materials found lacking under the more stringent requirements imposed on a prosthetic tricuspid valve, for example, are still likely to prove adequate in a base-tube, which outside the bloodstream, is not constantly washed over by blood or subject to calcification, for example (see, for example, Wang, Q., McGoron, A. J., Bianco, R., Kato, Y., Pinchuk, L., and Schoephoerster, R. T. 2010. "In-vivo Assessment of a Novel Polymer (SIBS) Trileaflet Heart Valve," *Journal of Heart Valve Disease* 19(4):499-505) or load-bearing, for example (see Pinchuk, L., Wilson, G. J., Barry, J. J., Schoephoerster, R. T., Parel, J. M., and Kennedy, J. P. 2008. "Medical Applications of Poly(styrene-block-isobutylene-block-styrene) ("SIBS")," *Biomaterials* 29(4): 448-460).

Tubing that is able to withstand the salinity of the intracorporeal environment can be extruded from pellets or diced Bionate® polycarbonate-urethane copolymer (see, for example, Ward, R. S. 2000. "Thermoplastic Silicone-Urethane Copolymers: A New Class of Biomedical Elastomers," *Medical Device and Diagnostic Industry* 22(4):68-77), produced by the Polymer Technology Group, Inc., Berkeley, Calif., previously sold under the tradename Corethane® Polycarbonate by Corvita, Inc. Other prospective base-tube polymers from the same company include Biospan® segmented polyurethane, Elasthane® thermoplastic polyetherurethane, PurSil®, silicone polyether urethane, and Carbosil® silicone polycarbonate urethane, and from Thoratec, Inc., Pleasanton, Calif., Thoralon® segmented polyetherurethaneurea blended with a siloxane that includes a surface-modifying additive. One such material exhibits a durometer D-scale per ASTM D2240-02 test, Shore A reading at 15 seconds of 55 (see also Müller-Glauser, W., Lehmann, K. H., Bittmann, P., Bay, U., Dittes, P., von Segesser, L., and Turina, M. 1988. "A Compliant Small-diameter Vascular Prosthesis Lined with Functional Venous Endothelial Cells," *American Society for Artificial Internal Organs Transactions* 34(3):528-531).

Implanted AorTech International, Wahroonga, New South Wales, Australia subsidiary AorTech Medical Devices, Rogers, Minn. Elast-Eon™ 2 80A, synthesized using poly (hexamethylene oxide) (PHMO) and poly(dimethylsiloxane) (PDMS) macrodiols, has been demonstrated to stand up well and with tolerable alteration in mechanical properties over time (Simmons, A., Hyvarinen, J., Odell, R. A., Martin, D. J., Gunatillake, P. A., Noble, K. R., and Poole-Warren, L. A. 2004. "Long-term in Vivo Biostability of Poly(dimethylsiloxane)/Poly(hexamethylene Oxide) Mixed Macrodiol-based Polyurethane Elastomers," *Biomaterials* 25(20):4887-4900; Martin, D. J., Warren, L. A., Gunatillake, P. A., McCarthy, S. J., Meijs, G. F., and Schindhelm, K. 2000. "Polydimethylsiloxane/Polyether-mixed Macrodiol-based Polyurethane Elastomers: Biostability," *Biomaterials* 21(10): 1021-1029).

Macrodiol-based polyurethane elastomers also withstand sterilization well, whether using gas plasma, steam, vapour phase liquid chemical, or even multiple cycles using ethylene oxide or gamma-irradiation (Simmons, A., Hyvarinen, J., and Poole-Warren, L. 2006. "The Effect of Sterilisation [sic] on a Poly(dimethylsiloxane)/Poly(hexamethylene oxide) Mixed Macrodiol-based Polyurethane Elastomer," *Biomaterials* 27(25):4484-4497.

The exposure of the base-tube or the matrix of a quasi-intrinsically magnetized stent-jacket placed about an artery within a sheath coursing through skeletal muscle, for example, is less than that of a polymer exposed to digestive or catabolic enzymes, for example. For this reason, the extraluminal component of the stent described herein is able to supplant endoluminal stents regardless of situation. However, the inner diameter of the base-tube or extraluminal component exceeds that of the outer diameter of the ductus by the thickness of the moisture barrier-coated viscoelastic polyurethane foam lining, and to allow the extraluminal component to encircle and expand and contract with the substrate artery, it is longitudinally slit along one side.

Since placed within a sheath, the outer corners of the bar magnets in an extrinsically magnetized stent-jacket of the discrete or spaced apart magnet type would pulsate against the enveloping or apposing tissue, for situation thus, a quasi-intrinsically magnetized stent-jacket is used instead. When protrusion by discrete magnets into the surrounding tissue is less prominent, abrasive or probing injury is avoided because the outer corners of the magnets are rounded and the magnets encapsulated together with the base-tube in a rubbery polymer of plastisol-like softness for bioinertness, hence longer life, and to prevent separation. An extraluminal stent in an extremity can be used not only to stent but to attract drug carrier nanoparticles from the passing blood into the wall of the artery, something an endoluminal stent cannot.

When the magnetic strength required of a stent-jacket or an impasse-jacket used for drug targeting in an extremity is greater than the space within the sheath would allow, the stent-jacket is worn externally. A cuff of this kind is a magnet-wrap used as an impasse-jacket and can be also be used as a kind of stent, such as temporarily to palliate tracheomalacia in an infant or collapsed trachea in a veterinary patient. The base-tubes of discrete magnet type and the matrixes of quasi-intrinsically magnetized stent-jackets can be extruded of individual or coextruded of different materials laminated or blended to obtain any functional restorative force.

I5. Protective Encapsulation of the Stent-Jacket

In an extrinsically magnetized stent-jacket, the magnets are bonded or fastened to the base-tube and the two encapsulated together as a unit before the moisture barrier-coated viscoelastic polyurethane foam lining is bonded inside. This adds an additional layer of protection against a release of toxic lanthanoid, thermal insulation, and reinforces the magnet-base-tube bond to prevent disconnection due to deterioration over time, a direct blow, or exposure to extremes of temperature. Tantalum contrast is applied to this outer coating.

This outer coating or casing can consist of biaxially-oriented polyethylene terephthalate (boPET) is applied (see, for example, Drobota, M., Aflori, M. and Barboiu, V. 2010. "Protein Immobilization on Poly(Ethylene Terephthalate) Films Modified by Plasma and Chemical Treatments," *Digest Journal of Nanomaterials and Biostructures* 5(1): 35-42), such as by heat-shrinking and heat sealing, the temperature thereof not high enough to affect the elasticity of the base-tube or magnetization of the bar magnets. Further jacketing within polyethylene to enhance puncture resistance is usually nonessential. Intrinsically and quasi-intrinsically magnetized stent-jackets seldom require encapsulation.

I6. Stent-Jackets with Sling String Pull Opener

The hook ends of stent-jacket insertion tools pivot to allow use at awkward angles. When the location makes retraction of the side-slit or side-slot and encirclement of the ductus difficult despite this, pull-strings can be attached. The pull-strings of higher tensile strength absorbable (such as glycolide-dioxanone-trimethylene carbonate) or nonabsorbable braided suture include strands or monofilaments that diverge or fan out hammock-style to attach to a strip of tape with a strong pressure sensitive backing. Prior to insertion, one strip of tape is attached parallel to and at a slight interval from each side of the slit or slot or side-slot. The pull-strings and a stent-jacket insertion tool are seldom used at the same time.

Both strings are pulled by one hand to open the stent-jacket and the tip of a probe, pliers, or hemostat, for example, used to press against the stent-jacket opposite the slit around the ductus. If awkward adjustments in angle make it necessary, surgical pliers are used to pull at one or more of the strands. Once the stent-jacket has been placed, the suture if nonabsorbable can be snipped away or if absorbable can be more thoroughly disintegrated if swabbed with hydrogen peroxide just prior withdrawal and closure. Absorbable materials are always subject to premature dissolution under conditions of fever, infection, or an accumulation of aqueous fluid as in edema or ascites.

I7. Stent and Shield-Jacket Protective Linings

I7a. Double-Wedge Stent- and Shield-Jacket Rebound-Directing Linings

I7a(1). Conformation of Double-Wedge Linings

Miniballs used in arteries are so small that a perforation quickly seals even with the platelet blocker administered. Those used in the gut are larger but proportionally so small that perforation does not result in leakage necessitating reentry. Prepositioned perforation shielding jackets are provided as an extra precaution in instances where perforation would pose a greater risk. Double-wedge stent-jacket linings have an inclined interface between an outer resilient or rubbery and a complementary inner moisture barrier-coated viscoelastic polyurethane foam layer. Alternatively, as shown in FIG. 12, when the base-tube is itself of suitable resilience and increases in thickness from one end to the other, then no resilient wedge-shaped layer between the base-tube and the complementary wedge-shaped moisture barrier-coated viscoelastic polyurethane foam lining may be necessary, the latter referred to as a wedged lining.

Thus, the outer wedge can be the base-tube of an extrinsically or matrix of a quasi-intrinsically magnetized stent-jacket or it can be an additional wedge of a rubbery polymer interposed between the base-tube and the foam inner lining. Although varying the thickness, material, and the use of coextrusions allow jacket elasticity for compliance to the expansion and contraction of the substrate (treated, encircled) ductus to be adjusted, a double-wedge insert lining segregates the properties that contribute to this physiological compliance from those that give the internal surface a resilience suitable for redirecting rebounds. The wedged layers can be directly molded or made from flat sheet stock razor shaved to the angle of inclination specified, then thermoformed into a tube with side-slit or slot as needed representing the gap between the sides as short of flush.

Figure 13:
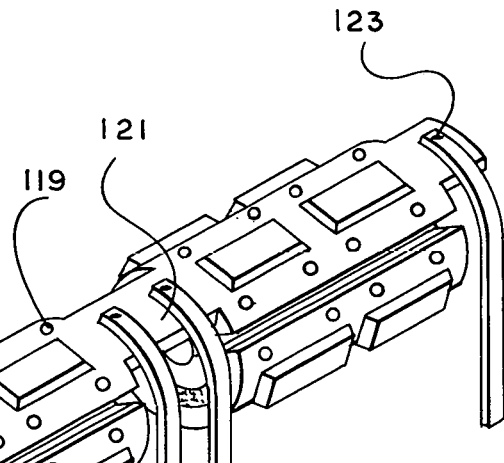
FIG. 13 is a perspective view of a chain stent-jacket of the segmented extrinsic spaced apart magnet type in the form of an iterative module substents along a continuous length of base-tubing from which one or more stent-jacket modules can be snipped off midway between the side-straps.

Any additional ingredients for cross-linking must be suitable for implantation. While the overall thickness of a lining intended to assist in the control of rebounds is unaffected, the density of the moisture barrier-coated viscoelastic polyurethane foam and more resilient outer wedge or internal surface of the base-tube must meet the primary desiderata of reducing the momentum of and redirecting or steering rebounds, which calls for certain relations between the material and surface geometry of both lining materials, and this is accomplished by means of a layer that consists of two sublayers at complementary angles as described. A segmented sectional stent-jacket, or one made from a continuous length of flexible tubing such as that shown in FIG. 13, is not of the latter type, which necessitates costly machining to manufacture but composed of individual unit or modular jackets wherein each has inserted within it a double-wedge of which the outer is not identical with the continuous tube.

Stent-jacket linings are devised to incorporate anti-migration, tissue infiltration or integration encouraging, and perforation preventing features in one and the same lining, a disproportionate requirement for one of these as opposed to the others arising infrequently. Moisture barrier-coated viscoelastic polyurethane foam, especially when treated to encourage infiltration serves these purposes. As addressed above in the section entitled Sequence of Stent-jacket Placement and Implantation, when the stent-jacket is placed prior to initiating discharge, a resilient lining of suitable conformation can avert the rebound of a perforating miniball into the lumen. Depending upon the force of impact (momentum) and resilience of the lining, a parallel or noninclined foam lining will trap a less forceful miniball but if backed by a rubbery base-tube, can rebound a more forceful one distally and medially, into the lumen.

A double-wedge can trap the one and redirect the rebound to implant the ductus wall shortly distal to the point intended but still functional for medicating or stenting the wall, for example. In the vascular tree, protection from the risk of embolization obtained by prepositioning a stent-jacket with a double-wedge lining can be reinforced by the additional preplacement downstream of an impasse-jacket, as addressed in the section above entitled Concept of the Impasse-jacket and below in the section entitled Miniball and Ferrofluid-borne Particle-impassable Jackets, or Impasse-jackets.

The need for additional percutaneous access to place a shield-jacket or impasse-jacket can be dispensed with when a powerful extracorporeal electromagnet with probe strategically aimed downstream to arrest a miniball loose in the bloodstream and extract it to a point outside the ductus to a location where it will be least risky to do so can be used, as addressed in section X2c below entitled Stereotactic Arrest and Extraction of a Circulating, Dangerously Mispositioned, or Embolizing Miniball. If the lines of force are directional and the probe distant from the intended implantation site, this has the added benefit of not risking dislodgement of nearby implants.

I7a(2). Functional Background to Double-Wedge Linings

A double-wedge lined radiation shield-jacket protects against perforation into the tissue surrounding the ductus of radiation seed-miniballs, although such use only expedites recovery if accidentally rebounding into the lumen; a trap impasse-jacket or jackets and prepositioned external electromagnet make such use additionally precautionary. While an impasse-jacket used strictly as a downstream trap is generally absorbable, one positioned over a lesioned segment to serve both immediately as a trap and to attract drug carrier nanoparticles into the vessel wall at any later date is nonabsorbable. An impasse-jacket originally placed for the purpose of drug targeting will generally negate the need to place an impasse-jacket as a protective trap in support of a later procedure.

This dual functionality is imparted by the facts that miniballs will always be of a diameter proportional to that of the vessel, and both trapping and drug targeting necessitate a strength of magnetization greater than that appropriate in most stent-jackets. By comparison, stent-jackets are intended to impose no greater tractive force than is needed to maintain patency without delamination or pull-through and are not conformed to allow immediate extraction of a trapped miniball with the aid of an extracorporeal electromagnet. The invasive factor of creating two or three entry incisions, one to insert the barrel-assembly, the second to insert the stent-jacket, and third to insert the impasse-jacket, is weighed against the small size of these implants and the paths required to gain access to the treatment site.

Application with an open surgical field makes placing stopping and stent-jackets a minor task. A double-wedge shield-jacket for placement about the segment to be implanted before initiating discharge to contain any perforations consists of a base-tube with double-wedge lining without magnetization whether with extrinsic discrete tiny bar magnets about the outer surface of the base-tube or by lamination with an outer quasi-intrinsically magnetized layer. It is suited to protecting against perforations, but unlike a shield-jacket with a thinner lining, less efficient at warming the substrate segment through heat induction when desired. The need for a shield-jacket purely to protect against perforations is seldom necessary; due to the small size of most miniballs, perforations pose little if any risk of significant much less serious injury.

Exceptional situations such as the possibility of striking a recurrent laryngeal nerve, for example, make provision of a shield necessary. Unpredictable with diseased tissue, a propensity for wall failure necessitates preliminary in situ testing as described in the section below entitled In situ Test on Endoluminal Approach for Susceptibility of the Ductus Wall to Puncture, Penetration, and Perforation. When an immediate source or sources of medication and/or radiation within the ductus wall would be advantageous over systemic or more dispersed treatment, miniballs that consist purely of medication and/or emit radiation can be implanted. When miniballs are chosen over placement of an impasse-jacket, precautions should be taken to prevent the loss of a miniball downstream and embolization.

This can take the form of an impasse-jacket prepositioned downstream and/or a double-wedge lined shield-jacket As is the case with prostatic brachytherapy, radiation spherules (seed miniballs, miniball seeds) are allowed to remain permanently, the thrombogenicity and invasiveness of a second procedure to remove these (through use of the recovery electromagnets) unnecessary. Medication miniballs are absorbed over time and any remainder of seeds left within the wall, and not released downstream. If the luminal wall is malacotic, then to implant medication miniballs should be discounted in favor of medication stays, which require only permural access, while ballistic implantation requires transluminal and additional permural access to insert a precautionary double-wedge shield and/or downstream trap impasse-jacket.

The inner wedge moisture barrier-coated viscoelastic polyurethane foam lining averts migration, and can be chosen and further treated to encourage tissue ingrowth and adhesion and can absorb and retain more of a perforation sealant and/or antibiotic, for example. The more acute is the angle of discharge in relation to the internal surface of the ductus, the weaker in magnitude is the vector normal to the intima that causes the miniball to penetrate the ductus wall and the greater the forward or down-lumen vector. Too acute an angle of discharge risks failure to penetrate, and a sclerotic condition, lesion, or mineral deposit of hydroxyapatite (hydroxylapatite) or salt increases the possibility for a glancing rebound. The angle of discharge is therefore limited and determines the angle of inclination of the double-wedge lining used with a given muzzle-head.

In increasing order of unwanted outcome with respect to an artery, nonfunctional discharges are those that terminate too far distad, perforate, or rebound into the lumen. Given the need to minimize the jacket diameter in order to avoid encroaching upon adjacent structures, the foam cannot simply be made so thick that it would retain any rebound within a jacket of smaller diameter. While consideration here is to an outer wedge of a resilience that preserves momentum to support rebound with reentry into the ductus, the conformation of elements described makes it no less possible to choose a material for the foam backing resilient surface that is absorbent thereby reducing the chance that a perforating miniball will reenter the ductus at any point.

Accordingly, a means for redirecting forcible rebounds so that the angle of rebound will not allow the miniball to penetrate into the lumen is necessary. Correction of the rebound angle necessitates an inclined resilient rebound surface outside the moisture barrier-coated viscoelastic polyurethane foam lining of complementary distolaterally increasing thickness base-tube. When a double-wedge lined shield-jacket is used with the placement of medicinal miniballs, only those with a trajectory terminus too distal in relation to the lesion to be treated will be nonfunctional. To impart an angle of rebound that will redirect the miniball to a functional or stent-encircled location requires the interposition of a resilient surface that distolaterally inclined, shifts the rebound abluminally.

When stenting miniballs are placed, the first object in the use of a double-wedge lined shield-jacket or stent-jacket is to prevent a miniball from rebounding into the lumen, and the second to redirect the miniball to a ductus-intramural location that although distal relative to the location intended, is still functional in falling within the stent-jacket. Reducing the acuteness of discharge thus reduces the tendency toward such nonfunctional discharges. The use of a double-wedge lining offsets a more stringent limitation on acuteness by imparting an angle of rebound that is sufficiently more acute than that of discharge to redirect the miniball to a point distal but still ductus-intramural; these considerations demand that the angle of discharge and the inclination of the lining be coordinated to result in a redirection of the miniball that is still functional.

Provided the lumen wall is not at the same time compressed as to be made too thin to implant, using an external electromagnet to draw the exit-hole flush against the endothelium may allow the angle of discharge to be made more acute; however, the magnetic field should be highly directional and care given not to extract implanted miniballs. Resistance to compression is usually present because the wall is sclerosed or contains a firm lesion. Energization of the facing recovery electromagnet during discharge can be used to slightly bend the trajectory, but the use of a high amplitude similarly risks the dislodging or extracting of nearby implants. An advantage in the arrest of a miniball downstream is distance from neighboring implants.

A powerful external electromagnet, as addressed in the preceding section entitled Conformation of Double-wedge Linings, can both arrest and extract a miniball from the lumen, while an impasse-jacket will trap and retain a miniball, which if necessary, can be extracted with the aid of a powerful external electromagnet. Stent-jackets and shield-jackets with or without a double-wedge lining do not allow extraction thus. When a high exit velocity and/or loss in intrinsic elasticity of the ductus wall due to disease increase the chance for a perforation or rebound into the lumen, the shield-jacket or stent-jacket is placed prior to initiating discharge. The use of a double-wedge lining is based upon the results of in situ testing, addressed below in the section entitled Testing and Tests, and complications to which the conditions present predispose.

With increasing momentum and suddenness of impact, wall resilience less predisposes to rebound but the chance of perforation is increased. Placing a jacket without a cushion lining about the ductus provides a rebound surface to prevent perforations but which must be angled to avoid the most unwanted consequence, which is a rebound into the lumen. The moisture barrier-coated viscoelastic polyurethane foam lining slows and can trap a miniball preventing rebound. Absent pathology that hardens the wall, such as a neoplasm or firm plaque, the wall will be compressible, so that a firm backing does not contribute to penetrability as would allow the exit velocity to be reduced; unless a miniball impacts with perforative force, the preplacement of the stent-jacket will make little difference. Moisture barrier-coated viscoelastic polyurethane foam linings are addressed below in the section entitled Stent and Shield-jacket Moisture barrier-coated viscoelastic polyurethane foam Linings.

The density, shock impact response, and thickness of the laminae of the wall and foam all contribute to the result, and since the tissue of the ductus may vary from one point to the next and the thickness of the foam must continuously change according to the angle of inclination dictated by the angle of discharge, complete control over the result of discharge can never be achieved. The additional layers of the shield or stent-jacket encircling the ductus can be produced to a high standard of consistency. However, the variability of the tissue and the fact that the double-wedge must be inclined for the angle of discharge so that it varies in thickness at every point along its length, means that slightly different conditions pertain depending upon the exact point of impact.

Every element subject to multiple variables, the complexity of the overall physical system, because it includes tissue consisting of laminae having different properties further altered by disease, precludes attaining certainty of outcome, but not predictability sufficient to allow effective treatment. Backed by a compliant foam lining, the residual momentum of the miniball, the strength and elasticity of the adventitia, and the density, shock impact response, and thickness of the foam lining, along the trajectory determine the result of discharge. The thickness of the inclined foam different for every point and angle of entry along the length of the jacket, these factors determine whether the miniball is:

1. Stopped without perforating the adventitia to remain subadventitial as desired.

2. Forcibly drives the adventitia through the foam lining to rebound off the resilient surface behind the foam lining without perforating but imparting negligible stretching injury to the adventitia.

3. Perforates the adventitia to become trapped in the lining with little rebound.

4. Does so but delivers a blow to the adventitia; or

5. Continues after rebound with sufficient residual momentum to perforate and reenter the ductus.

The angle, residual momentum, and penetrability of each layer of the ductus now determine whether the miniball is trapped within the ductus wall or reperforates into the lumen. If due to an irregularity such as a mineral deposit, the angle of rebound is deviated from equally and oppositely acute to obtuse, then entry into the lumen may result. If the residual momentum is high enough, such irregularities may be forced aside or perforated by the miniball. However, if the momentum has been dissipated and the irregularity larger, deflection will result. While the barrel-assembly is equipped with recovery electromagnets and a run-ahead trap-filter that would recover the miniball, and additional measures to include the prepositioning downstream of an impasse-jacket and/or extracorporeal electromagnet will be described, it is preferable to minimize if not eliminate nonfunctional discharges.

Thus, at every point along the trajectory, the angle of travel and the mechanical properties and the strength and thickness of each material encountered determine the exact path the trajectory will describe. The inclined and therefore continuously varying angle and thickness of the foam lining and its resilient backing of complementary or reciprocal inclination are based upon the angle of discharge to slow and steer the miniball away from the lumen. The thinner the foam at the point of impact, the less is the momentum depleted and the higher the likelihood for overextended travel. Consequently, a given muzzle-head must be used with double-wedge jackets devised for its angle of discharge. The angle of discharge for each exit-hole in a multiple barrel radial discharge barrel-assembly is the same.

However, provided the testing procedure reveals the conditions to confront and the probable result of discharge, the odds that significant deviations will go undetected will be less as the number of points tested is increased. Moreover, in situ testing precedes and can therefore determine the choice of a muzzle-head of a certain discharge angle, hence, the inclination of the double-wedge lining. Furthermore, the foam along the length of the shield or jacket can be varied to offset differences in thickness. Histological variability is usually not immutable, in situ testing also indicating the suitability of preparatory treatment with a sclerosant, tumefacient, or sealant, for example, which an ablation or angioplasty-capable barrel-assembly or a radial projection catheter can release into the lumen, swab onto the intima, or locally inject alone or in any combination.

In situ testing to establish the proper discharge exit-velocity that includes numerous testing points along the lumen wall will usually reveal any weak spots. Testing allows the discharge exit-velocity to be correctly set, so that perforations should seldom if ever occur. Provided a weak spot is missed and the trajectory passes through it, then a perforation will occur. Ordinarily, the small size and composition of a miniball means that a perforation will be innocuous, at worst nicking a nerve or ganglion or severing a nervelet resulting in temporary partial or localized dysfunction, or a larger vessel that because the puncture is small, promptly seals even with anticoagulant and/or antiplatelet blockade having been administered, or a small vessel, resulting in localized hemorrhage at a level where collateral circulation abundant. Nevertheless, certain circumstances necessitate means for preventing a perforation.

For example, high concentration dose medicinal or radiation-emitting miniballs, that perforate must be prevented from coming to rest in tissue where the medication or radiation would have the potential to do harm. Perforation can be prevented through the temporary placement of a shield-jacket or by prepositioning the stent-jacket. The problem then becomes preventing rebound into the lumen or infixion at a location too far distad to fall within the stent-jacket or to achieve the proximity required for effective uptake by the targeted lesion or segment of the medication or radiation; placing a shield prior to discharge prevents must not simply take the momentum that would have perforated to produce an outcome that is worse. The muzzle-head is configured to discharge at an acute angle, which is less amenable to perforation than would, to cite the extreme, discharge normal to the lumen wall.

The more acute is the angle of discharge, the less likely is a perforation, but a trajectory containing a uncharacteristically disproportionate amount of soft tissue can allow a perforation even though the exit velocity is properly set for the tissue as a whole. In general, provided the exit-velocity is high enough to overcome differences of tissue hardness along the trajectory, the angle of rebound off a hypothetical flat plate positioned parallel to the lumen would be substantially equal and opposite to the angle of impact. Even though rebound is equally and oppositely acute, if the momentum of the rebound is high enough and impedance by the media and internal elastic lamina inadequate, the miniball, could penetrate into the lumen. Angling the plate distolaterally shifts the angle of impact so that the equal but opposite rebound is likewise displaced distolaterally, hence shifted away from the lumen.

The internal surface of the actual shield not flat but circular, rebound is in two dimensions, but the vertical dimension will seldom if ever be that problematic. If rebound causes the miniball to continue into the ductus, a small concretion is unlikely to redirect a miniball with increased distal direction and sufficient momentum into the lumen. The distomedial reorientation of the rebound recovery leg is likely to bring the miniball to a terminus distal to that desired but within the wall. If this brings a medicinal miniball to distal to the target lesion, for example, or a stenting miniball to a point beyond the distal margin of the stent-jacket, then placement is nonfunctional. Thus, the odds of a problematic terminus are reduced and the operator afforded the opportunity to reduce the exit velocity with little harm before resuming discharge.

The next miniball may still not seat at a functional point; however, entry into the lumen should not result. By incorporating an inclined surface of suitable resilience to redirect the miniball with reduced momentum so that upon rebounding, the miniball will seat medially or subadventitially (perimedially), the risk of entry into the lumen should be all but eliminated. In a stent-jacket with double-wedge, the moisture barrier-coated viscoelastic polyurethane foam component of the inner or adluminal of the double-wedge protects the microstructures about the ductus, negating the compression on these that the magnetic field would otherwise impose. At its thinnest point proximally, the foam wedge must therefore be thick enough to accommodate the fine vessels and nerves of the adventitia or fibrosa.

Neither should the inner foam layer be so thick or resilient at the distal end that it prevents the miniball-displaced adventitia from contact with the inclined surface of the wedge-insert to provide rebound redirection without perforation of the adventitia. If the foam-wedge is too thick, the miniball is more likely to perforate the adventitia and come to rest in the foam where it would be harmless but nonfunctional. It is preferable to conserve the functionality resulting from each discharge as well as minimize the risk of perforation. The availability of materials that cover a wide range of resilience makes the thickness required of the outer or abluminal deflection bumper or bounce-wedge less stringent.

The angles of impact and inclination of the planar surface junction between the complementary wedges determine the angle of miniball rebound, while the firmness and shock response of both layers determine the effect on miniball momentum. If driving the adventitia into the outer bounce-wedge with a force of impact that is subperforating, the miniball does not enter the foam-wedge but is rebounded at an acute forward angle without escaping from within the wall of the ductus. The interposition of tissue, much less tissue that has been altered by disease, represents a given element of uncertainty that necessitates in situ testing, addressed below in the section entitle Testing and Tests.

A tendency of the ductus wall to delaminate, as addressed below in the section entitled In Situ Test upon Endoluminal Approach for Intra- or Inter-laminar Separation (Delamination) should be gauged as should its susceptibility based upon hardness as addressed below in the section entitled In Situ Testpon Endoluminal Approach for Susceptibility of the Ductus Wall to Puncture, Penetration, and Perforation. Provided a medicinal miniball that reenters the ductus wall does not stop too far beyond the lesion, it will still be functional. Similarly, so long as it does not pass the distal end of the stent-jacket, a stenting miniball will remain functional.

If partially perforating the adventitia without passing through it, then the miniball may eventually be pulled into the foam-wedge by the attraction of the magnets; if perforating, then the miniball is trapped within the foam and the adventitia returns to its predischarge average position with a tiny puncture wound that should soon heal and close. Both eventualities represent nonfunctional results. The foam-wedge can be wetted and infiltrated with an antibiotic, anti-inflammatory, antithrombogenic, or any other medication in liquid form. The use of an antibiotic thus in a spine and rib type stent-jacket for the gut, for example, militates against infection consequent to a minor spilling of contents.

Trapped within the foam, the miniball does not protrude into or rub against the adventitia as it would were the internal surface of the base-tube applied directly to the adventita. In manufacture, straight-line, that is, noninclined or nonwedged and double-wedge insert linings of different angles are produced for shield-jackets and stent-jackets of different internal diameter. Regardless of type, the jacket together with any added layer or bar magnets mounted to its outer surface is first encapsulated for chemical isolation. The insert is then introduced and bonded with an adhesive or by ultrasonic welding. The adhesive and use of heat to bond the wedge insert to the internal surface of the base-tube depends upon the materials, low viscosity Loctite® Indigo™ 3554™ usable for most.

Typically, the material of the rebound or bounce-wedge is silicone rubber or a thermoplastic polyurethane polymer with a durometer value, resilience, and shape selected for rebound and razor die cut to the angle or rebound desired. The ductus is tested before placing a shield-jacket or stent-jacket, and if perforated in testing, then with stent-jackets having linings that differ in resilience, the rebound imparted to the test rod translated into equivalent rebound of the miniball proposed for use. To achieve accurate discharge and minimize perforations, shield-jackets and stent-jackets are specified for a certain range of test results.

A ductus determined by testing, as will be described below, to include malacotic areas (areas that have become softened, weakened, by disease), which increase the chances for perforations, is treated by injection of a tissue binder and mantled about with a shield-jacket or stent-jacket before discharge. Such jackets are usually of the double-wedge type. Other measures to assist in achieving discharge accuracy apply regardless of the type jacket if any. For example, to avoid the motion as well as the increase in density, hence, effective hardness of the smooth muscle in the wall of a ductus during peristaltic contraction (rigor, contracture, stiffness) discharge is performed with the ductus quiescent, the discharges synchronized to the passage of the contractive waves, or when aperiodic as reduces the confidence of anticipation, with the ductus anesthetized.

If necessary, peristalsis can be subdued or slowed down with drugs such as loperamide, diphenoxylate, or arrested with spasmolytics such as butylbromide (hyoscine butylbromide/Buscopan®), hexamethonium, epinephrine, or sufentanil, with reversal by means of a prokinetic (properistaltic) such as metoclopramide (Paspertin®), cerulein, or neostigmine (see, for example, Thaina, P., Poonpanang, P. and Sawangjaroen, K. 2005. "Comparison of Spasmolytic Activities of Piper Longum, P. Sarmentosum and Quercus Infectoria Extracts with Loperamide and Verapamil in Rat and Guinea Pig Intestinal Tissues," in Acta Horticulturae 680: III, Secretariat of the International Union of Biological Sciences, International Society for Horticultural Science, World Conference on Medicinal and Aromatic Plants, Volume 6: Traditional Medicine and Nutraceuticals, 680:183-189 [available at http://www.actahort.org/books/680/680_28.htm]. See also the section below entitled Motional Stabilization of the Implant Insertion Site.

In arteries, discharge is triggered on the diastoles, where the resistance to penetration and perforation attributable to changes in vasotonicity are reflected in the results of testing as described in the section below entitled In situ Test on Endoluminal Approach for Susceptibility of the Ductus Wall to Puncture, Penetration, and Perforation. Means for dealing with an excessive rate and/or an arrythmia are addressed below in the section entitled Motional Stabilization of the Implant Insertion Site. When the shield or stent-jacket is placed prior to initiating discharge, there should be no effect on expansion with the pulse, and compression of the foam lining should be slight. To limit expansion on the systoles, a shield-, stent-, or other type jacket with a non-double-wedge moisture barrier-coated viscoelastic polyurethane foam lining and side-straps can be temporarily tightened during discharge, even to overlap the edges of the side-slit, but only if the lining is not compressed too thinly to trap a miniball that perforates.

This is less often permissible with a double-wedge lining where the thinner proximal end of foam wedge is usually compressed too thin. Since only expansion is constrained, this is of little value for stabilizing peristaltic action. The moisture barrier-coated viscoelastic polyurethane foam can be coated or suffused with such medication, as addressed below in the section entitled Double-wedge Stent- and Shield-jacket Rebound-directing Linings. When a miniball impacts against the adventitia with sufficient force to compress the moisture barrier-coated viscoelastic polyurethane foam flush against the internal surface of the base-tube but not to perforate the adventitia, the shock response, indentation force deflection, and recovery rate, or rate sensitivity, of the foam absorb the shock, with additional absorption of momentum or shock reduction provided by the resilient surface relatively small.

Figure 11:
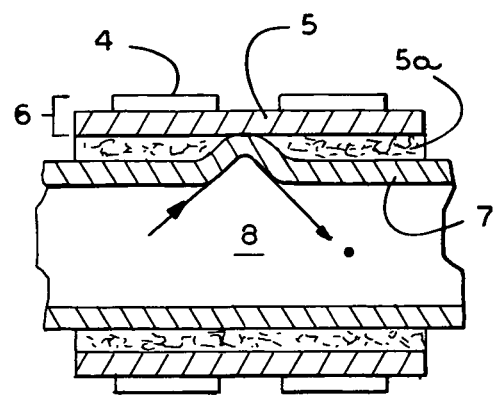
FIG. 11 is a diagrammatic longitudinal section view through a stent-jacket of the extrinsic spaced apart magnet type with a longitudinally noninclined lining of moisture barrier-coated viscoelastic polyurethane foam showing a miniball that has forced the adventitia through the foam lining up against the internal surface of the base-tube with sufficient momentum that the miniball has rebounded into the lumen.

This averts perforation through the adventitia, so that the miniball remains contained within the wall of the ductus. As shown in FIG. 10, a miniball that strikes the adventitia with sufficient force to perforate it will compress the moisture barrier-coated viscoelastic polyurethane foam lining, rebound off of the resilient inclined surface behind, come to rest, and remain trapped within the moisture barrier-coated viscoelastic polyurethane foam lining. If the momentum of the miniball on rebounding adluminally is not sufficient to perforate the intima, the miniball is retained within the wall of the ductus, and depending upon the strength of the wall layers, typically stopped perimedially (subadventitially) or in the media. However, as shown in FIG. 11, when the striking-point along the diseased ductus is atypical in having lost hardness or the momentum of rebound is great enough, the miniball can continue through the wall to perforate into the lumen.

Perforation with a foam-lined shield in position has less potential for complications than does containment within the wall. The miniball may drive the foam flush against the resilient inclined surface, which sustains sufficient momentum to allow perforation into the lumen. A conventional stent-jacket with only a parallel foam lining would trap the miniball preventing it from entering the lumen, but lack the ability to redirect a miniball to a location that would preserve a portion of its function. Whereas the extra-adventitial trapping of a miniball eliminates any risk it could pose, it does so with an increase in jacket diameter and fails to preserve the medicinal, radioactive, and/or magnetic attractive functionality of the discharge.

Whether this or the relative security of entrapment within the foam with little chance for a rebound into the lumen is a clinical judgment. When the adventitia has the elasticity and strength to thwart perforation so that the miniball forces the striking-point and surrounding tissue through the foam against the internal surface of the base-tube, a stent-jacket with a distolaterally (distoabluminally) inclined lining as shown in FIG. 12 can often redirect the rebound to a location within the wall of the ductus so that a medicinal miniball still comes to rest close enough to the targeted area to medicate it or a stenting miniball will still be enclosed by the stent-jacket.

I7a(3). Materials Suitable for Rebound-Directing Double-Wedge Linings

Circumstances recommending the use of a shield-jacket or preplacement of a stent-jacket with a double-wedge lining are addressed above in the section of like title. Double-wedge lined shield-jackets and stent-jackets for placement before initiating discharge are intended primarily to reduce the incidence of nonfunctional miniball placement and secondarily to prevent a perforation in exceptional circumstances when vulnerable anatomy might be struck. Jacket linings must exclude material that could fragment and injure neighboring tissue or introduced into the lumen by a rebound. The inner inclined layer or wedge is made of viscoelastic polyurethane moisture barrier-coated viscoelastic polyurethane foam, addressed above in the section entitled Necrosis and atherogenesis-noninducing conformation of stent-jackets, having properties suitable for the ductus.

This wedge may consist of a proximal-distal formation of adjacent sections of moisture barrier-coated viscoelastic polyurethane foam having miniball impact accommodation or shape compliance that varies in proportion to the thickness of that section. The adhesive used to bond the inner foam wedge to the outer more resilient wedge should be soft enough when cured that a miniball which strikes the outer layer without sufficient momentum to rebound will be trapped at the interface, whether moving along the interface before coming to a stop. The rebound characteristics at all points of impact along the double-wedge should be uniform. This will necessitate graduation in one or both the inner foam and outer bounce wedge components from proximal to the distal end. For both inner and outer wedges, polymers and copolymers that resist degradation in resilience due to cracking within the internal environment are required.

The outer or bounce-wedge can consist of silicone-urethane, for example. Assembling the inner foam wedge of sections graduated for rebound consistency will usually eliminate the need to similarly assemble the outer bounce-wedge of sections. The outer bounce-wedge or bumper should exhibit a firmer rubber-like hardness on the order of 70 Shore durometer A scale at normal body temperature (Yu, J-H., Dillard, D. A., and Lefebvre, D. R. 2001. "Pressure and Shear Stress Distributions of an Elastomer Constrained by a Cylinder of Finite Length," *International Journal of Solids and Structures* 38(38-39):6839-6849). Double bond polyurethane, available from Griffith Polymers Incorporated, Tualatin, Oreg., can also be used, as can the material specified in the section above entitled Internal Environment-resistant Base-tube Polymers, Metals, and Combinations Thereof in the appropriate hardness and resilience, which is more pertinent when the outer wedge is integral with the base-tube as its inner surface.

The inner layer should seldom if ever require any additional anti-migration surface treatment as addressed below in the section entitled Stent- and Shield-jacket Anti-migration Linings. Since the double-wedge lining is placed prior to initiating discharge, it must not contain any substance structural or coated thereon that might do harm were it inoculated into the wall of the ductus when a miniball rebounded to become embedded therein. To reduce the risk of migration, the internal surface of the double-wedge base-tube insert can be embossed or textured, but only to the extent that such relief or depression exercises little if any effect upon function and the direction of rebound.

The wedges are produced by dicing a sheet of the wedge material having a thickness equal to the length of the wedges with a razor-edged steel rule foam cutting die configured as a grid with numerous rectangles each diagonally bisected to create the complementary acute right triangular wedges in the cutting press. The use of heat or laser cutting should not be necessary for materials of appropriate density. The complementary halves must be bonded with an adhesive that upon curing will not fragment if subjected to relatively high density implantation by a multiple barrel radial discharge barrel-assembly in automatic discharge mode.

The complementary wedges can be bonded together and inserted into a tube if not the actual base-tube or shield-jacket to cure, although the extent of displacement at the interface when the wedge halves are rolled following curing of the adhesive should usually be too slight to require that the two be bonded only after having been rolled into a tube shape. Suitable adhesives include biocompatibly plasticized 2-octylcyanoacrylate, n-butyl, or a longer chain cyanoacrylate cement. Biocompatible plasticizers include acetyl tri-n-butyl citrate, acetyl trihexyl citrate, butyl benzyl phthalate, dibutyl phthalate, dioctyl phthalate, n-butryl tri-n-hexyl citrate, and diethylene glycol dibenzoate (Greff, R. J. and Byram, M. M. 1998. "Cyanoacrylate Compositions Comprising an Antimicrobial Agent," U.S. Pat. No. 5,783,177). The base-tube is not opened flat to insert the double-wedge lining.

Instead, the double-wedge lining is bonded having been inserted within the actual base-tube, or if a laminated jacket, then within a tube of equivalent diameter. Alternatively, the double-wedge lining is manually rolled around a mandrel that is slightly larger in diameter than the internal diameter of the equivalent base-tube and held in place with a tab of pressure-sensitive tape. Whether made as such or for insertion when needed by the operator, the outer surface of the double-wedge is coated with adhesive, and the base-tube or if a laminated type jacket, then a tube of equivalent diameter opened just enough to insert the lining so that the ends of the lining and base-tube align.

To inhibit the adhesion of macrophages and formation of foreign body giant cells that would degrade any implant with an outer surface of polyurethane (Labow, R. S., Sa, D., Matheson, L. A., Dinnes, D. L., and Santerre, J. P. 2005. "The Human Macrophage Response During Differentiation and Biodegradation on Polycarbonate-based Polyurethanes: Dependence on Hard Segment Chemistry," *Biomaterials* 26(35):7357-7166; Visai, L., Rindi, S., Speziale, P., Petrini, P., Fare, S., and Tanzi, M. C. 2002. "In Vitro Interactions of Biomedical Polyurethanes with Macrophages and Bacterial Cells," *Journal of Biomaterials Applications* 16(3):191-214) without at the same time impairing immune function that would continue to ward off infection throughout the life of the implant, polyurethanes in base-tubes, wedges, and outer encapsulating coatings thereof incorporate silicone into the soft segments and/or such surface modifying endgroups as further research will establish to be effective (Matheson, L. A., Santerre, J. P., and Labow, R. S. 2004. "Changes in Macrophage Function and Morphology Due to Biomedical Polyurethane Surfaces Undergoing Biodegradation," *Journal of Cellular Physiology* 199(1):8-19; Jones, J. A., Dadsetan, M., Collier, T. O., Ebert, M., Stokes, K. S., Ward, R. S., Hiltner, P. A., and Anderson, J. M. 2004. "Macrophage Behavior on Surface-modified Polyurethanes," *Journal of Biomaterials Science, Polymer Edition* 15(5):567-584; Christenson, E. M., Dadsetan, M., and Hiltner, A. 2005. "Biostability and Macrophage-mediated Foreign Body Reaction of Silicone-modified Polyurethanes," *Journal of Biomedical Materials Research Part A* 74(2):141-155; McBane, J., Santerre, P., and Labow, R. 2005. "Role of Protein Kinase C in the Monocyte-derived Macrophage-mediated Biodegradation of Polycarbonate-based Polyurethanes," *Journal of Biomedical Materials Research Part* 74(1):1-12).

To kill any bacteria that adhere to the implant after removal from the sterile package and before insertion, the implant is wetted with an antiseptic that specifically omits ciclosporin (cyclosporine) or any other immunosuppressant (see, for example, Thorat, S. P., Thane, U. M., Pai, N., and Dahanukar, S. A. 1994 "Inhibition of Phagocytes by Cyclosporin in Vitro," *Quarterly Journal of Medicine* 87(5): 311-314). Closely related research that relates to controlling the rate rather than the warding off of degradation pertains to materials for replacement through breakdown and cellular infiltration for tissue integration or where the object is to accelerate absorption (see, for example, Hong, Y., Guan, J., Fujimoto, K. L., Hashizume, R., Pelinescu, A. L., and Wagner, W. R. 2010. "Tailoring the Degradation Kinetics of Poly(ester Carbonate Urethane)Urea Thermoplastic Elastomers for Tissue Engineering Scaffolds," *Biomaterials* 31(15):4249-4258; McBane, J. E., Santerre, J. P., and Labow, R. 2009. "Effect of Phorbol Esters on the Macrophage-mediated Biodegradation of Polyurethanes via Protein Kinase C Activation and Other Pathways," *Journal of Biomaterials Science. Polymer Edition* 20(4):437-453).

I7a(4). Nonmagnetized Base-Tube and Double-Wedge Shield-Jackets

As shown in FIGS. 4, 5, and 10, to protect the fine vessels and nerves of the adventitia, the stent-jacket is provided with a lining of visco-elastic polyurethane, or temper moisture barrier-coated viscoelastic polyurethane foam. Placement of the jacket may result in injury to few in circumferential complexes in the way of the edges of the side-slit or side slot, not the majority that arise in the lumen and run longitudinally along the surface of the ductus wall, and those injured soon regenerate. The fenestrations or perforations through the jacket afford clearance for fine structured aligned to these. Further to leave intermittent segments of the ductus unencircled with no fine structures in these segments, the stent-jacket can be sectional as addressed below in the section entitled Sectional Extraluminal Stents, Segmented and Articulated or Chain-stents.

For durability and retention of mechanical properties, the foam is of high density. In a specific application, the foam can be surface-wetted or saturated with any liquid medication or coated with any in the form of a paste. Ordinarily, the stent-jacket is placed after the intraductal implants have been placed and therefore plays no part in the physics of ballistic implantation. Means for the recovery of a miniball when the jacket is nonmagnetized include the recovery electromagnets, a trap-jacket and/or an extracorporeal electromagnet with probe prepositioned downstream, and an embolic filter. Unlike a stent-jacket, the resilience and/or thickness of the polymers of each wedge or the adjacent segments comprising each wedge in a double-wedge insert lining for a shield-jacket need not be specified for the strength of magnetization.

Reasons for placing the stent-jacket before initiating discharge are addressed above in the section entitled Circumstances Recommending Preplacement of the Stent-jacket. Preplacing a stent-jacket with more powerful magnetization can result in abrupt displacements (yanking, jerking, deflection) of the muzzle-head, interfering with the accuracy of discharge. The problem is more likely with a stent-jacket having more powerful spaced apart (discrete extrinsic) bar magnets mounted about the outer surface of the base-tube, the need for which is exceptional and can often be avoided by using a more uniformly magnetized intrinsically or quasi-intrinscally magnetized stent-jacket. When the stent-jacket is the end-implant and its magnetization does not pull at the muzzle-head as interferes with achieving accuracy, it is preferable to preposition it from the outset, avoiding the additional risk of adventitial injury and irritation to the access wound.

Otherwise, a nonmagnetized temporary shield which has to be removed and replaced with the magnetized end-implant stent-jacket before closing is used. Using a muzzle-head of larger diameter reduces but does not eliminate abrupt yanking, but in some arteries, will obstruct circulation forcing hurried completion and withdrawal or cardiopulmonary bypass. When a multibarrel radial-discharge barrel-assembly is moved and discharged at high rate under the control of a positional control system, the preplaced stent-jacket will almost invariably be quasi-intrinsically and therefore more uniformly magnetized to no greater strength than is necessary to retract the lumen wall, reducing the problem to a level that can be adapted to and tolerated.

When it does occur, such deflection is sudden and unexpected as to permit response only after encountered and sometimes with limited ability to be counteracted by carefully repositioning the muzzle-head, adjusting the recovery electromagnets in the muzzle-head or with the aid of an extracorporeal electromagnet, or if necessary, withdrawing and reentering with a larger muzzle-head. When greater retractive force is required, however, the number of miniballs discharged and not positioned as desired may be significant, placing miniballs too closely together or bunched, causing a perforation. The field strengths (amplitudes, intensities) of the recovery electromagnets are continuously and separately adjustable and the polarities reversible, but bipolar. This is inherent and essential to allow the fields to be directed; however, bipolarity is eccentric rather than circumferential or radially symmetrical.

Unless exactly counterbalancing the pull, adjustments to greater field strengths than those of the jacket will only reverse the direction of the deflection and risk the extraction of miniballs already placed. Therefore, absent a compelling reason, such as those addressed above in the section entitled Circumstances Recommending Preplacement of the Stent-jacket, preplacement of a magnetized stent-jacket is deferred until after implantation, the provisions of the section above entitled Sequence of Stent-jacket Placement and Implantation in Relation to Trap-extractor (Recovery) Electromagnet Susceptibility and Field Intensity tried, or a temporary nonmagnetized shield-jacket used. When the only reason for placing a magnetized jacket, that is, a stent-jacket, prior to initiating discharge is to protect against perforations, the consequences of a perforation should be assessed, and if the preceding measures are decided against, the use of stays should be considered.

When higher density circumferential implantation is desired to obtain a more closely and uniformly placed formation of miniballs that will distribute the tractive force more evenly, the use of a perforation shield-jacket may be justified. This is usually the case when discharge is automatically executed under machine control at a rate that precludes stopping in time to intervene before many miniballs have been discharged. A perforation type shield-jacket is a temporary nonmagnetized base-tube or double-wedge lined jacket placed during implantation discharge and replaced with the magnetized stent-jacket as the absorbable or nonabsorbable end-implant before closing. Shield-jackets that include sufficient continuous ferromagnetic matter can provide warming of the substrate ductus by magnetic or electromagnetic heat induction.

Perforation shield-jackets are unusable as radiation shield-jackets, which are usually introduced as the outer absorbable layer of a laminated stent-jacket that must remain until decay has progressed to a level safe for surrounding tissue, whether dissolution is spontaneous or on demand, as addressed above in the sections entitled Implants that Radiate Heat on Demand and Noninvasive dissolution on demand of absorbable stent-jackets, base-tubes, radiation shields, and miniballs. Nonmagnetized radiation and perforation shield-jackets for use along the vascular tree usually depend upon a downstream external electromagnet and/or an impasse-jacket to intercept a miniball that accidently enters the circulation.

I7b. Stent- and Shield-Jacket Moisture Barrier-Coated Viscoelastic Polyurethane Foam Linings Viscoelastic polyurethane foam is addressed above in the sections entitled Preliminary Description of the Invention and Requirement for Moisture barrier-coated viscoelastic polyurethane foam Linings. Stent-jackets, shield-jackets, the inner wedge of double-wedge linings, impasse-jackets, and some magnet- and clasp-jackets have an inner lining of higher density moisture barrier-coated viscoelastic polyurethane foam. Even in nonhyperlipidemic subjects, obstruction of the vasa vasora by compression results in medial and intimal hypoxia and the undernutrition of cells in the luminal wall that leads to cellular necrosis and its associated immune response whereby leukocytes infiltrate the intima producing the chronic inflammation of atherosclerosis and endothelial dysfunction that impairs vasotonic control (references provided above in the section entitled Accommodation of the Adventitial Vasculature, Innervation, and Perivascular Fat).

Avoiding this disease process initiated by circumvascular compression is accomplished by providing the stent-jacket with a slit so that it expands and contracts with the ductus and affords an opening to the surrounding medium; perforations along the side; and by lining the stent-jacket with moisture barrier-coated viscoelastic polyurethane foam (low resilience polyurethane foam, visco-elastic polyurethane foam), which enfolds rather than compresses the vasa vasora and nervi vasora, whether the foam itself is compressed. Regardless of type, the lining is bonded to the inner surface of the outer layer or layers of the jacket after those have been encapsulated together for chemical isolation as an added precaution against any leakage of lanthanoid and attack by the immune system. The unencapsulated inner layer of moisture barrier-coated viscoelastic polyurethane foam is protected by the chemical Materials Suitable for Rebound-directing Double-wedge Linings.

The shape compliance of the foam is enhanced by the warmth of the internal environment and at the outer surface of the encircled ductus. Especially dense vasa provide greater warmth and are least disturbed or stifled by heat entrapment through the use of stent-jackets that minimize ensheathment by providing apertures or chain-stents that link the substents at intervals where the ductus is not encircled. The lining provides several advantages, to include accommodating small structural projections that as part of the stent-, impasse-, or shield-jacket would otherwise protrude into the adventitia, accommodating the out of roundness along a larger stent-jacket expansion insert used when the ductus is interim swollen.

This is addressed below in the section entitled Stent-jacket Expansion Inserts, and latitude in diameter that eliminates the need to recover a deliberately oversized jacket placed in later childhood for replacement following growth. In some instances where the wall of the ductus is too thin or weak to accommodate the placement of an extraluminal stent but is intimately associated with and adherent to surrounding tissue, it is possible to include a thickness of the surrounding tissue within the stent or jacket. One method for predetermining such a condition is intravascular or intraductal ultrasound. Thin walled veins are not susceptible to atherosclerosis; however, veins are suitable for the placement of impasse-jackets, which can include some surrounding adherent tissue when the vein itself is weak or weakened by disease.

The no-touch technique for harvesting the saphenous vein (see, for example, Sepehripour, A. H., Jarral, O. A., Shipolini, A. R., and McCormack, D. J. 2011. "Does a 'No-touch' Technique Result in Better Vein Patency?," *Interactive Cardiovascular and Thoracic Surgery* 13(6):626-630; Dashwood, M. R., Savage, K., Tsui, J. C., Dooley, A., Shaw, S. G., Fernández Alfonso, M. S., Bodin, L., and Souza, D. S. 2009. "Retaining Perivascular Tissue of Human Saphenous Vein Grafts Protects Against Surgical and Distention-induced Damage and Preserves Endothelial Nitric Oxide Synthase and Nitric Oxide Synthase Activity," *Journal of Thoracic and Cardiovascular Surgery* 138(2):334-340; Rueda, F., Souza, D., Lima Rde, C., Menezes, A., Johansson, B., and 5 others 2008. "Novel No-touch Technique of Harvesting the Saphenous Vein for Coronary Artery Bypass Grafting," [in English] *Arquivos Brasileiros de Cardiologia* 90(6):356-362) would appear to recommend minimizing direct contact with and handling of the vein even when unaffected by disease. For placing an impasse-jacket, the incision is not more than a few centimeters in length and a small fraction the length required to harvest the vein.

Conditions that would recommend the use of a stent in very young patients are rare and seldom long term. When the stent-jacket is placed prior to discharge, the interaction between the jacket, the diseased tissue it encircles, and the forces generated by discharge make for a more complex set of variables than when a jacket is uninvolved. Susceptibility to perforation due to degradation in the elasticity of the ductus is determinable using the testing procedure described below in the section entitled Test upon Endoluminal Approach for Susceptibility of the Ductus Wall to Puncture, Penetration, and Perforation and agents for causing the ductus wall to thicken under the section below entitled Attainment of Implantable Intramural Thickness. The jacket is made to a high standard of consistency, but missing a significant spot in in situ testing can result in nonfunctional positioning of miniballs if not entry into the lumen.

In any stent-jacket or perforation type shield-jacket, the moisture barrier-coated viscoelastic polyurethane foam lining must be thick enough to entrap a perforating miniball without allowing it to rebound. A double-wedge lining has the more complex function of trapping and decelerating a miniball that enters with insufficient momentum to rebound, but imparting a functional angle without excessive deceleration of a miniball that enters with sufficient momentum to rebound. A functional angle of rebound is imparted by the more resilient bounce-surface of the outer wedge of the double-wedge insert lining, and less often, by the inclined inner surface of the base-tube so that the insert lining includes only the foam wedge. In either case, the inner wedge of moisture barrier-coated viscoelastic polyurethane foam is of continuously changing thickness where the momentum on entry determines whether the miniball will be trapped or rebounded into the wall of the ductus.

Notwithstanding this variation in thickness, the foam must be thick enough to trap and retain a miniball that enters without protrusion into the adventitia, but thin enough to avoid absorbing too much momentum as would trap or improperly redirect a miniball of sufficient residual momentum to be rebounded to a functional location in the wall. To achieve this uniformity and avoid the need for a jacket of larger diameter as would encroach upon the surrounding tissue, when necessary, the foam wedge is assembled from adjacent segments of density to offset the difference in thickness. The resilience and/or thickness of the moisture barrier-coated viscoelastic polyurethane foam in a double-wedge lining insert must take into account whether the insert is to be used in a magnetized stent- or a nonmagnetized shield-jacket. The contribution to acceleration of a miniball nearing and deceleration when rebounding away from more powerful magnets vary according to the strength of magnetization.

If significant, the magnetic force can retard a rebound that would otherwise have resulted in a functional positioning of the miniball. To avoid such interference due to a needlessly powerful magnetic field, as well as to minimize the risk of pull-through or delamination, magnet selection is primarily based upon achieving luminal patency on a long-term basis with the minimum field strength necessary to maintain and secondarily on obtaining uniformity of attraction over the segment encircled. The resilience and/or thickness of the polymers of each wedge or the adjacent segments comprising each wedge in a double-wedge insert lining for a stent-jacket must be specified for the strength of magnetization. Neither the internal inclined or rebound surface of the outer wedge or of the base-tube nor the inner or outer surfaces of the foam wedge need ever require lamination with or an additional layer of another material to increase or decrease its resilience.

I7c. Stent- and Shield-Jacket Anti-Migration Linings

Migration is a concern with stent-jackets, which are implanted to remain in place for an indeterminate period if not life, but not temporary jackets such as perforation shield-jackets, which remain in use during discharge and perhaps a relatively short ensuing period when a shield-jacket capable of being warmed by heat induction is used for that additional purpose. When the outer surface of the stent- or shield-jacket is not in contact with neighboring tissue that moves in relation to it, the moisture barrier-coated viscoelastic polyurethane foam lining, end-ties, side-straps, and if a stent-jacket, the magnetic attraction on of the ductus-mural implants prevent migration, or the longitudinal displacement of the jacket along the ductus.

In most instances, the moisture barrier-coated viscoelastic polyurethane foam lining alone will afford sufficient resistance to lateral displacement so that no additional anti-migratory measures such as impressing the surface of the foam with a deep surface texture or overlaying the foam with gauze is necessary. Gauze used for this purpose should readily stretch and detract from the ability of the moisture barrier-coated viscoelastic polyurethane foam to enwrap the adventitial microstructures as little as possible. However, when the outer surface of the jacket is in moving contact against neighboring tissue so that side-straps rub against and abrade the tissue, the risk of erosion or fistulization to the neighboring tissue and migration of the jacket become concerns. If necessary, as when end-ties are not wanted, nonallergenic gossamer grade woven surgical gauze is bonded by means of a plastic adhesive to the inner surface of the moisture barrier-coated viscoelastic polyurethane foam regardless of whether the foam is the inner wedge of a rebound-redirecting double-wedge.

To avoid brittleness that would cause the gauze to become stiff, irritate the adventitia, and eventually disintegrate through the accumulation of microfractures, a surgically acceptable adhesive that remains pliable after curing, such as one polyurethane based (see, for example, Marois, Y. and Guidoin, R. 2001. "Biocompatibility of Polyurethanes," in Vermette, P., Griesser, H. J., Laroche, G. and Guidoin, R. (eds.), *Biomedical Applications of Polyurethanes*, Austin, Tex.: Landes Bioscience) is used. The adhesive should be absorbed into or adsorbed onto the fabric of the gauze without filling the interstices as too thick or filming due to surface tension as too thin. The adhesive is applied to the gauze at isolated spots at the periphery of the lining, the number kept to the minimum to least detract from the ability of the foam to comply with the surface anatomy of the adventitia, any filming over of gauze openings removed.

Suitable adhesives are specified below in this section. The delayed healing that has been observed with polyurethanes may be pertinent only when a stent-jacket with gauze covered lining is positioned prior to discharge. Accordingly, end-ties and where nonencroaching on neighboring tissue side-straps are preferable for prepositioned stent-jackets. When the jacket is placed after implantation, stay incision flaps or any perforations created during discharge will already have sealed. The stay incisions would already have been bonded shut by the tissue bonding agent dispensed by the tool onto the emerging stay, and a perforation would have been sealed almost entirely by the endoplasm released by the cells along the trajectory, blood, or serous fluid.

Thus, before the stent-jacket is placed, the external surface of the ductus recovers to a condition sufficiently intact to place the jacket despite previous microincisions or perforations. A perforation shield-jacket placed just prior to discharge or following stay insertion which contains sufficient continuous ferrous content to heat noninvasively by heat induction can be warmed to accelerate the coagulation of the exudates and body fluids that enter the perforation trajectories or the initial setting of the stay insertion incision bonding (infibulating, fusing) adhesive. The gauze is taken up by the foam but presents a grating in contact with the adventitia that resists migration, and may be enhanced by tissue infiltration. The base-tube is provided with 'breathing' holes or perforations for exposure to the environment.

When, exceptionally, a perforation could lead to a serious consequence such as striking a vulnerable ganglion, a rebound-directing or double-wedge lining, as described in the section above entitled Double-wedge Stent- and Shield-jacket Rebound-directing Linings, is used. With a ureter, which has an outer fibrosa, or a fallopian tube, an outer serosa, for example, the outer layer is not so densely innervated or supplied with vessels that a foam lining is necessary to protect this fine structure. The lining then serves as a perforation trap and anti-migration feature, whether in a straight line or double-wedge stent-jacket. For this reason, stent- and shield-jackets include a foam insert lining rather than an internal surface that is made only resistant to displacement by having been rib or ridge textured through embossing or the insertion and bonding of a grid, for example.

Imparting a deeply textured internal surface to the foam by relief or embossing increases its anti-migratory traction. When the stent-jacket is positioned prior to initiating discharge, the materials and conformation of a straight line lining prevents rebounding by entrapping the miniball. If of the double-wedge type, lower momentum miniballs are trapped but higher momentum ones rebounded to a ductus-intramural terminus that preserves function. The protective foam lining should come up to the edges of the side-slit or side-slot. Since any stent-jacket should include a protective lining that extends entirely to the edges of the side-slit or side-slot, the expansion insert is bonded along the slit or slot interface and a lapped over portion that extends a short distance along the outer surface of the jacket.

Expansion inserts of greater length include a straight-line, not a double-wedge, moisture barrier-coated viscoelastic polyurethane foam lining. An anti-migration deep texture surface pattern can be cut into the inner polyurethane moisture barrier-coated viscoelastic polyurethane foam layer of a double wedge lining or gossamer gauze applied to its adventitial contact inner surface. When the base-tube of the stent-jacket is made, for example, of Bionate® thermoplastic polycarbonate urethane copolymer tubing and a rebound lining as described above is not to be inserted, the gauze can be glued directly to the inner surface of the foam lining.

Suitable adhesives for bonding the gauze to the surface at a few isolated spots include plasticized long carbon chain cyanoacrylate cements, such as 2-octylcyanoacrylate, 4 Meta/MMA-TBB® 4-metacryloyloxyethyl trimellitate anhydride (4-META), prepared using methylmetacrylate (MMA) as monomers and tri-n-butyl borane (TBB) as an initiator, Histoacril® 2-cyanobutylacrylate, and Bucrylate® isobutylcyanoacrylate. Cyanoacrylate cement used to seal adventitial entry incisions produced by stay insertion (addressed below) are eventually broken down or absorbed and can be drug-releasing before infiltrated and replaced by tissue.

The placement of a double-wedge stent- or shield-jacket lining with a textured or gauze overlain surface to serve as an anti-migration lining prior to discharge in order to prevent a perforation from striking neighboring tissue should take into account the effect, if any, of the gauze or textured pattern on the rebound and trapping characteristics on the miniball. Different gauzes, mesh thicknesses, hole sizes, and adhesives can produce different rebound characteristics. If the range of rebound variance exceeds that tolerable or results in unacceptable rebounds in too high a percent, end-ties, addressed in the section that follows, must be depended upon to prevent migration.

I8. Radiation Shielded Stent-Jackets

Radiation shield-jackets, addressed above in the section entitled System Implant Magnetic Drug and Radiation Targeting, are distinct, whereas radiation shielding stent-jackets have an outer laminated layer bonded about an intrinsically or quasi-intrinsically magnetized stent-jacket. Shield-jackets used to prevent a perforating miniball from striking adjacent tissue rather than to allow postprocedural warming by noninvasive magnetic or electromagnetic heat induction are removed after discharge implantation before irradiation is allowed an interval for antiproliferative (antimitotic) or antiangiogenic or other antineoplastic uptake and are not radiation shielded.

The shield layer comprises an absorbable or degradable matrix containing heavy metal shielding particulate. To allow compliance when the shield is directly laminated to the outer surface of the stent-jacket, the shield must also be slit and rotated to the side opposite the source of radiation. The problem of a shield that to be compliant must leak is reduced by interposing closed cell moisture barrier-coated viscoelastic polyurethane foam cuffs at either end between stent-jacket and a larger diameter shield that does not expand and contract along with the stent-jacket it encircles and by extending the jacket and shield beyond the segment affected, gas exchange or 'breathing' afforded by the fenestrae.

Such a shield must be slit to fit over the ductus, but the slit is sealed with a suitable cement, usually cyanoacrylate. The digestive tract having to expand during the course of normal function, sufficient clearance is usually available to place such a larger diameter closed shielded stent. In a spine and ribs-configured stent-jacket placed along the esophagus, provided the thickness of the cuffs accommodate the expansion of a passing bolus, this allows the free and independent movement of the ribs within the outer shield. The matrix must be elastic for compliance with the expansion and contraction of the ductus, slit or slotted in alignment with the subjacent stenting, and the particulate elongated and overlapped or imbricated as least to detract from elasticity.

The particulate can consist of tungsten, gold, and/or osmium, for example, but not lead, platinum, or rhodium, which in such small quantity lack sufficient shielding effect. A shield for high dose-rate ductus-intramural implants with a long half-life to be the removed in a followup procedure at a time to be determined by imaging inspection so that the time is not predictable incorporates ferrous wire to allow breakdown on demand by heat induction. Brachytherapy that confines radiation to the lesion most damages targeted hyperproliferative and least damages nontargeted normoproliferative cells. The radiation can be delivered by seed stays or miniballs implanted within the wall of the ductus or by seed miniballs arrested in place within the lumen by a strongly magnetized stent-jacket with a radiation shield.

An impasse-jacket is designed to allow the noninvasive extraction of miniballs whether endoluminally suspended or ductus-intramurally implanted and is compatible with an the outer radiation shield layer only when the outer layer is destructible on demand by heat induction to expose the extraction grid to the extracorporeal extraction electromagnet, as addressed below in the section entitled Stereotactic Resituation of a Mispositioned Miniball, among others. Impasse- and more strongly magnetized stent-jackets with or without a radiation shield are suitable for suspending miniballs that release chemotherapeutic agents at the target segment. If the drug is carrier nanoparticle bound, the jacket will suspend the miniballs in place, may assist in miniball dissolution, and draw the drug into the wall of the ductus. Combined radiation and chemotherapy are obtained by interspersing seed and drug-releasing ductus-intramural implants.

I9. Jacket End-Ties and Side-Straps

A stent-jacket to be positioned at a site especially prone to migration has side-straps and/or end-ties added toward either end. Side-straps wrap around the jacket to elastically cinch and tighten its grip. Unlike end-ties or end-straps which stabilize the jacket in longitudinal position by tying directly to the ductus off to the sides of the jacket, side-straps tie about the jacket. Side-straps must therefore be fitted with the ductus quiescent and adjusted to not detract from compliance to expansion by adding significant resistance. Temporarily tightening a collar about a ductus such as side-straps, end-ties, or end-straps is a local or targeted means for suppressing ductus intrinsic or pulsatile motility that detracts from accuracy during discharge implantation.

A shield-jacket is rarely left in place long enough for migration to result. A shield- or stent-jacket with side-straps, end-straps, or end-ties placed before initiating discharge for the primary purpose of stopping and containing a perforating miniball can serve a secondary purpose of stabilizing the ductus to allow greater accuracy of implantation discharge, as well as a third purpose of allowing the jacket to be warmed by induction heating when the jacket contains sufficient continuous ferrous material. Side-straps can be rotated at the rivet fastening these to the jacket to serve as end-straps; however, to do so fails to achieve more secure stabilization or satisfy the requirement of end-ties, which is to achieve stabilization with little increase in jacket diameter.

Side-straps are made of braided multifilament spandex fabric woven loosely as to least interfere with breathability as a backing for hook and loop (touch-, burr-, Velcro®) fasteners, the hooks at the end on one side and loops on the other side of the backing. The spandex in side-straps should add as little as possible to resistance of the jacket to expansion. Side-straps are generally lined with segments of moisture barrier-coated viscoelastic polyurethane foam on the internal surface of the spandex backing that separate if the spandex is stretched.

End-ties are off-to-either-end outrigger tethers or end-tethers used as longitudinal position stabilizers at sites with inadequate periductal clearance for side-straps, which become thicker when not stretched and would protrude into, rub against, possibly erode, or even fistulize neighboring tissue. Only the hook and loop fastening end tab of the suture end-tie is made as are side-straps, and end-ties are fastened off to the sides rather than around the jacket. Except for the end fastening tab, end-ties are made of soft braided and loosely woven multifilament suture, such as Neobond®, coated polyester, or Durasil® silk suture, which is specified for absorbability (spontaneous dissolution responsive to enzymatic or hydrolytic action) or nonabsorbability, as is the jacket to which the end-ties are connected.

I9a. Form of End-Ties

Where a lack of clearance prompts the avoidance of side-straps, end-ties of woven (braided, multifilament, stranded) suture are used. Silk suture exhibits good elasticity but must be avoided in silk hypersensitive (allergic) patients, synthetic suture used in lieu thereof. The use of hard monofilament suture is discouraged. For a jacket of given length, end-ties pose the disadvantage of requiring a longer entry incision to apply. Other disadvantages of end-ties as compared to side-straps is that more time is necessary to fix the jacket in position with forceps. Suture is used only for tie lines, never to attach directly to the ductus, which even when attached with multiple turns, is likely to constrict, irritate, and could even strangulate the ductus.

As are lining and expansion inserts, side-straps and end-ties are usually attached to a jacket on an as needed basis. This allows tailoring of the jacket to the specific site and jacket standardization that reduces the production cost. Spandex side-straps and end-tie suture are fastened to the jacket, and end-tie suture fastened to the spandex end-tab that grasps the ductus, in the same way. The end connecting tabs of end-ties are made of the same layers as are the end-straps of a segmented stent but are attached not to the jacket but rather to suture that is attached to the jacket, and to clearly distinguish the two, are referred to as end-tabs, not end-straps. The term 'outrigger' also pertains to off at the ends impasse-jacket anchors, and should be qualified as pertaining to end-tie or impasse-jacket outriggers.

End-tabs A punch and riveting hand tool is used to insert wide-head nonbioabsorbable biocompatible rivets, such as of tantalum, toward the ends of the jacket or end-tab. To anchor the spandex band of a side-strap, the spandex is flush riveted against the jacket, and the suture of an end-tie wound about and knotted beneath the rivet head before the rivet is closed. The wires used to connect the jackets in articulated type chain stents are fastened toward the ends of the separate sections or substents in the same way as are end-straps to the extension tabs, the suture to the base-tube and to the ductus connecting, the difference between end-ties and segmental jacket connecting wires being that end-ties are made of suture.

The end-tabs of end-ties that cinch about the ductus must not be so narrow that the spandex backing digs into, cuts into, or constricts the ductus or is able to slide along the ductus without being made too tight or so that too few hooks and loops secure the straps in position. End-tie end-tabs for cinching the suture about the ductus are no different than side-straps in having a stretchable backing of spandex, hooks and loops on opposite sides and opposite ends of the tab, with portions of the tab in contact with the ductus lined with moisture barrier-coated viscoelastic polyurethane foam segmented as necessary to stretch with the spandex and faced with heavy gauged gossamer gauze to hold fast. As depicted in FIGS. 13 and 14, a unit stent-jacket cut from a continuous segmented-type chain-stent has tabs that project past the rest of the ends of the base-tube.

Such hook and loop end-tab fastening straps are made as are side-straps and fastened to the base-tube extension tab at each end by means of rivets, but cinching about the ductus rather than the jacket, are not side-straps, and not made of suture, are not end-ties, but rather end-straps. As many jacket segments as necessary are cut from the continuous strip, so that such a segmented jacket is able to follow an inflamed ductus however long or bending although increased length and bends necessitate wider exposure. To preclude the end corners and edges of the extension tabs from protruding into the adventitia, the moisture barrier-coated viscoelastic polyurethane foam lining with or without gauze facing within the main or circular part of the elastic polymeric base-tube is not discontinued along the inside of the tab.

Side-straps and end-straps may be singular so as to wrap entirely about the ductus and secure with hooks at the inside end of the strap and loops along the outside over the length where the hooks attach or double, so that the inner end segment of one has hooks and the outer face of the other loops. Since these are added for the application, either singular (unilateral) or double (bilateral, opposed) straps are chosen as allows placement most efficiently for the specific site. Whether one-sided (unilateral) or opposed (bilateral), straps or end-tie connecting tabs are kept as short as allows the ductus to be cinched securely and nonconstrictively without nonessential doubling or overlapping.

This is especially the case when the connecting hook and loop segments include the moisture barrier-coated viscoelastic polyurethane foam layer, which detracts from stretchability, hence, compliance to the action in the ductus as well as detracts from the surrounding clearance. For this reason, straps placed where clearance is minimal should be no longer than allows secure fastening, with the moisture barrier-coated viscoelastic polyurethane foam layer omitted from the hook and loop connecting segments. So that a nonoverlapped portion will be free to stretch in compliance, strap length is set for the quiescent circumference of the ductus. Due to the force of expansion of the ductus and the lack of resistance to the force of the side-slit or side-slot, a stent-jacket can vary over a range of elasticity without significant effect upon the substrate ductus, making stent-jackets usable with different type ductus of suitable diameter.

I9b. Use of End-Ties

The operator fastens the belt-straps when the ductus is quiescent or, if an artery, during diastole, being certain not to pull at so as to stretch the spandex-backing before engaging the hooks and loops. As addressed below in the section entitled Motional Stabilization of the Implant Insertion Site, when miniballs rather than stays are used so that the jacket can be positioned prior to implantation discharge, the stent-jacket can be used with or without drugs to suppress a pulse that is too fast and/or irregular to allow accuracy. The jacket is temporarily tightened during discharge and thereafter loosened to the functional tautness, which is confirmed before closing.

For this reason, the concurrent use of a cardioplegic or autonomic function suppressing drug such as an opioid or anticholininggic is deferred until the long-term tautness has been ascertained. Magnetic stent-jackets generally use end-ties or if segmented, end-straps, which are located past the ends of the jacket and fastened directly onto the substrate ductus, whereas nonmagnetic stent-jackets use side-straps, which gird about the stent-jacket itself. Unlike shield- and stent-jackets, to which straps and ties are added only when the location for positional stabilization poses a greater risk of migration, clasp-wraps and magnet-wraps lack a resilient layer and the binding value of attraction between intravascular and extravascular components, and are therefore secured by means of side-straps included in their basic structure.

When a stent-jacket had included an expansion insert since absorbed or lithotripsied as described below in the section entitled Expansion Inserts Absorbable, Meltable, and Comminutable for Time-discrete Decremental Contraction of Stent-Jackets, to have used side-straps toward the ends of the base-tube would add the strap stretching resistance to the resistance to expansion of the base-tube, and following contraction, the belt-straps would be loose. Since side-straps are not compatible with expansion inserts, end-ties are used instead. Also incompatible are side-straps that overlap rather than pass between discrete or separate magnets mounted about the outer surface of the base-tube, although, the fact that side-straps close about the jacket rather than the ductus, and for that reason, can often be made narrow enough to do this.

Side-straps that lap over the magnets will often produce an outer diameter for which sufficient clearance is lacking, and if too tight, can cause a thin base-tube to bulge inward. Spaced apart magnets are used where intense field strength is required; more often the distribution of evenly distributed minimal attractive force is appropriate and obtained with a quasi-intrinsically or intrinsically magnetized stent-jacket, which will usually admit of the added diameter. When side-straps would add too much to the diameter or affect the resultant resistance to stretching or the effective resilience of the jacket in response to the intrinsic expansion of the ductus, end-ties are used instead; the thickness or material of the base-tube is not changed to offset the use of thicker side-straps.

Articulated type chain-stents attached by wires usually stabilize each other; however, if intermediate anti-migration anchoring is desired, side-straps are connected with the same wide head rivets as fastens the wires or strong suture used to connect the substents. An chain-stent positioned along a flexing ductus is generally tethered at both its intermediate and terminal or end stent-jackets (end-stents) by end-straps if segmented or by terminal end-ties and if necessary, intermediate side-straps if articulated. The same wide-head rivets are used to secure both the side-straps and interjacket connecting wires. To prevent premature hook and loop connection during placement, a strip of pressure-sensitive tape is applied to either the hooks or loops before the jacket is inserted through the entry portal. As is the stent-jacket itself, side-straps are fitted to the ductus during diastole or smooth muscle inaction for expansion with the pulse or peristalsis as pertinent.

I10. Absorbable Extraluminal Magnetic Stent-Jackets and Materials

I10a. Absorbable Base-Tube and Stent-Jacket, Miniball, Stay, and Clasp-Magnet Matrix Materials An absorbable extraluminal magnetic stent-jacket is intended to maintain luminal patency without contact, the imposition of significant stress upon, or deformation of the internal (endothelial) surface of the lumen while the ductus heals and then disintegrate. It consists of subadventitially or subfibrosally placed miniballs and a stent-jacket that consist of an absorbable polymeric material of the kind used to make tissue engineering scaffolding and absorbable suture, as specified in the section below entitled Absorbable Stent-jacket Expansion Insert Materials with Relatively Short Breakdown Times, among others (see, for example, Nair, L. S. and Laurencin, C. T. 2006. "Polymers as Biomaterials for Tissue Engineering and Controlled Drug Delivery," *Advances in Biochemical Engineering and Biotechnology* 102:47-90; Gunatillake, P. A., and Adhikari, R. 2003. "Biodegradable Synthetic Polymers for Tissue Engineering," *European Cells and Materials* 5:1-16, available at http://www.ecmjournal.org/journal/papers/vol005/pdf/v005a01.pdf).

The miniballs include nonmagnetized superparamagnetic magnetite or maghemite nanoparticles or finely grained powder and the stent-jacket small magnetized neodymium lanthanoid grains or particulate encapsulated for permanent chemical isolation, usually within gold. Absorption may be spontaneous or as addressed in the section that follows, forced on demand. The need for an outer magnetized base-tube or stent-jacket is associated with a stenting and/or a drug carrier nanoparticle-attracting function. The large number of biocompatibility absorbable polymers afford a range of persistence in the internal environment, or degradation profiles that include bulk and surface erosion, sufficiently extensive to negate the need to modify these.

These include materials used in absorbable suture and tissue engineering scaffolding, addressed below in the section entitled Stent-jacket Expansion Inserts, which consist of polyesters, primarily homopolymers and copolymers of poly (lactic acid) and poly(glycolic acid) to poly(amino acids), polyanhydrides, polyorthoesters, polyurethanes, polycarbonates, copolyesters of ε-caprolactone, trimethylene carbonate, and para-dioxanone. In order of increasing interval pending disintegration sought, polyurethane elements, to include the moisture barrier-coated viscoelastic polyurethane foam lining in an absorbable or absorbable on demand jacket, is treated to encourage, is not treated, or is treated to prevent the formation of foreign body giant cells that would effect its breakdown.

A light dusting of the lining with virtually any foreign proteinaceous matter to which the patient has been determined not to be hypersensitive will invite attack reducing persistence, while means for discouraging the formation of foreign body giant cells on materials containing polyurethane, such as moisture barrier-coated viscoelastic polyurethane foam linings, are addressed above in the section entitled Materials Suitable for Rebound-directing Double-wedge Linings. Such treatment must be compatible with any medication that the lining is to release. When the period required for healing is predictable, the material of the base-tube or matrix of a disintegrable radiation shield-jacket is selected on the basis of spontaneously disintegrating at about the same time.

When the period required for healing is indeterminate, materials are incorporated into the absorbable stent so that it can be noninvasively disintegrated on demand, as addressed in the following section. For temporary conditions, absorbable endoluminal are preferable to nonabsorbable stents. Absorbable radiation shields can also be used to encircle an impasse-jacket, allowing extraction of radiation seed miniballs once depleted. Absorbable base-tube and matrix materials with the elasticity and resilience required are not intrinsically magnetizable (ferromagnetic), necessitating the addition of ferromagnetic material by embedment, doping, lamination, or coating.

Magnesium is suitable for use in a minimally compliant or noncompliant endoluminal stent (see, for example, Erbel, R., Di Mario, C., Bartunek, J., Bonnier, J., and 12 others 2007. "Temporary Scaffolding of Coronary Arteries with Bioabsorbable Magnesium Stents: A Prospective, Non-randomised Multicentre Trial," *Lancet* 369(9576):1839-1840, also referred to above in the section entitled Basic Strengths and Weaknesses of Prior Art Stenting in Vascular, Tracheobronchial, Gastrointestinal, and Urological Interventions).

The release of drugs during dissolution of absorbable materials is well over a decade in the making and under continued development (see, for example, Zhang, C., Chen, X., Liu, G., Chen, R., and Guo, S. 2016. "Mechanism and Kinetics of Drug Release from Poly(ε-Caprolactone) Based Extrudates Prepared by Hot-melt Extrusion," *Journal of Macromolecular Science. Part B, Physics* 55(3):285-298; Lenzi, E. K., Novatski, A., Farago, P. V., Almeida, M. A., Zawadzki, S. F., and Menechini Neto, R. 2016. "Diffusion Processes and Drug Release: Capsaicinoids—Loaded Poly (ε-caprolactone) Microparticles," *Public Library of Science One* 11(6):e0157662; Almeida, M. A., Nadal, J. M., Grassiolli, S., Paludo, K. S., Zawadzki, S. F., and 3 others 2014. "Enhanced Gastric Tolerability and Improved Anti-obesity Effect of Capsaicinoids-loaded PCL [polycaprolactone] Microparticles," *Materials Science and Engineering. C, Materials for Biological Applications* 40:345-356; Miladi, K., Ibraheem, D., Iqbal, M., Sfar, S., Fessi, H., and Elaissari, A. 2014. "Particles from Preformed Polymers as Carriers for Drug Delivery," *Experimental and Clinical Sciences Journal* 13:28-57; Seremeta, K. P., Chiappetta, D. A., and Sosnik, A. 2013. "Poly(ε-caprolactone), Eudragit® RS 100 and Poly(ε-Caprolactone)/Eudragit® RS 100 Blend Submicron Particles for the Sustained Release of the Antiretroviral Efavirenz," *Colloids and Surfaces. B, Biointerfaces* 102: 441-449; Puga, A. M., Rey-Rico, A., Magariños, B., Alvarez-Lorenzo, C., and Concheiro, A. 2012. "Hot Melt Poly-ε-caprolactone/Poloxamine Implantable Matrices for Sustained Delivery of Ciprofloxacin," *Acta Biomaterialia* 8(4):1507-1518; Lin, M., Meng, S., Zhong, W., Li, Z., Du, Q., and Tomasik, P. 2008. "Novel Biodegradable Blend Matrices for Controlled Drug Release," *Journal of Pharmaceutical Sciences* 97(10):4240-4248; Huatan, H., Collett, J. H., Attwood, D., and Booth, C. 1995. "Preparation and Characterization of Poly(epsilon-caprolactone) Polymer Blends for the Delivery of Proteins," *Biomaterials* 16(17): 1297-1303).

Heat inductive and chemical means addressed in the following section entitled Noninvasive Dissolution on Demand of Absorbable Stent-jackets, Base-tubes, Radiation Shields, and Miniballs can be used to release chemicals such as solvents incorporated into these materials within small capsules to accelerate dissolution and/or to release drugs, or the latter first when embedded at the surface. Magnesium can be alloyed to convert it from paramagnetic to ferromagnetic allowing its use in an absorbable impasse-jacket extraction-grid, but however alloyed while still remaining absorbable, magnesium lacks the sustained elasticity required for compliance with ductus motility required of an extraluminal stent, radiation shield matrix, or any other component that must not impede the expansion and contraction of the substrate ductus.

No single material that would allow making a stent-jacket which is intrinsically magnetized, absorbable without the incorporation of a second material, and flexible currently available, an absorbable quasi-intrinsically magnetized extraluminal stent with or without an outer absorbable radiation shield laminated is used to treat a ductus wall that is expected to require stenting only over a limited interval. For spontaneous dissolution, such a jacket consists of an absorbable polymeric or copolymeric material matrix selected on the basis of prospective absorption time with magnetized grains of lanthanoid such as of neodymium iron boron encapsulated for chemical isolation with gold, for example, embedded.

An absorbable radiation shield-jacket differs in incorporating isolation encapsulated grains of tungsten or osmium, for example, in overlapping relation to allow flexion. Since shielding materials are not magnetizable, an absorbable jacket to both retract subadventitial implants and to provide radiation shielding is laminated by bonding or fusing component lamina where the inner provides stenting and the outer shielding. Lamination and bonding must yield a jacket or chain type jacket of suitable flexibility for compliance with the least resistance to the movement in and of the ductus. The absolute sum mass of elemental iron particulate, for example, used in the implants depends upon the size of the ductus, the field strength required to maintain it patent, and the number of stents required.

When to allow complete absorption, iron particulate in the miniballs or stays is not encapsulated, the iron left behind following dissolution of the matrix or base will become toxic at about 350 micrograms per deciliter serum iron level (*The Merck Manual of Diagnosis and Therapy*, 18th edition, pages 2667-2668), which circumstance limits the sum mass in terms of number and size of unencapsulated iron miniballs that should be used in stenting. Iron toxicity is avoided by encapsulating the fraction of iron particulate that would exceed this level for chemical isolation within an outer shell of gold, for example. Encapsulated particulate or grains are deep surface textured to allow and coated to encourage tissue integration. If small enough, the entire miniball or stay is treated thus.

Alternatively, the iron particulate can be coated with polymers that are absorbable but differ in dissolution time and/or thickness, thus pre-staging in fractions the release of the overall burden and reducing the rate of uptake to less than that toxic. Magnetizable spring stainless steel particulate is not absorbed but remains after the absorbable matrix or base has disappeared; innocuous, no further treatment to remove the residue is needed. Whether applied by dipping, spraying, sputtering, vapor deposition, plating, or a combination of these, magnetic lanthanoid residue is toxic and encapsulated within a chemically inert and isolating nonabsorbable polymeric or metallic coating, usually of gold. Neodymium iron boron lanthanoid particulate, for example, allows replacing a much larger mass of an alternative material, but like those materials, must be nonabsorbably and biocompatibly encapsulated.

In an absorbable quasi-intrinsically magnetized stent-jacket or absorbable shield, the absorbable substance of the matrix is a glycolic acid-based copolymer, such as polylactic-coglycolic acid with the glycolide content increased as the brevity of intact life or persistence desired, and the resilience determined by the intrinsic properties of the copolymer, thickness of the layer or layers, the number and size of perforation, and whether the jacket is indented or fissured to create a hinging line of flexion. Whether disintegrated spontaneously or on demand as addressed in the section to follow, a temporary stent-jacket is not intrinsically magnetizable as are certain stainless steels and must be magnetized by adding bar magnets. These can consist of tiny magnets embedded within a matrix as in quasi-intrinsically magnetized permanent and destructible on demand stent-jackets or magnets mounted about the outer surface of the jacket.

As strongly magnetizable material is not absorbable, these are left behind after the matrix or base-tube disintegrates. However, neodymium iron boron lanthanoid magnets, with rounded corners if larger, encapsulated in gold are so small that irritation to neighboring tissue should seldom not arise. If it does, then the magnets are resituated or extracted by the stereotactic means addressed above in section entitled 4g Emergency Recovery of Miniballs and Stays and below in section X2c entitled Stereotactic Arrest and Extraction of a Dangerously Circulating, Mispositioned, or Embolizing Miniball. Encapsulation in gold plate, for example, is treated for surface contaminants and rid of surface defects such as microfractures and voids, if any, by means addressed in the section below entitled Miniature Ball Implants.

Encapsulated for chemical isolation, unless removed, the magnets may preclude the postimplantation use of magnetic resonance imaging; however, these need not be retrieved to accommodate more recent pacemaker or cardioverter resynchronization implants. The decision to use a permanent or absorbable jacket depends upon the prospects for the subsidence of occlusive proliferation and/or the recovery of wall strength. Inasmuch as the reduction or shrinking that usually follows treatment of an aneurysm is not associated with an eventual recovery of wall strength that would justify the explantation (removal) of an enlargement restraining jacket, a jacket to contain an incipient aneurysm, for example, should be nonabsorbable.

The same pertains to a stent-jacket used to restrain a collapsed trachea in veterinary practice, which will likewise remain weak. A magnetless side-slit polymeric base-tube affords greater strength, uniformity of inward restraint over the encircled segment than can an alternative wrap (bandage), and does so without concession to compliance with the pulse. In an abdominal aortic aneurysm where the surrounding clearance is adequate, for example, the jacket is secured with side-straps; otherwise, end-ties as addressed above in the section entitled Jacket End-ties and Side-straps are used.

I10b. Noninvasive Dissolution on Demand of Absorbable Stent-Jackets, Base-Tubes, Radiation Shields, and Miniballs A miniball may require to be eliminated for a number of reasons, some with the miniball positioned close to others, or because it has entered the bloodstream. This section will address both eventualities. The preceding section entitled Absorbable Extraluminal Magnetic Stent-jackets and Materials specified numerous absorbable materials suitable for use in an extraluminal stent. Situated outside the lumen, an extraluminal absorbable stent encircling a vessel is not constantly washed over by blood to accelerate its breakdown by hydrolytic and enzymatic action as would an endoluminal stent of like formulation. Moreover, unlike an endoluminal stent, which to exert the radially outward force necessary to prevent migration must be substantially noncompliant, the materials in an extraluminal stent must comply with the expansion and contraction of the ductus.

The required combination of elasticity, resilience, and absorbability to do this without leaving a toxic residue or revealing inadequate fatigue endurance eliminates most materials, to include magnesium and its alloys, for example. Materials that are absorbable on demand are absorbable materials which have been modified or supplemented to allow their immediate dissolution prior to reaching the normal term for spontaneous dissolution or which have been modified to extend the period for spontaneous dissolution as well as allow their immediate dissolution prior to reaching the extended term for spontaneous dissolution. One approach to varying the spontaneous interval preceding disintegration, addressed in the last section above, is a jacket or matrix formulation of glycolic acid-based copolymer, such as polylactic-coglycolic acid, with the glycolide content increased as the brevity of intact life or persistence desired.

A term exceeding that of a suitable absorbable material is then obtained by incorporating an agent of dissolution within a material that would otherwise be nonabsorbable. When not deeply implanted, the rate of dissolution of the material, whether absorbable or nonabsorbable, can be accelerated by direct heating over one or more intervals where the temperature is kept well below most actual melting points, which would injure tissue. For implants positioned more deeply as does not allow the direct application of heat, the implant is modified to remotely radiate heat from within by induction when the patient is placed in a radiofrequency alternating magnetic or electromagnetic field. This will induce heat in any ferrous object within the field, which will be limited in the extent to which it can be focused to select only one of a number of like miniballs, for example, for disintegration.

Where the need to disintegrate one of a number of otherwise similar implants is more likely, that implant is formulated to disintegrate at a lower temperature by means such as addressed below in this section. A miniball that is disintegrable on demand without significant insoluble or toxic residue affords the option of eliminating it from an accidental embolizing situation without the need for an impasse-jacket, as addressed below in the section entitled Miniball and Ferrofluid-impassable Jackets, or Impasse-jackets. Such modification consists of incorporating iron having sufficient continuity to support the induction of the eddy currents necessary to generate the temperature required. When the rate of dissolution responsive to a safe amount of heat alone is too low, the heat is used to first melt a biocompatible solvent which has been mixed into the matrix or jacket material in dispersed beads, or laminated with the matrix or jacket.

Using such means, provided both the material and solvent are biocompatible, nominally nonabsorbable materials can be rendered effectively absorbable. The most common example water for dissolving homopolymers and copolymers of polylactic and polyglycolic acid, a solvent liquid at room temperature must be kept separate until dissolution is initiated. A gel that releases water when heated or a biocompatible coating of a material with a lower melting point than the material of the matrix or jacket is used to contain the solvent. The solvent, here water, can also be released from dispersed beads by containment within a capsule or casing material of lower melting point than the solvent it contains. With water as a liquid solvent, encapsulation is within silicone wax with a melting point of 127 degrees.

The rate of absorption of an absorbable component, whether an extraluminal stent or a radiation shield needed only temporarily, for example, can be increased by chemically altering the polymer, and the absolute time required to effect dissolution, by introducing or increasing the number and area of perforations or increasing the thickness. Adjustments in chemistry, composition, and/or dimensions that affect resilience must be counterbalanced or offset to preserve compliance to the ductus motility or compensated for by the impressing of an indenting line (fissure, furrow, flex line, hinging line) or lines for increased flexion. For a given material, thickness, and proportion of perforations, the primary determinant of dissolution rate is the extent and type of tissue contact; in a body cavity, contact may be negligible compared to the relative lack of space surrounding a peripheral artery, for example.

The surface activity or metabolic rate of tissue is greater within tissue, such as the parenchyma or medulla of the organ than outside where a stent-jacket or absorbable patch-magnet, for example, would most often be placed. The longer rate of dissolution of a given absorbable material when contact with active tissue is less prompts the application of a method for inducing dissolution from outside the body on demand. Unlike the dissolution of an expansion insert, the dissolution of an absorbable stent-jacket or any other implant described herein is not incremental by virtue of addressing different layers used for this purpose but is absolute, to be effected at once.

Accordingly, whether the material is inherently absorbable or is nonabsorbable but adapted as indicated, when radiological examination reveals that the material has not degraded, it is actively disintegrated. If the jacket or matrix is made of a polylactic coglycolic acid, for example, it can be seeded for the noninvasive discretionary dissolution on demand with small pockets of bound or encapsulated water released when heated. The rate of dissolution is further accelerated when the solvent or enzyme is contained within a laminated layer and further accelerated still when the jacket or matrix is enclosed within an outer jacket containing the solvent or enzyme. The same method can be applied to numerous alternative materials where dissolution is effected through the discretionary timed release of a solvent or enzyme, for example.

One way to do this is to include a hydrogel along with ferromagnetic, medicinal, shielding, and/or any other particulates in a polylactic-coglycolic acid absorbable polymer matrix while in the amorphous or semimolten phase for extrusion. The hypoimmunologically processed gelatin-based hydrojel, for example, will retain its bound water when passed through the extruder. Using the hydrogel can provide the additional benefit that the material itself is absorbable. When the absorbable base-tube or radiation shield in which the water or other solvent binding gel is incorporated is later heated to its melting point below that of the surrounding matrix, the gel will release the solvent, which can include an enzyme, drug, or other therapeutic substance not destroyed during warming and extrusion.

Using this method, dissolution on demand is noninvasive whether the implant is placed shallow enough to heat directly with a hand dryer or placed more deeply, necessitates the inclusion of heat inductible matter and placing the patient in a radiofrequency alternating magnetic field. Invasively effecting dissolution by direct wetting with water, enzyme, or a chemical solvent is substantially limited to application in an open surgical field. The polymer matrix and/or the gel can incorporate medication released as the matrix is dissolved, and the water bound in the gel can include glycolytic enzymes and lactase, which will act to break down the polylactic coglycolic matrix, for example, but not the hydrogel. Biodegradable anhydrides have long been used to release drugs and bioactive substances incorporated within the polymer by entrapment or encapsulation.

Dissolution on demand applied to radiation shields, addressed in the section above entitled Radiation Shield-jackets and Radiation Shielded Stent-jackets Absorbable and Nonabsorbable, pertains to the matrix; if toxic, the particulate is encapsulated for chemical isolation. Formulating the solvent and or its outer coating in each implant, such as a miniball, to flow at a different temperature and/or incorporating different amounts of ferrous matter in each will allow the differential selection of all those that disintegrate at and below a certain temperature but will not select among these. The incorporation within a tiny miniball, for example, of a tuned circuit (Niwa, T., Takemura, Y., Inoue, T., Aida, N., Kurihara, H., and Hisa, T. 2008. "Implant Hyperthermia Resonant Circuit Produces Heat in Response to MRI Unit Radiofrequency Pulses," *British Journal of Radiology* 81(961):69-72, available at http://bjr.birjournals.org/cgi/content/full/81/961/69) faces the problems of inadequate space and incomplete absorbability.

For selectively destroying a miniball close to others, the tapered probe at the end of a powerful electromagnet with its polarity reversed at a radiofrequency will induce heat in any object containing ferrous material of sufficient continuity but, even though these are marked with bright contrast, may not be aimable with sufficient accuracy to assure the selectability of one miniball, for example, amid or proximate to others for disintegration. Provided a miniball incorporates ferrous content and means for its disintegration on demand by heat induction, an electromagnet energized with current continuously alternated at high frequency preprocedurally positioned downstream can disintegrate a miniball which escapes into the bloodstream regardless of its exact location, as addressed below in the section entitled Downstream Disintegration of a Circulating Miniball.

I10c. Absorbable and Nonabsorbable Circumvascular Jackets with Medicated Linings Atherosclerosis appearing at least in part adventitial in origin, as addressed above in the section entitled Accommodation of the Adventitial Vasculature, Innervation, and Perivascular Fat and below in this section, a moisture barrier-coated viscoelastic polyurethane foam lining can be wetted with a medicinal or bioactive liquid or facially impregnated with a cream or gel with negligible effect on its mechanical properties. While it would succeed in targeting a particular segment along the outer or adventitial surface of the ductus, the use of a magnetless nonabsorbable jacket is not preferred as requiring percutaneous access first to implant and then to recover or explant the jacket; single femoral, brachial, or cubital (radial) entry with transluminal placement of medication miniballs is preferred as less invasive.

When access is not difficult, a fully absorbable magnetless or nonmagnetic stent-jacket with the elasticity to comply with the autonomic action of the ductus or stays that consist exclusively of medication and are completely absorbed also eliminate the need for reentry at a later date. An absorbable stent-jacket with medicated lining and sufficiently susceptible medication miniballs or stays will release medication adventitially without and within, if indicated, under compressive force determined by the strength of jacket magnetization. The drugs used with absorbable jackets and absorbable medication stays would typically include or consist of statins, steroids, and antibiotics.

Fully absorbable jackets can be used with absorbable or nonabsorbable ferromagnetic miniballs. More aggressive treatment of a segment is simultaneously endoluminal as well as circumvascular through the use a holding impasse-jacket, as addressed above in the section entitled Concept of the Impasse-jacket and in the section to follow entitled below entitled Miniball and Ferrojluid-impassable Jackets, or Impasse-jackets. More powerfully magnetized stent-jackets, impasse-jackets, miniballs, and stays can be used in any combination to further attract drug carrier nanoparticles into the lesion. Where the localized circumvascular release of medication would be therapeutic, the use of an absorbable stent-jacket with a medicated lining may be indicated.

The progressively emerging implication of the adventitia in atherosclerosis and the adverse sequelae associated with its treatment make this probable (see, for example, Xu, X., Lin, H., Lv, H., Zhang, M., and Zhang, Y. 2007. "Adventitial Lymphatic Vessels—An Important Role in Atherosclerosis," *Medical Hypotheses* 69(6):1238-1241; Stern, N. and Marcus, Y. 2006. "Perivascular Fat: Innocent Bystander or Active Player in Vascular Disease?," *Journal of the Cardiometabolic Syndrome* 1(2):115-120; Plekhanova, O. S., Stepanova, V. V., Ratner, E. I., Bobik, A., Tkachuk, V. A., and Parfyonova, Y. V. 2006. "Urokinase Plasminogen Activator in Injured Adventitia Increases the Number of Myofibroblasts and Augments Early Proliferation," *Journal of Vascular Research* 43(5):437-446). Wilcox, J. N., Okamoto, E. I., Nakahara, K. I., and Vinten-Johansen, J. 2001. "Perivascular Responses after Angioplasty which May Contribute to Postangioplasty Restenosis: A Role for Circulating Myofibroblast Precursors?," *Annals of the New York Academy of Sciences* 947:68-92; Wilcox, J. N. and Scott, N. A. 1996. "Potential Role of the Adventitia in Arteritis and Atherosclerosis," *International Journal of Cardiology* 54 Supplement: S21-35).

Pathology that results from balloon overinflation injury should not pertain to the angioplasty apparatus described herein (see, for example, Wallner, K., Sharifi, B. G., Shah, P. K., Noguchi, S., DeLeon, H., and Wilcox, J. N. 2001. "Adventitial Remodeling After Angioplasty is Associated with Expression of Tenascin mRNA by Adventitial Myofibroblasts," *Journal of the American College of Cardiology* 37(2):655-661). The foregoing means, to include the use of stent-jackets with a medication-coated or impregnated lining and holding impasse-jackets, allow medication to be delivered to the targeted segment in far higher concentration than might be allowed to circulate.

Where therapeutic doses of a glucocorticosteroid to treat inflammation associated with a ductus, as in a regional enteritis, produces side effects of a severity that justifies placing a holding impasse-jacket or jackets, treatment as addressed in the section below entitled Chemical Control over Implants and Coated Implants, to Include Miniballs, Stays, and Prongs allows the systemic circulation, hence, the side effects, to be avoided. Acutely affected segments in systemic disorders such as panarteritis (polyarteritis nodosa, periarteritis nodosa, Kussmaul's disease, necrotizing arteritis), segmental arterial mediolysis, Churg-Straus disease, and microscopic polyangiitis, for example, can thus be provided with the focused delivery of corticosteroids, usually prednisone or prednisolone, in addition to the systemic medication essential to treatment, which can therefore be reduced, averting the onset of hypertension, for example.

Smaller doses can be time released. The use of strongly magnetized stent- and holding jackets allows the drug or drugs to be replenished through the periodic infusion or direct vascular injection of drug carrier nanoparticles. Given that bacteria such as Chlamydia pneumoniae may play a role in arteritis and atherosclerosis (see, for example, Hu, C. L., Xiang, J. Z., Hu, F. F., and Huang, C. X. 2007. "Adventitial Inflammation: A Possible Pathogenic Link to the Instability of Atherosclerotic Plaque," *Medical Hypotheses* 68(6): 1262-1264.), the medication targeted with a concurrent background of reduced system dose when possible can include or consist of antibiotics.

Perforations for avoiding complete enclosure that would obstruct gas and other chemical exchange at the outer surface of the vessel are included in the sections below on various circumvascular jackets. When the adventitia is diseased or injured, the stent-jacket can be placed prior to discharge or stays consisting of medication implanted. Absorbable stent-jackets can be continuously extruded and sliced or formed by transfer molding of materials specified under the section below entitled Stent-jacket expansion insert materials having relatively short breakdown times.

I11. Stent-Jacket Expansion Inserts

I11a. Expansion Inserts Absorbable, Meltable, and Comminutable for Time-Discrete Decremental Contraction of Stent-Jackets Saliently, the entire subject of size adaptability with no loss in compliance with expansion and contraction of the ductus is nonexistent with endoluminal stents. The insertion of an oversized absorbable endoluminal stent in a dilatated (extatic, distended) lumen is temporary. An expansion insert is intended to allow a stent- or impasse-jacketed ductus that is temporarily swollen or distended by disease to better accommodate the ductus by contracting in pace with the reduction in swelling, whereupon the stent-jacket remains as the extravascular component of the stent. The object in temporarily expanding the stent-jacket is to allow the placement of a stent-jacket that will continuously accommodate a substrate ductus which, any anti-inflammatory medication notwithstanding, will subside (resolve, detumesce, recede, regress) from an initially swollen condition over an extended period.

Following treatment, vessels swollen by disease, implantation, as the result of reperfusion, or incipiently aneurysmal should gradually revert to substantially normal dimensions. Elastic and lined with viscoelastic foam, stent-jackets adjust to reductions in ductus cross-sectional area or caliber over a limited range. This intrinsic latitude combined with physiological compliance throughout the period of subsidence is a significant advantage of an extraluminal over an endoluminal stent. Use of a somewhat oversized stent-jacket with thicker lining extends this spontaneous adaptability as well as allows for future growth in a child, but only up to a point. Beyond that point, to provide a self-contracting stent that will eliminate the need for a second procedure to place a smaller jacket requires the use of an expansion insert.

Contraction of the stent-jacket base-tube is due to the gradual dissolution and loss in compressive strength of the absorbable insert segment materials used. Ideally, dissolution proceeds without reintervention, and any need for reintervention is minimized as to degree of invasiveness. The swelling may be the result of the pathology treated, a tumefacient used to expand the lumen wall for implantation, as addressed above in the section entitled Ductus Wall Tumefacients, or implantation. Whether the substrate ductus or a segment thereof is enlarged due to inflammation resulting from chronic disease, injury associated with angioplasty, the direct result of injury associated with ballistic implantation, or some combination of these, a stent-jacket with expansion insert is devised to contract in step with subsidence in the temporary swelling.

A similar need for contraction over time may ensue when antiangiogenic medication, radiation, or ionizing radiopharmaceuticals in the form of irradiating miniballs and/or the stent-jacket lining, for example, are used to destroy neoplastic tissue that extends into the lumen. Materials to shrink in step with the subsidence in swelling of a ductus while maintaining consistent mechanical properties whether spontaneously or in response to heating remain to be developed. In this circumstance, an expansion insert effectively renders the stent-jacket self-contracting. Due to the resilience required of a stent-jacket, the ability to encircle a swollen ductus with a stent-jacket sized for the normal gauge without circumferential pressure points is limited and necessitates strong bonding of the expansion insert.

Layered (sectional, segmented) expansion inserts such as those shown FIGS. 8 and 9 can consist, for example, of but a single polyester such as polylactic acid interleaved with hydrogel water-releasing segments, bisected at either end or at the midline, and fastened to the free edges of the side-slit with absorbable ethyl 2-cyanoacrylate cement. Due to the doubling of free ends, midsectioning a bilaterally symmetrical succession of segments yields an acceleration in the rate of dissolution for each like pair of segments, whereas perforating only specified segments accelerates the rate for that segment alone. Incorporation of magnetically susceptible matter into a unitary (monolithic, nonsectional) expansion insert to allow dissolution to be accelerated is seldom advisable.

This is because the radio frequency alternating magnetic field used to effect heat induction will similarly affect other elements such as temporary stent-jackets, miniballs, and stays nonselectively (nonaddressably, nondiscriminately), the latter better claiming this option. Ferrous content to expedite arrest and recovery of a lost part with the aid of an impasse trap-jacket or external electromagnet, for example, is also better applied to parts which might enter the bloodstream, would prove more difficult to locate if dropped, or pose greater risk to remove. Alternatively, the expansion insert consists of a unitary succession of bonded segments, each capable of reducing expansion by a measured increment in a given chemical environment wherein each segment can be accelerated in rate of dissolution through bilateral symmetry or by perforation or the inclusion of magnetically susceptible matter.

The possible combinations of spontaneously and deliberately or on-demand disintegrated material types and dimensions are many and afford wide variability in the rate of dissolution, making it possible to accommodate conditions of inflammation, edema, or enlargement due to any cause where these resolve over widely different intervals. The range of such adaptation limited by material properties and geometry, expansion inserts where swelling is more considerable are used with an oversized stent-jacket with thicker moisture barrier-coated viscoelastic polyurethane foam lining Stent-jacket expansion inserts, shown in FIGS. 7 thru 9, can be used with stent-jackets of any type, whether intrinsically, quasi-intrinsically, or extrinsically magnetized, or segmental, as shown without insert in FIG. 13. The minimization of complications demands that the stent-jacket be adaptable in size as well as dependable in maintaining patency.

To develop materials that vary gradually in composition from end to end so that a nonsegmented insert will dissolve along a gradient would allow nonincremental or continuous shrinkage; however, the approximation of continuity that can be attained incrementally serves the need, and the cost to develop such materials for this limited purpose is unjustified. Disintegration on demand is obtained through the use of nonabsorbable layers when the subsidence and expansion period exceeds that obtainable using absorbable materials, and justifies a second procedure, which is preferably noninvasive through the application of heat directed from outside the body when the not deep or by induction in an alternating field. Nonabsorbable materials such as stone, are disintegrated noninvasively, while polymers are usually dissolved through the minimally invasive direct injection of a solvent.

Stone to absorbable polymer bonds are generally made with implantable grade cyanoacrylate cement. The need for a followup procedure of any kind least preferred and one that is invasive less preferred still, spontaneous dissolution should be used whenever the term for subsidence falls within the period attainable using absorbable materials. In a follow-up lithotripsy, unless the continuity through the depth of the tissue serves to relate the source of excitation to the insert as target, intracavitary infusion is necessary for the lithotriptor to pulverize the stone insert or the final stone segment. Pulsed laser lithotripsy through a laparoscopic sized entry wound should not be necessary. In most instances, negligible swelling can be accommodated by increasing the thickness of the moisture barrier-coated viscoelastic polyurethane foam lining in a jacket of larger duameter.

Upon subsidence, the ductus may then expand and contract within the thickness of the foam without opening and closing the side-slit or slot. Intermittent separation at the adventitial-foam interface due to slower conformation recovery is probably innocuous if not beneficial. The use of an oversized jacket with thicker foam lining is thus an additional measure if not an alternative to the use of an expansion insert. Were the thickness of the foam increased to the point where the strength of magnetization would have to be increased to offset the increase in the radial distance, then upon shrinking of the ductus with compression of the foam, the field strength could result in pull-through or delamination.

Since the mechanical properties of the ductus will change during healing as to defy prediction, the magnetic strength should be kept to little more than clinical judgment if not the actual testing of nearby like tissue shows can be withstood. While not shown in FIG. 9, the material or materials of the expansion insert must allow for an arcuate or bowed form to encircle without tangentially encroaching upon, pressing into, and irritating the swollen ductus. Bursting of a monolithic insert, or the bonds between the segments of a multisegment insert under the restorative force of the stent-jacket and autonomic function of the ductus is compensated for by increasing the bonding surface as shown in FIG. 8 and if necessary, the use of stronger materials. Before adjusting the formulation or the dimensions of the materials, which may alter the absorption time, different bonding surface angles are tested for bonding strength.

Whether pending or following subsidence, an out of round condition diametrically from the slit or slot or approaching and alongside the stent-jacket side-slit or side-slot can usually be disregarded. When felt preferable to more evenly distribute the forces, voids are accommodated by proportionally increasing the moisture barrier-coated viscoelastic polyurethane foam lining in thickness. Foam linings are addressed above in the sections entitled Requirement for Stent- and Shield-jacket Moisture barrier-coated viscoelastic polyurethane foam Lining and Stent- and Shield-jacket Moisture barrier-coated viscoelastic polyurethane foam Linings. Upon subsidence, this small added thickness of foam is readily compressed so that the jacket can return to a round cross section. Stent- and shield-jackets are packaged with expansion insert segments, or strips of various materials in different dimensions to be bonded side to side with cyanoacrylate cement for speed, and strips of moisture barrier-coated viscoelastic polyurethane foam to take up the out of round circumference toward the insert slit or slot.

Situated outside the bloodstream, the rate at which absorbable layers in an expansion insert disintegrate is slower than were the same material placed constantly washed over by the blood. When necessary, this is compensated for by incorporating constituents in the layer that will accelerate its dissolution when heated. Expansion inserts may be slit at the center, slit to one side, or exceptionally, glued shut after placement, pending initial absorption to produce free edges. Heating and the injection of a solvent, for example, change a layer or segment of the insert that would have been spontaneously or passively dissipated to one of controlled removal. When the insert material is absorbable, controlled removal induces absorption earlier in response to a radiological finding of early subsidence. When not absorbable, controlled removal is by means of comminution, as addressed below in the section that follows.

So that the operator or a technician can tailor a stent-jacket to the actual conditions encountered, as well as to reduce costs, stent-jackets are standardized based upon gauge. Since the spines in a spine and ribs type stent-jacket must expand and contract independently, an expansion insert for such a stent-jacket must be sectioned, or divided longitudinally, by independent bonding to each rib. As with the option to insert straight-line or double-wedge linings, expansion inserts are sold apart from the base stent-jacket. To allow the lining insert to extend to the edges of the side-slit or side-slot, the expansion insert is bonded along the facing edges of the slit or slot, the strength of bonding increased by lapping over and gluing the inset onto the outer surface of the stent-jacket alongside the slit or slot to the distance necessary.

A shield-jacket placed to allow warming by magnetic or electromagnetic heat induction postprocedurally is seldom temporary but rather a long-term if not permanent end-implant, for which the addition of an expansion insert may be appropriate. A shield-jacket used as a temporary implant, that is, used to prevent a perforation from striking neighboring tissue during discharge and removed prior to closing is sized for the gauge needed when used. When swelling is minor and expected to resolve quickly after a reasonably predictable interval, the expansion insert is relatively narrow, absorbable, usually a single layer or monolithic piece of an absorbable suture or tissue engineering scaffold material such as polyglycolic acid glued to the base-tube or the intrinsically or quasi-intrinsically magnetized stent-jacket.

When the term pending subsidence or resolution is brief, the expansion insert is usually bonded along one opposing edge of the side-slit or side-slot. Whether the slit in the insert is longitudinally centered or situated to one side, the segments or layers of the insert must dissipate in the order of removal from the slit. Since a center-slit allows layers of the same material to either side rather than a layer of double the width or thickness to one side, each successive layer can be halved, for example, in width or thickness with double the bonded edges. For this reason a center-slit generally provides greater dependability. When the insert slit is in the longitudinal center, the materials to either of its sides may be the same or different but must dissipate in the order of proximity to the respective free edge of the jacket slit.

By the same token, the materials and thicknesses of the expansion layers or segments to either side need not be the same, or bilaterally symmetrical. When swelling is more pronounced, the wider expansion insert required calls for the increased dependability of a center slit insert. When subsidence is anticipated to be in stages or incremental, the width of the layers is keyed to the anticipated duration of the stages. When the interval for subsidence is overall brief, the insert will usually be made to open along one edge. Longer intervals that call for wider layers are better divided to either side of a center-slit. When swelling is considerable, a wide insert such as shown in FIGS. 8 and 9 is center-slit, that is, made to open along the longitudinal center, receding laterally from which are progressively less quickly absorbed layers, usually polymeric.

When the overall time for subsidence is unpredictable or the prediction undependable, the layers for later stages of dissolution, which consecutively more approximate the free edges of the stent-jacket to one or both sides in the order of increasing durability or duration, are made for dissolution on demand. Such materials may be accelerated in breakdown time or initiated in breakdown by exposure to heat or an injectant. For dissolution on demand only, that is, where the interval for expansion cannot be predicted but will likely take a long time, the layers need not be absorbable at all but rather made of stone that allows discretionary removal by the clinician with the aid of a lithotriptor. Layer bonding agents are addressed below in this section. Since the absorbable components addressed herein are not embedded within tissue but rather positioned outside the ductus, exposure to serous fluid is present, but exposure to enzymes that would effect dissolution is not.

For this reason, another approach to dissolution on demand is the incorporation by embedment into the matrix of the expansion insert material of a solvent respective of the insert layer, which is liberated by remote heat induction. Such means are delineated above in the section entitled Noninvasive Dissolution on Demand of Absorbable Stent-jackets and Base-tubes, among others, and applies no less to the matrix of any absorbable component described herein, whether an expansion insert, layer thereof, stent-jacket, or radiation shield, for example. To allow the stent-jacket to expand and contract with the involuntary movement in the ductus throughout the period of subsidence, when the other side is to open, the expansion insert is placed inside and glued to the base-tube along one opposing edge of the side-slit or side-slot. When the center is to open, it is glued at both opposing edges.

Most expansion inserts are homogeneous, consisting of an absorbable material such as polylactic coglycolic polymer for dissolution over a certain relatively brief interval. When contraction is to be incremental over an extended period, the layers are bonded side to side in order of dissolution beginning with that first to disperse at the unglued end or ends. Spontaneous dissolution is only controllable to the extent that the layer or segment thickness affects the dissolution time, and the material can be modified to increase this interval. This assumes that the gap is large enough for the material to maintain parity with the rate of subsidence. Greater control is attained with materials having a longer dissolution time where dissolution can be accelerated by applying heat, a solvent, or some combination of these, for example.

In situations where subsidence cannot be predicted to occur within the interval for spontaneous dissolution of a material, a permanent material that can be disintegrated on demand is used where the material is susceptible to dissolution in reaction to a safe dissolvent or lithotriptor induced fragmentation. In addition to providing contraction that is spontaneous over a reasonably predeterminable interval, or controllable responsive to action by the operator, the materials can be combined for early spontaneity and later control. Materials rendered absorbable when warmed, for example, such as by a heat-window or windows in the muzzle-head of a minimally or fully ablation or angioplasty-capable barrel-assembly, are used for discretionary reduction in diameter contingent upon the confirmation of subsidence by imaging.

Stony materials provide expansion in diameter that will persist until such layers are disintegrated by lithotripsy (extracorporeal litholapaxy, ultrasonic lithotresis, mechanical litholysis, or lithodialysis) during a follow-up procedure. The dissolution of stony layers in an expansion insert can also be effected chemically. For this purpose, a solvent such as potassium citrate (see, for example, Frang, D. 1978. "A Comparative Study of Three Different Citrate Combinations of Litholytic Action," *International Urology and Nephrology* 10(3):195-199) or sodium bicarbonate is applied directly by injection under fluoroscopic observation rather than systemically over time. Quick dissolution for response to specified agents may necessitate synthetic stone specially formulated for the purpose.

The stent-jacket surrounding the ductus so that endoluminal access would necessitate perforating the lumen wall, a litholytic solution can be injected locally from outside the body. Exceptionally, where the transluminal placement of a conventional (endoluminal) absorbable stent to temporarily support an enlarged or collapsed ductus pending subsidence is impossible and entry by means of an angiotomy would result in greater trauma, completely absorbable stays used without a circumvascular stent-jacket, as will be described, may be preferred. Any instance of absorption can include the release of medication. The stent-jacket with expansion insert consisting of one or several expansion strips and eccentricity gap filling strips of moisture barrier-coated viscoelastic polyurethane foam can be prepared before the procedure, or, if the duration and rate and/or caliber required is not certain until entry, midprocedurally.

When the ductus is expected to recover to a normal condition with slight reduction in gauge following the temporary need for stenting, the extraluminal stent is devised to disintegrate over the period allowed for subsidence. Magnetic stents of the latter type are addressed above in the section entitled Absorbable Magnetic Stent-jackets with the miniballs used addressed Temporary (Absorbable) Ferromagnetic Miniballs and Other Implants. When continued stenting is needed and the reduction in gauge is slight, the foam lining in a permanent stent will accommodate the reduction in gauge. Expansion inserts can be made to disintegrate using heat, extracorporeal shock wave lithotripsy, or percutaneous (endoscopic) intracorporeal lithotripsy whether ultrasonic, electrohydraulic, laser, or pneumatic mechanical.

Intracorporeal (invasive) lithotripsy should be reserved for only those instances that do not respond to extracorporeal (noninvasive) lithotripsy where contraction of the stent-jacket is judged sufficiently important to justify it. Stone that can be prepared with a suitable chemical composition for safe dissolution with a solvent can be removed by injection, by release of the solvent from within the stent when heated from outside the body, or when heat induced in the stent when placed in a radio frequency alternating magnetic field. An extraluminal stent placed in childhood remain functional for many years.

Eventual failure will most likely result from a loss of base-tube resiliency, pull-through or delamination after much time less likely due to trajectory closure, tissue infiltration, and mechanosensory function (see, for example, Chiquet, M., Gelman, L., Lutz, R., and Maier, S. 2009. "From Mechanotransduction to Extracellular Matrix Gene Expression in Fibroblasts," *Biochimica et Biophysica Acta* 1793(5):911-920; Von Offenberg Sweeney, N., Cummins, P. M., Cotter, E. J., Fitzpatrick, P. A., Birney, Y. A., Redmond, E. M., and Cahill, P. A. 2005. "Cyclic Strain-mediated Regulation of Vascular Endothelial Cell Migration and Tube Formation," *Biochemical and Biophysical Research Communications* 329(2):573-582; Sarasa-Renedo, A. and Chiquet, M. 2005. "Mechanical Signals Regulating Extracellular Matrix Gene Expression in Fibroblasts," *Scandinavian Journal of Medical Science in Sports* 15(4):223-230; Shukla, A., Dunn, A. R., Moses, M. A., and Van Vliet, K. J. 2004. "Endothelial Cells as Mechanical Transducers: Enzymatic Activity and Network Formation under Cyclic Strain," *Mechanics and Chemistry of Biosystems* 1(4):279-290; Silver, F. H. and Siperko, L. M. 2003. "Mechanosensing and Mechanochemical Transduction: How is Mechanical Energy Sensed and Converted into Chemical Energy in an Extracellular Matrix?," *Critical Reviews in Biomedical Engineering* 31(4):255-331).

In addition to relatively short-term expansion inserts that allow for the initial resolution of swelling, expansion inserts can incorporate materials to be disintegrated by deliberate action. Expansion insert or insert layer materials to persist until intentionally removed on the basis of radiological findings generally consist of stone for destruction by lithotripsy. To prevent other components of the stent-jacket from being shocked or jarred possibly causing delamination of the adventitia or media and therewith patenting failure, the material or layers of the expansion insert are formulated or selected for greater susceptibility to disintegration. With or without loss of function, nonabsorbable stent-jackets that remain past the need for patenting can usually be left in place.

A loss in base-tube resilience, pull-through, or delamination do not predispose to the entry of miniballs into the circulation; the adaxial lamina will have long since healed behind the abaxial miniballs. However, where stone layers for removal by lithotripsy have been included, wide stays are used instead, or discounting the use of stays, an impasse-jacket is placed downstream from the miniballs at the same time that the stent-jacket is placed. Materials for destruction on demand are addressed below in the section entitled Lithotriptor-destructible Stone Stent-jacket Expansion inserts and Differentially Destructible Expansion insert Layers. For differential and therefore selectable destructability, harder or stony materials must exhibit a marked frangibility at the frequency of the pulses and level of power used.

Stent-jackets for use with an expansion insert that will undergo lithotripsy should be intrinsically or quasi-intrinsically magnetized, or if extrinsically magnetized, then should use magnets that are not susceptible to damage due to lithotripsy. A stent-jacket with stony layer should be oriented with the side-slit placed to expedite lithotripsy. When the positioning of a side-slot must conform to a prior requirement, such as to straddle a frenulum, this will not be possible, nor will rotating the jacket about the ductus with the aid of an external electromagnet. If readily accessible through a small incision, the expansion insert is removed manually by direct access. It will not be possible to rotate the stent-jacket about the substrate ductus by means of exerting tractive force on its discrete magnets with an external electromagnet. Base-tube expandability is limited by the increase in resistance to further expansion and in distortion from round.

The percent expansion is limited not only by the fact that the stent-jacket must sufficiently conform to the ductus once subsided but by the fact that magnetization must not be extended to the insert. Since the insert resists the restorative force of the base-tube, the capacity of the base-tube for further expansion in compliance with muscle action in the ductus in its swollen condition is reduced; that is, the use of an expansion insert partially uses and deducts from the overall expandability of the base-tube. This can be compensated for through the use of a larger diameter base-tube with thicker foam lining within the range of thickness that does not require an increase in strength of magnetization as could result in pull-through or delamination. In some instances, a larger jacket can be used alone.

Expansion inserts are bisected lengthwise as extend the base-tube in circumference while providing a side-slit or side-slot. As shown in FIG. 7, to allow the stent-jacket insertion tool (addressed below) to be slid along the edges upon insertion and avoid any inward protrusions as would irritate the ductus, the expansion insertion is bonded along the free edges of the side-slit or side-slot and lapped over onto the outer surface to provide a larger bonding surface. The free edges in any practical stent-jacket or any other implant described herein are always rounded. Any cut-outs in the stent-jacket that would be needed to clear anatomical side branches of the target ductus should be positioned away from the insert to avoid weakening it. Initial enlargement in a ductus can result from coexisting (comorbid, compounded, overlapping) conditions of which the period for the subsidence of each is separate in time so that the ductus recedes in steps.

Secondary enlargement in gauge of the ductus due to growth or hyperplasia generally recommends the use of a larger jacket with thicker foam lining and an expansion insert. When the time for these successive regressions is reasonably predictable, the object is to time the contraction of the stent to the reduction schedule anticipated. The time of dissolution of the adhesive used to bond each successive layer need not exhibit an absorption time equal to that of the material of its respective layer. While to make the base-tube itself of a material that shrinks at a desired average rate would sustain superior circumvascular circularity during subsidence, the material would at the same time have to present the correct combination of resilience or restorative force and shape memory, permanence, implantability, and dependability as to diameter when fully contracted to the end diameter.

The use of a temporary expansion insert based upon an absorbable material or layers of absorbable materials is indicated when 1. The condition is familiar as to afford a rate of subsidence that is substantially predictable, 2. Subsidence will occur over a relatively short interval, 3. The reduction in size will be relatively small, and 4. The potential consequences of miscalculation in timing and gauge are limited to a range that can be tolerated. Materials vary in degree of absorption time predictability. The dependability of the time of stent contraction as the result of dissolution of the expansion insert as a whole or in stages is increased by incorporating polyester-based materials that are more predictable than gut as to time of absorption as well as nonallergenic.

Similarly, absorbable adhesives used to bond expansion inserts to the free ends and outer surface of the stent-jacket side-slit and to bond different segments within the insert when present are better predictable as to dissolution time as well as tissue compatibility when consisting of a polyester-based synthetic such as specified below rather than a natural material, such as collagen, gelatin-resorcinol pentanedial, or gelatin-resorcinol ethanedial. The insert is glued along the side-slit or slot on one side, or if to open at an intervening point, then at both sides, allowed to cure, and bisected. For a base-tube of given elasticity, the breadth or reach of the expansion insert across the gap of the open side-slit will be limited by the need for the side-slit when expanded by the insertion tool to clear the diameter of the ductus without risk of the insert breaking loose or fracturing.

This can be overcome by using a base-tube having a somewhat larger diameter with a thicker foam lining rather than changing to a base-tube that lacks perforations believed beneficial for 'breathing,' is thinner, or made of less resilient material. The primary requirement of the base-tube is that it achieve good compliance with the smooth muscle function of the ductus without avoidable irritation or interference. Since for a given material, base-tube flexibility results from the intrinsic elasticity of the base-tube material, its thickness, and the shape and area of any perforations, preserving adequate resilience without going to a different material or larger base-tube necessitates increasing base-tube thickness and reducing or eliminating any perforations as the extent of expansion is increased.

Whether the insert is absorbable or destructible, inward protrusion as would protrude into the substrate ductus must be avoided. When a radial thickness of an insert segment of an irreplaceable material is needed as would extend radially outward to irritate neighboring tissue, no more of the segment should extend inward from the internal surface of the base-tube than can be accommodated by a separate moisture barrier-coated viscoelastic polyurethane foam lining. The overlap onto the outer surface of the base-tube to increase the bonding surface must not be so thick that it protrudes into neighboring tissue. Nor should it extend onto the external surface to a distance from the free edge that it displaces perforations which impart the resilience desired as well as allow the adventitia to 'breath.'

Also not to be displaced are any extrinsic magnets, which should remain radially aligned to their respective ductus-intramural implants during subsidence. The magnetic force between the intravascular and extravascular components will compensate for some loss in resilience or shape memory of the base-tube over time. Depending upon the exposure to the agents of dissolution, most often water and proteolytic enzymes, absorbable materials can include dried sugars, syrups, absorbable suture polymers, and less often, collagen (gut). The persistence of gut is increased through treatment with aldehyde solution and chromic salts (chromium trioxide), as is conventional with chromic catgut suture. As compared to synthetic materials, gut is more tolerant of variability in the surrounding environment giving it a wider range of application but less predictable in dissolution time.

The chemical environment of the expansion insert is, however, quite different than and more widely variable than that of suture, which unlike the expansion insert, courses through and remains in intimate contact with the surrounding tissue over its entire surface area, which is proportionately large in relation to its volume. The mechanical factors pertinent to suture also differ in that the edges of the tissue to be united remain coapted or are held in apposition despite swelling, and in that tensile strength, amenability to knotting, and capillarity that would permit entry by bacteria into the penetrated tissue are important. The expansion insert segments or layers and any agents for the dissolution of these to be embedded in them for release by heating, for example, are selected on the basis of the chemical environment at the side-slit.

Heating can be induced in a radio frequency alternating magnetic field or by using the heat-windows or feeding hot gas through an ablation or ablation or angioplasty-capable barrel-assembly. The former is preferable as noninvasive with the heat induced and radiated within the insert or insert layer, where the surrounding matrix provides thermal insulation. Yet another relatively unobtrusive technique is intracavitary (intraperitoneal, intrapericardial) fluid infusion such as used in ultrasonography with saline solution, where the fluid (water) contains the solvent or enzyme for dissolution. Heating if not of such long duration as to tax the patient can often prove effective to accelerate the dissolution of absorbable materials without the need for a heat-released embedded solvent or different solvents in each layer.

Water and native enzymes at the site break down their respective substrate insert or its layers. Unlike most implants, the stent-jacket is exposed to serous fluid and exudates rather than the enzymes within tissue. When a uniform exposure of the different portions of a given insert or its layers to the same chemical environment cannot be depended upon, compensatory increases in rate of dissolution can be embedded with encapsulated solvents that if necessary can be released to effect the dissolution of that layer. Agents of dissolution for absorbable layers include water and enzymes. Absorbable layers or segments with different dissolution times are sequenced in order of the quickest to dissolve at the free end and that next quick adjacent to it and closer to the bonded end.

When imaging reveals that a layer or layers should be eliminated before the period for spontaneous absorption has elapsed, a solvent respective of each such layer or segment is embedded within that layer for liberation by heating. Such dissolution agents generally consist of water to hydrolyze ester bond-based polymers and acid hydrolytic and proteolytic (collagenolytic) enzymes for gut (catgut, collagen); physiologically exposed polyglycolide is ordinarily broken down by enzymes that exhibit esterase activity. With either gut or polymers, a hydrogel may be used for the release of water to activate chemically constituent or mechanically included (enclosed, embedded) proteolytic enzymes or to nonenzymatically hydrolyze the ester bonds of alpha-polyester polymers.

Provided it has the requisite strength and bonding strength, a water releasing hydrogel adhesive or layers thereof interleaved among absorbable layers may be used to bond layers of water-degraded materials where each such layer moving toward the surface of the stent-jacket has a progressively longer degradation time. The adhesive hydrogel may additionally release medication to accelerate healing and subsidence, for example (see, for example, Vieira, V. M. P., Hay, L. L., and Smith, D. K. 2017. "Multi-component Hybrid Hydrogels—Understanding the Extent of Orthogonal Assembly and Its Impact on Controlled Release," *Chemical Science* 8(10):6981-6990; Chivers, P. R. A. and Smith, D. K. 2017. "Spatially-resolved Soft Materials for Controlled Release—Hybrid Hydrogels Combining a Robust Photo-activated Polymer Gel with an Interactive Supramolecular Gel," *Chemical Science* 8(10):7218-7227; Kioomars, S., Heidari, S.1, Malaekeh-Nikouei, B., Shayani Rad, M., Khameneh, B., and Mohajeri, S. A. 2017. "Ciprofloxacin-imprinted Hydrogels for Drug Sustained Release in Aqueous Media," *Pharmaceutical Develeopment and Technology* 22(1):122-129; Nakata, R., Osumi, Y., Miyagawa, S., Tachibana, A., and Tanabe, T. 2015. "Preparation of Keratin and Chemically Modified Keratin Hydrogels and Their Evaluation as Cell Substrate with Drug Releasing Ability," *Journal of Bioscience and Bioengineering* 120(1):111-116; Omranipour, H. M., Sajadi Tabassi, S. A., Kowsari, R., Rad, M. S., and Mohajeri, S. A. 2015. "Brimonidine Imprinted Hydrogels and Evaluation of Their Binding and Releasing Properties as New Ocular Drug Delivery Systems," *Current Drug Delivery* 12(6):717-725; Cornwell, D. J., Okesola, B. O., and Smith, D. K. 2014. "Multidomain Hybrid Hydrogels: Spatially Resolved Photopatterned Synthetic Nanomaterials Combining Polymer and Low-molecular-weight Gelators," *Angewandte Chemie* [Applied Chemistry] (International edition in English) 53(46):12461-12465; Laurén, P., Lou, Y. R., Raki, M., Urtti, A., Bergstrom, K., and Ylipert-tula, M. 2014. "Technetium-99m-labeled Nanofibrillar Cellulose Hydrogel for In Vivo Drug Release," *European Journal of Pharmaceutical Sciences* 65:79-88; Liechty, W. B., Kryscio, D. R., Slaughter, B. V., and Peppas, N. A. 2010. "Polymers for Drug Delivery Systems," *Annual Review of Chemical and Biomolecular Engineering* 1:149-173; van Bommel, K. J., Stuart, M. C., Feringa, B. L., and van Esch, J. 2005. "Two-stage Enzyme Mediated Drug Release from LMWG [low molecular weight gelator] Hydrogels," *Organic and Biomolecular Chemistry* 3(16):2917-2920; Roorda, W. E., Bodde, H. E., de Boer, A. G., Bouwstra, J. A., and Junginger, H. E. 1986. "Synthetic Hydrogels as Drug Delivery Systems," *Pharmacy World and Science* [*Pharmaceutisch Weekblad. Scientific Edition*] 8(3):165-189). By embedment or interleaving within collagen or absorbable polymers, medication can also be released upon dissolution of the absorbable materials. FIGS. 7, 8, and 9 show different expansion inserts, that in FIG. 7 short and those in FIGS. 8 and 9 long, where both are bisected to open at the point midway between the opposing edges of a stent-jacket side-slit.

Materials available having widely variable spontaneous dissolution times, or that are susceptible to breakdown on demand with the application of an agent of dissolution by embedment or layer apposition, or that can be disintegrated by lithotripsy, and an ability to combine these materials in different ways, expansion inserts can be provided to span over the expanded side-slit even when curved or wide, as shown in FIGS. 8 and 9. Requiring only to shrink in step with the postoperative resolution in swelling, most expansion inserts are simple in consisting of a single segment or layer rather than compound, and relatively narrow. When the persistence of swelling is factor is unpredictable, dissolution on demand materials are used. Smaller expansion inserts such as shown in FIG. 7 when layered as shown in FIG. 8 are intended to disintegrate in shorter or more tightly controlled intervals of equal or different duration.

When one or more of the layers are susceptible to on-demand (active, controlled) dissolution through the application of heat or disintegration by lithotripsy, allowing for a period of subsidence following the dissolution or disintegration of that layer requires that the remaining layers have the material and bonding strength to withstand the destruction process. In FIG. 7, the small insert is materially and geometrically bilaterally symmetrical. Bisection where one side or bridging arm is not encased within a layer of another material has no effect on the free-to-bonded-end order of dissolution of the materials; however, bisection at a point intervening between the bond to the free edge of the base-tube makes it possible to encapsulate the segments to the one side or the other so that dissolution on that side will commence or be initiated only after the other side has disintegrated.

While the stone layer will be the only one remaining of the one expansion insert, agitation of lithotripsy can accelerate the dissolution of a spontaneously absorbed elements implanted elsewhere. Reciprocally, agitation can be used to accelerate the dissolution of absorbable segments, although an ordinary hand vibrator serves the purpose. Artificial stone can be used to encase or envelop one arm or side so that its period for disintegration will commence only after the other side has already disintegrated. Alternatively, the casing or envelope can consist of a heat melted matrix with or without a heat released solvent or induction heatable particulate embedded. Artificial stone can also be formulated for differential stone segment disintegration where distinct periods of a duration too long for absorbable materials is expected. Substances that dissolve in serous fluid are dispersed most quickly, with materials used to make absorbable suture absorbed more slowly and formulable to shrink or waste at a rate that assures persistence beyond the probable period for subsidence. The latter incorporate a solvent embedded as small encapsulated inclusions released when heated. The direct injection of a solvent and vibration will also accelerate dissolution of absorbable materials. The dissolution times of both kinds of material are reduced by increasing the surface area by perforation or dimensioning or increased by presentation as a block of greater thickness. When subsidence is expected to take longer still or never, stone is used. The different materials and shapes can be sequenced and mixed to control the rate of stent-jacket contraction in accordance with the reduction in diameter anticipated.

In FIGS. 8 and 9, free-edge or free-end segments or layers 113 and 114 can consist, for example, of crystalline sucrose (rock candy') curved as to lap over the outer enzyme releasing hydrogel adhesive, for example. In FIGS. 8 and 9, free-end segments 113 and 114 can also consist of polyglycolic acid, backed by layers 115 and 116 of hydrogel adhesive, for example, then base-tube fastened segments 117 and 118 of glycolic-lactide copolymer, layers of hydrogel adhesive, polycaprolactone, and layers of hydrogel adhesive. Suitable stones for shock wave lithotripsy include crystalline calcium oxalate monohydrate or dihydrate, calcium phosphate, and ammonium magnesium phosphate salts synthesized for disintegration by lithotriptor-generated shock waves (for such distinctions in lithotriptor dosage essential to achieve the breaking up of different stones, see for example, Bouropoulos, N., Mouzakis, D. E., Bithelis, G., and Liatsikos, E. 2006. "Vickers Hardness Studies of Calcium Oxalate Monohydrate and Brushite Urinary Stones," *Journal of Endourology* 20(1):59-63, and Johrde, L. G. and Cocks, F. H. 1985. "Fracture Strength Studies of Renal Calculi," *Journal of Materials Science Letters* 4(10):1264-1265).

An expansion insert or segment thereof that overlays a lithotriptor-destructible material with a layer of an absorbable material is considered equivalent to positioning an absorbable layer side-slit free edge proximad to a gapward stone. When subsidence nor the rate of subsidence can be predicted, consecutive segments devised for selective destructability or differential disintegration are used. Non-absorbable, the layers of the insert are prepared for selective disintegration, and when stone, need not chemically duplicate stones of endogenous origin. Differential resistance to ultrasonic disintegration is obtained by chemistry, dimensioning, and extent of gas entrapment Vakil, N. and Everbach, E. C. 1991. "Gas in Gallstones: Quantitative Determinations and Possible Effects on Fragmentation by Shock Waves," *Gastroenterology* 101(6): 1628-1634).

To facilitate pulverization (disintegration, fragmentation), stone inserts or layers thereof can be prebored or pre-lithotripsied (pre-lithotresed). Lithotripsy cannot span an air gap and requires continuity of medium for transmission from the shockwave generator or source of excitation to the target. Unless fluid-filled, the intervention of a body cavity will truncate transmission of the waves, which must ensonify the target. To affect the dissolution of an expansion insert material in a stent-jacket surrounding an artery, synchronization to the systolic pulse should not be necessary, and the process should work with veins. In addition to pulverizing stony materials, lithotripsy can accelerate the dissolution of nearby absorbable materials, which can be used to advantage.

Since these neighboring non-stone materials can also release medication, agitation by means of ultrasonic, and possibly pulse laser lithotripsy can be used to release medication. Miniballs, stays, and expansion inserts or the segments of these can consist entirely of or incorporate absorbable materials that include medication. However, any application of lithotripsy must not dislodge miniballs or stays that have already been implanted within the wall of the substrate ductus. Sufficient superparamagnetic magnetite or maghemite nanoparticles or finely grained powder can be incorporated into any kind of miniball to allow its recovery by means of the recovery electromagnets in the muzzle-head or repositioning or holding in place with the aid of an extracorporeal hand-held or probe extension from an imaging electromagnet, as addressed above in section 4g entitled Emergency Recovery of Miniballs and Stays and section X below entitled Steering and Emergency Recovery of Implants with the aid of an External (Extracorporeal) Electromagnet, among others.

Stent-jacket expansion inserts are simple when consisting of a single span of uniform material and compound when consisting of segments of different materials. The apposition and bonding of segments of uniform internal composition affords sufficient incremental control in any situation, individual segments constituted for incremental dissolution internally unnecessary. Depending upon the chemistry and configuration of the material or materials of the insert and the medical condition of the patient, the rate in breakdown or absorption will vary whether attributable to enzymatic proteolysis (gut, collagen), hydrolysis (synthetics), liquid infiltration, or chemical combination. Perforations to allow the free passage of gas between the milieu and adventitia significantly reduce strength and increase the surface area, hence, the rate of dissolution.

These factors must be offset by the material used. In most instances, single ply Type A (plain, nonchromic) catgut sheet in the thickness needed to compensate for strength lost to any 'breathing' holes will achieve the breakdown time required, with mild or light chromic catgut (Type B), medium chromic catgut (Type C), or extra or heavy chromic (Type D) of like conformation extending the breakdown period for a stent-jacket to be placed about a small artery by about seven to ten additional days each in the order stated. While absorbable suture must possess tensile rather than compressive strength, experience with suture and more particularly tissue engineering scaffolding indicates the variability in persistence in different thicknesses of absorbed implantable materials under various medical conditions.

The chemical environment, can be significantly altered in disease and at a site of disease expression in particular, a given absorbable material can vary in rate of dissolution. Materials ordinarily used in absorbable suture vary in rate of dissolution among individuals, and more so in patients with disease. Adding to the unpredictability as to timing of subsidence, natural materials (collagen, usually bovine or sheep gut, whether treated with aldehyde solution and chromium trioxide to extend absorption time as 'chromic catgut'), degrade by proteolytic enzyme breakdown and vary more in absorption time than do polyester based synthetics, which degrade by nonenzymatic hydrolysis of ester bonds. Synthetics are thus preferred as reducing overall unpredictability as to the mean dissolution time of the materials to constitute the stent-jacket expansion insert.

The volume and concentration of water and enzymes under conditions of increased or reduced exudation or secretion, for example, may be significantly altered. For example, a significant factor in selecting short-term dissolution materials for incorporation into the temporary expansion absorbable insert is that the free water and enzymatic composition of serous fluid differs in disease (see, for example, Ben-Horin, S., Shinfeld, A., Kachel, E., Chetrit, A., and Livneh, A. 2005. "The Composition of Normal Pericardial Fluid and Its Implications for Diagnosing Pericardial Effusions," *American Journal of Medicine* 118(6): 636-640). Temperature also affects the rate of dissolution, a high fever accelerating, and an ice table to lessen fever, for example, reducing the rate.

When an extended period necessitates the use of an insert material or materials that ultrasonic agitation would not disintegrate, laser lithotripsy is used. Selecting the material and dimensions of insert segments allows these to be arranged so that base-tube contraction occurs in planned increments. An enlarged ductus will ordinarily revert to the normal or nearly normal diameter with healing over time. The same is true of an incipiently aneurysmal elastic artery where the stent-jacket is essentially an elastic bandage that consists of an ordinary polymeric or copolymeric base-tube or a spandex backing with hook and loop spandex straps without magnets or ductus intramural implants where the mild constraint prevents the ductus from further enlargement and encourages reduction.

To not seal off the outer surface of the ductus from the surrounding cavity, the base-tube of an extrinsically magnetized stent-jacket and the stent-jacket itself when intrinsically or quasi-intrinsically magnetized is perforated and lined with viscoelastic or moisture barrier-coated viscoelastic polyurethane foam. When the internal surface of the expansion insert is in contact with the ductus, these should be incorporated into the expansion insert as well. When the swelling or the extent thereof whether the result of implantation cannot be predicted with confidence, implantation can precede placement of the stent-jacket, which is the normal sequence and allows an interval to observe whether swelling ensues. However, as addressed above in the section entitled Circumstances Recommending the Use of a Shield-jacket or Preplacement of the Stent-jacket, when implantation is ballistic, there are numerous reasons for placing the stent-jacket before initiating discharge. In that situation, an oversized stent-jacket with thicker foam lining is used with or without expansion insert.

The stent-jacket is supplied with different unitary or monolithic expansion inserts to dissolve over different overall periods. Expansion inserts to yield different increments and/or overall periods for subsidence are also provided. These can be preassembled; however, it is much more flexible or adaptable to a given condition to provide an assortment of insert segments of different materials and dimensions with suitable cements for local assembly. Especially when high density implantation is used to uniformly and more widely distribute the magnetic traction in order to reduce the risk of pull-through or perforation of the ductus wall, which may lack normal hardness, swelling may ensue, necessitating wider retraction. If the ductus is so malacotic that ballistic implantation is contraindicated, the use of stays should be considered before replacement or bypass grafting.

I11b. Intracavitary Infusion of Fluid for Lithotriptor Dissolution of Long-Term Controlled Destruction-Time Expansion Inserts or a Final Stone Base-Tube Bonded Layer in Multilayered Expansion Inserts The use of stone to allow lithotripsy for controlling stent-jacket contraction requires a second procedure, is suited to sites where disintegration fragments can be retrieved or would be innocuous if not retrieved, and is therefore undertaken only when necessary. Long-term temporary stays used without a stent-jacket are never made of stone. The use of electrohydraulic probes to accomplish the lithotripsy is inadmissible. When not interposed by a body cavity (potential space), lithotripsy coupling is conventional (percutaneous, extracorporeal). This will rarely be the case, vasa treated by the means herein described running just beneath visceral serosae, and thus requiring cavitary infusion of a shock wave propagation medium to achieve coupling.

Cavitary infusion is achieved either by injecting and afterwards aspirating away the coupling medium with water or by inserting a tightly rolled empty silicone cushion membrane through a local laparoscopy sized entry wound, injecting the intracavitary membrane with the medium, when so contained, preferably ultrasonography jelly (Cartledge, J. J., Cross, W. R., Lloyd, S. N., and Joyce, A. D. 2001. "The Efficacy of a Range of Contact Media as Coupling Agents in Extracorporeal Shockwave Lithotripsy," *British Journal of Urology International* 88(4):321-324). Postlithotripsy, the medium is suctioned (aspirated) away and the cushion membrane if any retracted. Due to the risk of injury to the subjacent adventitia of shock wave destruction, stone inserts are recessed from the internal surface of the stent-jacket or base-tube.

I11c. Absorbable Stent-Jacket Expansion Insert Materials with Relatively Short Breakdown Times Shorter-term materials in order of increased time for dissolution or loss of compressive strength include:

1. Glucose, dextran-40 and disodium (1-4)-2-deoxy-2-sulfoamino-ß-D-glucopyranuronan (S-chitosan).
2. Poly(ethylene glycol) and sugar (Wang, X., Yan, Y., Zhang, R., Fan, Y. W., Cui, F. Z., Feng, Q. L., and Liang, X. D. 2004. "Anastomosis of Small Arteries Using a Soluble Stent and Bioglue," *Journal of Bioactive and Compatible Polymers* 19(5):409-419); and in order of increasing degradation.
3. Polyglycolic acid.
4. Polylactic acid.
5. Polycaprolactone (Benicewicz, B. C. and Hopper, P. K. 1990. "Polymers for Absorbable Surgical Sutures—Part I," *Journal of Bioactive and Compatible Polymers* 1(5):453-472; W. J. Ciccone II, C. Motz, C. Bentley, and J. P. Tasto 2001. "Bioabsorbable Implants in Orthopaedics: New Developments and Clinical Applications," *Journal of the American Academy of Orthopedic Surgery* 9(5): 280-288). Gut is not preferred, primarily because it is less predictable as to its breakdown time. Other suitable biocompatible and absorbable (biodegraded) aliphatic polyesters include, for example,
6. Poly D,L-lactic-co-glycolic acid, polyvalerolactone, polyhydroxybutyrate, polyhydroxyvalerate, polyhydroxybutyrate-hydroxyvalerate, and polyhydroxybutyrate-hydroxyvalerate copolymer reinforced with polyglactin 910 fibers.

Other stent-jacket expansion insert materials based upon materials used in bioabsorbable suture, staples, endoluminal stents, and tissue engineering scaffolds include: 1. Polyglactin 910, which can be treated for more rapid breakdown; 2. Polydioxanone; 3. Poliglecaprone 25 (copolymer of glycolide and E-caprolactone); and 4. Woven and various blends of polyglycolic acid. Others such materials include Poly(lactide-co-glycolide) and Poly(glycolide/L-lactide) (see also Jeong, S. I.; Kim, S. H.; Kim, Y. H.; Jung, Y.; Kwon, J. H.; et al. 2004. "Biodegradable PLCL Scaffolds for Mechano-active Vascular Tissue Engineering," *Journal of Biomaterials Science-Polymer Edition* 15(5):645-660; Grayson, A. C. R., Voskerician, G., Lynn. A., Anderson, J. M., Cima, M. J., et al. 2004. "Differential Degradation Rates in Vivo and in Vitro of Biocompatible Poly(lactic acid) and Poly(glycolic acid) Homo- and Co-polymers for a Polymeric Drug-delivery Microchip," *Journal of Biomaterials Science-Polymer Edition* 15 (10): 1281-1304; and Lee, S. J., Lee, I. W., Lee, Y. M., Lee, H. B., and Khang, G. 2004. "Macroporous Biodegradable Natural/Synthetic Hybrid Scaffolds as Small Intestine Submucosa Impregnated Poly(D,L-lactide-co-glycolide) for Tissue-engineered Bone," *Journal of Biomaterials Science-Polymer Edition* 15(8):1003-1017); polyhydroxybutarate valerate; polyorthoester; and polyethylenoxide/polybutylene terephthalate.

I11d. Lithotriptor-Destructible Stone Stent-Jacket Expansion Inserts and Differentially Destructible Expansion Insert Layers When subsidence is premature or cannot be predicted, the expansion insert or segments (layers) thereof must be dispersible on demand. The object is to the extent possible to make the stent-jacket self-contracting with the need for reintervention forestalled if not eliminated but readily possible if necessary. To avoid the need for further intervention, when subsidence is predictable, the expansion insert or first to go segments thereof are absorbable. Without further intervention, such as warming or injection of a solvent, an expansion insert dissipated through absorption will break down over a period that varies with the chemical environment. Absorbable segments dissolve without intervention but if necessary, can be dissipated on demand, as addressed in the preceding section. When the term for subsidence might exceed the persistence of absorbable materials, the expansion insert is made of stone.

Intermediate levels of predictability are reflected in the sequencing of segments, where only that terminal, made of stone, may require intervention at a much later date, if ever. For a given expansion insert, any absorbable segments will have been dispersed before the stone layer remains; however, when other absorbable elements are present, the effect upon these of the agitation induced by lithotripsy must be taken into account, as must the effect of energy and frequency or firing rate levels on pull-through and delamination, and shock wave induced injury to a vulnerable substrate ductus. Differential destructibility of absorbable segments is based upon differential susceptibility to a certain solvent, and/or heat, and/or vibration. Differential destructibility of stone segments is based upon differential susceptibility of different natural stones or differentially formulated artificial stone to lithotriptor types as electrohydraulic, laser, or pneumatic and settings.

To this end, natural or synthetic stone has the equivalent of weakening microcracks introduced into it in a density and in an intersecting pattern keyed to coalesce or nucleate so as to induce failure after a time interval, and when applicable, in a layer sequence preferred (Lokhandwalla, M. and Sturtevant, B. 2000. "Fracture Mechanics Model of Stone Comminution in ESWL [extracorporeal shock-wave lithotripsy] and Implications for Tissue Damage," *Physics in Medicine and Biology* 45(7):1923-1940; Rassweiler, J. J., Tailly; G. G., and Chaussy, C. 2005 "Progress in Lithotriptor Technology," *European Association of Urologists Update Series* 3(1):17-36; Zhu, S., Cocks, F. H., Preminger, G. M., and Zhong, P. 2002. "The Role of Stress Waves and Cavitation in Stone Comminution in Shock Wave Lithotripsy," *Ultrasound in Medicine and Biology* 28(5):661-671; Cleveland, R. O and McAteer, J. A. 2007. "The Physics of Shock Wave Lithotripsy," Part IV, Chapter 38 in Smith, A. D., Badlani, G. H., Bagley, D. H., Clayman, R. V., Docimo, S. G. and 6 others (eds.), Smith's Textbook of Endourology, St Louis, Mo.: Quality Medical Publishing Company, pages 326-328). Such micropassages can be cut through the insert or a layer thereof by means of pulsed laser microdrilling under multiaxial positional control (see, for example, Clarke, J. A. and Profeta, J. III 2004. "Laser Micro-Drilling Applications," in Roessler, D. and Uddin, N., *Proceedings of the 2004 Advanced Laser Applications Conference and Exposition*, Volume 2, Saline, Mich., available at http://www.aerotech.com/pressbox/pdf/clarke_alac.pdf. and http://www.metalase.com/Clarke-Profeta%20Paper.pdf).

Injury to tissue is reduced by lowering the amplitude and frequency of shock wave delivery (Evan, A. P., McAteer, J. A., Connors, B. A., Blomgren, P. M., and Lingeman, J. E. 2007. "Renal Injury During Shock Wave Lithotripsy is Significantly Reduced by Slowing the Rate of Shock Wave Delivery," *British Journal of Urology International* 100(3): 624-628). Injury to tissue and blood due to cavitation (see, for example, Bailey, M. R., Cleveland, R. O., Colonius, T., Crum, L. A., Evan, A. P. and 4 others 2003. "The Role of Cavitation in Tissue Injury and Stone Comminution in Shock Wave Lithotripsy," Session 1H-2, *Institute of Electrical and Electronics Engineers International Ultrasonics Symposium* Proceedings, *Transactions of the Institute of Electrical and Electronics Engineers Ultrasonics, Ferroelectrics, and Frequency Control Society*) is additionally suppressed when the shock waves are administered with a pressure release reflector insert placed in the standard brass ellipsoid reflector (Evan, A. P., Willis, L. R., McAteer, J. A., Bailey, M. R., Connors, B. A., and 5 others 2002. "Kidney Damage and Renal Functional Changes are Minimized by Waveform Control that Suppresses Cavitation in Shock Wave Lithotripsy," *Journal of Urology* 2002 168(4 Part 1):1556-1562). As does the use of the use of lower frequencies (McAteer, J. A., Evan, A. P., Williams, J. C. Jr., and Lingeman, J. E. 2009. "Treatment Protocols to Reduce Renal Injury During Shock Wave lithotripsy," *Current Opinion in Urology* 19(2):192-195), the use of a wide angle focal zone lithotriptor evidently improves the effectiveness of shock wave delivery at low frequency and amplitude levels (Evan, A. P., McAteer, J. A., Connors, B. A., Pishchalnikov, Y. A., Handa, and 5 others 2008. "Independent Assessment of a Wide-focus, Low-pressure Electromagnetic Lithotripter: Absence of Renal Bioeffects in the Pig," *British Journal of Urology International* 101(3):382-388).

Expansion inserts or segments for eventual extracorporeal shock wave lithotripsy are generally in the multimillimetric if not millimetric size range. Machined stones of biological or geological origin provide sufficient material for many. Gallstones (choleliths), which consist primarily either of cholesterol, or of bilirubin and calcium salts, and urinary tract (kidney, ureteric, and bladder) stones, which consist of calcium oxalate monohydrate (whewellite) or dihydrate (weddellite); magnesium ammonium phosphate hexahydrate (struvite), struvite-carbonate apatite, uric acid, calcium phosphate, or cystine, are routinely harvested by slaughter houses. Large urinary calculi such as renal staghorn calculi and large gallstones are economically harvested at lithotomy.

Natural stone tending to include defects, direct machining yields numerous rejects. Therefore, when natural stone is used, it is preferred to crush and reconstitute the stone under high pressure using a biocompatible polymer binder such as polylactic acid. The cost of different molds is avoided by producing a standard sized block which is sectioned into differently sized briquette blanks. Each blank is then micromachined to specification, to include the disintegration micropassages or tunneling indicated above. Provided it exhibits the brittleness or lack of elasticity to fail when lithotripsied, a mineral such as crushed hydroxyapatite (hydroxylapatite), obtainable in particulate form for molding, allows the preliminary process of reconstitution to be eliminated.

The adaptation of tissue engineering scaffold preparation techniques even allows casting with interconnected channels (see, for example, Ott, A. and Irlinger, F. 2009. "Hydroxyapatite Powder Used for Rapid Prototyping in Medical Engineering," *International Journal of Computer Applications in Technology* 36(1):32-37; Yang, S., Leong, K. F., Du, Z., and Chua, C. K. 2001. "The Design of Scaffolds for Use in Tissue Engineering. Part I. Traditional Factors," *Tissue Engineering* 7(6):679-689). To allow differential lithotripsy and thus controlled reduction in stent-jacket expansion at intervals determined on the basis of diagnostic imaging of the residual enlargement of the ductus, harvested and synthesized calculi for use in multi-stone layered stent-jacket expansion inserts, wherein the layers have different shock wave exposure breakdown times, can be chosen based upon composition.

Breakdown times are addressed in the literature (see, for example, Pelander, W. M. and Kaufman, J. M. 1980. "Complications of Electrohydraulic Lithotresis," *Urology* 16(2): 155-157). The greater resistance to lithotripsy of calcium oxalate monohydrate compared to dihydrate, for example, has long been recognized. Naturally formed calculi can be modified in mechanical properties through chemical treatment (see, for example, Johrde, L. G. and Cocks, F. H. 1986. "Effect of pH on the Microhardness of Renal Calculi," *Journal of Biomedical Materials Research* 20(7):945-950). The persistence of a change in hardness following implantation of a calculus obtained from nature as the result of having been chemically treated warrants investigation.

The extracorporeal preparation (synthesis) of calculi (see, for example, Grases, F., Millan, A., and Conte, A. 1990. "Production of Calcium Oxalate Monohydrate, Dihydrate or Trihydrate," *Urological Research* 18(1):17-20; Lepage, L. and Tawashi, R. 1982. "Growth and Characterization of Calcium Oxalate Dihydrate Crystals (Weddellite)," *Journal of Pharmaceutical Sciences* 71(9):1059-1062) can emulate the physiological conditions under which these are produced in the body (see, for example, Balaji, K. C. and Menon, M. 1997. "Mechanism of Stone Formation," *Urologic Clinics of North America* 4(1):1-11; Mandel, N. 1996. "Mechanism of Stone Formation," *Seminars in Nephrology* 16(5):364-374) or can introduce extracorporeal innovations such as, biocompatibility allowing, exercising control over the morphological development of calcium oxalate dihydrate crystals (see, for example, Zhang, D., Qi, L., Ma, J., and Cheng, H. 2002. "Morphological Control of Calcium Oxalate Dihydrate by a Double-Hydrophilic Block Copolymer," *Chemistry of Materials* 14 (6):2450-2457).

I11e. Expansion Insert Bonding Agents (Adhesives)

I11e(1). Intrinsic Shorter-Term Insert-to-Base-Tube and Segment-to-Segment Bonding Agents Where the materials to be bonded allow, an alternative to the use of an adhesive is ultrasonic welding (Troughton, M. J. (ed.) 2008. *Handbook of Plastics Joining, a Practical Guide*, "Ultrasonic Welding," Norwich, N.Y.: William Andrew Publishing, page 15). The strength of cement bonds is strengthened by scoring or roughing up the surfaces and the cement chosen for the materials to be bonded. Nonabsorbed cements must remain innocuous if left intact and not break down into harmful degradation products. Cyanoacrylate cements in accordance with the guidelines stated below in the section entitled Extrinsic Shorter-term (Absorbable) to Longer-term (Stone) Layer Bonding Agents have wide applicability. Absorbable adhesives include polylactic acid (Ren, J. (ed.) 2010. *Biodegradable Poly (Lactic Acid): Synthesis, Modification, Processing and Applications*, Beijing, China: Tsinghua University Press/Springer Verlag; Petrie, E. M. 2010. "Polylactic Acid Biopolymer Adhesives," *SpecialChem* 24 Mar. 2010, at http://www.specialchem4adhesives.com/resources/articles/article.aspx?id=3534), and polycaprolactone (Choi, W. Y., Lee, C. M., and Park, H. J. 2006. "Development of Biodegradable Hot-melt Adhesive Based on Poly-ε-caprolactone and Soy Protein Isolate for Food Packaging System," *LWT* [Lebensmittel Wissenschaft and Technologie, Schweizerische Gesellschaft für]—*Food Science and Technology* 39(6):591-597).

At established temperatures and with suitable catalysts if necessary, these and other absorbable materials commonly used for suture and tissue engineering scaffolding as specified above, when constituting the expansion insert segments to be bonded, exhibit tackiness that makes these materials suitable for direct fusion as hot-melt adhesives negating the need for an extrinsic glue (Ren, J. Op. cit, Chapter 6, Section 6.5, "Biodegradable Hot Melt Adhesive Based on PLA [Polylactic Acid] and Other Biodegradable Polymers, pages 229-233; Stolt, M., Viljanmaa, M., Södergård, A., and Törmälä, P 2003. "Blends of Poly(-caprolactone-b-lactic acid) and Poly(lactic acid) for Hot-melt Applications," *Journal of Applied Polymer Science* 91(1): 196-204; Viljanmaaa, M., Sodergårdc, A., and Törmäläa, P. 2002. "Lactic Acid Based Polymers as Hot Melt Adhesives for Packaging Applications," *International Journal of Adhesion and Adhesives* 22(3): 219-226; Leadbetter, K. J. and Shalaby, S. W. 1993. "Study of Interfacial Bonding in Fiber Reinforced Absorbable Composites," *Journal of Bioactive and Compatible Polymers* 8(2):132-141). In addition to synthetic glues and sealants such as cyanoacrylate, fibrin sealants and genetically engineered polymer protein glues are also available.

I11e(2). Longer-Term Expansion Insert-to-Base-Tube and Layer-to-Layer Bonding Agents Longer-term insert-to-base-tube and layer-to-layer bonding agents for bonding expansion inserts to persist over a longer period, such as polymethyl methacrylate, must, as must shorter term or absorbable adhesives, break down into harmless degradation products or remain intact but innocuous. The maximum time of segment persistence and the chemical environment of the material used to bond the expansion insert to the base-tube and segments together will be the primary determinants of the adhesive dissolution time, so that expansion inserts in less intimate contact with the environment are more likely to necessitate noninterventional interventional measures as indicated above due to persistence beyond the period desired. Long-term bonding agents are thus better suited to the bonding of stone inserts to be actively destroyed whenever desired. Persistence of adhesion in stone-to base-tube polymer bonds is thus pertinent.

I11e(3). Extrinsic Shorter-Term (Absorbable) to Longer-Term (Stone) Layer Bonding Agents Long carbon chain cyanoacrylate adhesives as short as butyl 2-cyanoacrylate (B2-CA) can be used to bond one absorbable segment to another, whether in the expansion insert or at the insert to stent-jacket base-tube interface. Exceptionally, isobutyl-2-cyanoacrylate (bucrylate) has been cited as a potential carcinogen (Haber 2004; Nursal et al. 2004; and Samson and Marshall 1986, cited above in the section above entitled Specification of Cyanoacrylate Tissue Sealants and Bonding Agents; Vinters, H. V. Balil, K. A., Lundie, M. J. and Kaufmann, J. C. 1985. "The Histotoxicity of Cyanoacrylates," *Neuroradiology* 27(4):279-291; Vinters, H. V., Debrun, G., Kaufmann, J. C., and Drake C. G. 1981. "Pathology of Arteriovenous Malformations Embolized with Isobutyl-2-cyanoacrylate (Bucrylate). Report of Two Cases," *Journal of Neurosurgery* 55(5):819-825), and should not be used. The use of cyanoacrylate cements is addressed below in the section entitled Specification of Cyanoacrylate Tissue Sealants and Bonding agents, as well as in other sections.

Depending upon the specific materials to be bonded and the area and conformation of the contact surface, this kind of adhesive will usually allow the bonding of an absorbable polymeric or copolymeric segment to a stone segment, a stone segment to another stone segment, or a stone segment to a stent-jacket base-tube. The bonding of an absorbable polymer to stone as is used, for example, when the stent-jacket is to remain for an indeterminate time. A layer of stone can be deposited onto such a polymer (see, for example, Yokoyama, Y., Oyane, A., and Ito, A. 2007. "Biomimetic Coating of an Apatite Layer on Poly(L-lactic Acid); Improvement of Adhesive Strength of the Coating," *Journal of Materials Science: Materials in Medicine* 18(9): 1727-1734).

I12. Retardation in the Dissolution of Absorbable Stent-Jackets, Stent-Jacket Expansion Inserts, and Stays Whether used to make stent-jackets, stent-jacket expansion inserts, or stays, absorbable materials suitable for implantation can be modified to retard dissolution (see, for example, Maquet, V., Boccaccini, A. R., Pravata, L, Notingher, I., Jérôme, R. 2004. "Porous Poly(alpha-hydroxyacid)/Bioglass Composite Scaffolds for Bone Tissue Engineering. I: Preparation and In Vitro Characterisation," *Biomaterials* 25(18):4185-4194; Maquet, V., Boccaccini, A. R., Pravata, L., Notingher, I., and Jérôme, R. 2003. "Preparation, Characterization, and In Vitro Degradation of Bioresorbable and Bioactive Composites Based on Bioglass-filled Polylactide Foams," *Journal of Biomedical Materials Research. Part A* 66(2):335-346; Slivka, M. A. and Chu, C. C. 1997. "Fiber-matrix Interface Studies on Bioabsorbable Composite Materials for Internal Fixation of Bone Fractures. II. A New Method Using Laser Scanning Confocal Microscopy," *Journal of Biomedical Materials Research* 37(3):353-362; Ibnabddjalil, M., Loh, I. H., Chu, C. C., Blumenthal, N., Alexander, H., and Turner, D. 1994. "Effect of Surface Plasma Treatment on the Chemical, Physical, Morphological, and Mechanical Properties of Totally Absorbable Bone Internal Fixation Devices," *Journal of Biomedical Materials Research* 28(3):289-301; Assimos, D. G., Smith, C., Schaeffer, A. J., Carone, F. A., and Grayhack, J. T. 1984. "Efficacy of Polyglycolic Acid (PGA) Tubing Stents in Ureteroureterostomies," *Urological Research* 12(6):291-293, and this in conjunction with the timed release of medication (see, for example, Tarcha, P. J. 1999. *Polymers for Controlled Drug Delivery*, Boca Raton, Fla.: Chemical Rubber Company Press division, Taylor & Francis). The immediate chemical environment of the material as used in stays or expansion inserts, for example, will be the primary determinant of the dissolution time. In little if any contact with tissue, expansion inserts, for example, are more likely to necessitate interventional measures due to persistence beyond the period desired.

I13. Alternative Procedure to the Use of Expansion Inserts

The use of an oversized jacket with thicker foam lining with or without an expansion insert is addressed in the section above entitled Expansion Inserts Absorbable, Meltable, and Comminutable for Time-discrete Decremental Contraction of Stent-jackets. As an alternative to the use of stent-jackets with expansion inserts, an off-the-shelf absorbable endoluminal stent with an appropriate dissolution time is placed for the period during which the ductus is expected to remain swollen following discharge implantation (see, for example, Waksman. R. 2007. "Promise and Challenges of Bioabsorbable Stents," *Catheterization and Cardiovascular Interventions* 2007 70(3):407-414; Waksman, R. 2006. "Biodegradable Stents: They Do Their Job and Disappear," *Journal of Invasive Cardiology* 18(2):70-74; Waksman, R. 2006. "Update on Bioabsorbable Stents: From Bench to Clinical," *Journal of Interventional Cardiology* 19(5):414-421.

Absorbable stents designed to minimize thrombogenesis and the release of embolizing debris have already been described (see, for example, Tamai, H., Igaki, K., Tsuji, T., Kyo, E., and four other authors 1999. "A Biodegradable Poly-l-lactic Acid Coronary Stent in the Porcine Coronary Artery," *Journal of Interventional Cardiology* 12(6):443-450; Stack, R. S. and Klopovik, Z. P. 1994. "Absorbable Stent," U.S. Pat. No. 5,306,286). Upon confirmation that the temporary device has completely disappeared as by computed tomography or intraductal ultrasound, a stent-jacket of the presumptive healed or end-condition internal diameter is placed in a followup procedure. If made, for example, of biodegradable poly-l-lactic acid, the second procedure would generally follow the first in about five months. In an artery, to reduce the risk of restenosis into the absorbable stent as it disintegrates, whereby substantial reocclusion would precede complete absorption making a transluminal approach risk embolism, the stent should incorporate in-stent intimal hyperplasia-suppressive medication (see for example, Tsuji, T. 1., Tamai, H. 1., Igaki, K., Kyo, E. and seven other authors 2003. "Biodegradable Stents as a Platform to Drug Loading," *International Journal of Cardiovascular Interventions* 5(1): 13-16).

Other ductus present similar considerations (see, for example, Tanaka, T., Takahashi, M., Nitta, N., Furukawa, A., Andoh, A., Saito, Y, Fujiyama, Y., and Murata, K. 2006. "Newly Developed Biodegradable Stents for Benign Gastrointestinal Tract Stenoses: A Preliminary Clinical Trial," *Digestion* 74(3-4):199-205; Saito Y, Tanaka T, Andoh A, Minematsu H, Hata K, Tsujikawa T, Nitta N, Murata K, Fujiyama Y. 2007. "Usefulness of Biodegradable Stents Constructed of Poly-l-lactic Acid Monofilaments in Patients with Benign Esophageal Stenosis," *World Journal of Gastroenterology* 13(29):3977-3980). An absorbable endoluminal stent can release medication such as steroidal to reduce any swelling. The absorbable stent will usually be coated with anesthetic and antiplatelet or anticoagulant medication as well. Medication is addressed below in the section entitled Medicated and Medication Miniballs.

The incorporation into absorbable stents of medication is under development (see, for example, Bünger, C. M., Grabow, N., Sternberg, K., Kröger, C., and seven other authors 2007. "Sirolimus-eluting Biodegradable Poly-L-lactide Stent for Peripheral Vascular Application: A Preliminary Study in Porcine Carotid Arteries," *Journal of Surgical Research* 139(1):77-82. Uurto, I., Mikkonen, J., Parkkinen, J., Keski-Nisula, L., Nevalainen, T., Kellomäki, M., Törmälä, P., and Salenius J P. 2005. "Drug-eluting Biodegradable Poly-D/L-lactic Acid Vascular Stents: An Experimental Pilot Study," *Journal of Endovascular Therapy* 12(3):371-379; Tsuji, T., Tamai, H., Igaki, K., Kyo, E., and seven other authors 2003. "Biodegradable Stents as a Platform to Drug-loading," *International Journal of Cardiovascular Interventions* 5(1):13-16). Exceptionally, in a ureter, where standard practice calls for the placement of a nonabsorbable metal endoluminal stent that clogs and must be replaced every few months and the interim use of an absorbable stent is not an option, implantation and the placement of an extraluminal stent are accomplished ab initio. The lumen is then free of any foreign object that would promote clogging and interfere with transluminal recanalization or recannulation.

I14. Sectional, or Chain-Stents, Segmented and Articulated

I14a. Purposes and Types of Chain-Stents

A sectional or chain-stent comprises a succession or train of tied substents as intermittent or serial. The subsidiary stent-jackets or substents connected by flexible ties, the stent as a whole is able to follow a curved segment of a ductus without distorting structure, and to accommodate movement about a hinge joint (ginglymus) or ball and socket joint (enarthrosis, spheroidea). Such a stent is intended to minimize interference with normal physiology and simplify extension to as yet unaffected (unlesioned) portions of a diseased ductus. As with a unitary extraluminal stent, a sectional stent overall and in each of its substents is comprised of intravascular and circumvascular components. Ordinarily, the ductus-intramural implants (miniballs or stays) are placed in apposite or complementary relation to the substents; however, when speed is essential, as when wishing to avoid the need for cardiopulmonary bypass, miniballs placed with the aid of machine-controlled transluminal advancement and discharge are laid down in a continuous formation.

As always, not all of the miniballs or stays associated with a given stent-jacket, here a substent-jacket, need be of like constitution. Miniballs can be placed before or after the stent-jacket, whereas stays must be placed first. Advantages in the use of articulated or chain-stents include entry through a single incision, eliminating the need for separate entry and locating the treatment site for each in a number of separate stent-jackets. Sectional or chain-stents are either segmented or connected end to end by suture or wire. Segmented chain-stents are cut into a continuous length of tubing with a narrow bridge portion left to connect the otherwise separate segments so that a given number can be snipped off or trimmed as needed. The tubing can be discretely, intrinsically, or quasi-intrinsically magnetized or laminated.

To resist the straightening urge of the elastic tubing, the bridge portions of a segmented stent are kept narrow. While the sub-stents in a segmented stent differ only in length or interval, the sub-stents in such an assembled chain-stent can differ in any or all properties. Substents in a segmented chain-stent will ordinarily be alike in length and distance from one to the next. Variability among substents is achieved by the free sequencing of separate jackets as modules or links into a chain connected end to end by suture or wire. In an assembled or nonsegmented chain-stent, the interval separating the substents is based upon the diagnosis and freely changeable from one substent to the next, each sustent-jacket in the train is presequenced to overly its intended location.

The variability among substents in a chain includes the internal and external diameters and length of each, whether the foam lining of each is wetted with the same or different drugs or other therapeutic substances, stent-jacket resilience, type as intrinsically, quasi-intrinsically, or extrinsically magnetized, the field strength and medication of each, and the distance separating each substent from the substent to its front and back. Except for segmented chain-stents, which are cut from a continuous length of tubing, the individual jackets or substents in a chain can be distinct in virtually any way that one jacket can differ from another, to include the use of side-straps, inclusion of an expansion insert, and so on.

Moreover, a chain can include impasse- as well as radiation shield-jackets and stent-jackets where each is matched to the condition of the ductus at its respective site. This allows the capability of each type jacket specified in the section above entitled System Implant Magnetic Drug and Radiation Targeting to be applied so as to maintain the ductus patent, drug-targeted, with the impasse-jacket-suspended medicinal miniball or miniballs, for example, noninvasively extractable to a safe location outside the ductus or entirely out of the body. Additional advantages of serial connection include multiple contact areas or anchoring that prevents migration and can expedite the locating of a failed substent if necessary.

Relatively free of the detractions pertaining to endoluminal stents, a chain-stent arouses less concern for complications in extension for prevention, such as to preempt a changing pattern of vasospasm (see, for example, Wada, M., Hara, H., and Nakamura, M. 2006. "A Change in the Pattern of Vasospasm after Stenting in a Patient with Vasospastic Angina," *Heart and Vessels* 21(6):388-391; Li, Y., Honye, J., Takayama, T., and Saito, S. 2007. "Generalized Spasm of the Right Coronary Artery after Successful Stent Implantation Provoked by Intracoronary Administration of Ergonovine," *International Journal of Cardiology* 119(2):251-254; Kaku, B., Honin, I. K., Horita, Y., Uno, Y., Yamazaki, T., Funada, A., and Ohka, T. 2005. "The Incidence of Stent-edge Spasm after Stent Implantation in Patients with or without Vasospastic Angina Pectoris," *International Heart Journal* 46(1):23-33), without added risk thus averting the need for later procedure.

Not limited to a diameter slightly greater than that of the lumen, an extraluminal stent to include a chain-stent is more adaptable than consecutive endoluminal stents. Unless an angioplasty is to precede placement, the use of stays eliminates a transluminal procedural component. At the same time, the lumen wall is nowhere restrained as prevents normal movement and overlain as prevents normal blood-endothelial chemical, such as hormonal, exchange. Not interfering with normal function and thus posing the risk of inducing pathology, extension for prevention using segmental and preventive use more generally, using separate extraluminal stents, are accomplished with less hesitancy. The same applies to other type ductus where the prognosis indicates that additional lesions are likely to appear in certain locations.

Another advantage in a segmented extraluminal stent wherein each substent can differ in length and distance from its neighbors is the ability to ride and/or straddle portions of ductus that flex or are more densely supplied with small blood vessels, for example. Articulated' chain stent-jackets are separately made stent-jackets that are secondarily connected or strung together into a train or chain, whereas 'segmented' stent-jackets are cut into a continuous length of tubing, with a connecting tab or band of the tube wall, the bridge, running continuously from one segment to the next from end to end. In an articulated or chain-stent, the ends of the sub-stent connecting wires are secured by short barrel wide head rivets situated toward the edges of the adjacent base-tubes so that the wires pass from the outer surface of one sub-stent to the next.

The distance from the end edges of adjacent sub-stent base-tubes that the rivets are placed depends upon the resistance to tearing of the base-tube based upon the strength and thickness, of the base-tube material. Expansion inserts can be used with any or every substent in a chain-stent of any kind. The rivets for the connecting wires must be longitudinally and circumferentially offset from the area of attachment of an expansion insert if present. Somewhat oversized segmented stent-jackets that incorporate thicker moisture barrier-coated viscoelastic polyurethane foam linings allow placement in childhood that need not be replaced to accommodate growth. Adjacent sub-stents render the chain less susceptible to migration; in most instances, the use of end-ties as addressed above in the section entitled Jacket end-ties and Side-straps is not necessary.

In the harsh internal environment, the yield strength of the bridge portions in a segmental chain-stent, with a large surface area-to-volume ratio may, depending upon the material of which the base-tube and integral bridge are made, degrade and fail. To prevent this and the migration that would ensue, a fine wire of nonmagnetic stainless steel attached by staples of the same metal at intervals is run across the outer surface of the segmented stent from end to end over the bridges. When the stent-jacket mounts magnets, a wire runs parallel to the sides of these along the bridges. The wire makes snipping off the number of substents needed a little more difficult but assists in advancing the segmented stent through the entry portal as addressed in the section to follow. However, the bridges are not strengthened by lamination with another layer of an elastic material nor increased in width, since this either reduces the flexibility of the chain.

The addition of a wire requires that the number of sub-stents to be used are cut off the continuous strip of substents with wire cutters rather than scissors. Other sectional stents are assembled for the specific application, the queue including jackets connected with suture or stainless steel wire and rivets in whatever sequence is wanted. The connecting wires extraluminal, similarity to a jointed Palmaz-Schatz stent is meaningless. In contrast to other sectional stent-jackets, segmented stent-jackets are identical from one to the next. The miniballs or stays associated with each substent-jacket, however, need not be the same. The potential range of therapeutic variability from one to the next is thus considerable, but less than that of other sectional stent-jackets, which are more costly and must be specially assembled for each patient.

To alter consecutive substent-jackets, as by varying the strength of magnetization from one to the next, undoes the economy of uniformity as an off the shelf device. As shown in FIG. 13, a segmented chain-stent-jacket base-tube is provided in the form of a continuous length of tubing 120 with the repetitive pattern of substent-jackets having been cut into it. Continuous connecting strip or bridge 121 runs along the top of the tube to connect the substent-jackets in the segmented stent-jacket. The material of the tube as shown is elastomeric with extrinsic magnets; however, a segmented stent-jacket can be intrinsically magnetized, in which case it is made of thin magnetizable stainless steel, quasi-intrinsically magnetized, or magnetized by lamination or coating, the constitution of each type addressed above in the section entitled Types of Stent-jacket.

Jacket antimigration cinching straps or belts 122, referred to as end-straps when fastened to connecting strip or bridge 121 portion cut off from a segmented chain-stent as shown in FIG. 14 and thus not overlapping the jacket, and side-straps when wrapping about the jacket as shown in FIG. 15, are ordinarily strips of hook and loop surfaced spandex. End and side-straps are fastened to the stent-jacket with wide-head rivets 123. To cut off one or as many continuous substent-jackets as the longitudinal extension or potential extension of the condition warrants, tube 120 with repetitive substent segments is cut with scissors or wire cutter midway between the end-straps 122.

I14b. Procedure for Placement of a Chain-Stent

In placing a segmented chain-stent, the ductus is imaged as necessary, any vessels or nerves to be left intact noted, and the ductus freed of surrounding tissue as necessary. Unless the length of the segment requiring treatment is extended, requires studied dissection, or the number of vessels or nerves to be avoided significant, two entry points are used. That proximal is used to insert and advance the first or most distal substent, which is moved past or advanced to lie directly beneath the more distal entry point. Using one of the hand tools described in the section below entitled Stent-jacket Insertion Tools, each successive substent is opened around the ductus beneath the distal incision.

The distal entry point is positioned to overlie a structure to be avoided when present, the substents provided with a side-slot of adequate width to pass the structure and one if not both side-straps removed at the substent junction to straddle the structure before entry. The insertion tool with illuminating endoscope lashed alongside as necessary is introduced through this second distal entry point where the leading substent is opened to encircle the ductus. When the vessel or nerve to be avoided is deep and not seen, the substents are marked to indicate the angle that places the side-slot on the far side so that it will straddle or clear and slide past the structure with the least contact.

The foam lining of the substents is wetted with a lubricant such as ACS Microslide®, Medtronic Enhance®, Bard Pro/Pel® or Hydro/Pel®, Cordis SLX®, or Rotaglide® if necessary, so that once in encircling relation, pulling the first substent while pushing the extracorporeal retinue or train of substents forward or farther distal slides the second substent into position for encirclement. The segmented stent is advanced by pushing the proximal while pulling the distal end-substent to slide the stent forward along the ductus until the next substent is positioned beneath the incision. Buckling when pushing the promial end is lessened by using a segmented stent with stainless steel wires running along the top of the substent junctions of bridge sections. When possible, drugs and any other therapeutic substances are applied in a form that also contributes to lubricity or is compatible with the lubricant.

The bridge sections can be of any length but are not increased in length to allow these to be pulled away from the underlying ductus for slipping one jaw of the cutting tool underneath; instead, the bridge sections should be cut through perpendicularly with only so much separation from the adventitia as is needed to prevent injury thereto. The substents are slid past the subsidiary structure until the substent junction or bridge segment with side-straps removed straddles the structure leaving it in the clear. When another subsidiary structure at a different angle is to be avoided, the incision for insertion of the chain is placed distal to it. Subsidiary structure that enter and depart the substrate ductus at different angles are accommodated by cutting the bridge between the adjacent substents and rotating these to allow passage of the subsidiary ductus at the side-slot of each.

The end side strap of one can be used to cinch the ductus and that of the other to attach to the other side-strap after having been trimmed of nonessential slack. Made with a spandex backing and covered with hooks and loops, the terminal side-straps of adjacent jackets that are separate with a subsidiary structure between them can be fastened directly to one another, thereby reducing any tendency to migrate. The number of substents required along any one segment is not cut off the strip until closing. An articulated chain-stent in a similar application is placed in the same way. However, since the number of substents are made for the application, a dummy proximal extension may be added if necessary to assist in pushing the substents along. Also when such a chain-stent must be advanced by pushing and pulling it along the ductus, wires of sufficient inflexibility to allow the chain to pushed forward are used.

I15. Miniball and Ferrofluid-Impassable Jackets, or Impasse-Jackets

I15a. Uses of Impasse-Jackets

Impasse-jackets, or impasse and extraction jackets, serve either of two purposes, and compound miniball-impassable jackets usually include at least one jacket to serve each purpose. One purpose is to act as a prepositioned endarterial, intravenous, or intrabronchial trap or guard, termed a trap-, guard-, stopping- -jacket or -collar, that will seize and prevent further passage of a miniball or miniballs that enter the circulation upsteam. The other purpose is as a holding jacket to suspend susceptible miniballs and nanoparticles in the lumen, this type more likely to be radially asymmetrical as to magnetic field strength to draw a drug carrier bound drug, for example, into an eccentric tumor, for example. Drug nanoparticles and drug carrier nanoparticles can be introduced upstream in a ferrofluid or released from a miniball.

Magnetically susceptible matter is drawn into the ductus wall while the nonsusceptible is carried forward. Thus, a miniball is drawn up against the ductus wall where it can initiate the timed release of drug carrier nonoparticles that will be drawn into the ductus wall over a segment contingent upon the holding jacket strength of magnetization or medication from that level for passage downstream. An impasse-jacket must not only stop but facilitate the extraction of a miniball without injury to the substrate (treated) ductus, almost always an artery. To avert the stopping of a miniball precariously at the ends of the jacket or the sudden levering or end-pushing of the jacket under the pull of the external extraction electromagnet, magnetization of the jacket is concentrated at its center and the jacket extended to encircle a longer segment of the ductus.

Moisture barrier-coated viscoelastic polyurethane foam end-cuff linings in the impasse-jacket and similarly lined dummy-collars or outriggers as described below, securely fit the jacket to the ductus while affording additional flexibility in ductus and/or jacket diameter resulting in good compliance while preventing injury to the ductus from the mesh. Dummy-collar type outriggers differ from end-tie outriggers or end-tabs in being braced, that is, bridged by stainless steel bridge pieces as seen in FIG. 16, extending the anti-levering stabilization out to the ends of the triad. The need for inflexibly or hard-braced impasse-jacket type outrigger anchors to resist levering or end-suture tethered end-tie type end-tabs (end-collars) to prevent migration along the ductus depends upon the preexisting strength of the connection of the ductus to the surrounding tissue.

A miniball loose in any other type ductus, such as in the airway, is not swept forward and is therefore quickly apprehended, rarely if ever allowing the need to preposition a trap-jacket downstream. Continued movement of a miniball through the circulation may bode the misdirection of radiation, medication, or another bioactive substance to tissue downstream from the level intended, and whether a permanent miniball or one absorbable but not disintegrable on demand, embolization. Of these, blockage poses the least risk; due to the small size of miniballs in proportion to the level along the vascular tree to which these are targeted, were a miniball loose in the circulation to proceed unchecked, embolization would result well downstream.

At this level, collateral circulation is almost always abundant, dispelling significant risk, and retraction to a safe internal location or extraction from the body relatively simple and safe, as addressed below in the section entitled Stereotactic Resituation of a Mispositioned Miniball. Whether to place an impasse-jacket is thus a matter of judgment based upon the potential adverse consequences of mispositioning a miniball of specific content. Impasse-jackets not only prevent such an eventuality midprocedurally, but if nonabsorbable, indefinitely. Any stent-, impasse-, or magnet-jacket can attract magnetically susceptible-bound matter and thus serve for magnetic drug-targeting when appropriate.

In some instances, the requirement for magnetic strength to accomplish this may disallow the concurrent use of the jacket for stenting, because the more powerful traction might result in pull-through and/or delamination. An impasse-jacket includes at least one ductus-encircling member, or jacket, which is magnetized in the radial direction relative to the long axis of the jacket. Since an impasse-jacket must trap a miniball that approaches it, impasse-jackets are chained only when a single jacket may lack the necessary space for plural miniballs and the blood is sufficient to force miniballs forward to the next jacket. When the jacket must allow the miniball trapped within it, usually one nonabsorbable, to be extracted, the strength of jacket magnetization is greatest at the center and dropped off moving toward the ends.

In longer specimens, the end segments are not magnetized. To prevent injury to the substrate ductus as the result of levering in a powerful magnetic field used for extraction, magnetization thus and the addition of securing and anti-levering outrigger jackets (end-cuffs, end-collars) essentially snipped off from the ends of the impasse-jacket or of the kind used with end-ties are applied. That is, these measures combine to secure and stabilize the ends of the impasse-jacket during an extraction so that the long axis of the jacket remains perpendicular or normal to the electromagnet and aligned, rather than levering, in relation to the substrate ductus. As gratuitously disallowing other uses in the future once placed, uniform magnetization end to end is generally discounted, even when the immediate application involves only absorbable miniballs.

Accordingly, the prospects for future treatment of the specific patient should decide whether an impasse-jacket will be absorbable or magnetized over its entire length. Extraction applies to the removal of a miniball that should be removed, such as one containing a radioisotope or a potent drug that was to have been targeted. A miniball trapped by the jacket having been dislodged upstream as the result of a direct blow or passing through a strong magnetic field, for example, can often be left in the jacket indefinitely. An impasse-jacket for use with high dose-rate seed miniballs can be provided with a radiation shield formulated to disintegrate on demand, thus exposing the underlying cribriform or sieve configured extraction grid (filter screen, grating) to allow extraction, as addressed above in the section entitled Noninvasive Dissolution on Demand of Absorbable Stent-jackets, Base-tubes, and Radiation Shields.

The mesh material of a nonabsorbable extraction grid can be made as is an intrinsically magnetized stent-jacket of spring stainless flat sheet stock, as addressed above in the section entitled Intrinsically Magnetized Stent-jackets. If the grid is to be coated, such as with a neodymium impregnated polymer, then the mesh size on die punching must take into account the reduction in mesh size imparted by the coating. Magnetization then is not uniform as in the case of the stent-jacket but rather stronger at the center and reduced moving out toward either end. The magnetized sheet is then sectioned with a shears and the halves of the impasse-jacket formed on a mandrel. Alternatively, each half-cylinder of the jacket can be magnetized separately.

The entire internal and external surfaces at and about the central circumference are of like polarity and repel so long as either side does not form a closed local magnetic circuit through miniballs within the jacket to either side. Accordingly, the restorative force of the spring-hinge that closes the jacket about the ductus is selected to overcome the tendency for opening due to the repulsion of the opposing poles at every diameter. Except for the removal of a high dose-rate seed or potent drug miniball, extraction is seldom if ever necessary. Moreover, even in the bloodstream, the jacket will retain a number of miniballs indefinitely, extraction needed to preclude obstruction when the result of improperly introducing a larger number of miniballs not destructible on demand than the jacket was designed to retain.

Impasse-jackets thus suspend radiation or medication miniballs in the circulation or prevent emergencies, allowing resituation or extraction of miniballs in unusual circumstances if and when these pose a risk. Provided extraction through the wall of the ductus is unlikely to spread sepsis that could not be quickly eradicated, an external electromagnet allows a miniball or miniballs trapped or held in an impasse-jacket—to be extracted noninvasively through the wall of the ductus and mesh, the extraction grid or extraction grating, of the impasse-jacket to a point outside the ductus where the miniball would be innocuous, or entirely to the magnet outside the body.

The means to accomplish this are addressed above in the section entitled Emergency Recovery of Miniballs and Stays and in section X2c below entitled Stereotactic Arrest and Extraction of a Circulating, Dangerously Mispositioned, or Embolizing Miniball. Whether the primary or later as an unforeseen object, once placed, a stent-jacket, impasse-jacket, or magnet-jacket constitutes not only a prepositioned magnetic miniball trap, but can be used as a radiation or drug-targeting device. In this capacity, it may be used alone or with other such jackets for staged targeting, as addressed below in the section entitled Cooperative Use of impasse-jackets in Pairs and Gradient Arrays.

Extraluminal, a stent- or impasse-jacket can incorporate a larger mass of magnetized material to present a much more powerful magnetic field than might a radiation-emitting endoluminal stent. The extraluminal stent is not only able to attract drug carrier nanoparticles, for example, from a ferrofluid infused upstream, but critically, because it is located behind rather than in front of the lesion such as a plaque in the lumen wall, the jacket draws the drug carrier nanoparticles, for example, into the lesion rather than stands between, attracts, and therefore precisely blocks the direct transendothelial path into the lesion.

An absorbable such as polyurethane based miniball or stay that releases ribonucleic acid nanoparticles resistant to enzymatic breakdown such as gene silencing can be directly infixed in the lumen wall to accomplish nonmagnetic transfection of small interfering ribonucleic acid, for example, in vivo (see, for example, Nelson, C. E., Gupta, M. K., Adolph, E. J., Shannon, J. M., Guelcher, S. A., and Duvall, C. L. 2012. "Sustained Local Delivery of siRNA from an Injectable Scaffold," *Biomaterials* 33(4):1154-1161; Tokatlian, T. and Segura, T. 2010. "siRNA Applications in Nanomedicine," *Wiley Interdisciplinary Reviews. Nanomedicine and Nanobiotechnology* 2(3):305-315; Higuchi, Y., Kawakami, S., and Hashida, M. 2010. "Strategies for in Vivo Delivery of siRNAs: Recent progress," *BioDrugs: Clinical Immunotherapeutics, Biopharmaceuticals, and Gene Therapy* 24(3): 195-205).

A ductus-intramural miniball or stay or a miniball formulated thus suspended within the lumen by a holding or stent-jacket can be used to release magnetic drug carrier-bound gene silencing ribonucleic acid nanoparticles thereby causing the medication to be drawn into the lesion or tumor by magnetically assisted transfection (see, for example, Plank, C., Zelphati, O., and Mykhaylyk, O. 2011. "Magnetically Enhanced Nucleic Acid Delivery. Ten Years of Magnetofection—Progress and Prospects," *Advanced Drug Delivery Reviews* 63(14-15):1300-1331; McBain S C, Yiu H H, Dobson J. 2008. "Magnetic Nanoparticles for Gene and Drug Delivery," *International Journal of Nanomedicine* 3(2):169-180; Bertram, J. 2006. "MATra—Magnet Assisted Transfection: Combining Nanotechnology and Magnetic Forces to Improve Intracellular Delivery of Nucleic Acids," *Current Pharmaceutical Biotechnology* 7(4)277-285; Takeda, S., Terazono, B., Mishima, F., Nakagami, H., Nishijima, S., and Kaneda, Y. 2006. "Novel Drug Delivery System by Surface Modified Magnetic Nanoparticles," *Journal of Nanoscience and Nanotechnology* 6(9-10):3269-3276; Morishita N, Nakagami H, Morishita R, Takeda S, Mishima F, and 4 others 2005. "Magnetic Nanoparticles with Surface Modification Enhanced Gene Delivery of HVJ-E Vector," *Biochemical and Biophysical Research Communications* 334(4):1121-1126; Plank, C., Schillinger, U., Scherer, F., Bergemann, C., Rémy, J. S., Krötz, F., Anton, M., Lausier, J., and Rosenecker, J. 2003. "The Magnetofection Method: Using Magnetic Force to Enhance Gene Delivery," *Biological Chemistry* 384(5):737-747).

Reference to silencing ribonucleic acid should not be taken to exclude the transfection of nucleic acid in other forms, to include deoxyribonucleic acid, messenger, double stranded, small or short hairpin ribonucleic acid, oligodeoxyribonucleotide, and that virus-bound. Single stage and multistage magnetic drug-targeting are addressed above in the section entitled System Implant Magnetic Drug and Radiation Targeting. An impasse-jacket that releases radiation and/or is used to retain radioactive miniballs at a certain level or segment of the ductus includes an encircling radiation shield. The shield is formulated either to spontaneously disintegrate according to the duration of irradiation prescribed or upon effective depletion of the radiation source seed-miniball or to be disintegrable on demand, as addressed above in the section entitled Noninvasive Dissolution on Demand of Absorbable Stent-jackets, Base-tubes, Radiation Shields, and Miniballs.

Most miniballs and stays are too small to incorporate a tuning or segregably addressable function such that only one in a group might be selectively disintegrated or otherwise controlled such as to steer it. Differential steerability, for example, would allow miniballs to be distributed to different points about the luminal circumference encircled by an impasse-jacket to preserve patency as a temporary stent with absorbable components or one for long term use where the miniballs are extracted. Graduating the magnetically susceptible content in miniballs affords a degree of selectability for entrapment within one in a succession of impasse-jackets where each exerts greater tractive force than that preceding it. Miniballs are addressed by aiming a magnetic field and limited to the focus thereof.

The interposition of tissue disallows the use of lasers and infrared transmission, for example, to control miniballs. An impasse-jacket can be used to trap and suspend in the lumen medicinal or irradiating miniballs at a selected level of a ductus, usually a blood vessel, in order to target treatment at and/or downstream from that level. The noninvasive disintegrability on demand if medicinal and/or extractability at will of the miniball or miniballs suspended thus also distinguish this approach from the use of either an internal or an external radiation or medication emitting collar or stent and makes possible the short-term use of a dose-rate higher than that of conventional seeds, which left to decay, must be limited in dose-rate and life.

Miniballs injected into an artery upstream of the jacket incorporate sufficient ferrous content for magnetic arrest, and when to be noninvasively heatable, this content has continuity. Upon reaching the jacket, the miniball is drawn against the lumen wall. With increased magnetic strength, the miniball pushes the wall outward, exerting a patenting or stenting effect without the need for ductus-intramural placement, but uncontrolled as to circumferential position. Where this does not matter, an isolated vasculitis-induced potentially necrotizing atresia, for example, can be held patent thus with both the impasse-jacket and miniball disintegrated when no longer needed.

The magnetic strength of an impasse-jacket is not set so high that an intact miniball would be drawn into a ductus-intramural lesion risking delamination and pull-through; rather, the drug carrier nanoparticles the miniball releases are drawn into the lesion. By heating a holding jacket used thus as addressed above in the section entitled Implants that Radiate Heat on Demand, it is possible to accelerate the dissolution of a drug or other therapeutic substance coating of the suspended miniball and the uptake or other action of this substance by the diseased tissue. The miniball can itself be made disintegrable on demand, as addressed above in the section entitled Noninvasive Dissolution on Demand of Absorbable Stent-jackets, Base-tubes, Radiation Shields, and Miniballs.

Holding jackets allow held medication miniballs to be extracted at any time. Suspended miniballs can dissolve spontaneously or on demand. Releasing a counteractant or neutralizer from a miniball or miniballs suspended by a holding jacket or holding jackets downstream from the releasing miniball or miniballs holding jacket makes it possible to mark off lengths of a ductus for targeted treatment by drugs in different combinations and in higher concentration than could be infused to circulate throughout the body. Shallow miniballs can be heated locally from outside the body and deep miniballs remotely to control the rate of drug release, and the segments jacketed can be heated to accelerate drug uptake. When extracorporeally energized by eddy-current induction or radiofrequency resonance, holding jackets, just as miniballs and stays, can be made to radiate heat.

Unless miniballs that can be controlled from outside the body or that spontaneously respond to the condition of the blood flowing past are used negating the need therefor, extraction permits instant extractability in the event of an adverse drug reaction. Assigning miniballs releasing different drugs to different holding jackets allows the discretionary extraction of any one drug or if one drug is divided among miniballs, reduction in the dose. Other methods for quickly retrieving a medication, bioactive substance, or radiation miniball which induces an adverse reaction are addressed in the section below entitled Cooperative Use of Impasse-jackets in Pairs and Gradient Arrays.

Except in dimensions, simple impasse-jackets and individual jackets in braced; compound (doubled, doublet); and chain, or triple or more impasse-jackets, addressed below in the section entitled Braced, Compound, and Chain Impasse-jackets, are identical in structure whether used to trap or to hold miniballs. Impasse-jackets for suspending drug and/or radiation delivery miniballs in the bloodstream, for example, can be made absorbable with a polymeric mesh (extraction grid, extraction grating) and magnetized with a chemically isolated lanthanoid (rare earth) substance, usually neodymium iron boron. A permanent mesh in a jacket less strongly magnetized can be made of magnetizable stainless steel wire magnetized in the centrally concentrated pattern indicated. Strongly magnetized impasse-jackets can be made of a nonabsorbable polymer which is impregnated or overlain with the encapsulated neodymium in the centrally concentrated pattern indicated.

In an absorbable impasse-jacket, the magnetized ferromagnetic material at the jacket midpoint must be encapsulated for chemical isolation upon breakdown. While isolated, the magnetized material is nonabsorbable, and the mesh grid wires cannot be made as fine as when made of intrinsically magnetized stainless steel. Should an absorbable device be preferred, suitable polymers for use in absorbable implants, to include impasse-jackets which can release substances on dissolution, are specified, for example, in the section above entitled Absorbable Base-tube and Stent-jacket, Miniball, Stay, and Clasp-magnet Matrix Materials and that below entitled Absorbable Stent-jacket Expansion Insert Materials with Relatively Short Breakdown Times, among others.

One-time dose applications should be supported by absorbable jackets with a life expectancy somewhat in excess of the interval for drug release. Ballistic delivery allows absorbable miniballs to be implanted in a dense formation. In order not to remain as a residue, an absorbable jacket hinge-spring must also be made of an absorbable polymer with intrinsic and/or conformation-imparted resilience and shape-memory. The moisture barrier-coated viscoelastic polyurethane foam lining is treated to encourage macrophage degradation, as addressed above in the section entitled Materials Suitable for Rebound-directing Double-wedge Linings, the absolute amount of 2,4-toluenediamine residue trapped within the barrier and far too little to act as a carcinogen, as addressed above in the section entitled Preliminary Description of the Invention.

To best fit the ductus treated, the individual jackets in a given compound or chain impasse-jacket can differ in length and diameter, for example, and those in a chain jacket can differ in the interval separating these constituent jackets. Impasse-jackets can be interposed among stent- or shield-jackets in a chain wherein every unit differs or serves a different purpose. For emergency interception and extraction midprocedurally using a preplaced impasse-jacket or an external electromagnet, sufficient ferromagnetic material must be dispersed throughout an absorbed, to include a drug-releasing miniball, so that its magnetic susceptibility does not degrade with its dissolution to the point where it is no longer extractable. For arrest and extraction, the ferrous material is ordinarily superparamagnetic magnetite or maghemite nanoparticles or finely grained powder; for heat induction, iron grains.

Uniform distribution also affords greater iron particulate surface area for absorption and eliminates any need to extract a relatively large core. When uniformly dispersed through the miniball, the residual iron content essential to preserve magnetic susceptibility attrites in step with the medication, the reduced mass and volume necessitating less tractive force to prevent being carried forward in the circulation. To allow immediate extraction to a safe location or extraction entirely out of the body at any moment, the extraction grid mesh size must be slightly larger than the original diameter of the miniball. More specifically, to allow the immediate removal of any miniball that might enter the jacket and to accommodate radioactive miniballs which do not dissolve, the mesh size of each impasse-jacket along a given ductus should be large enough to extract the largest miniball that might necessitate extraction from that jacket.

Miniballs that might enter the jacket are those for which a given jacket of reference will be that first encountered. Types and combinations of medication which can be incorporated into miniballs are generally indicated in the section above entitled Field of the Invention, and basic terms used to describe the different types of impasse-jackets defined at the end of the section above entitled Terminology. Individual impasse-jackets in simple and compound jackets and those incorporated into chains with stent-jackets are structurally alike but can differ in mesh size, overall dimensions, and function. Simple or non-compound impasse-jackets used to trap a miniball loose in the circulation are referred to functionally as simple-trap-jackets, while those used to suspend medication or a radioactive source in the lumen, even when drawn from the passing contents and thus trapped, are functionally referred to as simple holding jackets.

Trap and holding jackets may be structurally indistinguishable, but an asymmetrical holding jacket is eccentrically magnetized to draw medication into an eccentric lesion, whereas a trap-jacket is eccentrically magnetized to situate the trapped miniball or miniballs toward the body surface for extraction with the aid of an external electromagnet. However, when the lesion is medial (toward the midsaggital plane) or midfrontal (toward the midcoronal plane), the jacket is oriented accordingly, the field strength increased to pull the trapped miniball through the extraction grid along the greater distance from the opposite side of the body. While extraction can withdraw the miniball entirely outside the body, it is rarely beyond the closest safe location outside the ductus.

Either type impasse-jacket may omit magnetized content over all but a small arc entirely. Compound impasse-jackets used to hold medication are compound holding jackets, and compound holding jackets that include one or more trap-jackets are composite or mixed jackets. Numerous alternative terms for a simple holding jacket are possible, to include simple retention-jacket, simple retention-collar, simple holding-collar, simple-retainer, and simple holder, simple binding-jacket, and simple-binder. When not simple or simple-extended (braced), the terms compound, chain, and mixed or composite are substituted for 'simple.' Thus, one can have a simple-extended or braced impasse-jacket that includes only one trap or one holding jacket, a compound impasse-jacket that includes two trap or two holding jackets, a mixed compound jacket that includes one trap and one holding jacket, or a mixed chain that includes at least one trap and one holding jacket, the terms collar and jacket interchangeable.

For this reason, chain jackets can be triple traps, triple holders, or mixed triple, quadruple, and so on. With a holding jacket, radioactive miniballs introduced upstream can be suspended at jacket level in the lumen to emit radiation at that level, which depending upon the depth of radiation penetration, can involve the contents of the lumen, if any, the tunics of the lumen wall, and tissue surrounding the lumen wall. Radioactive and medicinal miniballs suspended in the vascular tree at the approach to a certain organ can medicate or irradiate the blood bound for that organ, for example. The need for a larger dose than one or a few miniballs can deliver, or the advisability of isolating each distinct type of therapeutic miniball is satisfied through the use of a compound hold and trap chain impasse-jacket, as addressed in the section to follow.

Isolation in a separate holding jacket allows differential access for extraction and post-insertion interaction such as by injecting substances just upstream from the isolating jacket. Compound and chain jackets can include component jackets to trap any miniballs that might, for example, be unintentionally released into the bloodstream during discharge or intentionally released to charge the jacket with a medication miniball, for example, by direct injection just upstream to the jacket. Impasse-jackets thus have primary functions as the object of implantation and afford protection from the loss downstream of a miniball during and following insertion. An impasse-jacket used as a guard or trap where the number of upstream miniballs could not occlude it need be no more than singular whether simple, braced, or a unit member in a compound.

While the release into the circulation of a miniball is unlikely, the strength of magnetization of any one trap-jacket should not be so extreme that the jacket could become occluded if overwhelmed by the entry of multiple miniballs over a brief interval. The ideal strength of magnetization allows both the retention of miniballs and attraction of drug carrier nanoparticles. The propulsive force of the contents must shortly dislodge those at the center of the lumen forcing these through the jacket to the next trap-jacket downstream. A situation whereby more miniballs are introduced into the bloodstream than the jackets available could accommodate is impermissible, no upstream number of miniballs should be allowed in any one unit member or component holding jacket in a compound impasse-jacket that would not be safely trapped by the next downstream component trap-jacket in the compound, and so on.

Broadly, no one jacket should be given potential exposure to more miniballs than it or the jacket which immediately follows it could stop without becoming obstructed. In a composite impasse-jacket used to maximize the dose by using a sufficient number of miniballs, or to clearly demarcate each type therapeutic agent by segregation into separate holding jackets, holding and trap jackets will usually alternate and the miniballs will be introduced by injection into the holding jackets through separate hypodermic syringes or catheters fitted with a hypotube at the distal tip between the proximate ends of the jacket fore and aft, that is, at the bridges which serve to connect the consecutive jackets in the compound.

The bridging in braced, compound, and mixed impasse-jackets allows spanning past anatomy such as attachments best left intact and points of flexion that would interfere with extending a simple jacket lengthwise for improved stability in an extraction. When the number of miniballs to be injected, whether a greater distance upstream or in the trap-jacket immediately preceding is small enough and the probability of a need for interception slight, only the last or most downstream of the component impasse-jackets need serve as a trap. Since a compound impasse-jacket is inherently elongated, hence, stabilized or braced, adding non-magnetized dummy-collars or outriggers at either end of the compound as might be needed to stabilize an isolated unit impasse-jacket through connection by means of rigid in-line mesh-edge to edge bridge-arms should not be necessary.

Unlike a compound or chain impasse-jacket which contains consecutive holding jackets, a compound or chain guard (chain guard-jacket, chain guard-collar) or chain-trap (chain trap-jacket, chain trap-collar) seldom has two or more impasse-jackets in succession; whether an isolated unit or member of a composite impasse-jacket, each trap-jacket must be capable of preventing the passage of any miniball that would otherwise pass. A compound impasse-jacket may thus contain more than one trap-jacket where each is intended to prevent the passage of miniballs released by the constituent holding jacket in the compound immediately upsteam to it should any be released during injection. Exceptionally, a compound jacket can use consecutive constitutent-jackets as traps when the first could become occluded.

In that case, the strength of magnetization of the first trap must be less than would be able to retain miniballs at the long axial center against the advancing force of the luminal contents, usually, that exerted by the blood pressure. Increasing the strength of jacket magnetization can be accomplished by using a thicker and/or more strongly magnetizable fabric (mesh material) or by coating the mesh with a polymer that incorporates an encapsulated lanthanoid particulate, usually of neodymium iron boron. In the bronchi, with embolization little threatening and readily remedied, the tractive and retentive field strength required is proportionally less. While impasse-jackets are intended primarily for use in the vascular tree, suitably configured impasse-jackets are no less applicable to other type ductus, regardless of the purpose intended or the conditions encountered.

For example, in the gut, where peristalsis exerts powerful contractive forces behind the bolus, which expands the ductus, an impasse-jacket is kept shorter to less restrain the longitudinal action under the relatively greater strength of magnetization required to keep the miniball or miniballs held in the lumen by the holding jacket from being pulled from the jacket and swept away by the passing bolus. The duration and longitudinal extent of the disruption relative to the severity of the disorder must determine each case on an individual basis. In the gastrointestinal tract, expulsion spontaneous, extraction of a mispositioned or dropped miniball that does not emit radiation should never be necessary. Nonabsorbable miniballs lodged in a diverticulum or ruga may require extraction, which can be accomplished transluminally.

If realized midprocedurally, recovery is with the same barrel-assembly used to discharge the miniball; if postprocedurally, the a barrel-assembly or a magnet probe ended catheter is used. When the injury risked is slight, a miniball containing potent medication that should not be misdirected or a high dose-rate miniball to have been suspended in a holding jacket with absorbable radiation shield with the potential to injure healthy tissue may require immediate transmural extraction raising concerns for the release of septic contents into the surrounding body cavity. When the holding impasse-jacket is placed prior to discharge, the radiation shield will also act as a perforation shield to prevent a perforating miniball from carrying septic contents out of the tract.

Even when the miniball does perforate into the cavity or must be transmurally extracted, the absolute amount of bacterial inoculum spread into the exit wound, much less any spillage into the surrounding cavity will be minute, certainly in relation to conventional procedures that incise an suture or staple (see, for example, Watanabe, A., Kohnoe, S., Shimabukuro, R., Yamanaka, T., Iso, Y., and 7 others 2008. "Risk Factors Associated with Surgical Site Infection in Upper and Lower Gastrointestinal Surgery," *Surgery Today* 38(5):404-412). The use of impasse-jackets as traps to extract loose miniballs from a ductus wherein the contents are septic, such as in the intestines or a vessel conveying infected blood, is therefore contingent upon the ability of the immune system and antibiotics to ward off infection.

Antimicrobials (antibiotics, viricides, fungicides or mycocides, and/or fungistats) can be delivered on and/or within the miniball itself as well as by other routes. Nonabsorbable miniballs are usually given a deeply textured surface to encourage tissue infiltration and adhesion. These tiny trenches retain a liquid such as an antibiotic wetted onto the surface by capillarity. When the perforation might liberate not just sepsis but metastatic seed cells, nonintrusive transluminal extraction with the aid of a powerful external (extracorporeal) electromagnet is discounted, recovery then transluminal with a catheter having a magnet at the tip or the recovery electromagnets in a radial discharge barrel-assembly.

The use of impasse-jackets to retain irradiating or medicinal miniballs at certain levels in the gut or in the treatment of a carcinoma in any ductus should always contemplate the need for emergency extraction using transluminal means. In situations where the dislodging of the miniball would pose the risk of adverse consequences, a perforation shield is used and the strength of magnetization increased. In a blood vessel, a nonabsorbable miniball that embolizes will do so at a gauge with collateral circulation, so that extraction is based on the discomfort or dysfunction experienced. If the miniball delivered medication or radiation where it would be harmful, it is extracted.

Introduced at a sharp angle to undercut and lodge beneath abluminal tissue, drawn outward by the stent-jacket, having a surface devised for infiltration by the surrounding tissue, and optionally bonded in position by means of a protein solder made to flow immediately after placement or a quick-setting surgical cement, a miniball or a radioactive seed core thereof, for example, is unlikely to enter the lumen. Nevertheless, a midprocedural equipment malfunction, human error during discharge, the rebound into the lumen off of the lining of a stent-jacket prepositioned to avert a perforation, later disease, or a direct blow, such as to a carotid or coronary artery, could result in luminal entry.

Such a circumstance warrants the downstream prepositioning of a means for preventing a miniball from passing a limit point and retaining it in a safe position for removal with minimal trauma. Postprocedural extraction is by trapping the miniball in a downstream impasse-jacket and using an external electromagnet to noninvasively pull the miniball out through the lumen wall and the magnetized mesh-surround (extraction grid) of the impasse-jacket to a safe location. A stent-jacket could trap and retain a miniball in a fixed position within the lumen, but its perforations are not configured to allow extraction. A trap-jacket is placed before the stent-jacket and initiating implantation discharge. However improbable the necessity, an impasse-jacket downstream from a stent with multiple miniballs must have the potential to remain fully functional despite repeated extractions, and without significant injury to the substrate ductus.

An impasse-jacket must not deform nor a chain-guard or chain impasse-jacket bow despite repeated extractions. Whether to serve as a trap (guard) or luminal retention device, the diameter of an impasse-jacket, which always has marginal or end cuff linings of moisture barrier-coated viscoelastic polyurethane foam, is chosen to allow the adventitial microvasculature, small nerves, and perivascular fat to be encircled without significant compression. The warmth of the tissue enhances the property of the foam of enwrapping or investing these surface features. While veins normally collapse during diastole, the foam end cuff linings are sized to prevent migration, even when the caliber at each end reflects tapering. Absorbable and nonabsorbable impasse-jackets can be used in coordination with or independently of ductus wall-infixed miniballs or stays.

The medication positioned can be layered, time-released, adjuvant or neutralizing in relation to drugs or bioactive substances systemic or released from other sources, and/or include a radioactive seed miniball at a fixed level. Holding jackets that release medication from suspended miniballs to work in a coordinated manner can define a segment of any length in the vascular tree where the downstream jacket may release a substance to neutralize that released by the first so as to define the intervening segment for treatment, or the second jacket can release an agent to activate the first for treatment initiated at its location. When this segment is relatively short, both or all jackets can be strung together in a chain. The constancy of circulation makes such coordinated use optimal in the circulatory system.

Placement of an impasse-jacket about a vessel is local using laparoscopic technique without a transluminal component, and the introduction upstream of the radioactive and/or medicinal miniball or miniballs is by injection. The gastrointestinal tract affords a corresponding washing over effect only when boli sweep past, but allows jacket charging and supplementation with other substances noninvasively through ingestion. While requiring laparoscopic insertion, an impasse-jacket can be used, for example, to position a radioactive seed-miniball alongside a tumor or inside the artery or arteries that supply it, then noninvasively extracted whenever desired, allowing a higher dose-rate than would the use of an endoluminal irradiating stent or seed, which left in place, must decay within a limited time, and will continue to disallow compliance with the pulse when the artery may itself have become diseased.

For example, rather than to ligate the gastroduodenal and/or hepatic arteries, a radioactive seed held within one or both vessels is used to irradiate blood going to the liver (see, for example, Bacchetti, S., Pasqual, E., Crozzolo, E., Pellarin, A., and Cagol, P. P. 2009. "Intra-arterial Hepatic Chemotherapy for Unresectable Colorectal Liver Metastases: A Review of Medical Devices Complications in 3172 Patients," *Medical Devices* (Auckland, New Zealand) 2:31-40; Homsi, J. and Garrett, C. R. 2006. "Hepatic Arterial Infusion of Chemotherapy for Hepatic Metastases from Colorectal Cancer," *Cancer Control* 13(1):42-47; Lee, Y. T. 1978. "Nonsystemic Treatment of Metastatic Tumors of the Liver—A Review," *Medical and Pediatric Oncology* 4(3): 185-203; Fortner, J. G., Mulcare, R. J., Solis, A., Watson, R. C., and Golbey, R. B. 1973. "Treatment of Primary and Secondary Liver Cancer by Hepatic Artery Ligation and Infusion Chemotherapy," *Annals of Surgery* 178(2):162-172). Local irradiation rather than ligation of the supply may prove safer (see, for example, Kanashima, R., Nagasue, N., Kobayashi, M., and Inokuchi, K. 1977. "Tumor Embolism in the Right Atrium after Hepatic Artery Ligation for Hepatoma," *Japanese Journal of Surgery* 7(4):246-252). Alternative methods require recovery of a strongly irradiating source surgically, and percutaneous needle injection of a radionuclide into the liver disperses without eradicating migratory cancer stem cells before these reach the liver.

Similarly, while primary carcinoma of a blood vessel is uncommon (see, for example, Blackmon, S. H., Rice, D. C., Correa, A. M., Mehran, R., and 8 others 2009. "Management of Primary Pulmonary Artery Sarcomas," *Annals of Thoracic Surgery* 87(3):977-984; Lygidakis, N. J., Bhagat, A. D., Sharma, S. K., Kefalourous, H., Porfiris, T., and 7 others 2007. "Leiomyosarcoma of the Inferior Vena Cava—An Unusual Case," *Hepatogastroenterology.* 54(75):710-717), to reduce the risk of metastasis to a supplied organ, the site of the lesion and a point or points along its drainage are irradiated. Migratory cancer stem cells (see, for example, Davis, S. J., Divi, V., Owen, J. H., Bradford, C. R., Carey, T. E., Papagerakis, S., and Prince, M. E. 2010. "Metastatic Potential of Cancer Stem Cells in Head and Neck Squamous Cell Carcinoma," *Archives of Otolaryngology—Head and Neck Surgery* 136(12):1260-1266) approaching an organ supplied through this artery are irradiated in transit, with the 'seed' miniball or miniballs noninvasively extracted on depletion.

Additionally placing a radiation emitting jacket with radiation shield fitted affords aggressive treatment. The impasse-jacket is inserted laparoscopically. For use along a ductus closed off to the exterior, such as a blood vessel, ureter, or vas deferens, miniballs to be suspended within the holding jacket are introduced by direct injection just upstream to the respective jacket, the procedure involving no transluminal component. The addition of miniballs may be deferred to a later procedure wherein the bright contrast dye marked jacket or jackets are located fluoroscopically, for example. Ordinary saline solution is used to advance the miniball or miniballs to be suspended within a given jacket to the tip of the hypodermic needle. The miniball or miniballs delivered through a given needle need be alike only in diameter; however, visibility wanting, each miniball whether the same is injected separately.

A single impasse-jacket on the esophagus or gut is charged by ingestion of food containing the miniball or miniballs. To pass a first or proximal jacket in order to charge one distal thereto requires the use of an endoscope, whereas tracheobronchial placement is accomplished with the aid of a tracheoscope or bronchoscope. When a compound or chain impasse-jacket that includes plural holding jackets is used to accommodate a larger number of miniballs or to isolate different medicinal or radioactive miniballs in different individual jackets, each miniball or load of miniballs is separately injected at a point along the component jacket-to-jacket bridge-arm just upstream from each respective target holding jacket.

A barrel-assembly may be used to the load a holding jacket placed about a ductus that should not be perforated by injection; however, multiple recharging is better accomplished through injection at more distant locations upstream. For one or a few charges, an absorbable impasse-jacket is used, while for treatments at any future time, a nonabsorbable impasse-jacket is used. In a holding impasse-jacket, the magnetic force retains the miniball in suspension, and when the miniball releases drug carrier nanoparticles, it attracts the nanoparticles into the ductus wall; otherwise, the drug is moved downstream. Since impasse-jackets have no endovascular component, these can be placed around a thin-walled vein or over a segment of a ductus too diseased to be implanted with miniballs or stays.

Such a jacket can be used to deploy and hold a radioactive seed, medicinal, or combination miniball introduced with the aid of a barrel-assembly to target a lesioned segment without infixion of the miniball within the lumen wall, allowing treatment of a ductus too malacotic for ductus-intramural implantation. Medicinal miniballs that dissolve in the passing blood are taken up according to their metabolic significance, so that some may be absorbed by the endothelium, which others taken up by a certain organ or gland. The dose progressively depleted thus, it is much reduced if not eliminated once cycled through the circulatory system. The choice of an absorbable or nonabsorbable impasse-jacket is based upon the duration of the longest prospective treatment and need for retreatment.

Absorbable impasse-jackets are made of neodymium iron boron particulate-impregnated materials such as those specified above in the sections entitled Field of the Invention and Absorbable Base-tube and Stent-jacket, Miniball, Stay, and Clasp-magnet Matrix Materials, and that below entitled Absorbable Stent-jacket Expansion insert Materials with Relatively Short Breakdown Times, among others, and provide the advantage of not requiring surgical recovery. To assure uniform magnetization, each half-cylinder comprising the impasse-jacket with encapsulated neodymium embedded in the absorbable matrix is rotated before the magnetizer.

In general, nonabsorbable miniballs and those absorbable re-administered over a long period are supported downstream by a nonabsorbable impasse-jacket, whereas absorbable miniballs containing only medicinal or other therapeutic ingredients to disintegrate postprocedurally are supported by an absorbable impasse-jacket. A miniball can be prevented from continued travel past a trap-jacket only so long as the impasse-jacket remains intact; were it to appear that this interval had been underestimated, the miniball could be extracted immediately in the same manner as would a stenting miniball stopped by a permanent impasse-jacket. An impasse-jacket must remain functional as long as it is required to prevent the loss downstream of a miniball.

Thus, when the period that a miniball with a dissolution time greater than the maximum that might be required is used and the time it is to be suspended is indeterminable, an absorbable impasse-jacket with a dissolution time in excess of the life of the miniball and not just the maximum prospective duration the drug will be required should apply. A nonabsorbable impasse-jacket is made with an extraction grid of fine magnetizable stainless steel wire. When the wire itself cannot be magnetized to provide the required field strength, chemically isolated premagnetized lanthanoid granules embedded in an adherent matrix polymer is coated onto the wire in the centrally concentrated pattern indicated, care taken to occlude as few mesh (extraction grid) openings as possible.

For use with a radiation emitting seed miniball, the holding jacket is provided with an absorbable radiation shield that protects the surrounding tissue and disintegrates to expose the underlying extraction grid when the miniball is to be noninvasively extracted to a point outside the ductus or the body with minimal trauma. Retrievability allows the use of an unconventionally high dose-rate. When multiple seed miniballs must be used in succession, the persistence of the shield extends over the succession and is then eliminated spontaneously or on demand to clear the way for the depleted miniballs to be removed. An absorbable impasse-jacket is itself absorbed or disintegrated, disallowing future use but eliminating any need for reinvasive retrieval. It must persist longer than the radioactive seed or successive seeds it is to retain, then the dissolution of its radiation shield, allow the seed or seeds to be noninvasively extracted.

An absorbable mesh is made of an absorbable polymer or copolymer such as those specified above in the section entitled Absorbable Base-tube and Stent-jacket, Miniball, Stay, and Clasp-magnet Matrix Materials, formulated for optimal strength and incorporating lanthanoid granules, for example. Comminutable and meltable materials are addressed below in the sections entitled Expansion Inserts Absorbable, Meltable, and Comminutable for Time-discrete Decremental Contraction of Stent-Jackets and Absorbable Stent-jacket Expansion insert Materials with Relatively Short Breakdown Times. Absorbable impasse-jackets are the same in configuration as the equivalent nonabsorbable impasse-jackets, to include the outriggers of braced impasse-jackets described below in the section entitled Braced, Compound, and Chain Impasse-jackets.

To protect against human error, such as mispositioning the needle when injecting miniballs for suspension in holding jackets or improperly setting the discharge velocity as to result in rebound into the lumen following discharge for ductus-intramural implantation, the release of any miniball in the vascular tree best takes the added precaution of prepositioning an adjustable external electromagnet downstream, which can stop and extract these, as addressed in the section above entitled Emergency Recovery of Miniballs and below in the section entitled Use of an External Electromagnet to Assist in Mishap Recovery. Whereas absorbable stent-jackets can be allowed to disintegrate following a treatment period during which the ductus heals whether ductus-intramural implants were absorbable or nonabsorbable, absorbable impasse-jackets without the backup of nonabsorbable trap impasse-jackets downstream must not be allowed that would disintegrate postprocedurally while a miniball remains suspended within it.

The mesh size should just frame about and allow the largest miniball to be suspended to pass through. During an extraction with an extracorporeal electromagnet prepositioned downstream, a trap-jacket restrains the ductus from being pulled, twisted, and stretched until the shear strength or resistance to extraction perforation of the wall is exceeded and the miniball is forced through. Significantly, since the strength of the magnetic field that can be directed at the miniball is extreme, a suddenness of outward acceleration that would fail to preclude any ability of the ductus wall to pose self-traumatizing resistance by stretching is a distinct improbability. Accordingly, the need for a jacket is proportional to the susceptibility of the ductus to injury. An in situ perforation resistance test to indicate suitable mesh size and the tractive force range essential to extract a miniball of given diameter at that point is provided below in the section entitled Testing and Tests.

Shock penetration through the sudden application of a powerful magnetic extractive force is essentially the opposite of ballistic insertion and prompted for the same reasons as specified above in the section entitled Preliminary Description of the Invention. Whereas the emergency interception and extraction of a miniball loose in the circulation by means of an external electromagnet with or without an impasse-jacket is noninvasive, placement of the impasse-jacket is invasive, as addressed above in the section entitled Emergency Recovery of Miniballs, and in section X2c below entitled Stereotactic Arrest and Extraction of a Dangerously Circulating, Mispositioned, or Embolizing Miniball. Usually a length of downstream ductus will be available for prepositioning a powerful external electromagnet that is well able to withstand extraction without the need for an impasse-jacket; however, once placed the jacket will continue to guard against embolizing miniballs and suspend any introduced for treatment.

While the miniball to be extracted is usually withdrawn in increments to a safe location just outside the ductus by pulsing the electromagnet, provided no vulnerable structure such as a ganglion is situated along the prospective extraction path, removal can be entirely outside of the body. If moved to a location unintended but safe, the miniball is allowed to remain. If lodged behind bone, tendon, or ligament, the miniball can usually be left in place; if not, then it is extracted in a different direction. Since the perforation path or trajectory is minute in diameter, usually about 0.4 millimeters, quickly seals, the electromagnet is adjustable to a field strength high enough to extract the miniball directly, and systemic platelet blockade is minimized as the targeting capability of the apparatus allows, small vessels intervening along the path that are torn soon heal.

The possibility that the a miniball on discharge with perforation or extraction will puncture and enter the lumen of a second vessel to enter the circulation is eliminated by the strength of the magnetic field, which pulls the miniball entirely through the intervening ductus regardless of the blood pressure, or in the gut, for example, the effective increase in tissue strength due to contraction or the propulsive force the bolus. Even polymer coated, the mesh in a nonabsorbable or absorbable impasse-jacket poses no issue of obtrusive thickness as would encroach upon or abrade neighboring tissue. It can therefore be made of strong materials in sufficient thickness and strongly magnetized.

The miniball must be extractable through the lumen wall and the mesh by a magnetic field of sufficient force to effect such action, which will depend primarily upon the strength of the ductus wall, for which an in situ test is provided in the section below entitled Testing and Tests. Stretching injury to the ductus is reduced when the mesh size as coated is just large enough to allow the miniball to pass through. In an artery, the impasse-jacket can be positioned as closely to the stent-jacket as any significant interaction between the magnetic fields of a prospective extraction electromagnet (qv.), the stent, and impasse-jacket would allow. A benefit in close placement or including both stent- and impasse-jackets as a braced pair is that both the stent and impasse-jacket can be inserted through the same if elongated entry wound.

To minimize injury to the substrate ductus and to the neighboring tissue, the impasse-jacket must not lurch or lever under the magnetic force that the extraction electromagnet must exert to overcome the perforation resistance of the lumen wall. Unless a mineralized deposit intervenes, this condition is easily met, even when the ductus is severely sclerosed due to disease. In the arterial tree, wherein the antegrade caliber of the vessels progressively diminishes centrifugally, or from the heart to the periphery, placement of the impasse-jacket as close as practicable to the stent-jacket can stop the miniball at a level where the impasse-jacket, whether simple or braced, can be longer and stronger both structurally and in magnetization and the miniball is still small in diameter relative to the caliber of the ductus. Extraction at this level is also located farther upstream from the level of eventual embolization and where the artery is more robust.

While generally thin-walled and unsuited to ductus-intramural or intraparietal implantation, these relations are reversed in veins, where continued antegrade travel moves the miniball through levels of increasing caliber. In the venous tree, positioning the impasse-jacket at a greater distance from the stent-jacket stops the miniball where it is closer to the center where the vein is larger, so that an extraction poses less risk of trauma at the immediate location and is more easily viewed. If the miniball did lodge in a lung, at about 0.4 at millimeters in diameter, its emergency extraction path, would almost certainly close spontaneously never to require extraction, and even if extraction, which from a lung must be passed through the pleura, were required, the risk of a pneumothorax or pneumoserothorax for a perforation of this diameter may be discounted.

Exceptionally, the use of a stent-jacket with rebound-directing lining in an artery, as addressed above in the section entitled Double-wedge Stent and Shield-jacket Rebound-directing Linings, may warrant backup by a miniball-impasse-jacket situated downstream from the stent-jacket to stop any miniball that rebounded into the lumen despite the intervening double-wedge. Symptoms improbable, prospective or prognostic consequences determine whether periodic imaging is advisable to detect the presence of a stopped miniball in an impasse-jacket that would justify extraction; provided the miniball is small for the lumen and tightly held by the magnetic field, it can usually be left.

Likewise in a vein, the average gauge of the ductus over the treatment segment, diameter of the miniballs used, and mesh size of the impasse-jacket will be proportional, and the degree of positional stability required of the impasse-jacket during an extraction dependent upon the force to be exerted by the extraction electromagnet. The extraction grid is intended to restrain the miniball from stretching To minimize the force of extraction needed and movement of the impasse-jacket, the mesh size with any coating should be optimized for the diameter of the miniball in relation to the perforation resistance of the ductus wall. While each case must differ in the degree of extractive force required, to ensure that the impasse-jacket and any bracing will not fracture, bow, or otherwise deform despite an unexpectedly untested sclerosed area of the wall, the material strength and thickness of the mesh is overrated.

Each half of the impasse-jacket magnetized normal to its long axis, its radially outward polarity will be uniform about the circumference of the completed jacket. The jacket thus presents a net repulsive moment in relation to the tractive force exerted by the external extraction electromagnet. This repulsion serves to push the impasse-jacket back against the subjacent tissue as the same force extracts the miniball. This stabilization by repulsion prevents traumatic levering, wrenching, kinking, stretching or choking off of the lumen at the jacket margins as well as the tearing of any underlying attachment desired to be kept intact. Stabilization by suturing, which would have to be deep, awkward through the small access portal, and increase the risk of infection, is thus unnecessary.

Since the extraction grid or mesh is configured for the least resistance to passage therethrough, the miniball is essentially restrained only by the resistance posed by the lumen wall that stands between it and the extraction electromagnet. Too large a mesh can allow a more elastic wall to resist extraction by stretching, for example. Properly sizing the mesh to the diameter of the miniball minimizes stretching injury to the wall. Extraction with the least tractive force reduces the risk of excessive jacket repulsion that could injure the ductus and/or damage the impasse-jacket itself. Jackets used to attract drug carrier nanoparticles must present greater field stength than those used to attract miniballs, which can include a much larger amount of susceptible content; however, only miniballs require extraction.

The strength of impasse-jacket magnetization may be limited by proximity to other implants susceptible to a magnetic field. This may force the prepositioning of an impasse-jacket in the arterial tree, for example, farther downstream and/or set a limit to how strongly the jacket can be magnetized. A jacket to be capable of attracting susceptible nanoparticles may have to be positioned farther downstream. However, the strength of magnetization must always be sufficient for the maximum momentum of a miniball or susceptible particulate that might enter the lumen upstream, in an artery, at the systolic blood pressure. More specifically, for a miniball of given mass and diameter, the maximum propulsive force exerted by the pulse depends upon the blood pressure and the effect of gravity at the location and position of the implantation site.

In the esophagus, the downward driving force on the bolus is the determinant. Most often, the application of stent and stopping jackets is not accomplished during open surgery, but rather through a laparoscopic entry wound or 'keyhole' incision of a few centimeters. Small joint arthroscopic type instruments—and exceptionally when a wider impasse-jacket is inserted with its two sides then having to be folded to encircle the ductus, a stent-jacket insertion tool, as described below—are used to insert and position the jacket. Access thus restricting the manipulative range of the operator, the conformation and placement of impasse-jackets are devised to minimize the manipulation needed even with braced impasse-jacket secured off to either end by a dummy-collar or outrigger, as will be described.

For example, to expedite placement where working space is lacking, any dummy-collars, or outriggers needed to reduce levering, as addressed below in the section entitled Braced Impasse-jackets, are structurally unitized with the impasse-jacket at the center and inserted as a unit. If placed with an open surgical field, end-tie type end-tabs can be used. Increased susceptibility to the tractive magnetic force exerted by the external extraction electromagnet on a miniball results from the concurrent repulsive force applied to the mesh, or extraction grid. Containing relatively little susceptible mass, the force required to extract drug carrier nanoparticles is higher. The distributed ferromagnetic grains or particulate within the miniball are advantageously given a prismatic conformation and adequate thickness.

The mesh size of the extraction grid is selected to allow the largest miniball to be used to pass through. How small a miniball directed to the same impasse-jacket depends upon the susceptibility to stretching injury of the ductus wall. The magnetized length of the impasse-jacket must brake and arrest any miniball that approaches. Thus, the mesh size must be matched to the ductus wall strength and miniball diameter so that it is not so small that excessive tractive force would be required to overcome the shear strength of the ductus wall nor so large that extraction would allow mesh pull-through with stretching or incision injury of the wall—factors that can be tested, as addressed below in the section entitled Testing and Tests.

The distortive straightening of a tortuous ductus to allow the use of a longer or braced impasse-jacket to counter levering should seldom be necessary, because, whether anomalous or varicose, a ductus formed thus has the slack and mobility to comply with levering without the need for end stabilizers in the form of dummy collar or by bracing. For that reason, the need for continuous dissection to free the ductus round and about should be unnecessary. The articulating wires or bridges of an impasse-jacket in a chain can span across segments that whether for mechanical, circulatory, or neurological reasons, would best be left attached. Once stopped by an impasse-jacket, the miniball is unable to proceed to a second impasse-jacket.

However, when the combined strength of magnetization of a jacket and the susceptible mass contained by a miniball is too slight, the blood pressure or bolus will propel the miniball through that jacket to the next. To a limited extent, and with the understanding that the increment in flux from one jacket to the next must be large, it is thus possible to target miniballs to different impasse-jackets in a chain, wherein the impasse-jackets are articulated as are stent-jackets. Accordingly, when the impasse-jackets in a chain increase in magnetic flux in antegrade sequence, the jackets are uniformly loaded or charged by successively introducing miniballs of less and less magnetic susceptibility. While not impasse-jackets, dummy-collars, or outriggers, can stabilize a chain or braced impasse-jacket by straddling segments not jacketed.

I15b. Structure of Impasse-Jackets

Just as all implants described herein must contain sufficient ferrous content to allow their quick retrieval if necessary, all impasse-jackets must support the extraction of a miniball or miniballs with an extraction grid and by virtue of secure attachment. Impasse-jackets are simple or compound. A simple impasse-jacket is positioned where no need for stabilization through bracing exists and the single jacket can accommodate the maximum load that may be required of it. This requires firm and strong adhesion or connection to neighboring tissue in lieu of outriggers or dummy-collars to secure either end and is therefore exceptional. A compound impasse-jacket consists of a magnetized impasse-jacket at the center connected by bridging arms to one or more unmagnetized dummy-collars, or outriggers, off to either end, or fore and aft.

An adhesive such as cyanoacrylate cement will not persist and must not be used to tack down the ductus off to either end of the jacket. The use of suture or when the interval pending use of the jacket allows, deliberately induced adhesions may serve as a useful adjunct. Compound jackets use bridging arms to join an individual impasse-jacket to unmagnetized dummy-collars or to other magnetized impasse- or stent-jackets in a series or chain, in which each jacket can differ from the others. When done for bracing, the implant overall is elongated or extended, or not compound, then provided with dummy-collars, and if necessary, sutured, to resist sudden traumatic displacements that could injure the substrate ductus in an extraction. When compounding is to allow more miniballs to be held in the lumen, a number of magnetized impasse-jackets are bridged together, in which case, stabilization is inherently provided as well.

FIG. 16 shows an impasse-jacket having dummy-collars or outrigger stabilizers 124 and therefore referred to as braced. By securing the jacket off to either end, these prevent sudden pulling and wrenching of the ductus during an extraction should it become necessary. The impasse-jacket proper at the center 125 consists of two mesh half-tubes, 126 and 127, that when closed form a complete tube for encircling the ductus, spring-hinges 128 which fasten the half-tubes together, and cuff-linings, 129 toward either end. Large jackets and outriggers of braced and compound jackets, addressed in the section to follow, can be made with a spring hinge or hinges integrally molded, as Weatherchem, Incorporated makes in polypropylene, for example.

The extraction grid then is made ferromagnetic by coating or lamination. The impasse-jacket is preferably press die cut or punched into thin gauge martensitic or precipitation carbon hardenable nickel free stainless steel flat sheet stock that is magnetized while still flat and before forming into a cylinder about a mandrel. Mesh fabric that is diagonal or cross-hatched but edged with right angular framing is not used, because when cut to size, such material does not provide a straight or right angular framing border. Any sharp protrusions about the edges must be ground away and burnished to provide a smooth outer border. Alternatively, fine gauge filter stock (screening, sieving) of like metallurgy can be used, if necessary with each intersection in the mesh, depending primarily on the dimensions, furnace brazed, braze welded, or resistance welded for increased strength and stiffness.

The material strength and gauge of the mesh, or extraction grid, follow from the strength that the grid will need to resist deformation in an extraction. The gauge is also a determinant in the amount of ferrous content, hence, the strength of magnetization the grid can sustain for retaining a miniball against the expulsive or dislodging force of the material propelled through the lumen. In an artery, that results from the pressure and viscosity of the blood. When the mesh is made from wire, the intersections may be twisted around to achieve increased magnetization and stiffness. Whether punched or made of screening, when the mesh or gridwork is to be overlain with a polymer incorporating ferromagnetic particles for increased magnetization and/or heat inducibility, for example, the bare metal mesh size must be increased to allow for the reduction in the openings by the overlain polymer.

Whether press die cut or made from screening fabric, the magnetized mesh is formed into a cylinder over a mandrel with the aid of heat as necessary. If the Curie temperature is exceeded and the strength of magnetization fails to return to its preheated value on cooling, then the cylinder is remagnetized in the two opposing complementary flush-fitting open-ended longitudinal mesh half-cylinders 126 and 127 into which the cylinder is cut. Another way to produce the extraction grid when existing mesh fabric of the required mesh size, gauge, and stiffness is unavailable, is to fabricate the mesh out of thin gauge iron or ferromagnetic noncorroding steel solid round stock (wire) with good stiffness, such as a 400 series hardened martensitic stainless.

The wire is bonded to create the bidirectional open geogrid mesh by furnace brazing or braze or resistance welding, for example. Each half-cylinder is hinged to its opposite as the last step in manufacture, that is, only after brazing or welding if involved, the addition of coatings if any, magnetization, and the insertion of moisture barrier-coated viscoelastic polyurethane foam cuff-linings. Bridges and outriggers are included when bonding to yield a unitized and fracture-resistant brazement or weldment. When the heat of bonding exceeds the Curie temperature so that magnetization of the mesh stock while still flat is not fully recovered on cooling, the mesh (extraction-grid) is prepared, impasse-jacket formed, end-cuff linings (of moisture barrier-coated viscoelastic polyurethane foam at the ends of the jacket) glued inside, and the application of a polymer when applicable, accomplished prior to hinging the half-tubes together and magnetization.

The all but magnetized and hinged together half-tubes are separately magnetized so that the external surfaces of each will be repelled by the field of the external extraction electromagnet. The mesh half-tubes are fastened together along their adjacent long side edge frame by crimping the side frames together with miniature eyeglass case type spring steel hinges of the kind that short of closing, gently complete the closing action. The complementary mesh half-tubes close together to form the hollow open-ended mesh tube of the jacket. For placement on a tapered ductus where the moisture barrier-coated viscoelastic polyurethane foam lining cannot accommodate the taper, a mandrel of like taper is used to fabricate the mesh half-tubes. Just as a stent-jacket, an impasse-jacket is sized for the diastolic or quiescent diameter of the artery and must expand with the pulse without resistance.

Peristaltic ductus are likewise sized for the quiescent diameter. There is no special type impasse-jacket for use along the gastrointestinal tract, which can also be fitted with a magnet-wrap for the same purpose. Compliance without compression of the adventitia over the uncuffed segment of the mesh is afforded through the use of hinge springs not greater in restorative force than yields to the pulse, and cuff-linings of moisture barrier-coated viscoelastic polyurethane foam afford additional flexibility in jacket diameter and pulse compliance. Increasing the thickness of the foam cuff linings also lifts the uncuffed or cuff-intervening portions of the mesh away from the adventitia. The jacket should be properly matched in size to the ductus.

Tightly rolling and pressing the edges that meet when the jacket is closed perpendicularly to the mesh or extraction grid or fastening small tabs along the closing edges of the jacket by crimping or with cyanoacrylate cement, for example, eliminates an overlapping of sharp edges when the jacket is oversized. Moisture barrier-coated viscoelastic polyurethane foam cuff linings of adequate thickness will also prevent significant overclosure at the edges that meet when the jacket is closed and noncompliance with the pulse or compression of vasa and nervi vasora and perivascular fat as a result. However, oversizing increases the distance to susceptible matter in the lumen and may require to be compensated for with increased strength of magnetization.

An undersized impasse-jacket is one that does not fully close despite the clearance provided by the foam cuff linings. The portion of the circumference where the closing edges do not meet will lack directly radial tractive coverage for susceptible matter in the lumen. If the strength of magnetization is high, the jacket will exert some compressive force on the ductus, interfering with the pulse and compressing the vasa and nervi vasora and perivascular fat or the equivalent in a nonvascular ductus. Impasse-jackets are not placed with a stent-jacket insertion tool but inserted with the jacket and if present, outriggers in the open position and placed to encircle the treatment ductus.

Moisture barrier-coated viscoelastic polyurethane foam cuff mesh half cuff linings 129 provide:

1. Flexibility in fitting according to lining thickness, hence some latitude for application to ductus that are uneven in diameter, become swollen, or have been fitted with a jacket that is slightly oversized.

2. A reduction in contact if not a slight separation of the mesh from the adventia that assists to
   a. Prevent compression of the outer tunic, adventitial vasculature, innervation, and perivascular fat, and
   b. Further implement compliance with the pulse even though the jacket is sized for the diastolic (quiescent or resting) diameter.

3. Loop suture around mesh strands over the cuff-linings when necessary to reduce any subjacent space without tying down the jacket so tightly that compliance with the pulse results thus preventing a blow under the repulsion of the extraction electromagnet.

4. Resistance to migration through sliding of the jacket along the ductus.

5. Cushioning against levering or pushing forces at the margins of the jacket when an external electromagnet is used to extract the trapped miniball through the lumen wall and surrounding mesh to a safe location outside the lumen, and 6. Reduces contact between the bridges described below and the adventitia, thus allowing less stringent tissue acceptance criteria to govern the use of some shape memory materials to include polymers and alloys.

Biocompatible and implantable shape memory alloys and polymers have attained an advanced stage of development (see, for example, Hassani, F. A., Peh, W. Y. X., Gammad, G. G. L., Mogan, R. P., Ng, T. K. 5., and 5 others 2017. "A 3D Printed Implantable Device for Voiding the Bladder Using Shape Memory Alloy (SMA) Actuators," *Advanced Science* (Weinheim, Baden-Württemberg, Germany) 4(11): 1700143; Miao, S., Zhu, W., Castro, N. J., Leng, J., and Zhang, L. G. 2016. "Four-dimensional Printing Hierarchy Scaffolds with Highly Biocompatible Smart Polymers for Tissue Engineering Applications," *Tissue Engineering. Part C, Methods* 22(10):952-963; van Hove, R. P., Sierevelt, I. N., van Royen, B. J., and Nolte, P. A. 2015. "Titanium-Nitride Coating of Orthopaedic Implants: A Review of the Literature," *BioMed Research International* 2015:485975; Tarniţă, D., Tarniţă, D. N., Bîzdoacă, N., Mîndrilă, I., and Vasilescu, M. 2009. "Properties and Medical Applications of Shape Memory Alloys," *Romanian Journal of Morphology and Embryology* 50(1):15-21; Yeung, K. W., Poon, R. W., Chu, P. K., Chung, C. Y., Liu, X. Y., and 5 others 2007. "Surface Mechanical Properties, Corrosion Resistance, and Cytocompatibility of Nitrogen Plasma-implanted Nickel-titanium Alloys: A Comparative Study with Commonly Used Medical Grade Materials," *Journal of Biomedical Materials Research. Part A* 82(2):403-414; Es-Souni, M., Es-Souni, M., and Fischer-Brandies, H. 2005. "Assessing the Biocompatibility of NiTi Shape Memory Alloys Used for Medical Applications," *Analytical and Bioanalytical Chemistry* 381(3):557-567; Li, Xia, Tang et al. below).

For relatively shallow but critical arteries such as the external carotids, pseudoelasticity that imparts instant reversion to the original conformation may be crucially important were the patient to receive a direct blow to the neck, for example. Shape memory alloys used on the external carotids do not (normally) require midprocedural bending to be fitted. Shape memory alloys are not preferred for more deeply situated arteries since midprocedural bending allows such tailoring by the operator without the need to precast the bridges with different curves. The dissolution of an absorbable impasse- or stent-jacket leaves behind the moisture barrier-coated viscoelastic polyurethane foam mesh as a residue, and an absorbable braced impasse-jacket as described below also leaves outrigger half-tube cuff linings; however, as addressed above in the section entitled Summary Description of the Invention, this residue will be far short of the quantity that could act as a carcinogen.

Exceptionally, radiation shielded stent-jackets for use with magnetically targeted drug or irradiating drug carrier-bound nanoparticles are not absorbable. Following fabrication and before any additional coating and magnetization, the magnetic field of the mesh half-tubes can often be increased in intensity if coated or plated with a ferromagnetic material such as nickel-iron (Li, X. P., Seet, H. L., Zhao, Z. J., and Kong, Y. K. 2005. "Development of High Permeability Nanocrystalline Ferromagnetic Materials by Pulse Plating," *Journal of Metastable and Nanocrystalline Materials* 23:163-166) amorphous $Fe_{75}Si_{15}B_{10}$ powder (Parker, F. T., Spada, F. E., Berkowitz, A. E., Vecchio, K. S., Lavernia, E. J., and Rodriguez, R. 2001. "Thick Amorphous Ferromagnetic Coatings via Thermal Spraying of Spark-eroded Powder," *Materials Letters* 48(3-4):184-187). Thereafter, the impasse-jacket can be further encapsulated, irradiated, or drug elution coated.

A polymer coating itself can incorporate ferromagnetic nanoparticles (Srikanth, H., Poddar, P., and Gass, J. 2005. "Materials Processing and Tunable Magnetism in Polymer Nanocomposites," in Gupta, M., Srivatsan, T. S., Lim, C. Y. H., and Varin, R. A. (eds.), *Processing and Fabrication of Advanced Materials XIII*, Volume 1, Singapore: Stallion Press, pages 367-376). A more strongly magnetizable polymer coating incorporates neodymium iron boron lanthanoid, for example. Especially if the polymer and impasse-jacket it coats are absorbable, and as safe practice in general, the lanthanoid is encapsulated for chemical isolation when eventually or unexpectedly released. When applied to enclose the vessel, the impasse-jacket should fit no more snugly than is necessary to prevent its migration by sliding along the ductus.

I15c. Braced, Compound, and Chain Impasse-Jackets

Moderately repelled by the extraction electromagnet, lengthening the impasse-jacket adds moments of resistance to suppress levering or margin-repulsion against the substrate ductus and/or subjacent tissue during an extraction. Lengthwise extension of the impasse-jacket that would distortively straighten a ductus which is normally tortuous or that would require extended continuous dissection to free the ductus round and about or from a subjacent attachment or adhesion, is avoided by straddling such segments. To these ends, the central magnetized stopping jacket is rigidly bridged margin to margin to nonmagnetized dummy jackets, or outriggers, placed in encircling relation to the segments situated beyond the unused or unusable intervening segments.

All impasse-jackets with outriggers are braced but referred to as chained only when connected to more than one outrigger at either end. The outriggers are the same in construction as the impasse-jacket proper but serving as stabilizers, are usually shorter. Outriggers can serve not only for antilevering stabilization but also as inlets and outlets for direct connection to an Ommaya-like reservoir or infusion set cannula at the body surface with catheter leading to the outrigger for direct delivery to the lumen of a drug, magnetic drug carrier ferrofluid-bound drug, or other therapeutic substance. Typically, the drug is infused through the upstream or entry outrigger, and if needed, a reversal agent through the distal segment of the jacket or downstream outrigger.

Unless the patient is alone and mentally impaired, infrequent dosing is by syringe. Otherwise, dosing is by means of a portable pump. Impasse-jackets are not chained as are stent-jackets wherein each substent is functional; to span over or straddle a segment that flexes, only one magnetized or functional impasse-jacket is used, outriggers when present provided as stabilizers. A braced impasse-jacket usually has the form of a unitized threesome, but more extended, can be a fivesome, for example. The appelation 'chain' still describes such an interrupted and concatenated conformation. Bridging utilizes a center magnetized impasse-jacket of maximum length for the anatomy.

Single-piece bridges rigidly connect the stopping jacket to the outrigger fore and aft, and if a second outrigger is included, the first to the second outrigger. An impasse-jacket in a chain otherwise comprised of stent-jackets is stabilized at each side by connection to the adjacent jackets, which may in turn be stabilized by means of side-straps, or if an end-stent, then an end-tie. Impasse-jackets can also be stabilized or rendered additionally resistant migration to migration by end-ties as are used with stent-jackets. In ordinary nonabsorbable braced impasse-jackets, bridges 130 consist of nonmagnetic stainless steel bridging arm 132 and edge-rims, or mesh half-tube edge-rims, 131.

Where beneficial, reduced mass without significant loss in biocompatibility, strength, noncorrodability, nonsusceptibility to the magnetic field, and permanence, the bridge pieces are cast from titanium alloy (see, for example, Lukomska-Symanska, M., Brzezinski, P. M., Zieliński, A., and Sokolowski, J. 2010. "The Connective Tissue Response to Ti, NiCr and AgPd Alloys," *Folia Histochemica et Cytobiologica* 30; 48(3):339-345; Lautenschlager, E. P. and Monaghan, P. 1993. "Titanium and Titanium Alloys as Dental Materials," *International Dental Journal* 43(3):245-253). Such alloys and presumably those exhibiting pseudoelasticity appear to be improved in biocompatibility when coated with a diamond-like carbon coating (Li, Q., Xia, Y. Y., Tang, J. C., Wang, R. Y., Bei, C. Y., and Zeng, Y. 2010. "In Vitro and In Vivo Biocompatibility Investigation of Diamond-like Carbon Coated Nickel-titanium Shape Memory Alloy," *Artificial Cells, Blood Substitutes, and Immobilization Biotechnology* 39(3): 137-142).

Alternately, a nonmagnetic stainless steel can be used. In FIG. 16, the braced impasse-jacket is assembled in two steps, the first consisting of connecting the ordinarily three half-tubes representing one half or one side of the completed cylindrical triple jacket together, and the second step of joining together two of these half triple cylinders into a spring loaded openable cylinder. Assembly thus allows uniform magnetization of the two halves in relation to the field of an extraction electromagnet that may be needed before fastening the two triple jacket half cylinders together. The triple mesh half cylinders are fastened together by connecting the approximating (neighboring, facing) end-edges or margins of the mesh half cylinders together by means of bridge-pieces or bridge-braces 130.

Fusion together of the mesh half-tubes to the semicircular arms 131 of brace bridges 130 is by furnace brazing or resistance welding. Outriggers 124 are constructed as is the impasse-jacket proper 125 at the center, to include end-margin cuff linings of moisture barrier-coated viscoelastic polyurethane foam 129, but are usually shorter. Now a unitized weldment, the three half-tubes representing each half or side of the completed cylindrical triple jacket is magnetized so that the outer surface of the completed impasse-jacket will have the same polarity as the extraction electromagnet.

So that the impasse-jacket and two outriggers will open and close along the same line, bridge arms 131 and the mesh half cylinder to either side are aligned. Once the three two mesh triple half cylinders have been magnetized with the same polarity, each is fastened to the other by crimping on spring-hinges 128 along one longitudinal meeting edge of each as defined by one end of the brace arms 131. Absorbable braced impasse-jackets are likewise made unitized of absorbable suture and tissue scaffold materials specified, for example, in the section above entitled Absorbable Stent-jacket Expansion Insert Materials with Relatively Short Breakdown Times.

Since the absolute distance separating the impasse-jacket from the outriggers is usually small enough, the chain-guard can be inserted as a unit with center jacket and outriggers in open position through a single access incision at the body surface and most likely without the need to lengthen the incision. All of the elements of an absorbable braced impasse-jacket, except for the moisture barrier-coated viscoelastic polyurethane foam cuff-linings of the center magnetized jacket and the complete foam linings of the outriggers, are absorbable, to include the mesh sheeting, rims and rim-connecting braces, which are made from one or more of the polymers specified above for the magnetizable steel mesh coatings of steel mesh jackets and in other sections herein. Following absorption, the moisture barrier-coated viscoelastic polyurethane foam cuff-linings remain as an innocuous residue, as explained above in the section entitled Summary Description of the Invention.

I15d. Cooperative Use of Impasse-Jackets in Pairs and Gradient Arrays

The use of magnetized ductus-intramural implants to define a segment of a ductus for delivery of a drug or drugs is the same as described in this section for impasse-jackets, patch-magnets and magnet-wraps, the latter limited to large ductus. Any of these arranged along a ductus can be used to define a segment for treatment by attracting a drug from the passing lumen contents. Segment and organ targeting, addressed above in sections entitled Field of the Invention and Concept of the Impasse-jacket among others, are discussed in relation to jackets and impasse-jackets in particular, because these afford more utility where the need for a reversal agent exists. An entry jacket at the inlet, usually arterial, allows targeting an organ with a drug.

If any outflow of the drug must be prevented, then an exit-jacket is placed at the outlet, usually venous to release a counteractant. The drug sequencing and targeting means addressed herein, and the use of exit-jackets in particular are intended to prompt the development of new pharmaceuticals. Other arrangements analogous to Halbach cylinders where the conformation of the field rather than high field strength is sought may be contemplated (see, for example, Coey, M. and Weaire, D. 1998. "Magnets, Markets, and Magic Cylinders" *Industrial Physicist*, September 34-36; Zhu, Z. Q. 2000. "Powder Alignment System for Anisotropic Bonded NdFeB Halbach Cylinders" *Institute of Electrical and Electronics Engineers Transactions on Magnetics* 36(5):3349-3352).

Usually too strongly magnetized, miniballs and stays and arrays thereof used to attract susceptible matter from the lumen are seldom integrable into a formation of miniballs or stays used for stenting. Magnetized stays are automatically oriented upon introduction; magnetized miniballs are delivered with the substrate ductus while temporarily encircled within a susceptible jacket which causes the miniballs to self-orient in the cytoplasm at the trajectory terminus. The use of magnetized miniballs, stays, and impasse-jackets for targeted chemotherapy or neoadjuvant chemotherapy preparatory to surgical resection through the application of magnetic force is addressed above in the section entitled Drug-releasing and Irradiating Miniballs, Stays, and Ferrofluids.

In terms of existing medication, the use of evenly spaced miniballs or stays along a ductus, arranged in order of increasing strength of magnetization in the antegrade direction, or of two or more impasse-jackets used thus to achieve selective segmental concentration of a drug. Usually the carrier will likewise include particles that are graduated in magnetic susceptibility. When passing such an array, the drug, a statin, or 3-hydroxy-3-methylglutaryl-coenzyme A (HMG-CoA) reductase inhibitor, for example, is drawn into the diseased segment. The carrier-bound drug is preferably administered orally in the form of a capsule but otherwise self-administered through a subcutaneously implanted infusion port placed to free the patient from the clinic.

Although concentrated for the treatment segment, a portion of the statin dose that might pass the array will be innocuous. The addition of an exit jacket to release a reversal agent or counteractant, however, introduces the possibility of using substances or concentrations previously considered too toxic for therapeutic use. The following section addresses direct lines to jacket whether magnetized. Most anticancer chemotherapeutics in common use are cytotoxic or vesicant (Verboom, M. C., Ouwerkerk, J., Steeghs, N., Lutjeboer, J., Martijn Kerst, J., and 4 others 2017. "Central Venous Access Related Adverse Events after Trabectedin Infusions in Soft Tissue Sarcoma Patients; Experience and Management in a Nationwide Multi-center Study," *Clinical Sarcoma Research* 7:2; Theman, T. A., Hartzell, T. L., Sinha, I., Polson, K., Morgan, J., and 3 others 2009. "Recognition of a New Chemotherapeutic Vesicant: Trabectedin (Ectei-nascidin-743) Extravasation with Skin and Soft Tissue Damage," *Journal of Clinical Oncology* 27(33):e198-200; Ener, R. A., Meglathery, S. B., and Styler, M. 2004. "Extravasation of Systemic Hemato-oncological Therapies," *Annals of Oncology* 15(6):858-862). The statin or other drug may or may not prevail against a background of the same or an adjuvant or counteracting drug introduced into the general circulation.

For example, atherosclerosis a systemic disease (see, for example, Toutouzas, K., Drakopoulou, M., Mitropoulos, J., Tsiamis, E., Vaina, S., and 4 others 2006. "Elevated Plaque Temperature in Non-culprit de Novo Atheromatous Lesions of Patients with Acute Coronary Syndromes," *Journal of the American College of Cardiology* 47(2):301-306), statins can evoke unwanted side effects as specified below, but have been recognized as exerting beneficial effects locally and not just when delivered through the bloodstream by inhibiting cholesterol biosynthesis in the liver that would otherwise be released into the systemic circulation (see, for example, Nissen, S. E., Tuzcu, E. M., Schoenhagen, P., Crowe, T., Sasiela, W. J., and 5 others 2005. "Statin Therapy, LDL Cholesterol, C-reactive Protein, and Coronary Artery Disease," *New England Journal of Medicine* 352(1):29-38; Erl, W. 2005. "Statin-induced Vascular Smooth Muscle Cell Apoptosis: A Possible Role in the Prevention of Restenosis?," *Current Drug Targets. Cardiovascular and Haematological Disorders* 5(2):135-144).

Substantially restricting exposure to a statin to only diseased tissue may allow individuals with adverse side effects to the drug when circulated at greater than a threshold concentration to avoid the unwanted effect. When the disease is systemic but acutely affects only circumscribed tissue, systemic delivery of the drug can be reduced while local delivery is raised to a level that if circulated would induce the side effects if not prove toxic (see, for example, McCarey, D. W., McInnes, I. B., Madhok, R., Hampson, R., Scherbakov, O., Ford, I., Capell, H. A., and Sattar, N. 2004. "Trial of Atorvastatin in Rheumatoid Arthritis (TARA): Double-blind, Randomised Placebo-controlled Trial," *Lancet* 363(9426):2015-2021; Klareskog, L. and Hamsten, A. 2004. "Statins in Rheumatoid Arthritis—Two Birds with One Stone?," *Lancet* 363(9426):2011-2012).

Drugs can also be concentrated for uptake by impasse-jacket straddled organs, for example. The cooperative use of impasse-jackets or stent-jackets, which can also be used to stent the drug the inlet or drug release segment and outlet or drug counteractant release segment, in pairs and higher combinations extends drug-targeting capability to definable lengths of ductus. The segment for treatment is defined by a start-of-segment entry jacket and an end-of-segment exit-jacket. Stent-jackets, patch-magnets, magnet-jackets, and magnetized stays and miniballs can be incorporated into a succession of carrier particle attracters or retainers along a ductus for dual or multistage drug-targeting.

In paired or plural use, impasse-jackets are positioned to mark off and thus define a treatment segment or stretch of a ductus using at least one jacket at the start and at least one at the end to define and treat the segment. Longer segments generally call for an entry jacket followed, according to the local need, by intervening jackets that are uniformly or nonuniformly spaced and contribute an additional complement of the same or a different drug before the exit jacket is reached. For drugs that can be directly counteracted (reversed, inactivated, neutralized) safely by another agent used as a direct chemical counteractant to be released from the exit jacket with or without heat, jackets can be paired to define the starting and ending levels along the lumen thereby to target only the segment selected for treatment.

Sequencing impasse-jackets with or without stent-jackets is addressed above in the section entitled System Implant Magnetic Drug and Radiation Targeting and Concept of the Impasse-jacket and below in the section Alternative Procedure to the Use of Expansion Inserts. Heating can be by direct contact at the treatment site, which is not tied to the clinic or by the placement of miniballs, stays, impasse-jackets, and stent-jackets in an alternating magnetic field which is. Since all of the implants will include magnetically susceptible content, differential heating if necessary is limited to elevated temperatures. When released by spontaneous dissolution, ingestion, or self-infusion through an implanted portal of a second agent, and/or by direct heating where a specific jacket need not or can be targeted or discriminated, the counteracting or neutralization of a drug released from a holding jacket or otherwise approaching from upstream is freed from the clinic.

Ionizing radiation is effective at breaking some chemical bonds, but only at levels much higher than can be generated within a tiny circumductal (circumvascular) collar. In additive interactive application, a drug released upon dissolution of or elution from a miniball held by a holding jacket upstream can be irradiated or combined with another drug farther downstream as the drug passes a radioactive or another drug-emitting miniball held in a downstream holding jacket. Whether the miniballs and holding jacket are unheated or heated from without and/or within, the holding jackets can suspend miniballs in the lumen that release drugs which will be absorbed through the adluminal layers separating the luminal from the implanted miniballs or stays thereby to produce the desired therapeutic effect by endoluminal/ductus-intramural interaction.

This could, but usually would not pertain to the component unit holding jackets of the same compound impasse-jacket with only a small interval between them. A compound impasse-jacket wherein consecutive individual impasse-jackets are used to retain a larger number of miniballs to increase the dose, or to isolate different type therapeutic substances, such as irradiating, medicating, or different containing drugs, is referred to as a composite or mixed impasse-jacket and is understood to be compound or paired, as addressed below. Such a jacket allows the differential extraction of the miniball or miniballs assigned to each jacket. The drug-targeting means described herein include the direct implantation of miniballs and stays, magnetic drug-targeting, and segment definition through suspension in the lumen of miniballs or ferrofluid-bound drugs by means of impasse-jackets, for example.

For drugs for which there is a counteractant that chemically acts directly on the drug rather than pharmacokinetically or metabolically (through drug-drug or drug-food interaction primarily in the liver) to yield innocuous products, the dose can be reduced or effectively stopped at the end of the segment; by positioning the holding jacket with the drug upstream from the holding jacket with its counteractant, only the intervening segment is medicated. In this way, a segment of almost any extent along a ductus, and not just a focal point, can be defined and targeted for treatment.

For experimental purposes, the ability to target a prescribed segment of an artery in vivo for exposure to a drug allows distinguishing between local and systemic or metabolic effects of the drug. Statins are among the most widely prescribed drugs, in itself indicating strong benefits and low incidence of adverse side effects; however, the size of the population also means that many patients (diabetics, pregnant and breastfeeding women) may be denied these benefits. One example of value in the ability to target a chosen segment of a ductus for medication with a much higher dose than could be allowed in the circulation as a general concept is that of statin drugs.

The ability to restrict exposure to high concentrations of statins in the renal arteries of diabetics to avert the myopathy or rhabdomyolysis associated with high doses in the circulation while preserving renal function (see, for example, Paulsen, L., Matthesen, S. K., Bech, J. N., Starklint, J., and Pedersen, E. B. 2010. "Acute Effects of Atorvastatin on Glomerular Filtration Rate, Tubular Function, Blood Pressure, and Vasoactive Hormones in Patients with Type 2 Diabetes," *Journal of Clinical Pharmacology* 50(7):816-822; Romayne Kurukulasuriya, L., Athappan, G., Saab, G., Whaley Connell, A., and Sowers, J. R. 2007. "HMG CoA Reductase Inhibitors and Renoprotection: The Weight of the Evidence," *Therapeutic Advances in Cardiovascular Disease* 1(1):49-59) warrants study.

While disputed for a population with established coronary artery disease rather than for the prevention of acute cardiac events in those with incipient dyslipidemia and only for the systemic dosage levels allowed, (see, for example, Robinson, J. G., Smith, B., Maheshwari, N., and Schrott, H. 2005. "Pleiotropic Effects of Statins: Benefit Beyond Cholesterol Reduction? A Meta-regression Analysis," *Journal of the American College of Cardiology* 46(10):1855-1862), statins are at least tentatively accepted by some as able to ameliorate atheromatous inflammation through mechanisms not necessarily tied to a reduction serum cholesterol (see, for example, Jones, P. H. and Farmer, J. A. 2008. "Adjunctive Interventions in Myocardial Infarction: The Role of Statin Therapy," *Current Atherosclerosis Reports* 10(2):142-148; Devaraj, S., Rogers, J., and Jialal, I. 2007. "Statins and Biomarkers of Inflammation," *Current Atherosclerosis Reports* 9(1):33-41; de Lorenzo, F., Feher, M., Martin, J., Collot-Teixeira, S., Dotsenko, O., and McGregor, J. L. 2006. "Statin Therapy—Evidence Beyond Lipid Lowering Contributing to Plaque Stability," *Current Medicinal Chemistry* 13(28):3385-3393; Rutishauser, J. 2006. "The Role of Statins in Clinical Medicine—LDL—Cholesterol Lowering and Beyond," *Swiss Medical Weekly* 136(3-4):41-49; Bellosta, S., Ferri, N., Arnaboldi, L., Bernini, F., Paoletti, R., and Corsini, A. 2000. "Pleiotropic Effects of Statins in Atherosclerosis and Diabetes," *Diabetes Care* 23 Supplement 2:B72-B78).

Holding jackets allow a statin drug, for example, in a concentration that if circulated would be myotoxic and in a diabetic could prove renotoxic, to be released at the start, and if desired, stopped at the end of a certain length (stretch, segment) of an artery that is lesioned or especially lesioned. Assuming its reduction in inflammation is not due entirely to the lowering in serum cholesterol but involves a direct mechanism or mechanisms as well (Glynn, R. J., Koenig, W., Nordestgaard, B. G., Shepherd, J., and Ridker, P. M. 2010. "Rosuvastatin for Primary Prevention in Older Persons with Elevated C-reactive Protein and Low to Average Low-density Lipoprotein Cholesterol Levels: Exploratory Analysis of a Randomized Trial," *Annals of Internal Medicine* 152(8):488-496, W174; Ridker, P. M., Danielson, E., Fonseca, F. A., Genest, J., Gotto, A. M. Jr., and 9 others; JUPITER Study Group 2008. "Rosuvastatin to Prevent Vascular Events in Men and Women with Elevated C-reactive Protein," *New England Journal of Medicine* 359(21): 2195-2207, available at http://www.nejm.org/doi/full/ 10.1056/NEJMoa0807646#t=article Top; Furberg, C. D. 1999. "Natural Statins and Stroke Risk," *Circulation* 99(2): 185-188, available at http://circ.ahajournals.org/cgi/content/ full/99/2/185), local release substantially confined to a defined segment would allow exposure to a statin drug, for example, with a local concentration far higher than could be prescribed for systemic administration but with an overall dose still minute and required over a shorter term.

Also, as addressed above in the section entitled Circulating Drug Blocking and Drug Interaction Avoidance, targeting a statin, notably, simvastatin, to a limited segment of an arterial lumen wall with a calcium channel blocker such as diltiazem or verapamil in the circulation or itself targeted for the coronary arteries, for example, should eliminate the myotoxic much less rhabdomyolytic consequences of the two when circulated together. The direct and circumscribed targeting of a segment of an artery with a statin avoids binding the statin in the gut by cholestyramine or colestipol, for example, as when both are administered orally. Drugs such as carnitine and coenzyme Q10 (ubiquinone, ubidicarenone) used systemically to counteract statin overdose resulting in myopathy, for example, tend to be large and continued over time. As pertains to almost any adverse drug-drug interaction dependent upon drugs where both are introduced into the bloodstream, so long as one does not require to be metabolized by the liver, that drug can be delivered directly to the lesion thus substantially if not entirely eliminating it from the circulation and therewith eliminating the interaction as well. With respect to statins, for example, to counter the elevated serum cholesterol and triglycerides that result as a side effect of a protease inhibitor given to treat hepatitis C or human immunodeficiency virus, the protease inhibitor is often co-administered with a statin for systemic circulation.

However, some statins used thus are associated with drug-drug interaction that results in a manyfold increase in statin exposure that can induce myopathy and even rhabdomyolysis leading to significant kidney damage or death ("FDA Drug Safety Communication: Interactions between Certain HIV or Hepatitis C Drugs and Cholesterol-lowering Statin Drugs Can Increase the Risk of Muscle Injury," available at http://www.fda.gov/Drugs/DrugSafety/ ucm293877.htm). Magnetized miniballs, stays, arrays thereof, and impasse-jackets make it possible to directly target atheromas with any statin contraindicated for co-circulation in any concentration. Statins specified as contraindicated for co-circulation with these protease inhibitors include atorvastatin (Lipitor®, Torvast®, Cardipill-LS®), lovastatin (Mevacor®, Altocor®, Altoprev®, Lipistat), rosuvastatin (Crestor®), and simvastatin (Zocor®, Lipex®).

Accordingly, using the means described herein allows the concentrated application of any disallowed statin directly at and substantially limited to the athermomatous segment treated at the same time that one of the statins approved for co-administration, specifically, pitavastatin (Livalo®, Pitava®) or pravastatin (Pravachol®, Selektine®, Lipostat®), is circulated with the protease inhibitor to counter an elevation in cholesterol and triglycerides levels without a concomitant surge in statin exposure as an unwanted side effect. Using a holding jacket or holding jackets, dosing can be continued using consecutively time-released miniballs in the number required. Using an entry impasse-jacket, an especially diseased and/or occluded segment of a ductus can be differentially treated.

For example, a statin drug in much higher concentration than could be prescribed systemically can be released locally at the start of the segment and either allowed to lose concentration by continued flow with the circulation, or, with the addition of an exit-jacket, can be removed as the exit-jacket is passed, the exit jacket dose usually adjusted to counteract the dose released at the entry-jacket. Furthermore, the use of impasse-jackets that incorporate extracorporeally energizable internal heating as addressed below makes it possible to heat the lumen wall and the medication releasing miniball or miniballs held by the entry jacket for accelerated dissolution and uptake, and if appropriate, to substantially extinguish these effects on passing the exit jacket of the pair.

Adverse sequelae have been associated with the metabolic mechanism that interferes with cholesterol synthesis (possibly as the result of overdosing), to include myositis and myalgia (see, for example, Joy, T. R. and Hegele, R. A. 2009. "Narrative Review: Statin-related Myopathy," *Annals of Internal Medicine* 150(12):858-868), possible liver damage in patients otherwise compromised (see, for example, Liu, Y., Cheng, Z., Ding, L., Fang, F., Cheng, K. A., Fang, Q., and Shi, G. P. 2010. "Atorvastatin-induced Acute Elevation of Hepatic Enzymes and the Absence of Cross-toxicity of Pravastatin," *International Journal of Clinical Pharmacology and Therapeutics* 48(12):798-802), as well as other adverse effects (see, for example, Kiortsis, D. N., Filippatos, T. D., Mikhailidis, D. P., Elisaf, M. S., and Liberopoulos, E. N. 2007. "Statin-associated Adverse Effects Beyond Muscle and Liver Toxicity," *Atherosclerosis* 195(1):7-16).

Targeting a statin to minimize pancreatic exposure may also reduce the 9 percent risk, primarily in older adults, of inducing type 2 diabetes (Sattar, N., Preiss, D., Murray, H. M., Welsh, P., and 29 collaborators 2010. "Statins and Risk of Incident Diabetes: A Collaborative Meta-analysis of Randomised Statin Trials," *Lancet* 375(9716):735-742). The benefit of statins as attriibutable to a reduction in plasma cholesterol has been disputed and even claimed to be harmful (see, for example, Ravnskov, U., Allen, C., Atrens, D., Enig, M. G., Groves, B., Kauffman, J. M., Kroneld, R., and 6 others 2002. "Studies of Dietary Fat and Heart Disease," *Science* 295(5559):1464-1466, available at http://www.ravnskov.nu/cholskept.links.responsetoGrundy.htm; Morrell, S. F. and Enig, M. G. 2000. "The Skinny on Fats," at http://www.westonaprice.org/know-your-fats/526-skinny-on-fats.html).

The inducement of liver damage in the absence of existing disease has not been conclusively determined (see, for example, Lewis, J. H. 2012. "Clinical Perspective: Statins and the Liver—Harmful or Helpful?," *Digestive Diseases and Sciences* May 12; Bergmann, O. M., Kristjansson, G., Jonasson, J. G., and Björnsson, E. S. 2011. "Jaundice Due to Suspected Statin Hepatotoxicity: A Case Series," *Digestive Diseases and Sciences November* 11; Bader, T. 2010. "The Myth of Statin-induced Hepatotoxicity," *American Journal of Gastroenterology* 105(5):978-980; Rajaram, M. 2009. "Hepatitis, Rhabdomyolysis and Multi-organ Failure Resulting from Statin Use," *British Medical Journal Case Reports* February 2009), but statin-associated hepatotoxicity as aggravating existing disease (see, for example, Calderon, R. M., Cubeddu, L. X., Goldberg, R. B., and Schiff, E. R. 2010. "Statins in the Treatment of Dyslipidemia in the Presence of Elevated Liver Aminotransferase Levels: A Therapeutic Dilemma," *Mayo Clinic Proceedings* 85(4):349-356; Russo, M. W., Scobey, M., and Bonkovsky, H. L. 2009. "Drug-induced Liver Injury Associated with Statins," *Seminars in Liver Disease* 29(4):412-22) is seldom disputed for specific preexisting conditions (see, for example, Madhoun, M. F. and Bader, T. 2010. "Statins Improve ALT Values in Chronic Hepatitis C Patients with Abnormal Values," *Digestive Diseases and Sciences* 55(3):870-871; Sorokin, A., Brown, J. L., and Thompson, P. D. 2007. "Primary Biliary Cirrhosis, Hyperlipidemia, and Atherosclerotic Risk: A Systematic Review," *Atherosclerosis* 194(2):293-299; Lowyck, I. and Fevery, J. 2007. "Statins in Hepatobiliary Diseases: Effects, Indications and Risks," *Acta Gastroenterologica Belgica* 70(4):381-388).

Administration of a statin in this targeted manner dispels the long-standing and unresolved concerns for teratogenic risk (see, for example, Taguchi, N., Rubin, E. T., Hosokawa, A., Choi, J., Ying, A. Y., Moretti, M. E., Koren, G., and Ito, S. 2008. "Prenatal Exposure to HMG-CoA Reductase Inhibitors: Effects on Fetal and Neonatal Outcomes," *Reproductive Toxicology* 26(2):175-177; Petersen, E. E., Mitchell, A. A., Carey, J. C., Werler, M. M., Louik, C., and Rasmussen, S. A. 2008. "Maternal Exposure to Statins and Risk for Birth Defects: A Case-Series Approach," *American Journal of Medical Genetics. Part A* 146A(20):2701-2705; Kazmin, A., Garcia-Bournissen, F., and Koren, G. 2007. "Risks of Statin Use during Pregnancy: A Systematic Review," *Journal of Obstetrics and Gynaecology Canada* 29(11):906-908).

However, entry jackets on the carotids and exit-jackets on the jugulars as addressed above in the section entitled Concept of the Impasse-jacket, should allow the prenatal use of thalidomide, other sedative-hypnotics, and any other kind of drug that must be kept from reaching the placenta. While an invasive procedure to place the trap array for the sole purpose of allowing the use of a statin will normally be discounted, the ability to use many other drugs in selected patients will justify the procedure. Also, since the drug is eliminated without being metabolized, adverse drug interactions are substantially eliminated, allowing drugs to be used together that otherwise would interact as to pose a risk.

There is no need to avoid prescribing antibiotics, antimycotics, antidepressants, immunosuppressants, colchicine (Sarullo, F. M., Americo, L., Di Franco, A., and Di Pasquale, P. 2010. "Rhabdomyolysis Induced by Co-administration of Fluvastatin (Lescol®) and Colchicine," *Monaldi Archives for Chest Disease* 74(3):147-149), fenofibrate (Buyukhatipoglu, H., Sezen, Y., Guntekin, U., Kirhan, I., and Dag, O. F. 2010. "Acute Renal Failure with the Combined Use of Rosuvastatin and Fenofibrate, *Renal Failure* 32(5):633-635), and gemfibrozil (Jones, P. H. and Davidson, M. H. 2005. "Reporting Rate of Rhabdomyolysis with Fenofibrate+Statin Versus Gemfibrozil+Any Statin," *American Journal of Cardiology* 95(1):120-122), for example, or advising the patient to avoid grapefruit or grapefruit juice, which impede statin metabolism resulting in higher plasma levels and can result in muscle damage, liver damage, and death.

If for some unforeseeable reason a statin counteractant is desired, the choice indicated is no more 3-hydroxy-3-methylglutaryl-coenzyme A reductase (Brown, M. S., Dana, S. E., Dietschy, J. M., and Siperstein, M. D. 1973. "3-Hydroxy-3-methylglutaryl Coenzyme A Reductase. Solubilization and Purification of a Cold-sensitive Microsomal Enzyme," *Journal of Biological Chemistry* 248(13):4731-4738, available at http://www.jbc.org/content/248/13/4731.full.pdf+html) than could be necessary to take up the reductase inhibitor. Similarly, pharmaceuticals such as enzymes that act upon a substrate substance, as does an inhibitor on a reductase, the substrate itself may serve as the reversal agent. Where a background of systemically distributed statin is wanted for the systemic condition, an impasse-jacket allows supplementing the systemic dose over an especially affected segment with no exit jacket used to counteract or neutralize the statin released locally.

5-fluorouracil formulated for delivery to an entry jacket or jacket-array along the gastrointestinal tract for magnetically targeted chemotherapy of the surrounding wall, for example, can be counteracted through the release from an exit jacket of Vistonuridine® (Wellstat Therapeutics Corporation). Leucovorin (folinic acid) alone and with glucarpidase (carboxypeptidase), thymidine, and folinic acid act counter to methotrexate. The number of reversal agents suitable for release from an exit jacket should increase over time. This sectioning off of the ductus (usually a blood vessel) into segments to define treatment zones for differential dosing, drugging, or other chemical treatment can be continued over much of the length of the ductus.

When necessary, a nonabsorbable jacket is used to allow for the reinjection of medication or radiation miniballs at intervals beyond the life expectancy of an absorbable jacket. A peripheral artery, for example, can be marked off in segments for differential medication and/or dosing of each segment, using jackets spaced at intervals that span past lesions such as atheromatous or as otherwise desired. If necessary, these jackets are nonabsorbable. Re-charging or re-dosing of any type holding jacket is currently by conventional hypodermic injection upstream from the holding jacket and used to increase, continue, or chemically disable the drug. Oral administration should become possible in the near future. Continued delivery is also possible by placing drug-eluting miniballs with consecutive release times at the entry level.

I15e. Direct Lines from the Body Surface to and from Impasse and Other Type Jackets Without means for creating safe, nonleaking, harmless, and smooth continuity between catheteric and native lumina to connect fluid and electrical lines, a standard to which indwelling catheters do not remotely rise, and tissue surface fluid and electrical line connectors likewise noninjurious, to provide a fully implanted automatic disorder response system capable of operating for many years is impossible. Direct piping to and from a tubular anatomical structure, or ductus, through a catheteric line entered from outside the body through a portal implanted at the body surface to a ductus side-entry or impasse-jacket for connection to a ductus or to a nonjacketing side-entry connector fastened to the surface of tissue or an organ can be conceived of as expanding upon the concept of a laparoenterostomy or a jejunostomy, for example, where a tube is surgically connected to the gut to provide nutrients when the digestive tract is obstructed proximad-, meaning above, or drainage when the bowel is obstructed below, or distad.

Copending applications 2016/0051806 and 20170197028 describe and illustrate the drug feedlines, connectors, and body surface ports used to effect connections far the directly pipe targeted delivery of drugs and other therapeutic substances. This drug targeting by means of direct piping applies to the jackets and wraps described herein as well as applications 2016/0051806 and 20170197028 An exemplary arm or channel of control in a hierarchically organized automatic disorder response system emplaced to treat comorbid conditions is addressed in section XX below and FIG. 107, with the organization and componentry addressed in section XXI and FIG. 108. Delivery of the drug, radionuclide, or other therapeutic substance to an impasse-jacket is preferably passive, that is, by injection, infusion, or ingestion followed by normal passage through the lumen. The need for direct delivery is satisfied by infusion through the surface port and into the feedline, thence to the target tissue whether a ductus, which is unsuitable for administration on an ongoing basis.

To treat interactive (trans-syndromal) and noninteractive (trans-nosological) conditions in comorbidity, a small port at the body surface, usually in the pectoral region with multiple openings for different drugs to admit drugs into subdermally positioned reservoirs for dispensing to any of a number of ductus side-entry jackets responsive to signals received from sensors processed by a prescription program driven microcontroller is administered by a fully implanted automatic adaptive hierarchical ambulatory prosthetic disorder response control system. Such a system, which can incorporate the telemetric transmission of data to the clinic (see, for example, Ferguson, J. E. and Redish, A. D. 2011, Op cit.), is described in copending application 20160051806, Ser. No. 14/121,365 entitled Ductus Side-entry Jackets and Prosthetic Disorder Response Systems and below in the sections entitled Exemplary Channel of Control in a Fully Implanted Ambulatory Adaptive Hierarchical Control System for Automatic Response to a Comorbid Condition and Fully Implanted Ambulatory Adaptive Hierarchical Control System for Automatic Response to a Comorbid Condition. Direct piping to each of a number of jackets also allows different segments of the same ductus to receive different drugs, doses, or both.

The direct metered delivery of each drug to its target jacket eliminates the potential vagaries of passive delivery where control is limited. Direct lines to and from magnetized impasse-jackets and other jackets from an infusion set cannula or cannulae at the body surface for connecting a syringe or pump serve to draw medication into the wall surrounding the lumen. By comparison, nonmagnetized jackets allow the direct delivery of therapeutic substances and the withdrawal of samples of luminal contents for analysis with little if any penetration into the surrounding wall. When not in use, the portal is sprayed with disinfectant and covered with a single use flesh colored bandage with pressure sensitive adhesive backing when dry. Driving the prescribed dose of each therapeutic substance ahead of a column of water assures that no portion of the dose is left within or can clog the line.

The syringe barrel refill cartridge or infusion pump delivers a measured volume of the therapeutic substance followed by a measured volume of water. Different substances can be brought by dilution with water, for example, to the same viscosity. In the clinic, the use of transparent tubing and contrast can assist to confirm that the therapeutic substance has been administered. When possible, the portal at the body surface are situated at a level higher than that of the jackets. An impasse-jacket and/or dummy collar with side-access (side-entry, side inlet, side-outlet) connector is used when the need for continuous or frequent dosing with the same or different drugs is known or likely to ensue. Aspiration to provide samples for analysis at any jacketed level along the ductus is practicable as well.

The direct piping of a lavage solution to an upstream jacket whether of the impasse-, stent-, magnet, or clasp-jacket type allows irrigation or samples to be drawn from any jacket downstream. Nonmagnetized jackets and dummy-collars can also be used thus. The dummy-collar braced downstream to an impasse-jacket can thus serve as a take-off for samples to confirm drug uptake within or release at the impasse-jacket. The inlet, and if a reversal agent is necessary, an outlet jacket can be unmagnetized. An impasse-jacket, its dummy collar or collars, or both can be provided with side-access lines for direct injection from a syringe through an Ommaya-like reservoir or infusion by a portable miniature pump through an infusion set cannula at the body surface of substances such as drug carrier nanoparticles, for example.

An independent direct line feed to each of several impasse-jackets overcomes the problem of selectively targeting each jacket with a different substance or substances, as well as simplifies higher rate intermittent or continuous administration of drugs to the segments, organ, or gland the impasse-jackets bound and define. A side-access connector can be incorporated into any impasse-jacket and/or dummy collar or outrigger, but unless needed, such use is uneconomic. Because it must be harvested, properly stitched in place, may stenose, shrink, occlude, increases the risk of infection, and makes attachment to the synthetic components more complicated, an autologous vein graft is not preferred for use as an impasse-jacket side-access line.

These steps introduce additional complications and risks and significantly protract a procedure. Many ductus treatable with one or more impasse-jackets are small, necessitating the use of microsurgical techniques. When directed not to the ductus but rather to an impasse-jacket or dummy collar, incorporation of a polymeric catheter connector in the jacket or collar eliminates the need for midprocedural steps. Instead, the jacket with connector is preassembled, insertion then consisting only of placing the jacket about the ductus. However, when connection of a side-access line is from the body surface to the ductus itself up- or downstream from the jacket, an autologous graft is preferred. The side-access connector consists of a length of transparent polymeric tubing only so long as extends from the internal surface of the lumen to a length beyond the outer tunic sufficient to connect a line.

The inner or ductus-ward rim about the luminal or adaxial end of the catheter connector tube is sharp and has a luminal-end valve that consists of a resilient polymer slit membrane which opens to the lumen only when drawn by a retrograde vacuum or pushed by antegrade pressure greater than that of the blood or other pressure in the lumen. So that a point of thrombogenic turbulence will not be created along the internal surface of the lumen wall, the sharp distal tip or rim is level with, not protrusive beyond, the slit membrane valve, and both are level with the internal surface of the ductus once the ductus wall is cut through and the wall plug extracted. On manufacture, the slit membrane is bonded within the end of the connector tube so that it will not tear loose under the antegrade, or forward, and retrograde, or aspirative, pressure to which the valve will be subjected.

The pressure will be imposed by a syringe or pump connected to the connection point at the surface of the body, such as an Ommaya-like reservoir or infusion set cannula and patch. A round hole to admit the connector tube is cut through the extraction grid and foam lining, and a flange surrounding the hole having a neck extending perpendicularly outward to afford a larger surface area for bonding to the tube is bonded to the extraction grid about the hole but not to the connector. The connector tube, and the inner or ductus-ward tip of the connector tube slid through the hole so that its distal or ductus-ward tip is brought flush level with the internal surface of the foam lining. Until placement, the connector tube fits through the hole in the flange, extraction grid, and foam lining through which it passes only so tightly as prevents it from falling out, and remains slidable therethrough.

Impasse-jacket compliance or expansion and contraction as the pulse passes is provided by the foam lining, and in excess of that permitted by the foam lining, by the spring-loaded hinge joining the halves so that these can open and close. Since the slit membrane valve is flush or level to the internal surface of the vessel or intima, while the foam lining and hinge are outside the adventitia, the point where the line leading from the connection point at the body surface enters the jacket can be placed anywhere but where the halves part. On placement, the outer surface of the ductus is wetted with contrast, the impasse-jacket or outrigger placed about the ductus, the adaxial end of the connector tube pushed flush against the outer surface of the ductus, and an aspiration line connected to the abaxial or radially outward end of the connector tube.

The adaxial end of the connector tube is slid through the flange into contact with the outer surface of the ductus, and the aspiration line used to cause the sharp rim of the connector tube, which protrudes forward when the resilient membrane is drawn backward, to incise into the wall of the ductus. The force of aspiration is raised until the plug cut into the ductus wall is drawn out through the membrane slit, the contrast and transparence of the connection tube allowing this process to be observed. This method for insertion of the supply or aspiration line through the side of the ductus with simultaneous plug extraction and line insertion allows application to an artery with little bleeding or hemodynamic interruption, and to the gut with little if any leakage of septic matter, and since it avoids the need to interrupt perfusion through clamping, ligature, or serrenoeuding, as well as allows contact at limited to the treatment point with single-sided approach, can be applied to a coronary or a carotid artery, for example.

The inner or adaxial end of the connector tube is then slid through the flange so as to be flush level with the internal surface of the lumen wall, and the flange, having been bonded to the extraction grid when manufactured, is then bonded to the connection tube. The outer or abaxial end of the side-connector now extends out of the side of the impasse-jacket to a length no greater than allows a body surface infusion set cannula connection catheter to be securely connected to it. The use of a quickly setting cyanoacrylate cement to bond the connection tube to the internal surface of the neck of the surrounding flange once its inner end has been brought flush to the internal surface of the lumen allows connection to the catheter supply line that will lead to the infusion set cannula and patch or Ommaya-like reservoir type connection at the body surface in a single procedure.

Whether or not connected to a catheteric supply and aspiration line during the procedure, the protruding end of the side connector has rounded and smoothed edges. When not connected, the surrounding tissue is additionally protected by placing tape over the exposed end until needed. Referring now to FIG. 16, it should now be clear that either end collar 124 can be accessed from the body surface through a side-access connector, so that if not completely taken up during the intervening segment and leaving a residue that could cause adverse side effects if carried beyond the diseased segment, a drug or other therapeutic substance introduced through the upstream collar can be neutralized or reversed by a reversal agent released from the downstream collar.

To allow an additional substance or substances to be delivered directly to it, impasse-jacket proper 125 can also be connected to the body surface. The use of plural side-access connectors to or from collars 124 or jacket 125 is plainly possible but not likely to be necessary. Magnetizing the adaxial end or segment by using a ferromagnetic flange or laminating or coating the connection tube with a polymer layer containing magnetized inclusions allows a magnetic nanoparticle carrier bound drug be held abaxially or short of the slit membrane outside of the ductus lumen, then forced through the slit membrane when the pressure imposed by the syringe or pump is sufficient to force it open. If prepositioned thus to avert a future accident but never needed, the prestored drug or other substance can be drawn for laboratory analysis by aspiration at the body surface connector.

Magnetic drug carrier particles that are ferro cobound, or indissolubly and/or temperature-independently bound to the medicinal component, are drawn toward the source of the magnetic force, and since the impasse-jacket surrounds the ductus, the particles are drawn into the wall surrounding the lumen. By comparison, drug carrier particles that are ferrobound are released to flow upstream, the magnetic force drawing only the ferromagnetic component of the conjoined ferrous and medicinal particles into the wall. To treat a discrete organ such as a kidney, the entry impasse-jacket is placed along the renal artery, the ferro-bound drug freed to pass into the parenchyma. If a residue is to be eliminated, then a jacket to release a reversal agent is placed along the renal vein.

Access and clearance sufficient to place these jackets requires dissection through the renal fat pad, artery, and, special care given to not transect the first branches of the artery and vein, which support the adrenal gland. Unlike a healthy artery free of atheromatous, dissecting, or other lesions, wherein the constituents of the blood, such as leukocytes and blood fats flow along the surrounding wall as it were a conduit with few such constituents drawn therein, in the kidney, flow is intrinsically to the parenchymal tissue, which may be diseased. In a diseased artery, however, encirclement with a magnetized jacket serves to draw the ferrobound drug into the diseased wall. With disease of the cortex, however, patch-magnets attached to the outer fibrous capsule, or with respect to organs more generally, the involucrum, will actively draw the drug outward and into the diseased tissue.

A substance piped from a syringe can be adjusted in temperature before delivery, one from a portable pump warmed by heating at or by the pump, and/or the impasse-jacket can be remotely warmed by placing the patient in a radiofrequency alternated magnetic field, as addressed in section X2c below entitled Stereotactic Arrest and Extraction of a Dangerously Circulating, Mispositioned, or Embolizing Miniball, among others. Stent-, impasse-, magnet-, and clasp-jackets large enough to incorporate conductive wire such as nichrome can be heated by wire connection at the body surface connector. Innumerable combinations of medicinal fluids additionally allow carrier release or neutralizing dissolution with continuation downstream.

The potential for iron overburden through accumulation of the carrier is addressed above in the section entitled Field of the Invention and should not be associated with the risk of transfusional hemosiderosis where the iron content is far higher. Iron overload might arise with a small patient in whom drug carrier-bound drugs are continually distributed to multiple jackets. In this event, monitoring and treatment by deferoxamine injection Desferal®, phlebotomy (see, for example, *The Merck Manual of Diagnosis and Therapy,* 18th Edition, pages 1132-1133) and/or chelation therapy (see, for example, *Harrison's Principles of Internal Medicine,* 16th Edition, page 600) constitute the standard of care response measures.

Fully implanted ambulatory adaptive hierarchical control systems for automatic response to comorbid conditions and an exemplary channel of control in an ambulatory adaptive hierarchical control system for automatic response to comorbid impairment are described in copending application Ser. No. 14/121,365 published as 20160051806 entitled Ductus Side-entry Jackets and Prosthetic Disorder Response Systems and below in the sections entitled Fully Implanted Ambulatory Adaptive Hierarchical Control Systems for Automatic Response to Comorbid Conditions and An Exemplary Channel of Control in an Ambulatory Adaptive Hierarchical Control System for Automatic Response to Comorbid Impairment.

I15f. Single and Plural Circuit Pumping through Direct Lines to Jackets

For placement along the vascular tree, a syringe or portable infusion pump delivers the substance to the impasse-jacket or dummy-collar. Depending upon the form of bond between the carrier and the drug, the jacket actively draws the magnetic drug carrier with the drug from the blood into the lumen wall or only the carrier is drawn to the jacket and the drug released to continue downstream. The strength of magnetization along the jacket, distance separating the carriers from the jacket, susceptibility of the carrier, and direction and pressure of the bloodstream thus set the direction, rate, and take-up of the carrier with the drug. If the drug is released to proceed upstream, then carrier separation rate must be considered. Drugs bound with the carrier to obtain both types of targeting can be included in the same or consecutive suspensions.

With conditions that present separated segments which require like treatment such as does regional enteritis and atheromatous plaques, multiple portals are not implanted at the body surface; rather, a wider diameter trunk coming off the surface portal branches to each jacket. The diameter of each branch allows differential distribution of a therapeutic substance to each segment. Physiological factors such as the blood pressure and pulse rate are not ordinarily manipulated for this purpose, distribution along the lumen wall left to the magnetic field strength at a given level relative to carrier distance and susceptibility and concentration at a given level. However concentrated, when the drug carrier is uniformly attached to the drug in one-for-one relation, the drug carriers and concentration are inherently matched, so that the rate and level of extraction from the passing blood is relatively constant on passing through an impasse-jacket of given magnetization gradient.

The point of entry of the delivery catheter, which can serve as a supply or aspiration line, into the jacket is ordinarily toward the upstream (entry, proximal) margin of the jacket. Hypothetically, this one-for-one relation should allow a given combination of a jacket and drug carrier with any drug and the complete uptake of a drug to be limited to a jacketed segment without continuation through the general circulation. The preferability to eliminate an unwanted residue, if any, from continuing downstream can be satisfied by placing a downstream impasse-jacket or a jacket with a magnetized, rather than a dummy exit collar with piped reversal agent, or a magnetized downstream outrigger to release a reversal agent.

Furthermore, because the risk of clogging the jacket disallows more than a moderate mass of a drug to be delivered at a given rate, and dilution within the circulation is high. These factors mean that the need for a reversal agent is exceptional. If advisable, a reversal agent can be piped through a second line entering the impasse-jacket toward its downstream end or the downstream outrigger or dummy-collar of the jacket. Similarly, the drug or radionuclide carrier can be delivered to its upstream dummy-collar or the upstream segment of the jacket. Ductus that can be briefly clamped to define a certain segment can be lavaged over that segment by introduction of plain water, antiseptic, or anti-fungal solution through a jacket whether magnetized at either end and its removal at the opposite end of the segment.

I16. Stent-Jacket Insertion Tools

I16a. Insertion Tool Structure

Stent-jacket insertion tools (stent-jacket openers, stent-jacket applicators, stent-jacket placement tools, stent-jacket implant tools, base-tube retractors, side-slit expanders, side-slit retractors, side-slot retractors, side-slit expanders, etc.), such as those shown in FIGS. 16 thru 19 are made of nonmagnetic metal or plastic and provided in a range of sizes to expand stent-jackets of different diameters and thicknesses for placement about (in surrounding relation to) vessels or ducts at different depths. The terms 'tube retractor' and 'tube expander' already in use for unrelated devices, terms such as 'base-tube (slit) expander' or 'base-tube slit-edge retractor' are necessary to distinguish such a stent-jacket base-tube expansion and placement device. Stent-jacket insertion tools are used to pry open the elastic jacket to encircle the ductus.

Impasse-jackets are inserted through the access incision while open, an insertion tool then limited to assisting in making adjustments following initial placement. Stent-jacket and stay insertion tools include side-clips for attaching an endoscope, laser, aspiration line, or other cabled ancillary device. When a separate incision is necessary to access the outside of a tubular structure that is inaccessible from outside the body, the minimization of trauma requires that the incision be small and that the component to be inserted be practically manipulable through the incision. Small joint arthroscopic tools are available, but not suited to opening the stent-jacket through the incision. Accordingly, special tools are provided to minimize the size of the access wound needed to apply a stent-jacket.

Compared to the length of the incision needed to suture prosthetic rings at intervals about the trachea, for example, that needed to insert and place a stent-jacket is small. To minimize procedural and general anesthetic time as well as trauma, even larger stent-jackets, chain-stents, and chain-guards (braced guards) must insert through minimal entry portals and do so readily. Stent-jacket insertion tools must be nonmagnetic, hence made, for example, of austenitic stainless steel, such as 18-8, 304, or 316 amenable of hardening in smaller thicknesses. Due to the need for absolute and dependable stiffness in the arms of these tools, the unacceptability of the parts coming apart in use, and the need to avoid any protrusions by joints or tightening screws, for example, the use of adapters to fit over the arms of existing surgical instruments is discounted.

For use in a robot, the 'fingers' of the claw hand are configured as are the arms of the insertion tool as described below. Such tools are made to conform to the many dimensional requirements of base-tubes having different thicknesses and the need for handles of a length adequate to access deeper locations within the body. To allow passage through as small an incision as possible, the tools are long-handled and narrow but with burnished edges and in a gauge unlikely to injure anatomy that must be moved aside to reach to target ductus. While any number of complex linkages, ratchets, or pulleys could be incorporated into such a tube slit expansion device, any of which could further be made adjustable for use with stent-jackets over a range of sizes, for the least expense and greatest dependability, the use of simple tools is preferred.

That stent-jacket insertion tools can be provided with handles suitable for use with a robot is considered obvious. That shown in FIG. 17 is essentially a small spring-tongs similar to a Finsen-type retractor for shallow placement, but with continuously flat and curved spatula-shaped blades 10 as in a Deaver retractor. Blades 10 are reversed or everted so that the major convex surfaces face outwards and the distal ends of the scoop-shaped blades are recurved or bent around to produce uniform, or hooking, ends 13 as seen in profile. Hooking ends 13 engage the edges of slit 9 in base-tube 5 as seen in FIG. 5. The minor convex surfaces of hooking ends 13 face medially inward toward one another and thus reversely relative to the balance of the blades 10.

In any spring type tongs or tweezers-configured stent-jacket insertion tool, rotary joints to facilitate access to the exterior of the ductus to be treated through a keyhole incision can be provided. These joints, which are placed just short of the distal point where the blades begin to curve outward at the working end on each side of the handle, allow the operator to forcibly pivot the blades together to either side perpendicularly to the direction of blade opposition. The rotary friction joints consist of a tight rivet with beryllium copper or austenitic stainless steel wave spring washer, for example. For a stent-jacket of given diameter, insertion tools are made in different lengths. Making hooking ends 13 somewhat rounded and open facilitates use of a single tool with base-tubes of different thickness without resistance to release of the side-slit or side-slot when the base-tube is to be released.

In most instances, however, there will not be sufficient space behind the ductus to allow disengagement thus, so that the tool must be gently pushed forward and slid off one or the other side edge. To prevent the hook-ends from catching into the moisture barrier-coated viscoelastic polyurethane foam lining will usually necessitate pre-wetting the lining with a lubricant such as ACS Microslide®, Medtronic Enhance®, Bard Pro/Pel® or Hydro/Pel®, Cordis SLX®, or Rotaglide.® This action is carried out with minimal injury to the peripheral blood and nervous supplies foremost; one reason to use a compound stent is the reduced distance to the side edges to disengage the insertion tool from any one sub-stent. That shown in FIG. 16 is a springs tong type for deeper lying ductus.

The tools are made of heavy gauge spring steel, which may be plated for corrosion resistance. Stent-jacket insertion tools for jacketing vessels, for example, are generally 2 to 3 millimeters in side-on thickness or width expanding to 4 to 5 millimeters across the hook ends. Those for expanding larger stent-jackets are proportional in thickness relative to overall dimensions. To avoid being caught along when slid over the edges of the stent-jacket side-slit during application to the ductus, the edges of the insertion tool hooking ends are rounded, and the hooking ends of smaller tools are coated with polytetrafluoroethylene. To prevent the snagging of neighboring anatomical structures, the outer edges are rounded as well. However, the incorporation of rollers to line the hook is not preferred as unnecessarily difficult to manufacture and costly.

The conformation of hooking tips 13 must allow free disengagement from the free edges of the stent-jacket side-slit by a quick forward movement. Nonmagnetic polytetrafluoroethylene coated hooking tips 13 retain the width of the blades 10 proximal or leading up to these. The handles or arms 11 are configured and united below at a junction 12, and since the tools would normally be made of one continuous piece of metal, this would usually be at least one but here shown as two sharp bends where the handles of the two sides join to enhance the outward springiness or restorative force that acts to expand the base-tube slit when not forcibly closed by squeezing the sides together.

Finger rests, or widened portions along handles 11 for the thumb and index finger to pinch the arms together could be added, but have not, because at uniformly five millimeters in width for a tool of average length, the lever handles are wide enough that the tool will not rotate between the fingers, especially when covered with gloves of neoprene, synthetic polyisoprene latex, or latex. To incorporate sliding finger rests that would allow taking advantage of the optimal moments of force in the surgical layout involved would be more a hindrance than aid, the operator intuitively moving to the position affording the best leverage. The working or blade portions distal to the crook in the handles can be joined to the straight portions of the handles by a rivet to create a swivel joint (not shown) that allows the angle between the straight portions and the working ends to be varied.

The rivets are tightened enough to prevent the ends from unintentional rotation. The stent-jacket placement tool shown in FIG. 18 is a scissors-tongs rather than a spring-tongs or tweezer-type configured embodiment for shallow placement that is similar to a Weitlaner type retractor just as the tweezers type is similar to a Finsen-type retractor, except that it is designed to pull in only two rather than three directions. The continuous flattened spoon or scoop-shaped retractor blades 14 are the same as those of the tongs-type retraction tool described immediately above. In any scissors or pliers-configured stent-jacket insertion tool, rotary joints to allow the blades to pivot perpendicularly to the direction of blade opposition consist of a tight rivet on each side of the handle positioned distal to the main rotary joint that joins and allows rotation of the handles.

The handles 15, made as single parts, are reversely bent so that closing the finger holes 16 opens rather than closes the end hooks 17. The scissors-tongs can be urged either open or closed by means of torsion or leaf springs, as is well known in the scissors-making industry. While the stent-jacket insertion tool shown in FIGS. 18 and 19 are not shown in an edge-on view, tools for jacketing vessels, for example, are generally 2 to 3 millimeters in side-on thickness or width expanding to 4 to 5 millimeters across the hook ends, while those for expanding larger stent-jackets are proportional in thickness relative to overall dimensions.

As with the tweezers type tool of FIGS. 16 and 17, to minimize the length of the incision necessary to access the vessel or duct from the outside for placement of the stent-jacket, the working ends distal to the handles can be joined to the handles by rotary joints or rivets 158 in FIG. 18 to create swivel joints that allow the angle between the handles and the hook-like tips 17 for engaging the free edges of the base-tube side-slit or slot to be varied when a probe is used to prod the base-tube to the angle required. The rivets are tightened enough to prevent the ends from other than intentional rotation. An embodiment configured as shown in FIG. 18 or as a pistol grip, for example, can be made with a ring that allows use of the index finger to adjust the angle of the working ends (not shown). The finger-ring retracts or pushes forward a rod connected to lever arms joined to the working ends distal to the swivel joints to change the working angle. The design of surgical retractors make such configurations familiar.

I16b. Use of the Stent-Jacket Insertion Tool

In use, the stent-jacket is placed on the insertion tool so that the free edges of the stent-jacket are held within the recurved distal working hook tips 17 of the tool and the side-slit is directed forward. In preliminary testing prior to application, depending upon its pliancy and length, the stent-jacket when pulled open at its midpoint will open sufficiently for placement along its entire length or only over the segment proximal to the hooking ends of the insertion tool. The expedite the release of the hook ends 13 from the edges of the stent-jacket, the end of the tool can be wetted with any suitable lubricant such as Medtronic Enhance®.

If expansion is limited in length, then the ease with which the hooking tips slide along the cut edges of the stent-jacket side-slit or side-slot with one end of the stent-jacket fixed in position is checked prior to insertion, and if, polytetrafluoroethylene coating notwithstanding, the tool resists being slid along the pulled apart edges of the side-slit, the working ends of the insertion tool are wetted with a lubricant (anti-adherent, glidant) such as those specified above in the preceding section entitled Sectional Extraluminal Stents, Segmented and Articulated or Chain-stents. The stent-jacket can be expanded (pulled open) for placement either prior to entry or upon reaching the target ductus.

Depending upon the angle of approach, length, the need to clear neighboring structures, and resilience of the stent-jacket, the end-hooks of the insertion tool are used to pull open the stent-jacket at its center or close to one or the other of its ends, ideally, prior to introduction through the entry wound. The stent-jacket is introduced through a small incision (microincision, 'keyhole,' bandaid; or laparoscopic incision) close to if not directly overlying the location for placement. The width of the entry wound required depends upon the size of the stent-jacket, whether it is pulled open prior to entry, and whether it can be inserted parallel to the handles of the insertion tool. Entry with the stent-jacket pulled open and parallel to the handles of the insertion tool allows passage through a smaller incision.

Whether the stent-jacket has been expanded prior to insertion, entry can be parallel to surface of the body, with one side of the stent-jacket placed through the entry wound at a time. Since the insertion tool hook-tips are rotatable, a sterile wooden stick probe can be used along the path to the target ductus to angle the stent-jacket as necessary to avoid neighboring structures. When the side-slit is proximal, facing, parallel to the target ductus, and the stent-jacket can be sufficiently expanded to apply it without further effort, it is pushed forward to encircle the substrate ductus. When the stent-jacket is longer or more pliant, use of the stent-jacket insertion tool can be made difficult by the tendency of the base-tube to contract over too short a length to the sides of the tool working tips.

More often a probe held against the closed end or one of the bar magnets will be needed to stabilize or push the stent-jacket so that the insertion tool hook ends slide along the free edges of the base-tube side-slit to progressively pull the stent-jacket open along its entire length for encirclement of the target ductus. That is, the insertion tool is slid along the free edges of the stent-jacket side-slit, or the free edges of the stent-jacket side-slit are slid through the hook-ends of the insertion tool, or these movements are used in combination as the anatomy and forces involved dictate.

II. Clasp-Magnets

II1. Subcutaneous, Suprapleural, and Other Organ-Attachable Clasp- or Patch-Magnets Clasp- or patch-magnets for exerting attractive force over greater distances mount discrete magnets on clasps for fastening to tissue. This is the type shown in FIGS. 25 and 26. For use over shorter distances, the clasp itself is magnetized and biocompatibility encapsulated for chemical isolation, various polymers, noble metals, and nonmagnetic stainless steels available for this purpose. Clasp-magnets are made as unobtrusive and with rounded edges to be as nonabrading to surrounding tissue as possible, hence, flatly conformed with rounded edges.

Clasp-magnets for attachment to tissue that includes small vessels and nerves or which diseased, for example, must not be compressed, are lined with viscoelastic polyurethane 'memory' foam as are the magnet-wrap shown in FIG. 21 and clasp-wrap shown in FIG. 24. Patch-magnets fastened to the outer layers of a discrete organ such as a kidney or the spleen can be used to draw a drug, and/or other therapeutic substances irradiating or not from the bloodstream into the parenchyma. For this purpose, biocompatibly encapsulated neodymium iron boron is strongly magnetized in a patch-magnet of the maximum dimensions as avoids significant encroachment on the surrounding tissue. Drug delivery by minispheres and nanoparticles is already well developed.

Magnets to remain in place indefinitely are internally undivided, whereas those to disintegrate as part of an absorbable implant consist of magnetized particles, ordinarily containing neodymium iron boron, bonded together but separately encapsulated for chemical isolation following disintegration with clasps made of absorbable material such as those specified in the section below entitled Stent-jacket Expansion Inserts, which enumerates substances that spontaneously disintegrate over a shorter period through hydrolytic and enzymatic action and long-term materials to be broken down by lithotripsy. Fastened at any level along the digestive tract the heart, or other organ, for example, by introducing the prongs or clasps through the outer serosal or pericardial layer, a clasp-magnet will trap and hold miniballs that incorporate sufficient ferrous or magnetically susceptible matter passing through the lumen.

While more quickly placed than an impasse-jacket to perform this function, the clasp-magnet is not configured to allow extraction with the aid of a powerful external electromagnet. In such use, the clasp-magnet or magnets can detain miniballs that are absorbable or contain a drug precursor released when exposed to a chemical activator or heat, for example, with others downstream holding miniballs that release a reversal agent when similarly activated, as addressed above in the section entitled Concept of the impasse-jacket and below in the section entitled Miniball and Ferrofluid-impassable Jackets, or Impasse-jackets, among others.

Clasp-magnets are used to effect a structural adjustment such as ductus patenting, ductus deflection, or tissue deflection in combination with any other implant described herein and with drug carrier bound nanoparticles ordinarily delivered in a ferrofluid to attract the drug into the substrate tissue. Used structurally, clasp-magnets placed circumtracheally to treat tracheal collapse can be situated suprapleurally or subcutaneously. Used for drug targeting, clasp-magnets are attached to the outside of an organ to draw drug carrier nanoparticles from the blood or other contents passing through a lumen, such as along the gastrointestinal tract.

These drugs are typically antineoplastic, and whether antimycotic (mycetogenetic, antifungal, fungicidal), antibacterial (bactericidal), antiprotozoal, antiviral (viricidal), antihelmintic (anthelminthic, anthelmintic, vermicide, verifuge), or broad-spectrum antibiotic or anti-infective, where the infection is localized to or concentrated in the organ, whether a background systemic dose, often reducible responsive to such targeting, is also administered. While muscle fascia is ill-defined from the subjacent epimycial fascia, so that pinching skeletal muscle fascia does not, for example, lift the fascia away from the underlying muscle, the integument is substantially free to move in relation to underlying skeletal muscle.

That is, the integument is loosely attached as to easily slide over the underlying muscle, which is stable in average position relative to the skeleton. Therefore, a thin permanent magnet with rounded corners that project at the top and sides attached to the muscle fascia moves with the muscle, the internal surface of the integument freely sliding over it. Like magnet-wraps, clasp-magnets are generally at a distance from the implants to be attracted, and therefore incorporate discrete permanent, rather than intrinsic, quasi-intrinsic, or laminated magnets, as described above in the section entitled Types of stent-jacket, which are, however, no less applicable in closer placement. The use of a moisture barrier-coated viscoelastic polyurethane foam lining in a patch-magnet depends upon the presence of microvasculature or nervelets on the surface of the substrate tissue.

A primary application of clasp- or patch-magnets is attachment to the surface of an organ to attract drug carrier nanoparticles from the blood, thereby overcoming the need to find substances that are naturally drawn to the organ as is iodine to the thyroid gland, for example. Natural attraction has the advantage of being noninvasive; however, the practical application of this approach depends upon the development of substances spontaneously drawn to the target organ. This use of clasp-magnets is addressed above in the section entitled System Implant Magnetic Drug and Radiation Targeting. In FIGS. 25 and 26, a patch-magnet is shown mounting a tiny permanent magnet, that is, as extrinsically magnetized, rather than in the form of a clasp made of intrinsically magnetized material.

While clasp-magnets can support a lesser strength of magnetization for use in stent-jackets, for example, where the magnetic energy product, or magnetic field strength per unit mass, of neodymium iron boron permanent magnets serves miniaturization for unobtrusiveness, here this material is used as much to produce a strong field to attract over a distance or to draw magnetically susceptible drug carrier nanoparticles from the blood or other luminal contents. Clasp-magnets as most of the other system components described herein can be provided in a form sufficiently disintegrable to be described as absorbable where dissolution of a chemically isolated encapsulated residue poses no problem.

The stent-jacket shown in FIGS. 1 thru 6 and 13 and the magnet-clarity wrap shown in FIG. 21 are likewise shown with permanent magnets mounted not only for illustrative but because the aligned domains within an integral permanent magnet allow for greater field strength essential to attract the susceptible implant over a distance. In actuality and in particular, when less field strength is required, intrinsically and quasi-intrinsically magnetized components, as defined above in the section entitled Types of stent-jacket, which are compact and free of protrusions, are used. Thus, the magnet-wrap shown in FIG. 21 might incorporate magnetized beads woven onto the backing, for example. Unless the permanent magnets are very small to include encapsulation for chemical isolation, clasp-magnets and magnet-wraps using these are not made to be absorbed.

Clasp-magnets for use with adjacent tissue can be produced in laminated form with an intrinsically or quasi-intrinsically magnetized layer, radiation shield, or absorbable radiation shield, as addressed above in the section entitled Noninvasive dissolution on demand of absorbable stent-jackets, base-tubes, radiation shields, and miniballs. The dissolution of any absorbable implant or part thereof can be used to release a drug or other therapeutic substance. Whether suspension is by means of patch-magnets, implants, or jackets, to avoid placing disruptive forces on the anterior (ventral) wall of the esophagus, the strength of the magnetic pull should be no greater than is necessary to prevent the dorsal membrane from being drawn down by the tidal flow of respiration.

A collapsed bronchial ceiling can thus be suspended using subcutaneous clasp-magnets, or patch-magnets, situated over the affected membrane to draw implanted miniballs or stays out of the lumen. In dogs, with collapsed bronchi, the insertion of ductus-intramural implants and patch-magnets involves little trauma and eliminates the need for endoluminal stents that must be reexamined and cleaned or replaced often. To accomplish the same end surgically requires a throracotomy. The magnets must be positioned so that the esophagus limits the distance that the tracheal ceiling can be drawn, and lung tissue limits the distance that the bronchi can be drawn and selected for a pulling force that effects suspension without imposing unnecessary force on these limiting tissues.

In such application, the magnets are attached to the outside of the skeletal muscle or to pleura above the bronchi to run parallel with the underlying miniball implants. Since the subcutaneous implants are more readily interchanged to ascertain the best strength magnet to use at points superjacent to the miniballs, the internal implants are generally placed first and the magnets placed thereafter. Since the miniballs are implanted with the patient supine, and have little mass, collapse is not aggravated during the interval until the magnets have been placed. Unless there has been asphyxiation, it should be possible to perform the implantation in one an initial procedure, and placement of the magnets in another. By pressing the magnets down to the level these would occupy once attached, this can be accomplished before incision.

Just before closing, the area surrounding the prongs is treated with a long-effect local anesthetic, such as lidocaine (lignocaine; Xylocaine®). Prongs 36 are preferably made of elgiloycobalt-chromium-nickel steel and perforated or deep-textured for tissue infiltration and wetted with phosphorylcholine, for example, to suppress an adverse tissue response. Retention of the clasp-magnet is mechanical and without the aid of an adhesive. While the opposition of the prongs toward either end of the clasp-magnet, or patch-magnet, makes dislodgement improbable, the prongs can also be coated with a solder that encourages tissue infiltration, the solder denatured by warming the patch-magnet once placed the efficacy of using a laser to denature the solder contingent upon the number and position of the prongs.

Because it immediately surrounds the affected ductus and inherently but flexibly limits wall excursion, when not otherwise contraindicated, the use of subadventitially implanted miniballs with a stent-jacket is preferred to alternative methods such as the use of a miniball jacket with stent-jacket, minimagnet with a miniball jacket or with implanted miniballs, or subcutaneous or superpleural magnets. Where a stent-jacket cannot be used, such placement can afford a suitable location for peripheral magnets to act upon more deeply implanted miniballs. Subcutaneous placement also allows retrieval with relatively little difficulty, but may require preventing the patient from lying beside some objects made of ferrous metal, such as a filing cabinet.

Referring now to FIGS. 24 and 25, shown is a patch-magnet or clasp-magnet that incorporates disk magnet 34 for attachment to the muscle fascia or pleura. The magnet 34 is bonded to subjacent strips 35, preferably made of an austenitic stainless steel such as 18-8, 304, or 316, cold-worked to full hardness to induce shape-memory or restorative force so as to act as a small nonmagnetic leaf-spring. These strips 35 run beneath and in tangential relation to the magnet 34 along its undersides and are cambered, with the magnet surmounting the center convexity on the upper surfaces. In manufacture, the die cut includes perforations in parts to contact tissue, especially the clasps, which typically penetrate the substrate tissue to a depth of 3-4 millimeters, which is intended to allow tissue infiltration and integration for increased retentive tenacity.

Since these elements will be completely encapsulated and isolated within a bioinert plastic jacket, the adhesive used to bond these elements pending encapsulation is not significant, but can be, for example, a cyanoacrylate cement or Loctite Hysol Cool Melt®, or a DYMAX Corporation 200-CTH-series cement. The encapsulated magnets are consistently mounted to the strips with either the north or south poles directed downwards. As is seen in FIG. 25, strips 35 end in recurved tines or prongs 36 with pointed sharp ends sized and configured for fastening the patch-magnet to the surface of the overlying fascial sheet by no deeper than to undercut and catch hold of or clasp the superficial muscle fascia, innervation avoided, causing the patient the least discomfort.

In use, an incision is cut into the integument only so large as necessary to introduce the magnet, which is then positioned, and pushed down, depressing the leaf spring supports. Upon releasing the downward force on the magnet, the leaf-spring seeks to recover to the curved form, engaging the end-prongs under the fascia. Some force on the prongs and possibly pinching of the fascia when the magnet is set in place are necessary to fully engage the prongs. The prongs stimulate the generation of cicatricial (scar) or fibrotic tissue that uninnervated, is numb, and sufficiently tough, resists shear, preventing further incision and discomfort. However, if following a suitable interval for healing, irritation due to the prongs persists, then the subcutaneous or suprapleural magnets are removed and the determination made whether to suture these in place would remedy the problem.

If not, then esophageal tacking (magnetic esophageal tracheopexy) to a magnet-wrap as described above is accomplished. The bonded magnet 34 and strips 35 unit is then encapsulated by dip-coating in a plastciser free nondegradable, hence biocompatible plastic, such as polyvinyl chloride, which depending upon finer chemical details, has a melting point that ranges from 175 to 212 degrees Fahrenheit, or highly polymerized (high molecular weight) polypropylene with a melting point of 320 degrees Fahrenheit. These are sub-demagnetizing melting points for the neodymium iron boron magnets, which depending upon the exact lanthanoid material, have a Curie temperature of around 590 degrees Fahrenheit.

The higher melting point of polypropylene has the additional advantage of allowing the maker to sterilize the magnet-patch by steam autoclave before placing it in the sterile package. The previously presumed nonbiocompatibility of the plasticizers used to make phthalate esters and polyvinyl chloride pliable has since been discredited by the American Council on Science and Health 1999 and the European Commission on Health and Consumer Protection Directorate-General 2002. In manufacture, once cured, the incisive ends of the prongs are exposed (denuded) by stripping away this coating. To gold anodize more than the exposed prongs of the unitized magnet with clip mounting prior to dip-coating is considered redundant for use in this subcutaneous environment, which in a patient free of subcutaneous disease, is substantially noncorrosive, nondegradative, and pathogen free.

II2. Chemical Isolation of Patch-Magnet and Other Implanted Components

Encapsulation to impart bioinertness to the miniballs, stent-jackets, miniball-magnets (magnetized miniballs; magnetized spherules) and subcutaneously or suprapleurally implanted patch-magnets (clasp-magnets) described in connection with extraluminal stenting is accomplished by overlayment with gold, tantalum, titanium, or a bioinert plastic polymer resin applied by dip-coating or lamination between sheets. Encapsulation to chemically isolate toxic inclusions is addressed in relation to clasp- or patch-magnets as usually incorporating a larger volume of magnetized; such matter must always be isolated. This is no less true when the material is incorporated as discontinuous to allow breakdown in an implant otherwise absorbable. The radiopacity of the miniballs notwithstanding, the tiny size of these encourages improvement through the addition of an outer coating of tantalum.

The further encapsulation of the tantalum layer with a medium, such as starch or sugar-based, for delivering medication upon dissolution does not detract from radiopacity. Of the various methods for applying a coating of gold to these components, conventional electrolytic barrel plating may produce a microporous surface not entirely free of plating bath solution chemicals (see Sahagian, R. 1999. "Critical Insight: Marking Devices with Radiopaque Coatings," *Medical Device and Diagnostic Industry Magazine*, Canon Communications, May 1999), in which case the coating fails to provide the biocompatibility that was its object. The materials and chemical isolation of the various components described herein are further addressed under the section devoted to each. Processes used to apply coatings to stents that are applicable to the coating of miniballs include, for example, ultrasonic spray technology such as the MediCoat and MicroMist systems developed by Sono-Tek Corporation, Milton, N.Y.

III. Magnet-Wraps

A magnet-wrap or magnet-jacket such as that shown in FIGS. 22 thru 24 is configured as is a stent-jacket in as many types but is generally larger with a shape-nonretentive or stretchable, such as spandex, backing. If laminated, the magnetized layer when not itself stretchable is segmented to allow expansion, putting it in the discretely magnetized category, as addressed above in the section entitled Types of Stent-jacket. A magnet-wrap can be used as can a stent-jacket, to attract susceptible implants or passing particles which it encircles or that lie outside and at a distance from it; however, the use of a magnet-wrap to attract encircled matter limits the pliancy of the backing, which is urged toward the susceptible matter and limits the field strength that can be used.

The magnetic poles along the wrap are usually uniform in orientation. The magnet-wrap is intended primarily for application of its radially outward tractive force on distant ferromagnetic implants using the ductus it encircles as a mounting platform. Concurrent use to treat the encircled ductus must coordinate the force requirements for these different functions. In unusual situations where the axially outward, or abaxial force of the inwardly, or adaxially directed poles of a stent-jacket and the axially inward, or adaxial, function of the outwardly or abaxially directed poles of a magnet-wrap are both desired, the relative prominence of either function and site suitability will determine which type jacket is to be used. Exceptionally, a magnet-wrap used as a cuff about an arm or leg, for example, is configured as a magnet-wrap even though it functions as a stent-jacket.

External placement avoids the need for dissection to locally encircle the ductus, usually an artery or vein. This is especially the case when relatively large magnets are needed to draw drug carrier particles from the blood into the ductus wall for a limited time, after which the cuff is removed, Magnet-wrap function is addressed above in the section entitled Concept of the Magnet-wrap. A magnet-wrap looks like a small cuff and is secured about the ductus used as a mounting platform by means of hook and loop straps. It is used, for example, when intervening structures preclude the use of suture to pull along the direction desired and when subcutaneous or suprapleural patch-magnets or clasp-magnets, addressed below in the section entitled Clasp-magnets, cannot be positioned as desired.

III1. Use of a Magnet-Wrap

Considerations that pertain to the fitting of a magnet-wrap to the substrate ductus are discussed in the previous section entitled Jacket End-ties and Side-straps. The dimensions of magnet-wraps vary with the size of the ductus to be encircled. For most blood vessels, magnet-wraps are fifteen millimeters in wrap around length and provided in two millimeter increments and generally mount bar magnets that exert a tractive force proportional to their dimensions. The width of the magnet-wrap is determined by the length of the segment of the substrate ductus to be encircled. The magnetic suspension of a collapsed dorsal tracheal membrane is discussed in this section, as well as those below entitled Subcutaneous and Suprapleural Clasp-magnets (Patch-magnets, Treatment of Tracheal Collapse in the Cervical Segments, i.e., Cephalad, or Anterior, to the Thoracic Inlet, and Use of a Magnet-wrap about the Esophagus to Treat Tracheal Collapse in a Small Dog.

The magnet-wrap is selected according to the circumference and length of the substrate support ductus to exert the minimum tractive force sufficient to attract the miniballs over the gap present. The tightly rolled magnet-wrap is inserted through a local incision or trocar portal. It is then unrolled and wrapped about the substrate structure only so taut that the elastic webbed surgical gauze 19, preferably made of polypropylene (Prolene®) is not impeded from compliance to the smooth muscle movements of the substrate vessel or duct and so that the magnets are directed toward the target implants. Finally, the paper release strip is stripped away from the hooks or loops, and end-flaps 24 are wrapped around the underlying substrate structure securing the magnet-wrap in place, the webbed texture of the gauze also assisting to reduce the risk of migration.

When necessary, adding end-ties of hook and loop backed by loosely braided multifilament spandex fabric specially woven for breathability elastomer strapping, or as described in the section on stent-jackets above, Durasil® suture (not shown), affords added resistance to migration. It is considered obvious that the attracted and attracting parts, herein magnets and ferromagnetic pieces, such as in any wrap device described herein, could be reversed in position to obtain a similar if not identical result. In man, esophageal tracheopexy (tracheofixation) for tracheal collapse, if not magnetic, is not without precedent (see, for example, Masters, I. B. and Chang, A. B. 2005. "Interventions for Primary (Intrinsic) Tracheomalacia in Children," *Cochrane [Online] Database of Systematic Reviews* 19(4):CD005304; Cohen, D. 1981. "Tracheopexy—Aorto-tracheal Suspension for Severe Tracheomalacia," *Austrailian Paediatric Journal* 17(2):117-21; Morabito, A., MacKinnon, E., Alizai, N., Asero, L., and Bianchi, A. 2000. "The Anterior Mediastinal Approach for Management of Tracheomalacia," *Journal of Pediatric Surgery* 35(10):1456-1458).

Such can be accomplished by suspending the dorsal membrane of the trachea once implanted with ferrous miniballs or stays from the esophagus, whether the latter is provided with a magnet-wrap as preferred or has magnetized miniballs or stays implanted. While unconventional, a magnetic esophageal tracheopexy to treat collapse or strictures of the airway seen in small dogs and small horses, for example, as cited in the section above entitled Magnetic Correction of Airway Collapse and described beginning with the section below entitled Treatment of Tracheal Collapse in the Cervical Segments, i.e., Cephalad, or Anterior, to the Thoracic Inlet, has precedents in esophagopexy (esophagofixation), tracheopexy, and the use of the esophagus to patch a tracheal defect to treat many different conditions (see, for example, (Han, Y., Liu, K., Li, X., Wang, X., Zhou, Y., and 6 others 2009. "Repair of Massive Stent-induced Tracheoesophageal Fistula," *Journal of Thoracic and Cardiovascular Surgery* 137(4):813-817; Freeman, D. E. 2005.

"Surgery for Obstruction of the Equine Oesophagus and Trachea," *Equine Veterinary Education* 17(3):135-141; Lillich, J. D., Frees, K. E., Warrington, K., van Harreveld, P. D., Gaughan, E. M., and Beard, W. L. 2001. "Esophagomyotomy and Esophagopexy to Create a Diverticulum for Treatment of Chronic Esophageal Stricture in 2 Horses," *Veterinary Surgery* 30(5):449-453).

The trauma associated with the implantation of sterile miniballs in the esophagus to accomplish a magnetic tracheopexy over the course of the esophagus dorsal to the trachea where no injury or pathology had affected the esophagus is too discontinuous to result in odynophagia, chest pain, or fibrotic or cicatricial contracture and stricture as more expansive infection and serious injury can produce in horses, for example (see, for example, Waguespack, R. W., Bolt, D. M., and Hubert, J. D. 2007. "Esophageal Strictures and Diverticula," *Compendium: Equine Edition* July/August 2007; Todhunter, R., Stick, J. A., Trotter, G. W., and Bowles, C. 1984. "Medical Management of Esophageal Stricture in Seven Horses," *Journal of the American Veterinary Medical Association* 185(7): 784-787).

Extraluminal stenting of Esophageal strictures following injury, much as a sabre trachea, will usually prove too resistant to alleviate by means of stenting (see, for example, Waguespack 2007 op cit: "Chronic strictures usually have progressed too far, and the cicatrix is too firm to yield to dilation;" Lillich, J. D., Frees, K. E., Warrington, K., Van Harreveld, P. D., Gaughan, E. M., and Beard, W. L. 2001. "Esophagomyotomy and Esophagopexy to Create a Diverticulum for Treatment of Chronic Esophageal Stricture in 2 Horses," *Veterinary Surgery* 30(5):449-453; Craig, D. and Todhunter, R. 1987: "Surgical Repair of an Esophageal Stricture in a Horse," *Veterinary Surgery* 16(4):251-254; Nixon, A. J., Aanes, W. A., Nelson, A. W., and Messer, N. T. 1983. "Esophagomyotomy for Relief of an Intrathoracic Esophageal Stricture in a Horse," *Journal of the American Veterinary Medical Association* 183(7):794-796). Since if extended, the tracheopexy may induce esophageal dysphagia, the length is limited to only the obstructive portion of the dorsal ligament, or membrane. The flaccid dorsal membrane of the trachea should accommodate the passage of a bolus and prove an annoyance only then. Placing the implants aside of the membrane minimizes stretching. The field force is set to allow more pronounced distention of the esophagus to momentarily separate the two.

III2. Magnet-Wrap Structure

As shown in FIG. 21, which shows the inner or substrate ductus-directed face of a discrete magnet magnet-wrap and a vertical section therethrough as seen edge on to its left side as drawn, that is, with the outer surface facing toward the left hand side, a magnet-wrap mounts magnets 18 that for minimum size, hence, least obtrusiveness or encroachment upon neighboring structures, are preferably made of high energy product sintered neodymium iron boron which have been encapsulated for biocompatibility as described below in the section on miniballs. A magnet-wrap to be placed about a ductus with an external or adventitial tunic with microvessels or nerves that must not be subjected to sustained compression must be provided with a moisture barrier-coated viscoelastic polyurethane foam lining, which is included in FIG. 21.

Four magnets 18 are shown only in an exemplary sense, the size, number per unit area, and shape of the magnets of sintered neodymium iron boron core for the maximum tractive force-to-magnet mass and size ratios all varying according to the application. Regardless of shape, magnets 18 are fixed in position by the same running stitch 23 which is reversed to fill in gaps of the first run for added strength, thus binding together the four plies of the magnet-wrap, two behind and two in front of the magnets. The backing or bandage portion of the magnet-wrap must be sufficiently elastic to move with the outer surface of the substrate ductus without loosening, bunching or migrating. Stitching 23 preferably consists of nonabsorbable synthetic, strength retaining, nonallergic thread or suture, single strand, or monofilament, to discourage colonization, preferably made of polypropylene (Prolene®) or nylon (Ethilon®) suture.

The two layers or plies to the rear (facing inside; toward the outer surface of the substrate support ductus) consisting of soft and elastic nonabsorbable, nonallergenic, and colonization-resistant fiber-based gossamer grade woven surgical gauze 19, preferably made of polypropylene. The inner of the two outer layers consists of a loosely braided multifilament spandex fabric layer 20 that is specially woven for breathability. The outer layer consists of a breathable biocompatible fabric, such as an open nylon webbing. The inner surface of the outer layer, which serves to wrap around the ductus and secure the magnet-wrap on the side opposite the magnets, is divided to omit the portion of the underlying spandex layer 20 that overlies magnets 18.

The portions of the outer layer divided thus are stitched against the outer surface of and toward the ends of spandex (elastane, Lycra®, Linel®, Elaspan® and Dorlastan®) layer 20. Small loops 21 on the outside (facing away from the outer surface of the substrate support ductus) and hooks 22 mounted on backing 24, usually made of nylon (polyamide, Zytel®) on the inside (facing toward the outer surface of the substrate support ductus) allow the end-ties or the two portions of the outer layer to be wrapped entirely around and securely fastened behind the substrate ductus. A silicone or wax coated paper release strip (not shown) is applied by means of a thin layer of an adhesive with low bond strength, such as corn starch, to either the hooks or loops to prevent unintended fastening during placement.

IV. Clasp-Patches and Clasp-Wraps

IV1. Creation of a Magnetically Retractable Surface Layer

Clasp-wraps (clasp wrap-surrounds, clasp-jackets, clasp-bandages) are bandages or wrap-surrounds with ferromagnetic clasps for engaging the outer tunic or tunics fastened to the inner surface. A clasp-wrap is used to encircle a larger ductus that due to disease, has collapsed or become stenostic and malacotic in its outer layers. A clasp-patch does not wrap around the ductus but is rather a local patch for fastening to the underlying tissue whether fascial, adventitial, fibrosal, capsular, or pericardial, for example. Clasp-wraps and the more localized clasp-patches are in effect artificial adventitial or fibrosal tunics, or outer capsules, lined when necessary with viscoelastic polyurethane foam to protect small vessels and nerves and with ferromagnetic clasps for fastening to the underlying tissue so that tissue can be magnetically retracted.

While stays have many uses unrelated to stenting, a clasp-wrap essentially duplicates the function of wide stays used for stenting that are fastened to a mantle or wrap-surround for encircling larger ductus to prevent pull-through of the ductus-intramural implants under the magnetic tractive force used to retract or distend and maintain the patency of the ductus. Absent the means for inducing tissue infiltration and adhesion described herein, miniballs have the least retentive potential, that is, the greatest propensity toward pull-through. Placing a miniball, then surrounding the ductus with a nonconstrictive elastic wrap compresses the tissue overlying the miniball, and reduces the tendency toward delamination.

Wetting the miniball with cement achieves adhesion only to the tissue in direct contact with the miniball without adding strength to the surrounding tissue. Additionally coating the inner surface of the wrap with a tissue hardening agent will make the overlying tissue less yielding or penetrable, reducing the tendency toward pull-through. Finally, fastening the miniball to the inner surface of the wrap by means of a small arm or clasp would impart additional retentive strength in relation to the tractive force imposed by a retracting magnet. However, the miniball is configured for ballistic insertion, making it less resistant to pull-through, and is introduced from within the lumen, making connection or bracing thus unfeasible. Stays have extension circumferentially and longitudinally to present significantly greater surface area for retention and attraction than does a miniball, and stays are introduced from outside the lumen.

However, inserted at an off-circumferential angle, connection to an arm perpendicular to the plane of entry following insertion followed by connection of the outer end of the arm to the inner surface of a wrap-surround is not feasible. Alternative approaches for imparting tunical integrity sufficient to allow retractive stenting are addressed below in the section entitled Clasp-wrap-Alternative Methods for Achieving Adhesion to the Outer Surface of the Ductus. FIGS. 22 thru 24 show a clasp-wrap. The clasps are oriented in a pattern that allows undercutting the outer layers of the ductus while mildly urged by the spandex backing in opposition The clasps are configured and can be coated to encourage tissue ingrowth, and the inner surface of the wrap can be coated with a cement that will provide temporary adhesion during tissue infiltration.

In a hypothetical situation where miniballs should not be coated with drugs to encourage tissue ingrowth or a cement and an interval would best be allowed before placement of the stent-jacket in a followup procedure, a clasp-wrap may allow stenting in one procedure. This is not the case with stays, since both the stays and stent-jacket are placed from outside the ductus through the same incision or access portal, which does eliminate the need for transluminal access and disruption to the inner tunics. Among ductus-intramural implants, wide stays, especially when configured with a deep outer texture that provides undercuts and ingrowth channels, have greater retentivity or resistance to pull-through, even without the stays and internal surface of the wrap wetted with an adhesive.

The magnetically susceptible material need not be confined to the clasps but can consist of threads incorporated into the stretchable backing, for example. As shown in FIG. 22, which shows the inner or substrate ductus directed surface-of a clasp-wrap, FIG. 23, which shows one of the ferromagnetic metal or ferrous metal particulate impregnated plastic clasps in detail, and FIG. 24, which shows a clasp in section, mechanical fastening is accomplished through the use of clasps 26, each with a single very sharp prong tip directed downward at an angle for undercutting the more superficial layers of the substrate ductus. In overall conformation, the prong is similar to but usually much smaller than those used in athletic bandages. A moisture barrier-coated viscoelastic polyurethane foam lining for placement about a ductus of which the vascular and nervous supply must not be subjected to sustained compression is shown at the bottom of FIG. 24.

Prongs 26 are preferably made of a magnetically susceptible stainless steel or elgiloy cobalt-chromium-nickel steel and perforated or deep-textured for tissue infiltration and wetted with phosphorylcholine, for example, to suppress an adverse tissue response. The application of a tissue cement is considered unnecessary. While the opposition of the prongs toward either end of the clasp-wrap makes dislodgement improbable, the prongs can also be coated with a solder that encourages tissue infiltration, the solder denatured by warming the clasp-wrap once placed, the efficacy of using a laser to denature the solder contingent upon the number and position of the prongs.

Due to cell turnover, coating the internal surface of such a wrap with an adhesive is a only a temporary measure for achieving adhesion to the adventitia or fibrosa until the clasps become ingrown by the surrounding tissue. The clasp-wrap can be retracted by a stent-jacket or clasp- or patch-magnets positioned about the periphery. The latter usually use larger neodymium magnets and can be positioned at a greater distance. This can be of value when clearance is a problem and/or a clear field is wished preserved for a prospective surgical procedure. The need for a clasp-wrap is usually due to weakness in the outer layers of the substrate ductus as disallows the retention of ductus-intramural implants. Any adhesive used to coat the inner surface of a clasp-wrap must be stretchable when cured.

The clasps used to engage the outer surface of the substrate ductus may be magnetically susceptible, or the intervening material, usually spandex, may be woven of magnetically susceptible coated fibers. When the collapse or stenosis is radially asymmetrical, the clasp-wrap can be made susceptible for use with clasp-magnets, magnet-wrap, or a stent-jacket of like asymmetry or asymmetrical positioning. A claspless wrap-surround incorporating magnetically susceptible and radially asymmetrically might be used to. A clasp-wrap must not arouse an adverse tissue reaction or disrupt autonomic function. Unless woven to be absorbable, of glycolic acid-based fibers, for example, with absorbable clasps of such matter in solid form, the wrap must not disintegrate.

While the clasps themselves are shown as the magnetically susceptible component, a clasp-wrap that incorporated magnetically susceptible matter by coating or lamination with encapsulation for chemical isolation of the toxic material following breakdown is an obvious alternative, as is making clasps and the material of the wrap itself susceptible. Such requires that it be sufficiently elastic to move with the surface during intrinsic and gross movement, and remain permeable to gas and moisture. A clasp-wrap to be placed about a ductus with a fibrosal (external, adventitial) tunic supplied by a microvasculature or nerves susceptible to injury from compression under a wrap-surround must be provided with a moisture barrier-coated viscoelastic polyurethane foam lining.

The use of clasp-wraps and magnet-wraps is subject to the results of the adventitia-media or intra- or inter-laminar separation (delamination) test described below under the section entitled In Situ Test on Extraluminal Approach for Intra- or Inter-laminar Separation (Delamination). As is true of stent-jackets and stays, a clasp-wrap has as one basic object compliance with the intrinsic movement in the wall of the vessel or duct. Clasp-wraps are used with more strongly magnetized components, namely magnet-wraps, patch-magnets, and more strongly magnetized impasse-jackets, and seldom if ever with stent-jackets and magnetized miniballs, stays, and arrays thereof, which are too weakly magnetized to attract clasp-wraps.

Clasp-wraps for temporary use, to include the clasps, are made entirely of absorbable materials such as those specified in the section entitled Absorbable Stent-jacket Expansion Insert Materials with Relatively Short Breakdown Times, among others. A clasp-wrap can be used with a stent-jacket to exert tractive force either eccentrically or entirely around the ductus with equal or different tractive forces over different arcs. Retracted by means of a distant rather than encircling source of magnetic attraction, such as a magnet-jacket (magnet-wrap) or a subcutaneous or suprapleural clasp magnet or by a plurality or some combination of these, the attractive field is angularly limited and therefore eccentric. When the ductus is malacotic (softened, weakened), miniballs and stays with too little contact area to adequately distribute or divide the force of attraction are likely to pull through.

When the malacia or intra- or inter-laminar separation (delamination) is superficial (peripheral, adventitial), the use of a conventional (endoluminal) stent (because it is medial or deep to the diseased outer layers) is indicated. When the diseased tissue is more medial (deeper in relation to the outside surface), an endoluminal stent should be avoided. A diseased ductus that is not implantable without perforation, pull-through, or intralaminar separation or delamination using less densely spaced apart implants can sometimes be grasped about through use of a clasp-wrap, which more evenly distributes the tractive force and thus is better able to resist detachment. Such use is especially appropriate where the ductus wall will remain in need of support after healing with the weakened condition having subsided, where the use of a wrap-around graft of stronger tissue would demand much time to heal, and an anastomotic graft would pose a risk of leakage as well as take time to heal.

More specifically, to avoid a lengthy preliminary interval for healing before a second procedure to implant miniballs or stays can be performed that the urgency of the condition may not allow, such a synthetic exogenous patch material is preferable to even an autogenous graft. Furthermore, any donor tissue would have to exhibit the properties of strength and elasticity substantially unique to the type tissue of the ductus. Made entirely of nonallergenic synthetics, a stent-jacket likewise requires no antecedent procedure and poses no risk of rejection. Without a second operator to harvest the donor tissue, the use of synthetic materials saves even more operating time as well as avoids specifically harvesting trauma. Approaches that would so strengthen the outer layers of a diseased ductus that miniball or stay implants could be used without the need for a clasp-jacket require further development.

These include a bioinert penetrating and hardening resin for wetting the outer surface of the ductus that would have sufficient pliancy upon curing as not to interfere with autonomic motility, and the use of radio frequency treated collagen (see, for example, Shields, C. A., Schechter, D. A., Tetzlaff, P., Baily, A. L., Dycus, S., and Cosgriff, N. 2004. "Method for Creating Ideal Tissue Fusion in Soft-tissue Structures Using Radio Frequency (RF) Energy," *Surgical Technology International* 13:49-55; Mohr, L. G. Jr. and Edwards, S. D. 1999. "Treating Aneurysms by Applying Hardening/Softening Agents to Hardenable/Softenable Substances," U.S. Pat. No. 5,921,954 (expired Jul. 16, 2003 for nonpayment of maintenance fees). The many tissue fixatives developed for microscopy do not exhibit both the pliancy and tissue compatibility essential for the present purpose.

Provided the ductus is not too malacotic, a clasp-wrap with a sufficient number of ferromagnetic clasps per unit area to undercut the outer layers of the ductus, especially when bonded to the surface of the ductus with a stretchable tissue adhesive and devised to allow tissue infiltration to compensate for the inevitable breakdown in the adhesive over time, can adhere longer than is allowed through the use of an adhesive alone. In the adverse chemical milieu inside the body, an adhesive breaks down quickly when the surface of the tissue to which it is bonded is replaced through normal cell turnover. Considerations pertinent to the securing of a clasp-wrap to the substrate ductus are addressed above in the section entitled Jacket End-ties and Side-straps.

The clasps alone are used to retain the clasp-wrap against the outer surface of the ductus; alternatively, the clasp-wrap, to include the prongs, can be coated entirely with an adhesive, preferably one that exhibits elasticity upon curing, or partially with an adhesive and partially with phosphorylcholine to reduce tissue reaction, or provided with hook and loop extension at either side to assist in retention. Clasp-wraps generally do not require supplementary stabilization by means of side-tethers as might stent-jackets. Synthetic and cleaned of any polymerization or environmental contaminants, spandex elastomer, which is a block copolymer of polyurethane segments alternating with segments of polyethylene glycol, is non-sensitizing and nonallergenic. A spandex backing to comply with expansion and contraction in the substrate ductus is applied for the quiescent diameter and can be used to expedite far side clasping on placement. As seen in FIG. 22, the clasp groups are oriented in opposition.

This not only produces a secure attachment once placed but facilitates placement by allowing the operator to pull at the ends with the spandex backing stretched while moving the wrap behind the ductus from side to side so that all clasps will remain engaged when the wrap is released. Care must be given to not stretching the backing to the degree that the ductus will be compressed while quiescent. Alternatively, the operator can pull at one end so the restorative force assists to engage the clasps with points facing in the same direction. Where the substrate structure is a cord or sheath of constant diameter, the restorative force of the spandex backing is used only to expedite clasping during placement and not for compression. As shown in FIGS. 21 thru 23, the clasp-jacket is made of layers of spandex or elastane 24. Spandex is sold under the trade names of Lycra®, Linel®, Elaspan® and Dorlastan®.

Such material is less susceptible to microfracture and brittleness over time than is natural rubber, and is thus able to resist the chemical insults associated with circumvascular placement for a long time. Spandex effectively does not disintegrate in circumvascular placement. It is considered obvious that the attracted and attracting parts, herein magnets and ferromagnetic pieces, such as in any wrap device described herein, could be reversed in position to obtain a similar if not the same result. As shown in FIG. 21, formations of individual clasps are mounted on woven stretchable backing 27 of spandex, which allows air to reach the surface of the substrate ductus. Backing 27 can also be made of plies of spandex alternating with plies of surgical gauze.

Alternatively, the inner surface of the miniball-jacket can be coated with a highly tacky pressure-sensitive hypoimmunologically processed adhesive consisting of a mixture of synthetic rubber, which has high initial bond strength that tends to degrade over time, and pressure sensitive acrylic emulsion polymer adhesive, which tends to increase in bond strength over time. Improved breathability is obtained by introducing small perforations in the backing. For such an adhesive to bond well may require that the outer surface of the ductus be dried with a blow dryer or by swabbing with an absorbent cloth. Clasps 30 with mutually facing prongs can be arranged in different formations, to include placing all facing in one direction as a group on one side of the internal surface with those facing in the opposite direction on the opposite side of the internal surface, or in rows wherein the prongs of adjacent clasps face one another in pairs.

As shown in FIGS. 22 and 23, an individual ferromagnetic clasp consists of a single prong 26 bent when die-cut to be continuous with a small stoop-like tab containing a hole. The dimensions of the stoop-tab 29 are determined by the properties of the spandex (elastane) or other stretchable and breathable clasp backing material 27 used, being made large the softer, more pliant so that the clasp is overly inclined under the tractive force of the magnets, and more subject to being torn is the intervening material. Rivet 28 is passed through this hole, through the intervening spandex sheeting and a flange cover-plate on the outer surface. Tab-stoop of prong 26, flange cover-plate 25, and rivet 28 thus cooperate to clamp spandex layer 27 and fix prong 26 in position.

The prongs, which depending upon the condition of the ductus are chosen in length to penetrate the adventitia or media (but not perforate into the lumen), are textured and fenestrated or punched to encourage tissue infiltration and are encapsulated for bioinertness as specified in the sections on miniballs and stays. Flange cover-plate 25, to include fenestrae and bends, and prongs 26 are die-cut, the angle of the bends varying with the overall dimensions according to the type substrate ductus and depth of penetration desired. Whereas a magnet-wrap need not firmly adhere to the outer surface of the neighboring ductus it mantles about, a clasp-wrap must adhere to the outer surface of its substrate ductus immediately upon placement despite magnetic traction on the clasps. To prevent irritation to the substrate ductus, all surfaces of the clasps facing inward, and to prevent irritation to neighboring tissue, all surfaces of the clasps facing outward, must be flat and smooth.

IV2. Use of a Clasp-Wrap

The clasp-wrap is inserted through a small incision in the body wall while still tightly rolled, and an adhesive if any lightly coated onto the fascia cleaned surface of the ductus. The clasp-wrap is then positioned perpendicularly to the ductus, stretched only enough to allow the prongs to fully engage the outer layers of the ductus without perforating into the lumen or restraining the intrinsic motility, then pushed down gently with a fingertip to assure good contact and adhesion. Provided the ductus is motile upon application, the use following the clearing away of diffuse fascia of a long-chain methacrylate cement in a light film to bond the clasp-jacket to the outer surface of the ductus need little impede stretching of backing 27 nor smooth muscle motility; the stretching of backing 27 notwithstanding, adhesion generally succeeds at a sufficient number of points to maintain the bond until such time as tissue integration of the prongs takes over adhesion when this is eventually lost due to tissue replacement. In some instances, the methacrylate is applied with a multi-dot applicator for improved spandex stretch compliance.

IV3. Clasp-Wrap-Alternative Methods for Achieving Adhesion to the Outer Surface of the Ductus IV3a. Stays Configured and/or Coated to Promote Tissue Infiltration and Adhesion Stays are addressed below in the section entitled Arcuate Stays. A malacotic ductus may be unsuited to treatment by ballistic means, and a severely malacotic or otherwise weakened ductus will be untreatable by any of the means and methods described herein with the possible exception of widely configured versions of nonferromagnetic stays with a broken surface to encourage tissue infiltration, adhesion, and cement as described below, all of the other means necessitating some resistance to tractive force applied from without. If endoluminal stenting must also be discounted, then a bypass graft is indicated. When malacia would not allow ballistic implantation but is not so severe or expected to progress to the degree that the wall of the ductus must not be grasped and retained under tension sufficient to maintain patency, then various nonballistic, or stay, methods and means, as addressed below in the section entitled Arcuate Stays, may apply.

IV3b. Injectable Magnetic Fluids

Existing injectable magnetic fluids (not ferrofluids) are meant for temporary use to assist in manipulation during delicate ophthalmic procedures (Dailey, J. P. Phillips, J. P., Li, C.; and Riffle, J. S. 1999. "Synthesis of Silicone Magnetic Fluid for Use in Eye Surgery," *Journal of Magnetism and Magnetic Materials* 194(1):140-148(9); and U.S. Pat. Nos. 6,464,968, 654,636, and 6,612,311). Quickly dissipated, such means are inapplicable for the present purposes. At the time of filing, a bioinert and therefore permanent injectable magnetic fluid was not available.

V. Miniballs

V1. Miniature Ball Implants

Miniballs (miniballs, spherules, minispheres) for use in simple pipe-type barrel-assemblies generally range in diameter from 0.7 to 2.4 millimeters, while those for use in radial discharge barrel assemblies for use other than in the airway range between 0.14 and 2.4 millimeters. With ferromagnetic miniballs, sphericity presents a poor gap for magnetic flux. This is compensated for through the use of neodymium iron boron lanthanoid magnets to attract these. Neodymium magnets afford the highest energy product and thus the smallest size and mass for the field strength exerted. The availability of minute magnets minimizes if not completely eliminates encroachment upon and abrasion against neighboring structures. Discomfort to the patient and the sequelae that can result from chronic irritation are thus eschewed.

At the same time, ballistic implantation, as described herein, is as clean, i.e., as bloodless and atraumatic as possible, while readily lending itself to aseptic delivery. Miniballs to serve as the intraductal component of a permanent extraluminal magnetic stent usually have a solid core of ferromagnetic metal that is encapsulated for chemical isolation. Otherwise, the miniball can contain ferromagnetic pieces dispersed in an absorbable matrix such as sugar where the matrix can include therapeutic substances, such as drugs, and the pieces are shaped to present proportionally more lateral surface area for magnetic attraction but include projections shaped to stop extraction through the adventitia under the magnetic force. Those for temporary magnetic stents have superparamagnetic magnetite or maghemite nanoparticles or finely grained powder dispersed in an absorbable matrix, such as polyglycolic acid.

Miniballs to be infixed at locations from which dislodgement is a possibility, especially along the arterial tree, are secured not only by being wedged in position but by tissue infiltration or by deliberately coating the miniball with an irritant to prompt the body to isolate or entrap the implant much as a cyst, with or without an adhesive outer coating that temporarily fixes the implant in position and contains the substance or substances to encourage such a reaction. Moreover, multiple means will be described for preventing a miniball that despite these measures enters the circulation from forming an embolism. A prepositioned impasse-jacket will arrest and retain a loose miniball mid- or postprocedurally and allow the miniball to be extracted to a safe location or outside the body.

Upon dissolution of the absorbable miniball, the iron is assimilated by the body. Magnetized miniballs can be used to attract drug and/or radionuclide carrier nanoparticles or microspheres, for example. The stenting, or ferrous, component of the miniballs, usually a unitary spherical core, is encapsulated to be biochemically inert, and may be outer-layered or coated with anti-inflammatory, antibiotic, blood coagulation-related, antiangionic, chemotherapeutic, or other medication, with or without a radionuclide or irradiated seed component. Drugs for delivery as miniballs to achieve focused concentration likewise have superparamagnetic magnetite or maghemite nanoparticles or finely grained powder dispersed to allow any mispositioned miniballs to be retrieved.

Absorbable miniballs can also be made to liberate medication during dissolution, and numerous combinations of medication and other type stays are possible. Recovery electromagnets are always situated in the muzzle-head proximate to the points of miniball insertion. Whether for sustained attraction, arrest and/or recoverability if entering the circulation, or for induction heating, virtually all miniballs contain ferrous content. Generally, absorbable miniballs consisting of medicinal or other therapeutic substances contain dispersed superparamagnetic magnetite or maghemite nanoparticles or finely grained powder which is gradually released as the miniballs dissolve, while permanent, or stenting, miniballs contain a core or larger distributed particles of rectangular prismoidal conformation for greater magnetic susceptibility.

Magnetic susceptibility is satisfied with the inclusion of sufficient superparamagnetic magnetite or maghemite nanoparticles or finely grained powder, which presenting a maximized surface area, is absorbed quickly. Incorporating larger grains of iron whether by sintering the powder allows heating a miniball by magnetic or electromagnetic induction. Heat has numerous applications, to include palliative warming of the surrounding tissue, accelerating its healing time, releasing and accelerating the uptake of a drug or other bioactive substance, and effecting and accelerating the disintegration of an absorbable miniball itself. If absorbable, the larger grains whether sintered still present much surface area for relatively quick uptake.

Miniballs for placement along the vascular tree as the intraductal component of an extraluminal magnetic stent have small projections at different angles with an undercut-textured surface which are embedded within a spherical outer casing or jacket such as one containing a sugar which is absorbed following placement. Once anchored by tissue infiltration, a direct blow that crushed or severed the vessel ending the flow of blood therethrough would not dislodge the tissue fused miniball. The site must then be entered for repair, whereupon the miniball is easily extracted with an electromagnet. In FIG. 27, core 37 can be an element in the intravascular component of an extraluminal magnetic stent or medicinal. With a core of either purpose, concentric overlaying layers 38,- 39, and 40 can consist of or incorporate drugs and/or other therapeutic substances, such as a surgical cement.

The section above entitled Field of the Invention and that below entitled Cooperative Use of Impasse-jackets in Pairs and Gradient Arrays, among others comprehend a core 37 which incorporates a resonant circuit responsive to a magnetic field alternating at radio frequency (see Niwa, T., Takemura, Y., Inoue, T., Aida, N., Kurihara, H., and Hisa, T. 2008. "Implant Hyperthermia Resonant Circuit Produces Heat in Response to MRI Unit Radiofrequency Pulses," *British Journal of Radiology* 81(961):69-72, available at http://bjr.birjournals.org/cgi/content/full/81/961/69). When the concentric layers are arranged in least to greatest melting and/or traction dissolution points from the periphery to the center, the layers can be released in this order, an alternating magnetic field used to effect heating and the constant tractive force exerted by the stent- or impasse-jacket, for example, extracorporeally or by remote control thereafter used to draw the drug and/or radioactive nanoparticles to and into the diseased tissue.

The successive layers or shells of the miniballs can be constituted to affect a layer previously released as adjuvant or neutralizing, and successive layers of multiple miniballs, such as held within an impasse-jacket can act on one another thus. Ductus entry and exit pairs can control the medicinal and other therapeutic substance exposure of a delimited segment of a ductus. When each concentric layer incorporates magnetically susceptible drug and/or radionuclide carrier nanoparticles, each layer can be shed in temperature and tractive force order of dissolution by remote control. Specifically, an alternating magnetic field will not only excite a resonant circuit within the core but the nanoparticles in each layer.

Once released within the bloodstream, for example, the constant magnetic tractive force exerted by a stent-jacket, impasse-jacket, or patch-magnet, for example, will draw the nanoparticles against and into the jacketed lesion in the lumen wall. Further to the risk of a release of implants into the bloodstream in the young, stenting temporarily stenosed vessels with an extraluminal stent made of chemically isolated absorbable and absorbable matrix-bound components using absorbable stays demands extraductal entry but avoids the threat of migration due to normal growth (see, for example, Epstein, M. L. 2004. "Does a "Split" Stent Make Sense?," *Catheterization and Cardiovascular Interventions* 62(4):511). The choice of miniballs as implants must consider the profile and strength of the lumen wall following or without an angioplasty.

Methods for testing the lumen wall in situ are addressed below in the section entitled In situ Test on Endoluminal Approach for Susceptibility of the Ductus Wall to Puncture, Penetration, and Perforation. Later degenerative conditions capable of adversely affecting or defeating an extraluminal stent would likely prove equally detrimental with an endoluminal stent. Such conditions include softening of the arteries (arteriomalacia, angiomalacia) associated with heart disease (see, for example, Bouhoutsos, J. and Morris, T. 1973. "Femoral Artery Complications after Diagnostic Procedures," *British Medical Journal* 3(5876):396-399.). The stent-jacket resists aneurysmal distention resulting from untreated hypertension. To defeat the stent, the condition would have to so weaken the tissue of the lumen wall that miniballs could be released out of the vessel through the adventitia, or despite the retractive force of the stent-jacket, into the circulation.

Patients with a degenerative condition that could reduce the retentive strength of the wall tissue may still warrant the use of wider stays before proceeding with a graft. The barrel-assembly includes means such as recovery electromagnets and an embolic filter to prevent the midprocedural loss of a miniball. Additional means for intercepting and resituating to a safe location or recovering a miniball are addressed below in the section entitled Steering and Emergency Recovery of Implants with the Aid of an External (Extracorporeal) Electromagnet. Producing a trajectory or path of insertion little wider than the miniball itself, implantation by such means is least disruptive to surrounding tissue. Cells along the trajectory and its terminus are crushed and release fluid contents; however, this injury is small in extent, highly localized, and the resulting inflammation is medically manageable.

Furthermore, the fluid released lubricates the spontaneous rolling around into optimal polar orientation of magnetized miniballs having a core of neodymium lanthanoid and expedites the delivery of medication from miniballs with an outer coating that contains a drug or drugs. However, implantation by such means requires projectiles that are spherical. As shown in the cross sections of FIGS. 26, a miniball consists of an iron or steel core 37. When tissue compatible, core 37 represents the sum total of the miniball; if not, the miniball is plated with gold, heated, and sputtered to remove contaminants (see Edelman, E. R., Seifert, P., Groothuis, A., Morss, A., Bornstein, D., and Rogers, C. 2001. "Gold-coated NIR Stents in Porcine Coronary Arteries," *Circulation*. 103(3):429-434).

Alternatively, stainless steel tending to afford relatively low radiopacity, the miniball is coated with tantalum, such as with Danfoss Tantalum Technologies Danfoss Coating®, in which case 38 represents the outermost coating, the additional layers in the figure not required. When patient life expectancy justifies the additional expense, the implants are encapsulated in gold, platinum, or tantalum, which are radiopaque. Other than for those having a neodymium lanthanoid core, the encapsulation of implants for bioinertness is precautionary. When the patient is expected to survive for years and the chemical breakdown of core 37 could release a nocuous constituent over time, then the core 37 is encapsulated for bioinertness by overlayment with gold, tantalum, titanium, all of which additionally contribute high radiopacity, or a bioinert plastic polymer resin shown as layer 38 surrounding the core.

Should core 37 be enhanced in radiopacity with a coating of tantalum before encapsulation in a resin for even greater isolation, the tantalum coating is represented by 38 and the resin by 39. If not itself of tantalum, which is bioinert and affords good radiopacity, layer 38 for chemically isolating the core can be coated with an additional layer 39 of tantalum. Still referring to FIG. 26, a steel-core 37 gold plated (layer 38), and microfused (layer 39) miniball may be further coated with a layer of tantalum 40. For magnetic optimization, core 37 is preferably made of a corrosion-resistant ferromagnetic stainless steel, and proportionally large as possible within the thickness constraints of the outer coating materials when present. Ferromagnetic stainless steels include those of 400 series and heavily cold worked 8 percent lanthanoid 316 in CF8M alloy.

Ferritic, martensitic, and to an extent, less austenitic stainless steels can also be used as cores. Since gold plate can present microfractures, unless an outer coating of tantalum already applied for improved radiopacity also fully seals the exterior, a process whereby additional gold is applied to completely seal the core, Microfusion®, is applied, or otherwise, replating, in which case layer 39 represents this layer. In addition to close inspection under a stereomicroscope, microfractures of the electroplated surface can be detected by standardized corrosion protection tests, such as the salt spray or salt fog test (American Society for Testing and Materials Standard B 117) and Kesternich (Deutsches Institut für Normung Standard 50018 or International Organization for Standardization Standard 3231) tests.

Thus, if gold-electroplated, surface contaminants must be eliminated and any voids filled by Microfusion® or vacuum deposition plating, which involve temperatures, typically 70-120 degrees Fahrenheit, well below the 590 degree Fahrenheit Curie or de-magnetizing temperature of neodymium iron boron lanthanoid magnets. An outer coating that consists of a polymer rather noble metal is applied by means of in-situ or matrix polymerization, which methods are widely used in the manufacturing of pharmaceuticals. Gold is of high specific gravity or density relative to water, but in the tiny amounts used, not such as would result in too heavy an intraductal component of an extraluminal stent.

For miniballs and miniball-magnets, however, adjustment in plating thickness allows precision in achieving a certain mass. Combined with variability in the material used to encapsulate these components, some variability in core and wide variability in plating thickness may be applied to achieve considerable exactitude in mass and aeroballistic performance. When the combination of concentric layers as depicted in FIG. 26 or 27 results in a diameter that is too large for the barrel-tubes, consideration should be given to use rotary magazine clips that have been loaded to provide irradiated and/or medication and ferromagnetic miniballs sequentially or in alternation, or miniballs that variously combine layers to provide adequate coverage over the area to be treated.

In the improbable circumstance that such becomes necessary, for arterial and venous application, miniballs must have an outer coating of sufficient tensile and shear strength to withstand stereotactic resituation into safe tissue or if superficial, extraction, as addressed below in the section entitled Steering and Emergency Recovery of Implants with the Aid of an External Electromagnet.

V2. Miniball Types, Radiation-Emitting, Medication, Drug-Eluting Magnetized, and Magnetized Temporary miniature balls and stays can consist entirely of absorbable medication, sealants, or mixtures of these and can be provided with concentric shells of different medications and/or sealants wherein each layer has a prescribed rate of release. Nonabsorbable miniature balls and stays used to deliver radiation at dose-rates higher than could safely be left in place can be coated with absorbable layers of medication or sealants so that only the superparamagnetic magnetite or maghemite nanoparticles or finely grained powder-coated radiation seed would subsequently be recovered, as addressed above under the section entitled Background of the Invention, 4. Necrosis- and atherogenesis-noninducing conformation.

For emergency interception and extraction midprocedurally using a preplaced impasse-jacket or an external electromagnet, sufficient ferromagnetic material must be dispersed throughout an absorbed, to include a drug-releasing miniball, so that its magnetic susceptibility does not degrade with its dissolution to the point where it is no longer extractable. For arrest and extraction, the ferrous material is ordinarily superparamagnetic magnetite or maghemite nanoparticles or finely grained powder; for heat induction, iron grains. Uniform distribution also affords greater iron particulate surface area for absorption and eliminates any need to extract a relatively large core.

Permanently implanted miniballs and stays that are ferromagnetic for use with a stent-jacket or which emit radiation can be overlain with multiple absorbable outer layers of medication and/or sealants, to include the release of genetic material (see, for example, Walter, D. H., Cejna, M., Diaz-Sandoval, L., Willis, S., and fifteen other authors 2004. "Local Gene Transfer of phVEGF-2 plasmid by Gene-eluting Stents: An Alternative Strategy for Inhibition of Restenosis," *Circulation* 110(1):36-45). The preparation of radioactive miniballs, whether for aeroballistic discharge or for bonding between the lining and base-tube of a stent-jacket, for example, can be accomplished by conventional means as used to prepare radioactive seeds or means such as those described by Good in Good, R. R. 1994. "Endocurietherapy," U.S. Pat. No. 5,342,283, with continuation-in-part Good, R. R. 2000. "Endocurietherapy," U.S. Pat. No. 6,099,457.

If necessary, the internal surface of the base-tube is scored or etched, and a suitable adhesive, such as Master Bond EP42HT-2ND2 used to bond the radiation microspheres in the number and type required between the base-tube and the foam lining. Hypothetically, absorbable stays consisting of medication in layers could be used as structural buttresses to support a stenosed or collapsed (malacotic) ductus during and for the purpose of promoting recovery. Any miniball or stay, temporary or permanent, can be coated with absorbable layers of medication, sealants, or combinations of these whether in a given layer. That these various factors as to miniball or stay, permanent or temporary, with or without outer layers of medication, sealants, or both, and so on, might be permutated into numberless specific combinations is considered obvious, as is the fact that different types of intramural implants could be used in a single ductus.

V3. Medication (Nonstent) Implants and Medication-Coated Miniballs, Implants, and Prongs Medication miniballs and stays are not used for magnetic stenting but to concentrate drugs at the treatment site. These consist predominantly if not entirely of medication. The contents may be absorbed entirely, or if an open or closed loop 'smart pill' and/or a radiation emitting seed which has been coated with medication, for example, may not be fully absorbed. Medication miniballs and stays contain sufficient, usually dispersed, ferromagnetic material (almost always superparamagnetic magnetite or maghemite nanoparticles or finely grained powder) to allow recovery if midprocedurally mispositioned, dropped, or lost. By contrast, medicated miniballs and stays are coated, doped with, or contain medication in the form of embedded particulates or microspheres, for example, primarily intended for use in extraluminal magnetic long-term if not permanent stenting.

These consist of a ferromagnetic core often coated with medication and/or other therapeutic substances. Miniballs for temporary magnetic stenting also have superparamagnetic magnetite or maghemite nanoparticles or finely grained powder dispersed throughout an absorbable matrix, which may or may release medication as it becomes absorbed. As addressed above in the section entitled Significance of Antixenic Sterile Tissue Reaction, to delay if not prevent a foreign body reaction, implants and prongs that penetrate tissue to secure implant backings in place are coated with reaction-suppressive substances, such as phosphorylcholine, dexamethasone, and/or curcumin. Except when no ferrous material is included in a medication miniball, the distinction between medication and medicated miniballs depends then, upon the relative proportion of nonferrous to ferrous ingredients.

Whereas the magnetically susceptible core of a medicated miniball for magnetic stenting is proportionally larger and enclosed within thinner coatings of medication, that of a medication miniball requires no more mass of susceptible material than is necessary to allow its retrievability were the miniball improperly placed. Whether in the form of a core or dispersed, the susceptible material included in a medication miniball, generally superparamagnetic magnetite or maghemite nanoparticles or finely grained powder, is usually prepared for complete dissolution so that the medication miniball is completely absorbed. Rotary magazine clips can be loaded to deliver ferromagnetic, medication, or medicated miniballs in any sequence.

Medication miniballs can consist of ingredients that have been interspersed, or mixed, or that consist of concentric layers of medication surrounding a core of another medication or a proportionally small core of ferrous metal. The ferrous core can be powdered for dissolution or encapsulated for magnetic stenting and tissue compatibility once denuded by absorption of the surrounding medication. The core can be an irradiating seed, one or a combination of drugs in the form of powder fused with or without an absorbable outer shell which shell can itself incorporate medication and/or determine dissolution time, and so on. Shot-groups about the rotary magazine clip can include the same or different kinds of miniballs.

The shot-groups can, for example, include miniballs having a ferromagnetic core that is or is not surrounded by medication, layers of different medication, within or not within an absorbable shell of which the dissolution time can be adjusted by altering the thickness or the material of which the shell is made as addressed above in the section entitled Stent-jacket Expansion insert Materials Having Relatively Short Breakdown Times. Controlled dissolution of the medication within a miniball following infixion is preferred to the release of smaller contained miniballs upon impact, which is less predictable and controllable. The delivery of medication squarely into the target tissue in the form of a spherical pill having a dissolution or release time set by means long established in the field of tablet manufacture allows a degree of localization, time release control, and—using the enclosed or torpedo-shaped muzzle-heads described herein—access to lumina of small diameter, which endoscopic injection cannot approach.

Provided the force of impact is tested as described below in the section entitled Pressure Registration Pretest, where the density of implantation is not high and the accuracy of implant location is not critical, medication miniballs can be implanted in the wall of a ductus or the medulla of an organ using a commercial air pistol modified as described below in the section entitled Modification of Commercial Airguns. When delivered through a trajectory of acute angle, the miniball, usually around 0.4 millimeters in diameter, undercuts the intact tissue along a direct path to the point of entry at the surface, and stuck in the proteinaceous exudate liberated from the cells crushed, becomes entrapped, making retrogression within the time until the miniball has been completely absorbed improbable.

When placed subadventitially in a blood vessel where release would result in an embolism, retreat can be prevented by the application of a continuous or discontinuous coating of a solid protein solder as described below in the section entitled Miniballs Coated with a Heat-activated (-melted, -denatured) Tissue Adhesive-hardener or Binder-fixative. Miniballs can be heated from inside the lumen using the heat-windows and heat-generating radial projection tool-inserts in the muzzle-head of the barrel-assembly. That is, the muzzle-head used to place the medication miniballs includes means for heat-denaturing (melting, flowing) this tissue bonding agent as described in the sections herein on heat-windows and 'cooling' (temperature changing) catheters.

Miniballs that lack a ferrous core, instead consisting exclusively of medication, can be used as an alternative option for the parenteral administration of medication where stenting is uninvolved. The procedure for the insertion of miniballs (as opposed to medication stays) completely transluminal, entry at the body surface (to place a stent-jacket) is uninvolved, and magnetic tractive force as might cause a ductus wall to fail by intra- or interlaminar separation (delamination) is thus uninvolved as well. However, the diseased ductus wall may lack strength without the application of force, which longitudinal, could allow overshots that would misplace the medication, and radial, could allow perforations where the absence of a prepositioned stent-jacket would also mean that a protective barrier was lacking.

As to the intrinsic strength of the ductus wall without regard to the application of tractive force, the consequences of misplacement due to excessive travel through a weakened or separated wall, such as medicating healthy tissue that could result in a sum overdose, should determine whether the preliminary test described below in the section entitled In Situ Test upon Endoluminal Approach for Intra- or Inter-laminar Separation (Delamination) is conducted. That a stent-jacket will not have been prepositioned to prevent a perforation, or a double-wedge lined stent-jacket to prevent a perforation or a rebound into the lumen, recommends conducting the test described below in the section entitled In Situ Test on Endoluminal Approach for Susceptibility of the Ductus Wall to Puncture, Penetration, and Perforation.

Spherules consisting of a core and concentric shells for ballistic implantation in the walls of diseased arteries, for example, can be produced using conventional methods in the pharmaceutical industry to include pan tumble coating, centrifugal extrusion, and spray-drying. For most formulations, the vibrational nozzle technique affords superior exactitude of sphericity, which is important for maintaining accurate control over the discharge velocity from the barrel-assembly in proportion to the distance the miniball must transit from the chamber of the airgun to the exit port in the muzzle-head. In every case, medication or tablet miniballs, with or without an encapsulated ferromagnetic or radiation source seed core, must be given an outer coating that will withstand the tangential shear stresses encountered in transmitting the barrel-tube.

In radial discharge barrel-assemblies, the barrel-tubes consist of a fluoro or another low friction polymer, or are lined with a fluoropolymer produced by coextrusion. The crushing-strength, disintegration time, porosity, and friability of tablets relating consistently (see, for example, de Jong, J. A. H. 2005. "Relations Between Tablet Properties," *Pharmacy World and Science* 9(1):24-28), resistance to the smaller impact forces of ordinary handling varies proportionally to the strength required to prevent miniball tablet fracture upon discharge. Discharge and travel through the barrel-tube subject miniball tablets to tangential shear forces that exceed those encountered by tablets in ordinary handling.

To prevent surface fractures, much less overt breakage during discharge, which could not only affect discharge but result in the deposition of debris along the barrel-tubes that might lead to jamming, miniball tablets are strongly compressed as true spheres and may be additionally covered with a fracture-resistant coating, such as an ester bond based bioabsorbable polymer, typically polyglycolic acid, polyester, or poly (p-dioxanone), which to present a low coefficient of friction is further coated with N-laurin and L-lysine. Overlying the core-encapsulating layer that imparts bioinertness in a miniball with a ferrous or lanthanoid core, such as produced by means of gold Microfusion®, miniballs for intraductal stenting can be further encapsulated with medication or contain an irradiating seed as a core.

Irradiating core miniballs are usually conventional seeds with titanium jackets typically lined with a ceramic but in spherical form, that are used apart from stenting function, which would necessitate the incorporation of ferrous material. Some stenosed conditions of a ductus may recommend seeds containing ferrous metal to alleviate the stenosis by means of encircling the ductus with a stent-jacket and to pinpoint the sources of radiation with the same material. A drug-releasing external layer can consist of polylactic acid (Dev, V., Eigler, N., Fishbein, M. C., Tian, Y., Hickey, A., Rechavia, E., Forrester, J. S., and Litvack, F. 1997. "Sustained Local Drug Delivery to the Arterial Wall via Biodegradable Microspheres," *Catheterization and Cardiovascular Diagnosis* 41(3):324-332), a sugar, starch, or syrup coating tumbled to assure sphericity while heat-blown or freeze-dried (lyophilized, cryodessicated).

The addition to implants of adverse tissue reducing substances is addressed above in the section entitled Tissue Acceptance of Ductus-intramural Implants. Neither a medicated coating that encapsulates and is meant to remain with the miniball until implanted nor the fixative cornstarch, rice starch, other syrup, molasses, acacia, methyl cellulose, povidone (polyvidone, polyvinyl pyrrolidone, PVP), or gelatin used to position the miniball in the ring-hole may be friable as to powder and leave a particulate residue along the barrel to any significant degree. Referring now to FIG. 27, some miniballs include all of the layers represented in FIG. 20, to include a core 37 and additional layers 38 thru 40, to which is now further added an outermost coating 41 representing a drug-delivering, drug-eluting, or radiation-emitting medium.

When subjacent layer 40 is a coating of tantalum for enhanced radiopacity, adding a medicated or irradiative outermost coating 41 does not annul this property. Within the overall range for its diameter, adjusting the relative thickness, or varying the relative diameter, of the five layers allows a miniball of specified diameter to be given a specified mass or magnetic susceptibility. Miniballs implanted in arteries can be medicated with, for example, antithrombogenic, anti-inflammatory, or antiseptic medication to reduce the risk and the severity of abrupt closure by spasmodic reflex to ballistic implantation. The addition in manufacture to an irradiating seed with a metallic, such as titanium, outer jacket of concentric shells containing medication by means of air-suspension is limited by the mass of the miniball.

Serious complications have been associated with drug-eluting intraductal stents. Often introduced as secondary endoluminal stents to reduce the reocclusion of a stent placed earlier, time-release drug-eluting stents have been implicated in clotting and restenosis requiring surgery and may lead to death. However, such complications as pain, rash, hives, itching, fever and changes in respiration or blood pressure are likely the result of allergic hypersensitivity to the specific drugs used. Such reactions are maximized when the stent is in the bloodstream, and when intended for local absorption rather than entry into the circulation, the blood level of the drug obtained from an extraluminal stent can be reduced to subclinical. A magnetized miniball, or miniball-magnet, differs from a miniball in having a core made of magnetized material, usually sintered neodymium iron boron rather than iron, steel, alnico, or alternative ceramics.

Owing to the relatively poor magnetic efficiency of a spherical contour, such miniballs must be somewhat larger for a given application than the equivalent ferromagnetic miniball that is attracted to a magnet. Unlike alternative magnets, which are mounted to an organ or vessel surface, a miniball-magnet like any miniball, can be implanted in deep tissue as well as coated with additional layers for the immediate or time-delayed delivery of medication. The crushing of cells along the trajectory of the miniball liberates the substantially aqueous protoplasmic contents to dissolve this outer coating releasing the medication, which may be an antibiotic, anti-inflammatory, or contain a particle or gamma ray-emitting radioactive isotope, into the surrounding tissues and bloodstream. Provided the stent-jacket or substitute magnetic field is applied, the fluid state at the trajectory terminus also allows magnetized miniballs to roll around into tractive orientation.

Such medication can be analgesic, antipyretic, anti-inflammatory; antibiotic; platelet blocking, anticoagulative, emit radiation, or some combination of these. There is some evidence to indicate that especially where the implants are outside the lumen, an outer coating of polylactide-co-sigma-caprolactone copolymer eluting paclitaxel, sirolimus, or dactinomycin, for example, would make possible sustained delivery to suppress neointimal hyperplasia for months after implantation and beyond the time for delivery of the drug to have been completed and the polymer to have dissipated (Drachman, D. E., Edelman, E. R., Seifert, P., Groothuis, A. R., Bornstein, D. A., Kamath, K. R., Palasis, M., Yang, D., Nott, S. H., and Rogers, C. 2000. "Neointimal Thickening after Stent Delivery of Paclitaxel: Change in Composition and Arrest of Growth over Six Months," *Journal of the American College of Cardiology* 36(7):2325-2332.

The layers in a miniball must be capable of sustaining the forces of expulsion without a loss in medical efficacy. This includes a hard, smooth, and spherical outer coating that avoids rolling resistance at curves dictated by the anatomy and nevertheless dissolves as required. Layers outside the bioinert layer that isolates the ferromagnetic core must thwart fracture, crushing, and deformation while disintegrating as desired. If the material of the layer cannot be made to the mechanical standards required, then intervening layers or adjuvants must be added. Unless sufficient hardness can be imparted to or about each added layer, implants that contain the same sequence of layers must be incorporated into and force the use of stays rather than miniballs.

A preferred method for incorporating medication for timed-release in the sugar-based outer coating of medicated miniballs is by liquid feed micro-encapsulation as may be produced using apparatus available from the Sono-Tek Corporation, Milton, N.Y. Depending upon the application, miniballs may be coated, as with ion exchange resins, for example, not just to deliver medication or radiation but to minimize the embologenicity of the metal surface. In order not to affect the penetration characteristics of the miniball in any significant way, such added coats must be hard.

Improved acceptance by the ductus of the miniball and stay implants described herein can be obtained by coating these with phosphorylcholine (Goreish, H. H., Lewis, A. L., Rose, S., and Lloyd, A. W. 2004. "The Effect of Phosphorylcholine-coated Materials on the Inflammatory Response and Fibrous Capsule Formation: in Vitro and in Vivo Observations," *Journal of Biomedical Materials Research. Part A* 68(1):1-9; Chen, C., Lumsden, A. B., Ofenloch, J. C., Noe, B., Campbell, E. J., Stratford, P. W., Yianni, Y. P., Taylor, A. S., and Hanson, S. R. 1997. "Phosphorylcholine Coating of ePTFE Grafts Reduces Neointimal Hyperplasia in Canine Model," *Annals of Vascular Surgery* 11(1):74-79; Whelan, D. M., van der Giessen, W. J., Krabbendam, S. C., van Vliet, E. A. Verdouw, P. D., Serruys, P. W., and van Beusekom, H. M. M. 2000. "Biocompatibility of Phosphorylcholine Coated Stents in Normal Porcine Coronary Arteries," *Heart* 83(3):338-345).

Recent evidence indicates that a coating of zinc oxide, especially in the form of nanorods, moderates an inflammatory (immune) response (see, for example, Zaveri, T. D., Dolgova, N. V., Chu, B. H., Lee, J., Wong, J., Lele, T. P., Ren, F., and Keselowsky, B. G. 2010. "Contributions of Surface Topography and Cytotoxicity to the Macrophage Response to Zinc Oxide Nanorods," *Biomaterials* 31(11): 2999-3007). Hydrogel polymers incorporating phosphorylcholine can be used as a bioinert medium for this medication (Lewis, A. L. 2006. "PC [Phosphorylcholine] Technology as a Platform for Drug Delivery: From Combination to Conjugation," *Expert Opinion on Drug Delivery* 3(2):289-298.

V4. Medication-Coated Miniballs, Stays, and Prongs with a Heat-Activated (-Melted, -Denatured) Tissue Adhesive-Hardener or Binder-Fixative Medication and stenting miniballs and stays can be concentrically coated with drugs and other therapeutic substances, such as adhesives, antiswelling agents, and drug resistance reversal agents. Intraparietal failure as the result of intralaminar or interlaminar separation is an eventuality that must always be considered, and when confirmed by testing, measures taken to prevent this outcome. Even when the disease process does not dispose the ductus thus, the very introduction of the implant can. Stays coated with a heat-activated tissue adhesive-hardener or binder-fixative such as a continuous or discontinuous solid protein solder layer about each stay to be melted once placed are discussed above under the section entitled Stays Coated with a Heat-activated (-melted, -denatured) Tissue Adhesive-Hardener. Such use is most effective applied to wide stays. The same solder is used to enclose miniballs.

When separation within the tissue of the ductus wall discovered through the test provided below in the section entitled In Situ Test on Extraluminal Approach for Intra- or Inter-laminar Separation (Delamination) indicates that:

a. Miniballs would be stopped only once having reached an outer tissue layer, which absorbing the force of impact by outward displacement, would separate from the subjacent layer allowing a miniball to insinuate itself within this space and continue traveling down through the wall along the inner surface of the outer layer to stop far distad of the target location, or that b. Intraparietal miniballs and the tissue of the ductus wall situated radially outward from the miniballs would be retracted by the stent-jacket bar magnets leaving the tissue axial (closer to the ductus central axis, adluminal) to the miniballs, hence, the stenosed or collapsed lumen unaffected, or that c. A less than severe malacia of the layers radially outward of the implants would allow the gradual penetration of the implants toward the stent-jacket magnets, that is, radial migration outwards until the implants released the layers bounding the lumen if not perforated the ductus, which phenomenon is referred to herein as pull-through.

Then stays with an outer coating of a solid protein solder should be used instead, or using miniballs, the stent-jacket must be positioned prior to initiating discharge as discussed in the sections entitled Sequence of Stent-jacket Placement and Implantation and Double-wedge Stent-jacket Rebound-directing Linings, and depending upon the results of the test upon extraluminal approach, the additional precaution is taken of using miniballs having an outer layer of solder less any coating thereupon, such as an antibiotic that does not detract from adhesion to the surrounding tissue or a lubricant that is dissipated at or below the denaturation temperature. Medication that withstands the temperature at which the solder denatures can be incorporated into the solder or a subjacent coating.

The test upon extraluminal approach in anticipation of implanting stays should be applied before and after implanting a single test stay. The test can also reveal the need to use stays coated with an adhesive-hardener and the amount of time that the particular solder will take to achieve initial set under heat until the stent-jacket can be placed. Such is not necessary with miniballs, hence with endoluminal approach testing, because with miniballs, it is possible to place the stent-jacket prior to initiating ballistic implantation. While unable to contend with malacia, when the lumen is filled and under pressure, preplacement of the stent-jacket as addressed below in the section entitled Sequence of Stent-jacket Placement and Implantation is usually sufficient in itself to reduce a separation.

Discharged at high enough of a velocity, a miniball will perforate entirely through the ductus wall regardless of a lack of cohesion within or between tunics or layers within the wall, an exception being those portions of the trachea subjacent to annular ligaments. At lower velocities, however, the miniball will pull apart and insinuate itself between layers in the wall of the ductus susceptible to separation. With miniballs, when the layers within the wall have been ascertained as prone to separate, the inter- or intralaminar failure or insinuation and continued travel distad of a miniball, along with the prevention of an eventual perforation, and/or the need to suppress a pulse that interferes with implantation, are among the reasons for prepositioning a snugly fitting stent-jacket prior to initiating discharge.

A ductus wall judged too malacotic to resist the eventual pull-through of implants under the tractive force exerted by a magnetic stent-jacket even when the implants have been solder-coated and heated is not a suitable candidate for treatment with the aid of intraparietal implants as described herein. For ductus that are not so weakened, plain or solid protein solder-coated stays, addressed below in the section entitled Arcuate Stent-stays (Stays, Stent-ribs, Ribs) for use with stent-jackets which present 1. A much larger surface area parallel to the ductus and thus better able to resist outward traction, 2. Able to deliver solder over a correspondingly larger area, and 3. Optionally coated with cyanoacrylate cement over the entire upper surface, will be more resistive to gradual pull-through than miniballs even solder-coated when not densely positioned.

While the application of cyanoacrylate cement contributes some additional strength, even when coated over the entire upper surface, stays are not dependent upon cyanoacrylate cement for intraparietal stabilization, but rather upon the solid solder adhesive coating over the entire surface. The cyanoacrylate, much of which is 'squeegeed' away upon incising the ductus, coats the upper surface of the adventitia or fibrosa and is intended primarily to seal the stay entry incision. That miniballs cannot be coated with cyanoacrylate cement in addition to a coating of antiplatelet or anticoagulant containing solder upon arrival is not a significant detraction.

Cyanoacrylate cement is never needed to seal the point of entry puncture wounds, and, while time-consuming without the position assistance of a servocontrolled linear stage, cyanoacrylate cement can be injected through a service-catheter passed down a free barrel-tube used as a service-channel once the miniballs have been implanted. Whether applied to stays or miniballs, the cement must have an open time even when heated that is sufficient to not encase the subjacent solder, which must be heated, suitable retardants such as glacial acetic acid having been specified in sections above, to include those entitled Description of the Preferred Embodiments and Stays Coated with a Solid Protein Solder Coating and Cyanoacrylate Cement. A miniball array such as implanted with the aid of a multiple barrel-tube barrel-assembly and positional control system is more quickly injected thus through a hypointimal or hypoendothelial radial projection unit tool-insert.

Figure 56:
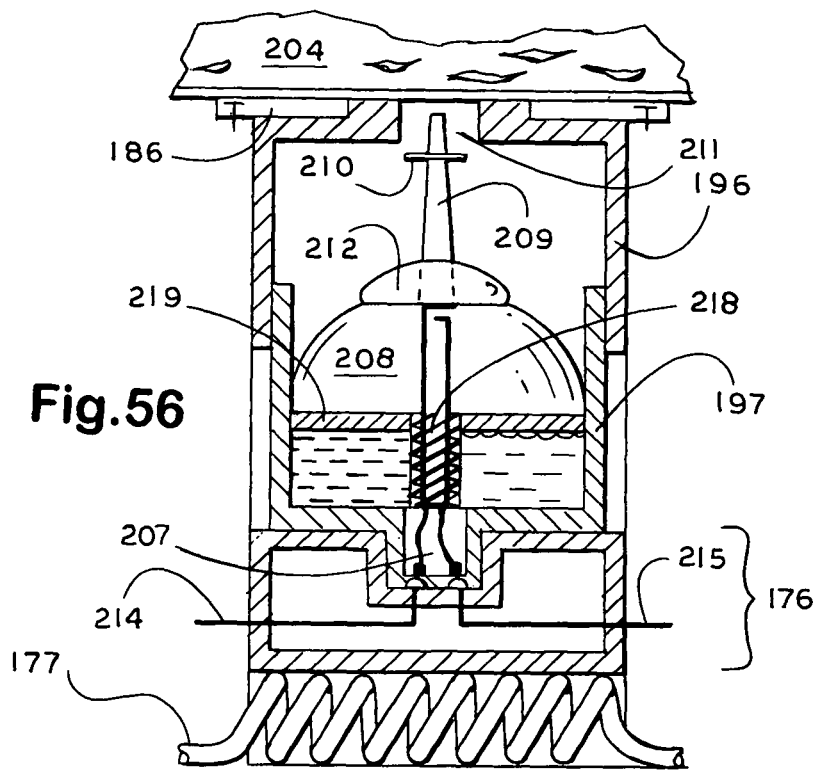
FIG. 56 shows a compound mechanical-electrochemically operated radial projection unit with an electrochemically lifted and discharged injection syringe tool-insert engaged, wherein the lifting expansion coil at the bottom of the lift-shaft beneath the lifting platform is not energized, the tool-insert instead lifted when contact of the needle point against the intima closes a circuit that causes current arriving through the socket to be passed through and melt the wax barrier separating chemicals that liberate a gas when mixed.

The distance that a tool-insert can be extended is proportional to the diameter of the lumen, hence, the barrel-assembly or radial projection unit catheter used, so that one in the esophagus, for example, can inject well into the submucosa. Coverage over a wider area of the lumen wall, whether to inject a bonding agent in order to harden malacotic tissue or to avert delamination, for example, or medication in order to cause the wall to swell for easier implantation, for example, is expedited through the use of a radial projection unit having a rear supply line and fitted with a hypointimal or hypoendothelial injection unit tool-insert, as shown in FIG. 56. When the tissue of the ductus wall has become malacotic rather than reduced in cohesion between its layers, preplacement of the stent-jacket only will not decrease the propensity toward pull-through.

That the preplacement of a magnetic stent-jacket means that magnetic traction will be exerted upon the miniballs immediately upon insertion emphasizes the limitation of such an approach to the prevention of perforation and intraparietal separation to the exception of pull-through. Provided the additional precaution is taken of using closely placed miniballs coated with a tissue adhesive-hardener or fixative that is solid at room temperature but denatures or melts and flows when heated, and then reaches initial set quickly, a negligible degree of malacia may still allow the use of a magnetic stent-jacket. This eventuality is due to the bonding among adjacent miniball adhesive-hardener fields that acts to divide the radially outward vector of magnetic traction between this vector and a vector to either side.

Unlike stays, miniballs cannot be additionally coated prior to implantation with cyanoacrylate cement, which setting more rapidly the lower is the viscosity, cannot be provided in a consistency sufficiently fluid at room temperature to act as a lubricant that will not clog the barrel-tubes. The addition of radiographic agent, tungsten powder, and/or glacial acetic acid can extend the open time of a cyanoacrylate adhesive, but the barrel-tubes are so small in gauge (typically 0.4 millimeters) that the presence of any fluid within these would result in obstruction.

While adhesives in contact with soft tissue are subject to enzymatic and hydrolytic breakdown that makes these ephemeral in adhesion retention, no more than two or so weeks is necessary to positionally stabilize a small implant by fibrous encapsulation. A separate (nonballoon) injection microcatheter passed down one of the two barrel-tubes used in a two-way muzzle-head as described below in the section entitled Service-channel Adhesive Delivery Line used as a service-channel can be used to inject cyanoacrylate cement about the miniball entry site following implantation (see, for example, Miyachi, S., Izumi, T., Satow, T., Srivatanakul, K., Matsumoto, Y., and 3 others 2017. "Effectiveness of Preradiosurgical Embolization with NBCA [N-butyl cyanoacrylate] for Arteriovenous Malformations—Retrospective Outcome Analysis in a Japanese Registry of 73 Patients (J-REAL study)," *Neurointervention* 12(2):100-109; Ellis, J. A. and Lavine, S. D. 2014. "Role of Embolization for Cerebral Arteriovenous Malformations," *Methodist Debakey Cardiovascular Journal* 10(4):234-239; Goto, K., Uda, K., and Ogata, N. 1998. "Embolization of Cerebral Arteriovenous Malformations (AVMs) [arteriovenous malformations]—Material Selection, Improved Technique, and Tactics in the Initial Therapy of Cerebral AVMs," *Neurologia Medico-chirurgica* (Tokyo) 38 Suppl:193-199); however, a reduction in the number of barrel-tubes reduces the rate of implant delivery. Proximity of the cyanoacrylate to the heat used to melt a solder layer would exacerbate its premature setting in any delivery line and following parietal injection.

Moreover, cyanoacrylate cement is not amenable of dilution or thinning through the use of a solvent, surfactant, or acetic acid, for example, although the latter can be used to retard it in initial set. Recovery electromagnets and antechambers are addressed below in the section entitled Multiple Radial Discharge Barrel-assemblies with One- to Four- or More-way Radial Discharge Muzzle-heads. Access to the exterior of the ductus obstructed when the stent-jacket has been placed previously, heat is applied to flow the solder by the muzzle-head electromagnet windings or a 'cooling catheter' as addressed below in the section entitled Cooling Catheters (Temperature-changing Catheters) snaked down the barrel-assembly that is connected to the hot air outlet of a nominally 'cold' air gun.

According to the material of the base-tube, the preplaced stent-jacket furnishes some heat containment or insulation value which is usually sufficient to necessitate the use of an endoluminal rather than extraluminal source of heat, but seldom sufficient to justify preplacement in itself. When placed with the aid of a positional control system, miniballs with a thicker coating of solder can be positioned closely enough together that upon heating, the tissue infused by the melted adhesive-hardener fixative or binder from each, its respective adhesive-hardener field, will merge with the field of the adjacent miniballs to cure as a solid unit structure that is able further to resist migration, to include by pull-through. For dealing with certain conditions, the attainment of stability thus can be the primary purpose in resorting to the use of machine controlled positioning.

Suitable plasticizers to reduce brittleness as might pose resistance to intrinsic motility are dimethyl sebacate, di-n-butyl sebacate, di-n-octyl phthalate, triethyl phosphate, triisobutyl phosphate, tri(2-ethylhexyl) phosphate, tri-p-cresyl phosphate, glyceryl triacetate, glyceryl tributyrate, diethyl sebacate (Coover, H. W. Jr. and Fassett, D. W. 1973. "Surgical Method," U.S. Pat. No. 3,759,264). Still other plasticizers were disclosed earlier (see, for example, Joyner, F. B. and Coover, H. W. Jr. 1957. "Plasticized Monomeric Adhesive Compositions and Articles Prepared Therefrom," U.S. Pat. No. 2,784,127; Shearer, N. H. Jr. and Coover, H. W. Jr. 1957. "Mixed Alpha-cyanoacrylate Adhesive Compositions, U.S. Pat. No. 2,776,232). When the condition of the ductus is one of malacia rather than laminar separation, the ability of the miniballs to resist outward migration may necessitate that the adhesive-hardener be allowed to fully cure before the magnetic stent-jacket is placed.

When filled with solder that can be predicted with reasonable confidence to gradually be replaced by continuous tissue, and the surface of the miniball is textured to allow tissue infiltration as will result in mechanical bonding, some residual laminar separation may be acceptable. The object in allowing the adhesive between miniballs to cure is to allow the formation of a longitudinally extended unit that is better able to resist outward migration. The thickness of the solid adhesive coating on the miniballs determines the proximity with which the miniballs must be placed to achieve such merger and unitization, and this in turn will determine whether the use of a positioning control system is needed to place the miniballs at the distance required.

Implanted transluminally, miniballs allow deferral to a later procedure of stent-jacket placement, which is by laparoscopic entry. When the restoration of patency is urgent, the use to treat a malacotic ductus of miniballs coated with a protein solder having a long curing time and thus forcing postponement in the placement of the stent-jacket, is unacceptable. To restore patency immediately, an anti-inflammatory such as a steroidal drug-eluting absorbable endoluminal stent is inserted after placing the miniballs. This endoluminal procedure as part of an endoluminal procedure makes it possible to defer the laparoscopic entry wound and placement of the stent-jacket for the period over which the absorbable stent can be depended upon, which period will be far longer than any required for the curing of an adhesive-hardener. The patient can thus be given an period of months before the need to perform the followup procedure.

V5. Heating Control Over Implants and Coated Implants, to Include Miniballs, Stays, and Prongs V5a. Heating of Implants and Coated Implants, to Include Miniballs, Stays, and Prongs Using Implant-Passive Ductus-External or Extrinsic Means Heat can be used to accelerate the dissolution and/or uptake of medication and/or a coating thereof, apply hyperthermic therapy, and accelerate the dissolution of absorbable components, for example. Magnetic or electromagnetic induction is used, the latter familiar as induction heating. Implanted miniballs that include medication, a bonding agent, or a tissue hardener, for example, can be passively heated using heating elements in the muzzle-head, to include heat-windows and radial projection unit tool-inserts, described below. Stays are passively heated from outside the adventitia, usually through the access wound. When the adventitia is exposed and would not suffer heat injury, heating from outside the ductus is possible. Entry through a small incision allows the insertion of a heating probe that can heat the subadventitial miniballs, stays, or prongs.

The Curie temperature is not reached and the implant not demagnetized. Access from outside the ductus is suited to stays and patch-magnets which are placed from outside the ductus and thus necessitate an incision to be inserted in any event. Ductus-external heating should not be confused with extracorporeal or remote heating using electromagnetic energy as addressed above in the section entitled Implants that Radiate Heat on Demand and the section immediately following. However, implants such as miniballs held within holding jackets, for example, which are proximate to implants that incorporate extracorporeally excitable elements can be warmed indirectly thus, the effect used, for example, to cause or accelerate the dissolution of a medicinal coating of a miniball or the dissolution of a medication miniball.

V5b. Extracorporeal Energization of Intrinsic Means for Radiating Heat from Within Medication Implants and Medication and/or the Tissue Bonding-Coatings of Implants All of the implants described herein, miniballs and stays in particular, can incorporate materials formulated and/or configured to allow these to generate and radiate heat from within by remote control as well as release medication. Extracorporeal or remote heating of the implants is mentioned above in the section entitled Implants that Radiate Heat on Demand. Miniballs and stays can be loaded with magnetically susceptible matter or magnetized to support both magnetic drug-targeting and heating in either order based upon the therapeutic objective (see, for example, Belyanina, I. V., Zamay, T. N., Zamay, G. S., Zamay, S. S., Kolovskaya, O. S., and 13 others 2017. "In Vivo Cancer Cells Elimination Guided by Aptamer-functionalized Gold-coated Magnetic Nanoparticles and Controlled with Low Frequency Alternating Magnetic Field," *Theranostics* 7(13): 3326-3337; Zamay, T. N., Zamay, G. S., Belyanina, I. V., Zamay, S. S., Denisenko, V. V., and 15 others 2017. "Noninvasive Microsurgery Using Aptamer-functionalized Magnetic Microdisks for Tumor Cell Eradication," *Nucleic Acid Therapeutics* 27(2):105-114; Vegerhof, A., Barnoy, E. A., Motiei, M., Malka, D., Danan, Y., Zalevsky, Z., and Popovtzer, R. 2016. "Targeted Magnetic Nanoparticles for Mechanical Lysis of Tumor Cells by Low-amplitude Alternating Magnetic Field," *Materials* (Basel, Switzerland) 9(11). pii: E943; Kobayashi, T. 2011. "Cancer Hyperthermia Using Magnetic Nanoparticles," *Biotechnology Journal* 6(11):1342-1347; Ivkov, R., DeNardo, S. J., Daum, W., Foreman, A. R., Goldstein, R. C., Nemkov, V. S., and DeNardo, G. L. 2005. "Application of High Amplitude Alternating Magnetic Fields for Heat Induction of Nanoparticles Localized in Cancer," *Clinical Cancer Research* 11(19 Part 2):7093s-7103s).

Miniballs and stays can be made that include a single medication, concentric layers of medication, or a single or multiple layers of medication that include a ferromagnetic or a radiation-emitting core, and heat used to effect or to accelerate the release of each layer, which if including magnetically susceptible matter, can also be magnetically targeted or spread. The same or different magnetically susceptible matter can be incorporated into the core or included in a matrix in the core or in layers surrounding the core, and any or all of these coated to codetermine with the matrix the temperature at which each will disintegrate. When the core of a miniball, for example, is constituted to radiate heat, applying successive concentric layers of medication or other therapeutic substances in melting point sequence moving outward from the core with that lowest outermost will cause that substance to be released first, with those beneath released in melting point sequence.

Cores and layers formulated to break down at a prescribed temperature can also serve to accelerate the release and uptake of the drug released or the action of a therapeutic substance. That separate miniballs can release substances to act upon one another and affect tissue individually or together is considered obvious. Intrinsic heat radiation that necessitates the incorporation of nonabsorbable elements is suitable for nonabsorbable implants and nonabsorbable implants with absorbable coatings, such as of medication. When nonabsorbable elements must be included for use in the bloodstream, then impasse-jackets, addressed above in the sections entitled Concept of the Impasse-jacket and Miniball and Ferrofluid-borne Particle-impassable Jackets, or Impasse-jackets are used to trap any magnetically susceptible nonabsorbable residue.

Medication introduced upstream from an impasse-jacket and suspended by the jacket in the lumen can incorporate drug carrier nanoparticles that allow both the remote release by heating and targeting of medication, for example. If necessary (which should be seldom) the residue is then extracted from the impasse-jacket with the aid of an external electromagnet, as addressed above in the section entitled Miniball and Ferrofluid-borne Particle-impassable Jackets, or Impasse-jackets and below in the section entitled Use of an External Electromagnet to Assist in Mishap Recovery. To assure retrievability in the event of a mishap, even medication miniballs and stays contain magnetically susceptible matter, if slowly absorbable, of iron powder, if absorbable or safely assimilable in the small amounts involved, of superparamagnetic magnetite or maghemite nanoparticles or finely grained powder.

When a miniball, stay, or other implant incorporates magnetically susceptible matter, the alternating magnetic field produced by a high power magnetic resonance machine or an alternating magnetic field applicator (Johannsen, M., Thiesen, B., Wust, P., and Jordan, A. 2010. "Magnetic Nanoparticle Hyperthermia for Prostate Cancer," *International Journal of Hyperthermia* 26(8):790-795; Latorre, M. and Rinaldi, C. 2009. "Applications of Magnetic Nanoparticles in Medicine: Magnetic Fluid Hyperthermia," *Puerto Rico Health Sciences Journal* 28(3):227-238) can be used to heat that matter such that intervening tissue beyond the zone of the heat radiated is unaffected. In this way, the core or layer-incorporated nanoparticles or microspheres allow control from outside the body over the release of medication from each layer. Any of the implants described herein, to include miniballs, stays, and prongs can be constituted to be heated by placing the patient in the alternating magnetic field, to include that of a high power magnetic resonance machine.

The heating of implants during imaging is normally considered from the standpoint of burn avoidance (see, for example, Maffei, E., Calcagnini, G., Censi, F., Triventi, M., and Bartolini, P. 2010. "Numerical Model for Estimating RF-induced Heating on a Pacemaker Implant during MRI: Experimental Validation," *Institute of Electrical and Electronics Engineers Transactions on Biomedical Engineering* 57(8):2045-2052; Busch, M. H., Vollmann, W., and Grönemeyer, D. H. 2006. "Finite Volume Analysis of Temperature Effects Induced by Active MRI Implants: 2. Defects on Active MRI Implants Causing Hot Spots," *Biomedical Engineering Online* 5:35; Leon-Villapalos, J., Kaniorou-Larai, M., and Dziewulski, P. 2005. "Full Thickness Abdominal Burn following Magnetic Resonance Guided Focused Ultrasound Therapy," *Burns* 31(8):1054-1055; Ruschulte, H., Piepenbrock, S., Münte, S., and Lotz, J. 2005. "Severe Burns during Magnetic Resonance Examination," *European Journal of Anaesthesiology* 22(4):319-320; Busch, M. H., Vollmann, W., and Grönemeyer, D. H. 2005. "Finite Volume Analysis of Temperature Effects Induced by Active MRI Implants with Cylindrical Symmetry: 1. Properly Working Devices," *Biomedical Engineering Online* 4(1):25; Karoo, R. O., Whitaker, I. S., Garrido, A., and Sharpe, D. T. 2004. "Full-thickness Burns Following Magnetic Resonance Imaging: A Discussion of the Dangers and Safety Suggestions," *Plastic and Reconstructive Surgery* 114(5):1344-1345; Smith, C. D., Nyenhuis, J. A., and Kildishev, A. V. 2001. "Health Effects of Induced Electrical Fields: Implications for Metallic Implants, in Shellock, F. G. (ed.), *Magnetic Resonance Procedure: Health Effects and Safety*, Boca Raton, Fla.: Chemical Rubber Company Press, pages 393-414).

Heating as the result of placing heat-intolerant implants in a high intensity alternating magnetic field is here used intentionally. Incorporating iron oxide, cobalt, iron, or cobalt-iron nanoparticles into the core or layers of a miniball, for example, improves the heating effect. A magnetic field alternated at radio frequencies can heat an implant containing such material through eddy-current induction, superparamagnetism, and Stoner-Wohlfarth magnetization reversal. When the viscosity of the matrix permits, alignment with the alternating magnetic field additionally exerts a heating effect, and an alternating electrical current will be induced in an implanted object that incorporates conductive wire.

Of these mechanisms for remote heating in an alternating magnetic field, some act on magnetically susceptible particles; burns, however, result from the induction of electrical current in conductive wire-shaped components such as artificial pacemaker leads when placed in a magnetic field alternated at radio frequency, especially when these components participate in a closed circuit (see, for example, Yamazaki, M., Yamada, E., Kusumi, K., Sahara, T., Higashida, M., and Motozuka, M. 2008. "Investigation of the Local Heating caused by a Closed Conducting Loop at Clinical MR Imaging: Phantom Study," [in Japanese; English abstract at http://www.jstage.jst.go.jp/article/jjrt/64/7/883/_pdf], *Nippon Hoshasen Gijutsu Gakkai Zasshi* 64(7): 883-885).

To deliberately intensify the heating effect, miniballs and stays incorporate electrically conductive material to form of a closed circuit, for example. The miniballs or stays are constituted so that these mechanisms singly or in combination make it possible to bring the implant or its currently outermost layer to the temperature desired. When the miniball, stay, or its outer layer consists in whole or in part of a protein solder devised to denature (melt, flow) at a low enough temperature to avoid injury to tissue, the nanoparticles or microspheres incorporated into the solder act to melt the solder or if passively heated by an outside source as addressed above in the section entitled Heating of Implants and Coated Implants, to Include Miniballs, Stays, and Prongs Using Implant-Passive Ductus-external or Extrinsic Means as well, then accelerate its melting from outside the body.

The same nanoparticles that in an alternating magnetic field serve to heat the matrix can support magnetic drug or other therapeutic substance targeting in the field of a strong hand-held electromagnet or the $B_0$ field of a magnetic resonance machine, as addressed below in section X2c entitled Stereotactic Arrest and Extraction of a Circulating, Dangerously Mispositioned, or Embolizing Miniball. While miniballs and stays must incorporate sufficient magnetically susceptible matter to allow emergency recovery if necessary, miniballs and stays used to implant medication consist predominantly of absorbable matter. A residue absorbed over time if ever is trapped and can be extracted.

As nonabsorbable, larger miniballs and stays used for long-term or permanent magnetic stenting or to emit radiation can alternatively or additionally incorporate a resonant circuit which is energized to generate heat when placed in magnetic field alternating at radio frequency. Implanted miniballs incorporating a resonant circuit can be heated from outside the body with an external source of radiofrequencies (see, for example, Niwa, T., Takemura, Y., Inoue, T., Aida, N., Kurihara, H., and Hisa, T. 2008. "Implant Hyperthermia Resonant Circuit Produces Heat in Response to MRI Unit Radiofrequency Pulses," *British Journal of Radiology* 81(961):69-72, available at http://bjr.birjournals.org/cgi/content/full/81/961/69); however, with ferromagnetic components implanted, radiofrequency generation can be obtained from the transmit only coil of a nuclear magnetic resonance machine.

Once refined to allow an increase in temperature greater than 12.6 degrees centigrade (55 degrees Fahrenheit), this capability will allow heating a miniball with a deeply textured undercut surface and an outer coating of a protein solder or solder and medication to denature (flow) the solder about it to secure the miniball in position against the constant if slight pull of the magnetic stent-jacket. The solder is then gradually replaced by infiltrating tissue to perpetuate the positional stability. The incorporation of nanoparticles in layers and/or coatings that envelope layers of medication expand the differential control by layer that can be exerted. The incorporation into miniballs, stays, and patch-magnets, for example, of extracorporeally energizable elements also pertains to impasse-jackets, wherewith miniballs held by the jacket and the encircled segment of the ductus, for example, can be heated.

For this purpose, the miniball will usually itself incorporate the extracorporeally heatable element, indirect heating by a surrounding stent or holding jacket being less effective. The resonant response to a time-varying magnetic field can be used to cause nanoparticles coating on a polymeric matrix to release heat into the surrounding tissue where the warming effect can be used to warm the treatment ductus, or accelerate dissolution and uptake of a drug, or the melting of a protein solder, for example (Namdeo, M., Saxena, S., Tankhiwale, R., Bajpai, M., Mohan, Y. M., and Bajpai, S. K. 2008. "Magnetic Nanoparticles for Drug Delivery Applications," *Journal of Nanoscience and Nanotechnology* 8(7): 3247-3271; Bastus, N. G., Puntes, V. F., Amigó, R., Batlle, X., Labarta, A., Kogan, M. J., Araya, E., Grillo-Bosch, D., Giralt, E., and Turiel, A. 2006. "Nanoparticles: Local And Remote Energy Sources," *European Material Research Society, Spring Meeting, Symposium A,* 29 May-2 June, Nice, France, text at http://www.nanospain.org/Workshop2/Files/Orales/Nanobiotechnology/Gomez_Neus.pdf, slides at www.nanospain.org/Workshop2/Files/Presentations/GomezBastus_Neus.pdf; published as Bastus, N. G., Kogan, M. J., Amigó, R., Grillo-Bosch, D., Araya, E., Turiel, A., Labarta, A., Giralt, E., and Puntes, V. F. 2007. "Gold Nanoparticles for Selective and Remote Heating of β-amyloid Protein Aggregates," *Materials Science and Engineering: C. Materials for Biological Applications* 27(5-8): 1236-1240; Alexiou, C., Jurgons, R., Seliger, C., and Iro, H. 2006. "Medical Applications of Magnetic Nanoparticles," *Journal of Nanoscience and Nanotechnology* 6(9-10):2762-2768). Nanoparticles can also be used to obtain different resonant responses from layers or shells of medication.

Nanoparticle-incorporating miniballs, stays, and coatings applied to any of the implants described herein to allow the noninvasive induction and radiation of heat can release drugs for magnetic drug-targeting, enabling multimodal ductus-intramural treatment (see, for example, Chen, B., Wu, W., and Wang, X. 2011. "Magnetic Iron Oxide Nanoparticles for Tumor-targeted Therapy," *Current Cancer Drug Targets* 11(2):184-189; Chen, Y. and Chen, B. A. 2010. "Application and Advancement of Magnetic Iron-oxide Nanoparticles in Tumor-targeted Therapy," *Chinese Journal of Cancer* 29(1):125-128 (in English as "Application and Development of Magnetic Iron-oxide Nanoparticles in Tumor-targeted Therapy," at http://www.cjcsysu.cn/ENpdf/2010/1/118.pdf); Purushotham, S., Chang, P. E., Rumpel, H., Kee, I. H., Ng, R. T., Chow, P. K., Tan, C. K., and Ramanujan, R. V. 2009. "Thermoresponsive Core-shell Magnetic Nanoparticles for Combined Modalities of Cancer Therapy," *Nanotechnology* 20(30):305101; Peng, X. H., Qian, X., Mao, H., Wang, A. Y., Chen, Z. G., Nie, S., and Shin, D. M. 2008. "Targeted Magnetic Iron Oxide Nanoparticles for Tumor Imaging and Therapy," *International Journal of Nanomedicine* 3(3):311-321). Medication and/or radiation miniballs and stays can incorporate any of differently constituted nanoparticles.

Unlike the magnetic targeting of a ferrofluid (Alexiou, C., Arnold, W., Klein, R. J., Parak, F. G., Hulin, P., Bergemann, C., Erhardt, W., Wagenpfeil, S., and Lübbe, A. S. 2000. "Locoregional Cancer Treatment with Magnetic Drug-targeting," *Cancer Research* 60(23):6641-6648), by secondary accumulation at the treatment site, delivery is to the target ab initio. While intrusive, implantation is preferable when the site must be exposed. The application of extracorporeal shock wave lithotripsy to the disintegration of miniballs or stays containing medication that had previously been implanted in the wall of a lumen is limited by the need to avoid dislodgement, delamination, or perforation into the lumen or through the adventitia.

V6. Chemical Control Over Implants and Coated Implants, to Include Miniballs, Stays, and Prongs Miniballs, impasse-jackets, and stays can incorporate drugs or other therapeutic substances for prepositioning in locations not previously accessible, to target a small surrounding area at a later date if and when the need for that substance or substances is confirmed. The encapsulating layer, or a specially prepared drug that remains physiologically inactive or metabolically inert until converted after implantation does not require encapsulation, or both are made nonbiodegradable or inert in the metabolic milieu until a second, or if both, two additional exogenous substances, are brought into contact with it. That is, unless the medication and/or other therapeutic substance can itself prepared in a nonbiodegradable or metabolically inert form, it is protected within a nonbiodegradable or metabolically inert capsule. In exceptional cases where premature or unnecessary activation of the drug would be harmful, a metabolically inert pharmaceutical is additionally encapsulated within a metabolically inert shell. More specifically, such drugs include:

1. Any prior art solid or liquid drug or therapeutic substance or combinations thereof within an endogenously (metabolically) inert (nondisintegratable, indissoluble, nonbiodegradable) surrounding outer chemically isolating capsule or shell that must be exposed to a biocompatible exogenous (nonmetabolic) solvent or disintegrating chemical such as an enzymatic breakdown agent to expose its contents;

2 A special class of nonencapsulated prodrug in solid form that remains endogenously (metabolically) inert and physiologically inactive until brought into contact with and converted by an exogenous biocompatible solvent or disintegrating chemical such as an enzymatic breakdown agent.

3. Such a prodrug, proenzyme (zymogen), protein precursor (pro-protein, pro-peptide) or prohormone, such as precursory prednisolone, for example, that would be injurious if released prematurely or unnecessarily can be additionally encapsulated as described, whereupon one exogenous dissoluting agent must be introduced to disperse the encapsulating layer and another to activate the contents.

A second substance either dissolves the capsule surrounding the conventional drug, or activates an unencapsulated prodrug, or if an encapsulated prodrug, then the next added or second substance disintegrates the capsule exposing the inert prodrug with the third substance added to activate it. Any type drug mentioned in the section above entitled Field of the Invention is included. When formulated for such use, such prodrugs and/or other therapeutic substances in miniballs, or in the concentric layers thereof, or microspheres suspended in the bloodstream by impasse- and exceptionally, by more strongly magnetized stent-jackets, for example, are converted or supplemented and thus activated. Different paired substances and the relative proportion of each allow selective control in response to follow-up diagnostics.

While ordinarily delivered directly to the implant or implants in the wall surrounding the gastrointestinal tract or through the blood stream by oral administration, alternative routes allow the amount of the activating or triggering substance or substances to be less. Whether introduced through the bloodstream or by direct injection, delivery can be through any lumen. The use of heat directly applied or induced is addressed above in the sections entitled Implants that Radiate Heat on Demand, Heating Control over Implants and Coated Implants, to Include Miniballs, Stays, and Prongs, among others. When direct or induced heat is additionally used, the solvent can be encapsulated and released by heating within the same or a neighboring implant.

Dissolution of the encapsulating layer can be accomplished by nonmetabolic chemical dissolution with or without heat. The placement in close formation of miniballs under machine control allows a mix of miniball types for response to different aspects of the disease process confronted. The dense spacing among implants required to satisfy such a combination of desiderata is but one circumstance that warrants the precision of discharge under machine control. If the encapsulated substance is a conventional drug or prodrug, then once the capsule has been disintegrated, the contents are activated and dispersed in the conventional manner through biotransformation, or spontaneous metabolic conversion. Preparation thus of both physiologically active and prodrugs differs only in requiring encapsulation within a material that only a biocompatible solvent not found in the body will dissolve or an exogenous agent will disintegrate.

The detailed formulation of paired encapsulating materials and substances to disintegrate these exceeds the present scope. One example for the use of medicinal implants as described is the site of an atheroma where the release of antimitotic and anti-inflammatory medication is best withheld until restenosing is confirmed. Implants to release medication are addressed above in the sections entitled Medicinal and Medicated Miniballs and Stays; Absorbable and Nonabsorbable Circumvascular Jackets with Medicated Linings; and Medication (Nonstent) Implants and Medication-coated Miniballs, Implants, and Prongs, among others, with control over release from outside the body addressed above in the section entitled Extracorporeal Energization of Intrinsic Means for Radiating Heat from Within Medication Implants and Medication and/or the Tissue Bonding-coatings of Implants, among others.

Both encapsulated and solid prodrug miniballs described can be prepositioned by suspension in the lumen by a holding jacket, or miniballs or stays of like formulation infixed within the wall surrounding the lumen. Suspended within a holding jacket, a drug ferrobound to magnetically susceptible particles will upon disintegration of the miniball be drawn into the wall of the lumen, whereas one ferro co-bound, that is, enclosed or compacted together with but not uncleavably bound to the drug will be freed to flow downstream with the susceptible matter needed for retention within the holding jacket if small enough drawn into the ductus wall and if too large to be drawn in, then held against the wall. Release of an encapsulated prodrug of the kind indicated is achieved by a solvent, liquefying agent, or converting enzyme for the encapsulating layer, and another agent such as a converting enzyme to convert the prodrug to the physiologically active state.

If and only if the second or second and third substances would not be absorbed from the lumen into the ductus wall, a miniball or stay prepositioned therein is accessed by injection with an injection tool-insert. In this circumstance, unless the triggering substances are to be added immediately (thus defeating much of the advantage), access to the miniballs or stays would necessitate a second procedure, although direct injection allows the amount of the activating substance to be minimized relative to alternative routes. In the gastrointestinal tract, suspension in a holding jacket allows the second and/or third complementary triggering substance to be introduced postprocedurally, and if accessed through the oral route, has the additional benefit of delivery at a later date simply by swallowing a pill.

Access to the vascular tree without the need to return to the clinic is preferably oral but can be accomplished through a subcutaneously implanted portal for a direct or central catheter. Other system ductus are accessed directly by implanted catheter with subcutaneous surface access portal. If intended to circulate, the substance must enter the bloodstream; thus, any such substance administered orally must pass through the gut as a ferrofluid, and if not specifically targeting the liver, must pass through the liver. While accomplished by injection or infusion without the need for a second invasive transluminal procedure, the need for frequent dosing recommends showing the patient how this is accomplished at home; however, one-time parenteral delivery of a later activating agent or agents is accomplished in the clinic.

Ideally, the activating substance is prepared as an orally administered liquid which the patient instructed to take by mouth at a set time and date following implantation. That treatment is targeted with the systemic circulation substantially avoided even when the nonimmunogenic activating substance or substances are transmitted by the circulation allows drugs to be combined that might produce adverse sequelae if not limited to a small area. Magnetically susceptible matter in blood borne miniballs or microspheres will be seized within the impasse- or stent-jacket so that it is drawn against and into the lesion. A drug and/or radionuclide bound to this matter will be drawn together with it, whereas unbound, these will be liberated and carried forward in the bloodstream leaving the magnetically susceptible matter within the jacket. If exceptionally necessary, an impasse-jacket will allow the accumulated magnetic matter to be extracted noninvasively, as addressed above in the section entitled Concept of the Impasse-jacket.

By contrast, removal from a stent-jacket which lacks an extraction grid, is by means of a guidewire with a tip magnetized strongly enough to overcome the pull of the jacket or the recovery electromagnets in the muzzle-head of a radial discharge barrel-assembly. Increasing the temperature of an implant by placing the patient in a radio frequency alternating magnetic field as may be used to disintegrate concentric layers of medication is addressed in the preceding section. The coordinated use of heating and the infusion, injection, or ingestion of activating substances affords control over the release of each layer. Control encompasses both the release and rate of release of drugs, therapeutic substances, and exceptionally, radionuclides from miniballs, layered miniballs, microspheres, and layered microspheres seized from the luminal contents and held within entry impasse- or stent-jackets.

Paired entry and exit-jackets, addressed above in the sections entitled Field of the Invention and Concept of the Impasse-jacket and below in the section entitled Cooperative Use of Impasse-jackets in Pairs and Gradient Arrays, among others, are used to designate (establish the limits of, denote, define, outline) a particular segment of a ductus or an organ for treatment. The exit jacket releases a counteractant or agent that counteracts (reverses, neutralizes) the substance released by the entry jacket by molecular cleavage, binding, inactivation, or inverse agonist release. The various means for controlling the release of substances from miniballs held in impasse-jackets afford the ability to differentially control the release or rate of release of an actant at the entry jacket and the counteractant at the exit-jacket.

V7. Radiation-Emitting (Brachytherapeutic, Endocurietherapeutic, Sealed Source Radiotherapeutic, Internal Radiation Therapy) Miniballs The ability to transluminally approach a level, that is, a certain distance along a ductus that is a site of disease, and infix within the lumen wall a discrete implant that emits radiation and/or medication affords advantages over the prior art, in that to accomplish a similar result, one previously had to introduce an endoluminal stent that brought with it the several problems discussed above. Of these, medical but not irradiating implants could be absorbable. Miniball implants can consist entirely of medication, which by concentric layering can be multiple, can include a core that is an irradiating seed, and miniballs implanted in adjacent relation can combine, separate, and alternate in medication and radiation. Tantalum or comparably vivid markings at the muzzle-port or ports is discussed elsewhere.

The placement of radiation-emitting seed miniballs by the means described herein is not intended for transluminal implantation of the prostate gland, which if introduced through the urethra would injure the epithelium exposed to urine and could injure the urethral verumontanum. Neither does ballistic implantation allow the suturing together of seeds for positional stability as does conventional needle insertion. When the muzzle-head can be brought beyond the distal extremities of the bronchi so that little more than manageable hemorrhaging would result, use of this method may be given consideration. The preparation of radiactive miniballs, whether for aeroballistic discharge or for bonding between the lining and base-tube of a stent-jacket, for example, is no part of the present invention and can be accomplished by means such as those described in Good, R. R. 1994. "Endocurietherapy," U.S. Pat. No. 5,342,283, with continuation-in-part Good, R. R. 2000. "Endocurietherapy," U.S. Pat. No. 6,099,457.

Conventionally, higher dose-rate radiation is administered either brachytherapeutically with an automated remote afterloader machine or by external beam radiation (see, for example, Waksman, R. (ed.) 2002. *Vascular Brachytherapy*, Hoboken, N.J.: Wiley-Blackwell). However, provided seeds are spherical, any barrel-assembly of matching gauge or caliber can be used to implant ceramic-titanium encapsulated radioisotopes of such radioisotopes (radionuclides) as cesium-131, iridium-192, bismuth-212, lead-212, iodine-125, gold-198, phosphorus-32, ytterbium-169, yttrium-90, or palladium-103 within the wall of a ductus. The primary object is to allow implantation of seeds in the walls of ductus not previously implantable thus and secondarily to allow the use of seeds that deliver a higher dose-rate which can be withdrawn at will.

Moreover, because the same apparatus or in some instances, an external hand-held electromagnet can be used to recover the seeds, higher dose-rate seeds can be implanted for a period determined on the basis of followup diagnostics and removed when desired. No endoluminal stent present, radiation seeding pertains to primary stenotic conditions best treated by highly localized sources rather than to reducing the risk of in-stent restenosis. The interstitial brachytherapeutic seeds required differ from those currently made by Implant Sciences Corporation, Wakefield, Mass., IsoRay Medical Incorporated, Richland, Wash., North American Scientific, Chatsworth, Calif., or C. R. Bard, Incorporated, Covington, Ga. only in being spherical.

The forces generated by airgun expulsion in medical use do not attain values as would jeopardize seed integrity as conventionally manufactured, so that no additional precautionary structural modifications to the seeds is required. Furthermore, whereas low-dose-rate seeds have been considered unrecoverable, by enclosing ferrous metal within the seeds, the recovery electromagnets, which just in front of (distal to) the muzzle-ports are immediately present to the implantation site, are present to retrieve any seeds that should become mispositioned. Depending upon the maximum diameter of the miniballs that can be used, the spherical seeds may be further encapsulated within layers of medication or sequentially time-released medication. In this connection, and with respect to the pure medication miniballs, a medical layer can contain a gamma-emitting isotope such as indium-111 or molybdenum-99.

Conventional intraductal brachytherapy is compatible with the use of a barrel-assembly. The intraductal brachytherapy catheter is passed down the barrel-assembly (as is a cooling catheter, addressed below in the section entitled Cooling Catheters (Temperature-changing Catheters). The same applies to a high-dose-rate source delivery catheter as controlled by an automated afterloader. When performed with another catheter-based procedure, radiation seeding by this means differs from intraductal brachytherapy in not requiring the withdrawal of one catheter and the introduction of another; only the extracorporeal rotary magazine clip in the airgun requiring to be changed.

V8. Temporary (Absorbable) Ferromagnetic Miniballs and Other Implants

In treating a temporary condition, when it is preferred that the miniballs used with a temporary stent-jacket or patch-magnets, magnet-jacket, or external magnet-jacket that will be removed when no longer needed not remain within the ductus wall but dissipate, the miniballs are made with superparamagnetic magnetite or maghemite nanoparticles or finely grained powder dispersed in an absorbable matrix. Absorbable ferromagnetic miniball implants can contain medication, a bonding agent, superparamagnetic magnetite or maghemite nanoparticles or finely grained powder for retrieval, a radiation emitting seed, or any of these in combination. The matrix can include or consist purely of medication. The absorbable materials, mostly the same as those used for absorbable suture and to make tissue engineering scaffolding are addressed above in the section entitled Stent-jacket expansion insert materials having relatively short breakdown times.

VI. Rotary Magazine Clips

FIG. 28 shows a seven-shot rotary magazine clip for use in a single barrel radial discharge barrel-assembly, and FIG. 29 a 10-shot rotary magazine clip for use in a four barrel or four-way radial discharge barrel-assembly. The single-shot rotary magazine clip can be adapted for use in a four barrel or four-way radial discharge barrel-assembly where only one barrel-tube is used, but the reverse. The miniball-holes 42 in each clip have been numbered for reference and do not appear on clips. The miniballs of each shot-group or discharge complement can each have a hole in a specially produced clip or a plug containing the smaller holes is inserted into the clip holes of the clip as manufactured. A beveled border surrounding each clip hole with the entry face directed back toward the valve body assists to contain and concentrate the propulsive against the miniballs.

The bevel is applied to the rim of the holes in the clip whether the miniballs have separate holes or are inserted into the clip hole as a group in a plug. The bevel edge is created by machine taper-reaming or by using the taper at the end of a drill bit in a drill press. Custom made clips include the bevel in the mold. If made by removing material around the clip hole, the bevel must not interfere with retention of the miniballs or the plug containing the shot-groups. To provide a deeper depression with an angled surround is readily accommodated in dedicated interventional airguns as addressed below in the section on airgun; however, to allow the use of thicker rotary clips or the placement of a beveled collar surround about each clip hole necessitates increasing the distance from the valve body outlet to the rear face of the clip, which may be impracticable.

The rotary magazine clips are separately sealed in a sterile airtight package and disposed of after use. An old and common device, rotary magazine clips are mounted by means of an axial hole at their center 43 to a hub or axle in the airgun and are rotated by the indexing action of an arm or pawl that rises to engage the circularly successive notches molded into the clip about its periphery or outer edge and pushes against each notch seen in FIGS. 30 and 31 but on the reverse or back side of the views provided and thus not seen in FIGS. 28 and 29) to obtain rotation as the sum of these rotational increments. Reloading the airgun is accomplished quickly, one rotary magazine clip pulled off the axle in the airgun and another inserted in its place.

The rotary magazine clips used in the airguns to be described are conventional in overall dimensions but situate one or more, usually up to four, miniballs for discharge at a single time. Barrel-assemblies which radially discharge eccentrically to treat eccentric lesions are fed from the same kind of rotary magazine clips with the changes in direction obtained by the course taken within the barrel-tubes. To more axially direct the propulsive force when the chamber is not airtight behind the barrel, and thus reduce diagonal vectors from the gas entry portal at the back of the chamber directed toward the rear of the slightly off-axis miniballs that are otherwise concentric thereto, the back hole can be drilled out to a larger diameter. Incorporation into the rotary clip holes of a slight circumferential ridge midway from the front to the back face prevents the miniballs from dropping out of the rotary magazine into the barrel before discharge.

The addition of this ridge allows the Model 617X airgun made by Maruzen Kabushiki Kaisha according to the specification of and sold by the Daisy Outdoor Products Company to shoot either miniballs or pellets, this model differing from the Model 622X of the same maker only in caliber and the ability to shoot miniballs as well as pellets. The rotary clips to be provided for use in an interventional airgun are unique in the caliber of the miniballs to be loaded. To spare the cost of preparing original molds to make the rotary clips, those in manufacture can be adapted by inserting a disk into the existing holes which contain the holes for the miniballs. When all the miniballs to be discharged at the same time are alike in mass, a slight midcircumferential ridge along the internal surface of each hole may be used.

Another way to retain the miniballs in the holes until discharge is to run povidone, cornstarch, syrup, molasses, acacia, methyl cellulose, or gelatin into the groove formed between the circumference of the miniball and the edge of the hole, allowing the syrup to form a uniform layer by surface tension, which is then freeze or quick dried by being passed under a heat lamp. Varying the formulation of the syrup in concentration and ingredients, such as sugars, starches, and the others just mentioned allows different degrees of adhesion that allow the loading of miniballs that differ in mass on the same rotary clip. Varying retentive adhesion inversely as the mass of the miniballs to be discharged together allows treatment of an eccentric distribution of lesions where some areas pose greater resistance to penetration or may require different medication in the form of an outer layer applied to the miniballs.

VII. Barrel-Assemblies

VII1. Types and Capabilities of Barrel-Assemblies

VII1a. Types of Barrel-Assemblies

Barrel assemblies and airguns differ in capabilities and suitability for a given procedure. To the extent possible, the apparatus is devised to cover a range of applications; however, no adjustment or attachment would allow a single apparatus to be used for widely different procedures. Supplementary radial projection units can be added to any barrel-assembly by ensheathment within a combination-form radial projection catheter, for example, but a given barrel-assembly must have a certain diameter, vary in radial projection units if any, and incorporate or lack gas pressure relief channels, for example. The functions involved not of the kind ordinarily performed on an intermittent or incidental basis during discharge implantation, combination-form barrel-assemblies are usually ablation or ablation and angioplasty-capable and seldom of the minimal ablation or angioplasty capability type.

Point to point diagnostic and therapeutic as well as diagnostic use of barrel-assemblies is addressed below in the section entitled Testing and Tests. Except for use in the bloodstream where gas embolism must be avoided, combination-form embodiments having an atherectomy cable running down the central channel to the distal tip can be supplemented by a back-end plug-in cold vaporization gas (carbon dioxide, nitrous oxide, or liquid nitrogen) spray can or cartridge, triggered spray can models CRYAC® and CRY-AC-3, available with an extension tip, supplied by Brymill Cryogenic Systems, Ellington, Conn., for example, being specially made for medical applications. The use of either heat or cold to treat different lesions is thus made possible.

Unused barrel-tubes used as service channels and radial projection unit ejection tool-inserts can eject contrast to confirm revascularization, an angiorelaxant such as nitroglycerin to aid passage, beta or calcium channel blockers, phosphorylcholine, and any number of other drugs locally at the site to be implanted. Barrel-assemblies can be classified into three essential types—those incapable of ablation or angioplasty, those having such capability only to the extent of serving during and as an adjunct to discharge implantation, and those capable of an ablation or angioplasty whether prior to and separately from or following engagement in the airgun. Use apart from the airgun denotes standalone or internal power and control rather than connection to the power supply and use of a control panel on the airgun.

The latter two types are also distinguished as usable or not usable in the bloodstream. Setting aside variability in diameter within any given type, barrel-assemblies are better defined as falling into one of eight classes, those more capable acceding to additional function by adding to the components required in simpler types. Those incapable of use independently of an airgun are:

a. Ablation and angioplasty-incapable, which include simple pipes and radial discharge Barrel-assemblies which lack heat-windows and radial projection units but must include a miniball recovery electromagnet, or trap-magnet, which requires connection to a power source. Radial discharge barrel-assemblies permanently enclose the barrel-tube for frontoradial discharge, and unlike simple pipe monobarrels, are not bendable.

b. Minimally or marginally ablation but not for use in the bloodstream much less angioplasty-capable, which often include heat-windows and radial projection units but do not require the pressurized gas diversion channels to prevent the entry of gas into the bloodstream (gas embolism), blood-grooves or blood-tunnels to allow some blood to pass reducing the risk of ischemia, but may include an embolic trap-filter as a backup dropped miniball recovery device.

c. Minimally or marginally ablation-capable, which for use in the bloodstream require gas embolism, thromboembolic, or ischemia averting features, such as pressurized gas diversion channels but are not angioplasty-capable. Such barrel-assemblies may incorporate an embolic trap-filter as a backup dropped miniball recovery device; an ablation and angioplasty-incapable barrel-assembly, meaning one incapable of use when disengaged from the airgun power source, when used in the bloodstream solely for discharge, must still incorporate gas diversion channels and be of radial discharge conformation.

d. Minimally or marginally ablation and angioplasty-capable, which require gas embolism, thromboembolic, and ischemia averting features, such as pressurized gas diversion channels and an embolic trap-filter. Ensheathment of a minimally ablation or ablation and angioplasty-capable barrel-assembly within a combination-form radial projection catheter of matching size effectively converts the barrel-assembly into a bipartite minimally ablation or ablation and angioplasty-capable barrel-assembly. It does not convert a minimally capable barrel-assembly into a fully capable one, because such a barrel-assembly draws power and is controlled from the airgun through terminal contacts in the end-plate such that removal from the airgun disconnects the barrel-assembly from its source of power. For clarity and to minimize human error, power and control are kept with the component served, so that a minimally capable barrel-assembly is not powered or controlled from the projection catheter power and control housing.

A minimally ablation or angioplasty-incapable barrel-assembly is self-contained to include an inmate power source and is therefore capable of independent manual use for every function but discharge, for which it is engaged in the airgun. It is, however, more expensive than a minimally ablation or angioplasty-capable barrel-assembly not intended for such versatile use and not equipped with an inmate power source. Electrical connection of the components within the barrel-assembly is ordinarily by connection made by engagement of the barrel-assembly in the airgun chamber. An embodiment of a minimally ablation or angioplasty-capable barrel-assembly intended to be capable of occasional manual use is connected to the airgun or another power supply by means of a small power patching cable, and is less costly than a fully capable barrel-assembly but is not usable as an independent apparatus.

Since such a barrel-assembly might be equipped with a battery, it will be seen that the transition from incapable to capable comprehends a continuous spectrum of embodiments comprehending every possible combination of features. Manually side-sweeping or side-swabbing the lumen walls transluminally with radial projection unit tool-inserts, the operator can stop and use the turret-motor to remotely rotate the brushes in order to better access the sides of the lumen not well covered because the barrel-assembly does not rotate manually with ease. The turret-motor can be used concurrently with manual use of the barrel-assembly. For example, the oscillatory mode, explained below in the section entitled Turret-motor Operational Modes, can be used with or without a lubricant released by ejection tool-inserts to assist in clearing tortuous stretches, and with side-sweeper type tool-inserts deployed, for example, a scrubbing, abrading, scraping, or shaving action.

The components within the barrel-assembly include tractive electromagnets to recover miniballs, a turret-motor, and in even a basic barrel-assembly intended for angioplasty, radial projection unit or units with trap-filter. Combination forms that include additional electrically operated components for transluminal use, such as a laser catheter or atherectomy burr, are operated with the barrel-assembly removed from the airgun during manual use. Such a barrel-assembly constitutes a means for ablation, or angioplasty to include atherectomy apart from its stenting function when inserted in the airgun. During discharge, the turret-motor can be used to rotate the muzzle-head, which can include one muzzle-port or multiple muzzle-ports (but rarely more than four) located about its circumference with radial symmetry or asymmetry.

As indicated, with an ablation or an ablation and angioplasty-capable barrel-assembly, the rotary mode of turret-motor operation can be used both during an ablation or an angioplasty with the barrel-assembly as an independent apparatus, or during implantation discharge, during which time the barrel-assembly is inserted into the airgun. Barrel-assemblies are intended to be usable in different type ductus. Those for use in blood vessels incorporate features to minimize procedural time, obstruction, and prevent gas embolism. Grooves and passages are provided to allow some blood to pass. Endoluminal time and obstruction is also minimized with the aid of a semiautomatic positioning system that allows miniballs to be placed more precisely in a relatively dense formation than might be achieved under manual control.

Nevertheless, the millimetric gauges of vessels can limit the embodiment employed to one containing but a single barrel-tube. Unlike a balloon, the muzzle-head of a barrel-assembly is not collapsible. For vascular applications, a radial discharge muzzle-head that includes from one to four barrels, usually two or four, referred to as two-way or four-way, is connected to the end of the barrel-catheter containing the barrel-tubes to form a unitized whole, or barrel-assembly. As explained below, a barrel-assembly to be used for placing implants at intervals too fine for manual control is automatically controlled in position if not the position-coordinated timing of the discharges.

Generally, a tight formation of miniballs is manually initiated, or triggered, and automatically executed. Whether intended for exclusively manual or for manual and automatic use, a barrel-assembly usually incorporates a forward drive and sag leveling and leveling and stabilizing device about the barrel-catheter, as described below in the section entitled Forward Drive and Sag Leveling and Stabilizing Device. One to three-way barrel-assemblies with barrel exit ports at different angles are used with vessels or other tubular structures that intimately attached to their substrate, resist dissection round and about without open surgery as would allow the vessel or duct to be completely surrounded by a full rather than a partial stent-jacket, whereas the four-way apparatus is used with structures readily freed from the substrate, allowing a full stent-jacket to completely surround or jacket the structure.

Generally, the obstruction posed by the barrel-assembly during a procedure in a coronary artery should not take more time than is required to achieve ischemic preconditioning (see, for example, Corcoran, D., Young, R., Cialdella, P., McCartney, P., Bajrangee, A., and 13 others 2018. "The Effects of Remote Ischaemic Preconditioning on Coronary Artery Function in Patients with Stable Coronary Artery Disease," *International Journal of Cardiology* 252:24-30; Zhou, C. C., Yao, W. T., Ge, Y. Z., Xu, L. W., Wu, R., and 13 others 2017. "Remote Ischemic Conditioning for the Prevention of Contrast-induced Acute Kidney Injury in Patients Undergoing Intravascular Contrast Administration: A Meta-analysis and Trial Sequential Analysis of 16 Randomized Controlled Trials," *Oncotarget* 8(45):79323-79336; Wang, S. Y., Cui, X. L., Xue, F. S., Duan, R., Li, R. P., and 3 others 2016. "Combined Morphine and Limb Remote Ischemic Perconditioning Provides an Enhanced Protection Against Myocardial Ischemia/Reperfusion Injury by Antiapoptosis," *Journal of Surgical Research* 202(1):13-25; Lu, X., Bi, Y. W., and Chen, K. B. 2015. "Olmesartan Restores the Protective Effect of Remote Ischemic Perconditioning Against Myocardial Ischemia/Reperfusion Injury in Spontaneously Hypertensive Rats," *Clinics* (Sao Paulo, Brazil) 70(7):500-507; Heusch, G., Bøtker, H. E., Przyklenk, K., Redington, A., and Yellon, D. 2015. "Remote Ischemic Conditioning," *Journal of the American College of Cardiology* 65(2):177-195; Zhu, S. B., Liu, Y., Zhu, Y., Yin, G. L., Wang, R. P., and 3 others 2013. "Remote Preconditioning, Perconditioning, and Postconditioning: A Comparative Study of Their Cardio-protective Properties in Rat Models," *Clinics* (Sao Paulo, Brazil) 68(2):263-268; Laskey, W. K. 2005. "Brief Repetitive Balloon Occlusions Enhance Reperfusion During Percutaneous Coronary Intervention for Acute Myocardial Infarction: A Pilot Study," *Catheterization and Cardiovascular Interventions* 65(3):361-367; Faircloth, M. E, Redwood, S. R., and Marber, M. S. 2004. "Ischaemic Preconditioning and Myocardial Adaptation to Serial Intracoronary Balloon Inflation: Cut from the Same Cloth?," *Heart* 90(4):358-360), extendible to 2½ to 3 minutes with the aid of medication (see, for example, Matsubara, T., Minatoguchi, S., Matsuo, H., Hayakawa, K., and 10 other authors, 2000. "Three Minute, But Not One Minute, Ischemia and Nicorandil Have a Preconditioning Effect in Patients with Coronary Artery Disease," *Journal of the American College of Cardiology* 35(2):345-351; Heidland, U. E., Heintzen, M. P., Michel, C. J., and Strauer, B. E. 2000. "Effect of Adjunctive Intracoronary Adenosine on Myocardial Ischemia, Hemodynamic Function and Left Ventricular Performance During Percutaneous Transluminal Coronary Angioplasty: Clinical Access to Ischemic Preconditioning?," *Coronary Artery Disease* 11(5):421-428).

Any application of outward radial force on the surrounding lumen, determined by the diameter of the muzzle-head, should not be continued longer than is intended to:

1. Reduce the risk of abrupt closure with or without concomitant vasospasm (vasoreflex, angiospasm) (see, for example, Arie, S., Checchi, H., Coelho, W. M., Bellotti, G., and Pileggi, F. 1990. "Coronary Angioplasty—Unstable Lesions and Prolonged Balloon Inflation Time," *Catheterization and Cardiovascular Diagnosis* 19(2):77-83).
2. Obtain more favorable morphological results (Zorger, N., Manke, C., Lenhart, M., Finkenzeller, T., Djavidani, B., Feuerbach, S., and Link, J. 2002. "Peripheral Arterial Balloon Angioplasty: Effect of Short Versus Long Balloon Inflation Times on the Morphologic Results," *Journal of Vascular and Interventional Radiology* 13(4):355-359), with reduced risk of restenosis (see, for example, Glazier, J. J., Varricchione, T. R., Ryan, T. J., Ruocco, N. A., Jacobs, A. K., and Faxon, D. P. 1989. "Factors Predicting Recurrent Restenosis after Percutaneous Transluminal Coronary Balloon Angioplasty," *American Journal of Cardiology* 63(13):902-905).

Using the noncollapsible muzzle-head, these occlusive durations should not necessitate the use of an extracorporeal perfusion system or chilling. If needed, however, newer cariopulmonary bypass machines incorporate filters that substantially eliminate the passage of microemboli to which sequelary intellectual deficits (postperfusion syndrome, postoperative cognitive dysfunction), renal insufficiency, and pulmonary dysfunction have been attributed (see, for example, Landreneau, R. J., Mack, M. J., Magovern, J. A., Acuff, T. A., Benckart, D. H., Sakert, T. A., Fetterman, L. S., and Griffith, B. P. 1996. "Keyhole" Coronary Artery Bypass Surgery," *Annals of Surgery* 224(4).453-462, also cited above).

However, if due to disruption of the blood-brain barrier secondary to the intervention, this would not remedy the condition (see Ogami, R., Nakahara, T., and Hamasaki, O. 2008. "Probable Blood-Brain Barrier Disruption after Carotid Artery Stenting—Case Report," *Neurologia Medico-chirurgica* 48 (3):121-125; Wang, Y., Kilic, E., Kilic, U., Weber, B., Bassetti, C. L., Marti, H. H., and Hermann, D. M. 2005. "VEGF Overexpression Induces Post-ischaemic Neuroprotection, but Facilitates Haemodynamic Steal Phenomena," *Brain* 128(Part 1):52-63; Latour, L. L., Kang, D. W., Ezzeddine, M. A., Chalela, J. A., and Warach, S: 2004. "Early Blood-brain Barrier Disruption in Human Focal Brain Ischemia," *Annals of Neurology* 56(4): 468-477; Warach, S. and Latour, L. L. 2004. "Evidence of Reperfusion Injury, Exacerbated by Thrombolytic Therapy, in Human Focal Brain Ischemia Using a Novel Imaging Marker of Early Blood-brain Barrier Disruption," *Stroke* 35(11):2659-2661).

Intermittent withdrawal, reentry, and resumption increases overall intracorporeal time thus defeating one object of invention. A combined angioplasty and implantation procedure in a carotid artery, for example, that requires the barrel-assembly to remain within the lumen for more than a minute may benefit from hypothermia. Continuing now the list of type barrel-assemblies thru d. begun toward the beginning of this section, those usable independently of an airgun draw power from an onboard power and control housing. In large caliber ablation and angioplasty-capable, that is, fully capable barrel-assemblies, which incorporate numerous built in features that require more control electronics and a high storage capacity power source, the housing if not well shaped for ambidextrous handling is provided with a hand-grip.

In fully capable Barrel-assemblies which are smaller in gauge, the housing itself can be configured as a pistol grip. Simpler and less capable embodiments can be configured as a pistol grip regardless of gauge. Regardless of conformation, the housing provides a control panel on its upper surface for instant viewability regardless of which hand is used. Continuing the discussion above ending with item d.:

e. Ablation but not angioplasty-capable, which incorporate within the muzzle-head and/or accommodate a bipartite radial projection system but is usually larger in gauge than an angioplasty-capable barrel-assembly and lacks the pressurized gas diversion channels, heat-window or windows for thermoplasty, blood passing channels, and embolic filter ischemia-preventive features essential for use in the bloodstream, or f. Ablation and angioplasty-capable, which include pressurized gas diversion and blood passing channels, a heat-window at the nose and often, an additional heat-window about the turret-motor or along the sides to burn potentially embolizing debris, and an embolic trap-filter (filter-trap, embolic filter), in addition to a radial projection system.

Angioplasty-capable barrel-assemblies are made in the millimetric gauge range. Within its size range, any barrel-assembly capable of performing an angioplasty is capable of performing an ablation but costs more to produce. An ablation and angioplasty-capable barrel-assembly includes at least one barrel-tube (qv.) and at least one radial projection system (qv.) in the muzzle-head as an aid to tracking. In a bipartite or duplex barrel-assembly, supplementary radial projection units are added to the barrel-assembly by sliding a through-bore or combination-form radial projection catheter over the barrel-catheter of the barrel-assembly before or after advancement to the treatment site.

g Ablation but not angioplasty-capable combination-form barrel-assembly, which is a through-bore radial discharge barrel-assembly with an edge-discharge muzzle-head and patent central channel through which a commercial cabled device such as a laser or rotational cutting tool or other catheteric device can be permanently or interchangeably inserted, that is, slid through the bore using the barrel-assembly in the manner of a guide catheter, midprocedurally with the barrel-assembly stationary in the lumen. An ablation but not angioplasty-capable combination-form barrel-assembly is usually equipped with a detachable snap-in nose-hole plug with torsion spring-loaded nose-hole cover to shut out debris during the exchange of cabled devices, lacks the pressurized gas diversion channels and ischemia averting features essential for use in the bloodstream, and is larger in gauge than a barrel-assembly that is also capable of an angioplasty. Ablation and ablation or ablation and angioplasty-capability is usually conferred by the incorporation of a radial projection system that is supplemented in a combination-form barrel-assembly with the addition of a laser or atherectomy cutter. Such a barrel-assembly is intrinsically ablation-capable, because its radial projection system imparts ablation capability even with the laser or cutter removed.

h. Ablation and angioplasty-capable combination-form, which is a millimetric range gauge through bore barrel-assembly. Like an ablation only combination-form barrel-assembly, an ablation or ablation and angioplasty-capable combination-form barrel-assembly has a patent central channel through which a commercial cabled device such as a laser or rotational cutter or other catheteric device can be permanently or interchangeably inserted. However, it also provides gas pressure diversion paths and ischemia countering features essential for use in the bloodstream, while omitting a nose-hole cover, which would close the central channel for blood to flow through when the channel is empty, and jut forward when open, risking incisions.

Within its generally smaller diameter range, combination-form barrel-assemblies capable of performing an angioplasty are understood to be capable of performing an ablation. Since ablation and angioplasty-capability is conferred by the incorporation of a radial projection system, the barrel-assembly is properly referred to as ablation or ablation and angioplasty-capable even with the cabled device removed. Combination-form barrel-assemblies are addressed in the section below of like title.

One object of the invention is to be able to accomplish both the removal of plaque or other obstructive matter and complete implanting the intraductal component of the extraluminal type stent described herein without the need to withdraw and reenter the lumen. An edge-discharge muzzle-head designed to contain a rotational burr or laser catheter at its center such as is incorporated into a combination-form barrel-assembly is equally capable of containing an endoluminal ultrasonographic probe or a cryogenic angioplasty balloon, numerous ablation and atherectomy devices on the market capable of being integrated into the barrel-assembly. Integration thus has as an object prepositioning to eliminate the need for withdrawal and reentry at times when these devices may be needed.

With an ablation or an ablation and angioplasty-capable barrel-assembly, a single vortex tube to provide cold or hot air, or a gas cylinder to provide cold gas of the required temperature, can be mounted at the rear of the barrel-assembly. To allow the cold or hot air or gas to reach the inner (rear, proximal) surface of the nose heat-window and circulate back into the central canal, the nose heat-window is separated from the outer surface of the ejection head and the gas delivery tube is smaller in diameter than the central canal. A nose window that is piped (provided to its rear with a barrel-tube diverted to serve as a supply line) may appear equally versatile in function to a piped radial projection unit; however, the value in an ability to project a fluid substance, change the temperature, or both, axially is limited.

The ability to disconnect the barrel-assembly from the interventional airgun and plug the vortex tube or gas cylinder into its proximal end at any moment makes possible ablation or angioplasty by the method preferred even mid-discharge, or following the initiation of stenting implantation. As indicated, when the central canal in an edge-discharge barrel-assembly is not occupied by a cold air gun or gas cylinder delivery tube, the distal end of the canal can be used to house a trap-filter silo by channeling recursive gas through gas-return paths that are outside (peripheral, radial) in relation to the barrel-tube or tubes.

The internal design of a barrel-assembly suitable for use in the vascular tree incorporates gas pressure relief means such as gas-return channels and a slit valve, so that the pressure of discharge is contained within the barrel-assembly; discharge with respect to the release of propulsive carbon dioxide gas or compressed air with the barrel-assembly in the vasculature, even when the airgun is not loaded, will not introduce gas into the bloodstream. The generally torpedo-shaped distal component of the barrel-assembly, or muzzle-head, supports the walls of a stenotic vessel or duct and is usually jointed to flex and grooved or furrowed to allow blood to pass over the surface. An ablation or angioplasty-capable barrel-assembly with a disconnectable control housing that has been disconnected is reduced to a minimally ablation or ablation and angioplasty-capable barrel-assembly.

That is, the feature that distinguishes a minimally from a fully capable barrel-assembly is the presence of a control housing. Because the central channel in a combination-form barrel-assembly can serve as a guide catheter for the insertion of a number of different cabled devices midprocedurally, it is preferred that any device inserted be interchangeable rather than built in. Because it must add some stiffness reducing trackability, a combination-form radial projection catheter is usually slid over the barrel-catheter of a barrel-assembly after the muzzle-head has been brought to the treatment site or level.

While the central component is a device such as an endoscope or thrombectomizer that cannot perform an ablation or an angioplasty, the apparatus is an ablation or angioplasty-incapable combination-form barrel-assembly. When the central component is a laser or atherectomy cutting tool, the apparatus is ablation or an ablation and angioplasty-capable combination-form barrel-assembly. Adding a radial projection system or peripheral component makes the combination-form barrel-assembly ablation or ablation and angioplasty-capable even when the central component does not impart this capability. For barrel-assemblies, pliancy for trackability is a primary desideratum. To allow a narrow gauge with pliancy for trackability, smaller ablation and ablation and angioplasty-capable barrel-assemblies generally incorporate only electrically operated radial projection units and only in the muzzle-head.

These radial projection units can be used to discharge a lubricant from ejection tool-inserts, adding slipperiness to narrowness, and the oscillatory mode of the turret-motor, can be used to assist in tracking. As addressed below in the section of like title, a combination-form radial projection catheter, or radial projection catheter with a central channel, can be slid over the extracorporeal or luminally prepositioned barrel-catheter as a kind of guide wire. The leading edge of the radial projection catheter is slip up to the rear of the muzzle-head. The coaxial pair can then have a reduced pliancy and increased gauge that would have prohibited luminal placement while at the same time extending radial projection units along the entire intracorporeal length. A combination-form radial projection catheter can be added to a barrel-assembly by being slid over the barrel-assembly barrel-catheter.

So that the front of a combination-form radial projection catheter can be slid forward over the barrel-catheter, an ablation or an ablation and angioplasty-capable barrel-assembly must provide a disconnectable power and control housing, or hand-grip configured battery-pack with the control panel mounted to the outside. Since most uses for a radial projection catheter do not relate to ballistic implantation, the catheter is made as an independent apparatus with its own power and control housing. When combined with the projection catheter slid fully forward so that its front edge abuts against the rear of the muzzle-head, the rear of the radial projection catheter power and control housing is slid back onto the barrel-catheter and flush against the rear of the projection catheter housing, the two in juxtaposed (adjacent, ganged) relation.

A small lock lever with cam detent at the bottom of each housing allows the housings to be slid along the barrel-catheter to any position and locked in place, much as the tail stop in a sliding pipe, pony, or bar clamp. Fixing the projection catheter housing in position prevents unintended sliding of the projection catheter along the barrel-catheter by contact with the lumen wall. Each apparatus made to be fully capable when independent of the other, the functions of each remains separate when the two are joined. Thus, electrically or fluidically connecting one into the other in order to eliminate one battery, for example, is not done. The combination is obtained with apparatuses of either type matched in gauge.

The power and control housing of the ablation or the ablation and angioplasty-capable barrel-assembly is disconnected, and the front end of the radial projection catheter is slid over the barrel-catheter of the barrel-assembly up into contact with the back of the muzzle-head. The interfaces, that is, front end of the radial projection catheter and rear of the muzzle-head complement in engaging relation that includes any electrical or fluid connectors. For trackability, the barrel-assembly is usually introduced without the radial projection catheter. If the lumen is too occluded for this, then a radial projection catheter of smaller gauge can be first be used independently to clear the way just enough so that the barrel-assembly can pass. Once in, the barrel-assembly is overlain by the radial projection catheter for its ablation or angioplasty functions.

If to be used during ballistic implantation, the radial projection catheter remains in place; otherwise it is withdrawn and the barrel-assembly used for placing the miniballs. To reduce the risk of injury when the radial projection catheter is introduced the outer edges at its leading end are rounded and any electrical or fluid connectors to the rear of the muzzle-head are placed medially (alongside the longitudinal axis). The combination of two such components is equivalent to an ablation or an ablation and angioplasty-capable barrel-assembly with integral radial projection catheter over its intracorporeal length, which is less versatile but less expensive. The combination can be thought of as an ablation or an ablation and angioplasty-capable barrel-assembly in two separable parts where for better trackability, the barrel-assembly can be introduced into the lumen first, then the radial projection catheter slid (advanced, tracked) over the barrel-catheter.

Bipartite barrel-assemblies are addressed below in the section entitled Distinction in Ablation or Angioplasty-capable Barrel-assemblies as Unitary or Bipartite. Barrel-assemblies are, however, substantially increased in capability when the barrel-catheter is encased within a surrounding jacket or sleeve that contains radially outward directed or side-looking tools such as injectors that allow the targeted release of medication into lesions, if necessary, at a preferred temperature, and cutting heads that can ablate or angioplasty. This capability is attained by introducing the barrel-assembly, situating the muzzle-head as necessary, and then using the barrel-catheter as a kind of guide wire to slide a combination-form radial projection catheter, as addressed below in the section of like title, until the distal or forward end of the latter abuts upon the proximal or rear end of the muzzle-head.

Electrical radial projection units in the muzzle-head can similarly use system-neutral syringe tool-inserts to reduce endothelial cling by ejecting a lubricant during transluminal and rotatory movement of the muzzle-head itself as well as to prepare the lumen for the covering of the barrel-catheter with a combination-form radial projection catheter. Electrical projection units in the muzzle-head are wired within the barrel-assembly. This allows their use independently of a radial projection catheter and avoids the need to torque (rotate) the barrel-assembly or to use the turret-motor to align electrical contacts at the leading edge of the projection catheter and rear of the muzzle-head in order to make the connection.

Fluid ejection tool-inserts or ejectors are not so limited being capable of emitting a fluid indefinitely; however, due to the greater space requirement that a fluid circuit imposes, these can only be incorporated into larger muzzle-heads. The terms ablation and ablation and angioplasty-capable are reserved for Barrel-assemblies which whether unitary or bipartite, include radial projection units. These units always accept interchangeable tool-inserts, and therefore always confer ablation or ablation and angioplasty-capability. Depending upon the device introduced into the central channel as the central component of a combination-form barrel-assembly, an ablation but not an ablation and angioplasty-capable barrel-assembly when the latter is used in the bloodstream can have fastened at the front a torsion spring-loaded nose-cover.

The different types of combination-form barrel-assemblies and use of hole-covers are addressed below in the section entitled Types of Combination form Barrel-assemblies. Characterization as to type is independent of the number of barrel-tubes. For optimal manipulability, airgun separable barrel-assemblies are preferably free-standing, or without connection to an external device such as by an electrical cord leading to a power source whether that within the airgun enclosure or housing. The combination-forms, however, when enclosing the cable of a laser, endoscope, and/or an atherectomizing device are tethered to the support electronics usually contained in a separate console.

VIIb. Capabilities of Different Type Barrel-Assemblies

A simple pipe consists exclusively of a ballistic component used to implant or recover miniballs. A simple pipe is a monobarrel without surrounding shell at the muzzle-head; shelled or jacketed at the muzzle-head, it would become a radial discharge monobarrel. Within the limits set by not constricting the bore, the muzzle-head of a simple pipe is also bendable prior to introduction, allowing adjustment for small apertures and awkward angles of approach to abut flush to the surface at the treatment site. Provision of a muzzle-head that is bendable after introduction is not addressed herein. Minimizing the entry cross sectional area, a simple pipe is intended for use where a flat-sided radially asymmetrical radial monobarrel of fixed cross sectional area would cause stretching injury to the laryngeal entry, for example, and a shell would interfere or prevent a clear view of the detailed anatomy at the aiming point.

Simple pipe barrel-assemblies will seldom be large enough in diameter to allow a service-catheter or miniature cabled device such as a laser or scope to be passed through the exit-hole or muzzle-port. However, to treat the lumen wall before or after discharge midprocedurally without the need to withdraw, larger simple pipes can be used thus. When not provided with a side-port, the barrel-assembly must be removed from the airgun to access its entry or proximal opening. Characterization of simple pipes as ablation and angioplasty-incapable is thus based upon a lack of intrinsic means therefor in the form of the radial projection units in capable barrel-assemblies.

Not only must the excimer laser or irreversible electroporation electrodes for ablating tissue addressed below in the section entitled Service Catheters pass through the muzzle-port but the operator must be provided with a clear view of the treatment area. This may necessitate the additional clearance to pass a subminiature fiberoptic endoscope. The same applies to all but the largest ablation or angioplasty-incapable radial discharge barrel-assemblies. The miniballs can consist of any kind of medication that can be prepared in the form of a tiny ball, and generally include adjuvant or implantation-supportive substances, to include a tumefacient, antibiotic, adhesive, tissue hardener, or surgical cement, for example.

Inserting such an isolated ballistic component barrel-assembly within the bore or central channel of a combination-form radial projection catheter effectively converts it into an ablation or an ablation and angioplasty-capable barrel-assembly despite the lack of radial projection units about the muzzle-head. Miniball constituents are organized for release in the sequence preferred. Miniballs not for use with a stent-jacket that despite high contrast might prove difficult to recover if misplaced or dropped, are provided with sufficient magnetically susceptible, usually ferrous material, if nonabsorbable, then encapsulated iron powder, if not, then superparamagnetic magnetite or maghemite nanoparticles or finely grained powder, to allow recovery with the electromagnets always present at the discharge end of every barrel-assembly.

Miniballs for stenting can consist entirely of magnetic stainless steel, usually encapsulated within layers of supportive medication or other therapeutic substances. A barrel-assembly with a peripheral component, or radial projection system, can use injection, ejection, inert bit cutting head, and temperature altering tool-inserts to prepare the treatment site for and/or provide followup treatment to ballistic implantation with single luminal entry. Preparation generally consists of removing diseased or obstructive tissue. It is the peripheral component that imparts ablation or angioplasty capability. Both preparation and followup can include the injection at a preferred temperature of a tumefacient, antibiotic, surgical cement, or tissue hardener, for example, into the lumen wall.

When ballistic implantation is not contemplated, an ablation or an ablation and angioplasty-capable barrel-assembly, combination-form barrel-assembly, separate radial projection catheter, or combination-form radial projection catheter can be used to clear and introduce any kind of injectable medication and/or other substance into the wall of a diseased or obstructed ductus. Barrel-assemblies and miniball implants have applications unrelated to stenting. A barrel-assembly without a peripheral component (radial projection system), can be used to implant medication ballistically, and barrel-assemblies with a peripheral component can be used to effect interventional measures such as the removal of diseased or obstructive tissue by cutting, thermoplasty, or cryoplasty, and the targeted introduction into lesions along the lumen wall of any fluid substance by injection as well as ballistically in any combination.

Either a simple pipe with an endoscope permanently fastened or lashed alongside or a radial discharge barrel-assembly with an attached or built in angioscope or fiberoptic endoscope is used to implant medication and/or radioactive seed miniballs in the wall surrounding the tracheobronchial airway, gastrointestinal tract, or a body cavity, for example. Much stenting of the airway will be veterinary or pediatric using a simple pipe with a padded distal end to prevent gouging. Radial discharge barrel-assemblies are intended for use primarily in ductus and vessels that tend to lack anatomical landmarks where the lumen transmits blood or other contents and the size of the vessel or duct is such that maneuverability and accurate positioning are difficult or impossible. Less well defined and extensive lesions will similarly present little structural differentiation. Stay insertion tools are readily applicable to structured and unstructured lumina.

To assure recoverability if dropped or mispositioned, medication miniballs and stays, which must fully disintegrate, incorporate superparamagnetic magnetite or magnemite. Minimally or marginally ablation or ablation and angioplasty-capable barrel-assemblies are intended to apply ablative or angioplastic action as adjunctive to implantation discharge, whether preceding, during, or succeeding discharge, and are airgun-dependent. More specifically, minimally capable barrel-assemblies are for noncomplex lesions where any vulnerable or unstable plaque would be destroyed by being swept over by a cautery prior to discharge. Such barrel-assemblies may substitute a nonmotor heating coil with wraparound heat-window for a turret-motor with heatable windings as a secondary function, and omit radial projection units.

These therefore lack an inmate source of power or an onboard control panel and are seldom equipped with all of the tissue reduction features of ablation or ablation and angioplasty-capable barrel-assemblies, whence the designation 'minimal.' Because a pistol allows greater manipulability, minimally capable barrel-assemblies for use with pistols warrant more of these features and may match capable embodiments in ablative ability. However, a pistol does not permit the control over exit velocity or precise placement as does a stage mounted interventional airgun. Thus, although not configured for separate manual use, minimally capable barrel-assemblies are not necessarily less well equipped or capable in the more limited ability to deliver heat or ablative action per se.

When not requiring to be distinguished as to usability in the bloodstream, minimally capable barrel-assemblies, as airgun dependent for powering the internal components and thus requiring electrical reconnection whenever removed from the airgun, are referred to collectively as minimally or marginally ablation or ablation and angioplasty-capable barrel-assemblies. Ablation and ablation and angioplasty-capable barrel-assemblies include the capabilities of minimally capable barrel-assemblies but are usable independently of an airgun. Unless duplicate controls are mounted on the airgun enclosure (for use by an assistant), the control panel is not placed there but rather immediately and ambidextrously on top of the grip-configured power and control housing.

The advantage in the ability to use the barrel-assembly independently of an airgun is the freedom of manipulation essential to accomplish the preparatory therapeutic measures for implantation and then, inserting the proximal end in the airgun, initiate implantation discharge without the need to move or withdraw. When discharge implantation is not contemplated, the barrel-assembly can be used as a separate apparatus or a radial projection catheter used instead. Distinguished as to usability in the bloodstream, both ablation and ablation and angioplasty-capable barrel-assemblies are equipped, internally powered, and usable apart from an airgun, the angioplasty-capable type comprehends the function of the equivalent ablation only barrel-assembly, but is limited to the range in size suitable for use in the bloodstream.

Since Barrel-assemblies which are capable of angioplasty as well as ablation encompass the function and can accomplish the work of the comparable ablation only or angioplasty-incapable type, and the difference between these consist of gas pressure diversion means, the figures depict the angioplasty-capable type. Simple pipe barrel-assemblies lack a torpedo-shaped body shell or jacket about the muzzle-head when this is unnecessary for preventing perforations expedite direct aiming in relation to the structured or differentiated anatomy inside the trachea, for example. Since this jacket is also needed to mount ablation or angioplasty components, a simple pipe is limited to the placement and recovery of miniballs. When disengaged from the airgun, a simple pipe can be used for aspiration, irrigation, or to deliver a therapeutic solution, for example.

Ablation or angioplasty-incapable barrel-assemblies serve as extensions to the airgun barrel that are configured to allow the delivery of implants into the wall of a lumen, or exceptionally, into the body wall (paries) or an internal organ. These include simple pipes and radial discharge Barrel-assemblies which lack the essential to features perform an ablation or an angioplasty, to include radial projection units, heat-windows, a trap-filter, all described in sections of like title to follow. Functionality inseparable from cost, this type can be made at least cost. Since adding features tends to increase diameter, certain circumstances may call for relinquishing nonessential features to allow greater clearance.

While no simple pipe, which is a barrel-assembly without a protective outer shell or jacket surrounding the muzzle-head, and not all radial discharge barrel-assemblies are ablation much less angioplasty-capable, all ablation or ablation and angioplasty-capable barrel-assemblies are of the radial discharge type. Minimally ablation or ablation and angioplasty-capable barrel-assemblies are meant to allow ablation or angioplasty intermittently or continuously during discharge. Seldom critical, the transit time for discharge can usually be set to match the optimal exposure time of the lumen wall to heat or other tissue removal shaving or abrasive action used.

Because the recovery electromagnets toward the nose of the muzzle-head should remain available for recovering any dropped miniballs during discharge, the conjoined processes are usually performed during retraction or withdrawal rather than advancement with an annular turret-motor winding heat-window supplying the heat. While not meant to be used apart from the airgun and not requiring a more elaborate side-socket for connecting different electrical and fluid lines, a minimally ablation or ablation and angioplasty-capable barrel-assembly still requires access down the central channel or a barrel-tube for the limited purpose of admitting a temperature-changing catheter or cold air gun line for quickly dropping the temperature down from that used to ablate or thermally angioplasty or elevate the temperature when terminating cryoablation or cryoplasty.

This is best accomplished without modification to the barrel-assembly by removal from the airgun and passing the temperature-changing catheter through the end-plate. Exceptionally, a simple side-socket with dedicated barrel-tube, preferably one diverted to serve as a radial projection unit pipe, can be incorporated. While ballistic discharge requires connection to an airgun, ablation and ablation and angioplasty-capable barrel-assemblies can be made fully self-sufficient for performing an ablation and/or angioplasty. The embedded microcontrollers and other components required follow from the features embodied. These can include a turret-motor and recovery electromagnets that can be switched from functioning as actuators to functioning as heating elements, electrical and/or fluidic radial projection systems, and a viscous or daspot damped solenoid deployed and retracted run-ahead embolic filter.

In a combination-form barrel-assembly, an electrical and/or fluidic side-socket allows the control console of the cabled device inserted to be operated by an assistant. A side-socket can also allow connection to a number of external canisters (cylinders, tanks) containing various medical and flush fluids that an internal reservoir not configured to accept refill containers for fluid delivery or cisterns for collection during aspiration cannot accommodate. When discharge requires the turret-motor to rotate the muzzle-head making the turret-motor unavailable as a heating element, hot-plate radial projection unit tool-inserts are used for this purpose. To minimize confusion and the risk of human error, controls are kept with the device controlled. With a minimally ablation or ablation and angioplasty-capable barrel-assembly, the controls for these, just as for radial projection units when shaving or abrading tool-inserts are used, are mounted to the airgun.

In barrel-assemblies which afford sufficient diameter, the nose can contain a heat window that encircles a cabled device, such as a fiberoptic endoscope or an embolic filter silo with deployment solenoid. Such a heat-window is a hemitoroidal dome with the convex surface directed forward (downstream, distad). In an embodiment that includes abrading or cutting (shaving) tool-inserts, either a laser or an embolic filter will serve to eradicate any debris that might risk embolization. An embolic filter can be simultaneously deployed when an atherectomizing tool is energized. To be certain that the filter is deployed before debris is generated, the tool receives current only after a brief delay. To avert the release into the lumen of debris from vulnerable or unstable plaque, the filter can also be deployed independently following introduction of the catheter.

When the tool is turned off and thus retracted (stowed), the filter is retracted into the silo following a brief delay. Also independently deployable and retractable, concern that debris may be liberated upon withdrawal is responded to by overriding automatic retraction. Should a minimally capable barrel-assembly be ensheathed within a combination-form radial projection catheter as a bipartite ablation or ablation and angioplasty-capable barrel-assembly, as addressed below in the section entitled Through-bore, or Combination-form, Radial Projection Catheters, then the controls are located at the top of the projection catheter power and control housing. The object in combining discharge and thermal angioplasty capabilities, for example, is to destroy vulnerable plaque and potentially embolizing debris before stenting as a routine precaution but more immediately, to preclude the fractures of fibrous caps by contact with the apparatus.

Hyperplastic sequelae are avoided by medicating and/or irradiating the miniballs, which inherently targeted, considerably reduces if not eliminates the need for systemic medication. While such a barrel-assembly incorporates means for ablation or angioplasty, it is not meant for use apart from the airgun. Accordingly, power for its internal components—turret-motor, recovery electromagnets, radial projection units, and trap-filter—is drawn from the airgun power supply, and the signals for controlling these components are set on the airgun control panel. The connections for both are made through the end-plate at the proximal end of the barrel-assembly when engaged in the airgun chamber.

In Barrel-assemblies which lack a side-socket, the end-plate must serve as an end-socket, as addressed below in the section entitled Ablation or Ablation and Angioplasty-capable Barrel-assembly End-socket, for the attachment of external devices, necessitating disengagement from the airgun and thus disabling discharge. By contrast, barrel-assemblies with a side-socket, as addressed below in the section entitled Ablation or Ablation and Angioplasty-capable Barrel-assembly Side-socket, can continue to discharge medication miniballs, for example, at any time during the primarily initial ablation or angioplasty procedure. Reciprocally, an end-socket disallows the application of chilled gas during discharge. To provide such a barrel-assembly with a side-socket that would maintain power while the barrel-assembly was removed from the airgun would impart greater functionality.

However, that would make it an ablation or ablation and angioplasty-capable type, as addressed below, but one inadept in remaining tethered and lacking the onboard power and control panel that yield the self-containment and gain in range and ease of use, or functionality, that make an ablation or ablation and angioplasty-capable barrel-assembly worth the additional expense. By contrast, a proper ablation or ablation and angioplasty-capable barrel-assembly need be tethered only when a combination-form, as addressed below, with commercial laser or a specially adapted rotational atherectomy burr, for example, installed. Since engagement in the airgun interferes with free manual use or manipulation, the discretionary use of such a barrel-assembly for use while connected to and drawing power from the airgun power supply before initiating medication and/or stenting miniball discharge is accomplished with the aid of the rate of advancement or retraction-setting linear positioning stage to which the airgun is mounted.

Separate use of the barrel-assembly before or removing it from the airgun during implantation discharge to allow free manipulation necessitates reconnection to a power source, usually reconnection to the airgun power supply through an external socket on the airgun enclosure. Ablation or ablation and angioplasty-capable barrel-assemblies are meant to be capable of performing an ablation or an angioplasty independently of an airgun. In so doing, the barrel-assembly supplants alternative methods of treatment, such as balloon angioplasty. Having completed this action, such a barrel-assembly can be inserted into an airgun to initiate stenting implantation discharge without the need for withdrawal from and reentry into the body.

Self-contained and able to attach additional components by means of a side-socket, ablation and ablation and angioplasty-capable barrel-assemblies can be freely inserted into or removed from an airgun whenever necessary and therefore allow discharge which can be intermittently interrupted for ablative or angioplastic use without the need to withdraw and reenter. Discharge can be to deliver medication miniballs preparatory to the ablation or angioplasty or pursuant to that just completed, or to emplace the intraductal component of an extraluminal stent. Different or multicoated miniballs can be used to accomplish medication, stenting, or both, and the operator can freely switch between angioplasty and discharge as desired.

While not preferred as losing the advantage in the ability to immediately shift between ablation or angioplasty and stenting without the need to withdraw, such a barrel-assembly can also be used to perform an angioplasty preparatory to conventional (endoluminal) stenting or to stent following conventional (balloon) angioplasty. Barrel-assemblies for use in the circulatory system must incorporate pressurized gas diversion and pressure dissipation channels, plural means for preventing a dropped miniball from being carried off by the bloodstream, and blood-grooves, blood-tunnels, and radial projection units as means for minimizing obstruction to the flow of blood. These components are described in sections of like title below. Angioplasty-capable barrel-assemblies thus usually exceed the complement of features required in Barrel-assemblies which are capable of ablation but not angioplasty.

Since these are made for use in the vascular tree, a narrow diameter is essential at the same time that gas return channels and usually blood-grooves must be provided. Combination-form barrel-assemblies are addressed below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy. Luminal diameter the limiting factor, combination-form barrel-assemblies for use in the vascular tree will usually be restricted to no more than two barrel-tubes. When the nose-hole of a combination-form barrel-assembly or a combination-form radial projection catheter is left uncapped when introduced into an artery, the central channel must first be allowed to fill with blood. This is accomplished by pausing with the proximal side-port or ports extracorporeal to vent air from the central channel.

Wetted with heparin solution, the central channel can then be a. Left unoccupied for blood to flow through, b. Used as a guideway for numerous different therapeutic and/or viewing interventional devices which can be changed midprocedurally without the need to withdraw the barrel-assembly, or c. Used to permanently enclose such a device or a form thereof adapted for the purpose. If occupied but leaving sufficient cross sectional clearance, the central channel may still allow some blood to pass. If the muzzle-head or radial projection catheter is smaller in outer diameter than the ductus, blood will flow past along its periphery. If fine enough in diameter, more than one device, such as one for viewing and another for performing work, can be accommodated.

If not inserted prior to entry, a singular catheteric or cabled device that matches the central channel in diameter is inserted gradually to minimize pumping pressure on the blood within the central channel, and when withdrawn with the combination-form remaining stationary within the lumen, then gradually to minimize the vacuum created. Commercial lasers and devices for intraductal ultrasound and endoscopy, for example, require connection to a remote control console, and thrombectomizing and atherectomizing devices are powered and controlled from a hand piece. Such devices are inserted distal end first into the combination-form through a larger proximal side-port that remains well extracorporeal and does not interfere with intermittent reinsertion of a barrel-assembly in the airgun if necessary for discharge or to take advantage of the precise transluminal positioning capability imparted by the airgun linear positioning stage.

For use in a ductus containing debris, such as in the gastrointestinal tract, especially when it is desired to exchange viewing devices, the central channel in a combination-form barrel-assembly or radial projection catheter should be prevented from obstruction. To this end, the nose-hole has inset a plug consisting of a surround extending rubbery or resilient fingers toward the center where the free ends meet. When retracted, the fingers wipe down the sides and front end of the protruded portion of the cabled device and close behind it to block the entry of debris. A snap-in spring-loaded nose-cap is not preferred as opening to one side and thus necessitating additional protrusion to attain an unobstructed field. Such self-closing mechanisms are unsuited to use in the bloodstream where it would obstruct the flow of blood or in the airway where it would obstruct the flow of air whenever the central channel was left empty, which in most instances is for this express purpose.

Ablation or ablation and angioplasty-capable barrel-assemblies are radial discharge barrel-assemblies with radial projection units and a turret-motor with windings that can be heated to perform a thermal angioplasty. Combination-form barrel-assemblies additionally incorporate a laser, endoscope, intraductal ultrasound, or other usually static component within the central canal or allow passage therethrough of a rotatory cutting tool. To enlarge the central canal, the barrel-tubes must be situated radially outwards, which configuration is referred to as edge-discharge. A configuration whereby the barrel-tubes are closer toward the central axis is referred to as center-discharge.

Ablation or ablation and angioplasty-capable barrel-assemblies generally confine radial projection units to the muzzle-head where these can be used, for example, to release a lubricant during transluminal movement rather than include a radial projection jacket that extends over the intracorporeal length that would adversely affect flexibility, hence, trackability. When an ablation or ablation and angioplasty-capable barrel-assembly with permanent radial projection jacket extending over its intracorporeal length lacks sufficient flexibility to track a curved or tortuous stretch, a radial discharge barrel-assembly without radial projection units other than in the muzzle-head is positioned in the lumen first and a combination-form radial projection catheter slid over the barrel-catheter in the manner of a guide wire.

Combination-form radial projection catheters are addressed below in the section below of like title. Ablation or ablation and angioplasty-capable barrel-assemblies comprised of a size-matched barrel-assembly and a combination-form radial projection catheters are addressed below in the section entitled Distinction in Ablation or Ablation and Angioplasty-capable Barrel-assemblies as Unitary or Bipartite. Neither type cable prevents flexion of a convoluted segment joining proximal and distal portions of a flexible muzzle-head. Thermoplasty-capable barrel-assemblies require a muzzle-head body (outer shell, jacket) with heat conductive and insulative properties to permit the heat generated within the body to be transient conducted toward the lesions, most often atheromatous, which are usually delimited longitudinally and radially asymmetrical, in a directed manner as described below.

Polytetrafluoroethylene-coated nonferromagnetic stainless steel affords the surface slippage to avert endothelial clinging. Whenever the turret-motor is joined to the more distal elements of the muzzle-head (ejection head, recovery electromagnet assembly) by a segment or joint of flexible convoluted tubing, the muzzle-head body shell must be divided between the portions of the muzzle-head distal and proximal to the flexible joint. While heat-windows, slits, or slots for thermal angioplasty (addressed below) heated by sending heating current to both the turret-motor and the electromagnet assembly in a center-discharge muzzle-head must be divided between the shells proximal and distal to the flexible joint, the path through the barrel-assembly for passing a capillary or filiform catheter for rapid cooling of the heated elements to body temperature through a spare barrel-tube (service-channel) or the central canal of the peribarrel space and up through the capillary catheter channel in the ejection head in only this type of barrel-assembly is continuous.

In a combination-form barrel-assembly, the central canal may be occupied by the cable of a therapeutic device, such as a laser, and/or viewing device such as an endoscope or intraductal ultrasound probe, making it unavailable for insertion of a cooling catheter. With this type of barrel-assembly, which requires an edge-discharge muzzle-head such as shown in FIG. 66, the cooling catheter must be passed down to the muzzle-head through an available barrel-tube. Because the internal diameter (caliber, gauge) of the barrel-tube can be on the order of 0.4 millimeters, the cooling catheter must be thin. To allow the cooling catheter to be fed down to the muzzle-head thus requires that it be made of a relatively rigid polymer, usually polytetrafluoroethylene.

In barrel-assemblies designed to use the turret-motor or tractive electromagnets as heating elements for thermal angioplasty, these same materials afford the effectively nonmagnetic properties and low thermal conductivities or heat transfer coefficients, so that by placing a pane of sheet silver or copper, which are high in thermal conductivity, in the muzzle-head body, allows heat regulated in temperature by controlling the current to the windings, to be directed, in effect beamed, from the body toward the lumen wall over a defined area. Unlike simple pipe barrel-assemblies, which are intended for use primarily in the airway, radial discharge barrel-assemblies are intended to be usable in the vascular system as well as small and structurally undifferentiated ducts. The latter factor and need for operative speed account for embodiments that are able to deliver multiple implants with each discharge.

Figures 43, 44, 45:
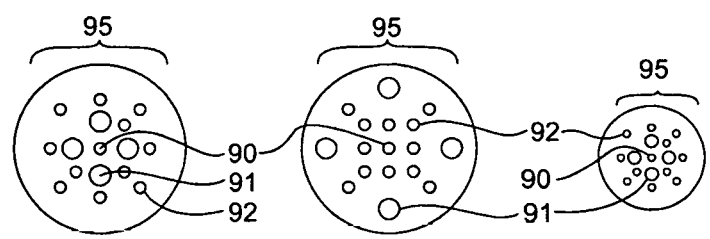
FIG. 43 is a full-face cross-section view along line G-G' in FIG. 41 through a centering device in a center-discharge ablation or angioplasty-incapable four barrel-tube radial discharge barrel-assembly wherein the barrel-catheter is relatively large in diameter.
FIG. 44 is a full-face cross-sectional view as if taken along line G-G' in FIG. 41 through a centering device in an ablation or angioplasty-incapable four-barrel radial discharge barrel-assembly suitable for use in an edge-discharge barrel-assembly or in a barrel-assembly that places the barrel-tubes more distant radially from the longitudinal axis of a relatively large diameter barrel-catheter.
FIG. 45 is a full-face cross-sectional view as if taken along line G-G' in FIG. 41 through a centering device of a center-discharge ablation or angioplasty-incapable four-barrel radial discharge barrel-assembly that places the barrel-tubes less distant radially from the longitudinal axis of a relatively small diameter barrel-catheter.

As opposed to use in a body cavity, the use of a simple pipe barrel-assembly in a ductus or vas in a human is essentially limited to the airway. Ablation or angioplasty-incapable (plain discharge, limited purpose) radial discharge barrel-assemblies as shown in FIGS. 34, 35, and 43 are limited to use with an airgun for implantation and might be used independently of an airgun only as an aspiration line. By contrast, ablation or ablation and angioplasty-capable barrel-assemblies (angioplasty barrel-assemblies, thermal angioplasty barrel-assemblies), such as those shown in FIGS. 44, 48, 49, 50, might be used solely to perform an angioplasty even when not planned to be followed by stenting, or might first be used independently of an airgun for angioplasty, and thereafter, without withdrawal from the patient, inserted at the free or proximal end into the barrel of an airgun to initiate stent implantation.

Unless it incorporates a rotatory atherectomy burr or laser catheter, an angioplasty barrel-catheter powered by a hand-grip shaped lithium-polymer or silver-zinc battery pack need not be tethered, or connected by hard wiring to a power supply whether inmate in the airgun or another. With either a rotational cutting burr or laser incorporated, local controls are included in the onboard barrel-assembly control panel, but the burr pneumatic drive and laser photoactivation components within the consoles of these cannot be miniaturized for incorporation into a barrel-assembly, which accordingly requires a pneumatic or fiberoptic cable connection. However, stenting always follows angioplasty, and the connection to either such drive, which is located at the proximal end of the angioplasty barrel-assembly, is designed to allow immediate disconnection from the console and reconnection to the airgun by means of the same connector fitting.

The barrel-assembly should be devised and chosen to avoid unnecessary length. Bends are eliminated from the initial period of discharge by providing the airgun with a barrel of some length, into which the proximal length of the barrel-assembly is inserted. In an angioplasty barrel-assembly, this would result in the length of the barrel-assembly to be inserted into the barrel of the airgun extending proximally past the hand-grip shaped battery pack with control panel mounted, thus denying use of this length when or while the barrel-assembly was used independently of the airgun for angioplasty. Rather than to allow the proximal segment of the barrel-assembly, or barrel insertion segment, to be denied for intraductal insertion, the hand-grip is slid backward or toward the proximal end of the barrel-assembly when the barrel-assembly is used independently of the airgun for angioplasty.

Angioplasty preceding stenting, the hand-grip is initially in the proximal position where it is in electrical contact with the terminals to each side-sweeping brush or other radial projection unit tool-insert lift raising thermal expansion wire as addressed below in the sections below entitled Radial Projection Units, Structure of Electrically Operated Radial Projection Units, and Radial Projection Unit Control and Control Panels, Elecrical and Fluidic or Piped, and the turret-motor and recovery electromagnets while used as heating elements for thermal angioplasty. When the barrel-assembly is to be inserted into the barrel of the airgun, the grip with forward drive and sag leveling and stabilizing device if present is slid forward or distally up to a detent or stop marking off the length of the airgun barrel and disconnecting the onboard battery pack from electrical contact with these terminals, which then can make contact with the terminals within the chamber of the airgun or attached to the hand-grip.

In use for implantation, the barrel-assembly is generally a passive component of the interventional airgun. When an ablation or an ablation and angioplasty-capable barrel-assembly is not needed for discharge implantation, the proximal end-plate need not be inserted into an airgun. An end-socket therefore allows connection to an external apparatus such as an aspiration pump, refrigerant line, or endoscope as necessary. If the barrel-assembly is of the combination-form type with a central channel, then commercial cabled devices can be incorporated also. When the barrel-assembly must remain engaged in the airgun, a side-socket is necessary. An ablation or ablation and angioplasty-capable barrel-assembly, which except for implant discharge can be used independently of an airgun, is powered by an on-board battery pack in the power and control housing and not tethered by an electrical cord.

It should seldom if ever be necessary to take power and electrical control signals through an electrical cable regardless of the number and type of components used. Current battery technology and an onboard servodrive or amplifier controller to execute programmed oscillation of the turret-motor as addressed below in the sections entitled Turret-motor Operational Modes on a sustained basis allow the barrel-assembly to remain portable and untethered. An ablation or ablation and angioplasty-capable barrel-assembly for use in an airgun but detachable therefrom as desired can take power from an onboard battery pack, a cable or cables, or from the airgun power supply through an extension cord and side-socket, as addressed below in the sections entitled Engagement of the Barrel-assembly in the Airgun and Barrel-assembly Side-socket and must relegate hosing to a fluid line connecting side-socket.

Completely separate and independent use is always preferred to external connection. For free manipulability, an ablation or ablation and angioplasty-capable barrel-assembly is kept free from outside connections, incorporating whatever electronic and fluidic components are needed, so that insertion in the airgun is necessary only to use the airgun linear positioning stage for precise transluminal movement or to initiate or reinitiate the discharge of medication or stenting miniballs. The use of lithium ion or thin-film batteries gains interior space. Small cylinders of pressurized gas are mounted on the barrel-assembly and attached directly to the end or side-socket as applicable.

When tethering is unavoidable, as when an outside sources of gas that uses a large cylinder or an auxiliary apparatus such as a laser or rotational atherectomy tool that uses its own control console is required, interference with free movement is minimized through the use of a side-socket having electrical connectors, a portal for admitting a fluid hose, and fluid couplings as necessary. A side-socket is preferred to an end-socket or plug at or beside the terminal plate as allowing the proximal end of the barrel-catheter to be freely entered and removed from the airgun so that the delivery of s gas or continued use of an external device can continue without interruption whenever the barrel-assembly is inserted into or removed from the airgun.

With the incorporation of a side-socket for electrical and/or fluid connection, insertion or removal of the barrel-assembly from the airgun has no affect on the delivery of power and fluids. If power is taken by connection within the airgun chamber to the airgun power supply, then to be able to remove the barrel-assembly without losing power necessitates that the barrel-assembly remain tethered to the airgun through an electrical cord that is connected to the barrel-assembly by means of a side-socket, usually one that includes both electrical and fluid connections. A barrel-assembly that is meant only for implantation discharge must still have a source of power for a recovery electromagnet that must be available to retrieve any misplaced or loose miniballs.

Since such a barrel-assembly is never used independently of an airgun, it draws power through the airgun chamber. The loss of an implant within the vascular tree unacceptable, means are provided to minimize the risk of such an eventuality and to recover the implant. Every barrel-assembly to be described is equipped with at least recovery electromagnets for retrieving loose and extracting mispositioned implants. The miniball recovery electromagnet or electromagnets in a simple, or ablation or angioplasty-incapable barrel-assembly, are electrically connected to the airgun power supply upon engagement of its proximal end in the airgun chamber.

The current to the recovery electromagnets in a simple barrel-assembly is accordingly controlled from the airgun control panel. Unlike a simple or incapable embodiment, a noncombination-form ablation or ablation and angioplasty-capable barrel-assembly not requiring outside connection must be capable of use as a self-contained apparatus. Incorporating radial projection units that must accommodate tool-inserts capable of different processes which must be coordinated, such a barrel-assembly requires its own onboard control panel. When only used to perform either an angioplasty or to introduce intraductal implants, conventional means are employed to perform the other procedure.

When the implants must be spaced too closely together for discharge to be controlled by hand, a positional control system is used to effect discharge automatically. Whereas ablation and ablation and angioplasty-capable barrel-assemblies can ablate or angioplasty as well as discharge implants, a stay insertion tool can only be used to introduce implants. When stenting is uninvolved, both miniball and stay implants can consist entirely of medication and/or irradiating seeds. The medication can be antiangiogenic, proangiogenic, proneurogenic, chemotherapeutic, oncolytic viral, antibiotic, nanotechnological, or gene therapeutic, and released at a controlled rate so that delivery is closely targeted for the diseased tissue. Outside of the circulatory system, the recovery of implants is seldom an emergency and accomplished readily.

Usually too small in diameter to induce a cerebral or myocardial infarction in an artery of exclusive or nonoverlapping territory with platelet blockade administered, the miniball implants used are of sizes as would result in end-circulation foreign body embolism were any to escape into the bloodstream (see, for example, Macdonald, R. L., Kowalczuk, A., and Johns, L. 1995. "Emboli Enter Penetrating Arteries of Monkey Brain in Relation to their Size," *Stroke* 26(7):1247-1251; Fisher, C. M. 1969. "The Arterial Lesions Underlying Lacunes," *Acta Neuropathologica* 12(1):1-15; Agranoff, A. B. and Wong, E. H. 2006. "Lacunar Stroke," http://www.emedicine.com/pmr/topic63.htm), making it imperative that means be incorporated into the muzzle-head to prevent such losses. Emergency extraction of an embolizing miniball is addressed in section X2c below entitled Stereotactic Arrest and Extraction of a Circulating, Dangerously Positioned, or Embolizing Miniball.

For this reason as well as to intentionally retract a mispositioned miniball after implantation, the muzzle-head of a radial discharge barrel-assembly for use in the bloodstream always includes a recovery and extraction miniball electromagnet assembly supported by a trap-filter, both of which run ahead, that is, are positioned distal to the muzzle-ports or holes through which the miniballs are projected and can usually remain energized during discharge. Recovery can also be accomplished by connection of a barrel-tube or the entire proximal end of the barrel-assembly to a vacuum pump, as addressed below in the section entitled Muzzlehead Access by Means of a Service-channel. Each of the diametrically oriented recovery electromagnets in the pair is separately controllable.

To allow the electromagnets to be deenergized (turned off) when not needed or to avoid the risk of unintentionally retracting a miniball that has been successfully implanted, each electromagnet is situated behind a spring-loaded plastic trap door that is pushed aside (inward) by the miniball as it is drawn toward the magnet. Once in the magnet-trap, or magnet antechamber, the spring closes the door behind, trapping the miniball in the magnet-trap allowing the magnet to be deenergized. To minimize the likelihood for the drawing of a miniball toward a magnet so that rather than to find its way through the trap door it becomes forcibly held or stuck against the outside of the muzzle-head requiring that the magnet be deenergized to release it, the area of the trap doors, or the doorway should be as large as possible to provide the least obstructed opening before the lines of force which are substantially oriented behind and across the doorway.

Recovery of the miniball necessitates either keeping the magnet fully energized until the barrel-assembly is withdrawn or energizing the other recovery electromagnet at the same instant that the magnet behind the missed doorway is deenergized in to draw the miniball into the contralateral magnet-trap. The turret-motor allows rotation of the muzzle-head to assist in this process. However, either of these actions will interfere with the ongoing procedure. Yet another way to retrieve a miniball is by connecting one or more barrel-tubes or the distal end of the barrel-assembly to a suction pump and vacuuming the miniball to the outside.

This technique is more appropriate for a simple pipe type barrel-assembly that lacks a turret-motor to allow rotation of the recovery electromagnet. A barrel-assembly that lacks a side entry socket or sockets as addressed below in the section entitled Muzzle-head Access through a Service-channel without the Aid of and by Means of Inserting a Service-catheter must be disconnected from the airgun. While a miniball adherent thus in the digestive tract, for example, would be without significance and simply released into the lumen, and one in a ureter, for example, would have to be too large in diameter to be spontaneously voided, this must never happen in the circulatory system.

In the airway, where usually a simple pipe type barrel-assembly without trap-filter is used, the recovery electromagnet is deenergised so that the miniball sticks along the surface of the lumen. Provided the miniballs have been wetted with contrast on the rotary magazine clip prior to insertion of the clip into the chamber, recovery of the miniball through the recovery electromagnet trap-door is a simple matter. It has already been stated that no barrel-assembly introduced into the vascular tree should lack a trap-filter, as addressed below in the section entitled Embolic Trap Filter in Radial Discharge Muzzle-heads for Use in the Vascular Tree.

VII2. Ablation and Angioplasty-Incapable Barrel-Assemblies

An ablation or angioplasty-incapable barrel-assembly is a catheter extension to the barrel of an interventional airgun that remains engaged in the airgun and is used for medication miniball and/or stent miniball implantation. Ablation or angioplasty-incapable barrel-assemblies consist of simple pipe and radial discharge type barrel-assemblies. The simple pipe is substantially limited to use in the airway, the exceptions being use in the esophagus or gut when larger in diameter. The radial discharge type is meant for use in bloodless ductus wherein the anatomy is not highly differentiated as it is in the airway. The features incorporated into a radial discharge barrel-assembly usually include a trap-filter, electrically heatable turret-motor and recovery electromagnet windings with overlying heat-windows, and non-piped, or electrically operated, radial projection units.

To allow piped or fluidically operated radial projection units to remain connected with the barrel-assembly engaged in the airgun or worked by hand, the fluid store and controls are usually attached by means of an end or side-socket (qv.), usually through lines to a remote canister and controls. The extent of fluid circuit internalization, variable, an entirely self-contained embodiment must include a miniaturized fluid reservoir and pump. Miniaturized fluid supply and pumping modules that attach to the barrel-assembly without the need for hoses connected to remote apparatus also free movement. A simple pipe or a radial discharge barrel-assembly without supplementation can only be used to implant miniballs.

However, miniballs can consist, for example, mostly of ferrous metal to serve as the intraductal component of an extraluminal stent, or almost entirely of medication and/or other therapeutic substances where stenting is uninvolved and implantation can be closely targeted. Ensheathing a simple pipe or a radial discharge barrel-assembly within the central channel of a combination-form radial projection catheter adds side-looking tools for ablation or angioplasty by cutting, abrading, heating, or chilling, or injecting any fluid substance into the lumen wall. The combination-form radial projection catheter is slid over the barrel-assembly beginning at the proximal end until the front or distal edge of the catheter is stopped by the muzzle-head.

The combined apparatus is effectively an ablation or an ablation and angioplasty-capable barrel-assembly that requires insertion into an airgun only during ballistic discharge. Except for stenting without angioplasty, addressed below in the section entitled Thermal Ablation or Angioplasty- (Lumen Wall Priming Searing- or Cautery-) capable Barrel-assemblies, now gaining some acceptance, to minimize the risks for plaque rupture and the release of embolizing debris by contact with the muzzle-head, an ablation or angioplasty-incapable barrel-assembly is meant for use in an artery only following an angioplasty or an atherectomy.

An ablation and angioplasty-capable barrel-assembly allowing both angioplasty and stenting discharge with single entry, an angioplasty or atherectomy preceding the use of an ablation or angioplasty-incapable barrel-assembly requires the use of prior art (conventional) means or a separate radial projection catheter as addressed below in the section of like title. Such barrel-assemblies generally include or make possible plural means for the recovery of a loose miniball, to include recovery electromagnets, which can be reoriented in rotational angle with the turret-motor and transluminally by hand or a linear stage, a trap-filter, and the attachment of a barrel-tube or the proximal end of the barrel-assembly as a whole to a vacuum pump.

The attachment of a barrel-tube or tubes to a pump without the need to remove the barrel-assembly from the airgun is made possible by incorporation of a side entry socket, as addressed below in the section entitled Muzzle-head Access by Means of a Service-channel. Intended for use mostly in ductus other than vascular, the use of an ablation or angioplasty-incapable barrel-assembly in the arterial tree to stent without an antecedent angioplasty, even with the addition of a distal embolic protective filter, is specifically renounced as risking the release of embolizing debris. Ablation or angioplasty-incapable barrel-assemblies include simple pipes and radial discharge mono- and multibarrel radial discharge barrel-assemblies.

No independent (intrinsic, inmate) thermal ablative or angioplasty means are incorporated to allow use as separate from the airgun for freedom of movement, and no on-board electrical components or connections for independent power or control are installed. However, as the turret-motor is required positionally and the recovery electromagnets are required to retrieve dropped or to extract misplaced miniballs during implantation discharge, ablation or angioplasty-incapable barrel-assemblies require electrical connection to the airgun power supply, and this is accomplished through the types of contacts shown in FIGS. 55 and 58.

The incorporation of radial projection units into the muzzle-head of an ablation or angioplasty-incapable barrel-assembly imparts a radial nudging capability as a part of positional control rather than serves an ablative or angioplastic function. Because a minimally capable ablation and angioplasty barrel-assembly will generally include few radial projection units for deploying various side-cutting (side-shaving), side-brushing (side-sweeping), and/or side-injecting tool-inserts (addressed below in the section entitled Radial Projection Units, et sequens), it will generally lack an on-board ablation and angioplasty control panel. A relatively simple control for deploying radial projection unit tool-inserts, for example, is then included in the positioning and discharge control panel on the airgun enclosure.

For this reason, when an ablation or ablation and angioplasty-capable barrel-assembly is used, the radial projection unit tool-insert lift-platforms can be deployed from either the ablation-angioplasty control panel on-board the barrel-assembly or the positional and discharge control panel mounted to the cabinet of the airgun. The use of controls on the component controlled reduces human error. Conversely, because insertion in the airgun prevents free and independent movement unless the electrical connections are by means of a side-socket as addressed below in the section entitled Barrel-assembly Side-socket and graphically depicted in FIG. 58 and there is sufficient slack (and not as shown in FIG. 55), an ablation or ablation and angioplasty-capable barrel-assembly is used for ablation or angioplasty before engagement in the airgun.

Therefore, the positional controls mounted to the airgun would not usually be those used to rotate an eccentric turret-motor slot or slit heat-window or to eccentrically deploy radial projection units during ablation or atherectomy. The controls for these are on-board the free-standing ablation or ablation and angioplasty-capable barrel-assembly, preferably on top of the power and control housing for ambidextrous use.

VII2a. Simple Pipe Barrel-Assemblies

When the anatomy within the lumen, such as in the trachea, is structurally differentiated necessitating the discriminatory placement of each implant and the distances separating successive discharges are large enough for manual placement, automatic transluminal movement and triggering in uniform measured increments as is appropriate in a structurally undifferentiated lumen of small diameter is unsuitable. The simple pipe type barrel-assembly is intended for targeted implantation in a surgically entered body cavity or in a ductus or vas that is open to the exterior and large enough to allow the muzzle-head to be maneuvered without the need for repeated withdrawal and reentry.

Since application in a structured lumen demands accuracy, a flexible endoscope, usually a fine fiberoptic angioscope, and laser sight or pointer are lashed or clipped alongside the barrel-assembly, the laser sight used to mark the target, with the endoscopic view displayed on a monitor. If a bounce-plate is used, these viewing means are provided to cover it as well. A simple pipe barrel-assembly consists of barrel-catheter 44 with muzzle-head 45 having a mildly arcuate or curved section toward its distal underside containing the recovery electromagnet 46 in housing 56 within electromagnet housing 56 that the operator can bend if necessary toward the distal end to direct the miniballs toward the tissue, usually at an angle of about 35 degrees.

In simple pipe and single miniball radial discharge barrel-assemblies, the barrel-catheter and barrel-tube are one and the same, except that the barrel-tube or tubes continue all the way to the exit-hole, whereas the polymeric barrel-catheter terminates and is joined to the usually nonmagnetic stainless steel muzzle-head at the distal end. To avert the completion of a closed magnetic circuit that would detract from the field strength available for the purpose of miniball recovery as well as to allow the muzzle-head to be straightened if desired, muzzle-head 45 is made of forcibly bendable nonferrous metal or nonmagnetic stainless steel tubing and magnet housing 56 of any suitable plastic.

For better 'feel,' that is, a firmer grip, or a sense of greater substantiality and security, especially along the proximal segment mounting the control, thin simple pipes can be built up in diameter. This is accomplished by applying a molded hand-grip or by passing a concentric thick walled catheter made about the barrel-assembly or a combination of catheters that match and friction fit in concentric external to internal diametric relation. Over the intracorporeal segment, the outermost catheter is made of a soft polymer, such as a thermoplastic polyurethane or silicone. The muzzle-head of the simple pipe curved, a bounce-plate allows the miniball trajectory to be deflected into another direction.

Any protrusion of the angle adjusting mechanism or its parts that would scratch or gouge the lumen wall is kept to the minimum, rounded, and softened. A simple pipe as shown in FIGS. 31 thru 33 consists of barrel-catheter 44 with nonmagnetic metal muzzle-head 45 connected at the distal working end. To minimize friction, barrel-catheter 44 ordinarily has a fluoropolymer lining and is coextruded with or laminated by heat-shrinking and/or bonding ensheathment within a polymeric outer layer or layers selected to impart only so much flexibility as allows the operator essential working maneuverability while minimizing sagging as detracts from exit velocity.

Rotary joint 133 allows muzzle-head 45 to be rotated without twisting barrel-catheter 44. For laparoscopic use when muzzle-head 45 is short enough, rotary joint 133 connects barrel-catheter to muzzle-head 45; otherwise rotary joint 133 is placed along barrel-catheter 44. Muzzle-head 45 is made of nonferrous metal such as copper or an austenitic or nickel-containing 300 series nonmagnetic stainless steel with a hardness and wall thickness as allows the operator to adjust the aim by bending it at the distal curve. Magnet housing 56 can have an upper surface with a channel to receive the muzzle-head tube and be fastened to the underside of the muzzle-head by resistance welds limited to its proximal portion so that the muzzle-head can be bent to a less curved angle without disconnecting the magnet housing.

The housing then serves as a cold bending form to return the muzzle-head to its fully curved conformation. The muzzle-head of a radial discharge barrel-assembly is always controlled remotely with the turret-motor for rotation, for example. In a simple pipe for use through a laparoscopic portal, the muzzle-head can attach to the barrel-catheter at an internally smooth rotary joint that extends outside the body, allowing the operator to rotate the muzzle-head as a handpiece. This does not apply to a simple pipe for use in the airway, where the rigid and anatomically noncompliant muzzle-head must be limited to a short distal segment. Housing 56 for the trap and extraction, or recovery, electromagnet 46, is fixed in position within the concavity or intrados described by the underside of curve 45.

Figure 72:
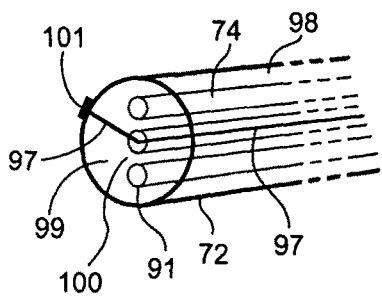
FIG. 72 is a detailed view of the proximal end-plate of a double barrel-tube radial discharge barrel-assembly showing the proximal terminal for the electrical connection of the components internal to the barrel-assembly, such as the recovery electromagnets and radial projection units, connection established when the barrel-assembly is engaged within the airgun chamber.
Figure 73:
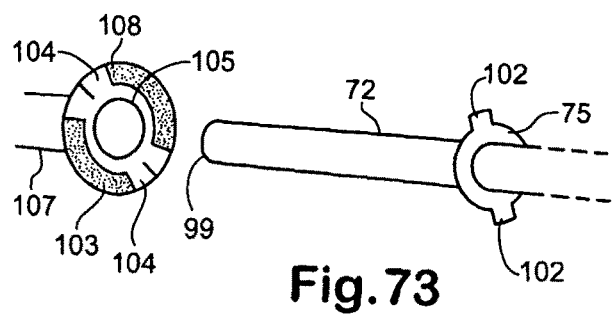
FIG. 73 is a detailed perspective view of a push and twist-to-lock connecting flange or flat bayonet type connector affixed to the muzzle of the airgun into which the male part of the connector is inserted then rotated to be engaged, such a connector used to lock a barrel-assembly of any kind within the barrel of any kind of interventional airgun with or without a forward drive and sag leveling and stabilizing device.

Inserting barrel-catheter 45 into barrel 57 of the airgun and locking engagement within the airgun chamber is by means of annular flange twist-to-lock connection fitting 47 in FIGS. 31 and 32, with detail provided in FIG. 73 establishes mechanical connection, with electrical connection to the airgun power supply established by an end- or terminal plate of the kind shown in detail in FIG. 72. Flange component 103 of the twist-to-lock connector fitted to the end of the airgun muzzle is friction fit to allow it to be rotated, so that to insert the barrel-assembly into the airgun after an angioplasty has been performed with the barrel-assembly already intraluminal and still separate from the airgun does not require rotation of the barrel-assembly in the lumen.

The equivalent connection with a radial discharge barrel-assembly shown as part 75 in FIGS. 39, 73 thru 75, and 78 can be freely rotated with a single barrel-tube barrel-assembly or monobarrel; however, the rotation of a radial discharge barrel-assembly having plural barrel-tubes at this joint may require that the rotary magazine clip also be rotated. The connecting flange can be forcibly rotated, but when different type miniballs, such as some pure medication and others ferromagnetic, are placed in each hole of the rotary clip, each must be discharged through the barrel-tube respective of each hole for aiming at the point of infixion intended. To accomplish the correct alignment between each barrel-tube and the hole in the clip respective of each barrel-tube may require manually rotating or indexing the rotary clip into the required position.

To maintain the correct alignment over consecutive discharges, the holes in the rotary clip are numbered to match the numbers assigned to the barrel-tubes. To allow the operator to slightly bend the muzzle-head when necessary, recovery electromagnet housing 56 is fastened to the underside of the muzzle-head 45 only along its more proximal upper surface interface with muzzle-head 45. Directly manipulated rather than remotely controlled by a positional control system, the simple pipe barrel-assembly is suitable for use in larger ductus that can be implanted with larger and more sparsely spaced miniballs with relatively little risk of pull-through.

In FIGS. 31, 32, and 34, in a simple pipe for use with laparascopic entry so that the muzzle-head 45 extends outside the body, muzzle-head 45 is joined to barrel-catheter 44 to serve as a handpiece which the operator can grasp and rotate by internally smooth rotary joint 133. In FIGS. 31 thru 33, rotary joint 133 is included only when the torsional resistance of barrel-catheter 44 hinders rotation of the muzzle-head or the lack thereof allows twisting deformation of barrel-catheter 44. Rotary joint 133 must rotate smoothly to allow the rotational angle to be set precisely and not be so loose that it then deviates or rotates unless a twisting force is applied to it.

In a simple pipe for use in the airway, where forcibly bendable but otherwise rigid muzzle-head 45 must be short as not to injure the, vocal folds (vocal cords, vocal ligaments), larynx, or airway, and cannot extend outside the body, joint 133 cannot join the muzzle-head to the barrel-catheter but must be positioned farther proximally along the barrel-catheter to provide a rotatable handpiece. This makes barrel-catheter 44 relatively long compared to muzzle-head 45, so that even though barrel-catheter 44 is made of or lined with a low friction fluoropolymer, such as polytetrafluoroethylene of relatively high torsional stiffness (ratio of applied torsion moment to resultant twisting), muzzle-head 45 can usually be rotated with little resistance as would interfere with accurate aiming. If not, a rotary joint is placed along barrel-catheter 44.

The simple pipe is intended primarily for use with a specially adapted relatively low cost air pistol for the treatment of tracheal collapse in veterinary practice. When the overall extent of transluminal or intracavitary travel is small and/or an assistant available, the barrel-assembly is connected to the airgun without an antisag-antiveer linkage as shown in FIG. 78 and described below in the section entitled Forward Drive and Sag Leveling and Stabilizing Device. When needed, the linkage is fastened at the airgun muzzle to extend over the barrel-catheter and keep it from sagging, veering, or buckling. The use of a continuous metal tube as barrel-catheter with a rotary joint to define and allow rotation of the distal segment as a muzzle-head avoids the expense of an antisag linkage but is too stiff to afford the operator any freedom of movement.

To minimize the risk of scrapes or gouges, the distal end of muzzle-head 45 is surrounded by elastomeric guard annulus 52, which covers the sharp edge of exit-hole (exit-port, ejection port) 55. Miniball recovery electromagnet housing 56 is nested within the mild curve toward the distal end of muzzle-head 45. The pipe is passed down the airway or through a laparoscopic entry portal with retractor or cannula to the treatment site. When the simple pipe is connected to a modified air pistol (hand airgun, air handgun) as described under the section below entitled Modification of Commercial Airguns, the gun, whether slid along a table top adjusted to the height of patient entry or held by an assistant, is allowed to move freely, and when the operator indicates that he is about to depress the trigger, the assistant is given a brief interval during which to make certain that the barrel-catheter is straight.

The barrel-catheter is not pulled straight as would displace the aimed muzzle-port but rather held level at the midpoint where it sags, the gun retracted only so much as is necessary to take up the slack. When the simple pipe is connected to an interventional airgun as described under the section below entitled Dedicated Interventional Airguns, the airgun is mounted on a wheeled tray or small dolly set on a table top adjusted to the height of patient entry, which the assistant allows to roll freely for the operator to indicate that he is about ready to trigger discharge, the assistant moving the table as well if necessary. When the operator indicates the intention to trigger discharge, the assistant assures that the barrel-catheter is straight and level by supporting the sag by hand and retracting the airgun only so much as is necessary to take up the slack.

The simple pipe can also be adjusted in sag or lateral curvature intentionally to reduce the exit velocity; however, this must never be done without first testing the airgun as described below with each such bend, and since to do this will require disconnecting the barrel-assembly from the airgun, such use in not preferred to adjustment that uses the sliding valve modification applied to the valve body also described below under the section entitled Modification of Commercial Airguns. When the veterinary patient with collapsed trachea is so small that the curve cannot be reduced sufficiently to avoid laryngeal injury, a radial discharge barrel-assembly with extracorporeal hand-held electromagnet should be considered.

If no barrel-assembly appears usable, then arcuate stays with a stent-jacket should be considered before proceeding with the standard procedure for suturing prosthetic rings about the trachea. For collapse that extends into the bronchi in tiny patients, implantation by means of a radial discharge barrel-assembly (addressed below) combined with subcutaneous patch-magnets (addressed above) is preferable as negligible in level of trauma compared to a thoracotomy. Procedures for correcting and ameliorating the symptoms of tracheal collapse are described below. While demanding more operative time, a simple pipe with modified commercial air pistol is adequate and inexpensive compared to more complex barrel-assemblies and special-purpose interventional airguns.

The combination of barrel-assembly and air pistol is primarily intended for use by veterinarians to repair tracheal collapse in small dogs. The simple pipe can also be used in a normally closed vessel or duct where accidental injury or a primary procedure has given access. Unlike a multibarrel radial discharge barrel-assembly, the simple pipe lends itself to loading from a spring-loaded or gravity-fed linear or queue-type no less than a rotary magazine clip. The limited diameter of most ductus makes a barrel-assembly with a single barrel radial discharge muzzle-head imperative to achieve an outer diameter of two millimeters. Otherwise, such an embodiment is not intended for use in any closed ductus and less still in the vasculature.

The airway does not pose the problems associated with the bloodstream, which include the need to prevent the backflow or entry of blood into the muzzle-head, and the risks of introducing gas into the blood, stretching injury, and inducing ischemia by obstructing the flow of blood. These factors and severely limited working room demand a speed of operation that the substantially undifferentiated structure of the lumen wall makes feasible. The simple pipe is suited to aiming within a lumen that is differentiated in structure, where speed is important but not of the essence, and requires no peripheral blood-grooves, tunnels, or means for the equalization of internal pressure as is necessary in radial discharge barrel-assemblies suitable for use in the vascular tree as described below. The treatment of tracheal collapse is addressed in greater detail below.

Multiple barrel barrel-assemblies with radial discharge muzzle-heads suitable for use in the vascular system are discussed thereafter. The simple pipe can be used with a flexible endoscope lashed alongside it, marked with contrast such as tantalum-based for viewability from without, or both. Unlike narrower ductus, the trachea, bronchi, and gut, for which the simple pipe is intended, are usually large enough to allow the elastomer bumper guard-encircled muzzle-port at the distal tip to be rotated with little risk of injury. Rotation is extracorporeal, the omission of a turret-motor allowing the muzzle-head to be narrower. If the lumen is too narrow for a simple pipe, a radial discharge barrel-assembly with protective outer shell and turret-motor is used.

The patient supine, or recumbent, loose miniballs stick to the lumen floor, and are retrieved either with the tractive electromagnet contained within recovery magnet housing 56 in the underside concavity of the muzzle-head seen in FIGS. 31 thru 34, or by connecting the distal end of the barrel-assembly to an aspiration pump. An aspiration line side-socket as addressed below in the section entitled Barrel-assembly Side-socket, or coupling mounted to the side of the barrel-catheter close to the airgun muzzle, allows the barrel-assembly to remain connected to an aspiration pump without the need to disengage the barrel-assembly from the airgun.

Shown in FIG. 33, spring-loaded trap-doors to either side of the recovery electromagnet are opened inward by the force of a loose miniball that is pulled into the housing, thus minimizing the rotation necessary to recover a loose or mispositioned miniball.

For the purpose of aiming implants, however, the muzzle-head of a simple pipe should rotate by not less than 120 degrees to either side with little resistance. Using a simple pipe barrel-assembly to treat a tracheal collapse, for example, the patient is positioned supine and the 'swing' to either side of straight downwards allows the placement of implants alongside the dorsal membrane to suspend it as addressed below in the section entitled Procedure for the Palliation of Tracheal Collapse in a Small Dog, among others. The patient is longitudinally rotated ("logrolled," rolled) into the supine position for the procedure before the simple pipe is introduced. This is not always necessary with a radial discharge barrel-assembly, which has a slippery (low friction) protective shell enclosing the muzzle-port (miniball exit-hole) or ports.

To reduce the width of the working end of the muzzle-head in a simple pipe type barrel-assembly, a single larger recovery electromagnet as shown in FIG. 33 is preferred. The inward-opening trap-doors to either side of the magnet are not shown as situated to the rear and fore of the plane of the drawing. Even though a simple pipe type barrel-assembly is primarily intended for use in the airway with the patient supine so that a loose contrast-wetted miniball sticks to the lumen surface where it is easily located, the side trap doors are made as large as possible to provide minimal obstruction to the most convergent lines of force that pass behind and across behind the doorways.

If, for example, the simple pipe is made of a substantially if not perfectly nonmagnetic stainless steel on the outside with an internal coating of polytetrafluoroethylene and the electromagnet housing 56 is made of a pliable polystyrene, then a suitable adhesive is a two part polyurethane, such as Loctite U-05FL, part number 29348, applied with mixer nozzle part number 98454 and dispensing gun part number 98472. Allowing some pliancy makes it possible for the operator to slightly bend the pipe at the curve if necessary. If altered, the pipe must be tested to ascertain the effect upon the exit velocity and consequent need to adjust the controls before use.

The simplest and most direct test is that described below in the section below entitled In situ Test on Endoluminal Approach for Susceptibility of the Ductus Wall to Puncture, Penetration, and Perforation. This universal connector for engaging a barrel-assembly in the barrel of an airgun, which differs only in diameter for Barrel-assemblies which contain multiple barrel-tubes, is described below under the section on the mechanical connection of the barrel-assembly to the airgun, and is shown in FIGS. 31, 32, 74, 75, and 78. This connector is the same as that used with radial discharge barrel-assemblies of which a detailed view is shown in FIG. 73. Should the detailed structure require, or the operator determine, that a second pass to implant miniballs in the reverse direction is needed, a bounce-plate is required.

A simple pipe with an integral or built in intracorporeally controllable bounce-plate allows the deployment, retraction, and angular adjustment in rebound angle without the need to withdraw and reintroduce the barrel-assembly. A bounce-plate attachment requires that the barrel-assembly be withdrawn to add, remove, or adjust the bounce-plate by bending before it is reintroduced. As an isolated occurrence, this is tolerable; however, repeated withdrawal and reentry is to be avoided as risking injury. A simple pipe is shown without a bounce-plate in FIG. 31, and with a bounce-plate attachment as addressed below in the section entitled Intracorporeally Nondeployable nor Adjustable Bounce plate Attachment and shown in FIG. 34. in FIG. 32, with intracorporeally controllable types shown in FIGS. 35 thru 37.

Bounce-plates which can be positioned from outside the body are described below in the sections entitled Intracorporeally Deployable and Rotatable Bounce plate with Slightly Adjustable Rebound Elevation and Intracorporeally Deployable and Rotatable Bounce plate with Precision Adjustable Rebound Elevation. A bounce-plate attachment, as opposed to a controllable bounce-plate addressed below in the sections entitled Extracorporeally Deployable Fixed Angle Bounce plate and Extracorporeally Deployable Adjustable Angle Bounce-plate, is made of a suitable plastic or a nonferrous metal such as copper or aluminum. As seen in greater detail in FIG. 34, in which the trajectory is represented as 54 and the distal end of the original muzzle-head 55 over which the bounce-plate has been slid, extends proximally along the top and sides of the barrel-catheter to a length sufficient to minimize if not eliminate recoil upon discharge, which length depends upon the material of which the barrel-catheter is made.

The simple pipe can be produced with an endoscope or with smooth surfaced clips for attaching an endoscope or similarly configured device, such as a laser or hot or cold air line. The endoscope is readily incorporated regardless of whether an endoluminal deflection-plate control mechanism as described below in the section entitled Intracorporeally Deployable and Rotatable Bounce plates is also present. Simple pipe barrel-assemblies for miniballs of 1 to 4 millimeters in outer diameter are made easier to manipulate if grips or an outer casing is added. For short segments, tape can be wrapped around the barrel-catheter.

To cover a longer segment, a catheter or catheters made of a soft polymer material such as silicone rubber latex that match in internal to external diameter as allows snugness in concentric relation are used. Referring now to FIGS. 31 and 32, shown are simple pipe type barrel-assemblies engaged in airguns. However, an intracorporeally deployable and rotatable bounce-plate, as addressed below in the section of like title, is sufficiently pliant and unobtrusive that it can extend from its distal end above the exit-hole backward (proximad) past the rotary joint, to a control slide-box that extends outside the body.

The distal portion of the barrel-assembly is curved to allow a miniball to be implanted, in tracheal application as will be described, at the anterior junction of each successive cartilage ring with the annular ligament, bilaterally, along imaginary lines that would demarcate the lateral edges of the dorsal quadrant of the trachea were it circular. Trap-extraction electromagnet 46 in FIG. 33 is of the same construction and electrical connection as is specified below for radial discharge muzzle-heads, but is singular, and as visualized in longitudinal cross-section, directed radially toward the tissue rather than paired where each is separately or jointly adjustable in field strength.

VII2b. Simple Pipe Ablation and Angioplasty-Incapable Barrel-Assembly Muzzle-Heads VII2b(1). Simple Pipe Barrel-Assembly with Bounce-Plate A barrel-assembly for use in the vascular tree must present a smooth and slippery surface, allow quick operation as one means for minimizing hypoxia, and incorporate features that minimize if not eliminate the need for withdrawal and reentry. This fact and the need to avoid any projections prompts enclosing the barrel-tubes of a radial discharge barrel-assembly in a slippery torpedo-shaped shell which is internally as well as externally protective in virtually eliminating gouging, incisions, and perforations, is position stabilizing, and strengthening. Compared to the structured trachea, the relatively undifferentiated gross structure of vascular, gastrointestinal, and urinogenital lumina lend themselves to multiple radial discharge, which places two or more miniballs at different radial angles with each discharge.

By contrast, the placement of miniballs in the trachea must be discretionary such that each miniball can be aimed at a specific point. This requires a single barrel that is not enclosed within a shell and can be clearly seen. A fine-gauged fiberoptic endoscope or angioscope and laser sight or pointer clipped alongside the barrel-assembly provide a view of the target site and indicate the aiming point for implantation that allows discharge to be accurate. FIG. 31 shows a simple pipe type barrel-assembly without a bounce-plate (deflection-plates, ricochet-plates; rebound-tips; rebound-plates, rebound deflection-plates, rebound angle deflection plates), and FIG. 32 shows one with an attachable bounce-plate, these embodiments omitting an intracorporeally controllable bounce-plate mechanism fastened along the upper surface toward the distal end of the pipe as shown in FIG. 35.

The portion of the barrel-assembly distal to the barrel-catheter 44 is muzzle-head 45. Optionally, to allow slight shifts or deviations in the aiming point or the point at which the miniball will penetrate the target tissue, the proximal face of a bounce-plate which is struck can be formed or ground with a concave contour. The concavity can be along the vertical or the horizontal axis or both. The controls provide calibrated gauges to support this capability. Unlike a radial discharge barrel-assembly, which can only be rotated over an arc determined by the eventual twisting of its barrel-tube or tubes, rotatory joint 133 allows muzzle-head 45 to be rotated endlessly. In a barrel-assembly for use without a bounce-plate or with a bounce-plate attachment described below, rotatory or swivel joint 133 must be placed at a level sufficiently proximal to allow muzzle-head 45 to be rotated in relation to the barrel-catheter.

In a barrel-assembly with an intracorporeally controllable bounce-plate mechanism described below, rotatory joint 133 must also be placed sufficiently proximal to allow clear access to the bounce-plate mechanism controls, which must be mounted to the top of muzzle-head 45 with which the mechanism rotates. The patient under general anesthesia, provided muzzle-head 45, which is inflexible from the distal (front) end to rotary joint 133 and includes a slight curvature toward the front end with recovery electromagnet 46 within magnet housing 56 nested therein can be passed through the vocal folds and larynx, for example with little risk of injury, rotary joint 133 will join muzzle-head 45 to barrel-catheter 44.

However, if the inflexibility of the muzzle-head interferes with safe clearance, then rotary joint 133 is placed more proximally to divide rather than join barrel-catheter 44 to muzzle-head 45. In this case, the materials of a bounce-plate mechanism must be flexible to comply with that of the barrel-catheter, which is readily accomplished with many different materials using a bevel gear but not a pulley arrangement within control tube 135 shown in FIG. 37. The division of the control sleeve into a proximal control slide-box portion 134 and distal controlled slide-box portion 140 is due to the requirement for control rod 135 to be rotatable, hence, cylindrical, whereas the distal bounce-plate 53 must have bilateral extension. Continuous sleeve or separate slide boxes 134 and 140 can be made of any suitable nonmagnetic metal or plastic with all corners and edges rounded or blunted.

Control slide-box 134 is lined with a material such as felt that imparts a smooth sliding action to slide-block 137, while controlled slide-box 140 is lined with an absorbent material such as gauze or a nonallergenic foam which can be wetted with a mucolytic such as acetylcysteine or a mucinolytic (mucinase, mucopolysaccharidase). The absolute amount of acetylcysteine is too small to cause stomatitis or induce nausea or rhinorrhea; however, to prevent bronchospasm, only light wetting is used in the distal airway. When made continuous, the proximal lumen must be circular to allow control tube 135 to be rotated, while the lumen of the distal controlled slide-box 140 must be horizontal to accommodate bounce-plate 53.

Thus, a lumen uniform in diameter or gauge from end to end would have to equal the width of bounce-plate 53, which will most often equal the diameter of exit-hole 55. This would double the cross-sectional area of muzzle-head 45 and bounce-plate mechanism combination. Fundamental objects being to minimize the muzzle-head to miniball diameter ratio and cost, separate proximal and distal lumina or slideways are provided as control slide-box 134 and controlled slide-box 140. The proximal end of bounce-plate control slide-box 134 then spans across a nonrotatable and intracorporeal joint between the inflexible muzzle-head 45 and the distal end of the barrel-catheter 44. Rotary joint 133 must then be sufficiently proximal to allow the barrel-assembly distal to it to be rotated and the bounce-plate to be controlled.

Since the bounce-plate mechanism does not span over rotary joint 133, the muzzle-head remains endlessly rotatable. Bounce-plates range in cost of manufacture and precision from a simple attachment to a built in precision mechanism that allows the discharge to be redirected without the need to move, much less remove, the muzzle-head from the body. Located in the concavity on the underside of the muzzle-head is the recovery electromagnet 46 within magnet housing 56. Rather than ejected perpendicularly to the surface of the lumen wall, the miniballs are delivered at an acute angle to be seated subadventitially or subfibrosally, or if necessary, medially or submedically (superintimally).

Entry thus seeks to wedge the miniball in place and avoid pull-through or delamination of tunic layers which may have been weakened by disease. Discharge at an acute angle also avoids a singular vector trajectory that normal to the intimal surface, would be more prone to rebound, possibly back into the lumen, if not perforate through the adventitia. For structured lumina or where for any reason it is advisable to reverse the direction of miniball entry, such as when entry orients the muzzle-head retrograde so that the passage of contents might eventually urge the miniball back into the lumen, a means for reversing the direction of entry is desirable.

While in some instances, such as for treating the trachea in a very small or 'teacup' sized dog where a simple pipe is too large for safe passage, an endoluminally deployable and retractable bounce-plate mechanism of a types now to be described can be added to a small gauge monobarrel radial discharge barrel-assembly. However, radial discharge barrel-assemblies are ordinarily intended for implanting substantially uniform gross anatomy as in virtually every other type of ductus (ureters, gastrointestinal tract, arteries) where exactitude in aiming is noncritical and multiple miniballs can be discharged simultaneously. To allow a clearer view of the exit-hole (muzzle), aiding aiming accuracy in relation to the differentiated structure within the trachea, simple pipes omit a shell (body, enclosure).

Barrel-assemblies for use within vessels, for example, provide a shell about the muzzle-head to protect the lumen wall, and are intended primarily for veterinary use to alleviate tracheal collapse, although the same conformation makes simple pipes more suited to applications outside of lumina than radial discharge barrel-assemblies. Since a simple pipe barrel-assembly with the endouminally deployable bounce-plate mechanism shown in FIG. 36 is passed through the larynx and down the trachea if not a bronchus with the bounce-plate retracted, a barrel-assembly that is equipped with an endoluminally controllable bounce-plate mechanism also reduces the risk of injury and thus the duration of general anesthetization.

Simple pipes can be made 1. To accept a simple bounce-plate attachment that to slip on and off requires removal from the patient and to change the vertical angle (elevation) requires bending and the rotational angle requires rotation of the muzzle-head; 2. With a substantially fixed rebound angle bounce-plate that can be slid forward into position or deployed and rotated while endoluminal whenever needed; or 3. So that vertical and rotational angular adjustments are under positive or direct mechanical control and calibrated for precision. The latter two are adjustable in downward inclination (elevation) of the bounce plate and thus the angle of rebound along the vertical axis of the muzzle-head.

By providing a calibrated control arm, that rotatable thus allows fine adjustment in the angle of discharge through a wide radially and longitudinally arcuate volume to its underside. When the muzzle-head can be long enough to extend outside the body, the forcibly bendable metal muzzle-head of the barrel-assembly is joined at its proximal end to the barrel-catheter by an internally smooth rotary joint for rotation as a handpiece. The intracorporeally adjustable bounce-plate configurations shown in FIGS. 35 thru 37 are then mounted to the upper surface of the muzzle-head. If not, the control spans over the junction between the muzzle-head and barrel-catheter. Either configuration allows the bounce-plate to be controlled while the barrel-assembly is in use to more quickly achieve fine control over the angle of discharge.

To reduce the risk of injury, permanent endoluminal bounce-plate control mechanisms must be as little protrusive as possible and have outer edges and corners that are blunted (rounded, curved). The use of a bounce-plate pertains only to simple pipe, not radial discharge type barrel-assemblies. The forward edge or rim of the pipe is generally cut an angle to allow flush placement against tissue to be implanted. The overhang generally accommodates the reverse discharge of miniballs when a bounce- or rebound deflection plate is attached. To minimize accidental injury, the tip of a simple pipe is covered with an elastomer guard. Protruding beyond the tip of the simple pipe, an overhang or roof-configured bounce-plate especially requires a protective guard.

Likewise for flush abutment, the tip of a walled-around bounce-plate is angled with the tip directed in the opposite direction. Walled-around, Krummlauf-type continuously curved barrels, and hybrid versions of the two for reversing the direction of discharge would allow good control over the trajectory but are impractical because of the enlargement if not hook conformation at the distal end of the pipe. Such ends make insertion and withdrawal difficult and more prone to cause laryngeal injury. The bounce-plate can be a friction-fitting attachment or a permanent feature. Because to observe the muzzle-port or ports is unintended and more difficult with a barrel radial discharge barrel-assembly, the simple pipe is preferred for use in the anatomically differentiated airway.

The single barrel radial discharge barrel-assembly is used only in the airway of the smallest dogs where there is not the space to manipulate a simple pipe and in distal segments of the bronchi where these are relatively undifferentiated. The structural differentiation and consequent need to place the implants in a discretionary manner can in some cases recommend the availability of a simple pipe barrel-assembly with bounce-plate (deflection-plate, ricochet-plate; rebound-tip; rebound-plate), which allows reversing the direction of the trajectory, that is, directing the miniballs back toward the operator or proximad. This capability can be beneficial, for example, in the trachea to introduce implants into the posterior junction of each successive cartilage ring with the annular ligament, as described below.

However, the avoidance of withdrawal and reentry in the airway is not onerous as it is in the bloodstream, and such a capability is often unnecessary. The single barrel radial discharge barrel-assembly and not the simple pipe is recommended when space is lacking to insert and withdraw the simple pipe without risk of injury to the larynx. In smaller patients, a simple pipe barrel-assembly may be usable for a distance towards the bronchi, down to which the diameter of the lumen becomes so restrictive that it becomes necessary to withdraw and replace the simple pipe with a single barrel radial discharge barrel-assembly. The bounce-plate is thus incorporated into a second simple pipe rather than as an option that would be opened or closed in a single embodiment.

Under such circumstances, withdrawal and reentry is preferable or essential, so that a single embodiment capable of discharge both distad and proximad, which to provide entails additional complexity and cost greater than the sum for separate barrel-assemblies where one does and the other does not have a bounce-plate, is not preferred. Accordingly, a simple pipe barrel-assembly that reverses the direction of the trajectory is provided in a separate barrel-assembly. FIGS. 32 and 34 show a simple pipe barrel-assembly with a manually attached bounce-plate at the distal end of the muzzle-head. An attachable bounce-plate is not deployable or retractable with the muzzle-head intracorporeal and is suitable only for occasional or isolated use for directional reversal of the trajectory when laryngeal clearance to admit the tip with bounce-plate is adequate.

Bounce-plates that allow insertion through the larynx then extension of the bounce-plate into position during use and retraction before withdrawal are described below in this section and shown in FIGS. 35 thru 37. Except for the addition of bounce-plate 53 and a soft protective annulus 52 adapted for the change in configuration of the muzzle-head that results from the bounce-plate, the simple pipe is the same as that shown in FIG. 31 with only a soft rubbery protective ring 52 surrounding the tip. Since the front portion of a full circle protective annulus 52 interferes with mounting bounce-plate 53, a hybrid annulus consisting of a soft or rubbery portion at the rear and bounce-plate portion at the front provided.

The bounce-plate portion may consist of bare metal or metal with an outer rubbery coat, which is then preferably unitary with the rubbery rear portion. A detailed view of the tractive electromagnet 46 mounted in the concavity on the underside of the simple pipe barrel-assembly in the curve 45 approaching its distal end is shown in FIGS. 31 thru 34. The loss of a miniball in the airway being unlikely and posing little risk even were it to occur, an antemagnet chamber as seen in magnet assemblies used in radial discharge barrel-assemblies for use in the bloodstream described below, is not used. In FIG. 33, recovery electromagnet 46 is enclosed within electromagnet housing 56 made of any hard plasticizer free resin and bonded in position by means of an adhesive that is pliable after curing as discussed in the preceding section.

When the airway is large enough that withdrawal of a muzzle-head without bounce-plate as shown in FIGS. 31 and 33 and reentry with a rebound muzzle-head or muzzle-head having a bounce-plate, such as those shown in FIGS. 32 and 34 poses minimal risk of injury, the separate embodiments are used. When the airway is not so small as to necessitate the use of a radial-discharge barrel-assembly, a simple pipe with a bounce-plate is used. The bounce-plate is a distal tip cap (crown, ferrule) friction-secured fitting that to attach or replace necessitates removal and reintroduction of the pipe; a bounce-plate that is endoluminally deployable and retractable addressed in the next section, and one that is endoluminally adjustable in angle addressed in the section following that.

If, for example, the simple pipe is polypropylene on the outside and the nonferrous metal of the bounce-plate is an alloy of aluminum, the adhesive, which must remain pliant after cured, is preferably a two part polyurethane, such as Loctite U-05FL, mentioned above in the preceding section entitled Simple Pipe Barrel-assembly. The angle of rebound equal and opposite to the angle at which the miniball strikes the bounce-plate upon exiting the original muzzle-port, seen in FIG. 34 as 55, the angle described between the trajectory upon colliding and rebound off of the bounce-plate is usually 45 degrees.

Rebound dissipates the kinetic energy and momentum or propulsive force imparted to the miniball necessitating adjustment of the airgun setting. Since the simple pipe barrel-assembly is intended for use in the trachea and the single-barrel radial discharge barrel-assembly for use in the tracheobronchial tree when the lumen diameter is confining, sections to follow the description of these single barrel barrel-assemblies will be directed to the application of these barrel-assemblies for use in the airway. Multiple discharge barrel-assemblies, which are not used in the airway but rather in vessels and ducts are described later.

The simplest type of rebound deflection plate, shown in FIGS. 32 and 34 consists of an angled tip that is slipped over the distal end of a pipe such as that shown in FIGS. 31 and 33 after pulling off the rubbery ring intended to protect surrounding tissue in the larynx and surrounding the lumen from gouging. Once introduced, it is not retractable and therefore suitable when insertion is unlikely to be repeated. The type shown in FIG. 36 is deployable and retractable, and that shown in FIG. 37 rotatable as well to adjust the radial angle of discharge more finely than is readily accomplished by rotating the muzzle-head as a whole while the muzzle-head is intracorporeal (inside the body).

VII2b(1)(a). Intracorporeally Nondeployable Nor Adjustable Bounce-Plate Attachment A bounce-plate attachment is suitable where a need for repeated adjustment once inside the body as would require withdrawal and reentry and thus increasing the risk for injury to the larynx, for example, can be discounted. When it cannot be discounted, an embodiment which can be adjusted without the need to withdraw, described in the sections to follow, is used. The portion of muzzle-head 45 in FIG. 34 corresponds to the terminal segment in FIG. 33, shown with elastomeric protective annulus 52. The intracorporeally nonadjustable bounce-plate attachment shown in FIG. 34 is slipped over the end of muzzle-head 45 after elastomeric protective annulus or guard 52 has been removed.

Adjustment to the elevation angle of the attachment is by forcibly bending its recurved distal end with bounce-plate 53. The angle of the slip on deflection plate causes the trajectory 54 to be directed proximad. A shape holding sleeve of copper, aluminum, or plastic can similarly serve this purpose in a simple pipe without a bounce-plate. If a plastic pipe is used at all, the preferability of a straight length of a more pliant tubing with the use of a bendable slip-over sheath is clear. The curve imparting sleeve can be temporary or bonded to the end of the muzzle-head by means of an adhesive. An intracorporeally nondeployable bounce-plate is an attachment for changing the angle of discharge as prefixed when slipped over the distal tip of the muzzle-head after the protective elastomeric annulus has been pulled off.

Where the intracorporeally adjustable embodiments described below are adjustable in bounce-plate angle of rebound elevation and rotation or azimuth without the need for withdrawal, to accomplish this with an attachment requires withdrawal, replacement of the attachment with another having the correct conformation or carefully bending the attachment to the exact conformation needed, and then reintroducing the muzzle-head through the airway. Since the exactitude of midprocedural adjustments in rebound angle that might be applied manually is limited and necessitates withdrawal, only occasional use for relatively simple procedures is indicated.

Since in order to remove the direction-reversing attachment, the muzzle-head must be withdrawn from the body, an intracorporeally nonadjustable bounce-plate is substantially limited to situations where the need for directional reversal alone is recognized prior to entry. Whereas an endoluminally deployable and retractable device imparts adaptability to unforeseen circumstances, a simple attachment that must be slipped over the distal end of the muzzle-head does not. For this reason, it is essentially limited to situations where only directional reversal at a fixed angle is needed. In contrast, intracorporeally adjustable bounce-plates eliminate the risk of injury in traversing the larynx repeatedly.

VII2b(1)(b). Intracorporeally Controllable Bounce-Plates

Enabling the operator to deploy and adjust a bounce-plate from outside the body without the need to withdraw and reintroduce the barrel-assembly every time it is necessary to make a routine adjustment reduces the risk of injury, the duration of the procedure, and therewith, the time the patient must be kept under general anesthesia. Routine adjustments include reversing the direction of implant discharge or the elevation or azimuthal angle of directional reversal. The intracorporeally controllable bounce-plate mechanism shown in FIG. 36 is less expensive to produce but limited to less demanding procedures where trajectory reversal can be obtained with less speed, convenience, and accuracy than would be afforded by the embodiment shown in FIG. 37. With any bounce-plate or rebound mechanism, control includes deployment and adjustment in the angles of rebound rotation (azimuth) and elevation.

Control in two dimensions with rotation at a rotary joint situated behind or proximal to the bounce-plate mechanism allows rebound to be directed to any point within the band subtended in enfilade; however, adjustment in elevation is not sufficiently fine to allow precise readjustments between aiming points to be made quickly. Finer adjustment in elevation is obtained at less cost than would incorporating a supplementary fine adjustment by forming the bounce-plate with a curved contour so that use of the bounce-plate mechanism rotation control to effect small changes in the vertical inclination or attitude of the bounce-plate proportionally shifts the orbit described for a given angle of elevation by rotating the muzzle-head about the rotary joint.

Referring now to FIGS. 33, 36, and 37, rotating the barrel-assembly as a whole or the muzzle-head 45 at rotary joint 133 seen in FIG. 33 situated proximal to the bounce-plate mechanisms shown in FIGS. 36 and 37 with bounce-plate 53 set at a fixed angle of elevation causes successive miniballs to enter into the surrounding lumen wall along a circle or circumference which represents the outer edge of the lower portion of a cone described by the successively discharged miniballs where bounce-plate strike-point as point of origin describes is rotated about a circle at a level beneath the cone apex or vertex. In a simple pipe as opposed to a radial discharge barrel-assembly where the barrel-tube or tubes would become twisted, rotary joint 133 allows muzzle-head 45 to be rotated in a complete circle repeatedly.

If the major axis of the muzzle-head is in or coaxial with the longitudinal axis of the lumen, then the outer edge of this cone will be circular, or describe the base of a right angle cone. If the muzzle-head is abaxial (off axis), then the edge of the cone will be off-circular or describe the base of an oblique cone, the miniballs directed toward the more distant wall of the lumen entering at a greater distance from the point of rebound origin. In FIG. 36, push-pull control rod and in FIG. 37, push-pull control tube 135 is fastened to control slide block 134 by journaling in the inner rotatable ring of bearing 136, of which the outer ring is securely fastened to block 137.

Rotation and horizontal reciprocation control lever 138 is retracted proximally to (behind) control slidebox 134 when bounce-plate 53 is not deployed, but moves forward into flush position against the rear of control slidebox 134 when bounce-plate 53 is deployed. Apposition thus brings control lever 138 into flush relation with the rotational calibration or scale inscribed along the upper surface or ledge of calibration or scale plate 143 applied to the rear of control slide-box 134, allowing control tube 135 to be rotated. Rotation allows rebound to be moved about an imaginary cone with apex or vertex at the strike-point. Grinding or otherwise forming the striking face of bounce-plate 53 so that it curves to either side of the central strike-point allows deviation from the orbital aiming point.

The extent of horizontal displacement forward or backward of bounce-plate 53 is shown by a calibration or scale engraved along the upper back ledge of slidebox rotation calibration 143 just in front of control lever 138. For use in structured lumina, a fine fiberoptic endoscope (angioscope, flexible boroscope) is clipped alongside the barrel-assembly to provide a clear view of the aiming point in any event. When the distal end of the bounce-plate is not clearly seen, a second scope is provided for the purpose. This and the fact that an elastomeric cap can cover the distal end of the bounce-plate minimize the risk of injury during bounce-plate deployment (ejection, unstowing) and use.

A bounce-plate which can be controlled from outside the body can be rotated independently of, and so long as it does not press against the lumen wall, without regard to, the position of the muzzle-head as a whole. In FIG. 36, division of control rod 135 sheath into proximal control slide-box 134 and distal controlled slide-box 140 allows bounce-plate 53 to be retracted into the unensheathed segment expediting its replacement, maintenance, or exceptionally, a need for midprocedural cleaning Bounce-plate 53 in the more costly embodiment of FIG. 37 provides the open segment not for the replacement or maintenance but rather to expedite midprocedural cleaning of permanent bounce-plate 53 should it become fouled with mucus, for example.

Where this eventuality is predicted, the need to withdraw and reenter is averted through the addition of a fine aspiration line clipped to run adjacent to the angioscope alongside muzzle-head 45 for the midprocedural clearing of debris. Rotation or azimuthal adjustment of the bounce-plate when it is fixed in angle of elevation will cause the miniballs to enter the lumen wall in an arc within the cone base described or outlined when the muzzle-head is rotated as a whole. More specifically, independent rotation of the bounce-plate occurs at a point along the circle described when the muzzle-head is rotated. The bounce-plate strike-point is the same whether rotated concentrically to the muzzle-head or about its own long axis.

Therefore, the movement of both the strike-point on the bounce-plate and the aiming points of rebound stand in epicyclic relation where rotating the bounce-plate draws the trajectory inward in relation to the circle of discharges. Rotation of the bounce-plate when flat-faced thus allows small local deviations from the larger arc obtained through overall rotation in the sense of allowing the larger circle to be drawn inward from the circular base or orbit and in this way enable fine and quick control over the limited arc for a specific point along the orbit when the muzzle-head is not rotated. The face of bounce-plate 53 can also be formed or ground to alter the rebound angle, thereby allowing the operator to deviate from the major orbit or 'cone base' more finely and quickly by rotating the bounce-plate than by adjusting the angle of elevation, and to do so without the need to adjust the angle of elevation for the orbit as a whole.

To eliminate an additional degree of freedom that would allow the bounce-plate 53 to be rotated about its vertical as well as its horizontal axis, the strike-face when spring steel is formed and when solid stock ground with a concavity of whereby the rate and extent of curvature determine to what distance the miniball trajectories can be diverted inward. The rebound trajectory can be diverted sideways or inside the major orbit set by the elevation according to the angle at which the miniball strikes bounce-plate 53, and may be increased by widening the bounce-plate. This displacement can be applied for individual discharges, or the setting of the rotational angle of bounce-plate 53 can be applied to the entire orbit to draw it inward.

Figure 83:
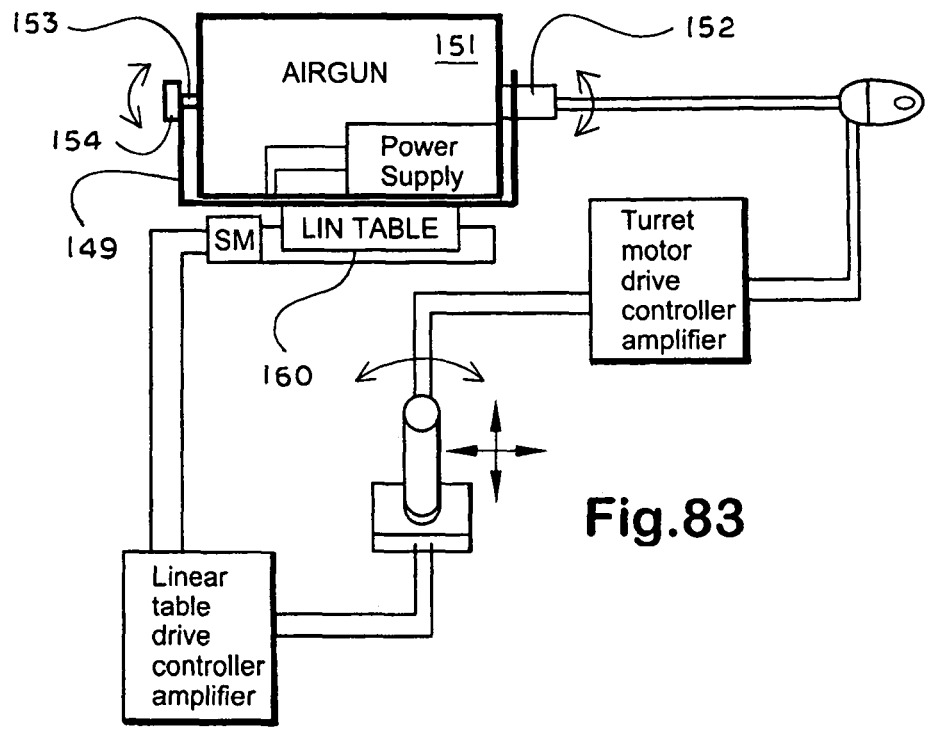
FIG. 83 shows a diagrammatic representation of an automatic positional control system for an interventional airgun, which can be a gravity fed monobarrel such as those shown in FIGS. 81 and 82 or equipped with a rotary clip magazine such as those shown in FIGS. 31 and 32 for use with multiple barrel-tube barrel-assemblies, which advances, withdraws, and rotates the muzzle-head in coordination with discharge to allow the uniform implantation of miniballs in close-formation.

With two levels of rotational freedom and a third contributed by the ability to rotate the bounce-plate, any rotational angle of the muzzle-head is readily attained: If nonrotatably mounted to the airgun muzzle at the twist-to-lock connector, then rotary joint 133 in FIGS. 31 thru 33 is used. If connected to an airgun mounted to a linear positioning stage on a swivel carriage as shown in FIG. 83, then a second point for rotation is available. The intracorporeally controllable bounce-plate mechanisms described in the following sections provide an additional adjustment for the rotational angle of rebound. Similarly, with an air pistol, the barrel-assembly is rotated as a whole or at joint 133. When rotated midprocedurally, the 'top' or 'upper surface' of a barrel-assembly is that of the muzzle-head, not that of the bounce-plate or the vertical axis.

Whether along a longer muzzle-head, the junction between barrel-catheter and muzzle-head, or at a level along the barrel-catheter, rotary joint 133 must be positioned sufficiently proximal along the barrel-assembly that it remains extracorporeal and accessible for manual adjustment. Since the bounce-plate mechanism must be continuous and its push-pull handle and rotation lever or arm 138 shown in FIGS. 35 thru 37 must also remain accessible, rotary joint 133 must be positioned proximal to the proximal end of the bounce-plate mechanism. Control slide-box or sheath 134 is ordinarily extended up to controlled slide-box or sleeve 140. Controlled slide-box 140 is advantageously identical to distinct bounce-plate 53 housing when bounce-plate 53 is of a shape that would result in added expense were it unitary or continuous with the bounce-plate mechanism proximal to it.

However, the primary requirement to avoid protrusion severely limits the outer dimensions of such a controlled sleeve, as well as necessitates withdrawal of the barrel-assembly to change the bounce-plate. Whether control rod 135 and bounce-plate 53 are ensheathed continuously or with a distinct controlled slide-box 140, the paired control and controlled slides move forwards and backwards together. Thus, pushing control lever 138 and control rod 135 forward advances and deploys, or unstows, bounce-plate 53. As shown in FIG. 35, an intracorporeally deployable and rotatable bounce-plate mechanism is mounted at the top of the simple pipe barrel-assembly, a less costly embodiment shown in FIG. 36 and a precision embodiment in FIG. 37. Both FIGS. 36 and 37 represent push-pull handle and rotation control lever 138 and slide-block 137 as moved to the most forward (distal) position.

FIG. 36 shows nonmagnetic spring stainless bounce-plate or tongue 53 retracted into control channel 145, while FIG. 37 shows solid nonmagnetic stainless steel slab bounce-plate 53 fully ejected in correspondence to the forward position of control lever 138. Whereas the embodiment shown in FIG. 36 passively adjusts the rebound angle of elevation in proportion to the extent that control rod 135 is advanced and bounce-plate 53 is ejected as a dependent variable, that shown in FIG. 37 provides an additional degree of control independent of the displacement of control tube 135, which must be fully advanced before control lever 138 can be used to adjust the angle of elevation of bounce-plate 53.

Another advantage in the embodiment shown in FIG. 37 is that bounce-plate 53 need not be changed midprocedurally to adjust for significant changes in the momentum of discharge to achieve penetration to a greater depth, into harder tissue, and/or because the mass of the miniballs is significantly changed with changes in composition. Since stenting miniballs can be coated with medication, significant changes in mass among miniballs should arise very seldom, especially in the veterinary applications for which a less costly bounce-plate mechanism is desirable for use with a less costly air pistol. A formation that intersperses stenting and drug delivering miniballs, for example, is usually avoidable but would necessitate bounce-plate replacement.

By contrast, the less costly embodiment shown in FIG. 36 requires that control rod 135 with spring stainless steel bounce-plate or tongue 53 be withdrawn through friction fitted rotary bearing 136 in order to exchange bounce-plate 53 with another that differs in its preformation or resilience whether due to materials, thickness, or both. No resistance posed to bounce-plate 53 during ejection, so long as it is springy, the preformation imparted to bounce-plate 53 in manufacture and not its resilience determines its decompression characteristics during ejection and conformation when fully ejected. Withdrawing push-pull handle and rotation control lever 138 as shown in either figure would expose control and rotation rod or tube 135.

Overlying the recovery electromagnet assembly shown in FIGS. 31 thru 33, the bounce-plate mechanism excludes magnetically susceptible materials. As seen in FIG. 35, when the simple pipe includes an intracorporeally controllable bounce-plate mechanism, elastomeric protective annulus or guard 52, provided to prevent scraping or gouging injury from the sharp edge of exit-hole 55 (seen without the mechanism in FIG. 33) extends entirely about to encircle the distal end of the bounce-plate mechanism. Control slide-box 134 contains slide-block 137 which journals push-pull and rotation control rod 135 within proximal rotary bearing 136, allowing control rod 135 to be rotated and slid forward and backward within the limits set by the space enclosed within control slide-box 134.

The lower cost of the embodiment shown in FIG. 36 is obtained through the use of a solid rod 135 to gradually push curved blade type bounce-plate 53 out of alignment sleeve or controlled slide-box 140 at the distal end where the extent of blade ejection passively sets the rebound angle of elevation without a third degree of freedom in the form of a lever to accurately adjust this angle. The calibration along the top of the lower cost embodiment indicates the angle of rebound at that position. The greater cost of the embodiment shown in FIG. 37 results primarily because control rod 135 is a hollow tube used to convey a shaft with bevel gears at either end or a pulley to allow bounce-plate 53 to be adjusted in elevation with precision and the calibration associated with such control.

Elevation angle is thus not a passive consequence of the extent of blade or bounce-plate 53 ejection but rather initiated only once joint 141 is pushed past opening 142. Slide-block 137 interfaces with the internal surfaces of control slide-box enclosure 134 to impart smooth travel with enough resistance to allow control rod 135 to be accurately controlled with control lever 138 while allowing control rod 135 to rotate within it. The resistance should be slight enough that any obstruction to the projection of bounce-plate 53 will immediately signal to the operator the need to slightly retract, adjust, and readvance before proceeding. Bounce-plate 53 in FIG. 36 may be used when partially deployed; however, to prevent jamming, in the fully forward position, bounce-plates 53 in both FIGS. 36 and 37 must extend beyond exit-hole 55 to a distance greater than the diameter of a miniball.

To prevent incisions, bounce-plate 53 is limited in length to the diameter of exit-hole 55, and must not extend past the lower edge of exit-hole 55. Control slide-box housing 134 can be transparent or opaque and continuous along the top of muzzle-head 45 to distal end 55 of muzzle-head 45 or since both control slide-box 134 and controlled slide-box 139 are fastened to the upper surface of muzzle-head 45, left unenclosed, in which case inert sleeve or controlled slide-box 140 toward the distal length of the mechanism as shown in FIGS. 36 and 37 is provided to constrain rod 135 to the correct position. Whether continuous or interrupted and continued with slide-box 140 as shown, the sleeve encircling control rod 135 is made of a low friction material such as polytetrafluoroethylene.

The extent of deviation from the major orbit is determined by the width and curvature of the bounce-plate. A separate distal sleeve or controlled slide-box 140 is used when the conformation of the bounce-plate makes manufacture simpler and quicker than machining or otherwise forming a different shape at the distal segment of a continuous bounce-plate control rod or tube sleeve. When present, a separate distal sheath requires neither slide-block nor rotary bearing.

As all other components of bounce-plate deployment and adjustment mechanisms, push-pull and rotation control rod 135 in FIG. 36 or tube 135 in FIG. 37, must be nonmagnetic, tortionally noncompliant as not to distort helically when the operator uses push-pull handle and rotation control lever 138 to adjust distal bounce-plate 53 in rotary angle or azimuth, must not fatigue fracture despite its small dimensions, or if a tube, its thin wall, and is therefore made of a strong nonferrous metal, alloy thereof, or a nonmagnetic stainless steel. When the material of control slide-box housing 134 is not transparent to allow a reference pointer at the top slide-block 137 to be seen as projected against a calibration along either side in the upper surface of control slide-box 134, pointer 139 projects up through and moves along a slot in the top of control-box 134 to indicate the extent to which control rod 135 is displaced forward, which is equal to the distance that bounce-plate 53 projects beyond the distal end of muzzle-head 45.

Similarly, the left edge of push-pull handle and rotation control lever 138 moves past rotary indicator calibration plate 143 between it and the rear of proximal end of control slide-box 134 to indicate the angle to which intracorporeal and unviewable bounce-plate 53 is rotated. Control over the angle of elevation in the first embodiment described below passive, push-pull handle and rotation control lever 138 is used to adjust the rebound angle of elevation by translation of control rod 135 forward or backward. By comparison, control lever 138 in the combodiment with positive control over elevation shown in FIG. 37 is pushed to rotate it forward to depress, and pulled to rotate lever 138 backward to raise, bounce-plate 53.

Accordingly, push-pull handle and rotation control lever 138 in FIG. 36 rotates only from side to side or along a imaginary x-axis, while that in FIG. 37 also rotates in the forward and backward or y-axis. Control over elevation in the embodiment of FIG. 37 thus requires a stationary elevation calibration plate mounted coaxially with the axle of control lever 138 which does not rotate. Calibration plate 143 and those indicating the angle of elevation fastened to either side of the of push-pull handle and rotation control lever 138 in FIG. 37 (not shown) are press formed with outer edge folded around to allow the calibration to continue from the vertical to the horizontal or horizontally tending surface for improved visibility.

Push-pull and rotation control rod 135 in the simpler embodiment of FIG. 36 and the push-pull and rotation control tube 135 of precision embodiment of FIG. 37 are journaled within rotary bearing 136 at the proximal end of control slide-block 137. Rotating push-pull handle and rotation control lever 138 thus allows push-pull and rotation control rod or tube 135 in the embodiments of FIGS. 36 and 37 to be rotated while remaining journaled within to move forward and backward with control slide-block 137 within control slide-box 134, so that pushing it forward advances, and pulling it out retracts control rod or tube 135.

In the less costly embodiment of FIG. 36, the angle of rebound elevation is adjustable to the extent allowed by retraction of curved bounce-plate 53 into terminal aligning sleeve 140. With elevation adjusted by this means, pointer 139 and associated calibration marked along the top of control slide-box 134 indicate the elevation. In the embodiment of FIG. 37, the elevation is adjusted with greater precision but only once joint 141 clears exit-muzzle-head 45 exit-hole 55. The angle of elevation is then adjusted with the calibration disks (not shown) fastened to either side of push-pull handle and rotation control lever 138 axle 144.

VII2b(1)(b)(i). Intracorporeally Controllable Bounce-Plate with Limited Adjustability in Elevation Turning now to FIG. 36, shown is a simple bounce-plate control mechanism which allows bounce-plate 53 to be deployed from outside the body with limited adjustability and accuracy in the rebound angle of elevation. Among suitable materials addressed below, bounce-plate 53 can be a nonmagnetic stainless spring steel tongue that is compressed or flattened when retracted into or stowed within controlled slide-box or distal sheath 140 by pulling out control lever 138 and returned to its curved shape by intrinsic restorative force or shape memory as decompressed upon being ejected through front opening 142. The resilience and restorative force of bounce-plate 53 is thus limited, and for that reason, it will maintain consistency in the angle of a miniball rebound off its surface only up to a certain strike momentum as determined by the exit velocity ('muzzle velocity' of the miniball).

Compared to the embodiment shown in FIG. 37, omitting the rebound angle of elevation as an axis or degree of freedom under control eliminates the need for a control lever that toggles, or rotates forward and backward, as well as side to side, the axle joint required for movement thus, a pulley or shaft with bevel gears at either end coursing through a control tube used to transmit the motion, and a precision machined bounce-plate. Specifically, in the less costly embodiment shown in FIG. 36, withdrawing control lever 138 is calibrated along the top of control slide-box 134 and adjusts the elevation angle of rebound as it retracts bounce-plate 53 into its distal sleeve or controlled slide-box 140. By comparison, in the embodiment described in the section to follow, precise control in the elevation angle is by calibration and operational only when lever 138 is fully forward wherewith bounce-plate 53 is fully deployed.

In FIG. 36, bounce-plate 53 is preformed of a springy metal and/or possibly strong plastic resin, usually a nonmagnetic spring stainless steel, within the range of restorative force that allows it to be retracted without such resistance as would cause muzzle-head 45 to jerk while in use. Steels capable of meeting the requirements are specified in the section above entitled Intrinsically Magnetized Stent-jackets with sources for such materials addressed below in the section entitled Independent and Subordinated Control of a Stay Insertion Tool Auxiliary Syringe Holding Frame. Intrinsic restorative force or springiness causes bounce-plate 53 to passively unbend as it is ejected out through controlled slide-box 140 front opening 142. According to the form and restorative force of bounce-plate 53, this gradually changes the effective elevation angle of rebound.

In To be noted is that the function of bounce-plate does not commence only once the length ejected passes over the center of the imaginary front tangent of a discharged miniball; lesser exposures can 'clip' the exiting miniball, sending it in a different trajectory than in the long axis of the 'muzzle.' Midprocedural accuracy demands preprocedural testing and recording of the exact settings used to achieve the trajectory desired. Different curvatures, materials unitary or laminated, widths, and thicknesses, hence, restorative forces can be imparted to bounce-plate 53. The longitudinal axial length of interchangeable bounce-plates are the same, subject to the constraint that the lower wall of muzzle-head 45 must not be overextended due to the risk of gouging injury.

Limitation in the overall length of the bounce-plate disallows elongating it to incorporate different curves along successive segments and therewith the adjustability in rebound angle of elevation available with such means. Withdrawing the barrel-assembly will allow the bounce-plate to be changed midprocedurally. Interchangeable bounce-plates made to the same length, the extension is shown on the calibration provided on the upper surface of control slide-box 134 (not shown), and the rebound angles that correspond to these distances are shown in a table provided with the bounce-plate. However, withdrawal and reentry is best avoided, leaving such an embodiment adequate for simpler procedures performed with a interventionally modified air pistol, for example, as addressed below in the section entitled Simple Airgun Modified to Allow Limited Application.

By contrast, the embodiment described in the section to follow incorporates a separate control to allow a permanent or built in bounce-plate to be adjusted in angle of elevation. This in turn does away with any need to exchange one bounce-plate for another, which may require withdrawing and reinserting the muzzle-head. Changes in exit momentum of such magnitude as necessitate changing bounce-plate 53 midprocedurally are determined by the hardness of the tissue to be implanted. In the trachea, this typically necessitates changing the bounce-plate once, all points to be implanted at one exit velocity implanted first and the other tissue second.

Interchangeable bounce-plates are made of nonmagnetic spring stainless steel and differ in resilience and conformation according to it preformation. Bounce-plate or tongue 53 can be used to shift the angle of rebound from the major orbit by rotating it with control lever 138 in proportion to its rate of curvature and width. As indicated in the preceding section, if necessary, control rod 135 with bounce-plate 53 is withdrawn through friction fitted rotary bearing 136 by pulling control lever 138 backward. The control rod-bounce-plate combination is then exchanged for another or bounce-plate 53 is disengaged from the distal end of control rod 135 and replaced with another bounce-plate. For this reason, control rod 135 is made in a wider diameter as will allow bounce-plate 53 to be withdrawn through its channel without the need to withdraw the barrel-assembly as a whole.

When bounce-plate 53 will pass through the channel to the outside, it is quickest to exchange the combined control lever 138, control rod 135, and bounce-plate 53 for another such combination. Alternatively, with the combination fully withdrawn, bounce-plate 53 is disconnected from conrol rod 135 by pushing axle pin 146 connecting it in pivoting relation to the end of control rod 135 out one side of spindle 147, and fixing the replacement bounce-plate by reinserting axle pin 146. If necessary, controlled slide-box 140 is exchanged for another that fits the replacement bounce-plate. To minimize the risk of trauma, the bounce-plate mechanism is kept as little protrusive in relation to the muzzle-head as possible.

When deployed, bounce-plate 53 spans across muzzle-opening 55 of muzzle-head 45 at an incline to the vertical and is therefore slightly longer than the bore (chase) or internal diameter of muzzle-head exit-hole or opening 55 plus the thickness of the upper wall muzzle-head 45. FIG. 36 shows bounce-plate control rod 135 in the fully forward position, which fully ejects bounce-plate 53 through front opening 142; however, for drawing compactness, bounce-plate 53 is shown retracted or stowed within controlled slide-box or sleeve 140. Bounce-plate 53 is never so narrow that it can be withdrawn through the control rod channel. This means that bounce-plate 53 cannot be retracted to the outside through the control channel, but requires withdrawing the barrel-assembly.

While the distal segment of the control rod sheath might be formed to enclose a bounce-plate of any dimensions, compared to the use of a continuous sleeve, a separate distal segment sheath, or controlled slide-box, simplifies manufacture as well as offers some practical advantage for maintenance. A separate controlled slide-box 140 requires that a bounce-plate too wide to pass through the sheath be removed only by withdrawing the barrel-assembly from the body as a whole. Control slide-box or sleeve 134 forward of slide-block 137 and its front wall stop can be extended entirely to the front end of bounce-plate mechanism 53 to present the appearance of a continuous sheath from end to end where bounce-plate 53 is withdrawn into the front end thereof.

Whether retracted into a distinct or continuous distal segment, the elevation or protrusion of the bounce-plate mechanism above the upper surface of muzzle-head 45 must not risk injury; instead, an overall smaller caliber barrel-assembly is used. Push-pull and rotation control rod 135 is joined at its proximal end toward the bottom of control lever 138 by single hammer head eye or dowel joint insertion and connected at its distal end to bounce-plate 53 by tightened machine screw with lock or Belleville disc ring spring washer, snap, or similar fastener 147. Continuing the rod through the back side of lever 138 provides an in-line or single vector push and pull grab for advancing and retracting bounce-plate 53.

Unlike the permanent rotary joint 147 of the embodiment next to be described, fastener 147 allows bounce-plate 53 to be disconnected and exchanged for another of different curvature and rebound characteristic. Exchanging a bounce-plate of one conformation for one of another allows the rebound angles of elevation obtained at different bounce-plate projections out front opening 142 to be changed. To change bounce-plate 53 midprocedurally requires withdrawing the barrel-assembly. For this reason, changing bounce-plates is preferred only for setting the rebound characteristic before the procedure is begun or when operating in a surgical field opened for another reason.

The embodiment next to be described allows sufficient control over rebound angle that the bounce-plate is permanent, so that adjustments can be made more quickly, conveniently, and without the need to withdraw the barrel-assembly. Control rod 135, of nonmagnetic stainless steel, nonferrous metal, or plastic such as styrene, passes through the proximal wall of controlled bounce-plate 53 sheath or slide-box 140 beyond which it is fastened to bounce-plate 53. The rear portion of control slide-block 137 extends proximally or backwards as ledge 148, which mounts projection or nub 139 into which is etched a reference line that passes along and projects up through a slot in the upper surface of control slide-box 134. The slot is marked off to either side with a calibrated scale that indicates the extent of forward displacement of bounce-plate 53.

The extent of forward displacement significant in a measured way, control slide-block 137 must move smoothly and positively without a detent along the entire throw within control slide-box 134. Bounce-plate 53 must have springiness and prompt 'shape memory' to the extent that when slid forward, the curved and/or creased conformation imparted to it can be substantially flattened when withdrawn into its distal controlled sleeve and return to its unflattened form as it is ejected. Preserving a cross sectional area small as possible expedites passing through the vocal cords and reduces the size of a laparoscopic access portal, for example. The flatter bounce-plate 53 compresses without deformation, the less will its sleeve or control slide-box 140 protrude above muzzle-head 45 and the smaller will be the cross sectional area.

By the same token, a thin springy tongue is easily deflected at higher exit velocities, which can result in the need to introduce a proportional correction factor in the angle setting. Suitable materials for tongue 53 are tin bronze SS 5428-7, beryllium copper CuBe 250, nickel-chromium-cobalt alloy, such as Special Metals Division, Precision Castparts Corporation Nimonic® 90 or Inconel® 718, or a nonmagnetic stainless spring steel (see, for example, Yamamoto, S. and Sato, K. 1981. "Non-magnetic Stainless Steel," U.S. Pat. No. 4,246,047). Spring blade or tongue-type bounce-plate 53 is checked prior to use and if found to have become deformed, is replaced.

The fastener used to attach bounce-plate 53 to the end of control rod 135 well secluded from the surrounding tissue, any suitable fastener, such as a small thumb machine screw, clasp, or latch should be usable without concern for injury. To prevent injury to the lumen wall, the distal and side edges of controlled or bounce-plate 53 are padded with a protective elastomer. When the bottom or hypotenuse of the right triangle formed by the plane perpendicular to the forward edge of the exit port (muzzle, muzzle-head exit-hole) and the plane of the bounce-plate is longer than the diameter of the miniball, the exit path will be clear. When shorter than the diameter of the miniballs but the exit velocity is high, the miniball will usually clear anyway. When shorter than the diameter of the miniballs so that discharge would be obstructed, the hypotenuse can be lengthened by cutting away a small portion of the lower rim of the muzzle-head.

A simple-pipe type barrel-assembly of unchangeable conformation fitted with an unexchangeable bounce-plate would limit the ability to target any point, especially where the anatomy affords inadequate space to maneuver. However, the ability to the bend muzzle-head and attach different bounce-plates reduces such limitation. Raising the bounce-plate to a higher elevation allows directing miniballs over an arc of rebound angles in the forward direction, and rotation of the bounce-plate allows nudging the aiming point aside of the unrotated position, just as smaller angles of elevation direct miniballs in the reverse direction where rotation of the bounce-plate likewise allows reaching points aside from the vertical axis. The points in the surrounding anatomy that can be targeted is thus significantly greater than the conformation of the muzzle-head alone would suggest.

VII2b(1)(b)(ii). Intracorporeally Controllable Bounce-Plate with Precision Adjustment in Rebound Elevation and Rotation Now to be described is a bounce-plate control mechanism that allows the bounce-plate to be deployed and retracted with precise adjustment in the rebound angle of elevation while the muzzle-head remains intracorporeal with no need to replace the bounce-plate midprocedurally. Such capability is advantageous when dealing with different tissues in hardness, that present nonuniform hardness as the result of disease, that present at different angles so that fine adjustments are needed to achieve accurate implant placement. To withdraw and reenter introduces unwanted delays, increases the risk of injury or irritation, especially to the entry point, the need for the operator to reorient, and extends the time the patient must be kept under general anesthesia.

By comparison, use of the embodiment described in the preceding section which provides only passive control over rebound angle of elevation for structured anatomy might necessitate withdrawal and reintroduction of the barrel-assembly repeatedly. To provide positive control over the rebound angle of elevation and not just the passive control provided by the spring tongue bounce-plate embodiment described in the preceding section, the push-pull and rotation control solid rod or shaft 135 in FIG. 36 is replaced with stationary or nonreciprocating and rotation control tube 135. In this embodiment, bounce-plate 53 is not positioned at intermediate horizontal positions (displacements, levels) as is the preceding embodiment shown in FIG. 36 but is either fully retracted (stowed) or fully deployed.

Ejection and retraction of bounce-plate 53 is accomplished inside control tube 135, which conveys a pulley belt between control and controlled pulleys or a shaft that joins control and controlled bevel gears at control lever 138 with controlled or distal pulley wheel or bevel gear at 141. Accordingly, advancing and withdrawing control tube 135 requires no calibration to measure horizontal displacement but does require a pointer on control lever 138 that moves against a calibrated scale mounted to control slide-box 134 to indicate the angle of elevation. Since with this embodiment the elevation is adjusted nonpassively by positive control only when bounce-plate 53 is deployed or fully forward, lever 138 will always be in the fully forward position flush to the rear of control slide-box 134. In this embodiment, when rotated fully back, control lever 138 fully raises bounce-plate 53 or deploys it when rotated all the way forward.

The calibration indicating the angle of elevation therefore need not move with lever 138. By comparison, control lever 138 in the embodiment shown in FIG. 36, where the angle of elevation is adjusted as the passive consequence of the extent of bounce-plate ejection or horizontal displacement, is not rotated forward and backward but pulled backward or pushed forward in a linear path. This embodiment therefore requires no projection 139 with a pointer or reference line that moves alongside a horizontal displacement calibration scale to either side as does that shown in FIG. 36. Numerous kinematic arrangements will allow control lever 138 when swung or rotated forward and backward to rotate the pulley wheel and belt or the bevel gear inside control tube 135 in turn is received into control lever 138 toward its lower end.

The pulley belt or shaft passes through control tube 135 to rotate the complementary distal pulley wheel or bevel gear that raises and lowers bounce-plate 53. That described here uses a pulley and is compatible with FIG. 37. Axle 144 is passed through one of two round diametrically opposed holes cut into the sides of control tube 135 toward its proximal end. These holes are slightly larger in diameter than the axle and allow the axle to rotate freely. Before axle 144 is passed through the opposing hole, the pulley wheel is slid over the axle to its center and the wheel set screw tightened. Its major portion having been passed forward through control tube 135, the proximal end of a pulley belt is looped about pulley wheel 141, and the axle passed through the opposite hole.

The ends of axle 144 now project through the openings in either side of control tube 135. Control lever 138 has holes at its lower sides for friction fitting receipt of the ends of axle 144. This is accomplished by slightly pulling apart the sides of lever 138, inserting the proximal end of control tube 135 between the sides of control lever 138, aligning the ends of the axle projecting from the side-holes in the control tube to the side-holes in the lever, and pressing the lever side holes onto the ends of axle 144. The axle is now immovably fastened at either side to the control lever, so that pushing lever 138 forward easily rotates axle 144, the pulley wheel, and pulley belt, thereby rotating controlled pulley wheel 141, lowering or depressing bounce-plate 53, and the reverse. When assembled thus, axle 144 serves also to strengthen control lever 138.

Since control lever 138 can adjust the angle of elevation only when bounce-plate 53 is fully deployed and therefore in the fully forward position and the most forward position of the lever is vertical when flush against the back of control slide-box 134, the forward throw or arc for lowering bounce-plate 53 generally commences at the bounce-plate fully raised position with lever 138 approximately horizontal.

Control slide-block 134 incorporates a detent to cue the operator to its position without the need to look at the mechanism. The detent consists of a small protrusion or stud at the bottom of slide-block 137 which seats with a distinct click into complementary depressions along the floor of slide-box 134, thereby confirming that bounce-plate 53 is fully retracted and bounce-plate 53 completely ensheathed or fully deployed and positioned for discharge, whereupon special care must be given to avoid gouging surrounding tissue.

VII2b(2). Trap and Extraction Recovery Tractive Electromagnets for the Recovery of Loose and Extraction of Mispositioned Miniballs A barrel-assembly of any kind must include means for both recovering any miniballs that are loose or that have been mispositioned upon implantation. To recover miniballs, the forward or distal end of a barrel-assembly, whether simple pipe or radial discharge, is equipped with an electromagnet assembly that consists of one direct-current tractive electromagnets in simple pipes and two in radial discharge barrel-assemblies, which are as large in size as the dimensions of the muzzle-head will allow. The U- or generally horseshoe-configured core with elongated bridge is made of vanadium permador (vanadium permendur) or silicon iron steel, and the winding in smaller gauge models of braided alumina-silica or alumina-boria-silica fiber ceramic-insulated silver wire.

In large gauged models for use in the airway and gut where the need for recovery is less urgent, the winding is copper. Whether disposed perpendically or parallel to the long axis of the barrel-assembly, miniball recovery electromagnets are polarized and trap-chambers or antechambers situated as shown in FIGS. 48 and 49. To improve the ability to select one miniball among others, the pulling pole is drawn to a needle point. For generating a field to trap loose miniballs, the electromagnets are controlled as a pair rather than independently.

Reversing the polarity of either exerts little practical effect, a miniball never remaining positioned exactly at a point where the fields theoretically null or cancel; instead, one or the other field will always dominate at the points described by the miniball, which will always be seized by that electromagnet. Continuously varying the amperage to the electromagnets allows varying the magnetic field strength and magnetomotive force from zero to the maximum. An optional laser catheter incorporated into the barrel-assembly by positioning it along the longitudinal axis to end at the center of the nose is without ferromagnetic content and unaffected by the magnetic fields it traverses.

Metal-capping the front ends (tips) of the optical fibers has been reported to yield better results (destruction or atheromatous lesions with least injury to the lumen wall) than bare-tipped fibers (Litvack, F., Grundfest, W. S., Papaioannou, T., Mohr, F. W., Jakubowski, A. T., and Forrester, J. S. 1988. "Role of Laser and Thermal Ablation Devices in the Treatment of Vascular Diseases," *American Journal of Cardiology* 61(14):81G-86G; Yang X M, Manninen H, Soimakallio S. 1991. "Laser Ablation Ability of Different Fiber Tips on Human Arteries. The Role of Photothermal Effect," *Chinese Medical Journal (English Edition)* 104(9): 721-727). A metal tip or probe for the present purpose must be nonferrous.

A means for trapping any loose miniballs must balance the forward extendibility toward a blind end or narrowing lumen diameter to which the muzzle-head can proceed with the need to retrieve any errant miniballs to this depth. The diameter of the muzzle-head varies according to the diameters of the lumens in which each is to be used. For use in the coronary arteries, these are on the order of 7-10 French. The tractive electromagnet in a simple pipe barrel-assembly, seen as 46 in FIG. 33 is enclosed within nonmagnetic housing 56 in FIGS. 31 thru 34, is singular, whereas the tractive electromagnets in radial discharge barrel-assemblies indicated in FIG. 39 and shown in FIGS. 48, 49, 65, 66, and 67 consist of a pair of individually controllable electromagnets positioned so that their attracting poles look outward to either side with polarities diametrically opposed.

Because the simple pipe is for use in the airway, wherein the recovery of a radiopaque loose miniball does not pose a risk of loss as in the bloodstream, providing the electromagnet with a spring-loaded door and antemagnet chamber is considered nonessential. The same basic magnet structure is used to trap any loose or to extract any misplaced miniballs, whether the barrel-assembly is of the simple pipe type with one electromagnet or a radial discharge type with two. The dimensions and maximum tractive force of the electromagnets is proportional to the respective barrel-assembly. The use of electromagnets allows adjusting the field strength to a steady or resting level to recover loose miniballs, raise the current and thus the field strength to extract implanted miniballs, then lower the field strength to zero and so prevent the dislodging of well placed miniballs as the barrel-assembly moves past these upon withdrawal.

Miniballs used in the airway or gastrointestinal tract are larger than those used in the vascular tree, for example, and individually discharged. The failure of a miniball to implant or to implant properly is thus noticed immediately, and since the patient is recumbent, a loose miniball will fall and adhere to the tacky lumen floor rather than drop into a lung. Accordingly, the recovery electromagnet can be left off or set to a steady protective trap or subextraction field strength, then raised to extraction field strength if needed. The fact that the barrel-assembly usually has an endoscope lashed alongside it, is equipped with a recovery electromagnet or electromagnets, and can readily be connected to an aspiration pump means that a mispositioned miniball is easily retrieved.

Discharge into the vascular system, however, is always performed with the tractive electromagnets set to a protective trap field strength to prevent a loose miniball from passing downstream. The resting field strength of the tractive electromagnets normally sweeps up any loose or lost miniball. However, where such an exigency would pose inordinate risk, the ability to locate a loose or lost miniball is increased by using miniballs coated with tantalum for increased radiopacity. In radial discharge barrel-assemblies, the electromagnet assembly, indicated as to relative position in FIG. 38 as 64 and shown as 80 in FIGS. 39 and 64 in FIG. 40, are mounted within chambers in a housing at the distal or forward end of the muzzle-head. To allow tantalum coated miniballs trapped in the magnet antechambers to be observed fluoroscopically, magnet housing is preferably made of a transparent material, such as polycarbonate.

Figure 38:
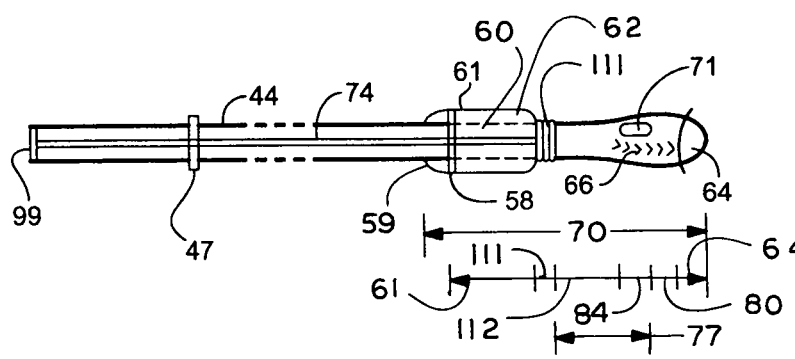
FIG. 38 is a longitudinal section view through the barrel-catheter of a single barrel, or monobarrel, radial-discharge barrel-assembly, the muzzle-head shown externally to allow its parts to be defined. An optional forward drive and sag leveling and stabilizing device distal to the twist-to-lock connecting flange is shown in FIGS. 77 and 78.
Figure 39:
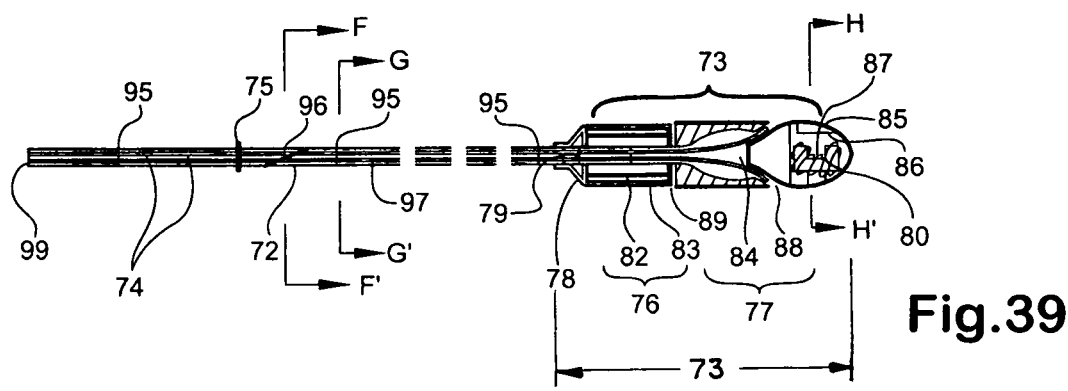
FIG. 39 is a longitudinal section through the barrel-catheter of a 2- or 4-barrel-tube multibarrel ablation or angioplasty-incapable (plain discharge, limited purpose) radial-discharge barrel-assembly, with a nearer than median view of the muzzle-head without a convoluted joining section and radial projection units of an ablation or an ablation and angioplasty-capable barrel-assembly as seen in FIGS. 48 and 49, showing the parts within the muzzle-head. An optional forward drive and sag leveling and stabilizing device distal to the twist-to-lock connecting flange is shown in FIGS. 77 and 78.
Figures 40, 41, 42:
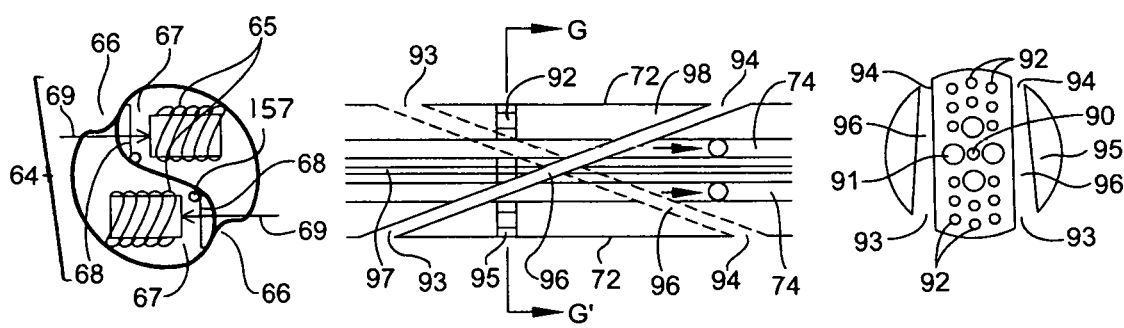
FIG. 40 is a cross-sectional view through the miniball recovery magnet chambers of a barrel-assembly taken along line H-H' in FIG. 39 with the muzzle-head rotated by 90 degrees.
FIG. 41 is a mid-longitudinal-section detail of the internal structure of a barrel-catheter as shown in FIG. 39 which has been longitudinally condensed to include both a blood-tunnel as in the plane indicated by line F-F' in FIG. 39 and a centering device as in the plane indicated by line G-G' in FIG. 39.
FIG. 42 is a view partly in cross-section along line G-G' in FIG. 41 through a centering device perforated by blood-tunnels which are depicted perspectively as receding into the distance in an ablation or angioplasty-incapable four-barrel radial discharge barrel-assembly.

Seen head-on in FIG. 40, the magnet assembly, indicated in FIGS. 38 and 40 as 64 and in FIG. 39 as 80, constitutes the most anterior or distal portion in any muzzle-head without, and the second most anterior portion in any muzzle-head with a heat-window in the nose, and is divided into two compartments, seen as upper and lower in FIG. 40. The horseshoe-configured single working face tractive electromagnets are contralaterally offset to allow a space in front of each which is enclosed behind corner plastic-hinged center-opening double doors that are recessed from the lumen wall, are stopped by opening further by contact with the magnets to the sides of the poles, and urged into closed position by means of plastic torsion springs at the hinges.

Small tabs prevent the torsion springs from opening the doors outwards or away from the magnet past the position to close the magnet antechambers. The force with which a loose or mispositioned miniball is drawn toward the magnet exceeds the restorative force of the torsion springs that otherwise urge the double doors into a closed position against the stop tabs. The strength of the magnetic field and restorative force of the torsion spring are sufficient to pull the miniball through and close the doors regardless of the entry into the antemagnet chamber of mucus, saliva, or blood. Recessing the double doors reduces the chance that these will be opened by brushing up against or scraping the lumen wall.

Since the attraction of a miniball already under recovery forces the double doors open, to provide a sensor to sound an alarm at the door hinge or spring is considered moot. As the front portion of the muzzle-head and barrel-assembly, all external angles of the magnet assembly are ground and polished smooth so that the front end, i.e., the distal nose or face, is completely convex or rounded, smooth, and continuous. Two of the blood-grooves that run longitudinally midway between the muzzle-ports are aligned to the spaces in front of each double door, and ground and polished so that the groove continues into the space smoothly. The other two blood-grooves are continued over the outside of the magnet assembly.

The muzzle-head, to include the motorized turret collar, port portion, and magnet assembly, is preferably encapsulated within a lubricious coating, such as those specified above in the preceding section entitled Sectional Extraluminal Stents, Segmented and Articulated or Chain-stents. The pistol grip or dedicated airgun controller thus has knobs to separately adjust the potentiometers that control the exit velocity and two others to adjust the field strength of the recovery electromagnets. Each magnet in the pair or magnet set is separately controllable over their range of magnetic field strength. For this reason, the same electromagnet set can be used with a low or resting field strength to catch any loose miniballs or to extract miniballs that have already been implanted but misplaced.

To extract a miniball that has already been implanted, one of the electromagnets is aligned alongside the misplaced miniball and the amperage raised until the miniball is pulled to the magnet. Increasing the amperage gradually to only the electromagnet positioned and directed toward the specific miniball to be extracted, the effect on other miniballs is minimized. The range of propulsive force available with any airgun and the immediate interchageability of different kinds of rotary magazine clips makes it possible to place a different number of barrel-tubes, each of variable diameter, within a barrel-catheter of given diameter for use in the same airgun.

Up to a certain limit in the diameters of the miniballs required, the barrel-catheter may be of a given size, which if exceeded, will require the use of an airgun of larger bore or the removal of a smaller and replacement with a larger diameter airgun barrel lining. With an airgun of maximum bore, airgun barrel lining adaptors and the ability to change the kind of rotary magazine clip in a moment allow connection to any barrel-assembly. In such a universal airgun, because the diameter of the airgun muzzle does not change but only different bore-reducing or increasing linings are inserted, the flange connector is of standard size such that any barrel-assembly can be connected to the same airgun. Accordingly, mechanical connection of the simple pipe barrel-assembly to the airgun is preferably the same as that to be described for single and multiple barrel radial discharge barrel-assemblies.

By removing one kind of rotary magazine clip and inserting another, the airgun can be quickly converted for use with barrel-assemblies having from one to four or more barrel-tubes that are alike. Different bores require changing the airgun barrel lining. Regardless of the number or diameter of the barrel-tubes, the barrel-assembly must always be precisely aligned so that each barrel-tube is positioned before its respective hole in the rotary magazine clip. The need to replace an airgun due to a malfunction should not necessitate the withdrawal of a barrel-assembly already placed within the lumen. To this end, interchangeability of a given barrel-assembly into different airguns is of distinct benefit. Reciprocally, when the diameter of the airway becomes too small for a simple pipe, to switch to a single barrel radial discharge barrel-assembly should not necessitate changing the airgun that is already adjusted to the proper setting.

Apart from these advantages in uniformity of connection, the expense to the practitioner is reduced. Barrel-assemblies should be interchageably connectable to an airgun regardless of whether the airgun has been modified from one sold on the market or was originally made for interventional use. The interchangeability of airguns and barrel-assemblies allows one and the same airgun to support any number of different barrel-assemblies, which is advantageous whether only one kind and size of barrel-assembly is used, other airguns being usable in the event of a malfunction, or barrel-assemblies of several different kinds and sizes are used, where each airgun can be equipped with a different bore reducing barrel lining Accordingly, a single flange-connector size according to the largest bore is preferred, a second airgun of still larger bore reserved for large zoo mammal veterinary use. The rotary flange or twist-to-lock connector limits the distance to which the barrel-assembly can be inserted into the barrel of the airgun. This places the end-plate before the rotary magazine clip with the least interval separating the proximal ends of the barrel-tubes and the hole in the rotary magazine clip respective of each barrel-tube.

VII2c. Application of Simple Pipe-Type Barrel-Assembly to the Magnetic Correction of Tracheal and Bronchial Collapse (Veterinary)

Suspension of the collapsed tracheal ceiling (dorsal membrane, dorsal ligament) is accomplished by placing miniballs or stays alongside the membrane for retraction by small but powerful permanent magnets. Depending upon the distribution of collapse and condition of the patient, the magnets are held in place by a segmental stent-jacket placed about the trachea itself, a clasp-jacket placed about the esophagus, infixion in the form of miniballs or stays in the floor or ventrum of the esophagus, subcutaneous patch magnets anchored in the fascia overlying the skeletal muscles of the back (posterior), or in a removable wrap (harness, halter) placed about the neck and/or withers, singly or in combination.

As addressed below, a clasp-jacket about or magnetic implants in the floor of the esophagus, a segmented stent-jacket, or subcutaneous patch-magnets can be used to suspend the tracheal ceiling. The extrapulmonary (primary) bronchi can be jacketed, but the intrapulmonary (secondary) bronchi must be patch-magnet suspended. In the airway embodiment, a simple pipe or single barrel (monobarrel) barrel-assembly as addressed below in the sections entitled Simple Pipe Type Barrel-assemblies and Limited purpose Single Barrel (Monobarrel) Radial Discharge Barrel-assembly, can be used to implant miniballs adjacent to collapsed cartilage rings along the dorsal tracheal membrane, or trachealis muscle.

Collapse of the tracheal ceiling is most often presented by toy breed dogs at mid-life see, for example, (Ettinger, S. J. and Feldman, E. C. 1995. *Textbook of Veterinary Internal Medicine*, Philadelphia, Pa.: W. B. Saunders), but is also seen in several other species, even adults, to include horses (see, for example, Ohnesorge, B., Gehlen, H., and Deegen, E. 2002. "Disorders of the Trachea in Horses," in *Equine Respiratory Diseases*, Ithaca, N.Y.: International Veterinary Information Service; Couetil, L. L., Gallatin, L. L., Blevins, W., and Khadra, I. 2004. "Treatment of Tracheal Collapse with an Intraluminal Stent in a Miniature Horse," *Journal of the American Veterinary Medical Association* 225(11): 1701-1702, 1727-1732), and goats (Belli, C. B., Benesi, F. J., Leal, M. L., and Nichi, M. 2003. "Trachael Collapse in an Adult Goat," *Canadian Veterinary Journal* 44(10):835-836).

Donkeys may have deformed tracheal cartilages (Powell, R. J., Du Toit, N., Burden, F. A. and Dixon, P. M. 2010. "Morphological Study of Tracheal Shape in Donkeys with and without Tracheal Obstruction," *Equine Veterinary Journal* 42(2): 136-141), and calves may acquire tracheal collapse due to dystocic trauma (Rings, D. M. 1995. "Tracheal Collapse," *Veterinary Clinics of North America. Food Animal Practice* 11(1):171-175; Fingland, R. B., Rings, D. M., and Vestweber, J. G. 1990. "The Etiology and Surgical Management of Tracheal Collapse in Calves," *Veterinary Surgery* 19(5)371-379). Provided the cartilages are sufficiently pliant and pulmonary complications are not involved, the stenting described herein will prevent asphyxia. By contrast, the tracheomalacia encountered in human neonates is almost always due to immature development with consequent lack of resilience, or chondromalacia, in the cartilage rings by the time of birth, which spontaneously resolves.

Ring resilience usually attained at 18-24 months (see, for example, Bluestone, C. D. 2005. "Humans are Born Too Soon: Impact on Pediatric Otolaryngology," *International Journal of Pediatric Otorhinolaryngology* 69(1):1-8), unless severe (McNamara, V. M. and Crabbe, D. C. G. 2004. "Tracheomalacia," *Paediatric Respiratory Reviews* 5(2): 147-154), unless suffocating, the treatment of tracheomalacia in neonates is avoided. When severe and segmented (localized) in neonates the use of a stent or stents to treat tracheomalacia is generally discounted in favor of bronchoscopically guided aortopexy (see, for example, Abdel-Rahman, U., Simon, A., Ahrens, P., Heller, K., Moritz, A., and Fieguth, H. G. 2007. "Aortopexy in Infants and Children—Long-term Follow-up in Twenty Patients," *World Journal of Surgery* 31(11):2255-2259; Dave, S. and Currie, B. G. 2006. "The Role of Aortopexy in Severe Tracheomalacia," *Journal of Pediatric Surgery* 41(3):533-537). Collapse pertaining to the tracheal ceiling or dorsum, and the aorta posteriad, aortopexy is inapplicable in dogs.

No claim herein addresses a bioabsorbable extraluminal stent for tracheomalacia as described by Hartig, G. K., Connor, N. P., Nalwa, S. S., and Sewall, G. K. 2003. "Bioabsorbable Exoluminal Stent," United States Patent Application 20030028255. Stents are used to treat the condition only when necessary (see, for example, Antón-Pacheco, J. L., Cabezali, D., Tejedor, R., López, M., Luna, C., Comas, J. V., and de Miguel, E. 2008. "The Role of Airway Stenting in Pediatric Tracheobronchial Obstruction." *European Journal of Cardiothoracic Surgery* 33(6): 1069-1075).

Sabre sheath or sabre tooth trachea in an adult with associated tracheomalacotic collapse the result of chronic obstructive pulmonary disease is likewise stentable, but due to the potential for development of erosive consequences, warrants periodic reexamination (de Trey, L. A., Dudley, J., Ismail-Koch, H., Durward, A., Bellsham-Revell, H., and 4 others 2016. "Treatment of Severe Tracheobronchomalacia: Ten-year Experience," *International Journal of Pediatric Otorhinolaryngology* 83:57-62; Perić, I., Paladin, I., Lozo Vukovac, E., Vela Ljubić, J., Gudelj, I., and Lozo, M. 2015. "Tracheomalatia, to Stent or Not to Stent," *Respiratory Medicine Case Reports* 16:137-139; Choudhary, C., Bandyopadhyay, D., Salman, R., Gildea, T., and Mehta, A. 2013. "Broncho-vascular Fistulas from Self-expanding Metallic Stents: A Retrospective Case Review," *Annals of Thoracic Medicine* 8(2):116-120; Ranu, H. and Madden, B. P. 2009. "Endobronchial Stenting in the Management of Large Airway Pathology," *Postgraduate Medical Journal* 85(1010): 682-687; Chin, C. S., Litle, V., Yun, J., Weiser, T., and Swanson, S. J. 2008. "Airway Stents," *Annals of Thoracic Surgery* 85(2):5792-5796; Saito, Y. and Imamura, H. 2005. "Airway Stenting," *Surgery Today* 35(4):265-270; Madden, B. P., Loke, T. K., and Sheth, A. C. 2006. "Do Expandable Metallic Airway Stents Have a Role in the Management of Patients with Benign Tracheobronchial Disease?," *Annals of Thoracic Surgery* 82(1):274-278; Fukai, I., Yamakawa, Y., Kiriyama, M., Kaji, M., Yano, M., Sasaki, H., and Fujii, Y. 2003. "Saber-sheath Malacic Trachea Remodeled and Fixed into a Normal Shape by Long-term Placement and then Removal of Gianturco Wire Stent," *Annals of Thoracic Surgery* 76(2):597-598; Wood, D. E. 2001. "Airway Stenting," *Chest Surgery Clinics of North America* 11(4):841-860), as may be certain cases of tracheopathia osteoplastica and other causes of airway stenosis (see Loo, D. K. and Allen, R., "Tracheopathia Osteoplastica Treated with Tracheal Stenting, *Chest* 126 Supplement:9658).

Remedy for some malformities and deformities without conventional stenting as such is under development (see, for example, Gao, M., Zhang, H., Dong, W., Bai, J., Gao, B., and 9 others 2017. "Tissue-engineered Trachea from a 3D-printed Scaffold Enhances Whole-segment Tracheal Repair," *Scientific Reports* 7(1):5246; Huang, L., Wang, L., He, J., Zhao, J., Zhong, D., and 7 others 2016. "Tracheal Suspension by Using 3-dimensional Printed Personalized Scaffold in a Patient with Tracheomalacia," *Journal of Thoracic Disease* 8(11):3323-3328).

While tracheal and bronchial stenosis in neonates, unlike that in toy dogs, for example, almost always subsides without treatment, thorascopic aortopexy is also the treatment of choice for tracheomalacia in older children, where prematurity of the cartilage rings at birth is not a factor (Durkin, E. T., Krawiec, M. E., and Shaaban, A. F. 2007. "Thoracoscopic Aortopexy for Primary Tracheomalacia in a 12-year-old," *Journal of Pediatric Surgery* 42(7):E15-E17; Carden, K. A., Boiselle, P. M., Waltz, D. A., and Ernst, A. 2005. "Tracheomalacia and Tracheobronchomalacia in Children and Adults: An In-depth Review," *Chest* 127(3):984-1005). Other procedures for ameliorating tracheomalacia are tracheopexy and esophagopexy addressed below in the section entitled Subcutaneous, Suprapleural, and Other Organ-attachable Clasp- or Patch-magnets.

Despite numerous complications, endoluminal stents have been used to treat severe tracheomalacia in children (see, for example, Antón-Pacheco, J. L., Cabezalí, D., Tejedor, R., López, M., Luna, C., Comas, J. V., and de Miguel, E. 2008. "The Role of Airway Stenting in Pediatric Tracheobronchial Obstruction," *European Journal of Cardiothoracic Surgery* 33(6):1069-1075) and adults (see, for example, Ernst, A., Majid, A., Feller-Kopman, D., Guerrero, J., Boiselle, P., and 6 others, 2007. "Airway Stabilization with Silicone Stents for Treating Adult Tracheobronchomalacia: A Prospective Observational Study," *Chest* 132 (2):609-616) in whom the condition may be associated with Morquio syndrome, Larsen syndrome, relapsing polychondritis, chronic obstructive pulmonary disease, intubation, goiter, goiter, vascular rings, and a number of other causes.

Other causes of obstructed breathing in neonates such as congenital tracheal stenosis, may recommend the combination of an extraluminal stent and surgery (see, for example, Hasaniya, N., el Zein, C. F., Mara, S., Barth, M. J., and Ilbawi, M. 2006. "Alternative Approach to the Surgical Management of Congenital Tracheal Stenosis," *Annals of Thoracic Surgery* 82(6):2305-2307). In a dog, however, tracheal collapse results when cartilage maintenance expressed as resilience begins to fail in middle age only to grow progressively worse. Accordingly, in man, pending spontaneous correction, the threat of suffocation in a severe case may warrant the temporary placement of an intraluminal stent.

Except where tracheobronchial constriction or collapse is permanent if not progressive, the procedure to be described for use in the airway is intended for veterinary application. Because the advancement of collapse is due primarily to increased ring infirmity and secondarily to stretching of the dorsal membrane from respiration that is made possible by and thus increases in proportion to the primary degradation in cartilage resilience, and because early intervention truncates stretching, an initial response should seek not to respond to the extreme collapse to which the condition would invariably progress were there no intervention, but rather to the condition as it exists.

While no tracheobronchial stent is etiotropic, or goes to the underlying etiology, but only nosotropic in alleviating an occlusion due to collapse of the airway, supporting the tracheheobroncial ceiling will intedict continued stretching of the collapsing dorsal membrane that the tidal flow of respiration, or constant push-pull action of breathing, would otherwise constantly aggravate. This action considerably increases collapse, which is primarily caused by a progressive loss of resilience in the cartilage rings due to a genetic defect expressed as an inadequacy of cartilage synthesis. Unless stopped, tracheal collapse eventually leads to inflammation and infection. For this reason, to persist in purely medical palliation with no mechanical intervention while the patient becomes more debilitated, and moreover, to then perform a radical procedure that may even include a thoracotomy, represents poor management.

Barring protracted dysphagia, but not a cough that commonly persists well after conventional procedures, annoyance exhibited by the patient due to unfamiliar forces on the trachea if any must be weighed against the risks of frequent suffocation leading to a loss of consciousness and even death were no invasive procedure performed. If not alleviated, residual symptoms are reduced in severity with medication. A definite error in the treatment of tracheal collapse is the detension in mechanical intervention and continued dependency upon medication that lacks the efficacy to terminate further progress of the condition. Surgery tends to be detained until the condition is advanced and as a result, the patient much impaired, and intervention with existing tracheal stents is properly detained because the stent itself creates complications by interfering with normal physiology at the lumen surface.

The existing classification of tracheal collapse (Tangner, C. H. and Hedlund, C. S. 1983. "Tracheal Surgery in the Dog—Part II," 5:738-762, reprinted in Ford, R. B. (ed.), 1999. *Head and Neck Medicine and Surgery in Small Animal Practice*, Yardley, Pa.: Veterinary Learning Systems, pages 236-246) assigns Grade I to a reduction in the lumen during respiration of 25 percent; Grade II to 50 percent, Grade III to 75 percent, and Grade IV to the substantial elimination of the lumen during respiration. In a dog with Grade I or II tracheal collapse (see, for example, Fossum, T. W. 2002. "Surgical Management of Tracheal Collapse". *Proceedings of the 27th World Congress of the World Small Animal Veterinary Association*, http://www.vin.com/proceedings/Proceedings.plx?CID=WSAVA2002&PID=2695; Johnson, L. R. 2001. "Diagnosis and Management of Tracheal Collapse in Dogs," *Waltham Focus* 11(2):3-8; Johnson, L. R. 2000. "Tracheal Collapse. Diagnosis and Medical and Surgical Treatment," *Veterinary Clinics of North America. Small Animal Practice* 30(6):1253-1266; King, L. G. 2004. *Textbook of Respiratory Disease in Dogs and Cats*, St. Louis, Mo.: Elservier/Saunders, page 354; Venker-van Haagen, A. J. 2005. *Ear, Nose, Throat, and Tracheobronchial Diseases in Dogs and Cats*, Hannover, Germany: Schluetersche), the sagging dorsal membrane can be suspended by means of ferromagnetic implants (miniballs) drawn by small neodymium permanent magnets, which depending upon the segment to be treated, the specific anatomy, and contextual medical condition, can be positioned with a stent-jacket or patch-magnets placed subcutaneously on the outer investing layer of the deep or muscle fascia overlying the implanted miniballs and/or suprapleurally, i.e., upon the serous membrane overlying the lungs.

At incipient grades of collapse, significant closure of the airway as the result of a diagonal folding flat of the trachea when the head is raised as revealed by fluoroscopic observation is unlikely, allowing an initial intervention that is minimal. The object being to minimize the trauma of stenting the collapse, the incision needed to feed through and subcutaneously place a longitudinally elongated open magnet-wrap without hooks and loops over the trachea or a flexible segmented stent-jacket, for example, is smaller than that needed to place stays, even with a stay insertion tool that incorporates side-tilting. For this reason, unless a malacotic condition recommends the use of wide stays, miniballs introduced from within the trachea are preferred.

If having already progressed to Grade III or IV collapse, the slack is pulled away laterally between ferromagnetic miniball implants in the ceiling of the trachea and magnets secured beneath the esophagus by means of a magnet-wrap as shown in FIGS. 10 and 11. The very malacia that demands correction renders the tracheal ceiling sufficiently compliant to move with the peristalsis of the esophagus during deglutition (swallowing) and without interference to the mucociliary function of the trachea. Since tautening the dorsal membrane alleviates the constant stretching action of breathing, it should seldom be necessary to retrieve the subcutaneous or suprapleural clasp magnets by means of an electromagnet and institute the second option.

However, such a conversion from the first option, directed to less progressed or lower grade collapse and the second to more progressed or higher grade collapse may be accomplished at a later date. Both procedures, placing fascial magnets and esophageal tacking, or magnetic esophageal tracheopexy, avert the acutely traumatic but nevertheless recommended procedures taught in every textbook of veterinary surgery at a time when the patient has become impaired by secondary sequelae, commonly ventricular and atrial enlargement and increased density of lung tissue, and is least likely to survive open surgery that may sever a thyroid artery or recurrent laryngeal nerve.

Expansion in the area treated at a later date is then made subject to actual eventualities, allowing trauma and risk to be minimized. Since an initial procedure can always be expanded upon at a later date when progress in the condition need not be presupposed, and an interval for recuperation is gained, the concept of extension for prevention is set aside. Furthermore, following any intervention, an interval should be allowed for the patient to learn to adapt to the new condition. If certain postures, such as raising the head past a certain angle, initiate the characteristic 'goose-honk' cough, then the patient is likely to associate this posture and coughing, and learn to avoid the posture. Unless movement is restricted unacceptably, or coughing on drinking or eating do not subside over time, reintervention is deferred.

Rather than to actually stent the structure it surrounds, a surrounding jacket can mount magnets to exert patenting traction upon miniballs implanted in an adjacent structure, notably by the esophagus upon miniballs implanted along dorsolateral longitudinal lines running along the ceiling of the collapsed trachea, for example. When a structure is not merely to support magnets for exerting force upon a neighboring structure but is itself to be stented, except that the endogenous outer layer of the structure to be stented lacks sufficient elasticity and strength to withstand puncture or retention of the miniballs, as may be true, for example, of diseased ductus and the normal esophagus, then reinforcement with an artificial or prosthetic 'adventitia' of the required properties is necessary.

Such a clasp-wrap or alternative means for introducing ferromagnetic implants in the wall of a ductus may be acted upon by either a more local stent-jacket or a magnet-wrap supported by a neighboring structure. However, a wall diseased as to retain little shear or tensile strength will present no substance to 'grab hold of' and will simply separate intra- or inter-laminarly (tunically delaminate) and collapse beneath the artificial adventitia. A structure so lacking in strength should be replaced with a graft or prosthesis. Placed outside the tubular structure, such a wrap-surround must be tissue compatible but requires no immunosuppressive drugs as would pertain to a homograft or xenograft.

When the miniballs can be mounted to a clasp-wrap (miniball wrap-surround) or alternative means for introducing ferromagnetic implants in the wall of a ductus, the need for implantation is eliminated and since lumen diameter need not be sufficient for transluminal access, ductus smaller in diameter than those implantable can be treated. However, to achieve continuous adhesion over the outer surface of the ductus that resists the traction of the magnets and yet complies with the intrinsic movement within the walls of the ductus, much less avoids interfering with such action, is elusive as not to eliminate the need for implantation capability. Because all bodily tissue, even the enamel of the teeth, is constantly replaced, long-term adhesion is a problem.

The use of a clasp-wrap is considered a relatively short-term solution unsuited to use in younger patients with a long life expectancy. Furthermore, the use of a wrap-surround, whether a clasp-wrap or a magnet-wrap, is limited to structures that are readily encircleable with few if any attachments that necessitate extensive dissection, and preferably with no more than loose surrounding fascia. The interposition of an artificial adventitia precludes the use of medication on the inner surface of the outer or magnet-mounting component or stent-jacket. However, the medication is then applied to the inside of the reinforcing wrap in contact with the structure.

Integration with the host tissue is not a desirable means for obtaining the adhesion of such an artificial adventitia to the outside of the ductus, because it requires an antecedent procedure, necessitates some negligible surface preparation scoring injury to the intrinsic adventitia of the ductus requiring time to heal, and usually results in bonding of insufficient strength to resist dislodgement by the tractive force exerted by the magnets over time, making adhesion undependable over the long term. Moreover, the need for treatment is usually urgent, making a procedure completed in a single operation imperative. The methods described herein are intended to avoid open surgery, some avoiding incision entirely, but do nothing to preclude reversal and the application of alternative treatment should results prove inadequate.

All of the procedures described herein for the repair of tracheal collapse are practically reversible, and neither in performance nor reversal nearly so traumatic or hazardous as are the standard procedures. If notwithstanding the use of magnetic field strength sufficient only to prevent the dorsal ligament from dropping down into the tracheal lumen and contrast to avoid injury to the vessels of the trachea and esophagus dysphagia or discomfort continues for more than 15 days following the esophageal tacking procedure or magnetic tracheopexy, then the miniball magnets are retrieved from the tracheal ceiling and esophageal floor by means of an electromagnet and intraluminal stents inserted in the trachea and bronchi as necessary.

Once magnets have been implanted, imaging other than magnetic resonance must be used, this technology now employed in veterinary practice. Other procedures described herein as might be applied to humans must consider that older technology heart pacing circuitry may be disrupted by proximity to magnets. An extraluminal stent, because it completely mantles about or surrounds and can seal an artery is better able to prevent rupture with hemorrhage than is an intraluminal stent having the form of an open mesh or grid. With a nonmagnetic stent-jacket, this reduces the risk of incipient aneurysmal rupture, whereas with a magnetic stent-jacket, weakening of the luminal wall with relatively high density miniball implantation is unlikely to result in a rupture.

Studies of the consequences of small puncture wounds to the internal elastic lamina have so far been limited to those produced by microsurgical needles and microelectrodes with no opportunity for healing. By comparison, the longitudinal segmentation of stent-jacket bar magnets or the use of specially made bar magnets that differ from those positioned longitudinally except arcuate in conformation to complement the outer contour of the ductus when vertically mounted to the outer surface of the base-tube and magnetized in the radial axis allows an extraluminal stent to comply with tonic (angiotonic), pulsatile, and peristaltic changes in gauge regardless of the anatomical tube treated or the length of the stent.

In addition to a systemic platelet blockade in arteries or anticoagulant in veins administered as a precaution in preparation for a transluminal procedure, the thrombogenic propensity of multiple if small (typically 0.2 to 0.4 millimeter) puncture wounds through the intima is additionally countered by coating the miniballs with the same or the same type of medication. The platelet blockade, anticoagulant, and other medication, such as an antibiotic, can be directly applied to the outside of otherwise unmedicated miniballs having a textured surface for tissue infiltration or to assist in the adhesion of a coating such as a solid protein solder.

The uncoated implant is thus able to imbibe the liquid by capillary action (capillarity, capillary motion, wicking), whereas an existing coat can already contain or absorb the medication. In either event, the addition of a platelet blockade or anticoagulant, for example, to miniballs would involve nothing more than wetting the miniballs in the rotary magazine clip with a small gauge eye dropper on insertion in the airgun chamber. The additive must be fully absorbed into the coating and not form a film or residue on the interior of the barrel-tubes as could result in jamming. Another reason that the additive should be fully absorbed is that penetration through the intima and at least some part of the media would wipe away or squeegee all but a small amount of the additive at the center of the rear surface of each miniball.

VII2c(1). Treatment of Tracheal Collapse in the Cervical Segments, i.e., Cephalad or Anterior to the Thoracic Inlet Tracheal collapse in the human neonate is almost always due to immaturity of the cartilages at the time of birth and spontaneously corrects itself over a brief interval; procedures delineated herein for the correction of tracheal collapse pertain to the progressively deteriorating condition encountered in veterinary practice. The treatment of tracheal collapse in anterior segments where the trachea has not yet entered into the surrounding mediastinal tissue can be accomplished in several ways, to include the placement of a stent-jacket about the trachea with lifting of the dorsal membrane or ligament by bilateral stays, a clasp-wrap, or ballistic miniball implantation with a simple pipe-type barrel-assembly to either side of the membrane, none of which suspend the membrane by a stent-jacket, magnet-wrap, or ductus intramural implants in the esophagus.

Clinical judgment should always veer toward the least traumatic, least risk prone, and shortest anesthetization time in a specific case. It is possible to place the clasp-jacket around, or implant stays or miniballs in the trachea and draw these upward with stent-jacket placed about the trachea or stent-jacket or magnet-wrap placed about the esophagus. The peritracheal stent-jacket can be of any type described in the section above entitled Types of stent-jacket. The magnetic force use is the minimum that serves to lift the membrane and the attracted and attracting elements—stays, clasps, and magnets if the jacket is extrinsically magnetized, are limited to the edges along the membrane and in tissue strong enough to minimize the risk of rupture.

Miniballs can be implanted in the trachea or esophagus by means of a modified commercial air pistol as addressed below in the section entitled Modification of Commercial Airguns, the cost of the apparatus low. The standard procedure involves the suturing of individual rings cut from high density polypropylene hypodermic syringe casings (see, for example, Hobson, H. P. 1998. "Trachea—Treatment of Tracheal Collapse: Ring Prosthesis Technique," in Bojrab, M. J. Ellison, G. W., and Slocum, B. (eds.), *Current Techniques in Small Animal Surgery*, Philadelphia, Pa.: Williams and Wilkins, Chapter 22; Buback, J. L., Booth, H. W., and Hobson, H. P. 1996. "Surgical Treatment of Tracheal Collapse in Dogs: 90 Cases (1983-1993)," *Journal of the American Veterinary Medical Association* 208(3):380-384; Tangner, C. H. and Hedlund, C. S. 1996. "Tracheal Surgery in the Dog," in Ford, R. B. (ed.), *Head and Neck Medicine and Surgery in Small Animal Practice*, (Reprints of articles published in 1983), pages 231-246; Hobson, H. P. 1976. "Total Ring Prosthesis for the Surgical Correction of a Collapsed Trachea," *Journal of the American Animal Hos-* pital Association 12:822-828), or less commonly, the polyvinyl chloride drip chamber of an intravenous administration set (Ayres, S. A. and Holmberg, D. L. 1999. "Surgical Treatment of Tracheal Collapse Using Pliable Total Ring Prostheses: Results in One Experimental and 4 Clinical Cases," Canadian Veterinary Journal 40(11):787-791), about the collapsed trachea to serve as prosthetic cartilage rings.

This necessitates access through open exposure, the entry incision extending over the entire length of the dorsal membrane treated, to which the patient already impaired by the condition should not be subjected. In calves, removal of the prosthetic rings is sometimes necessary and no less traumatic than is the procedure to place these Fingland, R. B., Rings, D. M., and Vestweber, J. G. 1990. "The Etiology and Surgical Management of Tracheal Collapse in Calves," Veterinary Surgery 19(5)371-379). In pronounced contrast to the trauma of a thoracotomy, the insertion of a stent-jacket, stent-jackets, or articulated stent-jacket is through the insertion of one end of the stent-jacket through relatively small incision at the level that defines either end of the stent-jacket.

This drastically reduces the trauma of placing prosthetic rings (see, for example, Woo, H. M., Kim, M. J., Lee, S. G., Nam, H. S., Kwak, H. H., Lee, J. S., Park, I. C., and Hyun, C. 2007. "Intraluminal Tracheal Stent Fracture in a Yorkshire Terrier," Canadian Veterinary Journal 48(10):1063-1066). The stent-jacket is held in position by its textured internal surface or gauze lining in relation to the intrinsic surface protuberances of the tracheal rings and by the magnetic attraction of ferrous implants just within the outer fibrous layer of the trachea. To secure a stent-jacket with end-ties may necessitate additional keyhole incisions.

The possible sequelae of such a procedure include infection, dysphagia, and stimulation of the cough reflex; however, these should prove medically manageable. Averting the risk of asphyxia is considered worth any discomfort due to magnetic attraction between tissues or, when magnets have been inserted subcutaneously or suprapleurally, in relation to metal objects in the environment, which the patient will never be too weak to leave and become conditioned to avoid. That any medical procedure must be tested extensively and over a long period is considered superfluous. If thought necessary to avert migration, the placement of suture is through and in line with this incision.

Requiring the extension of the incision to allow for suturing separate rings eliminated, insertion of the stent-jacket and its fixation in position are through an incision that is a small fraction of the length required for the conventional procedure, materially reducing trauma and extending treatment to patients too impaired to withstand the standard procedure. Extension of treatment to the distal bronchi is preferably by dorsolateral ballistic implantation into the bronchial ceiling with an eccentric two-way radial discharge barrel-assembly with the ceiling to be suspended by subcutaneously or suprapleurally implanted magnets (patch-magnets, clasp-magnets).

Dependent upon a small absolute diameter of the trachea for symptoms to appear, the patient suffering from tracheal collapse will almost always be a small dog. Distad, the lumens of the bronchi are likely to become reduced to no more than a few French. Such a severe reduction in working space may necessitate dispensing with a simple pipe and continuing with a one-way radial discharge or monobarrel-assembly of the kind ordinarily used for vascular and ureteric applications. Adaptability in the use of barrel-assemblies, and airguns that support different barrel-assemblies are significant cost reduction factors.

VII2c(1)(a). Use of a Magnet-Wrap About the Esophagus to Treat Tracheal Collapse in a Small Dog, for Example Where the esophagus and trachea course together in dorsoventral relation, tracheal collapse can be treated by the collapsed membrane (dorsal membrane; musculus trachealis; tracheal muscle) to the underside of the esophagus (magnetic esophageal tracheopexy). To suspend the dorsal membrane thus, a simple pipe barrel-assembly is used to implant miniballs at the junctions of the annular ligaments toward the dorsolateral edges of the cartilage rings. A compliant and nonconstricting magnet-wrap placed about the esophagus containing magnets at intervals along ventrolateral longitudinal lines suspends the miniballs. The esophageal magnets are not ballistically inserted magnetized miniballs, because the esophageal periphery tends not to be sufficiently hard and the otherwise unaffected esophagus should not be involved much less traumatized at the risk of inducing dysphagia.

If the testing means and method described below reveals that the ceiling is too weak or malacotic (soft) to prevent the implants from penetrating and perforating the tracheal ceiling, then the procedure is stopped and an endotracheal stent is inserted. While peristalsis moves the esophageal ventrum or floor vertically, which could pull against the dorsal membrane in a corresponding undulative wave, it moves the sides laterally, and this lateral movement affects the distance between the attractants slightly at most. If the tracheal implants are centered in relation to the lateral excursion of the peristaltic wave, then there will be no vertical displacement of the dorsal membrane, which is suspended as a side slung carriage.

Magnets within a magnet-wrap at intervals along ventrolateral longitudinal lines running beneath the esophagus are advantageous over subcutaneously or suprapleurally placed magnets in presenting a magnetic field much weaker and local to the treatment site and therefore effectively isolated from metal objects in the surroundings. The spherical contour of the implants essential for ballistic insertion presents a relatively poor gap for magnetic flux. When collapse has already extended to the bronchi, the decision to use subcutaneous or suprapleural magnets should be weighed against more conventional endobronchial stenting and the need for the patient to become conditioned to avoiding immediate contact with metal objects in the environment such as kitchen appliances.

This nuisance must be weighed against the obstruence of an endoluminal stent within the tiny secretory and macrophage-swept lumen. Any slack in the dorsal membrane resulting from the stretching caused by inspiration and expiration while the rings had continued to lose resilience and the ceiling increasingly collapsed is taken up and drawn out laterally between the dorsoventrally interfacing implants, draped over the side of the trachea, and thus clamped outside the lumen. As is true in other ductus, the use of a clasp-wrap to position miniballs along ventrolateral longitudinal lines along the esophagus is intended to avoid placing soft tissue under compression and restraining the passage of peristaltic contractive waves along the esophageal floor.

Whereas the trachea is active constantly, peristalsis normally occurs in the esophagus only during deglutition, and is substantially confined to its ventral or inferior (in man, anterior or rostral) two thirds. The very malacotic condition of the rings renders the tracheal ceiling sufficiently flaccid to comply with the peristaltic movement of the esophagus to which it has been suspended without interference to the mucociliary function of the trachea. Because the longitudinal lines of tracheal miniball implants are placed just within the outer fibrous sheath or adventitia of the trachea and the miniballs in the clasp-wrap are positioned along ventrolateral lines, esophageal peristalsis should be unaffected following healing, and coughing no longer presages eventual suffocation.

During deglutition, the peristaltic waves are impressed upon the tracheal dorsum; however, breathing is never simultaneous with deglutition and the very flaccidity of the collapsed trachea affords motile compliance. Nevertheless, some peristaltic induced coughing while eating is to be expected. If coughing is due to 'tickling' that triggers the cough reflex rather than to occlusion, then it is disregarded as a nonthreatening annoyance. If associated with residual occlusion, then ventrolateral implants can be placed over the segment affected or an intraluminal stent that is much shorter than would have been required were it the sole treatment is inserted. Barring immediate flush contact with a metal appliance or vehicle, the subcutaneous or suprapleural magnets are not so powerful as to prove problematic with metal objects in the surroundings.

The patient eventually becomes conditioned through experience to avoid snuggling up against such objects. In conditioning to avoid certain postures, acclimatization to new sensation, and to allow healing, the procedures to be described for the palliation of tracheal collapse, while reversible, should be allowed to remain in place until failure is certain. Where, as in the extremities, a vessel is embedded in tissue, some special consideration or complication must discourage the use of a conventional intraluminal stent to justify the use of a stent-jacket peripherally. The miniballs in the clasp-wrap placed about the esophagus are placed at the average anteroposterior interval by which the rings are separated and the trachea is then pulled slightly toward the anterior or posterior to align the tracheal and esophageal implants.

Even though both esophageal and tracheal miniball implants have been inserted through the mouth, the trachea has been restored to patency without significantly reducing the cross-sectional area to less than normal, coughing has been reduced, the threat of suffocation and the morbidity of incision and sutures has been eliminated, and once healed, esophageal function is not significantly affected. To accomplish the same repair by the conventional means of suturing prosthetic rings about the trachea requires approach through a cervical incision of considerable length, to place the sutures opposite to the incision is awkward extending the duration of the procedure, and when collapse has already progressed to extend into the bronchi, the lateral thoracotomy needed is untenably traumatic for the patient, whom the condition has long impaired.

Gross motility of the trachea in terms of overall bodily movement is reduced in detail by suspension from the esophagus; however, these normally move together. Most conditions of collapse should be remediated by a running dorsolateral magnetic tacking of miniballs implanted in the tracheal ceiling to a magnet-wrap about the esophagus as mentioned above. To avoid further stretching or ripping of the dorsal membrane, this is done through the annular ligament toward the ends of the rings. The existing grade of the condition, which is always progressive, should be projected to increase and extend posteriad over time. Therefore, regardless of the existing grade and distribution of collapse, treatment should be extended beyond the area affected.

Collapse of given grade at a level where the trachea is bent, especially when the convexity is directed to the posterior, can be more serious than when the course of the trachea is substantially vertical or the convexity anteriad. If more pronounced, a posterior convexity may necessitate the placement for a length along the bend maximum of implants along the edges of the ventrolateral quadrant of the tracheal floor as seen in cross-section, with subcutaneous magnets to draw these implants ventrolaterally, and esophageal tacking along the edges of the dorsolateral quadrant of the tracheal ceiling for the adjacent segments.

In advanced cases where collapse is such that the trachea becomes folded flat when the head is raised, combining the present method with the placement of prosthetic rings still makes it possible to considerably, perhaps critically, reduce the extent of surgery. Unless uniform tacking of the tracheal ceiling to the esophageal floor is insufficient, the use of subcutaneous magnets, especially in the cervical area, should be avoided as annoying the patient when the head is turned. Generally, following the tacking of the dorsal membrane as described herein, an interval should be allowed to see if the patient can simply learn to avoid aggravating postures before taking any further steps.

Single barrel discharge as used in the airway does not require the use of a rotary magazine clip which provides multibarrel discharge. Instead, semiautomatic operation is supported by a caliber-adapted spring-loaded or gravity fed magazine clip as described below. An otherwise ordinary gas operated pistol, or hand airgun, that has been adapted in caliber or gauge and lowered in exit velocity to the required range can be used. Next to a jointed stent-jacket immediately surrounding the implanted trachea, which is always preferred, the closest structure from which the collapsed dorsal membrane might be magnetically suspended is the floor of the esophagus.

VII2c(1)(b). Use of a Simple Pipe Barrel-Assembly to Treat Tracheal Collapse in a Small Dog, for Example Any procedure that involves placing implants in the esophagus or gut may result in the severing or injury of interconnecting neurons or fibers of the Auerbach (myenteric) or Meissner (submucosal) plexus; however, these have abundant interconnections and regenerate or heal quickly. A magnetic tracheopexy involves placing magnetic implants in the floor of the esophagus to suspend implants placed in the roof of the trachea is likely to induce dysphagia that should resolve by the second week following the procedure. In animal studies, complete transection and anastomosis of the gastroinstestinal tract was followed by regeneration of the myenteric plexus and nervous function within 2 to 8 weeks (Tokui, K., Sakanaka, M., and Kimura, S. 1994. "Progressive Reorganization of the Myenteric Plexus During One Year Following Reanastomosis of the Ileum of the Guinea Pig," *Cell and Tissue Research* 277(2):259-272; Solov'eva, I. A. and Atanasova, E. 1977. "Restoration of the Electrical Activity and Nervous Apparatus Following Section of the Stomach Wall in Dogs," (in Russian) *Fiziologicheskii Zhurnal SSSR [Soyuz Sovetskikh Sotsialisticheskikh Respublik* (Union of Soviet Socialist Republics) *Imeni I. M. Sechenova* [Sechenov Journal of Physiology of the Soviet Union] 63(5):723-734 (abstract in English at http://www.ncbi.nlm.nih.gov/pubmed/892079).

By comparison, ballistic implantation can do no more than infrequent and exiguous damage; functional impairment if any should be tolerable and dissipate within 4 weeks. While improbable, a perforation in the esophagus or trachea may damage fibers of the right or left branch of the recurrent laryngeal nerve inducing laryngeal spasm and respiratory distress (Tangner, C. H. and Hedlund, C. S. 1983. "Tracheal Surgery in the Dog—Part II," 5:738-762, reprinted in Ford, R. B. (ed.), 1999. *Head and Neck Medicine and Surgery in Small Animal Practice*, Yardley, Pa.: Veterinary Learning Systems, pages 236-246). Proximal damage to these branches can result in dysfunction of the upper esophageal sphincter and critical aspiration on swallowng (Orringer, M. B. "Tumors, Injuries, and Miscellaneous Conditions of the Esophagus," Chapter 19 in Greenfield, L. J. Mulholland, M., Oldham, K. T. Zdenock, G. B., and Lellemoe, K. D. (eds.) 1997. *Surgery—Scientific Principles and Practice* 2d ed., Philadelphia, Pa.: Lippincott-Raven.

Procedure for the palliation of tracheal collapse in a small dog:

1. The patient—usually a toy breed dog—is evaluated bronchoscopically and radiologically to confirm collapse as the cause of the symptoms and to observe the extent or grade of collapse as well as to determine the working diameter afforded by the anatomy. If the patient is too small, then the procedure is discontinued, and if justified by life expectancy and judged medically competent to withstand open surgery, the standard procedure to implant polypropylene prosthetic cartilage rings is performed. If not, then one or more deformation-resistant intraluminal stents are inserted. If not too small, the patient is evaluated for the variant of the procedure described herein, the medication to be used, and the dosages to apply.

2. A narrow gauge or small diameter pediatric bronchoscope is lashed to the barrel-catheter, care taken to avoid bending the catheter, and the patient preoxygenated. To clear the visual field for the operator, aspiration may have to be intermittent or "tubeless," spontaneous respiration used as the smallness of the airway dictates. Tiny patients may require percutaneous transtracheal jet ventilation or a preliminary tracheotomy with or without jet ventilation.

3. The patient is anesthetized and positioned supine on a cushion that allows the airway to be straightened with head dorsiducted or retroflexed and mouth gagged open as not to interfere with breathing or with mobility of the neck, which may then be positioned as necessary during the procedure. An adjustable stage or intervening platform with adjustable pitch for placement on the operating table gives improved access.

4. The bronchoscope is used to locate the cartilage rings and the conducting tube to insert one shot each into the anterior junction of each successive cartilage ring with the annular ligament bilaterally along the imaginary lines that demarcate the lateral edges of the dorsal quadrant of the trachea were it circular. Such placement not only takes advantage of the histology, but introduces prosthetic support at the normal intervals. To well seat the shot in each junction, the lamina propria is undercut by lightly pressing the 45 degree tip of the barrel-catheter flush against the endotracheal lining at a distance of ¼ inch anterior to each cartilage before triggering the shot. If the one miniball at each ring is suspected to sufficiently palliate the collapse and only dorsolateral subcutaneous or esophageal miniball magnets are to be used, then this concludes the endotracheal portion of the procedure, which should proceed directly to either the placement of the subcutaneous or esophageal magnets.

5. If increased suspension is considered urgent enough and worth the additional time and swelling in one procedure, then using a reverse 45 degree rebound tip or bounce-plate, a second pass is performed to insert one shot into the corresponding positions of each posterior junction bilaterally. The presence of a magnetic body inside the anterior and posterior junctions of each cartilage ring with the annular ligament through which the magnetic lines of force course lifts each ring under the pull of the magnets. The object is to arrange that the magnetic lines of force course through both shot implants of each ring to create a virtual bit, sling, or cross-pin that passes beneath and lifts each ring. If only dorsolateral subcutaneous disk or esophageal miniball magnets are to be used, then this concludes the endotracheal portion of the procedure, which should proceed directly to placement of either the subcutaneous disk or esophageal miniball magnets. If the need for double implants is not considered urgent, then a second set of posterior junction miniballs can be added at a later date; nonmagnetic, polarity will pose no problem.

6. If the collapse folds flat when the patient raises its head so that dorsal mending alone is predicted not to sufficiently palliate the collapse, then gag but not the bronchoscope or barrel-assembly left in place, the patient is now turned prone, chin resting, head dorsiducted with nonbinding support that allows the neck to be circumflexed. The same process is then used to insert implants in the same pattern along the imaginary lines that demarcate the lateral edges of the ventral quadrant of the trachea were it circular. This concludes the endotracheal portion of the procedure, which should proceed directly to the placement of the magnets whether subcutaneous or esophageal. 7. If the esophageal tacking method is intended and step 5 has been skipped, then gag left in place, the patient is now turned prone, chin resting, head dorsiducted with nonbinding support that allows the neck to be circumflexed. A magnet-wrap is introduced through an incision of minimal length as described above and placed about the esophagus so that the magnets are situated along imaginary lines that demarcate the lateral edges of the ventral quadrant of the esophagus. Fluoroscopy is used to assist in aligning the tracheal miniballs and esophageal miniball magnets in vertically interfacial relation.

8. If subcutaneous disk magnets are to be placed dorsoventrally or both dorso- and ventrolaterally, then to optimize the positioning, strength and size of each disk magnet placed dorso- or ventrolaterally, each magnet is first pressed downward into the muscle to the depth of the muscle fascia by a trained assistant while the operator observes the effect on the miniballs that have been implanted in the trachea. Since the disk magnets will be fastened to the laterally stable fascia, the repulsion of neighboring like poles is not felt and serves to isolate or render noninteractive the parallel magnetic circuits formed with the respective miniball implants; the coursing of the field from the same pole of one magnet to the same pole of an adjacent magnet of like orientation to produce a diagonal pulling force as resultant is precluded.

9. If neither a stent-jacket about the trachea or the use of a magnet-wrap about the esophagus is wanted, magnets to suspend the collapsed tracheal ceiling can be placed subcutaneously at an angle to draw the ceiling upwards with minimal compression to the esophageal ventrum. Fur that interferes with such preliminary positioning is trimmed away. Trying different magnets, the minimum pull required at each level is determined. Testing for different degrees of neck flexion, the operator uses the bronchoscope to observe which combination of smallest magnets urges the cartilage rings sufficiently erect to clear the airway, and marks the magnet to be placed in each position on the pelage and if necessary, on pressure sensitive adhesive backed labels temporarily placed on each magnet. Within the effective distance, raising the magnets reduces the pull, reducing, not increasing, any upward pressure upon the esophagus that would produce discomfort in swallowing. The fur is shaved at the prospective locations of magnet insertion. In the cervical region, use of the smallest magnets most dorsally positioned will eliminate or minimize the force of clamping sufficient to retain any dorsal membrane slack between the miniball and magnet when the neck is flexed. The same procedure is used to position ventrolateral magnets if needed.

10. A longitudinal incision through the integument on either side of the line of implants allows fastening the subcutaneous magnets to the surface of the muscle fascia. The prongs at the top or bottom are engaged and the fascia pinched so that the prongs at the other end engage when released. The incision is closed with surgically approved long-chain methacrylate cement and swabbed with antiseptic ending the procedure.

11. Routine recovery measures to include the administration of a local anesthetic to the prong sites as alertness is regained, oxygenation and the administration of anti-inflammatory medication are administered. If, as is common, steroids are to be avoided, then provided not otherwise contraindicated, postoperative swelling is managed with an NSAID such as Voltaren® (Novartis diclofenac sodium) or Cataflam® (Novartis diclofenac potassium) or a proteolitic enzyme NSAID such as Danzen® (Takeda Chemical Industries) in enterically coated tablet form or SerraZyme® (Health Australasia Limited serrapeptase; serratia peptidase). The administration of antibiotics is in accordance with routine. Once implants containing ferromagnetic metal have been implanted, magnetic resonance imaging must not be used when the implants must not be heated.

As with the conventional procedure, some coughing may persist for an interval or permanently, and here as well, a cough suppressant is administered at least pending healing. Once healed and any strange sensation subsides, coughing will likely be due to an incomplete resolution of the collapse, usually by virtue of omitting a collapsing segment. A followup procedure is considered if and only if the condition warrants. Before proceeding to conventional surgery or the introduction of an endotracheal stent or stents, the far less traumatic use of suprafacial clasp-magnets, a stent-jacket or stent-jackets, and esophageal tacking or magnetic esophageal tracheopexy should be tried, preferably, in separate procedures in that order.

If none of these proves effective and the patient is a poor candidate for surgery, then the miniball implants, if capable of spontaneous expulsion over time, are withdrawn with the aid of the simple pipe or a separate magnet, or if expulsion is not a concern, then simply left in place as bioinert, a magnet-wrap applied to the esophagus withdrawn, and a self-expanding nitinol stent or stents inserted (see Kim, J. Y., Han, H. J., Yun, H. Y., Lee, B., Jang, H. Y., Eom, K. D., Park, H. M., and Jeong, S. W. 2008. "The safety and Efficacy of A New Self-expandable Intratracheal Nitinol Stent for the Tracheal Collapse in Dogs," *Journal of Veterinary Science* 9(1):91-93; Moritz, A., Schneider, M., Bauer, N. 2004. "Management of Advanced Tracheal Collapse in Dogs Using Intraluminal Self-expanding Biliary Wallstents," *Journal of Veterinary Internal Medicine* 18(1):31-42; Gellasch, K. L., Da Costa Gomez, T., McAnulty, J. F, and Bjorling, D. E. 2002. "Use of Intraluminal Nitinol Stents in the Treatment of Tracheal Collapse in a Dog," *Journal of the American Veterinary Medical Association* 221(12):1714, 1719-1723; Hwang, J. C., Song, H.-Y., Kang, S.-G., Suh, J.-H., Ko, G.-Y., Lee, D. H., Kim, T.-H., Jeong, Y.-K., and Lee, J. H. 2001. "Covered Retrievable Tracheobronchial Hinged Stent: An Experimental Study in Dogs," *Journal of Vascular and Interventional Radiology* 12(12):1429-1436; and Sawada, S., Tanabe, Y., Fujiwara, Y., Koyama, T., Tanigawa, N., Kobayashi, M., Katsube, Y., and Nakamura, H. 1991. "Endotracheal Expandable Metallic Stent Placement in Dogs," *Acta Radiologica* 32(1):79-80).

In so doing, the type of stent must be chosen carefully (see, for example, Madden, B. P., Loke, T. K., and Sheth, A. C. 2006. "Do Expandable Metallic Airway Stents Have a Role in the Management of Patients with Benign Tracheobronchial Disease?," *Annals of Thoracic Surgery* 81(2):274-278; Radlinsky, M. G., Fossum, T. W., Walker, M. A., Aufdemorte, T. B., and Thompson, J. A. 1997. "Evaluation of the Palmaz Stent in the Trachea and Mainstem Bronchi of Normal Dogs," *Veterinary Surgery* 26(2):99-107; Fraga, J. C., Filler, R. M., Forte, V., Bahoric, A., and Smith, C. 1997. "Experimental Trial of Balloon-expandable, Metallic Palmaz Stent in the Trachea," *Archives of Otolaryngology—Head and Neck Surgery* 123(5):522-528). The insertion of an endoluminal stent should be resorted to only following failure of the procedure described above and demands frequent reexamination.

Surgery is preferred to the use of endotracheal stents, primarily, because these can fail (see, for example, Göbel, G., Karaiskaki, N., Gerlinger, I., and Mann, W. J. 2007. "Tracheal Ceramic Rings for Tracheomalacia: A Review after 17 Years," *Laryngoscope* 117(10):1741-1744; Mittleman et al. 2004; Woo, H. M., Kim, M. J., Lee, S. G., Nam, H. S., Kwak, H. H., Lee, J. S., Park, I. C., and Hyun, C. 2007. "Intraluminal Tracheal Stent Fracture in a Yorkshire Terrier," *Canadian Veterinary Journal* 48(10):1063-1066; Ouellet, M., Dunn, M. E., Lussier, B., Chailleux, N., and Helie, P. 2006. "Noninvasive Correction of a Fractured Endoluminal Nitinol Tracheal Stent in a Dog," *Journal of the American Animal Hospital Association* 42(6):467-471), the final recourse is to perform the prosthetic ring procedure.

Some prefer the use of a stent only for patients that are poor candidates for surgery (see, for example, Mittleman et al. 2004, cited above). Extraluminal stents afford superior results to endoluminal stents (Sewall, G. K., Warner, T., Connor, N. P., and Hartig, G. K. 2003. "Comparison of Resorbable Poly-L-lactic Acid-Polyglycolic Acid and Internal Palmaz stents for the Surgical Correction of Severe Tracheomalacia," *Annals of Otology, Rhinology, and Laryngology* 112(6):515-521, the form of stenting described in this specification, however, directed to progressive disease treated with nonabsorbable materials). An extraluminal stent cannot fracture, and the exposure essential to place the device is much smaller than that to place and suture plastic rings.

VII2c(2). Treatment of Tracheal Collapse in the Thoracic Segments, i.e., Caudad, or Posterior, to the Thoracic Inlet When suspension of the collapsed dorsal membrane is by esophageal tacking rather than through the use of a stent-jacket, once trachea and esophagus diverge, magnetic suspension is attained through the subcutaneous placement of magnets overlying the affected area. By contrast, a single stent-jacket may continue distally to the bronchial bifurcation, proximal portions of the bronchi as may be accessed without thoracotomy can be either stent-jacketed or suspended by subcutaneous magnets, or all portions of the bronchi can be supported by subcutaneous magnets. An object of the procedure is precisely to eliminate the need for a thoracotomy using a form of stent that is placed outside of the airway and od not susceptible to accumulating or clogging with mucus as to require reinspection, withdrawal, and replacement.

An evaluation of the procedure to be used must consider the course of the trachea in different body positions and not just when the patient stands or sits. When the trachea is recurved, subcutaneous magnets placed ventrolaterally to pull nonmagnetized or magnetized implants placed ventrolaterally in the anterior wall of the cervical trachea may occasionally be necessary to increase tracheal patency. Since this produces the annoyance of sudden clamping with movement, it is best avoided. Posterior to the neck, however, such use need not be discouraged.

The combination of methods, here the use of intraluminal stents in the bronchi, should always be considered. The following is limited to the repair of tracheal collapse without the need for incision of any kind or, if subcutaneous magnets are used, incisions that are very few, small, and shallow. The preferred treatment as delineated above requires a small incision through the integument along the bottom of the neck or cervical ventrum and insertion of a jointed stent-jacket. The best treatment for a given patient must rest with the clinical judgment of the veterinarian.

VII2d. Ablation and Angioplasty-Incapable Radial Discharge Barrel-Assemblies

A radial discharge barrel-assembly is intended for use in small diameter lumina such as arteries, the ureters, and bronchi where the wall of the lumen must not be gouged or incised. As seen by comparing the simple pipe barrel-assemblies shown engaged within an airgun in FIGS. 31 and 32 and with muzzle-head 45 in greater detail in FIGS. 33 and 34 to the radial discharge barrel-assemblies shown in FIGS. 38, 39, 48, and 49, a barrel-tube in a mono- or multibarrel radial discharge barrel-assembly as described below is equivalent to a simple pipe type barrel-assembly where an outer protective shell or torpedo-shaped body seen as 70 in the radial discharge monobarrel shown in FIG. 38 and as 73 in the radial multibarrel shown in FIG. 39 has been provided to enclose and surround the muzzle-port or ports.

Shell 70 or 73 assures smooth slippage through the lumen and protects the lumen wall by its shape, and if necessary, release of a lubricant through the barrel-tubes, a service-catheter fed down a barrel-tube, or a radial projection unit ejection tool-insert. The shell also serves to detain any miniball that due to striking a calcium deposit or otherwise sclerotic point, for example, fails to penetrate the lumen wall until it is seized by recovery electromagnet 80 as depicted in FIGS. 39 and 65 in FIGS. 48, 49,65, and 66. Caught within the interface between the lumen wall and the outer surface of the shell, the miniball is held within the depression it makes in the lumen wall and thus tends not to move as the shell slides over it.

However, even when the loose miniball rolls as the shell moves over it, the barrel-assembly can be withdrawn so as to position the tractive electromagnets to recover the loose miniball into a magnet antechamber. Except in the smallest patients, there is sufficient space in the trachea and bronchi to rotate the tip of a simple pipe type barrel-assembly. In dogs weighing less than about 7 pounds, it may be necessary to use a single barrel radial discharge barrel-assembly as described below in the section entitled Limited purpose Single barrel (Monobarrel) Radial Discharge Barrel-assembly. Essentially enclosing a simple pipe within a torpedo shaped shell, a radial discharge muzzle-head presents no sharp distal tip as necessitates sufficient space to maneuver it in order to avoid injuring the lumen wall.

The cylindrical conformation of a radial discharge muzzle-head allows its introduction into a lumen slightly smaller in diameter than the muzzle-head itself without the risk of stretching injury or the need for a angiotonic relaxant (angiotensin counteractant, hypotensive agent). The outer surface of the muzzle-head body is made lubricious to prevent clinging. Setting aside features of internal structure that can be used to vary flexibility using the same tubing, such as centering devices as addressed in the section below of like title, radial discharge barrel-assemblies can be made of many different tubing extrusions and coextrusions in any of numerous material and profiles to combine any desired flexibility with a slippery surface.

One way to both chemically isolate an outer surface that is potentially allergenic and impart slipperiness is to enclose the entire barrel-assembly in polytetrafluoroethylene shrink wrap. In a barrel-assembly that includes a turret-motor, a slit cut around the rotary joint or junction of motor to the proximal (rear) portion of the muzzle-head, which is fastened to the barrel-catheter, frees the forward portion to rotate, and film that would cover portals, such as muzzle ports, side-ports, and the tops of radial projection units, must be cut away. When made of nonferrous metal, to minimize adhesion to the lumen wall, the muzzle-head of any radial discharge barrel-assembly is preferably coated with a fluoropolymer such as polytetrafluroethylene.

When used in a structured lumen, such as the airway of a dog that is small enough to recommend avoiding the use of a simple pipe, and it is desired to introduce the implants in the retrograde direction (proximad, toward the operator), to avoid injury to the larynx and lumen by any protruding part, a radial discharge barrel-assembly can be used that is equipped with an endoluminal bounce-plate control mechanism as described above in the sections entitled Extracorporeally Deployable Bounce plate with Fixed Rebound Angle and Extracorporeally Deployable Bounce plate with Adjustable Rebound Angle. To minimize the risk of injury, the distal or front corners and edges must be rounded.

Since it is limited to one radius or maximally eccentric and relatively small in diameter, and thus less likely to exhibit strong resistance to twisting when torqued, but still includes tractive electromagnets, a radial discharge monobarrel benefits most from a turret-motor. The ability to aim the tractive electromagnets with facility allows the resting or steady-state trap retraction field force to be reduced reducing the risk for extracting a miniball that has been correctly implanted, and the radial projection units, installed normal to the longitudinal axis of the muzzle-head, can be used rotationally as well as during transluminal movement. Any radial discharge barrel-assembly must be usable in the vasculature and must therefore incorporate means for preventing:

1. The introduction of gas into the bloodstream during discharge.

2. Admitting an amount of blood into the muzzle-head sufficient to affect either the exit velocity or the internal equalization of pressure significantly, and 3. Preventing the loss of a miniball implant that could be carried downstream.

Accordingly, if the size of the patient or preliminary fluoroscopic examination reveals that the airway or distal portions thereof are too small in lumen diameter to manipulate a simple pipe, then a single barrel radial discharge barrel-assembly is used. Such a barrel-assembly is the same as one used in the vascular tree. Owing to the small diameter of most vessels and the eccentricity of most vascular lesions, the single barrel radial discharge barrel-assembly, because it can be made to the smallest diameter of any barrel-assembly, has the widest applicability, multibarrel embodiments serving to reduce operative time.

Even though working in the airway does not impose the demands for gas containment and nonsusceptibility to thrombose or clog that necessitates the use of a radial discharge device as in the bloodstream, lumen diameters that are too constraining to use a simple pipe necessitate the use of a radial discharge muzzle-head. Since the degree of anatomical differentiation in the airway becomes less distad, this is not a problem; however, an occasional dog with collapsed trachea will be so small that a simple pipe can be used for no more than the proximal segments.

The single barrel radial discharge barrel-assembly is similar to the simple pipe barrel-assembly in that the barrel-catheter and barrel are one and the same. The minimum diameter of the muzzle-head necessarily limited by the number of barrels, the single barrel radial discharge barrel-assembly allows access to vasculature and ductus very small in gauge, allowing treatment more deeply or distal into the vascular or tracheobronchial tree. Access to vessels and ducts less than a millimeter in lumen diameter also extends applicability to neonates and small veterinary patients. For this purpose, a rotary is more versatile than a linear feed magazine clip in allowing successive implants of different mass.

VII2d(1). Limited Purpose Single Barrel (Monobarrel) Radial Discharge Barrel-Assembly Extraordinary exceptions aside, neither limited purpose nor minimally capable barrel-assemblies can function independently of an interventional airgun. They differ in that a minimally capable barrel-assembly, as shown in FIG. 38, although a radial discharge monobarrel, is provided with a blood-groove along the side of the muzzle-head indicating that it also incorporates a heating element or laser in the nose for perfunctory preemptive or precautionary angioplasty to reduce the risk of releasing debris from plaque whether due to contact with the muzzle-head. More capable, it can be used to do the work of the limited purpose type.

A limited purpose barrel-assembly also differs from a multibarrel minimally capable type as shown in FIG. 39 in that it incorporates a single barrel. It is intended for use with a similarly inexpensive air pistol to alleviate tracheal collapse in a veterinary specialty practice, several different procedures for accomplishing this addressed herein, but also has uses in medical practice outside the vascular tree. Essentially limited to use outside the vascular tree when thermoablative capability is not essential, in smaller gauges, it is suitable for use inside the trachea of a dog too small to safely insert a simple pipe, or in a ureter, or in the reproductive tract, while in larger gauges, it can be used in the gastrointestinal tract.

VII2d(2). Multiple Radial Discharge Barrel-Assemblies with One- to Four- or More-Way Radial Discharge Muzzle-Heads Radial discharge barrel-assemblies for use in blood vessels must include gas return channels, and since Barrel-assemblies which can be used in a blood vessel can be used in any other kind of ductus, the figures reflect configurations suited to the more demanding application. Barrel-assemblies not suited for use in a blood vessel must be clearly marked as such, and can be made more simply and at less expense by omitting the gas return channels. Unlike balloons, solid catheteric devices such as a rotary burr, laser, or barrel-assembly cannot be deflated to allow resumption in the flow of blood past the device. This factor imposes a severe demand for miniaturization in the diametrical extension of the parts within the barrel-assembly, hence, the number and caliber of barrels.

The smaller the implants, the greater must be the distribution density to achieve a uniformity of pulling force that reduces to an acceptable level the risk of implants being gradually pulled through the adventitia with or without a portion of the subjacent layer or tunic leaving the lumen unaffected, for which contingency, preventive means will be described. Balloon-based deflatable or otherwise collapsible and re-extendible muzzle-heads and muzzle-heads having collapsible and re-extendible chambers would make possible the use of larger caliber implants, but would introduce much additional structural, materials, and bonding complexity where the embodiment would have to be fully dependable.

More significantly, a collapsible embodiment would unavoidably and unacceptably compromise the distal electromagnet assembly essential to trap loose and extract improperly positioned miniballs. For this reason, a deflatable or mechanical linkage-based collapsible muzzle-head is discounted, flow past the muzzle-head being achieved by keeping the muzzle-head diameter to a minimum not simply for this part of the barrel-assembly as a whole, but at each longitudinal level along its length and by providing pathways in the form of external blood-grooves and through-and-through tunnels that allow blood and contrast dye essential to confirm the reinstatement of patency to pass.

Preferred are mono and multibarrel Barrel-assemblies which are unitized components which include a proximal end-plate, the barrel-catheter containing the barrel-tubes, a motorized turret if present, and a muzzle-head which includes the proximal muzzle-ports through which the projectiles or miniballs are expelled and a distal tractive electromagnet set to recover any loose or misplaced miniballs, and a forward hemispherical nose to minimize the risk of perforations. For barrel-assemblies within a given range in diameter, simple pipe or single barrel and multiple barrel radial discharge embodiments are preferably engageable by the same airgun when the suitable airgun bore-reducing lining is inserted. The use of rotary magazine clips greatly facilitates the ability to change the caliber and thus allow one airgun to support numerous applications.

Muzzle-ports that face in opposite directions not only accelerate the process of implanting ductus that unlike the airway, lack structural differentiation, but inherently cancel the reaction to miniball discharge or recoil associated with transit through a curve to discharge when not counterbalanced. Turning now to FIG. 39, shown is a four-way or four barrel radial discharge barrel-assembly consisting of a barrel-catheter 72, muzzle-head 73, and four barrel-tubes 74 in FIGS. 39 and 41 of which only two are shown in these middle longitudinal sections, and stop-and-lock ring 75, which engages a ring with complementary interlocking projections on the muzzle of the airgun best seen in the detailed views of FIGS. 73 thru 75. Muzzle-head 73 includes turret-motor 76, and rotating muzzle spindle 77, which includes the tractive electromagnet assembly 80 at its front or distal end.

Turret-motor housing 78 is bonded to the outside of barrel-catheter 72 by clamping collar 81. When the barrel-catheter is of a material and thickness that becomes too soft when heated to 90 degrees centrigrade by the turret-motor stator while used for thermal angioplasty at during stall, clamping collar 59 is lined with a thermal insulant, such as polyurethane. At 95 are centering devices and at 96 a blood-tunnel, both described in sections that immediately follow. Muzzle-head body 73 is preferably micromachined in proximal (rear, turret-motor housing) and distal (front, ejection-head) portions under computer numerical control from a solid block of nonmagnetic stainless steel of material as specified above and hardened by heating and quenching.

en made thus, each pair of barrel and pressure relief channels, shown as 226 in FIGS. 48, 49, 65, and 66, are machine or laser-drilled diagonally and radially toward the longitudinal axis from the same aperture. Effectively a segment of the barrel, the outer surface of the proximal portion of the electromagnet assembly housing must be longitudinally aligned to the central arc of the barrel-channel. To prevent the gas pressure of discharge from forcing gas into the bloodstream, paths of least resistance to the flow of the pressurized gas are placed in communication with the muzzle-ports to return the gas to the peribarrel space. The cross-sectional area of the return path is equal to or larger than the sum of the cross-sectional areas of the barrel-tubes.

When appearing narrower than this in cross-section, it is because the barrel-channels are elliptical normal to the view. Material that is thicker than needed for the strength to resist deformation, fracture, and work hardening in normal use is avoided, especially in the spindle portion of the muzzle-head distal to the engagement of spindle neck 61 in FIG. 38 in the position of a shaft through in the through-bore torque turret-motor rotor 82 and the entry after distoradially diverging or splaying, that is, flaring outward, of barrel-tubes 74 into flush joints 84. To counter deformation of the barrel-tubes as would impede if not jam miniball ejection during or following rotation of the muzzle-head, the degree of rotation to either side is limited and the distal ends of the barrel-tubes are not tightly fit or gripped about but free to reciprocate.

As shown in FIGS. 39, 48, 49, 65, and 66, the abaxial or concentric rotational relation of the barrel-tubes to the barrel-catheter, which may be supported with centering devices, allows barrel-tubes 74 to continue through turret motor rotor 60 and 82 and spindle 77 in alignment, then to diverge and insert into the muzzle-exit holes with flush joint 84 that extend proximally from the exit-holes to allow reciprocal movement of the distal ends of barrel-tubes 74 when the muzzle-head is rotated provide at the front of ejection head 112. As shown in the same drawing figures, the proximal length of barrel-catheter 72, its contents, motor housing 78, and turret-motor stator 83 are fixed together and stationary.

That is, only spindle 77, consisting of flex-ring 111, and distal metal portions, which are unitized by bonding with the segment of the barrel-catheter journaled in rotor 82, rotate, the barrel-tubes continuous through the bore of motor rotor 82 and inserting at their distal ends into the ejection-head 84. Rotary joint 79 divides barrel-catheter 72 between the proximal portion clamped in clamp collar 81 fixing it in position and distal portion journaled within motor rotor 82. The distal portion of the barrel-catheter that is journaled in rotor 82 as the spindle stem or neck is bonded to the proximal end of convoluted tubing or elastic flex-ring 111. Clamp collar 81 fixed to the rear of through-bore configured turret-motor 76 locks pre-rotary joint proximal barrel-catheter 72 in coaxial relation with the distal segment of the barrel-catheter journaled in rotor 82 for rotation as the stem or neck of spindle 77.

For a four-way radial discharge muzzle-head, rotation is limited to 22.5 degrees in either direction for discharge and 90 degrees for electromagnet assembly extractions of misplaced miniballs. Muzzle-head detail FIG. 39 can also represent a two-way radial discharge muzzle-head, except that for the rotation of the barrel-tubes by 90 degrees, in either direction, the length, i.e., the recess and distance of reciprocation within flush joints must be slightly longer and the barrel-tube material used more pliant without deforming upon discharge. To prevent air from leaking out of the gas return channel and thus allowing blood to enter the muzzle-head, the barrel-assembly and airgun chamber must airtight except through the barrel.

The polymer of the barrel-tubes, which may consist of many different materials and compound tubing, must be sufficiently thick and strong that jerking and deformation do not significantly affect discharge. Preferably, there is little change in exit velocity as the rotational displacement is varied. Upon entry into the muzzle spindle 77, barrel-tubes 74 enter the splay-chamber, which allows the barrel-tubes to bend while flared centrifugally and to maintain the consistent association of each with its respective muzzle-port 88, situated about the periphery of the muzzle-head. Depending upon eccentricity of the lesions to be treated, the muzzle-ports may be equidistant or eccentric.

So that the barrel-tubes can counterdeformatively rotate and reciprocate, or move up and down within the barrel-channels in the muzzle spindle 77 sufficiently as not to become distorted or kink when the muzzle-spindle 77 rotates, the joint 84 between the terminus of the barrel-tubes and the metal spindle is flush fit but not fastened. The extent of this rotation and equivalent compensatory longitudinal excursion in the barrel-channel of the distal ends of the barrel-tubes, which terminate at muzzle-ports (that facing the viewer being 88), is slight, the maximum required being 180 degrees for the tractive electromagnets 80 to be directed at any angle.

Radially situated barrel-tubes 74 must be free to bend in response to the axial rotation of the spindle and therefore cannot be encased in metal. With nonessential metal removed, the proximal portion of the spindle between rotary joint 63 and the rotating and reciprocating flush joints 84 into which the distal ends of the barrel-tubes are inserted define a space, the splay-chamber, having a generally flared shape, the outer surface thus allowing blood to pass all round into blood-grooves 66 along the broadest segment and so entirely past the barrel-assembly.

As shown in FIGS. 48, 49, 65 and 66, a segment of convoluted tubing elastic flex-ring 111 to which the spindle is bonded with a long chain methacrylate cement just distal to its neck in the turret-motor rotor and the throat or level where the spindle flares radially and forward serves to:

1. Improve steerability by allowing radial flexion of the muzzle-head distal to the turret-motor at the convoluted segment.

2. Allow more blood to flow past.

3. Absorb and dampen the shock of discharge recoil, especially in an eccentric, hence, force-imbalanced, monobarrel or when ejection is eccentric or not precisely simultaneous in a radially symmetrical multibarrel.

4. Insulate and so temperature isolate the rear portion of the muzzle-head when heated by increasing the current to the turret-motor stator to allow thermal angioplasty.

5. Reduce the contact area of the external surface of the muzzle-head with the lumen wall, thus reducing any resistance to rotation of the muzzle-head by the turret-motor.

To both flex and damp as necessary, the material of the convoluted segment must comply with lateral forces applied gradually, such as in tracking, but resist those applied suddenly, such as discharge recoil. The flexion provided by this joint, which is made of tubing of a thickness and material, to include coextrusions, that is optimized for the barrel-assembly, affords improved steerability in tighter anatomical bends when the barrel-assembly is advanced or withdrawn. Since the amount of rotation for a given muzzle-port configuration is limited, the airgun can be discharged during semiautomatic control using the linear positioning table while the barrel-assembly continues moving, with no distortion of the barrel-tubes as might affect the exit velocity occuring.

More significant recoil shock absorption and damping is obtained by incorporating a second elastic disk or annulus between the ejection head and electromagnet assembly. To 'tune' this second damper for the multiple reaction modes essential to defray the recoil characteristics associated with discharge from one or a plurality of barrel-tubes from one and the same barrel-assembly, the second damper can be simple, i.e., comprise a single elastomer, or interpose different elastomers over its area, can be compounded or laminated, and be ridged, serrated, triangular, square, or sawtooth-waved in contour on one or both faces. Upon emerging from the neck of the spindle journaled within rotor 82, the barrel-tubes 74 remain unattached until engaged in flush joints or barrel-channels 84.

The barrel-tubes are accordingly rotated at their upper or distal points of attachment alone. Alternately, the barrel-tubes can be continuous up to and attached directly to the muzzle-ports without the interposition of an upper spindle portion; however, this tends to result in less than completely dependable bonding of the distal ends of the barrel-tubes to the muzzle-ports as required. When the barrel-tubes can be rotated by the turret-motor without distortion or kinking with their distal termini fixed in position, the junction with the barrel-channels in the spindle portion of the muzzle-head can be bonded as described below. In FIG. 39, roof 85 of upper recovery electromagnet chamber 87 of the diametrically opposed pair contains spring-loaded double or opera type door 86 leading to antemagnet chamber 87.

Nose i.e., the distal or front end 64 of the muzzle-head is like that of the radial discharge monobarrel seen in FIG. 40, which shows the positions of the recovery electromagnets in an ablation or angioplasty-incapable barrel-assembly lacking the trap-filter in the nose, radial projection units, laser, or burr radial discharge barrel-assembly shown in FIG. 67. With such a system, one to four or more miniball rotary magazine clips can be used in the same airgun and one to four or more miniball discharge barrel-catheters can be plugged into the airgun. By blanking out unneeded barrels at the rotary magazine clip, a barrel-assembly with more barrel-tubes than required can be used with fewer barrels.

In barrel-assemblies of three or more barrels, the muzzle-ports are generally equally spaced about the muzzle periphery. The applicability of equidistant muzzle-ports with and without blanked rotary magazine clips is considered sufficient to omit a capability to circumferentially situate muzzle-ports; for eccentric lesions, barrel-assemblies with muzzle-ports fixed in eccentric positions are used. Detachability of the muzzle-head from the barrel-catheter could pose a risk of detachment while deployed in a vessel, and with the muzzle-head unitized with the barrel-catheter, the durability of the two components in a unified embodiment is sufficient not to jeopardize losing the proportionately much greater value of the muzzle-head due to breakage.

For tight control under fluoroscopic and angioscopic viewing, the use of polytetrafluoroethylene in radial discharge barrel-assemblies, which consist of barrel-tubes, the barrel-catheter containing these, and the muzzle-head, should impart a torque or turning ratio approaching 1:1. Positioning is assisted by adding angular displacement indicating tick marks to the radiopaque markers about the barrel-catheter used to indicate the length of catheter introduced. Should recovery by means of an electromagnet be necessary, nonabsorbable miniballs are radiopaque and may additionally be contrast marked with tantalum, for example.

Miniballs that must break down, such as those consisting of or coated with medication and those with an outer coating of solder that is to flow after having been placed, contain sufficient ferromagnetic material to allow their recovery if dangerously mispositioned.

Such are not completely encased or sealed with contrast such as tantalum provided with separated markings at the surface to expedite locating. Length-of-entry graduations are a standard feature of angioplastic (angioplasty) guide-catheters. Polytetrafluoroethylene tubing is inherently flexible (Young's modulus=0.5 gigapascals); a barrel-assembly with a barrel-catheter and 4 barrel-tubes of the material is still sufficiently flexible for tracking. The flexibility can be reduced by coextrusion or coating of the barrel-catheter with polypropylene (1.5 to 2.0 gigapascals), for example. To provide low friction surfaces when coextruded to affect flexibility, the outer surface of the barrel-catheter and inner surfaces of the barrel-tubes are those made of polytetrafluoroethylene.

Steering within the range of curvature that does not flatten the barrel-tube or tubes so that these would jam can be assisted with the aid of an external electromagnet to urge the muzzle-head in the desired direction. To resist snagging and stretching injury, the muzzle-head is wetted with heparin-saline solution and/or lubricant, the rest of the barrel-assembly lubricated as specified below shortly. Since the magnet antechambers at the front of the muzzle-head are closed off by spring-loaded doors to present a continuous or monocoque outer contour without edges that would scrape against the intima, these are pushed open to allow wetting with heparin-saline solution.

To impart a mild curvature to the barrel-channels in a solid block of metal would require that the solid block first be halved and then be quartered along its long axis twice to allow half barrel-channels to be milled into either face of the mating faces. The quadrants would then have to be fastened back together by means of an adhesive, which is not preferred. Due primarily to the elasticity of the lumen wall in healthy tissue as a standard, the range of impact forces functional in implanting the miniballs subadventitially is wide; within this range, a difference in exit velocity affects the distance the miniball travels through the media and the length of the slit it cuts through the external elastic lamina, which is negligible when the force of impact is properly set.

That only diseased tissue warrants treatment, and such tissue is capable of wide and unpredictable deviation from the normal is responded to by preliminary tissue puncture resistance testing means described below. With tantalum coated miniballs, the distance traveled along the inner surface of the tunica adventitia or outer fibrous jacket of the structure is observable fluoroscopically. However, the close observation and recording of wound production by such means necessitates the use of a high-speed camera such as a Redlake's MotionPro® HS Series, EG&G 549-11 Microflash® or Cordin Dynafax® 350 using preautolytic excised tissue under laboratory conditions.

To minimize the risk of stretching injuries from resistance to advancement, withdrawal, and traversing a tortuous stretch of vessel especially when steering is assisted through use of an external (extracorporeal) electromagnet to attract the muzzle-head, barrel-assemblies made of materials other than polytetrafluoroethylene are coated with an external lubricious coating such as ACS Microslide®, Medtronic Enhance®, Bard Pro/Pel® or Hydro/Pel®, or Cordis SLX®. Just before introducing the barrel-assembly into the bloodstream, the muzzle-head is wetted with a heperine-saline solution, and if the barrel-catheter is not coated with or made of polytetrafluoroethylene, the rest of the barrel-assembly is wetted with a light coating of a well tolerated ophthalmic type lubricant such as 1% or 2% single-chain hyaluronic acid (sodium hyaluronate; oxycellulose; hydroxypropyl methylcellulose; hyaluronan) sold under such trade names as Healon®, Adatocel®, Amvisc®; IAL®, or Biolon® diluted with saline solution; or glycerin diluted with water.

For trackability or steerability to allow femoral or brachial entry and thus eliminate the need for open exposure, the tubing for a catheter to represent the barrel-tube in a single miniball discharging barrel-assembly with a radial discharge muzzle-head or a barrel-catheter containing multiple barrel-tubes, or the material used in both, to be described, ideally have high combined pliancy, or flexion without kinking or folding. The need for pliancy, usually expressed in terms of flexural strength or flexural modulus as defined by American Society for Testing and Materials standard Document D790-03 entitled "Standard Test Method for Flexural Properties of Unreinforced and Reinforced Plastics and Electrical Insulating Materials," rises with the number, diameter, and wall thickness of barrel-tubes, four barrel-tubes contained within a barrel-catheter, for example, posing a stringent flexibility requirement.

A number of medical grade, flexible, high fatigue strength, bioinert, nondegradable, uncoated, and nonleaching nonchemical-absorbing polymers that are free of polymerization process chemicals and do not give off acidic plasticizer gas when sterilized are suitable for use as barrel-catheters and tubes in barrel-assemblies. Suitable barrel-tube materials include polytetrafluoroethylene, which is lowest in friction but relatively stiff, polyamide such as Dupont Nylon Zytel®, or a polyurethane elastomer, such as Dow Pellethane® 2363 and numerous similar products. Due to the propulsive force of the airgun before the relief control retrofitted or built in is used to bleed off or moderate the pressure generated within the valve body, tubing material with a higher coefficient of friction than polytetrafluoroethylene but greater pliancy, such as low density polyethylene, vinyl, or nylon are readily usable through vascular bends, whereas stiffer tubing is not.

For anatomical bends that due to the relative stiffness of polytetrafluoroethylene tubing make steerability resistive, a superior solution is to use barrel-tubes of highly pliant polymers such as Nylon 12 and Nylon 66, already approved for use within the body, but lubricated as stated above and lined with a thin coating of polytetrafluoroethylene for low friction, or slipperiness. By varying the relative thickness of polytetrafluoroethylene and polyamide in compound tubing, combinations of pliancy and stiffness suitable for application to the apparatus to be described may be obtained in different diameters over a wide range of tube internal wall friction. Flexibility of the barrel-assembly over the length to remain outside the patient equal to that applicable to the length to be introduced is undesirable as gratuitously increasing the rolling resistance to the miniballs unpredictably.

At the same time, flexibility sufficient to track anatomical bends is imperative for distal lengths typically introduced into the body. If made of the same material, then according to the softness of this material, the internal barrel-tubes and barrel-catheter containing these must not exhibit friction in the 'bores' proportional to the pliancy. A suitable combination of pliancy and stiffness in the barrel-tubes can be obtained by coextruding an inner layer of polytetrafluoroethylene within a soft outer polymer where the relative thickness of the polytetrafluoroethylene diminishes, incrementally changes, or discretely changes at one distance distad. For increased stiffness, the barrel-catheter and barrel-tubes can be made of different polymers or coextrusions over the length of the barrel-assembly to remain outside the body.

The pliancy of the barrel-tubes can also be varied along the length of the barrel-assembly by using centering devices (FIGS. 39 and 41 thru 45) that vary the distance from the longitudinal central axis of the barrel-catheter to the central axes of the barrel-tubes. Specifically, over the distal length of the barrel-assembly where flexibility to track anatomical bends in the vascular system is essential, the barrel-tubes are perforated, imparting greater flexibility to this length. Reduction in stiffness in the distal portions of the barrel-assembly to be entered into the body is also obtained by perforation of the barrel-tubes and by using centering devices to be described to position the barrel-tubes farther from the longitudinal axis of the barrel-catheter.

The internal pressure generated by discharge of the airgun is dissipated by using barrel-tubes with perforations over the distal portion of the barrel-assembly to be introduced into the body. These pressure relief perforations provide a path for the relief of the airgun discharge pressure within the barrel-assembly that is less resistant than the pressure that would be required for the gas to enter the bloodstream. These perforations must be too few, too spaced apart, and too small to cause folding or kinking of the barrel-tubes as the barrel-assembly is advanced transluminally.

By situating these barrel-tube perforations toward the distal end of the barrel-assembly, the distal segment that must be more flexible to follow the curves of vessels are rendered more flexible. The number, shape, and location of these perforations is a factor in determining the pliancy of the barrel-tubes and the barrel-assembly as components therein. To place blood flow side-holes in the barrel-catheter as well and thus achieve even greater flexibility is disallowed by the need for this space to equalize the pressure within the barrel-assembly during discharge while immersed in blood without introducing gas as bubbles into the bloodstream.

While to reduce friability due to rotary magazine clip-hole adhesion or barrel friction and any tackiness, a light coating of a well tolerated ophthalmic type lubricant such as 1% or 2% single-chain hyaluronic acid (sodium hyaluronate; oxycellulose; hydroxypropyl methylcellulose; hyaluronan) Healon®, Adatocel®, Amvisc®; IAL®, or Biolon® diluted with saline solution; or glycerin diluted with water may be applied to miniballs with a medicated outer coating of dried syrup, separate lubrication as might variably accumulate along the barrels introducing mechanical uncertainties and possibly forming a film over the muzzle-port by surface tension that might additionally congeal not permissible.

Pliancy, however, tends to vary as twisting, hence, the turning or torque ratio, which with a passive or nonmotorized muzzle-head, is ideally 1:1, and the coefficient of friction of the barrel tubing material, which is significant as the guideway for the miniballs. The coefficient of friction is determined with the aid of an Instron® or similar tester, such results provided by the tube maker. Turning ratio is more significant when the implants must be placed at particular circumferential angles. Since the airguns used generate sufficient propulsive force to project almost any interventially functional number and diameter of miniballs through respective barrel-tubes from the point of entry, usually inguinal, to the treatment area, such as at the heart, through rolling resistance comprised of bends in polymeric tubing of any coefficient of friction, and this force can be controlled, pliancy is the dominant consideration.

As is conventional with guide-catheters, barrel-assemblies are marked off in distance increments and indicate resistance to rolling per unit length at a standardized degree of bending or radius of curvature that must be coordinated with required force of impact data for different tissues. Barrel-assemblies with plural barrel-tubes display a number or other distinctive marking for each produced by inclusion in the mold used to make the proximal end-cap and by engraving the same mark next to each muzzle-port. When the barrel-assembly must be coursed along a different route than the preparatory angioplasty, access through a separate incision is not significantly traumatic and has been made relatively safe.

Broadly, conventional stenting is preferable in geriatric and terminal patients, whereas application of the methods and apparatus described herein are preferable where life expectancy recommends avoiding sequelae. Barrel-assemblies with multiple barrel-tubes are for use in smaller diameter vessels and ducts, usually around 6 to 10 French, or 2 to 3.3 millimeters, especially in the arterial tree, where operating time should be kept to a minimum. For this reason, it is desirable to discharge multiple miniballs at once and in quick succession. The structure of the barrel-assembly thus allows radial discharge and the airgun is semiautomatic.

At the same time, dependable means for preventing miniballs from escaping into the bloodstream must be provided. Shown in FIG. 38, whether antegrade or retrograde, a barrel-assembly for use in the vascular tree displaces blood upon introduction into the bloodstream and must incorporate features to prevent ischemia due to obstruction to the flow of blood or a partial blockage that results in hypoxemia. The other type ductus where obstruction to oxygenation must be minimized is in the airway, where a radial discharge barrel-assembly must be advanceable and withdrawable within a lumen slightly larger in diameter than the muzzle-head.

Such a barrel-assembly must therefore provide paths for the blood or air to move past it. For this purpose, the muzzle-head is kept at least 10 percent smaller in outer diameter than the lumen. The same limitation does not apply to gastrointestinal or urinogenital (urogenital) ductus where oxygen dependency is less immediate and the lumen can be purged before entry. To allow some blood to pass even when the muzzle-head unexpectedly occludes or obturates the lumen, the muzzle-head is provided with longitudinal blood-grooves or furrows 66 on its outer surface midway between the barrel-tube 74 exit-holes 71. The blood-grooves continuous over the muzzle-head to include both the proximal or muzzle-port and distal or electromagnet sections allow some pulsation to pass the barrel-assembly.

Some limited transmission of the pulse through the barrel-assembly is obtained by means of side holes through the wall of the catheter barrel (see De Bruyne, B., Stockbroeckx, J., Demoor, D., Heyndrickx, G. R., Kern, M. J. 1994 "Role of Side Holes in Guide-catheters: Observations on Coronary Pressure and Flow," *Catheterization and Cardiovascular Diagnosis* 33(2):145-152). The side grooves or side hole tunnels are connected by means of peripheral tangential tunnels that course diagonally relative to the longitudinal axis. The placement and angles of these flow through tunnel tubes can also be used to buttress and stiffen the barrel-assembly over designated segments along its length. Several different materials and manufacturing techniques can be used to produce the one to four or more way radial discharge muzzle-head.

The preferred embodiment consists of micromachining and micropolishing a solid block of stainless steel into front or ejection head and rear motor housing portions. The structure of the muzzle-head is the same regardless of the number of barrels or circumferential angle of the barrel exit ports, and a variety of double barreled or two-way barrel-assemblies in various sizes may be necessary to allow variation in implantation angles. Passivation to remove surface contaminants or to improve the appearance of the muzzle-head, which is highly polished, is unnecessary, but is desirable for enhancing corrosion resistance. Made thus, the barrel-tube channels that contain the barrel-tubes in the muzzle-head are machine or micromachine drilled, hence, straight throughout their length.

To allow the mild curvature of the barrel-tubes necessary to diverge, that is, to splay or veer outwards to be redirected from the parallel orientation in the barrel-catheter to the circumferential placement of the muzzle-ports about the periphery of the muzzle-head, a splay space or splay chamber is interposed between the barrel-catheter receiving recess or socket at the proximal end of the muzzle-head and the entry of the distal ends of the barrel-tubes into their respective similar but smaller sockets in the proximal surface of the upper or distal portion of the muzzle-head which continues the barrels to the muzzle exit ports. The length of this space or splay chamber depends upon the wall thickness and pliancy of the barrel-tube material.

The underside of the upper, barrel-channel portion of the muzzle-head, or ceiling of the splay chamber has four openings to receive the four small gauge barrel-tubes one each into a barrel-channel. The proximal or bottom end of the muzzle-head includes a collar or neck to receive the barrel-catheter containing the barrel-tubes. Most often the pliancy of the barrel tubing material will necessitate that the distal ends of the barrel-tubes be able to rotate and reciprocate within flush joints containing barrel-channels 74 of the metal portion of the muzzle-head that terminates with the muzzle-ports or exit-holes.

However, provided the outer surfaces of the polytetrafluoroethylene barrel-tubes in contact with the walls of the barrel-channels are not excessively rotated and have sufficient slack to avoided distortion of their bores when rotated by the turret-motor, these are primed or etched with a special purpose chemical such as Acton Technologies, Inc. Fluoro-Etch® or W.L. Gore® and Associates, Inc. Tetra-Etch® or blown-ion air plasma type corona, or flame surface treated and coated with an adhesive suitable for bonding etched polytetrafluoroethylene to stainless steel, such as NuSil Technologies MED-1037 or MED3-4013 then threaded up through the bottom holes of the splay chamber ceiling until exiting the vertically oblong muzzle barrel openings.

The ends are then cut and polished flush to the surface of the muzzle. The barrel-catheter is then slipped over the set of four barrel-tubes until it is brought just short of the socket or receiver for it formed by the collar at the proximal or bottom end of the muzzle-head. The outer surface of the barrel-catheter to engage the socket at the bottom or proximal end of the barrel tip is etched and the same adhesive applied before its upper end is inserted into the socket. An alternative method for producing two and four-way muzzle-heads over a range of diameters from about 7 to 10 French is polytetrafluoroethylene thermoforming by resin transfer-molding, which is well known to those skilled in the art of plastic molding.

Made thus, the polymeric muzzle-head should nevertheless contain ferromagnetic inclusions to preserve steerability and abutment with the assistance of external electromagnet. Since the barrel-catheter and barrel-tubes as well as the barrel tip are all likely to be made of polytetrafluoroethylene, conventional polytetrafluoroethylene resists self-bonding, and the barrel-catheter and barrel-tubes would not be molded in one piece with the barrel tip, a special polytetrafluoroethylene molding material such as E.I. Dupont de Nemours Teflon NXT® is used. If the muzzle-head is cast, then positive inserts in the mold can be used to yield mildly curved barrel-tube channels eliminating the need for a splay space.

Preferred is a barrel-assembly which comprises the barrel-catheter and muzzle-head in a single unit that plugs into the barrel of the airgun. The barrel-assembly comes with rotary magazine clips containing test miniballs and should never be used with test miniballs of different specification. To incorporate the rotary magazine clip chamber at the proximal end of the barrel-catheter as unitized is not preferred, because this necessitates a communicating arm or intromitting pawl from the airgun. As a matter of terminology, the switch or trigger actuator and pressurized gas cylinder or canister represent the minimum distinctly airgun portions of the apparatus described herein.

The barrel-catheter and barrel-tube sockets consist of internal diameter flush joints, meaning the wall thickness of the inserted tubes is accommodated by the surrounding material of the receptacle so that there is no change in the internal diameter of the lumen at the joint. The end of the barrel and proximal end of the barrel-assembly are keyed to assure proper alignment, which the 1:1 turning ratio of the barrel-assembly supports. In an off the shelf airgun modified for use in accordance with the objects set forth herein, the barrel insert used to reduce the caliber stops half way down the barrel to allow the proximal end of the barrel-assembly to be inserted.

Barrel-channels that avoid angles throughout their course yield a smoother or more linear relation of propulsive force to exit velocity. An angle in the barrel-tubes too slight to stop the miniball at lower velocities nevertheless dissipates its momentum or propulsive force. While a steep gap in exit velocities separates implantation force of impact values from puncture of the outer fibrous layer of the ductus, variation in exit velocity directly effects the distance of miniball travel along the inner surface of the fibrous outer layer before it is brought to a stop. Overshooting or over-travel is readily compensated for by withdrawing the muzzle-head by the proportionally corresponding distance, but is to be avoided as imposing needless additional cell damage and edema.

Because the exit velocities smaller than that necessary to reach a nonspecific subadventitial position while not puncturing the outer fibrous jacket or tunic of the ductus cover a range of impact force values, adjustment in the exit velocity need not achieve inordinate exactitude merely to achieve subadventitial placement while not posing a risk of puncture. At the same time, changes in distance or depth into the vascular system are not accompanied by any change in the chamber to muzzle-head length of the barrel-assembly. Thus, the small decrements in depth required to withdraw the muzzle-head to place successive discharges exert no effect on the ability to place the miniballs at the prescribed relative distances along the ductus.

However, the subpuncture range of exit velocities equate to equivalent impact forces that while spread out in value by the tunica adventitia, or outer elastic lamina, and consistent from discharge to discharge as to allow successive termini to be accurately placed as to related position, nevertheless propel the miniballs to correspondingly different distances within the softer tunica media along its inner surface. To achieve a certain miniball trajectory terminus in relation to distance from the muzzle-head and therefore avoid needless smooth muscle trauma requires tight or precise control. This combination of factors means that from a risk of puncture standpoint, the initial discharge, while preferably purposeful in terms of treatment, is subcritical and allows the distance travelled by the miniballs to be noted with the aid of the several imaging techniques available.

Any over- or under-shooting is then corrected by adjusting the exit velocity in proportion to its extent. Since the pathology is likely to have changed the mechanical properties of the tissue, a preliminary test discharge at a distance from the lesion to be treated is not recommended. As any site aside from that diseased will present different properties, an initial test discharge anywhere but into the diseased tissue to be treated will not yield dependable data. For this reason, implantation is begun with the airgun set for the exit velocity or force of impact value predicted with the aid of tables supplied with the apparatus for tissue of like condition to seat the miniball subadventitially without overshooting along the inner surface of the fibrous outer layer.

Due to the tiny diameter and bioinertness of the miniballs, perforation through the adventita into a body cavity of a miniball should seldom result in any significant trauma, such as a hemorrhage or the leakage of lumen contents. In ductus other than arteries, inflammation, bleeding, and proteinaceous exudate quickly seals such a wound. In an artery, however, the internal pressure of the pulse and the fact that platelet blockade has been administered mean that perforations can lead to problematic bleeding that must be prevented. This is accomplished by prepositioning the stent-jacket or stent-jackets, which may be of the double-wedge type, as addressed above in the section entitled Double-wedge Stent and Shield-jacket Rebound-directing Linings. Provided a coagulant (hemostat) is applied to the internal surface of the prepositioned stent-jacket, bleeding is quickly stopped even if a perforation does occur.

Whether requiring to be coated for radiopacification, miniballs are highly radiopaque and retrievable by means of an endoscope introduced through the incision made to place the stent-jacket. The results of the initial airgun discharge are carefully evaluated and used to adjust the discharges to follow. The means for preventing the accidental release of a miniball within the tracheobronchial tree or vascular system and removing any spillage of intestinal contents or bile following inadvertent puncture is discussed below. Restraint of the ductus wall from radial excursion at and about the point of impact would reduce the impact force required to puncture the wall; however, both wall and material of the stent-jacket are sufficiently elastic to comply with movement of the wall at and about the point of impact.

The stent-jacket is compliant both internally as to absorb the displacement of the wall in response to the impact of implantation, and as a result of its overall conformation, which includes a slit cut entirely along one side, elastic in response to the gross movement of the smooth muscle in the ductus wall. Spillage of contents into the surrounding body cavity as the result of accidental puncture of the urinary tract or bile ducts is responded to by aspirating the spillage through the incision made to insert the stent-jacket. Since it is compliant, the stent-jacket, or extraductal surround component of the stent, can be placed either before or after the intraductal component consisting of the full complement of miniballs has been implanted.

Inserted before the miniballs, the stent-jacket may exert a slightly nonuniform effect upon terminal velocity and eccentric compression of the lumen wall about the lumen circumference against the muzzle-head but assists in retaining the miniballs. This attraction assists in preventing rebounds or failures of impact force as would release a miniball into the lumen. The accidental release into the lumen of a miniball is minimized when the muzzle-head fits snuggly within the lumen, damping eccentric reactive accelerations or recoils without compressing the wall. Excessive compression of the wall interferes with the ability of the wall to comply with the impact and thus the ability to properly implant the miniballs. The mechanical and electrical connections of barrel-assemblies to airguns is discussed under sections to follow.

VII2d(3). Ablation and Angioplasty-Incapable Radial Discharge Barrel-Assembly Muzzle-Heads The barrel-assembly is configured to minimize obstruction to the circulation. To allow sufficient torque, the windings of the turret-motor are elongated rather than widened. In center-discharge embodiments, the spindle can be narrowed to a flared throat, muzzle-heads larger in diameter provided with blood-grooves. Ablation and ablation and angioplasty-capable barrel-assemblies incorporate additional components such as radial projection units, heat-windows, and side-sockets that compete with the number of barrel-tubes for diameter. Otherwise, even combination forms as addressed below, are configured similarly.

The ability to perform certain endoluminal functions with single entry such as injection a significant adjunct to stenting implantation, practical barrel-assemblies generally include only the radial projection units and tool-inserts to perform this essential function. For stenting not to be preceded by an ablation or an angioplasty, the units and tool-inserts to perform this function can be eliminated. Bipartite construction, as addressed below in the section entitled Distinction in Ablation or Angioplasty-capable Barrel-assemblies as Unitary or Bipartite, can compensate for the inability to produce a general purpose device in the small diameters. In minimally and fully ablation and ablation and angioplasty-capable barrel-assemblies, push-arm blank tool-inserts can be used to nudge the muzzle-head aside clearing a path for blood to pass.

To prevent recoil deformation at the curves where the barrels approach the barrel-ports, which would dissipate much expulsive force (kinetic energy, momentum, impact force) according to the deformation, and brake (slow down) if not jam the spherules on exiting, polymer barrel-tubes are discontinued, the exit passages continued forward as barrel-channels drilled through an ejection-head machined from a solid block of nonferrous metal. The distal ends of the barrel-tubes that project into the barrel-channels are slightly smaller in diameter to allow these to move forward or backward upon, thus allowing, rotation.

Muzzle-heads conform to either of two configurations, one with barrel-tubes longitudinally centered, the other with barrel-tubes more peripheral to allow a laser catheter or rotary burr to be incorporated at the center. Both include a convoluted elastomeric segment that serves as a damper and point of flexion. Elongation of the muzzle-head through use of a turret-motor winding that is enlarged in length rather than diameter allows a level of torque to be developed that would otherwise deny access to narrower vessels or other ductus and results in a longer contact area with the lumen wall over which directable angioplasty tools such as thermal windows and side-sweeping brush type radial projection unit tool-inserts can be made to apply.

VII2d(3)(a). Monobarrel Radial Discharge Barrel-Assembly Muzzle-Heads

VII2d(3)(a)(i). Structure of Monobarrel Radial Discharge Barrel-Assembly Muzzle-Heads FIG. 38 shows an external view of a single barrel (barrel-tube) radial discharge barrel-assembly, and FIG. 39 a view partially in longitudinal section of a two or three barrel barrel-assembly. While a simple pipe type monobarrel barrel-assembly is intended for use primarily in the tracheobronchial tree and never in a duct or blood vessel, a radial discharge type barrel-assembly can be designed for use in a narrow ductus with substantially undifferentiated anatomy of the lumen wall, and provided certain features are added, in the bloodstream. Ischemia capable of inducing a midprocedural infarction a primary risk, a barrel-assembly for use in the bloodstream incorporates blood-tunnels, and in the muzzle-head, blood-grooves to minimize obstruction to the flow of blood.

The use of a multiple-barrel barrel-assembly, especially when automatically advanced, rotated, and withdrawn by means of a positional control system, is not sought only to achieve the uniform placement of the miniball implants in a formation and thus a more uniform distribution of forces, but to achieve operative speed in order to reduce the risk of infarction. Means for avoiding abrupt closure are discussed above in the section entitled Risk of Abrupt Closure. To be usable in the bloodstream, the gas pressures generated during discharge must be prevented from entering the bloodstream as gas embolisms. This necessitates enclosing or jacketing about the barrel-tubes over the entire length of the barrel-assembly and providing gas return channels so that such pressures are dissipated within the enclosure.

The barrel-catheter represents this jacket up to its distal extremity, and the ejection-head at the front of the muzzle-head contains gas return tubes to channel the pressures back into the barrel-catheter central canal. A one-way safety valve, usually an elastomeric slit-valve in end-plate 99 (not shown) is present to outlet higher pressures. In small diameter ductus, the muzzle-head enclosure additionally serves to prevent injury by an exposed pointed muzzle. The enclosure additionally incorporates a shock absorbing joint both to lend flexibility for tracking and dissipate any recoil upon discharge.

The parts shown in FIG. 38 are marked to clarify the parts of the distal (forward) portion of the barrel-assembly, or muzzle-head as consisting of:

1. A barrel-catheter 44 journaled within turret-motor clamping collar 59.
2. A turret-motor within housing 61.
3. A flex-joint 111.
4. A spindle 77, consisting of:
   a. A neck portion journalled within the rotor of the miniature through-bore torque type turret-motor, which is the separated distal segment of barrel-catheter 44.
   b. A spindle throat 112 beginning distal to the level of emergence from the turret-motor rotor, of which the forward portion wherein the barrel-tubes flare distoradially is designated the spindle flare frame or chamber. c. An ejection-head 112, which conveys the distal ends of barrel-tubes 74 to exit-holes 71, and
5. A muzzle-dome consisting of:
   a. A recovery electromagnet assembly (not shown in the outside view of FIG. 38 but situated short of nose 64), and
   b. Nose 64, of which the facing aspect is the nosing, which in most practical barrel-assemblies, encircles a scope that projects through the center of a heat-window.

Spindle 77 of muzzle-head 70 must be able to rotate through 180 degrees to either side, i.e., clockwise or counterclockwise. While a continuous length of very pliant tubing barrel made of a polymer such as vinyl and given enough slack can be rotated through a semicircular arc without distorting the 'bore,' most materials are not so flexible and therefore necessitate a rotary joint. When the momentum of the miniballs on exiting and the strength of the barrel-tubing material allows, both lumens of a double lumen extruded tube can proceed to the inner surface of muzzle-head 70 with only one of the two actually open to the exterior through muzzle-port 71 as barrel-tube 74. The second lumen is then sealed by the internal surface of the muzzle-head and is placed in communication with the first through a distal hole.

The pressure built up in the lumen used as a barrel-tube then returns through the second, sealed off lumen. The accompanying lumen adds strength; however, when the barrel-tubes are continuous from one end of the barrel-assembly to the other, a lengthier arc for bending required, deformation becomes more pronounced as the number of barrel-tubes is reduced and the angle of rotation increased, so that with one barrel-tube, reduction in exit muzzle-port 71 and a susceptibility to jamming increases in likelihood. This is ameliorated by providing a reciprocating and rotating flush joint wherein the internal diameter of the 'bore' remains constant in a less prominent or reduced ejection head.

Referring now to FIG. 38, rotary joint 58 is formed by transecting division of barrel-catheter 44 flush to the distal surface of clamping collar 59, clamping collar 59 in turn immovably affixed to the rear of throughbore turret-motor in housing 61 and stator 62, so that only the distal segment of barrel-catheter 44 separated to create a rotary joint and journaled within through-bore rotor 60 of the turret-motor rotates with rotor 60, and since muzzle-spindle 77 is attached to the distal end of the distal end of the distal segment, spindle 77 is rotated.

Viewed from the outside, rotation is seen only distal to the turret-motor in housing 61, comprising spindle 77 and the parts of the muzzle-head 70 distal to it, visibility of the rotor journaled distal segment as the rotor inserted stem portion of the of spindle 77 denied, creating the impression that the rotary joint is at the front of the turret-motor and spindle 77 rather than at the opposite or proximal end of the turret-motor. A simple pipe monobarrel-type barrel-assembly is manipulated by hand and does not incorporate a remote actuator to rotate muzzle-head 70 by wire remote control. In a single-barrel radial-discharge barrel-assembly, barrel-catheter 44 is synonymous with the one and only barrel-tube.

Whether such or conducting a plurality of barrel-tubes in a multiple barrel radial discharge barrel-assembly, the segment of barrel-catheter 44 distal to rotary joint 58 and journaled within through-bore rotor 60 of the turret-motor rotates in coaxial relation to the stationary segment of barrel-catheter 44, which is proximal to rotary joint 58 clamped by collar 59 to the rear of turret-motor housing 61. By contrast, the multiple barrel-tubes in a multiple barrel barrel-assembly (which is always of the radial discharge type), continue without break through the encircling rotary joint 58 in the barrel-catheter, passing therethrough off-center or arranged at a slight distance around the longitudinal center of barrel-catheter 44.

For this reason, when these insert into the ejection head at their distal ends, rotation of muzzle-ports 71 is driven by rotation of the ejection head Accordingly, the proximal segment of the barrel-catheter, clamping collar, and motor housing 61 remain stationary while the distal segment of the barrel-catheter that follow the rotary joint rotates. Since the barrel-tube or tubes are continuous through the rotary joint, the 'bore' or 'bores' for discharge are seamless. When barrel-catheter 44 in FIG. 38 is made of a material and in a thickness that becomes too soft when heated to 90 degrees centrigrade, such as by the turret-motor stator at stall while used for thermal angioplasty, clamping collar 59 is made of a low heat conductivity and transmissive polymeric material.

In larger embodiments, provided the flexibility of the barrel-catheter is not significantly affected, clamping collar 59 can be machined out of metal lined with a thermal insulant. In the largest embodiments, the insulation can be paper, cotton, pith, or felt. In embodiments of intermediate size, provided the barrel-catheter is thick enough as not to become limp or flaccid, the clamping collar can be bonded to the barrel-catheter with a synthetic elastomer insulating adhesive, which are numerous. The direct-current silver wire-wound subminiature through-bore torquer turret-motor is described in greater detail under the section on motorized turret muzzle-heads below. The neck or segment of the barrel-tube distal to this cut is journaled in the through-bore rotor 60 of the turret-motor and thus freely rotated by the turret-motor.

The elements of the muzzle-head distal to this joint are unitized or monolithic, so that the portion of the barrel-tube within rotor 60 functions as a shaft that rotates the spindle and electromagnet assembly as a unit. As seen in FIGS. 38, 39, 48, 49, 65, and 66, the unitized spindle and electromagnet assembly portions of the muzzle-head distal to the swivel motor rotate about joint 58. As shown in FIGS. 38, 48, 49, 65, and 66, a segment of convoluted tubing 111 intervenes between the spindle throat or level where the spindle flares radially outward and the neck, or segment of the barrel-catheter that is distal to the rotary joint and within the turret-motor rotor.

The multiple functions and bonding of this convoluted segment to the spindle and nect are described below. The amperage to the electromagnet is controlled by a precision multiturn digital potentiometer that allows the muzzle-head to be nudged against the lumen wall without additional field strength as could injure the wall or so compress the tunica media as to preclude undercutting it for subadventitial placement. Luminal wall compression can to an extent be compensated for through the use of a swellant. Alternatively, the muzzle-head spindle can be made of polytetrafluoroethylene, for example, by micromachining with or without prior transfer-molding.

Since unlike a simple pipe, some single barrel radial discharge barrel-assemblies must be usable in the vascular system where the loss of a miniball must be prevented, the tractive electromagnet assembly in a radial discharge barrel-assembly consists of two electromagnets of opposing polarity, of which only the magnet of the pair 64 closer to the viewer is shown in FIG. 39. The magnet assembly 64 and independent control of each electromagnet is described below in the section devoted to electromagnet assemblies. FIG. 40 is a cross section view of the nose or distal end of the single barrel radial discharge barrel-assembly showing the tractive electromagnets 65 and blood-grooves 66 to permit some passage of blood past the muzzle-head. Blood-grooves 66 can be made to pass midway between or over the barrel-tube exit-holes (muzzle-ports).

In FIG. 40, to clear magnets 65 when opening and closing, spring-loaded trap doors are paired, that is, of the double or opera type. Continuous with the indentation formed by the front of the two magnets 65 of the magnet assembly 64 indicated in FIG. 40, blood-grooves 66 are made as deep as possible to run longitudinally along the entire length of the muzzle-head without necessitating an increase in the outer diameter of the barrel-catheter or encroaching upon the barrel-tube, the muzzle-port 71 in FIG. 38, or magnet assembly 64. Because a radial discharge barrel-assembly such as that shown in FIG. 38 must enclose the parts equivalent to those in a simple pipe type barrel-assembly within a shell for use in smaller ductus wherein gases must be contained and rounded contours are imperative, barrel-tube 74 and barrel-catheter 44 are not one and the same as in the simple pipes of FIGS. 31 thru 34.

The magnet antechambers seen in FIG. 40 as 67 behind the spring-loaded trap double doors 68 are addressed below in the section entitled Factors that Affect Muzzle-head Nosing Length or Reach, Steerability, and Trackability. Arrows 69 indicate the path of a recovered miniball, which may have become loose or required to be extracted having been misplaced upon implantation through the double door to become trapped within magnet antechambers 67. The diameter of the barrel-assembly that can be used in any ductus is limited by the requirement to avoid stretching injury and in blood vessels, ischemia as well.

The lumina in the coronary arteries in adults vary between 1.5 and 5.0 millimeters (see, for example, Dodge, J. T. Jr., Brown, B. G., Bolson, E. L, and Dodge, H. T. 1992. "Lumen Diameter of Normal Human Coronary Arteries. Influence of Age, Sex, Anatomic Variation, and Left Ventricular Hypertrophy or Dilation," *Circulation* 86(1):232-246; Mosseri, M., Zolti, E., Rozenman, Y., Lotan, C., Ershov, T., Izak, T., Admon, D., and Gotsman, M. S. 1997. "The Diameter of the Epicardial Coronary Arteries in Patients with Dilated Cardiomyopathy," *International Journal of Cardiology* 62(2): 133-141), imposing a severe demand for miniaturization. This factor makes application for pediatric use difficult, barrel-assemblies suited to the smallest patients generally limited to a single barrel-tube, or monobarrel.

While the withdrawal of one barrel-assembly and insertion of another is acceptable in the airway when space affords unobstructed maneuverability and the possible complications of a luminal entry wound are not a factor, entry in the vascular system is best singular. Unless the benefit in operative speed gained with a multiple discharge radial barrel-assembly justifies replacing it with a barrel-assembly of smaller diameter having fewer barrels, minimizing the risk of entry point complications usually discourages such technique. Thus, even though a vessel or duct may admit a muzzle-head of larger diameter and more barrels upon entry, access to the smallest gauge of the vessel or duct should dictate the diameter of the barrel-assembly used; that is, treatment is best accomplished by using a muzzle-head of a diameter that will allow access throughout the length to be implanted.

VII2d(3)(a)(ii). Materials of Radial Discharge Barrel-Assembly Muzzle-Heads

The muzzle-head is preferably made of a nonmagnetic austenitic stainless steel, such as 18-8, 304, or 316 amenable of hardening in smaller thicknesses. Alternatively, numerous polymers can be used. The core of the tractive electromagnets at the distal end of the muzzle-head and components of the turret-motor if present, however, allows the use of an external hand-held electromagnet to expedite steering, and in a larger vessel, make possible the quick positioning of the round tip in stable abutting relation to at particular position along the lumen wall. When the brushes are separately controllable, the radial projection unit feature described below can also be used to nudge the muzzle-head eccentrically within a lumen, but only in a lumen little greater in diameter than the muzzle-head itself, and with the barrel-assembly stationary.

Limited thus, the potential utility of an external hand-held electromagnet stands. Alternatively, the muzzle-head can be made of any nonferrous metal of suitable hardness and tissue compatibility or a resin by transfer-molding. For precision and hardness, it is micromachined of a nonferromagnetic stainless steel such as austenitic 18-8 (18 percent chromium, 8 percent nickel), 304, or 316, and then given an outer coating of polytetrafluoroethylene (polytetrafluoroethene) (see, for example, Hanssen, H. H., Wetzels, G. M., Benzina, A., van der Veen, F. H., Lindhout, T., and Koole, L. H. 1999. "Metallic Wires with an Adherent Lubricious and Blood-compatible Polymeric Coating and Their Use in the Manufacture of Novel Slippery-when-wet Guidewires: Possible Applications Related to Controlled Local Drug Delivery," *Journal of Biomedical Materials Research* 48(6): 820-828).

A hydrophilic coating such as applied by the SlipSkin® reel-to-reel process, for example, allows a platelet blocker, for example, to be infused into the coating (see, for example, Koole, L. H. and Hanssen, J. H. L. 2001. "Wire, Tube or Catheter with Hydrophilic Coating," European Patent 1104681. Alternative coating processes such as plasma vapor deposition apply a coat that is thicker. Sputter coating erodes and plasma contaminates the surface of the steel (see, for example, Bastasz, R. and Thomas, G. J. 1978. "Surface Analysis of Sputtered Stainless Steel," *Journal of Nuclear Materials* 76-77:183-187; Clausing, R. E., Emerson, L. C., and Heatherly, L. 1978. "Sputtering and Chemical Attack of 304 Stainless Steel, Aluminum, and Gold by Hydrogen Ions of 100 eV Energy," *Journal of Nuclear Materials* 76-77: 199-201). This coating is applied to the entire outer surface of the muzzle-head, to include the interior surface of radial projection unit shafts, or wells.

The single barrel radial discharge barrel-assembly is similar to the multiple barrel radial discharge barrel-assemblies to be described in materials, in incorporating a motorized turret to rotate the tip, in having paired trap-extraction electromagnets 64, and in the overall form of the muzzle-head 70, which differs only in including but a single muzzle-port 71. As with a simple pipe barrel-assembly, the miniballs fed to such a single pipe barrel-assembly can be delivered from a linear queue type magazine clip, which unlike a rotary magazine clip is, however, limited to one miniball per discharge. It is the only barrel-assembly where rotation is by an axial rotary joint.

The barrel-catheter 44 of a radial discharge barrel-assembly such as shown in FIGS. 38, 39, 48, 49, 65, and 66 has a motorized turret to rotate the muzzle-head inside the lumen and therefore does not depend upon a particular choice or combination of tubing materials and/or thickness thereof as would interfere with trackability and torqueability. A single barrel radial discharge barrel-assembly made for use in the vascular tree can also be used in a secondary or tertiary bronchus or ureter, for example. When made of a sufficiently nonelastic and slippery material such as polytetrafluoroethylene having a larger wall thickness or as the outer layer in a coextrusion, the distal ends of the barrel-tubes are inserted with no bonding into the flush sockets that represent the start of the barrel-channels in the ejection-head.

This allows free rotation and reciprocation of the distal ends of the barrel-tubes. The inner edge of the sockets are beveled to minimize the effect upon the exit velocity of a miniball that might strike the edge. When, however, the barrel-tubing is sufficiently pliant that the bore is not unduly distorted or its distal end dislodged from the socket during discharge, bonding is essential. When made of polytetrafluoroethylene-coated nylon, the outer surface of the barrel-catheter is primed by etching with a special purpose chemical such as Acton Technologies, Inc. FluoroEtch® or W.L. Gore® and Associates, Inc. TetraEtch® or blown-ion air plasma type corona, or flame surface treated, and coated with an adhesive suitable for bonding etched polytetrafluoroethylene to stainless steel, such as NuSil Technologies MED-1037 or MED3-4013.

VII2d(3)(b). Muzzle-Head Turret-Motor (Turret-Servomotor)

A motor within the muzzle-head allows the barrel-assembly to be flexible for trackability without necessitating rotation that would result in excessive twisting. The turret-motor also provides quick and accurate rotation during automatic discharge, can used to oscillate the muzzle-head, aiding passage, and when suitably wired, can be used to warm the lumen. A motorized muzzle-head turret as shown in FIGS. 38, 48, 49, 65, and 66 comprises a turret-motor within motor housing 61 containing motor rotor 60 within motor stator 62, and a motorized muzzle-head multibarrel turret rotary joint 58, wherein motor housing 61 encloses motor stator 62 and rotor 60.

Switching recovery electromagnets 65 toward nose 64 of muzzle-head 70 between thermal ablative or angioplasty and miniball recovery functions and/or turret-motor within motor housing 61 between thermal ablative or angioplasty and rotary positioning functions is accomplished at the switch used to toggle between and thus select the function desired, the circuit of the function not selected being disconnected and thus disabled. One advantage in mounting the muzzle-head in a motorized turret is that remotely controllable, it is no longer necessary to rotate the entire barrel-assembly merely to rotate the muzzle-head, and this allows the use of more pliant materials in the barrel-assembly, so that trackability is attainable and maneuverability ceases to pose a significant risk of stretching injury.

Another advantage is that rotation of the muzzle-head allows combining the use of barrel-blanked clips with rotation making it possible to treat each successive segment of a vessel discriminately as to the circumferential placement of the implants with no need to withdraw an inserted barrel-assembly and replace it with another. If necessary, the muzzle-head, to include both port and magnet assembly portions, is wetted with a lubricious material to minimize resistance to rotation by the motor. Endothelial cling and resistance to passage by seizure are readily remedied when the barrel-assembly is endoluminal by ejecting a lubricant such as specified below in the section entitled Endothelial Cling and Seizure through the muzzle-ports, or if the barrel-assembly is so equipped, through perforated or injection-head radial projection unit tool-inserts.

Yet another benefit of the ability to rotate the muzzle-head by means of a motorized turret is elimination of the need for a variety of muzzle-heads having different numbers of muzzle-ports at different angles. A monobarrel barrel-assembly that is unassisted, that is, lacks a motorized pivot, or a multibarrel turret that lacks a motorized turret, requires a turning or torque ratio sufficient to rotate the port or ports to the potential target angle most distant angularly from its starting position without jamming during discharge. The section above on multibarrel radial discharge barrel-assemblies pointed out that a four-way muzzle-head, for example, demands to be rotated up to 22.5 degrees in either direction to target any circumferential angle about the lumen and its diametrically opposed two trap-extraction electromagnets up to 90 degrees in either direction to target a misplaced miniball implant for extraction, and this angle can be significantly larger with a barrel-assembly having eccentric barrels.

Since a means for recovering any loose or mispositioned miniballs is imperative, the lesser turning angle cited of 45 degrees to rotate a four-way muzzle-head for discharge is superfluous, an angle of rotation for the magnet assembly taking priority. This demands corresponding pliancy through the combined effect of the barrel tubing material and the length of the splay chamber. When the barrel-assembly is rotatable by means of a motorized rotary turret and any rotary magazine clips that reduce the number of miniballs discharged at a time as necessary are available, then any circumferential placement of miniballs up to the caliber that the lumen diameter will permit is possible without a significantly greater risk of intraluminal stretching injury or the need to withdraw and replace a barrel-assembly of one configuration in order to replace it with another mid-procedure.

With muzzle-heads with eccentric ports, the angular displacement of the muzzle-head is dependent upon the pliancy of the barrel tubing and the slack available in the splay chamber. The rolling resistance presented by increasing curvature as the ports are approached must be compensated for by adjustment of the airgun settings. Rotating the muzzle-head purely to reduce the exit velocity is not considered practical, the motorized turret provided to assist in accurately placing the miniballs into eccentric lesions. This notwithstanding, the incorporation of a motorized muzzle-head that can be rotated to any angle eliminates the need for rotating the barrel-assembly, and this has the advantage of allowing the barrel-assembly to be made of more pliant tubing material.

FIGS. 38, 39,48, 49 65, and 66 show barrel-assemblies with built in motors that allow the muzzle-head to be rotated. Such an apparatus allows the muzzle-head to be torqued at the treatment site without the need to rotate the barrel-catheter and irritate the lumen wall throughout its length, thus at all points proximal thereto, and do so without imposing the need for a barrel-catheter wall thickness that adversely affects trackability. While the angle of rotation is limited by the need to avoid an out of round condition of the barrel-tube lumina as would jam, a multibarrel barrel-assembly with diametrically placed exit-holes can implant the ductus at any rotational angle. When numerous lesions are situated at different angles about the length of the ductus lumen, the complete elimination of a need to torque the barrel-assembly significantly increases the speed of treatment and reduces the risk of complications.

The applicability of a motorized muzzle-head is limited by the diameter of the motor that can be achieved to generate the torque essential to rotate the muzzle bit through an arc in either direction of up to 44 degrees for the caliber of miniballs appropriate for the vessel to be treated. When a two-way or three-way muzzle-head with muzzle-ports at angles other than 90 degrees meets the procedural requirement so that withdrawal and replacement of the barrel-assembly will be unnecessary, then these are used. Otherwise, rather than to withdraw one barrel-assembly in order to replace it with another, a four-way barrel-assembly is used and torqued slightly to position the ports used by the rotary magazine clip as necessary.

VII2d(3)(c). Muzzle-Head Servomotor (Turret-Motor) Desiderata

As indicated in the preceding section entitled Turret-motor Operational Modes, the turret-motor must provide three modes of operation—heating, oscillation, and positional control. In a minimally capable barrel-assembly, these functions are selected and adjusted using selector switches mounted on the airgun enclosure and connected to the airgun power supply and the motor controller and/or amplifier (drive), which controls both the transluminal and rotatory position of the muzzle-head. In an ablation or an ablation and angioplasty-capable barrel-assembly, heating and oscillation must be controllable independently of an airgun. For freedom of movement, tethering by a cable or cord is avoided through use of an onboard control panel atop the power and control housing with the battery pack inside thereof.

Airgun positional controls are maximized for use with minimally capable barrel-assemblies and fully capable barrel-assemblies while inserted in the airgun. Mounted on the airgun enclosure, these pertain to use of the linear positioning stage to set the rate of transluminal movement during nonmanual thermoplasty or cryoplasty and also to control rotation of the muzzle-head during implant discharge. However, when an ablation or ablation and angioplasty-capable barrel-assembly is inserted in the airgun, it is controlled in the same way as a minimally capable barrel-assembly. By contrast, the need for free movement pertains to manual use, during which connection to the airgun and controller or servomotor amplifier is seldom if ever necessary.

That power is from a battery disallows conventional solutions, such as producing oscillatory performance by detuning the velocity loop in, or programming a set of oscillatory (vibratory) frequency modes to be executed by, the servocontroller without, for example, infrared transmission of the control signals. More specifically, these modes of operation include 1. Rotation in either direction as arc-limited according to the number and twisting limits of the barrel-tubes, 2. Use of the motor windings for heat generation to serve as a heating element for thermal angioplasty (whether in coordination with like use of the recovery electromagnets distal to the ejection head), and 3. Oscillation useful for a. Assisting to free the muzzle-head should it cling to or seize against the endothelium, or b. Imparting vibratory action to the radial projection unit tool-inserts.

Unless matched to combination-form radial projection catheters, minimally ablation and ablation and angioplasty-capable barrel-assembly controls for heating the windings and to use any radial projection units in the muzzle-head are mounted on the airgun. When matched thus, these controls are duplicated on top of the radial projection catheter power and control housing, which further includes the controls for the components in the radial projection catheter. Once an ablation or an ablation and angioplasty-capable barrel-assembly has been inserted into the airgun and discharge initiated, ablation or angioplasty should seldom demand resumption.

Should the desirability for further angioplasty arise, the control of angioplasty functions—individual or combined use of the turret-motor and recovery electromagnets as heating elements for thermal angioplasty and deployment and retraction of radial projection unit tool-inserts—can still be controlled from the control panel onboard the barrel-assembly as an independent apparatus. However, combination-forms that additionally incorporate a rotary burr or laser are more costly and less likely to be adapted for conventional console-remote control, and more likely to remain tethered prior to insertion into the airgun.

Unlike the linear positioning table or stage used to insert and retract the barrel-assembly in submanipulable millimetric increments as described below, which are available from many manufacturers incorporating several different techniques, turret-motors must be custom made to afford adequacy of through-bore internal diameter within the severely constrained and isolation of the magnetic fields within the motor from implants.

Older technology brushed through-bore torque motors of outrunner configuration are not preferred as incorporating a wound armature or rotor at the center and permanent magnet stator in surrounding relation thereto, which allows a through-bore of large diameter but encircles the windings amid the surrounding permanent magnets; the wound armature in a brushed motor of conventional or inrunner configuration is the rotor and in a brushless (electrically commutated) three-phase synchronous motor, the wound stator, the rotor being the field assembly. Direct drive brushless ring synchronous torque motors of inrunner configuration with a proportionally large through-bore are made in conventional sizes by Etel Incorporated, Motiers, Switzerland, for example.

For complete independence from the airgun, ablation and ablation and angioplasty-capable barrel-assemblies have an inmate polyphase controller and drive microcircuit. When this is not possible, a controller and-amplifier is provided in the airgun enclosure and connected to the barrel-assembly by a light cord. The brushless type torque motor with windings peripheral rather than encircled at the center is inherently better suited to the present application than is the brushed or mechanically commutated type in several key respects. Significantly increased power density, or power-to-size ratio, supports the extreme miniaturization essential, brushless operation provides much more precise and uniform control at low speed, and the peripheral location of the windings, if inadvertently, confers additional utility in allowing circumscribed areas at the surface of the muzzle-head (heat-windows) to be used for thermal angioplasty.

While in industrial applications the generation of heat peripherally is beneficial for dissipating the heat, here the reverse is true, the peripheral generation of heat used to advantage. As described below, a prepositioned or inserted rapid cooling catheter is introduced through the barrel-assembly to the muzzle-head to return the ablating surface to body temperature. Since positional use of the turret-motor is too intermittent to generate any significant heat and the motor is never used positionally and as a heating element at the same time, heat build up does not limit torque output. Sine wave driven brushless direct current (permanent magnet alternating current) through-bore torque motors have windings that encircle the permanent magnet rotor providing more direct transfer of heat through a heat-window (addressed below).

Such motors further distance the rotor magnets from the implants, adding a measure of protection against disruption due to magnetic leakage despite the closed magnetic circuit of the housing. Such a motor is able to provide a bore that is large enough to provide a gas pressure relief path (addressed above) and the passage of barrel-tubes. The small external diameter of the motor necessitates maximum torque for the size, dictating the use of a direct current (permanent magnet alternating current), motor, which for reasons already stated, is made long relative to width. The turret-servomotor is preferably a three-phase brushless direct current, direct-drive (transmissionless, gearless) limited angle through-bore torque motor or 'torquer' with high axial, radial, and torsional stiffness, and high stall torque (standstill torque; hold-fast torque) that develops its highest torque at low speed.

Although the high lubricity and nonthrombogenic outer surface of the muzzle-head keep resistance to turning of the muzzle-head by contact with the lumen wall to a minimum, high stall torque is imperative for the muzzle-head to rotate together with the barrel-catheter and maintain consistent rotary angular setting whenever the operator hand torques (rotates) the barrel-assembly. The closed-loop feedback signal is generated by three digital Hall-effect commutation sensors that indicate the instantaneous position of the rotor. A once-per-revolution index sensor indicates the reference angle (home angle, home location, rotational reference datum).

Alternatively, some control drive differentials or comparators require position and velocity feedback from a coaxially mounted resolver (analog) or optical encoder (digital), or a potentiometer. To generate sufficient torque in a motor that the portions of the arterial system most often demanding treatment can limit to 2.5 millimeters in outer diameter, the motor stator is wound with silver wire and the rotor and stator are made proportionally longer, (i.e., greater in axial length) relative to diameter, generally in the ratio of 5:1, such as 2.5 mm in diameter and 12.5 mm in length.

Such is unconventional in torquer motors, which are ordinarily 'pancake'-configured. Thermal ablation and ablation and angioplasty-capable muzzle-heads necessitate thermal insulation about the heat-window or windows which, consisting of outer coatings of silicon aerogel and polytetrafluoroethylene, for example, present minimal thickness to limit even more severely the diameter of the muzzle-head and therewith gauge of the vessel that may be treated.

To achieve contact all around the muzzle-head without stretching the lumen wall serves to assist in maintaining direct thermal window-lumen wall contact for thermal angioplasty that uses the turret-motor as the heating element while reducing the risk of thrombogenesis due to interposed blood and avoid 1. Discharge through intervening lumen contents allowing more equal impact force among miniballs discharged at different radii as applicable, 2. Compressing the media or the equivalent, making subadventitial placement difficult if not impossible, and 3. Stretching injury. Closed-loop control of the turret-motor is not intrinsically necessary but arises by default in that alternative through-bore remote positioners or drivers other than direct-current motors, such as torque synchros and stepper motors, have drilled shafts, which are unable to provide a through-bore of sufficient diameter in motors of the millimetrically incremented outer diameters required, generally 2.5 to 5 millimeters.

Additionally, through-bore direct-current torque motors are familiar, whereas through-bore torque synchros and stepper motors are novel, and would increase the design problems of miniaturization even if alternative drivers could be made with bores of sufficient diameter. Control of the turret-motor is accordingly closed-loop, digital incremental, and point to point. It being preferable for a given application to maintain contact with the lumen wall circumferentially, the turret-motor, hence, the barrel-assembly, is generally chosen on the basis of diameter as well as the functions required. Since a condition of sliding contact against the lumen wall entirely around the circumference must vary, the load placed on the motor will vary.

Except when used as a heating element in barrel-assemblies designed for thermal angioplasty as described in the section to follow, the turret-motor is connected only intermittently in positional use and therefore does not generate thrombogenic heat. The direct-drive motor provides the backlash-free operation to allow the servostiffness and bandwidth essential to achieve instant accelerations, stops, and settling times. This suddenness of operation affords the frictionless endothelial breakaway and quick stops necessary to preclude tissue adhesion and stretching injury, which the lubricity of the fluoropolymer coated muzzle-head enhances.

For such point-to-point control, a feedback loop for velocity is omitted, only displacement controlled. Additional operation of the turret-motor (and tractive electromagnets) for thermal angioplasty recommends quick heatability and dropping from the less thrombogenic temperature of 90 degrees centigrade (reference provided below). Elongation of the motor housing-lumen wall interface thus allows sufficient torque in a motor of small diameter making the device passable farther down the vascular tree at the same time that it affords more surface contact area in support of the angioplasty function.

In barrel-assemblies designed for thermal angioplasty, elongation of the muzzle-head not only compensates for the limitation imposed on motor power output by severe limitation in diameter, but allows heat to be generated from three more independently controllable sources of heat, as described below. In barrel-assemblies equipped with radial projection units, a longer muzzle-head not only compensates for the limitation imposed on motor power output by severe limitation in diameter but makes possible the use of longer longitudinally deployed side-brushes. Direct drive through-bore torque motors with limited angle control have been manufactured in conventional sizes and shapes by the Kollmorgen company (through-bore pancake torquer models S200 and S300 (not designations for controller-amplifiers), now a brand of Danaher Motion, Inc.

With a four-way motorized muzzle-head, the maximum angle of rotation required to direct the muzzle-ports is 44 degrees and the tractive (trap) electromagnets 90 degrees in either direction. The motor is made to fit a barrel-assembly of a certain diameter and required range in rotational angle, at most, one full circle, which allows aiming a radial discharge monobarrel in any direction and provided the barrel-tube is made of sufficiently pliant material, precludes rotation beyond the bore deformation tolerance before discharge becomes impeded or is prevented. The distal termini of the barrel-tubes, or muzzle-ports, can thus be remotely rotated through an arc while endoluminal to discharge at an angle to either side of a reference datum or 0 degree index at the center of the overall working arc.

A turret-motor thus not only serves to overcome the need to limit barrel-assembly flexibility to achieve the torqueability required, but eliminates the need for muzzle-heads with eccentric or radially asymmetrical muzzle-ports and does so without the complexity involved in complete rotation. When the circumference or the arcuate extent to either side of the center line of the lumen wall in enfilade is not overextended, a noneccentric multiple radial discharge barrel-assembly, that is, one with muzzle-ports equidistant entirely about the circumference, typically four), using fewer than all of the barrel-tubes, can be used for eccentric lesions. To do this, the barrel-assembly is supplied miniballs from a rotary magazine clip that lacks holes for the undesired barrel-tubes.

Figure 85:
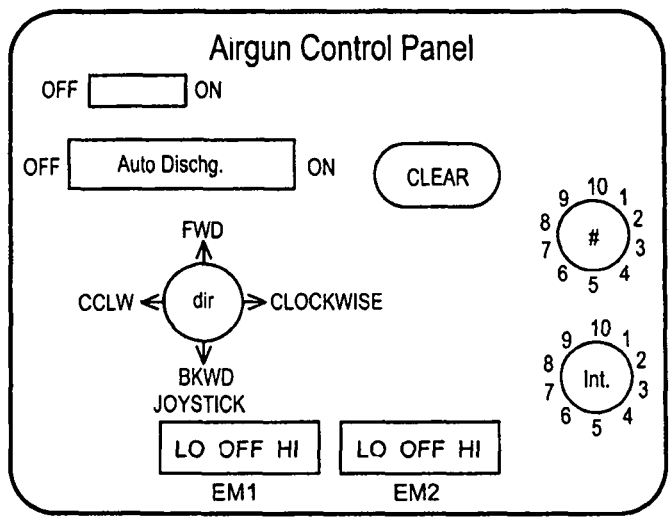
FIG. 85 shows a simple interventional airgun control panel suitable for use with an airgun such as that shown in FIG. 81 having multiple barrel-tubes and supported by componentry such as that shown in FIGS. 83 and 84 to allow the timing of discharges to be coordinated with the instantaneous rotational and transluminal position of the muzzle-head as an auxiliary function of the positional control system, the additional controls for plunger solenoid current and expulsive gas pressure as applies to the more capable airgun shown in FIG. 82 not shown.

The same approach is used to skirt or straddle a portion of the vessel along the line of its attachment by connective tissue. For use in an eccentric muzzle-head, the motor is restricted in rotary angle to allow the muzzle-ports to be directed to any angle. As shown in FIG. 85, a joystick is provided on the airgun control panel to control the rotation and transluminal displacement of the muzzle-head. For fine control over transluminal movement, the barrel-assembly must be inserted into an airgun mounted on a linear stage or connected to a separate linear stage, as addressed below in the section entitled Ablation or ablation and angioplasty-capable Barrel-assembly Control and Onboard Control Panel.

Since the rate of linear stage travel must be determined by the exposure time of the ablative or angioplasty action of the muzzle-head as it passes over the lumen wall, and discharge is not rate of travel sensitive, this rate, which likewise is controlled by the commercial controller-drive (amplifier) unit, can be fixed for any one type of angioplasty. Thus, whether the stage moves intermittently during discharge apart from a thermal angioplasty, for example, or continuously, as it must during an ablation whether concurrent with discharge or not, this rate is unchanged. If used for another process, such as a change from thermal to cryogenic angioplasty, for example, then the rate of travel must be changed accordingly.

VII2d(3)(d). Turret-Motor Operational Modes

In an ablation or an ablation and angioplasty-capable barrel-assembly, the turret-motor has three separate and distinct modes of operation—rotation, oscillation, and heating of the windings in the muzzle-head. With the barrel-assembly inserted in the airgun, any of these may further require control that is coordinated with transluminal movement executed by the linear positioning stage; control with the barrel-assembly in the airgun is by the drive controller amplifier inmate within the airgun enclosure, which has multiaxial and auxiliary function control capability. The stand-alone capability required of an ablation or an ablation and angioplasty-capable barrel-assembly when separated from the airgun is addressed above in the section entitled Muzzle-head Servomotor (Turret-motor) Desiderata.

VII2d(3)(d)(i). Turret-Motor Rotational Mode

The first is to rotate the muzzle-head, regardless of whether the barrel-assembly is under manual or automated control at the moment. Because ablation and angioplasty are primarily performed by manipulating the barrel-assembly, it is best that the barrel-assembly be self-contained and unconnected. The inmate battery allows use of the turret-motor to rotate, oscillate or heat the muzzle-head. Thus, except when some followup (slight 'touch-up') thermal angioplasty is desired after the barrel-assembly has already been inserted into the airgun, angioplasty with the barrel-assembly is manual with the barrel-assembly separate from (electrically and mechanically independent from, not inserted into) the airgun.

Minimally ablation and ablation and angioplasty-capable barrel-assemblies ablate or angioplasty to no greater extent than is immediately preparatory to implantation. For reasons of economy, minimally ablation and ablation and angioplasty-capable barrel-assemblies omit an internal source of power and a power and control housing. A matching combination-form radial projection catheter for use with such a barrel-assembly can incorporate additional controls for connection to the components within the muzzle-head as well as supply these with power.

While in use to perform an ablation or an angioplasty, minimally ablation and ablation and angioplasty-capable barrel-assemblies are dependent upon insertion in the airgun for connection to its power supply, hence, to positionally control the turret-motor and deliver power to other angioplasty related components. Otherwise, the proximal end is unconnected and freely movable. Diseased portions of the ductus usually extending beyond the margins of lesions as plainly apparent, transluminal precision of the kind essential to implant miniballs is generally not so critical that the ablation or angioplasty-capable barrel-assembly cannot be transluminally advanced and retracted by hand. An onboard electrically powered rail roller, for example, to advance and retract the barrel-catheter during manual use of the barrel-assembly as a separate apparatus would appear to offer little if any advantage.

More precise positioning is always available by temporarily inserting the barrel-assembly in the airgun to use its linear positioning stage. Once a barrel-assembly that incorporates a battery for independent power is inserted into the airgun to initiate stenting, the independent capability of the barrel-assembly can be made either to continue or be shut off depending upon whether the microminiature electrical connectors (jacks, female) within the airgun chamber into which the proximal end of the barrel-assembly plugs or, if applicable, those within the external cord, break battery contact upon engagement. with the power supply within the airgun cabinet. Provided the battery onboard the barrel-assembly has the storage capacity, switching is provided so that the airgun components can draw power from the battery.

VII2d(3)(d)(ii). Turret-Motor Oscillatory Mode

The second mode of operation is as a temperature controlled heating element for thermal angioplasty whereby the turret-motor at the rear of the muzzle-head at stall (and/or the tractive electromagnets toward the front of the muzzle-head) are designed to accept a surge amperage that quickly raises winding temperatures from body temperature at 36.8±0.7 degrees centigrade by 53 degrees centigrade or 98.2±1.3 degrees Fahrenheit higher by 96 degrees Fahrenheit past the intervening thrombogenic range of temperatures to 90 degrees centigrade or 194 degrees Fahrenheit. This temperature has been determined optimal for thermal angioplasty (Post et al. 1996, *Thrombosis and Haemostasis* 75(3):515-519), cited in the section below entitled Thermal Conduction Windows (Heat-windows) and Insulation of the Muzzle-head Body in Thermal Ablation and Thermal Ablation and Angioplasty Minimally or Fully Capable (Independently Usable) Barrel-assemblies.

Other temperatures will likely prove optimal for the endoluminal ablation of other kinds of tissue, which, by definition, will always be diseased, hence, sclerosed or malacotic and deviating from the corresponding normal tissue in the temperature required to ablate it. This temperature is considered not only optimal for thermal angioplasty, but sufficient to destroy the debris that passage of the muzzle-head could liberate, namely, lipid, macrophages, T cells, proteoglycans, smooth muscle cells, and collagen and calcified plaque particulates. Following this initially steep rise in current, the current is reduced to maintain a constant temperature of 90 degrees centigrade until no longer needed.

To avoid the thrombogenic temperatures upon reverting to body temperature, the muzzle-head is quickly cooled (defervesced) by means of either a cold air gun or a cooling catheter as addressed below in the section entitled Cooling Catheters (Temperature-changing Catheters). In an ablation or an ablation and angioplasty-capable barrel-assembly, to control the turret-motor and recovery electromagnets as heating elements independently requires that three heat servocontrol microcircuits be provided in the hand-grip with angioplasty control panel at the proximal end. With suitable thermal imaging equipment, momentarily heating the turret-motor stator or one of the recovery electromagnet windings can be used to assist in locating the muzzle-head.

Thermal ablation in ductus other than arteries is not limited to 90 degrees centigrade, so that different temperature settings are provided from 50 to 100 degrees centigrade in ten increments of five degrees centigrade each. It being difficult to incorporate temperature sensors into the muzzle-head, the temperature control microcircuits use the equivalent current respective of each heat-window as feedback. Variability in depth and the heat transfer characteristics and thickness of different tissues make emitted infrared radiation impractical for measuring the temperature of even a single heat-window.

When used upon initial passage through an artery known or suspected to harbor vulnerable plaque, the risk of rupture or the dislodgement of debris at points about the muzzle-head where it first makes contact with the surrounding lumen wall is minimized by effectively subjecting the wall to a preemptive thermal angioplasty. Such is not an angioplasty in the conventional sense, but rather a continuous pass over the lumen wall whereby heat is used to reduce the risk of rupture and embolism. For such an artery, only a barrel-assembly with heatable front end may be used and only with the windings of both recovery electromagnets heated.

The precautionary (preemptive, nondiscretionary) angioplasty with a minimally or fully angioplasty-capable barrel-assembly, in which the recovery electromagnet windings are used as heating elements, is used to preclude ruptures of vulnerable plaque by contact with the muzzle-head at body temperature during implantation discharge. A radial projection catheter can accomplish the same action using tool-insert heaters. Just distal to the barrel-ports, plaques are heated just in advance of discharge in one operation, usually with a single pass, without the need to withdraw and reenter.

By comparison, a balloon filled with a heated fluid must be advanced incrementally and cannot carry the stent to be implanted. Neointimal hyperplasia and restenosis is suppressed by implanting miniballs or stays coated with antiproliferative medication, such as paclitaxel or sirolimus, (gamma-) irradiating seeds, or antiproliferative medication-coated seeds. Concerns that the heat pretreatment will lead to intimal hyperplasia and stenosis in portions of the artery not to be stented can also be reduced by means of a prewithdrawal cryoplasty.

While not dependent upon an operative mode of the turret-motor, other temperature adjusting means which are usable as attachments to barrel-assemblies are closely related to this mode of operation and are therefore coherently introduced at this point. A cryogenic angioplasty, or cryoplasty (or a thermal ablation or angioplasty for that matter) can be accomplished by attaching a vortex tube cold air gun to the proximal end of the barrel-assembly. Means for accomplishing a cryogenic angioplasty preparatory to implantation are also provided. The incorporation of cryoplasty capability into barrel-assemblies is addressed below in the section entitled Minimally Thermal Ablation or Angioplasty-capable Barrel-assemblies.

Some researchers suggest that at least over the short term, cryoplasty reduces restenosis compared to conventional angioplasty (see, for example, Davies, M. G. and Anaya-Ayala, J. E. 2013. Endovascular Techniques in Limb Salvage: Cutting, Cryo, Brachy, and Drug-eluting Balloons," *Methodist Debakey Cardiovascular Journal* 9(2):69-72; Diaz, M. L., Urtasun, F., Barberena, J., Aranzadi, C., Guillen-Grima, F., and Bilbao, J. I. 2011. "Cryoplasty Versus Conventional Angioplasty in Femoropopliteal Arterial Recanalization: 3-year Analysis of Reintervention-free Survival by Treatment Received," *Cardiovascular and Interventional Radiology* 34(5):911-917; Lyden, S. P. 2006. "Indications and Results with Cryoplasty in the Treatment of Infrainguinal Arterial Occlusive Disease," *Vascular* 14(5):290-296; Samson, R. H., Showalter, D. P., Lepore, M. R. Jr., and Ames, S. 2006. "CryoPlasty Therapy of the Superficial Femoral and Popliteal Arteries: A Single Center Experience," *Vascular and Endovascular Surgery* 40(6):446-450; Laird, J. R., Biamino, G., McNamara, T., Scheinert, D., Zetterlund, P., Moen, E., Joye J D. 2006. "Cryoplasty for the Treatment of Femoropopliteal Arterial Disease: Extended Follow-up Results," *Journal of Endovascular Therapy* 13 Supplement 2:1152-1159; Laird, J., Michael, R. J., Biamino G., McNamara, T., Scheinert, D., Zetterlund, P., Moen, E., and Joye, J, D. 2005. "Cryoplasty for the Treatment of Femoropopliteal Arterial Disease: Results of a Prospective, Multicenter Registry," *Journal of Vascular and Interventional Radiology* 16(8):1067-1073; Lyden, S. P. 2006. "Indications and Results with Cryoplasty in the Treatment of Infrainguinal Arterial Occlusive Disease," *Vascular* 14(5):290-296; Fava, M., Loyola, S., Polydorou, A., Papapavlou, P., Polydorou, A., Mendiz, O., and Joye, J. D. 2004. "Cryoplasty for Femoropopliteal Arterial Disease: Late Angiographic Results of Initial Human Experience," *Journal of Vascular and Interventional Radiology* 15(11):1239-1243).

At least in certain conditions, the efficacy of cryoplasty has, however, been questioned if not contradicted (McCaslin, J. E., Andras, A., and Stansby, G. 2013. "Cryoplasty for Peripheral Arterial Disease," *Cochrane Database of Systematic Reviews* (8):CD005507; Shin, S. H., Baril, D. T., Chaer, R. A., Makaroun, M. S., and Marone, L. K. 2013. "Cryoplasty Offers No Advantage Over Standard Balloon Angioplasty for the Treatment of In-stent Stenosis," *Vascular* 21(6):349-354; Spiliopoulos, S., Katsanos, K., Karnabatidis, D., Diamantopoulos, A., Kagadis, G. C., Christeas, N., and Siablis, D. 2010. "Cryoplasty Versus Conventional Balloon Angioplasty of the Femoropopliteal Artery in Diabetic Patients: Long-term Results from a Prospective Randomized Single-center Controlled Trial," *Cardiovascular and Interventional Radiology* 33(5):929-938; Kessel, D. O. and Samson, R. H. 2008. "What is the Evidence for the Efficacy of Cryoplasty?," *Journal of Cardiovascular Surgery* (Turin, Italy) 49(2): 179-185;).

Current comparisons of available techniques for clearing infrainquinal vessels will be found, for example, in Ramaiah, V. 2008. "Endovascular Infrainguinal Revascularization: Technical Tips for Atherectomy Device Selection and Procedural Success," *Seminars in Vascular Surgery* 21(1):41-49; Shafique, S., Nachreiner, R. D., Murphy, M. P., Cikrit, D. F., Sawchuk, A. P., and Dalsing, M. C. 2007. "Recanalization of Infrainguinal Vessels: Silverhawk, Laser, and the Remote Superficial Femoral Artery Endarterectomy," *Seminars in Vascular Surgery* 20(1):29-36. The risk of releasing debris in an artery with either a minimally or fully capable barrel-assembly can be reduced by deploying a damped plunger solenoid controlled embolic trap filter, as described below in the section entitled Trap Filter Deployment and Retrieval Mechanism.

For preventing the recurrence of restenosis that appears following conventional treatment, cryoplasty appears no more effective than conventional endovascular methods (Karthik, S., Tuite, D. J., Nicholson, A. A., Patel, J. V., Shaw, D. R., McPherson, S. J., and Kessel, D. O. 2007. "Cryoplasty for Arterial Restenosis," *European Journal of Vascular and Endovascular Surgery* 33(1):40-43. While the winding of either recovery electromagnet is separately heatable, when used upon initial introduction and transluminal passage through an artery known or suspected to harbor vulnerable plaque, the windings of both recovery electromagnets are used to generate heat. Thus, in both minimally and fully ablation or ablation and angioplasty-capable barrel-assemblies, a heat-window fully encircles the recovery electromagnets as to extend over the distal (front) end or nose of the muzzle-head for heating the surrounding wall of the lumen.

Portions of the nose occupied by the distal embolic protective trap-filter and a laser or atherectomy burr if installed are omitted. Another heat-window can fully encircle the turret-motor. Preemptive thermoplasty during advancement (moving distad) with or without discharge is with the nose window. When discharge is performed during withdrawal, the turret-motor window can be used continuously or intermittently preceding discharge. During initial contact heating before switching to tractive use during discharge, the windings of both electromagnets are used as heating elements. For uniform coverage over the luminal circumference, the recovery electromagnet or nose heat-window must wrap entirely around the nose dome.

By contrast, during discretionary thermoplasty, either winding can be used independently to concentrate the heat directed toward an eccentric lesion. For applications that call for a more circumscribed heating area at the nose, a semi-hemispherical or slotted overlay is added to the nose, generally in the form of pre-cut press apply tape. Similarly, plaque usually eccentric and the turret-motor behind or proximal to the point where the muzzle-head makes initial contact with the lumen wall, the turret-motor heat-window can be reduced to an eccentric slit- or slot-shape to allow the differential direction of heat. It can have circumferentially delimited slits, slots, or an elongated rectangular heat-window for directing the heat over a certain level and arc (direction).

These likewise need not be fixed, but can be applied as cutout patterns in press apply tape. Since temperatures above and below 90 degrees centigrade have been determined to be thrombogenic (Post et al. 1996, *Thrombosis and Haemostasis* 75(3):515-519, cited below under the section entitled Thermal Conduction Windows (Heat-windows) and Insulation of the Muzzle-head Body in Minimally or Fully Thermal Ablation and Thermal Ablation and Angioplasty-capable (Independently Usable) Barrel-assemblies), heat-windows, whether enveloping, as at the nose (nose-cap, nose-dome), or circumferentially delimited (eccentric), as at the turret-motor, must to the extent possible be temperature isolated from the surrounding surface of the muzzle body.

This is accomplished by making the window of silver and thus creating a considerable differential in thermal conductivity between the heat-window and the regions bounding it. However, even when the areas adjacent to the heat-windows represent zones along a gradient of decreasing temperature, unless located beyond the level to which the focus of heat is moved, these adjacent areas are exposed to temperatures below 90 degrees centigrade only momentarily before exposed to the full 90 degree temperature over the window. That is, as the muzzle-head passes over the wall of the lumen, only the segments of the ductus distal and proximal to the area to be treated will 'see' temperatures between body temperature and 90 degrees centigrade; treated areas 'see' such temperatures only while the heat-window is approaching and departing.

The use of service-catheters to inject substances into the lumen wall is addressed below in the section entitled Preparation of Service-catheters for Use as Transbarrel-assembly Hypotubes. Another time that thrombogenic temperatures will occur is when the recovery electromagnets toward the front (distal end) of the muzzle-head are switched from the heating to the tractive mode upon initiating discharge. At this time, the magnets, usually along with the trap-filter, are kept on (energized) instead to intercept and recover any miniballs that would otherwise pass downstream.

The interval during the return from 90 degrees centrigrade back down to body temperature can be eliminated or minimized by prepositioning a cooling catheter as addressed below in the section entitled Cooling Catheters (Temperature-changing Catheters) in the central canal or a spare barrel-tube (service-channel) as addressed below under the sections entitled Muzzle-head Access through a Service-channel without the Aid of and by Means of Inserting a Service-catheter and Thermal Ablation or angioplasty- (Lumen Wall Priming Searing- or Cautery-) capable Barrel-assemblies.

A service-catheter configured as a cooling catheter for quickly returning the muzzle-head and the heat-window in particular as well as the heat-treated tissue to body temperature is used to conduct cooler if not chilled air generated by a vortex tube based cold air gun, vaporization from a small, typically 12 to 20 gram cartridge of liquified carbon ($CO_2$) or nitrous oxide (dinitrogen (mon)oxide), (actually $N_2O$ but usually designated $NO_2$) gas or high purity 1,1,1,2-tetrafluoroethane (R134a) cryogen spray over the treatment site. The delivery of gas or cold water, for example, down the service catheter or central canal must be through a nozzle that affords a return path so that pressure will not accumulate.

Due to the small gauge of the service catheter, this will usually be a double-lumen hypotube with a tip that flush fits into the proximal end of the service catheter. The relatively quick changes in temperature made possible with 'cooling' is essential for targeting circumscribed tissue for ablation (destruction, removal) and avoiding consequences of successive steps that differ in essential range if not optimal temperature. For example, if the muzzle-head remained above 50 degrees centigrade following its use to perform an angioplasty at 90 degrees centigrade, any solid protein solder coating on the miniballs used to make the extraluminal stent immediately thereafter would be caused to melt prematurely.

Making indentations in and texturing the surface of the solder both provides more surface area for quicker heating of the miniball or stay ferrous metal core initiating melting or denaturation more quickly and allows the take up of additional cyanoacrylate cement when used. By directing a stream of cold air at the back side of the muzzle-assembly nose-cap, the same apparatus can be used to perform a precautionary angioplasty. Unlike the delivery of heat to the nose, which can be generated intrinsically within the barrel-assembly by heating the windings or by connecting a source of hot gas such as a vortex tube to the end-plate, cold air is delivered by a cooling catheter or by connecting a source of cold gas to the end-plate.

Whether to conduct heat produced by means of a vortex tube or cold produced by a vortex tube (cold air gun) or by a $CO_2$ or $NO_2$ cartridge connected at the back of the barrel-assembly, the use of a cooling catheter is necessary only in Barrel-assemblies which would otherwise release gas into the bloodstream. This is avoided in an edge-discharge muzzle-head of which the central canal is used to house only a trap-filter silo with enclosed back at its distal end. A gas vaporization cold generating apparatus is described by Sellinger, M. S. and Currie, R. B. 1971. "Cryogenic Biological Apparatus," U.S. Pat. No. 3,630,203, incorporation into a barrel-assembly necessitating miniaturization of the parts that course through the barrel-assembly central canal.

The use of such portable cartridges, which are commonly used in airguns to provide the propulsive force for propelling the projectiles ($CO_2$) and in aerosol cans to dispense whipped cream ($NO_2$) for example, allows the cryogenic gas to be carried on-board the ablation or ablation and angioplasty-capable barrel-assembly, which thus remains free of a hose that would be needed for connection to a separate supply tank. While temperature inconstant over time and limited in charge and thus duration, such a free-standing flash expansion vaporization chilling means would rarely fail to meet the present needs. A discharged cartridge can be replaced with a charged one, but where constancy of temperature without interruption is desired, a vortex tube-based cold air gun, which necessitates connection to the end-plate at the back of the barrel-assembly by a small supply line or hose to a tank (cylinder, canister) of compressed air, is used (addressed below).

Vortex tubes can maintain temperature constancy to within one degree Fahrenheit using either the cold or hot air output. Connection by a small hose at the back (proximal end) of the barrel-assembly to a highly pliant hose leading to a supply of air is not as hindering as would be the need to manipulate an ablation or ablation and angioplasty-capable barrel-assembly that is relatively inflexible and inserted into the airgun. Both because it is not connected to function thus and is contained within the airgun cabinet necessitating connection to the barrel-assembly through a supply line, the cartridge used to power the airgun (i.e., to provide the propulsive gas used to expel the miniball implants) is not also used cryogenically.

Another reason for prepositioning a cooling catheter in the muzzle-head is to cool the push type plunger solenoid in the nose of the muzzle-head that is used to deploy a distal embolic protective trap-filter when optimal materials notwithstanding, the duty cycle with consequent buildup of heat would damage the solenoid. Heat sinked, and through use of the cooling catheter, the heat liberated by the solenoid is constrained to 90 degrees centigrade, any thermal thrombogenic effect thereby averted when used in the vascular tree. The ability to deliver cold air, typically at −10 degrees centigrade (14 degrees Fahrenheit), through a cooling catheter, allows the quick return to body temperature of the electromagnet and turret-motor coils when used for thermal angioplasty, and of the solenoid coil when energized to deploy the trap-filter.

The cooling catheter is closed off at its distal terminus, and the central canal and barrel-tubes are perforated to allow gas contained within the barrel-assembly to be internally recirculated. Gas is thus prevented from entry into the bloodstream, and the cryogenic gas is quickly returned to body temperature. The barrel-assemblies described herein are neither configured nor intended to be capable of cryogenic angioplasty through the incorporation of a cryoplasty balloon. Such balloons accomplish angioplasty when expanded in apposition to the surrounding wall of the lumen and left in place for 20 seconds at −10 degrees centigrade.

While such a balloon could be deployed through the center of the nose from the otherwise unoccupied central canal of an edge-discharge muzzle-head as addressed below, a process that required advancement of the balloon in increments of alternate inflation and deflation would take too much time. A cryogenic approach therefore directs nitrous oxide vaporized from a small cartridge of nitrous or carbon dioxide temporarily attached at the back (behind the end-plate) of the barrel-assembly while still detached from the airgun toward the internal or back side of an efficiently temperature conducting nose-cap window that is the same as used as the heat-window (addressed below). The barrel-assembly can then be slowly and continuously advanced or withdrawn without the need to alternately deploy and stow a cryogenic balloon incrementally.

Thus, in a precautionary angioplasty whereby the muzzle-head is slowly moved over the wall of a lumen suspected or known to harbor vulnerable plaque rather than directed at specific lesions, the operator must arrive at a clinical judgment as to whether the somewhat greater speed of using heat and reduced susceptibility of extraluminal stenting to intimal hyperplasia outweighs the relative freedom from consequent intimal hyperplasia of using cold or performing a cryoplasty instead. The outlet temperature of a vortex tube-based cold air gun is typically 70 degrees Fahrenheit lower than the inlet temperature, so that supplied with compressed air at 75 degrees Fahrenheit, for example, a vortex tube-based cold air gun can deliver air at 5 degrees Fahrenheit.

Absent an airgun, a barrel-assembly can serve as a single or multiple channel guide-catheter for the aspiration of soft plaque, the retrieval of tissue for analysis from along the inner surface of the ductus, the delivery of medication whether in the form of a liquid, powder, or gas, and/or to chill or heat highly circumscribed areas along the internal surface of the ductus or use a 'cooling' catheter to rapidly adjust the temperature of the muzzle-head. When used for the delivery of implants as well, the barrel-assembly allows the introducer sheath to be entered and withdrawn through but once for angioplasty, stenting, and the passage of smaller catheters for such other purposes thus minimizing irritation to the entry wound.

Unless a procedure will be completed in too little time for the inlet temperature to change, merely to prerefrigerate or preheat a canister of air or another suitable gas which is then allowed to gradually return to the ambient temperature in the operating room is not recommended, alternative means of providing gas of constant temperature available. Placing the compressed gas cylinder within a refrigeration or heating mantle or enclosure can be used separately or with a vortex tube to achieve colder temperatures. However, the cylinder must be close to the barrel-assembly end-plate, since moving through a long supply line will similarly allow gradual change to room temperature.

Thus, except occasionally for connection to a cold air gun, all ablation or ablation and angioplasty-capable barrel-assemblies, to include minimally thermal angioplasty (lumen wall priming searing or cautery-) capable barrel-assemblies and fully ablation or ablation and angioplasty (lumen wall priming searing or cautery-) capable barrel-assemblies, are used separately and independently of an airgun and inserted into the airgun only afterwards to initiate stent-implantation. Left connected throughout the angioplasty would seldom if ever impede the freedom of transluminal movement due to tethering but rather due to the relative immobility of the airgun even with the linear positional stage used to advance and withdraw the barrel-assembly over relatively small distances.

Small in gauge and pliant, the cold air supply line can be left connected until the barrel-assembly must be inserted into the airgun to commence stent implantation. A minimally ablation or ablation and angioplasty-capable barrel-assembly need be no more ablation or angioplasty capable than is necessary to preclude ruptures and destroy the debris underlying the fibrous cap of the atheromatous lesion or lesions through a preliminary preemptive searing of the lumen wall prior to commencing with ballistic implantation. However, even this level of function requires the accommodation of a cooling catheter or line from a cooling cylinder or $CO_2$ cartridge, for example, to quickly return the heated distal end, electromagnet heat-window, or nose heat-window back down to body temperature.

Insertion into an airgun will always follow and require but the quickly accomplished disconnection of the cooling catheter supply line. A fully ablation or ablation and angioplasty-capable barrel-assembly is all the more required to accommodate such a line, because its use to perform an ablation or an angioplasty may not be followed by stenting that uses the barrel-assembly. That is, a fully ablation or ablation and angioplasty-capable barrel-assembly can be used exclusively for transluminal ablation, atherectomy, or angioplasty without ever having its other function as a means for effecting implantation invoked.

As barrel-assemblies are not limited to use in the arterial system, and these heating and chilling features can be used for thermal (but not cryogenic) ablation in other type ductus, barrel-assemblies other than minimally ablation or ablation and angioplasty-capable contain controls to allow the selection of temperatures (winding currents) other than 90 degrees centigrade, usually from 50 to 100 degrees centigrade in ten increments of five degrees. With either type of barrel-assembly, as long as the connection of the line used to convey cold or hot air or gas is at the proximal end, that is, mounted to the end-plate, the line will obstruct insertion into the airgun barrel necessitating that it be disconnected ending its usability.

However, depending upon the type ductus to be treated, even when other lines fed to a fully ablation or ablation and angioplasty-capable barrel-assembly, such as a rotary atherectomy burr or laser cable, must be disconnected to allow insertion into the airgun, it can be of distinct advantage that access to chilled and heated air or gas remain uninterrupted when the proximal end is inserted into the airgun to initiate ballistic implantation. Whether both the cold and hot gas are obtained from a cold air gun, or the cold gas from carbon dioxide or nitrous oxide cylinder, tank, or cartridge, such as is used to power an airgun (powerlet, pistolet), and the hot gas from a separate source, such as a cold air gun, continuity of access makes it possible to briefly chill (not freeze) the tissue to be implanted.

Chilled tissue will be less mobile and chemically active. Chilling the luminal wall during discharge effectively hardens the target tissue, making higher velocity discharge possible than could be employed at body temperature. Thus, in order to make any given barrel-assembly as widely applicable to different type ductus as possible, the ability to quickly change the temperature of the target tissue during discharge is of value. Chilling becomes especially significant if the momentum of the miniball as discharged cannot be made sufficiently small to avoid perforation. Although miniball velocity must be high enough to achieve relatively clean puncture and penetration under any circumstances, reducing the mobility of the target tissue further reduces microtear injury and the risk of perforation.

The reduction in mobility of the tissue can also allow improvement in aiming precision and the ability to achieve the desired trajectory through, and depth of penetration into, the luminal wall. By retarding chemical activity, cryogenic ballistic implantation can also lessen the severity of sequelae, to include inflammation. Similarly, in the use of a stay insertion tool as addressed below in the section entitled Stay Insertion Tools, chilling can be used to achieve greater precision in placing the stays at the depth into the ductus wall desired whether medial or supramedial. Whether supplied to a barrel-catheter or a stay insertion hand tool, the use of a cold air gun has the advantage that warming to follow the chilling is obtained by switching from the cold to the hot air outlet of one and the same source mechanism.

One and the same open-ended cooling catheter or stay insertion tool line can be switched or transferred from a. A suction pump to the b. Cold or c. Hot outlet of a vortex tube, d. A compressed gas cartridge, or e. A tank containing adhesive delivery line flushing solvent or f. Distilled water. For the foregoing reasons, it is beneficial to provide a side access entry portal or side-socket in a barrel-assembly through which a cooling catheter or cold air gun output supply line in the form of a narrow hose or tube can be advanced down a (servicing) barrel-tube or the central canal of an edge-discharge barrel-assembly and a side-socket for connecting the hose.

Since the vortex tube cold air gun emits hot air at the opposite outlet, it can be used as an alternate source of heat for thermal angioplasty as well. With the qualification that the volume of air delivered by the vortex 'cold' air gun diminishes in proportion to the extremity of the temperature demanded, the overall range of temperatures that such a gun can deliver is dependent upon the temperature of the air supplied from the compressed air cylinder (tank, canister) and to a much lesser extent, the ambient temperature, but generally ranges from 15 to 250 degrees Fahrenheit, which range encompasses the temperatures used for ablation and angioplasty whether cryogenic or thermal. The degree of capability is also based upon whether each such heating element is independently controllable by a separate temperature servocontrol microcircuit in the hand-grip.

A more basic embodiment is distinguished from one of greater capability in that the latter also incorporates a positional servocontrol microcircuit in the hand-grip, positional use of the turret-motor while disconnected from the airgun limited to the support of angioplasty. Use of the turret-motor both as a heating element and mover necessitates the coordinated control of winding temperature. Cooling back down to body temperature past the thrombogenic range is accelerated by means of passing a special cooling catheter or rapid cooling catheter down the barrel-assembly or spare adjacent barrel-tube (service-channel) as addressed below under the sections entitled Muzzle-head Access through a Service-channel without the Aid of and by Means of Inserting a Service-catheter and Thermal Ablation or angioplasty- (Lumen Wall Priming Searing- or Cautery-) capable Barrel-assemblies to the turret-motor and/or electromagnets, as will be described.

VII2d(3)(d)(iii). Turret-Motor Heating Mode

The third mode of operation is oscillatory, obtained either by detuning the turret-motor drive velocity loop, in which case the oscillation is random, or if the movement is to be controlled, then by programming the reciprocal motion according to sinusoidal profiles which can be selected, s-ramping used to obtain smooth performance if desired. While in most instances, one or two frequencies and arcuate strokes (excursion) to either side are satisfactory, some radial projection unit tool brush type insert tips that function efficiently at a certain frequency or stoke may require more settings. The oscillatory mode is used mainly to aid in maneuvering the barrel-assembly or produce a vibratory action at the treatment site, such as to swab, brush, or abrade the lumen wall by increasing the frequency and/or vigor (forcefulness) of side-sweeping with radial projection unit tool-inserts.

While it has been devised for the maximum surface lubricity (slipperiness, slickness), should the muzzle-head nevertheless cling to the lumen wall, oscillatory movement can be used to free the muzzle-head, usually following delivery of a lubricant through a service-channel or to vibrate brush type radial projection unit tool-inserts, or side-sweeping brushes (side-sweepers), but never in an attempt to pass a tortuous stretch of a vessel, where such action can result in stretching injury or even perforation. Fever tends to reduce thrombogenicity and may be disregarded for the present purpose (see, for example, Groza, P., Artino-Rădulescu, M., Nicolescu, E., Munteanu, A., and Lungu, D. 1987. "Blood Coagulation and Fibrinolysis in Hyperthermic Rats," *Physiologic* 24(4):213-220).

The use of silver wire achieves the maximum electrical and thermal conductivity (transcalency, adiathermancy, athermancy) in both the turret-motor and tractive electromagnets, which in barrel-assemblies designed for thermal as well as mechanical angioplasty, also serve as temperature-controlled heating elements. High electrical conductivity equating to low resistance with less heat generated for a given level of current, silver wire windings require proportionally more current to be raised to 90 degrees Celsius; however, in no instance should an electrically separate outer coil of nichrome wire be needed as the heating element. Consistent with the use of insulation in electrical motors and magnets, the insulation must be effective electrically but thermally conductive.

The subminiature dimensions of the turret-motor necessitate that to achieve a reasonable service life, the winding varnish be made as thick as space will allow (see, for example, Grise, W. R. and Zargari, A. 1997. "Delamination and Cracking Failures in High-voltage Stator Winding Coatings," *Electrical Insulation Conference and Electrical Manufacturing and Coil Winding Technology Conference,* 1997, *Proceedings,* 22-25 Sep. 1997, pages 835-839); however, for ablation or angioplasty, the electrical insulation should minimally interfere with thermal conductivity (see, for example, Speer, D. R., Jr. 1997. "Thermal Conductivity Improvements for Electric Motors," *Electrical Insulation Conference and Electrical Manufacturing and Coil Winding Technology Conference,* 1997, *Proceedings,* 22-25 Sep. 1997, pages 723-725).

Finally, lesion removal and stenting in a single operation is significantly augmented with the incorporation into the barrel-assembly of conventionally independent means for the removal of highly calcified plaque, to include a rotational atherectomy burr or laser catheter. Provided the parameters appurtenant of the action are closely determined and controlled, the miniballs bioinert, and sterility achieved, the implantation by ballistic means of ferromagnetic miniballs just inside the tunica adventitia, subadventitially (perimedially), or medially is safe (for a histological description of the tracheal adventitia, see Ohkimoto K, Mouri M, Amatsu M, and Teraoka M. 1997, "Histological Study of the Tracheal Adventitia, Perichondrium and Annular Ligament (in Japanese with English abstract at http://www.ncbi.nlm.nih.gov/pubmed/9423323), *Nippon Jibiinkoka Gakkai Kaiho* (Japanese Journal of Otolaryngology) 100(11):1394-1400.

The oscillatory mode can be used to improve the speed and ease of side-sweeper use. Imparting an oscillatory action to the brushes allows material deposited on the lumen wall to be removed with more thoroughly and efficiently. When only ablative or angioplastic use is contemplated so that the barrel-assembly will not be inserted into an airgun, that is, when the barrel-tubes can be fouled, this sweeping or scraping action can be performed with the distal end of the barrel-assembly inserted into a vacuum pump to clear out debris as it is generated, the trap-filter available for this purpose as well. When this procedure is preparatory to discharge, any barrel-tubes used thus must be lined with a barrel-tube lining, or service-catheter.

The oscillatory mode can be used with side-sweepers to increase the sample yield for brush cytological biopsy, the material vacuumed out through the barrel-tubes or service-catheters. The oscillatory mode can also be used to more evenly apply medication that is driven down through the barrel-tubes by a syringe, bulb, or pump with or without the subsequent use of the same or the concurrent use of other barrel-tubes to vacuum away any excess. The concurrent use of one or more barrel-tubes to deliver, while one or more other barrel-tubes vacuum away or allow a path for the removal of lavage fluid, in a manner similar to many nasal irrigation devices—which may be used in support of one of the foregoing processes, such as the retrieval of tissue for diagnosis, with or without the aid of radial projection unit side-sweeper tool-inserts oscillated or rotated with the turret-motor or longitudinally (transluminally) reciprocated by hand or linear stage—is considered obvious.

Other than in a blood vessel, similar use of the barrel-assembly allows the application of an agent, such as an acid, for chemoablative therapy, flushing away of the agent with water, for example, and aspiration of the wash water. The object in such use is to prepare for stenting implantation without the need to withdraw the barrel-assembly, which can instead be directly inserted into the airgun. For that reason, even for the removal of diseased tissue at the lumen surface and not to eliminate the vessel as a whole, sclerotherapeutic methods of chemical ablation, such as the transendoscopic injection of ethanol or acetic acid, which involve a time-delay and almost always require more than a single treatment, are not suitable for such application.

Broadly, an ablation or an ablation and angioplasty-capable barrel-assembly will allow any transendoscopic procedure, to include the passage of ultrasound or laser microsurgical miniprobes, and the use of barrel-tube will bring the inserted device to the lumen wall whereas the use of the central canal in a combination form barrel-assembly will allow a straight ahead or lumen axial access; however, a combination-form barrel-assembly having an endoscope in the central canal or simpler barrel-assembly with an endoscope lashed alongside it must be used or an alternative means for viewing the process will be required.

VII2d(3)(e). Radial Discharge Barrel-Assembly Working Arc

The working arc is the practical range of rotational excursion of the muzzle-head to either side of the turret-motor set point as limited by the deformation tolerance of the barrel-tubes in use. The working arc is thus the arc through which the turret-motor is limited in rotating its specific muzzle-head or the distance to which the muzzle-port group can be rotated to either side of its center as point of reference and thus the arc of the lumen in enfilade, or the arc of the lumen circumference accessible to discharge, within the beaten zone. Since unlike radial discharge barrel-assemblies, a simple pipe-type muzzle-head does not a. Conduct barrel-tubes internally in concentric relation that must not be deformed (bent) at the curve preceding the muzzle-port to the extent that jamming results so that its rotation must be limited, or b.

Require remote rotation to either side of the center or zero-point of a positional control system, it can be freely rotated by hand, so that the concept of a working arc does not apply to it.

As addressed in the section above entitled Simple Pipe Type Barrel-assemblies, the flange component of the barrel-assembly to airgun twist-to-lock connector is friction fitted to the end of the airgun muzzle, allowing it to be rotated. In a multibarrel as opposed to a single barrel barrel-assembly, rotation of the barrel-assembly at this connector must be done in coordination with corresponding rotation of the rotary magazine clip. Otherwise, the alignment between the clip holes and the barrel-tubes respective of each is undone or each becomes aligned to the wrong clip hole, resulting in the discharge of consecutive miniballs in the wrong sequence where some may have consisted of medication and others of ferromagnetic material, for example.

In addition to allowing rotation of the working arc, insertion of the barrel-assembly once intraluminal, such as following an intraluminal ablation does not, therefore, require withdrawal and reentry or rotation of the barrel-assembly in the lumen. The limited rotatability of the muzzle-head cannot be overcome by any adjustment to the onboard components, such as by redefining or electronically moving the setpoint at the numerical position translator. The arcuate limit established by the twisting limit imposed by the barrel-tubes, adjustment by this means will only shift the setpoint so that a portion of the working arc that would have remained accessible had the setpoint not been shifted is removed from access.

A detent arm that projects from the rear rim of the muzzle-head and stop-tab secured to by ringing (banding) about the barrel-catheter prevents over-rotation of the turret-motor during direct manual control, the incorporation of a circuit breaker or warning signal for the purpose prevents overheating or burnout. When the muzzle-ports are placed about the muzzle-head equidistantly in radial symmetry, any port can be taken as the reference index for rotation. However, since an eccentric muzzle-head groups the muzzle-ports more closely about the circumference, this center point or reference index for turret-motor rotation is taken as aligned to the most central muzzle-port in the group.

Using four or more muzzle-ports places every point about the lumen circumference under the rotational arc of two muzzle-ports, which would eliminate the need to rotate the airgun were discharge limited to quadrant placement. The extent of muzzle-head rotation by the turret-motor limited to prevent distortion of the barrel-tubes as would interfere with discharge as addressed just above in this section, an eccentric muzzle-head having exit ports in closer proximity about the circumference is advantageously employed when the turret-motor is used to index between adjacent exit ports where each barrel-tube conveys a catheter directed toward accomplishing a different treatment option, such as for one to aspirate a tissue sample, the next to deliver a drying agent, the next to eject medication, and so on, as addressed in the section below entitled Rotation of Multibarrel-tube Muzzle-heads Used as Multiple Purpose Guide-catheters.

In fact, by blanking rotary magazine clip holes, performing one transluminal run, indexing the muzzle-head by the circumferential distance from the first run desired, then reversing direction in a second run, it is possible to lay down the implants in any pattern; since a lesser degree of rotation will bring one or another of the muzzle-ports to overlie or subtend any arc about the muzzle-head, increasing the number of evenly spaced muzzle-ports reduces the need to rotate the working arc. The use of rotary magazine clips is described below. However, an eccentric muzzle-head can gain the advantages of less complexity and greater speed, can, for example, lay down several closely spaced rows in a single run.

When it is difficult to ascertain whether a suitable starting angle (working arc center; control set point) as establishes the center of the working or treatment arc has been achieved, preliminary discharge for effect allows this angle to be determined, to reveal, for example, whether the correct two out of four rotary magazine clip-holes properly received the load. Within the working arc, the turret-motor provides finely adjusted rotation essential to uniformly place implants at intervals to evenly distribute the magnetic traction. While the muzzle-head must be rotatable, the barrel-tubes are continuous from the airgun chamber to the muzzle-ports and can be bent only so much before deformation interferes with discharge.

Furthermore, for safety and to achieve precision fitting, the components of the barrel-assembly are made unadjustable or fixed in rotational alignment, a means for gross rotational adjustment, that is, for rotating the assembly as a bodily whole is necessary. This limits the extent to which the muzzle-head may be rotated. With the proximal end of the barrel-assembly locked in position within the airgun, no free proximal end as can be manually rotated when a angioplasty capable barrel-assembly is used independently before connection to the airgun is present. To make eccentric barrel-assemblies with muzzle-port groups in different quadrants, for example, with the unrotatable stop-and-lock connection made is unacceptable, since with such working arc limited muzzle-heads, to rotate the working would necessitate removing the barrel-assembly arranged around one angle and replacing it with another.

VII2d(3)(f). Rotation of Working Arc

To avoid such limitation, the airgun is mounted to afford an additional degree of freedom, viz., the ability to rotate about the longitudinal axis passing through the center of the barrel-catheter, and therewith, rotate the working arc. Since the connector shown as 47 in simple pipes and 75 in radial discharge barrel-assemblies can be forcibly rotated by hand, this too can be used as a rotary joint to change the arc of the working arc. As shown in FIG. 83, rather than to rotate the barrel-catheter or airgun barrel separately, the mounting used to allow the barrel-catheter about the long axis through the airgun barrel preferably consists of inverted U-shaped cradle swing or swivel bracket 149 bent into heavy gauge strip steel stock by a brake. The vertical side to side connecting segment or bridge portion of the bracket is screwed down to the upper surface of the linear positioning table 150.

Airgun 151 rests on and can be locked at any rotational angle coaxial to the long axis of airgun barrel 152 in compression or tightenable swing cradle bracket 149. The cradle allows adjustability in the angle of rotation in the same way as the elevation adjusting device of a spotlight, except that the spotlight has tightening knobs at both sides while swing cradle bracket 149 has only one tightening knob 154 at the rear. The front component of the airgun enclosure-divided shaft that allows long axis airgun barrel 152 coaxial rotation of airgun 151 consists of airgun barrel 152 itself, while the rear portion consists of male threaded short stud 153 with upward directed pointer, resistance or spot-welded to the back of airgun cabinet 151.

A round scale with the rotational angle marked off in degrees is affixed by means of an adhesive to the rear surface of the rear arm of swing cradle bracket 149 in surrounding relation to the stud hole. Airgun barrel 152 and stud 153 fit through airgun barrel long axis-centered holes toward the upper ends of the front and rear arms of cradle-bracket 149. Rear stud 153 having been passed through the hole in the rear arm of cradle bracket 149, a Belleville disk ring spring washer is placed over the stud, centered in the angle scale and flush against the rear side of cradle bracket 149. Rotating airgun 151 thus rotates the pointer mounted on stud 153 over the scale, indicating the angle of rotation of airgun 151. Tightening knurled knob threaded over stud 153 compresses together the arms of cradle bracket 149 against the front and back of airgun 151 enclosure, fixing the airgun in rotational angle.

When, as shown in FIG. 83, spaces separate the knurled knob at the back and the front of airgun 151 enclosure from the swing cradle bracket, tube spacers (spacer sleeves, spacer tubes) are used to take up the intervals. The knob is tightened so that the rotational angle of the airgun, which is stabilized in angle of rotation by friction, can be adjusted by hand. At the front of the airgun cabinet, the barrel passes through a hole that journals by friction fit a ball bearing that holds the airgun barrel in surrounding relation. The axis of rotation for this airgun swing-type carriage mounting is thus coaxial with the airgun barrel and therefore allows adjustment in the working arc. To measure and render observable the extent of linear travel of the linear positioning table, horizontal joint between the base and moving platform of the linear positioning table 150 is calibrated in millimeters. A failure to discharge will be evident and thus can be distinguished externally, as discussed in the section below entitled Modes of Failure.

Less desirably, the airgun discharge components proper—$CO_2$ or compressed air cylinder, valve body, chamber, and barrel—can be separately mounted within the airgun cabinet for rotation on a U-bracket mounted on a linear positioning table, which then contained within the cabinet at the bottom, even when made of transparent polycarbonate plastic with a hinged or removable top that may be left open to allow access to allow adjustment to the valve body slide as described below, is then more likely to obscured from view by reflection. Such an arrangement thus reduces the observable action of the linear positioning table, of which the incremental moves, at both airgun barrel cabinet portal and entry into the body, are minute and not readily observable. Since this would make a malfunction less noticeable, it is not preferred.

VII2d(3)(g). Control of Muzzle-Head Turret-Motor Angle Within Working Arc

Due to the small size of the distances to separate the implants, control over the positioning of the turret-motor to adjust the muzzle-head rotational angle and airgun linear stage mounting to adjust the transluminal displacement, cannot be left to direct manual control. By contrast, transluminal positioning of the muzzle-head for purposes other than discharge can generally be left to direct manual control, or if necessary, connection to a linear stage whether by insertion in an airgun mounted to one or an independent stage. Instead, a numerical translator intervenes between the operator and the movements of the turret-motor and airgun table mounting. Such control is indirect and semiautomatic, in that the operator sets knobs for the action to be accomplished, and the controller and translator then execute the motion commanded.

Closed-loop control of the subminiature dc through-bore torque muzzle-head turret-motor is conventional, differing from programmed numerical control only in real-time setting of the angle by the operator. The same joystick is rotated clockwise or counterclockwise to the angular displacement of the turret-motor sought. When such point-to-point repositioning is to place the muzzle-head for successive discharges of the airgun, the duration at each intervening point need not be coordinated with miniball transit time, because the pause between the increments is preset to allow for the longest barrel length, typically 140 centimeters, this length being a critical factor in setting the exit velocity and provided with the apparatus. The output angle of the turret motor can be controlled with any digital motion controller and amplifier capable of driving a three phase brushless dc motor.

An exception pertains to the discharge of miniballs concurrent with an ablation or an angioplasty by an ablation or an ablation and angioplasty-capable barrel-assembly in the same pass. This generally comes about because medication miniballs are used to introduce medication concurrent with the traumatizing process. In this situation, exposure time to the ablative action fixes the uniform rate of travel at which the muzzle-head must move past the lumen wall, to which the rate of miniball discharge must be subordinated. Discharge at the airgun chamber is thus anticipatory by an interval contingent upon the velocity of the miniballs and overall length and uniform rate of transluminal travel of the barrel-assembly, so that the miniballs may be sent from the chamber well before the exit port reaches the target location or before the preceding miniball has penetrated.

Numerous full-sized two-axis off-the-shelf or commercially available controller-amplifiers are available for alternately allowing the a. Manual control of muzzle-head declination and level (depth of transluminal entry into the ductus) by means of a joystick or b. Manual control of automatic pattern control of the direct current turret-motor, the linear stage stepper motor, and discharge by the airgun in a coordinated manner as an auxiliary function much as the rotation of an interchangeable cutting tool turret on an automatic milling machine. When the ductus treated has been stabilized, as addressed below in the section entitled Motional Stabilization of the Implant Insertion Site, discharge is alleviated of the need to synchronize to intrinsic smooth muscle function.

When, however, the operator has no difficulty in anticipating the pulsation or contraction, stabilization of the action with medication or mechanical means is dispensed with, discharge synchronized to this action so that in an artery, for example, muzzle-head positioning is accomplished between and discharge during the diastoles. The airgun closed-loop semiautomatic system is to the extent possible assembled from commercially available components, to include a motor controller-amplifier, such as a Danaher Motion, Inc. S200 drive or comparable control apparatus from another manufacturer, such as Fanuc Robotics, Tolomatic Axiom, Yaskawa Electric Corporation, Parker Hannifin Corporation, Copley Controls Corporation, Baldor Electric Company, ACS Motion Control, and several hundred other companies, and controlled from the control panel mounted to the airgun.

Many such controller-drivers can exercise coordinated control over the turret-motor, linear stage, and discharge with the barrel-assembly engaged in the airgun mounted on a linear stage. The controller and amplifier for an ablation or an ablation and angioplasty-capable barrel-assembly with onboard control of the turret-motor requires a miniaturized controller and amplifier as indicated above in this section. To position the two diametrically directed electromagnets to face along any given diameter, rotatability of 90 degrees in either direction is required; however, to aim a monobarrel at any angle about the lumen circumference necessitates rotatability of 359 degrees. The material and thickness of the barrel-tube, and the curve it describes as it approaches the flush joint socket in the ejection-head must allow this degree of rotation without distortion to the bore as would retard or jam discharge.

When implantation discharge proceeds under motorized control, positional efficiency and longer turret-motor life are obtained by traversing the segment (length) of the ductus to be treated from end to end, discharging at intervals, then, when reaching the end of the 'run,' rotating the muzzle-head before reversing direction to place implants at an angle or angles other than that or those implanted on the first 'run.' That is, to discharge, rotate the muzzle-head, discharge, then advance or withdraw, discharge, rotate the muzzle-head, and so on, is not preferred. The transluminal (longitudinal)

movement on the first 'run' can be advancing or withdrawing. In more sophisticated use, longitudinal and rotary movement of the muzzle-head can be continuous throughout discharge, making possible implantation at high speed.

Nevertheless, for simplicity and because fast operation assumes the availability of imaging equipment that would instantly reveal a problem, the muzzle-head is best kept stationary during the interval that the miniballs traverse the barrel-tubes and enter the wall of the ductus. The turret-motor control circuit includes a circuit-breaker to prevent overload or burn-out. Excessive resistance to rotation arising within the mechanism or in the relation of the mechanism to the lumen wall is thus truncated. For example, resistance to the action of radial projection unit side-sweeping tool-inserts when present would typically be presented by plaque that was calcified outside the area cleared by atherectomy. Exceeding the torque limit value set for any reason would shut down the turret-motor averting dissection.

The distal end of the barrel-catheter is clamped within the collar at the proximal end of the through-bore turret-motor housing. In a radial discharge monobarrel, the barrel-catheter and singular barrel-tube are one and the same, and the distal curved segment of the barrel-tube is journaled within the rotor, which accordingly serves as a rotary joint. In a multiple barrel barrel-assembly, such axial rotation is not possible, so the neck of the spindle is journaled in the rotor. A motorized muzzle-head eliminating the need for a tighter turning ratio or turning torque in the barrel-assembly, more pliant materials can be used for the barrel-catheter, enhancing steerability and eliminating the possible if infrequent need for the aid of a hand-held external electromagnet.

The resistance to twisting more pliant barrel-tubes for the length of these in the splay chamber is less than with a stiffer tube material such as polytetrafluoroethylene. Dots of more brightly radiopaque contrast marker, such as Danfoss Tantalum Technologies Danfoss Coating® just beneath each muzzle-port, assists in positioning the muzzle-head. The greater pliancy of catheter tubing afforded by a motorized muzzle-head increases the potential for using conventional fixed shape guide-catheters as barrel-catheters. Vascular bends and angles of intersection or branching proximal to the lesion that are too acute to allow the smallest diameter barrel-assembly acceptable for stenting a given ductus to pass necessitate open exposure.

When the barrel-assembly is connected to a modified off-the-shelf hand airgun, power is provided to the motor from a remote power supply with connector mounted beneath the pistol grip. The placement of the power supply is different in modified and dedicated airguns as will be described under the section on airguns. Two small single pole single throw push button type switches are mounted to the pistol grip just above and beneath the ball of the thumb, so that slightly raising the thumb and depressing the upper allows the muzzle-head to be gradually and controllably rotated up to the rotational displacement necessary clockwise and depressing the lower switch allows rotation counterclockwise without the need to reposition or look at the airgun.

VII2d(3)(h). Factors that Affect Muzzle-Head Nosing Length or Reach, Steerability, and Trackability Whereas elongation in the nose or elements of the muzzle-head forward (distal, anterior) of the muzzle-ports reduces the forward reach or depth of access for discharging implants in a lumen of given diameter, elongation proximal to the muzzle-port or ports does not. Increasing the diameter, however, instantly limits passability down the vascular tree to deny access to smaller vessels. The incorporation into the muzzle-head of electrical radial projection units as addressed below in the section entitled Radial Projection Units, is limited in longitudinal extent by the resultant reduction in steerability.

A sufficient number of electrically operated radial projection units can be incorporated into the muzzle-head to allow the use of electrical/fluid system-neutral or self-contained spring-release syringe tool-inserts that can release a lubricant to aid passage or the use of side cutting tool-inserts to debulk obstructive tissue at the sides, and a nose heat-window as addressed below in the section entitled Thermal Conduction Windows (Heat-windows) and Insulation of the Muzzle-head Body in Thermal Ablation or Thermal Angioplasty Minimally or Fully (Independently Usable) Capable Barrel-assemblies can make it possible to pass through a heavily occluded ductus.

When the barrel-assembly incorporates radial projection units with side-shaving razor edged or sweeping ablation by abrasion brush tool-inserts engaged, the increased torque required is achieved by enlarging the motor windings longitudinally rather than diametrically. Fluid operated tool-inserts, which are capable of intermittent or continuous irrigation or aspiration, for example, require a fluid line that would demand an increase in the diameter of the muzzle-head. When the release of a fluid and its aspiration must be concurrent rather than alternating, two fluid lines are required. Untenable dimensions of the muzzle-head for use in a given type ductus are contained by relegating any that demand excessive longitudinal extent or breadth to a separate device that can be slid over the barrel-assembly after having been passed to treatment site.

Thus, the muzzle-head in an ablation or an ablation and angioplasty-capable barrel-assembly typically has only so many electrically operated radial projection units as necessary and is in effect one of a two part apparatus of which the outer can be added or withdrawn at any time. A loss in forward reach notwithstanding, embodiments that necessitate extension of the nose to house a trap-filter are extended when radial projection unit side-sweeping type tool-inserts are installed. As discussed above under the section entitled Concept of the Extraluminal Stent and the Means for Its Placement, the benefit in distal embolic protection filters remaining controversial, embodiments without side-sweepers installed are provided without a distal embolic protection filter, hence, without the loss in distal reach such incorporation produces in most muzzle-heads.

While ductus requiring treatment over much of their length will seldom be consistent in lumen diameter, to the extent possible, the muzzle-head body should match in diameter the most constricted or stenosed stretch of lumen. In an angioplasty-capable barrel-assembly, matching these diameters brings the heat-windows and muzzle-ports to the endothelium so that in a blood vessel, heat is conducted through the smallest amount of intervening blood, and the risk of a miniball being deflected prior to penetration is minimized. Also, side-sweeping radial projection unit brush type insert tolls then need protrude only slightly beyond the surface of the muzzle-head body, allowing the wells into which these are retracted to be shallower.

The primary limiting factor in reducing the diameter of the barrel-assembly is the diameter of the motor, which unlike the distal components of the barrel-assembly cannot be channeled or blood-grooved to allow at least some blood to flow past it. To reduce to the extent possible any opportunity for ischemic complications, the turret-motor is made somewhat smaller in diameter than the rest of the muzzle-head, and to compensate for the loss in torque that this reduction in diameter of the stator and rotor effects, the turret-motor is extended longitudinally rather than radially. The turret-motor is located at the rear of the muzzle-head to allow the components that require immediate access to the lumen to reach as far forward (distally) as possible and not deduct from the working reach of the muzzle-head down the vascular tree, especially when the lumen is decreasing in caliber.

Placed to the rear of the contacting components, the proportional increase in motor length essential to preserve torque does not precede the muzzle-ports to deny depth of access for implantation, for example. The administration of vasodilating medication allows some further access down the vascular tree, just as the administration of bronchodilating medication does so down the bronchi. When not circulating (systemic), such medication is injected through a service-channel Whether in center-discharge or combination-form angioplasty-capable barrel-assemblies, the incorporation of a radial projection units as discussed below, necessitates the installation of a distal thromboembolic protective trap-filter as well.

Since the release of debris when using radial projection unit cutting and brushing type tool-inserts is possible at any time, the trap-filter, as well as deployable simultaneously with the side-sweeper tool-type inserts, is deployable independently. Provided no laser or burr is installed, the distal portion of the central canal in a combination-form (edge-discharge) muzzle-head with longitudinally arranged recovery electromagnets is available as a sleeve or silo for storing the trap-filter, the overall length of the muzzle-head in that case reduced thus increasing the working reach compared to a muzzle-head with extended nose. However, installed thus, the central canal must not admit ductus contents whether blood into the ejection head even when the trap-filter is deployed. This kind of muzzle-head configuration can be used with either an edge- or center-discharge muzzle-head.

In a combination-form muzzle-head with a rotational atherectomy burr or laser cable installed, the central axial position is already occupied, so that a sleeve or silo recess into which the trap-filter can be retracted while not deployed must be placed adjacent to the burr or laser, which latter occupies the central canal, making the recess eccentric (off-center). Whether installed in the central canal or off-center to accommodate an excimer laser or atherectomy burr, the silo must have sufficient capacity to retract several miniballs. As seen in the cross-sections of FIG. 40 without, and in FIG. 67 with embolic trap filter, recovery electromagnets 65 are arranged perpendicularly to the longitudinal axis of the barrel-assembly with antechambers 67 situated in front of the outward directed poles of magnets 65.

Antechambers 67 are entered through spiral spring 157 spring-loaded trap doors 68, that shown in FIG. 40 double doors to allow clearance, that are drawn inwards to pass any ferromagnetic object drawn toward the magnet to either side. In both FIGS. 40 and 67, the arrows indicate the direction of miniball entry into antechambers 67. As seen in FIG. 67, the magnets are situated to allow the incorporation of the laser or burr cable in the central channel 155 while affording sufficient room between them and adjacent to the cable to place trap-filter silo 156. Accordingly, neither must one of the recovery electromagnets be reduced in size nor the nose elongated as would further reduce the working reach in comparison with the sidewise arranged electromagnets in the center-discharge muzzle-heads such as those shown in FIGS. 39, 48, 49, and 65.

VII2d(3)(i). Trap and Extraction Recovery Tractive Electromagnets in Radial Discharge Barrel-Assemblies for the Recovery of Loose and Extraction of Mispositioned Miniballs Recovery trap electromagnets in barrel-assemblies generally are addressed above in the section entitled Trap and Extraction Recovery Tractive Electromagnets for the Recovery of Loose and Extraction of Mispositioned Miniballs. Those for use in radial discharge barrel-assemblies are shown in FIGS. 39, 40, 48, 49, 65, 66, and 67. Radial discharge barrel-assemblies are usually small in gauge, and those for use in the arterial tree must have the capability to recover miniballs independently of the multiple backup trapping and recovery means addressed above in section 4g entitled Emergency Recovery of Miniballs and Stays and in section X below entitled Steering and Emergency Recovery of Implants with the Aid of an External (Extracorporeal) Electromagnet and subsections thereof, among others. Due to the limitations on size imposed by the gauge of the muzzle-head and the orientation required in embodiments such as those shown in FIGS. 65 and 66, for example, the coils or solenoids are usually wound with pure silver wire.

VII2d(3)(j). Blood-Grooves on Muzzle-Heads for Use in Blood Vessels

In a radial discharge monobarrel such as that shown in FIG. 38, the diameter of the barrel-assembly is small, posing less obstruction to the circulation in a vessel of given caliber than with multibarrel embodiments. By the same token, multibarrel embodiments minimize the period that the barrel-assembly must remain in the lumen, and when the muzzle-ports face in the opposite direction, cancel out most recoil. When the motor housing is already as narrow as possible, blood-grooves cannot be routed or impressed therein. Radial projection catheters need side grooves to pass blood no less than barrel-assemblies, although combination-form radial projection catheters need no side grooves so long as the bore remains empty.

When, however, muzzle-head 70 is deliberately chosen to fit flush within the lumen round and about, then as shown in FIGS. 38 and 40, blood-grooves 66, which serve as do side-holes in conventional catheters, are incorporated to expedite the flow of blood past the muzzle-head. Blood-grooves 66 are continuous with the ports and passages cut through the muzzle-head and when present, the spaces above the shelves represented by the floor of each enclosed tractive electromagnet chamber seen from the opposite side.

The depth of the groove or grooves varies in inverse proportion to the degree of artery wall radial excursion, which is dependent upon the elasticity of the wall and the blood pressure over the segment encircling the muzzle-head, and in direct proportion to its diameter and length, hence, volume of the muzzle-head up to the maximum dimensions indicated. Sclerosed arteries, for example, more constrain the muzzle-head in size and volume, reducing the number and type of components which might be included in the muzzle-head, limiting the number of barrel-tubes and radial projection units, for example.

One reason that the muzzle-head of a minimally or fully angioplasty-capable barrel-assembly includes a heat-window at the nose and usually one about the turret-motor or multiple heat-windows at the sides is to destroy vulnerable plaque before the increase in pressure due to intromission of the muzzle-head, even without coming into contact with the plaque, can cause the plaque to rupture. The eradication of plaque slightly augments the clearance surrounding the muzzle-head, reducing the flow-past resistance. The distinction in pressure before and after plaque eradication can be locally significant. So long as the bore remains empty, an angioplasty-capable combination-form barrel-assembly or radial projection catheter without side-groove or grooves should be usable off-pump in a sclerosed coronary artery.

VII2d(4). Forward Drive and Sag Leveling and Stabilizing Device

VII2d(4)(a). Use of a Forward Drive Stabilizer

The barrel-assembly must afford flexibility consistent with trackability, so that if left unsupported over the length that the degree of this flexibility determines, it will sag, any deviation from the longitudinal axis reducing the barrel-tube transit velocity proportionally until it results in jamming. This situation is not ameliorated by ensheathing the barrel-assembly within a size matched radial projection catheter, because these do not overlap in concentric relation over the extracorporeal segment proximal to the barrel-assembly power and control housing. During withdrawal, leveling is not a problem, because the barrel-catheter is pulled taut.

When the operator or an assistant advances and withdraws the barrel-assembly between discharges by moving the airgun, sagging and buckling of the extracorporeal length of the catheter can be prevented when the catheter can be supported by a free hand, the operator adjusting the controls. To minimize passive sagging due to unsupported length in excess of the self-supporting or intrinsic bridging stiffness of the barrel-catheter, the barrel-assembly should be chosen for minimal extracorporeal length and the airgun retracted rather than driven forward manually or with the linear stage if present if possible to achieve reasonable tautness and thus minimize this length.

The interposition of a forward drive and sag leveling and stabilizing device, or extracorporeal barrel-catheter straightener and deflection preventing extension linkage, arises when the transluminal distance to be traversed is large enough to allow the portion of the barrel-catheter between the airgun muzzle and entry wound to sag. To minimize nonpassive deviations of the extracorporeal barrel-catheter from the longitudinal axis, whether due to bending or buckling should the linear positioning table fail to achieve penetration in forward drive, transient deflections due to recoil during discharge, an extensible sleeve is incorporated to constrain the extracorporeal barrel-catheter to a straight condition.

During forward drive, or transluminal advancement, however, unless means are provided to prevent it, the resistance encountered will cause the barrel-catheter to suddenly flex or buckle, usually downward due to gravity. With an ablation or ablation and angioplasty-capable barrel-assembly, angioplasty, as opposed to implantation discharge, is usually accomplished manually with the barrel-assembly removed from an airgun. In use thus, the operator will grasp the barrel-assembly close enough to the entry wound to prevent the extracorporeal length of the barrel-catheter from bending, eliminating the need for a straightening device. A leveling and stabilizing device prevents passive sagging of the extracorporeal barrel-catheter while stationary and buckling during forward drive under the control of the positioning stage.

Figure 76A:
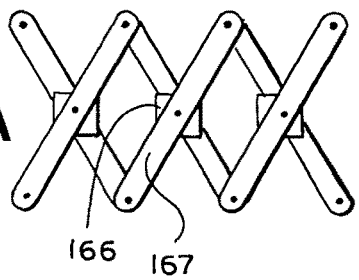
FIG. 76A is a side view of a scissors extension-type forward drive and sag leveling and stabilizing linkage device for interposition between the airgun and the barrel-assembly power and control housing for extension over the barrel-catheter to prevent sagging or sideways deviation when said device is expanded whether the airgun is moved by hand or a linear positioning stage as shown in FIG. 78C.
Figure 76B:
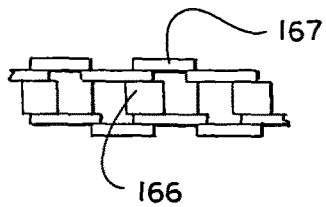
FIG. 76B is an overhead view of the scissors extension-type forward drive and sag leveling and stabilizing linkage device shown in FIG. 76A.
Figure 77A:
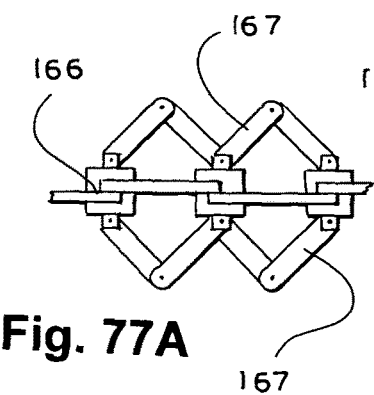
FIG. 77A shows an alternative forward drive, sag-leveling, and stabilizing linkage device to that shown in FIGS. 76A and 76B when fully extended, or expanded.
Figure 77B:
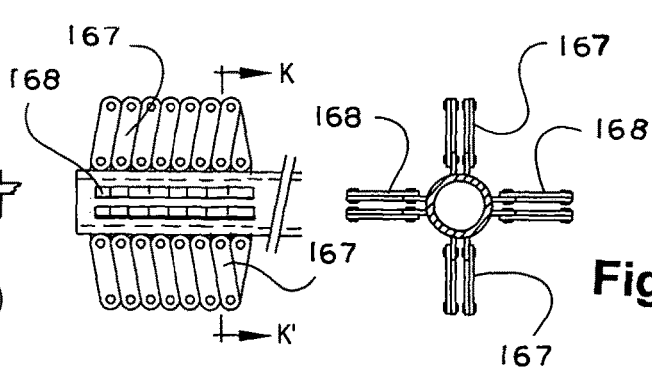
FIG. 77B shows the forward drive, sag-leveling, and stabilizing linkage device shown extended in FIG. 77A when fully retracted, or contracted.
Figure 77C:
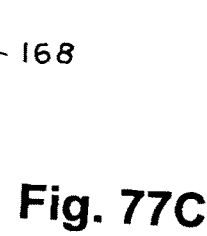
FIG. 77C shows a cross section of the forward drive, sag-leveling, and stabilizing linkage device shown in FIGS. 77A and 77B taken along line K-K' in FIG. 77B.

If the materials of the barrel-catheter and/or the barrel-tubes lack the necessary elasticity to continue bending, either or both can become unusably deformed, or kinked. FIGS. 76 and 77 show two kinds of linkage suitable for a forward drive sag leveling and stabilizing device. FIGS. 76 thru 78 provide detailed views of a forward drive sag leveling and stabilizing linkage device, 77*c* showing in cross-section the linkage depicted in FIGS. 77*a* and 77*b* taken along line K-K' in FIG. 77*b*. In FIG. 78, a fully contracted forward drive sag leveling and stabilizing linkage device incorporating the linkage shown in FIG. 76 is shown as used with an angioplasty-capable barrel-assembly.

A forward drive leveling and stabilizing linkage device is usually included as a part of any radial discharge barrel-assembly that must be usable with a linear positioning stage whether ablation or angioplasty-capable, minimally capable, or incapable. To reach to the depth required with the forward drive leveling and stabilizing device fully extended, the barrel-catheter must be correspondingly increased in length. Whereas the need to increase the discharge exit ('muzzle') velocity to pass anatomical bends to which the barrel-catheter must conform is established in advance, the reduction in exit velocity from incidental sagging or buckling of the barrel-catheter may occur unpredictably, and detracting from accuracy, is to be minimized, especially when placement of the miniballs in a tight formation under positional control must be precise.

The exit or barrel-tube muzzle velocity should be constant for tissue of like pretesting results, this testing addressed below in the section entitled Testing and Tests. Tissue that differs in hardness or resistance to penetration by a miniball along an anatomical bend should be implanted using the barrel-assembly manually; otherwise, the apparatus must be depended upon to adjust both the barrel-tube transit velocity and the exit velocity as an auxiliary function of the positional control system. When imaging shows the lumen to be free of bends and clearly passable with the barrel-assembly intended, then modulation of the barrel-tube transit velocity to compensate for bends and maintain a constant exit-velocity is unnecessary.

When moderate bends arouse slight doubt, the modulation of the barrel-tube transit velocity based upon a pretest recording of muzzle-head depth versus resistance may be dispensed with, such modulation then executed in real time. However when the diseased tissue lining the lumen is continuous and consistent so that the barrel-tube transit time must be modulated past curves to maintain a constant exit velocity, but the absolute degree of curvature arouses doubts about the use of a certain barrel-assembly, prerecording is used to modulate the barrel-tube transit velocity. More specifically, the pretest, described in the section below entitled Testing and Tests, calls for continuously measuring the resistance force encountered for the instantaneous displacement of the muzzle-head.

The test depends upon a proportionality between resistance to passage of the barrel-assembly and the resistance encountered by a miniball during discharge. The physics pertaining to these factors is different and the diameter of the muzzle-head and barrel-catheter along with several other factors are pertinent; however, the miniball does retrace the path taken by the barrel-assembly, and the relation, albeit approximate, is sufficient for practical use. This is accomplished by recording the output of a pressure sensor inserted in the stage drive train when passing the barrel-assembly to be used through the lumen to be treated under the control of the linear positioning stage to be used.

Rotary encoders substantially nullify any advantage in limiting the linear stage mover to an incremental or stepper motor merely to simplify translating motor shaft rotation into the equivalent distance. The test must simulate the actual pass contemplated, to include the release of a lubricant from the muzzle-head and use of the turret-motor oscillatory mode to clear a tighter bend, for example. Beginning at the same endoluminal starting position, the recording is then used to adjust, or modulate, the barrel-tube transit velocity of the airgun during the discharge pass.

Should the maximum allowable resistance reading be registered, further advancement through the bend is stopped as having a radius of curvature too sharp to negotiate with the barrel-assembly of the gauge and flexibility in use.

For the degree of resistance to correspond to the degree of bending, the driving force or torque of the stage motor is kept constant and resistance due to friction kept to a minimum; the resistance information is not used to modulate the linear stage motor torque. Except for curves smaller in length than the muzzle-head, the resistance registered will be slight; however this will serve as a sufficient indication of the need to adjust the barrel-tube transit velocity. A continuous recording of the resistance to a rod passed through a barrel-tube gives a somewhat closer approximation of the resistance encountered by a miniball as it transits the barrel-tube during discharge. The test rod is sufficiently flexible as not to give distorted results by straightening the barrel-catheter.

Since either means of testing is used to establish the miniball transit velocity required on the basis of the instantaneous resistance encountered, and this resistance represents the sum of the resistance presented by all of the curves through which the barrel-assembly has been passed, the instantaneous reading is usable for the purpose of adjusting the transit velocity. That is, at any level, the instantaneous resistance encountered is the sum of resistances passed through both for the muzzle-head and for the miniball. While the addition of a combination-form radial projection catheter in ensheathing relation to the barrel-assembly is disallowed, a more pliant barrel-assembly such as one with a shorter muzzle-head, and/or fewer barrel-tubes can be considered, or the decision made to use stays instead.

The torpedo-shaped muzzle-head nosing is not a significant factor in resistance and not advantageously changed. Unless intermittent ablation, angioplasty, or the use of injection or other tool-inserts is to remain enabled after discharge has been initiated, the power and control housing of an ablation or angioplasty-capable barrel-assembly is slid off. If left on the barrel-assembly and not kept proximal to the entry wound, its added weight will increase any tendency to sag. When the control of insertion and withdrawal are manual, the operator or an assistant supports the barrel-catheter, the slidable power and control housing if present kept close to the entry wound for the convenience of the operator and to minimize bending.

The power and control housing can be slid along splines about the outer surface of the barrel-catheter which also prevent its rotation and allows its use as a torquing (catheter rotation) device, or torquer during manual use when the barrel-assembly is disengaged from the airgun, such as to perform an angioplasty. Provided care is taken to make certain the barrel-catheter is not sagging behind the operator, that is, between the operator and the airgun, before each discharge is triggered, a stabilizer is not needed with a pipe-type barrel-assembly, which is always under manual control and never driven at a distance from the point of entry into the body by motorized means needed to achieve a precise placement over a tiny area.

When successive discharges are to be placed with a proximity and accuracy that cannot be accomplished manually, however, transluminal movement requires the use of a linear positioning stage. When executed by the linear positioning stage, it is usually because the intervals separating the discharges are in the millimetric range, numerous, and to minimize procedural duration, best delivered at a rate beyond the manual ability of a human operator. At such times, manual adjustments will usually prove not sufficiently timed or accurate to maintain the degree of exactitude necessary and may even contribute to inaccuracy. During manual control, the forward drive leveler and stabilizer can be separate from or as shown in FIG. 78, connected to the twist to lock connector mounted to the airgun muzzle.

When not connected at the front of the airgun, the stabilizer can be placed anywhere along the extracorporeal length of the barrel-catheter, making it usable whether a power and control housing is situated distal or proximal thereto when an ablation or angioplasty-capable barrel-assembly is used for an ablation or an angioplasty independently of an airgun. Shown fully contracted with the top and sides jackknife type linkage in FIG. 77b and with the scissors type linkage in FIG. 78, forward drive stabilizing leveling and extension linkage 159 consists of a succession of tubular segments for encircling the extracorporeal barrel-catheter and links to connect and maintain these tubular segments in longitudinal coaxial alignment as the linkage is pulled open or extended and pushed closed or contracted over the extracorporeal portion of the barrel-catheter.

The portion of the extracorporeal barrel-catheter encircled by the tubular segments over which the linkage is drawn are therefore likewise constrained to the longitudinal axis. When the linkage is used with a linear positioning stage, it is connected at the airgun muzzle and is usually connected to the rear of the ablation or angioplasty-capable barrel-assembly power and control housing. The linkage is therefore extended and contracted to the same degree and by virtue of the same attachment as the barrel-catheter to the linear stage-moved airgun. When used manually, the linkage can but need not be connected at either end.

Turning now to FIGS. 78 and 83, when under the control of a linear positioning stage or table, stationary base 150 of linear positioning stage 160 is connected to the distal end of forward drive stabilizing and leveling extension linkage 159 by bilateral (paired on the far side not shown) linking arms 161 so that the distal end of the linkage with connecting flange 162 is held stationary while proximal end connecting female component 103 and male component 75 as detailed in FIG. 73 of push and twist to lock constituting the flange connector and barrel-catheter 44 are pulled proximally, the barrel-assembly then withdrawn through the entry wound.

When positioning stage 160 drives barrel-catheter 44 forward, its slidable power and control housing 163 is held by arms 161, so that barrel-catheter-ensheathing radial projection catheter power and control housing 164, which is unitized with its more forward radial projection unit-containing barrel portion, moves forward and away from its initially juxtaposed position in contact with barrel-assembly power and control housing 164. Alternatively, flange 162 used to attach slidable barrel-assembly power and control housing 163 to holding arms 161 is made detachable so that the flange and not housing 163 itself is held by bilateral restraining arms 161, housing 163 then moving with housing 164 but freely slidable by hand.

That is, when linear stage 160 withdraws the barrel-assembly from the body, the receding stage simultaneously pulls linkage 159 open over the added length of barrel-catheter 44. In a duplex barrel-assembly, radial projection catheter power and control housing 164 is generally that housing the fluid pump if fluid controlled radial projection units are included. In so doing, the distance from the base of the stage to the distal end of forward drive stabilizing and leveling extension linkage 159 is held constant and sufficiently distad to prevent sagging or buckling. To allow the power and control housing to be slid along the barrel-catheter so that it can be kept close to the entry incision, it is not connected to the front or distal end of the linkage.

When ablation, angioplasty, or the use of radial projection assembly tool-insert injectors, for example, is to be alternated with implant discharge, the power and control housing is connected directly to the airgun muzzle with the leveling device distal to it. To allow either connection of the housing to keep it close to the entry wound or to the airgun, all of the interchangeable connectors are of the twist to lock connecting flange type, the housing having such a connecting flange fastened to its proximal or back side. While usually unnecessary, especially with an assistant, a leveling and stabilizing linkage can be used during manual control to steady the barrel-catheter, but it is then adjusted in extension and slid along by hand rather than connected at either end as when used as shown in FIGS. 78 and 83 with a positioning stage.

If the barrel-assembly is of the ablation or angioplasty-capable type with a power and control housing 163, distal end of forward drive stabilizing and leveling extension linkage 159 is fastened to proximal or rear face of housing 163, held close to the entry wound. Fastening of forward drive stabilizing and leveling extension linkage 159 at its proximal end to the distal (front) face of the twist-to-lock connection flange comprising female component 103 and male component 75 on the barrel-catheter 44 and at its distal end to flange 162 at the proximal face of barrel-assembly power and control housing 163 depends upon whether it is a permanent part of the barrel-assembly or an attachment.

As a permanent part of the barrel-assembly linkage 159 is resistance or spot welded if metal or glued if plastic at the stage base end but left temporarily fastenable at the housing flange to allow barrel-assembly power and control housing 163 to be slid off so that a combination-form radial projection catheter can be slipped over the barrel-assembly to constitute a duplex (composite, bipartite) barrel-assembly. Depending upon the application, the leveling device can be attached at either, neither, or both ends, neither when manually adjusted, and both under automatic positional control, for example, or can be situated in front of instead of behind the power and control housing.

Using a duplex barrel-assembly to place a tight formation of miniballs, the unsheathed barrel-assembly is passed, usually to the most distal site for treatment at the start of the procedure. Whether the leveling device is needed is decided based upon the likelihood that the extracorporeal unsheathed length of the barrel-catheter will bend. For any barrel-assembly, since a need to reverse direction can always arise, a barrel-assembly should always incorporate or allow the addition of a leveling and stabilizing linkage for its length plus the increase in length to accommodate the device. Barrel-assemblies intended for attachment as desired of an extension linkage should afford this extra length as well and allow removal of the barrel-catheter connecting flange to allow such a linkage to be slid over the proximal end.

Whether a permanent component or an attachment, the length of the linkage when extended should accommodate leveling for a barrel-assembly of given length without the need to add or remove links. Each consecutively delivered miniball discharge is then positioned by the control system in withdrawal. If the barrel-assembly is to be ensheathed within a radial projection catheter to use more tool-inserts than the number of radial projection units in the muzzlehead can accommodate, then only the unsheathed portion of the barrel-catheter need be supported by an expansion linkage.

Since the added sheath increases the diameter and stiffness and therefore reduces the trackability of the barrel-assembly over the length that the two overlap, support by the extension linkage is required during insertion of the unsheathed barrel-assembly, addition of the projection catheter usually eliminating the need for support or reinforcement and therewith, a supporting linkage. As an attachment, the linkage is added to the barrel-assembly by forcibly sliding off the friction fit connecting flange from the barrel-catheter and slipping the linkage over the barrel-catheter whether a power and control housing is distal thereto. If present, the housing is attached to the front (distal face) of the connecting flange at the distal end of the linkage.

Attachment of the linkage at its proximal end to the connecting flange at the airgun muzzle and at its distal end and to the connecting flange resistance or spot welded if metal or glued if plastic to the rear (proximal side) of the housing is by means of twist-to-lock connection flanges of the same kind as are used to fasten the barrel-assembly to the airgun muzzle. The paired flanges are likewise twisted to lock into ganged, or back to back, relation. To allow bilateral restraining arms 161 to be adjusted in length, these are made in two overlapping parts, one containing a central lengthwise slot to allow a threaded stud fastened to the other part to project through the slot so that it can be slid along the slot for tightening at the length to which the distal end of forward drive stabilizing and leveling extension linkage 159, and if present, power and control housing 163 is to be fixed in distance from positional stage base 150.

Wing nut 165 allows the parts of restraining arms 161 to be tightened at any point along the slot thus making the overall length of bilateral link arms 161 adjustable for leveling and stabilizing devices of different length on different barrel-assemblies. Bilateral restraining arms 161 allow housing 163 to be adjusted in position along barrel-catheter 44 regardless of whether forward drive stabilizing and leveling extension linkage 159 is fully contracted. The two parts of bilateral restraining arms 161 include on their facing side complementary detents in the form of a small elevation on one arm and complementary depression in the other that lock the two in linear relation when wing nut 165 is tightened. Distal leveling device connecting flange 162 has to either side small retractable spring-loaded studs that enter a hole toward the distal end of each restraining arm 161 when slid over it locking arms 161 in place against its sides.

The distal end is removed by depressing the studs with the end of a sharp object or gently separating the arms to either side. Ordinarily, bilateral arms 161 are permanently fastened to the base 150 of linear stage 160 by means of snugly fastened rivets that allow arms 161 to be rotated into position when needed. Since an emergency condition related or unrelated to the procedure might intervene to necessitate that the procedure be stopped at any moment, duplicate cancel (stop, abend) keys are provided on the barrel-assembly and airgun control panels. Either stops the linear positioning stage and discharge as tied thereto at the same instant. With discharge accomplished as an auxiliary function of the positional control system, should the barrel-assembly stop moving, discharge is abended, precluding perforation of the treated ductus as the result of multiple discharges at the point of the stoppage.

A forward drive stabilizer can be incorporated into any barrel-catheter, to include combination-forms that incorporate a rotational atherectomy burr or laser. These must, however, be confirmed as sufficiently flexible to avoid perforating the ductus during insertion or forward drive. Since no such atherectomizer is needed once the angioplasty portion of an operation has been completed, the free or proximal end of the barrel-assembly can be disconnected from the console cable for connection to the airgun. Removal of the side-socket connected cable assists in constraining the barrel-catheter to the longitudinal axis when connected to the airgun.

VII2d(4)(b). Structure of Forward Drive Stabilizing and Leveling Extension Linkage As shown in FIGS. 76 thru 78, leveling and stabilizing extension linkages constitute mixed kinematic chains, which overall open-ended, comprise series of closed kinematic chain segments in parallelogram loops, that of FIG. 76 connected at the sides of each tube segment 166, and that of FIG. 77 at the top, bottom and sides of each successive pair of tube segments 166. Since vertical links 167 attach to the top and bottom, and horizontal links 168 attach to the sides of each tube segment, the horizontal and vertical linkages do not obstruct with one another as would be the case were the top link of one tube segment and the bottom link of that adjacent unified and joined to each tube segment at the sides.

Alternative linking schemes, such as alternatively side then top and bottom linking successive tube segments is not preferred as yielding a structure with less longitudinal rigidity. The stiffness needed must not detract from the ease and smoothness of expansion and contraction. Tube segments 166 are cut from nonferromagnetic sheet stainless steel or a nonferrous metal such as copper or aluminum. To avoid seizing (catching, sticking) along the barrel-catheter, the internal surface of the tube segments 166 must be smooth and provide sufficient clearance from the outer surface of the barrel-catheter.

This clearance is too small to allow the use of a linkage with tube segments of given internal diameter to support barrel-catheters of different gauge. The linkage must be tight, that is, have little play, but be fully extendable and remain straight when fully extended when held at one end with no barrel-catheter passing through it. Links 167 in FIG. 76 and 167 and 168 in FIG. 77 of linkage 159 are die cut from sheet metal of the same material and joined by solid or clevis pin type round head rivets with spring washers, preferably of the Belleville disc ring type, interposed between the heads of the rivets and the arms of the linkage, or nylon bearings with compression fit heads, for example.

VII2d(5). Direction of Radial Discharge Barrel-Assembly Muzzle-Head on Discharge as Antegrade (Advancing, Forward, Distad, Prograde) or Retrograde (Withdrawing, Backward, Proximad)

The trap-extractor magnet assembly in a radial discharge barrel-assembly necessarily positioned distal to the muzzle-ports, prior to the first discharge when placement of the stent-jacket is to follow, the magnetic field generated by the trap-extractor magnet assembly intercepts the passage of any loose miniball down the lumen. To avoid the risk of disrupting any miniballs that have already been implanted, the barrel-assembly is advanced forward from discharge to discharge thus causing the magnetic field to move away from rather than to pass these. A parachute or trawler type fishing net configured filter (trap-filter, filter-trap) deployed ahead of (distal to) the leading end (nose) of the muzzle-head is also available to trap loose miniballs. When the procedure has been completed and the barrel-assembly is to be withdrawn, the amperage through the electromagnets is reduced to zero and the barrel-assembly withdrawn.

If any miniballs failed to implant, then the rotary magazine clip hole for the number a position or barrel-tube to implant the missed positions is used to place those missed when withdrawing. If a miniball or miniballs had been retrieved, then the amperage is reduced to the lowest value that will allow the trapped miniballs to be held through any radial accelerations or recoils of the muzzle-head to follow and the barrel-assembly to be withdrawn without disrupting the miniballs that have been implanted, and once these are past, the amperage may be returned to a higher value. If not matching the lumen in diameter, the barrel-assembly can be nudged into contract with the lumen wall with the aid of an external hand-held electromagnet as described below and blanked out rotary magazine clips used to implant only the side in contact.

VII2e. Simple Pipe and Radial Discharge Barrel-Assembly Common Elements

VII2e(1). Barrel-Catheters, Barrel-Tubes, and Barrel-Assemblies

The barrel-catheters of simple pipes, comprising a single barrel intended for use primarily in the airway are one and the same tube. Single (monobarrel) and multiple barrel (multibarrel) radial discharge barrel-assemblies are designed to be usable in the bloodstream where air embolism and fouling of the mechanism by the inflow of blood must be averted even were discharge inadvertent with no miniball ahead of the expulsive gas. The barrel-tubes in radial discharge barrel-assemblies must therefore be enclosed within a jacket, or barrel-catheter, that allows the internal equalization of differences in pressure. Whereas simple pipes are intended for use in vasa other than blood vessels so that the presentation of a thromogenic metal (stainless steel) surface is not an issue, radial discharge barrel-assemblies may be used in any type vas.

Those for use in the vascular tree must be coated with low friction fluoropolymer such as polytetrafluoroethylene. Flexibility, hence trackability, and see-through clarity are improved when the barrel-catheter consists of undyed tetrafluoroethylene-hexafluoropropylene-vinylidene fluoride terpolymer (THV resin), and pliancy increased when combined or coextruded with another fluoropolymer. Except at the muzzle-hole, a radial discharge barrel-catheter is otherwise substantially airtight. The introduction of gas into the bloodstream is averted by providing a return path of less resistance than is posed by the blood even in antegrade (downstream) flow.

This is achieved by perforating the barrel-tube or tubes so that gas may circulate within the enclosed barrel-assembly. The use of various tubing materials to include coextruded or compound tubing makes possible a wide range of pliancy and diameter in the unitary catheter, and this is significantly augmented in multiple barrel barrel-assemblies where the barrel-tubes may be made of different materials and adjusted in distance from the central axis. barrel-catheter of an ablation or angioplasty-capable barrel-assembly is splined with sliding contacts in the valleys so that a power and control housing can be slid along it.

The flexibility of multiple barrel-tube barrel-assemblies, such as those shown in FIGS. 39 and 41 thru 45 described below, is also affected by the distance from the longitudinal axis of the barrel-catheter of (noncoextruded) barrel-tubes 74 through the holes 91 in and intervals along the barrel-catheter separating the centering devices 95 used to position the barrel-tubes 74, as addressed below in the section entitled Centering Devices (Centering Disks); and the presence, materials, and angles of blood-tunnels 96 seen in FIGS. 39, 41, and 42, addressed below in the section entitled Hypoxia and Ischemia-averting Elements, 2. Blood-tunnels.

When the diameter is too small to incorporate tunnels as buttresses, these are made solid or omitted. For increased flexibility or trackability and/or to absorb the shock of recoil, the barrel-catheter can include convoluted segments at intervals variable in length, interval, and number. By discontinuously applying the convolution impressing mold to the straight-walled tubing as originally extruded, the tube manufacturer can make tubing with any pattern of alternately convoluted and straight-walled segments. The barrel-catheter also includes a convoluted segment for flexion and recoil absorption.

The torque ratio or resistance to twisting and bending deformation of the barrel-catheter depends upon several variables, to include:

1. The intrinsic pliancy of the material or if coextruded materials.
2. The wall thickness.
3. Diameter of the barrel-catheter.
4. The intrinsic pliancy of the material of which each barrel-tube is made.
5. The radial distance set by the centering devices of the barrel-tubes from the longitudinal axis.
6. The longitudinal interval separating adjacent centering devices.
7. Whether the barrel-catheter incorporates blood-tunnels.
8. Whether the operator chooses to preinsert a catheter or rod of widely variable pliancy down an available barrel-tube.
9. The incorporation into the barrel-catheter of convoluted segments, the lengths of and intervals separating any convoluted segments.
10. Whether the centering devices are left free to rotate at the edges or have been bonded to the barrel-tubes and the internal surface of the barrel-catheter, and
11. The resistance to twisting of any other lines running through the barrel-catheter, such as the wires to the turret-motor and the electromagnets and the optical fibers when a laser, for example, has been incorporated, and so on.

Bonding together the parts of barrel-assemblies and special radial projection unit catheters is preferably accomplished by means of ultrasonic welding. Alternatively, in addition to one-component tissue compatible cyanoacrylate cements, suitable adhesives for bonding together the component parts of barrel-assemblies include those cured with ultraviolet light, such as DYMAX Corporation, Torrington, Conn. 200-series catheter adhesives, more specifically, DYMAX 208 CTH-F. This single component adhesive cures in seconds with ultraviolet light curing systems that are also available from DYMAX Corporation, Torrington, Conn. Numerous other adhesives that might be used include Master Bond Polymer System EP3HTMED.

The use of materials and incorporation of internal structural features to be described and the selection of barrel-assemblies to avoid nonessential length allow approximating a 1:1 torque ratio. The muzzle-head is provided with tantalum markings for high radiopacity. Anatomy permitting, this allows even an exceptional muzzle-head that lacks a turret-motor to be accurately rotated to the desired position manually. The resistance to bending of the extracorporeal portion of the barrel-assembly is more significant in ablation and ablation and angioplasty-capable barrel-assemblies, which are removed from the airgun and forward drive and sag leveling and stabilizing device for independent use. Numerous means for reducing the flexibility of the barrel-assembly are provided herein.

These include the material or compound material such as coextruded tubing, thickness of the barrel-catheter and barrel-tubes, number of blood-tunnels if any, interval separating barrel-tube centering devices and whether these are peripherally bonded to the internal surface of the barrel-catheter. Since even with centering devices and blood-tunnels and without the weight of a power and control housing, excessive length causes sagging (drooping) if not kinking, overall barrel-assembly catheter length should be kept to a minimum. Sagging is further reduced through shifting the weight of a slidable power and control housing, as addressed below in the section entitled Slidable Ablation or Ablation and Angioplasty-capable Barrel-assembly Power and Control Housing.

Stiffening elements are more dense in the extracorporeal barrel-catheter. The intracorporeal barrel-catheter with blood-tunnels that prove excessively stiffening can be made more flexible or trackable by including convolutions or convoluted segments. The use of a cooling catheter to return the temperature of the turret-motor and/or recovery tractive electromagnets when sent heating current for thermal angioplasty, as will be described below, is more effective when the diameter or gauge of the cooling catheter can be larger as passable down the central canal of a center-discharge barrel-assembly rather than down a barrel-tube as is necessary when using a combination-form barrel-assembly that incorporates an atherectomy burr or laser cable at the center. The general concept of a cooling catheter is not new.

Considered in cross-section, the heat conduction path from within the otherwise insulative barrel-tube to the turret-motor and electromagnets is asymmetrical (off-center, eccentric); however, for equalizing the pressure of discharge to avoid arterial or venous gas embolism (air embolism) (see, for example, Mendenhall, M. L and Spain, D. A. 2007. "Venous Air Embolism and Pressure Infusion Devices," *Journal of Trauma* 63(1):246; Wittenberg, H. G. and Allison, J. R. 2006. "Venous Air Embolism," *eMedicine*, available at http://www.emedicine.com/emerg/topic787.htm) the barrel-tube has been perforated over the distal segment aligned to these heated elements, which perforations pass the heat. The exit velocity of the barrel-tubes within a barrel-assembly are not equalized as necessitates that all be perforated exactly alike.

VII2e(2). Connectors (Couplings) for Quick Release and Reconnection of the Barrel-Assembly to the Airgun with Proper Alignment An interventional airgun must accept any barrel-assembly of like gauge or caliber, whether a simple pipe or an ablation or ablation and angioplasty-capable barrel-assembly. Except for size, the mechanical connection of the barrel-assembly to the airgun is substantially the same in embodiments that otherwise differ. This connection must allow the operator to immediately disengage the barrel-assembly for manual transluminal advancement, withdrawal, or rotation and just as quickly reinsert it into the airgun barrel to resume discharge with the assurance that the security of connection and alignment of the barrel-tubes to the holes respective of each in the rotary magazine clip will be exact.

VII2e(3). Twist-to-Stop and Lock Connector (Twist Lock Connector, Keyed Spring Lock Connector)

In use, the barrel-assembly is selected and manually introduced into the lumen through a conventional incision and introducer sheath. There is no guidewire. Once the position along the lumen is reached, the proximal end of the barrel-assembly is engaged within the airgun barrel with the extracorporeal segment straight. If, depending upon the pliancy of the specific barrel-assembly, the extracorporeal length results in some downward bowing at the center, then the slack is taken up by backing up the muzzle-assembly with the linear stage as described below until the muzzle-head can just be seen to move. If the muzzle-head must be advanced or withdrawn midprocedure, the linear stage is used or the barrel-assembly can be disengaged from the airgun and manually repositioned.

When manually repositioned, upon reconnecting the barrel-assembly, the linear stage is used to 'trim off' or take up any slack and thus straighten the barrel-assembly. Unless deliberately activated, discharge remains disabled, eliminating the possibility that a bend might affect discharge. Use of the apparatus is described in greater detail following the section on the linear stage and in conjunction with a description of the control panel. This is accomplished through the use of a twist-to-lock joint or coupling that incorporates short spring steel tabs with central depressions to receive protrusions on the complementary tabs that are mounted about the barrel-assembly.

While a joint of the kind described requires a slight twist to connect or to disconnect, this is preferable to the relative lack of tight connection provided by more costly and complex joints that require no twisting motion, such as the quick disconnect hose couplings used in vacuum cleaners. In the simple pipe and air pistol, only one barrel-tube need be aligned. However, in a multiple barrel radial discharge barrel-assembly, an end-plate at the proximal end of the barrel-assembly is essential to stabilize the position of the proximal ends of the barrel-tubes, and the rotary distance or throw of the complementary tabs must be such that the stops situate the barrel-assembly in the airgun barrel with the barrel-tubes aligned to their respective holes in the rotary magazine clip.

To allow the precise fit (without play) of the barrel-assembly in the airgun barrel without sticking or seizing midprocedure, both the external surface of the portion of the barrel-assembly to be inserted into the airgun barrel and the internal surface of the airgun barrel, which must exactly match in diameter are made of low friction, generally fluoropolymer materials, such as polytetrafluoroethylene. Mechanical connection of the barrel-assembly within the barrel of the airgun by friction fitting is avoided as risking resistance to removal if unavoidable midprocedurally.

Regardless of caliber, type, or number of barrels, mechanical connection of the barrel-assembly to the airgun is by means of a push-and-rotate-to-engage keyed flange type connector or coupling, as shown in FIG. 73. Receiving or female component 103 of the flange connector is mounted to the front of airgun muzzle 105 (use of the term 'muzzle' should not lead to confusion with the muzzle-head or muzzle-probe at the distal end of the barrel-assembly seen as 70 in the radial monobarrel shown in FIG. 38 and as 73 in the radial multibarrel shown in FIG. 39). In FIG. 73, male component of twist to lock flange connector 75 is mounted around barrel-catheter 72 at the distance from end-plate 99 that barrel-assembly 72 is to enter airgun barrel 107.

Figure 74:
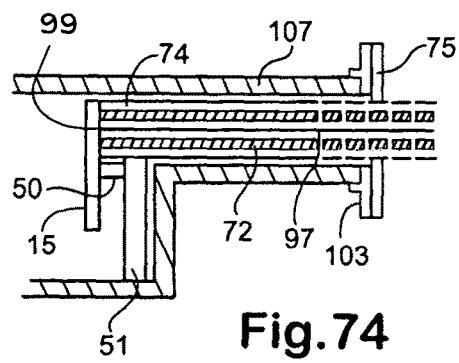
FIG. 74 is a longitudinal sectional view of the barrel-catheter of a double barrel-tube radial discharge barrel-assembly having an airgun connector such as that shown in FIG. 73 locked in position within the chamber of the airgun.

In a barrel-assembly not for use independently of the airgun that draws power not from an inmate power and control housing but rather by connection to the airgun power supply, or in an independently usable ablation or ablation and angioplasty-capable barrel-assembly also controllable from the airgun control panel, multiple electrical contact connector terminal set 101 seen in FIG. 72 is brought into contact with the counterpart electrical contacts within the airgun chamber, end-plate 99 then flush fit within the airgun chamber as seen in FIG. 74 just short of as not to impede the movement of the rotary magazine clip 15 in FIGS. 31, 32, and 74. To engage the barrel-assembly in the airgun barrel, tabs 102 are inserted into slots 104.

Rotating the end of the barrel-assembly clockwise causes the tabs to slide beneath the compressive ceiling overlying rotary slideway 108, which closed off at the extremity of rotation stops the tabs at the exact rotational angle at which the barrel-tubes in barrel-catheter 72 are aligned to their respective barrel holes in the rotary magazine clips shown as 15 in FIGS. 31, 32, and 74. Simple pipe and radial discharge monobarrels are most often used with the muzzle-port directed downwards. Monobarrels require no barrel-tube alignment.

Figure 75:
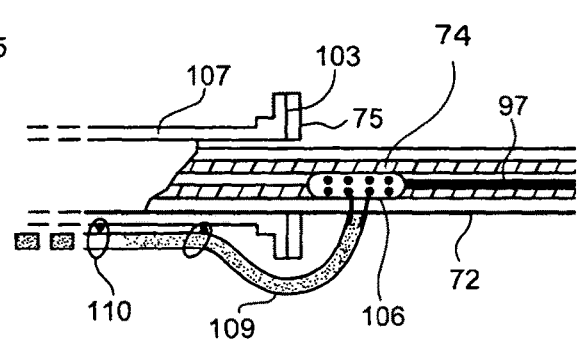
FIG. 75 is a longitudinal view, partly external and partly in section, of a side-socket electrical, fluid, or electrical and fluid connection as alternative or additional to the end-plate connection shown in FIGS. 73 and 74, which distal to and separate from the connection of the barrel-assembly made by engagement in the airgun chamber, can be used, for example, to render an ablation or ablation and angioplasty-capable barrel-assembly airgun-independent for power while allowing immediate access for coupling fluid lines or inserting cables such as endoscopic, laser, or cutting tool midprocedurally.

The component of the stop and lock ring component of the twist-to-lock connector fitting mounted about the barrel-catheter seen as 47 in the monobarrels of FIGS. 31, 32, and 38 and 75 of the multibarrel seen in FIGS. 39, 74, and 75 and the mono-multibarrel-neutral view of FIG. 73, has tabs 102 shown in FIG. 73 which fit into slots 103 in the complementary receiving or female component fitted about the front of the airgun muzzle, as shown in FIGS. 73 and 74. Twist-to-lock fitting 47 both establishes the limit of intromission of the barrel-assembly into the barrel of the airgun and locks the barrel-assembly in position with its distal end just short of as not to impede the movement of the rotary magazine clip 15 in FIGS. 31, 32, and 74.

In accordance with the industry convention for indexing or incrementally rotating clip 15 when the trigger is pulled, notches 48 about the outer edge of rotary magazine clip 15 in FIGS. 31, 32, and 74 are successively engaged by pawl 49. The rotary magazine clips are inserted by placing the center hole 43 over axle 50 mounted to supporting post 51. To remove one rotary clip and replace it with another whether to replenish a certain type miniball or change the type used is accomplished midoperatively in four seconds or less. These notches are on the reverse face of the rotary magazine clips and thus unseen in FIGS. 29 and 30.

Shown in FIGS. 31, 32, and 38 as part 47 and in FIGS. 39, 73, and 74 as 75, the male portion of stop and twist-to-lock connector, has at least two tabs that fit into the slots in a circular archway, or if the archway is divided for each, into the end-openings of the divided circular archway, that is mounted to the front of the airgun muzzle, so that once entered into the slots, twist-to-lock fitting 47 can be slid around through the circular slideway or slideways beneath the ceiling over the archway of the slideway to the slideway ends and so locked in position both angularly and longitudinally.

In all barrel-catheters, the proximal portion for entry into the airgun barrel has an outer diameter that precisely fills the airgun bore or inner diameter of the airgun barrel, whether the airgun barrel has been modified with, for example, a polytetrafluoroethylene lining added to cover (blanket over) the rifling as well as to reduce the caliber, or the barrel is original in a dedicated interventional airgun, as later described. Accordingly, engaged thus, the outer surface of simple pipe monobarrel barrel-catheter 44 in FIGS. 31 and 32 is flush throughout its airgun-intromitted length against the bore of airgun barrel 57 with the proximal end of the barrel-catheter 44 positioned immediately before the miniball hole or holes 42 in the rotary magazine clips shown in FIGS. 31, 32, and 74.

This means for engaging the proximal end of a barrel-assembly in an airgun is common to all barrel-assemblies and thus addressed in a separate section below. Barrel-catheter 44 is made of a single length of tubing with the curve toward the tip 45 maintained by the bond that unites the upper surface of the tractive electromagnet 46 housing 56 to the underside of the barrel-catheter 44. To minimize the risk of injury to the lumen wall or larynx by gouging, the pointed end of the simple pipe barrel-assembly is girdled about with a soft guard (bumper, shield) 52, similar to a dam used in dentistry. The guard is made of expanded polytetrafluoroethylene (ePTFE) or a pharmacologically active leachant and plasticizer-free engineered nylon polyether block amide resin such as Pebax® 3533 tubing.

It is stretched over and fixed in position about the barrel-catheter by its own restorative force. Guard 52 overextends the distal end of the barrel-catheter slightly, typically by 1 millimeter. To accurately rotate the muzzle-head requires that the barrel-assembly resist twisting, or have a torque ratio approaching 1:1. Since radial discharge barrel-assemblies present an outer contour that is rounded and smooth, are provided with a remotely controllable motorized muzzle-head turret, and the muzzle-head is routinely wetted with a lubricant such as those specified above in the section entitled Stent-jacket Insertion Tools, before entry, the risk of gouging, twisting, and stretching injury is avoided.

When a single barrel radial discharge barrel-assembly is used in the airway, mucus serves as a lubricant. When a combination-form muzzle-head includes an excimer laser (addressed below), the ends of the optical fibers can be wetted with lubricant as well, the laser quickly vaporizing this upon activation. The degradation products liberated by such vaporization must, of course, be innocuous in the bloodstream. Lubricant can interfere with the cutting action of a rotational atherectomy burr so that lubricant should be used sparingly to avoid the muzzle-head or probe nose.

The means of testing for endothelial adhesion and delivery of lubricant to the muzzle-head midprocedurally are described below under the section on testing. Broadly, whenever the risk of injury due to transluminal, manual, or motor torqueing (rotary) movement of the barrel-assembly is present, a lubricant is used. Whenever the barrel-catheter of a barrel-assembly used in the vascular tree approaches the diameter of the muzzle-head, the entire barrel-assembly is wetted with a lubricant. Depending upon the materials used to make the barrel-catheter and muzzle-head, the outer surface of both components can be coated with one of the lubricious materials specified below.

An outer coating of polytetrafluoroethylene will generally obviate the need for lubrication. Alternatively, silver-based coatings such as is available from Spire Corporation, Bedford, Mass. do not materially detract from lubricity but do appear to reduce the risks of Infection, thrombosis, and stenosis (see Bambauer, R., Mestres, P., Schiel, R., Schneidewind-Muller, J. M., Bambauer, S., and Sioshansi, P. 2001. "Large Bore Catheters with Surface Treatments Versus Untreated Catheters for Blood Access," *Journal of Vascular Access* 2(3):97-105).

VII2e(4). Engagement of the Barrel-Assembly in the Airgun

The barrel-assembly, such as a two or four-way barrel-assembly as depicted in FIG. 39, is capped off at its proximal end with an end-plate 99 that receives and holds the proximal ends of the barrel-tubes, which open through the end-plate, and must be positioned in precise alignment with their respective holes in the rotary magazine clip or in a mono-barrel barrel-assembly, to the fore the miniball to be discharged. In order to maintain this precise alignment, the end of the barrel-catheter must fit flush within the chamber of the airgun. In a noncombination-form barrel-assembly with center discharge muzzle-head, a slit valve in end-plate 99 is used for insertion of a cooling catheter or other external cable or line as described above in the section entitled Cooling Catheters (Temperature-changing Catheters).

However, because entry into the barrel-assembly at the rear rather than through the side by means of a side-socket obstructs the barrel-assembly from insertion into the airgun, such use of the end-plate as an end-socket does not allow, for example, chilled gas to be delivered to the treatment site to chemically and thus physiologically retard or stabilize the inner layers of the ductus during discharge. The incorporation of a side-socket into the battery pack allows the ablative and angioplasty capabilities of the barrel-assembly, such as a supplementary or 'touch up' ablation or angioplasty, to be applied during discharge without the need to disengage the barrel-assembly from the airgun, thus interrupting the procedure, possibly degrading precision when discharge is machine-controlled.

The barrel-catheter is inserted into the airgun barrel to a distance just short of, as not to come into contact with, the rotary magazine clip as it advances by indexed rotation from one discharge load to the next. Referring now to FIG. 74, barrel-catheter 72 is inserted into the barrel of the airgun 107 up to the limit allowed by stop-and-lock ring 75, which engaged within the female component of the twist-and-lock connector that is mounted to the muzzle of the airgun places the end-plate just short of contact with the rotary magazine clip 15 with barrel-tubes 74 perfectly aligned to the hole in the rotary magazine clip respective of each barrel-tube.

Increased interchangeability of barrel-assemblies and airguns raises the risk for a barrel-assembly not designed for use with a given airgun or an airgun that has been configured for different operation, such as the use of a different rotary magazine clip or different bore insert. Barrel-assemblies must therefore bear clear compatibility indicia. Since a tag will be removed, this is best accomplished by molding specification on every barrel-assembly and color coding adaptors for insertion in the airgun. Making the chamber of transparent plastic allows the color of the rotary magazine clip to be seen from the outside.

VII2e(5). Barrel-Assembly End-Plate

The centering device at the proximal end of the barrel-assembly is the end-plate (terminal plate), 99 shown in FIGS. 38, 39, 73, 74, with a detailed view provided in FIG. 72. Unlike the proximal ends of the gas return pressure relief channels, to maximize the propulsive force and minimize any opposing inflow of blood when the muzzle-ports at the sides of the muzzle-head are introduced into an arterial lumen, joint between the nozzle and rotary magazine clip should be tight and flush. That is, only the proximal end of the miniball propulsion joints need be airtight in the distal direction. By contrast, the proximal ends of the relief channels when proximally continuous all the way back to the end-plate must vent pressure not dissipated within the barrel-catheter.

Venting is usually by dissipation within the barrel-assembly, but can be at the terminal plate through or without a slit membrane or through holes or one-way valves in the extracorporeal segment of the barrel-catheter. When dissipated internally, the centering devices have holes to allow the back pressure gas to pass through proximad. In such a barrel-assembly, end-plate 99 in FIGS. 38, 39, 73, 74, with a detailed view provided in FIG. 72, usually incorporates a membrane slit valve, but not the gas pressure equalization vent or outlet holes 92 such as shown in FIGS. 41 thru 45. Since the airgun chamber must be airtight to prevent the loss of propulsive gas pressure, the proximal end (end-plate) of the barrel-assembly may be seen as redundant in this airtightness, which is precautionary.

More specifically, as clarified in the section above entitled Airgun and Electrical Connections and Controls of Barrel-assemblies by Functional Type, an ablation or angioplasty-incapable barrel-assembly is never used without its proximal end engaged in the airgun chamber. Reciprocally, so long as it remains in separate use during an angioplasty, an angioplasty-capable barrel-assembly never performs a discharge function as to generate internal pressures that must be dissipated within it to conserve propulsive gas pressure and to avoid gas embolism if discharged in the vascular tree. A barrel-assembly of latter type is provided with a slit-valve of a stiffer elastomeric sheeting material at its end-plate to allow entry into the central canal for use as a service-channel and affords an opening for a cooling catheter.

When engaged in the airgun chamber, the latter makes the proximal end of the barrel-assembly airtight. The end-plate fixes the barrel-tubes in position for exact alignment with their respective holes in the rotary magazine clip. Electrical conductors 97 that course through the longitudinal axis of the barrel-catheter exit proximally through central aperture 100, with the conductors passing radially in bonded relation to the face of end-plate 99 to end on terminal 101. End-plate 99, molded in any suitable plastic, such as polyethylene, polyethylene terephthalate, or polystyrene, contains a simple slit valve made of elastomeric sheet material, such as polyurethane, chlorosulfonated polyethylene, silicone, or fluorosilicone.

The slit valve serves both to relieve excess pressure in the peribarrel space and as an entryway through which to admit a test rod, lubrication injection catheter, or turret-motor and/or electromagnet assembly rapid cooling catheter (cooling capillary catheter) when necessary, as addressed above in the section entitled Cooling Catheters (Temperature-changing Catheters). For nonthermal angioplasty using side-brushes (above and below), the turret-motor is connected to the drive control electronics to rotate the muzzle-head only when the anatomy makes manual rotation difficult or risky.

Except that when the turret-motor stator has just been used as a heating element for thermal angioplasty, a brief interval must be allowed for cooling, end-plate connection of the turret-motor positional drive control electronics has the advantage of allowing a barrel-assembly that battery powered is nontethered and otherwise independent of the airgun to be immediately and intermittently connected to the drive controls only when the turret-motor is needed for rotation. During discharge, the turret-motor must be connected to the drive control electronics. Alternatively, the electrical connection of the barrel-assembly can be by means of terminals on the side of the barrel-assembly just distal to the proximal length of it inserted into the airgun barrel.

VII2e(6). Electrical Connection of the Barrel-Assembly to the Airgun

Turning now to FIGS. 74 and 75, barrel-tubes 74 must be positioned in proper alignment with their respective miniball loading holes in rotary clip 15. Clip 15 forcibly rotated by pawl 49 in FIGS. 31 and 32, making end-plate 99 or facing (veneering) it with polytetrafluoroethylene—except inside the miniball loading holes as would militate against miniball retention—allows flush abutment of end-plate 99 against the front of rotary clip 15 without impeding its rotation. To allow an ablation and angioplasty-incapable radial discharge barrel-assembly without an inmate power source to be removed and reinserted from the airgun for occasional manual use independently of the airgun without concurrent disconnection from the airgun power supply and a loss of power, electrical connection of the barrel-assembly within the airgun chamber is made to the electrical contacts within the airgun chamber by placement of connecting cable 109 in FIG. 75 on the outside of the barrel-assembly distal to or in front of its junction with the barrel of the airgun.

Mounting a rechargeable battery pack local to the electrical terminals at the outside of the barrel-assembly allows both the removal and reinsertion of the barrel-assembly as needed without the need for an external cable that dangles at the side if only when the barrel-assembly is inserted in the airgun when this is of little if any consequence. Whether the result is equivalent to an ablation and/or angioplasty-capable barrel-assembly depends upon the type and number of radial projection units built into the barrel-assembly or added by ensheathment within a combination-form radial projection catheter as constitutes a bipartite or duplex barrel-assembly.

Eliminating the need to remove the barrel-assembly from the airgun and connect it to a separate power supply or battery pack, then disconnect the power source and reinsert the barrel-assembly into the airgun, an external cable of adequate length that maintains connection to the airgun power supply throughout allows quicker alternation between use of the barrel-assembly for discharge and independent use than does either a power supply or battery. Intermittent 'touch-up' ablation, angioplasty, or drug delivery as necessary is thus quickly interjected during discharge implantation. Since free removal from and reinsertion into the airgun of the barrel-assembly without a loss of power requires that end-plate 99 remain clear, electrical connection of the external cable is through a set of electrical terminals mounted to the side of the barrel-assembly.

For visual clarity, FIG. 72 shows electrical terminal 101, which is brought into contact when the barrel-catheter is fully flush within the airgun chamber as shown in FIG. 74 and rotated at the twist to lock connector at the airgun muzzle, as thicker than actual; in order not to protrude as would require splining the airgun barrel, terminal 101 is actually countersunk into the wall of barrel-catheter 72. With such an electrical connection, the twist to lock connector shown in FIG. 73 consisting of stop and twist to lock lock ring 75 and muzzle fitting 103 establishes the correct rotational angle not only for aligning the barrels but also brings the electrical terminal shown or a multiplicity thereof into contact.

Simple pipe barrel-catheters such as those shown in FIGS. 31 thru 33 require no turret-motor, but are equipped with a tractive recovery electromagnet with antechamber trap assembly that requires connection to the airgun power supply by means of a two-conductor cable. Any of the exemplary connector types specified below for six conductor connectors, to include former military specification C-5015 subminiature D type connectors containing two conductors for each trap-extraction electromagnet, can be used. Power can also be drawn from a separate power supply or battery attached proximally to the barrel-catheter. This is usual with a simple air pistol that has been modified for interventional use as addressed above in the section entitled Simple Airgun Modified to Allow Limited Application, for example, but not in special-purpose interventional airguns.

In a modified air pistol, the electrical cable is continued down the front of the pistol grip to a separate power supply. In an interventional airgun built for that purpose, the power supply is contained within the same cabinet as the other components, with thermal insulation, heat sinks, and physical separation used to isolate sources that generate conflicting temperatures. The two wire conductor plugs into a socket toward the proximal end of the barrel-assembly where the latter exits past the outside of the airgun barrel. The wire is fixed to the underside of the barrel-catheter with cyanoacrylate cement, or a DYMAX Corporation 200-CTH-series cement. As with the electrical connection to a radial discharge or multiple barrel barrel-assembly, rather than allowed to drop from the side of the barrel-catheter, the wire or cable is held by clamps to the actuation handpiece or pistol grip.

The multiple barrel barrel-assembly has a turret-motor and trap-extraction electromagnet assembly, each of which must be independently controllable. The conventional six-conductor with circular connectors or discrete wire ribbon cable connected to the remote power supply contains two wires each for the turret-motor and each of the tractive electromagnets and terminates in a plug, which can be of the strip header or long latch and eject header kind. In a multibarrel radial discharge barrel-assembly such as those shown in FIGS. 39, 48, 49, 65, and 66, cable 97 shown in FIG. 75 includes eight-conductors and passes down through central channel 155, shown occupied by a laser 169 in FIG. 66, of the barrel-assembly to electrical terminal board 106.

Terminal board 106 mounted to the outside of the barrel-assembly at a small distance from the airgun muzzle includes eight points of connection or contact posts, preferably of the phono pin plug and jack type for quick changes midprocedurally as necessary, of which two each are for the turret-motor, two each for either separately adjustable electromagnet, and two are to actuate the radial projection unit. Once fully inserted into the airgn barrel, the entire slack of cable 109, centered on twist-to-lock connector consisting of 103 and 75 above, hangs down at the side of the airgun barrel. The slack is usually disregarded. If preferred, the slack is taken up by a small wire take-up spring reel that to avoid impeding the operator applies no greater retractive force than necessary.

The spring reel (not shown) is mounted to the airgun chamber close to a connection board and connectors similar to that on the barrel-assembly 106 thus connecting to the airgun power supply. Clip hangers 110 permanently affixed to the underside of the airgun barrel support the slack as it is taken up by the spring reel. This representation must be exemplary, the number of conductors actually required depending upon the number of components, the operative modes of each, and controls necessary to adjust these. When the type airgun is always paired with ablation and ablation or angioplasty-capable barrel-assemblies requiring the same number of connections, the separate plugs and jacks are replaced with a single multi pin plug and socket that makes and breaks the different connections at once and thus quickly.

For a barrel-assembly requiring 8 connections, an 8-pin DIN connector is used. A turret-motor, for example, can be used only as a mover or also as a heating element. Distad, the wires for the electromagnets continue past the port portion of the muzzle-head through the nose or anterport projection. These barrel and electrical connections end on the proximal outer surface of the barrel-assembly with a six-contact terminal which receives these lines from the remote power supply. While the trap-extraction electromagnets use ceramic woven insulated silver wire to generate magnetic field intensities sufficient to extract mispositioned miniballs despite their small size, the conductors connected to these are of greater gauge and not susceptible to melting by heat conduction.

The 6 conductor-3 pair plug and socket may be any of many kinds, to include those stated above for ribbon cable; minirectangular; modular; or registered RJ12 or RJ25. These electrical lines connect on the outside of the receiver-barrel-assembly junction by means of connectors. The power supply of a modified airgun is remote, whereas that in a dedicated airgun is an integral component. Inside the barrel-assembly, the cable is not ribbon but round and courses distad through the central canal defined by the barrel-tubes, the four conductors for the trap-extraction electromagnets continuing through the center of the muzzle-head splay chamber.

VII2f. Radial Discharge Barrel-Assembly Elements

VII2f(1). Tube Polymer Nonintrinsic Barrel-Catheter Flexibility (Bendability, Trackability) Setting and Altering Elements VII2f(1)(a). Tubing Materials for Barrel-Catheters and Radial Discharge Barrel-Tubes Suitable tubing for the barrel-catheter and the barrel-tubes that it conducts pose numerous possibilities. Depending upon the diameter of the ductus, hence, barrel-assembly, the number of barrel-tubes can be from one to four or more, and can be separate as to pass at variable radii from the center, or coextruded as a multiple-lumen tube of which the luminal tubes are separable for outward flaring toward the distal end. The incorporation of a. Blood-tunnels, as described below in the section entitled Hypoxia and Ischemia-averting Elements, 2. Blood-tunnels, and b. The spacing apart of non-coextruded barrel-tubes by means of centering devices, as described below in the section entitled Centering Devices (Centering Disks), introduces stiffness that must take the corresponding detraction in barrel-assembly intraoperative bendability (trackability) into account.

The number and type of these elements must therefore be coordinated with the other factors that affect trackability, such as the tube polymers, their wall thicknesses, diameters, and the distances from the longitudinal central axis of the barrel-catheter of the barrel-tubes. Depending upon the dimensions, rigidity, frictional character, and so on, sought in a given type of barrel-assembly, the material, or if coextruded or coated, the materials of the tubes in that type of barrel-assembly, are chosen on the basis of empirical testing. The central canal in a center-discharge barrel-assembly or any available barrel-tube in either a center or edge discharge barrel-assembly can be used to insert a hollow tube or solid rod of a diameter less than that of the path taken made of any polymer free of polymerization residue to alter the flexibility of the barrel-assembly at any time whether before or after entry into the body or before or after reaching the site for treatment, to include a cooling catheter or cooling capillary catheter as described below.

The torque ratio or twisting characteristic of the barrel-catheter can be increased with relatively little effect on flexibility by bonding the centering devices to the inner surface of the barrel-catheter. The tubing in any barrel-assembly should be neither so pliant as to bend with little lateral force and thus change the rolling resistance as to necessitate constant adjustment of the airgun, which invites human error, nor so stiff that the bends encountered with either brachial or femoral entry cause it to kink or injure the lumen wall. For transluminal advancement by the linear positioning table, bending is prevented by a sheathing about the extracorporeal length.

The tubing of the barrel-catheter 44 can be made of any of a number of materials, to include compound (coextruded) tubing to provide, for example, polytetrafluoroethylene within nylon, polytetrafluoroethylene within vinyl, polytetrafluoroethylene or nylon inside with polytetrafluoroethylene or medical grade vinyl outside, or an internal thin coating or thicker layer of polytetrafluoroethylene for 'bore' slipperiness and overall stiffness, coextruded with an outer layer of any of numerous materials, such as expanded polytetrafluoroethylene, Pebax®, or Tygon® S-50-HL for pliancy and soft contact with the larynx and tracheal lumen. Varying the relative thickness of each of these layers allows a continuous wide range of complementary pliancies and torqueabilities in the simple pipe barrel-catheter. Barrel tubing materials having a higher coefficient of friction recommend an inside barrel lining coat of polytetrafluoroethylene.

Polytetrafluoroethylene within vinyl, for example, affords relatively greater pliancy, but at the expense of stiff torqueability and greater friction. Nonessential bends in the barrel-catheter proximal to the patient will increase the rolling resistance for and reduce the exit velocity of the miniballs. To minimize nonaxial discharge, the least sufficient length of barrel-catheter between patient and airgun that allows the free manipulation of the barrel-assembly should be used. That is, the barrel-assembly should be as short as practicable. The incorporation into the muzzle-head of a 'chronometer' to actuate an alarm when as the result of rolling resistance, miniball velocity drops below a certain value, is discounted due to the lack of space available distal to the front of the electromagnet.

Whereas a radial discharge barrel-assembly will generally be used for high density implantation necessitating leveling of the extracorporeal length for use of the automatic interval increment table, with a simple pipe barrel-assembly, monitoring for bends in the barrel-catheter to prevent reductions in exit velocity can be directly and practicably accomplished by incorporating piezoresistive or optical fiber strain gauges along the barrel-assembly at intervals over the proximal length that remains outside the patient. A threshold excessive output voltage generated within these can be made to actuate an audible alarm.

However, vigilance by members of the operating team to any more than slight changes in the conformation of the barrel-assembly obviates the additional cost for a hyperflexed condition detection and alarm system. The 'bore' of the barrel-catheter varies with that of the miniballs to be discharged, generally ranging between 1.0 and 2.1 millimeters. Regardless of the procedure or type barrel-assembly in use, once the apparatus has been positioned and is in use, further movement, much as with a dental hand-piece, is slight and substantially limited to the working end or muzzle-head. The airgun is adjusted for the conformation of the barrel-catheter, and significant deviations from this conformation must be noted and the procedure interrupted to change the adjustment.

That once in use movement is limited to a short length of the barrel-assembly toward the distal end does not justify the interposition of a section of tubing that differs in pliancy from the rest. To assist in orientation and the gauging of distances, radiopaque calibrative markings are applied along the outside of the pipe by etching and applying tantalum. If the outside of the barrel-catheter is made of polytetrafluoroethylene, Acton Technologies, Inc. FluoroEtch® or W.L. Gore® and Associates, Inc. Tetra-Etch® or blown-ion air plasma type corona, or flame surface treated, for example, is used to prepare by scarifying the surface for improved adhesion of the tantalum coating. Further details regarding the mechanical connection, and the electrical connection, of the barrel-assembly to the airgun are described below.

VII2f(1)(b). Centering Devices (Centering Disks)

For fixing barrel-tubes in radial distance from the central axis of the barrel-catheter, a centering (or 'centring') device, as shown for use in a four-way radial discharge barrel-assembly in FIGS. 43 thru 45, is used. FIG. 42 shows a partially cross-section of a four-barrel radial-discharge barrel-assembly through a centering device taken along line G-G' in FIG. 41 where bilateral blood-tunnels 96 are shown in FIG. 42 as off-section and receding into the distance and peribarrel space 98 omitted as displaced by the blood-tunnels at the level depicted.

In FIGS. 43 thru 45, centering devices have a central hole 90 to pass the electrical conductor for supplying electrical or fluid power to the turret-motor and tractive electromagnets, barrel-tube holes 91 to pass the barrel-tubes, and gas pressure equalizing perforations 92, which allow the discharge pressure that escapes through the perforations in the length of the barrel-tubes within the body to access the entire peribarrel space 98 in FIGS. 48 and 49 as but overlain in the view of FIG. 42 and so become equalized within the barrel-catheter.

In a barrel-assembly with either a center- or edge-discharge muzzle-head that allows a cabled device such as a fiberoptic endoscope or laser to be passed down through the central channel to the nose, such as shown in FIG. 66, the centering devices include a center hole 90 of the larger diameter required, with side-holes then used for electrical or fluid conductors. Incorporation into the barrel-assembly of a central cabled device such as a fiberoptic endoscope or laser necessitates a larger center hole in the centering devices shown in FIGS. 43 thru 45 and a center hole in the nose as shown in FIG. 67 for a combination-form barrel-assembly that allows the exchanging of cabled devices during use.

FIG. 39 provides a side view of centering devices 95 along line G-G— as well as a blood-tunnel 96 along line F-F' in a two- or four-barrel radial discharge barrel-assembly where these have been longitudinally separated as not to superimpose. FIG. 41 then brings these together where the views along lines F-F' and G-G' in FIG. 39 could be longitudinally condensed and allow detail. At intervals along the barrel-assembly sufficient to prevent sagging of the barrel-tubes, the outer edges of the centering devices are bonded to the inside of the barrel-catheter, and the edges of the holes for the barrel-tubes 91 are bonded to the barrel-tubes by means of an adhesive. The center hole 90 when used to pass through wire insulation is not bonded.

Depending upon the materials of which the centering device, barrel-tubes, and barrel-catheter are made, the adhesive used is, for example, NuSil Technologies MED-1037 or MED3-4013, DYMAX Corporation 200-CTH-series cement, cyanoacrylate cement, Master Bond® EP42LV, or Loctite Hysol Cool Melt®. By allowing the radial spacing among the barrel-tubes to be increased as in FIG. 44, the centering devices not only keep the lines passing through at a constant distance from one another and the barrel-catheter but allow the flexibility as well as the torque ratio of the barrel-assembly to be reduced.

Along with the materials, which can be coextruded, and thickness of the barrel-catheter and barrel-tubes, this factor is used to reduce the tendency of portions of the barrel-assembly outside the body to flex and thus increase the rolling resistance to discharge of the miniballs. Trackability and the tendency to sag both due to flexibility, the number of centering devices used, whether these are made of less elastic material and glued to all tubes in contact can be used to adjust the flexibility if the barrel-assembly. A sufficient number where all are glued allows the barrel-assembly to support itself without sagging over shorter distances but reduces trackability but may not be adequate to negate the need for the antisag linkage device shown in FIG. 78 during automatically positioned discharge.

For barrel-tubes of given hardness, gradually reducing their radial distances as the leading or distal end of the barrel-assembly is approached enhances trackability around anatomical bends. If extended proximad past elastomeric joint 111 in FIGS. 48, 49, 65, and depending upon the flexibility of the cabled device, FIG. 66, the pressure equalization perforations in and toward the distal ends of the barrel-tubes contributes to flexibility as well. Flexibility and torque ratio can be adjusted over a wide range not just over the entire length but over different segments of the barrel-assembly according to the longitudinal interval separating the centering devices and whether these are bonded to the internal surface of the barrel-catheter and other lines that pass through.

Usually this is used to reduce the tendency for the extracorporeal length of the barrel-catheter to fold at the entry portal when the operator lets go, especially when the slidable power and control housing of an ablation or ablation and angioplasty-capable barrel-assembly is not advanced to the body so that the barrel-catheter folds under its weight. long with the materials and dimensions of the parts of the barrel-assembly and whether these are bonded, the flexibility and torqueability, or resistance to longitudinal twisting, of the barrel-assembly can be adjusted over the entire length of the barrel-assembly or different segments by gradually changing the radial spacing of the barrel-tubes.

This is done by using centering devices that incrementally separate (diverge, radially spread apart) or more centrally gather (converge) the barrel-tubes, as shown most convergent in FIG. 43 and least convergent in FIG. 44. To create paths for blood to pass, metal in the spindle distal to the spindle neck journaled in the through-bore rotor of the turret-motor is removed. The peripheral openings to these passages or blood-ports are machined for continuity with the blood-grooves described below that course longitudinally along the outside of the muzzle-head. Yet another method for obtaining greater flexibility with a given combination of barrel-tubes over the entire length or segments of the barrel-assembly is to reduce the diameter of the barrel-catheter.

When the barrel-catheter is not made thus, larger and smaller diameter barrel-catheters are joined by telescoping the end of the narrower into the wider, the joint bonded with an adhesive or by welding and externally bevelled and rounded to prevent abrasion of the lumen wall. Joining segments that differ in diameter such that these are not directly interdigitable or telescopable but sufficiently different as to necessitate the insertion of tubing of intervening diameter or pressure-sensitive tape is discouraged as likely to result in seizing or rubbing of the joint against the lumen wall regardless how ledgeless or nonabrupt the outer surface. If necessary, an external hand-held electromagnet is used to assist in steering the muzzle-head through sharper turns by attracting the turret-motor and magnet cores in the otherwise nonmagnetic muzzle-head.

The barrel-assembly is made stiffer by 1. Using a barrel-catheter of larger diameter, 2. Making the barrel-tubes and barrel-catheter of stiffer materials, 3. Distancing the barrel-tubes farther radially from the longitudinal axis, and 4. Incorporating blood-tunnels, as described below. Incorporation into the barrel-assembly of a photo-ablation laser also adds stiffness. The caliber of the implants is decided purely on the basis of the medical requirement and never manipulated merely to change the stiffness of the barrel-assembly. Change in these factors also changes the torque ratio of the barrel-assembly, which is further variable by leaving the outer edges of the centering devices unbonded or bonded to the internal surface of the barrel-catheter.

VII2f(2). Embolic Trap Filter in Radial Discharge Muzzle-Heads for Use in the Vascular Tree Preemptive angioplasty with the heat-windows and/or laser built into the muzzle-head should completely disintegrate any debris released from the fracture of vulnerable plaque by contact with the muzzle-head. Furthermore, since the muzzle-head discharges to the side and extends forward of the miniball exit-holes, a miniball cannot be discharged in the forward direction. However, in any off-pump procedure, should the recovery electromagnets remain unenergized through human error, a miniball that becomes loose between the side of the muzzle-head and the intima will be carried forward by the bloodstream. Since forward movement by this mean retains none of the momentum of discharge as would perforate it, a run-ahead or distal embolic filter can remain deployed throughout discharge to provide additional protection not only against thromboembolism but embolization by a miniball.

By intercepting and holding any miniball that would otherwise pass downstream, the filter supports the recovery electromagnets and any prepositioned external electromagnet midprocedurally. An impasse-jacket adds yet another means for trapping a miniball that enters the circulation midprocedurally, but is one that remains effective over any interval following the procedure. Most studies indicate that despite increased procedural time, the risk of special complications, and additional expense, distal embolic protective filters are withal beneficial (see section 4d(2) entitled Ductus Wall Tumefacients and Sprouse, L. R., Peeters, P., Bosiers, M. 2005. "The Capture of Visible Debris by Distal Cerebral Protection Filters During Carotid Artery Stenting: Is It Predictable?," *Journal of Vascular Surgery* 41(6):950-955; Wholey, M. H., Jarmolowski, C. R., Wholey, M. and Eles, G. R 2003. "Carotid Artery Stent Placement—Ready for Prime Time?," *Journal of Vascular and Interventional Radiology* 14(1): 1-10).

At the same time, others have shown that by causing intimal abrasion and denudation, distal filters actually generate much thromboembolic debris (see, for example, section 4d(2) entitled Ductus Wall Tumefacients and Müller-Hülsbeck, S., Stolzmann, P., Liess, C, Hedderich, J., Paulsen, F., Jahnke, T., and Heller M. 2005. "Vessel Wall Damage Caused by Cerebral Protection Devices: Ex Vivo Evaluation in Porcine Carotid Arteries," *Radiology* 235(2): 454-460; Maleux, G., Demaerel, P., Verbeken, E., Daenens, K., Heye, S., Van Sonhoven, F., Nevelsteen, A., and Wilms, G. 2006. "Cerebral Ischemia After Filter-protected Carotid Artery Stenting is Common and Cannot be Predicted by the Presence of Substantial Amount of Debris Captured by the Filter Device," *American Journal of Neuroradiology* 27(9): 1830-1833). Vasospasm, dissection, and guidewire entrapment have been reported (Vijayvergiya, R., Otaal, P. S., Bagga, S., and Modi, M. 2010. "Symptomatic Carotid Vasospasm Caused by a Distal-protection Device during Stent Angioplasty of the Right Internal Carotid Artery," *Texas Heart Institute Journal* 37(2):226-229).

The current consensus favors the use of a distal embolic protective filter when preliminary intraductal ultrasonography, computer-assisted pixel distribution analysis of duplex ultrasound scan images, palpography, thermography, catheter-based thermography, near-infrared spectroscopy, angioscopy indicates the presence if not the fine structure of vulnerable plaque (but see Wolff, M. R., Resar, J. R., Stuart, R. S., and Brinker, J. A. 1993. "Coronary Artery Rupture and Pseudoaneurysm Formation Resulting from Percutaneous Coronary Angioscopy," *Catheterization and Cardiovascular Diagnosis* 28(1):47-50), digital subtraction angiography, magnetic resonance imaging, computed tomography, multi-slice spiral computed tomography, nuclear methods, endoluminal means of imaging, or optical coherence tomography (see, for example, Lee, J. M., Bang, J. I., Koo, B. K., Hwang, D., Park, J., and 7 others 2017. "Clinical Relevance of 18F-Sodium Fluoride Positron-emission Tomography in Noninvasive Identification of High-risk Plaque in Patients with Coronary Artery Disease," *Circulation. Cardiovascular Imaging* 10(11). pii: e006704; Bec, J., Phipps, J. E., Gorpas, D., Ma, D., Fatakdawala, H., and 3 others 2017. "In Vivo Label-free Structural and Biochemical Imaging of Coronary Arteries Using an Integrated Ultrasound and Multispectral Fluorescence Lifetime Catheter System," *Scientific Reports* 7(1):8960; Wieringa WG1, Lexis CP1, Lipsic E1, van der Werf HW1, Burgerhof JG2, and 9 others 2017. "In Vivo Coronary Lesion Differentiation with Computed Tomography Angiography and Intravascular Ultrasound as Compared to Optical Coherence Tomography," *Journal of Cardiovascular Computed Tomography* 11(2):111-118; Lee, J. H., Hwang, Y. N., Kim, G. Y., Shin, E. S., and Kim, S. M. 2017. "Analysis of Cardiovascular Tissue Components for the Diagnosis of Coronary Vulnerable Plaque from Intravascular Ultrasound Images," *Journal of Healthcare Engineering* 2017:9837280; Costopoulos, C., Brown, A. J., Teng, Z., Hoole, S. P., West, N. E., Samady, H., and Bennett, M. R. 2016. "Intravascular Ultrasound and Optical Coherence Tomography Imaging of Ccoronary Atherosclerosis," *International Journal of Cardiovascular Imaging* 2016 32(1): 189-200; Ma, T., Zhou, B., Hsiai, T. K., and Shung, K. K. 2016. "A Review of Intravascular Ultrasound-based Multimodal Intravascular Imaging: The Synergistic Approach to Characterizing Vulnerable Plaques," *Ultrasonic Imaging* 38(5):314-331; Celeng, C., Takx, R. A., Ferencik, M., and Maurovich-Horvat, P. 2016. "Non-invasive and Invasive Imaging of Vulnerable Coronary Plaque," *Trends in Cardiovascular Medicine* 26(6):538-547; Ma, D., Bec, J., Yankelevich, D. R., Gorpas, D., Fatakdawala, H., and Marcu, L. 2014. "Rotational Multispectral Fluorescence Lifetime Imaging and Intravascular Ultrasound: Bimodal System for Intravascular Applications," *Journal of Biomedical Optics* 19(6):066004; Bec, J., Ma, D. M., Yankelevich, D. R., Liu, J., Ferrier, W. T., Southard, J., and Marcu, L. 2014. "Multispectral Fluorescence Lifetime Imaging System for Intravascular Diagnostics with Ultrasound Guidance: In Vivo Validation in Swine Arteries," *Journal of Biophotonics* 7(5):281-285; Ren, J., Zhang, J., Xu, N., Han, G., Geng, Q., and 4 others 2013. "Signature of Circulating MicroRNAs as Potential Biomarkers in Vulnerable Coronary Artery Disease," *Public Library of Science One* 8(12):e80738; García-García, H. M., Gonzalo, N., Granada, J. F., Regar, E., and Serruys, P. W. 2008. "Diagnosis and Treatment of Coronary Vulnerable Plaques," *Expert Review of Cardiovascular Therapy* 6(2):209-222; Schaar, J. A., Mastik, F., Regar, E., den Uil, C. A., Gijsen, F. J., and 3 others 2007. "Current Diagnostic Modalities for Vulnerable Plaque Detection," *Current Pharmaceutical Design* 13(10):995-1001; Hamdan, A., Assali, A., Fuchs, S., Battler, A., and Kornowski, R. 2007. "Imaging of Vulnerable Coronary Artery Plaques," *Catheterization and Cardiovascular Interventions* 70(1):65-74; Saia, F., Schaar, J., Regar, E., Rodriguez, G., De Feyter, P. J., and 8 others 2006. "Clinical Imaging of the Vulnerable Plaque in the Coronary Arteries: New Intracoronary Diagnostic Methods," *Journal of Cardiovascular Medicine* (Hagerstown, Md.) 7(1):21-28; Schaar, J. A., Mastik, F., Regar, E., den Uil, C. A., Gijsen, F. J., Wentzel, J. J., Serruys, P. W., and van der Stehen, A. F. 2007 "Current Diagnostic Modalities for Vulnerable Plaque Detection," *Current Pharmaceutical Design* 13(10):995-1001; Hamdan, A., Assali, A., Fuchs, S., Battler, A., and Kornowski, R. 2007 "Imaging of Vulnerable Coronary Artery Plaques," *Catheterization and Cardiovascular Interventions* 70(1):65-74).

In light of these findings and the fact that the incorporation of a trap-filter, even without the additional incorporation of radial projection units, reduces working depth down the vascular tree, the selection of a barrel-assembly that incorporates a trap-filter must rest upon clinical judgment made on a case by case basis through preliminary imaging of the specific condition to be treated. Since the apparatus described herein are not limited to use in the vascular tree, distal protection is not appropriate in every application or embodiment. However, the use of radial projection unit side-sweeping tool-insert brushes in the vascular tree would generate debris that an improved filter should eliminate without generating debris of its own. The release of debris by contact of the arterial wall with the muzzle-head is discussed below in the section entitled Thermal ablation or angioplasty- (Lumen Wall Priming Searing- or Cautery-) capable Barrel-assemblies.

Thus, at least the location and method for incorporating a filter into different embodiments to be described should be shown, regardless of whether a filter is actually incorporated in any one. Accordingly, this unresolved controversy is resolved by providing for the incorporation of a trap-filter in each of the various embodiments to be described. When not used following an angioplasty and on the first entry pass with an angioplasty-capable barrel-assembly, a muzzle-head with heat-window nose-cap can be used to release heat to the surrounding lumen wall preempting the release of potentially embolizing debris. When concern for the presence of vulnerable plaque distad to its reach is not an issue, the trap-filter can also be deployed to protect against the release of embolizing debris. Filter deployment is also independently controllable and the filter membrane selected for resistance to modification in material properties by exposure to the release of heat from the nose.

A number of recent advancements have been made toward the noninvasive detection of vulnerable plaque, to include multidetector row or multislice computed tomography scanning with iodinated nanoparticles dispersed with surfactant in a product called N1177 produced by Nanoscan Imaging of Lansdale, Pa. as contrast agent (see Hyafil, F., Cornily, J. C., Feig, J. E., Gordon, R., Vucic, E., Amirbekian, V., Fisher, E. A., Fuster, V., Feldman, L. J., and Fayad, Z. A. 2007. "Noninvasive Detection of Macrophages Using a Nanoparticulate Contrast Agent for Computed Tomography," *Nature Medicine* 13(5):636-641). Vulnerable plaque contains more macrophages and is higher in temperature and acidity than healthy arterial wall tissue. Means had already existed to detect plaque as reasonably prognostic for an acute event (see, for example, Gronholdt, M-L. M., Nordestgaard, B. G., Schroeder, T. V., Vorstrup, S., and Sillesen, H. 2001. "Ultrasonic Echolucent Carotid Plaques Predict Future Strokes," *Circulation* 104(1):68-73).

Newer noninvasive imaging methods can make arterial inflammation, neovascularization of the vasa vasorum, and/ or the extent of stenosis clear enough to signal the need for deploying a distal embolic protective filter. These include:

a. The use of gas filled microbubbles as ultrasonic contrast agents (see, for example, Feinstein, S. B. 2006. "Contrast Ultrasound Imaging of the Carotid Artery Vasa Vasorum and Atherosclerotic Plaque Neovascularization," *Journal of the American College of Cardiology* 48(2):236-243; Feinstein, S. B. 2004. "The Powerful Microbubble: From Bench to Bedside, from Intraductal Indicator to Therapeutic Delivery System, and Beyond," *American Journal of Physiology. Heart and Circulatory Physiology* 287(2):H450-H457; Dayton, P. A and Rychak, J. J. 2007. Molecular Ultrasound Imaging Using Microbubble Contrast Agents," *Frontiers in*

*Bioscience* 12:5124-142; Kaufmann, B. A. and Lindner, J. R. 2007. "Molecular Imaging with Targeted Contrast Ultrasound," *Current Opinion in Biotechnology* 18(1):11-16).

b. Magnetic molecular resonance imaging with gadopentetic acid (gadopentetate dimeglumine, Gd-DTPA) contrast agent (Briley-Saebo, K. C., Mulder, W. J., Mani, V., Hyafil, F., Amirbekian, V., Aguinaldo, J. G., Fisher, E. A., and Fayad, Z. A. 2007. "Magnetic Resonance Imaging of Vulnerable Atherosclerotic Plaques: Current Imaging Strategies and Molecular Imaging Probes," *Journal of Magnetic Resonance Imaging* 26(3):460-479; Amirbekian, V., Lipinski, M. J., Briley-Saebo, K. C., Amirbekian, S., Aguinaldo, J. G., Weinreb, D. B., Vucic, E., Frias, J. C., Hyafil, F., Mani, V., Fisher, E. A., Fayad, Z. A. 2007. "Detecting and Assessing Macrophages in Vivo to Evaluate Atherosclerosis Noninvasively Using Molecular MRI," *Proceedings of the National Academy of Sciences of the United States of America* 104(3): 961-966). c. Multichannel, high-resolution laser scanning fluorescence microscopy (see Pande, A. N., Kohler, R. H., Aikawa, E., Weissleder, R., and Jaffer, F. A. 2006. "Detection of Macrophage Activity in Atherosclerosis in Vivo Using Multichannel, High-Resolution Laser Scanning Fluorescence Microscopy," *Journal of Biomedical Optics* 11(2): 021009), d. Intraductal fluorescence spectroscopy (see Tawakol, A., Castano, A. P., Anatelli, F., Bashian, G., Stern, J., Zahra, T., Gad, F., Chirico, S., Ahmadi, A., Fischman, A. J., Muller, J. E., and Hamblin, M. R. 2006. "Photosensitizer Delivery to Vulnerable Atherosclerotic Plaque: Comparison of Macrophage-targeted Conjugate Versus Free Chlorin(e6)," *Journal of Biomedical Optics* 11(2):021008.).

e. Positron emission tomography (Tawakol, A., Migrino, R. Q., Bashian, G. G., Bedri, S., Vermylen, D., Cury, R. C., Yates, D., LaMuraglia, G. M., Furie, K., Houser, S., Gewirtz, H., Muller, J. E., Brady, T. J., and Fischman, A. J. 2006. "In Vivo 18F-fluorodeoxyglucose Positron Emission Tomography Imaging Provides a Noninvasive Measure of Carotid Plaque Inflammation in Patients," *Journal of the American College of Cardiology* 48(9):1818-1824; Elmaleh, D. R., Fischman, A. J., Tawakol, A., Zhu, A., Shoup, T. M., Hoffmann, U., Brownel,1 A. L., and Zamecnik, P. C. 2006. "Detection of Inflamed Atherosclerotic Lesions with Diadenosine-5',5'''-P1,P4-tetraphosphate (Ap4A) and Positron-emission Tomography," *Proceedings of the National Academy of Sciences of the United States of America* 103(43): 15992-15996).

f. Multidetector-row computed tomography (Alasnag, M., Umakanthan, B., and Foster, G. P. 2008. "Accurate Determination of High-risk Coronary Lesion Type by Multidetector Cardiac Computed Tomography," *Journal of Invasive Cardiology* 20(7):361-363; Mowatt, G., Cummins, E., Waugh, N., Walker, S., Cook, J., Jia, X., Hillis, G. S., and Fraser, C. 2008. "Systematic Review of the Clinical Effectiveness and Cost-effectiveness of 64-slice or Higher Computed Tomography Angiography as an Alternative to Invasive Coronary Angiography in the Investigation of Coronary Artery Disease," *Health Technology Assessment* 12(17):iii-iv, ix-143).

To prevent the passage downstream of dislodged atherothrombogenic debris as would result in distal embolization, deployment of shaving or brush-type tool-inserts is accompanied by the automatic deployment of a distal embolic protective trap-filter. The filter deployment mechanism is part of the barrel-assembly, no portion thereof discarded. Replacement filters are meant to be discarded after one-time that precedes the expiration date stamped on the package. Replacement filters are packaged after sterilization with ethylene oxide gas and attach toward the distal end of the vanadium permador (vanadium permendur) or silicon iron pin armature (slug, plunger, core) of the subminiature (micro) dc tubular plunger solenoid described in the section that follows. To achieve the necessary force of plunger expulsion, the coil is wound with silver wire. The prepositioning distally of a debris trap is especially important when performing an angioplasty on an artery with chronic total occlusion or a graft, often a saphenous vein, that has become occluded.

In these situations, a principal concern is the release of thromboemboli into the collateral circulation that had sustained perfusion despite the lack of canalization or luminal obstruction (see, for example, Meier, B. 1989 (reprinted 2005). "Angioplasty of Total Occlusions: Chronic Total Coronary Occlusion Angioplasty," *Catheterization and Cardiovascular Diagnosis* 17(4):212-217; Kahn, J. K. 1995 (reprinted 2005). "Collateral Injury by Total Occlusion Angioplasty: Biting the Hand that Feeds Us," *Catheterization and Cardiovascular Diagnosis* 34 (3): 65-66; Stone, G. W., Kandzari, D. E., Mehran, R. Colombo, A, and 23 other authors 2005. "Percutaneous Recanalization of Chronically Occluded Coronary Arteries: A Consensus Document: Part I," *Circulation* 112(15):2364-2372; Stone G W, Reifart N J, Moussa I, Hoye A, Cox D A, Colombo, A., Baim, D. S., Teirstein, P. S., and 19 other authors 2005. "Percutaneous Recanalization of Chronically Occluded Coronary Arteries: A Consensus Document: Part II," *Circulation* 112(16):2530-2537).

Furthermore, chronic total occlusion notably affects the coronary arteries, which grudging of working depth, discourage the use of a transluminal device that requires significant anteport extension longitudinal extension down the lumen. Accordingly, a long filter of the kind proposed in 2003, which sought to combine the strongest features of the best filters then on the market, at the least demands modification for use in the coronary vessels. In both edge and center-discharge barrel-assemblies, the recess or silo for storing the trap-filter and its deployment and retrieval or stowing solenoid is in the nose. The orientation of the recovery electromagnet windings must afford the clearance required. A combination-form muzzle-head, which requires an edge-discharge muzzle-head, without a cabled device such as a rotational burr or laser installed affords the bore or central channel for a trap-filter.

When the central channel will be unavailable, the nose is extended forward (distally) with the trap-filter recess located to a side of the distal terminus of the central channel, or nose-hole. The trap-filter deployment mechanism is disabled while an installed laser is in use. Electrically operated radial projection units, about the periphery of the muzzle-head can be raised into working position during an angioplasty that is performed with a unitary or bipartite angioplasty-capable barrel-assembly where the apparatus remains independent of an airgun unless and until the barrel-assembly is inserted into an airgun to initiate stenting, and must therefore be controllable from the onboard ablation and angioplasty control panel.

However, since trap-filter deployment can also prevent the escape of a miniball whenever the magnetic field strength of the recovery electromagnets must kept to a minimum, angioplasty-incapable radial projection barrel-assemblies whether used in the circulatory system may also justify the incorporation of a trap-filter (Hussain, F., Rusnak, B., and Tam, J. 2008. "Retrieval of a Detached Partially Expanded Stent Using the SpideRX and EnSnare Devices—A First Report," *Journal of Invasive Cardiology*

20(2):E44-E47). While discharge from a radial discharge barrel-assembly would normally never strike the filter element (mesh, membrane, basket), the risk of perforation is reduced by making the mesh thicker and of a material intrinsically strong such as nitinol.

For this reason, a second circuit independent of that used to energize the thermal expansion wires is provided to allow the deployment of the trap-filter independently of the radial projection units, hence, during discharge as added protection against the escape of a miniball into the bloodstream. Since a trap-filter reduces working depth when deployed, it is best stowed when not required but readily deployable and retrievable without the loss of debris. While a combination-form barrel-assembly that incorporates or has temporarily inserted a laser has the ability to disintegrate filter trappable debris, compulsory activation of the laser whenever the side-sweepers are used is unacceptable as posing a risk of perforation—not as destroying the filter it would then supplant.

Trap-filter-deployment solenoid end-of-travel impact shock as would tear the filter membrane and jolt the trap-filter so that the outer nitinol ring kicked the lumen wall, is checked by an elastomeric bumper-washer that surrounds the plunger exit orifice to lightly clutch about the plunger and thus slow down and dampen plunger ejection and spring return. Further to reduce the risk of tears and kicking, one continuous strand of polyurethane suture is diametrically wrapped entirely about the outside of the filter membrane to begin and end at the head of the solenoid plunger.

A second such wrapping around or continuation with the same strand at right angles to the first produces what appear to be four struts. Even though the trap-filter-deployment solenoid is enclosed within the ejection head as to release heat through the muzzle-head nose-cap, the periods of energization (duty cycle) involved would produce thrombogenic temperatures unless the bumper-washer cooperated with the rest of the solenoid recess lining as a thermal insulator, the solenoid is heat-sunk, and the cooling catheter is used to prevent over-, or for that matter, under-heating.

VII2f(2)(a). Trap Filter Deployment and Retrieval Mechanism

In minimally and fully ablation and angioplasty-capable muzzle-heads, the use of a filter conforms to that practiced since the 1970s. As shown in FIG. 50, thicker polyurethane or preferably nitinol filter mesh membrane 170 typically has 120 micrometer pores and is of a length that is recoverable or restowable into silo recess 171 with additional space for retracting several miniballs, albeit improbable of necessity. The trap-filter is deployed and retracted or stowed by microminiature silver wire-wound push- or punching-type solenoid 172 until the removal of current causes the extension spring within solenoid 172 to reseat the armature or plunger causing trap-filter 173 to retract or restow. Trap-filter 173 is separately deployable on demand with an independent switch, but is automatically deployed with depression of the trigger switch or activation of radial projection units 174 in FIGS. 49, 51 thru 63, 65, 66, 71, and 78.

Figure 81:
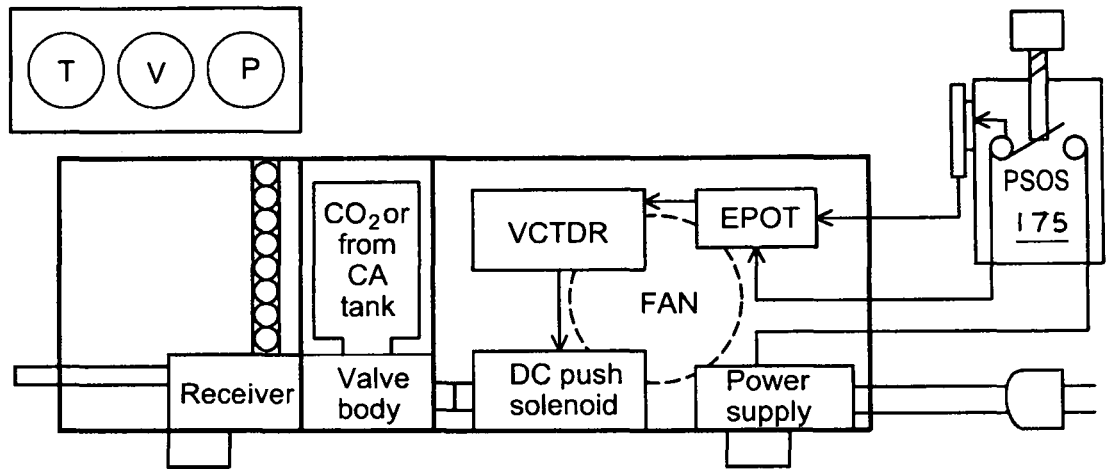
FIG. 81 shows a longitudinal section view of a gravity fed single barrel (single barrel-tube; monobarrel) interventional airgun which incorporates plural control points for adjusting the exit velocity over a range that allows its use for different tissues at different angles and to different depths in quick succession, shown with a plunger or dead-man switch type trigger.
Figure 82:
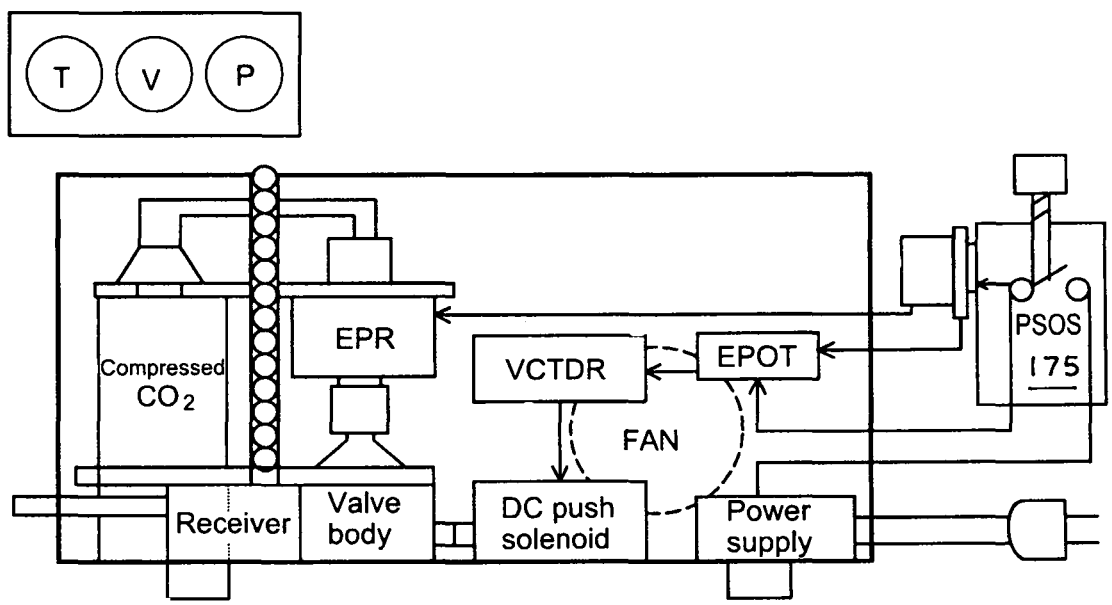
FIG. 82 shows a longitudinal section view of a gravity fed single barrel (single barrel-tube; monobarrel) interventional airgun with exit velocity control points in addition to those incorporated into the airgun shown in FIG. 81 to allow quick midprocedural adjustments, shown with a plunger or dead-man switch dead-man switch type trigger.

On depressing trigger switch 175 in FIGS. 81 and 82, discharge is deferred slightly, typically 5 milliseconds, by a time-delay relay, the signal to filter deployment solenoid 173 sent directly, whereas that for deployment of the radial projection units, incorporated atherectomizer, or discharge following at that interval delayed. With thermal expansion wire-lifted radial projection units as shown in FIGS. 51, 52*a*, 53*a*, and 54 thru 56, the heating interval delay intrinsic in the expansion wire mechanism delays the projection of tool-insert holding and lift-platform (tool holder, tool holding frame) 176 by a sufficient interval for trap-filter 173 to have been deployed, so that trap filter solenoid 172 is energized at the same time as is thermal expansion wire 177.

Self-expanding trap filter mesh membrane 170 frame struts 178, ordinarily made of nitinol wire, allow 360° apposition, or contact of the filter periphery with the lumen wall preventing bypass. To prevent the edges of filter mesh membrane 170 from catching on the rim of the solenoid shaft upon retraction, the filter struts must be peripheral to or outside the outer edge of filter mesh membrane 170. In an ablation and angioplasty-capable barrel-assembly used independently of an airgun, the trap-filter is controlled from the on-board control panel with power drawn from the inmate battery pack with circuitry likewise contained within the slidable onboard power and control housing. By contrast, an airgun-independent ablation or an ablation and angioplasty-incapable barrel-assembly is used independently of an airgun only occasionally.

VII2f(2)(b). Automatic Disabling of Implant-Discharge, Radial Projection Units, and Turret-Motor Barrel-assembly muzzle-head turret-motors are addressed above and radial projection units below in respective sections of like title. When used to perform an ablation or an angioplasty, barrel-assemblies are usually disconnected from the airgun, making accidental discharge impossible. An ablation and angioplasty-capable barrel-assembly can be used for an ablation or an angioplasty while engaged in the airgun; however, the hindrance of remaining connected will almost always prompt disengagement. With ablation and angioplasty-capable barrel-assemblies, the airgun and barrel-assembly control panels are separate, minimizing the risk of accidental discharge.

For use with minimally ablation or ablation and angioplasty-capable barrel-assemblies, the airgun control panel will usually include the ablation or angioplasty controls. Then to prevent an accidental discharge, discharge is mechanically or electrically disabled, the latter by switching off the trigger switch, for example. Such disconnection can be switched automatically upon use of the ablation or angioplasty controls. Enabling discharge during ablation or angioplasty then necessitates that disabling this automatic disconnection. If an assistant is assigned to operate the airgun while an ablation or ablation and angioplasty-capable barrel-assembly remains engaged therein, then a switch on the barrel-assembly control panel is used to disable the ablation or angioplasty control panel For freedom of movement, an ablation or ablation and angioplasty-capable barrel-assembly used while engaged in the airgun would normally be connected to a modified air pistol positioned behind the barrel-assembly hand-grip. As the apparatus is then held by the hand-grip with angioplasty control panel on its top side, the chance of an accidental discharge is slight even without the safety engaged or any magazine clip removed from the air pistol chamber. If unintentionally deployed during movement of the barrel-assembly, a shaving or abrading cutting tool-insert such as described below in the section entitled Radial Projection Unit Tool-inserts could injure the lumen wall.

To reduce the risk of scrapes (abrasions), gouges (punctures, perforations), or incisions, radial projection unit tool-inserts must be kept retracted whenever the barrel-assembly is resituated. To avert human error that would allow tool-inserts to remain in the raised position, the units are controlled as 'normally off' or retracted, requiring sustained depression of the control switch to remain raised. To this end, the ablation or angioplasty control panel spring-return push-to-actuate electrical switches, generally two, are supported by lift-platforms that are kept under the continuous downward (medial, retractive) urging of a strip-spring that to overcome requires intentional energization of the lifting mechanism by depressing the control switch. Multiple electrical units can be controlled, hence, disabled together according to how these are patched at the control panel to a given push-switch or to which preset combination of units the push control is switched.

Push-to-actuate control eliminates the need for logic circuitry, motion sensors, warning signals and switches to override these when the units are to remain projected during movement. The turret-motor motional control circuit incorporates a circuit-breaker to turn off the turret-motor if overloaded, which risks heat, mechanical, and in a blood vessel, thrombogenic injury. Deployment of the trap-filter can be appropriate during angioplasty or discharge; unsuited to automatic disabling, it is left discretionary except on energization of the laser in a combination-form barrel-assembly when the filter membrane would be destroyed. The filter deploying solenoid is disconnected when the laser in turned on. With a commercial laser, this cutout must be added to the laser on-switch.

VII2f(3). Blood-Tunnels

Blood-tunnels are tubes within the barrel-catheter that inlet at a point at the periphery of the barrel-catheter, and closing off the space these contain from the surrounding space within the barrel-catheter, or peribarrel space, course longitudinally at an angle or diagonally, to outlet at an arcuate or circumferentially removed end-point distal to the inlet. The blood able to pass through a blood-tunnel will largely depend upon its internal diameter, which thus becomes a factor in spacing the barrel-tubes by means of centering devices within and sizing the barrel-catheter. By and large, blood-tunnels gain significant effectiveness in large diameter barrel-assemblies. The barrel catheter is usually smaller in diameter than the muzzle-head, reducing the need to provide passages to allow oxygenated blood to pass the endoluminal component equivalent to the side or perfusion holes in conventional catheters.

The circumferential position, orientation, as well as the number of blood-tunnels can be used to affect stiffness. As do the number of centering devices and whether these are glued to the barrel-tubes, blood-tunnels also serve as tube polymer nonintrinsic barrel-catheter flexibility (bendability, trackability) altering elements and can be used to adjust barrel-catheter flexibility along the proximal or intermittent portions. In the proximal segment to remain extracorporeal, stiffening reduces drooping and kinking at the entry portal; however, stiffening of the intracorporeal length has little utility and is likely to produce stretching if not snagging injury, although these are avoidable by wetting stiffer sections with one of the lubricants specified in the section above entitled Insertion Tool Structure.

Blood-tunnels situated to one side of the barrel-catheter will promote flexing in the diametrically opposite direction. Provided the barrel-catheter has clearly visible contrast markings to indicate its rotational angle, this can improve trackability through a tighter curve. As shown in FIG. 41, blood tunnels are provided at opposite angles on either side of the barrel-catheter. Opposing angles thus generally make little if any difference for flow-through whether the barrel-assembly is advanced or withdrawn in antegrade or retrograde flow. Referring now to both FIGS. 39, 42, and seen in detail in FIG. 41, the flow of blood is antegrade from left to right, and the direction of miniball discharge, likewise left to right, is indicated with arrows, making the proximal inlets 93 of blood-tunnels 96 distinguishable from the distal outlets 94.

Barrels 74 in FIG. 41 pass through the barrel-tube holes 91 shown in FIG. 42 in the centering device 95 containing gas pressure relief holes 92 and central aperture 90 through which wires 97 in FIGS. 41, 72, 74, and 75 for the electromagnets, turret-motor, and radial projection units if present pass. The incorporation of blood-tunnels may necessitate the use of a larger diameter barrel-catheter, with the consequence that the flexibility of the barrel-assembly will be reduced both as widened and as incorporating blood-tunnels. While a barrel-catheter that is narrow may be increased in diameter to allow the incorporation of blood-tunnels, it must not exceed the muzzle-head in diameter, and the muzzle-head is not increased in diameter.

Larger diameter multibarrel radial discharge barrel-assemblies can incorporate both blood-grooves, shown as 66 in FIGS. 38 and 40, and blood-tunnels, shown as 96 in FIGS. 39, 41, and 42 within barrel-catheter 72, these elements described below. While a monobarrel radial discharge barrel-catheter can be small enough in outer diameter to serve as a kind of 'guidewire' for follow-on devices, devices that use guidewires normally serve functions that precede rather than succeed stenting; however, where the muzzle-head passes readily through the lumen as to dispel concerns about stretching, dissection, or perforation, the muzzle-head can be used to implant miniballs upon withdrawal.

Depending upon the angle at which the blood-tunnel tubes course through the barrel-catheter and the material or materials of which the blood-tunnel tubes are made, the blood-tunnels allow some transmission of the pulse through the barrel-catheter. Made of more rigid materials, the blood-tunnels can, according to number and spacing, also act as structural buttresses to stiffen the barrel-catheter. Placing blood-tunnels in longitudinal sequence along one radius of the barrel-catheter, for example, will bias the bendability of the barrel-assembly away from that direction toward the perpendicular or normal direction. Angular uniformity in the stiffness of the barrel-assembly thus requires a circumferentially complementary and balanced distribution of blood-tunnels.

When made of a pliant material or materials, such as vinyl, and bonded by means of an adhesive to the wall of the barrel-catheter with acutely angled mitered ends, the blood-tunnels can course in substantially adjacent relation to the concave surface of the barrel-catheter. Made of rigid material, such as polystyrene or high density polyethylene or polypropylene, the blood-tunnels are straight as to appear geometrical cords in cross-section, and buttress the wall of the barrel-catheter, making it stiffer. With the barrel-catheter and barrel-tubes bonded to the centering devices, no significant increase in stiffness is realized by coursing the blood-tunnel tubes through and bonding these to the centering devices.

In the portions of the barrel-assembly to remain outside of the patient, the elimination of nonfunctional bends that detract from control over the rolling resistance to the miniballs is necessary to achieve accurate exit velocity and impact force. Thus, when the materials of the barrel-catheter and barrel-tubes are highly pliant, the incorporation of blood-tunnels in the barrel-catheter serves to minimize flexion in the proximal portions of the barrel-assembly. By comparison, in the distal portions of the barrel-assembly introduced into the patient, flexibility sufficient to track anatomical bends with little resistance is preferable.

Accordingly, blood-tunnel tubes are not incorporated toward the fore; however, the flexibility sought for this portion recommends the use of centering devices that allow the diameter of the barrel-catheter to be smaller, and this in itself will allow some passage of the pulse up to and through the blood-grooves in the sides of the muzzle-head. The elimination of centering devices in the distal portions of the barrel-assembly does not negate the need for a peribarrel space sufficient in volume to relieve the pressure of discharge so that no gas will be ejected into the bloodstream. Since the barrel-catheter must accommodate this need for sufficient peribarrel space, a barrel-catheter of minimum internal diameter must be provided. The omission of centering devices thus has only the result of the dropping of the barrel-tubes to the floor of the barrel-catheter.

VII2f (4). Incorporation of a Bounce-Plate into Radial Discharge Barrel-Assemblies The value in a proximad redirection or trajectory reversal capability pertains primarily to advanced cases of collapse or stenosis of the trachea with its structured lumen wall that includes cartilage rings and ligaments necessitating the accurate placement of implants. Other ductus are not this structurally differentiated, so that the insertion of implants to given trajectory end-points or target locations can usually proceed unidirectionally with uniformly distad or forward-inclined trajectories and without the need for reversal to proximad or backward-inclined trajectories. To minimize the risk of injury, bounce-plate attachments and mechanisms made as part of the barrel-assembly must be as small and unobtrusive with rounded off edges as possible.

Furthermore, since for a given number of barrel-tubes, a radial discharge barrel-assembly should achieve minimization in the outer diameter of the muzzle-head, and the addition of bounce-plates, requiring the muzzle-ports to be recessed, would add diameter if within, and would be likely to cause scraping injury to the larynx or lumen wall if mounted to the outside of the muzzle-head. In a multiple discharge barrel-assembly, these consequences are unacceptable. For this reason a radial discharge barrel-assembly with an attached or permanent bounce-plate should be avoided. However, if equipped with an enclosed and nonprotrusive bounce-plate that can be deployed from outside the body, as described above in the sections entitled Extracorporeally Deployable Bounce-plate with Fixed Rebound Angle and Extracorporeally Deployable Bounce-plate with Adjustable Rebound Angle, a single barrel radial discharge barrel-assembly may be usable in the trachea of a tiny dog, for example.

Even the introduction and withdrawal of a simple pipe barrel-assembly provided with a protective rubber surround extension at the distal end through the larynx must be performed with caution. Requiring to avoid the need for multiple withdrawals and reentries that increase the chances for entry wound complications, a radial-discharge barrel-assembly configured for use in the circulatory system would demand remotely deployable bounce-plates. Of little value, these would add to the cost. The essential structural uniformity or homogeneity of the average lumen wall obviates the need for such a capability. The structured character of the tracheal lumen is larger than the structurally undifferentiated lumens of vessels and ducts, making observation of the tracheal lumen more important and less difficult.

The usefulness of radial discharge barrel-assemblies capable of reversing the direction of the trajectory in the vascular tree or in ducts, whether provided in a single embodiment or by changing to either of two embodiments, is thus recognized as feasible but anatomically unjustified. In the airway of a small dog or human neonate, such a radial discharge barrel-assembly could achieve precise aiming only tediously and laboriously, while in the vascular tree, no such reverse aiming capability is necessary. For these reasons, the incorporation of means for reversing the direction of the trajectory in radial discharge barrel-assemblies other than in a radial discharge monobarrel for the purpose stated is discounted.

VII2f(5). Use of Minimally and Fully Angioplasty-Capable Radial Discharge Barrel-Assemblies A minimally ablation or ablation and angioplasty-capable barrel-assembly with an embolic filter and radial projection units in the muzzle-head includes angioplasty components only to the extent needed for implantation discharge without complications. Unlike a fully capable barrel-assembly, it is not intended for disengagement from the airgun as an independent apparatus for free manipulation and cannot be used to perform an angioplasty when disconnected from an airgun. Drawing power and control from the airgun through end-plate connecting terminals such as shown in FIG. 72 and not ordinarily equipped with a side-port or side-socket, it is closed off for attaching a supportive device such as a gas cylinder or laser cable and is less versatile than a fully angioplasty-capable barrel-assembly.

Minimally and fully ablation and/or angioplasty-capable barrel-assemblies may be required to lay down a pattern of miniballs placed at millimetric distances along the lumen wall, and both barrel-assemblies and radial projection catheters usually have embolism-preventing heat-windows as addressed above in the section entitled Thermal Conduction Windows (Heat-windows) and Insulation of the Muzzle-head Body in Minimally or Fully Thermal Ablation and Thermal Ablation and Angioplasty-capable (Independently Usable) Barrel-assemblies and radially directed working tools as addressed above in the section entitled Radial Projection Units which must be passed over the lumen wall at a controlled rate. The use of these will generally require advancement or retraction of the barrel-assembly at a uniform rate by a semiautomatic positional control system, as addressed below in the section entitled Linear Positioning Stage or Table Airgun Mount.

Providing side-ports or side-sockets negating the economic advantage in producing a less than fully angioplasty-capable barrel-assembly, to connect an ancillary catheteric or cabled device necessitates disengaging the barrel-assembly from the airgun to gain access to a socket or side-port in the proximal end-plate. Disconnection from the airgun is also necessary to add a radial projection catheter. Engagement in the airgun allows precise transluminal positioning with the airgun linear positioning stage and rotary movement with the turret-motor but hinders freedom of movement. In more unpredictable and precarious situations, barrel-assemblies for use in blood vessels should incorporate an array of potential responses to possible midprocedural eventualities.

If bipartite, radial projection unit tool-inserts of any kind can be introduced using the barrel-catheter as a guide wire at any time during the procedure without requiring withdrawal. Unforeseeable eventualities aside, angioplasty-capable barrel-assemblies, functional apart from the airgun for every purpose but implantation discharge, with remotely (hand-grip) controllable radial projection units, deployable and retractable run-ahead trap-filter (embolic filter), heat-windows, and side-socket for connecting different fluid and electrical attachments, can be preconfigured for a specific procedure. Muzzle-head radial projection unit tool-inserts, for example, can be chosen for the purpose at hand, and the use of a combination-form barrel-assembly allows the prepositioning of a rotatory burr or excimer laser, for example.

Because a size-matched combination-form radial projection catheter can be introduced at any time, response to almost any contingency is possible. The incorporation of radial projection unit blank (push-arm, shoe) tool-inserts, as addressed below in the section entitled Radial Projection Unit Tool-inserts, allows the muzzle-head to be brought into flush relation with the side to be implanted without the application of an extraluminal force field or significantly adding to the cross-sectional area of the lumen that is obstructed. When provided about its entire circumference, the muzzle-head can restrain the lumen wall all around at the peak systolic diameter while suspending itself axially without obstructing the flow of blood, which passes around and/or through the tool-inserts.

This suppresses pulsation over the segment under treatment when the muzzle-head need not be brought into adjacent abutment against the lumen wall. The passage of blood is also aided by incorporating blood-grooves and blood-tunnels as addressed below in the section entitled Monobarrel Radial Discharge Muzzle-head. In most instances, implantation is facilitated if not enabled by suppressing rather than attempting to accommodate an interfering pulse or intrinsic motility. When it can be assumed that sufficient accuracy will be achieved manually without suppressing relative movement between the exit port and the target location, the manual discharge of miniballs in an artery is more accurate if the muzzle-head is positioned during the systoles, during which phase the expansion in lumen diameter expedites this resituation and reduces the risk of ischemia by moving blood past the muzzle-head.

Discharge is then effected with the artery relaxed at the end of the diastoles. Manual control is also aided through the use of medication to slow or temporarily arrest autonomic motility, as addressed below in the section entitled Motional Stabilization of the Implant Insertion Site. Even though ideally the muzzle-head lightly contacts the lumen wall during discharge, the pressurized air forced before the discharging miniballs must be given a path of least resistance to prevent air from being forced into the bloodstream upon discharge. At the same time, to prevent the back-flow into the barrel ports of blood when the muzzle-head is immersed in the bloodstream, resistance must be posed to the displacement of the air in the muzzle. In other words, the flow of gas must be biased in favor of nondisplacement from without while at rest and in favor of pressure diversion back into the barrel-assembly under conditions of the sudden pressurization of expulsion.

The volume of air in the barrel-assembly and chamber, together airtight except through the barrel, is constant. The higher pressure of the blood and angle of entry make complete prevention of blood backflow through the muzzle-ports at the moment of immersion difficult without barricading the muzzle-ports. Because the gas pressure diversion channels and relief space must become completely filled with blood before resistance to the passage of gas equals that presented by the column of blood at the muzzle-ports, blockage for this reason midprocedure is unlikely. Should the mechanism become fouled, the barrel-assembly is withdrawn and purged with pressurized distilled water. In most instances, because the barrel-assembly is airtight, this is accomplished by placing a finger over the muzzle-ports facing upwards and thus not allowing air to be displaced by blood.

When the placement of the muzzle-ports does not allow these to be blocked to the air with a fingertip, the muzzle-head is dipped into distilled water so that the muzzle-ports are filmed over by surface tension. The muzzle-head is then stored in a freezer. To be certain that the film does not break by cold contracture and is sufficiently thick, dipping and freezing may be repeated several times. Upon insertion in the bloodstream, an interval is allowed for the temperature of the blood to melt the film of ice and the muzzle-head to assume body temperature. In an embodiment that includes electrically operated radial projection units, the thermal expansion wires used to raise the tool-insert holding and lift platform can be sent current to accelerate melting. Whether the brushes remain deployed during transluminal movement to the diseased portion of the ductus is at the discretion of the operator.

Initial transluminal movement is usually to a point beyond the segment of the ductus to be treated with the procedure carried out in withdrawal with movement over larger distances directly manual, over small distances by manual control of the linear positioning table stepper motor, and discharge over lesions by manual direction of automatic sequences. Once immersed in the bloodstream, the airtightness of the barrel-assembly prevents the inflow of blood. A simple pipe barrel-assembly is not for use in small diameter lumina as risking injury and is additionally unsuited to use in the circulatory system as lacking internal paths for averting gas expulsion at the muzzle exit-ports or exit-holes with consequent embolization. The barrel-tubes in a radial discharge barrel-assembly suitable for use in the vascular tree are perforated, removing barriers within the spaces defined by the different tubes within the barrel-assembly.

The perforations present no burrs or irregularities on the inner surface of the barrel-tubes, which must be smooth. The air throughout the barrel-assembly now in communication or effectively continuous, the displacement of air anywhere within this space is minimally resistant to internal movement or redistribution. This diverts expulsive gas within the muzzle-head before exiting and minimizes recoil, thus both averting injury to the vessel and the dislodging of miniballs remaining on the rotary magazine clip.

As seen in FIGS. 48, 49, 65, and 66, gas pressure equalization (pressure relief, pressure diversion) channels 226 are drilled through the muzzle exit ports creating a path from each to the central channel. The gas pressure ahead of the discharging miniballs is thus bled off or diverted to the central channel as the path of least resistance compared to introfusion into the blood. Gas returned with sufficient force that it would jerk the barrel-tubes is released through an elastomeric membrane slit valve in the end-plate. The outflow of these pressure diversion channels is directed proximally or backwards to the canal formed by their convergence which is continuous with the central canal amid the barrel-tubes.

Following puncture and expansion of a vessel, the heparine-saline solution-wetted muzzle-head is introduced and advanced to the sites slightly short of preceding angioplastic treatment. Discharged at an acute angle, the shots then come to rest beneath the atheroma and removed plaque. The muzzle-head is chosen in a size equal or slightly larger in diameter than the internal diameter of the segment of the vessel short of the area to receive the miniball implants by the length of the trajectory. Since the placement of a conventional intraluminal stent may squeeze away remaining plaque, the preliminary angioplasty should be thorough. During angioplasty, rotation expedites aiming a heat-window radial projection unit tool-insert at an eccentric lesion.

Since an angioplasty is completed before ferromagnetic implants have been introduced, there are not yet implants present that the field strength of the windings associated with thermal use might reposition or extract. Disruption thus must, however, be considered in a retreatment that uses the means described. The rotatory use of the turret motor to direct a heat-window that is heated by passing current through one or both recovery electromagnet windings, which are seldom needed for recovery other than during discharge, remains enabled, allowing treatment of an eccentric lesion. Radial projection unit tool-inserts, to include those heat radiating, are powered independently of the other components in the barrel-assembly. When, however, the heat-window is heated with the winding of the turret-motor itself, the rotatory use of the motor is disabled.

During discharge, rotation is used to change the aiming point of a single, a particular, or radially asymmetrical set of muzzle-ports, or to rotate the tractive electromagnets to recover a mispositioned or stray miniball. The trap-filter shares with the turret-motor in its rotatory mode of operation use in both angioplasty and discharge. During angioplasty, the trap-filter stops potentially embolizing debris from being carried downstream, whereas during discharge, it affords the same protection against escaped miniballs, although the level of protection provided by the recovery electromagnets will usually prove sufficient. When it does prove sufficient, and additional protection is considered redundant if not an impediment, the trap-filter is not deployed.

VII2f(6). Ablation and Angioplasty-Incapable Barrel-Assembly Controls on the Airgun Airgun controls are mounted to airguns and barrel-assembly controls to barrel-assemblies, the exception being that pistols and dedicated airguns meant for use with minimally ablation or ablation and angioplasty-capable barrel-assemblies, which are used only while inserted in the airgun, generally include the controls for ablation or angioplasty on the airgun. The discharge controls required on the airgun respond to the exit velocity control points in the airgun, so that modified commercial pistols lack controls for adjusting the current to a plunger solenoid used in dedicated interventional airguns as a triggering mechanism, for example. Duplicate controls are exceptional, result when minimally-capable barrel-assemblies are provided with onboard controls, which does not involve a bulky duplication in battery packs.

Such results from pairing a modified air pistol having thermoplasty and other controls meant for use with a minimally ablation or ablation and angioplasty-capable barrel-assembly with an ablation or ablation and angioplasty-capable barrel-assembly that is self-contained for airgun-independent use. The controls for modified commercial air pistols are mounted to the hand-open side of the pistol-grip battery pack and control electronics downward extension, while those for dedicated interventional airguns are mounted to the airgun enclosure or cabinet. Lacking ablation or angioplasty capability, the controls are limited to those governing discharge.

Miniball recovery related to discharge rather than to ablation or angioplasty, pistols meant for use only with ablation and angioplasty-incapable barrel-assemblies require potentiometers to adjust the current through the recovery electromagnet or magnets for the purpose of adjusting the magnetic field strength. A simple pipe barrel-assembly is usually provided with one such magnet, while a radial discharge ablation or ablation and angioplasty-capable barrel-assembly is provided with two. Radial discharge ablation or angioplasty-incapable barrel-assemblies equipped with an embolic trap-filter as an additional safeguard against the escape of a miniball rather than to catch fractured plaque debris also require a solenoid control as addressed above in the section entitled Trap-filter Deployment and Retrieval Mechanism to deploy and retract the filter.

Pistols meant for use with both ablation or angioplasty-incapable and minimally capable barrel-assemblies must include the additional controls required for radial projection units, embolic trap-filter, and use of the windings in the muzzle-head as thermoplasty heating elements. Modified air pistols are not normally used with ablation or ablation and angioplasty-capable barrel-assemblies. Meant for use independently of the airgun, the latter have ablation or angioplasty controls mounted to a power and control housing which can be hand-grip-configured to contain a battery pack that is lacking in incapable and minimally capable barrel-assemblies.

VII2g. Minimally Ablation or Ablation and Angioplasty-Capable Barrel-Assemblies

Minimally ablation or ablation and angioplasty-capable barrel-assemblies are differentiated from other types of barrel-assembly in the section above entitled Types of Barrel-assembly. Compared to an ablation or ablation and angioplasty-capable barrel-assembly, the muzzle-head is substantially the same but is likely to incorporate fewer tissue reduction features, while the proximal engagement components of the barrel-assembly must be distinct. Accordingly, muzzle-heads for both types are addressed in this section. This type incorporates any or all of the components used to accomplish an ablation or an angioplasty, to include radial projection units and trap-filter, but is not configured for use independently of an airgun.

Without a side-socket, as addressed below in the section below entitled Barrel-assembly Side-socket, a minimally ablation or ablation and angioplasty-capable barrel-assembly must be removed from the airgun to allow the insertion of a cooling or medication delivering catheter into the central canal or a barrel-tube through the proximal terminal plate (end-plate). Since this breaks the electrical connection to its electrical components, it must then be reconnected to the airgun power supply through a socket mounted to the outside of the airgun enclosure or connected to an alternative source of power.

VII2g(1). Minimally Thermal Ablation or Angioplasty-Capable Barrel-Assemblies

As addressed here, thermoplastic ablation is intended to apply to vulnerable plaque. Calcified plaque and minimally inflamed endothelium are not to be treated thus as substantially stable, nonvulnerable, and treatable with oral medication. Discretionary searing of vulnerable plaque is intended to eliminate detritus (fibrin, necrotic atheromatous core, foam cells, cholesterol clefts, and thrombus (see, for example, section 4d(2) entitled Ductus Wall Tumefacients and Sangiorgi, G. and Colombo, A. 2003. "Embolic Protection Devices," *Heart* (London, England) 89(9):990-992) liable to enter the lumen. All apparatus described herein include heat and Peltier device cooling on-off switches adjacent to heating plates to allow quick heating and cooling so that heat does not continue past the vulnerable plaque once traversed. Searing is with fluoroscopic or computer tomographic guidance and a contrast media coated muzzle head.

Contrast dispersed in the bloodstream must not be implicated in nephropathy or have such tendency ameliorated (see, for example, Zhang, J. Z., Kang, X. J., Gao, Y., Zheng, Y. Y., Wu, T. T., and 6 others 2017. "Efficacy of Alprostadil for Preventing of Contrast-induced Nephropathy: A Meta-analysis," *Scientific Reports* 7(1):1045; Mohammadi, M., Hajhossein Talasaz, A., Alidoosti, M., Pour Hosseini, H. R., Gholami, K., Jalali, A., and Aryannejad, H. 2017. "Nephroprotective Effects of L-Carnitine against Contrast-Induced Nephropathy in Patients Undergoing Percutaneous Coronary Intervention: A Randomized Open-labeled Clinical Trial," *Journal of the Tehran Heart Center* 12(2):57-64; Ye, Z., Lu, H., Su, Q., Guo, W., Dai, W., Li, H., Yang, H., and Li, L. 2017. "Clinical Effect of Trimetazidine on Prevention of Contrast-induced Nephropathy in Patients with Renal Insufficiency: An Updated Systematic Review and Meta-analysis," *Medicine* (Baltimore, Md.) 96(9):e6059; Ye, Z., Lu, H., Guo, W., Dai, W., Li, H., Yang, H., and Li, L. 2016. "The Effect of Alprostadil on Preventing Contrast-induced Nephropathy for Percutaneous Coronary Intervention in Diabetic Patients: A Systematic Review and Meta-analysis," *Medicine* (Baltimore, Md.) 95(46):e5306; Golshahi, J., Nasri, H., and Gharipour, M. 2014. "Contrast-induced Nephropathy: A Literature Review," *Journal of Nephropathology* 3(2):51-56; Weikl, A. and Hubmann, M. 1982. "A Survey of Contrast Media Used in Coronary Angiography," *Cardiovascular and Interventional Radiology* 5(3-4):202-210). In any barrel-assembly for use in the arterial tree, the preliminary elimination of fibrous caps and subjacent detritus prevent a liberation of potentially embolizing debris when the muzzle-head, usually unheated during discharge, makes contact with the lumen wall (see, for example, Finet, G., Ohayon, J., Rioufol, G., Lefloch, S., Tracqui, P., Dubreuil, O., and Tabib, A. 2007. "Morphological and Biomechanical Aspects of Vulnerable Coronary Plaque," *Archives des Maladies du Coeur et des Vaisseaux* 100(6-7): 547-553; Bentzon, I. F. and Falk, E. 2001. "Coronary Plaques Calling for Action—Why, Where and How Many?," *European Heart Journal Supplements* 3(Supplement I):13-19).

However, the disease process and inflammation of atherosclerosis, if not the frank atheromatous lesions it produces where the arterial tree is wider in caliber or bifurcated, for example, extend throughout the larger gauge portions of the arterial tree, the systemic nature of endothelial activation, dysfunction, and atherosclerosis apparent from any of several perspectives (see, for example, Chu, D., Bakaeen, F. G., Wang, X. L., Dao, T. K., LeMaire, S. A., Coselli, J. S., and Huh, J. 2008. "The Impact of Peripheral Vascular Disease on Long-term Survival after Coronary Artery Bypass Graft Surgery," *Annals of Thoracic Surgery* 86(4): 1175-1180; Ridker, P. M. and Silvertown, J. D. 2008. "Inflammation, C-reactive Protein, and Atherothrombosis," *Journal of Periodontology* 79(8 Supplement):1544-1551; Mora, S. and Ridker, P. M. 2006. "Justification for the Use of Statins in Primary Prevention: An Intervention Trial Evaluating Rosuvastatin (JUPITER)—Can C-reactive Protein be Used to Target Statin Therapy in Primary Prevention?," *American Journal of Cardiology* 97(2A):33A-41A; Toutouzas, K, Drakopoulou, M., Mitropoulos, J., Tsiamis, E, Vaina, S, and 4 others 2006. "Elevated Plaque Temperature in Non-Culprit De Novo Atheromatous Lesions of Patients with Acute Coronary Syndromes," *Journal of the American College of Cardiology* 47(2) 301-306; Bhatt, D. L. and Topol, E. J. 2002. "Need to Test the Arterial Inflammation Hypothesis," *Circulation* 106(1):136-140; Heras, M. and Chamorro, A. 2000. "Atherosclerosis: A Systemic Condition that Requires a Global Approach," *European Heart Journal* 21(11):872-873; Eagle, K. A., Rihal, C. S., Foster, E. D., Mickel, M. C., and Gersh, B. J. 1994. "Long-term Survival in Patients with Coronary Artery Disease: Importance of Peripheral Vascular Disease. The Coronary Artery Surgery Study (CASS) Investigators," *Journal of the American College of Cardiology* 23(5):1091-1095; Balas, P. and Pangratis, N. 1990. "Panarterial Ultrasonography. A Non invasive Evaluation of the Peripheral Arterial System," *International Angiology* 9(1):4-7; Sumner, D. S. 1989. "Non-invasive Assessment of Peripheral Arterial Occlusive Disease," in Rutherford, R. B. (ed.), *Vascular Surgery*, 3d Edition, pages 61-111, Philadelphia, Pa.: W. B. Saunders; Carter, S. A. 1969. "Clinical Measurement of Systolic Pressures in Limbs with Arterial Occlusive Disease," *Journal of the American Medical Association* 207(10): 1869-1874).

That the chronic inflammation of endothelial activation is systemic recommends the systemic and targeted use of statins and conservative use of atherectormy or thermal angioplasty, for example, as limited to plaque. As addressed above in the introductory sections and that entitled Cooperative Use of Impasse-jackets in Pairs and Gradient Arrays, paired impasse-jackets allow targeting a statin, for example, to a delimited segment of an artery, for example, at a high concentration, at the same time that a background dose of the statin is administered conventionally. As addressed above in the section entitled Preliminary Description of the Invention, and others, the elimination of plaque is a factor in promoting recovery to normal function.

Where the primary drug is best circulated but uptake by the target organ or tissue is insufficient and located too deeply for release from a transdermal patch to deliver the dose sought deeply or quickly enough, the directly targeted delivery to the tissue or organ to can be accomplished through placement of a local jacket or nonjacketing side-entry connector, if necessary, with a small dose of dimethyl sulfoxide (DMSO) to expedite uptake. When a surface port is already in use, local delivery is through a ductus side-entry jacket or nonjacketing side-entry connector. Several combinations for systemic and pipe-targeted delivery are possible. When no surface port is present and the use thereof felt not warranted for this limited purpose, the infused drug to be circulated and not just taken up by a target organ or tissue can, for example, be introduced in part as a ferrofluid wherein the drug is carried by superparamagnet iron oxide nanoparticles with the jacket or connector inclusive of a magnetized layer.

The capability to perform a preemptive eradication of the potentially thromboembolizing lining of a more affected lumen thus has protective value. Such a barrel-assembly has a minimal thermoplasty capability. As applied here, thermal angioplasty or thermoplasty, addressed below in the section entitled Thermal Ablation and Angioplasty- (Lumen Wall Priming Searing- or Cautery-) Capable Barrel-assemblies, seeks to systematically and preemptively destroy vulnerable plaque through a leading end searing (cautery, electrocautery, singeing) of the endothelium upon contact with the heated muzzle-head, which unlike the use of a balloon, eliminates the vulnerable plaque as a threat postprocedurally.

An initial heating pass of the muzzle-head can be accomplished perfunctorily as a prophylactic or preventive measure when the presence of vulnerable plaque is suspected without having been confirmed. When possible, the thermoplasty is accomplished in the same pass as the other therapeutic action is applied. A prepositioned stent-jacket or shield-jacket containing sufficient continuous ferrous material can be noninvasively heated by placing the patient in a radiofrequency alternating magnetic or electromagnetic field, but thorough coverage must be transluminal or catheteric. Another reason for incorporating a nose radiofrequency probe or thermoplasty window is to fuse any ductus-intramural tunics confirmed through imaging to have delaminated, although this is better accomplished with the aid of a bonding agent injected by tool-insert injectors in a more capable barrel-assembly.

Compression during the application of heat is obtained by prepositioning the stent-jacket and steering the muzzle-head against the lumen wall with the aid of 1. Blank tool-inserts on the opposite side used as push-arms, 2. An extracorporeal electromagnet and/or 3. An oversized muzzle-head with blood bypass means in the form of blood-tunnels, blood-grooves, and/or a patent central channel (see, for example, Barry, K. J., Kaplan, J., Connolly, R. J., Nardella, P., Lee, B. I., Becker, G. J., Waller, B. F., and Callow, A. D. 1989. "The Effect of Radiofrequency-generated Thermal Energy on the Mechanical and Histologic Characteristics of the Arterial Wall in Vivo: Implications for Radiofrequency Angioplasty," *American Heart Journal* 117(2):332-341; Fram, D. B., Gillam, L. D., Aretz, T. A., Tangco, R. V., Mitchel, J. F., and 6 others 1993. "Low Pressure Radiofrequency Balloon Angioplasty: Evaluation in Porcine Peripheral Arteries," *Journal of the American College of Cardiology* 21(6):1512-1521).

To eliminate the need for withdrawal and reentry, thermal angioplasty must be performed with a minimal or fully ablation or ablation and angioplasty-capable barrel-assembly. Numerous means for accomplishing thermoplasty include an inmate radiofrequency probe or laser at the nose. Others are heatable motor and recovery electromagnet windings and connectable sources of hot gas-heated heat-windows, as described below in the section entitled Thermal Conduction Windows (Heat-windows) and Insulation of the Muzzle-head Body in Thermal Ablation or Thermal Angioplasty-capable Barrel-assemblies. Still others are an excimer laser or rotational atherectomy cutter installed in the central channel of a combination-form barrel-assembly (addressed below in the section entitled Combination-form Barrel-assemblies, et sequens).

Regardless of whether the heat-window is heated by the winding inside it or by connection to the hot air outlet of a vortex-tube cold air gun, for example, both the temperature and time of contact of the heat-window with the plaque are critical. Precise timing can be attained by insertion of the barrel-assembly in a an airgun mounted upon or to a separate linear stage. The recovery and turret-motor electromagnet windings can, however, be heated, such as to warm a coating of heat-activated tissue bonding agent applied to miniballs discharged through barrel-tubes kept chilled by a cooling catheter as the muzzle-head is withdrawn, as indicated above in the section entitled Circumstances Dissuading or Recommending the Application of Stays.

Cryoplasty seeks primarily to reduce intimal hyperplasia following the angioplasty. Cryoplasty is briefly addressed above under the section entitled Turret-motor Operational Modes. There are essentially three classes of barrel-assembly for use in the arterial tree: ablation or angioplasty-incapable, which are used only while engaged in the airgun and lacking means for thermoplasty are limited to treatment where a precautionary angioplasty has been discounted; minimally-capable, which incorporate a nose heat-window and are seldom if ever disengaged from the airgun to perform an angioplasty; and ablation or ablation and angioplasty-capable, which can be used independently of the airgun to accomplish preparatory treatment before implantation discharge.

A positioning control and discharge control panel is mounted on the airgun and described below under the section entitled Airgun Control Panel. A barrel-assembly of sufficient angioplasty capability for use while separated from the airgun as a free-standing apparatus until engaged in the airgun to initiate implantation discharge is provided with its own power and control housing with side mounted control panel for these separate functions. A universal power and control housing for fitting onto any angioplasty-capable barrel-assembly to include combination-forms must incorporate all the controls needed for any barrel-assembly making it costly and usable with only one barrel-assembly at a time.

The potential of thermal or cryogenic angioplasty, of a tissue bonding agent, or of these in combination to repair a propensity for separation between or within the layers or the tunics within the wall of a ductus warrants study. No laser-based apparatus similar to those used to reattach a retina appears available. When the intima or internal layer is the source of the stenosis, the apparatus and equipment described herein can be used only if it can be reattached to the media. Then any stent used must be endoluminal or conventional. To reduce costs, certain components that would be incorporated into a fully capable barrel-assembly but which are considered unnecessary for a specific procedure are omitted.

Intermediate forms for use while engaged in the airgun allow omission of an inmate power source (battery-pack), radial projection units, and the inclusion of fewer controls on the on-board control panel, but are limited to light and simple implantation discharge-preparatory angioplasty or ablation. If produced with connections at the rear rather than by means of a side-socket as addressed below in the section entitled Barrel-assembly Side-socket, these preclude attachment at the back of the barrel-assembly of a vortex tube, $CO_2$, or $NO_2$ cartridge for thermal angioplasty.

Electrical connection through the airgun to the power supply is either as shown in FIG. 72 with the proximal end-plate 99 engaged in the airgun chamber as shown in FIG. 74 so that multiple electrical contact connector terminal 101 is brought into contact or as shown in FIG. 75 by means of external extension cord 109. For a minimal capability barrel-assembly dependent upon connection to the airgun power supply for power, these connections include at the least those for rotatory and thermal control of the turret-motor and any other heat-windows and those to energize the miniball recovery electromagnets in the nose of the muzzle-head. In comparison, an ablation or ablation and angioplasty-capable barrel-assembly incorporates an inmate power source within the slidable power and control housing as not to depend upon the airgun power supply.

It can, however, include a multiple electrical contact connector terminal or electrical connection plate as does an incapable embodiment, in which case it can be controlled from either the control panel on the airgun or that on the power and control housing. In more capable barrel-assemblies, to minimize human error, the airgun control panel includes only controls for the airgun, and the power and control housing control panel includes only controls for mechanical and thermal ablation, angioplasty, and the use of radial projection units. A minimally-capable barrel-assembly that performs a preemptive thermoplasty at the nose ahead of the discharging muzzle-ports or exit-holes best uses a separately energized nose heat-window, the recovery electromagnets required for tractive use during discharge.

This heat-window, which still draws power from the airgun power supply, is best controlled on the barrel-assembly, such as a small control knob mounted to terminal plate 106 in FIG. 75. To stent without an antecedent angioplasty or where it is suspected that a previous angioplasty left rupturable plaque in place requires the addition of minimal angioplasty means to minimize the risk of releasing embolizing debris by contact with the muzzle-head. Accordingly, any time that a barrel-assembly is introduced into an atheromatous artery, especially one that has not been angioplastied or that a preceding angioplasty notwithstanding, is believed could retain rupturable plaque, thermal or cryogenic angioplasty is performed.

The application of heat to the lumen wall is for precluding to the extent possible, the rupture of plaque and not for altering the mechanical properties of the lumen wall in preparation for implantation, which requires only routine adjustments in ejection force or exit velocity. The means for achieving good thermal conductivity and focus are described below in the section entitled Thermal Conduction Windows (Heat-windows) and Insulation of the Muzzle-head Body in Thermal Ablation or Thermal Angioplasty-capable Barrel-assemblies. A minimal angioplasty capability is attained by making the windings already present in the implant spherule recovery electromagnets heatable to achieve a minimal thermal angioplasty capability.

While barrel-assemblies intended for use in both diseased arteries and stenosed ductus of other types provide temperature settings from 50 to 100 degrees centigrade in ten increments of five degrees each, barrel-assemblies for use limited to atheromatous arteries are set to 90 degrees centigrade. Such a precautionary angioplasty would best be accomplished passively as an ancillary or incidental function attendant upon, rather than as a separate procedure preliminary to, implantation. However, a. The recovery electromagnets toward the front of the muzzle-head cannot be heated and used tractively at one and the same time, b. The use of one recovery electromagnet to heat while the other is used to recover would represent a circumferential insufficiency on both scores, c. For both (1) Freedom of movement and (2) Access to the free end for insertion of a cooling catheter, the barrel-assembly, even when used for minimal thermal angioplasty- (lumen wall priming-searing or cautery capability, is best completely separately from and independently of the airgun.

Thus, even though such a precautionary angioplasty is not discretionary as is an angioplasty that targets atheromatous tissue, a minimal thermal angioplasty- (lumen wall priming searing- or cautery-) capable barrel-assembly is still used independently of an airgun and provided with an on-board hand-grip Barrel-assembly hand-grip, as addressed below in the section entitled Barrel-assembly Hand-grip, that contains a battery pack and mounts a control panel, as addressed below in the section entitled Ablation or Ablation and Angioplasty-capable Barrel-assembly Onboard Control Panel. The minimal capability angioplasty barrel-assembly is thus an abbreviated version of which the capabilities fall within the scope of those included in an angioplasty-capable barrel-assembly.

However, lacking a heatable turret-motor and radial projection units and therefore the means for performing a proper angioplasty, such an intermediate level barrel-assembly can be produced at lower cost. In the simplest and least expensive minimally capable barrel-assembly, which is not provided with onboard controls for use independently of the airgun, a separately powered nose-cap or nose-envelope heat-window at the front of the muzzle-head where contact is first made with the lumen wall is required; the turret-motor reserved for rotation of the muzzle-head during discharge. Such a barrel-assembly is seldom if ever used while removed from the airgun, when it still draws power from the airgun power supply and does not use the turret-motor as a heating element for thermoplasty.

Whether engaged in or removed from the airgun, the turret-motor in a more capable barrel-assembly can alternate between heating element for thermoplasty and to rotate the muzzle-head, although an interval for cooling, readily shortened by inserting a cooling catheter, is allowed. Rotation during use to heat pertains only to a heat-window in the form of a slit or slot such as 179 in FIG. 64 as unidirectional; a heat-window that completely encircles the turret-motor is omnidirectional (circumferential), negating the need for rotation. With the barrel-assembly disengaged from the airgun, rotation of a slit type heat-window while heating can usually be accomplished by hand. If not, then rotation of a directional heating source is accomplished with a radial projection heater tool-insert or a multiplicity thereof in any formation which uses the turret-motor for rotation.

The turret-motor is controlled with the airgun control panel during discharge and the barrel-assembly power and control housing during ablation or angioplasty when the barrel-assembly is disengaged from the airgun. Once an angioplasty-capable barrel-assembly is inserted into the airgun, the electrical connection used to energize the electromagnets and turret-motor are used almost exclusively in support of discharge rather than as heating elements, controls for ablation or angioplasty on the barrel-assembly power and control housing when the barrel-assembly is usually disengaged from the airgun, although angioplasty and the injection of medication, for example, may occasionally be interjected during the discharge phase. With such a barrel-assembly inserted in the airgun, discharge-related electrical connections are generally made automatically by engagement of the barrel-assembly in the airgun chamber as shown in FIGS. 72 and 74.

This does away with the tethering represented by cord 109 in FIG. 75 that is unobjectionable in a minimally-capable barrel-assembly for which, unlike the capable type, use when removed from the airgun is exceptional. An ablation or ablation and angioplasty-capable barrel-assembly may be tethered when a commercial cabled device with its own controls and power source, such as a linear atherectomy cutter is used; however, it is preferred that such devices be specially adapted for nonthethering attachment if not building into the power and control housing. In more capable ablation and atherectomy-capable barrel-assemblies, a side-socket can admit cabled devices and fluid lines.

VII2g(2). Minimally Ablation or Ablation and Angioplasty-Capable Barrel-Assembly Side-Socket Side-sockets are addressed below in the section entitled Ablation or ablation and angioplasty-capable Barrel-assembly Side-socket. Unlike an ablation or ablation and angioplasty-capable barrel-assembly, a minimally capable barrel-assembly is not devised for use as an independent apparatus and therefore has no power and control housing and hand grip that includes a side-socket. Electrical radial projection units in the muzzle-head are connected to the airgun power supply on engagement in the airgun chamber. When present, an electrical side-socket is mounted directly to the barrel-catheter in a small box or enclosure that can be slid along the barrel-catheter along sliding or brush contact strips.

The connectors consist of miniature or microminiature jacks or receptacles on a side of the box. Side-sockets not automatically closed by a one-way swing-away cover also serve as gas pressure relief outlets. Unlike the connection of the components within the barrel-assembly through the end-plate, the incorporation of a side-socket allows the continued connection and use of ablation, angioplasty, or intermittent (touch-up) intima stabilizing components and functions when the barrel-assembly is engaged in the airgun chamber. Such include side-sweeper type abrading radial projection unit tool-inserts with trap-filter, a 'cold' air gun for delivering cold or hot air, attached cylinders of compressed or liquified gas for chilling, and when installed in an edge-discharge barrel-assembly, a laser. Any fluid connection requires a fluid side-socket that provides a passageway for the pipe from the external source to enter the central canal.

The box, which is mounted as would a power and control housing, includes a levered cam engagement detent so that it can be slid along the barrel-catheter and temporarily fixed in position. The range in longitudinal position available is not limited to that of brush contact with the strips; however, electrical control is lost when the ends of the sliding contacts are overextended. Exceptionally, a minimally capable barrel-assembly can include a fluid operated radial projection circuit. Coupling of the incoming line to the circuit is then limited to a single position along the length of the barrel-catheter at which the openings on the inner surface of the housing and inlet to the circuit align, this position indicated by a circumferential tic alignment mark at that position.

The addition of an electrical side-socket allows a minimally ablation or ablation and angioplasty-capable barrel-assembly draw power while not engaged in the airgun. Tethered thus, freedom of movement is not equal to that of an ablation or ablation and angioplasty-capable barrel-assembly. Further supplementation such as an attachable battery pack with controls and control panel to operate the components within the barrel-assembly, or an open central canal as provided in a combination-form type ablation or ablation and angioplasty-capable barrel-assembly is considered as inferior approximation to an ablation or ablation and angioplasty-capable barrel-assembly produced as such.

VII2g(3). Minimally and Fully (Airgun-Independent) Ablation or Ablation and Angioplasty-Capable Radial Discharge Muzzle-Heads Muzzle-heads for use in blood vessels differ from those limited to use for ablation in requiring gas return channels to prevent the introduction of gas into the bloodstream. All but limited purpose embodiments incorporate a heating element or excimer laser at the nose for ablation or angioplasty, those small in gauge a heating element as this does not require a cable entirely through the axis as in a combination-form barrel-assembly with edge-discharge muzzle-head of the kind shown in FIG. 66.

VII2g(3)(a). Rapid Cooling Catheter and Cooling Capillary Catheter for Cooling Heated Turret-Motor, Electrically Operated Radial Projection Unit-Lifting Thermal Expansion Wire and Heaters, and Recovery Magnets To quickly return the thermal angioplasty turret-motor, one or both brush-lifting thermal expansion wires, and one or both recovery electromagnets of the recovery and extraction miniball electromagnet assembly to body temperature, a cooling catheter, as addressed below in the section entitled Cooling Catheters (Temperature-changing Service-catheters), is passed down the barrel-assembly so that its cold air is delivered in adjacent relation to these components. Because in a combination-form barrel-assembly, the longitudinal center is taken up by an atherectomy burr or excimer laser cable, an edge-discharge muzzle-head must be used, so that only a spare barrel-tube is available for passing the rapid cooling capillary catheter up to the turret-motor.

Fluid circuits can deliver a fluid prechilled or preheated to a target temperature, but electrical circuits cannot. A fluid circuit can be used to achieve and transmit heat, a thermoplasty temperature for example, more quickly than can an electrical circuit, but chilling, that is, reversion to body temperature or attaining cryoplasty temperature (−10 degrees centigrade) is not currently practicable using electrical means. Such means thus necessitate the pre- or midprocedural intromission in a barrel-tube or the central canal of a chilled rod, or cooling catheter. Cooling catheters can seal in a solution such as one part propanol to three parts water and thus remain pliable or can circulate a refrigerated coolant from a remote pump.

Since cooling catheters can also be preheated, designation as 'cooling' is nominal and based upon primary use to quickly cool an electrically heated component. The emergent field of electronic refrigeration may eventually supplant the need for cooling catheters, and the related field of electronic thermometry application to the control of winding temperatures to minimize thromogeneric temperatures during thermoplasty, that is, achieve 90 degrees centigrade quickly, hold that temperature during the thermoplasty, then revert to normal body temperature as soon as the thermoplasty is completed. Once made practicable, electronic refrigeration will have application to cooling catheters and electrically operated radial projection tool-insert cold plates for performing a cryoplasty, for example.

Currently pursued along various lines, electronic refrigeration has the potential to allow changes in temperature at a remote point, eliminating the need to pipe a heated liquid or gas to achieve thermoplasty or chilled liquid or gas to achieve cryoplasty temperature with a barrel-assembly (see, for example, Majumdar, A. 2009. "Thermoelectric Devices: Helping Chips to Keep their Cool," *Nature Nanotechnology* 4(4):214-215; Chowdhury, I., Prasher, R., Lofgreen, K., Chrysler, G., Narasimhan, S., Mahajan, R., Koester, D., Alley, R., and Venkatasubramanian, R. 2009. "On-chip Cooling by Superlattice-based Thin-film Thermoelectrics," *Nature Nanotechnology* 4(4):235-238; Petta, J. R. 2009. "Electronic Refrigeration on the Micron Scale" *Physics* 2,27; Prance, J. R., Smith, C. G., Griffiths, J. P., Chorley, S. J., Anderson, D., Jones, G. A. C., Farrer, I., and Ritchie, D. A. 2009. "Electronic Refrigeration of a Two-Dimensional Electron Gas," *Physical Review Letters* 102(14): 6602-6606; and Giazotto, F., Heikklä, T. T., Luukanen, A., Savin, A. M., and Pekola, J. P. 2006. Opportunities for Mesoscopics in Thermometry and Refrigeration: Physics and Applications," *Reviews of Modern Physics,* 78(1): 217-274, updated preprint to 2008 under title revised as "Thermal Properties in Mesoscopics: Physics and Applications from Thermometry to Refrigeration," available at http://arxiv.org/PS_cache/ cond-mat/pdf/0508/0508093v4.pdf; Edwards, H. L, Niu, Q., and de Lozanne, A. L. 1993. "A Quantum Dot Refrigerator," *Applied Physics Letters* 63(13): 1815-1817).

Related technology should make possible small-scale thermometry that can be incorporated into the onboard controls of ablation or ablation and angioplasty-capable barrel-assemblies for temperature control. A noncombination-form barrel-assembly with center-discharge muzzle-head, however, provides a central canal to allow a cooling catheter of larger diameter and an ejection-head channel for insertion of the distal end of the cooling catheter for more direct access to the recovery electromagnets. The gas return paths prevent cooling gas from entering the bloodstream. The mechanism by which the radial projection units are controlled is described under the sections below entitled Structure of Electrically Operated Radial Projection Units and Radial Projection Unit Control and Control Panels, Elecrical and Fluidic or Piped.

A cooling catheter is needed when the internal configuration of the muzzle-head fails to obstruct the release of pressurized gas into the bloodstream. Using a center-discharge muzzle-head, when the turret-motor is sent heating current to quickly raise to and hold the temperature at 90 degrees centigrade for thermal angioplasty, preferably the slit valve but possibly a spare barrel-tube is used to admit the rapid cooling extruded polytetrafluoroethylene capillary catheter. With such a muzzle-head, when one or both miniball recovery tractive electromagnets are used for thermal angioplasty, the rapid cooling capillary catheter is advanced up through the central canal and into the ejection head rapid cooling capillary catheter insertion channel.

In a combination-form angioplasty barrel-assembly, the slit valve is eccentric. Because the electromagnets are contained within chambers that directly communicate with the bloodstream beyond the gas return paths, blowing cold air directly on the electromagnets would risk introducing gas into the bloodstream. For this reason, the end of the capillary catheter is closed and side-holes are used. Cooling of the electromagnets is through the metal of the ejection head, the larger diameter of the insertion channel allowing the cooling gas to circulate against the interior walls of the insertion channel and exit through the central canal.

Using an edge-discharge muzzle-head as affords a central passageway for interchanging different cabled devices in a combination-form barrel-assembly or incorporating a fiberoptic endoscope, for example, the cooling catheter is moved forward until its distal tip closes off the muzzle-port of the barrel-tube through which the cooling catheter was passed. If only one electromagnet had been used to perform a thermal angioplasty, then the cooling catheter is passed through a barrel-tube proximal to that electromagnet, which can be identified, each barrel-tube marked on end-plate 99 in FIG. 72. The asymmetry of this position and separation by metal surrounding the electromagnets mean that the rate volume of chilled air delivery must be greater than in a center-discharge muzzle-head.

The use of more than one cooling catheter in an edge-discharge muzzle-head to ameliorate the less effective cooling associated with the asymmetry of cooling catheter placement is practicable when the caliber of the barrel-tube or barrel-tubes used for discharge are not affected. Combination-form barrel-assemblies with edge-discharge muzzle-heads can be deliberately designed to be cooled in this way. The functionality of providing a service-channel for access to the muzzle-head for various purposes is discussed above. Referring now to the detailed view of a center-discharge muzzle-head shown in FIG. 67 with laser 169 occupying central channel 155, and in FIG. 66 with central channel 155 unoccupied, for ease of insertion and passing down central channel 155 to ejection head 84 and recovery electromagnets 65 of a cooling catheter (rapid cooling catheter, rapid cooling capillary catheter), the distal end of cooling catheter 180 in FIG. 68 can be closed off and angled (chamfered, conical).

When cooling catheter 180 consists not of a prerefrigerated solid rod but instead releases a chilled fluid, cooling catheter 180 includes round side-holes 181 that surround and extend proximally over the length to be cooled. When radial projection units proximal to the muzzle-head need not also be cooled, this length will be that of the muzzle-head, thus including the turret-motor with through-bore torque turret-motor rotor 82 and stator 62 and recovery electromagnet 65 assembly.

Chilled air is delivered through the cooling catheter by connecting its free proximal end with a diameter-reducing adapter to the nozzle of a cold air gun using a vortex tube supplied with compressed air, such as manufactured by the Vortec Division, Illinois Tool Works Air Management; Airtx International; Exair; and Pelmar Engineering. The base of the cold air gun is fastened to the side of the interventional airgun cabinet. Alternatively, high purity 1,1,1,2-tetrafluoroethane (R134a) cryogen spray is blown through the cooling catheter side-holes under low pressure by inserting the free proximal end of the cooling catheter into the spray nozzle hole of the aerosol can containing the tetrafluoroethane, the need for a diameter-changing adapter depending upon the diameter of the cooling catheter.

Testing has revealed tetrafluoroethane to be safe (Emmen, H. H., Hoogendijk, E. M., Klöpping-Ketelaars, W. A., Muijser, H., Duistermaat, E., Ravensberg, J. C., Alexander, D. J., Borkhataria, D., Rusch, G. M., and Schmit, B. 2000. "Human Safety and Pharmacokinetics of the CFC Alternative Propellants HFC 134a (1,1,1,2-tetrafluoroethane) and HFC 227 (1,1,1,2,3,3,3-heptafluoropropane) Following Whole-body Exposure," *Regulatory Toxicology and Pharmacology* 32(1):22-35; Gunnare, S., Ernstgård, L., Sjögren, B., and Johanson, G. 2006. "Toxicokinetics of 1,1,1,2-tetrafluoroethane (HFC-134a) in Male Volunteers After Experimental Exposure," *Toxicolology Letters* 167(1):54-65).

To allow the rigidity necessary for very thin, for example, 0.39 millimeter, cooling catheters to be passed to the muzzle-head through an available barrel-tube, the cooling catheter is made of polytetrafluoroethylene. In a combination-form barrel-assembly that must have an edge-discharge muzzle-head the use of an available barrel-tube for this purpose is unavoidable. Although the effect is slight because of the small diameter of the cooling catheter, this affects the flexibility, hence, trackability of the barrel-catheter. Since inserting the cooling catheter can assist in advancing the barrel-assembly, so long as care is taken to avoid stretching injury, this can be used to advantage.

Tubes and solid rods made of many different materials and covering a wide range of flexibility can likewise be inserted to stiffen or straighten the distal end of the barrel-assembly. At relatively close distances, a powerful hand-held electromagnet, even if portative rather than tractive, can also be used to aid in steering the muzzle-head, the more so if the muzzle-head incorporates magnetically susceptible matter for this purpose. Connecting the $B_0$ magnet of a magnetic resonance imager as addressed below in the section entitled Use of an External Electromagnet to Assist in Mishap Recovery and Stereotactic Arrest and Extraction of a Circulating, Dangerously Mispositioned, or Embolizing Miniball allows not only muzzle-head steerability but also atheromatous lesions to be compressed much as does a balloon.

A dividing and diameter changing adaptor allows the use of multiple cooling catheters with a single cold air gun; the use of a separate cold air gun for each cooling catheter is generally not necessary. Provided trackability is not impaired, to eliminate insertion time and allow immediate retreat from the 90 degree centigrade target temperature for thermal angioplasty back down to body temperature, multiple cooling catheters are prepositioned. Otherwise as many cooling catheters are prepositioned as do not affect trackability. Using a center-discharge barrel-assembly, the main and larger diameter cooling catheter is passed down the central canal and into the ejection head channel with another, usually capillary gauge, cooling catheter passed down the barrel-tube closest to the heated element.

VII2g(3)(b). Turret-Motor and Recovery Electromagnet Insulation, Leads, and Control of Winding Temperatures when Used as Heating Elements in Ablation or Ablation and Angioplasty-Capable Barrel-Assemblies The thermoplasty resources in an ablation or ablation and angioplasty-capable barrel-assembly include the turret-motor and recovery electromagnet windings and any electrical and/or fluidic radial projection units. Those in a radial projection catheter include only electrical and/or fluidic radial projection units. Electrical heating elements, hence, electrical radial projection systems, allow only heating, not cooling; rapid cooling from the thermoplasty temperature, usually 90 degrees centigrade, back down to body temperature must be accomplished with chilled fluid. To rise from body temperature past thrombogenic temperatures to the procedural temperature as quickly as possible with an electrical heating element requires initially surging, continuously modulating, and sustaining the current so long as the target temperature is needed.

Turret-motors and tractive electromagnets to serve as a heating elements for thermal angioplasty must incorporate special features of thermal and electrical insulation, to include winding insulation that is effective as an electrical but not as a thermal insulator, such as Master Bond EP34AN epoxy adhesive/sealant (thermal conductivity 22-24 BTU/in/ft$^2$/hr/° F.), pyrolytic boron nitride, or boron nitride, for example. Efficient radiation to the endothelium of winding-generated heat is through heat-windows, addressed in the section to follow. Since atheromatous lesions are usually asymmetrical, restricting the radiation of heat from the muzzle-head allows less heat to be directed toward less affected radii, hence, more discretionary treatment.

This is approximated by providing that only a delimited arcuate sector of the proximal portion of the muzzle-head shell or body serving as motor housing will radiate heat, the balance of the housing being thermally insulating. The turret-motor as thermal angioplasty heating element can be supplemented through use of the tractive electromagnet(s) for the same purpose. Ideally, once the heat within the muzzle-head body met or exceeded 90 degrees centigrade, the heat transmission window would radiate only 90 degrees centigrade. The sparsely intermittent duty of the turret-motor in positional control and the fact that the motor is fed current only when needed mean that little heat is generated.

This allows a sector of the muzzle-head shell to exceptionally be made of a material without value as a thermal insulator. Since atheromatous lesions are usually asymmetrical, the capability to differentially heat the turret motor over a restricted arc of its circumference gives more discretionary control, but also requires that lower thrombogenic temperatures are not transmitted to the adjacent arcs, as discussed below. Silver and copper having been specified as the materials preferred for the heat-windows on the basis of maximum thermal conductivity, the selection and thickness of the materials used in heat-windows does not take into account such alteration in thermal conductivity as results from the fact that the exterior surface of the heat-window will be wetted with blood or some other bodily fluid.

The ideal turret-motor as heating element would quickly rise from room temperature to 90 degrees centigrade, quickly drop from 90 degrees to room temperature, and be enclosed within a motor housing having a copper window slot through which the heat would be conducted, other portions of the entire turret-motor housing surface made of a material such as polytetrafluoroethylene or stainless steel having a markedly greater heat transfer coefficient or thermal conductivity the motor tolerating the heat otherwise retained without significant radiation to the surrounding lumen. Angioplasty performed manually before initiating stenting by inserting the proximal end of the barrel-assembly into the airgun, the motor would not, however, be used to rotate the muzzle-head during use as a heater.

For use as a heating element for the thermal angioplasty of a delimited arc of the lumen wall, a substantially temperature isolated arc of the turret-motor must be quickly heatable from a cool condition to 90 degrees Centigrade, necessitating wire and winding insulation that resists melting failure in small gauges depending upon size, especially when platelet blocking or anticoagulant medication is contraindicated making the avoidance of thrombogenic temperatures intermediate between zero and 90 to be avoided. To keep the nonangioplastic operating temperature of the turret-motor well when used for positional control below thrombogenic levels, the control circuit delivers current to the motor only when the motor is used.

To avoid the intervening thromogenic temperatures, the subminiature silver wire turret-motor and recovery tractive electromagnet windings must be capable of being quickly elevated to 90 degrees centigrade, the initiating of heating commencing with a current surge that gradually levels off to maintain a constant temperature as mentioned in the preceding sections entitled Concept of the Extraluminal Stent and the Means for Its Placement and Thermal Conduction Windows (Heat-windows) and Insulation of the Muzzle-head Body in Thermal Ablation or Thermal Angioplasty-capable Barrel-assemblies. Overheating normally results from excessive starting torque or torque at elevated speeds, whereas here heat is deliberately applied when the motor is not in use as a driver. That heat must, however, be dealt with when the motor is used as a driver.

Since fluoropolymers are effective thermal insulators, when the muzzle-head is or coated with a thin layer of a fluoropolymer to obtain a no-stick surface, the turret-motor is given a thinner or no such coating. However, if the coating has microscopic gaps, a thinner coating over the motor may still allow sufficient heat to pass through to the lumen wall. Even though rotation is intermittent or discontinuous and angle-to-angle within a circle or semicircle, use as a rotary driver immediately following use as a thermal angioplasty heater is better accomplished with a turret-motor that dissipates the excessive heat previously required quickly and thus averts rotatory instability (see, for example, Basu, A., Moosavian, S. A., and Morandini, R. 2005. "Mechanical Optimization of Servo Motor," *Journal of Mechanical Design* 127(1):58-61).

Heating the stator to perform thermal angioplasty represents a separate mode of turret-motor operation and is not employed when it is necessary to rotate the muzzle-head. For example, to combine thermal and side-sweeping angioplasty, the action is carried out transluminally under manual control with one or both of the side-brushes—which may be the same or different in bristle stiffness and tip conformation—deployed at a fixed rotational angle with the turret-motor heated at stall. Then to rotate the side-brush or brushes, the manual action is suspended, the turret-motor switched for rotation, the brush or brushes rotated, and the turret-motor switched back to heat while stalled in order to resume thermal angioplasty at the new brush rotational angle.

The insulation of the turret-motor must tolerate sufficient current for thermal angioplasty without melting, and the turret-motor must be well temperature insulated from the more forward elements of the muzzle-head or extremes of temperature will produce a temperature gradient that will result in thrombogenic temperatures in these more forward elements at and around 50 degrees centrigrade (122 degrees Fahrenheit) (Post et al. 1996). For thermal angioplasty, the turret-motor stator must quickly pass the thrombogenic range and reach a temperature of 90 degrees centigrade when sent higher current while stalled, and must just as quickly cool to room temperature when the current is removed.

In a fully ablation or ablation and angioplasty-capable barrel-assembly, when current is sent to the turret-motor and/or either recovery electromagnet winding for use as a heating element, an interval or lag-time precedes the attainment and stabilization of the target temperature at the heat-window. The same pertains to electrical tool-insert heating elements, addressed in the section below entitled Temperature Control in Electrical Tool-inserts. Where fluid or piped heat-windows passed through insulated lines can deliver fluid already heated or chilled at the target temperature to effect rapid cooling, electrical heaters, unless just removed to stabilize medication in preloaded syringe tool-inserts, commence heating at between room and body temperature.

The more quickly can the thrombogenic temperatures separating the body and target or operative temperature be passed through and the target temperature stabilized, the less platelet blockade will be needed, and the less will be the risk of bleeding. Large barrel-assemblies for use in the trachea or bronchi and gastrointestinal tract, for example, can accommodate microminiature thermocouples to sense the temperature as such, allowing independent proportional-integral-derivative closed-loop control of the temperature at each heat-window.

A precision thermocouple consisting of a fine bimetallic thermal expansion strip, such as one made of invar steel and brass or aluminum, that thermomechanically completes the circuit for current flow-through by making contact-connection only when its temperature corresponds to over 50 degrees centigrade (122 degrees Fahrenheit) for thermal ablation (see, for example, Habash, R. W., Bansal, R., Krewski, D., and Alhafid, H. T. 2006. "Thermal Therapy, Part 1: An Introduction to Thermal Therapy," *Critical Reviews in Biomedical Engineering* 34(6):459-489; Diederich, C J. 2005. "Thermal Ablation and High-temperature Thermal Therapy: Overview of Technology and Clinical Implementation," *International Journal of Hyperthermia* 21(8):745-753) and 90 degrees centigrade (194 degrees Fahrenheit) for angioplasty at the heat-window-endothelial interface, can be used.

If external to the barrel-assembly, which is more likely with large gauge barrel-assemblies supported by commercial closed-loop temperature controllers, the controller is connected through an electrical side-socket. The temperature for other applications of heat addressed herein vary according to use for thermal hemostasis (thermocoagulation −70 degrees centigrade (see, for example, Conway, J. D., Adler, D. G., Diehl, D. L., Farraye, F. A., and 7 others 2009. "Endoscopic Hemostatic Devices," *Gastrointestinal Endoscopy* 69(6): 987-996), the specific adhesive heated to accelerate initial setting, or medication heated following electrical or fluidic radial projection unit syringe injection to accelerate a chemical reaction or uptake, for example.

As addressed below in the sections entitled Electrical Tool-inserts, to Include Gas Discharged Injection and Ejection Syringes and Fluidic Tool-inserts, to Include Ejector-irrigator-aspirators and Injectors, both electrical and fluidic radial projection unit syringe tool-inserts can warm, and fluidic syringes can chill medication prior to release within the lumen (ejection), or hypoendothelialor hypointimal injection. With independently heatable recovery electromagnets, three heat control circuits or channels are required in the hand-grip in addition to the preferably separate drive-control circuitry for the 3-phase turret-motor.

With either temperature (true closed-loop) or current (quasi closed open-loop or open-loop even with respect to current) control, each winding can be assigned its own embedded microcontroller, or one microcontroller can independently or jointly control the temperature outside each heat-window. While a larger microcontroller could be programmed to control the turret-motor and recovery electromagnet windings both for heating and electroactuation, the separate control of each magnet and the motor is preferred as affording the greater dependability of redundancy. Barrel-assemblies for use in small gauge lumina do not allocate space for a temperature sensor at the expense of working elements.

Instead, quick rise to and stabilization at the target temperature is accomplished indirectly and remotely, preferably through closed-loop regulation of the current or current feedback control, by a power and control housing, or battery-pack hand-grip, embedded microcontroller. Control can, however, be genuinely open-loop, meaning without current feedback. That is, a separate microcontroller for each of the three windings or one larger microcontroller is programmed to control the current by equivalence to temperature. The control of the current to each winding is thus close-loop, but control of the equivalent temperature is open-loop.

Rather than using feedback from a temperature sensor, the microcontrollers adjust the current to each each winding from the inmate battery-pack, the airgun power supply, or remote power supply through a digital potentiometer. Space for thermal insulation limited, protracted heating will eventually be conducted through the muzzle-head and must be reversed. Whether control is by temperature in a large or current feedback in a small barrel-assembly, to rise from body temperature outside each heat-window past thrombogenic temperatures to the target temperature as quickly as possible requires initially surging, then modulating the current to hold the temperature constant until shut off when the temperature must be brought back down to body temperature as quickly as possible.

With electrical heating, a cooling catheter or nearby fluidic radial projection fluid line must be used to quickly return a heated winding back down to body temperature. A negative feedback control microcircuit contained within the hand-grip shaped battery pack is used to surge the current when heating is begun and then gradually drop off the current with time, thus maintaining the temperature substantially constant until the cooling catheter is used to cool down the muzzle-head. The longer heating is continued, the more can heat accumulate within and be conducted through the muzzle-head.

Current feedback control in electrically operated radial projection tool-inserts, addressed below in the section entitled Electrical Tool-inserts, to Include Gas discharged Injection and Ejection Syringes, not only preserves the space that a temperature sensor would require but allows the control of all other electrical tool-insert functions, all current controllable. Redundancy for dependability equally important with electrically operated radial projection tool-inserts, these likewise are preferably controlled by separate microcontrollers. Incorporating different materials in different dimensions, each type muzzle-head will exhibit different temperature characteristics. The current requirements to quickly move between body and thermoplasty temperatures using each type embodiment will therefore be unique.

The control of temperature must therefore be determined on the basis of empirically testing each type if not each muzzle-head for current-to-temperature equivalency, the relation of temperature to current predetermined using the exact combination of components to be controlled. A specification sheet that states the times and temperatures for using heat and cooling catheters must be supplied with the specific barrel-assembly. The cooling catheter used for this can enclose a coolant and be refrigerated or provide a biluminal circuit for flowing a coolant, usually cool water. A side-socket allows the use of a remote commercial coolant pump and controls.

For free manipulability, however, ablation or ablation and angioplasty-capable barrel-assemblies whether large or small are preferably untethered by wires or hoses, control components such as temperature microcontrollers incorporated into the power and control housing, or hand-grip shaped battery-pack. Most often, the application of heat during a thermal angioplasty or to accelerate the initial setting time of a surgical cement, for example, cannot be kept so brief or intermittent that an objectional buildup of heat can be avoided. Especially in an angioplasty barrel-assembly for use to remove plaque so extensive that to treat it requires inordinate heat on-time, a cooling catheter is used to intermittently cool the muzzle-head.

Generally the turret-motor windings are not isolated for heat control; when used as a heating element, the turret-motor stator is energized as a unit despite having more than one winding with resistances between these. A heat-window can completely surround the turret-motor, or the radiation of heat can be constrained to circumscribed heat-windows which then aim the heat. Only muzzle-heads that are too small (other than for the low conductivity polymer shell) to insulate and thermally isotropic warrant limiting current to one motor winding.

VII2g(3)(c). Thermal Conduction Windows (Heat-Windows) and Insulation of the Muzzle-Head Body in Minimally or Fully Thermal Ablation and Thermal Ablation and Angioplasty Capable (Independently Usable) Barrel-Assemblies Thermal or "heat" windows, such as those shown in FIGS. 64 and 70 are heat radiating sectors in the muzzle-head body or shell. Heat-windows can be slit, slot, or all-around in form, the latter kept distal to the muzzle-ports or exit-holes. Peltier devices mounted to allow rotation can be used to furnish either heat or chilling. While not shown in FIG. 64, a heat-window is usually also present at the nose as seen in FIG. 70. A nose heat-window is given a toroidal cross-section to accommodate the distal tip of a nose-centered cabled device, such as a fiberoptic endoscope, for example, or the nose opening in a combination-form barrel-assembly.

While the thinness of the thermal insulation required in the body or shell of the muzzle-head makes thermal isolation difficult, the differential thermal conductivity of the window or windows in relation to the speed with which the control electronics and materials employed allow the target temperature to be attained and receded from affords a level of thermal isolation sufficient for thermal angioplasty with minimal risk of thrombogenicity due to heat retentive temperature gradients surrounding the radiative window or windows. For treating eccentric lesions, the heat-window or windows overlying a turret-motor can be reduced structurally or with tape to slits, slots, or rectangularly configured, rather than circumferential.

The term heat-window also applies to electrical and fluid tool-inserts, the latter even when used to conduct cold. Whereas electrical heat-window tool-inserts are limited to heating, generated by a coil, blank tool-inserts in piped radial projection units can be used as hot or cold plates. By exchanging the projection catheter or a tool-insert in the same projection catheter, electrical and fluid tool-inserts can be replaced with alternative tool-inserts that perform cutting (shaving), brushing, injection, infusion, or aspiration functions. A heat-window at the distal end of the muzzle-head is a blunt dome-shaped nose heat-window. Heat-windows are of two types—those heated by passing current through an actuator winding positioned just behind them, and piped radial projection units, addressed below in the section entitled Piped Radial Projection Units, which are heated or chilled by flowing a heated or chilled fluid against the inner side of a peripheral face-plate.

To afford a return path, the hot or cold gas, liquid, or gel used to heat or chill a piped face-plate type heat-window must be channeled through a dual lumen pipe or service-catheter passed down the pipe to the face-plate. This section relates to the operation of the heat-window or windows of the muzzle-head as can be separately placed about or made to surround the turret-motor and two recovery electromagnets in alternative use as heating elements rather than as motion control devices. Such use must be discretionary in that each of the three are usable at any time for either moving or heating as required. When connected to a source of hot gas, piped blank or flat-faced radial projection unit tool-inserts made of thermally conductive material looking outward toward the lumen wall and thermally insulated behind and to the sides (within the elevation shaft) can be used as heat-windows.

These are situated in front of (distal to) the turret-motor housing and to the rear of (proximal to) the muzzle-head flex joint, and not superjacent to the turret-motor and recovery electromagnet windings. The use of these together with winding heated heat-windows is possible. While actuator winding-heated heat-windows are limited to the conduction of heat, fluid (fluidic, piped) radial projection unit blank tool-inserts can be heated or chilled by delivering liquid or gas at the desired temperature to their rear face and are interchangeable with numerous alternative tool-inserts that allow the delivery of any fluid to the surface or subsurface of the lumen wall.

Thermal windows allow the use of fluidic or piped radial projection units to perform other functions. For the purpose of allowing the muzzle-head to be used for performing a thermal angioplasty, heat transfer from the windings within the muzzle-head is by conduction, the small internal diameter of the different systemic vasa to require treatment imposing stringent limitations upon winding diameters and the thickness of the insulation that can be used. The recovery electromagnets, turret-motor stator (armature), and subminiature trap-filter deployment solenoid windings all consisting of fine silver wire, ninety degrees centigrade is not so hot as to necessitate extraordinary insulation of the windings, connections, or cabling.

Even though these components are positionally disabled during thermal use, heat-conducting windows of silver, which has a heat transfer coefficient at 25 degrees centigrade of 429, or of copper, 401, in the otherwise thermally insulated muzzle-head body allows heat to be directed from the nose-cap (nose dome) heat-window to the surrounding lumen wall and from the turret-motor toward lesions that may be circumferentially asymmetrical or eccentric. The higher temperature of a heat-window allows its position to be viewed through thermal imaging, and, if redundantly, allows the deliberate heating of a certain winding to assist in pinpointing not only the location of the muzzle-head but the orientation of the window.

To allow blood to flow past a muzzle-head flush fit to the lumen, the turret motor must be smaller in diameter than the portions of the muzzle-head that lie to the fore. Contact with the wall of the lumen requires that the turret-motor heat-window slightly protrude with smooth edges beyond the rest of the circumference of the turret-motor. Some blood can then flow around the heat-window past the motor body into the blood-grooves to the fore. The nose-cap heat-window of the recovery electromagnets is flush-mounted to the muzzle-body. The turret-motor and tractive electromagnets represent three independently controllable heating elements, each in its own circuit, in relation to which the muzzle-head body can incorporate heat-radiating windows of any shape, extent, separation, or connection.

However, except for ablation or angioplasty-incapable barrel-assemblies, to avert the disruption of vulnerable plaque by contact with the muzzle-head, all muzzle-heads for use in the vascular tree have a heat-window in the form of a forward end encompassing nose-cap and directional or circumscribed turret-motor heat-window. While the heat-windows shown in FIG. 64 are slot-shaped and thus directional, most turret-motor heat-windows will collar about the muzzle-head entirely over the motor. The recovery electromagnet heat-window or windows will more often be slot-configured for directional use. Using the recovery electromagnets separately, band, strip, or slit-shaped windows along either segment of the muzzle-head body along one side behind (proximal to) the nosecap heat-windo, for example, can be heated by the motor proximally and/or the magnets distally.

Since in a combination-form barrel-assembly, the central canal is occupied by an atherectomy burr or laser cable, this space is unavailable, necessitating the use of an edge-discharge muzzle-head, which requires that a spare barrel-tube be used as a cooling catheter entry and service-channel. The need to appropriate a barrel-tube affects the maximum diameter of the barrel-tubes, hence, the caliber of the miniballs that may be used when all the barrel-tubes are to be used for the discharge of miniballs; however, the diameter of the miniballs to be implanted will seldom be forced smaller by this factor, and then only when a multiple discharge barrel-assembly is preferred.

When the central canal in a multiple-discharge barrel-assembly, such as a four-way radial edge-discharge barrel-assembly, is already occupied by a laser or burr cable or by a trap-filter, access to the central canal for use as a service-channel to insert a cooling catheter of larger diameter is preempted. This necessitates the use of a spare barrel-tube as service-channel, limiting the cooling catheter to capillary tube gauge, typically 0.38 millimeters in outer diameter. Even though made of polytetrafluoroethylene for rigidity, to feed this fine catheter down to the ejection head and confirm its correct position represents a distraction and interruption that is avoided by prepositioning the catheter. Whether used for cooling or the delivery of medication or a lubricant, catheters requiring access through a service-channel are prepositioned.

Solid rods of graduated stiffness preferred for the purpose, catheters would seldom be used merely to stiffen or straighten the barrel-assembly, as when having passed a tortuous stretch. Limitation to a barrel-tube for the insertion of a cooling catheter means that the conduction path for chilled air to the turret-motor, the radial projection units deployed by thermal expansion wires, and the recovery electromagnets is asymmetrical, gives less effective conduction to the recovery electromagnets, and since the material of the barrel-tube, even thin-walled, is thermally insulative, necessitates the extension of the gas return path perforations along the sides of the barrel-tube to include the entire segment of the barrel-tube parallel to the area to be cooled.

For these reasons, a center-discharge barrel-assembly with its larger diameter central canal and ejection head cooling catheter insertion channel is superior to an edge-discharge barrel-assembly for thermal angioplasty. The effect of a fever on clotting with clot-suppressing platelet blockers (antiaggregants) in arteries or anticoagulants ('blood thinners') in veins, and dissolving (thrombolytic, fibrinolytic, 'clot-busting') drugs (streptokinase; urokinase; tissue plasminogen activator as tenecteplase or reteplase; recombinant tissue plasminogen activator, or alteplase, anisolylated plasminogen activator, or anistreplase) as conventionally administered for an angioplasty warrants further research.

Disregarding the administration of such medication, which infrequently produces significant bleeding complications Cote, A. V, et al. 2001 and Jong, P. et al. 2001, cited shortly following the section above entitled Objects of the Invention), to reduce the thrombogenicity of the arterial wall when heated, a temperature of 90 degrees centigrade (Celsius; 194 degrees Fahrenheit) or more serves to denature collagen and von Willebrand factor (Post, M. J., de Graaf-Bos, A. N., Posthuma, G., de Groot, P. G., Sixma, J. J., and Borst, C. 1996. "Interventional Thermal Injury of the Arterial Wall: Unfolding of von Willebrand Factor and Its Increased Binding to Collagen After 55 Degrees C. Heating," *Thrombosis and Haemostasis* 75(3):515-519; Humphrey, J. D. 2003. "Continuum Thermomechanics and the Clinical Treatment of Disease and Injury," *Applied Mechanics Reviews* 56(2):231-260; Bos, A. N., Post, M. J., de Groot, P. G., Sixma, J. J., and Borst, C. 1993. "Both Increased and Decreased Platelet Adhesion to Thermally Injured Subendothelium is Caused by Denaturation of von Willebrand Factor," *Circulation* 88(3):1196-1204; Borst, C., Bos, A. N., Zwaginga, J. J., Rienks, R., de Groot, P. G., and Sixma, J. J. 1990. "Loss of Blood Platelet Adhesion After Heating Native and Cultured Human Subendothelium to 100 Degrees Celcius," *Cardiovasc Research* 24(8):665-668).

Thermal angioplasty, or thermoplasty, windows, window-slits, and window slots are microrouted or electrical discharge machined into the sides of the proximal (rear) and distal (front) muzzle-head shells in a center-discharge muzzle-head and the proximal shell in edge-discharge or combination-form barrel-assemblies. The window openings or apertures are then covered over with silver or copper sheet which is inset or lapped into the outer surface of the opening or openings to create an edge that is flush to the surface of the muzzle-head body. The turret-motor slit or slot heat-window slightly protrudes or stands in relief of the surrounding surface, while the nose heat-window is flush or filet fit.

The window overlays are bonded along the overlap with a long-chained cyanoacrylate, or a DYMAX Corporation 200-CTH-series cement not subject to liberate toxic substituents upon degrading. To allow good slippage, or the noninjurious movement of the muzzle-head body against the endothelium, the heat-windows are masked for immersion (dip), plasma vapor, or sputter coating with a thermal insulating polymer. A fluoropolymer is preferred for a low coefficient of friction and little tendency for clinging to the endothelium. Since to prevent a temperature gradient about the heat-windo is impossible, the use of thermal insulation is intended to better focus the heat.

Where the heat foci do not pass, a platelet blockade or anticoagulant as appropriate reduces the risk of thrombus formation due to temperatures that intervene between body temperature and 90 degrees centigrade (Post et al. 1996, *Thrombosis and Haemostasis* 75(3):515-519 cited above). While at 3 millimeters (9 French) in outer diameter, most muzzle-heads will not allow any further coating, for additional insulation, the polytetrafluoroethylene coating on the outer surface of portions of the muzzle-head shell other than those cut away for the heat-windows, slits, or slots may be further coated with a thin layer of silica aerogel.

Further to reduce the number of components that would consume precious space and an overall complexity that would significantly increase costs:

a. Rather than to provide a local current-actuable insulating layer or movable insulating cover in surrounding relation to the heating elements (turret-motor and recovery electromagnet housings), the momentary temperature rise-time is discounted, platelet blockade or anticoagulant medication, which can be delivered in higher than the circulating or systemic concentration through a catheter passed through a neighboring barrel-tube or service-channel (addressed below) depended upon to minimize unwanted coagulation; and b. The same rapid cooling catheter or cooling capillary catheter (following section) is used in center and edge discharge muzzle-heads within the range of common diameters (2.5-4.0 millimeters), the placement and interval of time using a specific vortex tube or other means for supplying cold air required in each instance to drop the temperature from 90 degrees centigrade, or if used for thermal ablation in a ductus other than vascular, then the temperature that pertains, back down to body temperature (98.2 degrees Fahrenheit or 36.8 degrees centigrade) provided on a specification sheet that is supplied with the apparatus for setting the vortex tube timer, which interval of time has been predetermined empirically based upon multiple trials.

The low thermal conductivity of the materials used; rate of cold air delivery from the cold air gun, $CO_2$ or $NO_2$ cartridge; tight fit of the rapid cooling capillary catheter within the passageway employed whether peribarrel space, gas-return path, or spare barrel-tube used as a service-channel; and interval to pressure equalization among the holes toward the distal end of the cooling catheter is such that in a combination-form edge-discharge muzzle-head as discussed in the section to follow, extension proximally of the perforated distal segment of the fully inserted rapid cooling catheter to the turret-motor does not result in a significant lessening of the cooling effect at the turret-motor.

VII2g(3)(d). Radial Projection Units

Radial projection units are lifting mechanisms that hold and extend interchangeable tools, or tool-inserts, radially outward from and about the periphery of a barrel-assembly muzzle-head or a separate (special, dedicated) radial projection catheter, as addressed below in the section of like title. The ability to extend hypoendothelial or hypointimal injection needles and the cutting faces of tool-insert bits, for example, from beneath the surface of the barrel-assembly or separate catheter and then fully retract these into this safe recess makes it possible to use sharp implements and resume transluminal movement with little risk of perforating or introducing incisions into the lumen wall.

Radial projection units can also aid luminal passage of the barrel-assembly by releasing drugs to dilate or decongestant the lumen. To avoid protrusions that could snag, gouge, or incise the inner surface of the lumen, the radially outward edges of radial projection units and the faces of the tool-inserts placed in these follow the surface contour as seen in cross section. This is not evident in longitudinal section, however. Tool-inserts such as shavers or brushes are open-faced, any material having entered expelled when the tool-insert is lifted. For use in the bloodstream, a run-ahead protective embolic filter is deployed from the nose of the muzzle-head or separate noncombination-form radial projection catheter during any process likely to generate potentially embolizing debris.

Radial projection circuits and units are either electrical or fluidic, those electrical less requiring an increase in the gauge and stiffness of the barrel-catheter. For this reason, only electrical units are incorporated into the muzzle-heads of narrower minimally and fully ablation or ablation and angioplasty-capable barrel-assemblies. Fluid circuits and units are incorporated into large muzzle-heads and separate combination-form radial projection catheters, which can be slid over barrel-assemblies of matching size at any time, as addressed in the section below entitled Radial Projection Catheters. Generally, electrical circuits allow the incorporation into small gauge barrel-assemblies and the muzzle-heads thereof of side-looking (radially outward or lumen wall facing) electrical tool-inserts where a fluid circuit would not fit.

Electrical and fluid tool-inserts share and have unique capabilities. Electrical tool-inserts can incorporate an actuator but must heat syringe contents locally and have limited ability at delivering fluids. A fluid injection tool-insert, or syringe injector, for example, can continue to inject without the need for repeated needle punctures. Fitting a tube the same in outer diameter as the muzzle-head about a barrel-catheter significantly affects pliancy or trackability, but depending upon its extent proximally, can yield up to the entire intracorporeal length of the barrel-assembly for incorporating tool-inserts. In small gauge barrel-assemblies, these will usually be limited to electrically operated units.

Self-contained electrical/fluid system-neutral syringes, fluid system syringes, and fluid continuous-feed tool-inserts as described below can all be used to eject into the lumen or inject into the lumen wall any type medication or other fluid therapeutic substance to include those specified in the section above entitled Field of the Invention, and can do so at a preferred temperature. Also ejectable by these means are lubricants, used with or without the oscillatory operational mode of the turret-motor to pass tortuous stretches along a vessel, for example, as addressed above in the section entitled Turret-motor Operational Modes. Also injectable are embolizing agents, molten protein solder of lower melting point, and surgical cement, for example.

Such lumen side-looking injection of an embolizing agent eschews the unwanted reflux and diffusion that can affect nontargeted tissue while leaving the tissue intended inadequately embolized (see, for example, Novak, D. 1990. "Embolization Materials," in Dondelinger, R. F., Rossi, P., and Kurdziel, J. C., *Interventional Radiology*, page 295). Injection tool-inserts can be kept from sufficient outward (radial) extension that the ductus could be perforated, and a spring-strip beneath the lift-platform assures that tool-inserts to include cutting, abrading, and injecting are automatically retracted into the tool-insert housing at the instant that power is cut off to the tool or tools.

Tool-inserts can be blanks used as plugs in fluid unit not to be used, push-arms, inert cutting bits, or controllable tools that incorporate various mechanical, electrical, chemical, or a combination of such components. Radial projection units can be used to nudge the catheter in a desired radial direction, release medication or other therapeutic substances into the lumen or inject these into the lumen wall, heat or chill these substances, or thermo- or cryoablate the lumen wall, as well as perform cutting and other operations. Since the internal structure of these tool-inserts is anteroposteriorly asymmetrical to perform as emitters or aspirators depending upon the direction of fluid flow, units in the same fluid circuit will emit or irrigate or aspirate depending upon anteroposterior orientation in the circuit.

That is, reversing this orientation thus reverses the action, whereas tool-inserts placed in separate circuits of flowing in opposite directions perform the same action when anteroposteriorly oriented alike. Reversal of flow through an emitter-irrigator-aspirator tool-insert reverses its action from emission or irrigation to aspiration and the reverse. Thus, for antegrade or retrograde flow through the same fluid circuit, the same kind of tool-insert if oriented in reverse will perform the opposite action. Under higher pressure, an aspirator can be used to recover a mispositioned miniball when the recovery electromagnets are in use for another purpose, such as heating. An external magnet is usually needed to abut the aspirator face-plate over the miniball entry hole.

Units can be coordinated, such as by using one to inject a surgical cement and another to apply heat at the site to accelerate initial setting. Radial projection units as tool-insert lifting mechanisms are either electrical or fluidic, neither as a rule affording connection to a source of the other type power in order to support a hypothetical tool-insert incorporating a component requiring the other type power. Electrical and fluidic units can be coordinated so that fluid units are used to irrigate and/or aspirate a site under treatment by other fluidically or electrically operated tool-inserts. Generally, differences in function and performance characteristics are obtained through the use of different interchangeable tool-inserts rather than by building these into the permanent elements of the fluid circuit where adjustment would be awkward.

Optimal functionality requiring that every unit have tool lifting and retraction capability, all are designed to serve as lifting mechanisms. Injectors must be projected beyond the periphery of the muzzle-head or radial projection catheter, as addressed below in the section of like title, and lifted as a whole, whereas in emitters, lifting is of a plunger within the tool-insert of which the body (housing, enclosure) is not lifted. Extension is not necessary to eject a fluid into, aspirate from the lumen or the endothelial lining of the lumen, or heat, for example. However, most tool-inserts require extension during use, and most, such as mechanical ablation and injection tools, must be retracted to prevent incisions upon the resumption of movement. Therefore, nonprojectability precludes the use of a given unit for a majority of interchangeable tool-inserts wherewith to perform diverse applications.

At the same time, the space available for incorporating units into most muzzle-heads will be limited. For these reasons, all units are made to project and retract, and all tool-inserts must be usable in these units. Since resistance to lifting could result in damage to the lifting mechanism, tool-inserts are not made to completely fill the lift-shaft. Tool-inserts to serve as blanks or plugs with a unitary body are recessed when not in use, while others telescope a narrower lower into a wider upper part. Tool-inserts which can remain level with the surface of the muzzle-head, such as electrical and fluidic heaters, and which must maintain connection to the electrical or fluidic circuit through a base-plug, are made in two sections of which the lower or radially inward, central, and slightly smaller telescopes up into the upper larger or radially outward.

In self-contained disposable injection syringe tool-inserts (injectors, piston or plunger syringe injectors), as described below in the section entitled Self-contained Electrical/fluid system-neutral Tool-inserts, to Include Injection and Ejection Syringes, this action is essential to project and retract the needle. To accommodate the lifting mechanism, an electrical/fluid system-neutral inert bit or a fluidic flow-through or mechanical syringe ejection tool-insert can be made either with a unitary body that remains recessed within the lift-shaft when not in use and raised during use or with a lower body section that rises or telescopes up into a wider upper or radial section of the body that remains stationary with its top or radial surface flush to the surface of the muzzle-head or separate radial projection catheter.

The top or radial surface of the latter remains closer to the surface of the muzzle-head or separate radial projection catheter and is less prone to accumulate debris. Lifting is essential to raise an injection needle, brush, or shaving face into contact with the lumen wall. The lifting mechanism consists of the tool-insert holding and lift-platform and shaft, more detailed descriptions of the lift mechanism and its control provided in the sections below entitled Structure of Radial Projection Units and Radial Projection Unit Control and Control Panels, Elecrical and Fluidic or Piped, respectively.

In an nonpiped, that is, an electrically operated circuit, the tool holding and lift-platforms are raised or projected by delivering current to non-high temperature nickel-manganese-lead high thermal expansion alloy wires (see, for example, Bauer, H. J. 1977. "Mechanical Motions in Small Inaccessible Volumes," *Journal of Physics E: Scientific Instruments* 10(4):332-334; Radvel, M. P. and Evdokimova, O. I. 2004. "Alloys with a High Coefficient of Thermal Expansion Based on the Mn—Pd System," *Metal Science and Heat Treatment* 16(5):403-405 [original in Russian 1974, *Metallovedenie i Termicheskaya Obrabotka Metallov* 5:36-38]). While close to the turret-motor and ferromagnetic, the securing in position, disposition, and function of the thermal expansion wires results in little interaction between these.

As shown in FIGS. 52a, 53a, 54, 55, and 56, each nonpiped or radial projection unit 174 that is deployed and retracted electrically consists of radially oriented lift-shaft or well 182, opening onto the surface of the muzzle-head; tool-insert holding or support (tool holder, tool holding frame) and lift-platform 176, which rides up and down lift-shaft 182; and coiled thermal expansion wire 177 along the floor of lift-shaft 182, used to raise lift-platform 176. More specifically, lift-platform 176 is pan- or tub-shaped as a holding and lift platform in FIG. 53 when the tool-insert is secured by friction fit therein, but flat at the top as a deck or lift-platform when retention within lift-shaft 182 is by means of rotatable hold-down arms 186.

Since radial projection units will usually be subjected to levering forces while in use and directed other than upwards, retraction into lift-shaft 182 when lift-platform 176 is not energized or de-energized is not left to gravity but by the fitting of a base-plug into a small socket in the top of lift-platform 176, making it a holding and lift-platform. When this plug is used without hold-down arms 186 only to secure tool-insert 184 in place rather than to provide connection to an electrical or fluid power line, it is a dummy projection or dummy-plug without power conductor; otherwise, it provides the electrical or fluid connection to the line that carries the electrical or fluid current use to operate internal components within tool-insert 184.

In a nonholding lift-platform, a small spring (not shown) may be used to retract tool-insert 184. Alternatively, friction fitting, screw-in, or snap-in engagement can be used to retain tool-insert 184 within lift-shaft 182. Hold-down arms 186 in FIGS. 52a, 52b,54 thru 56, 59, 60, and 63 are positioned adjacent to lift-shaft 182 on the surface of the receiving device, whether a muzzle-head or radial projection catheter. In FIG. 54, for example, interchangeable tool-insert 184 is retained within lift-shaft 182 supported beneath by tool-insert lift-platform 176 by hold-down arms 186, which rotate around or slide as latch bolts into depressions in the top of the tool-insert of like depth as those to which hold-down arms 186 are fastened.

Thermal expansion wire 177 is illustrated as a simple coil, but depending upon the coefficient of thermal expansion, may require to be densely wound. Lift-shaft 182 seen in FIGS. 52a, 52b, 54 thru 56, 59, 60, and 63 in vertical section, and the tool-inserts for use therein are usually rectangular in cross-section but can be given any shape. The piston-plunger-receiving component in an ejection or injection tool-insert, as seen in the foregoing figures, is referred to as the 'barrel' and the intromitted component as the plunger, regardless of cross section, whether circular, square, or rectangular. A strip-spring is a band of springy material that is used to impart elasticity to a joint between a platform or panel in flush parallel relation to the strip-spring and a stationary neighboring structure.

These are usually mounted for unidirectional function just beneath the lift-platform to hasten retraction of the lift-platform when the electrical or fluid lifting current is turned off. A strip-spring interposed between two structures can be used to hold the surfaces of these structures in flush relation with the joint between these elastic. More specifically, the strip-spring is fastened at its center to a stationery structure to one of its sides. The strip-spring is a unidirectional device that when used to cover over an opening in a fluid circuit serves as a unidirectional fluid resistor. On the other side, the strip-spring is fastened to a movable platform by rivets in the platform that slide along slots in and towards the ends of the strip-spring.

Once a force separating the surfaces is removed, the strip-spring will pull the platform into flush relation. The restorative force of the strip-spring depends upon its material and dimensions, which can be specified with exactitude, the more so in disposable tool-inserts not subject to alteration from repeated use or fatigue. The material properties of the strip-spring and the length of the slots do not permit a degree of deformation, hence, the elastic limit of the strip-spring, to be exceeded. The strip-spring thus establishes a threshold force below which the joint will not open. Provided the fluid is constrained from taking another course and the fluid pressure is less than that necessary to flex the strip-spring, the strip-spring will obstruct the fluid from passing through a hole in the platform.

A fluid pushing against the platform with the necessary force will flex the strip-spring separating the platform from the stationary structure and expose the hole so that fluid will force its way through the hole, here the entry to the base-plug. The absolute cross sectional area of the equipment lumina are so small that gravitational effects due to the rotational angle of the muzzle-head or radial projection catheter are insignificant. A two-way or bidirectional fluid resistor can consist of an elastomeric slit membrane valve, which is a sheet of a synthetic (nonallergenic) elastomeric material such as a silicone elastomer containing a straight, X shaped, or stellate slit or slits.

When placed across a fluid conduit, the fluid must reach a certain minimum pressure before the edges of the slit, or slits are forced open creating a path for the fluid to pass through to the other side. For fluids or greater viscosity, the membrane is cut or die punched with perforations of variable cross sectional area over a variable area of the membrane. A one-way or unidirectional fluid resistor in the base-plug of a fluid tool-insert allows the tool-insert to be used as an aspirator. Once such a break-seal or push-through stopper is eliminated from the fluid path, however, the tool-insert actuating pressure no longer confronts an incremental threshold over the line pressure as would remain the case with a two-way or bidirectional resistor such as a slit-membrane.

Strip-springs made of more resilient spring sheet metal and mounted to allow flexion to either side can replace elastic slit membranes for use in tool-inserts that must aspirate and would therefore clog. Membranes are is not sufficiently elastic to replace a strip-spring for the purpose of retracting an injector or cutting face, and while bidirectional, are readily clogged by debris and thus unsuitable for use in tool-inserts that must also be capable of aspiration as is preferred. Where rigidity rather than elasticity are desired, a similar passable pattern is molded or machined into a baffle plate of inelastic plastic or metal sheet. The material of the sheet used to make any type of fluid resistor or baffle and the dimensions and conformation of both sheet and cut are widely variable, allowing the rate of flow-through to be adjusted as necessary for the viscosity and pressure of the channeled fluid.

The same pertains to any fluid resistor or baffle whether a strip-spring, membrane, of baffle plate. Baffles are circular or rectangular according to the path in which these are positioned. When the circuit must be used with fluids of widely different viscosity, plastic plates with different sized apertures are used interchangeably. In tool-inserts, which must be interchangeable, perforated plates are used as fluid resistors or baffles to adjust lift-platform lifting force and rate of outflow through the tool-insert into the lumen. The perforated passive fluid resistor roof-plate would be a bidirectional resistor were it not hinged to lift out of the way to allow debris to move in the retrograde direction and to act as a venturi during aspiration as addressed below. In tool-inserts that aspirate, these are mounted to passively turn aside by an inflow.

In the permanent fluid unit lifting mechanism, which must accommodate tool-inserts that are capable of aspirating, a perforated plate hinged along the chamber outlet-directed edge is used to roof over the outlet chamber as a fluid resistor during antegrade flow. In retrograde flow (during aspiration), the extent to which the inward edge of the plate can rise is limited. This causes the fluid passing the aperture before the opening into the tool-insert base-plug opened by the lifting of the inner or medial edge of the plate to increase in velocity thus creating suction at the opening into the plug. A initial charge or prefilled fluid injection or ejection tool-insert must be discharged before the tool-insert can be used for aspiration. When such tool-inserts are used, an adjacent circuit must be used for aspiration, any unit not to aspirate having been plugged with a blank tool-insert.

To avoid clogging, the plate is passively lifted out of the way by a retrograde flow. For this reason, a barrel-assembly or radial projection catheter, as addressed below in the section of like title, having parallel fluid radial projection circuits is preferred. Procedures that generate significant debris recommend the use of a bipartite simple radial projection catheter or barrel-assembly with multiple interchangeable combination-form radial projection catheters each of which includes at lease one fluid circuit. A baffle or filter ahead of the roof baffle to trap larger debris is not preferred as inevitably clogged; however, if the velocity of retrograde flow during aspiration is not too great, the bottom portion of the outlet chamber will serve to trap particles of greater mass that drop down to the floor.

Where larger sized debris is anticipated, the use of units having deeper lifting mechanism chambers can avert clogging. Unlike rotatory atherectomy, the debris here is larger and should not be released into the bloodstream. Since aspiration or retrograde flow must inevitably accumulate debris, whenever possible, operations involving antegrade flow should always be conducted first; if retrograde is followed by antegrade flow, debris can be propelled forward clogging the circuit if not expelled our of the tool-insert. However, flushing through the circuit, first with a tissue solvent such as sodium hypochlorite (bleach) moderately concentrated for quick effect, immediately followed by water, allows antegrade flow to be resumed without the need to withdraw.

Neither need the flushing process unduly detain completion of the intervention. Since only the interior of the circuit contacts the solution, the concentration can be greater, hence, the duration for dissolution much reduced compared to the use of dilute tissue dissolution solvents in endodontic practice. The use of sodium hypochlorite, for example, in higher concentration increases the level of tissue toxicity, making it necessary to confirm that the fluidic circuit is free of any leaks.

If a resumption in antegrade flow must follow aspiration, then the circuit is flushed through with a tissue dissolving solution (see, for example, Christensen, C. E., McNeal, S. F., and Eleazer, P. 2008. "Effect of Lowering the pH of Sodium Hypochlorite on Dissolving Tissue in Vitro," *Journal or Endodontics* 34(4):449-452; Clarkson, R. M., Moule, A. J., Podlich, H., Kellaway, R., Macfarlane, R., Lewis D., and Rowell, J. 2006. "Dissolution of Porcine Incisor Pulps in Sodium Hypochlorite Solutions of Varying Compositions and Concentrations," *Australian Dental Journal* 51(3):245-251; Zehnder, M., Grawehr, M., Hasselgren, G., and Waltimo, T. 2003. "Tissue-dissolution Capacity and Dentin-disinfecting Potential of Calcium Hydroxide Mixed with Irrigating Solutions," *Surgery, Oral Medicine, Oral Pathology, Oral Radiology, and Endodontics*. 96(5):608-613; Zehnder, M., Kosicki, D., Luder, H., Sener, B., and Waltimo, T. 2002. "Tissue-dissolving Capacity and Antibacterial Effect of Buffered and Unbuffered Hypochlorite Solutions," *Oral Surgery, Oral Medicine, Oral Pathology, Oral Radiology, and Endodontics* 94(6):756-762; Okino, L. A., Siqueira, E. L., Santos, M., Bombana, A. C., and Figueiredo, J. A. 2004. "Dissolution of Pulp Tissue by Aqueous Solution of Chlorhexidine Digluconate and Chlorhexidine Digluconate Gel;" *International Endodontic Journal* 37(1):38-41; Yang, S. F., Rivera, E. M., Baumgardner, K. R., Walton, R. E., and Stanford, C. 1995. "Anaerobic Tissue-dissolving Abilities of Calcium Hydroxide and Sodium Hypochlorite," *Journal of Endodontics* 21(12):613-616) and water (see, for example, Motta, M. V., Chaves-Mendonca, M. A., Stirton, C. G., and Cardozo, H. F. 2009. "Accidental Injection with Sodium Hypochlorite: Report of a Case," *International Endodontic Journal* 42(2):175-182)) before resuming antegrade treatment.

Appurtenant of the lifting mechanism as the permanent part of the circuit built into the barrel-assembly or radial projection catheter, the use of strip-springs and of perforated plastic plates to cover over the outlet chambers in a fluid circuit are addressed in this section. By contrast, elastic membrane resistors are most often used within the interchangeable tool-insert components of the radial projection system, and are therefore addressed below in the section entitled Fluidic Tool-inserts, to Include Ejector-irrigator-aspirators and Injectors. Readily clogged by debris, elastic slit membrane resistors are limited to use within nonaspirating tool-inserts for the purpose of reducing the flow rate of discharge during ejection or irrigation with a light viscosity fluid.

While radial projection units per se only lift inert and self-contained syringe-type tool-inserts and can additionally provide electrical or fluid current to and/or through their respective types of tool-inserts, the functions performed by radial projection units cannot be addressed apart from the tool-inserts these support, the two working as a unit. There are essentially three types of tool-insert, 1. Mechanical, wherein a 'plug' extending downward from the base is not needed to fasten the tool-insert inside the projection unit, so that this type is usable in either type system, 2. Electrical, wherein the 'plug' is an electrical as well as a mechanical connector, and 3. Fluidic, wherein the 'plug' is a tube extension that is a fluid as well as a mechanical connector. Mechanical, electrical, and fluidic tool-inserts can be further categorized.

Mechanical tool-inserts that are self-contained as not to require connection to and thus equally usable in either an electrically or a fluidically controlled system, making these electrical/fluid system-neutral. Any 'plug' extending down from the base, if present, serves only to better stabilize the tool-insert in the projection unit. These include:

1. Simple mechanical tool-inserts, such as inert bits with shaving or abrading working faces that require radial extension during, and retraction immediately following use.

2. Compound mechanical, wherein the tool-insert, usually a syringe, includes a mechanical element, such as a spring used to release a fixed dose of medication or another therapeutic substance into the lumen or inject it into the lumen wall. Electrical tool-inserts, wherein the tool-insert base-plug is an electrical as well as a mechanical connector for connecting an electrical component enclosed within the tool-insert to a source of electrical power: These include:

3. Simple electrical, such as containing a heating element for applying heat to the lumen wall.

4. Compound mechanical-electrical, such as a heating coil in a compound mechanical syringe.

5. Compound mechanical-electrochemical, wherein, for example, resistance to penetration posed by the lumen wall to a flanged hypoendothelial or hypointimal injection needle is used to close a switch that initiates a current used to heat a filament which breaks down a barrier separating gas-generating components, such as acetic acid and sodium bicarbonate, causing the contents of a syringe to be expelled. Such a melt-barrier can also be used to separate chemicals from a solvent that when added generates heat.

6. Compound electromechanical, wherein, for example, a spring is released by passing a current through and melting a restraining wire, such that the electrical and mechanical elements are not one and the same.

7. Electromechanical, wherein the tool-insert includes an actuator such as a thermal expansion wire, polymer actuator, electric motor, or vibrator, such that the electrical and mechanical elements are one and the same. Fluidic tool-inserts, wherein the tool-insert base-plug serves as a fluid as well as a mechanical connector for admitting fluid from the control circuit into and through the tool-insert to be delivered into the lumen (ejector), the lumen wall (injector), or in a tool-insert capable or additionally capable of aspiration, from the lumen to the line, and if present, to power a component incorporated into the tool-insert:

8. Simple flow-through ejector-irrigator-aspirators, injectors, and aspirators without an entry elastomeric membrane slit valve or strip-spring as fluid resistance or regulator covering the internal opening into the plug at the base of the tool-insert, which thus passively and inseparably conduct fluid from the line (fluid circuit, pipeline, supply line) to the lumen from and in proportion to the extent to which the fluid pressure raises the lift-platform and propels the fluid. In a fluidic circuit that includes bypasses as described below in the section entitled Fluidic Tool-inserts, to Include Ejectors and Injectors, such a tool-insert, because it incorporates no fluid resistor, allows fluid to flow through it when the line pressure is little greater than necessary to close the fluid chamber partition aperture spring-loaded swing type wafer check or strip-spring mounted flapper valve closing the aperture and raising the lift-platform. The lack of an internal strip-spring or slit membrane also allows unrestricted flow-through in either direction, making possible use as an aspirator as well without the need for special spring valving to avoid clogging.

9. Compound fluidic- and mechanical flow-through injectors and ejector-irrigators (but not ejector-irrigator-aspirators) having an entry elastomeric slit membrane, hard resin slit or perforated fluid resistor, or strip-spring type of valve as fluid regulator covering the internal opening into the plug at the base of the tool-insert. Pressure in the line must first exceed that required to raise the lift-platform, then the additional pressure required to pass the entry elastomeric membrane slit or strip-spring valve or fluid resistor in the base of the tool-insert, allowing differential actuation of tool-inserts in the same circuit. For use in an ejector-irrigator-aspirator, a strip-spring would prevent intake flow, and a slit membrane would clog (see next listed). The flow-through resistance is a function of the viscosity and pressure of the fluid used.

10. Compound fluidic-mechanical flow-through tool-inserts having cutting faces with irrigation and/or aspiration integrated that must remain projected while in use, then retracted for safety, requiring a lift pressure setting strip-spring, and ejector-irrigators that additionally function as aspirators which use an internal strip-spring as a fluid valve regulator to set a flow-past pressure and rate of discharge. To aspirate as well as discharge and irrigate requires bidirectional function not afforded by a strip-spring, and reasonable resistance to clogging not provided by a slit membrane. Such function requires more complex bidirectional valving that not only sets the threshold pressure for rate of discharge for a fluid of variable viscosity in antegrade or outward flow but allows retrograde flow without clogging over an interval sufficient to complete the interventional procedure. Fluid used to flush through the line during aspiration moves through the circuit with negligible if any rising up into the tool-insert. Various fluids can be used to irrigate with the same or different fluids used to aspirate.

11. Initial dose or front-loaded simple flow-through ejector-irrigator-aspirators and injector-irrigators.

12. Initial dose or front-loaded compound fluidic-mechanical flow-through ejector-irrigator-aspirators and injector-irrigators.

13. Mechanofluidic—inert bit mechanical shaver or abrader (brush) with integral irrigator.

14. Mechanofluidic—inert bit mechanical shaver or abrader with integral aspirator.

While distinguishable on the basis of function thus, a single tool-insert can usually perform more than one function. For example, the initial dose expended, an initial dose or front-loaded injector can then be used as an intermittent or continuous injector. Not extending a needle, an initial dose ejector, once the initial dose has been expended, can be used not only as an intermittent or continuous ejector, but as an irrigator. This not only allows the different application of one and the same tool-insert for different purposes without the need to withdraw and reenter but also realizes economies and efficiency. Fluidic tool-inserts that include electrical function and thus require connection to a source of electrical as well as fluid power are not preferred. The need for heating is avoided by delivering the fluid already at the desired temperature.

With or without heating, oscillation to enhance the abrasive or shaving action of an inert bit is accomplished with the turret-motor or a neighboring electrical unit. Bits with paths for irrigation or aspiration require insertion in fluidic units. An abrading or shaving bit without integrated irrigation or aspiration is used in an electrical unit with neighboring fluidic units or service channel used for irrigation and/or aspiration. To avoid clogging the delivery of fluid to projecting and emitting tool-inserts, aspiration is relegated to a separate parallel circuit with independent pump. Thus either individual abrading and aspirating units can be used or electrical units can be used to abrade with neighboring fluidic aspirators used to clear away the tissue removed.

In some situations, aspirators can be used as suction cups or suckers to hold the muzzle-head or radial projection catheter against the lumen wall during injection by a projection unit injector or barrel-tube delivered hypotube. However, excessive suction force necessary to effect a seal is to be avoided. In the vascular tree, special care must be taken to prevent intimal trauma that would induce hyperplasia. The use of electrical tool-inserts can also be coordinated with fluid delivery and removal through barrel-tubes and the central canal, as addressed below in the section entitled Coordinated Use of Aspiration and Piped Radial Projection Units to Remove Diseased Tissue or Obtain Tissue Samples for Analysis.

Electrical and fluid projection units and their respective tool-inserts having unique as well as common capabilities, depending upon the application, electrical and fluid circuits can be incorporated into the same barrel-assembly. Then, however, for simplicity in manufacture and use, fluid and electrical circuits and components are not combined in the same units or tool-inserts. While tool-inserts using both electrical and fluidic connection would provide types of tool-inserts in addition to those listed above, laying out the fluid and electrical circuits in parallel allows using neighboring projection units from either circuit in a coordinated manner, making hybrid tool-inserts that require connection to both electrical and fluid circuits unnecessary.

Accordingly, electrical tool-inserts are used in electrical but not in fluidic projection units and may contain mechanical, chemical, electromechanical, or electrochemical but not fluidically operated components. Electrical tool-inserts are lifted and retracted electromechanically and contain an electrical component, such as a heating element or vibrator. Electrically operated radial projection units can be used to emit fluids only through mechanical or mechanical and electrical syringe tool-inserts. These can discharge a precise but small dose. Fluid systems can also use self-contained or enclosed syringe tool-inserts that include no electrical components, but can additionally use distinctively fluid tool-insert that deliver fluids from the circuit. For use in blood vessels, gases must be completely eliminated from the tool-insert.

Thus, fluid tool-inserts are likewise prefilled with an initial dose of the same medication as that to follow from the line or another substance, such as water, and except for the tube connector at the base, appear outwardly like enclosed syringes. Gas discharged tool-inserts must be completely 'airtight.' Once the prefill substance is expended, however, the fluid syringe type injector or ejector, unlike the enclosed syringes to which an electrical system is limited, can conduct fluid from the line, which can be fed fluid from a number of temperature controlled reservoirs. This allows any amount and number of fluid substances to be delivered in any sequence at any temperature.

By the same token, a fluid system cannot confine heating to the treatment site as can an electrical tool-insert, and it is less quick and flexible in terms of mechanical action within individual tool-inserts. Fluid tool-inserts are lifted fluidically, that is, electrohydraulically or electropneumatically, and when lifted, some allow fluid from the line to pass through and out the working face through apertures or hollow needles. Distinctly fluidic as opposed to enclosed syringe-type tool-inserts are therefore usable only in fluid system projection units, and may contain mechanical or chemical, but not electrical, electromechanical, or electrochemical components. Due to the essentially fluidic or electrical function of tool-inserts, those requiring connection to sources of both fluid and electrical power are exceptional, those fluid operated with inmate electrical heating element of this kind.

A radial projection catheter less limited in this regard, nonprojectable units can be included, but radial units in muzzle-heads are always projectable. The ability to inject a lumen wall by means of radially oriented or side-looking hypotube injectors, as addressed below in this section, has numerous potential applications preparatory to and prophylactic upon completing, an interventional procedure, to include implantation with or without stenting. If the muzzle-head in a barrel-assembly of larger gauge, such as for use in the gastrointestinal tract or trachea and bronchi, is not large enough to accommodate the number of radial projection units desired, additional units can be situated anywhere about the intracorporeal periphery of the barrel-catheter.

Radial projection and/or nonprojectable units can also be incorporated into an ablation, atherectomy, or angioplasty catheter without barrel-tubes as a separate and distinct device. Not having to accommodate one or more barrel-tubes much less the gas diversion channels required of a barrel-assembly, especially one for use in the vasculature, such a catheter can be made narrower in gauge than a barrel-assembly and much of its distal length can be used for radial projection units. Moreover, when made to the same diameter as the equivalent barrel-assembly but without the ballistic component (barrel-tubes, pressure relief channels), the area of the catheter lumen becomes available to increase the depth of the unit lift-shaft, so that self-contained syringe-type or injection tool-inserts (injectors), for example, can contain and deliver considerably more injectant.

Since units can be enlarged in the longitudinal and circumferential directions and units placed along the entire intracorporeal length of the catheter, the loss of depth is readily compensated. A separate radial projection catheter with central component such as a laser or rotatory cutter is referred to as a combination-form radial projection catheter. As with a combination-form barrel-assembly, the central component can be permanently installed or used to install different interchangeable cabled devices such as an atherectomy laser, endoscope, intraductal ultrasound device, or rotational thrombectomy tool. Using a combination-form radial projection catheter to ensheath a simple pipe or radial discharge barrel-assembly places the ballistic component in the central channel thus eliminating a central component.

The 'taller' unit shown in FIGS. 54, 56, 59, and 63, for example, are thus suitable in a radial projection catheter or barrel-assembly of large diameter and would be reduced in height when incorporated into a smaller device. The larger area available justifies the inclusion of nonprojectable units and freed internal diameter allows the use of piped units where a barrel-assembly would be limited to electrical units in vessels too narrow to admit a barrel-assembly. In both electrical and fluidic systems, these can be ejection syringe tool-inserts (ejectors) or heating elements. Electrical ejectors can additionally heat the contents of the syringe. Nonprojectable units in fluidic systems can deliver a fluid at a specified temperature of if not perforated, use the fluid to affect the temperature along the working face.

However, incorporating radial projection units into the muzzle-head allows any number of medical functions to be applied to the lumen wall at any moment in immediate coordination with implantation without the need to withdraw and reenter. As in a barrel-assembly, to contain the temperature, emitters both ejector and or injector, made of low temperature conductivity polymers, can additionally be insulated as can the supply line in a fluid system with an insulative coating. The lowering of injectors when not in use also reduces heat transfer. Ejectors can be controlled thus likewise. Both syringe and flow-through type radial injectors can be used to introduce substances preparatory to administering medication, other medication, or implantation, the latter not limited to the volume of fluid contained.

Implantation preparatory substances include, for example, medial tumefacients or swellants and tissue adhesive-hardeners or binder-fixatives. The placement of radiation seed implants with a barrel-assembly is ballistic. The two major types of radial projection unit, electrical or nonpiped, without connection to a fluid pipeline (line, supply line, conduit), and the fluidic or piped, are described below under the heading Structure of Radial Projection Units. Tool-inserts that do not require connection to a source of electrical or fluid current through the projection unit can be used interchangeably in either electrically or fluidically operated units of like size.

These include passive or inert tools that consist of a cutting head used to ablate tissue from the lumen wall by shaving or abrasion at body temperature, and syringes that release fluid stored within these. Other tool-inserts require connection to an electrical or fluidic line. Some functions can be performed only with one or the other type connection. Such actions that can be performed electrically can be accomplished within barrel-assemblies of smaller diameter, allowing application to narrower arteries, for example. Heated cutting heads and blank face hotplate tools can be either electrical or fluidic, while electronic (thermoelectric, Peltier effect) microrefrigeration, early in development and demanding unaccommodateable heat sinks, must be fluidic.

Electronic refrigeration is addressed above in the section entitled Rapid Cooling Catheter and Cooling Capillary Catheter for Cooling Heated Turret-motor, Electrically Operated Radial Projection Unit-lifting Thermal Expansion Wires and Heaters, and Recovery Magnets. Other electrical tool-inserts can incorporate electromechanical or electrochemical means to raise the working face with greater force or to a greater height, or electroactuator means to move the working face in relation to the treatment site. Fluidic tool-inserts can pass through fluid from the line into the lumen, or if provided with a hypointimal or hypoendothelial needle, inject the fluid into the lumen wall. Only tool-inserts for insertion into the units connected to a fluid supply line can additionally be used to emit a fluid on a continuous or intermittent basis or fluid that has been chilled.

A piped system and tool-insert can be used to deliver different liquids and/or gases from the line to the treatment site at the most effective temperature and/or to aspirate ablated tissue. and abrasive action can be accelerated by quickly rotating the muzzle-head with the turret-motor (qv.), which can accede to oscillatory frequency, or by reciprocating the barrel-assembly transluminally by hand if not with the aid of a linear positioning stage. Electrical tool-inserts for use in larger electrically operated projection units such as for use in the gastrointestinal tract or airway can incorporate a wobbling or reciprocating motor to accelerate the cutting action. Also usable with either type lifting mechanism are self-contained ejectors and injectors or syringes which contain rather than draw the fluid from the line.

Even though no tooling (cutting, brushing, or injection) function is performed, flat-faced tool-inserts, or blanks, such as are used as push arms, as well as fluid emitting tool-inserts in piped units are referred to as tool-inserts. Different tool-insert are used to ablate, angioplasty, or deliver fluid at the treatment site at a controlled temperature by conducting heated or chilled liquid or gas from a cylinder attached at a side-socket (qv.) or end-socket (qv.), or in the case of an ablation or ablation and angioplasty-capable barrel-assembly, from a self-contained internal circuit that includes a pump and reservoir, for example. Electrical units are elevated or projected into working position electrically, while piped or fluid-operated units are elevated by the force of the fluid against undersurface, that is, the inward or medial surface of the tool-insert holding and lift-platform.

The action using a liquid is hydraulic, and using a gas, pneumatic. Hybrid units that use fluid to raise the lift-platform and also connect electrical tool-inserts to a power source are unpreferred as needlessly complicated compared to electrical units. Electrical or fluidic, the distance lifted is proportional to the current through the pipeline. Additional lift by the radial projection unit itself as a lifting mechanism rather than by a device built into the tool-insert can be obtained by incorporating, for example, the scissors linkages described below in the section entitled Extended Projection Scissors Lift-platform Mechanisms. The lift-platform receptacle or socket in an electrical unit engages interchangeable tool-inserts electrically as well as mechanically.

Enabled only while in the raised position, the electrical tool is wired and controlled as a subcircuit of the expansion wire used to raise the lift-platform. As seen from above, the lift-platform socket in a fluid system is the same as that in an electrical system but always passes entirely through the lift-platform.

Since the fluid circuit is a permanent feature of the barrel-assembly or radial projection catheter, the resistance to lifting among units in the same circuit is best kept uniform. Differential lifting among the individual tool-inserts is then best accomplished by factors built into these. Differential actuation along the same circuit allows cutters, injectors, ejectors to be actuated before or after heating or chilling tool-inserts, for example.

To provide differential lifting among units in the same fluid circuit, the opening to the orifice (opening, ostium) leading up into the base-plug is covered over with any of several resistance. A one-way (unidirectional) resistance used where transition to aspiration is not required is generally a strip-spring covered orifice, break-away plug, or break seal. Two-way (bidirectional) resistances are usually slit-membranes or an offset strip-spring covered orifice. Strip-spring covered orifices admit fluid from the line up into the tool-insert only when the line pressure is sufficient to flex the strip-spring allowing fluid to enter the orifice, flow through the tool-insert, and out the working face.

In electrical tool-inserts, which are incapable of aspiration, the need for bidirectionality is not a factor and strip-springs used for differential resistance to lifting. Whether in a barrel-assembly or separate radial projection catheter, where a one-way resistance is used to establish a syringe discharge threshold pressure, aspiration prior to emission or the resumption of emission following aspiration is accomplished through use of a second parallel fluid circuit. The continuous delivery through the tool-insert of fluid requires first that the pressure in the line is sufficient to pass the strip-spring closing off the bottom of the lift-platform and second, the membrane slit or strip-spring at the inside opening to the base-plug.

However, in tool-inserts to additionally function as aspirators, alternative internal spring valving or regulating means are necessary to allow bidirectional operation without clogging. The radial projection unit can remain vacant until the line pressure exceeds the restorative force exerted by the lift-platform strip-spring. If exceeded while vacant, fluid will leak from the line out of the unit. If filled with an emitting fluid tool-insert, then the additional pressure necessary to overcome the ostial strip-spring must be exceeding for fluid to pass through the tool-insert. The delivery of heated and chilled gases and liquids, which may be fed to continuous or intermittent fluid ejectors and injectors or to closed surface tool-inserts for cryogenic or thermal use will alter somewhat the pressure at which each of these strip-springs yield.

A fully self-contained electrically operated tool-insert such as a heater, which draws power from a circuit independent of that supplying the electrically operated lifting mechanism, can operate independently of the lifting mechanism. However, self-contained compound mechanical syringe ejectors or injectors when used in an electrically operated radial projection system must be raised to function. In a fluid system, the tool-insert is usually both lifted and supplied with the ejectant or injectant by the fluid line. Such fluid tool-inserts are not self-contained.

Instead these function as dependent upon the lifting mechanism such that the rate of fluid release through the tool-insert is usually proportional to the pipeline pressure and thus the degree of lift. Thus, both self-contained or syringe and fluid transmitting type ejectors and injectors require to be lifted in order to discharge fluid. Whereas electrical systems operate these tool-inserts as a function of raising them, fluid systems do so only once the tool-insert has been being raised. While the reasons differ, the use of injectors and interchangeable ejectors is indissociable from operation in the raised position. However, minimal extension at low fluid pressure need not disable tool-insert use in a fluid system.

Any one tool-insert for insertion into a piped unit may require only to:

1. Be lifted into working position once the fluid attains a threshold pressure and thereafter remain extended to a distance proportional to the fluid pressure, then retract when the pressure drops below the lifting pressure, or 2. Expel fluid continuously once the fluid attains a threshold pressure and discharge or release the fluid in proportion to any higher pressure, or might be used to 3. Deliver an injection at a threshold pressure. In order to allow any unit along the pipeline to accommodate a fluidic (flow-through, non self-contained) ejector or injector, every fluid tool-insert holding and lift-platform has a hole in its underside that is kept closed by a tiny spring-loaded strip-spring valve that can only be opened by a short pipe that extends down from the base of a fluid delivering tool-insert.

Opening the spring valve then allows fluid to pass into the tool-insert from the pipeline, through the tool-insert, and out the perforation or needles on the tool-insert working face. Fluidically operated tool-inserts that are only to be lifted into position and not emit fluid do not have such a projection. Two types of ejection or injection tool-inserts can be used in a fluidic system, one unique to such a system, the other equally usable in an electrical system. The fluid type allows fluid from the pipeline to enter through a projection in the base that allows fluid in the line to enter, flow through the tool-insert (syringe-insert, syringe, injector), and out the face perforations or one or more needles.

A fluid injection or ejection syringe is capable of delivering the injectant or ejectant continuously or intermittently up to the amount of fluid available in the reservoir. External and cartridge refilled internal reservoirs allow unlimited delivery. An ablation or ablation and angioplasty-capable barrel-assembly with one or more internal fluidic circuits can incorporate multiple completely enclosed, heated, and insulated reservoirs, to include one containing distilled water for flushing the line before switching from one medication or other fluid reservoir to another. Refillable, refill cartridge-accepting, and switchable reservoirs overcome limitation in the amount of each fluid available.

The alternative is to draw fluid from an external reservoir or reservoirs, which eliminates the need for insulation, but tethers the barrel-assembly, which can hinder free manipulability. Fluid injectors can also be classified on the basis of whether these deliver the fluid whenever the line pressure is sufficient to overcome the resistance posed by an extension leaf spring in order to raise the unit lift-platform or the pressure must additionally exceed that necessary to overcome a second resistance whether posed by a push-through stopper, or break-away plug, break seal, or a second strip-spring that is offset and mounted to respond in the opposite direction.

Unlike push-through stoppers and break-seals, which are eliminated, a strip-spring covered inlet in the tool-insert base-plug can be used repeatedly. Unlike slit-membranes which are bidirectional, strip-springs are unidirectional. It therefore allows the fluid in the line to be changed while the ejector is not in use or the injector remains hypointimal or hypoendothelial. While usable repeatedly, however, a unidirectional fluid resistor prevents aspiration through the same tool-insert. The unidirectional limitation of a strip-spring covered fluid path can be overcome by providing a second passageway with the resistor mounted on the opposite side. Perforated plates and slit-membranes are examples of bidirectional fluid resistors.

Rather than to introduce nonuniformities among the lifting mechanisms in the same circuit, the differential lifting of injectors, for example, is accomplished by incorporating a mechanical or fluid resistor in each that yields to a different degree of force. The lifting pressure of a fluid tool-insert is set by the resistances of the chamber partition inlet valve, which belongs to the unit, and any fluid resistor in the tool-insert base-plug, which is included in the interchangeable tool-inserts. Of these, either or both can be varied in resistance or eliminated. The valve is a cupped flapper-stopper mounted at the end of a spring stainless steel arm or a swing type wafer check valve with the convexity positioned in front of the aperture that allows fluid to pass directly from the inlet through the partition to the outlet chamber.

When units in the same fluid circuit are preferably variable rather than uniform in response, the self-closing valve in front of the inlet or pump outlet side of each chamber partition is varied in resistance. Reciprocally, aspiration through ejector-aspirators can be actuated at different pressures by varying the resistance of the self-closing valve on the opposite side of the partition. A subactuating idle pressure allows circulation through the line and thus a quicker tool-insert response time. This self-closing valve is riveted to the side of the inlet chamber by means of a angle bent compression band of stainless spring steel. Since the material and dimension of the strip can vary widely, a wide range of restorative or closing force is possible.

Fluid current that presents a closing force that exceeds the restorative force or resistance of the spring arm causes the stopper to close the hole, leaving the extension strip-spring in the chamber ceiling as the path of least resistance, so that the tool-insert is lifted. This results in three levels of pressure: sublifting, lifting, and fluid emitting. As fluid units are designed to aspirate as well as actuate, a stopper of opposite placement is positioned on the antegrade outlet or retrograde inlet chamber. This second spring can be a helical compression spring, or depending primarily upon the displacement desired, a leaf, elliptical, or full elliptical compression spring, for example. This spring is usually situated between parts of the injector corresponding to the thumb rest and barrel bottom of a hypodermic syringe.

Leaf and elliptical springs are usually paired to either side of the extrabarrel portion of the plunger, whereas helical springs surround it. Ejectors and injectors for use in either fluidic or electrical units of a given size do not deliver fluid from the pipeline but like full sized syringes, contain a finite amount of ejectant or injectant which can be delivered continuously or intermittently. This type can be disposable or hold refill cartridges. When usable to deliver multiple individual injections in succession, a single injection or syringe tool-insert, because it still contains the liquid it discharges rather than draws the liquid from the pipeline is still referred to as a single injection type notwithstanding the fact that it too can be used intermittently.

Both injector types are pressure actuated, so that serially connected injectors with only the lift-platform strip-spring discharge at the same pressure with a medically insignificant time delay from one to the next moving downstream. By including a second spring within the individual injectors, different pressures in excess of the pressure to overcome that of the lift-platform are established. Adjusting the dimensions and material of this second spring internal to the tool-insert thus allows the differential control of the individual units along one and the same electrical or fluidic circuit; it is thus unnecessary that differently functioning units be provided with a dedicated circuit. Differential capability allows simultaneous or sequential ejection or injection by tool-inserts in the same circuit, for example.

Control in this manner optimizes the extremely limited space available in a barrel-assembly meant for use in the vascular tree, and can be used to govern the absolute threshold force to actuate each unit, the sequence in which the injectors or other tool-inserts along the line are raised into working position and then discharge or otherwise function, and the amplitude or extent of this function. Injectors proximal to the pump that are more resistant can be made to discharge or otherwise function later than injectors farther downstream which discharge under less force. Electrical tool-inserts can incorporate additional means electromechanical and electrochemical for affecting the force of actuation and sequence of operation along one and the same circuit, as addressed below in the section entitled Electrical Tool-inserts, to Include Gas Discharged Injection and Ejection Syringes.

The only difference between continuous delivery and one-time at pressure injectors is that the continuous type uses the strip-spring base-gate to allow fluid from the pipeline to flow through and out the needles or face perforations, whereas the single-injection type does not admit and inject fluid from the pipeline at all, but rather uses the pressure in the line to raise the strip-spring base-gate to admit fluid from the line once the expulsion pressure of the single-use or refillable cartridge that constitutes the tool-insert has been reached. The single injection type can thus be used in either an electrical or fluidic system of the same size. Exposure of the cartridge bottom plunger-plate to the fluid entering from the line at the pressure set by the strip-spring gate forces the plunger to expel the liquid contents of the cartridge through the openings at the working face and onto or into the lumen wall.

Because the liquid is contained locally within the tool-insert or the refill cartridge within the tool-insert rather than drawn from a pipeline, electrical units can also be used to position radial ejectors and injectors. As addressed below, these tool-inserts can be internally compartmentalized to deliver successive injections of the same substance at intervals, the same substance at different concentrations, or different substances such as medications upon exposure to increasing increments of pressure so that the moment when each is injected can be controlled by adjusting the line pressure. This becomes necessary when the muzzle-head, because its length must be kept limited for reasons of trackability and distal reach for treatment, cannot incorporate a sufficient number of radial units to deliver the number and type of medications desired.

Since each injector, whether a spring released self-contained or fluid syringe, is actuated by pressure in the fluid line, and this actuating pressure is readily set by the materials and dimensions of the unit self-closing fluid chamber valve and the tool-insert base-plug fluid resistor, fluid expulsion, such as injection or syringe tool-inserts can be made to act in any sequence regardless of type. Depending upon the application, this can be significant. In the continuous delivery at pressure-type, once the tool-insert holding and lift-platform has been raised, a second strip-spring or similar valving mechanism such as a spring loaded damper-like butterfly or poppet pressure valve at the base of the tool-insert is used to control the relation between the fluid pressure and the rate of fluid flow through the tool-insert.

When engaged by a blank, the lift-platform is raised in proportion to the resistance posed by the pipeline strip-spring to the instantaneous pipeline pressure. The use of different materials in different dimensions to make the strip-spring makes establishing a desired restorative force, hence, lifting characteristic, uncomplicated. Piped tool-inserts having perforations or hypotube nozzles include in their base an internal strip-spring or similar mechanism which serves as a second-order valve. With this second-order strip-spring omitted, the tool-insert passively discharges fluid in proportion to the fluid pressure used to raise the lift-platform and therefore proportionally to the degree of lift. That is, the rate of emission would varies as the current.

The incorporation of a second strip-spring in the base of the tool-insert isolates the rate of fluid release from the degree of lift; however, emission is still dependent upon lift and nonfunctional unless at lease some degree of lift exists. For practical purposes, this sufficiently approximates independent variability. If a piped unit tool-insert provides a passage with a spring-loaded valve entry leading from an aperture in the lift-platform through the valving mechanism and through a hole or holes in the base of the tool-insert, then fluid passed through the pipeline can be released through perforations or nozzles (hypotubes) in the tool-insert faceplate.

The hypointimal or hypoendothelial injection of medication, an implantation-preparatory ductus wall tumefacient as addressed above in the section of like title, or some other fluid through a fluid tool-insert can be performed in either of two ways. A constant output pressure pump and reservoir are used to deliver the fluid through the lift-shaft strip-spring and tool-insert base strip-spring or alternative injection or syringe tool-insert base gating device at a pressure or flow rate set by the pressure setting and the passing pressure or gauge of the hypotubes or nozzles. In the continuous delivery at the designated pressure mode of delivery, the unit can be stepped along at intervals to inject the fluid intermittently into a longer segment of the lumen wall.

There is thus an initial threshold pressure that must be reached before any of the injection or syringe tool-inserts or injectors pass the fluid, after which the line pressure and resistance to fluid entry of the individual injector determines which injector or injectors pass fluid, allowing a prescribed injection sequence to be established by selecting injectors having an entry or gating resistance proportional to the pressure for passing. To allow the use of an external hand-held electromagnet to draw the hypointimal or hypoendothelial injection needles or hypotubes up against and penetrate the lumen wall with minimal field strength, the needles of both continuous and single injection or syringe tool-inserts must contain ferromagnetic material whether a magnetic stainless steel or a polymer containing iron powder.

As the fluid is injected, the pump takes up more fluid from the reservoir to maintain constant pressure. The extent of treatment is limited only by the amount of fluid available from the reservoir. Filling the pipeline with costly medication of which little is to be injected is not done; costly medication is introduced by means of a tool-insert configured as a hypointimal or hypoendothelial injection device or injector which is disposable or accepts refill cartridges. A threshold force exerted against the tool-insert base breaks a seal or releases a catch that frees a spiral compression spring seated within the tool-insert base to suddenly drive the base upwards, ejecting the fluid.

The restorative force due to the thickness and material of the base strip-spring, the seal, or a tripping device determining the pressure at which fluid is allowed to pass and be injected, each tool-insert can be selected for discharge at a specific fluid pressure. If necessary, each unique injectant includes a distinctive contrast dye. Adjustment of the pressure thus allows the different tool-inserts to be infused into the lumen or injected into the lumen wall at the time desired, allowing injection in a preferred sequence. It will now be seen that any one tool-insert can be used to deliver a single dose, or if not actuated by a second order strip-spring, be made to release or inject medication intermittently by this means. Thus, injection or syringe tool-inserts, for example, can differ from one radial projection unit to the next.

This makes the administration of the same or different single-dose medication and injection that continues so long as the pressure is high enough freely intermixable. Since each tool-insert injector or group of injectors whether of the continuous or single discharge type is differentially actuable simply by adjusting the pump pressure, the differential injection and/or infusion of medication can be coordinated with controlled timing. Alternatively, a service-catheter with plunger and hypotube injection tip passed down a barrel-tube as service-channel. The medication occupies and is ejected from the distal end of the service-catheter. The onboard angioplasty control panel of an ablation or angioplasty barrel-assembly with self-contained fluid moving system includes a pressure control and gauge.

Electrically operated units are not associated with a pipeline for lifting or fluid delivery and are not used to emit a fluid or chill a blank tool-insert face plate. However, like fluid units, electrical units can heat when the tool-insert contains a heating element. Piped units are used with blank or closed-face tool-inserts to change the temperature at the tool-insert face-plate, or with perforated or nozzled face-plates to emit the fluid for ejection or injection. Since with a blank, the preheating or prechilling temperature of the fluid used determines the temperature over the face-plate, separating the lifting from the tool working function is unnecessary. Generally, fluidically elevated units are used with perforated or nozzled tool-inserts to deliver and/or aspirate fluids as a side function consistent with the lifting means.

In a fluidic unit, the need to vary lift and descent independently of the rate and timing of fluid ejection or aspiration would not appear to justify hybrid electrically operated units that include fluid lines to and from perforated or nozzled tool-inserts. Aspiration with piped units supported by a full circuit pump is by disconnecting the positive or pressurizing output line of the pump while leaving the return line connected to the unit pipeline. Ablation and ablation and angioplasty-capable barrel-assemblies are preferably self-contained with no tethering to a separate apparatus. When not required to deliver or recover an unlimited volume of a liquid, for example, fluid circuits are preferably incorporated into the barrel-assembly entirely, to include the fluid pump, reservoir, manifold, and electrically operated valves.

These are usually located in the power pack with a proximal portion configured as a pistol or similar hand-grip having the control panel mounted to its topside, for example, to avoid the need for right and left-handed models. Combination-form barrel-assemblies are ablation or angioplasty-type barrel-assemblies, but usually require at least intermittent connection through a cable to a remote console. Unperforated or blank tool-inserts in piped radial nonprojectable units can be used for cryoplasty or thermoplasty. Nonpiped or electrical units are always projectable but unlike piped units, need not be projected even slightly during tool use.

When perforated, the liquid or gas is emitted out of these apertures into the lumen or onto the surface of the lumen wall, and when nozzled, into the lumen wall. Radial projection unit side-sweeper type tool-inserts or brushes have no precedent in previous transluminal shaving or abrading devices such as directional, rotational, or orbital atherectomy devices, brushes meant for use to clear hemodialysis grafts, such as the Micro Therapeutics-Castañeda over-the-wire brush (Castañeda, F., Li, R., Patel, J., DeBord, J. R., and Swischuk, J. L. 2001. "Comparison of Three Mechanical Thrombus Removal Devices in Thrombosed Canine Iliac Arteries," *Radiology* 219(1):153-156), Cragg brush (Dolmatch, B. L., Casteneda, F., McNamara, T. O., Zemel, G., Lieber, M., and Cragg, A. H. 1999. "Synthetic Dialysis Shunts: Thrombolysis with the Cragg Thrombolytic Brush Catheter," *Radiology* 213(1):180-184) or any other brush-like device.

Brush-configured tool-inserts have individual projections or bristles that can vary widely in flexibility and have tips that differ in conformation. With the barrel-assembly moved manually, brush-configured tool-inserts can be extended to shave or abrade diseased tissue along the lumen wall, for example. Inert bit inserts with flat outer surface and rounded edges, or blanks, are used as pushing arms to force the muzzle-head in the opposite direction, to plug off or seal unused fluid units that would otherwise emit fluid at a threshold pressure, and to test for leaks in manufacture and prior to use when the blanks are to be used during the procedure.

Side-pushing action or nudging can be used to allow more blood to pass, to urge a tool-insert toward a preferred radial position or arc, to cause, for example, a brush or injection or syringe tool-insert on the opposite side to bear against the lumen wall with greater force, or to aid in steering. A more detailed description of nonpiped, or electrical, and piped, or fluidic, radial projection units is presented below in the section entitled Structure of Radial Projection Units. As shown in FIGS. 52a, 52b, 54, and 59 as exemplary for the two differently controlled types, tool-insert receiving units include a lift-shaft 182 containing tool-insert holding and lift platform 176 and are situated about the periphery of muzzle-head as 174 in FIG. 49, for example, between the front of turret-motor housing 61 to the rear, and elastomeric segment of convoluted tubing that serves as flex-joint (flexible joint) 111 to the fore.

Lift-shafts 182 are thus concentric to and distally coterminal with barrel-catheter 44 at the level where barrel-catheter 44 is joined to convoluted segment 111. In larger embodiments, units can also be situated about recovery electromagnet 65 housing. Hypothetically, in barrel-assemblies for use in blood vessels, situating units about the magnet assembly would place tool-inserts distal to the muzzle-ports for removing plaque when the barrel-assembly is moved forward. However, few vessels present sufficient internal diameter to allow a suitable path for electrical connection to nonpiped units, much less a fluid line for piped units. Provided the units contain no ferromagnetic elements, placement thus is unhindered by the effects of the tractive force and heat generated by the magnets on the lifting mechanism.

The barrel-assembly readily reversed in direction, ablative action can be readily accomplished with aspirating piped units situated just behind (proximal to) the flex-joint, with the deployment of an embolic trap-filter optional. The number of radial projection and nonprojectable units is increased by lengthening the flex-joint segment and/or by increasing the arcuate extent of separate units up to complete encirclement of the muzzle-head. For optimal use of the available space, adjacent units are rectangular in radial cross-section. The radial projection unit tool-inserts are inserted into lift-platforms each of which rises and descends within its own lift-shaft.

Individual units can also be made wider in relation to the long axis of the barrel-assembly, that is, extended circumferentially in arc, and provided with a tool-insert holding lift-platform that accepts multiple tool-inserts in adjacent relation. However, separate lift-platforms make it possible to control those along a given circuit or pipeline independently or in coordination with neighboring units. To aid observation, radial projection units can be marked with bright contrast, such as Danfoss Tantalum Technologies Danfoss Coating®. The arrangement of consecutive or in-line (series connected) units along a given line in relation to those in another line is unlimited with the exception that piped units must be situated to allow for clearance of the line. The sides of the lift-platform are made as low in friction as possible and to fit flush or 'airtight,' hence leak-proof, to the sides of the shaft.

In-line units are connected sequentially along a single line, or in series, and operate substantially in unison, the time delay moving down line being proportional to the magnitude of the current, which should be increased to the point that this delay becomes too slight to have any practical significance. The units along such a line can be equidistant or at unequal intervals, alike or unlike in dimensions, retain the same or different type tool-inserts, and units along different electrically or fluidically operated lines can be interspersed. In some nonpiped and in piped units as shown in FIGS. 52*b*, 59, 60, and 63, lift-platform 176 is forced upwards against the restraining (retracting, depressing, lowering, seating) force exerted by thin flat strip-spring 187, which is fastened at both of its ends to the underside of lift-platform 176 and at its center to the top of inflow (inlet, ingress, entry) chamber 194—outflow or egress chamber 195 compartmental partition 188.

Inflow-outflow compartmental partition 188 is vertically divided into upper portion 189 and lower portion 190 to allow flow through its center until the pressure of antegrade (forward, anterograde) fluid movement drives inflow flapper valve or spring plug 191 to stopper or plug the inlet, or the pressure of retrograde (reverse, backward) flow drives reversed inflow flapper valve or spring plug 192, against the communicating hole aperture 193 created by the division of partition 188 into upper portion 189 and lower portion 190. The restorative force of strip-spring 187 is exceeded by the upward driving force of the thermal expansion wire in nonpiped units and the pressure of the fluid in piped units.

Strip-spring 187 consist of a band of springy nonmagnetic spring stainless steel (stainless spring steel), which austenitic, is virtually nonmagnetic, or a polymer with a similar restorative characteristic, and is sufficiently wide to prevent the nonlevel or lopsided raising and lowering of lift-platform 176. Since the restorative force exerted by strip-spring 187 is widely variable by changing its thickness and/or material, an electrically (thermal expansion wire) controlled piped unit that failed to raise lift-platform 176 when a lower pressure is in use is unnecessary. Strip-spring 187 is included in nonpiped electrically operated units for automatically retracting lift-platform 176 as thermal expansion wire 177 contracts or an alternative motive means subsides when current is removed.

Figure 57:
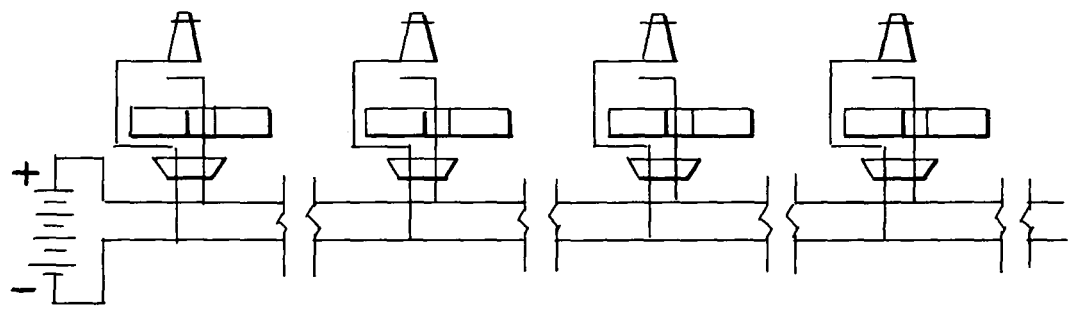
FIG. 57 depicts a series, rather than parallel or independently wired electrically energized tool-inserts, specifically, that of the compound mechanical-electrochemical tool-insert with gas generating reactive chemicals separated by a wax barrier melting wire such as one made of nichrome shown in FIG. 56, into which series-parallel paths and additional circuit elements can be introduced to energize alike or differentially one or more electrically or fluidically operated (lifted) radial projection unit tool-inserts or an electrochemically discharged injection tool-insert as shown in FIG. 56 or tool-inserts that heat their contents, for example.

In electrically operated radial projection units that use a strip-spring to provide lift-shaft and tool-insert retractive force, to avoid interference with the strip-spring by the thermal expansion wire even when cool, the strip-spring is oriented parallel to the coils in the expansion wire. As depicted in FIG. 57, on exiting through the opposite wall of the lift-shaft, the thermal expansion wire or an electrical power line used to energize elements internal to some or all of the tool-inserts can turn back to the power supply or battery, or continue to the next unit or another kind of electrical component. In piped units, as shown in FIGS. 52*b*, 52*c*, 58, 59, 60, and 63, reversing the external pump or switching the aesrosol canister or tank from one end of the line to the other reverses which chamber is the ingress and which the egress.

Centered within lift-shaft 182 and firmly secured to the bottom of lift-platform 176 at both ends, tilting of lift-platform 176 by the pressure of fluid entering inflow (inlet, ingress) chamber 194 with resultant jamming and leaking of the lift-platform is prevented. Due to the downward urging of the strip-spring 187, lift-platform 176 automatically descends when the upward force is removed. Since the electrical current in nonpiped, or electrically operated units, and the fluidic current (volume and pressure) in piped, or fluidically operated units, can be varied, the extent and duration of tool-insert elevation (projection) is jointly and continuously variable. In nonpiped units, the spring or springs pass between adjacent turns in a coiled thermal expansion wire.

In piped units, the pressurized liquid or gas flows past the spring or springs, which made of a stainless steel or a polymer, are little affected in restorative force by the temperatures and chemical environment encountered. Both nonpiped and piped units can be incorporated into minimally ablation or ablation and angioplasty-capable barrel-assemblies. However, with either type barrel-assembly engaged in the airgun, each projection unit pipeline must communicate with an external pump, aerosol can, or tank through a separate fluid coupling in a side-socket. The primary benefit of minimally capable barrel-assemblies being lower cost, multiply piped units requiring multi-port side-sockets are incorporated into minimally capable barrel-assemblies only on an exceptional basis.

VII2g(3)(d)(i). Structure of Radial Projection Units

An introductory description of electrically and fluidically operated units is provided above in the section entitled Radial Projection Units. For optimized functionality, the units in any given barrel-assembly or separate (special, dedicated) radial projection catheter, whether electrical or fluidic, are provided with all of the connections and components essential to accommodate any tool-insert of the type respective of each type circuit. More comprehensively, while certain applications may justify varied performance by differences in units rather than the tool-inserts these accept, the projection units in any one circuit are usually kept exactly alike.

Thus, even though an electrical/fluid system-neutral syringe (emission tool-insert, emitter, injection tool-insert, injector, ejection tool-insert, ejector) is self-contained and does not require connection to an electrical or fluidic circuit, the socket in the lift-platform at the bottom of the lift-shaft in either system includes the necessary electrical contacts or fluidic connections so that any other interchangeable tool-insert would be supported.

Space available for each radial projection unit a function of the diameter or gauge of the apparatus and the cross sectional area available for each radial projection unit, both electrical and fluidic circuits can be incorporated into the muzzle-head and/or barrel-catheter of a single barrel-assembly or special radial projection catheter. Smaller barrel-assemblies and special catheters can generally accommodate a single electrical radial projection circuit, a fluidic circuit requiring piping that demands more space. Unit lifting mechanisms can be assembled within a can or cup container which is then installed at the bottom of each lift-shaft, or can be installed without such a container, as shown in the figures.

VII2g(3)(d)(i)(1). Structure of Electrically Operated Radial Projection Units

Referring now to FIGS. 52*a*, 53*a*, 54, 55, and 56, thermal expansion wire 177 with elastic thermal insulation is wound no more tightly in an oblate (flattened) helix (coil) as necessary and passes along either long side of tool holding and lift-platform shaft (lift-shaft, well) 182. Lift platform 176 and lift-shaft 182 are made of or lined with low friction material, typically a fluoropolymer such as polytetrafluoroethylene. When to achieve precise fit of lift-platform 176 in lift-shaft 182 as avoids non-true radial travel and angling that results in jamming and tool inefficiency demands greater cost, lift platform 176 is constrained to level movement by prominences on the sides of lift-platform 176 that ride in channels in the walls of lift-shaft 182 as constitute sliding ways.

When necessary, an open-topped tool-insert 184 such as those depicted in FIGS. 53*a*, 53*b*, and 53*c* is prevented from being pulled out of lift-shaft 182 when swept over the lumen surface by overhanging or cantilevering swing-over hold-down arms 186 as shown in FIGS. 54 thru 56, 59, 60, and 63. With injection and ejection tool-inserts as shown in the foregoing figures, the end (terminus, roof) of syringe barrel 196 intervenes between the top of syringe plunger 197 and hold-down arms 186, serving as a stop limiting the distance of projection or excursion within tool-insert 184 and the outer surface of the muzzle-head or radial projection catheter.

To prevent the excursion or nonretraction of tool-insert holding and lift platform 176 apart from thermal expansion wire 177 such as by dropping to the extended position under gravity, coiled thermal expansion wire 177 is bonded to both the floor of lift-shaft 182 and the underside of lift platform 176. To withstand the temperature and deformation stresses involved, a silicone hot melt adhesive can be used, such as Dow Corning® HM-2500 Assembly Sealant. Jamming during lift or descent due to tilting of lift-platform 176 is prevented by making lift platform 176 and lift-shaft 182 with a low friction polymer, such as nylon or polytetrafluoroethylene.

Less slippery materials can be used when lift-platform 176 is additionally surrounded with a hemispherical standoff guard rail where lift-platform 176 is in contact with lift-shaft 182 (not shown). The alternative use of vertical bosses is addressed below in this section. Still referring to FIG. 53*a*, to preclude the levering forces encountered when the working tip of tool-insert 184 is applied to the lumen wall from pulling tool-insert 184 out of holding and lift-platform 176 or holding and lift platform 176 out of lift-shaft 182, tool-insert 184 must be securely engaged within receptacle-type lift-platform lift-platform 176 by spring-pin, screw-in, or friction fit, and lift-platform 176 prevented from being extracted from lift-shaft 182 by friction fit.

Tool-insert holding and lift platform 176 is in turn prevented from being pulled out by rotatable or swing-out retaining (hold-down, lock-down) arms 186 in FIGS. 52*a*, 52*b*, 54 thru 56, 59, 60, and 63, which rotate or slide over the upper edges of tool-insert 184 at the sides of lift-shaft or well 182 at the outer surface of the muzzle-head or radial projection catheter. Permanent and fixed, the fluid ejector, irrigator, and aspirator unit shown in FIG. 53*c* does not require hold-down arms and does not constitute a radial projection unit able to accommodate different tool-inserts. The depth of inset on the tool-insert and surface of the muzzle-head or dedicated catheter are equal, so that when tool-insert 184 is inserted into lift-shaft 182, the upper or radial surfaces of these are level.

Restrained by the floor beneath and the walls of lift-shaft 182 at the sides, coiled thermal expansion wire 177 is constrained to expand upwards, raising lift-platform 176. Heat generated by expansion wire 177 should be prevented from spreading beyond lift-shaft 182, and cold used for cryotherapy, cryoplasty, or to extend adhesive open time, for example, should be prevented from cooling expansion wire 177. If the muzzle-head polymer, usually a fluoropolymer (polytetrafluoroethyl-ene) does not intrinsically impart sufficient insulation to lift-shaft 182, then the internal surfaces of the muzzle-head aside from the heat-window or windows are coated with thermal insulation, such as squares of polytetrafluoroethylene impregnated thin glass fabric glued to the internal surface with high temperature silicone adhesive.

A piped lift-shaft may also require insulation from heat generated by the turret-motor and recovery electromagnet windings, especially when these are used as heating elements. The application of current to thermal expansion wire 177 overcomes the downward urging force exerted by strip-spring 187 causing insert-tool holding and lift-platform 176 to rise, extending the working face of tool-insert 184 beyond the periphery of the muzzle-head or radial projection catheter. The barrel-assembly can be rotated manually or with the turret-motor, and/or reciprocated manually or with the linear stage to exert a shaving or abrading action against the lumen wall.

Either or both the turret and linear stage motors can be used to impart oscillatory motion to the tool-inserts; however, the linear stage motor then must be closed loop controlled. The oscillatory mode of the turret-motor, as addressed above in the section entitled Turret-Motor Operational Modes, can be used to oscillate the muzzle-head at right angles to the cutting edges of a cutting tool, for example. The tool-inserts if left extended when unintended could injure the lumen wall. This is averted by virtue of the constant urging of strip-spring 187, which causes the radial projection units to automatically descend when not deliberately energized, eliminates the need for motion sensors and a control circuit to accomplish the same action.

In an nonpiped, that is, an electrically operated embodiment, the speed of retraction (lowering, withdrawal, descent) of lift-platform 176 is contingent upon the rate of cooling, hence, contraction (recession) of thermal expansion wire 177, whose lifting force of restraint against the downward urging of strip-spring 187 on lift-platform 176 strip-spring 187 cannot counteract unaided. If necessary, retraction can be accelerated by insertion of a cooling catheter or catheters though the barrel-tube closest to the unit or units. Continued elevation of lift-platform 176 is essential to allow a cutting or abrading tool-insert, for example, to continue in use.

The materials used of low thermal conductivity and with thermal insulation applied when necessary, exchanges in temperature between thermal expansion wire 177 and its surroundings are slight, and only extreme and protracted cold would be expected to cause thermal expansion wire 177 to contract allowing the lowering of tool-insert 184 while conducting current intended to maintain it in use. Contraction due to environmental cold must be considered 1. During the continued use of tool-insert 184, where tool-insert 184 must be kept in the extended position (projected, elevated) so long as current is sent through thermal expansion wire 177, and 2. As insufficient to assist in the prompt contraction of thermal expansion wire 177 once current has been cut off so that tool-insert 184 will retract.

Any insulation used to isolate thermal expansion wire 177 from the chilling surroundings during a cryoplasty, for example, will at the same time result in the need for colder or more extended chilling, such as by a cooling catheter, in order to accelerate withdrawal of the tool-insert once current is removed. Thus, quick retraction through the insertion of a cooling catheter limits the thermal insulation that can be used, but this factor must be weighed against the cold to which the wire is to be exposed with the tool-insert kept in use. Increasing the current to thermal expansion wire 177 in order to overcome the counteracting effect of surrounding cold is limited by the ampacity (current tolerance) of thermal expansion wire 177, which latter must remain relatively thin due to the dimensions of the radial projection unit overall.

Whether and to what extent thermal expansion wire 177 requires thermal insulation depends upon whether it is meant to allow a tool-insert to continue in use without retracting while the treatment area is chilled, as occurs when the a piped unit is used to supply cold gas during cryoplasty, for example, and the cold compensating increase in current that thermal expansion wire 177 can support without melting. When near to a piped unit or units or to a barrel-tube which is used to deliver chilling gas or liquid to the treatment site, thermal insulation may be necessary to counteract the heating environment and preserve independent operation so that inappropriate lowering of lift-platform 176 does not occur so long as the maximum allowable actuating current continues.

Any significant chilling of thermal expansion wire 177 will be dependent upon the specific configuration and dimensions of the unit elements, their proximity to the source of chilling, the thickness and thermal conductivity of the intervening materials, and the degree and duration in difference in temperatures between thermal expansion wire 177 and the chilling fluid. When necessary, thermal expansion wire 177 is insulated with elastic thermal insulation having a coefficient of linear thermal expansion determined according to American Society for Testing and Materials Standard D3386-94 Standard Test Method for Coefficient of Linear Thermal Expansion of Electrical Insulating Materials.

Accordingly, any insulation of thermal expansion wire 177 must be specific to the capabilities of the barrel-assembly, many of which will not be used for a cryoplasty, for example. Tool holding and lift-platform shaft 182 is flat and smooth walled, both it and the outer sides of lift-platform 176 made of low friction low heat conducting polymer, lift-shaft 182 normally machined into or lined with polytetrafluoroethylene as are contacting surfaces of lift-platform 176.

Referring to the view of FIG. 53*a*, were lift and descent not level without greater vertical constraint to prevent jamming, lift-platform 176 and lift-shaft 182 would be provided with leveling guides or slideway channels s in the form of vertically extended protrusive ways or bosses at the sides of lift-platform 176 with complementary receiving channels on the proximal and distal or inner sides of lift-shaft 182 that support all sliding contact at their interface. Such vertically oriented ways or channels are the same in vertical extent as the vertical distance moved by lift-platform 176. Lift-shaft 182 has hold-down arms 186 to prevent lift-platform 176 from being pulled out of lift-shaft 182 by the levering forces encountered by side-cutting or abrading tool-inserts. Specifically, lift-platform 176 is prevented from upward movement beyond the rim of lift-shaft 182 by swing-over hold-down arms or clamps 186.

To preserve the continuity of the muzzle-head, barrel-catheter, or radial projection catheter surface, swing-over hold-down arms 186 are inset within depressions at points about the perimeter, such as along the proximal and distal sides of lift-shaft 182 rim. Swing-over hold-down arms 186 are fastened at their outer ends to rotate into position over the tops and into complementary depressions in the upper surface of tool-insert 184, thus acting as swing over lock-down arms 186. A single hold-down arm 186 with the fastener similarly acting as the rotary joint at its center rather than toward one end, can secure adjacent tool-inserts. Such hold-down arms 186 are suitable only where tool-inserts are inserted in the adjacent lift-shafts, although a dummy tool-insert can be used to preserve continuity at the surface.

Half semicircular depressions in the upper edges of lift-platform 176 receive the swing-out arms in flush relation. Tool-insert holding and lift-platform 176 in FIG. 53*a* frames about the receptacle used for receiving interchangeable tool-inserts friction fitting into it such as those shown in FIGS. 53*b* and 53*c*.

The underside of holding and lift-platform 176, usually made of or veneered with polytetrafluoroethylene, is fastened to the thermal insulation enclosing thermal expansion wire 177, which in turn is fastened to the floor of lift-shaft 182 assuring descent with the contraction upon cooling of thermal expansion wire 177. While the radial projection units are shown with shafts and tool-inserts that are hexahedral or rectangular in vertical cross section, these could just as well have been circular or elliptical, for example.

To prevent lift-platform 176 from being pulled out of lift-shaft 182 by levering and expulsive forces encountered during tool-insert use and to allow the use in fluidic circuits of inert bits and syringes that block the outflow of fluid and allow the fluid to continue through the circuit as well as to avoid sharp projecting edges at the outer or radial surfaces of the muzzle-head or radial projection catheter, tool-insert holding and lift-platform 176 and tool-insert holding and lift-platform 176 have depressed areas for allowing slide- or swing-over hold-down arms 186 to be positioned over the outer or radial surface of tool-insert holding and lift-platform 176 in inset relation to the radial surface.

When present, these are positioned over the tops of side boss guides and channels. While not ordinarily needed with friction fit tool-inserts 184, hold-down arms 186 can be extended over the radial edges of these for increased retention. The depth of the depressed areas is the same as the vertical thickness of swing or slid out arms 186, so that the elsewhere the upper surface of lift-platform is level with the rim of lift-shaft 182 at the outer surface of the muzzle-head or radial projection catheter.

VII2g(3)(d)(i)(2). Structure of Fluidically and Microfluidically Operated Radial Projection Units As with electrically operated units, space optimization requires that every unit have maximum potential functionality to support any suitable tool-insert. Nevertheless, a unit of given specification will be able to accommodate fluids of different viscosity moved at different velocities only over a limited range. Thus, while units for use with non flow-through inert bits and syringes could be provided with a lift-platform that had no path for fluid to flow through, such gratuitous limitation is not preferred. Providing all fluid units with a lift platform that includes a hinged perforated cover over the outlet chamber and chamber partition that affords a passageway allows tool-inserts to be used for aspiration.

Liquids are generally superior for aspiration due to the momentum imparted to the debris, which is wetted and swept away with a washing effect. Propelling the debris through the line and components with greater force forestalls clogging and therewith the need to halt the procedure in order to flush the line with sodium hypochlorite, for example. Similar economies apply to fluidic tool-inserts, so that, for example, an initial dose or front-loaded fluid ejector is used as a noninitial dose intermittent or continuous fluid ejector and as an irrigator. Aspiration is addressed in the section above entitled Radial Projection Units and the section below entitled Use of Flow-reversible Tool-inserts for Microaspiration.

Both open and closed circuits can be adapted for miniaturization and incorporation into ablation or ablation and angioplasty-capable barrel-assemblies and radial projection catheters. Closed circuits are preferred for quicker response times and greater pressure range under potentially exigent circumstances. In a closed circuit, flow is past rather than directly to and from each unit tool-insert holding and lift-platform, necessitating the incorporation of a lifting mechanism adapted to alternately actuate during a passing antegrade flow and aspirate during a passing retrograde flow as often as desired. Radial projection units with hinged lifting chamber perforated passive fluid resistor roof-plates as described below thus pertain to tool-inserts capable of aspiration in a closed-circuit.

Referring now to FIG. 61, shown is a detail of the lifting mechanism of a fluid radial projection unit. To prevent the passive dropping away of lift-platform 176 under gravity when not lifted by the force of passing fluid and to achieve quick and positive return and seating of lift-platform 176 upon the cessation of flow, strip-spring 187 is used to elastically retract lift-platform 176 into flush relation with the top of fluid chamber separator 188. In antegrade operation, fluid enters and fills antegrade inflow or inlet chamber (entry chamber, ingress chamber) 194, pushes up against the underside of lift-platform 176 and upon exceeding the restraining force of strip-spring 187, forces lift-platform 176 to rise (radially outward).

The fluid-tight fit of lift-shaft 182 by tool-insert 184 prevents lift-platform 176 from being tilted upwards on the proximal inlet driven side, and to preclude jamming, the surfaces of lift-platform 176 and lift-shaft 182 that come into contact are made of or coated with a fluoropolymer or other slippery resin. For this reason, testing for operability and leaks prior to use must always be with a tool-insert installed in every unit. For testing in manufacture, inert blanks can be used; however, testing prior to a procedure should always be with the tool-inserts actually to be used regardless of type. Strip-spring 187 is fastened at its center to the top portion 189 of fluid chamber separator 188 by flat head pin, screw, or rivet 198.

For more secure attachment to the top of chamber separator 188, when upper portion 189 of chamber partition 188 is molded, pin, screw, or rivet 198 provided with a flange toward its embedded or distal end is inserted into the mold before injection. If necessary to avoid affecting the restorative force of strip-spring 187 by including it in a mold that includes pin or rivet 198 under high temperature, strip-spring 187 is fastened to the top of chamber partition (separator, divider, barrier) 188 through a hole at its center and the upper end of pin or rivet 198 flattened over it to create a head. If flattening by hammering or pressing would damage separator 188, then rivet 198 is extended to the bottom thereof so that rivet 198 rather than separator 188 sustains the force applied to flatten the head.

Strip-spring 187 has small slots toward either end so that the fasteners used to secure it to the underside of tool holding and lift-platform 176 can slide therein when lift-platform 176 moves up and down. Proper function requires that fluid from the supply line be properly apportioned between that forced up through the tool-insert and that continuing forward through the circuit. Fluid operated tool-inserts may have an actual cylindrical plug for insertion in the receptacle or socket atop the lift-platform or may provide only an opening that requires the lift-platform receptacle to supply the surrounding wall as a virtual plug.

The interposition of a fluid resistor in the path across the entry orifice (inlet, mouth) of the space for a fluid tool-insert inlet portal 201 through base entry and discharge portal or passageway 220 space or receptacle prevents fluid rushing past the orifice at a high rate from creating an unintentional vacuum at an ejection or injection tool-insert working face. Perforated plastic outlet chamber roof-plate 199 is therefore placed in the path of the fluid as a fluid resistor or flow resisting gate, referred to as roof-plate 199, with notch to clear strip-spring 187 and strip-spring securing pin, screw, or rivet 198 over outlet chamber 195. Roof-plate 199 is hinged along its upper distal edge by thinning short of its attachment to the chamber edge.

To limit the angle to which roof-plate 199 can rise so that fluids over a certain range are best accommodated, roof-plate 199 hinge 200 can include a stop. Differential response among tool-inserts best built into the tool-inserts rather than the lifting units, which should be uniform. If desired, however, differential resistance to lifting of the perforated passive fluid resistor roof-plate 199 during aspirative or retrograde flow can be obtained by varying the resistance to the lifting flow posed by each roof-hinge, whether by making the roof-plates of different materials or varying hinge thickness, the size range not permitting the use of separate torsion springs.

The extent of roof-plate 199 rising and size of its perforations are determined by the viscosity and velocity of the fluid or fluids employed during antegrade flow to actuate and retrograde flow to aspirate. An additional factor during aspiration is the anticipated size of the debris particles to be swept away. This can to a significant extent be controlled through the choice of inert bit or working face used to free the debris. When lift-platform has mounted thereupon a flow-through tool-insert rather than an inert bit blank, raising lift-platform 176 exposes tool-insert base-plug space entry orifice or receptacle opening 201 so that fluid can rise up into tool-insert 184.

Once lift-platform 176 is raised, fluid spills over the top of chamber partition 188, encounters fluid resistor 199 which raises the fluid pressure for lift-platform 176 to be driven higher forcing fluid up through base-plug space or receptacle opening 201. The composition of the fluid and velocity through the line determine the flow-through rate of roof-plate fluid resistor 199. Outlet (outflow, egress) chamber 195 fluid resistor roof-plate 199 has spanning from side to side along its underside near chamber partition 188 small roof-plate force-down blade 202 with bottom edge inclined toward chamber partition 188 that serves as a 2-way class II lever to assist in forcing roof-plate 199 down during antegrade flow (from left to right in FIGS. 59, 60, and 63) and up during retrograde flow.

It will now be apparent that during retrograde flow in aspiration, perforated passive roof-plate fluid resistor 199 also serves to increase the velocity of flow past opening or inlet 201 leading up into base-plug space, thus creating a pressure drop that results in an intake or aspirating force through any opening in the tool-insert working face. Fluid that is not diverted up through base-plug opening 201 flows through roof-plate fluid resistor 199 into outlet (ouflow, egress) chamber 195, thence down the line to the next ingress chamber, where the process is repeated. Lift-platform 176 is shown as having been raised by the surge of fluid over chamber divider (barrier, separator) 188.

Figure 58:
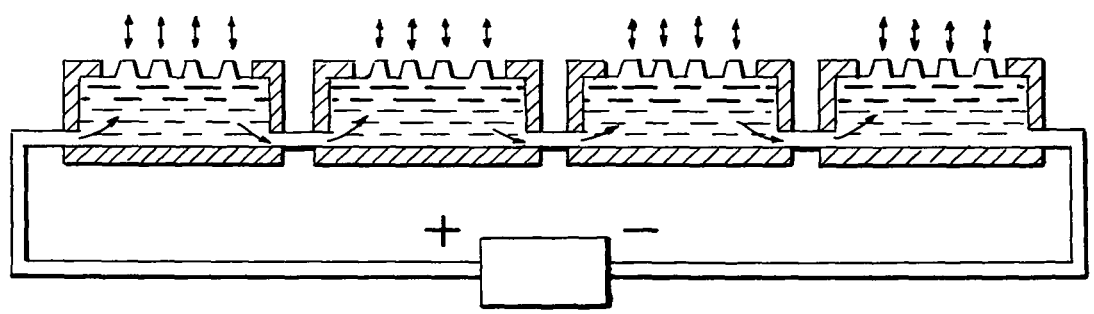
FIG. 58 depicts the equivalent fluidic circuit to the series wired electrical circuit shown in FIG. 57, such that all tool-inserts in the series must irrigate or aspirate in unison, whereas separate circuits would allow one, alternate, or all but one tool-inserts, for example, to flush the lumen wall at the same time that another, alternate, those following the irrigators, or others downstream aspirate the irrigation fluid whether water or a therapeutic solution.

Both nonpiped and piped pipelines function bidirectionally, and as depicted in FIGS. 57 and 58, in either, units can be arranged along a complete circuit or represent a singular, hence, independently controllable, end-unit, and various circuit elements might be introduced into the circuit to affect the units past that point. In barrel-assemblies and dedicated radial projection catheters used with fluids that cover a small range in viscosity, perforated plastic roof-plate fluid resistor 199 is permanently fastened along the upper edge of outlet or distal chamber 195 outlet, that is, atop the distal wall, by means of a flexible cloth tape hinge bonded by means of a suitable adhesive so that during antegrade flow, roof-plate 199 closes over the top of outlet chamber 195.

When the barrel-assembly or radial projection catheter must be usable with fluids covering a wide range in viscosity, outlet chamber roof-plate 199 is made interchangeable with plates of different pass-through conductance or permeability. Hinged attachment can be accomplished by means of watch band pring pin type fastening, which allows plates of different resistance to be interchanged by means of a tweezers or hemostat, for example. Reversing the direction of flow when the pump is reversed to initiate aspiration causes roof-plate 199, which would otherwise become clogged with aspirated debris, to lift up out of the path of the pumpward bound fluid.

When following aspiration this gate is in the lifted position, reversing the flow back into the forward direction will cause fluid to press against roof-plate force-down blade 202, levering roof-plate 199 back down into flush relation against the top of outlet chamber 195. During retrograde flow, the rush of fluid past base-plug entry orifice 201 imparts the vacuum effect desired at the working face of tool-insert 184. Accordingly, the roof of outlet chamber 195 is made of perforated plastic sheeting having a thickness, cross sectional area, and number of perforations responsive to the viscosity or range thereof. If always used with the same viscous fluid, the barrel-assembly or dedicated radial projection catheter is marked as intended for use in this viscosity range.

Preferably, the plastic plate, which to defer becoming clogged by debris during aspiration long enough to complete the procedure must be hinged to open, can be snapped in or out allowing the plate to be changed for use over a certain viscosity range. Both elastomeric membrane valves and strip-springs are spring valves. Both can be used to adjust tool-insert lifting force and control the rate of flow-through at a given line pressure. The specification herein of strip-springs is not to be interpreted in a limiting sense as to omit the use of equivalent elements, such as elastomeric membrane slit valves, for example.

Broadly, elastomeric membrane slit valves function bidirectionally, afford an area from central to peripheral for fixing the entry, and covering over an area independently of slit size or conformation, are suited for valving wide openings, whereas strip-springs function unidirectionally, are usually narrow, and are able to provide mechanical restorative force for returning the moving part loaded to its spring resting or starting position. Fluid at the minimum threshold pressure thus forces itself past the strip-spring up to its flexible limit. When the platform contains a hole and the fluid has no alternative path, a pressure head of sufficient force opens the joint allowing fluid to flow through the hole.

The strip-spring acts as a fluid valve or regulator which maintains a consistent relation of direct proportionality between the imposed pressure, extent of joint separation, and in a fluid circuit, rate of flow, which it does as the passive consequence of its intrinsic restorative force. As the pressure subsides until its force decreases below the threshold, the strip-spring pulls the platform back into closed flush relation with itself passively, proportionally and automatically. In a piped unit of the kind shown in FIGS. 59, 60, and 63, inflow-outflow chamber partition 188 serves not only to secure strip-spring 187 at the center, automatically retracting lift-platform 176 when the fluid current hence lifting force is removed, but to direct fluid entering through antegrade (left to right as shown) inlet line 203 against the underside of tool-insert 184, forcing the fluid over chamber partition 188.

When the base consists of a lift-platform that can be pushed up into a slightly wider upper body portion, as is essential in a continuous or non syringe injector, this lift-platform 176 is raised. A passive ejection tool-insert need not be lifted up against the lumen wall as must an injector or working face. Such a tool-insert has a unitary body. Fluid is thus driven up through the tool-insert and out the radial working face of the tool-insert. When the direction of flow is reversed in aspiration, outlet chamber roof-plate fluid resistor 199 is no differently raised by the inrush of fluid as in antegrade flow, and lift-platform 176 is lifted against the restraining force of strip-spring 187.

Hence, retrograde flow during aspiration does not significantly affect the lifting of lift-platform 176. Strip-spring 187 crosses over only the central portion the lower entry into base-plug 201 as shown, so that fluid pushes up against the bottom of lift-platform 176 to either side of strip-spring 187. Strip-springs used in fluid tool-inserts as a secondary resistance to injector lifting or to restrict a gap and thus the flow-through rate of an ejector used to deliver a low viscosity fluid, for example, can be given any conformation necessary. A loss in restorative force due to the need for cutouts, for example, is compensated for through the use of stiffer, plied, or thicker stock.

VII2g(3)(d)(i)(3). Extended Projection Scissors Lift-Platform Mechanism

In an electrically or a fluidically operated or nonpiped unit of adequate size, the distance of radial projection can be increased by incorporating a class I lever disposed in parallel relation to the floor of the lift-shaft to pull at the bottom end side-to-side cross beam of a stainless steel or tough surfactant-free polymer scissors lift thus causing the scissors lift to extend the tool-insert holding and lift-platform up from the floor of the lift-shaft. The use of a polymer is preferred as having a lower thermal coefficient. The lift is a microminiature version of a conventional workman's lift platform, the distance of lift dependent upon the length and number of scissors pivot arms. In an electrical unit, the scissors lift replaces the thermal expansion wire.

So that the lift will resist lateral deflection when the tool-insert it supports is in use, the pivot joints must be tight or free of play and rotate with minimal friction, and the rotary joints connecting the arms of the lever must resist vertical movement. The links of the scissors lift limit its descent to less than horizontal as would prevent a sidewise pulling force from causing the lift to rise. In a fluidically operated unit, the flow rate of fluid delivery must be adjusted apart from its adjunct use to raise the lift-platform to a height proportional to the instantaneous current or rate volume of fluid of flow-through. The lever is fulcrumed about a rotary joint or axle pivot by the anchoring or embedment of its lower end into the floor of the lift-shaft, an expanded head preventing the lever from upwards disengagement.

The shorter or effort arm of the lever is connected to a direct current spring-return intermittent duty push or punch type solenoid and longer or resistance arm connected to the scissors lift bottom side-to-side cross bar by a link having rotary joints at both ends. The scissors lift bottom side-to-side cross bar closer to the solenoid is unconnected to either the solenoid or the lever and free only to rotate about an axle securing it to a side rail. The bottom side-to-side cross bar of the scissors lift opposite from the solenoid is free to move but is constrained by short low friction cylindrical extensions or studs at either side that pass through and ride along slots in the side rail to either side, expanded heads at the extremities thereof constraining the motion of the lift platform.

So that the lift platform will be stable when raised and a tool-insert in use, all joints and ways must be free of play and low in friction. The lever reduces the stroke or throw required which allows the of a solenoid as an actuator of acceptable service life. The scissors lift extends the lift platform farther outward radially and beyond the outer surface of the muzzle-head. It thus precludes the use of hole-down or lock down arms 186 in the figures, dependent for stability in use instead upon secure anchoring into the floor of the lift-shaft and the rigidity of its joints.

Extension past the outer surface of the muzzle-head opens the lift-shaft to the entry of debris all around that would foul the scissors lift preventing it from retracting and seating properly. The lift-platform is therefore aproned entirely around with a thin and soft but strong polymer velum or film, such as of low density polyethylene or polypropylene. The apron is bonded at a slight distance from the periphery to the underside of the lift-platform. The upper edge of the lift-platform is routed to provide a recessed ledge all around into which the apron folds when the lift-platform is lowered.

VII2g(3)(e). Radial Projection Unit Tool-Inserts

Fluidically operated or piped tool-inserts draw fluid from or return fluid to the fluid control circuit on a continuous or intermittent basis, to which these therefore require direct connection. Delivery of fluid from the fluid circuit means that the fluid used for control and that to serve as a therapeutic agent are one and the same, with fluid in the line replenished by take-up from a reservoir. In an ablation or ablation and angioplasty-capable barrel-assembly, the fluid circuit to include reservoir can be built into the battery pack handgrip section. These are usable only in fluid units in a fluid circuit. By contrast, mechanical syringes are self-contained and enclose a finite amount of injectant or ejectant.

Neither these nor inert bits such as shavers and brushes require direct connection to the lift-platform control current. While the muzzle-head is endoluminal, individual tool-inserts cannot be changed. However, selecting tool-inserts with different electrical or fluid actuating current levels allows individual tool-inserts in the same circuit to be differentially and/or sequentially actuated, tool-inserts can belong to different circuits, fluid emitter-irrigator-aspirators can be changed in function or the fluid through a given circuit changed at the reservoir, and bipartite or duplex barrel-assemblies can be resheathed with alternative combination-form radial projection catheters as the peripheral component without the need to withdraw the ballistic component of the barrel-assembly.

Equally usable in either electrical or fluidic units, mechanical syringes and bits are referred to as electrical/ fluid system-neutral. The same mechanical injector or injection tool-insert shown inserted into an electrical projection unit in FIG. 54 is thus shown inserted in a fluidically operated unit in FIG. 59. A tool-insert which incorporates an electrically operated feature such as a heating coil that must be controllable independently of the thermal expansion wire requires connection to a separate electrical circuit. Electrical tool-inserts are therefore usable on in radial projection units that provide a source of electrical current other than that used to operate the lifting mechanism.

This can be provided in fluidically operated units; however, when an electrical function is desired, control is made simpler if a unit in a parallel electrical circuit is used. A tool-insert, such as a shaver or brush, which incorporates a fluidically operated feature such as jet irrigation is usable only in a fluid circuit. Fluid injectors and ejectors sold with an initial dose of medication or another therapeutic substance combine characteristics of mechanical syringes and fluid tool-inserts, most made for one time use and disposal. Electrical or nonpiped radial projection unit tool-inserts are either blanks that are flat-faced for use as pushing arms or caps to seal off piped outlets or nodes, or ablative tools that are equipped with microrazors; bristle projections, or diamond particles for abrading tissue from the lumen wall.

Cutting tool-inserts can be manually swept over the plaque, with or without the turret-motor oscillatory mode used to vibrate the working end of the tool against the lesion. One or several tool-inserts can be provided. Piped radial projection unit tool-inserts can be perforated for delivering or aspirating a fluid or include multiple hypotubes to allow hypointimal, hypoendothelial, or intramural injection. Piped radial projection units are addressed below in the section entitled Piped Radial Projection Unit Tool-inserts. Provided a diamond tipped tool generates debris of a size small too small to embolize, an electrical unit can be used; otherwise, a trap-filter and preferably fluidic unit with aspiration are used.

Different tool-inserts are used for brush cytology, removing uncalcified plaque by cutting or abrasion, to push the muzzle-head towards the opposite direction, inject medication into the lumen wall, chill or heat the lumen wall, and so on. While medication should make further means for countering platelet aggregation nonessential, using a piped radial projection unit, a gas or liquid coolant such as chilled water, saline solution, nitrous oxide, or freon, can be moved across the inner face of the cutting head to reduce any conduction of heat. The passing of the tool over the lumen surface may be referred to as 'side-sweeping' regardless of whether a brush type tool-insert is used. Brush-type radial projection unit tool-inserts can be made to cover a wide range of bristle tip configurations, so that the specific appearance of the brushes in a given barrel-assembly as shown must be taken as exemplary.

The radial projection units can contain one or more brushes of like or different kinds, the face dimensions contingent upon the openings in the lift-platforms into which these must be engaged. To aid observation, radial projection unit tool-inserts are marked with bright contrast. A closed-face or blank tool-insert is used to fill the lift platform opening when another tool-insert is not in use. A blank can be used to push or nudge the muzzle-head toward the opposite direction to increase the force applied to a shaving tool-insert on the opposite side, for example. A blank tool-insert in a piped unit, as addressed below in the section of like title, can serve as a heating or cold plate when hot or cold fluid is flowed over the inner face.

The temperature can be adjusted from the cryoplastic to the thermoplastic with temperature reversal and stabilization at any intervening point as needed. Radial projection unit tool-inserts for ablative or atherectomy application are brush-like in conformation, the shaft stiffness and bristle tips configured to provide selectable gradations in the aggressiveness of tissue swabbing (swiping) or removal. When inserted into the tool holding lift-platform in a radial projection unit having a rear supply and aspiration line, either type of tool-insert can be perforated to allow materials to pass to or from the lumen wall. In an artery, the ability to brush the lumen wall makes it possible to accomplish a percutaneous translumininal atherectomy and remove, rather than smash plaque up against the lumen wall, as does a balloon angioplasty.

An injection tool-insert such as shown in FIGS. 54 and 59 allows the introduction of a swelling or hardening (sclerosing) agent or medication preparatory to or following implantation. Brush tools with projections or bristles that unfold to greater length or that are biased to resist movement in one direction and fold in the opposite direction where different projections on adjacent tools could perform one action one way and another in the reverse direction are possible. Gradual retraction of the lift is passive, by the restorative force of the strip-spring upon the removal of current, and quick retraction active, by inserting a cooling catheter as addressed above in the section entitled Cooling Catheters (Temperature-changing Catheters).

Prone to the same complications as is every other means of intervention, the procedure can 1. Generate potentially embolizing debris, recommending the deployment of a run-ahead trap-filter, as addressed below in the section entitled Embolic Trap Filter in Radial Discharge Muzzle-heads for Use in the Vascular Tree, 2. Induce abrupt closure, recommending the administration of antithrombogenic and antispasmodic medication, as addressed above in the sections entitled Risk of Abrupt Closure and Stent- and Shield-jacket Moisture barrier-coated viscoelastic polyurethane foam Linings, and 3. Prompt intimal hyperplasia, recommending the administration of antirestenotic medication such as paclitaxel, rapamycin (sirolimus), and/or radiation, and immediate stenting.

Nonbristled inserts in the lift wells allow the muzzle-head to be nudged to a side of the lumen, clearing more cross-sectional area for contents to pass. In a blood vessel, minimizing occlusion time during an angioplasty has been demonstrated to lead to better results (Iliodromitis, E. K., Paraskevaidis, I. A., Fountoulaki, K., Farmakis, D., Andreadou, I., Antoniadis, A., Ikonomidis, I., Leftheriotis, D., and Kremastinos, D. T. 2008. "Staccato Reperfusion Prevents Reperfusion Injury in Patients Undergoing Coronary Angioplasty: A 1-Year Follow-up Pilot Study," *Atherosclerosis* 204(2):497-502). Hard mineral deposits can be removed during any procedure performed with a combination-form barrel-assembly, as addressed below in the section entitled Barrel-assembly with Exchangeable or Built in Rotational Atherectomy Burr.

Avoiding withdrawal and reentry reduces irritation at the entry wound but more particularly, allows the muzzle-port to remain in position over the sampled area for discharge. To allow the entire procedure to be performed without the need to withdraw and reenter, a combination-form barrel-assembly, as addressed below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy with either apparatus inserted is used. Such a barrel-assembly has a continuous central canal that opens at the muzzle-head nose that can be used as a kind of guide-catheter.

Except when hard mineral deposits such as calcified plaque in an artery must be removed, a noncombination-form ablation or ablation and angioplasty-capable barrel-assembly can be used. Using inmate radial projection units, the toughness of the material that may be abraded away or ablated depends upon the 1. Stiffness of the shafts and tip configuration of the individual projections (bristles, aristae, setulae, pectinatae) of the tool-inserts, such as those shown in FIGS. 51Ba and 51Bb, which function in a cutting manner similar to a conventional atherectomy catheter; 2. Output torque of the turret-motor on rotation; 3. Whether the turret-motor is used in oscillatory mode; and 4. Pushing and pulling force exerted by the operator or linear stage during transluminal displacement.

Due to differing tissue destructive action exposure times, the different ablative means incorporated into the muzzle-head are rarely if ever to be used simultaneously to perform an ablation or to eradicate liberated debris. More specifically, thermal ablation or atherectomy using recovery electromagnet heat-windows, or cryogenic ablation or atherectomy through connection to a source of cryogenic fluid, is not combined with abrasive side-brushing or shaving by tool-inserts. However, for use in ablation or ablation and angioplasty-capable barrel-assemblies, the potential utility for consecutive use of these processes justifies incorporating brushing, aspirating, and medication-delivering side-sweepers and heat-windows in muzzle-heads.

The speed and vigor of sweeping are increased through use of the vibratory, or oscillatory, mode of the turret-motor, as addressed in the section above entitled Turret-motor Operational Modes and that below entitled Modes of Failure. Use of the oscillatory mode generates a larger amount of debris in a given interval, recommending use with insert brushes that incorporate an aspirant evacuation path for use in a fluid-controlled line which can be reversed in the direction of flow to provide aspiration, such as those shown with injection tool-inserts in FIGS. 54 and 59. Except in a barrel-assembly marked 'Not to Be Used in Blood Vessels,' which will lack a run-ahead trap-filter, the current to abrading or brush type tool-inserts is shunted through a time delay relay, causing the radial projection unit to lift the tool into position or to deploy a moment after the trap-filter, which receives current directly.

In the gut or airway, provided the patient is recumbent, a dropped miniball sticks to the side of the lumen and is readily retrieved, making the use of a trap-filter unnecessary. Biopsy sample aspiration with or without the aid of brush or aspiration tool-inserts can be accomplished without the need for withdrawal and reentry in order to initiate the discharge of medication and/or stent miniballs. Withdrawal is avoided by aspirating the material, whether loosened with the aid of an abrading or shaving tool-insert, from the lumen surface through a service-catheter, as addressed in the sections below entitled Service-channel Adhesive Delivery Line and Muzzle-head Access by Means of a Service-channel.

Use of a barrel-assembly for aspiration is also addressed above in the section entitled Use of the Barrel-assembly as an Aspirator or Transluminal Extraction Catheter to Retrieve Biopsy Samples. The sample need be aspirated out through the inserted catheter only far enough to allow its recovery on withdrawal. While for most purposes, a barrel-tube that is not required for discharge can serve as a service-catheter rather than as the service-channel or conduit for a narrower service-catheter, this is not true when tissue must be recovered for analysis and not just removed by means of aspiration. This is because the vacuum pressure required to withdraw the sample, which will usually cling to the inside of the catheter, the entire distance to the proximal end will cause injury to if not perforate the treatment site.

Aspiration is ordinarily by bulb or syringe pipetting the sample into the distal end of the service-catheter with the least vacuum that will allow a viable sample to be retrieved. The catheter is then withdrawn and the sample blown onto a slide or into a petri or other sample dish, test tube, or crucible. Microtome-like tissue samples are obtained by inserting a shaving or razor head into a radial projection unit and drawing the shaving into the distal end of a service-catheter. To minimize damage to finely sliced samples, clinging to the inside walls of the service-catheter is made of polytetrafluoroethylene. A side-socket, as addressed below in the section entitled Ablation or Ablation and Angioplasty-capable Barrel-assembly Side-socket, for admitting the service-catheter into a barrel-tube, allows the barrel-assembly to remain engaged within the airgun without the need to move the muzzle-head.

This allows maintaining a steady position so that discharge is not redirected away from the same small target area just treated or sampled. By contrast, a barrel-assembly without a side-socket requires that the end-plate be used as a socket, or end-socket, which to attach an external source of gas, for example, requires removal from, then to initiate or reinitiate discharge, reinsertion in the airgun. Unless the treatment area is large or the muzzle-head stable in position without being attended to, removing and reinserting the barrel-assembly in the airgun can make recovery of the treatment site target time consuming whether the barrel-assembly is of the radial discharge or simple pipe type.

Recent developments in fiber or flexible endoscopes indicate that these should become available in diameters that will allow direct viewing of the lumen wall through a barrel-tube (Seibel, E. J. 2008. "1-mm Catheterscope," *Proceedings of the International Society for Optical Engineering* (Society of Photo-Optical Instrumentation Engineers SPIE), *Optical Fibers and Sensors for Medical Diagnostics and Treatment Applications VIII*, Gannot, I. (ed.), Progress in Biomedical Optics and Imaging 9:11, Session 6852, Presentation 7), with magnification possible that exceeds present requirements (Engelbrecht, C. J., Johnston, R. S., Seibel, E. J., and Helmchen, F. 2008. "Ultra-compact Fiber-optic Two-photon Microscope for Functional Fluorescence Imaging in Vivo," *Optics Express* 16(8):5556-5564).

The incorporation of radial projection units into any (minimally ablation or ablation and angioplasty-capable) muzzle-head confers an ablation and angioplasty capability, but has greater utility in ablation or ablation and angioplasty-capable barrel-assemblies, wherein the use of different tool-inserts can be coordinated with other ablative means, such as thermal and cryogenic. Combination-form ablation or ablation and angioplasty-capable barrel-assemblies can additionally accommodate interchangeable rotational or other atherectomy, thrombectomy, and endoscopic devices, for example, which have been modified for incorporation thus rather than for passage along a guide wire.

For this reason, radial projection units, while shown in the muzzle-head of FIGS. 49, 65, and 66 for example, are addressed when fully ablation or ablation and angioplasty-capable barrel-assemblies are described. Similarly, 'heat-windows, as addressed below in the section entitled Thermal conduction windows (heat-windows) and insulation of the muzzle-head body in thermal ablation or thermal angioplasty-capable barrel-assemblies, can be incorporated into any muzzle-head to impart a thermal and cryogenic ablation and atherectomy capability that is made more versatile when accompanied by the coordinated functions available in an ablation or ablation and angioplasty-capable barrel-assembly.

VII2g(3)(e)(i). Types and Functions of Radial Projection Unit Tool-Inserts, Electrical and Fluidic or Piped The radial projection unit must support the internal functions within the tool-insert; hence, the types of tool-insert had already to be addressed above in the section entitled Radial Projection Units. Tool-inserts that do not require connection through the radial projection unit to an electrical or to a fluid line but are self-contained, can be used in either electrically or fluidically operated radial projection units. Such self-contained and thus system-neutral tool-inserts can be either completely passive or inert, presenting no more than a cutting face, or can be syringes for discharging medication or surgical cement, for example, contained within the syringe once a threshold lifting force has been attained.

While a fluid powered ejection or injection tool-insert with break-seal or push-through plug in the base-plug can be prefilled to function as a syringe that will release a substance into the lumen or lumen wall other than that to follow from the line, a fully self-contained system-neutral syringe isolates its contents from the line. This a. Prevents unwanted intermingling of syringe and line substances and b. Allows use of the line fluid as an hydraulic fluid to actuate self-contained spring released injectors containing other substances while c. The line fluid itself serves as a larger volume injectant delivered through a fluid injector. The fluid in the line can, moreover, be changed by switching reservoirs as necessary with or without intervening flush liquid as necessary, and d. Allows the line fluid in a barrel-assembly or a radial projection catheter to be used purely as an hydraulic medium not requiring change or replenishment with each use.

Only sterilization is then required before proceeding to another procedure. Electrical tool-inserts are intended for use in electrically operated radial projection system units and exceptionally, in fluid system units that allow connection to a source of electrical power. Electrical power is supplied to the lift-platform socket in a fluid projection unit when only an electrically operated tool-insert can provide the function required and only a fluid projection system is present. Since fluid and electrical projection systems can run side by side, the need for electrical power in a fluid operated projection unit is exceptional. Distinctly fluid tool-inserts are not usable in an electrical projection system. Unlike a base-plug in an inert or compound mechanical tool-insert, the base-plug in an electrical tool-insert is not an optional mechanical connector but required as an electrical connector for insertion into the electrical receptacle or socket in the top of the lift-platform.

The need for electrical connection means that electrical tool-inserts are neither usable in a fluidic radial projection system nor self-contained. Whereas bit tool-inserts such as shavers, brushes, and flat-faced pushing arms with rounded edges are both inert and self-contained, electrical tool-inserts that contain a heating element, for example, lack moving parts and are in this sense inert or passive but not self-contained. Even though provided with electrical power line 214 and 215 to accommodate tool-inserts incorporating electrical features, base receptacle at the top of lift-platform 176 can be left vacant as shown in FIGS. 54 and 55 or can be used to accommodate a dummy tool-insert base-plug for securing the tool-insert within lift-platform shaft 182 by friction fit.

Electrical tool-inserts that incorporate a small motor to move the working face, for example, are neither inert or passive nor self-contained, as are gas discharged electrical syringe injectors and ejectors, especially those that gain space within the syringe for medication by using the lift-platform to house the gas generating chemicals, as described below. Both inert and motor-containing electrical tool-inserts can incorporate the same kind of membranes and springs to attain greater lift internally as can inert tool-inserts. Electrical tool-inserts can additionally incorporate gas-discharge and electrical spring release means to attain greater lift internally.

Self-contained compound mechanical syringe tool-insert injectors and ejectors are used by energizing the radial projection unit lifting mechanism with the unit or units on the side of the muzzle-head or radial projection catheter to be used positioned flush against the tissue treated, here that of lumen wall 204. Resistance by the wall is used to effect the release of syringe contents. For clear visibility, the injectant contains contrast dye. If not abutted against the lumen wall when the lifting mechanism is energized, injection can proceed only if proper positioning is achieved immediately thereafter; if not, then the needle must immediately be fully retracted into the unit shaft.

VII2g(3)(e)(ii). Self-Contained Electrical/Fluid System-Neutral Tool-Inserts, to Include Injection and Ejection Syringes Unlike flow-through fluid tool-inserts, which emit fluid into the lumen or lumen wall during antegrade pumping of the actuating fluid, electrical/fluid system-neutral tool-inserts or syringes are completely enclosed or self-contained and can therefore be used with any suitable actuating liquid or gas as the motive medium, and the fluid can be heated or chilled as necessary. This allows the use of air, for example, to actuate injection and ejection syringe tool-inserts in blood vessels. The fluids used to actuate tool-inserts or use these to aspirate need not be the same. Whereas inert bit and fluid tool-inserts are generally sterilized and reused, mechanical syringe injectors and ejectors, which are equally usable in electrically and fluidically controlled radial projection system units, are prefilled, used once, and discarded.

The dimensions, especially that radial (vertical) of a tool-insert are widely variable according to the depth of the lift-shaft or well. A relatively shallow unit such as that shown in FIG. 55 is suitable, for example, for a radial projection catheter for ensheathment of a barrel-assembly wherein the radial space available is limited, whereas a taller unit, such as that shown in FIG. 54 might be accommodated by a stand-alone radial projection catheter without barrel-tubes and more radial space Lifting-height lifting height (radial distance, excursion, radial throw), that is the distance from the bottom of the lift-shaft or well 182 that the tool-insert is raised is independent of lift-shaft height or the radial space available and has little significance for functionality.

FIG. 54 shows a compound mechanical injection and FIG. 55 a passive ejection syringe which do not require electrical connection through base-socket 205, while FIG. 59 shows the same compound mechanical injection syringe as that shown in FIG. 54 in a fluid-operated unit. Not requiring connection to an electrical or fluid line for its internal operation and neutral as to whether the lift platform is raised electrically or fluidically, these tool-inserts can be used interchangeably in either type circuit. Electrical/fluid system-neutral syringes lack a plug at the bottom because these self-contained tool-inserts require neither electrical nor fluidic power.

In the compound mechanical spring-discharged syringes shown in FIG. 54 of an injection tool-insert or injector and FIG. 55 of an ejection tool-insert or ejector, a heating coil positioned within compression spring 206 in FIG. 54 or within piston-plunger 197 in FIG. 55 would necessitate electrical connection, hence an electrical base-plug such as 207 in FIG. 56. The fluid system tool-insert drawing FIGS. 59, 60, and 63 depict the lift-platform as having already been raised off the fluid chamber divider or separator wall which serves as the resting base for the lift-platform. Lift resisting strip-spring 187, fastened at its center to the top of the separator and at its ends to the underside of the platform is therefore shown with its end curved upward.

That outlet or outflow chamber 195 roof-plate fluid resistor 199 is cut away to avoid contact by or obstruction of strip-spring 187 is not seen in a side view. Since it is functionally optimized to support any interchangeable tool-insert, the receptacle in every electrical unit includes electrical contacts. In the system-neutral syringe of FIG. 54, the lack of a heating coil means that the space within spring 206 can be filled with the lower portion of syringe therapeutic fluid holding bladder 208, increasing its capacity. The equivalent fluidic injection tool-insert such as seen in FIG. 59 requires neither a coil to warm nor a spring to discharge its contents and therefore optimizes the space available.

The need for electrical power would limit these syringes to an electrical projection unit. A heating coil added to the syringe shown in FIG. 54 would not only allow warming the contents but use of the elevated piston as a heating element whether a warmed ejectant had been discharged or the syringe empty. Sliding or swing-over tool-insert retaining arms (lock-arms, tool-insert lock-down arms, stops, tool-insert retaining clips) 186 are fastened in depressions at the surface of the muzzle-head or radial projection catheter about the opening into lift-shaft 182 within swing-way depressions located at opposite sides of lift-shaft 182 by rivets used as axles.

These depressions complement proximate depressions in the radial surface of tool-insert 184 such that swing-arms 186 can be rotated on opposite sides of tool-insert 184 to span over the joints separating the tool-insert from the muzzle-head to either side thus locking down tool-insert 184 within lift-shaft 182. One arm fore and one aft of the lift-shaft are usually sufficient to assure retention of the tool-insert. The depressions for hold- or lock-down arms 186 are equal in depth, so that the radial surfaces of tool-insert 184 and muzzle-head are level. Tool-insert lock-down arms 186 hold down tool-insert 184 within lift-shaft 182 both when lift-platform 176 is raised and when its working face is applied to the lumen wall and encounters tangential or shear forces that would dislodge it.

Receptacle or socket 205, empty with this mechanical tool-insert in use, is available as an electrical connector for use with an electrical tool-insert, which would have a plug extending downward from its base for insertion into socket or receptacle 205. Compound mechanical injection syringe tool-insert 184 is enclosed within two telescoping sections that protectively encase the tool-insert injectant, the upper section receiving the lower, opposing or interlocking rims serving to prevent the sections from separating. Syringe plunger or piston (the intromitting lower section as shown) 197 slides into syringe barrel (upper section as shown) 196 smoothly with the clearance essential without play.

Syringe barrel 196 contains at its top center aperture 211, which sealed by any suitable means before use, is just large enough in diameter to allow injection depth-limiting external flange or stop 210 surrounding hollow injection syringe needle 209 at a distance from the needle tip to pass through. The interior of the injector is kept sterile by a tab of plastic film or metal foil applied with a suitable temporary pressure-sensitive adhesive and discarded after use. Syringe injectors and ejectors are single-use disposable products packaged with the injectant or ejectant prefilled. To assure that syringes for use in the bloodstream contain the dose intended and no air, some injectant is passed entirely through the needle before packaging.

Both for safety and to maximize the size of dose that the syringe can accommodate, needle 209 is no longer than necessary. Gaining additional space through the use of a fold-down lie-flat needle such as one mounted to the syringe ceiling is not preferred as less dependable in retracting, more prone to leaking about the base, and possibly opening by accident. In a tool-insert supplied with electrical current such as shown in FIG. 56, a base-plug extending downward at the center from the bottom of the tool-insert serves to electrically connect the tool-insert into the electrical circuit. In a fluid tool-insert supplied with fluid current such as shown in FIGS. 59, 60 and 63, the outlet of the fluid circuit is configured as would a base-plug and capped off by a spring-loaded trap door that retains the fluid in the circuit when no tool-insert is present.

Fluid operated tool-inserts such as injection syringes that contain a preload for initial delivery are sealed at the bottom to retain the fluid contents within bladder 208. In a tool-insert not requiring internal power, base-plug 207 when not omitted as shown in FIGS. 54 and 55, can be a blank or dummy, which would insert into empty receptacle 205 in FIGS. 54, 55, 59, and 60, used to retain the tool-insert in the lift-platform receptacle by friction fit; otherwise, old-down arms or clips 186 serve to secure tool-insert 184 within lift-shaft 182. Helical compression spring 206 is fastened, down to the floor of syringe piston 197 with its upper end similarly fastened to the underside of syringe bladder 208, containing a measured dose, for example, of a medication, an amount of surgical cement, or a tumefacient.

To assure that the contents at the center of bladder 208 and not just the contents overlying syringe compression spring 206 about the circumference are fully ejected and the assigned dose released, either spring 206 drives the bottom of bladder 208 up and past syringe needle 209 and bladder puncturing lance (blade, lancet) 213 fastening hillock 212 or collapsible syringe bladder 208 has a central solid plate at the bottom for driving the overlying contents up and out. The material identity, density, and thickness of bladder 208 are selected based upon puncture resistance at the temperature for injection.

Syringes containing a heating element and those close to sources of heat such as from a parallel fluid circuit must be thicker or made of stronger thermoplastic sheet, generally 1.5 mil thick low density polyethylene. Those close to sources of cold must have a bladder that is less resistant to puncture at colder temperatures. Needle 209 must withdraw without resistance, and bladder 208 must not be so resilient that upon return to the retracted position or reseating by strip-spring 187, needle 209 can rebound through needle tip aperture 211. Surmounting injection syringe bladder 208 is hollow injection needle 209 with integral bladder puncturing lance (blade, lancet) 213 extending from its lower edge.

When bladder 208 is made of a material, typically polymer sheeting such as polyethylene or polypropylene, which punctures (Tabatabaeia, S. H., Carreau, P. J., a, and Ajji, A. 2009. "Structure and properties of MDO [Machine Direction Orientation] Stretched Polypropylene," *Polymer* 50(16): 3981-3989; Lange, J., Mokdad, H., and Wysery, Y. 2002. "Understanding *Puncture Resistance* and Perforation Behavior of Packaging Laminates," *Journal of Plastic Film and Sheeting* 18(4): 231-244) with much force against the tip of needle 209, needle 209 is mounted to a syringe bladder puncture seal of the desired puncture resistance mounted to the top of bladder 208.

Such a seal may replace the material of bladder 208 or increase resistance to puncture as an added layer. Needle 209 atop bladder 208 is held in the vertical position, sealed all around to prevent leaking, and fastened to the top of syringe bladder 208 or a syringe bladder puncture seal (unshown) by embedment within small encircling mass of gummy or rubbery adhesive caulk forming hillock 212 having the consistency of pliant silicone rubber. When energized or sent current from the control panel, thermal expansion wire 177 forces tool-insert holding and lift-platform 176 radially outwards against lumen wall 204, upwards as shown. Spring 206 is under no compression until lift-platform 176 begins to push needle 209 against lumen wall 204 through aperture 211.

For sufficient resistance to penetration of needle 209 into lumen wall 204 to cause bladder puncture lance or blade 213 to cut into the top of bladder 208 or the bladder puncture seal and to control the depth of injection or that needle 209 penetrates into and injects the tissue under treatment, here lumen wall 204, needle 209 is usually provided with external surrounding flange 210 at the distance from the tip of needle 209 desired. The depth of injection into lumen wall 204 is set by the distance thermal expansion wire 177 raises needle 209, and the length of needle 209 or the distance to the tip of needle 209 of needle-encircling injection depth limiting flange or stop 210. Flange 210 can be increased in width to reduce sinking into soft tissue as would necessitate more lift.

For a flange of given diameter, the softer is lumen wall 204, the less must be the force exerted by spring 206 and the greater the ease with which bladder puncture blade or lance 213 cuts through bladder 208 or the bladder puncture seal. To assure proper depth of injection, the resistance to penetration of the tissue under treatment, here lumen wall 204 by the tip of needle 209 at distances less than from the tip to the flange must be less than the force necessary for bladder puncture lance or blade 213 to puncture bladder 208. Except with mineralized accretions, this will be the case. As lift-platform 176 continues to rise driving tip of needle 209 followed by needle flange 210 against lumen wall 204, spring 206 continues to accumulate elastic potential energy, eventually causing syringe puncture lance or blade 213 to puncture syringe bladder 208 or syringe bladder puncture seal if present atop collapsible bladder 208.

This sudden reduction in resistance to compression of bladder 208 allows energized spring 206 to expand driving the syringe plunger plate if present radially outward or abluminally (upwards as drawn), causing bladder 208 to expel its contents through injection needle 209 and into the tissue under treatment, here that of lumen wall 204. The volume flow rate of emission is governed primarily by the dimensions of needle 209 and the diminishing force exerted by spring 206 in relation to the viscosity of the contents contained within bladder 208. These variables are all controllable, so that it should never be necessary with a low viscosity injectant to continue raising lift-platform 176 until syringe bladder 208 is fully emptied in order to preclude the premature extraction of needle 209 due to the sudden collapse when punctured of bladder 208; spring 206 should sustain the depth of needle penetration.

The density and strength of the tissue injected may also be adjusted by means of antecedent treatment accomplished with the aid of neighboring ejection or injection tool-inserts. Helical syringe spring 206 shown in FIGS. 54 and 59 can be replaced with springs different in number or kind. In an electrical radial projection system such as shown in FIG. 56, conductors are provided through lift-platform 176 that end in the electrical contact points or contacts at the surface of base-plug socket or receptacle into which base-plug 207 is inserted. Injection needle 209 must be fully retracted before resuming movement of the barrel-assembly or dedicated radial projection catheter.

The retraction of needle 209 is accomplished by recession of lift-platform 176 rather than by means within syringe tool-insert 184; that is, the nonretractable or irreversible means within the syringe used to raise syringe plunger 197 once bladder 208 is punctured, consisting of the helical compression spring 206 shown in FIGS. 54 and 59 or the gas release and expansion mechanism such as described below and shown in FIG. 56 is be used to retract needle 209. Ejectors do not require retraction; however, limiting a system to ejectors negates versatility of tool-insert interchangeability in a muzzle-head or radial projection catheter of given size. A system for use only with ejectors incapable of injection does not require radial projectors.

While genuinely independent control of each radial projection unit in an electrical or a fluidic system necessitates that each be connected in an independent circuit, one means for adjusting the order in which each unit lifts even when connected in series is to include in each unit a barrier that complies to a different degree of force. Here strip-spring 187 holding the apices of the coil turns of thermal expansion wire 177 up flush against the bottom of lift-platform 176 can be varied in dimensions and materials to obtain widely variable varied restorative forces or deformation resistance values. When radial projection units are sufficient in number, setting the mechanical properties of the units and tool-inserts in a given circuit assists in making arrays of contoured profile in cooperation with neighboring circuits whether electrical or fluidic.

For a given level of current, all units in the circuit that would actuate at a lower current level will lift; however, with syringes, earlier collapse of injection tool-insert syringe bladder 208 means that tip of needle 209 will now be receded so much lower within the injection syringe tool-insert that it can no longer emerge. This allows the individual units to be used in a preferred sequence. Turning now to FIG. 54, shown is a self-contained disposable electrical/fluid system-neutral compound mechanical ejection tool-insert (ejection syringe, syringe ejector). The same system neutral or interchangeable injection syringe is shown inserted into a fluid operated radial projection unit in FIG. 59.

Syringes that must keep warm or heat the contents of bladder 208 include a heating element connected to a source of electrical current through an electrical base-plug such as that shown as 207 in FIG. 56; otherwise, a base-plug is not needed, the receptacle where a base-plug would insert shown in 205 in FIGS. 54, 55, 59, and 60. The system-neutral injection syringe shown in FIGS. 54 55, and 59 requiring neither a power nor a dummy plug, lift-platform 176 electrical socket or receptacle for base-plug 207, provided by current through leads 214 and 215 as a permanent component of the lift-platform available for any interchangeable tool-insert requiring power for internal components, is accordingly shown empty as 205.

By comparison, a flow-through fluidic ejector is not self-contained, instead drawing fluid from the fluid circuit or line, so that the fluid can be delivered at any temperature preferred whether hot or cold. An ejector must begin to release its contents not once a certain depth of penetration into the lumen wall has been reached, but rather whenever the operator directs release. Not contingent upon a threshold contact force normal to its working face as is an injection syringe, ejection syringe actuation can be accomplished with a simpler mechanism without needle 209, bladder 208, or bladder puncture lance blade 213 under the direct control of the operator.

Figure 52A:
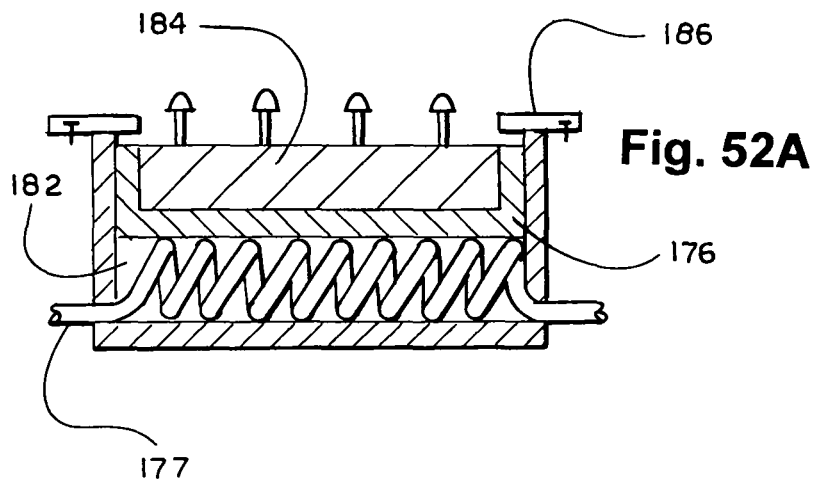
FIG. 52A is a diagrammatic longitudinal section view through an expansion wire-lifted electrically operated radial projection unit with curettage (evidement, scraper abrader-type) tool-insert shown in FIG. 51C engaged within the holding and lift-platform raised slightly short of the upward limit.
Figure 52B:
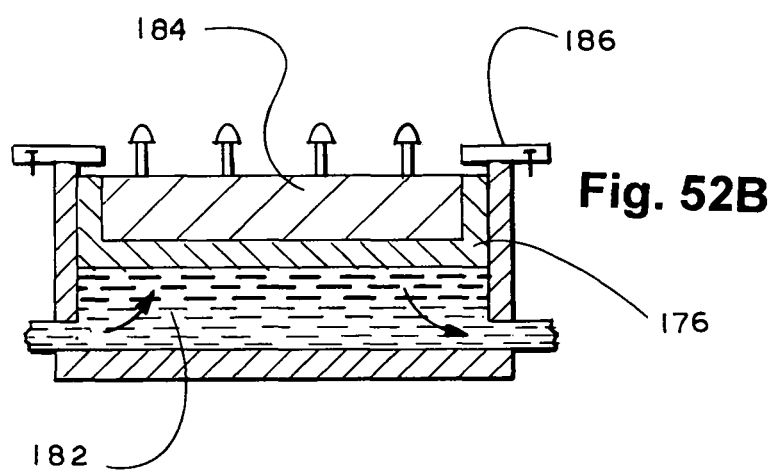
FIG. 52B is a diagrammatic longitudinal section view through a fluidically operated radial projection unit with the same curettage or evidement tool-insert shown in FIG. 51C engaged within the holding and lift-platform as that shown in FIG. 52A raised slightly short of the upward limit.
Figure 52C:
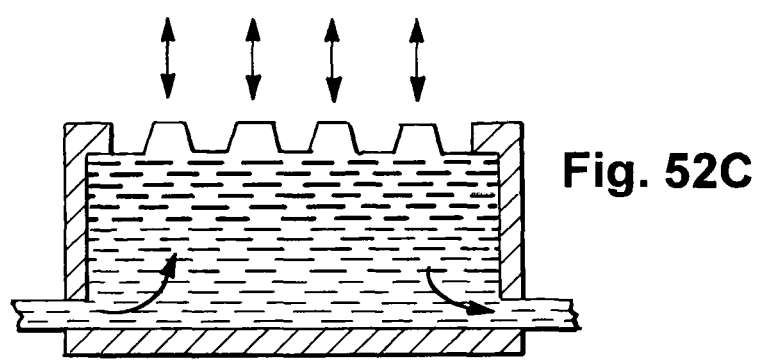
FIG. 52C is a nonprojecting or stationary fluidically operated ejection-irrigation aspiration unit, which unlike the interchangeable tool-insert accepting bidirectional units shown in FIGS. 59, 60, and 63, can aspirate only once the supply line and inflow and outflow chambers have been emptied.

The lack of a needle also eliminates the need to keep the point of emission safely retracted within the syringe body before and after use, and frees the radial space within the tool-insert occupied by a needle for storing a larger dose of medication or volume of liquid for the same sized syringe as compared to an injector. The syringe tool-insert is held down inside lift-shaft 182 by hold-down arms or lock-down clips 186. FIG. 52c shows a permanent or non tool-insert accepting fluid ejector, which releases fluid directly from the power supply line where the fluid can be water, a solvent containing a therapeutic substance in dissolution, or a liquid or gas fluid therapeutic substance.

An ejection syringe as shown in FIG. 55 consists of an upper or receiving body section, or barrel 196 into which syringe piston or plunger section 197 intromits or telescopes when lifted (radially projected) in this electrically operated radial projection system by lift-platform 176 under the force exerted by thermal expansion wire 177 when energized through leads 214 and 215, controlled at the ablation or angioplasty control panel. Syringe barrel 196 receives piston plunger 197 so that the ejectant housed within bladder 208 is prevented from leaking out the sides, these body sections prevented from separating and further sealed against leaking by complementary interlocking ridges about the rim of each.

As seen in FIGS. 55 and 63, roof or perforated emission working face 216 of syringe barrel 196 has holes 217 through which the medication or other therapeutic substance is forced out when syringe piston or plunger 197 is actuated. The ejectant is kept sterile and prevented from running out ejection holes 217 by a tab of plastic film or metal foil applied with a suitable temporary pressure-sensitive adhesive and discarded after use.

Electrical/fluid system-neutral syringe ejectors can incorporate additional or alternative principles of operation (see, for example, Yuk, S. H., Cho, S. H., and Lee, H. B. 1992. "Electric Current-sensitive Drug Delivery Systems Using Sodium Alginate/Polyacrylic Acid Composites," *Pharmaceutical Research* 9(7):955-957). An electrical syringe with internal heating element or coil can heat the contents to alter and/or effect its release into the lumen (see, for example, Shi, J., Liu, L., Sun, X., Cao, S., and Mano, J. F. 2008. "Biomineralized Polysaccharide Beads for Dual-stimuli-responsive Drug Delivery," *Macromolecular Bioscience* 8(3):260-267). When such specialized equipment is unavailable, syringe contents can be changed in temperature by submersion in a heating or chilling bath.

Both electrical and fluid systems can be used to cause polyelectrolyte gels to tumesce (swell) and/or liberate medication by changing the pH or by heating and/or wetting the primary injectant, fluid systems not limited to syringe delivery and thus able to provide a larger volume of liquid. Incorporation of a radial projection capability is intended to assist in the removal of tissue for biopsy and/or the removal of softer deposits or debris adherent to the lumen wall.

This includes any residual atheromatous tissue following the removal of calcified prominences by a primary atherectomy device, whether incorporated into a combination-form barrel-assembly as addressed below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy, or a separate laser or rotational burr used prior to initiating implantation discharge (see Safian, R. D., Freed, M., Lichtenberg, A., May, M. A., Juran, N., Grines, C. L., and O'Neill, W. W. 1993. "Are Residual Stenoses after Excimer Laser Angioplasty and Coronary Atherectomy Due to Inefficient or Small Devices? Comparison with Balloon Angioplasty," *Journal of the American College of Cardiology* 22(6): 1628-1634).

Radial projection unit tool-inserts and heat-windows can be used to remove ductus-lining or obstructing material or tissue whether in blood vessels or other ductus, such as salt deposits along the walls of the ureters. Perforated flat-faced tool-inserts can deliver heated or chilled gas to the treatment site. Since atheromatous detritus accumulates beneath the endothelium, to access and eliminate plaque must involve penetration through and thus injury to the endothelium. Intuitively, such injury that results in the actual elimination of the plaque should be preferable to endothelial tearing injury by a balloon that only crushes the plaque into the media.

Intimal hyperplasia and restenosis likely to ensue even when plaque has been fully eliminated, medication and usually stenting are used to promote patency regardless of the means employed to effect plaque removal. Side-sweeping brush-type radial projection unit tool-inserts do not appropriate so much of the luminal cross-sectional area as to completely check the flow of blood and are quickly retractable. A rotational atherectomy burr is superior for the removal of stoney plaque but can furrow or even perforate the lumen wall. Another device that can be used in a combination-form barrel-assembly, a laser, can perforate as well, but is effective with all but the hardest plaque.

A directional atherectomy cutter is unlikely to cause such injury, but requires a preliminary step, most guide wire-directed devices such as this generally incapable of incorporation into a combination-form barrel-assembly, or only so after modification to work without a guide wire. The incorporability of separate devices into a combination-form barrel-assembly is addressed below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy.

While the use of a barrel-assembly equipped with radial projection unit ablative tool-inserts and an embolic trap-filter could be used to perform an angioplasty in preparation for stenting by conventional balloon, using the barrel-assembly avoids the need for withdrawal and reentry and effects plaque elimination. Whereas a preliminary atherectomy to remove calcified plaque protruding into the lumen that had prevented (obstructed) a balloon angioplasty would ordinarily be followed by a balloon angioplasty, the barrel-assembly, especially a combination-form that includes a rotational burr, for example, is able to proceed to stenting discharge without the need for withdrawal and reentry.

When the plaque does not contain mineral deposits and the muzzle-head is not significantly smaller in diameter than the lumen, the muzzle-head itself compresses plaque against the lumen wall, albeit not with the radial force of a balloon. Ancillary magnetic steering, such as by means of an external hand-held electromagnet, addressed below in the section entitled Use of An External Hand-held Electromagnet, or a built in magnetic navigation system, as addressed above in the section entitled Comparison of Extraluminal with Endoluminal, or Conventional Stenting, can also be used to actively draw the muzzle-head up against the lumen wall. However, these methods in themselves accomplish only a limited kind of angioplasty in the conventional sense of crushing the atheroma.

The barrel-assembly will usually incorporate thermal means such as 'heat'-windows and sockets for connecting sources of cold gas to supplement ablation by means of radial projection unit tool-inserts. To preserve the reduction in operating time when more difficult plaque is present necessitates the incorporation of additional means for removing plaque, recommending the use of a combination-form, even though the larger diameter will limit the number of barrel-tubes. In clearing in a single sweep the lumen of adherent material, plaque, or hyperplastic tissue just in advance of miniball discharge so that implantation discharge can follow immediately, this application of multiple means minimizes operating time.

Unless the material is a hard mineral such as a salt in a ureter or hydroxyapatite (hydroxylapatite) in an artery, a barrel-assembly with radial projection tool-inserts and heat-windows will serve to remove it. While the means exist to ascertain the composition, and therewith, the hardness of the adherent material (see, for example, Baraga, J. J., Feld, M. S., and Rava, R. P. 1992. "In Situ Optical Histochemistry of Human Artery Using Near Infrared Fourier Transform Raman Spectroscopy," *Proceedings of the National Academy of Sciences of the United States of America* 89(8):3473-3477; Gopal, A. and Budoff, M. J. 2006. "Coronary Calcium Scanning," *American Heart Hospital Journal* 4(1):43-50; Budoff, M. J. and Gul, K. M. 2008. "Expert Review on Coronary Calcium.," *Vascular Health and Risk Management* 4(2):315-324), such are often unavailable.

If uncertain, abrading radial projection unit tool-inserts with differently configured projection tips can be placed in the radial projection unit lift-platforms thus eliminating the need to withdraw the barrel-assembly to change tool-inserts. Projecting blank or flat-faced tool-inserts makes it possible to push the muzzle-head in the opposite direction to allow blood or other lumen contents to pass, aid in steering, cover over and distance untargeted intimal arcs from treatment elsewhere about the muzzle-head, stabilize the muzzle-head in longitudinal position, adjust the distance between the lumen surface and treatment unit on the opposite side, or cause a brush tool-insert on the opposite side to be borne against the lumen wall with greater force.

The muzzle-head can be nudged in any radial location in either of two ways. With one or a few radial projection unit tool-insert holding and lift platforms or few to be raised, the turret-motor is first used with the lift-platforms retracted to rotate the muzzle-head to the desired rotational angle, and then the unit or units desired are actuated. Encircling units can achieve such action without preliminary rotation of the muzzle-head. The simultaneous extension of blank tool-inserts that encircle the muzzle-head to simulate the compressive action of inflating a balloon, if over a short segment, is discounted as merely crushing rather than actually removing plaque.

To minimize the risk of injury to the endothelium, a preliminary lumen wall strength test as described below in the section entitled In Situ Test on Endoluminal Approach for Susceptibility of the Ductus Wall to Puncture, Penetration, and Perforation is performed at sampling points over the area to be pressed against, with equivalency for the intervening area interpolated. The risk of incision, puncture, or perforation is reduced by increasing the area over which force is applied. The force exerted against the lumen wall on the pushing side can also be reduced by combining vectors contributed by arcuately separate groups of units pushing in unison.

The coordinated use of multiple units each with a small contact or interface area also allows the use individually or severally for different purposes, imparting greater utility during any one procedure as well as for allowing different treatment options. When raised, a group of multiple units is not limited to the circular contact surface contour or profile of a single large unit as when these are retracted. Extending the end unit platforms to a progressively greater height allows units extended from a smaller diameter muzzle-head to assume an arcuate form better adapted to a lumen that is disproportionately large in diameter compared to the muzzle-head.

The need for gradual adaptation to variation in the lumen diameter, for example, can come about continuously or when moving more centrally, such as from a branch into a common trunk, for example. Individual units can also be controlled bistably as off and retracted or fully on and fully elevated and variability in the distance of lift or height among units can be structural, according to the shaft height (depth) and/or optionally, the incorporation of an extension mechanism, such as the lift-platform. A rounded off or feathered contour toward the boundary of an array of units is obtained by incorporating units with shaft depths of less depth as the boundary is approached. Control that is more versatile in providing continuously variability in the extent of lift requires a precisely calibrated control, such as includes a vernier scale.

To reduce the risk of incisions when pushing the muzzle-head to a side while in motion requires a large flat tool-insert surface area with blunted boundary to distribute the force whether accomplished by coordinating the use of multiple smaller units or using a single unit having a large face area. In smaller lumina, the use of a separate laser or mechanical cutting tool may be necessary. In larger lumina, depending upon the specific condition, single entry and withdrawal can be achieved through the use of a combination-form barrel-assembly with laser or rotational burr, for example, inserted, as addressed below in the section entitled Through-bore, or Combination-form, Barrel-assemblies: Barrel-assemblies which Accommodate or Incorporate Means for Ablation, Thrombectomy, Atherectomy, Atherotomy, and/or Endoscopy.

When, as can occur in the intrapulmonary bronchi, matter such as fibrotic obstructs the lumen, the ablative function of an ablation or ablation and angioplasty-capable barrel-assembly equipped with thermal ablation and radial projection unit shaving tool-inserts allows clearing the lumen and stenting with single entry. Where the use of stent-jackets is precluded, subcutaneous and/or suprapleural patch-magnets are used. Combination-form barrel-assemblies, however, cannot be made to so small a gauge as can the equivalent barrel-assembly without a through-and-through central canal or bore. The preliminary use of a separate atherectomizing device as would necessitate entry and withdrawal prior to using the barrel-assembly should arise seldom if ever.

When the lumen diameter is too small to admit a combination-form barrel-assembly, either an ablation or ablation and angioplasty-capable barrel-assembly with only radial projection units and heat-windows is used. The use of a separate laser or burr or of an ablation, atherectomy, or angioplasty catheter containing radial projection and/or non-projection units without barrel-tubes as mentioned above will require an initial entry and withdrawal before entry for stenting discharge. However, if the condition demands rotational atherectomy or lasing, and the lumen diameter will admit a combination-form barrel-assembly, the need for a separate procedure prior to stenting will be averted. When implant discharge is to follow, use of the ablation-capable barrel-assembly is more expedient.

Even when not contemplated preprocedurally, a barrel-assembly, unlike an ablation or ablation and angioplasty-capable catheter that lacks barrel-tubes, affords the option to initiate the delivery of medication or stenting at any moment. Here the term 'brush' denotes a tool-insert with projections mounted in close proximity to the same backing or block where the detailed configuration of the ends or tips of the individual elements or filaments can be or can be other than bristle-like. These brushes, with various tip configurations over a wide range of stiffnesses, longitudinal and arcuate lengths, and projection extensions are swept over the lumen wall to remove diseased tissue or debris by cutting (shaving) or abrasive (scraping) action (whence the terms 'side-shaver,' side-sweeper,' and 'side-scraper').

When retracted, the outer or working tips of the brushes end flush to the surface of the muzzle-head. Radial projection unit tool-inserts with different tip configurations are interchangeable and fit into the same tool-insert holding and lift platform socket or receptacle. The radial projection units are not provided with lift-shaft cover hatches to present a continuous surface when retracted. When a tool-insert of with a working end having a smaller area than the tool holding and lift platform is inserted, to minimize the surrounding space available for the accumulation of debris, the space is filled by extending the base of the tool-insert upwards as high as does not interfere with the working end.

Radial projection unit tool holding and lift platforms can be configured to accommodate tool-inserts such as brushes of different shape and/or type, and different shapes and types can be installed in units entirely about the circumference, although usually only two to four units are incorporated. Units can be controlled individually or in groups. Individual tool-inserts such as brushes, can be flat (wallpaper brush-configured) or square with filaments, bristles, or inclined shaving edges angled according to the direction determined by the oscillatory function of the turret-motor. Thus, inserting brush or side-sweeping tool-inserts of different stiffnesses and tip configurations over different arcs about the barrel-assembly allows the discretionary differential treatment of eccentric lesions.

The turret-motor can be used to direct the independently controllable radial projection units toward eccentric lesions, radiopaque and independently heatable heat-windows available if needed to assist in viewing the rotational angle. Regardless whether control of the turret-motor is by a servocontroller-amplifier microcircuit inmate in the hand-grip as in an ablation or ablation and angioplasty-capable barrel-assembly or by connection through the airgun as with a minimally capable barrel-assembly, reciprocating action can be obtained either by detuning the velocity loop causing the motor to oscillate, or by programming the oscillatory movement.

In either case, the action can be used with radial projection unit-deployed shaving or abrading tool-inserts. While in an angioplasty-capable barrel-assembly in use for an angioplasty, the turret-motor is usually limited to use as a heating element, when the side-sweeping or shaving tool-inserts are divided between different radial projection units for use in sequence in the treatment of eccentric lesions, and the path to the treatment site precludes rotation of the barrel-assembly, the turret-motor is used to rotate and thus select the radial projection units for use at a given time. Otherwise, rotation is of the barrel-assembly as a whole by manual rotation (twisting, torqueing).

In a battery-powered angioplasty-capable barrel-assembly intended for use independently of an airgun to perform an angioplasty, rotation of the muzzle-head requires incorporating the positional control into the onboard control panel mounted to the hand-grip-shaped battery pack at the proximal end of the barrel-assembly. Then both manual and remotely switched motor-driven longitudinal and rotatory sweeping of the lumen wall are provided. Gross transluminal or rotatory movements are normally manual, finer longitudinal movements accomplished by means of the linear positioning table stepper motor, and rotational movements by means of the turret-motor.

Unlike an inflexible blade that sees the maximum resistance along its contact edge and would cause injury if obstructed by tenacious apatite, for example, a brush sweeps away plaque that is soft while sweeping over plaque that is hard compared to the bristle stiffness. The turret-motor circuit breaker prevents any extra-bristle source of resistance from producing tears of the endothelium and intima. Resisting side-sweeping tool-inserts, means for identifying the presence of mineral deposits with the potential to disallow the use of such tool-inserts are necessary.

Computed tomography allows plaque calcification and other kinds of adhesions or protrusions into the lumen not only to be qualitatively confirmed but characterized as to shoulder to base distribution and percent content of calcium and hydroxyapatite (see, for example, Raggi, P. and Berman, D. S. 2005. "Computed Tomography Coronary Calcium Screening and Myocardial Perfusion Imaging," *Journal of Nuclear Cardiology* 12(1):96-103; Huang, P. H., Chen, L. C., Leu, H. B., Ding, P. Y., Chen, J. W., Wu, T. C., and Lin, S. J. 2005. "Enhanced Coronary Calcification Determined by Electron Beam CT is Strongly Related to Endothelial Dysfunction in Patients with Suspected Coronary Artery Disease," *Chest* 128(2):810-815; Thompson, B. H. and Stanford, W. 2004. "Imaging of Coronary Calcification by Computed Tomography," *Journal of Magnetic Resonance Imaging* 19(6):720-733; Rumberger, J. A., Sheedy, P. F. 2nd, Breen, J. F., Fitzpatrick, L. A., and Schwartz, R. S. 1996. "Electron Beam Computed Tomography and Coronary Artery Disease: Scanning for Coronary Artery Calcification," *Mayo Clinic Proceedings* 71(4):369-377;) or multi-detector CT-angiography (Miralles, M., Merino, J., Busto, M., Perich, X., Barranco, C., and Vidal-Barraquer, F. 2006) "Quantification and Characterization of Carotid Calcium with Multi-detector CT-angiography," *European Journal of Vascular and Endovascular Surgery* 32(5):561-567.

The application of a magnetic field to the muzzle-head through use of an extracorporeal hand-held electromagnet as addressed below in the sections entitled Steering and Emergency Recovery of Implants with the Aid of an External (Extracorporeal) Electromagnet and the $B_0$ magnet of a magnetic resonance imager as addressed below in the sections entitled Use of an External Electromagnet to Assist in Mishap Recovery and Stereotactic Arrest and Extraction of a Circulating, Dangerously Mispositioned, or Embolizing Miniball allows atheromatous lesions to be compressed much as does a balloon. While always an option, like the simultaneous extension of encircling blank tool-inserts to simulate the compressive action of a balloon, treatment thus is discounted as merely crushing rather than actually removing plaque.

Provided no significant buildup of hardened plaque is seen, using a minimally ablation or ablation and angioplasty-capable barrel-assembly, an atherectomy and stenting can be accomplished with single entry. Abrasion and shaving with suitable tool-inserts is useful for localized lesions susceptible of removal thus, which, however, excludes hardened plaque. Dependent upon its prominence and extent, stoney plaque may necessitate a bypass graft or ablation by rotational or directional cutter. If a significant buildup of hardened plaque is seen and the lumen is too narrow to admit a combination-form barrel-assembly, then a preliminary atherectomy with a separate device such as a rotational burr or laser must precede stenting or a bypass graft is required.

The force with which the brushes are projected and held beyond the surrounding outer surface of the muzzle-head is limited by the force exerted and pliancy of the thermal expansion wire or bimetallic tang used to raise or project the lift platforms. The configuration, dimensions, and materials of the tool-inserts and these elements are devised to minimize the risk of gouging injury. A thermal expansion wire affords the highest coefficient of thermal expansion, hence, makes possible the greatest displacement or excursion of the lift-platform, for its size. Based upon the polarity of the applied voltage when maximum, a crystal, by comparison, typically changes from thicker to thinner by one thousandth (see, for example, http://www.micromanufacturing.com/showthread.php?t=517.

Alternative actuators based upon dielectric elastomers, electroconstrictive or conductive polymers, polymer gels (gel motors) or hydrogels may be substituted for a thermal expansion wire, which more stable and simpler, provides a usable coefficient of expansion (Bauer, H. J. 1977. "Mechanical Motions in Small Inaccessible Volumes," i Journal of Physics E: Scientific Instruments 10(4):332-334, page 333), even though it requires cooling to effect retraction quickly. The protrusion of the bristles beyond the plane of the muzzle-head can be controlled not by adjusting tool-insert excursion through control over the degree of thermal wire expansion alone but also through using a tool-insert with projections of the length required.

Thus, the depth of penetration into the lumen surface can be set, for example, by the length of the bristles in a side-sweeper brush-type tool-insert rather than by adjustment to the extent of lift allowed. The interchangeable tool-inserts can be variously configured as, for example, subminiature curved or semicircularly tipped wallpaper smoothing (smoothers) or square-head type brushes. Using different materials in different thicknesses and lengths, the rigidity of the bristles is widely variable. Abrasive bristles or razors for removing plaque of given hardness as predetermined by computed tomography are provided as interchangeable tool-inserts. A barrel-assembly with multiple radial projection units allows plaque of different hardness to be removed with single entry.

The bristles must not be friable or susceptible to fatigue fracture, polyamide (nylon) being but one of many suitable polymer materials for making these. Bristles made of plied materials or projections of coextruded tubing in different diameters expand the degree of abrasiveness attainable. When reversing direction would cause the bristles to impose vectors that would pierce the lumen lining, the tips are blunted. The sharpness around the periphery of each bristle may be varied to affect its action as a drag-scraper. When the bristle tips are round and sharp but the lesion is soft so that dragging such a tip along the surface of the lesion only undercuts the surface to either side without actually removing the plaque, the faces of the bristle tip normal to the long axis of the lumen can be formed into a sharp-edged cup with cutting edge as shown in FIGS. 51B and 51C.

If the plaque or obstructive tissue is indurated or the accreted material hard, then cup-configured bristles, which could grab hold of and pull at that matter, are not used.

Diametrically opposed brushes can differ in bristle materials, conformation to include thickness, and stiffness. As shown in FIG. 52, the entry into lift-shaft 182 includes rotating hold-down arms (checks, stops) to lock the insert within the lift-shaft and limit the radially outward distance to which the too holding and lift platform can be raised. These are rotated to lock the tool-insert in the lift-shaft and limit the distance that the working tips can extend beyond the outer surface of the muzzle-head.

To expedite the passage of blood when deployed, the separate projections or bristles of a brush type tool-insert can be grouped into separate ferruled bundles or plugs that flare outwardly from the point of insertion in the brush-block (rib, backing) to provide gaps. Multiple small hypointimal or hypoendothelial injections rather than the single axis injections obtained from service-catheters can be accomplished with a piped radial projection unit injection head tool-insert, as addressed below in the sections entitled Radial Projection Units and Radial Projection Unit Tool-inserts.

Use of a hypointimal or hypoendothelial injection head, or to treat the lumen surface, a perforated blank insert tool in a radial projection unit that is piped, or equipped with rear supply line, as addressed below in the section entitled Radial Projection Units, allows a wider area of the lumen surface to be covered. To prevent fouling of the pipe, conserve injectant, and allow good control over dosing even when delivered as sequential aliquots from a single load, the delivery of a liquid substance (medication, swellant, sclerosant, cement, and so on) is through a service-catheter inserted into the pipe, as addressed above in the section entitled Preparation of Service-catheters for Use as Trans-barrel-assembly Hypotubes.

A hypointimal or hypoendothelial injection or syringe tool-insert can be used to quickly treat a miniball array covering a larger area. When the treatment seeks to close and mend or bond a delamination of the lumen wall, an injection head tool-insert can be used to deliver the bonding agent locally over a wider area more quickly than can injection through a service-catheter. With thicker walled ductus, the use of a bonding agent dense with contrast dye having a setting time adjusted to a few seconds may allow the lamina or tunics bounding an implant or delamination (dissection) to be compressed into more tightly bonded relation. To do this, the bonding agent is injected through a service-catheter or a radial projection unit injection-head tool-insert, the tip of the injection-head advanced toward the radially outer lamina, and the injection device bulb or syringe pipetted or connected to an aspiration pump to draw the outer layer inward compressing the layers together.

To prevent the sharp injection tip from puncturing the outer layers, aspiration is not initiated until the injection device is retracted. The technique is not intended where visibility is inadequate, the operator unpracticed using a synthetic model, or for use in blood vessels. A piped radial projection unit can be capped off or stoppered with a blank tool-insert. An advantage of piped units is that accelerated retraction of the projected tool-insert can be achieved by feeding chilled gas through the pipe to chill and contract the thermal expansion wire, eliminating the need to insert a cooling catheter that could not have been prepositioned, as pertains to a minimal ablation or ablation and angioplasty-capable barrel-assembly without a side-socket.

The momentary application of cold is used to retract the projected tool-insert, whereas sustained cold is used for cryoplasty, for example. Since piped units require a side-socket for use whenever the barrel-assembly is engaged in the airgun, even though these can be incorporated into minimally ablation or ablation and angioplasty-capable barrel-assemblies, piped units are addressed here in conjunction with ablation or ablation and angioplasty-capable barrel-assemblies. A perforated tool-insert in a piped unit allows tissue or lumen surface materials to be aspirated or fed back from the lumen wall or fluids delivered or fed forward to the lumen wall.

During the application of any transluminal process, aspiration through these can be added to that through service-channels or the central canal in a combination-form barrel-assembly and trap-filter to eliminate potentially embolizing debris. Fluid medication or a therapeutic chemical to which the lumen should be exposed for only a prescribed or an optimal interval can be delivered to the lumen surface through one or a plurality of perforated tool-inserts and aspirated through the same tool-inserts, or a continuous flow over a controllable path can be established using certain perforated tool-inserts in piped radial projection units to deliver and others to aspirate the fluid.

When the barrel-assembly is moved backwards (proximally), perforated tool-inserts can be used to spray coat the lumen wall or release medication just before the exit ports pass and the miniballs are discharged. To reduce the risk of incisions, such spraying action during transluminal movement is normally performed with the perforated tool-insert retracted, which is the default switching position that must be turned off to allow spraying with the tool-insert extended (in the raised position). Moving the barrel-assembly is moved forwards (distally), unused barrel-tubes can serve this purpose. Use of the same barrel-tube to alternately discharge miniballs and other substances without a service-catheter to line the barrel-tube risks jamming.

To minimize the distance material must be drawn proximally with vacuum force applied, aspiration for diagnostic evaluation or treatment is usually through a service-catheter which is withdrawn from the pipeline as soon as a sufficient sample is drawn into the distal end. Another primary use for radial projection units is to allow the discretionary raising of cutting (side-cutter) or sweeping brush (side-sweeper) tool-inserts, which must be kept recessed when not in use. These include brush configured shaving tools that consist of a back-block holding many individual projection razor edged tips or having razor edged bridges mounted to its front side for shaving the lumen surface.

The same or different units can be used not only to retrieve test samples at any point, prepare the surface, apply medication, and so on, but also to provide more or less aggressive cutting heads during the procedure, typically an ablation or an angioplasty. Greater extension beyond the outer plane of the tool holding lift-platform is obtained by incorporating a telescoping tool holding lift-platform, an insulated thermal expansion wire of larger coil diameter required. Directing a barrel-tube to the rear of a radial projection unit rather than to an exit port, whether singular or plural, represents a minor modification to a barrel-assembly, which in larger diameter embodiments could have some barrel-tubes used for discharge and some as supply lines with only those with exit ports used for discharge.

However,

1. A means for switching what is in effect a diverted barrel-tube between aspiration and discharge configurations, for example, impractical.

2. The diversion of a barrel-tube eliminating its use for discharge.

3. Sufficient barrel-assembly internal diameter at a premium, and

4. The barrel-tubes and central canal available for aspiration or other use as service-channels, the need to divert barrel-tubes solely for aspiration would be infrequent and done for an array of functions this could provide. A piped radial projection unit with a side-cutter or side-sweeper tool-insert installed can be used to deliver medication or hot air at the same time that it is used to ablate the lumen wall, and the resultant brushed or shaved debris can be removed by aspiration into a service-catheter.

Using a barrel-tube with exit port instead, it is also possible to insert a service-catheter that slightly extends a sharp serrated or scalloped front edge beyond the muzzle-port to obtain scrapings that are then withdrawn by bulb or syringe pipetting or attaching the service-catheter to an aspiration pump, for example. It is also possible to use either the exit-port or radial projection unit tool-insert (side-cutter or side-sweeper) to remove tissue which is then aspirated through the other component. The use of a cutting or sweeping tool-insert with perforated back block allows fluids to be delivered to the treatment site or tissue to be aspirated away prior to or during ablation or angioplasty.

A perforated radial projection unit tool-insert, whether blank or conformed for a second purpose, can be used to discharge medication that is drawn past the cutting tool in a central radial projection unit and aspirated away into a barrel-tube or a service-catheter inserted in the barrel-tube. The direction of this action can be reversed. In feed-back use, the rear supply line or access channel allows aspirated material, whether tissue for biopsy or removal or the removal of excess lubricant, medication, fixative, or adhesive, for example, to be drawn into a service-catheter for withdrawal, as addressed below in the section entitled Radial Projection Unit Tool-inserts.

Feed-forward use of the rear access channel (pipe, pipeline, supply line) allows therapeutic and/or temperature changing gases or liquid medication, lubricants, or other chemical to be delivered to the treatment site at the lumen surface. An injection syringe tool-insert such as that shown in FIG. 54 can be horizontally chambered or compartmentalized with each compartment containing a different substance and provided with a separate injection needle. Substances not be mixed before but rather to react once injected can be delivered thus. Multiple miniature injection or ejection syringes or microneedles common to a single chamber or compartment injection syringe tool-insert achieve more uniform release into the lumen wall.

Depending upon the extension of the needle points beyond the mouth of the lift-shaft at the surface of the muzzle-head, the needles can serve as hypoendothelial, hypointimal, submucosal medial, or perimedial hypotube injectors. With such means, the lumen wall can be suffused subliminally or submucosally with one or more liquid or gas drugs, adjuvant, other therapeutic substances or tissue cement, by one or more injection tool-inserts while coated at the surface with these or other substances through ejection tool-inserts or a barrel-tube with or without service-catheter. In the vascular tree, abrasion or aspiration to remove diseased tissue can be accompanied by a run-ahead embolic filter-trap or trap-filter to catch any loose debris.

Another advantage in piped radial projection units is the quicker automatic retraction of extended tool-inserts upon resumption in transluminal movement to avert the risk of incisions by the direct delivery of chilled gas through the pipe to the thermal expansion wire used to raise the tool-insert. As explained below in the section entitled Automatic Disabling of Implant-Discharge, Radial Projection Units, and Turret-motor, motion sensors on the muzzle-head provide the actuating current to an electrical valve controlling the outlet from a cylinder of chilled or chilling gas that has been preconnected to the barrel-assembly. An electrical valve has the advantage that it allows the release of gas from the cylinder to be controlled in duration (open time) and pressure (aperture area).

The alternative of using the motion sensors to cause a warning light on the onboard ablation and angioplasty barrel-assembly control panel to flash is not preferred, as this results in a delay for the operator to manual respond. When the source of chilled gas, whether a cold air gun or small cylinder attached directly to the barrel-assembly without tethering cannot be preconnected, an additional delay results. Yet another advantage in piped radial projection units is the opportunity for tool-insert holding and lift platform projection or retraction fail recovery by bulb or syringe pipetting or connecting the pipe to an aspirating pump should the lift-platform for any reason fail to retract or descend as necessary, or reversing the pump to blow, forcing a nonelevating lift-platform to rise.

When the pipe need not be used to deliver chilled or heated gas, the small pump can be connected when the procedure commences. In some instances, the same gas used to affect the temperature at the treatment site can be used to force the lift-platform into the elevated position. A malfunctioning lift-platform in a nonpiped unit must have ferromagnetic material incorporated to be lifted by the magnetic attraction of an external hand-held electromagnet and lowered by reversal of the magnetic field, which depending upon the context, can disrupt implantation. Unless the piped units are provided with a dedicated independent line that may course the full length of the barrel-assembly in a loop, to pipe a radial projection unit coopts a barrel-tube that might otherwise have been used for discharge.

However, since the pipe does not continue forward into the muzzle-head, the diameter of the muzzle-head need not be that of the equivalent muzzle-head with an additional discharge exit port. Depending upon the absolute diameter of the pipe line required, when a bank of radial projection units are to be used together for the same purpose, each can receive a branch from a single pipe. Advantage is also taken of the supply line, with or without use of the lifting capability, to discharge chilled or heated gas against the rear face of a heat-window configured to be interchangeable with other tool-inserts. The enhanced utility afforded by the projection capability generally renders providing nonprojectable heat-windows with a rear supply line uneconomic as underutilizing the space taken.

The tool-insert holding lift-platform is permanently installed in the shaft, and the pipe connected to the rear of the platform moves up and down with the platform. When piped, the tool-insert is either unperforated to serve as a gas-operated hot (thermal, thermoablative) or cold (cryogenic, cryoablative) ablating 'heat-window or is perforated to allow materials to pass in either direction. A perforated blank allows coating the lumen wall with medication, for example. A tool-insert with inoculation nozzles allows the hypointimal or hypoendothelial injection of medication or a tissue swellant, sclerosant, or cement, for example.

For reasons stated in the section below entitled Slidable Ablation or ablation and angioplasty-capable Barrel-assembly Power and Control Housing, fluid operated radial projection units are not incorporated into narrower ablation or ablation and angioplasty-capable barrel-assemblies. Instead, the barrel-assembly is first introduced and advanced to the treatment site while most readily steerable and least resisted, and then if needed, a size-matched combination-form radial projection catheter with fluid units, as addressed below in the section entitled Radial Projection Catheters, is slid over the barrel-catheter as it were a guidewire. Fluid operated radial projection units can be provided in larger barrel-assemblies.

Whether built into the barrel-assembly or the radial projection catheter, a fluid line can operate fluid units, and can deliver and remove fluid materials to, through, and from units on an intermittent or continued basis that syringes cannot achieve. Connected to an aspiration pump, the line can be used to aspirate diseased tissue as the cutting or brushing tool-insert continues to remove the tissue. The tissue retrieved can be used for analysis. When in order to eliminate the need for hosing to and/or from the barrel-assembly a fluid system is built into the Power and control housing hand-grip, a cartridge system for fluid replenishment and removal is provided. Whether onboard or connected, reversal of the pump or a an attached aerosol canister allows the line to be used for cryogenic angioplasty, the delivery of medication, a swellant, sclerosant, and/or cement, for example.

A piped radial projection unit has the advantage that chilled gas can be delivered through the pipeline to retract the lift-platform more quickly than does the insertion of a cooling catheter down a barrel-tube or the central canal when the radial projection unit is not piped, unless the cooling catheter can be prepositioned within the line as not previously needed for another purpose. To avert the unintended retraction of a tool-insert used in conjunction with the delivery of a chilled gas, as during use of a perforated tool-insert to perform a cryoplasty, for example, the thermal expansion wire must be well thermally insulated and capable of conducting a compensatory increase in current.

VII2g(3)(e)(iii). Self-Contained Electrical/Fluid System-Neutral Tool-Insert Internal Stopping Membranes and Lifting Springs Whereas inert or passive self-contained tool-inserts require only to be lifted and retracted, self-contained syringe injection and ejection tool-inserts generally require to be lifted to expose the needle or needles, then have an internal syringe plunger-plate further lifted to eject the contents, and finally have the needle retracted to prevent injury upon resumption of movement in the lumen. In a mechanical syringe tool-insert, this action is achieved with the aid of a strip-spring situated at the bottom or 'thumbrest' end of the syringe plunger in the base of the tool-insert. In a mechanical syringe, when continued lift by the lifting mechanism encounters resistance, a compression spring beneath a syringe plunger-plate beneath the bladder containing the medication begins to store energy.

A flange encircling the needle at a distance from the tip corresponding to the depth into the lumen wall desired for injection serves to restrict needle penetration and increase the resistive force at this depth. Sufficient resistive force causes a downward directed cutting edge extension of the needle to puncture through the top of the bladder, freeing the spring to expand, expelling the contents of the bladder. Varying the resistance of this internal spring makes it possible to control the sequence in which the tool-inserts along a given electrical or fluidic line will be actuated. Where a spring serves both to resist further lift until the lifting force is able to deform it whereupon it continues the lifting, a membrane or surrounding seal thereof of prescribed bursting force can be used to prevent further lift unless and until this degree of force has been reached.

Within the variability in height of the lifting mechanism alone, a membrane can set the force at which the tool-insert will be raised. Since the internal spring can be flat, leaf, elliptical, full elliptical, or spiral, the relative timing, degree of lift, and outward radial force exerted by each tool-insert along a line can be significantly varied. Stacking or serially arranging springs allows the self-contained tool-insert to be raised incrementally as the resistance of each successive spring is overcome by the driving force exerted by the lift-platform. Distinctly electrical or fluidic self-contained tool-inserts can also incorporate such membranes and springs.

VII2g(3)(e)(iv). Electrical and Electrochemical Tool-Inserts, to Include Gas Discharged Injection and Ejection Syringes All tool-inserts for use in circuit nodes having a lifting mechanism must accommodate that mechanism regardless of whether the need to be lifted inheres in the tool-insert function. To avoid deforming the thermal expansion wires, electrical tool-inserts such as heaters, which do not require lifting and would best remain with working faces flush to the surface of the muzzle-head or dedicated radial projection catheter, are made to completely fill the lift-shaft but incorporate an electrical connector base-plug at the bottom end of a spring-loaded lower half that telescopes into the upper as seen in the system-neutral injection syringe described above. This allows the lift-platform to rise independently of and without lifting the tool-insert.

If made with a unitary body, these tool-inserts should be used in a separate circuit that provides only electrical current and excludes thermal expansion units. Turning now to FIG. 56, shown is a compound mechanical-electrochemical injection syringe tool-insert for use in an electrical radial projection system. Not using a spring, the internal arrangement of components is equivalent to that seen in the mechanical electrical/fluid system-neutral injection syringe inserted into the radial projection units shown in FIGS. 54 and 59 where compression spring 206 has been replaced by an electrically activated gas releasing and detrusion or expulsion mechanism.

As shown in FIG. 56, thermal expansion wire 177 plays no part in the action and is shown as a part of the projection unit available for raising the lift-platform when other interchangeable tool-inserts that use this action are in use. For such use, thermal expansion wire 177 must be on a separate circuit rather than wired in series with other electrically operated units. The syringe is forced outward not by lift-platform 176 but by the gas releasing reaction. The electrical power used is that supplied through wire 214 to the receptacle at the top center of lift-platform 176 into which electrical base-plug 207 is inserted.

While replacing thermal expansion wire 177 with a meltable wax partitioned chemical isolation chamber would allow a single expulsive or lifting action to raise both the lift-platform and the syringe piston, in which case the tool-insert body could be unitary rather than telescoping; this would lose the advantage of projection units that built into the muzzle-head or radial projection catheter will immediately accept a series of different type interchangeable tool-inserts. An alternative type radial projection unit and tool-insert system could incorporate lifting means whether spring or gas discharge based at the bottom of each tool-insert, but duplicating and expending the lifting mechanism with each tool-insert involves greater expense. An advantage of electrical units is that electrical resistance can be used along with differential mechanical resistance in the form of springs having different restorative forces to adjust the current needed to raise a given unit positioned anywhere along a series-wired circuit such as that shown in FIG. 57.

Syringes emptied by means of internally generated gas pressure such as that shown in FIG. 56 must be gas- as well as medicinal contents-tight. Switching on the circuit of the unit shown in FIG. 56 energizes thermal expansion wire 177, raising tool-insert holding and lift-platform 176, collapsible syringe bladder 208, and injection needle 209. With the outer surface of the tool-insert in contact with lumen wall 204, injection needle 209 is driven into lumen wall 204 to the depth allowed by depth limiting flange or stop 210. Filament microswitch embedding melt-barrier 218 is used to separate chemicals and that when combined generate the gas used to compress bladder 208, which contains the medication and/or other therapeutic agent, such as a tumefacient, surgical cement, protein solder, or any combination of these to be injected.

As needle 209 continues to penetrate tissue such as that of lumen wall 204, the mechanical resistance to further penetration, which is proportional to the strength of the tissue, diameter of depth limiting needle flange or stop 210, the flexibility resulting from the material and dimensions of the spring metal electrical contact arms of lever microswitch filament embedded in meltable wax chemical compartment partition (separating wall, melt-barrier) 218, and the lifting force exerted by coiled thermal expansion wire 177, increases, eventually forcing lever microswitch embedded in meltable wax chemical partition 218 to close, sending current through the microswitch embedded in meltable wax chemical partition 218. Disintegration by melting of wax partition 218 causes the chemicals to come into contact generating gas that drives plunger 197 outwards causing bladder 208 to expel its contents.

The net resistance posed by the foregoing factors of mechanical resistance that precede the closure of partition with embedded switch 218 and thus precede the initiation of heating is preferably made selectable on the basis of lumen wall hardness testing results, obtained as described below in the section entitled Testing and Tests. Lever microswitch can be made of any suitable heating filament material, to include Nichrome®, or Chromel®, Alumel®, copper, constantan, manganin, or platinum, the current set for the materials in the microswitch and wax used. Melt waxbarrier with embedded filament lever microswitch 218 continues upward to divide chemical separating chamber partition roof 219, so that when melted, the gas generated by the reaction escapes through the linear gap or aperture left behind in roof 219.

Provided the base plunger plate at the bottom of bladder 208 is flush about the switch arms, extension of the microswitch radially outwards past partition roof 219 allows its use to warm the contents of bladder 208 at temperatures below that which melts partition 218. Microswitch filament in partition 218 can be made of a material that melts, allowing it to act as a fuse, breaking the circuit in which it is wired and thus cutting off the continued generation of heat other than that contributed through conduction from thermal expansion wire 177. Lift-platform 176 can be made either of a highly heat conductive metal to gain additional warmth from thermal expansion wire 177 or of a heat insulative polymer to isolate this source of heat. To achieve a difference in temperature within bladder 208 and partition 218, the filament can be made in consecutive segments that differ as to material and the use of insulation within partition 218 and within bladder 208.

Depending upon the dictates for temperature in general, barrier melting time can be adjusted by chilling the muzzle-head or dedicated radial projection catheter prior to use or a cooling service catheter can be inserted through the closest barrel-tube. While mechanical and electrochemical syringes are shown as distinct for clarity, the mechanical injection syringe tool-insert of FIG. 54 and ejector of FIG. 55, provided with an electrical plug at its base, can also incorporate a heating wire to warm the contents of bladder 208. One example of chemicals for placement on opposite sides of chemical isolation partition or barrier 218 that generate a gas when partition 218 melts, bringing the chemicals into contact is acetic acid and sodium bicarbonate. These combine to yield sodium acetate and carbonic acid, the latter immediately breaking down into water and carbon dioxide gas.

Partition 218 can be made of numerous different materials or combinations of materials mixed and/or layered, to include various waxes, such as bayberry, soybean, paraffin, and blends and plies thereof, and in dimensions to melt or break down at the temperature reached by filament within partition 218. That the materials and dimensions of partition 218 and the switch filament embedded within can be combined to react over a wide range of current-induced temperatures allows a wide range of temperatures to be applied to the contents of bladder 208. Medication or other therapeutic substances can be kept warm, if solid at room temperature can be kept fluid, and this can include protein solder as addressed above in the section entitled Use of Solid Protein Solders, in a denatured or fluid state so that it can be injected.

An electrochemical tool-insert for delivering both gas for lifting and heat is constructed with an overlapping gas-tight cap, the roof of the lower capped over portion containing the chemical separation chambers up through which the melt-barrier extends through the roof. Plugged into an electrical projection unit, passing current through the heating wire embedded in the wax partition that separates the chemicals and runs up through the roof melts the barrier, allowing the chemicals to combine and opening the slot along the roof through which the partition had extended allowing the gas to push up the gas-tight cover. The time of heating and temperature reached prior to the melting of partition 218 and emptying of bladder 208, initiated upon closure of the lever switch filament embedded within partition 218, are widely adjustable, and depend upon the resistance to closure of embedded switch 218, the rate of temperature increase generated by lever switch filament within wax partition 218, and the melting point of partition 218.

Protein solder, for example, requires heating to a higher temperature over a longer period to be denatured to liquify and flow, and therefore requires more of a time delay, obtained primarily through the use of a barrier having a higher melting point. Heating time prior to barrier melting and expulsion contributes to the heat imparted to the contents of bladder 208. The heat generated during this interval will also affect the temperature of the expulsion gas, increasing its volume, hence pressure for emptying bladder 208. Heating affecting both the pressure of the expulsive gas and the viscosity of bladder contents, the factors affecting heating time must be balanced between the temperature within bladder 208 and the expulsive force sought. Upon melting of partition 218, the gas rushes out through an aperture in plunger-plate opened when partition 218 melts.

Filament lever switch embedded within partition 218 passes down through bladder 208 and partition 218 and therefore can be used to heat the contents of bladder 208 as well as to melt partition 218. Delayed delivery substances should be distinctly contrast dyed. The form and length of heating partition embedded filament 218 inside bladder 208, typically coiled with radius about one third to one half that of bladder 208, includes a number of turns of a diameter that is contingent upon the pattern of heat distribution desired. The pressure required depends upon the dimensions of needle 209 and the viscosity and volume of bladder contents to be expelled. Suitable materials for use as heating wires are specified above in this section. The melting of a barrier separating chemicals that when combined produce a reaction which produces a gas or a gas and heat by heating such a wire coursed through the barrier can be used to generate thrust and/or heat with greater speed and intensity than could be achieved with the wire alone.

The chemicals can be the same as those used in chemical heating pads, hand, and foot warmers. These incorporate a barrier that is broken manually to combine water and a supersaturated solution of sodium acetate, calcium chloride, or iron in the presence of an oxidation-accelerating catalyst. Because recharging the chemical compartments and replacing the melt-barrier in the nonremovable lifting mechanism at the bottom of a radial projection unit is tedious and time-consuming, electrochemical release of gas or gas and heat is relegated to tool-inserts rather than built into the radial projection unit lifting mechanism. Exothermic reactions that generate sufficient amounts of heat and gas can be used both to heat the heating tool-insert and raise the lift-platform into position.

The greater speed, force of thrust, and application of heat that can be obtained by such means are offset by the loss of control once the conditions for the reaction have been established and the chemicals combined. By contrast, a heating wire remains fully controllable, so that the heat it produces, or if an expansion wire that can also serve to lift the heating tool-insert, the displacement it imparts, remain continuously and reversibly adjustable. Radial projection units in multiple discharge barrel-assemblies can be chilled during use by inserting a cooling catheter through a nearby barrel-tube or flowing chilling fluid through a nearby fluid radial system supply line. The lifting mechanism such as a thermal expansion wire serves no less to withdraw the tool-insert on cooling than to elevate it when supplied current.

When the ability to adjust the tool-insert in radial extension or height is unimportant and the spontaneous recession of the tool-insert working face upon the collapse of syringe bladder 208 is sufficient for safety without the need for additional lowering, lift-platform 176 can be eliminated and its function combined with that of the tool-insert internal plunger-plate lifting means, such as a compression spring, in the form of larger gas generating chemical chambers at the bottom of lift-shaft 182. Emptying bladder 208, or a bladder divided into upper and lower compartments, and lowering lift-platform 176 retracts needle 209 to well within injection syringe tool-insert barrel 196.

Strip-spring 187 just below lift-platform 176 assists in retracting the tool-insert when current through thermal expansion wire 177 is stopped. This allows the use of a larger bladder that is capable of delivering a larger quantity of injectant or ejectant. Moreover, lengthening bladder puncture lance or blade 213 allows dividing this larger bladder into an upper section punctured first and a lower section punctured upon collapse of the upper section, where each section can contain a different substance or component to be mixed, such as those of a two-part surgical cement. Electrical actuation also allows adjusting the resisting force of the lever microswitch spring and the distance separating the contacts to delay discharge and allow additional warming time.

This delay allows heating the expulsion gas to attain a volume, hence pressure of gas sufficient to empty the bladder. The nichrome wire and melt-down partition separating the chemicals that generate gas when mixed are adjusted in chemistry and dimensions to bring the chemicals to a temperature that results in expansion of the gas produced sufficient to collapse the bladder. A potential but seldom needed advantage to a gas-expelled injector or ejector is the ability to place the compartments separating the chemicals that are combined to generate the expulsive gas within the tool-insert holding and lift platform of the lifting mechanism rather than within the syringe tool-insert, making available the space that would otherwise be taken up by a spring, for example.

However, positioning the syringe expulsion mechanism inside the lifting mechanism rather than within the disposable tool-insert creates the need for a lift-platform that can be removed for cleaning and refilling. Since an injection needle protrudes out through aperture 211 more than alternative tool-inserts, an injector is most likely to require to be further lowered with the aid of a lift-platform. However, due to the need for cleaning after each use and refilling for the next, consolidation of tool-insert lift-platform and expulsive lifting functions through means that generate a force sufficient both to lift and to force the bladder empty are more suited to one-time use disposable radial projection catheters. Such consolidation precludes finer control over tool-insert elevation and is not used to eliminate the lifting mechanism in barrel-assemblies and reusable radial projection catheters.

VII2g(3)(e)(v). Temperature Control in Electrical Tool-Inserts

The regulation of heat in electrical tool-inserts is accomplished by the same means as described above for the turret-motor and recovery electromagnet windings as heating elements in the section entitled Turret-motor and Recovery Electromagnet Insulation, Leads, and Control of Winding Temperatures when Used as Heating Elements in Ablation or ablation and angioplasty-capable Barrel-assemblies. Electrical heating has the disadvantage of lacking a practical cooling counterpart, necessitating the use of a cooling catheter to rapidly drop the temperature. Small scale electrical refrigeration is not sufficiently developed or economical for incorporation into electrical tool-inserts, pertinent references concerning various approaches provided above in the section entitled Rapid Cooling Catheter and Cooling Capillary Catheter for Cooling Heated Turret-motor, Electrically Operated Radial Projection Unit-lifting Thermal Expansion Wire, and Recovery magnets.

VII2g(3)(e)(vi). Fluid-Operated Tool-Inserts, to Include Ejector-Irrigator-Aspirators and Injectors Fluid operated radial projection units for use over a smaller range of fluid pressures generally include the lifting mechanism at the bottom. Since these are built into the units and disengageable from the fluid circuit, the units include the valving needed to switch between ejection with the fluid in the circuit flowing in one direction and aspiration in the other. Units in the muzzle-heads of barrel-assemblies and radial projection catheters are limited to components likely to be necessary with tool-inserts applicable to the type ductus for which the primary equipment is intended. Such comprehends the need for a wide range of capabilities, which will be reflected in the lift-aspiration mechanism valving.

For example, units that will not be used with tool-inserts capable of aspiration omit all fluid direction of flow switching valves. Various fluid operated tool-inserts incorporate internal means for projection and retraction. Ejection-aspiration switchable tool-inserts seldom call for lifting and retraction. Use of the term 'flow reversal' here is distinguished from use of the same term in conjunction with carotid angioplasty and stenting, addressed below in section VII2j(1) entitled Incorporation of Adscititious Capabilities into Barrel-assemblies, and aortic regurgitation on the diastoles due to aortic valve impairment. For this reason, the fluid-operated units and ejection-irrigation-aspiration tool-inserts shown incorporate switching valves and other elements not required in most practical fluid units and tool-inserts.

The operating pressures and direction of flow reversal capability for a certain combination of projection unit and tool-insert vary according to the specific conditions and functions to be encountered. Viewed normal to the long axis of the barrel-assembly or radial projection catheter, a fluid circuit operated tool-insert is bilaterally symmetrical.

It can therefore be rotated through 180 degrees to reverse its response to antegrade or retrograde flow through fluid supply line 203. At the same time, the fluid pump contained within the power and control housing is reversible. The norm adopted for descriptive purposes is that flow is antegrade and tool-insert projecting and/or actuating from left to right and retractive and/or aspirative when the flow through fluid supply line 203 is from right to left. With fluidically operated units, injection and ejection are not limited in volume as with a syringe, and continuous delivery or removal is not limited to injection or ejection. Fluid projection units are shown in FIGS. 52b, 52c, 59, 60, and 63, with injection tool-inserts shown inserted into those shown in FIGS. 59 and 60, and an ejection tool-insert in that shown in FIG. 63.

Provided the lifting mechanism incorporates the switching valve elements essential to support flow reversal, most ejectors will both irrigate and aspirate. Electrical syringes could be devised to decollapse and use the vacuum to draw in material, but limited to the internal volume of the syringe bladder, this is discounted. Injector or single exit orifice (end opening) type tool-inserts, which unlike syringes are not safely retracted back into the tool-insert once discharged, can be used to irrigate or aspirate only when integrated into a shaving or abrading tool face that surrounds the orifice, protecting the lumen wall from injury. Most fluid operated tool-inserts do not require an entry collar or neck extending down at the base for adaxial insertion in the lift-platform receptacle, but only an opening where the lift-platform effectively supplies the sides of an entry way or portal as a virtual plug.

Irrigation allows the continuous delivery of water or a therapeutic fluid at the treatment site. The use of aspirators and cutting or shaving aspirators in the arterial tree aspirates blood along with the debris; however, the absolute volume of blood is small, is not reintroduced, and the process not comparable to the use of a cardiopulmonary machine that reintroduces damaged blood cells. Irrigation or aspiration can also be accomplished through neighboring projection units or side-socket accessed barrel-tubes in an ablation or ablation and angioplasty-capable barrel-assembly. Ejector-irrigator-aspirators have working face holes sized according to the size of the debris particles the cutting or abrading tool generates. Depending upon the lifting forces and functions of other units in the same circuit, clogging can be forestalled by increasing the line pressure.

Once clogged, a larger muzzle-head or combination-form radial projection catheter without an available alternate circuit must be withdrawn and cleaned or exchanged. Procedures that generate much debris are more quickly accomplished with a bipartite radial projection catheter or ablation or ablation and angioplasty-capable barrel-assembly with multiple interchangeable radial projection catheters each containing two or more fluid circuits. Electrical shaving tool-inserts or shavers do not aspirate but store the debris removed in a chamber behind the cutting blades. By spacing the blades to configure the output streams and particle inlet clearance, an ejector-irrigator-aspirator with a cutting (shaving) face eliminates the need for face-holes; however, it must be lifted when shaving, necessitating an additional strip-spring with greater lift resistance.

Separating the shaving functions between different tool-inserts spares this added complexity. For example, an electrical shaver with internal storage can be supported by fluid aspirators and/or an embolic filter that remove residual debris. Fluid tool-inserts include initially charged or measured dose-prefilled flow-through injectors and ejectors, which deliver a preliminary or therapeutically preparatory amount of a fluid substance before transferring fluid directly from the line, and ejector-irrigator-aspirators whether integrated into tool-inserts with shaving or abrading faces. Both electrically and fluidically controlled projection units can use inert bits and self-contained syringe injectors and ejector irrigator aspirators; however, only fluidically operated projection units can use fluid tool-inserts. Following use to inject, injectors in the retracted position can be used to irrigate but generally have a gauge unsuitable for use to aspirate.

Such use and the use of ejector irrigator aspirators as suction devices for holding the surface against the lumen wall have the potential to cause injury. The ejector irrigator aspirator shown in FIG. 63, just as any fluidic tool-insert, is capable of intermittent or continuous fluid delivery. A fluid ejector or injector can be prefilled with a measured dose of medication other than that to follow from the line. In that case, the medication is sealed inside the tool-insert with pressure sensitive-backed foil or film at the base-plug inlet and face aperture outlet and stored at the prescribed temperature. Otherwise, the ejector or injector can deliver fluid intermittently or continuously as controlled.

In FIG. 63, syringe ejection tool-insert (defined to the left hand side of FIG. 54 as 184 with other major part numbers) is inserted into lift-shaft 182. Virtual flow-through base entry and discharge portal or passageway 220 is established by contact and continuity between the opening at the base of the tool-insert and the wall about the receptacle through the center of lift-platform 176, providing flow-through base entry and discharge portal or passageway 220. Retention within lift-shaft 182 is by means of hold-down or swing-out restraining or stop arms 186, so that an actual base-plug is not needed for friction fitting the tool-insert within lift-platform receptacle constituting virtual base-plug 201.

When the fluid pressure in supply line 203 is high enough, strip-spring valve 187 clears opening 201 leading into base entry and discharge portal or passageway 220, but is prevented from passing through the base of the tool-insert by spring door 221, so that lift-platform 176 raises ejection syringe plunger or piston 197, expelling syringe pre-load 222. That is, when the pressure in line 203 is only turned up enough to force strip-spring 187 to clear opening 201, the tool-insert functions as an ejection syringe. When the pressure in the fluid supply line 203 is increased enough to overcome the resistance to opening of spring-loaded trap door 221, the tool-insert becomes a continuous discharge ejector-irrigator for whatever fluid is run through supply line 203. At continuous flow-through pressures, the tool-insert can be devised to serve as an ejector when the flow through supply line 203 is in one direction and as an aspirator when the direction of flow is reversed.

Unless the ductus is large enough in diameter to accommodate a muzzle-head with or without ensheathment in a radial projection catheter (addressed below in the section entitled Radial Projection Catheters), which can accommodate independent fluid circuits with flow in opposite directions, to change from ejection to aspiration would necessitate withdrawing the barrel-assembly from the body, exchanging tool-inserts, and reacquiring the treatment site, all the time aggravating the entry wound as well as extending the procedure. The need for withdrawal and reentry is then further multiplied when a barrel-assembly is essential for ballistic implantation, but the ductus too small in diameter to allow the use of a muzzle-head that can incorporate the number of projection units required or a duplex, or bipartite, barrel-assembly as would provide whatever number of units were necessary, as addressed below in the section entitled Distinction in Ablation or Ablation and Angioplasty-capable Barrel-assemblies as Unitary or Bipartite.

Then an independent radial projection catheter, as addressed below in the section entitled Radial Projection Catheters would require to be withdrawn and exchanged with the barrel-assembly however many times this became necessary. In this situation, ejector-irrigators and cutting tools that are also capable of aspiration by reversing the direction of flow through supply line 203 are of significant advantage. Added versatility thus favors economy from the procedural duration, efficiency, and safety as well as the purchase price standpoint. Thus an upward flow through the tool-insert must pass through the perforations. In order to assure the prompt resumption of outward flow, which necessitates that the valve quickly close to the restrictive position, the valve axle includes a stop so that during aspirating flow through the circuit or line, that is, inflow through the tool-insert, the expansive side of the valve cannot assume a fully off-vertical position.

Instead, the expansive side is inclined toward its side or stop side and is quickly levered back up against the stop by any subsequent outflow. When incorporated into a prefilled injection or ejection syringe tool-insert, the perforations are sealed and the damper tacked in the closed position by a film such as of a dried sugar solution, for example. A film sets a threshold line fluid syringe tool-insert lifting force on actuation, and broken, leaves the base-hole or base-plug to pose no resistance to outflow back into the fluid circuit of the inflow through the perforations in the working face when the direction of flow through the fluid supply line is reversed to initiate aspiration. Provided only one such directional reversal to go from resistance to flow-through and threshold lifting force for the specific type tool-insert to aspiration with no resistance is necessary, a one time use film is adequate.

For uniformity in the radial projection unit lifting-mechanisms, variable elements such as this film are built into the tool-insert rather than the lifting-mechanism. However, it is preferable that actuation with flow in one direction and aspiration in the opposite direction be reversible without the need to exchange tool-inserts. Strip-spring 187 setting the lift-platform lifting pressure, a fluid resister to serve as an actuation and aspiration switching valve is added to set the tool-insert flow-through and syringe piston-plunger lifting pressures. The direction-of-flow responsive switching valve is automatically actuated by a reversal in the direction of flow through the fluid supply line and can be reversed as often as necessary.

This fluid resistor switch consists of polymeric baffle 199 with perforations sized for a sum cross-sectional area to impose the required resistance to flow-through based upon the viscosity of the fluid in the line, syringe contents viscosity and compressibility if any, and the sum cross-sectional area of the outlet pore or pores (apertures) in the working face. Also to allow reversal of the fluid pump in the power and control housing, to quickly reverse the directly of flow in fluid supply line 203, damper-configured baffle resistor ejection-aspiration switching valve 223 in FIG. 62, situated within base entry and discharge portal or passageway 220 leading into the tool-insert adaxial to or beneath spring loaded door 221 incorporates off-center integral (molded in) axle 224.

The ends of axle 224 are journaled in the sides of base entry and discharge portal or passageway 220. Axle 224 divides the baffle 223 into smaller and larger flap areas, axle 224 configured to urge baffle 223 into the closed condition against stop 225. Stop 225 is at the same level and diameterically opposite to baffle 223, so that when stopped from rotating radially outward, baffle 223 is straight across or disposed perpendicularly to the imposed column of fluid. When flow through the line is antegrade as shown in FIG. 62 panel A, the fluid column must pass the perforations in the fluid resistor baffle to flow through or lift the piston-plunger of a syringe. When the flow is reversed to aspirate as depicted in FIG. 62 panel B, the larger or flap side of the valve or baffle is pulled adaxially toward the long axis of the barrel-assembly or radial projection catheter, allowing fluid to flow unimpeded through the working face and body of the tool-insert and into the fluid supply line.

If fitted within a frame, the frame can serve as a shape adapter, so that provided it has a round frame, a square valve can be fitted into a round base-hole or base-plug, for example. That is, in the closed position, the baffle constrains fluid entering through the base-hole or base-plug with the design passage and lifting pressure to pass through its perforations lifting the tool-insert or driving the fluid syringe emitter outward causing its contents to be expelled. Reversal of flow through the fluid line, that is, retrograde or aspirative flow draws the side of the baffle with greater area downward but only to an angle such that re-reversal of the flow quickly rotates the hinged side up against the stop reinstating fluid resistance. Compared to the equivalent emitting tool-insert when not prefilled, the initial discharge will be somewhat more resistant due to the additional resistance posed by the ejectant or injectant.

During outflow, or outward (emissive) flow, the side of the disk with greater area is pushed so that the disk spans across the fluid path through the tool-insert to act as a fluid resistor, while during inflow, the stronger flow against the larger portion of the disk causes the disk to align with the flow and thus not become clogged by aspirated debris. The sum cross-sectional area of the perforations in any one injection or ejection tool-insert determine the viscosity range, hence, suitability of that tool-insert for use with a given fluid. A prefilled syringe type fluid tool-insert must be empty before it can be used to aspirate. Due to the lesser force of aspiration, the break seal, cap, or stopper used to retain and preserve the sterility of syringe contents is eliminated during syringe discharge before aspiration commences.

Preferably, the base of the tool-insert itself is glued to the upper surface of the lift-platform so as to separate at the desired pressure. Alternatively, a one-way rupture film or push-through cap or stopper over the internal or external opening of the base-plug can be used. A film should be thick and a plug resistive enough to allow an increase in line pressure sufficient to empty the forward syringe section of the tool-insert before yielding without clogging the syringe outlet. Such a one-way rupture film when thinner or push through plug when thicker can consist of a dried sugar, methylcellulose, or hypromellose (hydroxypropyl methylcellulose) with polyethylene glycol 400, or some mixture thereof, for example. The exact formulation of the cap depends upon the ambient temperature in which the tool-insert is used. Reciprocally, the composition of the cap can be set to hold fast until a certain temperature is reached.

An ejector can also deliver heated or chilled gas or liquid for ablative application to the lumen wall, alternative means for thermal or cryogenic treatment consisting of delivery through barrel-tubes or cooling catheters as addressed in the section above entitled Rapid Cooling Catheter and Cooling Capillary Catheter for Cooling Heated Turret-motor, Electrically Operated Radial Projection Unit Lifting Thermal Expansion Wire, and Recovery Magnets, or heating by means of heat-windows, as addressed in the section above entitled Thermal Conduction Windows (Heat-windows) and Insulation of the Muzzle-head Body in Thermal Ablation or Thermal Angioplasty Minimally or Fully (Independently Usable) Capable Barrel-assemblies. At higher line pressures, an ejector functions as an irrigator with antegrade flow or an aspirator with retrograde flow. The antegrade delivery of a chilling or heated gas with antegrade or irrigative flow can be used to ablate tissue.

An alternative method for obtaining local cooling (or heating) is a Peltier device, based upon the thermoelectric effect (see, for example, Ge, Z. H., Song, D., Chong, X., Zheng, F., Jin, L., and 6 others 2017. "Boosting the Thermoelectric Performance of (Na,K)-Codoped Polycrystalline SnSe by Synergistic Tailoring of the Band Structure and Atomic-Scale Defect Phonon Scattering," *Journal of the American Chemical Society* 139(28):9714-9720; Lin, C., Cheng, W., Guo, Z., Chai, G., and Zhang, H. 2017. "Exceptional Thermoelectric Performance of a "Star-like" SnSe Nanotube with Ultra-low Thermal Conductivity and a High Power Factor," *Physical Chemistry Chemical Physics* 19(34):23247-23253; Rowe, Zhao, D., Ning, J., Wu, D., and Zuo, M. 2016. "Enhanced Thermoelectric Performance of $Cu_2SnSe_3$-Based Composites Incorporated with Nano-Fullerene," *Materials* (Basel) 9(8). pii: E629; Merrill, D. R., Moore, D. B., Bauers, S. R., Falmbigl, M., and Johnson, D. C. 2015. "Misfit Layer Compounds and Ferecrystals: Model Systems for Thermoelectric Nanocomposites,' *Materials* (Basel) 8(4):2000-2029; D. M. 2005. *Thermoelectrics Handbook: Macro to Nano*, Boca Raton, Fla.: Chemical Rubber Company/Taylor and Francis; DiSalvo, F. J. 1999. "Thermoelectric Cooling and Power Generation," *Science* 285(5428):703-706; Ioffe, A. F 1957. *Semiconductor Thermoelements and Thermoelectric Cooling*. London, England: Infosearch). Peltier devices can also be used in heating devices addressed herein, such as heating windows.

With retrograde flow, a vacuum can be induced and debris carried away by circulating a liquid or a gas through the fluid circuit. During aspiration, the vacuum is created to the inlet chamber 194 side of outlet chamber 195 roof fluid resistance plate or baffle 199. Debris aspirated by this tool-insert is moved retrogradely (pumpward) until the next roof-plate is encountered where the particulates will eventually accumulate and necessitate flushing once clogged.

To cause a pressure increase that forces fluid up base-plug opening 201 during antegrade or tool-insert lifting and/or actuation flow and allow aspiration so that debris can freely move past roof-plate 199 during retrograde flow, perforated outlet chamber fluid resistor roof-plate 199 is hinged for up and down rotation to the fluid chamber 195 wall, chamber outlet chamber 195 being the outlet chamber with fluid in the supply line moving antegrade from left to right and the tool-insert engaged within the projection unit as depicted in FIGS. 59, 60, and 63. Since roof-plate 199 would be difficult to access and exchange with others having different slit or perforation cross sectional areas, barrel-assembly or radial projection catheter for use with fluids covering a wide range of viscosity incorporate separate fluid circuits with projection units.

Increasing the line pressure at the pump affords some latitude in viscosity with a given roof-plate 199, but quickly results in excessive pressure of ejection, aspiration, and breakage. The use of a. 1. A liquid or 2. Mixture of liquids, or b. 1. A gas or b. Mixture of gases followed by a liquid or mixture of liquids, is preferred as it flushes the circuit reducing the risk of clogging. With small particulates, this may allow continued use of a fluid circuit in either direction. A fluid injector can also function as an irrigator; however, unlike an injection syringe that collapses to a retracted position within the tool-insert once discharged, a fluid injector can discharge only when projected. Since this can result in injury to the lumen wall, single-orifice fluid tool-inserts are not used as irrigators unless integrated into a cutting (shaving or abrading working faced) tools.

Fluid injection needles are projected in use and unless integrated into working faces, not used as aspirators; the application of suction to assist needle penetration draws in debris, is unnecessary, and most often ineffective. The general structure of fluidically operated units is set forth above in the introductory section entitled Radial Projection Units. In FIGS. 59, 60, and 63, partition (dividing wall, separator) 188, comprising floor portion 190, aperture 193 closable in opposite directions by spring loaded passive flapper valves or stoppers 191 and 192, and roof portion 189 into which strip-spring 187 is secured down by fastener 198 separates fluid inlet chamber 194 from fluid outlet chamber 195. Outlet chamber 195 is roofed over by perforated roof-plate 199 Since the direction of fluid flow through supply line 203 is reversible, and a fluid tool-insert can be rotated to face in the opposite direction, inlet chamber 194 is not roofed over by a roof-plate.

Lift-platform retracting strip-spring 187 is fastened at its ends to the undersides of lift-platform 176. Roof-plate 199, covering outlet chamber 195, is cut out to clear strip-spring 187 at its center where strip-spring 187 is fastened to the top portion of chamber partition 188. Compound fluidic-mechanical flow-through tool-insert, to include ejector irrigator aspirators and injectors may present an additional resistance, consisting of an entry elastomeric membrane valve or strip-spring fluid valve or regulator covering the external or internal opening into the plug at the base of the tool-insert or a damper type valve as shown separately in FIG. 62. When the pressure in inlet chamber 194 exceeds the resistance posed by strip-spring 187, lift-platform 176, which is constrained to rectilinear or nontilted elevation or lift radially outward, and descent is forced radially outward (upward as shown).

Roof-plate 199 over outlet chamber 195 is of a flow through rate specified to resist flow sufficiently as not only to increase the pressure in the line to that required to raise lift-platform 176. Pressure greater than this will pass the entry elastomeric membrane slit valve or strip-spring valve in the base of the tool-insert or a damper type valve as shown separately in FIG. 62. Antegrade pressure thus causes fluid in the line to flow up through and out the tool-insert into the lumen or its wall as well as through outlet chamber roof-plate 199, while retrograde pressure on reversing the pump has the opposite effect. Specifically, pump reversal produces a partial vacuum on the near (pumpward) side of the line and thus draws fluid from the lumen into the tool-insert as well as through the membrane or damper type valve as shown separately in FIG. 62 in the line.

Outlet elastomeric roof-plate 199 must present sufficient resistance to flow to divide the flow between the lift-platform 176 and inlet chamber 194; that is, sufficient resistance to flow-through that lift-platform 176 with emitter or flow-through tool-insert such as an ejector or injector inserted is forced upward but sufficient flow continues past outlet chamber 195 roof-plate 199 that flow continues to the next unit. It must thus offset the combined resistances posed by strip-spring 187 and if present, the inlet roof membrane or damper type valve as shown separately in FIG. 62, as well as any optional elastomeric membrane or strip-spring valves present, whether inside the tool-insert plug or affixed to the roof of inlet chamber 194. Pump and circulation reversal then have the effect of posing less resistance to the withdrawal of fluid through the base entry and discharge portal or passageway 220 affording aspirating action.

Placing a mirror image or antipodal flapper valve on the antegrade outlet chamber 195 allows tool-inserts to be bypassed at subaspirating pressures. The proper balance between the relative resistances posed by the fluid path up through and out of the fluid ejection tool-insert, which includes the viscosity of the fluid in the tool-insert and the area of the apertures through which the fluid is emitted, and outlet roof cover roof-plate 199 allows some fluid to flow through roof cover roof-plate 199 thus allowing the passage of fluid to the next unit in the circuit. The higher resistance to fluid flow-through outlet chamber roof-plate fluid resistor valve 199 and plug entry or mouth roof-plate 199 causes fluid to flow against the less resistance up into tool-insert 184. Partition 188 separating inlet chamber 194 from outlet chamber 195 contains aperture 193 that allows fluid to bypass the unit without raising lift-shaft 182.

Facing fluid chamber partition 188 bypass passage 193 within inlet chamber 194 at either side (which represent either the inlet or outlet depending upon the direction of flow as antegrade and ejecting or retrograde and aspirating as set at the pump) are flapper valves 191 and 192. Flapper valves 191 and 192 consist of hemispherical or cup-shaped stoppers of any nonallergenic and surfactant free pliant or rubber-like material supported at the distal ends of elastomeric or metal wire or band spring-arms positioned with the convexity directed toward so as to seal or obturate the entry into partition bypass opening 193 at their respective sides. Thus, when the antegrade fluid pressure exceeds the resistance posed by spring-arm supported valve 191, for example, valve 191 is driven against and seals the entry into partition 188 bypass passage 193.

In fluid operated radial projection systems that must allow a wide range of fluid pressures, the lifting and fluid delivery portion (at the bottom in FIGS. 59, 60, and 63), otherwise built into the barrel-assembly muzzle-head or radial projection catheter for nonduplicative economy, is a part of the tool-insert. With such a bypass, fluid continues to flow past the unit until the line pressure exceeds the resistance of the flapper valve spring-arm of this particular projection unit, whereupon flapper valve 191 closes causing fluid to rise up over partition 188 lifting lift-platform 176. Once flapper valve 191 closes, the pressure acts against the bottom of lift-platform 176 forcing strip-spring valve 187 to flex, allowing fluid to pass and raise lift-platform 176.

An inert bit with cutting face or syringe tool-insert is lifted into working position, while a tool-insert with base-plug strip-spring valve poses a second tool-insert internal resistance to the passage of fluid from the line through the tool-insert. A bypass serves two major purposes in allowing
a. Fluid to be moved past units at low pressure at any time prior to use, thus eliminating the pump outlet to inlet chamber fluid transit time, reducing unit response time, and
b. Units provided with less stiffly sprung (weaker) bypass flappers and lift-platform strip-springs farther downstream to be actuated before units having stiffer springing more proximate to the pump outlet so that tool-inserts with lift-platforms that are bypassed are not raised much less pass through fluid.

Provided the barrel-assembly or dedicated radial projection unit catheter is free of bending, such as with the aid of an assistant during manual use or through the use of a linear positioning stage and forward drive and sag leveling and stabilizing device under motorized control, bypass makes it possible to start circulation through the circuit at pressures lower than required to close the weakest flapper in the circuit prior to entry. Comparing the pressure control gauge reading to the actuation of the units allows the pressure response of each unit to be tested prior to use. With the line pressure further increased, the fluid system ejector shown in FIGS. 52c, 58, and 63 serve as irrigators, and at high pressure as a miniature water or other liquid jets or tiny pressure washers.

Because the addition of shaving edges or an abrasive texture to the working face requires projection during and retraction following use as does an injection needle, the integration of irrigation into tool-inserts that include cutting faces requires a telescoping tool-insert (not shown) for use in injectors. Lifted at pressures lower than used for washing, these cannot be used as irrigators while retracted. Neighboring fluid ejectors are used for washing when cutting head tool-inserts are retracted. Fluidic tool-inserts use a plug-in base not only for mechanical connection to the upper surface of the lift-platform by insertion in a socket but also for fluidic connection to the fluidic circuit. When present, fluid tool-insert plugs are open at the bottom. Only fluid tool-inserts can directly transmit the fluid in the pipeline to the lumen or inject this fluid into the lumen wall.

An electrical/fluid system-neutral radial projection unit syringe injection or ejection tool-insert, such as that shown inserted in an electrically operated radial projection unit in FIG. 55, is self-contained, using the lifting mechanism at the base of the lift-shaft only for lifting into and retraction from the working position. Such a syringe tool-insert has the advantage of usability in any radial projection unit of matching dimensions but has the disadvantage of a finite volume of the therapeutic fluid. By contrast, the fluid operated counterpart shown in FIG. 63 can feed through fluid from supply line 203, in which case the line fluid is both the hydraulic and therapeutic fluid, and the syringe can contain an initial preload of a different or pre-treatment therapeutic fluid.

Fluidic tool-inserts can incorporate fluid resistor plate, membrane, and spring valves to achieve lift internally, allowing adjustment in the relative timing of fluid ejection or injection by each tool-insert along the fluid circuit. When this tool-insert is provided with a strip-spring covered bottom entry hatch, it can still be used in either type unit to discharge its content. In an electrically operated unit, the spring hatch is not used, and only the prefilled load is available. However, when inserted in a fluid operated radial projection unit, once its prefilled load has been emitted, the fluid ejector can pass through fluid from the line. A prefill (preload, initial load) of the same or another drug or therapeutic substance than that to follow from the line can be ejected ahead of that in the fluid supply line.

The fluid from the line can be used to dilute, irrigate, activate or be activated by, or act in combination with the initial load. A fluid operated injection syringe is of like structure but releases its content through an injection needle. Raising the line pressure above the lifting pressure forces lift-platform 176 lift away from strip-spring 187 that at lower pressures obturates the entry up into base-plug space 220, exposing the opening into the base-plug. The initial load or fluid preloaded in the emitter then flows through the tool-insert and out the working face. Further raising the line pressure then allows fluid to pass slit membrane damper fluid resistor ejection-aspiration switching valve as shown in FIG. 62, positioned within base-plug space 220 and spring loaded bottom hatch valve 221.

The fluid in the line then forces its way up through the tool-insert to be emitted through the pores in the working face, which are sealed with a fine film to retain the prefill prior to use. In fluid tool-inserts with a base-plug, syringe plunger 197 has a short projection on its undersurface that is the positive or male complement to base-plug space 220 in lift-platform 176, which latter receives this projection as the receptacle or female complement thereto. Insertion of this base-plug into cavity 220 to seize therein by frictional retention is accomplished with less force than drives plunger-plate upwards expelling the contents of chamber 203 through injection needle or hypotube 209. The outer surfaces of the syringe tool-insert body closely fit within lift-shaft 182, but lined with a low friction polymer such as a fluoropolymer, allow the lifting or expulsion driving means to freely raise and lower the tool-insert.

Electrical and fluid systems use radial projection unit and tool-inserts made to standardized incremental dimensions as sets with as much commonality of componentry as possible. While the conformation of electrical/fluid system neutral injection and ejection syringe tool-inserts as shown much limits the finite volume of fluid such a closed or self-contained syringe can deliver, the absolute volume can be considerably increased when consecutive radial projection units are separated by removable inserts so that the syringe tool-insert can span over two or more projection units. Expanding the syringe in muzzle-heads and radial projection catheters affording slight depth in the other two dimensions allows the delivery of a larger dose than might two separate syringes divided by a gap or gaps.

In electrical circuits with built in delays between consecutive units and in fluid operated circuits, the time delay between consecutive projection units cannot cause syringe plunger 197 to tilt and seize within syringe barrel 196, because these are faced if not made of a low friction polymer, and plunger 197 is constrained and forcibly aligned within syringe barrel 196. The height of the contents is equal to the excursion afforded by the lifting means, and once the lifting or expulsive force is removed, strip-spring 187 retracts the syringe pulling needle 209 within lift-shaft 182, preventing incisions upon resumption of transluminal or rotatory movement. Increasing the volume of injectant therefore requires a unit of longer radial excursion or larger cross section. Numerous configurative, textural, and materials means are well known for enhancing the frictional retention of a base-plug if present within cavity 220.

Provided the valving internal to the syringe tool-insert are gauged to respond at the pressures applied, the cross sectional shape and area of the base-plug and cavity 220 need not match that of the fluid supply line. Rotatable or swing-out hold-down or retaining arms 186 act as stops to the excursion radially outwards of the syringe. It will now be seen that lift-platform 176 first slides injection or syringe tool-insert radially outwards against the restorative force of strip-spring 187 until retaining arms or stops 186 prevent further outward movement. Needle 209 now extending beyond the surface of the muzzle-head, continued force against plunger—197 forces the contents of injection or syringe tool-insert 184 as indicated in FIG. 54 out through needle 209. Discontinuation of the lifting force frees strip-spring 187 to retract needle 209.

VII2g(3)(e)(vii). Use of Flow-Reversible Tool-Inserts for Microaspiration

Barrel-assemblies with a fluid side-socket allow connection of a fluid radial projection system to an aspiration pump even with the barrel-assembly engaged in the airgun during ballistic discharge. However, since the barrel-assembly is seldom if ever engaged in the airgun except during ballistic discharge, the proximal end of the barrel-assembly is accessible for connecting barrel-tubes to an aspiration pump. Flow-through tool-inserts, barrel-tubes, and an unoccupied central channel or passageway in a combination-form barrel-assembly can be connected to an aspiration pump and used to aspirate. The hinged and perforated fluid unit outlet chamber cover and opening through the chamber partition that allow retrograde flow are addressed above in the section entitled Radial Projection Units. Thrombectomy router/aspirators that remove thrombus and plaque by rotary cutting and the resulting debris by aspiration are common.

Rotary devices can be effective for the removal of thrombus and radially symmetrical plaque; however, radially indiscriminate, used to treat eccentric lesions; a microrouter can grate on, gouge, and even perforate a healthy portion of the lumen wall. This eventuality is usually protected against by using a router significantly undersized in diameter, resulting in the removal of the more medially protrusive, or cap-ward, portion of the plaque while allowing more abluminal or radially distant portions to remain with cut surface exposed. A critical need to restore flow can be satisfied, and the placement of an endoluminal stent can extend this patency, but restenosis is usually inevitable. Side-looking aspiration tool-inserts and barrel-tubes allow not just the aspiration of matter freed by cutting or abrading tools, but with suitable imaging and contrast markings on the apparatus, the direct, radially oriented removal of soft plaque and diseased tissue by microaspiration.

Whether used to remove debris released by angioplasty, deliberately remove material from the surface of the luman wall, or ablate diseased tissue, the force of aspiration must be appropriate for the purpose and closely controlled. The optimal force must be determined by spot-testing the actual tissue to be removed within a range that has been preestablished on the basis of experience with similar tissue. The aspiration of fluid with particles suspended will be limited by the rate at which the apertures in the lift mechanism become clogged. However, subject to the need to avoid obstruction in the treatment of blood vessels, clogging can be alleviated without the need to withdraw. This is accomplished by retrograde flushing of the line or lines under low pressure with sodium hypochlorite, then with water at higher pressure before resuming.

VII2g(3)(e)(viii). Temperature Control in Fluid (Piped) Tool-Inserts

Using a thermally insulated electrical syringe tool-insert, a small volume of fluid can be preheated and ejected into the lumen or injected into the lumen wall at the treatment site. While this capability will often have utility, the total volume of medication that can be preheated with prefilled electrical syringes is limited. Large barrel-assemblies and special radial projection catheters for use in the gastrointestinal tract, trachea, or bronchi where temperature is seldom critical will usually have sufficient clearance or recession from the lumen to initiate the heating of thermally insulated syringes or retracted hot-plate tool-inserts prior to application.

Moreover, for intermittent use, hot-plate type tool-inserts must directly interface with the lumen and cannot be thermally insulated over the working face at a reasonable cost. Especially in blood vessels, wherein temperature can be critical, the caliber of a vessel may be too restrictive to admit a barrel-assembly or special catheter having a diameter large enough to allow a hot-plate type tool-insert to be adequately retracted during preheating. Thermoplasty or melting implanted protein solder, for example, which use hot-plate type tool-inserts, are safer and more efficient when the operative temperature can be achieved and quickly reverted from at the treatment site.

Electrically heated tool-inserts require microcontroller regulation to pass through thrombogenic temperatures quickly and incapable of chilling, necessitate the use of a cooling catheter for quick return to body temperature. By contrast, a fluidic tool-inserts can chill as well as heat, and do either quickly by passing fluid through it that has already been brought to the target temperature at a location remote from the treatment site. fluid system also allows switching between water or any other fluid medication or therapeutic substance that has been preheated or prechilled to a target temperature and water, for example, to quickly return the tool-insert to body temperature.

A fully internalized fluid reservoir of a size that will fit into the power and control housing, or battery-pack handgrip part of an ablation or ablation and angioplasty-capable barrel-assembly or special radial projection catheter is likely to be too limited in fluid volume, and while heatable, is seldom chillable within the size constraints imposed without external connection. A Joule-Thomson microrefrigerator, for example, requires three connection lines. Interchangeable cartridge-configured fluid reservoirs can be inserted into the power and control housing in an ablation or ablation and angioplasty-capable barrel-assembly or special radial projection catheter with the fluid already heated or chilled to compensate for the drop or rise in temperature due to time delay and transmission line losses until the treatment site is reached.

This affords somewhat more freedom of movement than does connection to remote temperature controlled reservoirs through switchable hosing and a fluid side-socket. However, external connection removes limitations in number, volume, and temperature of different fluids that can be delivered. Chilled fluids in particular are best pumped from external refrigerated tanks with the temperature adjusted to compensate for delivery through the line to the treatment site. Fluid that is not itself medication for injection or ejection but is used only to control tool-insert temperature and/or to raise fluid unit lift-platforms is recirculated, hence not depleted. The heating and pumping of the fluid can therefore be small enough to incorporate within the apparatus.

VII2g(3)(e)(ix). Doublet Irrigator-Aspirator Tool-Inserts, or Point-Washers

The use of separate emitter-irrigator-aspirator tool-inserts to flow fluid over the lumen wall is addressed above in the section entitled Radial Projection Units. By contrast, a doublet consists of two identical or similar tool-inserts unitized in back to back relation intended to flow water or a therapeutic fluid over a focal treatment site. Back to back irrigator-aspirators, or point-washers, directly target and quickly aspirate water or a therapeutic fluid from a short segment of the lumen wall. This allows, for example, exposing the wall to a therapeutic substance or a thermoplastied segment to be returned to body temperature more quickly than if the fluid were released and aspirated over a larger area. The tool-inserts in a doublet differ from separate emitter-aspirators in having thicker face plates with perforations that are angled to aim the ejectant toward the aspirator and sharing a common inner wall.

Other doublets can include, for example, a cutting tool-insert and an aspirator. Particulate size, the rate at which the aspirator clogs, and time required to flush the line must be taken into account. The recovery of debris is improved as the number of aspirators in the same and different fluid circuits is increased. Since the internal structure of each tool-insert in the pair or doublet is anteroposteriorly asymmetrical to perform as an emitter-irrigator or as an aspirator depending upon the direction of flow through the fluid circuit, doublets in the same circuit will emit or irrigate or aspirate depending upon their anteroposterior anteroretrograde orientation in the circuit. Reversing this orientation thus reverses which subtool in the pair or doublet acts as the emitter and which acts as the aspirator and does not affect the function of the doublet as a unit.

Therefore, with one or a few doublets exposed to debris, clogging can be forestalled by periodically reversing the direction of flow through the fluid line to carry debris in the doublets to a filter in the power and control housing. Since a heated filter for burning the debris would raise the temperature of the line fluid, the filter is incorporated into the reservoir refill cartridges. When anteroposteriorly oriented alike, doublets in separate circuits wherein the line fluid is pumped in opposite directions perform the same action. Typically, the barrel-assembly will be halted to use an injection tool-insert, and washing action commence upon resumption of transluminal movement. Reversal in transluminal direction affects neither the direction of fluid flow through the fluid circuit nor the directions of irrigative and aspirative function of the doublet.

Reversing this orientation thus reverses the action, whereas tool-inserts placed in separate circuits of flowing in opposite directions perform the same action when anteroposteriorly oriented alike. Back to back irrigator-aspirators, or point-washers, direct at and quickly aspirate fluid from a small segment of the lumen wall, allowing, for example, exposure to a therapeutic substance or a thermoplastied segment to be returned to body temperature more quickly than if the fluid were released and aspirated over a larger distance. Typically, the barrel-assembly will be halted to use an injection tool-insert, and washing action commence upon resumption of transluminal movement.

Reversal in transluminal direction affects neither the direction of fluid flow through the fluid circuit nor the directions of irrigative and aspirative function of the paired or doublet tool-insert. Reversal of flow through the fluid circuit only reverses which unit in the doublet functions as the emitter or aspirator, which has no medical significance. Consecutively positioned doublets connected to separate circuits can intermittently or continuously wash the lumen wall with water or different therapeutic fluids, and these can be changed midprocedurally by connection to different reservoirs or radial projection catheter power and control housing and hand grip inmate reservoir refill cartridges. Reversing the direction of flow through doublets fore and aft of an injector, for example, will not affect the therapeutic action whether the doublets are connected to the same or different circuits.

VII2g(3)(e)(x). Elimination of Gases from Fluid Radial Projection Unit Lines

FIG. 58 shows a simplified diagrammatic view of a fluid or piped circuit where the pump is built into the power and control housing, and is analogous to the battery used to power electrical units as shown in FIG. 57. The liquid in the closed circuit that courses through the barrel-catheter to the units may constitute the substance to be delivered or represent its solvent or medium, such as water. In the vascular tree, no significant amount of gas should enter the bloodstream. The small lumen diameter of most blood vessels demands that further reduction in the diameter of pipes and service-catheters be avoided, effectively eliminating the use of double lumen tubing, for example.

Once the circuit has been filled, or charged with the liquid medication or medium with the column from the reservoir continuous, the entry of air into the line is a concern when different liquid substances must be switched from one source reservoir to another. Delivery of the fluid in the circuit is directly analogous to infusion through an intravenous drip chamber, which serves to eliminate any air, an infusion pump and rapid infuser used when necessary to increase the rate of delivery through any of several type well established connections. Metered ejection in measured doses per treatment site can be accomplished with a metered pump.

Figure 79:
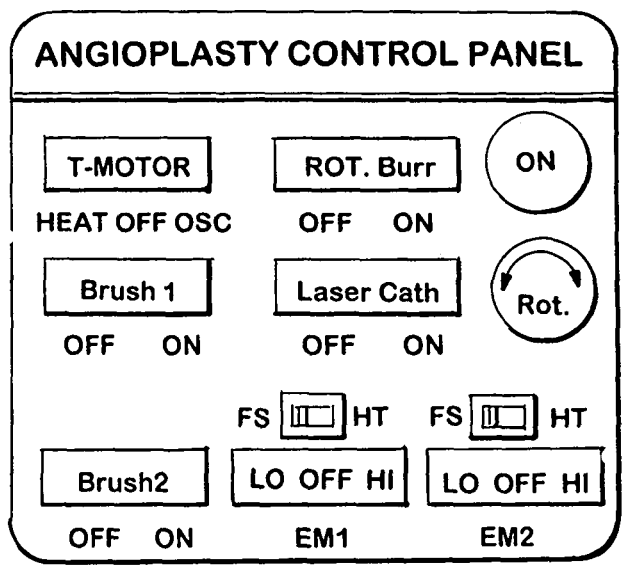
FIG. 79 shows a simple control panel for a combination-form ablation or ablation and angioplasty-capable barrel-assembly such as shown in FIGS. 71 and 78 with heatable turret-motor stator, heat-windows, evidement radial projection units, independently heatable recovery or electromagnet windings, which allows the insertion of an excimer laser, directional or rotary burr atherectomizer, or a fiberoptic endoscope, for example, in the central canal.

VII2g(3)(f). Radial Projection Unit Control and Control Panels, Elecrical and Fluidic or Piped FIG. 79 shows a control panel for a barrel-assembly or radial projection catheter which incorporates only electrically operated components for performing an angioplasty. Duplicate controls not mounted to the apparatus controlled may be provided for use by an assistant; however, to minimize operator error, interventional airgun, angioplasty, and ablation control panels are mounted to the respective apparatus the given panel controls. In a duplex or bipartite type barrel-assembly such as shown in FIG. 71, only the electrically controlled angioplasty components incorporated into the barrel-assembly proper at b. are controlled from control panel 163, and only the angioplasty components contained within the ensheathing radial projection catheter at a. are controlled from control panel 164.

That is, onboard control panel 163 includes only the controls for the power and control housing to which it is mounted, so that the apportionment of controls between the power and control housings reflects the apportionment of capabilities between the components of the duplex. Most often, the barrel-assembly without the ensheathing radial projection catheter will be at least minimally angioplasty-capable, with turret-motor and nose heat windows or laser for preemptory thermoplasty capability. Combination-form barrel-assemblies generally accept original equipment manufacturer produced cabled devices such as lasers and angioscopes supplied and used with a dedicated control console so that these controls may be separate and require the use of an assistant.

Self-contained ablation or angioplasty-capable barrel-assemblies and radial projection catheters can incorporate different components, so that combinations of these to comprise duplex barrel-assemblies will variously apportion the controls for the components contained within each between the respective power and control housing control panels. In barrel-assemblies and radial projection catheters for use in narrower ductus, this diversity is constrained not only due to the lack of space but the need for trackability. To optimize trackability in a duplex barrel-assembly, the unensheathed barrel-assembly proper or primary is minimized in diameter. This limits it to few, usually not more than four, electrical circuits to control the turret-motor, recovery electromagnets, and any radial projection units.

In barrel-assemblies for use in lumina that are less restrictive, the primary can include electrically and fluid controlled heat-windows and tool-inserts, and tool-inserts of either type may incorporate internal functions such as warming the contents of an injection syringe, which require additional circuits. Accordingly, the specific controls and the apportionment of these in ablation or angioplasty control panels of different barrel-assemblies and radial projection catheters vary considerably. For this reason, the control panel shown in FIG. 79 can be no more than exemplary. In a fluid circuit, current is used to control the electrohydraulic or electropneumatic control valve in each circuit fluid supply or pipe line.

The absolute distance of travel up and down and thus extension of the tool tip face beyond the outer surface of the muzzle-head is generally proportional to the diameter of the muzzle-head, which limits the depth of the radial projection unit lift-shaft 182. Within this gamut, the distance lift-platform 176 is raised is controlled by adjusting the electrical or fluid current. Upon the removal of current, thermal expansion wire 177 contracts to its dimensions at room temperature. Insertion of a chilled rod or cooling catheter down the adjacent barrel-tube will hasten retraction of the tool-insert. With a fluid circuit, a fluid control valve would shut off fluid flow causing lift-platform 176 to descend. While the control knobs are collocated on the control panel, independently controllable fluid circuits employ independent pumps.

Whether raised electrically or by fluid, retraction of lift-platform 176 is allowed by removal of the lifting current but effected by the downward urging of strip-spring 187, which prevents dissections by retracting the working face of tool-insert 184 to a position beneath the outer surface of the radial projection unit. When energized, thermal expansion wire 177 raises tool holding and lift-platform 176 to the top of lift-shaft 182 causing the working face of tool-insert 184 in FIG. 54 to radially extend beyond the surface of the muzzle-head. In a barrel-assembly for use in the vascular tree, the risk of embolization without the trap-filter deployed is reduced by limiting the excursion of the tool tip faces or upper edges of the tool-inserts beyond the outer surface of the muzzle-head to generally no more than 1.5 millimeters.

Incorporating a highly miniaturized electric scissors lift linkage, as described above in the section entitled Extended Projection Scissors Lift-platform Mechanism, allows the tip or working end of the tool-insert to be extended farther outwards. The trap-filter is automatically deployed upon energization of a radial projection unit even when no such height extension means is present. In piped or fluid operated circuits, elevation of lift-platform 176 requires no separate control but occurs on initiating fluid flow. If circulated at room temperature, the fluid is used to effect projection, such as of a closed-face or blank tool-insert for the purpose of nudging the muzzle-head in the opposite direction or to allow the tool face to be swept over the lumen wall.

The fluid can be chilled or heated for a number of purposes, to include accelerating or decelerating endogenous or introduced chemical action or, in an artery, for example, to ablate plaque. The delivery of solid solder miniballs lumen intraductally, for example, necessitates heating in order to denature the solder. The miniball is delivered through a barrel-tube, and as the muzzle continues distad, the radial projection unit moves behind to heat the miniball, which process can proceed continuously. Within the vascular tree, the projection of heat or cold is by applying a liquid to the rear of a blank metallic face-plate of high thermal conductivity. In other type ductus, the plate may be perforated to allow heated or chilled gas to be streamed over the lumen wall.

Since the duration of the procedure is a prime consideration and elevated ablative or abrasive type tool-inserts will preclude continued movement of the barrel-assembly until fully retracted (seated, stowed), a means for contracting the thermal expansion wire quickly once current is stopped is essential. To this end, strip-spring 187 assures that the recession (retraction, lowering) of lift-platform 176 is not limited in speed to the time it would take for expansion wire 177 to contract by passive cooling on deenergization, and thus eliminates the need to insert a cooling catheter. Piped units that are lifted coincident to fluid flow are also spring loaded for automatic return this way. Since temperatures above and below 90 degrees centigrade, which is effective for thermoplasty, are thrombogenic, the turret-motor and recovery electromagnets should heat the lumen wall through their housings to a temperature of 90 degrees centigrade with minimal rise and drop-off times.

Provided it is temperature isolated from the surface of the barrel-assembly except at the treatment face-plate, a fluid, because it can be preheated remotely from the muzzle-head and not have to build up or drop back in temperature right at the treatment site as must an electrically heated element, affords better control over temperature, which factor recommends piped radial projection units. The barrel-assembly will be capable of discharge and temperature ablation or angioplasty in alternation; however, the interval to allow dimensional stabilization will vary according to the materials and dimensions of the barrel-assembly. This interval must be specified and heeded.

In an electrical unit, the 90 degree-equivalent current used must be controlled to achieve this temperature, maintain it during use, then revert to body temperature as quickly as possible recommending microprocessor control over the current in each circuit. In both electrical and fluidic units, a spatial temperature gradient along the surface of the muzzle-head is prevented by placing insulation about at the margin of the intended lumen contact area. The 90 degree centigrade-equivalent limit current for the turret-motor windings and tractive electromagnets does not apply to thermal expansion wire 177, which is in an independent circuit and substantially temperature-isolated from the lumen wall by the intrinsic insulation value of the polymer material of or added lining in lift-shaft 182 and the thermal expansion wire 177 insulation.

The resultant ability to use a larger diameter expansion wire 177 with materials that exhibit a high thermal coefficient of expansion and melting point far higher than the temperature required, yield a high wire breakdown temperature and thus allow higher temperatures and degrees of wire expansion, hence, degrees of outward extension of lift-platform 176 for the tiny space available. In thermal ablation or ablation and angioplasty-capable and combination-form barrel-assemblies, the onboard electrical components draw current from the inmate battery in the hand-grip, radial projection units wired in series controlled together. Electrical components include those end-purpose at the treatment site, and those supporting piped units (see, for example, Yu, Z. Q., Hu, M. J., Pei, X., and Ruan, J. 2006. "Actuation and Control of a Micro Electrohydraulic Digital Servo Valve," *Journal of Physics: Conference Series: International Symposium on Instrumentation Science and Technology* 48:264-268).

A thermal ablation or ablation and angioplasty-capable or combination-form barrel-assembly with fully self-contained fluid pipe circuits requires a reservoir and micropump for each circuit. Low pulsation micropumps are currently available from many makers, to include Micropump Division, IDEX Corporation, Vancouver, Wash.; Cole Parmer, Vernon Hills, Ill.; TCS Micropumps Limited, Sittingbourne, Kent; ThinXXS Microtechnology, Zweibrücken; and Microfluidics Division, Frauenhofer Institut für Zuverlässigkeit and Mikrointegration, München [Frauenhofer Institute for Reliability and Microintegraton, Munich]. While inserted in the airgun, power can be drawn from the airgun power supply. Even if used in a coordinated manner, piped and nonpiped elements are generally not controlled together by wiring thermal expansion wires and fluid control valves in series.

Used in banks or groups, radial projection units can be used to nudge the muzzle-head eccentrically within the lumen to allow blood to pass. Unlike a balloon which dilates with radial symmetry, radial projection units can thrust sideways in any direction which their distribution will allow. When deflated, the balloon is, however, less obstructive and allows more blood to pass. Except for the upper corners, which are die-cut as rounded off at the upper ends to prevent cutting into the lumen lining, the upper edges of the faces and side edges are left squared. Swing out hold-down retaining arms 186 at the sides of lift-shaft 182 are recessed from the outer surface of the muzzle-head or radial projection catheter.

These are swung or slid aside to remove a tool-insert and swung over the upper edges of the lift-platform to retain it when in the raised working position. Otherwise, tool-insert 184 could be pulled out of lift-shaft 182 by the sideways levering forces of resistance at the tool working end it may encounter in use. Where an independent or barrel-assembly integral rotational atherectomy burr or an excimer laser has eliminated hardened prominences, radial projection unit tool-inserts can substitute for an angioplasty balloon in eliminating the balance of plaque when less calcified at the periphery. A supplementary plaque removal capability is of value, because both an excimer laser or a burr incorporated into the barrel-assembly must be centered in the muzzle-head and no larger in diameter than such devices are when independent.

Rotational burrs and lasers injuring the wall if used to too great a depth, the balloon angioplasty that would ordinarily be necessary to reduce residual plaque (atheromatous, diseased tissue) is here replaced by a variety of radial projection unit tool-inserts that can be used with the oscillatory mode of the turret-motor to cut or abrade this tissue away. In a barrel-assembly for use in the vascular tree, the risk of embolization is reduced by limiting the excursion of the tool tip faces or upper edges of the tool-inserts beyond the outer surface of the muzzle-head to generally no more than 1.5 millimeters.

Provided the action does not result in obstruction of the lumen longer than 2-3 minutes, where the muzzle-head exceeds the lumen in diameter, the muzzle-head can itself be used to compress soft plaque or soft plaque scraped off the lumen wall. This is done by advancing and withdrawing the muzzle-head over the scraped area. The incorporation of conventional means of atherectomy makes achieving a minimally occlusive diameter more difficult, but reduces operating time. Whether deployed during transluminal or rotatory movement, control of the radial projection units is by manual switching on the ablation and angioplasty onboard control panel. With a lumen wall that is malacotic and brushes that are harder, some tool-insert bristles could incise the lumen wall, the operator must specifically override the default retracted condition of the tool-insert lift-platform or platforms.

Thus, another limitation is that the radial blades should not be deployed while the barrel-assembly is advanced or withdrawn. Described below is a switching arrangement that instantly cuts off current to the scraper blades causing these to recede should the barrel-assembly be urged forward or backward as well as a circuit-breaker to stop current to the turret-motor when the set threshold value for maximum torque is exceeded. To allow somewhat greater depth of access into the vascular tree, when the muzzle-head reaches a segment wherein the lumen is the same in diameter, deployment of the radial projection unit tool-insert side-sweeper blades allows blood to pass. To orient the blades face- rather than edge-on to the bloodstream would further obstruct the flow of blood past the muzzle-head.

VII2g(3)(g). Coordinated Use of Aspiration and Piped Radial Projection Units to Remove Diseased Tissue or Obtain Tissue Samples for Analysis Tissue samples of greater volume and to a controllable depth are obtained by passing a side-cutting radial projection unit tool-insert having individual projections or 'bristles' and tips of the desired conformation as addressed below in the section entitled Radial Projection Unit Tool-inserts. Rotational and oscillatory action is obtained with the turret-motor or manually, and transluminal action manually or with the aid of a linear stage, which can also be driven to provide a vibratory effect. Scoring the area of the lumen wall to be treated with a radial projection unit brush tool-insert for the purpose of obtaining a tissue sample not only furnishes the tissue on the brush for brush cytology but also allows additional tissue to be recovered through aspiration.

In order to prevent the release of embolizing debris should the fibrous cap of an atheroma be ruptured, the apparatus automatically deploys a run-ahead trap-filter whenever a radial projection unit is energized (actuated). The considerable versatility in aspiration of fluids to, from, and over the treatment site before or during a procedure made possible through the coordinated use of supply and service-catheters, unlined barrel-tubes, and the central canal with piped radial projection units is addressed below under the section entitled Radial Projection Units.

VII2g(4). Minimally Ablation and Ablation and Angioplasty-Capable Barrel-Assembly Control Panels A minimally ablation or ablation and angioplasty-capable barrel-assembly is not used separately from an airgun. Such a barrel-assembly lacks an internal power source and is meant primarily to provide prophylactic cauterization attendant upon discharge implantation; that is, to preclude plaque rupture by the muzzle-head or miniballs that would result in a release of embolizing debris. While discharge controls go to the airgun and ablation or angioplasty controls go to the barrel-assembly, the controls for a minimally ablation or ablation and angioplasty-capable barrel-assembly, because it is airgun dependent, are exceptionally mounted to the airgun. That is, pistols and dedicated airguns meant for use with minimally ablation or ablation and angioplasty-capable barrel-assemblies, because these are used only while inserted in an airgun, include the controls for ablation or angioplasty on the airgun.

An air pistol paired with an ablation or ablation and angioplasty-capable barrel-assembly affords free manipulability as does an ablation or ablation and angioplasty-capable barrel-assembly when disengaged from the airgun; however, pistols are not well suited to mounting upon a linear positional stage to implement the discharge of implants in a close formation whether to distribute the magnetic load, increase the dose, or both at the treatment site. A minimally capable barrel-assembly usually takes power from the airgun power source. If a pistol, this consists of a battery pack in the form of a downward extension of the pistol grip. Modified commercial air pistols for use with minimally capable barrel-assemblies have any ablation or angioplasty controls mounted to the side of the power and control housing, or battery-pack grip extension, and far down enough as not to be covered over by the hand.

Any ablation or angioplasty controls are therefore mounted on the same control panel as the potentiometers used to control the recovery electromagnet field strength. So long as more flexible, finely graduated, or quickly achieved adjustment in the exit velocity is not required, and the implants need not be placed in so close a formation as to require placement under automatic positional control, such a pistol and minimal ablation capability barrel-assembly combination can achieve the ablation or angioplasty capability of an ablation or ablation and angioplasty-capable barrel-assembly, and in an equally compact form. However, high density implantation over the site for treatment may be essential to achieve the prescribed dosage level or combination of medications with medication miniballs, or to yield a uniform and nondissecting distribution in the magnetic tractive force.

For this reason, the combination of a dedicated interventional airgun with an ablation or ablation and angioplasty-capable barrel-assembly can provide the optimal ablation or angioplasty sufficiency, and discharge precision consistent with the greatest manipulability. Except for combination-form ablation or ablation and angioplasty-capable barrel-assemblies, a minimally ablation or ablation and angioplasty-capable barrel-assembly can provide all of the tissue reduction features of the capable or stage mountable configuration. Thus, unless discharges must be placed accurately, a pistol discharged minimally ablation or ablation and angioplasty-capable barrel-assembly, provided it incorporates the same features as a capable barrel-assembly, can accomplish the work of the latter at lower cost.

However, most minimally ablation or ablation and angioplasty-capable barrel-assemblies do not require and do not incorporate all of the tissue reduction features of ablation or ablation and angioplasty-capable barrel-assemblies. The control panel of a dedicated interventional airgun for use with minimally capable barrel-assemblies is mounted on the airgun enclosure. To use a nose-cap heat-window, for example, these control panels typically include controls for adjusting the current to either of the two recovery electromagnet windings, raising and lowering radial projection units, deploying and recovering an embolic trap-filter, and for controlling any other features the barrel-assembly incorporates. Generally, the controls specific to ablation and angioplasty are mounted on barrel-assemblies with this capability, whereas the controls for discharge positioning and discharge are mounted on the airgun.

For convenience, controls for the one type function can be co-located on the other device; however, a presentation that is functionally pure, that is, which keeps the controls for either function with the respective device, is conceived of as less amenable to human error. In a minimally ablation or ablation and angioplasty-capable barrel-assembly, the controls may be co-located making it desirable to disable the distinctly implant discharge related controls when not needed. Some original equipment manufacturer components, such as a vortex tube based cold air gun attached at the back of an ablation and angioplasty barrel-assembly include their own built in controls as well. In most instances, these will not be separable from the device itself, but the position of the device will result in a favorable situation of the controls.

Preclusion of a midprocedural loss in power imperative, should the inmate battery fail, a cable to allow the direct connection of the barrel-assembly to the airgun power supply without the need for engagement in the airgun barrel can be provided as a backup power source. To protect against power failures or loss in dependability, as from harmonic distortion, frequency variation, or voltage irregularity, the airgun includes an uninterruptible power source. This backup notwithstanding, in an embodiment that contains most or all of the components to be described, the battery in the hand-grip of the barrel-assembly should be sized to supply emergency current to power the airgun and the barrel-assembly were the uninterruptible power source runtime to elapse.

The controls to rotate the muzzle-head are therefore duplicated in the barrel-assembly and the airgun. Transluminal advancement or withdrawal with the aid of the linear positioning table requires insertion in the airgun, so that there is no need for a duplicate control onboard the barrel-assembly if resorted to during an ablation or an angioplasty; however, this implies that insertion in the airgun is true only over the relatively brief interval required to effect more precise transluminal movement by this means. From a mechanical standpoint, balloon cryoplasty and thermal angioplasty differ from balloon angioplasty in that the fluid used to inflate the balloon is chilled or heated.

Otherwise, the balloon is aligned to the lesion to be treated by hand and inflated for the interval desired just as in ordinary angioplasty. Not inflatable, the muzzle-head cannot use inflation time to reduce the exposure of blood and tissue to the thrombogenic temperatures that surround the target temperature. An external hand-held electromagnet can be used to draw a muzzle-head of smaller gauge than the lumen against the lesion. Along with the blood-grooves and tunnels built into the barrel-assembly to reduce the risk of ischemia, suitably directed 'heat-windows and quick temperature rise or drop and recovery times are important. For isolated exposure of a distinct lesion to the heat or cold, a muzzle-head containing a 'heat-window of suitable area and shape is used.

However, the knowledge that vulnerable plaque is not to be equated with a localized obstructive lesion but is more likely characteristic of the vessel over longer segments promotes a extension for prevention approach. For this purpose, the muzzle-head is drawn over the lumen surface at a constant temperature at a controlled rate. To accomplish an extensive treatment thus, a balloon must be inflated, then deflated, stepped forward or backward by its length, reinflated, deflated, and so on. The advantage in reduced operative time in the continuous passage of a muzzle-head over the lumen surface is significant enough to encourage extension for prevention.

Whether transluminal movement is by direct manipulation or a positional mode of the linear stage, when the turret-motor is not required for rotating the muzzle-head, use of its winding as a heat source allows thermal, cryogenic, and/or radial projection unit shaver, brush, or chemical discharge tool-insert angioplasty and ballistic discharge in the same pass. This is primarily intended for introducing absorbable medication miniballs during the angioplasty. Ordinarily, having been brought to the position for discharge, the barrel-assembly is stopped until the preceding miniballs have seated or become infixed. This allows the retrieval of any that may have been mispositioned before proceeding to the next discharge. In a combined angioplasty and discharge, to prevent overexposing the lumen wall to excessive ablative action, the muzzle-head must be moved at a specific uniform rate without pause.

The rate of passage during an ablation or an angioplasty is thus the dominant factor to which the rate of discharge, which is travel rate neutral, must defer. For this reason, when nonabsorbale (medication or other chemical) miniballs are implanted, close spacing may necessitate the initiation of successive discharges each before that preceding it has seated. Angioplasty that combines the use of radial projection unit tissue removing tool-inserts with thermal or cryogenic means is not contemplated whether apart from or in combination with discharge. Commercial controller-drivers such as those delineated in the section above entitled Control of Muzzle-head Turret-motor Angle Within Working Arc can control the travel rate and discharge, the latter as an auxiliary function.

With sufficient circumferential clearance, a 'cooling' catheter connected to a cold air gun passed down the central canal or a service channel as the source of hot or cold air does not interfere with rotatory use of the turret-motor. The recovery electromagnets and trap-filter are used to recover any mispositioned miniballs. Use of the most effective temperature for achieving the elimination of vulnerable plaque while avoiding thrombogenesis is also important for avoiding thrombosis and tackiness (stickiness, cling) as the muzzle-head progresses. The advisability of using platelet blockade, lubricants that afford the polytetrafluoroethylene-coated muzzle-head further slipperiness in the presence of clotting and that remain effective at the temperatures used, and medication to suppress hyperplasia is clear.

The process is not more traumatizing than alternative means for performing an atherectomy, to include rotating razors or cutting balloons. The initial positioning and final withdrawal of the barrel-assembly are performed manually. During the time that an ablation or ablation and angioplasty-capable barrel-assembly is used to perform an ablation or an angioplasty, either free manipulability or machine-control over the rate of advancement or retraction (withdrawal) may be of greater benefit. Whereas direct manipulation of the barrel-assembly affords quick intuitive control over transluminal positioning and the rate of movement, connection of the barrel-assembly to an airgun mounted on or to a separate linear stage affords precision in the transluminal translation rate. Engagement within a linear stage prevents direct manual control over the transluminal positioning of the barrel-assembly within the lumen.

Freedom of movement is best afforded by direct manipulation. However, when to minimize trauma to the lumen wall the time of contact with the heating, chilling, or ablative muzzle-head would best be precisely controlled, the use of the linear stage is preferable. When the distance between segments for treatment is not significant, the linear stage can be used to move from one to the next. Even when the entire procedure is automated, quick heating and cooling with cooling service-catheters and the use of attachments such as a cold air gun or $CO_2$ cylinder will require manual support through a side-socket as addressed below in the section entitled Barrel-assembly Side-socket. Lacking an internal transluminal mover, barrel-assemblies must be inserted into an airgun mounted on a linear stage or a separate linear stage for machine executed transluminal movement.

Coming after a manually controlled ablation or angioplasty, this does not represent a loss of functionality, because:

1. Transluminal advancement and withdrawal by minute increments is primarily needed to achieve a uniform close distribution pattern of miniballs containing ferrous material during implantation discharge so as to obtain an even distribution of the resultant stent magnetic force, and 2. The ablation or angioplasty usually involves one or well separated segments suited to direct manual control rather than movement by fine incremental steps.

Reciprocally, exactitude and consistency in the rate of passage is not important during discharge but may be of considerable importance during the use of ablation or a radial projection unit shaving or brush-type tissue removing tool-inserts, thermal tissue reduction (thermoplasty), or cryogenic angioplasty (cryoplasty), for example.

VII2h. Ablation and Ablation and Angioplasty-Capable Barrel-Assemblies

When slightly oversized, the muzzle-head body itself can exert balloon-like compression on protrusive plaque, but as is true with a balloon, this can dislodge vulnerable plaque, and the deployment of a embolic trap-filter ahead of the muzzle-head has itself been implicated in dislodging plaque. Angioplasty-capable barrel-assemblies may be used independently of an airgun to significantly reduce if not eliminate plaque prior to the insertion of a conventional or endoluminal stent, or following use for angioplasty independently of an airgun, can be inserted into an airgun to initiate stenting without withdrawal from the ductus. For both angioplasty and stenting functions, extreme limitation in diameter and a severe requirement for steerability as a functional combination of flexibility and stiffness represent the primary constraints imposed upon such components as may be devised.

Enhanced versatility and freedom of movement of the angioplasty-capable barrel-assembly as independent of the airgun imposes greater expense. That is, an angioplasty-capable barrel-assembly when optimized in free-standing ability requires insertion into the airgun only for discharge. During an angioplasty as a distinct procedure that may or may not be followed by stenting, the need to insert the barrel-assembly into the airgun to draw power from the power supply rather than an inmate battery or to connect the turret-0motor to a controller-amplifier within the cabinet of the airgun rather than to an onboard polyphase current-generating microcircuit, involves connection that reduces independence and freedom of movement. Except where connection must be continuous to draw power, such connection is temporary but still comes as an interruption.

For incorporation into an ablation or ablation and angioplasty-capable barrel-assembly so that it can be used independently of the airgun, miniaturized control electronics, such as are available, for example, from Data Device Corporation, Bohemia, N.Y., Precision MicroControl Corporation, Carlsbad, Calif., Galil Motion Control, Rocklin, Calif., among many others are available. Whether occlusion is associated with atherosclerosis, fibromuscular dysplasia, stenosis attributable to other vasculopathy, or a combination of causes, the susceptibility of an artery to obstruction varies inversely as the cross-sectional area of the lumen. The same may be said of many instances of stenosis in other type ductus, some treatable with the same apparatus, which is rarely if ever without concurrent medical (drug) treatment.

That the principal factor predisposing to occlusion is smallness in lumen diameter makes severe limitation in diameter the chief design constraint upon any catheter-based device. Any effective mechanical device for intervening in this occlusive process must be able to reach such sites. Because plaque tends to accumulate at points in the vasculature that are intrinsically subject to turbulent flow—at angular turns at the entries or ostia of branches, bifurcations, at convolutions and over tortuous stretches, in the extremities where increased distance from the heart results in the reduction of propulsive force and an increase in the effects of gravity—the protrusion of plaque into the lumen only makes flow past such points even more turbulent, hence, thrombogenic.

The propensity to favor twists and turns adds steerability to restriction in diameter as a basic requirement for barrel-assemblies; essentially, the more difficult it is to reach a certain point, the more probable is it that that will be a point that has to be reached. For post-acute event patients resistant to medical treatment, thrombectomy will usually be essential, and for any patient predisposed to an acute event by advanced occlusive disease, an atherectomy may be recommended. However, severe limitation in diameter precludes incorporating two different rotating tools, one for thrombectomy and the other for atherectomy, in the same barrel-assembly. Unlike power burrs, which are suited to removing hard plaque but not soft material, a laser can remove both thrombi and all but exceptionally calcified plaque.

This leaves only the occasional need to cut through very hard plaque as necessitating the antecedent use of a separate conventional rotational atherectomy or other mechanical rotational ablation, or rotablation, device. Simple balloons can compress softer plaque and place an expandable stent, but not in a single operation as would allow entry and withdrawal only once. Furthermore, the need for more than one stent is common, and to place these with a balloon necessitates reentry to place each stent. Using existing means for clearing the lumen and stenting, entry and withdrawal is required at least twice, because the lumen must be cleared of plaque before stenting can commence. A device that having been introduced transluminally but a single time can remove and not just crush plaque up against the lumen wall and can proceed to effect stenting at multiple locations along the same vessel clearly reduces operating time and the risk of complications.

Whereas balloon angioplasty is often performed to expand the vessel following thrombectomy, here the muzzle-head, while not forcibly inflated to risk dissections, still imparts some straightening and expansion likely to suffice in less refractory cases. When the balloon cannot pass the lesion without the need for rotablation, the residual plaque may still be too hard to safely mash against the lumen wall. The balloon may necessitate the preliminary opening of a channel large enough for the balloon to be entered, but then does not provide means for the intermediate removal of hard plaque following rotablation and preceding angioplasty. Here, in addition to initiating stenting, the barrel-assembly can provide ancillary means for expanding a post-rotablated lumen with less risk of producing dissections in the form of radial projection unit tool-inserts and a laser, and here too, the muzzle-head, while not inflated, in and of itself still imparts some straightening and expansion.

A stated object here is to minimize operating time and therewith the time of interrupted oxygenation. While extraluminal stenting necessitates separate access through an incision to place the stent-jacket, this is often possible under a regional if not local anesthetic at a later date. Over and above the desirability of reducing entries and withdrawals, when anesthesia is general, reducing procedure time is conducive to a more favorable outcome. Thus, currently no device combines an atherectomy or atherotomy and an angioplasty capability with the ability to initiate stenting in a single device as does a barrel-assembly with radial projection units as described below. Radial projection units are suited to assist a primary mechanism, whether a burr or laser, for the removal of occlusive matter.

Instances inevitably arising whereby to scrape all the peripheral plaque as may remain would simply take too much time, such use is always discretionary on the part of the operator. In integrating a means for the ablation of lesions atheromatous or otherwise into the muzzle-head, the cardinal desiderata remain safe trackability and minimized operative duration. While combining atherectomizing and the intraductal component of extraluminal stenting means in the same transluminal device can significantly reduce if not eliminate the need for withdrawal and reentry and thus reduce the duration of the procedure and the risk of entry wound complications, to accomplish this at the expense of increased risk of ischemia because the barrel-assembly has been increased in diameter is counterproductive.

The most widely accepted means for opening occluded vessels are the rotational atherectomy burr, such as made by Boston Scientific and the laser catheter, such as made by Spectranetics. Neither device can eliminate plaque up to the lumen wall, because to do so risks injury that can result in abrupt closure or perforation; the prior art makes it clear that the incorporation into the barrel-assembly of a laser is limited for practical reasons to the longitudinal or central axis of the barrel-assembly. This is no less true when either of these devices are incorporated into the barrel-assembly. However, the incorporation of radial projection units into the muzzle-head provides a followup mechanism for removing residual plaque once the burr or laser has passed.

Broadly, to afford clearance for the passage of the blood demands minimizing the diameter of the barrel-assembly, which in turn demands reduction in the number and/or diameter of barrels, hence, of the diameter of the miniballs that may be used. The need to use miniballs of smaller diameter in the wall of a vessel must always be compensated for with a higher density distribution in order to more uniformly distribute the magnetic traction and thus reduce the risk of an eventual vessel wall perforation by an isolated miniball of a tissue insinuative diameter under excessive magnetic traction. Essentially adapted from the high-speed drills used by dentists, rotational and directional atherectomy devices use a cutter rotated by an air turbine. Other examples of combined function devices are powered cutting balloons that atherectomize and passive rotational cutting balloons that atherotomize.

Powered rotational burrs, passive cryogenic, thermal, ultrasonic, and laser devices are single-function atherectomy devices that remove hard prominences, reducing the risk of dissections and restenosis as would otherwise be more likely to result from the angioplasty performed next (see Safian, R. D., Freed, M., Reddy, V., Kuntz, R. E., Baim, D. S., Grines, C. L., and O'Neill, W. W. 1996. "Do Excimer Laser Angioplasty and Rotational Atherectomy Facilitate Balloon Angioplasty? Implications for Lesion-specific Coronary Intervention," *Journal of the American College of Cardiology* 27(3):552-559). When the muzzle-head is of the type having the gas-return path rather than a laser catheter at the center, one to four separate laser catheters depending upon the unbranched diameter at the distal working tip pass through the barrel-catheter and midway between the barrel-channels to the nose. Short of terminating at the working end, the fibers of the separate cables can merge to form a unitary tip or divide and merge to form a unitary tip of larger diameter.

VII2h(1). Distinction in Ablation or Ablation and Angioplasty-Capable Barrel-Assemblies as Unitary or Bipartite Minimally ablation or ablation and angioplasty-capable barrel-assemblies are addressed in the preceding section. Averting the added cost for capabilities that are often unnecessary, minimally ablation or ablation and angioplasty-capable barrel-assemblies are primarily means for ballistic implantation that include a thermal ablation or angioplasty capability as an immediately available precaution for destroying potentially embolizing debris that contact with the muzzle-head could release and are not configured to function independently of an airgun to perform an intricate or extensive ablation or angioplasty. The bipartite (duplex, joint) barrel-assembly is paired and divisible.

Except when reentry and withdrawal through the entry wound is objectionable, the ability to use multiple differently equipped sheaths with the same barrel-assembly during a procedure removes any limitation on the number and type of radial projection unit tool-inserts that can be brought to bear on a lumen of given caliber. Such exchange uses the intracorporeal barrel-assembly as in effect a guide wire. Another application for ensheathment within a combination-form radial projection catheter of matching diameter is to allow a more fully capable ablation or angioplasty-capable barrel-assembly to more easily track a narrow lumen. Once endoluminal (intravascular), the barrel-assembly is supplemented by sliding the radial projection catheter over it to the treatment site.

A duplex barrel-assembly is diagrammatically represented in FIG. 71, wherein the barrel-assembly proper comprises power and control housing 163, barrel-catheter 44, and muzzle-head 73, with the angioplasty control panel 164 mounted to the matching ensheathing radial projection catheter. As indicated, a barrel-assembly proper may have any number of matching radial projection catheters where the barrel-assembly proper and its projection catheters comprise a set. Division into an axial or inner primary barrel-assembly or barrel-assembly proper and an ensheathing or secondary projection catheter allows reducing the primary or barrel-assembly proper, which is usually moved to the treatment site first, to the minimum number of inmate electrical components needed to perform a preemptive thermoplasty and to the minimum diameter, hence, optimal trackability.

First introducing the primary alone for expedited tracking, multiple combination-form radial projection catheters can then be used interchangeably by sliding off and thus withdrawing the one and then sliding another on the primary. Within the limitations imposed by the diameter of the lumen, the kinds, potential number, and combinations of tool-inserts (qv.) to which this allows access exceeds any needed for a practical procedure. The access to additional tool-inserts this provides increases the kinds and extent of mechanical action and the application of medication and adjuvant or other therapeutic substances that can be delivered to the treatment site.

Thus, once endoluminal (intravascular), the primary can be supplemented with an unlimited number of electrically and/or fluid-controlled side-looking injection, ejection, heating, chilling, abrading, ablating, irrigating and aspirating, or debriding, and other tool-inserts within the diameter of the lumen treated. The two components in such a duplex barrel-assembly can be used independently or together to combine the capabilities respective of each. Used separately, the combination-form radial projection catheter can accept not only a barrel-assembly but cabled devices, such as an angioscope, laser, or a rotary atherectomy or thrombectomy cutting tool, for example. Whether the normal anatomy, distended due to disease, or dilated with medication, an initially larger lumen that gradually narrows can be treated by sliding an outer combination-form radial projection catheter over an inner one.

An embolic filter can be incorporated in nose 64 of distal muzzle-head 73; however, the more so as the lumen narrows, the use thereof is usually not feasible, unnecessary, and as addressed below in the section entitled Embolic Trap Filter in Radial Discharge Muzzle-heads for Use in the Vascular Tree, may prove counterproductive. Simple pipe type barrel-assemblies may be duplex, but used only manually, do not incorporate a forward drive and sag leveling and stabilizing device. Thus, minimally capable barrel-assemblies angioplasty only as adjunctive to stenting implantation while remaining inserted in the airgun rather than as a distinct preliminary procedure during which the barrel-assembly is used prior to insetion in the airgun.

That is, thermoplasty capability is included only to the extent necessary to prevent or mitigate the consequences of any midprocedural ruptures of plaques, electrically operated radial projection units included in the muzzle-head to allow the use of spring-released syringe ejectors that emit a lubricant to aid in tracking or to inject the lumen wall with a therapeutic fluid such as a tumefacient and/or an antibiotic in preparation for implantation, for example. A nose heat-window that makes the additional inclusion of an embolic filter, which would require an increase in diameter and add to the cost at slight if any residual benefit, is provided.

Still minimally capable barrel-assemblies for vessels with a heavier burden of plaque warrant the addition of side heat-windows and ablative capability as inmate means that respond immediately without a power and control housing hand grip and therewith, the range of capability and the cost of independent sufficiency; however, such reliance pertains over a small range before the need for a fully capable barrel-assembly is indicated. Also to allow a smaller diameter and greater flexibility to the extent necessary, radial projection circuits in the muzzle-head are electrical rather than fluid. Actual barrel-assemblies transition over a wide spectrum from minimally to fully capable and self-contained, so that a barrel-assembly of intermediate size might well include a fluid circuit, for example.

By contrast, ablation or ablation and angioplasty-capable barrel-assemblies must be capable of performing an ablation or an angioplasty as a primary function, independently of an airgun, whether insertion in an airgun and ballistic implantation are to follow or not. Except with respect to those of larger diameter which incorporate as many radial projection circuits as necessary in the muzzle-head and/or along the sides of the barrel-catheter without the need to be ensheathed within and thus joined with a combination-form or through-bore type radial projection catheter, an ablation or ablation and angioplasty-capable barrel-assembly that must achieve a small diameter to expedite introduction and tracking once introduced is supplemented with a size-matched matching combination-form radial projection catheter.

A minimally capable barrel-assembly can be converted to a fully capable barrel-assembly by further adding a slidable power and control housing. An ablation or ablation and angioplasty-capable barrel-assembly allowed sufficient diameter incorporates all of the tools required and is unitary, whereas one that must pass through lumina so narrow that an embolic filter and radial projection units other than a nose heat-window and a few others to aid transluminal movement must be eliminated requires that additional tools be relegated to a separate sleeve or sheath. It is only when the diameter of the lumen becomes so narrow that the sheath or combination-form radial projection catheter can no longer be added that it becomes necessary to first enter with a projection catheter which must be withdrawn so that a radial discharge monobarrel can be introduced.

The separate sheath is a size-matched through-bore or combination-form radial projection catheter, which in any size can be used independently of a barrel-assembly. A combination-type projection catheter can be used with the bore empty or occupied by any of several different cabled devices or an embolic filter, for example. In using a duplex barrel-assembly, trackability is maximized by passing the muzzle-head to the most distal treatment site at the outset while not ensheathed within the radial projection catheter. If this action involves the use of the linear positioning stage, then the forward drive and sag leveling and stabilizing device is used.

Once the treatment site has been reached or at any other time, the projection catheter is slipped over the barrel-assembly using its barrel-catheter as a guide wire. The stiffness added by ensheathment within the radial projection catheter eliminates the need for a forward drive and sag leveling and stabilizing device over any extracorporeal length of the barrel-catheter to which the projection catheter proximally extends. Atheromatous arteries impose stringent constraints on diameter, necessitating pressure diversion channels, and when end-arterial or supplying an unshared territory such as the coronaries or mostly unshared territory such as the carotids, debris removal requires an embolic filter and/or nose heat-window and/or aspiration tool-inserts.

Atheromatous arteries impose stringent constraints on diameter, necessitating pressure diversion channels, and when end-arterial or supplying an unshared territory such as the coronaries or mostly unshared territory such as the carotids, debris removal requires an embolic filter and/or nose heat-window and/or aspiration tool-inserts. Using the apparatus described herein to perform an angioplasty and/or other therapy to be followed by ballistic stenting implantation without the need to withdraw and reenter, only the smallest arteries with critical fields may prohibit the use of even the narrowest monobarrel while ensheathed and thus require a first entry with a simple radial projection catheter for preparatory treatment followed by a second entry with a radial discharge monobarrel to place miniballs.

Except in this circumstance, stenting preliminary or preparatory treatment and stenting implantation are accomplished with a single entry. However, arteries of such small size should rarely present lesions that a radial discharge monobarrel with nose heat-window cannot treat without the need for ensheathment. When necessary to achieve a small enough diameter, radial projection units incorporated into the muzzle-head are limited to a few operated electrically used to emit a lubricant or medication while advancing toward, and/or injecting the lumen wall upon initial approach to, the treatment site.

Setting aside the need for a fiberoptic endoscope (see, for example, Miskolczi, L., Flaherty, J. D., Guterman, L. R., and Hopkins, L. N. 2001. "Case Report: Carbon Dioxide Column Angioscopy: A New Endovascular Imaging Technique," *American Journal of Neuroradiology* 22(10):1849-1853; Soper, T. D., Haynor, D. R., Glenny, R. W., and Seibel, E. J. 2010. "In Vivo Validation of a Hybrid Tracking System for Navigation of an Ultrathin Bronchoscope within Peripheral Airways,". *Institute of Electrical and Electronics Engineers Transactions on Biomedical Engineering.* 57(3):736-745) or other viewing device, and in embodiments for use to perform an angioplasty, an embolic filter, as well as the number of electrical or fluid radial projection circuits, the basic sequence of increasing diameters is:

1. Simple radial projection catheter followed by radial discharge monobarrel-assembly.

2. Joint, such as bipartite or duplex, angioplasty-capable barrel-assembly, the ballistic component usually introduced alone first for easier tracking, and 3. Unitary or integral angioplasty-capable barrel-assembly with only electrical radial projection circuits; and Unitary angioplasty-capable barrel-assembly with fluid radial projection circuits.

Rather than a combination-form radial projection catheter, the outer component in a bipartite ablation or ablation and angioplasty-capable barrel-assembly can be an inner and/or outer diameter adaptor and/or a heating or cooling jacket. These can uniformly warm or chill over the entire outer surface or be provided with heat-windows as addressed above in the section entitled Thermal Conduction Windows (Heat-windows) and Insulation of the Muzzle-head Body in Thermal Ablation or Thermal Angioplasty Minimally or Fully Capable (Independently Usable) Barrel-assemblies.

Uniformly distributed or regionalized pores in the surface can release a fluid continuously pumped through an end or side-socket of the kind addressed in the sections above entitled Ablation or ablation and angioplasty-capable Barrel-assembly End-socket and Ablation and Angioplasty-capable Barrel-assembly Side-socket. Such a steam jacket-like sheath is not internally differentiated or piped; topically distinct locations for fine and targeted control over release or aspiration are accomplished by means of radial projection units.

VII2h(2). Specific Advantages in the Elimination or Minimization of Connection to the Airgun (Tethering)

Since an ablation or angioplasty-incapable barrel-assembly is used only while engaged in an airgun, the elimination of tethering pertains only to angioplasty-capable barrel-assemblies. During an angioplasty, the barrel-assembly is powered from the on-board lithium-polymer or silver-zinc battery pack in the hand-grip at the proximal end, and as preferred for freedom of movement, untethered, hence, physically independent from the airgun or any other apparatus. Battery power is always used for the radial projection units and use of the turret-motor and/or electromagnet windings in their secondary nonpositional function as heat sources for thermal angioplasty. Angioplasty-capable barrel-assemblies must be tethered only when the source of high or low temperature is a vortex-tube based gun that must be supplied with compressed air from a canister (cylinder, air tank).

Such connection is not through the airgun but rather directly to the air tank through a very pliant hose. Placing all of the control electronics, the propulsive gas supply cartridge, and other components within the airgun cabinet, necessitating that the barrel-assembly be left engaged within the airgun barrel for these components to function would economize by avoiding the need for microminiaturization. However, the functional superiority of barrel-assembly operability independently of the airgun cabinet or chassis to perform an ablation or angioplasty outweighs any such economy; an ablation or ablation and angioplasty-capable barrel-assembly might always be used as an independent apparatus for these processes without ever being inserted into an airgun as its barrel for effecting implant discharge.

Thus, were an angioplasty-capable barrel-assembly to be dependent upon the airgun chassis as lacking inmate (on-board, self-constrained, internal) control electronics and an end-plug for connecting a nitrous or oxide or carbon dioxide cartridge, connection to the positional and temperature control components through the airgun during an angioplasty would be necessary frequently for:

1. Temporarily connecting the turret-motor to the controller and drive through the airgun to:

a. Rotate the muzzle-head in order to:

(1) Redirect a thermal window, especially when heating is eccentric through the use of a single electromagnet or motor winding.

(2) Redirect the radial projection units, so that a different type brush type tool-insert, for example, can be applied, such as rotating from one with microshavers to one with microbristles.

b. Oscillate the muzzle-head either by detuning the turret-motor drive velocity loop for random response, or as mentioned above in the section entitled Concept of the Extraluminal Stent and the Means for Its Placement, programming the servocontroller for controlled oscillation in order to:

(1) Free the muzzle-head if stuck, the use of a lubricant, if necessary, achieved by injection through a service-channel catheter.

(2) Assist in passing a tortuous course of the ductus if and only if the risk of serious injury is judged not to be present. The intrinsic lubricity of the muzzle-head and the ability to lubricate and oscillate the muzzle-head if necessary make the need for surgical removal hardly possible.

(3) Apply a radial projection unit tool-insert, such as a side-sweeper, in a vibratory manner.

However, a. Connection (coupling) of a laser, rotational, or other mechanical-type atherectomy cutting head cable in a combination-form or barrel-assembly that incorporates such (addressed below) is not through the airgun but rather to the respective control console.

b. Connection of a cooling catheter (addressed below), which if not permanently installed in the central canal of an edge-discharge barrel-assembly with nose-window is usually prepositioned within the barrel-assembly for immediate use, or connection without a cooling catheter directly to the central canal or a spare barrel-tube (addressed below) is directly to the vortex tube, which in turn is connected by a hose to a tank of compressed air or a nitrous oxide or carbon dioxide cartridge attached to the back (proximal) end of the barrel-assembly.

When a vortex tube (addressed below) is used for thermal or cryogenic ablation or angioplasty, it is mounted to the outside of the interventional airgun cabinet (enclosure). The air tank or canister containing the filtered compressed air for the cold (or hot) air gun is mounted to the airgun cabinet supporting stand. Exceptionally, the use of a vortex tube does not allow an ablation or ablation and angioplasty-capable barrel-assembly to be completely disconnected; however, connection by a pliant hose to the air tank need not impede freedom of movement. Thus, except in this circumstance, the proximal end of the barrel-assembly is unconnected and freely movable.

In an angioplasty-capable barrel-assembly with a 3-phase motor drive servocontrol microchip incorporated into the hand-grip shaped battery pack, the muzzle-head can be oscillated or rotated without the need to insert and thus electrically connect it through the airgun. Of these three functions that necessitate the predischarge insertion of the barrel-assembly into the airgun or connection of the barrel-assembly to a cable, the first, to draw control current for rotating the turret-motor, can be eliminated by incorporating a nonvariable speed microcircuit controller and drive that draw power from the inmate battery into the hand-grip.

Companies that produce or are able to produce micromotors and microcircuit controllers include Maxon Miniature Motors, Burlingame, Calif.; Solitron Devices, West Palm Beach, Fla.; Contec Microelectronics, Osaka, Japan (San Jose, Calif.); Micromot Controls, Maharashtra, India; Precision MicroControl Corporation, Carlsbad, Calif.; Precision MicroDynamics Incorporated, Victoria, British Columbia; ProDex Incorporated, Santa Ana, Calif.; and the Xajong company, Taichung, Taiwan. Considering each in turn:

1. When for simplicity and economy, the incorporation into the hand-grip of an auxiliary controller and drive consisting of a highly miniaturized version of the Data Device Corporation PWR-82332 or SatCon 8314C type, for example, for delivering polyphase current to the turret-motor windings to rotate the turret-motor is not contemplated, and the muzzle-head cannot be manually rotated with the necessary or without risk of stretching injury or dissections, then rotating the muzzle-head requires temporary connection of the turret-motor to the controller and drive housed within the cabinet of the interventional airgun. Temporary connection of the turret-motor to the airgun power supply is through contacts located at the proximal end of the barrel-catheter as shown in FIG. 72 when the barrel-assembly is engaged in the airgun chamber as shown in FIG. 74. When connection is through a cable located at the front of the airgun muzzle as shown in FIG. 75, connection need not be broken by removal of the barrel-assembly. Such an angioplasty-capable barrel-assembly is suitable for procedures not likely to require rotation of the muzzle-head.

2. A combination-form angioplasty-capable barrel-assembly that incorporates a rotary burr or excimer laser requires a power cable that terminates proximally at the bottom of the barrel-assembly or in a socket at the rear (proximal) end of the central canal for temporary connection to the control console. Albeit inconsequentially, during intervals when the atherectomy component is connected, complete freedom of movement is curtailed.

3. If the turret-motor and/or tractive electromagnet windings had just been used for thermal angioplasty, the counter-thrombogenic requirement to immediately cool the muzzle-head down to body temperature following thermal use applies no less in this situation.

VII2h(3). The Radial Discharge Barrel-Assembly as a Separate and Independent Angioplasty Device An object of the invention is to provide a single means for angioplasty and stenting such that the barrel-assembly having been introduced for angioplasty even when stenting had not been planned, stenting can nevertheless proceed without the need for withdrawal and reentry. To proceed with stenting must require no more than to insert the free (extracorporeal, proximal) end of the barrel-assembly into the airgun. Accordingly, to the extent that such compatibility allows, the radial discharge barrel-assembly is devised to be usable as a separate device for angioplasty without the need to reconfigure it in order to allow its use with an airgun to initiate stenting.

Angioplasty-capable barrel-assemblies, to include those incorporating radial projection unit side-shaving or abrading-brush type tool-inserts, means for thermal angioplasty, and combination-forms that incorporate a rotary burr or excimer laser are described below under the section entitled Types of Combination form Barrel-assemblies. Rather than inefficiently and awkwardly tethered by gas and electrical lines, the ablation or ablation and angioplasty-capable barrel-assembly has directly attached to it a small gas cylinder connected through the end or side-socket, as addressed in the section above entitled Engagement of the Barrel-assembly in the Airgun and the section below entitled Barrel-assembly Side-socket.

If piped, the chilled gas is delivered directly to the radial projection unit from the preconnected cylinder through the pipe. In that case, substances previously delivered through the pipe may necessitate the delivery through a service-catheter passed down the pipe. Nonpiped radial projection units must be chilled by a preconnected cylinder and cooling catheter. The direct exposure to the chilling gas makes piped units retract more quickly. For example, the body of the muzzle-head distal to the turret-motor is not made inflatable, various balloons having finger or bristle-like protrusions having long been available.

In use for angioplasty, the barrel-tubes serve with the blood-tunnels, centering devices, and the free insertion or removal down unused barrel-tubes or the central canal of the barrel-assembly of separate tubing of any pliancy, and such use of a cooling catheter as described above in the section entitled Cooling Catheters (Temperature-changing Catheters) as passive stiffeners, the number, material, wall thickness, and diameters of barrel-tubes and absent number, the same variables as pertain to the barrel-catheter representing various variables that contribute to barrel-catheter stiffness, which accordingly covers a wide spectrum. Use independently of the airgun for ablation, angioplasty, or to actuate radial projection unit injection or ejection tool-inserts, for example, requires that the barrel-assembly be provided with onboard and airgun-independent sources of electrical power and control.

Figure 80:
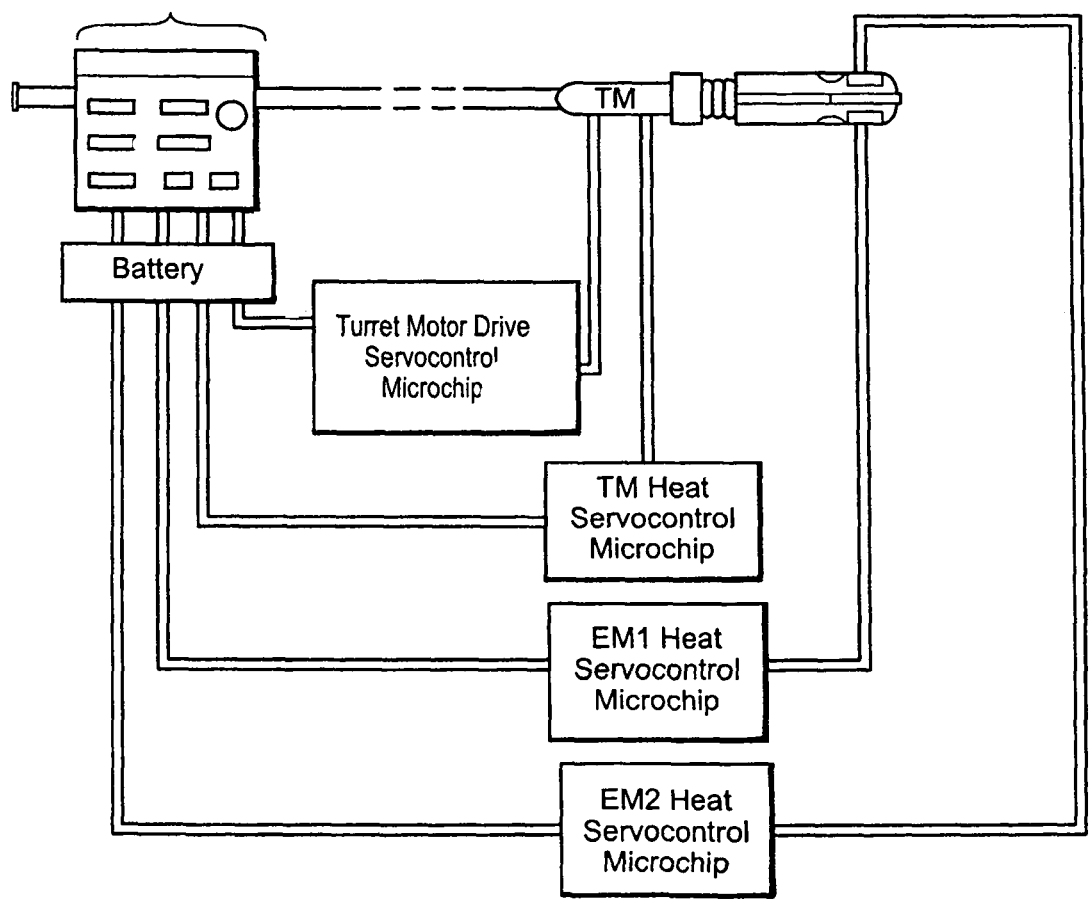
FIG. 80 shows a diagrammatic representation of the control components and connections within the power and control housing of a combination-form ablation or ablation and angioplasty-capable barrel-assembly such as shown in FIGS. 71 and 78, wherein each function is assigned to a separate rather than joint microcontroller, the onboard control panel shown in FIG. 79.

As shown in FIGS. 71*b* and 80, a barrel-assembly for use independently of the airgun is provided with an onboard power and control housing with generally indicated integral control panel, which can be slid along and off the proximal end of the barrel-catheter. When the power and control housing is unique to a specific barrel-assembly, the controls exactly match the non-discharge ablation or angioplasty components to be controlled in that barrel-assembly. A universal power and control housing includes controls for use with any barrel-assembly all of which would actually be needed only with a fully ablation and angioplasty-capable barrel-assembly.

FIG. 79 shows a dedicated control panel on the power and control housing specific to an ablation or angioplasty barrel-assembly having two shaver or abrading brush-type tool-inserts, recovery electromagnet and turret-motor windings that can also be used as heating elements, but not fluid radial projection units, an embolic filter, inmate laser, or rotational atherectomy cutting tool, for example. Except when it is desired to do some 'touching-up' after having initiated discharge, an ablation or ablation and angioplasty-capable barrel-assembly is used to perform an angioplasty manually, with the barrel-assembly independent of an airgun. Rotation and transluminal reciprocation of the radial projection units is normally manual.

The conformation and bristle or individual projection tip type as shown in FIG. 51B determine the kind of action that should be applied. The oscillatory mode of the turret-motor addressed above in the section entitled Turret-motor Operational Modes can be used to increase the vigor or brushing. For the ablation or angioplasty, power to the turret-motor might be needed to heat the windings for thermal angioplasty or to drive the motor in one or more of its oscillatory or vibratory modes in order to increase the vigor of abrasion. Combining or overlapping these different responses so that the motor can be used both to heat and rotate the muzzle-head simultaneously is precluded by the mutually exclusive controls for each function.

Figure 84:
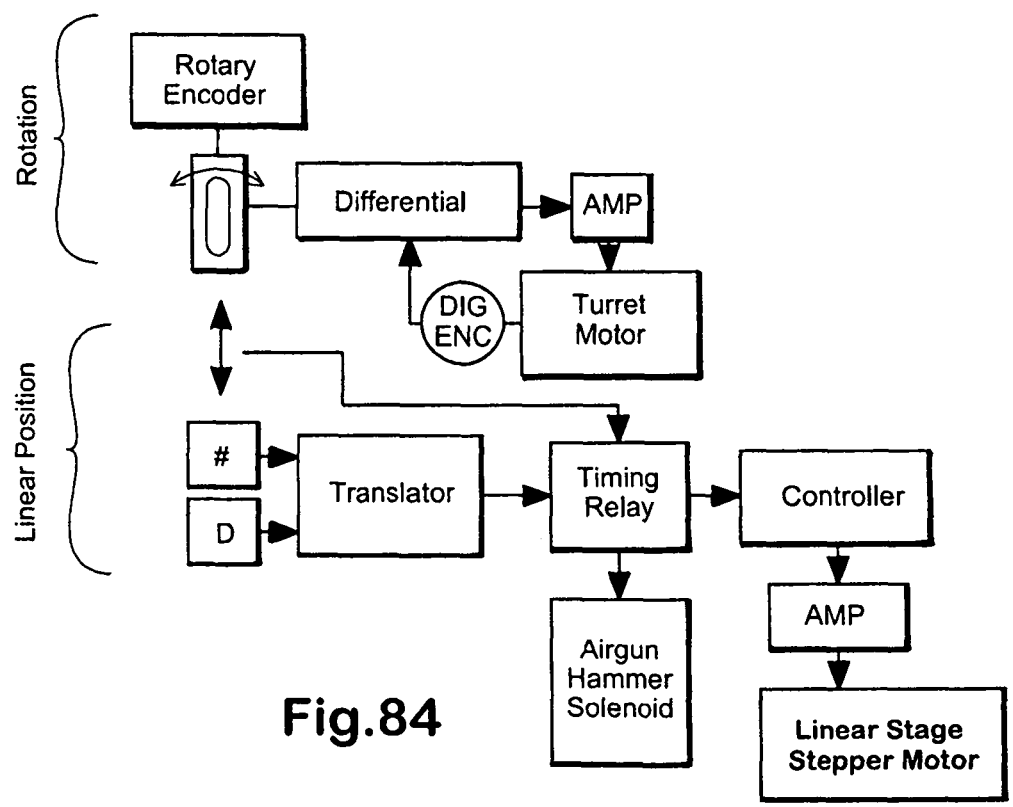
FIG. 84 shows a diagrammatic representation of the timing and positional componentry used to coordinate the automatic discharge as an auxiliary function and instantaneous positioning in transluminal displacement and rotational angle of the muzzle-head of an airgun such as those shown in FIGS. 81 and 82 but equipped with a rotary clip magazine such as those shown in FIGS. 31 and 32 for use with multiple barrel-tubes to allow the accurate implantation of miniballs in a close formation.

The turret-motor is incapable of significant abrasive action in its rotary mode, so that in situations where the barrel-assembly is readily rotated by hand, this mode is not needed in the barrel-assembly as independent from the airgun. Since reciprocal transluminal action is manual as well, no joystick control as shown in FIG. 83 and functionally depicted in FIG. 84 is needed. Instead, as shown in FIG. 79, the angioplasty control panel motor control rocker switch marked 'T-motor' in the upper left-hand corner switches between the heating and oscillatory modes. Any different oscillatory modes programmed are cycled through by re-depressing the right-hand side of the rocker switch and thus not seen in the control panel shown in FIG. 79.

To minimize extracorporeal extension, the barrel-assembly is selected according to the actual intracorporeal length required, the forward drive and sag leveling and stabilizing device described below assisting to avert extracorporeal bends or kinks as would result from the mass posed by the electrical connections or a battery pack and onboard angioplasty control panel toward the free end. Whether connected to an external source of power by a power cord or incorporating an inmate battery pack, ordinarily lithium-polymer with current battery technology, the barrel-catheter can continue as independently powered even when inserted into an airgun.

VII2h(4). Componentry Required for Airgun-Independent Use

An ablation or ablation and angioplasty-capable barrel-assembly is self-contained and capable of performing an ablation or angioplasty as separate and independent of an airgun. An angioplasty-capable barrel-assembly encompasses the capability of an ablation-capable embodiment, but additionally includes gas return channels to prevent gas from entering the bloodstream. This factor of internal structure is not reflected in the controls seen on the onboard control panel, which are the same for both types; however, barrel-assemblies for use in the bloodstream are equipped with a run-ahead trap-filter, as addressed above in the section entitled Embolic Trap Filter in Radial Discharge Muzzle-heads for Use in the Vascular Tree, with the trap-filter control on the panel.

As usually do minimally ablation and angioplasty-capable barrel-assemblies, barrel-assemblies independently capable incorporate radial projection units, addressed below in the section entitled Muzzle-head Radial Projection Units heat-windows, below under Thermal Conduction Windows (Heat-windows) and Insulation of the Muzzle-head Body in Thermal Ablation or Thermal Angioplasty-capable Barrel-assemblies, a trap-filter, and has connectors for fluid lines. In independent use, rotation and transluminal movement with an ablation or ablation and angioplasty-capable barrel-assembly is manual. Fine directional control can be of assistance in controlling slot-configured or directional heat-windows, and oscillatory control for use with radial projection units.

A turret-motor always contained in the muzzle-head, the onboard controls can include the different turret-motor operational modes independently of the motor control electronics in the airgun enclosure. Turret-motor operational modes include rotation, oscillation, and use of the turret-motor field rotating winding to supply heat, as described above in the section entitled Turret-motor Operational Modes. For procedures where speed is of the essence, the additional expense for adding these controls is justified. However, not contained within the barrel-assembly, the use of a linear stage for fine control over transluminal movement will still require insertion into an airgun mounted on a linear stage or into a separate linear stage as addressed below in the section entitled Ablation or ablation and angioplasty-capable Barrel-assembly Control and Onboard Control Panel.

A thermal angioplasty, or vascular thermoplasty, capable barrel-assembly need only be adjusted in the temperature of its heat-windows or other heating elements to allow its use for a thermal ablation, or thermoablation, in a nonvascular ductus. A barrel-assembly that is ablation-capable only is not designed for and is not for use in the vascular tree. The addition of radial projection units to a thermal angioplasty-capable barrel-assembly extends this range of function to include cutting and abrasive tools that can be used without heat for ablation or angioplasty.

Except for limited purpose and minimally-capable barrel-assemblies not provided with an internal power source, such barrel-assemblies can be used independently of the airgun to perform an ablation or angioplasty, and can do so regardless of whether this procedure is followed by conventional stenting by means of inserting the barrel-assembly in an interventional airgun for stenting implantation. Performance of an ablation or an angioplasty imposes no need to withdraw from and reenter through the introducer sheath and irritation to the entry wound; without withdrawing, the proximal end of the barrel-catheter is inserted in the airgun.

For use independently of an airgun, the barrel-assembly must be fully self-contained with distal embolic protective filter, on-board power pack, and ablation-angioplasty control panel. In addition to recovery electromagnets, which can be reoriented in rotary angle with the turret-motor and transluminally by hand or with a linear positioning stage, connection of a barrel-tube or the distal end of the barrel-assembly as a whole to a vacuum (aspiration) pump, and a trap-filter, such a barrel-assembly can recover a miniball through use of the radial projection units to reposition the miniball by means of a brushing action.

Such a barrel-assembly requires insertion into an interventional airgun if and only if to be used for stenting implantation. For thermal ablation of ductus other than vascular, temperatures other than 90 degrees centrigrade must be provided. Combination-form fully angioplasty-capable barrel-assemblies additionally incorporate an atherectomy burr to cut through calcified plaque if necessary or a laser to perform an atherectomy in any type ductus. All fully angioplasty-capable barrel-assemblies incorporate a distal embolic protective trap-filter in the nose that can be remotely deployed or retracted.

VII2h(5). Thermal Ablation and Angioplasty- (Lumen Wall Priming Searing- or Cautery-) Capable Barrel-Assemblies Clinical findings that address the relative value in angioplasty or atherectomy alone, the same plus stenting, or stenting alone, inevitably introduce so many variables as to afford little in the way of clear information. Instead, findings are specific to particular vessels, particular devices, certain adverse sequelae to the disregard of others, particular medical conditions such as a previous acute cardiovascular event of a specific type, details concerning the procedures used, and so on. Some implications of endothelial dysfunction are addressed above in the sections entitled Field of the Invention, Concept of the Extraluminal Stent, Abrupt Closure with Thrombus and Vasospasm, and Medicinal and Medicated Miniballs and Stays, among others. Vulnerable plaque within a delimited segment can pose an imminent threat as demands its elimination regardless of the potential of the limited extent of treated tissue to regain normal endothelial function.

The concept delineated here consists of using statins to expedite the healing of less severely inflamed and metaplastic tissue, with plaque spot-treated to reduce the risk of an acute event. Numerous methods available for spot-treating atheromas (see, for example, Waller, B. F. 1989. "Crackers, Breakers, Stretchers, Drillers, Scrapers, Shavers, Burners, Welders and Melters"—The Future Treatment of Atherosclerotic Coronary Artery Disease? A Clinical-morphologic Assessment," *Journal of the American College of Cardiology* 13(5):969-987), a method that least detracts from eventual healing is clearly to be preferred. A catheteric device with a quickly and independently heated and cooled tip and side windows affords a level of control over the ablative process as to allow only so much exposure to the device as is necessary to eliminate the threat tissue, thus predisposing to eventual recovery to the extent possible.

As addressed herein, thermal angioplasty has the object of destroying vulnerable plaque (see, for example, Virmani, R., Burke, A. P., Farb, A., and Kolodgie, F. D. 2006. "Pathology of the Vulnerable Plaque," *Journal of the American College of Cardiology* 47(8 Suppl):C13-C18; Virmani, R., Kolodgie, F. D., Burke, A. P., Finn, A. V., Gold, H. K., Tulenko, T. N., Wrenn, S. P., and Narula, J. 2005. "Atherosclerotic Plaque Progression and Vulnerability to Rupture: Angiogenesis as a Source of Intraplaque Hemorrhage," *Arteriosclerosis, Thrombosis, and Vascular Biology* 25(10):2054-2061 Kolodgie, F. D., Burke, A. P., Farb, A., Gold, H. K., Yuan, J., Narula, J., Finn, A. V., and Virmani, R. 2001. "The Thin-cap Fibroatheroma: A Type of Vulnerable Plaque: The Major Precursor Lesion to Acute Coronary Syndromes," *Current Opinion in Cardiology* 16(5):285-292) with heat and must be tightly controllable to minimize injury to subjacent layers.

The endoluminal application of heat may also effect repair of the ductus wall (see, for example, Resar, J. R., Wolff, M. E., Hruban, R. H., and Brinker, J. A. 1993. "Endoluminal Sealing of Vascular Wall Disruptions with Radiofrequency-heated Balloon Angioplasty," *Catheterization and Cardiovascular Diagnosis* 29(2):161-167; Kaplan, J., Barry, K. J., Connolly, R. J., Nardella, P. C., Hayes, L. L., and 4 others 1993. "Healing after Arterial Dilatation with Radiofrequency Thermal and Nonthermal Balloon Angioplasty Systems," *Journal of Investigative Surgery* 6(1):33-52; Barry, K. J., Kaplan, J., Connolly, R. J., Nardella, P., Lee, B. I., Becker, G. J., Waller, B. F., and Callow, A. D. 1989. "The Effect of Radiofrequency-generated Thermal Energy on the Mechanical and Histologic Characteristics of the Arterial Wall in Vivo: Implications for Radiofrequency Angioplasty," *American Heart Journal* 117(2): 332-341).

When a calcified cap is present, consideration must be given to whether the cap serves a protective function so that to eliminate it would be counterproductive; extraluminal stenting, especially by means of stays, which avoid the lumen entirely, makes it possible to stent regardless of a moderate amount of more highly calcified plaque without angioplasty or atherectomy. Calcified plaque sufficiently prominent to restrict flow may necessitate a preparatory ablation as by means of a rotatory ablator, which can be built into an angioplasty-capable barrel-assembly.

The trend toward stenting without first performing an angioplasty, usually in the carotid arteries, especially when vulnerable plaque is present (see, for example, Barrera, J. G., Rojas, K. E., Balestrini, C., Espinel, C., Figueredo, A., and 3 others 2013. "Early Results after Synchronous Carotid Stent Placement and Coronary Artery Bypass Graft in Patients with Asymptomatic Carotid Stenosis," *Journal of Vascular Surgery* 57(2 Supplement):58S-63S; García-Nielsen, L., Carreira, J. M., Rabellino, M., Baldi, S., Zander, T., and 3 others 2013. "Hemodynamic Depression in Carotid Artery Stent without Angioplasty," in Spanish with English abstract at Pubmed, *Revista De Neurologia* [Journal of Neurology] 56(4):200-204; Baldi, S., Zander, T., Rabellino, M., González, G., and Maynar, M. 2011. "Carotid Artery Stenting without Angioplasty and Cerebral Protection: A Single-center Experience with Up to 7 Years' Follow-up," *American Journal of Neuroradiology* 32(4):759-763; Rabellino, M., Garcia-Nielsen, L., Baldi, S., Zander, T., Casasola, C., and 3 others 2010. "Non-protected Carotid Artery Stent without Angioplasty in High-risk Patients with Carotid and Coronary Artery Disease Undergoing Cardiac Surgery," *Minimally Invasive Therapy and Allied Technologies* 19(3): 184-188; Leonardi, M., Dall'olio, M., Raffi, L., Cenni, P., Simonetti, L., Marasco, R., and Giagnorio, F. 2008. "Carotid Stenting without Angioplasty and without Protection: The Advantages of a Less Invasive Procedure," *Interventional Neuroradiology* 14(2):153-163;" Pelz, D. M. and Lownie, S. P. 2008. "Letter—Re: Primary Carotid Stenting without Angioplasty," *Interventional Neuroradiology* 14(4):473; Maynar, M., Baldi, S., Rostagno, R., Zander, T., Rabellino, M., Llorens, R., Alvarez, J., and Barajas F. 2007. "Carotid Stenting without Use of Balloon Angioplasty and Distal Protection Devices: Preliminary Experience in 100 Cases," *American Journal of Neuroradiology* 28(7):1378-1383; Lownie, S. P., Pelz, D. M., Lee, D. H., Men, S., Gulka, I., and Kalapos, P. 2005. "Efficacy of Treatment of Severe Carotid Bifurcation Stenosis by Using Self-expanding Stents without Deliberate Use of Angioplasty Balloons," *American Journal of Neuroradiology* 26(5):1241-1248; Nakatani, M., Takeyama, Y., Shibata, M., Yorozuya, M., Suzuki, H., Koba, S., and Katagiri, T. 2003. "Mechanisms of Restenosis after Coronary Intervention: Difference Between Plain Old Balloon Angioplasty and Stenting," *Cardiovascular Pathology* 12(1):40-48; Men, S., Lownie, S. P., and Pelz, D. M. 2002. "Carotid Stenting Without Angioplasty," *Canadian Journal of Neurological Sciences* 29(2):175-179; Harnek, J., Zoucas, E., Stenram, U., and Cwikiel, W. 2002. "Insertion of Self-expandable Nitinol Stents without Previous Balloon Angioplasty Reduces Restenosis Compared with PTA Prior to Stenting," *Cardiovascular and Interventional Radiology* 25(5):430-436;) makes taking measures to avoid disrupting vulnerable plaque using the apparatus for stenting to be described all the more significant.

Initial contact by a muzzle-head with the wall of an atheromatous artery occurs both with an ablation or angioplasty-incapable barrel-assembly and an ablation or ablation and angioplasty-capable barrel-assembly. Barrel-assemblies are usually selected to flush-fit the segment of the lumen to be treated and are thus frequently in contact with the lumen wall. Furthermore, though blood-grooves and other passages ameliorate the problem, the muzzle-head substantially obstructs the lumen, promoting means and techniques to hasten completion of the procedure, such as the providing multiple barrel tubes and automated discharge at preselectable specific intervals. In effect, mere contact with the barrel-assembly as it passes along the lumen wall exerts a weak or deficient angioplasty effect, in that it can release debris, making the use of a trap-filter requisite.

The combination of contact with the lumen wall and haste would risk the release of debris more were not an onboard trap-filter incorporated. Accordingly, using the means described herein to stent without a previous angioplasty is not recommended, and using the means described herein to perform the angioplasty assumes the use of the onboard trap-filter. These include providing the muzzle-head with a nose-cap heat-window that is heated by running current through the windings of both recovery electromagnets. Since a distal embolic protective trap-filter would also be capable of disrupting plaque, none is deployed when the presence of vulnerable plaque is suspected if not confirmed. A nose-cap heat-window is thus necessary in all but ablation or angioplasty-incapable Barrel-assemblies which are used only to stent implant where plaque is not present.

In addition to a nose heat-window, a fully angioplasty-capable barrel-assembly usually has heat-windows that conduct heat produced by passing current through the windings of the turret-motor. Whereas the recovery electromagnet nose heat-window must deliver heat round and about, those over the turret-motor in an angioplasty-capable barrel-assembly are in the form of circumferential or arcuate slits, slots, or rectangles that can be directed toward eccentric plaque or other type lesions. Because temperatures other than 90 degrees centigrade tend to be thrombogenic, the insulation surrounding heat-windows whether omnidirectional or directional (eccentric) must minimize the generation of thrombogenic heat in the gradient areas bounding the heat-windows.

Because of the severe restriction in thickness, perfect insulation cannot be achieved; however, because the 90 degree focal area continuously passes over the lumen wall, areas within the cooling gradient bounding the heat-window within the segment of the artery to be treated are instantly exposed to the target temperature. Thus, the insulation is made as effective as possible but not perfect. There will always be end of treatment areas where the muzzle-head will not pass, and thrombolytic medication, which is always to be administered in the smallest dose effective, must be relied upon to protect against thromboembolisms. The same applies when only one recovery electromagnet or the turret-motor are used directionally to treat eccentric lesions in a blood vessel.

A probability if not the confirmation of vulnerable plaque warrants additional protection against the release of atheromatous detritus. This is attained by incorporating a distal embolic protective filter. Although not fully angioplasty-capable, such a barrel-assembly can and therefore is made capable of performing a thermal angioplasty independently of an airgun. Since it follows the nose-cap thermal window at an interval, making the turret-motor heatable is subsidiary in the preventing ruptures. To function as a thermal angioplasty- (lumen wall priming searing- or cautery-) capable barrel-assembly requires connection to either a. The power supply using the side-socket or plug and socket arrangement shown in FIG. 75 with a power cord of sufficient length to allow freedom of movement, or b. That the barrel-assembly be made completely separate and independent of an airgun with on-board power and controls to perform a thermal angioplasty.

Both configurations allow access to a service-channel whether the central canal or a spare barrel-tube to introduce a catheter down to a muzzle-port in order to deliver medication or a lubricant. Whether power is derived through connection to the airgun power supply or from an on-board battery pack, to allow its use while physically separated from the airgun, an ablation or ablation and angioplasty-capable barrel-assembly is provided with an on-board thermal angioplasty control panel, as addressed below in the section entitled Ablation or ablation and angioplasty-capable Barrel-assembly Onboard Control Panel.

In barrel-assemblies for use not limited to atheromatous arteries, thermal ablative temperatures other than 90 degrees centigrade are provided. Once completed, the proximal end of the barrel-assembly is engaged in the airgun and implantation initiated. The equal applicability of semi-tethered and nontethered means for drawing power reflects the transitional status of such a barrel-assembly as between angioplasty functionality that is slavish or is independent, the choice in componentry depending upon whether the barrel-assembly is to be usable independently.

VII2h(6). Ablation and Ablation and Angioplasty-Capable Barrel-Assembly End-Sockets An end-socket is the end-plate of a barrel-assembly, which normally used to establish barrel-tube and electrical (but not fluid) line connections when engaged in the airgun chamber as a kind of compound jack or plug, is used instead to make fluid line as well as electrical connections when removed from the airgun. Electrical contact is made by engagement in the airgun chamber, fluid attachment necessitating removal from the airgun. Outside the airgun, an end-socket allows connection to components in the muzzle-head defined in the glossary below, such as radial projection units, heat-windows, and a trap-filter, to a source of electrical power and/or various kinds of fluid moving devices, such as an aspiration pump, cold air gun, or an auxiliary device placed in the central canal or a barrel-tube. End-sockets not automatically closed by a one-way swing-away cover also serve as gas pressure relief outlets.

Ablation or ablation and angioplasty-capable and combination-form barrel assemblies are generally equipped with a side-socket to allow fluid and electrical connection to various attachments whether the barrel-assembly is or is not inserted in the airgun. Unlike a side-socket, connection through an end-socket requires removing the barrel-assembly from the airgun, disabling discharge, so that discharge and ablative functions cannot be freely interspersed. Electrical and fluid connections to the end-plate as a socket, or end-socket, is by means of miniature connectors. Furthermore, not requiring a configuration that allows connection within the airgun chamber, the side-socket is flexible in configuration. That is, whereas connection to an end-socket requires that the connecting cord or cable be of accommodating conformation, in a side-socket, the socket can be adapted to participate in connection. See also side-socket, service-catheter.

VII2h(7). Ablation and Ablation and Angioplasty-Capable Barrel-Assembly Side-Sockets A side-socket is a receptacle in the side of a barrel-assembly power and control housing that allows connection of components or tubes in the muzzle-head to a source of electrical power and/or various kinds of fluid moving devices, such as an aspiration pump or cold air gun or in a combination-form barrel-assembly, for admitting or allowing connection to an auxiliary device in the central canal without regard to whether the barrel-assembly is engaged in the chamber of an airgun. Unlike an end-socket, it does not establish connection within the airgun chamber, and can therefore incorporate collars or size adapters, for example, to accommodate input lines. Side-sockets not automatically closed by a one-way swing-away cover also serve as gas pressure relief outlets.

Depending upon the specific barrel-assembly, access can be to the central canal, one or more barrel-tubes for use as service-channels or service-catheters, or both. Fluid connections may require that the end-plate at the proximal end of the barrel-assembly be capped. Since placement thus allows use independently and regardless of engagement in the airgun, cooling or heating air or gas can be delivered whether the barrel-assembly is separate from the airgun or during discharge; side entry, side entry socket. See also end-socket, service-catheter. An ablation or angioplasty-incapable barrel-assembly, such as a simple pipe, can be used apart from an airgun for bulb or syringe pipetting or connection to a vacuum pump for aspiration or to deliver medication, but is otherwise always used while inserted in an airgun.

Therefore, these barrel-assemblies lose little utility when the electrical connection needed to power the recovery electromagnet is established upon mechanical engagement of the barrel-assembly with contacts in the end-plate as shown in FIG. 72 in an airgun chamber as shown in FIG. 74. Removal of a simple barrel-assembly from the airgun for aspiration or fluid delivery discontinues only its functions of miniball discharge and recovery, which are not needed for these purposes; the delivery of liquid medication during discharge requires a multibarrel-tube ablation or ablation and angioplasty-capable barrel-assembly, usually by insertion of a service-catheter. The delivery of medication with a simple pipe is limited to the use of medication and medicated miniballs.

Since a simple barrel-assembly need not be usable in multiple ways apart from or while inserted into the airgun, access to its proximal end for connection to various attachments offers no benefit. However, an ablation or ablation and angioplasty-capable barrel-assembly, which can be used to perform an angioplasty that might be followed by conventional stenting so that it is never inserted into an airgun, for example, improves in utility the more it can be used independently of the airgun. Moreover, side connections allow any functions connected thus to continue whether the barrel-assembly is inserted into the airgun or not. For this reason, in such a barrel-assembly, it is best to provide electrical connectors or both electrical and hosing connections at the side and distal enough as not to interfere with insertion of the barrel-assembly into the airgun.

Because it does not obstruct the proximal end of the barrel-assembly and thus does not interfere with insertion down the barrel of the airgun and engagement in its chamber, a side-socket allows auxiliary devices, such a rotary burr or laser atherectomy cable, but primarily a line delivering cold air, to remain connected even during discharge. The side-socket, like an end-plate socket, must have an adjacent one-way pressure relief valve or adjustable vent, which is usually mounted in a circular plate that seen side-on is arcuate to fit against the side of the barrel-assembly. A side-socket can be incorporated into any barrel-assembly but is most useful in an edge-discharge barrel-assembly, which can be made with built in cooling catheter that directs cold (or hot) air against the proximal face and wall of a nose-window.

Alternatively, an edge-discharge barrel-assembly can use attachments, so that the socket passes an atherectomy cable or cooling catheter that is introduced at the socket and fed or snaked down to the front (distal) end so that differently equipped combination form barrel-assemblies can be assembled using the same basic or shell barrel-assembly. An end-plate that includes an end-socket allows almost every form of use but not with continued access to ablative or angioplasty functions when the barrel-assembly must be inserted into the airgun to initiate ballistic discharge, at which time any attachments at the proximal end (rear) must be removed. Without a side-socket, the intima cannot be chill stabilized during discharge, for example.

VII2h(8). Barrel-Assembly Power and Control Housing

Whereas a minimally ablation or ablation and angioplasty-capable barrel-assembly is dependent upon the airgun for power and control, an ablation or ablation and angioplasty-capable barrel-assembly, whether a combination-form, must be usable independently of an airgun. This necessitates a self-contained or onboard source of power and control. In order to allow a combination-form radial projection catheter of matching size, to be slid over the barrel-catheter of such an independent apparatus, the power and control housing must be disconnectable. The power and control housing of an ablation or angioplasty-capable barrel-assembly or radial projection catheter can be slid along splines around the barrel or projection-catheter integral to the tubing extrusion.

Electrical connection of the working components to the airgun power supply and/or battery pack in the housing is maintained by contacts lining the catheter hole in the housing that ride along contacts glued into the valleys between the splines. In larger barrel-assemblies for use in the gastrointestinal tract, for example, some or all electrical connection can be internal to the housing. Fluid connections generally enter through a side-port and travel through the center of the barrel-catheter or radial projection catheter tubing. The barrel-assembly is equipped with an ambidextral hand-grip for grasping and to serve as a torquing device or torquer. The hand-grip is coated for traction, such as with vinyl or a nonallergenic synthetic rubber. In an ablation or ablation and angioplasty-capable barrel-assembly, the hand-grip contains a battery within and mounts an independent angioplasty control panel on the outside.

The battery pack in an ablation or ablation and angioplasty-capable barrel-assembly hand-grip is preferably of the lithium polymer type and concentrically elongated along the barrel-catheter for high storage capacity without being obtrusive. Also with respect to ablation or ablation and angioplasty-capable barrel-assemblies, a side-socket, as addressed above in the section entitled Barrel-assembly Side-socket, is preferred to an end-socket. Placed along the barrel-catheter or through the hand-grip and thus beyond or distal to the airgun muzzle when the barrel-assembly is inserted into the airgun, a side-socket allows the cabling, piping, or wires of external apparatus used during the ablation or angioplasty to remain connected whether the barrel-assembly is inserted into or used separately from the airgun. External apparatus includes gas cylinders, endoscopy viewing screens, laser control consoles, and so on.

VII2h(8)(a). Connection of the Power and Control Housing to the Airgun

The power and control housing includes a battery pack, eliminating the need for connection to the airgun power supply. Mechanical connection of the power and control housing to the airgun in ablation or angioplasty-capable and minimally-capable barrel-assemblies and radial projection catheters when applicable is by means of a portion of barrel-catheter extending out the proximal side of the housing which is equal in length to the airgun barrel. Connection to the airgun muzzle is by means of a twist to lock connector mounted to the front of the airgun muzzle, as addressed above in the section entitled Twist-to-stop and Lock Connector (Twist Lock Connector, Keyed Spring Lock Connector). An ablation or ablation and angioplasty-capable barrel-assembly with its housing removed (slipped off) or disconnected is equivalent to a minimally ablation or ablation and angioplasty-capable barrel-assembly. The power and control housing of a radial projection catheter need never be disconnectable or slidable.

VII2h(8)(b). Slidable Ablation or Ablation and Angioplasty-Capable Barrel-Assembly Power and Control Housing An ablation or ablation and angioplasty-capable barrel-assembly should be optimally navigable, usable independently of an airgun, remain insertable in the airgun whether to resume implantation discharge and/or to gain use of the linear positioning stage, and allow sliding over the barrel-catheter with a combination-form radial projection catheter at any moment. These desiderata recommend the elimination of any component that would lessen steerability or trackability, impede removal or insertion in the airgun, or interfere with placing the radial projection catheter. A practical ablation or ablation and angioplasty-capable barrel-assembly allows both quick insertion and removal from the airgun to the rear and quick disconnection and removal of a radial projection catheter to the fore.

A barrel-assembly power and control housing affixed at a distance along the barrel-catheter with a rear or proximal length of barrel-catheter for insertion in the airgun would not move on introduction into and withdrawal from the body and would require disconnection from the forward or distal portion of the barrel-catheter to allow insertion in the airgun by means of a plug type connector that would demand placing joints in the barrel-tubes. A housing at some point forward thereof, or distal to the proximal or end of the barrel-catheter inserted in the airgun, would likewise require disconnection by a plug type connector that would demand placing joints in the barrel-tubes.

Moreover, when introduction of the barrel-assembly commenced, a power and control housing hand-grip fixed in position would have the extracorporeal length of the barrel-catheter to its fore (distally) making use awkward and inviting excessive bowing or buckling if not kinking over the intervening length. Disconnectability of the power and control housing allows a combination-form radial projection catheter to be advanced over the barrel-assembly barrel-catheter midprocedurally whether before or after entering the body. Incorporating fluid radial projection units in narrower muzzle-heads and about narrower barrel-catheters is discounted as demanding an increase in gauge, reducing the flexibility of the barrel-assembly, requiring points of fluid connection that unlike electrical connections are immobile and obstructive, and demanding the use of plug type connection that requires placing a joint in the barrel-tube or tubes.

An ablation or ablation and angioplasty-capable barrel-assembly does not require onboard fluid control, because: 1. While the barrel-assembly is not inserted in the airgun, an external source of a gas or liquid can be fed through an end-port in the terminal plate into a barrel-tube for emission in the lumen, 2. Whether to lubricate passage or administer medication or another therapeutic liquid substance, the electrically operated radial projection units in the muzzle-head can use spring discharge syringe tool-inserts to eject the liquid substance in the lumen or inject it into the lumen wall, and 3. A combination-form radial projection catheter matched in gauge and length to the barrel-assembly is not inserted in the airgun, is passable over the previously situated barrel-catheter used as a guidewire, can thus readily accommodate a fluid circuit or circuits with power and controls for these within its own power and control housing, and 4. The projection catheter can be advanced over or removed from the barrel-catheter at any time before or after the barrel-assembly is inserted in the airgun and the end-port is not in use.

Thus, for the radial projection units in the muzzle-head, purely electrical operation is not just necessary but superior. Muzzle-head units are favorably limited to electrical units, a need for fluid units relegated to a matching radial projection catheter. Electrically operated radial projection units about the muzzle-head can use tool-inserts that can perform any endoluminal procedure that does not involve the continuous delivery or removal of an ejectant or injectant. For example, electrical/fluid system-neutral ejection syringe tool-inserts, or spring release syringe ejectors, can be used to release a lubricant to expedite navigation. By pushing or pulling the barrel-catheter through it, a slidable electrical power and control housing can be moved as the barrel-assembly is introduced and withdrawn and thus kept at a consistent distance from the introducer sheath.

The housing includes a levered cam detent that allows it to be slid to and locked in any position along the barrel-catheter. Holding the housing stationary with the detent open, the barrel-catheter can be slid through it, while locking the housing in position allows its use as a grip. Upon withdrawal, a power and control housing hand-grip that is fixed in position along the length of the barrel-catheter increases the extracorporeal length of the barrel-catheter between the hand-grip to the introducer sheath. The chances for kinking are increased when a barrel-assembly having a longer barrel-catheter than necessary is used. Kinking or creasing the barrel-tubes disallows the use of these for further discharge, necessitating withdrawal to replace the barrel-assembly.

More specifically, when disengaged from the airgun and the housings stand in ganged relation with the power and control housing of the barrel-assembly held in place, the power and control housing of the radial projection catheter can be pushed forward against the rear of the muzzle-head carrying the barrel-assembly forward. Provided the barrel-assembly housing is held and its detent in closed position, when the previously advanced radial projection catheter is pulled back, the barrel-assembly will remain in the forward position. Holding the radial projection catheter housing in place while pushing the barrel-catheter through the slidable power housing of the barrel-assembly advanced the muzzle-head through the stationary radial projection catheter.

The housing is given an overall conformation that includes bilaterally symmetrical finger indentations or a pistol grip for ambidextral grasping and has the control panel for the barrel-assembly components mounted to its upper surface. Electrical contacts inside the housing collar clutch about the barrel-catheter. The inward faces of these contacts slide on separate strips of silver oriented longitudinally about the periphery of the barrel-catheter to provide continuous electrical contact during movement. A sliding housing is used only on barrel-assemblies, not on radial projection catheters, and includes only electrical, not fluidic components. Neither does it include electrical controls for a separate housing containing a fluid pump and reservoir. A matching combination-form radial projection catheter complements the barrel-assembly with a stationary power and control housing that can contain onboard fluid components.

With the barrel-assembly removed from the airgun, lubrication, irrigation, and aspiration, for example, can be accomplished through an end-socket connected to a barrel-tube or tubes. When not engaged in an airgun, a barrel-assembly with an end-socket can be connected to an external source of gas or liquid. A radial projection catheter with a side-socket in its power and control housing also allows connection from an external source of a gas or liquid to one or more of its fluid tool-inserts. The use of a power cord in lieu of a battery, whether connecting to the airgun or to another power supply, is not preferred as hindering free movement considerably more than does the weight and size increase that results from including the batteries onboard.

For separate and independent function, as well as logical and intuitive consistency to ward off human error, the airgun, barrel-assembly, and combination-form radial projection controls not duplicated on one of the other apparatuses are kept with the respective apparatus. For example, the linear positioning stage controls go to the airgun and are on the airgun. When a joystick or cyclic-type control is used, rotation of the turret-motor is by rotating or sidewise motion and control of the linear stage by push-pull movement. The control panel, and contains the control circuitry and power source, usually a thin film or lithium-polymer battery. The controls omit those related to discharge, which go to the airgun, and include those used for separate use of the barrel-assembly.

Controls for radial projection units in ablation or angioplasty minimally capable barrel-assemblies, which do not have a power and control housing for use apart from an airgun are included in the airgun control panel, so that use of the airgun with a more capable barrel-assembly will result in duplicate controls for barrel-assembly functions. For optimal flexibility and use by an assistant, barrel-assembly controls on the airgun are not disabled when available on the barrel-assembly. Functions involved both in ballistic discharge and separate use of the barrel-assembly, such as setting the rotatory angle of radial projection units in the muzzle-head, are duplicated in the airgun and barrel-assembly control panels. An angioplasty-capable barrel-assembly is thus made so that the hand-grip can be slid over any portion of the barrel-catheter likely to become extracorporeal during any given procedure.

Since the barrel-assembly must be immediately insertable into the airgun to commence implant discharge, the conductors cannot, for example, exit at the end-plate and fold around to a housing that slides over the barrel-catheter. An arrangement of sliding contacts (electrical contact shoes, paddle shoes, brushes, wire slide-shoes) within the housing collar, one for each electrical connection required, are directed toward the central axis. These contacts slide over longitudinal linear contact strips (linear electrical contacts, hot rails, linear slip-'rings') about the circumference of the barrel-catheter that run along the outer surface of the barrel-catheter at circumferential intervals one for each electrical connection required so that components within the barrel-assembly to function in unison share such a contact pair.

The contact strips are made of silver or coated with sputter deposited micrometric silver islands (Salomoni, R., Léo, P., Montemor, A. F., Rinaldi, B. G., and Rodrigues, M. 2017. "Antibacterial Effect of Silver Nanoparticles in Pseudomonas aeruginosa," *Nanotechnology, Science and Applications* 10:115-121; Pérez-Tanoira, R., Pérez-Jorge, C., Endrino, J. L., Gomez-Barrena, E., Horwat, D., Pierson, J. F., and Esteban, J. 2012. "Bacterial Adhesion on Biomedical Surfaces Covered by Micrometric Silver Islands," *Journal of Biomedical Materials Research. Part A* 100(6):1521-1528; Monteiro, D. R., Gorup, L. F., Takamiya, A. S., Ruvollo-Filho, A. C., de Camargo, E. R., and Barbosa, D. B. 2009. "The Growing Importance of Materials that Prevent Microbial Adhesion: Antimicrobial Effect of Medical Devices Containing Silver," *International Journal of Antimicrobial Agents* 34(2):103-110; Böswald, M., Mende, K., Bernschneider, W., Bonakdar, S., Ruder, H., Kissler, H., Sieber, E., and Guggenbichler, J. P. 1999. "Biocompatibility Testing of a New Silver-impregnated Catheter In Vivo," *Infection* 27 Supplement 1:S38-S42; Guggenbichler, J. P., Böswald, M., Lugauer, S., and Krall, T. 1999. "A New Technology of Microdispersed Silver in Polyurethane Induces Antimicrobial Activity in Central Venous Catheters," *Infection* 27 Supplement 1:S16-S23; Oloffs, A., Grosse-Siestrup, C., Bisson, S., Rinck, M., Rudolph, R., and Gross, U. 1994. "Biocompatibility of Silver-coated Polyurethane Catheters and Silver-coated Dacron Material," *Biomaterials* 15(10): 753-758).

Copper contact strips are not used (Mandinov, L., Mandinova, A., Kyurkchiev, S., Kyurkchiev, and 11 others 2003. "Copper Chelation Represses the Vascular Response to Injury" *Proceedings of the National Academy of Sciences of the United States of America* 100(11):6700-6705). The contact strips must remain flush to the outer surface of the barrel-catheter and not separate when the the barrel-catheter is flexed. Bonding the strips to the barrel-catheter, which will be made of or have an outer coextruded surface of a fluoropolymer or polyamide, requiring surface preparation to be bonded is by etching. (see also Brewis, D. M. and Dahm, R. H. 2006. *Adhesion to Fluoropolymers, Report* 183, 16:3; Shropshire, England: Smithers Rapra Publishing; Maynard W. C. 1996. "Process for Bonding a Fluoropolymer to a Metal," *Metal Finishing* 94(6):161). Following surface preparation by Acton Technologies, Inc. Fluoro-Etch® or W.L. Gore® and Associates, Inc. TetraEtch® or blown-ion air plasma type corona, or flame surface treated, the applicable bonding agents include NuSil Technologies MED-1037 or MED3-4013.

A sliding hand-grip is provided by bringing the conductors within the barrel-assembly to end-plate terminals that match the terminals on the inside of a transparent friction fitting removable cap keyed to align the electrical terminals. The separately insulated bundled conductors leading from these terminals continue through the top of the cap in a coiled extension or power cord that leads to the hand-grip in slidable encircling relation to the barrel-catheter. The cap contains holes to allow access through a spare barrel-tube or the central canal as a service-channel Thus, for example, when access through the central canal to the muzzle-head is desired, the power cord emerges out of the top of the cap off-center. The cylindrical passageway through the center of the hand-grip is frictionally fitted for positionally stable sliding movement along the barrel-catheter.

VII2h(8)(c). Universal Barrel-Assembly Power and Control Housing

Airgun-independent incapable barrel-assemblies such as simple pipes and ablation and angioplasty-incapable radial discharge barrel-assemblies have no electrical components beyond a turret-motor and recovery electromagnets, which remain in use during discharge when the barrel-assembly is engaged in the airgun. Minimally-capable barrel-assemblies generally include heat-windows and radial projection units. To power the turret-motor and recovery electromagnets, all barrel-assemblies must draw power during discharge. For reasons of economy, airgun-independent incapable barrel-assemblies are made to draw power continuously through connection to the airgun power supply. Airgun-independent incapable and capable barrel-assemblies of like diameter can use the same removable slidable power and control housing, and insert adapters allow the same power and control housing to be shared among barrel-assemblies of different diameter.

Thus, considerable economy can still be attained through the use of a shared power and control housing, especially when provided with diameter adapters. However, because it must include the controls for the numerous different components incorporated into different barrel-assemblies, a universal power and control housing, addressed below in the section entitled Universal Barrel-assembly Power and Control Housing, tends to reduce any economic advantage, the more so because unlike a plurality of simpler housings, it can be used with only one barrel-assembly at a time. During discharge, the turret-motor and recovery electromagnets serve discharge and are therefore controlled from the discharge control panel mounted to the airgun, connection to the airgun power supply as depicted in FIGS. 72 and 74 or FIG. 75.

When connection to the airgun power supply is by contact within the airgun chamber when the barrel-assembly is engaged as depicted in FIGS. 72 and 74, disconnection upon withdrawing the barrel-assembly to slide on the power and control housing causes a temporary loss of power, whereas when connection is through a cable as shown in FIG. 75, the housing can be slid on making connection while the barrel-assembly continues to draw power from the power supply. In airgun-independent capable embodiments, the cost for additional onboard control electronics makes the cost for a dedicated power source proportionally negligible. Depending upon the application, the miniature embolic filter (filter-trap, trap-filter) shown in FIG. 50 as parachute or umbrella-shaped might just as easily be windsock, drag, or trawler type fishing net-shaped.

VII2h(8)(d). Rechargeable Battery Pack Local to the Electrical Terminals

An ablation or ablation and angioplasty-capable barrel-assembly must be usable independently of the power supply in the airgun. To provide the longest life with the least weight, the battery pack onboard the barrel-assembly is of the rechargeable thin-film, silver-zinc, lithium-ion, or lithium-ion polymer type (see, for example, Son, I. H., Park, J. H. 3, Park, S., Park, K., Han, S., and 5 others 2017. "Graphene Balls for Lithium Rechargeable Batteries with Fast Charging and High Volumetric Energy Densities," *Nature Communications* 8(1):1561; Cheng, Q., Okamoto, Y., Tamura, N., Tsuji, M., Maruyama, S., and Matsuo, Y. 2017. "Graphene-like graphite as Fast-chargeable and High-capacity Anode Materials for Lithium Ion Batteries," *Scientific Reports* 7(1):14782; Hu, P., Wang, H., Yang, Y., Yang, J., Lin, J., and Guo, L. 2016. "Renewable Biomolecule-based Full Lithium-Ion Batteries," *Advanced Materials* (Deerfield Beach, Fla.) 28(18):3486-3492; Zhang, R., Chen, Y., and Montazami1, R. 2015. "Ionic Liquid-doped Gel Polymer Electrolyte for Flexible Lithium-Ion Polymer Batteries," *Materials* (Basel, Switzerland) 8(5):2735-2748; Ben Amar, A., Kouki, A. B., and Cao, H. 2015. "Power Approaches for Implantable Medical Devices," *Sensors* (Basel, Switzerland) 15(11):28889-28914; Mond, H. G. and Freitag, G. 2014. "The Cardiac Implantable Electronic Device Power Source: Evolution and Revolution," *Pacing and Clinical Electrophysiology* 37(12):1728-1745; Hassoun, J., Bonaccorso, F., Agostini, M., Angelucci, M., Betti, M. G., and 6 others 2014. "An Advanced Lithium-ion Battery Based on a Graphene Anode and a Lithium Iron Phosphate Cathode," *Nano Letters* 14(8):4901-4906; Bock, D. C., Marschilok, A. C., Takeuchi, K. J., and Takeuchi, E. S. 2012. "Batteries Used to Power Implantable Biomedical Devices," *Electrochimica Acta* 84).

VII2h(9)(e). Ablation and Ablation and Angioplasty-Capable Onboard Barrel-Assembly Control As addressed in the section above entitled Minimally Ablation or Ablation and Angioplasty-capable Barrel-assembly Control Panel, insertion in an airgun mounted on a motional control platform allows the rate of transluminal exposure to ablative action to be closely controlled, but interferes with free manipulability, which requires removing the barrel-assembly from the airgun or use of an air pistol. When, as during an ablative process, the rate of transluminal movement is significant, a minimally ablation or ablation and angioplasty-capable barrel-assembly connected to a pistol affords free but not tightly controlled movement. Situations that demand both close control over discharge and the rate of transluminal movement require the combination of a barrel-assembly that can be freely manipulated and engaged in a positional control stage-mounted interventional airgun as necessary.

For this reason, the barrel-assembly is made to be usable independently of an airgun but insertable into an airgun for machine controlled transluminal movement at any time. The need for precise transluminal motion exceptional, the transluminal axis of the joystick control, as addressed in the section that follows, is made operational only when the barrel-assembly is engaged in an airgun. Any tethering during an ablation or angioplasty consists of a laser or rotational atherectomy burr cable in a combination-form barrel-assembly. Electrically operated components other than a linear stage are wholly contained on-board the barrel-assembly, and means for chilling the barrel-assembly itself with or without a cool air catheter or for performing a cryoablation (cold air gun, $CO_2$ cartridge) are with most embodiments connected through a side-socket and attached to the proximal end-plate.

Transluminal positioning of the muzzle-head for discharge that is not demanding of precision, as in moving to or between more widely separated starting positions, can be controlled by hand; whenever use of the linear stage for achieving millimetrically uniform incremental positioning is not necessary, the barrel-assembly can be removed from the airgun for free manipulation. Whether the barrel-assembly is controlled by hand or the linear stage, the forward drive and sag leveling and stabilizing device is used to prevent deflection of the extracorporeal barrel-assembly. When numerous starting positions for finer positioning are relatively distant, it is quicker to push or pull the airgun with the barrel-assembly inserted than to intermittently remove the barrel-assembly for direct manual control and reposition the airgun for insertion of the barrel-assembly.

A linear stage having an overall travel sufficient to allow transluminal movement over a greater distance allows coarse (approximate, rough) positioning up to one or more widely separated starting positions without the need for handling the barrel-assembly. The joystick is used for continuous forward (distad, advancing) or backward (proximad, withdrawing, retracting) moving to the starting point. If the stage travel is too short for continuous operation thus, then the starting position is advanced to by manually moving the barrel-assembly, usually while removed from engagement with the linear stage or airgun mounted thereon.

If reaching a satisfactory starting point by hand is likely to result in over and undershots, then once the approximate starting point is reached by hand, exactitude in transluminal positioning to reach the starting point is accomplished with the step-number and step size (distance, interval, increment) control knobs on the angioplasty control panel, the joystick used to indicate whether the movement is forward or backward. These same controls are used for individual successive discharges across the segment to be treated, each transluminal repositioning being followed by a discharge.

A uniform close formation of miniballs is achieved through use of the step number and step size control knobs with the joystick in discharge mode so that each step or a successive number of steps is followed by a discharge. Unless combined with an angioplasty in the same pass, the rate of transluminal movement during discharge is not critical. For an angioplasty, whether thermal, cryogenic, and/or with radial projection tool-inserts, the rate of movement is a basic ablative action exposure factor, hence, critical. Controller-drives such as those cited above, to include, for example, a Baldor Flex+Drive II allow control of linear stage speed. The speed must be suitable for the specific ablative process.

VII2h(9)(f). Ablation and Ablation and Angioplasty-Capable Barrel-Assembly Onboard Control Panel Devised for use independently of an airgun an ablation or ablation and angioplasty-capable barrel-assembly is equipped with an onboard control panel that includes the controls needed for an ablation or angioplasty. Since the latter may include the need to use the onboard actuators, the onboard angioplasty control panel includes positional controls. In addition to on-off and stop action switches, the controls required on the control panel of an ablation or ablation and angioplasty-capable barrel-assembly include those for:

1. Turret-motor temperature (current).
2. Electromagnet winding 1 temperature (current).
3. Electromagnet winding 2 temperature (current).
4. Turret-motor rotation (typically by means of a digital encoder manually rotated with a knob having a pointer that moves over an upper semicircular calibration with apical or centered 0-point and marked off in 5 degree increments to either side).
5. Radial projection unit tool-insert 1 deployment (release, extension, unstow)-retraction (recovery, stow).
6. Radial projection unit tool-insert 2 (or if more than 2, then the appliable number) deployment (release, extension, unstow)-retraction (recovery, stow).
7. Trap-filter (release, extension, unstow)-retraction (recovery, stow); and possibly.
8. An on-off switch to control a warning lamp on the control panel that flashes when motion sensors on the muzzle-head detect movement while the radial projection units are extended.

If, for example, the tool-inserts are used to remove diseased tissue from alongside the lumen wall by manual reciprocation of the muzzle-head over the lesion, then the radial projection units are not retracted by switching on the motion sensor circuit. The need for rotation of the muzzle-head arises when the turret-motor heat-window may be in the form of a slot or slit, hence directional, and because the radial projection tool-inserts may be different and the lesion eccentric. Since more angioplasty-capable barrel-assemblies are used manually before insertion into and while separate from the airgun, the on-board control panel does not have a control for the linear positioning table, which is used for the precise intraluminal positioning required for higher density implantation.

A vortex tube cold or hot air gun or cryogenic gas ($CO_2$ or $NO_2$) cartridge connected to the back end of the barrel-assembly will usually have controls for these mounted on those devices, as will the laser, atherectomy, or thrombectomy devices incorporated into combination-forms as described below under the section entitled Through-bore or combination form Barrel-assemblies: Barrel-assemblies which Accommodate or Incorporate Means for Ablation, Thrombectomy, Atherectomy, or Atherotomy and/or Endoscopy. Within a given segment of about 15 centimeters, endoluminal advancement and withdrawal is accomplished with the minimal capability barrel-assembly in the airgun using the linear stage.

An intermediate capability barrel-assembly is generally used for ablation or angioplasty prior to insertion into the airgun and therefore has an on-board power and control housing mounting the separate ablation or ablation or angioplasty control panel. A power and control housing made to be used with the barrel-assembly includes only the controls needed for that barrel-assembly, hence, fewer than would be required in a fully capable barrel-assembly control panel. A control panel on a universal barrel-assembly power and control housing usable with any radial discharge barrel-assembly must include the controls for the components in any one of these.

FIG. 71b shows barrel-assembly power and control housing 163 with a graphically depicted onboard control panel such as that more fully shown in FIG. 79, mounted at the side for illustrative purposes; more often, for optimal operator viewability, the control panel is mounted to the upper surface of housing 163. This may place the control panel beside an inlet into the fluid circuit for a drip line when present, for example. A muzzle-head positioning and airgun discharge control panel such as that shown in FIG. 85 is mounted in the top of the airgun cabinet to present the joystick and control knobs at a height adjustable for the individual operator. Preferably, the turret-motor and recovery electromagnet controls on the barrel-assembly power and control housing are keyed to the use of these components for ablation and/or angioplasty according to the capability of the barrel-assembly, whereas those on the airgun control panel pertain to these same components for discharge-related motion control.

Made for a particular barrel-assembly rather than universal, or meant for use with any barrel-assembly, the ablation or ablation or angioplasty control panel shown in FIG. 79 provides controls for setting the current to the turret-motor stator when used as a thermal angioplasty heating element, and either of two electrical radial projection unit thermal expansion wires used to raise brush-type abrasion angioplasty tool-inserts into working position. The run-ahead or downstream trap-filter is simultaneously deployed with any tool-insert such as a side sweeper-scraper that generates debris.

VII2h(10). Control of Transluminal Rate of Translation

Whether thermal and/or by means of radial projection unit shaving or brush-type tool-inserts, exposure to atherectomizing action consists of controlling the on time or the rate at which the atherectomizing component is swept over the diseased segment. For treating long segments suspected or confirmed to harbor vulnerable plaque, the muzzle-head must be swept over the lumen surface at a uniform controlled rate. When it is preferred to control the rate more precisely than can be achieved by direct manipulation of the barrel-assembly, a linear stage is used. The rate of transluminal passage is that of linear stage travel Most controller-drive (servoamplifier) units, such as those named in the section above entitled Control of Muzzle-head Turret-motor Angle Within Working Arc will allow the control of linear table motor speed regardless of the type motor used. Since the barrel-assembly is engaged in the airgun, the controls for the linear stage can be incorporated into the airgun control panel and omitted from the angioplasty control panel onboard the barrel-assembly, which includes the controls for the ablation or ablation and angioplasty-capable barrel-assembly as an apparatus that can be used independently of an airgun or ballistic implantation.

VII2i. Procedure for the Extraluminal Stenting of a Smaller Vas Using the Apparatus Described Herein While the radial artery is too narrow to pass all but the most basic barrel-assemblies, the decision tree and techniques routinely attendant upon angioplasty and stenting, such as whether to enter percutaneously through the radial, brachial, or femoral artery, or through open exposure of the femoral, popliteal, or brachial artery generally remain applicable. The intravenous administration of antibiotics and antithrombogenics typically includes 20,000 units of heparin and 81 milligrams of aspirin, 1% lidocaine (lignocaine) injection in the puncture area.

The point of entry is a consideration in whether to use a particular combination of fluoroscopy or biplane fluoroscopy, angioscopy, intraductal ultrasound, magnetic resonance angiography, carbon dioxide angiography, endovascular ultrasonography, spiral computed tomography, and more recently, optical coherence tomography (see, for example, Monroy, G. L., Won, J., Spillman, D. R., Dsouza, R., and Boppart, S. A. 2017. "Clinical Translation of Handheld Optical Coherence Tomography: Practical Considerations and Recent Advancements," *Journal of Biomedical Optics* 22(12):1-30; Xu, J., Song, S., Men, S., and Wang, R. K. 2017. "Long Ranging Swept-source Optical Coherence Tomography-based Angiography Outperforms Its Spectral-domain Counterpart in Imaging Human Skin Microcirculations," *Journal of Biomedical Optics* 22(11):1-11; Hagag, A. M., Gao, S. S., Jia, Y., and Huang, D. 2017. "Optical Coherence Tomography Angiography: Technical Principles and Clinical Applications in Ophthalmology," *Taiwan Journal of Ophthalmology* 7(3):115-129; Gao, S. S., Jia, Y., Zhang, M., Su, J. P., Liu, G., and 3 others 2016. "Optical Coherence Tomography Angiography," *Investigative Ophthalmology and Visual Science* 57(9): October 27-36; Kubo, T., Imanishi, T., Takarada, S., Kuroi, A., and nine other authors 2007. "Assessment of Culprit Lesion Morphology in Acute Myocardial Infarction: Ability of Optical Coherence Tomography Compared with Intraductal Ultrasound and Coronary Angioscopy," *Journal of the American College of Cardiology* 50(10): 933-939).

Little affected are guidelines such as entry through a small stab wound using a Number 11 scalpel; the use of a mosquito clamp to expand the puncture site; of open arterial access to avert embolization and control outflow arteries; and so on. Here, however, the entry site is widened to admit the muzzle-head and barrel-catheter. The combination of angioscopy and intraductal ultrasound computerized processing is recommended as allowing greater accuracy than does any external imaging technique. However, the ability to target tissue for medication using medication miniballs, medicated miniballs, or hypoendothelial injection tool-inserts can significantly reduce the dose if not supplant systemic medication administered enterally or parenterally.

In intraductal use, as the site of the lesion is approached, the introduction and advancement of the apparatus provides peripheral blood-grooves to serve much as the blood flow or perfusion side-holes in catheters or, as with a balloon, deflation to reduce the diameter, for preventing the complete cessation of blood flow along its length. Nevertheless, by keeping operating time to a minimum, the risks of thrombogenesis and ischemia are reduced. To allow operative speed, the interventional airguns to be described are designed for semiautomatic repeat action radial discharge of from one to four or more miniball implants and adjustability to the exact exit velocity sought without criticality in the use of one control.

To accomplish this, the apparatus intercepts the means of airgun propulsive force development at numerous points and introduces a control at each. Also to avert thrombogenesis, heparin alone or in combination with the drugs specified above is administered until the activated clotting or coagulation time (ACT) rises above 300, as has been routine with two guidewires and a balloon in use. At the same time, the dosage of the platelet blocker or anticoagulant must seek to avoid complications at the entry site. Also routine is the application of the medication to the tip of the catheter, here the muzzle-head of the barrel-assembly. Preoxygenation through an oxygen mask is recommended.

VII2j. Through-Bore, or Combination-Form, Barrel-Assemblies

Through-bore, or combination-form, barrel-assemblies allow cabled devices for ablation, thrombectomy, atherectomy, or endoscopy, for example, to be interchangeably passed down through the central channel and out the nose midprocedurally. A barrel-assembly with built in angioscope or fiberoptic endoscope is the same in general structure but not used and therefore not referred to thus. When not containing a cabled device and wetted with heparin, such a barrel-assembly allows some blood to pass through its side-port or ports, and down the central channel to emerge out the nose.

VII2j(1). Incorporation of Adscititious Capabilities into Barrel-Assemblies

A combination-form barrel-assembly is an ablation or an ablation and angioplasty-capable barrel-assembly with a central passageway or channel for the temporary or permanent insertion of a cabled or a catheteric endoluminal device. The tubular passageway is isolated and accessed through an extracorporeal side-port that leads through a frontomedially curved section to the central axis of the barrel-assembly where it continues forward until it ends as a nose-hole at the front end of the muzzle-head. To create this passageway, a combination-form barrel-assembly, as must a barrel-assembly with built in angioscope or fiberoptic endoscope, for example, uses an edge-discharge muzzle-head with a recovery electromagnet pair of through-bore configuration, as depicted in FIG. 66.

Much of what pertains to combination-form barrel-assemblies applies equally to combination-form radial projection catheters, addressed below in the section of like title. Atheromatous tissue that is extensive or complex is removed with a radial projection catheter or an ablation or angioplasty-capable barrel-assembly, which by definition, is capable of functioning independently of an airgun for this purpose. The end-thickness and mechanical properties of the vascular wall for the stenting to follow must be considered, and in some instances, it may be preferable to dispense with angioplasty in any form as preclusive of stenting and to directly stent.

However, when the condition is less extensive or not present, a side-socket allows the transluminal component or barrel-assembly to be passed through the introducer sheath but a single time from the initiation of angioplasty to the completion of ballistic implantation. Furthermore, when the barrel-assembly is of a combination-form or edge-discharge type with a side-socket, different attachments such as for atherectomy and chilling can be interchangeably withdrawn from and advanced down the barrel-assembly central canal midprocedurally without the need to withdraw the barrel-assembly from its position within the lumen. This imparts a wide range of response options for whatever contingencies arise during the procedure.

In such function, the endoluminal barrel-assembly is a kind of transluminal guide that sheaths about devices introduced and withdrawn as opposed to the ensheathed configuration of a guide wire. Exceptionally, to minimize the diameter of a combination-form barrel-assembly, no more than one or two juxtaposed barrel-tubes are incorporated. Shifting these to one side allows the use of a single recovery electromagnet and the canal to pass through and out the nose in an otherwise center-discharge configured embodiment. For use in the circulatory system, such a barrel-assembly includes a solenoid deployed and retracted embolic protective filter that automatically deploys when discharge is triggered or the turret-motor is used in oscillatory mode.

Due to the extreme constraint upon diameter imposed by the small gauge of blood vessels and the different processes available for treating these, reserving a pathway for luminal access is especially valuable as well as constrained in an embodiment meant for use in the vascular tree. Unless inducing ischemia, the cabled or catheteric device inserted need not be withdrawn. For a barrel-assembly of given diameter with diametrically arranged barrel-tubes, the edge-discharge configuration, because it provides a clear a path along the central axis, must force some reduction in the caliber of the barrel-tubes compared to the center-discharge type.

As seen in FIGS. 38, 39, 40, 48 49, 64, and 65, a center-discharge muzzle-head allows positioning the recovery electromagnets in the path of what would be the central channel in a combination-form barrel-assembly. For use in the bloodstream, angioplasty-capable combination-form barrel-assemblies must additionally provide gas pressure relief channels shown as 226 in FIGS. 48, 49, 65 and 66. In the bloodstream, the pressure of expulsion clears blood from exit-holes 71 but is more resistant to the expulsive gas than is the open paths provided by pressure relief channels 226. The nose of the muzzle-head can be wetted with heparin before use, and service catheters can inject heparin through the barrel-tubes 74.

Even in a noncombination-form barrel-assembly, to meet these requirements within an external diameter suited to use in most of the arterial tree allows no more than two barrel-tubes of which one will typically be needed for use as a service-channel. For use in the circulatory system, the increase in diameter that results from providing a clear way to the lumen that is significantly larger in diameter than the barrel-tube or tubes limits most combination-forms to larger vessels. The canal can be left empty or used to accommodate any of numerous different cabled or catheter-based devices, to include endoscopic, intraductal ultrasonographic, and/or operative.

The passageway or canal is thus a service channel which is wider than a barrel-tube and exits out the nose rather than to a side of the muzzle-head. When unoccupied, the central canal in an ablation but not ablation or ablation and angioplasty-capable barrel-assembly is closed at the front end by a spring-loaded nose-cap (lid, cover). When the central canal is unoccupied, the nose-cap prevents blood or other luminal contents from entering in front. The distal end of an inserted cable is pushed through this cover and into the lumen far enough to afford a clear field. When to minimize the diameter of the barrel-assembly the barrel-tubes are placed to the same side of the canal, the canal and nose-cap are offset or eccentric.

Because eccentric tubes, whether barrel-tubes or an off centered canal, whether in a center or edge-discharge configured muzzle-head, are pliant, pass through the center bore of the turret-motor loosely with no attachment, to attach only at their distal extremities to the inside of the muzzle-head, resistance to the torque generated within its limited arcuate range by the turret-motor is slight. If the cable is smaller in diameter than the canal, such as must be the case with a rotational atherectomy burr as addressed below in this section, for example, the sidewise noncompressive urging of the spring against the side of the sheath or casing surrounding the drive shaft when the burr is in working position serves to stabilize the cable sheath in position by holding it against the side of the canal.

When the central channel is not fully occupied, sufficient clearance may be available to allow blood to flow through, as addressed below in the section entitled Flow-through Barrel-assembly for Use in Blood Vessels. The central channel and sheath surrounding the drive shaft must have been thoroughly wetted with heparin. The rim of the nose-cap that is applied to the side of the cable sheath or casing must not impede the retraction of the cable to behind the nose-cap. If the nose-cap is metal, then its edge must be rounded. The nose-cap must be pushed into the held open position or released therefrom while the barrel-assembly is extracorporeal.

The nose-hole in an ablation or ablation and angioplasty-capable barrel-assembly is sealed off by means of a snap-in hole-plug, as addressed A central or side canal allows the exchange or permanent installation of almost any cabled endoluminal (intraductal) device. A guide wire is not used. Permanent incorporation requires few if any modifications. However, appropriation of the canal denies its availability for additional treatment options through the midprocedural exchange of various cabled and catheteric devices that not only use the barrel-assembly as a guideway, but add processes immediately applicable to different procedures.

When not locked in the open position, the spring-loaded nose-cap serves either to close off the distal end of the canal or to urge and thus stabilize a cable or the sheath of a rotating cutting tool mounted at the distal end, for example, by forcing it against the rim of the canal. With a rotational burr, for example, the sheath about the drive shaft of a rotating atherectomy tool is narrower than the burr, and the canal must be wide enough for the burr to pass through. Thus, the sheath is narrower than the canal, so that unless held down by the spring-cap, the burr would wobble. Due to the low torque of the high speed drive shaft, the restorative force of the spring is minimal.

If two barrel-tubes are included in an angioplasty-capable barrel-assembly, then the barrel-tubes are positioned with their long axes contained within the same cross sectional semicircle or quadrant, the canal offset as a side-canal. Hence, the configuration for minimizing the outer diameter for use in the vascular tree, already offset, complements the incorporation of rotatory, such as atherectomy devices, which to allow abutment against the luminal wall, must be offset. In most instances, the device inserted or permanently installed will be static, such as a laser or endoscope. The distal or front end of the inserted device extends past the nose just enough to push aside the nose-cap and provide a clear field of view. The central canal can also be used to access the lumen with a catheter.

The catheter must possess a shaft of sufficient strength to push through the spring-loaded nose-cap When the canal will not otherwise be used, the spring loaded nose-cap can be locked open to pass blood, the central canal preprocedurally flushed with heparin, for example, if necessary. Plaque removal capability is added to combination-form or edge-discharge muzzle-head type ablation or ablation and angioplasty-capable barrel-assemblies by interchanging atherectomy rotating burrs and lasers, for example, along the unobstructed central canal which passes through the longitudinal axis to end at a hole in the center of the nose. Receding into flush relation to the surrounding outer surface of the muzzle-head when not in use, the incorporation of radial projection unit shaving type tool-inserts as addressed above in the section entitled Radial Projection Unit Tool-inserts, for example, does not increase the diameter of the muzzle-head when the tool-inserts are not deployed.

Cabled devices include lasers and other types of ablating (cutting), and abrading or scraping (attriting) tools, to include low-level radio-frequency and microwave energy and rotational atherectomy devices. For these, the central canal serves as a guide-catheter from which one device can be withdrawn and another inserted. Without a side-port to allow access to the central channel, midprocedural insertion, withdrawal, or replacement of a cabled device requires that the barrel-assembly be removed from the airgun. With a side-port, cabled devices can be introduced and removed midprocedurally whether the barrel-assembly is inserted in the airgun or not. When not needed, the nose-hole can be obturated with a plug.

A spring-loaded cap can be used to nudge a cutting tool against the lumen wall. Another reason for using an open-ended central canal is to minimize obstruction to the flow of blood, as addressed below in the section entitled Flow-through Barrel-assembly for Use in Blood Vessels. This configuration can be incorporated into an otherwise ablation or angioplasty-incapable barrel-assembly, but is usually incorporated into capable types. Whenever disengaged from the airgun, the central canal is open to the atmosphere. When one device is withdrawn and another inserted, retraction should be done slowly to minimize the vacuum that will draw blood up behind the retreating cable until it has been removed exposing the central canal to the atmosphere.

Similarly, inserting another device should be done slowly to avoid forcibly pumping blood that had been drawn up into the central canal. Changing the relative height of the extracorporeal portions of the apparatus and patient allows the use of hydrostatic pressure to affect the intracorporeal pressures. The forces involved will usually result from an orientation of the barrel-assembly that is retrograde to the flow of blood, and will increase when the barrel-assembly is advanced, and reduced when retracted. While unoccupied, the central canal can be used to allow blood to course through the barrel-assembly and out the front (distal) end. This is explained in the section below entitled Flow-through Barrel-assembly for Use in Blood Vessels.

However, since a combination-form barrel-assembly is larger in outer diameter than the equivalent noncombination-type having the same number of barrel-tubes, gaining this capability reduces the number of barrel-tubes that can be used in a blood vessel of given diameter. Accordingly, this type is not for use in blood vessels when the central canal is not used for blood flow-through or to insert the cable of a commercial device. In other type ductus, the nose-hole can be closed by means of a snap-in end cap or plug. However, the flow-through advantage of the combination-form barrel-assembly can be retained with a monobarrel with adjacent central canal that will accommodate a laser or rotatory burr cable, for example and still present an outer diameter that will allow it to be used in most vessels of larger in gauge than those with collateral circulation.

A commercial device such as a laser or a rotational burr that is needed frequently may be permanently installed within the central channel More often, the central channel is used to allow various devices to be interchanged or as a service-catheter of wider gauge than the barrel-tubes. For use in the bloodstream, to allow some blood to flow through, the muzzle-head nose-hole is normally left open. This also allows the interchange of different cabled or catheteric devices without the need for midprocedural withdrawal of the barrel-assembly as a whole rather than just the devices inserted. For use other than in blood vessels, a torsion spring-loaded nose-hatch (nose-cover, nose-cap) keeps the central channel free of debris while different cabled or catheteric devices are interchanged.

The nose-hatch is pushed open and aside by the leading end of the device, and automatically closes as the leading end recedes behind the hole. The device must project sufficiently forward (distal to) the spring cover that the to avoid interference with its mechanical or viewing performance. Except in blood vessels, the addition of a torsion spring-loaded hatch cover or nose-cap over the opening at the distal terminus (front end, nose) allows different devices to be withdrawn and inserted midprocedurally; however, the limitation placed upon the outer diameter in order to avoid anoxia limits the use of multibarrels having radial symmetry. Gathering barrel-tubes and exit-ports eccentrically allows the diameter to be reduced but necessitates additional discharges to achieve circumferential coverage.

Inserting a tube down the central canal allows lavage fluid to be delivered or recovered axially, barrel-tubes and/or radial projection unit perforated tool-inserts used to perform the opposite function. Medication can be applied in the same way, with concurrent aspiration used to take up any unwanted excess. The relative merits of balloon angioplasty and atherectomy pertinent to the means described herein are briefly addressed above in the section entitled Basic Strengths and Weaknesses of Prior Art Stenting in Vascular, Tracheobronchial, Gastrointestinal, and Urological Interventions.

While alternatives to balloon angioplasty, such as rotational atherectomy, have been cited as "exhibiting a "lack of compelling trial data suggesting that the atherectomy devices offer better outcomes in a stand-alone or even an adjunctive role," (Carrozza, J. P. 2006. "Coronary Complications of Coronary Atherectomy and Excimer Laser Angioplasty," *UpToDate* http://patients.uptodate.com/topic.asp?file=chd/17957), others differ with this position (see, for example, Sandoval, Y. and Brilakis, E. S. 2017. "The Role of Rotational Atherectomy in Contemporary Chronic Total Occlusion Percutaneous Coronary Intervention," *Catheterization and Cardiovascular Interventions* 89(5):829-831; Yu, M., Li, Y., Li, W., Lu, Z., Wei, M., and Zhang, J. 2017. "Calcification Remodeling Index Characterized by Cardiac CT as a Novel Parameter to Predict the Use of Rotational Atherectomy for Coronary Intervention of Lesions with Moderate to Severe Calcification," *Korean Journal of Radiology* 18(5):753-762; Kawata, M., Kato, Y., Takada, H., Kamemura, K., Matsuura, A., and Sakamoto, S. 2016. "Successful Rotational Atherectomy for a Repetitive Restenosis Lesion with Underexpansion of Double Layer Drug-eluting Stents Due to Heavily Calcified Plaque," *Cardiovascular Intervention and Therapeutics* 31(1):65-69; Tomey, M. I., Kini, A. S., and Sharma, S. K. 2014. "Current Status of Rotational Atherectomy," *Journal of the American College of Cardiology Cardiovascular Interventions* 7(4): 345-353; Yin, W. H. 2013. "Rotational Atherectomy: An Update," *Journal of Geriatric Cardiology* 10(3):211-212;

Fang, H. Y., Fang, C. Y., Hussein, H., Hsueh, S. K., Yang, C. H., and 5 others 2010. "Can a Penetration Catheter (Tornus) Substitute [replace] Traditional Rotational Atherectomy for Recanalizing Chronic Total Occlusions?," *International Heart Journal* 51(3):147-152; Lee, S. W., Park, S. W., Hong, M. K., Lee, J. H., Kim, Y. H., Moon, D. H., Oh, S. J., Lee, C. W., Kim, J. J., and Park, S. J. 2005. "Comparison of Angiographic and Clinical Outcomes Between Rotational Atherectomy Versus Balloon Angioplasty Followed by Radiation Therapy with a Rhenium-188-Mercaptoacetyltri-glycine-filled Balloon in the Treatment of Diffuse In-stent Restenosis," *International Journal of Cardiology* 102(2): 179-185; Sharma, S. K., Kini, A., Mehran, R., Lansky, A., Kobayashi, Y., and Marmur, J. D. 2004. "Randomized Trial of Rotational Atherectomy Versus Balloon Angioplasty for Diffuse In-stent Restenosis (ROSTER)," *American Heart Journal* 147(1):16-22) or do so for atherectomy as applied to a certain patient population (see, for example, Moustapha, A., Assali, A. R., Sdringola, S., Vaughn, W. K., and six other authors, 2001. "Percutaneous and Surgical Interventions for In-stent Restenosis: Long-term Outcomes and Effect of Diabetes Mellitus," *Journal of the American College of Cardiology* 37(7):1877-1882; Saland, K. E., Cigarroa, J. E., Lang, e R. A., and Hillis, L. D. 2000. "Rotational Atherectomy," *Cardiology in Review* 8(3):174-179).

Jamming or seizing the major risk in the use of rotablation, or rotational atherectomy (see, for example, Sulimov, D. S., Abdel-Wahab, M., Toelg, R., Kassner, G., Geist, V., and Richardt, G. 2013. "Stuck Rotablator: The Nightmare of Rotational Atherectomy," *EuroIntervention* 9(2):251-258; Lin, C. P., Wang, J. H., Lee, W. L., Ku, P. M., Yin, W. H., Tsao, T. P., and Chang, C. J. 2013. "Mechanism and Management of Burr Entrapment: A Nightmare of Interventional Cardiologists," *Journal of Geriatric Cardiology* 10(3):230-234), is remediable (see, for example, Ruzsa, Z., Lux, Á., Édes, I. F., Molnár, L., and Merkely, B. 2017. "Successful Removal of Entrapped Burr with Sheathless Guiding During Stent Rotablation," *Anatolian Journal of Cardiology* 17(2): 156-157; Chiang, C. H. and Liu, S. C. 2017. "Successful Retrieval of an Entrapped Rotablator Burr by Using a Guideliner Guiding Catheter and a Snare," *Acta Cardiologica Sinica* 33(1):96-98; Kanazawa, T., Kadota, K., and Mitsudo, K. 2015. "Successful Rescue of Stuck Rotablator Burr Entrapment Using a Kiwami Straight Catheter," *Catheterization and Cardiovascular Interventions* 86(5):942-945; Tanaka, Y. and Saito, S. 2016. "Successful Retrieval of a Firmly Stuck Rotablator Burr by Using a Modified STAR [subintimal tracking and reentry] Technique, *Catheterization and Cardiovascular Interventions* 87(4):749-756; Dandouh, Z., Abdel-Massih, T., Roule, V., Sarkis, A., and Grollier, G. 2013. "Rotational Atherectomy as Endovascular Haute Couture: A Road Map of Tools and Techniques for the Interventional Management of Burr Entrapment" *Journal of Interventional Cardiology* 26(6):586-595; Kosowski, M., Zimoch, W., Kübler, P., Wojtczak, M., Telichowski, A., and Reczuch, K. 2013. "Percutaneous Retrieval of a Detached Rotational Atherectomy Burr," Postępy w Kardiologii Interwencyjnej [Advances in interventional cardiology] 9(3): 301-303; Cunnington, M. and Egred, M. 2012. "GuideLiner, a Child-in-a-mother Catheter for Successful Retrieval of an Entrapped Rotablator Burr," *Catheterization and Cardiovascular Interventions* 79(2):271-273; Kimura, M., Shiraishi, J., and Kohno, Y. 2011. "Successful Retrieval of an Entrapped Rotablator Burr Using 5 Fr Guiding Catheter," *Catheterization and Cardiovascular Interventions* 78(4): 558-564; Sakakura, K., Ako, J., and Momomura, S. 2011. "Successful Removal of an Entrapped Rotablation Burr by Extracting Drive Shaft Sheath Followed by Balloon Dilatation," *Catheterization and Cardiovascular Interventions* 78(4):567-570).

That an extraluminal stent leaves nothing in the lumen is a significant improvement over endoluminal stents as important in alleviating or reducing postprocedural in-stent restenosis of an endoluminal stent and in having left nothing in the lumen that would interfere with followup transluminal procedures which necessitate a clear path through the lumen. Intractable inflammatory arterial disease can make the ability to perform a followup transluminal procedure without hindrance critically important (see, for example, Fournier, S., Iglesias, J. F., Zuffi, A., Eeckhout, E., Tozzi, P., and Muller, O. 2016. "Entrapment of Rotational Atherectomy Burrs in Freshly Implanted Stents: First Illustration of the Rolled-Up Phenomenon," *Journal of Invasive Cardiology* 28(11):E132-E133; Roy, J., Lucking, A., Strange, J., and Sprat, J. C. 2016. "The Difference Between Success and Failure: Subintimal Stenting Around an Occluded Stent for Treatment of a Chronic Total Occlusion Due to In-stent Restenosis," *Journal of Invasive Cardiology* 28(11):E136-E138; Sapontis, J., Christopoulos, G., Grantham, J. A., Wyman, R. M., Alaswad, K., and 11 others 2015. "Procedural Failure of Chronic total Occlusion Percutaneous Coronary Intervention: Insights from a Multicenter US Registry," *Catheterization and Cardiovascular Interventions* 85(7): 1115-1122; Christopoulos, G., Karmpaliotis, D., Alaswad, K., Lombardi, W. L., Grantham, J. A., and 11 others 2014. "The Efficacy of "Hybrid" Percutaneous Coronary Intervention in Chronic Total Occlusions Caused by In-stent Restenosis: Insights from a US Multicenter Registry," *Catheterization and Cardiovascular Interventions* 84(4):646-651; Ohya, H., Kyo, E., and Katoh, O. 2013. "Successful Bypass Restenting Across the Struts of an Occluded Subintimal Stent in Chronic Total Occlusion Using a Retrograde Approach," *Catheterization and Cardiovascular Interventions* 82(5):E678-E683).

For treating most plaque and restenosis, most studies find little difference in the long-term outcome of balloon angioplasty, cutting or scoring balloons, and rotational atherectomy. However, hard plaque can not be passed with a conventional balloon, and even when passable, is incapable of compressing hard calcified plaque against the lumen wall, and is likely to cause dissections. A fusiform (spindle or football-shaped) abrading diamond rotary cutting or grinding burr is likely superior to alternative means for passing highly calcified plaque, although by generating grinding debris, poses a risk of embolization, and if preceded by an embolic filter, poses a risk of clogging the filter and critically restraining flow-through (see, for example, section 4d(2) entitled Ductus Wall Tumefacients and Nii, K., Tsutsumi, M., Maeda, H., Aikawa, H., Inoue, R., and 5 others 2016. "Comparison of Flow Impairment during Carotid Artery Stenting Using Two Types of Eccentric Filter Embolic Protection Devices," *Neurologia Medico-Chirurgica* (Tokyo, Japan) 56(12):759-765; Iko, M., Aikawa, H., Go, Y., Nakai, K., Tsutsumi, M., and 8 others 2014. "Treatment Outcomes of Carotid Artery Stenting with Two Types of Distal Protection Filter Device," *SpringerPlus* 3:132). Additionally, the cutter can unexpectedly and nondisengagably catch or seize within a prepositioned stent, necessitating a long and life-threatening cut-down incision to be recovered, which eventuality could never obtain were there no stent in the lumen in the first place (Fournier, S., Iglesias, J. F., Zuffi, A., Eeckhout, E., Tozzi, P., and Muller, O, 2016, Op cit.). Such risk can be averted through the use of an excimer laser or a combination-form barrel-assembly that incorporates such an excimer laser; however, an laser is incapable of reducing hard calcified, or hydroxyapatite, plaque.

Use of the term 'flow reversal' here does not refer to use of the same term in conjunction with aortic regurgitation on the diastoles due to aortic valve impairment of switching from inflow to outflow in the use of tool-inserts but rather the deliberate reversal of bloodflow by the interventionist to prevent the flow of procedurally liberated atherogenic debris from passing craniad through the internal carotid artery to cause a cerebral infarction as described by Criado, E., Doblas, M., Fontcuberta, J., Orgaz, A., and Flores, A. 2004, cited below.

Transluminal or transcervical angioplasty of the carotids does appear to result in reduced incidents of thromboembolism induced ischemic stroke with blood flow reversal, which is compatible with the use of the transluminal devices to include barrel-assemblies, combination-form barrel-assemblies, and radial projection catheters described herein (see, for example, Paraskevas, K. I. and Veith, F. J. 2017. "Transcervical Access, Reversal of Flow and Mesh-covered Stents: New Options in the Armamentarium of Carotid Artery Stenting," *World Journal of Cardiology* 9(5):416-421; Cully, E. H., Trapp, B. M., and Vonesh, M. J. 2017. Single Access Flow-reversal Catheter Devices and Methods, U.S. Pat. No. 9,668,743; Kwolek, C. J., Jaff, M. R., Leal, J. I., Hopkins, L. N., Shah, R. M., and 3 others 2015. "Results of the ROADSTER [Safety and Efficacy Study for Reverse Flow Used During Carotid Artery Stenting Procedure] Multicenter Trial of Transcarotid Stenting with Dynamic Flow Reversal," *Journal of Vascular Surgery* 62(5):1227-1234; Clair, D. G., Hopkins, L. N., Mehta, M., Kasirajan, K., Schermerhorn, M. and 5 others with 19 collaborators 2011. "Neuroprotection During Carotid Artery Stenting Using the GORE [W.L. Gore and Associates Incorporated, Newark, Del.] Flow Reversal System: 30-day Outcomes in the EMPiRE Clinical Study," *Catheterization and Cardiovascular Interventions* 77(3):420-429; Kelso, R. and Clair, D. G. 2008. "Flow Reversal for Cerebral Protection in Carotid Artery Stenting: A Review," *Perspectives in Vascular Surgery and Endovascular Therapy* 20(3):282-290; Parodi, J. 2008. "Commentary on "Flow Reversal for Cerebral Protection in Carotid Artery Stenting: A Review," *Perspectives in Vascular Surgery and Endovascular Therapy* 20(3):291-292; Criado, E., Doblas, M., Fontcuberta, J., Orgaz, A., Flores, A., and 5 others 2004. "Transcervical Carotid Stenting with Internal Carotid Artery Flow Reversal: Feasibility and Preliminary Results," *Journal of Vascular Surgery* 40(3):476-483; Criado, E., Doblas, M., Fontcuberta, J., Orgaz, A., and Flores, A. 2004. "Transcervical Carotid Artery Angioplasty and Stenting with Carotid Flow Reversal: Surgical Technique," *Annals of Vascular Surgery* 18(2): 257-261).

VII2j(2). Accommodation of Rotational Ablating or Atherectomizing Side-Cutting Devices in Combination-Forms Through-bore or combination-form barrel-assemblies and radial projection catheters, as addressed below in the section of like title, must allow the use of rotational or linear side-cutting devices and allow these to be retracted into the central channel when not in use so that the combination-form device can itself remain stationary within the lumen. In an artery, rotating burrs and razors are used to perform an atherectomy (see, for example, Fornell, D. 2010. "New Tools to Debulk Lesions: Combo Cutting/Aspiration Catheter and Laser Systems Offer New Atherectomy Choices," *Diagnostic and Interventional Cardiology* 50(1):16-17), and comparable devices to perform an ablation in other type ductus can be anticipated. Means for bringing the cutting end into functional alignment against the lumen wall are therefore necessary both in arteries and in the airway, where the entry of debris is not a problem, and in the gastrointestinal tract, for example, where it is.

A barrel-assembly with an eccentric bore allows a cabled rotational device to abut against the lumen wall in substantially parallel relation to remove accreted or diseased tissue. However, an eccentric bore also precludes rotation of the muzzle-head by the turret-motor, and depending upon the diameter of its cable, limits if not precludes the incorporation of radial projection units over the periphery in the sector over the segment occupied by the rotational device. By the same token, the use of a central bore requires a mechanism to urge the cutter sideways into functional contact with the lumen wall. A snap-in spring-loaded nose-cap to cover over the nose-hole when the central channel or bore is unoccupied is addressed above in the section entitled Capabilities of Different Type Barrel-assemblies.

When the rotational or linear device is passed through the bore and up to or out through the nose-hole, the push-through or snap-in spring-loaded nose-cap is pushed open and aside. Such a spring-loaded nose-cap can be used to push against the sheath urging the cutter into contact with the lumen wall with the force set by the spring. When the cutter is retracted, the spring-loaded cap closes behind it. For the purpose of closing off the nose-hole to prevent the entry of debris, a surround extending wiper fingers, likewise addressed above in the section entitled Capabilities of Different Type Barrel-assemblies, is equally effective as a nose-cap and far better at wiping down and keeping out debris as the working end of the cutting device is retracted behind it.

In the gut, for example, a spring-loaded nose-cap can serve favorably both to urge the cutting tool against the lumen wall and to close off the nose-hole when the tool is retracted. The inseparability of sidewise urging and closure means, however, that a second instrument such as an endoscope will also be deflected as well as obstructed unless fully protruded. Moreover, in an artery, a patent central channel allows some blood to flow through, and in the airway, some air. For most applications, urging against the lumen wall, cleaning upon closure, and sealing off of the central channel as the cutter recedes must be separated.

A spring-loaded arm mounted off to a side of the nose-hole rather than a cap does not close off the nose-hole to block the lumen. However, attached as is a cap to the muzzle-head rather than to the inserted device, unless the extent to which the tool can be advanced is limited, the arm will cause the cutter to veer more aside (abluminally, radially outward) as it is advanced and will remain even after the tool has been withdrawn to obstruct the view through an endoscope used after and not just together with the cutting tool. A stop or detent about the sheath of the cutting tool, which can take the form of an annular depression caught by the free end of the spring-arm.

When keeping debris out is an object, a rubbery surround that extends wiper fingers toward the center where the tips of the free ends meet is more effective, while a spring arm attached to the muzzle-head can be used at the same time to urge the cutter into the proper working angle relative to the lumen wall. Another problem with a cap is that when it is open and the barrel-assembly or radial projection catheter is advanced, even provided with an elastomeric surround, the edge could gouge or incise the lumen wall. A spring attached to the sheath of a cutting tool with one arm compressed by the central channel while contained therein will serve to urge the distal end of the sheath to the side against the lumen wall, and fastened to the specific tool rather than to the muzzle-head, is not left to interfere with the use of any other tool.

More specifically, in a radially symmetrical barrel-assembly intended for general use, the eccentricity required to use a rotational cutting tool is obtained by cinch-clamping a bent spring steel or torsion spring about the sheath of the rotational burr or razor so that when the rotational device is passed through the bore as a guide catheter and forward out through the nose, the bore continues to compress and the arms of the spring flat until the upper arm passes through the nose, and free to close, urges the sheath of the device toward the lumen wall. The distance to which the distal end of the cutting tool can be extended past the nose-hole and its consequent abluminal reach are set by the level along the tool shaft at which the spring is fastened and is limited by a lug stopped by a nose-hole detent.

The detent consists of a slight inward ledge rim about the nose-hole that catches a projection on the spring and thus stops the sheath from advancing further. The spring must be clamped about the sheath at a distance sufficiently proximal to the nose to allow the cutting head to achieve a working angle relative to the lumen wall. The proximal portion of the cable-mounted spring thus remains within the bore and sets the limit to forward and abluminal extension. For use in the gut, for example, such a spring is combined with a fingered surround for wipe-down and closure. Upon retraction, the fingers first sweep over the surface of the spring, then the rotating tool, and once the tool is retracted, close off the nose-hole to debris. The bore is therefore clean allowing insertion of another cabled device.

VII2j(3). Types of Combination-Form Barrel-Assemblies

Combination-form barrel-assemblies are ablation-capable or ablation and angioplasty-capable, such classification not further divided according to the number of barrel-tubes or incorporation of different cabled or catheter devices. Angioplasty-capable barrel-assemblies are always capable of ablation, but due to the sever limitation on size and requirement for pressure relief, the reverse need not be true. Ablation-capable barrel-assemblies are generally larger, do not need to allot space for gas pressure diversion channels, or shift barrel-tubes to the same side of the canal to achieve a smaller cross section. These therefore tend to use the edge-discharge configuration shown in FIG. 66.

Distinction based upon structure as edge or center-discharge is substantially pertinent only to angioplasty-capable barrel-assemblies. The nose-holes of ablation, ablation and angioplasty-capable barrel-assemblies, and combination-form radial projection catheters when the latter two are used in the bloodstream are not covered. This allows some blood to flow through and eliminates a lid or hatch opened to the front that even with an elastomeric surround risks incisions when advanced. The torsion spring closed hole-cover or lid has a base made like an electronic chassis hole-plug with prongs about the circumference that hold the lid in the nose-hole by radial restorative force.

VII2j(4). Forward-Directed Clearing (Ablation and/or Angioplasty) Means for Integration into the Muzzle-Head The rearward extension of the muzzle-head imparts a longitudinal aligning effect, and the barrel-catheter with internal components is made sufficiently stiff to track with no buckling without the need for a guide or 'buddy' wire, the muzzle assembly itself effectively a fixed wire, as opposed to an over the-wire device. Any catheter-based means for the removal of plaque can be integrated into the muzzle-head at the front end so that the implantation of the miniballs can follow immediately upon the removal of plaque. However, a preferable means would not necessitate either thermal insulation or extension in length of the muzzle-head as to deny depth of implantation access, as addressed above in the section entitled Factors that Affect Muzzle-head Nosing Length or Reach, Steerability, and Trackability.

While the longitudinal elongation exerts a canal-aligning effect that reduces the risk for an exposed sharp rotational atherectomy cutter or burr at the front end to go off-course producing furrows if not perforations, so long as the burr remains exposed, this would always loom as a possibility. Thus, to use a rotational burr, the muzzle-head would have to be extended forward in length so that the burr could be held within a recess at the front end until used. While such extension would consist of only about six millimeters, this length could prove significant if moving down the vascular tree, the lumen diameter had become sufficiently narrow to require stretching and the likelihood of dissection if advancement were to continue.

Incorporating an excimer laser substantially avoids the risk of embolism, hence, the need for a protective device such as an embolic filter, but is unsuited for reducing the hardest calcified plaque, is capable of dissections and perforations, and is associated with more frequent restenosis (Liu, W., Zhang, Y., Yu, C. M., Ji, Q. W., Cai, M., Zhao, Y. X., and Zhou, Y. J. 2015. "Current Understanding of Coronary Artery Calcification," *Journal of Geriatric Cardiology* 12(6):668-675; Bittl, J. A., Chew, D. P., Topol, E. J., Kong, D. F., and Califf, R. M. 2004. "Meta-analysis of Randomized Trials of Percutaneous Transluminal Coronary Angioplasty versus Atherectomy, Cutting Balloon Atherotomy, or Laser Angioplasty," *Journal of the American College of Cardiology* 43(6): 936-942).

Incorporation of a rotational atherectomy burr makes it possible to cut a path through the hardest mineralized obstructions and thus affords a critical capability over alternative devices. Conventional or balloon-based thermal and cryogenic devices introduce temperature and thus dimensional instability that to protect against erratic performance would necessitate the incorporation of insulation for which space is lacking. In the coronary arteries, for example, placing balloon based devices in tandem with the muzzle-head would untenably deny depth of access.

The least obtrusive and disruptive means of ablation suitable for integration into the muzzle-head are ultraviolet xenon-chlorine excited dimer or 'excimer' lasers and continuous wave neodymium yttrium aluminum garnet or Nd:YAG, and carbon dioxide or $CO_2$ lasers. Nevertheless, demanding an increase in the outer diameter of the muzzle-head, incorporating a laser does reduce the lumen diameter, hence, the extent of the vascular tree that may be accessed with any one muzzle-head. For this reason, the incorporation of a laser into a barrel-assembly relates more to those with one or a few barrels. In contrast to thermal and cryogenic balloons, the optical fibers connected to the console leading to the small diameter probe tip are mechanically and thermally passive.

VII2j(5). Barrel-Assembly with Built in Excimer Laser

While various mid-course divisions or divergences and confluences of laser fiber optics would allow the fibers to be coursed about other components, incorporation of an excimer laser into a barrel-assembly is advantageously and preferably obtained without the need to significantly modify an off-the-shelf laser catheter. Laser atherectomy actually cavitates and vaporizes all but highly calcified plaque rather than merely compressing plaque as does balloon angioplasty, which is, however, accomplished more quickly. In the present context, however, the radial projection unit side-sweeping capability, the laser in variable sequences, and—when the lumen diameter is the same or smaller than that of the muzzle-head—coordinated use of the muzzle-head much as a balloon, allow greater speed of tissue reduction and removal than any of these components alone.

All catheter-based procedures can induce abrupt closure by spasm. Other problems encountered with lasers alone, notably the inducement of spasm and promotion of fibrin deposition, are similarly moderated by immediate follow-up with implants (spherules, miniballs) that have been medicated to counteract these complications. Since both laser atherectomy and ballistic implantation can induce such responses, making antispasmodic and antiplatelet or anticoagulant-coated miniballs routinely available is advisable. Referring now to FIG. 67, shown is the front or distal end of an edge-discharge muzzle-head for a combination-form barrel-assembly which incorporates a pulsed ultraviolet photo-ablation excimer laser having optical fibers, each consisting of a core, cladding, buffer, and containing sheath or catheter, with distal end centered in the nose.

Additionally incorporated adjacent to the laser is an embolic filter, which is controlled by switching to automatically deploy when a radial projection unit is used and disabled whenever the laser is in use. To prevent plaque that extends to the center of the lumen from being undercut closer to the lumen wall and freed as pieces toward the lumen axis to pass down the bloodstream intact, the distal ends of the optical fibers close to the surface of the muzzle-head can be made to follow the outer contour of the muzzle-head slightly bent toward the central axis, while the outer fibers are directed straight ahead. The muzzle-head of a barrel-assembly that incorporates a laser must have a nosing that places the distal ends of the optical fibers at a distance from the front end and the plaque to be fully effective.

The optical fibers are omitted from positions about the circumference that would cause the fibers to course over blood-grooves, blood-tunnels, the entry ledges before the doors on the traction electromagnet chambers, the muzzle-ports, and side-scraper ablators. Remote rotation of the muzzle-spindle by means of a swivel or turret-motor requires that the optical fibers be cut at the level of the rotary joint between the distal end of the motor and proximal end of the muzzle-spindle. However, since rotation is no part of the plaque removal process but rather part of the stenting function which does not commence until plaque removal has been completed, the proximal and distal portions of each fiber do not move in relation to one another until their use has ended.

To minimize losses to refraction and scattering at the interface where the portions meet, the segments of the fibers are made to interface as flush as will not interfere with the use of the swivel or turret-motor. For atherectomy by means of photo-ablation, the xenon-chlorine laser is set to a wavelength of 308 nanometers with a rate of pulsation ranging between 25 and 80 repetitions per minute. The fiber optics in the barrel-assembly are connected to an excimer laser control console, such as the Spectranetics CVX-300® excimer laser system. Since the laser vaporizes plaque laying directly to the front of the distal ends of the fibers, better coverage is obtained when the fibers are more radially distributed about the nose of the muzzle-head.

Generally, the use of a laser to destroy atherosclerotic material and hinder subsequent hyperplasia can be potentiated when the target tissue has been primed through the preprocedural administration and accumulation in the target tissue of a photosensitive drug (see, for example, Jain, M., Zellweger, M., Wagnières, G., van den Bergh, H., Cook, S., and Giraud, M. N. 2017. "Photodynamic Therapy for the Treatment of Atherosclerotic Plaque: Lost in Translation?," *Cardiovascular Therapy* 35(2); Chou, T. M., Woodburn, K. W., Cheong, W. F., Lacy, S. A., Sudhir, K., Adelman, D. C., and Wahr, D. 2002. "Photodynamic Therapy: Applications in Atherosclerotic Vascular Disease with Motexafin Lutetium," *Catheterization and Cardiovascular Interventions* 57(3):387-394; Chen, Z., Woodburn, K. W., Shi, C., Adelman, D. C., Rogers, C., and Simon, D. I. 2001. "Photodynamic Therapy with Motexafin Lutetium Induces Redox-sensitive Apoptosis of Vascular Cells," *Arteriosclerosis, Thrombosis, and Vascular Biology* 21(5):759-764; Rockson, S. G., Lorenz, D. P., Cheong, W. F., and Woodburn, K. W. 2000. "Photoangioplasty: An Emerging Clinical Cardiovascular Role for Photodynamic Therapy," *Circulation* 102(5): 591-596) to reduce the restrained atheroma and any restenosing tissue by the time the stent has been absorbed. Impermanent, absorbable stents are unsuited to interdictory use on an extended basis, such sites largely identifiable, as addressed in the section above entitled Comparison of Extraluminal with Endoluminal, or Conventional, Stenting.

VII2j(6). Barrel-Assembly with Exchangeable or Built in Rotational Atherectomy Burr As addressed above in the section entitled Radial projection unit tool-inserts, a radial projection unit tool-insert with diamond particle covered cutting surface that is reciprocated at high speed by the turret-motor in oscillatory mode can abrade mineralized plaque. However, a rotational burr can achieve a faster cutting rate, making expedient the incorporability of such a device into a combination-form barrel-assembly. A rotational atherectomy burr is best inserted temporarily so that it can be interchanged with alternative cabled devices for viewing or treatment. The canal itself service as the guideway, a guide wire not used. If step up burr technique is to be used, then the canal must accommodate the widest of the burrs to be used. The addition of medication to the drive shaft coolant and administration of medication, such as abciximab, aspirin, calcium channel blockers, heparin, and so on, are unremarkable.

The use of cabled and catheteric devices with combination-form barrel-assemblies is addressed above in the section entitled Incorporation of Adscititious Capabilities into Barrel-assemblies. The burr is inserted into the barrel-assembly through a side-socket and fed through the canal until the tip of the burr is positioned just inside the nose, which position is marked on the casing or sheath before use. The tethering is that of the commercial device. Alternative use of the barrel-assembly can precede use of the burr, which to use is advanced through the barrel-assembly to a second mark on the casing at which point one arm of a spring mounted to the outer sheath of the cable exits urging the burr against the lumen wall. The burr can be freely deployed or retracted (withdrawn, stowed) at any time the barrel-assembly is in use.

VII2j(7). Flow-Through Barrel-Assembly for Use in Blood Vessels

Any edge-discharge type barrel-assembly can be furnished with a patent central channel as a combination-form barrel-assembly for use in the bloodstream. Provided the central canal is unoccupied or affords sufficient clearance, a combination-form barrel-assembly can allow blood to course through it. When antegrade, flow is through side-ports equivalent to the side-holes in conventional catheters at the surface along the distal barrel-catheter that lead through frontomedially directed tunnel-tubes past any intervening barrel-tubes or pressurized gas diversion channel into the central channel or bore and out the nose-hole. When retrograde, blood enters through the nose-hole and exits out the side-ports. The pressure of flow depends upon the blood pressure and cross-sectional area over this path.

See also the section below entitled Flow-through Bore in Combination form Barrel-assemblies and Combination form Radial Projection Catheters Used in Blood Vessels. More specifically, the central canal communicates at an acute angle with the surrounding lumen through short tubes over the intracorporeal length, each leading to an opening on the outer surface of the barrel-catheter. The use of multiple side-holes makes it possible to use the same barrel-assembly over a range of intraluminal lengths; otherwise, a single such channel, placed for the intracorporeal length actually involved, which is slightly easier to work with, is used. The holes and central canal should be dimensioned and configured so that flow through those distal does not detract from the rate of inflow into those more proximal and impede the flowrate down the central canal.

So long as the central canal is unoccupied, the elliptical entry and exit portals and short length of the connecting tubes expedite the flow-through of blood. Inserting a cable through the central canal closes off these side-tubes or passages. The peribarrel space surrounding each barrel-tube and therefore, the ability of the barrel-assembly to prevent the expulsion of gas into the bloodstream is unaffected whether the central canal is or is not occupied. Coagulation on the barrel-assembly is avoided by submerging the barrel-assembly in an anticoagulant, such as heparin-saline, acid-citrate-dextrose, or ethylenediaminetetraacetic acid solution, then, dipping the nose-hole in the solution, using a bulb or syringe pipette to draw solution up through the service canal until solution begins to spill from the side or entry portal most distad.

The bulb or syringe having been left attached to its proximal end, the entry of gas into the bloodstream is avoided by then inserting the barrel-assembly through the introducer sheath, a fingertip used to prevent the solution from spilling out through the distal entry portal. As this first and subsequent (more proximal) entry portals enter, the bulb or syringe is used to draw the Ringer's solution and blood up to the next entry portal until the intracorporeal length is reached. The insertion and withdrawal of interchangeable cabled devices with the barrel-assembly remaining endouminal is addressed below in the section entitled Incorporation of Supplementary Capabilities VII2j(8). Widely Applicable Barrel-Assembly The versatility of a side-socketed barrel-assembly is addressed in the section above entitled Concept of the Extraluminal Stent and the Means for Its Placement. A side-socketed combination-form, or edge-discharge, barrel-assembly is versatile in accepting commercial cabled auxiliary devices and attachments, making it widely adaptable at added cost. Combination-form barrel-assemblies always have a side-socket that includes a portal for admitting the cable of various viewing, atherectomy and other cabled devices. One or more cabled device is inserted through the central bore or channel to or past the muzzle-head nose hole.

In order to allow the central canal to accommodate either the cable of a commercial atherectomy device or a cooling catheter during discharge without the need to withdraw the barrel-assembly at any time from the commencement of the angioplasty to completion of discharge, the need for a nose-window (nose 'heat-window) must be eliminated, since the distal end of the barrel-assembly is inaccessible from the outside. If not the concurrent attachment of a nose 'heat-window installed on a temporary basis, then a cooling catheter requires a coolant inflatable balloon to project out of the front of the central canal. Since the balloon is distal to the muzzle-ports, chilling to stabilize the target tissue would then follow rather than precede discharge, limiting discharge to transluminal advancement.

The various cables and catheters used as hoses to be fed down the central canal of a wide use barrel-assembly must have a tick mark at the proximal end to show exactly to what depth the device is to be snaked (fed, advanced) down the central canal, and must also be guided to the proper ending position. This requires but a flared central hole (aperture) in each centering device to act as a funnel. An annulus with front flange or detent projections to prevent further forward insertion at the front opening of the central canal or the rear (proximal edge) of the nose-window if attached engages the distal end of the cooling catheter thus centering it at the correct distance from its proximal surface. If the source of cold air is a vortex tube cold air gun, switching to the hot outlet allows the quick return to body temperature.

Antithrombogenic medication should be administered when using elevated or lowered temperatures in the bloodstream. The highly localized introduction of implants that consist purely of medication is more quickly and less traumatically accomplished by means of ballistic discharge than by inserting stays one at a time through an incision. The lack of an incision through which the ductus might be approached from outside or extraluminally does, however, require that if used, cold be delivered endoluminally. In an artery of sufficient luminal diameter, this is accomplished with an ablation or ablation and angioplasty-capable barrel-assembly equipped with a fluid radial projection system. The use of a snap-in hole-plug when it is preferred to keep the nose-hole closed is addressed above in the section entitled Types of Barrel-assemblies.

VIII. Radial Projection Catheters

VIII1. Types of Radial Projection Catheters.

Eliminating radial projection units from the barrel-assembly, especially fluid units from the muzzle-head, makes possible a significant reduction in gauge and stiffness that allows a more navigable barrel-assembly to pass through narrower ductus or reach farther down into the vascular tree. Relegating projection units to a removable sheath (sleeve, mantle) of matching size with its own power and control housing which can be slid over or removed from the barrel-assembly at any time also allows the muzzle-head to be made shorter, imparting greater steerability that makes it possible to pass sharper curves. Lacking a ballistic component, a separate radial projection catheter is not a barrel-assembly. When used alone or as primary with other catheteric devices inserted through the central bore, it is referred to as radial projection assembly.

Very narrow ductus require relegation to a separate non-combinable radial projection catheter without an available central bore referred to as a simple radial projection catheter. Abutment of a much narrower projection catheter against the lumen wall is by 1. Ensheathing the intraluminal projection catheter within one of larger diameter, 2. Using an external magnet to draw a ferromagnetic cord that has been built into or is temporarily inserted into the barrel-catheter or the projection catheter, or 3. Using push-arm blanks mounted or not mounted on a scissors-lift platform, as addressed above in the section entitled Extended Projection Scissors Lift-platform Mechanism.

All radial projection catheters, to include combination-forms made for combined use with a barrel-assembly, radial projection catheter of smaller diameter, or a cabled device, include a power and control housing and can be used independently. If provided with side-ports, the unoccupied bore can be used to allow some blood to flow through. Ablation or ablation and angioplasty-capable Barrel-assemblies which ensheath a barrel-assembly as ballistic component within a combination-form radial projection catheter as a supplementary or adjunct peripheral component relative to that in the muzzle-head constitute joint or divisible, (with two components, bipartite or duplex) ablation or ablation and angioplasty-capable barrel-assemblies. In any such combination, only the peripheral component is augmented, but the endoluminal device is rendered bipartite or duplex.

A conventional guide wire, simple radial projection catheter, or a barrel-assembly can be ensheathed within a combination-form barrel-assembly having a distal through-bore or edge-discharge type muzzle-head. Rather than a distal muzzle-head, a combination-form barrel-assembly can include exit ports at another level or at different levels along its length, thus incorporating the nominally ballistic component within the peripheral component. Supplementation of the ballistic component in the muzzle-head by ensheathment to obtain a larger diameter for discharge or to increase the caliber of the miniballs, making the ballistic the peripheral component, is discounted as nonessential and introducing complications such as proximal spillage from the lumen of the central component requiring plugging before insertion in the airgun, for example.

The use of interchangeable combination-form radial projection catheters with the same central component means that the clogging of even several fluid circuits during aspiration can be responded to by exchanging only the peripheral or outer component. This avoids the need to withdraw and retract the central component, which is left in place as a guide wire. Any number of outer projection catheters, each differently equipped or differing in outer diameter, can be exchanged (replaced, 'swapped'). When fully ensheathed, the rear of the catheter housing fits flush to the front of the barrel-assembly housing, which is slid proximally (backward) to allow the projection catheter to slide separately.

When a combination-form radial projection catheter of larger diameter is slid over or withdrawn from one of smaller diameter, the power and control housings of the intervening projection catheter is slid off the proximal end of the projection catheter. As shown in FIG. 71, in a duplex ablation or ablation and angioplasty-capable barrel-assembly, the length as well as concentrically matched sizes mean that the power and control housing of the ensheathed barrel-assembly and that of the outer projection catheter juxtapose flush in ganged relation. When advanced and withdrawn with the aid of the linkage shown in FIG. 78, the encircling projection catheter with its housing moves forward with the barrel-catheter, the barrel-assembly housing held in position by the connecting arm that extends from the base of the linear positioning stage.

Since only the intracorporeal portion of the duplex is doubled decreasing its flexibility, the need for the extension linkage to prevent sagging of the extracorporeal length remains. The power and control housing of an ensheathed radial projection catheter is unused and removed by being slid off its proximal or rear end. The housing of an ensheathed barrel-assembly is proximal and juxtaposed against the rear of the outermost combination-form projection catheter housing when fully ensheathed. Removal is by sliding the housing off the proximal end of the intervening projection catheter as addressed below in the section entitled Slidable Radial Projection Catheter Power and Control Housing.

Ensheathment must always take trackability into account, so that one or another of these concentrically fitted catheteric devices can be partially withdrawn when moving through a curve, for example. For economy, small diameter minimally ablation or ablation and angioplasty-capable barrel-assemblies can be made fully ablation or ablation and angioplasty-capable by sliding the projection catheter over the barrel-assembly when disengaged from the airgun. However, since a minimally capable barrel-assembly lacks a power and control housing, the functions normally controlled from the housing must be incorporated into the housing of the projection catheter despite the fact that for clarity and to reduce human error, it is always preferred to mount controls to the component to which the controls pertain.

Larger diameter embodiments can be made integral or entire with radial projection units incorporated into the muzzle-head and/or about the barrel-catheter without the need for supplementation through use of a sheath. Because lumen diameters limit the components that can be incorporated into a radial projection catheter, simple radial projection injection catheters are usually limited to a fiberoptic endoscope and hemitoroidal heat-window at the nose. Simple radial projection catheters with unit lift-shafts configured to allow the engagement of tool-inserts for performing an ablation or an angioplasty have a punch or plunger solenoid deployed and stowed embolic filter as, and if space will allow, a fiberoptic endoscope, centered in the hemitoroidal heat-window surrounding it at the nose.

To expedite crossing curves, the radial projection catheter can be held back while the muzzle-head is pushed forward. Numerous interchangeable combination-form radial projection catheters that match the barrel-catheter of a given barrel-assembly in diameter, can differ widely in outer diameter and the electrical and fluid circuits each contains. Since such immediate adaptation to changes in lumen diameter can use projection catheters of a prescribed flexibility and fitted with tool-inserts of the same or different kinds of tool-inserts, difference in diameter resulting from lesions that protrude into the lumen, for example, can be responded to by exchanging projection catheters as appropriate.

This makes possible wide variability in the flexibility, diameter, and capabilities of a barrel-assembly and the specific matching projection catheter combined at a given time; using the barrel-assembly as a guide wire introduced and advanced to a treatment site first, combination-form projection catheters of different diameters and capabilities can be exchanged as the diameter and condition of the lumen changes. Whether a barrel-assembly is at the center, in lumina of sufficient diameter, combination-form projection catheters with bores matched to receive narrower projection catheters allow the successive withdrawal of the outer projection catheter as the lumen becomes gradually narrower.

That is, since the more central projection catheters are in effect prepositioned, the number of introductions through the entry wound is reduced; however, in the vascular tree, introducing the outer projection catheter not prefilled thus makes the central channel available for blood to pass. To preclude human error that would result in the use of an ablative tool-insert in an injection catheter that lacked effective means for intercepting potentially embolic debris, for example, these different tool-inserts and made in slightly different sizes or with keys to prevent insertion in an unintended catheter.

For these reasons, radial projection units not needed to eject a lubricant into the lumen or inject lesions on initial approach, and fluid units in particular, are consigned to a separate sheath that can be slid over a barrel-assembly or cabled device such as a separate fiberoptic endoscope or thrombectomy cutter at any time before of after the device has been introduced into the body. Radial projection catheters of either kind are self-contained, internally powered, and controlled independently of the barrel-assembly. A simple or noncombination-form radial projection catheter is used independently of a barrel-assembly to ablate, angioplasty, or eject a fluid substance into the lumen or inject the substance into the lumen wall.

This allows a smaller outer diameter than a combination-form, which must accommodate cabled devices through a central channel or through and through bore. Simple projection catheter that must achieve an outer diameter that is too small to allow the incorporation of both a scope and an embolic filter are differentiated as injection or ablation in type, the former including a viewing device such as a fiberoptic endoscope, the latter an embolic filter at the nose center. A combination-form differs from a simple radial projection catheter in having a central channel, or bore, which allows it to be slid over the barrel-catheter of a barrel-assembly or pass a cabled device up to or through the nose-hole.

When unoccupied or not too fully occupied by any diagnostic or therapeutic instrument and the nose-hole at the distal end of the projection catheter is not plugged by means of a snap-in nose-cap, the central channel may afford sufficient clearance for some blood to pass to or from a side-port. The constraints on diameter are, however, such as to limit any practical ischemia averting consequences to only larger vessels. Omitting a ballistic component, a non-combination-form radial projection catheter can deliver a level of functionality to lumina too narrow or tightly curved to admit a barrel-assembly equipped with the same radial projection units. In less narrow ductus, it can also incorporate fluid radial projection units and perform endoluminal procedures such as ablation and injection independently of a barrel-assembly.

Combination-form radial projection catheters with radial projection units that do not accept tool-inserts of ablation size or keying and marked for injection only can be made especially narrow. Not generating debris, it relies upon the nose heat-window and omits an embolic filter at the nose to incorporate a built in angioscope or fiberoptic endoscope for precise injection. By contrast, a combination-form radial projection catheter can be used separately or to add functionality to a barrel-assembly. It can be slid over the barrel-catheter of the barrel-assembly used as a kind of guide wire, or removed as necessary whether the barrel-assembly is extracorporeal or endoluminal.

VIII2. Simple, or Noncombination-Form, Radial Projection Catheters

Simple radial projection catheters differ from combination-form or through-bore radial projection catheters in that a central channel if any is too small and unavailable for insertion of a cabled device or the barrel-catheter of a barrel-assembly. One exception is that a fine fiberoptic endoscope may be permanently fixed in position along the longitudinal central axis. As a matter of definition, however, embodiments with a central channel large enough to accommodate a cabled device such as an endoscope, laser, or rotational atherectomizer, for example, are combination-form radial projection catheters. The capabilities of a simple radial projection catheter can include the ejection of medication or other therapeutic substances to coat the lumen wall, infuse a vein, inject a fluid therapeutic substance into the lumen wall, thermoplasty, and ablate with cutting (shaving) or abrading tools.

A radial projection catheter equipped with fluid units can additionally cryoplasty, sequentially or concurrently irrigate and aspirate using water or another therapeutic solution, or inject or eject fluid substances intermittently or continuously in any amount. All radial projection catheters whether simple or combination-form have a proximal power and control housing, which unlike that of a barrel-assembly, is not slidable. Simple, or noncombination-form, radial projection catheters may have a central channel for wires of fluid lines. A separate or simple (noncombination-form) projection catheter that incorporates only electrically controlled radial projection units can be made narrower and more flexible than one with one or more fluid circuits.

Using side-looking injectors, or if the small diameter and strength of the ductus allow, emitter-irrigator-aspirator fluid tool-inserts, numerous procedures possible with a simple radial projection catheter need have no relation to ballistic implantation or stenting of any kind. When, for example, the need for miniballs consisting of medication or a sclerosant, for example, can be satisfied by injection tool-inserts, the use of a radial projection catheter allows the procedure to be completed with a single luminal entry. Larger ductus such as those of the gastrointestinal tract and the trachea and bronchi allow the use of combination-form radial projection catheter-ensheathed barrel-assemblies and combination-form barrel-assembly-ensheathed cabled devices such as a laser.

However, when a lumen requiring an ablation or an angioplasty prior to stenting is too narrow to admit even a muzzle-head that includes both the necessary radial projection units and the number of barrel-tubes desired, a simple radial projection catheter can be used first, followed by a narrow barrel-assembly having a radial discharge monobarrel muzzle-head, for example. To do so does, however, lose the advantage of both preparatory therapy and implantation with single entry. To achieve the narrowest diameter rules out a central channel Simple radial projection catheters that lack the tool-inserts to act as side pushing arms use the channel to incorporate a ferromagnetic cord that facilitates abutment of the tool-insert faces against the lumen wall with the aid of an external electromagnet.

Varying the cord as solid or braided and the material and thickness of the solid cord or each braid allows adjusting catheter flexibility for the best balance between trackability and sufficient stiffness to prevent injury to the lumen wall when the external magnet is used. For use in the arterial tree, a simple or noncombination-form that is used to deliver medication and not used to perform an atherectomy usually includes a nichrome coil heated hemitoroidal dome configured heat-window at the nose with the convex surface directed downstream, or distad.

When switched on, the heat-window sears the caps of vulnerable plaques and burns the potentially embolizing contents as the muzzle-head passes. Centered within this annular heat-window, the hole in the nose is commonly occupied by the distal end of a fine fiberoptic endoscope. Because radial projection units in independent circuits assigned to different radial angles are situated about its circumference, the turret-motor of a ballistic component is not required.

VIII3. Through-Bore, or Combination-Form, Radial Projection Catheters

A combination-form radial projection catheter has a through-and-through central axial channel or bore for retaining, or for conveying in the manner of a guide catheter, a cabled device such as a laser, an endoscope, or diameter allowing, more than one such device. Using the barrel-catheter of the barrel-assembly in the manner of a guide wire, the combination-form radial projection catheter is slid leading (distal) end first over the proximal end of the barrel-catheter. Because the power and control housing hand-grip of an ablation or ablation and angioplasty-capable barrel-assembly can be slid off the proximal end of the barrel-catheter, a radial projection catheter of matching size can be added at any time before or after a fully ablation or ablation and angioplasty-capable barrel-assembly has been introduced into the body.

When not used independently, a combination-form radial projection catheter slips over the ensheathed device such as a barrel-assembly. However, a combination-form radial projection catheter can be used apart from the ensheathed device with or without a nose-hole plug. For a barrel-assembly, steerability, trackability, and navigability in general are expedited by allowing reduction in the longitudinal extent of the radial projection units at the sides of the muzzle-head, which can thus be shorter. With the aid of an external magnet to aid in steering the muzzle-head, high pliancy and a short muzzle-head make it possible to navigate through tight curves. However, the same barrel-assembly in a less restrictive ductus would gain considerable capability through the addition of the projection catheter.

Because the radii of curvature and strength properties of different type ductus vary, multiple combination-form radial projection catheters with different degrees of flexibility can be provided for use with an ablation or ablation and angioplasty-capable barrel-assembly of given size. Structural factors that also affect flexibility are addressed below in the section entitled Fabrication of Radial Projection Catheters. For a given outer diameter, the material or materials and wall thicknesses, even when kept uniform as preferred, is variable as well, so that the flexibility of a radial projection catheter noncombination-form or combination-form can be specified over a wide range.

Reduced rotatability due to an increase in diameter with the addition of a combination-form radial projection catheter is compensated for by providing the distal end of the projection catheter with forward directed dentate keys about the rim which fit into corresponding recesses at the back of the muzzle-head when aligned. These are kept medial, or flush against the sides of the barrel-catheter to prevent chiseling into the lumen wall. Rotation is with the power and control housings of the barrel-assembly and projection catheter juxtaposed or ganged and used as a single handle, rotating the combination as a unit. The combination-form projection catheter can be withdrawn to any extent from just enough to free the muzzle-head for easier sidewise bending, to extracorporeal.

It can remain stationary while the more steerable and trackable barrel-assembly when unsheathed is advanced, and once the muzzle-head has reached the treatment site, again slid over the barrel-catheter to any distance up to the rear of the muzzle-head to add function. When not, a narrow gauged radial discharge barrel-assembly must also be used. Such limitation due to the narrow gauge of the ductus is simply given. For precise transluminal positioning, a radial projection catheter, like an ablation or ablation and angioplasty-capable barrel-assembly, can be inserted into a linear positioning stage-mounted airgun as addressed below in the section entitled Linear Positioning Stage or Table Airgun Mount.

Also like a combination-form barrel-assembly, a combination-form radial projection catheter can be designed to allow blood to flow through the central channel when unoccupied. The nose-hole is used but the side-port through which the cabled device is led is extracorporeal, so that distal or intracorporeal (endoluminal, intraductal, endovascular,) side-port or ports are required. A simple radial projection catheter consists of a pliant tube with radial projection units facing radially outward about the circumference over the intracorporeal length. The units are powered and controlled within the self-contained apparatus from a hand-grip enclosure at the rear or proximal end.

When a cabled device is not installed in the lumen, the tube is closed off at the distal or far end by a convex snap-in nose-plug as addressed in the next section entitled Throughbore, or Combination form, Radial Projection Catheters. With cabled device such as a laser or endoscope permanently installed in the lumen, the apparatus is a combination-form radial projection catheter, likewise addressed in the next section. Combination-form radial projection catheters that represent the peripheral component of a bipartite or duplex ablation or ablation and angioplasty-capable barrel-assembly and/or which can also be slid over a simple radial projection catheter must not only match the device to be ensheathed in size but in providing cutouts to avoid obstructing openings such as side-ports and blood-tunnels in the subjacent device.

Tick marks or rings etched into the outside of the barrel-catheter indicate that the openings in the ensheathed or subjacent barrel-assembly or projection catheter are in alignment with the cutout or a plurality thereof. Providing multiple cutouts at intervals allows the ensheathed device to be advanced or the projection catheter partially withdrawn without obstructing the openings. With either a combination-form radial projection catheter for use in the bloodstream or a combination-form ablation or ablation and angioplasty-capable barrel-assembly, a snap-in hole-plug that is dome-shaped but otherwise similar to those used in an electronic chassis is used to close off the nose-hole when the central channel or bore is to remain unoccupied. With the device intracorporeal, the plug is not removable. In the circulatory system, this prevents blood from passing through the central channel.

The device must be withdrawn, the plug removed, and the device reintroduced. A nose-cap is not used in the circulatory system because it prevents blood from passing when closed, obstructs viewing devices not projected past (beyond, distal to) it on the side on the opened cap side, and risks incisions. Except in the circulatory system, when the central channel of either an ablation (but not angioplasty) -capable combination-form barrel-assembly or a combination-form radial projection catheter must be kept free of debris and the flow through of blood is not preferred, a spring-loaded nose-cap is used that is swung open to a side by a cabled device as it pushes past the nose-cap and closes as the cabled devices recede behind the nose-cap.

The polymer material lining the central channel is non-thrombogenic and wetted with a an anticoagulant, such as heparin, or fibrinolytic, such as streptokinase, prior to insertion. A service catheter coated with this solution is inserted through the channel prior to entry into the vessel and whenever one cabled or catheteric device is exchanged for another. Neither the snap-in hole-plug nor spring-loaded nose-cap covers are removable with the device intracorporeal. The space available does not allow for withdrawal of a cap into the muzzle-head or the components to accomplish opening and closing by remote control. A nose-cap that can be snapped in when desired according to the procedure can avert some of these problems, but is not removable with the combination-form barrel-assembly or the projection catheter intraluminal.

Use of a spring-loaded nose-cap, to include one that can be snapped in, solely to nudge a rotational cutter sideways is objectionable in configuring the muzzle-head for only one of several different cabled devices when this could interfere with the use of other devices. For these reasons, the central channel is usually left without a nose-cap, sidewise urging of a rotational cutter accomplished by a spring device attached to the cutter without affecting the muzzle-head or other cabled devices that might be used. When the gauge (diameter) of the lumen allows use of a combination-form radial projection catheter with a barrel-assembly inserted, the oscillatory mode of the turret-motor can be used to reinforce the action of ablation shaving tool-inserts, for example.

For use in a blood vessel, the barrel-assembly must incorporate an embolic filter, as addressed above in the section entitled Trap-filter in Angioplasty-incapable Radial Discharge Muzzle-heads for Use in the Vascular Tree. Devices so equipped can be used with the central channel occupied or vacant. A minimally ablation or ablation and angioplasty-capable barrel-assembly is not intended for use independently of an airgun, and lacking a housing, poses no obstruction to use thus. The separability between barrel-assembly and projection catheter allows the barrel-assembly, while narrow in gauge and more pliant for better steerability and trackability, to be advanced to the treatment site first, and once placed, act as a 'guide wire' for the radial projection catheter that can add radial projection units to extend over the entire intracorporeal (endoluminal) length.

Steerability of the barrel-assembly may be implemented with the aid of an external electromagnet, by limiting the muzzle-head in length thus constraining the neck area available for electrical radial projection units, and by avoiding fluid units that require fluid lines and thus reduce flexibility. When the barrel-assembly is a tight fit, a combination-form radial projection catheter will not be usable. However, the same barrel-assembly in a less restrictive ductus would gain considerable capability through the overlayment of the projection catheter. Because the radii of curvature and strength properties of different type ductus vary, multiple combination-form radial projection catheters with different degrees of flexibility are made for use with an ablation or ablation and angioplasty-capable barrel-assembly of given size.

In addition to the factors that affect flexibility addressed below in the section entitled Fabrication of Radial Projection Catheters, the projection catheter can include any number and type of fluid lines and units whether electrical or fluid operated. Fluid operated radial projection units are not incorporated into any but the largest barrel-assemblies. Size-matched or paired barrel-assemblies and radial projection catheters are in effect Barrel-assemblies which to optimize endoluminal entry and functional range are made in two parts. This requires that the power and control housing of the barrel-assembly be disconnected. When the housing is reconnected, the housing of the radial projection catheter and that of the barrel-assembly are position in ganged relation.

The power and controls of each device, which can be used independently, are juxtaposed, so that patching between the two in order to share functions is unnecessary, When the barrel-assembly is introduced first, electrical/fluid system-neutral or spring released ejection tool-inserts in the muzzle-head can further contribute to trackability by releasing a lubricant with or without use of the oscillatory mode of the turret-motor. The radial projection catheter can likewise emit a lubricant whether slid over the barrel-assembly before or after introduction. Combining a combination form radial projection catheter with a combination-form barrel-assembly in this way is practicable only in larger ductus.

Fluoropolymers low in friction but higher in stiffness, these requirements can be met, for example, through the use of a highly pliant polymer which is given an outer coating of polytetrafluoroethylene or made as a coextrusion to produce a similar result. Further to minimize the risk of injury, when the muzzle-head incorporates electrically operated radial projection units with electrical/fluid system-neutral (spring-released, spring-discharged) syringe emitters loaded therein, these can be used with syringe ejection tool-inserts, or ejectors, to release a lubricant such as ACS Microslide®, Medtronic Enhance®, Bard Pro/Pel® or Hydro/Pel®, or Cordis SLX into the lumen to reduce clinging and the risk of injury during rotation and when passing curves.

This is limited, however, to the muzzle-head, whereas a radial projection catheter, simple or combination-form, can extend the emission of a lubricant throughout its length. Due to the minimal gauge attainable, such application in the arterial tree is limited. Because ablation or ablation and angioplasty-capable barrel-assemblies and radial projection catheters have numerous capabilities independently of one another, optimal functionality is obtained by making these in matched sets designed for use together according to gauge. Rather than abbreviating either for use as an attachment for the other, the paired apparatuses are made to be fully usable as independent but well matched when used together.

Rather than to incorporate controls in either to support the other as an attachment, the power and control housing, or battery-pack and hand-grip, with control panel of each contains the full complement of controls necessary to support its respective apparatus as independent. When combined, each retains its respective power and control housing with control panel. Combining the two thus combines the entire functionality of either. When the two are combined, retaining the full range of capabilities of either apparatus is not only necessary, but combination significantly multiplies the capabilities of the pair as such. When the combination-form radial projection catheter is introduced first, it can be used as a guide catheter for different cabled devices midprocedurally, and when a cabled device is introduced first, the cabled device can serve as a guide wire for the combination-form radial projection catheter.

However, due to the larger diameter of the muzzle-head, a barrel-assembly must be introduced first and thereafter jacketed with a radial projection catheter; only a disproportionately large combination-form radial projection catheter usable as a guide catheter for a barrel-assembly. The radial projection catheter can then be withdrawn before or together with the barrel-assembly. For the treatment of larger lumina such as the gastrointestinal tract, a combination-form radial projection catheter or a combination-form barrel-assembly can be used as a guide catheter for narrow catheteric and cabled devices. A combination-form barrel-assembly can be introduced first, used as a guide catheter, and as a guide wire for a radial projection catheter.

The catheteric and cabled devices can be freely interchanged in any sequence, and the radial projection catheter can be withdrawn before the barrel-assembly, but the muzzle-head will prevent the barrel-assembly from being withdrawn without the projection catheter. A combination-form radial projection catheter is effectively an ablation or ablation and angioplasty-capable combination-form barrel-assembly with the same outward conformation but without a ballistic component. As with a combination-form barrel-assembly, the device, such as a laser or endoscope, can be installed permanently or a lumen provided for accepting interchangeable cabled devices.

Such interchangeability can have much value, because it allows cabled devices to be changed not just midprocedurally but while the catheter remains intracorporeal. The pliancy, hence, trackability of the catheter will vary with each different type cabled device or with none in the lumen. Withdrawing the cabled device without transluminal movement of the catheter can therefore allow the catheter to be passed through a curve before the cabled device is reinserted. To reduce the risk of incisions or perforations, the radial projection catheter must present a leading edge that is blunted, an outer surface that is slippery, and be highly pliant.

VIII4. Slidable Projection Catheter Power and Control Housing

To allow ensheathment and the ability to maintain a consistent distance from the entry wound, the power and control housing hand-grips of barrel-assemblies and projection catheters ensheathable within a combination-form radial projection catheter of larger diameter must be slidable and removable by being slid off the proximal end of the barrel-catheter. The housing thus functions in the same manner as one in an angioplasty-capable barrel-assembly, as addressed above in the section entitled Slidable Ablation or ablation and angioplasty-capable Barrel-assembly Power and Control Housing.

VIII5. Fabrication of Radial Projection Catheters

One cross section profile suitable for an extrusion to be made into a radial projection catheter has circular or rectangular lumina in the number required positioned at equal angles about the central longitudinal axis. To expedite extrusion, longitudinally separating, inner, and outer walls are the same in thickness. This profile makes possible the narrowest projection catheters and is preferred when only electrical projection units, which demand less diameter than fluid units, are to be included. Combination-form radial projection catheters are generally larger in diameter and more readily accommodate fluid circuits. Non-combination and combination-form radial projection catheters differ only in that the central channel or lumen in the latter is large enough to accommodate a cabled device such as an endoscope or laser, for example.

Radial projection catheters are made of custom extruded multiluminal tubing. For more problem free production, the wall thicknesses, to include the inner, outer, and those separating the lumina, which can have any shape as seen in cross section, are kept the same. Since the outer surface of the radial projection catheter can be coated or shrink-wrapped in polytetrafluoroethylene film, the underlying tubing is chemically isolated and can therefore consist of any pliant material or materials, even those allergenic on direct contact. The extrusion used being the difference, the two types are fabricated alike. A narrow projection catheter for use in blood vessels usually includes a hemispherical heat-window at the nose with convexity or dome directed forward (downstream, distad) to thermoplasty any vulnerable plaque and burn any debris that rupture of the plaque cap would liberate.

An extrusion profile that better accommodates fluid circuits consists of a central and two radially outward concentric lumina. The center and outer lumina are connected by radial arms that are longitudinally extended. These running partitions or walls divide the outer lumina into arcuate passageways. When the diameter is less restrictive, the simple projection catheter includes a central lumen leading distally up to the hole at the center of a hemitoroidal heat-window with convexity or dome directed forward. In a small diameter embodiment to be used solely for injection, for example, and not expected to generate more debris than the heat-window can destroy, the central lumen and hole are used to hold a fiberoptic endoscope or other aid to viewing.

If a projection catheter that is limited to a small diameter is to be used with ablative or abrasive tool-inserts that generate debris, the central lumen and hole are used to hold an embolic filter silo with deployment and stowing solenoid as that shown in FIG. 50. A still less restrictive diameter allows the central lumen and hole in the nose-window to house both a fiberoptic endoscope and embolic filter side by side. Using the kind of extrusion preferred for an electrical or a fluid circuit as appropriate, the radial holes for the lift-shafts are drilled into the side of the extrusion while it is stabilized in a grooved jig of applicable diameter which is clamped down onto the table of a drill press and advanced or positioned sidewise by means of a slide screw.

For low volume production, sidewise positioning of the jig to align the catheter to the drill bit is manual by rotating the slide screw, while for higher volumes, the jig is advanced by means of a linear positioning stage driven by a point to point or discrete (noncontinuous path) numerically controlled stepper motor. Square lift-shafts are drilled with a Reuleaux triangular bit in an eccentric or floating chuck such as produced by the Watts Brothers Tool Works, Wilmerding, Pa. For precise machining, catheters made of rubbery material that resist drilling are first frozen. Whether electrical or fluid, the circuit is preassembled by connection in series into a string or chain of projection units with intervening conductors.

Exceptionally, the receiving lift-shaft holes and units for insertion into these can have different cross sections. The string is pushed through its lumen so that each unit is vertically aligned to its respective hole and the rear or proximal end of each conductor projects past or overextends the rear end of the catheter. A rod of the diameter required to bring the upper edges of the units flush to the outer surface of the catheter having a front end tapered to expedite sliding under each unit is then pushed through the lumen successively driving each unit up into its respective hole wherein it is retained by friction fit. Any difficulty in sliding the front end of the lifting rod beneath a unit is dealt with by lifting the unit from the outside by means of a pin with a nonallergenic pressure sensitive adhesive at its tip.

The nose heat-window, fiberoptic endoscope, embolic filter, and/or other viewing or treatment device, and a ferromagnetic cord to expedite steering and abutment against the lumen wall by means of a hand held electromagnet are preassembled into a joint holder which is inserted at the forward or distal end of the projection catheter, the conductor pushed down through the lumen first, then the holder at the distal end pushed into a premachined opening in which the holder is retained by friction fit. The rear or proximal end of the projection catheter ends in a terminal plate with the contact or fluid port for each circuit.

The terminal or end plate, which has a hole with surrounding toroidal electrical contact for each conductor, is then heated so that the toroid surrounded hole for each conductor is sufficiently expanded to allow the projecting ends of the conductors to be passed through its respective hole. The end plate is pushed over the projecting ends of the conductors and flush against the rear end of the catheter. Cooling can be accelerated by means of a vortex cold air gun, for example. Upon cooling, the conductors are locked into their respective holes and the end plate held flush against the rear of the catheter by contraction seizure at room temperature.

The excess conductors are snipped off flush to the rear faces of the holes. The end plate is now a plug which fits into the corresponding socket at the front of the power and control housing hand grip. Since circumferentially discretionary control requires that each circuit be separately controllable, it is important that each conductor be connected to the correct contact in the socket. Proper alignment of the plug in the socket is obtained by aligning a tick mark or scratch on the side of the rear end of the catheter with another at the edge of the socket.

IX. Side-Ports

IX1. Proximal Side-Ports in Angioplasty-Capable Barrel-Assemblies

Barrel-assemblies for use in the vascular tree must incorporate discharge gas pressure diversion channels that vent to the exterior to prevent the introduction of gas into the bloodstream. Venting through a slit membrane of suitable resilience at the proximal end of the barrel-catheter would release the gas into the airtight chamber of the airgun. Thus, a side-port (side-hole) in an extracorporeal segment (a segment outside the patient, proximal to the entry wound) of the barrel-catheter, with a one-way outlet valve serves as discharge gas pressure relief vent. The side-port, similar to a side-hole in a conventional catheter, communicates with the peribarrel space (qv.) or gas pressure diversion channel inside the barrel-catheter.

IX2. Proximal Side-Ports in Combination-Form Barrel-Assemblies and Combination-Form Radial Projection Catheters Generally larger in diameter than a vent and leading via a frontomedially directed passageway into the central channel or (qv.) bore of a combination-form (qv.) barrel-assembly or a combination-form radial projection catheter, a side-port can serve to pass a cabled device or devices, such as a fiberoptic endoscope or a laser, into the central channel so that it can be moved up to or through the nose or front end. Especially with respect to such use, a side-port should not be confused with a side-socket (qv.) which, also limited to placement in an extracorporeal (extraductal, proximal) segment or on the side of the combination-form barrel-assembly or radial projection catheter power and control housing, is an electrical and/or fluid line connector, that is, a receptacle.

IX3. Distal Side-Ports in Combination-Form Barrel-Assemblies and Combination-Form Radial Projection Catheters In an intracorporeal (endovascular, intraductal, distal) segment of a combination-form barrel-assembly or a combination-form radial projection catheter facing antegrade, or with the flow of blood, a side-port allows blood to flow through the unoccupied bore or central channel (qv.) and out the nose or front end. More specifically, the blood flows into the side-port, thence through an anteromedial tunnel-tube that isolates blood or other ductus contents from gases past any intervening barrel-tube into the central channel, and is thus essentially equivalent to a side hole in an existing catheter.

X. Steering and Emergency Recovery of Implants with the Aid of an External (Extracorporeal) Electromagnet X1. Use of an External Electromagnet to Assist in Steering or in Freeing the Muzzle-Head Conventional hand-held electromagnets are portative, not tractive, that is, made to carry magnetically susceptible matter when in direct contact, not to draw susceptible matter over a distance. Such magnets can generally exert tractive force out to a distance of about 3 inches (76.2). This is generally sufficient for a separation function such as lifting away susceptible debris from parts moving past the magnet or magnets suspended above a conveyor belt, but inadequate to extract a susceptible object from within the body where interventing tissue will resist extraction and the depth into tissue may be considerably greater than 3 inches.

There are three ways to overcome this limitation, the first described below in section X2c, entitled Stereotactic Arrest and Extraction of a Circulating, Dangerously Mispositioned, or Embolizing Miniball. Essentially, the $B_0$ magnet of a magnetic resonance imaging machine is connected by a silver wire cable to a hand-held probe. In most instances, this greater tractive force is more dependable and available in any center where intravascular procedures are routinely performed. The second method is the use of a custom made floor machine-independent hand-held electromagnet with a core or armature of pure iron or fused iron-silicon (Si—Fe) crystals wound about with insulated silver wire. Spherule detention pertains both to emergency and nonemergency conditions.

Si—Fe crystals are readily and economically obtained and more susceptible to magnetic force than other materials (Stoller, H. M., Austin, F. E., and Seeger, E. W. 1920. *Small Motors, Transformers, Electromagnets*, Chicago, Ill.: American Technical Society, page 21 on (not to be confused with the same authors' *Small Motors, Transformers, Electromagnets: A Practical Presentation of Design and Construction Data for Small Motors, Small Low-and High-tension Transformers, Electromagnets, and Induction Coils*; Haus, H. A., and Melcher, J. R. 1989. *Electromagnetic Fields and Energy*, Englewood Cliffs, N.J.: Prentice-Hall, also available at Massachusetts Institute of Technology OpenCourseWare http://ocw.mit.edu, Chapter 9; see also Wu, Q., He, W., Liu, H. L., Ye, J., Zhang, X. Q., Yang, H. T., Chen, Z. Y., and Cheng, Z. H. 2013. "Tuning Magnetic Anisotropies of Fe films on Si(111) Substrate via Direction Variation of Heating Current," *Scientific Reports* 3:1547; Ye, J., He, W., Wu, Q., Liu, H. L., Zhang, X. Q., Chen, Z. Y., and Cheng, Z. H. 2013. "Determination of Magnetic Anisotropy Constants in Fe Ultrathin Film on Vicinal Si(111) by Anisotropic Magnetoresistance," *Scientific Reports* 3:2148; Chang, H. W., Tsay, J. S., Hung, Y. C., Chan, W. Y., Su, W. B., Chang, C. S., and Yao, Y. D. 2011. "Investigation of Magnetic Properties and Microstructure of Ultrathin Co Films Grown on Si(111)-7×7 Surface," *Journal of Nanoscience and Nanotechnology* 11(3):2696-2699; Sorbello, F., Hughes, G. M., Lejcek, P., Heard, P. J., and Flewitt, P. E. 2009. "Preparation of Location-specific Thin Foils from Fe-3% Si Bi- and Tri-crystals for Examination in a FEG-STEM [field emission gun scanning transmission electron microscope]," *Ultramicroscopy* 109(2):147-153; Andreev, A. V., Yoshii, S., Kuz'min, M. D., de Boer, F. R., Kindo, K., and Hagiwara, M. 2009. "A High-field Magnetization Study of a Nd(2)Fe(14)Si(3) Single Crystal," *Journal of Physics. Condensed Matter* 21(14):146005; Hashi, S., Ishiyama, K., Arai, K. I., Kawasaki, M., and Yamashiro, Y. 1996. "Study on the Deformation of 3% Si—Fe Single Crystal with Magnetic Field Being Deviated from [001]," *Institute of Electrical and Electronics Engineers Transactions on Magnetics* 32(5):4848-4850; Tanaka, T., Takahashi, M., Wakiyama, T., Yamato, M., and Watanabe, D. 1985. "Magnetic Properties of 6.5 wt % Si—Fe Alloy Single Crystal with Phase Separation," *Institute of Electrical and Electronics Engineers Translation Journal on Magnetics in Japan* 1(5): 548-549).

When a magnetic resonance imaging machine is not available, the use of such a magnet necessitates the incorporation of iron-silicon crystals in implants to be drawn or barrel-assembly muzzle-head to be rendered steerable by application of external tractive force. An electromagnet is used to allow adjustment of the field strength to the minimum essential to steer the muzzle-head or to stabilize it in position by abutment against the luminal wall.

The muzzle-head recovery tractive electromagnets are themselves magnetically susceptible and make possible the use of an external electromagnet to steer the barrel-assembly (see also Mathieu, J-B., Soulez, G., Beaudoin, G., Felfoul, O., Chanu, A., and Martel, S. 2008. "Steering and Tracking of Magnetic Catheters Using MRI Systems," *Abstract No. 76, Journal of Vascular and Interventional Radiology* 19(2): S31-S31; Tamaz, S., Chanu, A., Mathieu, J.-B., Gourdeau, R., and Martel, S. 2008. "Real-time MRI-based Control of a Ferromagnetic Core for Endovascular Navigation," *Institute of Electrical and Electronics Engineers Transactions on Biomedical Engineering* 55(7):1854-1863; Chanu A., Felfoul O., Beaudoin G., and Martel S. 2008 "Adapting the Software Platform of MRI for the Real-time Navigation of Endovascular Untethered Ferromagnetic Devices," *Magnetic Resonance in Medicine* 59(6):1287-1297; Grady, M. S., Howard, M. A. 3rd, Dacey, R. G. Jr., Blume, W., Lawson, M., Werp, P., and Ritter, R. C. 2000. "Experimental Study of the Magnetic Stereotaxis System for Catheter Manipulation within the Brain," *Journal of Neurosurgery* 93(2):282-288). Radial projection catheters and combination-form radial projection catheters accept a snap-in nose-cap containing ferrous metal for the purpose.

Recently a promising third category of means for magnetically steering nanotherapeutics to a nidus or lesion deep within the body has emerged and continues under intensive research (Mahajan, K. D., Ruan, G., Dorcéna, C. J., Vieira, G., Nabar, G., and 5 others 2016. "Steering Microtubule Shuttle Transport with Dynamically Controlled Magnetic Fields," *Royal Society of Chemistry Nanoscale Issue* 16; Mohammed, L., Ragab, D., and Gomaa, H. 2016. "Bioactivity of Hybrid Polymeric Magnetic Nanoparticles and Their Applications in Drug Delivery," *Current Pharmaceutical Design* 22(22):3332-3352; Nacev, A., Weinberg, I. N., Stepanov, P. Y., Kupfer, S., Mair, L. O., and 4 others 2015. "Dynamic Inversion Enables External Magnets to Concentrate Ferromagnetic Rods to a Central Target," *American Chemical Society Nano Letters* 15(1):359-364; Estelrich, J., Escribano, E., Queralt, J., and Busquets, M. A. 2015. "Iron Oxide Nanoparticles for Magnetically-Guided and Magnetically-Responsive Drug Delivery," *International Journal of Molecular Sciences* 16(4):8070-8101; Mardinoglu, A. and Cregg, P. J. 2015. "Modelling the Effect of SPION [superparamagnetic iron oxide nanoparticles] Size in a Stent Assisted Magnetic Drug Targeting System with Interparticle Interactions," *Scientific World Journal* 2015:618658; Laurent, S., Saei, A. A., Behzadi, S., Panahifar, A., and Mahmoudi, M. 2014. "Superparamagnetic Iron Oxide Nanoparticles for Delivery of Therapeutic Agents: Opportunities and Challenges," *Expert Opinion on Drug Delivery* 11(9): 1449-1470; Kumar, A., Jena, P. K., Behera, S., Lockey, R. F., Mohapatra, S., and Mohapatra, S. 2010. "Multifunctional Magnetic Nanoparticles for Targeted Delivery," *Nanomedicine* 6(1):64-69; Shapiro, B. 2009. "Towards Dynamic Control of Magnetic Fields to Focus Magnetic Carriers to Targets Deep Inside the Body," *Journal of Magnetism and Magnetic Materials* 321(10):1594-1599; Polyak, B. and Friedman, G. 2009. "Magnetic Targeting for Site-specific Drug Delivery: Applications and Clinical Potential," *Expert Opinion on Drug Delivery* 6(1):53-70; Chen, H., Kaminski, M. D., Pytel, P., Macdonald, L., and Rosengart, A. J. 2008. "Capture of Magnetic Carriers within Large Arteries Using External Magnetic Fields," *Journal of Drug Targeting* 16(4): 262-268).

Yet another method for cavitating or breakdown lyzing of microemboli, which applies only to miniballs consisting of a magnetically susceptible nanoparticulate embedded in a reducible matrix, is microtripsy (see, for example, Zhang, X., Jin, L., Vlaisavljevich, E., Owens, G. E., Gurm, H. S., Cain, C. A., and Xu, Z. 2015. "Noninvasive Thrombolysis Using Microtripsy: A Parameter Study," *Institute of Electrical and Electronics Engineers Transaction on Ultrasonics, Ferroelectrics, and Frequency Control* 62(12):2092-2105; Zhang, X., Owens, G. E., Gurm, H. S., Ding, Y., Cain, C. A., and Xu, Z. 2015. "Noninvasive Thrombolysis Using Histotripsy Beyond the Intrinsic Threshold (Microtripsy)," *Institute of Electrical and Electronics Engineers Transaction on Ultrasonics, Ferroelectrics, and Frequency Control* 62(7): 1342-1355' Lin, K. W., Kim, Y., Maxwell, A. D., Wang, T. Y., Hall, T. L., Xu, Z., Fowlkes, J. B., and Cain, C. A. 2014. "Histotripsy Beyond the Intrinsic Cavitation Threshold Using Very Short Ultrasound Pulses: Microtripsy," *Institute of Electrical and Electronics Engineers Transaction on Ultrasonics, Ferroelectrics, and Frequency Control* 61(2): 251-265).

While the small electromagnets within stent-jackets and impasse-jackets used to draw spherules into the intima are wound with silver wire about an iron core, these are generally proximate enough as not to necessitate further modification. Stabilization in this way rarely pertains to discharge but rather to imaging whether of an onboard fiberoptic endoscope, for example, or an external viewing device. An external tractive or separator-type electromagnet with a core or armature as a narrow tapered, or subulate, probe ending in a narrow tip is used to focus the magnetic force reducing the risk of disrupting any implants. The same device can be used to free the muzzle-head were it to cling to the lumen wall. Using an external magnet or a tool-insert, a clinging muzzle-head can be pushed aside for a syringe ejection tool-insert to release a lubricant into the gap. The turret-motor is then used to rotate or if necessary, to oscillate and thus free the muzzle-head.

X2. Use of an External Electromagnet to Assist in Mishap Recovery

X2a. Interception and Recovery of a Miniball Entering the Circulation

Potentially embolizing miniballs released into the circulation midprocedurally are seized with the aid of the recovery electromagnets in the muzzle-head, a run-ahead embolic filter, an external electromagnet, and an impasse-jacket prepositioned downstream of the implantation site, which latter can be left in place indefinitely to prevent embolization postprocedurally. Deterrents to embolization by due to the loss of a miniball in the circulation are incorporated into barrel-assemblies and stent-jackets as well as the miniballs. Its mass and the effect of gravity usually negligible, a miniball released into the bloodstream will continue to move with the current despite collateral factors, such as the blood pressure and position position of the body. A stenting miniball that enters the circulation must do so during or following discharge.

While highly improbable, this could happen due to an airgun malfunction, discharge that is faulty due to human error, or failure of the magnetic stent-jacket, such as an interim migration due to improper fixation, all of which can be observed with the proper imaging equipment. The arresting, safe resituation to a location outside the vessel, and if necessary, extraction entirely outside the body of a miniball is accomplished with downstream magnets. Those implanted incorporate permanent magnets and are absorbable or permanent according to the application. While impasse-jackets are specialized to trap and/or hold miniballs, any more strongly magnetized downstream stent-jacket will trap a miniball loose in the circulation and continue to hold the miniball unless the strength of jacket magnetization were to drop beneath that required to do so, which the use of neodymium lanthanoid virtually eliminates.

Exceptionally, an absorbable radiation shield-jacket, used to suspend seed miniballs in the lumen alongside the lesion or stent-jacket used to shield ductus-intramurally implanted seed miniballs only so long as necessary, will allow a miniball to be extracted when necessary. Such jackets have an absorbable outer radiation shield, as addressed above in the section entitled Radiation Shield-jackets and Radiation Shielded Stent-jackets Absorbable and Nonabsorbable, about an extraction grid, usually made of a magnesium alloy formulated to be absorbed over a longer period when not permanent. Extracorporeal interception, relocation, and extraction is by means of an electromagnet.

A permanent impasse-jacket protects against miniball embolization at any time and will suspend medication miniballs or draw drug carrier nanoparticles from a ferrofluid administered at any later date. Medication miniballs are absorbed, limiting the risk of embolization to a more or less predictable interval, and contain sufficient ferromagnetic content to allow prompt emergency retrieval if necessary. Irradiating miniballs are likewise preloaded with superparamagnetic magnetite or maghemite nanoparticles or finely grained powder. The utility of any external magnet whether hand-held or through adaptation of the $B_0$ magnet of a magnetic resonance machine, as addressed in section X2c below entitled Stereotactic Arrest and Extraction of a Circulating, Dangerously Mispositioned, or Embolizing Miniball, is critically dependent upon and directly proportional to the focus or targeting ability of the magnetic field.

The means for achieving a tight focus are described, this factor critical to establishing the clearance required to nearby implants containing ferrous matter in order not to disrupt these. The type field used for magnetic heat induction, which may likewise make use of magnetic resonance machine magnets, is alternating, not static. Powerful static fields can attract ferrous objects as to pose a projectile hazard and alternating fields will induce heat in unintended objects containing ferrous metal (see, for example, Hartwig, V., Giovannetti, G., Vanello, N., Lombardi, M., Landini, L., and Simi, S. 2009. "Biological Effects and Safety in Magnetic Resonance Imaging: A Review," *International Journal of Environmental Research and Public Health* 6(6):1778-1798; Schenck, J. F. 2000. "Safety of Strong, Static Magnetic Fields," *Journal of Magnetic Resonance Imaging* 12(1): 2-19).

Mere attentiveness precludes such mishaps. Once a miniball with deep surface texture becomes infiltrated with tissue, it can be left in place indefinitely. If for any reason this is not wanted, then a sudden pulse from a powerful external electromagnet is used to pull the miniball outside the ductus to a safe location within or entirely out of the body. Sudden extraction by this means should impose minimal trauma, which can be assured when an impasse-jacket, as addressed above in the sections entitled Concept of the Impasse-jacket and Miniball and Ferrofluid-borne Particle-impassable Jackets, or Impasse-jackets, has been prepositioned about the miniball at the time of introduction.

While necessitating minor surgery to preposition, an impasse-jacket can spare the need for any other measures to intercept, hold, and extract the miniball. Once trapped in the jacket, unless radioactive, releasing a drug or drugs that would be mistargeted, or a need for resonance imaging without burning the site arises, the miniball need not be extracted. When the extractive force is less than shocking to the surrounding tissue, the grid of an impasse-jacket, because it frames about the miniball, protects against the tearing of adjacent tissue. The removal of a tissue integrated miniball or stay should never require excision.

The third method for steering or drawing nano and microtherapeutics deep within the body using an extracorporeal magnetic field is addressed shortly above. Stopping a larger miniball from continued travel is similar to drawing drug carrier nanoparticles from the blood where obtaining a locoregionally high-gradient magnetic field is an ongoing area of research for targeting drug delivery (see, for example, Shapiro, B. 2009, Op cit.; Polyak, B. and Friedman, G. 2009 Op cit.; Chen, H., Kaminski, M. D., Pytel, P., Macdonald, L., and Rosengart, A. J. 2008, Op cit.).

Barrel-assemblies for use in the vascular tree incorporate recovery electromagnets and a run-ahead embolic filter that significantly reduce the risk of a miniball entering the bloodstream. Should it occur, a miniball released into the circulation miniball is intercepted and relocated or recovered before it can embolize. If it does so, then it can be promptly removed. Magnetic stent-jackets incorporate multiple features to resist gradual migration and sudden dislodgement and are formulated, then encapsulated, to resist chemical breakdown and preserve unit integrity.

X2a(1). Midprocedural Interception and Recovery of a Miniball Entering the Circulation Since, whether due to human error or malfunction, the magnets in the muzzle-head may be unenergized or the filter undeployed, measures must be provided to intercept and recover a miniball released into the bloodstream, these precautions notwithstanding. Precautionary measures against the risk of embolization consist of prepositioning interception magnets downstream. When the risk will persist postprocedurally, impasse-jackets are implanted. Where possible, the preabsorption life of these is keyed to the potential duration of the risk. Risk pertinent midprocedurally is protected against with an external electromagnet and any impasse-jacket or more powerfully magnetized stent-jacket prepositioned downstream.

The spherical surface of the miniball and its relatively small mass of ferromagnetic material, especially when not meant for stenting, require the use of a powerful tractive or separator-type electromagnet. Platelet blockade having been administered, an extracorporeal tractive electromagnet with field concentrating and directing subulate probe is prepositioned sufficiently downstream from other implants to seize and hold any miniball that flows past.

The miniball is held against the lumen wall, the muzzle-head brought up alongside, and its recovery electromagnets used to retrieve the miniball. Periodic imaging of the segment of the ductus in the magnetic path also discloses a failure to successfully implant that might otherwise go undetected. If this is impossible, as when the lumen will not admit the muzzle-head, then the miniball is prevented from circulating by retracting it into or through the lumen wall. If through and the blood is infected, an antibiotic is used. By definition, the miniball will be minute relative to the ductus in which it was to have been implanted, so that a breach will spontaneously close promptly if not immediately.

If the wall is thick and reentry into the lumen implausible, then the sterile and minute miniball is allowed to remain. If the wall is thin, then the miniball is forcibly extracted into the neighboring tissue where, if innocuous, it is allowed to remain. If the end position poses a danger, then the miniball is forcibly extracted entirely out of the body over the most direct and safe path, as described in section X2c below entitled Stereotactic Arrest and Extraction of a Circulating, Dangerously Positioned or Embolizing Miniball. Provided a safe path is available, forcible extraction from within the body is an option whether during discharge or thereafter.

X2a(2). Postprocedural Recovery of a Miniball in the Vascular Tree

Once placed, an impasse-jacket will stop a miniball from continued travel through the bloodstream whether mid- or postprocedurally. The impasse-jacket can be left in place and should not significantly demagnetize over the life of the patient. In the very young, the possibility of demagnetization over time may be compensated for with stronger magnetization. The same does not apply to stent-jackets, magnet-jackets, and patch-magnets, for example, which act directly on tissue in such a way that excessive traction can result in perforation or delamination, for example.

Miniballs are too small to occlude the lumen at the level targeted, and subjacent to adluminal tissue of the lumen wall while drawn abluminally (radially outward away from the lumen) by the magnetic stent-jacket, are not likely to enter the bloodstream; however, were such to occur, the miniball would have to be stopped before it became an embolism. The small miniball-to-lumen diameter ratio means that miniballs are far upstream from an eventual point of occlusion, affording a significant distance over which one or more stopping-magnets can be prepositioned. Where the situation warrants, one or more miniball impasse-jackets as addressed above in the section entitled Miniball Impasse-jackets or Guards are prepositioned downstream.

The asymptomatic release from the treatment stent of a miniball is detected with the aid of a periodic radiograph. Removal or extraction is a clinical judgment based upon the possible consequences of inaction. If necessary, the miniball is removed by means such as described below in section X2c entitled Stereotactic Arrest and Extraction of a Circulating, Dangerously Mispositioned, or Embolizing Miniball. As addressed above in the sections entitled (The Intraductal Component of the Extraluminal Stent and the Means for Its Insertion and Double-wedge Stent-jacket Rebound-directing Linings), the risk of perforation as a deterrent can be avoided by prepositioning the stent-jacket. Previous exposure of the ductus nullifies any objection to the separate percutaneous access required.

When the barrel-assembly is used to target a lesion for the delivery of medication unrelated to stenting, however, separate access is avoided. Whether by rebounding off a prepositioned stent-jacket, some other midprocedural mishap, or the later sustaining of a direct blow, entry into the circulation of one or more miniballs must have countermeasures. Miniballs are inserted beneath the adventitia at an acute antegrade angle to undercut the inner layers of the lumen wall, additional retentive strength or anchoring imparted when a textured surface is infiltrated by the surrounding tissue. Mechanical retention can be increased through the use of miniballs coated with a protein solder that is heated just after implantation. In a magnetic stent-jacket, the pull of the magnets additionally acts to retain the miniballs in position.

Moreover, the stent-jacket is held in position by its resilience, attraction of its magnets to the intraductal miniballs, and end-ties. As addressed in the section above entitled Protective Encapsulation of the Stent-jacket, the base-tube with magnets is encapsulated for chemical isolation and to bind the elements of the extraductal component of the stent into a unit that make the migration or dropping away of the retentive magnets improbable. These factors militate against the accidental release of miniballs into the lumen even were the stent to take a direct blow.

Several methods exist to prevent miniball embolization, especially significant in carotid stenting where emboli can pass to the brain. Distal and proximal protective embolic filters, balloon barriers, and the application of an external magnetic field or focused ultrasonic beam are addressed above in section X1 entitled Use of An External Electromagnet to Assist in Steering or in Freeing the Muzzle-head, and the magnetic content of miniballs allows such alternative methods of breakdown in addition to conventional means of filtration and mechanical blockage. Only the smallest miniballs fall within the size range of microemboli which are irretrievable and believed to cause silent watershed or border zone microinfarcts (see Momjian-Mayor, I. and Baron, J. C. 2005. "The Pathophysiology of Watershed Infarction in Internal Carotid Artery Disease: Review of Cerebral Perfusion Studies," *Stroke* 36(3):567-577).

Additionally, even when as small as an embolus resulting from an atherothrombogenic plaque fracture, or as the spontaneous result of an emboligenic disorder, or through release during a transluminal procedure to effect blockage at a level which results in a cerebral infarction, a miniball released into the vascular tree will be singular or few in number and not likely to educe a consequence associated with the release of a large number of thromboemboli. Unless formulated to remain temporarily, a miniball used to stent is not, however, resorbable or susceptible to thrombolytic medication, so that its landing site will determine whether it should be left undisturbed as innocuous, or must be resituated or extracted as addressed above in sections 12 entitled Concept of the Impasse-jacket and I15 entitled Miniball and Ferrofluid-impassable Jackets, or Impasse-jackets.

Infarction tends to be proportional to the level of stenosis regardless of cause, whether atherothrombogenic and local or cardioembolic (see, for example, Polito, V., La Piana, R., Del Pilar Cortes, M., and Tampieri, D. 2017. "Assessment of Clot Length with Multiphase CT Angiography in Patients with Acute Ischemic Stroke," *Neuroradiology Journal* 30(6):593-599; Seitz, R. J. and Donnan, G. A. 2015. "Recovery Potential after Acute Stroke," *Frontiers in Neurology* 6:238; Thanvi, B. and Robinson, T. 2007. "Complete Occlusion of Extracranial Internal Carotid Artery: Clinical Features, Pathophysiology, Diagnosis and Management," *Postgraduate Medical Journal* 83(976):95-99; Lodder, J., Hupperts, R., Boreas, A., and Kessels, F. 1996. "The Size of Territorial Brain Infarction on CT Relates to the Degree of Internal Carotid Artery Obstruction," *Journal of Neurology* 243(4):345-349; Olsen, T. S., Skriver, E. B., and Herning, M. 1985. "Cause of Cerebral Infarction in the Carotid Territory. Its Relation to the Size and the Location of the Infarct and to the Underlying Vascular Lesion," *Stroke* 16(3):459-466). Furthermore, the stent is usually placed following an angioplasty that removed or debulked the stricture, so that only an embolus larger than a miniball could occlude the lumen. Midprocedural growth in the potential obstruction by clot adhesion to the miniball is suppressed medically.

Restenosis suppressive measures should perpetuate this patency. The miniball is likely to be stopped at a level that if lacking collateral circulation, still has a small extent of dependency. Postprocedural administration of anticoagulant medication need not continue past anchoring by tissue infiltration. Where collateral circulation is lacking, an embolizing miniball is either drawn into a safe location as described above, or is extracted as described in section X2c below entitled Stereotactic Arrest and Extraction of a Circulating, Dangerously Positioned, or Embolizing Miniball. Stays should rarely if ever necessitate retrieval by such means, even as the result of a direct blow.

X2b. Stereotactic Resituation of a Mispositioned Miniball

In many if not most instances, a mispositioned miniball, which will usually be a fraction of a millimeter in diameter, is best left undisturbed. The ability to resituate a mispositioned miniball with an external electromagnet depends upon the relation between the resistance to penetration by the miniball of the tissue and the strength of the magnetic field. A hand-held electromagnet is adequate to extract a miniball through soft and tissue and aponeuroses, for example. A magnetic resonance machine adapted as described below will extract a miniball trapped behind the hardest tissue. The magnet is pulsed at an apposite level of current to incrementally draw the miniball into the target location. The same method can be used to nudge a closely misplaced miniball into the desired location.

The miniball can be drawn into the circulation with a second magnet prepositioned to incept it, then the interception magnet used to pulse the miniball into the surrounding tissue if not the desired location. For emergency interception and extraction midprocedurally using a preplaced impasse-jacket or an external electromagnet, sufficient ferromagnetic material must be dispersed throughout an absorbed, to include a drug-releasing miniball, so that its magnetic susceptibility does not degrade with its dissolution to the point where it is no longer extractable. For arrest and extraction, the magnetically susceptible material, ordinarily superparamagnetic magnetite or maghemite nanoparticles or finely grained powder; or for heat induction, iron grains.

Uniform distribution also affords greater iron particulate surface area for absorption and eliminates any need to extract a relatively large core. A miniball in the brain is pulse-drawn into a vessel that will allow it to be intercepted by a prepositioned magnet once no longer intracranial, or if judged too risky, then into a ventricle or the subarachnoid space. Extravasation attendant upon the perforation of an intracranial vessel by a miniball less than one millimeter in diameter is not comparable to that following the rupture of an arteriovenous malformation or an aneurysm.

Any volume of blood released thereby should resorb in a day (Kim, J. Y. and Bae, H. J. 2017. "Spontaneous Intracerebral Hemorrhage: Management," *Journal of Stroke* 19(1):28-39; Maugeri, R., Anderson, D. G., Graziano, F., Meccio, F., Visocchi, M., and Iacopino, D. G. 2015. "Conservative vs. Surgical Management of Post-traumatic Epidural Hematoma: A Case and Review of Literature," *American Journal of Case Reports* 16:811-817; Sahni, R. and Weinberger, J. 2007. "Management of Intracerebral Hemorrhage," *Vascular Health and Risk Management* 3(5):701-709; Dabrowska, E., Jagodziński, Z., and Michalak, W. 1992. "Remarks on Conservative Treatment of Cerebral Hematoma," (in Polish with English abstract at Pubmed), *Neurologia i Neurochirurgia Polska* [Polish Neurology and Neurosurgery] Supplement 1:276-282; Koziarski, A. 1991. "Conservative Treatment of Post-traumatic Intracerebral Hematoma," (in Polish with English abstract at Pubmed), *Neurologia i Neurochirurgia Polska* [Polish Neurology and Neurosurgery] 25(2):230-237; Bidziński, J., Koziarski, A., and Frankiewicz, E. 1989. "Conservative Treatment of Intracranial Hematomas and the Dynamics of their Resorption," (in Polish with abstract in English at Pubmed) *Neurologia i Neurochirurgia Polska* [Polish Neurology and Neurosurgery] 23(1):27-34). Except in the brain, a suitably located miniball not containing a metal or metal containing shell or magnetized lanthanoid can be 'lithotripsied' in place. The brain excepted, if the attempt to move the miniball to a more effective or safe location fails, it can be extracted entirely outside of the body as addressed in the following section entitled Stereotactic Arrest and Extraction of a Circulating, Dangerously Positioned, or Embolizing Miniball.

X2c. Stereotactic Arrest and Extraction of a Circulating, Dangerously Mispositioned, or Embolizing Miniball As addressed at numerous points throughout this specification, an errant miniball is recoverable in any circumstance. With sufficient field force, a magnet can draw a miniball entirely outside the body. While the risk for significant trauma with such small implants is slight, the path is predetermined to minimize injury to intervening tissue. Rather than entirely outside the body, the miniball, which is not harmful to untargeted tissue, is extracted to an extraluminal but intracorporeal location, preferably, just outside the ductus. The action is intended to preempt any ability of the tissue to resist extraction and may be thought of a the reverse or reciprocal of ballistic implantation, which similarly seeks to effect infixion with such suddenness that minimal disruption or trauma results. Except in the brain, a suitably located miniball not containing a metal shell or magnetized lanthanoid can be lithotripsied in place. The brain excepted, if the attempt to move the miniball to a more effective or safe location fails, it can be extracted entirely outside of the body as addressed in section X2c entitled Stereotactic Arrest and Extraction of a Circulating, Dangerously Positioned, or Embolizing Miniball.

The fine probe, which concentrates the flux to avoid nontargeted implants, consists of a soft iron core or armature supported by strong bracing on a strong cart that allows an extension of the core to be rolled into central axial relation with the tunnel (bore, gantry) of a magnetic resonance machine. A miniball that rebounds into the lumen of an artery is carried away from the other miniballs reducing the difficulty in singling it out for arrest and extraction. The miniball is resituated to a safe location within, or if necessary as when the miniball is a high dose-rate radiation seed, extracted entirely out of the body. To control the end point, extraction is generally pulsed to retract the miniball in increments determined by the resistance of the tissue to penetration.

Only the outer or $B_0$ magnet is used. The need to effect extraction along a predetermined path is only slightly greater in the improbable event that a stay requires forcible extraction, as addressed above in section 4g entitled Emergency Recovery of Miniballs and Stays. The cart is then bolted or otherwise securely fastened to anchors welded or otherwise securely fastened to the machine. The core is stepped down in diameter at intervals by division into two or more arms connected by airgapless gimbal or hinge joints at right angles to each other. These joints as well as the cart, can be motorized, the cart can move along rails, and the process controlled from a distance. The terminal arm ends in a narrow section that concentrates the lines of force so that these can be focused by pointing in any forward direction.

Materials testing results for the perforation resistance of human tissue to a miniball of given diameter when drawn by a magnetic field obtained as indicated are wanting; however, that a magnetic resonance machine is able to generate a field of sufficient strength to extract a miniball through hard tissue much less the integument, for example, should leave little doubt as to the functionality of this approach for miniball resituation or extraction. Analogous studies suggest approaches to the study of penetration and perforation of different ductus walls other than those set forth below in section XVII entitled Testing and Tests (see, for example, Nolan, G., Hainsworth, S. V., and Rutty, G. N. 2018. "Forces Generated in Stabbing Attacks: An Evaluation of the Utility of the Mild, Moderate and Severe Scale," *International Journal of Legal Medicine* 132(1):229-236; MacManus, D. B., Gilchrist, M. D., and Murphy, J. G. 2017. "An Empirical Measure of Nonlinear Strain for Soft Tissue Indentation," *Royal Society of England Open Science* 4(11):170894; Beekmans, S. V., Emanuel, K. S., Smit, T. H., and Iannuzzi, D. 2017. "Minimally Invasive Micro-indentation: Mapping Tissue Mechanics at the Tip of an 18G Needle," *Scientific Reports* 7(1):11364; Limbert, G. 2017. "Mathematical and Computational Modelling of Skin Biophysics: A Review," *Proceedings of the Royal Society of London, Series A. Mathematical, Physical, and Engineering Sciences* 473 (2203):20170257; Griffin, M., Premakumar, Y., Seifalian, A., Butler, P. E., and Szarko, M. 2016. "Biomechanical Characterization of Human Soft Tissues Using Indentation and Tensile Testing," *Journal of Visualized Experiments* (118); Li, W. and Luo, X. Y. 2016. "An Invariant-based Damage Model for Human and Animal Skins," *Annals of Biomedical Engineering* 44(10):3109-3122; Ní Annaidh, A., Cassidy, M., Curtis, M., Destrade, M., and Gilchrist, M. D. 2015. "Toward a Predictive Assessment of Stab-penetration Forces," *American Journal of Forensic Medicine and Pathology* 36(3):162-166; Budday, S., Nay, R., de Rooij, R., Steinmann, P., Wyrobek, T., Ovaert, T. C., and Kuhl, E. 2015. "Mechanical Properties of Gray and White Matter Brain Tissue by Indentation," *Journal of Mechanical Behavior of Biomedical Materials* 46:318-330; Weisbecker, H., Unterberger, M. J., and Holzapfel, G. A. 2015. "Constitutive Modelling of Arteries Considering Fibre Recruitment and Three-dimensional Fibre Distribution," *Journal of the Royal Society of England Interface* 12(105). pii: 20150111; Ní Annaidh, A. N., Cassidy, M., Curtis, M., Destrade, M., and Gilchrist, M. D. 2013. "A Combined Experimental and Numerical Study of Stab-penetration Forces," *Forensic Science International* 233(1-3):7-13; Parmar, K., Hainsworth, S. V., and Rutty, G. N. 2012. "Quantification of Forces Required for Stabbing with Screwdrivers and Other Blunter Instruments," *International Journal of Legal Medicine* 126 (1):43-53; van Dommelen, J. A., van der Sande, T. P., Hrapko, M., and Peters, G. W. 2010. "Mechanical Properties of Brain Tissue by Indentation: Interregional Variation," *Journal of the Mechanical Behavior of Biomedical Materials* 3(2):158-166; Ankersen, J., Birkbeck, A. E., Thomson, R. D., and Vanezis, P. 1999. "Puncture Resistance and Tensile Strength of Skin Simulants," *Proceeding of the Institution of Mechanical Engineers. Part H, Journal of Engineering in Medicine* 213(6):493-501; Jussila, J., Leppäniemi, A., Paronen, M., and Kulomäki, E. 2005. "Ballistic Skin Simulant," *Forensic Science International* 150(1):63-71).

Medication and radiation seed miniballs and stays are used without a stent-jacket and are not blocked by a jacket from outward (axifugal, abluminal) recovery. When avoidable, direct percutaneous (acrotic, integumentary) incision is not preferred as risking luminal entry. Outward removal of stent miniballs and stays must allow for the interposition of the jacket. Miniballs are drawn through the outer tunic or tunics and into the moisture barrier-coated viscoelastic polyurethane foam lining of the base-tube with the aid of a powerful external (extracorporeal) electromagnet. Recovery without breaching the intima means that there is less difficulty and risk than there is in the recovery of an endoluminal stent. Stays are not recoverable thus; however, fixed in place with a coating of cement and integrated into the surrounding tissue, are not susceptible to migration, and should not require removal, which is surgical.

X2d. Downstream Disintegration of a Circulating Miniball

The preprocedural positioning of a powerful electromagnet along the vascular tree downstream from the treatment site allows any miniball without toxic, radioactive, or nonabsorbable content that incorporates ferrous content and means for its disintegration that enters the circulation to be disintegrated on demand without awareness as to its exact location. For this purpose, all miniballs already incorporate sufficient magnetically susceptible, typically ferrous, content to permit arrest and extraction should conditions necessitate. Adequate susceptibility to magnetic traction is satisfied with the incorporation of sufficient superparamagnetic superparamagnetic magnetite or maghemite nanoparticles or finely grained powder.

With these, the greatest surface area is that optimal and yields the quickest absorption time. Induction is more efficient with larger grains of iron, which may be obtained by sintering sufficient superparamagnetic magnetite or maghemite nanoparticles or finely grained powder but is more often solid. The iron content is absorbable over time, extractable if microembolizing as to cause discomfort, and rarely if ever sufficient in quantity to reach the toxic level at about 350 micrograms per deciliter serum iron (*The Merck Manual of Diagnosis and Therapy*, 18th edition, pages 2667-2668). Means incorporated into miniballs to allow their destruction by heat induction are addressed above in the section entitled Noninvasive dissolution on demand of absorbable stent-jackets, base-tubes, radiation shields, and miniballs.

X3. Perforations Along the Gastrointestinal Tract

Perforation along the digestive or gastrointestinal tract can occur during implantation discharge as accidental but not as the result of an intentional extraction, which owing to the gauge of the ductus, can always be accomplished endoluminally. Compared to other iatrogenic and to pathological perforations, those caused by miniballs are tiny, close spontaneously, and do not allow flora to be released in large numbers through spillage. Pathogens in lower numbers will, however, be carried forward into the surrounding cavity on septic debris forced ahead of and adherent to the relatively tiny miniball when it exits. Gastrointestinal perforation treated of in the literature involves much larger wounds and the discharge of relatively large volumes of septic debris. Reference to the literature below pertain only to such breaches when severe, such as the result of resecting a malignancy or typhoid perforation.

Provided the subject is immunocompetent, infection from the tiny breach should eventuate slowly with a severity responsive to antibiotics (Min, B. S. 2016. "Intestinal Perforation: A Surgeon's Nightmare Enlightened by Scientific Research," *Annals of Coloproctology* 32(6):205; Shin, R., Lee, S. M., Sohn, B., Lee, D. W., Song, I., and 6 others 2016. "Predictors of Morbidity and Mortality after Surgery for Intestinal Perforation," *Annals of Coloproctology* 32(6):221-227; Medina, E. 2010. "Murine Model of Polymicrobial Septic Peritonitis Using Cecal Ligation and Puncture (CLP)," *Methods in Molecular Biology* 602:411-415; Agarwal, N., Saha, S., Srivastava, A., Chumber, S., Dhar, A., and Garg, S. 2007. "Peritonitis: 10 Years' Experience in a Single Surgical Unit," *Tropical Gastroenterology* 28(3):117-120; Wong, P. F., Gilliam, A. D., Kumar, S., Shenfine, J., O'Dair, G. N., and Leaper, D. J. 2005. "Antibiotic Regimens for Secondary Peritonitis of Gastrointestinal Origin in Adults," *Cochrane Database of Systematic Reviews* (2):CD004539), and respond to antibiotic therapy without the need for surgical intervention.

XI. Hypoxia and Ischemia-Averting Elements

The dimensional restrictions for adequate therapeutic maneuvering are generally severe even when allowances for oxygen to pass need not be considered, as in a ureter, for example, and is the incentive for Barrel-assemblies which incorporate hypoxia countering features and those that achieve ablation or angioplasty capability as bipartite where the outer or ensheathing projection catheter is interim withdrawable as necessary.

The features incorporated into a barrel-assembly to minimize the cutoff of oxygen (hypoxia, mionexia, anoxia) in the bronchi or in blood vessels through angiemphraxis vary depending upon the maximum outer diameter permissible, the functional capabilities that must be accommodated within this diameter, the degree of flexibility essential to track the type ductus, and the type of barrel-assembly. Even with the features addressed below, the muzzle-head should never be so broad as to prevent blood from flowing past it on the systoles.

For example, provided unobstructed side-ports are present, the unoccupied through-bore can be used to allow blood to pass through a combination-form barrel-assembly or radial projection catheter. Blood-tunnels allow some flow through the barrel-catheter, but other components unaffected, reduce flexibility when inclined longitudinally to allow some flow-through. If deep enough, blood-grooves on the muzzle-head can allow sufficient blood to pass, or to pass when a combination-form radial projection catheter is withdrawn.

When angioplasty in a coronary artery is to be followed by stenting discharge to place the implants, the barrel-assembly is not withdrawn following angioplasty but inserted into the airgun to initiate stenting. Then, even though the apparatus has been devised to minimize procedural time and present a minimal cross-sectional area, unless active means are incorporated for minimizing hypoxia, the risk of an infarction is unacceptable. While preferably avoided, the use of newer bypass machines, as mentioned above, should not result in the neurocognitive deficits observed in the past.

XI1. Blood-Grooves

Blood-grooves pertain to the radial discharge muzzle-heads addressed above in the section entitled Blood-grooves on muzzle-heads for use in blood vessels.

XI2. Blood-Tunnels

Blood-tunnels pertain to barrel-catheters and are addressed above in the section of like title beneath the heading Radial discharge barrel-assembly elements. Blood-tunnels also serve as tube polymer-nonintrinsic barrel-catheter flexibility (bendability, trackability) altering elements. The alternative use of lining or casing lengths of metal tubing concentric with the barrel-catheter is considered obvious.

XI3. Flow-Through Bore in Combination-Form Barrel-Assemblies and Combination-Form Radial Projection Catheters Used in Blood Vessels While unoccupied and disposed either antegrade or retrograde to the flow of blood, the central channel of a combination-form barrel-assembly or a combination-form radial projection catheter can be used to allow blood to flow between a side-port or ports and the nose or front end. When antegrade, blood flows into the side-ports and out the nose-hole, whereas when retrograde, flow is into the nose-hole and out the side-ports. This is addressed above in the sections entitled Side-ports, Flow-through Barrel-assembly for Use in Blood Vessels, Through-bore, or Combination-form, Radial Projection Catheters, and Through-bore, or Combination-form, Barrel-assemblies: Barrel-assemblies which Accommodate or Incorporate Means for Ablation, Thrombectomy, Atherectomy, Atherotomy, and/or Endoscopy. Such use can be aided by push-arm tool-inserts used to provide greater clearance between the outside of the catheter and the lumen wall.

XI4. Push-Arm Radial Projection Unit Tool-Inserts

Radial projection units are incorporated into radial discharge muzzle-heads, addressed above in the section entitled Muzzle-head radial projection units, and combination-form radial projection catheters. While blank-faced push-arm tool-inserts are specifically intended to allow the muzzle-head to be pushed in the opposite direction allowing blood to pass, almost any tool-insert without sharp projections on the pushing face can be used to accomplish such action. In a combination-form barrel-assembly or radial projection catheter with distal side-ports to allow blood to flow through the central channel or bore, the push-arms not only provide some peripheral clearance but give better access of the blood to the side-ports.

XII. Service-Catheters

A service-catheter is led (snaked, fed) down through a barrel-tube to access the lumen or lumen wall at the exit-hole or exit-port while intracorporeal, that is, midprocedurally, without the need for withdrawal and reentry. In so doing, the barrel-tube is used as a guide catheter. A service-catheter can be used, for example, to conduct a fluid for release at the exit-hole; if provided with an injection needle at the distal end, then to serve as a hypotube for injecting the lumen wall; to convey electrodes for nonthermal irreversible electroporation ablation addressed just below, or electrochemotherapy (Hampton, T. 2011. "Electric Pulses Help with Chemotherapy, May Open New Paths for Other Agents," Journal of the American Medical Association 305(6):549-551; Möller, M. G., Salwa, S., Soden, D. M., and O'Sullivan, G. C. 2009. "Electrochemotherapy as an Adjunct or Alternative to Other Treatments for Unresectable or In-transit Melanoma," *Expert Reviews of Anticancer Therapy* 9 (11): 1611-1630; Sersa, G., Miklavcic, D., Cemazar, M., Rudolf, Z., Pucihar, G., and Snoj, M. 2008. "Electrochemotherapy in Treatment of Tumours," *European Journal of Surgical Oncology* 34(2): 232-240), or any small cabled device, such as a laser or scope. The proximity of the recovery electromagnets negates the need for service-catheters with a magnet tip.

Service-catheters are applicable to simple pipe-type barrel-assemblies with a luminal diameter that will accommodate a laser or scope fed through a proximal barrel-catheter side-port or through the proximal end of the barrel-assembly when disconnected from the airgun. Miniaturization allows the insertion within a luminal wall to ablate diseased tissue therein, such as a tumor, of a nonthermal electric pulse conducting probe tool-insert (see, for example, Arena, C., Sano, M., Rossmeisl, J., Caldwell, J., Garcia, P., Rylander, M., and Davalos, R. 2011. "High-Frequency Irreversible Electroporation (H-fire) for Non-thermal Ablation without Muscle Contraction," *BioMedical Engineering OnLine* 10(102):1-20; Neal, R. E. 2nd, Singh, R., Hatcher, H. C., Kock, N. D., Torti, S. V., and Davalos, R. V. 2010. "Treatment of Breast Cancer through the Application of Irreversible Electroporation Using a Novel Minimally Invasive Single Needle Electrode," *Breast Cancer Research and Treatment* 123(1):295-301; Al-Sakere, B., André, F., Bernat, C., Connault, E., Opolon, P., Davalos, R. V., Rubinsky, B., and Mir, L. M. 2007. "Tumor Ablation with Irreversible Electroporation," *Public Library of Science One* 2(11): e1135; Davalos, R. V., Mir, I. L., and Rubinsky, B. 2005. "Tissue Ablation with Irreversible Electroporation," *Annals of Biomedical Engineering* 33(2):223-231).

XIII. Service-Catheters, Service-Channels, and Use of the Barrel-Assembly as a Guide-Catheter A barrel-tube that is not needed for discharge can serve as the service-catheter itself. For brush cytological purposes, however, a service-catheter allows obtaining a sufficient tissue sample for brush cytology without the need to maintain vacuum force to retrieve the sample. The sample need be withdrawn no more than past the distal end of the service-catheter, whereupon the catheter is removed, and the sample blown onto the test medium. A barrel-tube that will be needed for discharge is not fouled when lined with a service-catheter. Service-catheters can serve as conduits for pumping through fluid therapeutic substances into the lumen, or, with a prefilled hypoendothelial or hypointimal injection needle (hypotube) at the distal end, into the lumen wall. The latter can be actuated by a manual plunger piston as in a hypodermic syringe or powered in any of a number of ways.

More specifically, in feed-forward use, a service-catheter can be used for drying, wetting, chilling, or heating (by connection to a cold air gun, for example), to ablate, spray a powder, liquid, or gas against the surface of the lumen, or inject a fluid substance through the endothelium. In feedback use, aspirated materials can be tissue or any agent applied through feed forward use. In use as a guide-catheter, a multiple barrel-tube barrel-assembly can be rotated endoluminally with the turret-motor to apply these processes in any desired sequence at a single tissue target or as many targets as there are barrel-tubes. When connected to an aspiration pump or bulb or syringe pipetted, a service-catheter with a scalloped front edge can be used to shave, scrape, or brush the lumen surface to obtain tissue samples.

Otherwise unused barrel-tubes or service-catheters can be used in coordination with perforated radial projection unit tool-inserts so that a fluid delivered through either can be drawn toward and aspirated away by the other. Using tool-inserts in longitudinally and/or circumferentially separated radial projection units and service-catheters to deliver and/or aspirate a fluid allows the direction and path or areal path of flow over the lumen wall to be controlled. When the tool-insert aspirates itself, the controlled flow of fluid over the lumen wall terminates at the treatment site. Piped radial projection units have a rear pipeline or communicating conduit that allows the forward throughput of chilling gas, for example, and reverse throughput or aspiration of detritus or excess medication, cement, swelling or sclerosing agent, for example.

These are addressed below in the sections entitled Piped radial projection units and radial projection unit tool-inserts. When the tool-insert, such as a side-cutter (side-cutting shaver), is not piped and used to aspirate and is positioned between the fluid inlet, such as a service-catheter, for example, and an outlet such as a piped projection unit located on the opposite side of the treatment site, for example, the flow between the two outer components can be made to move over the intervening treatment site. Lavage or the deposition of medication can be accomplished in a similar manner, using either the barrel-tubes or perforated radial projection unit tool-inserts to deliver and the other to draw off the fluid, which can be heated or chilled. Perforated tool-inserts can be used to deliver heated or chilled gas. When the fluid would foul the barrel-tubes, a service-catheter is inserted down to the exit port.

With a combination-form barrel-assembly, the fluid can be delivered or drawn off through a tube passed down the central canal to the nose, and use of a dual lumen tube frees the barrel-tubes and tool-inserts for other functions. Tight controllability over an area of the lumen wall can be attained in the application of medication, change in temperature, or both in coordination. Longitudinally separated temperature changing devices, whether barrel-tubes, blank radial projection unit tool-inserts, or electrical winding-heated heat-windows, can be used to emit and take up a fluid and/or to establish a change from a higher to a lower temperature at an intervening treatment site which may serve thermal or cryogenic ablation or angioplasty in lieu of a heat-window and cooling catheter, or the work of an intervening radial projection tool.

Since radial projection units can encircle the muzzle-head, the linear or areal extent of the lumen wall over which a temperature gradient with or without medication can apply whether past an intervening working tool-insert is unrestricted. Whereas heat-windows can be used only to heat and require to be controlled from a barrel-assembly-onboard ablation and angioplasty control panel, radial projection units are more capable, the control of medication, temperature, or both, for example, readily controlled by heating or chilling the source cylinder connected to the delivering side- or end-socket. The insulation value of the polymeric barrel-catheter isolates the temperature change from the lumen wall until emitted; however, the source must be temperature compensated for the loss in cold or heat moving toward the exit points.

The rate of heat loss moving forward down the barrel-tube is increased if metal centering devices are used as these act as heat sinks. Since the barrel-assembly is limited in rotation by means of the turret-motor, that is, in working arc (qv.), a muzzle-head with muzzle-ports in close circumferential relation can be used. The working arc is rotated by rotating the barrel-assembly. When not needed for discharge, any barrel-tube can itself be used as, rather than used to conduit, a service-catheter. A side-socket (qv.) that allows service-catheters to be inserted into and withdrawn from the barrel-tubes without disconnection from the airgun allows medication and/or an adhesive to be applied to the lumen surface or subendothelially through a service-catheter such that the implant discharged will pass through the same point; barrel-tube lining.

XII2. Muzzle-Head Access Through a Service-Channel Without the Aid of and by Means of Inserting a Service-Catheter A service-channel is a barrel-tube or central canal used itself or as a guide-catheter for a narrower service-catheter to allow distal access for the delivery or aspiration of a fluid substance. Service-catheters are essential as linings to prevent fouling a barrel-tube that is to be used for discharge, and any number and type may be used in succession in any one or a plurality of barrel-tubes. A spare or extra barrel-tube and muzzle-port as already contained within the barrel-assembly allow access to the muzzle-head for the delivery of fluid substances, generally, with a simple pipe, medication and with a radial discharge barrel-assembly, medication or a lubricant.

A liquid is delivered through a catheter, or service-catheter, to a syringe connected at the proximal end. The use of a service-channel requires that the barrel-assembly be disconnected from the airgun or that a proximal side entry portal or socket be provided. Disconnection allows the same barrel-tube to be used for discharge. Use of the central canal as a service-channel in an edge-discharge barrel-assembly to be used in the circulatory system is discounted as risking the clogging of the air pressure equalization holes essential to avoid allows the delivery of medication, for example, into the lumen, A side barrel-tube entry socket is analogous to an ostomy where the proximal end of the barrel-tube is diverted out the side of the barrel-catheter where a syringe, bulb, pump, or any other delivery or retrieval mechanism can be inserted as necessary.

A switch to allow changing connection of the service-catheter from the airgun chamber to the side entry socket without disconnecting the barrel-assembly from the airgun is considered nonessential. In an ablation or ablation and angioplasty-capable barrel-assembly, the barrel-tube side entry socket can be incorporated into the electrical side-socket is present. A ramrod or testing rod (addressed below) with outer diameter just smaller than the internal diameter of this muzzle-head service-channel, whether the central canal or a spare barrel-tube, allows the substance to be delivered to the muzzle-head by pushing the rod behind the substance down the barrel. To minimize the loss of material by spreading along the inner wall of the barrel, the ramrod is preferably made of a fluoropolymer such as polytetrafluoroethylene.

Since any barrel-tube and muzzle-port can be used for discharge, when a barrel-tube is to be reserved for such use, a barrel-assembly including one more barrel-tubes than needed for discharge is used. That is, barrel-assemblies are not made to include a barrel-tube in excess of those that can be used for discharge. Selecting a barrel-assembly with one more barrel-tubes than is needed for discharge is then preferable to the use of a barrel-tube used for discharge, because unless an additional cleaning step is undertaken, the deposition of a film along the walls and its accumulation along the bottom of the barrel-tube will affect exit velocity and carry some of the deposited material into the intratissue or wound trajectory.

Thus, when the number of barrel-tubes needed for discharge and diameter of the implants necessitate a barrel-assembly that with an extra barrel-tube would bring the barrel-assembly to too large a diameter, one or more of the discharge barrel-tubes is used and any problematic film coating left along the inside of the discharge barrel-tube or tubes is wiped down with a second ramrod having an absorbent felt or cotton covering. The use of a service-channel to accomplish the intraductal injection or infusion of medication into the lumen, or with the aid of a service-catheter used as an injection-tube passed down a service-channel as described above in the sections entitled Turret-motor Operational Modes and Miniballs Coated with a Heat-activated (-melted, -denatured) Tissue Adhesive-hardener or Binder-fixative, into the ductus wall is considered obvious.

Outside the circulatory system, where service-channel injectant or medicinal ejecta would not be immediately swept downstream, a ductus wall swelling agent as addressed under the section below entitled Muzzle-head Access through a Service-channel Without the Aid of and by Means of Inserting a Service-Catheter can be released. Such include, for example, acetone, of which the use is not permissible in the airway, within proximity of the eyes, or in the bloodstream, or CO2 as drying agents; and CO2 or a cold air gun for delivering cold. The use of a service-channel or channels as guide-catheters or sleeves through which to advance a catheter or catheters into the lumen or against the lumen wall for the purpose of removing debris by connection to an aspirator pump is addressed below in the section entitled Use of the Barrel-assembly as an Aspirator or Transluminal Extraction Catheter for the Removal of Soft Plaque or Mispositioned Miniballs.

The use of a service-channel to obtain biopsy samples, to include those obtained by brush cytology (see, for example, Boberg, K. M., Jebsen, P., Clausen, O. P., Foss, A., Aabakken, L., and Schrumpf, E. 2006. "Diagnostic Benefit of Biliary Brush Cytology in Cholangiocarcinoma in Primary Sclerosing Cholangitis," *Journal of Hepatology* 45(4): 568-574) accomplished with the side-brushes is addressed below in the section entitled Use of the Barrel-assembly as an Aspirator or Transluminal Extraction Catheter to Retrieve Biopsy Samples. Whereas the retrieval of tissue samples obtained by shaving or brush-type radial projection unit side-sweeper tool-inserts necessitate withdrawal of the barrel-assembly, samples obtained by aspiration do not. Absent an airgun, any barrel-assembly can be used purely as a single or multiple channel guide-catheter for the taking of tissue samples and/or the application of medication along the internal surface of the lumen.

While having been positioned endoluminally for another primary purpose, larger barrel-tubes, to include simple pipes, can be used secondarily as guiding catheters for a bioptome (see, for example, Terasaki, K., Wittich, G. R., Lycke, G., Walter, R., Nowels, K., Swanson, D., and Lucas, D. 1991. "Percutaneous Transluminal Biopsy of Biliary Strictures with a Bioptome," *American Journal of Roentgenology* 156(1):77-78) without the need to withdraw the barrel-assembly, which can accordingly remain prepositioned along the lumen to initiate discharge when the laboratory results can be obtained quickly. Radial projection unit side-sweeper type tool-inserts having projections that are configured as mushroom shaped anchors, or downwardly directed hollow domes to function much as an atherectomy catheter, such as those shown in FIGS. 51*a* and 51*b*, allow the retrieval of more material for analysis than those having projections of bristled conformation.

XII3. Cyanoacrylate Cement Injection Service-Catheter

However mixed and low in viscosity, cyanoacrylate cement must not be allowed to coat the interior of the barrel-tubes through which miniballs are discharged. When the use of cyanoacrylate is desired, consideration should be given first to the use of stays. It is possible, however, to pass a service-catheter (microcatheter) down an unused barrel-tube serving as service-channel and inject cyanoacrylate cement after the miniballs have been implanted. Such use is unintended and discouraged in the vascular tree wherein it must never be attempted without a trap-filter of sufficient capacity to prevent an embolism. To better comply with the motility intrinsic in the ductus, the cyanoacrylate cement should contain plasticizer, several having been specified in the section above entitled Miniballs Coated with a Heat-activated (-melted, -denatured) Tissue Adhesive-hardener or Binder-fixative, for better stability, the cyanoacrylate should be injected midway between the implanted miniballs, and for viewability, the cyanoacrylate must contain radiographic contrast.

To prevent the introduction of any cement into the bloodstream as well as impart greater radiolucency, a proportion of the mix must consist of superparamagnetic magnetite or maghemite nanoparticles or finely grained powder, recovery by the recovery electromagnets distal to the muzzle-ports trapping any cement that may escape. Eliminating the need to attach a separate hypodermic needle, the tip of the microcatheter is itself beveled, the bevel standard, short, or true short depending upon its wall thickness and strength. When discharge is under machine control so that positioning the microcatheter between the miniballs exceeds manual capability, the positional control system is used to place the tip of the microcatheter; however, the operator must manually inject the cement.

The microcatheter must be fed the adhesive from a metering pump and have a detent to limit the extension of the distal point past the muzzle-port. When the microcatheter is used in an artery, the cyanoacrylate adhesive is prevented from escaping downstream as an embolism by mixing it with a small proportion of superparamagnetic magnetite or maghemite nanoparticles or finely grained powder. The relation between the initial setting time and retention within a drop of cement of ferromagnetic particles so that magnetic attraction can be used to recover the entire drop rather than merely to extract the particles is addressed above in the section entitled Arcuate stent-stays (stays, stent-ribs, ribs) or Stays for use with stent-jackets.

The greater susceptibility to entry into the bloodstream of endoluminal access through the intima as opposed to extraluminal access through the adventitia with stays is counterbalanced by the greater ease with which the transluminal apparatus allows retrieval. A powerful hand-held permanent magnet or tractive electromagnet can be used to prevent an adhesive containing superparamagnetic magnetite or maghemite nanoparticles or finely grained powder from passing downstream. The magnet is prepositioned extracorporeally to intercept any ferrous material that might pass until the recovery electromagnets in the muzzle-head are brought up to retrieve the drop.

In so doing, the current to the extracorporeal magnet is reduced as that of the recovery electromagnets in the muzzle-head are increased, causing the drop to instantly trap itself within a recovery electromagnet antechamber behind a recovery magnet hinged door. Void of ferromagnetic material, pure medication miniballs and any cement used the more securely to fix these in position are not susceptible to inadvertent extraction once implanted through the use nearby of an electromagnet to recover a lost or extract a misplaced stay or miniball; however, the same lack of magnetic attractability could free these elements to embolize.

Accordingly, loss downstream of nonferrous elements such as pure medication miniballs or cement is prevented by incorporating into these sufficient sterile superparamagnetic magnetite or maghemite nanoparticles or finely grained powder to overcome their mass under the propulsive force of the bloodstream and thus allow these to be trapped. Insoluble and lower in specific gravity than blood serum, cyanoacrylate cement in blood coheres and floats. With the pulse tending to drive the self-coherent drop forward and buoyancy tending to drive it upward, the drop rises to the top of the artery where, soft but intact, the drop will tend to become stuck along the intima-lined ceiling for mechanical rather than chemical reasons.

Instantly beginning to polymerize in the aqueous environment of the blood, and thus trapping any particles of a ferrous metal such as superparamagnetic magnetite or maghemite nanoparticles or finely grained powder within it, the engagement of portions at the boundary of the drop of cyanoacrylate that have become lodged against the upper intima in the direction of current flow allows the electromagnets to retrieve the drop easily against the current. Even when the drop sets (polymerizes) in the form of a film having an outer edge that is larger than the recovery electromagnet antechamber doors, the ability of the adhesive to set to any firmness before the magnets can retrieve them is lacking. At the same time, the adhesive must have set to the extent that the iron particles will remain trapped within the drop rather than be attracted to the magnets leaving the drop to escape.

Since the cyanoacrylate contains contrast, the operator will be aware of such a release or leak. When intraparietal bonding and hardening are necessary, as when the wall to be implanted contains a separation, a second occurrence of such a leak should prompt the operator to end microcatheter injection in favor of dependence upon solder. The maximum safe capacity of the antechambers for miniballs of a given diameter can be stated accurately. However, semisolidified drops of cyanoacrylate are irregular and varied in conformation, and depending upon how one retrieved previously happened to settle within the antechamber, can interfere with antechamber door closure. The probability of door interference rises the longer the drop is in the antechamber and is able to gain hardness.

XII4. Service-Channel Adhesive Delivery Line

The injection of sclerosants using a flexible endoscope to treat variceal hemorrhages has been practiced for well over half a century. In order to adapt the technique for use with a barrel-assembly to introduce cyanoacrylate cement about the implanted miniballs as a tissue adhesive-hardener, the gauge of the service-catheter used as an injection catheter must be fine enough to pass down a barrel-tube and round the curve toward its distal terminus in the approach to the muzzle-port. To enhance visibility and retard premature setting, the adhesive is mixed with radiographic contrast such as Lipiodol™.

XII5. Cooling Catheters (Temperature-Changing Service-Catheters)

Cooling or temperature-changing catheters can be used either to heat or cool the tissue under treatment or parts of the apparatus. There are several types, some for attachment to stay insertion tools and having holes on the sides and/or the distal end. Some are distally close-ended with side-holes for snaking down the central canal or a barrel-tube in order to cool down the turret-motor and/or recovery electromagnet windings. Anticlotting agents administered notwithstanding, following the use of heat for thermal ablation or angioplasty, active cooling allows the thrombogenic range of temperatures that stand between angioplastic and room temperatures to be passed through more quickly. Other cooling catheters for use in ductus other than blood vessels are open-ended at the distal tip for emitting a chilling gas against the lumen wall.

Cooling or temperature-changing service catheters fall into two categories, depending upon whether a chilled gas or liquid is made to flow through the catheter to direct the cold or heat for therapeutic chilling or heating of the lumen wall or an enclosed chamber at the distal end contains a refrigerant gel or liquid that can retain cold or heat. The use of piped gas or liquid for controlling temperature is substantially limited to the use of muzzle-head and piped radial projection unit temperature-changing 'heat'-windows and when the temperature must be controllably adjusted midprocedurally. Gels are available that retain either heat or cold, so that withdrawal and insertion in a hot or cold bath, for example, will allow the temperature to be quickly changed for reentry into the barrel-assembly without the addition of water, allowing permanent encasement of the gel within a chamber at the distal closed off end of the cooling catheter.

These are generally cellulose or crosslinked sodium polymer based. Companies specialized in the use of such materials include Cold Ice, Incorporated, Oakland, Calif. and Zero-Pak Products, Richmond, British Columbia. Because the proximal end-plate of the barrel-assembly is engaged in the airgun chamber during discharge, the application of cold to assist in stabilizing tissue during discharge, for example, requires that the entry socket (receptacle, union, coupling) into the barrel-assembly be of the side- rather than the end-mounted type. A cooling (or heating) catheter of capillary gauge, or cooling capillary catheter, is passed down a spare barrel-tube (service-channel) or the narrower central canal of a center-discharge barrel-assembly. When unoccupied by an atherectomy cable, the central canal of a center-discharge barrel-assembly will accommodate a cooling (or heating) catheter of larger diameter, which can be a permanent part of a barrel-assembly equipped with a nose-window.

Alternatively, to allow the use of different devices, the central canal is left available so that a cooling catheter must be inserted through the end or side-socket. A similarly temporary nose-window must be inserted into the distal opening of the central canal at the same time. Temperature changing gas delivery catheters are also distinguished as capped (closed off, close-ended) or capless (open, open-ended). To prevent gas embolism, those for use in the bloodstream when the distal end is not blocked off from the bloodstream by engagement in the cooling catheter insertion channel of the ejection head are capped or if capless (open-ended), must be direct the cold air from a vortex cold air gun or liquified gas cartridge or hot air from the other outlet of the cold air gun against toward the backside of a nose-window (qv.), or nose heat-window.

XI16. Preparation of Service-Catheters for Use as Trans-barrel-Assembly Hypotubes Protection against thrombosis using the means described herein is conventional as to systemic medication, but can also be local by using anticlotting or antiplatelet-coated miniball (or stay) implants or local injection through a service-catheter equipped with a hypotube at the distal end. Delivery that is direct, targeted, and local allows the use of a much smaller dose that not administered enterally or parenterally is distributed minimally if at all to organs unamenable to the medication used. Except for a slight narrowing taper toward the distal tip to prevent the plug to be described from ejecting after the injectant has been expended, the service-catheter is consistent in diameter from end to end and fine enough to penetrate the lumen lining.

A separate hypotube extension, preferably made of a nonmagnetic material, is inserted into the distal end of the service-catheter only when the diameter of the service-catheter is large enough in diameter that its distal end is not already effectively a hypointimal or hypoendothelial needle and such that the terminal taper must be too steep or long. Conventional diameter reduction hypotubes for insertion into the distal end of larger diameter service-catheters are obtainable from numerous suppliers, to include IncisionTech Division, Specialty Blades, Incorporated, Staunton, Va., for example.

A service-catheter passed down a service-channel can be used to inject a wall-thickening (swelling) or tissue hardening agent and/or any other kind of medication or a surgical cement prior to discharge about a miniball after it has been placed. The service-catheter is passed down a service-channel (spare barrel-tube) as addressed immediately below and also below in the sections entitled Muzzle-head Access through a Service-channel without the Aid of and by Means of Inserting a Service-catheter and Thermal Ablation or Angioplasty- (Lumen Wall Priming Searing- or Cautery-) capable Barrel-assemblies.

A plug just to the rear of the injectant at the distal end of the service-catheter 1. Prevents the injectant from flowing proximad along the internal surface of the service-catheter as would preclude control over dose delivery by adjustment in the duration and pressure per puff of applied gas pressure. Since such a plug also 2. Allows controlled or metered release of the injectant and 3. Prevents the propulsive gas from emitting once the injectant has been expended, it is applied despite the stabilizing effect of surface tension and capillarity in service-catheter of small gauge. If stored, the plug also serves to 4. Seal out contaminants; the tip of the service-catheter is also dipped in a sealant that to prevent allergic responses, may consist of any suitable synthetic resin. The tip sealant should pull off in a single piece for discarding when the service-catheter is to be used. To prevent the loss of injectant when the tip sealant is pulled away; the surface tension The plug is produced by drawing up a suitable lumen-plugging material while molten under suction just ahead of the injectant. The coefficient of friction between the lumen lining and the plug when molten and when solidified is set through the choice of tubing and plug materials. When molten, the plug must ascend the service-catheter under vacuum pressure controllably without disintegrating and while maintaining a seal all about at a temperature that will not alter the injectant. A suitable plugging material must also be biocompatible and effectively insoluble in the injectant. To avert the breakup of the molten plug as it expands when drawn up the taper from the distal end, the taper is kept to a minimum and a plug material used that has the necessary cohesion. Upon solidifying, the plug must controllably slide down the lumen ahead of the column of pressurized gas which it is seals off from the substance to be injected to its fore and must be hard enough to preclude being ejected through the distal end of the service-catheter.

For procedures requiring the application of heat or cold, the plug material must not significantly alter in flow or frangibility at the temperatures to be used. For procedures that require more than 85 degrees centigrade, most synthetic (nonallergenic) waxes will not be usable as plugs, necessitating the use of polymers. Once the molten plug material has been drawn up into the distal tip of the service-catheter under vacuum pressure, the tip is wiped flat and dipped into the substance to be injected. This injectant is then drawn up into the lumen continuously behind the plug, which is positioned level with a tick mark so that the portion of the service-catheter between its distal surface and the distal tip of the service-catheter will contain the desired volume of injectant, such as medication, a swelling agent, lubricant, or surgical cement, for example, contrast dye added for enhanced imaging.

The calibration must allow for deformity in the front or distal face of the plug and the taper at the tip that prevents the plug from ejecting when the injectant is expended. The injectant is delivered (advanced) by applying a puff of air or other gas. When only one injection is to be made with the service-catheter, the pressure and duration of the puff can vary over a range and thus be applied by mouth, with a bulb, or syringe. When, however, the service-catheter must deliver consecutive injections in the correct dose without having to be withdrawn and another preloaded service-catheter inserted for each injection, a precision aspiration pump reversed to blow must be used to deliver puffs that are metered in pressure and duration. When the application does not necessitate exactitude, a conventional manual sphygmomanometer can be adapted for the purpose.

XI17. Use of the Barrel-Assembly as an Aspirator or Transluminal Extraction Catheter for the Removal of Soft Plaque or Mispositioned Miniballs Aspiration using a barrel-assembly is addressed above in the section entitled Turret-motor Operational Modes. Once every miniball has been implanted, rather than to withdraw the barrel-assembly and introduce a separate aspiration line to remove debris, the barrel-assembly can be directly bulb or syringe pipetted or connected to a Beral pipette with bulb emptied or to a vacuum aspirator. If provided with a side-socket as addressed below in the section entitled Barrel-assembly Side-socket, the barrel-assembly need not first be disconnected from the airgun. Upon withdrawal following aspiration, the barrel-assembly can be left connected to the vacuum pump, flushed with warm water, and then sterilized with ethylene oxide gas, as addressed below in the section on sterilization.

When the object is to retract debris and not to obtain a biopsy sample, the use of a catheter to line the barrel-tube is not essential. Except for use in the largest diameter ductus, to incorporate additional components into the barrel-assembly as would allow it to also function as an ultrasonic aspirator handpiece for the fragmentation and emulsification of tissue currently exceeds practical limits of miniaturization. Aspiration that uses the barrel-tube or tubes as vacuum lines without a catheter must immediately precede withdrawal or the debris retrieved will foul the barrel-tubes. This is no less the case if the barrel-tube used is a service-channel as addressed above in the section entitled Muzzle-head Access by Means of a Service-channel. However, with more than one barrel-tube available, the barrel-tubes can be separately used as aspiration lines, service-channels, or for discharging miniballs.

Then the barrel-tubes reserved as vacuum lines can be used with the radial projection unit tool-inserts to remove material from the inner surface of the ductus wall, after which barrel-tubes not used thus can be used for discharge. For the most part, the incorporation of plural barrel-tubes is limited to barrel-assemblies of larger diameter. A barrel-tube used as an aspiration line can serve as a means in addition to the recovery electromagnets and trap-filter for recovering a mispositioned miniball. Yet another method for the recovery of implants whether miniballs or stays is addressed above in the section entitled Non-endoluminal Recovery of Miniballs To recover a miniball, the closest muzzle-port is placed over the intima at the point where the miniball penetrated the ductus wall and the vacuum applied.

Preferably this will back out the miniball through the same angular trajectory as it entered, retrieval thus rather than normal to the trajectory end-point less injurious to the inner layers of the ductus wall. Since the inclination of the barrel-tubes is that used to discharge the miniball, placing the muzzle-port over the entry perforation results in the application of the retractive force at the same angle as the entry trajectory. Wetting the miniballs in the rotary magazine clip with contrast before inserting the clip into the chamber aids in locating the insertion perforation. If miniball recovery is sufficiently free of line-fouling debris, as can be accomplished when different barrel-tubes were used for the aspiration of debris, then once retrieved into the barrel-tube, the barrel-tube can be removed from the vacuum line and reconnected for discharge to reposition the miniball within the ductus wall.

XI18. Use of the Barrel-Assembly as an Aspirator or Transluminal Extraction Catheter to Retrieve Biopsy Samples Apart from implant delivery, any barrel-assembly can be used to obtain tissue samples for analysis from along the inside of the lumen wall, eliminating the need for entry more than once. For such use, a vacuum pump can be connected directly to a barrel-tube or bulb or syringe pipetting or a syringe can be used. However, in most instances, the treatment site will not allow a vacuum pressure sufficient to retract the tissue without the need to withdraw from the lumen. Unless this is the only or the last procedure to be performed, it is desirable to leave the barrel-assembly in position and avoid the need for a forced withdrawal. This is accomplished by using the barrel-tube as a guide-catheter or conduit for slightly narrower catheters.

The sampling catheters withdrawn as desired, aspiration then need not draw tissue more than a few millimeters into these. The use of service-catheters to withdraw ablated tissue and samples for analysis can be combined with use of the radial projection unit tool-inserts to remove hardened (indurated, sclerotic) or toughened tissue more quickly, as addressed below in the sections entitled Coordinated Use of Aspiration and Piped Radial Projection and Radial Projection Unit Tool-inserts. Additional means for obtaining biopsy samples is the use of a piped radial projection tool-insert, as addressed below in the section entitled Coordinated Use of Aspiration and Piped Radial Projection Units to Remove Diseased Tissue or Obtain Tissue Samples for Analysis.

XI19. Rotation of Muzzle-Heads with Unused Barrel-Tubes for Use as a Guide-Catheters With a single barrel-tube, such as in a simple pipe or a monobarrel radial discharge barrel-assembly, use of the barrel-assembly as a guide-catheter for different procedures, such as the delivery of medication, taking of biopsy samples, application of heat or cold, for example, must be done in succession. The insertion and withdrawal of catheters one at a time down a single channel takes more time, but the lack of sufficient lumen diameter can impose this limitation. A multiple barrel-tube barrel-assembly allows each barrel-tube to serve as a guide-catheter for a different procedure.

For example, one barrel-tube can be used for atherectomy by means of suction ablation and another to apply medication in the form of a gas, powder, or liquid, or to apply heat or cold, in any sequence, to include alternation between ablation and medication and alternation to change the medication. With a multiple barrel-tube barrel-assembly, the turret-motor can be used to rotate successive catheters into position without the need to withdraw one catheter and insert another, so that switching from one catheter to the next is accomplished immediately. A larger diameter barrel-tube allows the use of a bioptome.

Since in order to prevent distortion of the barrel-tubes to an extent as would interfere with discharge, the muzzle-head incorporates a detent to prevent excessive rotation, the use of separate barrel-tubes to convey catheters for accomplishing a different but related treatment option with each is best performed with an eccentric muzzle-head wherein the exit ports are closer together than in a muzzle-head with an equidistant configuration. This allows related functions to be quickly applied in a prescribed sequence. Since the use of each catheter is sequential, the fact that aiming each successive exit port with the manual means provided more accurately than within a quadrant of the ductus circumference is of nugatory pertinence. Greater aiming accuracy is obtained through the use of contrast and adequate imaging technology.

XII10. Delivery of a Measured Quantity of a Liquid Through a Service-Channel

A catheter for delivery of a liquid, such as a medication, surgical cement, or a mixture of diverse substances through a service-channel is provided by inserting syringe thumb plunger with a plunger shaft calibrated in milliliters into the proximal end of the catheter, dipping the distal end of the catheter into the liquid, and using the plunger to draw in a measured quantity of the substance through the distal end of the catheter. The calibration is then used to eject the desired amount. A similar calibration at the distal end can be used to confirm delivery of the desired dose after withdrawal. The application of a liquid through or upon the intima within the vascular tree requires that the substance be innocuous, that it not enter the bloodstream in medically significant amount, or that the clinical context justifies the risk. The use of a trap-filter is addressed above in the section entitled Cyanoacrylate Injection Catheter. Depending upon the medication and the caliber and length of the service-catheter, a high pressure metered dose inhaler or an electronic or jet nebulizer (atomizer) can be connected to the service-catheter to deliver the medication as an aerosol.

XII11. Delivery of a Measured Quantity of a Gas Through a Service-Channel

The metered release of a gas through a catheter that is passed down a service-channel to abut upon the target tissue along the internal surface of the lumen is by means of a modified commercial gas-operated pistol as described below in the section entitled Modification of Commercial Airguns. The air pistol is connected to the catheter in the same manner as it would be connected to a simple pipe barrel-assembly, for example. When not liquified $CO_2$ to chill the target tissue, the compressed gas in the cylinder must have eliminated any lubricant as may have been incorporated into a conventional powerlet as to consist of or include the therapeutic gas to be delivered (which will be liquified only if the boiling point is below the room temperature). Regardless of phase transition, the gas is delivered from a pressurized canister.

In a commercial air pistol suitable for use with a simple pipe barrel-assembly when modified as described below in the section entitled Simple Airgun with Limited Application, the medicating gas expelled with each discharge is determined by the gas pressure, the valve body open time, and the cross-sectional area of the gas passage or circular aperture surrounding the pin through the valve. The spring-loaded valve body pin generally conical, aperture area and open time depend upon the force of impact by the hammer, pin conformation, and the restorative force of the valve body spring.

These built in factors inherently meter the gas discharged with each pull of the trigger, the valve body slide valve modification described below in the section entitled Dedicated Interventional Airguns allowing variability in the valve body pressure. In the more versatile embodiments described in the section below entitled Dedicated Interventional Airguns, the incorporation of a punch solenoid in place of a spring loaded mechanical hammer affords a means for controlling valve body open time in addition to the slide-valve incorporated into the side of the valve body. Adjustment in the solenoid current varies the force of impact, hence, the excursion of the valve body pin when struck.

XII12. Delivery of a Measured Quantity of a Powder Through a Service-Channel

Therapeutic dry powders, aerogel powders, and aerosol delivered powders encompass a wide spectrum of medication types (see, for example, Claim 22, Lechuga-Ballesteros, D. and Kuo, M-C. 2003. "Dry Powder Compositions Having Improved Dispersivity," U.S. Pat. No. 6,518,239; Lee, K. P. and Gould, G. L. 2006. "Aerogel Powder Therapeutic Agents," U.S. Pat. No. 6,994,842). Methods for achieving uniformly dispersible powders for pulmonary drug delivery that can be adapted for delivery through a catheter continue under development (see, for example, Lechuga-Ballesteros, D., Charan, C., Stults, C. L., Stevenson, C. L., Miller, D. P., Vehring, R., Tep, V., and Kuo, M. C. 2008. "Trileucine Improves Aerosol Performance and Stability of Spray-dried Powders for Inhalation," *Journal of Pharmaceutical Sciences* 97(1):287-302 and http://www.nektar.com/pdf/dried_powder.pdf; Seville, P. C., Li, H. Y., and Learoyd, T. P. 2007. "Spray-dried Powders for Pulmonary Drug Delivery," *Critical Reviews in Therapeutic Drug Carrier Systems* 24(4): 307-360; Louey, M. D., Zijlstra, G. S., Hinrichs, W. L. J., de Boer, A. H., and Frijlink, H. W. 2004. "The Role of Particle Engineering in Relation to Formulation and De-agglomeration Principle in the Development of a Dry Powder Formulation for Inhalation of Cetrorelix," *European Journal of Pharmaceutical Sciences* 23(2):139-149; Van Oort, M., and Hickey, A. J. 2004. "Aerosol Dispersion of Respirable Particles in Narrow Size Distributions Produced by Jet-milling and Spray-drying Techniques," *Pharmaceutical Research* 21(7):1200-1206; Platz, R. M., Kimura, S., Satoh, Y-I., and Foster, L. C. 2000. "Methods and Compositions for the Dry Powder Formulation of Interferons" U.S. Pat. No. 6,123,936).

To avoid the risk of gas embolism, the endoluminal application of a gas or gas-propelled powder, albeit small in volume and directed into as to be substantially contained within the lumen wall, is substantially limited to use outside of the vascular tree. This is true even when delivery of a dry powder through a finer catheter to a considerable distance that necessitates higher pressure is uninvolved. A dry powder inhaler of conventional design does not generate the propulsive force required to move the powder down the catheter and therefore requires a to be adapted by incorporation into the supply line of a ventilator.

A larger sized precedent applied to an endotracheal tube of 9 millimeters in internal diameter having already been described in the literature (Everard, M. L., Devadason, S. G., and Le Souëf, P. N. 1996. "In Vitro Assessment of Drug Delivery Through an Endotracheal Tube Using a Dry Powder Inhaler Delivery System," *Thorax* 51(1):75-77), only miniaturization is necessary for use with a service-catheter. When some of the powder adheres to the proximal internal surface of the catheter with each actuation, the number of times that this apparatus can be used without the need to replace the catheter will be limited by the accumulated buildup of powder along the inside of the catheter walls. The actual number of actuations needed in a practical procedure should only rarely necessitate replacing the catheter.

XII13. Midprocedural Delivery of Lubricant to the Muzzle-Head

If despite the measures incorporated to minimize such an eventuality, adhesion of the muzzle-head to the endothelium occurs, a hypodermic syringe is used to inject lubricant into the proximal end of a barrel-tube or tubes used as a distal access barrel-tube as described above in the section entitled Muzzle-head Access by Means of a Service-channel, and a ramrod or test rod used to push the lubricant out through the muzzle-port. Rotation with the turret-motor as preferred for controllably minimizing the rotational displacement or by hand is then used to work the lubricant around the muzzle-head. A felt or cotton-coated ramrod is then used to remove any residual film from the walls of the barrel-tube or tubes.

XIII. Airguns

XIII1. Operational Requirements

From one distance along the ductus to the next, the tissue of a lumen wall can be either substantially uniform in mechanical properties, as is usually true of the subacute or pre-Grade IV collapsed trachea, or variable, as when vascular disease has differentially affected different portions of the arterial or venous wall. For the trachea, which is relatively large in internal diameter, a single miniball discharging airgun is appropriate. In the trachea, the miniballs are implanted along a dorsolateral longitudinal line in relation to the cartilage rings, relatively seldom at other points about the lumen circumference, and the working space affords maneuverability. In advanced collapse where secondary inflammation and infection may have altered the mechanical properties of the tissue, miniballs of one kind are implanted in one pass, and those different in a second pass.

Alternatively, if distinctions in mechanical properties of the tracheal tissue are present due to a different level of expression of primary pathology or due to independent, or trans-nosological, comorbidity with areas that exhibit various conditions, then the single-shot airgun load queue can be strictly sequenced according to a prescribed load list to include miniballs of different mass coated with different medications. Of these approaches, the first is to be preferred as minimizing the need for frequent adjustment of the airgun propulsive force resulting in a longer operation with increased possibility of errors. Because the barrel-assembly will obstruct blood flow, the time of any procedure in arteries, the coronary arteries in particular, is acutely time sensitive. While in the bloodstream, the barrel-assembly must not be discharged unloaded.

Unlike the rotary magazine clip which makes it possible to apply a consistent propulsive force to miniballs that differ in mass by means of securing each miniball in its clip hole with a dried solution or syrup of sugars, corn starch, or molasses (treacle) of a formulation and thickness to offset the lesser resistance to expulsion of any miniball or miniballs in a set to be discharged together, a single-shot airgun must be adjusted in propulsive force every time there is a change in the mass of the miniball to be ejected. With a rotary clip, the propulsive force may have to be varied with the sum of miniball masses. The solution or syrup is run about the groove formed by the perimeter of the miniballs and rotary clip holes by surface tension, and to prevent debris from moving down the barrel, the composition of this adhesive should have good self-adhesion.

Except in hole pattern, which is generally for a group of miniballs rather than one, the rotary magazine clips are conventional. Except in the circulatory system, where once introduced the one barrel-assembly, even though demanding adjustment for different miniballs, should not be removed and replaced, changes in miniball mass are accomplished by withdrawing the barrel-assembly and introducing one of another airgun. Alternatively, the barrel-catheter can be removed and one of different caliber connected to a second airgun of like caliber. While prior to fixation of the miniball within the rotary clip ring hole and as a separate operation, medication can be applied in a sugar or syrup coating that has been heat- or freeze-dried, the miniballs are produced to meet such special requirements.

The construction of the airgun includes a conventional rocker-arm stop that prevents the premature entry of a miniball into the barrel at the same time that it prevents a second miniball from partially entering the chamber before the chambered miniball has been expelled. A single 'shot' semiautomatic airgun can be queued with miniballs of like caliber but different mass, but were differences in mass to exceed the range over which the impact force would implant the miniball subadventitially without unacceptable under- or overshooting, the procedure must be interrupted to adjust the propulsive force. To adjust the single 'shot' airgun after one or a few discharges, is, however, not recommended as contrary to minimizing operative time; to minimize the number of adjustments, hence time necessary, all implant discharges of like mass are completed before proceeding to miniballs of different mass.

Using a simple airgun, the propulsive force can be adjusted after the complement of miniballs of like mass have been implanted or the barrel-assembly, which in the trachea consists of a simple catheter pipe barrel, is left in the patient, and the proximal end of the barrel-assembly is detached from the airgun and inserted into another airgun preadjusted to discharge miniballs of different mass. To change the caliber, however, requires withdrawing the barrel-catheter and inserting another of the new caliber. The same airgun can be adjusted or another already connected to the barrel-catheter can be used. Using a single shot airgun, the more complicated matters of mixing miniballs of different mass in a single shot as differentially distributing the propulsive force does not arise, because the airgun is not capable of multiball discharge.

At the extreme of demand is the diseased coronary vessel where to avert the risks posed by interruption in the circulation much less the use of a heart and lung machine, the time of the procedure must be kept to a minimum under considerably more difficult working conditions. This justifies the expense of certain refinements that make it possible to discharge multiple miniballs simultaneously in a radial pattern, to do this with quick repeatability, and to change the exit velocity to a value desired quickly by alternative means of control used individually or in combination. This is accomplished by a radial discharge muzzle-head that delivers a plurality of miniballs, usually four, one each into each quadrant of the circumference. The requirement to vent the air inside the barrels with the muzzle-head immersed in the bloodstream without introducing any gas into the bloodstream precludes the use of side holes as allow the blood to continue to flow if obstructed in guide-catheters.

Such an airgun is loaded by inserting the miniballs in a rotary or wheel magazine clip, that indexes the miniballs into 'firing' position in front of the propulsive gas outlet. The barrel-assembly built as an integral unit, and the muzzle-head usually radially symmetrical in internal structure, the caliber of the barrel-tubes and their respective muzzle-head exit ports in any one muzzle assembly are the same, even though specialized rotary magazine clips and barrel-assemblies could be made to combine different calibers in each discharge. Any change in the caliber or mass of one or more miniballs in the set to be discharged together must be offset by adjusting the resistance to propulsion of each miniball by changing the consistency of ingredients of a quick-dried syrup used to hold or clinch the miniballs in the rotary clip holes.

Every rotary magazine clip loaded into the airgun should be visually inspected and lightly shaked to be certain no miniball is loose. Vigilance exercised, premature entry of a miniball into a barrel is unlikely to result from looseness in the rotary clip hole, but rather because of imperceptible inequalities in the clip hold retentiveness of the miniballs of a set to be discharged at the same time, which can allow the propulsive gas to leave chambered or dislodge miniballs other than one offering critically less resistance. The improper apportionment of resistance to expulsion is minimized though rigorous testing and tight quality control. The miniball is retrieved by disconnecting the barrel-assembly from the airgun and passing a mildly magnetized guidewire down the barrel-tube.

The calibers of the miniballs in a given rotary magazine clip and the barrel-assembly must match, individual discharges that include miniballs different in caliber requiring the use of a special purpose clip and barrel-assembly to match these in caliber. Differences in mass for any reason, to include the addition of an outer layer to deliver medication or radiation, can be accommodated in single discharges. Since the propulsive gas will find the path of least resistance, miniballs of less mass must be equalized in clip hole retention by syrup bonding. Simultaneous discharge assumes that the distinction in mass is negligible; if the difference in mass is significant, the more massive miniball may not be propelled at all. The parallel use of different airguns to propel the miniballs in the different holes of the discharge set is not contemplated.

Reloading by inserting a new rotary clip or by detaching the barrel-assembly from one airgun and inserting it into another can be done quickly. To change the caliber, however, requires withdrawing the barrel-assembly and introducing another, and this negates the practicality in an airgun with multiple output ports or barrel-assembly fittings of different caliber. With the barrel-assembly exchanged, a rotary clip containing miniballs of different caliber can be inserted in the same airgun. Barrel-assemblies and rotary clips can be produced to discharge from one to four or more miniballs in a radial pattern. The ability to produce barrel-assemblies and matching rotary clips other than radially symmetrical increases the lower is the number of barrels or barrel-tubes.

In situations where the number of miniballs to be discharged at a time changes, proceeding with the barrel-assembly already in position is preferable to withdrawal and insertion of another. Changing the number of miniballs to be discharged at once is physically similar to differences in mass among a complete set, which likewise differentially distributes the sum propulsive force. In this case, however, the difference in mass will require an adjustment in propulsive force, which may take the form of adjusting the airgun in use or switching to an airgun preset to the required value. When the number of miniballs to be discharged at one time is less than the number of barrel-tubes in the barrel-assembly, a miniball mounting hole on the rotary clip is not left vacant but rather reduced in diameter to bring the force applied to the miniballs that are present to a sum value within the range that this would have been were a miniball present.

XII2. Modification of Commercial Airguns

Certain air pistols modified as specified below are loaded or fed miniballs from a line-feed type magazine clip. These are limited in use to single miniball or monobarrel discharge, specifically, simple pipe and single miniball radial discharge barrel-assemblies. An airgun that uses a rotary magazine clip can accept any barrel-assembly whether a simple pipe or a multibarrel radial discharge barrel-assembly. A modified commercial air pistol allows use of a simple pipe, and thus low implant density magnetic stenting and the targeted placement of medication miniballs within the ductus wall with injury limited to the diameter of the miniball trajectory and at minimal expense. A monobarrel is adequate for any application that calls for the discharge of no more than one miniball at a time.

The trachea and bronchi, which present differentiated anatomy, are best treated with a readily aimable simple pipe, or if too small in diameter, a radial discharge monobarrel, which is essentially a simple pipe with a wrap-around protective jacket, is suited for use in any ductus that is too small in diameter to admit a simple pipe. The tracheal collapse encountered in veterinary practice is often associated with bacterial infection; while an angioplasty-capable radial discharge barrel-assembly could be used to introduce an antibiotic directly into the diseased tissue, the proclivity of bacteria toward dispersion recommends systemic administration. Even the simplest pipe-type barrel-assembly must include a recovery electromagnet close to the exit-hole or exit-portal in the muzzle-head.

When not obtrusive or adding significant weight, the battery is preferably contained within the electromagnet housing and the control knob at a proximal or extracorporeal position on the barrel-catheter. The barrel-assembly can be provided with a slidable and removable power and control housing as a radial discharge-type barrel-assembly, but this adds much cost without justification, positioning the battery and control on the pistol equally functional. The battery is usually added at the bottom of the pistol grip and the control knob at the side of the chamber, the electrical connection made to avoid the gun barrel as shown in FIG. 75. Rather than using an electrical plunger switch as the trigger, a modified commercially available air pistol (hand airgun, air handgun) uses the original mechanical triggering mechanism.

The battery is attached as a downward extension of the pistol grip, with a potentiometer and knob for adjusting the current through, hence, the field strength of the tractive recovery electromagnet, attached to a control panel mounted to the inner face of the grip. Alternatively, the potentiometer can be mounted along the slide, or lacking a slide, the corresponding location, and a three-way toggle switch with fixed settings for recovery magnet off, recover (a dropped miniball), and extract (a mispositioned miniball) used in lieu of the continuously variable potentiometer. Modified air pistols for use with minimally ablation or ablation and angioplasty-capable barrel-assemblies must have a control panel that includes any controls needed to operate any additional features of the barrel-assembly, such as radial projection units or an embolic filter.

The first of the two modified commercially available air pistols now to be described uses a queue or linear sequential spring-loaded clip and is therefore suitable for use with monobarrel barrel-assemblies whether of simple pipe or radial discharge type. The more capable air pistol to follow achieves greater versatility by virtue of incorporating a rotary magazine clip, which allows either a single or a number of miniballs to be discharged at one time and thus the ability to support either a monobarrel or multibarrel tube barrel-assembly. Additionally, a rotary magazine clip type airgun allows the portion of the airgun overlying the chamber to be removed and replaced with transparent plastic allowing the failure of one or more of a set of miniballs to be discharged at once to be seen.

However, the discharge mechanism of an airgun that loads queued miniballs one at a time is incapable of multiple miniball discharge, and the failure of a single miniball to discharge would be immediately evident without such viewability. A rotary clip makes possible the projection of multiple miniballs per discharge and therewith. Whereas the successful projection of a single miniball is instantly evident, the failure of one of four to be propelled is not. Fluoroscopy and angioscopy used to confirm the placement of miniballs, it is additionally helpful to have the chamber retrofitted with a roof made of a suitable transparent polymer such as polycarbonate. This allows inevidence of a miniball to implant properly to be immediately traced to a failure within the airgun rather than loss in the patient.

XIII2a. Simple Airgun Modified to Allow Limited Application

The barrel-catheter in a simple pipe being the one barrel-tube, no course through the interior of the barrel-catheter or along the outer surface of the barrel-catheter to be inserted into the airgun is available for running the conductors for the recovery electromagnet. Since the external surface of the simple pipe comes into contact with the airway lining, the simple pipe-type barrel-assembly must not present any sharp edges or protrusions. The electromagnet in the muzzle-head is therefore connected to the battery mounted at the bottom of the pistol grip by fine wires attached to the outside of the barrel-catheter by means of a nonallergenic adhesive having the consistency of caulk. Since the recovery electromagnet wires and any bounce-plate device in addition to a viewing device must not be inserted into the airgun barrel, fiberoptic connections are made as shown in FIG. 75, circumventing the airgun barrel.

Barrel-catheter tube stock of sufficient thickness allows the countersinking of a wire-way with connection inside the chamber comparable to that depicted for a radial discharge barrel-assembly in FIGS. 72 and 74. Energization of the electromagnet is similar to that described above in the section entitled Stay insertion tools. The primary object in such an embodiment is to provide veterinary specialists with a simple and relatively inexpensive hand-held airgun that with suitable imaging equipment and a barrel-assembly with clearly visible markers can be used to ameliorate the intermittent asphyxia (suffocation) or airway throttling symptomatic of collapsed trachea in small dogs without the need for a thoracotomy.

The simplest airgun usable with the methods described herein delivers one miniball per discharge and connected to a simple pipe barrel-assembly, is suitable only for procedures in structures such as the trachea, while connected to single-barrel radial discharge barrel-assembly or monobarrel, is suitable for use in closed ducts and vessels. Ductus that are relatively large in diameter and open to the exterior afford greater accessibility and maneuverability but exhibit differentiated histological and anatomical structure. Speed in the airway must always remain consistent with a distinct aiming capability. The lumen of a closed vessel that is additionally diseased is accessed with relative difficulty, affords significantly less maneuverability, and is substantially undifferentiated with respect to its normal condition.

The closed vessel therefore poses the opposite set of factors for attaining operative speed. For the latter, speed that comes with multiple simultaneous radial discharge of miniballs in rapid succession. A modified airgun of the queue loaded or line-fed type is not suitable for applications in the vascular system where the ductus is closed to the exterior, the lumen diameter is usually two or three millimeters, and the disruption to the delivery to the cells of oxygen by the circulation calls for completion of the procedure in the least amount of time. A single shot per discharge semiautomatic repeat action airgun can be provided by modifying an off-the-shelf or commercially available hand airgun in bore to project small caliber miniballs and allow the propulsive force to be variably controlled.

Of airguns currently available, the Daisy 93/693 is suitable as clip-loading 15 shots, minimizing interruption for reloading midprocedure and as not presenting a reciprocating slide to interfere with the addition of a permanently positioned control lever. The break breech design also makes the insertion of a testing rod shortly to be described simpler, the rod inserted at the back of the barrel, making insertion of the key easier. Change to the bore can be effected by placing a sleeve inside the barrel to reduce the internal diameter or by increasing the thickness of the barrel-catheter. The use of a sleeve is preferred as not affecting the barrel-catheter flexibility, hence, material. The chamber must also be adapted for the smaller caliber. Such an airgun can be provided by modifying an off-the-shelf or commercially available semiautomatic repeat action single miniball discharge hand airgun to project small caliber miniballs.

The modification of commercially available airguns must be carried out by trained personnel in a special facility subject to stringent quality control. Such modification is discussed with greatest applicably in generic terms, actual models available being many, differing in inconsequential details, and constantly subject to discontinuation, while new models are frequently introduced. There are two major types of off-the-shelf or commercially available single miniball discharging hand airguns or air pistols, the first made to discharge gauge BB ball shot, the second pellets. Both kinds accomplish repeat action semiautomatically, the first by admitting or feeding one miniball at a time into the chamber from a queue or line contained within a spring-loaded loading clip into the chamber by the action of the preceding discharge.

A conventional rocker check-arm prevents the entry into the chamber (but not the barrel-tubes) of more than one miniball at a time. The adaptation of higher power airguns allows higher exit velocities for sclerotic and resistive tissue, such as that considerably calcified or ossified in patients for whom resection or excision is inadvisable. The higher propulsive force of such airguns is readily reduced to any lesser force by bleeding off the propulsive gas as will be described or by increasing the rolling resistance. No suggestion is intended that less forceful airguns, referred to as 'airsoft' or 'softair,' or that use the force of a spring to propel the spherule or 'BB,' or that are used to play paintball cannot be adapted for applications that demand impact forces less than the maximum for the airguns specified.

Representative of the many spring-clip line-fed miniball hand airguns are those manufactured by Maruzen Kabushiki Kaisha according to the specifications of and sold by the Daisy Outdoor Products Company. That bearing model number 15XT requires loading the miniballs one at a time; model number 93 since discontinued; and model number 693, now redesignated model number 93/693, which is clip loaded, and the Crosman-Walther PPK/S, all semiautomatic 4.5 millimeter (.177 caliber) and powered by a 12 gram $CO_2$ cylinder (canister, cartridge, tank), which the manufacturer will refer to as a 'powerlet' or 'pistolet.' An advantage of using the spring-loaded line feeding type clip to chamber successive miniballs semiautomatically, airguns designed to discharge miniballs rather than pellets are capable of a larger number of successive discharges or 'shots' without reloading, typically fifteen.

Some makes or models of line-fed or spring loaded linear queue type magazine clip loaded miniball hand airguns, such as the Industrias el Gamo V3, also semiautomatic, 4.5 millimeter (.177 caliber), and 12 gram $CO_2$ cylinder-powered, incorporate a triggering mechanism that to simulate the appearance and action of an actual automatic pistol firearm, includes a reciprocating slide that travels over the valve body and chamber, which are integral to the clip at the top thereof, the valve body above the gas cylinder and the chamber above the miniball queue. This slide does not preclude the retrofitting of a simple low-cost control mechanism presenting a lever to the outside of the airgun to allow the propulsive force or exit velocity to be adjusted without the need to remove the clip; however, because two layers of plastic slide past one another, the view into the chamber even with transparent material is obscured.

The modification of any commercial airgun includes the mounting to the front end of the muzzle of a barrel-assembly connecting socket as described above. To modify the Gamo-type mechanism is more difficult than the models that do not have a reciprocating slide. Daisy model 15XT has no reciprocating slide making it easier to modify, but unlike Daisy model 93/693, is not clip loaded, instead requiring that the miniballs be loaded one at a time, effectively necessitating that several be preloaded for any one procedure. Clip loaded and lacking a slide, Daisy model 93/693 is superior for use with a simple pipe barrel-catheter for tracheobronchial procedures. While it is easily within the capability of a rotary magazine clip airgun to be described, to use different caliber miniballs with one and the same spring-loaded queue fed airgun would require changing the inserts throughout the miniball delivery path inviting inaccuracy and malfunction. Such a low cost embodiment is preferably sold as permanently modified for use with a fixed caliber not to be changed by the purchaser.

XIII2b. Simple Airgun Modified to Allow Wider Application

The second type of airgun, some originally made to shoot pellets, uses a rotary magazine or wheel clip that typically provides fewer discharges than the line-loaded type clip, typically six successive 'shots' or discharges, before a spent clip must be replaced with a loaded one; however, replacing a spent rotary clip takes but a moment. Modified as described below, the rotary magazine clip can be used to discharge from one to four or more miniballs per discharge, making it considerably more versatile for realizing the objects stated above. As previously described, using either type of clip, different miniballs can be variously coated to deliver medication or radiation. A means for adapting either a spring-loaded queue or a rotary magazine clip type airgun with a testing mechanism is described under the heading 'universal means of testing' that follows.

Rotary clip airguns made in the form of rifles rather than handguns generally use rotary magazine clips that typically hold twelve pellets, and therefore use rotary magazine clips that are larger in diameter, affording a larger number of multiple miniball discharges and reducing the frequency of reloading regardless of the fact that custom clips are used. An example is the Crosman Model 1077, likewise semiautomatic, 4.5 millimeter (.177 caliber), and powered by a 12 gram $CO_2$ cylinder, with an AirSource® adaptor available for 88 gram (3.1 ounce) AirSource® cylinders. Yet other airguns, such as the model 617X made by Maruzen Kabushiki Kaisha according to the specification of and sold by the Daisy Outdoor Products Company, are available that are capable of shooting either miniballs or pellets, the added capability due to the mere incorporation into the rotary clips of a slight circumferential ridge to prevent miniballs from rolling out into the barrel before discharge.

All airguns that are able to discharge either pellets or miniballs use rotary clips that hold either miniballs or pellets of like caliber; none changes the repeat action to switch from clip rotation to discharge pellets to fixing the rotary clip in position for the opening aligned to the valve body outlet to serve as a miniball chamber. Daisy model number 622X, which shoots .22 caliber pellets, is identical to Daisy model number 617X, which shoots .177 caliber pellets or miniballs using the same rotary clips, and except for the fact that the rotary magazine clips supplied for the 622X lack a slight circumferential ridge at half the distance through the bore, would be equally able to shoot .22 caliber miniballs using the same clips. Provided with a slightly larger caliber, the 622X also uses clips that larger in diameter, afford greater latitude in the multiple miniball sets per discharge and caliber of the miniballs that can be accommodated in the custom rotary magazine clips to replace the original.

The following description of the modifications essential to make a commercially available airgun suitable for the repair of tracheal collapse by veterinarians as previously described presupposes a semiautomatic repeat action hand airgun wherein the miniballs are successively forced up into the chamber by a spring-loaded line-feed clip. To this end, the models specified above are mentioned in a purely exemplary sense; similar airguns produced by several manufacturers exhibiting much the same construction and capable of being modified to serve the present object equally well. Modification of the existing hand airgun is accomplished by placing caliber-reducing polytetraflouroethylene tube inserts in the spring-fed clip and barrel, and a caliber-reducing lining plugged into the chamber loading tube, which is situated toward the forward end of and integral with the clip.

The clip insert requires that the spring and plunger that drives the line of miniballs upwards into the chamber when the rocker arm lifts be replaced by proportionately smaller versions. Reducing the caliber from the original 4.5 millimeters to 1.0 millimeter, for example, increases the number of miniballs that can be loaded from 15 to 67. The number of cartilage rings in the dog trachea being 40 plus or minus 5, an extensive procedure necessitates reloading twice. The quickest way to accomplish this mid-procedure is to disconnect the barrel catheter from the airgun without removing it from the patient and reconnecting it to another fully loaded airgun, whereupon the first airgun is reloaded. A smaller hole through which to reload miniballs and a side slot to return the spring and allow the number of miniballs loaded to be seen must be cut into this tube, which is positioned concentric to the original loading hole or entry into the chamber at the top of the chamber loading tube.

If the wall thickness of the inserts placed in the barrel and miniball feeding channel in the spring-loaded line-feed clip in the grip does not center these as concentric within the original diameters, then tape is used at intervals along the length about the circumference to achieve a snug fit. Alternatively thin sheet of a polymer with a low coefficient of friction such as polytetraflouroethylene can be wrapped about the insert tubing to avoid the bunching up at the entry experienced with other materials. The barrel insert tubes used to reduce the caliber of the barrel stops half way down the barrel to allow the proximal end of the barrel-assembly to be inserted. The insertion of the caliber-reducing polytetraflouroethylene tube insert in the barrel covers over the rifling. The chamber insert lining properly centers the smaller miniball in relation to the propulsive gas entry hole directed to its apex at the rear, the miniball entry hole in the chamber floor, and the barrel to the fore.

The small finger at the top of the loading spring that pushes the last miniball up into the chamber through the floor must be replaced with one that is longer to pass the smaller miniball up through the hole in the chamber floor which has been made thicker by the lining. The original rocker check arm that admits only a single ball into the chamber at a time at the front bottom of the chamber must be removed and replaced with another proportionately smaller in size in the equivalent position to lap over the exit or muzzleward hole floor drop off at the center front of the chamber insert lining. The chamber insert lining has a hole at the center of the rear through which the propulsive gas is released from the valve body directly against the rear of and causing the miniball to travel down the barrel. This hole is proportionately smaller than the original hole behind it, the two holes positioned in flush concentric relation.

The small $CO_2$ cylinder or canister that fits into the clip adjacent to the spring-loaded miniball feed line is engaged by forcing it up against a hypodermic-type inlet pipe of the valve body at the bottom thereof by means of a screw beneath the cylinder. This connection by intromission affords no junction as would allow the insertion of a valve or regulator. This leaves the components that affect the propulsive force after the propulsive $CO_2$ has entered the valve body and chamber to introduce means for adjusting the propulsive force and therewith the exit velocity. Of the various means for effecting a reduction in the exit velocity in such a retrofit of a manufactured airgun, examined from the standpoint of greatest simplicity have been reducing the delivery of propulsive gas from the valve body as affected by the time and force of depression of the valve pin by the hammer.

Others have been to effectively increase the volumetric dimensions of the valve body and so reduce the pressure inside of it by means of a bleed slot continuously variable in area, a similar slot cut into the chamber, and lengthening and curving the barrel-assembly to increase rolling resistance disproportionately to the increased propulsive force of the extention in barrel length represented by the barrel-assembly. Of these possible points of interception to obtain the control necessary, replacing the hammer with a reciprocating armature (plunger, punching, push-type) solenoid of which the striking force and time is variable and introducing a bleed opening with adjustable cover in the chamber have been discounted as needlessly complex and costly in a modified airgun intended to be merchantable at relatively low cost.

The former is employed in more precise multipurpose embodiments originally produced to obtain the present objects, and the latter discounted as resulting in a mechanism so tiny as to be too difficult to readily adjust and test manually during an interventional procedure. Introducing a slot with sliding cover in the side of the valve body, however, allows a mechanism sufficiently large for practical use and can be added at reasonable expense. For precise and quickly reproducible adjustment, the sliding cover is positioned by means of a knurled turns ratio knob fitted with a vernier scale, the exact arrangement thereof contingent upon that of the air pistol modified.

XIII2c. Control of Propulsive Force (Exit Velocity) by Means of a Calibrated Slide Cover Over a Slit Cut into the Valve Body In modifying an airgun, the internal structure of the valve body remains unaffected, the addition of an external control being less complicated and more readily accomplished. That the modification is least variable from one model airgun to the next is a significant factor in reducing errors. As seen in FIG. 47, fine slot 227 covering an area to deplete the pressure delivered from the valve body 228 to a value below that required to produce the miniball impact force desired, such as 2 millimeters in width and 1.5 centimeters in length, is cut longitudinally into the valve body toward its front end.

The dimensions of slot 227 depend upon the pressure in the valve body, so that, for example, fine slot 227 in a Crosman 1077 based modification would be larger than that in a Daisy 622X.

The 12 gram cylinders in standardized use with commerically available miniball airguns deliver $CO_2$ at a pressure of 837 psi at 70 degrees Fahrenheit; however, the exact dimensions of the slot depend upon the volume of valve body 228 or its adjustment by the maker, which varies from one model airgun to the next. In an airgun with a reciprocating slide, valve body 228 is integral with the $CO_2$ cylinder beneath it in the clip, pushing ledge 229 must consist of a lever that is disengagable or foldable to allow the magazine clip to be removed from the grip for reloading, or a pin must be placed through a slot and into a depression in the slide. A slide frame or slideway in which the slide will be contained and longitudinally slid to continuously open and close the slot in a manner similar to some flat sliding door bolts is, in a retrofit as opposed to an original design, applied to the outer surface of the valve body.

The slideway is produced by die cutting and mold pressing thin stainless steel sheet to the curvature of the valve body. The sides or wings of the slideway extend outward enough to include a calibration in the pressing. A die-cut rectangular slide or tang is pressed to flush conform to the curvature of the valve body side wall and the slide frame. The slide includes a calibration mark and a hole in which to insert and fasten a small control handle, the extension of the handle on the underside acting as a stop. To minimize sticking resistance, the slideway and slide or tang may be given a thin coating of polytetrafluoroethylene; however, the closeness of fit of the slideway and slide must be such that resistance to being slid must never allow the sudden jolt of discharge to displace the slide.

The slide is positioned over the slot and covered over by the slideway, which is then fastened to the valve body by blind or pop rivets of 1.0-20 millimeters in flange outer diameter, in any of several types manufactured by Textron Fastening Systems, Emhart Division of Black and Decker, and other manufacturers, or threaded inserts made by Emhart. The slide is now retained within the slide frame against the outer surface of the valve body so as to freely slide forward and backward over the slot. Retracting the slide uncovers the slot from a fully closed hermetically sealed position to a continuously variable open position that allows $CO_2$ to bleed out of the valve body reducing the propulsive force driving the miniball through the barrel. In arteries, the direction of blood flow as antegrade or retrograde is proportionally negligible enough to disregard as a determinant of miniball impact or striking momentum.

The use of engaging depressions or dimples in the slideway and protuberances in the slide to act as detents at the calibration marks is discounted as suggesting that these settings have a favorable status. The height of the slideway above the outside of the valve body is such as not to come into contact with the gun body. In an airgun such as the Gamo V3 with a reciprocating slide on the receiver, a slot can be cut in the side of the airgun body slide to clear a handle of the pressure adjusting slide. However, as a handle would have to be removed or folded to withdraw the clip from the grip, a depression close to its leading edge or slot closing end can be made to allow a pin to be inserted as a removable handle to adjust the slide by aligning the calibration on it to that alongside the slideway and to act as a stop.

To introduce a miniature electric motor inside the valve body to move the slide that is powered by a battery and control at the butt of the grip is discounted as inconsistent with the object of providing a simple limited purpose retrofit at relatively low cost. The modified airgun is sold with a table relating the calibration to the exit velocity and indicating the range of settings suitable for the tissue to be treated in a patient of given species and size, and providing instructions for measuring and finding the best impact force to use. A printed table that sets forth the settings for a given tissue affected by specific disease is consulted and the airgun adjusted to this setting. The end position of the first implant is carefully observed fluoroscopically and if in a vessel, angioscopically, to confirm the setting and to apply any adjustment needed before proceeding to the next discharge.

In use, the table is consulted for the recommended exit velocity and impact force data for the barrel-assembly and miniballs to be used for the tissue to be treated, the airgun is test discharged against impact force registration paper (pressure sensitive paper, tactile pressure indicating sensor film, pressure sensitive film, Fuji Paper or Fuji Prescale) or Pressurex® produced by Sensor Products, Incorporated, Madison, N.J., which is a film of Mylar®, E.I. du Pont de Nemours and Company, for biaxially oriented polyethylene terephthalate (boPET) polyester film treated to provide a certain color indicative of the "pressure" (impact force). For higher resolution, a ballistic pendulum is used to measure the impact force. Then the exit velocity is adjusted by means of the slot slide introduced into the valve body, and the airgun output measured again.

This process is repeated until the impact force has been optimized for the tissue within the predictable limits. To expedite adjustment in use, preliminary testing must also plot the relation between the slide adjustment and the impact force. The effect of the initial discharge is carefully examined before proceeding and the exit velocity adjusted accordingly. Such viewability also allows confirming the precise alignment of the barrel-assembly with the configuration of the miniballs in the rotary magazine clip. Airguns in current production that use rotary magazine clips do not have a slide that reciprocates forward and backward along the top of the receiver making it possible to retrofit the chamber with a roof made of a suitable transparent polymer such as polycarbonate.

The simplest airgun for use with a simple pipe barrel-assembly must be equipped with a potentiometer having a control knob where the thumb contacts the grip or alternatively, a three-way toggle switch with settings for recovery magnet off, retrieve (a dropped miniball), and retract (a mispositioned miniball). to adjust the magnetic field strength of either trap-extraction tractive electromagnet in the most distal portion of the muzzle-head from zero to the maximum. For use with a barrel-assembly with a motorized turret to rotate the muzzle-head, a bidirectional rotation control is also required in this location. A critical increase in versatility is provided in commercially available hand airguns suitable for modification that provide semiautomatic operation by means of a rotary magazine clip or wheel clip rather than a single ball advancing spring-loaded feed line.

With a rotary magazine clip, multiple miniballs can be positioned in front of the barrel-tubes at a single time. Rotary magazine clips are intended for projecting pellets rather than balls but can of For projecting plural miniballs simultaneously, or multishot semiautomatic operation, the use of a rotary magazine clip is preferred. A representative example of such a hand airgun is made by Maruzen Kabushiki Kaisha to the specifications of and sold in the United States by the Daisy Outdoor Products Company under the trade name Powerline 622X. This model is designed to shoot 0.220 inch (5.5 millimeter) pellets.

The rotary magazine clips provided with this airgun are designed to hold pellets rather than miniballs, but as is demonstrated by Daisy model 617X requires only the addition of a slight midcircumferential ridge along the internal surface of the hole to achieve retention of a miniball rather than a pellet. Interchangeable the rotary magazine clip mechanism is the more versatile, allowing one to four miniballs to be poised for discharge at a time. If a rotary magazine clip that is conventional in diameter but adapted to hold millimeter miniballs will not allow the number of discharges required for a procedure, then the rotary magazine clip must be replaced during the procedure, an automatic mechanism to remove and replace the rotary magazine clip exceeding the present scope.

XIII2d. Docking Stations for Modified Commercial Airguns

Airguns can be prepared for interventional use by modification of commercial airguns. For applications requiring miniball precise placement, a 'docking station' that includes a linear positioning stage for automated incremental transluminal movement is provided. However, the limitations in control over discharge velocity limit the application of modified airguns to applications in the airway and larger ductus. A modified air pistol is suitable for use with a simple pipe in veterinary practice to alleviate tracheal collapse.

XIII2e. Positioning Modes of Operation

Positioning and operation of the muzzle-head at any given time may be manual, manual with direct control over the linear positioning table airgun mounting and/or turret-motor, or manual in initiating automatic sequences or discharge groups wherein once selected by the operator, the rotary angles and/or distance separating the individual discharges is accomplished automatically. During manual, as opposed to automatic transluminal movement, the turret-motor and discharge remain disabled. The controls onboard an ablation or ablation and angioplasty-capable barrel-assembly allow the operator to switch the automatic retraction of extended tool-inserts with trap-filter deployed on or off as desired.

The urgency to minimize ischemia while achieving a closely positioned formation of miniball implants may recommend the concurrent use of the turret-motor during discharge synchronized to the transluminal movement of the barrel-assembly by the linear positioning stage. The control over transluminal movement by a clocked linear stage allows the exposure time to atherectomizing action of a laser or rotational burr to be tightly governed. Timed discharge is controlled as an auxiliary function of the positional system controller.

XIII2e(1). Positioning with a Simple Pipe

Because the structured anatomy demands the discretionary placement of each implant, use of a simple pipe in the airway is always under direct manual and never automatic control. The airway in all but the tiniest (veterinary or premature birth) patients affords sufficient space to maneuver the handpiece, the structures involved are observable endoscopically, ultrasonographically, or fluoroscopically. The tractive electromagnet is hand-operated. Airgun (not positional) operation in this or similar environment is semiautomatic as not to require reloading mid-magazine clip.

Other than not having to reload the airgun between clips and energization of the tractive electromagnet, the simple pipe lacks the auxiliary functions required in a radial discharge embodiment suitable for use in the bloodstream which demands very fine and fail-safe retraction or deployment during transluminal movement near or over a lesion, which accordingly, is automated. Control of the tractive electromagnet, and the transluminal advancement, withdrawal, and rotation of the simple pipe are thus completely manual.

XIII2e(2). Automated Positioning with a Radial Discharge Barrel-Assembly

Most extraluminal stenting will, however, pertain to ductus no larger in lumen diameter than 3 millimeters, and except for the segments that necessitate treatment, have a relatively uniform structure. Discharge in smaller ductus seldom involves individual longitudinally disparate shots but rather the uniform incremental implant-carpeting of a lesion or the entire lumen. In this environment, safety measures to avert downstream embolization by escaped miniballs or plaque debris are actuated automatically even when longitudinal or rotary movement of the barrel-assembly is manual. When longitudinal or rotary increments no greater than 2 millimeters are required, control over transluminal displacement, the rotary angle of the muzzle-head and thus the direction of the muzzle-ports, recovery tractive electromagnets, and radial projection units demand measured control of machine accuracy.

For this reason, manual control as it pertains to the vascular system, for example, is substantially limited to discretionary direction over gross transluminal distances such as from the introducer sheath to the lesioned segment and back, angular displacement when noncritical, and the larger transluminal distances separating lesions. Manual control is otherwise pertinent to operator commanded automated actions, to include the distance separating successive discharges to apply across a given lesion and optionally, the number of individual discharges to constitute the discharge sequence or group. The airgun is provided with controls for the operator to direct discharge in groups or discrete sequences where each such group comprises a selected number and uniform spacing of individual discharges.

The duration of the manually controlled automatically unfolded operations is usually brief, the length of the ductus to be treated limited to the segments that are diseased or to be stented. Control of the airgun in executing these automatic discharge sequences is accomplished by switching relay and time delay components extrinsic to the airgun mechanism proper and is unrelated to the fully automatic operation of firearms. While the operator selects the number and distances to separate the discharges (individual shot or shot-groups) in a set, the coordinated timing of discharge and action of the linear positioning table stepper (or hybrid stepper) motor in incrementally moving the barrel-assembly and, if applicable, the turret-motor in angling the muzzle-head in each discharge group, is electronically coordinated.

In addition to positional adjustments of the muzzle-head that exceed the manual capability to directly manipulate or the imaging capability to clearly see, safety factors relating to the prevention of inappropriate discharge and the actuation of auxiliary functions, such as the deployment and retraction of side-sweepers and trap filter, disablement of the trigger-switch, inactivation of the linear positioning table stepper motor and radial projection units, if present, during discharge, are not left to operator memory. However, not all functions are preferably automated, those configurational with respect to the apparatus applied preprocedurally for reasons of simplicity and economy.

Thus, as described above, the number of muzzle-ports and any eccentricity in the trajectories to characterize each discharge are achieved by preselecting a barrel-assembly of suitable configuration, while the number, caliber, and type of implants is prearranged by the choice of clips, the miniballs and blanks in each clip position, and the barrel-assembly used. While changes in the exit velocity could be automated to execute during a discharge set pattern, such adjustment is seldom required from one lesion to the next or even during a procedure, and to impart this function increases the cost of the airgun. Accordingly, if necessary, the exit velocity is adjusted once a short term automatic routine has terminated. A malfunction mid-routine abends the routine and disables the airgun. Immediately upon completion of the routine, the trigger switch is reenabled.

Thus, once the apparatus has been preconfigured for the specific procedure, manual control of a radial discharge barrel-assembly consists of gross transluminal movements to bring the muzzle-head within or away from close reach of the site to be treated, selecting the exit velocity, the number, and the distance of uniform increments to separate the automatically positioned and timed successive discharges applied to a given lesion, the deployment of radial projection units if present, direct remote manual control over the transluminal position of the muzzle-head and rotational angle of the muzzle-head when not radially symmetrical, and the electromagnet settings. For reasons of safety, the energization of the electromagnets at the resting trap-recovery field strength during discharge and the deployment of the trap filter at the same time as the radial projection units when tissue removing tool-inserts have been installed are, however, not left to memory but made automatic.

XIII3. Dedicated Interventional Airguns

XIII3a. Operational Requirements

Airguns dedicated for interventional use must respond to operative and human factors design desiderata, to include expeditious and immediate control under operative conditions, consistent performance without deviation from the control settings, and ergonomics, or optimization and comfort in manipulability. Properly configured, an interventional airgun reduces operative times by providing multiple points for quickly adjusting the exit velocity or impact force between successive discharges, the recovery electromagnet field strength to retrieve a mispositioned or loose miniball, and usually provides duplicate control panels to allow control by an assistant when circumstances take the attention of the operator from discharge parameters as such. Dedicated interventional airguns include control points in addition to a slidably adjustable slot as pressure relief valve in the valve body.

Due to the variability in mechanical properties of diseased tissue, unless the operator is confident of consistency from one target point to the next, adjustment in exit velocity should be based upon testing the target tissue as described below in section XVII entitled Testing and Tests below as pertain to internal approach. A single standard 12 gram disposable liquified $CO_2$ cylinder, usually referred to as a powerlet or pistolet, will suffice for most procedures. When inadequate, the cylinder is replaced before the depletion of pressure affects power output and performance, which factor is paramount and will vary with the specific embodiment. The need to replace a cylinder is reduced about twenty-fold and usually eliminated through use of an 88 gram cylinder, sold under the trade name Crosman AirSource®) or the equivalent, and may be sold in England as relabeled with the brand name SMK.

Shown in FIGS. 81 and 82 are interventional airguns with gravity-fed queue, or sequential-feed miniball loading, hence, capable of discharging but a single miniball at a time. With such a gravity or spring advanced clip queue, a small rocker lever arm of the same kind as is used in conventional air pistols is used to admit only one miniball at a time for discharge. These airguns are suitable for use with simple pipe-type or radial discharge single or monobarrel barrel-assemblies. The type of miniballs used is changed by removing the hopper, shute, silo, or clip containing one type of miniball and replacing it with one containing another type of miniball. Feed that allows miniballs to be queued allows varying the successive type miniballs of the same diameter in the queue. Monobarrel radial discharge barrel-assemblies lack means for pressure equalization, making these unsuitable for use in the bloodstream.

Unlike the fully capable embodiment described below, simple pipes are for manual use and are not used in conjunction with a positional control system. When connected to a basic interventional airgun rather than a modified air pistol, the simple pipe is still discharged as with more advanced airguns by depressing a plunger or dead-man trigger switch. Simple pipes and airguns are suitable for use in veterinary practice to repair a collapsed trachea, and may be used to administer subcutaneous drug miniballs in humans. A simple pipe inserted in a modified air pistol or a simpler dedicated interventional airgun is primarily intended for use in the airway or in any ductus for which the distancing between successive implant discharges does not demand a level of precision beyond that attainable by hand.

Airguns for supporting monobarrels whether simple pipes or radial discharge barrel-assemblies can be either gravity fed as shown in FIGS. 81 and 82, a rocker arm (not shown) used to admit one miniball into the chamber at a time, or rotary clip fed. Radial discharge Barrel-assemblies which discharge two or more miniballs per discharge use a rotary clip feed. Accordingly, the dedicated interventional airguns shown in FIGS. 81 and 82, especially the latter, might have been depicted with the rotay clip feed mechanism as shown in FIGS. 31 and 32. Very small dogs, for example, are however, treated with a monobarrel radial discharge barrel-assembly, which surrounds the pipe as barrel-tube within a protective shell, allows more than a single miniball to be discharged at a time, and when discharged as an auxiliary function of a positional controller, achieves precise incremental placement.

Whether simple or advanced, dedicated interventional airguns provide a toggle switch to energize the electromagnet, a potentiometer control knob for adjusting the solenoid timing, and a manually adjustable slide-cover in the valve body. With any barrel-assembly, controls must be conveniently placed to allow immediate adjustment in the recovery electromagnet field strength. In a radial discharge barrel-assembly, two recovery electromagnets are used, and each is separately controllable. Typically, the controls for recovery electromagnets comprise a rocker switch marked 'Off' to one side and 'On' to the other, and an adjacent rotating knob activated only when the rocker switch is in the 'On' position to continuously vary the field strength, the provision of presets considered obvious.

The simplest interventional airgun is thus more versatile and adept than is a modified air pistol Not pertinent to the use of a simple pipe barrel-assembly are, for example, the need to accept rotary magazine clips, which pertain to use with radial discharge barrel-assemblies with two or more barrels (barrel-tubes), to accommodate much less provide controls for a linear positioning stage or table, as well as other components such as a turret-motor, required in radial discharge barrel-assemblies for use in small vessels and ducts. FIGS. 31 and 32 show the use of a rotary magazine clip which can index one or more miniballs into position for discharge at a time. Such a feed is usable with a simple pipe barrel-assembly, which has but a single barrel-tube, when one miniball is loaded in each hole in the clip. Loading more than one miniball per hole is pertinent only to radial discharge barrel-assemblies.

Even though simple pipes and radial discharge barrel-assemblies with one barrel-tube are both monobarrels, an airgun for use with the latter requires controls for positional control when used. As described above, modified air pistols provide fewer points of control than do dedicated interventional airguns. To incorporate multiple controls in an air pistol and provide a stable mount for attachment to a linear stage is discounted as defeating the lower selling price that is its primary object. Manual positioning necessitates some freedom of movement, and as with a modified air pistol, this is attained by providing adjustability in the exit velocity to compensate for some bending in the barrel-assembly. Such presumes that the operator has fully tested the exit velocity or impact force at various levels of sag prior to operating. Dedicated interventional airguns incorporate the same valve-body slideway as modified airguns as the basic means of control, but to expedite and refine adjustments, offer additional control points.

XIII3b. Interventional Airgun with Liquid Vaporization-Upon-Release Cartridge or Compressed Gas Cylinder Connected Directly to the Valve Body Inlet Suitable for Use Over a Range of Exit Velocities (Forces of Penetration) in Quick Succession with Moderate Redundancy as to Points of Control Over Discharge Gradual curves in the barrel-assembly reduce the exit velocity and sharper curves can do so to a significant extent by percent in relation to the range of exit velocities effective in placing the miniballs subadventitially before puncturing the outer fibrous layer of the ductus. The use of thicker tubing in the barrel-catheter and barrel-tubes, a larger diameter barrel-catheter, use of centering devices to place the barrel-tubes farther from the central axis, and blood-tunnels to increase the stiffness of the barrel-catheter over the length usually not required inside the body have been mentioned above. A description of an interventional airgun that incorporates automatic positional control will be found following a description of components such as a linear positioning table used to execute the positioning. The incorporation of a photo-ablation excimer laser also adds stiffness to the barrel-assembly.

A radius of curvature that is severe without kinking or distorting the barrel-tube in internal diameter demands greater propulsive force to achieve the same exit velocity as were the barrel straight. Operative speed being a crucial factor in achieving a good result, to expedite adjustment of the apparatus to achieve the exact exit velocity desired, provided are interventional airguns with several control points, some redundant. Interventional airguns are always to be provided with guidelines for selecting and testing exit velocity for a specific application. Due to the greater variability in mechanical properties of tissue once diseased, the automated coordination of the separate controls of dedicated interventional airguns to instantly bring the gun to preset exit velocities must afford fine adjustment if not continuous variability. Such control would not be particularly advantageous, and is not considered to be worth the additional expense.

In a simple embodiment intended for use with a refillable cylinder of compressed air that has been pressurized for use with a tissue of certain properties as shown in FIG. 81, an electropneumatic valve consisting of a plunger solenoid actuator and valve body is used to admit and within a small range compared to a regulator, control the pressure of the gas used to propel the shots, hence the exit velocity and force of impact. The control knob adjusts the voltages that regulate the extent and duration that the electropneumatic valve opens to the pressurized gas. Providing dedicated interventional airguns with an additional foot control switch to trigger discharge is not preferred. A conventional electrical foot-switch must be adapted to incorporate a safety pin that must be released by depressing a lever with the toe of the opposite foot, and limited to triggering only, the foot switch is too limited.

The incorporation into a foot operated control panel of all the controls necessary to use the apparatus is rejected as inviting unintended actuation. FIG. 81 is a block diagram, not to proportion, of a gas-operated surgical miniball implant insertion airgun with compressed gas cylinder connected directly to the valve body inlet. While represented this and the dedicated interventional airgun next to be described are represented as gravity fed as suited to use with a simple pipe barrel-assembly, it is to be understood that either can also use rotary magazine clips and so accommodate any kind of barrel-assembly. In addition to the valve controls provided, different delivery tubes friction fit to the end of the barrel can be used to variously reduce the barrel exit velocity, hence, the force of impact.

Such an embodiment, using a single cylinder of compressed gas without the additional expense of a regulator, is suitable for use where the a range of exit velocities or forces of penetration is required, as when treating a single tissue to a single depth. Under normal circumstances, a disposable delivery catheter designed for the particular application is provided. A device as shown above and in the following FIG. 82 allows continuous variability in the force impact, which expedites testing tissues for the purpose of disposable catheter design. The compressed gas can be supplied, for example, from either an internal prefilled disposable $CO_2$ or by means of piping from an external CA compressed air cylinder. Whereas $CO_2$ delivers 837 psi at 70 degrees fahrenheit, a compressed air cylinder can be filled to a preferred pressure.

With the interposition of a small adaptor, either a $CO_2$ or CA cylinder can be connected to the valve body inlet. Using a single source of compressed gas without regulator keeps the design simple and economical. A small $CO_2$ cylinder inserted within the enclosure makes the single-purpose airgun self-contained and compact. Containing nonliquified gas, a compressed air cylinder is larger and therefore connected from outside through a hose but can be filled to any pressure within its design specification. With or without a regulator, control with a single source of compressed gas is limited to reduction in the outlet pressure (also referred to as a canister or tank). With this basic design, variability in shot impact force is limited to adjustment in the field strength and duration of plunger solenoid actuation.

Preserving this simplicity and economy limits the pressure-reducing features that can be built into the airgun. Nevertheless, by connecting compressed air cylinders filled to different pressures, even the simple airgun can be used to treat different tissues to different depths of penetration. In such use, multiple cylinders of compressed air are connected and switched among manually by means of a pneumatic or electronically by means of an electropneumatic station valve. This can be done at no great expense when switching is manual; however, the parts necessary to switch among different cylinders with electronic valves loses the economic edge over a design that affords continuous variability in pressure through the use of a regulator. A warming jacket containing a heating element or coil about the gas delivery tube with thermostat or pyrometer control can be used to change the temperature and so adjust the pressure.

Since conventional $CO_2$ cylinders are rated for up to 1800 pounds per square inch (psi), the range of pressure control gained in this manner is much less than it is with compressed gas cylinders, which can withstand thousands of psi. For clarity, FIGS. 81 and 82 show the pressure gauge P, temperature gauge or pyrometer T, and voltmeter V housed separately from the table-top or stanchion-mounted main unit. PSOS is a full-wave rectified regulated power supply output switch. The take-offs for the different components are voltage divided by a bleeder resistor, each circuit controlled by a variable resistor. EPOT is a electronic potentiometer remotely operated from the remote hand control. In a simpler version, the potentiometer is mechanical, in the same position in the circuit, but mounted on the chassis rather than the hand control, and VCTDR is a voltage-controlled time-delay relay.

Essentially, there are two circuits, one pneumatic, the other valving the passage of gas through the pneumatic circuit. The combination of the plunger solenoid and the gas valve constitute a special purpose impulse-actuated electropneumatic valve. Whereas a enclosure-mounted manually operated potentiometer is less costly and assumes operation by an assistant, an electronic potentiometer in the remote hand control affords the operator direct control; both can be connected in series. Depressing the remote control 'deadman' or plunger type trigger switch at the top of the joystick control connects the power supply through the EPOT and VCTDR to the undamped direct current powered plunger solenoid, energizing the solenoid coil. This causes the solenoid plunger (slug, armature) to strike or punch the spring-loaded valve inlet pin forcing open the valve within the valve body for the interval set by the VCTDR.

Use of the plunger switch trigger requires release of the safety by retracting a pin intromitted into the side of the control button or key which is placed at one end of a spring-loaded lever retracted by pressing the opposite end with the ball of the index finger. The gas thus admitted to the rear of the mini ball implant in the receiver propels the implant as a projectile through the barrel and delivery tube at the target tissue. Adjustment in the output of the power supply through the potentiometer varies the actuation field strength of the solenoid, varying the punching force of the solenoid plunger against the valve pin. Increasing the force of plunger impact upon the valve pin also slightly increases pin excursion, hence, valve open-time. Valve open-time is thus determined both by the interval that the switch connects the solenoid to the power supply and by the voltage. This timing may be controlled as a structural or mechanical feature of the switch contacts or through a separate electronic time-delay relay.

Absent such a solenoid actuation time mechanism, the solenoid plunger would not retract until the switch was released, which interval is too long. The discontinuous character of the function, which involves the intermittent discharge of sudden shots, does not lend itself to servomechanical control; instead, a V voltmeter indicating EPOT output on the enclosure serves to implement human feedback. The acrylonitrile butadiene styrene (ABS) enclosure with a thermal conductivity between 0.14 and 0.21 W/mK and 97 cubic feet per minute (cfm) fan with plastic vanes and frame prevent the undesired buildup of heat that could materially alter the gas pressure and therefore terminal ballistics. Adjusting the fan speed and thus the volume of air moved through the enclosure by means of a thermostat is another way that the temperature of the gas can be controlled to obtain variability in pressure.

Conventional means exist for preventing the temperature to exceed a set limit, and even were such to malfunction, all compressed gas cylinders incorporate a pressure relief mechanism. Thus, even using a single cylinder, and even when the cylinder contains $CO_2$, which is not normally viewed as affording variability in pressure, numerous variables are available to control the pressure and therefore the force of impact and depth to which the shot will penetrate given tissue. Of these, the least costly embodiment shown here employs those variables that govern valve open time. In an embodiment that must afford a wide range of penetration forces for a single procedure, a regulator capable of continuously adjusting the gas pressure is used. Whereas a regulator and the control means shown allow pressures less than that to which the cylinder is pressurized, increasing the temperature allows the cylinder pressure to be exceeded.

The power controlled from the remote control hand piece is represented as controlling both the output from the power supply through the electronic potentiometer and the input power proportional time delay. That is, the same potentiometer is used to vary the input to the solenoid and the time-delay relay to continuously vary the force and interval that the valve is held open, both of which factors increase valve open-time. Separate control of the time delay does not significantly extend control variability. Whether manually adjusted in a simpler model or electronically in one more costly, a regulator is usually controlled separately. In such an embodiment, the regulator is in effect the gross adjustment, whereas the controls shown here serve for fine adjustment. To avert disruption due to malfunction, more than one such relatively simple apparatus, each adjusted to the same settings, should be present. If more than two are available, differently adjusting these in pairs allows treating different tissues.

XIII3c. Interventional Airgun Suitable for Procedures Involving the Treatment of Different Tissues to Different Depths in Quick Succession with Redundant Points of Control to Adjust the Exit Velocity FIG. 82 is a block diagram, not to proportion, of a gas-operated interventional airgun suitable for procedures involving tissues that differ widely in resistance to penetration where there is the need to penetrate to different depths, necessitating adjustability over a wide range of shot impact forces. The airgun is shown with a gravity queue-fed magazine implying use with a simple pipe, but is capable of loading rotary magazine clips. The use of an interventional airgun that lacks automatic positional control where precise distancing between successive discharges is essential, as is often true in the vascular tree, for example, is not preferred. Such an airgun is suitable for use, for example, with a simple pipe-type barrel-assembly in the airway or in any ductus operable manually as not to demand precise distancing between successive implant discharges.

While shown in FIGS. 81 and 82 as gravity loaded, such airguns can be loaded with rotary magazine clips that allow multiple miniballs, usually two, aimed diametrically, to be discharged at a time. As previously described, such clips allow the mixing and matching of different type miniballs, some of which may consist entirely of medication or any of numerous other type substances. The barrel-assembly can, for example, be used to introduce miniballs that consist entirely of medication or irradiating seeds, which may constitute the entire purpose of the procedure, or such may be done on an initial pass, an interval allowed to pass for the preparatory medication to take effect, then the barrel-assembly reversed in direction to infix the implants. That is, reloading at the proximal extracorporeal end of the apparatus eliminates the need to withdraw and reintroduce the barrel-assembly.

Interchangeable single, or individual 'BB,' and multiple-shot or shotgun shell-adapted pellet casing loading mechanisms allow the same propulsion apparatus to be used analogously to a rifle or shotgun, where the object is likewise similar—either to deliver individual shots with discretionary placement in suture mode or distribute shots over an area in stent mode. The latter is far more frequent, uniform distribution spreading the magnetic attraction and therewith any risk of pull-through, and with the need for precision reduced. For improved visibility, the large digital pressure gauge P, temperature gauge or pyrometer T, and voltmeter V are housed separately from the table-top or stanchion-mounted main unit.

The following acronyms are used. PSOS—power supply output switch. EPOT—electronic potentiometer remotely operated from the remote hand control. In a simpler version, the potentiometer is mechanical, in the same position in the circuit, but mounted on the chassis rather than the hand control. VCTDR—voltage-controlled time-delay relay. EPR—remotely controlled electropneumatic regulator; as with the potentiometer, using a manual regulator with control knob mounted on the enclosure considerably reduces the cost of the apparatus. Whereas manual control makes maximum use of an assistant, remote control allows immediate adjustment by the operator. The compressed gas is stored in a disposable $CO_2$ cylinder prepressurized and unrefillable at 837 psi at 70 degrees Fahrenheit.

$CO_2$ cylinders are available in a variety of sizes, to include 9, 12, and 88 grams or 9, 12, or 20 ounces. The cylinder is connected to the valve body through a continuously variable regulator that allows a range of gas pressures for use with any suitable tissue. A manual regulator can be used for economy but an electrically controlled regulator allows direct control by the operator. The use of a regulator eliminates the need to connect differently pressurized cylinders or change the temperature whenever treatment moves from one tissue to another. A time-delay relay is still required to limit the interval that the solenoid is actuated, but a potentiometer, while still desirable, is not essential for control.

While less costly, a manual system that interswitches among plural cylinders does not achieve equivalent continuity or smoothness of operation. To employ an electrical means of switching among cylinders would lose much of the economic advantage of switching compared to a manual if not an electrical regulator. A manually operated regulator can be controlled by means of a knob on the enclosure. To avert disruption due to malfunction, more than one apparatus should be present and adjusted to the same settings as the procedure unfolds. With a regulator, other means for altering the force of impact, as by changing the delivery tube to one of different length or a material of different coefficient of friction are unnecessary.

XIII3d. Interventional Airgun with Multiple Exit Velocity Control Points for Quick Midprocedural Adjustment, Using Rotary Magazine Clips, and with an Automatic Positional Control System Suitable for Implanting the Wall of a Blood Vessel An interventional airgun suitable for use in the vascular tree incorporates automatic positional control that allows successive discharges to be placed at smaller distances than can be attained manually with accuracy. To achieve uniformly equidistant separation of the implants in a formation and thus reduce the risk of pull-through within a ductus having a caliber the size of the average artery, for example, necessitates automatic operation, the muzzle-head as 'tool' advancing or rotating, discharging, and continuing according to the control input of the operator. Such an airgun is the same as that last described but supplemented with positional drives and controls and a rotary magazine clip that unlike the queue or linear succession spring-loaded clips in many commercial hand air pistols if not that type described above as more capable, and gravity-fed loading in the preceding interventional embodiments, which are meant for use with a simple pipe-type barrel-assembly, can load multiple miniballs in any combination for simultaneous discharge.

Since the second of the two kinds of modified commercial air pistols described above uses a rotary magazine clip, it is capable of discharging more than a single miniball at a time; however, lacking a positional control system, the targeting of each discharge must be achieved manually, which taking time, is unsuited to use in the circulatory system and in the coronary arteries in particular, where quickness is imperative for averting the ischemia that can induce a myocardial infarction. The same may be said of use in the carotid arteries where the risk of a cerebral infarction must be minimized. Of the two types of interventional airgun described above, neither uses a rotary magazine clip as allows the use of more than a single barrel-tube. In the second and more capable air pistol, the rotary magazine clip is rotated by a pawl that is mechanically linked to the trigger and engages notches about the circumference of the magazine.

In the mechanical system seen in a conventional airgun that uses a rotary magazine clip, the pawl that rotates the clip is moved when the trigger is pulled back, so that the rotary magazine clip has already rotated or indexed to place the next load before the $CO_2$ inlet when the trigger reaches the end of its travel (excursion, throw), at which point the hammer is released to strike the valve body pin effecting discharge. Here, the same sequence is reproduced through the use of a plunger switch that when partially depressed completes the circuit through a small electromagnet, and when fully depressed, completes the circuit through the push or punching solenoid used as a hammer.

When triggering is electrical, the rotary magazine clip and pawl are no different than those used in a mechanical linkage to the trigger but differ in that the pawl is actuated by the small electromagnet that is energized by depressing the spring returned trigger consisting of a raised plunger (pushbutton, dead-man) double pole double throw normally open momentary close contact switch mounted within the top of the joystick. One point of control in this airgun governs valve body pin depression time. While this interval could be affected at the trigger switch, more precise and replicable control is achieved by the means to be specified.

XIII3e. Linear Positioning Stage or Table Airgun Mount

The airgun linear positioning table (linear platform, linear stage) mounting is purchased as a complete subassembly, to include both the linear positioning table and actuator. Numerous types of linear positioning tables are available, some open-loop controlled with stepper motors, others closed-loop controlled with dc servomotors. The actuator can be linear or rotary, and in either category, any of several different kinds. The table itself requires no modification; rather, adaptation for the present purpose consists of its positional control programming. A linear positioning table is no less useful for precisely positioning a radial projection system injection tool-insert, for example, whether the injector is an electrical/fluid system-neutral or spring discharged syringe in the muzzle-head of the barrel-assembly or a fluid injector in a separate radial projection catheter.

The Parker Hannifin MX80S miniature linear motor stage with stepper motor under open-loop point-to-point control used with a Compumotor® 6K controller represents one suitable linear stage. The operator brings the muzzle-port or ports to the starting position for the programmed discharge pattern and sets the point-to-point distance (interval) to separate the successive equidistant discharges and the overall length (segment, stretch) of the duct or vessel to be implanted. Such is translated as increments to separate the starting and ending positions of the linear stage. The operator then uses a joystick or cyclic-like control arm as described below to initiate the execution of this number and distance of moves forward or backward. Once the pattern is confirmed to have been set correctly, the joystick is used to indicate the direction, the safety is removed from the plunger switch at the top of the joystick, and the plunger switch depressed to execute the pattern that was set.

Control is addressed in the section below entitled Airgun stenting (position and discharge) control panel. The patterns may consist of discharges along a straight line or lines (advancing or withdrawing), or straight lines followed by rotation and return (reversal of direction), or the repetition of the latter after the muzzle-head has been rotated to longitudinally (transluminally) pass over unimplanted arcs. While the use of a muzzle-head having a larger number of radially directed muzzle-ports so that all arcs are implanted simultaneously is preferred, such rotation and reversal allows the use of a barrel-head containing fewer barrel-tubes, which may be larger in diameter and thus allow the delivery of larger miniballs.

XIII3f. Positioning of the Barrel-Assembly with the Linear Positioning Table and Turret-Motor XIII3f(1). Type and Efficiency of Control Turning now to FIGS. 83, 84, and 85, both the closed-loop control of the turret-motor and open-loop control of the linear stage are initiated by the operator with the joystick, forward to move the table forward, backward to move it backward, and clockwise or counterclockwise to move the turret motor to the corresponding angle. Move and discharge operation is limited to the linear stage or transluminal positioner. Transluminal runs consisting of translation by the linear stage, holding fast while the timing relay signals the airgun hammer direct current powered plunger solenoid to operate, then executes the following increment, are performed one at a time, direct observation and action cancellation or override by the operator taking precedence over any automatic function.

There is, therefore, no stack or register to store successive transluminal discharge runs, and no provision for the programming of successive runs is allowed. When it is desired to induce oscillation in the translatory or transluminal axis, the linear stage is controlled in a closed loop that may be intentionally derivative gain overdriven or overamplified. Unless made to progress at a very slow rate, continuous positional control, whether by direct analogy whereby the muzzle-head would be made to move say, one millimeter for each move at the control of a centimeter, or by continuous directional incrementing, so that the muzzle-head would continue to increment in the direction of the control until the control was retracted, are both subject to constant overshooting.

The form of control must not permit a condition such that every change in position requires to be corrected, much less several times. Wasted motion would soon fatigue, prompting sloppiness where this must not be tolerated. While the first of these forms of control is the most intuitive or consistent with spontaneous eye-hand coordination, and the second is more intuitive than control that is based upon strict adherence to a previous setting of controls to specify the number, size, and direction of the increments to be executed automatically, for interventional application, where losses in efficiency based upon essential design factors are unacceptable and impatience with constant overshooting might induce carelessness, the first of these forms of control is rejected and the second reserved for quickly positioning the muzzle-head at the starting position for automatic discharge.

Once initiated, however, the system requires that the number and size of the increments to comprise each movement be entered first and the joystick or cyclic used to indicate the direction of movement, the latter being singular in any one such discharge-run or compound action. The apparatus then automatically switches between the movers (turret-motor and linear stage) and the airgun direct current powered plunger solenoid used to strike the valve body pin, stopping long enough between increments to allow the implants to travel to the trajectory termini. Shifting the joystick forward moves the linear stage stepper motor distad, backward proximad, tilting to the right or rotating clockwise moves the turret-motor clockwise, and tilting to the left or rotating counterclockwise moves the turret-motor counterclockwise.

The joystick has a central null position through which changes from forward (distad) to backward (proximad) direction of the airgun mounting linear positioning table must pass, so that reversal cannot be immediate. Similarly, rotation of the turret-motor cannot be reversed immediately, because a null region separates clockwise from counterclockwise contact, and since forward-backward excursion passes through the rotatory null region, simultaneous actuation of the turret-motor and linear stage is impossible. Actuating the automatic discharge (autodischarge) rocker switch shown in FIG. 85 causes the time delay relay shown in FIG. 84 to alternately switch between either the linear stage stepper or turret-motor as mover to the airgun solenoid that when energized strikes the valve-body pin releasing $CO_2$ into the airgun chamber causing the implants to be ejected.

The airgun is mounted on a linear positioning table that by moving the airgun bodily, transluminally advances or retracts (withdraws) the muzzle-head. The linear positioning table can be used to a. Accurately reposition the muzzle-head once the barrel-assembly has been inserted into the airgun barrel, which involves only control over the linear stage and turret-motor as movers, b. Reposition the muzzle-head and then effect discharge semiautomatically, the operator manually triggering each discharge, which alternates between positional control and discharge, or c. Direct automatic repositioning and discharge, in which compound action the muzzle-head is manually directed to reposition by uniform distances (increments, stretches) stop at each conjunction by a fixed time that is long enough for the airgun to discharge with the longest barrel-assembly, and then discharge automatically at each stop, which requires the automatic and coordinated control of the movers and the airgun.

Turning now to the airgun control panel shown in FIG. 85, once angioplasty has been completed, the barrel-assembly is inserted into the airgun. The power supply is activated by pressing the ON-OFF toggle switch to the 'ON' button. To bring the muzzle-head to the starting position for discharge, the joystick is held in the direction required until the linear stage and the turret-motor have incremented toward and positioned it thus. Semiautomatic discharge is appropriate for isolated discharge, but implantation for stenting demands a proximity and accuracy of adjacent placement that only machine controlled automatic discharge allows to be attained. Once the starting position has been reached, the airgun can be a. Discharged manually or semiautomatically by releasing the safety on the dead-man trigger switch and depressing the trigger, or b. Semiautomatic discharge initiated by using the upper dial to set the number of increments and the lower dial to set the length in millimeters of each increment.

The automatic discharge rocker switch is then shifted to the on position, and the direction of automatically executed discharge is commanded by shifting the joystick for the equivalent or analogous intraluminal movement, meaning forward for transluminal advancement, backward for retraction, rotated clockwise for clockwise rotation of the turret-motor, or rotated counterclockwise for counterclockwise rotation of the turret-motor. Since the preparatory angioplasty is generally carried out manually with the barrel-assembly independent of the airgun, automated positioning with the table ordinarily commences with insertion into the airgun barrel of the barrel-assembly for the purpose of placing the intraductal stent implants. So long as the barrel-assembly is used independently of the airgun for angioplasty, the turret-motor is seldom if ever used as a mover but rather as a means for generating heat for thermal angioplasty.

When the barrel-assembly resists rotation manually, then depending upon whether connection of the control electronics to the barrel-assembly is at the end-plate or in front of the airgun muzzle, the free proximal end of the barrel-assembly can be temporarily inserted into the airgun to connect the turret-motor. The uniform increments, each a sum of component point-to-point steps of the table stepper motor, can be used to produce motion that is continuous while the airgun intermittently discharges, or the movement can be keyed, meaning coordinated in timing to, the successive discharges of the airgun, so that the muzzle-head is made to intermittently travel a certain distance, wait in place until the one discharge is completed, then resume travel to the next implantation site.

In fact, the length of the pause in such intermittent movement is variable from complete cessation that is initiated before each individual discharge is triggered until after the discharge has been completed to only a portion of the discharge cycle, such as during recoil when, for example, it is more likely that a miniball might escape. When positioning is not keyed to the individual discharges, the overall distance and number of discharges within this distance are specified. Provided a threshold for the minimum interval to separate implants is not violated, the control mechanism then spaces this number of discharges at equal intervals within this distance.

To signal that implants have been placed too close together in linear sequence requires an ability to relate the action of the positioning table to the discharge of the airgun and consequent points of successive implantation and to use an out of tolerance condition to actuate an alerting device. As indicated, when positioning is keyed to the individual discharges rather than continuous, the positional cycle consists of movement in discrete translational sub-incremental steps of the stepper motor as table actuator from implantation site to implantation site, the muzzle-head held stationary while the airgun discharges before proceeding to the next implantation site. Intermittent action comprehends two sub-cycles, which the positional control system is used to coordinate.

One subcycle consists of the timing relations in the operation of the airgun and barrel-assembly, which are only slightly variable. The airgun is fully variable in the timing of the initiation of discharges but not in the time of each discharge (which depends upon the length of the barrel-tubes, hence, transit time). The other subcycle consists of the pattern of transluminal movement, which is fully variable. The airgun cycle consists of the release of $CO_2$ into the chamber, the transmitting of the barrel-tubes by the miniballs, the ejection of the miniballs through the muzzle-head, and the time for the miniballs to penetrate to the trajectory terminus.

The transit time varies as the length of the barrel-tubes, but the absolute duration of this interval compared to that of the fixed rate of transluminal repositioning is small. Since control over the airgun mounting is fully variable while control over the airgun mechanism is only variable in its intragun discharge cycle characteristics and thus only slightly in the absolute overall duration of the cycle, the operation of the airgun mounting is made to subserve the timing dictated by individual discharge from chamber to implantation end-point.

In intermittent operation, the movement of the muzzle-head or the fixed duration of each stop can be keyed either to the actual or to the highest rate of discharge, or more specifically, to the full, some portional, or the maximum time for an individual discharge, the last providing an interval of time slightly greater than needed with the longest barrel-assembly, thus eliminating the need for adjustment in the feedrate and achieving relative simplicity. That is, fixing the muzzle-head pause time for the maximum discharge time, which is determined mostly by the barrel-tube transit time, eliminates the need to adjust the pause time even though with shorter barrel-tubes or a higher discharge velocity the duration of this pause could be reduced. Accordingly, to preclude human error, the pause time is fixed at the maximum needed for the longest barrel-assembly Because the perforated barrel-tubes disallow any buildup of gas pressure, whether the result of premature discharge or in discharge with continuous movement of the muzzle-head, the shot-groups of successive discharges exert no effect upon the exit velocity of one another even though the miniballs of the previous discharge or discharges have not yet exited. Furthermore, with continuous movement of the linear stage and muzzle-head during discharge, a malfunction resulting in premature follow-on discharge so that more than one shot-group traversed the barrel-tubes simultaneously would have no jamming effect. Accordingly premature discharge is to be avoided exclusively due to the misplacement of implants that results.

XIII3f(2). Airgun Control Panel

To minimize human error, controls are mounted to the apparatus controlled or to a separate base, but not to other apparatus which may be in use simultaneously. The airgun control panel therefore includes the controls for minimally ablation or ablation and angioplasty-capable barrel-assemblies, which lack a built in source of power and are dependent upon the airgun power supply. Minimally ablation or ablation and angioplasty-capable barrel-assemblies for use in blood vessels will usually incorporate heat-windows and an embolic filter and sometimes radial projection units built into the muzzle-head requiring controls in the airgun control panel, other features such as blood-grooves, blood-tunnels, and gas pressure diversion channels passive and requiring no controls.

A radial projection catheter, whether used with a minimally or fully ablation or angioplasty-capable barrel-assembly, will similarly have its own controls. Regardless of the type of barrel-assembly used, discharge and the transluminal and rotational movement associated with successive discharge occurs only while the barrel-assembly is inserted in the airgun. Accordingly, the control panel for these functions is mounted not on the barrel-assembly but as separate (remote) from the airgun, at the top of a stanchion with weighted base and stand that may be raised to the height most comfortable for the operator, or on the airgun. So that the operator can call for immediate assistance, duplicate airgun control panels are preferably in both locations, those mounted to the airgun requiring enablement from the stanchion control panel.

The airgun itself may be mounted at the top of a stanchion or set on a table, but must be adjustable in height to level the barrel-assembly with the patient. In contradistinction to positional control for discharge, the functions assigned to the barrel-assembly and more especially a fully ablation or ablation and angioplasty-capable barrel-assembly—such as the deployment of a radial projection units in order to nudge the muzzle-head to one side of the lumen—are assigned to the control panel onboard the barrel-assembly. Discharge is either a. 1. Concurrent or 2. Delayed, and b. 1. Directly manual or 2. By executing preestablished patterns, described as semiautomatic, in that once the equidistant discharges have been manually set as to increment (distance of separation), indicating the direction for the action and depressing the plunger switch at the top of the joystick causes the pattern to execute.

Concurrent manual control over movement is obtained by holding down the plunger or dead-man switch at the top of the joystick at the same time that the joystick is used to move the barrel-assembly or rotate the muzzle-head, while delayed movement is obtained by first positioning the joystick forward to intraluminally advance, backward to withdraw, or to a preset angle to rotate the muzzle-head, and thereafter depressing the plunger switch. As a mode of semiautomatic operation, delayed execution is used to reduce the risk of human error in the form of overshots that would necessitate frequent if not irritating transluminal reversals in direction.

The section above entitled Single Axis Linear Positioning Table Airgun Mount specified that the operator first sets the number and distance of point-to-point increments to separate the starting and ending positions for the linear stage and then uses the joystick to initiate the automatic execution of this pattern. The apparatus then automatically moves the muzzle-ports forward or backward to the successive target locations for discharge, with or without rotation of the muzzle-head. More specifically, the control panel includes control settings for initiating programs that automatically discharge miniballs in preestablished formations, that is, in preset discharge patterns that execute as unit routines. The patterns are obtained by coordinating the transluminal movement of the linear stage and rotation of the muzzle-head with discharge.

Positional control thus involves the coordination of the two drive axes, the one an open-loop controlled stepper motor that moves the linear positioning table for transluminal movement, and the other, a closed-loop controlled dc servomotor that rotates the muzzle-head with actuation of the airgun push solenoid used as a hammer to strike the valve body pin. Such action is obtained through a programmed sequencer or stack register that stores the sequence of instructions for executing the pattern as a collective stream unit or routine. The sequencer controls the two servodrive controllers-amplifiers. In practice, the servodrive is usually a two-axis unit that is able to control a closed and an open loop simultaneously. As indicated, a pattern can include transluminal and rotational reversal, with discharge effected at each stop.

An automatic pattern is selected with a control knob having a pointer that is moved to the pattern chosen, and then the direction as forward (intraluminally advancing) or withdrawing (intraluminally retreating) is indicated by moving the joystick forward of backward respectively, and the action initiated only after the plunger switch atop the joystick is taken off safety and depressed, at which time the sequence consisting of moves to a succession of discharge points proceeds automatically. Pushing a cancel or check button on the control panel instantly stops (abends) this action. Rotational repositioning of the muzzle-head is directed by the program and executes, and coordinated timing exceeding the capability of the operator, without the need to rotate the joystick.

Rather than serving as a move execution switch to reposition the muzzle-head, in the control of discharge, whether directly manual to discharge one or a plurality of miniball implants or to initiate an automatic discharge pattern, the function of the plunger switch is as a trigger, and each terminus of travel a point for discharge. Whether to move or discharge, the on-off switch must be set to 'on,' and depressing the plunger switch always necessitates unlocking the safety. As additional safeguards, discharge during movement is electronically disabled, and a check-action or cancellation button positioned beneath the thumb of the operator on the joystick handle instantly truncates the ongoing action.

More specifically, depressing the 'cancel' button stops the flow of current to the turret-motor (rotatory axis), airgun linear stage (transluminal axis), the pattern instruction program, and airgun discharge actuating push solenoid to instantly arrest action commanded before or once initiated. While discharge could proceed so that miniballs were released while the muzzle-head continued to move, needless complexity and risk is avoided by not allowing movement and discharge simultaneously; rather, movement electronically disables discharge, which is automatically enabled on reaching the end of travel. The positional controls mounted to the airgun are for use only with the barrel-assembly inserted and are intended solely to move the muzzle-head from one location for implant discharge to the next.

As indicated, when the implants must be placed too closely together for manual control, upon depressing the trigger, transluminal movements of several millimeters or degrees of muzzle-head rotation are accomplished semiautomatically. In addition to the on-off switch, plunger switch safety lock, and action cancellation button, the airgun or stenting control panel typically includes controls for positioning:

1. Turret-motor rotation (typically by means of a digital encoder manually rotated by the rotary or tilt right or left component of the joystick (cyclic) with a pointer moved above an upper semicircular calibration with apical or centered 0-point (set point) and marked off in 5 degree error signal increments to either side).

2. An advancement and withdrawal control for direct manual transluminal movement with the linear positioning table by preset increments of a number of millimeters, the direction and execution controlled by moving the joystick forward to advance or backward to withdraw.

3. Advancing the intraluminal barrel-assembly in increments of two millimeters with the linear positioning table by pushing the joystick forward or backwards to withdraw.

4. Action cancellation or checking switch to instantly truncate the action whether mid-repositioning or mid-discharge, regardless of whether the action is direct manual or semiautomatic as a patterned sequence or collective unit formation; and controls for discharge.

5. Discharge pushbutton or plunger type switch at the top of the joystick for executing positional, discharge, and semiautomatic control.

6. Automatic discharge pattern selection knobs, transluminal (linear stage) positioning generally in increments of two millimeters and rotation (turret-motor) generally in increments of 5 degrees; and 7. Recovery (tractive) electromagnets 1 and 2 low-off-hi toggles. The cancel and actuation keys on both the control console and an angioplasty barrel-assembly pose sufficient resistance to depression to minimize the risk of unintentional depression.

XIII3f(3). Relation of Control Panels to the Turret-Motor and Airgun Linear Positional Table Axes, to Discharge, and to One Another Control of the airgun linear positioning table consists of using the switches and joystick on the airgun control panel, which is mounted on a bottom-weighted stanchion. Although the barrel-assembly can be inserted into the airgun barrel for motor controlled positioning at any time, angioplasty can be entirely manual, the operator manipulating the barrel-assembly at its free proximal end. Motor controlled advancement and withdrawal of the intracorporeal barrel-assembly is thus essentially limited to implant discharge or stenting use of the barrel-assembly. That is, while some conditions will recommend stent-jacketing prior to implantation, in most instances, stenting will follow use of the barrel-assembly manually with the proximal end freely movable.

Implantation then requires insertion of the barrel-assembly into the airgun, the rest of the transluminal positioning of the barrel-assembly performed by means of the linear positioning table, and rotation of the muzzle-head by means of the turret-motor. As seen on the airgun control panel shown in FIG. 85, the operator or an assistant can use the table to advance or withdraw the muzzle-head continuously or by a certain number of steps where the size of each step is set with a neighboring control knob. The airgun linear positioning table is preferably of the stepper motor-driven lead screw kind under open-loop control. A four-way radially symmetrical muzzle-head advanced by the linear positioning table will lay down lines of implants at uniform longitudinal distances to define the quadrants of the ductus.

As shown in FIG. 85, to produce a close formation of implants in order to evenly distribute the tractive force, the turret-motor and linear stage can be semiautomatically controlled to advance or reverse transluminal movement, the operator directing each run by entering the linear distance and number of discharges desired. At the end of each linear run, the turret-motor is used to adjust the rotational angle and the linear stage is then used to linearly distance the discharges in the reverse direction. Alternatively, the turret-motor can be used to rotate the muzzle-ports at each level without reversing direction so that the muzzle-head advances intermittently but consistently distad or withdraws thus proximad.

XIII3f(4). Automatic Close-Formation Pattern Implantation

While stereotypical or iterative pattern generation is a mainstay of numerical control in piecepart manufacturing, the functionality of automatic pattern generation for the present purposes would be inappropriate. In a clinical setting, complete flexibility subject to the medical judgment and immediate control of the operator is paramount. Detailed medical aspects of the actual lesions demanding treatment represent the primary factor in the decision process, mere niceties of technology impertinent. Discharge patterns would have to exist in so many variations of overall size and shot density that an absolute number of such patterns would be needed as would promote human error in selection.

Any such capability would most likely promote a dependence upon a generalized patterns where these were not properly applied. In order to be adapted for any real set of lesions, prepackaged patterns would have to be variable in omitting or adding implants to an extent that would render the nominal patterns useless. Accordingly, even though it would be a relatively simple matter to make discharge of entire formations execute automatically as a complete pattern, the concept is discounted in principle.

XII14. Pairing of Barrel-Assembly and Airgun

Provided the gauges match, any barrel-assembly can be connected to any airgun. For any given procedure, the requirements for precision in discharge independently determine the suitability of a given airgun, and the requirements for versatility and precision in ablation or angioplasty independently determine the suitability of a given barrel-assembly. Depending upon the procedure, either may be simple while the other complex. Both airguns and barrel-assemblies are applicable to procedures that demands less complexity and expense. The reverse is not true, in that a simple airgun will not allow the degree or speed of control in exit velocity essential for moving directly and without testing between histologically or pathologically different tissues, and to perform an ablation or angioplasty requires a barrel-assembly made for this purpose.

The opposing extremes in application are represented by differentiated anatomy, such as that in the trachea, which requires point-to-point discharge under the direct manual control of the operator without the need to clear the lumen of obstructive tissue, and a requirement for an even distribution of miniballs to uniformly distribute stent-jacket magnetic force over an area of undifferentiated anatomy in a straight arterial segment after the lumen has been cleared of stony plaques. Reversal of a collapsed dorsal membrane by a veterinarian, for example, can be accomplished with a simple pipe, as addressed above in the section entitled Simple Pipe-type Barrel-assemblies, connected to a suitably modified air pistol, as addressed above in the sections entitled Simple Airgun with Limited Application and Modified Simple Airgun of Wider Application, et seq.

The former uses a basic barrel-assembly and airgun, but depends upon a high degree of skill on the part of the operator, whereas the latter demands not only skill but an airgun that affords finely and quickly adjustable control over the timing, placement, and force of discharge and a barrel-assembly that provides multiple means for preparing the lumen to be implanted. Using the simple pipe with modified handgun, off to a side discharge with force impact registration film can be used to adjust the exit velocity with the valve body slide, as addressed in the section entitled Control of Propulsive Force or Exit Velocity by Means of a Calibrated Slide Cover over a Slot Cut into the Valve Body.

An ablation or ablation and angioplasty-capable barrel-assembly is intended to be usable with or without stenting. When used for stenting, work in the vascular tree demands a precision airgun mounted to a linear positioning stage with the controls appurtenant thereof included in its control panel. Directly manipulable barrel-assemblies include simple pipes, which only used for discharge implantation, are always connected to an airgun, minimally ablation or ablation and angioplasty-capable barrel-assemblies, which meant for simpler ablation or angioplasty during implantation, are also used while connected to an airgun, and ablation or ablation and angioplasty-capable barrel-assemblies, which are removed from the airgun when used to perform an ablation or an angioplasty, regardless of whether implantation discharge is to follow.

For freedom of movement when the implants do not require to be placed so close together as to exceed manual guidance, direct manipulation of the minimally capable barrel-assembly, like the simple pipe, is accomplished with an air pistol. The power required for the recovery electromagnets, turret-motor, and any radial projection units is provided by a battery pack is contained within a housing that extends the butt of the pistol grip downwards. Control microcircuits for heat-windows that use actuator windings as the heat source and control of the turret-motor are likewise contained within this housing, with the control panel mounted to its side.

By contrast, in an ablation or ablation and angioplasty-capable barrel-assembly, these components are associated not with an indissociable airgun, but rather with the barrel-assembly. The control panel is described in the sections entitled Airgun control panel and Relation of Control Panels to the Turret-motor and Airgun Linear Positioning Table Axes, to Discharge, and to One Another. The pairing of modified air pistol with an ablation or ablation and angioplasty-capable barrel-assembly is not preferred as awkwardly involving duplicate battery packs, hand grips, and controls.

XIII5. Remote Controls

The size of the pack that must be added to a modified commercial air pistol for supplying power to the powered components in a minimally ablation or ablation and angioplasty-capable barrel-assembly or to the hand-grip of an ablation or ablation and angioplasty-capable barrel-assembly can be reduced if the controls and microcircuit outputs generated through use of these controls are separately housed with the microcircuits in a remote control unit. A hand-held remote control unit for use with a minimally capable barrel-assembly is faced by the control panel therefor and detachably mounted to the enclosure of the obligatory airgun. That for an ablation or ablation and angioplasty-capable barrel-assembly is detachably mounted to the onboard battery pack for use in-situ or at a distance by an assistant. The transduction and infrared transmission of such signals is well known from the prior art.

XIV. Modes of Failure

The likelihood of a failure to implement suitable precautions because the operator was unaware that a vulnerable structure lay along the trajectory and failed to take prescribed measures for accommodating this condition is slight, the size of the projectile limits the injury that could be inflicted, and perforations tend to seal quickly. A primary reason for ballistic implantation is precisely the fact that the trajectory through the tissue to the target location is no larger in diameter than is the implant, and therefore quickly seals and quickly heals. Moreover, once placed, the ductus-intramural implants to be described become integrated into, move with, and effectively become a part of the surrounding tissue.

XIV1. Failure to Properly Discharge

Use of the in situ test described below, which intrinsically tests the exit velocity of the apparatus to be used in relation to the tissue it is to be used upon, should avert incorrect settings of the exit velocity.

1. If the exit velocity is set too low, the miniball may fail to eject. Retrieval of the miniball is accomplished by running a barrel-tube ramrod with mildly magnetized tip down the barrel-tube.

2. If the miniball ejects without sufficient momentum to penetrate the lumen wall, whether it becomes stuck between the muzzle-head and the internal surface of the lumen wall or drops into the lumen, if not embedded within the soft inner layer by the outward force of the smooth muscle action of the passing pulse or peristaltic wave, the miniball is retrieved by the recovery electromagnets or trap filter, deployment of the latter being imperative in the bloodstream. To time discharge for impact to occur at just the right moment when the wave passes is unrealistically difficult until several discharges allow this interval to be clocked.

3. If the miniball penetrates the lumen wall to too shallow a depth, it is extracted and recovered by increasing the current to the closer recovery electromagnet.

4. The reasons for placing a stent-jacket before initiating discharge are stated above under the section entitled Double-wedge Stent and Shield-jacket Rebound-directing Linings. If the miniball just punctures the adventitia at a tangent point, then its functionality for retracting the wall of the ductus cannot be depended upon and it must be replaced nearby.

5. If the miniball punctures the adventitia without sufficient momentum to rebound, it becomes embedded within the lining, and since the stent-jacket is applied to encircle the substrate ductus at its quiescent diameter, entrapment within the lining is accelerated by the outward forces of the smooth muscle action within the ductus. If the miniball interim finds a gap between the adventitia and lining, it innocuously either becomes trapped between the two and either forced into the inner softer layer of the lining or dropped into the body cavity.

6. If the miniball perforates the substrate ductus with sufficient residual momentum to strike the harder outer layer of the lining that is inclined (canted) outwards (centrifugally) moving ahead (forward, downstream, distad), the miniball will rebound to a functional location distal to that intended. The exit velocity is corrected and the miniball replaced. If the miniball is one of a plurality of miniballs radially discharged together, then depending upon the density of implants, the failure is disregarded or a rotary magazine clip with all but the one miniball position blanked is used with adjusted exit velocity to replace the miniball. Miniballs discharged in automated mode are by definition sufficiently dense to discount isolated discharge failures.

XIV2. Shallow Termination Into the Lumen Wall or Other Tissue of the Trajectory

The miniballs are discharged to enter the ductus wall at an acute forward angle, so that an unexpectedly malacotic or delaminated segment would result in an overshot, meaning penetration to a terminus that is too distant from the position intended both radially, or as to depth into the wall, and longitudinally, meaning continuation too distant in the antegrade direction. Depending upon the distribution of any sclerotic tissue within the segment, the miniball could fail to reach the depth intended, and a heavily calcified plaque or salt-encrusted ureter, for example, could cause a rebound into the lumen.

The means for averting and neutralizing these eventualities have been addressed in numerous sections, to include those pertaining to pretesting tissue hardness under section XVII below entitled Testing and Tests, the preplacement of shield or other jacket, double-wedge jacket linings, impasse-jackets, and the use of tissue hardness altering agents, among others. Trajectory terminus is readily discernible by passing a fine catheteric solid state Hall effect magnetometer microprobe through the access incision and along the adventitia, a high cost superconducting quantum interference device or a physical properties measurement system not necessary for the purpose as well as requiring temperatures injurious to tissue.

Provided the muzzle-head has been degaussed, such a sensor can be passed down an unused barrel-tube as service-channel and the muzzle-head passed over the length of the ductus to the maximum distance that the miniball might have penetrated. Even if coated with highly radiopaque tantalum, the miniballs are very small, generally 1.14 to 1.52 millimeters in diameter, making confirmation of successful implantation with imaging equipment difficult. However, since there is a range of forces that will substantially assure penetration through the luminal wall as not to terminate short of the more penetration-resistant outer tunic, which is harder and more elastic than the tissue subjacent to it, and since a value toward the upper end of this range is chosen to minimize the chance of shallow placement, only airgun malfunction or human error in setting its controls can result in shallow placement.

Miniballs and stays are given a coating of adhesive or protein solder to avert dislodgement into the lumen, and a down-tract or downstream trap-jacket, as addressed above in the section entitled Concept of the Impasse-jacket will prevent continued travel. For abaxial tissue within the wall of the ductus, the tractive force on the misplaced miniball should not be sufficient to induce compression necrosis. Necrotic tissue abaxial to the miniball should allow it to pass through and out of the wall, nullifying its value for stenting but not capable of causing harm. Again, means for predetermining the propensity of target tissue toward such an eventuality and means for neutralizing any complication that would result are addressed in numerous sections.

Provided antibiotics are administered this is a self-correcting problem, the perforation spontaneously healing. Unless contaminated through negligence or mishap, all of the components involved are sterile, and antibiotics are routinely administered as a precautionary measure in any event. Fistulization occurs when infection or tissue necrotic due to chronic irritation erodes a pathway to the exterior and drains. Shallow termination does not, therefore, pose any significant risk. When the operator sees that a miniball has landed short and negligible risk notwithstanding prefers to extract it, a tractive electromagnet at the front end of the muzzle-head is directed at the defective implant with the muzzle-head turret-motor, and the current to the electromagnet gradually increased until the miniball dislodges and becomes trapped in the tractive magnet antechamber.

When the treated ductus abuts upon an interposed structure that limits its gross movement toward the direction of traction, and the implants are eccentric or toward one side, or in the longitudinal half of the lumen but not the other side, it is also feasible to pass an external electromagnet such as that described below over the defective implant, as addressed above in the section entitled Mishap Recovery. Since the miniball or miniballs short of the termination intended will be lodged in softer, usually smooth muscle tissue, these can be pulled into the correct position, whereas those correctly placed will be prevented from perforating by abutment against the harder and more elastic adventitia.

This process therefore has the effect of selectively forcing a shallow miniball or miniballs out to, but not through, the outer tunic. Trajectory overshot with perforation. Provided antibiotics are administered to control bacteria that are always within the body, this is a self-correcting problem, the perforation spontaneously sealing then healing. The miniballs are bioinert and sterile. If an overshot could penetrate another vessel to enter the bloodstream, then the stent-jacket or clasp-wrap to be used with a stent-jacket and the stent-jacket are applied before commencing to place the miniballs. Loss of a miniball or miniballs in the lumen. So long as the trap-extraction electromagnets in the front end of the muzzle-head are set to trap field strength throughout the procedure, any miniball or miniballs that become loose in the lumen are swept into an electromagnet antechamber.

The proper functioning and setting of the trap-extraction electromagnets are confirmed preoperatively, and once the barrel-assembly has been introduced, the ammeter on the airgun, as will be described, will immediately reveal a loss of current. Since in exceptional instances when collateral circulation is lacking the loss of a miniball in the circulatory system could result in ischemia and necrosis, a transfer switch to a temporary power source such as an automotive battery may be used to sustain current to the electromagnets in the muzzle-head during the interval until the generator comes on. This merely states that an emergency uninterreuptible power source should always be on hand. The use of an external electromagnet of the kind described below can be positioned downstream to seize hold of any loose miniball or miniballs, which are then recovered by increasing the current to the electromagnets in the muzzle-head while reducing the current to the external electromagnet.

XIV3. Perforations

Perforations are not usually the result of equipment malfunction but rather human error—errors in testing, diagnosis, or adjustment of the controls. When anticipated, perforations are precluded by prepositioning of the stent-jacket, which is usually of the double-wedge rebound type as described above in the section entitled Double-wedge Stent- and Shield-jacket Rebound-directing Linings. Without prepositioning the stent-jacket, perforations by miniballs of 0.4 to 1.0 millimeters in diameter still have limited potential to cause significant injury. For the ductus treated, the site of puncture will be no more thrombogenic or less medically manageable than when implantation is successful. In the vascular tree, the prepositioning of a stent-jacket to prevent perforations may warrant the additional prepositioning downstream of an impasse-jacket to seize any miniball that rebounds into the bloodstream.

Perforations of the gastrointestinal tract are addressed above in the section of like title. Barring human error in having set the exit velocity far too high, the residual momentum of the miniball after it has penetrated through the wall of the ductus treated is not likely to pose a significant threat for neighboring structures. For such an error to be so extreme that the miniball could penetrate to the interior of a neighboring vessel to become an embolism, for example, is fanciful. Such injury as could result is more realistically associated with nervous structures. See also the section above entitled Concept of the Extraluminal Stent and the Means for Its Placement.

XIV4. Jamming

Jamming is associated with firearms where the round (cartridge, projectile) is cylindrical and engaged in a rifled barrel, so that deviation from concentricity can cause the casing to seize against the inside of the barrel. Here, in marked contrast, the barrel-tubes are completely smooth, usually lined with a coating of polytetrafluoroethylene, and the miniballs spherical. This makes jamming extremely unlikely. Moreover, because the rotary or linear feed magazine clip is readily examined, the failure of a miniball to eject is immediately discernible. Except for the interior of the barrel-assembly not engaged within the barrel of a modified commercially sold airgun, a jam inside a barrel-tube is readily viewable fluoroscopically.

XIV5. Premature Follow-On Discharge

Premature follow-on discharge with the muzzle-head moving from implantation point to point so that more than one shot-group traversed the barrel-tubes at the same time would not result in detention of the follow-on discharge. The perforated barrel-tubes disallow a buildup of gas pressure before the follow-on miniballs that could affect exit velocity even though the previous discharge had not yet exited. Premature discharge would, however, result in implant misplacement.

XIV6. Endothelial Cling and Seizure

The muzzle-head is surfaced for slipperiness, usually with a fluoropolymer such as polytetrafluoroethylene. Because the diameter of the apparatus is preselected for the ductus to be treated, and the surface material of the muzzle-head is lubricious and may additionally be wetted with a lubricant, clinging or seizure of the muzzle-head against the surrounding lumen is improbable. Should such occur nevertheless, a lubricant such as ACS Microslide®, Medtronic Enhance®, Bard Pro/Pel® or Hydro/Pel®, or Cordis SLX® is ejected through a catheter passed down a service-channel, or the central channel in a combination-form barrel-assembly, or by means of an electric-fluid system-neutral or fluid ejection tool-insert and an interval allowed for the lubricant to disperse.

The same is done when a radial projection catheter or combination-form radial projection catheter becomes stuck. The turret-motor is then used in oscillatory or chatter mode to further spread the lubricant in between the lumen wall and the muzzle-head. The same is done to expedite passing the barrel-assembly through tighter curves. Such eliminates the need for gross movements of the barrel-assembly that would be more likely to cause injury. Once confirmed free, the barrel-assembly is withdrawn. See also the section below entitled In situ Muzzle-head Adhesion Test.

XIV7. Radial Projection Unit Lift-Platform Malfunction

If the radial projection unit is piped, then retraction can be forced by bulb or syringe pipetting or connecting it to an aspiration pump at the proximal end, whether end or side-socketed. Lift-platforms for use in nonpiped units must incorporate ferromagnetic material for retraction (lowering) and raising by means of the magnetic force exerted by an external hand-held electromagnet.

XIV8. Entry of a Miniball Into the Bloodstream

The interception from continued travel and retrieval of a miniball that enters into the bloodstream is addressed above in the sections entitled Concept of the Impasse-jacket and Interception and Recovery of a Miniball Entering the Circulation, among others.

XV. Arcuate Stays

Arcuate (arciform, arcate) stays are implants that are inserted nonballistically beneath the surface of an organ, body wall, or the wall of a collapsed or stenotic ductus by means of special hand tools to be described. Some stays consist entirely of medication and are completely absorbed, while others used to provide mechanical support as buttresses may be absorbable when self supportability is expected to return, or permanent (nonabsorbable), or permanent and coated with absorbable substances such as medication, hardening, or bonding agents. Whereas medicinal miniballs require no stent-jacket and therefore require entry to insert the barrel-assembly, stays exclude a transluminal component but require an access incision local to the point of insertion.

In an ideal stay, the arms, or extensions of the stay from the midline, would flex as do those in an unstrung archer's bow; however, a number of prior considerations for treating a given condition often preclude formulation of the stay to meet this requirement. When flexibility is lacking, the tips of a stay will resist movement of the surrounding tissue in proportion to the length or arcuate extent of the stay about the wall of the ductus for the degree of change in lumen caliber or circumference. When this is true, inflexible stays are kept short and made larger in width to present a larger and more uniformly distributed area to the tractive force.

Stays are inserted one at a time from outside the ductus through the local incision, which takes longer but allows each insertion to be of a different kind or size of stay and for each to be confirmed as properly positioned before proceeding to the next. Stays of any kind pose less potential for retrieval problems than do miniballs, but to allow retraction with the electromagnet built into the insertion tool should insertion deviate from the path intended, even medicinal stays, which are completely absorbed, include some ferromagnetic matter. Stays referred to as stent-stays are used with a circumvascular stent-jacket or more distant magnet-wrap, subcutaneous, or suprapleural clasp magnets, and some of which are nonmagnetic to maintain luminal patency.

XV1. Medication or Radiation (Nonstent), and Medication-Coated Stays

Stays can be formulated to consist entirely of medication, of different kinds of medication in concentric layers where each consecutive subjacent layer is time-released spontaneously or by extracorporeal action, as has been delineated for miniball implants. Other nonstent stays can emit radiation from a core seed or following irradiation. Absorbable stays can release medication as these dissolve and serve with or without a stent-jacket as temporary buttresses or structural supports over the period of healing and dissolution. Nonabsorbable stays can be drug eluting, or if incorporating a chemically isolated core of strongly magnetized neodymium iron boron, can serve to attract drug carrier particles from the passing lumen contents into the intervening wall of the ductus.

Stays generally contain sufficient superparamagnetic magnetite or maghemite nanoparticles or finely grained powder to allow recovery with a hand-held electromagnet if misplaced or dropped, and when meant for stenting use, have a ferrous core or distributed encapsulated ferrous material for use as magnetic stent-stays. Like miniballs, addressed above in the section of like title, stays can be given outer coatings which can be affected by passive heating, and size allowing, can incorporate internal means for generating heat. If magnetized, stays like miniballs can be used to attract magnetically susceptible drug carrier particles up to the depth into the ductus wall. Impasse-jackets and stent-jackets are not limited thus nor in the mass of magnetized material that these can incorporate. Ductus-intramural implants are therefore suited to the treatment of lesions which are small, circumscribed, and shallow (adluminal).

XV2. Arcuate Stent-Stays (Stent-Ribs) for Use with Magnetic Stent-Jackets

Stays to serve as the intraductal component of a permanent extraluminal magnetic stent have a solid core or dispersed cores of ferrous metal encapsulated for chemical isolation. Those for temporary magnetic stents have superparamagnetic magnetite or maghemite nanoparticles or finely grained powder dispersed in an absorbable matrix, such as polyglycolic acid. Upon dissolution of the absorbable stay, the iron is assimilated by the body. Drugs for delivery as stays to achieve focused concentration likewise include sufficient dispersed superparamagnetic magnetite or maghemite nanoparticles or finely grained powder to allow any that become mispositioned to be easily retrieved.

The stay insertion tool described below includes an electromagnet for the quick retrieval of these. Absorbable stays can also be made to liberate medication during dissolution, and numerous combinations of medication in different type stays are possible. Broadly, whether for sustained attractability or for one time recoverability virtually all stays contain some ferrous content. While compared to ballistic implantation, using stays will usually lengthen overall procedural time, depending upon the specific condition to be treated, stays can present significant advantages over ballistic implantation.

Peripheral arteries may allow stays to be implanted with or without clamping, but unless the heart has already been shunted (bypassed) for an open heart procedure, stays are not for use at or close to the heart. While constant movement will affect the precision of miniball placement, this is unlikely to result in adverse consequences. This is because the increased force of impact to perforate and not just penetrate is large, and miniballs misplaced in level can be disregarded or the stent-jacket extended to include these. The discrepancy may call for the use of a segmented stent-jacket.

XV3. Structure of Stays

Stays have either razor sharp pointed or flat edges at the leading edge or at both the leading and trailing edge. Stays with flat front and rear edges are preferred as affording a greater area that delivers a larger quantity of medication and/or preserves concentricity with the wall of the ductus. Straight edged stays are driven forward by a stay insertion tool having an ejection tongue that has a flat front edge. Flat-edged stays are not wider midway along their length as to require engagement by the leading edge of the insert tool ejection tongue to ensure straight ejection. Stays with a pointed rear edge are used to gain penetration and/or to avoid vulnerable periductal microstructure and are driven forward by a stay insertion tool having an ejection tongue that has a forward v-shape with the apex of the v pointing rearwards to complement to the rear-pointing edge of the stay.

The fit and depth of tongue overlap must cause the stays to eject without veering. The advantages in the use of stays, mostly related to avoidance of the lumen, are addressed below in the section entitled Circumstances Dissuading or Recommending the Application of Stays. Even though the insertion tool is configured for a minimal girth so that it can be slipped down through a small surface incision and is equipped with clips to attach an endoscope, because stays are inserted from without the ductus through the adventitia, the application of these implants is least hindered and quickest when used during a procedure that calls for open exposure in any event.

When a magnetic stent to extend over a small segment of the ductus is required, the fact that to place the stent-jacket requires access to the ductus from without makes the use of stent-stays quicker, eliminates the need for a collateral transluminal procedure, and means that the lumen is not entered. Some eccentric or radially asymmetrical conditions are correctible ferromagnetically whether implanted ballistically or applied nonballistically with clasp-wraps or stays while others do not warrant ballistic implantation or magnetic traction. The latter can be corrected with stays made of plain plastic, nonmagnetic use being peculiar to nonmagnetic stays.

As is true with magnet and clasp-wraps, when the ductus to be treated is extensively attached by connective tissue, circumferential implantation may have to be intraluminal or ballistic. Stays are usually textured and/or perforated for added stabilization by tissue infiltration over time. A deeper surface texture also allows more medication or cement to be introduced ductus-intraparietally (ductus-intramurally) by the stay as it passes through the insertion incision produced by its leading tip. The tissue gradually supplants the substance adherent within the surface grooves or depressions.

Such a surface texture is no less applicable to nonmagnetic implants, such as nonstent-stays, that is, miniballs and stays not meant for use with a stent-jacket, but rather consisting entirely of medication, an irradiating seed, both, or stays that are introduced to support, or buttress, a collapsing ductus. When not temporary as absorbed, temporary placement may still be desirable. For example, irradiating seeds implanted on a temporary basis, allow a certain dose-rate exposure over a certain period of time. That stays are extracted as well as introduced from outside the lumen can be advantageous. In an artery, this avoids the need to administer systemic platelet blockade or anticoagulants, while in the colon, the risk of infection is reduced.

The depth of surface texture and any outer coating respond to the probable term that the implant will remain in place as well as the condition treated. While necessitating reentry at a later date, stays can be extracted with the same tool that is used to place these with or without stays loaded. This allows any kind of nonabsorbable stay, such as an irradiating seed stay of higher dose-rate, to remain in place over a limited period. Stays for later recovery contain ferrous metal, either as a core or as dispersed, to allow magnetic retrieval. Extraction is accomplished with the aid of a slitting edge that is retracted into the bottom of the tool butt when not in use.

The slitting edge is released by means of a spring button located within a recess at the side of the tool butt which requires inserting and pushing with the point of a pin to release. To extract a stay, the cutting edge is used to slit the overlying adventitia, the insertion tool retractive electromagnet to withdraw the stay, and the inmate cement line to seal the slit. Extraction less demanding of normal approach than insertion, use of a tool with the tilt-end component addressed below in the section entitled Stay Insertion Tool with Pivoting Base, wherein the slitting edge is retracted into the butt-pad, addressed in the section below entitled Butt-pad with Retractable Slitting Edge, is advantageous.

Since a stay that has been extracted will be retained at the bottom of the tool until withdrawn from the body, when each retraction slit is to be re-sealed with cement, the extracted stay will interfere with the extraction of more than one stay at a time. When the extraction slits need not be re-sealed, as when insertion was relatively close to the periphery, the number of stays that can be extracted at one time depends upon the field strength of the magnet. As shown in FIGS. 86 and 92 thru 94, stays are mildly curved (bowed, cambered) strips or bands made of a nonmagnetic material, such as thin and flexible stainless steel or polyester, that is hard enough to allow a leading edge to incise through the external surface of the ductus.

To provide a superior surface for the adhesion of medicated coatings or adhesives that will also promote tissue infiltration, the surfaces of the ductus-intramural implants described herein, stays and miniballs, are textured. When ferromagnetic, a soft iron disk is chemically isolated as embedded at the center of the stay and so that the force exerted on the disk will not cause the stay to rotate injuring the lumen wall. As can miniballs, and clasp-wraps, ferromagnetic stays can be used with stent-jackets or magnet-wraps. Whether implantation is of spherules ballistically or stays manually, the stent-jacket employed is unaffected, the content herein unified in this regard.

Stays can be coated as described for miniballs, either of which may also be surface coated with an antibiotic polymer such as produced by Covalon Technologies, Mississauga, Ontario. In some instances, stays are applicable without a stent-jacket, hence, the need to include ferromagnetic material. Stay insertion tools are described below in the section entitled Stay Insertion Tools and the use thereof below in the section entitled Use of Stay Insertion Tool (Stay Inserter). As addressed below in the section entitled Stay Insertion Tool with Pivoting Base, the insertion tool may incorporate a flexible joint toward the working tip that by making possible some lateral reach to adjacent segments of the ductus, allows the use of smaller and fewer stay entry incisions.

Stays for use with a tool incorporating a pivot joint should have a periphery or surrounding edge sufficiently rounded and upper and lower surfaces that are sufficiently flat so that each stay will track past the bend under the force of the stay compression spring without resistance or misalignment as would jam the line and seat flatly against the floor of the ejection slot. All types of stays, whether including ferromagnetic material for use with a magnetic stent-jacket or consisting entirely of medication, some combination of these, or including an irradiating seed, can be perforated, surface textured, porous, ribbed, raised-rimmed, or dished out on the front and back surfaces to thwart migration and promote adhesion and tissue infiltration.

To allow retraction by means of the electromagnet built into the stay insertion tool as described below in the section entitled Stay Insertion Tool Inmate Stay Recall (Retraction) and Recovery Electromagnet or recovery using the inmate or an external magnet, stays of virtually every kind, to include those designated 'pure medication stays,' contain some superparamagnetic magnetite or maghemite nanoparticles or finely grained powder. When it is desired to coat stays with cyanoacrylate cement, for example, in addition to a solid protein solder or another adhesive coating, but too much of the cyanoacrylate cement is wiped or squeegeed off the upper surface of the stay upon insertion through the adventitia, a tool of the kind that ejects the cement prior to each stay as shown in FIGS. 87 thru 91 is used with stays having a grooved or ribbed and textured surface which carries more adhesive forward as it passes through the adhesive into the wall of the ductus.

It is also possible to attach a microcatheter of the kind described below in the section entitled Cyanoacrylate Injection Catheter to the stay insertion tool by means of the spring clips described in the section below entitled Binding of Lines and Cables Alongside the Stay Insertion Tool. However, the secondary injection of an adhesive such as a cyanoacrylate is not recommended when the ductus and stays are so small that the adhesive cannot be introduced through the same incision as was made by insertion of the stay, or the stay insertion incision. The insertion tool recovery electromagnet energizable with reduced field strength throughout the insertion process, stays with a ferromagnetic core pose little risk of entry into the lumen.

For ease of retrieval, structural support stays that would otherwise consist entirely of absorbable aliphatic esters and stays that would otherwise consist entirely of medication are admixed with superparamagnetic magnetite or maghemite nanoparticles or finely grained powder. Coating each stay with cyanoacrylate cement as it is ejected reduces the risk that a stay will penetrate through the intima and escape into the lumen. Since this would squeegee away cement from the leading or incisive tip of the stay causing the cement to be retained intraparietally, entry into the lumen of cement, much less a stay, poses little risk. Moreover, unless the time to initial set has been much extended with retardants, cyanoacrylate cements will have 'locked up' superparamagnetic magnetite or maghemite nanoparticles or finely grained powder allowing retrieval of the drop and not just the iron particulates.

Even greater precaution against entry into the lumen is achieved by prewarming the ductus or initiating warming upon introducing the cement. A 'cooling' catheter fastened alongside the insertion tool as described below in the section entitled Binding of Lines and Cables Alongside the Stay Insertion Tool is used to deliver heated air. Thus, coating each stay with cyanoacrylate cement mixed with superparamagnetic magnetite or maghemite nanoparticles or finely grained powder and radiographic contrast, even without warming the ductus for a few seconds before, much less twenty seconds following insertion, the risk of escape into the bloodstream is small enough that stays can be used in arteries. Less desirable as a precaution against penetration into the lumen is the use of intraductal ultrasound.

While allowing penetration into the lumen of even the tip of a stay to be observed, to use this endoluminal technique would negate a principle advantage in the use of stays over miniballs, which is precisely the avoidance of the lumen entirely. Whether encapsulated within a layer or layers of medication, stent-stays for use with a stent-jacket are, by definition, ferromagnetic, whereas stays used as mechanical buttresses to support a collapsed or constricted ductus need not be ferromagnetic. Stays used to deliver medication may consist solely of medication but nevertheless lend mechanical support until absorbed. Stays can serve irradiative, medicative, and mechanical requirements in any combination, and different types of stays may suit different segments of one and the same ductus.

Where the wall of the ductus has become weakened, the nonimpactive placement and wider expanse of stent-stays makes these preferable to the ballistic placement of miniballs, which could perforate when discharged or pull through after placement. Due to a preliminary ablation or atherectomy or erosion of the arterial wall as the result of remodelling, weakening will be common. In vessels wherein the loss of a miniball, however designed against and improbable, would create a delay in completion of the procedure, portend an interval to the development of collateral circulation that is unacceptable, or would otherwise represent a complication that was simply inadmissible, stent-stays can be used.

Since incisive entry is necessary to place the stent-jacket anyway, the ability to insert the intraductal implants through the same incision and do away with the need for a transluminal component is attractive, and the more so when a preliminary angioplasty is judged unnecessary. Directly related to the elimination of a transluminal component is the fact that when skillfully inserted, stays do not puncture the intima or lining of the ductus treated, thus not weakening the ductus wall and rendering moot questions concerning the risks of ischemia, thrombogenesis, and intimal infection.

Further, the stay insertion tool described below in the section below entitled Stay Insertion Tools applies a tissue sealant to the stay as it is ejected through the adventitia, reducing the risk of a intraluminal separation within or delamination from the internal tunic of the lumen leaving it without retraction in an outward radial direction. Whereas miniballs are spherical, stays can be relatively thin and large in extent longitudinally and circumferentially, that is, in facing surface area. For this reason, more expansive stays are considerably more resistant to pull-through than are miniballs, making these usable in tissue that is too malacotic for ballistic implantation.

This expansiveness is also useful for replacing high density implantation effected by means of a positional control system, especially when the luminal wall might become so weakened as to aneuryse, although this is averted when the stent-jacket is placed prior to ballistic implantation. Stays can be absorbable whether consisting purely of medication or medication coating an irradiating seed; however, where the implants are nonmagnetic, ballistic implantation can achieve extensive longitudinal coverage in much less time. Regardless of whether the ductal intraparietal implants are for use with a magnetic stent-jacket, ballistic placement can be accomplished more quickly.

Once an arcuate stay-shaped core has been produced such as by pouring the liquid medication into a mold to dry, stays that consist entirely of medication or medication in successive investment of subjacent layers of medication can be produced by the same methods stated for the making of medication miniballs below, which include pan tumble coating, centrifugal extrusion, vibrational nozzle technique, and spray-drying. Similarly, a stent-stay may consist of a radiation source seed core and investing medication. Thus, the core of a stent-stay can be an absorbable or nonabsorbable polymer, a drug, or a radiation seed.

To minimize the risk of penetrating the lumen, stays are never to be used except 1. In sufficiently thick-walled ductus, 2. Unless insertion is constantly monitored for endothelial puncture with endoluminal endoscopy or endoluminal ultrasonography (intraductal untrasonography (IVUS), ultrasound probe sonography; ultrasound catheter probe-assisted endosonography; catheter probe assisted endoluminal ultrasonography), and 3. The stays are highly visible, whether with the aid of orally administered pronase (Sakai, N., Tatsuta, M. Iishi, H. and Nakaizumi, A. 2003. "Pre-medication with Pronase Reduces Artefacts During Endoscopic Ultrasonography," *Alimentary Pharmacology & Therapeutics* 18 (3) 327-332).

In some instances, plastic stays, coated with tantalum for high radiopacity and usually phosphorylcholine to reduce tissue reaction can maintain the patency of a ductus without the need for a stent-jacket. With conditions unpredictable as to the eventuality much less the time of subsidence, the stays employed can still contain a ferromagnetic disk to allow the application of a stent-jacket at a later date if necessary; otherwise, both magnetic disk and stent-jacket are optional; however, stays should always be radiopaque, and the inclusion of ferromagnetic material is preferred as expediting recovery if necessary. With predictable subsidence, stays can be absorbable, partially absorbable, or self-shrinking, and can release medication associated with the process of dissolution, as described below.

The applications of stays can be completely unrelated to the use of magnet traction to retract a ductus wall outwards towards a stent-jacket or magnet-jacket (magnet-wrap). The stay insertion tool as described below in the section entitled Stay Insertion Tools can also be used to introduce stays that consist entirely of medication or radiation seeds in the form of stays into the wall of a ductus. Stays used to localize medication or radiation within the lumen wall can be absorbable, in which case, the same materials used in absorbable suture and most tissue engineering scaffolding are used, as described below. The stays are curved for concentricity to the resting circumference of the ductus and, depending upon the condition to be treated, variable in proportional length to the diameter of the ductus to be implanted, but seldom longer than the radius of the ductus from the lumen center to the surface, or half of the outer diameter.

Since the materials used for the various types of stays tend to be inelastic, when the percent increase in diameter of the ductus requires, the ends of the stays are turned back outwards or everted in order to preclude a puncturing through the internal layers of the wall by the tips of the stay when the ductus expands. Once an antecedent angioplasty, if any, has been completed, stay insertion is without transluminal component, access accomplished by local exposure. The external surface of the adventitia in contact with the internal surface of the stent-jacket, and the implanted stay closely subjacent thereto, the stay is unable to move in a manner as would cut the media.

The camber of the stay is such that upon insertion along a tangent normal or perpendicular to the axis of the ductus with the convex side directed outwardly (radially), the stay remains substantially concentric to the ductus, that is, parallel to the ductus longitudinally and concentric to it perpendicularly, with bowing contrary to such bodily displacement slight at most. Substantial concentricity with the circumference of the ductus causes the stay to move with the rest of the lumen wall preventing its ends from incising the wall medially toward the lumen. Once implanted, the risk for escape into the surrounding body cavity or tissue is small, and once the stent-jacket has been applied, stays are prevented by magnetic attraction from escaping into the lumen and by physical obstruction by the stent-jacket from perforating outward.

While the risk for a stay to drop away from the ductus, much less become lost to view in the usually moist environment strongly adherent for it is slight to nonexistent, the stay insertion tools described below in the section entitled Stay Insertion Tools also serve as hand-held electromagnets that would allow a dropped stay to be recovered. Situated outside the lumen, no implant described herein should ever be heated by an alternating current-powered hand-held electromagnet as a noninvasive means for accomplishing followup thermal angioplasty to treat restenosis. To do so would burn extraluminal tissue.

Shorter stays are meant to achieve lumen patency by attraction to the surrounding stent-jacket, while, depending upon the condition to be treated, longer stays without an embedded ferromagnetic disk at the center can be used to exert a patenting effect without the need for a circumvascular stent-jacket. To the extent that it does not result in a degree of flexibility that allows deflective bending during the making of the adventitial or fibrosal entry incision, the stays are made thinner toward the ends to be flexible for compliance with the contractile action of the ductus. The stays are inserted through the external surface of the ductus to undercut the adventitia with a special insertion tool described below in the section entitled Stay Insertion Tools and are can be cold process plasma vapor deposition or sputter-coated with tantalum, for example, for increased radiopacity.

For improved tissue acceptance, a coating of phosphorylcholine or a polymeric blend thereof (see Lewis, A. L., Vick, T. A., Collias, A. C. M., Hughes, L. G., Palmer, R. R., Leppard, S. W., Furze, J. D., Taylor, A. S., and Stratford, P. W. 2001. "Phosphorylcholine-based Polymer Coatings for Stent Drug Delivery," *Journal of Materials Science: Materials in Medicine* 12(10-12):865-870(6); Jones, S. A., Stratford, P. W., and Rimmer, S., assignors to Biocompatibles Limited, Uxbridge, England 2000. "Polymeric Blends with Zwitterionic Groups," U.S. Pat. No. 6,150,432) is then applied to the tantalum and can also be added to the concentrated sugar solution used to bond and position the stays together in strips.

The use of a specific formulation of phosphorylcholine is secondary to the requirement for noninterference with the tackiness essential to seal the adventitia entry slit or for the cohesion of the stays within a strip for insertion in the stay insertion tool (addressed below). Polyester affords arcuate shape-holding ability consistent with flexibility, a low coefficient of friction, implantability without concern for substituent toxicity in the event of degradation, and tantalum coatability. Other polymers usable are polyethylene terephtalate with or without glass fiber and polystyrene.

If, as determined by the empirical probe-rod test described in the section below entitled In Situ Test on Extraluminal Approach for Intra- or Inter-laminar Separation (Delamination), the susceptibility of a lamina, such as the adventitia to delaminate or separate interlaminarly (radially fail, dissect) over time is ascertained to occur at a tractive force that is less than that to be exerted by the stent-jacket, then the stay is inserted to a greater depth, that is, into the media, which is accomplished by applying slightly greater downward force upon the insertion tool, the action more clearly viewable with the aid of an attached endoscope, for example, as described below.

Due to the continuous replacement of connective tissue, the adventitial or medial insertion incision adhesive-sealant automatically ejected with each stay by the insertion tool (of which little need reach the underside of the stay in any event) will not afford long term adhesion as would prevent adventitial or external elastic lamina delamination, for example, over more than several months (although the rate may be retardable—see Han, M., Wen, J. K., and Zhou, X. X. 2004 "Effect of Yiqi Huoxue Huayu Recipe on Vascular Collagen Turnover and Relevant Gene Expression," [in Chinese with abstract in English at Pubmed], *Zhongguo Zhong Xi Yi Jie He Za Zhi* [Chinese Journal of Integrated Traditional and Western Medicine] 24(2):136-139).

The surface of the stay is therefore grooved or ribbed and given a surface texture to encourage the gradual replacement of the adhesive with tissue that will infiltrate and adhere to its surface. Since the stent-jacket is chosen for the minimum effective attractive force, the choice of a stent-jacket having magnets that are so weak as to avert delamination (intralaminar separation) will have been precluded. Shown in FIG. 86, stays are a little wider at the center for increased surface area and thus more forceful retraction with reduced tendency for pull-through or becoming displaced. Upon ejection, each stay is maintained in rectilinear position to assure linear feed through the insertion tool ejection slot. Stays typically measure 2-3 millimeters in width by 4-5 millimeters in length, with rounded or blunted corners and honed edges at the ends.

Figure 93:
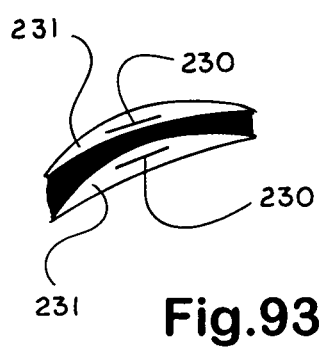
FIG. 93 shows a longitudinal section through two consecutive stent-stays, or stays containing ferromagnetic cores, in a refill strip, showing the binding agent used to hold the stay refill in one continuous strip from which the stay at the bottom is the next to be ejected.
Figure 94:
FIG. 94 shows a diagrammatic longitudinal sectional view of a portion of a stay refill strip showing various layered coatings that can be applied to a stay wherein the thickness of each layer is exaggerated for clarity.

Symmetrical, the rear edge is configured for engagement by the v-notch at the driving forward edge of the highly flexible spring steel or polyester-ferromagnetic steel laminate insertion tool plunger-blade (addressed below). In FIG. 93, soft iron cores 230 embedded at the center of each stay 231 by having been included in the mold are chemically isolated. The stays flexible except at the center but incapable of rotation as would lacerate the tissue surrounding the edges and tips, surface texture or embossing can be molded into the stay to promote tissue infiltration for stronger positional fixedness once implanted, it. Texturing the surface also allows better temporary adhesion of the sugar used as a bonding agent between adjacent stays to fasten these together into a strip in which the position of each is stable for ejection.

Figure 92:
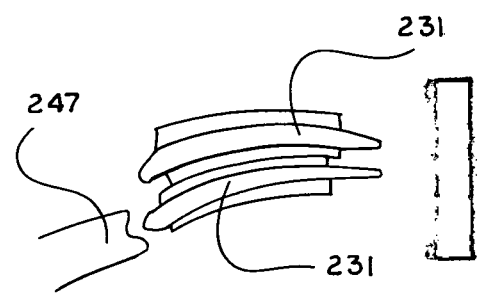
FIG. 92 further enlarges the working end of the stay insertion tool shown in FIG. 91 to show the articulation of a stay by the tip of the stay ejection blade (stay ejection tongue, plunger blade) at the working or ejection end of stay insertion tools whether of the control syringe-configured release to eject type shown in FIG. 87 or the pistol-configured pull-trigger to eject type shown in FIG. 88.

As shown in FIGS. 92 and 93, stays are separably connected into strips for sequential ejection similarly to staples. The floor of the ejection slot and surrounding walls of the stay magazine serving to substantially position the stays for sequential ejection, the stays are weakly tacked face to face to allow insertion in the magazine as a clip of several at a time and to more exactly align and separate the stays 231, which bowed and thinner toward the ends than at the center must nevertheless be stacked at the correct angle for sequential concentric implantation and engagement by ejection tongue or plunger-blade 247 along the rear edge. The stays are tacked together into a unified strip so that each can be separated from the those remaining above it in a manner analogous to the queued dispensing from a strip of office staples.

A sterile concentrated solution of sugar is brushed along either side of the stays stacked in the magazine so that capillarity draws the solution into the recesses between adjacent stays formed by the thinner end portions. On drying, the strips are sealed in sterile packages with inflexible sides as prevent breaking the strips. Once conveniently placed within the insertion tool magazine in a strip rather than individually, the stays are correctly positioned, breaking of the sugar bonds by the downward compressive force of the magazine spring no longer mattering. For the number of stays in a strip, the residue that accumulates at the bottom of the stay insertion tool magazine is not sufficient to jam the tool.

Almost all of the sugar that accumulates at the bottom of the stay insertion tool magazine is pushed out of the ejection slot by the next stay upon ejection, is swept to either side of the ductus entry incision, and falls away into the body cavity wherein it is harmless, trace amounts entering the ductus being likewise harmless. The nuisance of inserting each individually into the insertion tool magazine notwithstanding, unused stays are best sterilized with ethylene oxide gas, peroxide plasma, or gamma radiation. It is obvious that the attracter-attractant relation could be reversed so that the soft iron or other ferromagnetic disks within the stays could be magnetized axially, in which case encapsulated soft iron or other nonmagnetized ferromagnetic material would be mounted in place of small bar magnets about the surface of the stent-jacket.

XV4. Partially and Completely Absorbed Stays

Stent-stays that would accommodate a detumescing (resolving, subsiding) ductus by correspondingly shrinking without changing in conformation are discounted as demanding substantial constancy in retractive effect despite change in the mechanical properties of the ductus as the ductus continued to decrease in size, which would present equally intractable problems as contracting stent-jacket base-tubes. Substantially the same alterations in conformation can be obtained through the use of partially absorbed stays.

Stays can interleave material used for absorbable suture or staples (see Ravo, B., Rosales, C., Serino, F., and Castagneto, M. 1991. "The Use of Absorbable Staples for Construction of a Bladder Tube," Surgery, Gynecology, and Obstetrics 173(1):29-32) with the agents of their dissolution, so that catgut (collagen) is interleaved with a proteolytic enzyme or a synthetic with a water releasing hydrogel, and completely or partially absorbed stays for maintaining patency during the course of a temporary or subsiding condition can embed or interleave medication that is liberated by absorption.

The cyanoacrylate cement, such as ethyl 2-cyanoacrylate tissue adhesive or hydrogel (addressed above), used to bond plies of an absorbable or partially absorbable stay can be absorbable, release medication, or both. Anticlotting medication administered, it is feasible to initiate the absorption of a stay (or miniball, but not a stent-jacket expansion insert, which lies out of effective reach), its release of medication, or both in the bloodstream by thermal angioplasty with a barrel-assembly or thermal balloon catheter. Absorbable inserts implantable by means of the stay insertion tool can consist purely of medication compacted with or without an excipient base, medication applied to an absorbable base-stay, or absorbable material and medication particulates intermixed and compacted into a tablet of insertable shape.

When not collaterally serving a lumen patenting or stenting function, such implants can be shorter than the shape of a patenting stay as described above. When the material of the tablet otherwise lacks sufficient hardness to provide a honed leading edge of penetration strength, a rim surround of absorbable material is used to provide this strength. Medicating and/or irradiating stays can be produced with the medication coated onto the stay, which is made of the same materials as specified in the section above entitled Stent-jacket Expansion Insert Materials Having Relatively Short Breakdown Times that are used to make absorbable suture for more immediate release whether timed, or the medication can be interleaved with or interspersed through the absorbable material for more extensive timed release.

XV5. Circumstances Dissuading or Recommending the Use of Stays

Properly applied and inserted, stays avoid the lumen entirely. Stays are inserted into the wall of the ductus from outside the ductus so that the lumen is avoided, and can consist of or include medication, an irradiating seed, and/or ferromagnetic material for the radially outward retraction of the ductus wall by a stent-jacket. Since neither stays nor the placement of stays require entry into the lumen, stays are preferable when contact with the interior surface of the wall surrounding the lumen would best be avoided. The use of stays also eliminates the need to pass through tortuous stretches, which can be stented with a chain-stent (articulated stent-jacket) with segments as short as necessary.

Stays are individually inserted by hand and therefore take longer to apply than miniballs, which even without the aid of automatic apparatus can be introduced at a faster rate; however, stays avoid the risk of perforation and the need to preposition the stent-jacket or a specially devised stent-jacket to avert a rebound into the lumen due to having set the miniball discharge exit velocity too high. While stays can be inserted with a force determined on the basis of testing the tissue to be implanted, to do so is rarely essential. As addressed below in the sections entitled Stay Insertion Tools and Testing and Tests, this means that testing and the incorporation of a calibrated thumb-shaft return-spring screw adjustment in the stay insertion tool can be discounted, resulting in significant savings in procedural time and the cost of equipment.

Inserted one at a time, stays take more time than miniball discharge. Successive miniballs can differ in composition. By sequencing successive shots in the magazine or gravity line feed and not deviating from this during placement, miniballs that differ in composition, mass, and diameter, to match conditions shown by imaging need not slow down discharge. Similarly, to treat a ductus that exhibits frequent differences in pathology and strength, each stay can differ in any or all attributes. When perivascular fat, an attachment, or an adhesion can be resected expeditiously without significant injury to allow insertion, stays can be used. When even small amounts of such tissue should not be resected, stays are avoided.

The relative mid- and post-procedural disruption in function and the term of that disruption likely to result from external approach is weighed against the disruption likely to result from internal approach. Short segments are generally treated more conveniently with stays, which have the additional advantage of single entry with the lumen avoided altogether. While stays and stent-jackets are both inserted percutaneously through the same incision, stays require unobstructed access to the outer adventitial or fibrosal surface whereas stent-jackets may specifically include such tissue as essential for normal function.

As addressed above in the section entitled Field of the Invention, a small amount of perivascular fat supports normal intravascular function nutritive, respiratory or blood gas exchange, and endothelial, whereas an excessive amount results in malfunction and disease. Prospective benefit relative to risk is the deciding basis, attachments such as omental or mesenteric are seldom so vulnerable that the small interruptions needed to allow stays to be inserted would prove problematic. Stays can consist entirely of or be coated with medication and/or other therapeutic substances, and can be absorbable or nonabsorbable. Adjacent stays can be the same in size, shape, and composition or differ in these regards. Larger stays can incorporate radioactive seeds, telemetric sensors, or resonant circuits, for example (see, for example, Ferguson, J. E. and Redish, A. D. 2011, Op cit.).

Since stays are inserted subadventitially from outside the artery as to avoid the lumen, the serum concentration of platelet blockade if any can be reduced. Thus, in instances where the prospect is greater that bypass grafting will prove necessary, stays not only reduce potential bleeding during a following graft procedure, but depending upon the position of the treatment site or sites, may be insertable through an incision placed to allow for an endoscopic bypass procedure should the need therefor become apparent. The use of stays thus avoids penetration through the intima from inside the lumen, leaves no internal wounds as might thrombose or become irritated or infected, allowing implants to escape into the lumen, and is independent of transluminal entry to perform an angioplasty or for any other purpose.

This is especially advantageous in the treatment of blood vessels, allowing a reduction in the dose or elimination of a platelet blockade in arteries, for example, and for use in the ureters and gastrointestinal tract, which are affected by pathology more associated with the inward or adluminal than the outer tunic and where endoluminal stents invariably become clogged requiring periodic replacement. Stays are preferable when the lumen contents are infectious or septic so that the tiny perforations produced during ballistic implantation would expedite the spread of infection. Alternatively, miniballs are implanted with the stent-jacket, double-wedge lined stent-jacket, shield-jacket, or impasse-jacket within an absorbable shield-jacket placed to prevent perforations.

The inner surface of jackets used thus are wetted with an antiseptic. To protect against the spread of infection through leakage from an accidental perforation, stays are coated with an antibiotic. In the lower gut, for example, the systemic antibiotic administered can be lower in dose and less likely to destroy intestinal flaura essential for the normal clotting of blood and digestion. Implanted without entry into the lumen, stays are preferable for 'direct stenting' without site preparation in the form of an ablation or angioplasty of the diseased tissue within the lumen. Since stays have circumferential extension, these are easier to overlay with the magnets mounted to the base-tube than are miniballs.

When magnet overlay alignment is problematic, an intrinsically magnetized stent-jacket is used. Stays afford a factor of immediate accessibility to the treatment site. Simply stated, this means that stays are better suited to ductus readily accessible from outside the adventitia, whereas miniballs are better suited to ductus readily accessed from within the lumen. Tactile feedback (touch) and a direct view through an endoscope attached alongside the stay insertion tool by means of the clips addressed below in the section entitled Binding of Lines and Cables Alongside the Stay Insertion Tool stays eliminate the need, as in the discharge of miniballs, to adjust for any delay following triggering for the miniball to exit while the ductus wall continues to move.

This makes it easier for the operator to anticipate the moments for insertion Stays are suited to use in superficial ductus where little dissection is required to achieve insertion, whereas miniballs can be delivered to any location. Stays must be disproportionately thick in relation to the thickness of the ductus wall to increase the thickness thereof to any physiologically significant extent. Significant short-term swelling if any following the infixion of miniballs or stays warrants coating the implants with a steroid drug, for example. When the ductus is superficial but plunges, procedural brevity is served by using miniballs throughout, unless the segment accessible at the surface is malacotic as to recommend the use of wide stays.

Obstruction of the gastroduodenal or bile duct using stays to accomplish the stenting involves a relatively minor surgical procedure compared to a double gastric and biliary bypass operation, and while more invasive than the endoscopic placement of an endoluminal stent; an extraluminal stent is less likely to clog (see, for example, *The Merck Manual of Diagnosis and Therapy,* 18th edition, 2006, Section 2, Gastrointestinal Disorders, "Pancreatic Cancer," page 179). Furthermore and critically, once placed, the extraluminal stent is in position to attract magnetically targeted clog-dissolution, drug, and/or radiation carrier particles that will draw the agent up against and into the lumen wall and not to itself as a diversionary obstruction to such contact.

Stays are equally applicable to lumina such as the trachea, which presents a structured anatomy, and those such as the esophagus and arteries, which are relatively undifferentiated. Inserted from outside the adventitia, stays do not require the preparatory removal of calcified plaque lining an artery or oxalate salt accretions lining a ureter, for example, in order to allow the underlying lumen wall to be implanted within. While more pronounced mineral prominences should be removed, the complete removal of such deposits can prove counterproductive; hardening of the cap over an atheromatous plaque, for example, can actually serve to reduce its vulnerability to rupture.

A less thorough removal of calcified plaque also lowers the risk for a perforation that a burr can cause. Unlike miniballs used in the arterial tree, stays need not be coated with antithrombogenic, intimal hyperplasia-reducing, or anti-inflammatory medication. Should implants be needed that are to be temporary but not completely absorbable, as occurs, for example, in the placing of irradiating seed-cored stays, an advantage is gained once again at the time the stays must be recovered. When intraductal ultrasound, for example, reveals that remodelling has reduced the media so that even with the use of a tumefacient as addressed above in the section entitled Ductus Wall Tumefacients the wall remains too thin to implant ballistically, stays may still be able to undercut the adventitia and allow the placement of an extraluminal stent.

The conformation of stays is more efficient from the standpoint of providing for a higher flux density through the magnetic circuit allowing the use lower field strengths. Where magnetic stent circuit leakage flux (flux leakage, flux spillover) is essential to attract drug carrier particles from the passing blood, stays can project greater tractive force and are generally preferable to miniballs. The deliberate inclusion of pits or rust in miniballs used to both stent and attract magnetic drug carrier particles thereby to produce leakage flux is considered evident to those skilled in magnetic circuitry. In such use, the strength of the ductus wall must be confirmed as capable of sustaining the tractive force used for stenting before drug attraction as an attendant or ancillary use can be considered.

Although stays and miniballs may be equally applicable in certain circumstances, the provision of two different kinds of intramural implants, either of which can consist of or include medication, numerous other therapeutic substances, or radiation as well as complement a stent-jacket makes possible the choice of one or the other for responding to different anatomical and medical conditions. The overall system described herein similarly provides alternative approaches, methods, and apparatus. In muscular arteries, tumefacients that work by contracting the smooth muscle of the lumen wall will also reduce the luminal diameter.

Radially outward retraction of the lumen wall achieved by attracting subadventitially or perimedially placed implants is more effective when the type disease or previous ablation of diseased tissue lining the lumen makes postprocedural obstruction by adluminal swelling less likely. In instances where contact with the intima with a transluminal device is likely to promote swelling, stays may be better suited to stenting without a preliminary angioplasty, atherectomy, or ablation of the lumen lining and therewith, complete avoidance of a need to enter the lumen. For example, stays can be used where the removal of less significantly protrusive calcified plaque is contraindicated.

However, an accretion, plaque, or lesion will then have been left to protrude into the lumen, which may recommend the use of a stent-jacket slightly larger in diameter. This will distend the ductus to a degree slightly larger than its resting or diastolic diameter, interfering with smooth muscle function over the stented segment. However, wide stays, especially if coated with cyanoacrylate cement, for example, are far less susceptible to pull-through or delamination than are miniballs. This may represent a factor that would affect the diameter of a muzzle-head or radial projection catheter used in the segment to be treated but will rarely if ever affect the use of stays.

Due to the need to minimize the disruption of plaque by the antegrade rise in blood pressure caused by obstruction of the lumen and contact with the muzzle-head, a thermal angioplasty or an atherectomy is usually considered prerequisite to the transluminal (ballistic) implantation of spherules, or miniballs, within the lumen wall. However, angioplasty-capable barrel-assemblies incorporate heat-windows and radial projection units to accomplish this without a preparatory conventional balloon angioplasty. A combination-form angioplasty-capable barrel-assembly or radial projection catheter can also accommodate an excimer laser or rotatory burr, for example; however, the constraint on diameter for off-pump use is severe.

For introducing medication into the luminal wall, even in a coronary artery off-pump, the endoluminal barrel-assembly is superior, because a secondary entry to access the outside of the ductus is unnecessary, movement along the vessel is substantially unimpeded, and insertion whether by injection tool-insert or miniballs is quick. Where stenting is contemplated, a second entry to allow access from outside the vessel is still necessary. Reciprocally, in avoiding the lumen altogether, stays can pose a distinct advantage. When a magnetic stent is to be applied without preliminary therapy, angioplasty, or atherectomy, endoluminal access can be avoided entirely.

However, inserted from outside an off-pump coronary artery, stays do not move with the substrate vessel with sufficient stability as would a muzzle-head within the lumen. For this reason, the use of stays in coronary arteries is done on-pump. Stays are best used on other type ductus following open exposure where even a keyhole incision is not needed to gain access. The nose of a barrel-assembly for use in the bloodstream contains an electrical heat-window to thermoplasty the luminal wall in advance of the exit ports to destroy any debris that might pass downstream. For this reason, unless stays do not allow dispensing with any transluminal part of the procedure, a significant advantage stays afford is lost.

By contrast, as transluminal, the use of miniballs in arteries is provided with means to avert cerebral and cardiac vascular accidents. In arteries, stays are suitable where there is less risk of plaque ruptures so that angioplasty can be omitted; otherwise the forces applied to the ductus wall in inserting a stay could dislodge fragile matter. However, especially with respect to the carotids and coronaries arteries, where a release of embolizing debris during a balloon angioplasty could prove catastrophic, a recent trend has been to avoid an angioplasty even with the use of a forward deployed or run-ahead embolic filter (references appear in the section below entitled Thermal ablation or angioplasty-(Lumen Wall Priming Searing- or Cautery-capable Barrel-assemblies).

Since the stent-jacket can be placed before discharge is initiated, the use of stays is not compelled due to proximity to a nerve, ganglion, or other critical structure. As addressed below in the section entitled Concept of the Extraluminal Stent and the Means for Its Placement), an angioplasty-capable barrel-assembly does include a trap-filter (embolic filter, filter-trap). Inserted from the body surface and through the adventitia, stays can often be introduced through the same relatively small incision as a smaller stent-jacket. Stays are most easily used in an open surgical field exposed for some collateral purpose. Then the operator can increment the insertion tool along the ductus at right angles.

Entering through a short incision at the body surface, a stay insertion tool with pivot head, addressed below in the section entitled Insertion Tool with Laterally Pivoting Foot-joint (End-pivot, Tilt-end, Foot-pivot), can maintain a right angle relation to the ductus over a short segment of the ductus at shallow depths. Otherwise, unless the length of the stent is small or the ductus can be pulled up to and sideways beneath the entry incision, stent-stays necessitate an incision longer than that required just to place the stent-jacket. This limitation does not apply to medication and/or radiation stays, which are made wider to contain a larger dose.

Depending upon the length of the entry incision and need for dissection, ballistic implantation can reduce overall trauma. Nevertheless, the use of stent-stays allows the transluminal component in the placement of an extraluminal stent to be eliminated, and therewith, the risks associated with ischemia, stretching injury, the disruption of plaque, and so on. These considerations pertain to arteries as to demand accommodation in the design of the apparatus to be described.

However, since absorbable implants for delivering medication and/or radiation locally within the wall of the ductus (see, for example, Waksman, R., Laird, J. R., Jurkovitz, C. T., Lansky, A. J., Gerrits, F., Kosinski, A. S., Murrah, N., and Weintraub, W. S. 2001. "Intraductal Radiation Therapy after Balloon Angioplasty of Narrowed Femoropopliteal Arteries to Prevent Restenosis: Results of the PARIS Feasibility Clinical Trial," *Journal of Vascular and Interventional Radiology* 12(8):915-921) do not involve the use of a stent-jacket, ballistic implantation is superior to absorbable stays for this purpose, stays necessitating access to the exterior of the ductus through incisions.

For arteries invested within muscle, this poses a risk of incising, possibly even transecting the ductus. Medication stays are therefore reserved for use in an open. surgical field where the site has already been exposed. Even disregarding the time needed to access each target spot or point to be implanted, ballistic implantation is accomplished much more quickly. Situation in the lumen of an ablation or an ablation and angioplasty-capable barrel-assembly also allows the application of numerous procedures that cannot be used from outside the ductus, such as endoscopy, aspiration, the delivery of heat or cold by different means, brush cytology, and so on, as addressed below in the section entitled Ablation and Ablation and Angioplasty-capable Barrel-assemblies.

These functions can often be augmented through the use of a combination-form barrel-assembly, as addressed below in the section entitled Combination form Barrel-assemblies: Barrel-assemblies which Accommodate or Incorporate Means for Ablation, Thrombectomy, Atherectomy, Atherotomy, and/or Endoscopy, which allows devices such as an aspiration line, endoscope, laser, or atherectomy cutter to be inserted through the central canal to the nose of the edge-discharge muzzle-head. Use of the inserted device or devices does not affect the simultaneous use of other implements, such as radial projection unit tool-inserts, located about the periphery of the muzzle-head.

The larger aspiration line that the central canal will accommodate expedites the preliminary removal from a ductus of any debris that could interfere with treatment, for example. Another advantage of ballistic implantation is that the ductus need not be placed under torsion or twisted around to face the operator, which may necessitate more dissection than is necessary merely to place a slotted stent-jacket. Depending upon its length and the depth of the treatment site, a stent-jacket can usually be introduced through an opening and maneuvered into position about the ductus through one or two small incisions held open by means of a miniature retractor, such as one similar to an omni-bearing retractor used in abdominal surgery.

Stays, however, must be placed with the insertion tool in substantially perpendicular relation to the ductus, which generally necessitates incisions somewhat longer than is needed merely to place the stent-jacket. An analogous situation in that the approach to the treatment site must be normal is seen in the conventional procedure for placing prosthetic tracheal rings about the collapsed trachea of a small dog. This results in extensive trauma that alternative treatments to be described avoid. Prior art stents that are sutured to the outer surface of a ductus may appear similar to a stent-jacket, but these do not comply in both flexion and intrinsic motility such as peristaltic or tonic while affording circumvascular support. Moreover, the suture employed will usually course into the lumen, and to introduce such extraluminal stents demands open exposure.

By contrast, the stents to be described are entirely extraluminal, and compliant, allow placement of the outer component or stent-jacket through a relatively small opening. These stents differ fundamentally from previous stents in being neither entirely endoluminal nor circumvascular. To place such stents requires some additional procedural time and trauma; however, as will be explained, the advantages of such stents, physiological compliance, more than compensate for these detractions. The stay insertion tool is designed to prevent the entry of a stay into the lumen, and is so weighted and configured that the operator must intentionally apply downward force in excess of the passive weight of the tool on the ductus to obtain a greater depth of insertion.

With stent-stays, which usually permanent, have a ferromagnetic core for use with a magnetic stent-jacket, both the stays and the stent-jacket are introduced into the body through the same small incision that is used to pre-test the tissue at the treatment site, as described below in the section entitled In Situ Test upon Extraluminal Approach for Intra- or Inter-laminar Separation (Delamination). Abluminal, sterile stays should never enter the lumen. If such a risk is suspected due to later infection, a systemically distributed antibiotic is administered. Applied at or near to the treatment site, stays allow a ductus with problematically pronounced intrinsic autonomic motility to be visually gauged in rate and excursion and implanted by hand.

Lumina inaccessible to a barrel-assembly, such as in the common bile duct and coronary arteries may be suitable for stays, medication to increase ductus wall treatment, if necessary, addressed above in the section entitled Attainment of Implantable Intramural Thickness. When a barrel-assembly would meet with interference and the segment sought to be treated and/or stented is accessible without undue trauma from without, stays can provide a superior solution. Not entering the lumen, if the pulse interferes with insertion, stays can allow an artery to be clamped only so long as it is necessary to insert the stay. To similarly suppress an interfering pulse with a barrel-assembly, however, does not require clamping.

Instead, the artery is temporarily cuffed by preplacing the stent-jacket and initially tightening the hook and loop secured belt-straps during discharge so that the stent-jacket cannot comply with the pulse by expansion at the side-slit or side-slot. Once the implants are in place, the belt-straps are loosened to allow compliance with the pulse. The stent-jacket used is usually of the double-wedge type as addressed above in the section entitled Double-wedge Stent- and Shield-jacket Rebound-directing Linings. Preplacement of a stent-jacket at the treatment site is inapplicable to the use of stays. Extended circumferentially and longitudinally, stays present far more surface area to the lamina to either side.

This can be used to distribute and reduce the tractive force per unit area, to present larger surfaces bonded to adjacent layers, and the flatter profile will resist perforation by pull-through more than would a spherule. Even though using ballistic means a malacotic luminal wall can be prepared or primed with a strengthening (hardening) agent such as a tissue cement injected through a service-catheter of through a radial projection unit tool-insert injection head, the stay is thus from the outset and will remain more resistive to pull-through at once and over time. The larger surface area of the stay allows more bonding agent and superior adhesion through tissue infiltration of a textured surface.

For example, when the wall of the ductus requires reinforcement with a tissue bonding and hardening agent (adhesive-hardener) and the type of lesion should not be subjected to heat, the fact that stays can be coated with such an agent as cyanoacrylate cement, which bonds quickly without the need for heating allows stays to be applied to a wider diversity of lesion types than does ballistic implantation. By contrast, coating miniballs with cyanoacrylate cement, which is addressed below in the section entitled Cyanoacrylate Injection Catheter is a process secondary to ballistic implantation which adds time and tedium to the procedure.

Ballistic implantation without the use of cyanoacrylate is quick, likely to result in less injury should a miniball have to be extracted, does not necessitate superjacent entry above each miniball implant, and requires no incision at all when pure medication miniballs, for example, which require no extraductal stent-jacket are to be implanted. Whereas stay insertion, even with an insertion tool that includes a flex-joint, requires access and approach in the direction that is substantially normal (perpendicular) to the insertion site, a stent-jacket can be introduced through an incision that is smaller in length than the stent-jacket itself. In an artery, ballistic discharge is normally reserved for the diastoles when the vessel wall is relaxed (undistended) and closer with less blood interposed, whereas the insertion of stays, since it is accomplished from outside the vessel, is usually reserved for the systoles when the distended condition of the vessel makes insertion easiest.

An endoscope mounted alongside the stay insertion tool allows viewing the expansion of the ductus. The section above entitled Motional Stabilization of the Implant Insertion Site addresses the means for dealing with problematically fast and/or irregular smooth muscle action. Where it is believed that a calcified cap actually serves a protective function, extraluminal, unlike endoluminal stenting, allows plaque that does not occlude to remain, and whereas the presence of calcified plaque may preclude ballistic implantation, stays are inserted from outside the ductus. The vulnerability of plaque appears to vary with the strength of its roof as barrier separating the blood from the debris within.

Thus, vulnerability or susceptibility to rupture seems to increase in the order of no fibrous cap to thin and then thick fibrous cap, and from caps with less to more extensive calcification (Li, Z. Y., Howarth, S., Tang, T., Graves, M., U-King-Im, J., and Gillard, J. H. 2007. "Does Calcium Deposition Play a Role in the Stability of Atheroma? Location May be the Key," *Cerebrovascular Diseases* 24(5):452-459). Unlike miniballs, which can be quickly implanted in different directions about the lumen at once, stays are manually implanted one at a time from outside the ductus with the aid of a stay insertion tool as described below entitled Stay Insertion Tools through a laparoscopic or keyhole incision.

Using an automatic positional control system synchronized to airgun discharge, implantation can be accomplished even more quickly and accurately. When the site for treatment is more extensive, this can make the operative time required a significant consideration. A spherical surface such as that of a miniball or the core in a stay, which is effectively a miniball embedded at the center of a curved flange, is relatively inefficient as a magnetic interface. However, the extension of the flange makes it possible to disperse the ferromagnetic material in the stay, and whether left in the form of a core or distributed, the ferromagnetic material can be varied in surface geometry and oriented.

The more extensive area of the stay that is flush to the layers of the tunic or lamina separating the stay from the magnet distributes the tractive force, making the stay less susceptible than miniballs to pull-through or delamination, and the front and back surfaces of a stay allow more adhesive to be applied the further to resist delamination. For a ductus weakened by disease these factors can mean that stays would be effective where miniballs would not. The area coated with adhesive, its subsequent replacement by tissue, and adhesion of the tissue are adjusted by controlling the depth and detailed configuration of the texture at the surface, permanent stays deeply undercut in surface texture, temporary stays, such as irradiating seeds, smooth at the surface.

Temporary implants are retrieved with an electromagnet, usually that a part of the insertion device (barrel-assembly or stay insertion tool) that was used to place the implants or another electromagnet. For quick extraction with the least tissue damage upon retrieval, temporary stays, which are used apart from a magnetic stent-jacket, are also made with the ferromagnetic material concentrated at the tip which will be nearer to the probe of the magnet used for extraction. Stays are well suited to near-sided lesions in ductus of which the far side is secured by connective tissue as not to require a partial, or slotted, rather than a full stent-jacket.

The use of stays can be safely accomplished under intraductal ultrasound, especially when each stay ejected is given a coating of surgical cement, which action is performed automatically by the stay insertion tool. Because a primary advantage in using stays is the avoidance of the lumen entirely, the concurrent use of a transluminal device such as for intraductal ultrasound is reserved for more worrisome worksites, such as in the coronary arteries. When used, the intraductal ultrasound head can be made more manipulable by applying a disc of ferrous material to its outside, which then allows it to be directed by means of a hand-held electromagnet. When not a cyanoacrylate that attains sufficient bond strength within seconds, the adhesive is then warmed for about twenty seconds.

The risk of a stay entering the bloodstream is then very slight, but were such to occur, the insertion tool providing means for retracting and safely trapping a stay were it to enter the lumen. In general, the use of stays avoids endoluminal entry and the need for intimal perforation, indeed, avoids injury to the endothelium not offered by any current means of treatment, which the endoluminal approach of ballistic implantation does not. So long as clamping can be avoided, circulation through an artery continues without interruption. Except for an artery, however, which is under pressure from within, and where stay insertion is on the systoles, which are readily viewable with an endoscope mounted alongside the stay insertion tool, circumstances can arise that necessitate both extra- and endoluminal access.

A ductus wall that presents an intractable tendency to collapse under the stay insertion tool despite the use of an aspiration line clipped alongside the insertion tool to support it may require the stationing of a conventional balloon or a muzzle-head with circumferential radial projection units inside the lumen at the level to be implanted. This is done by using the turret-motor to position the side sweepers so that deploying these will elevate the wall of the ductus in the arc desired. In such a situation where entry is both endoluminal and extraductal, warming to initiate setting of the adhesive can likewise be endoluminal using the electromagnets or a line connected to the hot air outlet of a vortex tube based 'cold' air gun in the barrel-assembly, that is, a cooling catheter running heated air, or extraductal, using the same kind of line attached to a side of the insertion tool by means of the spring clips.

Bringing the adhesive coating implants, whether stays or miniballs, to an initial set by warming right after implantation also reduces the risk of extraction by a passing magnet or a prepositioned emergency recovery electromagnet. Adhesive is used when tissue separation or migration are of greater concern than is the more extensive injury that results when an implant must be recovered. Greater ease of extraction is an advantage of miniballs. The use of stays is indicated when, whether due to injury by the antecedent angioplasty or pathology, the intima must or would best be avoided, or where the limited time predicted for continued adhesion of a clasp-wrap to the adventitia would fail to provide extended effectiveness as required.

Stays can be used in combination with ballistic implantation to treat only certain segments of a ductus for which ballistic implantation is contraindicated. Under these circumstances, stays afford a suitable expedient when only the accessible side requires treatment or when the ductus is accessible for encirclement without the need for excessive dissection or torsion to allow access to sides in abutment with adjacent tissue. Stays are most useful where the underside of the ductus is firmly attached and only the facing side (arc) requires lifting support. In this situation, stays positioned to support the 'ceiling' will sometimes serve to maintain patency without the need for a stent-jacket.

With or without a stent-jacket, stays should be avoided where placement is near to the body surface without sufficient surrounding soft tissue to absorb a strong accidental blow as in the carotid artery, which could result in perforation into the lumen. Securing a magnetic stent-jacket with belt-straps will prevent stays or miniballs from entry into the bloodstream, making miniballs, which have no piercing potential, preferable in this context. As with ballistically implanted miniballs, while neodymium lanthanoid magnets afford considerable energy products, retention of a stent-jacket should not depend upon magnetic attraction alone but be afforded sufficient circumference to reliably engage the ductus mechanically through the resilience of the tube base material with or without the aid of suture or hook and loop spandex elastomer strapping end-ties.

Stays can be medicated or irradiative as discussed under the section on miniball implants above. It is worth noting that endoluminal stents pose a danger as the result of a direct blow. While later infection that weakened the ductus wall might conceivably lead to tunical delamination or the pull-through of ductus-intramural implants so that these come to abut upon the internal surface of the stent-jacket resulting in a loss in patency, retention in place by the magnets—even though the magnetic field strength is minimized to prevent delamination or pull-through—should prevent the entry of the implants into the lumen. Any significant loss in patency must assume that anti-infection medication had not been administered when the condition became apparent.

A similar ductus-intramural implant retention factor pertains should the ductus wall weaken later due to disease. Stays avoid the bloodstream as a source of contamination. Miniballs, however, may become contaminated by pathogens picked up from infected blood or other luminal contents during discharge, creating an entry path into or inoculating the ductus wall. Since such means are proposed for use with respect to tissue types as diverse as blood vessels, ducts, the airway, and gastrointestinal tract, such risk is widely variable, from the relatively sanitary condition inside the bloodstream in health to the extreme burden of bacteria in the colon.

Contamination through the endothelium can be protected against by wetting miniballs with a suitable antiseptic or antibiotic, although some of this as well as the pathogen is 'squeegeed' away as the miniball passes through the inner layers of the ductus wall. Suction decompression of an ophthalmic segment aneurysm and where the implants must not radiate heat to the surrounding tissue, the use of magnetic resonance imaging will require temporary removal of an extraluminal magnetic stent.

Amelioration through the administration of calcium channel blockers notwithstanding (Gulmez, O., Atar, I., Ozin, B., Korkmaz, M. E., Atar, A., Aydinalp, A., Yildirir, A., and Muderrisoglu, H. 2008. "The Effects of Prior Calcium Channel Blocker Therapy on Creatine Kinase-MB Levels after Percutaneous Coronary Interventions," *Vascular Health and Risk Management* 4(6):1417-1422), due to the potential consequences of myocardial or cerebral ischemia if not abrupt closure and infarction as the result of obstruction by the barrel-assembly of a coronary artery (see, for example, Andron, M., Stables, R. H., Egred, M., Alahmar, A. E., Shaw, M. A., Roberts, E., Albouaini, K., Grayson, A. D., Perry, R. A., and Palmer, N. D. 2008. "Impact of Periprocedural Creatine Kinase-MB Isoenzyme Release on Long-term Mortality in Contemporary Percutaneous Coronary Intervention," *Journal of Invasive Cardiology* 2008 20(3):108-112; Javaid, A., Buch, A. N., Steinberg, D. H., Pinto Slottow, T., Roy, P., Pichard, A. D., Satler, L. F., Kent, K. M., Gevorkian, N., Xue, Z., Suddath, W. O., and Waksman, R. 2007. "Does Creatine Kinase-MB (CK-MB) Isoenzyme Elevation Following Percutaneous Coronary Intervention with Drug-eluting Stents Impact Late Clinical Outcome?," *Catheterization and Cardiovascular Interventions* 70(6):826-831), or a carotid artery respectively (see, for example, Nakahara, T., Sakamoto, S., Hamasaki, O., and Sakoda, K. 2003. "Double Wire Technique for Intracranial Stent Navigation," *Journal of Vascular and Interventional Radiology* 14(5):667-668; Qureshi, A. I., Suri, M. F., Ali, Z., Kim, S. H., Lanzino, G., Fessler, R. D., Ringer, A. J., Guterman, L. R., and Hopkins, L. N. 2002. "Carotid Angioplasty and Stent Placement: A Prospective Analysis of Perioperative Complications and Impact of Intravenously Administered Abciximab," *Neurosurgery* 50(3):466-475; Veeraswamy, R. K., Rubin, B. G., Sanchez, L. A., Curi, M. A., Geraghty, P. J., Parodi, J. C., and Sicard, G. A. 2007. "Complications of Carotid Artery Stenting are Largely Preventable: A Retrospective Error Analysis," *Perspectives in Vascular Surgery and Endovascular Therapy* 19(4):403-408) or vertebrobasilar artery (see, for example, Qureshi, A. I., Suri, M. F., Khan, J., Fessler, R. D., Guterman, L. R., and Hopkins, L. N. 2000. "Abciximab as an Adjunct to High-risk Carotid or Vertebrobasilar Angioplasty: Preliminary Experience," *Neurosur-*

*gery* 46(6):1316-1325; Rasmussen, P. A., Perl, J. 2nd, Barr, J. D., Markarian, G. Z., Katzan, I., Sila, C., Krieger, D., Furlan, A. J., and Masaryk, T. J. 2000. "Stent-assisted Angioplasty of Intracranial Vertebrobasilar Atherosclerosis: An Initial Experience," *Journal of Neurosurgery* 92(5):771-778), the application of an extraluminal stent to these vessels may recommend the use of stays rather than miniballs.

However, when stays are used, avoidance of the lumen during insertion as well as thereafter means that unless the decision is made to dispense with angioplasty and only stent, an antecedent angioplasty will be necessary. By contrast, while accomplished transluminally, miniballs are implanted with the same device that is able to perform an angioplasty. When usable, the maximum diameter of the muzzle-head that can be used is still likely to prove preclusive of the level of barrel-assembly capability desired. However, when a barrel-assembly can be used, the need for an antecedent balloon angioplasty will have been averted, and the advantages of higher implant insertion rate and precision in close placement of the implants will have been gained. With less central vessels that can be mantled about or largely so, reduced procedural time and accomplishing a uniform distribution of implants quickly will usually favor the use of a barrel-assembly.

XV6. Stays Coated with a Heat-Activated (-Melted, -Denatured) Tissue Adhesive-Hardener, or Binder-Fixative Miniballs coated with a heat-activated (-melted, -denatured) tissue adhesive-hardener or binder and fixative such as a solid protein solder are described below under the section entitled Miniballs Coated with a Heat-activated (-melted, -denatured) Tissue Adhesive-Hardener. Whereas the solders used to invest miniballs should flow at lower temperatures for heating with the coils in the muzzle-head of the angioplasty-capable barrel-assembly, a laser for flowing stay solder can be attached alongside the stay insertion tool. One advantage in the use of stays is that access to the ductus for preliminary testing, for inserting the stays, for applying heat to flow and set a tissue adhesive-hardener if applicable, and for placing the stent-jacket are all done through an incision through the adventitia and thus outside the lumen.

Where the greater speed of ballistic implantation with miniballs had been opted for, results of the preliminary test described below in the section entitled In Situ Test upon Endoluminal Approach for Intra- or Inter-laminar Separation (Delamination) will sometimes have indicated that to avoid the risk of continued travel of a miniball between layers within the wall, either the stent-jacket or double-wedge type stent-jacket as described in the section above entitled Double-wedge Stent- and Shield-jacket Rebound-directing Linings must be placed prior to initiating discharge, or stays must be used instead, the choice made based upon the specifics of the medical condition as susceptible of less immediate trauma and freedom from sequelae by the one method or the other, the detailed implications of which are many.

More often it will be the lumen that would best be avoided, so that the choice of stays over ballistic implantation is more likely. If following curing, the tissue adhesive-hardener does not allow gradual infiltration at its boundary to a depth within it that sustains bonding relation to the replacement tissue, then whether a stay or a miniball, adhesion to the implant will be limited to the turnover rate of the fibers to which the adhesive coating the implant initially bonded. This factor is of central importance when intralaminar and interlaminar bonding that includes the radially outward and inward surfaces of the implants is essential to sustain the intraparietal integrity essential for the implants to maintain the lumen patent.

Ideally, the tissue adhesive hardener behaves similarly to scaffolding materials used in tissue engineering. It should be 1. Tissue-infiltratable, 2. Susceptible to enzyme degradation as necessary, and 3. Maintain adhesion as the tissue that was originally bonded chemically is replaced, making necessary mechanical bonding or the formation of new chemical bonds. Implants to remain over many years should have nondegradably textured surfaces that will allow mechanical bonding to the surrounding tissue by infiltration once so much if not all of the tissue adhesive-hardening agent subject to disintegration has disappeared.

For the period preceding the complete deterioration of the agent, the separation between adjacent miniballs or stays must be adequate to distribute the bonding agent extensively enough to preserve bonding during tissue renewal. The tissue once knit together around and to the surface of the implant must possess the required strength to withstand the tractive force. Stays provide much greater bonding surface for knitting intraparietal separations but do not allow a snugly fitting stent-jacket to be placed about the ductus prior to implantation. With miniballs, this measure can sufficiently reduce a separation as to allow dispensing with additional measures.

Provided tissue replacement of the adhesive-hardener is predictable, some slight inter- or intraparietal separation as is filled with the adhesive-hardener is acceptable. Any tissue hardener as might be injected into the weakened wall through the local incision to prepare it for implantation would have to meet the foregoing requirements and not prove excessively resistive to the insertion of stays, although if not too hard, ballistic implantation can achieve a suddenness and force of impact that along with the small diameter, typically 0.4 millimeters, will achieve penetration. The application to stays of a delayed tack glue or tissue bonding agent is accomplished by adaptation of the insertion hand tool, and is therefore described under the section entitled The ability to completely avoid the lumen an advantage of stays, a die injection test that avoids luminal entry, described below in the section entitled In Situ Test upon Extraluminal Approach for Intra- or Inter-laminar Separation (Delamination), is provided to detect a propensity for intraparietal separation. The test is intended to indicate the magnetic traction the material of the ductus wall can withstand before and after impregnation with an adhesive-hardener and if needed, whether the same must be allowed to fully cure before the stent-jacket is placed and the implants brought under the magnetic traction of the stent-jacket. If so, then stays should not be used.

With stays, the entire procedure, to include pre-testing, placement of the implants, heating to melt a solder coating or cooling by means of a 'cooling' catheter on the insertion tool when applicable, and placement of the stent-jacket are all through the same incision, and thus most advantageous when accomplished during a single procedure. For this reason, the ability to eliminate any cause for deferring placement of the stent-jacket is advantageous. When the ductus shows a propensity for intraparietal separation, placement of the stent-jacket may have to be deferred until the tissue adhesive-hardener has fully cured. This interval should not exceed 24 hours, which while more than the time for one procedure, is not excessive for preserving the ductus access incision and thus allowing the use of stays.

The need for reincision at the same or usually a nearby location is to be avoided. Longer curing times assume that the need to restore patency is not urgent, which usually is not the case. When urgent, to restore patency immediately, an anti-inflammatory such as steroidal drug-eluting absorbable endoluminal stent is inserted after placing miniballs. This allows deferring placement of the stent-jacket for the period over which the absorbable stent can be depended upon. Unless presenting some distinct advantage on medical grounds, a tissue adhesive-hardener requiring longer than 24 hours to fully cure should be discounted. Instead, the prepositioning of the stent-jacket for use with miniballs is considered.

If the choice is for stays, then the test already performed should supply conversion data as eliminates the need for a second preliminary test described below under the section entitled In Situ Test upon Extraluminal Approach for Intra- or Inter-laminar Separation (Delamination), which is used when stays are opted for ab initio to assess 1. The least outward radial tractive force or magnetic field strength, hence, the least expensive, smallest, and least obtrusive bar magnets and magnetic stent-jacket that would serve to maintain luminal patency as least to encroach upon or abrade against adjacent tissue, and 2. Whether the tunics or layers within the ductus wall would a. Withstand a tractive force exerted upon the implanted stays or miniballs by the bar magnets about the outer surface of the stent-jacket base-tube that is sufficient to maintain the lumen patent without separating within or between (delaminating) the layers or tunics, or b. Whether to prevent the wall from separating internally, the force required will necessitate the use of stays or miniballs having an outer coating of a tissue adhesive-hardener, such as a solid protein solder.

The thickness of the solder coating must not exceed the distance the stay can be allowed to be pulled radially outward within the wall of the ductus placing it closer to the stent-jacket. Neither can the coating be so thick that during the melting of the solder the stay is able to move significantly away from a substantially concentric orientation. In contrast to the use of stays having a coating of solid protein solder, the application of a cyanoacrylate cement to the trailing end of each stay to seal the incision made through the adventitia by the stay upon insertion, or the stay insertion incision, is built into the stay insertion tool to proceed automatically so long as an adhesive vial or cartridge is installed in the tool, regardless of whether the stays used are coated with a solid tissue adhesive-hardener.

Predenaturation having been determined to 'significantly reduce the solubility and consequently improve the handling characteristics of protein solder' (McNally, K. M., Sorg, B. S., and Welch, A. J. 2000. "Novel Solid Protein Solder Designs for Laser-assisted Tissue Repair," *Lasers in Surgery and Medicine* 27(2):147-157), application by air-suspension, pan tumble coating, spray-drying, vibrational nozzle, plasma vapor, sputter-coating, or any other process used in the pharmaceutical industry to apply a coating of a material while fluid to a troche (pill, tablet) can be used to apply the solder coat.

While denaturation of the solder so that it will flow into, bond with, and infiltrate into the interstices of the tissue surrounding the stay (or miniball) is not by heating through the absorption of the energy cast by a laser beam by chromophores dispersed through the solder or an absorbable polymer substrate membrane, to preserve the know-how acquired, a porous layer of an absorbable polymer can be applied to the implant as a substrate. To be as reliable as the inherent variability through time of the disease under treatment will allow, the test must be applied to the actual tissue to be implanted. If any preliminary treatment of the target tissue will alter its mechanical properties, the tissue must be tested in the condition at implantation for the results of the test to have any predictive value.

For example, when the ductus is affected over so short a segment that stays to either side of the weakened tissue would maintain its patency, to avoid aggravating and further weakening the affected tissue with both the test and the implantation, the test is performed on the stronger tissue to either side, which is the tissue to be implanted. If the operator believes that the injury to and weakening of the stronger tissue will leave that tissue incapable of withstanding the tractive force of a magnetic stent-jacket of the tractive force required without reinforcement, or the ductus is uniformly weakened over a segment that is too large to straddle and support the weakened portion at its sides, then stays encapsulated with solid protein solder must be used and warmed following insertion.

Because the stent-jacket is inserted through the same incision as the stays, the treatment must leave the ductus with sufficient strength to withstand the minimum tractive force sufficient to maintain the lumen patent within the time of a single procedure. The intraparietal use of a tissue adhesive-hardener assumes that the prognosis is for stability if not improvement in the strength of the ductus wall. For ductus that unlike arteries, for example (see, for example, Dirsch, O., Dahmen, et al. 2004, cited above in the section entitled Description of the Prior Art and Conventional Practice in Vascular, Tracheobronchial, and Urological Interventions), are poor in adapting to motile restraint, the use of a stent-jacket lined with a cyanoacrylate or solder adhesive is discouraged.

This is because unlike the use of a magnetic stent-jacket with minimal tractive force, except for the ductus wall under the stent-jacket side-slit or side-slot and therefore not bonded, the use of an adhesive restrains the ductus in circumferential expansion, and because any adhesive will become ineffective according to the turnover rate of the substrate adventitial tissue, the use of an adhesive in this way is limited to more short-term diseases when the lumen is expected to recover patency once healed.

XV7. Stays coated with a solid protein solder coating and cyanoacrylate cement

Collagen and albumin based solders that will act in combination with cyanoacrylate cement to flow and penetrate into the interstices of the surrounding tissue at 55 degrees centigrade (131 degrees Fahrenheit), then cool to act as a tissue hardener with strong bonding to the surrounding tissue have already been developed. To protect the surrounding tissue, these are recommended for pinpoint heating by means of a laser (see, for example, Soltz, B. A., Devore, D. P., Devore, B. P., Soltz, R. and Soltz, M. A. 2005. "Composite Tissue Adhesive," U.S. Pat. No. 6,939,364). While heating solder-coated implants following insertion may be an option, to do so exposes the tissue to heat over a longer period.

For this reason, it is preferred to use electrically or fluidically controlled solder injection-syringe tool-inserts such as shown in FIGS. 54 and 59 respectively, which can heat and maintain the syringe contents at a constant temperature. Injection-syringe tool-inserts are addressed below in the section entitled Radial Projection Units. To coat stays as each ejects from a stay insertion tool having a heated chamber is rejected as little of the solder would pass through with the stay. To reduce the removal of adhesive or medication, the surface of the stay is textured and grooved or ribbed.

Newer tissue cements developed for corneal application include Dextran Aldehyde-PEG Amine (see, for example, Chenault, H. K., Bhatia, S. K., Dimaio, W. G., Vincent, G. L., Camacho, W., and Behrens, A. 2011. "Sealing and Healing of Clear Corneal Incisions with an Improved Dextran Aldehyde-PEG Amine Tissue Adhesive," *Current Eye Research* 36(11):997-1004) and chondroitin sulfate-polyethylene glycol (Strehin, I., Ambrose, W. M., Schein, O., Salahuddin, A., and Elisseeff, J. 2009. "Synthesis and Characterization of a Chondroitin Sulfate-polyethylene Glycol Corneal Adhesive," *Journal of Cataract and Refractive Surgery* 35(3):567-576). As described below in the section entitled Mechanism for Adjustment in Stay Insertion Tool Ejection Cycle Inmate Cement Delivery Interval, when the cyanoacrylate is ejected just prior to insertion of the stay, the stay passes through the adhesive and into the wall of the ductus.

Such a surface treatment thus allows an increase in the amount of adhesive that is carried forward into the wall. As addressed below in this section, the addition of a retardant such as glacial acetic acid will extend the open time of a cyanoacrylate cement, and the addition of radiographic contrast will extend the open time even more. However, in the present application, where the solder coats the stay and becomes enclosed past the stay insertion incision so that pinpoint heating with a laser is not possible, the temperature should not exceed 49 degrees Celsius (120 degrees Fahrenheit) when the solder must continue to be heated for a period of minutes, or about 54.4 degrees centigrade (130 degrees Fahrenheit) when sufficient infiltration of the melted solder into the surrounding tissue takes less than half a minute.

Due to the minuteness in absolute amount, small ratio of volume to surface area, and proximity to the source of heat of the solder, flow and penetration can be achieved within this interval. Admixture with a solid albumin solder can be used to increase bond strength (see, for example, McNally, Sorg, and Welch 2000, Op cit.). The advent of solid rather than merely viscous or thick syrupy protein solders eliminates the need for a porous polymer membrane scaffold as would raise the melting point (see Maitz, P. K. M., Trickett, R. I., Tos, P., Lanzetta, M., Owen, E. R., Dekker, P., Dawes, J. M., and Pipet, J. A. 2000. "Tissue Repairs Using a Biodegradeable Laser-activated Solid Protein Solder," Conference on Lasers and Electro-Optics, page(s):446-447; McNally, K. M., Dawes, J. M., Parker A. E., Lauto, A., Piper, J. A., and Owen, E. R. 1999. "Laser-activated Solid Protein Solder for Nerve Repair: In Vitro Studies of Tensile Strength and Solder/Tissue Temperature," *Lasers in Medical Science* 14(3):228-237).

The contradictory representations made concerning cyanoacrylate cements and the controversy concerning butyl cyanoacrylate cement in particular are addressed in the section above entitled Specification of Cyanoacrylate Tissue Sealants and Bonding Agents.

Almost all surgical adhesives currently available, to include short carbon chain cyanoacrylates, albumin-glutaraldehyde-based glue (Azadani, A. N., Matthews, P. B., Ge, L., Shen, Y., Jhun, C. S., Guy, T. S., and Tseng, E. E. 2009. "Mechanical Properties of Surgical Glues Used in Aortic Root Replacement," *Annals of Thoracic Surgery* 87(4): 1154-1160; Wippermann et al. cited above; Schiller, W., Rudorf, H., Welzel, C. B., Kiderlen, M. J., Probst, C., Dewald, O., and Welz, A. 2007. "Sutureless Anastomoses of Rabbit Carotid Arteries with BioGlue," *Journal of Thoracic and Cardiovascular Surgery* 134(6):1513-1518; Schiller, W., Rudorf, H., Kiderlen, M. J., Welzel, C. B., Schmitz, C., Probst, C., and Welz, A. 2007. "Short-term Tissue Response of Lapine Carotid Artery Microanastomoses to BioGlue," *Thoracic and Cardiovascular Surgery* 55(5):298-303) and gelatin-resorcinol-formaldehyde-based glue (Izutani, H., Shibukawa, T., Kawamoto, J., Ishibashi, K., and Nishikawa, D. 2007. "Devastating Late Complication for Repair of Type A Acute Aortic Dissection with Usage of Gelatin-Resorcinol-Formalin Glue," *Interactive Cardiovascular and Thoracic Surgery* 6(2):240-242; Hata, H., Takano, H., Matsumiya, G., Fukushima, N., Kawaguchi, N., and Sawa, Y. 2007. "Late Complications of Gelatin-Resorcin-Formalin Glue in the Repair of Acute Type A Aortic Dissection," *Annals of Thoracic Surgery* 83(5):1621-1627; Kamada, T., Nakajima, T., Izumoto, H., Sugai, T., Yoshioka, K., and Kawazoe, K. 2005. "Late Complications Following Surgery for Type A Acute Aortic Dissection Using Gelatin-Resorcin-Formaldehyde Glue: Report of Two Cases," *Surgery Today* 35(11):996-999) have been impugned (see, for example, Bernabeu, E., Castellá, M., Barriuso, C., and Mulet, J. 2005. "Acute Limb Ischemia Due to Embolization of Biological Glue after Repair of Type A Aortic Dissection," *Interactive Cardiovascular and Thoracic Surgery* 4(4):329-331).

However, some workers may not have adequately distinguished between superficial inflammation at the application site and interference with healing (see, for example, Buijsrogge, M. P., Verlaan, C. W., van Rijen, M. H., Grundeman, P. F., and Borst, C. 2002. "Coronary End-to-side Sleeve Anastomosis Using Adhesive in Off-pump Bypass Grafting in the Pig," *Annals of Thoracic Surgery* 73(5):1451-1456), and some may not have employed proper application techniques (Fehrenbacher, J. W. and Siderys, H. 2006. "Use of BioGlue in Aortic Surgery: Proper Application Techniques and Results in 92 Patients," *Heart Surgery Forum* 9(5): E794-E799; Nishimori, H., Hata, A., and Sasaguri, S. 2000. "Optimal Application of Gelatin-resorcin-formaldehyde Glue with Special Reference to the Quality of Mixing," *Annals of Thoracic Surgery* 69(4):1299).

The use of a relatively low viscosity tissue cement (tissue sealant, surgical cement) or medicament allows the complexity, precision, power, and expense of advancement mechanisms used to drive high viscosity materials such as caulk and grease guns to be avoided and the distal portions of the tool for insertion into the body kept narrow to allow minimal entry incisions. Air pump piston-plunger 233 is seen most clearly in FIGS. 87 and 102, with additional views appearing in FIGS. 89, 95, 97, 98, 99. The use of low viscosity tissue cement requires the prevention of backup seepage about the edges of cement or medication refill cartridge plunger-plug 234 at the top of cement refill cartridge 235 (not to be confused with air pump piston-plunger 233 used to eject adhesive 236), which would disable air pump piston-plunger 233.

The adhesive delivery line that is built into the stay insertion tool thus consists of a single channel for the delivery of a one-part (single-component) only cement, such as Ethicon Omnex™ cyanoacrylate surgical sealant. Cyanoacrylate cements, with or without a retardant and radiographic contrast added, tend toward thinness in consistency and are more readily delivered through tubing of capillary diameter than are numerous alternative adhesives, to include some tissue sealants that consist of more than one component. Nevertheless, the immediate availability of a thicker tissue sealant for use as a hemostatic is desirable.

An auxiliary adhesive delivery line attached alongside the tool by means of a holder described below in the section entitled Powered Stay Insertion Tool Holder for the Attachment of Medication or Tissue Sealant Syringes Whether Single, Dual, or Multi-chambered as Supplied for Tool Slave-follower or Independent Use can be larger in diameter and thus conduct adhesives or any syringe-deliverable (fluid) adhesive or medication that is thicker in consistency. The holder can be used to control the delivery of this substance either independently of or as operationally linked or timing locked to stay insertion. These may consist of two or more components which must be kept separate until polymerization (setting) is to be initiated.

Such adhesive-sealants are typically sold in dual-chambered syringe dispensers which are best integrated into the operation of the tool without modification or only such modification as is essential. The use of an attached syringe to supply a hemostat to the treatment site requires function independent of the stay insertion function, as will be described below in the section entitled Use of Attached Adhesive Syringes Independently of Stay Insertion. At the same time, a single component adhesive eliminates component combination time as a variable affecting the interval prior to reaching initial set, and such an adhesive is delivered by means of the line contained within the insertion tool.

Once the components have been combined, an interruption in the procedure, depending upon its duration, may make it necessary to replace the syringe and line. The cyanoacrylate cement will solidify at the end of the delivery tube; however, a needle and an acetone-soaked piece of gauze, not the need to replace the applicator, allow continuation. Moreover, by the time of filing, no two- or more-part (multiple-component, multi-component, multi-part) adhesive had approached several commercially available cyanoacrylate cements in such key factors as strength of bond, quickness of setting time without a retardant (as discussed above in the section entitled Specification of Cyanoacrylate Tissue Sealants and Bonding Agents), and low viscosity that with the addition of a retardant allows good penetration of tissue interstices.

Since new developments could change that, and the internal mechanism of the insertion tool is meant to support only the use of single component adhesives, provision is made for the attachment of commercial multi-component tissue adhesive-hardener dispensers or applicators, as described below in the section entitled Powered Stay Insertion Tool Holder for the Attachment of Medication or Tissue Sealant Syringes Whether Single, Dual, or Multi-chambered as Supplied for Tool Slave-follower or Independent Use. A 'cooling' catheter with side-holes and/or a small end-hole can also be attached to a dual syringe, for example, to extend the adhesive open time when blown with cold air, $CO_2$, or $N_2O$, or reducing the open time when blown with heated air.

In practice, the preliminary test referred to above, which is described below in the section entitled In Situ Test upon Extraluminal Approach for Intra- or Inter-laminar Separation (Delamination), is required only when the medical condition of the ductus makes the use of an adhesive-hardener that must be heated to melt objectionable. Then, either a. The intrinsic strength of the wall must have been confirmed to be adequate in strength to sustain the tractive force of the magnetic stent-jacket without reinforcement by an adhesive-hardener, or b. The amount of cyanoacrylate cement applied to the stays must be increased to not only seal the stay insertion incision but compensate for the lack of a solid protein solder as a binding and hardening agent or fixative that requires the application of a higher temperature to use.

Because ballistic implantation precludes the initial and quick use of any fluid cement, recourse to an alternative tissue bonding and hardening agent such as a cyanoacrylate cement that need not be denatured (heated until melted) is an advantage in the use of stays, which can be applied to the treatment of a larger diversity of lesion types to include those which should not be heated. The use of cyanoacrylate cement to bind miniballs to and harden the tissue surrounding them, as discussed below in the section entitled Cyanoacrylate Injection Catheter, is secondary, and if the treatment site is extensive or multiple, may become time-consuming and tedious.

The mechanism for adjusting the adhesive emission interval, thus allowing adjustment in the amount of adhesive applied to each stay is described below in the section entitled Mechanism for Adjustment in Stay Insertion Tool Ejection Cycle Cement Delivery Interval. When either a. The condition will allow the use of stays having an outer layer of albumin-collagen solder that must be heated or b. The use of additional cyanoacrylate in lieu of solder is unobjectionable, then procedural time can be reduced by assuming from the outset that the layers within the wall of the ductus will separate, proceed to use adhesive as a perfunctory step barring special circumstances, and dispense with preliminary testing.

To flow into the interstices or intraparietal intra- or interlaminar separations in the tissue surrounding the stays, the ideal cyanoacrylate cement would be both thin (low in viscosity) and remain fluid (open) long enough to saturate these. More specifically, in unexceptional circumstances, any adhesive used to seal the stay insertion incision and, if necessary, serve as a tissue bonding and hardening agent is preferably:

1. Single-component.
2. Not soluble in body fluids.
3. In the absence of moisture, remains fluid (thin, light) at room temperature or while chilled to extend the open time so that even when the tool must be long to reach a more considerable working depth, the adhesive when mixed with the radiographic agent Lipiodol™ and tungsten powder (Suh, D. C., Shi, H. B., Park, S. S., Lee, M. S., and Choi, H. Y. 2000. "Change of Spontaneous Reaction of Glue and Lipiodol Mixture During Embolization after the Addition of Tungsten Powder: In Vitro Study," *American Journal of Neuroradiology* 21(7):1277-1279) will pass entirely through without clogging the insertion tool delivery line.
4. Fluid, if necessary, with the aid of chilling once intraparietal as essential for infiltrating and wetting the surrounding tissue, but which
5. Sets quickly when heated, and
6. Is not susceptible to enzyme degradation when such occurs too rapidly for the connective tissue to displace the adhesive, allowing the stay insertion incision and the tissue subjacent to it to mend.

However, the thinner a cyanoacrylate cement is, the shorter is its open time, and while chilling a cyanoacrylate cement will retard its initial setting time, to do so also increases its thickness (viscosity), likewise reducing if not negating its ability to continue to flow until it has fully penetrated the tissue. These factors make the use of cyanoacrylate cement to coat miniballs, and therewith the ability to avoid heating the tissue treated as required by a solid solder coating, impracticable, reducing the number of lesion types treatable with miniballs compared to stays. Moreover, since cyanoacrylate cement is not solvent based, its fluidity and open time are substantially unaffected by adding solvents such as acetone and super glue removers or surface active agents (wetting agents, surfactants, tensides), which are nontoxic, especially in the minute amounts that pertain, but in relation to which cyanoacrylate cement lose bond strength and are immiscible.

The established ways to extend the open time of a cyanoacrylate cement are to or mix the cement with radiographic contrast or acetic acid or to pre-coat the surface to be bonded with acetic acid; the latter not practicable for applications described herein. Accordingly, the use of an approved surgical cyanoacrylate, currently Ethicon Omnex™ cyanoacrylate surgical sealant in the U.S., is preferred without modification that is not clearly essential. The cement is packaged in stay insertion tool cartridges with fluidity and curing characteristics at various temperatures specified. Consisting of a single component, cyanoacrylate cement also allows simplification in requiring no more than one line (tube, lumen, channel) for delivery to the upper surface of each stay as it emerges from the ejection slot of the stay insertion tool.

For reasons of reaching initial set quickly and end bond strength, cyanoacrylate cement will be preferable to dual component adhesives under most circumstances. Future two-component tissue sealants may have faster curing times once the components are combined to initiate setting through polymerization. This would be readily accommodated by segregating the components in separate lines would detain blending until the components were within close reach of the end opening above the stay ejection slot. A miniature version of the type mixing nozzle used to mix epoxy cements is used to thoroughly blend the components. Such a nozzle is seen in the BioGlue® (CryoLife) dual syringe.

The mechanism for adjusting the cyanoacrylate emission interval, thus allowing adjustment in the moment of initiation and the amount of adhesive applied to each stay is described below in the section entitled Mechanism for Adjustment in Stay Insertion Tool Ejection Cycle Cement Delivery Interval. An alternative form of control for two-component adhesives is described below in the section entitled Powered Stay Insertion Tool Holder for the Attachment of Medication or Tissue Sealant Syringes Whether Single, Dual, or Multi-chambered as Supplied for Tool Slave-follower or Independent Use. Both the built in single-component and attached two-component adhesive delivery devices can have a 'cooling' (temperature changing) catheter with side and/or end hole for cooling or heating the tissue under treatment attached alongside.

While a cooling catheter must have side perforations if not an end perforation, a line for the delivery of hot or cold air, cold gas, or suction to the target tissue, unless needed at the same time, can all be through the same line or tube attached to the insertion tool by means of clips. Otherwise, one line is attached for suction, another for heating, and so on. Cyanoacrylate cements achieve initial set more quickly the more thin in consistency, or less viscous. Premature setting as would clog an adhesive delivery line whether inmate or attached to an insertion tool and thus interfere with implantation can, however, be averted.

Mixing the cyanoacrylate with Lipiodol™, tungsten powder (Suh, Shi, Park, Lee, and Choi 2000. as cited above) and/or acetic acid and/or with the aid of a cooling catheter having side-holes installed in the insertion tool side clips as described below under the section entitled Stay Insertion Tool Mounting Spring Clips; the use of cooling will retard setting but increase the viscosity or thickness of the cyanoacrylate cement. Any accumulation must be periodically purged or flushed, which can be through an aspiration line independent of the tool, a syringe with catheter connected directly to refill cartridge puncture pin seen as 237 in FIGS. 87 and 102, a refill cartridge containing a cleaning agent such as acetone or a commercial cyanoacrylate cleaning solution as specified in the below section entitled Use of Stay Insertion Tool, or if not needed at the same time, the same line used as a suction line or end-delivery cooling catheter, meaning a tube having only a hole or holes at its distal end for blowing chilled air or gas, or heated air at the treatment site.

To do this, the refill cartridge chamber side-entry snap-cover as described below in the section entitled Sealant Cartridges and Sealants (Adhesives) is removed, the attached line pulled out of the spring clips, its distal end placed over the adhesive cartridge puncture pin at the top of the adhesive line 237, and the cleaning solution injected at the proximal end of the line by means of a syringe. Once reattached, the line can be used to accelerate setting or curing, heated air can be delivered to the working spot on the outside of the ductus by a tube or hose connected to the hot outlet of a cold air gun with its own temperature control. The line can also be periodically flushed with a cartridge that contains cleaning fluid, a small hose, or a hypodermic needle used to inject acetone into adhesive cartridge puncture pin 237, as described below in the section entitled Use of Stay Insertion Tool (Stay Inserter) with the aid of cartridges filled with a solvent such as acetone to prevent or remedy any buildup of adhesive.

While most surgical adhesives initially set in about 24 seconds, the quickest to cure, cyanoacrylate cements, require at least two hours to reach full bonding strength, and non-acrylate based adhesives, because these initially set to form a weaker bond (García Páez, J. M., Jorge Herrero, E., Rocha, A., Maestro, M., Castillo-Olivares, J. L., Millan, I., Carrera Sanmartin, A., and Cordon, A. 2004. "Comparative Study of the Mechanical Behaviour of a Cyanoacrylate and a Bioadhesive," *Journal of Materials Science. Materials in Medicine* 15(2):109-115; García Páez, J. M., Jorge Herrero, E., Millán, I., Rocha, A., Maestro, M., Castillo-Olivares, J. L., Carrera Sanmartin, A., and Cordon, A. 2004. "Resistance to Tensile Stress of a Bioadhesive Utilized for Medical Purposes: Loctite 4011," *Journal of Biomaterials Applications* 18(3):179-192), make necessary means alongside the insertion tool for applying heat to accelerate curing.

XV8. Use of Cement and Solder Coated Stays

The use of cement and of solder-coated stays is primarily intended for use when preliminary testing as described below in the section entitled In Situ Test upon Extraluminal Approach for Intra- or Inter-laminar Separation (Delamination) reveals that the wall is predisposed toward intra or interlaminar separation. The adhesive will fail during a period shorter than the turnover rate of the majority of the cells at the bond interface; however, depending upon the condition, the replacement cells will usually supplant cement and/or solder as continuous tissue before the latter is dissipated.

A stay inserter can be used to implant any kind of stays, whether stent-stays containing ferrous metal for use with a stent-jacket or magnet-wrap, or stays that consist purely of medication, of time-released layers of medication, stays that include an irradiating seed, or serve as an absorbable temporary or a nonabsorbable permanent structural support to avert the collapse of a ductus. Stays can be prepared that combine these features, and stay refill-strip can be prepared to queue different type stays in any sequence, thus allowing the operator to alternate the type stays implanted along the ductus. Since stent-jackets are not recommended for ductus invested in tissue such as skeletal muscle, stent-stays are not used for such structures; however, stays can be used to implant medication or a source of radiation ductus intramurally.

In this circumstance, when the segment of the ductus to be implanted would necessitate multiple entry wounds to access the ductus at the substantially right angle required by an ordinary inserter, the number of entry wounds is reduced by using an inserter with a flexible joint as described below in the section entitled Insertion Tool with Flexible Joint. When the decision to introduce implants must pend a close visual examination of the proposed treatment site, a stay inserter can be used as a delivery platform for the endoscope and aspirator which because it can also mount alongside a laser, affords the immediate options for treatment by laser and/or the insertion of stays.

The cyanoacrylate cement is usually mixed with contrast agent and acetic acid, which detain initial setting to allow a solid protein solder coating on the stay to be melted by means of a temperature-changing or 'cooling' catheter attached to the tool. The use of a curing accelerator or primer is unaccommodated as an impediment. The attachment of ancillary lines to a stay insertion tool is addressed below in the section entitled Binding of Lines and Cables Alongside the Stay Insertion Tool. Ductus-intramural separation testing in preparation to implant stays is addressed below in the section entitled In Situ Test upon Extraluminal Approach for Intra- or Inter-laminar Separation (Delamination).

The stay insertion tool to be described in the following section allows switching from cement-ahead to cement-follow operation at any moment during a procedure and allows the amount of cement applied in either mode to be varied. In cement-follow operation, cement can be applied to only the trailing end of the upper surface of each stay and thus only for the purpose of bonding the stay insertion incision closed. This allows cement to be limited to only the trailing tip of each stay for the purpose of sealing its insertion incision into the wall of the ductus.

Figures 88, 89:
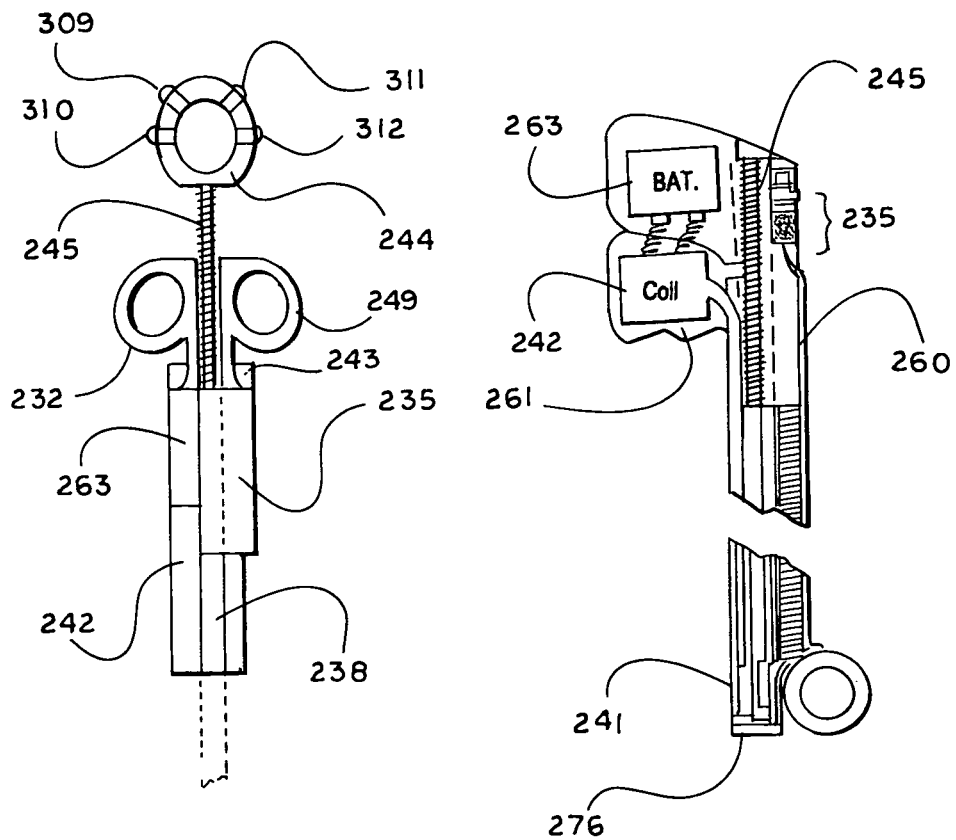
FIG. 88 shows a full face front view of the upper portion of the control syringe-configured stay insertion tool shown in FIG. 87.
FIG. 89 shows a longitudinal section through a pistol-configured pull-type, active, or pull trigger to eject tissue sealant, then inject a stay-type stay insertion tool.

Coating the entire surface of a stay will generally allow the cement to spread at its periphery contributing to the temporary resistance to separation. The tool shown in FIG. 89 is of pistol configuration that ejects cement over a variable length of the upper surface of the stay and injects the stay when the 'trigger' is pulled back. Using a pistol configured stay insertion tool, the movement of the operator is the reverse of that with the syringe-configured tool even though the ejection mechanism as such is the same.

XV9. Specification of Cyanoacrylate Tissue Sealants and Bonding Agents

The citation of short or long-chain cyanoacrylate cement herein is subject to continued research with regard to histotoxicity and carcinogenicity. In direct contact with tissue rather than used in fabricating the implant, such as to fasten the bar magnets about the outer surface of the base-tube, some have described long-chain plastic glues such as butyl 2-cyanoacrylate and octyl-cyanoacrylate as more slowly degraded with some incision line encrustation or microcrystallization residue remaining but less histotoxic than short-chain glues such as methyl- and ethyl-cyanoacrylate (Toriumi, D. M., Raslan, W. F., Friedman, M. and Tardy, M. E. 1990. "Histotoxicity of Cyanoacrylate Tissue Adhesives. A Comparative Study," *Archives of Otolaryngology—Head and Neck Surgery* 116(5):546-550; Levrier, O., Mekkaoui, C., Rolland, P. H., Murphy, K., Cabrol, P., Moulin, G., Bartoli, J. M., and Raybaud, C.2003. "Efficacy and Low Vascular Toxicity of Embolization with Radical Versus Anionic Polymerization of n-butyl-2-cyanoacrylate (NBCA). An Experimental Study in the Swine," *Journal of Neuroradiology* 30(2):95-102; comment by Haber, G. B. 2004. "Tissue Glue for Pancreatic Fistula," *Gastrointestinal Endoscopy* 59(4):535-537 concerning Seewald et al. cited in following paragraph; Pachulski, R., Sabbour, H., Gupta, R., Adkins, D., Mirza, H., and Cone, J. 2005. "Cardiac Device Implant Wound Closure with 2-octyl Cyanoacrylate," *Journal of Interventional Cardiology* 18(3):185-187.). Long-chain advocates do, however, reject isobutyl-2-cyanoacrylate (bucrylate) as a potential carcinogen (Vinters, H. V. Balil, K. A., Lundie, M. J. and Kaufmann, J. C. 1985. "The Histotoxicity of Cyanoacrylates," *Neuroradiology* 27(4): 279-291; Vinters, H. V., Debrun, G., Kaufmann, J. C., and Drake C. G. 1981. "Pathology of Arteriovenous Malformations Embolized with Isobutyl-2-cyanoacrylate (Bucrylate). Report of Two Cases," *Journal of Neurosurgery* 55(5):819-825). Cyanoacrylate cement is also addressed in the section below entitled Sealing of Stay Insertion Incisions.

While preferred as an alternative to ultrasonic welding for fabricating some of the nonimplanted apparatus described herein, butyl 2-cyanoacrylate (B2-CA) cement is not preferred for sealing a stay insertion incision wound as nonbioabsorbable, in the gut, at least, bioincompatible (see, for example, Nursal, T. Z., Anarat, R., Bircan, S., Yildirim, S., Tarim, A., and Haberal, M. 2004. "The Effect of Tissue Adhesive, Octyl-cyanoacrylate, on the Healing of Experimental High-risk and Normal Colonic Anastomoses," *American Journal of Surgery* 187(1):28-32), and believed by some, to be potentially carcinogenic (comment by Haber, G. B. 2004 cited in preceding paragraph; Vinters et al. 1985 cited in preceding paragraph; Samson, D. and Marshall, D. 1986. "The Carcinogenic Potential of Iso-butyl-2 Cyanoacrylate," (Letter) *Journal of Neurosurgery* 65:571-572), which others do not report despite lengthy followup to the same use (Seewald, S., Brand, B., Groth, S., Omar, S., and eight other authors 2004. "Endoscopic Sealing of Pancreatic Fistula by Using N-butyl-2-cyanoacrylate," *Gastrointestinal Endoscopy* 2004 59(4):463-470) or a different use (Saba et al. cited above; Tebala, G. D., Ceriati, F., Ceriati, E., Vecchioli, A., and Nori, S. 1995. "The Use of Cyanoacrylate Tissue Adhesive in High-risk Intestinal Anastomoses," *Surgery Today* 25(12):1069-1072; Brown, L. D.; Smith, C. D.; Lollini, L. O.; and Korte, Don W., Jr 1988. "A Carcinogenicity Bioassay of Isobutyl 2-Cyanoacrylate (IBC) in Fischer-344 Rats—One-Year Interim Sacrifice Report. Volume 2. Part 1," Defense Technical Information Center Accession Number ADA201448 [available at http://stinet.dtic.mil/oai/oai?verb=getRecord&metadataPrefix=html&identifier=ADA201448]).

The indictment of short-chain or absorbable cyanoacrylates as tissue adhesives has also been contradicted by researchers who report that ethyl 2-cyanoacrylate is excreted from the body intact, with no mention of degradation or the liberation of formaldehyde as does Haber cited in the preceding paragraph (see, for example, Kaplan, M., Oral, B., Rollas, S., Kut, M. S., and Demirtas, M. M. 2004. "Absorption of Ethyl 2-cyanoacrylate Tissue Adhesive," *European Journal of Drug Metabolism and Pharmacokinetics* 29(2): 77-81). Moreover, the same group has asserted that ethyl 2-cyanoacrylate can be used in vascular, myocardial and pulmonary surgery without concern for toxicity (Kaplan, M., Bozkurt, S., Kut, M. S., Kullu, S., and Demirtas, M. M. 2004. "Histopathological Effects of Ethyl 2-cyanoacrylate Tissue Adhesive Following Surgical Application: An Experimental Study," *European Journal of Cardio-thoracic Surgery* 25(2): 167-172).

In small amounts used superficially, as when closing following the placement of subcutaneous clasp magnets, butyl 2-cyanoacrylate would appear to be relatively risk free (see, for example, Canonico, S., Campitiello, F., Santoriello, A., Canonico, R., Ciarleglio, F. A., and Russo, G. 2001. "Sutureless Skin Closure in Varicose Vein Surgery: Preliminary Results," *Dermatologic Surgery* 27(3):306-308), while for closing stay insertion tool adventitial or medial incisions, insistence upon a longer chain adhesive such as octyl-cyanoacrylate appears warranted until such time as a cyanoacrylate cement which is absorbable and nonencrusting becomes available (Seifman, B. D., Rubin, M. A., Williams, A. L., and Wolf, J. S. 2002. "Use of Absorbable Cyanoacrylate Glue to Repair an Open Cystotomy," *Journal of Urology* 167(4):1872-1875).

Given contradictory information, the adhesive used to bond the lining to the internal surface of the base-tube, which is fully cured during manufacture and as cured involves little tissue contact, is based upon the materials of which the components to be bonded are made. Since octyl-cyanoacrylate and N-butyl-2-cyanoacrylate are generally agreed upon as posing the least risk, these, along with tissue sealants of different chemistry specified in the section below entitled Sealant Cartridges and Sealants (Adhesives) are preferred for all applications described herein that involve sealing tissue rather than an extracorporeal assembly of components with cyanocrylate cements not brought into extended or intimate contact with tissue.

Provided heat is applied to accelerate curing, vascular graft closure 2-octyl cyanoacrylate adhesives produced by the Closure Medical division, Johnson & Johnson Ethicon (Ethicon Omnex™ Surgical Sealant), approved in the U.S., which is preferred or alternately Glubran 2 N-butyl-2-cyanoacrylate and methacryloxysulfolane produced by Gem Viareggio, Lucca Italy, approved in Europe, Neuracryl™ 2-hexyl cyanoacrylate (see, for example, Krall, R. E, Kerber, C. W., and Knox, K. 2002. "Compositions for Creating Embolic Agents and Uses Thereof," U.S. Pat. No. 6,476, 069), Histoacryl™ n-butyl 2 cyanoacrylate produced by B. Braun Surgical GmBH (see Krall et al. just cited; Rosin, D., Rosenthal, R. J., Kuriansky, J., Brasesco, O., Shabtai, M., and Ayalon, A. 2001. Closure of Laparoscopic Trocar Site Wounds with Cyanoacrylate Tissue Glue: A Simple Technical Solution, *Journal of Laparoendoscopic and Advanced Surgical Techniques* 11(3): 157-159) for example, appear to meet if not exceed the requirements for sealing stay insertion incision wounds (see, for example, Brunkwall, J., Ruemenapf, G., Florek, H. J., Lang, W., and Schmitz-Rixen, T. 2007. "A Single Arm, Prospective Study of an Absorbable Cyanoacrylate Surgical Sealant for Use in Vascular Reconstructions as an Adjunct to Conventional Techniques to Achieve Haemostasis," *Journal of Cardiovascular Surgery* (Turin, Italy) 48(4):471-476; Lumsden, A. B. and Heyman, E. R. 2006 "Prospective Randomized Study Evaluating an Absorbable Cyanoacrylate for Use in Vascular Reconstructions," *Journal of Vascular Surgery* 44(5):1002-1009).

To enhance visibility and retard premature setting, surgical cyanoacrylate adhesives are routinely mixed with a radiographic contrast agent such as Lipiodol™, to which may be added tungsten powder (Suh, D. C., Shi, H. B., Park, S. S., Lee, M. S., and Choi, H. Y. 2000. "Change of Spontaneous Reaction of Glue and Lipiodol Mixture During Embolization After the Addition of Tungsten Powder: In Vitro Study," *American Journal of Neuroradiology* 21(7): 1277-1279), or acetic acid. The acetic acid may additionally induce the formation of an encapsulating layer of dense collagenous (scar) tissue to increase the resistance of the implant to pull-through under the magnetic force of the stent-jacket. However, this potential benefit of scar tissue only gains strength over much time.

The relative proportion of acetic acid used must consider that scar tissue is initially formed by the infilling of the injured tissue by a proteinaceous exudate that while it will eventually assist in anchoring and isolating the implant, will for a time weaken the interface surrounding the implant. Auxiliary syringes attached to a stay insertion tool make it possible to simultaneously or sequentially deliver agents for temporarily increasing the thickness of the ductus wall (in an artery, the intimal-medial thickness or IMT) and inducing the formation of scar tissue.

The cements specified herein for implantation, to include cyanoacrylate cement for intraparietal injection to bond miniballs, for example, and a solid protein solder as an outermost layer or coating for miniballs, for example, can be provided in modified formulations that will allow use to assemble absorbable implant components. Placed in contact with tissue, these should not evoke more than a tolerable adverse tissue reaction, which a release of medication by the cement as it disintegrates can ameliorate. Absorbable components are preferably bonded with absorbable cements of like breakdown time; although a slight residue, even nonabsorbable should pose little risk.

These cements also include both hydrogels but only when the swelling that follows application that is largely responsible for its hemostatic effect valued in alternative applications can be accommodated by applying a proportionately smaller amount (see, for example, Yin, L., Fei, L., Cui, F., Tang, C., and Yin, C. 2007. "Superporous Hydrogels Containing Poly(acrylic acid-co-acrylamide)/O-carboxymethyl Chitosan Interpenetrating Polymer Networks," *Biomaterials* 28(6):1258-1266; Ishihara, M., Fujita, M., Obara, K., Hattori, H., Nakamura, S., Nambu, M., Kiyosawa, T., Kanatani, Y., Takase, B., Kikuchi, M., and Maehara, T. 2006. "Controlled Releases of FGF-2 and Paclitaxel from Chitosan Hydrogels and Their Subsequent Effects on Wound Repair, Angiogenesis, and Tumor Growth," *Current Drug Delivery* 3(4):351-358; Ishihara, M., Obara, K., Nakamura, S., Fujita, M., Masuoka, K., Kanatani, Y., Takase, B., Hattori, H., Morimoto, Y., Ishihara, M., Maehara, T., and Kikuchi, M. 2006. "Chitosan Hydrogel as a Drug Delivery Carrier to Control Angiogenesis," *Journal of Artificial Organs* 9(1):8-16; Serra, L., Domenech, J, and Peppas, N. A. 2006. "Design of Poly(ethylene Glycol)-tethered Copolymers as Novel Mucoadhesive Drug Delivery Systems," *European Journal of Pharmaceutics and Biopharmaceutics* 63(1):11-18; Hu, B. H. and Messersmith, P. B. 2005. "Enzymatically Cross-linked Hydrogels and Their Adhesive Strength to Biosurfaces," *Orthodontics and Craniofacial Research* 8(3):145-149; Roorda, W. E., Bodde, H. E., de Boer, A. G., Bouwstra, J. A., and Junginger, H. E. 1986. "Synthetic Hydrogels as Drug Delivery Systems," *Pharmacy World and Science* [*Pharmaceutisch Weekblad. Scientific Edition*] 8(3):165-189) and cyanoacrylates, (see, for example, "Local Delivery of Vancomycin for the Prophylaxis of Prosthetic Device-related Infections,"; Eskandari M M, Ozturk O G, Eskandari H G, Balli E, and Yilmaz C. 2006. "Cyanoacrylate Adhesive Provides Efficient Local Drug Delivery," *Clinical Orthopaedics and Related Research* 451:242-250).

Cyanoacrylate cements referred to in this specification can, as has long been practiced, be mixed with a radiographic contrast agent, such as Lipiodol™ or Lipiodol Ultra Fluid™ ethiodol, or ethiodized oil, which additionally improves viewability, and may include tungsten powder (see, for example, Suh, D. C., Shi, H. B., Park, S. S., Lee, M. S., and Choi, H. Y. 2000. "Change of Spontaneous Reaction of Glue and Lipiodol Mixture During Embolization After the Addition of Tungsten Powder: In Vitro Study," *American Journal of Neuroradiology* 21(7):1277-1279; Stoesslein, F., Ditscherlein, G., and Romaniuk, P. A. 1982. "Experimental Studies on New Liquid Embolization Mixtures (Histoacryl-lipiodol, Histoacryl-panthopaque)," *Cardiovascular and Interventional Radiology 5(5):264-267; Papo, J., Baratz, M., and Merimsky, E. 1981. "Infarction of Renal Tumors Using Isobutyl-2 Cyanoacrylate and Lipiodol," American Journal of Roentgenology 137(4):781-785) or a subcorrosive percent of glacial (pure, water free) acetic (ethanoic) acid ($CH_3COOH$) (see, for example, Lieber, B. B., Wakhloo, A. K., Siekmann, R., Gounis, M. J. 2005. "Acute and Chronic Swine Rete Arteriovenous Malformation Models: Effect of Ethiodol and Glacial Acetic Acid on Penetration, Dispersion, and Injection Force of N-butyl 2-cyanoacrylate," American Journal of Neuroradiology 26(7):1707-1714; Rosen, R. J. and Contractor, S. 2004. "The Use of Cyanoacrylate Adhesives in the Management of Congenital Vascular Malformations," Seminars in Interventional Radiology 21: 59-66; Gounis, M. J., Lieber, B. B., Wakhloo, A. K., Siekmann, R., and Hopkins, L N. 2002. "Effect of Glacial Acetic Acid and Ethiodized Oil Concentration on Embolization with N-butyl 2-Cyanoacrylate: An In Vivo Investigation," American Journal of Neuroradiology 23(6):938-944) both for enhanced viewability and to retard premature setting as would clog the delivery line.

The addition of esterified fatty acid and gold particles similarly retards polymerization and provides radiopacity (see Pollak, J. S. and White, R. I. Jr. 2001. "The Use of Cyanoacrylate Adhesives in Peripheral Embolization," Journal of Vascular and Interventional Radiology 12(8):907-913). The use of retardants must always consider the open time of the adhesive during passage through the delivery line to avoid clogging, following injection (implantation), as well as the effect these will have on open time in the proximity of the various components described herein for the delivery of heat or cold, whether directly to the adhesive, to tissue, or to a component near to the adhesive.

Increasing the proportion in the mix of glacial acetic acid extends cyanoacrylate cement open time reducing the tendency for the cement delivery line to become clogged, and equally significant, results in improved tissue penetration, something that increasing the proportion of the Lipiodol tends to reduce (Lieber et al. 2005 just cited). Several reviews of surgical adhesives, tissue sealants, and hemostatic agents are available (see, for example, Pursifull, N. F. and Morey, A. F. 2007. "Tissue Glues and Nonsuturing Techniques," Current Opinion in Urology 17(6):396-401; Evans, L. A. and Morey, A. F. 2006. "Hemostatic Agents and Tissue Glues in Urologic Injuries and Wound Healing," Urologic Clinics of North America 33(1):1-12; Traver, M. A. and Assimos, D. G. 2006. "New Generation Tissue Sealants and Hemostatic Agents: Innovative Urologic Applications," Reviews in Urology 8(3):104-111; Copeland, D. C. and Ramakumar, S. 2003. "Tissue Sealants and Hemostats: Innovative Urologic Applications," Contemporary Urology 15(10)61-73; Baxt, S. 2001. "Tissue Glue," Plastic and Reconstructive Surgery 107(5):1311-1312). Techniques for hemostasis in laparoscopic entry as pertinent hereto are likewise available (see, for example, Lattouf, J. B., Beri, A., Klinger, C. H., Jeschke, S., and Janetschek, G. 2007. "Practical Hints for Hemostasis in Laparoscopic Surgery," Minimally Invasive Therapy and Allied Technologies 16(1):45-51; Entezari, K., Hoffmann, P., Goris, M., Peltier, A., and Van Velthoven, R. 2007. "A Review of Currently Available Vessel Sealing Systems," Minimally Invasive Therapy and Allied Technologies 16(1):52-57).

The much stronger bond, much shorter curing time at room temperature, and acceptable histological disposition of cyanoacrylate cement (see, for example, Saba, D., Yilmaz, M., Yavuz, H., Noyan, S., Avci, B., Ercan, A., Ozkan, H., and Cengiz, M. 2007. "Sutureless Vascular Anastomoses by N-butyl-2 cyanoacrylate Adhesive: An Experimental Animal Study," European Surgical Research 2007 39(4):239-244; Kaplan, M., Bozkurt, S., Kut, M. S., Kullu, S., and Demirtas, M. M. 2004. "Histopathological Effects of Ethyl 2-cyanoacrylate Tissue Adhesive Following Surgical Application: An Experimental Study," European Journal of Cardiothoracic Surgery 25(2):167-172) as compared to any other kind of surgical adhesive currently available is desirable for assuring the sealing of each stay insertion incision before withdrawal.

The superior tissue infiltration allowed by an alternative surgical sealant still or not yet under study (see, for example, Ozmen, M. M., Ozalp, N., Zulfikaroglu, B., Abbasoglu, L., Kacar, A., Seckin, S., and Koc, M. 2004. "Histoacryl Blue versus Sutured Left Colonic Anastomosis: Experimental Study," Australian and New Zealand Journal of Surgery 74(12):1107-1110), perhaps a gelatin-resorcinol-formaldehyde-based glue of the kind made by Cardial, Technopole, Sainte-Etienne, France (see Wippermann, J., Konstas, C., Breuer, M., Kosmehl, H., Wahlers, T, and Albes, J. M. 2006. "Long-term Effects in Distal Coronary Anastomoses Using Different Adhesives in a Porcine Off-pump Model," Journal of Thoracic and Cardiovascular Surgery 132(2):325-331) that would better promote the actual mending or union of the connective tissue as it was replaced might best be taken advantage of instead.

XV10. Practitioner Preference for Cyanoacrylate Tissue Sealant

Small-chain cyanoacrylates absorbed but suspected to be toxic and long-chain cyanoacrylates considered less toxic but slowly and not fully absorbed, ongoing work on investigational atoxic absorbable surgical cyanoacrylate cements seeking complete atoxicity and absorption may have the effect of further improving cyanoacrylate cements (see, for example, Schenk, W. G. 3rd, Spotnitz, W. D., Burks, S. G., Lin, P. H., Bush, R. L., and Lumsden A. B. 2005. "Absorbable Cyanoacrylate as a Vascular Hemostatic Sealant: A Preliminary Trial," American Surgeon 71(8):658-661; Lumsden, A. B. and Heyman, E. R. 2006, cited above Ellman, P. I., Brett Reece, T., Maxey, T. S., Tache-Leon, C., Taylor, J. L., Spinosa, D. J., Pineros-Fernandez, A. C., Rodeheaver, G. T., and Kern, J. A. 2005. "Evaluation of An Absorbable Cyanoacrylate Adhesive as a Suture Line Sealant," Journal of Surgical Research 125(2):161-167; Seifman, B. D., Rubin, M. A., Williams, A. L., and Wolf, J. S. 2002. "Use of Absorbable Cyanoacrylate Glue to Repair an Open Cystotomy," Journal of Urology 167(4):1872-1875).

XVI. Stay Insertion Tools

Figure 86:
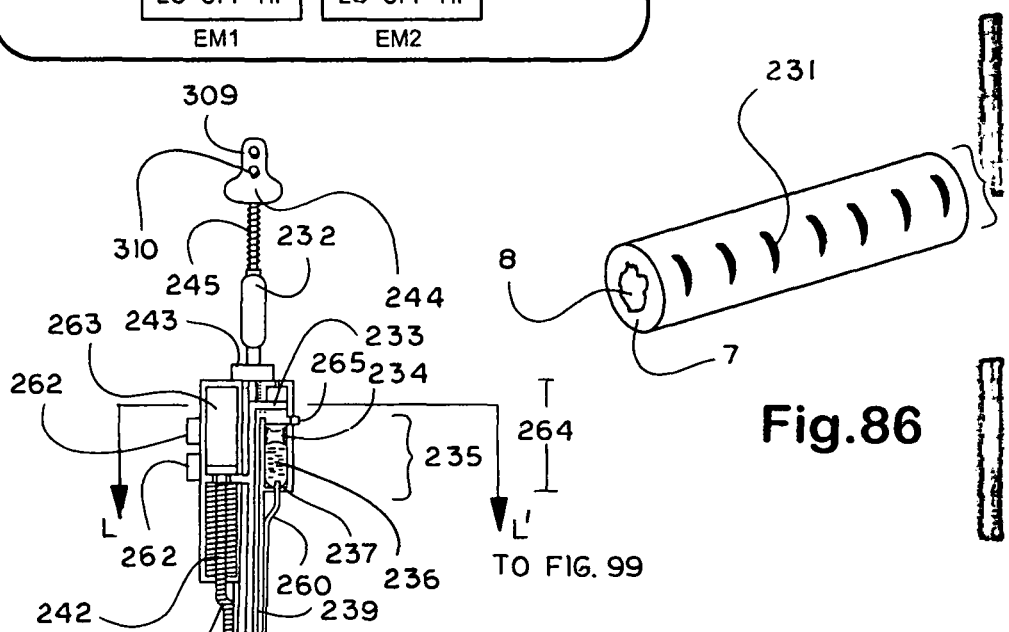
FIG. 86 shows a diagrammatic perspective view of a ductus that has been implanted with stays, whether ferromagnetic for encirclement by a stent-jacket, medicinal, radiation seeds, some combination thereof, or as structural buttresses, absorbable or nonabsorbable.

Stay insertion tools are shown in FIGS. 87 thru 91, 95, and 102, with internal workings of a mechanical embodiment shown in greater detail in FIGS. 91, 93, 95, 96 thru 99, 102, and 103. Stay insertion tools can be produced with different degrees of automation to control the stay ejection cycle. Except for stay retention, retraction, and recovery electromagnet 242, most stay insertion tools are mechanical. In such a substantially mechanical embodiment, stay retention, retraction, and recovery electromagnet 242, remains unenergized from the instant the operator confirms that stay 231 has been properly inserted as shown in FIG. 86.

The operator then releases thumb-ring 244, allowing thumb plunger-rod spring 245 to return thumb plunger-rod 238 to the raised position, completing the ejection stroke or phase of the ejection cycle. Control syringe-configured tools such as shown in FIGS. 87, 88, 90, and 102, apply force to the stay not as imposed by the operator but rather as set by the force of spring return when the thumb is lifted. With any control syringe-configured embodiment, the operator can use the thumb to restrain thumb plunger rod 238 from returning under the unimpeded force of spring 245, or can suddenly remove the thumb, allowing thumb plunger rod 238 to return under the force and speed determined by spring 245.

Accordingly, when the force of stay insertion is considered a significant outcome factor, the restorative force of rod-spring 245 is made adjustable through use of a tool with a calibrated screw thumb-plunger rod 238 return spring 245 tightener-loosener that allows translating test values into equivalent spring forces. Such a screw adjustment typically comprises a knurled knob with threaded center hole that rotates about and at right angles to the threaded thumb plunger-rod 238 in FIGS. 87, 88, 90, and 102. To allow instant access by touch, the knob is usually located between finger rings 232 and 249 and cap 243. To distinguish between surface hardness as indicated by indentation and ductus wall or organ cortex or capsule elasticity requires direct viewability.

This does not, however, equate to a need for high cost imaging but rather use of an attached or incorporated angioscope. With no stays loaded, the calibration measures indentation and applied force against the tip of the stay ejection blade or tongue 247 for direct translation into the return stay insertion spring force to be set. Automatic adjustment of the spring tautness in response to the resistance to penetration found is not incorporated as adding too much expense. When the adventitia is malacotic, a blunt blade tip with projection that friction fits in a hole at the center of the blade fork tip protects against puncture through the ductus. The calibrated scale is etched to encircle an upward extension of transparent plastic tool barrel 239 which is notched to avoid obstruction of thumb-ring 244 when depressed.

In contrast, a pistol-grip configured tool as shown in FIG. 89 inserts stays under the direct intuitive strength of trigger pull force exerted by the operator and is unamenable to the quantifying of this force. The insertion of stays based upon the quantified results of testing therefore requires infixion by means of a control syringe-configured stay insertion tool. Because the placement of stays poses relatively little risk and stay by stay placement responsive to testing would unduly prolong the procedure, most stay insertion tools take the quantified results of in situ tissue testing as addressed below in section XVII entitled Testing and Tests and use these as an intuitive guide.

Figure 87:
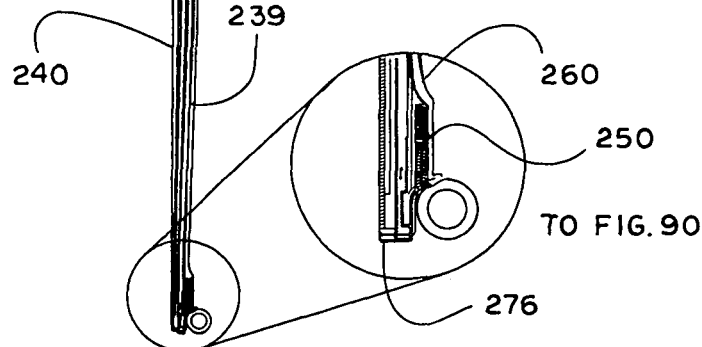
FIG. 87 shows a right side-view partly in section as well as a detailed view of the lower or working end of a control syringe-configured depress-to-eject tissue sealant/release-to-insert a stay, insertion passive-type stay insertion tool which allows tissue sealant to be applied to the stays upon ejection and the force of insertion to be set by the restorative force of the plunger or slide return compression spring but also allows force to be reduced or increased manually (front and side mounting spring clips not shown).
Figure 90:
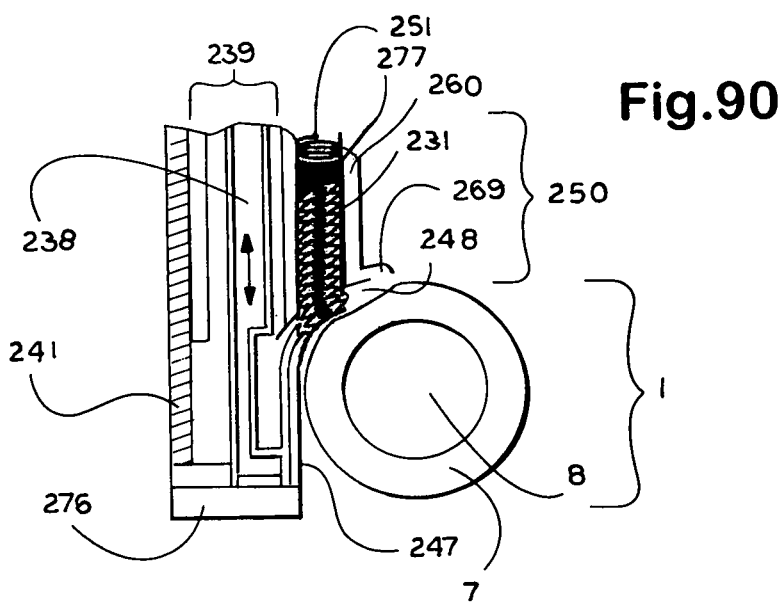
FIG. 90 shows an enlarged view of the working or ejection end of a stay insertion tool whether of the control syringe-configured release to eject type shown in FIG. 87 or the pistol-configured pull-trigger to eject type shown in FIG. 88 at the end of the stay loading phase of the ejection cycle with stay ejection blade fully retracted.
Figure 91:
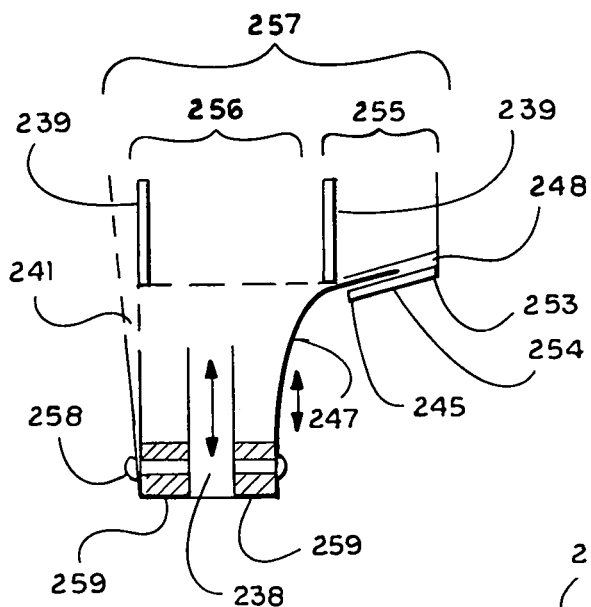
FIG. 91 shows a further enlarged view of the working or ejection end of the stay insertion tool shown in FIG. 90 to allow the parts thereof to be clearly seen.

As shown in FIGS. 87, 90, and 91, when thumb-ring 244 is depressed in the control syringe configured embodiment shown in FIG. 87, the thumb plunger-rod 238 retracts stay ejection blade or tongue 247 downward, and except for its tip, down out of ejection slot 248, allowing stay refill strip or clip 250 advancement spring 251 to seat the next stay 231 in the strip, completing the stay loading phase of the cycle. Exactitude in the force of stay insertion rarely critical, the nonquantified or intuitive force of penetration applied by the operator is almost always satisfactory. Elimination of the need for testing when allowable and the added expense of omitting a calibrated return spring screw adjustment from the tool represent advantages of time and cost over alternative methods for infixing ductus-intramural implants.

To gain a clear view of the small field, a cabled lamp, endoscope, or angioscope, not included in the drawing figures, is clipped or lashed alongside the tool, as may an excimer laser or radiofrequency scalpel to expedite dissection or assist in gaining access to the target ductus or tissue. As may be seen in FIG. 90, the lower end of stay advancement spring 251 is capped by stay advancement spring end-cap 277. End-cap 277 is configured to interface with the uppermost stay in refill strip 250 so as to keep the strip aligned. To assure that the uppermost or last stay in the refill strip is advanced flush to the floor of ejection slot 248 even past a moderate angle in a tool with pivot, as addressed below in the section entitled Stay Insertion Tool with Pivoting Base, the face of cap 277 where it apposes or nestles the uppermost stay is elevated.

The bond used to queue the stays into refill strip or clip of stays 231, ordinarily provided by dried sugar, is easily broken with the stays axially rotating at and continuing past the bend to seat firmly against the floor of ejection slot 248 properly for ejection. Due to the difficulty in introducing a flexible joint along thumb plunger-rod 238, a stay insertion tool with a pivotable base, as addressed below in the section of like title, is not controlled mechanically. In such an embodiment, except for control by the operator of the ejection cycle as a whole, the subsidiary functions encompassed within the ejection cycle are not controlled by the operator or mechanically but rather by the battery 263 and damped solenoids under the control of an inmate (embedded) microcontroller.

Suitable microcontrollers are available from Microchip Technology, Atmel, Freescale Semiconductor and Texas Instruments corporations, for example. Instead of up and down reciprocating thumb plunger-rod 238 to operate the stay ejection blade 247, a plunger solenoid in the tool base 257 in FIG. 91 is used to perform this function, and instead of the internal chain pulley and ratchet mechanism shown in FIGS. 96 thru 98 to control the tissue cement air pump 264 piston 233 shown in FIGS. 87, 95 thru 99 and 102 when the operator rotates thumb-ring 244, a rotary solenoid is used. When the operator releases thumb-ring 244, plunger-rod 238 rises under the restorative force of spring 245, pulling stay ejection blade 247 up through ejection slot 248, ejecting a stay 231, completing the insertion phase of the cycle.

Stay insertion tools are precision instruments made to insert stays of a specific shape and dimensions; the ejection blade and slot lining are not removable to allow use with stays of another shape or size. The ejection overall comprehends not only the stay insertion component but attendant components of electromagnet control and stay coating tissue cement ejection. In a tool with inmate microcontroller, these functions are automatically controlled as well. Once satisfied that the stay 231 has been properly positioned, the operator releases the ejection control knob (switch, button), or the upper of the two shown as 262 in FIGS. 87 and 102.

When pushed in, the upper control knob sends current from the battery 263 to stay retention, retraction, and recovery electromagnet 242. While pushed in, the upper knob is rotated to vary the current and magnetic strength. When pushed in again, the knob returns to its undepressed position whereupon the current is shut off. The lower of the two control knobs works in the same way to control the magnetic circuit with the polarity reversed. So long as the magnetic strength need not be adjusted, operation of the tool is single-handed. While such an embodiment is the least costly to produce, when the magnetic strength must be adjusted, such a mechanical embodiment poses the drawbacks of requiring 2-handed operation and necessitating the coordinated depression and lifting of thumb-ring 244 with the control of the electromagnet.

For example, if the field strength is set too high, and/or the operator withdraws the tool from the insertion site prematurely so that the cyanoacrylate cement does not cause the stay to adhere where placed, unless the magnetic force is reduced, the stay could stick to the end of ejection blade 247 and be unintentionally retracted despite having been well placed as shown in FIG. 86. If mispositioned, the magnetic strength is deliberately turned up to retract the stay, and to reposition the stay in ejection slot 148 for rejection requires that the magnetic strength be set high.

To negate the need for practicing the coordination required and to avert the human error to which the criticality of perfect coordination predisposes, most practical tools incorporate a microchip controller to coordinate the sending of current to stay retention, retraction, and recovery electromagnet 242, with the position of thumb plunger-rod 238 and the ejection blade 247 or the phase in the ejection cycle. The stay ejection blade 247 retracted, the stay refill strip 250 advancement spring 251 forces the next stay 231 in the strip down onto the floor of the ejection slot 248 and in position to be ejected.

In an embodiment that is mechanical in using only an electromagnet to generate the magnetic force and not incorporating an electromechanical actuator in the form of a plunger solenoid, for example, and therefore without the aid of an embedded microcontroller to accomplish the action automatically, the polarity of to stay retention, retraction, and recovery electromagnet 242, is not ordinarily reversed for a moment after being retracted to assure that residual magnetization of the ejection blade 247 does not accumulate in the ejection blade 247 or cause a stay 231 to adhere to its tip. Instead, a polarity reversal control knob, the lower of the two knobs shown as 262 in FIGS. 87 and 102 is provided for periodic demagnetization, confirmable by checking whether the stay ejection blade 247 attracts a loose stay 231 from a table top.

Demagnetization of the ejection blade 247 is usually accomplished by reversing the polarity of stay retention, retraction, and recovery electromagnet 242, the ejection blade 247 representing the terminal component in the magnetic circuit, each stay 231 added at the end thereof once articulated by the during insertion. Control of the battery 263 supplying current to stay retention, retraction, and recovery electromagnet 242 in strength and polarity is ordinarily controlled manually, but as indicated, is more often supported by an embedded microcontroller that automatically adjusts the field strength in coordination with the ejection cycle. In this instance, the polarity is automatically reversed for an instant to assure that no buildup of magnetization takes place.

In a fully electrified embodiment wherein ejection is effected by a damped direct current plunger solenoid, power for the solenoid is taken from the same onboard battery 263, such as lithium ion, that powers stay retention, retraction, and recovery electromagnet 242 under the control of the same microchip as controls the battery component of the ejection cycle. In an embodiment that ues a solenoid without an embedded microcontroller, a plunger-rod 238 connects the solenoid positioned down in the tool base 257 to the inmate stay coating pump piston 233 but not to the plunger-rod thumb-ring 244, which is stationary rather than depressed and raised as is that of a syringe.

With such an embodiment, the field strength set before use, the operator positions the tool on the ductus, pushes the upper triggering control knob, and if satisfied that the stay is properly inserted, pushes the same control knob again to deenergize the electromagnet and leave the stay as positioned. When the ejection cycle is under the control of a microcontroller, the microcontroller adjusts the field strength. Because the auxiliary syringe is more often used on an intermittent, discretionary basis to dispense surgical cement or another fluid therapeutic substance independently of the stay insertion cycle, control over an auxiliary syringe attachment, as shown in FIGS. 101 thru 103 and addressed below in the section entitled Stay Insertion-Tool Auxiliary Syringes, is not usually integrated into the ejection cycle as an automatic component thereof.

A switch on thumb-ring 244 allows switching control of an auxiliary syringe between integrated into or independent of the ejection cycle. The auxiliary syringe is controlled by depressing buttons mounted about the outside of thumb-ring 244 as shown in FIGS. 87, 88, and 102. By contrast, the inmate (normally long chain cyanoacrylate) cement stay coating air pump 264 comprising piston 233 and cement tissue cement/surgical adhesive-sealant refill cartridge 236 in refill cartridge compartment 235 shown in FIGS. 87, 88, and 102 with inner workings shown in FIGS. 95 thru 100, is seldom omitted from the stay ejection cycle. The microchip coordinates the ejection cycle with respect to both energization of the electromagnet and the solenoid.

If the operator is dissatisfied with the insertion, the ejection control button is not released, the electromagnet is not turned off, and the spring or solenoid is used to retract the stay. Since to retract the stay entirely into the ejection slot to its starting position against the downward force of the stay refill strip 250 advancement spring 251 as preferred requires considerable magnetic force, such a semiautomatic embodiment is provided with a high capacity battery and a powerful electromagnet. The position of the battery and electromagnet compartments high up on the tool place these well clear of the entry incision, only the small working end of the tool and a portion of the shaft needed to reach down to the ductus introduced intracorporeally.

The size of the battery and electromagnet are thus limited only by the need to avoid blocking the sight lines of the operator, so that these can be made as large as necessary. An aborted and retracted stay is placed sufficiently to a side of the initial incision to minimize trauma to the ductus. The ejection blade can be returned by a spring as in the mechanical embodiment or by reversal of the solenoid in an electrical embodiment whether by a solenoid spring return or reversal of polarity.

Rather than by a direct mechanical connection, a stay insertion tool with pivoting base, as addressed below in the section of like title, uses a direct current plunger solenoid to move the stay ejection blade. Although actuation of the onboard tissue cement (or other therapeutic fluid) pump is by direct mechanical connection to the solenoid that pulls up the stay ejection blade, the level of electrification already incorporated prompts further incorporation of a microchip to coordinate the ejection cycle.

XVI1. Stay Insertion Tool Structure

Access to the exterior of the ductus wall in order to insert a stay with a pliers-type tool such as a crile or needle forceps at the correct angle necessitates a needlessly long incision. A special stay insertion tool (stay infixion tool, stay inserter) that allows the wall to be implanted with the tool normal to the outer surface of the ductus makes insertion possible through a keyhole incision. Inserting stays from within the lumen with endoscopic forceps is similar to placing suture with a curved needle held with a needle forceps where the needle can be perpendicular to the tool making rotation of the wrist sufficient to insert the needle laterally.

When access to the ductus is clear so that the surrounding tissue does not come in contact with the tool, as in an open surgical field, the tool will ride up and down with the pulse or intrinsic motility providing the operator with tactile (tactual, haptic) cues to the proper moment for insertion. A stay insertion tool is essentially a stapler-type mechanism arranged vertically, with ancillary means for coating each stay as it is ejected, illuminating the treatment site when necessary, and configured to negotiate a surface that is curved and compliant rather than planar and hard.

Whether the stays are ejected mechanically or electrically, the predominant object in the design of a stay insertion tool is to minimize the size of the entry wound. Rather than modular or interchangeable, stay insertion tools are made for common combinations of stays and cements. Attachment to the stay-insertion tool of an auxiliary syringe as addressed below in the section entitled Stay Insertion-Tool Auxiliary Syringes allows use of the tool as either a stay ejector, syringe, or both without the need to retract the tool once positioned on the substrate ductus.

Either or both the inmate cement or stay refill cartridge chambers can be left empty, or both can be filled and an auxiliary syringe attached to deliver stays coated with cement or any liquid or semiliquid therapeutic substance with additional liquid substances delivered from the auxiliary syringe in any sequence relative to stay ejection if applicable. Thus, the tool without a stay refill cartridge inserted can function as a syringe able to deliver multiple substances. Most stay insertion tools are mechanical an use an onboard battery to power electrical components, such as the stay recovery and retraction electromagnet and a fiberoptic lamp or other electrically powered cabled device clipped alongside the tool.

However, mechanical embodiments unable to flex without introducing costly joints, an alternative solenoid powered embodiment is described below in the section entitled Stay Insertion Tool with Pivoting Base. It is considered obvious that solenoid power need not be reserved for a pivoting model and might be used in any such tool. While demanding skill, spatial clearance is afforded without making it necessary to lengthen an incision to more acutely angle the proximal end of the tool, so that this lateral approach is more readily accomplished than if the tip of the tool had to remain substantially normal to the ductus. FIGS. 87 and 88 show a control syringe-configured, while FIG. 89 shows a pistol-configured stay insertion tool.

The stay insertion tool ideally has a weight such that when rested upon the ductus, the tool rides up and down in compliance with the ductus intrinsic motility without compressing the ductus, exerting the downward bearing force adequate for implantation. The variability among ductus especially when diseased and the difficulty of effecting implantation without the addition of downward force make this ideal elusive. While both inmate stay and cement ejection functions might be accomplished electrically, a mechanical embodiment allows the tool to be provided at less cost.

By contrast, unless positioned off to a side, a supplementary, or auxiliary, syringe, as addressed below in the section entitled Stay Insertion Tool Auxiliary Syringes, attached to the tool, such as one containing a two-component tissue sealant, would interfere with a clear view of the treatment site, which separation at a distance makes the electrical operation of attached syringes advantageous. When a cement or medication cartridge is inserted into the air pump 264 chamber, a push type, or control syringe configured embodiment stay insertion tool such as that shown in FIG. 87 can be set to eject a cyanoacrylate cement or a tissue sealant, for example, upon depression of the thumb-ring 244 and inject the stay 231 when thumb-ring 244 is released.

Except that the ejection mechanisms of the push or syringe and the pistol configured stay insertion tools work in reverse, the internal structure and attachment of auxiliary syringes are equivalent if not identical. Whereas the inmate stay ejection and surgical cement or other fluid or semifluid therapeutic substance delivery mechanisms are locked together so that use for one or the other required leaving one of the refill cartridge chambers empty, attachment of an auxiliary syringe or syringes not only allows additional therapeutic substances to be delivered to the treatment site without the need to retract the tool once positioned on the substrate ductus, but isolates syringe from ejection function.

The control syringe configuration of the tool makes it possible for the operator to extend the interval over which either or both of these actions last. Additionally, as addressed in the section below entitled Mechanism for Adjustment in Stay Insertion Tool Ejection Cycle Inmate Cement Delivery Interval, the moments of onset, duration, and cutoff of adhesive delivery are adjustable In cement-ahead operation, the cement is ejected onto the adventitia first and the stay is passes through the cement as it enters the wall of the ductus. Even though most of the cement is wasted or 'squeegeed' away as the stay penetrates, the use of cement or medication containing a thickener and stays having a deeply textured surface allows a significant pickup of the cement or medication.

A deeply textured surface also assists to conduct heat through the stay, which expedites bonding with the application of heat. Tool barrel 239 in which thumb rod 238 is centered and moves up and down is the stationary body of the tool and runs from just beneath top cap 243 to toe 253 of foot 255. The tool with adhesive cartridge 236, air pump piston-plunger 233, tissue cement or therapeutic fluid delivery line 260 oriented as shown in FIG. 87 is configured to allow coating the upper surface of each stay.

As shown in FIGS. 87, 88, 90, 97 99, 102, and 106, with the exception of tissue sealant (tissue adhesive-hardener) air pump 264 piston-plunger 233, which is connected to and moves with thumb rod (thumb plunger-rod, plunger-rod, shaft) 238, the parts of the stay insertion tool seen to the right of thumb plunger-rod or shaft 238 remain stationary, whereas the parts of the tool seen to the left ride along the outside of the tool barrel or shank 239 down when the operator depresses, then up when the operator ceases to apply downward force with his thumb against thumb plunger-rod or shaft 238. The portion of the tool between the ejection control syringe-type or trigger control at the proximal end or top and the distal or working end is shank 240, which includes soft iron magnetic conductor and probe 241.

To minimize the dimensions of the portion of the tool for insertion intracorporeally, tool barrel or shank 239 is drawn down to as low a cross-section as does not impede thumb plunger-rod or shaft 238. To use the stay insertion tool, the ductus is accessed through a small incision, which can be held open by retractors, such as a miniature version of an omni-bearing retractor or a cannula. The size of the insertion tool necessarily gauged to the diameter of the ductus to be treated, the distal end of the insertion tool is typically 5 millimeters wide and 8 millimeters from front to back. In FIG. 87, cap 243 is not bonded to the components to the left-hand side of thumb plunger-rod or shaft 238 but is bonded to those on the right-hand side.

Referring now to FIGS. 90 and 91, parts of the stay insertion tool beneath cap 243 shown to the left side in FIG. 87 move down when the operator depresses thumb-ring 244 and return upwards by plunger-rod 238 return spring 245 when thumb-ring 244 is released. Thus, distal tip of soft iron magnetic conductor and probe 241 moves up and down with stay retention, retraction, and recovery electromagnet 242 and heel 246 of stay ejection blade or tongue 247 as one. In FIGS. 87, 89, and 90, the ductus is 1, its wall 7, and lumen 8 consistent with FIGS. 2 thru 5 Alternatively, the distal end of the soft iron magnetic conductor and probe 241 could be slid against an upright contact strip at the back of stay ejection blade 247, thereby to conduct the magnetic force used to retain the stay.

Then the parts of the tool to the left would remain stationary allowing better depth clearance for the butt portion behind the foot of the insertion tool base. Devising the mechanism to present reciprocal movement externally makes it possible to mount a sliding contact used to control the delivery of a tissue sealant from an attached dual-chamber syringe. In an embodiment in which the parts shown to the left are stationary, the sliding contact is placed along thumb plunger-rod or shaft 238 with the stationary contact mounted to the internal surface of the tool barrel or shank 239. Such an internal sliding contact can be positioned anywhere along thumb plunger-rod or shaft 238. However, internal location makes the sliding contact inaccessible without disassembly of the tool.

While another such internal contact could be used to control the motorized expulsion of the inmate (internal) surgical cement syringe that would simplify the reversal of cement delivery between cement-ahead (of stay ejection) and cement-follow modes of operation, a relatively simple mechanical system makes it possible to provide the tool at less expense. When thumb plunger-rod or shaft 238 is fully depressed, the front end of the ejection tongue must remain intromittent or threaded within a portion of stay ejection slot 248 far enough to the rear as not to interfere with the seating of the next stay to be ejected, and when the thumb plunger is released, the front end of the ejection tongue must extend past the front edge of stay ejection slot 248 by the distance that the trailing tip of the stay is to be countersunk within the wall of the ductus.

Thumb plunger-rod or shaft 238, made of a nonmagnetic stainless steel, such as one of those specified below in the section entitled Subcutaneous, Suprapleural, and Other Organ-attachable Clasp- or Patch-magnets, must have reciprocating travel sufficient to fully retract plunger-blade or stay 231 ejection blade or ejection tongue 247, and when returned by thumb plunger-rod compression spring 245, drive stay 231 through stay ejection slot 248 and into ductus 1 wall 7. Since the operator is able to control the return of thumb plunger-rod 238 under the restorative force of thumb plunger-rod 238 compression coil spring 245, this spring is chosen for just enough force to allow stay ejection blade or tongue 247 to penetrate the most resistant diseased ductus.

While stays 231 do not extend to the lumen, calcification of layers through which a stay 231 must pass disallow the use of stays (or miniballs) and call for resection and anastomosis of the segment affected thus. Thumb plunger-rod 238 is centered within tool barrel 239 by attachment to the finger rings above and ejection blade or tongue 247 below. Shown in FIGS. 87 and 90, Stay refill clip compartment 250 consists of stay advancement compression spring 251 which bears down on the clip of stays 231 loaded into stay refill clip compartment 251. The spring circular, and the stays torpedo in cross section, the spring matches the stays 231 in length and has a lower end-cap with a circular top and bottom configured to complement the upper surface of stays 231.

In a control syringe-configured push-type stay insertion tool such as shown in FIGS. 87 and 88, which does not allow switching between cement-ahead and cement-follower operation, the thumb, index, and middle finger rings all freely rotate about a vertical axis, a rotary joint (not shown) on level with the bottom of cap 243 for thumb plunger-rod 238 allowing the upper portion of thumb plunger-rod 238 to rotate without affecting the lower portion. This allows maximum comfort and the least fatigue over the course of longer procedures with minimal displacement of the distal or working end of the tool for either a right- or left-handed operator when the operator must switch hands or is forced by the anatomy to adopt an awkward angle.

Index finger ring 232 and middle finger ring 249 are journaled about vertical pins that allow these to be rotated. In an embodiment of like configuration that does allow switching between cement-ahead and cement-follower operation, thumb-ring 244 similarly rotates freely through an arc of about 45 degrees to either side of center without effecting the rotational angle of thumb plunger-rod 238. Referring now to FIGS. 96, 97, and 98, in such a switching embodiment, exceeding this arc at either end causes thumb-ring 244 to rotate thumb plunger-rod or shaft 238 causing rod 238 to click into engagement with the detent just past each end of the arc.

This corresponds to the rotation of thumb plunger-rod 238 such that the pin used to switch between sides of sprocket chain 252 is engaged in the sprocket link to one or the other side, which side determining whether air pump 264 piston-plunger 233 is driven downward with the thumb plunger-rod in cement-ahead operation or when thumb plunger-rod 238 is released to return to the top position under the force of thumb plunger-rod compression spring 245. Matching the strokes of thumb plunger-rod or shaft 238 and cement or medication air pump 264 piston-plunger 233 eliminates the need for an additional mechanism for limiting the portion of thumb rod stroke used to move air pump 264 piston-plunger 233.

The length of thumb plunger-rod 238 which passes through cap 243 when depressed has a shallow longitudinal groove (running concavity) or spline-cut that can be rotated between groove complementary protrusions or elevations on the inside of cap 243. A r rotary joint above the level of stay ejection blade or tongue 247 allows the lower portion of thumb plunger-rod 238 to remain at a fixed rotational angle despite first free rotation of thumb-ring 244, then rotation with the thumb ring of thumb plunger-rod or shaft 238 above the level of the rotary joint.

To allow the sliding and rotation of a thumb switch or switches mounted to thumb-ring 244 to any position along thumb-ring 244 for the immediate control of any auxiliary devices in use, which is addressed in the section below entitled Connection of the Holding Frame to the Stay Insertion Tool, such as an outrigger syringe holding frame, laser, or suction line, thumb-ring 244 is uniform in cross section. Small depressions and its complementary elevations on the internal circumference of cap 243 (not shown) serve as detents that allow thumb plunger-rod or shaft 238 to be positively engaged at the rotational angle of one or the other of the two ridges; however, the depth of engagement between the elevations and depressions, or detents, allow rotation to and detention at either rotational angle with relative ease.

The free rotation about its longitudinal axis of thumb-ring 244 between these detent protrusions (along with the free rotatability of the index and middle finger rings 232 and 249) as addressed below in the section entitled Mechanism for Switching from Cement-ahead to Cement-follower Operation produces no rotation of thumb plunger-rod 238. The rear outer surface of stay refill-strip compartment 250 is concave to complement the front surface of tool barrel 239 for a flush fit, these two surfaces bonded together by means of an adhesive such as a cyanoacrylate cement. The bottom or floor end of stay refill-strip compartment 250 is curved upward from back to front, and the underside of the stay ejection slot 248 floor is the tool foot, which is deep textured to resist slippage when set in complementary relation to the outside of the ductus to be implanted.

As shown in FIG. 93, the front tip of stay ejection blade or tongue 247 is indented to engage the rear end of stay 231 and extends into the rear of stay ejection slot 248 but not into the chamber within as would obstruct the descent of each stay in the refill strip or clip of stays 231 in turn down against the floor under the downward force of stay advancement compression spring 251. When the wall of tool barrel 239 is too thin to assure that the front tip of stay ejection blade or tongue 247 will be retained in the correct position to push through each stay 231, a rearward extension in the form of a lip surrounding stay ejection slot 248 rear is applied by gluing tiny strips of a plastic to form a framing rearward extension to stay ejection slot 248 opening.

Each stay in turn is thus constrained to the correct seating and exit path under the downward force of spring 245 and the sides of stay refill clip compartment 250. In FIGS. 90 and 91, the entrance for the stay ejection blade 247 into the stay ejection slot 248 extends just below the lower edge of the front wall of tool barrel 239, which is level with the upper surface of the stay against the lower surface or floor of stay ejection slot 248. Releasing thumb-ring 244 thus causes the front tip of stay ejection blade 247 to engage the rear tip of the stay pressed down against the lower surface or floor of stay ejection slot 248 driving stay 231 through the front opening of ejection slot 248 and into the outer tunic of ductus wall 7 or adventitia 1 shown in FIGS. 2 thru 5 as 2.

The downward force exerted by stay advancement compression spring 251 and complementary contours of the stay body and floor of stay ejection slot 248 prevent the front stay-engaging end of stay ejection tongue 247 from applying an ejection slot-deviating or nonaligned upward angular vector against the rear of stay 231 as would angle the stay to one side, resulting in resistance to ejection and nonperpendicular entry into ductus wall 7. Still referring to FIGS. 90 and 91, in both the push or control injection syringe-configured embodiment shown in FIGS. 87 and 88 and the pull or pistol-configured embodiment shown in FIG. 89, magnetic conductor and probe 241, lower end of thumb plunger-rod or shaft 238, and lower end of ejection tongue 247 are fastened together by magnetically conductive rivet 258 and spaced apart from one another along the barrel of rivet 258 by spacing tubes, washers, or ferrules 259.

Fastened together thus, magnetic conductor and probe 241 slides up and down against the rear outside wall of stationary tool barrel 239, the lower end of thumb plunger-rod 238 moves down and up within and extends below the lower end of tool barrel 239, and the lower end of ejection tongue 247 extends below the front wall of the bottom end of tool barrel 239 and stay refill-strip compartment 250. As best seen in the detail of the tool bottom in FIG. 91, the bottom portions of these reciprocating parts are punched or drilled to pass through and joined together by magnetically conductive rivet 258 with stay ejection tongue 247 at the front, thumb rod thumb rod 238 at the center, and magnetic probe 241 at the rear, these three parts separated by spacing tubes, washers, or ferrules 259 and comprising the rear reciprocating butt portion 256 of the stay insertion tool.

Magnetically conductive rivet 258 binds together rear butt portion 256 of the tool by passing through these parts and through spacing tubes, washers, or ferrules 259 used to space these parts apart. Rivet 258 thus includes magnet conductor and probe 241, spacing tubes, washers, or ferrules 259, and stay ejection tongue 247. Upon depression of thumb rod 238, butt 256 moves up and down or reciprocally past the stationary bottom or distal margin of tool barrel 239 and stationary barrel 239 with foot 255 fastened to its front. In FIGS. 87, 89, and 90, the bottom of the reciprocating butt portion 256 of base 257 is additionally covered by a protective pad of surfactant and other tissue irritating material free neoprene or similar cushioning material.

If and only if a slitting edge attached beneath a permanent bottom protective cushion 276 presents no sharp edges, a separate stay extraction slitting edge as addressed below in the section entitled Butt-pad with Retractable Slitting Edge may be fitted flush therebeneath. In a mechanical embodiment, butt 256 reciprocates up and down by the small distance equal to that of stay ejection blade 247 past the lower border of stationary barrel 239. Use of a vertically reciprocating mechanism allows a smaller tool diameter and thus entry wound than do rotatory mechanisms that use a miniature electrical motor and a crank or cam shaft to convert the rotary to horizontal reciprocation of the ejection blade.

The latter allow a rotating vertical shaft with the motion converting mechanism at the lower or distal end to eject stays at a very high rate; however, high speed whether fully or semiautomatic is specifically rejected as militating against the considered placement of each stay as essential for medical reasons. The electrically operated tool addressed below in the section entitled Stay Insertion Tool with Pivoting Base substitutes a plunger solenoid actuated by a control button on thumb-ring 244 for vertical reciprocation by depression of thumb-rod 238; however, the small reciprocal movement of ejection blade 247 remains vertical. Provided it does not increase the diameter of the tool untenably, an ejection blade directly connected to a plunger solenoid can avoid vertical reciprocation.

However, for stability during and more accurate insertion, some extension by a butt placed against the proximal circumference of the target ductus is still provided, although the 'butt' extension is then shorter. To minimize the risk of injury to adjacent tissue, tool butt 256 is kept as short as practicable whether reciprocal action is accomplished with or without an electromechanical actuator. In the mechanical embodiment shown in FIGS. 87, 90, 91, and 102, foot 255 is rested on the ductus to be implanted with a stay or stays. Depression of butt 256 retracts stay ejection blade or tongue 247 to the position just before the entrance to stay ejection slot 248. The reciprocal action serves to insert the successive stays.

This semiautomatic operation whereby each stay is seated for ejection upon ejection of the stay preceding it reduces procedural time without the need to withdraw and reinsert the tool increasing the chances for infection. Except for tools that incorporate a laterally pivoting foot joint as addressed below in the section of like title, the orientation of ejection slot 248 is fixed (nonadjustable). Within the degree of flexion allowed by stay ejection tongue or blade 247 introducing suitable rotatory joints would allow stay ejection slot 248 and stay refill strip or clip compartment 250 to be canted (inclined, angled) from back to front or side to side; however, this is discounted as needlessly expensive compared to standardized models.

Except for its front end portion, forcing thumb-ring 244 downward retracts stay ejection blade 247 from from ejection slot 248, and releasing syringe thumb-ring 244 allows thumb plunger-rod 238 compression spring 245 to retract the lower ends of magnetic conductor and probe 241, thumb plunger-rod or shaft 238, and ejection blade or tongue 247, fastened together beneath the lower end of tool-barrel 239 until these are stopped by the lower end of tool barrel 239 or slightly short of that height when stay ejection blade or tongue 247 resists bending or its exact position prevents the top of the butt from flush relation with the lower end of tool barrel 239.

Pushing down on thumb-ring and thus thumb-plunger-rod 238 thus pulls down to withdraw ejection blade or tongue 247 from stay ejection slot 248, the front end of ejection blade or tongue 247, as indicated above, always remaining engaged and aligned within stay ejection slot 248 even when withdrawn to the extent allowed. The insertion tool must minimally interfere with imaging equipment needed to confirm satisfactory concentricity of insertion. In the push-type embodiment described first, the adhesive delivery mechanism is in line with the stay magazine and the stay retention, retraction, and recovery electromagnet 242 is situated behind the tool. Placing both beneath the wrist of the operator resulting in minimal obstruction to vision and manipulation.

Provided insertion results in substantial concentricity, even a suddenness and amplitude of pulse or peristaltic action that exerts considerable outward compressive force upon a lumen wall reduced in elasticity by disease will not cause the stay to incise toward the lumen. The insertion tool must therefore introduce the stays to be concentric to the ductus. While a growing resistance posed by adhesive buildup will become apparent tactually, and the application of adhesive to each stay and proper sealing of each adventitia entry incision can be seen with the binocular telescopes and head-lamp when the tool is lifted aside from each stay insertion site, an endoscope allows proper operation of the tool to be confirmed without the need for removal.

The material must also be strong enough that at typically 5 millimeter wide and 8 millimeter from front to back with sides 1.5 millimeter thick, the working end will not fracture or fall inside the body. In addition to providing transparency, the nonferromagnetic plastic body serves to prevent interference with the onboard stay retraction or recall device to be described. For these reasons, the tool is typically made 18 centimeters or more in length of transparent polyethylene terephthalate, polystyrene, high-density polyethylene, or acrylonitrile butadiene styrene. Methyl methacrylate (acrylic) is too brittle to preclude fracture at the small working or distal end. Transparent parts tend to interfere less with views of the work area from different angles.

Two embodiments are provided, one, shown in FIG. 87, a control syringe-configured push-type or passive inserter with thumb and finger holes that allows the force of insertion to be set by the restorative force of the plunger or plunger-slide return spring with force added by the operator if necessary, and a pistol-configured pull type or active inserter shown in FIG. 89, which allows the operator to control the force of insertion. In FIG. 88, thumb 244, index 232, and third or middle finger 249 rings allows thumb-ring plunger-rod 238 in the push-type to be pulled up as well as depressed, this representing a key object of control-type or finger-ring configured syringes.

Since the stay magazine must queue the stays for contact with the ductus at the same time that clearance must be allowed for the ductus itself, a reversed arrangement of the parts as would give better access to the bottom of the far side of the ductus is ruled out. Using the embodiments shown, reorientation of the insertion tool is limited by the dimensions of the incision normal to the ductus and the attachment of the ductus along its deeper or far side. In the detail of the tool base shown in FIG. 91, the stay insertion tool is applied to the ductus at bottom ribbed arcuate sole 254, which ending in the back at heel 246 and the front at toe 253 must be matched in diameter to the ductus.

Toe 253, sole 254, and heel 246 comprise the front portion or foot 255 of tool base 257 situated to front of barrel 239, while the portion to the rear thereof is butt 256 consisting of tool barrel 239 and recovery and retraction magnet conductor 241. Foot 255 thus rests as substantially stationary upon ductus 1, while butt 256 reciprocates between the downward stroke that retracts stay ejection tongue 247 allowing stay refill strip 250 advancement spring 251 to force down the next stay 231 into stay ejection slot 248, and the upstroke that causes stay 231 to be ejected under the restorative force of thumb rod spring 245.

The surface of insertion tool sole 254 is indented, ribbed, grooved or covered with small dentate or round pillbox projections from toe to heel to stabilize the ductus by nonslidably engaging the stay insertion tool against the surface of ductus 2. Fully circumferential access requires that the ductus be detachable over a sufficient segment and sufficiently torsional or twistable without injury to allow otherwise inaccessible arcs to be implanted. However, attachment at the far side may serve to retract the rear wall of the lumen with only the proximate side requiring retraction by means of a partial stent-jacket. If not and far-side implantation is necessary, the far side will usually be implantable endoluminally by means of a barrel-assembly.

Referring now to FIG. 88, for maximum comfort and minimal disruption at the working end of the tool during use in any embodiment of the control syringe push-type whether switchable between cement-ahead and cement-follower operation, thumb, index, and middle finger rings of the push-type insertion tool are mounted for free rotation such that all three rings can, for example, be rotated by up to 45 degrees clockwise by a right-handed operator or counter-clockwise by a left-handed operator. For minimal interference with viewability, stay retention, recovery, and retraction electromagnet 242 with probe extension 241 are placed at the side that faces away from the ductus or back of the tool.

Allowing sufficient tool length beneath stay retention, recovery, and retraction electromagnet 242 and surgical cement, fluid therapeutic, medication, tissue hardener, or fixative tissue cement/surgical adhesive-sealant refill cartridge 236 in refill cartridge compartment 235 tends to keep the tool extracorporeal, reducing the need for a longer incision to achieve entry to the necessary depth without encroachment upon the edges of the entry wound. FIG. 91 shows butt 256 and foot 255 portions of tool base 257.

Placing the index and middle fingers under finger holes 232 and 249 using the thumb to depress thumb-ring 244 and thumb-ring rod 238 causes compression spring-returned thumb plunger-rod or shaft 238, which slides through plunger sleeve or tool barrel 239 as in a hypodermic syringe, to retract plunger-blade or tongue 247 from ejection slot 248 to a point behind the queue to clear the way for the compression spring to seat the next stay from the queue but with the forward edge of stay ejection tongue or blade 247 remaining inserted within the rearward extension of stay ejection slot 248, which extends the roof sides, and floor of stay ejection slot 248 to the rear.

Stay ejection tongue or blade 247 and stays 231, are ordinarily inflexible, adjustment in the angle of ejection requiring the tool as a whole to be tilted or the use of a tool with a tiltable foot, as addressed below in the section entitled Stay Insertion Tool with Pivoting Base. Stay ejection tongue or blade 247 is made of magnetically conductive (ferromagnetic) spring steel, a polyester coated with flexible ferromagnetic metal, or a polyester interleaved with ferromagnetic bands or laminations of flexible ferromagnetic metal. This allows stay ejection tongue 247 to conduct the magnetic force originating in stay retention, retraction, and recovery electromagnet 242 and passed through magnetic conductor 241 thence stay ejection tongue 247 to ferrous core 230 or alternative internal distribution of ferrous content embedded within stay seen in FIG. 93 as 231.

This allows the use of polarity and current controls 262 mounted at the side of battery compartment 263 shown in FIGS. 87 and 102 to regulate the magnetic force exerted upon stay 231. By adjusting magnet controls 262 mounted to the outside of battery compartment 263, the operator can cause stay ejection tongue or blade 247 to retain, release, or repel stay 231. This allows the operator to confirm that stay 231 has been properly inserted within wall 7 of ductus 1 before proceeding to the next insertion if any. Thus, a stay that is dropped can be recovered and one that enters other than true or normal to ductus 1 can be retracted. The polarity reversing control can be used, for example, to prevent residual magnetism from holding a stay wished released.

The recall magnetic circuit as shown in FIGS. 87, 90, and 91 thus comprehends stay retention, retraction, and recovery electromagnet 242, energizing power source (battery) in battery compartment 263, controls 262, magnetic conductor 241, rivet 258, and stay ejection tongue 247. Stay ejection tongue 247 is fastened at its lower or distal rear end by magnetically conductive (ferromagnetic) rivet 258 to magnetic conductor or probe 241, these parts comprising butt 256. Heel 246 is bonded to the front at the bottom of stationary tool barrel 239, and fixes the ejection path of stay insertion tongue 247. Thumb rod 238 is fastened to and moves or reciprocates battery in battery compartment 263, stay retention, retraction, and recovery electromagnet 242, and magnetic conductor or probe 241 up and down in relation to heel 246 to the fore.

To prevent undesired incisions as could result from involuntary deflection of the tool sideways during insertion, the front corners of plunger-blade or tongue 247 are blunted or rounded. So that the front edge of the plunger-blade (addressed below) engages rather than just abuts upon the back edge of the stay so that separation of the two would leave the stay mispositioned or loose, the plunger-blade is thicker than the stays and v-notched along its front edge to span and encompass the stays. To accommodate this distinction in thickness, the stays are coated with freeze-dried sugar that is absorbed and metabolized shortly after implantation, which process is not significantly impeded by the cement used to seal the entry incision.

This retention within the rear portion of the ejection slot when plunger-blade or tongue 247 is retracted prevents the plunger-blade from becoming disengaged and misdirected from ejection slot 248. The front, back, and sides along the path followed by the stays through the magazine and ejection slot fit flush to the sides of the stays. In order to countersink the near edge of the stay once implanted so that it will come to lie beyond the entry incision through the surface of the ductus sufficient to prevent backup through the same path and allow placement concentric as possible, plunger-blade or tongue 247 extends sufficiently down the side of the ductus and beyond the slight extension of ejection slot 248.

A plunger-blade or tongue 247 shield or guard encloses the exposed portion of plunger-blade or tongue 247 from and thus prevents displacement or pinching of the ductus 1. The plunger-blade or tongue 247 shield or guard is continuous with the floor of ejection slot 248, which is fastened at the bottom to the sides of stay cartridge by ethyl cyanoacrylate, 2-octylcyanoacrylate, n-butyl cyanoacrylate, or a DYMAX Corporation 200-CTH-series cement and thus remains stationary as plunger-blade or tongue 247 moves up and down behind it. Withdrawing plunger-blade or tongue 247 allows stay advancement compression spring 245 to expand inserting the next stay from the magazine load queue to be seated on the floor of the ejection slot lining.

Releasing thumb plunger-rod 238 then causes compression spring 245 to retract plunger-blade or tongue 247 back up through ejection slot 248 ejecting stay 231 out the front end of ejection slot 248. At the forward or exit end, ejection slot 248 beyond the outer surface of the strip or clip of stays 231 omits the floor of the ejection slot but preserves the sides and roof. The side walls and roof of the forward extension of ejection slot lining angle downwards to remain flush to the surface of the ductus. The honed leading edge of the stay thus emerges from the lining in contact with the surface of the ductus, and the stay is prevented from veering aside or upwards before the honed front edge of the stay penetrates ductus 1.

The pistol or pistol grip-configured pull-type insertion tool shown in FIG. 89 has the same stay ejection mechanism as does the control syringe-configured tool shown in FIGS. 90, 91, and 93 but reverses the action of the insertion tool shown in FIG. 87 by using plunger-rod compression spring 245 to return trigger 261 to its forward position, which pulls plunger-blade or tongue 247 up into ejection slot 248 to eject stay 231. Since it would interfere with the descent of the next higher stay in the clip from being advanced (depressed) flush to the bottom of ejection slot 248, plunger-slide (thumb plunger-rod) 238 cannot be slidably engaged against the floor of ejection slot 248 by means of a guideway consisting of either positive or negative side tracks or rails.

Pulling back trigger 261 then draws plunger-blade or tongue 247 past the entry extension of the walls lining ejection slot 248, forcing the next stay 231 in the strip or clip of stays out the front end of stay ejection slot 248. Except for placement of battery 263 in the pistol grip portion and stay retention, retraction, and recovery electromagnet 242, of which the tip of magnetic conductor or probe 241 of stay retention, retraction and recovery electromagnet 242 must remain in contact with butt 256 rivet 258 during movement, the stay insertion mechanism—to include ejection slot 248 entry and exit extensions, stay tissue cement or other therapeutic fluid applicator air pump 264 tissue cement or other therapeutic fluid supply line (cement feed line, outflow line, applicator tube) 260, and end tip—is the same as that described for the control syringe-configured or push-type insertion tool shown in FIGS. 87, 88, and 102.

XVI2. Stay Insertion Tool Inmate Stay Recall (Retraction) and Recovery Electromagnet Because the insertion tool is devised to securely hold and move the stay during the ejection process, mispositioning will more often be due to operator error in choosing the insertion site than to malfunctioning of the tool. To allow a mispositioning stay to be recalled or returned into ejection slot 248 at any point during insertion prior to withdrawal or the insertion tool, the insertion tool is provided with inmate stay retention, retraction, and recovery electromagnet 242. A similar but larger (6 7/16 inches in length) and less specialized battery-powered electromagnetic probe 241 was described by Crawford, W. A. 1976. "Hand-held Electromagnet-probe," *American Mineralogist* 61(1-2):173, available at http://www.minsocam.org/ammin/AM61/AM61_173.pdf.

Depending upon the length of the tool, any outward bowing of the soft iron magnet probe 241 is prevented by restraint to its interface with the tool by means of a longitudinal rail-configured groove tuning along its back side which in assembly is slid over one or two complementary undercut projections, essentially railway track in cross-section, on the probe-facing side of tool barrel 239. Any sticking or excessive friction is prevented by coating these parts with polytetrafluoroethylene or nylon. Stay recovery and retraction probe 241 is not held to the side of tool barrel 239 by strapping it about to avoid an accumulation of debris or the creation of an opportunity for abrasive injury to the margin of the entry wound or other tissue adjacent to such a strap or straps.

Stay insertion tool stay retention, retraction, and recovery electromagnet 242 can be used in either of two ways: a. Normally on, and b. Normally off: Normally on operation consists of applying a steady magnetic field, generally of medium strength, throughout the stay ejection and insertion process. This maintains contact with the stay at every moment leading up to its acceptable placement at which time the current from the battery can be turned off. Maintaining the field up to that point prevents the loss of a stay in the body cavity and the need to locate it, and also makes possible its immediate retraction if it should incise or penetrate the ductus in any manner other than that desired.

At maximum field strength, it is possible to extract the stay even when fully implanted; however, the decision to retract is best made while still in contact with the stay so that it need not be relocated. Since increasing the field strength is accomplished in an instant, maintaining the field strength at extraction level needlessly drains battery 263. Normally off operation consists of energizing stay retention, retraction, and recovery electromagnet 242 as needed to the field stength appropriate, so that a moderate current is used to prevent a stay from dropping and high current used to retrieve a dropped stay or extract a stay that has already been mispositioned.

Battery 263, stay retention, retraction, and recovery electromagnet 242, and soft iron stay retention, retraction, and recovery electromagnet 242 conductor or core and probe 241 are connected to and move with thumb plunger-rod or shaft 238. Except in small sized tools, which use silver wire to generate the same magnetic field force in less space, stay retention, retraction, and recovery electromagnet 242 is wound with copper magnet wire. The armature or core of stay retention, retraction, and recovery electromagnet 242 extends downward (distad) as magnetic conductor or probe 241, connected by ferromagnetic (magnetoconductive) rivet 258 that runs through distal working end or base 257 to connect at its front end to plunger-blade or tongue 247.

As shown in FIGS. 91 and 92, adhesion of stay 231 within the notch in the tip of stay ejection blade 247 and the recovery of a dropped stay or extraction of a stay not properly inserted as shown in FIG. 86 is obtained by manual adjustment of upper control knob 262 shown in FIGS. 87 and 102, which adjusts the current supplied by battery 263 through a variable resistor, and therewith, the magnetomotive force generated, to the field strength required. In an embodiment that uses an embedded microcontroller to adjust the magnetic strength at each phase of the ejection cycle, control of magnetic strength is automated, use of upper knob 262 only required to override the automatic setting as when a stay must be retreived.

Stay retention, retraction, and recovery electromagnet 242 and battery 263 generate sufficient field strength for recovery without the need for a power supply and socket for connection of the same as an alternative power source. When rotated, upper knob 262 adjusts a miniature follower arm potentiometer of a kind obtainable from Placid Industries, Lake Placid, N.Y. that controls the current drawn from battery 263. For control simplicity and to reduce the risk of inadvertent actuation or inactivation of stay recovery and retraction electromagnet 242, rotation of control knob 262 counterclockwise reduces the current down to zero. When not in use battery 263 is simply removed from its socket within the battery 263 compartment.

The instantaneous need to increase the field strength unpredictable, control of stay retention, retraction, and recovery electromagnet 242 is never relegated to automatic operation such as would, for example, shut down the current when stay ejection blade or tongue 247 begins to withdraw back into its slot. To demagnetize the probe, the variable resistor current control is turned all the way down and the polarity momentarily reversed. The stay insertion tool can be used as a hand-held tractive electromagnet to retrieve or portative electromagnet to move any small ferromagnetic object in or out of the body.

Once implantation is complete, even if the insertion tool has not yet been removed, extraction is least injurious by incision and closure with a suitable adhesive, such as butyl 2-cyanoacrylate or, which consists of a single component or Bioglue® Surgical Adhesive (CryoLife, Incorporated, Kennesaw, Ga.), which consists of two components and must therefore be delivered through an auxiliary two—the use of an harmonic scalpel avoided as thrombogenic. Further to allow plunger-blade or tongue 247 to be incorporated into a magnetic circuit that allows stays which have not inserted concentrically (misinserted, mispositioned) to be withdrawn, the parts about the plunger-blade or tongue 247 are formed of nonferromagnetic material, such as the plastic resins specified above.

XVI3. Stay Insertion Tool Inmate Tissue Sealant and/or Medication Delivery Line

The stay insertion tool has a built in exit-coating (inmate tissue sealant and/or medication delivery line (ductus insertion incision and/or ductus-intramural adhesive-sealant delivery mechanism, inmate slit-sealer; inmate adhesive applicator) feature which is usually used to coat surgical cement onto the stays on exiting but can also be used to coat the stays with any kind of medication that can be prepared in a semiliquid or paste-like consistency. As addressed above in the section entitled Stay Insertion Tools, subsection Structure of Stay Insertion Tools, FIG. 87 shows a stay insertion tool with a built in (integral, inmate) adhesive (tissue cement, surgical cement), delivery line. This line can be used to deliver medication or medication mixed into the tissue cement.

Such medication includes antibiotics, antispasmodics, platelet blockers, anticoagulants, anti-inflammatory drugs, and so on. Medication for dispensing upon stay insertion may require the addition of a thickening or gelling agent, such as polysorbate 80 or monoglycerides of saturated or unsaturated higher carbon atom (12 to 20) fatty acids, such as stearic acid, palmitic acid, or oleic acid. Any use of the inmate tissue cement and/or medication delivery line can be coordinated with the dispensing of medication or a sealant from an auxiliary syringe or syringes as introduced above in the section entitled Administration of Target and Target-adjacent Implantation Preparatory Substances and addressed below in the section entitled Powered Stay Insertion Tool Holder for the Attachment of Medication or Tissue Sealant Syringes Whether Single, Dual, or Multi-chambered as Supplied, for Tool Slave-follower or Independent Use.

As described below in the section entitled Mechanism for Switching from Cement-ahead to Cement-follower Operation, the inmate delivery line can be used to coat both or only the upper surface of each stay with cement or medication. As described below in the section below entitled Mechanism for Adjustment in Stay Insertion Tool Ejection Cycle Inmate Cement Delivery Interval, when set to cement-follower operation, the onset of cement or medication discharge can be varied to coat the entire upper surface or only a portion of the trailing end of each stay.

As addressed above in the section entitled Arcuate Stent-stays (Stays, Stent-ribs, Ribs) or Stays for Use with Stent-jackets, stays for such use are usually given a deep surface texture to reduce the amount of adhesive that is wiped or squeegeed away when the stay penetrates the outer surface and moves through the ductus wall. The ability to carry forward a sufficient coating of adhesive ductus-intramurally can make it possible to apply an extraluminal stent even when the pre-test described below in the section entitled In Situ Test upon Endoluminal Approach for Intra- or Inter-laminar Separation (Delamination) reveals a lack of cohesion among the layers of the wall that would otherwise result in separation failure.

For this reason, cement or medication refill cartridge plunger-plug 234 (not to be confused with inmate cement or medication delivery line air pump 264 piston-plunger 233), is of the multiple elastomeric flange kind used in syringes. Piston-plunger 233 is intermittently driven forward under air pressure developed through the reciprocal action of the stay insertion tool, which as explained below, is adapted to provide integral air pump 264 shown in FIGS. 95 and 102. To reduce off-axis deflection and jamming of piston-plunger 233 in its channel, the upper surface of piston-plunger 233 is dished or hollowed out to concentrate the air pressure at the center.

The cartridges are individually sealed in sterile envelope packages and discarded following use. To allow the removal and insertion of adhesive and solvent flush cartridges, tool cap 243 is removable from the upper end of the tool and has an elastomer surround to compression airtight fit. The distal end of tissue cement/surgical adhesive-sealant refill cartridge 236 in refill cartridge compartment 235 is pressed onto and punctured by hollow puncture pin 237, and thumb-ring 244 is depressed until adhesive is brought to the tip of transparent adhesive delivery line 260, which filled is referred to as primed or charged.

Referring now to FIGS. 87, 90, 95, and 102, an inmate sealant (adhesive) application mechanism for sealing the incision through the adventitia produced by insertion of the stay eliminates the need for the alternate insertion and removal of a separate device through the access incision or cannula. With an inmate gluing mechanism, the seal can be accomplished as part of the insertion cycle without the need to relocate each incision. To this end, the reciprocating configuration of these tools lends themselves to the operation of air pump 264, which allows the elimination of numerous mechanical parts.

The ductus entry incision sealing mechanism consists of surgical cement, fluid therapeutic, medication, tissue hardener, or fixative tissue cement/surgical adhesive-sealant refill cartridge 236 in refill cartridge compartment 235, which accepts disposable surgical adhesive-sealant refill cartridges 236 in refill cartridge compartment 235. To allow air pump 266 to draw air without vacuuming cement back up through line 260, reciprocating air pump 266, seen as the upper portion of inmate tissue cement refill cartridge compartment 264 incorporates one-way or unidirectional air valve 265.

Air pump 266 comprises piston-plunger 233, connected to thumb plunger-rod 238 by tissue cement air pump piston arm or handle 267 that passes through a longitudinal slot in the side of the tool barrel 239, and adhesive delivery line or tube 260, which extends from cartridge puncture pin 237 to a forward extension overlying ejection slot 248. Sealing of the incision is completed by lightly pressing down on the insertion tool to tamp down the incision. Since the stays are significantly countersunk by the plunger-blade or tongue 247, which is longer, this may require cocking or inclining the tool forward or axially rotating it full circle to the opposite side of the ductus.

To function as a bellows-type air pump 266 without an air bladder, the longitudinal slot must be airtight. This is accomplished by molding air pump piston arm or handle 267 as integral with, and centered in as to appear to pass transversely through, a sliding cover 268, which extends up and down by half the length of the slot when air pump piston arm or handle 267 is positioned half way up or down the slot, and which is convex to the side facing pump 266 to flush fit against the inside of tube barrel 239. Since the sliding cover is twice as long as the slot, it will obturate all of the slot whether the arm is all the way up or down.

Figure 95:
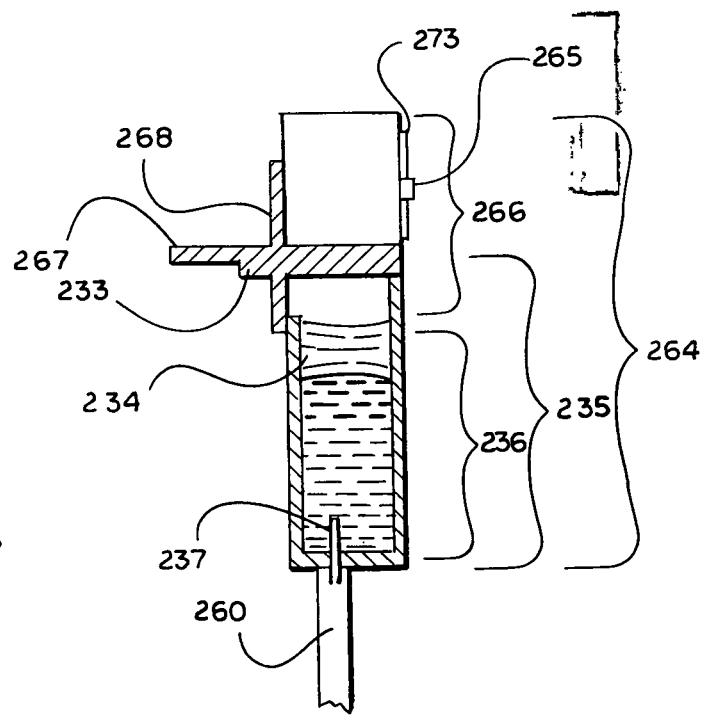
FIG. 95 shows a detailed section view of the sliding hole pressure relief mechanism used to reverse the direction of the starting height at which the cement or medication chamber pressurization piston in a stay insertion tool exerts air pressure on the column of cement or medication in the cement refill cartridge, thus initiating ejection of the cement or medication.

More specifically, as seen in FIG. 95, to prevent air from escaping through the slot along which tool cement chamber air pump 264 piston arm or handle 267 moves up and down, air pump piston arm or handle 267 has shorter airtight extensions at either side, an upward extension that is long enough to cover the upper portion of the slot when the piston is at its lowest position along the slot, and a downward extension that is long enough to cover the lower portion of the slot when air pump 264 piston-plunger 233 is at its highest position along the slot. Air pump piston arm or handle 267 passes through or is molded as integral with slot cover 268. These extension thus constitute a sliding slot cover with integral piston handle.

For low friction and strength, sliding cover and air pump piston arm or handle 267 is molded in one piece of nylon or a polymer especially formulated to make bearings, such as Iglide® or Drylin® polymer (not to be confused with the antibiotic of the same name) obtainable from Igus® Incorporated, East Providence, R.I. Sliding cover 268 is maintained in a straight up and down path and held flush to the internal wall of tool barrel 239 so that air is prevented from moving through the underlying slot by a strong and low friction nylon or Iglide® polymer frame that overfolds the edges of sliding cover 268 and serves as a slide-way.

The extension upward and downward from plunger-rod 239 to cement air pump piston 233 arm or handle 267, which is vertically centered on the outer surface (surface flush to the internal surface of tool barrel 239) of sliding cover 268 also serves to prevent air pump piston arm or handle 267 from deflecting or yielding to moment loads that would take piston arm out of perpendicularity with the central axis of the tool either vertically or horizontally. In a stay insertion tool capable only of cement-ahead operation, air pump piston arm or handle 267 is directly connected to thumb plunger-rod 238.

In embodiments that are capable of switching from cement-ahead to cement-follower operation, connection of the communicating arm with the thumb plunger-rod 238 is not direct but mediated through sprocket chain 252 that allows the direction up or down of the inmate cement air pump 264 piston-plunger 233 to be reversed according to which side of the sprocket chain 252 that pins extending from the plunger-rod 238 are made to engage. Then cement air pump 264 piston arm or handle 267 is connected through tool barrel 239 to sprocket chain 252 used to move air pump piston-plunger 233 up and down. The operator determines which side by twisting thumb-ring 244 one way or the other.

As described below in the section entitled Mechanism for Adjustment in Stay Insertion Tool Ejection Cycle Inmate Cement Delivery Interval, to set the height at which air can no longer escape from inmate cement air pump 266 upper portion of cement refill cartridge compartment 264, stay insertion tools capable of cement-follower operation are also equipped with a second slot and sliding cover. As an adjustable pressure relief valve, this second slot is airtight only when air pump 264 piston-plunger 233 approaches within the distance from the top of tissue cement/surgical adhesive-sealant refill cartridge 236 in refill cartridge compartment 235 at which the upper edge of the sliding cover has been set to cut off the escape of air thereby initiating pressurization against the refill cartridge refill plug plunger.

The substantially constant temperature and humidity in the catheter laboratory obviate the need for compensation in the air pump 264 mechanism. One-way air valve 265 admits a volume of air into air pump 266 upper portion of cement refill cartridge compartment 264, the pressure pushing down against air pump 264 piston-plunger 233, forcing refill cartridge 236 plunger-plug 234 downward incrementally with each additional incremental volume of air. This causes adhesive-sealant or medication refill cartridge air pump 264 piston-plunger 233 to expel adhesive-sealant within refill cartridge 236 down delivery tube 260 to the point of emission poised or positioned just above ejection slot forward extension 269 in FIG. 90, causing each stay 231 to be coated with adhesive upon ejection.

One-way air valve 265 not only serves to keep the pump airtight during the downstroke but allows piston 233 to freely return under the force of plunger-rod spring 245 to its elevated starting position without resistance due to a vacuum created by the occlusion of tissue cement supply line by cement. Purging of line 260 by means of flushing by connection to a syringe or cleaning cartridge containing a solvent is addressed in the sections above entitled Stays Coated with a Heat-activated (-melted, -denatured) Tissue Adhesive-Hardener, or Binder-Fixative and that below entitled Use of Stay Insertion Tool.

Provided its dimensions allow, attachment alongside the stay insertion tool of an electrical cautery or harmonic scalpel by attachment with the clips addressed below in the section entitled Binding of Lines and Cables Alongside the Stay Insertion Tool is practicable, as is the attachment of a laser, lamp, or endoscope, the number of auxiliary cabled devices limited by the size of the entry portal. Unnecessary complexity is eliminated by allowing the direction of the air pump 264 piston-plunger 233 to move integrally with thumb plunger-rod 238 rather than to be reversed by alternative means such as gears, rack, ratchet, or levers, much less an electromechanical actuator.

With cement-ahead operation, the tissue cement or other fluid therapeutic substance within refill cartridge 236 is thus caused to discharge during the loading phase of the ejection cycle when the next stay 231 is seated in ejection slot 248 rather than during the ejection phase of the tool reciprocating action cycle. Any excess adhesive applied to the stays is then skimmed or squeegeed away by the upper lip of the ductus entry incision where it is easily wiped away if thought consequential or otherwise desired. Backward displacement of air pump 264 piston-plunger 233 during the stay insertion portion of the cycle exhausts air behind air pump 264 piston-plunger 233 through pressure equalization or exhaust one-way valve 235 while drawing air through one-way air valve 265.

As shown in FIGS. 87, 95 and 99, the insertion tool inmate adhesive delivery mechanism consists of integral air pump 264, chamber for the insertion of adhesive cartridges as described, and a path for the delivery to the stays upon implantation of adhesive. As shown in FIG. 90, tissue cement within refill cartridge 236 passes through puncture pin 237 and down cement delivery (supply, feed) line or tube 260 to its distal terminus 269, overhanging the outlet of ejection slot 248.

Fastened along the front of the tool by means of an adhesive, cement delivery (supply, feed) line or tube 260 is made of any suitable polymer tubing and continues from adhesive puncture pin 237 over the top of stay refill strip compartment 250, down past the front of stay advancement compression spring 251 thence down the front of stay refill strip compartment 250, where it reaches down to overhang stay ejection slot 248 as overhang extension shown as 269 in FIG. 90. Shown in detail in FIG. 87 in the enlarged inset at the bottom and FIG. 90, which provides a further enlarged view, the distal tip or adhesive emitting end of adhesive delivery tube 260 is aligned to and overhangs ejection slot 248 front extension and in position to coat the upper surface of each stay with adhesive as each is ejected.

Forward displacement of air pump 264 piston-plunger 233 in the stay seating portion of the cycle then forces the air trapped in air-tight refill cartridge compartment 264 in FIG. 95 between the front of air pump 264 piston-plunger 233 and the surface of adhesive cement or medication refill cartridge 236 plunger-plug 234 against tissue cement air pump plunger-piston 233 driving tissue cement refill cartridge plunger-plug 234 farther down into surgical cement, fluid therapeutic, medication, tissue hardener, or fixative refill cartridge compartment 235 causing the equivalent volume of tissue cement in refill cartridge 236 through adhesive delivery line 260 and through ejection slot 248 overhanging outlet tip 269.

Each time air pump 264 piston 233 is retracted, an additional volume amount of air is introduced through one-way air valve 265 into air pump 266 upper portion of inmate tissue cement compartment 264. Thus, air pump 264 piston-plunger 233 is incrementally driven forward by an equivalent distance for each volume of air added to the air column trapped in air pump 264. Access to the battery 263, adhesive-sealant cartridge, and stay refill chambers, of which the interiors are contoured to conform to and thus secure the refills, is through side entry snap covers of the kind used to cover the compartment used to contain the replaceable battery in the back of a pocket calculator, that for the adhesive cartridge (not shown) requiring to be airtight.

XVI4. Sealing of Stay Insertion Incisions

Studies of the efficacy of cyanoacrylate cements for tissue-tissue and tissue-implant bonding can disagree, such studies mostly limited to a specific application of a specific cyanoacrylate cement, with none related to the repair contemplated herein (see, for example, Halli, R., Joshi, A., Kini, Y., Kharkar, V., and Hebbale, M. 2012. "Retrospective Analysis of Sutureless Skin Closure in Cleft Lip Repair," *Journal of Craniofacial Surgery* 23(1):e40-44; Fortelny, R. H., Petter-Puchner, A. H., Walder, N., Mittermayr, R., Ohlinger, W., Heinze, A., and Redl, H. 2007. "Cyanoacrylate Tissue Sealant Impairs Tissue Integration of Macroporous Mesh in Experimental Hernia Repair," *Surgical Endoscopy* 21(10):1781-1785; Paajanen, H., Kossi, J., Silvasti, S., Hulmi, T., and Hakala, T. 2011. "Randomized Clinical Trial of Tissue Glue Versus Absorbable Sutures for Mesh Fixation in Local Anaesthetic Lichtenstein Hernia Repair," *British Journal of Surgery* 98(9):1245-1251; Testini, M., Lissidini, G., Poli, E., Gurrado, A., Lardo, D., and Piccinni, G. 2010. "A Single-surgeon Randomized Trial Comparing Sutures, N-butyl-2-cyanoacrylate and Human Fibrin Glue for Mesh Fixation during Primary Inguinal Hernia Repair," *Canadian Journal of Surgery* 53(3):155-160; Dilege, E., Deveci, U., Erbil, Y., Dinççağ, A., Seven, R., Ozarmagan, S., Mercan, S., and Barbaros, U. 2010. "N-butyl Cyanoacrylate Versus Conventional Suturing for Fixation of Meshes in an Incisional Hernia Model," *Journal of Investigative Surgery* 23(5):262-266). Accordingly, reference to the sealing of stay incisions with a cyanoacrylate cement rather than a fibrin tissue adhesive, for example, is exemplary.

Reviews of the different type adhesives are, however available (see, for example, Duarte, A. P., Coelho, J. F., Bordado, J. C., Cidade, M. T., and Gil, M. H. 2011. "Surgical Adhesives: Systematic Review of the Main Types and Development Forecast," *Progress in Polymer Science* Published online by Elsevier, December 2011; Peng, H. T. and Pang, N. S. 2010. "Novel Wound Sealants: Biomaterials and Applications," *Expert Reviews* 7 5): 639-659; Ryou, M. and Thompson, C. C. 2006. "Tissue Adhesives: A Review," *Techniques in Gastrointestinal Endoscopy* 8(1):33-37).

When a tissue adhesive-hardener refill cartridge is inserted into the bottom of inmate cement air pump 264, in FIGS. 95 and 102 the stay insertion tool applies a fluid adhesive, such as Ethicon Omnex™ cyanoacrylate surgical sealant, in cement-ahead operation, to the outer surface of the ductus before each stay is ejected, or in cement-follower operation, to a variable length along the upper surface of each stay as it exits the insertion tool ejection slot. The means for varying the moment of onset for cement or medication discharge when the tool is set to cement-follower operation is described below in the section entitled Mechanism for Adjustment in Stay Insertion Tool Ejection Cycle Inmate Cement Delivery Interval.

The adhesive is used to a. Quickly seal the incision made by the stay as it passes through the outer surface of and into the ductus, or the stay insertion incision, and in conjunction with an encapsulating solid collagen and/or albumin solder adhesive-tissue hardener that jackets about stays configured thus and remains solid at room temperature but flows (melts, denatures) when heated, b. Securely bond the stay between the layers embedding it within the lumen wall and thus reduce the possibility for 1. Intra- or inter-laminar separation within the wall of the ductus as would draw the stay and layers radially outward to the stay toward the bar magnets about the stent-jacket leaving the lumen unaffected, or in a nonferromagnetic stay that is not kept under outward radial tractive force, such as a medication stay, 2. Gradual migration through penetration adaxially (toward the long axis lumen, inward) as could eventually lead to intimal perforation if not the entry of a stay into the lumen before the stay became completely absorbed.

The risk for a stay to penetrate into the lumen as the result of an accidental blow (rather than the intrinsic motility in the wall of the ductus) varies inversely as the quantity of tissue intervening between the stays and the exterior. The solid protein solder is formulated as a cool melt to flow at a temperature lower than would injure the surrounding tissue. For consistency with and familiarity to the prior art, the solder can be applied to pores within a thin membranous coating of an absorbable polymer about the stay that can release medication as it is absorbed, for example. Applied as indicated, the exothermy of polymerization and vapor of cyanoacrylate cement are considered insignificant.

XVI4a. Cement-Before Insertion (Cement-Ahead Operation)

Cement-ahead operation is the coating of the ductus to be stayed with cement just before the stay is ejected through the cement into the wall of the ductus. To reduce run-away, cements and medication for such use should be thicker or incrassated and viscid. The stay thus carries forward cement into the ductus. The apparatus to be described incorporates mechanical means for applying cement or any other fluid substance such as medication via the inmate tissue cement delivery line. Cement-ahead operation with an attached or auxiliary syringe is achieved by adjusting the timing of auxiliary syringe discharge relative to the stay ejection cycle of the tool.

The wiping away or squeegee effect of the top and bottom surfaces of the stay as it sweeps past the edges of its adventitial incision or stay insertion incision as it enters the ductus can be lessened by using implants that have indentations, ribs, or grooves and a textured surface that retains and carry forward adhesive. This is especially advantageous in cement-ahead or cement-before insertion operation whereby surgical cement is expelled onto the surface of the ductus just prior to passing the stay through the adventitia to carry some of the cement forward into the ductus wall thus reducing the risk of laminar separation under the tractive force exerted by a magnetic stent-jacket.

Preliminary tests for quantifying a ductus-intramural propensity for laminar separation are described below for both endoluminal (miniball, ballistic) and extraluminal (stay) approach. Such surfacing also allows increased uptake of adhesive and the quicker transmission of heat, which is used, for example, to denature or melt a coating of solid solder adhesive-hardener used when the wall of the ductus is found by one of the test to be described as internally weakened. The preparation of anticoagulants in lyophilized (freeze-dried) form, to include heparin salts such as heparin lithium, the lithium salt of heparinic acid prepared using ion-exchange technology from heparin sodium, has long been practiced for preserving blood (see, for example, Shimizu, A. and Ichikawa, T. 1986. "Blood Collector," U.S. Pat. No. 4,595,021).

Lyophilized warfarin sodium is sold as a powder for intravenous injection following reconstitution. Whether the more proximate placement of miniballs obtained using machine controlled discharge imparts a weakening of the intima and media as disposes toward aneurysmal failure requires study; if so, then the stent-jacket should be placed in position prior to initiating discharge, just as it should when aneurysm looms for any reason. Because the stent-jacket is compliant and the distance slight, that the magnets act in a bistable way as to abruptly seize or 'yank' a ferromagnetic object when the field strength meets a certain value does not mean that an extraluminal stent interferes with the normal motility intrinsic in the ductus wall.

Essentially, the lumen wall is drawn little, or if previously occlusive tissue has been ablated, no farther outward than in normal function and under less and less rapidly changing force, so that the risks of the media if not the adventitia in which the miniballs have been implanted intra- or inter-laminarly separating (delaminating) and of stretching injury are slight. To be certain that the normal relaxed or quiescent diameter of the ductus plus any additional diameter that may be needed to achieve luminal patency over the affected segment is not significantly exceeded by the internal diameter of the stent-jacket to be applied, the ductus should be measured with a caliper and the reading matched to the internal diameter specified on the stent-jacket package.

Slightly additional retraction to a larger diameter of the ductus may sometimes be necessary, but if not kept to the minimum, will begin to undo the advantage over a nonendoluminal stent of avoiding interference with the normal function of the smooth muscle. If the ductus is only temporarily swollen, a stent-jacket with an expansion insert is used, as described in the section below entitled Expansion inserts for Tme-discrete Decremental contraction of stent-jackets, comminutable and Meltable. Nevertheless, in basic contrast with endoluminal stents, the extraluminal stent will be more compliant with the intrinsic motility or involuntary smooth muscle action passing through the wall of the substrate ductus.

Even when a stenotic condition necessitates retraction to a wider diameter, a magnetic stent-jacket will yield, albeit with increased circumferential resistance, to the further expansion of the ductus, that is, even when owing to the greater magnetic field strength required, compliance must be somewhat reduced. Circumferential compliance will be somewhat reduced when the use of a stent-jacket with expansion insert has incorporated more powerful magnets. Unless the internal surface of the stent-jacket presents much friction or the magnets used are strong, the circumferential mobility of the diffuse outer adventitia and the lesser resistance of a magnetic field to sidewise deflection should afford some compliance.

Absent extenuating circumstances, such as the presence of a tacky exudate, extravasated blood, or the like, a nonmagnetic stent-jacket, especially when the internal surface of the base-tube is low in friction and without a lining as would resist circumferential displacement or a sliding relation between the adventitia and internal surface of the base-tube at their interface can usually move with the walls of the lumen. From the moment of insertion, the extraluminal stent is immediately and instantly compliant in a way that a slowly and limitedly shape adaptive nitinol stent cannot approach.

Between its longitudinal bars of neodymium lanthanoid, of which each can be magnetized parallel to their thickness to provide more than one pole directed radially towards the central axis of the lumen, the base tubing of an extraluminal stent-jacket can be slitted, perforated, or slotted to enhance compliance with smooth muscle action, and perforation or slotting will also serve to expose the outer surface of the ductus to its normal chemical environment. Small, delimited, and distantly spaced punctures of the internal elastic lamina do not represent injury equivalent to the running dissection of a vessel as the result of balloon overinflation which can lead to shrinkage, intimal hyperplasia, and restenosis, and is certainly not equivalent to rupture. Stress relief afforded by an extraluminal stent (see Berry, et al. 2002, cited above) is not approachable by an intraluminal stent.

In contrast to this least initial trauma of endoluminal stents, the extraluminal stenting to be described requires not only transluminal access to place an intraductal component subadventitially, but extraductal entry through a separate incision or entry wound to allow permural access for placement of an extraductal component, or stent-jacket. The intraductal component consists of miniature ferromagnetic balls that implanted ballistically, produce some tearing and bruising that can result in inflammation, which is, however, medically manageable and short lived. The detailed responses of the lumen wall to ballistic implantation of internal origin are distinct from the form of injury, edematous swelling, and ensuing inflammation that are seen following injury to tissue exposed to the environment where dermal and muscle cells are crushed in depth and many tiny vessels torn.

Except where percutaneous access is unavoidable using conventional means as in the ureters, this situates extraluminal stenting on the trauma scale as intermediate between intraluminal stenting and open surgery. Essentially, conventional or intraluminal stenting trades initial placement with relatively little trauma but the probability of complications that will increase in severity over time for short-term inflammation as the result of some cell-crushing, tearing and bruising, edematous swelling, in larger vessels, some vasa vasorum bleeding, and the need for an arteriotomy to place the stent-jacket, but thereafter, as with high-quality dental restorations, relative freedom from long-term complications.

In fact, just as might the methods described herein, conventional methods occasionally result in unpredictable injury and adverse sequelae, no procedure known being capable of avoiding this prospect. Since medical surveillance is close while the patient is still in the hospital and immediately following discharge, the earlier unavoidable sequelae appear, the more will there be the opportunity for successful management. In addition to the administration of a systemic platelet blocker or anticoagulant, miniballs may have to be wetted or coated with such medication; however, continued irritation from an endoluminal stent will not follow, so that such medication can soon be discontinued.

Introduced from outside the vessel, stays avoid the lumen entirely, making platelet blockade or an anticoagulant unnecessary. In blood vessels, the introduction of multiple punctures into the media is more thrombogenic than are an angioplasty and the insertion of an endoluminal stent. The apparatus and methods described herein are applicable to ductus other than vascular, but the risk of thrombogenesis pertains to blood vessels. Nevertheless, when access to the outer surface of an artery would necessitate much dissection or the extension of disease does not permit using the slower process of inserting stays, miniballs are implanted quickly with a barrel-assembly.

This applies whether the implants are to remain permanently or temporarily; it is necessary to distinguish between the extraction and the complete removal from the body of implants. As noted above, the apparatus allows the use of radioactive implants on a temporary basis. These must not merely be extracted from the implantation site but removed from the body entirely. The same may apply to erroneously placed medication miniballs.

XVI4b. Sealant Cartridges and Sealants (Adhesives)

This section will address adhesive or sealant cartridges for insertion into stay insertion tools. An auxiliary adapter for attaching an additional commercial dual or other multichamber (multicompartmental) syringe alongside the tool is described below in the section entitled Powered Stay Insertion Tool Holder for the Attachment of Medication or Tissue Sealant Syringes Whether Single, Dual, or Multi-chambered as Supplied for Tool Slave-follower or Independent Use. As shown in FIG. 87, the disposable refill cartridges or capsules 236 combine features of disposable hypodermic syringes, refill tubes used in caulking and greasing guns, and airgun $CO_2$ canisters (cartridges, 'pistolets,' 'powerlets').

Cement refill cartridges 236 are essentially shortened and miniaturized caulk tubes that are punctured at the outflow end by means of hollow hypodermic type needle type puncture pin or needle 237 fixed in position at the bottom or distal end of the adhesive refill chamber. FIG. 87 shows a single glue column for a single-component adhesive, which pending the availability of fully absorbed cyanoacrylate-based cements, is preferably octyl-cyanoacrylate or N-butyl-2-cyanoacrylate cement, if not a longer chain acrylate cement. Long-chain cyanoacrylate cements have the advantages of consisting of a single component, which makes the use of the single puncture needle 237 possible and providing significantly greater bond strength than any other type of adhesive.

XVI4c. Mechanism for Adjustment in Stay Insertion Tool Ejection Cycle Inmate Cement Delivery Interval The initiation and duration or interval in the stay ejection cycle during which the adhesive is ejected can be adjusted to coat only the trailing end of each stay, so that only the incision through which the stay entered the ductus will receive glue, or to coat the entire upper (convex) surface of each stay as it is ejected from the insertion tool. The latter is used when it will serve the better to bond the stay and the layers embedding it together or when the heat to denature a solid protein solder would best be avoided, except that owing to a propensity toward separation among the layers in the ductus wall, additional cyanoacrylate cement is essential to compensate for this omission.

In connection with adjustment in the interval and timing of sealant ejection relative to magnetic stent stay ejection and cement-follower operation, the fact that the adhesive has not set when the stent-jacket is later placed is inconsequential. Adhesives that set before the stent-jacket can be placed should not be permitted to present a protrusive contour, however. For this reason, quick-setting adhesives should routinely be smoothed flush to the adventitial surface while still fluid. The same applies to the use of any adhesive, such as one applied with the aid of an auxiliary syringe as is described below. Turning now to FIG. 95, one-way or check air intake valve 265 will allow air to move only into adhesive air pump 266 in the upper portion of cement refill cartridge compartment 264 when cement or medication air pump piston-plunger 233 ascends.

Unless it is preferred to use air pump 266 piston 233 as a one-way intake valve that allows blow-by about its periphery upon ascending analogous to the unidirectional compression seen in a bicycle tire air pump piston, the fit within adhesive air pump cylinder constituting the portion of compartment 266 beneath cement piston plunger 233 of cement or medication air pump piston-plunger 233 is airtight. When the operator pushes down on thumb-ring 244, air pump piston-plunger 233 is pushed down, causing the pressure built up in adhesive air pump cylinder constituting compartment 266 beneath cement piston plunger 233 to be channeled through cement refill cartridge puncture pin 237 forcing adhesive or other fluid 236 down tissue cement or therapeutic fluid delivery line 260 and out at its lower end overhang 269 just above stay ejection slot 248.

Thus, to coat a stay over its upper surface, one-way air intake valve 265 is closed throughout the pressurized downstroke of the stay loading phase or stroke of the ejection cycle and open on the spring-return of air pump piston-plunger 233 during the upstroke or ejection phase of the cycle. Still referring to FIG. 95, the excursion (stroke, displacement) of pump piston 233 fixed as part of the ejection mechanism, the cement delivery interval is made adjustable by placing the aperture of one-way air intake valve 265 at the center of A vertically oriented sliding panel or slot cover 273. To prevent air from leaking out of the pump 266 compartment while the volume is adjusted, sliding panel or slot cover 273 has upward and downward extensions that cover over portions of the slot that would otherwise be open to the outside.

Sliding slot cover 273 is mounted on the outside of the upper portion of tissue cement refill cartridge compartment 264 air pump 266 so as to slide up and down along a vertical way. Sliding extensions 268 of pump piston 233 and one-way air intake valve 265 function independently and cannot be combined, a valve positioned thus inaccessible to the operator or outside air. One-way air intake valve 265 hole-slide 273 moves over a vertical slot in the side wall of adhesive air pump cylinder 266 and thus prevents any buildup of pressure against the top of surgical cement, fluid therapeutic, medication, tissue hardener, or fixative cement plunger plug 234 until air pump piston-plunger 233 has descended alongside the hole to cover it over, at which level the air within the cylinder begins to be compressed as piston-plunger 233 and tissue cement refill cartridge plunger-plug 234 continues to travel downwards.

The moment of onset and duration within the insertion tool cycle that pressure is applied to surgical cement, fluid therapeutic, medication, tissue hardener, or fixative refill cartridge compartment 235 piston-plug 234 and adhesive continues to be ejected can thus be varied according to how high up the side wall of inmate cement air pump cylinder or compartment 266 side hole 265 is slid. As other sliding controls herein to include that incorporated into the valve body of airguns, one-way air valve 265 in vertically oriented sliding panel or slot cover 273 is calibrated or graduated to allow precisely repeatable settings.

An isolated hole for the purpose of coating only the trailing end of each stay as it ejected through ejection slot 248 would require inordinate precision increasing the cost to provide the tool, whereas incorporating a slidable cover over a much elongated hole or slot contributes not only 'trimmer' adjustability for such use but equally important, allows the extent of the upper surface of each stay to receive adhesive to be varied. Accordingly, slidable slot cover 273 is similar in conformation to that incorporated into the valve body of the airgun for adjusting the exit velocity seen in FIG. 47 but smaller.

The airtight sliding slot cover is oriented so that the slot is progressively covered (obturated) moving upwards, in which case only the rear tip of each stay will receive cement. By continuing to move air valve 265 in vertically oriented sliding panel or slot cover 273 upwards, the length of piston stroke downward through cement air pump or air pressure cylinder 266 until the piston covers the side opening to prevent the escape of air is reduced, thus initiating the imposition of pressure on puncture pin 237 earlier in the insertion tool ejection cycle.

The cement is thus caused to cover each stay as it is ejected beginning at a distance along the stay that is at or more closely toward its forward (leading, incisive) end. Pushing down the sliding slot cover reduces the adhesive ejection portion of the stoke. When pushed all the way down, the ejection of adhesive is limited to the trailing tip of each stay. To avoid the use of an adhesive entirely, the adhesive cartridge is not inserted into the tool or is removed at the point in the procedure where the use of adhesive is no longer desired.

XVI4d. Control Over the Quantity of Fluid Discharged

The mechanism described above for adjusting the length of the stroke from the bottom up to the point along the chamber where the sliding hole one way intake and exhaust air valve 265 is placed to initiate pressurization and the discharge of contents from the chamber when the piston descends past this point not only satisfies the requirement for a volume or quantity control, but effects discharge with the timing preferred. Specifically, in cement-ahead operation, during which the cement or medication is emitted during the downstroke of thumb plunger-rod 238, to make the quantity of substance emitted dependent upon the height of the closing segment of the stroke results in the less than full stroke amount of cement or medication being delivered toward the end of the stroke minimizing run-away.

In cement-follower operation, during which the cement or medication is emitted during the return of thumb plunger-rod 238 to its undepressed or starting position, setting the initiation of pressurization closer and closer to the end of the stroke results in the deposition of cement or medication in correspondingly smaller and smaller amounts and closer and closer to the trailing tip of the stay. Set to the lowest point, the least cement or medication will be deposited to seal the insertion incision made by the stay upon entering the ductus. Since the trailing tip will be the primary if not the only target for the deposition of cement, that in cement-ahead operation the mechanism cannot deposit cement farther ahead onto the upper surface of the stay while omitting cement at the trailing tip is not disadvantageous. There would appear never to be a reason for coating only portions of the stay ahead of the trailing tip.

XVI4e. Mechanism for Switching from Cement-Ahead to Cement-Follower Operation

Referring now to FIGS. 97 thru 99, in a stay insertion tool embodiment that is capable only of cement-ahead or cement-follower operation but not switchable between the two, air pump piston arm or handle 267 of stay insertion tool inmate sealant or medication delivery system air pump piston-plunger 233 is directly connected to thumb plunger-rod 238 with the piston starting position at the top of the cylinder (cement chamber) so that cement is emitted on the downstrokes before stay ejection or on the spring returned upstrokes during ejection respectively. In an embodiment that allows switching between these two modes of operation, the piston starting position is midway along the stroke.

Still referring to FIGS. 97 thru 99, the ability to switch between cement-ahead and cement-follower operation is obtained through the interposition between thumb plunger-rod 238 and air pump piston-plunger 233 of a direction-reversing rope ladder-configured sprocket chain 252 made of a tough and inflexible bearing polymer, such as polyoxymethylene homo (DuPont Delrin®) or copolymer (Korea Engineering Plastics Company Kepital®, Celanese Corporation Celcon® and Hostaform®, or Mitsubishi Engineering-Plastics Lupital®, engineering grade polyacetal resins available from many firms under many tradenames) which determines whether depressing thumb plunger-rod 238 will drive air pump piston-plunger 233 upwards or downwards. Inmate tissue cement air pump 266 piston 233, shown in detail in FIG. 95 and in situ in FIGS. 87 and 102, is permanently fastened to one run of sprocket chain 252 by air pump piston arm or handle 267.

Connection of sprocket chain 252 to thumb plunger-rod 238 is by sprocket chain engagement arm 272, such that rotating thumb-ring 244 with thumb plunger-rod 238 and sprocket chain engagement arm 272 through 360 degrees rotates sprocket engagement arm 272 to engage the opposite run of sprocket chain 252, so that inmate tissue cement air pump piston 233 is raised or lowered accordingly, whereas rotating thumb-ring 244 180 degrees to the center position disengages thumb plunger-rod 238 from sprocket chain 252, disabling inmate tissue cement air pump 264. Sprocket chain or belt engagement arm 272 is permanently fastened to, and therefore rises, descends, and rotates with thumb-ring 244 and thumb plunger-rod 238.

Shown in FIGS. 96 and 97, sprocket chain engagement arm 272 engages sprocket chain 252 at either end of a tee or perpendicular cross-piece at its distal end, or that end facing sprocket chain 252, only when thumb-ring 244 and thumb plunger-rod 238 are fully rotated either clockwise or counterclockwise, the pointed ends of the cross-piece then fitting into spaces separating consecutive rungs in sprocket chain 252. Unless engaged by rotation of thumb-ring 244 and thumb plunger-rod 238, sprocket to air pump piston 233 arm or handle 267 and sprocket chain 252 remain motionless, inmate stay tissue cement coating air pump then disconnected from thumb plunger-rod 238 and therefore disabled.

Sprocket chain engagement arm 272 with distal tee cross-piece is preferably machined, cast, or die-cut in one piece. Alternatively, the end tee cross-piece can be a hard fine rod or wire passed through or fastened toward or at the distal end of arm 272. Rotating thumb-ring 244 and thumb-rod 238 clockwise or counterclockwise through 360 degrees thus rotates sprocket chain engagement arm 272 so that it engages switches engagement of arm 272 between the oppositely directed runs of sprocket chain 252, thus driving sprocket chain 252 either up or down and reversing the direction of inmate tissue cement air pump piston 233.

Thus, the operator determines whether the direction of air pump piston-plunger 233 will be upwards or downwards by rotating thumb-ring 244 beyond its freely rotated arc to either side (clockwise or counterwise), and in so doing, determines which side of sprocket chain 252 will be engaged and driven downward by thumb plunger-rod 238, by intromission into the right or left sprocket run of either the right or left tip of the upper cross-piece of tee-configured sprocket belt engagement arm 272 that extends from thumb plunger-rod 238. To this end, air pump piston 233 arm or handle 267 is permanently fastened to one side of sprocket chain 252, this junction being inflexible and the run of sprocket chain 252 used centered on air pump piston 233 arm or handle 267.

Unless the tool is unusually long, thumb plunger-rod 238 remains centered within tool barrel 239 by its connections above and below. If necessary, intervening spacing washers or ferrules bonded about their circumference to the internal surface of tool barrel 239 are used to center thumb plunger-rod 238. Upper sprocket wheel 270 and lower sprocket wheel 271 are made of a strong and low friction polymer used to make bearings, such as Iglide® or Drylin,® obtainable from Igus® Incorporated, East Providence, R.I. or nylon. Sliding air valve 265 sliding panel or slot cover 273 as such is identical to that used in an embodiment which is incapable of switching between cement-ahead and cement follower operation.

However, air pump piston arm or handle 267 is not attached directly to thumb plunger-rod 238 but instead fastened to sprocket chain 252, which can be engaged by thumb plunger-rod 238 on its run at either side. Relating this action to switching between cement or following operation, the rotational angles of the two detent ridges beyond the ends of the free rotation of thumb-ring 244 are the same as the angles at which either side-looking point facing out from the end of sprocket chain communicating arm 272 engages the run of sprocket chain 252 to either side.

As indicated, rotating thumb-ring 244 clockwise as seen from above thus rotates thumb plunger-rod 238 and air pump piston arm or handle 267 causing the right-hand extension of piston arm 267 to engage the right-hand run of sprocket chain 252, which moving in the same direction as thumb plunger-rod 238 causes cement air pump piston-plunger 233 to descend in cement-ahead mode. Rotating thumb-ring 244 in the opposite direction causes air pump piston arm 267 to engage the rising run of sprocket chain 252 so that thumb plunger-rod 238 and air pump piston-plunger 233 move in opposite directions in cement-follow mode.

That is, when the side or run of sprocket chain 252, to which piston arm 267 is permanently fastened, is engaged by either side-looking point facing out from the end of sprocket chain communicating arm 272, which is permanently fastened to thumb plunger-rod 238, downstroke of thumb plunger-rod 238 moves air pump piston-plunger 233 downwards, resulting in cement-ahead operation. When either side-looking point facing out from the end of sprocket chain communicating arm 272 engages the sprocket chain 252 at the other side, downstroke of thumb plunger-rod 238 moves air pump piston-plunger 233 upwards, so that it the air in cement air pump 264 is pressurized when the operator releases downward force on thumb plunger-rod 238, which then returns to its raised position under the restorative force of thumb rod return compression spring 245.

As shown in FIGS. 97, 98, and 99, upper sprocket wheel 270 and lower sprocket wheel 271 are securely anchored to the inner wall of tool barrel 239, one above the upper reach of the upward extension of one-way air valve sliding slot cover 273 and the other below the lower reach of the downward extension. During ejection of refill cartridge 235, air pump piston 233 is resisted by the friction posed by cement refill cartridge plug-piston 234, the resistance to outflow imposed by the small aperture of puncture pin 237, and the small diameter of cement feed or supply line 260. To resist moment loads that would lever and break off or jam air pump piston 233 under this resistance, air pump piston arm 267 is kept short and the attachments of arm 267 to sprocket chain 252 and air pump piston arm 267 made strong and rigid.

The permanent connection between cement air pump air pump piston-plunger 233 and its side of sprocket chain 252 must be rigid to minimize nonperpendicular movement of air pump piston-plunger 233 as could result in seizing against the sides of cement compartment 264. Upper sprocket wheel 270 and lower sprocket wheel 271 are accordingly offset to the same side. Rather than using a separate ferrule spacer, upper sprocket wheel 270 and lower sprocket wheel 271 have integral hubs that axially extend from the rear of each sprocket wheel 270 and 271 to the inner wall of tool barrel 239. The spacing afforded by these hubs prevent the teeth of sprocket wheels 270 and 271 from coming into contact with the internal surface of tool barrel 239.

Sprocket wheels 270 and 271 are fastened to tool barrel 239 by means of nonmagnetic stainless steel wide-head rivets 274 and 275 shown in FIG. 96 that serve as axles. Made of a metal or plastic, tool barrel 239 must be sufficiently thick and tough to secure rivets 274 and 275, which can be countersunk flush to the outer surface of tool barrel 239. Which side of sprocket chain 252 moves up and which down is arbitrary, but for uniformity, that to the left can be chosen for downward movement along with thumb plunger-rod 238 and thus cement-ahead operation. The counterclockwise detent reached by twisting thumb-ring 244 to engage the left hand run of sprocket chain 252 is indicated by engraving or embossing cap 243 with a tick-mark labeled "C-A" for cement-ahead operation.

For smooth movement as well as airtightness, cement or medication air pump piston-plunger 233 has a surrounding elastomeric annulus. To minimize tool girth and therewith the length of the incisions required to insert an insertion tool of given length to its maximum intracorporeal depth as well as to stabilize and reduce play in the sprocket belt 252 and the parts that engage sprocket chain 252, tool barrel 239 is the smallest diameter that allows sprocket chain 252 free movement. Below the upper segment that accommodates the foregoing mechanism, the diameter of tool barrel 239 is reduced to serve as a sleeve for the reciprocal movement of thumb plunger-rod 238.

The mechanism for adjusting the moment of cement ejection onset and duration is described above in the section entitled Mechanism for Adjustment in Stay Insertion Tool Ejection Cycle Inmate Cement Delivery Interval. Accordingly, by rotating thumb-ring 244 from one rotatory detent position to the other, the direction as up or down of cement air pump piston-plunger (cement piston, cement pressurization piston) 233 upon depression of thumb-ring 244 and thumb plunger-rod 238 is reversed allowing immediate conversion from cement-ahead to cement-follower operation, which is addressed above in the section entitled Cement-before Insertion or Cement-ahead Operation.

Upon the release of downward force by the operator of thumb-ring 244, compression spring 245 returns thumb rod or shaft 238 to the top stop position. If the restorative force encounters a condition of adventitial sclerosis, the operator forcibly pulls up his thumb against the superjacent (upper, overlying) arc of thumb-ring 244. So that a stay may continue to be recalled (retrieved, retracted, recovered) at any moment preceding its satisfactory placement, stay retention, retraction, and recovery electromagnet 242 conductor or probe 241 must remain in contact with heel 246 of stay ejection blade or tongue 247.

Thus, whereas the top of battery and magnet in stay retention, retraction, and recovery electromagnet 242 compartment to the left moves down and up in relation to cap 243 at the top of its run, the top of adhesive compartment 235 is affixed to cap 243. It does this by releasing cement onto the ductus when stay ejection blade or tongue 247, viewable in FIGS. 90 and 91, is drawn out from ejection slot 248 just before thumb rod or thumb plunger-rod 238 is released, allowing stay refill strip advancement compression spring 245 to draw stay ejection blade 247 up through ejection slot 248, thereby driving the next stay in stay refill strip or clip 250 into ductus 1.

By setting cement ejection to a slight interval before each stay is ejected, some is deposited on the adventitia so that the stay is coated on its underside. When the cement delivery system is configured thus, the adhesive interval adjustment described below in the section entitled Mechanism for Adjustment in Stay Insertion Tool Ejection Cycle Inmate Cement Delivery Interval is used to adjust the amount of cement applied to the outer surface of the ductus. By contrast, the configuration, hence, operation of the inverted cement delivery system incorporated in the embodiment of FIG. 89 is the reverse of that shown in FIGS. 90; 91, 95, and 102, in that cement is ejected when thumb plunger-rod 238 is returned to the raised position, retracting rather than advancing ejection blade 247 through ejection slot 248.

Cement delivery by the cement air pump mechanism in a pistol-configured embodiment may accordingly be characterized as a cement-ahead system, whereas that provided by the control syringe-configured embodiment shown in FIGS. 87, 90, 95, and 102 is a cement-follower system. Accordingly, unless the adhesive interval adjustment described above is used to forestall the initiation of cement outflow, cement will eject in synchrony with the ejection of stay 231, that is, throughout the interval that stay 231 continues to eject. The adhesive interval adjustment described below thus allows the detention of cement delivery onto a rearward extent of the upper surface of each stay 231, which extent is variable. Reversed operation expels cement only during stay ejection.

The mechanism described below in the section entitled Mechanism for Adjustment in Stay Insertion Tool Ejection Cycle Inmate Cement Delivery Interval is intended to allow adjustment in the moment in the tool operational cycle for the start and duration of cement delivery. With cement-ahead operation, stay 231 is inserted subadventitially into ductus 1 by pointed incision through the predeposited cement or tissue adhesive-hardener. Much of the cement is squeegeed away, but a thin coating is carried forward into the ductus. For an airtight fit within adhesive air pump 264, adhesive air pump piston-plunger 233 has an elastomeric surrounding annulus. While the use of a one-way air valve is specified below, this annulus could itself serve as a one-way air valve in the manner of that used in a bicycle tire air pump.

XVI5. Stay Insertion Tool with Pivoting Base

Except in an exposed field opened for a primary purpose, the entry or access incision for insertion of the tool is made as small and parallel to the ductus to be treated as practicable. The initial breach of the integument represents the substantive systemic immune stimulant, extension of the incision or the addition of incisions imparting additional trauma. To assure true concentricity or normal alignment of stay insertion subadventitially or medially, stay insertion tools are made with parts rigidly assembled. To alter the angle of insertion, a tool without a joint or pivot such as a gimbal or lateral hinge or folding joint must be tilted to a side, or forward, or backward, and/or rotated, as a whole.

However, a ductus may veer, deviate, or plunge at an angle that exceeds the degree to which the tool can be tilted to achieve normal (perpendicular, rectilinear) access. However, if the tool incorporates a point of flexion or joint, expansion of the entry incision to properly dispose the tool in relation to the ductus can often be avoided. That is, when the rectilinear apposition required to allow circumferential insertion cannot be achieved without lengthening the access incision and to do so would best if not necessarily be avoided, a special stay insertion tool with pivoting base is provided. Referring now to FIG. 91, the downward extension of tool butt 256 below the level of tool barrel 239 and ejection slot 248 affords adequate leverage moments to flex or abduct the tip by nudging it to a side.

The insertion of a probe alongside any insertion tool should not be necessary, all parts of butt 257 that come into contact with neighboring tissue rounded and smooth. When the tool incorporates an end-pivot as may necessitate pushing the distal end or working end against neighboring tissue to adjust the angle, use in especially vulnerable sites, such as a vascular bed, is with the butt additionally padded. Ordinarily unnecessary, a protective pad seen as 276 in the inset to FIG. 87 and in FIGS. 89 and 90 may be attached to the bottom of butt by pressing it onto the bottom of the tool. The pad is permanent, however, when a separate slitting edge to assist in extracting temporary stays such as higher dose-rate seeds is mounted flush beneath pad 276, as addressed in the section that follows.

Use of a tool with pivot is justified when speed and avoiding frequent withdrawal, exchanging of tools, and reinsertion are central. The parts immediately associated with stay ejection below the level of stay refill strip 250 advancement spring 251 mechanical, these must remain in fixed relation throughout the range of angular adjustment. Therefore, were ejection achieved by direct mechanical connection as in the fixed embodiment made to the foregoing description, the incorporation of a joint or pivot, depending upon the degrees of freedom, would have to allow the coordinated flexion of all of the parts that must vertically continue through the joint. Such would cost as much if not more than several tools made to different angles.

To allow the distal portion of the tool to pivot without a loss in stiffness among the parts at reasonable cost, ejection by means of direct mechanical connection to thumb-ring 244 is dispensed with, and an electrical fly by wire approach used to effect ejection regardless of the angle at the joint. While not specifically shown in the drawings, the structure of a stay insertion tool with pivot is easily understood in relation to the mechanical embodiment shown. This involves substituting for vertically reciprocating thumb plunger-rod 238, one that is stationary and fastened at its lower end to the ball of a ball joint. The ball joint thus separates the upper fixed (nonreciprocating, stationary) portion of the tool from the lower pivotable or tiltable base seen as 257 in FIG. 91, the parts thereof rigidly fastened together to move as one.

In an omnidirectionally pivoting tool with ball joint, joint tightness is set by the tightness of fit of the ball in the socket as manufactured; alternatively, a small screw in the socket accessible through a hole in the body of the tool is used to adjust the joint in tightness as necessary. The joint in the magnetic probe 241 at the level of the ball joint in rod 238 is woven of soft iron wire, and must be loose enough to offer little resistance to omnidirectional movement. The body of the tool mimics the joint with an upper segment that overlaps the lower where interface at complementary curved rims. The latter is seldom necessary, a ball joint with proper internal lining and properly pressed in manufacture affording smooth action of moderate tightness for years.

An electrical wire running alongside or wound around the rod connects a control button on the outside of the thumb-ring 244 in FIGS. 87, 88, and 102 to battery 263 and direct current-powered plunger (reciprocating armature or slug, punching, push-type) solenoid. The solenoid is fastened to the ball above by connection to the socket of the ball joint and rivet 258 below. To prevent abrupt snapping action that would pose the risk of injury to the ductus and surrounding tissue, the solenoid is viscous, or dashpot, damped. When energized, the solenoid pulls up rivet 258, causing ejection tongue 247 to push the next stay in the strip through ejection slot 248.

To minimize the need to tilt the upper portion of the tool as would necessitate enlargement of the entry wound (access incision), the ball joint and solenoid are placed as far down in tool base 257 in FIG. 91 as possible. To place the joint as far down on the tool as possible, stay 231 compartment 250, to include stay refill strip 250 advancement spring 251 and the stay strip or clip are generally shorter than in a mechanical embodiment. So that it will bend in any direction, flexion of magnetic conductor 241 is achieved by interposition of a segment of soft iron wire woven cable. The distal tiltable portion of the tool is adjusted in angle with the aid of a separate probe.

Power for stay retention, retraction, and recovery electromagnet 242, a fiberoptic lamp, for example, if clipped to the tool, and in any embodiment, whether or not incorporating a base that pivots, a solenoid to eject stays 231, is preferably obtained from an onboard battery as untethered by a power cord to afford the operator freedom of movement. So that it will remain extracorporeal, the battery compartment is positioned high up on the tool, allowing it to be as large as necessary. Unless the power is metered or modulated in a manner that makes disconnection from the control console impracticable, original equipment that uses a power supply is best powered instead by battery 263, which high up on the tool, remains extracorporeal.

Whether incorporating an omnidirectional pivot ball or a hinge joint, soft iron recovery and retraction electromagnet probe 241 is flexibly jointed by introducing a short segment of soft iron wire woven to allow bending with no more than moderate force and minimal loss in magnetic strength across the joint. Thumb plunger-rod 238 is then jointed by a rounded expansion preceding its lower margin or lip and complementary receiving expansion at the top of the lower or distal segment, these serving to impart omnidirectional flexibility as an integral ball joint. In an embodiment with only laterally pivoting butt 256, thumb plunger-rod 238 contains a hinge joint below the lower edge of the shortened tool barrel 239 and just above the level of ejection slot 248.

The component joints in otherwise rigid vertically disposed parts to include those internal and the tool body are at the same vertical level and include stay refill clip compartment 250 at or slightly above stay 231 seated against the floor of ejection slot 248. Only the hinge joint at the outside of the tool body need be adjustable in tightness; internal joints in thumb plunger-rod 238 and above ejection slot 248 can flex freely. To allow the tightness of the joint at the outside of the body of a tool with lateral hinge or folding joint pivot to be adjusted, the axle uses a pin with end caps that screw-on over wave washers.

Resistance to flexion set by the force with which the end-caps compress the articulating ends of the upper and lower segments of the tool body or barrel 239 together, the end-threaded axle pin with end-caps slotted allows this resistance to be adjusted with a small screwdriver. Only the outer (external, tool barrel) hinge joint need be adjustable, those internal necessitating a hole in barrel 239 to allow access with a screwdriver. The internal lateral hinge joints of the internal vertical members usually consist of one sided pressure sensitive tape. Adjustability in the internal hinge joints is not preferred, each necessitating a hole through tool barrel 239 just above its lower margin aligned to it to allow access for adjustment with a small screwdriver. The tool is not disassembled.

XVI6. Butt-Pad with Retractable Slitting Edge

Stays for later recovery contain ferrous metal, either as a core or as dispersed, to allow magnetic retrieval. While necessitating reentry at a later date, stays can be extracted with the same tool that is used to place these with or without stays loaded. To retrieve the stay or stays necessitates reentry and must be justified by the severity of the pathology, but allows any kind of nonabsorbable stay, such as an irradiating seed stay of high dose-rate, to remain in place over a prescribed period. More tenaciously ingrown stays, such as irradiating seed stays for nonpermanent implantation, as addressed above in the section entitled Arcuate Stent-stays (Stays, Stent-ribs, Ribs) or Stays for Use with Stent-jackets), may necessitate slight incision before the tool magnet will be able to extract these.

A nonabsorbable stay intended for temporary use is not given a deep outer texture, wetted to encourage tissue ingrowth, or coated with a strong cement for retention pending extraction. When the magnetic strength generated by stay retention, retraction, and recovery electromagnet 242 is insufficient to extract the stay, rechargeable battery 263 can be removed and the connector to an external power supply inserted. Extraction can also be expedited through the use of a retractable cutting edge at the bottom of the tool to incise the tissue blocking the extraction path. To avoid the needless tearing of tissue, extraction is along the same path as was insertion.

The simplest way to provide a slitting or cutting edge to assist in clearing the way to a previously implanted stay is to hone and slightly extend the upper edge of the ejection blade 247 notch or groove at its distal tip seen in FIG. 93. Use of the upper edge reduces the risk of inadvertent incisions into the adventitia. The indentation at the distal tip of ejection blade 247 can be a straight line groove or multisided depression formed to complement, receive, and stabilize the proximal tip of stay 231. A shallow ridge or nub along thumb plunger-rod 238 and depression receiving it serve to signal the operator that the ejection stroke has been completed and further depressing thumb-ring 244 will cause ejection blade 247 to continue out ejection slot 248 so that it can be used incisively.

Stay extraction can also be accomplished by means of a separate slitting edge or knife attached flush beneath tool butt 256 or for retraction into a slot midway in a protective pad of neoprene or similar cushioning material. A blade with slitting edge and release-retraction button located in a recess at the side of the tool butt so that a probe must be inserted alongside the tool to depress the button is not preferred. A small swing-out knife with semilunar or crescent-shaped cutting edge as in a chavetas (cigar maker's knife) attached flush beneath butt 256 as shown in FIG. 91 can be deployed to slash, or predeployed for controlled incision by rotating the tool.

The knife is rotated into and out of the deployed or cutting position by a microminiature rotary solenoid actuated by depressing an electrical button switch on thumb-ring 244. The solenoid is mounted within and wired through the vertical space separating thumb-ring plunger-rod 238 and magnetic conductor probe 241. To extract a stay, the cutting edge is used to slit the obstructive overlying tissue, the insertion tool retractive electromagnet is used to withdraw the stay, and inmate cement line 260 used to seal the slit. Such a slitting edge mechanism is equally applicable to any stay insertion tool, including one with an end-pivot, as addressed in the preceding section XVII. Stay Insertion Tool-Inserts and Extension Devices The distal girth of the tool sets the practical working depth for an entry wound of given length. That is, the access incision is kept smaller the longer the lower narrow portion of the tool is. To admit the portions up to the upper margin of the electromagnet triples the length of the incision. Unless the tool can be used in an open field rather than through an incision, increasing the distance between cap 243 and finger rings 232 and 249 of a control syringe-configured stay insertion tool such as shown in FIGS. 87, 88, and 102 only lengthens the extracorporeal length of the tool and does not contribute to the intracorporeal reach or working depth, set by the lower ends of stay retention, retraction, and recovery electromagnet 242 and then air pump 264. Producing tools in different lengths is preferred to extension devices in different lengths for insertion between the magnet and air pump compartments above and the working end below.

The latter can be made but are needlessly complicated and expensive. This is because the inmate cement delivery line and any other lines attached alongside the tool for irrigation, aspiration, a laser to flow solder on stays, and so on, would have to be disconnected and reconnected, and to do this would be more disruptive and potentially aggravating for the entry wound than simply to withdraw one tool and insert another of different configuration. Interchangeable distal segments for changing the stay size or type using the same upper portions of the tool would not be usable midprocedurally. All such inserts and adapters are discounted as unusable midprocedurally as well as offering at best little economic advantage.

XVI8. Use of Multiple Component Adhesives with a Stay Insertion Tool

This section pertains to the attachment to the stay insertion tool of a commercial syringe or plural syringes. These syringes may dispense medication or a sealant cement used as a hemostat and/or to bond stays ductus-intramurally, for example. Delivery from auxiliary syringes is distinct from the inmate cyanoacrylate delivery line described above. However, internal and attached delivery lines can and usually will be used in coordination. The primary purpose in a syringe holder attachment for the insertion tool is to provide a tissue sealant other than that delivered through the inmate line, which will almost always be a cyanoacrylate cement. Tissue sealants are provided in syringes that differ in configuration, and rather than to modify the syringes or contents, a means is provided for mounting any syringe to the insertion tool.

While addressed in terms of supplementary tissue sealants, the attachment may be used to deliver any kind of medication that can be delivered by syringe. As commonly seen in epoxy injectors (applicators, dispensers) several types of surgical adhesives available for use as hemostat sealants and/or to seal ductus stay insertion incisions consist of two-components, such as gelatin-dialdehyde (Geister Gluetiss) or hydrogels, the syringe applicator being dual-chambered, with one chamber for each component. Until single component fibrin sealants and other tissue glues that provide significant bond strength and not just hemostasis become available, this form of fibrin sealant is likely to remain preferable.

For the present application, a one-component adhesive such as Ethicon OMNEX is preferred; however, two component fibrin biomatrix sealants supplied in four separate vials, even when requiring temperature or other different preparation for each of the four constituents, such as with Baxter Tisseel VH® S/D (see Lowe, J., Luber, J., Levitsky, S., Hantak, E., Montgomery, J., Schiestl, N., Schofield, N., and Marra, S. 2007. "Evaluation of the Topical Hemostatic Efficacy and Safety of TISSEEL VH S/D Fibrin Sealant Compared with Currently Licensed TISSEEL VH in Patients Undergoing Cardiac Surgery: A Phase 3, Randomized, Double-blind Clinical Study," *Journal of Cardiovascular Surgery* (Turin, Italy) 48(3):323-331), can be used by attaching the commercial dual-chamber syringe to the insertion tool by means of a holder described below in the sections entitled Powered Stay Insertion Tool Holder for the Attachment of Medication or Tissue Sealant Syringes Whether Single, Dual, or Multi-chambered as Supplied for Tool Slave-follower or Independent Use and Binding of Lines and Cables Alongside the Stay Insertion Tool.

To use the inmate cyanoacrylate delivery line to seal the incisions made by the stay when inserted through the adventitia (stay insertion incisions) at the same time that an attached commercial dual-chamber syringe is used as a body entry-incision hemostat sealant is foreseeable and requires that these be independently controllable. When the commercial dual-chamber syringe is used in lieu of the inmate cyanoacrylate delivery line to seal the stay insertion incisions, its function must be integrated into the stay insertion function of the tool. When attached for immediacy as a body entry-incision hemostat, the commercial dual-chamber syringe must function independently of the stay insertion function of the tool.

When the attached syringe is to be freely usable for either or both purposes, its operation must be instantly switchable from coordinated to independent use, and such alternate operation is indeed accounted for in its control as described below in the section entitled Powered Stay Insertion Tool Holder for the Attachment of Medication or Tissue Sealant Syringes Whether Single, Dual, or Multi-chambered as Supplied for Tool Slave-follower or Independent Use. When unnecessary for either purpose and increasing the intracorporeally intromitted girth of the tool necessitating longer incisions to insert its distal working end into the body, a dual-chamber syringe is not attached.

Attaching a dual-chamber syringe as a backup hemostat or safeguard in general is justified when the extension provided by the maker does not contribute objectionable girth, or when warming thins out the adhesive long enough for conduction through a delivery line of smaller diameter and the girth added by combining this narrower delivery line with a temperature-changing ('cooling') catheter is less than that of the usual delivery extension alone. If inconsistency in heating is not objectionable, an assistant can use a hot air gun or similar electrical heating device to warm the attached adhesive delivery line and a cooling catheter dispensed with. A given stay insertion tool is made for ductus within a small range of sizes that use the same size stays.

Extension inserts as addressed in the section above entitled Stay Insertion Tool Extension Inserts presenting limitations, tools to insert stays of a given size are generally also made in shorter and longer tool barrel lengths to facilitate working at superficial or at various depths within the body. In overall configuration, however, the tool is standardized, to include a single lumen adhesive delivery line that ejects the adhesive over the stay ejection slot at the front of the tool. To allow the use of adhesives that require the combining of two or more components to initiate curing (setting, polymerization), the marketed dispenser or applicator, typically dual chambered, is attached alongside the tool for actuation by the same thumb-ring.

However, if to do so interferes with viewability, then the holder is clamped to a ring stand in a remote location, and the contents driven through an extension line, actuation necessitating the addition of an electrical switch to detect depression of the thumb-ring. The dual component adhesive product is preferably used with no deviation from the instructions provided by the maker. Thus, ordinarily, whether the syringe holder is directly attached alongside the insertion tool or is remote, the extension is connected to the outlet of the syringe applicator, the components having already been combined. To retard setting a cooling catheter with side-holes can be lashed alongside the delivery extension line.

The commercial syringe holder and the rest of the mounting additionally allows for aligning a 'cooling' catheter with side holes aligned to the syringes and/or an end-hole for warming or chilling the components or the adhesive as mixed prior to, upon, or following application. Attached outside the tool, the line can be significantly larger in diameter than could an internal line and thus deliver an adhesive that is higher in viscosity. Furthermore, the use of attachments allows reducing the basic tool to models that differ only in the width of the stays used and in the length of the tool required to reach down to different working depths. Using dual-chambered syringes with little if any modification as purchased, such as to snip off part of a long outlet tube, makes it possible to significantly reduce the complexity and expense of manufacture.

Dual chamber syringe adhesives provided by the maker in dispensers attached to the tool using the device described in the section below entitled Powered Stay Insertion Tool Holder for the Attachment of Medication or Tissue Sealant Syringes Whether Single, Dual, or Multi-chambered as Supplied for Tool Slave-follower or Independent Use include Baxter CoSeal® (Angiodevice International/Baxter Biosurgery Division, Baxter Healthcare Corporation, Deerfield, Ill.), which consists of two polyethylene glycols and dilute solutions of hydrogen chloride and sodium phosphate with sodium carbonate, and BioGlue® (CryoLife, Incorporated, Kennesaw, Ga.), which consists of solutions of purified bovine serum albumin (BSA) and glutaraldehyde.

As can other kinds of delivery, irrigation, and aspiration lines, dual-chambered syringe adhesive dispensers are attached to the tool with the aid of clips, as described below in the sections entitled Binding of Lines and Cables Alongside the Stay Insertion Tool and Use of Stay Insertion Tool Mounting Clips to Fasten an Adhesive Delivery Line. While the stay insertion tool must be used in substantially normal relation to the ductus so that extensive conditions will necessitate numerous incisions, attachments are devised to least contribute additional tool girth as would necessitate longer incisions. Suction and temperature-changing ('cooling' catheter) lines attached alongside the tool affect the diameter only slightly.

XVI9. Powered Stay Insertion Tool Holder for the Attachment of Medication or Tissue Sealant Syringes Whether Single, Dual, or Multi-Chambered as Supplied, for Tool Slave-Follower or Independent Use XVI9a. Use of Commercial Syringes and Extension Tubes For inmate cement delivery line control, both switching between cement-ahead and cement-follower or cement-during operation and the timing within this cyclical relation of cement ejection are controlled mechanically. The first of these is accomplished by the engagement of thumb plunger-rod 238 to sprocket belt connecting arm 272 by rotation of thumb plunger-rod 238 into the adjacent opening on one or the other side in the sprocket chain 252 shown in FIGS. 96 and 97, the other through adjustment in the height of slidable air pressure relief one-way valve shown as 265 in FIG. 95 mounted in the side of air pump 264. Contained within the tool, no need to control a remote function is present.

This differs from the control of the auxiliary syringe holding frame, which to control at the remote device (with controls mounted on the holder) would necessitate glancing away from the treatment site. Observation of the treatment site almost always accomplished with the aid of an endoscope mounted to the side of the insertion tool, a need to adjust any controls that had been mounted to the auxiliary syringe holding frame would necessitate momentary diverting of the eyes and the removal of one hand from the tool. [2882] While the tool will almost always be stabilized by the edges of the small entry wound made to admit it, and the operator would ordinarily maintain the working end of the tool in the correct position, the need to glance sideways and remove one hand can result in jerks and displacement.

Accordingly, timing control of the auxiliary syringe holder is accomplished electrically through controls mounted on the tool itself and not on the auxiliary syringe holder. This operation consists of adjusting an initial delay and ensuing on-time interval as described below in the section entitled Control of Auxiliary Syringe Ejection Time. As addressed below in the section entitled Binding of Lines and Cables Alongside the Stay Insertion Tool, for control by touch alone as does not detract from maintaining the tool in a stable position, attachments to the insertion tool such as a small liquid nitrogen ($LN_2$), nitrous oxide, or $CO_2$ can or a cartridge with spring loaded trigger to release chilled air into a side- and/or end-hole cooling catheter attached with clips alongside the tool can be clipped at the side or front of the gown or attached to a waistband.

Dependent upon gauge, connection of a cryotherapeutic liquid nitrogen spray can to the cooling catheter clipped alongside the insertion tool is by means of conventional intravenous or other medical tube connectors. The ability to manipulate controls by touch alone as when attached thus is less likely to affect tool stability. The chilling effect of devices for attachment to barrel-assemblies and stay insertion tools can be moderated in temperature and reduced in exit rate by means of numerous existing kinds of cryosurgical and cryotherapeutic apparatus, to include the use of a thermal barrier (see, for example, Holland, T. D., Joye, J., Williams, R., and Williams, R. 2004. "Safety Cryotherapy Catheter," U.S. Pat. No. 6,811,550.

When the operator has determined that the stays can each be inserted with an action that is consistent in time from one to the next, the dual interval (interval off or delay followed by an interval on) timer is adjusted to effect a change from cement-before to cement-during operation. However, unless medication of inordinate cost is being delivered, the consequence of unanticipatable hesitation or discovery amounts to no more than an inappropriately timed release. If necessary, the substance released, whether medication, tissue adhesive, or both is swabbed away. If consistency appears improbable, a tool that incorporates break contacts at the top and bottom of the thumb rod stroke is used to establish the start of cycle times for release before or release after the downstroke operation, thus reducing the incidence of inappropriate discharge.

The substitution of electrical for mechanical control over the inmate cement delivery line to switch from cement-ahead to cement-during operation would allow dispensing with the twist-right twist-left sprocket and air pump sliding pressure relief aperture elements but necessitate incorporating a dual adjustable interval relay module into the tool. Furthermore, the sprocket mechanism cannot be misadjusted to misassign action to release-ahead to release-after action. Furthermore, at least as of the time of filing, the state of the art relay module measures 2 inches on a side with corners projecting on both sides of the tool, which circumstance was felt best avoided. Two or more component adhesives are not applied with one component delivered through the inmate line and the other component delivered through a line or lines attached to the side or front of the tool.

Similarly, to coordinate the application of adhesives so that the single lumen line built into the stay insertion tool is used to apply a coating of cyanoacrylate cement to the trailing end of the upper surface of each stay for sealing the ductus entry incision, while a commercial tissue sealant, typically dispensed from a dual-chambered syringe, is used to apply a two-component adhesive-hardener to the front and middle portions of the upper surface of each stay is considered to be justified only with the advent of cements that from the standpoint of promoting the recovery of integrity within the ductus wall are superior to any currently available.

If the extension provided by the maker is rigid and not conformant to the tool, it is replaced with flexible tubing. Two-component tissue sealants that demand pressing together of the surfaces to be bonded for two minutes or longer are too slow to serve as stay insertion incision adhesives, much less ductus-intraparietal stay and laminar bonding agents. The preferability of cyanoacrylate cement to these is clear. The attached line for delivering tissue sealant can be used independently of the stay insertion function for use as a hemostat or in direct support in and timed to stay insertion. Whereas the inmate line for the delivery of a bonding agent or tissue sealant, usually cyanoacrylate cement, cannot be used independently of stay insertion, a separate syringe of cyanoacrylate can be added using the commercial tissue sealant holder described below.

Numerous modifications of the holder to be described are considered obvious. Increasing the width of the holder and using a more powerful motor or separate motors and leadscrews to either side of the syringes, or using an increased gear reduction ratio with one or two motors makes it possible to load a syringe or combination of syringes that require greater force to depress the plunger or plungers. Such can be used to control multiple single or dual-chambered syringes in adjacent relation in one holder where the delivery line is shared, each syringe supplying a different substance to the treatment site. A dual-chambered syringe can be used to mix and dispense components of one endsubstance, such as a two-component tissue cement, or to provide different substances whether these consist of medication or tissue sealants, provided these can be passed down a common delivery line.

Very thick (viscous, viscid, heavy) fluent substances may be unsuited to integration into the stay insertion sequence and while dispensable using an auxiliary syringe equipped with motors of adequate power, may have to be separately controlled. The additional force essential to expel less viscous substances from the syringe may necessitate separate motors and lead screws to either side of the syringe. The use of multiple syringes with any one insertion tool must therefore consider the efficacy of the contents of each syringe when mixed and fed through a common delivery line. Compatible contents can be merged from a separate input line from each syringe or dual-chambered syringe. Unless operator errors would be inconsequential, a second plural auxiliary syringe holder for use independently of the other is inserted into a second socket mounted to the opposite side of the tool inmate cement chamber (cement air pump and cartridge housing).

The use to one side of more than one auxiliary syringe holder when one of these can be attached at the opposite side is discouraged as conducive to operator error and depending upon the additional weight to the one side, manual fatigue. Procedures should seldom last long enough that the weight of even two relatively powerful small gearbox motors on the holder to one side without a counterbalancing weight on the other side should result in manual fatigue. Switchable operation from stay insertion tool slave-follower or tool stay ejection synchronous to independent mode is unaffected by the number or kind of syringes loaded. Holders can be attached to either side of the tool to provide right and left-handed models with the thumb-ring switches for the holders either attached to the thumb-ring for slidable rotation to the opposite side, as preferred, or the switches duplicated at either side of the thumb-ring.

The conductors for the thumb-ring switches must have sufficient slack to allow the thumb-ring to be rotated. For medication or cement to be introduced intraincisionally, that is, carried forward on the surface of the stay into the incision as the stay enters into the wall of the ductus, the terminus of any auxiliary syringe delivery line must be positioned directly above the stay ejection slot, which must therefore be interchangeable in position with that of the inmate cement delivery line. Additional auxiliary syringes attached by means of a holding frame must terminate at points adjacent or nearby that over the ejection slot. With this understanding, holders can be attached to both sides of the tool inmate cement housing, with one or both of these sides used in slave-follower or independent mode.

Placement of the outlet ends or the termination of auxiliary syringe delivery lines at the sides of the tool foot allow the application of medication, such as anti-inflammatory, anti-infective, or analgesic, just before or after stay insertion. The simultaneous use and evacuation into a common delivery line of plural syringes assumes that the contents of each syringe is compatible with that of the other syringes as not to require segregation in separate delivery lines or in separate lumens of multilumen tubing, and that no degradation in the efficacy of any ingredient will result from the fact that the entire delivery line from syringe to the distal line terminus is charged with this mixture.

As medication applied to a. Both the upper and lower surfaces of the stay in cement-ahead operation and b. An adjustable extent of the upper surface in cement-during operation is largely removed by squeegeeing, that is, swept away by brushing against the sides of the incision as the stay penetrates into the ductus wall, the addition to the medication of a thick and adherent substance will sometimes assist in introducing more of the medication into the wall of the ductus. Provided withdrawal is unobjectionable or avoidable through the use of a probe, delivery line termini can be bound for interchangeable positioning directly above the stay ejection slot by means of a small tissue compatible elastic band.

In a tool wherein the retention and recovery electromagnet reciprocates down and up along with the thumb-ring, this will add some resistance to movement and likely require occasional withdrawal in order to adjust the elastic band. Even though it would allow more flexibility in the use of auxiliary syringes without the need for withdrawal, the incorporation of a turret mechanism for rotating different syringe and delivery lines or for aligning separate syringe outputs to different tube extensions for rotation into position above the stay ejection slot is discouraged as distracting and conducive to human error as well as introducing a unjustified complexity and expense.

Auxiliary syringe holders on opposite sides of the tool can share a dual interval relay as well as the break contact terminals as addressed below in the section entitled Control of Auxiliary Syringes when inset into only one side of the cement air pump and cartridge housing. However, this will cause the holder motors to either side to conform to the same cycle even though the deposition to one side of an antiinfective, for example, must be deposited just before the deposition of a sealant, for example. By contrast, incorporating a timing relay into each holding frame as an integral component allows each auxiliary syringe to be synchronized to the tool stay ejection cycle with different timing, for which the increased cost is considered justified on the basis of uniformity and the independent usability of the holders, as well as the additional flexibility imparted.

If the action overall is slightly acyclical or aperiodic so that the relation between the subcycles to either side progressively changes or desynchronizes, the control on one of the dual interval timing modules must be adjusted midprocedurally. Furthermore, to duplicate the contacts on both sides is no more costly than to provide incorporate conductors for a holder on the opposite side. For clear distinction in use, tissue sealant can be segregated in the holder attached to one side of the tool, while medication is provided by the holder attached to the other side. Either or both holders can be set for slave-follower or stay ejection cycle independent, that is, operator discretionary direct, control.

The specific types of substances and timing control between the sides that are possible represent a large number of combinations and permutations. Provided an unused delivery line is clipped in position for nonintaincisional application, the proximal end of the delivery line previously in use can be disconnected at the bottom of the socket and the unused line connected. Usually the connection point will be far enough above the entry wound to allow this without the need to withdraw the tool. In this way, an assistant can connect or replace syringes containing certain substances with others as the procedure progresses. Otherwise, changing delivery lines requires withdrawal of the tool and replacement of the line or lines.

Rather than to manipulate different delivery lines providing substances intended for intraincisional application midprocedurally (ordinarily the inmate cement and an auxiliary syringe line), it will usually be preferable to withdraw one tool and exchange it for another that has been configured for continuation of the procedure as desired. With an assistant to configure the tool as necessary, rotating two tools will allow any response within the operational limits of such tools. One object of the invention being to accomplish an improved form of stenting with the least trauma, stay insertion tools are long and narrow to allow deep access through small incisions.

Hence, auxilliary delivery lines and clips as described below in the section entitled Stay Insertion Tool Mounting Spring Clips for attaching these are mounted to sides of the tool only as required for the specific procedure. Whether operated as a. A passive (slave, follower, dependent, tool cycle synchronized) function tied to tool function for providing a discharge of a tissue sealant coordinated with stay insertion for sealing stay insertion incisions, b. Independently (tool cycle nonsynchronized) to stay insertion as a hemostat sealant, anti-infective, anti-inflammatory, or other medication, or c. As switchable between either kind of operation, a two-component or dual-chambered syringe must be mounted off to a side, or it will interfere with direct viewability of the site to be treated.

An attached endoscope can be used to view the toe of the tool foot but not portions of the tool at higher levels. As described below in the section entitled Powered Stay Insertion Tool Holder for the Attachment of Medication or Tissue Sealant Syringes Whether Single, Dual, or Multi-chambered as Supplied for Tool Slave-follower or Independent Use, since dual-chambered syringe applicators or dispensers provided with dual-component adhesives, for example, may interfere with viewability of the treatment site when attached to the insertion tool in adjacent relation, these are raised and set off to a side of the tool at an angle. Making the dual syringe holder of transparent material having optical clarity can contribute some viewability, but since the holder can be rotated, transparency is unnecessary. The amount of adhesive remaining is easily seen.

XVI9b. Avoidance of Remote Syringe Placement and Long Adhesive Delivery Lines

To keep the components of a two-component tissue cement separated would necessitate modification of the double chamber syringe, the attachment to each chamber of an extension line, and filling each line with a component. Insufficient cement likely to fill longer extension lines and much cement likely to remain following the procedure, avoiding waste would necessitate attaching the extension lines and then introducing an inert filler material at the top of the chambers to drive the components down line to a distal segment of column length somewhat longer than that to be used. Compared to cyanoacrylate cements, two-component adhesives are slow to achieve initial set.

Thus, under normal circumstances, even when the parts have already been mixed, the additional transit time to move over the increased distance from the syringe outlet to the treatment site is noncritical in that it does not significantly reduce the open time available to promote clogging of the delivery line. Rather than to enhance flowability, the use of a 'cooling' catheter to warm the line will more likely accelerate setting (polymerization), which is, however, useful to accelerate curing once the sealant has been applied. Whether chilling the line to retard polymerization will allow the use of a narrower line depends upon the concurrent effect on viscosity, which is likely to be the increase thereof.

Ordinarily, an auxiliary holder syringe-contributed two-component sealant is used as a hemostat under independent or tool stay insertion cycle nonsynchronous operation and as a stay insertion incision sealer and ductus intraparietal stay binder when switched to synchronous operation. Thus, the time following mixing of the components and initiation of polymerization that the cement is left to linger before use is shorter with the mix kept moving. However, if used only to seal stay insertion incisions, the rate of consumption, even without an added length of tubing, invites incrassating or congealing, the slower delivery prompting clogging. The quantity of adhesive to fill long lines is wasteful.

For these reasons, a position for a dual-chamber syringe that is more remote from the insertion tool, such as one pumped from an adjacent stand through a relatively long extension line rather than attached to the tool and offset at an angle as will be described is discounted. This mounting satisfies the requirement to position the holder proximate to, without visually obstructing, the point of application and surrounding treatment site. To avoid the cost and complexity of actually integrating the delivery of two or more component adhesives into the mechanism of the insertion tool as has been done to include a single-component adhesive-hardener delivery line, marketed applicators are made usable without the need to modify or repackage these beyond snipping off a portion of an extension tip or "applicator" when too long.

Attachment to a stay insertion tool of a commercial surgical adhesive dispensing device such as a dual-chambered syringe will be described in relation to the control, or thumb and finger ring-type syringes shown in FIGS. 87 and 88, the auxiliary syringe attachment shown in FIGS. 101 thru 103. Two-component adhesives such as CoSeal® (Angiodevice International/Baxter Biosurgery) and BioGlue® (CryoLife), are sold with dispensers or applicators that have been configured for the specific ingredients that each uses. The dispensers are therefore different in dimensions, conformation, amount of adhesive expelled per unit distance of plunger depression, and so on.

Nevertheless, a single holder must allow any given syringe to be attached to the stay insertion tool. The use with minimal if any modification to off the shelf adhesives and applicators eliminates complexity, as does controlling the attached syringe electrically rather than through a complicated mechanical linkage. As addressed above in the sections entitled Multiple Component Adhesives and Use of Commercial Syringes and Extension Tubes, auxiliary syringes, typically dual-chambered, or conventional syringes containing medication or a commercial tissue sealant, are attached to a stay insertion tool by means of a holding frame, or holder.

XVI9c. Stay Insertion Tool Auxiliary Syringes
XVI9c(1). Control of Auxiliary Syringes Unlike the cement delivery line built into the tool, commercial syringes for attachment to a stay insertion tool must be positioned off to a side of the tool. This in itself makes the control of the syringe by mechanical means complicated. Since commercial syringes are self-contained devices that do not conform to prescribed dimensions, any one holding frame must accept syringes over a range of shapes and sizes. Commercial syringe chambers and tips differ in internal diameter and the contents in viscosity, so that the amount of adhesive expelled for a given downward movement of the plunger or plungers is different for each.

An auxiliary syringe holder is a battery powered syringe driver or syringe pump for attachment to a stay insertion tool. It can be used to dispense a two or more part adhesive, therapeutic solution, fluid medication, or component syringes can be divided to deliver cement and a medicinal substance simultaneously in the relative proportion desired. At the same time, the stroke of the stay insertion tool plunger-rod 238 and the timing of its detrusion (depression) is dictated by its stay feeding and ejection function, which is tied to the length of the stays the tool is meant to insert, and to this extent is the same regardless of the overall length of the tool.

Nevertheless, differences in stroke and the variability required in the timing and quantity of syringe expulsion relative to tool plunger-rod 238 depression with various commercial syringe plungers militates against a mechanical linkage of the syringe to the tool; no simple, unobtrusive, dependable, and easily maintained mechanical linkage or cabling would allow even one auxiliary commercial syringe to be connected and controlled with the variability in timing and the amount of discharge required when the tool plunger-rod 238 is depressed. By contrast, to coordinate the action of a commercial dual-chambered syringe to that of the insertion tool by electrical means is relatively straightforward and inexpensive.

In place of the intricacies of applying adjustments with a mechanical system, timing relations are applied empirically by adjustment to the dual interval timing relay or relays during testing before use. Such timing control makes it possible to initiate the onset of adhesive outflow onto the surface of the ductus just prior to the ejection of a deep surface-textured stay which then carries the adhesive forward into the ductus wall on both its upper and lower surfaces, or cement-ahead operation. If initiated during stay ejection, then the onset and duration of adhesive outflow is timed to vary the extent of the upper surface of the stay that is coated, which is referred to as cement-follower operation.

Emptying of the syringe or syringes in a given holder must be variably synchronizable to the stay ejection cycle, as well as switchable to independent operation whenever the operator wishes to apply medication or sealant in a discretionary manner. In some instances, as when the deposition of a local anesthetic or anti-infective must precede the deposition of a sealant, collateral synchronization as to sequence and the amount of substance expelled between the syringes attached to either side of the tool will matter. While the operator may choose to use auxiliary syringes in an exclusively discretionary manner for an entire procedure, for greater applicability and to cover numerous contingencies, the apparatus must be capable of switching from independent function to the variable and differential synchronizing to the stay insertion cycle of two attached holders.

For a syringe chamber, outlet, and extension or delivery line of given internal diameter used to dispense a fluid of given viscosity, the amount of the fluid expelled (discharged) is determined by the distance of syringe plunger downward travel or excursion (distance depressed). This is determined by the speed of the frame motor, the time that the motor is on, and the pitch of the lead screw thread. Of these, only the interval over which the frame motor is on is normally varied, this by adjusting the settings on the dual-interval relay. Otherwise, the operator can switch to direct control independent of the stay ejection cycle at which time the motor will draw current directly from the battery, the relay then shunted (bypassed).

Substances not sold in syringes afford some choice of syringe and extension or delivery line, but once the syringes and delivery lines to be used have been chosen, to mix the contents of syringes attached to either side of the tool in a certain proportion will require adjusting the side-to-side related onsets, durations, and terminations that each holding frame motor is on. More reliably as well as more flexibly, the holder is driven by a lead screw which is rotated by a miniature direct current spur gear head motor of the type manufactured, for example, by Lynxmotion, Inc., Pekin, Ill. The motor is actuated upon separation of the break contact terminals mounted at the junction between the stationary cement and the reciprocating battery-electromagnet housings.

The motor or motors are used at constant speed, control over the quantity of material discharged by the syringe or syringes being determined by the interval over which the plunger is depressed. Using motor speed to compensate for variation in the speed with which the operator depresses the thumb-ring is considered an unnecessary complication and expense. The occasional misdeposition of medication or cement due to hesitation or distraction may require swabbing or the use of an attached suction line (aspirator) but poses no risk. For general hemostatic use, a simple momentary contact push button switch is used. Switching from direct operator (independent, discretionary) to slave control introduces break contacts and a double interval timing module into the circuit such that separating the contacts by depressing the tool thumb-ring sends current to the timing module which controls the motor on the holding frame.

In this way, the timing module is used to coordinate the ejection of adhesive or tissue sealant by the auxiliary syringe or syringes in the holder to the mechanical stay insertion tool ejection cycle. Otherwise, recovering excess adhesive by means of an attached aspirator line dispenses with the need to insert a swab through the small entry wound. To coordinate the release of adhesive to stay ejection, the break contact terminals on the tool and an interval timing module are used to eject a settable amount of adhesive only when the thumb-ring and central spring shaft of the insertion tool move either up or down. The amount of adhesive and segment of the tool operational cycle over which the ejection of the adhesive occurs is variable according to the interval settings applied to the module.

XVI9c(2). Tissue Sealant Syringe Holder (Holding Frame) and Attachment

When attached to the stay insertion tool, a commercial tissue sealant syringe must be usable both for hemostasis independently of the stay insertion function of the tool, as well as in direct and closely coordinated support of stay insertion. Control over the small electrical motor used to depress the syringe plunger must therefore be switchable between independent and tool-driven (locked, tied, follower) use. The viscosity at the end opening (nozzle, spout, outlet, ejection tip) will usually allow use in the small amounts required for coordination with stay ejection; if not, an end-opening adapter to reduce the diameter (reducer) is used.

Excessive internal cohesion or surface tension (Plateau-Rayleigh instability) that results in the formation at the end-opening of adherent beads (globules, drops) of sealant which interfere with the smooth flow essential for fine use may necessitate the addition of a diluent to either or both components or the need to periodically withdraw and dip if not agitate the end of the tool in a diluent or solvent. Differing in configuration and dimensions, some syringes or combinations of syringes may require a special holding frame. Making the distance between upper and lower compressive plates in the frame large enough to accommodate most commercial syringe products and using the onboard motor to bring the plates used together to clamp the specific syringe between the two plates will, however, accommodate almost every commonly sold syringe, the majority about 3½ inches long with "needle" or "tip" removed or trimmed.

Commercial syringes may be dual-chambered to separate two components that when mixed together initiate curing within the syringe before reaching the end opening Extensions are usually available from the syringe producer, and the syringes contain a sufficient amount of each component to fill the extension and last the procedure. The extension provided by the maker can usually be used as the fluid channel that passes through the outer bendable metal jacket of the support arm and connecting cable described below. If this is too short, ordinary catheter tubing can be used.

Although the components are mixed initiating curing (polymerization) within the syringe mixing chamber or mixing nozzle, the setting time of commonly available such products is not so fast as to require that the length of the extension needed to mount the syringe to the stay insertion tool be kept to a minimum. The delivery line can thus be allowed sufficient length to position the holding frame unobtrusively off to a side. While the syringe is always mounted prior to the procedure, the setting time will determine whether the extension tube is filled with the mixed components before the procedure is underway or the need therefor arises.

Although the sealant is not likely to reach initial set, in order to not detain the procedure, the small motor used to drive the plunger must be capable of short-term continuous-duty torque output sufficient to fill the line quickly. To allow the use of either the inmate or attached sealant for ductus-intramural stay bonding, an elastomeric ring is used as the most distad attachment of the two lines at the front of the tool, and a probe is used to shift the tip of either line into position directly above the stay ejection slot. When the attached syringe is used as a hemostat, the tip of the inmate cement line is left in position above the ejection slot.

XVI9c(3). Structure of Tissue Sealant Syringe Holder
XVI9c(4). Stay Insertion Tool Auxiliary Syringe Holding Frame Attachment Since only the syringe and enough of its outlet 'needle' or 'tip' to engage the socket described below are used, a holding frame or holder of reasonably standardized size can be provided that will allow adjustment to accommodate almost any one single or dual chambered syringe. Bio-Glue®, Tisseel®, and CoSeal®, for example, are dispensed from dual-chambered syringes that mix the components internally, whereas Gluetiss® is dispensed from two separate syringes, one larger for the gelatin-resorcinol solution component, the other smaller for the aqueous glutardialdehyde and glyoxal hardening solution component.

Holders configured for these and future tissue sealant syringes are made out of any suitable plastic by molding, or fabricated out of half-inch wide plastic or nonferrous metal flat strip stock, for example. Gluetiss® is mixed on the treatment tissue, with a 20:1 to 10:1 ratio of glue to hardener. While the syringe that contains the hardener is smaller in diameter and length, it is not designed to deliver its component in the appropriate proportion when the plungers are depressed alongside one another to the same depth as would allow the holder mechanism to be made in a relatively simple form as preferred.

More specifically, the correspondingly disproportionate rates of depression between the two syringe plungers required to expel the components in the correct proportion would necessitate adding a reduction gearbox in addition to a mixing nozzle. Excessive open time precluding the immediate sealing of incisions, surgical adhesives other than cyanoacrylate cement may require the addition of an accelerator to reduce the interval prior to initial set. With the appearance of dual syringe tissue sealants that set more quickly and release the contents of the syringes in the prescribed proportion for a given downstroke of the syringe pistons (piston plungers, plungers), the holder is made as is one for a single (usually dual-chambered) syringe.

Turning now to FIGS. 101 thru 103, this is in the form of a miniature press or vertically disposed vise having an upper plate or 'jaw' that drives the syringe piston plungers down by means of a lead screw, so that even when not united as shown in FIGS. 101 thru 103, the syringe pistons are driven down together. The shaft of motor 286 is connected to gear reduction box 288 by means of an unseen full coupling union consisting of an ordinary starter joint-shaped joint-encircling metal sheath having a keyed internal cross section complementary to that of the motor shaft. Gear reduction box 288 is in turn connected to lead screw 278 by full coupling union 287.

Auxiliary syringe holding frame 284 accommodates dual-chambered commercial syringes such as that sold under the BioGlue® label, with internal mixing nozzle 292 and single or unified bottom-opening exit-hole 279. Auxiliary syringe holding frame 284 incorporates no onboard controls, allowing its reversal for connection to the line entry socket on the opposite side of the tool without impeding use by a nonambidextrous operator or assistant. Dual chambered commercial syringes 280 and 281 are made to mix the components of the tissue sealant in the correct proportion automatically when the single thumb rest depresses both plungers.

The upper halves of holding frame 284 sides 282 and 283 are slotted down the center from near to the top to half way down to serve as guideways to complementary projections at the sides of screw 278 follower crosspiece 285. To allow the syringe to be replaced midprocedurally, side pieces 282 and 283 of auxiliary syringe holding frame 284 are not folded inward. Small extensions from follower strip or lead screw 278 follower crosspiece 285 insert through the slots cut down the center of each side of auxiliary syringe holding frame 284. Follower crosspiece 285 thus rides up and down the side slots as guideways when small direct current gear head motor 286 rotates lead screw 278 driving lead screw follower block 285, which is resistance welded to the bottom of carriage plunger depressing follower crosspiece 285.

As shown in FIG. 101, lead screw 278 extends down through upper frame crosspiece 285 and press-down crosspiece strip with integral lead screw follower block 289 with integral lead screw follower block having end projections that fit into and ride down the slot guideways in sides 282 and 283. Upper frame crosspiece 285 spans across the top of auxiliary syringe holding frame 284 from side 282 to side 283, is folded over, and resistance welded to sides 282 and 283 of frame 284. The thread of lead screw or bolt 278 extends down enough to allow the syringe to be fully emptied.

Bottom crosspiece 291 has a hole at the center to admit dual syringe mixing nozzle 292 and thus support dual syringe including barrels 280 and 281 from beneath when dual syringe thumb rest 294 is forced downward by pressdown crosspiece strip with integral lead screw follower block 289. Auxiliary syringe holding frame 284 lower crosspiece 291 supports and passes through the bottom dual syringe unified outlet 279 in which the components from either barrel are mixed, some portion of the exit nozzle 292 distal thereto retained for insertion and friction fit into the upper end of cable connecting delivery extension line or auxiliary syringe holding frame 284 supporting arm and connecting cable 290.

A mixing nozzle such as seen in the CryoLife BioGlue® syringe has the spreading tip removed but is otherwise left intact. Since during a procedure, press-down crosspiece strip with integral lead screw follower block 289 is moved upwards only to replace a spent with a full syringe, the syringe is secured in position. Just as the frame bottom crosspiece 291, the ends of frame top crosspiece 285 are folded down over as to be vertically flush, and resistance welded to the upper ends toward the tops of frame sides 282 and 283. To insert a new syringe into the holder, motor 286 is used to drive press-down crosspiece strip with integral lead screw follower block 289 upward enough to allow the spent syringe to be removed and the new syringe inserted.

Dual syringe mixing nozzle 292 through the center hole, motor 286 is reversed to clamp the syringe between bottom crosspiece 291 and press-down crosspiece strip with integral lead screw follower block 289. Further depression of pressdown crosspiece strip with integral lead screw follower block 289 and dual syringe thumb-rest 294 causes dual syringe barrels 280 and 281 to expel their contents. The parts must be sufficiently robust that off-axis lead screw or bolt 278, hence eccentric (moment arm, lever arm) application of compressive force, will not achieve a magnitude sufficient to jam the end protrusions of press-down crosspiece strip with integral lead screw follower block 289 in its side guideways.

XVI9c(5). Connection of the Holding Frame to the Stay Insertion Tool

As shown in FIG. 102, attachment of auxiliary syringe holding frame 284 to the stay insertion tool is by means of auxiliary syringe holding frame supporting arm and connecting cable 290 shown in FIG. 105 with upper end engaged by dual syringe exit mixing nozzle 292 and lower end engaged in stay insertion tool auxiliary syringe holding frame supporting arm and connecting cable socket 296 shown in FIG. 106. Auxiliary syringe holding frame supporting arm and connecting cable socket 296 is mounted within auxiliary syringe socket block 297 to the side of vertically stationary cement air pump and refill cartridge housing 264, with delivery of the mixed cement, drug, or other therapeutic substance passing down to the work site through polymer auxiliary syringe delivery line 298.

As shown in FIG. 105, auxiliary syringe holding frame supporting arm and connecting cable 290 consists of outer bendable preferably hexagonal structural casing or sheath 299, containing polymer syringe extension tube or cement and therapeutic substance delivery channel 300 and electrical conductors 301 thru 306 leading and from auxiliary syringe holding frame motor 286 and dual interval timing relay 293 to stay insertion tool inmate battery 263. Auxiliary syringe holding frame supporting arm and connecting cable socket 296 includes electrical contacts at its bottom for connection to electrical conductors 301 thru 306. 102.

FIG. 106 shows the position of auxiliary syringe holding frame supporting arm and connecting cable 290 socket 296 when attached to the right hand side as shown in FIG. Dual interval timing relay 293 substantially eliminates the need for a microcontroller onboard the auxiliary syringe holding frame to coordinate the timing of stay insertion and auxiliary syringe discharge when not separately controlled by the operator. If auxiliary syringe ejection is synchronized with or at an interval in relation to inmate tissue cement pump 264 so that delivery line 298 shown in FIG. 102 should discharge as close to ejection slot forward extension 269 of inmate tissue cement pump at the front of the tool as shown as 264 in FIG. 102, then line 298 is rotated from its ordinary position in separate or unsynchronized use whereby it courses down the side of the tool.

The clips or nonallergenic elastic bands used to secure delivery line 298 to the side of the tool make moving the delivery line 298 ejection opening around into adjacent relation to ejection slot forward extension 269 quick and simple. Small ring rubber bands allow the two delivery lines from two auxiliary syringes to be quickly rotated around the tool to any position desired, allow either line to be crossed over the other, and since the delivery lines can branch, the area coated can be increased with the branches rotated to any peripheral position surrounding the tool.

In a stay insertion tool with a second socket for attachment of an auxiliary syringe holding frame on the left hand side, a second auxiliary syringe holding frame supporting arm and connecting cable socket 296 is mounted on the opposite side of inmate tissue cement air pump 264 as shown in FIG. 106. In FIG. 106, the structures surrounding thumb plunger-rod 238 and auxiliary syringe delivery line 298 such as the tool barrel 239 seen in FIG. 102 have been omitted for simplicity. Auxiliary syringe holding frame supporting arm and connecting cable 290 thus serves both for structural support and electrical connection to the insertion tool auxiliary syringe holding frame 284 components, with electrical current drawn from battery 263 in the upper compartment of battery and stay retention, retraction, and recovery electromagnet 242 compartment.

As a distinct component, auxiliary syringe holding frame supporting arm and connecting cable 290 is thus a miniature combined fluid and electrical conduit. As a structural element, casing or sheath 299 of auxiliary syringe holding frame supporting arm and connecting cable 290 is preferably made of nonferrous metal such as aluminum with sufficient flexibility for its wall thickness, diameter, and as shown in FIG. 104, typically of hexagonal cross-section allows the operator to bend it if necessary in order to obtain both manual clearance and a better view of the working field and syringe or syringes during operation.

XVI9c(6). Supporting Arm and Connecting Cable

FIG. 102 shows an auxiliary syringe holding frame containing a double syringe 284 with supporting arm and connecting cable 290 positioned for use, while FIG. 104 shows a supporting arm and connecting cable 290 before having been bent by the operator to gain the best line of sight and clearance to the working site. Auxiliary syringe holding frame supporting arm and connecting cable 290 is radially and bilaterally symmetrical. Further to obtain a clear view, a cabled lamp, endoscope, or angioscope, not shown in the drawing figures, is clipped or lashed alongside the tool.

Since the viewing angle may change during the procedure, auxiliary syringe holding frame with double syringe 284, supporting arm and connecting cable 290, and conductors 301 thru 306 are sufficiently pliable to allow frequent bending without fatigue fracture. In FIGS. 104 and 105, auxiliary syringe supporting arm and connecting cable 290 conductors 301 thru 306 have end contact pins secured in position at either end by protrusion through holes in end caps 307 and 308, through which conductors 301 thru 306 protrude with intervening electrical insulation.

FIG. 105 shows an auxiliary syringe supporting arm and connecting cable 290 in cross section or with either end-cap removed. At either end, auxiliary syringe holding frame supporting arm and connecting cable 290 thus resembles the base of a vacuum tube, but with a central opening for polymer syringe extension tube or cement and therapeutic substance delivery channel 300. This configuration allows end caps 307 and 308 to key the engagement of auxiliary syringe holding frame supporting arm and connecting cable 290 in auxiliary syringe holding frame supporting arm and connecting cable socket 296 and stay insertion tool inlet socket 296 mounted to the side of inmate cement pump 264 compartment.

The fluid delivery line within is made either from an extension provided by the syringe maker or a length of catheter polymer tubing. End-caps 307 and 308, which must securely position and insulate the fluid and electrical conductors inside it can be made of any strong plastic or mica, for example, these parts bonded together by means of a commercial adhesive selected for the specific materials used. The engagement of auxiliary syringe supporting arm and connecting cable 290 end-caps 307 and 308 in the upper and lower sockets can be viewed as tenons keyed by the protruding pin contacts, with the fluid channel at the center inserted into sockets considered complementary mortises somewhat similar to the connection of the stem to the shank of a smoking pipe.

To rigidly support auxiliary syringe holding frame 284, the upper or holder end of auxiliary syringe holding frame 284 supporting arm and connecting cable 290 must be firmly bonded by means of a strong adhesive to frame 284 about the syringe outlet which protrudes through holding frame bottom crosspiece 291, and which socket block 297 surrounds. To avoid the need for socket blocks with a different internal conformation at the upper or inlet end for each different kind of syringe, the inlet is funnel-shaped. Conductors 301 thru 306 to double or dual interval relay module 293, thence to motor 286 are bonded along the inside of frame 284 by intermittent application of a hot melt adhesive or small top or side acceptance spring arm clamps bonded to frame 284 with cyanoacrylate or hot melt adhesive depending upon the specific materials used.

In FIGS. 101a and 103, 294 is the dual syringe thumb-rest and 295 the finger stops. In the embodiment depicted in FIGS. 101 thru 105, battery and stay retention, retraction, and recovery electromagnet 242 compartment moves down and up with thumb-ring 244. In this embodiment, auxiliary syringe holding frame 284 supporting arm and connecting cable 290 is attached by insertion of its tool end into a socket that is bonded to the outside of stationary cement cartridge and air pump 264 compartment seen in FIG. 102. As represented in these figures, socket block 297 is mounted the left-hand side of the cement cartridge and air pump 264 compartment. Due to the levering forces imposed by auxiliary syringe holding frame supporting arm and connecting cable 290 as would break this bond, auxiliary syringe holding frame supporting arm and connecting cable socket 296 is joined to the tool with contacting parts scored or etched and a high bond strength epoxy cement, such as Aeropoxy ES6209.

Further to allow optimal viewability and also mounting stability and quick attachment or detachment, auxiliary syringe holding frame supporting arm and connecting cable socket 296 has an internal conformation that is multi-point, generally 6-point or 8-point, in the manner of a wrench socket to also accommodate six conductors. This configuration allows the tool end of auxiliary syringe holding frame supporting arm and connecting cable 290 to be inserted into auxiliary syringe holding frame supporting arm and connecting cable socket 296 at any of several different angles, redundant wires (six) and/or electrical terminal pin receptacles provided so that electrical connection is made regardless of which rotational orientation is chosen to support this positional flexibility.

The portion of the fluid delivery line from socket 296 to the front of the tool above ejection slot 248 consists of a length of tubing that is attached alongside the tool with the clips described below with its upper end plugged into the bottom of socket 296. When the thickness of the auxiliary cement or other fluid does not necessitate the use of a delivery line of any significant diameter, the portion of the line extension clip mounted alongside the tool can be left in position and sterilized with ethylene oxide gas (epoxyethane, oxirane, dimethylene oxide) along with the tool.

XVI9c(7). Control of Auxiliary Syringe Eject-Ahead or Eject-After with Determinate Timing The electrical components mounted to the back of and used to control stay insertion tool auxiliary syringe holding frame 284 as shown in FIGS. 101 thru 103 include surmounting miniature gear head dc motor 286 and adjustable delay/adjustable interval double or dual interval relay module 293, such as the Model TGCL Delayed Interval Relay Timer, Dual Adjustable, made by the Pelco Component Technologies division, Airotronics Timers and Controls, Cazenovia, N.Y. Stay insertion tool auxiliary holding frame 284 might incorporate a separate onboard battery to power dual interval relay module 293 and motor 286; thus reducing the number of conductors shown as 301 thru 306 in FIGS. 104 and 105 used to carry current to and from insertion tool on-board battery 263.

However, a separate battery incorporated into frame 284, while adding little to its size or weight, would not eliminate the need for conductors to carry the holding frame control signal from the break contact terminals shown in the inset to FIG. 106 as 313 and 314 on the tool to motor 286 and dual interval relay module 293 on holding frame 284 in any event, as would allow all of conductors 301 thru 306 to be eliminated. When auxiliary syringe holding frame dual delay interval timing relay module 293 break-contacts are separated by depression of thumb-ring 244, module 293 initiates an adjustable delay followed by an adjustable ON-time interval.

Dual delay interval relay module 293 applies the same timing control regardless of whether the tool has be set to cement-ahead (cement-before)- or cement follower(cement-during) operation. Accordingly, adjusting dual delay interval relay module 293 allows control over the timing of cement ejection and thus the extent of the stay that is coated. Dual interval relay module 293 being of the variable external type that is remotely controlled electrically, usually separate potentiometers with control knob 262 mounted on the tool above recovery electromagnet control knob 262 are used to control the delay and on-time intervals.

Alternatively, dual delay interval timing relay 293 is set so that the sum of these intervals corresponds to the average time that thumb plunger-rod 238 travels downward, and, potentiometer control knob located above lower control knob 262, which is used to adjust the field strength of stay retention, retraction, and recovery electromagnet 242, is used to adjust the relative proportion within the sum of these component intervals.

The compound angle and bendability of auxiliary syringe holding frame supporting arm and connecting cable 290 contribute to an adjustability essential to obtain a clear view of the operative field. The conductive pathways from break-contact terminals 313 and 314 to tool end-socket 236 are of the copper etched or printed circuit (printed or etched wiring board) type, laminated onto the non-conductive plastic tool, remaining portions of the circuit completed with wire.

XVI9c(8). Independent and Subordinated Control of a Stay Insertion Tool Auxiliary Syringe Holding Frame The stay insertion tool is ideally configured to serve as a mounting platform for tissue cement dispensers whether used in conjunction with the infixion of stays or not. Specifically, the configuration allows the operator to access a deep work site through a small incision, and the tool is ordinarily provided with a cabled lamp, fiber optic endoscope, angioscope, and/or excimer laser clipped or lashed alongside. Whereas in dependent or slave-follower use, current flows through dual interval relay module 293 and thence directly to motor 286, the switch then having circuited the current through dual interval relay module 293 and motor 286 in series, in use of auxiliary syringe holding frame 284 to discharge tissue cement or another therapeutic substance independently of the tool to which it is mounted, the circuit bypasses dual delay interval relay module 293, current flowing directly to motor 286.

As shown in FIGS. 87, 88, and 102, switch control buttons, such as slave-follower-to-independent and the reverse function switch are mounted on the outer side of thumb-ring 244. The wires run through thumb plunger rod 238 to hexagonal auxiliary syringe holding frame supporting arm and connecting cable socket 296 shown in FIG. 106 with inset enlargement. This switch may be one of several, where each switch is used to control a different auxiliary device, whether a laser, suction line, or an auxiliary syringe holder. In the slave or passive follower control mode, thumb-switches 309 thru 312 seen in FIGS. 87, 88, and 102 are not used, dual interval relay module 293 locking the operation of the auxiliary syringe holding frame 284 to the stay ejection cycle of the tool in timing function.

Several miniature switch types are suitable, to include bounceless (debounced) toggle, rocker, and slide types; however, those that provide a depressible button are preferred as expeditious. As shown in FIGS. 87, 88, and 102, so that the operator can move button switches 309 thru 312 as desired, the mounting of this and other miniature switches encircle as to be slidable or shiftably clampable along and rotatable around thumb-ring 244. The mounting of thumb-switches 309 thru 312 can be by means of fastening the switch to a miniature clamp ferrule of the screw-tightened kind made, for example, by the Wenzhou Jubang Light Industry Machine Company, Wenzhou, China.

However, for quicker and less distracting repositioning midprocedurally, a spring loaded shaft or spring steel pinch-type clamp ferrule that allows instant release and reattachment is preferred to lever or screw tightened types. The bases of thumb-switches 309 thru 312 are fastened to the outer surface of the slidable clamp ferrules with an adhesive specifically chosen for the metal or polymer materials at the interface to be bonded Lining the internal surface of the clamp ferrule with an elastomer will take up any space between the external surface of thumb-ring 244 and the facing surface of the slidable clamp ferrule, thus reducing any tendency of the switch to rock save by a completely exacting fit.

The motor or motors wired in series following dual interval relay module 293, independent control shunts the relay to control the motor or motors directly. The switch used should toggle, rock, or slide between independent and slave control positions, and additionally allow moderate thumb pressure placed upon the spring loaded switch while set to independent control to directly, that is, by shunting around dual interval relay module 293, actuate holder motor 286. Unlike a flange or straight handle index and middle finger stops, finger-rings 232 and 249 seen in FIG. 88 make it possible for the operator to remove his thumb from thumb-ring 244 to actuate switches 309 thru 312 by feel.

To this end, each of the switches 309 thru 312 are slid along thumb-ring 244 to the position of most comfort with least movement required to use these. As indicated when more auxiliary functions operated by means of an electrical switch are attached to the tool, each switch is of the same kind, any function being instantly selectable and controllable through a slight movement of the thumb. Holders can be mounted to both sides of the tool. This allows, for example, the application of medication under independent or direct operator control from the syringe or syringes to one side, and the application of tissue sealant from the syringe or syringes to the other side under tool slave-follower control.

Switches for auxiliary syringe holder 284 are mounted to the side of thumb-ring 244 to which the auxiliary syringe holder is attached, those for the side shown in FIG. 102 shown therein as 309 and 310, with those for use with a second auxiliary syringe holder attached to the other side seen in FIG. 88 as 311 and 312. Several switches can be mounted thus and slid for convenient use by the thumb, one switch each for each auxiliary device, such as an aspirator or laser, attached to the stay insertion tool that is electrically operated. The operator chooses the side and position of the switches for greatest right or left hand comfort and clarity.

For quick connect and quick disconnect capability, the upper end of auxiliary syringe holding frame 284 supporting arm and connecting cable 290 is pressed over the lower end of syringe mixing nozzle 292 shown in FIGS. 102 and 103, and the bottom end inserted into auxiliary syringe holding frame supporting arm and connecting cable socket 296, shown in FIG. 106. To allow socket 296 to be found instantly by touch, socket block 297 is mounted so that socket 296 stands proud at an incline from the side of the tool. Socket 296 is preferably molded integrally with, but can be bonded, using a strong and steam autoclave resistant adhesive to the rear side of inmate cement air pump and refill cartridge compartment 264, as shown in FIG. 102, a contralateral socket block if provided, bonded to the back side of the tool as depicted in FIG. 106.

A left-hand auxiliary syringe holding frame mounted contralateral to that shown to the right in FIG. 102 also has its own delivery line running down the opposite side of the tool as depicted in FIG. 106. Shown in FIG. 102, auxiliary syringe holding frame 284 is connected at the right-hand side of the stay insertion tool. The stay insertion tool can provide right and left-hand line entry sockets shown as 296 in FIG. 106 for attachment of auxiliary syringe frame 284 supporting arm and connecting cable 290 at either or both sides of the tool. Ordinarily, either supporting arm and connecting cable 290 provides a single lumen, the outflow of compatible contents from the syringes inserted into frame 284 at the moment transmitted together.

That is, compatible contents of plural auxiliary syringes can be conveyed together through the ordinarily single lumen shown in FIGS. 102 thru 105 of auxiliary syringe holding frame 284 supporting arm and connecting cable 290 connected at that respective syringe side of the stay insertion tool. Since the syringe contents to a given side of the stay insertion tool would be mixed when entering a common line, keeping these separate necessitates that line entry socket 296 and line 298 continue the luminal exclusivity and that syringes be inserted and removed from frame 284 as necessary.

Outer casing or conduit 299 shown in FIGS. 104 and 105 of auxiliary syringe frame 284 supporting arm and connecting cable 290 is not continued down to ejection slot 248, which is usually reserved for the ejection synchronized outflow of cyanoacrylate cement from pump 264. Instead, small ring nonallergenic elastic bands or small wire ties are used to position the outlet of each line about the distal or working end of the stay insertion tool.

XVI10. Binding of Lines and Cables Alongside the Stay Insertion Tool

XVI10a. Uses of Stay Insertion Tool Mounting Clips and Bands

Stay cement coating pump 264 and line 260 to eject or emit just above ejection slot 248 beneath ejection slot-overextended delivery line 260 tip 269 is not by attachment; these are integral parts of the tool. Incorporation whether by primary molding or secondary bonding is permanent. By contrast, the lines leading down to the working end of the tool from auxiliary syringes and the cables of devices such as angioscopes, laser pointers, aspiration lines, plain water or therapeutic solution irrigation lines, excimer ablation lasers, vortex cold air guns, and so on, when necessary, must be freely attachable and detachable from the tool.

When the tool is used for a single or similar procedures, these lines and attachments are more securely attached alongside the shaft of the stay insertion tool by means of clips suitable for long-term or permanent attachment. When any of a number of different lines and cables may need to be interchangeably fastened alongside the tool, small nonallergenic elastic rings or wire ties least add to the diameter of the tool at the working end, and low in cost, can be quickly snipped off and discarded. Except for the distal cinching of the adhesive delivery lines above the stay ejection slot, which can be accomplished simply with an elastic band to allow an auxiliary line to discharge beside or with a small length of bent tubing attached at the distal end, just to the front of the slot when shifted over with the end of a probe, attachment of the delivery lines to the tool is usually by means of clips.

Clips are mounted to the sides of the insertion tool to allow the permanent or semipermanent attachment of a variety of auxiliary devices alongside, that is, in long coaxial relation to the tool shaft. These would typically include rigid boroscopes or flexible fiberoptic endoscopes, angioscopes, ablation and light-activated surgical protein solder lasers, a suction (aspiration) and/or irrigation line, or a 'cooling' catheter for delivering hot or cold air from a vortex tube, or cold gas from a compressed and liquified cold air cylinder. Vortex tube-based 'cold' air guns have onboard (internal) controls. Cabled devices usually have a cable that leads to a control console from which the cable may or may not be disconnectable, or if connectable is so at the console and remote from the tool.

When the cabled device is always needed, as when the tool is used to repeatedly perform the same procedure, the cable can be permanently fastened alongside the tool with non-quick release clips. Otherwise, unless the cable can be quickly detached from the tool or a joint introduced in the cable for connection at the top of the tool, the tool must remain tethered to the console, even when the cabled device is not in use. For most cabled devices, the introduction of a joint poses considerable expense. Rather than the introduction of a joint that would leave the distal portion of the cable permanently occupying a position on the tool, making that position unavailable for attaching any other line or cable, quick disconnectibility is provided through the use of quick release clips or elastic bands.

Unlike an auxiliary syringe holder as addressed above in the section entitled Use of Commercial Syringes and Extension Tubes, controls for autonomous apparatus, at least when these are obtrusive, are not mounted on the insertion tool, the availability of an assistant assumed. Clips are more suited to use with stay insertion tools that are limited to a repeated procedure, so that the number of lines and their location relative to stay ejection slot 248 is consistent. Otherwise, small nonallergenic elastic bands are used, as addressed in the paragraph to follow. For this reason, and because clips are familiar, clips have been omitted from the drawing figures.

The number of cabled devices that can be run alongside the stay insertion tool is neither indicated by or limited to the front or side clips provided; additional devices can be mounted with tape, ties, or nonallergenic elastic bands, for example, the determinant being the need to avoid hindrance in access to the work site. Controls for lines attached to the tool that can be manipulated by touch alone and clamped directly onto the gown or to a belt. With a lamp or endoscope and cold and hot air line attached, for example, the stay insertion tool can be used to apply heat or cold to a ductus from without. Because thrombogenic temperatures cannot be avoided, doing this with an artery assumes that a platelet blocker or a vein that an anticoagulant has been administered.

However, such medication is always administered in interventional procedures, and here, because no foreign object is left in the vessel, the need for such medication should not extend beyond the periprocedural. Any lines used to deliver or remove materials from the work site arrive and depart at the top of the tool through "stay away" extended grommets of a nonallergenic elastic of the kind seen in steam irons or a wire helix as not to interfere with passing the tool through the entry wound and with the lines least obtrusive when extended over the patient to the opposite side. Fasteners for holding lines alongside the tool can be any of several types.

One is a conventional spring clutching rounded arm type clip, such as the type used to fasten wires to circuit boards, or "body clips" made, for example, by Traxxas, L. P., Plano, Tex. Other types are miniature side or top acceptance cable clamps or wire phone clips made of stainless spring steel, plastic with pressure sensitive adhesive backing, multiple wire to wall fastening strips, strips of tape, or small ring gauge nonallergenic elastic bands. Of these, small bands are preferred as allowing any number of lines in any arrangement to be held against the sides of the stay insertion tool, and allowing these to be rotated about the perimeter so that the substance discharged can be made to emit at a certain location in relation to ejection slot 248.

Clips for holding can be either of two types. The first type are conventional spring clutching rounded arm types, such as the type used to fasten wires to circuit boards "body clips" made, for example, by Traxxas, L. P., Plano, Tex., or side or top acceptance clips made of stainless spring steel. The latter are made in the form of simple curved leaf springs fastened at one end by a rivet to allow rotation and having a short length to the front that is bent slightly upward to assist in lifting each spring clip up and over the tube to be inserted beneath it.

The clips ideally include rounded arch-shaped elevations that have been sized to hold down tubes of at least the two most common size ranges, to include microcatheters and rigid endoscopes. The U-configured type spring clip that clutches about the tube is unsuitable as little adaptive to more than minor changes in the diameter of the tube to be held. Various tubular attachments are discussed below. Stainless spring steel can be obtained from numerous companies, to include Sandvik Materials Technology, Sandviken, Sweden, and finished clips of the kind described can be provided by numerous companies, to include the Newcomb Spring Corporation, Decatur, Ga.

XVI10b. Use of Stay Insertion Tool Side Mounting Clips to Laterally Juxtaposition (Fasten Alongside) an Endoscope An endoscope (medical borescope) or an angioscope, whether rigid or a fiberscope, with viewing end (objective lens) at the foot of the stay instion tool can allow the working area and the functioning of the tool to be observed through a small entry wound. Approaching from outside the ductus, stay insertion is best when the insertion arc is in expansion. For work in the arterial tree, viewing the rhythm of the systoles, to which peak the insertion of the stay is best timed, is made easier. Advancement in rigid endoscopes allow a sufficient field of vision or the view to be manipulated with mirrors and/or prisms, and an inline plate with flat screen monitor and manipulation controls is ergonomically advantageous compared to the use of a video monitor. The means for adapting to a pulse that is too fast and/or irregular are addressed above in the section entitled Motional Stabilization of the Implant Insertion Site.

The diameter of such endoscopes, made, for example, by Ethicon Endosurgery, Cincinnati, Ohio, is one centimeter (see, for example, Kim, K., Kim, D., Matsumiya, K., Kobayashi, E., and Dohi, T. 2005. "Wide FOV [Field of Vision] Wedge Prism Endoscope," *Institute of Electrical and Electronics Engineers Engineering in Medicine and Biology Society Conference Proceedings* 6:5758-5761; Ryndin, I., Lukasewycz, S., Hoffman, N., Nakib, N. A., Best, S., and Monga, M. 2005. "Impact of Heads-up Display Imaging on Endoscopic Task Performance," *Journal of Endourology* 19(8):964-967; Kobayashi, E., Sakuma, I., Konishi, K., Hashizume, M., and Dohi, T. 2004. "A Robotic Wide-angle View Endoscope Using Wedge Prisms," *Surgical Endoscopy* 18(9):1396-1399; Schier, F., Beyerlein, S., and Gauderer, M. W. 2002 "Imaging for Endoscopic Surgery: New Developments Applicable to Pediatric Surgical Interventions," *Pediatric Surgery International* 18(5-6):459-462; Kobayashi, E., Daeyong, K., Sakuma, I., and Dohi, T. 2001. "A New Wide-angle View Endoscopic Robot Using Wedge Prisms," *Computer Assisted Radiology and Surgery* 1230:149-153). Some current wireless video fiberscopes (flexible boroscopes), such as the Tactical Electronics and Military Supply L.L.C., Broken Arrow, Okla. Model VFS 2 can be attached.

Examination of the insertion tool when not functioning smoothly is generally determined and any build up of adhesive accomplished by withdrawal of the tool from the work area for direct viewing, which the transparency of the materials used allows. When the entry wound is large enough, the overhead lamps and head lamp should provide adequate illumination down through the entry wound, and binocular telescopes should afford sufficient magnification; however, to minimize trauma, means are applied to allow access and visibility with the least incision. Using the side mounting clips, small downward directed lamp that draws power from the internal battery can be attached to the side of the tool.

An endoscope can, however, provide a more detailed view of the work area. To allow a closer view, a conventional flexible or fiber optic endoscope with light delivery system can be affixed alongside the tool. To attach the endoscope, the clips are positioned at intervals down the sides of the stay insertion tool. The endoscope can target the ductus to receive the stay implants or to discover that adhesive is not properly applied before this becomes apparent through clogging sensed tactually, the front edge of the ejection slot roof. The roof of ejection slot stay ejection slot 248 and the sides of the insertion tool are transparent, allowing the reflective liquid adhesive to be distinguished from the flat tantalum coating of the stays.

XVI10c. Use of Stay Insertion Tool Side Mounting Clips to Juxtaposition (Fasten Alongside) a Vacuum (Aspiration, Suction) Line The incorporation into the stay inserter of an onboard wholly contained miniature aspirator pump to drive a closed circuit suction line with suction inlet at the foot of the tool to allow drawing a collapsed or receding near ductus wall up to the foot or sole of the inserter with the object of eliminating a piped aspiration line is discounted as constantly fouled by the entry of body fluids. Clips on the side of the stay insertion tool opposite those for the attachment of an endoscope allow a vacuum (aspiration, suction) line to be fastened alongside the tool. While the suction line is available for the conventional removal of fluid that obscures the view, its primary a means for supporting the ductus so that it can be implanted without collapsing beneath the tool as discussed above in the section entitled Arcuate Stent-stays (Stays, Stent-ribs, Ribs) or Stays for Use with Stent-jackets. When suction works, it eliminates the need to station a muzzle-head at the level of implantation as, thus preserving a major advantage in the use of stays as opposed to miniballs.

To distribute the force of suction on the outer surface of the ductus to be treated, the distal soft tip of the suction tube may be flared outward towards the sides as aligned to the long axis of the ductus. A collapsed or collapsing ductus can then be drawn up toward the sole of the tool to allow the stays to be inserted to the depth sought. The disposal of used vacuum tubes and control of the vacuum level as, for example, by means of a magnetoresistive or Hall effect flow meter, lies outside the present scope. Bands and clips for fastening various kinds of lines, such as those of cold air gun and vacuum lines alongside the stay insertion tool are addressed in the section to follow.

A small-gauge length of tubing can, for example, be secured to the side of the insertion tool with its outlet fixed in position beside the stay ejection slot. This tube can be transferred from the cold or hot air outlet of a vortex tube, or 'cold air gun,' for example, to a vacuum pump to serve as a suction (aspiration) line, for example. This can be accomplished either by redirecting or switching the proximal end of the tube through an air switch valve or by physically disconnecting the end of the tube and reconnecting it to the pump.

The couplings (joints, unions) and valves for such purpose well known. As specified in the section above entitled Turret-motor Operational Modes, reducing the mobility and the level of chemical activity in the tissue to be implanted can allow greater precision and a lessening if not the avoidance of unwanted immediate and postprocedural reactions such as swelling. Although the use of stays should not result in contact with the intima, the stabilization afforded by cold pertains to the media as well. A cold air gun or supply line in the form of a narrow hose or tube from a source of cold air allows the tissue for treatment to be stabilized.

XVI10d. Use of Stay Insertion Tool Side Mounting Clips to Juxtaposition (Fasten Alongside) a $CO_2$ Cylinder or Cold Air Gun Line Unlike ballistic implantation, where the exit velocity and not the restorative force of the thumb plunger rod return spring 245 in a control syringe-configured stay insertion tool as shown in FIGS. 87 and 88 or the direct tactile control of a pistol-configured tool as shown in FIG. 89 determines the force and depth of penetration, the increased hardness of the tissue has little consequence with a hand tool. Excessive or inadequate restorative force of the spring in a control syringe-configured tool is easily adjusted with the thumb. Temperature change with or without application of a supporting solution can sometimes be used to affect tissue hardness.

To counteract the retardation in the rate of curing of the tissue sealant or adhesive applied by the stay insertion tool during implantation (addressed above) that chilling would also effect, an immediate source of warm air to follow the cold air is necessary. Furthermore, an immediate remedy should be available if through human error the temperature were set so low that it would freeze and not just chill tissue. Quickly returning the tissue to a warmer temperature is accomplished by switching the air supply line from the cold to the hot outlet of the same cold air gun, existing means for accomplishing such numerous.

Provided an assistant is present, for this immediate reversibility between cold and hot temperatures, the use of a cold air gun is preferred. The unassisted use of cold gas is most easily and least divertingly obtained by fastening a medical cryospray gun, can, or $CO_2$ cartridge with attached nozzle and connector to the proximal end of a delivery line (length of catheter) clipped alongside the insertion tool. Fastening the gun or can at the side or front of the gown and allowing sufficient slack, tethering hindrance and the need for more than touch alone are virtually eliminated.

XVI11. Use of Stay Insertion Tool

The use of stay insertion tool mounting clips is addressed above in separate sections. Stay retention, retraction, and recovery electromagnet 242 and magnet controls 262 are tested on a small ferrous metal object that poses the same resisance to attraction. Any auxiliary lines, whether for temperature-changing ('cooling' catheter), aspiration, or a cabled device such as an endoscope cable, lamp, or a holder and delivery line for an auxiliary dual-cartridge as addressed above in the section entitled Stay Insertion Tool Auxiliary Syringes are attached and tested. When cyanoacrylate cement is to be used, a cartridge containing acetic acid can be used first to flush through the delivery line.

As a retardant, acetic acid reduces the tendency for the cement to cake and clog at the distal tip. To avoid wasting stays, this and the step that follows must done before a clip of stays is introduced into the stay chamber (stay bay). Shown in FIG. 87, surgical cement, a fluid pharmaceutical or therapeutic, medication, tissue hardener, or fixative refill cartridge 236 is inserted into the refill cartridge compartment 235, lower end first. Pushing the upper end of refill cartridge 236 into refill cartridge compartment 235 causes hollow tissue cement or therapeutic fluid delivery line 260 inlet hollow puncture needle 237, which protrudes up through the floor of refill cartridge compartment 235 at the inception or upper end of the surgical cement or other fluid supply line 260, to puncture the bottom of the refill cartridge 236 much as does loading a $CO_2$ cartridge into an airgun.

In FIGS. 87 and 90, tissue cement or therapeutic fluid delivery line 260 conducts fluid from fluid refill cartridge 236 down the front of the stay insertion tool to an overhang at the stay ejection slot 248. Repeatedly depressing thumb rod ring 244 and thus thumb rod 238 when rod 238 is engaged with pump piston 233—or with the pistol-configured embodiment shown in FIG. 89—repeatedly pulling trigger 261, causes cement compartment pump piston 233, to advance cement or other fluid 236 down through fluid feed line 260 in increments until cement begins to emerge at the lower or distal end of fluid feed line 260 to coat each stay as it is ejected.

The tip of the adhesive line is wiped clean with a sterile acetone-soaked cloth. To allow refill cartridge 236 to be inserted into refill cartridge compartment 235 easily, the top of refill cartridge 236 and/or upper ledge or lip of fluid refill cartridge compartment 235 interface or meet at a slight incline. Since a separate syringe can be connected directly to inlet hollow puncture needle 237 or preliminary cartridges used to prime fluid feed line 260 so that fluid will emerge with the first stay to be ejected, the capacity of refill cartridge 236 in refill cartridge compartment 235 is not governed by the volume of fluid needed to fill fluid feed line 260 before stays 231 are coated.

Such a separate syringe or multiple refill cartridges 236 can be used to preload, prime, or flush fluid feed line 260. The lower or distal portion of feed line 260 passes through the entry incision, and to allow the incision to be as small as practicable and take up the least volume of fluid from the smallest practicable refill cartridge 236, is held to the smallest usable diameter. The cyanoacrylate cement loaded is usually light in viscosity and consistent with a feed line of slightly greater than capillary diameter. If necessary, fluid feed line 260 is flushed of set cement by removal from the patient and insertion of a refill cartridge 236 in refill cartridge compartment 235 containing acetone, which is run through the line.

A cement cartridge is then fully discharged through the line before the tool is reintroduced into the patient. A clip or strip of stays 231 is inserted into stay refill cartridge compartment 250. The setting and response of dual interval relay module 293 is checked and if necessary, adjusted. Two or more stays are ejected to test the tool for properly coordinated timing between stay and cement ejection before introducing the working end of the insertion tool through the entry wound. If necessary, the adhesive ejection timing slide valve in the side of the cement air pump and refill cartridge holding chamber (cylinder) is used to adjust the moment of inception for adhesive ejection.

If the tool still does not perform correctly, the transparent tool allows the cause of malfunction to be directly observed. If used, auxiliary syringes in holding frames must be charged (filled) down to the exit tip or tips. The setting on an attached commercial tissue sealant or medication holding frame or frames must be tested, as must any other attachments used. As applicable, the timing coordination between an auxiliary syringe or syringes in relation to the stay ejection cycle and another holding frame if present must be tested to the accuracy actually needed. The amount of substance released determined by the duration of discharge, timing must be adjusted to control this factor as well as to properly coordinate the action of the holding frame or frames with that of the tool.

A small diameter endoscope and aspirator line will almost always be used and should be pretested. When the preliminary tests described below for inter- and intralaminar separation are omitted, a dental probe-hook is should still be used to evaluate the pliancy of the ductus. Upon completion of the procedure, the stay refill-strip and adhesive cartridge are removed, discarded, and inmate adhesive delivery line or tube 260 flushed through with a refill cartridge containing acetone or a commercial long chain cyanocrylate glue remover or solvent such as Duro® Super Glue Remover, or acetone, which may be in the form of nail polish remover.

Alternatively, the line can be flushed through by placing the distal end of a tube connected to a syringe containing the solvent over stay cement supply feed line or applicator tube 260 inlet hollow puncture needle 237. The tool must always be sterilized immediately following and preceding use. Referring to FIG. 91, taking care to slip toe 253 through the entry wound (incision, portal) first, the stay insertion tool is passed through the entry wound and positioned on the ductus with toe 253 and arcuate bottom of the working end flush. The depth of implantation is set by adjusting the downward force on the ductus.

When properly employed on a ductus of the prescribed diameter for the specific tool used, setting positioning sole 254 with no more downward force than is necessary to keep the tool from shifting will achieve subadventitial placement. The attachment of a suction hose (aspiration line) as discussed above in the section entitled Use of Stay Insertion Tool Side Mounting Clips to Laterally Juxtaposition (Fasten Alongside) a Vacuum (Aspiration, Suction) Line and cold air line as discussed above in the section entitled Use of Stay Insertion Tool Side Mounting Clips to Laterally Juxtaposition (Fasten Alongside) a Cold Air Gun Line can assist in reducing any tendency for an empty ductus to collapse under the tool.

The tool can be used to direct cold or hot air at the outside of a ductus through the incision made to insert the stays and/or the stent-jacket, and since it can be quickly switched between hot and cold air (or gas), is conveniently used thus even when the intraductal implants are miniballs. Applying somewhat more force will cause the stays to enter more deeply into the media as is unavoidable should upon testing as described under the section below entitled Site-test on Extraluminal Approach for Intra- or Inter-laminar Separation (Delamination) the adventitia reveal a propensity to delaminate from the subjacent tunic.

Whenever the inmate cyanoacrylate or an auxiliary syringe containing tissue sealant is used to automatically apply cement to each stay as it exits, retracting a stay that failed to enter true back into the ejection slot would introduce cement into and likely clog the ejection slot. However, once a stay has completely ejected, even though turning up the magnetic field strength (battery current) allows it to be withdrawn and retained on the tool, the stay cannot be returned to the attitude necessary to cause it to reenter into the ejection slot; gravity pulls the stay downward. precluding reverse reentry.

No attempt should be made to reenter the stay into the ejection slot, and the operator should not allow the restorative force of the thumb plunger spring to cause the stay to drop off the end of the tool before the tool has been completely withdrawn from the body and the clingling stay removed. The front of the ejection slot should then be cleaned of any cement. Any concern that the tool may not eject properly should prompt the discharge of a test stay. The amount of downward force might be quantified with a built in digital force gauge or scale; however, clinical experience is preferable, the recommendation of specific forces for variable conditions ill advised. While improbable, a ductus that slides or rolls aside despite the indented sole of the tool is stabilized with the aid of a probe.

The stay is inserted. To tamp down and seal the incision, the tool is moved slightly forward or reversed, and a slight downward force applied. If implantation is suspected to be mispositioned prior to ejection, the recall magnet is energized to withdraw the stay and the tool tested outside the body. The operator confirms the successful sealing of each before proceeding to the next. If the ductus stay insertion incision is not sealed, the tool is removed and a long chain methacrylate adhesive introduced into the ductus stay insertion incision by means of a microcatheter as described above in the section entitled 378.3 or at the tip of a narrow probe. The stay insertion tool is tested outside the body.

In situ, transparency serves not only to improve the viewability of the work area from different angles to confirm proper contact and circumferential relation of the tool sole to the ductus surface, but with the aid of an optionally attachable endoscope, allows the stays to be observed as these pass through stay ejection slot shown in FIG. 90 as 248. Should the ductus to be stay-implanted be collapsed or collapse under the stay insertion tool or waver due to smooth muscle action, a vacuum (aspiration, suction) line fastened to the side of the tool opposite the endoscope is used to better stabilize and achieve the tool-ductus relation required. In some instances, an artery may require to be immobilized with a forceps or hemostat.

XVII. Testing and Tests

XVIII. Need of a Means for Testing the Resistance to Puncture, Perforation, and Delamination of Tissue Requiring Treatment Testing pertains to equipment manufacture and its application in the clinic or catheter laboratory. Quality control testing during and after manufacture adheres to established medical equipment manufacturing procedures. As in differential diagnosis and therapy generally, the number of variables is large, some may be unknown, and if known, difficult or impossible to gauge, and more difficult still to gauge in context. To some extent, the variables will be peculiar to the individual patient, whose condition overall may add comorbidities, and as always, nonawareness of or discounting a significant variable could result in a misapplication of data. Data that can be immediately put to practical use with reasonable confidence is sought, and data collected and tested ex vivo with precision equipment in a laboratory disregarded despite its theoretical value.

The results of such testing appear in the literature. Preprocedural and postprocedural examination is with noninvasive imaging equipment, intravascular ultrasound (which is invasive) used only when indicated by the imaging results and/or the prospective procedure is invasive in any event. The diagnosis spoken of here is that pertinent to mechanical properties of tissue under evaluation for ballistic implantation; however, the development of sensors that allow chemical analysis to identify different conditions of disease expands the zone of diagnostic utility. The midprocedural use of intravascular ultrasound allows susceptibility to and de facto intramural delamination to be evaluated before and after treatment.

Provided treatment can is accomplished and obtain the result needed quickly, the need for a followup invasive procedure is eliminated. Delamination, for example, can be accomplished by passing a fine aspiration line leading to a highly sensitive vacuum gauge able to distinguish fine differences in vacuum pressure through the access incision and up against the adventitia or perivascular tissue adherent thereto. Provided examination can be completed before a serious risk of ischemia obtains, the prospective radially outward retractive force to be exerted by a stent-jacket, for example, is applied, preferably at several points, the consequences observed over an interval, another catheter with hypotube used to deliver therapy, and the intravascular ultrasound used to view the result.

Such testing is made more dependable through the use of an aspiration catheter equipped with a suction pad having aspirating holes spaced as does the prospective stent-jacket. The delamination can be responded to by using wide cyanoacrylate cement coated stays, time allowed for the cement to set, and the delamination reexamined. Alternative methods for responding to delaminations, to include the use of miniballs coated with a lower temperature denatured or flowed protein solder and the application of heat are set forth above.

At least for procedures that will necessitate endoluminal entry, the use of a multibarrel radial discharge barrel-assembly for diagnosis and therapy, as a tool in itself and regardless of whether use thus is followed by miniball discharge, is considerable, and rises in proportion to the extent of the software support afforded. While the testing and treatment accomplished are ordinarily intended to precede ballistic implantation using the same barrel-assembly, a multibarrel radial discharge barrel-assembly, especially one driven by an automatic positional control system, can serve purely as a diagnostic and/or therapeutic tool capable of immediate treatment responsive to the point to point findings obtained.

This integral diagnostic and therapeutic capability is not shared by conventional means such as balloon catheters and rotational atherectomizers, for example, which must rely upon the support of imaging means incapable of providing treatment and may, as would therapeutic means such as a laser or rotatory ablation device, necessitate separate endoluminal entry. Machine positional control allows the muzzle-head to immediately and accurately return to the point tested with a therapeutic catheter or an exit-hole for discharge. Diagnostic software can eliminate the time a human operator or assistant would need to convert each test finding into the appropriate therapeutic response and then bring the therapeutic catheter to the correct position.

The positional control system provides quick and accurate repositioning of the muzzle-head to each point tested for treatment, and if intended, implantation, with followup testing at each point if desired. Even when the system is operated manually in a semiautomatic mode to diagnose and treat a simple condition, the advancement and retraction of injection catheters, for example, can be controlled by the controller as an auxiliary function using conventional miniature electrically or pneumatically operated pistons. Eliminating direct control by the operator eliminates human error that could, for example, allow the tip of an injection needle to remain projected during transluminal movement, and further contribute to making the barrel-assembly a potent tool for diagnosis and treatment.

Operated under fully automatic control by coordinated diagnostic, therapeutic decision-making, and critical path software, the barrel-assembly is instantly and accurately repositioned in a fully coordinated sequence among a plurality of points to be tested and treated. The critical path software distinguishes among the points so that each is tested and treated independently and coherently; however, by coordinating the point to point sequence of movements according to least overall time criteria, the software optimizes the efficiency of motion control so that the separate points are in effect, treated concurrently, the resultant action blended as to appear continuous.

Software to function thus can be devised for a specific syndrome or condition, such as ileocolitis or atherosclerosis, and reduces the response and procedural times that a human operator could achieve to a degree that makes treatment thus practicable; that is, the time a human operator with the support of assistants would need to accomplish the same end would usually disallow such a procedure as too complicated, too lengthy, and too expensive. The testing addressed here is that intraprocedural for immediate application to implant insertion and that postinsertion to confirm successful insertion. Quantitative findings are intended as a simple adjunct to clinical judgment, and not to suggest a level of confidence that no data, regardless of its precision, complexity, or cost, could provide.

The section above entitled Airguns contains some information on converting test values into equivalent exit velocities. Because diseased tissue considerably exceeds in range of variation that found in normal tissue effectively negating the data anyway, and because the tissue may be in transition, that is, undergoing change or metaplasia, means for testing the mechanical properties of the tissue to be treated are accomplished using the simplest and least expensive equipment available. To this end, stay insertion tools and barrel-assemblies can carry onboard the testing equipment needed for their use, either by attachment or incorporation.

Either can attach an angioscope to allow a view that is clear enough to distinguish surface indentation and ductus wall elasticity, for example. If that relation is consistent and no visual evidence to the contrary is seen over the segment, then elasticity is inferred on the basis of indentation. Testing necessitates additional time and money and when possible is avoided entirely or kept to the minimum, using relatively simple and inexpensive means for obtaining essential measurements. Generally, the placement of wide stays coated with cyanoacrylate cement seldom warrants testing for tunical or intratunical delamination or for pull-through; a quick probing to rule out malacotic areas should be all that is needed.

A ductus too malacotic to retain these over time despite treatment with a tissue hardening or sclerosing agent indicates the need for replacement with a graft. When testing is felt warranted, a stay insertion tool equipped as addressed above in the section entitled Stay Insertion Tools, can itself be used to test for extraluminal approach or a mechanical force and indentation service catheter can be passed through the incision at the body surface Stent-jacket resilience is inferred on an intuitive basis using the information available, to include visual and any acquired through simple testing to determine tissue hardness. Preprocedural imaging that does not furnish mechanical information to indicate implant suitability and retainability is of little practical value for the purpose at hand.

Concerns that a stent-jacket may lack sufficient flexibility for close compliance with the distention and contraction of the ductus is better responded to by using a more pliant jacket than by initiating an intricate and time-consuming investigation; the use of intravascular ultrasound to determine arterial wall elasticity in relation to blood pressure, for example, measures a mechanical property with a potential benefit only as time and money permit. For preinsertion or pre-placement testing whether extraluminal to place stays or endoluminal to place miniballs, testing is preferably by means of relatively inexpensive catheteric mechanical and magnetic sensing probes. These include catheteric force gauge and magnetometer probes, and preferably, probes that combine these functions, eliminating the need to withdraw one tool and insert another.

Such consolidation of functions has the additional advantage of making possible the immediate interconvertibility between the different types of data when necessary. Means that provide positional as well as mechanical information provide such information with less time, complexity, and expense. With extraluminal approach, the probe, usually attached alongside the stay insertion tool, is inserted through the access incision at the body surface and applied to the adventitia. With endoluminal approach, the probe is passed through an unused barrel-tube as service-channel or the central channel of the barrel-assembly, thereby eliminating the need for entry more than once through the entry wound.

Routine postprocedural testing where no adverse sequelae have appeared is by noninvasive imaging. Whereas angioscopes, aspiration lines connected to vacuum gauges, and combination magnetometer/force-measurement probes, for example, can be passed through an available barrel-tube as service-channel or through the central channel, an intravascular ultrasound probe and/or excimer laser must be passed down the central channel to look out coaxially at the center of the nose. Larger gauge barrel-assemblies can incorporate an intravascular ultrasound probe and/or excimer laser in side by side relation, the degree of abaxially inconsequential.

The ability to incorporate catheteric probes diminishes with decreasing gauge according to the miniaturization that might be achieved; however, the coronary arteries of a neonate, tiny and end-arterial excepted, small vessels do not require treatment thus. Stay insertion tools can attach angioscopes, aspiration lines, and combination magnetometer/force-measurement probes, for example. Rather than to allow the tool to be tethered by the remote connections of these, the lines attach to connectors at the tool. The use of costly imaging midprocedurally is avoided. For example, when stays are used without an ablation or an angioplasty, intravascular ultrasound is the only circumstance that necessitates luminal entry.

By the same token, since the lumen must be entered to place miniballs in any event, intravascular ultrasound may, however, prove of value in endoluminal approach by revealing conditions that would increase susceptibility or resistance to penetration, delamination, or pull-through. Intravascular ultrasound catheters have achieved a thinness of a few French that allows these to be passed down the central channel or an edge-discharge muzzle-head so that the need for separate entry for imaging and therapy is eliminated. Combination-form barrel-assemblies can incorporate or allow the insertion of such a viewing aid, and larger barrel-assemblies can have an angioscope and/or intravascular ultrasound probe built in to look out from the center of the nose.

For placing stays, no more is necessary than a quick check to confirm that the ductus wall is not so malacotic that ductus-intramural implants must not be used. When quantitative testing is necessary, as when the degree of sclerosis should determine the force and speed with which stays are inserted; a control syringe-configured stay insertion tool with built in calibrated compression spring adjustment and testing device as addressed above in the section entitled Stay Insertion Tools, can be used. In contrast, control with a noncalibrated control syringe-configured stay insertion tool is limited to the intuitive reduction in speed of insertion that the operator can achieve by not allowing the compression spring to expand according to its intrinsic expansion (restorative, return) force.

The operator does this by slowly lifting his thumb to moderate the speed with which the spring, hence, the thumb plunger-rod with attached ejection blade, and thus the momentum of insertion, is allowed to expand. Alternatively, to insert the stay through and/or into harder, or sclerosed tissue, the operator can remove his thumb, allowing the spring to snap back and insert the stay at the momentum inherent in its expansion force. A stay insertion tool can be produced to automatically adjust the thumb plunger rod spring tension into the parameters of stay insertion; however, the infrequent need for such a feature makes it cost ineffective. The mechanical properties of the tissue to be treated and the structures surrounding this tissue are primary concerns.

Since compared to healthy tissue, the mechanical properties of diseased tissue vary over a much wider range, a means for testing the actual tissue considered for treatment in situ may be imperative. For example, most vascular disease atherosclerotic, degradation in elasticity of the arterial wall due to infiltration by white blood cells that activate collagen and elastin-degrading proteases, and the prognosis for this degradation to continue with the administration of protease resistant medication (see, for example, Nichols, T. C., Busby, W. H., Merricks, E., Sipos, J., Rowland, M., Sitko, K., and Clemmons, D. R. 2007. "Protease Resistant IGFBP-4 Inhibits IGF-I Actions and Neointimal Expansion in a Porcine Model of Neointimal Hyperplasia," *Endocrinology* 147(12):5634-5640, that does not interfere with the clearing of fibrin, (see, for example, Sachs, B. D., Baillie, G. S., McCall, J. R., Passino, M. A., and 13 other authors 2007. "p75 Neurotrophin Receptor Regulates Tissue Fibrosis Through Inhibition of Plasminogen Activation via a PDE4/cAMP/PKA Pathway," *Journal of Cell Biology* 177(6):1119-1132) requires ascertaining whether the arterial wall has retained sufficient strength to proceed with implantation, and if so, with miniballs introduced using an airgun or nonimpactively inserted stays introduced with a special hand-tool, as addressed above in the section entitled Stay Insertion Tools.

Due to variability in the mechanical properties of diseased tissue from:

a. Condition to condition and in severity or stage of advancement (see, for example, Maurice, R. L., Dandah, N., and Tremblay, J. 2012. "Imaging-based Biomarkers: Characterization of Post-Kawasaki Vasculitis in Infants and Hypertension Phenotype in Rat Model," *International Journal of Vascular Medicine* at http://www.hindawi.com/journals/ijvm/2012/364145; Cho, I. J., Shim, C. Y., Yang, W. I., Kim, S. A., Chang, H. J., Jang, Y., Chung, N., and Ha, J. W. 2010. "Assessment of Mechanical Properties of Common Carotid Artery in Takayasu's Arteritis Using Velocity Vector Imaging," *Circulation Journal* 74(7):1465-1470; Cheung, Y. F., Brogan, P. A., Pilla, C. B., Dillon, M. J., and Redington, A. N. 2002. "Arterial Distensibility in Children and Teenagers: Normal Evolution and the Effect of Childhood Vasculitis," *Archives of Disease in Childhood* 87(4):348-351), b. Age to age (see, for example, Maurice et al. 2012 Op cit.; Majumdar, A. P., Jaszewski, R., and Dubick, M. A. 1997. "Effect of Aging on the Gastrointestinal Tract and the Pancreas," *Proceedings of the Society for Experimental Biology and Medicine* 215(2):134-144);

c. Sex to sex (see, for example, Benetos, A., Waeber, B., Izzo, J., Mitchell, G., Resnick, L., Asmar, R., and Safar, M.

2002. "Influence of Age, Risk Factors, and Cardiovascular and Renal Disease on Arterial Stiffness: Clinical Applications," *American Journal of Hypertension* 15(12):1101-1108);

d. Individual to individual (see, for example, Augst, A. D., Ariff, B., McG Thom, S. A., Xu, X. Y., and Hughes, A. D. 2007. "Analysis of Complex Flow and the Relationship Between Blood Pressure, Wall Shear Stress, and Intima-media Thickness in the Human Carotid Artery," *American Journal of Physiology. Heart and Circulatory Physiology* 293(2):H1031-H1037; Kornet, L., Lambregts, J., Hoeks, A. P., and Reneman, R. S. 1998. "Differences in Near-wall Shear Rate in the Carotid Artery within Subjects are Associated with Different Intima-Media Thicknesses," *Arteriosclerosis, Thrombosis, and Vascular Biology* 18(12): 1877-1884);

e. Location to location (see, for example, Umale, S., Chatelin, S., Bourdet, N., Deck, C., Diana, M., and 4 others 2011. "Experimental in Vitro Mechanical Characterization of Porcine Glisson's Capsule and Hepatic Veins," *Journal of Biomechanics* 44(9):1678-1683; Egorov, V. I., Schastlivtsev, I. V., Prut, E. V., Baranov, A. O., and Turusov, R. A. 2002. "Mechanical Properties of the Human Gastrointestinal Tract," *Journal of Biomechanics* 35(10):1417-1425; Tseders, É. É. and Purinya, B. A. 1975. "The Mechanical Properties of Human Blood Vessels Relative to their Location," *Mechanics of Composite Materials* 11(2):271-275; Kaski, J. C. 2003. "Atheromatous Plaque Location and Arterial Remodelling," *European Heart Journal* 24(4):291-293); and f. Preceding or following an intervention (see, for example, Giannattasio, C., Failla, M., Grappiolo, A., Bigoni, M., Carugo, S., Denti, M., and Mancia, G. 1998. "Effects of Prolonged Immobilization of the Limb on Radial Artery Mechanical Properties." *Hypertension* 32(3):584-587), a test that goes directly to the actual tissue and equipment used is beneficial and often essential to decide upon a course of treatment.

Since elevated protease levels are suspected to contribute to the rupture of plaque leading to acute cardiovascular events (Chen, J., Tung, C. H., Mahmood, U., Ntziachristos, V., Gyurko, R., Fishman, M. C., Huang, P. L., and Weissleder, R. 2002. "In Vivo Imaging of Proteolytic Activity in Atherosclerosis," *Circulation* 105(23):2766-2771), at least when angioplasty and stenting are elective, medication that moderates the action of proteases may have been initiated well beforehand. Whether or how to stent the artery by the various methods described, whether medication would allow a retention in elasticity, and so on, can determine whether such treatment should proceed.

That plaque tends to become progressively calcified is meaningful according to how much of it remains following the steps taken to eliminate it. The resistance of the tissue to be treated to puncture, perforation, and delamination can be critical for success. Even with antithrombogenic medication administered, punctures produce swelling that serves to provide spontaneous self-sealing, and the inside of the stent-jacket may be wetted with a topical coagulant such as Gelfoam®, Gelfoam® with thrombin, Oxycel®, Surgicel®, FloSeal®, Avitene®, bipolar cautery, or argon beam coagulation to assist in sealing a puncture.

Nevertheless, a puncture will be associated with an errant discharge that could injure surrounding structures, possibly damage nerves, and is to be prevented. In testing, a continuous rod sees the expulsive force at its proximal end and directly transmits that force to the tissue at the distal end. There is little transmission loss in velocity, hence force of impact. By contrast, the miniballs are more subject to losses in momentum due to any differences in the bends and rolling resistance of the barrel-assembly that distinguish the conditions of the test from those of actual use.

Provided the test is conducted under the same conditions of barrel-assembly bends and length as in the actual use for which the test is conducted, this can be compensated for by taking the test result as proportional For this reason, it is essential that the test be conducted under the conditions of bending of the barrel-assembly to apply in actual use. In situations where the consequences of a puncture are less important than procedural speed, a preliminary discharge of a single miniball at the affected tissue with the force presumed necessary is performed, the result evaluated, and the appropriate adjustment made.

Otherwise, no discharge of miniballs into diseased tissue should precede puncture strength testing. While intraoperative time constraints may preclude pretesting for each individual miniball to be implanted, the puncture strength of the specific lesioned tissue in the specific patient should be determined. This value is ascertained by reproducing as closely as possible the effect of a miniball on the tissue to be implanted, and in this way, obtaining information reliable as may be had concerning its penetrability and puncture resistance. The longitudinal and radial strength of the lumen wall and its resistance to separate intra- or inter-laminarly (tunically delaminate) central in determining the applicability of the means described herein, a malacotic condition of the outer layer or layers of any type ductus will present multiple symptoms and seldom go undiagnosed.

The limitation of such a condition to the outer layers is not an aspect of the recognized vasculitides (see, for example, www.nhlbi.nih.gov/ . . . /Diseases/vas/vas_all.html), and a test for wall strength is provided in the section below entitled In Situ Test on Endoluminal Approach for Susceptibility of the Ductus Wall to Puncture, Penetration, and Perforation. Since testing is prescribed for aeroballistic implantation regardless of whether the implant will then be subjected to magnetic traction, a deviant condition could escape detection only when the test is not performed or is performed on tissue that is in transition, or at test points that are too distant from and thus not representative of the tissue actually to be implanted.

Diseased tissue is more variable than healthy tissue in its mechanical properties, and is additionally capable or becoming altered as the result of having undergone an angioplasty or an atherectomy. The test is intended to determine whether the ductus wall is of sufficient strength to be implantable with either miniballs or stays, and if so, the depth necessary to avoid pull-through; or the gradual pulling through of the implant radially outwards until it perforates through the adventitia under magnetic traction.

As will be described, to reduce the risk of pull-through, miniballs of any kind can be deep surface textured and coated with a tissue adhesive-hardener; usually a cyanoacrylate tissue cement to gain the advantage of quick initial set. So that adhesion persists after the adhesive has broken down, the adhesive used should break down in pace with the ingrowth of surrounding tissue into the undercut furrows at the surface. However, because the strength of tissue in transition may weaken, the efficacy of such means is contingent upon the sufficiency of the prognosis. Generally, preinsertion testing is extraluminal to place stays and endoluminal to place miniballs.

Preinsertion testing for ductus-intramural implants checks for tissue strength, whereas postprocedural or followup diagnosis checks for dislodgement, infection, and notwithstanding the fact that nonallergenic materials are used throughout, an unanticipated or idiopathic tissue response. Where postprocedural symptoms have appeared, testing treatment with either miniballs or stays might be endoluminal or extraluminal. The numerous considerations involved to properly place patient inconvenience and imposition high on the list; absent symptoms, postprocedural diagnostics should be limited to noninvasive imaging.

XVII2. Midprocedural Preinsertion Testing

For endoluminal approach, imaging methods that provide an indication as to the strength of the wall surrounding the lumen has significant value. For the placement of stays and miniballs, the primary concern is tissue hardness, which is inseparable from penetrability and elasticity. Unless extreme, lumen wall distention for proper matching with a stent-jacket of suitable resilience or an impasse-jacket with suitable closing spring force can usually be dispensed with, as can testing before placing wide stays coated with cyanoacrylate cement.

Midprocedural testing is by the simplest and quickest means available, the use of intravascular ultrasound, for example, reserved for endoluminal approach, and preferably, where a fine probe can be passed down the central channel of a combination-form barrel-assembly. For the purpose of stenting, stays are substantially less susceptible to pathological alteration in tissue strength than are miniballs, so that no more than a quick probing to rule out an area of extreme malacosis is necessary.

Methods for gauging the mechanical properties of ductus walls in situ (see, for example, Restrepo, M. B. 2010. *Ultrasound Study of the Mechanical Properties of the Arterial Wall*, Doctoral Dissertation, Mayo Medical School, Rochester, Minn.; Glozman, T. and Azhari, H. 2010. "A Method for Characterization of Tissue Elastic Properties Combining Ultrasonic Computed Tomography with Elastography," *Journal of Ultrasound in Medicine* 29(3):387-398; Williams, M. J., Stewart, R. A., Low, C. J., and Wilkins, G. T. 1999. "Assessment of the Mechanical Properties of Coronary Arteries Using Intravascular Ultrasound: An In vivo Study," *International Journal of Cardiac Imaging* 15(4):287-294) are suitable for obtaining less point-specific lumen-circumferential mechanical information concerning the condition to be treated, and the time and cost therefor can usually be avoided.

In a procedure that requires endoluminal entry, information obtained with intravascular ultrasound may be valuable as background to immediate mechanical information concerning the point to be implanted. However, the probe is preferably not inserted before and after insertion of the barrel-assembly, but rather at once by insertion through the central channel of a combination-form barrel-assembly or as built into a small gauge radial discharge barrel-assembly. To achieve predictive value, the test must be directly performed on the tissue to be implanted, or if testing would prove damaging to that tissue, then adjacent tissue in what appears with confidence to be in the same condition.

The test also must be performed in a manner that allows the quantitative readings to be translated into equivalent settings for adjustment in the discharge velocity of miniballs or the spring tension in a control syringe-configured stay insertion tool with calibrated thumb-rod return spring screw adjustment. As addressed above in the section entitled Stay Insertion Tools, such a stay insertion tool uses its ejection blade with protective cap as a test probe to obtain readings directly applicable to adjustment in the spring tension, which function can be controlled by an inmate microcontroller. An intricate and expensive tool of this kind is, however, justified only for use with pathology that presents frequent and significant distinctions in mechanical properties from one small segment or area to the next.

Exactitude in the force of stay insertion rarely critical, the nonquantified or intuitive force of penetration applied by the operator is almost always satisfactory. A primary advantage in the use of wider stays, especially when coated with a quick setting tissue cement, is precisely that testing can often be dispensed with, reducing procedural time. The equivalency sought through quick checks includes that between the resistance to penetration reading and the setting of the exit velocity for miniball discharge, which requires that separate tables be prepared for miniballs of different diameter and mass. The readings are preferably obtained with a special mechanical microprobe force gauge service catheter passed down a service channel and thus following the same path as would a miniball.

The microprobe service catheter registers force and indentation in a manner similar to a auto tire pressure gauge in that the expelled length of the gauge is calibrated. To distinguish between surface hardness as indicated by indentation and ductus wall or organ cortex or capsule elasticity, for example, requires direct viewability. This does not, however, equate to a need for high cost imaging but rather use of an attached or incorporated angioscope. Alternatively, a resistance force measuring strain gauge tipped microprobe can be used. If ensheathed within a spring-loaded and calibrated outer tube, this can also furnish indentation and elasticity data.

Quantitative findings found with a mechanical microprobe, for example, which registers force indentation for the force indicated, are referred to a table of indentation and deflection-equivalent exit velocities for the type miniball used. Apart from apparatus-related factors, due to the shock impact and velocity of penetration of a miniball, the response characteristics of the tissue tested will differ from the values obtained with a manually projected probe such that accurate and dependable equivalency is not achieved; however, such testing is not to obtain equivalency of scientific exactitude but only a quantification sufficient for the immediate practical purpose. When the results of testing indicate a malacotic condition so that a perforation might occur even with the setting low, the use of stays is indicated.

If limited to a small segment not to be skipped or straddled, stays are used in that segment. Alternatively, when procedural time is to be kept to a minimum and the exceptional segment is small, a shield or double-wedge jacket can be placed about the malacotic segment and discharge continued without interruption, the interjection, or followup placement of stays in the deviant segment. Unless hemostasis has been impeded through administration of a potent platelet blockade or antiaggregate such as abciximab within the preceding 12 hours (see, for example, Emmer, J. H. Jr. 2000. "Clinical Experience in Coronary Bypass Surgery for Abciximab-treated Patients," *Annals of Thoracic Surgery* 70(2 Supplement):S33-S37), a little more than pinhole-sized perforation produced by a miniball will spontaneously seal quickly.

Alternative methods can, however, play a supplementary role in assessing tissue. While suitable for diagnosing the disease, for followup examination, and alerting to trouble spots, neither testing methods that employ extracorporeal or intravascular imaging provide the level of practical and immediate mechanical information needed. The conditions indicated necessitate spot-testing—testing that is simple, empirical, and quick, with the use of imaging equipment invoked only when necessary. Testing for ballistic implantation is for susceptibility to perforation, delamination, and pull-through, whereas stays, especially when more expansive and coated with tissue cement when inserted, are not susceptible to perforation and are less susceptible than are miniballs to pull-through or delamination.

Routine diagnostic testing of ductus wall segments would best be nonintravascular; but here, the disease has been diagnosed, testing is to ascertain the response of the tissue not in general terms but rather in terms of the methods for implant infixion described herein, and the need for invasive therapy has been determined, much depleting noninvasiveness of the value it normally has. Certain delimited areas proposed for implantation may lie adjacent to a ganglion, node, or other structure that could incur injury were testing to result in an accidental strike or an unexpected perforation. When a particular spot proposed for implantation is not to be tested, nearby tissue in what appears to be the same condition but outside the area for such a consequence is tested.

Any preliminary treatment affecting the mechanical properties of the tissue must be included in the test. Testing minimizes the need for empirical 'inching' or 'edging' up to the most effective exit velocity, which process is less safe, time-consuming, and is not usable where the tissue to be treated is too small in area to allow such a maybe right, maybe not approach. Materials testing of luminal wall strength in the laboratory is relatively well established (see, for example, Sommer, G. 2010. *Mechanical Properties of Healthy and Diseased Human Arteries: Insights into Human Arterial Biomechanics and Related Material Modeling*, Graz, Austria: Verlag der Technische Universität Graz) but not applicable to in vivo testing.

XVII3. Confirmation of Terminus

Whether due to irregularities in hardness of the ductus wall, weak adhesion among its tunics, or improper adjustment of the exit velocity, a miniball over- or under-shot, that is, falls short or overextends the end of trajectory intended, can be nonfunctional. Medicinal miniballs seldom require more than close approximation to the target tissue. Stenting miniballs, however, must not fall short or overextend the segment to be subtended by the stent-jacket. The trajectory terminus is quickly discerned by passing a fine catheteric magnetometer probe through the access incision and along the adventitia.

Provided the muzzle-head has just been degaussed, such a sensor can be passed down an unused barrel-tube as service-channel and the muzzle-head passed over the length of the ductus to the maximum distance that the miniball might have penetrated. This is usually not justification for a preliminary test discharge for effect but rather following the first discharge at any target point that might deviate in hardness from the tissue surrounding it to a degree more than negligible. For ballistic implantation, tissue hardness, or resistance to penetration, is the principal factor. The sudden shock delivery of ballistic infixion allows elasticity to be disregarded.

A catheteric magnetometer probe can reveal ductus-intramural implant positioning either by extraluminal approach by insertion through the access incision at the body surface or by endoluminal approach by passage through an unused barrel-tube as service-channel Sudden displacement as overcomes elasticity but can result in an improper end of trajectory is achieved not only by ballistic infixion, but by the sudden release of the thumb ring of a control syringe-configured stay insertion tool, and the abrupt attraction of a miniball by a powerful extracorporeal electromagnet, which pulsed, however, allows sufficient control over miniball repositioning. While a nonadjustable control syringe-configured stay insertion tool allows the operator to gradually raise his thumb, reducing the force and speed of stay insertion, such use of the tool while almost always dependable, is intuitive.

If the operator removes his thumb from the thumb-ring, the ejection blade will deliver the stay with the force and speed set by the thumb plunger-rod return spring. This property is built into, inherent in the tool, and unadjustable. By contrast, an adjustable control syringe-configured stay insertion tool allows the force and speed of stay insertion on sudden release to be adjusted. This is of some advantage when a long sequence of stays must be placed in the least amount of time and/or an inadvertent release of the thumb-ring could result in the intravasation or the tearing of a stay through the adventitia, possibly perforating into another structure.

Using ballistic infixion, the operator or an assistant uses a graph or table that translates tissue hardness for various tissues in various states of disease into the equivalent miniball discharge exit velocity or force of impact for use with miniballs of given diameter and mass. The exit velocity can be quickly checked by test discharge against a pressure registration paper such as Pressurex®. An equivalent graph or table for converting the tissue properties into the setting for an adjustable stay insertion tool is provided with the tool.

XVII4. In Situ Test on Endoluminal Approach for Susceptibility of the Ductus Wall to Puncture, Penetration, and Perforation These susceptibilities are automatically revealed and quantified when the force gauge or strain gauge-tipped catheter probe used to test tissue hardness and elasticity punctures, penetrates, or causes a through and through perforation of the ductus wall or organ capsule. These probes can be passed down an unused barrel-tube as service-channel or attached alongside the stay insertion tool. Provided time allows, these consequences are avoidable by avoiding endoluminal approach and instead placing wide cyanoacrylate cement-coated stays. Endoluminal approach denotes the use of a barrel-assembly, which is transluminal (through the lumen to be treated), as opposed to the use of a stay insertion tool, which inserts stay type ductus-intramural implants from outside the ductus, characterized as an extraluminal approach.

Atheromatous lesions are not simply unique due to these variables but may be intrinsically lesion-specific (see, for example, Kaski, J. C. 2003. "Atheromatous Plaque Location and Arterial Remodelling," *European Heart Journal* 24(4): 291-293). A preliminary extracorporeal method that involves first consulting a table for the probable range of exit velocity and impact force data for the barrel-assembly and miniballs to be used for the type and the condition of the tissue to be treated can provide no more than a reasonable approximation for initially setting the airgun exit velocity, the airgun then test discharged against a ballistic pendulum or against impact force registration paper as described above in the section entitled Control of Propulsive Force or Exit Velocity by Means of a Calibrated Slide Cover over a Slot Cut into the Valve Body.

The pretest provided is based on the principle that the momentum out is equal to the momentum in less friction, where friction is reduced to the point that for a practical spot check, it may be disregarded. Without a means for pretesting the lumen wall by the means specified, literal testing would require actually discharging for effect a miniball such as one of like diameter made of sugar with superparamagnetic magnetite or maghemite nanoparticles or finely grained powder to match the mass of the miniballs to be used.

An indication as to the strength of the lumen wall is also essential when the use of an external hand-held electromagnet and the field strength that may be applied to pull the muzzle-head in a preferred direction with this aid must be assessed lest an impact by the muzzle-head tear or tear through the wall. For preempting miniball perforations or a weakening of the lumen wall by high density implantation as might result in an aneurysmal failure of the wall, the results of such a test can also indicate the need to position the stent-jacket prior to initiating ballistic implantation. Another use for such a test is in order to evaluate whether the ductus is so malacotic that a graft is required, or if not so weakened, whether stays of wider than usual facing area can be used.

Because this area can be considerably greater than that of a miniball, the use of stays may make the application of an extraluminal stent possible where miniballs could not. Unless a preparatory angioplasty is felt essential, stays can also be used to eliminate any transluminal procedure, both stays and stent-jacket being introducible through the same one or two small incisions. When the disease process is progressively malacotic so that the immediate result given by a lumen wall strength test would likely become invalid soon, the transluminal methods described herein, to include pretesting, ballistic implantation, and the use of an external magnet to pull the muzzle-head in a preferred direction should be discounted and a graft, the use of conventional endoluminal methods, or of large surface area stays for resisting pull-through considered.

This allows the hardness of the lumen wall, which disease changes, to be evaluated quickly (empirically) without a need for calibration, computation, or conversion. While quantitative findings would appear to be more dependable, not every point along the lumen wall to be implanted can be tested, and the hardness of diseased tissue is subject to wide variability that actually makes confidence in findings obtained from a different point ill-advised. Furthermore, by actually employing the discharge mechanism, the reading obtained from a force measuring gauge, mechanical force tester, or mechanical puncture tester need not be translated into the corresponding exit velocity opening the way for human error.

The test is devised for simple, direct, and immediate results on an empirical and qualitative basis for practical use and makes no pretense to a level of precision required in the laboratory. To be described now is an empirical or purely observational means for quickly testing the penetrability and puncture strength of tissue in situ with any kind of airgun, regardless of the kind of clip used to load the airgun. Provided the operator initiates testing with exit velocities too slight to cause injury, increases the initial velocity slightly for each successive discharge, and avoids repeated testing at precisely the same spot, test discharge or discharge for effect, because it is empirical, that is, uses the actual tissue to be implanted and the actual apparatus to effect implantation, can afford dependable results quickly.

Testing is never conducted other than immediately preceding actual discharge under precisely the set of physical conditions and depth of general anesthetization and any other medication to apply, and the projectile used for testing is different only to the extent essential to prevent its unrestrained projection beyond the muzzle-head. Where differences in tonus, pulse, or peristalsis sufficient to affect the test are possible, the operator should wait for the same moment in the action cycle to discharge the airgun. While significant nonuniformities in the thickness, degree of calcification, and so on, of the diseased tissue warrant retesting before resumption, rather than to unduly detain completion of the procedure, lesions of a kind are assumed to have the same penetration resistance.

To preclude flexion, a surrogate projectile limited in forward displaceability having a length equal to that of the chamber plus that of the barrel-tube is made of a solid rod or closed ended thick walled tube of self-bondable E.I. Dupont de Nemours Teflon NXT® polytetrafluoroethylene that matches in caliber or diameter the miniballs used with the barrel-tube. Using a tube, a miniball of the same diameter is bonded onto the front end of the tube by means of an adhesive such as surgical cyanoacrylate cement. Using a solid rod, the front end of the rod is shaped into a hemisphere to simulate a miniball, with radiopacity achieved by plating or capping the tip, first etching the interior of the cap with, for example, Acton Technologies, Inc., FluoroEtch® or W.L. Gore® and Associates, Inc. TetraEtch® or blown-ion air plasma type corona, or flame surface treated, then bonding the cap onto the front of the rod with an adhesive such as Loctite Hysol Cool Melt®.

Whereas the leading end is shaped like the miniball for penetrative effect, the back end is likewise to react similarly to the propulsive gas. Since the miniball is massive if tiny (typically 0.4 millimeters), the test rod or tube of plastic, such as polytetrafluoroethylene to minimize friction, can be made to substantially the same mass. The rod or tube can be inserted into the proximal end of the barrel-assembly when disconnected from the airgun, removal from and replacement in the airgun barrel of the barrel-assembly as needed accomplished quickly. The test rod or tube must be sufficiently pliant to pass entirely through the barrel-assembly without exerting any straightening effect as would distort the result, and should not interfere with rotation of the turret-motor.

The testing rod or tube has a dorsal extension, a tab or key, toward its rear or proximal end within the chamber and is provided with a depth gauge type calibration over its distal segment. The key is made by inserting and bonding a tab of polytetrafluoroethylene that is pliant at the base of its faces into a slot cut into the rod or tube. The adhesive used to bond a cap at the front end and key toward the rear is Loctite Hysol Cool Melt®. The key has rounded and polished edges and fits into or engages a slot or groove milled or routed into the ceiling which begins at the distal end of the chamber so that the key can be inserted into and slid along the groove with no more than the intermittent and slight friction of aligning contact.

In a specially constructed interventional airgun intended to achieve deeper penetration, the ceiling groove must be longer and may extend past the front of the chamber into the barrel. The groove and key are made narrow as not to affect discharge. With a break-breech airgun, the test rod or tube is inserted into the barrel from the rear leaving enough length to insert the pliant key or tab toward into the slot or slideway in the valve body. The testing rod is pushed back into the chamber and the breech closed so that the front of the testing rod or tube is flush with the muzzle-port. Accordingly, the testing rod is inserted in the barrel-assembly prior to initial insertion into the vessel or duct to be treated.

Thereafter, the testing rod can be freely removed or reintroduced whenever the target diseased tissue appears different in penetrability. When the design of the gun is such that the rear of the test barrel is inaccessible, the testing rod is inserted through the muzzle, then twisted until the key engages the slideway. The ends or lands of the groove, typically on the order of two millimeters apart, thus represent stops that establish the limits of forward and backward movement or throw of the testing tube or rod and therewith the distance that the tube or rod can protrude out of the front end opening of the barrel-tube, or muzzle-port.

When a motorized muzzle-head is to be used to rotate or torque the muzzle-head, the barrel-tubes will have a rotary curve superimposed upon or compounded with the curve that directs these from the axis to the outer edge. The rotary curve compounded with the splay curve poses additional rolling resistance for the miniballs, so that testing should also be conducted with the muzzle-head rotated to angles to be used in the procedure. In use, a table provided with the factory-calibrated airgun is consulted for the optimal impact force and range of impact force settings that proved optimal for such diseased tissue at immediate autopsy, to include those at various rotary positions of the muzzle-head.

Since the settings are determined by the maker for the specific model airgun by comparison of its discharge at each setting to the impact force values obtained with the aid of a ballistic pendulum at autopsy, no compensation for barrel-tubes of higher friction is needed. Normally, the force imparted to the testing rod or tube is transferred with insignificant loss to the diseased tissue to be tested. However, when, for example, entry is inguinal and the target coronary, the barrel-assembly and testing rod follow a long and tortuous path that can dissipate a proportion of the momentum sufficient to invalidate the impact upon the target tissue as a basis for setting the controls on the airgun.

Such nonuniform resistance to projection of the testing rod or tube compared to a miniball are reflected in proportionally higher control settings specified in the table provided by the manufacturer. If the most common value in the range specified by the table results in puncture of the tunica adventitia, then the operator goes to the lowest value in the range. If the lowest value in the range still punctures through the adventitia, then the operator goes to the lowest value of the airgun. The results of the test discharge are carefully noted, and as few as possible adjustments made until the depth sought is attained. The proper value for the instant diseased tissue is arrived at in this strictly observational manner, preliminary value gathering, quantification, and computation accomplished by the maker, so that testing conducted mid-procedure is always strictly observational or empirical and takes the least time.

The use of tethered miniballs as testing devices is discounted as usable only over short distances along straight paths. Contacting the internal wall of the barrel-tube, which is unavoidable in a curve, tethered miniballs suddenly roll, begin to wrap their tether around them, which clogs and rubs against the barrel wall, abruptly and unpredictably yanking and braking the miniball. Such action unpredictably and unreproducibly consumes miniball momentum, completely invalidating the results of testing by such means. The testing method and apparatus described constitute a means of durometer testing living tissues whether normal or diseased in situ.

XVII5. In Situ Test on Endoluminal Approach for Intra- or Inter-Laminar Separation (Delamination, Laminar Avulsion)

Midprocedural susceptibility to tunical or intratunical delamination and postprocedural confirmation of delamination can both be ascertained with the aid of intravascular ultrasound. In the vascular tree, both pertain to the use of ductus-intramural implants in extraluminal stent-jackets, not those used to implant medication and not subject to an outward radial force. In the gastrointestinal tract, the more complex and forceful action of the muscle within the ductus wall means that the wall will be strong when normal, but recommends susceptibility testing in disease.

Preinsertion susceptibility in the vascular tree is checked by inserting a fine aspiration line through the access incision at the body surface and applying a vacuum equal in tractive force to that to be exerted by the stent-jacket; delamination is overcome by injecting a quickly setting tissue binder-hardener and retesting. Even if only a small portion of the segment to be stented is initially susceptible, a stent-jacket of maximum flexibility is placed. This may disallow the use of intrinsically and quasi-intrinsically magnetized stent-jackets. In health, the layers or tunics in the wall of a ductus cohere by gradual transition from the tissue type of each to that of the other at their interface despite tonic, pulsatile, or peristaltic contraction and relaxation of the smooth muscle at the center of the wall and the orthogonal shear generated by the travel of this action along the wall.

In disease, this cohesion may become weakened or undone. Atheromatous plaque, for example, separates the intima from the media. Therapeutic measures such as balloons and lasers can also affect this cohesion. In stenosed or constricted conditions where outward retraction of the outer layer or layers relieves the inward stenosing force that originates in these so that the force of the fluid within is then able to restore substantial patency, delamination, whether preexistent or caused by the vascular endomural implants may not matter. Since the ductus-intramural implants to serve as the intraductal component of a magnetic stent are preferably situated between the outer tunics of the ductus, for these to be pulled apart by the implant or to have been pulled apart by disease would result in the outer layers being held to the stent-jacket with the periluminal layer little if at all affected.

Because this would nullify the patenting effect intended, extraordinary measures are taken to avoid this eventuality, to include the coating of implants with various tissue strengthening and binding agents. The repair of delamination (laminar avulsion) warrants close study. The tests to be described must all be performed at the site and time of implantation. That is, unless the ductus is in the condition it will be when implanted, test results are of no value. Thus, for example, the application of an agent to cause the ductus wall to swell for ease in the insertion of stays will alter the properties of the wall, invalidating any test results that would have been obtained prior to having caused the ductus wall to swell.

Because the placing of implants, whether stays or miniballs, will inherently separate the radially outward from the inward layers in immediate contact with each implant, as well as to minimize testing time, both the endoluminal and extraluminal approach tests, which should be performed prior to the use of miniballs or stays respectively, should be performed after an implant coated with a solid protein solder has been placed and kept warm long enough to achieve a strength of bonding sufficient to resist separation under the magnetic traction exerted by the stent-jacket. This interval can be determined empirically by applying the stent-jacket of the lowest field strength that will open the lumen at intervals following implantation of the test implant.

If the interval for curing sufficient to withstand the stent-jacket exceeds that over which the ductus access wound should be kept from knitting, then the use of stays is discouraged as requiring reincision at or beside the original access incision. Unless contraindicated for reasons of tissue compatibility, testing should always use implants with a coating of a tissue adhesive-hardener from the outset. The time for denaturing and reaching initial set of a solid tissue adhesive-hardener if used is allowed and the prospective stent-jacket tentatively positioned to observe whether magnetic traction imposes a degree of intraparietal separation that is too pronounced for the adhesive-hardener to support.

With a ductus such as an artery, which is always filled and thus subject to outward, or centrifugal, force, a snug (not tight) stent-jacket will often reduce a separation without the need for an adhesive. The distinction in degree is something the test should reveal. One advantage in ballistic insertion is that sudden impact and momentum can conceal inconsistencies or nonuniformities in the target tissue that would redirect a miniball delivered at a lower but still functional velocity. When such an nonuniformity consists of an interface between layers in the wall of the ductus such that unless a stent-jacket were placed prior to initiating discharge the miniball would lift the outer layers leaving the inner layers unaffected, the results of the preceding test will conceal this fact necessitating another test performed at a low velocity in order to uncover such a condition.

Wide stays coated with cyanoacrylate cement should prevent delamination. If felt necessary, multigate color Doppler imaging (see, for example, Mitchell, D. G. 1990. "Color Doppler Imaging: Principles, Limitations, and Artifacts," *Radiology* 177(1):1-10) is used to view the ductus while an aspiration line inserted through the access incision is used to draw the adventitia outward. A sudden abaxial displacement of the adventitia is indicative of tunical or intertunical delamination. The ductus must withstand forces imposed by the sum of hemodynamic and magnetic retractive forces. Testing at lower velocities also gives a much better if time-limited indication as to the propensity for pull-through where the preceding test will report pull-through only as instantaneous, that is, as a perforation.

Accordingly, whether endo- or extraluminally, testing for intraparietal separation or delamination (laminar avulsion) should be performed before the preceding test for perforation and puncture. Whereas this endoluminal test is suitable for miniballs, the test next to be described, which is performed from the outside of the ductus, is suitable for stays, which then allow the lumen to be avoided both in preliminary testing and implantation. Neither test for intraparietal separation performed at high speed, conversion data sufficient to allow eliminating the need to perform the extraluminal test for separation next to be described when the endoluminal test described here had already been performed can be provided.

When the luminal constriction is attributable to an inner (adluminal) tunic or layer, however, unless extraluminal implants can be placed to undercut and lift this inner layer, delamination is likely to result in the insinuation and continued travel of miniballs between the parted layers or a useless retraction of the outer layers under the constant if mild tractive force exerted by the transversely magnetized metallic jacket or similarly magnetized bar magnets mounted about the outer surface of the base-tube that would leave the diameter of the lumen unaffected.

Depending upon the specifics of the condition then, it may be best to obtain an indication as to the cohesion of the layers in the luminal wall. To empirically check the tunic and laminae for susceptibility to delamination from within the lumen, an adhesive delivery-capable testing catheter of the same diameter as the miniballs for insertion, typically 0.4 millimeters, with hemispherical tip at the front and exceeding the barrel-tube length by two to five millimeters is passed through the barrel-tube that is closest to the lumen wall on the side to be implanted.

Such a test serves to determine whether a. A tissue adhesive-hardener is needed, b. To use miniballs or stays, and c. If miniballs, whether to place the stent-jacket prior to initiating discharge. The hollow test rod can be used to inject a commercially available radiopaque solution that will then fill the void in any separation between layers. While kept under view tomographically, the test rod or adhesive delivery-capable catheter is slowly forced through the intima and media to the adventitia-media interface.

Continued force then reveals whether the adventitia will separate from the subjacent media under the force that would be exerted by a stent-jacket that would exert the minimum tractive force essential to make the ductus patent. In situations where an accidental perforation would not spontaneously seal itself promptly and it is not desired to access the exterior of the ductus through a keyhole incision, preferably the original, but alternatively another test catheter having a lumen through which a long-chain methacrylate tissue cement can be injected is used.

XVII6. Endoluminal Approach Test for Intra- or Inter-Laminar Separation Following the Insertion of a Test Miniball The use of a fine catheteric aspiration line is addressed above in this section. This test pertains when the ductus wall will be subjected to a radially outward retractive force no greater than the encircling stent-jacket must exert to maintain the ductus in a patent state. Since to place the stent-jacket in encircling relation to the ductus requires entry through a small incision at the body surface, the test requires no additional invasive entry. For this reason, the test is the same as that for extraluminal approach as addressed in the section that follows.

XVIII. In Situ Test on Extraluminal Approach for Intra- or Inter-Laminar Separation (Delamination, Avulsion)

As stated in the preceding section entitled In Situ Test upon Endoluminal Approach for Intra- or Inter-laminar Separation (Delamination, Laminar Avulsion) delamination is of concern when the stenotic condition is attributable to an inner layer that cannot be undercut for outward retraction so that to draw the outer layers outward would have no effect on the diameter of the lumen. When the exterior of the ductus can be accessed through a keyhole incision, a commercially available radiopaque solution is injected into the lumen wall with a very fine hypodermic needle.

The ensuing pattern should allow a disproportionate lateral spreading through and characteristic of a separation between the layers in the wall of the ductus to be distinguished from entry and flow with other contents through the lumen. Even if an accidental injury or open surgery has fully exposed the ductus, to reliably evaluate any delamination between its layers using only a forceps or probe and without transecting it is impossible, making the need for contrast clear. Ideally, conversion data are provided to allow eliminating a need to perform the endoluminal test for separation described in the preceding section when the this endoluminal test had already been performed.

A simple method for evaluating susceptibility to delamination is addressed above in this section. The procedure call for passing a fine catheteric aspiration line connected to a precision vacuum gauge through the access incision at the body surface to apply a retractive force not significantly greater than that to be exerted by the stent-jacket. An assessment as to the outward radial tractive force that the wall can withstand is obtained by engaging the adventitia to the least depth possible with a miniature skin hook connected to a small precision or laboratory grade digital force gauge or high quality hand scale, such as one strain gauge based.

The pattern of infiltration between layers of the injected fluid and the pulling force on the scale indicate the magnetic traction that would be withstood prior to applying a tissue adhesive-hardener to the stays interventional measures delineated under the section above entitled Miniballs and Stays Coated with a Heat-activated (-melted, -denatured) Tissue Adhesive-Hardener. The acquisition of data as to the range of tolerance for force of magnetic retraction without and with impregnation of the intraparietal connective tissue with a tissue adhesive-hardener in which the implants are likewise disposed or embedded so that the implanta and surrounding tissue are effectively bonded together may be expected to accumulate.

XVII8. In Situ Test on Endoluminal Approach for Intra- or Inter-Laminar Separation Following the Insertion of a Test Miniball Delamination warrants testing only when the ductus will be subjected to the encircling retractive force of a stent-jacket, not when the miniballs or stays are medicinal, consist of other therapeutic substances, and/or radionuclides where no jacket is placed. The use of a fine aspiration line on extraluminal approach is addressed above in this section. If extraluminal access would impose no additional trauma, then that route is preferable for ascertaining whether a ductus-intramural implant has migrated indicating a delamination.

Delamination on endoluminal approach may occur if the stent-jacket had been prepositioned, in which case the jacket will block approach from outside, so that testing must be endoluminal. If the barrel-assembly does not incorporate an intravascular ultrasound probe or an angioscope and is a combination-form barrel-assembly as would allow such a probe to be inserted through the central channel to the nose, then to view whether the miniball is displaced requires extracorporeal imaging.

Later during the same procedure, after an interval not less than that for a coating of cement or protein solder if used to set, the muzzle-head is moved to a position at a longitudinal distance from the usually miniball or stay, which should be tantalum contrast coated. The recovery electromagnet to that side is energized, and the implant viewed to see whether it is displaced. If the electromagnets are not marked as to that to one side and that to the other, then the rotational angle is obtained from the machine controller, which in an ablation or angioplasty-capable barrel-assembly will be the inmate microcontroller. This will indicate which magnet is closest to the site.

XVII9. In Situ Test on Extraluminal Approach for Resistance to Centrifugal Pull-Through.

Wide cyanoacrylate coated stays pose no risk of pull-through as would warrant testing. If a stent- or shield-jacket is prepositioned blocking access through the incision through which it was inserted, then tissue that returns the same test results is used for testing. To target the test miniball and not affect nearby implants, the fine probe of an extracorporeal electromagnet is used to extract the same kind of miniball as a test miniball out through the adventitia.

If the force of attraction at which pull-through occurs is not significantly greater than that to be exerted by the stent-jacket, then miniballs with protein solder are used and heated to flow the solder into the surrounding tissue. Miniballs with a surface that is textured and undercut for tissue ingrowth to replace the solder over the time the solder breaks down is addressed in numerous sections above. Also addressed is the use of injection hypotube tipped catheters as service-catheters and injection tool-inserts to inject cyanoacrylate cement to flow about the miniball.

XVII10. Interconvertibility of Results Among Tests

The use of a combination mechanical force and magnetometer probe is addressed above in this section. Tools that inherently provide force readings convertible between mechanical, magnetic, and air moving push (exhaust, blowing) and pull (vacuum) forces expedite and generalize the interpretation of measurements as among these forces. To the extent that the endoluminal test for perforation and penetration and that for intraparietal separation duplicate steps, these steps ought not require to be repeated.

Furthermore, since one finding that either the endoluminal or extraluminal approach test for intraparietal separation might provide is the preferability of the opposite approach (extraluminal or endoluminal) and type implant (stays or miniballs respectively) is better suited to the ductus, it ought not to be necessary to perform a second test before the opposite procedure is initiated. It is therefore, desirable that the results for these tests be interconvertible. This is established by empirical testing with the different tests of the same ductus.

XVII11. In Situ Muzzle-Head Adhesion Test

Since the implants are generally to be positioned uniformly at close intervals, clinging or adhesion of the endothelium to the sides of the muzzle-head, despite its nonthrombogenic fluoropolymer coating, with the risk of rotational stretching injury, must be avoided. The avoidance of adhesion is especially important during automatic discharge, which can proceed so quickly that the operator does not realize the problem to push the cancel button. For this reason, smooth movement over the run segment is confirmed before automatic discharge is initiated. A muzzle-head with fluoropolymeric coating is intrinsically lubricious and, if necessary, can additionally be coated with a lubricant as specified above prior to introduction.

When the diameter of the lumen wall at the level to be implanted becomes smaller relative to that of the muzzle-head, especially when the condition of the wall promotes adhesion, additional lubricant may be necessary. Once at an appropriate depth into the vascular tree, rather than to test for adhesion by manually rotating the barrel-assembly risking rotational injury to the lumen wall, the turret-motor is used for controlled rotation too slight for such injury to become significant. When the muzzle-head reaches the level of the ductus for implantation, the effect of attempting to rotate the muzzle-head to either side with the turret-motor is observed for free movement, the tantalum markings or indices on the muzzle-head assisting in this determination.

While with either an angioplasty or nonangioplasty barrel-assembly, the turret-motor is not normally used before discharge, hence, before the barrel-assembly is connected to the airgun, the test for adhesion of the lumen wall to the muzzle-head and procedure for spreading lubricant about the muzzle-head once introduced through a muzzle-port makes use of the turret-motor prior to insertion in the airgun. Use of the turret-motor to check adhesion or to spread lubricant or medication prior to initiating discharge represents a distinct function of the turret-motor. If previously connected to the airgun, the barrel-assembly may be disconnected for such purpose.

The muzzle-head is rotated under closed-loop control and moved transluminally or longitudinally by the linear stage stepper motor under open-loop control. Resistance to rotation for any reason will be quickly apparent as the lagging behind or cessation of adherence to the instantaneous set point. Provided the barrel-assembly is equipped with a fine angioscope or intravascular ultrasound probe at the nose, resistance to transluminal motion will be seen in the video image monitor.

When observed, the turret-motor is stopped and a service-catheter, or if available, an ejection tool-insert, is used to eject a lubricant such as ACS Microslide®, Medtronic Enhance®, Bard Pro/Pel® or Hydro/Pel®, Cordis SLX®, or Rotaglide® into the interface between the outer surface of the muzzle-head and the endothelium. The turret-motor is then rotated to either side (clockwise and counterclockwise) and transluminal movement reattempted. If the barrel-assembly provides no inmate viewing means, it is best to use a muzzle-head with a contrast dye or tantalum coating which will be easily seen with an extracorporeal imagining machine.

XVIII. Followup Examination

Once implanted, the status of stent-jackets, stent-stays, clasp-magnets, clasp-wraps, and magnet-wraps should be periodically reinspected. While every precaution is taken to prevent such occurrences, stent-jackets may lose resilience, vascular intramural implants (miniature balls, stays) and clasp prongs can be pulled through the intervening substance of the vascular wall, and magnetically retracted tunic or tunics may delaminate. The embrittlement of a nonmagnetic stent-jacket would necessitate its replacement.

Every stent known is subject to structural failure, migration, or both. Endoluminal (conventional) ureteral stents, for example, are known at the time of placement to require replacement, but are nevertheless often disregarded if not forgotten. One purpose of reexamination is to determine the extent if any of reocclusion and use the remote heating capability of the extraluminal stent to reopen the lumen by means of noninvasive thermoplasty. The operator who realizes that he has stretched the lumen can place a chain-stent over the affected area without ductus-intramural implants for later noninvasive thermoplasty.

That compared to an endoluminal stent, the failure and/or migration of a stent outside the ductus poses little threat of occlusion is inarguable; however, the loss in patency is no less serious. For examining an extraluminal implant, intraductal ultrasonography is of little value. However, advances such as dual-energy contrast-enhanced computed tomography allow visualizing the current status of the different implants described herein, with or without a die or tantalum indices on the surfaces of the implants, noninvasively.

XIX. Sterilization

All of the components described herein, to include sequential or line-feed preloaded clips; rotary magazine clips; stent-jackets; subcutaneous encapsulated magnets; barrel-assemblies, which may include a motorized turret; test rotary magazine clips, airguns, stays, and stay insertion tools, are packaged sterile. Miniballs are preferably dispensed in preloaded clips as units with package markings to indicate proper use, rather than sold loose or in bulk. Sterilization is most preferred by radiation, followed by a gas, such as ethylene oxide, a liquid, such as glutaraldehyde, and, when the apparatus contains no bonds that heat might undo, boiling, steam autoclaving, and heating.

Fibrous wraps are meant for one time use and eventual disposal; however, if precautionary sterilization is to avert the possibility of contamination following removal from the sterile package, sterilization is by filtering through sterilizing gas or liquid through the interstices or exposure to ionizing radiation. Of the foregoing, sequential or line-feed preloaded clips, rotary magazine clips, stent-jackets, and subcutaneous encapsulated magnets are sold in sealed fully labelled paper envelopes with laminated foil interior, are meant to be implanted, and not sterilized after opening.

A more specialized and costly stent-jacket or subcutaneous magnet that is opened in error can nevertheless be sterilized chemically, as with ethylene oxide gas or radiation (reference, International Standards Organization standard 11135, *Medical Devices—Validation and Routine Control of Ethylene Oxide Sterilization*, peroxide plasma, electron beam, or gamma radiation). Alternative methods of sterilization should not be used with magnets. The high temperatures of boiling or steam autoclaving can degrade magnets, as can beta or gamma particle irradiation. Barrel-assemblies, test clips, and airguns are permanent and require sterilization by nondestructive means.

Barrel-assemblies are made of plastics, primarily fluoropolymers, with muzzle-heads usually made of nonmagnetic stainless steel and possibly motors that contain magnets; test clips consist of plastics and metals; and airguns include canisters containing compressed air or $CO_2$, the latter a liquid while contained and a gas when released, metals, plastics, and solenoids containing magnets. Chemical sterilization is preferred as applicable to all components. Suitable sterilizing agents include ethylene oxide gas, glutaraldehyde, chlorine dioxide, and other chlorine preparations, to include Dakins solution and Javelle water. Potentially irritating sterilizing agents are thoroughly removed by washing in soap and water and rinsing before use or packaging. Chemical sterilization cabinets, or chemiclaves, generally generate heat that falls safely below the Curie temperature of neodymium iron boron magnets.

XX. Exemplary Channel of Control in a Fully Implanted Ambulatory Adaptive Hierarchical Control System for Automatic Response to a Comorbid Condition Without safe and secure means of connection to tubular anatomical structures such as vessels, ducts, and the gut (ductus) which remain free of degradation or leaks over a period of years, an implantable automatic disorder response system is impossible. With discomfort minimized during placement, such systems will supplant current means of therapy for more serious chronic disease, especially comorbid, and especially in patients not prescription regimen compliance dependable. FIG. 107 shows an exemplary channel, or arm, of control in a fully implanted real time adaptive ('self-tuned,' learning-capable) and predictive hierarchical control system for the monitoring of physiological indicia pertinent to morbidity and comorbidity and the automatic dispensing of drugs, metabolic substances, heat, and/or cold responsive thereto to the sites or nidi of morbidity.

The benefits of direct pipe-targeting in preventing side effects, drug-drug interactions, and isolating each drug, allowing the qualitative and quantitative evaluation of the effect of each, the effect of each in relation to each of the others, and in the context of the homeostatic condition of the patient notwithstanding, unless the schedule for self-administration of a number of drugs is so complicated that it constitutes a nuisance likely to result in unintentional noncompliance, an implanted system is inappropriate for a competent adult patient for whom a safe and effective therapeutic regimen already exists. Another justification in such a patient that electrical or mechanical devices are to be implanted in any event, so that to include electrical and fluid lines to afford adjunctive treatment and service these primary implants without the need to reopen the patient is only common sense.

As shown in FIG. 108, the one of two or more channels of morbidity responsive control assigned to the urinary tract is treated in coordination with the other comorbidity or comorbidities. In practice, additional levels of control are necessary to deal with comorbidities, FIG. 108 simplified in this regard. FIG. 107 shows the system fully implanted except for surface ports, whereas FIG. 108 shows a system intended for shorter term use and therefore withholding components that need not be implanted housed within a power and control pack suspended from a waist belt. Biotelemetry is addressed in this section and indicated as one of a number of implanted microcircuit elements in FIG. 107, but discussed in conjunction with FIG. 108 in relation to data transmitted to the clinic or medical center.

This coordination, vertical from implanted [bio]sensors up through the nodes of control for the urinary tract, down from the master node for effector commands, and lateral for the other morbidities which affect other organ systems at other sites, is administered by the master node, executed by an implant microcontroller as master controller. Materials developed since the early 2000s consolidate sensor, or detector, and drug release response functions in a single material; however, much as drug eluting stents, these have nonreplenishable, hence limited, drug delivery capability. Most such materials respond by directly and spontaneously releasing medication pertinent to the exciting or triggering stimulus without the ability to provide a control signal, hence, are exclusively chemical, not really sensors, while others have this ability.

This would remain so were the 'nanocontainers' absorbable and drug release inclusive of dissolution of the sensor/container itself, something the ability to attract superparaagnetic iron oxide nanoparticle-carried drugs infused as a nanofluid—which stent- and impasse-jackets allow—would overcome (see, for example, Trousil, J., Filippov, S. K., Hrubý, M., Mazel, T., Syrová, Z., and 10 others 2017. "System with Embedded Drug Release and Nanoparticle Degradation Sensor Showing Efficient Rifampicin Delivery into Macrophages," *Nanomedicine* 13(1):307-315; Wang, J., Kaplan, J. A., Colson, Y. L., and Grinstaff, M. W. 2017. "Mechanoresponsive Materials for Drug Delivery: Harnessing Forces for Controlled Release," *Advanced Drug Delivery Reviews* 108:68-82; Wang, J., Colson, Y. L., and Grinstaff, M. W. 2017. "Tension-activated Delivery of Small Molecules and Proteins from Superhydrophobic Composites," *Advanced Healthcare Materials* December 27; Zhao, L., Huang, Q., Liu, Y., Wang, Q., Wang, L., and 3 others 2017. "Boronic Acid as Glucose-sensitive Agent Regulates Drug Delivery for Diabetes Treatment," *Materials* (Basel, Switzerland) 10(2). pii: E170; Wu, J. Z., Williams, G. R., Li, H. Y., Wang, D., Wu, H., Li, S. D., and Zhu, L. M. 2017. "Glucose- and Temperature-sensitive Nanoparticles for Insulin Delivery," *International Journal of Nanomedicine* 12:4037-4057; Matea, C. T., Mocan, T., Tabaran, F., Pop, T., Mosteanu, O., and 3 others 2017. "Quantum Dots in Imaging, Drug Delivery and Sensor Applications," *International Journal of Nanomedicine* 12:5421-5431;Zhao, L., Xiao, C., Wang, L., Gai, G., and Ding, J. 2016. "Glucose-sensitive Polymer Nanoparticles for Self-regulated Drug Delivery," *Chemical Communications* (Cambridge, England) 52(49): 7633-7652; Tziveleka, L. A., Bilalis, P., Chatzipavlidis, A., Boukos, N., and Kordas, G. 2014. "Development of Multiple Stimuli Responsive Magnetic Polymer Nanocontainers as Efficient Drug Delivery Systems," *Macromolecular Bioscience* 14(1):131-141; Siegel, R. A. 2014. "Stimuli Sensitive Polymers and Self Regulated Drug Delivery Systems: A Very Partial Review," *Journal of Controlled Release* 190: 337-351; Ngoepe, M., Choonara, Y. E., Tyagi, C., Tomar, L. K., du Toit, L. C., and 3 others 2013. "Integration of Biosensors and Drug Delivery Technologies for Early Detection and Chronic Management of Illness," *Sensors* (Basel, Switzerland) 13(6):7680-7713; Vakili, H., Genina, N., Ehlers, H., Bobacka, J., and Sandler, N. 2012. "Using Ion-selective Electrodes to Study the Drug Release from Porous Cellulose Matrices," *Pharmaceutics* 4(3):366-376; Bawa, P., Pillay, V., Choonara, Y. E., and du Toit, L. C. 2009. "Stimuli-responsive Polymers and Their Applications in Drug Delivery," *Biomedical Materials* (Bristol, England) 4(2):022001; Qu, J., Chu, L., Li, Y., Chen, W., and Zheng, C. 2004. "Intelligent Polymeric Systems for Glucose-responsive Insulin Delivery," in Chinese with English abstract at Pubmed, *Sheng Wu Yi Xue Gong Cheng Xue Za Zhi* [Journal of Biomedical Engineering] 21(6):1028-1030).

The lowest level nodes that execute direct control consist of microcontrollers, the hierarchical levels above these of equal or progressively increased computing power, the master controller generally that most powerful a microprocessor. Except at the direct control level, the ascription of 'supervisory' or coordinative functions vertically and horizontally is not fixed, so that side-by-side comparison can vary as to execution at the same or next higher level. The microcontrollers as nodes can be positioned in a distributed arrangement, but ultrahigh density electronics makes possible consolidation within a common enclosure.

This form of control is further described below and in copending application Ser. No. 14/121,365. Urological problems a frequent comorbidity in the elderly, the example shown in FIG. 107 pertains to the urinary tract. FIG. 107 shows nonjacketing side-entry connector 325 fastened toward the front of the inferolateral surface of the urinary bladder where it is positioned to treat any of a number of bladder dysfunctions. Such connectors, equivalent to ductus side-entry jackets where connection is to a tissue surface rather than a jacketable structure are also described in copending application Ser. No. 14/121,365. Whereas ductus side-entry jackets are used to connect fluid and electrical lines to vessels and other tubular anatomical structures, nonjacketing side-entry connectors are used to connect fluid and electrical lines to the outer surface of an organ or to tissue.

Nonjacketing side-entry connectors can incorporate hollow electrified anchoring needles for the injection of drugs and other agents into the substrate anchoring tissue, here the wall of the bladder, and the distal end of line 317 can be used to instill medication into the bladder cavity. In FIG. 107, part number 315 is a body surface port, here shown as positioned subdermally, so that drugs are introduced into reservoir 316 by hypodermic needle injection or jet injector. In a nonpermanent application, part number 315 is generally a portacath or mediport. When the surface port includes an outflow, or excurrent, opening, such as that shown as part number 323 to emit urine, or a compartment to house a button cell type battery or rechargeable button cell, or electrical socket to recharge an implanted battery, these if not all openings in the port are mounted cutaneously, that is, on rather than beneath, the skin.

While unlikely, should the power requirements, or the number of reservoirs or pumps become prohibitive of implantation, these are relegated to a belt- or thigh-worn control, power, and pump pack. Generally, once one of these becomes too large or numerous, the wearing of an external pack required in any event, the other components are likewise relegated to the pack, only the sensors requiring to be implanted. The power requirement permitting, a compartment in an above-skin-mounted, or cutaneous, port at the body surface to store one or more button cell batteries or rechargeable batteries, or an electrical socket to allow connection to a power supply, eliminates the need for transdermal, or 'transcutaneous,' energy transfer and the need to implant the reception and energy conversion circuitry associated therewith.

With a competent patient, this is usually to be preferred, both because it eliminates the additional implanted componentry and makes possible essentially uninterrupted duty by having the patient carry a small self-contained battery charger, power supply, or spare batteries. When smaller, such as a rechargeable button cell, the battery can be implanted, and as indicated above, recharged either through a socket in the surface port or transcutaneously recharged. An external (extracorporeal) control, power, and pump pack can include a larger battery or power supply with power cord to plug in the cutaneous body surface port, or can avoid the need for a cord with transcutaneous transmission circuitry. Generally, the current limitations of orientation, distance, and the need to implant a reception antenna make transcutaneous recharging less desirable, the more so in a cognitively impaired or very young patient. Simultaneous transdermal energy transfer and data transmission/instruction reception is addressed below in this section.

When no port at the body surface is used, recharging of implants is by transdermal or transcutaneous energy transfer (see, for example, Agarwal, K., Jegadeesan, R., Guo, Y. X., and Thakor, N. V. 2017. "Wireless Power Transfer Strategies for Implantable Bioelectronics," *Institute of Electrical and Electronics Engineers Reviews in Biomedical Engineering* 10:136-161; Bocan, K. N., Mickle, M. H., and Sejdic, E. 2017. "Tissue Variability and Antennas for Power Transfer to Wireless Implantable Medical Devices," *Institute of Electrical and Electronics Engineers Journal of Translational Engineering in Health and Medicine* 5:2700111; Agarwal, K., Jegadeesan, R., Guo, Y. X., and Thakor, N. V. 2017. "Wireless Power Transfer Strategies for Implantable Bioelectronics: Methodological Review," *Institute of Electrical and Electronics Engineers Reviews in Biomedical Engineering* March 16 (in press); Mirbozorgi, S. A., Yeon, P., and Ghovanloo, M. 2017. "Robust Wireless Power Transmission to mm-Sized Free-floating Distributed Implants," *Institute of Electrical and Electronics Engineers Transactions on Biomedical Circuits and Systems* 11(3):692-702; Bocan, K. N. and Sejdić, E. 2016. "Adaptive Transcutaneous Power Transfer to Implantable Devices: A State of the Art Review," *Sensors* (Basel, Switzerland) 16(3). pii: E393; Schormans, M., Valente, V., and Demosthenous, A. 2016. "Frequency Splitting Analysis and Compensation Method for Inductive Wireless Powering of Implantable Biosensors, *Sensors* (Basel, Switzerland) 16(8). pii: E1229; Ahn, D. and Ghovanloo, M. 2016. "Optimal Design of Wireless Power Transmission Links for Millimeter-sized Biomedical Implants," *Institute of Electrical and Electronics Engineers Transactions on Biomedical Circuits and Systems* 10(1): 125-137; Radziemski, L. and Makin, I. R. 2016. "In Vivo Demonstration of Ultrasound Power Delivery to Charge Implanted Medical Devices via Acute and Survival Porcine Studies," *Ultrasonics* 64:1-9; Ibrahim, A. and Kiani, M. 2016. "A Figure-of-Merit for Design and Optimization of Inductive Power Transmission Links for Millimeter-sized Biomedical Implants," *Institute of Electrical and Electronics Engineers Transactions on Biomedical Circuits and Systems* 10(6): 1100-1111; Ibrahim, A. and Kiani, M. 2016. "Inductive Power Transmission to Millimeter-sized Biomedical Implants Using Printed Spiral Coils," *Conference Proceedings Institute of Electrical and Electronics Engineers Engineering in Medicine and Biology Society* 2016:4800-4803; Miao, M. and Kiani, M. 2016. "Optimal Resonance Configuration for Ultrasonic Wireless Power Transmission to Millimeter-sized Biomedical Implants," *Conference Proceedings Institute of Electrical and Electronics Engineers Engineering in Medicine and Biology Society* 2016:1934-1937; Godfraind, C., Debelle, A., Lonys, L., Acuña, V., Doguet, P., and Nonclercq, A. 2016. "Inductive Powering of Subcutaneous Stimulators: Key Parameters and Their Impact on the Design Methodology," *European Journal of Translational Myology* 26(2):6040; Schormans, M., Valente, V., and Demosthenous, A. 2015. "Efficiency Optimization of Class-D Biomedical Inductive Wireless Power Transfer Systems by Means of Frequency Adjustment," *Conference Proceedings Institute of Electrical and Electronics Engineers Engineering in Medicine and Biology Society* 2015: 5473-5476; Ben Amar, A., Kouki, A. B., and Cao, H. 2015. "Power Approaches for Implantable Medical Devices," *Sensors* (Basel, Switzerland) 15(11):28889-28914; Ibrahim, A. and Kiani, M. 2015. "Safe Inductive Power Transmission to Millimeter-sized Implantable Microelectronics Devices," *Conference Proceedings of the Annual International Conference of the Institute of Electrical and Electronics Engineers Engineering in Medicine and Biology Society* 2015: 817-820; RamRakhyani, A. K. and Lazzi, G. 2014. "Multi-coil Approach to Reduce Electromagnetic Energy Absorption for Wirelessly Powered Implants," *Healthcare Technology Letters* 1(1):21-25; Ho, J. S., Yeh, A. J., Neofytou, E., Kim, S., Tanabe, Y., Patlolla, B., Beygui, R. E., and Poon, A. S. 2014. "Wireless Power transfer to Deep-tissue Microimplants," *Proceedings of the National Academy of Sciences of the United States of America* 111(22):7974-7979; Eom, K., Jeong, J., Lee, T. H., Lee, S. E., Jun, S. B., and Kim, S. J. 2013. "Columnar Transmitter Based Wireless Power Delivery System for Implantable Device in Freely Moving Animals," *Conference Proceedings Institute of Electrical and Electronics Engineers Engineering in Medicine and Biology Society* 2013:1859-1862; Li, X., Zhang, H., Peng, F., Li, Y., Yang, T., Wang, B., and Fang, D. 2012. "A Wireless Magnetic Resonance Energy Transfer System for Micro Implantable Medical Sensors," *Sensors* (Basel, Switzerland) 12(8):10292-10308; Artan, N., Vanjani, H., Vashist, G., Fu, Z., Bhakthavatsala, S., Ludvig, N., Medveczky, G., and Chao, H. 2010. "A High-performance Transcutaneous Battery Charger for Medical Implants," *Proceedings of the Institute of Electrical and Electronics Engineers Engineering in Medicine and Biology Society Annual Conference* 2010:1581-1584; Zhang, F., Hackworth, S. A., Liu, X., Chen, H., Sclabassi, R. J., and Sun, M. 2009. "Wireless Energy Transfer Platform for Medical Sensors and Implantable Devices," *Annual Conference Proceedings of the Institute of Electrical and Electronics Engineers Engineering in Medicine and Biology Society* 2009:1045-1048) to recharge an implanted battery.

The need for openings to the exterior for excurrent flow, to withdraw test samples, or to house a battery or electrical socket, for example, does not mean that other portions of the port are not positioned subdermally. Cutaneous ports include a protective cover and configuration to facilitate the wetting of all drug entry openings with antimicrobials or anti-inflammatories as necessary. Additionally, in FIG. 107, part number 317 is the catheteric line conveying drugs, for example, from reservoir outlet pump 318 to and through nonjacketing side-entry connecter 325. Reversible pump 318 allows the incurrent, or inflow, delivery of drugs and the excurrent, or outflow, recovery, or aspiration, of diagnostic test samples.

Connection of a more powerful suction pump to an opening in the external port allows the withdrawal of test samples from within the wall of the bladder; such use pertinent to diagnosis of a neoplasm or interstitial cystitis, for example. In incurrent use, line 317 can pass miniature cabled devices into the cavity of the bladder. Battery 322 is of the miniature button cell type, which to yield more power can be ganged. To meet the power requirements where numerous conditions necessitate numerous power consuming components, these are connected in series or parallel as appropriate with little combined weight to cause discomfort. Whether implanted as shown in FIG. 107 or housed in a compartment within surface port 315, battery 322 supplies the current responsive to the switching commands of microcontroller implant 321.

Microcontroller implant 321 is shown housed together with transdermal charging circuitry 319, and can be secured by suture or in a pocket, if necessary, created by tissue expansion cognizant of the risks associated therewith (Razzak, M. A., Hossain, M. S., Radzi, Z. B., Yahya, N. A., Czernuszka, J., and Rahman, M. T. 2016. "Cellular and Molecular Responses to Mechanical Expansion of Tissue," *Frontiers in Physiology* 7:540; Yu, Q., Sheng, L., Yang, M., Zhu, M., Huang, X., and Li, Q. 2014. "Tanshinon IIA Injection Accelerates Tissue Expansion by Reducing the Formation of the Fibrous Capsule," *Public Library of Science One* 9(8):e105756) in the pectoral region or sutured within the abdominal cavity. Part numbers 319, 321, and 327 have nominal component designations but should be understood as embracing a number of different components which vary according to the specific application. Representation thus spares the visual clutter that minimizes the actual space the anatomy provides for positioning these, since there is not just the two dimensional space of a drawing but any number of positions for placement in depth.

Wireless, or Bluetooth, ultra-low energy transmission and reception between sensors and primary nodes and among nodes to eliminate wires as addressed below in section XXI. is one type of componentry that may be understood as encompassed in any of these part numbers (see, for example, Walsh, J., Roberts, R., Morris, R., and Heinemann, L. 2015. "Device Connectivity: The Next Big Wave in Diabetes," *Journal of Diabetes Science and Technology* 9(3):701-705; Omre, A. H. 2010. "Bluetooth Low Energy: Wireless Connectivity for Medical Monitoring," *Journal of Diabetes Science and Technology* 4(2):457-463; Gomez, C, Oller, J., and Paradells, J. 2012. "Overview and Evaluation of Bluetooth Low Energy: An Emerging Low-Power Wireless Technology," *Sensors* (Basel, Switzerland) 12(9):11734-11753).

Typically, part number 327 would represent an intracorporeal, or within the body, transdermal battery charging and receiving circuitry and secondary coil or antenna, and optionally, a diagnostic [bio]sensor output data transceiver and biotelemetry antenna (see, for example, Mao, S., Wang, H., Zhu, C., Mao, Z. H., and Sun, M. 2017. "Simultaneous Wireless Power Transfer and Data Communication Using Synchronous Pulse-controlled Load Modulation," *Measurement* (London, England) 109:316-325; Bradley, P. D. 2011. "Wireless Medical Implant Technology—Recent Advances and Future Developments," Proceedings of the European Solid-State Device Research Conference, at http://ieeexplore.ieee.org/document/6044235/; Sharma, V., McCreery, D. B., Han, M., and Pikov, V. 2010. "Bidirectional Telemetry Controller for Neuroprosthetic Devices," *Institute of Electrical and Electronics Engineers Transactions on Neural Systems and Rehabilitation Engineering* 18(1):67-74; Young, D. J. 2009. "Wireless Powering and Data Telemetry for Biomedical Implants," *Institute of Electrical and Electronics Engineers Engineering in Medicine and Biology Society Annual Conference Proceedings* 2009:3221-3224; Panescu, D. 2008. "Wireless Communication Systems for Implantable Medical Devices," *Institute of Electrical and Electronics Engineers Engineering in Medicine and Biology Magazine* 27(2):96-101; Farshchi, S., Pesterev, A., Nuyujukian, P. H., Mody, I., and Judy, J. W. 2007. "Bi-Fi: An Embedded Sensor/System Architecture for REMOTE Biological Monitoring," *Institute of Electrical and Electronics Engineers Transactions on Information Technology in Biomedicine* 11(6):611-618; Farshchi, S., Nuyujukian, P. H., Pesterev, A., Mody, I., and Judy, J. W. 2006. "A TinyOS-enabled MICA2-based Wireless Neural Interface," *Institute of Electrical and Electronics Engineers Transactions on Biomedical Engineering* 53(7):1416-1424; Neihart, N. M. and Harrison, R. R. 2005. "Micropower Circuits for Bidirectional Wireless Telemetry in Neural Recording Applications," *Institute of Electrical and Electronics Engineers Transactions on Biomedical Engineering* 53(7):1416-1424; 52(11):1950-1959; Valdastri, P., Menciassi, A., Arena, A., Caccamo, C., and Dario, P. 2004. "An Implantable Telemetry Platform System for In Vivo Monitoring of Physiological Parameters," *Institute of Electrical and Electronics Engineers Transactions on Information Technology in Biomedicine* 8(3):271-278; Guler, N. F. and Ubeyli, E. D. 2002. "Theory and Applications of Biotelemetry," *Journal of Medical Systems* 26(2):159-178;). Side-entry jackets housing sensors that require a detectable reagent or reagents to be taken up by the blood or urine, for example, flowing past as to necessitate periodic replenishment are supported by release through a ductus side-entry jacket positioned upstream. Such a sensor or sensors housed within nonjacketing side-entry connectors are fed the reagents through the integral accessory channel In cases of comorbidity which can be treated and diagnosed without the need for a surface port with external openings, implanting a transdermally rechargeable battery allows full, or closed-skin, implantation. Part number 320 is a catheteric line to pass urine from the bladder through nonjacketing side-entry connector 326 to and through cutaneous surface outlet port 323 and into external urinary drainage collection bag 324. Where delivery through the connector to the treatment site of radioactive fluids would be sufficiently advantageous, the delivery apparatus from body surface port to and through the connector, to include reservoirs, feedlines, and connectors, are radiation shielded with relatively light weight tungsten shielding.

Referring to FIG. 107, nonjacketing side-entry connector 325 when placed to treat an overactive, or 'nervous,' bladder would most often deliver electrical current through its electrified anchoring needles and/or incorporate an electrode to pass current into fibers of the superior and inferior hypogastric plexuses and parasympathetic fibers of the pelvic splanchnic nerves, and/or a catheteric line with hypotube to inject botulinum toxin (electrical neurostimulation, electrostimulation). Current used thus is often pulsed, this function generated by the implant microcontroller. Overactive bladder has significant prevalence both as a separate entity and as a comorbidity, commonly with diabetes.

Ductus side-entry jackets and nonjacketing side-entry connectors make possible leak-free, and ductus side-entry jackets make possible shear stress-free continuity between the lumina of one or more catheters and those native without injuring the small vessels and nerves about the adventitia and therefore the urothelium. Both are therefore able to incorporate and stabilize in position as necessary, condition-pertinent [bio]sensors, miniature cabled diagnostic and therapeutic devices such as a laser, temperature [bio]sensor/heating or cooling devices, electrostimulatory electrode, intravascular ultrasound probe, or any styloid diagnostic device.

As shown in FIG. 107, effectors, or actuators, other than those positioned aside from the side-entry connector or jacket comprise drug reservoir outlet pump 318 connecting reservoir 316 to nonjacketing side-entry connector 325. Other such lines not shown simultaneously feed other nonjacketing side-entry connectors and ductus side-entry jackets. That is, a more inclusive view of the implant system overall than that shown in FIG. 107 would show ductus side-entry jackets, impasse-jackets, and nonjacketing side-entry connectors assigned and positioned to treat morbidity affecting other organ systems at separate locations via adjacent channels of control in the hierarchy coordinated with that urinary shown.

The prescription program uses these components in a coordinated manner to return abnormal function to as normal overall as can be attained with the anatomy given. Common instances of comorbidity include asthma, often found together with " . . . coronary artery disease, diabetes, dyslipidemia, hypertension, epilepsy, inflammatory bowel disease, rheumatic diseases, and severe psychiatric disease," the incidence of such comorbidity increasing with age (Kauppi, P., Linna, M., Jantunen, J., Martikainen, J. E., Haahtela, T., Pelkonen, A., and Mäkelä, M. 2015. "Chronic Comorbidities Contribute to the Burden and Costs of Persistent Asthma," Mediators of Inflammation 2015:819194). Asthma associated with allergic rhinitis and atopic eczema, constitutes the relatively common condition of atopy. All of these comorbidities can be severe enough to justify treatment with a fully implanted system of the kind described. The asthma may or may not have been triggered or aggravated by the comorbidity.

Taking asthma as a comorbidity, treatment varies according to the frequency of exacerbations or flare-ups. When not severe, a drug compliance competent patient can ameliorate the obstruction and distress with the aid of inhalants and oral drugs, so that if the patient does not react adversely to an anti-asthmatic drug that would help, the asthmatic drug delivery component can be omitted from the implanted system. However, because in comorbidity, the summary effect on the overall physiology of the patient of the drugs taken must be monitored, coordinated, and the optimal regimen continuously adjusted, the sensors and master controller program must be included. Also targeted must be radiocontrast agents to view bronchospasm if the use thereof induces nephropathy, thyroid dysfunction, adverse drug-drug, drug-food, interactions, and/or hypersensitivity reactions not readily avoidable by abstaining from food that provokes allergic reactions.

Because the morbidities in a comorbid condition are treated with minimal presuppositions as to the various designations of disease, the system will respond whether bronchospasm, for example, is excited by asthma, emphysema, or chronic obstructive pulmonary disease. This materially reduces the acuity of treatment to dependency on a preliminary diagnosis. When the drugs that would best treat the symptoms and diagnostic agents that would best bring an adverse reaction to view were the patient not constitutionally dyspathetic to these, the drugs and agents are directly pipe-targeted to the connector at the treatment site, with a bronchospasm provoking condition such as asthma, primarily ductus side-entry jackets on the bronchi and main pulmonary arteries.

Where medicinal inhalants, even when formulated for immediate uptake, are absorbed directly into the venous tree and other drugs into the arterial tree for dispersal throughout the circulatory system, directly piping drugs to the major supply arteries, even without the use of magnetized ductus side-entry jackets as described in copending application Ser. No. 14,121,365, now 20160051806, isolates the drug or drugs from the blood stream until released directly at the target tissue (see, for example, Ali, M. E., McConville, J. T., and Lamprecht, A. 2015. "Pulmonary Delivery of Anti-inflammatory Agents," Expert Opinion on Drug Delivery 12(6):929-945; Lee, W. H., Loo, C. Y., Traini, D., and Young, P. M. 2015. "Nano- and Micro-based Inhaled Drug Delivery Systems for Targeting Alveolar Macrophages," Expert Opinion on Drug Delivery 12(6):1009-1026; Ibrahim, M. and Garcia-Contreras, L. 2013. "Mechanisms of Absorption and Elimination of Drugs Administered by Inhalation," Therapeutic Delivery 4(8):1027-1045; Labiris, N. R. and Dolovich, M. B. 2003. "Pulmonary Drug Delivery. Part I: Physiological Factors Affecting Therapeutic Effectiveness of Aerosolized Medications," British Journal of Clinical Pharmacology 56(6):588-599; Labiris, N. R. and Dolovich, M. B. 2003. "Pulmonary Drug Delivery. Part II: The Role of Inhalant Delivery Devices and Drug Formulations in Therapeutic Effectiveness of Aerosolized Medications," British Journal of Clinical Pharmacology 56(6):600-612; Lipworth, B. J. 1996. "Pharmacokinetics of Inhaled Drugs," British Journal of Clinical Pharmacology 42(6):697-705;). Little residue continuing forward through the circulation, side effects and interactions with other drugs or food are considerably reduced if not eliminated.

As is true of all drugs to be targeted to a specific organ or tissue, all drugs to include those delivered in nanoparticulate form, magnetically susceptibly carried or not, for delivery to the lungs are more effectively delivered when directly piped. Release within the lungs by these means are applicable to any intrapulmonary disorder and any drugs used conventionally to treat each condition, radiation shielded lines and ductus side-entry connectors allowing the direct targeting of a malignancy (see, for example, Mangal, S., Gao, W., Li, T., and Zhou, Q. T. 2017. "Pulmonary Delivery of Nanoparticle Chemotherapy for the Treatment of Lung Cancers: Challenges and Opportunities," Acta Pharmacologica Sinica 38(6):782-797; Longest, P. W. and Hindle, M. 2017. "Small Airway Absorption and Microdosimetry of Inhaled Corticosteroid Particles after Deposition," Pharmaceutical Research 34(10):2049-2065; Din, F. U., Aman, W., Ullah, I., Qureshi, O. S., Mustapha, O., Shafique, S., and Zeb, A. 2017. "Effective Use of Nanocarriers as Drug Delivery Systems for the Treatment of Selected Tumors," International Journal of Nanomedicine 12:7291-7309; Ferraz-Carvalho, R. S., Pereira, M. A., Linhares, L. A., Lira-Nogueira, M. C., Cavalcanti, I. M., Santos-Magalhães, N. S., and Montenegro, L. M. 2016. "Effects of the Encapsulation of Usnic Acid into Liposomes and Interactions with Antituberculous Agents Against Multidrug-resistant Tuberculosis Clinical Isolates," Memórias do Instituto Oswaldo Cruz [Memoirs of the Oswaldo Cruz Institute] 111(5):330-334; Brandt, C., Thronicke, A., Roehmel, J. F., Krannich, A., Staab, D., and Schwarz, C. 2016. "Impact of Long-Term Tiotropium Bromide Therapy on Annual Lung Function Decline in Adult Patients with Cystic Fibrosis," Public Library of Science One 11(6):e0158193; Pérez-Herrero, E. and Fernández-Medarde, A. 2015. "Advanced Targeted Therapies in Cancer: Drug Nanocarriers, the Future of Chemotherapy," *European Journal of Pharmaceutics and Biopharmaceutics* 93:52-79; Ali, M. E., McConville, J. T., and Lamprecht, A. 2015. "Pulmonary Delivery of Anti-inflammatory Agents," *Expert Opinion on Drug Delivery* 12(6):929-945; Pham, D. D., Fatal, E., and Tsapis, N. 2015. "Pulmonary Drug Delivery Systems for Tuberculosis Treatment," *International Journal of Pharmaceutics* 478(2):517-529; Barnes, P. J. 2013. "Development of New Drugs for COPD," *Current Medicinal Chemistry* 20(12):1531-1540; Bailey, M. M. and Berkland, C. J. 2009. "Nanoparticle Formulations in Pulmonary Drug Delivery," *Medical Research Reviews* 29(1):196-212; Sung, J. C., Pulliam, B. L., and Edwards, D, A. 2007. "Nanoparticles for Drug Delivery to the Lungs," *Trends in Biotechnology* 25(12): 563-570).

Simple or comorbid, no disease, to include pulmonary, fails to present plural physiological indicia for each of which sensors cannot be devised to diagnose the condition, and with a form factor to allow mounting within ductus side-entry jackets and nonjacketing side-entry connectors. Pertinently, the small precise sensors currently under development either necessitate or would be materially improved by means such as nonjacketing side-entry connectors and ductus side-entry jackets to fix these in intracorporeal position as safely and stably as can be accomplished (see, for example, Yang, Q. F., Lu, T. T., Shu, C. M., Feng, L. F., Chang, H. T., and Ji, Q. Y. 2017. "Eosinophilic Biomarkers for Detection of Acute Exacerbation of Chronic Obstructive Pulmonary Disease with or without Pulmonary Embolism," *Experimental and Therapeutic Medicine* 14(4):3198-3206; Robison, H. M. and Bailey, R. C. 2017. "A Guide to Quantitative Biomarker Assay Development Using Whispering Gallery Mode Biosensors," *Current Protocols in Chemical Biology* 9(3):158-173; Kim, E., Baaske, M. D., and Vollmer, F. 2017. "Towards Next-generation Label-free Biosensors: Recent Advances in Whispering Gallery Mode Sensors," *Lab on a Chip* 17(7):1190-1205; Su, J. 2017. "Label-free Biological and Chemical Sensing Using Whispering Gallery Mode Optical Resonators: Past, Present, and Future," *Sensors* (Basel, Switzerland) 17(3). pii: E540; Dell'Olio, F., Conteduca, D., De Palo, M., and Ciminelli, C. 2017. "Design of a New Ultracompact Resonant Plasmonic Multi-Analyte Label-free Biosensing Platform," *Sensors* (Basel, Switzerland) 17(8). pii: E1810; Pongruengkiat, W. and Pechprasarn, S. 2017. "Whispering-gallery Mode Resonators for Detecting Cancer," *Sensors* (Basel, Switzerland) 17(9). pii: E2095; Luo, B., Wu, S., Zhang, Z., Zou, W., Shi, S., and 8 others 2016. "Human Heart Failure Biomarker Immunosensor Based on Excessively Tilted Fiber Gratings," *Biomedical Optics Express* 8(1):57-67; Bianucci, P. 2016. "Optical Microbottle Resonators for Sensing," *Sensors* (Basel, Switzerland) 16(11). pii: E1841; Bakakos, P, Patentalakis, G., and Papi, A. 2016. "Vascular Biomarkers in Asthma and COPD," *Current Topics in Medicinal Chemistry* 16(14): 1599-1609; Washburn, A. L., Shia, W. W., Lenkeit, K. A., Lee, S. H., and Bailey, R. C. 2016. "Multiplexed Cancer Biomarker Detection Using Chip-integrated Silicon Photonic Sensor Arrays," *Analyst* 141(18):5358-5365; Righini, G. C. and Soria, S. 2016. "Biosensing by WGM [whispering gallery mode] Microspherical Resonators," *Sensors* (Basel, Switzerland) 16(6). pii: E905; Dell'Olio, F., Conteduca, D., Ciminelli, C., and Armenise, M. N. 2015. "New Ultrasensitive Resonant Photonic Platform for Label-free Biosensing," *Optics Express* 23(22):28593-28604; Soteropulos, C. E. and Hunt, H. K. 2012. "Attaching Biological Probes to Silica Optical Biosensors Using Silane Coupling Agents," *Journal of Visualized Experiments* (63):e3866).

Drugs used to alleviate bronchospasm include muscarinic acetylcholine receptor antagonists such as ipratropium bromide, oxitropium bromide, and tiotropium bromide, conventionally administered by inhaler or nebulizer, and beta 2 agonists such as terbutaline, salbutamol, and fenoterol for shorter, salmeterol for longer duration treatment, and epinephrine. Limiting consideration to these few drugs, as a smooth muscle contracting, or positive inotropic agent, ipratropium bromide can induce urinary outflow obstruction, especially in men with prostatic hypertrophy (Lozewicz, S. 1989. "Bladder Outflow Obstruction Induced by Ipratropium Bromide," *Postgraduate Medical Journal* 65(762): 260-261), supraventricular tachycardia (O'Driscoll, B. R. 1989. "Supraventricular Tachycardia Caused by Nebulised Ipratropium Bromide," *Thorax* 44(4):312), bronchoconstriction (Rafferty, P., Beasley, R., Howarth, P. H., Mann, J. S., and Holgate, S. T. 1986. "Bronchoconstriction Induced by Nebulised Ipratropium Bromide: Relation to the Bromide Ion," *British Medical Journal* (Clinical Research Edition) 293(6561):1538-1539; Mann, J. S., Howarth, P. H., Holgate, S. T. 1984. "Bronchoconstriction Induced by Ipratropium Bromide in Asthma: Relation to Hypotonicity," *British Medical Journal* (Clinical Research Edition) 289(6443): 469), and less commonly, secretory suppressive side effects, to include inhibition of salivation, ocular effects such as pupil size, visual acuity, intraocular pressure, and hemodynamic effects such as heart rate, blood pressure, and blood gas changes (Anderson, W. M. 1986. "Hemodynamic and Non-bronchial Effects of Ipratropium Bromide," *American Journal of Medicine* 81(5A):45-53).

In asthmatic children, the short-acting beta 2 agonists terbutaline, salbutamol, and fenoterol induce tremor within 5 minutes, more intense with salbutamol. Terbutaline induces bradycardia, whereas salbutamol and fenoterol induce tachycardia more intense than the bradycardia induced by terbutaline. A double dose of salbutamol compared to the other two is equally effective, but at the expense of more intense tremor and tachycardia (Vangveeravong, M. 2008. "A Comparative Study of Efficacy of Salbutamol via Metered Dose Inhaler with Volumatic Spacer and via Dry Powder Inhaler, Easyhaler, to Nebulization in Mild to Moderate Severity Acute Asthma Exacerbation in Childhood," *Journal of the Medical Association of Thailand* 91 Supplement 3:S115-S123; Scalabrin, D. M., Solé, D., and Naspitz, C. K. 1996. "Efficacy and Side Effects of Beta 2-agonists by Inhaled Route in Acute Asthma in Children: Comparison of Salbutamol, Terbutaline, and Fenoterol," *Journal of Asthma* 33(6):407-415; "Newhouse, M. T., Dolovich, M. B., and Kazim, F. 1994. "Dose-effect Relationship of the Beta-agonists Fenoterol and Salbutamol in Patients with Asthma," *Chest* 105(6):1738-1742; Scalabrin, D. M. and Naspitz, C. K. 1993. "Efficacy and Side Effects of Salbutamol in Acute Asthma in Children: Comparison of Oral Route and Two Different Nebulizer Systems," *Journal of Asthma* 30(1):51-59; Wong, C. S., Pavord, I. D., Williams, J., Britton, J. R., and Tattersfield, A. E. 1990. "Bronchodilator, Cardiovascular, and Hypokalaemic Effects of Fenoterol, Salbutamol, and Terbutaline in Asthma," *Lancet* 336(8728):1396-1399; Budmiger H, Kyd K, and Scherrer, M.1978. "The Bronchospasmolytics Salbutamol, Fenoterol, Terbutaline and Reproterol. Their Effects and Side Effects in Asthmatics after Inhalation with an Electric Nebulizer," (in German with English abstract at Pubmed), *Schweizerische Medizinische Wochenschrift* [Swiss Medical Weekly] 108(31):1190-1197; Watson, J. M. and Richens, A. 1974. "The Effects of Salbutamol and Terbutaline on Physiological Tremor, Bronchial Tone and Heart Rate," *British Journal of Clinical Pharmacology* 1(3):223-227).

Even in a patient without a special sensitivity to it, the sympathomimetic amine epinephrine can induce a pronounced sense of agitation or disquietude, and in response to even a small overdose, pronounced distress. These are not, strictly speaking, adverse side effects, but rather the normal consequences of releasing the hormone into the bloodstream. By significantly reducing if not eliminating the release into the general circulation of epinephrine, for example, directly targeted delivery can alleviate such reactions no less than adverse reactions. Adverse side effects are associated with use in patients with known hypersensitivity and in patients with narrow angle, or angle closure, glaucoma, these too avoided by the substantial sequestration from the bloodstream provided by direct pipe-targeting.

Epinephrine can, however, react with certain foods and anesthetics with alarming, potentially fatal, consequences (see, for example, Lasemi, E., Sezavar, M., Habibi, L., Hemmat, S., Sarkarat, F., and Nematollahi, Z. 2015. "Articaine (4%) with Epinephrine (1:100,000 or 1:200,000) in Inferior Alveolar Nerve Block: Effects on the Vital Signs and Onset, and Duration of Anesthesia," *Journal of Dental Anesthesia and Pain Medicine* 15(4):201-205; Abu-Mostafa, N., Al-Showaikhat, F., Al-Shubbar, F., Al-Zawad, K., and Al-Zawad, F. 2015. "Hemodynamic Changes Following Injection of Local Anesthetics with Different Concentrations of Epinephrine During Simple Tooth Extraction: A Prospective Randomized Clinical Trial," *Journal of Clinical and Experimental Dentistry* 7(4):e471-e476; Abu-Mostafa, N., Aldawssary, A., Assari, A., Alnujaidy, S., and Almutlaq, A. 2015. "A Prospective Randomized Clinical Trial Compared the Effect of Various Types of Local Anesthetics Cartridges on Hypertensive Patients During Dental Extraction," *Journal of Clinical and Experimental Dentistry* 7(1):e84-e88; Steinfort, D. P., Herth, F. J., Eberhardt, R., and Irving, L. B. 2013. "Reply: Endobronchial Epinephrine: Confusion is in the Air," *American Journal of Respiratory and Critical Care Medicine* 187(10):1138; Khoo, K. L., Lee, P., and Mehta, A. C. 2013. "Endobronchial Epinephrine: Confusion is in the Air," *American Journal of Respiratory and Critical Care Medicine* 187(10):1137-1138; Steinfort, D. P., Herth, F. J., Eberhardt, R., and Irving, L. B. 2012. "Potentially Fatal Arrhythmia Complicating Endobronchial Epinephrine for Control of Iatrogenic Bleeding," *American Journal of Respiratory and Critical Care Medicine* 185(9):1028-1030; Becker, D. E. 2012. "Basic and Clinical Pharmacology of Autonomic Drugs," *Anesthesia Progress* 59(4):159-169; Becker, D. E. 2011. "Adverse Drug Interactions," *Anesthesia Progress* 58(1):31-41; Bushra, R., Aslam, N., and Khan, A. Y. 2011. "Food-drug Interactions," *Oman Medical Journal* 26(2):77-83; Hersh, E. V. and Giannakopoulos, H. 2010. "Beta-adrenergic Blocking Agents and Dental Vasoconstrictors," *Dental Clinics of North America* 54(4):687-696; Centeno, R. F. and Yu, Y. L. 2003. "The Propanolol-epinephrine Interaction Revisited: A Serious and Potentially Catastrophic Adverse Drug Interaction in Facial Plastic Surgery," *Plastic and Reconstructive Surgery* 111(2):944-945; Gandy, W. 1989. "Severe Epinephrine-propranolol Interaction," [in Lithuanian with cursory abstract in English at Pubmed], *Annals of Emergency Medicine* 18(1):98-99; Karl, H. W., Atlee, J. L. 3rd and Roberts, F. L. 1986. "Thiopental and Epinephrine-induced Dysrhythmias in Dogs Anesthetized with Enflurane or Isoflurane," *Anesthesia and Analgesia* 65(5):437-443; Swedlow, D. B., Lee, K. W., and Downes, J. J. 1983. "Epinephrine-halothane Interactions in Children," *Anesthesiology* 58(2):142-145; Sumikawa, K., Ishizaka, N., and Suzaki, M. 1983. "Arrhythmogenic Plasma Levels of Epinephrine During Halothane, Enflurane, and Pentobarbital Anesthesia in the Dog," *Anesthesiology* 58(4):322-325; Reisner, L. S. and Lippmann, M. 1975. "Ventricular Arrhythmias after Epinephrine Injection in Enflurane and in Halothane Anesthesia," *Anesthesia and Analgesia* 54(4): 468-470; British Medical Journal 1958. "DEATH after Adrenaline Injection," *British Medical Journal* 1(5072): 716). Directly targeted rather than introduced into the bloodstream by injection, infusion, or inhalation, the drug passes through the body with negligible if any distribution to tissue other than that at the treatment site, significantly reducing if not eliminating adverse side effects.

Sensors can make it possible to identify incipient indications of a concerning symptom at onset, in response to which the automatic system can initiate the directly pipe-targeted delivery of remedial medication to suppress or reverse the condition before it becomes apparent to consciousness. In the case of asthma, for example, when the patient is asleep with an exacerbation burgeoning that would call for the use of an inhaler, the automatic system would sense and respond to the incipient mucous occlusion and inflammation, ideally, so early that the episode might be averted while the patient continued to sleep. That is, from its inchoate indications, the automatic system anticipates an exacerbation and suppresses it before the patient would otherwise use an inhaler or take medication. Contrariwise, the system serves to dissuade an alert patient apprehensive about the possibility of an imminent acute event from taking a potent drug carrying the risk of adverse side effects needlessly, eliminating the problem of 'false alarms.'

With respect to any chronic component morbidity, justification for implanting an automatically operated direct fluid piping and/or wired electrostimulatory or thermal treatment system, for example, are the relative degree of risk without it, the health advantage in automatic monitoring and response, and the optimized use of drugs in even ordinarily drug regimen noncompliant patients by combining, when appropriate, a lower background dose with more concentrated doses directly targeted to the nidi rather than released into the general circulation. Drugs to treat asthma are usually inspired; in which case an implanted channel of control is not considered; however, where the patient is incapable of self-care, drugs can be delivered to the lungs through ductus side-entry jackets on the pulmonary arteries. Congenitally anomalous or malformed anatomy and physical trauma of the bladder surgically repairable, the gross anatomy when the implantation of such a system is considered will be normal or postsurgical.

Assigned to the bladder, this arm or channel of control detects the need for and regulates the release of drugs, metabolites, hormones, enzymes, medicinal reagents, and/or delivers electrostimulation through an electrode in the non-jacketing connector directly into the wall or the cavity of the bladder, or through a ductus jacket into the superior and/or inferior vesical artery, electrostimulatory or chemical neuromodulation if appropriate of the superior and/or hypogastric nerve and/or inferior parasympathetic nerve fibers. To allow direct observation if appropriate, the jacket or connector can incorporate miniature cabled devices such as a fiber cystoscope or therapeutic device such as a laser, the latter automatically actuated much as a drug or drugs would be released.

Copending application Ser. No. 14/121,365 addresses electrified round needle connector anchoring that allows myostimulation and tungsten radiation shielding to allow the use of low to moderate dose radioactive substances. Where nonlocal metabolic factors such as hormonal or enzymatic are involved in the bladder dysfunction, these are addressed through ductus side-entry jackets or nonjacketing side-entry connectors local to this site or these sites. Full implantation where the power requirement exceeds that currently obtained from within the body, such as from an arrangement employing miniature devices at the ankles to generate power when the patient walks, used either immediately without storage or battery-stored, necessitates a means of transmitting energy transdermally, or transcutaneously.

This technology, especially beneficial when the patient for any reason is not drug regimen compliant or unruly, is currently undergoing considerable advancement (see, for example, Bocan, K. N., Mickle, M. H., and Sejdic, E. 2017. "Tissue Variability and Antennas for Power Transfer to Wireless Implantable Medical Devices," *Institute of Electrical and Electronics Engineers Journal of Translational Engineering in Health and Medicine* 5:2700111; Agrawal, D. R., Tanabe, Y., Weng, D., Ma, A., Hsu, S., and 9 others 2017. "Conformal Phased Surfaces for Wireless Powering of Bioelectronic Microdevices," *Nature Biomedical Engineering* 2017; 1. pii: 0043 (in press); Tanabe, Y., Ho, J. S., Liu, J., Liao, S. Y., Zhen, Z., and 8 others 2017. "High-performance Wireless Powering for Peripheral Nerve Neuromodulation Systems," *Public Library of Science One* 12(10): e0186698; Mei, H., Thackston, K. A., Bercich, R. A., Jefferys, J. G., and Irazoqui, P. P. 2017. "Cavity Resonator Wireless Power Transfer System for Freely Moving Animal Experiments," *Institute of Electrical and Electronics Engineers Transactions in Biomedical Engineering* 64(4):775-785; Bocan, K. N. and Sejdić, E. 2016. "Adaptive Transcutaneous Power Transfer to Implantable Devices: A State of the Art Review," *Sensors* (Basel, Switzerland) 16(3). pii: E393; Schormans, M., Valente, V., and Demosthenous, A. 2016. "Frequency Splitting Analysis and Compensation Method for Inductive Wireless Powering of Implantable Biosensors," *Sensors* (Basel, Switzerland) 16(8). pii: E1229; Ahn, D. and Ghovanloo, M. 2016. "Optimal Design of Wireless Power Transmission Links for Millimeter-sized Biomedical Implants," *Institute of Electrical and Electronics Engineers Transactions on Biomedical Circuits and Systems* 10(1):125-137; Ibrahim, A. and Kiani, M. 2016. "A Figure-of-Merit for Design and Optimization of Inductive Power Transmission Links for Millimeter-sized Biomedical Implants," *Institute of Electrical and Electronics Engineers Transactions on Biomedical Circuits and Systems* 10(6): 1100-1111; Miao, M. and Kiani, M. 2016. "Optimal Resonance Configuration for Ultrasonic Wireless Power Transmission to Millimeter-sized Biomedical Implants," *Conference Proceedings Institute of Electrical and Electronics Engineers Engineering in Medicine and Biology Society* 2016:1934-1937; Ibrahim, A. and Kiani, M. 2016. "Inductive Power Transmission to Millimeter-sized Biomedical Implants Using Printed Spiral Coils," *Conference Proceedings of the Institute of Electrical and Electronics Engineers Engineering in Medicine and Biology Society* 2016:4800-4803; Gougheri, H. S. and Kiani, M. 2016. "Optimal Frequency for Powering Millimeter-sized Biomedical Implants Inside an Inductively-powered Homecage," *Conference Proceedings of the Institute of Electrical and Electronics Engineers Engineering in Medicine and Biology Society* 2016:4804-4807; Ibrahim, A. and Kiani, M. 2015. "Safe Inductive Power Transmission to Millimeter-sized Implantable Microelectronics Devices," *Conference Proceedings Institute of Electrical and Electronics Engineers Engineering in Medicine and Biology Society* 2015:32015:817-820; Zargham, M. and Gulak, P. G. 2015. "Fully Integrated On-chip Coil in 0.13 μm CMOS [complementary metal-oxide-semiconductor] for Wireless Power Transfer Through Biological Media," *Institute of Electrical and Electronics Engineers Transactions on Biomedical Circuits and Systems* 9(2):259-271; Schormans, M., Valente, V., and Demosthenous, A. 2015. "Efficiency Optimization of Class-D Biomedical Inductive Wireless Power Transfer Systems by Means of Frequency Adjustment," *Conference Proceedings Institute of Electrical and Electronics Engineers Engineering in Medicine and Biology Society* 2015:5473-5476; Eom, K., Jeong, J., Lee, T. H., Lee, S. E., Jun, S. B., and Kim, S. J. 2013. "Columnar Transmitter Based Wireless Power Delivery System for Implantable Device in Freely Moving Animals," *Conference Proceedings Institute of Electrical and Electronics Engineers Engineering in Medicine and Biology Society* 2013:1859-1862; Patel, S., Park, H., Bonato, P., Chan, L., and Rodgers, M. 2012. "A Review of Wearable Sensors and Systems with Application in Rehabilitation," *Journal of Neuroengineering and Rehabilitation* 9:21).

Recent developments pertain to circuitry that combines transdermal energy and data transfer (Mao, S., Wang, H., Zhu, C., Mao, Z. H., and Sun, M. 2017. "Simultaneous Wireless Power Transfer and Data Communication Using Synchronous Pulse-controlled Load Modulation," *Measurement* (London, England) 109:316-325, Op cit.; Gong, C., Liu, D., Miao, Z., and Li, M. 2017. "A Magnetic-balanced Inductive Link for the Simultaneous Uplink Data and Power Telemetry," *Sensors* (Basel, Switzerland) 17(8). pii: E1768; Lee, J. H., Sohn, I., and Kim, Y. H. 2017. "Simultaneous Wireless Power Transfer and Secure Multicasting in Cooperative Decode-and-Forward Relay Networks," *Sensors* (Basel, Switzerland) 17(5). pii: E1128; Hu, H., Gao, Z., Liao, X., and Leung, V. C. M. 2017. "Secure Communications in CIoT [Cognitive Internet of Things] Networks with a Wireless Energy Harvesting Untrusted Relay," *Sensors* (Basel, Switzerland) 17(9). pii: E2023; Jia, Y., Mirbozorgi, S. A., Wang, Z., Hsu, C. C., Madsen, T. E., Rainnie, D., and Ghovanloo, M. 2017. "Position and Orientation Insensitive Wireless Power Transmission for EnerCage-Homecage System," *Institute of Electrical and Elecronics Engineers Transactions on Biomedical Engineering* 64(10):2439-2449; Kiani, M. and Ghovanloo, M. 2015. "A 13.56-mbps Pulse Delay Modulation Based Transceiver for Simultaneous Near-field Data and Power Transmission," *Institute of Electrical and Electronics Engineers Transactions on Biomedical Circuits and Systems* 9(1):1-11; Boaventura, A. S. and Carvalho, N. B. 2015. "Evaluation of Simultaneous Wireless Power Transfer and Backscattering Data Communication Through Multisine Signals," *Institute of Electrical and Electronics Engineers Wireless Power Transfer Conference*, at http://ieeexplore.ieee.org/document/7139129/; Yang, D. X., Hu, Z., Zhao, H., Hu, H. F., Sun, Y. Z., Hou, B. J. 2015. "Through-metal-wall Power Delivery and Data Transmission for Enclosed Sensors: A Review," *Sensors* (Basel, Switzerland) 15(12):31581-31605; Lawry, T. J., Wilt, K. R., Ashdown, J. D., Scarton, H. A., and Saulnier, G. J. 2013. "A High-performance Ultrasonic System for the Simultaneous Transmission of Data and Power Through Solid Metal Barriers," *Institute of Electrical and Electronics Engineers Transactions on Ultrasonics, Ferroelectrics, and Frequency Control* 60(1):194-203; Ashdown, J., Wilt, K. R., Lawry, T. J., Saulnier, G. J., Shoudy, D. A., Scarton, H. A., and Gavens, A. J. 2013. "A Full-duplex Ultrasonic Through-wall Communication and Power Delivery System," *Institute of Electrical and Electronics Engineers Transactions on Ultra-* sonics, Ferroelectrics, and Frequency Control 60(3):587-595; Young, D. J. 2009. "Wireless Powering and Data Telemetry for Biomedical Implants," *Institute of Electrical and Electronics Engineers Engineering in Medicine and Biology Society Annual Conference Proceedings* 2009: 3221-3224, Op cit.).

As contemplated here, a body area, or body sensor, network is primarily intended for implementation in an ambulatory self-contained, self-sufficient, and if possible, fully implanted medical management system to allow a microprocessor to direct the targeted delivery of drugs and apply other therapeutic means responsive to sensor inputs according to a prescription program. With such a system, negative feedback allows the processor to confirm the efficacy of treatment, so that dependency upon clinicians in a remote clinic or medical center arises only if the system malfunctions or the prescription program does not comprehend an extreme condition.

The transmission problems encountered with long-range biotelemetry from a body network as documented below whereby the output of sensor implants is transmitted directly to the clinic do not pertain to such a fully contained short-range system implanted within a single patient. While a long range transceiver can be implanted, it is likely to generate a level of heat that recommends relegating it to an external pack, making it best avoided in favor of self-contained medical management. Another option is to interpose a secure cellular or satellite telephone or website to pass sensor data to the clinic and allow the patient to communicate with the medical staff.

That the system is entirely contained within or on the patient means that a cardinal problem with body area networks not circumscribed thus, internetwork interference and the unpredictability of patient bodily movement as negatively affecting network performance is avoided (Le, T. T. T. and Moh, S. 2017. "Link Scheduling Algorithm with Interference Prediction for Multiple Mobile WBANs [wireless body area networks]," *Sensors* (Basel, Switzerland) 17(10). pii: E2231; Sahoo, P. K., Pattanaik, S. R., and Wu, S. L. 2017. "A Reliable Data Transmission Model for IEEE 802.15.4e Enabled Wireless Sensor Network under WiFi Interference," *Sensors* (Basel, Switzerland) 17(6). pii: E1320; Sahoo, P. K., Pattanaik, S. R., and Wu, S. L. 2017. "Design and Analysis of a Low Latency Deterministic Network MAC [medium access control] for Wireless Sensor Networks," *Sensors* (Basel, Switzerland) 17(10). pii: E2185; Sarkar, S. and Misra, S. 2016. "From Micro to Nano: The Evolution of Wireless Sensor-Based Health Care," *Institute of Electrical and Electronics Engineers Pulse* 7(1):21-25; Le, T. T. and Moh, S. 2016. "An Interference-aware Traffic-priority-based Link Scheduling Algorithm for Interference Mitigation in Multiple Wireless Body Area Networks," *Sensors* (Basel, Switzerland) 16(12). pii: E2190; Kim, J. W., Barrado, J. R., and Jeon, D. K. 2016. "Time and Energy Efficient Relay Transmission for Multi-hop Wireless Sensor Networks," *Sensors* (Basel, Switzerland) 16(7). pii: E985; Bhandari, S. and Moh, S. 2016. "A Priority-based Adaptive MAC [medium access control] Protocol for Wireless Body Area Networks," *Sensors* (Basel, Switzerland) 16(3). pii: E401). These are technical reasons for the current inadequacy of non-self-contained systems, with nontechnical problems of staff unavailability and automation failures awaiting as equal if not greater problems. This lack of dependability is further mentioned below.

While limited to the reporting of symptoms to medical center-based diagnosticians rather than to a microprocessor implanted within the patient to provide an immediate therapeutic response, short-range Bluetooth ultra-low energy transception from sensor implants or a wireless body area network (see, for example, Cai, Z., Seyedi, M., Zhang, W., Rivet, F., and Lai, D. T. H. 2017. "Characterization of Impulse Radio Intrabody Communication System for Wireless Body Area Networks," *Journal of Medical and Biological Engineering* 37(1):74-84; Rehan, W., Fischer, S., and Rehan, M. 2017. "A Critical Review of Surveys Emphasizing Routing in Wireless Sensor Networks—An Anatomization under a General Survey Design Framework," *Sensors* (Basel, Switzerland) 17(8). pii: E1713; Rangarajan, A. 2016. "Emerging Trends in Healthcare Adoption of Wireless Body Area Networks," *Biomedical Instrumentation and Technology* 50(4):264-276; Effatparvar, M., Dehghan, M., and Rahmani, A. M. 2016. "A Comprehensive Survey of Energy-aware Routing Protocols in Wireless Body Area Sensor Networks," *Journal of Medical Systems* 40(9):201; Movassaghi, S., Abolhasan, M., Lipman, J., Smith, D., and Jamalipour, A. 2014. "Wireless Body Area Networks: A Survey," *Institute of Electrical and Electronics Engineers Communications Surveys and Tutorials;* Seyedi, M., Kibret, B., Lai, D. T., and Faulkner, M. 2013. "A Survey on Intrabody Communications for Body Area Network Applications," *Institute of Electrical and Electronics Engineers Transactions on Biomedical Engineering* 60(8):2067-2079; Katsu, K., Anzai, D., and Wang, J. 2013. "System Development and Performance Evaluation on Detection Schemes for UWB-IR [ultra wideband-impulse radio] Implant Communications," *Proceedings of the Institute of Electrical and Electronics Engineers Engineering in Medicine and Biology Society* 2013: 1234-1237; Ullah, S., Higgins, H., Braem, B., Latre, B., Blondia, C., and 4 others 2012. "A Comprehensive Survey of Wireless Body Area Networks: On PHY [physical], MAC [medium access control], and Network Layers Solutions," *Journal of Medical Systems* 36(3):1065-1094; Custodio, V., Herrera, F. J., López, G., and Moreno, J. I. 2012. "A Review on Architectures and Communications Technologies for Wearable Health-monitoring Systems," *Sensors* (Basel, Switzerland) 12(10):13907-13946; Lin, W., Lei, S., Wei, C., Li, C., and Wang, C. 2012. "Advances in Sensor Node and Wireless Communication Technology of Body Sensor Network," (in Chinese with English abstract at Pubmed), *Sheng Wu Yi Xue Gong Cheng Xue Za Zhi* [Journal of Biomedical Engineering] 29(3):568-573; Egbogah, E. E. and Fapojuwo, A. O. 2011. "A Survey of System Architecture Requirements for Health Care-based Wireless Sensor Networks," *Sensors* (Basel, Switzerland) 11(5):4875-4898; Bhattacharyya, D., Kim, T. H., and Pal, S. 2010. "A Comparative Study of Wireless Sensor Networks and Their Routing Protocols," *Sensors* (Basel, Switzerland) 10(12):10506-10523; van Halteren, A., Bults, R., Wac, K., Dokovsky, N., Koprinkov, G., and 4 others 2004. "Wireless Body Area Networks for Healthcare: The MobiHealth Project," *Studies in Health Technology and Informatics* 108:181-193) to a proximate cellular or satellite mobile telephone or internet terminal provided it is secure, for long-range transmission and reception eliminates the need to implant direct radio-based biotelemetric circuitry.

However, human as well as electronic communications-dependent, such an option is subject to much, possibly critical, delay in response, with application of the remedial measures decided dependent upon reaching a qualified physician with access to such means (see, for example, Stone, J. A. 2017. "Mobile Medicine: Digital Dynamo or Virtual Vaporware," *Canadian Journal of Cardiology* 33(2):216-218; Balasingam, M., Ebrahim, J., and Ariffin, I. A. 2017. "Tele-echocardiography—Made for Astronauts, Now in Hospitals," *Indian Heart Journal* 69(2):252-254; Shinbane, J. S. and Saxon, L. A. 2016. "Digital Monitoring and Care: Virtual Medicine," *Trends in Cardiovascular Medicine* 26(8):722-730; Mackintosh, N., Terblanche, M., Maharaj, R., Xyrichis, A., Franklin, K., and 7 others 2016. "Telemedicine with Clinical Decision Support for Critical Care: A Systematic Review," *Systematic Reviews* 5(1):176; Venkataraman, R. and Ramakrishnan, N. 2015. "Outcomes Related to Telemedicine in the Intensive Care Unit: What We Know and Would Like to Know," *Critical Care Clinics* 31(2):225-237; Subbarao, I. and Cooper, G. P. Jr. 2015. "Drone-based Telemedicine: A Brave but Necessary New World," *Journal of the American Osteopathic Association* 115(12):700-701; Hao, J. F., Cui, H. M., Han, J. M., Bai, J. X., Song, X., and Cao, N. 2014. "Tele-ICU: The Way Forward in Geriatric Care?," *Aging Clinical and Experimental Research* 26(6): 575-582; Ramnath, V. R., Ho, L., Maggio, L. A., and Khazeni, N. 2014. "Centralized Monitoring and Virtual Consultant Models of Tele-ICU Care: A Systematic Review," *Telemedicine Journal and E-Health* 20(10):936-961; Ramnath, V. R. and Khazeni, N. 2014. "Centralized Monitoring and Virtual Consultant Models of Tele-ICU Care: A Side-by-side Review," *Telemedicine Journal and E-Health* 20(10):962-971; Hsieh, J. C., Li, A. H., and Yang, C. C. 2013. "Mobile, Cloud, and Big Data Computing: Contributions, Challenges, and New Directions in Telecardiology," *International Journal of Environmental Research and Public Health* 10(11):6131-6153; Zhang, Y. and Xiao, H. 2009. "Bluetooth-based Sensor Networks for Remotely Monitoring the Physiological Signals of a Patient," *Institute of Electrical and Electronics Engineers Transactions on Information Technology in Biomedicine* 13(6):1040-1048; Yousef, J. and Lars, A. N. 2005. "Validation of a Real-time Wireless Telemedicine System Using Bluetooth Protocol and a Mobile Phone for Remote Monitoring Patient in Medical Practice," *European Journal of Medical Research* 10(6):254-262; Rasid, M. F. and Woodward, B. 2005. "Bluetooth Telemedicine Processor for Multichannel Biomedical Signal Transmission via Mobile Cellular Networks," *Institute of Electrical and Electronics Engineers Transactions on Information Technology in Biomedicine* 9(1):35-43). Compared to the implanted automatic and self-sufficient system described herein, these means are rudimentary and lacking in capability to respond promptly and effectively.

XXI. Fully Implanted Ambulatory Adaptive Hierarchical Control Systems for Automatic Response to a Comorbid Condition While a form of artificial intelligence, as addressed herein, adaptive and predictive hierarchical control is not an example of conventional intelligent decision software-based medical diagnostics, proposed therapy, or robotic surgery (see, for example, Hamet, P. and Tremblay, J. 2017. "Artificial Intelligence in Medicine," *Metabolism: Clinical and Experimental* 69S:S36-S40; Ashrafian, H., Darzi, A., and Athanasiou, T. 2015. "A Novel Modification of the Turing test for Artificial Intelligence and Robotics in Healthcare," *International Journal of Medical Robotics and Computer Assisted Surgery* 11(1):38-43; Bennett, C. C. and Hauser, K. 2013. "Artificial Intelligence Framework for Simulating Clinical Decision-making: A Markov Decision Process Approach," *Artificial Intelligence in Medicine* 57(1):9-19) as may eventually be obtained with programs such as Microsoft Hanover, (Microsoft Research 2016. "AI for Precision Medicine," at http://hanover.azurewebsites.net/; Tung, L. 2016. "Microsoft's Next Big AI Project? Helping 'Solve' Cancer," at http://www.zdnet.com/article/microsofts-next-big-ai-project-helping-solve-cancer/; Vincent, J. 2016. "Microsoft Announces New AI-powered Health Care Initiatives Targeting Cancer," at https://www.theverge.com/2016/9/20/12986314/microsoft-ai-healthcare-project-hanover-cancer [[which seek to identify the optimal drugs for the treatment of a diagnosed disease such as myeloid leukemia]).

Rather, applied to interdependent morbidities in the present context, an automatic disorder response system is used to evaluate deviations from optimal physiological function, substance concentrations, and imbalances in chemical processing activity. The substances and processes chosen for monitoring each morbidity are determined not on the basis of established syndromes whether eponymous, but rather empirically, on the basis of initial screening tests, several identified below, to identify the cause or causes for the signs and symptoms, eliminating errors due to symptom mimicry and any presuppositions of the medical staff. On this basis, the sensors are placed, deviations from the normal range noted, and drugs and doses appurtenant of each to return the values of these physiological indicia to within the normal range identified. The target organs and tissues, and agents to be used, and whether these can be delivered through the same feedlines then determine the detailed configuration and composition of the fluid and electrical lines, jackets, and nonjacketing connectors, and surface port if any to be used.

Significantly, such a system is self-corrective across plural morbidities, the more important where the interactions among these morbidities, especially those seldom seen in a single patient, has not been established with any definitude. From this standpoint, the system empirically sidesteps any misconceptions of the attendings to contribute new information concerning the interaction among such comorbidities. Additionally, because drug delivery is piped and kept from entry into the circulation until released at the treatment site, the action of each drug in relation to each of the others is substantially isolated, allowing qualitative and quantitative evaluation of the effect of each in the context of the homeostatic condition of the patient.

In practice, for each of the component morbidities, a sufficient number of implicated indicia are monitored, and each sensor input is first evaluated in isolation, then in relation to each of the others. A turret mechanism for taking different drugs from a number of vials respective of each is described and illustrated in copending application Ser. No. 14/121,365. Such a system responds to the exact deficit of the problematic drug, enzyme, or hormone, assuring proper dosage and in so doing, avoids the risks of over- or underdosage. In acting thus, the system acts in effect as a backup, supplementary, or adjunct immune system for deficient or missing analytes or metabolites.

In adapting spontaneously, the system is able to generate the data needed to correct numerous inborn errors or congenital defects of metabolism, that is, inherited or random mutation-based congenital metabolic diseases (see, for example, Journal of Inborn Errors of Metabolism and Screening 2017. "Abstracts presented at the 13th International Congress of Inborn Errors of Metabolism," *Journal of Inborn Errors of Metabolism and Screening*, at http://journals.sagepub.com/doi/full/10.1177/2326409817722292 [includes 919 ample abstracts]; Vernon, H. J. 2015. "Inborn Errors of Metabolism: Advances in Diagnosis and Therapy," *Journal of the American Medical Association Pediatrics* 169(8):778-782).

Such disorders, initially recognized clinically and identified by means of screening tests using mass spectrometry, gas chromatography-mass spectrometry, liquid ion-exchange chromatography, quantification of amino acids in various body fluids, ninhydrin paper chromatography, ferric chloride testing, and less frequently, tissue biopsy or DNA testing, include numerous defects of mitochondrial, carbohydrate, purine, pyrimidine, porphyrin, lysosomal storage, and steroid function, among many others. Most such disorders can be controlled through diet, enzyme replacement, gene therapy, and organ transplantation. This screening determines the type sensors to implant.

The initial identification of significant functions, pathways, metabolites, and sensors needed must follow from standard diagnostic tests. To avert misinterpretation and misdirection, more than one diagnostician should always be consulted, and the impulse to settle on a diagnosis before testing has been completed suppressed. The results of this review are used to decide which indicia should be pursued— with limiting presuppositions set aside. If clear-cut, recognition of a syndrome is helpful; if ambiguous, it may partially or entirely mislead. When the ascription of symptoms is obscure or indefinite, sidestepping the nomenclature and going straight to the physiological indicia serves to avert errors. The direct detection of deviation from normal values of physiological indicia does not apply to many conditions; however, where it does, misdiagnoses can be prevented from the outset.

Where, however, the patient is too young, too old, or incapacitated, or the regimen more involved, disorders managed through enzyme replacement in particular are readily supported. If the defective metabolite, usually an enzyme, is completely ineffective, the response is to provide that metabolite, in which case the delivery system is effectively 'bionic.' If the metabolite is partially ineffective or insufficient, the delivery system is used to provide the missing fraction thereof. If the number of drugs and/or size of each dose does not permit of implantation of the reservoirs, typically subdermally in the pectoral region, because these would intrude upon neighboring tissue, then the drug turret switching mechanism is relegated to a belt-suspended power and pump pack.

Alternatively, the pack can be worn about a thigh much as a urine collection bag. Generally, only components that cannot be comfortably implanted are relegated to an extracorporeal or worn pack. When the overall condition of the patient is nonexigent as to afford sufficient time, tissue expansion can be used to create the space essential to achieve full implantation. Urgency and the suitability of the patient to undergo implantation deciding factors, when time is not available to accomplish more than sensor or full implantation at the outset, or to accomplish the same with tissue expansion, the process can proceed with the patient temporarily provided with an external pack that includes only the larger or more difficult components to place intracorporeally. If necessary, the extracorporeal pack can include all but the sensors, that is, the control, power, and pumps; in a decentralized or distributed hierarchical control system, even lower level nodes can transmit data to the external pack by wireless radio, addressed below.

The response of the set to a drug is then gauged as to the efficiency of which that drug affects the set. The adaptive system 'learns' which drug or combination thereof most closely restore the patient to homeostatic equipoise. Such a reference model architecture-based real-time control system emulates the nervous system in vertebrates, in that sensory data assigned to every location in the body is resolved locally by the immune and/or endocrine systems, and the 'data' streamed upward through the spinal cord and bloodstream to the appropriate level or levels in the brain, primarily the hypothalamus, this form of organization with negative feedback reiterated at every level of the organism from the cellular to the metabolic to the gross anatomic features of the nervous and endocrine systems where the conditions at each level educes complementary structure and function at every other level.

Here, sites of different morbidity are each assigned a channel of control which passes up through the hierarchical tree to the master controller, while commands proceed from the master controller down through the nodes of the tree to effectors, here mostly small pumps at the outlets of small flat drug reservoirs implanted subdermally in the pectoral region (see, for example, Grasman, J., Callender, H. L., and Mensink, M. 2017. "Proportional Insulin Infusion in Closed-Loop Control of Blood Glucose," *Public Library of Science One* 12(1):e0169135; Scheidel, J., Lindauer, K., Ackermann, J., and Koch, I. 2015. "Quasi-Steady-state Analysis Based on Structural Modules and Timed Petri Net Predict System's Dynamics: The Life Cycle of the Insulin Receptor," *Metabolites* 5(4):766-793; Alcocer-Cuarón, C., Rivera, A. L., and Castaño, V. M. 2014. "Hierarchical Structure of Biological Systems: A Bioengineering Approach, *Bioengineered* 5(2):73-79; Vasil'ev, G. F. 2013. "Cybernetics and Biology," (in Russian with abstract in English at Pubmed), *Biofizika* 58(4):732-736; Noble, D. 2012. "A Theory of Biological Relativity: No Privileged Level of Causation," *Interface Focus* 2(1):55-64; Bortfeldt, R. H., Schuster, S., and Koch, I. 2011. "Exhaustive Analysis of the Modular Structure of the Spliceosomal Assembly Network: A Petri Net Approach," *Studies in Health Technology and Informatics* 162:244-278; Gianchandani, E. P., Chavali, A. K., and Papin, J. A. 2010. "The Application of Flux Balance Analysis in Systems Biology," *Wiley Interdisciplinary Reviews. Systems Biology and Medicine* 2(3):372-382; Liu, W. and Tang, F. 2008. "Modeling a Simplified Regulatory System of Blood Glucose at Molecular Levels," *Journal of Theoretical Biology* 252(4):608-620; Grafahrend-Belau, E., Schreiber, F., Heiner, M., Sackmann, A., Junker, B. H., and 4 others 2008. "Modularization of Biochemical Networks Based on Classification of Petri Net T-invariants," *BioMed Central Bioinformatics* 9:90; Auffray, C. and Nottale, L. 2008. "Scale Relativity Theory and Integrative Systems Biology: 1. Founding Principles and Scale Laws," *Progress in Biophysics and Molecular Biology* 97(1):79-114; Nottale, L. and Auffray, C. 2008. "Scale Relativity Theory and Integrative Systems Biology: 2. Macroscopic Quantum-type Mechanics," *Progress in Biophysics and Molecular Biology* 97(1):115-157; Nederbragt, H. 1997. "Hierarchical Organization of Biological Systems and the Structure of Adaptation in Evolution and Tumorigenesis," *Journal of Theoretical Biology* 184(2): 149-156).

It is also analogous to the command and control tree of a large organization, where orders pass down through subordinate levels in the hierarchy and reports flow back up to the chief executive officer. In practice, responsive measures are not limited to the selection, dosing, and release or drugs but might include the local application of warmth, chilling, or electrical stimulation, for example. Moving up the control nodes, this process is applied to each morbidity, then extended to include each of the other morbidities, so that 'aware' of all sensor inputs and effector outputs for each drug or drugs tried across the set of morbidities, for example, the master node is able to accumulate 'experience' as to gradually ascertain and apply the optimal combination of responses to each component morbidity and therefore the optimal combination of measures to apply in order to return the set of morbidities to as normal a condition that the remedial measures available, following any necessary surgery, will allow.

The master node microprocessor continuously monitors the homeostatic status of the patient, continuously adjusting the release of drugs. In a hierarchically organized system of control, each level in the hierarchy is situated along a vertically, component morbidity-dedicated, and horizontally concomitant morbidity-related node in an organizational tree. Since FIG. 108 is drawn to reflect that the initial step is obtaining sensor data, that is, drawn from the 'sensory' rather than the 'motor' view) which then flows up through the tree, the command view which places the master controller at the top and the tree as a whole appears as inverted. Note that FIG. 108 shows effectors and control components housed in an extracorporeal power and control pack, usually suspended from a pants or skirt belt, suitable where the necessity therefor is predicted to be not sufficiently long term to warrant implantation, whereas FIG. 107, shows these components as implanted.

For relative simplicity, FIG. 108 shows only three hierarchical levels so that three levels of nodes are shown; the upper two of the three modules—that implanted in the body shown in the box at the top of the drawing—comprising the sensors and effectors represent the lowest level, with the three levels superior to these shown in the boxed about module at the bottom of the drawing. Four sensors are assigned to each arm or channel of control, with each set of four and the two intervening levels of control or nodes assigned to either of the two morbidities present and the master controller exercising control over the sum of physiological indicia monitored. The need for sensors determined by the condition to be monitored, the showing of four sensors to monitor each of two component morbidities in FIG. 108 is arbitrary. Since only serious chronic conditions warrant the placement of such a system, for functioning sensors to be replaced or resituated after initial placement is very unlikely.

The number of sensors required depends upon the least number of physiological indicia or low level (initiative, foundational) symptoms essential to adequately characterize the component malfunction or morbidity, the complexity of control rising with the addition of sensors and computational burden of coordinating these inputs in the context of overall patient homeostasis, necessitating the addition of hierarchical control levels, hence, nodes, and increasing the power and heat generation of the master node microprocessor. For this reason, a system assigned to monitor and respond to several comorbid conditions, especially when these interact, will likely necessitate an externally worn control, power, and pump pack, both due to the number of components required and the heat generated by the master node microprocessor and perhaps the higher subordinate node microcontrollers.

As depicted in FIG. 108, sensory data responsive to the antecedent remediating command, continuously flows up the tree from subordinate to superior nodes, and commands adjusted on the basis of this feedback are more precisely aligned to the overall tasks and goals to be achieved, which continuously flow down the tree from superior to subordinate nodes. Each node is thus both semiautonomous but at the same time, responsive to the data flowing up and down through it, with the penultimate level communicating laterally as well. Broadly, the master node is a microprocessor and the subordinate nodes microcontrollers.

The penultimate nodes, that is, those subordinate to the master node, are assigned responsibility over each morbidity and terminate in sensors and effectors responsive to their assigned component morbidity. The tasks assigned to both sensors and effectors at the lowest or immediate, local level are simplest and take the least time to discharge, while each successively higher level in the hierarchy is coordinative at a more encompassing level. That is, each step up the hierarchical levels involves greater and greater data correlation, integration, extraction, and command input processing. For this reason, each higher level in the tree requires somewhat more processing time than that just beneath it.

In some instances, like data from multiple sensors is combined " . . . to form a unified picture." (Khaleghi, B., Khamis, A., and Karray, F. O., and Razavi, S. N. 2011. "Multisensor Data Fusion: A Review of the State of the Art," *Information Fusion* 14(1):28-44; see also Liu, B., Zhan, X., and Zhu, Z. H. 2017. "Multisensor Parallel Largest Ellipsoid Distributed Data Fusion with Unknown Cross-Covariances," *Sensors* (Basel, Switzerland) 17(7). pii: E1526; Jain, K. 2017. "Use of Failure Mode Effect Analysis (FMEA) to Improve Medication Management Process," *International Journal of Health Care Quality Assurance* 30(2):175-186; Jiang, W., Zhuang, M., and Xie, C. 2017. "A Reliability-based Method to Sensor Data Fusion," *Sensors* (Basel, Switzerland) 17(7). pii: E1575; Jain, K. 2017. "Use of Failure Mode Effect Analysis (FMEA) to Improve Medication Management Process," *International Journal of Health Care Quality Assurance* 30(2):175-186; Deng X. and Jiang, W. 2017. "Fuzzy Risk Evaluation in Failure Mode and Effects Analysis Using a D Numbers Based Multi-Sensor Information Fusion Method," *Sensors* (Basel, Switzerland) 17(9). pii: E2086; Bakr, M. A. and Lee, S. 2017. "Distributed Multisensor Data Fusion under Unknown Correlation and Data Inconsistency," *Sensors* (Basel, Switzerland) 17(11). pii: E2472; Askari, R., Shafii, M., Rafiei, S., Abolhassani, M. S., and Salarikhah, E. 2017. "Failure Mode and Effect Analysis: Improving Intensive Care Unit Risk Management Processes," *International Journal of Health Care Quality Assurance* 30(3):208-215; Pires, I. M., Garcia, N. M., Pombo, N., and Flórez-Revuelta, F. 2016. "From Data Acquisition to Data Fusion: A Comprehensive Review and a Roadmap for the Identification of Activities of Daily Living Using Mobile Devices," *Sensors* (Basel, Switzerland) 16(2):184; Abdi, Z., Ravaghi, H., Abbasi, M., Delgoshaei, B., and Esfandiari, S. 2016. "Application of Bowtie Methodology to Improve Patient Safety," *International Journal of Health Care Quality Assurance* 29(4):425-440; Jiang, W., Xie, C., Zhuang, M., Shou, Y., and Tang, Y. 2016. "Sensor Data Fusion with Z-Numbers and Its Application in Fault Diagnosis," *Sensors* (Basel, Switzerland) 16(9). pii: E1509; Klonoff, D. C. and Kerr, D. 2016. "Digital Diabetes Communication: There's an App for That," *Journal of Diabetes Science and Technology* 10(5):1003-1005; Shen, B., Liu, Y., Fu, J. S. 2014. "An Integrated Model for Robust Multisensor Data Fusion," *Sensors* (Basel, Switzerland) 14(10):19669-19686; Max Planck Institute for Dynamics of Complex Technical Systems Magdeburg; 2017. "Hierarchical Control Theory," at http://www.mpi-magdeburg.mpg.de/95036/Hierarchical-Control-Theory; "Hybrid Control Systems, at http://www.mpi-magdeburg.mpg.de/90434/Hybrid-Control-Systems).

However, practically speaking, the data in most medical applications require data extraction, fusion, and reduction with the prediction of consequential ensuing direction through methods such as Kálmán and Kálmán-derived filtering, or linear quadratic estimation to trigger the release of drugs in anticipation of a predictable tendency (see, for example, Su, J., Li, B., and Chen, W.-H. 2015. "On Existence, Optimality and Asymptotic Stability of the Kalman Filter with Partially Observed Inputs," *Automatica* 53: 149-154; Kálmán, R. E. and Bucy, R. S. 1961. "New Results in Linear Filtering and Prediction Theory," *Transactions of the American Society of Mechanical Engineers* 83(D. Basic Engineering):95-108; Kálmán, R. E. 1960. "A New Approach to Linear Filtering and Prediction Problems," *Transactions of the American Society of Mechanical Engineering* 82(D. Basic Engineering):35-45), or Bayesian inference only when numerous components are involved necessitating summarization, such as a disorder resulting from deficiencies or defects in cytochromes P450-containing enzymes in electron transfer chain hemoproteins.

Since here the prescription program is not just intended to optimize the treatment for each component morbidity but also to return the patient to as healthy a status as can be achieved across the entire complement or constellation of component morbidities, the nodes subordinate to the master node exchange their data laterally with the other nodes. This can be accomplished at the subordinate nodes or the master controller node. Over time, the master controller accumulates sufficient summary data concerning the overall homeostatic status across the sum of sensor inputs of the patient to infer the consequences of various possible responses in the form of commands to be passed down through the tree to the local effectors. It thus is able to dynamically adapt to the combination of circumstances confronting it; that is, it effectively 'learns,' adapts, gradually tailoring its response commands with greater and greater precision.

Such prescription programs are designed to first use generalized data which pertains less than precisely to the disease presented by the specific patient, and then by degrees where the results of antecedent system results, adjust the detailed response to achieve personalized, or 'precision,' medicine (see, for example, Sharafoddini, A., Dubin, J., and Lee, J. 2017. "Patient Similarity in Prediction Models Based on Health Data: A Scoping Review," *Journal of Medical Internet Research Medical Informatics* 5(1):e7; Schuck, R. N., Charlab, R., and Blumenthal, G. M. 2017. "Leveraging Genomic Factors to Improve Benefit-Risk," *Clinical and Translational Science* 10(2):78-83; Caraballo, P. J., Hodge, L. S., Bielinski, S. J., Stewart, A. K., Farrugia, G., and 11 others 2017. "Multidisciplinary Model to Implement Pharmacogenomics at the Point of Care," *Genetics in Medicine* 19(4):421-429; Cousin, M. A., Matey, E. T., Blackburn, P. R., Boczek, N. J., McAllister, T. M., and 4 others 2017. "Pharmacogenomic Findings from Clinical Whole Exome Sequencing of Diagnostic Odyssey Patients," *Molecular Genetics and Genomic Medicine* 5(3):269-279; Hinderer, M., Boeker, M., Wagner, S. A., Lablans, M., Newe, S., and 7 others 2017. "Integrating Clinical Decision Support Systems for Pharmacogenomic Testing into Clinical Routine—a Scoping Review of Designs of User-System Interactions in Recent System Development," *BioMed Central Medical Informatics and Decision Making* 17(1):81; Pacanowski, M. A. 2017. "Translating Precision," *Clinical and Translational Science* 10(2):56-57; Chakrabarti, S., Sen, A., Huser, V., Hruby, G. W., Rusanov, A., Albers, D. J., and Weng, C. 2017. "An Interoperable Similarity-based Cohort Identification Method Using the OMOP [Observational Medical Outcomes Partnership] Common Data Model Version 5.0," *Journal of Healthcare Informatics Research* 1(1):1-18; Ji, Y., Skierka, J. M., Blommel, J. H., Moore, B. E., VanCuyk, D. L., and 14 others 2016. "Preemptive Pharmacogenomic Testing for Precision Medicine: A Comprehensive Analysis of Five Actionable Pharmacogenomic Genes Using Next-Generation DNA Sequencing and a Customized CYP2D6 [cytochrome P450 2D6 enzyme, encoded by the CYP2D6 gene important in the metabolizing of xenobiotics, such as drugs and toxins] Genotyping Cascade," *Journal of Molecular Diagnostics* 18(3):438-445; Al-Mozaini, M. A. and Mansour, M. K. 2016. "Personalized Medicine. Is It Time for Infectious Diseases?," *Saudi Medical Journal* 37(12):1309-1311; Brown, S. A. 2016. "Patient Similarity: Emerging Concepts in Systems and Precision Medicine," *Frontiers in Physiology* 7:561; Formea, C. M., Nicholson, W. T., and Vitek, C. R. 2015. "An Inter-professional Approach to Personalized Medicine Education: One Institution's Experience," *Personalized Medicine* 12(2):129-138; Agyeman, A. A. and Ofori-Asenso, R. 2015. "Perspective: Does Personalized Medicine Hold the Future for Medicine?," *Journal of Pharmacy and Bioallied Sciences* 7(3):239-244; Blaus, A., Madabushi, R., Pacanowski, M., Rose, M., Schuck, R. N., Stockbridge, N., Temple, R., and Unger, E. F. 2015. "Personalized Cardiovascular Medicine Today: A Food and Drug Administration/Center for Drug Evaluation and Research Perspective," *Circulation* 132(15):1425-1432; Zhang, P., Wang, F., Hu, J., and Sorrentino, R. 2014. "Towards Personalized Medicine: Leveraging Patient Similarity and Drug Similarity Analytics," *American Medical Informatics Association Joint Summits on Translational Science Proceedings* 2014:132-136; Bielinski, S. J., Olson, J. E., Pathak, J., Weinshilboum, R. M., Wang, L., Lyke, K. J., Ryu, E., and 28 others 2014. "Preemptive Genotyping for Personalized Medicine: Design of the Right Drug, Right Dose, Right Time-using Genomic Data to Individualize Treatment Protocol," *Mayo Clinic Proceedings* 89(1):25-33; Kullo, I. J., Jarvik, G. P., Manolio, T. A., Williams, M. S., and Roden, D. M. 2013. "Leveraging the Electronic Health Record to Implement Genomic Medicine," *Genetics in Medicine* 15(4):270-271).

Shortcomings for precision or personalized medicine should, however, subside with experience in machine coordination of genomic and integrated medical record data (see, for example, He, K. Y., Ge, D., and He, M. M. 2017. "Big Data Analytics for Genomic Medicine," *International Journal of Molecular Sciences* 18(2). pii: E412; Wu, P. Y., Cheng, C. W., Kaddi, C. D., Venugopalan, J., Hoffman, R., and Wang, M. D. 2017. "-Omic and Electronic Health Record Big Data Analytics for Precision Medicine," Institute of Electrical and Electronics Engineers Transaction on Biomedical Engineering 64(2):263-273; Wu, P. Y., Cheng, C. W., Kaddi, C., Venugopalan, J., Hoffman, R., and Wang, M. D. 2016. "Advanced Big Data Analytics for -Omic Data and Electronic Health Records: Toward Precision Medicine," *Institute of Electrical and Electronics Engineers Transactions on Biomedical Engineering* October (in press); Carter, T. C. and He, M. M. 2016. "Challenges of Identifying Clinically Actionable Genetic Variants for Precision Medicine," *Journal of Healthcare Engineering Article* 3617572; He, K. Y., Zhao, Y., McPherson, E. W., Li, Q., Xia, F., Weng, C., Wang, K., and He, M. M. 2016. "Pathogenic Mutations in Cancer-predisposing Genes: A Survey of 300 Patients with Whole-genome Sequencing and Lifetime Electronic Health Records," *Public Library of Science One* 11(12): e0167847; Hovelson, D. H., McDaniel, A. S., Cani, A. K., Johnson, B., Rhodes, K., and 28 others 2015. "Development and Validation of a Scalable Next-generation Sequencing System for Assessing Relevant Somatic Variants in Solid Tumors," *Neoplasia* (NYC) 17(4):385-399; Zhang, L. and Hong, H. 2015. "Genomic Discoveries and Personalized Medicine in Neurological Diseases," *Pharmaceutics* 7(4): 542-553; Ye, H., Meehan, J., Tong, W., and Hong, H. 2015. "Alignment of Short Reads: A Crucial Step for Application of Next-Generation Sequencing Data in Precision Medicine," *Pharmaceutics* 7(4):523-541; Dubchak, I., Balasubramanian, S., Wang, S., Cem, M., Sulakhe, D., and 15 others 2014. "An Integrative Computational Approach for Prioritization of Genomic Variants," *Public Library of Science One* 9(12):e114903; Chen, G. and Shi, T. 2013. "Next-generation Sequencing Technologies for Personalized Medicine: Promising but Challenging," *Science China. Life Sciences* 56(2):101-103; Hong, H., Zhang, W., Shen, J., Su, Z., Ning, B., Han, T., Perkins, R., Shi, L., and Tong, W. 2013. "Critical Role of Bioinformatics in Translating Huge Amounts of Next-generation Sequencing Data into Personalized Medicine," *Science China. Life Sciences* 56(2):110-118).

Adaptive and predictive real time hierarchical control as pertains here uses a system of negative feedback loops with electronics fully implanted for very long-term use, but relegated to a belt-worn power and control pack for lesser periods, each feedback loop sourced in one or more, usually several different sensors assigned to an organ system or physiological pathway, feeding data to the next higher hierarchical level, each level in the hierarchy comparing and coordinating the data at that hierarchical level, up to the highest level of the master controller.

At that level, a prescription program under the control of an implanted master microprocessor node directs the dispensing of drugs to return the values read to within the normal range or homeostatic set point empirically, without regard to semantic or eponymous designation associated with the out-of-range readings as a named syndrome, classification, or idiopathic condition, especially since comorbidity can make the interrelation of symptoms obscure, but not to a system that quantifies the component physiological indicia without apportioning these among identified disorders and evaluates the response of each and the set of indicia as a whole to the drugs administered (see, for example, Mounce, L. T. A., Price, S., Valderas, J. M., and Hamilton, W. 2017. "Comorbid Conditions Delay Diagnosis of Colorectal Cancer: A Cohort Study Using Electronic Primary Care Records," *British Journal of Cancer* 116(12):1536-1543; Cai, J., Yuan, Z., and Zhang, S. 2015. "Abdominal Pain, Diarrhea, Constipation—Which Symptom is More Indispensable to Have a Colonoscopy?," *International Journal of Clinical and Experimental Pathology* 8(1):938-942; Eusebi, P. 2013. "Diagnostic Accuracy Measures," *Cerebrovascular Diseases* (Basel, Switzerland) 36(4):267-272; Pope, J. V. and Edlow, J. A. 2012. "Avoiding Misdiagnosis in Patients with Neurological Emergencies," *Emergency Medicine International* 2012:949275; Adelstein, B. A., Macaskill, P., Chan, S. F., Katelaris, P. H., and Irwig, L. 2011. "Most Bowel Cancer Symptoms Do Not Indicate Colorectal Cancer and Polyps: A Systematic Review," *BioMed Central Gastroenterology* 11:65).

Eliminated are the impulses to classify the component morbidities, the relationship between or among the diseases noted, identify an index condition, or determine whether the comorbidities subscribe to a more encompassing or common underlying disorder, for example (see, for example, Valderas, J. M., Starfield, B., Sibbald, B., Salisbury, C., and Roland, M. 2009. "Defining Comorbidity: Implications for Understanding Health and Health Services," *Annals of Family Medicine* 7(4):357-363; Rhee, S. H., Hewitt, J. K., Lessem, J. M., Stallings, M. C., Corley, R. P., and Neale, M. C. 2004. "The Validity of the Neale and Kendler Model-fitting Approach in Examining the Etiology of Comorbidity," *Behavior Genetics* 34(3):251-265; Schellevis, F. G., van der Velden, J., van de Lisdonk, E., van Eijk, J. T., and van Weel, C. 1993. "Comorbidity of Chronic Diseases in General Practice," *Journal of Clinical Epidemiology* 46(5): 469-473).

In dealing with comorbidity of which one or more of the component disorders are idiopathic and the number of possible chemical deficiencies, excesses, and other out of range indicia such as neuropsychological or endocrine malfunctions are too numerous to allow implanting an equivalent number of sensors, economic necessity mandates a reduction in this number by withdrawing from the detailed to a summary level. In this circumstance, the master node is provided with a library of detailed chemical interrelations within the scope of each sensor output as summary. By successive differential drug delivery as moves the focus among the component interrelated chemical pathways, the penultimate and master nodes gradually accumulate the data essential to interpolate or infer the detailed causes and effects comprehended within the sensor outputs.

At a higher level, the master node is entrusted with inferring the sum of reactions among the sensors assigned to a given component morbidity to have produced the summary result for the component morbidity, and from there, the set of component morbidities as a whole. For comorbidity of which each component disorder is diagnosed and substantially noninteractive with each of the others, the isolated targeting of drugs by direct piping avoids drug-drug interactions and adverse side effects, to include potential harm to uninvolved tissues and processes, while automated release assures compliance in patients who are debilitated or incompetent. From an economic standpoint, drug dispensing thus significantly reduces the time and attendance to patients of clinic or retirement community workers to occasional reservoir replenishment.

The system passes lower level site specific sensor data to the next higher level in the hierarchy and so on up through as many higher coordinative levels as necessary to best approximate homeostasis with the number of morbidities to be addressed (see, for example, Yang, K. and Haibo, J. 2017. "Adaptive Hierarchical Control for Output Feedback Systems," *International Journal of Control* 90(11):2317-2325; Kulkarni, A. and Kumar, A. 2016. "Adaptive Control Solution for a Class of MIMO [multiinput/multioutput] Uncertain Underactuated Systems with Saturating Inputs," *International Journal of Intelligent Systems and Application in Engineering* 4(4):135-144; Meng, L. 2015. *Hierarchical Control for Optimal and Distributed Operation of Microgrid Systems*, Copenhagen, Denmark: Aalborg University Press. Kulkarni, A. and Kumar, A. 2015. "Adaptive Hierarchical Control for a Class of Uncertain Underactuated Systems with Actuator Saturation," *Journal of Electrical Engineering*; Kulkarni, A. and Kumar, A. 2014. "Adaptive Hierarchical Control for a Class of MIMO [multiinput/multioutput] Uncertain Underactuated Systems," presented at the 2014 *Institute of Electrical and Electronics Engineers International Conference on Computational Intelligence and Computing Research*; Samsonovich, A. V., Jóhannsdóttir, K. R., Chella, A, and Goertzel, B. (eds) 2010. *Biologically Inspired Cognitive Architectures* 2010: *Proceedings of the First Annual Meeting of the BICA* [Biologically Inspired Cognitive Architectures] *Society*, Volume 221, *Frontiers in Artificial Intelligence and Applications*, Amsterdam, Holland: Scientific Programming Journal (IOS) Press); Zhang, Y., Wu, C., Xue, D., and Xiao, W. 2008. "Design and Implementation of a Hierarchical Control System for Wheeled Mobile Robot," *Institute of Electrical and Electronics Engineers Conference on Industrial Electronics and Applications*, at http://Institute of Electrical and Electronic Engineers Xplore, Institute of Electrical and Electronic Engineers.org/document/4582534/; Cavarischia, L. and Lanari, L. 2007. "Hierarchical Control Implementation," in 46*th Institute of Electrical and Electronics Engineers Conference on Decision and Control*, pages 3733-3738; Albus, J. S., Bostelman, R., Chang, T., Hong, T., Shackleford, W., and Shneier, M. 2006. "Learning in a Hierarchical Control System: 4D/RCS [Four dimensional/Real-time Control System], in the DARPA LAGR Program, "in International Conference on Informatics in Control, Automation, and Robotics 2006, at http://citeseerx.ist.psu.edu/viewdoc/download?doi=10.1.1.78.2266&rep=rep1&type=pdf; Meystel, A. M. and Albus, J. S. 2002. *Intelligent Systems*, New York, N.Y.: John Wiley and Sons, pages 30-31; Albus, J. S. 2002. "4D/RCS [Four dimensional/Real-time Control System]: A Reference Model Architecture for Intelligent Unmanned Ground Vehicles," *Proceedings of the Society of Photographic Instrumentation Engineers* 16*th Annual International Symposium on Aerospace/Defense Sensing, Simulation, and Controls*, at https://web.archive.org/web/20040725051856/http://www.isd.mel.nist.gov/documents/albus/4DRCS .pdf; Meystel, A. M. and Albus, J. S. 2001. Engineering of Mind: An Introduction to the Science of Intelligent Systems, New York, N.Y.: John Wiley and Sons; Chatha, K. S. and Vemuri, R. 2001. "MAGELLAN: Multiway Hardware Software Partitioning and Scheduling for Latency Minimization of Hierarchical Control-Dataflow Task Graphs," in Institute of Electrical and Electronics Engineers, Proceedings of the Ninth International Symposium on Hardware/Software Codesign; Albus, J. S. 2000. "4-D/RCS [Four dimensional/Real-time Control System] Reference Model Architecture for Unmanned Ground Vehicles," *Proceedings of the* 2000 *Institute of Electrical and Electronics Engineers International Conference on Robotics and Automation*; San Francisco, Calif., 24-28 Apr. 2000; Takahashi, Y. and Asada, M. 1999. "Behavior Acquisition by Multi-layered Reinforcement Learning," in *Proceedings of the* 1999 *Institute of Electrical and Electronics Engineers International Conference on Systems, Man, and Cybernetics*, Tokyo, 12-15 Oct. 1999, pages 716-721; Balakirsky, S. 1999. "Vehicle Level World Model Manager Interface Description," National Bureau of Standards NIST [National Institute of Standards and Technology] Research Library Volume NISTIR [National Institute of Standards and Technology Internal Report] 6441, at https://www.nist.gov/publications/vehicle-level-world-model-manager-interface-description; Takeda, Y., Dohi, Y., Murakoshi, H., Adachi, T., and Funakubo, N. 1999. "Resource Management Scheme by Petri Nets for Multiprocessors," in *Proceedings of the 25th Annual Institute of Electrical and Electronics Engineers Industrial Electronics Society International Conference on Industrial Electronics, Control, and Instrumentation*, Volume 2, pages 692-697; Dickmanns, E. D. 1998. "Vehicles Capable of Dynamic Vision: A New Breed of Technical Beings?," Artificial Intelligence 103(1-2):49-76, at http://www.science direct.com/science/article/pii/S000437029800071X; Albus, J. S. 1996. "The Engineering of Mind," "From Animals to Animats 4," in Maes, P., Mataric, M. J., Meyer, J.-A., Pollack, J., and Wilson, S. W. (eds), *Proceedings of the Fourth International Conference on Simulation of Adaptive Behavior (Complex Adaptive Systems)*, Cambridge, Mass.: Massachusetts Institute of Technology Press; Albus, J. S. 1993. "A Reference Model Architecture for Intelligent Systems Design," in Antsaklis, P. J. and Passino, K. M. (eds.), *An Introduction to Intelligent and Autonomous Control*, Dordrecht, Holland: Kluwer Academic Publishers, chapter 2, pages 27-56; Murakoshi, H., Kondo, T., Dohi Y., Anzai, F., N. Kawahara, Takei, T., and Watanabe, T. 1993. "Hardware Architecture for Hierarchical Control of Large Petri Net," in *Proceedings of the International Conference on Industrial Electronics, Control, and Instrumentation*, 1993; Hayes-Roth, F., Erman, L., and Terry, A. 1992. "Distributed Intelligent Control and Management (DICAM) Applications and Support for Semi-automated Development," *Working Notes from the* 1992 *AAAI* [Association for the Advancement of Artificial Intelligence] Workshop on Automating Software Design, Moffett Federal Airfield, California: U.S. National Aeronautics and Space Administration Ames Research Center, pages 66-70; Bryne, R. H. 1992. "A Practical Implementation of a Hierarchical Control System for Telerobotic Land Vehicles," in *Proceedings of the Institute of Electrical and Electronics Engineers National Conference on Telesystems*, pages 10/1-10/5; Jafari, M. A. and Meredith, G. A. 1991. "Analysis of Hierarchical Control Architectures: A Petri Net Approach," in Proceedings of the *Institute of Electrical and Electronics Engineers* International Conference on Robotics and Automation, 1991; Leonides, C. T. (ed.) 1991. *Manufacturing and Automation Systems: Techniques and Technologies*, (in 5 volume parts), San Diego, Calif.: Academic Press; Babary, J.-P. and LeLetty, L. (eds.) 1982. *Control of Distributed Parameter Systems* 1982, Proceedings of the Third IFAC [International Federation of Automatic Control] Symposium, Oxford, England: Pergamon Press; Findeisen, W., Bailey, F. N., Bryds, M. A., Malinowski, A., Tatjewski, P., and Wozniak, A. 1980. *Control and Coordination in Hierarchical Systems* (*International Series on Applied Systems Analysis*), Chichester, England: John Wiley and Sons Ltd.; Barrero, L., Binder, Z. Eynard, J. P., and Rey, D. 1979. "A Microprocessor Controller for Decentralised Hierarchical Control," *IFAC* [International Federation of Automatic Control] *Proceedings* 12(3):63-68; Risch, D. M. and Goar, D. 1978. "A Microprocessor Based Hierarchical Control System for Gas Turbines," *ASME* [American Society of Mechanical Engineers] 1978 *International Gas Turbine Conference and Products Show*, Paper 78-GT-124, pp. V01BT02A024, 18 pages, at http://proceedings.asmedigitalcollection.asme.org/proceeding.aspx?articleid=2277586).

As an example of the advantages offered by direct piping and release at the treatment site, few singular conditions, such as incipient diabetes mellitus type 2 before it affects other functions warrant directly targeted drug therapy through an implanted piping system, much less an implanted system of automatic control to react appropriately to a complex set of parameters; properly dosed, cited is the biguanide-derivative antihyperglycemic metformin hydrochloride oral, mostly marketed under the generic trade name 'Glucophage' from several makers. Some fraction of the metformin dose must be delivered throughout the body but is concentrated in the liver when a ductus side-entry jacket is used to infuse the drug directly into the portal vein for first pass delivery.

Where applicable, direct piping can avert the numerous adverse side effects associated with metformin or any other drug or reagent (see, for example, Wu, T, Horowitz, M., and Rayner, C. K. 2017. "New Insights into the Anti-diabetic Actions of Metformin: From the Liver to the Gut," *Expert Review of Gastroenterology and Hepatology* 11(2):157-166; Wang, Y., He, S. J., Feng, X., Cheng, J., Luo, Y. T., Tian, L., and Huang, Q. 2017. "Metformin: A Review of Its Potential Indications," *Drug Design, Development, and Therapy* 11:2421-2429; Sanchez-Rangel, E. and Inzucchi, S. E. 2017. "Metformin: Clinical Use in Type 2 Diabetes," *Diabetologia* August 2 (in press); Rena, G., Hardie, D. G., and Pearson, E. R. 2017. "The Mechanisms of Action of Metformin," *Diabetologia* August 3 (in press); Cameron, A. R., Logie, L., Patel, K., Erhardt, S., Bacon, S., and 13 others 2017. "Metformin Selectively Targets Redox Control of Complex I Energy Transduction," *Redox Biology* 14:187-197; Uddin, R., Nur-E-Habiba, Rena, G., Hwu, E. T., and Boisen, A. 2017. "New Evidence for the Mechanism of Action of a Type-2 Diabetes Drug Using a Magnetic Bead-based Automated Biosensing Platform," *American Chemical Society Sensors* 2(9):1329-1336; An, H. and He L. 2016. "Current Understanding of Metformin Effect on the Control of Hyperglycemia in Diabetes," *Journal of Endocrinology* 228(3): R97-106; Damião, C. P., Rodrigues, A. O., Pinheiro, M. F., Cruz Filho, R. A., Cardoso, G. P., Taboada, G. F., and Lima, G. A. 2016. "Prevalence of Vitamin B12 Deficiency in Type 2 Diabetic Patients Using Metformin: A Cross-sectional Study," *Sao Paulo Medical Journal* June 3. pii: S1516-31802016005004103 (in press); Zdilla, M. J. 2015. "Metformin with Either Histamine H2-receptor Antagonists or Proton Pump Inhibitors: A Polypharmacy Recipe for Neuropathy via Vitamin B12 Depletion," *Clinical Diabetes* 33(2):90-95 (also cited above under Background of the Invention); McCreight, L. J., Bailey, C. J., and Pearson, E. R. 2016. "Metformin and the Gastrointestinal Tract," *Diabetologia* 59(3):426-435; Pernicova, I. and Korbonits, M. 2014. "Metformin—Mode of Action and Clinical Implications for Diabetes and Cancer," *Nature Reviews. Endocrinology* 10(3):143-156; Pernicova, I. and Korbonits, M. 2014. "Metformin—Mode of Action and Clinical Implications for Diabetes and Cancer," *Nature Reviews. Endocrinology* 10(3):143-156; Nasri, H. and Rafieian-Kopaei, M. 2014. "Metformin: Current Knowledge," *Journal of Research in Medical Sciences* 19(7):658-664; Madiraju, A. K., Erion, D. M., Rahimi, Y., Zhang, X. M., and Braddock, D. T. 2014. "Metformin Suppresses Gluconeogenesis by Inhibiting Mitochondrial Glycerophosphate Dehydrogenase," *Nature* 510(7506):542-546; Viollet, B. and Foretz, M. 2013. "Revisiting the Mechanisms of Metformin Action in the Liver," *Annales d' Endocrinologie* (Paris, France) 74(2): 123-129; Viollet, B., Guigas, B., Sanz Garcia, N., Leclerc, J., Foretz, M., and Andreelli, F. 2012. "Cellular and Molecular Mechanisms of Metformin: An Overview," *Clinical Science* (London, England) 122(6):253-270; Isik, S., Ozcan, H. N., Ozuguz, U., Berker, D., Tutuncu, Y., Akbaba, G., and Guler, S. 2012. "Impaired Gallbladder motility and the Effect of metformin Therapy in patients with polycystic Ovary Syndrome," *Clinical Endocrinology* (Oxford, England) 76(3): 373-378) is of limited risk.

To treat diabetes, metformin must pass through the general circulation in some dose to affect all tissues in any event, and is known to favorably affect polycystic ovary syndrome and improve fertility, the more so when combined with clomifene (see, for example, Practice Committee of the American Society for Reproductive Medicine with 20 collaborators 2017. "Role of Metformin for Ovulation Induction in Infertile Patients with Polycystic Ovary Syndrome (PCOS): A Guideline," *Fertility and Sterility* 108(3):426-441; Clement, N. S., Oliver, T. R., Shiwani, H., Sanner, J. R., Mulvaney, C. A., and Atiomo, W. 2017. "Metformin for Endometrial Hyperplasia," *Cochrane Database of Systematic Reviews* 10:CD012214; Nwanodi, O. 2017. "Progestin Intrauterine Devices and Metformin: Endometrial Hyperplasia and Early Stage Endometrial Cancer Medical Management," *Healthcare* (Basel, Switzerland) 5(3). pii: E30; Al-Ruthia, Y. S., Al-Mandeel, H., AlSanawi, H., Mansy, W., AlGasem, R., and AlMutairi, L. 2017. "Ovulation Induction by Metformin among Obese Versus Non-obese Women with Polycystic Ovary Syndrome," *Saudi Pharmaceutical Journal* 25(5):795-800; Guo, Z., Sevrioukova, I. F., Denisov, I. G., Zhang, X., Chiu, T. L., and 32 others 2017. "Heme Binding Biguanides Target Cytochrome P450-Dependent Cancer Cell Mitochondria," *Cell Chemical Biology* 24(10): 1259-1275.e6; Ferreira, C., Sousa, M., Rabaça, A., Oliveira, P. F., Alves, M. G., and Sá, R. 2015. "Impact of Metformin on Male Reproduction," *Current Pharmaceutical Design* 21(25):3621-3633; Naderpoor, N., Shorakae, S., de Courten, B., Misso, M. L., Moran, L. J., and Teede, H. J. 2015. "Metformin and Lifestyle Modification in Polycystic Ovary Syndrome: Systematic Review and Meta-analysis," *Human Reproduction Update* 21(5):560-574; Alves, M. G., Martins, A. D., Vaz, C. V., Correia, S., Moreira, P. I., Oliveira, P. F., and Socorro, S. 2014. "Metformin and Male Reproduction: Effects on Sertoli Cell Metabolism," *British Journal of Pharmacology* 171(4):1033-1042; Johnson, N. P. 2014. "Metformin Use in Women with Polycystic Ovary Syndrome," *Annals of Translational Medicine* 2(6):56; Lashen, H. 2010. "Role of Metformin in the Management of Polycystic Ovary Syndrome," *Therapeutic Advances in Endocrinology and Metabolism* 1(3): 117-128).

The benefits in direct tissue or organ nidus or lesion targeting to avoid significant contact with unintended tissues and organs apply to most drugs. For exemplary purposes, metformin is addressed here because in the United States alone, it is prescribed for about 65 million patients per year. While the literature is frequently contradictory, mixing indications and contraindications, especially where sleep disorders such as nightmares, insomnia, sleepwalking, and sleep apnea are concerned, metformin can be said to have beneficial effects for numerous diseases, and pending wider confirmation, beneficial in man as well as lower vertebrates used for testing as cited below. Some researchers claim that metformin alleviates, while others claim it aggravates sleep disorders. It is also claimed that metformin alleviates sleep apnea. Despite at least 18 thousand published articles, numerous applications for metformin, alone or combined with other drugs, remain indecisive with trials ongoing (see, for example, Clement, N. S., Oliver, T. R., Shiwani, H., Sanner, J. R., Mulvaney, C. A., and Atiomo, W. 2017. "Metformin for Endometrial Hyperplasia," *Cochrane Database of Systematic Reviews* 10:CD012214).

Thus, widely prescribed and inordinately elusive of clear characterization as either completely beneficial or deleterious, references explicitly or implicitly pertaining to the sleep effects of metformin are segregated here for citation (Petrie, J. R., Chaturvedi, N., Ford, I., Brouwers, M. C. G. J., and Greenlaw, N., 11 others and 145 collaborators 2017. "Cardiovascular and Metabolic Effects of Metformin in Patients with Type 1 Diabetes (REMOVAL) [REducing with MetfOrmin Vascular Adverse Lesions in Type 1 Diabetes]: A Double-blind, Randomised, Placebo-controlled Trial," *Lancet. Diabetes and Endocrinology* 5(8):597-609; Schnell, O., Rydén, L., Standl, E., and Ceriello, A. 2017. "Updates on Cardiovascular Outcome Trials in Diabetes," *Cardiovascular Diabetology* 16(1):128; Elmaraezy, A., Abushouk, A. I., Emara, A., Elshahat, O., Ahmed, H., and I Mostafa, M. 2017. "Effect of Metformin on Maternal and Neonatal Outcomes in Pregnant Obese Non-diabetic Women: A Meta-analysis," *International Journal of Reproductive Biomedicine (Yazd, Iran)* 15(8):461-470; Sośnicki, S., Kapral, M., and Węglarz, L. 2016. "Molecular Targets of Metformin Antitumor Action," *Pharmacological Reports* 68(5):918-925; Doumit, J. and Prasad, B. 2016. "Sleep Apnea in Type 2 Diabetes," *Diabetes Spectrum* 29(1):14-19; Lin, D., Rein, L., Tarima, S., Woodson, B. T., and Meurer, J. R. 2015. "The Relationship Between Metformin and Obstructive Sleep Apnea," *Journal of Sleep Medicine and Disorders* 2(4). pii: 1027; Wiernsperger, N. 2015. "Metformin as a Cellular Protector: A Synoptic View of Modern Evidences," *Journal of Nephropharmacology* 4(1):31-36. eCollection 2015; Priou, P., Le Vaillant, M., Meslier, N., Chollet, S. 4, Pigeanne, T., 6 others, and 15 collaborators 2015. "Association Between Obstructive Sleep Apnea Severity and Gglucose Control in Patients with Untreated Versus Treated Diabetes," *Journal of Sleep Research* 24(4):425-431; Kajbaf, F., Fendri, S., Basille-Fantinato, A., Diouf, M., Rose, D., Jounieaux, V., and Lalau, J. D. 2014. "The Relationship Between Metformin Therapy and Sleep Quantity and Quality in Patients with Type 2 Diabetes Referred for Potential Sleep Disorders," *Diabetic Medicine* 31(5):577-580; Inzucchi, S. E., Lipska, K. J., Mayo, H., Bailey, C. J., and McGuire, D. K. 2014. "Metformin in Patients with Type 2 Diabetes and Kidney Disease: A Systematic Review," *Journal of the American Medical Association* 312(24):2668-2675; Sivalingam, V. N., Myers, J., Nicholas, S., Balen, A. H., and Crosbie, E. J. 2014. "Metformin in Reproductive Health, Pregnancy and Gynaecological Cancer: Established and Emerging Indications," *Human Reproduction Update* 20(6): 853-868; El-Sharkawy, A. A., Abdelmotaleb, G. S., Aly, M. K., and Kabel, A. M. 2014. "Effect of Metformin on Sleep Disorders in Adolescent Girls with Polycystic Ovarian Syndrome," *Journal of Pediatric and Adolescent Gynecology* 27(6):347-352; Kajbaf, F., Fendri, S., Basille-Fantinato, A., Diouf, M., Rose, D., Jounieaux, V., and Lalau, J. D. 2014. "The Relationship Between Metformin Therapy and Sleep Quantity and Quality in Patients with Type 2 Diabetes Referred for Potential Sleep Disorders," *Diabetic Medicine* 31(5):577-580; Grimaldi, D., Beccuti, G., Touma, C., Van Cauter, E., and Mokhlesi, B. 2014. "Association of Obstructive Sleep Apnea in Rapid Eye Movement Sleep with Reduced Glycemic Control in Type 2 Diabetes: Therapeutic Implications," *Diabetes Care* 37(2):355-363; Shohrati, M., Karbasi-Afshar, R., and Saburi, A. 2012. "Remarks in Metformin and Sleep Disorders in Diabetic Patients," *Indian Journal of Endocrinology and Metabolism* 16(4):675-676; Wiwanitkit, S. and Wiwanitkit, V. 2012. "Metformin and Sleep Disorders," *Indian Journal of Endocrinology and Metabolism* 16 Supplement 1:S63-S64; Ramadan, W., Petitjean, M., Loos, N., Geloen, A., Vardon, G., Delanaud, S., Gros, F., and Dewasmes, G. 2006. "Effect of High-fat Diet and Metformin Treatment on Ventilation and Sleep Apnea in Non-obese Rats," *Respiration Physiology and Neurobiology* 150(1):52-65).

Where potentially deleterious effects must be prevented and the beneficial effect is local to the nidus, the clear indication is to use direct piping to the treatment site through a ductus side-entry jacket or nonjacketing side-entry connector. For nondiabetic disease, directly piped targeting may open the way for the preventive use of antidiabetic drugs in nondiabetics (see, for example, Tseng, C. H. 2017. "Metformin is Associated with a Lower Risk of Colorectal Cancer in Taiwanese Patients with Type 2 Diabetes: A Retrospective Cohort Analysis," *Diabetes and Metabolism* 43(5):438-445; Tseng, C. H. 2017. "Metformin and Lung Cancer Risk in Patients with Type 2 Diabetes Mellitus," *Oncotarget* 8(25):41132-41142; Tseng, C. H. 2016. "Metformin Use and Cervical Cancer Risk in Female Patients with Type 2 Diabetes," *Oncotarget* 7(37):59548-59555; Zhang, C. Y., Yuan, W. G., He, P., Lei, J. H., and Wang, C. X. 2016. "Liver Fibrosis and Hepatic Stellate Cells: Etiology, Pathological Hallmarks and Therapeutic Targets," *World Journal of Gastroenterology* 22(48):10512-10522). Use of metformin in nondiabetic parturients, however, is contraindicated (Elmaraezy, A., Abushouk, A. I., Emara, A., Elshahat, O., Ahmed, H., and I Mostafa, M. 2017, cited below).

For nondiabetics, the potential applications of drugs currently approved as antidiabetics for use by diabetics has been found to affect a large number of other disorders related and unrelated to insulin level (see, for example, Liang, Z., Li, T., Jiang, S., Xu, J., Di, W., Yang, Z., Hu, W., and Yang, Y. 2017. AMPK [adenosine monophosphate-activated protein kinase]: A Novel Target for Treating Hepatic Fibrosis," *Oncotarget* 8(37):62780-62792; Kim, H., Moon, S. Y., Kim, J. S., Baek, C. H., Kim, M., Min, J. Y., and Lee, S. K. 2015. "Activation of AMP [adenosine monophosphate]—activated Protein Kinase Inhibits ER [endoplasmic reticulum] Stress and Renal Fibrosis," *American Journal of Physiology. Renal Physiology* 308(3):F226-F236; Ghosh, P. 2017. "The Stress Polarity Pathway: AMPK 'GIV'-es [AMP-activated protein kinase G-alpha interacting vesicle associated protein, trade name Girdin] Protection Against Metabolic Insults," *Aging* (Albany, N.Y.) 9(2):303-314; Li, X., Liu, R., Zhang, L., and Jiang, Z. 2017. "The Emerging Role of AMP [adenosine monophosphate]-activated Protein Kinase in Cholestatic Liver Diseases," *Pharmacological Research* 125(Part B):105-113; Liao, K. F., Chuang, H. Y., and Lai, S. W. 2017. "Metformin Use Correlates with Reduced Risk of Gallstones in Diabetic Patients: A 12-Year Follow-up Study," *Frontiers in Pharmacology* 8:765; Dasgupta, A., Trucco, M., Rainusso, N., Bernardi, R. J., Shuck, R., Kurenbekova, L., Loeb, D. M., and Yustein, J. T. 2017. "Metabolic Modulation of Ewing Sarcoma Cells Inhibits Tumor Growth and Stem Cell Properties," *Oncotarget* 8(44):77292-77308; Wang, J., Zhu, L., Hu, K, Tang, Y., Zeng, X., Liu, J., and Xu, J. 2017. "Effects of Metformin Treatment on Serum Levels of C-reactive Protein and Interleukin-6 in Women with Polycystic Ovary Syndrome: A Meta-analysis: A PRISMA [preferred reporting items for systematic reviews and meta-analyses]-compliant Article," *Medicine* (Baltimore, Md.) 96(39): e8183; Udhane, S. S., Legeza, B., Marti, N., Hertig, D., Diserens, G., Nuoffer, J. M., Vermathen, P., and Flück, C. E. 2017. "Combined Transcriptome and Metabolome Analyses of Metformin Effects Reveal Novel Links Between Metabolic Networks in Steroidogenic Systems," *Scientific Reports* 7(1):8652; Horiuchi, T., Sakata, N., Narumi, Y., Kimura, T., Hayashi, T., and 8 others 2017. "Metformin Directly Binds the Alarmin HMGB1 [high mobility group box 1] and Inhibits Its Proinflammatory Activity," *Journal of Biological Chemistry* 292(20):8436-8446; Imam, T. H. 2017. "Changes in Metformin Use in Chronic Kidney Disease," *Clinical Kidney Journal* 10(3):301-304.; Matsiukevich, D., Piraino, G., Lahni, P., Hake, P. W., Wolfe, V., O'Connor, M., James, J., and Zingarelli, B. 2017. "Metformin Ameliorates Gender- and Age-dependent Hemodynamic Instability and Myocardial Injury in Murine Hemorrhagic Shock," *Biochimica et Biophysica Acta* 1863(10 Part B):2680-2691; Bell, S., Farran, B., McGurnaghan, S., McCrimmon, R. J., Leese, G. P., and 8 others 2017. "Risk of Acute Kidney Injury and Survival in Patients Treated with Metformin: An Observational Cohort Study," *BioMed Central Nephrology* 18(1):163; Tseng, C. H. 2017. "Metformin and Lung Cancer Risk in Patients with Type 2 Diabetes Mellitus," *Oncotarget* 8(25):41132-41142; Yousef, M. and Tsiani, E. 2017. "Metformin in Lung Cancer: Review of in Vitro and in Vivo Animal Studies," *Cancers* (Basel, Switzerland) 9(5). pii: E45; Kim, P., Piraino, G., O'Connor, M., Hake, P. W., Wolfe, V., Lahni, P., and Zingarelli, B. 2017. "Metformin Exerts Beneficial Effects in Hemorrhagic Shock in an Ampkα1 [AMP-activated protein kinase]-independent Manner," *Shock* September 14 (in press); Zhang, S., Xu, H., Yu, X., Wu., Y., and Sui, D. 2017. "Metformin Ameliorates Diabetic Nephropathy in a Rat Model of Low-dose Streptozotocin-induced Diabetes," *Experimental and Therapeutic Medicine* 14(1):383-390; Calip, G. S., Yu, O., Elmore, J. G., and Boudreau, D. M. 2016. "Comparative Safety of Diabetes Medications and Risk of Incident Invasive Breast Cancer: A Population-based Cohort study," *Cancer Causes and Control* 27(5):709-720; Tseng, C. H. 2016. "Metformin Reduces Gastric Cancer Risk in Patients with Type 2 Diabetes Mellitus," *Aging* (Albany, N.Y.) 8(8):1636-1649; Du, K., Ramachandran, A., Weemhoff, J. L., Chavan, H., Xie, Y., Krishnamurthy, P., and Jaeschke, H. 2016. "Editor's Highlight: Metformin Protects Against Acetaminophen Hepatotoxicity by Attenuation of Mitochondrial Oxidant Stress and Dysfunction," *Toxicological Sciences* 154(2):214-226; Singh, J., Olle, B., Suhail, H., Felicella, M. M., and Giri, S. 2016. "Metformin-induced Mitochondrial Function and ABCD2 Up-regulation in X-linked Adrenoleukodystrophy Involves AMP-activated Protein Kinase," *Journal of Neurochemistry* 138(1):86-100; Chen, W., Liu, X., and Ye, S. 2016. "Effects of Metformin on Blood and Urine Proinflammatory Mediators in Patients with Type 2 Diabetes," *Journal of Inflammation* (London, England) 13:34. eCollection 2016; Siskind, D. J., Leung, J., Russell, A. W., Wysoczanski, D., and Kisely, S. 2016. "Metformin for Clozapine Associated Obesity: A Systematic Review and Meta-Analysis," *Public Library of Science One* 11(6):e0156208; Sakoda, L. C., Ferrara, A., Achacoso, N. S., Peng, T., Ehrlich, S. F., Quesenberry, C. P. Jr., and Habel, L. A. 2015. "Metformin Use and Lung Cancer Risk in Patients with Diabetes," *Cancer Prevention Research* (Philadelphia, Pa.) 8(2):174-179; Kim, Y. H., Hwang, J. H., Kim, K. S., Noh, J. R., Choi, D. H., and 5 others 2015. "Metformin Ameliorates Acetaminophen Hepatotoxicity via Gadd45β-dependent [growth arrest and DNA damage-inducible 45 beta proteindependent] Regulation of JNK [c-Jun N-terminal kinase] Signaling in Mice," *Journal of Hepatology* 63(1):75-82; Ryu, R. J., Hays, K. E., and Hebert, M. F. 2014. "Gestational Diabetes Mellitus Management with Oral Hypoglycemic Agents, Seminars in Perinatology 38(8):508-515; Zhao, R. R., Xu, X. C., Xu, F., Zhang, W. L., Zhang, W. L., Liu, L. M. 4, and Wang, W. P. 2014. "Metformin Protects Against Seizures, Learning and Memory Impairments and Oxidative Damage Induced by Pentylenetetrazole-induced Kindling in Mice," *Biochemical and Biophysical Research Communications* 2014 448(4):414-417; Maruthini, D., Harris, S. E., Barth, J. H., Balen, A. H., Campbell, B. K., and Picton, H. M. 2014. "The Effect of Metformin Treatment in Vivo on Acute and Long-term Energy Metabolism and Progesterone Production in Vitro by Granulosa Cells from Women with Polycystic Ovary Syndrome," *Human Reproduction* 29(10): 2302-2316; Nie, S. P., Chen, H., Zhuang, M. Q., and Lu, M. 2014. "Anti-diabetic Medications Do Not Influence Risk of Lung Cancer in Patients with Diabetes Mellitus: A Systematic Review and Meta-analysis," *Asian Pacific Journal of Cancer Prevention* 15(16):6863-6869; Luo, Q., Hu, D., Hu, S., Yan, M., Sun, Z., and Chen, F. 2012. "In Vitro and in Vivo Anti-tumor Effect of Metformin as a Novel Therapeutic Agent in Human Oral Squamous Cell Carcinoma," *BioMed Central Cancer* 12:517; "Hirsch, A., Hahn, D., Kempná, P., Hofer, G., Nuoffer, J. M., Mullis, P. E., and Flück, C. E. 2012. "Metformin Inhibits Human Androgen Production by Regulating Steroidogenic Enzymes HSD3B2 and CYP17A1 and Complex I Activity of the Respiratory Chain," *Endocrinology* 153(9):4354-4366; Lai, S. W., Björkhem-Bergman, L., Asplund, A. B., and Lindh, J. D. 2011. "Metformin for Weight Reduction in Non-diabetic Patients on Antipsychotic Drugs: A Systematic Review and Meta-analysis," *Journal of Psychopharmacology* (Oxford, England) 25(3): 299-305; Muo, C. H., Liao, K. F., Sung, F. C., and Chen, P. C. 2011. "Risk of Acute Pancreatitis in Type 2 Diabetes and Risk Reduction on Anti-diabetic Drugs: A Population-based Cohort Study in Taiwan," *American Journal of Gastroenterology* 106(9):1697-1704; Gonzalez-Perez, A., Schlienger, R. G., and Rodríguez, L. A. 2010. "Acute Pancreatitis in Association with type 2 Diabetes and Antidiabetic Drugs: A Population-based Cohort Study," *Diabetes Care* 33(12): 2580-2585).

By the same token, emplacing a directly pipe-targeting system with downstream reversal or neutralization if necessary can make possible the freer use of metformin in patients in whom solely systemic dispersal would otherwise provoke adverse reactions, questionably, as documented below, in those with kidney, liver, and lung disease, but also in those without such preconditions made nauseous, diarrheic, rarely, lactic acidotic, and according to some but disputed by others who, directly contradictory, ascribe to metformin a protective role, impaired mental function more pronounced than that attributable to diabetes alone, in the elderly partially reversible with the administration of vitamin $B_{12}$, (cobalmin), (Bornstein, S., Moschetta, M., Kawano, Y., Sacco, A., Huynh, D., and 12 others 2017. "Metformin Affects Cortical Bone Mass and Marrow Adiposity in Diet-induced Obesity in Male Mice," *Endocrinology* 158(10):3369-3385; Herath, P. M., Cherbuin, N., Eramudugolla, R., and Anstey, K. J. 2016. "The Effect of Diabetes Medication on Cognitive Function: Evidence from the PATH [population-based cohort study in Australia] Through Life Study," *Biomed Research International* 2016: 7208429; Cholerton, B., Baker, L. D., Montine, T. J., and Craft, S. 2016. "Type 2 Diabetes, Cognition, and Dementia in Older Adults: Toward a Precision Health Approach," *Diabetes Spectrum* 29(4):210-219; Hemmingsen, B., Sonne, D. P., Metzendorf, M. I., and Richter, B. 2016. "Insulin Secretagogues for Prevention or Delay of Type 2 Diabetes Mellitus and Its Associated Complications in Persons at Increased Risk for the Development of type 2 Diabetes Mellitus," *Cochrane Database of Systematic Reviews* 10:CD012151; Feinkohl, I., Price, J. F., Strachan, M. W., and Frier, B. M. 2015. "The Impact of Diabetes on Cognitive Decline: Potential Vascular, Metabolic, and Psychosocial Risk Factors," *Alzheimer's Research and Therapy* 7(1):46; Guo, M., Mi, J., Jiang, Q. M., Xu, J. M., Tang, Y. Y., Tian, G., and Wang, B. 2014. "Metformin May Produce Antidepressant Effects Through Improvement of Cognitive Function Among Depressed Patients with Diabetes Mellitus," *Clinical and Experimental Pharmacology and Physiology* 41(9):650-656; Ng, T. P., Feng, L., Yap, K. B., Lee, T. S., Tan, C. H., and Winblad, B. 2014. "Long-term Metformin Usage and Cognitive Function Among Older Adults with Diabetes," *Journal of Alzheimer's Disease* 41(1):61-68; Moore, E. M., Mander, A. G., Ames, D., Kotowicz, M. A., Came, R. P., 10 others, and 150 collaborators 2013. "Increased Risk of Cognitive Impairment in Patients with Diabetes is Associated with Metformin," *Diabetes Care* 36(10):2981-2987; Chapman, L. E., Darling, A. L., and Brown, J. E. 2016, cited below; Ahmed, M. A. 2016, cited below; Saedi, E., Gheini, M. R., Faiz, F., and Arami, M. A. 2016. "Diabetes Mellitus and Cognitive Impairments," *World Journal of Diabetes* 7(17):412-422), in the elderly, administered parenterally or in the form of sublingual microlozenges for absorption through the oral mucosa (but see Zhao, R. R., Xu, X. C., Xu, F., Zhang, W. L., Zhang, W. L., Liu, L. M. 4, and Wang, W. P. 2014, cited above), where the bulk of the dose is directly targeted in a higher concentration with a reduced dose if necessary infused into the general circulation through a ductus side-entry jacket about the portal vein, for example, (see, for example, Thangthaeng, N., Rutledge, M., Wong, J. M., Vann, P. H., Forster, M. J., and Sumien, N. 2017. "Metformin Impairs Spatial Memory and Visual Acuity in Old Male Mice," *Aging and Disease* 8(1):17-30; Khan, A., Shafiq, I., and Hassan Shah, M. 2017. "Prevalence of Vitamin B12 Deficiency in Patients with Type II Diabetes Mellitus on Metformin: A Study from Khyber Pakhtunkhwa," *Cureus* 9(8):e1577; Camilleri, M., Malhi, H., and Acosta, A. 2017. "Gastrointestinal Complications of Obesity," *Gastroenterology* 152(7):1656-1670; Weinrauch, L. A., Segal, A. R., Bayliss, G. P., Liu, J., Wisniewski, E., and D'Elia, J. A. 2017. "Changes in Treatment of Hyperglycemia in a Hypertensive Type 2 Diabetes Population as Renal Function Declines," *Clinical Kidney Journal* 10(5):661-665; Bicsak, T. A., Walsh, B., and Fineman M. 2017. "Metformin-associated Lactic Acidosis: Moving Towards a New Paradigm?," *Diabetes, Obesity, and Metabolism* 19(11):1499-1501; Gangopadhyay, K. K. and Singh, P. 2017. "Consensus Statement on Dose Modifications of Antidiabetic Agents in Patients with Hepatic Impairment," *Indian Journal of Endocrinology and Metabolism* 21(2):341-354; Lalau, J. D., Kajbaf, F., Protti, A., Christensen, M. M., De Broe, M. E., and Wiernsperger, N. 2017. "Metformin-associated Lactic Acidosis (MALA): Moving Towards a New Paradigm," *Diabetes, Obesity, and Metabolism* 19(11):1502-1512; Yang, J. S., Lu, C. C., Kuo, S. C., Hsu, Y. M., Tsai, S. C., and 11 others 2017. "Autophagy and Its Link to Type II Diabetes Mellitus," *Biomedicine* (Taipei, Taiwan) 7(2):8; Siavash, M., Tabbakhian, M., Sabzghabaee, A. M., and Razavi, N. 2017. "Severity of Gastrointestinal Side Effects of Metformin Tablet Compared to Metformin Capsule in Type 2 Diabetes Mellitus Patients," *Journal of Research in Pharmaceutical Practice* 6(2):73-76; Bonnet, F. and Scheen, A. 2017. "Understanding and Overcoming Metformin Gastrointestinal Intolerance," *Diabetes, Obesity, and Metabolism* 19(4):473-481; Abdelgadir, E., Ali, R., Rashid, F., and Bashier, A. 2017. "Effect of Metformin on Different Non-diabetes Related Conditions, a Special Focus on Malignant Conditions: Review of Literature," *Journal of Clinical Medicine Research* 9(5):388-395; Connelly, P. J., Lonergan, M., Soto-Pedre, E., Donnelly, L., Zhou, K., and Pearson, E. R. 2017. "Acute Kidney Injury, Plasma Lactate Concentrations and Lactic Acidosis in Metformin Users: A GoDarts [Genetics of Diabetes Audit and Research Tayside cohort] Study," *Diabetes, Obesity, and Metabolism* 19(11): 1579-1586; Lo, C., Jun, M., Badve, S. V., Pilmore, H., White, S. L., and 4 others 2017. "Glucose-lowering Agents for Treating Pre-existing and New-onset Diabetes in Kidney Transplant Recipients," *Cochrane Database of Systematic Reviews* 2:CD009966; McCreight, L. J., Bailey, C. J., and Pearson, E. R. 2016. "Metformin and the Gastrointestinal Tract," *Diabetologia* 59(3):426-435; Chapman, L. E., Darling, A. L., and Brown, J. E. 2016. "Association Between Metformin and Vitamin B12 Deficiency in Patients with Type 2 Diabetes: A systematic Review and Meta-analysis," *Diabetes and Metabolism* 42(5):316-327; Ahmed, M. A. 2016. "Metformin and Vitamin B12 Deficiency: Where Do We Stand?," *Journal of Pharmacy and Pharmaceutical Sciences* 19(3):382-398; Vos, R. C., van Avendonk, M. J., Jansen, H., Goudswaard, A. N., van den Donk, M., Gorter, K., Kerssen, A., and Rutten, G. E. 2016. "Insulin Monotherapy Compared with the Addition of Oral Glucose-lowering Agents to Insulin for People with Type 2 Diabetes Already on Insulin Therapy and Inadequate Glycaemic Control," *Cochrane Database of Systematic Reviews* 9:CD006992; Sakoda, L. C., Ferrara, A., Achacoso, N. S., Peng, T., Ehrlich, S. F., Quesenberry, C. P. Jr., and Habel, L. A. 2015. "Metformin Use and Lung Cancer Risk in Patients with Diabetes," *Cancer Prevention Research* (Philadelphia, Pa.) 2015 8(2):174-179; Lalau, J. D., Arnouts, P., Sharif, A., and De Broe, M. E. 2015. "Metformin and Other Antidiabetic Agents in Renal Failure Patients," *Kidney International* 87(2):308-322; i, L., Zinman, B., Patel, S., Ji, J., Bailes, Z., Thiemann, S., and Seck, T. 2015. "Efficacy and Safety of Linagliptin Co-administered with Low-dose Metformin Once Daily Versus High-dose Metformin Twice Daily in Treatment-naïve Patients with Type 2 Diabetes: A Double-blind Randomized Trial," *Advances in Therapy* 32(3):201-215; Heaf, J. 2014. "Metformin in Chronic Kidney Disease: Time for a Rethink," *Peritoneal Dialysis International* 34(4):353-357; Rocha, A., Almeida, M., Santos, J., and Carvalho, A. 2013. "Metformin in Patients with Chronic Kidney Disease: Strengths and Weaknesses," *Journal of Nephrology* 26(1):55-60; Saadi, T., Waterman, M., Yassin, H., and Baruch, Y. 2013. "Metformin-induced Mixed Hepatocellular and Cholestatic Hepatic Injury: Case Report and Literature Review," *International Journal of General Medicine* 6:703-706; Alsubaie, S. and Almalki, M. H. 2013. "Metformin Induced Acute Pancreatitis," *Dermatoendocrinology* 5(2):317-318; Boland, B. S., Edelman, S. V., and Wolosin, J. D. 2013. "Gastrointestinal Complications of Diabetes," *Endocrinology and Metabolic Clinics of North America* 42(4):809-83; Rafieian-Kopaie, M. 2013. "Metformin and Renal Injury Protection," *Journal of Renal Injury Prevention* 2(3):91-92; Bouchoucha, M., Uzzan, B., and Cohen, R. 2011. "Metformin and Digestive Disorders," *Diabetes and Metabolism* 37(2):90-96; Brackett, C. C. 2010. "Clarifying Metformin's Role and Risks in Liver Dysfunction," *Journal of the American Pharmacists Association* (2003) 50(3):407-410; Decensi, A., Puntoni, M., Goodwin, P., Cazzaniga, M., Gennari, A., Bonanni, B., and Gandini, S. 2010. "Metformin and Cancer Risk in Diabetic Patients: A Systematic Review and Meta-analysis," *Cancer Prevention Research* (Philadelphia, Pa.) 3(11):1451-1461; Hoffmann, I. S., Roa, M., Torrico, F., and Cubeddu, L. X. 2003. "Ondansetron and Metformin-induced Gastrointestinal Side Effects," *American Journal of Therapeutics* 10(6):447-451). Such a system is also beneficial where concentrated doses to target sites allow the systemic dose to be much reduced. That view that metformin is contraindicated in patients with chronic kidney disease is currently undergoing transition.

Other drugs for the treatment of Type 2 diabetes, such as the glucagon-like peptide 1 receptor agonist dipeptidyl peptidase-4 (DPP-4) inhibitors sitagliptin (Januvia®, Merck), liraglutide (Victoza®, Saxenda® Novo Nordisk), exenatide (Byetta®, Bydureon® AstraZeneca), dulaglutide (Trulicity®, Eli Lilly and Company), and the newer semaglutide (Ozempic®, Novo Nordisk), as almost all drugs can produce adverse side effects that would be substantially reduced if not indiscriminately dispersed at the effective dose throughout the body rather than differentially delivered to target tissue, to include kidney and pancreatic damage, and equivocally, thyroid cancer.

This includes semaglutide, effective for its intended purposes, and possibly preferable for heart patients (see, for example, Cosmi, F., Laini, R., and Nicolucci, A. 2017. "Semaglutide and Cardiovascular Outcomes in Patients with Type 2 Diabetes," *New England Journal of Medicine* 376 (9):890; Ipp, E., Genter, P., and Childress, K. 2017. "Semaglutide and Cardiovascular Outcomes in Patients with Type 2 Diabetes," *New England Journal of Medicine* 376(9):890-891; Williams, T. C. and Stewart, E. 2017. "Semaglutide and Cardiovascular Outcomes in Patients with Type 2 Diabetes," *New England Journal of Medicine* 376(9):891; Marso, S. P., Holst, A. G., and Vilsboll, T. 2017. "Semaglutide and Cardiovascular Outcomes in Patients with Type 2 Diabetes," *New England Journal of Medicine* 376(9):891-892; Marso, S. P., Bain, S. C., Consoli, A., Eliaschewitz, F. G., Jódar, E., and 10 others 2016. "Semaglutide and Cardiovascular Outcomes in Patients with Type 2 Diabetes," *New England Journal of Medicine* 375(19):1834-1844); but not free of adverse side effects, such as gastrointestinal (see, for example, Htike, Z. Z., Zaccardi, F., Papamargaritis, D., Webb, D. R., Khunti, K., and Davies M. J. 2017. "Efficacy and Safety of Glucagon-like Peptide-1 Receptor Agonists in Type 2 Diabetes: A Systematic Review and Mixed-Treatment Comparison Analysis," *Diabetes, Obesity, and Metabolism* 19(4):524-536; Tan, X., Cao, X., Zhou, M., Zou, P., and Hu, J. 2017. "Efficacy and Safety of Once-weekly Semaglutide for the Treatment of Type 2 Diabetes," *Expert Opinion on Investigational Drugs* 26(9):1083-1089; Xue, X., Ren, Z., Zhang, A., Yang, Q., Zhang, W., and Liu, F. 2016. "Efficacy and Safety of Once-weekly Glucagon-like Peptide-1 Receptor Agonists Compared with Exenatide and Liraglutide in Type 2 Diabetes: A Systemic Review of Randomised Controlled Trials," *Internatonal Journal of Clinical Practice* 70(8):649-656; Nauck, M. A., Petrie, J. R., Sesti, G., Mannucci, E., Courrèges, J. P., Lindegaard, M. L., Jensen, C. B., and Atkin, S. L. 2016. "A Phase 2, Randomized, Dose-Finding Study of the Novel Once-Weekly Human GLP-1 Analog, Semaglutide, Compared with Placebo and Open-label Liraglutide in Patients with Type 2 Diabetes," *Diabetes Care* 39(2):231-241).

However, exceptions pertain to immunosuppressive, anti-inflammatory, antimicrobial, and anticancer drugs which bode significant side effects for unintended tissue, and therefore serve better when targeted. The applications contemplated pertain to comorbidity, where either substantially independent or noninteractive morbidities coexist or interdependent disease conditions associated with one or more organs, tissues, and/or chemical pathways interact in so complex a manner as to warrant automated computation to define or characterize and control the targeted delivery of drugs to various loci to best achieve optimal health given the overall condition of the patient.

The long term use of steroids without isolation from nontargeted tissue by directly piped delivery to the nidus or site of treatment can create the opportunity for infection, produce or aggravate a morbidity or comorbidity, such as chronic airway congestive conditions addressed above, or when used to ameliorate inflammation in solid organ transplantation where systemic immunosuppressants cooperate to render the patient especially susceptible to infection, and can provoke serious endocrine, musculoskeletal, central nervous system, and cardiovascular effects (see, for example, Malvezzi, P., Jouve, T., and Rostaing, L. 2017. "Long-Term Steroid-Based Therapy: Risk of Infectious Complications in Immunosuppressed Kidney-Transplant Recipients as Compared to the General Population," *Journal of Urology & Nephrology* 2( )2:000124; Chaudhary, N. S. 2, Donnelly, J. P. 2, Moore, J. X., Baddley, J. W., Safford, M. M., and Wang, H. E. 2017. "Association of Baseline Steroid Use with Long-term Rates of Infection and Sepsis in the REGARDS [reasons for geographic and racial differences in stroke] Cohort," *Critical Care* (London, England) 21(1):185; Dalal, A. A., Duh, M. S., Gozalo, L., Robitaille, M. N., Albers, F., and 5 others 2016. "Dose-Response Relationship Between Long-term Systemic Corticosteroid Use and Related Complications in Patients with Severe Asthma," *Journal of Managed Care and Specialty Pharmacy* 22(7):833-847; Rostaing, L. and Malvezzi, P. 2016. "Steroid-based Therapy and Risk of Infectious Complications," *Public Library of Science Medicine* 13(5):e1002025; Youssef, J., Novosad, S. A., and Winthrop, K. L. 2016. "Infection Risk and Safety of Corticosteroid Use," *Rheumatic Diseases Clinics of North America* 42(1):157-176, ix-x; Lefebvre, P., Duh, M. S., Lafeuille, M. H., Gozalo, L., Desai, U., and 7 others 2015. "Acute and Chronic Systemic Corticosteroid-related Complications in Patients with Severe Asthma," *Journal of Allergy and Clinical Immunology* 136(6):1488-1495; Cukuranovic, J., Ugrenovic, S., Jovanovic, I., Visnjic, M., and Stefanovic, V. 2012. "Viral Infection in Renal Transplant Recipients," *Scientific World Journal* 2012:820621; Moghadam-Kia, S. and Werth, V. P. 2010. "Prevention and Treatment of Systemic Glucocorticoid Side Effects," *International Journal of Dermatology* 49(3):239-248).

Hundreds of such examples might be adduced, to include the use of corticosteroids to ameliorate the symptoms of inflammatory bowel disease. Delivery to the lungs of a corticosteroid is generally through ductus side-entry jackets on the pulmonary arteries. Rather, the applications for a fully implanted hierarchical drug dispensing control system contemplated pertain to comorbidity, where either substantially independent morbidity exists or interdependent diseased conditions of one or more organs, tissues, and/or chemical pathways interact. FIG. 107 shows the use of a nonjacketing side-entry connector to channel drugs directly into the bladder wall and/or cavity. An antibiotic destructive to the intestinal microbiota is eliminated from the gut. At the gut, a corticosteroid used to reduce the inflammation of an inflammatory bowel disease is kept from steroid-susceptible tissues and those the steroid renders susceptible to infection.

Then the object is to return each loop and substrate pathway to its normal set point, and in so doing, remediate the totality of malfunction in its interactive consequences. In complex situations where the number of sensors required to adequately monitor different substances or pathways is not feasible, the object is to identify, monitor, and treat one or more sources common to these. To eliminate nonessential components, extensive diagnostic testing is performed before the detailed hardware requirements are specified, and known causes or results of pathology such as a lesion is treated before fitting; for example, when operable, a tumor is resected and if possible, an interval allowed for full recovery.

Because the organ is dysfunctional or has become decompensated, numerous conditions will not respond to a dynamically targeted dispensing of drugs to different sites of disease. Where feasible and dependable, a centralized computer in the medical center could receive sensor inputs and administer the prescription programs of each center patient by telemetric remote control through a transceiver implanted in the patient, thus eliminating the need for an implant microcontroller. However, on the basis of current dependability of such automation and the possibility of malicious intrusion, entrusting such a critical function to a computer and communication by radio, even over a relatively small area, is premature. In the future, a centralized supercomputer in a specialty medical center could control all such implant systems at a high level of patient inclusion, even nationwide.

Generally, when transmitted to a center, the output of individual sensors are sufficient to indicate the associated symptoms, and by recording these over time allow the diagnosticians to infer the action required to return the pertinent values to within the normal ranges (see, for example, Lo, Y. K., Kuan, Y. C., Culaclii, S., Kim, B., Wang, P. M., and 7 others 2017. "A Fully Integrated Wireless SoC [system-on-a-chip] for Motor Function Recovery after Spinal Cord Injury," *Institute of Electrical and Electronics Engineers Transactions on Biomedical Circuits and Systems* 11(3):497-509; Mirbozorgi, S. A., Bahrami, H., Sawan, M., Rusch, L. A., and Gosselin, B. 2016. "A Single-Chip Full-duplex High Speed Transceiver for Multi-site Stimulating and Recording Neural Implants," *Institute of Electrical and Electronics Engineers Transactions on Biomedical Circuits and Systems* 10(3):643-653 (also cited above in the section entitled Background of the Invention. Field of the Invention); Khan, S. R. and Choi, G. 2016. "Analysis and Optimization of Four-coil Planar Magnetically Coupled Printed Spiral Resonators," *Sensors* (Basel, Switzerland) 16(8). pii: E1219; Kuan, Y. C., Lo, Y. K., Kim, Y., Chang, M. C., an Liu, W. 2015. "Wireless Gigabit Data Telemetry for Large-scale Neural Recording," *Institute of Electrical and Electronics Engineers Journal of Biomedical Health Informatics* 19(3):949-957; Jegadeesan, R., Nag, S., Agarwal, K., Thakor, N. V., and Guo, Y. X. 2015. "Enabling Wireless Powering and Telemetry for Peripheral Nerve Implants," *Institute of Electrical and Electronics Engineers Journal of Biomedical Health Informatics* 19(3):958-970; Giagka, V., Eder, C., Donaldson, N., and Demosthenous, A. 2015. "An Implantable Versatile Electrode-driving ASIC [application specific integrated circuit] for Chronic Epidural Stimulation in Rats," *Institute of Electrical and Electronics Engineers Transactions on Biomedical Circuits and Systems* 9(3):387-400; Tang, S. C., Jolesz, F. A., and Clement, G. T. 2011. "A Wireless Batteryless Deep-seated Implantable Ultrasonic Pulser-receiver Powered by Magnetic Coupling," *Institute of Electrical and Electronics Engineers Transactions on Ultrasonics, Ferroelectrics, and Frequency Control* 58(6):1211-1221; Qiu, Y., Haley, D., and Chen, Y. 2014. "Energy-efficient Adaptive Modulation in Wireless Communication for Implanted Medical Devices," *Conference Proceedings of the Institute of Electrical and Electronics Engineers Engineering in Medicine and Biology Society* 2014:918-921; Kiourti, A., Psathas, K. A., and Nikita, K. S. 2014. "Implantable and Ingestible Medical Devices with Wireless Telemetry Functionalities: A Review of Current Status and Challenges," *Bioelectromagnetics* 35(1):1-15; Mutashar, S., Hannan, M. A., Samad, S. A., and Hussain, A. 2014. "Analysis and Optimization of Spiral Circular Inductive Coupling Link for Bio-implanted Applications on Air and Within Human Tissue," *Sensors* (Basel, Switzerland) 14(7): 11522-11541Tang, S. C., Jolesz, F. A., and Clement, G. T. 2011. "A Wireless Batteryless Deep-seated Implantable Ultrasonic Pulser-receiver Powered by Magnetic Coupling," *Institute of Electrical and Electronics Engineers Transactions on Ultrasonics, Ferroelectrics, and Frequency Control* 58(6):1211-1221; Ferguson, J. E. and Redish, A. D. 2011, Op cit.; Ramrakhyani, A. K., Mirabbasi, S., and Mu Chiao 2011. "Design and Optimization of Resonance-based Efficient Wireless Power Delivery Systems for Biomedical Implants," *Institute of Electrical and Electronics Engineers Transactions on Biomedical Circuits and Systems* 5(1):48-63).

In that case, this primary pathology must first be remedied such as by transplantation. If this restores homeostasis, then the adaptive hierarchical control implant system serves to control the targeted dispensing of immunosuppressives to the transplant and monitor any sequelae in the transplant and native organs. The inputs to the lowest level comprise sensors that detect specific indicia of physiological function at each site of morbidity. A master controller programed to measure deviations from the normal value for each function takes the subfinally processed data from the next lower level in the hierarchy oversees and coordinates the entirety of data, extracting the consequences of administering a given drug at each site. This identifies the interrelated consequences among the sites or nidi of a certain drug when targeted at one of the sites.

Note that such diagnosis:

1. Makes the directly targeted delivery, release, traceability, and local consequence of use of each drug certain as to identity and volume as substantially segregated from other drugs in concurrent use.

2. At the same time isolates drugs, minimizing exposure to other tissue and minimizing or eliminating side effects while allowing higher doses at the target site.

3. The implementation of such a system is dependent upon the availability of connectors to vessels, to other bodily ductus, and to nonductal tissue which unlike indwelling catheters and other connectors cannot become dislodged, compress vasa or nervi vasora, and will not leak or deteriorate so that these can remain fully implanted to the end of life.

Such connectors, described in copending application Ser. Nos. 14/121,365 and 14/998,495, are devised to minimize the trauma of placement, prevent leaks, and impose as little adverse effect on substrate tissue as the unavoidable need for physical contact will allow. This includes subsidiary lines to maintain the connectors and to treat any adverse sequelae such as unwanted tissue reactions as might arise. The lack of dependable connectors is the ultimate factor preventing the implementation of artificial intelligence in fully implantable systems to aright correctible deviations from normal function to within the normal range when remediable. In some cases, this will require preliminary surgery or transplantation before such a system can be applied.

The direct targeting to the sites or nidi of disease spares nontargeted tissue from exposure, so that provided it does not arouse more adverse consequences than it eliminates, a fully implanted, ambulatory, and automatic scheme of direct piping will usually surpass the systemic administration of drugs, certainly for diagnostic purposes. If administering a certain drug at any one site results in no significant shifting toward or away from the normal or homeostatic value at each of the other sites, then the component morbidities are effectively independent, that is, related only tenuously, as one would expect of part in a unit organism. If significant, the comorbidity is interdependent.

Numerous instances of dependent (secondary, sequelary) impairment such as the cardiorenal syndrome have long been recognized. If adaptive (self-tuning, capable of learning'), then when confronted with interdependent comorbid conditions, the master controller registers the effect of administering a drug at one site upon each of the detected variables and sum of the others. By determining and delivering the combination of drugs that accomplishes homeostasis as might best be approximated, this accumulated 'experience' makes possible the optimization in overall condition of the patient.

FIG. 108 shows the hierarchical control system as contained within an extracorporeal control, power, and pump pack attached to a waist belt or belt cinched about a thigh. While sensors must be implanted, the contents of the control, power, and pump pack are generally implanted when and to the extent that the size of the components and the condition of the patient permit. To take up the least space, especially in a prenate, neonate, or young child, full implantation will usually be decentralized or distributed rather than centralized. Even in a late term prenate, this affords wide latitude in positioning the separate tiny encased nodal microcontroller chips not depictable in two dimensions without numerous two dimensional sectional views, and accordingly omitted in FIG. 107.

In a prenate or neonate, the elimination of wires is accomplished with ultra-low energy Bluetooth transception. This not only eliminates the risk of organ or tissue strangulation as it would in an adult, but eliminates the need for rewiring as the baby grows. Also to allow for growth, the fluid lines for the direct pipe-targeting of drugs are made of coiled extendable plastic catheters which are able to lengthen considerably when the extension imposed by growth causes their attachments to recede from one another, the lines then urged to their smallest freely reached length (see Reum, D. J. 1978. Method for Producing a Spirally Wound Plastic Article, U.S. Pat. No. 4,120,929). The spring loaded stent-jackets and relatively thick foam lining of stent-jackets, impasse-jackets, and nonjacketing side-entry connectors also afford sufficient latitude to accommodate growth over a lengthy interval.

Whereas FIG. 107 shows a fully implanted automatic disorder response system, FIG. 108 shows such a system in generalized and simplified schematic form wherein only the sensors and side-entry jackets are implanted. In a practical system, both side-entry jackets and nonjacketing side-entry connectors would almost always be used, and these might or might not incorporate and position the sensors. These implanted components are shown at the top of FIG. 108 in the box labeled 'body.' Connection to the belt-worn power, control, and pump/reservoir pack includes electrical lines schematically shown as single and/or fluid lines shown as double or tubular, which plug into a small port at the body surface schematically indicated by the word 'port' between the top and center boxes. Generally, the master node is a microprocessor and the subordinate nodes small chip microcontrollers.

In the arrangement shown in FIG. 108, the sensors and jackets at the top of the drawing are depicted as collocated if not integrated, that is, with sensors incorporated within the jacket, electrical signals originating with the sensors and drug delivery directed to the same or a nearby location. The actual implanted components variable and the connections of these to the components in the extracorporeal (external) pack variously necessitating electrical and/or fluid connections, single and double lines rather than a pictorial representation is used to indicate these respectively. FIG. 108 necessarily generalized and simplified, included are only two channels or legs of control, each monitored by four symptom or physiological indicia sensors directed to either of the separate morbidities, which may of may not interact to a significant degree.

Each set of sensors generate signals which pass to a node respective of each sensor as shown in the boxed about portion of the schematic at the bottom of the drawing. These first order processing nodes pass their data to an intermediate set of nodes in communication with the primary nodes individually and severally. These intermediate level microcontroller nodes at the summary level of the morbidity respective of each pass their data to the master node microprocessor responsible for integrating the data across both morbidities to regulate the delivery of drugs from small implant reservoirs in a coordinated manner to achieve the optimal homeostatic result for the patient. When the system is placed prior to surgery that would correct a defect or defects which significantly contribute to the sensory data profile, the prescription program and arrangement of components must be adjusted accordingly.

When the surgery pertains to anatomy that had earlier been provided with sensors, adjustments in sensors and their positioning is accomplished during the surgery. When these factors do not coincide, the rearrangement can be accomplished after an interval, but not if continuation of the existing regimen would prove injurious with the anatomical changes introduced. In many instances, some components and the prescription program will require change during the same procedure while others will be deferred. Because the delivery of therapeutic means whether drugs, heating, or electrostimulation, for example, is targeted, depending upon the interdependency of data for any two morbidities, coordination for the master node may be lessened.

This does not apply, for example, to an endocrine axis such pituitary-adrenal or anywhere else that glandular communication is not limited to detectable changes in reasonably detectable blood chemistry, blood pressure, or a change in temperature. FIG. 108 is simplified, in that only two comorbid conditions are represented, four sensors are assigned to each, and the therapeutic means (in the center box) are limited to drug therapy. In actuality, any number of sensors can be assigned to any one morbidity, the response might include the application of measures to include or exclude drugs. As the complexity of the system rises with the addition of each sensor, the number of these should be kept to a minimum. Were four coexisting morbidities present and two or more of these were interactive, the burden, processing time, energy consumption, and heat generation of the master node microprocessor would be increased.

This in turn imposes the need for thermal insulation and the additional if slight space this would require, reducing the number of sites for placement. If the master node is not to be relegated to an external pack, then time permitting, tissue expansion should be accomplished in a preliminary procedure. For this reason, it is important that the internist clearly specify the need for sensors and nodes for the prescription programmer. Morbid conditions vary considerably in the need for more than one or two sensors, and substantially noninteractive morbidities should not be assigned the degree of data coordination appropriate for interactive morbidities. Since ultimately the output or all sensors must be coordinated with each of the others, the addition of any nonessential sensor materially increases the overall complexity and cost of the system.

Sensor and internodal communication is exclusively electrical, denoted by single connecting lines, while pump jacket connections are shown with double lines to indicate that these connections are tubular for moving fluid. FIG. 108 assumes that the small reservoir pump motors are steppers, eliminating the need for closed loop feedback to the directing master node. The capability of the master node to direct any of a number of drugs by means of indexing a turret mechanism to place the drug wanted in the delivery line is described in copending application Ser. No. 14/121,365. As shown, the drug turrets are contained within an external control, power, and pump pack attached to a waist belt or cinched about a thigh.

When drug volumes and the number thereof allow, these too are implanted, the goal to achieve as close to a fully implanted system as can be managed. At the interface between the nodes and pumps between the two lower boxed-about sections in a body pack, the connections are electrical, the projections meant to indicate the plugs or jacks and the depressions sockets. In FIG. 108, these are relegated to the external (extracorporeal) control, power, and pump pack. In less complex systems where all of the components are implanted, the only visible component is a small port at the body surface needed to house button cells and provide openings through which to pass miniature fiber optic and other cables. Electrical connections to the port are required only when an implanted battery is to be recharged through a power supply rather than by transdermal or transcutaneous energy transfer or a test instrument is used to evaluate the function of the component attached to the port socket. Replenishment of the implanted drug reservoirs does not require external openings, small tattoos used to indicate the injection points.

Consistency allowing simplification and assuring minimal space uptake in prenates and neonates, for example, for implanted use across all body sizes, every component, to include those used to achieve wireless internodal communication, must be reduced to the smallest size possible. This makes possible the elimination or wires even in prenates and neonates. The patient must not experience internal sensations associated with system componentry that rubs against if not abrades neighboring tissue, even if this later subsides once the parts become encapsulated within fibrous tissue. In most instances, this eliminates the need for a preliminary and time-consuming procedure of creating a pocket or pockets to contain one or more components by means of tissue expansion.

Moreover, to provide a system wherein highly concentrated drugs are diluted prior to delivery likewise demanding a larger water or liquid reagent supply reservoir and mechanism and means for switching this among a number of drug vials in any event, a more elaborate fully implanted real time automatic ambulatory adaptive/predictive system for response to a number of comorbid conditions must include some components of which the dimensions must follow from the absolute volume of the fluid drugs required. In this circumstance, the hierarchical control system componentry is best decentralized or distributed rather than centralized, thus reducing the need for larger spaces to house the required system modules.

However, whereas a decentralized hierarchical control system in an industrial application can usually connect the system sensors, nodes, and effectors by wire, data intercommunication among a plurality of components within the body poses a problem, in that any fluid and electrical line must be routed to assure that organs and tissues are never strangulated. This may prove difficult, may require the use of suture, staples, or clips, all prone to result in discomfort if not pain or more serious complications, as well as demanding much additional procedural time to place, even if no unexpected complications arise during the operation.

The application of wireless transmission in lieu of hard wiring to interconnect the decentralized components complements the application of very large scale integrated, and eventually, molecular electronics to make the implant system least obtrusive in relation to older technology hardware implementation of a hierarchical control system (where the application pertains to high power or large scale industrial systems, the essential concepts should be understood as applicable by analogy to microelectronics in the service of medicine, see for example, Forrester, J. K. 2016. *An Overview of Molecular Electronics*, Seattle, Wash.: Amazon/CreateSpace Publishing; Karroach, R. 2016. *Nanoelectronics: Molecular Electronics*, Seattle, Wash.: Amazon/Create Space Publishing; Zenke, A. 2016. Molecular Electronics: Advanced Topics in Nanotechnology, Seattle, Wash.: Amazon/CreateSpace Publishing; Durna, E., Çevik, Y., Karagöz, M., and Civil, A. 2016. "Design and Implementation of a Hierarchical Control System Architecture for a Modular Pulsed Power Supply System," *Institute of Electrical and Electronics Engineers International Power Modulator and High Voltage Conference*, 2016, at http://ieeexplore.ieee.org/document/8012916/; Kong, Z., Pi, D., Wang, X., Wang, H., and Chen, S. 2016. "Design and Evaluation of a Hierarchical Control Algorithm for an Electric Active Stabilizer Bar System," *Journal of Mechanical Engineering* (Ljubljana, Slovenia) 63(12): 565-576; Baldea, L. 2015. *Molecular Electronics: An Experimental And Theoretical Approach*, Boca Raton, Fla.: Chemical Rubber Company Press; Cuevas, J. C. and Scheer, E. 2010. *Molecular Electronics: An Introduction to Theory and Experiment* (Nanotechnology and Nanoscience), (World Scientific Series in Nanotechnology and Nanoscience), Singapore: World Scientific Publishing Company; Scattolini, R. 2009. "Architectures for Distributed and Hierarchical Model Predictive Control—A Review," *Journal of Process Control* 19:723-731; Mahler, G., May, V., and Schreiber, M. 1996. *Molecular Electronics: Properties, Dynamics, and Applications*, Boca Raton, Fla.: Chemical Rubber Company Press; Bloor, D., Bryce, M. R., and Petty, M. C. (eds.) 1994. *Introduction to Molecular Electronics*, Oxford, England: Butterworth-Heinemann; Murakoshi, H., Kondo, T., Dohi, Y., Anzai, F., Kawahara, N., Takei, T., and Watanabe, T. 1993. "Hardware Architecture for Hierarchical Control of Large Petri Net," *Proceedings of the International Conference on Industrial Electronics, Control, and Instrumentation*, 1993, available at http://ieeexplore.ieee.org/document/339096/?reload=true; Jones, A. T. and McLean, C. R. 1986. "A Proposed Hierarchical Control Model for Automated Manufacturing Systems," *Journal of Manufacturing Systems* 5(1):15-25; Schweppe, F. C. 1978. "Power Systems '2000': "Hierarchical Control Strategies," *Institute of Electrical and Electronics Engineers Spectrum Magazine* 15(7), in that not only the components but their interconnections are rendered least obtrusive.

Not only is the space required to house the various system components reduced to the minimum, but the additional procedural time, difficulties that might arise during placement, and the possibility of numerous postoperative complications are much reduced if not eliminated. Equally important, wireless connection among sensors and nodes is unaffected by growth, allowing placement in neonates and small children without concern over the possibility of catching, entrapment, or organ strangulation by electrical lines during growth. If for any reason, wireless connection is not advisable, the fluid and electrical lines used are coiled to allow extension sufficient to last for years before replacement, that of the electrical lines preferably with wireless interconnections.

Components of the implanted body-embedded system network such as a microprocessor master node, if implanted, microcontroller subordinate nodes, biotelemetric and ultra-low energy 'Bluetooth' radio frequency module internodal transceivers, can be expected to initially provoke an adverse tissue reaction, recommending an outer layer of anti-inflammatory medication, usually steroidal. This will subside and the components become encapsulated by fibrous tissue. In a fetus, neonate, or child, growth will furnish additional tissue to dissipate any residual radiated heat. Even after enclosure to cover over sharp edges and corners, wireless 'bluetooth' ultra-low energy, low power transceiver chips typically measuring 6×6 millimeters pose no heating or space accommodation problem.

For implantation, however, any component which operates sensibly above body temperature should be packaged to prevent heat radiation at this level. Means for quantifying heat generation are available (Sajith, V. and Sobhan, C. B. P. 2012. "Characterization of Heat Dissipation from a Microprocessor Chip Using Digital Interferometry," *Institute of Electrical and Electrical Engineers Transactions on Components, Packaging and Manufacturing Technology* 2(8): 1298-1306; Mahajan, R., Chiu, C., and Chrysler, G. 2006. "Cooling a Microprocessor Chip," *Proceedings of the Institute of Electrical and Electronics Engineers* 94(8):1476-1486; Viswanath, R., Wakharkar, V., Watwe, A., and Lebonheur, V. 2000. "Thermal Performance Challenges from Silicon to Systems," *Intel Technology Journal*, at http://www.intel.com/technology/itj/q32000/articles/art_4.htm). While general purpose high capacity central processing units such as the Intel i7 series have an average maximum operating temperature of 142 degrees Fahrenheit, the full-load temperature will normally average about 45 degrees Fahrenheit, well within the acceptable range.

The risk of excessive heat is substantially pertinent to only the highest capacity processing units and then only when these are under intensive use, that is, operated under a constant full workload (Stone, D. 2017. "What is the Average Temperature of an Intel i7 Processor?," Hearst Newspapers *Chron*, at http://smallbusiness.chron.com/average-temperature-intel-i7-processor-81659.html). It is improbable that any but a master node controller, a special rather than general purpose processor, would pose a problem of excessive heat. Other microprocessors in a distributed node system are lighter duty and pose little risk of excessive heat. If in fact numerous comorbidities are involved and the remedies proposed below do not resolve the problem, the master node controller can be worn on the outside of the body. The reciprocal condition—the effect of the temperature of the body on the processor is not a problem Lifelong implantation of microcircuits requires that heat dissipation be reduced to the extent possible, both to preserve the service life of the circuitry itself and to prevent the transfer of heat to the surrounding tissue, which if significantly higher from microcircuits not intentionally intended to do double service for thermoplasty, would prohibit implantation. Implantation circuity to support an implanted automatic disorder response system as described herein and in copending application Ser. No. 14,121,365 now 20160051806 and Ser. No. 14/998,495 now 20170197028, consists of the master and control nodes, biomedical, and wireless internodal transceivers.

Quite apart from the prospect of implantation, means for minimizing the generation of heat to extend processor service life have been ongoing for years, heat sinks, heat spreaders and thermal/ground pads, for example, long in use. To enclose a component within an insulating shell prevents heat from radiating into the surrounding tissue but traps the heat inside the shell, reducing service life. One approach is to counter the heat by including Peltier devices, cascaded if necessary, with hot sides attached to heat sinks.

Other than to cover over sharp edges and corners, few master node microprocessors, much less subordinate node microcontrollers, biotelemetric or ultra-low energy 'Bluetooth' transceivers, or system on a chip modules unifying a node with its transceiver should require the enclosure to provide thermal insulation. The space taken up by the thicker wall this necessitates takes up space that more significantly in a fetus, neonate, or small experimental animal risks encroachment upon neighboring tissue. To avoid deviations in operating frequency due to inconsistencies in the power supplied as the battery discharges, only superheterodyne receivers are used. To avoid electrostatic discharge which can damage integrated circuits, it is essential that handling, system assembly in preparation for implantation, and implantation in a precautionary manner.

At full load, transceivers other than ultra-low power Bluetooth can generate heat well above that suitable for implantation. To specify whether implantation or implantation with the ameliorative measures specified above is an option, or the transceiver module must be worn outside of the body, the maximum potential workload for the specific system and functions proposed for implantation must be known. The shell in this case serves to cover over the sharp edges and corners of the nodal microcontrollers and transceivers, if any (Incropera, F. P. 1988. "Convection Heat Transfer in Electronic Equipment Cooling," *Journal of Heat Transfer* 110(4b): 1097-1111).

Small scale microprocessors programmed as nodes incorporate heat reduction means and should not pose a heat problem, despite the need to enclose these within a nonallergenic plastic shell to cover over sharp edges and corners. Replacing metal wires with optical fibers remains to yield cooler running microcircuits or core communications (Templeton, G. 2016. "Here's Why We Don't Have Light-based Computing Just Yet," at https://www.extremetech.com/extreme/223671-heres-why-we-dont-have-light-based-computing-just-yet.

When the tissues or organs to be treated are not deep and the patient is a competent adult, system placement—even when including numerous components—can usually be accomplished using local anesthetic nerve blocks, thus averting the persistent numbness associated with neurolytic block, the high risk for postprocedural deafferentation or neuronal pain following neurectomy or the crushing of sensory fibers, and the cognitive problems associated with the use of general anesthesia.

Implanted electrical lines are eliminated through wireless transmission. Here, in contrast to the intracorporeal use thereof to date, which is to transmit from within the body to the exterior (see, for example, White, J. and Tumlin, K. 2013. *Apparatus and Method for Sensor Deployment and Fixation*, U.S. Pat. No. 8,355,777; Gilad, Z. 2012. System for In Vivo Detection of a Body Lumen, Japanese Patent 5,039,378), the use of ultra-low energy wireless, or 'Bluetooth' transmission is used to allow data transfer among sensors and control nodes when some or all are implanted within the body. The form factors and absolute size of wireless transmitter-receivers now makes it possible to use these even in near term prenates. The wide discrepancy in carrier frequencies used for wireless and biotelemetric transmission substantially eliminates the possibility of interference between the two, to include their harmonics (see, for example, Laskovski, A. N. and Yuce, M. R. 2008. "Harmonics-based Bio-implantable Telemetry System," *Proceedings of the Annual Conference of the Institute of Electrical and Electronics Engineers Engineering in Medicine and Biology Society* 3196-3199).

In the United States, Bluetooth ultra-high frequency (UHF) ultra-low energy short-range radio carriers are assigned the industrial, scientific and medical (ISM) band from 2.4 to 2.485 gigahertz. Biotelemetric transmission to the clinic is assigned to a long-range biotelemetric radio frequency band from 608 to 614 MHz, or from 1395 to 1400 MHz; or from 1427 to 1432 MHz, shared with non-medical telemetry operations. In the United States, different frequency ranges apply in different regions; however, whichever is used, interference between biotelemetric and ultra-low energy Bluetooth signals or their harmonics does not occur. Neither should carrier frequencies assigned to garage door openers or keyless door entry systems, for example, hopping or rolling coded between 300 to 400 MHz, ever cause interference.

XXII. Glossary of Terms

Ablation-capable barrel-assembly—A radial discharge barrel-assembly (qv.), or airgun barrel-extending catheter, that can apply heat (electrocautery; thermal cautery), cold (cryogenic cautery; cryocautery), and/or shaving or abrading action to ablate lumen-obstructive matter in any type of ductus. Lacking internal gas pressure relief passages to prevent gas embolism, often using different thermal or cryogenic temperatures, and lacking an ischemia-averting outward conformation, it is not for use in the vascular tree. Except in diameters suited for use in narrower bronchi and ureters, it is also too large in diameter for use in blood vessels. By contrast, a smaller gauge device, an ablation and angioplasty-capable barrel-assembly (qv.), includes these features, and is always capable of performing an ablation in a nonvascular ductus. A minimally-capable embodiment is meant to ablate minimally as immediately preparatory to implantation in a single procedure if not a single pass. For economy, a minimally-capable embodiment is not usable apart from and dependent upon connection to the airgun power supply through contacts at its end-plate through an end-socket (qv.). By contrast, a fully capable unit, whether bipartite (qv.) by combining a minimally-capable unit with a matching combination-form radial projection catheter (qv.) or as a self-contained apparatus, can be used to perform an ablation while physically independent from the airgun and without regard to whether it will thereafter be inserted into an airgun to initiate stenting discharge; airgun-independent capable barrel-assembly. Cf. angioplasty-capable barrel-assembly; ablation and angioplasty-capable barrel-assembly.

Ablation and angioplasty-capable barrel-assembly—A radial discharge barrel-assembly (qv.), or interventional airgun barrel extension-catheter, which is capable of performing an ablation or an angioplasty while separate from an airgun. Such capability requires either one or more radial projection systems (qv.) about the muzzle-head, or if bipartite (qv.), accession to these components through ensheathment within a matching combination-form (qv.) radial projection catheter (qv.), or a central channel (qv.) for accepting a cabled ablation or atherectomy device, such as a laser or atherectomy cutter. Because it provides a central channel for a cabled apparatus, the latter is referred to as a through-bore or combination-form (qv.) ablation and angioplasty-capable barrel-assembly with radial projection system. Only a barrel-assembly of millimetric gauge that include gas pressure relief channels is also capable of performing an angioplasty. For both ablative and angioplasty capability, the barrel-assembly must also be equipped with radial projection units (qv.) and tool-inserts (qv.) having the temperature and material removal rates required for either process. Incorporating a control panel atop the onboard power and control housing, it is self-contained and can be used separately from or while engaged in an airgun. While in the airgun, its is generally controlled from the airgun control panel; when separate, from the control panel atop its power and control housing. This allows both free movement and implant discharge capability without the need for withdrawal from the lumen; airgun-independent capable barrel-assembly. Cf. ablation-capable barrel-assembly, angioplasty-capable barrel-assembly, combination-form radial projection catheter.

Ablation and angioplasty-incapable barrel-assembly—A barrel-assembly (qv.), such as a simple pipe or solely discharge radial discharge barrel-assembly for insertion in an airgun as an endoluminally insertable extension of the airgun barrel and lacking features used for ablation and angioplasty; plain discharge barrel-assembly, limited purpose barrel-assembly; airgun-independent incapable barrel-assembly.

Active delivery [to an impasse-jacket, outrigger, or other type jacket]—Direct injection or infusion into an impasse- or other type jacket or the substrate (encircled, treated) ductus upsteam from the jacket. Includes the use of a catheter to the jacket from an infusion set cannula and patch, Ommaya reservoir, or similar portal positioned cutaneously, subcutaneously (subdermally), or having openings both cutaneous and subcutaneous at the body surface. This serves as a conduit to supply or evacuate (aspirate) an impasse-jacket (qv.) or outrigger (qv.) by a syringe or portable pump when passive delivery by the bloodstream or other ductus contents is inadequate. Inadequacy may, for example, involve dosing, timing, or the need to supply multiple impasse-jackets with different drugs in different concentrations at different intervals, making passive or statistical apportionment unreliable when even possible. Both active and passive delivery apply no less to nonmagnetized jackets. Cf. passive delivery.

Actuation-aspiration switching valves—A perforated plate or baffle positioned in the path of a flowing fluid that is mounted to act as a resistor when flow is in one direction and lever aside when the direction of flow is reversed. One is positioned in the roof of the outlet chamber of the radial projection unit lifting mechanism. During actuation or antegrade flow through the supply line, that valve closes increasing resistance to continued flow through the line causing the inflowing fluid to be diverted up against the base of the tool-insert (qv.). During aspirative or retrograde flow, the inflowing fluid pushes the valve that opens at an angle at its outlet side allowing particulate debris to flow through, at the same time that it forces the line fluid to rush past the opening that leads up into the tool-insert thus creating a vacuum. This primary valve can be reversed repeatedly until the buildup of debris forces flushing the line with sodium hypochlorite then water at high pressure or switching to the use of a separate fluid circuit. A second fluid resistor in the base hole or base-plug of the tool-insert consisting of a thin wafer or film of sugar, for example, will pose a tool-insert-specific secondary resistance opposing flow up through the tool-insert but once. To allow tool-inserts along the line to alternate between actuation and aspiration repeatedly, this secondary resistor is likewise made as a reversible valve. The perforated plate or baffle resistor shuts during radially outward (actuative, antegrade) flow and opens at an angle during inward (aspirative, retrograde) flow. Cf. aspirator, baffle.

Adhesive-hardener—A binder and fixative applied to miniball and stay implants to knit together the implant and the loose (diffuse) or weakened tissue surrounding it.

Adhesive-hardener field—The region surrounding the intraparietal implant through which the adhesive-hardener (qv.) coating it upon being implanted extends once cured. When positioned closely together, adjacent fields may coalesce or merge together to form a unitized scaffold embedded within the wall of the ductus that serves to reduce migrability.

Adjusting stent-jacket—A stent-jacket (qv.) with an expansion insert (qv.) along one or both free edges facing across the side-slit (qv.). Using absorbable materials in order of absorption, the stent-jacket is made to close over time, ideally, in step with subsidence in the initially enlarged ductus; contracting stent-jacket.

[Interventional] Airgun—An airgun adapted or specially devised to introduce or infix temporary drug-releasing or circumvascular stent retracting ferromagnetic implants into the wall of a ductus, for example. Angioplasty-capable barrel-assembly—A radial discharge barrel-assembly (qv.) that unlike a simple pipe or a solely discharge or limited purpose radial discharge barrel-assembly, can serve to perform an angioplasty without regard to subsequent insertion in an airgun to initiate stenting discharge. An angioplasty-capable barrel-assembly may incorporate only radial projection units (qv.) with trap-filter (qv.) or it can be of a combination-form type that also incorporates a laser or rotational burr. When the temperature range of its radial projection units and material removal rates of its tool-inserts is sufficient for ablation, the same apparatus can be used for an ablation in lumina of similar diameter. Used manually without insertion in the airgun and prior to insertion in the airgun when ballistic implantation stenting is to follow, an angioplasty-capable barrel-assembly has a free extracorporeal end, and independently powered, is untethered for free and independent manual use. Should the barrel-assembly require advancement or retraction in increments too small for manual control, the free end of the barrel-assembly is inserted into the airgun barrel and the linear positioning stage used; angioplasty barrel-assembly. Cf. ablation-capable barrel-assembly, ablation and angioplasty-capable barrel-assembly.

Antemagnet chamber—The enclosed space in front of a miniball recovery and extraction recovery tractive electromagnet and behind the spring-loaded door, which is flush with the outer surface of the muzzle-head. The door springs urge the door to re-close outwardly after a loose or extracted miniball, drawn into and trapped within the space by attraction to the magnet, has pushed the door open; magnet-trap (as opposed to filter-trap (qv.).

Anteport extension—The portion of the muzzle-head, and when pertinent, the distance of trap-filter projection distal to the exit ports and length thereof. The extension fixes the distal reach or limit out to which the muzzle-head can discharge.

Anti-migration lining—A layer applied to the internal surface of a stent-jacket (qv.) in order to reduce if not eliminate lateral displacement. When the muscular forces intrinsic in the substrate ductus or its exposure to external forces recommend, additional protection against migration is obtained through the use of stent-jacket end tethers (qv.).

Anti-perforation lining—A layer applied to the internal surface of a stent-jacket (qv.) in order to eliminate the risk of escape outside the ductus and to reduce if not eliminate the intensity or residual momentum of rebound as could cause the miniball (qv.) to enter the lumen.

[Stay-] arms—The extensions from the perpendicular midline of a stay (qv.). Stay must be kept short in proportion to the change in luminal circumference during expansion and contraction and the inflexibility of the arms. An ideal stay bends with changes in diameter of the ductus wall as would a tiny unstrung archer's bow; however, antecedent claims on the constitution of most practical stays usually disallow unrestrained compliance thus.

Articulated stent-jacket—A chain-stent (qv.) consisting of separate sub-stents connected, for example, by nonmagnetic stainless steel wire links to allow flexion or to bridge over a segment or segments of the ductus not to be stented. Different sub-stents can have side-slots (qv.) rather than side-slits (qv.) to allow a subjacent attachment to remain. Unlike a segmented stent-jacket (qv.), the substents can be very different in structure and distance to the next closest sub-stent. Cf. chain-stent, mixed chain-stent.

Aspirator—A barrel-tube (qv.) port, nose-hole at the distal terminus of the central channel (qv.), or a fluid radial projection tool-insert (qv.) when used to create a vacuum for the removal of ablation or angioplasty generated debris or excess ejectant or to retrieve misplaced miniballs (qv.). At subinjurious pressures, port vacuum can aid in stabilizing the muzzle-head in contact relation against the lumen wall. Ejector-irrigator-tool-inserts capable of alternately ejecting or irrigating and aspirating repeatedly must be equipped with actuation-aspiration switching valves (qv.).

Auxiliary syringe—A syringe or syringes containing medication, tissue sealant, a tumefacient, or intimal-medial swelling agent, scar tissue inducing agent or any of these in combination, attached to a stay (qv) insertion tool (qv) by means of a holding frame (qv). The unloading of syringes, which may be dual- or other multi-syringed, can be directly controlled by the operator or by an interval timing relay. When the latter, the unloading of syringes attached to the right and left of the stay insertion tool (qv.) may require to be independently coordinated in relation to the stay insertion tool (qv) ejection cycle (qv). When operation of auxiliary syringe is to be integral with the ejection cycle (qv.), control is under an inmate mixed-signal microcontroller embedded in the tool (not the auxiliary syringe attachment; the inmate microcontroller can be reprogrammed to accommodate different auxiliary syringe ejection cycles). The various types of substances applied can be mixed or segregated in syringes mounted at either side of the insertion tool for clear distinction in use.

Baffle—A fluid resistor consisting of a plate containing slits or perforations which is situated in the path of the fluid moving through a fluid radial projection system (qv.) or fluid circuit. Within a lifting mechanism a square baffle is used as a hinged roof over the outlet chamber (qv.) that serves to divide an antegrade flow so that a portion is forced to continue up into the tool-insert (qv.) and the rest continue down the circuit. During aspiration or retrograde flow, the baffle lifts up out of the path of the fluid thus minimizing clogging by aspirated debris. One or more baffles can be positioned along the throat of a fluid tool-insert base-plug (qv.) to increase the force acting to raise the lift-platform and/or to reduce the rate of tool-insert flow through. The shape of the baffle or baffles vary with the cross section of the throat or fluid path through the base-plug. Cf. actuation-aspiration switching valve, aspirator.

Ballistic component—In a barrel-assembly (qv.), the component that consists of the barrel-tube or tubes, recovery tractive or trap-extractor electromagnets, and if for use in the bloodstream, gas pressure diversion channels. Distinguished from the central component (qv.) when present, which is a channel along the central axis of the catheter for receiving a cabled device, and from the peripheral component when present (qv.), which consists of a radial projection circuit or circuits (qv.) about the periphery of the barrel-assembly. In monobarrels (qv.), whether simple pipes (qv.) or radial discharge barrel-assemblies, the ballistic component may be solitary or combined with a peripheral component. A radial discharge monobarrel for use in vessels may include all three components. A barrel-assembly with peripheral component, with or without a central component, is an ablation or ablation and angioplasty-capable barrel-assembly. When all three components are present, a barrel-assembly that includes a central component is more precisely described as a through-bore or ablation or ablation and angioplasty-capable combination-form (qv.) barrel-assembly. With or without a peripheral component, a barrel-assembly with a central component is a combination-form barrel-assembly. The lack of a ballistic component defines a separate radial projection catheter.

Barrel-assembly—An airgun barrel-extending catheter devised for performing interventional procedures. When ablative or angioplasty-capable, this apparatus functions in such capacity as physically separate from and independently of the airgun, then must be engaged in the airgun for implant discharge. Insertion in the airgun chassis (qv.) or cabinet makes the barrel-assembly the barrel of the airgun for the purpose of discharging tiny miniball implants, usually, into through the internal surface of a ductus lumen. A barrel-catheter (qv.) with muzzle-head (qv.) as a unit. An angioplasty-capable barrel-assembly includes components so that it can be used for angioplasty without regard to subsequent stenting, whereas a limited purpose barrel-assembly can only be used to deliver miniballs. Cf. ablation or ablation and angioplasty-capable barrel-assembly; minimally ablation or ablation and angioplasty-capable barrel-assembly.

Barrel-catheter—The larger tube in a barrel-assembly (qv.) that contains the barrel-tubes (qv.). In a simple pipe type (qv.) barrel-assembly, the barrel-catheter, and barrel-tube are one and the same, whereas in a compound barrel-assembly, which contains two or more barrel-tubes, the need to distinguish between the barrels within and the larger diameter tube containing these exists. In a duplex (composite, bipartite) (qv.) angioplasty-capable barrel-assembly, the barrel-catheter serves in effect as a guidewire over which the complementary radial projection catheter is slid into concentric relation as a sleeve that adds radial projection units.

Barrel-channel—The portion of each barrel following or distal to the terminus of the barrel-tubes where continuation is through the rotating nonmagnetic metal or spindle portion of the muzzle-head. The junction of the barrel-tubes with the barrel-channels is always by a joint of constant internal diameter across the junction which is slidable or reciprocating when the pliancy of the barrel-tubes or a lack of sufficient slack results in distortion or kinking of the barrel-tubes but is otherwise bonded.

Barrel insertion segment—The proximal length of an angioplasty barrel-assembly that is inserted into the barrel of the airgun to initiate ballistic implantation. Arranging that the hand-grip shaped onboard battery pack, which is used to power the barrel-assembly while used independently of the airgun and the airgun or a separate power supply for angioplasty, can be slid proximally along the barrel-catheter allows the proximal segment of the barrel-assembly to be used intracorporeally, reducing the overall length of the barrel-assembly required for a given procedure; overhang.

Barrel-tube—An airgun miniball propulsion and directing channel analogous to the barrel of a firearm. In a simple pipe, the one barrel-tube comprises the sum of the barrel-assembly, which consists of a single barrel-catheter, whereas in a two or four-way radial discharge barrel-assembly, the generally two to four barrel-tubes are contained within the barrel-catheter. Its distal end is the muzzle-head. A barrel-tube to be used as a service-channel (qv.) prior its use for discharge must be lined by a service-catheter (qv.); otherwise, it can serve as the service-catheter itself.

Base-layer—The layer to which another layer or layers is laminated to add resilience, remote heatability, or radiation shielding, for example. Lamination is by chemical adhesive bonding, heat sealing, or heating a ferromagnetic doped coating by induction heating, for example.

Base-plug—An extension down from the bottom of a tool-insert that in an electrical radial projection circuit provides the electrical connection to power the electrical component or components internal to the electrically operated tool-insert but not raise and lower the lift-platform, and in a fluid circuit provides connection to the fluid line to raise and lower as well as provide power to the fluid operated component of components internal to the fluid operated tool-insert. In a tool-insert without internal components that are electrically or fluid operated, a dummy base-plug without connectors to the power line serves to secure the tool-insert in the holding and lift-platform by friction fit.

Base-tube—In a stent-jacket (qv.), the segment of tubing that serves as the pliant platform upon which the perpendicularly magnetized bar magnets are mounted. Its inner surface serves to set the limit to the excursion or distance from the central axis of the lumen to which the ductus wall can be drawn, and no more distant from the external surface of the ductus than is necessary to effect sufficient patency or normal blood (TIMI III) flow, prevents stretching injury.

Base-tube (slit) expander—A stent-jacket base-tube slit expanding hand-tool used to expedite placement into a surrounding or circumvascular relation of a stent-jacket and a vessel or duct.

Bipartite [ablation or ablation and angioplasty-capable] barrel-assembly—A barrel-assembly (qv.) comprising an inner axial barrel-assembly proper, the primary, and an ensheathing or ensleeving secondary slide-over or slide-on through-bore, or combination-form (qv.), radial projection catheter (qv.), that adds additional capabilities. Standardized diameters allow matching any number of otherwise independent radial projection catheters of like size to a given barrel-assembly proper, or primary, as secondaries, or slide-overs, which can be exchanged or 'swapped' midprocedurally using the intracorporeal primary in the manner of a guide wire. Other type ensheathing catheters are used to increase the diameter of the barrel-assembly and/or jacket the primary within a heating or chilling mantle. Sliding one radial projection catheter over another can be used when a proximal segment of the ductus is distended; the outer projection catheter is withdrawn before the narrower stretch is entered. Nesting radial projection catheters is possible because tool-inserts withdraw beneath the outer surface to leave the surface of the inner projection catheter smooth; composite barrel-assembly, duplex barrel-assembly.

Blank [tool-insert]—A tool-insert with a continuous flat inert working face, unperforated and without cutting or injecting parts. Blanks used to nudge the muzzle-head into the opposite radial direction elevate and retract. The working faces of temperature changing blanks generally remain flush to the surface of the muzzle-head (qv.) or radial projection catheter (qv.). Electrical blanks containing a coil can only heat, whereas fluid circuit blanks can deliver heat or cold according to the temperature of the fluid in the supply line. Only nonblank tool-inserts can deliver the fluid, which can be a drug as well as driving medium, into the lumen or lumen wall.

Blanked [rotary magazine] clip—a rotary clip inserted to eliminate a number of barrel-tubes of the barrel-assembly from use, usually to treat eccentric lesions. The holes in the clip that would normally retain the miniball or miniballs for barrel-tubes to be eliminated are reduced in diameter or eliminated.

Blood-groove—Longitudinal furrows or running depressions that run along the outer surface of the barrel-catheter and muzzle-head portions of the barrel-assembly to allow some circulation of blood. The blood-grooves or depressions are made as deep and as wide as the requirement to not encroach upon the internal barrel-channels allows.

Blood-port—An open space in the muzzle-head through which blood can flow created by removing nonessential metal.

Blood-tunnel—A channel through the barrel-catheter to provide a passage for the flow of blood that also stiffens the catheter.

Bounce-plate—An angled surface mounted to the end of the muzzle-head of a simple pipe barrel-assembly to alter, generally reverse, the angle of discharge. The simplest bounce-plates necessitate withdrawal of the barrel-assembly to attach or adjust. To reduce procedure and anesthetization times, mechanisms that allow the deployment and retraction, and in more capable forms, adjustment in the angle, of a bounce-plate intracorporeally are provided; rebound angle deflection plate, rebound deflection-plate, deflection-plate, rebound-plate; ricochet-plate; strike-plate; rebound-tip; ricochet-tip; rebound strike-tip. Cf. Strike-point.

Bounce-wedge—The outer or abluminal component of a double-wedge insert lining (q.v.) for a shield-jacket (q.v.) or a stent-jacket (q.v.) that serves as a rebound surface of specified angle and resilience to shift the trajectory of the miniball away from the lumen toward a terminus within the wall of the ductus where it can afford function. A special purpose base-tube can be made that increases in thickness from end to end, eliminating this element; however, a universally applicable insert for a section of any tubing material is more versatile and economical; bumper, bumper-wedge, deflection-wedge, rebound-wedge. Cf. foam-wedge.

Braced impasse-jacket—A simple trap- (guard-) or holding-impasse-jacket (qv.), which includes one trap or one holding jacket (qv.) or collar, stabilized against abrupt and potentially injurious displacement during an extraction through elongation by fastening unmagnetized dummy-collars, or outriggers, at either or both ends by means of rigid bendable bridge-arms (qv.). The structure overall constitutes a unitized weldment or brazement which can be bent to follow a curve, for example. A braced impasse-jacket with more than one dummy-collar at either end is one type of chain impasse-jacket. Another type includes more than two magnetized jackets, each used either to retain miniballs as a holding jacket or stop miniballs from passing as a trap-jacket, and yet another combines one or more stent-jackets and an impasse-jacket. The lengthened structure better resists sudden repulsion-normal or ductus-transverse displacement (qv.) and margin-levering (qv.) when repelled by a powerful external electromagnet during an extraction and allows spanning over or straddling segments that may be severely lesioned, must flex, or would best be left attached to neighboring tissue. Since compound (qv.) and chain impasse-jackets (qv.) are inherently braced, the term 'braced' is used to denote a simple-extended or individual trap or holding impasse-jacket with at least one dummy-collar at one end; simple-extended impasse-jacket.

Break-seal—A film or plate used to block the entry into a fluid injection or ejection tool-insert (qv.) in order to set a threshold line pressure to assure local and circuit flow-through. When singular, it is placed at the bottom or top of the base-plug (qv.). Break up of the seal allows the tool-insert to be used as an aspirator upon reversing the direction of flow through the fluid supply line. The film must break so that when pushed into the syringe, the pieces will not clog the hypoendothelial or hypointimal injection needle or the outlets of the ejector. Antegrade flow can be reinitiated following retrograde or aspirative flow, but with the seal having been removed, no preliminary threshold pressure will precede emission. When aspiration generates sufficient force, a 2-way slit or otherwise perforated membrane allows directional reversal to allow actuative or antegrade and aspirative or retrograde flow to be alternated. Cf. push-through stopper; slit-membrane. [Impasse-jacket] Bridge-arms—Extension spans connecting the sections of a multipartite or multicomponent impasse-jacket. Cf. Braced impasse-jacket, compound impasse-jacket, chain impasse-jacket.

Capillary cooling catheter—A fine service-catheter (qv.) for quickly returning the turret-motor, miniball recovery electromagnets, and/or heated radial projection unit tool-inserts to normal body temperature. It can enclose a coolant and have been refrigerated, then passed down the barrel-assembly when needed, or have a closed distal end and side-holes through which chilled air or high purity 1,1,1,2-tetrafluoroethane (R134a) cryogen spray, for example, is pumped at low pressure; cooling capillary catheter; capillary chilling catheter, temperature changing capillary catheter (qv.).

Butt-pad—A cushion at the bottom of the butt to prevent injury to adjacent and subjacent tissue.

Cement-ahead operation—In a stay insertion tool (qv.), the control of cement delivery to initiate outflow between stay ejections. The deeply surface textured stays that are usually used to reduce squeegeeing during entry pass through the cement while being inserted into the wall of the ductus, thus carrying cement forward and ductus-intramurally on both upper and lower surfaces. Bonding to the subjacent and superjacent layers of the tunics lessens the risk of laminar separation. An adjustable cement air pump pressure relief aperture allows varying the amount of cement released; cement-before operation. See also medication-ahead operation.

Cement-follower operation—In a stay insertion tool (qv.), the control of cement delivery to initiate outflow over an interval during the insertion of the stay through the wall of the ductus. An adjustable cement air pump pressure relief aperture allows varying the moment of cement outflow initiation and duration onto the upper surface of each stay. For sealing the stay insertion incision, cement is applied only to the tail end of the stay. To retain more of the cement during insertion, the portion of the upper surface of the stay is deeply textured; cement-during (stay insertion, stay infixion) operation. See also medication-follower operation.

Center discharge barrel-assembly—A barrel-assembly lacking a burr or laser atherectomy cable running down its center, which is thus free for use as peribarrel space, and the closer positioning together longitudinally of the barrel-tubes.

Center discharge muzzle-head—The muzzle-head (qv.) in a center discharge barrel-assembly (qv.).

Centering device—A disk with holes placed at intervals along the barrel-assembly, which is used to space the longitudinally disposed barrel-tubes that course through it at the concentric distances desired. The intervals along the barrel-assembly and slidability or bonding of the barrel-tubes to these allows considerable variability in the flexibility and torqueability of a barrel-assembly made of tubes of a given material; centring disks.

Central canal—In a barrel-assembly (qv.), the longitudinal axial space that extends from the terminal plate (qv.) to or through the muzzle-head (qv.). In a non-combination-form barrel-assembly, the central canal ends distally at the back of the ejection head and is used for pressure equalization to prevent gas embolism. It contains the wires to the turret-motor (qv.) and recovery electromagnets. See also side-canal.

Central channel—The bore through a combination-form (qv.) barrel-assembly (qv.) or radial projection catheter (qv.) for passing a permanently installed or interchangeable cabled device so that it emerges at the nose. Combination-form radial projection catheters that ensheath a barrel-assembly of like diameter yield a bipartite (or divisible) ablation or ablation and angioplasty-capable barrel-assembly (qv.).

Central component—A commercial device such as an endoscope, intraductal ultrasonograph, laser, atherectomizer, or thrombectomizer incorporated into a barrel-assembly (qv.). When more than one barrel-tube is present, this component is usually placed between or amid these, hence, the designation central. If the commercial device imparts ablative or angioplastic capability, the barrel-assembly is ablation or ablation and angioplasty-capable. The addition of a radial projection system can enhance this capability.

Chain-guard [miniball impasse-jacket]—Either a miniball impasse-jacket (qv.) that includes more than the two magnetized impasse-jackets used to trap miniballs provided by a compound-guard Impasse-jacket, or a braced (qv.) trap-jacket (qv.) that includes more than one dummy-collar or outrigger at either end of the single magnetized jacket at the center to trap miniballs; chain-trap.

Chain [miniball] holding jacket—Either a miniball impasse-jacket (qv.) that includes more than the two constituent magnetized jackets used to hold medication and/or radiation miniballs in suspension within the lumen (usually in the bloodstream) provided by a compound holding jacket, or a braced (qv.) holding jacket (qv.), that includes only one magnetized impasse-jacket and more than the one position-stabilizing unmagnetized dummy-collar or outrigger provided by a braced holding jacket. Chain jackets that include more than two magnetized impasse-jackets are triple, quadruple, and so on, where each jacket can serve the same purpose as a trap or holding jacket, or differ in this, being mixed triple or mixed quadruple chain-jackets, for example. The dimensions and interval separating consecutive jackets in a chain depends on the anatomy involved.

Chain [miniball] impasse-jacket—A—braced impasse-jacket (qv.) which includes more than one unmagnetized dummy-collar, or outrigger, at either end, or a compound impasse-jacket (qv.) that includes more than two impasse-jackets. In any jacket, the constituent magnetized and unmagnetized jackets are joined at their ends by bridging arms fastened by resistance welding or furnace brazing. The unitized weldment or brazement allows lengthening the structure overall to resist end or margin-levering by a jacket-repelling/miniball-attracting extraction electromagnet (qv.), and to span across (straddle, skip over) segments of the ductus, usually an artery, that are diseased, curved, must flex, or would best be left attached. In the compound type, all of the individual or constituent jackets, although structurally the same except perhaps in dimensions, may be used as holding or trap-jackets. Most compound and chain impasse-jackets include holding jackets (qv.) with one or two trap-jackets and are therefore said to be mixed or composite impasse-jackets. Chain impasse-jackets are inherently braced (qv.) for positional stabilization in the even of the need to extract a miniball from the jacket with the aid of an external electromagnet. Most chain impasse-jackets include holding jackets (qv.) with at most one or two trap-jackets; impasse and extraction jacket. Cf. braced impasse-jacket, bridged-guard, braced-guard.

Chain-stent—Collective term for articulated (qv.) and segmented (qv.) stent-jackets (qv.). Chain-stents consist of a serial formation or train of individual stents, or substents (sub-stents), each connected to the next at either end with those at the end of the formation connected at only one end. Chain-stents allow stenting that spans across (skips over, straddles) segments of ductus that curve or flex with body movement, or do not require or should not be stented, or which have attachments or adhesions that should not be dissected. Articulated chain-stents connect the substents by means of fine nonmagnetic wires so that the interval separating the substents can be different and each chosen for the segment which that substent is to encircle. Segmented chain-stents are cut or molded into a continuous length of polymeric tubing at various but regular intervals with a connecting or bridging strip running the entire length of the chain along one side. Any number of consecutive substents can be snipped off for use, and except for the continuous connecting strip, which can be left intact to impart greater resistance to migration, segments to be omitted can be snipped away; sectional stent-jacket, serial stent. Cf. mixed chain-stent.

Charge—The magnetically susceptible bound or encapsulated pharmaceutical or load or its delivery to an impasse-jacket, leaving it charged or loaded; load.

[Airgun] chassis—The cabinet containing the propulsive and control means for turning a barrel-assembly into the barrel of an interventional airgun when the barrel-assembly is inserted therein.

Clamp-collar—A round clamp at the rear or proximal end of the turret-motor for securing the end of the barrel-catheter.

Clasp-magnet—A permanent magnet encapsulated within a chemically isolating envelope of plastic or metal and mounted on a base with prongs for engagement into the muscle fascia or pleura; patch-magnet.

Clasp-patch—A bandage consisting of a spandex or similar elastic backing having ferromagnetic clasps as points for undercutting the subjacent surface tissue, whether organ capsular, fibrosal, adventitial, or pericardial, or fascial. Conceptually, it is the counterpart to a patch-magnet (clasp-magnet); in that it provides the attracted as opposed to the attracting component. Cf. clasp-wrap.

Clasp-wrap—A wrap-surround (qv.) or bandage consisting of a spandex or similar elastic backing having ferromagnetic clasps with points for undercutting surface tissue, such as organ capsular, fibrosal or adventitial tunical, or pericardial. Patches not intended to wrap around a ductus but rather fasten to subjacent tissue are clasp-patches. The points are arranged in an opposing formation or formations to undercut the fibrosa or adventitia, for example. A clasp-wrap can sometimes be used when the ductus would not retain separate ductus-intramural implants or would not do so quickly enough. Once placed, a stent-jacket or patch-magnets are used as the extravascular (circumductal, periductal, circumvascular, perivascular) component of a stent, for example. The clasps are given a deep outer texture, a perforation, and may be wetted with a solution to encourage tissue infiltration for long-term retention. The internal surface of the backing may be coated with an elastic adhesive; however, an adhesive is limited to serving as an interim measure to bridge the period during which tissue infiltration and adhesion develop. As a prosthetic outer layer or tunic, it may be considered intravascular or intraductal; clasp wrap-surround, clasp-bandage, clasp-jacket. Cf. clasp-patch.

Close-ended—Said of a cooling catheter or cooling capillary catheter having side-holes but closed off at the distal end for delivering cooling air or gas or heating air to the adjacent tissue or components. A cooling catheter for cooling an adhesive to extend its open time can have both side holes and a small hole at the distal end. Unrelated to close-backed as designating an nonpiped radial projection unit.

Combination-form—An ablation or ablation and angioplasty-capable barrel-assembly (qv.) or a radial projection catheter (qv.) with a central channel (bore, passageway) through which a prior art cabled device or devices such as a fiberoptic endoscope, laser, or rotational atherectomy, thrombectomy cutter, or similar device can be passed. A proximally (extracorporeally, extraductally) placed side-port (qv.) leading to the central channel through a frontomedially directed tunnel-tube allows a cabled device or devices to be inserted into and through the bore and up to or through the nose or distal end. When the central channel is at least partially empty, distally (intracorporeally, endovascularly) placed side-ports, or side holes, leading to the central channel through frontomedially directed tunnel-tubes allow blood to pass through the central channel between the front end or nose and the side-port; through-bored.

Combination-form barrel-assembly—A barrel-assembly (qv.) that accommodates commercial cabled devices, such as a laser, endoscope, thrombectomy, or atherectomy cutter, along its central axis to its distal end as central component. Interchangeability of such devices imparts greater versatility to the barrel-assembly in allowing different views and procedures during the course of a single entry endoluminal procedure as well as in expanding the zone of applicability to different operations. When augmented thus, a barrel-assembly with a peripheral component (qv.), or radial projection system (qv.), is increased in ablation or angioplasty capability. To afford a channel for the central component, such a barrel-assembly, referred to as a combination-form ablation or ablation and angioplasty-capable barrel-assembly, requires the use of an edge discharge muzzle-head (qv.); through-bore barrel-assembly. Cf. bipartite ablation or ablation and angioplasty-capable barrel-assembly.

Combination-form muzzle-head—The edge-discharge muzzle-head (qv.) in a combination-form barrel-assembly; through-bore muzzle-head.

Combination-form radial projection catheter—A sheath (sleeve, tube) without a ballistic component (barrel-tube) that incorporates one or more electrical and or fluid radial projection systems (qv.) and includes a central (longitudinal axial) channel for installing a permanent cabled device or for accepting interchangeable commercial cabled devices, such as an endoscope or laser. When this device is a laser or atherectomy cutter, the ablation or ablation and angioplasty-capability of the device is enhanced; however, since tool-inserts (qv.) are interchangeable, any radial projection catheter (qv.) is ablation and/or angioplasty-capable. Inserting a simple pipe or radial discharge barrel-assembly in the central channel yields a barrel-assembly with ballistic and peripheral components (qv.) where the central component has been displaced by the ballistic component. To obtain optimal functionality from an ablation or ablation and angioplasty-capable barrel-assembly and a combination-form radial projection catheter as independent when the two are used together, these are made as a matching set for a given gauge. The power and control housing of the barrel-assembly is disconnected and the radial projection catheter slid over the barrel-catheter of the barrel-assembly and the power and control housing of the barrel-assembly reconnected so that the housings stand in ganged relation; through-bore radial projection catheter. Cf. Radial projection catheter, bipartite ablation or ablation and angioplasty-capable barrel-assembly, power and control housing.

Complete stent-jacket—A full-round stent-jacket (qv.) with side-slit rather than a side-slot to clear an anatomical attachment.

Compound impasse-jacket—A braced (qv.) impasse-jacket with more than one dummy-collar, or outrigger, at either end of a singular magnetized Impasse-jacket at the center or a double impasse-jacket, which includes more than one magnetized impasse-jacket rigidly fastened end to end by bendable bridging arms to allow straddling over or spanning intervening segments which flex, are severely malacotic, or should remain attached to neighboring tissue. Compound and chain impasse-jackets are inherently braced (qv.) without the need for unmagnetized dummy-collars at one or both ends. A compound impasse-jacket is the same in structure regardless of whether a given constituent jacket is used as a trap (qv.) or holding jacket (qv.). When one jacket is used to hold and the other to trap miniballs, the jacket is mixed or composite; double impasse-jacket.

Compound-guard [miniball] impasse-jacket—A double impasse-jacket (qv.) with two magnetized jackets where both are used to stop any miniball or miniballs that might originate upstream. The need for more than one guard or trap-jacket indicates that more miniballs are to be protected against than the first jacket could stop without becoming occluded. The strength of magnetization of the first jacket is accordingly adjusted so that the pressure exerted the lumen contents when obstruction would occur is sufficient to force the miniball or miniballs at the center forward to the next trap-jacket. This pattern of graduated field strength in the direction of flow is iterated in a chain trap-jacket; compound trap-jacket; double guard impasse-jacket.

Compound [miniball] holding jacket—An impasse-jacket (qv.) that includes two magnetized jackets to hold medication or radiation-emitting miniballs suspended in the lumen. Impasse-jackets that include more than two holding jackets as double are chain holding jackets that are triple, quadruple, and so on. Where compound-guard impasse-jackets are implanted empty, holding jackets are loaded with the miniball or miniballs to be held, by injection at the bridge (qv.) through the same access portal; double holding impasse-jacket.

Compound mechanical tool-insert—A tool-insert (qv.) that when its tip is brought into contact with the lumen wall is actuated by internal means, usually a spring. Contract with the lumen wall is usually produced by the raising of the tool-insert by the tool-insert holding and lift platform, and discharge typically involves the release of an injectant into the wall.

Compound mechanical-electrical tool-insert—A tool-insert (qv.) that is both lifted into contact with the lumen wall and discharged by internal means rather than by the tool-insert holding and lift platform (qv.), usually through the generation of a gas by allowing chemicals to mix that had been kept separate by an intervening barrier or wall such as of wax until melted by the flow of current in an electrical heating filament coursing through this separating barrier. When the flow of current is initiated automatically or locally without the need to use a switch, the outer tip of the tool-insert, which is a spring-loaded contact of a switch, must be close enough to the surface so that when pressed against the lumen wall, the tip is pressed downward (toward the floor of the tool-insert holding and lift-shaft) bringing it into contact with the other contact and thus closing the circuit.

Compound tubing—highly pliant polymeric tubing lined with a thin layer of polytetrafluoroethylene approved for medical use; co-extruded tubing; a coextrusion.

[Barrel-assembly power and] Control housing—The part of an ablation or ablation and angioplasty-capable barrel-assembly or a radial projection catheter containing the battery or batteries, control electronics, and having a control panel mounted on its upper surface for ease of view and use with either hand. For ease of manipulation, it is generally configured as, or to include, a pistol grip. To obtain optimal functionality from an ablation or ablation and angioplasty-capable barrel-assembly and a through-bore or combination-form radial projection catheter as independent so that the two can be used together, these are made as a matching set for a given gauge. With the control housing of the barrel-assembly disconnected, the barrel-assembly is a minimally capable ablation or angioplasty barrel-assembly. The radial projection catheter can then be slid over the barrel-catheter of the barrel-assembly and the power and control housing of the barrel-assembly reconnected so that the housings stand in ganged relation. For trackability, the barrel-assembly is introduced first, and the radial projection catheter is then slid over its barrel-catheter as a kind of guide wire after the muzzle-head has been moved to the treatment site. Further to enhance trackability, the muzzle-head can emit a lubricant for use with the oscillatory mode of the turret-motor; battery pack and control housing [with hand-grip], control box. A universal power and control housing that can be used with any barrel-assembly requires controls for every function and limited to use with only one at a time.

Control panel—1. The positioning and discharge set of controls mounted to the airgun or 2. The ablation and atherectomy set of controls mounted on-board an ablation or ablation and angioplasty-capable barrel-assembly (qv.); barrel-assembly control panel. Cf. [Barrel-assembly power and] Control housing.

Cooling rod or catheter—1. A prewarmed or chilled solid rod or a tube (conduit) that is prepositioned or is passed down the central canal (qv.) of a barrel-assembly (qv.) barrel-tube (qv.), central canal (qv.), or central channel (qv.) or down the central canal or channel in a special radial projection catheter (qv.) for altering the temperature of the components therein. 2. A tube mounted alongside an adhesive delivery line inmate or attached to a stay insertion tool (qv.) for conducting cold air or gas or hot air to the tissue adhesive, the tissue treated, or parts of the apparatus itself. A cooling catheter of a caliber to allow insertion into a small barrel-tube is referred to as a capillary cooling rod or catheter. Where no barrier would prevent the entry of heating or chilling fluid into the bloodstream, the cooling catheter must be closed-ended or a solid rod. To restrict the temperature change to a preferred segment of the lumen wall, the wall of a tubular cooling catheter can be perforated over only a certain segment along the length. A cooling catheter miming down the center or alongside an adhesive delivery line attached to a stay insertion tool has side-holes, while one attached to cool the ductus is open at the distal end. Cf. service catheter.

Cooling [capillary] catheter—A tube with a chamfered or conical front (distal) closed end and side-holes over the distal segment, which is positioned alongside or just short of the recovery electromagnets, radial projection unit brush-type tool-inserts, and turret-motor when fully inserted into the central canal of a center-discharge or the barrel-tube of a center or edge-discharge barrel-assembly. The appellation 'capillary' pertains to cooling catheters for passing down a barrel-tube, which must be very small in diameter. To quickly return the heated components to body temperature, vortex tube-generated cold air is passed through the side-holes of the cooling catheter; rapid cooling catheter; chilling catheter.

Cooling catheter insertion channel—A passage cut along the central axis proximal to the recovery electromagnets in a center-discharge muzzle-head ejection head for acceptance of the distal end of a cooling catheter.

Composite barrel-assembly—Same as bipartite barrel-assembly (qv.); duplex barrel-assembly.

Discharge set—A plurality of successive discharges belonging to a discrete sequence or group unit directed at a specific segment or lesion along the lumen. With a multiple barrel barrel-assembly, each discharge may implant multiple miniballs; discharge group; discharge sequence.

Discharge stack—An instruction stack that coordinates a. The two drivers consisting of open-loop controlled stepper motor operating the linear positioning table for transluminal movement and the closed-loop controlled dc servomotor that rotates the muzzle-head with b. Actuation of the airgun undamped direct current powered plunger solenoid (used as a hammer to strike the valve body pin) through the program sequencer and servocontroller in order to execute a preset discharge pattern.

Distal—Farther from the operator than the point of reference.

Double wedge insert lining—An insert lining for a temporary shield-jacket (qv.) or a prepositioned spaced apart magnet-type base-tube (qv.), or an intrinsically (qv.) or quasi-intrinsically magnetized (qv.) stent-jacket (qv.) consisting of complementarily inclined layers joined at a distolaterally inclined plane. The inner wedge of moisture barrier-coated viscoelastic polyurethane foam protects the adventitia and dissipates momentum of the miniball, while the outer of a resilient nonallergenic rubbery elastic material redirects the miniball to a trajectory less inclined toward the lumen to a functional subadvential or medial location; cf. bounce-wedge, foam-wedge.

Ductus-intramural—Within the wall of a ductus; ductus-intraparietal.

[Impasse-jacket] Ductus-transverse displacement—Sudden downward thrust, usually of an artery, against subjacent tissue under the repulsion of an external miniball extraction electromagnet (qv.) used to noninvasively extract a miniball from the lumen of the artery and through the mesh of the impasse-jacket (qv.) encircling it. Such can occur when the ductus does not lie flat against subjacent tissue that extends beyond the end-edges of the impasse-jacket and that tissue is not sufficiently firm to cushion the thrust. An artery that overlies a space, soft tissue, or lies superjacent at a distance to hard tissue and experiences a sudden thrust can be injured by flexion and stretching at the end-edges or margins of the impasse-jacket prompting medial and intimal hyperplasia, restenosis, and the need for reperfusion. Potentially injurious displacement is averted by elongating and thus positionally stabilizing the jacket. A simple jacket (qv.) can be elongated, or if an intervening segment must be spanned across (skipped, straddled), then a braced (qv.) or compound (qv.) impasse-jacket is used, and if multiple segments must be spanned across, then a chained impasse-jacket (qv.) is used. If necessary, the jacket is additionally tied down by looping suture around mesh strands over the end-cuffs (qv.) of the jacket and any unmagnetized dummy-collars or outriggers (qv.) and tying the ends thereof to neighboring, usually subjacent tissue of sufficient strength under a pulling force sufficient to close the gap but not interfere with pulse compliance; ductus thrust, ductus-normal displacement, extraction-thrust; repulsion-normal displacement. Cf. margin-levering, chain-guard, braced impasse-jacket, compound impasse-jacket, chain impasse-jacket.

[Impasse-jacket] Dummy-collar—An unmagnetized impasse-jacket (qv.) outrigger (qv.). A braced entry-collar is a dummy-collar used when necessary to minimize levering of the impasse-jacket. A braced exit-collar may serve this purpose and be magnetized to take up any magnetic carrier bonded drug to be stopped from passing the impasse-jacket. Since it is magnetized, it is not a dummy-collar but an impasse-jacket outrigger, which can be an unmagnetized or dummy-collar or magnetized.

Duplex barrel-assembly—Same as bipartite barrel-assembly (qv.); composite barrel-assembly.

Edge discharge barrel-assembly—A barrel-assembly having a burr or laser atherectomy cable running down its center, so that a central canal is unavailable for use as a portion of the peribarrel space that in a center-discharge barrel-assembly (qv.) can be used to insert a cooling capillary catheter (qv.) past the turret-motor (qv.) and into the ejection-head to cool these components when used as heating elements for thermal angioplasty; combination-form barrel-assembly, through-bore barrel-assembly.

Edge discharge muzzle-head—The muzzle-head (qv.) in an edge discharge (combination-form, through-bore) barrel-assembly (qv.) wherein the axial center is occupied by an atherectomy burr or laser cable; combination-form muzzle-head, through-bore muzzle-head.

[Muzzle-head] Ejection head—The solid nonmagnetic metal distal or front portion of the muzzle-head (qv.), which accepts and fixes in position the distal ends of the barrel-tubes.

Ejection tool-insert—An emitter (qv.) type radial projection unit (qv.) tool-insert (qv.) for releasing fluid into the lumen rather than injecting it into the lumen wall. The self-contained syringe type can be used in either an electrically or a fluidically operated system, but is limited to the amount and type of fluid it contains. By contrast, a fluidically operated flow-through (qv.) ejector fed from one or more reservoirs outside the barrel-assembly is not so limited. Interchangeable and/or switchable reservoir refill cartridges allow a wholly contained fluid system in an ablation or ablation and angioplasty-capable barrel-assembly to provide any number of fluids in any amount and sequence. Unlike injectors (qv.), ejectors are usually not raised and lowered but instead kept flush to the surface of the muzzle-head by a gap that separates the base of the ejector from the lifting mechanism; ejection syringe tool-insert; ejector Cf. emitter, electrical ejector, fluid system ejector, flow-through ejector, injector, electrical injector, fluid system injector, electrical tool-insert, fluid tool-insert, flow-through injector.

Electrical emitter—A syringe-type noninjecting ejector or injecting injector tool-insert (qv.) that is electrically connected when inserted into the lift-platform (qv.) of a radial projection unit (qv.). It is used in a fluid or piped system when the injectant is other than that passing through the line. The electrical connection allows the contents to be heated until used. Cf. ejector, electrical ejector, fluid system ejector, injector.

Electrical injector—A syringe-type self-contained injection tool-insert (qv.) containing a heating element that is electrically connected when inserted into the lift-platform (qv.) of a radial projection unit (qv.). It is not usable in a fluid or piped system. When an injectant other than that passing through the line is to be delivered, a nonelectrical syringe injector is used and the temperature controlled by passing temperature-adjusted fluid through the fluid line. Injectors and lines can be insulated. In an electrically operated radial projection system (qv.), the electrical connection allows contents such as protein solder, surgical cement, a tumefacient, vasodilator, or other medication to be heated until used. Cf. emitter, ejector, electrical ejector, fluid system ejector, injector. Emitter [tool-insert]—A tool-insert (qv.) that is used to eject or inject a fluid. An ejector has perforations in a flat working face for releasing fluid medication into the lumen at the treatment site, whereas an injector delivers a fluid into the lumen wall through a hollow needle or needles. A self-contained syringe type tool-insert emitter can deliver no more fluid than it can hold. If connected electrically, the emitter can heat the fluid to a preferred temperature. An ejector can be insulated and/or positioned stationary as flush to the surface of the muzzle-head or retracted to more quickly remove the heat or cold, and lowering the emitter to a barrel-tube containing a cooling catheter further accelerates cooling. A fluid system flow-through (qv.) type emitter (qv.) affords greater capability in administering fluids, because an unlimited amount and any number of different fluids can be delivered quickly at the temperature desired. The temperature is, moreover, quickly adjusted by changing the temperature of the fluid in the line; ejector, injector. Cf. electrical ejector, fluid system ejector, flow-through (qv.) ejector, injector, electrical injector, fluid system injector, electrical tool-insert, fluid tool-insert, flow-through emitter.

Electrical tool-insert—A tool-insert for use in an electrical radial projection system (qv.). Engaging the projection that extends down from the center bottom of the base into the socket on the lift-platform also connects the tool-insert electrically. The electrical connection can be used to warm the contents of a syringe ejector (qv.) or injector (qv.) or power a motor inside the tool-insert. Fluid operated radial projection systems are generally not provided with a source of electrical power and cannot accept electrical tool-inserts. Cf. emission tool-insert, injector.

Emission tool-insert—An ejection tool-insert or ejector (qv.) or an injection tool-insert or injector (qv.); emitter.

Emitting pressure—In a fluidic radial projection unit (qv.) circuit, that line pressure greater than the idle pressure (qv.), then the lifting pressure (qv.), that forces an emitting tool-insert to release fluid, or discharge; the reciprocal of the aspirating or intake pressure (qv.). The term is pertinent to antegrade (forward) or actuating flow, the term intake pressure pertaining to retrograde (reverse) or aspirative flow.

Since each tool-insert can be made to discharge at a different pressure, this factor pertains to the individual tool-insert. The emitting pressure is equal to the idle pressure plus the additional pressure necessary to raise the lift-platform, or the lifting pressure, plus any additional pressure that is necessary to cause the individual tool-insert to discharge.

End-cap—In a barrel-assembly (qv.), a plate at the distal end of the barrel-assembly but which will almost always be attached to the proximal end of the spindle neck (qv.) that is excluded in most embodiments. In a supporting arm and connecting cable used to connect an auxiliary syringe (qv.) frame or holder to a stay insertion tool (qv.) for independent or coordinated operation, the conductor positioning covers at the ends of the connecting cable.

[Impasse-jacket] End-cuffs—Linings of viscoelastic, usually polyurethane, moisture barrier-coated viscoelastic polyurethane foam at the ends of impasse-jackets (qv.) and any dummy-collars or outriggers (qv.). End-cuffs provide 1. End-cushioning and a gap between the adventitia and the jacket mesh that protects against adventitial, vasa and nervi vasoral incisions by the wires of the mesh, 2. Some latitude in caliber of the impasse-jacket required for a specific segment, thus a. Eliminating the need to produce jackets in many intervening calibers, and b. Saving much midprocedural time to obtain a good fit for unrestricted compliance with the pulse or intrinsic muscle action, and 3. A space to allow suture to be looped over or beside a mesh strand above the end-cuff to allow the use of tie-downs (qv.) if necessary.

End-implant—A corrective or prosthetic device, such as a magnetic stent-jacket (qv.), which is left in place after withdrawal and closure. Opposed to a device such as a perforation shield-jacket (qv.) that is placed temporarily to prevent a perforation during discharge and removed before closure. Implants completely or partially absorbed after closure, such as radiation shield-jackets, are nonpermanent end-implants. Cf. temporary implant.

End of segment—The distal or downstream level for ending exposure of the delimited or defined length (segment) of the ductus upstream (proximal) thereto to the action of the drug, radionuclide, and/or other therapeutic substance released at the start of segment (qv.). An exit impasse-jacket, or exit jacket (qv.), is used when uptake of the drug within the segment is subtotal and the residue is to be eliminated. The inactivating substance is released from a time-released miniball whether the result of dissolution of its shell or the miniball itself, which releases a ferrofluid or microspheres that release magnetically susceptible drug carrying nanoparticles in turn. Miniball or microsphere dissolution can be initiated by heating an entry or exit-jacket, or through the use of a miniball that is a 'smart-pill," so that once ingested, it delivers medication according to its programmed responses to the conditions it encounters. The inactivating substance may combine with or cleave the active drug molecule with or without the addition of another substance and/or the application of heat. The release of an inactivant-activating substance from the entry or at the exit jacket or the inactivating substance from the exit jacket can be triggered by a third substance and/or heating. Release at the exit jacket is usually simultaneous with release at the entry-jacket. Cf. start of segment.

End-pivot—A joint that allows the working end of a stay insertion tool (qv.) to be tilted so that the handle can be at an angle; allowing a longer segment of a ductus to be treated through a small entry incision; tilt-end, tilt-pivot, pivot-base, base-pivot, pivot-end.

Endoluminal approach—Approach to the wall of the ductus from inside the lumen; the approach used to inserts miniballs. Approach thus calls for endoluminal in situ testing. Cf. extraluminal approach.

End-plate—The proximal terminus of the barrel-assembly when connection to the airgun power supply is made by engagement in the airgun chamber. It is not only a compound plug but a terminal centering device.

Endothelial breakaway—The ability of a muzzle-head (qv.) to move without clinging to or seizing against the interior of the lumen. Sufficient lubricity and avoidance of a muzzle-head that is too large in diameter for the lumen minimize entrapment by adherence. A lubricant can be delivered to the stuck muzzle-head through a service-channel (qv.). In more elaborate embodiments, the muzzle-head can also be oscillated to work it loose.

End port—A fluid connector in an end-socket (qv.), that is, in the end- or terminal plate (qv.) of the barrel-assembly that allows connection of an external source of pressurized fluid to a barrel-tube (qv.) in a barrel-assembly (qv.) or to a fluid radial projection circuit (qv.) in a radial projection catheter (qv.) for discharge into the lumen.

End-socket—A socket in the end-plate (qv.) when used to connect external devices. It can include electrical, fluid, or both types of connectors; end connector.

End-stent—The first or last stent in a chain-stent (qv.). Cf. chain-stent, articulated and segmented stent-jacket.

End straps—Ductus binding (girding, cinching) anti-migration straps (qv.) when fastened to and extending from the end interconnecting extension-tabs on a segmented-type sectional or chain-stent, so that the ductus itself and not the jacket is girded about, thus requiring a lining of expansion jointed moisture barrier-coated viscoelastic polyurethane foam sometimes faced in gauze to protect the adventitia; except midprocedurally, suture is not wound around a ductus. Side-straps (qv.) do not require such a lining. Wider end-straps are perforated to allow the surface of the ductus to 'breath' and engage in ion exchange. End-straps and side-straps are singular (one-sided) or two-sided toward either end of the jacket according to the difficulty of use, whereas end-ties (qv.) are usually one-sided. These are added to the individual or segmented jacket based upon the application, allowing jacket standardization and reduced cost. Cf. side-straps, end-ties.

End-tabs—The outrigger (qv.) cuffs or collars used to secure end-ties(qv.). The antilevering outriggers used with impasse-jackets (qv.) are not made of suture but rather stiff metal braced. End-tabs assist to prevent migration along the ductus, but do not extend anti-levering stabilization to the outer margins of the outriggers as do the outriggers of impasse-jackets.

End-ties—Anti-migration tethers usually used when circumvascular clearance would result in the abrasion, erosion, or fistulization of neighboring tissue or to add further stabilization to a stent-jacket or impasse-jacket positioned in a location of pronounced movement. End-ties consist of strong woven suture, passed through or prefastened to an eyelet or wrapped about and knotted beneath the head of a wide head rivet toward the ends of the jacket, or in a magnet-jacket, tabs sewn onto the jacket, that extend off to either side of the jacket to gird about the ductus. The girding end-tabs have hook and loop fasteners with a backing of spandex and an internal or ductus contacting surface of expansion-jointed moisture barrier-coated viscoelastic polyurethane foam and if additional resistance to sliding along the ductus is needed, a facing of gauze. The suture is fastened to end-tabs in the same way as it is fastened to the jacket. If greater resistance to sidewise sliding along the ductus is desired, the moisture barrier-coated viscoelastic polyurethane foam is faced with gauze to impart some ribbing. End-tie end-tab type outriggers (qv.) are end-anchors tethered by suture that serve to resist migration along the ductus and can do so about a point of flexion, for example, whereas impasse-jacket type outriggers are metal bridged, or hard-braced, end-anchors that serve primarily to resist levering of the impasse-jacket in an extraction and secondarily its migration. End-ties can unilateral or bilateral; end-belts, shackles. Cf. side-straps, end-straps.

[Radial projection] End-unit—An electrically or fluidically operated radial projection unit (qv.) with its own electrical or fluid pipeline, making it independently controllable. Whereas nonpiped (electrical) units are projectable, piped units can be projectable or unprojectable.

Endoluminal approach—Approach to the wall of the ductus from inside the adventitia; the approach used to implant miniballs.

[Stay] Entry incision—The cut made through the adventitia or fibrosa by the stay as it enters into the wall of the ductus. Term used to distinguish this intracorporeal incision from the incision or trocar puncture used to access the ductus from outside the body, which latter is referred to as the entry wound (qv.).

[Impasse-jacket] Entry collar—An unmagnetized or dummy-collar braced to the entry end of an Impasse-jacket to minimize levering of the impasse-jacket. A corresponding exit-collar if magnetized is by definition not a dummy-collar but an impasse-jacket outrigger (qv.), which term applies to impasse-jacket braced side-collars whether magnetized.

[Miniball] Entry- [impasse- or stent-] jacket—A holding jacket (qv.) encircling a treated ductus, usually a blood vessel, at the start of segment (qv.) identified for differential treatment or at the inlet to a target organ. When targeting is not inherent or physiological, as is iodine to the thyroid gland, confinement to the targeted segment or organ is achieved by binding the therapeutic agent to magnetically susceptible drug and/or radionuclide carrier particles or nanoparticles. A jacket upstream from the start of segment to release a drug activating agent, for example, is not at the start of segment and is not an entry-jacket. Magnetic drug carriers also allow the use of an externally generated radio frequency alternating magnetic field to heat the particles and thus increase the rates of dissolution and uptake, further concentrating the dose beyond what could be prescribed systemically. The jacket can be loaded by injection, infusion, or ingestion of a drug and/or radionuclide magnetic carrier nanoparticle ferrofluid, or in the form of miniballs or microspheres that by dissolving in the bloodstream, affected a by the introduction of a followup agent, and under magnetic traction release the therapeutic substance. The miniball or microsphere-contained agent may be formulated for release at the entry jacket only upon exposed to another substance that serves as a solvent, affording dose and timing control, which is ingested or injected or infused upstream. Locally released and inactivated, the agent can be applied in a higher concentration than were it delivered through the systemic circulation. To pass through the jacket, the residue must be either magnetically nonsusceptible or not so susceptible that the propulsive force of the contents does not overcome the magnetic attraction of the jacket. Unless this force is excessive (such as might occur in rare cases of malignant hypertension, for example), or magnetic uptake by the intervening jacket or jackets is deficient, little of the active drug should continue past the end of segment (qv.) as to require the use of a preplaced exit-jacket (qv.) to release a drug inactivating or neutralizing agent; inflow-jacket, inlet-jacket. Cf. [Miniball] exit- [impasse-] jacket, start of segment.

[Stay] Entry wound—An incision or trocar puncture, usually laparoscopic or 'keyhole' sized, made to access the ductus from outside the body. Term used in contradistinction to the following incision made through the outer layer (tunica adventitia, tunica fibrosa) of the ductus by the stay as it is inserted or injected subadventitially or medially by the stay insertion tool (qv.), which latter is referred to as the stay insertion incision or stay injection incision (qv.). Pretesting, stay injection, and stent-jacket insertion are all through the same entry wound. A single incision will usually allow the leading end of the stent-jacket (qv.), of which the internal surface will usually have been lubricated, to be inserted and expanded about the ductus to achieve circumvascular placement. A longer stent-jacket may require a second incision over the distal end point to secure the distal end-tie of a magnetic stent-jacket or the distal belt-strap (qv.) of a nonmagnetic stent-jacket.

Esophageal tacking—The support of a collapsed tracheal ceiling by attraction to magnets retained along ventrolateral lines within a magnet-wrap (qv.) placed parallel to the segment of trachea affected about the esophagus; magnetic esophageal tracheopexy.

Exit-coating feature—In a stay insertion too (qv.)1, a miniature pump line with terminus positioned over the point of stay ejection to allow stays to be coated with a semiliquid substance.

[Miniball, microsphere, or ferrofluid] Exit- [impasse- or stent-] jacket—A holding jacket (qv.) placed to encircle a ductus at the terminus of a drug and/or radionuclide-targeted segment (length) or at the outflow of a target organ. For treatment within the lumen, the drug and/or radionuclide is ferrobound (qv.) and can be delivered as a ferrofluid. For treatment of an organ, it is separable from the magnetic vehicle or ferro co-bound (qv.) by, for example, containment within microspheres (qv.) or miniballs (qv.) that also contain ferrous content or are contained within a shell (casing, outer coat) containing ferrous content. Whether infused, injected, or swallowed, ferrobound agents are used in ductus to draw the medicinal component against and/or into the lumen wall under the tractive force of a first or entry holding magnetic extraluminal stent or impasse-jacket (qv.), whereas in co-bound agents, only the magnetically susceptible component is drawn to the magnetized jacket, the co-bound drug and/or radionuclide freed to flow downstream when the shell containing both is disintegrated by dissolution, chemical cleavage or binding by another agent, magnetic traction, and/or the application of heat. The medicinal agent released at the entry-jacket, that is, at the start of the segment or inflow to an organ is taken up by the targeted tissue. An exit jacket is only needed when a medicinal and/or radioactive component must be limited to the target segment or organ, uptake by the target is incomplete, and dilution upon passing the target, such as into the general circulation, is insufficient. Neutralization of the agent released upstream can be by heating the exit jacket in an alternating magnetic field and/or binding, cleaving, or other action by an agent or agents released from the exit jacket with or without heat. The agent is thus magnetically held and released by one or more of the foregoing means at the entry jacket as starting point and destroyed by heat or by the release of a neutralizing agent at the exit-jacket as ending point. Cf. [Miniball, microsphere, or ferrofluid] entry- [impasse-] jacket.

Exit-hole—The aperture through which the miniball is ejected; exit-port, muzzle-head port, muzzleport. The term 'muzzle' is not used to avoid confusion with the muzzle of the airgun.

Exit velocity—The instantaneous velocity of the miniball upon discharge at the muzzle-port (qv.); the muzzle velocity upon ejection from the muzzle-head. The term is necessitated by the fact that the barrel-assembly muzzle-head and original muzzle are different parts; insertion of a barrel-assembly into the airgun barrel extends the point of exit distad from the original muzzle; discharge velocity.

[Stent-jacket] Expansion insert—An arcuate segment of absorbable or percutaneous ultrasonic lithotriptor-destructible material applied to an edge of a stent-jacket side-slit or side-slot to allow the stent-jacket to gradually decrease in diameter as an originally enlarged condition of the substrate ductus subsides; stent-insert; stent-insert.

Expansion slit—The cut-line along the side of a stent-jacket (qv.) that providing free edges, allows compliance of the elastic base-tube (qv.) with movement in the wall of the vessel or duct; side-slit. Cf expansion-slot, side-slot.

Expansion-slot—The longitudinal gap along the side of a stent-jacket (qv.) that providing free edges, allows compliance of the elastic base-tube (qv.) with movement in the wall of the vessel or duct; side-gap.

Expansion-strip—One of several bands (strips, lengths) each made of a different polymeric or stoney material cut to the same length, which are supplied with a stent-jacket (qv.). The polymeric strips have a different absorption rate, while those of stone allow disintegration upon demand by lithotripsy. The strips can be cemented alone or in any combination to the edge or edges of the stent-jacket (qv.) base-tube (qv.) side-slit (qv.) or side-slot (qv.) in order of absorption time with the strip at the open edge breaking down first, and so on. When the ductus treated is swollen and the rate of subsidence is reasonably predictable, absorbable strips allow the side-slit or side-slot to be expanded for gradual subsidence in reasonable pace with the ductus, whereas when disintegration is to be subject to direct control based upon imaging, stoney strips allow disintegration by lithotripsy.

Extended adjustment stent-jacket—A stent-jacket (qv.) with a stent expansion insert that includes constituents that take a longer time to be absorbed or require deliberate action, such as the use of a lithotriptor, to break down; extended contraction-time stent-jacket, adjustment stent-jacket.

Extraction electromagnet—A powerful extracorporeal electromagnet used to withdraw a miniball trapped or held within an impasse-jacket through the wall of the ductus and a hole in the mesh thereof to a safe location outside the ductus or entirely outside the body. A method for adapting a nuclear magnetic resonance imaging machine for this purpose even when the miniball is lodged behind bone, a tendon, ligament, or aponeurosis is described in section X2c entitled Stereotactic Arrest and Extraction of a Circulating, Dangerously Mispositioned, or Embolizing Miniball. The field strength is usually set to allow the magnet to be briefly pulsed, thereby extracting the miniball in a controlled incremental manner; however, when the miniball lies behind hard tissue, the field force required may result in extraction entirely outside the body.

Extraction grid—The open mesh or grating-surround of an impasse-jacket that allows the use of an external (extracorporeal) extraction electromagnet to noninvasively extract miniballs suspended in the jacketed lumen through the ductus wall and the mesh to a safe location outside the ductus. Depending upon the strength of magnetization required, a nonabsorbable grid may consist of intrinsically magnetized stainless steel or a metal cage overlain with a neodymium iron boron grain impregnated polymer or copolymer, for example. A nonabsorbable impasse-jacket or one with an absorption period longer than the time to depletion of a high dose rate emitting seed miniball it is to suspend may include an absorbable radiation shield of less persistence than the extraction grid. Since an absorbable extraction grid must withstand the force exerted by the external magnet, unless it has been primed for dissolution on demand, it must not commence disintegrating for a period following extraction. Dissolution on demand is usually effected by heat induction of embedded ferrous granules that melts its matrix and/or releases a solvent to accelerate dissolution.

Extraction [field] intensity; extraction field strength—the magnetic field strength used to remove a miniball that had been misplaced upon implantation.

Extraction perforation—The passage torn through the wall of a ductus and additional tissue by the forcible extraction of a miniball with the aid of an external electromagnet. The extraction perforation is the same in diameter as the miniball extracted, minimizing trauma. In an artery, extraction through the grid of an impasse-jacket (qv.) is at a level proximate to the source so that the perforation is small in relation to the diameter of the ductus and usually remote from the level of eventual embolization. In a vein, greater separation between the source and the impasse-jacket is used. Cf. stereotactic extraction.

Extraluminal approach—Approach to the wall of the ductus from outside the adventitia; the approach used to inserts stays. Approach thus calls for extraluminal in situ testing. Cf. endoluminal approach.

Extraluminal stent—A stent that consists of subadventitially implanted intraductal sperules referred to as miniature balls or miniballs and a periductal (circumductal, circumvascular, perivascular) magnet surround, or stent-jacket.

Extrinsically magnetized stent-jacket—An elastic polymeric or copolymeric base-tube with bar-magnets mounted to its outer surface, hence, discretely magnetized, or laminated (qv.) with an intrinsically (qv.) or quasi-intrinsically (qv.) magnetized layer bonded to its outer surface. An extrinsically magnetized stent-jacket that includes a radiation shield is laminated, with the magnets fastened to the shield layer which in turn, is bonded to the outside of the base-tube. These are encapsulated together for chemical isolation and cushioning before bonding the moisture barrier-coated viscoelastic polyurethane foam lining. Cf. intrinsically magnetized stent-jacket; quasi-intrinsically magnetized stent-jacket; laminated stent-jacket; radiation shielded stent-jacket.

Feed-forward use—The use of a service-catheter (qv.) to deliver a temperature change or substance to the muzzle-head, to the surface of the lumen, or to a point within the lumen wall.

Feed-back use—The use of a service-catheter (qv.) to withdraw tissue, whether ablated, for biopsy, or both.

Fill-coat—A layer applied about a miniball (qv.) or stay (qv.) to increase the ductus wall thickness after implantation. If necessary, implantation-preparatory thickening of the wall is accomplished through the use of a tumefacient. Following implantation, the fill-coat may itself tumesce, or remain passive and become absorbed. The fill-coat may consist of autologous tissue and/or synthetic material to allow or promote infiltration by the surrounding tissue. Otherwise, liposuctioned fat, for example, can be injected through a service-catheter (qv.) with hypotube, or with an injection tool-insert (qv.) before implantation.

Ferrobound—Said of a drug, radionuclide, and/or other therapeutic substance which is chemically bound to a magnetically susceptible carrier particle or nanoparticle and therefore drawn to a magnet along with the susceptible component. The substance can be infused, injected, or ingested as a ferrofluid without containment within and apportionment among a number of miniballs or microspheres, for example. When the ferrofluid approaches a holding jacket (qv.), the carrier particles are drawn to the lumen wall encircled by the holding jacket. Ferrobound agents are used to treat lesions of the lumen wall, whereas ferro co-bound agents are used to target tissue, lesions, or organs downstream. When apportioned among miniballs or microspheres, dissolution of the encapsulating layer or coat, which can be spontaneous or controlled using heat or another chemical, has the same effect. Cf. ferro co-bound.

Ferro co-bound—Said of a drug, radionuclide, and/or other therapeutic substance which is accompanied by, that is, mechanically but not chemically bound together with a magnetically susceptible carrier particle or nanoparticle. When enclosed together within a miniball or microsphere, or held within a miniball or microsphere having an outer shell or coating that contains magnetically susceptible matter, for example, the therapeutic substance remains with the susceptible matter until the shell dissolves or is broken down by heating and/or the introduction of a solvent or enzyme, for example. No longer bound to the susceptible matter, the substance is freed to continue moving through the ductus, such as in the bloodstream, gut, or ureter. Cf. ferrobound.

Filter-deployment solenoid—A subminiature dc powered plunger solenoid in the nose of the muzzle-head (qv.) located behind the stowage silo of the trap-filter used to eject or deploy and retrieve the trap-filter after use. It is dampened to prevent abrupt jerks or jolts that could result in injury to the wall of the lumen.

Fixed [radial projection] unit—A fluidically operated radial projection unit with ejection-irrigation-aspiration function inherent in its structure. Without a tool-insert holding and lift platform and unable to accept tool-inserts, it is variable in the rate and direction of flow-through passively as set at the external control panel, but internally dumb, or invariable in function.

Flex-joint—A ring of elastic material interposed between metal portions of the spindle (qv.) in the turret motor rotor and the splay chamber (qv.) to allow a predetermined amount of flexion; flex-ring.

Flow-through ejector—A flow-through emission tool-insert or emitter (qv.) for releasing a fluid into the lumen rather than injecting it into the lumen wall. By distinction from an electrical/fluid system-neutral or purely self-contained type ejector. Lifting pressure (qv.) forces the lift-platform to rise (move radially outward) uncovering the opening up into the base-plug (qv.) inserted therein thus admitting fluid up into, through, and out the working face of the tool-insert. A flow-through ejection tool-insert can be prefilled as a syringe with an initial load of medication to be ejected or injected ahead of the line medication. Thereafter, different fluids can be drawn from any number of reservoirs in any sequence each at a preferred temperature with the line flushed as necessary; flow-through ejection tool-insert. Cf. in-line radial projection unit.

Flow-through emitter—A flow-through ejection tool-insert (qv.) or ejector, or an injection tool-insert, or injector. By distinction from an electrical/fluid system-neutral or purely self-contained type emitter, which is limited to the type and amount of fluid it contains but is therefore usable in an electrical radial projection unit, a flow-through emitter delivers fluid from a fluid line. Lifting pressure (qv.) forces the lift-platform to rise (move radially outward) uncovering the opening up into the base-plug (qv.) inserted therein thus admitting fluid up into, through, and out the working face of the tool-insert. The tool-insert can be prefilled as a syringe with an initial load of medication to be ejected or injected ahead of the line medication. Thereafter, whether an ejector or injector, different therapeutic fluids can be drawn from any number of reservoirs in any sequence, each at the preferred therapeutic temperature. In an ablation or ablation and angioplasty-capable barrel-assembly, reservoirs can be internal or external, the former imposing space limitations that may require the use of reservoir refill cartridges, the latter requiring lines that may reduce manipulative freedom. Flow-through emitters and fluid lines may require temperature insulation. Cf. injection tool-insert, injector, ejection tool-insert, ejector, emitter, flow-through ejector, flow-through injector.

Flow-through injector—A flow-through emitter (qv.) for delivering a fluid through a hollow needle or multiple hypotubes into the lumen wall. Lifting pressure (qv.) forces the lift-platform to rise (move radially outward) uncovering the opening up into the base-plug (qv.) inserted therein thus admitting fluid up into, through, and out the working face of the tool-insert. The internal chamber can be prefilled with a medication other than that in the line, the initial load, which thus injects ahead of the line medication. Thereafter, whether an ejector or injector, switching among any number of reservoirs in any sequence allows different therapeutic fluids to be injected, each at the preferred therapeutic temperature. Flow-through injectors thus avoid the limitations in quantity and temperature of injectant that apply to syringe-type injection tool-inserts or injectors. Cf. tool-insert, emitter, flow-through emitter, in-line radial projection unit.

Flow-past resistance—The rise in antegrade blood pressure due to obstruction by the muzzle-head (qv.) as a fluid resistor.

Fluid system ejector—An emission tool-insert (qv.) or emitter (qv.) for use in a fluid operated radial projection system (qv.) to emit a fluid into the lumen. These can be either completely self-contained electrical/fluid system-neutral syringes, which in a fluid system, cannot heat the contents, or distinctly fluidic flow-through (qv.) tool-inserts. A flow-through ejection tool-insert can be prefilled as a syringe with an initial load of medication to be ejected or injected ahead of the line medication. Thereafter, different fluids can be drawn from any number of reservoirs in any sequence, each at a preferred temperature. Larger amounts of one or a number of fluids at the same or different temperatures can be delivered through a flow-through ejector via the fluid line, which can be flushed as necessary. Cf. ejector, in-line radial projection unit, flow-through ejection tool-insert, flow-through emitter, fluid system injector.

Fluid system injector—An emission tool-insert (qv.) for use in a fluid (fluidic) radial projection unit to introduce an injectant into the lumen wall. These can be either electrical/fluid system-neutral syringes, which self-contained, are limited to injecting a specific dose of medication or another substance while remaining separate from the fluid or electrical circuit, or distinctly fluidic flow-through (qv.) type tool-inserts. In a flow-through (qv.) type injector (qv.), the base-plug (qv.) connects the tool-insert to the fluid circuit but generally not to an electrical circuit. Lifting pressure (qv.) forces the lift-platform to rise (move radially outward) uncovering the opening up into the base-plug (qv.) inserted therein thus admitting fluid up into, through, and out the hypoendothelial or hypointimal injection needle at the working face. Cf. emission tool-insert, emitter, fluid system ejector, flow-through ejector, electrical injector, electrical tool-insert, electrical emitter, fluid tool-insert.

Fluid tool-insert—A tool-insert that must be connected to a fluid circuit in order to be lifted or discharge fluid into the lumen or lumen wall. By contrast with completely self-contained or system unconnected electrical-fluidic system neutral tool-inserts, which are used in fluid radial projection systems to emit a fluid other than that in the line. A fluid emitter can also be prefilled as a syringe with a fluid other than that in the line but does not isolate the emittant (ejectant or injectant) from the fluid in the line, which prevents fluids from mixing when undesired and allows the fluid in the line to be used purely as an hydraulic medium not necessarily requiring change with every procedure. Cf. fluid system injector, flow-through emitter, in-line radial projection unit.

Foam-wedge—The inner or adluminal component of a double-wedge insert lining (q.v.) for a shield-jacket (q.v.) or a stent-jacket (q.v.) that serves to protect the adventitial microstructures (vasa and nervi vasora) reduce the momentum of a miniball, and trap any miniballs that perforate the adventitia. Cf. bounce-wedge.

Forward drive and sag leveling and stabilizing device—An extendable longitudinal scaffold or framework that holds the barrel-catheter straight, as is essential to eliminate sag and off-axis deflection when the airgun linear positioning table advances the airgun to set the distance between successive discharges; leveling and stabilizing linkage device, extracorporeal barrel-catheter straightener and deflection preventing extension linkage.

Full-round stent-jacket—A stent-jacket that except for a side-slit (qv.) to allow it to expand in diameter, is completely circular (cylindrical) to allow encirclement of a ductus (a vessel or a duct). It is made of resilient tubing to maintain clutching contact with the outer surface of the ductus, and has a side-slit that allows full compliance with the smooth muscle action in the ductus wall; full stent-jacket, complete stent-jacket (as contrasted with a partial stent-jacket (qv.).

Gas pressure relief channel—The portion of the gas pressure relief path (qv.) that consists of a passageway machined into the metal portion of the muzzle-head (qv.) spindle (qv.). In multibarrel embodiments, each barrel channel is provided with a feeder branch to the central channel in the muzzle-head (qv.) and peribarrel space (qv.). The channel serves to divert the gas pressure that builds up in the barrel-channel or channels (qv.) during discharge, preventing the gas from entering the bloodstream; gas return channel.

Gas pressure relief path—The passageway that diverts gas pressurized during discharge from being expelled into the bloodstream producing an air embolism. It takes the pressurized gas through the gas pressure relief or gas return channel (qv.) and then through the gas return tube continuous therewith and end-cap (qv.) for return to the peribarrel space; gas return path; gas return path.

Gas return tube end-cap—A least resistance path or set of paths for relieving the expulsive pressure of the miniballs as these exit the barrel-tube or tubes, thus averting the injection of gas embolism into the bloodstream. Also to dissipate a buildup of pressure, the barrel-tubes contain perforations along their length.

Hand-grip—The addition of an ambidextrous pistol grip or the imparting of an overall conformation to the power and control housing of an ablation or an ablation and angioplasty-capable barrel-assembly, a combination-form ablation or ablation and angioplasty-capable barrel-assembly, a radial projection catheter, or combination-form radial projection catheter to ambidextrously fit the hand.

Heat-window—1. A thin silver or copper sheet area of high heat conductivity in the surface of the muzzle-head (qv.) for allowing heat to flow from the turret-motor (qv.) and/or recovery electromagnet (qv.) windings when circuited to allow secondary use for radiating heat when sent a surge-current. Used to apply heat for any purpose, but primarily to achieve preemptive thermal angioplasty of fatty atheromas and fibrous caps and contents to prevent the release of debris from vulnerable plaques. For this reason, the windows surround the muzzle-head, even though the windings are separately heatable, adhesive backed biaxially-oriented polyethylene terephthalate polyester film (Mylar®) (thermal resistivity 1040) heat shield tape used to reduce window area. 2. Another type of temperature changing window consists of a tool-insert (qv.) blank (qv.). Whether the winding cover or tool-insert type, electrical heat-windows can provide only heat, whereas fluid operated 'heat'-windows are temperature changing tool-insert blanks that can provide both heat as hot plates or cold as cold plates. Directional or radially asymmetrical windows are slit or slot-shaped; thermal window; temperature-changing window; thermal angioplasty window, thermal window-slit, thermal window-slot.

[Tool-insert] Hold-down arms—Small levers used to retain a tool-insert within the lift-shaft (qv.) against the force of gravity and levering forces of contact with the lumen wall at the tool-insert working face encountered in use. Hold-down arms are positioned in depressions adjacent to the opening of the lift-shaft at the surface of the muzzle-head (qv.) or radial projection catheter (qv.). The levers rotate about or slide into complementary round or linear depressions at the top of the tool-insert; swing-over hold-down arms; hold-down clips, lock-down clips.

[Miniball or ferrofluid] Holding jacket—An impasse- or stent-jacket for retaining, releasing, or heat-controlled releasing of a therapeutic substance within a lumen, usually a blood vessel. The substance can be formulated for delivery as a ferrofluid, within microspheres, or a miniball with or without a magnetic casing to remain bound to the carrier particle and thus drawn abaxially against the lumen wall and into the intramural lesion or to be separable from the carrier at the entry (inlet) or exit (outlet) of the target organ. The particles include magnetically susceptible matter which is bound to the therapeutic substance or substances, so that the holding jacket draws the particles against and into the targeted structure. The incorporation of magnetically susceptible matter also allows the particles to be heated from outside the body by an alternating magnetic field to accelerate dissolution and/or uptake. Impasse- as opposed to stent-jackets used as holding jackets have side walls of a fine wire mesh which allows the use of an external electromagnet to extract miniballs or microspheres through the lumen wall to a point outside the lumen or outside the body. A holding jacket can be used to remove or reduce an endogenous, infused, injected, or ingested substance carried by the bloodstream. Cf. margin-levering, [impasse-jacket] tie-downs, [miniball] entry- [impasse- or stent-] jacket, [miniball] exit- [impasse- or stent-] jacket.

[Clip] Hole-group—A group of holes positioned around a rotary magazine clip for simultaneous discharge. The miniballs in any or all groups can be the same or of different kinds, so that ferromagnetic and medication miniballs, for example, can be discharged together. Since each miniball is ejected through a separate barrel-tube, the different type miniballs will be implanted at different radial angles, so that to alternatively implant the different types along the same longitudinal lines about the circumference of the lumen or tracks necessitates rotating the muzzle-head (qv.) with the turret-motor (qv.).

Idle flow—Flow of the line fluid in a fluid radial projection unit circuit, or system, at too low a pressure to close the least resistive check valve along the circuit and therefore continues to flow through the circuit without actuating the most pressure sensitive projection unit in the circuit. Cf. idle pressure.

Idle pressure—In a fluidic radial projection unit (qv.) circuit, a line pressure that is too low to close any of the fluid chamber partition check valves so that fluid flows past these and through the entire circuit. Pertaining to the radial projection system or circuit as a whole, the idle pressure is established by the valve that closes under less pressure than any other, although normally, the units in a system are made to respond alike. The term pertains to the line pressure whether antegrade or retrograde. Increasing the line pressure over the idle pressure in the antegrade direction precedes the lifting pressure (qv.) followed by the emitting pressure (qv.), whereas doing so in the retrograde direction leads to the lifting pressure followed by the intake or aspirating pressure. Flow at idle pressure, or idle flow, allows the direction of line fluid flow to be reversed without actuating any units. The time to reach the unit actuating pressure in the opposite direction is increased, but directional reversal at low pressure substantially eliminates any tendency of the line to whip or jerk that if extreme could cause stretching injury. Instead, the response to an increase in pressure to the lifting pressure is concentrated in the projection units reducing unit response time and allowing sudden reversals that can be used to forestall clogging, for example. Reversal in the direction of flow presumes that tool-inserts in the circuit will not be actuated other than as intended, so that, for example, an emitter which is not meant to function as an aspirator is made to aspirate.

[Miniball or ferrofluid] impasse-jacket—A magnetic holding or trap collar or mantle, prepositioned about a ductus, for drug targeting a certain segment of a ductus or an organ or for placement downstream from a magnetic stent-jacket encircling an artery to prevent a miniball from passing. Impasse-jackets provide an extraction grid (qv.) to allow noninvasive removal of the suspended miniball in the lumen with the aid of an extracorporeal electromagnet. For this reason, an impasse-jacket can incorporate an outer radiation shield only when the shield is destructible on demand by heat induction. The distinction between holding and trap impasse-jackets is functional, not structural. A stent-jacket can be used as a holding jacket but does not allow the noninvasive extraction of a held or trapped miniball from outside the body. By contrast, an impasse-jacket is configured to allow the use of an external electromagnet to extract a held or seized miniball through the lumen wall to a safe location. Its strength of magnetization, focused at its center, must be sufficient to overcome the ability of the pulse and gravity to force a miniball past it regardless of patient posture. In the arterial tree, preserving proportionality of size among lumen, miniball, and impasse-jacket allows trapping the miniball while it is smaller in relation to the diameter of the lumen. This minimizes the potential for embolization and proportionally reduces the diameter of the extraction perforation (qv.) or trajectory. The impasse-jacket is therefore placed as close downstream to the prospective level of miniball release as interference between the magnetic fields of the source and impasse-jackets will allow. Proximity also allows incorporation of a larger mass of magnetizable content to stop the miniball while still distant from the level of embolization; impasse and extraction jacket, trap-jacket, extraction jacket, stopping-collar, guard. Cf. margin-levering, [impasse-jacket] tie-downs, [miniball] entry- [impasse- or stent-] jacket, [miniball] exit- [impasse- or stent-] jacket.

[Intramural] implant—A very small body inclusive of sufficient magnetically susceptible matter to assure tractability or recoverability, and usually including if not consisting predominantly of medication. Extraordinarily, a surgical cement or protein solder, rendered molten with the aid of a heating element in the nose of the barrel-assembly (qv.), for example, if not the predominant constituent, is included. The implant is delivered into the wall surrounding a tubular anatomical structure of any kind (vas, vessel, ductus, gut, airway) by 1. Infixion through a small incision at the body surface with the aid of a stay insertion tool (qv.), 2. Aeroballistic discharge with the aid of a barrel-assembly (qv.), 3. Injection with the aid of an injection tool-insert (qv.) in either a radial projection catheter (qv.) or an ablation and angioplasty-capable barrel-assembly (qv.), or 4. Magnetic attraction from the lumen as ferrofluid-borne nano or microparticles which once intramural. fuse together to form a concrete mass. This multiplicity of options, which can be changed at different levels along a ductus, allows the placement of implants in even a deep and tortuous vessel, for example. Using the last of these methods, introduction into the luminal flow of a vein, for example, can be by conventional infusion or infusion through a small body surface port (qv.) of ferrofluid-borne magnetically susceptible-carried drug nanoparticles, or microparticles. Incorporation into the lumen wall is with the aid of a stent-jacket equipped with tiny electromagnets energized in sequence where constitution of the intramural implants is by aggregation from the passing blood, for example. Cf. periductal implant.

Injection tool-insert—A radial projection unit tool-insert (qv.) with at least one hypointimal, hypoendothelial, subintimal, hypomucosal or submucosal injection needle. Spring-return of the tool-insert (qv.) and recession by the lift-platform assure that the tool working face needle or needles are fully retracted when not in use. Self-contained syringe injectors that do not require connection to a source of electrical or fluid power can be used in either electrically or fluidically operated systems of given size. Self-contained syringe injectors are, however, limited to the amount and type of fluid these store within. When the bottom boss or protrusion inserted into the mechanical retaining socket in the tool-insert holding and lift-platform and the lift-platform also establish electrical or fluidic connection, the contained fluid can be warmed. Fluidic systems can also chill the contents. Injectors can be insulated. Electrical connection can be used to power motive means within the injector. Fluid system flow-through injectors can be switched among multiple reservoirs containing different fluids, to include flush water or carbon dioxide; injector. Cf. Radial projection system, radial projection unit, in-line radial projection unit, emitter, ejector, electrical ejector, fluid system ejector, flow-through injector, flow-through ejector, injector, injection tool-insert, electrical injector, electrical tool-insert, fluid tool-insert, fluid system injector, syringe tool-insert, syringe injector, syringe ejector.

In-line radial projection unit—A series-connected radial projection unit (qv.) in an electrical or fluid circuit. While jointly controlled as on or off and in electrical or fluid current, exceptionally and strategically incorporating a different lifting resistance into each tool-insert holding and lift-platform (qv.) makes it possible for each unit to respond differently in timing and force of elevation to the same current, and for fluid emitters (qv.), in the force and volume of fluid ejection or injection. To optimize functionality, all units, whether electrically or fluid operated are capable of projection (elevation). When this resistance is built into unremovable units so that it cannot be changed, identical response from every unit cannot be obtained, so that units of different resistance in a muzzle-head or separate catheter are marked to indicate the resistance of each. When a response that varies from the rest is not to be used, the unit can be capped with a plug. Tool-inserts such as ejectors, electrical heating, and fluid heating and chilling face-plates meant to remain flush to the surface of the muzzle-head are separated from the lifting mechanism by a gap. However, especially in an electrical system, where fluid of opposite temperature cannot be quickly introduced, retractability can assist to accelerate removal of the extreme temperature, even when retraction does not bring the emitter closer to a temperature changing service-, or 'cooling' catheter. Cf. emitter,

[Stay] Insertion incision—the slit made through the tunica fibrosa, tunica external, or adventitia by a stay as it enters the wall of the ductus; term used to distinguish this incision from that used to gain intracorporeal access, which is referred to as the entry wound.

In situ test—A test to predetermine the exit velocity (force of discharge) suitable for implanting miniballs into a given segment of a ductus with minimal risk of perforation. Due to the unpredictability of diseased tissue, in situ testing is necessitated regardless of whether a stent-jacket is to be placed prior to discharge. Implanting drug releasing and irradiating seed miniballs does not call for a stent-jacket, which could be justified only where a perforation could do serious harm.

Intake pressure—In a fluid radial projection system, the line pressure in the retrograde direction at which a given tool-insert is forced to aspirate. The intake pressure follows first the idle pressure (qv.) then the lifting pressure (qv.) and is the reciprocal of the emitting pressure (qv.); aspirating pressure.

Interventional airgun—A special-purpose gas-operated implement for implanting ferromagnetic, medicated, or gamma radiation emitting seed spherules into tissue by projection. Proper adjustment in the force of impact critical and capable of changing from point to point along the tissue, in situ tissue testing and the ability to reset the airgun quickly and precisely midprocedurally can be critical, prompting the development of special-purpose airguns having multiple control points for quick resetting.

Intrinsically magnetized stent-jacket—A homogeneous single layer, such as one consisting of thin sheet stock magnetized stainless steel or a magnetic polymer or copolymer, that provides the magnetization and structural properties required in a stent-jacket (qv.). An intrinsically magnetized layer bonded to the base-tube of an extrinsically (qv.) or intrinsically magnetized stent-jacket to increase its magnetic force or resilience and not usable independently as a stent-jacket is a layer in a laminated stent-jacket, not a stent-jacket. Radiation shielding materials such as tungsten paramagnetic and thus unable to provide the magnetization needed in a stent-jacket that except for the moisture barrier-coated viscoelastic polyurethane foam lining consists of a single layer, the addition of radiation shielding is by lamination. Cf. extrinsically magnetized stent-jacket; quasi-intrinsically magnetized stent-jacket; laminated stent-jacket; radiation shielded stent-jacket.

Jacket—The component device used to collar about or encircle a ductus whether vascular, endocrine, gastrointestinal, or pulmonary; stent-jacket.

Joint [barrel-assembly or projection catheter]—A divisible ablation or ablation and angioplasty-capable barrel-assembly or a radial projection catheter consisting of two components where the more peripheral or outer is slid over and ensheaths the more central or inner, the two then used as one. For use in larger lumina, the use of a third or fourth ensheathing projection catheter is possible. By definition, an outer or ensheathing component is a combination-form (qv.), while the inner may be either simple (qv.) or itself a combination-form. The outer or outermost component can be exchanged (switched, 'swapped') among any number of others differently equipped as to radial projection circuits (qv.), tool-inserts(qv.), and preloaded medication, for example. Midprocedural ensheathment can be purely to increase the outer diameter, and removal or disensheathment of the outer or outermost to reduce stiffness, but more often uses ensheathment to deliver a capability or therapeutic substance not preloaded in the more inward or central component. When there is one outer component, the joint device is bipartite, when three, tripartite, and so on. Cf. combination-form radial projection catheter.

Jointed stent-jacket—A stent-jacket that consists of separate segments of tubing articulated to allow flexion as to preclude any buckling in the side-slits (qv.); articulated stent-jacket.

Laminated stent-jacket—Any stent-jacket that except for a universally required moisture barrier-coated viscoelastic polyurethane foam lining, consists of more than a single layer. This excludes extrinsically magnetized base-tubes, intrinsically, quasi-intrinsically magnetized, and radiation shielded stent-jackets. Radiation shielding materials such as tungsten paramagnetic and thus unable to provide the magnetization needed in a stent-jacket that except for the foam lining consists of a single layer, the addition of radiation shielding is by lamination. The laminated layers are usually encapsulated for chemical isolation from the internal environment and to provide cushioning. Cf. extrinsically magnetized stent-jacket; intrinsically magnetized stent-jacket; quasi-intrinsically magnetized stent-jacket; radiation shielded stent-jacket.

Lifting height—The distance the tool-insert (qv.) is lifted. Lifting height varies independently of tool-insert height; radial distance, excursion, radial throw.

Lifting pressure—In a fluid radial projection system or circuit, that pressure sufficient to raise a tool-insert into working position. While each unit could be made to rise at a different pressure, differential operation among units in a circuit is generally relegated to the individual tool-inserts, so that this factor usually pertains to the radial projection system or circuit as a whole. Varying the resistance of the chamber partition check valve and/or the lift-platform strip-spring would cause each unit to rise in a preferred sequence; however, the units in a system are usually made uniform. A lifting pressure is equal to the idle pressure plus any additional pressure necessary to overcome the resistance posed by the lift-platform strip-spring, and is thus intermediate between the idle pressure (qv.), and, during antegrade flow, the emitting pressure (qv.), during retrograde flow, the effective intake pressure (qv.).

[Radial projection unit tool-insert holding and] Lift-platform. The tool-insert (qv.) raising, and lowering deck at the bottom of the lift-shaft (qv.) in a radial projection unit (qv.). When the tool-insert is friction fit into a receptacle in the lift-platform or deck, the part is a tool-insert holding as well as lift-platform. The lift-platform raises the tool-insert into working position and retains it within the lift-shaft when not in use. When also used to retain the tool-insert by friction fit as a tool-insert holding and lift-platform, the lift-platform has rising walls about to provide a socket. The lift-platform may incorporate internal elements such as a socket to receive a tool-insert base-plug (qv.), which in an electrically operated unit provides the electrical and in a fluid unit the fluid connection to the circuit. The socket can also serve to friction fit tool-inserts when swing-over hold-down arms (qv.) are not provided at the surface of the muzzle-head (qv.) or separate (special) radial projection catheter (qv.). The lift-platform is raised by a thermal expansion wire or the electrically actuated release of a gas in electrical units and by fluid pressure in fluid units. Retraction in both type units is by a strip-sping (qv.) beneath the platform of which the force must be overcome by the lifting mechanism.

[Radial projection unit] Lift-shaft—A small elevator shaft or well in which a small elevator or lift-platform with a receptacle for inserting any of a number of interchangeable tool-inserts (qv.) rides up and down to either extend the working face of the tool radially outwards or retract it within.

Limited purpose barrel-assembly—A radial discharge barrel-assembly (qv.) which lacks components essential to perform an ablation or an angioplasty.

Magnetic stent-jacket—A resilient tube or base-tube with a slit cut along its side, small bar magnets mounted about its outer surface, and intramural ferromagnetic implants for retracting an implantable ductus wall, such as that bounding an artery. Depending upon the application, may incorporate side-straps or belt-straps to assist in preventing migration.

Magnetless stent-jacket—A resilient tube or base-tube without magnets or intramural ferromagnetic implants for the circumvascular restraint of an unimplantable ductus wall such as that bounding an aneurysm or similar bulging or outpocketing of a ductus. Lacking magnetic attractive support, the intrinsic resilience of the base-tube, belt-type straps or belt-straps, and belt-strap tightness used to secure the base-tube about the defect become significant. The stretchability of the straps essentially substitutes for a portion of the adherence that in a magnetic stent-jacket is provided by magnetic attraction.

Magnet-trap—The miniball trap-chamber or antechamber of a recovery electromagnet, or trap-magnet, used to enclose and retain recovered miniballs. Distinguished from a filter trap (trap-filter, embolic filter). Cf. trap-extraction magnet assembly, trap-filter.

Magnet-wrap—A wrap-surround (qv.), or bandage, in the form of a stretchable collar or cuff for encircling a ductus, ordinarily, one neighboring another ductus or other tissue requiring retraction whether due to stenosis, collapse, or encroachment by or on neighboring tissue. The magnet-wrap mounts permanent magnets for attracting ferromagnetic implants in or attachments to the failed ductus, for example. On a neighboring ductus such as the esophagus relative to the trachea, the wrap situates the permanent magnet or magnets parallel to the ferromagnetic implanted area in the trachea to lift the dorsal membrane or ligament. Only the facing arcs of the ductus or other tissue carry the attractable implants or magnets. Use in a small dog of the esophagus as a platform to support a collapsed trachea where these are juxtaposed is but one application; magnet-wrap-surround, magnet-cuff, magnet-bandage, magnet-jacket, magnetic collar.

[Impasse-jacket] Margin levering—Sudden downward thrust at one end of an impasse-jacket (qv.) under the repulsive force of an extraction electromagnet (qv.). If not suppressed, margin levering, just as ductus-transverse displacement (qv.), can result in sudden wrenching, or flexion and stretching injury to the substrate (encircled) artery. When extension in length to present a greater moment of resistance to lopsided displacement at either side by one continuous impasse-jacket is disallowed by segments along the ductus that are diseased, curved, tortuous, have attachment to neighboring tissue wished preserved, or span a level that must be free to flex, the length is effectively extended by spanning over these segments. Such spanning for elongation is achieved through the use of an interrupted or braced stopping-jacket (qv.), wherein only the impasse-jacket itself at the center is magnetized. If necessary, the impasse-jacket and outriggers (qv.) can be sutured down to subjacent tissue thereby reducing any space or tenuous connective tissue overlying hard tissue; levering; edge-thrusting, edge-pushing, margin-pushing. Cf chain-guard, braced impasse-jacket, [impasse-jacket] tie-downs, ductus-transverse displacement.

Medicated miniball—A spherule for implantation, usually within the wall of a vessel, that incorporates medication which may surround a spherical seed type source of particulate or gamma radiation as a medicated seed miniball (qv.).

Medicated stay—A stay (qv.) for implantation within the wall of a vessel that incorporates medication normally as the outer coating thereof but which may surround a spherical seed type source of gamma radiation as a medicated seed stay; tablet stay. Cf. medication stay, medicated miniball, medication miniball.

Medication-ahead operation—The use of a stay insertion tool (qv.) auxiliary syringe (qv.) to discharge semiliquid medication onto the outer surface of a ductus so that the stay in passing through carries a coating of the medication on both its upper and lower surfaces into the ductus wall; medication-before operation. Cements and therapeutic substances that are too light or low in viscosity ('thin,' 'runny') may require thickening. Cf. cement-ahead operation.

Medication-follower operation—The use of a stay insertion tool (qv.) auxiliary syringe (qv.) to discharge semiliquid medication onto a portion of the upper surface of each stay as it exits. The longitudinal extent of the coating is controlled by adjusting the timing of auxiliary syringe motor actuation, and while adjustable from stay to stay, is normally kept uniform from one stay to the next; medication-after operation. Cements and therapeutic substances that are too light or low in viscosity ('thin,' 'runny') may require thickening. Cf. cement-follower operation.

Medication miniball—A miniball that consists solely of medication; pill-miniball. Cf. medicated miniball.

Medication stay—A stay (qv.) that consists solely of medication and is fully absorbed. Cf. medicated stay.

Melt-barrier—A partition, usually made of wax, used to divide and thus create separate chambers in an electrochemical tool-insert (qv.) so that each chamber can be filled with a reagent that when mixed with the other reacts to produce heat and/or release a gas. The barrier extends up through a slot-shaped opening running along the top of the roof, so that when the wax barrier is melted, the slot serves as an outlet for the gas generated. To mix the reagents, the barrier is melted by passing current through a heating wire, such as one made of nichrome, embedded in the partition and running through the plug in the base of the tool-insert to plug into the socket at the bottom of the lift-shaft (qv.). When used to lift a separate syringe tool-insert (qv.) into the injection position, the syringe sits atop this double compartment; when the working face of the tool-insert itself is to lift into position against the lumen wall to apply heat under pressure, a gas-tight cap overlapping the roof of the lower chambered portion of the tool-insert is elevated by the gas. Such a tool-insert essentially includes its own lift-platform.

Miniball [Miniature ball]—A spherule projectile such as that used in 'BB' guns but much smaller, for use in man, for example, generally ranging in diameter from 0.25 to 2.0 millimeters, and most often 1.14 to 1.52 millimeters. Manufactured in large volume, miniballs are used in bearings, ballscrews, and ballpoint pens, and can be ferromagnetic or magnetic. consist entirely of medication, represent small spherical irradiating seeds, or within the caliber usable, combine these in concentric layers; spherule, miniature sphere, minisphere; spherule, minisphere.

Miniball-hole—The opening in a rotary magazine clip in which a miniball is fixed in position for discharge. The distal and proximal holes describe the openings to a tunnel that runs through the clip, and an internal circumferential ridge midway along the tunnel prevents the miniball from dropping into the barrel. Various dried solutions of sugars and starches that differ in retentive strength are used for added adhesion until discharge or to differentially adjust the relative propulsive force essential to initiate the ejection, hence, the muzzle velocity, of a given miniball in a set of miniballs for simultaneous discharge as a set.

Miniball-magnet—A magnetized miniball, which can additionally be coated for the delivery of medication or radiation.

Minimally ablation or ablation and angioplasty-capable barrel-assembly—An airgun barrel-extending catheter, or barrel-assembly (qv.), devised to allow intermittent or continuous ablative or angioplastic treatment during discharge implantation; minimally airgun-independent capable barrel-assembly.

Mixed [chain-stent]—An articulated rather than a segmented unitary chain-stent wherein the sub-stents (qv.) differ to meet the different requirements of the segment encircled by each. Thus, consecutive sub-stents may incorporate magnetized metallic base-tubes or magnet-mounting polymeric or nonmagnetic metallic base-tubes, for example. Cf. articulated and segmented [chain-stents].

Mixed shot-group—A shot-group (qv.) containing more than one kind of miniball (qv.), such as one ferromagnetic for use with a magnetic stent-jacket (qv.) and one that consists of medication. Either consistent assignment of given type miniballs to a specific barrel-tube or use of the turret-motor (qv.) is used to include the different types along different tracks (qv.).

Monobarrel [barrel-assembly]—A barrel-assembly having one barrel-tube. A monobarrel can be of the simple pipe kind and thus end-discharging through a singular muzzle-port at the distal end or housed within a more or less shuttlecock or torpedo-shaped muzzle-head with the muzzle-port or ports about the circumference referred to as a radial discharge monobarrel type barrel-assembly. Whereas a simple pipe is for use in the airway, a radial discharge barrel-assembly is for use in ductus and embodiments for use in blood vessels must incorporate features to prevent the backflow of blood into the muzzle-head or the injection of gas into the bloodstream during discharge. Such features include pressure relief means in the form of a barrel-catheter (qv.) to provide a peribarrel space (qv.) within, and an extracorporeal one-way safety valve at the proximal end of the barrel-catheter, and gas return channels (qv.) in the spindle (qv.) to bleed off excessive gas pressures before these can arrive at the muzzle-port.

Motorized swivel joint—A remotely rotated junction in a radial discharge monobarrel (qv.). With only the one barrel-tube, rotation is concentric with no rotatory deflection.

Motorized turret joint—A remotely rotated junction in a radial discharge multibarrel (qv.). Since plural barrels must be off-center, rotation imparts a rotatory deformation and longitudinal foreshortening to the barrel-tubes, which must be compensated by pliancy, slack in the splay chamber (qv.), and reciprocal movement in the barrel-tube-(qv.) barrel-channel (qv.) joints.

Multibarrel [barrel-assembly]—A barrel-assembly with multiple (plural) barrel-tubes, which is always of the radial-discharge type; multiple barrel barrel-assembly.

Multistage magnetic drug-targeting—Encirclement with magnetic collars (jackets, mantles, wrap-surrounds) which are compliant with the intrinsic smooth muscle action of the ductus or the positioning of magnetized miniballs or stays at successive points along the path of a bodily substance or a gland or organ associated with the substance for the purpose of accelerating the uptake of a drug or other therapeutic agent by the target substance, gland, or organ. Mantling thus comprehends primarily impasse-jackets, but also stent-jackets and magnet-wraps, and mantling at the successive can use that type jacket best suited to the anatomy. Patch-magnets are suited to such use only when resistance to contraction of the ductus is permissible. For example, a first impasse-jacket at a level of the gut shown by magnetic marker monitoring to best absorb the drug would serve to draw the magnetized nanoparticle-bound drug against the villi for quicker passage into the bloodstream, for example, while a second impasse-jacket mantling about the main artery leading to the targeted gland, organ, lesion, or neoplasm would draw the drug into that lesion, for example. Cf. single stage magnetic drug-targeting.

Muzzle—The distal terminus of the airgun, not to be confused with that of the muzzle-port(s) or extended muzzle(s).

Muzzle barrel—The portion of a barrel distal to the insertion and end of the plastic barrel-tube into its muzzle-head flush joint socket and start of the metal portion of the barrel.

Muzzle-head—The component mounted at the front or distal end of the barrel-assembly barrel-catheter (qv.) containing the barrel exit port or ports and the trap-extraction magnet assembly; muzzle-probe. A distinct muzzle-head is characteristic of radial discharge barrel-assemblies; however, the term applies to simple pipe barrel-assemblies as well, in which distinction as the muzzle-head consists of no more than a rotary joint in the barrel-catheter.

Muzzle-head access barrel—A barrel-tube used, for example, to allow a lubricant or medication to be delivered to the endothelium through a muzzle-port or a cooling catheter to be aligned in closer adjacency to a heated element; service-channel, barrel-assembly distal access barrel-tube.

Muzzle-port—A miniball exit-hole at the distal terminus of a simple pipe muzzle-head or short of the tractive electromagnet set in a radial discharge barrel-assembly barrel-tube; ejection port.

[Muzzled-] spindle—The rotating part of the muzzle-head distal to the turret-motor housing; muzzle-head spindle.

Muzzle velocity—The velocity upon exiting the muzzle-head exit portal, or muzzle-port. Since the term would conventionally apply to the velocity of the projectile as it exits the muzzle of the airgun rather than the muzzle-port at the distal end of the barrel-assembly, the term exit velocity is preferred.

Needle-switch—A normally open single pole double throw miniature lever switch on an electrical syringe injector (qv.), which is closed by the force of obstruction against the needle-flange.

Nose—The front end, or more restrictedly, the face-on aspect of the front end, of a barrel-assembly (qv.) or radial projection catheter(qv.). Except in thermal angioplasty or ablation-incapable and combination-form (edge-discharge, through-bore) barrel-assemblies (qv.) and radial projection catheters, it is usually occupied by a heat-window (qv.) for minimizing the risk of disrupting vulnerable plaque on contact. A fiberoptic endoscope may be centered in the heat-window. Cf. nosing, nose-cap.

Nosing—The treatment at the nose of a barrel-assembly (qv.) or radial projection catheter(qv.). A combination-form will have an opening, or nose-hole (qv.), that depending upon the application, may remain open, such as to allow blood to pass through, or is occupied by a laser, atherectomy, or other commercial cabled device. A rotatory or directional atherectomizer is kept receded behind the nose-hole, which remains open and is urged against the lumen wall when a spring at a distance behind the nose emerges. The nose of a simple (noncombination-form, boreless) radial projection catheter will usually have a fine fiberoptic endoscope centered within a heat-window (qv.). In larger embodiments for use in the gastrointestinal tract or trachea and bronchi way where debris must be prevented from entering when the bore is vacant, a push-through annular brush or a snap-in spring-loaded nose-hole plug, or nose-cap, is used to seal the nose. The nose-hole will usually by encircled by a heat-window for searing vulnerable plaque and any potentially embolizing debris liberated. For an improved field, cabled devices for viewing and lasering usually protrude somewhat forward of the nose center. Cf. Nose.

Nose-cap—A plug for sealing the opening at the front end of the central channel (bore) or nose-hole (qv.) in a combination-form (qv.) radial projection catheter (qv.) or in the edge-discharge (qv.) muzzle-head of a combination-form (through-bore, edge-discharge) barrel-assembly. Snapping in with prongs that undercut a slight rim surrounding the nose-hole, and having a spring-loaded hinged cap that automatically closes when not forced open, it is removable to allow the central channel to be passable only when outside the body. While competitive in cost, it is not preferred either for preventing the entry of debris into the central channel in the gastrointestinal tract, for example, where a push-through surround of wiping fingers cleans the retracting distal end of the device uniformly all about and closes off the nose-hole behind the retracted device as preferred, nor for urging a centered side-cutting device such as a rotational burr or linear shaver, for example, into approximately parallel abutting relation with the lumen wall in an artery or with any similar ablation device in the airway, for example.

Nose-hole—The opening at the distal (front) end or nose of the muzzle-head in a combination-form (through-bore, edge-discharge) barrel-assembly or a combination-form (through-bore) radial projection catheter. Cf. nose-cap.

One-over barrel-assembly—A barrel-assembly (qv.) with at least one barrel-tube more than is needed for implantation. The additional barrel-tube serves as a service-channel, that is, allows adjunct function or service catheters, such as a test rod (qv.) or cooling capillary catheter (qv.) to be passed down to the muzzle-head. For cooling, this is significant with edge-discharge (combination-form, through-bore) barrel-assemblies, which lack a central canal.

[Impasse-jacket] Outrigger—A shorter collar end-braced to an impasse-jacket (qv.). An upstream or entry outrigger is unmagnetized, and when used only to minimize levering of the impasse-jacket, the exit-outrigger or exit-collar is unmagnetized as well. If to prevent any drug that was not taken up by the impasse-jacket from passing downstream, the exit-collar is magnetized, it is not a dummy-collar, which is an unmagnetized outrigger.

[End-tie] Outriggers—The binding straps connected to the ends of the suture tie-lines of end-ties (qv.) used to bind the lines to the ductus off to either end of the jacket. Whether unilateral or bilateral, the straps attach with hooks and loops. These and any other straps applied directly to a ductus have a backing of a highly elastic and porous or 'breathing' fabric such as spandex, and to protect the adventitia, an internal lining of expansion-jointed moisture barrier-coated viscoelastic polyurethane foam. If the stretching open of the joints between the foam segments is too brief for 'breathing' or ion exchange, then the strap is perforated. End-tie end-tab type outriggers are end-anchors tethered by suture that serve to resist migration and can do so about a point of flexion, for example, whereas impasse-jacket type outriggers are metal bridged, or hard-braced, end-anchors that serve primarily to resist levering of the impasse-jacket in an extraction and secondarily its migration. To afford ribbing for improved traction or grip when the closed strap is especially susceptible to sliding, the internal or binding surface is overlain with wide mesh gauze; end-collar, end-cuff, end-tab.

[Impasse-jacket] Outriggers—Nonmagnetized or dummy-collars connected by rigid bridge-arms to the ends of a center impasse-jacket. The outriggers are constructed as is the impasse-jacket of two mesh half-tubes connected by spring-hinges with moisture barrier-coated viscoelastic polyurethane foam cuff-linings but are usually shorter than the impasse-jacket and not magnetized. This produces a longer structure that is less susceptible to impasse-jacket margin levering (qv.), and interrupted or noncontinuous, allows segments of the ductus to be rigidly spanned across (straddled, skipped over) when diseased, the attachment thereto is to be preserved, the segments are tortuous, or must be free to flex. When necessary, the outrigger end-cuffs (qv.), as those of the impasse-jacket itself, can be tied down with suture to the closest neighboring tissue of sufficient strength to disallow ductus-transverse displacement (qv.); however, this will usually require lengthening the access incision; dummy-collars. Cf. [impasse-jacket] ductus-transverse displacement, levering, chain-guard, rim-bridge.

Paired jacket release and neutralization—The use one impasse- or other type jacket to trap drug carrier bound magnetically susceptible nanoparticles, usually from the blood, and into the wall of the ductus encircled by the jacket. When the drug is not bound directly to as ferrobound but rather ferro-cobound, upon dissolution of the common encapsulating layer, the carrier is drawn against or into the lumen wall and the drug freed to continue upstream. A second exit jacket then performs the corresponding process to neutralize the action of the drug limiting its action to the segment or organ separating the exit from the entry jacket. Cf. Single jacket release, single stage magnetic drug-targeting, paired jacket release and neutralization.

Partial stent-jacket—A stent-jacket with a longitudinal band or slot of the base-tube removed to expand the slide-slit into a side-slot needed to clear an obstruction such as a running attachment of connective tissue. A cutout to admit a branch or an expansion insert (qv.) can be applied to any base-tube, whether full-round or partial; slotted stent-jacket. Used in contradistinction to a complete or full-round stent-jacket (qv.).

Passive delivery [to an impasse-jacket, outrigger, or other type jacket]—Introduction of a drug carrier into an impasse-jacket (qv.), outrigger (qv.), or other type jacket through the enteral path, or by normal flow through the ductus rather than by injection or infusion. Both active and passive delivery apply no less to nonmagnetized jackets. Cf. active delivery.

Patch-magnets—A usually disk shaped more powerful neodymium iron boron permanent magnet that is magnetized in its diametrically central axis and encapsulated within a bioinert jacket mounted on a base with prongs or clasps for attachment to the tissue surrounding a ductus, an organ or deep (muscle) fascia. Patch-magnets are used where stronger magnetic field strength is needed to draw wide stays implanted at a distance or drug carrier particles passing at that level into the ductus wall or organ. In gastrointestinal and tracheobronchial applications, placement is by clasp or prong undercut attachment into the outer layer or layers of the substrate structure or organ, subcutaneous, or to connective tissue such as deep or muscle fascia overlying implanted wide stays, miniballs, or clasp-wrap (qv.) to be attracted. Patch-magnets like segmented stent-jackets can be provided in a continuous strip from which any number can be removed for use; clasp-magnets, magnet-clasps.

Perforation—The through-and-through penetration or puncture of the lumen wall as the result of excessive exit velocity (momentum) or impact force.

Peribarrel[-tube] space—The space surrounding the barrel-tubes in the barrel-catheter. Made accessible to the gas that is pressurized during discharge of the airgun through perforations in portions of the barrel-tubes and centering devices inside the patient, this space allows the pressure to be transmitted from the front to the sides and back of the advancing miniball and thus equalized within the barrel-catheter without the release of gas into the bloodstream.

[Periductal] implant—An absorbable or nonabsorbable stent-jacket (qv.) or impasse-jacket (qv.) Cf intramural implant. When placement is not in a field opened for other surgical purposes, periductal implants are placed endoscopically with the aid of insertion tools described herein through a small incision at the body surface. Access to the coronary vessels is by trephining through the scapula.

Peripheral component—In a barrel-assembly (qv.), the radial projection system circuit or circuits about the periphery of the muzzle-head and all but the exit port or ports of the ballistic component (qv.). In a barrel-assembly of large gauge such as for use in the trachea, bronchi, or gastrointestinal tract, the peripheral component can extend over the intracorporeal length. In a through-bore or combination-form radial projection catheter (qv.), the radial projection system circuit or circuits about the central (cable) component (qv.). The peripheral component includes either or both electrical and fluidic radial projection system circuits.

Piped [radial projection] unit—A radial projection unit (qv.) with supply line (supply tube, passageway, lumen, channel, conduit) which allows perforated ejection or injection tool-inserts (qv.) to release into the lumen, inject into the lumen wall, or aspirate fluids. The fluid can be a drug, hot or cold gas, or drug delivered at a certain temperature, for example. Piped radial projection units have a wider range of function than electrically operated nonpiped units, which are able to lift cutting and heating tool-inserts, for example, into working position, but can deliver only so much fluid as the syringe can hold. Fluid operated units can eject or inject as well as use the line fluid to raise the lift-platform (qv.); fluid operated [radial projection] unit.

Plunger-piston—The multiflanged elastomeric cap-plug at the top of the adhesive cartridge that is inserted into the chamber above the stay load queue. It is forced deeper into the barrel of the cartridge to expel a constant aliquot of adhesive by air pump action; piston-plunger, air pump piston-plunger.

Point to point diagnosis and therapy—The use of a multibarrel radial discharge (qv.) barrel-assembly (qv.) as a diagnostic and/or therapeutic tool whereby its barrel-tubes (qv.) are used as service-channels (qv.) to pass diagnostic sensing probes and therapeutic catheters down to the exit-holes. Such a catheter is typically equipped with a distal or front-end hypotube injection needle, for example. Other catheteric therapeutic devices chill, heat, burn, cut, apply an electrical current, and so on. The turret-motor (qv.) is used to rotate the muzzle-head at that level (longitudinal position, translational displacement) along the lumen so that the therapeutic exit-hole (qv.) is brought to the same point where the diagnostic finding was obtained, and used to deliver the therapeutic substance the finding indicated. The same or another diagnostic probe can then be rotated to face the same point to confirm that the effect intended was obtained, and so on. This process is critically accelerated under the automated control of a positional control system, which controls the linear stage as translation mover, the turret-motor as rotational angle driver; and coordinates the retraction, projection, and ejection of the hypotubes or the functions of other type analytic and therapeutic devices as auxiliary functions. Machine control allows each probe and catheter to be returned to the exact same spot. When used for implantation as well as to diagnose and treat, the muzzle-head alternately rotates a diagnostic probe to the point, if the finding or findings indicate the necessity therefor, the findings-responsive followup therapeutic probe or probes indicated to the same point, a post-treatment confirmatory diagnostic probe if appropriate to that point, and when used for implantation as well as diagnosis, the exit-hole (qv.) for ballistic discharge to that point. When laying down a tighter formation of miniballs, such as to evenly distribute the retractive force of a stent-jacket, the use of automatic means for controlling the process is necessary both for time and precision. Combining syndrome-dedicated and critical path software allows response to the diagnostics such that several different points are tested and treated concurrently; imparting a level of coordination and efficiency that minimizes procedural time and eschews the human error that more complicated sequencing would likely educe; point-to-point diagnosis [or diagnostics], point-to-point diagnosis [or diagnostics] and therapeutics.

Point-washer—A fluid circuit line antegrade-retrograde flow bidirectional tool-insert consisting of an irrigator and an aspirator unified in back to back relation. Reversing the line flow reverses which subunit of the tool-insert is the emitter and which the aspirator. Water or any sufficiently fluid therapeutic solution can be passed through the line. Point-washers can follow ejectors or injectors to quickly remove excess emittant, for example; doublet, back-back tool-insert, back-to-back doublet tool-insert.

[Body surface] port—A small body with openings positioned cutaneously, subcutaneously (subdermally), or both to allow the introduction of medication or other medicinal agents or the withdrawal of diagnostic biopsy test samples in patients with a serious chronic condition, especially when the patient is incapable or drug regimen compliance, necessitating automatic administration. Outflow to the exterior such as to pass urine to a collection bag requires an external opening, while openings for incurrent delivery by infusion are subdermal and marked on the skin with a tiny tattoo.

Power and control housing (and hand-grip)—An enclosure that slides along the barrel-catheter of an ablation or ablation and angioplasty-capable barrel-assembly (qv.). It contains a battery or batteries and control circuitry that allow use of the barrel-assembly as an independent apparatus for performing an ablation or an angioplasty or to inject medication, for example, into the lumen wall. Airgun-independent incapable and capable barrel-assemblies of like diameter can use the same removable slidable power and control housing, and insert adapters can allow the same power and control housing to be shared among barrel-assemblies of different diameter. Any electrical lines for connection to the barrel-assembly plug into a set or bank of jacks or receptacles, a side-socket (qv.), mounted to the housing. Cabled and fluid equipment are connected with a passageway into the barrel-assembly central canal (qv.) through a separate housing about the barrel-catheter that is fixed in position, or if incorporated into the slidable housing, limit the housing to the connection point until disconnected. The components of inmate fluidic systems, to include refillable reservoirs and pumps, are permanently connected, either through lines that afford the necessary slack or as contained within a separate housing fixed in position proximal to the slidable housing. The components within the separate fluid supply housing can, however, be controlled electrically from the slidable housing.

Probe-rod—A fine rod for passing down a barrel-tube so that the lumen wall can be prodded to test its penetrability or deliberately punctured to a limited depth in order to ascertain the susceptibility for the layers of the ductus or tunics to delaminate. A measuring instrument may be used at the driven end to quantify these results.

Proximal—Closer to the operator than the point of reference.

Pull-through—The outward or centrifugal extraction of miniballs or stays through the superjacent layers of the lumen wall that separate these from the internal surface of the stent-jacket under the sustained pull of the circumsurfacial magnets of the stent-jacket over time or under the sudden intense force of a vasospasm. The use of broad cyanoacrylate-coated stays minimizes the risk of pull-through, which can result from sustained nonuniform or disproportionate distribution of magnetic traction on one or a few miniballs of a formation. Less tractive force is responded to by strengthening of the stressed tissue (references at section Stent-jacket Expansion Inserts). Centripetal pull-through into the lumen can result from the improper use of the tractive electromagnets in the muzzle-head, which are intended to recover mispositioned or loose miniballs; tear-through.

[Air] Pump-piston—A disk closely fitted into the longitudinal chamber behind the stay load queue that is moved by an extension or trip connected to or continuous with the trigger or plunger insertion mechanism, which action causes it to reciprocate. This allows it to act as the air compressing surface of an air pump that is used to expel the adhesive used to seal the stay insertion incisions.

Push arm—A blank tool-insert (qv.) for nudging the muzzle-head or radial projection catheter in the opposite direction when extended. For increased reach (lift, distance), it is used in a radial projection unit that incorporates a scissors lift mechanism.

Push-through stopper—A plug used to block the entry into a fluid injector or ejector tool-insert in order to set a threshold line pressure for flow-through. Push-through into the syringe of the stopper allows the tool-insert to be used as an aspirator upon reversing the direction of flow through the fluid supply line. Antegrade flow can be reinitiated following retrograde or aspirative flow, but with the stopper having been removed, no preliminary threshold pressure will precede emission. When aspiration generates sufficient force, a 2-way slit or otherwise perforated membrane allows directional reversal to allow actuative or antegrade and aspriative or retrograde flow to be alternated; break-away plug. Cf. break-seal, slit-membrane.

Quasi-intrinsically magnetized stent-jacket—A single layer of a resilient polymer or copolymer having a magnetized particulate dispersed through or otherwise embedded within it as matrix, such that the one layer provides the magnetization and structural properties required in a stent-jacket (qv.). A quasi-intrinsically magnetized layer bonded to the base-tube of an extrinsically (qv.) or intrinsically magnetized stent-jacket to increase its magnetic force or resilience which is not usable independently as a stent-jacket is a layer in a laminated stent-jacket, not a stent-jacket. The addition of radiation shielding is by lamination, not the additional embedding of overlapping shielding particulate along with the magnetized particulate, shielding materials such as tungsten paramagnetic and thus unable to provide the magnetization needed in a stent-jacket that except for the moisture barrier-coated viscoelastic polyurethane foam lining, consists of a single layer. Cf. extrinsically magnetized stent-jacket; intrinsically magnetized stent-jacket; laminated stent-jacket; radiation shielded stent-jacket.

Radial discharge muzzle-head—A barrel-assembly (qv.) wherein the barrel-tube or tubes (qv.) bend radially within the muzzle-head as to be unseen, and are therefore seen to discharge at the circumference and not, as in a simple pipe, which is exposed to present a sharp tip as needed to obtain accurate aim in an anatomically nonuniform or structured lumen, out the distal end. To uncut the tunicae intima and media, the barrel or barrel-tubes are angled forward. A radial discharge barrel-assembly is not compatible with the use of a bounce-plate; however, the latter would be benefit only in the airway of the smallest dogs.

Radial discharge barrel-assembly—A barrel-assembly with a radial discharge muzzle-head (qv.). It may be of the monobarrel (qv.) or multibarrel (qv.) kind.

Radial discharge monobarrel—A single barrel radial discharge barrel-assembly (qv.) (radial discharge monobarrel, radial m-barrel).

Radial projection catheter—A narrow tube (sheath, sleeve) containing one or more radial projection system (qv.) circuits electrical, fluidic, or both. Lacking a ballistic component (qv.), it is not a barrel-assembly (qv.). With a central channel or central component (qv.) which is available for insertion of a laser or atherectomy device, it is a combination form radial projection catheter. With a central channel that is permanently occupied by a fiberoptic endoscope with surrounding heat-window (qv.), for example, or is absent, it is a simple (noncombination-form, separate, special) radial projection catheter. With the necessary tool-inserts (qv.) installed, radial projection catheters can ablate, angioplasty, atherectomize, inject, eject, and infuse at any therapeutic temperature in any combination or sequence. A radial projection catheter can have projection units situated all along its intracorporeal length, and the units can be enlarged in the longitudinal and circumferential dimensions. The reduction in radial depth for accommodating projection units that results from including a central component is therefore inconsequential; radial projection assembly. A radial projection catheter can be used to inject susceptible matter, to include or omit medication, into the intima. Cf. Combination-form radial projection catheter.

Radial projection circuit—A path for conducting an electrical or fluid current. used to power a radial projection unit (qv.). When multiple, as in a radial projection catheter with both electrical and fluid circuits, or addressed collectively, the circuits are referred to as the radial projection system.

Radial projection system—An electrical or fluid circuit or combination of such circuits with series connected lift-mechanisms or nodes at intervals for accepting tool-inserts (qv.). The capabilities of the two types of system and the tool-inserts these support overlap in the use of electrical/fluid system-neutral syringe injection and ejection tool-inserts but otherwise differ. Cf. in-line radial projection unit, emitter, injector, radial projection circuit.

Radial projection unit—A lifting mechanism about the periphery of a muzzle-head for extending any of a number of differently configured interchangeable snap-in or friction fitted tool-inserts (qv.) radially outward toward the lumen wall. Each unit consists of a simple or telescoping tool-insert holding lift-platform that is raised or lowered inside a small elevation shaft (recess, well) either electrically, by a coiled thermal expansion wire that runs along the floor of the shaft, or fluidically, by the pressure in a fluid line. Recession (lowering, descent) is by reducing or shutting off the electrical or fluid current and the urging of a spring; radial extension unit, radial projector, radial tool elevator, tool-lift, projection unit, radial projection node, radial projection station. Cf. [radial projection unit] tool-insert, [radial projection unit tool-insert holding and] lift-platform, electrical tool-insert, fluid tool-insert, in-line radial projection unit.

Radiation shielded stent-jacket—A stent-jacket with a radiation shield, such as of tungsten sheet, added by lamination. The added layer is applied to a sufficient stent-jacket rather than used to contribute greater magnetization or resilience. Cf. extrinsically magnetized stent-jacket; intrinsically magnetized stent-jacket; quasi-intrinsically magnetized stent-jacket; laminated stent-jacket.

Ramrod—A tube or solid rod with a mildly magnetized tip for retrieving a miniball accidentally discharged from the airgun chamber with too little force to eject from the muzzle-head. A test shaft is never magnetized, and a ramrod is never used for in situ tissue testing; ram-rod.

Rebound lining—A shock absorbent layer applied to the internal surface of a stent-jacket, especially one intended for placement prior to discharge in order to avert the risk of perforation or rebound into the lumen. The resilience of the layer is based upon the thickness of the wall of the vessel, the angle of entry, to which the angle of rebound will be equal in the opposite direction, and the force of impact.

Recovery and extraction miniball electromagnet assembly—An electromagnet or pair of tractive electromagnets at the front end of the barrel-assembly, one in a simple pipe and two in radial discharge barrel-assemblies for recovering loose or extracting mispositioned miniballs. 'Assembly' denotes the magnet or magnets with housing as a distinct component. For trapping operation, or to prevent a loose miniball from passing down the vascular or tracheobronchial tree, these are set to a resting field strength. When paired, the oppositely oriented electromagnets are referred to as a magnet assembly. To allow the extraction of a miniball that settles in an unintended position, the magnets are adjustable together or individually; trap extraction magnet assembly (qv.), trap and extraction electromagnet, tractive electromagnet assembly, recovery electromagnet assembly, magnet assembly.

Recovery electromagnet—Tractive electromagnets used in muzzle-heads and stay insertion tools (qv.) for retracting any mispositioned or retrieving any escaped miniballs; trap-magnet; recovery and retraction electromagnet.

[Impasse-jacket] Rim-bridge—An arm used to connect an impasse-jacket (qv.) to its outrigger (qv.). It is preferably made in one piece, to include a mesh edge half-rim at either end and a cross bar connecting the two. The mesh edge half-rims are crimp fastened and/or otherwise bonded to the mesh edges by solder, for example.

Roof-plate—In a fluid radial projection unit (qv.), a fluid resistor over the outlet chamber of the lifting mechanism to restrict antegrade flow thus forcing fluid up (radially outward) to raise the lift-platform (qv.) and in a fluid tool-insert (qv.) causes the fluid to rise up into the tool-insert and out the working face(qv.). Hinged along the antegrade distal edge of the outlet chamber (qv.) to allow the inner edge of the roof-plate to rise only to a limited extent during retrograde or aspirative flow, the roof-plate serves both to allow debris to pass without clogging the perforations in the plate and cause the flow of fluid to accelerate past and thus create a drop in pressure across the mouth or opening up into the base-plug (qv.) so that the tool-insert functions as an aspirator.

Rotary magazine clip hole—The hole for each miniball in the rotary magazine clip; clip hole.

Seed-core—A miniball or stay containing an irradiating seed at its center, usually overlain with layers of related therapeutic substances. Flatter stays distribute the radioactive content. Both miniballs and stays can also be given a radioactive coating.

Seed-miniball—A usually gamma radiation emitting spherule for implantation within the walls of vessels, the gastrointestinal tract, or the airway to highly localize minimize the region irradiated. Radiation exposure to passing blood is negligible and short-lived. A seed miniball can be jacketed or multiply coated with medication; miniball seed.

Seed-stay—A stay containing a radiation-emitting seed. It may also be covered with one to several coats of medication each of which may dissolve spontaneously or when activated by exposure to an extreme in temperature, making possible the initiation of delivery by the heat of a thermal or cold of a cryogenic ablation or ablation and angioplasty-capable barrel-assembly (which can be the same apparatus). Within the interval that the barrel-assembly can be permitted to remain intraluminal, this makes it possible to monitor the patient for the need of the medication before initiating its release without its withdrawal and reintroduction; stay-seed.

Segmented stent-jacket—A chain-stent (qv.), or sectional stent-jacket (qv.), made from a continuous length of tubing wherein each segment is a substent (sub-stent) continuous with the next through a narrow bridging strip or connecting section that runs the entire length of the tubing. The chain can be used intact, or a certain number of substents cut off for use, or particular substents snipped away leaving only the connecting strip. For example, cutting away a sub-stent except for the connecting strip allows spanning the space intervening between the proximal and distal sub-stents (qv.) while preserving the connection between these to counter migration. Individual sub-stents or any sequential number thereof can be cut off for use as separate stent-jackets. An alternative form of chain-stent (qv.) is articulated, consisting of a train of substents (qv.) attached in a series by wires. Cf. articulated stent-jacket, chain-stent.

Service-canal—The central or side canal in a combination-form (through-bore, edge-discharge) barrel-assembly.

Service-catheter—A tube that is passed down through an unused barrel-tube used as a service-channel (qv.), to access the muzzle-port or to penetrate into the tissue beyond the muzzle-port. It can be used to deliver heat or cold or, with a syringe connected at its proximal end, substances such as medication, adhesives, or lubricants, or to withdraw tissue samples. Its distal end can be directed at, used to swab or scrape, or to penetrate the lumen surface.

Service-channel—A barrel-tube (qv.) or central canal (qv.) used as a guide-catheter for a service-catheter (qv.), or as a catheter itself. A service-channel allows access to the muzzle-head for rapid heating or cooling. Use of a barrel-tube allows access to the lumen wall through a muzzle-port (qv.) for delivery of a lubricant or medication, and/or aspiration. Antiplatelet medication or an anticoagulant can be delivered during thermal angioplasty with heat-windows, for example; muzzle-head access barrel.

[Perforation/Radiation] Shield-jacket—1. A guard in the form of a slit or slotted collar placed about a segment to be discharge implanted temporarily to prevent the continued travel of a perforating miniball, or 2. A jacket or collar for encircling a ductus to shield against radially inward or outward radiation whether the jacket is laminated with a magnetized layer making it a stent-jacket. The radiation shield is generally absorbable over the same period as shielding is required. When the ductus is to be stented, it must be replaced with a magnetized stent-jacket. It is used in lieu of placing the magnetized jacket at the outset only when the jacket magnetization uncontrollably deflects or jerks aside the muzzle-head, interfering with discharge aiming accuracy, and the application of counterbalancing magnetic traction by the recovery electromagnets in the muzzle-head or an extracorporeal electromagnet do not allow the instability to be tolerated. A shield-jacket made to counter perforations is removed immediately following discharge and therefore omits a radiation shield, which must be left in place until the source of radiation decays to a level that does not require shielding, at which time it may as appropriate, spontaneously break down, can be noninvasively disintegrated by chemical means or heat induction, or simply left in place. If incorporating continuous ferromagnetic material, it can be heated to warm the segment it encircles noninvasively by magnetic or electromagnetic induction. It consists of a slit length of pliant tubing or base-tube (qv.), or a double-wedge (qv.) lined base-tube. Since the most efficient radiation shield materials are those densest and nonconductive, to additionally incorporate matter for heat induction results in a jacket too massive for some locations. Cf. Radiation shielded stent-jacket.

[Rotary magazine clip] Shot-group—The set of miniballs to be discharged together from the separate hole clusters (qv.) provided for these in the rotary magazine clip. The meaning is unrelated to use of the term shot-group to denote a set of holes in a target produced with a firearm set to certain aiming adjustments; shot-group. Cf. mixed shot-group.

[Impasse-jacket] Side-access connector—A short tube extending radially outward from an impasse-jacket (qv.) and/or one or more of its dummy collars or outriggers (qv.) that allows a catheter attached to an infusion set cannula or Ommaya-like reservoir at the body surface to deliver a drug or other therapeutic substance from a syringe or portable pump, for example, or a sample of the lumen contents to be aspirated for analysis. The slit membrane separating the lumina of ductus and connected catheter opens only when the threshold pressure needed to open it is presented; side-entry connector, side-inlet, side-outlet.

Side-canal A central canal (qv.) which in order to minimize the outer diameter of the muzzle-head is positioned at the periphery, usually with two barrel-tubes to one side. A combination-form barrel-assembly (qv.) for use in the bloodstream has edge-discharge placed gas return channels allowing the central canal to be used for inserting a commercial device such as an excimer laser, endoscope, or rotational burr permanently or for exchanging with other devices midprocedurally.

Side-clips—Fasteners spaced along the length of stent-jacket and stay insertion tools (qv.) for attaching an endoscope, lamp, laser, aspiration line, or other cabled device.

Side-looking—Directed radially outward toward the lumen wall from the longitudinal axis of the lumen or catheteric device, such as a barrel-assembly or radial projection catheter.

Side-port—A side hole in the barrel-catheter (qv.) of a barrel-assembly (qv.) or in a combination-form (qv.) radial projection catheter (qv.). When situated in an extracorporeal (extraductal, proximal) segment of an angioplasty-capable barrel-assembly, the side-hole communicates with the peribarrel space (qv.) or a pressurized gas diversion channel to serve as a discharge pressure relief vent with or without a one-way outlet valve. Generally larger and communicating via a frontomedially directed tube with the central channel or (qv.) bore in a combination-form (qv.) barrel-assembly or in a combination-form radial projection catheter, it serves as a portal for passing through a cabled device, such as a fiberoptic endoscope or laser down to or through the nose or front end. In an intracorporeal (endovascular, intraductal, distal) segment of a combination-form barrel-assembly or a combination-form radial projection catheter, a side-port allows blood to flow into and through the unoccupied or partially occupied bore or central channel (qv.) and out the nose-hole or front end when antegrade, that is, facing into the direction of blood flow and allows flow into the nose-hole and out the side-port when retrograde.

Side-slit—The longitudinal cut along one side of a stent-jacket (qv.) to allow its free expansion and contraction in response to changes in gauge due to tonic, pulsatile, or peristaltic forces. In a partial stent-jacket (qv.), the side-slit is expanded to clear the attachment of the vessel or duct to adjacent tissue following the clearing away of loose superficial fascia; stent-jacket side-slit. Cf. slit-gap, slot-gap, expansion insert.

Side-slot—In a stent-jacket, a side-slit that has been enlarged to clear a connective attachment or a branch of the ductus; a circumferential extension into a longitudinal arcuate gap of the side-slit (qv.) sufficient to clear a ductus attachment or a branch of the ductus; stent-jacket side-slot. Cf. slot-gap.

Side-socket—An electrical and/or fluid line connection receptacle in an extracorporeal (extraductal, proximal) segment of a barrel-assembly (qv.), a radial projection catheter (qv.), or stay insertion tool (qv.). In barrel-assemblies and radial projection catheters, it may serve, for example, to connect devices such as the power supply in the airgun or another power supply, a cold air gun, laser, or gas cylinder to corresponding lines within the barrel-assembly or radial projection catheter. In an ablation or an ablation and angioplasty-capable barrel-assembly, side-sockets are placed in front of (distal to) or on the side or bottom of the power and control housing hand-grip; side-connector. In stay insertion tools, the side-socket allows connection of an auxiliary syringe (qv.) holder or holding frame. Cf. end-socket.

Side-straps—Hook and loop tab fastened belts (bands, strips) on a backing of stretchable, usually spandex fabric for girding about (cinching, binding about) the jacket surrounding the substrate ductus rather than the ductus itself and therefore not requiring a lining of expansion-jointed moisture barrier-coated viscoelastic polyurethane foam and anti-migration gauze to protect the adventitia as do end-straps (qv.) and end-ties (qv.). When the jacket is unmagnetized, resistance to expansion of the ductus is determined by the resilience of the base-tube if any, which is intrinsic in the material or materials of which the base-tube is made, and any resistance added by adjusting the tautness of the side-straps. Side straps can be one-sided where a longer strap has hook and loop tabs to fasten to itself or two-sided where the sides fasten together. To allow uniform adjustment in the force of restraint applied to an incipient aneurysm, side-straps are added to jackets with a base-tube, but seldom to other type nonmagnetized jackets such as perforation shield-jackets (qv.). The side-straps connect to the jacket as do end-straps (qv.) toward either end by means of wide-head rivets. The ability to add these, just as expansion inserts and double-wedge insert linings, for example, to any jacket promotes jacket standardization, reducing the cost of production. Whether used to secure nonmagnetized or magnet-less shield-jackets, magnetized stent-jackets, clasp-jackets (clasp-wraps), or magnet-jackets (magnet-wraps), side-straps, end-ties, end-straps, and the links that connect substents (qv.) in a chain-stent (qv.), for example, are all attached toward the ends of the jacket by wide-head rivets; belt-straps.

Simple—A barrel-assembly or radial projection catheter without a central channel or bore available to receive a cabled device, such as an excimer laser, endoscope, rotational atherectomy or atheroblation burr, or to allow blood to flow through. Eliminating the bore, or minimizing the bore by permanently installing a fiberoptic endoscope of small diameter therein, for example, makes possible a significant reduction in outer diameter; noncombination-form. Cf. combination-form, combination-form barrel-assembly, combination-form radial projection catheter.

Simple impasse-jacket—A miniball impasse-jacket that includes a single length of mesh which is magnetized at the center. When not cushioned beneath, it must be elongated for positional stability to resist ductus-transverse displacement (qv.) and margin levering (:qv.) when an external electromagnet is used to extract a miniball from the jacket. Elongation across intervening segments of the ductus that are severely diseased, curved, must flex, or would best be left attached are by means of bracing (qv.) or the use of a compound (qv.) or chain (qv.) impasse-jacket.

Simple pipe [barrel-assembly]—A single barrel or monobarrel barrel-assembly (qv.) with curved distal portion and a single trap-miniball recovery and extraction tractive electromagnet. A simple pipe may include a bounce plate for reversing the direction of the trajectory. The simple pipe barrel-assembly corresponds to a barrel-tube within a radial discharge muzzle-head (qv.) but is independent and larger. It can be made as a single length of tubing or as one length or segment for the main part of the barrel-catheter, a bent segment of stainless steel, for example, and soft elastomeric distal tip.

Simple stent-jacket—A stent-jacket (qv.) consisting of a single segment of tubing, i.e., a stent-jacket that is not multisegmental and jointed, or articulated.

Single [double-, triple-, quadruple-, multiple-]-discharge—Said of a barrel-assembly with respect to the number of barrel-tubes, hence, the number of miniballs that may be discharged at the same time, not repeating ability.

Single jacket release—The continued delivery over time of a magnetically susceptible drug carrier to an impasse or other type jacket which traps the nanoparticles. A ferrobound (qv.) drug or one bound to the susceptible component is thence drawn into the ductus wall encircled by the jacket, while a ferro-cobound drug is released at that level. By contrast, release and reversal paired jackets release the drug at one level or at the inlet to an organ by an entry jacket (qv.) and counteract or neutralize the drug at a downstream level or at the organ outlet by an exit jacket (qv.). The substrate tubiform structure may be a larger blood vessel, gastrointestinal, urinogenital, or any other. Introduction is preferably oral to allow self administration but except for treatment along the gastrointestinal tract will usually be by direct injection; if by infusion, the small amount of the drug required to deliver it in high concentration for the treatment demands high dilution. The number of potential applications for such use of impasse-jackets with or without a reversal exit jacket (qv.) by type, much less specifically, are myriad. Multiple or array jacket release with or without a terminal or exit-jacket to eliminate the drug or its ability to act at a certain point or level require the graduated distribution among jackets of the carrier-bound drug or drugs by varying the magnetic strength of the jackets and/or the magnetic susceptibility of the carriers along the treated segment Cf. Single stage magnetic drug-targeting, paired jacket release and neutralization.

Single stage magnetic drug-targeting—The use of an impasse-jacket, stent-jacket, or magnet-jacket to draw ferromagnetic or superparamagnetic drug carrier nanoparticles passing through the lumen through the endothelium and into the lesion or neoplasm, for example, in the lumen wall. The most obvious example is placement about an artery to draw medication into an atheromatous lesion. Cf. Multistage magnetic drug-targeting.

Slit-gap—The distance separating the edges of the side-slit (qv.) in a stent-jacket (qv.). When the slit-gap is temporarily lengthened due to the use of an expansion insert (qv.), the out of round (eccentricity) running its length and just inside the base-tube (qv.) is taken up with strips of additional moisture barrier-coated viscoelastic polyurethane foam supplied along with the expansion strips that come with the stent-jacket. Cf. slot-gap.

Slit-membrane—An elastic film used as a two-way or bidirectional fluid resistor. Slit-membranes can be used at the proximal end of the central canal (qv.) of a barrel-assembly (qv.) or in the base-plug (qv.) of a fluid tool-insert. By contrast, a break-seal(qv.) or a push-through stopper (qv.) is one-way (unidirectional). A two-way resistor allows reversal in the direction of the fluid flow through the circuit more than once so that retrograde or aspirative flow can alternate with actuative or antegrade flow repeatedly.

Slitting edge—A retractable razor edge used with a recovery electromagnet to assist in freeing a stay meant for temporary implantation, such as a radiation emitting seed of dose-rate higher than is left in place. When the stay insertion tool (qv.) lacks a bottom end-pivot (qv.) or tilting base-end, the slitting edge is retracted into the butt of the tool. In a tool with an end-pivot, the edge is retracted into the butt-pad that can be used to nudge the butt to a side using neighboring tissue to avoid the need for repeated intracorporeal withdrawal and reentry.

Slot-gap—The distance separating the edges of the side-slot (qv.) in a stent-jacket (qv.). When the slot-gap is temporarily increased due to the use of an expansion insert (qv.), the out of round (eccentricity) running its length and just inside the base-tube (qv.) is taken up with strips of additional moisture barrier-coated viscoelastic polyurethane foam supplied along with the expansion strips that come with the stent-jacket. Cf. slit-gap.

Slotted stent-jacket—A stent-jacket (qv.) having a longitudinal arc of the base-tube (qv.) removed to accommodate a running connective tissue attachment along one side of the vas or ductus stented.

Spindle—The middle portion of the muzzle-head that receives the barrel-tubes and continues these toward the muzzle-ports as the barrel channels. It is usually machined from a single piece of nonmagnetic stainless steel, then through-hardened.

[Muzzle-head] Spindle neck—The portion of the spindle that is journaled within the rotor of the turret-motor.

[Muzzle-head] Spindle throat—the portion of the muzzle-head spindle between the neck journaled within the rotor of the turret-motor and the ejection-head.

Spine and ribs-configured stent-jacket—A stent-jacket (qv.) specially configured to comply with peristalsis along the digestive tract. It can be used to retract the lumen wall radially outward and/or to draw magnetically susceptible drug carrier nanoparticles from a swallowed ferrofluid into a tumor along the esophagus, for example, to accomplish the drawing against or into the lumen wall of a drug, or effect magnetic assisted transfection of small interfering (short interfering, silencing) ribonucleic acid into a tumor, for example; rib-jacket.

Splay chamber—In the proximal portion of a muzzle-head, a cavity distal to the collar securing the muzzle-head to the distal end of the barrel-catheter that allows the barrel-tubes to bend or veer radially outward toward the muzzle-ports gradually as not to kink; barrel-tube splay-chamber.

Start of segment—The proximal or upstream starting level as the starting point for the exposure of a defined length or segment of a ductus to the action of an active drug and/or other therapeutic substance. It is established by injecting or infusing the active substance or by placement of an entry impasse-jacket (qv.), or entry jacket (qv.), containing the drug in inactive form until it is activated at the start of segment entry jacket as the result of the injection of a drug-activating substance upstream. That is, when the physiologically active substance is introduced upstream, that marks the start of segment; when a substance is injected upstream to activate a drug downstream, the latter marks the start of segment. The active drug is usually in the form of a ferrofluid that contains drug carrier particles. When incorporated into a shell such as a microsphere or miniball, the particles are released when the shell breaks down, either by spontaneous (unaided) dissolution or as the result of injecting a breakdown inducing substance upstream. Cf. end of segment.

[Arcuate] Stay—An slightly bowed or arcuate rib or band for insertion into a collapsing or stenotic ductus to correct the condition. A stay that contains ferromagnetic material such as a core of soft iron for implantation into a ductus wall so that the wall will be retracted by an encircling stent-jacket carrying permanent magnets on its outer surface is a stent-stay. Stays lacking ferrous metal that consist of medication, contain an irradiating seed, or that encapsulate a seed with medication are used without a stent-jacket for the purpose of delivery that is local rather than systemic and concentrated are referred to simply as stays. Stays containing ferrous metal for use with a magnetic stent-jacket to expand (retract, destenose, uncollapse) a ductus are referred to as stent-stays; stent-ribs, ribs. Cf. miniball, medication stay, medicated miniball, medicated stay.

Stay insertion incision—The incision made through the outer layer (tunica adventitia, tunica fibrosa) of the ductus by the stay when inserted subadventitially or medially, not the previous incision made to access the ductus from outside the body, which is the stay entry incision (qv.); stay injection incision.

Stay insertion tool—A syringe (push-type) or pistol (pull-type)-configured hand tool for inserting stent or other kinds of stays (qv.) such as drug containing perimedially (subadventitially) or medially through the outer surface and into the wall of a ductus by incisional entry; stay insertion tool, stay infixion tool, stay inserter. Stay insertion tools may be manually operated, but coordinated use of stay coating devices will then require the use of both hands. For this reason, most stay insertion tools incorporate an embedded microcontroller to control all aspects of the stay ejection cycle (qv.) except initiation of each ejection or triggering by the operator. since to coordinate the of the ejection cycle.

Stay insertion tool base—The parts along the bottom or distal working end, of a stay insertion tool (qv.), of which the front portion or foot, which is bonded to the front of the tool barrel is stationary and rested upon the ductus, while the rear portion or butt is depressed during the loading phase or stroke, and raised during the ejection phase of the stay ejection cycle (qv.). These comprise a forward portion or foot, and a rear portion or butt. The front of the foot is the toe, the rear the heel, and the middle, the sole. The distal tip of a cement or medication delivery line terminates just above the front opening of the stay ejection slot at the toe. The foot continues rearward as the sole, the rear edge of which is the heel, situated just below the entry opening into the stay ejection slot. The stay ejection tongue drops down to the butt where it is riveted as the forward element of the butt. The butt consists of the ejection tongue at the front, distal end of the thumb plunger-rod in the middle and distal tip of the magnet probe at the rear, these three elements fastened together by means of a rivet that passes through these and ferrules used to space these three elements apart.

[Stay insertion tool] ejection cycle—The coordinated sequence and timing of component actions in the operation of a stay insertion tool (qv.), comprising loading and ejection phases or strokes. Since the application of cement and medication usually need to be coordinated with stay insertion (injection), means are provided for accomplishing the synchronized unloading of the cement delivery line internal to the tool. With a mechanical embodiment, so long as the inmate stay coating mechanism is engaged by rotating the thumb plunger rod, depressing and releasing the spring-returned thumb-ring and plunger-rod will effect stay coating automatically, the inmate stay coating means then connected as a slave follower. However, were the magnetic strength left high and the operator to withdraw the tool from the insertion site prematurely so that the cyanoacrylate cement had not sufficient time to prevent retraction of the stay with the blade, or were an auxiliary syringe to be incorporated into the ejection cycle, for example, unless the magnetic strength were reduced, the stay could stick to and be retracted by the stay ejection blade. However, to lower the magnetic field force, the operator must use both hands. To avoid the need for 2-handed coordination, avert any excess or reduction in the release of medication or sealant from the inmate or an attached auxiliary syringe due to abrupt thumb plunger-rod downstroke or return by the operator, and to place the operation of an auxiliary syringe (qv.) under ejection cycle-coordinated rather than independent control when desired, more versatile embodiments incorporate an embedded microcontroller to govern all aspects of the cycle except actuation.

[Stay insertion tool auxiliary syringe] Holding frame—A brace or arm for attaching and controllably unloading, or emptying over an interval adjustable in initiation and duration, an auxiliary syringe (qv.) or syringes containing a tissue sealant or medication; [syringe] holder.

Stent-implant—A miniball (qv.) or stay (qv.) with ferromagnetic core that has been infixed within the wall of a ductus for retraction by a stent-jacket (qv.). When the implants are miniballs, which are implanted ballistically, and vulnerable structures surround the ductus that could be injured were a miniball to penetrate entirely through the wall of the ductus, a double-wedge stent-jacket (qv.) that deflects such an otherwise penetrating discharge to an acceptable location in the wall of the ductus is placed first.

Stent implantation—The placement of ferromagnetic miniballs (qv.) or stays (qv.) in the wall of a ductus for retraction by a stent-jacket (qv.).

Stent-jacket—The extraductal (circumductal, periductal, circumvascular, perivascular) component, or base-tube, of an extraluminal stent. A full or fully round stent-jacket entirely surrounds the vessel or duct, whereas a partial stent-jacket encloses only that circumferential extent of the vessel or duct that is exposed without the need to dissect a line of connective tissue that attaches the structure to another or to avoid a branch such as one that plunges to greater depth. Stent-jackets are also characterized as magnetic or magnetless, the former sometimes in the form of a chain or made up of a series (train, string) of separate stents. To minimize the effect of the extraluminal stent upon relatively undiseased portions of an eccentric angiosclerotic lesion, the complete or partial extraluminal stent can be blanked out for the unaffected arcuate segment. In a magnetic stent-jacket, this is accomplished by using a rotary magazine clip in the chamber of the interventional airgun that has the miniball loading holes for the unused sector empty (blank) and omitting the implanting of miniballs and positioning bar magnets in this segment. In a magnetic stent-jacket, limited areas are cut out as necessary. A magnetic stent-jacket is a kind of magnet-wrap (qv.) in the literal sense, but incorporates a resilient base-tube as substrate rather than gauze and a biocompatible stretchable fabric such as spandex and thus is not a kind of bandage or wrap-surround. Cf. magnetic stent-jacket; chain-jacket; magnetless stent-jacket; extrinsically magnetized stent-jacket; intrinsically magnetized stent-jacket; laminated stent-jacket; radiation shielded stent-jacket.

Stent-jacket applicator—A tool, usually a hand-tool, for opening the stent-jacket for encircling the substrate ductus. It may be designed for ease of use endoscopically or robotically rather than manually; base-tube retractor, side-slit retractor, side-slot retractor, stent-jacket expander.

Stent shot-group—An aggregation of miniballs implanted in close formation to prevent pull-through (qv.).

Stent-stay—A band of ferromagnetic metal cambered for concentricity with the ductus into which it is to be inserted subadventitially (perimedially) by means of a special insertion tool for retraction of the ductus wall by an encircling stent-jacket. Stays that do not include concentrated ferromagnetic matter are simply stays, not stent-stays.

Stereotactic or stereotaxic extraction—The immediate resituation to a safe location or removal of an ischemiatizing, or the interception of a potentionally embolizing miniball that cannot be readily dissolved or destroyed. The recovery electromagnets (qv.) and trap-filter (qv.) built into the muzzle-head make the need for an emergency bail-out or last measure unlikely. To assure retrievability, insoluble miniballs include encapsulated grains of iron powder and dissoluble miniballs superparamagnetic magnetite or maghemite. A high field strength external electromagnet or MRI machine is used to withdraw the miniball along a path calculated to least affect intervening structures and thus minimize trauma. Forcible magnetic extraction is generally into the proximate body cavity, skeletal muscle, or other relatively safe nearby location where the minute, sterile, and biocompatible miniball can usually remain. Extraction completely out of the body is rarely contemplated. If necessary, the Ba magnetic resonance imaging machine is used to draw the miniball out to the exterior through the intervening tissue; stereotactic recovery.

Stop-and-lock ring—A nonmagnetic metal annulus about the barrel-catheter that fixes the distance that the barrel-assembly can be pushed into the barrel of the airgun. Tabs that project from the ring periphery fit into slots within a complementary fitting affixed to the airgun muzzle. These tabs slide through ways to engage the barrel-assembly to the airgun. With tabs twisted into the rotary slideway in the female component of the twist-to-lock connector (qv.), the barrel-assembly is locked in position with its proximal end immediately before the face of the rotary magazine clip or miniball to be discharged and in the correct alignment.

Striking-point—The locus or spot where the miniball impacts against the target tissue.

Stopping-magnet—A magnet prepositioned to stop a miniball from continued movement, usually, through the bloodstream. A stopping-magnet used midprocedurally is usually a powerful adjustable external electromagnet that allows the miniball to be stopped and stereotactically extracted through the lumen wall and into a safe location, or if necessary, removed from the body. Postprocedural stopping magnets are usually mounted on special miniball-impasse-jackets (qv.) fitted to the same ductus and configured to least interfere with miniball removal; otherwise, such magnets are mounted to an adjacent structure on a magnet-jacket or patch-magnet. Since the miniball to ductus ratio decreased as the miniball travels downstream in an artery, for example, an effort is made to position stopping-points as proximal to the insertion points as possible; backup magnet, holding magnet.

Stopping-point—The position and level or aiming point of a stop-magnet (qv.) probe. Proximity to the point or point intended of implant insertion stops the miniball while it is smallest relative to the lumen and makes the proportionally smallest extraction perforation if removed by means of stereotactic extraction (qv.).

Subadventitial—just within the external elastic lamina or tunica adventitia as the outer layers of a ductus; perimedial.

Straight-line lining—A lining for a stent-jacket (qv.), which in contradistinction to a double-wedge insert as the alternative, omits an outer resilient bounce-wedge (qv.) about the moisture barrier-coated viscoelastic polyurethane foam. The foam is noninclined but rather disposed parallel to the ductus. Either a straight-line or double-wedge type lining can be inserted along with an expansion insert if necessary upon manufacture or by the operator; parallel lining.

Strike-point—The spot on a bounce-plate (qv.) where the miniball impacts and is rebounded. When rotated concentrically about the long axis of the barrel-assembly and muzzle-head, the trajectories of the successively discharged and rebounded miniballs describe a conical pattern where the strike-point is revolving a distance short of the cone apex and the circular formation of miniballs describes the base of the cone. Since the strike-point establishes the trajectory for rebound whether it is revolved when the muzzle-head is rotated or the bounce-plate is rotated about its own long axis, the latter movement draws the trajectories of the miniballs inward relative to the base of the cone. This allows the operator to nudge the miniballs slightly inward of the larger cycle.

Substent [-jacket]—One component stent-jacket (qv.) in a chain- (serial, compound) stent-jacket. When linked in an articulated stent-jacket (qv.), the connecting wires can be snipped and when a segment in a segmented stent (qv.), the connecting band can be cut with scissors midway between the side-straps at either end to provide a unit stent. Stent-jackets could be routinely marketed as chain-stents.

Substrate [ductus]—The vessel or ductus mantled about by a stent-jacket (qv.), clasp-wrap (qv.), or magnet-wrap (qv.).

Suture loop or suture eyelet—Small optional handles integral with the stent-jacket for passing through suture in order to stabilize the stent-jacket in position by attachment to neighboring tissue in locations where pronounced vasotonic, peristaltic, and/or bodily movement might otherwise cause the stent-jacket to become displaced, or migrate.

Swelling agent—A substance used to temporarily increase the thickness of a ductus wall to make implantation less difficult; tumefacient, swellant.

Swing over lock down arms—Bars that rotate to engage and hold a tool-insert within the tool-insert holding and lift-platform (qv.).

Swivel-motor—The motor used to rotate the muzzle-head in a single barrel or monobarrel radial discharge barrel-assembly, wherein rotation is of one centered or axial barrel-tube, rather than two or more barrel-tubes radial to the central axis; single barrel turret-motor; single barrel turret-servomotor.

Syringe ejector—An ejection tool-insert (qv.). Mechanical ejectors are electrical-fluidic radial projection system-neutral, whereas electrical ejectors are usable only in electrical systems and fluidically operated ejectors are usable only in fluidic systems; syringe ejection tool-insert. Cf. emission tool-insert, emitter.

Syringe injector—A hollow needle or inoculation-type device used to deliver a limited volume of a drug or cement, for example, into or outside the inner lamina of the lumen wall. Mechanical or spring-released injectors are electrical-fluidic radial projection system-neutral, whereas electrical injectors are usable only in electrical systems and fluidic injectors are usable only in fluidic systems. Fluidically operated injectors can deliver a prefilled dose, then continue with fluid from the supply line; syringe injection tool-insert. Cf. emission tool-insert, emitter.

Tablet miniball—A spherule for ballistic implantation, usually into the wall of a ductus, that consists of homogeneous or layered medication. It can include a radiation emitting core. In contrast to a medicated miniball, (qv.), it is not usable for magnetic stenting (qv.). Cf. medicated miniball, medication stay, tablet stay.

Tablet stay—An arcuate stay (qv.) or rib for implantation, usually into the wall of a ductus, that consists of homogeneous or layered medication. It can include a radiation-emitting core or seed. In contrast to a medicated stay (qv.), it is not usable for magnetic stenting (qv.); medication stay. Magnetically susceptible matter, usually superparamagnetic magnetite or maghemite nanoparticles or finely grained powder, is incorporated only if loss within the body poses some risk that makes necessary its retrievability with the aid of a powerful magnet. Cf. medicated stay, medication miniball, tablet miniball.

Temporary implant—A midprocedural protective device, such as a shield-jacket (qv.), placed temporarily to prevent a perforation during discharge and removed before closure. Opposed to an end-implant, such as a magnetic stent-jacket (qv.), that will remain in position after closure. Implants completely or partially absorbed after closure, such as radiation shield-jackets, are never removed and therefore not characterized as temporary but rather nonpermanent end-implants. The term applies to the manner of use of the implant, not to anything intrinsic in it, so that a shield-jacket placed for postprocedural warming by heat-induction at any later date, for example, is not a temporary but rather an end-implant. Cf. temporary implant.

Test shaft—A solid rod or tube (catheter) placed in a barrel-tube to take the place of an implant projectile in order to allow the penetrative force corresponding to the exit velocity to which the airgun is set to be evaluated.

Thumb-ring—In a control-type syringe configured stay insertion tool (qv.), the annulus surrounding the thumb hole. To allow immediate access by touch, controls for auxiliary syringes are mounted about it.

Thumb switch—In a stay insertion tool, a switch mounted to and facing or conveniently situated relative to the thumb of the operator for the immediate manual control of any electrically powered auxiliary function, to include the use of an attached medication or tissue cement dispensing syringe holding frame, suction line, or laser. On the grip of a modified commercial air pistol, a switch situated for immediate use by the thumb.

[Impasse-jacket] Tie-downs—Lengths of suture looped around a peripherally directed (operator-facing) mesh strand (wire, gridline) or strands overlying the foam end-cuffs (qv.) of an impasse-jacket (qv.), and the end-cuffs of any unmagnetized dummy-collars, or outriggers (qv.), to fix the impasse-jacket to neighboring (usually underlying or subjacent) tissue for positional stability during an extraction. Tie-downs prevent forceful impasse-jacket ductus-transverse displacements (qv.) and margin-levering (qv.) of the encircled ductus (usually an artery) into a subjacent space or against ineffectively cushioning or hard tissue during an extraction under the repulsive force of the external extraction electromagnet (qv.). Such movement can wrench the ductus at the end-edges or margins of the impasse-jacket, causing trauma that can lead to restenosis. The suture must not more than mildly bend the ductus at the margins or be so tight that it impairs compliance of the jacket to the pulse or if applied to another type ductus, then the intrinsic muscle action appurtenant thereto. Infirm support from beneath may justify the interposition of a biocompatible cushion as a prop (bolster pad). Cf. [impasse-jacket] ductus-transverse displacement, ductus-normal displacement, margin-thrust, bracing, chain impasse-jacket, chain-guard, chain holding jacket.

[Radial projection unit] Tool-insert—A cutting, abrading, aspirating, gas-ejecting, spraying, or injecting modular working implement for engagement in a tool-holding and lift-platform (qv.) of a radial projection unit (qv.). The insert can also be a blank used as a pushing arm or a plug that disables lifting in that unit. Functionally diverse tools interchangeably fit the opening in a tool-insert holding lift-platform (qv.) of given dimensions. Tool-inserts that require connection to a power source are enertized either electrically or fluidically. Cf. ejector, injector, syringe injector, fluid tool-insert, electrical tool-insert, radial projection system, in-line radial projection unit.

Tool-insert holding and lift-platform—The receptacle for retaining interchangeable tool-inserts in the lift-shaft of a radial projection unit (qv.).

Track—A longitudinal line along a rotational angle about the circumference of a ductus wall for implantation or the implants situated along such a line.

[Miniball] Trap-jacket—An impasse-jacket (qv.) whether simple (qv.) and used in isolation, or braced (qv.), or a component in a compound or a chain impasse-jacket. A trap is used to seize a miniball or miniballs from further passage through the bloodstream (simple-guard, simple guard-jacket, simple trap-collar, simple-trap).

Trap-extraction magnet assembly—An electromagnet or pair of electromagnets mounted to the front of the muzzle-head, of which the individual or combined field strengths can be varied to prevent the escape of miniballs downstream or to retract miniballs that have already been implanted. It is unitized with and integral to every muzzle-head; miniball recovery and extraction tractive electromagnet assembly; recovery electromagnets, retrieval electromagnets, tractive electromagnets, trap-magnet.

Trap-filter—An embolic filter adapted for installation in the nose of an angioplasty-capable barrel-assembly (qv.), usually at the center of a nose heat-window that surrounds it. That is, a miniature filter having the form of a trawling type fishing net, windsock, parachute, or umbrella that is used with shaving or abrading radial projection unit tool-inserts, for example, to prevent distal embolization by intercepting any angioplasty produced debris or a miniball that midprocedurally escapes downstream. The trap-filter is deployed from and withdrawn into a concavity by a miniature dc plunger solenoid set into the muzzle-head nose (qv.). It can be purchased as a commercial product and adapted for incorporation into the nose of the muzzle-head; embolic filter, run-ahead filter, run-ahead trap-filter, filter-trap. Cf. magnet-trap.

Trapping [field] intensity—the low or resting magnetic field strength of the miniball recovery tractive electromagnets used to trap any miniballs that fall into the lumen; trapping field strength.

[Muzzle-head] Turret-motor—In a mono- or multibarrel radial discharge barrel-assembly, the motor used to rotate the muzzle-head at the rotary joint connecting the muzzle-head to the barrel-catheter. Rotation of the off-center barrel-tubes twists these, so that the motor must be limited to an arc through which the barrel-tubes do not deform causing jams upon discharge; t-motor, turret-servomotor, rotation servomotor.

Twist-to-lock connector—A connector consisting of a male with sliding tabs stop-and-lock ring (qv.) mounted about the barrel-catheter at the distance from the end-plate (qv.) to which the barrel-catheter is to be inserted into the airgun barrel, and a female fitting mounted to the front of the airgun muzzle having slots and channels in which the tabs of the stop-and-lock ring are slid around beneath a compressive ceiling until stopped from further rotation. This connects the barrel-assembly to the airgun at the correct rotational angle. In an angioplasty barrel-assembly, the twist-to-lock connector serves as the proximal stop for the hand-grip shaped power or battery pack and control housing when slid back to perform an angioplasty prior to inserting the barrel-assembly in the interventional airgun for stenting; twist to engage connector, twist lock connector.

Working arc—the range of muzzle-head rotation to either side of the center reference point or zero angle of turret-motor rotation as limited by the inception of discharge-obstructive deformation of the barrel-tubes in use, hence, the arc through which the turret-motor is limited in rotating a specific muzzle-head. To rotate the muzzle-head outside this arc necessitates rotation of the barrel-assembly as a whole intraluminally and at the rotating flange component of the twist-and-lock connector affixed to the muzzle of the airgun.

Wrap-surround—A special bandage used to position magnets or ferromagnetic miniballs around a tubular anatomical structure. One mounting miniballs is a clasp-wrap (qv.), which is used when the ductus wall is incapable of being implanted with or retaining miniballs. It is in turn surrounded by a stent-jacket (qv.). One mounting magnets used to exert patenting tractive force upon the miniballs implanted in a neighboring, usually parallel, structure is a magnet-wrap (qv.), which serves in lieu of an immediate stent-jacket. A stent-jacket provides a firm platform to which the ductus-intramural implants are attracted and is not a kind of bandage or wrap-surround.

The invention claimed is:

1. A jacket for encircling a tubular anatomical structure, wherein said jacket comprises i) complementary open-ended semi cylindrical shells fastened together along one long edge by spring-loaded hinges to urge said semi cylindrical shells into a cylindrical conformation when closed, ii) one or more outrigger stabilizers, and iii) a bridge connecting said stabilizer to one of the semi cylindrical shells, said bridge comprising aligned semicircular arms; wherein said jacket is lined with a shape-compliant material and incorporating material magnetized perpendicularly to the long axis of said tubular anatomical structure to draw magnetically susceptible matter within said structure abaxially outward toward said jacket.

2. A jacket according to claim 1 wherein said jacket derives its magnetism by incorporation from the group of magnetic materials comprising an intrinsically magnetic metal, an intrinsically magnetic polymer, small permanent magnets fastened about the outer surface of said jacket, and these in combinations to draw magnetically susceptible matter from a ferrofluid coursing through said lumen of said tubular anatomical structure and hold said matter up against the lumen lining of said structure.

3. A jacket according to claim 1 wherein said jacket uses magnetism obtained by selection from the group comprising an intrinsically magnetic metal, and intrinsically magnetic polymer, and small permanent magnets fastened about the outer surface of said jacket to exercise a stenting function by drawing small magnetically susceptible bodies infixed within the wall of said tubular anatomical structure radially outward.

4. A jacket according to claim 1 wherein the magnetized material of said jacket draws magnetically susceptible matter from a ferrofluid coursing through said lumen and hold said matter up against the lumen lining of said structure.

5. A jacket according to claim 1 wherein said jacket uses magnetism provided by electromagnets fastened about the outer surface of said jacket to draw magnetically susceptible matter from a ferrofluid coursing through said lumen and draw said matter into the lumen wall of said structure.

6. A jacket according to claim 5 wherein said electromagnets are adjusted in field strength in response to a prescription program executed by a microprocessor.

* * * * *